US011505778B2

(12) United States Patent
Shimodaira et al.

(10) Patent No.: US 11,505,778 B2
(45) Date of Patent: Nov. 22, 2022

(54) CONTROL DEVICE, CONTROL METHOD, COMPUTER PROGRAM, AND METHOD FOR PRODUCING ORGANIC COMPOUND

(71) Applicant: AJINOMOTO CO., INC., Tokyo (JP)

(72) Inventors: Yoshiki Shimodaira, Kawasaki (JP); Hiroki Kobayashi, Kawasaki (JP); Takahiro Terawaki, Kawasaki (JP); Yasuhiro Kusunose, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 388 days.

(21) Appl. No.: 16/829,737

(22) Filed: Mar. 25, 2020

(65) Prior Publication Data

US 2020/0308529 A1   Oct. 1, 2020

(30) Foreign Application Priority Data

Mar. 29, 2019   (JP) .............................. JP2019-068866

(51) Int. Cl.
*C12M 1/34* (2006.01)
*C07C 227/28* (2006.01)
(Continued)

(52) U.S. Cl.
CPC ........... *C12M 41/32* (2013.01); *C07C 227/28* (2013.01); *C12M 41/12* (2013.01); *C12M 41/26* (2013.01); *C12P 13/08* (2013.01); *G05B 15/02* (2013.01)

(58) Field of Classification Search
CPC ........ C12P 13/08; C12M 41/26; C12M 41/12; C12M 41/32; G16C 20/70; G16C 20/10; G07C 227/28; G05B 15/02
See application file for complete search history.

(56) References Cited

U.S. PATENT DOCUMENTS

| | | | | |
|---|---|---|---|---|
| 8,406,928 B2 * | 3/2013 | Gupta | ..................... | C08F 10/02 700/282 |
| 8,433,443 B2 * | 4/2013 | Hagerty | ................. | C08F 10/00 526/60 |
| 8,818,562 B2 * | 8/2014 | Bluck | .................... | C12M 41/00 436/24 |

FOREIGN PATENT DOCUMENTS

| | | |
|---|---|---|
| CN | 104616072 A | 5/2015 |
| CN | 106701846 A | 5/2017 |

OTHER PUBLICATIONS

Extended European Search Report dated Aug. 14, 2020 in Patent Application No. 20164165.1, 9 pages.
(Continued)

*Primary Examiner* — Shogo Sasaki
(74) *Attorney, Agent, or Firm* — Oblon, McClelland, Maier & Neustadt, L.L.P.

(57) ABSTRACT

A control device performs control of a culture condition in production of an organic compound by a fermentation method. The control device executes processing a plurality of times to acquire culture data, to calculate, using the acquired culture data, a plurality of candidates for a culture condition set in advance, and a linear model set in advance that outputs a production amount of an organic compound at a future time, the production amount at the future time for each of the candidates, to determine an optimum candidate out of the candidates using the calculated production amount at the future time for each of the candidates and a target production amount of the organic compound at the future time set in advance, and to change the culture condition to the determined candidate. The linear model and the target production amount are set for each time.

15 Claims, 15 Drawing Sheets

(51) Int. Cl.
      *C12P 13/08*      (2006.01)
      *G05B 15/02*      (2006.01)

(56) References Cited

OTHER PUBLICATIONS

Nam Keun Lee, "Statistical Optimization of Medium and Fermentation Conditions of Recombinant *Pichia pastoris* for the Production of Xylanase" Biotechnology and Bioprocess Engineering, XP036460688, vol. 23, No. 1, Mar. 16, 2018, pp. 55-63.

Yachun Sheng, et al., "Optimization of Culture Conditions for Enhanced Butanol Production by a High Butanol Tolerant *Clostridium beijerinckii* F-6" Energy Procedia, XP085634217, vol. 158, Aug. 22, 2018, pp. 471-476.

Xu Rui, et al., "Optimizing Production of Asperolide A, a Potential Anti-Tumor Tetranorditerpenoid Originally Produced by the Algal-Derived Endophytic Fungus *Aspergillus wentii* EN-48" Chinese Journal of Oceanology and Limnology, Science Press, Beijing, CN, XP036205227, vol. 35, No. 3, Jul. 28, 2016, pp. 658-663.

\* cited by examiner

FIG.4

| | CONTROL | RANGE | | INTERVAL 1 | INTERVAL 2 | INTERVAL 3 | INTERVAL 4 | INTERVAL 5 | INTERVAL 6 |
|---|---|---|---|---|---|---|---|---|---|
| No.1 (STANDARD EXPERIMENTAL CONDITION) | NO CONTROL | NO CONTROL | pH | 1 | 1 | 1 | 1 | 1 | 1 |
| | | | TEMPERATURE | | | | | | |
| | | | PHOSPHORIC ACID CONCENTRATION TO BE SUPPLIED | 1 | 1 | 1 | 1 | 1 | 1 |
| No.2 (EXPERIMENTAL CONDITION CORRESPONDING TO TARGET PRODUCTION AMOUNT) | NO CONTROL | NO CONTROL | pH | 1 | 1 | 1 | 1 | 1 | 1 |
| | | | TEMPERATURE | 1 | 1 | 1 | 1 | 1 | 1 |
| | | | PHOSPHORIC ACID CONCENTRATION TO BE SUPPLIED | 1.33 | 1.33 | 1.33 | 1.33 | 1.33 | 1.33 |
| No.3 (EXPERIMENTAL CONDITION WITH OPERATING CONDITION CHANGED) | ADJUST WITH CONTROL | WIDE RANGE | pH | 1 | 1.05 | 0.96 | 0.96 | 1.05 | 1.05 |
| | | | TEMPERATURE | 1 | 1.08 | 1.08 | 0.90 | | |
| | | | PHOSPHORIC ACID CONCENTRATION TO BE SUPPLIED | 1.33 | 3.89 | 3.89 | 3.89 | 3.89 | 3.89 |

| CASE 1 OF TOP1000 SIGN OF MODELS | ΔLys INTERVAL 1 | ΔLys INTERVAL 2 | ΔLys INTERVAL 3 | ΔLys INTERVAL 4 | ΔLys INTERVAL 5 | ΔLys INTERVAL 6 |
|---|---|---|---|---|---|---|
| pH | + | + | - | - | + | + |
| TEMPERATURE | + | + | + | - | - | - |
| PHOSPHORIC ACID CONCENTRATION TO BE SUPPLIED | + | + | + | + | + | + |

| | -- | - | STANDARD VALUE | + | ++ |
|---|---|---|---|---|---|
| pH | 0.96 | 0.97 | 1 | 1.03 | 1.05 |
| TEMPERATURE | 0.90 | 0.95 | 1 | 1.03 | 1.08 |
| PHOSPHORIC ACID CONCENTRATION TO BE SUPPLIED | 0 | 0.67 | 1 | 1.33 | 3.89 |

FIG.7

| | CONTROL | RANGE | 0 | INTERVAL 1 | INTERVAL 2 | INTERVAL 3 | INTERVAL 4 | INTERVAL 5 | INTERVAL 6 |
|---|---|---|---|---|---|---|---|---|---|
| No.1 (STANDARD EXPERIMENTAL CONDITION) | NO CONTROL | NO CONTROL | 0.000000 | 6.046662 | 25.189887 | 49.160148 | 63.215710 | 78.599051 | 87.513892 |
| No.2 (EXPERIMENTAL CONDITION CORRESPONDING TO TARGET PRODUCTION AMOUNT) | NO CONTROL | NO CONTROL | 0.000000 | 6.241579 | 30.520546 | 59.590175 | 75.609422 | 92.530943 | 100.000000 |
| No.3 (EXPERIMENTAL CONDITION WITH OPERATING CONDITION CHANGED) | ADJUST WITH COLTROL | WIDE RANGE | 0.000000 | 5.744614 | 27.042701 | 65.130183 | 77.872633 | 90.339057 | 98.251936 |

FIG.9

| No. | CONTROL | RANGE | | | AT START OF CULTURE | INTERVAL 1 | INTERVAL 2 | INTERVAL 3 | INTERVAL 4 | INTERVAL 5 | INTERVAL 6 |
|---|---|---|---|---|---|---|---|---|---|---|---|
| No.51 (EXPERIMENTAL CONDITION CORRESPONDING TO TARGET PRODUCTION AMOUNT) | NO CONTROL | NO CONTROL | P SOURCE | pH | 1 | 1 | 1 | 1 | 1 | 1 | 1 |
| | | | AMINO ACID | TEMPERATURE | 1 | 1 | 1 | 1 | 1 | 1 | 1 |
| | | | N SOURCE | PHOSPHORIC ACID CONCENTRATION TO BE SUPPLIED | 1 | 1 | 1 | 1 | 1 | 1 | 1 |
| No.52 (EXPERIMENTAL CONDITION CORRESPONDING TO TARGET PRODUCTION AMOUNT) | NO CONTROL | NO CONTROL | P SOURCE | pH | 1.41 | 1 | 1 | 1 | 1 | 1 | 1 |
| | | | AMINO ACID | TEMPERATURE | 1 | 1 | 1 | 1 | 1 | 1 | 1 |
| | | | N SOURCE | PHOSPHORIC ACID CONCENTRATION TO BE SUPPLIED | 1 | 1.33 | 1.33 | 1.33 | 1.33 | 1.33 | 1.33 |
| No.53 (EXPERIMENTAL CONDITION WITH OPERATING CONDITION CHANGED) | ADJUST WITH CONTROL | WIDE RANGE | P SOURCE | pH | 0.82 | 1 | 1.05 | 0.96 | 1 | 1 | 1 |
| | | | AMINO ACID | TEMPERATURE | 1 | 1 | 1.05 | 1.05 | 1 | 1 | 1 |
| | | | N SOURCE | PHOSPHORIC ACID CONCENTRATION TO BE SUPPLIED | 1 | 1.33 | 3.89 | 3.89 | 1.33 | 1.33 | 1.33 |
| No.54 (EXPERIMENTAL CONDITION WITH OPERATING CONDITION UNCHANGED) | NO CONTROL | NO CONTROL | P SOURCE | pH | 0.82 | 1 | 1 | 1 | 1 | 1 | 1 |
| | | | AMINO ACID | TEMPERATURE | 1 | 1 | 1 | 1 | 1 | 1 | 1 |
| | | | N SOURCE | PHOSPHORIC ACID CONCENTRATION TO BE SUPPLIED | 1 | 1.33 | 1.33 | 1.33 | 1.33 | 1.33 | 1.33 |
| No.55 (EXPERIMENTAL CONDITION WITH OPERATING CONDITION CHANGED) | ADJUST WITH CONTROL | WIDE RANGE | P SOURCE | pH | 1.97 | 1 | 1 | 0.95 | 1.05 | 0.96 | 0.96 |
| | | | AMINO ACID | TEMPERATURE | 1 | 1 | 1 | 1 | 1 | 1 | 1 |
| | | | N SOURCE | PHOSPHORIC ACID CONCENTRATION TO BE SUPPLIED | 1 | 1 | 1 | 0.33 | 0.33 | 0.33 | 0.33 |
| No.56 (EXPERIMENTAL CONDITION WITH OPERATING CONDITION UNCHANGED) | NO CONTROL | NO CONTROL | P SOURCE | pH | 1.97 | 1 | 1 | 1 | 1 | 1 | 1 |
| | | | AMINO ACID | TEMPERATURE | 1 | 1 | 1 | 1 | 1 | 1 | 1 |
| | | | N SOURCE | PHOSPHORIC ACID CONCENTRATION TO BE SUPPLIED | 1 | 1 | 1 | 1 | 1 | 1 | 1 |
| No.57 (EXPERIMENTAL CONDITION WITH OPERATING CONDITION CHANGED) | ADJUST WITH CONTROL | WIDE RANGE | P SOURCE | pH | 1 | 1 | 1 | 1 | 1 | 1 | 1 |
| | | | AMINO ACID | TEMPERATURE | 1 | 1 | 1 | 1 | 1.33 | 3.89 | 3.89 |
| | | | N SOURCE | PHOSPHORIC ACID CONCENTRATION TO BE SUPPLIED | 1 | 1.33 | 3.89 | 3.89 | 1.33 | 1.33 | 1.33 |
| No.58 (EXPERIMENTAL CONDITION WITH OPERATING CONDITION UNCHANGED) | NO CONTROL | NO CONTROL | P SOURCE | pH | 1 | 1 | 1 | 1 | 1 | 1 | 1 |
| | | | AMINO ACID | TEMPERATURE | 1 | 1 | 1 | 1 | 1 | 1 | 1 |
| | | | N SOURCE | PHOSPHORIC ACID CONCENTRATION TO BE SUPPLIED | 1 | 1.33 | 1.33 | 1.33 | 1.33 | 1.33 | 1.33 |

| CASE 1 OF TOP1000 SIGN OF MODELS | ΔLys INTERVAL 1 | ΔLys INTERVAL 2 | ΔLys INTERVAL 3 | ΔLys INTERVAL 4 | ΔLys INTERVAL 5 | ΔLys INTERVAL 6 |
|---|---|---|---|---|---|---|
| pH | + | + | − | − | + | + |
| TEMPERATURE | + | + | + | − | − | − |
| PHOSPHORIC ACID CONCENTRATION TO BE SUPPLIED | + | + | + | + | + | + |

| | −− | − | STANDARD VALUE | + | ++ |
|---|---|---|---|---|---|
| pH | 0.96 | 0.97 | 1 | 1.03 | 1.05 |
| TEMPERATURE | 0.95 | 0.97 | 1 | 1.03 | 1.05 |
| PHOSPHORIC ACID CONCENTRATION TO BE SUPPLIED | 0.33 | 0.67 | 1 | 1.33 | 3.89 |

FIG.12

| | CONTROL | RANGE | 0 | INTER-VAL 1 | INTER-VAL 2 | INTER-VAL 3 | INTER-VAL 4 | INTER-VAL 5 | INTER-VAL 6 |
|---|---|---|---|---|---|---|---|---|---|
| No.51 (EXPERIMENTAL CONDITION CORRESPONDING TO TARGET PRODUCTION AMOUNT) | NO CONTROL | NO CONTROL | 0.000 | 5.395 | 21.608 | 48.683 | 62.082 | 72.196 | 82.984 |
| No.52 (EXPERIMENTAL CONDITION CORRESPONDING TO TARGET PRODUCTION AMOUNT) | NO CONTROL | NO CONTROL | 0.000 | 5.187 | 25.331 | 57.570 | 72.429 | 86.239 | 100.000 |
| No.53 (EXPERIMENTAL CONDITION WITH OPERATING CONDITION CHANGED) | ADJUST WITH CONTROL | WIDE RANGE | 0.000 | 5.362 | 24.946 | 62.543 | 76.303 | 95.705 | |
| No.54 (EXPERIMENTAL CONDITION WITH OPERATING CONDITION UNCHANGED) | NO CONTROL | NO CONTROL | 0.000 | 5.028 | 19.302 | 48.517 | 62.617 | 80.640 | |
| No.55 (EXPERIMENTAL CONDITION WITH OPERATING CONDITION CHANGED) | ADJUST WITH CONTROL | WIDE RANGE | 0.000 | 5.313 | 22.383 | 53.248 | 62.039 | 72.978 | |
| No.56 (EXPERIMENTAL CONDITION WITH OPERATING CONDITION UNCHANGED) | ADJUST WITH CONTROL | NO CONTROL | 0.000 | 4.758 | 21.717 | 54.743 | 66.316 | 82.122 | |
| No.57 (EXPERIMENTAL CONDITION WITH OPERATING CONDITION CHANGED) | ADJUST WITH CONTROL | WIDE RANGE | 0.000 | 5.359 | 22.416 | 56.540 | 68.344 | 85.826 | |
| No.58 (EXPERIMENTAL CONDITION WITH OPERATING CONDITION UNCHANGED) | NO CONTROL | NO CONTROL | 0.000 | 5.172 | 20.225 | 47.572 | 61.192 | 80.028 | |

| INTERVAL | J1 TARGET | | J5 VERIFICATION | |
|---|---|---|---|---|
| | TEMPERATURE | pH | TEMPERATURE | pH |
| - | °C | - | °C | - |
| INTERVAL 1 | 1 | 1 | 1 | 1 |
| INTERVAL 2 | 1 | 1 | 0.97 | 0.97 |
| INTERVAL 3 | 1 | 1 | 0.97 | 1 |
| INTERVAL 4 | 1 | 1 | 1.03 | 1.03 |
| INTERVAL 5 | 1 | 1 | 1 | 1.03 |
| INTERVAL 6 | 1 | 1 | 0.97 | 1.03 |
| INTERVAL 7 | 1 | 1 | 1 | 1.03 |
| INTERVAL 8 | 1 | 1 | 1 | 1 |
| INTERVAL 9 | 1 | 1 | 1.03 | 0.97 |
| INTERVAL 10 | 1 | 1 | 1 | 1 |

| INTERVAL | TEMPERATURE | pH |
|---|---|---|
| INTERVAL 1 | + | + |
| INTERVAL 2 | + | + |
| INTERVAL 3 | + | - |
| INTERVAL 4 | + | + |
| INTERVAL 5 | + | + |
| INTERVAL 6 | - | - |
| INTERVAL 7 | + | + |
| INTERVAL 8 | - | - |
| INTERVAL 9 | - | + |
| INTERVAL 10 | - | - |

|  | - | STANDARD VALUE | + |
|---|---|---|---|
| TEMPERATURE | 0.94 | 1 | 1.06 |
| pH | 0.94 | 1 | 1.06 |

FIG.19

| INTERVAL | SIGN OF COEFFICIENT MEDIAN | | J5 CONTROL CONDITION | | INTERVAL | J5 CONTROL DESCRIPTION | | Arg AMOUNT [%] | | |
|---|---|---|---|---|---|---|---|---|---|---|
| | TEMPER-ATURE | pH | TEMPER-ATURE | pH | | TEMPER-ATURE | pH | J1 TARGET | J5 CON-TROLLED | J5-J1 DIFFER-ENCE |
| INTERVAL 1 | + | + | 1 | 1 | 0 | | | 1.22 | 1.29 | 0.07 |
| INTERVAL 2 | + | + | 0.97 | 0.97 | INTERVAL 1 | NONE | NONE | 2.25 | 2.24 | -0.01 |
| INTERVAL 3 | + | - | 0.97 | 1 | INTERVAL 2 | DECREASE | DECREASE | 6.40 | 6.14 | -2.26 |
| INTERVAL 4 | + | + | 1.03 | 1.03 | INTERVAL 3 | DECREASE | NONE | 17.07 | 16.71 | -0.36 |
| INTERVAL 5 | + | + | 1 | 1.03 | INTERVAL 4 | INCREASE | INCREASE | 23.56 | 29.66 | 4.30 |
| INTERVAL 6 | - | - | 0.97 | 1.03 | INTERVAL 5 | NONE | INCREASE | 38.31 | 41.92 | 3.61 |
| INTERVAL 7 | + | + | 1 | 1 | INTERVAL 6 | INCREASE | DECREASE | 51.78 | 53.11 | 1.34 |
| INTERVAL 8 | - | - | 1 | 1 | INTERVAL 7 | NONE | INCREASE | 64.17 | 68.26 | 4.09 |
| INTERVAL 9 | - | + | 1.03 | 0.97 | INTERVAL 8 | NONE | NONE | 76.87 | 84.62 | 7.75 |
| INTERVAL 10 | - | - | 1 | 1 | INTERVAL 9 | DECREASE | DECREASE | 88.71 | 92.91 | 4.21 |
| | | | | | INTERVAL 10 | NONE | NONE | 100 | 96.56 | -3.44 |

CONTROL DEVICE, CONTROL METHOD, COMPUTER PROGRAM, AND METHOD FOR PRODUCING ORGANIC COMPOUND

CROSS-REFERENCE TO RELATED APPLICATION

This application claims priority to Japanese Patent Application No. 2019-068866, filed Mar. 29, 2019, which is incorporated herein by reference in its entirety.

BACKGROUND OF THE INVENTION

Field of the Invention

The present invention relates to control devices, control methods, computer programs, and method for producing an organic compound.

Discussion of the Background

Method A and Method B below are main methods for stabilizing amino acid production by a fermentation method.

Method A: A method that optimizes conditions on, for example, a sugar concentration and a nutritional source concentration before the start of culture based on information on, for example, raw materials, which is known before the start of culture.

Method B: A method that repeats culture on the same condition and optimizes conditions on, for example, culture temperature, pH, and the amount of aeration based on a tendency of a plurality of production results in a trial-and-error manner before the start of culture.

However, Method A and Method B require that the conditions be set before the start of culture and cannot thus perform real-time control of the conditions according to situations during culture. It is considered that, for real-time control of the conditions, a model that estimates a future culture result is required.

In general, Method C and Method D below are main methods for developing the model.

Method C: A method that corrects general formulae based on fermentation technology and metabolic technology such as the Monod expression.

Method D: A method using a black box-like learning model such as a genetic algorithm or a neural network.

CN-B-104616072, which is incorporated herein by reference in its entirety, describes a technique on production of glutamic acid by a fermentation method. Specifically, CN-B-104616072 describes a technique that determines a glutamic acid concentration during fermentation from a history of pH, temperature, the amount of aeration, and the like and determines pH, temperature, the amount of aeration optimum for optimizing the glutamic acid concentration using a three-layer neural network learned by back propagation.

However, in actual production, there are many factors such as raw materials, and an expression obtained by Method C, which does not consider the factors, cannot achieve real-time control of the conditions according to situations during culture. In Method D, because a black box-like learning model is used, nobody can know what factor has a large influence on a culture result. That is, Method D is not readable. Consequently, it is unclear how the conditions should be controlled based on a result obtained by Method D.

SUMMARY OF THE INVENTION

Accordingly, it is an object of the present invention to at least partially solve the problems in the conventional technology.

This and other objects, which will become apparent during the following detailed description, have been achieved by:

A control device according to one aspect of the present invention is a control device that performs control of a culture condition in production of an organic compound by a fermentation method, the control device executing processing a plurality of times to acquire culture data, to calculate, using the acquired culture data, a plurality of candidates for a culture condition set in advance, and a linear model set in advance that outputs a production amount of an organic compound at a future time, the production amount at the future time for each of the candidates, to determine an optimum candidate out of the candidates using the calculated production amount at the future time for each of the candidates and a target production amount of the organic compound at the future time set in advance, and to change the culture condition to the determined candidate, and the linear model and the target production amount being set for each time.

A control method according to one aspect of the present invention is a control method executed by a control device that performs control of a culture condition in production of an organic compound by a fermentation method, the control device executing processing a plurality of times to acquire culture data, to calculate, using the acquired culture data, a plurality of candidates for a culture condition set in advance, and a linear model set in advance that outputs a production amount of an organic compound at a future time, the production amount at the future time for each of the candidates, to determine an optimum candidate out of the candidates using the calculated production amount at the future time for each of the candidates and a target production amount of the organic compound at the future time set in advance, and to change the culture condition to the determined candidate, and the linear model and the target production amount being set for each time.

A computer program according to one aspect of the present invention is a computer program causing a control device that performs control of a culture condition in production of an organic compound by a fermentation method to execute, the computer program causing the control device to execute processing a plurality of times to acquire culture data, to calculate, using the acquired culture data, a plurality of candidates for a culture condition set in advance, and a linear model set in advance that outputs a production amount of an organic compound at a future time, the production amount at the future time for each of the candidates, to determine an optimum candidate out of the candidates using the calculated production amount at the future time for each of the candidates and a target production amount of the organic compound at the future time set in advance, and to change the culture condition to the determined candidate, and the linear model and the target production amount being set for each time.

A method for producing an organic compound according to one aspect of the present invention includes a step of producing an organic compound with a production system having the control device.

BRIEF DESCRIPTION OF THE DRAWINGS

A more complete appreciation of the invention and many of the attendant advantages thereof will be readily obtained

FIG. 4 is a diagram of exemplary operating conditions;

FIG. 7 is a diagram of an exemplary Lys culture result;

FIG. 9 is a diagram of exemplary operating conditions;

FIG. 12 is a diagram of an exemplary Lys culture result;

FIG. 19 is a diagram of an exemplary Arg culture result; and

DETAILED DESCRIPTION OF THE PREFERRED EMBODIMENTS

The following explains an embodiment of a control device, a control method, a computer program, and a method for producing an organic compound according to the present invention in detail based on the accompanying drawings. The present embodiment does not limit the present invention.

1. Configuration

Figure 1:
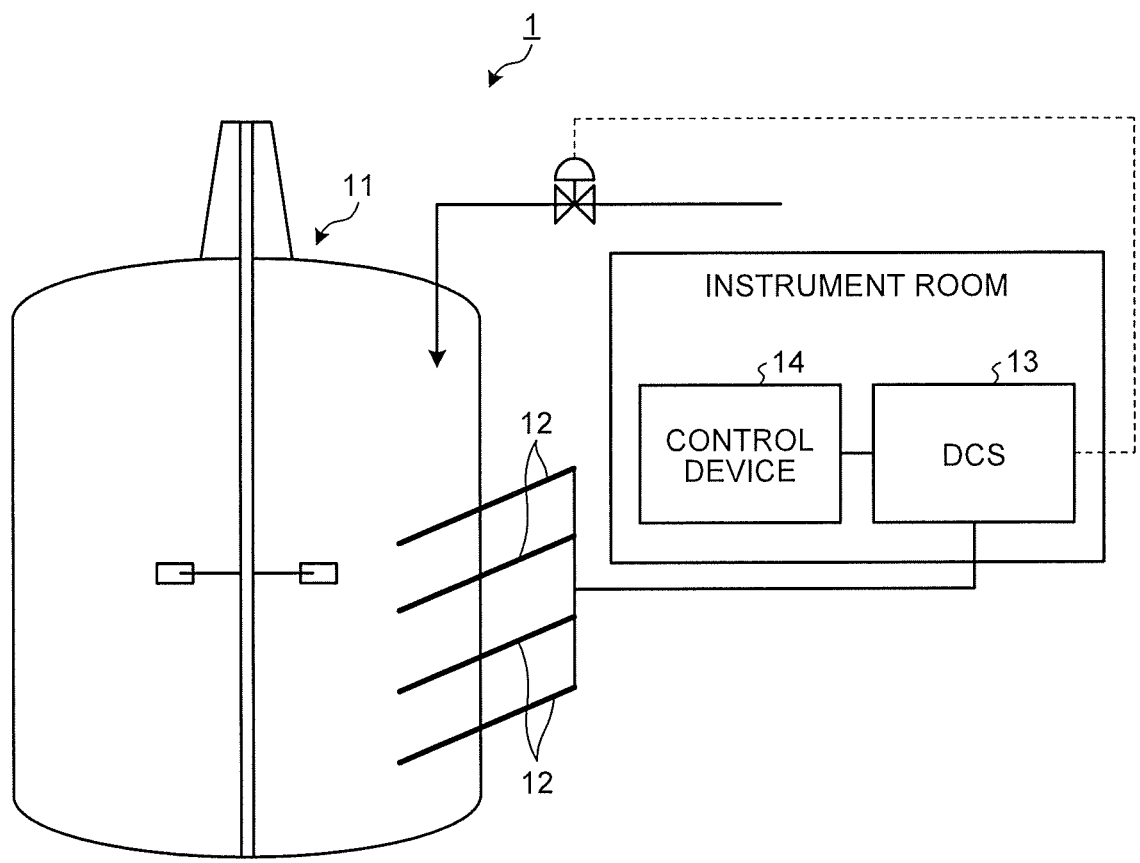
FIG. 1 is diagram of an exemplary configuration of a culture system 1.
Figure 2:
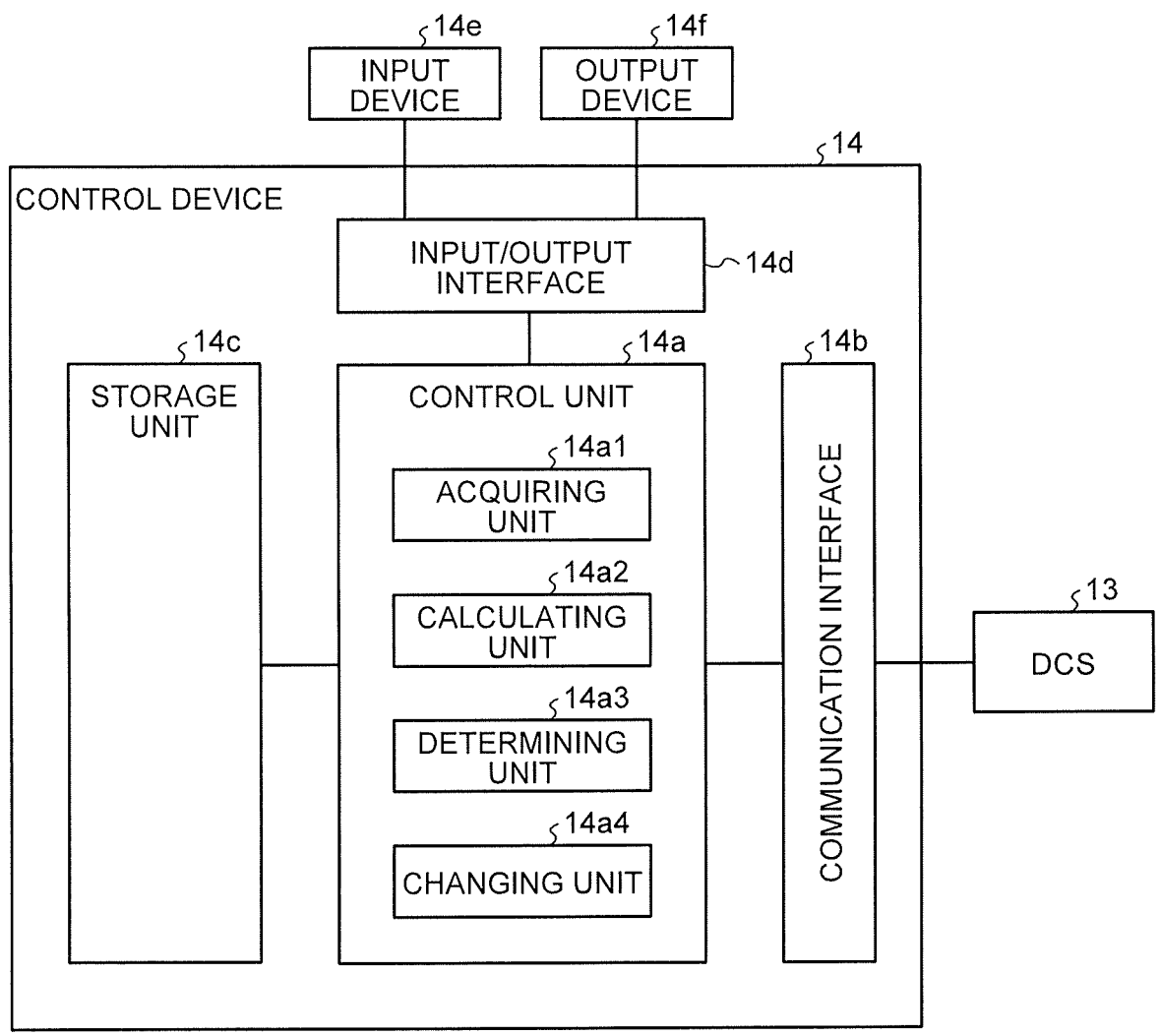
FIG. 2 is a diagram of an exemplary configuration of a control device 14.

The following explains a configuration of a culture system 1 (corresponding to an exemplary production system) according to the present embodiment in detail with reference to FIG. 1 and FIG. 2. FIG. 1 is a diagram of an exemplary configuration of the culture system 1 according to the present embodiment. FIG. 2 is diagram of an exemplary configuration of a control device 14.

The culture system 1 mainly includes a culture tank 11, sensors 12, a distributed control system (DCS) 13, and the control device 14.

The culture tank 11 and the DCS 13 are included in a general culture device (specifically, a jar fermenter). The sensors 12 are for acquiring culture data and are included in a general culture device as a standard or added thereto. The culture data includes operation data (temperature, pH, or sugar supply amount, for example), near-infrared reflectance (NIR) data on a near infrared spectrum of a fermentation liquid, or property values (refractive index, conductivity, viscosity, or capacitance, for example), for example. The culture data may include pH, temperature, turbidity, a dissolved oxygen concentration, an ammonia nitrogen concentration, a sulfuric acid ion concentration, a nitrogen source concentration, a lactic acid concentration, a phosphorous source concentration, an ammonium sulfate concentration, an ammonium sulfate supply amount, a sugar-ammonium sulfate mixed liquid supply amount, an extracting liquid amount, an extracting cell amount, an amino acid concentration, amino acid yield, amino acid productivity, a phosphoric acid concentration, a phosphoric acid ion concentration, a phosphoric acid ion addition amount, a phosphoric acid ion consumption amount, a cell concentration, cell yield, a cell amount, a sugar concentration, a sugar consumption rate, a sugar supply amount, a specific multiplication rate, a specific sugar consumption rate, a specific production rate, an emission gas concentration, an oxygen consumption amount, oxygen demand, a carbon dioxide generation amount, respiratory quotient, rab, or a sugar liquid amount, for example.

The culture data may include values themselves acquired from the operation data or the like (pH, temperature, and a dissolved oxygen concentration, for example), analytical values obtained using other analyzers that are not included in the culture device such as HPLC (amino acid concentration and lactic acid concentration, for example), values obtained by performing arithmetic operations based on the values contained in the culture data (specific multiplication rate, amino acid productivity, and respiratory quotient, for example), or accumulated values of respective values from the start of culture to each culture interval calculated based on the values contained in the culture data (accumulated oxygen consumption amount, culture temperature accumulated value, specific multiplication rate accumulated value, and the like). Furthermore, the culture data may be acquired by soft sensors, for example. A statistical analytical method of soft sensors may be Partial Least Squares (PLS), Random Forest (RF), Extremely Randomized Trees (ERT), Least Absolute Shrinkage and Selection Operator (LASSO), Ridge, Elastic Net (EN), Linear Support Vector Regression (LSVR), Non-Linear Support Vector Regression (NLSVR), Gaussian Process (GP), Gene Algorithm-based Partial Least Squares (GA_PLS), Adaptive Boosting (AdaBoost), eXtreme Gradient Boosting (XGBoost), or Deep Neural Network (DNN), for example. Examples of technical literature on soft sensing include CN-A-107391851, WO 2018/007394, CN-A-107653274, CN-A-106444377, and CN-A-106022532, which are incorporated herein by reference in their entireties.

Examples of a carbon source include carbohydrates such as starch, various sugars such as glucose and sucrose, and various organic acids. According to the type of anabolism of a selected microorganism, alcohol including ethanol and glycerol may be used.

Examples used as a nitrogen supply source include ammonia and various ammonium salts such as ammonium sulfate, other nitrogen compounds such as amine, and natural nitrogen sources such as peptone, soybean hydrolysates, and fermentable microorganism-digested objects.

Examples used as a phosphorous supply source include phosphoric acid, phosphates such as dipotassium monohydrogen phosphate and potassium dihydrogen phosphate, and phosphorous compounds such as myo-inositol.

The organic compound by a fermentation method is a product of a fermentation-and-culture process and is specifically selected from the group consisting of amino acids, organic acids, polysaccharides, proteins, antibiotics, alcohols, and microbial cells.

Examples of amino acids include glycine, alanine, valine, leucine, isoleucine, serine, threonine, cysteine, cystine, methionine, phenylalanine, tyrosine, tryptophan, proline, hydroxy proline, asparagine, glutamine, aspartic acid, glutamic acid, lysine, histidine, and arginine. The amino acids can be classified into any of an acidic amino acid, a basic amino acid, and a neutral amino acid depending on difference in their side chain. Specifically, glutamic acid and aspartic acid can be classified into the acidic amino acid, lysine, arginine, and histidine can be classified into the basic amino acid, and glycine, alanine, threonine, methionine, cysteine, serine, valine, leucine, isoleucine, tryptophan, phenylalanine, tyrosine, proline, glutamine, and asparagine can be classified into the neutral amino acid.

Examples of organic acids include acetic acid, lactic acid, pelvic acid, succinic acid, malic acid, itaconic acid, citric acid, acrylic acid, propionic acid, and fumaric acid. Examples of polysaccharides include xanthan, dextran, alginates, hyaluronic acid, curdlan, gellan, scleroglucan, and pullulan. Examples of proteins include hormones, lymphokine, interferon, enzymes (such as amylase, glucoamylase, invertase, lactase, protease, and lipase). Examples of antibiotics include antimicrobial agents (such as β-lactam, macrolide, ansamycin, tetracycline, chloramphenicol, peptide antibiotics, and aminoglycoside), antimold agents (such as polyoxin B, griseofulvin, and polyene macrolide), anticancer agents (such as daunomycin, adriamycin, dactinomycin, mithramycin, and bleomycin), protease/peptidase inhibitors (such as leupeptin, antipain, and pepstatin), and cholesterol biosynthesis inhibitors (such as compactin, lovastatin, and pravastatin). Examples of alcohols include ethanol, isopropanol (2-propanol), glycerin, propylene glycol, trimethylene glycol, 1-butanol, and sorbite. Examples of other organic compounds produced by a fermentation method include organic compounds such as acrylamide, diene compounds (such as isoprene), and pentanediamine. Techniques that produce the organic compounds by culturing microorganisms having organic compound productivity are widely known. The present embodiment can widely be applied to such microbial fermentation techniques. In microbial fermentation, microorganisms multiply themselves using a carbon source, a nitrogen source, or the like. In such a meaning, in the present embodiment, a fermentation product also includes microbial cells. Examples of microbial cells include any microorganisms having organic compound productivity.

Microorganisms having organic compound productivity include both 1) microorganisms that originally have organic compound productivity and 2) microorganisms that do not have or do not substantially have organic compound productivity originally but have had organic compound productivity a posteriori owing to an organic compound producing gene introduced by genetic modification. As to microorganisms having organic compound productivity, various kinds of microorganisms are known depending on the kind of organic compounds; in the present embodiment, these known microorganisms may widely be used. As far as ammonia can be used as a nitrogen source or a pH regulator in culture, the present embodiment can widely also be applied to microorganisms to be developed in the future.

As microorganisms, which are not limited to particular microorganisms so long as they have organic compound productivity, bacteria or fungi are preferred. Examples of bacteria include bacteria belonging to the genus *Escherichia*, bacteria belonging to the genus *Pantoea*, bacteria belonging to the genus *Corynebacterium*, bacteria belonging to the genus *Enterobacter*, bacteria belonging to the genus *Clostridium*, bacteria belonging to the genus *Bacillus*, bacteria belonging to the genus *Lactobacillus*, bacteria belonging to the genus *Streptomyces*, bacteria belonging to the genus *Streptococcus*, and bacteria belonging to the genus *Pseudomonas*. Examples of fungi include fungi belonging to the genus *Saccharomyces*, fungi belonging to the genus *Schizosaccharomyces*, fungi belonging to the genus *Yarrowia*, fungi belonging to the genus *Trichoderma*, fungi belonging to the genus *Aspergillus*, fungi belonging to the genus *Fusarium*, and fungi belonging to the genus *Mucor*.

Examples of bacteria belonging to the genus *Escherichia* include *Escherichia coli*. Examples of bacteria belonging to the genus *Pantoea* include *Pantoea ananatis*. Examples of bacteria belonging to the genus *Corynebacterium* include *Corynebacterium glutamicum* and *Corynebacterium ammoniagenes*. Examples of bacteria belonging to the genus *Enterobacter* include *Enterobacter aerogenes*. Examples of bacteria belonging to the genus *Clostridium* include *Clostridium acetobutylicum*. Examples of bacteria belonging to the genus *Bacillus* include *Bacillus subtilis* and *Bacillus amyloliquefaciens*. Examples of bacteria belonging to the genus *Lactobacillus* include *Lactobacillus yamanashiensis, Lactobacillus animalis, Lactobacillus hilgardii*, and *Lactobacillus brevis*. Examples of bacteria belonging to the genus *Streptomyces* include *Streptomyces clavuligerus, Streptomyces venezuelae*, and *Streptomyces peucetius*. Examples of bacteria belonging to the genus *Streptococcus* include *Streptococcus equi* and *Streptococcus mutans*. Examples of bacteria belonging to the genus *Pseudomonas* include *Pseudomonas fluorescens, Pseudomonas aeruginosa, Pseudomonas elodea*, and *Pseudomonas putida*. Examples of fungi include fungi belonging to the genus *Saccharomyces* include *Saccharomyces cerevisiae*. Examples of fungi belonging to the genus *Schizosaccharomyces* include *Schizosaccharomyces pombe*. Examples of fungi belonging to the genus *Yarrowia* include *Yarrowia lipolytica*. Examples of fungi belonging to the genus *Trichoderma* include *Trichoderma reesei*. Examples of fungi belonging to the genus *Aspergillus* include *Aspergullus terreus* and *Aspergillus oryzae*. Examples of fungi belonging to the genus *Fusarium* include *Fusarium hetereosporum*. Examples of fungi belonging to the genus *Mucor* include *Mucor javanicus*.

When an amino acid is produced in the present embodiment, examples of microorganisms that can suitably be used include the following. For example, when a target substance is L-lysine, examples include *Escherichia coli* AJ11442 (NRRL B-12185, FERM BP-1543) (refer to U.S. Pat. No. 4,346,170, which is incorporated herein by reference in its entirety), *Brevibacterium lactofermentum* AJ3990 (ATCC31269) (refer to U.S. Pat. No. 4,066,501, which is incorporated herein by reference in its entirety), and Lys-producing bacteria WC196LC/pCABD2 (WO 2010/061890, which is incorporated herein by reference in its entirety). WC196ΔcadAΔldc is a strain constructed by destroying cadA and ldcC genes, which encode lysine decarboxylase, from the WC196 strain. WC196ΔcadAΔldc/pCABD2 is a strain constructed by introducing the plasmid pCABD2 containing lysine biosynthesis genes (U.S. Pat. No. 6,040,160, which is incorporated herein by reference in its entirety) into WC196ΔcadAΔldc. WC196ΔcadAΔldc was designated AJ110692 and was deposited at the national research and development agency, National Institute of Advanced Industrial Science and Technology, International Patent Organism Depositary (currently the independent administrative agency, National Institute of Technology and Evaluation, International Patent Organism Depositary, #120, 2-5-8 Kazusakamatari, Kisarazu-shi, Chiba, 292-0818, Japan) as an accession number of FERM BP-11027 on Oct. 7, 2008. In the case of L-threonine, examples include *Escherichia coli* VKPM B-3996 (RIA 1867, VKPM B-3996) (refer to U.S. Pat. No. 5,175,107, which is incorporated herein by reference in its entirety) and *Corynebacterium acetoacidophilum* AJ12318 (FERM BP-1172) (refer to U.S. Pat. No. 5,188,949, which is incorporated herein by reference in its entirety). In the case of L-phenylalanine, examples include *Escherichia coli* AJ12604 (FERM BP-3579) (refer to EP-A-488424, which is incorporated herein by reference in its entirety) and *Brevibacterium lactofermentum* AJ12637 (FERM BP-4160) (refer to FR-A-2686898, which is incorporated herein by reference in its entirett). In the case of L-glutamic acid, examples include *Escherichia coli* AJ12624 (FERM BP-3853) (refer to FR-A-2680178, which is incorporated herein by reference in its entirety), *Brevibacterium lactofermentum* AJ12475 (FERM BP-2922) (refer to U.S. Pat. No. 5,272,067, which is incorporated herein by reference in its entirety), and 2256ΔldhAΔsucAyggB* created with *Corynebacterium glutamicum* ATCC13869 as a mother strain (WO 2014/185430, which is incorporated herein by reference in its entirety). In the case of L-leucine, examples include *Escherichia coli* AJ11478 (FERM P-5274) (refer to JP-B-62-34397, which is incorporated herein by reference in its entirety) and *Brevibacterium lactofermentum* AJ3718 (FERM P-2516) (refer to U.S. Pat. No. 3,970,519, which is incorporated herein by reference in its entirety). In the case of L-isoleucine, examples include *Escherichia coli* KX141 (VKPM B-4781) (refer to EP-A-519113, which is incorporated herein by reference in its entirety) and *Brevibacterium flavum* AJ12149 (FERM BP-759) (refer to U.S. Pat. No. 4,656,135, which is incorporated herein by reference in its entirety). In the case of L-valine, examples include *Escherichia coli* VL1970 (VKPM B-4411) (refer to EP-A-519113, which is incorporated herein by reference in its entirety) and *Brevibacterium lactofermentum* AJ12341 (FERM BP-1763) (refer to U.S. Pat. No. 5,188,948, which is incorporated herein by reference in its entirety). In the case of L-arginine, examples include strains belonging to the genus *Escherichia* such as *Escherichia coli* 237 strain (VKPM B-7925) (US-A1-2002/058315, which is incorporated herein by reference in its entirety), a derivative strain thereof holding modified N-acetylglutamate synthase (RU-A-2001112869, which is incorporated herein by reference in its entirety), *Escherichia coli* 382 strain (VKPM B-7926) (EP-A1-1170358, which is incorporated herein by reference in its entirety), and an arginine-producing strain into which the argA gene encoding N-acetylglutamate synthase is introduced (EP-A1-1170361, which is incorporated herein by reference in its entirety); all of these examples are not limiting.

When an organic acid is produced in the present embodiment, examples of microorganisms that can suitably be used include the following. For example, when a target substance is L-lactic acid, examples include *Lactobacillus yamanashiensis*, *Lactobacillus animalis*, and *Saccharomyces cerevisiae*. In the case of pyruvic acid, examples include *Escherichia coli* and *Pseudomonas fluorescens*. In the case of succinic acid, examples include *Escherichia coli* and *Pantoea ananatis*. In the case of itaconic acid, examples include *Aspergillus terreus*. In the case of citric acid, examples include *Escherichia coli* (refer to WO 2007/097260 and JP-A-2010-187542, which are incorporated herein by reference in their entireties, for example).

When polysaccharides are produced in the present embodiment, examples of microorganisms that can suitably be used include the following. For example, when a target substance is dextran, examples include *Lactobacillus hilgardii* and *Streptococcus mutans*. In the case of alginates, examples include *Pseudomonas aeruginosa*. In the case of hyaluronic acid, examples include *Streptococcus equi* and *Streptococcus mutans*. In the case of gellan, examples include *Pseudomonas elodea* (refer to JP-A-2011-116825 and JP-A-2007-9092, which are incorporated herein by reference in their entireties, for example).

When a protein is produced in the present embodiment, examples of microorganisms that can suitably be used include the following. For example, when a target substance is various kinds of hormones or interferon, examples include *Saccharomyces cerevisiae*. In the case of amylase, glucoamylase, protease, or lipase, examples include *Bacillus subtilis* and *Aspergillus oryzae*. In the case of invertase and lactase, examples include *Saccharomyces cerevisiae* and *Aspergillus oryzae* (refer to WO 2006/67511 and JP-A-2003-153696, which are incorporated herein by reference in their entireties, for example).

When an antibiotic is produced in the present embodiment, examples of microorganisms that can suitably be used include the following. For example, when a target substance is β-lactam such as penicillin, examples include *Pseudomonas putida* and *Streptomyces clavuligerus*. In the case of macrolide such as erythromycin and azithromycin, examples include *Streptomyces venezuelae*. In the case of daunomycin, examples include *Streptomyces peucetius*. In the case of pravastatin, examples include *Streptomyces clavuligerus* (refer to WO 96/10084, JP-A-2002-53589, WO 2005/54265, and WO 2007/147827, which are incorporated herein by reference in their entireties, for example).

When an alcohol is produced in the present embodiment, examples of microorganisms that can suitably be used include the following. For example, when a target substance is ethanol, examples include *Saccharomyces cerevisiae*, *Schizosaccharomyces pombe*, and *Lactobacillus brevis*. In the case of trimethylene glycol, examples include *Escherichia coli* (refer to WO 2007/97260, which is incorporated herein by reference in its entirety, for example).

The sensors 12 and the DCS 13 are connected to each other in a communicable manner via a wired or wireless communication line. The DCS 13 and the control device 14 are connected to each other in a communicable manner via a wired or wireless communication line. The number of the sensors 12 is not limited to four as depicted. The control device 14 may be present as a separate casing from the DCS 13 as depicted or present as the same casing as the DCS 13.

The control device 14 performs control of a culture condition in production of an organic compound by a fermentation method. The control device 14 executes processing a plurality of times to acquire culture data, to calculate, using the acquired culture data, a plurality of candidates for a culture condition set in advance, and a linear model set in advance that outputs a production amount of an organic compound at a future time, the production amount at the future time for each of the candidates, to determine an optimum candidate out of the candidates using the calculated production amount at the future time for each of the candidates and a target production amount of the organic compound at the future time set in advance, and to change the culture condition to the determined candidate. In the control device 14, the linear model and the target production amount are set for each time. A time interval between a time when an nth (n is an integer of equal to or more than 1) processing is executed and a time when an (n+1)th processing is executed may be any time interval.

The control device 14 includes a control unit 14a, such as CPU (Central Processing Unit), that integrally controls the device, a communication interface 14b that connects the device to the DCS 13 in a communicable manner via a wired or wireless communication line, a storage unit 14c that stores various databases, tables, files and others, and an input/output interface 14d connected to an input device 14e and an output device 14f. These units included in the control device 14 are connected to each other in a communicable manner via any communication channel.

A keyboard, a mouse, a microphone, a monitor functioning as a pointing device together with a mouse, a touch screen, or the like may be used as the input device 14d. A monitor, a speaker, a printer, or the like may be used as the output device 14f.

The storage unit 14c is a storage means. A memory device such as RAM (Random Access Memory) and ROM (Read Only Memory), a fixed disk drive such as a hard disk, a flexible disk, an optical disk, or the like may be used as the storage unit 14c. The storage unit 14c may store computer programs giving instructions to the CPU for various processings, together with OS (Operating System).

The control unit 14a has an internal memory storing control programs such as OS, programs for various processing procedures, and needed data, and performs various information processings according to these programs.

The control unit 14a functionally conceptually includes an acquiring unit 14a1, a calculating unit 14a2, a determining unit 14a3, and a changing unit 14a4. The control unit 14a operates the acquiring unit 14a1, the calculating unit 14a2, the determining unit 14a3, and the changing unit 14a4 a plurality of times.

The acquiring unit 14a1 is an information processing unit that acquires the culture data. The acquiring unit 14a1 may acquire the culture data measured by the sensors 12 acquired by, for example, the DCS 13 from the DCS 13.

The calculating unit 14a2 is an information processing unit that calculates, using the culture data acquired by the acquiring unit 14a1, a plurality of candidates for a culture condition set in advance, and a linear model set in advance that outputs a production amount of an organic compound at a future time, the production amount at the future time for each of the candidates. The future time may be a time when next time processing is executed, for example. A plurality of the linear models may be set for each time, for example. The linear model may be a multiple regression formula, for example. The candidates for the culture condition may be configured by culture conditions for respective times (a first culture condition, a second culture condition, . . . ), for example. The culture condition may be an operating condition of a general culture device, for example. The culture condition may be a condition on temperature, pH, or a phosphoric acid concentration, for example.

The determining unit 14a3 is an information processing unit that determines an optimum candidate out of the candidates for the culture condition using the production amount at the future time for each of the candidates calculated by the calculating unit 14a2 and a target production amount of the organic compound at the future time set in advance. When the linear models are set for each time, the determining unit 14a3 may determine the optimum candidate out of the candidates using a sample statistical amount (an average, for example) for each of the candidates based on a plurality of production amounts at the future time for each of the candidates and the target production amount, for example. The determining unit 14a3 may determine a candidate corresponding to a production amount at the future time closest to the target production amount or the sample statistical amount to be the optimum candidate, for example. The sample statistical amount refers to a value representing a characteristic of data such as an average.

The changing unit 14a4 is an information processing unit that changes the culture condition to the candidate determined by the determining unit 14a3. When the culture condition is an operating condition of the culture device, the changing unit 14a4 may change the operating condition set in the DCS 13 to the candidate determined by the determining unit 14a3, for example.

2. Processing

Figure 3:
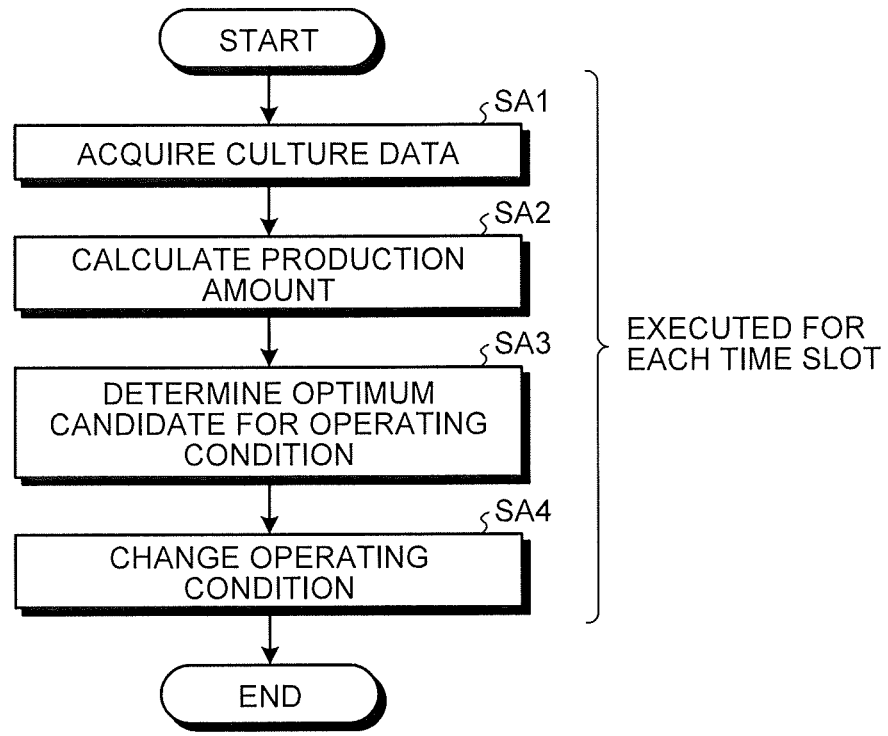
FIG. 3 is a diagram of an exemplary flowchart about control processing.

The following explains exemplary control processing executed by the control device 14 with reference to FIG. 3. It is premised in the present explanation that a time schedule based on a time elapsed from the start of culture (culture start $N_1$ time, culture start $N_2$ ($N_1 < N_2$) time, culture start $N_3$ ($N_2 < N_3$) time, . . . , for example) is set. It is also premised in the present explanation that each of the candidates for the operating condition of the culture device includes the operating condition for each time set in the time schedule.

First, upon a first time in the time schedule, the control unit 14a causes the acquiring unit 14a1 to operate, and the acquiring unit 14a1 acquires culture data corresponding to the first time from the DCS 13 (Step SA1).

Next, the calculating unit 14a2 inputs the culture data acquired at Step SA1 and a plurality of candidates for the operating condition to a linear model that outputs a production amount of an organic compound at a second time in the time schedule to calculate a production amount of the organic compound at the second time for each of the candidates (Step SA2).

Next, the determining unit 14a3 compares the production amount for each of the candidates calculated at Step SA2 and a target production amount at the second time in the time schedule with each other in magnitude and determines a candidate corresponding to a production amount closest to the target production amount to be an optimum candidate (Step SA3).

Next, the changing unit 14a4 changes the operating condition set in the DCS 13 to the candidate for the operating condition determined at Step SA3 (Step SA4).

Then, the control unit 14a repeatedly executes the processing from Step SA1 to Step SA4 according to the time schedule.

3. Summary of Present Embodiment

As explained in the foregoing, the present embodiment repeatedly executes a series of processing including (1) acquisition of the culture data, (2) calculation of the future production amount for each of the candidates using the linear model, (3) determination of the optimum candidate for the culture condition, and (4) change of the culture condition according to, for example, the time schedule during culture and can determine an optimum, readable culture condition in real time and control a production result in production of an organic compound by a fermentation method. The present embodiment can achieve real-time control of the culture condition based on high estimation accuracy. The present embodiment can optimize a production amount of the organic compound by, for example, optimizing the operating condition in real time during culture operation, and by extension, enables stable production of the organic compound throughout the year in a plant.

The linear model used in the present embodiment is created based on the data during culture (is created by executing Processing 1 through Processing 6 below, for example), and the present embodiment can cope with various production situations that cannot be represented by general formulae based on fermentation technology and metabolic technology such as the Monod expression. That is, the present embodiment enables not only control on a laboratory level but also enables control on a bench plant scale, a pilot plant scale, or an actual device scale.

The linear model used in the present embodiment can be created by executing Processing 1 through Processing 6 below, for example.

[Processing 1] Data during culture is collected. As to the data to be collected, not only variables indicating a fermentation state (amino acid concentration, sugar concentration, cell concentration, or the like) but also data on infinitesimal components in a liquid (other amino acids or organic acids) is acquired. Specifically, NIR data, operation data, or property value data is acquired. For the operating condition, which is not the same operating condition, data is acquired on various conditions (variable temperature, pH, or the like). When an experimental condition is determined, thought is given to make variables close to a normal distribution.

[Processing 2] A response variable to be modeled (amino acid production amount) and explanatory variables to be used in the model are determined.

[Processing 3] Coefficients of correlation of the response variable and the explanatory variables are calculated to select explanatory variables with a high coefficient of correlation.

[Processing 4] Using Akaike's Information Criterion (AIC), the explanatory variables are narrowed down by the stepwise method.

[Processing 5] Based on the narrowed down explanatory variables, models are created by the variable coverage method.

[Processing 6] Models with a high coefficient of correlation (top 1,000 models or models with a coefficient of correlation of equal to or more than 0.7, for example) are extracted.

4. Other Embodiments

In addition to the embodiment described above, the present invention can be practiced in various different embodiments within the technological scope of the claims.

Of the processings described in the embodiment, all or a part of the processings described as automatically performed ones may be manually performed, or all or a part of the processings described as manually performed ones may be also automatically performed by known methods.

The components of the devices shown in the figures are functionally conceptual and therefore not be physically configured as shown in the figures. A specific configuration of dispersion or integration of the system is not limited to the shown one. The system can be configured by functionally or physically dispersing or integrating the devices in arbitrary units.

For the operational functions provided in the control device 14, in particular, for the operational functions performed in the control unit 14a, all or part thereof may be implemented by the CPU and programs interpreted and executed in the CPU. The program is recorded in a non-transitory tangible computer-readable recording medium including programmed instructions for making an information processing apparatus execute the control method according to the present invention, and is mechanically read as needed by the control device 14. More specifically, computer programs to give instructions to the CPU in cooperation with the OS to perform various processes are recorded in the storage unit 14c such as ROM or a HDD (hard disk drive). The computer programs are executed by being loaded to RAM, and form the control unit in cooperation with the CPU.

The control program according to the present invention may be stored in the non-transitory tangible computer-readable recording medium, or can be configured as a program product. The "recording medium" mentioned here includes any "portable physical medium" such as a memory card, a USB (universal serial bus) memory, an SD (secure digital) card, a flexible disk, a magneto-optical disc, ROM, EPROM (erasable programmable read only memory), EEPROM (registered trademark) (electronically erasable and programmable read only memory), CD-ROM (compact disk read only memory), MO (magneto-optical disk), DVD (digital versatile disk), and Blu-ray (registered trademark) Disc.

The present invention produces an effect of making it possible to determine an optimum, readable culture condition in real time and control a production result in production of an organic compound by a fermentation method. The present invention also produces an effect of making it possible to achieve stable production of an organic compound by a fermentation method.

Example 1

In Example 1, the operating condition was optimized using a linear model (specifically, a multiple regression formula) on a lysine production amount, whereby control of the lysine production amount was performed. The linear model used in Example 1 was created by a statistical method explained in the present embodiment based on experimental data to model a lysine fermentation process.

1. Control Method

A culture time from the start of culture to the end of culture was divided into six intervals (Interval 1, Interval 2, Interval 3, Interval 4, Interval 5, and Interval 6), and control of the operating condition indicated by (1) through (4) below was performed. Before the start of culture, a lysine production amount as a target production amount was set at the end of each interval (at the end of the current interval, for example). Before the start of culture, candidates (about eight candidates) for the operating condition were determined for each interval. In the examples described in the present specification, the length of a time of each interval may be any time; the length of the time is preferably 2 hours or more and 12 hours or less, and more preferably 4 hours or more and 8 hours or less.

(1) Measurement or analysis of pH, temperature, a phosphoric acid concentration, a sulfuric acid concentration, a nitrogen source concentration, a sugar supply amount, a sampling amount, an extracting liquid amount, a lysine concentration, turbidity (OD), a sugar concentration, an ammonium sulfate supply amount, an emission gas concentration, and a dissolved oxygen concentration is performed at the beginning of the current interval (corresponding to the processing performed by the acquiring unit 14a1 described in the embodiment). Using the obtained measurement result or analysis result, all items as variables of the linear model are calculated.

(2) Using the obtained analysis data, data on the current operating condition, and a linear model that predicts a lysine production amount at the end of the current interval, the lysine production amount at the end is predicted (corresponding to the processing performed by the calculating unit 14a2 described in the embodiment). The linear model incorporates the operating condition as a variable, and the predicted value of the lysine production amount varies for each of the candidates for the operating condition. The linear model is set for each interval.

(3) The operating condition on which the predicted value is the closest to the lysine production amount as the target production amount at the end is selected (corresponding to the processing performed by the determining unit 14a3 described in the embodiment).

(4) The operating condition is changed to the selected operating condition (corresponding to the processing performed by the changing unit 14a4 described in the embodiment).

2. Experimental Conditions

FIG. 4 depicts experimental conditions. The No. 1 row shows a standard experimental condition. The No. 2 row shows an experimental condition corresponding to the target production amount. In FIG. 4, the values of the operating condition are represented as relative values to the values of the No. 1 operating condition.

The No. 3 row shows an experimental condition with the operating condition changed from Interval 2 with a fermentation result obtained on the No. 2 experimental condition as the target production amount. By comparing the No. 2 and No. 3 results with each other, the effect of optimization of the operating condition is confirmed.

3. Used Linear Model

Figures 5, 6:
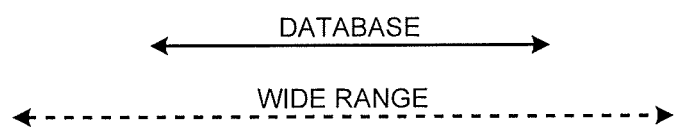
FIG. 5 is a diagram of exemplary arithmetic signs ("+" or "−") to be attached to variables of an operating condition contained in a linear model.
FIG. 6 is a diagram of an exemplary operating condition range.

FIG. 5 depicts arithmetic signs ("+" or "–") to be attached to control variables (specifically, pH, temperature, and phosphoric acid concentration to be supplied) contained in a used linear model. The used linear model maximizes estimation performance explored by multiple regression analysis (the variable coverage method based on AIC minimum criterion) and was evaluated by an adjusted coefficient of determination with leave-one-out cross-validation performed and a coefficient of correlation with leave-one-out cross-validation performed.

In a linear model that predicts a lysine production amount at the end of Interval 1 (the amount of lysine produced in the culture time of Interval 1) based on data at the beginning of Interval 1 (top 1,000 expressions with a high adjusted coefficient of determination with leave-one-out cross-validation performed and a high coefficient of correlation with leave-one-out cross-validation performed), the arithmetic sign of the median of the coefficient of each control variable was "+." The top 1,000 expressions are described in [11. Linear Model that Predicts Lysine Production Amount in Interval 1].

In a linear model that predicts a lysine production amount at the end of Interval 2 (the amount of lysine produced in the culture time of Interval 2) based on data at the beginning of Interval 2 (top 1,000 expressions with a high adjusted coefficient of determination with leave-one-out cross-validation performed and a high coefficient of correlation with leave-one-out cross-validation performed), the arithmetic sign of the median of the coefficient of each control variable was "+." The top 1,000 expressions are described in [12. Linear Model that Predicts Lysine Production Amount in Interval 2].

In a linear model that predicts a lysine production amount at the end of Interval 3 (the amount of lysine produced in the culture time of Interval 3) based on data at the beginning of Interval 3 (top 1,000 expressions with a high adjusted coefficient of determination with leave-one-out cross-validation performed and a high coefficient of correlation with leave-one-out cross-validation performed), the arithmetic sign of the median of the coefficient of pH as a control variable was "–," whereas the arithmetic sign of the median of the coefficients of temperature and a phosphoric acid concentration to be supplied as control variables was "+." A list of the top 1,000 expressions is described in [13. Linear Model that Predicts Lysine Production Amount in Interval 3].

In a linear model that predicts a lysine production amount at the end of Interval 4 (the amount of lysine produced in the culture time of Interval 4) based on data at the beginning of Interval 4 (top 1,000 expressions with a high adjusted coefficient of determination with leave-one-out cross-validation performed and a high coefficient of correlation with leave-one-out cross-validation performed), the arithmetic sign of the median of the coefficients of pH and temperature as control variables was "–," whereas the arithmetic sign of the median of the coefficient of a phosphoric acid concentration to be supplied as a control variable was "+." A list of the top 1,000 expressions is described in [14. Linear Model that Predicts Lysine Production Amount in Interval 4].

In a linear model that predicts a lysine production amount at the end of Interval 5 (the amount of lysine produced in the culture time of Interval 5) based on data at the beginning of Interval 5 (top 1,000 expressions with a high adjusted coefficient of determination with leave-one-out cross-validation performed and a high coefficient of correlation with leave-one-out cross-validation performed), the arithmetic sign of the median of the coefficient of temperature as a control variable was "–," whereas the arithmetic sign of the median of the coefficients of pH and a phosphoric acid concentration to be supplied as control variables was "+." A list of the top 1,000 expressions is described in [15. Linear Model that Predicts Lysine Production Amount in Interval 5].

In a linear model that predicts a lysine production amount at the end of Interval 6 (the amount of lysine produced in the culture time of Interval 6) based on data at the beginning of Interval 6 (top 1,000 expressions with a high adjusted coefficient of determination with leave-one-out cross-validation performed and a high coefficient of correlation with leave-one-out cross-validation performed), the arithmetic sign of the median of the coefficient of temperature as a control variable was "–," whereas the arithmetic sign of the median of the coefficients of pH and a phosphoric acid concentration to be supplied as control variables was "+." A list of the top 1,000 expressions is described in [16. Linear Model that Predicts Lysine Production Amount in Interval 6].

4. Operating Condition Range

The control variables changed during fermentation operation were pH, temperature, and a phosphoric acid concentration to be supplied. FIG. 6 depicts an operating condition range. For the creation of the linear model, data acquired within a range denoted as "DATABASE" in FIG. 6 was used. In view of the prediction accuracy of the linear model, the data acquired within this range is preferably used, but data acquired outside this range (one by extrapolation) may also be used. By increasing the change range of the operating condition, the effect of a change of the operating condition on fermentation may be able to be increased, and in Example 1 the operating condition was changed within a range denoted as "WIDE RANGE" in FIG. 6 (a range wider than the range denoted as "DATABASE" in FIG. 6), which is considered to be hard to affect fermentation from the past knowledge in fermentation process development. In FIG. 6, the values of the operating condition are represented as relative values to the values of the No. 1 operating condition depicted in FIG. 4.

5. Lysine Concentration Analysis

As a lysine concentration, one measured by a biosensor was used. To prevent difference in an analytical system from having influence, as a fermentation result as a target also, an analytical value of the biosensor was used. For the creation of the linear model, a lysine concentration measured by high performance liquid chromatography (HPLC) was used.

6. Results and Discussion

Figure 8:
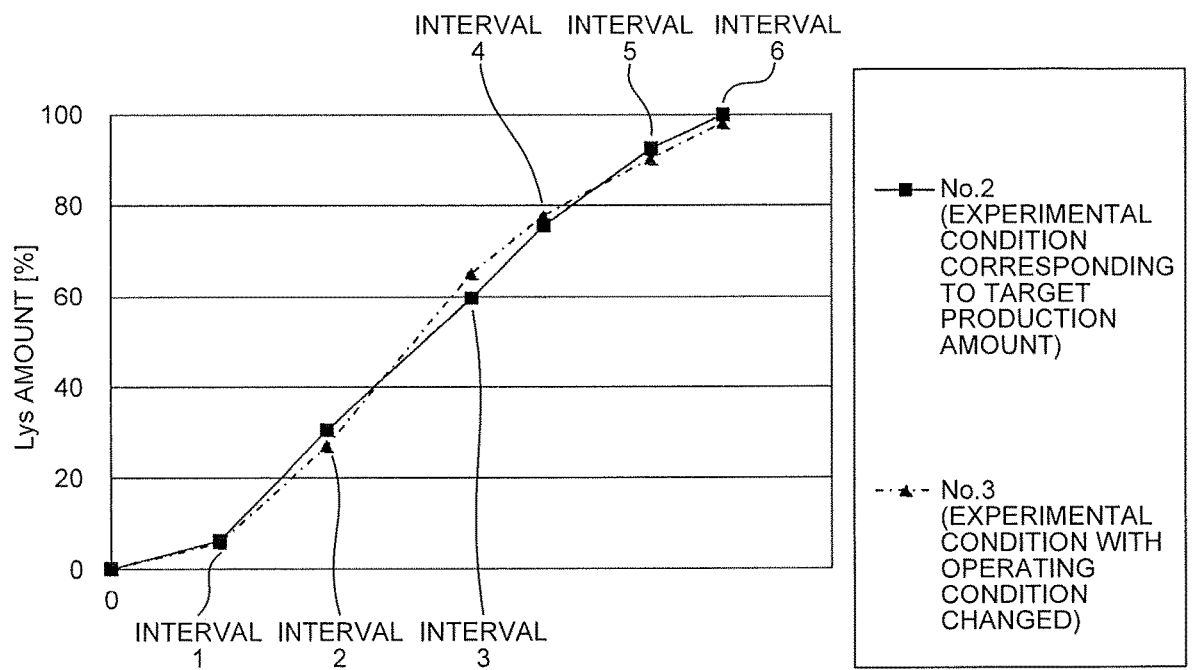
FIG. 8 is a diagram of an exemplary graph of the Lys culture result.

FIG. 7 and FIG. 8 depict culture results by the respective experimental conditions.

Optimization of the No. 3 operating condition was performed from Interval 2 with the lysine production amount obtained on the No. 2 operating condition as the target production amount. Consequently, the No. 3 operating condition was changed to increase the lysine production amount from Interval 2 to Interval 6 (refer to the solid line frame in FIG. 4).

The lysine production amount obtained on the No. 3 experimental condition changed with substantially the same values as the lysine production amount obtained on the No. 2 experimental condition. It is considered that this result means that controlling the lysine production amount to a value close to the target production amount succeeded by performing optimization of the operating condition using the linear model from Interval 2.

Example 2

In Example 2, the operating condition was optimized using the linear model of Example 1 to renew control of the lysine production amount.

1. Control Method

The details are explained in Example 1 and are omitted.

2. Experimental Conditions

FIG. 9 depicts experimental conditions. The No. 51 row shows an experimental condition corresponding to the target production amount. The No. 52 row shows an experimental condition corresponding to the target production amount (the same as the No. 2 experimental condition in FIG. 4), which was the largest in the lysine production amount in the experiment with the culture device (the jar fermentor) described in Example 1. In FIG. 9, the values of the operating condition are represented as relative values to the values of the No. 51 operating condition.

The No. 53 row shows an experimental condition with the operating condition changed from Interval 2 with a fermentation result obtained on the No. 52 experimental condition (the same as the No. 2 experimental condition in FIG. 4) as the target production amount. The No. 54 row shows an experimental condition with the operating condition in Interval 1 the same as that of No. 53 and with the operating condition unchanged from Interval 2 on. The No. 54 experimental condition is one with which the No. 53 experimental condition is compared. The phosphoric acid concentration at the start of culture contained in the No. 53 experimental condition is lower than that contained in the No. 52 experimental condition (refer to FIG. 9). For this reason, the lysine production amount at the early state of culture on the No. 53 experimental condition is expected to be smaller than that on the No. 52 experimental condition. Given this, whether a lysine production amount comparable to the lysine production amount obtained on the No. 52 experimental condition can be obtained on the No. 53 experimental condition is confirmed by performing optimization of the operating condition from a state in which the lysine production amount is small.

The No. 55 row shows an experimental condition with the operating condition changed from Interval 2 with a fermentation result obtained on the No. 51 experimental condition as the target production amount. The No. 56 row shows an experimental condition with the operating condition in Interval 1 the same as that of No. 55 and with the operating condition unchanged from Interval 2 on. The No. 56 experimental condition is one with which the No. 55 experimental condition is compared. The phosphoric acid concentration at the start of culture contained in the No. 55 experimental condition is higher than that contained in the No. 51 experimental condition (refer to FIG. 9). For this reason, the lysine production amount at the early state of culture on the No. 55 experimental condition is expected to be larger than that on the No. 51 experimental condition. Given this, whether the lysine production amount can be reduced on the No. 55 experimental condition, which changes the operating condition, is confirmed.

The No. 57 row shows an experimental condition with the operating condition changed from Interval 2 with the fermentation result obtained on the No. 52 experimental condition as the target production amount. The No. 58 row shows an experimental condition with the operating condition in Interval 1 the same as that of No. 57 and with the operating condition unchanged from Interval 2 on. The No. 58 experimental condition is one with which the No. 57 experimental condition is compared. The No. 53 experimental condition and the No. 57 experimental condition are different from each other in that the No. 53 experimental condition simultaneously changes all the control variables (pH, temperature, and phosphoric acid concentration to be supplied), whereas the No. 57 experimental condition changes only the phosphoric acid concentration to be supplied.

3. Used Linear Model

Figures 10, 11:
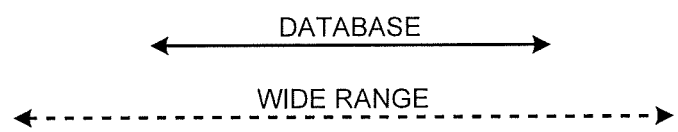
FIG. 10 is a diagram of exemplary arithmetic signs ("+" or "−") to be attached to the variables of the operating condition contained in the linear model.
FIG. 11 is a diagram of an exemplary operating condition range.

FIG. 10 depicts arithmetic signs ("+" or "−") to be attached to control variables contained in a used linear model. The details are explained in Example 1 and are omitted.

4. Operating Condition Range

The control variables changed during fermentation operation were pH, temperature, and a phosphoric acid concentration to be supplied. FIG. 11 depicts an operating condition range. For the creation of the linear model, data acquired within a range denoted as "DATABASE" in FIG. 11 was used. In view of the prediction accuracy of the linear model, the data acquired within this range is preferably used, but data acquired outside this range (one by extrapolation) may also be used. By increasing the change range of the operating condition, the effect of a change of the operating condition on fermentation may be able to be increased, and in Example 2 the operating condition was changed within a range denoted as "WIDE RANGE" in FIG. 11 (a range wider than the range denoted as "DATABASE" in FIG. 11), which is considered to be hard to affect fermentation from the past knowledge in fermentation process development. In FIG. 11, the values of the operating condition are represented as relative values to the values of the No. 51 operating condition depicted in FIG. 9.

5. Lysine Concentration Analysis

The details are explained in Example 1 and are omitted.

6. Results and Discussion

FIGS. 12 to 15 depict culture results by the respective experimental conditions.

6-1. Results and Discussion of No. 53 and No. 54

Optimization of the No. 53 operating condition was performed from Interval 2 with a lysine production amount obtained on the No. 52 operating condition as the target production amount. Consequently, the No. 53 operating condition was changed to increase the lysine production amount in Interval 2 and Interval 3 (refer to the solid line frame in FIG. 9).

Figure 13:
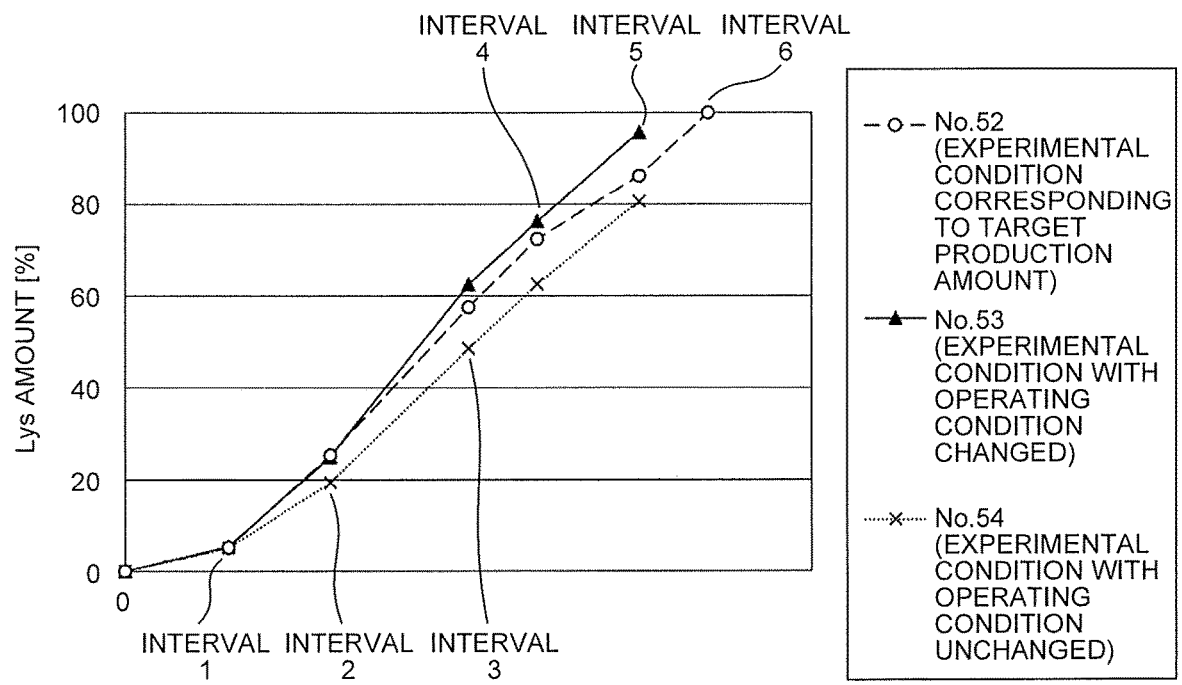
FIG. 13 is a diagram of an exemplary graph of Lys culture results.

FIG. 12 and FIG. 13 depict culture results. The lysine production amount obtained on the No. 54 experimental condition (without any change of the operating condition) was smaller than the lysine production amount obtained on the No. 52 experimental condition. It is considered that this result is caused by intentionally decreasing the phosphoric acid concentration at the start of culture. On the other hand, the lysine production amount obtained on the No. 53 experimental condition, which was the same as the No. 54 experimental condition in the phosphoric acid concentration at the start of culture, was larger than the lysine production amount obtained on the No. 52 experimental condition from the middle stage of culture on. It is considered that this result means that increasing the lysine production amount succeeded by performing optimization of the operating condition using the linear model from Interval 2.

6-2. Results and Discussion of No. 55 and No. 56

Optimization of the No. 55 operating condition was performed from Interval 2 with a lysine production amount obtained on the No. 51 operating condition as the target production amount. Consequently, the No. 55 operating condition was changed to decrease the lysine production amount from Interval 3 on (refer to the solid line frame in FIG. 9).

Figure 14:
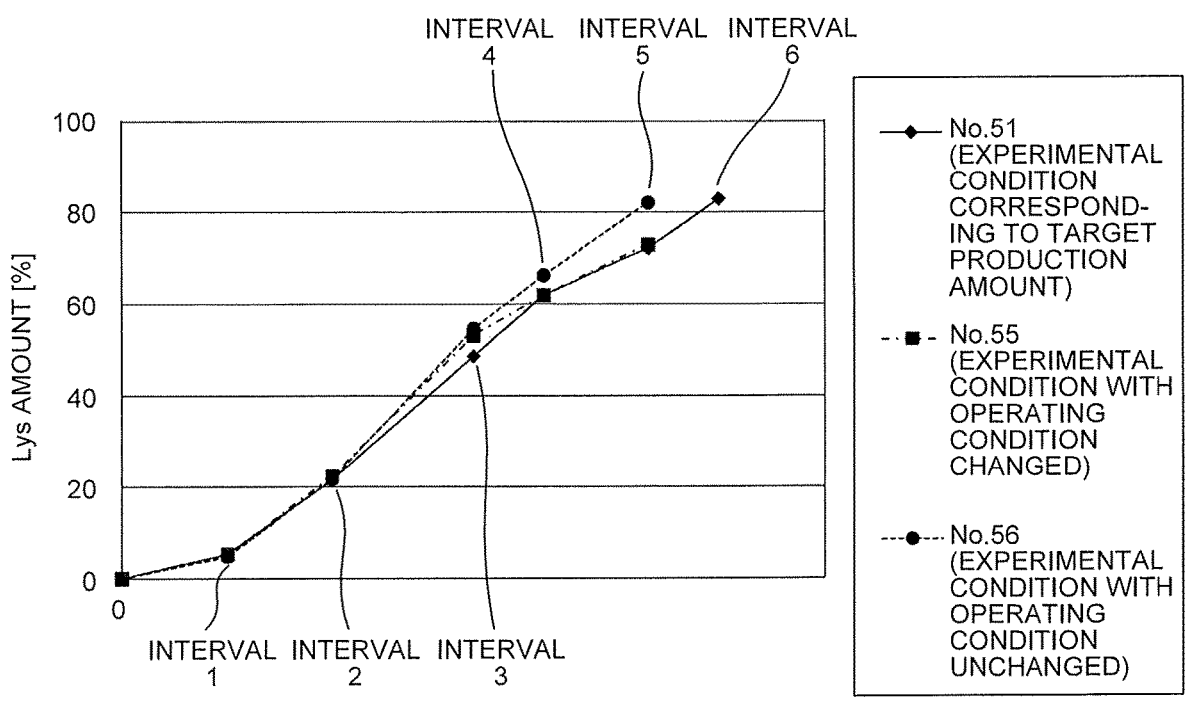
FIG. 14 is a diagram of an exemplary graph of Lys culture results.

FIG. 12 and FIG. 14 depict culture results. The lysine production amount obtained on the No. 56 experimental condition (without any change of the operating condition) was smaller than the lysine production amount obtained on the No. 51 experimental condition. It is considered that this result is caused by increasing the phosphoric acid concentration at the start of culture. On the other hand, the lysine production amount obtained on the No. 55 experimental condition, which was the same as the No. 56 experimental condition in the phosphoric acid concentration at the start of culture, was comparable to the lysine production amount obtained on the No. 51 experimental condition from the middle stage of culture on. It is considered that this result means that decreasing the lysine production amount succeeded by changing the operating condition using the linear model from Interval 2.

That is, it is confirmed that the present embodiment can both increase and decrease the lysine production amount.

6-3. Results and Discussion of No. 57 and No. 58

Optimization of the No. 57 operating condition was performed from Interval 2 with the lysine production amount obtained on the No. 52 operating condition as the target production amount. Consequently, the No. 57 operating condition was changed to increase the lysine production amount in Interval 2, Interval 3, Interval 5, and Interval 6 (refer to the solid line frame in FIG. 9).

Figures 15, 16:
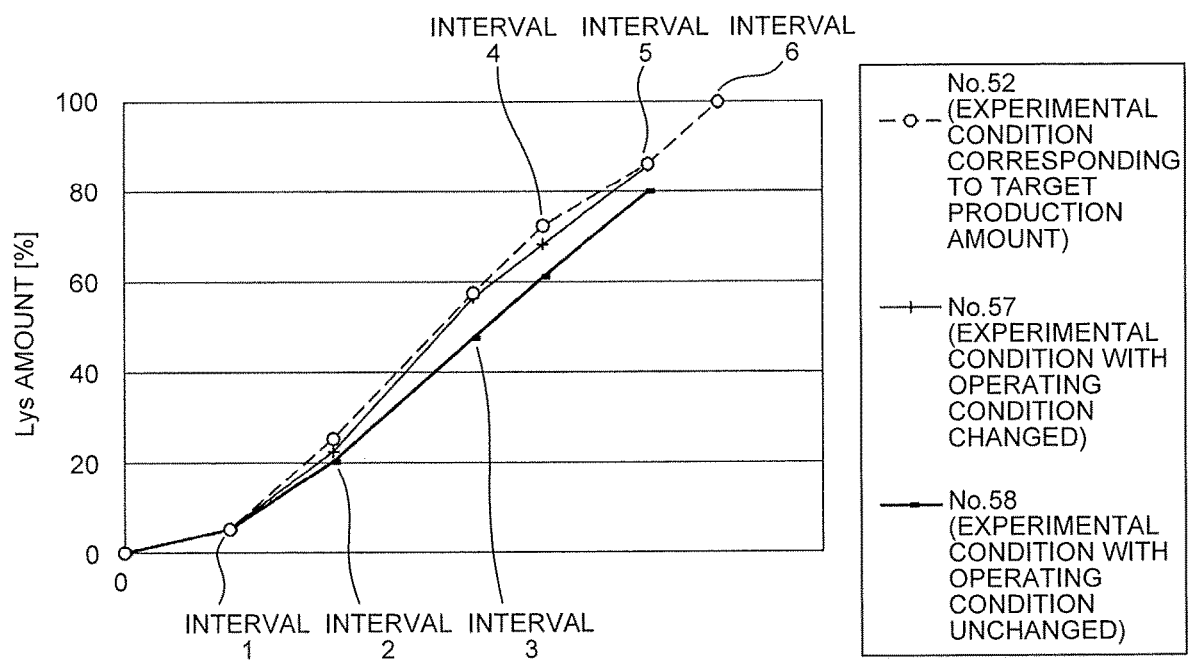
FIG. 15 is a diagram of an exemplary graph of Lys culture results.
FIG. 16 is a diagram of exemplary operating conditions.

FIG. 12 and FIG. 15 depict culture results. The lysine production amount obtained on the No. 58 experimental condition (without any change of the operating condition) was smaller than the lysine production amount obtained on the No. 52 experimental condition. It is considered that this result is caused by decreasing the phosphoric acid concentration at the start of culture. On the other hand, the lysine production amount obtained on the No. 57 experimental condition, which was the same as the No. 58 experimental condition in the phosphoric acid concentration at the start of culture, was comparable to the lysine production amount obtained on the No. 52 experimental condition from the middle stage of culture on. It is considered that this result means that increasing the lysine production amount succeeded by performing optimization of the operating condition using the linear model from Interval 2.

Example 3

In Example 3, the operating condition was optimized using the linear model (specifically, the multiple regression formula) on an arginine production amount, whereby control of the arginine production amount was performed. The linear model used in Example 3 is created by the statistical method explained in the present embodiment based on experimental data to model an arginine fermentation process.

1. Control Method

A culture time from the start of culture to the end of culture was divided into ten intervals (Interval 1, Interval 2, Interval 3, Interval 4, Interval 5, Interval 6, Interval 7, Interval 8, Interval 9, and Interval 10), and control of the operating condition indicated by (1) through (4) below was performed. Before the start of culture, an arginine production amount as a target production amount was set at the end of each interval (at the end of the current interval, for example). Before the start of culture, candidates (about eight candidates) for the operating condition were determined for each interval.

(1) Measurement or analysis of pH, temperature, a sugar supply amount, an ammonium sulfate supply amount, a sampling amount, an arginine concentration, turbidity (OD), a sugar concentration, and an ammonium sulfate concentration is performed at the beginning of the current interval (corresponding to the processing performed by the acquiring unit $14a1$ described in the embodiment). Using the obtained measurement result or analysis result, all items as variables of the linear model (specific multiplication rate, specific production rate, sugar consumption rate, and the like) are calculated.

(2) Using the obtained analysis data, data on the current operating condition, and a linear model that predicts an arginine production amount at the end of the current interval, the arginine production amount at the end is predicted (corresponding to the processing performed by the calculating unit 14a2 described in the embodiment). The linear model incorporates the operating condition as a variable, and the predicted value of the arginine production amount varies for each of the candidates for the operating condition. The linear model is set for each interval.

(3) The operating condition on which the predicted value is the closest to the arginine production amount as the target production amount at the end is selected (corresponding to the processing performed by the determining unit 14a3 described in the embodiment). Specifically, culture was started on the same condition as that of the target, that the arginine production amount increases or decreases relative to the target based on the predicted value of the linear model was confirmed, and that the arginine production amount comparable to the target was given in the end was verified.

(4) The operating condition is changed to the selected operating condition (corresponding to the processing performed by the changing unit 14a4 described in the embodiment).

2. Experimental Conditions

FIG. 16 depicts experimental conditions. The row denoted as J1 target shows an experimental condition corresponding to the target production amount. The row denoted as J5 verification shows an experimental condition with the operating condition changed from Interval 2 with a fermentation result obtained on the experimental condition of J1 target as the target production amount. By comparing the results of J1 target and J5 verification with each other, the effect of optimization of the operating condition is confirmed. In FIG. 16, the values of the operating condition are represented as relative values to the values of the operating condition of J1 target.

3. Used Linear Model

Figures 17, 18:
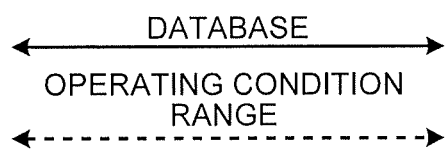
FIG. 17 is a diagram of exemplary arithmetic signs ("+" or "−") to be attached to the variables of the operating condition contained in the linear model.
FIG. 18 is a diagram of an exemplary operating condition range.

FIG. 17 depicts arithmetic signs ("+" or "−") to be attached to control variables (specifically, pH and temperature) contained in a used linear model. The used linear model maximizes estimation performance explored by multiple regression analysis (the variable coverage method based on AIC minimum criterion) and was evaluated by an adjusted coefficient of determination with leave-one-out cross-validation performed and a coefficient of correlation with leave-one-out cross-validation performed.

In a linear model that predicts an arginine production amount at the end of Interval 1 (the amount of arginine produced in the culture time of Interval 1) based on data at the beginning of Interval 1 (top 1,000 expressions with a high adjusted coefficient of determination with leave-one-out cross-validation performed and a high coefficient of correlation with leave-one-out cross-validation performed), the arithmetic sign of the median of the coefficient of temperature as a control variable was "+," and the arithmetic sign of the median of the coefficient of pH as a control variable was "+." The top 1,000 expressions are described in [201. Linear Model that Predicts Arginine Production Amount in Interval 1].

In a linear model that predicts an arginine production amount at the end of Interval 2 (the amount of arginine produced in the culture time of Interval 2) based on data at the beginning of Interval 2 (top 1,000 expressions with a high adjusted coefficient of determination with leave-one-out cross-validation performed and a high coefficient of correlation with leave-one-out cross-validation performed), the arithmetic sign of the median of the coefficient of temperature as a control variable was "+," and the arithmetic sign of the median of the coefficient of pH as a control variable was "+." The top 1,000 expressions are described in [202. Linear Model that Predicts Arginine Production Amount in Interval 2].

In a linear model that predicts an arginine production amount at the end of Interval 3 (the amount of arginine produced in the culture time of Interval 3) based on data at the beginning of Interval 3 (top 1,000 expressions with a high adjusted coefficient of determination with leave-one-out cross-validation performed and a high coefficient of correlation with leave-one-out cross-validation performed), the arithmetic sign of the median of the coefficient of temperature as a control variable was "+," whereas the arithmetic sign of the median of the coefficient of pH as a control variable was "−." A list of the top 1,000 expressions is described in [203. Linear Model that Predicts Arginine Production Amount in Interval 3].

In a linear model that predicts an arginine production amount at the end of Interval 4 (the amount of arginine produced in the culture time of Interval 4) based on data at the beginning of Interval 4 (top 1,000 expressions with a high adjusted coefficient of determination with leave-one-out cross-validation performed and a high coefficient of correlation with leave-one-out cross-validation performed), the arithmetic sign of the median of the coefficient of temperature as a control variable was "+," and the arithmetic sign of the median of the coefficient of pH as a control variable was "+." A list of the top 1,000 expressions is described in [204. Linear Model that Predicts Arginine Production Amount in Interval 4].

In a linear model that predicts an arginine production amount at the end of Interval 5 (the amount of arginine produced in the culture time of Interval 5) based on data at the beginning of Interval 5 (top 1,000 expressions with a high adjusted coefficient of determination with leave-one-out cross-validation performed and a high coefficient of correlation with leave-one-out cross-validation performed), the arithmetic sign of the median of the coefficient of temperature as a control variable was "+," and the arithmetic sign of the median of the coefficient of pH as a control variable was "+." A list of the top 1,000 expressions is described in [205. Linear Model that Predicts Arginine Production Amount in Interval 5].

In a linear model that predicts an arginine production amount at the end of Interval 6 (the amount of arginine produced in the culture time of Interval 6) based on data at the beginning of Interval 6 (top 1,000 expressions with a high adjusted coefficient of determination with leave-one-out cross-validation performed and a high coefficient of correlation with leave-one-out cross-validation performed), the arithmetic sign of the median of the coefficient of temperature as a control variable was "−," and the arithmetic sign of the median of the coefficient of pH as a control variable was "−." A list of the top 1,000 expressions is described in [206. Linear Model that Predicts Arginine Production Amount in Interval 6].

In a linear model that predicts an arginine production amount at the end of Interval 7 (the amount of arginine produced in the culture time of Interval 7) based on data at the beginning of Interval 7 (top 1,000 expressions with a high adjusted coefficient of determination with leave-one-out cross-validation performed and a high coefficient of correlation with leave-one-out cross-validation performed), the arithmetic sign of the median of the coefficient of temperature as a control variable was "+," and the arithmetic sign of the median of the coefficient of pH as a control variable was "+." A list of the top 1,000 expressions is described in [207. Linear Model that Predicts Arginine Production Amount in Interval 7].

In a linear model that predicts an arginine production amount at the end of Interval 8 (the amount of arginine produced in the culture time of Interval 8) based on data at the beginning of Interval 8 (top 1,000 expressions with a high adjusted coefficient of determination with leave-one-out cross-validation performed and a high coefficient of correlation with leave-one-out cross-validation performed), the arithmetic sign of the median of the coefficient of temperature as a control variable was "−," and the arithmetic sign of the median of the coefficient of pH as a control variable was "−." A list of the top 1,000 expressions is described in [208. Linear Model that Predicts Arginine Production Amount in Interval 8].

In a linear model that predicts an arginine production amount at the end of Interval 9 (the amount of arginine produced in the culture time of Interval 9) based on data at the beginning of Interval 9 (top 1,000 expressions with a high adjusted coefficient of determination with leave-one-out cross-validation performed and a high coefficient of correlation with leave-one-out cross-validation performed), the arithmetic sign of the median of the coefficient of temperature as a control variable was "−," whereas the arithmetic sign of the median of the coefficient of pH as a control variable was "+." A list of the top 1,000 expressions is described in [209. Linear Model that Predicts Arginine Production Amount in Interval 9].

In a linear model that predicts an arginine production amount at the end of Interval 10 (the amount of arginine produced in the culture time of Interval 10) based on data at the beginning of Interval 10 (top 1,000 expressions with a high adjusted coefficient of determination with leave-one-out cross-validation performed and a high coefficient of correlation with leave-one-out cross-validation performed), the arithmetic sign of the median of the coefficient of temperature as a control variable was "−," and the arithmetic sign of the median of the coefficient of pH as a control variable was "−." A list of the top 1,000 expressions is described in [210. Linear Model that Predicts Arginine Production Amount in Interval 10].

4. Operating Condition Range

The control variables changed during fermentation operation were pH and temperature. FIG. 18 depicts an operating condition range. For the creation of the linear model, data acquired within a range denoted as "DATABASE" in FIG. 18 was used. In Example 3, the operating condition was changed within a range denoted as "OPERATING CONDITION RANGE" in FIG. 18 (the same range as the range denoted as "DATABASE" in FIG. 18). In FIG. 18, the values of the operating condition are represented as relative values to the value of the operating condition of J1 target depicted in FIG. 16.

5. Arginine Concentration Analysis

During culture control, an arginine concentration measured by the biosensor was used. Then, in the stage of determining a final result of the fermentation result, recalculation was performed using an arginine concentration measured by HPLC. For the creation of the linear model, the arginine concentration measured by HPLC was used.

6. Results and Discussion

Figure 20:
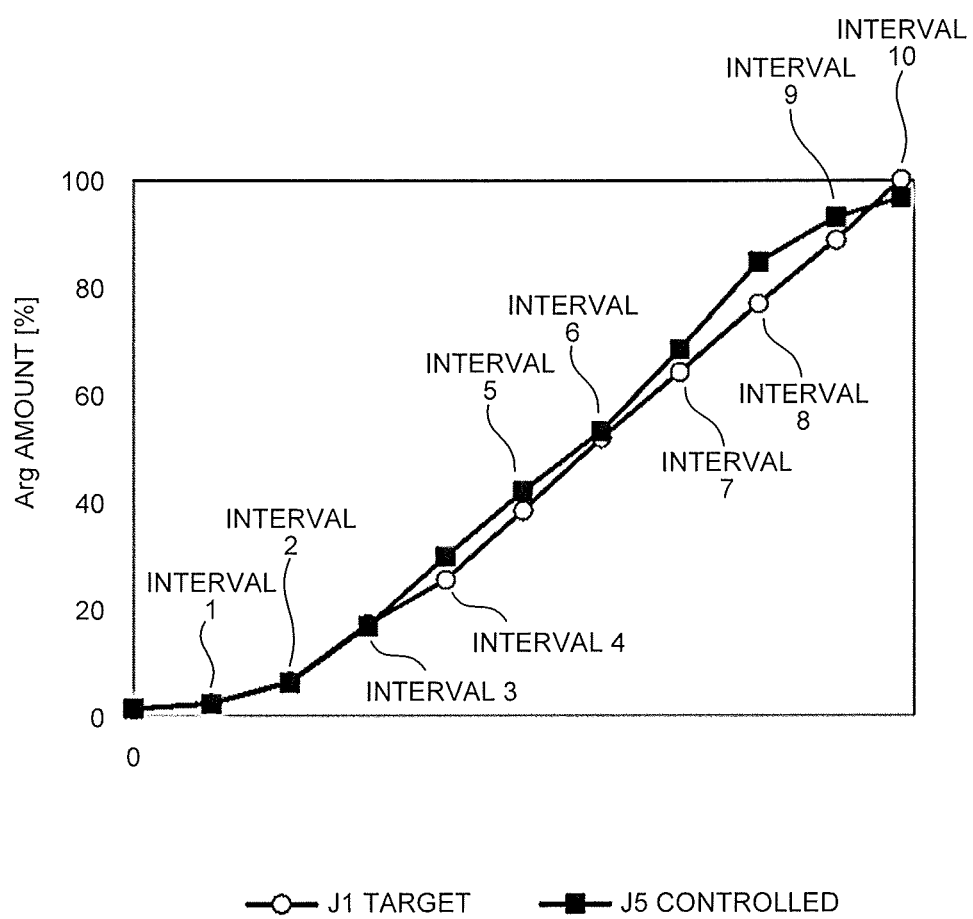
FIG. 20 is a diagram of an exemplary graph of the Arg culture result.

FIG. 19 and FIG. 20 depict culture results by the respective experimental conditions.

FIG. 19 depicts the sign of the median of the coefficients of the control variables of the linear model described in FIG. 17, J5 control condition, which performed control, described in FIG. 16, J5 control description, arginine amounts of J1, which did not perform control, and arginine amounts of J5, which performed control.

An arithmetic sign "+" described in the column of the sign of the coefficient median in FIG. 19 means that the arginine production amount in the next interval can be increased by making temperature higher or pH higher than that of the standard condition in FIG. 18. An arithmetic sign "−" described means that the arginine production amount in the next interval can be increased by making temperature lower or pH lower than that of the standard condition in FIG. 18.

By comparing J5 control condition in FIG. 19 and J1 standard condition in FIG. 16 with each other, the control performed by J5 can be classified into three control descriptions including increasing the arginine production amount, decreasing it, and having no influence on J1. The column of J5 control description in FIG. 19 describes "INCREASE" in the case of a control description of increasing the arginine production amount compared with J1, "DECREASE" in the case of a control description of decreasing the arginine production amount compared with J1, and "NONE" in the case of a control description making the arginine production amount comparable to J1 (the control description of Interval 1 has an influence on the fermentation result of Interval 1, and FIG. 19 is represented with the part up to the fifth column from the left and the part from the sixth column on from the left staggered by one row).

To confirm the control result, the results of J1 and J5 were compared with each other. In the column of difference of J5-J1 in FIG. 19, when the control description is "DECREASE," a negative value is given, whereas when the control description is "INCREASE," a positive value is given, and it is considered that control as estimated can be achieved using the linear model.

In the present specification, various kinds of explanatory variables are mainly denoted by abbreviations; their formal names are as follows.

Abbreviation of explanatory variable (Formal name)
tmp: Culture medium temperature
tmp_cumulo: Culture medium temperature accumulated value
pH: Culture medium pH
pH_cumulo: Culture medium pH accumulated value
PL: Dissolved oxygen concentration in culture medium
PL_cumulo: Accumulated value of dissolved oxygen concentration in culture medium
AN: Ammonia nitrogen concentration in culture medium
AN_cumulo: Accumulated value of ammonia nitrogen concentration in culture medium
interval_yield: Interval arginine yield
interval_Pdt.: Interval arginine productivity
OD: Culture medium turbidity
RS: Sugar_concentration in culture medium
Feed_Vol: Sugar-ammonium sulfate mixed liquid feed amount mu_cumulo: Specific multiplication rate accumulated value
nu_cumulo: Specific sugar consumption rate accumulated value
rho_cumulo: Specific production rate accumulated value
nu_per_rho_cumulo: Specific multiplication rate/specific production rate accumulated value
RS_cumulo: Accumulated value of sugar concentration in culture medium
Sugar_consuming_rate_cumulo: Sugar consumption rate accumulated value
Arg_conc._cumulo: Accumulated value of arginine concentration in culture medium
cell_yield_cumulo: Cell yield accumulated value
Cell_conc._cumulo: Cell concentration accumulated value
Cell_conc._interval: Cell concentration difference between intervals
rab_integral: Average oxygen demand
RQ_integral: Average respiratory quotient
Accum._Yield: Accumulated yield
Arg_conc.: Arginine concentration in culture medium
AS_Vol.: Ammonium sulfate feed amount (added amount)
emission_O2: Oxygen concentration in emission gas
emission_CO2: Carbon dioxide concentration in emission gas
consum_O2: Oxygen consumption amount
interval_O2: Accumulated oxygen consumption amount
generate_CO2: Carbon dioxide generation amount
interval_CO2: Accumulated carbon dioxide generation amount
RQ: Respiratory quotient
rab: Oxygen demand
Main.P-Source.Conc.: Phosphorous source concentration in culture medium at the start of culture
P-Source.Feed.conc.: Phosphorous source concentration in culture fed-batch liquid
Main.Thr.Conc.: Threonine concentration in culture medium at the start of culture
Nitrogen.Conc.: Nitrogen source concentration in culture medium at the start of culture
Lys_conc.: Lysine concentration in culture medium
feed.Sugar: Fed-batch sugar liquid amount
X.F.Sugar: Fed-batch sugar liquid amount per interval
Cell: Cell amount in culture medium
X.VXdt: Integrated cell amount
total.Vol: Total culture medium amount
total.cell: Total cell amount
total.sugar: Total sugar consumption amount
yield: Product yield
Thr: Threonine concentration in culture medium
His: Histidine concentration in culture medium
lactate: Lactic acid concentration in culture medium
SO4.ferm.: Sulfuric acid ion concentration in culture medium
PO4.ferm.: Phosphoric acid ion concentration in culture medium
PO4.apporte: Phosphoric acid ion added amount during culture
PO4.utilise: Phosphoric acid ion consumption amount during culture

[11. Linear Model that Predicts Lysine Production Amount in Interval 1]
0.647, 0.828, pH+tmp+Main.P-Source.Conc.+Nitrogen.Conc.+Thr+lactate+PO4.apporte; 0.652, 0.827, tmp+Main.P-Source.Conc.+Nitrogen.Conc.+Thr+lactate+PO4.apporte; 0.646, 0.827, tmp+Main.P-Source.Conc.+P-Source.Feed.conc.+Nitrogen.Conc.+Thr+lactate+PO4.apporte; 0.636, 0.825, pH+tmp+Main.P-Source.Conc.+Nitrogen.Conc.+total.Vol+Thr+lactate+PO4.apporte; 0.636, 0.825, pH+tmp+Main.P-Source.Conc.+Nitrogen.Conc.+emission_O2+Thr+lactate+PO4.apporte; 0.636, 0.825, pH+tmp+Main.P-Source.Conc.+P-Source.Feed.conc.+Nitrogen.Conc.+Thr+lactate+PO4.apporte; 0.635, 0.825, pH+tmp+Main.P-Source.Conc.+Nitrogen.Conc.+PL+Thr+lactate+PO4.apporte; 0.634, 0.824, tmp+Main.P-Source.Conc.+P-Source.Feed.conc.+Nitrogen.Conc.+emission_O2+Thr+lactate+PO4.apporte; 0.641, 0.824, tmp+Main.P-Source.Conc.+Nitrogen.Conc.+emission_O2+Thr+lactate+PO4.apporte; 0.634, 0.824, pH+tmp+Main.P-Source.Conc.+Nitrogen.Conc.+emission_CO2+Thr+lactate+PO4.apporte; 0.640, 0.824, tmp+Main.P-Source.Conc.+Nitrogen.Conc.+PL+Thr+lactate+PO4.apporte; 0.638, 0.823, tmp+Main.P-Source.Conc.+Main.Thr.Conc.+Nitrogen.Conc.+Thr+lactate+PO4.apporte; 0.625, 0.823, pH+tmp+Main.P-Source.Conc.+Nitrogen.Conc.+emission_O2+emission_CO2+Thr+lactate+PO4.apporte; 0.638, 0.823, tmp+Main.P-Source.Conc.+Nitrogen.Conc.+Thr+His+lactate+PO4.apporte; 0.625, 0.823, pH+tmp+Main.P-Source.Conc.+Nitrogen.Conc.+total.Vol+emission_O2+Thr+lactate+PO4.apporte; 0.631, 0.823, tmp+Main.P-Source.Conc.+P-Source.Feed.conc.+Nitrogen.Conc.+PL+Thr+lactate+PO4.apporte; 0.638, 0.823, tmp+Main.P-Source.Conc.+Nitrogen.Conc.+total.Vol+Thr+lactate+PO4.apporte; 0.631, 0.823, pH+tmp+Main.P-Source.Conc.+Nitrogen.Conc.+Thr+His+lactate+PO4.apporte; 0.631, 0.823, pH+tmp+Main.P-Source.Conc.+Main.Thr.Conc.+Nitrogen.Conc.+Thr+lactate+PO4.apporte; 0.631, 0.822, tmp+Main.P-Source.Conc.+P-Source.Feed.conc.+Nitrogen.Conc.+emission_CO2+Thr+lactate+PO4.apporte; 0.624, 0.822, pH+tmp+Main.P-Source.Conc.+P-Source.Feed.conc.+Nitrogen.Conc.+emission_O2+Thr+lactate+PO4.apporte; 0.624, 0.822, pH+tmp+Main.P-Source.Conc.+Nitrogen.Conc.+PL+emission_O2+Thr+lactate+PO4.apporte; 0.637, 0.822, tmp+Main.P-Source.Conc.+Nitrogen.Conc.+total.sugar+Thr+lactate+PO4.apporte; 0.624, 0.822, pH+tmp+Main.P-Source.Conc.+Nitrogen.Conc.+total.Vol+PL+Thr+lactate+PO4.apporte; 0.630, 0.822, pH+tmp+Main.P-Source.Conc.+Nitrogen.Conc.+total.sugar+Thr+lactate+PO4.apporte; 0.637, 0.822, tmp+Main.P-Source.Conc.+Nitrogen.Conc.+emission_CO2+Thr+lactate+PO4.apporte; 0.624, 0.822, pH+tmp+Main.P-Source.Conc.+Nitrogen. Conc.+total.Vol+emission_CO2+Thr+lactate+PO4.apporte; 0.623, 0.822, tmp+Main.P-Source.Conc.+P-Source.Feed.conc.+Nitrogen.Conc.+emission_O2+emission_CO2+Thr+lactate+PO4.apporte; 0.630, 0.822, tmp+Main.P-Source.Conc.+P-Source.Feed.conc.+Main.Thr.Conc.+Nitrogen.Conc.+Thr+lactate+PO4.apporte; 0.629, 0.822, tmp+Main.P-Source.Conc.+P-Source.Feed.conc.+Nitrogen.Conc.+Thr+His+lactate+PO4.apporte; 0.616, 0.822, pH+tmp+Main.P-Source.Conc.+Nitrogen.Conc.+total.Vol+emission_O2+emission_CO2+Thr+lactate+PO4.apporte; 0.629, 0.821, tmp+Main.P-Source.Conc.+P-Source.Feed.conc.+Nitrogen.Conc.+total.Vol+Thr+lactate+PO4.apporte; 0.622, 0.821, pH+tmp+Main.P-Source.Conc.+P-Source.Feed.conc.+Nitrogen.Conc.+emission_CO2+Thr+lactate+PO4.apporte; 0.622, 0.821, pH+tmp+Main.P-Source.Conc.+P-Source.Feed.conc.+Nitrogen.Conc.+total.Vol+Thr+lactate+PO4.apporte; 0.622, 0.821, pH+tmp+Main.P-Source.Conc.+Nitrogen.Conc.+PL+emission_CO2+Thr+lactate+PO4.apporte; 0.622, 0.821, pH+tmp+Main.P-Source.Conc.+P-Source.Feed.conc.+Nitrogen.Conc.+PL+Thr+lactate+PO4.apporte; 0.628, 0.821, tmp+Main.P-Source.Conc.+Nitrogen.Conc.+emission_O2+emission_CO2+Thr+lactate+PO4.apporte; 0.614, 0.821, pH+tmp+Main.P-Source.Conc.+P-Source.Feed.conc.+Nitrogen.Conc.+emission_O2+emission_CO2+Thr+lactate+PO4.apporte; 0.628, 0.821, tmp+Main.P-Source.Conc.+Nitrogen.Conc.+PL+emission_O2+Thr+lactate+PO4.apporte; 0.621, 0.821, tmp+Main.P-Source.Conc.+P-Source.Feed.conc.+Nitrogen.Conc.+emission_CO2+rab+Thr+lactate+PO4.apporte; 0.621, 0.820, pH+tmp+Main.P-Source.Conc.+Main.Thr.Conc.+Nitrogen.Conc.+total.Vol+Thr+lactate+PO4.apporte; 0.627, 0.820, tmp+Main.P-Source.Conc.+P-Source.Feed.conc.+Nitrogen.Conc.+total.sugar+Thr+lactate+PO4.apporte; 0.613, 0.820, pH+tmp+Main.P-Source.Conc.+Nitrogen.Conc.+PL+emission_O2+emission_CO2+Thr+lactate+PO4.apporte; 0.627, 0.820, tmp+Main.P-Source.Conc.+Nitrogen.Conc.+emission_CO2+rab+Thr+lactate+PO4.apporte; 0.620, 0.820, pH+tmp+Main.P-Source.Conc.+Nitrogen.Conc.+emission_O2+Thr+His+lactate+PO4.apporte; 0.620, 0.820, pH+tmp+Main.P-Source.Conc.+Nitrogen.Conc.+total.Vol+Thr+His+lactate+PO4.apporte; 0.620, 0.820, pH+tmp+Main.P-Source.Conc.+Main.Thr.Conc.+Nitrogen.Conc.+emission_O2+Thr+lactate+PO4.apporte; 0.626, 0.820, tmp+Main.P-Source.Conc.+Main.Thr.Conc.+Nitrogen.Conc.+emission_O2+Thr+lactate+PO4.apporte; 0.619, 0.820, tmp+Main.P-Source.Conc.+P-Source.Feed.conc.+Nitrogen.Conc.+PL+emission_O2+Thr+lactate+PO4.apporte; 0.619, 0.820, pH+tmp+Main.P-Source.Conc.+P-Source.Feed.conc.+Main.Thr.Conc.+Nitrogen.Conc.+Thr+lactate+PO4.apporte; 0.626, 0.820, tmp+Main.P-Source.Conc.+Nitrogen.Conc.+emission_O2+Thr+His+lactate+PO4.apporte; 0.612, 0.819, pH+tmp+Main.P-Source.Conc.+Nitrogen.Conc.+total.Vol+emission_CO2+rab+Thr+lactate+PO4.apporte; 0.625, 0.819, tmp+Main.P-Source.Conc.+Nitrogen.Conc.+total.Vol+emission_O2+Thr+lactate+PO4.apporte; 0.618, 0.819, pH+tmp+Main.P-Source.Conc.+Main.Thr.Conc.+Nitrogen.Conc.+PL+Thr+lactate+PO4.apporte; 0.625, 0.819, tmp+Main.P-Source.Conc.+Main.Thr.Conc.+Nitrogen.Conc.+PL+Thr+lactate+PO4.apporte; 0.611, 0.819, pH+tmp+Main.P-Source.Conc.+Nitrogen.Conc.+total.Vol+PL+emission_O2+Thr+lactate+PO4.apporte; 0.618, 0.819, pH+tmp+Main.P-Source.Conc.+P-Source.Feed.conc.+Nitrogen.Conc.+Thr+His+lactate+PO4.apporte; 0.618, 0.819, pH+tmp+Main.P-Source.Conc.+Nitrogen.Conc.+total.sugar+emission_O2+Thr+lactate+PO4.apporte; 0.618, 0.819, pH+tmp+Main.P-Source.Conc.+Nitrogen.Conc.+PL+Thr+His+lactate+PO4.apporte; 0.618, 0.819, pH+tmp+Main.P-Source.Conc.+Nitrogen.Conc.+total.sugar+PL+Thr+lactate+PO4.apporte; 0.618, 0.819, pH+tmp+Main.P-Source.Conc.+Main.Thr.Conc.+Nitrogen.Conc.+total.sugar+Thr+lactate+PO4.apporte; 0.618, 0.819, pH+tmp+Main.P-Source.Conc.+Main.Thr.Conc.+Nitrogen.Conc.+emission_CO2+Thr+lactate+PO4.apporte; 0.618, 0.819, tmp+Main.P-Source.Conc.+P-Source.Feed.conc.+Nitrogen.Conc.+emission_O2+Thr+His+lactate+PO4.apporte; 0.618, 0.819, tmp+Main.P-Source.Conc.+P-Source.Feed.conc.+Main.Thr.Conc.+Nitrogen.Conc.+emission_O2+Thr+lactate+PO4.apporte; 0.617, 0.819, pH+tmp+Main.P-Source.Conc.+Nitrogen.Conc.+PL+rab+Thr+lactate+PO4.apporte; 0.624, 0.819, pH+tmp+Main.P-Source.Conc.+Nitrogen.Conc.+rab+Thr+lactate+PO4.apporte; 0.617, 0.819, pH+tmp+Main.P-Source.Conc.+Nitrogen.Conc.+emission_CO2+Thr+His+lactate+PO4.apporte; 0.610, 0.819, pH+tmp+Main.P-Source.Conc.+Nitrogen.Conc.+total.Vol+emission_CO2+Thr+lactate+PO4.apporte; 0.624, 0.819, tmp+Main.P-Source.Conc.+Nitrogen.Conc.+PL+emission_CO2+Thr+lactate+PO4.apporte; 0.624, 0.819, tmp+Main.P-Source.Conc.+Nitrogen.Conc.+PL+Thr+His+lactate+PO4.apporte; 0.624, 0.819, tmp+Main.P-Source.Conc.+Nitrogen.Conc.+total.sugar+emission_O2+Thr+lactate+PO4.apporte; 0.624, 0.819, tmp+Main.P-Source.Conc.+Nitrogen.Conc.+total.Vol+PL+Thr+lactate+PO4.apporte; 0.624, 0.819, tmp+Main.P-Source.Conc.+Nitrogen.Conc.+total.sugar+PL+Thr+lactate+PO4.apporte; 0.624, 0.818, tmp+Main.P-Source.Conc.+Main.Thr.Conc.+Nitrogen.Conc.+total.sugar+Thr+lactate+PO4.apporte; 0.624, 0.818, tmp+Main.P-Source.Conc.+Main.Thr.Conc.+Nitrogen.Conc.+total.Vol+Thr+lactate+PO4.apporte; 0.617, 0.818, tmp+Main.P-Source.Conc.+P-Source.Feed.conc.+Nitrogen.Conc.+total.Vol+emission_O2+Thr+lactate+PO4.apporte; 0.617, 0.818, pH+tmp+Main.P-Source.Conc.+P-Source.Feed.conc.+Nitrogen.Conc.+total.sugar+Thr+lactate+PO4.apporte; 0.610, 0.818, pH+tmp+Main.P-Source.Conc.+P-Source.Feed.conc.+Nitrogen.Conc.+PL+emission_O2+Thr+lactate+PO4.apporte; 0.609, 0.818, pH+tmp+Main.P-Source.Conc.+P-Source.Feed.conc.+Nitrogen.Conc.+total.Vol+emission_O2+Thr+lactate+PO4.apporte; 0.616, 0.818, tmp+Main.P-Source.Conc.+Nitrogen.Conc.+PL+emission_CO2+rab+Thr+lactate+PO4.apporte; 0.623, 0.818, tmp+Main.P-Source.Conc.+Nitrogen.Conc.+total.sugar+Thr+His+lactate+PO4.apporte; 0.623, 0.818, tmp+Main.P-Source.Conc.+Main.Thr.Conc.+Nitrogen.Conc.+Thr+His+lactate+PO4.apporte; 0.616, 0.818, pH+tmp+Main.P-Source.Conc.+Nitrogen.Conc.+emission_CO2+rab+Thr+lactate+PO4.apporte; 0.616, 0.818, tmp+Main.P-Source.Conc.+P-Source.Feed.conc.+Nitrogen.Conc.+PL+emission_CO2+Thr+lactate+PO4.apporte; 0.616, 0.818, pH+tmp+Main.P-Source.Conc.+Nitrogen.Conc.+total.Vol+total.sugar+Thr+lactate+PO4.apporte; 0.609, 0.818, pH+tmp+Main.P-Source.Conc.+P-Source.Feed.conc.+Nitrogen.Conc.+total.Vol+emission_CO2+Thr+lactate+PO4.apporte; 0.616, 0.818, tmp+Main.P-Source.Conc.+Nitrogen.Conc.+PL+emission_O2+emission_CO2+Thr+lactate+PO4.apporte; 0.622, 0.818, tmp+Main.P-Source.Conc.+Nitrogen.Conc.+total.Vol+Thr+His+lactate+PO4.apporte; 0.609, 0.818, pH+tmp+Main.P-Source.Conc.+Main.Thr.Conc.+Nitrogen.Conc.+emission_O2+emission_CO2+Thr+lactate+PO4.apporte; 0.609, 0.818, pH+tmp+Main.P-Source.Conc.+Main.Thr.Conc.+Nitrogen.Conc.+total.Vol+emission_O2+Thr+lactate+PO4.apporte; 0.615, 0.818, pH+tmp+Main.P-Source.Conc.+Nitrogen.Conc.+total.sugar+Thr+His+lactate+PO4.apporte; 0.608, 0.818, pH+tmp+Main.P-Source.Conc.+Nitrogen.Conc.+emission_O2+emission_CO2+Thr+His+lactate+PO4.apporte; 0.615, 0.818, pH+tmp+Main.P-Source.Conc.+Main.Thr.Conc.+Nitrogen.Conc.+Thr+His+lactate+PO4.apporte; 0.608, 0.818, pH+tmp+Main.P-Source.Conc.+Nitrogen.Conc.+total.Vol+emission_O2+Thr+His+lactate+PO4.apporte; 0.622, 0.817, tmp+Main.P-Source.Conc.+Main.Thr.Conc.+Nitrogen.Conc.+emission_CO2+Thr+lactate+PO4.apporte; 0.601, 0.817, pH+tmp+Main.P-Source.Conc.+Nitrogen.Conc.+total.Vol+PL+emission_O2+emission_CO2+Thr+lactate+PO4.apporte; 0.601, 0.817, pH+tmp+Main.P-Source.Conc.+P-Source.Feed.conc.+Nitrogen.Conc.+total.Vol+emission_O2+emission_CO2+Thr+lactate+PO4.apporte; 0.608, 0.817, pH+tmp+Main.P-Source.Conc.+P-Source.Feed.conc.+Nitrogen.Conc.+total.Vol+PL+Thr+lactate+PO4.apporte; 0.608, 0.817, pH+tmp+Main.P-Source.Conc.+P-Source.Feed.conc.+Nitrogen.Conc.+PL+emission_CO2+Thr+lactate+PO4.apporte; 0.608, 0.817, tmp+Main.P-Source.Conc.+P-Source.Feed.conc.+Nitrogen.Conc.+PL+emission_O2+emission_CO2+Thr+lactate+PO4.apporte; 0.628, 0.817, tmp+Main.P-Source.Conc.+Nitrogen.Conc.+ rab+Thr+lactate+PO4.apporte; 0.615, 0.817, tmp+Main.P-Source.Conc.+P-Source.Feed.conc.+Nitrogen.Conc.+total. sugar+emission_O2+Thr+lactate+PO4.apporte; 0.621, 0.817, tmp+Main.P-Source.Conc.+Nitrogen.Conc.+total. Vol+emission_CO2+Thr+lactate+PO4.apporte; 0.607, 0.817, pH+tmp+Main.P-Source.Conc.+Main.Thr.Conc.+ Nitrogen.Conc.+total.Vol+emission_CO2+Thr+lactate+ PO4.apporte; 0.621, 0.817, tmp+Main.P-Source.Conc.+Nitrogen.Conc.+PL+rab+Thr+lactate+PO4.apporte; 0.607, 0.817, pH+tmp+Main.P-Source.Conc.+Nitrogen.Conc.+ PL+emission_CO2+rab+Thr+lactate+PO4.apporte; 0.621, 0.817, tmp+Main.P-Source.Conc.+Nitrogen.Conc.+emission_CO2+Thr+His+lactate+PO4.apporte; 0.607, 0.817, pH+tmp+Main.P-Source.Conc.+Main.Thr.Conc.+Nitrogen. Conc.+total.Vol+PL+Thr+lactate+PO4.apporte; 0.614, 0.817, tmp+Main.P-Source.Conc.+P-Source.Feed.conc.+ Main.Thr.Conc.+Nitrogen.Conc.+emission_CO2+Thr+lactate+PO4.apporte; 0.607, 0.817, pH+tmp+Main.P-Source.Conc.+P-Source.Feed.conc.+Main.Thr.Conc.+ Nitrogen.Conc.+emission_O2+Thr+lactate+PO4.apporte; 0.614, 0.817, tmp+Main.P-Source.Conc.+P-Source.Feed. conc.+Nitrogen.Conc.+emission_CO2+Thr+His+lactate+ PO4.apporte; 0.614, 0.817, tmp+Main.P-Source.Conc.+P-Source.Feed.conc.+Main.Thr.Conc.+Nitrogen.Conc.+PL+ Thr+lactate+PO4.apporte; 0.614, 0.817, tmp+Main.P-Source.Conc.+P-Source.Feed.conc.+Nitrogen.Conc.+ total.Vol+emission_CO2+Thr+lactate+PO4.apporte; 0.607, 0.817, tmp+Main.P-Source.Conc.+P-Source.Feed.conc.+ Nitrogen.Conc.+PL+emission_CO2+rab+Thr+lactate+ PO4.apporte; 0.607, 0.817, pH+tmp+Main.P-Source.Conc.+ P-Source.Feed.conc.+Nitrogen.Conc.+emission_CO2+rab+ Thr+lactate+PO4.apporte; 0.607, 0.817, pH+tmp+Main.P-Source.Conc.+Main.Thr.Conc.+Nitrogen.Conc.+PL+ emission_O2+Thr+lactate+PO4.apporte; 0.607, 0.817, pH+tmp+Main.P-Source.Conc.+Nitrogen.Conc.+total.Vol+ emission_CO2+Thr+His+lactate+PO4.apporte; 0.607, 0.817, pH+tmp+Main.P-Source.Conc.+P-Source.Feed. conc.+Nitrogen.Conc.+emission_O2+Thr+His+lactate+ PO4.apporte; 0.614, 0.817, pH+tmp+Main.P-Source.Conc.+ Nitrogen.Conc.+total.sugar+emission_CO2+Thr+lactate+ PO4.apporte; 0.607, 0.817, pH+tmp+Main.P-Source.Conc.+ Nitrogen.Conc.+PL+emission_O2+Thr+His+lactate+ PO4.apporte; 0.599, 0.817, pH+tmp+Main.P-Source.Conc.+ Main.Thr.Conc.+Nitrogen.Conc.+total.Vol+emission_O2+ emission_CO2+Thr+lactate+PO4.apporte; 0.599, 0.817, pH+tmp+Main.P-Source.Conc.+P-Source.Feed.conc.+Nitrogen.Conc.+PL+emission_O2+emission_CO2+Thr+lactate+PO4.apporte; 0.613, 0.817, tmp+Main.P-Source.Conc.+P-Source.Feed.conc.+Nitrogen.Conc.+PL+ Thr+His+lactate+PO4.apporte; 0.613, 0.817, tmp+Main.P-Source.Conc.+P-Source.Feed.conc.+Nitrogen.Conc.+ total.Vol+PL+Thr+lactate+PO4.apporte; 0.620, 0.817, tmp+ Main.P-Source.Conc.+P-Source.Feed.conc.+ Nitrogen.Conc.+rab+Thr+lactate+PO4.apporte; 0.613, 0.817, tmp+Main.P-Source.Conc.+Nitrogen.Conc.+total. Vol+emission_O2+emission_CO2+Thr+lactate+ PO4.apporte; 0.606, 0.817, tmp+Main.P-Source.Conc.+P-Source.Feed.conc.+Main.Thr.Conc.+Nitrogen.Conc.+emission_O2+emission_CO2+Thr+lactate+PO4.apporte; 0.606, 0.816, tmp+Main.P-Source.Conc.+P-Source.Feed.conc.+ Nitrogen.Conc.+emission_O2+emission_CO2+Thr+His+ lactate+PO4.apporte; 0.613, 0.816, tmp+Main.P-Source.Conc.+Nitrogen.Conc.+total.Vol+emission_CO2+ rab+Thr+lactate+PO4.apporte; 0.613, 0.816, tmp+Main.P-Source.Conc.+P-Source.Feed.conc.+Main.Thr.Conc.+ Nitrogen.Conc.+Thr+His+lactate+PO4.apporte; 0.606, 0.816, pH+tmp+Main.P-Source.Conc.+Nitrogen.Conc.+total.Vol+PL+Thr+His+lactate+PO4.apporte; 0.613, 0.816, tmp+Main.P-Source.Conc.+Main.Thr.Conc.+Nitrogen. Conc.+emission_O2+emission_CO2+Thr+lactate+ PO4.apporte; 0.606, 0.816, tmp+Main.P-Source.Conc.+P-Source.Feed.conc.+Nitrogen.Conc.+total.Vol+emission_O2+emission_CO2+Thr+lactate+PO4.apporte; 0.598, 0.816, pH+tmp+Main.P-Source.Conc.+Nitrogen. Conc.+total.Vol+emission_O2+emission_CO2+Thr+His+lactate+ PO4.apporte; 0.613, 0.816, tmp+Main.P-Source.Conc.+P-Source.Feed.conc.+Main.Thr.Conc.+Nitrogen.Conc.+ total.Vol+Thr+lactate+PO4.apporte; 0.613, 0.816, pH+tmp+ Main.P-Source.Conc.+P-Source.Feed. conc.+ Nitrogen.Conc.+rab+Thr+lactate+PO4.apporte; 0.619, 0.816, tmp+Main.P-Source.Conc.+Nitrogen.Conc.+total. Vol+total.sugar+Thr+lactate+PO4.apporte; 0.612, 0.816, tmp+Main.P-Source.Conc.+Main.Thr.Conc.+Nitrogen. Conc.+PL+emission_O2+Thr+lactate+PO4.apporte; 0.612, 0.816, tmp+Main.P-Source.Conc.+P-Source.Feed.conc.+ Nitrogen.Conc.+total.sugar+Thr+His+lactate+PO4.apporte; 0.612, 0.816, tmp+Main.P-Source.Conc.+P-Source.Feed. conc.+Main.Thr.Conc.+Nitrogen.Conc.+total.sugar+Thr+ lactate+PO4.apporte; 0.605, 0.816, pH+tmp+Main.P-Source.Conc.+P-Source.Feed.conc.+Main.Thr.Conc.+Nitrogen.Conc.+emission_CO2+Thr+lactate+PO4.apporte; 0.605, 0.816, pH+tmp+Main.P-Source.Conc.+Nitrogen. Conc.+total.sugar+PL+emission_O2+Thr+lactate+ PO4.apporte; 0.598, 0.816, pH+tmp+Main.P-Source.Conc.+ Nitrogen.Conc.+total.Vol+PL+emission_CO2+rab+Thr+ lactate+PO4.apporte; 0.612, 0.816, tmp+Main.P-Source.Conc.+Nitrogen.Conc.+emission_O2+ emission_CO2+Thr+His+lactate+PO4.apporte; 0.605, 0.816, pH+tmp+Main.P-Source.Conc.+P-Source.Feed. conc.+Main.Thr.Conc.+Nitrogen.Conc.+total.Vol+Thr+lactate+PO4.apporte; 0.605, 0.816, pH+tmp+Main.P-Source.Conc.+Main.Thr.Conc.+Nitrogen.Conc.+total. sugar+emission_O2+Thr+lactate+PO4.apporte; 0.612, 0.816, tmp+Main.P-Source.Conc.+P-Source.Feed.conc.+ Nitrogen.Conc.+total.Vol+Thr+His+lactate+PO4.apporte; 0.605, 0.816, pH+tmp+Main.P-Source.Conc.+Nitrogen. Conc.+total.sugar+emission_O2+emission_CO2+Thr+lactate+PO4.apporte; 0.604, 0.816, pH+tmp+Main.P-Source.Conc.+Main.Thr.Conc.+Nitrogen.Conc.+PL+emission_CO2+Thr+lactate+PO4.apporte; 0.604, 0.816, pH+tmp+Main.P-Source.Conc.+P-Source.Feed.conc.+Nitrogen.Conc.+emission_CO2+Thr+His+lactate+ PO4.apporte; 0.611, 0.816, tmp+Main.P-Source.Conc.+Nitrogen.Conc.+PL+emission_O2+Thr+His+lactate+ PO4.apporte; 0.604, 0.816, pH+tmp+Main.P-Source.Conc.+ P-Source.Feed.conc.+Nitrogen.Conc.+total.sugar+ emission_O2+Thr+lactate+PO4.apporte; 0.611, 0.816, tmp+ Main.P-Source.Conc.+P-Source.Feed.conc.+ Nitrogen.Conc.+total.sugar+PL+Thr+lactate+PO4.apporte; 0.597, 0.816, pH+tmp+Main.P-Source.Conc.+P-Source. Feed.conc.+Main.Thr.Conc.+Nitrogen.Conc.+emission_O2+emission_CO2+Thr+lactate+PO4.apporte; 0.604, 0.815, pH+tmp+Main.P-Source.Conc.+P-Source.Feed. conc.+Nitrogen.Conc.+total.Vol+Thr+His+lactate+ PO4.apporte; 0.604, 0.815, pH+tmp+Main.P-Source.Conc.+ Main.Thr.Conc.+Nitrogen.Conc.+total.sugar+PL+Thr+lactate+PO4.apporte; 0.611, 0.815, tmp+Main.P-Source.Conc.+Main.Thr.Conc.+Nitrogen.Conc.+ emission_CO2+rab+Thr+lactate+PO4.apporte; 0.604, 0.815, pH+tmp+Main.P-Source.Conc.+Nitrogen.Conc.+ PL+emission_CO2+Thr+His+lactate+PO4.apporte; 0.596, 0.815, pH+tmp+Main.P-Source.Conc.+P-Source.Feed. conc.+Nitrogen.Conc.+total.Vol+emission_CO2+rab+Thr+ lactate+PO4.apporte; 0.604, 0.815, pH+tmp+Main.P-

Source.Conc.+Main.Thr.Conc.+Nitrogen.Conc.+total.Vol+ Thr+His+lactate+PO4.apporte; 0.611, 0.815, tmp+Main.P-Source.Conc.+Nitrogen.Conc.+total.Vol+PL+ emission_O2+Thr+lactate+PO4.apporte; 0.604, 0.815, tmp+Main.P-Source.Conc.+P-Source.Feed.conc.+ Nitrogen.Conc.+total.Vol+emission_CO2+rab+Thr+ lactate+PO4.apporte; 0.604, 0.815, pH+tmp+Main.P-Source.Conc.+P-Source.Feed.conc.+Main.Thr.Conc.+ Nitrogen.Conc.+PL+Thr+lactate+PO4.apporte; 0.604, 0.815, pH+tmp+Main.P-Source.Conc.+Main.Thr.Conc.+ Nitrogen.Conc.+emission_O2+Thr+His+lactate+ PO4.apporte; 0.611, 0.815, tmp+Main.P-Source.Conc.+ Main.Thr.Conc.+Nitrogen.Conc.+total.Vol+emission_O2+ Thr+lactate+PO4.apporte; 0.596, 0.815, pH+tmp+Main.P-Source.Conc.+P-Source.Feed.conc.+Nitrogen.Conc.+ emission_O2+emission_CO2+Thr+His+lactate+ PO4.apporte; 0.603, 0.815, tmp+Main.P-Source.Conc.+P-Source.Feed.conc.+Main.Thr.Conc.+Nitrogen.Conc.+ emission_CO2+rab+Thr+lactate+PO4.apporte; 0.603, 0.815, pH+tmp+Main.P-Source.Conc.+Nitrogen.Conc.+total.Vol+total.sugar+emission_O2+Thr+lactate+ PO4.apporte; 0.617, 0.815, tmp+Main.P-Source.Conc.+Nitrogen.Conc.+total.sugar+emission_CO2+Thr+lactate+ PO4.apporte; 0.610, 0.815, tmp+Main.P-Source.Conc.+P-Source.Feed.conc.+Nitrogen.Conc.+PL+rab+Thr+lactate+ PO4.apporte; 0.610, 0.815, tmp+Main.P-Source.Conc.+ Nitrogen.Conc.+total.sugar+PL+emission_O2+Thr+ lactate+PO4.apporte; 0.603, 0.815, pH+tmp+Main.P-Source.Conc.+Nitrogen.Conc.+total.sugar+emission_O2+ Thr+His+lactate+PO4.apporte; 0.596, 0.815, pH+tmp+Main.P-Source.Conc.+Main.Thr.Conc.+Nitrogen.Conc.+ PL+emission_O2+emission_CO2+Thr+lactate+ PO4.apporte; 0.610, 0.815, tmp+Main.P-Source.Conc.+ Main.Thr.Conc.+Nitrogen.Conc.+emission_O2+Thr+His+ lactate+PO4.apporte; 0.603, 0.815, pH+tmp+Main.P-Source.Conc.+P-Source.Feed.conc.+Main.Thr.Conc.+ Nitrogen.Conc.+total.sugar+Thr+lactate+PO4.apporte; 0.610, 0.815, tmp+Main.P-Source.Conc.+Main.Thr.Conc.+ Nitrogen.Conc.+total.sugar+emission_O2+Thr+lactate+ PO4.apporte; 0.603, 0.815, pH+tmp+Main.P-Source.Conc.+ P-Source.Feed.conc.+Nitrogen.Conc.+PL+rab+Thr+ lactate+PO4.apporte; 0.603, 0.815, pH+tmp+Main.P-Source.Conc.+P-Source.Feed.conc.+Nitrogen.Conc.+PL+ Thr+His+lactate+PO4.apporte; 0.595, 0.815, pH+tmp+Main.P-Source.Conc.+Nitrogen.Conc.+PL+emission_O2+ emission_CO2+Thr+His+lactate+PO4.apporte; 0.610, 0.815, tmp+Main.P-Source.Conc.+Nitrogen.Conc.+total. Vol+emission_O2+Thr+His+lactate+PO4.apporte; 0.609, 0.815, tmp+Main.P-Source.Conc.+Main.Thr.Conc.+Nitrogen.Conc.+total.sugar+PL+Thr+lactate+PO4.apporte; 0.602, 0.814, pH+tmp+Main.P-Source.Conc.+Nitrogen. Conc.+total.Vol+total.sugar+PL+Thr+lactate+PO4.apporte; 0.609, 0.814, tmp+Main.P-Source.Conc.+Nitrogen.Conc.+ total.sugar+emission_O2+Thr+His+lactate+PO4.apporte; 0.609, 0.814, tmp+Main.P-Source.Conc.+P-Source.Feed. conc.+Nitrogen.Conc.+total.sugar+emission_CO2+Thr+ lactate+PO4.apporte; 0.609, 0.814, tmp+Main.P-Source.Conc.+Main.Thr.Conc.+Nitrogen.Conc.+total.Vol+ PL+Thr+lactate+PO4.apporte; 0.602, 0.814, pH+tmp+Main.P-Source.Conc.+Main.Thr.Conc.+Nitrogen.Conc.+ total.Vol+total.sugar+Thr+lactate+PO4.apporte; 0.602, 0.814, tmp+Main.P-Source.Conc.+P-Source.Feed.conc.+ Nitrogen.Conc.+emission_CO2+rab+Thr+His+lactate+ PO4.apporte; 0.595, 0.814, pH+tmp+Main.P-Source.Conc.+ Main.Thr.Conc.+Nitrogen.Conc.+total.Vol+ emission_CO2+rab+Thr+lactate+PO4.apporte; 0.602, 0.814, pH+tmp+Main.P-Source.Conc.+Main.Thr.Conc.+ Nitrogen.Conc.+total.sugar+Thr+His+lactate+PO4.apporte; 0.601, 0.814, pH+tmp+Main.P-Source.Conc.+P-Source. Feed.conc.+Main.Thr.Conc.+Nitrogen.Conc.+Thr+His+lactate+PO4.apporte; 0.594, 0.814, pH+tmp+Main.P-Source.Conc.+P-Source.Feed.conc.+Nitrogen.Conc.+total. Vol+PL+emission_O2+Thr+lactate+PO4.apporte; 0.594, 0.814, pH+tmp+Main.P-Source.Conc.+Main.Thr. Conc.+ Nitrogen.Conc.+total.Vol+PL+emission_O2+Thr+lactate+ PO4.apporte; 0.608, 0.814, tmp+Main.P-Source.Conc.+Nitrogen.Conc.+emission_CO2+rab+Thr+His+lactate+ PO4.apporte; 0.601, 0.814, pH+tmp+Main.P-Source.Conc.+ P-Source.Feed.conc.+Nitrogen.Conc.+total.sugar+PL+Thr+ lactate+PO4.apporte; 0.594, 0.814, pH+tmp+Main.P-Source.Conc.+P-Source. Feed.conc.+Nitrogen.Conc.+PL+ emission_CO2+rab+Thr+lactate+PO4.apporte; 0.601, 0.814, tmp+Main.P-Source.Conc.+P-Source.Feed.conc.+ Main.Thr.Conc.+Nitrogen.Conc.+PL+emission_O2+Thr+ lactate+PO4.apporte; 0.601, 0.814, tmp+Main.P-Source.Conc.+P-Source.Feed.conc.+Nitrogen.Conc.+PL+ emission_O2+Thr+His+lactate+PO4.apporte; 0.608, 0.814, tmp+Main.P-Source.Conc.+Nitrogen.Conc.+total.sugar+ emission_O2+emission_CO2+Thr+lactate+PO4.apporte; 0.601, 0.814, tmp+Main.P-Source.Conc.+P-Source.Feed. conc.+Nitrogen.Conc.+total.sugar+emission_O2+emission_CO2+Thr+lactate+PO4.apporte; 0.601, 0.814, pH+tmp+Main.P-Source.Conc.+Main.Thr.Conc.+Nitrogen. Conc.+emission_CO2+Thr+His+lactate+PO4.apporte; 0.594, 0.814, pH+tmp+Main.P-Source.Conc.+P-Source. Feed.conc.+Nitrogen.Conc.+total.Vol+PL+emission_CO2+ Thr+lactate+PO4.apporte; 0.608, 0.814, tmp+Main.P-Source.Conc.+Main.Thr.Conc.+Nitrogen.Conc.+PL+emission_CO2+Thr+lactate+PO4.apporte; 0.608, 0.814, tmp+Main.P-Source.Conc.+P-Source.Feed.conc.+Nitrogen. Conc.+total.Vol+total.sugar+Thr+lactate+PO4.apporte; 0.601, 0.814, pH+tmp+Main.P-Source.Conc.+P-Source. Feed.conc.+Nitrogen.Conc.+total.sugar+Thr+His+lactate+ PO4.apporte; 0.608, 0.814, tmp+Main.P-Source.Conc.+ Main.Thr.Conc.+Nitrogen.Conc.+total.sugar+Thr+His+lactate+PO4.apporte; 0.601, 0.814, pH+tmp+Main.P-Source.Conc.+Nitrogen.Conc.+total.sugar+PL+Thr+His+ lactate+PO4.apporte; 0.608, 0.814, pH+tmp+Main.P-Source.Conc.+Main.Thr.Conc.+Nitrogen.Conc.+rab+Thr+ lactate+PO4.apporte; 0.601, 0.814, tmp+Main.P-Source.Conc.+P-Source.Feed.conc.+Main.Thr.Conc.+ Nitrogen.Conc.+emission_O2+Thr+His+lactate+ PO4.apporte; 0.593, 0.814, pH+tmp+Main.P-Source.Conc.+ Main.Thr.Conc.+Nitrogen.Conc.+total.Vol+PL+ emission_CO2+Thr+lactate+PO4.apporte; 0.601, 0.814, pH+tmp+Main.P-Source.Conc.+Nitrogen.Conc.+total. sugar+PL+emission_CO2+Thr+lactate+PO4.apporte; 0.601, 0.814, pH+tmp+Main.P-Source.Conc.+Nitrogen. Conc.+total.Vol+total.sugar+emission_CO2+Thr+lactate+ PO4.apporte; 0.600, 0.814, pH+tmp+Main.P-Source.Conc.+ P-Source.Feed.conc.+Nitrogen.Conc.+total.sugar+emission_CO2+Thr+lactate+PO4.apporte; 0.593, 0.814, pH+tmp+Main.P-Source.Conc.+Nitrogen.Conc.+total.Vol+ PL+emission_O2+Thr+His+lactate+PO4.apporte; 0.608, 0.814, tmp+Main.P-Source.Conc.+Nitrogen.Conc.+total. sugar+PL+Thr+His+lactate+PO4.apporte; 0.600, 0.814, pH+tmp+Main.P-Source.Conc.+Nitrogen.Conc.+total.Vol+ total.sugar+Thr+His+lactate+PO4.apporte; 0.608, 0.814, tmp+Main.P-Source.Conc.+Main.Thr.Conc.+Nitrogen. Conc.+PL+Thr+His+lactate+PO4.apporte; 0.600, 0.814, pH+tmp+Main.P-Source.Conc.+P-Source.Feed.conc.+Nitrogen.Conc.+total.Vol+total.sugar+Thr+lactate+ PO4.apporte; 0.593, 0.813, pH+tmp+Main.P-Source.Conc.+

Nitrogen.Conc.+total.Vol+emission_CO2+rab+Thr+His+lactate+PO4.apporte; 0.600, 0.813, tmp+Main.P-Source.Conc.+P-Source.Feed.conc.+Nitrogen.Conc.+total.Vol+PL+emission_O2+Thr+lactate+PO4.apporte; 0.600, 0.813, pH+tmp+Main.P-Source.Conc.+Main.Thr.Conc.+Nitrogen.Conc.+total.sugar+emission_CO2+Thr+lactate+PO4.apporte; 0.600, 0.813, pH+tmp+Main.P-Source.Conc.+Main.Thr.Conc.+Nitrogen.Conc.+PL+Thr+His+lactate+PO4.apporte; 0.607, 0.813, tmp+Main.P-Source.Conc.+Main.Thr.Conc.+Nitrogen.Conc.+total.Vol+Thr+His+lactate+PO4.apporte; 0.607, 0.813, tmp+Main.P-Source.Conc.+Nitrogen.Conc.+total.Vol+PL+emission_CO2+Thr+lactate+PO4.apporte; 0.600, 0.813, tmp+Main.P-Source.Conc.+Main.Thr.Conc.+Nitrogen.Conc.+PL+emission_CO2+rab+Thr+lactate+PO4.apporte; 0.607, 0.813, tmp+Main.P-Source.Conc.+Nitrogen.Conc.+PL+emission_CO2+Thr+His+lactate+PO4.apporte; 0.607, 0.813, tmp+Main.P-Source.Conc.+Nitrogen.Conc.+total.Vol+PL+Thr+His+lactate+PO4.apporte; 0.600, 0.813, pH+tmp+Main.P-Source.Conc.+Main.Thr.Conc.+Nitrogen.Conc.+PL+rab+Thr+lactate+PO4.apporte; 0.600, 0.813, tmp+Main.P-Source.Conc.+P-Source.Feed.conc.+Main.Thr.Conc.+Nitrogen.Conc.+total.Vol+emission_O2+Thr+lactate+PO4.apporte; 0.592, 0.813, pH+tmp+Main.P-Source.Conc.+Nitrogen.Conc.+total.Vol+total.sugar+emission_O2+emission_CO2+Thr+lactate+PO4.apporte; 0.600, 0.813, tmp+Main.P-Source.Conc.+P-Source.Feed.conc.+Nitrogen.Conc.+total.sugar+emission_O2+Thr+His+lactate+PO4.apporte; 0.592, 0.813, pH+tmp+Main.P-Source.Conc.+P-Source.Feed.conc.+Main.Thr.Conc.+Nitrogen.Conc.+total.Vol+emission_O2+Thr+lactate+PO4.apporte; 0.592, 0.813, pH+tmp+Main.P-Source.Conc.+P-Source.Feed.conc.+Nitrogen.Conc.+total.sugar+emission_O2+emission_CO2+Thr+lactate+PO4.apporte; 0.599, 0.813, tmp+Main.P-Source.Conc.+Main.Thr.Conc.+Nitrogen.Conc.+PL+emission_O2+emission_CO2+Thr+lactate+PO4.apporte; 0.607, 0.813, tmp+Main.P-Source.Conc.+Main.Thr.Conc.+Nitrogen.Conc.+total.Vol+emission_CO2+Thr+lactate+PO4.apporte; 0.599, 0.813, tmp+Main.P-Source.Conc.+P-Source.Feed.conc.+Nitrogen.Conc.+total.Vol+emission_O2+Thr+His+lactate+PO4.apporte; 0.592, 0.813, pH+tmp+Main.P-Source.Conc.+Nitrogen.Conc.+total.sugar+PL+emission_O2+emission_CO2+Thr+lactate+PO4.apporte; 0.592, 0.813, pH+tmp+Main.P-Source.Conc.+Nitrogen.Conc.+total.Vol+PL+emission_CO2+Thr+His+lactate+PO4.apporte; 0.599, 0.813, tmp+Main.P-Source.Conc.+P-Source.Feed.conc.+Main.Thr.Conc.+Nitrogen.Conc.+total.sugar+emission_O2+Thr+lactate+PO4.apporte; 0.592, 0.813, pH+tmp+Main.P-Source.Conc.+P-Source.Feed.conc.+Main.Thr.Conc.+Nitrogen.Conc.+total.Vol+emission_CO2+Thr+lactate+PO4.apporte; 0.592, 0.813, pH+tmp+Main.P-Source.Conc.+Main.Thr.Conc.+Nitrogen.Conc.+emission_O2+emission_CO2+Thr+His+lactate+PO4.apporte; 0.599, 0.813, pH+tmp+Main.P-Source.Conc.+Main.Thr.Conc.+Nitrogen.Conc.+emission_CO2+rab+Thr+lactate+PO4.apporte; 0.591, 0.813, pH+tmp+Main.P-Source.Conc.+Main.Thr.Conc.+Nitrogen.Conc.+total.Vol+emission_O2+Thr+His+lactate+PO4.apporte; 0.599, 0.813, pH+tmp+Main.P-Source.Conc.+Nitrogen.Conc.+total.Vol+PL+rab+Thr+lactate+PO4.apporte; 0.591, 0.813, pH+tmp+Main.P-Source.Conc.+P-Source.Feed.conc.+Nitrogen.Conc.+total.Vol+emission_O2+Thr+His+lactate+PO4.apporte; 0.599, 0.813, pH+tmp+Main.P-Source.Conc.+Nitrogen.Conc.+total.sugar+emission_CO2+Thr+His+lactate+PO4.apporte; 0.606, 0.813, tmp+Main.P-Source.Conc.+Nitrogen.Conc.+total.Vol+total.sugar+emission_O2+Thr+lactate+PO4.apporte; 0.591, 0.813, pH+tmp+Main.P-Source.Conc.+P-Source.Feed.conc.+Main.Thr.Conc.+Nitrogen.Conc.+PL+emission_O2+Thr+lactate+PO4.apporte; 0.598, 0.812, tmp+Main.P-Source.Conc.+Main.Thr.Conc.+Nitrogen.Conc.+total.Vol+emission_CO2+rab+Thr+lactate+PO4.apporte; 0.583, 0.812, pH+tmp+Main.P-Source.Conc.+Main.Thr.Conc.+Nitrogen.Conc.+total.Vol+PL+emission_O2+emission_CO2+Thr+lactate+PO4.apporte; 0.605, 0.812, tmp+Main.P-Source.Conc.+Main.Thr.Conc.+Nitrogen.Conc.+emission_CO2+Thr+His+lactate+PO4.apporte; 0.598, 0.812, tmp+Main.P-Source.Conc.+Nitrogen.Conc.+PL+emission_O2+emission_CO2+Thr+His+lactate+PO4.apporte; 0.591, 0.812, pH+tmp+Main.P-Source.Conc.+Main.Thr.Conc.+Nitrogen.Conc.+total.sugar+PL+emission_O2+Thr+lactate+PO4.apporte; 0.605, 0.812, tmp+Main.P-Source.Conc.+Nitrogen.Conc.+total.Vol+emission_CO2+Thr+His+lactate+PO4.apporte; 0.598, 0.812, tmp+Main.P-Source.Conc.+Main.Thr.Conc.+Nitrogen.Conc.+total.Vol+emission_O2+emission_CO2+Thr+lactate+PO4.apporte; 0.583, 0.812, pH+tmp+Main.P-Source.Conc.+P-Source.Feed.conc.+Nitrogen.Conc.+total.Vol+PL+emission_O2+emission_CO2+Thr+lactate+PO4.apporte; 0.583, 0.812, pH+tmp+Main.P-Source.Conc.+P-Source.Feed.conc.+Main.Thr.Conc.+Nitrogen.Conc.+total.Vol+emission_O2+emission_CO2+Thr+lactate+PO4.apporte; 0.591, 0.812, pH+tmp+Main.P-Source.Conc.+Main.Thr.Conc.+Nitrogen.Conc.+total.sugar+emission_O2+emission_CO2+Thr+lactate+PO4.apporte; 0.591, 0.812, pH+tmp+Main.P-Source.Conc.+P-Source.Feed.conc.+Nitrogen.Conc.+total.Vol+emission_CO2+Thr+His+lactate+PO4.apporte; 0.598, 0.812, tmp+Main.P-Source.Conc.+Nitrogen.Conc.+total.Vol+PL+emission_O2+emission_CO2+Thr+lactate+PO4.apporte; 0.598, 0.812, tmp+Main.P-Source.Conc.+P-Source.Feed.conc.+Nitrogen.Conc.+total.sugar+PL+emission_O2+Thr+lactate+PO4.apporte; 0.598, 0.812, tmp+Main.P-Source.Conc.+P-Source.Feed.conc.+Main.Thr.Conc.+Nitrogen.Conc.+PL+emission_CO2+Thr+lactate+PO4.apporte; 0.605, 0.812, pH+tmp+Main.P-Source.Conc.+Nitrogen.Conc.+total.Vol+rab+Thr+lactate+PO4.apporte; 0.590, 0.812, pH+tmp+Main.P-Source.Conc.+P-Source.Feed.conc.+Nitrogen.Conc.+PL+emission_O2+Thr+His+lactate+PO4.apporte; 0.598, 0.812, tmp+Main.P-Source.Conc.+P-Source.Feed.conc.+Nitrogen.Conc.+PL+emission_CO2+Thr+His+lactate+PO4.apporte; 0.590, 0.812, pH+tmp+Main.P-Source.Conc.+Main.Thr.Conc.+Nitrogen.Conc.+total.Vol+emission_CO2+Thr+His+lactate+PO4.apporte; 0.605, 0.812, tmp+Main.P-Source.Conc.+Main.Thr.Conc.+Nitrogen.Conc.+total.Vol+total.sugar+Thr+lactate+PO4.apporte; 0.598, 0.812, tmp+Main.P-Source.Conc.+P-Source.Feed.conc.+Nitrogen.Conc.+total.Vol+PL+emission_CO2+Thr+lactate+PO4.apporte; 0.590, 0.812, pH+tmp+Main.P-Source.Conc.+P-Source.Feed.conc.+Main.Thr.Conc.+Nitrogen.Conc.+total.Vol+PL+Thr+lactate+PO4.apporte; 0.582, 0.812, pH+tmp+Main.P-Source.Conc.+P-Source.Feed.conc.+Nitrogen.Conc.+total.Vol+emission_O2+emission_CO2+Thr+His+lactate+PO4.apporte; 0.597, 0.812, tmp+Main.P-Source.Conc.+Nitrogen.Conc.+PL+emission_CO2+rab+Thr+His+lactate+PO4.apporte; 0.597, 0.812, tmp+Main.P-Source.Conc.+P-Source.Feed.conc.+Main.Thr.Conc.+Nitrogen.Conc.+emission_CO2+Thr+His+lactate+PO4.apporte; 0.590, 0.812, pH+tmp+Main.P-Source.Conc.+P-Source.Feed.conc.+Main.Thr.Conc.+Nitrogen.Conc.+total.sugar+emission_O2+Thr+lactate+PO4.apporte; 0.582, 0.812, pH+tmp+Main.P-Source.Conc.+

Nitrogen.Conc.+total.Vol+PL+emission_O2+emission_CO2+Thr+His+lactate+PO4.apporte; 0.604, 0.812, tmp+Main.P-Source.Conc.+Nitrogen.Conc.+total.Vol+total.sugar+Thr+His+lactate+PO4.apporte; 0.597, 0.812, tmp+Main.P-Source.Conc.+Nitrogen.Conc.+total.Vol+PL+emission_CO2+rab+Thr+lactate+PO4.apporte; 0.597, 0.812, tmp+Main.P-Source.Conc.+Nitrogen.Conc.+total.Vol+emission_O2+emission_CO2+Thr+His+lactate+PO4.apporte; 0.597, 0.812, tmp+Main.P-Source.Conc.+P-Source.Feed.conc.+Main.Thr.Conc.+Nitrogen.Conc.+total.Vol+emission_CO2+Thr+lactate+PO4.apporte; 0.582, 0.812, pH+tmp+Main.P-Source.Conc.+Main.Thr.Conc.+Nitrogen.Conc.+total.Vol+emission_O2+emission_CO2+Thr+His+lactate+PO4.apporte; 0.589, 0.812, pH+tmp+Main.P-Source.Conc.+P-Source.Feed.conc.+Main.Thr.Conc.+Nitrogen.Conc.+emission_O2+Thr+His+lactate+PO4.apporte; 0.604, 0.812, tmp+Main.P-Source.Conc.+Nitrogen.Conc.+total.Vol+total.sugar+PL+Thr+lactate+PO4.apporte; 0.597, 0.812, tmp+Main.P-Source.Conc.+Nitrogen.Conc.+total.Vol+emission_CO2+rab+Thr+His+lactate+PO4.apporte; 0.589, 0.812, pH+tmp+Main.P-Source.Conc.+P-Source.Feed.conc.+Main.Thr.Conc.+Nitrogen.Conc.+PL+emission_CO2+Thr+lactate+PO4.apporte; 0.589, 0.812, pH+tmp+Main.P-Source.Conc.+P-Source.Feed.conc.+Main.Thr.Conc.+Nitrogen.Conc.+emission_CO2+rab+Thr+lactate+PO4.apporte; 0.597, 0.812, pH+tmp+Main.P-Source.Conc.+P-Source.Feed.conc.+Main.Thr.Conc.+Nitrogen.Conc.+rab+Thr+lactate+PO4.apporte; 0.597, 0.812, tmp+Main.P-Source.Conc.+P-Source.Feed.conc.+Main.Thr.Conc.+Nitrogen.Conc.+total.sugar+Thr+His+lactate+PO4.apporte; 0.589, 0.812, pH+tmp+Main.P-Source.Conc.+Nitrogen.Conc.+total.sugar+emission_O2+emission_CO2+Thr+His+lactate+PO4.apporte; 0.589, 0.812, tmp+Main.P-Source.Conc.+P-Source.Feed.conc.+Main.Thr.Conc.+Nitrogen.Conc.+PL+emission_O2+emission_CO2+Thr+lactate+PO4.apporte; 0.604, 0.812, tmp+Main.P-Source.Conc.+Nitrogen.Conc.+total.sugar+PL+emission_CO2+Thr+lactate+PO4.apporte; 0.589, 0.812, pH+tmp+Main.P-Source.Conc.+Main.Thr.Conc.+Nitrogen.Conc.+PL+emission_CO2+rab+Thr+lactate+PO4.apporte; 0.589, 0.811, pH+tmp+Main.P-Source.Conc.+Main.Thr.Conc.+Nitrogen.Conc.+total.Vol+total.sugar+emission_O2+Thr+lactate+PO4.apporte; 0.596, 0.811, tmp+Main.P-Source.Conc.+P-Source.Feed.conc.+Main.Thr.Conc.+Nitrogen.Conc.+total.Vol+PL+Thr+lactate+PO4.apporte; 0.596, 0.811, tmp+Main.P-Source.Conc.+P-Source.Feed.conc.+Nitrogen.Conc.+total.Vol+emission_CO2+Thr+His+lactate+PO4.apporte; 0.589, 0.811, tmp+Main.P-Source.Conc.+P-Source.Feed. conc.+Nitrogen.Conc.+PL+emission_O2+emission_CO2+Thr+His+lactate+PO4.apporte; 0.589, 0.811, tmp+Main.P-Source.Conc.+P-Source.Feed.conc.+Main.Thr.Conc.+Nitrogen.Conc.+emission_O2+emission_CO2+Thr+His+lactate+PO4.apporte; 0.589, 0.811, pH+tmp+Main.P-Source.Conc.+Main.Thr.Conc.+Nitrogen.Conc.+total.sugar+emission_O2+Thr+His+lactate+PO4.apporte; 0.596, 0.811, tmp+Main.P-Source.Conc.+P-Source.Feed.conc.+Nitrogen.Conc.+total.sugar+emission_CO2+rab+Thr+lactate+PO4.apporte; 0.589, 0.811, pH+tmp+Main.P-Source.Conc.+Nitrogen.Conc.+total.Vol+total.sugar+PL+emission_O2+Thr+lactate+PO4.apporte; 0.596, 0.811, tmp+Main.P-Source.Conc.+Main.Thr.Conc.+Nitrogen.Conc.+emission_O2+emission_CO2+Thr+His+lactate+PO4.apporte; 0.596, 0.811, tmp+Main.P-Source.Conc.+P-Source.Feed.conc.+Main.Thr.Conc.+Nitrogen.Conc.+PL+Thr+His+lactate+PO4.apporte; 0.610, 0.811, tmp+Main.P-Source.Conc.+Main.Thr.Conc.+Nitrogen.Conc.+rab+Thr+lactate+PO4.apporte; 0.603, 0.811, tmp+Main.P-Source.Conc.+Main.Thr.Conc.+Nitrogen.Conc.+total.sugar+emission_CO2+Thr+lactate+PO4.apporte; 0.596, 0.811, tmp+Main.P-Source.Conc.+P-Source.Feed.conc.+Main.Thr.Conc.+Nitrogen.Conc.+total.sugar+PL+Thr+lactate+PO4.apporte; 0.588, 0.811, pH+tmp+Main.P-Source.Conc.+P-Source.Feed.conc.+Nitrogen.Conc.+total.sugar+emission_O2+Thr+His+lactate+PO4.apporte; 0.580, 0.811, pH+tmp+Main.P-Source.Conc.+P-Source.Feed.conc.+Nitrogen.Conc.+total.Vol+PL+emission_CO2+rab+Thr+lactate+PO4.apporte; 0.588, 0.811, tmp+Main.P-Source.Conc.+P-Source.Feed.conc.+Main.Thr.Conc.+Nitrogen.Conc.+total.Vol+emission_O2+emission_CO2+Thr+lactate+PO4.apporte; 0.588, 0.811, pH+tmp+Main.P-Source.Conc.+P-Source.Feed.conc.+Nitrogen.Conc.+total.sugar+PL+emission_O2+Thr+lactate+PO4.apporte; 0.588, 0.811, pH+tmp+Main.P-Source.Conc.+Main.Thr.Conc.+Nitrogen.Conc.+total.Vol+PL+Thr+His+lactate+PO4.apporte; 0.588, 0.811, pH+tmp+Main.P-Source.Conc.+P-Source.Feed.conc.+Nitrogen.Conc.+PL+emission_CO2+Thr+His+lactate+PO4.apporte; 0.588, 0.811, tmp+Main.P-Source.Conc.+P-Source.Feed.conc.+Main.Thr.Conc.+Nitrogen.Conc.+PL+emission_CO2+rab+Thr+lactate+PO4.apporte; 0.588, 0.811, pH+tmp+Main.P-Source.Conc.+P-Source.Feed.conc.+Nitrogen.Conc.+total.Vol+PL+Thr+His+lactate+PO4.apporte; 0.588, 0.811, pH+tmp+Main.P-Source.Conc.+Nitrogen.Conc.+total.sugar+PL+emission_O2+Thr+His+lactate+PO4.apporte; 0.588, 0.811, pH+tmp+Main.P-Source.Conc.+Main.Thr.Conc.+Nitrogen.Conc.+PL+emission_O2+Thr+His+lactate+PO4.apporte; 0.595, 0.811, tmp+Main.P-Source.Conc.+P-Source.Feed.conc.+Main.Thr.Conc.+Nitrogen.Conc.+total.Vol+Thr+His+lactate+PO4.apporte; 0.603, 0.811, tmp+Main.P-Source.Conc.+Nitrogen.Conc.+total.sugar+emission_CO2+Thr+His+lactate+PO4.apporte; 0.603, 0.811, tmp+Main.P-Source.Conc.+Main.Thr.Conc.+Nitrogen.Conc.+PL+rab+Thr+lactate+PO4.apporte; 0.595, 0.811, tmp+Main.P-Source.Conc.+Main.Thr.Conc.+Nitrogen.Conc.+total.Vol+PL+emission_O2+Thr+lactate+PO4.apporte; 0.580, 0.811, pH+tmp+Main.P-Source.Conc.+P-Source.Feed.conc.+Main.Thr.Conc.+Nitrogen.Conc.+PL+emission_O2+emission_CO2+Thr+lactate+PO4.apporte; 0.588, 0.811, tmp+Main.P-Source.Conc.+P-Source.Feed.conc.+Nitrogen.Conc.+total.Vol+emission_O2+emission_CO2+Thr+His+lactate+PO4.apporte; 0.595, 0.811, tmp+Main.P-Source.Conc.+Main.Thr.Conc.+Nitrogen.Conc.+total.sugar+PL+emission_O2+Thr+lactate+PO4.apporte; 0.580, 0.811, pH+tmp+Main.P-Source.Conc.+Main.Thr.Conc.+Nitrogen.Conc.+total.Vol+PL+emission_CO2+rab+Thr+lactate+PO4.apporte; 0.588, 0.811, pH+tmp+Main.P-Source.Conc.+Nitrogen.Conc.+total.Vol+total.sugar+emission_O2+Thr+His+lactate+PO4.apporte; 0.588, 0.811, pH+tmp+Main.P-Source.Conc.+Main.Thr.Conc.+Nitrogen.Conc.+total.Vol+total.sugar+PL+Thr+lactate+PO4.apporte; 0.595, 0.811, pH+tmp+Main.P-Source.Conc.+Nitrogen.Conc.+emission_CO2+rab+Thr+His+lactate+PO4.apporte; 0.595, 0.811, tmp+Main.P-Source.Conc.+P-Source.Feed.conc.+Nitrogen.Conc.+total.sugar+PL+Thr+His+lactate+PO4.apporte; 0.587, 0.811, tmp+Main.P-Source.Conc.+P-Source.Feed.conc.+Nitrogen.Conc.+total.Vol+PL+emission_O2+emission_CO2+Thr+lactate+PO4.apporte; 0.595, 0.811, tmp+Main.P-Source.Conc.+P-Source.Feed. conc.+Nitrogen.Conc.+total.Vol+PL+Thr+His+lactate+PO4.apporte; 0.595, 0.811, tmp+Main.P-Source.Conc.+Nitrogen.Conc.+total.sugar+PL+emission_O2+emission_CO2+Thr+lactate+PO4.apporte; 0.587, 0.811, pH+tmp+Main.P-Source.Conc.+P-Source.Feed.conc.+ Main.Thr.Conc.+Nitrogen.Conc.+emission_CO2+Thr+ His+lactate+PO4.apporte; 0.602, 0.811, tmp+Main.P-Source.Conc.+Nitrogen.Conc.+total.sugar+emission_CO2+ rab+Thr+lactate+PO4.apporte; 0.595, 0.811, tmp+Main.P-Source.Conc.+P-Source.Feed.conc.+Nitrogen.Conc.+ total.Vol+total.sugar+emission_O2+Thr+lactate+ PO4.apporte; 0.587, 0.811, pH+tmp+Main.P-Source.Conc.+ P-Source.Feed.conc.+Main.Thr.Conc.+Nitrogen.Conc.+ total.Vol+Thr+His+lactate+PO4.apporte; 0.587, 0.811, pH+tmp+Main.P-Source.Conc.+P-Source.Feed.conc.+Nitrogen.Conc.+total.Vol+total.sugar+emission_O2+Thr+lactate+PO4.apporte; 0.594, 0.810, tmp+Main.P-Source.Conc.+Main.Thr.Conc.+Nitrogen.Conc.+PL+ emission_O2+Thr+His+lactate+PO4.apporte; 0.602, 0.810, tmp+Main.P-Source.Conc.+P-Source.Feed.conc.+ Main.Thr.Conc.+Nitrogen.Conc.+rab+Thr+lactate+ PO4.apporte; 0.579, 0.810, pH+tmp+Main.P-Source.Conc.+ P-Source.Feed.conc.+Nitrogen.Conc.+PL+emission_O2+ emission_CO2+Thr+His+lactate+PO4.apporte; 0.594, 0.810, tmp+Main.P-Source.Conc.+P-Source.Feed.conc.+ Nitrogen.Conc.+total.sugar+emission_CO2+Thr+His+lactate+PO4.apporte; 0.579, 0.810, pH+tmp+Main.P-Source.Conc.+Nitrogen.Conc.+total.Vol+PL+ emission_CO2+rab+Thr+His+lactate+PO4.apporte; 0.594, 0.810, tmp+Main.P-Source.Conc.+Main.Thr.Conc.+Nitrogen.Conc.+total.sugar+emission_O2+Thr+His+lactate+ PO4.apporte; 0.594, 0.810, pH+tmp+Main.P-Source.Conc.+ Nitrogen.Conc.+PL+rab+Thr+His+lactate+PO4.apporte; 0.586, 0.810, pH+tmp+Main.P-Source.Conc.+P-Source. Feed.conc.+Main.Thr.Conc.+Nitrogen.Conc.+total.sugar+ PL+Thr+lactate+PO4.apporte; 0.579, 0.810, pH+tmp+ Main.P-Source.Conc.+P-Source.Feed.conc.+Main.Thr. Conc.+Nitrogen.Conc.+emission_O2+emission_CO2+Thr+ His+lactate+PO4.apporte; 0.586, 0.810, tmp+Main.P-Source.Conc.+P-Source.Feed.conc.+Nitrogen.Conc.+PL+ emission_CO2+rab+Thr+His+lactate+PO4.apporte; 0.594, 0.810, tmp+Main.P-Source.Conc.+P-Source.Feed.conc.+ Main.Thr.Conc.+Nitrogen.Conc.+total.sugar+emission_CO2+Thr+lactate+PO4.apporte; 0.586, 0.810, pH+tmp+Main.P-Source.Conc.+Nitrogen. Conc.+total.Vol+ total.sugar+emission_CO2+rab+Thr+lactate+PO4.apporte; 0.594, 0.810, tmp+Main.P-Source.Conc.+Main.Thr.Conc.+ Nitrogen.Conc.+total.sugar+emission_O2+emission_CO2+ Thr+lactate+PO4.apporte; 0.594, 0.810, tmp+Main.P-Source.Conc.+Nitrogen.Conc.+total.sugar+PL+ emission_O2+Thr+His+lactate+PO4.apporte; 0.594, 0.810, tmp+Main.P-Source.Conc.+Main.Thr.Conc.+Nitrogen. Conc.+total.Vol+emission_O2+Thr+His+lactate+ PO4.apporte; 0.586, 0.810, tmp+Main.P-Source.Conc.+P-Source.Feed.conc.+Main. Thr.Conc.+Nitrogen.Conc.+total. Vol+emission_CO2+rab+Thr+lactate+PO4.apporte; 0.578, 0.810, pH+tmp+Main.P-Source.Conc.+P-Source. Feed. conc.+Main.Thr.Conc.+Nitrogen.Conc.+total.Vol+emission_CO2+rab+Thr+lactate+PO4.apporte; 0.586, 0.810, pH+tmp+Main.P-Source.Conc.+Nitrogen.Conc.+total.Vol+ total.sugar+PL+emission_CO2+Thr+lactate+PO4.apporte; 0.586, 0.810, pH+tmp+Main.P-Source.Conc.+P-Source. Feed.conc.+Nitrogen.Conc.+emission_CO2+rab+Thr+His+ lactate+PO4.apporte; 0.586, 0.810, pH+tmp+Main.P-Source.Conc.+Nitrogen.Conc.+PL+emission_CO2+rab+ Thr+His+lactate+PO4.apporte; 0.594, 0.810, tmp+Main.P-Source.Conc.+Nitrogen.Conc.+ total.Vol+PL+emission_O2+Thr+His+lactate+PO4.apporte; 0.586, 0.810, pH+tmp+Main.P-Source.Conc.+Main.Thr. Conc.+Nitrogen.Conc.+total.sugar+PL+emission_CO2+ Thr+lactate+PO4.apporte; 0.586, 0.810, pH+tmp+Main.P-Source.Conc.+Main.Thr.Conc.+Nitrogen.Conc.+total.Vol+ total.sugar+emission_CO2+Thr+lactate+PO4.apporte; 0.593, 0.810, pH+tmp+Main.P-Source.Conc.+Nitrogen. Conc.+total.sugar+PL+rab+Thr+lactate+PO4.apporte; 0.586, 0.810, pH+tmp+Main.P-Source.Conc.+P-Source. Feed.conc.+Main.Thr.Conc.+Nitrogen.Conc.+total.sugar+ Thr+His+lactate+PO4.apporte; 0.593, 0.810, tmp+Main.P-Source.Conc.+Nitrogen.Conc.+total.sugar+emission_O2+ emission_CO2+Thr+His+lactate+PO4.apporte; 0.586, 0.810, pH+tmp+Main.P-Source.Conc.+P-Source.Feed. conc.+Main.Thr.Conc.+Nitrogen.Conc.+total.sugar+emission_CO2+Thr+lactate+PO4.apporte; 0.586, 0.810, tmp+ Main.P-Source.Conc.+P-Source.Feed.conc.+Nitrogen. Conc.+total.sugar+emission_O2+emission_CO2+Thr+His+ lactate+PO4.apporte; 0.586, 0.810, tmp+Main.P-Source.Conc.+P-Source.Feed.conc.+Nitrogen.Conc.+total. Vol+PL+emission_CO2+rab+Thr+lactate+PO4.apporte; 0.585, 0.810, pH+tmp+Main.P-Source.Conc.+Main.Thr. Conc.+Nitrogen.Conc.+PL+emission_CO2+Thr+His+lactate+PO4.apporte; 0.585, 0.810, pH+tmp+Main.P-Source.Conc.+P-Source.Feed.conc.+Main.Thr.Conc.+Nitrogen.Conc.+total.Vol+total.sugar+Thr+lactate+ PO4.apporte; 0.585, 0.810, pH+tmp+Main.P-Source.Conc.+ Main.Thr.Conc.+Nitrogen.Conc.+total.sugar+PL+Thr+ His+lactate+PO4.apporte; 0.593, 0.810, tmp+Main.P-Source.Conc.+P-Source.Feed.conc.+Nitrogen.Conc.+ total.sugar+PL+emission_CO2+Thr+lactate+PO4.apporte; 0.600, 0.810, pH+tmp+Main.P-Source.Conc.+Nitrogen. Conc.+rab+Thr+His+lactate+PO4.apporte; 0.600, 0.810, tmp+Main.P-Source.Conc.+P-Source.Feed.conc.+Nitrogen. Conc.+rab+Thr+His+lactate+PO4.apporte; 0.585, 0.810, tmp+Main.P-Source.Conc.+P-Source.Feed.conc.+Main. Thr.Conc.+Nitrogen.Conc.+total.sugar+emission_O2+ emission_CO2+Thr+lactate+PO4.apporte; 0.593, 0.810, tmp+Main.P-Source.Conc.+P-Source.Feed.conc.+Main. Thr.Conc.+Nitrogen.Conc.+total.Vol+total.sugar+Thr+lactate+PO4.apporte; 0.593, 0.810, tmp+Main.P-Source.Conc.+P-Source.Feed.conc.+Nitrogen.Conc.+total. Vol+total.sugar+Thr+His+lactate+PO4.apporte; 0.585, 0.810, pH+tmp+Main.P-Source.Conc.+Main.Thr.Conc.+ Nitrogen.Conc.+total.Vol+total.sugar+Thr+His+lactate+ PO4.apporte; 0.585, 0.809, pH+tmp+Main.P-Source.Conc.+ P-Source.Feed.conc.+Nitrogen.Conc.+total.Vol+ total.sugar+emission_CO2+Thr+lactate+PO4.apporte; 0.585, 0.809, pH+tmp+Main.P-Source.Conc.+Nitrogen. Conc.+total.Vol+total.sugar+emission_CO2+Thr+His+lactate+PO4.apporte; 0.600, 0.809, pH+tmp+Main.P-Source.Conc.+Nitrogen.Conc.+total.sugar+rab+Thr+lactate+PO4.apporte; 0.577, 0.809, pH+tmp+Main.P-Source.Conc.+Main.Thr.Conc.+Nitrogen.Conc.+total.Vol+ total.sugar+emission_O2+emission_CO2+Thr+lactate+ PO4.apporte; 0.600, 0.809, tmp+Main.P-Source.Conc.+ Nitrogen.Conc.+total.Vol+total.sugar+emission_CO2+Thr+ lactate+PO4.apporte; 0.585, 0.809, tmp+Main.P-Source.Conc.+P-Source.Feed.conc.+Nitrogen.Conc.+ total.Vol+emission_CO2+rab+Thr+His+lactate+ PO4.apporte; 0.592, 0.809, tmp+Main.P-Source.Conc.+ Main.Thr.Conc.+Nitrogen.Conc.+emission_CO2+rab+Thr+ His+lactate+PO4.apporte; 0.585, 0.809, pH+tmp+Main.P-Source.Conc.+P-Source.Feed.conc.+Main.Thr.Conc.+ Nitrogen.Conc.+PL+rab+Thr+lactate+PO4.apporte; 0.584, 0.809, tmp+Main.P-Source.Conc.+P-Source.Feed.conc.+ Main.Thr.Conc.+Nitrogen.Conc.+emission_CO2+rab+Thr+ His+lactate+PO4.apporte; 0.613, 0.809, pH+tmp+Main.P-Source.Conc.+Nitrogen.Conc.+total.sugar+Thr+ PO4.apporte; 0.577, 0.809, pH+tmp+Main.P-Source.Conc.+ P-Source.Feed.conc.+Main.Thr.Conc.+Nitrogen.Conc.+ total.sugar+emission_O2+emission_CO2+Thr+lactate+PO4.apporte; 0.584, 0.809, pH+tmp+Main.P-Source.Conc.+P-Source.Feed.conc.+Nitrogen.Conc.+total.sugar+PL+emission_CO2+Thr+lactate+PO4.apporte; 0.584, 0.809, pH+tmp+Main.P-Source.Conc.+P-Source.Feed.conc.+Nitrogen.Conc.+total.sugar+emission_CO2+Thr+His+lactate+PO4.apporte; 0.577, 0.809, pH+tmp+Main.P-Source.Conc.+Main.Thr.Conc.+Nitrogen.Conc.+total.sugar+PL+emission_O2+emission_CO2+Thr+lactate+PO4.apporte; 0.584, 0.809, pH+tmp+Main.P-Source.Conc.+P-Source.Feed.conc.+Nitrogen.Conc.+total.Vol+total.sugar+PL+Thr+lactate+PO4.apporte; 0.576, 0.809, pH+tmp+Main.P-Source.Conc.+P-Source.Feed.conc.+Nitrogen.Conc.+total.Vol+emission_CO2+rab+Thr+His+lactate+PO4.apporte; 0.592, 0.809, tmp+Main.P-Source.Conc.+Nitrogen.Conc.+total.sugar+PL+emission_CO2+rab+Thr+lactate+PO4.apporte; 0.592, 0.809, tmp+Main.P-Source.Conc.+Main.Thr.Conc.+Nitrogen.Conc.+total.sugar+PL+Thr+His+lactate+PO4.apporte; 0.592, 0.809, pH+tmp+Main.P-Source.Conc.+P-Source.Feed.conc.+Nitrogen.Conc.+total.Vol+rab+Thr+lactate+PO4.apporte; 0.576, 0.809, pH+tmp+Main.P-Source.Conc.+Nitrogen.Conc.+total.Vol+total.sugar+emission_O2+emission_CO2+Thr+His+lactate+PO4.apporte; 0.576, 0.809, pH+tmp+Main.P-Source.Conc.+P-Source.Feed. conc.+Nitrogen.Conc.+total.Vol+total.sugar+emission_O2+emission_CO2+Thr+lactate+PO4.apporte; 0.592, 0.809, tmp+Main.P-Source.Conc.+Main.Thr.Conc.+Nitrogen.Conc.+total.Vol+PL+emission_CO2+Thr+lactate+PO4.apporte; 0.576, 0.809, pH+tmp+Main.P-Source.Conc.+Main.Thr.Conc.+Nitrogen.Conc.+PL+emission_O2+emission_CO2+Thr+His+lactate+PO4.apporte; 0.591, 0.809, pH+tmp+Main.P-Source.Conc.+P-Source.Feed.conc.+Nitrogen.Conc.+rab+Thr+His+lactate+PO4.apporte; 0.606, 0.809, tmp+Main.P-Source.Conc.+Nitrogen.Conc.+total.Vol+rab+Thr+lactate+PO4.apporte; 0.584, 0.809, pH+tmp+Main.P-Source.Conc.+P-Source.Feed.conc.+Nitrogen.Conc.+total.Vol+total.sugar+Thr+His+lactate+PO4.apporte; 0.584, 0.809, pH+tmp+Main.P-Source.Conc.+Main.Thr.Conc.+Nitrogen.Conc.+total.sugar+emission_CO2+Thr+His+lactate+PO4.apporte; 0.584, 0.809, tmp+Main.P-Source.Conc.+P-Source.Feed.conc.+Nitrogen.Conc.+total.sugar+PL+emission_O2+emission_CO2+Thr+lactate+PO4.apporte; 0.584, 0.809, pH+tmp+Main.P-Source.Conc.+Nitrogen.Conc.+total.Vol+total.sugar+PL+Thr+His+lactate+PO4.apporte; 0.584, 0.809, pH+tmp+Main.P-Source.Conc.+P-Source.Feed.conc.+Main.Thr.Conc.+Nitrogen.Conc.+PL+Thr+His+lactate+PO4.apporte; 0.599, 0.809, tmp+Main.P-Source.Conc.+Nitrogen.Conc.+total.Vol+PL+rab+Thr+lactate+PO4.apporte; 0.576, 0.809, pH+tmp+Main.P-Source.Conc.+Nitrogen.Conc.+total.Vol+total.sugar+PL+emission_O2+emission_CO2+Thr+lactate+PO4.apporte; 0.584, 0.809, pH+tmp+Main.P-Source.Conc.+P-Source.Feed.conc.+Nitrogen.Conc.+total.sugar+PL+Thr+His+lactate+PO4.apporte; 0.584, 0.809, pH+tmp+Main.P-Source.Conc.+Nitrogen.Conc.+total.sugar+PL+emission_CO2+Thr+His+lactate+PO4.apporte; 0.591, 0.809, tmp+Main.P-Source.Conc.+Nitrogen.Conc.+total.Vol+total.sugar+emission_O2+emission_CO2+Thr+lactate+PO4.apporte; 0.576, 0.809, pH+tmp+Main.P-Source.Conc.+P-Source.Feed.conc.+Main.Thr.Conc.+Nitrogen.Conc.+total.Vol+PL+emission_CO2+Thr+lactate+PO4.apporte; 0.576, 0.809, pH+tmp+Main.P-Source.Conc.+P-Source.Feed.conc.+Main.Thr.Conc.+Nitrogen.Conc.+total.Vol+PL+Thr+lactate+PO4.apporte; 0.576, 0.809, pH+tmp+Main.P-Source.Conc.+P-Source.Feed.conc.+Nitrogen.Conc.+total.sugar+emission_O2+emission_CO2+Thr+His+lactate+PO4.apporte; 0.576, 0.809, pH+tmp+Main.P-Source.Conc.+Main.Thr.Conc.+Nitrogen.Conc.+total.Vol+emission_CO2+rab+Thr+His+lactate+PO4.apporte; 0.591, 0.809, tmp+Main.P-Source.Conc.+Main.Thr.Conc.+Nitrogen.Conc.+total.Vol+PL+Thr+His+lactate+PO4.apporte; 0.575, 0.809, pH+tmp+Main.P-Source.Conc.+P-Source.Feed.conc.+Nitrogen.Conc.+total.sugar+PL+emission_O2+emission_CO2+Thr+lactate+PO4.apporte; 0.591, 0.809, tmp+Main.P-Source.Conc.+Main.Thr.Conc.+Nitrogen.Conc.+total.Vol+total.sugar+emission_O2+Thr+lactate+PO4.apporte; 0.591, 0.809, tmp+Main.P-Source.Conc.+P-Source.Feed.conc.+Nitrogen.Conc.+total.Vol+total.sugar+PL+Thr+lactate+PO4.apporte; 0.583, 0.808, tmp+Main.P-Source.Conc.+P-Source.Feed.conc.+Main.Thr.Conc.+Nitrogen.Conc.+total.sugar+emission_O2+Thr+His+lactate+PO4.apporte; 0.583, 0.808, tmp+Main.P-Source.Conc.+P-Source.Feed.conc.+Main.Thr.Conc.+Nitrogen.Conc.+PL+emission_O2+Thr+His+lactate+PO4.apporte; 0.598, 0.808, tmp+Main.P-Source.Conc.+P-Source.Feed.conc.+Nitrogen.Conc.+total.Vol+rab+Thr+lactate+PO4.apporte; 0.590, 0.808, tmp+Main.P-Source.Conc.+P-Source.Feed.conc.+Nitrogen.Conc.+total.Vol+total.sugar+emission_CO2+Thr+lactate+PO4.apporte; 0.590, 0.808, tmp+Main.P-Source.Conc.+P-Source.Feed.conc.+Main.Thr.Conc.+Nitrogen.Conc.+PL+rab+Thr+lactate+PO4.apporte; 0.590, 0.808, tmp+Main.P-Source.Conc.+Nitrogen.Conc.+total.Vol+total.sugar+emission_O2+Thr+His+lactate+PO4.apporte; 0.583, 0.808, pH+tmp+Main.P-Source.Conc.+P-Source.Feed.conc.+Nitrogen.Conc.+total.Vol+PL+rab+Thr+lactate+PO4.apporte; 0.598, 0.808, tmp+Main.P-Source.Conc.+Nitrogen.Conc.+PL+rab+Thr+His+lactate+PO4.apporte; 0.575, 0.808, pH+tmp+Main.P-Source.Conc.+Main.Thr.Conc.+Nitrogen.Conc.+total.Vol+PL+emission_O2+Thr+His+lactate+PO4.apporte; 0.575, 0.808, pH+tmp+Main.P-Source.Conc.+P-Source.Feed.conc.+Main.Thr.Conc.+Nitrogen.Conc.+PL+emission_CO2+rab+Thr+lactate+PO4.apporte; 0.582, 0.808, tmp+Main.P-Source.Conc.+Main.Thr.Conc.+Nitrogen.Conc.+total.Vol+PL+emission_CO2+rab+Thr+lactate+PO4.apporte; 0.590, 0.808, tmp+Main.P-Source.Conc.+Main.Thr.Conc.+Nitrogen.Conc.+PL+emission_CO2+Thr+His+lactate+PO4.apporte; 0.590, 0.808, tmp+Main.P-Source.Conc.+Nitrogen.Conc.+total.Vol+total.sugar+emission_CO2+rab+Thr+lactate+PO4.apporte; 0.582, 0.808, tmp+Main.P-Source.Conc.+P-Source.Feed.conc.+Main.Thr.Conc.+Nitrogen.Conc.+total.Vol+PL+emission_O2+Thr+lactate+PO4.apporte; 0.590, 0.808, tmp+Main.P-Source.Conc.+Nitrogen.Conc.+total.Vol+total.sugar+PL+emission_O2+Thr+lactate+PO4.apporte; 0.574, 0.808, pH+tmp+Main.P-Source.Conc.+Nitrogen.Conc.+total.sugar+PL+emission_O2+emission_CO2+Thr+His+lactate+PO4.apporte; 0.582, 0.808, tmp+Main.P-Source.Conc.+P-Source.Feed.conc.+Main.Thr.Conc.+Nitrogen.Conc.+total.Vol+emission_O2+Thr+His+lactate+PO4.apporte; 0.574, 0.808, pH+tmp+Main.P-Source.Conc.+P-Source.Feed.conc.+Nitrogen.Conc.+total.Vol+PL+emission_O2+Thr+His+lactate+PO4.apporte; 0.582, 0.808, tmp+Main.P-Source.Conc.+Main.Thr.Conc.+Nitrogen.Conc.+total.Vol+PL+emission_O2+emission_CO2+Thr+lactate+PO4.apporte; 0.590, 0.808, tmp+Main.P-Source.Conc.+Nitrogen.Conc.+total.Vol+PL+emission_CO2+Thr+His+lactate+PO4.apporte; 0.590, 0.808, tmp+Main.P-Source.Conc.+Main.Thr.Conc.+Nitrogen.Conc.+total.Vol+emission_CO2+Thr+His+lactate+PO4.apporte; 0.582, 0.808, tmp+Main.P-Source.Conc.+P-

Source.Feed.conc.+Main.Thr.Conc.+Nitrogen.Conc.+ total.sugar+PL+emission_O2+Thr+lactate+PO4.apporte; 0.574, 0.808, pH+tmp+Main.P-Source.Conc.+P-Source. Feed.conc.+Main.Thr.Conc.+Nitrogen.Conc.+total.Vol+ emission_O2+Thr+His+lactate+PO4.apporte; 0.604, 0.808, tmp+Main.P-Source.Conc.+Nitrogen.Conc.+rab+Thr+His+ lactate+PO4.apporte; 0.574, 0.808, pH+tmp+Main.P-Source.Conc.+Main.Thr.Conc.+Nitrogen.Conc.+total. sugar+emission_O2+emission_CO2+Thr+His+lactate+ PO4.apporte; 0.597, 0.808, tmp+Main.P-Source.Conc.+Nitrogen.Conc.+total.sugar+PL+rab+Thr+lactate+ PO4.apporte; 0.589, 0.808, tmp+Main.P-Source.Conc.+ Main.Thr.Conc.+Nitrogen.Conc.+total.Vol+total.sugar+ PL+Thr+lactate+PO4.apporte; 0.582, 0.808, tmp+Main.P-Source.Conc.+P-Source.Feed.conc.+Nitrogen.Conc.+ total.Vol+total.sugar+emission_O2+emission_CO2+Thr+ lactate+PO4.apporte; 0.574, 0.808, pH+tmp+Main.P-Source.Conc.+Main.Thr.Conc.+Nitrogen.Conc.+total.Vol+ PL+emission_CO2+Thr+His+lactate+PO4.apporte; 0.597, 0.808, tmp+Main.P-Source.Conc.+P-Source.Feed.conc.+ Nitrogen.Conc.+total.sugar+rab+Thr+lactate+PO4.apporte; 0.589, 0.808, pH+tmp+Main.P-Source.Conc.+P-Source. Feed.conc.+Nitrogen.Conc.+total.sugar+rab+Thr+lactate+ PO4.apporte; 0.589, 0.808, tmp+Main.P-Source.Conc.+P-Source.Feed.conc.+Nitrogen.Conc.+PL+rab+Thr+His+lac- tate+PO4.apporte; 0.574, 0.808, pH+tmp+Main.P-Source.Conc.+P-Source.Feed.conc.+Nitrogen.Conc.+ total.Vol+PL+emission_CO2+Thr+His+lactate+ PO4.apporte; 0.581, 0.808, tmp+Main.P-Source.Conc.+P-Source.Feed.conc.+Nitrogen.Conc.+total.sugar+PL+ emission_O2+Thr+His+lactate+PO4.apporte; 0.573, 0.808, pH+tmp+Main.P-Source.Conc.+Main.Thr.Conc.+Nitrogen. Conc.+total.Vol+total.sugar+PL+emission_O2+Thr+lac- tate+PO4.apporte; 0.581, 0.808, tmp+Main.P-Source.Conc.+P-Source.Feed.conc.+Nitrogen.Conc.+total. Vol+PL+emission_O2+Thr+His+lactate+PO4.apporte; 0.589, 0.808, pH+tmp+Main.P-Source.Conc.+Nitrogen. Conc.+total.sugar+emission_CO2+rab+Thr+lactate+ PO4.apporte; 0.573, 0.808, pH+tmp+Main.P-Source.Conc.+ P-Source.Feed.conc.+Main.Thr.Conc.+Nitrogen.Conc.+to- tal.Vol+emission_CO2+Thr+His+lactate+PO4.apporte; 0.603, 0.807, tmp+Main.P-Source.Conc.+Nitrogen.Conc.+ total.sugar+rab+Thr+lactate+PO4.apporte; 0.589, 0.807, tmp+Main.P-Source.Conc.+Main.Thr.Conc.+Nitrogen. Conc.+total.sugar+PL+emission_CO2+Thr+lactate+ PO4.apporte; 0.603, 0.807, pH+tmp+Main.P-Source.Conc.+ Main.Thr.Conc.+Nitrogen.Conc.+total.sugar+Thr+ PO4.apporte; 0.581, 0.807, tmp+Main.P-Source.Conc.+P-Source.Feed.conc.+Nitrogen.Conc.+total.sugar+PL+ emission_CO2+rab+Thr+lactate+PO4.apporte; 0.588, 0.807, pH+tmp+Main.P-Source.Conc.+Main.Thr.Conc.+ Nitrogen.Conc.+total.sugar+rab+Thr+lactate+PO4.apporte; 0.581, 0.807, tmp+Main.P-Source.Conc.+Main.Thr.Conc.+ Nitrogen.Conc.+PL+emission_O2+emission_CO2+Thr+ His+lactate+PO4.apporte; 0.581, 0.807, pH+tmp+Main.P-Source.Conc.+Nitrogen.Conc.+total.sugar+PL+ emission_CO2+rab+Thr+lactate+PO4.apporte; 0.588, 0.807, tmp+Main.P-Source.Conc.+Main.Thr.Conc.+Nitro- gen.Conc.+total.Vol+total.sugar+Thr+His+lactate+ PO4.apporte; 0.581, 0.807, tmp+Main.P-Source.Conc.+ Main.Thr.Conc.+Nitrogen.Conc.+total.Vol+emission_O2+ emission_CO2+Thr+His+lactate+PO4.apporte; 0.581, 0.807, pH+tmp+Main.P-Source.Conc.+P-Source.Feed. conc.+Nitrogen.Conc.+total.sugar+emission_CO2+rab+ Thr+lactate+PO4.apporte; 0.581, 0.807, pH+tmp+Main.P-Source.Conc.+P-Source.Feed.conc.+Nitrogen.Conc.+PL+ rab+Thr+His+lactate+PO4.apporte; 0.581, 0.807, tmp+ Main.P-Source.Conc.+Main.Thr.Conc.+Nitrogen.Conc.+ total.Vol+emission_CO2+rab+Thr+His+lactate+ PO4.apporte; 0.573, 0.807, pH+tmp+Main.P-Source.Conc.+ Nitrogen.Conc.+total.Vol+total.sugar+PL+emission_CO2+ rab+Thr+lactate+PO4.apporte; 0.564, 0.807, pH+tmp+ Main.P-Source.Conc.+P-Source.Feed.conc.+ Main.Thr.Conc.+Nitrogen.Conc.+total.Vol+PL+ emission_O2+emission_CO2+Thr+lactate+PO4.apporte; 0.564, 0.807, pH+tmp+Main.P-Source.Conc.+P-Source. Feed.conc.+Main.Thr.Conc.+Nitrogen.Conc.+total.Vol+ emission_O2+emission_CO2+Thr+His+lactate+ PO4.apporte; 0.573, 0.807, pH+tmp+Main.P-Source.Conc.+ P-Source.Feed.conc.+Main.Thr.Conc.+Nitrogen.Conc.+ total.sugar+PL+emission_O2+Thr+lactate+PO4.apporte; 0.572, 0.807, pH+tmp+Main.P-Source.Conc.+P-Source. Feed.conc.+Main.Thr.Conc.+Nitrogen.Conc.+total.sugar+ emission_O2+Thr+His+lactate+PO4.apporte; 0.580, 0.807, tmp+Main.P-Source.Conc.+P-Source.Feed.conc.+Main. Thr.Conc.+Nitrogen.Conc.+total.sugar+emission_CO2+ rab+Thr+lactate+PO4.apporte; 0.580, 0.807, tmp+Main.P-Source.Conc.+Nitrogen.Conc.+total.Vol+PL+emis- sion_CO2+rab+Thr+His+lactate+PO4.apporte; 0.580, 0.807, tmp+Main.P-Source.Conc.+Nitrogen.Conc.+total. Vol+PL+emission_O2+emission_CO2+Thr+His+lactate+ PO4.apporte; 0.588, 0.807, tmp+Main.P-Source.Conc.+ Main.Thr.Conc.+Nitrogen.Conc.+total.sugar+emis- sion_CO2+rab+Thr+lactate+PO4.apporte; 0.580, 0.807, pH+tmp+Main.P-Source.Conc.+Main.Thr.Conc.+Nitrogen. Conc.+total.sugar+PL+rab+Thr+lactate+PO4.apporte; 0.572, 0.807, pH+tmp+Main.P-Source.Conc.+P-Source. Feed.conc.+Nitrogen.Conc.+PL+emission_CO2+rab+Thr+ His+lactate+PO4.apporte; 0.580, 0.807, tmp+Main.P-Source.Conc.+Main.Thr.Conc.+Nitrogen.Conc.+PL+emis- sion_CO2+rab+Thr+His+lactate+PO4.apporte; 0.572, 0.807, pH+tmp+Main.P-Source.Conc.+Main.Thr.Conc.+ Nitrogen.Conc.+total.sugar+PL+emission_O2+Thr+His+ lactate+PO4.apporte; 0.572, 0.807, pH+tmp+Main.P-Source.Conc.+Main.Thr.Conc.+Nitrogen.Conc.+total.Vol+ total.sugar+emission_O2+Thr+His+lactate+PO4.apporte; 0.580, 0.807, tmp+Main.P-Source.Conc.+P-Source.Feed. conc.+Main.Thr.Conc.+Nitrogen.Conc.+total.Vol+PL+ emission_CO2+Thr+lactate+PO4.apporte; 0.587, 0.807, tmp+Main.P-Source.Conc.+P-Source.Feed.conc.+Nitrogen. Conc.+total.Vol+PL+rab+Thr+lactate+PO4.apporte; 0.587, 0.807, tmp+Main.P-Source.Conc.+Nitrogen.Conc.+total. sugar+PL+emission_CO2+Thr+His+lactate+PO4.apporte; 0.580, 0.807, tmp+Main.P-Source.Conc.+P-Source.Feed. conc.+Nitrogen.Conc.+total.sugar+emission_CO2+rab+ Thr+His+lactate+PO4.apporte; 0.615, 0.807, tmp+Main.P-Source.Conc.+Nitrogen.Conc.+total.sugar+Thr+ PO4.apporte; 0.572, 0.807, pH+tmp+Main.P-Source.Conc.+ P-Source.Feed.conc.+Main.Thr.Conc.+Nitrogen.Conc.+ total.Vol+total.sugar+emission_O2+Thr+lactate+ PO4.apporte; 0.587, 0.807, tmp+Main.P-Source.Conc.+ Main.Thr.Conc.+Nitrogen.Conc.+total.sugar+ emission_CO2+Thr+His+lactate+PO4.apporte; 0.580, 0.807, tmp+Main.P-Source.Conc.+P-Source.Feed.conc.+ Main.Thr.Conc.+Nitrogen.Conc.+PL+emission_CO2+Thr+ His+lactate+PO4.apporte; 0.563, 0.807, pH+tmp+Main.P-Source.Conc.+Main.Thr.Conc.+Nitrogen.Conc.+total.Vol+ PL+emission_O2+emission_CO2+Thr+His+lactate+ PO4.apporte; 0.579, 0.807, tmp+Main.P-Source.Conc.+ Main.Thr.Conc.+Nitrogen.Conc.+total.sugar+PL+ emission_O2+emission_CO2+Thr+lactate+PO4.apporte; 0.587, 0.807, pH+tmp+Main.P-Source.Conc.+Main.Thr. Conc.+Nitrogen.Conc.+total.Vol+rab+Thr+lactate+ PO4.apporte; 0.579, 0.807, pH+tmp+Main.P-Source.Conc.+

Main.Thr.Conc.+Nitrogen.Conc.+total.Vol+PL+rab+Thr+lactate+PO4.apporte; 0.594, 0.807, pH+tmp+Main.P-Source.Conc.+Main.Thr.Conc.+Nitrogen.Conc.+total.Vol+total.sugar+lactate+PO4.apporte; 0.608, 0.806, tmp+Main.P-Source.Conc.+P-Source.Feed.conc.+Nitrogen.Conc.+His+lactate+PO4.apporte; 0.579, 0.806, tmp+Main.P-Source.Conc.+P-Source.Feed.conc.+Main.Thr.Conc.+Nitrogen.Conc.+total.Vol+emission_CO2+Thr+His+lactate+PO4.apporte; 0.571, 0.806, pH+tmp+Main.P-Source.Conc.+Main.Thr.Conc.+Nitrogen.Conc.+total.Vol+total.sugar+emission_CO2+rab+Thr+lactate+PO4.apporte; 0.587, 0.806, tmp+Main.P-Source.Conc.+Nitrogen.Conc.+total.Vol+total.sugar+PL+Thr+His+lactate+PO4.apporte; 0.571, 0.806, pH+tmp+Main.P-Source.Conc.+Main.Thr.Conc.+Nitrogen.Conc.+total.Vol+total.sugar+PL+emission_CO2+Thr+lactate+PO4.apporte; 0.571, 0.806, pH+tmp+Main.P-Source.Conc.+P-Source.Feed.conc.+Main.Thr.Conc.+Nitrogen.Conc.+PL+emission_O2+Thr+His+lactate+PO4.apporte; 0.579, 0.806, tmp+Main.P-Source.Conc.+P-Source.Feed.conc.+Nitrogen.Conc.+total.Vol+total.sugar+emission_O2+Thr+His+lactate+PO4.apporte; 0.571, 0.806, pH+tmp+Main.P-Source.Conc.+P-Source.Feed.conc.+Nitrogen.Conc.+total.Vol+total.sugar+emission_CO2+rab+Thr+lactate+PO4.apporte; 0.563, 0.806, pH+tmp+Main.P-Source.Conc.+P-Source.Feed.conc.+Nitrogen.Conc.+total.Vol+PL+emission_O2+emission_CO2+Thr+His+lactate+PO4.apporte; 0.579, 0.806, tmp+Main.P-Source.Conc.+P-Source.Feed.conc.+Main.Thr.Conc.+Nitrogen.Conc.+total.Vol+total.sugar+emission_O2+Thr+lactate+PO4.apporte; 0.601, 0.806, pH+tmp+Main.P-Source.Conc.+Nitrogen.Conc.+total.Vol+total.sugar+lactate+PO4.apporte; 0.579, 0.806, tmp+Main.P-Source.Conc.+P-Source.Feed.conc.+Nitrogen.Conc.+total.Vol+total.sugar+emission_CO2+rab+Thr+lactate+PO4.apporte; 0.579, 0.806, tmp+Main.P-Source.Conc.+P-Source.Feed.conc.+Nitrogen.Conc.+total.Vol+PL+emission_CO2+Thr+His+lactate+PO4.apporte; 0.586, 0.806, tmp+Main.P-Source.Conc.+Nitrogen.Conc.+total.sugar+emission_CO2+rab+Thr+His+lactate+PO4.apporte; 0.578, 0.806, pH+tmp+Main.P-Source.Conc.+Main.Thr.Conc.+Nitrogen.Conc.+emission_CO2+rab+Thr+His+lactate+PO4.apporte; 0.578, 0.806, pH+tmp+Main.P-Source.Conc.+P-Source.Feed. conc.+Nitrogen.Conc.+total.sugar+PL+rab+Thr+lactate+PO4.apporte; 0.570, 0.806, pH+tmp+Main.P-Source.Conc.+P-Source.Feed.conc.+Nitrogen.Conc.+total.Vol+total.sugar+emission_O2+Thr+His+lactate+PO4.apporte; 0.578, 0.806, tmp+Main.P-Source.Conc.+P-Source.Feed. conc.+Main. Thr.Conc.+Nitrogen.Conc.+total.sugar+PL+Thr+His+lactate+PO4.apporte; 0.570, 0.806, pH+tmp+Main.P-Source.Conc.+P-Source.Feed.conc.+Nitrogen.Conc.+total.sugar+PL+emission_O2+Thr+His+lactate+PO4.apporte; 0.570, 0.806, tmp+Main.P-Source.Conc.+P-Source.Feed.conc.+Main.Thr.Conc.+Nitrogen.Conc.+total.Vol+emission_O2+emission_CO2+Thr+His+lactate+PO4.apporte; 0.570, 0.806, tmp+Main.P-Source.Conc.+P-Source.Feed.conc.+Main.Thr.Conc.+Nitrogen.Conc.+PL+emission_O2+emission_CO2+Thr+His+lactate+PO4.apporte; 0.570, 0.806, pH+tmp+Main.P-Source.Conc.+Nitrogen.Conc.+total.Vol+total.sugar+PL+emission_O2+Thr+His+lactate+PO4.apporte; 0.586, 0.806, pH+tmp+Main.P-Source.Conc.+Main.Thr.Conc.+Nitrogen. Conc.+total.Vol+total.sugar+emission_CO2+lactate+PO4.apporte; 0.578, 0.806, tmp+Main.P-Source.Conc.+Nitrogen.Conc.+total.sugar+PL+emission_O2+emission_CO2+Thr+His+lactate+PO4.apporte; 0.586, 0.806, tmp+Main.P-Source.Conc.+P-Source.Feed.conc.+Nitrogen.Conc.+total.sugar+PL+rab+Thr+lactate+PO4.apporte; 0.570, 0.806, pH+tmp+Main.P-Source.Conc.+P-Source.Feed. conc.+Nitrogen.Conc.+total.Vol+total.sugar+PL+emission_O2+Thr+lactate+PO4.apporte; 0.561, 0.806, pH+tmp+Main.P-Source.Conc.+P-Source. Feed.conc.+Main.Thr.Conc.+Nitrogen.Conc.+total.Vol+PL+emission_CO2+rab+Thr+lactate+PO4.apporte; 0.607, 0.806, pH+tmp+Main.P-Source.Conc.+Nitrogen.Conc.+His+lactate+PO4.apporte; 0.578, 0.806, tmp+Main.P-Source.Conc.+P-Source.Feed.conc.+Main. Thr.Conc.+Nitrogen.Conc.+total.sugar+emission_CO2+Thr+His+lactate+PO4.apporte; 0.570, 0.806, pH+tmp+Main.P-Source.Conc.+Nitrogen.Conc.+total.Vol+total.sugar+emission_CO2+rab+Thr+His+lactate+PO4.apporte; 0.600, 0.806, pH+tmp+Main.P-Source.Conc.+P-Source.Feed.conc.+Nitrogen.Conc.+His+lactate+PO4.apporte; 0.600, 0.806, tmp+Main.P-Source.Conc.+P-Source.Feed.conc.+Main.Thr.Conc.+Nitrogen.Conc.+total.sugar+lactate+PO4.apporte; 0.569, 0.806, pH+tmp+Main.P-Source.Conc.+P-Source.Feed.conc.+Main.Thr.Conc.+Nitrogen.Conc.+total.Vol+total.sugar+emission_CO2+Thr+lactate+PO4.apporte; 0.577, 0.806, tmp+Main.P-Source.Conc.+P-Source.Feed.conc.+Main. Thr.Conc.+Nitrogen.Conc.+total.Vol+PL+Thr+His+lactate+PO4.apporte; 0.577, 0.806, pH+tmp+Main.P-Source.Conc.+Main.Thr.Conc.+Nitrogen.Conc.+total.Vol+total.sugar+emission_O2+emission_CO2+lactate+PO4.apporte; 0.577, 0.806, tmp+Main.P-Source.Conc.+Main.Thr.Conc.+Nitrogen.Conc.+total.sugar+PL+emission_O2+Thr+His+lactate+PO4.apporte; 0.569, 0.806, pH+tmp+Main.P-Source.Conc.+P-Source.Feed.conc.+Main.Thr.Conc.+Nitrogen.Conc.+total.Vol+PL+Thr+His+lactate+PO4.apporte; 0.577, 0.806, tmp+Main.P-Source.Conc.+Main.Thr.Conc.+Nitrogen. Conc.+total.sugar+emission_O2+emission_CO2+Thr+His+lactate+PO4.apporte; 0.600, 0.805, tmp+Main.P-Source.Conc.+P-Source.Feed.conc.+Nitrogen.Conc.+total.sugar+His+lactate+PO4.apporte; 0.592, 0.805, pH+tmp+Main.P-Source.Conc.+Nitrogen.Conc.+total.Vol+total.sugar+emission_CO2+lactate+PO4.apporte; 0.585, 0.805, pH+tmp+Main.P-Source.Conc.+Main.Thr.Conc.+Nitrogen.Conc.+rab+Thr+His+lactate+PO4.apporte; 0.585, 0.805, tmp+Main.P-Source.Conc.+Main.Thr.Conc.+Nitrogen.Conc.+total.Vol+total.sugar+emission_CO2+Thr+lactate+PO4.apporte; 0.577, 0.805, tmp+Main.P-Source.Conc.+Main.Thr.Conc.+Nitrogen.Conc.+total.sugar+PL+emission_CO2+rab+Thr+lactate+PO4.apporte; 0.569, 0.805, pH+tmp+Main.P-Source.Conc.+P-Source.Feed.conc.+Main.Thr.Conc.+Nitrogen.Conc.+PL+emission_CO2+Thr+His+lactate+PO4.apporte; 0.569, 0.805, tmp+Main.P-Source.Conc.+P-Source.Feed.conc.+Main.Thr.Conc.+Nitrogen.Conc.+total.Vol+PL+emission_O2+emission_CO2+Thr+lactate+PO4.apporte; 0.606, 0.805, pH+tmp+Main.P-Source.Conc.+Nitrogen.Conc.+total.sugar+lactate+PO4.apporte; 0.599, 0.805, tmp+Main.P-Source.Conc.+P-Source.Feed.conc.+Nitrogen.Conc.+rab+His+lactate+PO4.apporte; 0.569, 0.805, pH+tmp+Main.P-Source.Conc.+P-Source.Feed.conc.+Main.Thr.Conc.+Nitrogen.Conc.+total.Vol+total.sugar+PL+Thr+lactate+PO4.apporte; 0.569, 0.805, pH+tmp+Main.P-Source.Conc.+Main.Thr.Conc.+Nitrogen.Conc.+total.Vol+total.sugar+emission_CO2+Thr+His+lactate+PO4.apporte; 0.577, 0.805, tmp+Main.P-Source.Conc.+Main.Thr.Conc.+Nitrogen.Conc.+total.Vol+PL+emission_O2+Thr+His+lactate+PO4.apporte; 0.584, 0.805, tmp+Main.P-Source.Conc.+Nitrogen.Conc.+total.Vol+total.sugar+emission_CO2+Thr+His+lactate+PO4.apporte; 0.577, 0.805, tmp+Main.P-Source.Conc.+P-Source.Feed.conc.+Main.Thr.Conc.+

Nitrogen.Conc.+total.sugar+PL+emission_CO2+Thr+ lactate+PO4.apporte; 0.569, 0.805, pH+tmp+Main.P-Source.Conc.+P-Source.Feed.conc.+Main.Thr.Conc.+ Nitrogen.Conc.+emission_CO2+rab+Thr+His+lactate+ PO4.apporte; 0.584, 0.805, pH+tmp+Main.P-Source.Conc.+ Nitrogen.Conc.+total.Vol+total.sugar+emission_O2+ emission_CO2+lactate+PO4.apporte; 0.560, 0.805, pH+tmp+Main.P-Source.Conc.+Main.Thr.Conc.+Nitrogen. Conc.+total.Vol+total.sugar+PL+emission_O2+emission_ CO2+Thr+lactate+PO4.apporte; 0.569, 0.805, pH+tmp+ Main.P-Source.Conc.+P-Source.Feed.conc.+Main.Thr. Conc.+Nitrogen.Conc.+total.sugar+PL+emission_CO2+ Thr+lactate+PO4.apporte; 0.606, 0.805, tmp+Main.P-Source.Conc.+P-Source.Feed.conc.+Nitrogen.Conc.+total. sugar+lactate+PO4.apporte; 0.560, 0.805, pH+tmp+Main.P-Source.Conc.+P-Source.Feed. conc.+Main.Thr.Conc.+ Nitrogen.Conc.+total.Vol+total. sugar+emission_O2+ emission_CO2+Thr+lactate+PO4.apporte; 0.569, 0.805, tmp+Main.P-Source.Conc.+P-Source.Feed.conc.+Main. Thr.Conc.+Nitrogen.Conc.+total. sugar+emission_O2+ emission_CO2+Thr+His+lactate+PO4.apporte; 0.576, 0.805, pH+tmp+Main.P-Source.Conc.+P-Source.Feed. conc.+Main.Thr.Conc.+Nitrogen.Conc.+total.sugar+rab+ Thr+lactate+PO4.apporte; 0.568, 0.805, pH+tmp+Main.P-Source.Conc.+P-Source. Feed.conc.+Nitrogen.Conc.+total. Vol+total.sugar+emission_CO2+Thr+His+lactate+PO4. apporte; 0.584, 0.805, tmp+Main.P-Source.Conc.+Nitrogen. Conc.+total.Vol+total.sugar+PL+emission_CO2+Thr+ lactate+PO4.apporte; 0.568, 0.805, pH+tmp+Main.P-Source.Conc.+P-Source. Feed.conc.+Main.Thr.Conc.+ Nitrogen.Conc.+total.sugar+emission_CO2+Thr+His+ lactate+PO4.apporte; 0.576, 0.805, tmp+Main.P-Source. Conc.+P-Source.Feed.conc.+Nitrogen. Conc.+total.Vol+ total.sugar+PL+emission_O2+Thr+lactate+PO4.apporte; 0.599, 0.805, pH+tmp+Main.P-Source.Conc.+P-Source. Feed.conc.+Nitrogen.Conc.+total. sugar+Thr+PO4.apporte; 0.599, 0.805, pH+tmp+Main.P-Source.Conc.+Nitrogen. Conc.+total.Vol+His+lactate+PO4.apporte; 0.568, 0.805, pH+tmp+Main.P-Source.Conc.+P-Source.Feed.conc.+Nitrogen.Conc.+total.Vol+total.sugar+PL+emission_CO2+ Thr+lactate+PO4.apporte; 0.599, 0.805, tmp+Main.P-Source.Conc.+P-Source.Feed.conc.+Nitrogen.Conc.+total. sugar+rab+lactate+PO4.apporte; 0.576, 0.805, tmp+Main.P-Source.Conc.+P-Source.Feed.conc.+Nitrogen.Conc.+total. sugar+PL+emission_CO2+Thr+His+lactate+PO4.apporte; 0.560, 0.805, pH+tmp+Main.P-Source.Conc.+Main.Thr. Conc.+Nitrogen.Conc.+total.Vol+PL+emission_CO2+rab+ Thr+His+lactate+PO4.apporte; 0.576, 0.805, pH+tmp+ Main.P-Source.Conc.+Main.Thr.Conc.+Nitrogen.Conc.+ PL+rab+Thr+His+lactate+PO4.apporte; 0.598, 0.805, pH+tmp+Main.P-Source.Conc.+Nitrogen. Conc.+total. sugar+emission_O2+Thr+PO4.apporte; 0.598, 0.805, tmp+ Main.P-Source.Conc.+P-Source.Feed.conc.+Main.Thr. Conc.+Nitrogen.Conc.+His+lactate+PO4.apporte; 0.612, 0.805, pH+tmp+Main.P-Source.Conc.+Nitrogen.Conc.+ Thr+PO4.apporte; 0.560, 0.805, pH+tmp+Main.P-Source. Conc.+Main.Thr.Conc.+Nitrogen.Conc.+total.Vol+total. sugar+emission_O2+emission_CO2+Thr+His+lactate+ PO4.apporte; 0.568, 0.805, tmp+Main.P-Source.Conc.+P-Source.Feed.conc.+Nitrogen.Conc.+total.Vol+PL+ emission_O2+emission_CO2+Thr+His+lactate+PO4. apporte; 0.576, 0.805, tmp+Main.P-Source.Conc.+P-Source.Feed.conc.+Main.Thr.Conc.+Nitrogen.Conc.+total. Vol+total.sugar+Thr+His+lactate+PO4.apporte; 0.576, 0.805, tmp+Main.P-Source.Conc.+Main.Thr.Conc.+Nitrogen.Conc.+total.Vol+total.sugar+emission_O2+emission_ CO2+Thr+lactate+PO4.apporte; 0.559, 0.805, pH+tmp+ Main.P-Source.Conc.+P-Source. Feed.conc.+Main.Thr. Conc.+Nitrogen.Conc.+PL+emission_O2+emission_CO2+ Thr+His+lactate+PO4.apporte; 0.568, 0.805, pH+tmp+ Main.P-Source.Conc.+Nitrogen. Conc.+total.Vol+total. sugar+PL+emission_CO2+Thr+His+lactate+PO4.apporte; 0.568, 0.805, tmp+Main.P-Source.Conc.+P-Source.Feed. conc.+Main.Thr.Conc.+Nitrogen.Conc.+total.Vol+PL+ emission_CO2+rab+Thr+lactate+PO4.apporte; 0.568, 0.805, pH+tmp+Main.P-Source.Conc.+Main.Thr.Conc.+ Nitrogen.Conc.+total.Vol+total.sugar+PL+Thr+His+lactate+PO4.apporte; 0.598, 0.805, tmp+Main.P-Source. Conc.+P-Source.Feed.conc.+Nitrogen.Conc.+emission_ O2+His+lactate+PO4.apporte; 0.568, 0.805, pH+tmp+ Main.P-Source.Conc.+P-Source. Feed.conc.+Main.Thr. Conc.+Nitrogen.Conc.+total.Vol+total.sugar+Thr+His+ lactate+PO4.apporte; 0.559, 0.805, pH+tmp+Main.P-Source.Conc.+P-Source.Feed.conc.+Nitrogen.Conc.+total. Vol+total.sugar+emission_O2+emission_CO2+Thr+His+ lactate+PO4.apporte; 0.591, 0.805, tmp+Main.P-Source. Conc.+P-Source.Feed.conc.+Main. Thr.Conc.+Nitrogen. Conc.+total.sugar+His+lactate+PO4.apporte; 0.568, 0.805, tmp+Main.P-Source.Conc.+P-Source.Feed.conc.+Main. Thr.Conc.+Nitrogen.Conc.+PL+emission_CO2+rab+Thr+ His+lactate+PO4.apporte; 0.583, 0.805, pH+tmp+Main.P-Source.Conc.+Main.Thr.Conc.+Nitrogen.Conc.+total.Vol+ total.sugar+emission_O2+lactate+PO4.apporte; 0.598, 0.805, pH+tmp+Main.P-Source.Conc.+P-Source.Feed. conc.+Nitrogen.Conc.+total.sugar+lactate+PO4.apporte; 0.575, 0.805, pH+tmp+Main.P-Source.Conc.+P-Source. Feed.conc.+Main.Thr.Conc.+Nitrogen.Conc.+rab+Thr+ His+lactate+PO4.apporte; 0.575, 0.805, tmp+Main.P-Source.Conc.+Nitrogen.Conc.+total.Vol+total.sugar+ emission_O2+emission_CO2+Thr+His+lactate+PO4. apporte; 0.559, 0.804, pH+tmp+Main.P-Source.Conc.+P-Source.Feed. conc.+Nitrogen.Conc.+total.Vol+PL+ emission_CO2+rab+Thr+His+lactate+PO4.apporte; 0.559, 0.804, pH+tmp+Main.P-Source.Conc.+P-Source.Feed. conc.+Main.Thr. Conc.+Nitrogen.Conc.+total.sugar+emission_O2+emission_CO2+Thr+His+lactate+PO4.apporte; 0.567, 0.804, pH+tmp+Main.P-Source.Conc.+Main.Thr. Conc.+Nitrogen. Conc.+total.sugar+PL+emission_CO2+ Thr+His+lactate+PO4.apporte; 0.567, 0.804, pH+tmp+ Main.P-Source.Conc.+Main.Thr.Conc.+Nitrogen.Conc.+ PL+emission_CO2+rab+Thr+His+lactate+PO4.apporte; 0.590, 0.804, tmp+Main.P-Source.Conc.+P-Source.Feed. conc.+Nitrogen.Conc.+total.sugar+rab+His+lactate+PO4. apporte; 0.567, 0.804, tmp+Main.P-Source.Conc.+P-Source.Feed. conc.+Main. Thr.Conc.+Nitrogen.Conc.+total. sugar+PL+emission_O2+emission_CO2+Thr+lactate+PO4. apporte; 0.559, 0.804, pH+tmp+Main.P-Source.Conc.+P-Source. Feed.conc.+Main.Thr.Conc.+Nitrogen.Conc.+total. sugar+PL+emission_O2+emission_CO2+Thr+lactate+PO4. apporte; 0.590, 0.804, pH+tmp+Main.P-Source.Conc.+ Nitrogen.Conc.+total.Vol+total.sugar+emission_O2+ lactate+PO4.apporte; 0.590, 0.804, pH+tmp+Main.P-Source.Conc.+Nitrogen. Conc.+total.Vol+total.sugar+rab+ lactate+PO4.apporte; 0.575, 0.804, tmp+Main.P-Source. Conc.+Main.Thr.Conc.+Nitrogen.Conc.+total.Vol+total. sugar+emission_CO2+rab+Thr+lactate+PO4.apporte; 0.575, 0.804, tmp+Main.P-Source.Conc.+P-Source.Feed. conc.+Main.Thr.Conc.+Nitrogen.Conc.+total.Vol+total. sugar+PL+Thr+lactate+PO4.apporte; 0.567, 0.804, pH+tmp+Main.P-Source.Conc.+P-Source. Feed.conc.+Nitrogen.Conc.+total.sugar+PL+emission_ CO2+rab+Thr+lactate+PO4.apporte; 0.567, 0.804, tmp+Main.P-Source.Conc.+P-Source.Feed.conc.+

Main.Thr.Conc.+Nitrogen.Conc.+total.Vol+emission_CO2+rab+Thr+His+lactate+PO4.apporte; 0.567, 0.804, pH+tmp+Main.P-Source.Conc.+P-Source.Feed.conc.+Main.Thr.Conc.+Nitrogen.Conc.+total.sugar+PL+Thr+His+lactate+PO4.apporte; 0.604, 0.804, tmp+Main.P-Source.Conc.+Main.Thr.Conc.+Nitrogen.Conc.+total.sugar+lactate+PO4.apporte; 0.604, 0.804, pH+tmp+Main.P-Source.Conc.+Nitrogen.Conc.+Thr+His+PO4.apporte; 0.597, 0.804, pH+tmp+Main.P-Source.Conc.+Nitrogen.Conc.+total.sugar+rab+lactate+PO4.apporte; 0.597, 0.804, tmp+Main.P-Source.Conc.+P-Source.Feed. conc.+Nitrogen.Conc.+emission_CO2+His+lactate+PO4.apporte; 0.582, 0.804, tmp+Main.P-Source.Conc.+P-Source.Feed.conc.+Main.Thr.Conc.+Nitrogen.Conc.+rab+Thr+His+lactate+PO4.apporte; 0.558, 0.804, pH+tmp+Main.P-Source.Conc.+P-Source.Feed.conc.+Main.Thr.Conc.+Nitrogen.Conc.+total.Vol+emission_CO2+rab+Thr+His+lactate+PO4.apporte; 0.597, 0.804, pH+tmp+Main.P-Source.Conc.+Nitrogen.Conc.+total.sugar+Thr+His+PO4.apporte; 0.567, 0.804, tmp+Main.P-Source.Conc.+P-Source.Feed.conc.+Nitrogen. Conc.+total.sugar+PL+emission_O2+emission_CO2+Thr+His+lactate+PO4.apporte; 0.575, 0.804, tmp+Main.P-Source.Conc.+Main.Thr.Conc.+Nitrogen.Conc.+total.Vol+total.sugar+PL+emission_O2+Thr+lactate+PO4.apporte; 0.590, 0.804, pH+tmp+Main.P-Source.Conc.+P-Source. Feed.conc.+Nitrogen.Conc.+total.sugar+His+lactate+PO4.apporte; 0.597, 0.804, pH+tmp+Main.P-Source.Conc.+Nitrogen.Conc.+rab+His+lactate+PO4.apporte; 0.574, 0.804, tmp+Main.P-Source.Conc.+Nitrogen.Conc.+total.Vol+total.sugar+PL+emission_O2+emission_CO2+Thr+lactate+PO4.apporte; 0.566, 0.804, pH+tmp+Main.P-Source.Conc.+P-Source.Feed.conc.+Nitrogen.Conc.+total.sugar+PL+emission_CO2+Thr+His+lactate+PO4.apporte; 0.574, 0.804, tmp+Main.P-Source.Conc.+P-Source.Feed.conc.+Main.Thr.Conc.+Nitrogen.Conc.+total.Vol+total.sugar+emission_CO2+Thr+lactate+PO4.apporte; 0.574, 0.804, tmp+Main.P-Source.Conc.+P-Source.Feed.conc.+Nitrogen.Conc.+total.Vol+total.sugar+emission_CO2+Thr+His+lactate+PO4.apporte; 0.574, 0.804, pH+tmp+Main.P-Source.Conc.+Main.Thr.Conc.+Nitrogen.Conc.+total.sugar+emission_CO2+rab+Thr+lactate+PO4.apporte; 0.597, 0.804, pH+tmp+Main.P-Source.Conc.+Main.Thr.Conc.+Nitrogen.Conc.+total.sugar+lactate+PO4.apporte; 0.590, 0.804, tmp+Main.P-Source.Conc.+P-Source.Feed.conc.+Nitrogen.Conc.+total.sugar+emission_O2+His+lactate+PO4.apporte; 0.597, 0.804, pH+tmp+Main.P-Source.Conc.+Nitrogen.Conc.+total.sugar+emission_CO2+lactate+PO4.apporte; 0.589, 0.804, tmp+Main.P-Source.Conc.+P-Source.Feed.conc.+Main.Thr.Conc.+Nitrogen.Conc.+total.sugar+emission_O2+lactate+PO4.apporte; 0.589, 0.804, tmp+Main.P-Source.Conc.+P-Source.Feed.conc.+Main.Thr.Conc.+Nitrogen.Conc.+rab+His+lactate+PO4.apporte; 0.589, 0.804, tmp+Main.P-Source.Conc.+P-Source.Feed.conc.+Main.Thr.Conc.+Nitrogen.Conc.+total.sugar+rab+lactate+PO4.apporte; 0.589, 0.804, pH+tmp+Main.P-Source.Conc.+P-Source.Feed.conc.+Nitrogen.Conc.+rab+His+lactate+PO4.apporte; 0.574, 0.804, tmp+Main.P-Source.Conc.+Nitrogen.Conc.+total.Vol+total.sugar+PL+emission_CO2+rab+Thr+lactate+PO4.apporte; 0.589, 0.804, tmp+Main.P-Source.Conc.+Main.Thr.Conc.+Nitrogen.Conc.+total.sugar+rab+Thr+lactate+PO4.apporte; 0.596, 0.804, pH+tmp+Main.P-Source.Conc.+Nitrogen.Conc.+emission_O2+emission_CO2+Thr+PO4.apporte; 0.574, 0.804, pH+tmp+Main.P-Source.Conc.+P-Source.Feed.conc.+Main.Thr.Conc.+Nitrogen.Conc.+total.Vol+rab+Thr+lactate+PO4.apporte; 0.582, 0.804, tmp+Main.P-Source.Conc.+Main.Thr.Conc.+Nitrogen.Conc.+total.sugar+PL+rab+Thr+lactate+PO4.apporte; 0.589, 0.804, pH+tmp+Main.P-Source.Conc.+Nitrogen.Conc.+total.Vol+rab+His+lactate+PO4.apporte; 0.596, 0.804, pH+tmp+Main.P-Source.Conc.+Nitrogen.Conc.+total.sugar+His+lactate+PO4.apporte; 0.589, 0.804, tmp+Main.P-Source.Conc.+P-Source.Feed.conc.+Main.Thr.Conc.+Nitrogen.Conc.+total.sugar+emission_CO2+lactate+PO4.apporte; 0.596, 0.804, pH+tmp+Main.P-Source.Conc.+Nitrogen.Conc.+emission_O2+His+lactate+PO4.apporte; 0.596, 0.804, pH+tmp+Main.P-Source.Conc.+Nitrogen.Conc.+total.sugar+emission_O2+lactate+PO4.apporte; 0.574, 0.804, tmp+Main.P-Source.Conc.+Nitrogen.Conc.+total.sugar+PL+emission_CO2+rab+Thr+His+lactate+PO4.apporte; 0.574, 0.804, tmp+Main.P-Source.Conc.+Main.Thr.Conc.+Nitrogen.Conc.+total.Vol+total.sugar+emission_O2+Thr+His+lactate+PO4.apporte; 0.589, 0.804, pH+tmp+Main.P-Source.Conc.+Nitrogen.Conc.+total.Vol+total.sugar+His+lactate+PO4.apporte; 0.596, 0.804, tmp+Main.P-Source.Conc.+P-Source.Feed.conc.+Nitrogen.Conc.+total.sugar+emission_O2+lactate+PO4.apporte; 0.574, 0.804, pH+tmp+Main.P-Source.Conc.+Nitrogen.Conc.+total.Vol+PL+rab+Thr+His+lactate+PO4.apporte; 0.574, 0.804, tmp+Main.P-Source.Conc.+Nitrogen.Conc.+total.Vol+total.sugar+emission_CO2+rab+Thr+His+lactate+PO4.apporte; 0.596, 0.804, pH+tmp+Main.P-Source.Conc.+Nitrogen.Conc.+emission_CO2+His+lactate+PO4.apporte; 0.557, 0.804, pH+tmp+Main.P-Source.Conc.+Main.Thr.Conc.+Nitrogen.Conc.+total.sugar+PL+emission_O2+emission_CO2+Thr+His+lactate+PO4.apporte; 0.574, 0.804, pH+tmp+Main.P-Source.Conc.+Nitrogen.Conc.+total.sugar+PL+rab+Thr+His+lactate+PO4.apporte; 0.589, 0.804, tmp+Main.P-Source.Conc.+P-Source.Feed.conc.+Nitrogen.Conc.+total.sugar+emission_CO2+His+lactate+PO4.apporte; 0.581, 0.804, tmp+Main.P-Source.Conc.+P-Source.Feed.conc.+Main.Thr.Conc.+Nitrogen.Conc.+total.sugar+rab+Thr+lactate+PO4.apporte; 0.596, 0.804, tmp+Main.P-Source.Conc.+P-Source.Feed.conc.+Nitrogen.Conc.+total.sugar+emission_CO2+lactate+PO4.apporte; 0.589, 0.804, pH+tmp+Main.P-Source.Conc.+P-Source.Feed. conc.+Nitrogen.Conc.+emission_O2+His+lactate+PO4.apporte; 0.557, 0.804, pH+tmp+Main.P-Source.Conc.+Nitrogen.Conc.+total.Vol+total.sugar+PL+emission_O2+emission_CO2+Thr+His+lactate+PO4.apporte; 0.557, 0.803, pH+tmp+Main.P-Source.Conc.+Main.Thr.Conc.+Nitrogen.Conc.+total.Vol+total.sugar+PL+emission_CO2+rab+Thr+lactate+PO4.apporte; 0.589, 0.803, pH+tmp+Main.P-Source.Conc.+Nitrogen.Conc.+total.Vol+emission_CO2+His+lactate+PO4.apporte; 0.565, 0.803, tmp+Main.P-Source.Conc.+P-Source.Feed.conc.+Nitrogen. Conc.+total.Vol+total.sugar+emission_O2+emission_CO2+Thr+His+lactate+PO4.apporte; 0.565, 0.803, tmp+Main.P-Source.Conc.+P-Source.Feed.conc.+Main.Thr.Conc.+Nitrogen.Conc.+total.Vol+total.sugar+emission_O2+emission_CO2+Thr+lactate+PO4.apporte; 0.557, 0.803, pH+tmp+Main.P-Source.Conc.+P-Source.Feed.conc.+Nitrogen.Conc.+total.Vol+total.sugar+PL+emission_O2+emission_CO2+Thr+lactate+PO4.apporte; 0.588, 0.803, pH+tmp+Main.P-Source.Conc.+P-Source.Feed.conc.+Nitrogen.Conc.+emission_CO2+His+lactate+PO4.apporte; 0.565, 0.803, pH+tmp+Main.P-Source.Conc.+Main.Thr.Conc.+Nitrogen.Conc.+total.sugar+PL+emission_CO2+rab+Thr+lactate+PO4.apporte; 0.588, 0.803, pH+tmp+Main.P-Source.Conc.+P-Source.Feed.conc.+Nitrogen. Conc.+total.sugar+rab+lactate+PO4.apporte; 0.603, 0.803, tmp+Main.P-Source.Conc.+Main.Thr.Conc.+Nitrogen. Conc.+total.sugar+Thr+PO4.apporte; 0.581, 0.803, tmp+Main.P-Source.Conc.+P-Source.Feed.conc.+Main.Thr. Conc.+Nitrogen.Conc.+total.sugar+rab+His+lactate+ PO4.apporte; 0.581, 0.803, pH+tmp+Main.P-Source.Conc.+ Nitrogen.Conc.+total.sugar+rab+Thr+His+lactate+ PO4.apporte; 0.557, 0.803, pH+tmp+Main.P-Source.Conc.+ P-Source.Feed.conc.+Nitrogen.Conc.+total.sugar+PL+ emission_O2+emission_CO2+Thr+His+lactate+ PO4.apporte; 0.573, 0.803, pH+tmp+Main.P-Source.Conc.+ Nitrogen.Conc.+total.Vol+total.sugar+PL+rab+Thr+ lactate+PO4.apporte; 0.573, 0.803, tmp+Main.P-Source.Conc.+P-Source.Feed.conc.+Nitrogen.Conc.+ total.Vol+total.sugar+PL+Thr+His+lactate+PO4.apporte; 0.581, 0.803, tmp+Main.P-Source.Conc.+P-Source.Feed. conc.+Main.Thr.Conc.+Nitrogen.Conc.+total.sugar+emission_O2+emission_CO2+lactate+PO4.apporte; 0.588, 0.803, tmp+Main.P-Source.Conc.+P-Source.Feed.conc.+ Nitrogen.Conc.+emission_O2+emission_CO2+His+lactate+PO4.apporte; 0.565, 0.803, tmp+Main.P-Source.Conc.+P-Source.Feed.conc.+Nitrogen.Conc.+ total.Vol+PL+emission_CO2+rab+Thr+His+lactate+ PO4.apporte; 0.565, 0.803, pH+tmp+Main.P-Source.Conc.+ P-Source.Feed.conc.+Main.Thr.Conc.+Nitrogen.Conc.+ total.sugar+emission_CO2+rab+Thr+lactate+PO4.apporte; 0.565, 0.803, pH+tmp+Main.P-Source.Conc.+P-Source. Feed.conc.+Nitrogen.Conc.+total.Vol+total.sugar+PL+Thr+ His+lactate+PO4.apporte; 0.588, 0.803, pH+tmp+Main.P-Source.Conc.+Nitrogen.Conc.+total.sugar+emission_O2+ emission_CO2+Thr+PO4.apporte; 0.573, 0.803, tmp+ Main.P-Source.Conc.+Main.Thr.Conc.+Nitrogen.Conc.+ total.Vol+PL+emission_CO2+Thr+His+lactate+ PO4.apporte; 0.588, 0.803, pH+tmp+Main.P-Source.Conc.+ Main.Thr.Conc.+Nitrogen.Conc.+total.Vol+His+lactate+ PO4.apporte; 0.588, 0.803, pH+tmp+Main.P-Source.Conc.+ P-Source.Feed.conc.+Nitrogen.Conc.+total.sugar+ emission_CO2+lactate+PO4.apporte; 0.580, 0.803, pH+tmp+Main.P-Source.Conc.+Main.Thr.Conc.+Nitrogen. Conc.+total.Vol+total.sugar+His+lactate+PO4.apporte; 0.595, 0.803, pH+tmp+Main.P-Source.Conc.+Main.Thr. Conc.+Nitrogen.Conc.+His+lactate+PO4.apporte; 0.565, 0.803, tmp+Main.P-Source.Conc.+P-Source.Feed.conc.+ Main.Thr.Conc.+Nitrogen.Conc.+total.sugar+PL+emission_CO2+Thr+lactate+PO4.apporte; 0.588, 0.803, tmp+Main.P-Source.Conc.+P-Source.Feed.conc.+Nitrogen. Conc.+total.sugar+emission_O2+emission_CO2+lactate+ PO4.apporte; 0.602, 0.803, pH+tmp+Main.P-Source.Conc.+ Nitrogen.Conc.+rab+Thr+PO4.apporte; 0.580, 0.803, tmp+ Main.P-Source.Conc.+P-Source.Feed.conc.+ Nitrogen.Conc.+total.sugar+rab+Thr His+lactate+ PO4.apporte; 0.588, 0.803, pH+tmp+Main.P-Source.Conc.+ P-Source.Feed.conc.+Nitrogen.Conc.+total.sugar+ emission_O2+lactate+PO4.apporte; 0.602, 0.803, tmp+ Main.P-Source.Conc.+P-Source.Feed.conc.+ Nitrogen.Conc.+total.sugar+Thr+PO4.apporte; 0.595, 0.803, tmp+Main.P-Source.Conc.+Main.Thr.Conc.+Nitrogen.Conc.+total.Vol+total.sugar+lactate+PO4.apporte; 0.580, 0.803, tmp+Main.P-Source.Conc.+P-Source.Feed. conc.+Nitrogen.Conc.+total.sugar+emission_O2+emission_CO2+His+lactate+PO4.apporte; 0.572, 0.803, pH+tmp+Main.P-Source.Conc.+Nitrogen.Conc.+total. sugar+emission_CO2+rab+Thr+His+lactate+PO4.apporte; 0.587, 0.803, pH+tmp+Main.P-Source.Conc.+P-Source. Feed.conc.+Main.Thr.Conc.+Nitrogen.Conc.+total.sugar+ Thr+PO4.apporte; 0.564, 0.803, tmp+Main.P-Source.Conc.+P-Source.Feed.conc.+Main.Thr.Conc.+Nitrogen.Conc.+total.sugar+PL+emission_O2+Thr+His+ lactate+PO4.apporte; 0.580, 0.803, tmp+Main.P-Source. Conc.+P-Source.Feed.conc.+Main.Thr.Conc.+Nitrogen. Conc.+total.sugar+emission_O2+His+lactate+PO4.apporte; 0.587, 0.803, pH+tmp+Main.P-Source.Conc.+P-Source. Feed.conc.+Main.Thr.Conc.+Nitrogen.Conc.+total.sugar+ lactate+PO4.apporte; 0.587, 0.803, pH+tmp+Main.P-Source.Conc.+P-Source.Feed.conc.+Nitrogen.Conc.+total. Vol+total.sugar+lactate+PO4.apporte; 0.572, 0.803, tmp+ Main.P-Source.Conc.+P-Source.Feed. conc.+Nitrogen. Conc.+total.Vol+total.sugar+PL+emission_CO2+Thr+ lactate+PO4.apporte; 0.580, 0.803, pH+tmp+Main.P-Source.Conc.+Nitrogen.Conc.+total.Vol+emission_O2+ emission_CO2+His+lactate+PO4.apporte; 0.572, 0.803, tmp+Main.P-Source.Conc.+Nitrogen.Conc.+total.Vol+total. sugar+PL+emission_O2+Thr+His+lactate+PO4.apporte; 0.580, 0.803, pH+tmp+Main.P-Source.Conc.+Nitrogen. Conc.+total.Vol+total.sugar+rab+Thr+lactate+PO4.apporte; 0.580, 0.803, pH+tmp+Main.P-Source.Conc.+Nitrogen. Conc.+total.Vol+total.sugar+emission_CO2+His+lactate+ PO4.apporte; 0.587, 0.803, pH+tmp+Main.P-Source.Conc.+ Main.Thr.Conc.+Nitrogen.Conc.+total.sugar+emission_ O2+Thr+PO4.apporte; 0.587, 0.803, tmp+Main.P-Source. Conc.+Main.Thr.Conc.+Nitrogen. Conc.+rab+Thr+His+ lactate+PO4.apporte; 0.595, 0.803, tmp+Main.P-Source. Conc.+Main.Thr.Conc.+Nitrogen. Conc.+total.sugar+rab+ lactate+PO4.apporte; 0.587, 0.803, pH+tmp+Main.P-Source.Conc.+Nitrogen.Conc.+total.Vol+emission_O2+ His+lactate+PO4.apporte; 0.580, 0.803, tmp+Main.P-Source.Conc.+Main.Thr.Conc.+Nitrogen.Conc.+PL+rab+ Thr+His+lactate+PO4.apporte; 0.564, 0.803, pH+tmp+ Main.P-Source.Conc.+P-Source.Feed.conc.+Main.Thr. Conc.+Nitrogen.Conc.+total.sugar+PL+rab+Thr+lactate+ PO4.apporte; 0.572, 0.803, pH+tmp+Main.P-Source.Conc.+ P-Source.Feed.conc.+Nitrogen.Conc.+total.sugar+rab+ Thr+His+lactate+PO4.apporte; 0.580, 0.803, pH+tmp+ Main.P-Source.Conc.+P-Source.Feed. conc.+Main.Thr. Conc.+Nitrogen.Conc.+total.Vol+total. sugar+lactate+PO4. apporte; 0.580, 0.803, pH+tmp+Main.P-Source.Conc.+P-Source.Feed.conc.+Nitrogen.Conc.+emission_O2+ emission_CO2+His+lactate+PO4.apporte; 0.580, 0.803, pH+tmp+Main.P-Source.Conc.+P-Source.Feed.conc.+Nitrogen.Conc.+total.sugar+emission_O2+emission_CO2+ lactate+PO4.apporte; 0.587, 0.803, tmp+Main.P-Source. Conc.+P-Source.Feed.conc.+Main.Thr.Conc.+Nitrogen. Conc.+emission_O2+His+lactate+PO4.apporte; 0.587, 0.803, pH+tmp+Main.P-Source.Conc.+P-Source.Feed. conc.+Main.Thr.Conc.+Nitrogen.Conc.+His+lactate+PO4. apporte; 0.564, 0.803, tmp+Main.P-Source.Conc.+Main. Thr.Conc.+Nitrogen. Conc.+total.Vol+PL+emission_CO2+ rab+Thr+His+lactate+PO4.apporte; 0.587, 0.803, pH+tmp+ Main.P-Source.Conc.+Nitrogen.Conc.+total.sugar+ emission_O2+emission_CO2+lactate+PO4.apporte; 0.563, 0.803, pH+tmp+Main.P-Source.Conc.+P-Source.Feed. conc.+Nitrogen.Conc.+total.sugar+emission_CO2+rab+ Thr+His+lactate+PO4.apporte; 0.587, 0.803, pH+tmp+ Main.P-Source.Conc.+P-Source.Feed.conc.+Nitrogen. Conc.+total.Vol+His+lactate+PO4.apporte; 0.587, 0.802, pH+tmp+Main.P-Source.Conc.+Main.Thr.Conc.+Nitrogen. Conc.+total.sugar+emission_CO2+lactate+PO4.apporte; 0.555, 0.802, pH+tmp+Main.P-Source.Conc.+P-Source. Feed. conc.+Main.Thr.Conc.+Nitrogen.Conc.+total.Vol+ PL+emission_O2+Thr+His+lactate+PO4.apporte; 0.587, 0.802, pH+tmp+Main.P-Source.Conc.+ Nitrogen.Conc.+emission_O2+emission_CO2+His+ lactate+PO4.apporte; 0.579, 0.802, pH+tmp+ Main.P-Source.Conc.+Nitrogen.Conc.+total.Vol+ rab+Thr+His+lactate+PO4.apporte; 0.555, 0.802, pH+tmp+Main.P-Source.Conc.+P-Source.Feed.conc.+Main.Thr.Conc.+Nitrogen.Conc.+total.Vol+total.sugar+emission_CO2+rab+Thr+lactate+PO4.apporte; 0.601, 0.802, tmp+Main.P-Source.Conc.+Main.Thr.Conc.+Nitrogen.Conc.+His+lactate+PO4.apporte; 0.579, 0.802, tmp+Main.P-Source.Conc.+P-Source.Feed.conc.+Main.Thr.Conc.+Nitrogen.Conc.+total.sugar+emission_CO2+His+lactate+PO4.apporte; 0.601, 0.802, pH+tmp+Main.P-Source.Conc.+Nitrogen.Conc.+emission_O2+Thr+PO4.apporte; 0.579, 0.802, pH+tmp+Main.P-Source.Conc.+P-Source.Feed.conc.+Nitrogen.Conc.+total.sugar+emission_O2+His+lactate+PO4.apporte; 0.563, 0.802, pH+tmp+Main.P-Source.Conc.+P-Source.Feed.conc.+Main.Thr.Conc.+Nitrogen.Conc.+total.Vol+PL+rab+Thr+lactate+PO4.apporte; 0.555, 0.802, pH+tmp+Main.P-Source.Conc.+P-Source.Feed.conc.+Main.Thr.Conc.+Nitrogen.Conc.+total.Vol+PL+emission_CO2+Thr+His+lactate+PO4.apporte; 0.586, 0.802, pH+tmp+Main.P-Source.Conc.+Main.Thr.Conc.+Nitrogen.Conc.+total.sugar+emission_O2+lactate+PO4.apporte; 0.563, 0.802, tmp+Main.P-Source.Conc.+P-Source.Feed.conc.+Main.Thr.Conc.+Nitrogen.Conc.+total.Vol+PL+emission_O2+Thr+His+lactate+PO4.apporte; 0.571, 0.802, pH+tmp+Main.P-Source.Conc.+Nitrogen.Conc.+total.Vol+total.sugar+emission_O2+emission_CO2+His+lactate+PO4.apporte; 0.586, 0.802, tmp+Main.P-Source.Conc.+P-Source.Feed.conc.+Main.Thr.Conc.+Nitrogen.Conc.+total.Vol+total.sugar+lactate+PO4.apporte; 0.579, 0.802, pH+tmp+Main.P-Source.Conc.+P-Source.Feed.conc.+Nitrogen.Conc.+total.sugar+emission_CO2+His+lactate+PO4.apporte; 0.601, 0.802, tmp+Main.P-Source.Conc.+Nitrogen.Conc.+total.sugar+rab+lactate+PO4.apporte; 0.579, 0.802, pH+tmp+Main.P-Source.Conc.+Nitrogen.Conc.+total.Vol+total.sugar+rab+His+lactate+PO4.apporte; 0.563, 0.802, tmp+Main.P-Source.Conc.+Main.Thr.Conc.+Nitrogen.Conc.+total.Vol+PL+emission_O2+emission_CO2+Thr+His+lactate+PO4.apporte; 0.579, 0.802, pH+tmp+Main.P-Source.Conc.+P-Source.Feed.conc.+Nitrogen.Conc.+total.sugar+rab+His+lactate+PO4.apporte; 0.586, 0.802, pH+tmp+Main.P-Source.Conc.+Main.Thr.Conc.+Nitrogen.Conc.+total.sugar+rab+lactate+PO4.apporte; 0.586, 0.802, pH+tmp+Main.P-Source.Conc.+Nitrogen.Conc.+total.sugar+rab+His+lactate+PO4.apporte; 0.571, 0.802, tmp+Main.P-Source.Conc.+Main.Thr.Conc.+Nitrogen.Conc.+total.sugar+PL+emission_CO2+Thr+His+lactate+PO4.apporte; 0.586, 0.802, pH+tmp+Main.P-Source.Conc.+Nitrogen.Conc.+total.sugar+emission_CO2+His+lactate+PO4.apporte; 0.586, 0.802, pH+tmp+Main.P-Source.Conc.+Nitrogen.Conc.+emission_O2+emission_CO2+Thr+His+PO4.apporte; 0.586, 0.802, pH+tmp+Main.P-Source.Conc.+Nitrogen.Conc.+total.sugar+emission_O2+His+lactate+PO4.apporte; 0.607, 0.802, tmp+Main.P-Source.Conc.+Nitrogen.Conc.+His+lactate+PO4.apporte; 0.571, 0.802, pH+tmp+Main.P-Source.Conc.+Main.Thr.Conc.+Nitrogen.Conc.+total.Vol+total.sugar+emission_CO2+His+lactate+PO4.apporte; 0.586, 0.802, tmp+Main.P-Source.Conc.+P-Source.Feed.conc.+Main.Thr.Conc.+Nitrogen.Conc.+emission_CO2+His+lactate+PO4.apporte; 0.600, 0.802, tmp+Main.P-Source.Conc.+Nitrogen.Conc.+total.sugar+emission_O2+Thr+PO4.apporte; 0.571, 0.802, pH+tmp+Main.P-Source.Conc.+P-Source.Feed.conc.+Main.Thr.Conc.+Nitrogen.Conc.+total.Vol+total.sugar+emission_CO2+lactate+PO4.apporte; 0.562, 0.802, tmp+Main.P-Source.Conc.+P-Source.Feed.conc.+Main.Thr.Conc.+Nitrogen.Conc.+total.sugar+emission_CO2+rab+Thr+His+lactate+PO4.apporte; 0.571, 0.802, tmp+Main.P-Source.Conc.+Main.Thr.Conc.+Nitrogen.Conc.+total.Vol+total.sugar+PL+Thr+His+lactate+PO4.apporte; 0.593, 0.802, tmp+Main.P-Source.Conc.+Main.Thr.Conc.+Nitrogen.Conc.+total.sugar+emission_O2+lactate+PO4.apporte; 0.578, 0.802, pH+tmp+Main.P-Source.Conc.+P-Source.Feed.conc.+Nitrogen.Conc.+total.Vol+total.sugar+emission_CO2+lactate+PO4.apporte; 0.562, 0.802, tmp+Main.P-Source.Conc.+P-Source.Feed.conc.+Nitrogen.Conc.+total.sugar+PL+emission_CO2+rab+Thr+His+lactate+PO4.apporte; 0.593, 0.802, tmp+Main.P-Source.Conc.+Main.Thr.Conc.+Nitrogen.Conc.+total.sugar+His+lactate+PO4.apporte; 0.562, 0.802, tmp+Main.P-Source.Conc.+P-Source.Feed.conc.+Main.Thr.Conc.+Nitrogen.Conc.+total.Vol+total.sugar+emission_CO2+rab+Thr+lactate+PO4.apporte; 0.578, 0.802, pH+tmp+Main.P-Source.Conc.+Nitrogen.Conc.+total.Vol+total.sugar+emission_O2+His+lactate+PO4.apporte; 0.554, 0.802, pH+tmp+Main.P-Source.Conc.+P-Source.Feed.conc.+Main.Thr.Conc.+Nitrogen.Conc.+total.Vol+total.sugar+PL+emission_O2+Thr+lactate+PO4.apporte; 0.578, 0.802, pH+tmp+Main.P-Source.Conc.+P-Source.Feed.conc.+Nitrogen.Conc.+total.Vol+rab+His+lactate+PO4.apporte; 0.570, 0.802, tmp+Main.P-Source.Conc.+P-Source.Feed.conc.+Main.Thr.Conc.+Nitrogen.Conc.+PL+rab+Thr+His+lactate+PO4.apporte; 0.562, 0.802, pH+tmp+Main.P-Source.Conc.+Nitrogen.Conc.+total.sugar+PL+emission_CO2+rab+Thr+His+lactate+PO4.apporte; 0.570, 0.802, tmp+Main.P-Source.Conc.+Main.Thr.Conc.+Nitrogen.Conc.+total.sugar+emission_CO2+rab+Thr+His+lactate+PO4.apporte; 0.586, 0.802, pH+tmp+Main.P-Source.Conc.+Main.Thr.Conc.+Nitrogen.Conc.+rab+His+lactate+PO4.apporte; 0.554, 0.802, pH+tmp+Main.P-Source.Conc.+P-Source.Feed.conc.+Nitrogen.Conc.+total.Vol+total.sugar+PL+emission_CO2+rab+Thr+lactate+PO4.apporte; 0.562, 0.802, pH+tmp+Main.P-Source.Conc.+P-Source.Feed.conc.+Main.Thr.Conc.+Nitrogen.Conc.+PL+rab+Thr+His+lactate+PO4.apporte; 0.570, 0.802, tmp+Main.P-Source.Conc.+P-Source.Feed.conc.+Main.Thr.Conc.+Nitrogen.Conc.+total.sugar+emission_O2+emission_CO2+His+lactate+PO4.apporte; 0.554, 0.802, pH+tmp+Main.P-Source.Conc.+P-Source.Feed.conc.+Main.Thr.Conc.+Nitrogen.Conc.+total.Vol+total.sugar+emission_O2+Thr+His+lactate+PO4.apporte; 0.606, 0.802, tmp+Main.P-Source.Conc.+Nitrogen.Conc.+total.sugar+lactate+PO4.apporte; 0.570, 0.802, pH+tmp+Main.P-Source.Conc.+P-Source.Feed.conc.+Nitrogen.Conc.+total.sugar+emission_O2+emission_CO2+His+lactate+PO4.apporte; 0.553, 0.802, pH+tmp+Main.P-Source.Conc.+Main.Thr.Conc.+Nitrogen.Conc.+total.Vol+total.sugar+PL+emission_O2+Thr+His+lactate+PO4.apporte; 0.562, 0.802, pH+tmp+Main.P-Source.Conc.+Main.Thr.Conc.+Nitrogen.Conc.+total.Vol+total.sugar+emission_O2+emission_CO2+His+lactate+PO4.apporte; 0.592, 0.802, tmp+Main.P-Source.Conc.+Main.Thr.Conc.+Nitrogen.Conc.+rab+His+lactate+PO4.apporte; 0.599, 0.802, tmp+Main.P-Source.Conc.+Nitrogen.Conc.+rab+His+lactate+PO4.apporte; 0.585, 0.802, tmp+Main.P-Source.Conc.+Main.Thr.Conc.+Nitrogen.Conc.+total.Vol+rab+Thr+lactate+PO4.apporte; 0.562, 0.802, tmp+Main.P-Source.Conc.+P-Source.Feed.conc.+Main.Thr.Conc.+Nitrogen.Conc.+total.Vol+total.sugar+emission_O2+Thr+His+lactate+PO4.apporte; 0.585, 0.802, pH+tmp+Main.P-Source.Conc.+Main.Thr.Conc.+Nitrogen.Conc.+total.sugar+Thr+His+PO4.apporte; 0.599, 0.802, tmp+Main.P-Source.Conc.+Nitrogen.Conc.+total.sugar+Thr+His+PO4.apporte; 0.562, 0.802, tmp+Main.P-Source.Conc.+P-Source.Feed.conc.+Nitrogen.Conc.+ total.Vol+total.sugar+PL+emission_O2+emission_CO2+ Thr+lactate+PO4.apporte; 0.577, 0.802, pH+tmp+Main.P-Source.Conc.+P-Source.Feed.conc.+Main.Thr.Conc.+ Nitrogen.Conc.+total.sugar+emission_CO2+lactate+ PO4.apporte; 0.577, 0.802, tmp+Main.P-Source.Conc.+ Main.Thr.Conc.+Nitrogen.Conc.+total.Vol+PL+rab+Thr+ lactate+PO4.apporte; 0.577, 0.802, pH+tmp+Main.P-Source.Conc.+Main.Thr.Conc.+Nitrogen.Conc.+total.Vol+ emission_CO2+His+lactate+PO4.apporte; 0.585, 0.802, pH+tmp+Main.P-Source.Conc.+Main.Thr.Conc.+Nitrogen. Conc.+total.sugar+His+lactate+PO4.apporte; 0.561, 0.801, pH+tmp+Main.P-Source.Conc.+P-Source.Feed.conc.+ Main.Thr.Conc.+Nitrogen.Conc.+total.Vol+total.sugar+ emission_O2+emission_CO2+lactate+PO4.apporte; 0.577, 0.801, pH+tmp+Main.P-Source.Conc.+P-Source.Feed. conc.+Main.Thr.Conc.+Nitrogen.Conc.+rab+His+lactate+ PO4.apporte; 0.577, 0.801, pH+tmp+Main.P-Source.Conc.+ P-Source.Feed.conc.+Nitrogen.Conc.+total.Vol+total. sugar+rab+lactate+PO4.apporte; 0.592, 0.801, pH+tmp+ Main.P-Source.Conc.+Nitrogen.Conc.+total. sugar+PL+ Thr+PO4.apporte; 0.553, 0.801, pH+tmp+Main.P-Source.Conc.+Nitrogen.Conc.+total.Vol+total. sugar+PL+ emission_CO2+rab+Thr+His+lactate+PO4.apporte; 0.577, 0.801, pH+tmp+Main.P-Source.Conc.+P-Source.Feed. conc.+Main.Thr.Conc.+Nitrogen.Conc.+total.sugar+His+ lactate+PO4.apporte; 0.553, 0.801, pH+tmp+Main.P-Source.Conc.+P-Source.Feed.conc.+Nitrogen.Conc.+total. Vol+total.sugar+emission_CO2+rab+Thr+His+lactate+ PO4.apporte; 0.569, 0.801, tmp+Main.P-Source.Conc.+P-Source.Feed.conc.+Main.Thr.Conc.+Nitrogen.Conc.+ total.sugar+PL+rab+Thr+lactate+PO4.apporte; 0.599, 0.801, pH+tmp+Main.P-Source.Conc.+P-Source.Feed. conc.+Nitrogen.Conc.+Thr+PO4.apporte; 0.553, 0.801, pH+tmp+Main.P-Source.Conc.+P-Source. Feed.conc.+ Main.Thr.Conc.+Nitrogen.Conc.+total.sugar+PL+emission_CO2+Thr+His+lactate+PO4.apporte; 0.553, 0.801, pH+tmp+Main.P-Source.Conc.+Main.Thr.Conc.+Nitrogen. Conc.+total.Vol+total.sugar+emission_CO2+rab+Thr+His+ lactate+PO4.apporte; 0.592, 0.801, pH+tmp+Main.P-Source.Conc.+Nitrogen.Conc.+emission_O2+Thr+His+ PO4.apporte; 0.569, 0.801, pH+tmp+Main.P-Source.Conc.+ P-Source.Feed.conc.+Nitrogen.Conc.+total.Vol+ total.sugar+emission_O2+emission_CO2+lactate+ PO4.apporte; 0.561, 0.801, tmp+Main.P-Source.Conc.+P-Source.Feed.conc.+Nitrogen.Conc.+total.Vol+total.sugar+ emission_CO2+rab+Thr+His+lactate+PO4.apporte; 0.577, 0.801, tmp+Main.P-Source.Conc.+Nitrogen.Conc.+total. sugar+PL+rab+Thr+His+lactate+PO4.apporte; 0.577, 0.801, tmp+Main.P-Source.Conc.+P-Source.Feed.conc.+ Main.Thr.Conc.+Nitrogen.Conc.+emission_O2+emission_CO2+His+lactate+PO4.apporte; 0.569, 0.801, tmp+ Main.P-Source.Conc.+Main.Thr.Conc.+Nitrogen.Conc.+ total.Vol+total.sugar+PL+emission_CO2+Thr+lactate+ PO4.apporte; 0.584, 0.801, tmp+Main.P-Source.Conc.+ Nitrogen.Conc.+total.sugar+rab+Thr+His+lactate+ PO4.apporte; 0.577, 0.801, pH+tmp+Main.P-Source.Conc.+ P-Source.Feed. conc.+Nitrogen.Conc.+total.Vol+ total.sugar+His+lactate+PO4.apporte; 0.577, 0.801, pH+tmp+Main.P-Source.Conc.+P-Source.Feed.conc.+ Main.Thr.Conc.+Nitrogen.Conc.+total.sugar+emission_CO2+lactate+PO4.apporte; 0.561, 0.801, tmp+Main.P-Source.Conc.+Main.Thr.Conc.+Nitrogen.Conc.+ total.sugar+PL+emission_O2+emission_CO2+Thr+His+ lactate+PO4.apporte; 0.584, 0.801, pH+tmp+Main.P-Source.Conc.+P-Source.Feed.conc.+Nitrogen.Conc.+ emission_O2+emission_CO2+Thr+PO4.apporte; 0.592, 0.801, tmp+Main.P-Source.Conc.+Main.Thr.Conc.+Nitrogen.Conc.+total.sugar+emission_CO2+lactate+ PO4.apporte; 0.577, 0.801, pH+tmp+Main.P-Source.Conc.+ P-Source.Feed.conc.+Main.Thr.Conc.+Nitrogen.Conc.+ total.sugar+rab+lactate+PO4.apporte; 0.592, 0.801, pH+tmp+Main.P-Source.Conc.+Nitrogen.Conc.+total. sugar+rab+Thr+PO4.apporte; 0.577, 0.801, tmp+Main.P-Source.Conc.+P-Source.Feed.conc.+Main.Thr.Conc.+Nitrogen.Conc.+total.Vol+rab+Thr+lactate+PO4.apporte; 0.552, 0.801, pH+tmp+Main.P-Source.Conc.+P-Source. Feed.conc.+Main.Thr.Conc.+Nitrogen.Conc.+PL+emission_CO2+rab+Thr+His+lactate+PO4.apporte; 0.599, 0.801, pH+tmp+Main.P-Source.Conc.+Nitrogen.Conc.+ emission_CO2+Thr+PO4.apporte; 0.569, 0.801, pH+tmp+ Main.P-Source.Conc.+Main.Thr.Conc.+Nitrogen.Conc.+total.Vol+total.sugar+emission_O2+His+lactate+ PO4.apporte; 0.577, 0.801, pH+tmp+Main.P-Source.Conc.+ Main.Thr.Conc.+Nitrogen.Conc.+total.sugar+ emission_O2+emission_CO2+lactate+PO4.apporte; 0.552, 0.801, pH+tmp+Main.P-Source.Conc.+P-Source.Feed. conc.+Main.Thr.Conc.+Nitrogen.Conc.+total.Vol+total. sugar+PL+emission_CO2+Thr+lactate+PO4.apporte; 0.591, 0.801, pH+tmp+Main.P-Source.Conc.+Nitrogen. Conc.+total.sugar+emission_CO2+Thr+PO4.apporte; 0.569, 0.801, pH+tmp+Main.P-Source.Conc.+P-Source. Feed.conc.+Main.Thr.Conc.+Nitrogen.Conc.+total.sugar+ emission_O2+emission_CO2+lactate+PO4.apporte; 0.612, 0.801, pH+tmp+Main.P-Source.Conc.+Nitrogen.Conc.+ PO4.apporte; 0.598, 0.801, pH+tmp+Main.P-Source.Conc.+ Main.Thr.Conc.+Nitrogen.Conc.+Thr+PO4.apporte; 0.605, 0.801, tmp+Main.P-Source.Conc.+Nitrogen.Conc.+rab+ Thr+PO4.apporte; 0.584, 0.801, pH+tmp+Main.P-Source.Conc.+Main.Thr. Conc.+Nitrogen.Conc.+emission_O2+His+lactate+PO4.apporte; 0.560, 0.801, tmp+ Main.P-Source.Conc.+P-Source.Feed.conc.+ Main.Thr.Conc.+Nitrogen.Conc.+total.Vol+PL+ emission_CO2+Thr+His+lactate+PO4.apporte; 0.569, 0.801, pH+tmp+Main.P-Source.Conc.+Main.Thr.Conc.+ Nitrogen.Conc.+total.Vol+emission_O2+emission_CO2+ His+lactate+PO4.apporte; 0.576, 0.801, pH+tmp+Main.P-Source.Conc.+Main.Thr.Conc.+Nitrogen. Conc.+total.Vol+ total.sugar+PL+lactate+PO4.apporte; 0.543, 0.801, pH+tmp+Main.P-Source.Conc.+P-Source.Feed.conc.+ Main.Thr.Conc.+Nitrogen.Conc.+total.Vol+PL+emission_O2+emission_CO2+Thr+His+lactate+PO4.apporte; 0.591, 0.801, tmp+Main.P-Source.Conc.+P-Source.Feed. conc.+Nitrogen.Conc.+total.Vol+His+lactate+PO4.apporte; 0.568, 0.801, pH+tmp+Main.P-Source.Conc.+P-Source. Feed.conc.+Nitrogen.Conc.+total.Vol+rab+Thr+His+lactate+PO4.apporte; 0.605, 0.801, tmp+Main.P-Source.Conc.+Nitrogen.Conc.+Thr+His+PO4.apporte; 0.576, 0.801, pH+tmp+Main.P-Source.Conc.+Main.Thr. Conc.+Nitrogen.Conc.+total.sugar+emission_O2+emission_CO2+Thr+PO4.apporte; 0.611, 0.801, tmp+Main.P-Source.Conc.+Nitrogen.Conc.+Thr+PO4.apporte; 0.560, 0.801, tmp+Main.P-Source.Conc.+P-Source.Feed.conc.+ Main.Thr.Conc.+Nitrogen.Conc.+total.Vol+total.sugar+ PL+emission_O2+Thr+lactate+PO4.apporte; 0.576, 0.801, pH+tmp+Main.P-Source.Conc.+Nitrogen.Conc.+total. sugar+emission_O2+emission_CO2+His+lactate+ PO4.apporte; 0.568, 0.801, pH+tmp+Main.P-Source.Conc.+ Main.Thr.Conc.+Nitrogen.Conc.+total.sugar+rab+Thr+ His+lactate+PO4.apporte; 0.584, 0.801, pH+tmp+Main.P-Source.Conc.+Main.Thr.Conc.+Nitrogen.Conc.+ emission_CO2+His+lactate+PO4.apporte; 0.598, 0.801, pH+tmp+Main.P-Source.Conc.+Nitrogen.Conc.+emission_O2+emission_CO2+PO4.apporte; 0.584, 0.801, pH+tmp+Main.P-Source.Conc.+Main.Thr.Conc.+Nitrogen- .Conc.+total.sugar+rab+Thr+PO4.apporte; 0.576, 0.801, pH+tmp+Main.P-Source.Conc.+Main.Thr.Conc.+Nitrogen.Conc.+total.Vol+emission_O2+His+lactate+PO4.apporte; 0.598, 0.801, tmp+Main.P-Source.Conc.+Nitrogen.Conc.+total.sugar+His+lactate+PO4.apporte; 0.583, 0.801, tmp+Main.P-Source.Conc.+Main.Thr.Conc.+Nitrogen.Conc.+total.sugar+rab+His+lactate+PO4.apporte; 0.576, 0.801, pH+tmp+Main.P-Source.Conc.+P-Source.Feed.conc.+Nitrogen.Conc.+total.Vol+emission_CO2+His+lactate+PO4.apporte; 0.576, 0.801, pH+tmp+Main.P-Source.Conc.+P-Source.Feed.conc.+Nitrogen.Conc.+total.Vol+total.sugar+emission_O2+lactate+PO4.apporte; 0.551, 0.801, pH+tmp+Main.P-Source.Conc.+P-Source.Feed.conc.+Main.Thr.Conc.+Nitrogen.Conc.+total.Vol+total.sugar+emission_CO2+Thr+His+lactate+PO4.apporte; 0.568, 0.801, tmp+Main.P-Source.Conc.+Main.Thr.Conc.+Nitrogen.Conc.+total.Vol+total.sugar+emission_CO2+Thr+His+lactate+PO4.apporte; 0.576, 0.801, tmp+Main.P-Source.Conc.+P-Source.Feed.conc.+Nitrogen.Conc.+total.Vol+rab+Thr+His+lactate+PO4.apporte; 0.576, 0.801, tmp+Main.P-Source.Conc.+P-Source.Feed.conc.+Main.Thr.Conc.+Nitrogen.Conc.+total.Vol+total.sugar+emission_CO2+lactate+PO4.apporte; 0.591, 0.801, tmp+Main.P-Source.Conc.+P-Source.Feed.conc.+Nitrogen.Conc.+PL+His+lactate+PO4.apporte; 0.568, 0.801, tmp+Main.P-Source.Conc.+P-Source.Feed.conc.+Nitrogen.Conc.+total.sugar+PL+rab+Thr+His+lactate+PO4.apporte; 0.590, 0.801, pH+tmp+Main.P-Source.Conc.+Nitrogen.Conc.+total.Vol+total.sugar+Thr+PO4.apporte; 0.590, 0.801, tmp+Main.P-Source.Conc.+Nitrogen.Conc.+total.sugar+rab+His+lactate+PO4.apporte; 0.568, 0.800, pH+tmp+Main.P-Source.Conc.+P-Source.Feed.conc.+Nitrogen.Conc.+total.Vol+total.sugar+rab+Thr+lactate+PO4.apporte; 0.551, 0.800, pH+tmp+Main.P-Source.Conc.+Main.Thr.Conc.+Nitrogen.Conc.+total.Vol+total.sugar+PL+emission_CO2+Thr+His+lactate+PO4.apporte; 0.559, 0.800, pH+tmp+Main.P-Source.Conc.+P-Source.Feed.conc.+Nitrogen.Conc.+total.sugar+PL+rab+Thr+His+lactate+PO4.apporte; 0.568, 0.800, pH+tmp+Main.P-Source.Conc.+P-Source.Feed.conc.+Main.Thr.Conc.+Nitrogen.Conc.+total.Vol+total.sugar+emission_O2+lactate+PO4.apporte; 0.604, 0.800, pH+tmp+Main.P-Source.Conc.+Nitrogen.Conc.+lactate+PO4.apporte; 0.559, 0.800, tmp+Main.P-Source.Conc.+P-Source.Feed.conc.+Nitrogen.Conc.+total.Vol+total.sugar+PL+emission_CO2+rab+Thr+lactate+PO4.apporte; 0.583, 0.800, tmp+Main.P-Source.Conc.+Main.Thr.Conc.+Nitrogen.Conc.+total.Vol+total.sugar+emission_O2+lactate+PO4.apporte; 0.575, 0.800, tmp+Main.P-Source.Conc.+P-Source.Feed.conc.+Main.Thr.Conc.+Nitrogen.Conc.+total.Vol+total.sugar+His+lactate+PO4.apporte; 0.575, 0.800, pH+tmp+Main.P-Source.Conc.+P-Source.Feed.conc.+Main.Thr.Conc.+Nitrogen.Conc.+emission_O2+His+lactate+PO4.apporte; 0.583, 0.800, pH+tmp+Main.P-Source.Conc.+P-Source.Feed.conc.+Nitrogen.Conc.+total.sugar+emission_O2+Thr+PO4.apporte; 0.575, 0.800, pH+tmp+Main.P-Source.Conc.+P-Source.Feed.conc.+Main.Thr.Conc.+Nitrogen.Conc.+emission_CO2+His+lactate+PO4.apporte; 0.542, 0.800, pH+tmp+Main.P-Source.Conc.+P-Source.Feed.conc.+Main.Thr.Conc.+Nitrogen.Conc.+total.Vol+total.sugar+emission_O2+emission_CO2+Thr+His+lactate+PO4.apporte; 0.567, 0.800, pH+tmp+Main.P-Source.Conc.+P-Source.Feed.conc.+Nitrogen.Conc.+total.Vol+total.sugar+rab+His+lactate+PO4.apporte; 0.550, 0.800, pH+tmp+Main.P-Source.Conc.+P-Source.Feed.conc.+Main.Thr.Conc.+Nitrogen.Conc.+total.sugar+PL+emission_CO2+rab+Thr+lactate+PO4.apporte; 0.559, 0.800, tmp+Main.P-Source.Conc.+Main.Thr.Conc.+Nitrogen.Conc.+total.Vol+total.sugar+PL+emission_O2+emission_CO2+Thr+lactate+PO4.apporte; 0.567, 0.800, pH+tmp+Main.P-Source.Conc.+Main.Thr.Conc.+Nitrogen.Conc.+total.Vol+total.sugar+PL+emission_CO2+lactate+PO4.apporte; 0.575, 0.800, pH+tmp+Main.P-Source.Conc.+P-Source.Feed.conc.+Main.Thr.Conc.+Nitrogen.Conc.+total.Vol+His+lactate+PO4.apporte; 0.582, 0.800, tmp+Main.P-Source.Conc.+P-Source.Feed.conc.+Nitrogen.Conc.+total.Vol+rab+His+lactate+PO4.apporte; 0.559, 0.800, tmp+Main.P-Source.Conc.+P-Source.Feed.conc.+Main.Thr.Conc.+Nitrogen.Conc.+total.sugar+PL+emission_CO2+Thr+His+lactate+PO4.apporte; 0.582, 0.800, tmp+Main.P-Source.Conc.+Main.Thr.Conc.+Nitrogen.Conc.+total.Vol+total.sugar+emission_CO2+lactate+PO4.apporte; 0.582, 0.800, pH+tmp+Main.P-Source.Conc.+Nitrogen.Conc.+total.sugar+emission_O2+Thr+His+PO4.apporte; 0.550, 0.800, pH+tmp+Main.P-Source.Conc.+P-Source.Feed.conc.+Nitrogen.Conc.+total.Vol+total.sugar+PL+emission_O2+Thr+His+lactate+PO4.apporte; 0.590, 0.800, pH+tmp+Main.P-Source.Conc.+Nitrogen.Conc.+emission_CO2+Thr+His+PO4.apporte; 0.567, 0.800, pH+tmp+Main.P-Source.Conc.+P-Source.Feed.conc.+Main.Thr.Conc.+Nitrogen.Conc.+total.sugar+rab+His+lactate+PO4.apporte; 0.559, 0.800, tmp+Main.P-Source.Conc.+Main.Thr.Conc.+Nitrogen.Conc.+total.Vol+total.sugar+PL+emission_CO2+rab+Thr+lactate+PO4.apporte; 0.567, 0.800, pH+tmp+Main.P-Source.Conc.+P-Source.Feed.conc.+Main.Thr.Conc.+Nitrogen.Conc.+total.Vol+total.sugar+His+lactate+PO4.apporte; 0.590, 0.800, tmp+Main.P-Source.Conc.+P-Source.Feed.conc.+Nitrogen.Conc.+total.Vol+total.sugar+lactate+PO4.apporte; 0.590, 0.800, pH+tmp+Main.P-Source.Conc.+P-Source.Feed.conc.+Nitrogen.Conc.+Thr+His+PO4.apporte; 0.567, 0.800, pH+tmp+Main.P-Source.Conc.+P-Source.Feed.conc.+Nitrogen.Conc.+total.Vol+total.sugar+emission_CO2+His+lactate+PO4.apporte; 0.567, 0.800, tmp+Main.P-Source.Conc.+P-Source.Feed.conc.+Main.Thr.Conc.+Nitrogen.Conc.+total.Vol+total.sugar+emission_O2+emission_CO2+lactate+PO4.apporte; 0.575, 0.800, tmp+Main.P-Source.Conc.+P-Source.Feed.conc.+Main.Thr.Conc.+Nitrogen.Conc.+total.Vol+total.sugar+emission_O2+lactate+PO4.apporte; 0.558, 0.800, tmp+Main.P-Source.Conc.+Main.Thr.Conc.+Nitrogen.Conc.+total.Vol+total.sugar+emission_O2+emission_CO2+Thr+His+lactate+PO4.apporte; 0.558, 0.800, pH+tmp+Main.P-Source.Conc.+Main.Thr.Conc.+Nitrogen.Conc.+total.sugar+PL+rab+Thr+His+lactate+PO4.apporte; 0.582, 0.800, tmp+Main.P-Source.Conc.+P-Source.Feed.conc.+Main.Thr.Conc.+Nitrogen.Conc.+total.Vol+His+lactate+PO4.apporte; 0.558, 0.800, tmp+Main.P-Source.Conc.+P-Source.Feed.conc.+Nitrogen.Conc.+total.Vol+total.sugar+PL+emission_O2+Thr+His+lactate+PO4.apporte; 0.558, 0.800, pH+tmp+Main.P-Source.Conc.+P-Source.Feed.conc.+Nitrogen.Conc.+total.Vol+PL+rab+Thr+His+lactate+PO4.apporte; 0.566, 0.800, tmp+Main.P-Source.Conc.+Nitrogen.Conc.+total.Vol+total.sugar+PL+emission_CO2+Thr+His+lactate+PO4.apporte; 0.582, 0.800, pH+tmp+Main.P-Source.Conc.+Main.Thr.Conc.+Nitrogen.Conc.+emission_O2+emission_CO2+Thr+PO4.apporte; 0.574, 0.800, pH+tmp+Main.P-Source.Conc.+Main.Thr.Conc.+Nitrogen.Conc.+total.sugar+rab+His+lactate+PO4.apporte; 0.582, 0.800, tmp+Main.P-Source.Conc.+Main.Thr.Conc.+Nitrogen.Conc.+total.sugar+emission_O2+emission_CO2+lactate+PO4.apporte; 0.603, 0.800, pH+tmp+Main.P-Source.Conc.+Nitrogen.Conc.+rab+PO4.apporte; 0.574, 0.800, pH+tmp+Main.P-Source.Conc.+P-Source.

Feed.conc.+Nitrogen.Conc.+total.Vol+emission_O2+His+lactate+PO4.apporte; 0.574, 0.800, tmp+Main.P-Source.Conc.+Main.Thr.Conc.+Nitrogen.Conc.+total.Vol+total.sugar+emission_O2+emission_CO2+lactate+PO4.apporte; 0.558, 0.800, pH+tmp+Main.P-Source.Conc.+Main.Thr.Conc.+Nitrogen.Conc.+total.Vol+total.sugar+PL+rab+Thr+lactate+PO4.apporte; 0.574, 0.800, pH+tmp+Main.P-Source.Conc.+Main.Thr.Conc.+Nitrogen.Conc.+total.Vol+total.sugar+rab+lactate+PO4.apporte; 0.589, 0.800, tmp+Main.P-Source.Conc.+Main.Thr.Conc.+Nitrogen.Conc.+emission_O2+His+lactate+PO4.apporte; 0.582, 0.800, tmp+Main.P-Source.Conc.+P-Source.Feed.conc.+Nitrogen.Conc.+total.Vol+total.sugar+His+lactate+PO4.apporte; 0.574, 0.800, pH+tmp+Main.P-Source.Conc.+Main.Thr.Conc.+Nitrogen.Conc.+total.sugar+emission_O2+His+lactate+PO4.apporte; 0.582, 0.800, tmp+Main.P-Source.Conc.+Main.Thr.Conc.+Nitrogen.Conc.+total.Vol+total.sugar+His+lactate+PO4.apporte; 0.582, 0.800, pH+tmp+Main.P-Source.Conc.+P-Source.Feed.conc.+Nitrogen.Conc.+total.sugar+Thr+His+PO4.apporte; 0.566, 0.800, pH+tmp+Main.P-Source.Conc.+P-Source.Feed.conc.+Main.Thr.Conc.+Nitrogen.Conc.+total.sugar+emission_CO2+His+lactate+PO4.apporte; 0.566, 0.800, pH+tmp+Main.P-Source.Conc.+P-Source.Feed.conc.+Main.Thr.Conc.+Nitrogen.Conc.+total.sugar+emission_O2+His+lactate+PO4.apporte; 0.589, 0.800, pH+tmp+Main.P-Source.Conc.+Main.Thr.Conc.+Nitrogen.Conc.+rab+Thr+PO4.apporte; 0.596, 0.800, tmp+Main.P-Source.Conc.+Nitrogen.Conc.+emission_O2+His+lactate+PO4.apporte; 0.574, 0.800, pH+tmp+Main.P-Source.Conc.+Main.Thr.Conc.+Nitrogen.Conc.+emission_O2+emission_CO2+His+lactate+PO4.apporte; 0.566, 0.800, pH+tmp+Main.P-Source.Conc.+P-Source.Feed.conc.+Main.Thr.Conc.+Nitrogen.Conc.+emission_O2+emission_CO2+His+lactate+PO4.apporte; 0.574, 0.800, pH+tmp+Main.P-Source.Conc.+Main.Thr.Conc.+Nitrogen.Conc.+total.sugar+emission_CO2+His+lactate+PO4.apporte; 0.566, 0.800, pH+tmp+Main.P-Source.Conc.+Main.Thr.Conc.+Nitrogen.Conc.+total.Vol+total.sugar+rab+Thr+lactate+PO4.apporte; 0.540, 0.800, pH+tmp+Main.P-Source.Conc.+P-Source.Feed.conc.+Main.Thr.Conc.+Nitrogen.Conc.+total.Vol+total.sugar+PL+emission_O2+emission_CO2+Thr+lactate+PO4.apporte; 0.574, 0.800, pH+tmp+Main.P-Source.Conc.+P-Source.Feed.conc.+Nitrogen.Conc.+total.sugar+emission_O2+emission_CO2+Thr+PO4.apporte; 0.581, 0.800, pH+tmp+Main.P-Source.Conc.+Main.Thr.Conc.+Nitrogen.Conc.+total.sugar+PL+Thr+PO4.apporte; 0.581, 0.800, tmp+Main.P-Source.Conc.+Main.Thr.Conc.+Nitrogen.Conc.+total.sugar+emission_O2+His+lactate+PO4.apporte; 0.589, 0.800, pH+tmp+Main.P-Source.Conc.+P-Source.Feed.conc.+Nitrogen.Conc.+rab+Thr+PO4.apporte; 0.581, 0.800, tmp+Main.P-Source.Conc.+P-Source.Feed.conc.+Nitrogen.Conc.+total.sugar+PL+His+lactate+PO4.apporte; 0.549, 0.800, tmp+Main.P-Source.Conc.+P-Source.Feed.conc.+Main.Thr.Conc.+Nitrogen.Conc.+total.Vol+PL+emission_O2+emission_CO2+Thr+His+lactate+PO4.apporte; 0.574, 0.800, tmp+Main.P-Source.Conc.+Nitrogen.Conc.+total.Vol+PL+rab+Thr+His+lactate+PO4.apporte; 0.558, 0.800, pH+tmp+Main.P-Source.Conc.+P-Source.Feed.conc.+Main.Thr.Conc.+Nitrogen.Conc.+total.sugar+rab+Thr+His+lactate+PO4.apporte; 0.581, 0.799, pH+tmp+Main.P-Source.Conc.+P-Source.Feed.conc.+Nitrogen.Conc.+PL+His+lactate+PO4.apporte; 0.596, 0.799, tmp+Main.P-Source.Conc.+Nitrogen.Conc.+total.sugar+emission_O2+lactate+PO4.apporte; 0.581, 0.799, tmp+Main.P-Source.Conc.+P-Source.Feed.conc.+Main.Thr.Conc.+Nitrogen.Conc.+total.sugar+PL+lactate+PO4.apporte; 0.581, 0.799, tmp+Main.P-Source.Conc.+P-Source.Feed.conc.+Nitrogen.Conc.+PL+rab+His+lactate+PO4.apporte; 0.566, 0.799, pH+tmp+Main.P-Source.Conc.+P-Source.Feed.conc.+Nitrogen.Conc.+total.Vol+emission_O2+emission_CO2+His+lactate+PO4.apporte; 0.549, 0.799, pH+tmp+Main.P-Source.Conc.+P-Source.Feed.conc.+Main.Thr.Conc.+Nitrogen.Conc.+total.sugar+PL+emission_CO2+Thr+His+lactate+PO4.apporte; 0.588, 0.799, tmp+Main.P-Source.Conc.+P-Source.Feed.conc.+Main.Thr.Conc.+Nitrogen.Conc.+total.sugar+Thr+PO4.apporte; 0.602, 0.799, pH+tmp+Main.P-Source.Conc.+Nitrogen.Conc.+emission_CO2+PO4.apporte; 0.557, 0.799, tmp+Main.P-Source.Conc.+Main.Thr.Conc.+Nitrogen.Conc.+total.sugar+PL+emission_CO2+rab+Thr+His+lactate+PO4.apporte; 0.549, 0.799, tmp+Main.P-Source.Conc.+P-Source.Feed.conc.+Main.Thr.Conc.+Nitrogen.Conc.+total.sugar+PL+emission_O2+emission_CO2+Thr+His+lactate+PO4.apporte; 0.573, 0.799, pH+tmp+Main.P-Source.Conc.+Main.Thr.Conc.+Nitrogen.Conc.+total.Vol+rab+His+lactate+PO4.apporte; 0.557, 0.799, tmp+Main.P-Source.Conc.+P-Source.Feed.conc.+Main.Thr.Conc.+Nitrogen.Conc.+total.Vol+total.sugar+emission_CO2+Thr+His+lactate+PO4.apporte; 0.573, 0.799, tmp+Main.P-Source.Conc.+P-Source.Feed.conc.+Nitrogen.Conc.+total.Vol+total.sugar+rab+Thr+lactate+PO4.apporte; 0.581, 0.799, tmp+Main.P-Source.Conc.+P-Source.Feed.conc.+Nitrogen.Conc.+total.Vol+total.sugar+rab+lactate+PO4.apporte; 0.595, 0.799, pH+tmp+Main.P-Source.Conc.+Nitrogen.Conc.+emission_CO2+lactate+PO4.apporte; 0.549, 0.799, pH+tmp+Main.P-Source.Conc.+P-Source.Feed.conc.+Nitrogen.Conc.+total.Vol+total.sugar+PL+emission_CO2+Thr+His+lactate+PO4.apporte; 0.602, 0.799, pH+tmp+Main.P-Source.Conc.+Main.Thr.Conc.+Nitrogen.Conc.+PO4.apporte; 0.540, 0.799, pH+tmp+Main.P-Source.Conc.+Main.Thr.Conc.+Nitrogen.Conc.+total.Vol+total.sugar+PL+emission_O2+emission_CO2+Thr+His+lactate+PO4.apporte; 0.557, 0.799, pH+tmp+Main.P-Source.Conc.+Main.Thr.Conc.+Nitrogen.Conc.+total.Vol+total.sugar+PL+emission_O2+emission_CO2+lactate+PO4.apporte; 0.557, 0.799, tmp+Main.P-Source.Conc.+Main.Thr.Conc.+Nitrogen.Conc.+total.Vol+total.sugar+emission_CO2+rab+Thr+His+lactate+PO4.apporte; 0.602, 0.799, pH+tmp+Main.P-Source.Conc.+Nitrogen.Conc.+emission_O2+PO4.apporte; 0.588, 0.799, pH+tmp+Main.P-Source.Conc.+Nitrogen.Conc.+PL+His+lactate+PO4.apporte; 0.565, 0.799, tmp+Main.P-Source.Conc.+P-Source.Feed.conc.+Main.Thr.Conc.+Nitrogen.Conc.+total.Vol+PL+rab+Thr+lactate+PO4.apporte; 0.557, 0.799, pH+tmp+Main.P-Source.Conc.+P-Source.Feed.conc.+Nitrogen.Conc.+total.Vol+total.sugar+PL+rab+Thr+lactate+PO4.apporte; 0.602, 0.799, tmp+Main.P-Source.Conc.+P-Source.Feed.conc.+Nitrogen.Conc.+Thr+PO4.apporte; 0.557, 0.799, pH+tmp+Main.P-Source.Conc.+P-Source.Feed.conc.+Main.Thr.Conc.+Nitrogen.Conc.+total.sugar+emission_O2+emission_CO2+His+lactate+PO4.apporte; 0.580, 0.799, tmp+Main.P-Source.Conc.+Nitrogen.Conc.+total.Vol+total.sugar+rab+Thr+lactate+PO4.apporte; 0.573, 0.799, tmp+Main.P-Source.Conc.+Nitrogen.Conc.+total.Vol+total.sugar+PL+rab+Thr+lactate+PO4.apporte; 0.557, 0.799, pH+tmp+Main.P-Source.Conc.+P-Source.Feed.conc.+Nitrogen.Conc.+total.Vol+total.sugar+emission_O2+emission_CO2+His+lactate+PO4.apporte; 0.588, 0.799, tmp+Main.P-Source.Conc.+Main.Thr.Conc.+Nitrogen.Conc.+total.Vol+His+lactate+PO4.apporte; 0.565, 0.799, pH+tmp+Main.P-Source.Conc.+P-Source.Feed.conc.+Nitrogen.Conc.+total.Vol+total.sugar+emission_O2+His+lactate+PO4.apporte; 0.573, 0.799, tmp+Main.P-Source.Conc.+P-Source.Feed.conc.+Nitrogen.Conc.+total.Vol+total.sugar+rab+His+lactate+PO4.apporte; 0.539, 0.799, pH+tmp+Main.P-Source.Conc.+P-Source.Feed.conc.+Main.Thr.Conc.+Nitrogen.Conc.+total.Vol+PL+emission_CO2+rab+Thr+His+lactate+PO4.apporte; 0.556, 0.799, pH+tmp+Main.P-Source.Conc.+P-Source.Feed.conc.+Main.Thr.Conc.+Nitrogen.Conc.+total.Vol+total.sugar+emission_CO2+His+lactate+PO4.apporte; 0.580, 0.799, pH+tmp+Main.P-Source.Conc.+Nitrogen.Conc.+total.Vol+total.sugar+PL+lactate+PO4.apporte; 0.580, 0.799, tmp+Main.P-Source.Conc.+Nitrogen.Conc.+total.Vol+rab+Thr+His+lactate+PO4.apporte; 0.548, 0.799, pH+tmp+Main.P-Source.Conc.+P-Source.Feed.conc.+Main.Thr.Conc.+Nitrogen.Conc.+total.Vol+total.sugar+PL+Thr+His+lactate+PO4.apporte; 0.573, 0.799, pH+tmp+Main.P-Source.Conc.+Nitrogen.Conc.+total.sugar+emission_O2+emission_CO2+Thr+His+PO4.apporte; 0.556, 0.799, tmp+Main.P-Source.Conc.+Nitrogen.Conc.+total.Vol+total.sugar+PL+emission_O2+emission_CO2+Thr+His+lactate+PO4.apporte; 0.580, 0.799, pH+tmp+Main.P-Source.Conc.+Main.Thr.Conc.+Nitrogen.Conc.+total.sugar+emission_CO2+Thr+PO4.apporte; 0.564, 0.799, tmp+Main.P-Source.Conc.+P-Source.Feed.conc.+Nitrogen.Conc.+total.Vol+PL+rab+Thr+His+lactate+PO4.apporte; 0.572, 0.799, tmp+Main.P-Source.Conc.+P-Source.Feed.conc.+Main.Thr.Conc.+Nitrogen.Conc.+total.sugar+PL+His+lactate+PO4.apporte; 0.548, 0.799, pH+tmp+Main.P-Source.Conc.+P-Source.Feed.conc.+Nitrogen.Conc.+total.sugar+PL+emission_CO2+rab+Thr+His+lactate+PO4.apporte; 0.556, 0.799, tmp+Main.P-Source.Conc.+P-Source.Feed.conc.+Main.Thr.Conc.+Nitrogen.Conc.+total.Vol+total.sugar+PL+Thr+His+lactate+PO4.apporte; 0.587, 0.799, pH+tmp+Main.P-Source.Conc.+Main.Thr.Conc.+Nitrogen.Conc.+emission_O2+emission_CO2+PO4.apporte; 0.556, 0.799, pH+tmp+Main.P-Source.Conc.+Main.Thr.Conc.+Nitrogen.Conc.+total.sugar+emission_CO2+rab+Thr+His+lactate+PO4.apporte; 0.556, 0.799, tmp+Main.P-Source.Conc.+P-Source.Feed.conc.+Main.Thr.Conc.+Nitrogen.Conc.+total.Vol+total.sugar+PL+emission_CO2+Thr+lactate+PO4.apporte; 0.564, 0.799, pH+tmp+Main.P-Source.Conc.+Main.Thr.Conc.+Nitrogen.Conc.+total.Vol+total.sugar+PL+emission_O2+lactate+PO4.apporte; 0.594, 0.799, tmp+Main.P-Source.Conc.+P-Source.Feed.conc.+Nitrogen.Conc.+rab+Thr+PO4.apporte; 0.587, 0.799, tmp+Main.P-Source.Conc.+Nitrogen.Conc.+total.sugar+emission_O2+emission_CO2+Thr+PO4.apporte; 0.548, 0.799, tmp+Main.P-Source.Conc.+P-Source.Feed.conc.+Main.Thr.Conc.+Nitrogen.Conc.+total.Vol+total.sugar+emission_O2+emission_CO2+Thr+His+lactate+PO4.apporte; 0.594, 0.799, tmp+Main.P-Source.Conc.+Nitrogen.Conc.+total.sugar+emission_CO2+lactate+PO4.apporte; 0.539, 0.799, pH+tmp+Main.P-Source.Conc.+P-Source.Feed.conc.+Main.Thr.Conc.+Nitrogen.Conc.+total.sugar+PL+emission_O2+emission_CO2+Thr+His+lactate+PO4.apporte; 0.594, 0.799, pH+tmp+Main.P-Source.Conc.+Nitrogen.Conc.+emission_O2+lactate+PO4.apporte; 0.587, 0.799, tmp+Main.P-Source.Conc.+P-Source.Feed.conc.+Nitrogen.Conc.+total.sugar+PL+lactate+PO4.apporte; 0.580, 0.799, tmp+Main.P-Source.Conc.+P-Source.Feed.conc.+Nitrogen.Conc.+PL+emission_O2+His+lactate+PO4.apporte; 0.587, 0.799, pH+tmp+Main.P-Source.Conc.+P-Source.Feed.conc.+Nitrogen.Conc.+emission_O2+Thr+PO4.apporte; 0.587, 0.799, tmp+Main.P-Source.Conc.+Main.Thr.Conc.+Nitrogen.Conc.+total.sugar+emission_O2+Thr+PO4.apporte; 0.580, 0.799, tmp+Main.P-Source.Conc.+P-Source.Feed.conc.+Nitrogen.Conc.+total.Vol+emission_CO2+His+lactate+PO4.apporte; 0.580, 0.799, tmp+Main.P-Source.Conc.+P-Source.Feed.conc.+Nitrogen.Conc.+total.Vol+total.sugar+emission_CO2+lactate+PO4.apporte; 0.594, 0.799, tmp+Main.P-Source.Conc.+Nitrogen.Conc.+emission_CO2+His+lactate+PO4.apporte; 0.579, 0.799, tmp+Main.P-Source.Conc.+P-Source.Feed.conc.+Nitrogen.Conc.+total.Vol+emission_O2+His+lactate+PO4.apporte; 0.594, 0.799, tmp+Main.P-Source.Conc.+Main.Thr.Conc.+Nitrogen.Conc.+rab+Thr+PO4.apporte; 0.564, 0.799, tmp+Main.P-Source.Conc.+P-Source.Feed.conc.+Main.Thr.Conc.+Nitrogen.Conc.+total.sugar+rab+Thr+His+lactate+PO4.apporte; 0.579, 0.799, tmp+Main.P-Source.Conc.+P-Source.Feed.conc.+Main.Thr.Conc.+Nitrogen.Conc.+PL+His+lactate+PO4.apporte; 0.594, 0.799, tmp+Main.P-Source.Conc.+Nitrogen.Conc.+total. sugar+PL+Thr+PO4.apporte; 0.601, 0.799, tmp+Main.P-Source.Conc.+Main.Thr.Conc.+Nitrogen.Conc.+Thr+PO4.apporte; 0.579, 0.799, tmp+Main.P-Source.Conc.+Main.Thr.Conc.+Nitrogen.Conc.+total.sugar+emission_CO2+His+lactate+PO4.apporte; 0.587, 0.798, tmp+Main.P-Source.Conc.+Main.Thr.Conc.+Nitrogen.Conc.+emission_CO2+His+lactate+PO4.apporte; 0.579, 0.798, tmp+Main.P-Source.Conc.+P-Source.Feed.conc.+Nitrogen.Conc.+total.sugar+PL+rab+lactate+PO4.apporte; 0.587, 0.798, tmp+Main.P-Source.Conc.+P-Source.Feed.conc.+Nitrogen.Conc.+emission_O2+emission_CO2+Thr+PO4.apporte; 0.587, 0.798, pH+tmp+Main.P-Source.Conc.+Nitrogen.Conc.+total.sugar+PL+lactate+PO4.apporte; 0.555, 0.798, tmp+Main.P-Source.Conc.+Main.Thr.Conc.+Nitrogen.Conc.+total.Vol+total.sugar+PL+emission_O2+Thr+His+lactate+PO4.apporte; 0.587, 0.798, tmp+Main.P-Source.Conc.+Nitrogen.Conc.+total.sugar+emission_O2+His+lactate+PO4.apporte; 0.601, 0.798, tmp+Main.P-Source.Conc.+Nitrogen.Conc.+emission_O2+Thr+PO4.apporte; 0.572, 0.798, pH+tmp+Main.P-Source.Conc.+P-Source.Feed.conc.+Nitrogen.Conc.+emission_O2+emission_CO2+Thr+His+PO4.apporte; 0.564, 0.798, pH+tmp+Main.P-Source.Conc.+P-Source.Feed.conc.+Main.Thr.Conc.+Nitrogen.Conc.+total.Vol+emission_CO2+His+lactate+PO4.apporte; 0.587, 0.798, tmp+Main.P-Source.Conc.+P-Source.Feed.conc.+Nitrogen.Conc.+total.sugar+emission_O2+Thr+PO4.apporte; 0.594, 0.798, tmp+Main.P-Source.Conc.+Nitrogen.Conc.+emission_O2+emission_CO2+Thr+PO4.apporte; 0.587, 0.798, pH+tmp+Main.P-Source.Conc.+Nitrogen.Conc.+emission_O2+emission_CO2+lactate+PO4.apporte; 0.594, 0.798, pH+tmp+Main.P-Source.Conc.+Nitrogen.Conc.+total.Vol+lactate+PO4.apporte; 0.555, 0.798, tmp+Main.P-Source.Conc.+Nitrogen.Conc.+total.Vol+total.sugar+PL+emission_CO2+rab+Thr+His+lactate+PO4.apporte; 0.563, 0.798, pH+tmp+Main.P-Source.Conc.+Main.Thr.Conc.+Nitrogen.Conc.+total.sugar+emission_O2+emission_CO2+His+lactate+PO4.apporte; 0.594, 0.798, pH+tmp+Main.P-Source.Conc.+Nitrogen.Conc.+rab+lactate+PO4.apporte; 0.571, 0.798, tmp+Main.P-Source.Conc.+P-Source.Feed.conc.+Nitrogen.Conc.+total. sugar+PL+rab+His+lactate+PO4.apporte; 0.586, 0.798, pH+tmp+Main.P-Source.Conc.+Main.Thr.Conc.+Nitrogen.Conc.+emission_O2+Thr+PO4.apporte; 0.571, 0.798, tmp+Main.P-Source.Conc.+P-Source.Feed.conc.+Main.Thr.Conc.+Nitrogen.Conc.+total.sugar+PL+rab+lactate+PO4.apporte; 0.547, 0.798, tmp+Main.P-Source.Conc.+P-Source.Feed.conc.+Main.Thr.Conc.+Nitrogen.Conc.+total.Vol+PL+emission_CO2+rab+Thr+His+lactate+

PO4.apporte; 0.555, 0.798, pH+tmp+Main.P-Source.Conc.+Main.Thr.Conc.+Nitrogen.Conc.+total.Vol+PL+rab+Thr+His+lactate+PO4.apporte; 0.563, 0.798, tmp+Main.P-Source.Conc.+P-Source.Feed.conc.+Main.Thr.Conc.+Nitrogen.Conc.+total.Vol+total.sugar+emission_CO2+His+lactate+PO4.apporte; 0.586, 0.798, pH+tmp+Main.P-Source.Conc.+Main.Thr.Conc.+Nitrogen.Conc.+Thr+His+PO4.apporte; 0.593, 0.798, tmp+Main.P-Source.Conc.+Nitrogen.Conc.+total.Vol+total.sugar+lactate+PO4.apporte; 0.579, 0.798, pH+tmp+Main.P-Source.Conc.+Main.Thr.Conc.+Nitrogen.Conc.+total.Vol+total.sugar+Thr+PO4.apporte; 0.579, 0.798, tmp+Main.P-Source.Conc.+P-Source.Feed.conc.+Nitrogen.Conc.+PL+emission_CO2+His+lactate+PO4.apporte; 0.579, 0.798, tmp+Main.P-Source.Conc.+P-Source.Feed.conc.+Nitrogen.Conc.+total.Vol+total.sugar+emission_O2+lactate+PO4.apporte; 0.586, 0.798, tmp+Main.P-Source.Conc.+Main.Thr.Conc.+Nitrogen.Conc.+total.sugar+PL+lactate+PO4.apporte; 0.546, 0.798, pH+tmp+Main.P-Source.Conc.+P-Source.Feed.conc.+Main.Thr.Conc.+Nitrogen.Conc.+total.sugar+emission_CO2+rab+Thr+His+lactate+PO4.apporte; 0.546, 0.798, pH+tmp+Main.P-Source.Conc.+P-Source.Feed.conc.+Main.Thr.Conc.+Nitrogen.Conc.+total.Vol+total.sugar+emission_O2+emission_CO2+His+lactate+PO4.apporte; 0.571, 0.798, pH+tmp+Main.P-Source.Conc.+Nitrogen.Conc.+total.Vol+total.sugar+PL+emission_CO2+lactate+PO4.apporte; 0.563, 0.798, tmp+Main.P-Source.Conc.+P-Source.Feed.conc.+Main.Thr.Conc.+Nitrogen.Conc.+total.Vol+total.sugar+emission_O2+His+lactate+PO4.apporte; 0.579, 0.798, pH+tmp+Main.P-Source.Conc.+Nitrogen.Conc.+total.Vol+emission_O2+emission_CO2+lactate+PO4.apporte

[12. Linear Model that Predicts Lysine Production Amount in Interval 2]

0.775, 0.900, tmp+Main.P-Source.Conc.+Nitrogen.Conc.+total.Vol+PL+emission_CO2+His+lactate+PO4.ferm.+PO4.apporte; 0.770, 0.900, tmp+Main.P-Source.Conc.+Nitrogen.Conc.+total.Vol+PL+emission_O2+emission_CO2+His+lactate+PO4.ferm.+PO4.apporte; 0.774, 0.899, tmp+Main.P-Source.Conc.+Nitrogen.Conc.+total.Vol+PL+emission_CO2+His+lactate+PO4.apporte+PO4.utilise; 0.766, 0.899, tmp+Main.P-Source.Conc.+Nitrogen.Conc.+total.Vol+PL+emission_O2+emission_CO2+Thr+His+lactate+PO4.ferm.+PO4.apporte; 0.770, 0.899, tmp+Main.P-Source.Conc.+Nitrogen.Conc.+total.Vol+PL+emission_CO2+rab+His+lactate+PO4.ferm.+PO4.apporte; 0.770, 0.899, tmp+Main.P-Source.Conc.+Nitrogen.Conc.+total.Vol+PL+emission_O2+emission_CO2+His+lactate+PO4.apporte+PO4.utilise; 0.778, 0.899, Main.P-Source.Conc.+Nitrogen.Conc.+total.Vol+PL+emission_CO2+His+lactate+PO4.ferm.+PO4.apporte; 0.769, 0.899, tmp+Main.P-Source.Conc.+Nitrogen.Conc.+total.Vol+PL+emission_CO2+Thr+His+lactate+PO4.ferm.+PO4.apporte; 0.778, 0.899, Main.P-Source.Conc.+Nitrogen.Conc.+total.Vol+PL+emission_CO2+His+lactate+PO4.apporte+PO4.utilise; 0.765, 0.899, tmp+Main.P-Source.Conc.+Nitrogen.Conc.+total.Vol+PL+emission_O2+emission_CO2+Thr+His+lactate+PO4.apporte+PO4.utilise; 0.769, 0.899, tmp+Main.P-Source.Conc.+Nitrogen.Conc.+total.Vol+PL+emission_CO2+rab+His+lactate+PO4.apporte+PO4.utilise; 0.769, 0.899, tmp+Main.P-Source.Conc.+Nitrogen.Conc.+total.Vol+PL+emission_CO2+Thr+His+lactate+PO4.apporte+PO4.utilise; 0.781, 0.899, Main.P-Source.Conc.+Nitrogen.Conc.+total.Vol+PL+emission_CO2+His+lactate+PO4.apporte; 0.764, 0.899, tmp+Main.P-Source.Conc.+Nitrogen.Conc.+total.Vol+PL+emission_CO2+rab+Thr+His+lactate+PO4.ferm.+PO4.apporte; 0.764, 0.898, tmp+Main.P-Source.Conc.+Nitrogen.Conc.+total.Vol+PL+emission_CO2+rab+Thr+His+lactate+PO4.apporte+PO4.utilise; 0.775, 0.898, tmp+Main.P-Source.Conc.+Nitrogen.Conc.+total.Vol+PL+emission_CO2+His+lactate+PO4.apporte; 0.766, 0.898, pH+tmp+Main.P-Source.Conc.+Nitrogen.Conc.+total.Vol+PL+emission_CO2+His+lactate+PO4.ferm.+PO4.apporte; 0.770, 0.898, tmp+Main.P-Source.Conc.+Nitrogen.Conc.+total.Vol+emission_CO2+rab+His+lactate+PO4.ferm.+PO4.apporte; 0.770, 0.898, tmp+Main.P-Source.Conc.+Nitrogen.Conc.+total.Vol+emission_O2+emission_CO2+His+lactate+PO4.ferm.+PO4.apporte; 0.774, 0.897, pH+Main.P-Source.Conc.+Nitrogen.Conc.+total.Vol+PL+emission_CO2+His+lactate+PO4.apporte; 0.766, 0.897, pH+tmp+Main.P-Source.Conc.+Nitrogen.Conc.+total.Vol+PL+emission_CO2+His+lactate+PO4.apporte+PO4.utilise; 0.761, 0.897, pH+tmp+Main.P-Source.Conc.+Nitrogen.Conc.+total.Vol+PL+emission_O2+emission_CO2+His+lactate+PO4.ferm.+PO4.apporte; 0.756, 0.897, tmp+Main.P-Source.Conc.+P-Source.Feed.conc.+Nitrogen.Conc.+total.Vol+PL+emission_O2+emission_CO2+Thr+His+lactate+PO4.ferm.+PO4.apporte; 0.765, 0.897, tmp+Main.P-Source.Conc.+Nitrogen.Conc.+OD+total.Vol+PL+emission_CO2+His+lactate+PO4.ferm.+PO4.apporte; 0.769, 0.897, tmp+Main.P-Source.Conc.+Nitrogen.Conc.+total.Vol+emission_O2+emission_CO2+His+lactate+PO4.apporte+PO4.utilise; 0.769, 0.897, tmp+Main.P-Source.Conc.+Nitrogen.Conc.+total.Vol+emission_CO2+rab+His+lactate+PO4.apporte+PO4.utilise; 0.773, 0.897, Main.P-Source.Conc.+Nitrogen.Conc.+OD+total.Vol+PL+emission_CO2+His+lactate+PO4.apporte; 0.769, 0.897, pH+Main.P-Source.Conc.+Nitrogen.Conc.+total.Vol+PL+emission_CO2+His+lactate+PO4.ferm.+PO4.apporte; 0.760, 0.897, pH+tmp+Main.P-Source.Conc.+Nitrogen.Conc.+total.Vol+PL+emission_CO2+rab+His+lactate+PO4.ferm.+PO4.apporte; 0.765, 0.897, tmp+Main.P-Source.Conc.+Nitrogen.Conc.+total.Vol+PL+emission_O2+emission_CO2+Thr+lactate+PO4.ferm.+PO4.apporte; 0.769, 0.897, pH+Main.P-Source.Conc.+Nitrogen.Conc.+total.Vol+PL+emission_CO2+His+lactate+PO4.apporte+PO4.utilise; 0.773, 0.897, tmp+P-Source.Feed.conc.+PL+emission_CO2+Thr+His+lactate+PO4.apporte+PO4.utilise; 0.756, 0.897, tmp+Main.P-Source.Conc.+P-Source.Feed.conc.+Nitrogen.Conc.+total.Vol+PL+emission_O2+emission_CO2+Thr+His+lactate+PO4.apporte+PO4.utilise; 0.760, 0.897, pH+tmp+Main.P-Source.Conc.+Nitrogen.Conc.+total.Vol+PL+emission_O2+emission_CO2+His+lactate+PO4.apporte+PO4.utilise; 0.760, 0.897, pH+tmp+Main.P-Source.Conc.+Nitrogen.Conc.+total.Vol+PL+emission_CO2+Thr+His+lactate+PO4.ferm.+PO4.apporte; 0.764, 0.897, tmp+Main.P-Source.Conc.+Nitrogen.Conc.+OD+total.Vol+PL+emission_CO2+His+lactate+PO4.apporte+PO4.utilise; 0.773, 0.897, tmp+Main.P-Source.Conc.+Nitrogen.Conc.+total.Vol+emission_O2+emission_CO2+lactate+PO4.ferm.+PO4.apporte; 0.773, 0.897, tmp+Main.P-Source.Conc.+Nitrogen.Conc.+total.Vol+emission_CO2+rab+lactate+PO4.ferm.+PO4.apporte; 0.760, 0.897, tmp+Main.P-Source.Conc.+Nitrogen.Conc.+OD+total.Vol+PL+emission_O2+emission_CO2+His+lactate+PO4.ferm.+PO4.apporte; 0.769, 0.897, tmp+Main.P-Source.Conc.+Nitrogen.Conc.+OD+PL+emission_CO2+His+lactate+PO4.ferm.+PO4.apporte; 0.773, 0.897, tmp+P-Source.Feed.conc.+PL+emission_CO2+Thr+His+lactate+PO4.ferm.+PO4.apporte; 0.760, 0.897, pH+tmp+Main.P-Source.Conc.+Nitrogen.Conc.+total.Vol+PL+ emission_CO2+rab+His+lactate+PO4.apporte+PO4.utilise; 0.768, 0.897, tmp+Main.P-Source.Conc.+Nitrogen.Conc.+total.Vol+PL+emission_CO2+Thr+His+lactate+PO4.apporte; 0.773, 0.897, tmp+Main.P-Source.Conc.+Nitrogen.Conc.+total.Vol+emission_CO2+His+lactate+PO4.ferm.+PO4.apporte; 0.760, 0.897, pH+tmp+Main.P-Source.Conc.+Nitrogen.Conc.+total.Vol+PL+emission_CO2+Thr+His+lactate+PO4.apporte+PO4.utilise; 0.764, 0.897, tmp+Main.P-Source.Conc.+Nitrogen.Conc.+total.Vol+PL+emission_O2+emission_CO2+Thr+lactate+PO4.apporte+PO4.utilise; 0.755, 0.897, pH+tmp+Main.P-Source.Conc.+Nitrogen.Conc.+total.Vol+PL+emission_O2+emission_CO2+Thr+His+lactate+PO4.ferm.+PO4.apporte; 0.768, 0.897, Main.P-Source.Conc.+Nitrogen.Conc.+OD+total.Vol+PL+emission_CO2+His+lactate+PO4.ferm.+PO4.apporte; 0.764, 0.897, tmp+Main.P-Source.Conc.+Nitrogen.Conc.+total.Vol+yield+PL+emission_CO2+His+lactate+PO4.ferm.+PO4.apporte; 0.768, 0.897, tmp+Main.P-Source.Conc.+Nitrogen.Conc.+OD+PL+emission_CO2+His+lactate+PO4.apporte+PO4.utilise; 0.759, 0.897, tmp+Main.P-Source.Conc.+P-Source.Feed.conc.+Nitrogen.Conc.+total.Vol+PL+emission_CO2+Thr+His+lactate+PO4.ferm.+PO4.apporte; 0.772, 0.897, tmp+Main.P-Source.Conc.+Nitrogen.Conc.+OD+PL+emission_CO2+His+lactate+PO4.apporte; 0.776, 0.897, tmp+P-Source.Feed.conc.+PL+emission_CO2+Thr+His+lactate+PO4.apporte; 0.764, 0.897, tmp+Main.P-Source.Conc.+Nitrogen.Conc.+total.Vol+yield+PL+emission_CO2+His+lactate+PO4.apporte+PO4.utilise; 0.768, 0.897, Main.P-Source.Conc.+Nitrogen.Conc.+OD+total.Vol+PL+emission_CO2+His+lactate+PO4.apporte+PO4.utilise; 0.776, 0.897, Main.P-Source.Conc.+Nitrogen.Conc.+OD+PL+emission_CO2+His+lactate+PO4.apporte; 0.759, 0.897, tmp+Main.P-Source.Conc.+P-Source.Feed.conc.+Nitrogen.Conc.+total.Vol+PL+emission_CO2+Thr+His+lactate+PO4.apporte+PO4.utilise; 0.768, 0.896, pH+tmp+Main.P-Source.Conc.+Nitrogen.Conc.+total.Vol+PL+emission_CO2+His+lactate+PO4.apporte; 0.755, 0.896, tmp+Main.P-Source.Conc.+P-Source.Feed.conc.+Nitrogen.Conc.+total.Vol+PL+emission_CO2+rab+Thr+His+lactate+PO4.ferm.+PO4.apporte; 0.772, 0.896, tmp+P-Source.Feed.conc.+PL+emission_CO2+Thr+His+lactate+PO4.ferm.+PO4.utilise; 0.759, 0.896, tmp+Main.P-Source.Conc.+Nitrogen.Conc.+OD+total.Vol+PL+emission_O2+emission_CO2+His+lactate+PO4.apporte+PO4.utilise; 0.759, 0.896, tmp+Main.P-Source.Conc.+Nitrogen.Conc.+OD+total.Vol+PL+emission_CO2+rab+His+lactate+PO4.ferm.+PO4.apporte; 0.772, 0.896, tmp+Main.P-Source.Conc.+Nitrogen.Conc.+total.Vol+emission_O2+emission_CO2+lactate+PO4.apporte+PO4.utilise; 0.754, 0.896, pH+tmp+Main.P-Source.Conc.+Nitrogen.Conc.+total.Vol+PL+emission_O2+emission_CO2+Thr+His+lactate+PO4.apporte+PO4.utilise; 0.763, 0.896, tmp+Main.P-Source.Conc.+Main.Thr.Conc.+Nitrogen.Conc.+total.Vol+emission_O2+emission_CO2+His+lactate+PO4.ferm.+PO4.apporte; 0.772, 0.896, tmp+Main.P-Source.Conc.+Nitrogen.Conc.+total.Vol+emission_CO2+rab+lactate+PO4.apporte+PO4.utilise; 0.772, 0.896, tmp+Main.P-Source.Conc.+Nitrogen.Conc.+total.Vol+emission_CO2+His+lactate+PO4.apporte+PO4.utilise; 0.768, 0.896, tmp+Main.P-Source.Conc.+Main.Thr.Conc.+Nitrogen.Conc.+total.Vol+emission_O2+emission_CO2+lactate+PO4.ferm.+PO4.apporte; 0.763, 0.896, tmp+Main.P-Source.Conc.+Nitrogen.Conc.+total.Vol+PL+emission_CO2+rab+Thr+lactate+PO4.ferm.+PO4.apporte; 0.772, 0.896, Main.P-Source.Conc.+Nitrogen.Conc.+OD+yield+PL+emission_CO2+His+lactate+PO4.apporte; 0.754, 0.896, tmp+Main.P-Source.Conc.+P-Source.Feed.conc.+Nitrogen.Conc.+total.Vol+PL+emission_CO2+rab+Thr+His+lactate+PO4.apporte+PO4.utilise; 0.768, 0.896, Main.P-Source.Conc.+Nitrogen.Conc.+total.Vol+yield+PL+emission_CO2+His+lactate+PO4.ferm.+PO4.apporte; 0.763, 0.896, tmp+Main.P-Source.Conc.+Main.Thr.Conc.+Nitrogen.Conc.+total.Vol+emission_CO2+rab+His+lactate+PO4.ferm.+PO4.apporte; 0.768, 0.896, Main.P-Source.Conc.+Nitrogen.Conc.+total.Vol+yield+PL+emission_CO2+His+lactate+PO4.apporte+PO4.utilise; 0.767, 0.896, tmp+Main.P-Source.Conc.+Main.Thr.Conc.+Nitrogen.Conc.+total.Vol+emission_CO2+rab+lactate+PO4.ferm.+PO4.apporte; 0.759, 0.896, tmp+Main.P-Source.Conc.+Nitrogen.Conc.+total.Vol+yield+PL+emission_O2+emission_CO2+His+lactate+PO4.apporte+PO4.utilise; 0.759, 0.896, tmp+Main.P-Source.Conc.+Nitrogen.Conc.+total.Vol+yield+PL+emission_O2+emission_CO2+His+lactate+PO4.ferm.+PO4.apporte; 0.767, 0.896, tmp+Main.P-Source.Conc.+Nitrogen.Conc.+OD+yield+PL+emission_CO2+His+lactate+PO4.apporte; 0.767, 0.896, Main.P-Source.Conc.+Nitrogen.Conc.+total.Vol+PL+emission_CO2+Thr+His+lactate+PO4.ferm.+PO4.apporte; 0.763, 0.896, tmp+Main.P-Source.Conc.+Nitrogen.Conc.+OD+yield+PL+emission_CO2+His+lactate+PO4.apporte+PO4.utilise; 0.767, 0.896, tmp+Main.P-Source.Conc.+Main.Thr.Conc.+Nitrogen.Conc.+total.Vol+emission_O2+emission_CO2+lactate+PO4.apporte+PO4.utilise; 0.763, 0.896, tmp+Main.P-Source.Conc.+Nitrogen.Conc.+OD+yield+PL+emission_CO2+His+lactate+PO4.ferm.+PO4.apporte; 0.767, 0.896, Main.P-Source.Conc.+P-Source.Feed.conc.+Nitrogen.Conc.+total.Vol+PL+emission_CO2+His+lactate+PO4.ferm.+PO4.apporte; 0.763, 0.896, tmp+Main.P-Source.Conc.+Main.Thr.Conc.+Nitrogen.Conc.+total.Vol+emission_O2+emission_CO2+His+lactate+PO4.apporte+PO4.utilise; 0.758, 0.896, tmp+Main.P-Source.Conc.+P-Source.Feed.conc.+Nitrogen.Conc.+PL+emission_O2+emission_CO2+Thr+His+lactate+PO4.apporte+PO4.utilise; 0.758, 0.896, tmp+Main.P-Source.Conc.+Nitrogen.Conc.+OD+total.Vol+PL+emission_CO2+Thr+His+lactate+PO4.ferm.+PO4.apporte; 0.754, 0.896, pH+tmp+Main.P-Source.Conc.+Nitrogen.Conc.+total.Vol+PL+emission_CO2+rab+Thr+His+lactate+PO4.ferm.+PO4.apporte; 0.767, 0.896, tmp+Main.P-Source.Conc.+Nitrogen.Conc.+total.Vol+PL+emission_CO2+His+lactate+PO4.ferm.+PO4.utilise; 0.767, 0.896, Main.P-Source.Conc.+Nitrogen.Conc.+total.Vol+PL+emission_CO2+Thr+His+lactate+PO4.apporte+PO4.utilise; 0.758, 0.896, tmp+Main.P-Source.Conc.+Nitrogen.Conc.+OD+total.Vol+PL+emission_CO2+rab+His+lactate+PO4.apporte+PO4.utilise; 0.767, 0.896, tmp+Main.P-Source.Conc.+Nitrogen.Conc.+OD+total.Vol+PL+emission_CO2+His+lactate+PO4.apporte; 0.758, 0.896, tmp+Main.P-Source.Conc.+P-Source.Feed.conc.+Nitrogen.Conc.+PL+emission_O2+emission_CO2+Thr+His+lactate+PO4.ferm.+PO4.apporte; 0.767, 0.896, tmp+Main.P-Source.Conc.+Main.Thr.Conc.+Nitrogen.Conc.+total.Vol+emission_CO2+rab+lactate+PO4.apporte+PO4.utilise; 0.767, 0.896, tmp+Main.P-Source.Conc.+Nitrogen.Conc.+total.Vol+emission_O2+emission_CO2+Thr+lactate+PO4.ferm.+PO4.apporte; 0.758, 0.896, tmp+Main.P-Source.Conc.+Nitrogen.Conc.+total.Vol+yield+PL+emission_CO2+Thr+His+lactate+PO4.ferm.+PO4.apporte; 0.763, 0.896, tmp+Main.P-Source.Conc.+Main.Thr.Conc.+Nitrogen.Conc.+total.Vol+ emission_CO2+rab+His+lactate+PO4.apporte+PO4.utilise; 0.754, 0.896, tmp+Main.P-Source.Conc.+Nitrogen.Conc.+ OD+total.Vol+PL+emission_O2+emission_CO2+Thr+His+ lactate+PO4.ferm.+PO4.apporte; 0.767, 0.896, tmp+ Main.P-Source.Conc.+Nitrogen.Conc.+total.Vol+PL+ emission_O2+emission_CO2+lactate+PO4.ferm.+ PO4.apporte; 0.763, 0.896, tmp+Main.P-Source.Conc.+ Nitrogen.Conc.+total.Vol+PL+emission_CO2+rab+Thr+ lactate+PO4.apporte+PO4.utilise; 0.758, 0.896, tmp+ Main.P-Source.Conc.+P-Source.Feed.conc.+ Nitrogen.Conc.+PL+emission_CO2+rab+Thr+His+lactate+ PO4.apporte+PO4.utilise; 0.758, 0.896, tmp+Main.P-Source.Conc.+Nitrogen.Conc.+total.Vol+yield+PL+ emission_CO2+Thr+His+lactate+PO4.apporte+PO4.utilise; 0.767, 0.896, Main.P-Source.Conc.+P-Source.Feed.conc.+ Nitrogen.Conc.+total.Vol+PL+emission_CO2+His+lactate+ PO4.apporte+PO4.utilise; 0.758, 0.896, tmp+Main.P-Source.Conc.+Main.Thr.Conc.+Nitrogen.Conc.+total.Vol+ PL+emission_O2+emission_CO2+His+lactate+PO4.ferm.+ PO4.apporte; 0.758, 0.896, tmp+Main.P-Source.Conc.+P-Source.Feed.conc.+Nitrogen.Conc.+PL+emission_CO2+ rab+Thr+His+lactate+PO4.ferm.+PO4.apporte; 0.758, 0.896, tmp+Main.P-Source.Conc.+Nitrogen.Conc.+total. Vol+yield+PL+emission_CO2+rab+His+lactate+ PO4.apporte+PO4.utilise; 0.758, 0.896, tmp+Main.P-Source.Conc.+Nitrogen.Conc.+total.Vol+yield+PL+emission_CO2+rab+His+lactate+PO4.ferm.+PO4.apporte; 0.758, 0.896, tmp+Main.P-Source.Conc.+Nitrogen.Conc.+ OD+total.Vol+PL+emission_CO2+Thr+His+lactate+ PO4.apporte+PO4.utilise; 0.758, 0.896, tmp+Main.P-Source.Conc.+P-Source.Feed.conc.+Nitrogen.Conc.+ total.Vol+PL+emission_O2+emission_CO2+His+lactate+ PO4.ferm.+PO4.apporte; 0.753, 0.896, tmp+Main.P-Source.Conc.+Nitrogen.Conc.+total.Vol+PL+ emission_O2+emission_CO2+rab+Thr+His+lactate+ PO4.ferm.+PO4.apporte; 0.762, 0.896, tmp+Main.P-Source.Conc.+P-Source.Feed.conc.+Nitrogen.Conc.+PL+ emission_CO2+Thr+His+lactate+PO4.apporte+PO4.utilise; 0.758, 0.896, tmp+Main.P-Source.Conc.+Nitrogen.Conc.+ Lys_conc.+total.Vol+PL+emission_O2+emission_CO2+ His+lactate+PO4.ferm.+PO4.apporte; 0.767, 0.896, Main.P-Source.Conc.+Nitrogen.Conc.+total.Vol+PL+ emission_O2+emission_CO2+His+lactate+PO4.ferm.+ PO4.apporte; 0.775, 0.896, tmp+Main.P-Source.Conc.+ Nitrogen.Conc.+total.Vol+emission_CO2+His+lactate+ PO4.apporte; 0.758, 0.896, tmp+Main.P-Source.Conc.+ Main.Thr.Conc.+Nitrogen.Conc.+total.Vol+PL+ emission_O2+emission_CO2+His+lactate+PO4.apporte+ PO4.utilise; 0.753, 0.896, pH+tmp+Main.P-Source.Conc.+ Nitrogen.Conc.+total.Vol+PL+emission_CO2+rab+Thr+ His+lactate+PO4.apporte+PO4.utilise; 0.767, 0.896, tmp+ Main.P-Source.Conc.+Nitrogen.Conc.+total.Vol+PL+ emission_CO2+rab+lactate+PO4.ferm.+PO4.apporte; 0.758, 0.896, tmp+Main.P-Source.Conc.+Nitrogen.Conc.+ total.Vol+PL+emission_O2+emission_CO2+His+lactate+ SO4.ferm.+PO4.ferm.+PO4.apporte; 0.762, 0.896, tmp+ Main.P-Source.Conc.+P-Source.Feed.conc.+ Nitrogen.Conc.+total.Vol+PL+emission_CO2+His+lactate+ PO4.ferm.+PO4.apporte; 0.762, 0.896, tmp+Main.P-Source.Conc.+P-Source.Feed.conc.+Nitrogen.Conc.+PL+ emission_CO2+Thr+His+lactate+PO4.ferm.+PO4.apporte; 0.767, 0.896, tmp+P-Source.Feed.conc.+PL+emission_O2+ emission_CO2+Thr+His+lactate+PO4.apporte+PO4.utilise; 0.753, 0.896, tmp+Main.P-Source.Conc.+Nitrogen.Conc.+ Lys_conc.+total.Vol+PL+emission_O2+emission_CO2+ Thr+His+lactate+PO4.ferm.+PO4.apporte; 0.758, 0.896, tmp+Main.P-Source.Conc.+P-Source.Feed.conc.+ Nitrogen.Conc.+total.Vol+PL+emission_CO2+rab+His+ lactate+PO4.ferm.+PO4.apporte; 0.762, 0.896, tmp+ Main.P-Source.Conc.+Nitrogen.Conc.+total.Vol+emission_O2+emission_CO2+Thr+His+lactate+PO4.ferm.+ PO4.apporte; 0.753, 0.896, tmp+Main.P-Source.Conc.+ Nitrogen.Conc.+OD+total.Vol+PL+emission_O2+ emission_CO2+Thr+His+lactate+PO4.apporte+PO4.utilise; 0.766, 0.896, Main.P-Source.Conc.+Nitrogen.Conc.+total. Vol+PL+emission_O2+emission_CO2+His+lactate+ PO4.apporte+PO4.utilise; 0.770, 0.896, Main.P-Source.Conc.+Nitrogen.Conc.+total.Vol+yield+PL+emission_CO2+His+lactate+PO4.apporte; 0.757, 0.896, tmp+ Main.P-Source.Conc.+Nitrogen.Conc.+total.Vol+PL+ emission_CO2+rab+His+lactate+SO4.ferm.+PO4.ferm.+ PO4.apporte; 0.753, 0.896, tmp+Main.P-Source.Conc.+ Nitrogen.Conc.+total.Vol+PL+emission_O2+ emission_CO2+rab+Thr+His+lactate+PO4.apporte+ PO4.utilise; 0.766, 0.896, tmp+Main.P-Source.Conc.+ Nitrogen.Conc.+total. Vol+PL+emission_O2+ emission_CO2+lactate+PO4.apporte+PO4.utilise; 0.757, 0.896, tmp+Main.P-Source.Conc.+Main.Thr.Conc.+Nitrogen.Conc.+total.Vol+PL+emission_CO2+rab+His+lactate+ PO4.ferm.+PO4.apporte; 0.757, 0.896, tmp+Main.P-Source.Conc.+P-Source.Feed.conc.+Nitrogen.Conc.+ total.Vol+PL+emission_O2+emission_CO2+His+lactate+ PO4.apporte+PO4.utilise; 0.766, 0.896, pH+Main.P-Source.Conc.+Nitrogen.Conc.+OD+total.Vol+PL+ emission_CO2+His+lactate+PO4.apporte; 0.753, 0.896, tmp+Main.P-Source.Conc.+Nitrogen.Conc.+total.Vol+PL+ emission_O2+emission_CO2+Thr+His+lactate+ SO4.ferm.+PO4.ferm.+PO4.apporte; 0.762, 0.896, tmp+ Main.P-Source.Conc.+P-Source.Feed.conc.+ Nitrogen.Conc.+total.Vol+PL+emission_CO2+His+lactate+ PO4.apporte+PO4.utilise; 0.762, 0.896, tmp+Main.P-Source.Conc.+Nitrogen.Conc.+total.Vol+PL+ emission_CO2+His+lactate+SO4.ferm.+PO4.ferm.+ PO4.apporte; 0.766, 0.896, tmp+Main.P-Source.Conc.+ Nitrogen.Conc.+total.Vol+emission_CO2+rab+Thr+ lactate+PO4.ferm.+PO4.apporte; 0.766, 0.896, tmp+ Main.P-Source.Conc.+Nitrogen.Conc.+total.Vol+ emission_O2+emission_CO2+Thr+lactate+PO4.apporte+ PO4.utilise; 0.753, 0.896, tmp+Main.P-Source.Conc.+ Nitrogen.Conc.+total.Vol+yield+PL+emission_O2+ emission_CO2+Thr+His+lactate+PO4.apporte+PO4.utilise; 0.762, 0.896, tmp+Main.P-Source.Conc.+Nitrogen.Conc.+ OD+PL+emission_O2+emission_CO2+His+lactate+ PO4.ferm.+PO4.apporte; 0.757, 0.896, tmp+Main.P-Source.Conc.+Nitrogen.Conc.+total.Vol+PL+ emission_O2+emission_CO2+His+lactate+SO4.ferm.+ PO4.apporte+PO4.utilise; 0.757, 0.896, tmp+Main.P-Source.Conc.+Nitrogen.Conc.+OD+yield+PL+ emission_O2+emission_CO2+His+lactate+PO4.apporte+ PO4.utilise; 0.757, 0.896, tmp+Main.P-Source.Conc.+ Main.Thr.Conc.+Nitrogen.Conc.+total.Vol+PL+ emission_CO2+rab+His+lactate+PO4.apporte+PO4.utilise; 0.766, 0.895, tmp+Main.P-Source.Conc.+Nitrogen.Conc.+ total.Vol+PL+emission_CO2+rab+lactate+PO4.apporte+ PO4.utilise; 0.757, 0.895, tmp+Main.P-Source.Conc.+P-Source.Feed.conc.+Nitrogen.Conc.+total.Vol+PL+ emission_CO2+rab+His+lactate+PO4.apporte+PO4.utilise; 0.761, 0.895, tmp+Main.P-Source.Conc.+Nitrogen.Conc.+ OD+PL+emission_CO2+Thr+His+lactate+PO4.ferm.+ PO4.apporte; 0.761, 0.895, tmp+Main.P-Source.Conc.+Nitrogen.Conc.+OD+PL+emission_CO2+rab+His+lactate+ PO4.ferm.+PO4.apporte; 0.766, 0.895, tmp+P-Source.Feed.conc.+PL+emission_O2+emission_CO2+Thr+ His+lactate+PO4.ferm.+PO4.apporte; 0.761, 0.895, tmp+

Main.P-Source.Conc.+Nitrogen.Conc.+total.Vol+PL+emission_CO2+His+lactate+SO4.ferm.+PO4.apporte+PO4.utilise; 0.766, 0.895, tmp+Main.P-Source.Conc.+Nitrogen.Conc.+total.Vol+PL+emission_CO2+Thr+lactate+PO4.ferm.+PO4.apporte; 0.766, 0.895, tmp+Main.P-Source.Conc.+Nitrogen.Conc.+total.Vol+PL+emission_O2+emission_CO2+His+lactate+PO4.apporte; 0.752, 0.895, tmp+Main.P-Source.Conc.+Nitrogen.Conc.+total.Vol+yield+PL+emission_O2+emission_CO2+Thr+His+lactate+PO4.ferm.+PO4.apporte; 0.757, 0.895, tmp+Main.P-Source.Conc.+Nitrogen.Conc.+Lys_conc.+total.Vol+PL+emission_O2+emission_CO2+His+lactate+PO4.apporte+PO4.utilise; 0.757, 0.895, tmp+Main.P-Source.Conc.+Nitrogen.Conc.+total.Vol+PL+emission_CO2+rab+His+lactate+SO4.ferm.+PO4.apporte+PO4.utilise; 0.766, 0.895, Main.P-Source.Conc.+Nitrogen.Conc.+total.Vol+PL+emission_CO2+rab+His+lactate+PO4.ferm.+PO4.apporte; 0.752, 0.895, tmp+Main.P-Source.Conc.+Nitrogen.Conc.+total.Vol+PL+emission_O2+emission_CO2+Thr+His+lactate+SO4.ferm.+PO4.apporte+PO4.utilise; 0.757, 0.895, tmp+Main.P-Source.Conc.+Nitrogen.Conc.+OD+yield+PL+emission_O2+emission_CO2+His+lactate+PO4.ferm.+PO4.apporte; 0.766, 0.895, tmp+Main.P-Source.Conc.+Nitrogen.Conc.+total.Vol+PL+emission_CO2+rab+His+lactate+PO4.apporte; 0.752, 0.895, tmp+Main.P-Source.Conc.+Nitrogen.Conc.+Lys_conc.+total.Vol+PL+emission_O2+emission_CO2+Thr+His+lactate+PO4.apporte+PO4.utilise; 0.761, 0.895, tmp+Main.P-Source.Conc.+Nitrogen.Conc.+total.Vol+emission_CO2+rab+Thr+His+lactate+PO4.ferm.+PO4.apporte; 0.766, 0.895, pH+tmp+Main.P-Source.Conc.+Nitrogen.Conc.+OD+PL emission_CO2+His+lactate+PO4.apporte; 0.757, 0.895, tmp+Main.P-Source.Conc.+Nitrogen.Conc.+OD+yield+PL+emission_CO2+rab+His+lactate+PO4.apporte+PO4.utilise; 0.761, 0.895, tmp+Main.P-Source.Conc.+Nitrogen.Conc.+total.Vol+PL+emission_O2+emission_CO2+His+lactate+PO4.ferm.+PO4.utilise; 0.757, 0.895, tmp+Main.P-Source.Conc.+Nitrogen.Conc.+Lys_conc.+total.Vol+PL+emission_CO2+rab+His+lactate+PO4.ferm.+PO4.apporte; 0.770, 0.895, Main.P-Source.Conc.+Nitrogen.Conc.+total.Vol+PL+emission_CO2+Thr+His+lactate+PO4.apporte; 0.761, 0.895, tmp+Main.P-Source.Conc.+Nitrogen.Conc.+OD+PL+emission_CO2+Thr+His+lactate+PO4.apporte+PO4.utilise; 0.757, 0.895, tmp+Main.P-Source.Conc.+Nitrogen.Conc.+total.Vol+PL+emission_O2+emission_CO2+rab+His+lactate+PO4.ferm.+PO4.apporte; 0.778, 0.895, Main.P-Source.Conc.+Nitrogen.Conc.+total.Vol+emission_CO2+His+lactate+PO4.apporte; 0.761, 0.895, tmp+Main.P-Source.Conc.+Nitrogen.Conc.+OD+PL+emission_O2+emission_CO2+His+lactate+PO4.apporte+PO4.utilise; 0.757, 0.895, pH+tmp+Main.P-Source.Conc.+Nitrogen.Conc.+OD+total.Vol+PL+emission_CO2+His+lactate+PO4.ferm.+PO4.apporte; 0.752, 0.895, tmp+Main.P-Source.Conc.+Nitrogen.Conc.+OD+total.Vol+PL+emission_CO2+rab+Thr+His+lactate+PO4.ferm.+PO4.apporte; 0.765, 0.895, tmp+P-Source.Feed.conc.+PL+emission_CO2+rab+Thr+His+lactate+PO4.apporte+PO4.utilise; 0.761, 0.895, tmp+Main.P-Source.Conc.+Nitrogen.Conc.+total.Vol+PL+emission_CO2+rab+His+lactate+PO4.ferm.+PO4.utilise; 0.765, 0.895, Main.P-Source.Conc.+Nitrogen.Conc.+total.Vol+PL+emission_CO2+rab+His+lactate+PO4.apporte+PO4.utilise; 0.777, 0.895, tmp+Main.P-Source.Conc.+Nitrogen.Conc.+total.Vol+emission_CO2+lactate+PO4.apporte; 0.761, 0.895, tmp+Main.P-Source.Conc.+Nitrogen.Conc.+total.Vol+emission_O2+emission_CO2+Thr+His+lactate+PO4.apporte+PO4.utilise; 0.765, 0.895, tmp+Main.P-Source.Conc.+Nitrogen.Conc.+total.Vol+PL+emission_CO2+Thr+lactate+PO4.apporte+PO4.utilise; 0.770, 0.895, Main.P-Source.Conc.+Nitrogen.Conc.+OD+PL+emission_CO2+His+lactate+PO4.ferm.+PO4.apporte; 0.756, 0.895, tmp+Main.P-Source.Conc.+Nitrogen.Conc.+OD+yield+PL+emission_CO2+rab+His+lactate+PO4.ferm.+PO4.apporte; 0.770, 0.895, tmp+Main.P-Source.Conc.+Main.Thr.Conc.+Nitrogen.Conc.+emission_CO2+rab+lactate+PO4.apporte+PO4.utilise; 0.761, 0.895, tmp+Main.P-Source.Conc.+Nitrogen.Conc.+OD+total.Vol+emission_CO2+rab+His+lactate+PO4.ferm.+PO4.apporte; 0.761, 0.895, tmp+Main.P-Source.Conc.+Nitrogen.Conc.+OD+total.Vol+emission_O2+emission_CO2+His+lactate+PO4.ferm.+PO4.apporte; 0.761, 0.895, tmp+Main.P-Source.Conc.+Nitrogen.Conc.+OD+PL+emission_CO2+rab+His+lactate+PO4.apporte+PO4.utilise; 0.769, 0.895, Main.P-Source.Conc.+Nitrogen.Conc.+total.Vol+PL+emission_O2+emission_CO2+His+lactate+PO4.apporte; 0.769, 0.895, tmp+Main.P-Source.Conc.+Main.Thr.Conc.+Nitrogen.Conc.+emission_CO2+rab+lactate+PO4.ferm.+PO4.apporte; 0.756, 0.895, tmp+Main.P-Source.Conc.+Nitrogen.Conc.+total.Vol+PL+emission_CO2+Thr+His+lactate+SO4.ferm.+PO4.ferm.+PO4.apporte; 0.769, 0.895, Main.P-Source.Conc.+Nitrogen.Conc.+OD+PL+emission_CO2+His+lactate+PO4.apporte+PO4.utilise; 0.765, 0.895, Main.P-Source.Conc.+Main.Thr.Conc.+Nitrogen.Conc.+total.Vol+PL+emission_CO2+His+lactate+PO4.ferm.+PO4.apporte; 0.765, 0.895, tmp+Main.P-Source.Conc.+Nitrogen.Conc.+total.Vol+emission_CO2+rab+Thr+lactate+PO4.apporte+PO4.utilise; 0.777, 0.895, Main.P-Source.Conc.+Nitrogen.Conc.+total.Vol+PL+emission_CO2+lactate+PO4.apporte; 0.773, 0.895, tmp+Main.P-Source.Conc.+Nitrogen.Conc.+total.Vol+emission_CO2+lactate+PO4.ferm.+PO4.apporte; 0.769, 0.895, pH+Main.P-Source.Conc.+Nitrogen.Conc.+OD+PL+emission_CO2+His+lactate+PO4.apporte; 0.761, 0.895, pH+tmp+Main.P-Source.Conc.+Nitrogen.Conc.+OD+yield+PL+emission_CO2+His+lactate+PO4.apporte; 0.769, 0.895, Main.P-Source.Conc.+P-Source.Feed.conc.+Nitrogen.Conc.+total.Vol+PL+emission_CO2+His+lactate+PO4.apporte; 0.756, 0.895, pH+tmp+Main.P-Source.Conc.+Nitrogen.Conc.+OD+total.Vol+PL+emission_CO2+His+lactate+PO4.apporte+PO4.utilise; 0.765, 0.895, tmp+Main.P-Source.Conc.+P-Source.Feed.conc.+Nitrogen.Conc.+PL+emission_CO2+Thr+His+lactate+PO4.apporte; 0.761, 0.895, pH+tmp+Main.P-Source.Conc.+Nitrogen.Conc.+OD+PL+emission_CO2+His+lactate+PO4.ferm.+PO4.apporte; 0.781, 0.895, Main.P-Source.Conc.+Nitrogen.Conc.+total.Vol+emission_CO2+lactate+PO4.apporte; 0.751, 0.895, tmp+Main.P-Source.Conc.+Nitrogen.Conc.+total.Vol+PL+emission_CO2+rab+Thr+His+lactate+SO4.ferm.+PO4.ferm.+PO4.apporte; 0.765, 0.895, tmp+P-Source.Feed.conc.+PL+emission_O2+emission_CO2+Thr+His+lactate+PO4.ferm.+PO4.utilise; 0.765, 0.895, Main.P-Source.Conc.+Main.Thr.Conc.+Nitrogen.Conc.+total.Vol+PL+emission_CO2+His+lactate+PO4.apporte+PO4.utilise; 0.756, 0.895, tmp+Main.P-Source.Conc.+Nitrogen.Conc.+total.Vol+PL+emission_O2+emission_CO2+rab+His+lactate+PO4.apporte+PO4.utilise; 0.756, 0.895, tmp+Main.P-Source.Conc.+Nitrogen.Conc.+total.Vol+PL+emission_CO2+Thr+His+lactate+SO4.ferm.+PO4.apporte+PO4.utilise; 0.751, 0.895, tmp+Main.P-Source.Conc.+Nitrogen.Conc.+OD+total.Vol+PL+emission_CO2+rab+Thr+His+lactate+PO4.apporte+PO4.utilise; 0.769, 0.895, Main.P-Source.Conc.+Nitrogen.Conc.+total.Vol+PL+emission_CO2+His+lactate+PO4.ferm.+PO4.utilise; 0.765, 0.895, Main.P-Source.Conc.+Nitrogen.Conc.+OD+yield+PL+emission_CO2+His+lactate+PO4.apporte+PO4.utilise; 0.751, 0.895, tmp+Main.P-Source.Conc.+Nitrogen.Conc.+total.Vol+yield+PL+emission_CO2+rab+Thr+His+lactate+PO4.apporte+PO4.utilise; 0.765, 0.895, tmp+P-Source.Feed.conc.+PL+emission_CO2+rab+Thr+His+lactate+PO4.ferm.+PO4.apporte; 0.765, 0.895, Main.P-Source.Conc.+Nitrogen.Conc.+OD+yield+PL+emission_CO2+His+lactate+PO4.ferm.+PO4.apporte; 0.760, 0.895, pH+tmp+Main.P-Source.Conc.+Nitrogen.Conc.+total.Vol+PL+emission_CO2+Thr+His+lactate+PO4.apporte; 0.765, 0.895, pH+Main.P-Source.Conc.+Nitrogen.Conc.+OD+yield+PL+emission_CO2+His+lactate+PO4.apporte; 0.760, 0.895, pH+tmp+Main.P-Source.Conc.+Nitrogen.Conc.+OD+PL+emission_CO2+His+lactate+PO4.apporte+PO4.utilise; 0.751, 0.895, tmp+Main.P-Source.Conc.+Nitrogen.Conc.+total.Vol+yield+PL+emission_CO2+rab+Thr+His+lactate+PO4.ferm.+PO4.apporte; 0.760, 0.895, tmp+Main.P-Source.Conc.+Nitrogen.Conc.+total.Vol+emission_CO2+rab+Thr+His+lactate+PO4.apporte+PO4.utilise; 0.756, 0.895, tmp+Main.P-Source.Conc.+Nitrogen.Conc.+Lys_conc.+total.Vol+PL+emission_CO2+rab+His+lactate+PO4.apporte+PO4.utilise; 0.760, 0.895, pH+tmp+Main.P-Source.Conc.+Nitrogen.Conc.+total.Vol+emission_CO2+rab+His+lactate+PO4.ferm.+PO4.apporte; 0.760, 0.895, tmp+Main.P-Source.Conc.+Nitrogen.Conc.+OD+total.Vol+emission_CO2+rab+His+lactate+PO4.apporte+PO4.utilise; 0.773, 0.895, tmp+Main.P-Source.Conc.+Nitrogen.Conc.+total.Vol+emission_CO2+lactate+PO4.apporte+PO4.utilise; 0.760, 0.895, pH+tmp+Main.P-Source.Conc.+Nitrogen.Conc.+OD+total.Vol+PL+emission_CO2+His+lactate+PO4.apporte; 0.760, 0.895, tmp+Main.P-Source.Conc.+Nitrogen.Conc.+OD+total.Vol+emission_O2+emission_CO2+His+lactate+PO4.apporte+PO4.utilise; 0.751, 0.895, tmp+Main.P-Source.Conc.+Nitrogen.Conc.+Lys_conc.+total.Vol+PL+emission_CO2+rab+Thr+His+lactate+PO4.ferm.+PO4.apporte; 0.751, 0.895, tmp+Main.P-Source.Conc.+Nitrogen.Conc.+total.Vol+PL+emission_CO2+rab+Thr+His+lactate+SO4.ferm.+PO4.apporte+PO4.utilise; 0.760, 0.895, pH+Main.P-Source.Conc.+Nitrogen.Conc.+OD+total.Vol+PL+emission_CO2+His+lactate+PO4.ferm.+PO4.apporte; 0.764, 0.895, tmp+Main.P-Source.Conc.+Nitrogen.Conc.+OD+PL+emission_CO2+Thr+His+lactate+PO4.apporte; 0.760, 0.895, tmp+Main.P-Source.Conc.+Nitrogen.Conc.+total.Vol+PL+emission_CO2+Thr+His+lactate+PO4.ferm.+PO4.utilise; 0.769, 0.895, Main.P-Source.Conc.+Nitrogen.Conc.+total.Vol+PL+emission_CO2+rab+His+lactate+PO4.apporte; 0.760, 0.895, pH+tmp+Main.P-Source.Conc.+Nitrogen.Conc.+total.Vol+emission_O2+emission_CO2+His+lactate+PO4.ferm.+PO4.apporte; 0.768, 0.895, tmp+Main.P-Source.Conc.+Nitrogen.Conc.+total.Vol+PL+emission_CO2+lactate+PO4.ferm.+PO4.apporte; 0.768, 0.895, pH+tmp+P-Source.Feed.conc.+PL+emission_CO2+Thr+His+lactate+PO4.apporte; 0.760, 0.895, tmp+Main.P-Source.Conc.+Nitrogen.Conc.+total.Vol+PL+emission_O2+rab+His+lactate+PO4.ferm.+PO4.apporte; 0.760, 0.895, tmp+Main.P-Source.Conc.+P-Source.Feed.conc.+Nitrogen.Conc.+total.Vol+PL+emission_CO2+Thr+His+lactate+PO4.apporte; 0.768, 0.895, tmp+Main.P-Source.Conc.+Main.Thr.Conc.+Nitrogen.Conc.+emission_O2+emission_CO2+lactate+PO4.apporte+PO4.utilise; 0.755, 0.895, pH+tmp+Main.P-Source.Conc.+Nitrogen.Conc.+total.Vol+yield+PL+emission_CO2+His+lactate+PO4.ferm.+PO4.apporte; 0.764, 0.895, Main.P-Source.Conc.+Nitrogen.Conc.+OD+total.Vol+yield+PL+emission_CO2+His+lactate+PO4.apporte; 0.760, 0.895, tmp+Main.P-Source.Conc.+Main.Thr.Conc.+Nitrogen.Conc.+total.Vol+PL+emission_CO2+His+lactate+PO4.ferm.+PO4.apporte; 0.760, 0.895, pH+Main.P-Source.Conc.+Nitrogen.Conc.+OD+total.Vol+PL+emission_CO2+His+lactate+PO4.apporte+PO4.utilise; 0.772, 0.895, Main.P-Source.Conc.+Nitrogen.Conc.+total.Vol+emission_CO2+His+lactate+PO4.ferm.+PO4.apporte; 0.768, 0.895, tmp+Main.P-Source.Conc.+Nitrogen.Conc.+total.Vol+emission_CO2+His+lactate+PO4.ferm.+PO4.utilise; 0.768, 0.895, tmp+Main.P-Source.Conc.+Main.Thr.Conc.+Nitrogen.Conc.+emission_O2+emission_CO2+lactate+PO4.ferm.+PO4.apporte; 0.750, 0.895, pH+tmp+Main.P-Source.Conc.+Nitrogen.Conc.+OD+total.Vol+PL+emission_O2+emission_CO2+His+lactate+PO4.ferm.+PO4.apporte; 0.764, 0.895, tmp+P-Source.Feed.conc.+PL+emission_CO2+rab+Thr+His+lactate+PO4.ferm.+PO4.utilise; 0.760, 0.895, tmp+Main.P-Source.Conc.+Nitrogen.Conc.+Lys_conc.+total.Vol+PL+emission_CO2+His+lactate+PO4.ferm.+PO4.apporte; 0.750, 0.895, tmp+Main.P-Source.Conc.+Nitrogen.Conc.+OD+Lys_conc.+total.Vol+PL+emission_O2+emission_CO2+His+lactate+PO4.ferm.+PO4.apporte; 0.755, 0.895, pH+tmp+Main.P-Source.Conc.+Nitrogen.Conc.+total.Vol+yield+PL+emission_CO2+His+lactate+PO4.apporte+PO4.utilise; 0.768, 0.895, tmp+Main.P-Source.Conc.+Nitrogen.Conc.+total.Vol+PL+emission_CO2+lactate+PO4.apporte+PO4.utilise; 0.772, 0.895, tmp+Main.P-Source.Conc.+Nitrogen.Conc.+total.Vol+emission_CO2+rab+lactate+PO4.apporte; 0.750, 0.895, tmp+Main.P-Source.Conc.+Main.Thr.Conc.+Nitrogen.Conc.+total.Vol+PL+emission_O2+emission_CO2+Thr+His+lactate+PO4.ferm.+PO4.apporte; 0.764, 0.895, tmp+Main.P-Source.Conc.+Nitrogen.Conc.+OD+total.Vol+emission_CO2+rab+lactate+PO4.ferm.+PO4.apporte; 0.764, 0.894, tmp+Main.P-Source.Conc.+Nitrogen.Conc.+total.Vol+emission_CO2+Thr+His+lactate+PO4.ferm.+PO4.apporte; 0.764, 0.894, tmp+Main.P-Source.Conc.+Nitrogen.Conc.+total.Vol+yield+PL+emission_CO2+His+lactate+PO4.apporte; 0.764, 0.894, tmp+Main.P-Source.Conc.+Nitrogen.Conc.+OD+total.Vol+emission_O2+emission_CO2+lactate+PO4.ferm.+PO4.apporte; 0.764, 0.894, tmp+Main.P-Source.Conc.+Nitrogen.Conc.+total.Vol+emission_CO2+rab+His+lactate+PO4.ferm.+PO4.utilise; 0.759, 0.894, tmp+Main.P-Source.Conc.+Nitrogen.Conc.+total.Vol+PL+emission_O2+emission_CO2+Thr+His+lactate+PO4.apporte; 0.759, 0.894, tmp+Main.P-Source.Conc.+Nitrogen.Conc.+OD+total.Vol+PL+emission_CO2+Thr+His+lactate+PO4.apporte; 0.759, 0.894, tmp+Main.P-Source.Conc.+Main.Thr.Conc.+Nitrogen.Conc.+total.Vol+PL+emission_CO2+His+lactate+PO4.apporte+PO4.utilise; 0.759, 0.894, tmp+Main.P-Source.Conc.+Nitrogen.Conc.+total.Vol+PL+emission_O2+rab+His+lactate+PO4.apporte+PO4.utilise; 0.755, 0.894, tmp+Main.P-Source.Conc.+Nitrogen.Conc.+OD+total.Vol+yield+PL+emission_CO2+His+lactate+PO4.ferm.+PO4.apporte; 0.772, 0.894, tmp+Main.P-Source.Conc.+Nitrogen.Conc.+total.Vol+emission_O2+emission_CO2+lactate+PO4.apporte; 0.764, 0.894, tmp+P-Source.Feed.conc.+total.Vol+PL+emission_CO2+Thr+His+lactate+PO4.apporte+PO4.utilise; 0.755, 0.894, tmp+Main.P-Source.Conc.+Nitrogen.Conc.+OD+PL+emission_O2+emission_CO2+Thr+His+lactate+PO4.ferm.+PO4.apporte; 0.763, 0.894, tmp+Main.P-Source.Conc.+Nitrogen.Conc.+total.Vol+emission_O2+ emission_CO2+His+lactate+PO4.ferm.+PO4.utilise; 0.750, 0.894, tmp+Main.P-Source.Conc.+Nitrogen.Conc.+Lys_conc.+total.Vol+PL+emission_CO2+rab+Thr+His+lactate+PO4.apporte+PO4.utilise; 0.755, 0.894, tmp+Main.P-Source.Conc.+Nitrogen.Conc.+OD+total.Vol+yield+PL+emission_CO2+His+lactate+PO4.apporte+PO4.utilise; 0.755, 0.894, tmp+Main.P-Source.Conc.+Nitrogen.Conc.+OD+yield+PL+emission_CO2+Thr+His+lactate+PO4.apporte+PO4.utilise; 0.755, 0.894, tmp+Main.P-Source.Conc.+Main.Thr.Conc.+Nitrogen.Conc.+total.Vol+PL+emission_CO2+Thr+His+lactate+PO4.ferm.+PO4.apporte; 0.772, 0.894, Main.P-Source.Conc.+Nitrogen.Conc.+total.Vol+emission_CO2+His+lactate+PO4.apporte+PO4.utilise; 0.759, 0.894, pH+tmp+Main.P-Source.Conc.+Nitrogen.Conc.+total.Vol+emission_CO2+rab+His+lactate+PO4.apporte+PO4.utilise; 0.755, 0.894, pH+tmp+Main.P-Source.Conc.+Nitrogen.Conc.+OD+yield+PL+emission_CO2+His+lactate+PO4.apporte+PO4.utilise; 0.755, 0.894, pH+tmp+Main.P-Source.Conc.+Nitrogen.Conc.+OD+yield+PL+emission_CO2+His+lactate+PO4.ferm.+PO4.apporte; 0.755, 0.894, pH+tmp+Main.P-Source.Conc.+Nitrogen.Conc.+total.Vol+PL+emission_O2+emission_CO2+Thr+lactate+PO4.ferm.+PO4.apporte; 0.750, 0.894, tmp+Main.P-Source.Conc.+Main.Thr.Conc.+Nitrogen.Conc.+total.Vol+PL+emission_O2+emission_CO2+Thr+His+lactate+PO4.apporte+PO4.utilise; 0.768, 0.894, tmp+Main.P-Source.Conc.+Nitrogen.Conc.+total.Vol+PL+emission_CO2+Thr+lactate+PO4.apporte; 0.772, 0.894, Main.P-Source.Conc.+Nitrogen.Conc.+total.Vol+PL+emission_CO2+lactate+PO4.ferm.+PO4.apporte; 0.750, 0.894, pH+tmp+Main.P-Source.Conc.+Nitrogen.Conc.+OD+total.Vol+PL+emission_CO2+rab+His+lactate+PO4.ferm.+PO4.apporte; 0.754, 0.894, tmp+Main.P-Source.Conc.+Nitrogen.Conc.+OD+yield+PL+emission_CO2+Thr+His+lactate+PO4.ferm.+PO4.apporte; 0.759, 0.894, pH+tmp+Main.P-Source.Conc.+Nitrogen.Conc.+total.Vol+PL+emission_O2+emission_CO2+His+lactate+PO4.apporte; 0.754, 0.894, tmp+Main.P-Source.Conc.+Nitrogen.Conc.+Lys_conc.+total.Vol+PL+emission_CO2+Thr+His+lactate+PO4.ferm.+PO4.apporte; 0.768, 0.894, tmp+P-Source.Feed.conc.+PL+emission_O2+emission_CO2+Thr+His+lactate+PO4.apporte; 0.759, 0.894, tmp+Main.P-Source.Conc.+Nitrogen.Conc.+Lys_conc.+total.Vol+PL+emission_CO2+His+lactate+PO4.apporte+PO4.utilise; 0.759, 0.894, pH+tmp+Main.P-Source.Conc.+Nitrogen.Conc.+total.Vol+emission_O2+emission_CO2+His+lactate+PO4.apporte+PO4.utilise; 0.759, 0.894, tmp+Main.P-Source.Conc.+Nitrogen.Conc.+total.Vol+yield+emission_O2+emission_CO2+His+lactate+PO4.ferm.+PO4.apporte; 0.772, 0.894, tmp+Main.P-Source.Conc.+Nitrogen.Conc.+total.Vol+PL+emission_CO2+lactate+PO4.apporte; 0.759, 0.894, tmp+Main.P-Source.Conc.+Nitrogen.Conc.+total.Vol+yield+emission_CO2+rab+His+lactate+PO4.ferm.+PO4.apporte; 0.759, 0.894, pH+tmp+Main.P-Source.Conc.+Nitrogen.Conc.+total.Vol+PL+emission_CO2+rab+His+lactate+PO4.apporte; 0.763, 0.894, pH+tmp+Main.P-Source.Conc.+Nitrogen.Conc.+total.Vol+emission_CO2+His+lactate+PO4.ferm.+PO4.apporte; 0.750, 0.894, pH+tmp+Main.P-Source.Conc.+Nitrogen.Conc.+OD+total.Vol+PL+emission_O2+emission_CO2+His+lactate+PO4.apporte+PO4.utilise; 0.763, 0.894, pH+Main.P-Source.Conc.+Nitrogen.Conc.+total.Vol+yield+PL+emission_CO2+His+lactate+PO4.apporte; 0.745, 0.894, pH+tmp+Main.P-Source.Conc.+P-Source.Feed.conc.+Nitrogen.Conc.+total.Vol+PL+emission_O2+emission_CO2+Thr+His+lactate+PO4.ferm.+PO4.apporte; 0.759, 0.894, pH+Main.P-Source.Conc.+Nitrogen.Conc.+total.Vol+yield+PL+emission_CO2+His+lactate+PO4.ferm.+PO4.apporte; 0.750, 0.894, pH+tmp+Main.P-Source.Conc.+P-Source.Feed.conc.+Nitrogen.Conc.+total.Vol+PL+emission_CO2+Thr+His+lactate+PO4.ferm.+PO4.apporte; 0.763, 0.894, tmp+P-Source.Feed.conc.+total.Vol+PL+emission_CO2+Thr+His+lactate+PO4.ferm.+PO4.apporte; 0.763, 0.894, pH+tmp+Main.P-Source.Conc.+Nitrogen.Conc.+total.Vol+emission_CO2+rab+lactate+PO4.ferm.+PO4.apporte; 0.771, 0.894, Main.P-Source.Conc.+Nitrogen.Conc.+total.Vol+PL+emission_CO2+lactate+PO4.apporte+PO4.utilise; 0.759, 0.894, pH+Main.P-Source.Conc.+Nitrogen.Conc.+total.Vol+yield+PL+emission_CO2+His+lactate+PO4.apporte+PO4.utilise; 0.767, 0.894, pH+tmp+Main.P-Source.Conc.+Nitrogen.Conc.+total.Vol+emission_CO2+His+lactate+PO4.apporte; 0.749, 0.894, pH+tmp+Main.P-Source.Conc.+Nitrogen.Conc.+OD+total.Vol+PL+emission_CO2+Thr+His+lactate+PO4.ferm.+PO4.apporte; 0.763, 0.894, pH+tmp+P-Source.Feed.conc.+PL+emission_CO2+Thr+His+lactate+PO4.apporte+PO4.utilise; 0.749, 0.894, tmp+Main.P-Source.Conc.+Nitrogen.Conc.+OD+total.Vol+yield+PL+emission_O2+emission_CO2+His+lactate+PO4.apporte+PO4.utilise; 0.763, 0.894, pH+tmp+Main.P-Source.Conc.+Nitrogen.Conc.+total.Vol+emission_O2+emission_CO2+lactate+PO4.ferm.+PO4.apporte; 0.763, 0.894, tmp+Main.P-Source.Conc.+Nitrogen.Conc.+OD+total.Vol+emission_CO2+rab+lactate+PO4.apporte+PO4.utilise; 0.754, 0.894, tmp+Main.P-Source.Conc.+Nitrogen.Conc.+OD+PL+emission_O2+emission_CO2+Thr+His+lactate+PO4.apporte+PO4.utilise; 0.754, 0.894, tmp+Main.P-Source.Conc.+Nitrogen.Conc.+total.Vol+PL+emission_O2+emission_CO2+Thr+His+lactate+PO4.ferm.+PO4.utilise; 0.759, 0.894, tmp+Main.P-Source.Conc.+Nitrogen.Conc.+total.Vol+PL+emission_CO2+rab+Thr+His+lactate+PO4.apporte; 0.763, 0.894, tmp+Main.P-Source.Conc.+Nitrogen.Conc.+OD+total.Vol+emission_O2+emission_CO2+lactate+PO4.apporte+PO4.utilise; 0.749, 0.894, pH+tmp+Main.P-Source.Conc.+P-Source.Feed.conc.+Nitrogen.Conc.+total.Vol+PL+emission_CO2+Thr+His+lactate+PO4.apporte+PO4.utilise; 0.754, 0.894, tmp+Main.P-Source.Conc.+Main.Thr.Conc.+Nitrogen.Conc.+total.Vol+PL+emission_CO2+Thr+His+lactate+PO4.apporte+PO4.utilise; 0.763, 0.894, tmp+Main.P-Source.Conc.+Nitrogen.Conc.+total.Vol+emission_CO2+Thr+His+lactate+PO4.apporte+PO4.utilise; 0.749, 0.894, tmp+Main.P-Source.Conc.+Nitrogen.Conc.+OD+total.Vol+yield+PL+emission_O2+emission_CO2+His+lactate+PO4.ferm.+PO4.apporte; 0.759, 0.894, tmp+Main.P-Source.Conc.+Nitrogen.Conc.+total.Vol+yield+emission_O2+emission_CO2+His+lactate+PO4.apporte+PO4.utilise; 0.767, 0.894, Main.P-Source.Conc.+Main.Thr.Conc.+Nitrogen.Conc.+total.Vol+PL+emission_CO2+His+lactate+PO4.apporte; 0.758, 0.894, tmp+Main.P-Source.Conc.+Nitrogen.Conc.+total.Vol+yield+emission_CO2+rab+His+lactate+PO4.apporte+PO4.utilise; 0.758, 0.894, Main.P-Source.Conc.+Nitrogen.Conc.+OD+total.Vol+yield+PL+emission_CO2+His+lactate+PO4.ferm.+PO4.apporte; 0.767, 0.894, tmp+Main.P-Source.Conc.+Nitrogen.Conc.+total.Vol+emission_CO2+rab+His+lactate+PO4.apporte; 0.744, 0.894, pH+tmp+Main.P-Source.Conc.+P-Source.Feed.conc.+Nitrogen.Conc.+total.Vol+PL+emission_O2+emission_CO2+Thr+His+lactate+PO4.apporte+PO4.utilise; 0.758, 0.894, Main.P-Source.Conc.+Nitrogen.Conc.+OD+total.Vol+ yield+PL+emission_CO2+His+lactate+PO4.apporte+ PO4.utilise; 0.754, 0.894, tmp+Main.P-Source.Conc.+Nitrogen.Conc.+Lys_conc.+total.Vol+PL+emission_CO2+ Thr+His+lactate+PO4.apporte+PO4.utilise; 0.763, 0.894, tmp+Main.P-Source.Conc.+Main.Thr.Conc.+Nitrogen. Conc.+emission_CO2+rab+His+lactate+PO4.apporte+ PO4.utilise; 0.754, 0.894, pH+tmp+Main.P-Source.Conc.+ Nitrogen.Conc.+total.Vol+PL+emission_O2+emission_CO2+Thr+lactate+PO4.apporte+PO4.utilise; 0.767, 0.894, tmp+P-Source.Feed.conc.+total.Vol+PL+emission_CO2+Thr+His+lactate+PO4.apporte; 0.763, 0.894, tmp+Main.P-Source.Conc.+Nitrogen.Conc.+OD+total.Vol+ emission_CO2+His+lactate+PO4.ferm.+PO4.apporte; 0.758, 0.894, pH+tmp+Main.P-Source.Conc.+Nitrogen. Conc.+total.Vol+PL+emission_CO2+His+lactate+ PO4.ferm.+PO4.utilise; 0.763, 0.894, tmp+Main.P-Source.Conc.+P-Source.Feed.conc.+Nitrogen.Conc.+ total.Vol+PL+emission_CO2+His+lactate+PO4.apporte; 0.749, 0.894, tmp+Main.P-Source.Conc.+Nitrogen.Conc.+ OD+Lys_conc.+total.Vol+PL+emission_O2+emission_CO2+His+lactate+PO4.apporte+PO4.utilise; 0.771, 0.894, tmp+Main.P-Source.Conc.+Nitrogen.Conc.+emission_CO2+rab+lactate+PO4.ferm.+PO4.apporte; 0.758, 0.894, tmp+Main.P-Source.Conc.+Nitrogen.Conc.+OD+total.Vol+emission_O2+emission_CO2+Thr+lactate+ PO4.ferm.+PO4.apporte; 0.763, 0.894, tmp+Main.P-Source.Conc.+Main.Thr.Conc.+Nitrogen.Conc.+ emission_CO2+rab+His+lactate+PO4.ferm.+PO4.apporte; 0.767, 0.894, tmp+P-Source.Feed.conc.+PL+emission_CO2+rab+Thr+His+lactate+PO4.apporte; 0.758, 0.894, pH+Main.P-Source.Conc.+P-Source.Feed.conc.+Nitrogen.Conc.+total.Vol+PL+emission_CO2+His+lactate+ PO4.ferm.+PO4.apporte; 0.763, 0.894, pH+tmp+P-Source. Feed.conc.+PL+emission_CO2+Thr+His+lactate+ PO4.ferm.+PO4.apporte; 0.767, 0.894, tmp+Main.P-Source.Conc.+Nitrogen.Conc.+total.Vol+emission_O2+ emission_CO2+His+lactate+PO4.apporte; 0.749, 0.894, pH+tmp+Main.P-Source.Conc.+Nitrogen.Conc.+OD+ total.Vol+PL+emission_CO2+Thr+His+lactate+ PO4.apporte+PO4.utilise; 0.767, 0.894, tmp+Main.P-Source.Conc.+Nitrogen.Conc.+total.Vol+emission_CO2+ Thr+lactate+PO4.ferm.+PO4.apporte; 0.763, 0.894, tmp+P-Source.Feed.conc.+total.Vol+PL+emission_CO2+Thr+His+ lactate+PO4.ferm.+PO4.utilise; 0.758, 0.894, tmp+Main.P-Source.Conc.+P-Source.Feed.conc.+Nitrogen.Conc.+ total.Vol+emission_CO2+rab+His+lactate+PO4.ferm.+ PO4.apporte; 0.763, 0.894, Main.P-Source.Conc.+ Nitrogen.Conc.+total.Vol+PL+emission_CO2+His+lactate+ SO4.ferm.+PO4.ferm.+PO4.apporte; 0.749, 0.894, pH+tmp+Main.P-Source.Conc.+Nitrogen.Conc.+total.Vol+ yield+PL+emission_CO2+Thr+His+lactate+PO4.ferm.+ PO4.apporte; 0.749, 0.894, pH+tmp+Main.P-Source.Conc.+ Nitrogen.Conc.+Lys_conc.+total.Vol+PL+emission_O2+ emission_CO2+His+lactate+PO4.ferm.+PO4.apporte; 0.749, 0.894, pH+tmp+Main.P-Source.Conc.+Nitrogen. Conc.+OD+total.Vol+PL+emission_CO2+rab+His+lactate+ PO4.apporte+PO4.utilise; 0.754, 0.894, tmp+Main.P-Source.Conc.+P-Source.Feed.conc.+Nitrogen.Conc.+ total.Vol+PL+emission_O2+emission_CO2+Thr+lactate+ PO4.ferm.+PO4.apporte; 0.754, 0.894, tmp+Main.P-Source.Conc.+Nitrogen.Conc.+OD+PL+emission_CO2+ rab+Thr+His+lactate+PO4.ferm.+PO4.apporte; 0.754, 0.894, tmp+Main.P-Source.Conc.+P-Source.Feed.conc.+ Nitrogen.Conc.+OD+PL+emission_CO2+Thr+His+lactate+PO4.apporte+PO4.utilise; 0.754, 0.894, tmp+Main.P-Source.Conc.+P-Source.Feed.conc.+Nitrogen.Conc.+OD+ PL+emission_CO2+Thr+His+lactate+PO4.ferm.+ PO4.apporte; 0.758, 0.894, tmp+Main.P-Source.Conc.+P-Source.Feed.conc.+Nitrogen.Conc.+total.Vol+ emission_O2+emission_CO2+His+lactate+PO4.ferm.+ PO4.apporte; 0.749, 0.894, pH+tmp+Main.P-Source.Conc.+ Nitrogen.Conc.+total.Vol+yield+PL+emission_CO2+Thr+ His+lactate+PO4.apporte+PO4.utilise; 0.762, 0.894, pH+tmp+Main.P-Source.Conc.+Nitrogen.Conc.+total.Vol+ emission_CO2+His+lactate+PO4.apporte+PO4.utilise; 0.762, 0.894, tmp+Main.P-Source.Conc.+Nitrogen.Conc.+ OD+PL+emission_O2+emission_CO2+His+lactate+ PO4.apporte; 0.762, 0.894, tmp+Main.P-Source.Conc.+Nitrogen.Conc.+OD+PL+emission_CO2+rab+His+lactate+ PO4.apporte; 0.758, 0.894, tmp+Main.P-Source.Conc.+ Nitrogen.Conc.+OD+yield+PL+emission_CO2+Thr+His+ lactate+PO4.apporte; 0.762, 0.894, Main.P-Source.Conc.+ Nitrogen.Conc.+total.Vol+PL+emission_CO2+His+lactate+ SO4.ferm.+PO4.apporte+PO4.utilise; 0.749, 0.894, tmp+ Main.P-Source.Conc.+Main.Thr.Conc.+Nitrogen.Conc.+ total.Vol+PL+emission_CO2+rab+Thr+His+lactate+ PO4.ferm.+PO4.apporte; 0.758, 0.894, pH+Main.P-Source.Conc.+P-Source.Feed.conc.+Nitrogen.Conc.+ total.Vol+PL+emission_CO2+His+lactate+PO4.apporte+ PO4.utilise; 0.749, 0.894, tmp+Main.P-Source.Conc.+ Nitrogen.Conc.+OD+Lys_conc.+total.Vol+PL+ emission_CO2+rab+His+lactate+PO4.ferm.+PO4.apporte; 0.762, 0.894, pH+tmp+Main.P-Source.Conc.+Nitrogen. Conc.+total.Vol+emission_CO2+rab+lactate+PO4.apporte+ PO4.utilise; 0.758, 0.894, pH+Main.P-Source.Conc.+Nitrogen.Conc.+total.Vol+PL+emission_CO2+Thr+His+lactate+ PO4.ferm.+PO4.apporte; 0.749, 0.894, pH+tmp+Main.P-Source.Conc.+Nitrogen.Conc.+total.Vol+yield+PL+ emission_O2+emission_CO2+His+lactate+PO4.apporte+ PO4.utilise; 0.753, 0.894, pH+tmp+Main.P-Source.Conc.+ Nitrogen.Conc.+OD+PL+emission_CO2+Thr+His+ lactate+PO4.ferm.+PO4.apporte; 0.748, 0.894, tmp+ Main.P-Source.Conc.+Nitrogen.Conc.+OD+total.Vol+ yield+PL+emission_CO2+rab+His+lactate+PO4.apporte+ PO4.utilise; 0.748, 0.894, pH+tmp+Main.P-Source.Conc.+ Nitrogen.Conc.+total.Vol+yield+PL+emission_O2+ emission_CO2+His+lactate+PO4.ferm.+PO4.apporte; 0.758, 0.894, tmp+Main.P-Source.Conc.+Nitrogen.Conc.+ total.Vol+emission_O2+emission_CO2+rab+His+lactate+ PO4.ferm.+PO4.apporte; 0.753, 0.894, pH+tmp+Main.P-Source.Conc.+Nitrogen.Conc.+total.Vol+PL+ emission_CO2+rab+Thr+lactate+PO4.ferm.+PO4.apporte; 0.753, 0.894, tmp+Main.P-Source.Conc.+Nitrogen.Conc.+ total.Vol+PL+emission_CO2+rab+Thr+His+lactate+ PO4.ferm.+PO4.utilise; 0.771, 0.894, tmp+Main.P-Source.Conc.+Nitrogen.Conc.+emission_CO2+rab+ lactate+PO4.apporte+PO4.utilise; 0.748, 0.894, tmp+ Main.P-Source.Conc.+Nitrogen.Conc.+OD+total.Vol+ yield+PL+emission_CO2+rab+His+lactate+PO4.ferm.+ PO4.apporte; 0.744, 0.894, tmp+Main.P-Source.Conc.+ Nitrogen.Conc.+OD+Lys_conc.+total.Vol+PL+ emission_O2+emission_CO2+Thr+His+lactate+ PO4.ferm.+PO4.apporte; 0.762, 0.894, pH+tmp+Main.P-Source.Conc.+Nitrogen.Conc.+total.Vol+emission_O2+ emission_CO2+lactate+PO4.apporte+PO4.utilise; 0.762, 0.894, tmp+Main.P-Source.Conc.+Nitrogen.Conc.+total. Vol+yield+emission_CO2+His+lactate+PO4.ferm.+ PO4.apporte; 0.758, 0.894, pH+tmp+Main.P-Source.Conc.+ Main.Thr.Conc.+Nitrogen.Conc.+total.Vol+emission_O2+ emission_CO2+lactate+PO4.ferm.+PO4.apporte; 0.758, 0.894, tmp+Main.P-Source.Conc.+Nitrogen.Conc.+OD+ yield+PL+emission_O2+emission_CO2+His+lactate+ PO4.apporte; 0.753, 0.894, tmp+Main.P-Source.Conc.+ P-Source.Feed.conc.+Nitrogen.Conc.+total.Vol+PL+ emission_O2+emission_CO2+Thr+lactate+PO4.apporte+ PO4.utilise; 0.758, 0.894, tmp+Main.P-Source.Conc.+ Main.Thr.Conc.+Nitrogen.Conc.+total.Vol+emission_O2+ emission_CO2+Thr+lactate+PO4.ferm.+PO4.apporte; 0.762, 0.894, pH+tmp+P-Source.Feed.conc.+PL+emission_CO2+Thr+His+lactate+PO4.ferm.+PO4.utilise; 0.758, 0.894, pH+tmp+Main.P-Source.Conc.+Main.Thr.Conc.+ Nitrogen.Conc.+total.Vol+emission_CO2+rab+lactate+ PO4.ferm.+PO4.apporte; 0.762, 0.894, tmp+Main.P-Source.Conc.+Nitrogen.Conc.+OD+total.Vol+ emission_CO2+His+lactate+PO4.apporte+PO4.utilise; 0.743, 0.894, tmp+Main.P-Source.Conc.+P-Source.Feed. conc.+Nitrogen.Conc.+total.Vol+PL+emission_O2+emission_CO2+rab+Thr+His+lactate+PO4.ferm.+PO4.apporte; 0.753, 0.894, tmp+Main.P-Source.Conc.+Nitrogen.Conc.+ OD+PL+emission_CO2+rab+Thr+His+lactate+ PO4.apporte+PO4.utilise; 0.753, 0.894, tmp+Main.P-Source.Conc.+Main.Thr.Conc.+Nitrogen.Conc.+OD+ total.Vol+emission_O2+emission_CO2+His+lactate+ PO4.ferm.+PO4.apporte; 0.758, 0.894, pH+Main.P-Source.Conc.+Nitrogen.Conc.+total.Vol+PL+ emission_CO2+Thr+His+lactate+PO4.apporte+PO4.utilise; 0.743, 0.894, pH+tmp+Main.P-Source.Conc.+P-Source. Feed.conc.+Nitrogen.Conc.+total.Vol+PL+emission_CO2+ rab+Thr+His+lactate+PO4.ferm.+PO4.apporte; 0.758, 0.894, tmp+Main.P-Source.Conc.+P-Source.Feed.conc.+ Nitrogen.Conc.+PL+emission_O2+emission_CO2+Thr+ lactate+PO4.ferm.+PO4.apporte; 0.748, 0.894, tmp+ Main.P-Source.Conc.+Main.Thr.Conc.+Nitrogen.Conc.+ total.Vol+PL+emission_O2+emission_CO2+His+lactate+ SO4.ferm.+PO4.apporte+PO4.utilise; 0.758, 0.894, tmp+ Main.P-Source.Conc.+Nitrogen.Conc.+OD+total.Vol+ emission_O2+emission_CO2+Thr+lactate+PO4.apporte+ PO4.utilise; 0.770, 0.894, tmp+Main.P-Source.Conc.+ Nitrogen.Conc.+total.Vol+emission_CO2+Thr+lactate+ PO4.apporte; 0.753, 0.894, pH+tmp+Main.P-Source.Conc.+ Main.Thr.Conc.+Nitrogen.Conc.+total.Vol+emission_O2+ emission_CO2+His+lactate+PO4.ferm.+PO4.apporte; 0.753, 0.894, tmp+Main.P-Source.Conc.+Nitrogen.Conc.+ OD+total.Vol+emission_O2+emission_CO2+Thr+His+lactate+PO4.ferm.+PO4.apporte; 0.766, 0.894, tmp+Main.P-Source.Conc.+Nitrogen.Conc.+total.Vol+emission_CO2+ Thr+lactate+PO4.apporte+PO4.utilise; 0.758, 0.894, tmp+ Main.P-Source.Conc.+P-Source.Feed.conc.+ Nitrogen.Conc.+PL+emission_O2+emission_CO2+Thr+ lactate+PO4.apporte+PO4.utilise; 0.758, 0.894, tmp+ Main.P-Source.Conc.+Nitrogen.Conc.+OD+total.Vol+ yield+PL+emission_CO2+His+lactate+PO4.apporte; 0.753, 0.894, pH+tmp+Main.P-Source.Conc.+Nitrogen.Conc.+ OD+PL+emission_CO2+Thr+His+lactate+PO4.apporte+ PO4.utilise; 0.758, 0.894, tmp+Main.P-Source.Conc.+Nitrogen.Conc.+OD+yield+PL+emission_CO2+rab+His+ lactate+PO4.apporte; 0.753, 0.894, pH+tmp+Main.P-Source.Conc.+P-Source.Feed.conc.+Nitrogen.Conc.+ total.Vol+PL+emission_CO2+His+lactate+PO4.ferm.+ PO4.apporte; 0.757, 0.894, tmp+Main.P-Source.Conc.+P-Source.Feed.conc.+Nitrogen.Conc.+PL+emission_CO2+ rab+His+lactate+PO4.ferm.+PO4.apporte; 0.753, 0.894, tmp+Main.P-Source.Conc.+Nitrogen.Conc.+total.Vol+PL+ emission_O2+emission_CO2+Thr+lactate+SO4.ferm.+ PO4.ferm.+PO4.apporte; 0.748, 0.894, tmp+Main.P-Source.Conc.+Main.Thr.Conc.+Nitrogen.Conc.+total.Vol+ PL+emission_O2+emission_CO2+His+lactate+SO4.ferm.+ PO4.ferm.+PO4.apporte; 0.766, 0.894, tmp+Main.P-Source.Conc.+P-Source.Feed.conc.+PL+emission_CO2+ Thr+His+lactate+PO4.ferm.; 0.753, 0.894, pH+tmp+ Main.P-Source.Conc.+Main.Thr.Conc.+Nitrogen.Conc.+ total.Vol+emission_CO2+rab+His+lactate+PO4.ferm.+ PO4.apporte; 0.757, 0.894, pH+tmp+Main.P-Source.Conc.+ Nitrogen.Conc.+total.Vol+PL+emission_O2+ emission_CO2+lactate+PO4.ferm.+PO4.apporte; 0.753, 0.894, pH+tmp+Main.P-Source.Conc.+Nitrogen.Conc.+ OD+PL+emission_O2+emission_CO2+His+lactate+ PO4.ferm.+PO4.apporte; 0.757, 0.894, tmp+Main.P-Source.Conc.+P-Source.Feed.conc.+Nitrogen.Conc.+PL+ emission_CO2+rab+His+lactate+PO4.apporte+PO4.utilise; 0.748, 0.894, tmp+Main.P-Source.Conc.+Main.Thr.Conc.+ Nitrogen.Conc.+total.Vol+PL+emission_CO2+rab+Thr+ His+lactate+PO4.apporte+PO4.utilise; 0.743, 0.894, tmp+ Main.P-Source.Conc.+P-Source.Feed.conc.+ Nitrogen.Conc.+total.Vol+PL+emission_O2+ emission_CO2+rab+Thr+His+lactate+PO4.apporte+ PO4.utilise; 0.757, 0.894, tmp+Main.P-Source.Conc.+ Main.Thr.Conc.+Nitrogen.Conc.+OD+total.Vol+ emission_O2+emission_CO2+lactate+PO4.ferm.+ PO4.apporte; 0.757, 0.894, tmp+Main.P-Source.Conc.+ Nitrogen.Conc.+OD+total.Vol+emission_CO2+rab+Thr+ lactate+PO4.ferm.+PO4.apporte; 0.753, 0.894, tmp+ Main.P-Source.Conc.+Main.Thr.Conc.+Nitrogen.Conc.+ OD+total.Vol+emission_CO2+rab+His+lactate+ PO4.ferm.+PO4.apporte; 0.753, 0.894, tmp+Main.P-Source.Conc.+Nitrogen.Conc.+Lys_conc.+total.Vol+PL+ emission_O2+emission_CO2+Thr+lactate+PO4.ferm.+ PO4.apporte; 0.748, 0.894, pH+tmp+Main.P-Source.Conc.+ Nitrogen.Conc.+total.Vol+yield+PL+emission_CO2+rab+ His+lactate+PO4.ferm.+PO4.apporte; 0.762, 0.894, tmp+P-Source.Feed.conc.+OD+PL+emission_CO2+Thr+His+ lactate+PO4.apporte+PO4.utilise; 0.757, 0.894, tmp+ Main.P-Source.Conc.+P-Source.Feed.conc.+ Nitrogen.Conc.+PL+emission_CO2+rab+Thr+lactate+ PO4.ferm.+PO4.apporte; 0.770, 0.894, pH+tmp+Main.P-Source.Conc.+Nitrogen.Conc.+total.Vol+emission_CO2+ lactate+PO4.apporte; 0.757, 0.894, pH+tmp+Main.P-Source.Conc.+Main.Thr.Conc.+Nitrogen.Conc.+total.Vol+ emission_O2+emission_CO2+lactate+PO4.apporte+ PO4.utilise; 0.748, 0.894, pH+tmp+Main.P-Source.Conc.+ Nitrogen.Conc.+total.Vol+yield+PL+emission_CO2+rab+ His+lactate+PO4.apporte+PO4.utilise; 0.762, 0.894, tmp+ Main.P-Source.Conc.+P-Source.Feed.conc.+ Nitrogen.Conc.+total.Vol+emission_O2+emission_CO2+ lactate+PO4.ferm.+PO4.apporte; 0.753, 0.894, pH+tmp+ Main.P-Source.Conc.+Nitrogen.Conc.+OD+PL+ emission_CO2+rab+His+lactate+PO4.ferm.+PO4.apporte; 0.743, 0.894, tmp+Main.P-Source.Conc.+P-Source.Feed. conc.+Nitrogen.Conc.+OD+total.Vol+PL+emission_O2+ emission_CO2+Thr+His+lactate+PO4.ferm.+PO4.apporte; 0.753, 0.894, tmp+Main.P-Source.Conc.+Nitrogen.Conc.+ OD+total.Vol+PL+emission_O2+emission_CO2+Thr+lactate+PO4.ferm.+PO4.apporte; 0.743, 0.893, pH+tmp+ Main.P-Source.Conc.+Nitrogen.Conc.+OD+total.Vol+PL+ emission_O2+emission_CO2+Thr+His+lactate+ PO4.ferm.+PO4.apporte; 0.762, 0.893, tmp+P-Source.Feed.conc.+yield+PL+emission_CO2+Thr+His+ lactate+PO4.apporte+PO4.utilise; 0.770, 0.893, pH+Main.P-Source.Conc.+Nitrogen.Conc.+total.Vol+PL+ emission_CO2+lactate+PO4.apporte; 0.743, 0.893, pH+tmp+Main.P-Source.Conc.+P-Source.Feed.conc.+Nitrogen.Conc.+total.Vol+PL+emission_CO2+rab+Thr+His+ lactate+PO4.apporte+PO4.utilise; 0.757, 0.893, tmp+ Main.P-Source.Conc.+P-Source.Feed.conc.+ Nitrogen.Conc.+total.Vol+emission_CO2+rab+His+ lactate+PO4.apporte+PO4.utilise; 0.762, 0.893, pH+Main.P-Source.Conc.+Nitrogen.Conc.+total.Vol+PL+ emission_CO2+Thr+His+lactate+PO4.apporte; 0.774, 0.893, Main.P-Source.Conc.+Nitrogen.Conc.+total.Vol+emission_CO2+lactate+PO4.ferm.+PO4.apporte; 0.762, 0.893, pH+Main.P-Source.Conc.+P-Source.Feed.conc.+Nitrogen.Conc.+total.Vol+PL+emission_CO2+His+lactate+PO4.apporte; 0.757, 0.893, pH+tmp+Main.P-Source.Conc.+Main.Thr.Conc.+Nitrogen.Conc.+total.Vol+emission_CO2+rab+lactate+PO4.apporte+PO4.utilise; 0.757, 0.893, tmp+Main.P-Source.Conc.+Main.Thr.Conc.+Nitrogen.Conc.+OD+total.Vol+emission_CO2+rab+lactate+PO4.ferm.+PO4.apporte; 0.762, 0.893, pH+Main.P-Source.Conc.+Nitrogen.Conc.+total.Vol+PL+emission_O2+emission_CO2+His+lactate+PO4.apporte; 0.753, 0.893, tmp+Main.P-Source.Conc.+Main.Thr.Conc.+Nitrogen.Conc.+OD+total.Vol+emission_O2+emission_CO2+His+lactate+PO4.apporte+PO4.utilise; 0.748, 0.893, tmp+Main.P-Source.Conc.+P-Source.Feed.conc.+Nitrogen.Conc.+total.Vol+yield+PL+emission_CO2+Thr+His+lactate+PO4.apporte+PO4.utilise; 0.762, 0.893, tmp+P-Source.Feed.conc.+Main.Thr.Conc.+PL+emission_CO2+Thr+His+lactate+PO4.apporte+PO4.utilise; 0.766, 0.893, tmp+Main.P-Source.Conc.+Main.Thr.Conc.+Nitrogen.Conc.+total.Vol+emission_CO2+rab+lactate+PO4.apporte; 0.757, 0.893, tmp+Main.P-Source.Conc.+Nitrogen.Conc.+OD+total.Vol+PL+emission_CO2+His+lactate+PO4.ferm.+PO4.utilise; 0.757, 0.893, tmp+Main.P-Source.Conc.+P-Source.Feed.conc.+Nitrogen.Conc.+PL+emission_CO2+rab+Thr+lactate+PO4.apporte+PO4.utilise; 0.757, 0.893, pH+tmp+Main.P-Source.Conc.+Nitrogen.Conc.+total.Vol+PL+emission_CO2+rab+lactate+PO4.ferm.+PO4.apporte; 0.762, 0.893, tmp+Main.P-Source.Conc.+P-Source.Feed.conc.+Nitrogen.Conc.+total.Vol+emission_CO2+rab+lactate+PO4.ferm.+PO4.apporte; 0.748, 0.893, tmp+Main.P-Source.Conc.+P-Source.Feed.conc.+Nitrogen.Conc.+total.Vol+yield+PL+emission_CO2+Thr+His+lactate+PO4.ferm.+PO4.apporte; 0.757, 0.893, tmp+Main.P-Source.Conc.+Main.Thr.Conc.+Nitrogen.Conc.+total.Vol+PL+emission_O2+emission_CO2+lactate+PO4.ferm.+PO4.apporte; 0.748, 0.893, pH+tmp+Main.P-Source.Conc.+Main.Thr.Conc.+Nitrogen.Conc.+total.Vol+PL+emission_O2+emission_CO2+His+lactate+PO4.ferm.+PO4.apporte; 0.757, 0.893, tmp+Main.P-Source.Conc.+P-Source.Feed.conc.+Nitrogen.Conc.+OD+PL+emission_CO2+Thr+His+lactate+PO4.apporte; 0.757, 0.893, tmp+Main.P-Source.Conc.+Nitrogen.Conc.+OD+total.Vol+PL+emission_O2+emission_CO2+His+lactate+PO4.apporte; 0.748, 0.893, tmp+Main.P-Source.Conc.+P-Source.Feed.conc.+Nitrogen.Conc.+OD+PL+emission_O2+emission_CO2+Thr+His+lactate+PO4.apporte+PO4.utilise; 0.748, 0.893, tmp+Main.P-Source.Conc.+P-Source.Feed.conc.+Nitrogen.Conc.+OD+PL+emission_O2+emission_CO2+Thr+His+lactate+PO4.ferm.+PO4.apporte; 0.753, 0.893, pH+tmp+Main.P-Source.Conc.+Nitrogen.Conc.+total.Vol+PL+emission_CO2+rab+Thr+lactate+PO4.apporte+PO4.utilise; 0.757, 0.893, tmp+Main.P-Source.Conc.+Main.Thr.Conc.+Nitrogen.Conc.+OD+total.Vol+emission_O2+emission_CO2+lactate+PO4.apporte+PO4.utilise; 0.757, 0.893, tmp+Main.P-Source.Conc.+P-Source.Feed.conc.+Nitrogen.Conc.+total.Vol+emission_O2+emission_CO2+His+lactate+PO4.apporte+PO4.utilise; 0.753, 0.893, pH+tmp+Main.P-Source.Conc.+P-Source.Feed.conc.+Nitrogen.Conc.+total.Vol+PL+emission_CO2+His+lactate+PO4.apporte+PO4.utilise; 0.770, 0.893, pH+Main.P-Source.Conc.+Nitrogen.Conc.+total.Vol+emission_CO2+His+lactate+PO4.apporte; 0.748, 0.893, pH+tmp+Main.P-Source.Conc.+P-Source.Feed.conc.+Nitrogen.Conc.+total.Vol+PL+emission_O2+emission_CO2+His+lactate+PO4.ferm.+PO4.apporte; 0.757, 0.893, tmp+Main.P-Source.Conc.+Main.Thr.Conc.+Nitrogen.Conc.+total.Vol+emission_O2+emission_CO2+Thr+lactate+PO4.apporte+PO4.utilise; 0.761, 0.893, tmp+Main.P-Source.Conc.+Nitrogen.Conc.+total.Vol+yield+emission_CO2+His+lactate+PO4.apporte+PO4.utilise; 0.757, 0.893, tmp+P-Source.Feed.conc.+PL+emission_O2+emission_CO2+rab+Thr+His+lactate+PO4.apporte+PO4.utilise; 0.752, 0.893, pH+tmp+Main.P-Source.Conc.+Main.Thr.Conc.+Nitrogen.Conc.+total.Vol+emission_O2+emission_CO2+His+lactate+PO4.apporte+PO4.utilise; 0.748, 0.893, pH+tmp+Main.P-Source.Conc.+Nitrogen.Conc.+Lys_conc.+total.Vol+PL+emission_O2+emission_CO2+His+lactate+PO4.apporte+PO4.utilise; 0.743, 0.893, tmp+Main.P-Source.Conc.+P-Source.Feed.conc.+Nitrogen.Conc.+OD+total.Vol+PL+emission_O2+emission_CO2+Thr+His+lactate+PO4.apporte+PO4.utilise; 0.748, 0.893, pH+tmp+Main.P-Source.Conc.+Nitrogen.Conc.+OD+yield+PL+emission_O2+emission_CO2+His+lactate+PO4.apporte+PO4.utilise; 0.766, 0.893, tmp+Main.P-Source.Conc.+Main.Thr.Conc.+Nitrogen.Conc.+total.Vol+emission_O2+emission_CO2+lactate+PO4.apporte; 0.748, 0.893, tmp+Main.P-Source.Conc.+P-Source.Feed.conc.+Nitrogen.Conc.+PL+emission_O2+emission_CO2+rab+Thr+His+lactate+PO4.apporte+PO4.utilise; 0.757, 0.893, pH+Main.P-Source.Conc.+Nitrogen.Conc.+total.Vol+PL+emission_O2+emission_CO2+His+lactate+PO4.ferm.+PO4.apporte; 0.761, 0.893, tmp+Main.P-Source.Conc.+Main.Thr.Conc.+Nitrogen.Conc.+emission_O2+emission_CO2+His+lactate+PO4.apporte+PO4.utilise; 0.757, 0.893, Main.P-Source.Conc.+P-Source.Feed.conc.+Nitrogen.Conc.+OD+total.Vol+PL+emission_CO2+His+lactate+PO4.ferm.+PO4.apporte; 0.748, 0.893, tmp+Main.P-Source.Conc.+Nitrogen.Conc.+OD+yield+PL+emission_O2+emission_CO2+Thr+His+lactate+PO4.apporte+PO4.utilise; 0.748, 0.893, pH+tmp+Main.P-Source.Conc.+Nitrogen.Conc.+Lys_conc.+total.Vol+PL+emission_CO2+rab+His+lactate+PO4.ferm.+PO4.apporte; 0.752, 0.893, tmp+Main.P-Source.Conc.+Nitrogen.Conc.+total.Vol+PL+emission_O2+emission_CO2+rab+Thr+lactate+PO4.ferm.+PO4.apporte; 0.770, 0.893, tmp+Main.P-Source.Conc.+Nitrogen.Conc.+emission_O2+emission_CO2+lactate+PO4.ferm.+PO4.apporte; 0.743, 0.893, tmp+Main.P-Source.Conc.+P-Source.Feed.conc.+Nitrogen.Conc.+total.Vol+PL+emission_O2+emission_CO2+Thr+His+lactate+SO4.ferm.+PO4.ferm.+PO4.apporte; 0.757, 0.893, Main.P-Source.Conc.+P-Source.Feed.conc.+Nitrogen.Conc.+total.Vol+yield+PL+emission_CO2+His+lactate+PO4.ferm.+PO4.apporte; 0.752, 0.893, pH+tmp+Main.P-Source.Conc.+Nitrogen.Conc.+total.Vol+PL+emission_CO2+His+lactate+SO4.ferm.+PO4.ferm.+PO4.apporte; 0.752, 0.893, tmp+Main.P-Source.Conc.+Main.Thr.Conc.+Nitrogen.Conc.+OD+total.Vol+emission_CO2+rab+His+lactate+PO4.apporte+PO4.utilise; 0.752, 0.893, pH+tmp+Main.P-Source.Conc.+Main.Thr.Conc.+Nitrogen.Conc.+total.Vol+emission_CO2+rab+His+lactate+PO4.apporte+PO4.utilise; 0.752, 0.893, tmp+Main.P-Source.Conc.+Nitrogen.Conc.+total.Vol+PL+emission_O2+emission_CO2+Thr+lactate+SO4.ferm.+PO4.apporte+PO4.utilise; 0.757, 0.893, tmp+Main.P-Source.Conc.+Main.Thr.Conc.+Nitrogen.Conc.+OD+total.Vol+emission_CO2+rab+lactate+PO4.apporte+PO4.utilise; 0.748, 0.893, pH+tmp+Main.P-Source.Conc.+P-Source.Feed.conc.+total.Vol+PL+emission_CO2+rab+His+lactate+PO4.ferm.+PO4.apporte; 0.757, 0.893, tmp+Main.P-Source.Conc.+Main.Thr.Conc.+

Nitrogen.Conc.+total.Vol+emission_O2+emission_CO2+lactate+SO4.ferm.+PO4.ferm.+PO4.apporte; 0.757, 0.893, tmp+Main.P-Source.Conc.+Main.Thr.Conc.+Nitrogen.Conc.+total.Vol+PL+emission_O2+emission_CO2+lactate+PO4.apporte+PO4.utilise; 0.752, 0.893, pH+tmp+Main.P-Source.Conc.+Nitrogen.Conc.+OD+PL+emission_O2+emission_CO2+His+lactate+PO4.apporte+PO4.utilise; 0.747, 0.893, pH+tmp+Main.P-Source.Conc.+Main.Thr.Conc.+Nitrogen.Conc.+total.Vol+PL+emission_O2+emission_CO2+His+lactate+PO4.apporte+PO4.utilise; 0.747, 0.893, tmp+Main.P-Source.Conc.+Nitrogen.Conc.+OD+total.Vol+yield+PL+emission_CO2+Thr+His+lactate+PO4.ferm.+PO4.apporte; 0.757, 0.893, pH+tmp+Main.P-Source.Conc.+Nitrogen.Conc.+OD+PL+emission_CO2+Thr+His+lactate+PO4.apporte; 0.761, 0.893, pH+Main.P-Source.Conc.+Nitrogen.Conc.+OD+PL+emission_CO2+His+lactate+PO4.ferm.+PO4.apporte; 0.757, 0.893, tmp+Main.P-Source.Conc.+Nitrogen.Conc.+total.Vol+yield+PL+emission_CO2+Thr+His+lactate+PO4.apporte; 0.765, 0.893, tmp+Main.P-Source.Conc.+Nitrogen.Conc.+total.Vol+emission_CO2+Thr+His+lactate+PO4.apporte; 0.757, 0.893, tmp+P-Source.Feed.conc.+total.Vol+PL+emission_O2+emission_CO2+Thr+His+lactate+PO4.apporte+PO4.utilise; 0.747, 0.893, tmp+Main.P-Source.Conc.+P-Source.Feed.conc.+Nitrogen.Conc.+OD+total.Vol+PL+emission_CO2+Thr+His+lactate+PO4.ferm.+PO4.apporte; 0.747, 0.893, pH+tmp+Main.P-Source.Conc.+Nitrogen.Conc.+OD+yield+PL+emission_O2+emission_CO2+His+lactate+PO4.ferm.+PO4.apporte; 0.757, 0.893, tmp+Main.P-Source.Conc.+Nitrogen.Conc.+OD+total.Vol+PL+emission_CO2+rab+His+lactate+PO4.apporte; 0.742, 0.893, tmp+Main.P-Source.Conc.+Nitrogen.Conc.+OD+Lys_conc.+total.Vol+PL+emission_O2+emission_CO2+Thr+His+lactate+PO4.apporte+PO4.utilise; 0.761, 0.893, tmp+P-Source.Feed.conc.+Main.Thr.Conc.+PL+emission_CO2+Thr+His+lactate+PO4.ferm.+PO4.apporte; 0.774, 0.893, Main.P-Source.Conc.+Nitrogen.Conc.+total.Vol+emission_CO2+lactate+PO4.apporte+PO4.utilise; 0.747, 0.893, tmp+Main.P-Source.Conc.+P-Source.Feed.conc.+Nitrogen.Conc.+PL+emission_O2+emission_CO2+rab+Thr+His+lactate+PO4.ferm.+PO4.apporte; 0.747, 0.893, pH+tmp+Main.P-Source.Conc.+Nitrogen.Conc.+OD+yield+PL+emission_CO2+rab+His+lactate+PO4.apporte+PO4.utilise; 0.761, 0.893, tmp+P-Source.Feed.conc.+OD+PL+emission_CO2+Thr+His+lactate+PO4.ferm.+PO4.apporte; 0.752, 0.893, tmp+Main.P-Source.Conc.+P-Source.Feed.conc.+Nitrogen.Conc.+total.Vol+PL+emission_CO2+rab+Thr+lactate+PO4.ferm.+PO4.apporte; 0.752, 0.893, tmp+Main.P-Source.Conc.+Nitrogen.Conc.+OD+total.Vol+emission_CO2+rab+Thr+His+lactate+PO4.ferm.+PO4.apporte; 0.747, 0.893, tmp+Main.P-Source.Conc.+Nitrogen.Conc.+OD+total.Vol+yield+PL+emission_CO2+Thr+His+lactate+PO4.apporte+PO4.utilise; 0.761, 0.893, tmp+Main.P-Source.Conc.+Nitrogen.Conc.+total.Vol+PL+emission_O2+emission_CO2+Thr+lactate+PO4.apporte; 0.757, 0.893, pH+tmp+Main.P-Source.Conc.+Nitrogen.Conc.+total.Vol+PL+emission_CO2+Thr+lactate+PO4.ferm.+PO4.apporte; 0.752, 0.893, tmp+Main.P-Source.Conc.+Nitrogen.Conc.+OD+total.Vol+emission_O2+emission_CO2+Thr+His+lactate+PO4.apporte+PO4.utilise; 0.757, 0.893, pH+tmp+Main.P-Source.Conc.+Nitrogen.Conc.+total.Vol+yield+PL+emission_CO2+His+lactate+PO4.apporte; 0.757, 0.893, Main.P-Source.Conc.+P-Source.Feed.conc.+Nitrogen.Conc.+total.Vol+yield+PL+emission_CO2+His+lactate+PO4.apporte+PO4.utilise; 0.757, 0.893, Main.P-Source.Conc.+Nitrogen.Conc.+OD+total.Vol+PL+emission_CO2+Thr+His+lactate+PO4.ferm.+PO4.apporte; 0.752, 0.893, tmp+Main.P-Source.Conc.+Nitrogen.Conc.+OD+total.Vol+PL+emission_O2+emission_CO2+Thr+lactate+PO4.apporte+PO4.utilise; 0.757, 0.893, pH+tmp+Main.P-Source.Conc.+Nitrogen.Conc.+total.Vol+PL+emission_O2+emission_CO2+lactate+PO4.apporte+PO4.utilise; 0.747, 0.893, tmp+Main.P-Source.Conc.+Nitrogen.Conc.+OD+Lys_conc.+total.Vol+PL+emission_CO2+rab+His+lactate+PO4.apporte+PO4.utilise; 0.761, 0.893, tmp+Main.P-Source.Conc.+Main.Thr.Conc.+Nitrogen.Conc.+emission_O2+emission_CO2+His+lactate+PO4.ferm.+PO4.apporte; 0.757, 0.893, tmp+Main.P-Source.Conc.+Nitrogen.Conc.+total.Vol+emission_O2+emission_CO2+rab+His+lactate+PO4.apporte+PO4.utilise; 0.752, 0.893, pH+tmp+Main.P-Source.Conc.+Nitrogen.Conc.+total.Vol+PL+emission_O2+emission_CO2+His+lactate+PO4.ferm.+PO4.utilise; 0.742, 0.893, tmp+Main.P-Source.Conc.+P-Source.Feed.conc.+Nitrogen.Conc.+total.Vol+PL+emission_O2+emission_CO2+Thr+His+lactate+SO4.ferm.+PO4.apporte+PO4.utilise; 0.757, 0.893, tmp+Main.P-Source.Conc.+Nitrogen.Conc.+OD+total.Vol+emission_CO2+rab+Thr+lactate+PO4.apporte+PO4.utilise; 0.757, 0.893, pH+Main.P-Source.Conc.+Nitrogen.Conc.+total.Vol+PL+emission_O2+emission_CO2+His+lactate+PO4.apporte+PO4.utilise; 0.752, 0.893, pH+tmp+Main.P-Source.Conc.+Nitrogen.Conc.+OD+PL+emission_CO2+rab+His+lactate+PO4.apporte+PO4.utilise; 0.765, 0.893, tmp+Main.P-Source.Conc.+Nitrogen.Conc.+total.Vol+emission_CO2+rab+lactate+PO4.ferm.+PO4.utilise; 0.747, 0.893, pH+tmp+Main.P-Source.Conc.+P-Source.Feed.conc.+Nitrogen.Conc.+PL+emission_O2+emission_CO2+Thr+His+lactate+PO4.apporte+PO4.utilise; 0.765, 0.893, Main.P-Source.Conc.+Nitrogen.Conc.+total.Vol+PL+emission_CO2+His+lactate+SO4.ferm.+PO4.apporte; 0.757, 0.893, tmp+Main.P-Source.Conc.+Main.Thr.Conc.+Nitrogen.Conc.+total.Vol+emission_O2+emission_CO2+lactate+SO4.ferm.+PO4.apporte+PO4.utilise; 0.752, 0.893, pH+tmp+Main.P-Source.Conc.+P-Source.Feed.conc.+Nitrogen.Conc.+PL+emission_CO2+Thr+His+lactate+PO4.apporte+PO4.utilise; 0.747, 0.893, tmp+Main.P-Source.Conc.+Main.Thr.Conc.+Nitrogen.Conc.+OD+total.Vol+PL+emission_O2+emission_CO2+His+lactate+PO4.ferm.+PO4.apporte; 0.747, 0.893, pH+tmp+Main.P-Source.Conc.+Nitrogen.Conc.+total.Vol+PL+emission_O2+emission_CO2+His+lactate+SO4.ferm.+PO4.ferm.+PO4.apporte; 0.747, 0.893, pH+tmp+Main.P-Source.Conc.+Main.Thr.Conc.+Nitrogen.Conc.+total.Vol+PL+emission_CO2+rab+His+lactate+PO4.ferm.+PO4.apporte; 0.757, 0.893, Main.P-Source.Conc.+Nitrogen.Conc.+total.Vol+yield+PL+emission_CO2+Thr+His+lactate+PO4.ferm.+PO4.apporte; 0.761, 0.893, pH+Main.P-Source.Conc.+Nitrogen.Conc.+OD+PL+emission_CO2+His+lactate+PO4.apporte+PO4.utilise; 0.757, 0.893, tmp+Main.P-Source.Conc.+Main.Thr.Conc.+Nitrogen.Conc.+total.Vol+PL+emission_CO2+rab+lactate+PO4.ferm.+PO4.apporte; 0.752, 0.893, pH+tmp+Main.P-Source.Conc.+Nitrogen.Conc.+total.Vol+PL+emission_CO2+rab+His+lactate+PO4.ferm.+PO4.utilise; 0.752, 0.893, tmp+Main.P-Source.Conc.+Nitrogen.Conc.+OD+Lys_conc.+total.Vol+PL+emission_CO2+His+lactate+PO4.ferm.+PO4.apporte; 0.742, 0.893, pH+tmp+Main.P-Source.Conc.+Nitrogen.Conc.+OD+total.Vol+PL+emission_O2+emission_CO2+Thr+His+lactate+PO4.apporte+PO4.utilise; 0.747, 0.893, tmp+Main.P-Source.Conc.+P-Source.Feed.conc.+Nitrogen.Conc.+OD+total.Vol+PL+emission_CO2+Thr+His+lactate+

PO4.apporte+PO4.utilise; 0.757, 0.893, Main.P-Source.Conc.+Nitrogen.Conc.+total.Vol+yield+PL+emission_CO2+Thr+His+lactate+PO4.apporte+PO4.utilise; 0.765, 0.893, tmp+P-Source.Feed.conc.+OD+PL+emission_CO2+Thr+His+lactate+PO4.apporte; 0.761, 0.893, tmp+P-Source.Feed.conc.+yield+PL+emission_CO2+Thr+His+lactate+PO4.ferm.+PO4.apporte; 0.757, 0.893, pH+Main.P-Source.Conc.+Nitrogen.Conc.+OD+total.Vol+yield+PL+emission_CO2+His+lactate+PO4.apporte; 0.761, 0.893, Main.P-Source.Conc.+Nitrogen.Conc.+OD+total.Vol+PL+emission_CO2+Thr+His+lactate+PO4.apporte; 0.747, 0.893, pH+tmp+Main.P-Source.Conc.+Nitrogen.Conc.+OD+yield+PL+emission_CO2+rab+His+lactate+PO4.ferm.+PO4.apporte; 0.742, 0.893, tmp+Main.P-Source.Conc.+P-Source.Feed.conc.+Nitrogen.Conc.+total.Vol+yield+PL+emission_O2+emission_CO2+Thr+His+lactate+PO4.apporte+PO4.utilise; 0.757, 0.893, tmp+Main.P-Source.Conc.+Main.Thr.Conc.+Nitrogen.Conc.+total.Vol+emission_CO2+rab+Thr+lactate+PO4.ferm.+PO4.apporte; 0.747, 0.893, pH+tmp+Main.P-Source.Conc.+Nitrogen.Conc.+total.Vol+PL+emission_CO2+rab+His+lactate+SO4.ferm.+PO4.ferm.+PO4.apporte; 0.765, 0.893, tmp+P-Source.Feed.conc.+Lys_conc.+PL+emission_CO2+Thr+His+lactate+PO4.apporte; 0.747, 0.893, pH+tmp+Main.P-Source.Conc.+P-Source.Feed.conc.+Nitrogen.Conc.+PL+emission_O2+emission_CO2+Thr+His+lactate+PO4.ferm.+PO4.apporte; 0.761, 0.893, tmp+Main.P-Source.Conc.+P-Source.Feed.conc.+Nitrogen.Conc.+PL+emission_CO2+His+lactate+PO4.apporte+PO4.utilise; 0.773, 0.893, pH+Main.P-Source.Conc.+Nitrogen.Conc.+total.Vol+emission_CO2+lactate+PO4.apporte; 0.761, 0.893, tmp+Main.P-Source.Conc.+Nitrogen.Conc.+total.Vol+yield+emission_O2+emission_CO2+lactate+PO4.ferm.+PO4.apporte; 0.757, 0.893, pH+tmp+Main.P-Source.Conc.+Nitrogen.Conc.+total.Vol+emission_O2+emission_CO2+Thr+lactate+PO4.ferm.+PO4.apporte; 0.761, 0.893, tmp+P-Source.Feed.conc.+Lys_conc.+PL+emission_CO2+Thr+His+lactate+PO4.apporte+PO4.utilise; 0.757, 0.893, pH+tmp+Main.P-Source.Conc.+P-Source.Feed.conc.+Nitrogen.Conc.+PL+emission_CO2+Thr+His+lactate+PO4.apporte; 0.761, 0.893, tmp+P-Source.Feed.conc.+Main.Thr.Conc.+PL+emission_CO2+Thr+His+lactate+PO4.ferm.+PO4.utilise; 0.757, 0.893, Main.P-Source.Conc.+P-Source.Feed.conc.+Nitrogen.Conc.+OD+total.Vol+PL+emission_CO2+His+lactate+PO4.apporte+PO4.utilise; 0.747, 0.893, pH+tmp+Main.P-Source.Conc.+P-Source.Feed.conc.+Nitrogen.Conc.+PL+emission_CO2+rab+Thr+His+lactate+PO4.apporte+PO4.utilise; 0.752, 0.893, pH+tmp+Main.P-Source.Conc.+Nitrogen.Conc.+total.Vol+PL+emission_CO2+His+lactate+SO4.ferm.+PO4.apporte+PO4.utilise; 0.761, 0.893, Main.P-Source.Conc.+Nitrogen.Conc.+OD+total.Vol+PL+emission_O2+emission_CO2+His+lactate+PO4.apporte; 0.765, 0.893, tmp+Main.P-Source.Conc.+Nitrogen.Conc.+total.Vol+PL+emission_O2+emission_CO2+lactate+PO4.apporte; 0.769, 0.893, tmp+Main.P-Source.Conc.+Nitrogen.Conc.+emission_O2+emission_CO2+lactate+PO4.apporte+PO4.utilise; 0.761, 0.893, tmp+Main.P-Source.Conc.+P-Source.Feed.conc.+Nitrogen.Conc.+PL+emission_CO2+His+lactate+PO4.ferm.+PO4.apporte; 0.747, 0.893, tmp+Main.P-Source.Conc.+Nitrogen.Conc.+OD+yield+PL+emission_O2+emission_CO2+Thr+His+lactate+PO4.ferm.+PO4.apporte; 0.747, 0.893, pH+tmp+Main.P-Source.Conc.+P-Source.Feed.conc.+Nitrogen.Conc.+total.Vol+PL+emission_O2+emission_CO2+His+lactate+PO4.apporte+PO4.utilise; 0.752, 0.893, pH+tmp+Main.P-Source.Conc.+P-Source.Feed.conc.+Nitrogen.Conc.+PL+emission_CO2+Thr+His+lactate+PO4.ferm.+PO4.apporte; 0.761, 0.893, tmp+Main.P-Source.Conc.+P-Source.Feed.conc.+Main.Thr.Conc.+Nitrogen.Conc.+emission_CO2+rab+lactate+PO4.apporte+PO4.utilise; 0.765, 0.893, tmp+Main.P-Source.Conc.+Nitrogen.Conc.+total.Vol+PL+emission_CO2+rab+lactate+PO4.apporte; 0.747, 0.893, pH+tmp+Main.P-Source.Conc.+P-Source.Feed.conc.+Nitrogen.Conc.+PL+emission_CO2+rab+Thr+His+lactate+PO4.ferm.+PO4.apporte; 0.742, 0.893, pH+tmp+Main.P-Source.Conc.+Nitrogen.Conc.+total.Vol+PL+emission_O2+emission_CO2+rab+Thr+His+lactate+PO4.ferm.+PO4.apporte; 0.756, 0.893, pH+tmp+Main.P-Source.Conc.+Nitrogen.Conc.+total.Vol+PL+emission_CO2+rab+lactate+PO4.apporte+PO4.utilise; 0.761, 0.893, tmp+Main.P-Source.Conc.+Nitrogen.Conc.+total.Vol+yield+emission_CO2+rab+lactate+PO4.ferm.+PO4.apporte; 0.765, 0.893, tmp+Main.P-Source.Conc.+Nitrogen.Conc.+total.Vol+emission_O2+emission_CO2+lactate+PO4.ferm.+PO4.utilise; 0.756, 0.893, Main.P-Source.Conc.+Nitrogen.Conc.+OD+total.Vol+PL+emission_CO2+Thr+His+lactate+PO4.apporte+PO4.utilise; 0.765, 0.893, tmp+Main.P-Source.Conc.+Nitrogen.Conc.+PL+emission_CO2+His+lactate+PO4.apporte+PO4.utilise; 0.761, 0.893, tmp+Main.P-Source.Conc.+Nitrogen.Conc.+OD+PL+emission_CO2+His+lactate+PO4.ferm.+PO4.utilise; 0.765, 0.893, tmp+Main.P-Source.Conc.+Nitrogen.Conc.+PL+emission_CO2+His+lactate+PO4.ferm.+PO4.apporte; 0.756, 0.893, tmp+Main.P-Source.Conc.+P-Source.Feed.conc.+Nitrogen.Conc.+PL+emission_O2+emission_CO2+Thr+His+lactate+PO4.apporte; 0.761, 0.893, tmp+Main.P-Source.Conc.+P-Source.Feed.conc.+Main.Thr.Conc.+Nitrogen.Conc.+emission_CO2+rab+lactate+PO4.ferm.+PO4.apporte; 0.756, 0.893, tmp+Main.P-Source.Conc.+P-Source.Feed.conc.+Nitrogen.Conc.+PL+emission_O2+emission_CO2+His+lactate+PO4.ferm.+PO4.apporte; 0.761, 0.893, tmp+Main.P-Source.Conc.+Nitrogen.Conc.+PL+emission_CO2+rab+His+lactate+PO4.ferm.+PO4.apporte; 0.752, 0.893, tmp+Main.P-Source.Conc.+Nitrogen.Conc.+total.Vol+PL+emission_O2+emission_CO2+rab+Thr+lactate+PO4.apporte+PO4.utilise; 0.752, 0.893, tmp+Main.P-Source.Conc.+P-Source.Feed.conc.+Nitrogen.Conc.+total.Vol+PL+emission_CO2+Thr+His+lactate+PO4.ferm.+PO4.utilise; 0.761, 0.893, tmp+Main.P-Source.Conc.+Nitrogen.Conc.+total.Vol+yield+emission_O2+emission_CO2+lactate+PO4.apporte+PO4.utilise; 0.761, 0.893, pH+Main.P-Source.Conc.+Nitrogen.Conc.+total.Vol+PL+emission_CO2+rab+His+lactate+PO4.apporte; 0.756, 0.893, tmp+Main.P-Source.Conc.+P-Source.Feed.conc.+Nitrogen.Conc.+PL+emission_O2+emission_CO2+His+lactate+PO4.apporte+PO4.utilise; 0.742, 0.893, pH+tmp+Main.P-Source.Conc.+Nitrogen.Conc.+Lys_conc.+total.Vol+PL+emission_O2+emission_CO2+Thr+His+lactate+PO4.ferm.+PO4.apporte; 0.752, 0.893, tmp+Main.P-Source.Conc.+Nitrogen.Conc.+Lys_conc.+total.Vol+PL+emission_O2+emission_CO2+Thr+lactate+PO4.apporte+PO4.utilise; 0.761, 0.893, tmp+Main.P-Source.Conc.+P-Source.Feed.conc.+Nitrogen.Conc.+total.Vol+emission_O2+emission_CO2+lactate+PO4.apporte+PO4.utilise; 0.756, 0.893, tmp+Main.P-Source.Conc.+P-Source.Feed.conc.+Nitrogen.Conc.+PL+emission_CO2+rab+Thr+His+lactate+PO4.apporte; 0.756, 0.893, tmp+Main.P-Source.Conc.+P-Source.Feed.conc.+Main.Thr.Conc.+Nitrogen.Conc.+total.Vol+emission_O2+emission_CO2+lactate+PO4.ferm.+PO4.apporte; 0.765, 0.893, pH+tmp+Main.P-Source.Conc.+Nitrogen.Conc.+total.Vol+emission_O2+rab+lactate+PO4.apporte; 0.747, 0.893, tmp+Main.P-Source.Conc.+Main.Thr.Conc.+Nitrogen.Conc.+OD+total.Vol+PL+emission_O2+emission_CO2+His+lactate+PO4.apporte+PO4.utilise; 0.756, 0.893, pH+tmp+Main.P-Source.Conc.+Nitrogen.Conc.+total.Vol+PL+emission_CO2+Thr+lactate+PO4.apporte+PO4.utilise; 0.747, 0.893, pH+tmp+Main.P-Source.Conc.+Main.Thr.Conc.+Nitrogen.Conc.+total.Vol+PL+emission_CO2+rab+His+lactate+PO4.apporte+PO4.utilise; 0.765, 0.893, tmp+Main.P-Source.Conc.+Nitrogen.Conc.+OD+total.Vol+emission_CO2+His+lactate+PO4.apporte; 0.756, 0.893, tmp+Main.P-Source.Conc.+Main.Thr.Conc.+Nitrogen.Conc.+total.Vol+PL+emission_CO2+rab+lactate+PO4.apporte+PO4.utilise; 0.752, 0.893, tmp+Main.P-Source.Conc.+Main.Thr.Conc.+Nitrogen.Conc.+total.Vol+emission_O2+emission_CO2+Thr+His+lactate+PO4.ferm.+PO4.apporte; 0.761, 0.893, Main.P-Source.Conc.+P-Source.Feed.conc.+Nitrogen.Conc.+OD+total.Vol+PL+emission_CO2+His+lactate+PO4.apporte; 0.747, 0.893, pH+tmp+Main.P-Source.Conc.+P-Source.Feed.conc.+Nitrogen.Conc.+total.Vol+PL+emission_CO2+rab+His+lactate+PO4.apporte+PO4.utilise; 0.752, 0.893, tmp+Main.P-Source.Conc.+P-Source.Feed.conc.+Nitrogen.Conc.+total.Vol+PL+emission_CO2+rab+Thr+lactate+PO4.apporte+PO4.utilise; 0.747, 0.893, tmp+Main.P-Source.Conc.+Main.Thr.Conc.+Nitrogen.Conc.+total.Vol+PL+emission_CO2+rab+His+lactate+SO4.ferm.+PO4.ferm.+PO4.apporte; 0.761, 0.893, tmp+Main.P-Source.Conc.+Nitrogen.Conc.+total.Vol+emission_O2+rab+His+lactate+PO4.ferm.+PO4.apporte; 0.761, 0.893, tmp+Main.P-Source.Conc.+P-Source.Feed.conc.+Nitrogen.Conc.+total.Vol+emission_CO2+rab+lactate+PO4.apporte+PO4.utilise; 0.761, 0.893, tmp+Main.P-Source.Conc.+Nitrogen.Conc.+total.Vol+yield+emission_CO2+rab+lactate+PO4.apporte+PO4.utilise; 0.747, 0.893, tmp+Main.P-Source.Conc.+Main.Thr.Conc.+Nitrogen.Conc.+total.Vol+PL+emission_CO2+rab+His+lactate+SO4.ferm.+PO4.apporte+PO4.utilise; 0.756, 0.893, tmp+P-Source.Feed.conc.+PL+emission_O2+emission_CO2+rab+Thr+His+lactate+PO4.ferm.+PO4.apporte; 0.761, 0.893, tmp+Main.P-Source.Conc.+Nitrogen.Conc.+PL+emission_CO2+rab+His+lactate+PO4.apporte+PO4.utilise; 0.752, 0.893, tmp+Main.P-Source.Conc.+Nitrogen.Conc.+total.Vol+PL+emission_CO2+rab+Thr+lactate+SO4.ferm.+PO4.ferm.+PO4.apporte; 0.747, 0.893, tmp+Main.P-Source.Conc.+P-Source.Feed.conc.+Nitrogen.Conc.+OD+PL+emission_CO2+rab+Thr+His+lactate+PO4.ferm.+PO4.apporte; 0.752, 0.893, tmp+Main.P-Source.Conc.+P-Source.Feed.conc.+Nitrogen.Conc.+OD+total.Vol+PL+emission_CO2+His+lactate+PO4.ferm.+PO4.apporte; 0.761, 0.893, Main.P-Source.Conc.+Nitrogen.Conc.+Lys_conc.+total.Vol+PL+emission_CO2+His+lactate+PO4.ferm.+PO4.apporte; 0.747, 0.893, tmp+Main.P-Source.Conc.+P-Source.Feed.conc.+Nitrogen.Conc.+OD+PL+emission_CO2+rab+Thr+His+lactate+PO4.apporte+PO4.utilise; 0.742, 0.893, tmp+Main.P-Source.Conc.+P-Source.Feed.conc.+Nitrogen.Conc.+total.Vol+yield+PL+emission_O2+emission_CO2+Thr+His+lactate+PO4.ferm.+PO4.apporte; 0.777, 0.893, tmp+Main.P-Source.Conc.+Nitrogen.Conc.+emission_CO2+lactate+PO4.apporte; 0.761, 0.893, tmp+Main.P-Source.Conc.+Nitrogen.Conc.+total.Vol+PL+emission_CO2+rab+Thr+lactate+PO4.apporte; 0.756, 0.893, Main.P-Source.Conc.+P-Source.Feed.conc.+Nitrogen.Conc.+total.Vol+PL+emission_CO2+Thr+His+lactate+PO4.ferm.+PO4.apporte; 0.756, 0.893, pH+Main.P-Source.Conc.+Nitrogen.Conc.+total.Vol+PL+emission_CO2+rab+His+lactate+PO4.ferm.+PO4.apporte; 0.761, 0.893, tmp+P-Source.Feed.conc.+Lys_conc.+PL+emission_CO2+Thr+His+lactate+PO4.ferm.+PO4.apporte; 0.756, 0.893, tmp+P-Source.Feed.conc.+total.Vol+PL+emission_O2+emission_CO2+Thr+His+lactate+PO4.ferm.+PO4.apporte; 0.765, 0.893, tmp+Main.P-Source.Conc.+Nitrogen.Conc.+total.Vol+emission_O2+emission_CO2+Thr+lactate+PO4.apporte; 0.747, 0.893, tmp+Main.P-Source.Conc.+P-Source.Feed.conc.+Nitrogen.Conc.+total.Vol+PL+emission_O2+emission_CO2+Thr+His+lactate+PO4.ferm.+PO4.utilise; 0.747, 0.893, tmp+Main.P-Source.Conc.+Nitrogen.Conc.+OD+yield+PL+emission_CO2+rab+Thr+His+lactate+PO4.apporte+PO4.utilise; 0.760, 0.893, tmp+Main.P-Source.Conc.+Nitrogen.Conc.+total.Vol+PL+emission_CO2+His+lactate+SO4.ferm.+PO4.apporte; 0.756, 0.893, Main.P-Source.Conc.+P-Source.Feed.conc.+Nitrogen.Conc.+total.Vol+PL+emission_O2+emission_CO2+His+lactate+PO4.ferm.+PO4.apporte; 0.765, 0.893, pH+tmp+Main.P-Source.Conc.+Nitrogen.Conc.+total.Vol+emission_O2+emission_CO2+lactate+PO4.apporte; 0.747, 0.893, tmp+Main.P-Source.Conc.+P-Source.Feed.conc.+Nitrogen.Conc.+OD+total.Vol+PL+emission_O2+emission_CO2+His+lactate+PO4.ferm.+PO4.apporte; 0.756, 0.893, tmp+Main.P-Source.Conc.+P-Source.Feed.conc.+Main.Thr.Conc.+Nitrogen.Conc.+total.Vol+emission_CO2+rab+lactate+PO4.ferm.+PO4.apporte; 0.756, 0.893, Main.P-Source.Conc.+Nitrogen.Conc.+OD+total.Vol+PL+emission_O2+emission_CO2+His+lactate+PO4.ferm.+PO4.apporte; 0.747, 0.893, pH+tmp+Main.P-Source.Conc.+Nitrogen.Conc.+total.Vol+PL+emission_CO2+His+lactate+SO4.ferm.+PO4.apporte+PO4.utilise; 0.756, 0.893, tmp+Main.P-Source.Conc.+Main.Thr.Conc.+Nitrogen.Conc.+total.Vol+emission_CO2+rab+lactate+SO4.ferm.+PO4.ferm.+PO4.apporte; 0.760, 0.893, tmp+Main.P-Source.Conc.+P-Source.Feed.conc.+Nitrogen.Conc.+total.Vol+emission_CO2+His+lactate+PO4.ferm.+PO4.apporte; 0.756, 0.893, pH+Main.P-Source.Conc.+Nitrogen.Conc.+OD+yield+PL+emission_CO2+His+lactate+PO4.apporte+PO4.utilise; 0.756, 0.893, tmp+Main.P-Source.Conc.+Nitrogen.Conc.+total.Vol+PL+emission_O2+emission_CO2+lactate+SO4.ferm.+PO4.ferm.+PO4.apporte; 0.742, 0.893, pH+tmp+Main.P-Source.Conc.+Nitrogen.Conc.+total.Vol+PL+emission_O2+emission_CO2+rab+Thr+His+lactate+PO4.apporte+PO4.utilise; 0.751, 0.893, tmp+Main.P-Source.Conc.+Nitrogen.Conc.+OD+total.Vol+emission_CO2+rab+Thr+His+lactate+PO4.apporte+PO4.utilise; 0.747, 0.893, pH+tmp+Main.P-Source.Conc.+Nitrogen.Conc.+total.Vol+PL+emission_CO2+rab+His+lactate+SO4.ferm.+PO4.apporte+PO4.utilise; 0.756, 0.893, tmp+Main.P-Source.Conc.+Nitrogen.Conc.+total.Vol+PL+emission_CO2+His+lactate+PO4.ferm.+PO4.apporte+PO4.utilise; 0.756, 0.893, tmp+Main.P-Source.Conc.+Main.Thr.Conc.+Nitrogen.Conc.+total.Vol+emission_CO2+rab+Thr+lactate+PO4.apporte+PO4.utilise; 0.751, 0.893, tmp+Main.P-Source.Conc.+Nitrogen.Conc.+OD+Lys_conc.+total.Vol+PL+emission_CO2+His+lactate+PO4.apporte+PO4.utilise; 0.756, 0.893, tmp+Main.P-Source.Conc.+P-Source.Feed.conc.+Main.Thr.Conc.+Nitrogen.Conc.+total.Vol+emission_O2+emission_CO2+lactate+PO4.apporte+PO4.utilise; 0.756, 0.893, pH+Main.P-Source.Conc.+Nitrogen.Conc.+OD+yield+PL+emission_CO2+His+lactate+PO4.ferm.+PO4.apporte; 0.751, 0.893, tmp+Main.P-Source.Conc.+Nitrogen.Conc.+total.Vol+PL+emission_O2+rab+Thr+His+lactate+PO4.ferm.+PO4.apporte; 0.741, 0.893, pH+tmp+Main.P-

Source.Conc.+Nitrogen.Conc.+OD+total.Vol+PL+ emission_CO2+rab+Thr+His+lactate+PO4.ferm.+ PO4.apporte; 0.751, 0.893, pH+tmp+Main.P-Source.Conc.+ Nitrogen.Conc.+OD+total.Vol+PL+emission_CO2+Thr+ His+lactate+PO4.apporte; 0.760, 0.893, Main.P-Source.Conc.+Nitrogen.Conc.+Lys_conc.+total.Vol+PL+ emission_CO2+His+lactate+PO4.apporte+PO4.utilise; 0.760, 0.893, tmp+Main.P-Source.Conc.+Nitrogen.Conc.+ PL+emission_CO2+Thr+His+lactate+PO4.apporte+ PO4.utilise; 0.756, 0.893, tmp+Main.P-Source.Conc.+P-Source.Feed.conc.+Nitrogen.Conc.+OD+PL+ emission_CO2+His+lactate+PO4.ferm.+PO4.apporte; 0.741, 0.893, tmp+Main.P-Source.Conc.+P-Source.Feed. conc.+Nitrogen.Conc.+Lys_conc.+total.Vol+PL+emission_O2+emission_CO2+Thr+His+lactate+PO4.ferm.+ PO4.apporte; 0.756, 0.893, pH+Main.P-Source.Conc.+Nitrogen.Conc.+total.Vol+PL+emission_CO2+rab+His+ lactate+PO4.apporte+PO4.utilise; 0.741, 0.893, tmp+ Main.P-Source.Conc.+Nitrogen.Conc.+OD+total.Vol+ yield+PL+emission_O2+emission_CO2+Thr+His+lactate+ PO4.apporte+PO4.utilise; 0.746, 0.893, pH+tmp+Main.P-Source.Conc.+Nitrogen.Conc.+Lys_conc.+total.Vol+PL+ emission_CO2+rab+His+lactate+PO4.apporte+PO4.utilise; 0.769, 0.893, tmp+Main.P-Source.Conc.+Main.Thr.Conc.+ Nitrogen.Conc.+total.Vol+emission_CO2+lactate+ PO4.apporte; 0.756, 0.893, Main.P-Source.Conc.+P-Source.Feed.conc.+Nitrogen.Conc.+total.Vol+PL+ emission_CO2+Thr+His+lactate+PO4.apporte+PO4.utilise; 0.760, 0.893, tmp+Main.P-Source.Conc.+P-Source.Feed. conc.+Nitrogen.Conc.+OD+PL+emission_CO2+His+lactate+PO4.apporte; 0.756, 0.893, tmp+Main.P-Source.Conc.+Nitrogen.Conc.+OD+total.Vol+PL+emission_O2+emission_CO2+lactate+PO4.ferm.+PO4.apporte; 0.741, 0.893, tmp+Main.P-Source.Conc.+P-Source.Feed. conc.+Nitrogen.Conc.+OD+total.Vol+PL+emission_CO2+ rab+Thr+His+lactate+PO4.ferm.+PO4.apporte; 0.756, 0.893, pH+tmp+Main.P-Source.Conc.+Nitrogen.Conc.+total.Vol+emission_CO2+rab+Thr+lactate+PO4.ferm.+ PO4.apporte; 0.751, 0.893, tmp+Main.P-Source.Conc.+P-Source.Feed.conc.+Nitrogen.Conc.+total.Vol+yield+PL+ emission_CO2+His+lactate+PO4.ferm.+PO4.apporte; 0.746, 0.893, pH+tmp+Main.P-Source.Conc.+Nitrogen. Conc.+total.Vol+PL+emission_O2+emission_CO2+rab+ His+lactate+PO4.ferm.+PO4.apporte; 0.764, 0.893, Main.P-Source.Conc.+P-Source.Feed.conc.+Nitrogen.Conc.+ total.Vol+PL+emission_CO2+lactate+PO4.ferm.+ PO4.apporte; 0.751, 0.893, tmp+Main.P-Source.Conc.+P-Source.Feed.conc.+Nitrogen.Conc.+OD+total.Vol+PL+ emission_CO2+His+lactate+PO4.apporte+PO4.utilise; 0.751, 0.893, tmp+Main.P-Source.Conc.+Nitrogen.Conc.+ OD+total.Vol+PL+emission_CO2+rab+Thr+lactate+ PO4.ferm.+PO4.apporte; 0.764, 0.893, tmp+P-Source. Feed.conc.+Main.Thr.Conc.+PL+emission_CO2+Thr+His+ lactate+PO4.apporte; 0.760, 0.893, tmp+Main.P-Source.Conc.+Nitrogen.Conc.+PL+emission_CO2+Thr+ His+lactate+PO4.ferm.+PO4.apporte; 0.756, 0.893, pH+tmp+P-Source.Feed.conc.+PL+emission_O2+emission_CO2+Thr+His+lactate+PO4.apporte+PO4.utilise; 0.756, 0.893, pH+Main.P-Source.Conc.+ Main.Thr.Conc.+Nitrogen.Conc.+total.Vol+PL+emission_CO2+His+lactate+PO4.ferm.+PO4.apporte; 0.773, 0.893, tmp+P-Source.Feed.conc.+PL+emission_CO2+His+ lactate+PO4.apporte; 0.741, 0.893, pH+tmp+Main.P-Source.Conc.+Nitrogen.Conc.+total.Vol+yield+PL+emission_O2+emission_CO2+Thr+His+lactate+PO4.apporte+ PO4.utilise; 0.769, 0.893, tmp+Main.P-Source.Conc.+ Main.Thr.Conc.+Nitrogen.Conc.+emission_CO2+rab+ lactate+PO4.apporte; 0.756, 0.893, tmp+Main.P-Source.Conc.+Main.Thr.Conc.+Nitrogen.Conc.+total.Vol+ emission_CO2+rab+lactate+SO4.ferm.+PO4.apporte+ PO4.utilise; 0.756, 0.893, tmp+Main.P-Source.Conc.+ Nitrogen.Conc.+total.Vol+PL+emission_CO2+rab+lactate+ SO4.ferm.+PO4.ferm.+PO4.apporte; 0.764, 0.893, tmp+ Main.P-Source.Conc.+Nitrogen.Conc.+total.Vol+ emission_CO2+rab+Thr+lactate+PO4.apporte; 0.760, 0.893, tmp+P-Source.Feed.conc.+OD+PL+emission_CO2+ Thr+His+lactate+PO4.ferm.+PO4.utilise; 0.746, 0.893, tmp+Main.P-Source.Conc.+Nitrogen.Conc.+OD+yield+ PL+emission_CO2+rab+Thr+His+lactate+PO4.ferm.+ PO4.apporte; 0.746, 0.893, tmp+Main.P-Source.Conc.+ Main.Thr.Conc.+Nitrogen.Conc.+OD+total.Vol+PL+ emission_CO2+rab+His+lactate+PO4.ferm.+PO4.apporte; 0.764, 0.893, tmp+P-Source.Feed.conc.+yield+PL+emission_CO2+Thr+His+lactate+PO4.apporte; 0.760, 0.893, pH+Main.P-Source.Conc.+Nitrogen.Conc.+total.Vol+PL+ emission_CO2+His+lactate+PO4.ferm.+PO4.utilise; 0.760, 0.893, tmp+Main.P-Source.Conc.+Main.Thr.Conc.+Nitrogen.Conc.+OD+emission_CO2+rab+lactate+PO4.ferm.+ PO4.apporte; 0.756, 0.893, tmp+Main.P-Source.Conc.+P-Source.Feed.conc.+Nitrogen.Conc.+OD+PL+ emission_CO2+His+lactate+PO4.apporte+PO4.utilise; 0.764, 0.893, tmp+Main.P-Source.Conc.+P-Source.Feed. conc.+Nitrogen.Conc.+PL+emission_CO2+His+lactate+ PO4.apporte; 0.760, 0.893, tmp+P-Source.Feed.conc.+Lys_conc.+PL+emission_CO2+Thr+His+lactate+PO4.ferm.+ PO4.utilise; 0.746, 0.893, pH+tmp+Main.P-Source.Conc.+ Nitrogen.Conc.+total.Vol+PL+emission_CO2+Thr+His+ lactate+SO4.ferm.+PO4.ferm.+PO4.apporte; 0.756, 0.893, Main.P-Source.Conc.+Nitrogen.Conc.+OD+total.Vol+PL+ emission_O2+emission_CO2+His+lactate+PO4.apporte+ PO4.utilise; 0.764, 0.893, pH+tmp+Main.P-Source.Conc.+ Nitrogen.Conc.+total.Vol+PL+emission_CO2+lactate+ PO4.apporte; 0.751, 0.893, tmp+Main.P-Source.Conc.+ Main.Thr.Conc.+Nitrogen.Conc.+total.Vol+emission_O2+ emission_CO2+Thr+His+lactate+PO4.apporte+PO4.utilise; 0.751, 0.893, pH+tmp+Main.P-Source.Conc.+Nitrogen. Conc.+total.Vol+emission_O2+emission_CO2+Thr+His+ lactate+PO4.ferm.+PO4.apporte; 0.764, 0.893, pH+tmp+ Main.P-Source.Conc.+Nitrogen.Conc.+total.Vol+emission_CO2+lactate+PO4.ferm.+PO4.apporte; 0.756, 0.893, pH+tmp+Main.P-Source.Conc.+Nitrogen.Conc.+total.Vol+ emission_O2+emission_CO2+Thr+lactate+PO4.apporte+ PO4.utilise; 0.751, 0.893, tmp+Main.P-Source.Conc.+Nitrogen.Conc.+total.Vol+PL+emission_CO2+rab+Thr+ lactate+SO4.ferm.+PO4.apporte+PO4.utilise; 0.756, 0.893, tmp+Main.P-Source.Conc.+P-Source.Feed.conc.+Main. Thr.Conc.+Nitrogen.Conc.+total.Vol+emission_CO2+rab+ lactate+PO4.apporte+PO4.utilise; 0.756, 0.893, tmp+ Main.P-Source.Conc.+P-Source.Feed.conc.+Nitrogen. Conc.+total.Vol+PL+emission_O2+emission_CO2+lactate+PO4.ferm.+PO4.apporte; 0.741, 0.893, tmp+Main.P-Source.Conc.+Nitrogen.Conc.+OD+total.Vol+yield+PL+ emission_O2+emission_CO2+Thr+His+lactate+ PO4.ferm.+PO4.apporte; 0.741, 0.893, tmp+Main.P-Source.Conc.+P-Source.Feed. conc.+Nitrogen.Conc.+ total.Vol+PL+emission_CO2+rab+Thr+His+lactate+ SO4.ferm.+PO4.ferm.+PO4.apporte; 0.756, 0.893, Main.P-Source.Conc.+Main.Thr.Conc.+Nitrogen. Conc.+OD+ total.Vol+PL+emission_CO2+His+lactate+PO4.ferm.+ PO4.apporte; 0.751, 0.893, tmp+Main.P-Source.Conc.+P-Source.Feed.conc.+Nitrogen.Conc.+total.Vol+yield+PL+ emission_CO2+His+lactate+PO4.apporte+PO4.utilise; 0.760, 0.893, tmp+Main.P-Source.Conc.+Main.Thr.Conc.+ Nitrogen.Conc.+OD+emission_CO2+rab+lactate+

PO4.apporte+PO4.utilise; 0.751, 0.893, tmp+Main.P-Source.Conc.+P-Source.Feed.conc.+Nitrogen.Conc.+total.Vol+PL+emission_O2+emission_CO2+Thr+His+lactate+PO4.apporte; 0.741, 0.893, pH+tmp+Main.P-Source.Conc.+Nitrogen.Conc.+OD+Lys_conc.+total.Vol+PL+emission_O2+emission_CO2+His+lactate+PO4.ferm.+PO4.apporte; 0.760, 0.893, Main.P-Source.Conc.+Nitrogen.Conc.+OD+total.Vol+PL+emission_CO2+rab+His+lactate+PO4.apporte; 0.760, 0.893, tmp+Main.P-Source.Conc.+Nitrogen.Conc.+total.Vol+PL+emission_O2+rab+His+lactate+PO4.apporte; 0.764, 0.893, tmp+Main.P-Source.Conc.+Nitrogen.Conc.+total.Vol+yield+emission_CO2+His+lactate+PO4.apporte; 0.755, 0.893, Main.P-Source.Conc.+P-Source.Feed.conc.+Nitrogen.Conc.+total.Vol+PL+emission_O2+emission_CO2+His+lactate+PO4.apporte+PO4.utilise; 0.741, 0.893, tmp+Main.P-Source.Conc.+P-Source.Feed.conc.+Nitrogen.Conc.+OD+total.Vol+PL+emission_CO2+rab+Thr+His+lactate+PO4.apporte+PO4.utilise; 0.751, 0.893, pH+tmp+Main.P-Source.Conc.+P-Source.Feed.conc.+Nitrogen.Conc.+total.Vol+PL+emission_CO2+Thr+His+lactate+PO4.apporte; 0.741, 0.893, pH+tmp+Main.P-Source.Conc.+Nitrogen.Conc.+total.Vol+yield+PL+emission_O2+emission_CO2+Thr+His+lactate+PO4.ferm.+PO4.apporte; 0.751, 0.893, pH+tmp+Main.P-Source.Conc.+Nitrogen.Conc.+total.Vol+PL+emission_O2+emission_CO2+Thr+His+lactate+PO4.apporte; 0.760, 0.893, pH+tmp+Main.P-Source.Conc.+Nitrogen.Conc.+total.Vol+emission_CO2+rab+His+lactate+PO4.apporte; 0.760, 0.893, tmp+Main.P-Source.Conc.+Nitrogen.Conc.+total.Vol+emission_O2+emission_CO2+rab+lactate+PO4.ferm.+PO4.apporte; 0.760, 0.893, pH+tmp+Main.P-Source.Conc.+Main.Thr. Conc.+Nitrogen.Conc.+emission_CO2+rab+lactate+PO4.apporte+PO4.utilise; 0.751, 0.893, tmp+Main.P-Source.Conc.+Main.Thr.Conc.+Nitrogen.Conc.+total.Vol+emission_O2+emission_CO2+His+lactate+SO4.ferm.+PO4.ferm.+PO4.apporte; 0.746, 0.893, tmp+Main.P-Source.Conc.+P-Source.Feed.conc.+Nitrogen.Conc.+OD+total.Vol+PL+emission_CO2+rab+His+lactate+PO4.ferm.+PO4.apporte; 0.755, 0.893, pH+Main.P-Source.Conc.+Main.Thr.Conc.+Nitrogen.Conc.+total.Vol+PL+emission_CO2+His+lactate+PO4.apporte+PO4.utilise; 0.760, 0.893, tmp+P-Source.Feed.conc.+yield+PL+emission_CO2+Thr+His+lactate+PO4.ferm.+PO4.utilise; 0.751, 0.893, pH+tmp+Main.P-Source.Conc.+Nitrogen.Conc.+OD+yield+PL+emission_O2+emission_CO2+His+lactate+PO4.apporte; 0.760, 0.893, pH+tmp+Main.P-Source.Conc.+Main.Thr.Conc.+Nitrogen.Conc.+emission_CO2+rab+lactate+PO4.ferm.+PO4.apporte; 0.764, 0.893, Main.P-Source.Conc.+Nitrogen.Conc.+OD+PL+emission_O2+emission_CO2+His+lactate+PO4.apporte; 0.746, 0.893, tmp+Main.P-Source.Conc.+P-Source.Feed.conc.+Nitrogen.Conc.+OD+total.Vol+PL+emission_O2+emission_CO2+His+lactate+PO4.apporte+PO4.utilise; 0.751, 0.893, tmp+Main.P-Source.Conc.+Main.Thr.Conc.+Nitrogen.Conc.+total.Vol+PL+emission_O2+emission_CO2+Thr+lactate+PO4.ferm.+PO4.apporte; 0.741, 0.893, pH+tmp+Main.P-Source.Conc.+Nitrogen.Conc.+total.Vol+PL+emission_O2+emission_CO2+Thr+His+lactate+SO4.ferm.+PO4.ferm.+PO4.apporte; 0.751, 0.893, tmp+Main.P-Source.Conc.+Nitrogen.Conc.+total.Vol+yield+PL+emission_O2+emission_CO2+Thr+lactate+PO4.apporte+PO4.utilise; 0.751, 0.893, tmp+Main.P-Source.Conc.+Nitrogen.Conc.+total.Vol+PL+emission_O2+emission_CO2+rab+Thr+His+lactate+PO4.apporte+PO4.utilise; 0.746, 0.893, tmp+Main.P-Source.Conc.+P-Source.Feed.conc.+Nitrogen.Conc.+total.Vol+yield+PL+emission_O2+emission_CO2+His+lactate+PO4.apporte+PO4.utilise; 0.741, 0.893, pH+tmp+Main.P-Source.Conc.+Nitrogen.Conc.+Lys_conc.+total.Vol+PL+emission_O2+emission_CO2+Thr+His+lactate+PO4.apporte+PO4.utilise; 0.746, 0.893, tmp+Main.P-Source.Conc.+P-Source.Feed. conc.+Nitrogen.Conc.+total.Vol+yield+PL+emission_O2+emission_CO2+His+lactate+PO4.ferm.+PO4.apporte; 0.741, 0.893, tmp+Main.P-Source.Conc.+Nitrogen.Conc.+OD+Lys_conc.+total.Vol+PL+emission_CO2+rab+Thr+His+lactate+PO4.ferm.+PO4.apporte; 0.751, 0.893, tmp+Main.P-Source.Conc.+Nitrogen.Conc.+total.Vol+yield+PL+emission_CO2+His+lactate+SO4.ferm.+PO4.ferm.+PO4.apporte; 0.760, 0.893, tmp+Main.P-Source.Conc.+P-Source.Feed.conc.+Main.Thr.Conc.+Nitrogen.Conc.+emission_O2+emission_CO2+lactate+PO4.apporte+PO4.utilise; 0.768, 0.893, Main.P-Source.Conc.+Nitrogen.Conc.+OD+total.Vol+emission_CO2+His+lactate+PO4.apporte; 0.755, 0.893, tmp+Main.P-Source.Conc.+Nitrogen.Conc.+PL+emission_CO2+rab+Thr+His+lactate+PO4.ferm.+PO4.apporte; 0.755, 0.893, tmp+P-Source.Feed.conc.+total.Vol+PL+emission_CO2+rab+Thr+His+lactate+PO4.apporte+PO4.utilise; 0.760, 0.893, tmp+Main.P-Source.Conc.+Nitrogen.Conc.+total.Vol+emission_O2+rab+His+lactate+PO4.apporte+PO4.utilise; 0.764, 0.893, tmp+Main.P-Source.Conc.+Nitrogen.Conc.+emission_CO2+rab+His+lactate+PO4.ferm.+PO4.apporte; 0.760, 0.893, tmp+Main.P-Source.Conc.+Nitrogen.Conc.+PL+emission_O2+emission_CO2+His+lactate+PO4.ferm.+PO4.apporte; 0.755, 0.893, tmp+P-Source.Feed.conc.+PL+emission_O2+emission_CO2+rab+Thr+His+lactate+PO4.ferm.+PO4.utilise; 0.741, 0.893, tmp+Main.P-Source.Conc.+P-Source.Feed.conc.+Nitrogen.Conc.+total.Vol+yield+PL+emission_CO2+rab+Thr+His+lactate+PO4.apporte+PO4.utilise; 0.755, 0.893, pH+tmp+Main.P-Source.Conc.+P-Source.Feed.conc.+Nitrogen.Conc.+total.Vol+PL+emission_CO2+His+lactate+PO4.apporte; 0.755, 0.893, pH+tmp+Main.P-Source.Conc.+Nitrogen.Conc.+OD+PL+emission_O2+emission_CO2+His+lactate+PO4.apporte; 0.746, 0.893, pH+tmp+Main.P-Source.Conc.+Nitrogen.Conc.+total.Vol+PL+emission_CO2+Thr+His+lactate+SO4.ferm.+PO4.apporte+PO4.utilise; 0.755, 0.893, tmp+Main.P-Source.Conc.+Nitrogen.Conc.+total.Vol+PL+emission_O2+emission_CO2+lactate+SO4.ferm.+PO4.apporte+PO4.utilise; 0.751, 0.893, pH+tmp+Main.P-Source.Conc.+Nitrogen.Conc.+OD+yield+PL+emission_CO2+rab+His+lactate+PO4.apporte; 0.741, 0.893, tmp+Main.P-Source.Conc.+P-Source.Feed.conc.+Nitrogen.Conc.+total.Vol+PL+emission_CO2+rab+Thr+His+lactate+SO4.ferm.+PO4.apporte+PO4.utilise; 0.746, 0.893, tmp+Main.P-Source.Conc.+Main.Thr.Conc.+Nitrogen.Conc.+OD+total.Vol+PL+emission_CO2+rab+His+lactate+PO4.apporte+PO4.utilise; 0.764, 0.893, Main.P-Source.Conc.+P-Source.Feed.conc.+Nitrogen.Conc.+total.Vol+PL+emission_CO2+lactate+PO4.apporte+PO4.utilise; 0.746, 0.893, pH+tmp+Main.P-Source.Conc.+Nitrogen.Conc.+OD+total.Vol+yield+PL+emission_CO2+His+lactate+PO4.ferm.+PO4.apporte; 0.751, 0.893, tmp+Main.P-Source.Conc.+Main.Thr.Conc.+Nitrogen.Conc.+total.Vol+emission_CO2+rab+Thr+His+lactate+PO4.ferm.+PO4.apporte; 0.760, 0.893, pH+tmp+Main.P-Source.Conc.+Nitrogen.Conc.+total.Vol+PL+emission_CO2+lactate+PO4.ferm.+PO4.apporte; 0.755, 0.893, tmp+Main.P-Source.Conc.+Nitrogen.Conc.+OD+total.Vol+PL+emission_CO2+rab+lactate+PO4.ferm.+PO4.apporte; 0.755, 0.893, pH+tmp+Main.P-Source.Conc.+

Nitrogen.Conc.+OD+PL+emission_CO2+rab+His+lactate+PO4.apporte; 0.760, 0.893, Main.P-Source.Conc.+Nitrogen.Conc.+total.Vol+PL+emission_CO2+His+lactate+PO4.ferm.+PO4.apporte+PO4.utilise; 0.755, 0.893, tmp+Main.P-Source.Conc.+Nitrogen.Conc.+PL+emission_CO2+rab+Thr+His+lactate+PO4.apporte+PO4.utilise; 0.760, 0.893, tmp+Main.P-Source.Conc.+P-Source.Feed.conc.+Nitrogen.Conc.+total.Vol+emission_CO2+His+lactate+PO4.apporte+PO4.utilise; 0.751, 0.893, pH+tmp+Main.P-Source.Conc.+Nitrogen.Conc.+OD+total.Vol+emission_CO2+rab+His+lactate+PO4.ferm.+PO4.apporte; 0.760, 0.893, Main.P-Source.Conc.+Main.Thr.Conc.+Nitrogen.Conc.+OD+total.Vol+PL+emission_CO2+His+lactate+PO4.apporte; 0.755, 0.893, tmp+P-Source.Feed.conc.+total.Vol+PL+emission_O2+emission_CO2+Thr+His+lactate+PO4.ferm.+PO4.utilise; 0.741, 0.893, pH+tmp+Main.P-Source.Conc.+Nitrogen.Conc.+OD+total.Vol+PL+emission_CO2+rab+Thr+His+lactate+PO4.apporte+PO4.utilise; 0.755, 0.893, Main.P-Source.Conc.+Main.Thr.Conc.+Nitrogen.Conc.+OD+total.Vol+PL+emission_CO2+His+lactate+PO4.apporte+PO4.utilise; 0.746, 0.893, tmp+Main.P-Source.Conc.+Nitrogen.Conc.+total.Vol+yield+PL+emission_O2+emission_CO2+His+lactate+SO4.ferm.+PO4.apporte+PO4.utilise; 0.746, 0.893, tmp+Main.P-Source.Conc.+P-Source.Feed.conc.+Nitrogen.Conc.+total.Vol+PL+emission_CO2+Thr+His+lactate+SO4.ferm.+PO4.ferm.+PO4.apporte; 0.746, 0.893, tmp+Main.P-Source.Conc.+P-Source.Feed.conc.+Nitrogen.Conc.+total.Vol+PL+emission_CO2+rab+Thr+His+lactate+PO4.ferm.+PO4.utilise; 0.760, 0.893, tmp+Main.P-Source.Conc.+Nitrogen.Conc.+PL+emission_O2+emission_CO2+His+lactate+PO4.apporte+PO4.utilise; 0.755, 0.893, tmp+Main.P-Source.Conc.+P-Source.Feed.conc.+Nitrogen.Conc.+total.Vol+emission_O2+emission_CO2+Thr+lactate+PO4.ferm.+PO4.apporte; 0.760, 0.893, tmp+Main.P-Source.Conc.+P-Source.Feed.conc.+Main.Thr.Conc.+Nitrogen.Conc.+emission_O2+emission_CO2+lactate+PO4.ferm.+PO4.apporte; 0.751, 0.893, tmp+Main.P-Source.Conc.+Nitrogen.Conc.+total.Vol+yield+PL+emission_CO2+His+lactate+SO4.ferm.+PO4.apporte+PO4.utilise; 0.751, 0.893, tmp+Main.P-Source.Conc.+Nitrogen.Conc.+OD+total.Vol+PL+emission_CO2+rab+Thr+lactate+PO4.apporte+PO4.utilise; 0.760, 0.893, pH+tmp+P-Source.Feed.conc.+PL+emission_O2+emission_CO2+Thr+His+lactate+PO4.apporte; 0.760, 0.892, pH+tmp+Main.P-Source.Conc.+Nitrogen.Conc.+total.Vol+emission_O2+emission_CO2+His+lactate+PO4.apporte; 0.760, 0.892, tmp+Main.P-Source.Conc.+Main.Thr.Conc.+Nitrogen.Conc.+total.Vol+emission_CO2+His+lactate+PO4.ferm.+PO4.apporte; 0.760, 0.892, tmp+Main.P-Source.Conc.+Main.Thr.Conc.+Nitrogen.Conc.+OD+emission_O2+emission_CO2+lactate+PO4.ferm.+PO4.apporte; 0.750, 0.892, tmp+Main.P-Source.Conc.+Nitrogen.Conc.+Lys_conc.+total.Vol+PL+emission_CO2+rab+Thr+lactate+PO4.ferm.+PO4.apporte; 0.746, 0.892, tmp+Main.P-Source.Conc.+Nitrogen.Conc.+Lys_conc.+total.Vol+yield+PL+emission_O2+emission_CO2+His+lactate+PO4.ferm.+PO4.apporte; 0.746, 0.892, pH+tmp+Main.P-Source.Conc.+Nitrogen.Conc.+OD+yield+PL+emission_CO2+Thr+His+lactate+PO4.apporte+PO4.utilise; 0.750, 0.892, tmp+Main.P-Source.Conc.+P-Source.Feed.conc.+Nitrogen.Conc.+total.Vol+emission_O2+emission_CO2+Thr+His+lactate+PO4.ferm.+PO4.apporte; 0.741, 0.892, tmp+Main.P-Source.Conc.+P-Source.Feed.conc.+Nitrogen.Conc.+Lys_conc.+total.Vol+PL+emission_O2+emission_CO2+Thr+His+lactate+PO4.apporte+PO4.utilise; 0.755, 0.892, Main.P-Source.Conc.+Nitrogen.Conc.+total.Vol+yield+PL+emission_O2+emission_CO2+His+lactate+PO4.ferm.+PO4.apporte; 0.750, 0.892, tmp+Main.P-Source.Conc.+P-Source.Feed.conc.+Nitrogen.Conc.+yield+PL+emission_CO2+Thr+His+lactate+PO4.apporte+PO4.utilise; 0.755, 0.892, tmp+Main.P-Source.Conc.+Nitrogen.Conc.+total.Vol+emission_CO2+rab+His+lactate+SO4.ferm.+PO4.ferm.+PO4.apporte; 0.755, 0.892, Main.P-Source.Conc.+Nitrogen.Conc.+total.Vol+PL+emission_O2+emission_CO2+Thr+His+lactate+PO4.ferm.+PO4.apporte; 0.746, 0.892, pH+tmp+Main.P-Source.Conc.+Nitrogen.Conc.+OD+total.Vol+yield+PL+emission_CO2+His+lactate+PO4.apporte+PO4.utilise; 0.755, 0.892, tmp+Main.P-Source.Conc.+Nitrogen.Conc.+PL+emission_O2+emission_CO2+Thr+His+lactate+PO4.ferm.+PO4.apporte; 0.750, 0.892, pH+tmp+Main.P-Source.Conc.+Nitrogen.Conc.+OD+yield+PL+emission_CO2+Thr+His+lactate+PO4.apporte; 0.750, 0.892, tmp+Main.P-Source.Conc.+Main.Thr.Conc.+Nitrogen.Conc.+total.Vol+emission_O2+emission_CO2+His+lactate+SO4.ferm.+PO4.apporte+PO4.utilise; 0.755, 0.892, tmp+Main.P-Source.Conc.+P-Source.Feed.conc.+Nitrogen.Conc.+total.Vol+PL+emission_CO2+rab+lactate+PO4.ferm.+PO4.apporte; 0.760, 0.892, tmp+Main.P-Source.Conc.+Main.Thr.Conc.+Nitrogen.Conc.+OD+emission_O2+emission_CO2+lactate+PO4.apporte+PO4.utilise; 0.755, 0.892, tmp+Main.P-Source.Conc.+Nitrogen.Conc.+OD+total.Vol+PL+emission_O2+emission_CO2+lactate+PO4.apporte+PO4.utilise; 0.746, 0.892, pH+tmp+Main.P-Source.Conc.+Nitrogen.Conc.+total.Vol+PL+emission_O2+emission_CO2+rab+His+lactate+PO4.apporte+PO4.utilise; 0.755, 0.892, tmp+Main.P-Source.Conc.+Nitrogen.Conc.+PL+emission_O2+emission_CO2+Thr+His+lactate+PO4.apporte+PO4.utilise; 0.746, 0.892, tmp+Main.P-Source.Conc.+P-Source.Feed.conc.+Nitrogen.Conc.+total.Vol+PL+emission_CO2+Thr+His+lactate+SO4.ferm.+PO4.apporte+PO4.utilise; 0.755, 0.892, pH+tmp+P-Source.Feed.conc.+PL+emission_O2+emission_CO2+Thr+His+lactate+PO4.ferm.+PO4.apporte; 0.750, 0.892, tmp+Main.P-Source.Conc.+Nitrogen.Conc.+total.Vol+yield+PL+emission_O2+emission_CO2+Thr+lactate+PO4.ferm.+PO4.apporte; 0.755, 0.892, Main.P-Source.Conc.+Nitrogen.Conc.+total.Vol+yield+PL+emission_O2+emission_CO2+His+lactate+PO4.apporte+PO4.utilise; 0.750, 0.892, tmp+Main.P-Source.Conc.+Main.Thr.Conc.+Nitrogen.Conc.+total.Vol+emission_O2+emission_CO2+rab+His+lactate+PO4.ferm.+PO4.apporte; 0.746, 0.892, tmp+Main.P-Source.Conc.+Nitrogen.Conc.+total.Vol+yield+PL+emission_O2+emission_CO2+His+lactate+SO4.ferm.+PO4.ferm.+PO4.apporte; 0.746, 0.892, pH+tmp+Main.P-Source.Conc.+Nitrogen.Conc.+OD+yield+PL+emission_CO2+Thr+His+lactate+PO4.ferm.+PO4.apporte; 0.759, 0.892, pH+tmp+Main.P-Source.Conc.+Nitrogen.Conc.+total.Vol+PL+emission_CO2+Thr+lactate+PO4.apporte; 0.750, 0.892, tmp+Main.P-Source.Conc.+Main.Thr.Conc.+Nitrogen.Conc.+OD+PL+emission_O2+emission_CO2+His+lactate+PO4.ferm.+PO4.apporte; 0.755, 0.892, tmp+Main.P-Source.Conc.+Nitrogen.Conc.+total.Vol+PL+emission_CO2+rab+lactate+SO4.ferm.+PO4.apporte+PO4.utilise; 0.759, 0.892, tmp+Main.P-Source.Conc.+Nitrogen.Conc.+PL+emission_CO2+rab+Thr+lactate+PO4.ferm.+PO4.apporte; 0.755, 0.892, Main.P-Source.Conc.+P-Source.Feed.conc.+Nitrogen.Conc.+total.Vol+PL+emission_CO2+rab+His+lactate+PO4.ferm.+PO4.apporte; 0.750, 0.892, pH+tmp+Main.P-Source.Conc.+Nitrogen.Conc.+OD+total.Vol+ yield+PL+emission_CO2+His+lactate+PO4.apporte; 0.764, 0.892, Main.P-Source.Conc.+P-Source.Feed.conc.+Nitrogen.Conc.+total.Vol+emission_CO2+His+lactate+PO4.ferm.+PO4.apporte; 0.750, 0.892, pH+tmp+Main.P-Source.Conc.+Nitrogen.Conc.+Lys_conc.+total.Vol+PL+emission_CO2+His+lactate+PO4.ferm.+PO4.apporte; 0.759, 0.892, pH+Main.P-Source.Conc.+Main.Thr.Conc.+Nitrogen.Conc.+total.Vol+PL+emission_CO2+His+lactate+PO4.apporte; 0.741, 0.892, tmp+Main.P-Source.Conc.+P-Source.Feed.conc.+Nitrogen.Conc.+total.Vol+yield+PL+emission_CO2+rab+Thr+His+lactate+PO4.ferm.+PO4.apporte; 0.750, 0.892, tmp+Main.P-Source.Conc.+P-Source.Feed.conc.+Main.Thr.Conc.+Nitrogen.Conc.+total.Vol+emission_O2+emission_CO2+His+lactate+PO4.ferm.+PO4.apporte; 0.750, 0.892, pH+tmp+Main.P-Source.Conc.+Nitrogen.Conc.+OD+total.Vol+emission_O2+emission_CO2+His+lactate+PO4.ferm.+PO4.apporte; 0.750, 0.892, tmp+Main.P-Source.Conc.+Main.Thr.Conc.+Nitrogen.Conc.+OD+PL+emission_O2+emission_CO2+His+lactate+PO4.apporte+PO4.utilise; 0.768, 0.892, Main.P-Source.Conc.+P-Source.Feed.conc.+Nitrogen.Conc.+total.Vol+emission_CO2+lactate+PO4.ferm.+PO4.apporte; 0.750, 0.892, tmp+Main.P-Source.Conc.+Main.Thr.Conc.+Nitrogen.Conc.+total.Vol+PL+emission_O2+emission_CO2+Thr+lactate+PO4.apporte+PO4.utilise; 0.764, 0.892, pH+tmp+Main.P-Source.Conc.+Nitrogen.Conc.+total.Vol+emission_CO2+lactate+PO4.apporte+PO4.utilise; 0.745, 0.892, tmp+Main.P-Source.Conc.+Nitrogen.Conc.+OD+Lys_conc.+total.Vol+PL+emission_CO2+Thr+His+lactate+PO4.ferm.+PO4.apporte; 0.772, 0.892, tmp+Main.P-Source.Conc.+Nitrogen.Conc.+emission_CO2+rab+lactate+PO4.apporte; 0.764, 0.892, tmp+Main.P-Source.Conc.+Nitrogen.Conc.+PL+emission_CO2+rab+lactate+PO4.ferm.+PO4.apporte; 0.750, 0.892, pH+tmp+Main.P-Source.Conc.+Nitrogen.Conc.+total.Vol+PL+emission_O2+rab+His+lactate+PO4.ferm.+PO4.apporte; 0.759, 0.892, Main.P-Source.Conc.+Nitrogen.Conc.+OD+total.Vol+PL+emission_CO2+His+lactate+PO4.ferm.+PO4.utilise; 0.755, 0.892, tmp+Main.P-Source.Conc.+P-Source.Feed.conc.+Nitrogen.Conc.+PL+emission_CO2+Thr+His+lactate+PO4.ferm.+PO4.utilise; 0.750, 0.892, pH+tmp+Main.P-Source.Conc.+Nitrogen.Conc.+total.Vol+emission_CO2+rab+Thr+His+lactate+PO4.ferm.+PO4.apporte; 0.755, 0.892, Main.P-Source.Conc.+Nitrogen.Conc.+OD+total.Vol+PL+emission_CO2+rab+His+lactate+PO4.ferm.+PO4.apporte; 0.759, 0.892, tmp+Main.P-Source.Conc.+Nitrogen.Conc.+PL+emission_O2+emission_CO2+Thr+lactate+PO4.ferm.+PO4.apporte; 0.755, 0.892, tmp+Main.P-Source.Conc.+Nitrogen.Conc.+Lys_conc.+total.Vol+PL+emission_O2+emission_CO2+lactate+PO4.ferm.+PO4.apporte; 0.750, 0.892, tmp+Main.P-Source.Conc.+Main.Thr.Conc.+Nitrogen.Conc.+total.Vol+yield+emission_O2+emission_CO2+His+lactate+PO4.apporte+PO4.utilise; 0.745, 0.892, tmp+Main.P-Source.Conc.+P-Source.Feed.conc.+Main.Thr.Conc.+Nitrogen.Conc.+total.Vol+PL+emission_CO2+Thr+His+lactate+PO4.ferm.+PO4.apporte; 0.764, 0.892, tmp+Main.P-Source.Conc.+Nitrogen.Conc.+emission_CO2+rab+Thr+lactate+PO4.ferm.+PO4.apporte; 0.755, 0.892, tmp+Main.P-Source.Conc.+Nitrogen.Conc.+total.Vol+emission_O2+emission_CO2+His+lactate+SO4.ferm.+PO4.ferm.+PO4.apporte; 0.740, 0.892, tmp+Main.P-Source.Conc.+Nitrogen.Conc.+Lys_conc.+total.Vol+PL+emission_O2+emission_CO2+rab+Thr+His+lactate+PO4.ferm.+PO4.apporte; 0.750, 0.892, tmp+Main.P-Source.Conc.+P-Source.Feed.conc.+Main.Thr.Conc.+Nitrogen.Conc.+total.Vol+emission_CO2+rab+His+lactate+PO4.ferm.+PO4.apporte; 0.768, 0.892, tmp+Main.P-Source.Conc.+Nitrogen.Conc.+total.Vol+emission_CO2+lactate+PO4.ferm.+PO4.utilise; 0.740, 0.892, pH+tmp+Main.P-Source.Conc.+Nitrogen.Conc.+total.Vol+PL+emission_O2+emission_CO2+Thr+His+lactate+SO4.ferm.+PO4.apporte+PO4.utilise; 0.750, 0.892, tmp+Main.P-Source.Conc.+P-Source.Feed.conc.+Nitrogen.Conc.+total.Vol+PL+emission_CO2+rab+Thr+His+lactate+PO4.apporte; 0.750, 0.892, pH+tmp+Main.P-Source.Conc.+Nitrogen.Conc.+total.Vol+PL+emission_CO2+rab+Thr+His+lactate+PO4.apporte; 0.772, 0.892, Main.P-Source.Conc.+P-Source.Feed.conc.+Nitrogen.Conc.+total.Vol+emission_CO2+lactate+PO4.apporte; 0.755, 0.892, Main.P-Source.Conc.+Nitrogen.Conc.+total.Vol+PL+emission_O2+emission_CO2+Thr+His+lactate+PO4.apporte+PO4.utilise; 0.759, 0.892, pH+tmp+Main.P-Source.Conc.+Nitrogen.Conc.+total.Vol+PL+emission_CO2+lactate+PO4.apporte+PO4.utilise; 0.745, 0.892, tmp+Main.P-Source.Conc.+P-Source.Feed.conc.+Nitrogen.Conc.+total.Vol+yield+PL+emission_CO2+rab+His+lactate+PO4.ferm.+PO4.apporte; 0.755, 0.892, pH+tmp+Main.P-Source.Conc.+Nitrogen.Conc.+total.Vol+emission_CO2+rab+Thr+lactate+PO4.apporte+PO4.utilise; 0.745, 0.892, tmp+Main.P-Source.Conc.+P-Source.Feed.conc.+Nitrogen.Conc.+total.Vol+yield+PL+emission_CO2+rab+His+lactate+PO4.apporte+PO4.utilise; 0.764, 0.892, tmp+Main.P-Source.Conc.+Nitrogen.Conc.+emission_CO2+rab+His+lactate+PO4.apporte+PO4.utilise; 0.745, 0.892, tmp+Main.P-Source.Conc.+P-Source.Feed.conc.+Nitrogen.Conc.+OD+total.Vol+PL+emission_CO2+rab+His+lactate+PO4.apporte+PO4.utilise; 0.755, 0.892, tmp+Main.P-Source.Conc.+P-Source.Feed.conc.+Nitrogen.Conc.+total.Vol+PL+emission_O2+emission_CO2+lactate+PO4.apporte+PO4.utilise; 0.759, 0.892, tmp+Main.P-Source.Conc.+Nitrogen.Conc.+PL+emission_CO2+rab+Thr+lactate+PO4.apporte+PO4.utilise; 0.745, 0.892, tmp+Main.P-Source.Conc.+Nitrogen.Conc.+Lys_conc.+total.Vol+PL+emission_O2+emission_CO2+His+lactate+SO4.ferm.+PO4.ferm.+PO4.apporte; 0.755, 0.892, tmp+Main.P-Source.Conc.+P-Source.Feed.conc.+Nitrogen.Conc.+total.Vol+PL+emission_CO2+His+lactate+PO4.ferm.+PO4.utilise; 0.745, 0.892, tmp+Main.P-Source.Conc.+Nitrogen.Conc.+total.Vol+yield+PL+emission_CO2+rab+His+lactate+SO4.ferm.+PO4.apporte+PO4.utilise; 0.755, 0.892, tmp+Main.P-Source.Conc.+Nitrogen.Conc.+total.Vol+emission_O2+emission_CO2+rab+Thr+lactate+PO4.ferm.+PO4.apporte; 0.759, 0.892, tmp+Main.P-Source.Conc.+Main.Thr.Conc.+Nitrogen.Conc.+total.Vol+PL+emission_CO2+His+lactate+PO4.apporte; 0.759, 0.892, tmp+Main.P-Source.Conc.+Nitrogen.Conc.+PL+emission_O2+emission_CO2+Thr+lactate+PO4.apporte+PO4.utilise; 0.740, 0.892, tmp+Main.P-Source.Conc.+P-Source.Feed.conc.+Main.Thr.Conc.+Nitrogen.Conc.+total.Vol+PL+emission_O2+emission_CO2+Thr+His+lactate+PO4.ferm.+PO4.apporte; 0.750, 0.892, tmp+Main.P-Source.Conc.+Main.Thr.Conc.+Nitrogen.Conc.+total.Vol+yield+emission_CO2+rab+His+lactate+PO4.apporte+PO4.utilise; 0.745, 0.892, tmp+Main.P-Source.Conc.+Main.Thr.Conc.+Nitrogen.Conc.+total.Vol+yield+PL+emission_O2+emission_CO2+His+lactate+PO4.apporte+PO4.utilise; 0.755, 0.892, tmp+P-Source.Feed.conc.+OD+PL+emission_O2+emission_CO2+Thr+His+lactate+PO4.apporte+PO4.utilise; 0.750, 0.892, pH+tmp+Main.P-Source.Conc.+Main.Thr.Conc.+Nitrogen.Conc.+total.Vol+PL+emission_CO2+His+lactate+PO4.ferm.+PO4.apporte; 0.763, 0.892, tmp+Main.P-

Source.Conc.+Main.Thr.Conc.+Nitrogen.Conc.+total.Vol+ emission_CO2+lactate+PO4.ferm.+PO4.apporte; 0.750, 0.892, tmp+Main.P-Source.Conc.+P-Source.Feed.conc.+ Nitrogen.Conc.+yield+PL+emission_CO2+Thr+His+lactate+PO4.ferm.+PO4.apporte; 0.755, 0.892, pH+tmp+P-Source.Feed.conc.+PL+emission_CO2+rab+Thr+His+ lactate+PO4.apporte+PO4.utilise; 0.745, 0.892, tmp+ Main.P-Source.Conc.+P-Source.Feed.conc.+ Nitrogen.Conc.+total.Vol+PL+emission_O2+ emission_CO2+His+lactate+SO4.ferm.+PO4.ferm.+ PO4.apporte; 0.745, 0.892, tmp+Main.P-Source.Conc.+ Nitrogen.Conc.+total.Vol+yield+PL+emission_CO2+rab+ His+lactate+SO4.ferm.+PO4.ferm.+PO4.apporte; 0.772, 0.892, tmp+Main.P-Source.Conc.+Nitrogen.Conc.+emission_CO2+lactate+PO4.ferm.+PO4.apporte; 0.755, 0.892, tmp+P-Source.Feed.conc.+total.Vol+PL+emission_CO2+ rab+Thr+His+lactate+PO4.ferm.+PO4.apporte; 0.763, 0.892, Main.P-Source.Conc.+Nitrogen.Conc.+OD+PL+ emission_CO2+rab+His+lactate+PO4.apporte; 0.745, 0.892, pH+tmp+Main.P-Source.Conc.+Nitrogen.Conc.+ OD+PL+emission_O2+emission_CO2+Thr+His+lactate+ PO4.ferm.+PO4.apporte; 0.750, 0.892, tmp+Main.P-Source.Conc.+Main.Thr.Conc.+Nitrogen.Conc.+total.Vol+ emission_CO2+rab+His+lactate+SO4.ferm.+PO4.ferm.+ PO4.apporte; 0.763, 0.892, tmp+Main.P-Source.Conc.+ Nitrogen.Conc.+PL+emission_CO2+rab+lactate+ PO4.apporte+PO4.utilise; 0.745, 0.892, tmp+Main.P-Source.Conc.+Nitrogen.Conc.+Lys_conc.+total.Vol+yield+ PL+emission_O2+emission_CO2+His+lactate+ PO4.apporte+PO4.utilise; 0.750, 0.892, tmp+Main.P-Source.Conc.+Main.Thr.Conc.+Nitrogen.Conc.+total.Vol+ yield+emission_O2+emission_CO2+His+lactate+ PO4.ferm.+PO4.apporte; 0.740, 0.892, pH+tmp+Main.P-Source.Conc.+Nitrogen.Conc.+total.Vol+yield+PL+ emission_CO2+rab+Thr+His+lactate+PO4.apporte+ PO4.utilise; 0.759, 0.892, tmp+Main.P-Source.Conc.+P-Source.Feed.conc.+Nitrogen.Conc.+emission_CO2+rab+ Thr+lactate+PO4.ferm.+PO4.apporte; 0.763, 0.892, tmp+ Main.P-Source.Conc.+P-Source.Feed.conc.+ Nitrogen.Conc.+emission_CO2+rab+lactate+PO4.ferm.+ PO4.apporte; 0.750, 0.892, pH+tmp+Main.P-Source.Conc.+ Nitrogen.Conc.+total.Vol+PL+emission_CO2+Thr+His+ lactate+PO4.ferm.+PO4.utilise; 0.759, 0.892, tmp+Main.P-Source.Conc.+Nitrogen.Conc.+total.Vol+emission_CO2+ rab+lactate+SO4.ferm.+PO4.ferm.+PO4.apporte; 0.759, 0.892, Main.P-Source.Conc.+P-Source.Feed.conc.+Nitrogen.Conc.+OD+yield+PL+emission_CO2+His+lactate+ PO4.apporte; 0.767, 0.892, tmp+Main.P-Source.Conc.+ Main.Thr.Conc.+Nitrogen.Conc.+emission_O2+ emission_CO2+lactate+PO4.apporte; 0.750, 0.892, tmp+ Main.P-Source.Conc.+Main.Thr.Conc.+Nitrogen.Conc.+ total.Vol+emission_CO2+rab+Thr+His+lactate+ PO4.apporte+PO4.utilise; 0.745, 0.892, tmp+Main.P-Source.Conc.+P-Source.Feed.conc.+Main.Thr.Conc.+ Nitrogen.Conc.+total.Vol+PL+emission_CO2+Thr+His+ lactate+PO4.apporte+PO4.utilise; 0.750, 0.892, pH+tmp+ Main.P-Source.Conc.+Nitrogen.Conc.+total.Vol+ emission_O2+emission_CO2+Thr+His+lactate+ PO4.apporte+PO4.utilise; 0.750, 0.892, tmp+Main.P-Source.Conc.+Main.Thr.Conc.+Nitrogen.Conc.+total.Vol+ emission_O2+emission_CO2+rab+His+lactate+ PO4.apporte+PO4.utilise; 0.750, 0.892, tmp+Main.P-Source.Conc.+Main.Thr.Conc.+Nitrogen.Conc.+total.Vol+ yield+emission_CO2+His+lactate+PO4.ferm.+ PO4.apporte; 0.754, 0.892, tmp+Main.P-Source.Conc.+ Nitrogen.Conc.+OD+total.Vol+PL+emission_CO2+rab+ lactate+PO4.apporte+PO4.utilise; 0.754, 0.892, tmp+ Main.P-Source.Conc.+P-Source.Feed.conc.+ Nitrogen.Conc.+total.Vol+PL+emission_CO2+Thr+ lactate+PO4.ferm.+PO4.apporte; 0.767, 0.892, Main.P-Source.Conc.+P-Source.Feed.conc.+Nitrogen.Conc.+ total.Vol+PL+emission_CO2+lactate+PO4.apporte; 0.763, 0.892, tmp+Main.P-Source.Conc.+P-Source.Feed.conc.+ Nitrogen.Conc.+PL+emission_CO2+Thr+lactate+ PO4.apporte; 0.767, 0.892, Main.P-Source.Conc.+ Nitrogen.Conc.+total.Vol+yield+emission_CO2+His+lactate+PO4.apporte; 0.750, 0.892, tmp+Main.P-Source.Conc.+Nitrogen.Conc.+total.Vol+emission_O2+ emission_CO2+rab+Thr+His+lactate+PO4.ferm.+ PO4.apporte; 0.750, 0.892, tmp+Main.P-Source.Conc.+ Main.Thr.Conc.+Nitrogen.Conc.+OD+PL+emission_CO2+ rab+His+lactate+PO4.ferm.+PO4.apporte; 0.754, 0.892, Main.P-Source.Conc.+Main.Thr.Conc.+Nitrogen.Conc.+total.Vol+yield+PL+emission_CO2+His+lactate+PO4.ferm.+ PO4.apporte; 0.745, 0.892, tmp+Main.P-Source.Conc.+ Main.Thr.Conc.+Nitrogen.Conc.+Lys_conc.+total.Vol+PL+ emission_O2+emission_CO2+His+lactate+PO4.ferm.+ PO4.apporte; 0.767, 0.892, tmp+P-Source.Feed.conc.+PL+ emission_CO2+His+lactate+PO4.apporte+PO4.utilise; 0.754, 0.892, Main.P-Source.Conc.+Nitrogen.Conc.+OD+ total.Vol+PL+emission_CO2+rab+His+lactate+ PO4.apporte+PO4.utilise; 0.750, 0.892, tmp+Main.P-Source.Conc.+P-Source.Feed.conc.+Main.Thr.Conc.+ Nitrogen.Conc.+total.Vol+emission_O2+emission_CO2+ His+lactate+PO4.apporte+PO4.utilise; 0.750, 0.892, pH+tmp+Main.P-Source.Conc.+Nitrogen.Conc.+OD+ total.Vol+PL+emission_O2+emission_CO2+His+lactate+ PO4.apporte; 0.759, 0.892, tmp+Main.P-Source.Conc.+Nitrogen.Conc.+total.Vol+emission_O2+emission_CO2+rab+ lactate+PO4.apporte+PO4.utilise; 0.754, 0.892, tmp+ Main.P-Source.Conc.+Nitrogen.Conc.+total.Vol+yield+ PL+emission_O2+emission_CO2+lactate+PO4.apporte+ PO4.utilise; 0.740, 0.892, tmp+Main.P-Source.Conc.+P-Source.Feed.conc.+Main.Thr.Conc.+Nitrogen.Conc.+ total.Vol+PL+emission_O2+emission_CO2+Thr+His+ lactate+PO4.apporte+PO4.utilise; 0.763, 0.892, tmp+ Main.P-Source.Conc.+Nitrogen.Conc.+OD+total.Vol+ emission_CO2+lactate+PO4.ferm.+PO4.apporte; 0.754, 0.892, tmp+Main.P-Source.Conc.+Nitrogen.Conc.+Lys_conc.+total.Vol+emission_O2+emission_CO2+His+lactate+PO4.ferm.+PO4.apporte; 0.759, 0.892, tmp+Main.P-Source.Conc.+Main.Thr.Conc.+Nitrogen.Conc.+total.Vol+ emission_CO2+His+lactate+PO4.apporte+PO4.utilise; 0.745, 0.892, tmp+Main.P-Source.Conc.+P-Source.Feed. conc.+Nitrogen.Conc.+total.Vol+PL+emission_CO2+rab+ His+lactate+SO4.ferm.+PO4.ferm.+PO4.apporte; 0.740, 0.892, pH+tmp+Main.P-Source.Conc.+Nitrogen.Conc.+total.Vol+yield+PL+emission_CO2+rab+Thr+His+lactate+ PO4.ferm.+PO4.apporte; 0.759, 0.892, pH+tmp+P-Source.Feed.conc.+PL+emission_CO2+rab+Thr+His+lactate+PO4.apporte; 0.754, 0.892, tmp+Main.P-Source.Conc.+Nitrogen.Conc.+total.Vol+yield+PL+emission_O2+emission_CO2+lactate+PO4.ferm.+PO4.apporte; 0.759, 0.892, Main.P-Source.Conc.+Nitrogen.Conc.+OD+ yield+PL+emission_O2+emission_CO2+His+lactate+ PO4.apporte; 0.754, 0.892, Main.P-Source.Conc.+P-Source.Feed.conc.+Nitrogen.Conc.+total.Vol+PL+ emission_CO2+rab+His+lactate+PO4.apporte+PO4.utilise; 0.750, 0.892, tmp+Main.P-Source.Conc.+Main.Thr.Conc.+ Nitrogen.Conc.+OD+PL+emission_CO2+rab+His+lactate+ PO4.apporte+PO4.utilise; 0.750, 0.892, tmp+Main.P-Source.Conc.+P-Source.Feed.conc.+Nitrogen.Conc.+OD+ PL+emission_CO2+rab+His+lactate+PO4.ferm.+ PO4.apporte; 0.750, 0.892, tmp+Main.P-Source.Conc.+P-

Source.Feed.conc.+Nitrogen.Conc.+total.Vol+ emission_CO2+rab+Thr+His+lactate+PO4.ferm.+ PO4.apporte; 0.740, 0.892, tmp+Main.P-Source.Conc.+ Nitrogen.Conc.+OD+Lys_conc.+total.Vol+PL+ emission_CO2+rab+Thr+His+lactate+PO4.apporte+ PO4.utilise; 0.754, 0.892, Main.P-Source.Conc.+ Main.Thr.Conc.+Nitrogen.Conc.+total.Vol+yield+PL+ emission_CO2+His+lactate+PO4.apporte+PO4.utilise; 0.759, 0.892, tmp+Main.P-Source.Conc.+Nitrogen.Conc.+ total.Vol+emission_O2+emission_CO2+lactate+ SO4.ferm.+PO4.ferm.+PO4.apporte; 0.750, 0.892, tmp+ Main.P-Source.Conc.+P-Source.Feed.conc.+ Nitrogen.Conc.+OD+PL+emission_O2+emission_CO2+ His+lactate+PO4.ferm.+PO4.apporte; 0.750, 0.892, pH+tmp+Main.P-Source.Conc.+Nitrogen.Conc.+Lys_conc.+total.Vol+PL+emission_CO2+His+lactate+ PO4.apporte+PO4.utilise; 0.745, 0.892, tmp+Main.P-Source.Conc.+Nitrogen.Conc.+OD+Lys_conc.+total.Vol+ PL+emission_CO2+Thr+His+lactate+PO4.apporte+ PO4.utilise; 0.759, 0.892, pH+tmp+Main.P-Source.Conc.+ Nitrogen.Conc.+total.Vol+emission_CO2+His+lactate+ PO4.ferm.+PO4.utilise; 0.750, 0.892, pH+tmp+Main.P-Source.Conc.+Nitrogen.Conc.+OD+total.Vol+ emission_CO2+rab+His+lactate+PO4.apporte+PO4.utilise; 0.740, 0.892, tmp+Main.P-Source.Conc.+Nitrogen.Conc.+ OD+total.Vol+yield+PL+emission_CO2+rab+Thr+His+lactate+PO4.apporte+PO4.utilise; 0.759, 0.892, tmp+Main.P-Source.Conc.+P-Source.Feed.conc.+Nitrogen.Conc.+ emission_O2+emission_CO2+Thr+lactate+PO4.ferm.+ PO4.apporte; 0.750, 0.892, tmp+Main.P-Source.Conc.+P-Source.Feed.conc.+Nitrogen.Conc.+PL+emission_CO2+ rab+Thr+His+lactate+PO4.ferm.+PO4.utilise; 0.750, 0.892, pH+tmp+Main.P-Source.Conc.+Nitrogen.Conc.+total.Vol+ PL+emission_O2+rab+His+lactate+PO4.apporte+ PO4.utilise; 0.763, 0.892, tmp+Main.P-Source.Conc.+Nitrogen.Conc.+emission_O2+emission_CO2+Thr+lactate+ PO4.ferm.+PO4.apporte; 0.771, 0.892, Main.P-Source.Conc.+Nitrogen.Conc.+OD+total.Vol+ emission_CO2+lactate+PO4.apporte; 0.750, 0.892, tmp+ Main.P-Source.Conc.+P-Source.Feed.conc.+ Main.Thr.Conc.+Nitrogen.Conc.+total.Vol+ emission_CO2+rab+His+lactate+PO4.apporte+PO4.utilise; 0.763, 0.892, tmp+Main.P-Source.Conc.+Nitrogen.Conc.+ emission_CO2+Thr+lactate+PO4.apporte+PO4.utilise; 0.740, 0.892, pH+tmp+Main.P-Source.Conc.+Nitrogen. Conc.+total.Vol+PL+emission_CO2+rab+Thr+His+lactate+ SO4.ferm.+PO4.ferm.+PO4.apporte; 0.771, 0.892, tmp+ Main.P-Source.Conc.+Nitrogen.Conc.+emission_CO2+lactate+PO4.apporte+PO4.utilise; 0.754, 0.892, tmp+Main.P-Source.Conc.+P-Source.Feed.conc.+ Nitrogen.Conc.+total.Vol+emission_O2+emission_CO2+ Thr+lactate+PO4.apporte+PO4.utilise; 0.750, 0.892, pH+tmp+Main.P-Source.Conc.+Main.Thr.Conc.+ Nitrogen.Conc.+total.Vol+PL+emission_CO2+His+lactate+ PO4.apporte+PO4.utilise; 0.754, 0.892, tmp+Main.P-Source.Conc.+P-Source.Feed.conc.+Nitrogen.Conc.+ total.Vol+PL+emission_CO2+rab+lactate+PO4.apporte+ PO4.utilise; 0.750, 0.892, tmp+Main.P-Source.Conc.+P-Source.Feed.conc.+Nitrogen.Conc.+PL+emission_O2+ emission_CO2+Thr+His+lactate+PO4.ferm.+PO4.utilise; 0.767, 0.892, Main.P-Source.Conc.+Nitrogen.Conc.+OD+ total.Vol+PL+emission_CO2+lactate+PO4.apporte; 0.763, 0.892, Main.P-Source.Conc.+Nitrogen.Conc.+OD+PL+ emission_CO2+Thr+His+lactate+PO4.apporte; 0.767, 0.892, tmp+Main.P-Source.Conc.+Nitrogen.Conc.+OD+total.Vol+emission_CO2+lactate+PO4.apporte; 0.759, 0.892, Main.P-Source.Conc.+Nitrogen.Conc.+total.Vol+yield+ PL+emission_CO2+Thr+His+lactate+PO4.apporte; 0.754, 0.892, tmp+Main.P-Source.Conc.+Main.Thr.Conc.+Nitrogen.Conc.+total.Vol+emission_O2+emission_CO2+rab+ lactate+PO4.ferm.+PO4.apporte; 0.767, 0.892, Main.P-Source.Conc.+Nitrogen.Conc.+total.Vol+PL+ emission_O2+emission_CO2+lactate+PO4.apporte; 0.750, 0.892, tmp+Main.P-Source.Conc.+Nitrogen.Conc.+OD+total.Vol+PL+emission_O2+emission_CO2+His+lactate+ PO4.ferm.+PO4.utilise; 0.767, 0.892, Main.P-Source.Conc.+P-Source.Feed.conc.+Nitrogen.Conc.+ total.Vol+emission_CO2+lactate+PO4.apporte+PO4.utilise; 0.754, 0.892, Main.P-Source.Conc.+Nitrogen.Conc.+total. Vol+PL+emission_CO2+rab+Thr+His+lactate+PO4.ferm.+ PO4.apporte; 0.740, 0.892, pH+tmp+Main.P-Source.Conc.+ Nitrogen.Conc.+OD+Lys_conc.+total.Vol+PL+emission_O2+emission_CO2+His+lactate+PO4.apporte+ PO4.utilise; 0.763, 0.892, Main.P-Source.Conc.+P-Source.Feed.conc.+Nitrogen.Conc.+total.Vol+ emission_CO2+His+lactate+PO4.apporte+PO4.utilise; 0.754, 0.892, tmp+Main.P-Source.Conc.+Nitrogen.Conc.+ OD+total.Vol+emission_CO2+Thr+His+lactate+ PO4.ferm.+PO4.apporte; 0.740, 0.892, tmp+Main.P-Source.Conc.+Nitrogen.Conc.+Lys_conc.+total.Vol+PL+ emission_O2+emission_CO2+Thr+His+lactate+ SO4.ferm.+PO4.ferm.+PO4.apporte; 0.754, 0.892, tmp+ Main.P-Source.Conc.+P-Source.Feed.conc.+ Nitrogen.Conc.+total.Vol+emission_CO2+rab+Thr+ lactate+PO4.ferm.+PO4.apporte; 0.759, 0.892, pH+tmp+P-Source.Feed.conc.+total.Vol+PL+emission_CO2+Thr+His+ lactate+PO4.apporte; 0.763, 0.892, pH+Main.P-Source.Conc.+Nitrogen.Conc.+total.Vol+PL+ emission_CO2+lactate+PO4.ferm.+PO4.apporte; 0.767, 0.892, Main.P-Source.Conc.+Nitrogen.Conc.+total.Vol+ PL+emission_CO2+Thr+lactate+PO4.apporte; 0.745, 0.892, tmp+Main.P-Source.Conc.+Main.Thr.Conc.+Nitrogen.Conc.+total.Vol+yield+PL+emission_O2+emission_CO2+His+lactate+PO4.ferm.+PO4.apporte; 0.750, 0.892, pH+Main.P-Source.Conc.+Nitrogen.Conc.+OD+total.Vol+yield+PL+emission_CO2+His+lactate+PO4.ferm.+ PO4.apporte; 0.754, 0.892, pH+tmp+Main.P-Source.Conc.+ Nitrogen.Conc.+total.Vol+emission_CO2+rab+His+ lactate+PO4.ferm.+PO4.utilise; 0.740, 0.892, tmp+Main.P-Source.Conc.+Nitrogen.Conc.+OD+total.Vol+yield+PL+ emission_CO2+rab+Thr+His+lactate+PO4.ferm.+ PO4.apporte; 0.754, 0.892, pH+tmp+P-Source.Feed.conc.+ PL+emission_O2+emission_CO2+Thr+His+lactate+ PO4.ferm.+PO4.utilise; 0.759, 0.892, Main.P-Source.Conc.+P-Source.Feed.conc.+Nitrogen.Conc.+ total.Vol+yield+PL+emission_CO2+His+lactate+ PO4.apporte; 0.754, 0.892, tmp+Main.P-Source.Conc.+P-Source.Feed.conc.+Nitrogen.Conc.+total.Vol+PL+ emission_CO2+Thr+lactate+PO4.apporte+PO4.utilise; 0.750, 0.892, tmp+Main.P-Source.Conc.+Main.Thr.Conc.+ Nitrogen.Conc.+OD+total.Vol+PL+emission_CO2+His+ lactate+PO4.ferm.+PO4.apporte; 0.763, 0.892, tmp+ Main.P-Source.Conc.+Main.Thr.Conc.+Nitrogen.Conc.+ total.Vol+emission_CO2+lactate+PO4.apporte+PO4.utilise; 0.749, 0.892, tmp+Main.P-Source.Conc.+P-Source.Feed. conc.+Nitrogen.Conc.+total.Vol+emission_O2+emission_CO2+Thr+His+lactate+PO4.apporte+PO4.utilise; 0.740, 0.892, pH+tmp+Main.P-Source.Conc.+Nitrogen. Conc.+Lys_conc.+total.Vol+PL+emission_CO2+rab+Thr+ His+lactate+PO4.ferm.+PO4.apporte; 0.754, 0.892, tmp+ Main.P-Source.Conc.+Main.Thr.Conc.+Nitrogen.Conc.+ OD+emission_CO2+rab+His+lactate+PO4.ferm.+ PO4.apporte; 0.749, 0.892, pH+tmp+Main.P-Source.Conc.+ Nitrogen.Conc.+OD+total.Vol+PL+emission_CO2+rab+

His+lactate+PO4.apporte; 0.749, 0.892, pH+Main.P-Source.Conc.+Nitrogen.Conc.+OD+total.Vol+yield+PL+emission_CO2+His+lactate+PO4.apporte+PO4.utilise; 0.749, 0.892, tmp+Main.P-Source.Conc.+Main.Thr.Conc.+Nitrogen.Conc.+total.Vol+emission_CO2+rab+His+lactate+SO4.ferm.+PO4.apporte+PO4.utilise; 0.759, 0.892, pH+tmp+Main.P-Source.Conc.+Main.Thr.Conc.+Nitrogen.Conc.+emission_O2+emission_CO2+lactate+PO4.apporte+PO4.utilise; 0.745, 0.892, pH+tmp+Main.P-Source.Conc.+Nitrogen.Conc.+OD+PL+emission_O2+emission_CO2+Thr+His+lactate+PO4.apporte+PO4.utilise; 0.759, 0.892, tmp+Main.P-Source.Conc.+P-Source.Feed.conc.+Nitrogen.Conc.+PL+emission_CO2+Thr+lactate+PO4.ferm.+PO4.apporte; 0.740, 0.892, tmp+Main.P-Source.Conc.+Nitrogen.Conc.+OD+total.Vol+PL+emission_O2+emission_CO2+rab+Thr+His+lactate+PO4.ferm.+PO4.apporte; 0.745, 0.892, tmp+Main.P-Source.Conc.+P-Source.Feed.conc.+Nitrogen.Conc.+total.Vol+PL+emission_O2+emission_CO2+His+lactate+SO4.ferm.+PO4.apporte+PO4.utilise; 0.763, 0.892, tmp+Main.P-Source.Conc.+P-Source.Feed.conc.+Nitrogen.Conc.+emission_CO2+rab+lactate+PO4.apporte+PO4.utilise; 0.759, 0.892, tmp+Main.P-Source.Conc.+P-Source.Feed.conc.+Nitrogen.Conc.+PL+emission_CO2+Thr+lactate+PO4.apporte+PO4.utilise; 0.759, 0.892, tmp+Main.P-Source.Conc.+Nitrogen.Conc.+total.Vol+emission_CO2+His+lactate+SO4.ferm.+PO4.ferm.+PO4.apporte; 0.759, 0.892, tmp+Main.P-Source.Conc.+P-Source.Feed.conc.+Nitrogen.Conc.+emission_CO2+rab+Thr+lactate+PO4.apporte+PO4.utilise; 0.749, 0.892, tmp+Main.P-Source.Conc.+Nitrogen.Conc.+Lys_conc.+total.Vol+PL+emission_CO2+rab+Thr+lactate+PO4.apporte+PO4.utilise; 0.740, 0.892, tmp+Main.P-Source.Conc.+Nitrogen.Conc.+Lys_conc.+total.Vol+PL+emission_O2+emission_CO2+rab+Thr+His+lactate+PO4.apporte+PO4.utilise; 0.754, 0.892, tmp+Main.P-Source.Conc.+Nitrogen.Conc.+total.Vol+PL+emission_CO2+Thr+His+lactate+SO4.ferm.+PO4.apporte; 0.754, 0.892, pH+tmp+Main.P-Source.Conc.+Nitrogen.Conc.+total.Vol+emission_CO2+Thr+His+lactate+PO4.ferm.+PO4.apporte; 0.749, 0.892, pH+tmp+Main.P-Source.Conc.+Nitrogen.Conc.+OD+total.Vol+emission_O2+emission_CO2+His+lactate+PO4.apporte+PO4.utilise; 0.745, 0.892, pH+tmp+Main.P-Source.Conc.+P-Source.Feed.conc.+Nitrogen.Conc.+OD+PL+emission_CO2+Thr+His+lactate+PO4.apporte+PO4.utilise; 0.754, 0.892, tmp+Main.P-Source.Conc.+Nitrogen.Conc.+total.Vol+yield+PL+emission_CO2+Thr+lactate+PO4.ferm.+PO4.apporte; 0.745, 0.892, tmp+Main.P-Source.Conc.+Nitrogen.Conc.+total.Vol+yield+PL+emission_CO2+Thr+His+lactate+SO4.ferm.+PO4.ferm.+PO4.apporte; 0.745, 0.892, tmp+Main.P-Source.Conc.+Main.Thr.Conc.+Nitrogen.Conc.+total.Vol+yield+PL+emission_CO2+rab+His+lactate+PO4.apporte+PO4.utilise; 0.745, 0.892, pH+tmp+Main.P-Source.Conc.+P-Source.Feed.conc.+Nitrogen.Conc.+OD+PL+emission_CO2+Thr+His+lactate+PO4.ferm.+PO4.apporte; 0.754, 0.892, tmp+Main.P-Source.Conc.+Nitrogen.Conc.+OD+PL+emission_O2+emission_CO2+Thr+His+lactate+PO4.apporte; 0.754, 0.892, tmp+Main.P-Source.Conc.+Main.Thr.Conc.+Nitrogen.Conc.+total.Vol+yield+emission_O2+emission_CO2+lactate+PO4.apporte+PO4.utilise; 0.749, 0.892, tmp+Main.P-Source.Conc.+Nitrogen.Conc.+total.Vol+yield+PL+emission_CO2+rab+Thr+lactate+PO4.apporte+PO4.utilise; 0.754, 0.892, pH+tmp+P-Source.Feed.conc.+PL+emission_CO2+rab+Thr+His+lactate+PO4.ferm.+PO4.apporte; 0.767, 0.892, tmp+Main.P-Source.Conc.+Nitrogen.Conc.+OD+PL+emission_CO2+lactate+PO4.apporte; 0.749, 0.892, tmp+Main.P-Source.Conc.+P-Source.Feed.conc.+Nitrogen.Conc.+OD+PL+emission_CO2+rab+His+lactate+PO4.apporte+PO4.utilise; 0.745, 0.892, tmp+Main.P-Source.Conc.+Nitrogen.Conc.+OD+total.Vol+PL+emission_O2+emission_CO2+His+lactate+SO4.ferm.+PO4.ferm.+PO4.apporte; 0.758, 0.892, tmp+Main.P-Source.Conc.+P-Source.Feed.conc.+PL+emission_O2+emission_CO2+Thr+His+lactate+PO4.ferm.; 0.749, 0.892, tmp+Main.P-Source.Conc.+P-Source.Feed.conc.+Nitrogen.Conc.+OD+PL+emission_O2+emission_CO2+His+lactate+PO4.apporte+PO4.utilise; 0.763, 0.892, Main.P-Source.Conc.+P-Source.Feed.conc.+Nitrogen.Conc.+OD+PL+emission_CO2+His+lactate+PO4.apporte; 0.758, 0.892, pH+tmp+Main.P-Source.Conc.+Main.Thr.Conc.+Nitrogen.Conc.+total.Vol+emission_CO2+rab+lactate+PO4.apporte; 0.758, 0.892, pH+tmp+Main.P-Source.Conc.+Main.Thr.Conc.+Nitrogen.Conc.+emission_O2+emission_CO2+lactate+PO4.ferm.+PO4.apporte; 0.745, 0.892, tmp+Main.P-Source.Conc.+Nitrogen.Conc.+total.Vol+yield+PL+emission_CO2+Thr+His+lactate+SO4.ferm.+PO4.apporte+PO4.utilise; 0.754, 0.892, tmp+Main.P-Source.Conc.+Main.Thr.Conc.+Nitrogen.Conc.+OD+emission_CO2+rab+His+lactate+PO4.apporte+PO4.utilise; 0.754, 0.892, tmp+Main.P-Source.Conc.+P-Source.Feed.conc.+Main.Thr.Conc.+Nitrogen.Conc.+emission_CO2+rab+His+lactate+PO4.apporte+PO4.utilise; 0.744, 0.892, pH+tmp+Main.P-Source.Conc.+Main.Thr.Conc.+Nitrogen.Conc.+total.Vol+PL+emission_CO2+Thr+His+lactate+PO4.ferm.+PO4.apporte; 0.754, 0.892, tmp+Main.P-Source.Conc.+Nitrogen.Conc.+total.Vol+emission_CO2+rab+His+lactate+SO4.ferm.+PO4.apporte+PO4.utilise; 0.763, 0.892, pH+Main.P-Source.Conc.+Nitrogen.Conc.+total.Vol+emission_CO2+His+lactate+PO4.ferm.+PO4.apporte; 0.763, 0.892, pH+Main.P-Source.Conc.+Nitrogen.Conc.+total.Vol+PL+emission_CO2+lactate+PO4.apporte+PO4.utilise; 0.749, 0.892, tmp+Main.P-Source.Conc.+Nitrogen.Conc.+OD+total.Vol+PL+emission_CO2+His+lactate+SO4.ferm.+PO4.ferm.+PO4.apporte; 0.771, 0.892, Main.P-Source.Conc.+Nitrogen.Conc.+total.Vol+emission_O2+emission_CO2+lactate+PO4.apporte; 0.754, 0.892, Main.P-Source.Conc.+Nitrogen.Conc.+total.Vol+PL+emission_CO2+rab+Thr+His+lactate+PO4.apporte+PO4.utilise; 0.744, 0.892, tmp+Main.P-Source.Conc.+Main.Thr.Conc.+Nitrogen.Conc.+Lys_conc.+total.Vol+PL+emission_O2+emission_CO2+His+lactate+PO4.apporte+PO4.utilise; 0.767, 0.892, tmp+P-Source.Feed.conc.+PL+emission_CO2+His+lactate+PO4.ferm.+PO4.apporte; 0.763, 0.892, tmp+Main.P-Source.Conc.+Nitrogen.Conc.+PL+emission_O2+emission_CO2+lactate+PO4.ferm.+PO4.apporte; 0.763, 0.892, tmp+Main.P-Source.Conc.+P-Source.Feed.conc.+Nitrogen.Conc.+total.Vol+emission_CO2+His+lactate+PO4.apporte; 0.758, 0.892, tmp+Main.P-Source.Conc.+P-Source.Feed.conc.+Nitrogen.Conc.+emission_CO2+rab+His+lactate+PO4.ferm.+PO4.apporte; 0.744, 0.892, pH+tmp+Main.P-Source.Conc.+Nitrogen.Conc.+Lys_conc.+total.Vol+PL+emission_CO2+Thr+His+lactate+PO4.ferm.+PO4.apporte; 0.767, 0.892, tmp+Main.P-Source.Conc.+Nitrogen.Conc.+PL+emission_CO2+His+lactate+PO4.apporte; 0.754, 0.892, tmp+Main.P-Source.Conc.+Nitrogen.Conc.+total.Vol+yield+PL+emission_CO2+Thr+lactate+PO4.apporte+PO4.utilise; 0.771, 0.892, Main.P-Source.Conc.+Main.Thr.Conc.+Nitrogen.Conc.+total.Vol+emission_CO2+lactate+PO4.apporte; 0.754, 0.892, tmp+Main.P-Source.Conc.+Main.Thr.Conc.+Nitrogen.Conc.+total.Vol+ yield+emission_CO2+rab+lactate+PO4.apporte+ PO4.utilise; 0.754, 0.892, tmp+Main.P-Source.Conc.+ Nitrogen.Conc.+total.Vol+yield+PL+emission_CO2+rab+ lactate+PO4.ferm.+PO4.apporte; 0.754, 0.892, tmp+ Main.P-Source.Conc.+Nitrogen.Conc.+Lys_conc.+ total.Vol+emission_CO2+rab+His+lactate+PO4.ferm.+ PO4.apporte; 0.754, 0.892, pH+tmp+Main.P-Source.Conc.+ Nitrogen.Conc.+OD+total.Vol+emission_CO2+rab+ lactate+PO4.ferm.+PO4.apporte; 0.744, 0.892, tmp+ Main.P-Source.Conc.+P-Source.Feed.conc.+ Nitrogen.Conc.+total.Vol+PL+emission_CO2+rab+His+ lactate+SO4.ferm.+PO4.apporte+PO4.utilise; 0.754, 0.892, Main.P-Source.Conc.+Nitrogen.Conc.+total.Vol+yield+ PL+emission_CO2+rab+His+lactate+PO4.ferm.+ PO4.apporte; 0.758, 0.892, tmp+Main.P-Source.Conc.+P-Source.Feed.conc.+Nitrogen.Conc.+emission_O2+ emission_CO2+Thr+lactate+PO4.apporte+PO4.utilise; 0.754, 0.892, tmp+Main.P-Source.Conc.+Nitrogen.Conc.+ total.Vol+yield+PL+emission_CO2+rab+lactate+ PO4.apporte+PO4.utilise

[13. Linear Model that Predicts Lysine Production Amount in Interval 3]

0.474, 0.728, tmp+P-Source.Feed.conc.+Main.Thr.Conc.+ Nitrogen.Conc.+Lys_conc.+SO4.ferm.+PO4.apporte; 0.482, 0.728, tmp+P-Source.Feed.conc.+Main.Thr.Conc.+ Lys_conc.+SO4.ferm.+PO4.apporte; 0.459, 0.725, pH+tmp+P-Source.Feed.conc.+Main.Thr.Conc.+Nitrogen. Conc.+Lys_conc.+SO4.ferm.+PO4.apporte; 0.467, 0.724, pH+tmp+P-Source.Feed.conc.+Main.Thr.Conc.+Lys_conc.+SO4.ferm.+PO4.apporte; 0.467, 0.724, tmp+P-Source.Feed.conc.+Main.Thr.Conc.+Lys_conc.+lactate+ SO4.ferm.+PO4.apporte; 0.456, 0.723, tmp+P-Source.Feed.conc.+Main.Thr.Conc.+Nitrogen.Conc.+ Lys_conc.+lactate+SO4.ferm.+PO4.apporte; 0.464, 0.722, tmp+P-Source.Feed.conc.+Main.Thr.Conc.+Lys_conc.+ yield+SO4.ferm.+PO4.apporte; 0.454, 0.722, tmp+Main.P-Source.Conc.+P-Source.Feed.conc.+Main.Thr.Conc.+Nitrogen.Conc.+Lys_conc.+SO4.ferm.+PO4.apporte; 0.454, 0.722, tmp+P-Source.Feed.conc.+Main.Thr.Conc.+Nitrogen.Conc.+Lys_conc.+yield+SO4.ferm.+PO4.apporte; 0.451, 0.720, tmp+P-Source.Feed.conc.+Main.Thr.Conc.+ Nitrogen.Conc.+Lys_conc.+His+SO4.ferm.+PO4.apporte; 0.460, 0.720, tmp+P-Source.Feed.conc.+Main.Thr.Conc.+ Lys_conc.+PL+SO4.ferm.+PO4.apporte; 0.450, 0.720, pH+tmp+P-Source.Feed.conc.+Main.Thr.Conc.+Lys_conc.+lactate+SO4.ferm.+PO4.apporte; 0.450, 0.720, tmp+P-Source.Feed.conc.+Main.Thr.Conc.+Nitrogen. Conc.+Lys_conc.+PL+SO4.ferm.+PO4.apporte; 0.459, 0.720, tmp+P-Source.Feed.conc.+Main.Thr.Conc.+OD+Lys_conc.+SO4.ferm.+PO4.apporte; 0.440, 0.719, pH+tmp+ Main.P-Source.Conc.+P-Source.Feed.conc.+Main.Thr. Conc.+Nitrogen.Conc.+Lys_conc.+SO4.ferm.+ PO4.apporte; 0.439, 0.719, pH+tmp+P-Source.Feed.conc.+ Main.Thr.Conc.+Nitrogen.Conc.+Lys_conc.+lactate+ SO4.ferm.+PO4.apporte; 0.449, 0.719, tmp+P-Source.Feed.conc.+Main.Thr.Conc.+Nitrogen.Conc.+OD+ Lys_conc.+SO4.ferm.+PO4.apporte; 0.458, 0.718, tmp+ Main.P-Source.Conc.+P-Source.Feed.conc.+ Main.Thr.Conc.+Lys_conc.+504.ferm.+PO4.apporte; 0.447, 0.718, tmp+P-Source.Feed.conc.+Main.Thr.Conc.+Lys_conc.+yield+lactate+SO4.ferm.+PO4.apporte; 0.457, 0.718, tmp+P-Source.Feed.conc.+Main.Thr.Conc.+Lys_conc.+His+SO4.ferm.+PO4.apporte; 0.447, 0.718, pH+tmp+P-Source.Feed.conc.+Main.Thr.Conc.+Lys_conc.+yield+SO4.ferm.+PO4.apporte; 0.437, 0.717, pH+tmp+P-Source.Feed.conc.+Main.Thr.Conc.+Nitrogen. Conc.+Lys_conc.+yield+SO4.ferm.+PO4.apporte; 0.436, 0.717, tmp+P-Source.Feed.conc.+Main.Thr.Conc.+Nitrogen.Conc.+Lys_conc.+yield+lactate+SO4.ferm.+PO4.apporte; 0.445, 0.717, pH+tmp+P-Source.Feed.conc.+Main. Thr.Conc.+OD+Lys_conc.+SO4.ferm.+PO4.apporte; 0.445, 0.717, tmp+P-Source.Feed.conc.+Main.Thr.Conc.+Lys_conc.+PL+lactate+SO4.ferm.+PO4.apporte; 0.435, 0.716, tmp+Main.P-Source.Conc.+P-Source.Feed.conc.+Main. Thr.Conc.+Nitrogen.Conc.+Lys_conc.+lactate+SO4.ferm.+ PO4.apporte; 0.434, 0.716, pH+tmp+P-Source. Feed.conc.+ Main.Thr.Conc.+Nitrogen.Conc.+Lys_conc.+His+SO4. ferm.+PO4.apporte; 0.443, 0716, tmp+P-Source.Feed.conc.+Main.Thr.Conc.+OD+Lys_conc.+yield+ SO4.ferm.+PO4.apporte; 0.433, 0.715, pH+tmp+P-Source.Feed.conc.+Main.Thr.Conc.+Nitrogen.Conc.+OD+ Lys_conc.+SO4.ferm.+PO4.apporte; 0.443, 0.715, tmp+P-Source.Feed.conc.+Main.Thr.Conc.+OD+Lys_conc.+lactate+SO4.ferm.+PO4.apporte; 0.443, 0.715, pH+tmp+P-Source.Feed.conc.+Main.Thr.Conc.+Lys_conc.+PL+SO4. ferm.+PO4.apporte; 0.433, 0.715, tmp+Main.P-Source. Conc.+P-Source.Feed.conc.+Main.Thr.Conc.+Nitrogen. Conc.+Lys_conc.+yield+SO4.ferm.+PO4.apporte; 0.452, 0.715, tmp+P-Source.Feed.conc.+Main.Thr.Conc.+Lys_conc.+SO4.ferm.+PO4.apporte+PO4.utilise; 0.432, 0.715, pH+tmp+P-Source.Feed.conc.+Main.Thr.Conc.+Nitrogen. Conc.+Lys_conc.+PL+SO4.ferm.+PO4.apporte; 0.442, 0.714, pH+tmp+Main.P-Source.Conc.+P-Source. Feed. conc.+Main.Thr.Conc.+Lys_conc.+SO4.ferm.+PO4.apporte; 0.451, 0.714, tmp+P-Source.Feed.conc.+Main.Thr. Conc.+Lys_conc.+SO4.ferm.+PO4.ferm.+PO4.apporte; 0.432, 0.714, tmp+Main.P-Source.Conc.+P-Source.Feed. conc.+Main.Thr.Conc.+Nitrogen.Conc.+Lys_conc.+His+ SO4.ferm.+PO4.apporte; 0.432, 0.714, tmp+P-Source.Feed. conc.+Main.Thr.Conc.+Nitrogen. Conc.+Lys_conc.+PL+ lactate+SO4.ferm.+PO4.apporte; 0.441, 0.714, tmp+P-Source.Feed.conc.+Main.Thr.Conc.+Nitrogen.Conc.+Lys_conc.+SO4.ferm.+PO4.apporte+PO4.utilise; 0.441, 0.714, tmp+Main.P-Source.Conc.+P-Source.Feed.conc.+Main. Thr.Conc.+Lys_conc.+lactate+SO4.ferm.+PO4.apporte; 0.451, 0.714, tmp+P-Source.Feed.conc.+Main.Thr.Conc.+ Lys_conc.+SO4.ferm.+PO4.ferm.+PO4.utilise; 0.441, 0.714, tmp+P-Source.Feed.conc.+Main.Thr.Conc.+Nitrogen.Conc.+Lys_conc.+SO4.ferm.+PO4.ferm.+PO4.apporte; 0.440, 0.714, tmp+P-Source.Feed.conc.+Main.Thr.Conc.+ OD+Lys_conc.+His+SO4.ferm.+PO4.apporte; 0.440, 0.714, tmp+P-Source.Feed.conc.+Main.Thr.Conc.+Lys_conc.+ yield+PL+SO4.ferm.+PO4.apporte; 0.430, 0.713, tmp+P-Source.Feed.conc.+Main.Thr.Conc.+Nitrogen.Conc.+OD+ Lys_conc.+lactate+SO4.ferm.+PO4.apporte; 0.440, 0.713, pH+tmp+P-Source.Feed.conc.+Main.Thr.Conc.+Lys_conc.+His+SO4.ferm.+PO4.apporte; 0.440, 0.713, tmp+P-Source.Feed.conc.+Main.Thr.Conc.+Nitrogen.Conc.+Lys_conc.+SO4.ferm.+PO4.ferm.+PO4.utilise; 0.419, 0.713, pH+tmp+Main.P-Source.Conc.+P-Source.Feed.conc.+ Main.Thr.Conc.+Nitrogen.Conc.+Lys_conc.+lactate+SO4. ferm.+PO4.apporte; 0.429, 0.713, pH+tmp+P-Source. Feed. conc.+Main.Thr.Conc.+Lys_conc.+yield+lactate+SO4. ferm.+PO4.apporte; 0.429, 0.713, tmp+Main.P-Source. Conc.+P-Source.Feed.conc.+Main.Thr.Conc.+Nitrogen. Conc.+Lys_conc.+PL+SO4.ferm.+PO4.apporte; 0.429, 0.713, tmp+P-Source.Feed.conc.+Main.Thr.Conc.+Nitrogen.Conc.+Lys_conc.+yield+PL+SO4.ferm.+PO4.apporte; 0.428, 0.712, tmp+P-Source.Feed.conc.+Main.Thr.Conc.+ Nitrogen.Conc.+OD+Lys_conc.+His+SO4.ferm.+PO4.apporte; 0.438, 0.712, tmp+Main.P-Source.Conc.+ P-Source.Feed.conc.+Main.Thr.Conc.+Lys_conc.+yield+SO4.ferm.+PO4.apporte; 0.428, 0.712, tmp+P-Source.Feed.conc.+Main.Thr.Conc.+Nitrogen. Conc.+OD+Lys_conc.+yield+SO4.ferm.+PO4.apporte; 0.457, 0.712, tmp+P-Source.Feed.conc.+Main.Thr.Conc.+ Nitrogen.Conc.+Lys_conc.+PO4.apporte; 0.417, 0.712, pH+tmp+P-Source.Feed.conc.+Main.Thr.Conc.+ Nitrogen.Conc.+Lys_conc.+yield+lactate+SO4.ferm.+ PO4.apporte; 0.427, 0.712, pH+tmp+P-Source.Feed.conc.+ Main.Thr.Conc.+OD+Lys_conc.+yield+SO4.ferm.+ PO4.apporte; 0.437, 0.712, tmp+P-Source.Feed.conc.+ Main.Thr.Conc.+OD+Lys_conc.+PL+SO4.ferm.+ PO4.apporte; 0.416, 0.712, pH+tmp+Main.P-Source.Conc.+ P-Source.Feed.conc.+Main.Thr.Conc.+Nitrogen.Conc.+ Lys_conc.+yield+SO4.ferm.+PO4.apporte; 0.427, 0.711, tmp+P-Source.Feed.conc.+Main.Thr.Conc.+Nitrogen. Conc.+Lys_conc.+PL+His+SO4.ferm.+PO4.apporte; 0.427, 0.711, pH+tmp+P-Source.Feed.conc.+Main.Thr. Conc.+ OD+Lys_conc.+lactate+SO4.ferm.+PO4.apporte; 0.446, 0.711, pH+tmp+P-Source.Feed.conc.+Main.Thr.Conc.+Ni- trogen.Conc.+Lys_conc.+PO4.apporte; 0.426, 0.711, tmp+ Main.P-Source.Conc.+P-Source.Feed.conc.+Main.Thr. Conc.+Nitrogen.Conc.+OD+Lys_conc.+SO4.ferm.+ PO4.apporte; 0.416, 0.711, pH+tmp+Main.P-Source.Conc.+ P-Source.Feed.conc.+Main.Thr.Conc.+Nitrogen.Conc.+Ly- s_conc.+His+SO4.ferm.+PO4.apporte; 0.436, 0.711, tmp+ P-Source.Feed.conc.+Main.Thr.Conc.+Lys_conc.+lactate+ SO4.ferm.+PO4.apporte+PO4.utilise; 0.436, 0.711, pH+tmp+P-Source.Feed.conc.+Main.Thr.Conc.+Ly- s_conc.+SO4.ferm.+PO4.apporte+PO4.utilise; 0.426, 0.711, pH+tmp+P-Source.Feed.conc.+Main.Thr.Conc.+Ly- s_conc.+PL+lactate+SO4.ferm.+PO4.apporte; 0.436, 0.711, tmp+P-Source.Feed.conc.+Main.Thr.Conc.+Lys_conc.+lac- tate+SO4.ferm.+PO4.ferm.+PO4.apporte; 0.436, 0.711, pH+tmp+P-Source.Feed.conc.+Main.Thr.Conc.+Ly- s_conc.+SO4.ferm.+PO4.ferm.+PO4.apporte; 0.425, 0.711, pH+tmp+P-Source.Feed.conc.+Main.Thr.Conc.+OD+Ly- s_conc.+His+SO4.ferm.+PO4.apporte; 0.425, 0.710, pH+tmp+P-Source.Feed.conc.+Main.Thr.Conc.+Nitrogen. Conc.+Lys_conc.+SO4.ferm.+PO4.apporte+PO4.utilise; 0.435, 0.710, tmp+P-Source.Feed.conc.+Main.Thr.Conc.+ Lys_conc.+lactate+SO4.ferm.+PO4.ferm.+PO4.utilise; 0.435, 0.710, pH+tmp+P-Source.Feed.conc.+Main.Thr. Conc.+Lys_conc.+SO4.ferm.+PO4.ferm.+PO4.utilise; 0.435, 0.710, tmp+P-Source.Feed.conc.+Main.Thr.Conc.+ Lys_conc.+PL+His+SO4.ferm.+PO4.apporte; 0.425, 0.710, pH+tmp+P-Source.Feed.conc.+Main.Thr.Conc.+Nitrogen. Conc.+Lys_conc.+SO4.ferm.+PO4.ferm.+PO4.apporte; 0.425, 0.710, tmp+P-Source.Feed.conc.+Main.Thr.Conc.+ OD+Lys_conc.+yield+lactate+SO4.ferm.+PO4.apporte; 0.435, 0.710, tmp+Main.P-Source.Conc.+P-Source.Feed. conc.+Main.Thr.Conc.+Lys_conc.+PL+SO4.ferm.+ PO4.apporte; 0.425, 0.710, tmp+P-Source.Feed.conc.+ Main.Thr.Conc.+Nitrogen.Conc.+Lys_conc.+SO4.ferm.+ PO4.ferm.+PO4.apporte+PO4.utilise; 0.414, 0.710, tmp+ Main.P-Source.Conc.+P-Source.Feed.conc.+ Main.Thr.Conc.+Nitrogen.Conc.+Lys_conc.+yield+lactate+ SO4.ferm.+PO4.apporte; 0.424, 0.710, tmp+P- Source.Feed.conc.+Main.Thr.Conc.+Lys_conc.+yield+PL+ lactate+SO4.ferm.+PO4.apporte; 0.424, 0.710, pH+tmp+P- Source.Feed.conc.+Main.Thr.Conc.+Nitrogen.Conc.+ Lys_conc.+SO4.ferm.+PO4.ferm.+PO4.utilise; 0.423, 0.709, pH+tmp+Main.P-Source.Conc.+P-Source.Feed. conc.+Main.Thr.Conc.+Lys_conc.+lactate+SO4.ferm.+ PO4.apporte; 0.433, 0.709, tmp+P-Source.Feed.conc.+ Main.Thr.Conc.+Lys_conc.+SO4.ferm.+PO4.ferm.+ PO4.apporte+PO4.utilise; 0.423, 0.709, tmp+P- Source.Feed.conc.+Main.Thr.Conc.+Nitrogen.Conc.+OD+ Lys_conc.+PL+SO4.ferm.+PO4.apporte; 0.412, 0.709, pH+tmp+P-Source.Feed.conc.+Main.Thr.Conc.+ Nitrogen.Conc.+OD+Lys_conc.+lactate+SO4.ferm.+ PO4.apporte; 0.433, 0.709, tmp+Main.P-Source.Conc.+P- Source.Feed.conc.+Main.Thr.Conc.+OD+Lys_conc.+ SO4.ferm.+PO4.apporte; 0.412, 0.709, pH+tmp+P- Source.Feed.conc.+Main.Thr.Conc.+Nitrogen.Conc.+OD+ Lys_conc.+His+SO4.ferm.+PO4.apporte; 0.423, 0.709, tmp+P-Source.Feed.conc.+Main.Thr.Conc.+Nitrogen. Conc.+Lys_conc.+lactate+SO4.ferm.+PO4.apporte+ PO4.utilise; 0.422, 0.709, tmp+Main.P-Source.Conc.+P- Source.Feed.conc.+Main.Thr.Conc.+Nitrogen.Conc.+Ly- s_conc.+SO4.ferm.+PO4.apporte+PO4.utilise; 0.422, 0.709, tmp+Main.P-Source.Conc.+P-Source.Feed.conc.+ Main.Thr.Conc.+Nitrogen.Conc.+Lys_conc.+SO4.ferm.+ PO4.ferm.+PO4.apporte; 0.412, 0.709, pH+tmp+P- Source.Feed.conc.+Main.Thr.Conc.+Nitrogen.Conc.+Ly- s_conc.+PL+lactate+SO4.ferm.+PO4.apporte; 0.422, 0.709, tmp+P-Source.Feed.conc.+Main.Thr.Conc.+Nitrogen. Conc.+Lys_conc.+lactate+SO4.ferm.+PO4.ferm.+ PO4.apporte; 0.411, 0.708, pH+tmp+Main.P-Source.Conc.+ P-Source.Feed.conc.+Main.Thr.Conc.+Nitrogen.Conc.+Ly- s_conc.+PL+SO4.ferm.+PO4.apporte; 0.432, 0.708, tmp+ Main.P-Source.Conc.+P-Source.Feed.conc.+Main. Thr.Conc.+Lys_conc.+His+SO4.ferm.+PO4.apporte; 0.411, 0.708, pH+tmp+Main.P-Source.Conc.+P-Source.Feed. conc.+Main.Thr.Conc.+Nitrogen.Conc.+OD+Lys_conc.+ SO4.ferm.+PO4.apporte; 0.432, 0.708, tmp+P-Source.Feed. conc.+Main.Thr.Conc.+Lys_conc.+yield+SO4.ferm.+ PO4.apporte+PO4.utilise; 0.432, 0.708, tmp+P-Source. Feed.conc.+Main.Thr.Conc.+Lys_conc.+yield+SO4.ferm.+ PO4.ferm.+PO4.apporte; 0.431, 0.708, tmp+P-Source. Feed.conc.+Main.Thr.Conc.+Lys_conc.+yield+SO4.ferm.+ PO4.ferm.+PO4.utilise; 0.421, 0.708, tmp+P-Source.Feed. conc.+Main.Thr.Conc.+Nitrogen.Conc.+Lys_conc.+lac- tate+SO4.ferm.+PO4.ferm.+PO4.utilise; 0.411, 0.708, pH+tmp+P-Source.Feed.conc.+Main.Thr. Conc.+Nitrogen. Conc.+OD+Lys_conc.+yield+SO4.ferm.+PO4.apporte; 0.431, 0.708, pH+tmp+Main.P-Source.Conc.+P-Source. Feed.conc.+Main.Thr.Conc.+Nitrogen.Conc.+Lys_conc.+ SO4.ferm.; 0.441, 0.708, tmp+Main.P-Source.Conc.+P- Source.Feed.conc.+Main.Thr.Conc.+Nitrogen.Conc.+Ly- s_conc.+SO4.ferm.; 0.421, 0.708, pH+tmp+P- Source.Feed.conc.+Main.Thr.Conc.+Lys_conc.+yield+PL+ SO4.ferm.+PO4.apporte; 0.410, 0.708, tmp+P- Source.Feed.conc.+Main.Thr.Conc.+Nitrogen. Conc.+ Lys_conc.+yield+PL+lactate+SO4.ferm.+PO4.apporte; 0.421, 0.708, tmp+Main.P-Source.Conc.+P-Source.Feed. conc.+Main.Thr.Conc.+Lys_conc.+yield+lactate+ SO4.ferm.+PO4.apporte; 0.421, 0.708, tmp+Main.P- Source.Conc.+P-Source.Feed.conc.+Main.Thr.Conc.+Ni- trogen.Conc.+Lys_conc.+SO4.ferm.+PO4.ferm.+ PO4.utilise; 0.440, 0.707, tmp+P-Source.Feed.conc.+ Main.Thr.Conc.+Nitrogen.Conc.+Lys_conc.+yield+ PO4.apporte; 0.420, 0.707, tmp+P-Source.Feed.conc.+ Main.Thr.Conc.+OD+Lys_conc.+PL+lactate+SO4.ferm.+ PO4.apporte; 0.420, 0.707, pH+tmp+Main.P-Source.Conc.+ P-Source.Feed.conc.+Main.Thr.Conc.+Lys_conc.+yield+ SO4.ferm.+PO4.apporte; 0.410, 0.707, tmp+Main.P- Source.Conc.+P-Source.Feed.conc.+Main.Thr.Conc.+ Nitrogen.Conc.+Lys_conc.+SO4.ferm.+PO4.ferm.+ PO4.apporte+PO4.utilise; 0.420, 0.707, pH+tmp+P- Source.Feed.conc.+Main.Thr.Conc.+OD+Lys_conc.+PL+ SO4.ferm.+PO4.apporte; 0.420, 0.707, tmp+P- Source.Feed.conc.+Main.Thr.Conc.+Nitrogen.Conc.+ Lys_conc.+His+lactate+SO4.ferm.+PO4.apporte; 0.409, 0.707, tmp+Main.P-Source.Conc.+P-Source.Feed.conc.+ Main.Thr.Conc.+Nitrogen.Conc.+Lys_conc.+PL+lactate+

SO4.ferm.+PO4.apporte; 0.409, 0.707, pH+tmp+P-Source. Feed.conc.+Main.Thr.Conc.+Nitrogen.Conc.+Lys_conc.+ yield+PL+SO4.ferm.+PO4.apporte; 0.419, 0.707, tmp+P-Source.Feed.conc.+Main.Thr.Conc.+Nitrogen.Conc.+Lys_conc.+yield+SO4.ferm.+PO4.apporte+PO4.utilise; 0.429, 0.707, tmp+P-Source.Feed.conc.+Main.Thr.Conc.+OD+Lys_conc.+His+SO4.ferm.+PO4.utilise; 0.419, 0.707, tmp+P-Source.Feed.conc.+Main.Thr.Conc.+OD+Lys_conc.+yield+PL+SO4.ferm.+PO4.apporte; 0.429, 0.707, tmp+P-Source.Feed.conc.+Main.Thr.Conc.+Lys_conc.+PL+SO4.ferm.+PO4.apporte+PO4.utilise; 0.409, 0.707, tmp+P-Source.Feed.conc.+Main.Thr.Conc.+Nitrogen. Conc.+OD+Lys_conc.+yield+lactate+SO4.ferm.+PO4.apporte; 0.419, 0.707, tmp+P-Source.Feed.conc.+Main.Thr.Conc.+Nitrogen.Conc.+Lys_conc.+yield+SO4.ferm.+PO4.ferm.+PO4.apporte; 0.419, 0.707, tmp+P-Source.Feed.conc.+Main.Thr.Conc.+OD+Lys_conc.+PL+His+SO4.ferm.+PO4.apporte; 0.429, 0.707, tmp+P-Source.Feed.conc.+Main.Thr.Conc.+Lys_conc.+PL+SO4.ferm.+PO4.ferm.+PO4.apporte; 0.419, 0.707, pH+tmp+P-Source.Feed.conc.+Main.Thr.Conc.+Lys_conc.+lactate+SO4.ferm.+PO4.apporte+PO4.utilise; 0.429, 0.706, tmp+Main.P-Source.Conc.+P-Source.Feed.conc.+Main.Thr.Conc.+Lys_conc.+SO4.ferm.+PO4.apporte+PO4.utilise; 0.418, 0.706, pH+tmp+P-Source.Feed.conc.+Main.Thr.Conc.+Lys_conc.+lactate+SO4.ferm.+PO4.ferm.+PO4.apporte; 0.429, 0.706, tmp+Main.P-Source.Conc.+P-Source.Feed.conc.+Main.Thr.Conc.+Lys_conc.+SO4.ferm.+PO4.ferm.+PO4.apporte; 0.429, 0.706, tmp+P-Source.Feed.conc.+Main.Thr.Conc.+Lys_conc.+PL+SO4.ferm.+PO4.ferm.+PO4.utilise; 0.418, 0.706, tmp+P-Source.Feed.conc.+Main.Thr.Conc.+Nitrogen.Conc.+Lys_conc.+yield+SO4.ferm.+PO4.ferm.+PO4.utilise; 0.438, 0.706, tmp+P-Source.Feed.conc.+Main.Thr.Conc.+Nitrogen.Conc.+Lys_conc.+lactate+PO4.apporte; 0.418, 0.706, pH+tmp+P-Source.Feed.conc.+Main.Thr.Conc.+Lys_conc.+lactate+SO4.ferm.+PO4.ferm.+PO4.utilise; 0.407, 0.706, pH+tmp+Main.P-Source.Conc.+P-Source.Feed.conc.+Main.Thr.Conc.+Nitrogen.Conc.+Lys_conc.+SO4.ferm.+PO4.apporte+PO4.utilise; 0.407, 0.706, pH+tmp+Main.P-Source.Conc.+P-Source.Feed.conc.+Main.Thr.Conc.+Nitrogen.Conc.+Lys_conc.+SO4.ferm.+PO4.ferm.+PO4.apporte; 0.418, 0.706, tmp+Main.P-Source.Conc.+P-Source.Feed.conc.+Main.Thr.Conc.+Lys_conc.+PL+lactate+SO4.ferm.+PO4.apporte; 0.396, 0.706, pH+tmp+Main.P-Source.Conc.+P-Source.Feed.conc.+Main.Thr.Conc.+Nitrogen.Conc.+Lys_conc.+yield+lactate+SO4.ferm.+PO4.apporte; 0.418, 0.706, pH+tmp+Main.P-Source.Conc.+P-Source.Feed.conc.+Main.Thr.Conc.+OD+Lys_conc.+SO4.ferm.+PO4.apporte; 0.428, 0.706, tmp+Main.P-Source.Conc.+P-Source.Feed.conc.+Main.Thr.Conc.+Lys_conc.+SO4.ferm.+PO4.ferm.+PO4.utilise; 0.407, 0.706, pH+tmp+P-Source.Feed.conc.+Main.Thr.Conc.+OD+Lys_conc.+yield+lactate+SO4.ferm.+PO4.apporte; 0.407, 0.706, pH+tmp+P-Source.Feed.conc.+Main.Thr.Conc.+Nitrogen.Conc.+Lys_conc.+SO4.ferm.+PO4.ferm.+PO4.apporte+PO4.utilise; 0.406, 0.705, tmp+Main.P-Source.Conc.+P-Source.Feed.conc.+Main.Thr.Conc.+Nitrogen.Conc.+Lys_conc.+PL+His+SO4.ferm.+PO4.apporte; 0.427, 0.705, tmp+P-Source.Feed.conc.+Main.Thr.Conc.+OD+Lys_conc.+yield+SO4.ferm.+PO4.utilise; 0.456, 0.705, tmp+P-Source.Feed.conc.+Main.Thr.Conc.+Lys_conc.+PO4.apporte; 0.406, 0.705, tmp+Main.P-Source.Conc.+P-Source.Feed.conc.+Main.Thr.Conc.+Nitrogen.Conc.+OD+Lys_conc.+lactate+SO4.ferm.+PO4.apporte; 0.406, 0.705, pH+tmp+P-Source.Feed.conc.+Main.Thr.Conc.+Nitrogen.Conc.+Lys_conc.+PL+His+SO4.ferm.+PO4.apporte; 0.406, 0.705, tmp+Main.P-Source.Conc.+P-Source.Feed.conc.+Main.Thr.Conc.+Nitrogen.Conc.+Lys_conc.+yield+PL+SO4.ferm.+PO4.apporte; 0.416, 0.705, tmp+P-Source.Feed.conc.+Main.Thr.Conc.+Lys_conc.+lactate+SO4.ferm.+PO4.ferm.+PO4.apporte+PO4.utilise; 0.416, 0.705, pH+tmp+P-Source.Feed.conc.+Main.Thr.Conc.+Lys_conc.+SO4.ferm.+PO4.ferm.+PO4.apporte+PO4.utilise; 0.406, 0.705, pH+tmp+Main.P-Source.Conc.+P-Source.Feed.conc.+Main.Thr.Conc.+Nitrogen.Conc.+Lys_conc.+SO4.ferm.+PO4.ferm.+PO4.utilise; 0.416, 0.705, tmp+P-Source.Feed.conc.+Main.Thr.Conc.+Nitrogen.Conc.+Lys_conc.+PL+SO4.ferm.+PO4.apporte+PO4.utilise; 0.416, 0.705, pH+tmp+Main.P-Source.Conc.+P-Source.Feed.conc.+Main.Thr.Conc.+Lys_conc.+PL+SO4.ferm.+PO4.apporte; 0.405, 0.705, pH+tmp+P-Source.Feed.conc.+Main.Thr.Conc.+Nitrogen.Conc.+Lys_conc.+lactate+SO4.ferm.+PO4.apporte+PO4.utilise; 0.416, 0.705, tmp+P-Source.Feed.conc.+Main.Thr.Conc.+Nitrogen.Conc.+Lys_conc.+His+SO4.ferm.+PO4.ferm.+PO4.apporte; 0.416, 0.705, tmp+P-Source.Feed.conc.+Main.Thr.Conc.+Nitrogen.Conc.+Lys_conc.+His+SO4.ferm.+PO4.ferm.+PO4.utilise; 0.416, 0.705, tmp+P-Source.Feed.conc.+Main.Thr.Conc.+Nitrogen.Conc.+Lys_conc.+PL+SO4.ferm.+PO4.ferm.+PO4.apporte; 0.426, 0.705, tmp+Main.P-Source.Conc.+P-Source.Feed.conc.+Main.Thr.Conc.+Nitrogen.Conc.+Lys_conc.+yield+SO4.ferm.; 0.416, 0.705, tmp+P-Source.Feed.conc.+Main.Thr.Conc.+Nitrogen.Conc.+Lys_conc.+His+SO4.ferm.+PO4.apporte+PO4.utilise; 0.426, 0.705, tmp+P-Source.Feed.conc.+Main.Thr.Conc.+Lys_conc.+His+SO4.ferm.+PO4.ferm.+PO4.utilise; 0.445, 0.705, pH+tmp+P-Source.Feed.conc.+Main.Thr.Conc.+Lys_conc.+PO4.apporte; 0.416, 0.705, tmp+Main.P-Source.Conc.+P-Source.Feed.conc.+Main.Thr.Conc.+OD+Lys_conc.+yield+SO4.ferm.+PO4.apporte; 0.405, 0.705, pH+tmp+P-Source.Feed.conc.+Main.Thr.Conc.+Nitrogen.Conc.+Lys_conc.+lactate+SO4.ferm.+PO4.ferm.+PO4.apporte; 0.405, 0.705, pH+tmp+P-Source.Feed.conc.+Main.Thr.Conc.+Nitrogen.Conc.+OD+Lys_conc.+PL+SO4.ferm.+PO4.apporte; 0.426, 0.705, tmp+P-Source.Feed.conc.+Main.Thr.Conc.+Lys_conc.+His+lactate+SO4.ferm.+PO4.apporte; 0.426, 0.705, tmp+P-Source.Feed.conc.+Main.Thr.Conc.+OD+Lys_conc.+SO4.ferm.+PO4.apporte+PO4.utilise; 0.415, 0.705, tmp+P-Source.Feed.conc.+Main.Thr.Conc.+Nitrogen.Conc.+Lys_conc.+yield+His+SO4.ferm.+PO4.apporte; 0.415, 0.704, tmp+P-Source.Feed.conc.+Main.Thr.Conc.+Lys_conc.+yield+lactate+SO4.ferm.+PO4.apporte+PO4.utilise; 0.415, 0.704, tmp+P-Source.Feed.conc.+Main.Thr.Conc.+Lys_conc.+yield+lactate+SO4.ferm.+PO4.ferm.+PO4.apporte; 0.415, 0.704, tmp+P-Source.Feed.conc.+Main.Thr.Conc.+Lys_conc.+yield+lactate+SO4.ferm.+PO4.ferm.+PO4.utilise; 0.393, 0.704, pH+tmp+Main.P-Source.Conc.+P-Source.Feed.conc.+Main.Thr.Conc.+Nitrogen.Conc.+Lys_conc.+SO4.ferm.+PO4.ferm.+PO4.apporte+PO4.utilise; 0.425, 0.704, pH+tmp+P-Source.Feed.conc.+Main.Thr.Conc.+Nitrogen. Conc.+Lys_conc.+lactate+PO4.apporte; 0.425, 0.704, pH+tmp+P-Source.Feed.conc.+Main.Thr.Conc.+Nitrogen.Conc.+Lys_conc.+yield+PO4.apporte; 0.425, 0.704, tmp+P-Source.Feed.conc.+Main.Thr.Conc.+Lys_conc.+His+SO4.ferm.+PO4.ferm.+PO4.apporte; 0.425, 0.704, tmp+P-Source.Feed.conc.+Main.Thr.Conc.+Lys_conc.+His+SO4.ferm.+PO4.apporte+PO4.utilise; 0.425, 0.704, tmp+P-Source.Feed.conc.+Main.Thr.Conc.+OD+Lys_conc.+SO4.ferm.+PO4.ferm.+PO4.apporte; 0.445, 0.704, tmp+P-

Source.Feed.conc.+Main.Thr.Conc.+Lys_conc.+yield+PO4.apporte; 0.415, 0.704, tmp+P-Source.Feed.conc.+Main.Thr.Conc.+Nitrogen.Conc.+Lys_conc.+PL+SO4.ferm.+PO4.ferm.+PO4.utilise; 0.415, 0.704, pH+tmp+P-Source.Feed.conc.+Main.Thr.Conc.+Lys_conc.+PL+His+SO4.ferm.+PO4.apporte; 0.404, 0.704, pH+tmp+P-Source.Feed.conc.+Main.Thr.Conc.+Nitrogen.Conc.+Lys_conc.+lactate+SO4.ferm.+PO4.ferm.+PO4.utilise; 0.404, 0.704, tmp+P-Source.Feed.conc.+Main.Thr.Conc.+Nitrogen.Conc.+Lys_conc.+lactate+SO4.ferm.+PO4.ferm.+PO4.apporte+PO4.utilise; 0.414, 0.704, tmp+Main.P-Source.Conc.+P-Source.Feed.conc.+Main.Thr.Conc.+OD+Lys_conc.+lactate+SO4.ferm.+PO4.apporte; 0.404, 0.704, tmp+Main.P-Source.Conc.+P-Source.Feed.conc.+Main.Thr.Conc.+Nitrogen.Conc.+Lys_conc.+lactate+SO4.ferm.+PO4.ferm.+PO4.apporte; 0.403, 0.704, tmp+Main.P-Source.Conc.+P-Source.Feed.conc.+Main.Thr.Conc.+Nitrogen.Conc.+Lys_conc.+lactate+SO4.ferm.+PO4.apporte+PO4.utilise; 0.403, 0.704, tmp+Main.P-Source.Conc.+P-Source.Feed.conc.+Main.Thr.Conc.+Nitrogen.Conc.+OD+Lys_conc.+His+SO4.ferm.+PO4.apporte; 0.414, 0.704, pH+tmp+Main.P-Source.Conc.+P-Source.Feed.conc.+Main.Thr.Conc.+Lys_conc.+His+SO4.ferm.+PO4.apporte; 0.403, 0.704, tmp+Main.P-Source.Conc.+P-Source.Feed.conc.+Main.Thr.Conc.+Nitrogen.Conc.+OD+Lys_conc.+yield+SO4.ferm.+PO4.apporte; 0.403, 0.704, tmp+P-Source.Feed.conc.+Main.Thr.Conc.+Nitrogen.Conc.+OD+Lys_conc.+PL+lactate+SO4.ferm.+PO4.apporte; 0.414, 0.704, pH+tmp+P-Source.Feed.conc.+Main.Thr.Conc.+Lys_conc.+yield+SO4.ferm.+PO4.apporte+PO4.utilise; 0.424, 0.703, tmp+P-Source.Feed.conc.+Main.Thr.Conc.+OD+Lys_conc.+SO4.ferm.+PO4.ferm.+PO4.utilise; 0.414, 0.703, pH+tmp+P-Source.Feed.conc.+Main.Thr.Conc.+Lys_conc.+yield+SO4.ferm.+PO4.ferm.+PO4.apporte; 0.403, 0.703, pH+tmp+P-Source.Feed.conc.+Main.Thr.Conc.+Lys_conc.+yield+PL+lactate+SO4.ferm.+PO4.apporte; 0.414, 0.703, pH+tmp+P-Source.Feed.conc.+Main.Thr.Conc.+Lys_conc.+yield+SO4.ferm.+PO4.ferm.+PO4.utilise; 0.424, 0.703, tmp+Main.P-Source.Conc.+P-Source.Feed.conc.+Main.Thr.Conc.+Nitrogen.Conc.+Lys_conc.+SO4.ferm.+PO4.utilise; 0.413, 0.703, pH+tmp+P-Source.Feed.conc.+Main.Thr.Conc.+OD+Lys_conc.+His+SO4.ferm.+PO4.utilise; 0.413, 0.703, tmp+Main.P-Source.Conc.+P-Source.Feed.conc.+Main.Thr.Conc.+Lys_conc.+yield+PL+SO4.ferm.+PO4.apporte; 0.413, 0.703, tmp+Main.P-Source.Conc.+P-Source.Feed.conc.+Main.Thr.Conc.+OD+Lys_conc.+His+SO4.ferm.+PO4.apporte; 0.413, 0.703, tmp+P-Source.Feed.conc.+Main.Thr.Conc.+Lys_conc.+PL+lactate+SO4.ferm.+PO4.apporte+PO4.utilise; 0.403, 0.703, tmp+P-Source.Feed.conc.+Main.Thr.Conc.+Nitrogen.Conc.+OD+Lys_conc.+PL+His+SO4.ferm.+PO4.apporte; 0.413, 0.703, tmp+P-Source.Feed.conc.+Main.Thr.Conc.+Nitrogen.Conc.+OD+Lys_conc.+SO4.ferm.+PO4.apporte+PO4.utilise; 0.433, 0.703, tmp+Main.P-Source.Conc.+P-Source.Feed.conc.+Main.Thr.Conc.+Nitrogen.Conc.+Lys_conc.+PO4.apporte; 0.413, 0.703, tmp+P-Source.Feed.conc.+Main.Thr.Conc.+Lys_conc.+PL+lactate+SO4.ferm.+PO4.ferm.+PO4.apporte; 0.413, 0.703, tmp+P-Source.Feed.conc.+Main.Thr.Conc.+Lys_conc.+PL+lactate+SO4.ferm.+PO4.ferm.+PO4.utilise; 0.413, 0.703, tmp+Main.P-Source.Conc.+P-Source.Feed.conc.+Main.Thr.Conc.+Nitrogen.Conc.+OD+Lys_conc.+SO4.ferm.+PO4.ferm.+PO4.apporte; 0.433, 0.703, tmp+P-Source.Feed.conc.+Main.Thr.Conc.+Nitrogen.Conc.+Lys_conc.+His+PO4.apporte; 0.402, 0.703, tmp+Main.P-Source.Conc.+P-Source.Feed.conc.+Main.Thr.Conc.+Nitrogen.Conc.+Lys_conc.+lactate+SO4.ferm.+PO4.ferm.+PO4.utilise; 0.412, 0.703, tmp+Main.P-Source.Conc.+P-Source.Feed.conc.+Main.Thr.Conc.+Lys_conc.+lactate+SO4.ferm.+PO4.apporte+PO4.utilise; 0.412, 0.703, tmp+Main.P-Source.Conc.+P-Source.Feed.conc.+Main.Thr.Conc.+Lys_conc.+lactate+SO4.ferm.+PO4.ferm.+PO4.apporte; 0.401, 0.702, pH+tmp+P-Source.Feed.conc.+Main.Thr.Conc.+Nitrogen.Conc.+Lys_conc.+yield+SO4.ferm.+PO4.apporte+PO4.utilise; 0.401, 0.702, pH+tmp+P-Source.Feed.conc.+Main.Thr.Conc.+Nitrogen.Conc.+Lys_conc.+His+lactate+SO4.ferm.+PO4.apporte; 0.412, 0.702, pH+tmp+Main.P-Source.Conc.+P-Source.Feed.conc.+Main.Thr.Conc.+Lys_conc.+SO4.ferm.+PO4.apporte+PO4.utilise; 0.401, 0.702, pH+tmp+P-Source.Feed.conc.+Main.Thr.Conc.+Nitrogen.Conc.+Lys_conc.+yield+SO4.ferm.+PO4.ferm.+PO4.apporte; 0.412, 0.702, pH+tmp+Main.P-Source.Conc.+P-Source.Feed.conc.+Main.Thr.Conc.+Nitrogen.Conc.+Lys_conc.+yield+SO4.ferm.; 0.412, 0.702, pH+tmp+Main.P-Source.Conc.+P-Source.Feed.conc.+Main.Thr.Conc.+Lys_conc.+SO4.ferm.+PO4.ferm.+PO4.apporte; 0.412, 0.702, tmp+P-Source.Feed.conc.+Main.Thr.Conc.+Lys_conc.+yield+SO4.ferm.+PO4.ferm.+PO4.apporte+PO4.utilise; 0.401, 0.702, pH+tmp+Main.P-Source.Conc.+P-Source.Feed.conc.+Main.Thr.Conc.+Lys_conc.+yield+lactate+SO4.ferm.+PO4.apporte; 0.401, 0.702, pH+tmp+P-Source.Feed.conc.+Main.Thr.Conc.+OD+Lys_conc.+PL+lactate+SO4.ferm.+PO4.apporte; 0.432, 0.702, tmp+P-Source.Feed.conc.+Main.Thr.Conc.+Nitrogen.Conc.+Lys_conc.+PL+PO4.apporte; 0.401, 0.702, tmp+P-Source.Feed.conc.+Main.Thr.Conc.+Nitrogen.Conc.+Lys_conc.+yield+lactate+SO4.ferm.+PO4.apporte+PO4.utilise; 0.401, 0.702, tmp+P-Source.Feed.conc.+Main.Thr.Conc.+Nitrogen.Conc.+Lys_conc.+yield+lactate+SO4.ferm.+PO4.ferm.+PO4.apporte; 0.390, 0.702, pH+tmp+Main.P-Source.Conc.+P-Source.Feed.conc.+Main.Thr.Conc.+Nitrogen.Conc.+Lys_conc.+PL+lactate+SO4.ferm.+PO4.apporte; 0.422, 0.702, tmp+P-Source.Feed.conc.+Main.Thr.Conc.+Nitrogen.Conc.+Lys_conc.+yield+lactate+PO4.apporte; 0.390, 0.702, pH+tmp+P-Source.Feed.conc.+Main.Thr.Conc.+Nitrogen.Conc.+OD+Lys_conc.+yield+lactate+SO4.ferm.+PO4.apporte; 0.401, 0.702, tmp+P-Source.Feed.conc.+Main.Thr.Conc.+Nitrogen.Conc.+OD+Lys_conc.+yield+PL+SO4.ferm.+PO4.apporte; 0.411, 0.702, tmp+Main.P-Source.Conc.+P-Source.Feed.conc.+Main.Thr.Conc.+Lys_conc.+lactate+SO4.ferm.+PO4.ferm.+PO4.utilise; 0.411, 0.702, tmp+P-Source.Feed.conc.+Main.Thr.Conc.+Nitrogen.Conc.+OD+Lys_conc.+SO4.ferm.+PO4.ferm.+PO4.utilise; 0.401, 0.702, pH+tmp+P-Source.Feed.conc.+Main.Thr.Conc.+OD+Lys_conc.+PL+His+SO4.ferm.+PO4.apporte; 0.400, 0.702, pH+tmp+P-Source.Feed.conc.+Main.Thr.Conc.+Nitrogen.Conc.+Lys_conc.+yield+SO4.ferm.+PO4.ferm.+PO4.utilise; 0.400, 0.702, tmp+P-Source.Feed.conc.+Main.Thr.Conc.+OD+Lys_conc.+yield+PL+lactate+SO4.ferm.+PO4.apporte; 0.411, 0.702, pH+tmp+Main.P-Source.Conc.+P-Source.Feed.conc.+Main.Thr.Conc.+Lys_conc.+SO4.ferm.+PO4.ferm.+PO4.utilise; 0.400, 0.702, pH+tmp+P-Source.Feed.conc.+Main.Thr.Conc.+OD+Lys_conc.+yield+PL+SO4.ferm.+PO4.apporte; 0.389, 0.702, pH+tmp+Main.P-Source.Conc.+P-Source.Feed.conc.+Main.Thr.Conc.+Nitrogen.Conc.+OD+Lys_conc.+lactate+SO4.ferm.+PO4.apporte; 0.400, 0.702, tmp+P-Source.Feed.conc.+Main.Thr.Conc.+Nitrogen.Conc.+Lys_conc.+yield+lactate+SO4.ferm.+PO4.ferm.+PO4.utilise; 0.411, 0.702, pH+tmp+P-Source.Feed.conc.+Main.Thr.Conc.+OD+Lys_conc.+SO4.ferm.+PO4.apporte+PO4.utilise; 0.421, 0.702, pH+tmp+Main.P-

Source.Conc.+P-Source.Feed.conc.+Main.Thr.Conc.+ Nitrogen.Conc.+Lys_conc.+PO4.apporte; 0.400, 0.702, tmp+Main.P-Source.Conc.+P-Source.Feed.conc.+ Main.Thr.Conc.+Nitrogen.Conc.+Lys_conc.+yield+ SO4.ferm.+PO4.ferm.+PO4.apporte; 0.431, 0.702, tmp+P-Source.Feed.conc.+Main.Thr.Conc.+Nitrogen.Conc.+OD+ Lys_conc.+PO4.apporte; 0.400, 0.702, tmp+Main.P-Source.Conc.+P-Source.Feed.conc.+Main.Thr.Conc.+ Nitrogen.Conc.+Lys_conc.+yield+SO4.ferm.+ PO4.apporte+PO4.utilise; 0.389, 0.702, pH+tmp+P-Source.Feed.conc.+Main.Thr.Conc.+Nitrogen.Conc.+ Lys_conc.+yield+PL+lactate+SO4.ferm.+PO4.apporte; 0.411, 0.702, pH+tmp+P-Source.Feed.conc.+Main.Thr. Conc.+Lys_conc.+PL+SO4.ferm.+PO4.apporte+ PO4.utilise; 0.400, 0.702, tmp+Main.P-Source.Conc.+P-Source.Feed.conc.+Main.Thr.Conc.+Nitrogen.Conc.+Lys_conc.+His+lactate+SO4.ferm.+PO4.apporte; 0.410, 0.701, pH+tmp+P-Source.Feed.conc.+Main.Thr.Conc.+Lys_conc.+PL+SO4.ferm.+PO4.ferm.+PO4.apporte; 0.421, 0.701, tmp+Main.P-Source.Conc.+P-Source.Feed.conc.+ Main.Thr.Conc.+Nitrogen.Conc.+Lys_conc.+lactate+ SO4.ferm.; 0.431, 0.701, tmp+P-Source.Feed.conc.+ Main.Thr.Conc.+OD+Lys_conc.+yield+PO4.apporte; 0.421, 0.701, pH+tmp+P-Source.Feed.conc.+Main.Thr. Conc.+Nitrogen.Conc.+OD+Lys_conc.+PO4.apporte; 0.410, 0.701, pH+tmp+Main.P-Source.Conc.+P-Source.Feed.conc.+Main.Thr.Conc.+Nitrogen.Conc.+Lys_conc.+SO4.ferm.+PO4.utilise; 0.410, 0.701, tmp+P-Source.Feed.conc.+Main.Thr.Conc.+Nitrogen.Conc.+OD+ Lys_conc.+His+SO4.ferm.+PO4.utilise; 0.410, 0.701, tmp+P-Source.Feed.conc.+Main.Thr.Conc.+Lys_conc.+PL+ SO4.ferm.+PO4.ferm.+PO4.apporte+PO4.utilise; 0.410, 0.701, pH+tmp+P-Source.Feed.conc.+Main.Thr.Conc.+ OD+Lys_conc.+504.ferm.+PO4.ferm.+PO4.apporte; 0.399, 0.701, tmp+P-Source.Feed.conc.+Main.Thr.Conc.+Nitrogen.Conc.+Lys_conc.+yield+SO4.ferm.+PO4.ferm.+ PO4.apporte+PO4.utilise; 0.410, 0.701, pH+tmp+P-Source.Feed.conc.+Main.Thr.Conc.+Lys_conc.+PL+ SO4.ferm.+PO4.ferm.+PO4.utilise; 0.388, 0.701, tmp+ Main.P-Source.Conc.+P-Source.Feed.conc.+Main.Thr. Conc.+Nitrogen.Conc.+Lys_conc.+lactate+SO4.ferm.+ PO4.ferm.+PO4.apporte+PO4.utilise; 0.399, 0.701, tmp+ Main.P-Source.Conc.+P-Source.Feed.conc.+Main.Thr. Conc.+Nitrogen.Conc.+Lys_conc.+His+SO4.ferm.+ PO4.ferm.+PO4.apporte; 0.420, 0.701, pH+tmp+P-Source.Feed.conc.+Main.Thr.Conc.+Nitrogen.Conc.+Lys_conc.+His+PO4.apporte; 0.388, 0.701, pH+tmp+Main.P-Source.Conc.+P-Source.Feed.conc.+Main.Thr.Conc.+Nitrogen.Conc.+OD+Lys_conc.+His+SO4.ferm.+ PO4.apporte; 0.399, 0.701, tmp+Main.P-Source.Conc.+P-Source.Feed.conc.+Main.Thr.Conc.+Nitrogen.Conc.+ Lys_conc.+His+SO4.ferm.+PO4.apporte+PO4.utilise; 0.439, 0.701, tmp+P-Source.Feed.conc.+Main.Thr.Conc.+ Lys_conc.+lactate+PO4.apporte; 0.398, 0.701, tmp+ Main.P-Source.Conc.+P-Source.Feed.conc.+Main.Thr. Conc.+Nitrogen.Conc.+Lys_conc.+yield+SO4.ferm.+ PO4.ferm.+PO4.utilise; 0.430, 0.701, pH+tmp+P-Source.Feed.conc.+Main.Thr.Conc.+Lys_conc.+yield+ PO4.apporte; 0.409, 0.701, pH+tmp+Main.P-Source.Conc.+ P-Source.Feed.conc.+Main.Thr.Conc.+Nitrogen.Conc.+Lys_conc.+lactate+SO4.ferm.; 0.409, 0.701, pH+tmp+P-Source.Feed.conc.+Main.Thr.Conc.+OD+Lys_conc.+yield+ SO4.ferm.+PO4.utilise; 0.409, 0.701, pH+tmp+P-Source.Feed.conc.+Main.Thr.Conc.+OD+Lys_conc.+ SO4.ferm.+PO4.ferm.+PO4.utilise; 0.398, 0.701, tmp+ Main.P-Source.Conc.+P-Source.Feed.conc.+ Main.Thr.Conc.+OD+Lys_conc.+PL+
SO4.ferm.+PO4.apporte; 0.448, 0.701, tmp+Main.Thr. Conc.+Lys_conc.+SO4.ferm.+PO4.apporte; 0.398, 0.701, pH+tmp+Main.P-Source.Conc.+P-Source. Feed.conc.+ Main.Thr.Conc.+OD+Lys_conc.+yield+SO4.ferm.+ PO4.apporte; 0.409, 0.701, tmp+Main.P-Source.Conc.+P-Source.Feed.conc.+Main.Thr.Conc.+Lys_conc.+PL+His+ SO4.ferm.+PO4.apporte; 0.398, 0.701, tmp+P-Source.Feed.conc.+Main.Thr.Conc.+Nitrogen. Conc.+ Lys_conc.+PL+SO4.ferm.+PO4.ferm.+PO4.apporte+ PO4.utilise; 0.409, 0.700, tmp+Main.P-Source.Conc.+P-Source.Feed.conc.+Main.Thr.Conc.+OD+Lys_conc.+PL+ SO4.ferm.+PO4.apporte; 0.387, 0.700, pH+tmp+Main.P-Source.Conc.+P-Source.Feed.conc.+Main.Thr.Conc.+ Nitrogen.Conc.+Lys_conc.+yield+PL+SO4.ferm.+ PO4.apporte; 0.398, 0.700, tmp+Main.P-Source.Conc.+P-Source.Feed.conc.+Main.Thr.Conc.+Nitrogen.Conc.+ Lys_conc.+His+SO4.ferm.+PO4.ferm.+PO4.utilise; 0.387, 0.700, pH+tmp+Main.P-Source.Conc.+P-Source.Feed. conc.+Main.Thr.Conc.+Nitrogen.Conc.+Lys_conc.+lactate+SO4.ferm.+PO4.ferm.+PO4.apporte; 0.387, 0.700, pH+tmp+Main.P-Source.Conc.+P-Source. Feed.conc.+ Main.Thr.Conc.+Nitrogen.Conc.+Lys_conc.+lactate+ SO4.ferm.+PO4.apporte+PO4.utilise; 0.387, 0.700, pH+tmp+Main.P-Source.Conc.+P-Source.Feed.conc.+ Main.Thr.Conc.+Nitrogen.Conc.+OD+Lys_conc.+yield+ SO4.ferm.+PO4.apporte; 0.387, 0.700, tmp+Main.P-Source.Conc.+P-Source.Feed.conc.+Main.Thr.Conc.+ Nitrogen.Conc.+Lys_conc.+yield+PL+lactate+SO4.ferm.+ PO4.apporte; 0.419, 0.700, tmp+P-Source.Feed.conc.+ Main.Thr.Conc.+Nitrogen.Conc.+Lys_conc.+PO4.ferm.+ PO4.apporte+PO4.utilise; 0.408, 0.700, tmp+P-Source.Feed.conc.+Main.Thr.Conc.+OD+Lys_conc.+PL+ His+SO4.ferm.+PO4.utilise; 0.408, 0.700, tmp+P-Source.Feed.conc.+Main.Thr.Conc.+OD+Lys_conc.+ lactate+SO4.ferm.+PO4.apporte+PO4.utilise; 0.408, 0.700, tmp+P-Source.Feed.conc.+Main.Thr.Conc.+OD+Lys_conc.+yield+lactate+SO4.ferm.+PO4.utilise; 0.386, 0.700, pH+tmp+Main.P-Source.Conc.+P-Source.Feed. conc.+Main.Thr.Conc.+Nitrogen.Conc.+Lys_conc.+PL+ His+SO4.ferm.+PO4.apporte; 0.419, 0.700, pH+tmp+P-Source.Feed.conc.+Main.Thr.Conc.+Nitrogen.Conc.+Lys_conc.+PL+PO4.apporte; 0.428, 0.700, tmp+P-Source.Feed.conc.+Main.Thr.Conc.+OD+Lys_conc.+ SO4.ferm.+PO4.utilise; 0.418, 0.700, tmp+P-Source.Feed.conc.+Main.Thr.Conc.+Lys_conc.+yield+His+ SO4.ferm.+PO4.apporte; 0.397, 0.700, pH+tmp+P-Source.Feed.conc.+Main.Thr.Conc.+Nitrogen.Conc.+ Lys_conc.+yield+His+SO4.ferm.+PO4.apporte; 0.397, 0.700, pH+tmp+P-Source.Feed.conc.+Main.Thr.Conc.+Nitrogen.Conc.+Lys_conc.+His+SO4.ferm.+PO4.ferm.+ PO4.utilise; 0.408, 0.700, tmp+P-Source.Feed.conc.+Main. Thr.Conc.+OD+Lys_conc.+lactate+SO4.ferm.+PO4.ferm.+ PO4.apporte; 0.397, 0.700, pH+tmp+P-Source.Feed.conc.+ Main.Thr.Conc.+Lys_conc.+lactate+SO4.ferm.+ PO4.ferm.+PO4.apporte+PO4.utilise; 0.408, 0.700, tmp+ Main.P-Source.Conc.+P-Source.Feed.conc.+ Main.Thr.Conc.+Nitrogen.Conc.+Lys_conc.+lactate+ SO4.ferm.+PO4.utilise; 0.408, 0.700, tmp+Main.P-Source.Conc.+P-Source.Feed.conc.+Main.Thr.Conc.+ Lys_conc.+yield+SO4.ferm.+PO4.apporte+PO4.utilise; 0.397, 0.700, pH+tmp+Main.P-Source.Conc.+P-Source. Feed.conc.+Main.Thr.Conc.+OD+Lys_conc.+His+ SO4.ferm.+PO4.apporte; 0.408, 0.700, tmp+Main.P-Source.Conc.+P-Source.Feed.conc.+Main.Thr.Conc.+Lys_conc.+yield+SO4.ferm.+PO4.ferm.+PO4.apporte; 0.397, 0.700, pH+tmp+Main.P-Source.Conc.+P-Source.Feed. conc.+Main.Thr.Conc.+Lys_conc.+PL+lactate+SO4.ferm.+

PO4.apporte; 0.397, 0.700, pH+tmp+P-Source.Feed.conc.+ Main.Thr.Conc.+Nitrogen.Conc.+Lys_conc.+His+ SO4.ferm.+PO4.ferm.+PO4.apporte; 0.397, 0.700, pH+tmp+P-Source.Feed.conc.+Main.Thr.Conc.+ Nitrogen.Conc.+Lys_conc.+His+SO4.ferm.+PO4.apporte+ PO4.utilise; 0.397, 0.700, pH+tmp+P-Source.Feed.conc.+ Main.Thr.Conc.+Nitrogen.Conc.+Lys_conc.+PL+ SO4.ferm.+PO4.apporte+PO4.utilise; 0.397, 0.700, pH+tmp+Main.P-Source.Conc.+P-Source.Feed.conc.+ Main.Thr.Conc.+OD+Lys_conc.+lactate+SO4.ferm.+ PO4.apporte; 0.408, 0.700, tmp+P-Source.Feed.conc.+ Main.Thr.Conc.+Lys_conc.+yield+PL+SO4.ferm.+ PO4.apporte+PO4.utilise; 0.408, 0.700, pH+tmp+P-Source.Feed.conc.+Main.Thr.Conc.+Lys_conc.+His+ SO4.ferm.+PO4.ferm.+PO4.utilise; 0.397, 0.700, pH+tmp+ P-Source.Feed.conc.+Main.Thr.Conc.+Nitrogen.Conc.+ OD+Lys_conc.+SO4.ferm.+PO4.apporte+PO4.utilise; 0.407, 0.700, tmp+P-Source.Feed.conc.+Main.Thr.Conc.+ Lys_conc.+yield+PL+SO4.ferm.+PO4.ferm.+PO4.apporte; 0.407, 0.700, tmp+P-Source.Feed.conc.+Main.Thr.Conc.+ Lys_conc.+yield+PL+SO4.ferm.+PO4.ferm.+PO4.utilise; 0.397, 0.700, tmp+P-Source.Feed.conc.+Main.Thr.Conc.+ Nitrogen.Conc.+Lys_conc.+PL+lactate+SO4.ferm.+ PO4.apporte+PO4.utilise; 0.407, 0.700, pH+tmp+P-Source.Feed.conc.+Main.Thr.Conc.+Lys_conc.+His+lactate+SO4.ferm.+PO4.apporte; 0.397, 0.700, pH+tmp+P-Source.Feed.conc.+Main.Thr.Conc.+Nitrogen.Conc.+Lys_conc.+PL+SO4.ferm.+PO4.ferm.+PO4.apporte; 0.407, 0.700, tmp+Main.P-Source.Conc.+P-Source.Feed.conc.+ Main.Thr.Conc.+Lys_conc.+yield+SO4.ferm.+PO4.ferm.+ PO4.utilise; 0.407, 0.699, tmp+Main.P-Source.Conc.+P-Source.Feed.conc.+Main.Thr.Conc.+Nitrogen.Conc.+ Lys_conc.+His+SO4.ferm.+PO4.utilise; 0.396, 0.699, tmp+ P-Source.Feed.conc.+Main.Thr.Conc.+Nitrogen.Conc.+ Lys_conc.+PL+lactate+SO4.ferm.+PO4.ferm.+ PO4.apporte; 0.407, 0.699, tmp+P-Source.Feed.conc.+ Main.Thr.Conc.+OD+Lys_conc.+yield+His+SO4.ferm.+ PO4.apporte; 0.385, 0.699, pH+tmp+Main.P-Source.Conc.+ P-Source.Feed.conc.+Main.Thr.Conc.+Nitrogen.Conc.+ Lys_conc.+lactate+SO4.ferm.+PO4.ferm.+PO4.utilise; 0.407, 0.699, tmp+P-Source.Feed.conc.+Main.Thr.Conc.+ OD+Lys_conc.+lactate+SO4.ferm.+PO4.ferm.+PO4.utilise; 0.396, 0.699, pH+tmp+P-Source.Feed.conc.+Main.Thr. Conc.+Lys_conc.+yield+lactate+SO4.ferm.+PO4.apporte+ PO4.utilise; 0.407, 0.699, tmp+Main.P-Source.Conc.+P-Source.Feed.conc.+Main.Thr.Conc.+Lys_conc.+ SO4.ferm.+PO4.ferm.+PO4.apporte+PO4.utilise; 0.396, 0.699, pH+tmp+P-Source.Feed.conc.+Main.Thr.Conc.+Nitrogen.Conc.+OD+Lys_conc.+SO4.ferm.+PO4.ferm.+ PO4.apporte; 0.417, 0.699, pH+tmp+P-Source.Feed.conc.+ Main.Thr.Conc.+OD+Lys_conc.+yield+PO4.apporte; 0.396, 0.699, pH+tmp+P-Source.Feed.conc.+Main.Thr. Conc.+Lys_conc.+yield+lactate+SO4.ferm.+PO4.ferm.+ PO4.apporte; 0.407, 0.699, pH+tmp+P-Source.Feed.conc.+ Main.Thr.Conc.+Lys_conc.+His+SO4.ferm.+PO4.ferm.+ PO4.apporte; 0.407, 0.699, tmp+P-Source.Feed.conc.+ Main.Thr.Conc.+OD+Lys_conc.+yield+SO4.ferm.+ PO4.apporte+PO4.utilise; 0.396, 0.699, pH+tmp+P-Source.Feed.conc.+Main.Thr.Conc.+Lys_conc.+yield+ lactate+SO4.ferm.+PO4.ferm.+PO4.utilise; 0.407, 0.699, pH+tmp+P-Source.Feed.conc.+Main.Thr.Conc.+Lys_conc.+His+SO4.ferm.+PO4.apporte+PO4.utilise; 0.396, 0.699, tmp+Main.P-Source.Conc.+P-Source.Feed.conc.+ Main.Thr.Conc.+Lys_conc.+yield+PL+lactate+SO4.ferm.+ PO4.apporte; 0.396, 0.699, pH+tmp+P-Source.Feed.conc.+ Main.Thr.Conc.+Nitrogen.Conc.+PL+ SO4.ferm.+PO4.ferm.+PO4.utilise; 0.407, 0.699, tmp+P-Source.Feed.conc.+Main.Thr.Conc.+OD+Lys_conc.+His+ SO4.ferm.+PO4.apporte+PO4.utilise; 0.406, 0.699, tmp+P-Source.Feed.conc.+Main.Thr.Conc.+OD+Lys_conc.+His+ SO4.ferm.+PO4.ferm.+PO4.apporte; 0.396, 0.699, tmp+ Main.P-Source.Conc.+P-Source.Feed.conc.+ Main.Thr.Conc.+Nitrogen.Conc.+Lys_conc.+PL+ SO4.ferm.+PO4.apporte+PO4.utilise; 0.396, 0.699, tmp+ Main.P-Source.Conc.+P-Source.Feed.conc.+ Main.Thr.Conc.+Nitrogen.Conc.+Lys_conc.+PL+ SO4.ferm.+PO4.ferm.+PO4.apporte; 0.427, 0.699, pH+tmp+P-Source.Feed.conc.+Main.Thr.Conc.+Lys_conc.+lactate+PO4.apporte; 0.406, 0.699, tmp+P-Source.Feed.conc.+Main.Thr.Conc.+OD+Lys_conc.+yield+ SO4.ferm.+PO4.ferm.+PO4.apporte; 0.395, 0.699, tmp+P-Source.Feed.conc.+Main.Thr.Conc.+Nitrogen.Conc.+Lys_conc.+PL+lactate+SO4.ferm.+PO4.ferm.+PO4.utilise; 0.384, 0.699, pH+tmp+P-Source.Feed.conc.+Main.Thr. Conc.+Nitrogen.Conc.+Lys_conc.+lactate+SO4.ferm.+ PO4.ferm.+PO4.apporte+PO4.utilise; 0.406, 0.699, tmp+P-Source.Feed.conc.+Main.Thr.Conc.+OD+Lys_conc.+His+ SO4.ferm.+PO4.ferm.+PO4.utilise; 0.406, 0.699, tmp+P-Source.Feed.conc.+Main.Thr.Conc.+OD+Lys_conc.+His+ lactate+SO4.ferm.+PO4.utilise; 0.395, 0.699, tmp+P-Source.Feed.conc.+Main.Thr.Conc.+Nitrogen.Conc.+ Lys_conc.+PL+His+lactate+SO4.ferm.+PO4.apporte; 0.416, 0.699, tmp+Main.P-Source.Conc.+P-Source.Feed. conc.+Main.Thr.Conc.+Nitrogen.Conc.+Lys_conc.+PL+ SO4.ferm.; 0.427, 0.699, tmp+P-Source.Feed.conc.+Main. Thr.Conc.+Lys_conc.+yield+lactate+PO4.apporte; 0.395, 0.699, tmp+Main.P-Source.Conc.+P-Source.Feed.conc.+ Main.Thr.Conc.+OD+Lys_conc.+yield+lactate+SO4.ferm.+ PO4.apporte; 0.406, 0.699, tmp+P-Source.Feed.conc.+ Main.Thr.Conc.+OD+Lys_conc.+His+lactate+SO4.ferm.+ PO4.apporte; 0.406, 0.699, tmp+P-Source.Feed.conc.+ Main.Thr.Conc.+OD+Lys_conc.+SO4.ferm.+PO4.ferm.+ PO4.apporte+PO4.utilise; 0.406, 0.699, tmp+P-Source.Feed.conc.+Main.Thr.Conc.+OD+Lys_conc.+yield+ SO4.ferm.+PO4.ferm.+PO4.utilise; 0.426, 0.699, pH+tmp+ P-Source.Feed.conc.+Main.Thr.Conc.+OD+Lys_conc.+ PO4.apporte; 0.395, 0.699, pH+tmp+P-Source.Feed.conc.+ Main.Thr.Conc.+Nitrogen.Conc.+OD+Lys_conc.+ SO4.ferm.+PO4.ferm.+PO4.utilise; 0.406, 0.698, tmp+P-Source.Feed.conc.+Main.Thr.Conc.+OD+Lys_conc.+yield+ His+SO4.ferm.+PO4.utilise; 0.426, 0.698, tmp+P-Source.Feed.conc.+Main.Thr.Conc.+Nitrogen.Conc.+ Lys_conc.+SO4.ferm.+PO4.utilise; 0.405, 0.698, pH+tmp+ P-Source.Feed.conc.+Main.Thr.Conc.+Nitrogen.Conc.+ Lys_conc.+yield+lactate+PO4.apporte; 0.383, 0.698, pH+tmp+P-Source.Feed.conc.+Main.Thr.Conc.+ Nitrogen.Conc.+OD+Lys_conc.+PL+His+SO4.ferm.+ PO4.apporte; 0.394, 0.698, tmp+P-Source.Feed.conc.+ Main.Thr.Conc.+Nitrogen.Conc.+OD+Lys_conc.+ SO4.ferm.+PO4.ferm.+PO4.apporte+PO4.utilise; 0.416, 0.698, tmp+P-Source.Feed.conc.+Main.Thr.Conc.+Nitrogen.Conc.+OD+Lys_conc.+yield+PO4.apporte; 0.405, 0.698, tmp+Main.P-Source.Conc.+P-Source.Feed.conc.+ Main.Thr.Conc.+Nitrogen.Conc.+Lys_conc.+yield+lactate+ SO4.ferm.; 0.383, 0.698, pH+tmp+P-Source.Feed.conc.+ Main.Thr.Conc.+Nitrogen.Conc.+OD+Lys_conc.+PL+ lactate+SO4.ferm.+PO4.apporte; 0.415, 0.698, tmp+P-Source.Feed.conc.+Main.Thr.Conc.+OD+Lys_conc.+ lactate+SO4.ferm.+PO4.utilise; 0.383, 0.698, tmp+Main.P-Source.Conc.+P-Source.Feed.conc.+Main.Thr.Conc.+ Nitrogen.Conc.+OD+Lys_conc.+yield+lactate+SO4.ferm.+ PO4.apporte; 0.383, 0.698, pH+tmp+Main.P-Source.Conc.+ P-Source.Feed.conc.+Main.Thr.Conc.+Nitrogen.Conc.+ Lys_conc.+yield+SO4.ferm.+PO4.ferm.+PO4.apporte;

0.383, 0.698, pH+tmp+Main.P-Source.Conc.+P-Source.Feed.conc.+Main.Thr.Conc.+Nitrogen.Conc.+Lys_conc.+yield+SO4.ferm.+PO4.apporte+PO4.utilise; 0.394, 0.698, tmp+Main.P-Source.Conc.+P-Source.Feed.conc.+Main.Thr.Conc.+Nitrogen.Conc.+Lys_conc.+PL+SO4.ferm.+PO4.ferm.+PO4.utilise; 0.405, 0.698, tmp+Main.P-Source.Conc.+P-Source.Feed.conc.+Main.Thr.Conc.+Lys_conc.+PL+SO4.ferm.+PO4.apporte+PO4.utilise; 0.394, 0.698, tmp+P-Source.Feed.conc.+Main.Thr.Conc.+Lys_conc.+yield+lactate+SO4.ferm.+PO4.ferm.+PO4.apporte+PO4.utilise; 0.405, 0.698, tmp+Main.P-Source.Conc.+P-Source.Feed.conc.+Main.Thr.Conc.+Lys_conc.+PL+SO4.ferm.+PO4.ferm.+PO4.apporte; 0.405, 0.698, tmp+Main.P-Source.Conc.+P-Source.Feed.conc.+Main.Thr.Conc.+Nitrogen.Conc.+Lys_conc.+yield+SO4.ferm.+PO4.utilise; 0.394, 0.698, pH+tmp+Main.P-Source.Conc.+P-Source.Feed.conc.+Main.Thr.Conc.+Lys_conc.+lactate+SO4.ferm.+PO4.apporte+PO4.utilise; 0.394, 0.698, tmp+P-Source.Feed.conc.+Main.Thr.Conc.+Nitrogen.Conc.+OD+Lys_conc.+yield+His+SO4.ferm.+PO4.apporte; 0.394, 0.698, pH+tmp+Main.P-Source.Conc.+P-Source.Feed.conc.+Main.Thr.Conc.+Lys_conc.+lactate+SO4.ferm.+PO4.ferm.+PO4.apporte; 0.415, 0.698, tmp+Main.P-Source.Conc.+P-Source.Feed.conc.+Main.Thr.Conc.+Nitrogen.Conc.+Lys_conc.+yield+PO4.apporte; 0.404, 0.698, tmp+P-Source.Feed.conc.+Main.Thr.Conc.+Nitrogen.Conc.+OD+Lys_conc.+yield+SO4.ferm.+PO4.utilise; 0.404, 0.698, tmp+P-Source.Feed.conc.+Main.Thr.Conc.+Lys_conc.+PL+His+lactate+SO4.ferm.+PO4.apporte; 0.414, 0.698, tmp+Main.P-Source.Conc.+P-Source.Feed.conc.+Main.Thr.Conc.+Nitrogen.Conc.+Lys_conc.+His+SO4.ferm.; 0.434, 0.698, tmp+P-Source.Feed.conc.+Main.Thr.Conc.+OD+Lys_conc.+PO4.apporte; 0.393, 0.698, tmp+Main.P-Source.Conc.+P-Source.Feed.conc.+Main.Thr.Conc.+Nitrogen.Conc.+Lys_conc.+yield+His+SO4.ferm.+PO4.apporte; 0.382, 0.698, pH+tmp+Main.P-Source.Conc.+P-Source.Feed.conc.+Main.Thr.Conc.+Nitrogen.Conc.+Lys_conc.+His+lactate+SO4.ferm.+PO4.apporte; 0.382, 0.697, pH+tmp+P-Source.Feed.conc.+Main.Thr.Conc.+Nitrogen.Conc.+Lys_conc.+yield+lactate+SO4.ferm.+PO4.apporte+PO4.utilise; 0.393, 0.697, tmp+P-Source.Feed.conc.+Main.Thr.Conc.+Nitrogen.Conc.+OD+Lys_conc.+His+lactate+SO4.ferm.+PO4.apporte; 0.434, 0.697, tmp+Main.P-Source.Conc.+P-Source.Feed.conc.+Main.Thr.Conc.+Lys_conc.+PO4.apporte; 0.414, 0.697, tmp+P-Source.Feed.conc.+Main.Thr.Conc.+Nitrogen.Conc.+Lys_conc.+yield+PL+PO4.apporte; 0.404, 0.697, tmp+Main.P-Source.Conc.+P-Source.Feed.conc.+Main.Thr.Conc.+Lys_conc.+PL+SO4.ferm.+PO4.ferm.+PO4.utilise; 0.393, 0.697, tmp+P-Source.Feed.conc.+Main.Thr.Conc.+Nitrogen.Conc.+Lys_conc.+yield+PL+SO4.ferm.+PO4.apporte+PO4.utilise; 0.393, 0.697, pH+tmp+P-Source.Feed.conc.+Main.Thr.Conc.+Lys_conc.+PL+lactate+SO4.ferm.+PO4.apporte+PO4.utilise; 0.382, 0.697, pH+tmp+P-Source.Feed.conc.+Main.Thr.Conc.+Nitrogen.Conc.+Lys_conc.+yield+lactate+SO4.ferm.+PO4.ferm.+PO4.apporte; 0.370, 0.697, pH+tmp+Main.P-Source.Conc.+P-Source.Feed.conc.+Main.Thr.Conc.+Nitrogen.Conc.+Lys_conc.+lactate+SO4.ferm.+PO4.ferm.+PO4.apporte+PO4.utilise; 0.393, 0.697, pH+tmp+P-Source.Feed.conc.+Main.Thr.Conc.+Nitrogen.Conc.+OD+Lys_conc.+His+SO4.ferm.+PO4.utilise; 0.393, 0.697, pH+tmp+P-Source.Feed.conc.+Main.Thr.Conc.+Lys_conc.+yield+SO4.ferm.+PO4.ferm.+PO4.apporte+PO4.utilise; 0.382, 0.697, pH+tmp+Main.P-Source.Conc.+P-Source.Feed.conc.+Main.Thr.Conc.+Nitrogen.Conc.+Lys_conc.+His+SO4.ferm.+PO4.ferm.+PO4.apporte; 0.393, 0.697, tmp+P-Source.Feed.conc.+Main.Thr.Conc.+Nitrogen.Conc.+OD+Lys_conc.+lactate+SO4.ferm.+PO4.apporte+PO4.utilise; 0.414, 0.697, tmp+P-Source.Feed.conc.+Main.Thr.Conc.+Nitrogen.Conc.+Lys_conc.+rab+SO4.ferm.+PO4.apporte; 0.404, 0.697, tmp+P-Source.Feed.conc.+Main.Thr.Conc.+Lys_conc.+PL+His+SO4.ferm.+PO4.ferm.+PO4.utilise; 0.393, 0.697, pH+tmp+Main.P-Source.Conc.+P-Source.Feed.conc.+Main.Thr.Conc.+Lys_conc.+lactate+SO4.ferm.+PO4.ferm.+PO4.utilise; 0.393, 0.697, tmp+P-Source.Feed.conc.+Main.Thr.Conc.+Nitrogen.Conc.+Lys_conc.+yield+PL+SO4.ferm.+PO4.ferm.+PO4.apporte; 0.393, 0.697, tmp+P-Source.Feed.conc.+Main.Thr.Conc.+Lys_conc.+PL+lactate+SO4.ferm.+PO4.ferm.+PO4.apporte+PO4.utilise; 0.393, 0.697, pH+tmp+Main.P-Source.Conc.+P-Source.Feed.conc.+Main.Thr.Conc.+Lys_conc.+yield+PL+SO4.ferm.+PO4.apporte; 0.393, 0.697, pH+tmp+P-Source.Feed.conc.+Main.Thr.Conc.+Lys_conc.+PL+lactate+SO4.ferm.+PO4.ferm.+PO4.apporte; 0.381, 0.697, pH+tmp+Main.P-Source.Conc.+P-Source.Feed.conc.+Main.Thr.Conc.+Nitrogen.Conc.+Lys_conc.+yield+SO4.ferm.+PO4.ferm.+PO4.utilise; 0.381, 0.697, tmp+Main.P-Source.Conc.+P-Source.Feed.conc.+Main.Thr.Conc.+Nitrogen.Conc.+Lys_conc.+yield+lactate+SO4.ferm.+PO4.ferm.+PO4.apporte; 0.392, 0.697, pH+tmp+P-Source.Feed.conc.+Main.Thr.Conc.+Lys_conc.+PL+lactate+SO4.ferm.+PO4.ferm.+PO4.utilise; 0.381, 0.697, tmp+Main.P-Source.Conc.+P-Source.Feed.conc.+Main.Thr.Conc.+Nitrogen.Conc.+Lys_conc.+yield+lactate+SO4.ferm.+PO4.apporte+PO4.utilise; 0.381, 0.697, tmp+Main.P-Source.Conc.+P-Source.Feed.conc.+Main.Thr.Conc.+Nitrogen.Conc.+Lys_conc.+yield+SO4.ferm.+PO4.ferm.+PO4.apporte+PO4.utilise; 0.403, 0.697, pH+tmp+Main.P-Source.Conc.+P-Source.Feed.conc.+Main.Thr.Conc.+Nitrogen.Conc.+Lys_conc.+PL+SO4.ferm.; 0.403, 0.697, tmp+P-Source.Feed.conc.+Main.Thr.Conc.+OD+Lys_conc.+yield+PL+SO4.ferm.+PO4.utilise; 0.381, 0.697, pH+tmp+Main.P-Source.Conc.+P-Source.Feed.conc.+Main.Thr.Conc.+Nitrogen.Conc.+Lys_conc.+His+SO4.ferm.+PO4.apporte+PO4.utilise; 0.414, 0.697, tmp+Main.P-Source.Conc.+P-Source.Feed.conc.+Main.Thr.Conc.+Nitrogen.Conc.+Lys_conc.+lactate+PO4.apporte; 0.403, 0.697, pH+tmp+Main.P-Source.Conc.+P-Source.Feed.conc.+Main.Thr.Conc.+Nitrogen.Conc.+OD+Lys_conc.+SO4.ferm.; 0.392, 0.697, tmp+P-Source.Feed.conc.+Main.Thr.Conc.+Nitrogen.Conc.+OD+Lys_conc.+lactate+SO4.ferm.+PO4.ferm.+PO4.apporte; 0.424, 0.697, tmp+P-Source.Feed.conc.+Main.Thr.Conc.+Nitrogen.Conc.+Lys_conc.+PO4.apporte+PO4.utilise; 0.381, 0.697, pH+tmp+P-Source.Feed.conc.+Main.Thr.Conc.+Nitrogen.Conc.+Lys_conc.+yield+lactate+SO4.ferm.+PO4.ferm.+PO4.utilise; 0.381, 0.697, tmp+P-Source.Feed.conc.+Main.Thr.Conc.+Nitrogen.Conc.+OD+Lys_conc.+yield+PL+lactate+SO4.ferm.+PO4.apporte; 0.403, 0.697, pH+tmp+Main.P-Source.Conc.+P-Source.Feed.conc.+Main.Thr.Conc.+Nitrogen.Conc.+Lys_conc.+His+SO4.ferm.; 0.381, 0.697, pH+tmp+P-Source.Feed.conc.+Main.Thr.Conc.+Nitrogen.Conc.+OD+Lys_conc.+yield+PL+SO4.ferm.+PO4.apporte; 0.392, 0.697, tmp+P-Source.Feed.conc.+Main.Thr.Conc.+Nitrogen.Conc.+Lys_conc.+yield+PL+SO4.ferm.+PO4.ferm.+PO4.utilise; 0.381, 0.697, tmp+Main.P-Source.Conc.+P-Source.Feed.conc.+Main.Thr.Conc.+Nitrogen.Conc.+Lys_conc.+PL+SO4.ferm.+PO4.ferm.+PO4.apporte+PO4.utilise; 0.413, 0.697, pH+tmp+P-Source.Feed.conc.+Main.Thr.Conc.+OD+Lys_conc.+SO4.ferm.+PO4.utilise; 0.381, 0.697, pH+tmp+Main.P-Source.Conc.+P-Source.Feed.conc.+ Main.Thr.Conc.+Nitrogen.Conc.+OD+Lys_conc.+PL+ SO4.ferm.+PO4.apporte; 0.403, 0.697, tmp+P-Source. Feed.conc.+Main.Thr.Conc.+Lys_conc.+PL+His+ SO4.ferm.+PO4.ferm.+PO4.apporte; 0.403, 0.697, tmp+ Main.P-Source.Conc.+P-Source.Feed.conc.+Main.Thr. Conc.+Lys_conc.+His+SO4.ferm.+PO4.ferm.+PO4.utilise; 0.403, 0.697, tmp+P-Source.Feed.conc.+Main.Thr.Conc.+ Lys_conc.+PL+His+SO4.ferm.+PO4.apporte+PO4.utilise; 0.413, 0.697, tmp+Main.P-Source.Conc.+P-Source. Feed.conc.+Main.Thr.Conc.+Nitrogen.Conc.+OD+Lys_conc.+SO4.ferm.; 0.403, 0.697, tmp+Main.P-Source.Conc.+P-Source.Feed.conc.+Main.Thr.Conc.+Lys_conc.+His+SO4.ferm.+PO4.ferm.+PO4.apporte; 0.392, 0.697, pH+tmp+Main.P-Source.Conc.+P-Source.Feed. conc.+Main.Thr.Conc.+Nitrogen.Conc.+Lys_conc.+lactate+SO4.ferm.+PO4.utilise; 0.380, 0.697, pH+tmp+ Main.P-Source.Conc.+P-Source.Feed.conc.+Main.Thr. Conc.+Nitrogen.Conc.+Lys_conc.+His+SO4.ferm.+ PO4.ferm.+PO4.utilise; 0.423, 0.697, tmp+P-Source. Feed.conc.+Main.Thr.Conc.+Lys_conc.+yield+SO4.ferm.+ PO4.utilise; 0.413, 0.697, tmp+P-Source.Feed.conc.+Main. Thr.Conc.+Nitrogen.Conc.+OD+Lys_conc.+SO4.ferm.+ PO4.utilise; 0.423, 0.697, tmp+P-Source.Feed.conc.+ Main.Thr.Conc.+Lys_conc.+lactate+SO4.ferm.+ PO4.utilise; 0.392, 0.697, pH+tmp+P-Source.Feed.conc.+ Main.Thr.Conc.+OD+Lys_conc.+lactate+SO4.ferm.+ PO4.apporte+PO4.utilise; 0.402, 0.697, tmp+Main.P-Source.Conc.+P-Source.Feed.conc.+Main. Thr.Conc.+ Lys_conc.+His+SO4.ferm.+PO4.apporte+PO4.utilise; 0.402, 0.696, pH+tmp+P-Source.Feed.conc.+Main.Thr. Conc.+Nitrogen.Conc.+Lys_conc.+PO4.ferm.+ PO4.apporte+PO4.utilise; 0.433, 0.696, tmp+P-Source. Feed.conc.+Main.Thr.Conc.+Lys_conc.+SO4.ferm.+ PO4.utilise; 0.380, 0.696, pH+tmp+P-Source.Feed.conc.+ Main.Thr.Conc.+Nitrogen.Conc.+Lys_conc.+yield+ SO4.ferm.+PO4.ferm.+PO4.apporte+PO4.utilise; 0.413, 0.696, pH+tmp+P-Source.Feed.conc.+Main.Thr.Conc.+Nitrogen.Conc.+Lys_conc.+PO4.apporte+PO4.utilise; 0.402, 0.696, tmp+P-Source.Feed.conc.+Main.Thr.Conc.+OD+Lys_conc.+PL+SO4.ferm.+PO4.apporte+PO4.utilise; 0.423, 0.696, tmp+P-Source.Feed.conc.+Main.Thr.Conc.+Nitrogen.Conc.+Lys_conc.+PO4.ferm.+PO4.apporte; 0.391, 0.696, pH+tmp+P-Source.Feed.conc.+Main.Thr.Conc.+ OD+Lys_conc.+lactate+SO4.ferm.+PO4.ferm.+ PO4.apporte; 0.380, 0.696, tmp+Main.P-Source.Conc.+P-Source.Feed.conc.+Main.Thr.Conc.+Nitrogen.Conc.+ Lys_conc.+yield+lactate+SO4.ferm.+PO4.ferm.+ PO4.utilise; 0.391, 0.696, pH+tmp+Main.P-Source.Conc.+ P-Source.Feed.conc.+Main.Thr.Conc.+Nitrogen.Conc.+ Lys_conc.+His+SO4.ferm.+PO4.utilise; 0.391, 0.696, tmp+ P-Source.Feed.conc.+Main.Thr.Conc.+Lys_conc.+yield+ PL+lactate+SO4.ferm.+PO4.apporte+PO4.utilise; 0.412, 0.696, tmp+P-Source.Feed.conc.+Main.Thr.Conc.+Nitrogen.Conc.+Lys_conc.+PL+lactate+PO4.apporte; 0.391, 0.696, tmp+P-Source.Feed.conc.+Main.Thr.Conc.+Nitrogen.Conc.+OD+Lys_conc.+lactate+SO4.ferm.+PO4.ferm.+ PO4.utilise; 0.391, 0.696, tmp+P-Source.Feed.conc.+ Main.Thr.Conc.+Lys_conc.+yield+PL+lactate+SO4.ferm.+ PO4.ferm.+PO4.utilise; 0.391, 0.696, tmp+P-Source.Feed. conc.+Main.Thr.Conc.+Lys_conc.+yield+PL+lactate+ SO4.ferm.+PO4.ferm.+PO4.apporte; 0.412, 0.696, tmp+P-Source.Feed.conc.+Main.Thr.Conc.+Nitrogen.Conc.+Lys_conc.+yield+SO4.ferm.+PO4.utilise; 0.379, 0.696, pH+tmp+P-Source.Feed.conc.+Main.Thr.Conc.+OD+Lys_conc.+yield+PL+lactate+SO4.ferm.+PO4.apporte; 0.391, 0.696, pH+tmp+P-Source.Feed.conc.+Main.Thr.Conc.+ OD+Lys_conc.+yield+His+SO4.ferm.+PO4.apporte; 0.402, 0.696, tmp+Main.P-Source.Conc.+P-Source.Feed.conc.+ Main.Thr.Conc.+Nitrogen.Conc.+Lys_conc.+PO4.ferm.+ PO4.apporte+PO4.utilise; 0.402, 0.696, tmp+P-Source. Feed.conc.+Main.Thr.Conc.+OD+Lys_conc.+PL+ SO4.ferm.+PO4.ferm.+PO4.apporte; 0.391, 0.696, pH+tmp+Main.P-Source.Conc.+P-Source.Feed.conc.+ Main.Thr.Conc.+OD+Lys_conc.+PL+SO4.ferm.+ PO4.apporte; 0.391, 0.696, tmp+Main.P-Source.Conc.+P-Source.Feed.conc.+Main.Thr.Conc.+Lys_conc.+yield+ lactate+SO4.ferm.+PO4.apporte+PO4.utilise; 0.432, 0.696, tmp+Main.P-Source.Conc.+Main.Thr.Conc.+Lys_conc.+ SO4.ferm.+PO4.apporte; 0.391, 0.696, tmp+Main.P-Source.Conc.+P-Source.Feed.conc.+Main.Thr.Conc.+Lys_conc.+yield+lactate+SO4.ferm.+PO4.ferm.+ PO4.apporte; 0.401, 0.696, pH+tmp+P-Source.Feed.conc.+ Main.Thr.Conc.+Nitrogen.Conc.+OD+Lys_conc.+yield+ PO4.apporte; 0.390, 0.696, pH+tmp+P-Source.Feed.conc.+ Main.Thr.Conc.+OD+Lys_conc.+His+lactate+SO4.ferm.+ PO4.apporte; 0.390, 0.696, tmp+P-Source.Feed.conc.+ Main.Thr.Conc.+Nitrogen.Conc.+Lys_conc.+PL+His+ SO4.ferm.+PO4.ferm.+PO4.utilise; 0.390, 0.696, pH+tmp+ P-Source.Feed.conc.+Main.Thr.Conc.+OD+Lys_conc.+ His+SO4.ferm.+PO4.apporte+PO4.utilise; 0.412, 0.696, pH+tmp+P-Source.Feed.conc.+Main.Thr.Conc.+ Nitrogen.Conc.+Lys_conc.+PO4.ferm.+PO4.apporte; 0.390, 0.696, pH+tmp+P-Source.Feed.conc.+Main.Thr. Conc.+OD+Lys_conc.+His+SO4.ferm.+PO4.ferm.+ PO4.apporte; 0.390, 0.696, tmp+Main.P-Source.Conc.+P-Source.Feed.conc.+Main.Thr.Conc.+OD+Lys_conc.+PL+ His+SO4.ferm.+PO4.apporte; 0.390, 0.696, tmp+P-Source.Feed.conc.+Main.Thr.Conc.+Nitrogen.Conc.+ Lys_conc.+PL+His+SO4.ferm.+PO4.ferm.+PO4.apporte; 0.390, 0.696, tmp+Main.P-Source.Conc.+P-Source.Feed. conc.+Main.Thr.Conc.+Nitrogen.Conc.+OD+Lys_conc.+ SO4.ferm.+PO4.apporte+PO4.utilise; 0.432, 0.696, tmp+P-Source.Feed.conc.+Main.Thr.Conc.+Lys_conc.+PL+ PO4.apporte; 0.379, 0.696, tmp+P-Source.Feed.conc.+ Main.Thr.Conc.+Nitrogen.Conc.+Lys_conc.+yield+lactate+ SO4.ferm.+PO4.ferm.+PO4.apporte+PO4.utilise; 0.390, 0.696, tmp+P-Source.Feed.conc.+Main.Thr.Conc.+Nitrogen.Conc.+Lys_conc.+PL+His+SO4.ferm.+PO4.apporte+ PO4.utilise; 0.412, 0.696, tmp+P-Source.Feed.conc.+ Main.Thr.Conc.+Nitrogen.Conc.+Lys_conc.+lactate+ SO4.ferm.+PO4.utilise; 0.390, 0.696, tmp+Main.P-Source.Conc.+P-Source.Feed.conc.+Main.Thr.Conc.+Lys_conc.+yield+lactate+SO4.ferm.+PO4.ferm.+PO4.utilise; 0.390, 0.696, tmp+Main.P-Source.Conc.+P-Source. Feed.conc.+Main.Thr.Conc.+OD+Lys_conc.+PL+lactate+ SO4.ferm.+PO4.apporte; 0.390, 0.696, pH+tmp+P-Source. Feed.conc.+Main.Thr.Conc.+OD+Lys_conc.+lactate+ SO4.ferm.+PO4.ferm.+PO4.utilise; 0.390, 0.696, pH+tmp+ P-Source.Feed.conc.+Main.Thr.Conc.+OD+Lys_conc.+ His+SO4.ferm.+PO4.ferm.+PO4.utilise; 0.390, 0.696, tmp+ Main.P-Source.Conc.+P-Source.Feed.conc.+ Main.Thr.Conc.+Nitrogen.Conc.+OD+Lys_conc.+ SO4.ferm.+PO4.ferm.+PO4.apporte; 0.390, 0.696, pH+tmp+Feed.conc.+Main.Thr.Conc.+OD+Lys_conc.+ PL+His+SO4.ferm.+PO4.utilise; 0.411, 0.696, tmp+P-Source.Feed.conc.+Main.Thr.Conc.+OD+Lys_conc.+yield+ lactate+PO4.apporte; 0.390, 0.696, pH+tmp+P-Source.Feed.conc.+Main.Thr.Conc.+Lys_conc.+PL+ SO4.ferm.+PO4.ferm.+PO4.apporte+PO4.utilise; 0.411, 0.695, tmp+P-Source.Feed.conc.+Main.Thr.Conc.+Nitrogen.Conc.+Lys_conc.+emission_O2+SO4.ferm.+ PO4.apporte; 0.390, 0.695, tmp+Main.P-Source.Conc.+P-

Source.Feed.conc.+Main.Thr.Conc.+OD+Lys_conc.+yield+PL+SO4.ferm.+PO4.apporte; 0.431, 0.695, tmp+Main.Thr.Conc.+Nitrogen.Conc.+Lys_conc.+SO4.ferm.+PO4.apporte; 0.390, 0.695, pH+tmp+Main.P-Source.Conc.+P-Source.Feed.conc.+Main.Thr.Conc.+Nitrogen.Conc.+Lys_conc.+yield+lactate+SO4.ferm.; 0.431, 0.695, tmp+P-Source.Feed.conc.+Main.Thr.Conc.+Lys_conc.+Thr+PO4.apporte; 0.411, 0.695, tmp+P-Source.Feed.conc.+Main.Thr.Conc.+Nitrogen.Conc.+OD+Lys_conc.+lactate+PO4.apporte; 0.401, 0.695, tmp+P-Source.Feed.conc.+Main.Thr.Conc.+OD+Lys_conc.+PL+SO4.ferm.+PO4.ferm.+PO4.utilise; 0.390, 0.695, pH+tmp+P-Source.Feed.conc.+Main.Thr.Conc.+OD+Lys_conc.+SO4.ferm.+PO4.ferm.+PO4.apporte+PO4.utilise; 0.400, 0.695, pH+tmp+P-Source.Feed.conc.+Main.Thr.Conc.+Lys_conc.+yield+His+SO4.ferm.+PO4.apporte; 0.400, 0.695, tmp+P-Source.Feed.conc.+Main.Thr.Conc.+Nitrogen.Conc.+Lys_conc.+lactate+PO4.ferm.+PO4.apporte+PO4.utilise; 0.389, 0.695, pH+tmp+P-Source.Feed.conc.+Main.Thr.Conc.+OD+Lys_conc.+yield+SO4.ferm.+PO4.apporte+PO4.utilise; 0.389, 0.695, tmp+Main.P-Source.Conc.+P-Source.Feed.conc.+Main.Thr.Conc.+Lys_conc.+lactate+SO4.ferm.+PO4.ferm.+PO4.apporte+PO4.utilise; 0.389, 0.695, tmp+P-Source.Feed.conc.+Main.Thr.Conc.+Nitrogen.Conc.+Lys_conc.+His+SO4.ferm.+PO4.ferm.+PO4.apporte+PO4.utilise; 0.421, 0.695, tmp+P-Source.Feed.conc.+Main.Thr.Conc.+Lys_conc.+rab+SO4.ferm.+PO4.apporte; 0.400, 0.695, tmp+Main.P-Source.Conc.+P-Source.Feed.conc.+Main.Thr.Conc.+OD+Lys_conc.+SO4.ferm.+PO4.apporte+PO4.utilise; 0.389, 0.695, pH+tmp+P-Source.Feed.conc.+Main.Thr.Conc.+OD+Lys_conc.+yield+lactate+SO4.ferm.+PO4.utilise; 0.400, 0.695, tmp+Main.P-Source.Conc.+P-Source.Feed.conc.+Main.Thr.Conc.+OD+Lys_conc.+His+SO4.ferm.+PO4.utilise; 0.389, 0.695, pH+P-Source.Feed.conc.+Main.Thr.Conc.+OD+Lys_conc.+yield+SO4.ferm.+PO4.ferm.+PO4.apporte; 0.400, 0.695, tmp+Main.P-Source.Conc.+P-Source.Feed.conc.+Main.Thr.Conc.+OD+Lys_conc.+SO4.ferm.+PO4.ferm.+PO4.apporte; 0.389, 0.695, pH+tmp+Main.P-Source.Conc.+P-Source.Feed.conc.+Main.Thr.Conc.+Lys_conc.+yield+SO4.ferm.+PO4.apporte+PO4.utilise; 0.389, 0.695, pH+tmp+Main.P-Source.Conc.+P-Source.Feed.conc.+Main.Thr.Conc.+Lys_conc.+SO4.ferm.+PO4.ferm.+PO4.apporte+PO4.utilise; 0.389, 0.695, pH+tmp+Main.P-Source.Conc.+P-Source.Feed.conc.+Main.Thr.Conc.+Lys_conc.+yield+SO4.ferm.+PO4.ferm.+PO4.apporte; 0.400, 0.695, tmp+P-Source.Feed.conc.+Main.Thr.Conc.+Lys_conc.+His+SO4.ferm.+PO4.ferm.+PO4.apporte+PO4.utilise; 0.389, 0.695, pH+tmp+P-Source.Feed.conc.+Main.Thr.Conc.+OD+Lys_conc.+His+lactate+SO4.ferm.+PO4.utilise; 0.377, 0.695, pH+tmp+Main.P-Source.Conc.+P-Source.Feed.conc.+Main.Thr.Conc.+Nitrogen.Conc.+Lys_conc.+PL+SO4.ferm.+PO4.apporte+PO4.utilise; 0.400, 0.695, tmp+Main.P-Source.Conc.+P-Source.Feed.conc.+Main.Thr.Conc.+Nitrogen.Conc.+Lys_conc.+yield+PL+SO4.ferm.; 0.377, 0.695, pH+tmp+Main.P-Source.Conc.+P-Source.Feed.conc.+Main.Thr.Conc.+Nitrogen.Conc.+Lys_conc.+PL+SO4.ferm.+PO4.ferm.+PO4.apporte; 0.366, 0.695, pH+tmp+Main.P-Source.Conc.+P-Source.Feed.conc.+Main.Thr.Conc.+Nitrogen.Conc.+Lys_conc.+yield+PL+lactate+SO4.ferm.+PO4.apporte; 0.377, 0.695, tmp+Main.P-Source.Conc.+P-Source.Feed.conc.+Main.Thr.Conc.+Nitrogen.Conc.+OD+Lys_conc.+PL+lactate+SO4.ferm.+PO4.apporte; 0.399, 0.695, tmp+Main.P-Source.Conc.+P-Source.Feed.conc.+Main.Thr.Conc.+Lys_conc.+His+lactate+SO4.ferm.+PO4.apporte;

0.389, 0.695, pH+tmp+P-Source.Feed.conc.+Main.Thr.Conc.+OD+Lys_conc.+yield+SO4.ferm.+PO4.ferm.+PO4.utilise; 0.377, 0.695, tmp+Main.P-Source.Conc.+P-Source.Feed.conc.+Main.Thr.Conc.+Nitrogen.Conc.+OD+Lys_conc.+SO4.ferm.+PO4.ferm.+PO4.apporte+PO4.utilise; 0.399, 0.695, pH+tmp+Main.P-Source.Conc.+P-Source.Feed.conc.+Main.Thr.Conc.+Nitrogen.Conc.+Lys_conc.+SO4.ferm.+PO4.ferm.; 0.399, 0.695, pH+tmp+Main.P-Source.Conc.+P-Source.Feed. conc.+Main.Thr.Conc.+Nitrogen.Conc.+Lys_conc.+yield+PO4.apporte; 0.410, 0.695, pH+tmp+P-Source.Feed.conc.+Main.Thr.Conc.+Lys_conc.+yield+lactate+PO4.apporte; 0.410, 0.695, tmp+Main.P-Source.Conc.+P-Source.Feed. conc.+Main.Thr.Conc.+Nitrogen.Conc.+Lys_conc.+SO4.ferm.+PO4.ferm.; 0.388, 0.695, pH+tmp+Main.P-Source.Conc.+P-Source.Feed.conc.+Main.Thr.Conc.+Lys_conc.+yield+SO4.ferm.+PO4.ferm.+PO4.utilise; 0.388, 0.695, tmp+Main.P-Source.Conc.+P-Source.Feed. conc.+Main.Thr.Conc.+Nitrogen.Conc.+OD+Lys_conc.+SO4.ferm.+PO4.ferm.+PO4.utilise; 0.377, 0.695, pH+tmp+P-Source.Feed.conc.+Main.Thr.Conc.+Nitrogen.Conc.+Lys_conc.+PL+SO4.ferm.+PO4.ferm.+PO4.apporte+PO4.utilise; 0.388, 0.694, tmp+P-Source.Feed.conc.+Main.Thr.Conc.+OD+Lys_conc.+yield+lactate+SO4.ferm.+PO4.apporte+PO4.utilise; 0.399, 0.694, pH+tmp+Main.P-Source.Conc.+P-Source.Feed.conc.+Main.Thr.Conc.+Nitrogen.Conc.+Lys_conc.+lactate+PO4.apporte; 0.388, 0.694, tmp+P-Source.Feed.conc.+Main.Thr.Conc.+OD+Lys_conc.+PL+His+lactate+SO4.ferm.+PO4.utilise; 0.388, 0.694, pH+tmp+Main.P-Source.Conc.+P-Source.Feed. conc.+Main.Thr.Conc.+Nitrogen.Conc.+Lys_conc.+yield+SO4.ferm.+PO4.utilise; 0.388, 0.694, tmp+Main.P-Source.Conc.+P-Source.Feed.conc.+Main.Thr.Conc.+Lys_conc.+PL+lactate+SO4.ferm.+PO4.apporte+PO4.utilise; 0.419, 0.694, pH+tmp+Main.P-Source.Conc.+P-Source.Feed.conc.+Main.Thr.Conc.+Lys_conc.+PO4.apporte; 0.388, 0.694, tmp+Main.P-Source.Conc.+P-Source.Feed. conc.+Main.Thr.Conc.+Lys_conc.+PL+lactate+SO4.ferm.+PO4.ferm.+PO4.apporte; 0.388, 0.694, tmp+P-Source.Feed. conc.+Main.Thr.Conc.+OD+Lys_conc.+yield+lactate+SO4.ferm.+PO4.ferm.+PO4.apporte; 0.388, 0.694, tmp+P-Source.Feed.conc.+Main.Thr.Conc.+Nitrogen. Conc.+OD+Lys_conc.+yield+SO4.ferm.+PO4.apporte+PO4.utilise; 0.376, 0.694, tmp+P-Source.Feed.conc.+Main. Thr.Conc.+Nitrogen.Conc.+Lys_conc.+PL+lactate+SO4.ferm.+PO4.ferm.+PO4.apporte+PO4.utilise; 0.399, 0.694, pH+tmp+P-Source.Feed.conc.+Main.Thr.Conc.+Nitrogen. Conc.+OD+Lys_conc.+lactate+PO4.apporte; 0.399, 0.694, tmp+Main.P-Source.Conc.+P-Source.Feed.conc.+Main. Thr.Conc.+OD+Lys_conc.+SO4.ferm.+PO4.ferm.+PO4.utilise; 0.376, 0.694, pH+tmp+P-Source.Feed.conc.+Main.Thr.Conc.+Nitrogen.Conc.+OD+Lys_conc.+His+lactate+SO4.ferm.+PO4.apporte; 0.376, 0.694, pH+tmp+P-Source.Feed.conc.+Main.Thr.Conc.+Nitrogen.Conc.+OD+Lys_conc.+yield+His+SO4.ferm.+PO4.apporte; 0.388, 0.694, pH+tmp+P-Source.Feed.conc.+Main.Thr.Conc.+OD+Lys_conc.+yield+His+SO4.ferm.+PO4.utilise; 0.376, 0.694, pH+tmp+P-Source.Feed.conc.+Main.Thr.Conc.+Nitrogen.Conc.+OD+Lys_conc.+SO4.ferm.+PO4.ferm.+PO4.apporte+PO4.utilise; 0.398, 0.694, tmp+Main.P-Source.Conc.+P-Source.Feed.conc.+Main.Thr.Conc.+Nitrogen.Conc.+OD+Lys_conc.+yield+SO4.ferm.; 0.409, 0.694, tmp+Main.P-Source.Conc.+P-Source.Feed.conc.+Main.Thr.Conc.+Nitrogen.Conc.+Lys_conc.+His+PO4.apporte; 0.364, 0.694, pH+tmp+Main.P-Source.Conc.+P-Source.Feed.conc.+Main.Thr.Conc.+Nitrogen.Conc.+

OD+Lys_conc.+yield+lactate+SO4.ferm.+PO4.apporte; 0.376, 0.694, pH+tmp+Main.P-Source.Conc.+P-Source.Feed.conc.+Main.Thr.Conc.+OD+Lys_conc.+yield+lactate+SO4.ferm.+PO4.apporte; 0.387, 0.694, pH+tmp+Main.P-Source.Conc.+P-Source.Feed.conc.+Main.Thr.Conc.+Lys_conc.+PL+His+SO4.ferm.+PO4.apporte; 0.387, 0.694, tmp+Main.P-Source.Conc.+P-Source.Feed.conc.+Main.Thr.Conc.+Nitrogen.Conc.+Lys_conc.+yield+lactate+SO4.ferm.+PO4.utilise; 0.376, 0.694, tmp+Main.P-Source.Conc.+P-Source.Feed.conc.+Main.Thr.Conc.+Nitrogen.Conc.+Lys_conc.+PL+lactate+SO4.ferm.+PO4.ferm.+PO4.apporte; 0.387, 0.694, tmp+P-Source.Feed.conc.+Main.Thr.Conc.+Nitrogen.Conc.+Lys_conc.+yield+PL+His+SO4.ferm.+PO4.apporte; 0.419, 0.694, tmp+Main.P-Source.Conc.+P-Source.Feed.conc.+Main.Thr.Conc.+Lys_conc.+SO4.ferm.+PO4.utilise; 0.387, 0.694, tmp+P-Source.Feed.conc.+Main.Thr.Conc.+Nitrogen.Conc.+OD+Lys_conc.+yield+SO4.ferm.+PO4.ferm.+PO4.apporte; 0.419, 0.694, tmp+P-Source.Feed.conc.+Main.Thr.Conc.+Lys_conc.+yield+PL+PO4.apporte; 0.387, 0.694, tmp+P-Source.Feed.conc.+Main.Thr.Conc.+OD+Lys_conc.+yield+lactate+SO4.ferm.+PO4.ferm.+PO4.utilise; 0.376, 0.694, pH+tmp+P-Source.Feed.conc.+Main.Thr.Conc.+Nitrogen.Conc.+Lys_conc.+PL+lactate+SO4.ferm.+PO4.apporte+PO4.utilise; 0.409, 0.694, tmp+P-Source.Feed.conc.+Main.Thr.Conc.+Nitrogen.Conc.+OD+Lys_conc.+His+PO4.apporte; 0.376, 0.694, tmp+Main.P-Source.Conc.+P-Source.Feed.conc.+Main.Thr.Conc.+Nitrogen.Conc.+Lys_conc.+PL+lactate+SO4.ferm.+PO4.apporte+PO4.utilise; 0.419, 0.694, tmp+Main.P-Source.Conc.+P-Source.Feed.conc.+Main.Thr.Conc.+Lys_conc.+yield+PO4.apporte; 0.376, 0.694, pH+tmp+Main.P-Source.Conc.+P-Source.Feed.conc.+Main.Thr.Conc.+Nitrogen.Conc.+Lys_conc.+yield+His+SO4.ferm.+PO4.apporte; 0.398, 0.694, pH+tmp+P-Source.Feed.conc.+Main.Thr.Conc.+Nitrogen.Conc.+OD+Lys_conc.+His+PO4.apporte; 0.429, 0.694, tmp+Main.Thr.Conc.+Lys_conc.+PL+SO4.ferm.+PO4.apporte; 0.376, 0.694, pH+tmp+Main.P-Source.Conc.+P-Source.Feed.conc.+Main.Thr.Conc.+Nitrogen.Conc.+Lys_conc.+PL+SO4.ferm.+PO4.ferm.+PO4.utilise; 0.387, 0.694, tmp+Main.P-Source.Conc.+P-Source.Feed.conc.+Main.Thr.Conc.+Lys_conc.+PL+lactate+SO4.ferm.+PO4.ferm.+PO4.utilise; 0.376, 0.694, tmp+Main.P-Source.Conc.+P-Source.Feed.conc.+Main.Thr.Conc.+Nitrogen.Conc.+OD+Lys_conc.+PL+His+SO4.ferm.+PO4.apporte; 0.376, 0.694, pH+tmp+P-Source.Feed.conc.+Main.Thr.Conc.+Nitrogen.Conc.+Lys_conc.+PL+lactate+SO4.ferm.+PO4.ferm.+PO4.apporte; 0.387, 0.694, tmp+P-Source.Feed.conc.+Main.Thr.Conc.+Nitrogen.Conc.+OD+Lys_conc.+His+SO4.ferm.+PO4.ferm.+PO4.apporte; 0.419, 0.694, tmp+P-Source.Feed.conc.+Main.Thr.Conc.+Nitrogen.Conc.+Lys_conc.+PO4.ferm.+PO4.utilise; 0.398, 0.694, tmp+Main.P-Source.Conc.+P-Source.Feed.conc.+Main.Thr.Conc.+Nitrogen.Conc.+Lys_conc.+PL+SO4.ferm.+PO4.utilise; 0.398, 0.694, pH+tmp+P-Source.Feed.conc.+Main.Thr.Conc.+OD+Lys_conc.+lactate+SO4.ferm.+PO4.utilise; 0.387, 0.694, tmp+P-Source.Feed.conc.+Main.Thr.Conc.+Nitrogen.Conc.+OD+Lys_conc.+His+SO4.ferm.+PO4.apporte+PO4.utilise; 0.387, 0.694, pH+tmp+P-Source.Feed.conc.+Main.Thr.Conc.+Lys_conc.+yield+PL+SO4.ferm.+PO4.apporte+PO4.utilise; 0.387, 0.694, pH+tmp+Main.P-Source.Conc.+P-Source.Feed.conc.+Main.Thr.Conc.+Nitrogen.Conc.+Lys_conc.+PO4.ferm.+PO4.apporte+PO4.utilise; 0.408, 0.694, tmp+P-Source.Feed.conc.+Main.Thr.Conc.+OD+Lys_conc.+PL+SO4.ferm.+PO4.utilise; 0.408, 0.694, tmp+P-Source.Feed.conc.+Main.Thr.Conc.+Lys_conc.+yield+lactate+SO4.ferm.+PO4.utilise; 0.419, 0.694, pH+tmp+P-Source.Feed.conc.+Main.Thr.Conc.+Lys_conc.+PL+PO4.apporte; 0.387, 0.694, pH+tmp+P-Source.Feed.conc.+Main.Thr.Conc.+Lys_conc.+yield+PL+SO4.ferm.+PO4.ferm.+PO4.utilise; 0.387, 0.694, pH+tmp+P-Source.Feed.conc.+Main.Thr.Conc.+Lys_conc.+yield+PL+SO4.ferm.+PO4.ferm.+PO4.apporte; 0.364, 0.694, pH+tmp+Main.P-Source.Conc.+P-Source.Feed.conc.+Main.Thr.Conc.+Nitrogen.Conc.+Lys_conc.+yield+SO4.ferm.+PO4.ferm.+PO4.apporte+PO4.utilise; 0.387, 0.694, tmp+P-Source.Feed.conc.+Main.Thr.Conc.+Nitrogen.Conc.+OD+Lys_conc.+His+SO4.ferm.+PO4.ferm.+PO4.utilise; 0.408, 0.694, tmp+Main.P-Source.Conc.+P-Source.Feed.conc.+Main.Thr.Conc.+Lys_conc.+lactate+SO4.ferm.+PO4.utilise; 0.408, 0.694, pH+tmp+P-Source.Feed.conc.+Main.Thr.Conc.+Nitrogen.Conc.+Lys_conc.+PO4.ferm.+PO4.utilise; 0.398, 0.694, pH+tmp+P-Source.Feed.conc.+Main.Thr.Conc.+Nitrogen.Conc.+Lys_conc.+rab+SO4.ferm.+PO4.apporte; 0.428, 0.694, pH+tmp+Main.Thr.Conc.+Lys_conc.+SO4.ferm.+PO4.apporte; 0.387, 0.694, tmp+P-Source.Feed.conc.+Main.Thr.Conc.+Lys_conc.+yield+PL+SO4.ferm.+PO4.ferm.+PO4.apporte+PO4.utilise; 0.387, 0.693, tmp+P-Source.Feed.conc.+Main.Thr.Conc.+Nitrogen.Conc.+OD+Lys_conc.+yield+SO4.ferm.+PO4.ferm.+PO4.utilise; 0.418, 0.693, tmp+P-Source.Feed.conc.+Main.Thr.Conc.+Lys_conc.+emission_O2+SO4.ferm.+PO4.apporte; 0.386, 0.693, tmp+P-Source.Feed.conc.+Main.Thr.Conc.+OD+Lys_conc.+lactate+SO4.ferm.+PO4.ferm.+PO4.apporte+PO4.utilise; 0.408, 0.693, tmp+P-Source.Feed.conc.+Main.Thr.Conc.+Nitrogen.Conc.+Lys_conc.+His+SO4.ferm.+PO4.utilise; 0.428, 0.693, tmp+Main.Thr.Conc.+Lys_conc.+lactate+SO4.ferm.+PO4.apporte; 0.375, 0.693, pH+tmp+P-Source.Feed.conc.+Main.Thr.Conc.+Nitrogen.Conc.+Lys_conc.+PL+lactate+SO4.ferm.+PO4.ferm.+PO4.utilise; 0.375, 0.693, pH+tmp+P-Source.Feed.conc.+Main.Thr.Conc.+Nitrogen.Conc.+OD+Lys_conc.+lactate+SO4.ferm.+PO4.apporte+PO4.utilise; 0.397, 0.693, pH+tmp+P-Source.Feed.conc.+Main.Thr.Conc.+Nitrogen.Conc.+Lys_conc.+yield+PL+PO4.apporte; 0.428, 0.693, tmp+P-Source.Feed.conc.+Main.Thr.Conc.+Lys_conc.+His+PO4.apporte; 0.397, 0.693, pH+tmp+P-Source.Feed.conc.+Main.Thr.Conc.+Nitrogen.Conc.+Lys_conc.+PL+lactate+PO4.apporte; 0.374, 0.693, pH+tmp+Main.P-Source.Conc.+P-Source.Feed.conc.+Main.Thr.Conc.+Nitrogen.Conc.+OD+Lys_conc.+SO4.ferm.+PO4.apporte+PO4.utilise; 0.374, 0.693, tmp+Main.P-Source.Conc.+P-Source.Feed.conc.+Main.Thr.Conc.+Nitrogen.Conc.+Lys_conc.+PL+lactate+SO4.ferm.+PO4.ferm.+PO4.utilise; 0.363, 0.693, pH+tmp+Main.P-Source.Conc.+P-Source.Feed.conc.+Main.Thr.Conc.+Nitrogen.Conc.+Lys_conc.+yield+lactate+SO4.ferm.+PO4.ferm.+PO4.apporte; 0.386, 0.693, tmp+P-Source.Feed.conc.+Main.Thr.Conc.+Nitrogen.Conc.+OD+Lys_conc.+PL+His+SO4.ferm.+PO4.utilise; 0.407, 0.693, tmp+Main.P-Source.Conc.+P-Source.Feed.conc.+Main.Thr.Conc.+Nitrogen.Conc.+Lys_conc.+PL+PO4.apporte; 0.362, 0.693, pH+tmp+Main.P-Source.Conc.+P-Source.Feed.conc.+Main.Thr.Conc.+Nitrogen.Conc.+Lys_conc.+yield+lactate+SO4.ferm.+PO4.apporte+PO4.utilise; 0.374, 0.693, tmp+Main.P-Source.Conc.+P-Source.Feed.conc.+Main.Thr.Conc.+Nitrogen.Conc.+OD+Lys_conc.+yield+PL+SO4.ferm.+PO4.apporte; 0.386, 0.693, tmp+P-Source.Feed.conc.+Main.Thr.Conc.+Nitrogen.Conc.+Lys_conc.+His+lactate+SO4.ferm.+PO4.ferm.+PO4.utilise; 0.374, 0.693, pH+tmp+Main.P-Source.Conc.+P-Source.Feed. conc.+Main.Thr.Conc.+Nitrogen.Conc.+OD+Lys_conc.+ SO4.ferm.+PO4.ferm.+PO4.apporte; 0.427, 0.693, tmp+ Main.Thr.Conc.+Lys_conc.+yield+SO4.ferm.+ PO4.apporte; 0.374, 0.693, pH+tmp+P-Source.Feed.conc.+ Main.Thr.Conc.+Nitrogen.Conc.+OD+Lys_conc.+lactate+ SO4.ferm.+PO4.ferm.+PO4.apporte; 0.397, 0.693, pH+tmp+P-Source.Feed.conc.+Main.Thr.Conc.+OD+Lys_conc.+yield+lactate+PO4.apporte; 0.385, 0.693, tmp+P-Source.Feed.conc.+Main.Thr.Conc.+Nitrogen.Conc.+Lys_conc.+His+lactate+SO4.ferm.+PO4.ferm.+PO4.apporte; 0.385, 0.693, tmp+P-Source.Feed.conc.+Main.Thr.Conc.+Nitrogen.Conc.+Lys_conc.+His+lactate+SO4.ferm.+PO4.apporte+PO4.utilise; 0.385, 0.693, tmp+P-Source.Feed.conc.+Main.Thr.Conc.+Nitrogen.Conc.+OD+Lys_conc.+PL+SO4.ferm.+PO4.apporte+PO4.utilise; 0.374, 0.693, tmp+Main.P-Source.Conc.+P-Source.Feed.conc.+Main.Thr.Conc.+Nitrogen.Conc.+Lys_conc.+PL+His+lactate+SO4.ferm.+PO4.apporte; 0.385, 0.693, tmp+P-Source.Feed.conc.+Main.Thr.Conc.+OD+Lys_conc.+yield+ SO4.ferm.+PO4.ferm.+PO4.apporte+PO4.utilise; 0.385, 0.693, pH+tmp+P-Source.Feed.conc.+Main.Thr.Conc.+Nitrogen.Conc.+OD+Lys_conc.+yield+SO4.ferm.+ PO4.utilise; 0.396, 0.693, pH+tmp+P-Source.Feed.conc.+ Main.Thr.Conc.+Nitrogen.Conc.+OD+Lys_conc.+ SO4.ferm.+PO4.utilise; 0.396, 0.693, tmp+P-Source.Feed.conc.+Main.Thr.Conc.+Lys_conc.+His+ lactate+SO4.ferm.+PO4.ferm.+PO4.utilise; 0.374, 0.693, tmp+P-Source.Feed.conc.+Main.Thr.Conc.+Nitrogen. Conc.+Lys_conc.+yield+PL+lactate+SO4.ferm.+ PO4.apporte+PO4.utilise; 0.396, 0.693, tmp+P-Source. Feed.conc.+Main.Thr.Conc.+Nitrogen.Conc.+OD+Lys_conc.+yield+lactate+PO4.apporte; 0.407, 0.693, pH+tmp+P-Source.Feed.conc.+Main.Thr.Conc.+Nitrogen. Conc.+Lys_conc.+SO4.ferm.+PO4.utilise; 0.385, 0.693, tmp+P-Source.Feed.conc.+Main.Thr.Conc.+Nitrogen. Conc.+Lys_conc.+yield+His+lactate+SO4.ferm.+ PO4.apporte; 0.417, 0.693, tmp+P-Source.Feed.conc.+ Main.Thr.Conc.+OD+Lys_conc.+lactate+PO4.apporte; 0.374, 0.693, tmp+P-Source.Feed.conc.+Main.Thr.Conc.+ Nitrogen.Conc.+Lys_conc.+yield+PL+lactate+SO4.ferm.+ PO4.ferm.+PO4.apporte; 0.396, 0.692, tmp+P-Source.Feed. conc.+Main.Thr.Conc.+Nitrogen.Conc.+OD+Lys_conc.+ lactate+SO4.ferm.+PO4.utilise; 0.385, 0.692, tmp+P-Source.Feed.conc.+Main.Thr.Conc.+OD+Lys_conc.+PL+ His+lactate+SO4.ferm.+PO4.apporte; 0.406, 0.692, pH+tmp+P-Source.Feed.conc.+Main.Thr.Conc.+OD+Lys_conc.+lactate+PO4.apporte; 0.385, 0.692, tmp+P-Source.Feed.conc.+Main.Thr.Conc.+OD+Lys_conc.+yield+ PL+lactate+SO4.ferm.+PO4.utilise; 0.385, 0.692, tmp+P-Source.Feed.conc.+Main.Thr.Conc.+Nitrogen.Conc.+OD+ Lys_conc.+PL+SO4.ferm.+PO4.ferm.+PO4.apporte; 0.385, 0.692, pH+tmp+Main.P-Source.Conc.+P-Source.Feed. conc.+Main.Thr.Conc.+Lys_conc.+PL+SO4.ferm.+ PO4.apporte+PO4.utilise; 0.396, 0.692, tmp+Main.P-Source.Conc.+P-Source.Feed.conc.+Main.Thr.Conc.+Nitrogen.Conc.+Lys_conc.+yield+lactate+PO4.apporte; 0.396, 0.692, tmp+Main.P-Source.Conc.+P-Source.Feed. conc.+Main.Thr.Conc.+Nitrogen.Conc.+Lys_conc.+PL+ lactate+SO4.ferm.; 0.385, 0.692, pH+tmp+Main.P-Source.Conc.+P-Source.Feed.conc.+Main.Thr.Conc.+Lys_conc.+PL+SO4.ferm.+PO4.ferm.+PO4.apporte; 0.373, 0.692, pH+tmp+Main.P-Source.Conc.+P-Source.Feed. conc.+Main.Thr.Conc.+Lys_conc.+yield+PL+lactate+ SO4.ferm.+PO4.apporte; 0.396, 0.692, tmp+Main.P-Source.Conc.+P-Source.Feed.conc.+Main.Thr.Conc.+OD+ Lys_conc.+yield+SO4.ferm.+PO4.utilise; 0.385, 0.692, tmp+P-Source.Feed.conc.+Main.Thr.Conc.+OD+Lys_conc.+PL+lactate+SO4.ferm.+PO4.apporte+PO4.utilise; 0.396, 0.692, tmp+P-Source.Feed.conc.+Main.Thr.Conc.+ OD+Lys_conc.+PL+lactate+SO4.ferm.+PO4.utilise; 0.385, 0.692, pH+tmp+Main.P-Source.Conc.+P-Source.Feed. conc.+Main.Thr.Conc.+Nitrogen.Conc.+OD+Lys_conc.+ yield+SO4.ferm.; 0.373, 0.692, pH+tmp+P-Source. Feed.conc.+Main.Thr.Conc.+Lys_conc.+yield+lactate+ SO4.ferm.+PO4.ferm.+PO4.apporte+PO4.utilise; 0.395, 0.692, tmp+Main.P-Source.Conc.+P-Source.Feed.conc.+ Main.Thr.Conc.+Nitrogen.Conc.+Lys_conc.+rab+ SO4.ferm.+PO4.apporte; 0.384, 0.692, pH+tmp+Main.P-Source.Conc.+P-Source.Feed.conc.+Main.Thr.Conc.+OD+ Lys_conc.+His+SO4.ferm.+PO4.utilise; 0.373, 0.692, pH+tmp+P-Source.Feed.conc.+Main.Thr.Conc.+Nitrogen. Conc.+Lys_conc.+PL+His+lactate+SO4.ferm.+ PO4.apporte; 0.406, 0.692, tmp+P-Source.Feed.conc.+ Main.Thr.Conc.+Nitrogen.Conc.+Lys_conc.+PL+His+ PO4.apporte; 0.373, 0.692, tmp+P-Source.Feed.conc.+ Main.Thr.Conc.+Nitrogen.Conc.+Lys_conc.+yield+PL+ lactate+SO4.ferm.+PO4.ferm.+PO4.utilise; 0.395, 0.692, tmp+P-Source.Feed.conc.+Main.Thr.Conc.+Lys_conc.+ His+lactate+SO4.ferm.+PO4.apporte+PO4.utilise; 0.416, 0.692, tmp+Main.P-Source.Conc.+P-Source.Feed.conc.+ Main.Thr.Conc.+Lys_conc.+lactate+PO4.apporte; 0.373, 0.692, pH+tmp+P-Source.Feed.conc.+Main.Thr.Conc.+Nitrogen.Conc.+OD+Lys_conc.+lactate+SO4.ferm.+ PO4.ferm.+PO4.utilise; 0.384, 0.692, tmp+P-Source. Feed.conc.+Main.Thr.Conc.+OD+Lys_conc.+PL+His+ SO4.ferm.+PO4.apporte+PO4.utilise; 0.395, 0.692, tmp+P-Source.Feed.conc.+Main.Thr.Conc.+Lys_conc.+His+lactate+SO4.ferm.+PO4.ferm.+PO4.apporte; 0.361, 0.692, pH+tmp+Main.P-Source.Conc.+P-Source.Feed.conc.+ Main.Thr.Conc.+Nitrogen.Conc.+Lys_conc.+yield+lactate+ SO4.ferm.+PO4.ferm.+PO4.utilise; 0.361, 0.692, pH+tmp+ Main.P-Source.Conc.+P-Source.Feed.conc.+ Main.Thr.Conc.+Nitrogen.Conc.+OD+Lys_conc.+ SO4.ferm.+PO4.ferm.+PO4.apporte+PO4.utilise; 0.384, 0.692, tmp+P-Source.Feed.conc.+Main.Thr.Conc.+OD+Lys_conc.+PL+His+SO4.ferm.+PO4.ferm.+PO4.apporte; 0.395, 0.692, pH+tmp+Main.P-Source.Conc.+P-Source. Feed.conc.+Main.Thr.Conc.+Nitrogen.Conc.+Lys_conc.+ His+PO4.apporte; 0.384, 0.692, tmp+P-Source.Feed.conc.+ Main.Thr.Conc.+OD+Lys_conc.+PL+lactate+SO4.ferm.+ PO4.ferm.+PO4.apporte; 0.384, 0.692, pH+tmp+P-Source.Feed.conc.+Main.Thr.Conc.+OD+Lys_conc.+PL+ SO4.ferm.+PO4.apporte+PO4.utilise; 0.361, 0.692, pH+tmp+Main.P-Source.Conc.+P-Source.Feed.conc.+ Main.Thr.Conc.+Nitrogen.Conc.+Lys_conc.+PL+ SO4.ferm.+PO4.ferm.+PO4.apporte+PO4.utilise; 0.384, 0.692, tmp+P-Source.Feed.conc.+Main.Thr.Conc.+Nitrogen.Conc.+OD+Lys_conc.+yield+lactate+SO4.ferm.+ PO4.utilise; 0.384, 0.692, tmp+P-Source.Feed.conc.+ Main.Thr.Conc.+OD+Lys_conc.+PL+His+SO4.ferm.+ PO4.ferm.+PO4.utilise; 0.384, 0.692, pH+tmp+Main.P-Source.Conc.+P-Source.Feed.conc.+Main.Thr.Conc.+OD+ Lys_conc.+SO4.ferm.+PO4.apporte+PO4.utilise; 0.372, 0.692, pH+tmp+Main.P-Source.Conc.+P-Source.Feed. conc.+Main.Thr.Conc.+Nitrogen.Conc.+OD+Lys_conc.+ SO4.ferm.+PO4.ferm.+PO4.utilise; 0.384, 0.692, pH+tmp+ Main.P-Source.Conc.+P-Source.Feed.conc.+Main.Thr. Conc.+Lys_conc.+PL+SO4.ferm.+PO4.ferm.+PO4.utilise; 0.384, 0.692, tmp+P-Source.Feed.conc.+Main.Thr.Conc.+ Nitrogen.Conc.+OD+Lys_conc.+His+lactate+SO4.ferm.+ PO4.utilise; 0.395, 0.692, tmp+P-Source.Feed.conc.+ Main.Thr.Conc.+Nitrogen.Conc.+Lys_conc.+yield+lactate+ SO4.ferm.+PO4.utilise; 0.372, 0.692, tmp+Main.P-

Source.Conc.+P-Source.Feed.conc.+Main.Thr.Conc.+Nitrogen.Conc.+Lys_conc.+PL+His+SO4.ferm.+PO4.ferm.+PO4.apporte; 0.416, 0.692, tmp+P-Source.Feed.conc.+Main.Thr.Conc.+Lys_conc.+PO4.ferm.+PO4.apporte+PO4.utilise; 0.405, 0.692, tmp+P-Source.Feed.conc.+Main.Thr.Conc.+Nitrogen.Conc.+Lys_conc.+lactate+PO4.apporte+PO4.utilise; 0.405, 0.692, tmp+Main.P-Source.Conc.+P-Source.Feed.conc.+Main.Thr.Conc.+Lys_conc.+yield+SO4.ferm.+PO4.utilise; 0.384, 0.692, pH+tmp+Main.P-Source.Conc.+P-Source.Feed.conc.+Main.Thr.Conc.+OD+Lys_conc.+SO4.ferm.+PO4.ferm.+PO4.apporte; 0.395, 0.692, tmp+P-Source.Feed.conc.+Main.Thr.Conc.+Nitrogen.Conc.+Lys_conc.+yield+PL+lactate+PO4.apporte; 0.405, 0.692, tmp+Main.P-Source.Conc.+P-Source.Feed.conc.+Main.Thr.Conc.+OD+Lys_conc.+yield+PO4.apporte; 0.384, 0.692, tmp+P-Source.Feed.conc.+Main.Thr.Conc.+Nitrogen.Conc.+OD+Lys_conc.+PL+SO4.ferm.+PO4.ferm.+PO4.utilise; 0.372, 0.692, pH+tmp+P-Source.Feed.conc.+Main.Thr.Conc.+Nitrogen.Conc.+Lys_conc.+yield+PL+SO4.ferm.+PO4.apporte+PO4.utilise; 0.395, 0.692, tmp+Main.P-Source.Conc.+P-Source.Feed.conc.+Main.Thr.Conc.+Nitrogen.Conc.+OD+Lys_conc.+SO4.ferm.+PO4.utilise; 0.383, 0.692, pH+tmp+P-Source.Feed.conc.+Main.Thr.Conc.+OD+Lys_conc.+PL+SO4.ferm.+PO4.ferm.+PO4.apporte; 0.372, 0.692, tmp+Main.P-Source.Conc.+P-Source.Feed.conc.+Main.Thr.Conc.+Nitrogen.Conc.+Lys_conc.+yield+PL+SO4.ferm.+PO4.ferm.+PO4.apporte; 0.372, 0.692, tmp+Main.P-Source.Conc.+P-Source.Feed.conc.+Main.Thr.Conc.+Nitrogen.Conc.+Lys_conc.+yield+PL+SO4.ferm.+PO4.apporte+PO4.utilise; 0.360, 0.692, tmp+Main.P-Source.Conc.+P-Source.Feed.conc.+Main.Thr.Conc.+Nitrogen.Conc.+Lys_conc.+yield+lactate+SO4.ferm.+PO4.ferm.+PO4.apporte+PO4.utilise; 0.415, 0.692, pH+tmp+P-Source.Feed.conc.+Main.Thr.Conc.+Lys_conc.+His+PO4.apporte; 0.394, 0.692, pH+tmp+P-Source.Feed.conc.+Main.Thr.Conc.+Nitrogen.Conc.+Lys_conc.+emission_O2+SO4.ferm.+PO4.apporte; 0.405, 0.692, tmp+P-Source.Feed.conc.+Main.Thr.Conc.+Nitrogen.Conc.+Lys_conc.+yield+PO4.apporte+PO4.utilise; 0.372, 0.692, pH+tmp+P-Source.Feed.conc.+Main.Thr.Conc.+Nitrogen.Conc.+Lys_conc.+yield+PL+SO4.ferm.+PO4.ferm.+PO4.apporte; 0.372, 0.691, tmp+Main.P-Source.Conc.+P-Source.Feed.conc.+Main.Thr.Conc.+Nitrogen.Conc.+Lys_conc.+PL+His+SO4.ferm.+PO4.apporte+PO4.utilise; 0.405, 0.691, tmp+Main.P-Source.Conc.+P-Source.Feed.conc.+Main.Thr.Conc.+Nitrogen.Conc.+OD+Lys_conc.+PO4.apporte; 0.383, 0.691, tmp+Main.P-Source.Conc.+P-Source.Feed.conc.+Main.Thr.Conc.+Lys_conc.+yield+SO4.ferm.+PO4.ferm.+PO4.apporte+PO4.utilise; 0.383, 0.691, tmp+P-Source.Feed.conc.+Main.Thr.Conc.+OD+Lys_conc.+PL+lactate+SO4.ferm.+PO4.ferm.+PO4.utilise; 0.383, 0.691, pH+tmp+Main.P-Source.Conc.+P-Source.Feed.conc.+Main.Thr.Conc.+Lys_conc.+His+SO4.ferm.+PO4.ferm.+PO4.utilise; 0.425, 0.691, tmp+Main.Thr.Conc.+OD+Lys_conc.+SO4.ferm.+PO4.apporte; 0.383, 0.691, pH+tmp+P-Source.Feed.conc.+Main.Thr.Conc.+OD+Lys_conc.+yield+PL+SO4.ferm.+PO4.utilise; 0.372, 0.691, tmp+P-Source.Feed.conc.+Main.Thr.Conc.+Nitrogen.Conc.+Lys_conc.+yield+PL+SO4.ferm.+PO4.ferm.+PO4.apporte+PO4.utilise; 0.415, 0.691, pH+tmp+P-Source.Feed.conc.+Main.Thr.Conc.+Lys_conc.+SO4.ferm.+PO4.utilise; 0.383, 0.691, pH+tmp+Main.P-Source.Feed.conc.+Main.Thr.Conc.+Lys_conc.+His+SO4.ferm.+PO4.ferm.+PO4.apporte; 0.372, 0.691, tmp+P-Source.Feed.conc.+Main.Thr.Conc.+Nitrogen.Conc.+OD+Lys_conc.+lactate+SO4.ferm.+PO4.ferm.+PO4.apporte+PO4.utilise; 0.394, 0.691, tmp+P-Source.Feed.conc.+Main.Thr.Conc.+Nitrogen.Conc.+Lys_conc.+yield+PO4.ferm.+PO4.apporte+PO4.utilise; 0.405, 0.691, tmp+P-Source.Feed.conc.+Main.Thr.Conc.+Nitrogen.Conc.+Lys_conc.+lactate+PO4.ferm.+PO4.apporte; 0.415, 0.691, tmp+P-Source.Feed.conc.+Main.Thr.Conc.+Lys_conc.+PL+lactate+PO4.apporte; 0.404, 0.691, pH+tmp+P-Source.Feed.conc.+Main.Thr.Conc.+Lys_conc.+rab+SO4.ferm.+PO4.apporte; 0.383, 0.691, pH+tmp+Main.P-Source.Conc.+P-Source.Feed.conc.+Main.Thr.Conc.+Lys_conc.+His+SO4.ferm.+PO4.apporte+PO4.utilise; 0.371, 0.691, tmp+Main.P-Source.Conc.+P-Source.Feed.conc.+Main.Thr.Conc.+Nitrogen.Conc.+Lys_conc.+PL+His+SO4.ferm.+PO4.ferm.+PO4.utilise; 0.404, 0.691, tmp+P-Source.Feed.conc.+Main.Thr.Conc.+Nitrogen.Conc.+Lys_conc.+yield+PO4.ferm.+PO4.apporte; 0.415, 0.691, tmp+P-Source.Feed.conc.+Main.Thr.Conc.+Lys_conc.+His+SO4.ferm.+PO4.utilise; 0.383, 0.691, tmp+P-Source.Feed.conc.+Main.Thr.Conc.+OD+Lys_conc.+yield+PL+His+SO4.ferm.+PO4.utilise; 0.383, 0.691, pH+tmp+Main.P-Source.Conc.+P-Source.Feed.conc.+Main.Thr.Conc.+Nitrogen.Conc.+Lys_conc.+yield+PL+SO4.ferm.; 0.371, 0.691, pH+tmp+P-Source.Feed.conc.+Main.Thr.Conc.+Nitrogen.Conc.+Lys_conc.+yield+PL+SO4.ferm.+PO4.ferm.+PO4.utilise; 0.404, 0.691, pH+tmp+P-Source.Feed.conc.+Main.Thr.Conc.+Lys_conc.+lactate+SO4.ferm.+PO4.utilise; 0.383, 0.691, tmp+Main.P-Source.Conc.+P-Source.Feed.conc.+Main.Thr.Conc.+Nitrogen.Conc.+Lys_conc.+lactate+PO4.ferm.+PO4.apporte+PO4.utilise; 0.383, 0.691, pH+tmp+P-Source.Feed.conc.+Main.Thr.Conc.+Nitrogen.Conc.+Lys_conc.+lactate+PO4.ferm.+PO4.apporte+PO4.utilise; 0.383, 0.691, pH+tmp+P-Source.Feed.conc.+Main.Thr.Conc.+OD+Lys_conc.+PL+SO4.ferm.+PO4.ferm.+PO4.utilise; 0.393, 0.691, tmp+P-Source.Feed.conc.+Main.Thr.Conc.+Nitrogen.Conc.+Lys_conc.+emission_O2+rab+SO4.ferm.+PO4.apporte; 0.359, 0.691, pH+tmp+P-Source.Feed.conc.+Main.Thr.Conc.+Nitrogen.Conc.+OD+Lys_conc.+yield+PL+lactate+SO4.ferm.+PO4.apporte; 0.382, 0.691, pH+tmp+Main.P-Source.Conc.+P-Source.Feed.conc.+Main.Thr.Conc.+OD+Lys_conc.+SO4.ferm.+PO4.ferm.+PO4.utilise; 0.382, 0.691, tmp+Main.P-Source.Conc.+P-Source.Feed.conc.+Main.Thr.Conc.+Lys_conc.+yield+PL+SO4.ferm.+PO4.apporte+PO4.utilise; 0.382, 0.691, tmp+Main.P-Source.Conc.+P-Source.Feed.conc.+Main.Thr.Conc.+Nitrogen.Conc.+OD+Lys_conc.+His+SO4.ferm.+PO4.utilise; 0.382, 0.691, tmp+Main.P-Source.Conc.+P-Source.Feed.conc.+Main.Thr.Conc.+Lys_conc.+yield+PL+SO4.ferm.+PO4.ferm.+PO4.apporte; 0.382, 0.691, tmp+P-Source.Feed.conc.+Main.Thr.Conc.+OD+Lys_conc.+His+SO4.ferm.+PO4.ferm.+PO4.apporte+PO4.utilise; 0.382, 0.691, pH+tmp+P-Source.Feed.conc.+Main.Thr.Conc.+Lys_conc.+PL+His+lactate+SO4.ferm.+PO4.apporte; 0.404, 0.691, tmp+P-Source.Feed.conc.+Main.Thr.Conc.+OD+Lys_conc.+yield+PL+PO4.apporte; 0.404, 0.691, pH+tmp+P-Source.Feed.conc.+Main.Thr.Conc.+OD+Lys_conc.+His+PO4.apporte; 0.371, 0.691, tmp+Main.P-Source.Conc.+P-Source.Feed.conc.+Main.Thr.Conc.+Nitrogen.Conc.+Lys_conc.+yield+PL+SO4.ferm.+PO4.ferm.+PO4.utilise; 0.393, 0.691, pH+tmp+P-Source.Feed.conc.+Main.Thr.Conc.+Nitrogen.Conc.+Lys_conc.+lactate+PO4.apporte+PO4.utilise; 0.393, 0.691, pH+tmp+Main.P-Source.Conc.+P-Source.Feed.conc.+Main.Thr.Conc.+Nitrogen.Conc.+OD+Lys_conc.+PO4.apporte; 0.414, 0.691, tmp+P-Source.Feed.conc.+Main.Thr.Conc.+OD+Lys_conc.+yield+

PO4.utilise; 0.393, 0.691, tmp+Main.P-Source.Conc.+P-Source.Feed.conc.+Main.Thr.Conc.+Nitrogen.Conc.+Lys_conc.+yield+SO4.ferm.+PO4.ferm.; 0.370, 0.691, pH+tmp+Main.P-Source.Conc.+P-Source.Feed.conc.+Main.Thr.Conc.+OD+Lys_conc.+PL+His+SO4.ferm.+PO4.apporte; 0.382, 0.691, tmp+Main.P-Source.Conc.+P-Source.Feed.conc.+Main.Thr.Conc.+Lys_conc.+yield+PL+SO4.ferm.+PO4.ferm.+PO4.utilise; 0.382, 0.691, tmp+P-Source.Feed.conc.+Main.Thr.Conc.+OD+Lys_conc.+yield+PL+His+SO4.ferm.+PO4.apporte; 0.382, 0.691, pH+tmp+P-Source.Feed.conc.+Main.Thr.Conc.+Lys_conc.+PL+His+SO4.ferm.+PO4.ferm.+PO4.utilise; 0.382, 0.691, tmp+Main.P-Source.Conc.+P-Source.Feed.conc.+Main.Thr.Conc.+OD+Lys_conc.+lactate+SO4.ferm.+PO4.apporte+PO4.utilise; 0.393, 0.691, tmp+Main.P-Source.Conc.+P-Source.Feed.conc.+Main.Thr.Conc.+Nitrogen.Conc.+Lys_conc.+emission_O2+SO4.ferm.+PO4.apporte; 0.382, 0.690, tmp+Main.P-Source.Conc.+P-Source.Feed.conc.+Main.Thr.Conc.+Nitrogen.Conc.+Lys_conc.+PL+lactate+SO4.ferm.+PO4.utilise; 0.382, 0.690, pH+tmp+Main.P-Source.Conc.+P-Source.Feed.conc.+Main.Thr.Conc.+Nitrogen.Conc.+Lys_conc.+PL+SO4.ferm.+PO4.utilise; 0.424, 0.690, tmp+P-Source.Feed.conc.+Main.Thr.Conc.+Lys_conc.+PO4.apporte+PO4.utilise; 0.403, 0.690, pH+tmp+Main.P-Source.Conc.+P-Source.Feed.conc.+Main.Thr.Conc.+Lys_conc.+SO4.ferm.+PO4.utilise; 0.382, 0.690, tmp+Main.P-Source.Conc.+P-Source.Feed.conc.+Main.Thr.Conc.+OD+Lys_conc.+lactate+SO4.ferm.+PO4.ferm.+PO4.apporte; 0.382, 0.690, tmp+Main.P-Source.Conc.+P-Source.Feed.conc.+Main.Thr.Conc.+Nitrogen.Conc.+Lys_conc.+PL+His+SO4.ferm.+PO4.utilise; 0.403, 0.690, tmp+P-Source.Feed.conc.+Main.Thr.Conc.+Nitrogen.Conc.+OD+Lys_conc.+PL+PO4.apporte; 0.382, 0.690, tmp+Main.P-Source.Conc.+P-Source.Feed.conc.+Main.Thr.Conc.+Lys_conc.+PL+SO4.ferm.+PO4.ferm.+PO4.apporte+PO4.utilise; 0.403, 0.690, pH+tmp+P-Source.Feed.conc.+Main.Thr.Conc.+Lys_conc.+yield+SO4.ferm.+PO4.utilise; 0.370, 0.690, pH+tmp+P-Source.Feed.conc.+Main.Thr.Conc.+Lys_conc.+PL+lactate+SO4.ferm.+PO4.ferm.+PO4.apporte+PO4.utilise; 0.393, 0.690, tmp+P-Source.Feed.conc.+Main.Thr.Conc.+Nitrogen.Conc.+Lys_conc.+rab+lactate+SO4.ferm.+PO4.apporte; 0.370, 0.690, pH+tmp+Main.P-Source.Conc.+P-Source.Feed.conc.+Main.Thr.Conc.+Lys_conc.+yield+lactate+SO4.ferm.+PO4.apporte+PO4.utilise; 0.370, 0.690, pH+tmp+Main.P-Source.Conc.+P-Source.Feed.conc.+Main.Thr.Conc.+Lys_conc.+yield+lactate+SO4.ferm.+PO4.ferm.+PO4.apporte; 0.358, 0.690, tmp+Main.P-Source.Conc.+P-Source.Feed.conc.+Main.Thr.Conc.+Nitrogen.Conc.+Lys_conc.+PL+lactate+SO4.ferm.+PO4.ferm.+PO4.apporte+PO4.utilise; 0.358, 0.690, pH+tmp+P-Source.Feed.conc.+Main.Thr.Conc.+Nitrogen.Conc.+Lys_conc.+yield+lactate+SO4.ferm.+PO4.ferm.+PO4.apporte+PO4.utilise; 0.413, 0.690, tmp+Main.P-Source.Conc.+P-Source.Feed.conc.+Main.Thr.Conc.+OD+Lys_conc.+PO4.apporte; 0.381, 0.690, tmp+P-Source.Feed.conc.+Main.Thr.Conc.+OD+Lys_conc.+yield+PL+SO4.ferm.+PO4.apporte+PO4.utilise; 0.413, 0.690, tmp+P-Source.Feed.conc.+Main.Thr.Conc.+OD+Lys_conc.+Thr+PO4.apporte; 0.381, 0.690, tmp+P-Source.Feed.conc.+Main.Thr.Conc.+OD+Lys_conc.+PL+SO4.ferm.+PO4.ferm.+PO4.apporte+PO4.utilise; 0.392, 0.690, tmp+P-Source.Feed.conc.+Main.Thr.Conc.+Ly-s_conc.+yield+PL+His+SO4.ferm.+PO4.apporte; 0.392, 0.690, pH+tmp+Main.P-Source.Conc.+P-Source.Feed.conc.+Main.Thr.Conc.+Nitrogen.Conc.+Lys_conc.+PL+PO4.apporte; 0.392, 0.690, pH+tmp+P-Source.Feed.conc.+Main.Thr.Conc.+Nitrogen.Conc.+Lys_conc.+lactate+PO4.ferm.+PO4.apporte; 0.370, 0.690, tmp+Main.P-Source.Conc.+P-Source.Feed.conc.+Main.Thr.Conc.+Nitrogen.Conc.+OD+Lys_conc.+lactate+SO4.ferm.+PO4.apporte+PO4.utilise; 0.381, 0.690, tmp+P-Source.Feed.conc.+Main.Thr.Conc.+Nitrogen.Conc.+OD+Lys_conc.+yield+His+SO4.ferm.+PO4.utilise; 0.381, 0.690, pH+tmp+Main.P-Source.Conc.+P-Source.Feed.conc.+Main.Thr.Conc.+Nitrogen.Conc.+OD+Lys_conc.+SO4.ferm.+PO4.utilise; 0.413, 0.690, pH+tmp+P-Source.Feed.conc.+Main.Thr.Conc.+Lys_conc.+PO4.apporte+PO4.utilise; 0.370, 0.690, tmp+Main.P-Source.Conc.+P-Source.Feed.conc.+Main.Thr.Conc.+Nitrogen.Conc.+OD+Lys_conc.+lactate+SO4.ferm.+PO4.ferm.+PO4.apporte; 0.381, 0.690, tmp+Main.P-Source.Conc.+P-Source.Feed.conc.+Main.Thr.Conc.+OD+Lys_conc.+His+SO4.ferm.+PO4.ferm.+PO4.apporte; 0.370, 0.690, pH+tmp+P-Source.Feed.conc.+Main.Thr.Conc.+Nitrogen.Conc.+OD+Lys_conc.+His+SO4.ferm.+PO4.ferm.+PO4.apporte; 0.381, 0.690, tmp+P-Source.Feed.conc.+Main.Thr.Conc.+OD+Lys_conc.+yield+PL+SO4.ferm.+PO4.ferm.+PO4.apporte; 0.370, 0.690, pH+tmp+P-Source.Feed.conc.+Main.Thr.Conc.+Nitrogen.Conc.+OD+Lys_conc.+His+SO4.ferm.+PO4.apporte+PO4.utilise; 0.370, 0.690, pH+tmp+Main.P-Source.Conc.+P-Source.Feed.conc.+Main.Thr.Conc.+OD+Lys_conc.+yield+PL+SO4.ferm.+PO4.apporte; 0.369, 0.690, pH+tmp+Main.P-Source.Conc.+P-Source.Feed.conc.+Main.Thr.Conc.+Lys_conc.+yield+lactate+SO4.ferm.+PO4.ferm.+PO4.utilise; 0.369, 0.690, pH+tmp+Main.P-Source.Conc.+P-Source.Feed.conc.+Main.Thr.Conc.+OD+Lys_conc.+PL+lactate+SO4.ferm.+PO4.apporte; 0.403, 0.690, tmp+Main.P-Source.Conc.+P-Source.Feed.conc.+Main.Thr.Conc.+OD+Lys_conc.+SO4.ferm.+PO4.utilise; 0.423, 0.690, tmp+P-Source.Feed.conc.+Main.Thr.Conc.+Lys_conc.+PO4.ferm.+PO4.apporte; 0.369, 0.690, pH+tmp+P-Source.Feed.conc.+Main.Thr.Conc.+Nitrogen.Conc.+OD+Lys_conc.+yield+SO4.ferm.+PO4.apporte+PO4.utilise; 0.369, 0.690, pH+tmp+P-Source.Feed.conc.+Main.Thr.Conc.+OD+Lys_conc.+yield+lactate+SO4.ferm.+PO4.apporte+PO4.utilise; 0.381, 0.690, tmp+Main.P-Source.Conc.+P-Source.Feed.conc.+Main.Thr.Conc.+OD+Lys_conc.+His+SO4.ferm.+PO4.apporte+PO4.utilise; 0.357, 0.690, pH+tmp+Main.P-Source.Conc.+P-Source.Feed.conc.+Main.Thr.Conc.+Nitrogen.Conc.+OD+Lys_conc.+PL+lactate+SO4.ferm.+PO4.apporte; 0.381, 0.690, pH+tmp+P-Source.Feed.conc.+Main.Thr.Conc.+Lys_conc.+PL+His+SO4.ferm.+PO4.ferm.+PO4.apporte; 0.369, 0.690, pH+tmp+P-Source.Feed.conc.+Main.Thr.Conc.+Nitrogen.Conc.+OD+Lys_conc.+His+SO4.ferm.+PO4.ferm.+PO4.utilise; 0.381, 0.690, pH+tmp+P-Source.Feed.conc.+Main.Thr.Conc.+Lys_conc.+PL+His+SO4.ferm.+PO4.apporte+PO4.utilise; 0.369, 0.690, pH+tmp+P-Source.Feed.conc.+Main.Thr.Conc.+Nitrogen.Conc.+Lys_conc.+His+SO4.ferm.+PO4.ferm.+PO4.apporte+PO4.utilise; 0.381, 0.690, tmp+P-Source.Feed.conc.+Main.Thr.Conc.+OD+Lys_conc.+yield+PL+SO4.ferm.+PO4.ferm.+PO4.utilise; 0.369, 0.690, tmp+Main.P-Source.Conc.+P-Source.Feed.conc.+Main.Thr.Conc.+OD+Lys_conc.+yield+PL+lactate+SO4.ferm.+PO4.apporte; 0.381, 0.690, tmp+Main.P-Source.Conc.+P-Source.Feed.conc.+Main.Thr.Conc.+OD+Lys_conc.+His+SO4.ferm.+PO4.ferm.+PO4.utilise; 0.392, 0.690, pH+tmp+P-Source.Feed.conc.+Main.Thr.Conc.+Nitrogen.Conc.+Lys_conc.+lactate+SO4.ferm.+PO4.utilise; 0.392, 0.690, tmp+P-Source.Feed.conc.+Main.Thr.Conc.+Nitrogen.

Conc.+OD+Lys_conc.+PO4.ferm.+PO4.apporte+PO4.utilise; 0.369, 0.690, pH+tmp+Main.P-Source.Conc.+P-Source.Feed.conc.+Main.Thr.Conc.+Nitrogen.Conc.+Lys_conc.+yield+lactate+SO4.ferm.+PO4.utilise; 0.369, 0.690, pH+tmp+P-Source.Feed.conc.+Main.Thr.Conc.+Nitrogen.Conc.+OD+Lys_conc.+yield+SO4.ferm.+PO4.ferm.+PO4.apporte; 0.381, 0.690, pH+tmp+P-Source.Feed.conc.+Main.Thr.Conc.+Nitrogen.Conc.+OD+Lys_conc.+yield+lactate+PO4.apporte; 0.369, 0.690, pH+tmp+P-Source.Feed.conc.+Main.Thr.Conc.+OD+Lys_conc.+yield+lactate+SO4.ferm.+PO4.ferm.+PO4.apporte; 0.380, 0.690, tmp+Main.P-Source.Conc.+P-Source.Feed.conc.+Main.Thr.Conc.+OD+Lys_conc.+yield+SO4.ferm.+PO4.apporte+PO4.utilise; 0.432, 0.690, tmp+Main.P-Source.Conc.+Main.Thr.Conc.+Lys_conc.+PO4.apporte; 0.380, 0.690, tmp+Main.P-Source.Conc.+P-Source.Feed.conc.+Main.Thr.Conc.+OD+Lys_conc.+lactate+SO4.ferm.+PO4.ferm.+PO4.utilise; 0.402, 0.690, tmp+P-Source.Feed.conc.+Main.Thr.Conc.+Lys_conc.+PL+lactate+SO4.ferm.+PO4.utilise; 0.402, 0.690, tmp+P-Source.Feed.conc.+Main.Thr.Conc.+Lys_conc.+rab+lactate+SO4.ferm.+PO4.apporte; 0.380, 0.690, pH+tmp+Main.P-Source.Conc.+P-Source.Feed.conc.+Main.Thr.Conc.+Nitrogen.Conc.+Lys_conc.+PL+lactate+SO4.ferm.; 0.380, 0.690, pH+tmp+P-Source.Feed.conc.+Main.Thr.Conc.+Lys_conc.+His+SO4.ferm.+PO4.ferm.+PO4.apporte+PO4.utilise; 0.412, 0.690, pH+tmp+P-Source.Feed.conc.+Main.Thr.Conc.+Lys_conc.+PO4.ferm.+PO4.apporte; 0.402, 0.690, tmp+P-Source.Feed.conc.+Main.Thr.Conc.+Nitrogen.Conc.+Lys_conc.+PL+SO4.ferm.+PO4.utilise; 0.391, 0.690, tmp+Main.P-Source.Conc.+P-Source.Feed.conc.+Main.Thr.Conc.+Nitrogen.Conc.+Lys_conc.+PL+His+SO4.ferm.; 0.412, 0.690, pH+tmp+P-Source.Feed.conc.+Main.Thr.Conc.+Lys_conc.+Thr+PO4.apporte; 0.380, 0.690, tmp+Main.P-Source.Conc.+P-Source.Feed.conc.+Main.Thr.Conc.+OD+Lys_conc.+yield+SO4.ferm.+PO4.ferm.+PO4.apporte; 0.369, 0.690, pH+tmp+P-Source.Feed.conc.+Main.Thr.Conc.+Lys_conc.+yield+PL+lactate+SO4.ferm.+PO4.apporte+PO4.utilise; 0.391, 0.690, tmp+P-Source.Feed.conc.+Main.Thr.Conc.+Nitrogen. Conc.+Lys_conc.+PL+PO4.ferm.+PO4.apporte+PO4.utilise; 0.391, 0.690, tmp+Main.P-Source.Conc.+P-Source.Feed.conc.+Main.Thr.Conc.+Nitrogen.Conc.+OD+Lys_conc.+lactate+SO4.ferm.; 0.402, 0.690, tmp+P-Source.Feed.conc.+Main.Thr.Conc.+Nitrogen.Conc.+Lys_conc.+yield+PO4.ferm.+PO4.utilise; 0.369, 0.690, pH+tmp+P-Source.Feed.conc.+Main.Thr.Conc.+Lys_conc.+yield+PL+lactate+SO4.ferm.+PO4.ferm.+PO4.utilise; 0.369, 0.690, tmp+Main.P-Source.Conc.+P-Source.Feed.conc.+Main.Thr.Conc.+Nitrogen.Conc.+Lys_conc.+His+lactate+SO4.ferm.+PO4.ferm.+PO4.apporte; 0.369, 0.690, pH+tmp+P-Source.Feed.conc.+Main.Thr.Conc.+Lys_conc.+yield+PL+lactate+SO4.ferm.+PO4.ferm.+PO4.apporte; 0.369, 0.690, pH+tmp+Main.P-Source.Conc.+P-Source.Feed.conc.+Main.Thr.Conc.+Lys_conc.+lactate+SO4.ferm.+PO4.ferm.+PO4.apporte+PO4.utilise; 0.412, 0.690, tmp+P-Source.Feed.conc.+Main.Thr.Conc.+OD+Lys_conc.+His+PO4.apporte; 0.391, 0.690, pH+tmp+P-Source.Feed.conc.+Main.Thr.Conc.+Nitrogen.Conc.+Lys_conc.+yield+SO4.ferm.+PO4.utilise; 0.391, 0.690, tmp+Main.P-Source.Conc.+P-Source.Feed.conc.+Main.Thr.Conc.+Lys_conc.+yield+His+SO4.ferm.+PO4.apporte; 0.369, 0.690, pH+tmp+P-Source.Feed.conc.+Main.Thr.Conc.+OD+Lys_conc.+yield+lactate+SO4.ferm.+PO4.ferm.+PO4.utilise; 0.357, 0.689, pH+tmp+Main.P-Source.Conc.+P-Source.Feed.conc.+Main.Thr.Conc.+Nitrogen.Conc.+OD+Lys_conc.+PL+His+SO4.ferm.+PO4.apporte; 0.402, 0.689, pH+tmp+P-Source.Feed.conc.+Main.Thr.Conc.+Lys_conc.+emission_O2+SO4.ferm.+PO4.apporte; 0.368, 0.689, tmp+P-Source.Feed.conc.+Main.Thr.Conc.+Lys_conc.+yield+PL+lactate+SO4.ferm.+PO4.ferm.+PO4.apporte+PO4.utilise; 0.368, 0.689, pH+tmp+P-Source.Feed.conc.+Main.Thr.Conc.+Nitrogen.Conc.+Lys_conc.+PL+His+SO4.ferm.+PO4.ferm.+PO4.utilise; 0.380, 0.689, tmp+Main.P-Source.Conc.+P-Source.Feed.conc.+Main.Thr.Conc.+OD+Lys_conc.+yield+SO4.ferm.+PO4.ferm.+PO4.utilise; 0.380, 0.689, pH+tmp+Main.P-Source.Conc.+P-Source.Feed.conc.+Main.Thr.Conc.+Lys_conc.+His+lactate+SO4.ferm.+PO4.apporte; 0.368, 0.689, tmp+Main.P-Source.Conc.+P-Source.Feed.conc.+Main.Thr.Conc.+Nitrogen.Conc.+Lys_conc.+His+lactate+SO4.ferm.+PO4.apporte+PO4.utilise; 0.401, 0.689, pH+tmp+P-Source.Feed.conc.+Main.Thr.Conc.+Lys_conc.+yield+PL+PO4.apporte; 0.368, 0.689, pH+tmp+P-Source.Feed.conc.+Main.Thr.Conc.+Nitrogen.Conc.+OD+Lys_conc.+yield+SO4.ferm.+PO4.ferm.+PO4.utilise; 0.391, 0.689, pH+tmp+P-Source.Feed.conc.+Main.Thr.Conc.+OD+Lys_conc.+PL+SO4.ferm.+PO4.utilise; 0.412, 0.689, tmp+Main.P-Source.Conc.+Main.Thr.Conc.+Lys_conc.+lactate+SO4.ferm.+PO4.apporte; 0.391, 0.689, tmp+P-Source.Feed.conc.+Main.Thr.Conc.+Nitrogen.Conc.+Lys_conc.+PL+rab+SO4.ferm.+PO4.apporte; 0.401, 0.689, tmp+Main.P-Source.Conc.+P-Source.Feed.conc.+Main.Thr.Conc.+Lys_conc.+His+SO4.ferm.+PO4.utilise; 0.368, 0.689, pH+tmp+P-Source.Feed.conc.+Main.Thr.Conc.+Nitrogen.Conc.+Lys_conc.+PL+His+SO4.ferm.+PO4.ferm.+PO4.apporte; 0.368, 0.689, pH+tmp+P-Source.Feed.conc.+Main.Thr.Conc.+OD+Lys_conc.+PL+His+lactate+SO4.ferm.+PO4.utilise; 0.401, 0.689, pH+tmp+Main.P-Source.Conc.+P-Source.Feed.conc.+Main.Thr.Conc.+Lys_conc.+yield+PO4.apporte; 0.368, 0.689, tmp+P-Source.Feed.conc.+Main.Thr.Conc.+Nitrogen.Conc.+OD+Lys_conc.+yield+lactate+SO4.ferm.+PO4.apporte+PO4.utilise; 0.390, 0.689, pH+tmp+P-Source.Feed.conc.+Main.Thr.Conc.+Nitrogen.Conc.+OD+Lys_conc.+PL+PO4.apporte; 0.411, 0.689, tmp+P-Source.Feed.conc.+Main.Thr.Conc.+Lys_conc.+PL+SO4.ferm.+PO4.utilise; 0.368, 0.689, tmp+Main.P-Source.Conc.+P-Source.Feed.conc.+Main.Thr.Conc.+Nitrogen.Conc.+OD+Lys_conc.+lactate+SO4.ferm.+PO4.ferm.+PO4.utilise; 0.356, 0.689, pH+tmp+Main.P-Source.Conc.+P-Source.Feed.conc.+Main.Thr.Conc.+Nitrogen.Conc.+Lys_conc.+PL+lactate+SO4.ferm.+PO4.ferm.+PO4.apporte; 0.368, 0.689, pH+tmp+P-Source.Feed.conc.+Main.Thr.Conc.+OD+Lys_conc.+lactate+SO4.ferm.+PO4.ferm.+PO4.apporte+PO4.utilise; 0.368, 0.689, pH+tmp+P-Source.Feed.conc.+Main.Thr.Conc.+Nitrogen.Conc.+Lys_conc.+PL+His+SO4.ferm.+PO4.apporte+PO4.utilise; 0.379, 0.689, pH+tmp+Main.P-Source.Conc.+P-Source.Feed.conc.+Main.Thr.Conc.+Nitrogen.Conc.+OD+Lys_conc.+lactate+SO4.ferm.; 0.356, 0.689, pH+tmp+Main.P-Source.Conc.+P-Source.Feed.conc.+Main.Thr.Conc.+Nitrogen.Conc.+Lys_conc.+PL+lactate+SO4.ferm.+PO4.apporte+PO4.utilise; 0.401, 0.689, tmp+P-Source.Feed.conc.+Main.Thr.Conc.+Lys_conc.+emission_O2+rab+SO4.ferm.+PO4.apporte; 0.379, 0.689, pH+tmp+Main.P-Source.Conc.+P-Source.Feed.conc.+Main.Thr.Conc.+Nitrogen.Conc.+Lys_conc.+rab+SO4.ferm.+PO4.apporte; 0.390, 0.689, tmp+P-Source.Feed.conc.+Main.Thr.Conc.+Nitrogen. Conc.+Lys_conc.+emission_O2+lactate+SO4.ferm.+PO4.apporte; 0.368, 0.689, tmp+P-Source.Feed.conc.+Main.Thr.Conc.+Nitrogen.Conc.+OD+Lys_conc.+yield+ lactate+SO4.ferm.+PO4.ferm.+PO4.apporte; 0.368, 0.689, tmp+Main.P-Source.Conc.+P-Source.Feed.conc.+Main. Thr.Conc.+Nitrogen.Conc.+Lys_conc.+His+lactate+ SO4.ferm.+PO4.ferm.+PO4.utilise; 0.390, 0.689, tmp+ Main.P-Source.Conc.+P-Source.Feed.conc.+Main.Thr. Conc.+Lys_conc.+yield+lactate+SO4.ferm.+PO4.utilise; 0.367, 0.689, pH+tmp+Main.P-Source.Conc.+P-Source. Feed.conc.+Main.Thr.Conc.+Nitrogen.Conc.+OD+Lys_conc.+His+SO4.ferm.+PO4.utilise; 0.390, 0.689, pH+tmp+Main.P-Source.Conc.+P-Source.Feed.conc.+ Main.Thr.Conc.+Lys_conc.+lactate+SO4.ferm.+ PO4.utilise; 0.411, 0.689, tmp+P-Source.Feed.conc.+ Main.Thr.Conc.+Lys_conc.+yield+PO4.apporte+ PO4.utilise; 0.379, 0.689, tmp+Main.P-Source.Conc.+P-Source.Feed.conc.+Main.Thr.Conc.+Lys_conc.+PL+His+ SO4.ferm.+PO4.ferm.+PO4.utilise; 0.411, 0.689, tmp+ Main.P-Source.Conc.+Main.Thr.Conc.+Lys_conc.+yield+ SO4.ferm.+PO4.apporte; 0.401, 0.689, tmp+Main.P-Source.Conc.+P-Source.Feed.conc.+Main.Thr.Conc.+ Nitrogen.Conc.+Lys_conc.+PO4.apporte+PO4.utilise; 0.390, 0.689, pH+tmp+P-Source.Feed.conc.+Main.Thr. Conc.+Nitrogen.Conc.+Lys_conc.+PL+His+PO4.apporte; 0.401, 0.689, pH+tmp+Main.P-Source.Conc.+P-Source. Feed.conc.+Main.Thr.Conc.+OD+Lys_conc.+PO4.apporte; 0.401, 0.689, tmp+Main.P-Source.Conc.+P-Source.Feed. conc.+Main.Thr.Conc.+Lys_conc.+rab+SO4.ferm.+ PO4.apporte; 0.390, 0.689, tmp+Main.P-Source.Conc.+P-Source.Feed.conc.+Main.Thr.Conc.+Nitrogen.Conc.+Lys_conc.+lactate+SO4.ferm.+PO4.ferm.; 0.390, 0.689, pH+tmp+P-Source.Feed.conc.+Main.Thr.Conc.+ Nitrogen.Conc.+Lys_conc.+yield+PO4.apporte+ PO4.utilise; 0.400, 0.689, tmp+P-Source.Feed.conc.+ Main.Thr.Conc.+Lys_conc.+PL+rab+SO4.ferm.+ PO4.apporte; 0.400, 0.689, tmp+P-Source.Feed.conc.+ Main.Thr.Conc.+Nitrogen.Conc.+Lys_conc.+lactate+ PO4.ferm.+PO4.utilise; 0.379, 0.689, tmp+Main.P-Source.Conc.+P-Source.Feed.conc.+Main.Thr.Conc.+ Lys_conc.+PL+His+SO4.ferm.+PO4.ferm.+PO4.apporte; 0.379, 0.689, tmp+Main.P-Source.Conc.+P-Source.Feed. conc.+Main.Thr.Conc.+OD+Lys_conc.+SO4.ferm.+ PO4.ferm.+PO4.apporte+PO4.utilise; 0.400, 0.689, tmp+P-Source.Feed.conc.+Main.Thr.Conc.+Lys_conc.+emission_O2+lactate+SO4.ferm.+PO4.apporte; 0.411, 0.689, tmp+P-Source.Feed.conc.+Main.Thr.Conc.+Lys_conc.+ yield+PO4.ferm.+PO4.apporte; 0.400, 0.689, pH+tmp+P-Source.Feed.conc.+Main.Thr.Conc.+Lys_conc.+ PO4.ferm.+PO4.apporte+PO4.utilise; 0.367, 0.689, pH+tmp+Main.P-Source.Conc.+P-Source.Feed.conc.+ Main.Thr.Conc.+Nitrogen.Conc.+Lys_conc.+lactate+ PO4.ferm.+PO4.apporte+PO4.utilise; 0.400, 0.689, tmp+ Main.P-Source.Conc.+P-Source.Feed.conc.+ Main.Thr.Conc.+Lys_conc.+yield+lactate+PO4.apporte; 0.367, 0.689, pH+tmp+P-Source.Feed.conc.+Main.Thr. Conc.+OD+Lys_conc.+yield+SO4.ferm.+PO4.ferm.+ PO4.apporte+PO4.utilise; 0.378, 0.688, tmp+Main.P-Source.Conc.+P-Source.Feed.conc.+Main.Thr.Conc.+Lys_conc.+PL+His+SO4.ferm.+PO4.apporte+PO4.utilise; 0.378, 0.688, pH+tmp+Main.P-Source.Conc.+P-Source. Feed.conc.+Main.Thr.Conc.+Nitrogen.Conc.+Lys_conc.+ yield+lactate+PO4.apporte; 0.378, 0.688, pH+tmp+Main.P-Source.Conc.+P-Source.Feed.conc.+Main.Thr.Conc.+OD+ Lys_conc.+yield+SO4.ferm.+PO4.utilise; 0.355, 0.688, pH+tmp+Main.P-Source.Conc.+P-Source.Feed.conc.+ Main.Thr.Conc.+Nitrogen.Conc.+OD+Lys_conc.+yield+ PL+SO4.ferm.+PO4.apporte; 0.400, 0.688, tmp+Main.P-Source.Conc.+P-Source.Feed.conc.+Main.Thr.Conc.+ Nitrogen.Conc.+Lys_conc.+PO4.ferm.+PO4.apporte; 0.367, 0.688, tmp+P-Source.Feed.conc.+Main.Thr.Conc.+ Nitrogen.Conc.+OD+Lys_conc.+yield+SO4.ferm.+ PO4.ferm.+PO4.apporte+PO4.utilise; 0.367, 0.688, tmp+P-Source.Feed.conc.+Main.Thr.Conc.+Nitrogen.Conc.+OD+ Lys_conc.+yield+lactate+SO4.ferm.+PO4.ferm.+ PO4.utilise; 0.367, 0.688, tmp+P-Source.Feed.conc.+ Main.Thr.Conc.+Nitrogen.Conc.+OD+Lys_conc.+PL+His+ lactate+SO4.ferm.+PO4.apporte; 0.400, 0.688, tmp+P-Source.Feed.conc.+Main.Thr.Conc.+Lys_conc.+yield+PL+ lactate+PO4.apporte; 0.410, 0.688, tmp+Main.P-Source.Conc.+Main.Thr.Conc.+Lys_conc.+PL+SO4.ferm.+ PO4.apporte; 0.389, 0.688, pH+tmp+P-Source.Feed.conc.+ Main.Thr.Conc.+Nitrogen.Conc.+Lys_conc.+yield+ PO4.ferm.+PO4.apporte; 0.410, 0.688, pH+tmp+ Main.Thr.Conc.+Nitrogen.Conc.+Lys_conc.+SO4.ferm.+ PO4.apporte; 0.378, 0.688, tmp+Main.P-Source.Conc.+P-Source.Feed.conc.+Main.Thr.Conc.+Nitrogen.Conc.+ Lys_conc.+yield+PL+lactate+SO4.ferm.; 0.366, 0.688, tmp+Main.P-Source.Conc.+P-Source.Feed.conc.+Main. Thr.Conc.+Nitrogen.Conc.+Lys_conc.+His+SO4.ferm.+ PO4.ferm.+PO4.apporte+PO4.utilise; 0.378, 0.688, pH+tmp+Main.P-Source.Conc.+P-Source.Feed.conc.+ Main.Thr.Conc.+Nitrogen.Conc.+Lys_conc.+yield+ SO4.ferm.+PO4.ferm.; 0.389, 0.688, tmp+P-Source. Feed.conc.+Main.Thr.Conc.+Nitrogen.Conc.+OD+Lys_conc.+PL+SO4.ferm.+PO4.utilise; 0.389, 0.688, tmp+P-Source.Feed.conc.+Main.Thr.Conc.+Nitrogen.Conc.+Lys_conc.+yield+rab+SO4.ferm.+PO4.apporte; 0.389, 0.688, pH+tmp+P-Source.Feed.conc.+P-Source.Feed.conc.+ Main.Thr.Conc.+OD+Lys_conc.+yield+PO4.apporte; 0.378, 0.688, tmp+Main.P-Source.Conc.+P-Source.Feed. conc.+Main.Thr.Conc.+OD+Lys_conc.+PL+His+ SO4.ferm.+PO4.utilise; 0.378, 0.688, tmp+P-Source. Feed.conc.+Main.Thr.Conc.+Nitrogen.Conc.+OD+Lys_conc.+yield+PL+SO4.ferm.+PO4.utilise; 0.378, 0.688, tmp+Main.P-Source.Conc.+P-Source.Feed.conc.+Main. Thr.Conc.+OD+Lys_conc.+yield+His+SO4.ferm.+ PO4.apporte; 0.354, 0.688, pH+tmp+Main.P-Source.Conc.+ P-Source.Feed.conc.+Main.Thr.Conc.+Nitrogen.Conc.+Lys_conc.+PL+lactate+SO4.ferm.+PO4.ferm.+PO4.utilise; 0.378, 0.688, pH+tmp+Main.P-Source.Conc.+P-Source. Feed.conc.+Main.Thr.Conc.+Nitrogen.Conc.+Lys_conc.+ lactate+SO4.ferm.+PO4.ferm.; 0.399, 0.688, pH+tmp+P-Source.Feed.conc.+Main.Thr.Conc.+Lys_conc.+PL+lactate+PO4.apporte; 0.366, 0.688, pH+tmp+P-Source.Feed.conc.+Main.Thr.Conc.+Nitrogen.Conc.+OD+ Lys_conc.+PL+His+SO4.ferm.+PO4.utilise; 0.399, 0.688, pH+tmp+Main.P-Source.Conc.+P-Source.Feed.conc.+ Main.Thr.Conc.+Lys_conc.+lactate+PO4.apporte; 0.366, 0.688, pH+tmp+P-Source.Feed.conc.+Main.Thr.Conc.+Nitrogen.Conc.+Lys_conc.+His+lactate+SO4.ferm.+ PO4.ferm.+PO4.utilise; 0.366, 0.688, pH+tmp+Main.P-Source.Conc.+P-Source.Feed.conc.+Main.Thr.Conc.+ Lys_conc.+PL+lactate+SO4.ferm.+PO4.apporte+ PO4.utilise; 0.389, 0.688, pH+tmp+Main.P-Source.Conc.+ P-Source.Feed.conc.+Main.Thr.Conc.+OD+Lys_conc.+ SO4.ferm.+PO4.utilise; 0.366, 0.688, pH+tmp+Main.P-Source.Conc.+P-Source.Feed.conc.+Main.Thr.Conc.+ Lys_conc.+PL+lactate+SO4.ferm.+PO4.ferm.+ PO4.apporte; 0.366, 0.688, pH+tmp+P-Source.Feed.conc.+ Main.Thr.Conc.+Nitrogen.Conc.+OD+Lys_conc.+PL+ SO4.ferm.+PO4.apporte+PO4.utilise; 0.410, 0.688, pH+tmp+Main.P-Source.Conc.+Main.Thr.Conc.+Lys_conc.+SO4.ferm.+PO4.apporte; 0.439, 0.688, tmp+ Main.Thr.Conc.+Lys_conc.+PO4.apporte; 0.366, 0.688, pH+tmp+P-Source.Feed.conc.+Main.Thr.Conc.+Nitrogen. Conc.+Lys_conc.+yield+His+lactate+SO4.ferm.+

PO4.apporte; 0.366, 0.688, pH+tmp+P-Source.Feed.conc.+Main.Thr.Conc.+Nitrogen.Conc.+Lys_conc.+His+lactate+SO4.ferm.+PO4.ferm.+PO4.apporte; 0.354, 0.688, tmp+Main.P-Source.Conc.+P-Source.Feed.conc.+Main.Thr.Conc.+Nitrogen.Conc.+OD+Lys_conc.+lactate+SO4.ferm.+PO4.ferm.+PO4.apporte+PO4.utilise; 0.399, 0.688, tmp+P-Source.Feed.conc.+Main.Thr.Conc.+Lys_conc.+yield+PL+SO4.ferm.+PO4.utilise; 0.366, 0.688, pH+tmp+P-Source.Feed.conc.+Main.Thr.Conc.+Nitrogen.Conc.+Lys_conc.+His+lactate+SO4.ferm.+PO4.apporte+PO4.utilise; 0.388, 0.688, pH+tmp+P-Source.Feed.conc.+Main.Thr.Conc.+Nitrogen.Conc.+Lys_conc.+lactate+PO4.ferm.+PO4.utilise; 0.388, 0.688, tmp+P-Source.Feed.conc.+Main.Thr.Conc.+Nitrogen.Conc.+Lys_conc.+PL+emission_O2+SO4.ferm.+PO4.apporte; 0.377, 0.688, pH+tmp+P-Source.Feed.conc.+Main.Thr.Conc.+Nitrogen.Conc.+OD+Lys_conc.+lactate+SO4.ferm.+PO4.utilise; 0.429, 0.688, tmp+Main.Thr.Conc.+Nitrogen.Conc.+Lys_conc.+PO4.apporte; 0.388, 0.688, tmp+Main.P-Source.Conc.+P-Source.Feed.conc.+Main.Thr.Conc.+OD+Lys_conc.+lactate+SO4.ferm.+PO4.utilise; 0.366, 0.688, pH+tmp+P-Source.Feed.conc.+Main.Thr.Conc.+Nitrogen.Conc.+Lys_conc.+yield+PL+His+SO4.ferm.+PO4.apporte; 0.366, 0.688, tmp+Main.P-Source.Conc.+P-Source.Feed.conc.+Main.Thr.Conc.+Nitrogen.Conc.+OD+Lys_conc.+yield+His+SO4.ferm.+PO4.apporte; 0.377, 0.688, tmp+Main.P-Source.Conc.+P-Source.Feed.conc.+Main.Thr.Conc.+Nitrogen.Conc.+Lys_conc.+yield+PL+SO4.ferm.+PO4.utilise; 0.377, 0.688, tmp+P-Source.Feed.conc.+Main.Thr.Conc.+Nitrogen.Conc.+Lys_conc.+yield+His+SO4.ferm.+PO4.ferm.+PO4.apporte; 0.366, 0.688, pH+tmp+P-Source.Feed.conc.+Main.Thr.Conc.+OD+Lys_conc.+PL+His+lactate+SO4.ferm.+PO4.apporte; 0.409, 0.688, tmp+Main.Thr.Conc.+Nitrogen.Conc.+Lys_conc.+yield+SO4.ferm.+PO4.apporte; 0.399, 0.688, tmp+Main.P-Source.Conc.+P-Source.Feed.conc.+Main.Thr.Conc.+OD+Lys_conc.+yield+SO4.ferm.; 0.377, 0.688, tmp+Main.P-Source.Conc.+P-Source.Feed.conc.+Main.Thr.Conc.+Nitrogen.Conc.+Lys_conc.+His+lactate+SO4.ferm.+PO4.utilise; 0.399, 0.688, pH+tmp+P-Source.Feed.conc.+Main.Thr.Conc.+OD+Lys_conc.+yield+PO4.utilise; 0.377, 0.688, pH+tmp+Main.P-Source.Conc.+P-Source.Feed.conc.+Main.Thr.Conc.+Nitrogen.Conc.+OD+Lys_conc.+His+SO4.ferm.; 0.388, 0.688, tmp+P-Source.Feed.conc.+Main.Thr.Conc.+Nitrogen.Conc.+Lys_conc.+yield+emission_O2+SO4.ferm.+PO4.apporte; 0.377, 0.688, tmp+P-Source.Feed.conc.+Main.Thr.Conc.+Nitrogen.Conc.+Lys_conc.+yield+His+SO4.ferm.+PO4.apporte+PO4.utilise; 0.409, 0.688, tmp+P-Source.Feed.conc.+Main.Thr.Conc.+OD+Lys_conc.+PL+PO4.apporte; 0.388, 0.688, pH+tmp+P-Source.Feed.conc.+Main.Thr.Conc.+Nitrogen.Conc.+Lys_conc.+His+SO4.ferm.+PO4.utilise; 0.341, 0.688, pH+tmp+Main.P-Source.Conc.+P-Source.Feed.conc.+Main.Thr.Conc.+Nitrogen.Conc.+Lys_conc.+yield+lactate+SO4.ferm.+PO4.ferm.+PO4.apporte+PO4.utilise; 0.388, 0.688, pH+tmp+P-Source.Feed.conc.+Main.Thr.Conc.+Lys_conc.+yield+lactate+SO4.ferm.+PO4.utilise; 0.365, 0.688, pH+tmp+P-Source.Feed.conc.+Main.Thr.Conc.+Nitrogen.Conc.+OD+Lys_conc.+His+lactate+SO4.ferm.+PO4.utilise; 0.365, 0.688, tmp+P-Source.Feed.conc.+Main.Thr.Conc.+Nitrogen.Conc.+OD+Lys_conc.+PL+SO4.ferm.+PO4.ferm.+PO4.apporte+PO4.utilise; 0.365, 0.688, pH+tmp+P-Source.Feed.conc.+Main.Thr.Conc.+Nitrogen.Conc.+OD+Lys_conc.+PL+SO4.ferm.+PO4.ferm.+PO4.apporte; 0.377, 0.688, tmp+Main.P-Source.Conc.+P-Source.Feed.conc.+Main.Thr.Conc.+Nitrogen.Conc.+OD+Lys_conc.+lactate+SO4.ferm.+PO4.utilise; 0.388, 0.688, tmp+Main.P-Source.Conc.+P-Source.Feed.conc.+Main.Thr.Conc.+Nitrogen.Conc.+OD+Lys_conc.+yield+PO4.apporte; 0.365, 0.688, pH+tmp+Main.P-Source.Conc.+P-Source.Feed.conc.+Main.Thr.Conc.+Lys_conc.+PL+lactate+SO4.ferm.+PO4.ferm.+PO4.utilise; 0.419, 0.688, tmp+Main.Thr.Conc.+Lys_conc.+SO4.ferm.+PO4.ferm.+PO4.utilise; 0.353, 0.688, tmp+Main.P-Source.Conc.+P-Source.Feed.conc.+Main.Thr.Conc.+Nitrogen.Conc.+OD+Lys_conc.+yield+PL+lactate+SO4.ferm.+PO4.apporte; 0.353, 0.687, pH+tmp+P-Source.Feed.conc.+Main.Thr.Conc.+Nitrogen.Conc.+Lys_conc.+PL+lactate+SO4.ferm.+PO4.ferm.+PO4.apporte+PO4.utilise; 0.388, 0.687, tmp+P-Source.Feed.conc.+Main.Thr.Conc.+Nitrogen.Conc.+Lys_conc.+PL+lactate+SO4.ferm.+PO4.utilise; 0.388, 0.687, tmp+P-Source.Feed.conc.+Main.Thr.Conc.+Lys_conc.+yield+His+lactate+SO4.ferm.+PO4.apporte; 0.377, 0.687, tmp+Main.P-Source.Conc.+P-Source.Feed.conc.+Main.Thr.Conc.+Lys_conc.+PL+His+lactate+SO4.ferm.+PO4.apporte; 0.377, 0.687, tmp+P-Source.Feed.conc.+Main.Thr.Conc.+Nitrogen.Conc.+Lys_conc.+yield+His+SO4.ferm.+PO4.ferm.+PO4.utilise; 0.388, 0.687, pH+tmp+Main.P-Source.Conc.+P-Source.Feed.conc.+Main.Thr.Conc.+Nitrogen.Conc.+Lys_conc.+PO4.apporte+PO4.utilise; 0.409, 0.687, tmp+Main.P-Source.Conc.+P-Source.Feed.conc.+Main.Thr.Conc.+Lys_conc.+PL+PO4.apporte; 0.399, 0.687, tmp+P-Source.Feed.conc.+Main.Thr.Conc.+Lys_conc.+PL+emission_O2+SO4.ferm.+PO4.apporte; 0.377, 0.687, pH+tmp+P-Source.Feed.conc.+Main.Thr.Conc.+Lys_conc.+His+lactate+SO4.ferm.+PO4.ferm.+PO4.utilise; 0.388, 0.687, pH+tmp+P-Source.Feed.conc.+Main.Thr.Conc.+OD+Lys_conc.+yield+PL+PO4.apporte; 0.365, 0.687, pH+tmp+P-Source.Feed.conc.+Main.Thr.Conc.+OD+Lys_conc.+His+SO4.ferm.+PO4.ferm.+PO4.apporte+PO4.utilise; 0.419, 0.687, tmp+P-Source.Feed.conc.+Main.Thr.Conc.+Lys_conc.+PO4.ferm.+PO4.utilise; 0.409, 0.687, pH+tmp+P-Source.Feed.conc.+Main.Thr.Conc.+Lys_conc.+PO4.ferm.+PO4.utilise; 0.409, 0.687, tmp+P-Source.Feed.conc.+Main.Thr.Conc.+Lys_conc.+yield+PO4.ferm.+PO4.utilise; 0.377, 0.687, tmp+Main.P-Source.Conc.+P-Source.Feed.conc.+Main.Thr.Conc.+Nitrogen.Conc.+OD+Lys_conc.+yield+SO4.ferm.+PO4.utilise; 0.409, 0.687, tmp+Main.P-Source.Conc.+Main.Thr.Conc.+Nitrogen.Conc.+Lys_conc.+SO4.ferm.+PO4.apporte; 0.388, 0.687, tmp+P-Source.Feed.conc.+Main.Thr.Conc.+Nitrogen.Conc.+Lys_conc.+rab+SO4.ferm.+PO4.ferm.+PO4.apporte; 0.365, 0.687, tmp+P-Source.Feed.conc.+Main.Thr.Conc.+OD+Lys_conc.+yield+lactate+SO4.ferm.+PO4.ferm.+PO4.apporte+PO4.utilise; 0.376, 0.687, pH+tmp+P-Source.Feed.conc.+Main.Thr.Conc.+Nitrogen.Conc.+Lys_conc.+yield+PO4.ferm.+PO4.apporte+PO4.utilise; 0.388, 0.687, tmp+Main.P-Source.Conc.+P-Source.Feed.conc.+Main.Thr.Conc.+Nitrogen.Conc.+Lys_conc.+yield+PL+PO4.apporte; 0.398, 0.687, pH+tmp+P-Source.Feed.conc.+Main.Thr.Conc.+OD+Lys_conc.+PL+PO4.apporte; 0.365, 0.687, pH+tmp+P-Source.Feed.conc.+Main.Thr.Conc.+Lys_conc.+yield+PL+SO4.ferm.+PO4.ferm.+PO4.apporte+PO4.utilise; 0.365, 0.687, tmp+P-Source.Feed.conc.+Main.Thr.Conc.+Nitrogen.Conc.+OD+Lys_conc.+yield+PL+His+SO4.ferm.+PO4.apporte; 0.387, 0.687, tmp+Main.P-Source.Conc.+P-Source.Feed.conc.+Main.Thr.Conc.+Nitrogen.Conc.+OD+Lys_conc.+His+SO4.ferm.; 0.387, 0.687, tmp+P-Source.Feed.conc.+Main.Thr.Conc.+Nitrogen.Conc.+Lys_conc.+yield+lactate+PO4.apporte+

PO4.utilise; 0.376, 0.687, tmp+Main.P-Source.Conc.+P-Source.Feed.conc.+Main.Thr.Conc.+OD+Lys_conc.+yield+lactate+SO4.ferm.+PO4.utilise; 0.387, 0.687, tmp+P-Source.Feed.conc.+Main.Thr.Conc.+Nitrogen.Conc.+Lys_conc.+rab+SO4.ferm.+PO4.apporte+PO4.utilise; 0.376, 0.687, pH+tmp+Main.P-Source.Conc.+P-Source.Feed.conc.+Main.Thr.Conc.+Nitrogen.Conc.+Lys_conc.+emission_O2+SO4.ferm.+PO4.apporte; 0.376, 0.687, pH+tmp+P-Source.Feed.conc.+Main.Thr.Conc.+Nitrogen.Conc.+Lys_conc.+emission_O2+rab+SO4.ferm.+PO4.apporte; 0.376, 0.687, tmp+P-Source.Feed.conc.+Main.Thr.Conc.+Lys_conc.+PL+His+SO4.ferm.+PO4.ferm.+PO4.apporte+PO4.utilise; 0.376, 0.687, tmp+Main.P-Source.Conc.+P-Source.Feed.conc.+Main.Thr.Conc.+OD+Lys_conc.+His+lactate+SO4.ferm.+PO4.apporte; 0.376, 0.687, tmp+P-Source.Feed.conc.+Main.Thr.Conc.+OD+Lys_conc.+yield+His+lactate+SO4.ferm.+PO4.utilise; 0.365, 0.687, tmp+Main.P-Source.Conc.+P-Source.Feed.conc.+Main.Thr.Conc.+Lys_conc.+yield+PL+lactate+SO4.ferm.+PO4.apporte+PO4.utilise; 0.408, 0.687, tmp+Main.Thr.Conc.+Nitrogen.Conc.+Lys_conc.+PL+SO4.ferm.+PO4.apporte; 0.365, 0.687, tmp+Main.P-Source.Conc.+P-Source.Feed.conc.+Main.Thr.Conc.+Lys_conc.+yield+lactate+SO4.ferm.+PO4.ferm.+PO4.apporte+PO4.utilise; 0.365, 0.687, tmp+Main.P-Source.Conc.+P-Source.Feed.conc.+Main.Thr.Conc.+Lys_conc.+yield+PL+lactate+SO4.ferm.+PO4.ferm.+PO4.apporte; 0.365, 0.687, pH+tmp+P-Source.Feed.conc.+Main.Thr.Conc.+OD+Lys_conc.+PL+lactate+SO4.ferm.+PO4.apporte+PO4.utilise; 0.353, 0.687, tmp+Main.P-Source.Conc.+P-Source.Feed.conc.+Main.Thr.Conc.+Nitrogen.Conc.+Lys_conc.+yield+PL+lactate+SO4.ferm.+PO4.ferm.+PO4.apporte; 0.418, 0.687, tmp+Main.Thr.Conc.+Lys_conc.+SO4.ferm.+PO4.apporte+PO4.utilise; 0.387, 0.687, pH+tmp+Main.P-Source.Conc.+P-Source.Feed.conc.+Main.Thr.Conc.+Nitrogen.Conc.+Lys_conc.+PO4.ferm.+PO4.apporte; 0.352, 0.687, tmp+Main.P-Source.Conc.+P-Source.Feed.conc.+Main.Thr.Conc.+Nitrogen.Conc.+Lys_conc.+yield+PL+lactate+SO4.ferm.+PO4.apporte+PO4.utilise; 0.364, 0.687, pH+tmp+P-Source.Feed.conc.+Main.Thr.Conc.+OD+Lys_conc.+PL+His+SO4.ferm.+PO4.apporte+PO4.utilise; 0.408, 0.687, tmp+Main.Thr.Conc.+Nitrogen.Conc.+Lys_conc.+lactate+SO4.ferm.+PO4.apporte; 0.408, 0.687, tmp+Main.Thr.Conc.+Lys_conc.+PL+lactate+SO4.ferm.+PO4.apporte; 0.418, 0.687, tmp+Main.Thr.Conc.+Lys_conc.+SO4.ferm.+PO4.ferm.+PO4.apporte; 0.364, 0.687, pH+tmp+P-Source.Feed.conc.+Main.Thr.Conc.+OD+Lys_conc.+PL+His+SO4.ferm.+PO4.ferm.+PO4.apporte; 0.376, 0.687, pH+tmp+P-Source.Feed.conc.+Main.Thr.Conc.+Nitrogen.Conc.+OD+Lys_conc.+PO4.ferm.+PO4.apporte+PO4.utilise; 0.408, 0.687, tmp+Main.P-Source.Conc.+P-Source.Feed.conc.+Main.Thr.Conc.+Lys_conc.+yield+SO4.ferm.; 0.376, 0.687, pH+tmp+Main.P-Source.Conc.+P-Source.Feed.conc.+Main.Thr.Conc.+Nitrogen.Conc.+Lys_conc.+PL+His+SO4.ferm.; 0.364, 0.687, pH+tmp+P-Source.Feed.conc.+Main.Thr.Conc.+OD+Lys_conc.+PL+His+SO4.ferm.+PO4.ferm.+PO4.utilise; 0.364, 0.687, tmp+Main.P-Source.Conc.+P-Source.Feed.conc.+Main.Thr.Conc.+Lys_conc.+yield+PL+lactate+SO4.ferm.+PO4.ferm.+PO4.utilise; 0.398, 0.687, tmp+P-Source.Feed.conc.+Main.Thr.Conc.+Lys_conc.+yield+rab+SO4.ferm.+PO4.apporte; 0.376, 0.687, pH+tmp+P-Source.Feed.conc.+Main.Thr.Conc.+OD+Lys_conc.+PL+lactate+SO4.ferm.+PO4.utilise; 0.398, 0.687, tmp+P-Source.Feed.conc.+Main.Thr.Conc.+Lys_conc.+lactate+PO4.ferm.+PO4.apporte+PO4.utilise; 0.364, 0.687, pH+tmp+P-Source.Feed.conc.+Main.Thr.Conc.+Nitrogen.Conc.+OD+Lys_conc.+PL+SO4.ferm.+PO4.ferm.+PO4.utilise; 0.387, 0.687, tmp+P-Source.Feed.conc.+Main.Thr.Conc.+Nitrogen.Conc.+Lys_conc.+yield+lactate+PO4.ferm.+PO4.apporte; 0.398, 0.687, tmp+Main.P-Source.Conc.+P-Source.Feed.conc.+Main.Thr.Conc.+Lys_conc.+emission_O2+SO4.ferm.+PO4.apporte; 0.387, 0.687, tmp+P-Source.Feed.conc.+Main.Thr.Conc.+Nitrogen.Conc.+OD+Lys_conc.+yield+PL+PO4.apporte; 0.398, 0.687, tmp+P-Source.Feed.conc.+Main.Thr.Conc.+Nitrogen.Conc.+Lys_conc.+His+lactate+PO4.apporte; 0.398, 0.687, tmp+P-Source.Feed.conc.+Main.Thr.Conc.+Lys_conc.+yield+emission_O2+SO4.ferm.+PO4.apporte; 0.376, 0.687, tmp+P-Source.Feed.conc.+Main.Thr.Conc.+Nitrogen.Conc.+Lys_conc.+yield+lactate+PO4.ferm.+PO4.apporte+PO4.utilise; 0.352, 0.687, pH+tmp+Main.P-Source.Conc.+P-Source.Feed.conc.+Main.Thr.Conc.+Nitrogen.Conc.+Lys_conc.+PL+His+lactate+SO4.ferm.+PO4.apporte; 0.376, 0.687, pH+tmp+P-Source.Feed.conc.+Main.Thr.Conc.+Lys_conc.+His+lactate+SO4.ferm.+PO4.apporte+PO4.utilise; 0.352, 0.687, pH+tmp+Main.P-Source.Conc.+P-Source.Feed.conc.+Main.Thr.Conc.+Nitrogen.Conc.+OD+Lys_conc.+lactate+SO4.ferm.+PO4.apporte+PO4.utilise; 0.364, 0.687, tmp+P-Source.Feed.conc.+Main.Thr.Conc.+Nitrogen.Conc.+OD+Lys_conc.+PL+lactate+SO4.ferm.+PO4.apporte+PO4.utilise; 0.387, 0.687, tmp+Main.P-Source.Conc.+P-Source.Feed.conc.+Main.Thr.Conc.+Nitrogen.Conc.+OD+Lys_conc.+PL+SO4.ferm.; 0.398, 0.687, pH+tmp+P-Source.Feed.conc.+Main.Thr.Conc.+OD+Lys_conc.+Thr+PO4.apporte; 0.364, 0.687, pH+tmp+P-Source.Feed.conc.+Main.Thr.Conc.+OD+Lys_conc.+PL+lactate+SO4.ferm.+PO4.ferm.+PO4.apporte; 0.387, 0.687, pH+tmp+P-Source.Feed.conc.+Main.Thr.Conc.+Nitrogen.Conc.+Lys_conc.+yield+PO4.ferm.+PO4.utilise; 0.364, 0.687, tmp+Main.P-Source.Conc.+P-Source.Feed.conc.+Main.Thr.Conc.+Nitrogen.Conc.+Lys_conc.+yield+PL+His+SO4.ferm.+PO4.apporte; 0.352, 0.687, pH+tmp+Main.P-Source.Conc.+P-Source.Feed.conc.+Main.Thr.Conc.+Ni-trogen.Conc.+OD+Lys_conc.+lactate+SO4.ferm.+PO4.ferm.+PO4.apporte; 0.376, 0.687, pH+tmp+P-Source.Feed.conc.+Main.Thr.Conc.+Nitrogen.Conc.+Lys_conc.+yield+PL+lactate+PO4.apporte; 0.397, 0.687, tmp+P-Source.Feed.conc.+Main.Thr.Conc.+Nitrogen.Conc.+Lys_conc.+PL+PO4.apporte+PO4.utilise; 0.418, 0.687, tmp+Main.Thr.Conc.+Lys_conc.+His+SO4.ferm.+PO4.apporte; 0.408, 0.687, tmp+Main.Thr.Conc.+Nitrogen.Conc.+OD+Lys_conc.+SO4.ferm.+PO4.apporte; 0.376, 0.687, pH+tmp+P-Source.Feed.conc.+Main.Thr.Conc.+Lys_conc.+His+lactate+SO4.ferm.+PO4.ferm.+PO4.apporte; 0.387, 0.687, pH+tmp+Main.P-Source.Conc.+P-Source.Feed.conc.+Main.Thr.Conc.+Lys_conc.+yield+SO4.ferm.+PO4.utilise; 0.387, 0.687, tmp+P-Source.Feed.conc.+Main.Thr.Conc.+Nitrogen.Conc.+OD+Lys_conc.+rab+SO4.ferm.+PO4.apporte; 0.387, 0.687, tmp+P-Source.Feed.conc.+Main.Thr.Conc.+Nitrogen.Conc.+Lys_conc.+yield+PL+SO4.ferm.+PO4.utilise; 0.352, 0.687, pH+tmp+Main.P-Source.Conc.+P-Source.Feed.conc.+Main.Thr.Conc.+Nitrogen.Conc.+Lys_conc.+yield+PL+SO4.ferm.+PO4.ferm.+PO4.apporte; 0.352, 0.687, pH+tmp+Main.P-Source.Conc.+P-Source.Feed.conc.+Main.Thr.Conc.+Ni-trogen.Conc.+Lys_conc.+yield+PL+SO4.ferm.+PO4.apporte+PO4.utilise; 0.408, 0.687, tmp+P-Source.Feed.conc.+Main.Thr.Conc.+Lys_conc.+lactate+PO4.apporte+PO4.utilise; 0.375, 0.687, tmp+Main.P-Source.Conc.+P-Source.Feed.conc.+Main.Thr.Conc.+Nitrogen.Conc.+OD+Lys_conc.+yield+lactate+SO4.ferm.;

0.364, 0.687, pH+tmp+P-Source.Feed.conc.+Main.Thr.Conc.+Nitrogen.Conc.+OD+Lys_conc.+yield+lactate+SO4.ferm.+PO4.utilise; 0.364, 0.687, pH+tmp+Main.P-Source.Conc.+P-Source.Feed.conc.+Main.Thr.Conc.+OD+Lys_conc.+His+SO4.ferm.+PO4.ferm.+PO4.apporte; 0.352, 0.687, pH+tmp+P-Source.Feed.conc.+Main.Thr.Conc.+Nitrogen.Conc.+OD+Lys_conc.+lactate+SO4.ferm.+PO4.ferm.+PO4.apporte+PO4.utilise; 0.364, 0.687, tmp+Main.P-Source.Conc.+P-Source.Feed.conc.+Main.Thr.Conc.+Nitrogen.Conc.+OD+Lys_conc.+yield+SO4.ferm.+PO4.ferm.+PO4.apporte; 0.352, 0.687, pH+tmp+P-Source.Feed.conc.+Main.Thr.Conc.+Nitrogen.Conc.+Lys_conc.+yield+PL+lactate+SO4.ferm.+PO4.apporte+PO4.utilise; 0.364, 0.687, pH+tmp+Main.P-Source.Conc.+P-Source.Feed.conc.+Main.Thr.Conc.+OD+Lys_conc.+lactate+SO4.ferm.+PO4.apporte+PO4.utilise; 0.386, 0.687, tmp+Main.P-Source.Conc.+P-Source.Feed.conc.+Main.Thr.Conc.+Nitrogen.Conc.+Lys_conc.+PL+lactate+PO4.apporte; 0.364, 0.687, tmp+Main.P-Source.Conc.+P-Source.Feed.conc.+Main.Thr.Conc.+Nitrogen.Conc.+OD+Lys_conc.+His+lactate+SO4.ferm.+PO4.apporte; 0.364, 0.686, tmp+P-Source.Feed.conc.+Main.Thr.Conc.+Nitrogen.Conc.+OD+Lys_conc.+PL+lactate+SO4.ferm.+PO4.ferm.+PO4.apporte; 0.352, 0.686, pH+tmp+P-Source.Feed.conc.+Main.Thr.Conc.+Nitrogen.Conc.+Lys_conc.+yield+PL+lactate+SO4.ferm.+PO4.ferm.+PO4.apporte; 0.364, 0.686, tmp+Main.P-Source.Conc.+P-Source.Feed.conc.+Main.Thr.Conc.+Nitrogen.Conc.+OD+Lys_conc.+yield+SO4.ferm.+PO4.apporte+PO4.utilise; 0.363, 0.686, pH+tmp+Main.P-Source.Conc.+P-Source.Feed.conc.+Main.Thr.Conc.+OD+Lys_conc.+His+SO4.ferm.+PO4.apporte+PO4.utilise; 0.407, 0.686, tmp+P-Source.Feed.conc.+Main.Thr.Conc.+OD+Lys_conc.+yield+SO4.ferm.; 0.363, 0.686, pH+tmp+Main.P-Source.Conc.+P-Source.Feed.conc.+Main.Thr.Conc.+OD+Lys_conc.+lactate+SO4.ferm.+PO4.ferm.+PO4.apporte; 0.363, 0.686, pH+tmp+P-Source.Feed.conc.+Main.Thr.Conc.+OD+Lys_conc.+yield+PL+lactate+SO4.ferm.+PO4.utilise; 0.407, 0.686, tmp+Main.P-Source.Conc.+Main.Thr.Conc.+OD+Lys_conc.+SO4.ferm.+PO4.apporte; 0.397, 0.686, tmp+P-Source.Feed.conc.+Main.Thr.Conc.+Lys_conc.+rab+SO4.ferm.+PO4.ferm.+PO4.apporte; 0.363, 0.686, tmp+Main.P-Source.Conc.+P-Source.Feed.conc.+Main.Thr.Conc.+Lys_conc.+PL+lactate+SO4.ferm.+PO4.ferm.+PO4.apporte+PO4.utilise; 0.407, 0.686, tmp+P-Source.Feed.conc.+Main.Thr.Conc.+Lys_conc.+lactate+PO4.ferm.+PO4.apporte; 0.363, 0.686, pH+tmp+P-Source.Feed.conc.+Main.Thr.Conc.+OD+Lys_conc.+PL+lactate+SO4.ferm.+PO4.ferm.+PO4.utilise; 0.363, 0.686, pH+tmp+Main.P-Source.Conc.+P-Source.Feed.conc.+Main.Thr.Conc.+OD+Lys_conc.+His+SO4.ferm.+PO4.ferm.+PO4.utilise; 0.375, 0.686, tmp+Main.P-Source.Conc.+P-Source.Feed.conc.+Main.Thr.Conc.+OD+Lys_conc.+PL+SO4.ferm.+PO4.apporte+PO4.utilise; 0.351, 0.686, tmp+Main.P-Source.Conc.+P-Source.Feed.conc.+Main.Thr.Conc.+Nitrogen.Conc.+Lys_conc.+yield+PL+lactate+SO4.ferm.+PO4.ferm.+PO4.utilise; 0.397, 0.686, tmp+P-Source.Feed.conc.+Main.Thr.Conc.+Nitrogen.Conc.+Lys_conc.+PL+PO4.ferm.+PO4.apporte; 0.397, 0.686, tmp+Main.P-Source.Conc.+P-Source.Feed.conc.+Main.Thr.Conc.+Lys_conc.+PL+SO4.ferm.+PO4.utilise; 0.407, 0.686, tmp+Main.Thr.Conc.+Lys_conc.+yield+PL+SO4.ferm.+PO4.apporte

[14. Linear Model that Predicts Lysine Production Amount in Interval 4]

0.343, 0.643, Main.P-Source.Conc.+P-Source.Feed.conc.+X.F.Suc+PL+rab+SO4.ferm.+PO4.utilise; 0.329, 0.642, pH+Main.P-Source.Conc.+P-Source.Feed.conc.+X.F.Suc+PL+rab+SO4.ferm.+PO4.utilise; 0.340, 0.641, Main.P-Source.Conc.+P-Source.Feed.conc.+X.F.Suc+PL+emission_O2+SO4.ferm.+PO4.utilise; 0.326, 0.639, Main.P-Source.Conc.+P-Source.Feed.conc.+X.F.Suc+PL+rab+Thr+SO4.ferm.+PO4.utilise; 0.325, 0.639, pH+Main.P-Source.Conc.+P-Source.Feed.conc.+X.F.Suc+PL+emission_O2+SO4.ferm.+PO4.utilise; 0.311, 0.637, pH+Main.P-Source.Conc.+P-Source.Feed.conc.+X.F.Suc+PL+rab+Thr+SO4.ferm.+PO4.utilise; 0.321, 0.636, Main.P-Source.Conc.+P-Source.Feed.conc.+X.F.Suc+PL+emission_O2+Thr+SO4.ferm.+PO4.utilise; 0.320, 0.635, Main.P-Source.Conc.+P-Source.Feed.conc.+X.F.Suc+PL+rab+His+SO4.ferm.+PO4.utilise; 0.307, 0.634, pH+Main.P-Source.Conc.+P-Source.Feed.conc.+X.F.Suc+X.VXdt+PL+rab+SO4.ferm.+PO4.utilise; 0.341, 0.634, Main.P-Source.Conc.+P-Source.Feed.conc.+X.F.Suc+rab+SO4.ferm.+PO4.utilise; 0.318, 0.634, Main.P-Source.Conc.+P-Source.Feed.conc.+X.F.Suc+X.VXdt+PL+rab+SO4.ferm.+PO4.utilise; 0.305, 0.634, pH+Main.P-Source.Conc.+P-Source.Feed.conc.+X.F.Suc+PL+rab+His+SO4.ferm.+PO4.utilise; 0.305, 0.633, pH+Main.P-Source.Conc.+P-Source.Feed.conc.+X.F.Suc+PL+emission_O2+Thr+SO4.ferm.+PO4.utilise; 0.317, 0.633, Main.P-Source.Conc.+P-Source.Feed.conc.+X.F.Suc+PL+emission_O2+His+SO4.ferm.+PO4.utilise; 0.317, 0.633, tmp+Main.P-Source.Conc.+P-Source.Feed.conc.+X.F.Suc+PL+rab+SO4.ferm.+PO4.utilise; 0.316, 0.632, Main.P-Source.Conc.+P-Source.Feed.conc.+X.F.Suc+total.Vol+PL+rab+SO4.ferm.+PO4.utilise; 0.339, 0.632, Main.P-Source.Conc.+P-Source.Feed.conc.+X.F.Suc+emission_O2+SO4.ferm.+PO4.utilise; 0.315, 0.632, Main.P-Source.Conc.+P-Source.Feed.conc.+X.F.Suc+PL+rab+SO4.ferm.+PO4.ferm.+PO4.utilise; 0.302, 0.632, Main.P-Source.Conc.+P-Source.Feed.conc.+X.F.Suc+PL+rab+Thr+His+SO4.ferm.+PO4.utilise; 0.302, 0.632, tmp+Main.P-Source.Conc.+P-Source.Feed.conc.+X.F.Suc+PL+rab+Thr+SO4.ferm.+PO4.utilise; 0.302, 0.631, pH+Main.P-Source.Conc.+P-Source.Feed.conc.+X.F.Suc+PL+emission_O2+His+SO4.ferm.+PO4.utilise; 0.302, 0.631, pH+Main.P-Source.Conc.+P-Source.Feed.conc.+X.F.Suc+PL+rab+SO4.ferm.+PO4.ferm.+PO4.utilise; 0.289, 0.631, pH+Main.P-Source.Conc.+P-Source.Feed.conc.+X.F.Suc+X.VXdt+total.Vol+PL+rab+SO4.ferm.+PO4.utilise; 0.301, 0.631, pH+tmp+Main.P-Source.Conc.+P-Source.Feed.conc.+X.F.Suc+PL+rab+SO4.ferm.+PO4.utilise; 0.301, 0.631, pH+Main.P-Source.Conc.+P-Source.Feed.conc.+X.F.Suc+total.Vol+PL+rab+SO4.ferm.+PO4.utilise; 0.325, 0.631, tmp+Main.P-Source.Conc.+P-Source.Feed.conc.+X.F.Suc+PL+SO4.ferm.+PO4.utilise; 0.313, 0.631, pH+tmp+Main.P-Source.Conc.+P-Source.Feed.conc.+X.F.Suc+PL+SO4.ferm.+PO4.utilise; 0.325, 0.631, Main.P-Source.Conc.+P-Source.Feed.conc.+X.F.Suc+rab+Thr+SO4.ferm.+PO4.utilise; 0.312, 0.630, tmp+Main.P-Source.Conc.+P-Source.Feed.conc.+X.F.Suc+PL+emission_O2+SO4.ferm.+PO4.utilise; 0.286, 0.629, pH+tmp+Main.P-Source.Conc.+P-Source.Feed.conc.+X.F.Suc+X.VXdt+PL+rab+SO4.ferm.+PO4.utilise; 0.311, 0.629, Main.P-Source.Conc.+P-Source.Feed.conc.+X.F.Suc+total.Vol+PL+emission_O2+SO4.ferm.+PO4.utilise; 0.299, 0.629, pH+Main.P-Source.Conc.+P-Source.Feed.conc.+X.F.Suc+X.VXdt+PL+emission_O2+SO4.ferm.+PO4.utilise; 0.311, 0.629, Main.P-Source.Conc.+P-Source.Feed.conc.+X.F.Suc+X.VXdt+PL+emission_O2+SO4.ferm.+PO4.utilise; 0.286, 0.629, pH+Main.P-Source.Conc.+P-Source.Feed.conc.+X.F.Suc+ PL+rab+Thr+His+SO4.ferm.+PO4.utilise; 0.285, 0.629, pH+tmp+Main.P-Source.Conc.+P-Source.Feed.conc.+ X.F.Suc+PL+rab+Thr+SO4.ferm.+PO4.utilise; 0.310, 0.629, Main.P-Source.Conc.+P-Source.Feed.conc.+ X.F.Suc+PL+emission_O2+SO4.ferm.+PO4.ferm.+ PO4.utilise; 0.310, 0.629, tmp+Main.P-Source.Conc.+P-Source.Feed.conc.+X.F.Suc+PL+Thr+SO4.ferm.+ PO4.utilise; 0.298, 0.629, tmp+Main.P-Source.Conc.+P-Source.Feed.conc.+X.F.Suc+X.VXdt+PL+rab+SO4.ferm.+ PO4.utilise; 0.298, 0.628, Main.P-Source.Conc.+P-Source.Feed.conc.+X.F.Suc+total.Vol+PL+rab+Thr+ SO4.ferm.+PO4.utilise; 0.297, 0.628, Main.P-Source.Conc.+P-Source.Feed.conc.+X.F.Suc+X.VXdt+ total.Vol+PL+rab+SO4.ferm.+PO4.utilise; 0.297, 0.628, tmp+Main.P-Source.Conc.+P-Source.Feed.conc.+X.F.Suc+ PL+emission_O2+Thr+SO4.ferm.+PO4.utilise; 0.297, 0.628, Main.P-Source.Conc.+P-Source.Feed.conc.+ X.F.Suc+PL+emission_O2+Thr+His+SO4.ferm.+ PO4.utilise; 0.297, 0.628, pH+tmp+Main.P-Source.Conc.+ P-Source.Feed.conc.+X.F.Suc+PL+emission_O2+ SO4.ferm.+PO4.utilise; 0.321, 0.628, Main.P-Source.Conc.+P-Source.Feed.conc.+X.F.Suc+rab+His+ SO4.ferm.+PO4.utilise; 0.297, 0.628, pH+Main.P-Source.Conc.+P-Source.Feed.conc.+X.F.Suc+total.Vol+ PL+emission_O2+SO4.ferm.+PO4.utilise; 0.321, 0.628, pH+Main.P-Source.Conc.+P-Source.Feed.conc.+X.F.Suc+ rab+SO4.ferm.+PO4.utilise; 0.320, 0.627, Main.P-Source.Conc.+P-Source.Feed.conc.+X.F.Suc+emission_O2+Thr+SO4.ferm.+PO4.utilise; 0.296, 0.627, pH+Main.P-Source.Conc.+P-Source.Feed.conc.+X.F.Suc+ PL+emission_O2+SO4.ferm.+PO4.ferm.+PO4.utilise; 0.296, 0.627, pH+tmp+Main.P-Source.Conc.+P-Source. Feed.conc.+X.F.Suc+PL+Thr+SO4.ferm.+PO4.utilise; 0.283, 0.627, pH+Main.P-Source.Conc.+P-Source.Feed. conc.+X.F.Suc+X.VXdt+total.Vol+PL+emission_O2+ SO4.ferm.+PO4.utilise; 0.282, 0.627, pH+Main.P-Source.Conc.+P-Source.Feed.conc.+X.F.Suc+X.VXdt+PL+ rab+His+SO4.ferm.+PO4.utilise; 0.295, 0.626, tmp+ Main.P-Source.Conc.+P-Source.Feed.conc.+X.F.Suc+ total.Vol+PL+rab+SO4.ferm.+PO4.utilise; 0.295, 0.626, Main.P-Source.Conc.+P-Source.Feed.conc.+X.F.Suc+ X.VXdt+PL+rab+His+SO4.ferm.+PO4.utilise; 0.294, 0.626, pH+tmp+Main.P-Source.Conc.+P-Source.Feed. conc.+X.F.Suc+X.VXdt+PL+SO4.ferm.+PO4.utilise; 0.318, 0.626, Main.P-Source.Conc.+P-Source.Feed.conc.+ X.F.Suc+emission_O2+His+SO4.ferm.+PO4.utilise; 0.318, 0.626, pH+Main.P-Source.Conc.+P-Source.Feed.conc.+ X.F.Suc+emission_O2+SO4.ferm.+PO4.utilise; 0.294, 0.626, tmp+Main.P-Source.Conc.+P-Source.Feed.conc.+ X.F.Suc+PL+rab+His+SO4.ferm.+PO4.utilise; 0.281, 0.626, pH+Main.P-Source.Conc.+P-Source.Feed.conc.+ X.F.Suc+total.Vol+PL+rab+Thr+SO4.ferm.+PO4.utilise; 0.280, 0.625, pH+tmp+Main.P-Source.Conc.+P-Source. Feed.conc.+X.F.Suc+PL+emission_O2+Thr+SO4.ferm.+ PO4.utilise; 0.280, 0.625, pH+Main.P-Source.Conc.+P-Source.Feed.conc.+X.F.Suc+PL+emission_O2+Thr+His+ SO4.ferm.+PO4.utilise; 0.280, 0.625, pH+tmp+Main.P-Source.Conc.+P-Source.Feed.conc.+X.F.Suc+X.VXdt+PL+ emission_O2+SO4.ferm.+PO4.utilise; 0.279, 0.625, pH+Main.P-Source.Conc.+P-Source.Feed.conc.+X.F.Suc+ X.VXdt+PL+rab+SO4.ferm.+PO4.ferm.+PO4.utilise; 0.305, 0.625, Main.P-Source.Conc.+P-Source.Feed.conc.+ Nitrogen.Conc.+X.F.Suc+PL+rab+SO4.ferm.+PO4.utilise; 0.279, 0.625, pH+tmp+Main.P-Source.Conc.+P-Source.Feed.conc.+X.F.Suc+total.Vol+PL+rab+SO4.ferm.+ PO4.utilise; 0.292, 0.624, Main.P-Source.Conc.+P-Source.Feed.conc.+X.F.Suc+X.VXdt+total.Vol+PL+emission_O2+SO4.ferm.+PO4.utilise; 0.292, 0.624, Main.P-Source.Conc.+P-Source.Feed.conc.+X.F.Suc+total.Vol+ PL+rab+His+SO4.ferm.+PO4.utilise; 0.328, 0.624, tmp+ Main.P-Source.Conc.+P-Source.Feed.conc.+X.F.Suc+ SO4.ferm.+PO4.utilise; 0.292, 0.624, Main.P-Source.Conc.+P-Source.Feed.conc.+X.F.Suc+total.Vol+ PL+emission_O2+Thr+SO4.ferm.+PO4.utilise; 0.291, 0.624, tmp+Main.P-Source.Conc.+P-Source.Feed.conc.+ X.F.Suc+PL+rab+SO4.ferm.+PO4.ferm.+PO4.utilise; 0.291, 0.624, tmp+Main.P-Source.Conc.+P-Source.Feed. conc.+X.F.Suc+X.VXdt+PL+emission_O2+SO4.ferm.+ PO4.utilise; 0.278, 0.624, tmp+Main.P-Source.Conc.+P-Source.Feed.conc.+X.F.Suc+PL+rab+Thr+His+SO4.ferm.+ PO4.utilise; 0.315, 0.624, Main.P-Source.Conc.+P-Source.Feed.conc.+X.F.Suc+total.Vol+rab+SO4.ferm.+ PO4.utilise; 0.303, 0.624, pH+Main.P-Source.Conc.+P-Source.Feed.conc.+X.F.Suc+rab+Thr+SO4.ferm.+ PO4.utilise; 0.303, 0.624, tmp+Main.P-Source.Conc.+P-Source.Feed.conc.+X.F.Suc+PL+His+SO4.ferm.+ PO4.utilise; 0.291, 0.624, pH+Main.P-Source.Conc.+P-Source.Feed.conc.+Nitrogen.Conc.+X.F.Suc+PL+rab+ SO4.ferm.+PO4.utilise; 0.303, 0.624, Main.P-Source.Conc.+P-Source.Feed.conc.+X.F.Suc+rab+Thr+ His+SO4.ferm.+PO4.utilise; 0.291, 0.624, Main.P-Source.Conc.+P-Source.Feed.conc.+X.F.Suc+X.VXdt+PL+ rab+SO4.ferm.+PO4.ferm.+PO4.utilise; 0.264, 0.623, pH+Main.P-Source.Conc.+P-Source.Feed.conc.+X.F.Suc+ X.VXdt+total.Vol+PL+rab+His+SO4.ferm.+PO4.utilise; 0.315, 0.623, tmp+Main.P-Source.Conc.+P-Source.Feed. conc.+X.F.Suc+rab+SO4.ferm.+PO4.utilise; 0.303, 0.623, tmp+Main.P-Source.Conc.+P-Source.Feed.conc.+X.F.Suc+ X.VXdt+PL+SO4.ferm.+PO4.utilise; 0.290, 0.623, pH+tmp+Main.P-Source.Conc.+P-Source.Feed.conc.+ X.F.Suc+total.Vol+PL+SO4.ferm.+PO4.utilise; 0.277, 0.623, tmp+Main.P-Source.Conc.+P-Source.Feed.conc.+ X.F.Suc+total.Vol+PL+rab+Thr+504.ferm.+PO4.utilise; 0.277, 0.623, pH+tmp+Main.P-Source.Conc.+P-Source. Feed.conc.+X.F.Suc+PL+rab+His+SO4.ferm.+PO4.utilise; 0.303, 0.623, tmp+Main.P-Source.Conc.+P-Source.Feed. conc.+X.F.Suc+total.Vol+PL+SO4.ferm.+PO4.utilise; 0.290, 0.623, pH+tmp+Main.P-Source.Conc.+P-Source. Feed.conc.+X.F.Suc+PL+His+SO4.ferm.+PO4.utilise; 0.290, 0.623, tmp+Main.P-Source.Conc.+P-Source.Feed. conc.+X.F.Suc+total.Vol+PL+emission_O2+SO4.ferm.+ PO4.utilise; 0.290, 0.623, Main.P-Source.Conc.+P-Source. Feed.conc.+X.F.Suc+PL+rab+Thr+SO4.ferm.+PO4.ferm.+ PO4.utilise; 0.277, 0.623, pH+tmp+Main.P-Source.Conc.+ P-Source.Feed.conc.+X.F.Suc+PL+rab+SO4.ferm.+ PO4.ferm.+PO4.utilise; 0.289, 0.623, Main.P-Source.Conc.+P-Source.Feed.conc.+X.F.Suc+PL+rab+His+ SO4.ferm.+PO4.ferm.+PO4.utilise; 0.289, 0.623, tmp+ Main.P-Source.Conc.+P-Source.Feed.conc.+X.F.Suc+PL+ emission_O2+His+SO4.ferm.+PO4.utilise; 0.276, 0.623, pH+Main.P-Source.Conc.+P-Source.Feed.conc.+X.F.Suc+ total.Vol+PL+rab+His+SO4.ferm.+PO4.utilise; 0.289, 0.622, pH+tmp+Main.P-Source.Conc.+P-Source.Feed. conc.+X.F.Suc+PL+SO4.ferm.+PO4.ferm.+PO4.utilise; 0.301, 0.622, Main.P-Source.Conc.+P-Source.Feed.conc.+ Nitrogen.Conc.+X.F.Suc+PL+emission_O2+SO4.ferm.+ PO4.utilise; 0.262, 0.622, pH+tmp+Main.P-Source.Conc.+ P-Source.Feed.conc.+X.F.Suc+X.VXdt+PL+rab+His+ SO4.ferm.+PO4.utilise; 0.262, 0.622, pH+Main.P-Source.Conc.+P-Source.Feed.conc.+OD+X.F.Suc+ total.Vol+total.cell+PL+rab+SO4.ferm.+PO4.utilise; 0.300, 0.622, tmp+Main.P-Source.Conc.+P-Source.Feed.conc.+ X.F.Suc+PL+SO4.ferm.+PO4.ferm.+PO4.utilise; 0.288, 0.622, Main.P-Source.Conc.+P-Source.Feed.conc.+ X.F.Suc+total.Vol+PL+rab+SO4.ferm.+PO4.ferm.+ PO4.utilise; 0.275, 0.622, pH+Main.P-Source.Conc.+P-Source.Feed.conc.+X.F.Suc+PL+rab+His+SO4.ferm.+ PO4.ferm.+PO4.utilise; 0.275, 0.621, tmp+Main.P-Source.Conc.+P-Source.Feed.conc.+X.F.Suc+X.VXdt+PL+ rab+His+SO4.ferm.+PO4.utilise; 0.287, 0.621, Main.P-Source.Conc.+P-Source.Feed.conc.+X.F.Suc+X.VXdt+PL+ emission_O2+His+SO4.ferm.+PO4.utilise; 0.274, 0.621, pH+tmp+Main.P-Source.Conc.+P-Source.Feed.conc.+ X.F.Suc+total.Vol+PL+emission_O2+SO4.ferm.+ PO4.utilise; 0.312, 0.621, Main.P-Source.Conc.+P-Source.Feed.conc.+X.F.Suc+total.Vol+emission_O2+ SO4.ferm.+PO4.utilise; 0.300, 0.621, tmp+Main.P-Source.Conc.+P-Source.Feed.conc.+X.F.Suc+rab+Thr+ SO4.ferm.+PO4.utilise; 0.274, 0.621, pH+Main.P-Source.Conc.+P-Source.Feed.conc.+X.F.Suc+total.Vol+ PL+rab+SO4.ferm.+PO4.ferm.+PO4.utilise; 0.274, 0.621, pH+Main.P-Source.Conc.+P-Source.Feed.conc.+X.F.Suc+ X.VXdt+PL+emission_O2+His+SO4.ferm.+PO4.utilise; 0.287, 0.621, Main.P-Source.Conc.+P-Source.Feed.conc.+ X.F.Suc+total.Vol+PL+emission_O2+His+SO4.ferm.+ PO4.utilise; 0.300, 0.621, pH+Main.P-Source.Conc.+P-Source.Feed.conc.+X.F.Suc+rab+His+SO4.ferm.+ PO4.utilise; 0.287, 0.621, tmp+Main.P-Source.Conc.+P-Source.Feed.conc.+X.F.Suc+PL+Thr+His+SO4.ferm.+ PO4.utilise; 0.312, 0.621, tmp+Main.P-Source.Conc.+P-Source.Feed.conc.+X.F.Suc+Thr+SO4.ferm.+PO4.utilise; 0.274, 0.621, pH+Main.P-Source.Conc.+P-Source.Feed. conc.+X.F.Suc+total.Vol+PL+emission_O2+Thr+ SO4.ferm.+PO4.utilise; 0.274, 0.621, Main.P-Source.Conc.+P-Source.Feed.conc.+X.F.Suc+X.VXdt+to-tal.Vol+PL+rab+His+SO4.ferm.+PO4.utilise; 0.287, 0.621, pH+Main.P-Source.Conc.+P-Source.Feed.conc.+Nitrogen. Conc.+X.F.Suc+PL+emission_O2+SO4.ferm.+PO4.utilise; 0.274, 0.621, tmp+Main.P-Source.Conc.+P-Source.Feed. conc.+X.F.Suc+PL+emission_O2+Thr+His+SO4.ferm.+ PO4.utilise; 0.260, 0.621, pH+tmp+Main.P-Source.Conc.+ P-Source.Feed.conc.+X.F.Suc+PL+rab+Thr+His+ SO4.ferm.+PO4.utilise; 0.299, 0.621, pH+Main.P-Source.Conc.+P-Source.Feed.conc.+X.F.Suc+ emission_O2+Thr+SO4.ferm.+PO4.utilise; 0.286, 0.621, tmp+Main.P-Source.Conc.+P-Source.Feed.conc.+X.F.Suc+ PL+emission_O2+SO4.ferm.+PO4.ferm.+PO4.utilise; 0.299, 0.620, Main.P-Source.Conc.+P-Source.Feed.conc.+ X.F.Suc+total.cell+PL+rab+SO4.ferm.+PO4.utilise; 0.311, 0.620, Main.P-Source.Conc.+P-Source.Feed.conc.+ X.F.Suc+X.VXdt+rab+SO4.ferm.+PO4.utilise; 0.298, 0.620, Main.P-Source.Conc.+P-Source.Feed.conc.+ X.F.Suc+emission_O2+Thr+His+SO4.ferm.+PO4.utilise; 0.259, 0.620, pH+tmp+Main.P-Source.Conc.+P-Source. Feed.conc.+X.F.Suc+total.Vol+PL+rab+Thr+SO4.ferm.+ PO4.utilise; 0.273, 0.620, pH+tmp+Main.P-Source.Conc.+ P-Source.Feed.conc.+X.F.Suc+PL+emission_O2+His+ SO4.ferm.+PO4.utilise; 0.286, 0.620, pH+Main.P-Source.Conc.+P-Source.Feed.conc.+X.F.Suc+total.cell+ PL+rab+SO4.ferm.+PO4.utilise; 0.272, 0.620, pH+Main.P-Source.Conc.+P-Source.Feed.conc.+X.F.Suc+PL+rab+ Thr+SO4.ferm.+PO4.ferm.+PO4.utilise; 0.272, 0.620, Main.P-Source.Conc.+P-Source.Feed.conc.+X.F.Suc+ total.Vol+PL+rab+Thr+His+SO4.ferm.+PO4.utilise; 0.285, 0.620, Main.P-Source.Conc.+P-Source.Feed.conc.+Nitro-gen.Conc.+X.F.Suc+PL+rab+Thr+SO4.ferm.+PO4.utilise; 0.298, 0.620, Main.P-Source.Conc.+P-Source.Feed.conc.+ X.F.Suc+total.Vol+rab+Thr+SO4.ferm.+PO4.utilise; 0.310, 0.620, tmp+Main.P-Source.Conc.+P-Source.Feed.conc.+ X.F.Suc+emission_O2+SO4.ferm.+PO4.utilise; 0.272, 0.620, pH+Main.P-Source.Conc.+P-Source.Feed.conc.+ X.F.Suc+X.VXdt+PL+emission_O2+SO4.ferm.+ PO4.ferm.+PO4.utilise; 0.272, 0.620, tmp+Main.P-Source.Conc.+P-Source.Feed.conc.+X.F.Suc+total.Vol+ PL+emission_O2+Thr+SO4.ferm.+PO4.utilise; 0.297, 0.619, pH+Main.P-Source.Conc.+P-Source.Feed.conc.+ X.F.Suc+emission_O2+His+SO4.ferm.+PO4.utilise; 0.309, 0.619, Main.P-Source.Conc.+P-Source.Feed.conc.+ X.F.Suc+rab+SO4.ferm.+PO4.ferm.+PO4.utilise; 0.272, 0.619, pH+tmp+Main.P-Source.Conc.+P-Source.Feed. conc.+X.F.Suc+PL+emission_O2+SO4.ferm.+PO4.ferm.+ PO4.utilise; 0.271, 0.619, tmp+Main.P-Source.Conc.+P-Source.Feed.conc.+X.F.Suc+total.Vol+PL+rab+His+ SO4.ferm.+PO4.utilise; 0.258, 0.619, pH+Main.P-Source.Conc.+P-Source.Feed.conc.+X.F.Suc+X.VXdt+ total.Vol+PL+emission_O2+His+SO4.ferm.+PO4.utilise; 0.284, 0.619, Main.P-Source.Conc.+P-Source.Feed.conc.+ X.F.Suc+X.VXdt+PL+emission_O2+SO4.ferm.+ PO4.ferm.+PO4.utilise; 0.258, 0.619, pH+Main.P-Source.Conc.+P-Source.Feed.conc.+X.F.Suc+X.VXdt+ total.Vol+PL+rab+SO4.ferm.+PO4.ferm.+PO4.utilise; 0.271, 0.619, pH+tmp+Main.P-Source.Conc.+P-Source. Feed.conc.+X.F.Suc+PL+Thr+His+SO4.ferm.+PO4.utilise; 0.258, 0.619, pH+tmp+Main.P-Source.Conc.+P-Source. Feed.conc.+X.F.Suc+X.VXdt+PL+rab+SO4.ferm.+ PO4.ferm.+PO4.utilise; 0.271, 0.619, pH+Main.P-Source.Conc.+P-Source.Feed.conc.+X.F.Suc+total.Vol+ PL+emission_O2+His+SO4.ferm.+PO4.utilise; 0.271, 0.619, pH+tmp+Main.P-Source.Conc.+P-Source.Feed. conc.+X.F.Suc+X.VXdt+PL+His+SO4.ferm.+PO4.utilise; 0.284, 0.619, Main.P-Source.Conc.+P-Source.Feed.conc.+ X.F.Suc+total.Vol+PL+emission_O2+SO4.ferm.+ PO4.ferm.+PO4.utilise; 0.284, 0.619, Main.P-Source.Conc.+P-Source.Feed.conc.+X.F.Suc+PL+ emission_O2+His+SO4.ferm.+PO4.ferm.+PO4.utilise; 0.284, 0.619, tmp+Main.P-Source.Conc.+P-Source.Feed. conc.+X.F.Suc+total.Vol+PL+Thr+SO4.ferm.+PO4.utilise; 0.284, 0.619, Main.P-Source.Conc.+P-Source.Feed.conc.+ X.F.Suc+X.VXdt+PL+rab+Thr+SO4.ferm.+PO4.utilise; 0.296, 0.619, Main.P-Source.Conc.+P-Source.Feed.conc.+ Main.Thr.Conc.+X.F.Suc+PL+rab+SO4.ferm.+PO4.utilise; 0.308, 0.619, tmp+Main.P-Source.Conc.+P-Source.Feed. conc.+X.F.Suc+His+SO4.ferm.+PO4.utilise; 0.296, 0.619, Main.P-Source.Conc.+P-Source.Feed.conc.+Lys_conc.+ X.F.Suc+PL+emission_O2+SO4.ferm.+PO4.utilise; 0.308, 0.618, pH+tmp+Main.P-Source.Conc.+P-Source.Feed. conc.+X.F.Suc+SO4.ferm.+PO4.utilise; 0.296, 0.618, Main.P-Source.Conc.+P-Source.Feed.conc.+X.F.Suc+Cell+ PL+rab+SO4.ferm.+PO4.utilise; 0.270, 0.618, pH+Main.P-Source.Conc.+P-Source.Feed.conc.+Nitrogen.Conc.+ X.F.Suc+PL+rab+Thr+SO4.ferm.+PO4.utilise; 0.270, 0.618, pH+Main.P-Source.Conc.+P-Source.Feed.conc.+ X.F.Suc+total.Vol+PL+emission_O2+SO4.ferm.+ PO4.ferm.+PO4.utilise; 0.283, 0.618, pH+Main.P-Source.Conc.+P-Source.Feed.conc.+X.F.Suc+Cell+PL+ rab+SO4.ferm.+PO4.utilise; 0.295, 0.618, Main.P-Source.Conc.+P-Source.Feed.conc.+Main.Thr.Conc.+ X.F.Suc+PL+emission_O2+SO4.ferm.+PO4.utilise; 0.283, 0.618, Main.P-Source.Conc.+P-Source.Feed.conc.+ X.F.Suc+PL+emission_O2+Thr+SO4.ferm.+PO4.ferm.+ PO4.utilise; 0.283, 0.618, pH+Main.P-Source.Conc.+P-Source.Feed.conc.+Main.Thr.Conc.+X.F.Suc+PL+rab+ SO4.ferm.+PO4.utilise; 0.269, 0.618, tmp+Main.P-Source.Conc.+P-Source.Feed.conc.+X.F.Suc+X.VXdt+PL+ rab+SO4.ferm.+PO4.ferm.+PO4.utilise; 0.269, 0.618, tmp+ Main.P-Source.Conc.+P-Source.Feed.conc.+X.F.Suc+PL+ rab+Thr+SO4.ferm.+PO4.ferm.+PO4.utilise; 0.256, 0.618, pH+tmp+Main.P-Source.Conc.+P-Source.Feed.conc.+ X.F.Suc+X.VXdt+PL+emission_O2+His+SO4.ferm.+ PO4.utilise; 0.269, 0.618, Main.P-Source.Conc.+P-Source.Feed.conc.+OD+X.F.Suc+total.Vol+total.cell+PL+rab+SO4.ferm.+PO4.utilise; 0.295, 0.618, Main.P-Source.Conc.+P-Source.Feed.conc.+Lys_conc.+X.F.Suc+PL+rab+SO4.ferm.+PO4.utilise; 0.295, 0.618, tmp+Main.P-Source.Conc.+P-Source.Feed.conc.+X.F.Suc+emission_O2+Thr+SO4.ferm.+PO4.utilise; 0.307, 0.617, Main.P-Source.Conc.+P-Source.Feed.conc.+X.F.Suc+emission_O2+SO4.ferm.+PO4.ferm.+PO4.utilise; 0.282, 0.617, pH+Main.P-Source.Conc.+P-Source.Feed.conc.+Main.Thr.Conc.+X.F.Suc+PL+emission_O2+SO4.ferm.+PO4.utilise; 0.269, 0.617, pH+Main.P-Source.Conc.+P-Source.Feed.conc.+Nitrogen.Conc.+X.F.Suc+X.VXdt+PL+rab+SO4.ferm.+PO4.utilise; 0.269, 0.617, pH+Main.P-Source.Conc.+P-Source.Feed.conc.+X.F.Suc+PL+emission_O2+His+SO4.ferm.+PO4.ferm.+PO4.utilise; 0.294, 0.617, pH+Main.P-Source.Conc.+P-Source.Feed.conc.+X.F.Suc+total.Vol+rab+SO4.ferm.+PO4.utilise; 0.255, 0.617, pH+tmp+Main.P-Source.Conc.+P-Source.Feed.conc.+X.F.Suc+PL+emission_O2+Thr+His+SO4.ferm.+PO4.utilise; 0.269, 0.617, pH+Main.P-Source.Conc.+P-Source.Feed.conc.+X.F.Suc+X.VXdt+total.cell+PL+rab+SO4.ferm.+PO4.utilise; 0.294, 0.617, tmp+Main.P-Source.Conc.+P-Source.Feed.conc.+X.F.Suc+rab+His+SO4.ferm.+PO4.utilise; 0.268, 0.617, pH+tmp+Main.P-Source.Conc.+P-Source.Feed.conc.+X.F.Suc+total.Vol+PL+Thr+SO4.ferm.+PO4.utilise; 0.268, 0.617, tmp+Main.P-Source.Conc.+P-Source.Feed.conc.+X.F.Suc+X.VXdt+PL+emission_O2+His+SO4.ferm.+PO4.utilise; 0.255, 0.617, pH+tmp+Main.P-Source.Conc.+P-Source.Feed.conc.+X.F.Suc+total.Vol+PL+rab+His+SO4.ferm.+PO4.utilise; 0.268, 0.617, tmp+Main.P-Source.Conc.+P-Source.Feed.conc.+X.F.Suc+X.VXdt+PL+rab+Thr+SO4.ferm.+PO4.utilise; 0.281, 0.617, pH+Main.P-Source.Conc.+P-Source.Feed.conc.+Lys_conc.+X.F.Suc+PL+emission_O2+SO4.ferm.+PO4.utilise; 0.281, 0.617, pH+Main.P-Source.Conc.+P-Source.Feed.conc.+X.F.Suc+PL+rab+lactate+SO4.ferm.+PO4.utilise; 0.281, 0.617, tmp+Main.P-Source.Conc.+P-Source.Feed.conc.+X.F.Suc+total.Vol+PL+His+SO4.ferm.+PO4.utilise; 0.306, 0.617, Main.P-Source.Conc.+P-Source.Feed.conc.+X.F.Suc+X.VXdt+emission_O2+SO4.ferm.+PO4.utilise; 0.268, 0.617, Main.P-Source.Conc.+P-Source.Feed.conc.+X.F.Suc+X.VXdt+total.Vol+PL+emission_O2+His+SO4.ferm.+PO4.utilise; 0.294, 0.617, Main.P-Source.Conc.+P-Source.Feed.conc.+X.F.Suc+total.Vol+rab+His+SO4.ferm.+PO4.utilise; 0.281, 0.617, tmp+Main.P-Source.Conc.+P-Source.Feed.conc.+X.F.Suc+X.VXdt+PL+His+SO4.ferm.+PO4.utilise; 0.281, 0.617, pH+Main.P-Source.Conc.+P-Source.Feed.conc.+X.F.Suc+rab+Thr+His+SO4.ferm.+PO4.utilise; 0.281, 0.617, pH+Main.P-Source.Conc.+P-Source.Feed.conc.+Lys_conc.+X.F.Suc+PL+rab+SO4.ferm.+PO4.utilise; 0.254, 0.617, pH+Main.P-Source.Conc.+P-Source.Feed.conc.+X.F.Suc+total.Vol+PL+rab+Thr+His+SO4.ferm.+PO4.utilise; 0.281, 0.617, Main.P-Source.Conc.+P-Source.Feed.conc.+Main.Thr.Conc.+X.F.Suc+PL+rab+Thr+SO4.ferm.+PO4.utilise; 0.254, 0.617, pH+Main.P-Source.Conc.+P-Source.Feed.conc.+X.F.Suc+X.VXdt+PL+rab+Thr+lactate+SO4.ferm.+PO4.utilise; 0.254, 0.617, pH+tmp+Main.P-Source.Conc.+P-Source.Feed.conc.+Nitrogen.Conc.+X.F.Suc+X.VXdt+PL+rab+SO4.ferm.+PO4.utilise; 0.267, 0.616, pH+tmp+Main.P-Source.Conc.+P-Source.Feed.conc.+X.F.Suc+total.Vol+PL+His+SO4.ferm.+PO4.utilise; 0.254, 0.616, pH+tmp+Main.P-Source.Conc.+P-Source.Feed.conc.+X.F.Suc+total.Vol+PL+emission_O2+Thr+SO4.ferm.+PO4.utilise; 0.254, 0.616, pH+Main.P-Source.Conc.+P-Source.Feed.conc.+Nitrogen.Conc.+X.F.Suc+X.VXdt+total.Vol+PL+rab+SO4.ferm.+PO4.utilise; 0.280, 0.616, Main.P-Source.Conc.+P-Source.Feed.conc.+Nitrogen.Conc.+X.F.Suc+X.VXdt+PL+rab+SO4.ferm.+PO4.utilise; 0.254, 0.616, pH+Main.P-Source.Conc.+P-Source.Feed.conc.+OD+X.F.Suc+total.Vol+total.cell+PL+emission_O2+SO4.ferm.+PO4.utilise; 0.293, 0.616, Main.P-Source.Conc.+P-Source.Feed.conc.+X.F.Suc+total.Vol+emission_O2+Thr+SO4.ferm.+PO4.utilise; 0.267, 0.616, tmp+Main.P-Source.Conc.+P-Source.Feed.conc.+X.F.Suc+total.Vol+PL+emission_O2+His+SO4.ferm.+PO4.utilise; 0.267, 0.616, Main.P-Source.Conc.+P-Source.Feed.conc.+X.F.Suc+X.VXdt+total.Vol+PL+rab+SO4.ferm.+PO4.ferm.+PO4.utilise; 0.253, 0.616, pH+tmp+Main.P-Source.Conc.+P-Source.Feed.conc.+X.F.Suc+X.VXdt+total.Vol+PL+rab+SO4.ferm.+PO4.utilise; 0.267, 0.616, pH+Main.P-Source.Conc.+P-Source.Feed.conc.+Main.Thr.Conc.+X.F.Suc+X.VXdt+PL+rab+SO4.ferm.+PO4.utilise; 0.280, 0.616, Main.P-Source.Conc.+P-Source.Feed.conc.+Nitrogen.Conc.+X.F.Suc+PL+emission_O2+Thr+SO4.ferm.+PO4.utilise; 0.292, 0.616, pH+tmp+Main.P-Source.Conc.+P-Source.Feed.conc.+X.F.Suc+rab+SO4.ferm.+PO4.utilise; 0.266, 0.616, pH+Main.P-Source.Conc.+P-Source.Feed.conc.+X.F.Suc+X.VXdt+PL+rab+lactate+SO4.ferm.+PO4.utilise; 0.279, 0.616, Main.P-Source.Conc.+P-Source.Feed.conc.+X.F.Suc+X.VXdt+total.cell+PL+rab+SO4.ferm.+PO4.utilise; 0.266, 0.616, pH+Main.P-Source.Conc.+P-Source.Feed.conc.+Main.Thr.Conc.+X.F.Suc+PL+rab+Thr+SO4.ferm.+PO4.utilise; 0.266, 0.616, Main.P-Source.Conc.+P-Source.Feed.conc.+X.F.Suc+total.Vol+PL+emission_O2+Thr+His+SO4.ferm.+PO4.utilise; 0.253, 0.616, tmp+Main.P-Source.Conc.+P-Source.Feed.conc.+X.F.Suc+total.Vol+PL+rab+Thr+His+SO4.ferm.+PO4.utilise; 0.304, 0.616, tmp+Main.P-Source.Conc.+P-Source.Feed.conc.+X.F.Suc+total.Vol+SO4.ferm.+PO4.utilise; 0.252, 0.616, pH+Main.P-Source.Conc.+P-Source.Feed.conc.+X.F.Suc+X.VXdt+total.Vol+PL+emission_O2+SO4.ferm.+PO4.ferm.+PO4.utilise; 0.266, 0.616, tmp+Main.P-Source.Conc.+P-Source.Feed.conc.+X.F.Suc+PL+rab+His+SO4.ferm.+PO4.ferm.+PO4.utilise; 0.292, 0.615, Main.P-Source.Conc.+P-Source.Feed.conc.+X.F.Suc+total.cell+PL+emission_O2+SO4.ferm.+PO4.utilise; 0.279, 0.615, tmp+Main.P-Source.Conc.+P-Source.Feed.conc.+Nitrogen.Conc.+X.F.Suc+PL+rab+SO4.ferm.+PO4.utilise; 0.252, 0.615, pH+Main.P-Source.Conc.+P-Source.Feed.conc.+X.F.Suc+X.VXdt+PL+rab+His+SO4.ferm.+PO4.ferm.+PO4.utilise; 0.266, 0.615, tmp+Main.P-Source.Conc.+P-Source.Feed.conc.+Nitrogen.Conc.+X.F.Suc+X.VXdt+PL+rab+SO4.ferm.+PO4.utilise; 0.266, 0.615, pH+tmp+Main.P-Source.Conc.+P-Source.Feed.conc.+X.F.Suc+X.VXdt+PL+SO4.ferm.+PO4.ferm.+PO4.utilise; 0.291, 0.615, tmp+Main.P-Source.Conc.+P-Source.Feed.conc.+X.F.Suc+total.Vol+rab+SO4.ferm.+PO4.utilise; 0.252, 0.615, pH+Main.P-Source.Conc.+P-Source.Feed.conc.+Main.Thr.Conc.+X.F.Suc+X.VXdt+total.Vol+PL+rab+SO4.ferm.+PO4.utilise; 0.252, 0.615, pH+tmp+Main.P-Source.Conc.+P-Source.Feed.conc.+X.F.Suc+X.VXdt+PL+emission_O2+SO4.ferm.+PO4.ferm.+PO4.utilise; 0.278, 0.615, Main.P-Source.Conc.+P-Source.Feed.conc.+Main.Thr.Conc.+X.F.Suc+PL+emission_O2+Thr+SO4.ferm.+PO4.utilise; 0.291, 0.615, Main.P-Source.Conc.+P-Source.Feed.conc.+X.F.Suc+PL+rab+lactate+SO4.ferm.+PO4.utilise; 0.265, 0.615, tmp+Main.P-Source.Conc.+P-Source.Feed.conc.+X. F.Suc+X.VXdt+total.Vol+PL+rab+SO4.ferm.+PO4.utilise; 0.291, 0.615, pH+Main.P-Source.Conc.+P-Source.Feed. conc.+X.F.Suc+total.Vol+emission_O2+SO4.ferm.+PO4. utilise; 0.265, 0.615, pH+Main.P-Source.Conc.+P-Source. Feed.conc.+X.F.Suc+PL+rab+Thr+lactate+SO4.ferm.+ PO4.utilise; 0.291, 0.615, Main.P-Source.Conc.+P-Source. Feed.conc.+yield+PL+rab+SO4.ferm.+PO4.ferm.+PO4. utilise; 0.291, 0.615, tmp+Main.P-Source.Conc.+P-Source. Feed.conc.+yield+PL+SO4.ferm.+PO4.ferm.+PO4.utilise; 0.278, 0.615, Main.P-Source.Conc.+P-Source.Feed.conc.+ Lys_conc.+X.F.Suc+PL+rab+Thr+SO4.ferm.+PO4.utilise; 0.278, 0.615, pH+Main.P-Source.Conc.+P-Source.Feed. conc.+X.F.Suc+total.cell+PL+emission_O2+SO4.ferm.+ PO4.utilise; 0.278, 0.615, pH+tmp+Main.P-Source.Conc.+ P-Source.Feed. conc.+yield+PL+SO4.ferm.+PO4.ferm.+ PO4.utilise; 0.290, 0.615, tmp+Main.P-Source.Conc.+P-Source.Feed. conc.+X.F.Suc+Thr+His+SO4.ferm.+PO4. utilise; 0.278, 0.615, tmp+Main.P-Source.Conc.+P-Source. Feed.conc.+X.F.Suc+rab+Thr+His+SO4.ferm.+PO4.utilise; 0.264, 0.614, Main.P-Source.Conc.+P-Source.Feed.conc.+ X.F.Suc+X.VXdt+total.Vol+PL+rab+Thr+SO4.ferm.+PO4. utilise; 0.264, 0.614, pH+Main.P-Source.Conc.+P-Source. Feed.conc.+X.F.Suc+PL+emission_O2+Thr+SO4.ferm.+ PO4.ferm.+PO4.utilise; 0.264, 0.614, Main.P-Source. Conc.+P-Source.Feed.conc.+X.F.Suc+X.VXdt+PL+rab+ His+SO4.ferm.+PO4.ferm.+PO4.utilise; 0.251, 0.614, pH+tmp+Main.P-Source.Conc.+P-Source.Feed.conc.+X.F. Suc+PL+rab+Thr+SO4.ferm.+PO4.ferm.+PO4.utilise; 0.290, 0.614, Main.P-Source.Conc.+P-Source.Feed.conc.+ X.F.Suc+Cell+PL+emission_O2+SO4.ferm.+PO4.utilise; 0.264, 0.614, tmp+Main.P-Source.Conc.+P-Source.Feed. conc.+X.F.Suc+PL+emission_O2+Thr+SO4.ferm.+PO4. ferm.+PO4.utilise; 0.264, 0.614, pH+tmp+Main.P-Source. Conc.+P-Source.Feed.conc.+X.F.Suc+PL+His+SO4.ferm.+ PO4.ferm.+PO4.utilise; 0.290, 0.614, Main.P-Source. Conc.+P-Source.Feed.conc.+X.F.Suc+total.Vol+emission_ O2+His+SO4.ferm.+PO4.utilise; 0.290, 0.614, pH+tmp+ Main.P-Source.Conc.+P-Source.Feed.conc.+X.F.Suc+Thr+ SO4.ferm.+PO4.utilise; 0.277, 0.614, Main.P-Source. Conc.+P-Source.Feed.conc.+Lys_conc.+X.F.Suc+PL+ emission_O2+Thr+SO4.ferm.+PO4.utilise; 0.250, 0.614, pH+tmp+Main.P-Source.Conc.+P-Source. Feed.conc.+X.F. Suc+total.Vol+PL+emission_O2+His+SO4.ferm.+PO4.utilise; 0.277, 0.614, tmp+Main.P-Source.Conc.+P-Source. Feed.conc.+X.F.Suc+PL+His+SO4.ferm.+PO4.ferm.+PO4. utilise; 0.290, 0.614, pH+Main.P-Source.Conc.+P-Source. Feed.conc.+X.F.Suc+X.VXdt+rab+SO4.ferm.+PO4.utilise; 0.290, 0.614, tmp+Main.P-Source.Conc.+P-Source.Feed. conc.+X.F.Suc+emission_O2+His+SO4.ferm.+PO4.utilise; 0.264, 0.614, pH+Main.P-Source.Conc.+P-Source.Feed. conc.+X.F.Suc+PL+emission_O2+Thr+lactate+SO4.ferm.+ PO4.utilise; 0.289, 0.614, Main.P-Source.Conc.+P-Source. Feed.conc.+OD+X.F.Suc+PL+rab+SO4.ferm.+PO4.utilise; 0.277, 0.614, pH+Main.P-Source.Conc.+P-Source.Feed. conc.+X.F.Suc+PL+emission_O2+lactate+SO4.ferm.+PO4. utilise; 0.250, 0.614, pH+tmp+Main.P-Source.Conc.+P-Source. Feed.conc.+X.F.Suc+PL+rab+His+SO4.ferm.+ PO4.ferm.+PO4.utilise; 0.264, 0.614, pH+Main.P-Source. Conc.+P-Source.Feed.conc.+Main.Thr.Conc.+X.F.Suc+ PL+emission_O2+Thr+SO4.ferm.+PO4.utilise; 0.264, 0.614, tmp+Main.P-Source.Conc.+P-Source.Feed.conc.+X. F.Suc+X.VXdt+PL+emission_O2+SO4.ferm.+PO4.ferm.+ PO4.utilise; 0.264, 0.614, pH+Main.P-Source.Conc.+ P-Source.Feed.conc.+Nitrogen.Conc.+X.F.Suc+PL+ emission_O2+Thr+SO4.ferm.+PO4.utilise; 0.277, 0.614, pH+Main.P-Source.Conc.+P-Source.Feed.conc.+X.F.Suc+ Cell+PL+emission_O2+SO4.ferm.+PO4.utilise; 0.277, 0.614, Main.P-Source.Conc.+P-Source.Feed.conc.+Nitrogen.Conc.+X.F.Suc+total.Vol+PL+rab+SO4.ferm.+ PO4.utilise; 0.301, 0.614, Main.P-Source.Conc.+P-Source. Feed.conc.+Nitrogen.Conc.+X.F.Suc+rab+SO4.ferm.+ PO4.utilise; 0.289, 0.614, Main.P-Source.Conc.+P-Source. Feed.conc.+X.F.Suc+X.VXdt+rab+His+SO4.ferm.+ PO4.utilise; 0.301, 0.614, Main.P-Source.Conc.+P-Source.Feed.conc.+yield+PL+rab+SO4.ferm.+PO4.utilise; 0.249, 0.614, pH+Main.P-Source.Conc.+P-Source.Feed. conc.+X.F.Suc+X.VXdt+total.Vol+total.cell+PL+rab+ SO4.ferm.+PO4.utilise; 0.276, 0.613, pH+Main.P-Source.Conc.+P-Source.Feed.conc.+OD+X.F.Suc+PL+ rab+SO4.ferm.+PO4.utilise; 0.263, 0.613, pH+tmp+ Main.P-Source.Conc.+P-Source.Feed.conc.+ Nitrogen.Conc.+X.F.Suc+PL+rab+SO4.ferm.+PO4.utilise; 0.276, 0.613, pH+Main.P-Source.Conc.+P-Source.Feed. conc.+X.F.Suc+emission_O2+Thr+His+SO4.ferm.+ PO4.utilise; 0.249, 0.613, pH+Main.P-Source.Conc.+P-Source.Feed.conc.+Main.Thr.Conc.+X.F.Suc+X.VXdt+total.Vol+PL+emission_O2+SO4.ferm.+PO4.utilise; 0.276, 0.613, Main.P-Source.Conc.+P-Source.Feed.conc.+Nitrogen.Conc.+X.F.Suc+PL+rab+His+SO4.ferm.+PO4.utilise; 0.263, 0.613, Main.P-Source.Conc.+P-Source.Feed.conc.+ X.F.Suc+total.Vol+PL+rab+Thr+SO4.ferm.+PO4.ferm.+ PO4.utilise; 0.263, 0.613, pH+Main.P-Source.Conc.+P-Source.Feed.conc.+Lys_conc.+X.F.Suc+PL+rab+Thr+ SO4.ferm.+PO4.utilise; 0.263, 0.613, pH+tmp+Main.P-Source.Conc.+P-Source.Feed.conc.+Nitrogen.Conc.+ X.F.Suc+X.VXdt+PL+SO4.ferm.+PO4.utilise; 0.262, 0.613, pH+Main.P-Source.Conc.+P-Source.Feed.conc.+ Main.Thr.Conc.+X.F.Suc+X.VXdt+PL+emission_O2+ SO4.ferm.+PO4.utilise; 0.276, 0.613, pH+tmp+Main.P-Source.Conc.+P-Source.Feed.conc.+X.F.Suc+rab+Thr+ SO4.ferm.+PO4.utilise; 0.300, 0.613, Main.P-Source.Conc.+P-Source.Feed.conc.+yield+PL+ emission_O2+SO4.ferm.+PO4.utilise; 0.288, 0.613, pH+Main.P-Source.Conc.+P-Source.Feed.conc.+X.F.Suc+ rab+SO4.ferm.+PO4.ferm.+PO4.utilise; 0.249, 0.613, pH+Main.P-Source.Conc.+P-Source.Feed.conc.+OD+ X.F.Suc+X.VXdt+total.Vol+PL+rab+SO4.ferm.+ PO4.utilise; 0.262, 0.613, Main.P-Source.Conc.+P-Source. Feed.conc.+X.F.Suc+X.VXdt+total.Vol+PL+emission_O2+ SO4.ferm.+PO4.ferm.+PO4.utilise; 0.275, 0.613, tmp+ Main.P-Source.Conc.+P-Source.Feed.conc.+X.F.Suc+PL+ Thr+SO4.ferm.+PO4.ferm.+PO4.utilise; 0.275, 0.613, Main.P-Source.Conc.+P-Source.Feed.conc.+Main.Thr. Conc.+X.F.Suc+X.VXdt+PL+rab+SO4.ferm.+PO4.utilise; 0.262, 0.613, pH+Main.P-Source.Conc.+P-Source.Feed. conc.+Nitrogen.Conc.+X.F.Suc+total.Vol+PL+rab+ SO4.ferm.+PO4.utilise; 0.288, 0.613, Main.P-Source.Conc.+P-Source.Feed.conc.+X.F.Suc+rab+Thr+ SO4.ferm.+PO4.ferm.+PO4.utilise; 0.234, 0.613, pH+Main.P-Source.Conc.+P-Source.Feed.conc.+X.F.Suc+ X.VXdt+total.Vol+PL+rab+Thr+lactate+SO4.ferm.+ PO4.utilise; 0.288, 0.613, tmp+Main.P-Source.Conc.+P-Source.Feed.conc.+Nitrogen.Conc.+X.F.Suc+PL+ SO4.ferm.+PO4.utilise; 0.262, 0.613, Main.P-Source.Conc.+P-Source.Feed.conc.+OD+X.F.Suc+ total.Vol+total.cell+PL+emission_O2+SO4.ferm.+ PO4.utilise; 0.275, 0.613, pH+tmp+Main.P-Source.Conc.+ P-Source.Feed.conc.+Nitrogen.Conc.+X.F.Suc+PL+ SO4.ferm.+PO4.utilise; 0.275, 0.613, pH+Main.P-Source.Conc.+P-Source.Feed.conc.+X.F.Suc+total.Vol+ rab+Thr+SO4.ferm.+PO4.utilise; 0.288, 0.613, pH+tmp+

Main.P-Source.Conc.+P-Source.Feed.conc.+X.F.Suc+ emission_O2+SO4.ferm.+PO4.utilise; 0.288, 0.613, pH+tmp+Main.P-Source.Conc.+P-Source.Feed.conc.+ X.F.Suc+His+SO4.ferm.+PO4.utilise; 0.275, 0.613, tmp+ Main.P-Source.Conc.+P-Source.Feed.conc.+X.F.Suc+ total.cell+PL+rab+SO4.ferm.+PO4.utilise; 0.288, 0.613, tmp+Main.P-Source.Conc.+P-Source.Feed.conc.+X.F.Suc+ X.VXdt+rab+SO4.ferm.+PO4.utilise; 0.262, 0.613, Main.P-Source.Conc.+P-Source.Feed.conc.+Nitrogen.Conc.+ X.F.Suc+X.VXdt+total.Vol+PL+rab+SO4.ferm.+ PO4.utilise; 0.300, 0.613, tmp+Main.P-Source.Conc.+P-Source.Feed.conc.+X.F.Suc+X.VXdt+SO4.ferm.+ PO4.utilise; 0.262, 0.613, tmp+Main.P-Source.Conc.+P-Source.Feed.conc.+Nitrogen.Conc.+X.F.Suc+PL+rab+Thr+ SO4.ferm.+PO4.utilise; 0.262, 0.613, pH+Main.P-Source.Conc.+P-Source.Feed.conc.+X.F.Suc+PL+rab+ lactate+SO4.ferm.+PO4.ferm.+PO4.utilise; 0.287, 0.613, Main.P-Source.Conc.+P-Source.Feed.conc.+X.F.Suc+PL+ emission_O2+lactate+804.ferm.+PO4.utilise; 0.248, 0.612, pH+Main.P-Source.Conc.+P-Source.Feed.conc.+X.F.Suc+ PL+rab+Thr+lactate+SO4.ferm.+PO4.ferm.+PO4.utilise; 0.261, 0.612, Main.P-Source.Conc.+P-Source.Feed.conc.+ X.F.Suc+PL+rab+Thr+His+SO4.ferm.+PO4.ferm.+ PO4.utilise; 0.275, 0.612, pH+Main.P-Source.Conc.+P-Source.Feed.conc.+yield+PL+rab+SO4.ferm.+PO4.ferm.+ PO4.utilise; 0.323, 0.612, Main.P-Source.Conc.+P-Source.Feed.conc.+yield+SO4.ferm.+PO4.utilise; 0.274, 0.612, tmp+Main.P-Source.Conc.+P-Source.Feed.conc.+ X.F.Suc+X.VXdt+PL+SO4.ferm.+PO4.ferm.+PO4.utilise; 0.261, 0.612, Main.P-Source.Conc.+P-Source.Feed.conc.+ X.F.Suc+total.Vol+PL+rab+His+SO4.ferm.+PO4.ferm.+ PO4.utilise; 0.248, 0.612, tmp+Main.P-Source.Conc.+P-Source.Feed.conc.+X.F.Suc+total.Vol+PL+emission_O2+ Thr+His+SO4.ferm.+PO4.utilise; 0.287, 0.612, Main.P-Source.Conc.+P-Source.Feed.conc.+X.F.Suc+X.VXdt+ total.Vol+rab+SO4.ferm.+PO4.utilise; 0.247, 0.612, pH+tmp+Main.P-Source.Conc.+P-Source.Feed.conc.+Ni-trogen.Conc.+X.F.Suc+X.VXdt+PL+emission_O2+ SO4.ferm.+PO4.utilise; 0.261, 0.612, pH+Main.P-Source.Conc.+P-Source.Feed.conc.+Nitrogen.Conc.+ X.F.Suc+PL+rab+His+SO4.ferm.+PO4.utilise; 0.287, 0.612, Main.P-Source.Conc.+P-Source.Feed.conc.+yield+ PL+emission_O2+SO4.ferm.+PO4.ferm.+PO4.utilise; 0.274, 0.612, Main.P-Source.Conc.+P-Source.Feed.conc.+ Nitrogen.Conc.+X.F.Suc+PL+rab+SO4.ferm.+PO4.ferm.+ PO4.utilise; 0.274, 0.612, Main.P-Source.Conc.+P-Source. Feed.conc.+X.F.Suc+total.Vol+rab+Thr+His+SO4.ferm.+ PO4.utilise; 0.261, 0.612, tmp+Main.P-Source.Conc.+P-Source.Feed.conc.+X.F.Suc+PL+emission_O2+His+ SO4.ferm.+PO4.ferm.+PO4.utilise; 0.233, 0.612, pH+tmp+ Main.P-Source.Conc.+P-Source.Feed.conc.+X.F.Suc+ X.VXdt+PL+rab+Thr+lactate+SO4.ferm.+PO4.utilise; 0.261, 0.612, pH+Main.P-Source.Conc.+P-Source.Feed. conc.+X.F.Suc+X.VXdt+PL+rab+Thr+SO4.ferm.+ PO4.utilise; 0.233, 0.612, pH+tmp+Main.P-Source.Conc.+ P-Source.Feed.conc.+X.F.Suc+total.Vol+PL+rab+Thr+His+ SO4.ferm.+PO4.utilise; 0.274, 0.612, tmp+Main.P-Source.Conc.+P-Source.Feed.conc.+X.F.Suc+total.Vol+ rab+Thr+SO4.ferm.+PO4.utilise; 0.261, 0.612, tmp+ Main.P-Source.Conc.+P-Source.Feed.conc.+X.F.Suc+ X.VXdt+PL+emission_O2+Thr+SO4.ferm.+PO4.utilise; 0.261, 0.612, Main.P-Source.Conc.+P-Source.Feed.conc.+ X.F.Suc+X.VXdt+PL+rab+Thr+lactate+SO4.ferm.+ PO4.utilise; 0.233, 0.612, pH+Main.P-Source.Conc.+P-Source.Feed.conc.+OD+X.F.Suc+X.VXdt+total.Vol+ total.cell+PL+rab+SO4.ferm.+PO4.utilise; 0.247, 0.612, pH+Main.P-Source.Conc.+P-Source.Feed.conc.+X.F.Suc+ total.Vol+PL+emission_O2+Thr+His+SO4.ferm.+ PO4.utilise; 0.274, 0.612, tmp+Main.P-Source.Conc.+P-Source.Feed.conc.+Nitrogen.Conc.+X.F.Suc+PL+ emission_O2+SO4.ferm.+PO4.utilise; 0.261, 0.612, pH+tmp+Main.P-Source.Conc.+P-Source.Feed.conc.+ X.F.Suc+total.cell+PL+rab+SO4.ferm.+PO4.utilise; 0.247, 0.612, pH+Main.P-Source.Conc.+P-Source.Feed.conc.+ X.F.Suc+X.VXdt+total.Vol+PL+rab+lactate+SO4.ferm.+ PO4.utilise; 0.260, 0.612, pH+Main.P-Source.Conc.+P-Source.Feed.conc.+OD+X.F.Suc+X.VXdt+PL+rab+ SO4.ferm.+PO4.utilise; 0.286, 0.612, tmp+Main.P-Source.Conc.+P-Source.Feed.conc.+X.F.Suc+total.Vol+ emission_O2+SO4.ferm.+PO4.utilise; 0.260, 0.612, pH+Main.P-Source.Conc.+P-Source.Feed.conc.+Ly-s_conc.+X.F.Suc+PL+emission_O2+Thr+SO4.ferm.+ PO4.utilise; 0.247, 0.612, pH+tmp+Main.P-Source.Conc.+ P-Source.Feed.conc.+Main.Thr.Conc.+X.F.Suc+X.VXdt+ PL+rab+SO4.ferm.+PO4.utilise; 0.286, 0.612, tmp+Main.P-Source.Conc.+P-Source.Feed.conc.+total.Vol+yield+PL+ SO4.ferm.+PO4.utilise; 0.260, 0.612, tmp+Main.P-Source.Conc.+P-Source.Feed.conc.+X.F.Suc+total.Vol+ PL+Thr+His+SO4.ferm.+PO4.utilise; 0.273, 0.612, pH+tmp+Main.P-Source.Conc.+P-Source.Feed.conc.+ total.Vol+yield+PL+SO4.ferm.+PO4.utilise; 0.260, 0.612, pH+tmp+Main.P-Source.Conc.+P-Source.Feed.conc.+ X.F.Suc+X.VXdt+total.Vol+PL+SO4.ferm.+PO4.utilise; 0.247, 0.612, pH+Main.P-Source.Conc.+P-Source.Feed. conc.+X.F.Suc+total.Vol+PL+rab+His+SO4.ferm.+ PO4.ferm.+PO4.utilise; 0.298, 0.612, Main.P-Source.Conc.+P-Source.Feed.conc.+Nitrogen.Conc.+ X.F.Suc+emission_O2+SO4.ferm.+PO4.utilise; 0.246, 0.612, pH+Main.P-Source.Conc.+P-Source.Feed.conc.+Ni-trogen.Conc.+X.F.Suc+X.VXdt+total.Vol+PL+emis-sion_O2+SO4.ferm.+PO4.utilise; 0.260, 0.612, pH+Main.P-Source.Conc.+P-Source.Feed.conc.+ Nitrogen.Conc.+X.F.Suc+PL+rab+SO4.ferm.+PO4.ferm.+ PO4.utilise; 0.273, 0.612, Main.P-Source.Conc.+P-Source. Feed.conc.+X.F.Suc+X.VXdt+PL+emission_O2+Thr+ SO4.ferm.+PO4.utilise; 0.310, 0.612, tmp+Main.P-Source.Conc.+P-Source.Feed.conc.+yield+SO4.ferm.+ PO4.utilise; 0.246, 0.611, pH+tmp+Main.P-Source.Conc.+ P-Source.Feed.conc.+X.F.Suc+X.VXdt+PL+rab+lactate+ SO4.ferm.+PO4.utilise; 0.232, 0.611, pH+Main.P-Source.Conc.+P-Source.Feed.conc.+OD+X.F.Suc+ total.Vol+total.cell+PL+rab+SO4.ferm.+PO4.ferm.+ PO4.utilise; 0.273, 0.611, tmp+Main.P-Source.Conc.+P-Source.Feed.conc.+Main.Thr.Conc.+X.F.Suc+PL+rab+ SO4.ferm.+PO4.utilise; 0.310, 0.611, Main.P-Source.Conc.+P-Source.Feed.conc.+yield+rab+SO4.ferm.+ PO4.utilise; 0.273, 0.611, Main.P-Source.Conc.+P-Source.Feed.conc.+X.F.Suc+total.cell+PL+rab+SO4.ferm.+ PO4.ferm.+PO4.utilise; 0.273, 0.611, tmp+Main.P-Source.Conc.+P-Source.Feed.conc.+yield+PL+His+ SO4.ferm.+PO4.ferm.+PO4.utilise; 0.246, 0.611, pH+Main.P-Source.Conc.+P-Source.Feed.conc.+X.F.Suc+ X.VXdt+PL+emission_O2+Thr+lactate+SO4.ferm.+ PO4.utilise; 0.246, 0.611, pH+tmp+Main.P-Source.Conc.+ P-Source.Feed.conc.+X.F.Suc+X.VXdt+total.cell+PL+rab+ SO4.ferm.+PO4.utilise; 0.260, 0.611, pH+Main.P-Source.Conc.+P-Source.Feed.conc.+X.F.Suc+X.VXdt+ total.cell+PL+emission_O2+SO4.ferm.+PO4.utilise; 0.202, 0.611, pH+Main.P-Source.Conc.+P-Source.Feed.conc.+ Main.Thr.Conc.+OD+Lys_conc.+Cell+total.Vol+total.cell+ yield+PL+rab+SO4.ferm.+PO4.utilise; 0.286, 0.611, pH+Main.P-Source.Conc.+P-Source.Feed.conc.+X.F.Suc+ emission_O2+SO4.ferm.+PO4.ferm.+PO4.utilise; 0.273, 0.611, tmp+Main.P-Source.Conc.+P-Source.Feed.conc.+

X.F.Suc+emission_O2+Thr+His+SO4.ferm.+PO4.utilise; 0.259, 0.611, pH+Main.P-Source.Conc.+P-Source.Feed.conc.+X.F.Suc+total.cell+PL+rab+SO4.ferm.+PO4.ferm.+PO4.utilise; 0.259, 0.611, tmp+Main.P-Source.Conc.+P-Source.Feed.conc.+Nitrogen.Conc.+X.F.Suc+X.VXdt+PL+emission_O2+SO4.ferm.+PO4.utilise; 0.298, 0.611, tmp+Main.P-Source.Conc.+P-Source.Feed.conc.+total.Vol+yield+SO4.ferm.+PO4.utilise; 0.272, 0.611, Main.P-Source.Conc.+P-Source.Feed.conc.+X.F.Suc+total.cell+PL+rab+Thr+SO4.ferm.+PO4.utilise; 0.272, 0.611, Main.P-Source.Conc.+P-Source.Feed.conc.+X.F.Suc+X.VXdt+PL+rab+lactate+SO4.ferm.+PO4.utilise; 0.259, 0.611, pH+Main.P-Source.Conc.+P-Source.Feed.conc.+Nitrogen.Conc.+X.F.Suc+X.VXdt+PL+emission_O2+SO4.ferm.+PO4.utilise; 0.272, 0.611, Main.P-Source.Conc.+P-Source.Feed.conc.+Nitrogen.Conc.+X.F.Suc+PL+emission_O2+His+SO4.ferm.+PO4.utilise; 0.272, 0.611, tmp+Main.P-Source.Conc.+P-Source.Feed.conc.+Nitrogen.Conc.+yield+PL+SO4.ferm.+PO4.ferm.+PO4.utilise; 0.272, 0.611, Main.P-Source.Conc.+P-Source.Feed.conc.+Lys_conc.+X.F.Suc+PL+emission_O2+His+SO4.ferm.+PO4.utilise; 0.245, 0.611, pH+tmp+Main.P-Source.Conc.+P-Source.Feed.conc.+X.F.Suc+X.VXdt+total.Vol+PL+emission_O2+SO4.ferm.+PO4.utilise; 0.245, 0.611, pH+Main.P-Source.Conc.+P-Source.Feed.conc.+X.F.Suc+total.Vol+PL+rab+Thr+SO4.ferm.+PO4.ferm.+PO4.utilise; 0.245, 0.611, pH+tmp+Main.P-Source.Conc.+P-Source.Feed.conc.+X.F.Suc+X.VXdt+PL+rab+Thr+SO4.ferm.+PO4.utilise; 0.259, 0.611, pH+tmp+Main.P-Source.Conc.+P-Source.Feed.conc.+yield+PL+His+SO4.ferm.+PO4.ferm.+PO4.utilise; 0.297, 0.611, tmp+Main.P-Source.Conc.+P-Source.Feed.conc.+X.F.Suc+SO4.ferm.+PO4.ferm.+PO4.utilise; 0.272, 0.611, tmp+Main.P-Source.Conc.+P-Source.Feed.conc.+Main.Thr.Conc.+X.F.Suc+PL+emission_O2+SO4.ferm.+PO4.utilise; 0.285, 0.611, tmp+Main.P-Source.Conc.+P-Source.Feed.conc.+X.F.Suc+total.Vol+Thr+SO4.ferm.+PO4.utilise; 0.309, 0.611, Main.P-Source.Conc.+P-Source.Feed.conc.+yield+emission_O2+SO4.ferm.+PO4.utilise; 0.285, 0.611, Main.P-Source.Conc.+P-Source.Feed.conc.+X.F.Suc+rab+His+SO4.ferm.+PO4.ferm.+PO4.utilise; 0.285, 0.611, pH+Main.P-Source.Conc.+P-Source.Feed.conc.+X.F.Suc+X.VXdt+emission_O2+SO4.ferm.+PO4.utilise; 0.245, 0.611, pH+tmp+Main.P-Source.Conc.+P-Source.Feed.conc.+X.F.Suc+PL+emission_O2+Thr+SO4.ferm.+PO4.ferm.+PO4.utilise; 0.245, 0.611, pH+tmp+Main.P-Source.Conc.+P-Source.Feed.conc.+X.F.Suc+PL+emission_O2+His+SO4.ferm.+PO4.ferm.+PO4.utilise; 0.259, 0.611, pH+Main.P-Source.Conc.+P-Source.Feed.conc.+Main.Thr.Conc.+X.F.Suc+PL+rab+SO4.ferm.+PO4.ferm.+PO4.utilise; 0.272, 0.611, Main.P-Source.Conc.+P-Source.Feed.conc.+OD+X.F.Suc+X.VXdt+PL+rab+SO4.ferm.+PO4.utilise; 0.259, 0.610, pH+tmp+Main.P-Source.Conc.+P-Source.Feed.conc.+X.F.Suc+PL+Thr+SO4.ferm.+PO4.ferm.+PO4.utilise; 0.320, 0.610, Main.P-Source.Conc.+P-Source.Feed.conc.+X.F.Suc+SO4.ferm.+PO4.utilise; 0.272, 0.610, pH+Main.P-Source.Conc.+P-Source.Feed.conc.+X.F.Suc+total.Vol+rab+His+SO4.ferm.+PO4.utilise; 0.272, 0.610, Main.P-Source.Conc.+P-Source.Feed.conc.+Nitrogen.Conc.+X.F.Suc+total.Vol+PL+emission_O2+SO4.ferm.+PO4.utilise; 0.272, 0.610, tmp+Main.P-Source.Conc.+P-Source.Feed.conc.+Nitrogen.Conc.+X.F.Suc+X.VXdt+PL+SO4.ferm.+PO4.utilise; 0.309, 0.610, Main.P-Source.Conc.+P-Source.Feed.conc.+X.F.Suc+PL+SO4.ferm.+PO4.utilise; 0.258, 0.610, tmp+Main.P-Source.Conc.+P-Source.Feed.conc.+Main.Thr.Conc.+X.F.Suc+PL+rab+Thr+SO4.ferm.+PO4.utilise; 0.230, 0.610, pH+tmp+Main.P-Source.Conc.+P-Source.Feed.conc.+X.F.Suc+X.VXdt+PL+rab+His+SO4.ferm.+PO4.ferm.+PO4.utilise; 0.245, 0.610, pH+Main.P-Source.Conc.+P-Source.Feed.conc.+X.F.Suc+X.VXdt+PL+emission_O2+His+SO4.ferm.+PO4.ferm.+PO4.utilise; 0.245, 0.610, pH+Main.P-Source.Conc.+P-Source.Feed.conc.+X.F.Suc+X.VXdt+total.Vol+PL+rab+Thr+SO4.ferm.+PO4.utilise; 0.272, 0.610, Main.P-Source.Conc.+P-Source.Feed.conc.+Nitrogen.Conc.+X.F.Suc+X.VXdt+PL+emission_O2+SO4.ferm.+PO4.utilise; 0.258, 0.610, Main.P-Source.Conc.+P-Source.Feed.conc.+X.F.Suc+X.VXdt+PL+rab+Thr+His+SO4.ferm.+PO4.utilise; 0.244, 0.610, pH+tmp+Main.P-Source.Conc.+P-Source.Feed.conc.+Main.Thr.Conc.+X.F.Suc+X.VXdt+PL+emission_O2+SO4.ferm.+PO4.utilise; 0.271, 0.610, Main.P-Source.Conc.+P-Source.Feed.conc.+X.F.Suc+total.cell+PL+rab+His+SO4.ferm.+PO4.utilise; 0.284, 0.610, pH+Main.P-Source.Conc.+P-Source.Feed.conc.+yield+PL+rab+SO4.ferm.+PO4.utilise; 0.284, 0.610, Main.P-Source.Conc.+P-Source.Feed.conc.+OD+X.F.Suc+PL+emission_O2+SO4.ferm.+PO4.utilise; 0.271, 0.610, Main.P-Source.Conc.+P-Source.Feed.conc.+X.F.Suc+X.VXdt+total.cell+PL+emission_O2+SO4.ferm.+PO4.utilise; 0.271, 0.610, Main.P-Source.Conc.+P-Source.Feed.conc.+X.F.Suc+PL+rab+Thr+lactate+SO4.ferm.+PO4.utilise; 0.284, 0.610, tmp+Main.P-Source.Conc.+P-Source.Feed.conc.+X.F.Suc+total.Vol+His+SO4.ferm.+PO4.utilise; 0.271, 0.610, Main.P-Source.Conc.+P-Source.Feed.conc.+Main.Thr.Conc.+X.F.Suc+X.VXdt+PL+emission_O2+SO4.ferm.+PO4.utilise; 0.271, 0.610, Main.P-Source.Conc.+P-Source.Feed.conc.+X.F.Suc+PL+emission_O2+Thr+lactate+SO4.ferm.+PO4.utilise; 0.258, 0.610, pH+tmp+Main.P-Source.Conc.+P-Source.Feed.conc.+Main.Thr.Conc.+X.F.Suc+PL+rab+SO4.ferm.+PO4.utilise; 0.230, 0.610, pH+Main.P-Source.Conc.+P-Source.Feed.conc.+X.F.Suc+X.VXdt+total.Vol+PL+rab+His+SO4.ferm.+PO4.ferm.+PO4.utilise; 0.284, 0.610, tmp+Main.P-Source.Conc.+P-Source.Feed.conc.+X.F.Suc+rab+SO4.ferm.+PO4.ferm.+PO4.utilise; 0.258, 0.610, pH+Main.P-Source.Conc.+P-Source.Feed.conc.+X.F.Suc+X.VXdt+PL+emission_O2+lactate+SO4.ferm.+PO4.utilise; 0.258, 0.610, pH+tmp+Main.P-Source.Feed.conc.+Nitrogen.Conc.+X.F.Suc+PL+emission_O2+SO4.ferm.+PO4.utilise; 0.271, 0.610, tmp+Main.P-Source.Conc.+P-Source.Feed.conc.+X.F.Suc+X.VXdt+PL+Thr+SO4.ferm.+PO4.utilise; 0.271, 0.610, Main.P-Source.Conc.+P-Source.Feed.conc.+Lys_conc.+X.F.Suc+PL+rab+His+SO4.ferm.+PO4.utilise; 0.296, 0.610, tmp+Main.P-Source.Conc.+P-Source.Feed.conc.+yield+PL+SO4.ferm.+PO4.utilise; 0.284, 0.610, Main.P-Source.Conc.+P-Source.Feed.conc.+X.F.Suc+X.VXdt+emission_O2+His+SO4.ferm.+PO4.utilise; 0.258, 0.610, Main.P-Source.Conc.+P-Source.Feed.conc.+X.F.Suc+X.VXdt+PL+emission_O2+His+SO4.ferm.+PO4.ferm.+PO4.utilise; 0.271, 0.610, Main.P-Source.Conc.+P-Source.Feed.conc.+Main.Thr.Conc.+X.F.Suc+PL+rab+SO4.ferm.+PO4.ferm.+PO4.utilise; 0.296, 0.610, Main.P-Source.Conc.+P-Source.Feed.conc.+Lys_conc.+X.F.Suc+emission_O2+SO4.ferm.+PO4.utilise; 0.244, 0.610, pH+tmp+Main.P-Source.Conc.+P-Source.Feed.conc.+Nitrogen.Conc.+X.F.Suc+PL+rab+Thr+SO4.ferm.+PO4.utilise; 0.284, 0.610, Main.P-Source.Conc.+P-Source.Feed.conc.+X.F.Suc+emission_O2+Thr+SO4.ferm.+

PO4.ferm.+PO4.utilise; 0.284, 0.610, pH+tmp+Main.P-Source.Conc.+P-Source.Feed.conc.+X.F.Suc+total.Vol+SO4.ferm.+PO4.utilise; 0.271, 0.610, pH+tmp+Main.P-Source.Conc.+P-Source.Feed.conc.+X.F.Suc+rab+His+SO4.ferm.+PO4.utilise; 0.284, 0.610, Main.P-Source.Conc.+P-Source.Feed.conc.+X.F.Suc+X.VXdt+total.Vol+emission_O2+SO4.ferm.+PO4.utilise; 0.271, 0.610, Main.P-Source.Conc.+P-Source.Feed.conc.+X.F.Suc+PL+rab+lactate+SO4.ferm.+PO4.ferm.+PO4.utilise; 0.257, 0.610, pH+tmp+Main.P-Source.Conc.+P-Source.Feed.conc.+Main.Thr.Conc.+X.F.Suc+PL+emission_O2+SO4.ferm.+PO4.utilise; 0.257, 0.610, pH+tmp+Main.P-Source.Conc.+P-Source.Feed.conc.+X.F.Suc+X.VXdt+total.cell+PL+SO4.ferm.+PO4.utilise; 0.296, 0.610, Main.P-Source.Conc.+P-Source.Feed.conc.+X.F.Suc+rab+lactate+SO4.ferm.+PO4.utilise; 0.257, 0.610, tmp+Main.P-Source.Conc.+P-Source.Feed.conc.+Main.Thr.Conc.+X.F.Suc+PL+emission_O2+Thr+SO4.ferm.+PO4.utilise; 0.271, 0.610, pH+tmp+Main.P-Source.Conc.+P-Source.Feed.conc.+X.F.Suc+total.cell+PL+SO4.ferm.+PO4.utilise; 0.257, 0.610, tmp+Main.P-Source.Conc.+P-Source.Feed.conc.+X.F.Suc+X.VXdt+total.Vol+PL+emission_O2+SO4.ferm.+PO4.utilise; 0.271, 0.610, Main.P-Source.Conc.+P-Source.Feed.conc.+yield+PL+rab+His+SO4.ferm.+PO4.ferm.+PO4.utilise; 0.257, 0.610, pH+tmp+Main.P-Source.Conc.+P-Source.Feed.conc.+Nitrogen.Conc.+yield+PL+SO4.ferm.+PO4.ferm.+PO4.utilise; 0.257, 0.610, Main.P-Source.Conc.+P-Source.Feed.conc.+X.F.Suc+X.VXdt+total.Vol+total.cell+PL+rab+SO4.ferm.+PO4.utilise; 0.257, 0.610, pH+Main.P-Source.Conc.+P-Source.Feed.conc.+X.F.Suc+total.cell+PL+rab+His+SO4.ferm.+PO4.utilise; 0.270, 0.609, pH+tmp+Main.P-Source.Conc.+P-Source.Feed.conc.+X.F.Suc+emission_O2+Thr+SO4.ferm.+PO4.utilise; 0.257, 0.609, pH+Main.P-Source.Conc.+P-Source.Feed.conc.+X.F.Suc+Cell+X.VXdt+PL+rab+SO4.ferm.+PO4.utilise; 0.270, 0.609, tmp+Main.P-Source.Conc.+P-Source.Feed.conc.+Nitrogen.Conc.+X.F.Suc+PL+Thr+SO4.ferm.+PO4.utilise; 0.257, 0.609, Main.P-Source.Conc.+P-Source.Feed.conc.+X.F.Suc+total.Vol+PL+emission_O2+Thr+SO4.ferm.+PO4.ferm.+PO4.utilise; 0.296, 0.609, pH+Main.P-Source.Conc.+P-Source.Feed.conc.+X.F.Suc+PL+SO4.ferm.+PO4.utilise; 0.257, 0.609, tmp+Main.P-Source.Conc.+P-Source.Feed.conc.+X.F.Suc+X.VXdt+total.cell+PL+rab+SO4.ferm.+PO4.utilise; 0.283, 0.609, Main.P-Source.Conc.+P-Source.Feed.conc.+total.Vol+yield+PL+rab+SO4.ferm.+PO4.utilise; 0.257, 0.609, pH+Main.P-Source.Conc.+P-Source.Feed.conc.+Nitrogen.Conc.+X.F.Suc+PL+emission_O2+His+SO4.ferm.+PO4.utilise; 0.257, 0.609, Main.P-Source.Conc.+P-Source.Feed.conc.+X.F.Suc+total.Vol+PL+emission_O2+His+SO4.ferm.+PO4.ferm.+PO4.utilise; 0.229, 0.609, pH+tmp+Main.P-Source.Conc.+P-Source.Feed.conc.+X.F.Suc+X.VXdt+total.Vol+PL+rab+His+SO4.ferm.+PO4.utilise; 0.270, 0.609, pH+Main.P-Source.Conc.+P-Source.Feed.conc.+yield+PL+emission_O2+SO4.ferm.+PO4.ferm.+PO4.utilise; 0.307, 0.609, Main.P-Source.Conc.+P-Source.Feed.conc.+yield+His+SO4.ferm.+PO4.utilise; 0.243, 0.609, tmp+Main.P-Source.Conc.+P-Source.Feed.conc.+X.F.Suc+X.VXdt+PL+rab+His+SO4.ferm.+PO4.ferm.+PO4.utilise; 0.270, 0.609, pH+Main.P-Source.Conc.+P-Source.Feed.conc.+OD+X.F.Suc+PL+emission_O2+SO4.ferm.+PO4.utilise; 0.257, 0.609, Main.P-Source.Conc.+P-Source.Feed.conc.+X.F.Suc+X.VXdt+PL+rab+Thr+SO4.ferm.+PO4.ferm.+PO4.utilise; 0.283, 0.609, pH+Main.P-Source.Conc.+P-Source.Feed.conc.+yield+PL+emission_O2+SO4.ferm.+PO4.utilise; 0.283, 0.609, tmp+Main.P-Source.Conc.+P-Source.Feed.conc.+total. Vol+yield+His+SO4.ferm.+PO4.utilise; 0.283, 0.609, Main.P-Source.Conc.+P-Source.Feed.conc.+X.F.Suc+X.VXdt+rab+SO4.ferm.+PO4.ferm.+PO4.utilise; 0.270, 0.609, pH+tmp+Main.P-Source.Conc.+P-Source.Feed. conc.+Main.Thr.Conc.+X.F.Suc+PL+SO4.ferm.+PO4.utilise; 0.257, 0.609, pH+Main.P-Source.Conc.+P-Source.Feed.conc.+Nitrogen.Conc.+X.F.Suc+total.Vol+PL+emission_O2+SO4.ferm.+PO4.utilise; 0.270, 0.609, tmp+Main.P-Source.Conc.+P-Source.Feed.conc.+X.F.Suc+total.Vol+rab+His+SO4.ferm.+PO4.utilise; 0.283, 0.609, tmp+Main.P-Source.Conc.+P-Source.Feed.conc.+Main.Thr.Conc.+X.F.Suc+PL+SO4.ferm.+PO4.utilise; 0.243, 0.609, pH+tmp+Main.P-Source.Conc.+P-Source.Feed. conc.+X.F.Suc+total.Vol+PL+Thr+His+SO4.ferm.+PO4.utilise; 0.243, 0.609, tmp+Main.P-Source.Conc.+P-Source.Feed.conc.+X.F.Suc+X.VXdt+PL+rab+Thr+His+SO4.ferm.+PO4.utilise; 0.283, 0.609, Main.P-Source.Conc.+P-Source.Feed.conc.+Nitrogen.Conc.+X.F.Suc+rab+Thr+SO4.ferm.+PO4.utilise; 0.295, 0.609, Main.P-Source.Conc.+P-Source.Feed.conc.+Main.Thr.Conc.+X.F.Suc+rab+SO4.ferm.+PO4.utilise; 0.283, 0.609, Main.P-Source.Conc.+P-Source.Feed.conc.+total.Vol+yield+PL+emission_O2+SO4.ferm.+PO4.utilise; 0.270, 0.609, pH+Main.P-Source.Conc.+P-Source.Feed.conc.+X.F.Suc+total.Vol+emission_O2+Thr+SO4.ferm.+PO4.utilise; 0.229, 0.609, pH+tmp+Main.P-Source.Conc.+P-Source.Feed.conc.+X.F.Suc+X.VXdt+PL+emission_O2+Thr+lactate+SO4.ferm.+PO4.utilise; 0.257, 0.609, pH+Main.P-Source.Conc.+P-Source.Feed.conc.+X.F.Suc+PL+rab+His+lactate+SO4.ferm.+PO4.utilise; 0.295, 0.609, tmp+Main.P-Source.Conc.+P-Source.Feed.conc.+yield+SO4.ferm.+PO4.ferm.+PO4.utilise; 0.256, 0.609, tmp+Main.P-Source.Conc.+P-Source.Feed.conc.+Nitrogen. Conc.+X.F.Suc+PL+emission_O2+Thr+SO4.ferm.+PO4.utilise; 0.283, 0.609, pH+tmp+Main.P-Source.Conc.+P-Source.Feed.conc.+yield+PL+SO4.ferm.+PO4.utilise; 0.295, 0.609, Main.P-Source.Conc.+P-Source.Feed.conc.+Main.Thr.Conc.+X.F.Suc+emission_O2+SO4.ferm.+PO4.utilise; 0.256, 0.609, pH+Main.P-Source.Conc.+P-Source.Feed.conc.+Lys_conc.+X.F.Suc+PL+emission_O2+His+SO4.ferm.+PO4.utilise; 0.243, 0.609, pH+Main.P-Source.Conc.+P-Source.Feed.conc.+X.F.Suc+X.VXdt+total.Vol+total.cell+PL+emission_O2+SO4.ferm.+PO4.utilise; 0.228, 0.609, pH+Main.P-Source.Conc.+P-Source.Feed.conc.+X.F.Suc+X.VXdt+PL+rab+Thr+His+lactate+SO4.ferm.+PO4.utilise; 0.243, 0.609, pH+Main.P-Source.Conc.+P-Source.Feed.conc.+X.F.Suc+PL+rab+Thr+His+SO4.ferm.+PO4.ferm.+PO4.utilise; 0.270, 0.609, pH+Main.P-Source.Conc.+P-Source.Feed.conc.+X.F.Suc+total.Vol+PL+SO4.ferm.+PO4.ferm.+PO4.utilise; 0.242, 0.609, pH+Main.P-Source.Conc.+P-Source.Feed.conc.+X.F.Suc+PL+emission_O2+Thr+lactate+SO4.ferm.+PO4.ferm.+PO4.utilise; 0.256, 0.609, tmp+Main.P-Source.Conc.+P-Source.Feed.conc.+Nitrogen.Conc.+X.F.Suc+total.Vol+PL+rab+SO4.ferm.+PO4.utilise; 0.256, 0.609, tmp+Main.P-Source.Conc.+P-Source.Feed.conc.+X.F.Suc+total.Vol+PL+rab+SO4.ferm.+PO4.ferm.+PO4.utilise; 0.228, 0.609, pH+Main.P-Source.Conc.+P-Source.Feed.conc.+X.F.Suc+X.VXdt+total.Vol+PL+emission_O2+Thr+lactate+SO4.ferm.+PO4.utilise; 0.228, 0.609, pH+Main.P-Source.Conc.+P-Source.Feed.conc.+OD+X.F.Suc+total.Vol+total.cell+PL+rab+lactate+SO4.ferm.+PO4.utilise; 0.282, 0.609, tmp+Main.P-Source.Conc.+P-Source.Feed.conc.+X.F.Suc+total.cell+PL+SO4.ferm.+PO4.utilise; 0.282, 0.609, tmp+Main.P-Source.Conc.+P-Source.Feed.conc.+X.F.Suc+X.VXdt+ emission_O2+SO4.ferm.+PO4.utilise; 0.256, 0.609, Main.P-Source.Conc.+P-Source.Feed.conc.+OD+X.F.Suc+ X.VXdt+total.Vol+PL+rab+SO4.ferm.+PO4.utilise; 0.256, 0.609, pH+Main.P-Source.Conc.+P-Source.Feed.conc.+ X.F.Suc+total.cell+PL+rab+Thr+SO4.ferm.+PO4.utilise; 0.256, 0.609, pH+Main.P-Source.Conc.+P-Source.Feed. conc.+Lys_conc.+X.F.Suc+PL+rab+His+SO4.ferm.+ PO4.utilise; 0.242, 0.609, tmp+Main.P-Source.Conc.+P-Source.Feed.conc.+X.F.Suc+X.VXdt+total.Vol+PL+rab+ His+SO4.ferm.+PO4.utilise; 0.269, 0.609, tmp+Main.P-Source.Conc.+P-Source.Feed.conc.+X.F.Suc+X.VXdt+ total.Vol+PL+SO4.ferm.+PO4.utilise; 0.256, 0.609, Main.P-Source.Conc.+P-Source.Feed.conc.+Nitrogen.Conc.+ X.F.Suc+total.Vol+PL+rab+Thr+SO4.ferm.+PO4.utilise; 0.256, 0.609, Main.P-Source.Conc.+P-Source.Feed.conc.+ X.F.Suc+X.VXdt+total.Vol+PL+emission_O2+Thr+ SO4.ferm.+PO4.utilise; 0.256, 0.609, tmp+Main.P-Source.Conc.+P-Source.Feed.conc.+Main.Thr.Conc.+ X.F.Suc+X.VXdt+PL+rab+SO4.ferm.+PO4.utilise; 0.228, 0.609, pH+tmp+Main.P-Source.Conc.+P-Source.Feed. conc.+X.F.Suc+total.Vol+PL+emission_O2+Thr+His+ SO4.ferm.+PO4.utilise; 0.242, 0.608, pH+Main.P-Source.Conc.+P-Source.Feed.conc.+X.F.Suc+X.VXdt+PL+ rab+His+lactate+SO4.ferm.+PO4.utilise; 0.242, 0.608, pH+tmp+Main.P-Source.Conc.+P-Source.Feed.conc.+ Main.Thr.Conc.+X.F.Suc+PL+rab+Thr+SO4.ferm.+ PO4.utilise; 0.282, 0.608, Main.P-Source.Conc.+P-Source.Feed.conc.+X.F.Suc+emission_O2+His+ SO4.ferm.+PO4.ferm.+PO4.utilise; 0.269, 0.608, pH+Main.P-Source.Conc.+P-Source.Feed.conc.+X.F.Suc+ X.VXdt+total.Vol+PL+SO4.ferm.+PO4.utilise; 0.294, 0.608, Main.P-Source.Conc.+P-Source.Feed.conc.+Lys_conc.+X.F.Suc+rab+SO4.ferm.+PO4.utilise; 0.256, 0.608, pH+Main.P-Source.Conc.+P-Source.Feed.conc.+ X.F.Suc+total.Vol+total.cell+PL+rab+SO4.ferm.+ PO4.utilise; 0.269, 0.608, Main.P-Source.Conc.+P-Source.Feed.conc.+X.F.Suc+total.Vol+emission_O2+Thr+ His+SO4.ferm.+PO4.utilise; 0.294, 0.608, tmp+Main.P-Source.Conc.+P-Source.Feed.conc.+yield+His+SO4.ferm.+ PO4.utilise; 0.256, 0.608, pH+Main.P-Source.Conc.+P-Source.Feed.conc.+Main.Thr.Conc.+X.F.Suc+PL+ emission_O2+SO4.ferm.+PO4.ferm.+PO4.utilise; 0.242, 0.608, pH+Main.P-Source.Conc.+P-Source.Feed.conc.+ X.F.Suc+total.Vol+PL+emission_O2+His+SO4.ferm.+ PO4.ferm.+PO4.utilise; 0.269, 0.608, tmp+Main.P-Source.Conc.+P-Source.Feed.conc.+X.F.Suc+total.Vol+ emission_O2+Thr+SO4.ferm.+PO4.utilise; 0.269, 0.608, Main.P-Source.Conc.+P-Source.Feed.conc.+X.F.Suc+ total.Vol+total.cell+PL+rab+SO4.ferm.+PO4.utilise; 0.269, 0.608, tmp+Main.P-Source.Conc.+P-Source.Feed.conc.+total.Vol+yield+PL+His+SO4.ferm.+PO4.utilise; 0.255, 0.608, pH+tmp+Main.P-Source.Conc.+P-Source.Feed. conc.+Nitrogen.Conc.+X.F.Suc+PL+Thr+SO4.ferm.+ PO4.utilise; 0.269, 0.608, Main.P-Source.Conc.+P-Source.Feed.conc.+X.F.Suc+Cell+total.Vol+PL+rab+SO4.ferm.+ PO4.utilise; 0.269, 0.608, Main.P-Source.Conc.+P-Source.Feed.conc.+X.F.Suc+Cell+X.VXdt+PL+rab+ SO4.ferm.+PO4.utilise; 0.241, 0.608, tmp+Main.P-Source.Conc.+P-Source.Feed.conc.+X.F.Suc+PL+rab+ Thr+His+SO4.ferm.+PO4.ferm.+PO4.utilise; 0.281, 0.608, Main.P-Source.Conc.+P-Source.Feed.conc.+X.F.Suc+ X.VXdt+rab+Thr+SO4.ferm.+PO4.utilise; 0.294, 0.608, Main.P-Source.Conc.+P-Source.Feed.conc.+X.F.Suc+ total.cell+rab+SO4.ferm.+PO4.utilise; 0.241, 0.608, pH+Main.P-Source.Conc.+P-Source.Feed.conc.+OD+ X.F.Suc+X.VXdt+total.Vol+PL+emission_O2+SO4.ferm.+ PO4.utilise; 0.268, 0.608, Main.P-Source.Conc.+P-Source.Feed.conc.+Nitrogen.Conc.+X.F.Suc+PL+emission_O2+SO4.ferm.+PO4.ferm.+PO4.utilise; 0.281, 0.608, Main.P-Source.Conc.+P-Source.Feed.conc.+X.F.Suc+ total.Vol+rab+SO4.ferm.+PO4.ferm.+PO4.utilise; 0.255, 0.608, Main.P-Source.Conc.+P-Source.Feed.conc.+Main. Thr.Conc.+X.F.Suc+X.VXdt+total.Vol+PL+rab+ SO4.ferm.+PO4.utilise; 0.255, 0.608, pH+Main.P-Source.Conc.+P-Source.Feed.conc.+X.F.Suc+Cell+total. Vol+PL+rab+SO4.ferm.+PO4.utilise; 0.212, 0.608, pH+Main.P-Source.Conc.+P-Source.Feed.conc.+OD+ X.F.Suc+total.Vol+total.cell+PL+rab+Thr+lactate+ SO4.ferm.+PO4.utilise; 0.241, 0.608, pH+tmp+Main.P-Source.Conc.+P-Source.Feed.conc.+X.F.Suc+X.VXdt+PL+ emission_O2+lactate+SO4.ferm.+PO4.utilise; 0.255, 0.608, Main.P-Source.Conc.+P-Source.Feed.conc.+Nitrogen. Conc.+X.F.Suc+X.VXdt+total.Vol+PL+emission_O2+ SO4.ferm.+PO4.utilise; 0.281, 0.608, Main.P-Source.Conc.+P-Source.Feed.conc.+Lys_conc.+yield+PL+ emission_O2+SO4.ferm.+PO4.utilise; 0.255, 0.608, Main.P-Source.Conc.+P-Source.Feed.conc.+X.F.Suc+ X.VXdt+PL+emission_O2+Thr+lactate+SO4.ferm.+ PO4.utilise; 0.268, 0.608, Main.P-Source.Conc.+P-Source.Feed.conc.+Main.Thr.Conc.+X.F.Suc+PL+emission_O2+SO4.ferm.+PO4.ferm.+PO4.utilise; 0.268, 0.608, pH+Main.P-Source.Conc.+P-Source.Feed.conc.+X.F.Suc+ total.Vol+emission_O2+His+SO4.ferm.+PO4.utilise; 0.241, 0.608, pH+tmp+Main.P-Source.Conc.+P-Source.Feed. conc.+Main.Thr.Conc.+X.F.Suc+PL+emission_O2+Thr+ SO4.ferm.+PO4.utilise; 0.268, 0.608, pH+tmp+Main.P-Source.Conc.+P-Source.Feed.conc.+X.F.Suc+total.Vol+ rab+SO4.ferm.+PO4.utilise; 0.293, 0.608, Main.P-Source.Conc.+P-Source.Feed.conc.+X.F.Suc+ emission_O2+lactate+SO4.ferm.+PO4.utilise; 0.305, 0.608, Main.P-Source.Conc.+P-Source.Feed.conc.+yield+PL+ SO4.ferm.+PO4.utilise; 0.255, 0.608, pH+tmp+Main.P-Source.Conc.+P-Source.Feed.conc.+total.Vol+yield+PL+ His+SO4.ferm.+PO4.utilise; 0.293, 0.608, Main.P-Source.Conc.+P-Source.Feed.conc.+yield+rab+His+ SO4.ferm.+PO4.utilise; 0.255, 0.608, Main.P-Source.Conc.+P-Source.Feed.conc.+Nitrogen.Conc.+ X.F.Suc+PL+rab+Thr+His+SO4.ferm.+PO4.utilise; 0.241, 0.608, pH+tmp+Main.P-Source.Conc.+P-Source.Feed. conc.+X.F.Suc+total.Vol+PL+rab+SO4.ferm.+PO4.ferm.+ PO4.utilise; 0.255, 0.608, Main.P-Source.Conc.+P-Source.Feed.conc.+X.F.Suc+PL+rab+Thr+lactate+ SO4.ferm.+PO4.ferm.+PO4.utilise; 0.268, 0.608, tmp+ Main.P-Source.Conc.+P-Source.Feed.conc.+X.F.Suc+ total.cell+PL+emission_O2+SO4.ferm.+PO4.utilise; 0.196, 0.608, pH+Main.P-Source.Conc.+P-Source.Feed.conc.+ Main.Thr.Conc.+OD+Lys_conc.+Cell+total.Vol+total.cell+ yield+PL+emission_O2+SO4.ferm.+PO4.utilise; 0.241, 0.608, pH+Main.P-Source.Conc.+P-Source.Feed.conc.+ X.F.Suc+Cell+X.VXdt+total.Vol+PL+rab+SO4.ferm.+ PO4.utilise; 0.293, 0.608, Main.P-Source.Conc.+P-Source.Feed.conc.+total.Vol+yield+rab+SO4.ferm.+ PO4.utilise; 0.268, 0.608, Main.P-Source.Conc.+P-Source.Feed.conc.+X.F.Suc+Cell+PL+rab+His+ SO4.ferm.+PO4.utilise; 0.254, 0.608, pH+Main.P-Source.Conc.+P-Source.Feed.conc.+X.F.Suc+PL+emission_O2+lactate+SO4.ferm.+PO4.ferm.+PO4.utilise; 0.281, 0.608, Main.P-Source.Conc.+P-Source.Feed.conc.+ X.F.Suc+total.Vol+PL+SO4.ferm.+PO4.ferm.+PO4.utilise; 0.241, 0.608, Main.P-Source.Conc.+P-Source.Feed.conc.+ OD+X.F.Suc+total.Vol+total.cell+PL+rab+SO4.ferm.+ PO4.ferm.+PO4.utilise; 0.281, 0.608, Main.P-Source.Conc.+P-Source.Feed.conc.+yield+PL+rab+His+ SO4.ferm.+PO4.utilise; 0.281, 0.608, Main.P-Source.Conc.+P-Source.Feed.conc.+Lys_conc.+yield+PL+ rab+SO4.ferm.+PO4.utilise; 0.268, 0.608, Main.P-Source.Conc.+P-Source.Feed.conc.+Main.Thr.Conc.+X.F.Suc+PL+rab+His+SO4.ferm.+PO4.utilise; 0.226, 0.608, pH+Main.P-Source.Conc.+P-Source.Feed.conc.+OD+X.F.Suc+total.Vol+total.cell+PL+rab+His+SO4.ferm.+PO4.utilise; 0.305, 0.607, Main.P-Source.Conc.+P-Source.Feed.conc.+yield+SO4.ferm.+PO4.ferm.+PO4.utilise; 0.268, 0.607, pH+tmp+Main.P-Source.Conc.+P-Source.Feed.conc.+X.F.Suc+Thr+His+SO4.ferm.+PO4.utilise; 0.240, 0.607, pH+Main.P-Source.Conc.+P-Source.Feed.conc.+Nitrogen.Conc.+X.F.Suc+X.VXdt+PL+rab+SO4.ferm.+PO4.ferm.+PO4.utilise; 0.293, 0.607, Main.P-Source.Conc.+P-Source.Feed.conc.+total.Vol+yield+emission_O2+SO4.ferm.+PO4.utilise; 0.268, 0.607, Main.P-Source.Conc.+P-Source.Feed.conc.+X.F.Suc+PL+rab+His+lactate+SO4.ferm.+PO4.utilise; 0.226, 0.607, pH+Main.P-Source.Conc.+P-Source.Feed.conc.+X.F.Suc+X.VXdt+PL+rab+Thr+lactate+SO4.ferm.+PO4.ferm.+PO4.utilise; 0.240, 0.607, pH+Main.P-Source.Conc.+P-Source.Feed.conc.+X.F.Suc+X.VXdt+total.cell+PL+rab+SO4.ferm.+PO4.ferm.+PO4.utilise; 0.254, 0.607, Main.P-Source.Conc.+P-Source.Feed.conc.+X.F.Suc+PL+emission_O2+Thr+His+SO4.ferm.+PO4.ferm.+PO4.utilise; 0.240, 0.607, pH+Main.P-Source.Conc.+P-Source.Feed.conc.+X.F.Suc+PL+rab+Thr+His+lactate+SO4.ferm.+PO4.utilise; 0.293, 0.607, Main.P-Source.Conc.+P-Source.Feed.conc.+yield+PL+SO4.ferm.+PO4.ferm.+PO4.utilise; 0.280, 0.607, tmp+Main.P-Source.Conc.+P-Source.Feed.conc.+X.F.Suc+emission_O2+SO4.ferm.+PO4.ferm.+PO4.utilise; 0.240, 0.607, pH+tmp+Main.P-Source.Conc.+P-Source.Feed.conc.+X.F.Suc+X.VXdt+PL+His+SO4.ferm.+PO4.ferm.+PO4.utilise; 0.240, 0.607, pH+Main.P-Source.Conc.+P-Source.Feed.conc.+X.F.Suc+X.VXdt+total.Vol+PL+emission_O2+lactate+SO4.ferm.+PO4.utilise; 0.280, 0.607, Main.P-Source.Conc.+P-Source.Feed.conc.+Main.Thr.Conc.+X.F.Suc+rab+Thr+SO4.ferm.+PO4.utilise; 0.267, 0.607, tmp+Main.P-Source.Conc.+P-Source.Feed.conc.+Main.Thr.Conc.+X.F.Suc+PL+Thr+SO4.ferm.+PO4.utilise; 0.254, 0.607, pH+Main.P-Source.Conc.+P-Source.Feed.conc.+X.F.Suc+Cell+PL+rab+SO4.ferm.+PO4.ferm.+PO4.utilise; 0.254, 0.607, pH+Main.P-Source.Conc.+P-Source.Feed.conc.+X.F.Suc+Cell+PL+rab+His+SO4.ferm.+PO4.utilise; 0.280, 0.607, pH+Main.P-Source.Conc.+P-Source.Feed.conc.+Nitrogen.Conc.+X.F.Suc+rab+SO4.ferm.+PO4.utilise; 0.240, 0.607, Main.P-Source.Conc.+P-Source.Feed.conc.+X.F.Suc+X.VXdt+total.Vol+PL+rab+His+SO4.ferm.+PO4.ferm.+PO4.utilise; 0.254, 0.607, pH+tmp+Main.P-Source.Conc.+P-Source.Feed.conc.+X.F.Suc+total.Vol+PL+SO4.ferm.+PO4.ferm.+PO4.utilise; 0.240, 0.607, tmp+Main.P-Source.Conc.+P-Source.Feed.conc.+X.F.Suc+X.VXdt+PL+rab+Thr+SO4.ferm.+PO4.ferm.+PO4.utilise; 0.267, 0.607, pH+Main.P-Source.Conc.+P-Source.Feed.conc.+X.F.Suc+X.VXdt+rab+His+SO4.ferm.+PO4.utilise; 0.226, 0.607, pH+tmp+Main.P-Source.Conc.+P-Source.Feed.conc.+OD+X.F.Suc+total.Vol+total.cell+PL+rab+SO4.ferm.+PO4.utilise; 0.280, 0.607, Main.P-Source.Conc.+P-Source.Feed.conc.+X.F.Suc+emission_O2+Thr+lactate+SO4.ferm.+PO4.utilise; 0.267, 0.607, Main.P-Source.Conc.+P-Source.Feed.conc.+Main.Thr.Conc.+X.F.Suc+total.Vol+PL+rab+SO4.ferm.+PO4.utilise; 0.254, 0.607, pH+Main.P-Source.Conc.+P-Source.Feed.conc.+Nitrogen.Conc.+X.F.Suc+PL+emission_O2+SO4.ferm.+PO4.ferm.+PO4.utilise; 0.292, 0.607, tmp+Main.P-Source.Conc.+P-Source.Feed.conc.+total.Vol+PL+SO4.ferm.+PO4.utilise; 0.240, 0.607, pH+Main.P-Source.Conc.+P-Source.Feed.conc.+X.F.Suc+X.VXdt+total.cell+PL+rab+His+SO4.ferm.+PO4.utilise; 0.267, 0.607, tmp+Main.P-Source.Conc.+P-Source.Feed.conc.+total.Vol+yield+PL+rab+SO4.ferm.+PO4.utilise; 0.280, 0.607, Main.P-Source.Conc.+P-Source.Feed.conc.+X.F.Suc+total.Vol+emission_O2+SO4.ferm.+PO4.ferm.+PO4.utilise; 0.280, 0.607, pH+tmp+Main.P-Source.Conc.+P-Source.Feed.conc.+total.Vol+PL+SO4.ferm.+PO4.utilise; 0.292, 0.607, Main.P-Source.Conc.+P-Source.Feed.conc.+yield+emission_O2+His+SO4.ferm.+PO4.utilise; 0.280, 0.607, pH+tmp+Main.P-Source.Conc.+P-Source.Feed.conc.+X.F.Suc+X.VXdt+SO4.ferm.+PO4.utilise; 0.254, 0.607, pH+tmp+Main.P-Source.Conc.+P-Source.Feed.conc.+X.F.Suc+total.cell+PL+emission_O2+SO4.ferm.+PO4.utilise; 0.240, 0.607, pH+tmp+Main.P-Source.Conc.+P-Source.Feed.conc.+Nitrogen.Conc.+X.F.Suc+total.Vol+PL+rab+SO4.ferm.+PO4.utilise; 0.280, 0.607, Main.P-Source.Conc.+P-Source.Feed.conc.+yield+PL+emission_O2+His+SO4.ferm.+PO4.utilise; 0.254, 0.607, pH+Main.P-Source.Conc.+P-Source.Feed.conc.+X.F.Suc+total.Vol+PL+rab+lactate+SO4.ferm.+PO4.utilise; 0.254, 0.607, pH+tmp+Main.P-Source.Conc.+P-Source.Feed.conc.+X.F.Suc+PL+rab+lactate+SO4.ferm.+PO4.utilise; 0.267, 0.607, Main.P-Source.Conc.+P-Source.Feed.conc.+X.F.Suc+Cell+PL+rab+SO4.ferm.+PO4.ferm.+PO4.utilise; 0.240, 0.607, pH+Main.P-Source.Conc.+P-Source.Feed.conc.+Nitrogen.Conc.+X.F.Suc+X.VXdt+PL+rab+His+SO4.ferm.+PO4.utilise; 0.280, 0.607, tmp+Main.P-Source.Conc.+P-Source.Feed.conc.+yield+His+SO4.ferm.+PO4.ferm.+PO4.utilise; 0.267, 0.607, Main.P-Source.Conc.+P-Source.Feed.conc.+OD+X.F.Suc+PL+rab+SO4.ferm.+PO4.ferm.+PO4.utilise; 0.253, 0.607, Main.P-Source.Conc.+P-Source.Feed.conc.+Lys_conc.+X.F.Suc+PL+rab+Thr+His+SO4.ferm.+PO4.utilise; 0.253, 0.607, tmp+Main.P-Source.Conc.+P-Source.Feed.conc.+Main.Thr.Conc.+X.F.Suc+X.VXdt+PL+emission_O2+SO4.ferm.+PO4.utilise; 0.253, 0.607, pH+Main.P-Source.Conc.+P-Source.Feed.conc.+yield+PL+rab+His+SO4.ferm.+PO4.ferm.+PO4.utilise; 0.267, 0.607, pH+tmp+Main.P-Source.Conc.+P-Source.Feed.conc.+X.F.Suc+emission_O2+His+SO4.ferm.+PO4.utilise; 0.267, 0.607, tmp+Main.P-Source.Conc.+P-Source.Feed.conc.+yield+PL+rab+SO4.ferm.+PO4.ferm.+PO4.utilise; 0.225, 0.607, pH+Main.P-Source.Conc.+P-Source.Feed.conc.+Nitrogen.Conc.+X.F.Suc+X.VXdt+total.Vol+PL+rab+His+SO4.ferm.+PO4.utilise; 0.279, 0.607, Main.P-Source.Conc.+P-Source.Feed.conc.+X.F.Suc+rab+Thr+lactate+SO4.ferm.+PO4.utilise; 0.239, 0.607, Main.P-Source.Conc.+P-Source.Feed.conc.+OD+X.F.Suc+X.VXdt+total.Vol+total.cell+PL+rab+SO4.ferm.+PO4.utilise; 0.279, 0.607, tmp+Main.P-Source.Conc.+P-Source.Feed.conc.+X.F.Suc+X.VXdt+His+SO4.ferm.+PO4.utilise; 0.253, 0.607, pH+Main.P-Source.Conc.+P-Source.Feed.conc.+Main.Thr.Conc.+X.F.Suc+total.Vol+PL+rab+SO4.ferm.+PO4.utilise; 0.292, 0.607, Main.P-Source.Conc.+P-Source.Feed.conc.+Lys_conc.+yield+emission_O2+SO4.ferm.+PO4.utilise; 0.253, 0.607, tmp+Main.P-Source.Conc.+P-Source.Feed.conc.+Nitrogen.Conc.+X.F.Suc+PL+rab+SO4.ferm.+PO4.ferm.+PO4.utilise; 0.266, 0.607, Main.P-Source.Conc.+P-Source.Feed.conc.+yield+PL+emission_O2+His+SO4.ferm.+PO4.ferm.+PO4.utilise; 0.266, 0.607, pH+Main.P-Source.Conc.+P-Source.Feed.conc.+X.F.Suc+X.VXdt+total.Vol+rab+SO4.ferm.+PO4.utilise; 0.279, 0.607, pH+Main.P-Source.Conc.+P-Source.Feed.conc.+X.F.Suc+rab+lactate+SO4.ferm.+PO4.utilise; 0.225, 0.607, pH+Main.P-Source.Conc.+P-Source.Feed.conc.+OD+X.F.Suc+total.Vol+total.cell+PL+emission_O2+SO4.ferm.+

PO4.ferm.+PO4.utilise; 0.266, 0.607, tmp+Main.P-Source.Conc.+P-Source.Feed.conc.+X.F.Suc+total.Vol+PL+SO4.ferm.+PO4.utilise; 0.210, 0.606, Main.P-Source.Conc.+P-Source.Feed.conc.+Main.Thr.Conc.+OD+Lys_conc.+Cell+total.Vol+total.cell+yield+PL+rab+SO4.ferm.+PO4.utilise; 0.225, 0.606, pH+tmp+Main.P-Source.Conc.+P-Source.Feed.conc.+X.F.Suc+X.VXdt+PL+emission_O2+His+SO4.ferm.+PO4.ferm.+PO4.utilise; 0.266, 0.606, pH+Main.P-Source.Conc.+P-Source.Feed.conc.+total.Vol+yield+PL+rab+SO4.ferm.+PO4.utilise; 0.253, 0.606, pH+Main.P-Source.Conc.+P-Source.Feed.conc.+OD+X.F.Suc+PL+rab+SO4.ferm.+PO4.ferm.+PO4.utilise; 0.253, 0.606, tmp+Main.P-Source.Conc.+P-Source.Feed.conc.+X.F.Suc+X.VXdt+PL+rab+lactate+SO4.ferm.+PO4.utilise; 0.266, 0.606, Main.P-Source.Conc.+P-Source.Feed.conc.+Nitrogen.Conc.+yield+PL+rab+SO4.ferm.+PO4.ferm.+PO4.utilise; 0.279, 0.606, Main.P-Source.Conc.+P-Source.Feed.conc.+X.F.Suc+X.VXdt+emission_O2+SO4.ferm.+PO4.ferm.+PO4.utilise; 0.239, 0.606, Main.P-Source.Conc.+P-Source.Feed.conc.+X.F.Suc+X.VXdt+total.Vol+PL+rab+Thr+His+SO4.ferm.+PO4.utilise; 0.266, 0.606, Main.P-Source.Conc.+P-Source.Feed.conc.+OD+X.F.Suc+total.cell+PL+rab+SO4.ferm.+PO4.utilise; 0.266, 0.606, Main.P-Source.Conc.+P-Source.Feed.conc.+X.F.Suc+total.cell+PL+emission_O2+SO4.ferm.+PO4.ferm.+PO4.utilise; 0.266, 0.606, Main.P-Source.Conc.+P-Source.Feed.conc.+X.F.Suc+Cell+PL+rab+Thr+SO4.ferm.+PO4.utilise; 0.239, 0.606, pH+Main.P-Source.Conc.+P-Source.Feed.conc.+X.F.Suc+X.VXdt+PL+rab+lactate+SO4.ferm.+PO4.ferm.+PO4.utilise; 0.239, 0.606, pH+Main.P-Source.Conc.+P-Source.Feed.conc.+X.F.Suc+total.Vol+PL+emission_O2+Thr+SO4.ferm.+PO4.ferm.+PO4.utilise; 0.291, 0.606, Main.P-Source.Conc.+P-Source.Feed.conc.+total.Vol+PL+rab+SO4.ferm.+PO4.utilise; 0.239, 0.606, pH+Main.P-Source.Conc.+P-Source.Feed.conc.+X.F.Suc+PL+emission_O2+Thr+His+lactate+SO4.ferm.+PO4.utilise; 0.253, 0.606, pH+tmp+Main.P-Source.Conc.+P-Source.Feed.conc.+Main.Thr.Conc.+X.F.Suc+X.VXdt+PL+SO4.ferm.+PO4.utilise; 0.303, 0.606, Main.P-Source.Conc.+P-Source.Feed.conc.+X.F.Suc+total.Vol+SO4.ferm.+PO4.utilise; 0.266, 0.606, Main.P-Source.Conc.+P-Source.Feed.conc.+Main.Thr.Conc.+X.F.Suc+PL+emission_O2+His+SO4.ferm.+PO4.utilise; 0.224, 0.606, pH+Main.P-Source.Conc.+P-Source.Feed.conc.+OD+X.F.Suc+X.VXdt+total.Vol+total.cell+PL+emission_O2+SO4.ferm.+PO4.utilise; 0.239, 0.606, pH+Main.P-Source.Conc.+P-Source.Feed.conc.+Nitrogen.Conc.+X.F.Suc+total.Vol+PL+rab+Thr+SO4.ferm.+PO4.utilise; 0.252, 0.606, Main.P-Source.Conc.+P-Source.Feed.conc.+Main.Thr.Conc.+X.F.Suc+X.VXdt+total.Vol+PL+emission_O2+SO4.ferm.+PO4.utilise; 0.252, 0.606, pH+tmp+Main.P-Source.Conc.+P-Source.Feed.conc.+Main.Thr.Conc.+X.F.Suc+PL+Thr+SO4.ferm.+PO4.utilise; 0.252, 0.606, pH+tmp+Main.P-Source.Conc.+P-Source.Feed.conc.+X.F.Suc+rab+Thr+His+SO4.ferm.+PO4.utilise; 0.252, 0.606, pH+Main.P-Source.Conc.+P-Source.Feed.conc.+OD+X.F.Suc+X.VXdt+PL+emission_O2+SO4.ferm.+PO4.utilise; 0.266, 0.606, tmp+Main.P-Source.Conc.+P-Source.Feed.conc.+X.F.Suc+X.VXdt+rab+His+SO4.ferm.+PO4.utilise; 0.224, 0.606, pH+Main.P-Source.Conc.+P-Source.Feed.conc.+X.F.Suc+X.VXdt+total.Vol+PL+emission_O2+His+SO4.ferm.+PO4.ferm.+PO4.utilise; 0.279, 0.606, Main.P-Source.Conc.+P-Source.Feed.conc.+Main.Thr.Conc.+X.F.Suc+emission_O2+Thr+SO4.ferm.+PO4.utilise; 0.239, 0.606, pH+tmp+Main.P-Source.Conc.+P-Source.Feed.conc.+Nitrogen.Conc.+X.F.Suc+PL+emission_O2+Thr+SO4.ferm.+PO4.utilise; 0.291, 0.606, Main.P-Source.Conc.+P-Source.Feed.conc.+X.F.Suc+total.Vol+PL+SO4.ferm.+PO4.utilise; 0.266, 0.606, pH+Main.P-Source.Conc.+P-Source.Feed.conc.+X.F.Suc+rab+Thr+lactate+SO4.ferm.+PO4.utilise; 0.266, 0.606, pH+Main.P-Source.Conc.+P-Source.Feed.conc.+X.F.Suc+emission_O2+Thr+lactate+SO4.ferm.+PO4.utilise; 0.252, 0.606, Main.P-Source.Conc.+P-Source.Feed.conc.+Lys_conc.+X.F.Suc+PL+emission_O2+Thr+His+SO4.ferm.+PO4.utilise; 0.224, 0.606, pH+tmp+Main.P-Source.Conc.+P-Source.Feed.conc.+Nitrogen.Conc.+X.F.Suc+X.VXdt+PL+rab+SO4.ferm.+PO4.ferm.+PO4.utilise; 0.252, 0.606, pH+Main.P-Source.Conc.+P-Source.Feed.conc.+X.F.Suc+PL+emission_O2+His+lactate+SO4.ferm.+PO4.utilise; 0.238, 0.606, pH+tmp+Main.P-Source.Conc.+P-Source.Feed.conc.+X.F.Suc+X.VXdt+total.cell+PL+emission_O2+SO4.ferm.+PO4.utilise; 0.266, 0.606, tmp+Main.P-Source.Conc.+P-Source.Feed.conc.+X.F.Suc+PL+rab+lactate+SO4.ferm.+PO4.utilise; 0.238, 0.606, pH+Main.P-Source.Conc.+P-Source.Feed.conc.+Main.Thr.Conc.+X.F.Suc+X.VXdt+PL+rab+SO4.ferm.+PO4.ferm.+PO4.utilise; 0.266, 0.606, tmp+Main.P-Source.Conc.+P-Source.Feed.conc.+X.F.Suc+X.VXdt+total.cell+PL+SO4.ferm.+PO4.utilise; 0.252, 0.606, pH+Main.P-Source.Conc.+P-Source.Feed.conc.+Main.Thr.Conc.+X.F.Suc+PL+rab+His+SO4.ferm.+PO4.utilise; 0.252, 0.606, Main.P-Source.Conc.+P-Source.Feed.conc.+Nitrogen.Conc.+X.F.Suc+X.VXdt+PL+rab+His+SO4.ferm.+PO4.utilise; 0.238, 0.606, tmp+Main.P-Source.Conc.+P-Source.Feed.conc.+X.F.Suc+X.VXdt+PL+rab+Thr+lactate+SO4.ferm.+PO4.utilise; 0.265, 0.606, tmp+Main.P-Source.Conc.+P-Source.Feed.conc.+X.F.Suc+total.Vol+emission_O2+His+SO4.ferm.+PO4.utilise; 0.238, 0.606, pH+Main.P-Source.Conc.+P-Source.Feed.conc.+Nitrogen.Conc.+X.F.Suc+PL+rab+Thr+His+SO4.ferm.+PO4.utilise; 0.265, 0.606, pH+Main.P-Source.Conc.+P-Source.Feed.conc.+X.F.Suc+rab+Thr+SO4.ferm.+PO4.ferm.+PO4.utilise; 0.278, 0.606, Main.P-Source.Conc.+P-Source.Feed.conc.+Lys_conc.+X.F.Suc+rab+Thr+SO4.ferm.+PO4.utilise; 0.278, 0.606, tmp+Main.P-Source.Conc.+P-Source.Feed.conc.+total.Vol+PL+rab+SO4.ferm.+PO4.utilise; 0.265, 0.606, Main.P-Source.Conc.+P-Source.Feed.conc.+X.F.Suc+X.VXdt+PL+emission_O2+lactate+SO4.ferm.+PO4.utilise; 0.265, 0.606, Main.P-Source.Conc.+P-Source.Feed.conc.+Main.Thr.Conc.+X.F.Suc+total.Vol+PL+emission_O2+SO4.ferm.+PO4.utilise; 0.291, 0.606, Main.P-Source.Conc.+P-Source.Feed.conc.+Lys_conc.+yield+rab+SO4.ferm.+PO4.utilise; 0.252, 0.606, pH+Main.P-Source.Conc.+P-Source.Feed.conc.+OD+X.F.Suc+total.cell+PL+rab+SO4.ferm.+PO4.utilise; 0.303, 0.606, pH+Main.P-Source.Conc.+P-Source.Feed.conc.+X.F.Suc+SO4.ferm.+PO4.utilise; 0.265, 0.606, tmp+Main.P-Source.Conc.+P-Source.Feed.conc.+Nitrogen.Conc.+X.F.Suc+total.Vol+PL+SO4.ferm.+PO4.utilise; 0.224, 0.606, pH+tmp+Main.P-Source.Conc.+P-Source.Feed.conc.+Nitrogen.Conc.+X.F.Suc+X.VXdt+PL+rab+His+SO4.ferm.+PO4.utilise; 0.278, 0.606, Main.P-Source.Conc.+P-Source.Feed.conc.+Nitrogen.Conc.+X.F.Suc+emission_O2+Thr+SO4.ferm.+PO4.utilise; 0.265, 0.606, pH+Main.P-Source.Conc.+P-Source.Feed.conc.+total.Vol+yield+PL+emission_O2+SO4.ferm.+PO4.utilise; 0.252, 0.606, pH+Main.P-Source.Conc.+P-Source.Feed.conc.+X.F.Suc+total.cell+PL+emission_O2+SO4.ferm.+PO4.ferm.+PO4.utilise; 0.252, 0.606, pH+tmp+Main.P-Source.Conc.+P-Source.Feed.conc.+Nitrogen.Conc.+X.F.Suc+total.Vol+PL+SO4.ferm.+PO4.utilise; 0.278, 0.606, Main.P-

Source.Conc.+P-Source.Feed.conc.+Lys_conc.+X.F.Suc+ emission_O2+Thr+SO4.ferm.+PO4.utilise; 0.278, 0.606, pH+Main.P-Source.Conc.+P-Source.Feed.conc.+X.F.Suc+ total.Vol+PL+SO4.ferm.+PO4.utilise; 0.238, 0.606, tmp+ Main.P-Source.Conc.+P-Source.Feed.conc.+X.F.Suc+ X.VXdt+PL+emission_O2+His+SO4.ferm.+PO4.ferm.+ PO4.utilise; 0.265, 0.606, Main.P-Source.Conc.+P-Source.Feed.conc.+OD+X.F.Suc+X.VXdt+PL+ emission_O2+SO4.ferm.+PO4.utilise; 0.265, 0.606, Main.P-Source.Conc.+P-Source.Feed.conc.+X.F.Suc+ X.VXdt+total.Vol+rab+His+SO4.ferm.+PO4.utilise; 0.238, 0.606, pH+Main.P-Source.Conc.+P-Source.Feed.conc.+ X.F.Suc+total.Vol+PL+rab+Thr+lactate+SO4.ferm.+ PO4.utilise; 0.251, 0.606, Main.P-Source.Conc.+P-Source. Feed.conc.+X.F.Suc+X.VXdt+total.cell+PL+rab+His+ SO4.ferm.+PO4.utilise; 0.302, 0.606, pH+Main.P-Source.Conc.+P-Source.Feed.conc.+yield+SO4.ferm.+ PO4.utilise; 0.208, 0.605, pH+Main.P-Source.Conc.+P-Source.Feed.conc.+X.F.Suc+X.VXdt+total.Vol+PL+rab+ Thr+His+lactate+SO4.ferm.+PO4.utilise; 0.238, 0.605, pH+tmp+Main.P-Source.Conc.+P-Source.Feed.conc.+ X.F.Suc+X.VXdt+PL+emission_O2+Thr+SO4.ferm.+ PO4.utilise; 0.251, 0.605, Main.P-Source.Conc.+P-Source. Feed.conc.+Main.Thr.Conc.+X.F.Suc+PL+rab+Thr+His+ SO4.ferm.+PO4.utilise; 0.251, 0.605, Main.P-Source.Conc.+P-Source.Feed.conc.+Nitrogen.Conc.+ X.F.Suc+X.VXdt+PL+rab+SO4.ferm.+PO4.ferm.+ PO4.utilise; 0.251, 0.605, tmp+Main.P-Source.Conc.+P-Source.Feed.conc.+X.F.Suc+total.Vol+PL+emission_O2+ SO4.ferm.+PO4.ferm.+PO4.utilise; 0.265, 0.605, pH+tmp+ Main.P-Source.Conc.+P-Source.Feed.conc.+X.F.Suc+ X.VXdt+rab+SO4.ferm.+PO4.utilise; 0.290, 0.605, Main.P-Source.Conc.+P-Source.Feed.conc.+yield+rab+SO4.ferm.+ PO4.ferm.+PO4.utilise; 0.251, 0.605, pH+Main.P-Source.Conc.+P-Source.Feed.conc.+X.F.Suc+Cell+PL+ rab+Thr+SO4.ferm.+PO4.utilise; 0.265, 0.605, Main.P-Source.Conc.+P-Source.Feed.conc.+X.F.Suc+PL+ emission_O2+lactate+SO4.ferm.+PO4.ferm.+PO4.utilise; 0.251, 0.605, tmp+Main.P-Source.Conc.+P-Source.Feed. conc.+Nitrogen.Conc.+X.F.Suc+total.Vol+PL+emission_O2+SO4.ferm.+PO4.utilise; 0.277, 0.605, pH+Main.P-Source.Conc.+P-Source.Feed.conc.+yield+ PL+SO4.ferm.+PO4.ferm.+PO4.utilise; 0.277, 0.605, tmp+ Main.P-Source.Conc.+P-Source.Feed.conc.+Lys_conc.+ yield+PL+SO4.ferm.+PO4.utilise; 0.265, 0.605, pH+tmp+ Main.P-Source.Conc.+P-Source.Feed.conc.+Lys_conc.+ yield+PL+SO4.ferm.+PO4.utilise; 0.251, 0.605, pH+Main.P-Source.Conc.+P-Source.Feed.conc.+Main.Thr. Conc.+X.F.Suc+total.Vol+PL+emission_O2+SO4.ferm.+ PO4.utilise; 0.223, 0.605, pH+Main.P-Source.Conc.+P-Source.Feed.conc.+OD+X.F.Suc+total.Vol+total.cell+PL+ rab+Thr+SO4.ferm.+PO4.utilise; 0.290, 0.605, tmp+ Main.P-Source.Conc.+P-Source.Feed.conc.+Lys_conc.+ yield+SO4.ferm.+PO4.utilise; 0.251, 0.605, Main.P-Source.Conc.+P-Source.Feed.conc.+X.F.Suc+X.VXdt+ total.cell+PL+rab+SO4.ferm.+PO4.ferm.+PO4.utilise; 0.237, 0.605, pH+tmp+Main.P-Source.Conc.+P-Source. Feed.conc.+OD+X.F.Suc+total.Vol+total.cell+PL+ SO4.ferm.+PO4.utilise; 0.237, 0.605, pH+tmp+Main.P-Source.Conc.+P-Source.Feed.conc.+Nitrogen.Conc.+ X.F.Suc+PL+rab+SO4.ferm.+PO4.ferm.+PO4.utilise; 0.251, 0.605, Main.P-Source.Conc.+P-Source.Feed.conc.+ X.F.Suc+X.VXdt+total.Vol+total.cell+PL+emission_O2+ SO4.ferm.+PO4.utilise; 0.237, 0.605, pH+tmp+Main.P-Source.Conc.+P-Source.Feed.conc.+X.F.Suc+PL+rab+ lactate+SO4.ferm.+PO4.ferm.+PO4.utilise; 0.264, 0.605, Main.P-Source.Conc.+P-Source.Feed.conc.+X.F.Suc+ total.cell+PL+emission_O2+His+SO4.ferm.+PO4.utilise; 0.237, 0.605, pH+tmp+Main.P-Source.Conc.+P-Source. Feed.conc.+X.F.Suc+X.VXdt+total.Vol+PL+His+ SO4.ferm.+PO4.utilise; 0.277, 0.605, pH+Main.P-Source.Conc.+P-Source.Feed.conc.+Nitrogen.Conc.+ X.F.Suc+emission_O2+SO4.ferm.+PO4.utilise; 0.290, 0.605, pH+Main.P-Source.Conc.+P-Source.Feed.conc.+ yield+PL+SO4.ferm.+PO4.utilise; 0.223, 0.605, Main.P-Source.Conc.+P-Source.Feed.conc.+OD+Lys_conc.+Cell+ total.Vol+total.cell+yield+PL+rab+SO4.ferm.+PO4.utilise; 0.264, 0.605, Main.P-Source.Conc.+P-Source.Feed.conc.+ X.F.Suc+total.Vol+PL+rab+lactate+SO4.ferm.+PO4.utilise; 0.251, 0.605, tmp+Main.P-Source.Conc.+P-Source.Feed. conc.+X.F.Suc+total.cell+PL+rab+Thr+SO4.ferm.+ PO4.utilise; 0.251, 0.605, pH+tmp+Main.P-Source.Conc.+ P-Source.Feed.conc.+Nitrogen.Conc.+X.F.Suc+PL+ SO4.ferm.+PO4.ferm.+PO4.utilise; 0.264, 0.605, tmp+ Main.P-Source.Conc.+P-Source.Feed.conc.+X.F.Suc+Cell+ PL+rab+SO4.ferm.+PO4.utilise; 0.290, 0.605, Main.P-Source.Conc.+P-Source.Feed.conc.+yield+His+SO4.ferm.+ PO4.ferm.+PO4.utilise; 0.277, 0.605, pH+tmp+Main.P-Source.Conc.+P-Source.Feed.conc.+X.F.Suc+SO4.ferm.+ PO4.ferm.+PO4.utilise; 0.264, 0.605, Main.P-Source.Conc.+P-Source.Feed.conc.+X.F.Suc+PL+ emission_O2+His+lactate+SO4.ferm.+PO4.utilise; 0.237, 0.605, tmp+Main.P-Source.Conc.+P-Source.Feed.conc.+ OD+X.F.Suc+total.Vol+total.cell+PL+rab+SO4.ferm.+ PO4.utilise; 0.301, 0.605, Main.P-Source.Conc.+P-Source. Feed.conc.+X.F.Suc+His+SO4.ferm.+PO4.utilise; 0.264, 0.605, tmp+Main.P-Source.Conc.+P-Source.Feed.conc.+ X.F.Suc+rab+Thr+SO4.ferm.+PO4.ferm.+PO4.utilise; 0.277, 0.605, tmp+Main.P-Source.Conc.+P-Source.Feed. conc.+total.Vol+PL+His+SO4.ferm.+PO4.utilise; 0.207, 0.605, pH+tmp+Main.P-Source.Conc.+P-Source.Feed. conc.+X.F.Suc+X.VXdt+PL+rab+Thr+His+lactate+ SO4.ferm.+PO4.utilise; 0.251, 0.605, tmp+Main.P-Source.Conc.+P-Source.Feed.conc.+X.F.Suc+total.Vol+ rab+Thr+His+SO4.ferm.+PO4.utilise; 0.237, 0.605, Main.P-Source.Conc.+P-Source.Feed.conc.+OD+X.F.Suc+ total.Vol+total.cell+PL+rab+Thr+SO4.ferm.+PO4.utilise; 0.251, 0.605, Main.P-Source.Conc.+P-Source.Feed.conc.+ X.F.Suc+PL+emission_O2+Thr+lactate+SO4.ferm.+ PO4.ferm.+PO4.utilise; 0.250, 0.605, tmp+Main.P-Source.Conc.+P-Source.Feed.conc.+X.F.Suc+X.VXdt+PL+ His+SO4.ferm.+PO4.ferm.+PO4.utilise; 0.250, 0.605, pH+tmp+Main.P-Source.Conc.+P-Source.Feed.conc.+total. Vol+yield+PL+rab+SO4.ferm.+PO4.utilise; 0.222, 0.605, pH+Main.P-Source.Conc.+P-Source.Feed.conc.+X.F.Suc+ X.VXdt+total.Vol+PL+rab+His+lactate+SO4.ferm.+ PO4.utilise; 0.237, 0.605, Main.P-Source.Conc.+P-Source. Feed.conc.+X.F.Suc+X.VXdt+total.Vol+PL+rab+Thr+lactate+SO4.ferm.+PO4.utilise; 0.277, 0.605, tmp+Main.P-Source.Conc.+P-Source.Feed.conc.+yield+PL+His+ SO4.ferm.+PO4.utilise; 0.264, 0.605, tmp+Main.P-Source.Conc.+P-Source.Feed.conc.+Nitrogen.Conc.+ X.F.Suc+PL+SO4.ferm.+PO4.utilise; 0.236, 0.605, pH+Main.P-Source.Conc.+P-Source.Feed.conc.+Lys_conc.+X.F.Suc+PL+rab+Thr+His+SO4.ferm.+ PO4.utilise; 0.236, 0.605, pH+tmp+Main.P-Source.Conc.+ P-Source.Feed.conc.+OD+X.F.Suc+X.VXdt+PL+rab+ SO4.ferm.+PO4.utilise; 0.236, 0.605, Main.P-Source.Conc.+P-Source.Feed.conc.+X.F.Suc+X.VXdt+PL+ rab+Thr+His+lactate+SO4.ferm.+PO4.utilise; 0.236, 0.605, tmp+Main.P-Source.Conc.+P-Source.Feed.conc.+X.F.Suc+ PL+emission_O2+Thr+His+SO4.ferm.+PO4.ferm.+ PO4.utilise; 0.250, 0.605, pH+Main.P-Source.Conc.+P-Source.Feed.conc.+X.F.Suc+total.Vol+rab+Thr+His+

SO4.ferm.+PO4.utilise; 0.236, 0.605, tmp+Main.P-Source.Conc.+P-Source.Feed.conc.+Nitrogen.Conc.+X.F.Suc+X.VXdt+PL+rab+His+SO4.ferm.+PO4.utilise; 0.250, 0.605, Main.P-Source.Conc.+P-Source.Feed.conc.+Main.Thr.Conc.+X.F.Suc+total.Vol+PL+rab+Thr+SO4.ferm.+PO4.utilise; 0.222, 0.605, pH+tmp+Main.P-Source.Conc.+P-Source.Feed.conc.+Main.Thr.Conc.+X.F.Suc+X.VXdt+total.Vol+PL+rab+SO4.ferm.+PO4.utilise; 0.236, 0.605, tmp+Main.P-Source.Conc.+P-Source.Feed.conc.+Nitrogen.Conc.+X.F.Suc+total.Vol+PL+rab+Thr+SO4.ferm.+PO4.utilise; 0.277, 0.605, Main.P-Source.Conc.+P-Source.Feed.conc.+total.Vol+yield+rab+His+SO4.ferm.+PO4.utilise; 0.277, 0.605, pH+Main.P-Source.Conc.+P-Source.Feed.conc.+X.F.Suc+emission_O2+lactate+SO4.ferm.+PO4.utilise; 0.264, 0.605, pH+tmp+Main.P-Source.Conc.+P-Source.Feed.conc.+X.F.Suc+total.Vol+emission_O2+SO4.ferm.+PO4.utilise; 0.175, 0.605, pH+Main.P-Source.Conc.+P-Source.Feed.conc.+Main.Thr.Conc.+OD+Lys_conc.+Cell+total.Vol+total.cell+yield+PL+rab+SO4.ferm.+PO4.ferm.+PO4.utilise; 0.250, 0.605, pH+Main.P-Source.Conc.+P-Source.Feed.conc.+Main.Thr.Conc.+X.F.Suc+PL+emission_O2+His+SO4.ferm.+PO4.utilise; 0.250, 0.605, pH+tmp+Main.P-Source.Conc.+P-Source.Feed.conc.+X.F.Suc+PL+emission_O2+lactate+SO4.ferm.+PO4.utilise; 0.263, 0.605, Main.P-Source.Conc.+P-Source.Feed.conc.+X.F.Suc+total.cell+PL+emission_O2+Thr+SO4.ferm.+PO4.utilise; 0.250, 0.604, tmp+Main.P-Source.Conc.+P-Source.Feed.conc.+Main.Thr.Conc.+X.F.Suc+total.Vol+PL+rab+SO4.ferm.+PO4.utilise; 0.222, 0.604, pH+tmp+Main.P-Source.Conc.+P-Source.Feed.conc.+X.F.Suc+X.VXdt+PL+rab+His+lactate+SO4.ferm.+PO4.utilise; 0.276, 0.604, pH+Main.P-Source.Conc.+P-Source.Feed.conc.+total.Vol+PL+rab+SO4.ferm.+PO4.utilise; 0.263, 0.604, Main.P-Source.Conc.+P-Source.Feed.conc.+X.F.Suc+total.Vol+total.cell+PL+emission_O2+SO4.ferm.+PO4.utilise; 0.250, 0.604, pH+Main.P-Source.Conc.+P-Source.Feed.conc.+X.F.Suc+Cell+X.VXdt+PL+emission_O2+SO4.ferm.+PO4.utilise; 0.263, 0.604, pH+Main.P-Source.Conc.+P-Source.Feed.conc.+Lys_conc.+yield+PL+rab+SO4.ferm.+PO4.utilise; 0.276, 0.604, Main.P-Source.Conc.+P-Source.Feed.conc.+Nitrogen.Conc.+yield+PL+rab+SO4.ferm.+PO4.utilise; 0.236, 0.604, pH+tmp+Main.P-Source.Conc.+P-Source.Feed.conc.+X.F.Suc+total.Vol+PL+emission_O2+SO4.ferm.+PO4.ferm.+PO4.utilise; 0.263, 0.604, pH+Main.P-Source.Conc.+P-Source.Feed.conc.+X.F.Suc+X.VXdt+total.Vol+emission_O2+SO4.ferm.+PO4.utilise; 0.250, 0.604, pH+tmp+Main.P-Source.Conc.+P-Source.Feed.conc.+X.F.Suc+X.VXdt+PL+Thr+SO4.ferm.+PO4.utilise; 0.289, 0.604, Main.P-Source.Conc.+P-Source.Feed.conc.+X.F.Suc+total.cell+emission_O2+SO4.ferm.+PO4.utilise; 0.289, 0.604, tmp+Main.P-Source.Conc.+P-Source.Feed.conc.+Nitrogen.Conc.+X.F.Suc+SO4.ferm.+PO4.utilise; 0.221, 0.604, pH+tmp+Main.P-Source.Conc.+P-Source.Feed.conc.+X.F.Suc+X.VXdt+total.Vol+PL+emission_O2+His+SO4.ferm.+PO4.utilise; 0.276, 0.604, Main.P-Source.Conc.+P-Source.Feed.conc.+total.Vol+yield+emission_O2+His+SO4.ferm.+PO4.utilise; 0.236, 0.604, tmp+Main.P-Source.Conc.+P-Source.Feed.conc.+X.F.Suc+X.VXdt+PL+emission_O2+Thr+His+SO4.ferm.+PO4.utilise; 0.263, 0.604, tmp+Main.P-Source.Conc.+P-Source.Feed.conc.+total.Vol+yield+PL+emission_O2+SO4.ferm.+PO4.utilise; 0.236, 0.604, tmp+Main.P-Source.Conc.+P-Source.Feed.conc.+X.F.Suc+X.VXdt+total.Vol+PL+rab+Thr+SO4.ferm.+PO4.utilise; 0.250, 0.604, pH+Main.P-Source.Conc.+P-Source.Feed.conc.+X.F.Suc+total.Vol+total.cell+PL+emission_O2+SO4.ferm.+PO4.utilise; 0.263, 0.604, pH+Main.P-Source.Conc.+P-Source.Feed.conc.+Lys_conc.+yield+PL+emission_O2+SO4.ferm.+PO4.utilise; 0.263, 0.604, pH+Main.P-Source.Conc.+P-Source.Feed.conc.+X.F.Suc+rab+His+SO4.ferm.+PO4.ferm.+PO4.utilise; 0.250, 0.604, Main.P-Source.Conc.+P-Source.Feed.conc.+X.F.Suc+X.VXdt+total.Vol+PL+rab+lactate+SO4.ferm.+PO4.utilise; 0.263, 0.604, pH+tmp+Main.P-Source.Conc.+P-Source.Feed.conc.+X.F.Suc+total.Vol+His+SO4.ferm.+PO4.utilise; 0.263, 0.604, Main.P-Source.Conc.+P-Source.Feed.conc.+X.F.Suc+Cell+total.Vol+PL+emission_O2+SO4.ferm.+PO4.utilise; 0.263, 0.604, pH+Main.P-Source.Conc.+P-Source.Feed.conc.+total.Vol+PL+His+SO4.ferm.+PO4.utilise; 0.250, 0.604, pH+tmp+Main.P-Source.Conc.+P-Source.Feed.conc.+yield+PL+rab+SO4.ferm.+PO4.ferm.+PO4.utilise; 0.263, 0.604, Main.P-Source.Conc.+P-Source.Feed.conc.+total.Vol+yield+PL+rab+His+SO4.ferm.+PO4.utilise; 0.263, 0.604, Main.P-Source.Conc.+P-Source.Feed.conc.+X.F.Suc+X.VXdt+rab+Thr+lactate+SO4.ferm.+PO4.utilise; 0.236, 0.604, pH+Main.P-Source.Conc.+P-Source.Feed.conc.+X.F.Suc+total.Vol+PL+emission_O2+Thr+lactate+SO4.ferm.+PO4.utilise; 0.249, 0.604, Main.P-Source.Conc.+P-Source.Feed.conc.+OD+X.F.Suc+X.VXdt+total.Vol+PL+emission_O2+SO4.ferm.+PO4.utilise; 0.249, 0.604, tmp+Main.P-Source.Conc.+P-Source.Feed.conc.+X.F.Suc+X.VXdt+total.cell+PL+emission_O2+SO4.ferm.+PO4.utilise; 0.249, 0.604, pH+Main.P-Source.Conc.+P-Source.Feed.conc.+X.F.Suc+total.cell+PL+emission_O2+His+SO4.ferm.+PO4.utilise; 0.236, 0.604, tmp+Main.P-Source.Conc.+P-Source.Feed.conc.+Nitrogen.Conc.+X.F.Suc+X.VXdt+PL+rab+SO4.ferm.+PO4.ferm.+PO4.utilise; 0.249, 0.604, Main.P-Source.Conc.+P-Source.Feed.conc.+Nitrogen.Conc.+X.F.Suc+total.Vol+PL+emission_O2+Thr+SO4.ferm.+PO4.utilise; 0.249, 0.604, pH+Main.P-Source.Conc.+P-Source.Feed.conc.+X.F.Suc+X.VXdt+PL+emission_O2+Thr+SO4.ferm.+PO4.utilise; 0.221, 0.604, pH+tmp+Main.P-Source.Conc.+P-Source.Feed.conc.+X.F.Suc+PL+rab+Thr+His+SO4.ferm.+PO4.ferm.+PO4.utilise; 0.235, 0.604, pH+Main.P-Source.Conc.+P-Source.Feed.conc.+Main.Thr.Conc.+X.F.Suc+X.VXdt+PL+rab+His+SO4.ferm.+PO4.utilise; 0.221, 0.604, pH+Main.P-Source.Conc.+P-Source.Feed.conc.+X.F.Suc+PL+rab+Thr+His+lactate+SO4.ferm.+PO4.ferm.+PO4.utilise; 0.288, 0.604, pH+tmp+Main.P-Source.Conc.+P-Source.Feed.conc.+yield+SO4.ferm.+PO4.utilise; 0.276, 0.604, tmp+Main.P-Source.Conc.+P-Source.Feed.conc.+Lys_conc.+total.Vol+PL+SO4.ferm.+PO4.utilise; 0.235, 0.604, pH+Main.P-Source.Conc.+P-Source.Feed.conc.+X.F.Suc+PL+rab+His+lactate+SO4.ferm.+PO4.ferm.+PO4.utilise; 0.249, 0.604, pH+tmp+Main.P-Source.Conc.+P-Source.Feed.conc.+X.F.Suc+Cell+PL+rab+SO4.ferm.+PO4.utilise; 0.249, 0.604, Main.P-Source.Conc.+P-Source.Feed.conc.+Nitrogen.Conc.+X.F.Suc+PL+emission_O2+Thr+His+SO4.ferm.+PO4.utilise; 0.288, 0.604, Main.P-Source.Conc.+P-Source.Feed.conc.+X.F.Suc+PL+His+SO4.ferm.+PO4.utilise; 0.276, 0.604, pH+tmp+Main.P-Source.Conc.+P-Source.Feed.conc.+total.Vol+yield+SO4.ferm.+PO4.utilise; 0.249, 0.604, pH+tmp+Main.P-Source.Conc.+P-Source.Feed.conc.+X.F.Suc+total.Vol+rab+Thr+SO4.ferm.+PO4.utilise; 0.249, 0.604, pH+tmp+Main.P-Source.Conc.+P-Source.Feed.conc.+Nitrogen.Conc.+X.VXdt+yield+PL+SO4.ferm.+PO4.utilise; 0.275, 0.604, Main.P-Source.Conc.+P-Source.Feed.conc.+yield+PL+His+SO4.ferm.+PO4.ferm.+

PO4.utilise; 0.249, 0.604, tmp+Main.P-Source.Conc.+P-Source.Feed.conc.+Main.Thr.Conc.+X.F.Suc+total.Vol+PL+emission_O2+SO4.ferm.+PO4.utilise; 0.262, 0.604, tmp+Main.P-Source.Conc.+P-Source.Feed.conc.+X.F.Suc+PL+emission_O2+lactate+SO4.ferm.+PO4.utilise; 0.249, 0.604, tmp+Main.P-Source.Conc.+P-Source.Feed.conc.+Nitrogen.Conc.+X.F.Suc+PL+rab+His+SO4.ferm.+PO4.utilise; 0.262, 0.604, tmp+Main.P-Source.Conc.+P-Source.Feed.conc.+X.F.Suc+total.Vol+Thr+His+SO4.ferm.+PO4.utilise; 0.235, 0.604, pH+Main.P-Source.Conc.+P-Source.Feed.conc.+X.F.Suc+X.VXdt+total.Vol+PL+emission_O2+Thr+SO4.ferm.+PO4.utilise; 0.235, 0.604, Main.P-Source.Conc.+P-Source.Feed.conc.+X.F.Suc+X.VXdt+total.Vol+PL+emission_O2+His+SO4.ferm.+PO4.ferm.+PO4.utilise; 0.288, 0.604, Main.P-Source.Conc.+P-Source.Feed.conc.+yield+emission_O2+SO4.ferm.+PO4.ferm.+PO4.utilise; 0.262, 0.604, pH+Main.P-Source.Conc.+P-Source.Feed.conc.+yield+PL+rab+His+SO4.ferm.+PO4.utilise; 0.249, 0.604, pH+Main.P-Source.Conc.+P-Source.Feed.conc.+X.F.Suc+Cell+total.Vol+PL+emission_O2+SO4.ferm.+PO4.utilise; 0.235, 0.604, pH+Main.P-Source.Conc.+P-Source.Feed.conc.+X.F.Suc+X.VXdt+PL+rab+Thr+SO4.ferm.+PO4.ferm.+PO4.utilise; 0.221, 0.604, pH+Main.P-Source.Conc.+P-Source.Feed.conc.+X.F.Suc+X.VXdt+total.Vol+total.cell+PL+rab+His+SO4.ferm.+PO4.utilise; 0.262, 0.604, Main.P-Source.Conc.+P-Source.Feed.conc.+OD+X.F.Suc+PL+rab+Thr+SO4.ferm.+PO4.utilise; 0.262, 0.604, pH+tmp+Main.P-Source.Conc.+P-Source.Feed.conc.+Lys_conc.+total.Vol+PL+SO4.ferm.+PO4.utilise; 0.262, 0.604, Main.P-Source.Conc.+P-Source.Feed.conc.+X.F.Suc+Cell+X.VXdt+PL+emission_O2+SO4.ferm.+PO4.utilise; 0.249, 0.604, pH+Main.P-Source.Conc.+P-Source.Feed.conc.+X.F.Suc+total.Vol+PL+emission_O2+lactate+SO4.ferm.+PO4.utilise; 0.249, 0.604, Main.P-Source.Conc.+P-Source.Feed.conc.+X.F.Suc+X.VXdt+PL+rab+His+lactate+SO4.ferm.+PO4.utilise; 0.275, 0.604, pH+Main.P-Source.Conc.+P-Source.Feed.conc.+Lys_conc.+X.F.Suc+emission_O2+SO4.ferm.+PO4.utilise; 0.262, 0.604, pH+tmp+Main.P-Source.Conc.+P-Source.Feed.conc.+X.VXdt+yield+PL+SO4.ferm.+PO4.utilise; 0.262, 0.604, pH+tmp+Main.P-Source.Conc.+P-Source.Feed.conc.+X.F.Suc+total.Vol+Thr+SO4.ferm.+PO4.utilise; 0.262, 0.604, pH+Main.P-Source.Conc.+P-Source.Feed.conc.+X.F.Suc+X.VXdt+emission_O2+His+SO4.ferm.+PO4.utilise; 0.275, 0.604, Main.P-Source.Conc.+P-Source.Feed.conc.+X.F.Suc+X.VXdt+total.Vol+PL+SO4.ferm.+PO4.utilise; 0.220, 0.604, pH+Main.P-Source.Conc.+P-Source.Feed.conc.+OD+X.F.Suc+Cell+total.Vol+total.cell+PL+rab+SO4.ferm.+PO4.utilise; 0.249, 0.604, tmp+Main.P-Source.Conc.+P-Source.Feed.conc.+X.F.Suc+PL+Thr+His+SO4.ferm.+PO4.ferm.+PO4.utilise; 0.262, 0.604, Main.P-Source.Conc.+P-Source.Feed.conc.+X.F.Suc+Cell+PL+emission_O2+His+SO4.ferm.+PO4.utilise; 0.262, 0.604, Main.P-Source.Conc.+P-Source.Feed.conc.+total.Vol+yield+PL+emission_O2+His+SO4.ferm.+PO4.utilise; 0.235, 0.604, pH+Main.P-Source.Conc.+P-Source.Feed.conc.+Main.Thr.Conc.+X.F.Suc+PL+rab+Thr+His+SO4.ferm.+PO4.utilise; 0.275, 0.604, Main.P-Source.Conc.+P-Source.Feed.conc.+Nitrogen.Conc.+yield+PL+emission_O2+SO4.ferm.+PO4.utilise; 0.220, 0.604, pH+Main.P-Source.Conc.+P-Source.Feed.conc.+Nitrogen.Conc.+X.F.Suc+X.VXdt+total.Vol+PL+rab+SO4.ferm.+PO4.ferm.+PO4.utilise; 0.235, 0.604, pH+tmp+Main.P-Source.Conc.+P-Source.Feed.conc.+Nitrogen.Conc.+X.F.Suc+total.Vol+PL+emission_O2+SO4.ferm.+PO4.utilise; 0.262, 0.604, Main.P-Source.Conc.+P-Source.Feed.conc.+OD+X.F.Suc+total.Vol+PL+rab+SO4.ferm.+PO4.utilise; 0.235, 0.604, pH+Main.P-Source.Conc.+P-Source.Feed.conc.+Main.Thr.Conc.+X.F.Suc+X.VXdt+PL+emission_O2+SO4.ferm.+PO4.ferm.+PO4.utilise; 0.220, 0.604, pH+Main.P-Source.Conc.+P-Source.Feed.conc.+X.F.Suc+X.VXdt+PL+emission_O2+Thr+His+lactate+SO4.ferm.+PO4.utilise; 0.220, 0.603, pH+Main.P-Source.Conc.+P-Source.Feed.conc.+Main.Thr.Conc.+OD+X.F.Suc+total.Vol+total.cell+PL+rab+SO4.ferm.+PO4.utilise; 0.275, 0.603, tmp+Main.P-Source.Conc.+P-Source.Feed.conc.+X.F.Suc+His+SO4.ferm.+PO4.ferm.+PO4.utilise; 0.249, 0.603, pH+Main.P-Source.Conc.+P-Source.Feed.conc.+yield+PL+emission_O2+His+SO4.ferm.+PO4.ferm.+PO4.utilise; 0.275, 0.603, tmp+Main.P-Source.Conc.+P-Source.Feed.conc.+Nitrogen.Conc.+X.F.Suc+rab+SO4.ferm.+PO4.utilise; 0.262, 0.603, pH+tmp+Main.P-Source.Conc.+P-Source.Feed.conc.+total.Vol+PL+rab+SO4.ferm.+PO4.utilise; 0.235, 0.603, tmp+Main.P-Source.Conc.+P-Source.Feed.conc.+X.F.Suc+X.VXdt+total.Vol+PL+emission_O2+His+SO4.ferm.+PO4.utilise; 0.235, 0.603, pH+tmp+Main.P-Source.Conc.+P-Source.Feed.conc.+Main.Thr.Conc.+X.F.Suc+PL+rab+SO4.ferm.+PO4.ferm.+PO4.utilise; 0.248, 0.603, pH+Main.P-Source.Conc.+P-Source.Feed.conc.+Nitrogen.Conc.+yield+PL+rab+SO4.ferm.+PO4.ferm.+PO4.utilise; 0.248, 0.603, Main.P-Source.Conc.+P-Source.Feed.conc.+Main.Thr.Conc.+X.F.Suc+PL+emission_O2+Thr+His+SO4.ferm.+PO4.utilise; 0.205, 0.603, pH+Main.P-Source.Conc.+P-Source.Feed.conc.+OD+X.F.Suc+total.Vol+total.cell+PL+emission_O2+Thr+lactate+SO4.ferm.+PO4.utilise; 0.235, 0.603, tmp+Main.P-Source.Conc.+P-Source.Feed.conc.+X.F.Suc+X.VXdt+PL+emission_O2+Thr+lactate+SO4.ferm.+PO4.utilise; 0.248, 0.603, tmp+Main.P-Source.Conc.+P-Source.Feed.conc.+OD+X.F.Suc+X.VXdt+PL+rab+SO4.ferm.+PO4.utilise; 0.248, 0.603, pH+tmp+Main.P-Source.Conc.+P-Source.Feed.conc.+OD+X.F.Suc+X.VXdt+PL+SO4.ferm.+PO4.utilise; 0.205, 0.603, Main.P-Source.Conc.+P-Source.Feed.conc.+Main.Thr.Conc.+OD+Lys_conc.+Cell+total.Vol+total.cell+yield+PL+emission_O2+SO4.ferm.+PO4.utilise; 0.234, 0.603, pH+tmp+Main.P-Source.Conc.+P-Source.Feed.conc.+Main.Thr.Conc.+X.F.Suc+total.Vol+PL+rab+SO4.ferm.+PO4.utilise; 0.275, 0.603, Main.P-Source.Conc.+P-Source.Feed.conc.+Nitrogen.Conc.+X.F.Suc+total.Vol+rab+SO4.ferm.+PO4.utilise; 0.220, 0.603, pH+Main.P-Source.Conc.+P-Source.Feed.conc.+Main.Thr.Conc.+X.F.Suc+X.VXdt+total.Vol+PL+rab+His+SO4.ferm.+PO4.utilise; 0.275, 0.603, Main.P-Source.Conc.+P-Source.Feed.conc.+Lys_conc.+X.F.Suc+emission_O2+His+SO4.ferm.+PO4.utilise; 0.220, 0.603, pH+tmp+Main.P-Source.Conc.+P-Source.Feed.conc.+Nitrogen.Conc.+X.F.Suc+X.VXdt+total.Vol+PL+rab+SO4.ferm.+PO4.utilise; 0.220, 0.603, pH+tmp+Main.P-Source.Conc.+P-Source.Feed.conc.+X.F.Suc+PL+rab+Thr+lactate+SO4.ferm.+PO4.ferm.+PO4.utilise; 0.234, 0.603, pH+Main.P-Source.Conc.+P-Source.Feed.conc.+Lys_conc.+X.F.Suc+PL+emission_O2+Thr+His+SO4.ferm.+PO4.utilise; 0.220, 0.603, pH+Main.P-Source.Conc.+P-Source.Feed.conc.+OD+X.F.Suc+total.Vol+total.cell+PL+emission_O2+lactate+SO4.ferm.+PO4.utilise; 0.262, 0.603, pH+tmp+Main.P-Source.Conc.+P-Source.Feed.conc.+yield+PL+His+SO4.ferm.+PO4.utilise; 0.287, 0.603, Main.P-Source.Conc.+P-Source.Feed.conc.+yield+PL+His+SO4.ferm.+PO4.utilise; 0.262, 0.603, Main.P-Source.Conc.+P-Source.Feed.conc.+Nitrogen.Conc.+yield+

PL+emission_O2+SO4.ferm.+PO4.ferm.+PO4.utilise; 0.262, 0.603, Main.P-Source.Conc.+P-Source.Feed.conc.+ X.F.Suc+Cell+PL+emission_O2+SO4.ferm.+PO4.ferm.+ PO4.utilise; 0.262, 0.603, pH+Main.P-Source.Conc.+P-Source.Feed.conc.+X.F.Suc+X.VXdt+rab+SO4.ferm.+ PO4.ferm.+PO4.utilise; 0.275, 0.603, Main.P-Source.Conc.+P-Source.Feed.conc.+Lys_conc.+yield+ emission_O2+His+SO4.ferm.+PO4.utilise; 0.234, 0.603, pH+Main.P-Source.Conc.+P-Source.Feed.conc.+Main.Thr. Conc.+X.F.Suc+total.Vol+PL+rab+Thr+SO4.ferm.+ PO4.utilise; 0.248, 0.603, tmp+Main.P-Source.Conc.+P-Source.Feed.conc.+Main.Thr.Conc.+X.F.Suc+PL+rab+ SO4.ferm.+PO4.ferm.+PO4.utilise; 0.275, 0.603, pH+Main.P-Source.Conc.+P-Source.Feed.conc.+Main.Thr. Conc.+X.F.Suc+rab+SO4.ferm.+PO4.utilise; 0.248, 0.603, Main.P-Source.Conc.+P-Source.Feed.conc.+X.F.Suc+ X.VXdt+PL+emission_O2+Thr+SO4.ferm.+PO4.ferm.+ PO4.utilise; 0.234, 0.603, Main.P-Source.Conc.+P-Source. Feed.conc.+OD+X.F.Suc+total.Vol+total.cell+PL+emission_O2+SO4.ferm.+PO4.ferm.+PO4.utilise; 0.220, 0.603, pH+tmp+Main.P-Source.Conc.+P-Source.Feed. conc.+ X.F.Suc+X.VXdt+total.Vol+PL+rab+SO4.ferm.+ PO4.ferm.+PO4.utilise; 0.274, 0.603, tmp+Main.P-Source.Conc.+P-Source.Feed.conc.+total.Vol+yield+rab+ SO4.ferm.+PO4.utilise; 0.205, 0.603, pH+Main.P-Source.Conc.+P-Source.Feed.conc.+OD+Lys_conc.+Cell+ total.Vol+total.cell+yield+PL+rab+SO4.ferm.+PO4.utilise; 0.234, 0.603, pH+Main.P-Source.Conc.+P-Source.Feed. conc.+X.F.Suc+PL+emission_O2+Thr+His+SO4.ferm.+ PO4.ferm.+PO4.utilise; 0.248, 0.603, tmp+Main.P-Source.Conc.+P-Source.Feed.conc.+X.F.Suc+X.VXdt+PL+ emission_O2+lactate+SO4.ferm.+PO4.utilise; 0.248, 0.603, pH+Main.P-Source.Conc.+P-Source.Feed.conc.+X.F.Suc+ X.VXdt+rab+Thr+lactate+SO4.ferm.+PO4.utilise; 0.248, 0.603, tmp+Main.P-Source.Conc.+P-Source.Feed.conc.+ X.F.Suc+total.cell+PL+rab+SO4.ferm.+PO4.ferm.+ PO4.utilise; 0.274, 0.603, pH+Main.P-Source.Conc.+P-Source.Feed.conc.+Main.Thr.Conc.+X.F.Suc+ emission_O2+SO4.ferm.+PO4.utilise; 0.234, 0.603, pH+Main.P-Source.Conc.+P-Source.Feed.conc.+X.F.Suc+ X.VXdt+PL+rab+Thr+His+SO4.ferm.+PO4.utilise; 0.248, 0.603, Main.P-Source.Conc.+P-Source.Feed.conc.+ X.F.Suc+Cell+X.VXdt+total.Vol+PL+rab+SO4.ferm.+ PO4.utilise; 0.248, 0.603, pH+Main.P-Source.Conc.+P-Source.Feed.conc.+OD+X.F.Suc+total.Vol+PL+rab+ SO4.ferm.+PO4.utilise; 0.274, 0.603, tmp+Main.P-Source.Conc.+P-Source.Feed.conc.+Lys_conc.+yield+His+ SO4.ferm.+PO4.utilise; 0.248, 0.603, Main.P-Source.Conc.+P-Source.Feed.conc.+X.F.Suc+X.VXdt+PL+ emission_O2+Thr+His+SO4.ferm.+PO4.utilise; 0.248, 0.603, tmp+Main.P-Source.Conc.+P-Source.Feed.conc.+total.Vol+yield+PL+rab+His+SO4.ferm.+PO4.utilise; 0.274, 0.603, Main.P-Source.Conc.+P-Source.Feed.conc.+Nitrogen.Conc.+X.F.Suc+rab+His+SO4.ferm.+PO4.utilise; 0.274, 0.603, tmp+Main.P-Source.Conc.+P-Source.Feed. conc.+Nitrogen.Conc.+yield+SO4.ferm.+PO4.ferm.+ PO4.utilise; 0.248, 0.603, Main.P-Source.Conc.+P-Source.Feed.conc.+X.F.Suc+PL+rab+Thr+His+lactate+ SO4.ferm.+PO4.utilise; 0.248, 0.603, tmp+Main.P-Source.Conc.+P-Source.Feed.conc.+Nitrogen.Conc.+ X.F.Suc+PL+emission_O2+SO4.ferm.+PO4.ferm.+ PO4.utilise; 0.248, 0.603, pH+Main.P-Source.Conc.+P-Source.Feed.conc.+X.F.Suc+Cell+PL+emission_O2+ SO4.ferm.+PO4.ferm.+PO4.utilise; 0.248, 0.603, tmp+ Main.P-Source.Conc.+P-Source.Feed.conc.+X.F.Suc+PL+ rab+lactate+SO4.ferm.+PO4.ferm.+PO4.utilise; 0.234, 0.603, pH+tmp+Main.P-Source.Conc.+P-Source. Feed.conc.+Main.Thr.Conc.+X.F.Suc+total.Vol+PL+emission_O2+SO4.ferm.+PO4.utilise; 0.261, 0.603, Main.P-Source.Conc.+P-Source.Feed.conc.+X.F.Suc+X.VXdt+total.Vol+emission_O2+His+SO4.ferm.+PO4.utilise; 0.248, 0.603, pH+tmp+Main.P-Source.Conc.+P-Source.Feed. conc.+X.F.Suc+emission_O2+Thr+His+SO4.ferm.+ PO4.utilise; 0.234, 0.603, tmp+Main.P-Source.Conc.+P-Source.Feed.conc.+X.F.Suc+total.Vol+PL+rab+Thr+ SO4.ferm.+PO4.ferm.+PO4.utilise; 0.248, 0.603, pH+Main.P-Source.Conc.+P-Source.Feed.conc.+X.F.Suc+ Cell+PL+emission_O2+His+SO4.ferm.+PO4.utilise; 0.248, 0.603, pH+tmp+Main.P-Source.Conc.+P-Source.Feed. conc.+X.F.Suc+total.cell+PL+SO4.ferm.+PO4.ferm.+ PO4.utilise; 0.234, 0.603, pH+Main.P-Source.Conc.+P-Source.Feed.conc.+X.F.Suc+Cell+X.VXdt+total.Vol+PL+ emission_O2+SO4.ferm.+PO4.utilise; 0.248, 0.603, Main.P-Source.Conc.+P-Source.Feed.conc.+X.F.Suc+PL+ emission_O2+Thr+His+lactate+SO4.ferm.+PO4.utilise; 0.261, 0.603, tmp+Main.P-Source.Conc.+P-Source.Feed. conc.+yield+PL+emission_O2+SO4.ferm.+PO4.ferm.+ PO4.utilise; 0.261, 0.603, pH+Main.P-Source.Conc.+P-Source.Feed.conc.+X.F.Suc+emission_O2+Thr+ SO4.ferm.+PO4.ferm.+PO4.utilise; 0.274, 0.603, Main.P-Source.Conc.+P-Source.Feed.conc.+X.F.Suc+rab+His+ lactate+SO4.ferm.+PO4.utilise; 0.234, 0.603, tmp+Main.P-Source.Conc.+P-Source.Feed.conc.+X.F.Suc+X.VXdt+PL+ emission_O2+Thr+SO4.ferm.+PO4.ferm.+PO4.utilise; 0.234, 0.603, Main.P-Source.Conc.+P-Source.Feed.conc.+ X.F.Suc+total.Vol+PL+rab+Thr+His+SO4.ferm.+ PO4.ferm.+PO4.utilise; 0.248, 0.603, tmp+Main.P-Source.Conc.+P-Source.Feed.conc.+X.F.Suc+total.cell+ PL+rab+His+SO4.ferm.+PO4.utilise; 0.261, 0.603, pH+Main.P-Source.Conc.+P-Source.Feed.conc.+yield+ PL+emission_O2+His+SO4.ferm.+PO4.utilise; 0.274, 0.603, tmp+Main.P-Source.Conc.+P-Source.Feed.conc.+ X.F.Suc+Thr+SO4.ferm.+PO4.ferm.+PO4.utilise; 0.234, 0.603, Main.P-Source.Conc.+P-Source.Feed.conc.+Nitrogen.Conc.+X.F.Suc+X.VXdt+total.Vol+PL+rab+His+ SO4.ferm.+PO4.utilise; 0.219, 0.603, pH+Main.P-Source.Conc.+P-Source.Feed.conc.+Main.Thr.Conc.+ X.F.Suc+X.VXdt+total.Vol+PL+rab+SO4.ferm.+ PO4.ferm.+PO4.utilise; 0.234, 0.603, pH+Main.P-Source.Conc.+P-Source.Feed.conc.+OD+X.F.Suc+ X.VXdt+total.cell+PL+rab+SO4.ferm.+PO4.utilise; 0.274, 0.603, Main.P-Source.Conc.+P-Source.Feed.conc.+ X.F.Suc+X.VXdt+emission_O2+Thr+SO4.ferm.+ PO4.utilise; 0.219, 0.603, pH+Main.P-Source.Conc.+P-Source.Feed.conc.+X.F.Suc+X.VXdt+PL+emission_O2+ Thr+lactate+SO4.ferm.+PO4.ferm.+PO4.utilise; 0.261, 0.603, Main.P-Source.Conc.+P-Source.Feed.conc.+OD+ X.F.Suc+PL+emission_O2+SO4.ferm.+PO4.ferm.+ PO4.utilise; 0.234, 0.603, Main.P-Source.Conc.+P-Source. Feed.conc.+X.F.Suc+X.VXdt+total.Vol+PL+rab+Thr+ SO4.ferm.+PO4.ferm.+PO4.utilise; 0.219, 0.603, pH+Main.P-Source.Conc.+P-Source.Feed.conc.+X.F.Suc+ X.VXdt+total.Vol+total.cell+PL+rab+SO4.ferm.+ PO4.ferm.+PO4.utilise; 0.261, 0.603, Main.P-Source.Conc.+P-Source.Feed.conc.+X.F.Suc+rab+Thr+ His+SO4.ferm.+PO4.ferm.+PO4.utilise; 0.286, 0.603, Main.P-Source.Conc.+P-Source.Feed.conc.+X.F.Suc+Cell+ rab+SO4.ferm.+PO4.utilise; 0.247, 0.603, Main.P-Source.Conc.+P-Source.Feed.conc.+Main.Thr.Conc.+ X.F.Suc+total.Vol+PL+emission_O2+Thr+SO4.ferm.+ PO4.utilise; 0.247, 0.603, tmp+Main.P-Source.Conc.+P-Source.Feed.conc.+X.F.Suc+X.VXdt+total.Vol+PL+His+ SO4.ferm.+PO4.utilise; 0.274, 0.603, tmp+Main.P-Source.Conc.+P-Source.Feed.conc.+yield+PL+rab+

SO4.ferm.+PO4.utilise; 0.274, 0.603, Main.P-Source.Conc.+P-Source.Feed.conc.+Lys_conc.+yield+rab+His+SO4.ferm.+PO4.utilise; 0.261, 0.603, pH+tmp+Main.P-Source.Conc.+P-Source.Feed.conc.+X.F.Suc+rab+SO4.ferm.+PO4.ferm.+PO4.utilise; 0.233, 0.603, pH+Main.P-Source.Conc.+P-Source.Feed.conc.+X.F.Suc+X.VXdt+PL+emission_O2+His+lactate+SO4.ferm.+PO4.utilise; 0.261, 0.603, tmp+Main.P-Source.Conc.+P-Source.Feed.conc.+Main.Thr.Conc.+X.F.Suc+X.VXdt+PL+SO4.ferm.+PO4.utilise; 0.286, 0.603, tmp+Main.P-Source.Conc.+P-Source.Feed.conc.+Nitrogen.Conc.+yield+SO4.ferm.+PO4.utilise; 0.286, 0.603, Main.P-Source.Conc.+P-Source.Feed.conc.+total.Vol+PL+emission_O2+SO4.ferm.+PO4.utilise; 0.233, 0.603, Main.P-Source.Conc.+P-Source.Feed.conc.+OD+X.F.Suc+total.Vol+total.cell+PL+rab+His+SO4.ferm.+PO4.utilise; 0.286, 0.603, Main.P-Source.Conc.+P-Source.Feed.conc.+PL+rab+SO4.ferm.+PO4.ferm.+PO4.utilise; 0.286, 0.602, pH+Main.P-Source.Conc.+P-Source.Feed.conc.+yield+His+SO4.ferm.+PO4.utilise; 0.261, 0.602, tmp+Main.P-Source.Conc.+P-Source.Feed.conc.+X.F.Suc+X.VXdt+emission_O2+His+SO4.ferm.+PO4.utilise; 0.261, 0.602, tmp+Main.P-Source.Conc.+P-Source.Feed.conc.+Lys_conc.+yield+PL+rab+SO4.ferm.+PO4.utilise; 0.233, 0.602, pH+tmp+Main.P-Source.Conc.+P-Source.Feed.conc.+X.F.Suc+total.cell+PL+rab+Thr+SO4.ferm.+PO4.utilise; 0.247, 0.602, Main.P-Source.Conc.+P-Source.Feed.conc.+Main.Thr.Conc.+X.F.Suc+PL+rab+Thr+SO4.ferm.+PO4.ferm.+PO4.utilise; 0.204, 0.602, pH+tmp+Main.P-Source.Conc.+P-Source.Feed.conc.+X.F.Suc+X.VXdt+PL+rab+Thr+lactate+SO4.ferm.+PO4.ferm.+PO4.utilise; 0.260, 0.602, tmp+Main.P-Source.Conc.+P-Source.Feed.conc.+OD+X.F.Suc+PL+rab+SO4.ferm.+PO4.utilise; 0.260, 0.602, Main.P-Source.Conc.+P-Source.Feed.conc.+total.Vol+PL+rab+His+SO4.ferm.+PO4.utilise; 0.233, 0.602, pH+tmp+Main.P-Source.Conc.+P-Source.Feed.conc.+X.F.Suc+total.cell+PL+rab+SO4.ferm.+PO4.ferm.+PO4.utilise; 0.260, 0.602, tmp+Main.P-Source.Conc.+P-Source.Feed.conc.+X.F.Suc+X.VXdt+rab+Thr+SO4.ferm.+PO4.utilise; 0.247, 0.602, Main.P-Source.Conc.+P-Source.Feed.conc.+Main.Thr.Conc.+X.F.Suc+X.VXdt+PL+rab+SO4.ferm.+PO4.ferm.+PO4.utilise; 0.260, 0.602, pH+tmp+Main.P-Source.Conc.+P-Source.Feed.conc.+total.Vol+yield+His+SO4.ferm.+PO4.utilise; 0.273, 0.602, pH+Main.P-Source.Conc.+P-Source.Feed.conc.+X.F.Suc+PL+His+SO4.ferm.+PO4.utilise; 0.260, 0.602, pH+Main.P-Source.Conc.+P-Source.Feed.conc.+Nitrogen.Conc.+X.F.Suc+rab+Thr+SO4.ferm.+PO4.utilise; 0.233, 0.602, pH+tmp+Main.P-Source.Conc.+P-Source.Feed.conc.+Main.Thr.Conc.+X.F.Suc+PL+emission_O2+SO4.ferm.+PO4.ferm.+PO4.utilise; 0.260, 0.602, Main.P-Source.Conc.+P-Source.Feed.conc.+X.F.Suc+total.Vol+PL+emission_O2+lactate+SO4.ferm.+PO4.utilise; 0.260, 0.602, Main.P-Source.Conc.+P-Source.Feed.conc.+Lys_conc.+yield+PL+emission_O2+His+SO4.ferm.+PO4.utilise; 0.247, 0.602, tmp+Main.P-Source.Conc.+P-Source.Feed.conc.+yield+PL+rab+His+SO4.ferm.+PO4.ferm.+PO4.utilise; 0.260, 0.602, tmp+Main.P-Source.Conc.+P-Source.Feed.conc.+X.F.Suc+emission_O2+Thr+SO4.ferm.+PO4.ferm.+PO4.utilise; 0.247, 0.602, pH+tmp+Main.P-Source.Conc.+P-Source.Feed.conc.+total.Vol+yield+PL+emission_O2+SO4.ferm.+PO4.utilise; 0.247, 0.602, pH+Main.P-Source.Conc.+P-Source.Feed.conc.+OD+X.F.Suc+PL+rab+Thr+SO4.ferm.+PO4.utilise; 0.273, 0.602, pH+Main.P-Source.Conc.+P-Source.Feed.conc.+Lys_conc.+X.F.Suc+rab+SO4.ferm.+PO4.utilise; 0.260, 0.602, tmp+Main.P-Source.Conc.+P-Source.Feed.conc.+Nitrogen.Conc.+total.Vol+yield+PL+SO4.ferm.+PO4.utilise; 0.218, 0.602, pH+Main.P-Source.Conc.+P-Source.Feed.conc.+OD+X.F.Suc+total.Vol+total.cell+PL+emission_O2+His+SO4.ferm.+PO4.utilise; 0.218, 0.602, pH+tmp+Main.P-Source.Conc.+P-Source.Feed.conc.+X.F.Suc+X.VXdt+PL+rab+Thr+His+SO4.ferm.+PO4.utilise; 0.233, 0.602, Main.P-Source.Conc.+P-Source.Feed.conc.+X.F.Suc+X.VXdt+PL+rab+Thr+lactate+SO4.ferm.+PO4.ferm.+PO4.utilise; 0.260, 0.602, Main.P-Source.Conc.+P-Source.Feed.conc.+Lys_conc.+yield+PL+rab+His+SO4.ferm.+PO4.utilise; 0.218, 0.602, pH+Main.P-Source.Conc.+P-Source.Feed.conc.+Nitrogen.Conc.+OD+X.F.Suc+total.Vol+total.cell+PL+rab+SO4.ferm.+PO4.utilise; 0.247, 0.602, tmp+Main.P-Source.Conc.+P-Source.Feed.conc.+Nitrogen.Conc.+yield+PL+His+SO4.ferm.+PO4.ferm.+PO4.utilise; 0.260, 0.602, Main.P-Source.Conc.+P-Source.Feed.conc.+OD+X.F.Suc+total.cell+PL+emission_O2+SO4.ferm.+PO4.utilise; 0.260, 0.602, tmp+Main.P-Source.Conc.+P-Source.Feed.conc.+X.F.Suc+total.cell+PL+SO4.ferm.+PO4.ferm.+PO4.utilise; 0.273, 0.602, Main.P-Source.Conc.+P-Source.Feed.conc.+X.F.Suc+total.cell+rab+Thr+SO4.ferm.+PO4.utilise; 0.233, 0.602, pH+tmp+Main.P-Source.Conc.+P-Source.Feed.conc.+Nitrogen.Conc.+X.F.Suc+X.VXdt+PL+His+SO4.ferm.+PO4.utilise; 0.260, 0.602, pH+Main.P-Source.Conc.+P-Source.Feed.conc.+X.F.Suc+emission_O2+His+SO4.ferm.+PO4.ferm.+PO4.utilise; 0.218, 0.602, pH+tmp+Main.P-Source.Conc.+P-Source.Feed.conc.+Nitrogen.Conc.+X.F.Suc+X.VXdt+PL+emission_O2+SO4.ferm.+PO4.ferm.+PO4.utilise; 0.171, 0.602, pH+Main.P-Source.Conc.+P-Source.Feed.conc.+Main.Thr.Conc.+OD+Lys_conc.+Cell+total.Vol+total.cell+yield+PL+emission_O2+SO4.ferm.+PO4.ferm.+PO4.utilise; 0.218, 0.602, pH+Main.P-Source.Conc.+P-Source.Feed.conc.+OD+X.F.Suc+X.VXdt+total.Vol+PL+rab+SO4.ferm.+PO4.ferm.+PO4.utilise; 0.273, 0.602, Main.P-Source.Conc.+P-Source.Feed.conc.+yield+rab+His+SO4.ferm.+PO4.ferm.+PO4.utilise; 0.273, 0.602, Main.P-Source.Conc.+P-Source.Feed.conc.+Lys_conc.+X.F.Suc+rab+His+SO4.ferm.+PO4.utilise; 0.260, 0.602, Main.P-Source.Conc.+P-Source.Feed.conc.+X.F.Suc+X.VXdt+emission_O2+Thr+lactate+SO4.ferm.+PO4.utilise; 0.285, 0.602, pH+Main.P-Source.Conc.+P-Source.Feed.conc.+yield+rab+SO4.ferm.+PO4.utilise; 0.260, 0.602, tmp+Main.P-Source.Conc.+P-Source.Feed.conc.+Main.Thr.Conc.+X.F.Suc+total.Vol+PL+SO4.ferm.+PO4.utilise; 0.273, 0.602, Main.P-Source.Conc.+P-Source.Feed.conc.+X.F.Suc+X.VXdt+rab+lactate+SO4.ferm.+PO4.utilise; 0.246, 0.602, pH+tmp+Main.P-Source.Conc.+P-Source.Feed.conc.+Main.Thr.Conc.+X.F.Suc+total.Vol+PL+SO4.ferm.+PO4.utilise; 0.246, 0.602, tmp+Main.P-Source.Conc.+P-Source.Feed.conc.+X.F.Suc+X.VXdt+PL+Thr+His+SO4.ferm.+PO4.utilise; 0.285, 0.602, pH+Main.P-Source.Conc.+P-Source.Feed.conc.+X.F.Suc+total.Vol+SO4.ferm.+PO4.utilise; 0.203, 0.602, pH+tmp+Main.P-Source.Conc.+P-Source.Feed.conc.+X.F.Suc+X.VXdt+PL+emission_O2+Thr+His+lactate+SO4.ferm.+PO4.utilise; 0.246, 0.602, Main.P-Source.Conc.+P-Source.Feed.conc.+Nitrogen.Conc.+X.F.Suc+total.Vol+PL+rab+His+SO4.ferm.+PO4.utilise; 0.273, 0.602, tmp+Main.P-Source.Conc.+P-Source.Feed.conc.+Nitrogen.Conc.+yield+PL+SO4.ferm.+PO4.utilise; 0.232, 0.602, Main.P-Source.Conc.+P-Source.Feed.conc.+X.F.Suc+X.VXdt+total.Vol+PL+emission_O2+Thr+lactate+SO4.ferm.+PO4.utilise; 0.246, 0.602, tmp+Main.P-Source.Conc.+P-Source.Feed.conc.+Main.Thr.Conc.+

X.F.Suc+PL+emission_O2+SO4.ferm.+PO4.ferm.+ PO4.utilise; 0.232, 0.602, pH+tmp+Main.P-Source.Conc.+ P-Source.Feed.conc.+X.F.Suc+PL+rab+Thr+lactate+ SO4.ferm.+PO4.utilise; 0.218, 0.602, pH+Main.P-Source.Conc.+P-Source.Feed.conc.+Nitrogen.Conc.+ X.F.Suc+X.VXdt+total.Vol+PL+emission_O2+His+ SO4.ferm.+PO4.utilise; 0.232, 0.602, pH+tmp+Main.P-Source.Conc.+P-Source.Feed.conc.+X.F.Suc+total.Vol+ PL+rab+lactate+SO4.ferm.+PO4.utilise; 0.218, 0.602, pH+tmp+Main.P-Source.Conc.+P-Source.Feed.conc.+ Main.Thr.Conc.+X.F.Suc+X.VXdt+total.Vol+PL+emission_O2+SO4.ferm.+PO4.utilise; 0.246, 0.602, pH+Main.P-Source.Conc.+P-Source.Feed.conc.+OD+ X.F.Suc+PL+emission_O2+SO4.ferm.+PO4.ferm.+ PO4.utilise; 0.232, 0.602, pH+Main.P-Source.Conc.+P-Source.Feed.conc.+OD+X.F.Suc+X.VXdt+PL+rab+ SO4.ferm.+PO4.ferm.+PO4.utilise; 0.232, 0.602, pH+tmp+ Main.P-Source.Conc.+P-Source.Feed.conc.+X.F.Suc+PL+ emission_O2+lactate+SO4.ferm.+PO4.ferm.+PO4.utilise; 0.260, 0.602, pH+tmp+Main.P-Source.Conc.+P-Source. Feed.conc.+X.F.Suc+X.VXdt+emission_O2+SO4.ferm.+ PO4.utilise; 0.246, 0.602, pH+tmp+Main.P-Source.Conc.+ P-Source.Feed.conc.+Main.Thr.Conc.+X.F.Suc+PL+ SO4.ferm.+PO4.ferm.+PO4.utilise; 0.260, 0.602, Main.P-Source.Conc.+P-Source.Feed.conc.+X.F.Suc+Cell+ total.cell+PL+rab+SO4.ferm.+PO4.utilise; 0.232, 0.602, tmp+Main.P-Source.Conc.+P-Source.Feed.conc.+Main. Thr.Conc.+X.F.Suc+total.Vol+PL+rab+Thr+SO4.ferm.+ PO4.utilise; 0.260, 0.602, tmp+Main.P-Source.Conc.+P-Source.Feed.conc.+X.F.Suc+rab+His+SO4.ferm.+ PO4.ferm.+PO4.utilise; 0.218, 0.602, pH+Main.P-Source.Conc.+P-Source.Feed.conc.+X.F.Suc+X.VXdt+ total.Vol+PL+rab+Thr+His+SO4.ferm.+PO4.utilise; 0.273, 0.602, pH+Main.P-Source.Conc.+P-Source.Feed.conc.+ X.F.Suc+total.cell+rab+SO4.ferm.+PO4.utilise; 0.260, 0.602, Main.P-Source.Conc.+P-Source.Feed.conc.+OD+ X.F.Suc+PL+rab+His+SO4.ferm.+PO4.utilise; 0.246, 0.602, pH+Main.P-Source.Conc.+P-Source.Feed.conc.+ X.F.Suc+total.cell+PL+emission_O2+Thr+SO4.ferm.+ PO4.utilise; 0.246, 0.602, Main.P-Source.Conc.+P-Source. Feed.conc.+Main.Thr.Conc.+X.F.Suc+X.VXdt+PL+rab+ His+SO4.ferm.+PO4.utilise; 0.246, 0.602, Main.P-Source.Conc.+P-Source.Feed.conc.+Nitrogen.Conc.+ X.F.Suc+PL+rab+Thr+SO4.ferm.+PO4.ferm.+PO4.utilise; 0.272, 0.602, Main.P-Source.Conc.+P-Source.Feed.conc.+ X.F.Suc+X.VXdt+total.cell+rab+SO4.ferm.+PO4.utilise; 0.259, 0.602, Main.P-Source.Conc.+P-Source.Feed.conc.+ X.F.Suc+total.Vol+rab+Thr+SO4.ferm.+PO4.ferm.+ PO4.utilise; 0.232, 0.602, pH+tmp+Main.P-Source.Conc.+ P-Source.Feed.conc.+X.F.Suc+total.cell+PL+rab+His+ SO4.ferm.+PO4.utilise; 0.218, 0.602, pH+tmp+Main.P-Source.Conc.+P-Source.Feed.conc.+X.F.Suc+X.VXdt+PL+ rab+Thr+SO4.ferm.+PO4.ferm.+PO4.utilise; 0.232, 0.602, pH+Main.P-Source.Conc.+P-Source.Feed.conc.+X.F.Suc+ total.Vol+PL+rab+lactate+SO4.ferm.+PO4.ferm.+ PO4.utilise; 0.218, 0.602, pH+tmp+Main.P-Source.Conc.+ P-Source.Feed.conc.+Nitrogen.Conc.+X.F.Suc+total.Vol+ PL+rab+Thr+SO4.ferm.+PO4.utilise; 0.232, 0.602, pH+tmp+Main.P-Source.Conc.+P-Source.Feed.conc.+Nitrogen.Conc.+X.F.Suc+PL+emission_O2+SO4.ferm.+ PO4.ferm.+PO4.utilise; 0.246, 0.602, pH+tmp+Main.P-Source.Conc.+P-Source.Feed.conc.+X.F.Suc+total.Vol+ rab+His+SO4.ferm.+PO4.utilise; 0.285, 0.602, Main.P-Source.Conc.+P-Source.Feed.conc.+Nitrogen.Conc.+yield+ rab+SO4.ferm.+PO4.utilise; 0.217, 0.602, pH+tmp+ Main.P-Source.Conc.+P-Source.Feed.conc.+X.F.Suc+ X.VXdt+PL+rab+lactate+SO4.ferm.+PO4.ferm.+ PO4.utilise; 0.217, 0.602, pH+tmp+Main.P-Source.Conc.+ P-Source.Feed.conc.+Nitrogen.Conc.+X.F.Suc+X.VXdt+ PL+emission_O2+His+SO4.ferm.+PO4.utilise; 0.232, 0.602, pH+tmp+Main.P-Source.Conc.+P-Source.Feed. conc.+Nitrogen.Conc.+X.F.Suc+PL+rab+His+SO4.ferm.+ PO4.utilise; 0.259, 0.602, pH+Main.P-Source.Conc.+P-Source.Feed.conc.+X.F.Suc+total.Vol+rab+SO4.ferm.+ PO4.ferm.+PO4.utilise; 0.217, 0.602, pH+Main.P-Source.Conc.+P-Source.Feed.conc.+OD+X.F.Suc+ X.VXdt+total.Vol+PL+rab+His+SO4.ferm.+PO4.utilise; 0.232, 0.602, pH+tmp+Main.P-Source.Conc.+P-Source. Feed.conc.+Nitrogen.Conc.+X.F.Suc+X.VXdt+PL+ SO4.ferm.+PO4.ferm.+PO4.utilise; 0.285, 0.602, Main.P-Source.Conc.+P-Source.Feed.conc.+OD+X.F.Suc+rab+ SO4.ferm.+PO4.utilise; 0.259, 0.602, tmp+Main.P-Source.Conc.+P-Source.Feed.conc.+Lys_conc.+total.Vol+ PL+His+SO4.ferm.+PO4.utilise; 0.232, 0.602, pH+Main.P-Source.Conc.+P-Source.Feed.conc.+Nitrogen.Conc.+ X.F.Suc+PL+emission_O2+Thr+His+SO4.ferm.+ PO4.utilise; 0.272, 0.602, pH+Main.P-Source.Conc.+P-Source.Feed.conc.+PL+rab+SO4.ferm.+PO4.ferm.+ PO4.utilise; 0.232, 0.602, pH+Main.P-Source.Conc.+P-Source.Feed.conc.+Nitrogen.Conc.+X.F.Suc+X.VXdt+PL+ emission_O2+SO4.ferm.+PO4.ferm.+PO4.utilise; 0.246, 0.602, pH+Main.P-Source.Conc.+P-Source.Feed.conc.+ X.F.Suc+X.VXdt+PL+emission_O2+rab+SO4.ferm.+ PO4.utilise; 0.232, 0.602, pH+tmp+Main.P-Source.Conc.+ P-Source.Feed.conc.+X.F.Suc+X.VXdt+PL+Thr+lactate+ SO4.ferm.+PO4.utilise; 0.232, 0.601, pH+Main.P-Source.Conc.+P-Source.Feed.conc.+X.F.Suc+X.VXdt+ total.cell+PL+emission_O2+SO4.ferm.+PO4.ferm.+ PO4.utilise; 0.202, 0.601, pH+Main.P-Source.Conc.+P-Source.Feed.conc.+X.F.Suc+X.VXdt+total.Vol+PL+rab+ Thr+lactate+SO4.ferm.+PO4.ferm.+PO4.utilise; 0.246, 0.601, tmp+Main.P-Source.Conc.+P-Source.Feed.conc.+ Nitrogen.Conc.+yield+PL+rab+SO4.ferm.+PO4.ferm.+ PO4.utilise; 0.246, 0.601, pH+Main.P-Source.Conc.+P-Source.Feed.conc.+X.F.Suc+PL+emission_O2+rab+ SO4.ferm.+PO4.ferm.+PO4.utilise; 0.246, 0.601, pH+tmp+ Main.P-Source.Conc.+P-Source.Feed.conc.+ Nitrogen.Conc.+total.Vol+yield+PL+SO4.ferm.+ PO4.utilise; 0.232, 0.601, tmp+Main.P-Source.Conc.+P-Source.Feed.conc.+X.F.Suc+X.VXdt+total.Vol+PL+rab+ SO4.ferm.+PO4.ferm.+PO4.utilise; 0.246, 0.601, pH+tmp+ Main.P-Source.Conc.+P-Source.Feed.conc.+X.F.Suc+ X.VXdt+PL+lactate+SO4.ferm.+PO4.utilise; 0.217, 0.601, pH+tmp+Main.P-Source.Conc.+P-Source.Feed.conc.+ X.F.Suc+X.VXdt+total.cell+PL+rab+His+SO4.ferm.+ PO4.utilise; 0.285, 0.601, pH+Main.P-Source.Conc.+P-Source.Feed.conc.+yield+emission_O2+SO4.ferm.+ PO4.utilise; 0.259, 0.601, tmp+Main.P-Source.Conc.+P-Source.Feed.conc.+Lys_conc.+yield+PL+His+SO4.ferm.+ PO4.utilise; 0.246, 0.601, tmp+Main.P-Source.Conc.+P-Source.Feed.conc.+X.F.Suc+total.Vol+emission_O2+Thr+ His+SO4.ferm.+PO4.utilise; 0.202, 0.601, pH+Main.P-Source.Conc.+P-Source.Feed.conc.+X.F.Suc+X.VXdt+ total.Vol+PL+emission_O2+Thr+His+lactate+SO4.ferm.+ PO4.utilise; 0.217, 0.601, pH+tmp+Main.P-Source.Conc.+ P-Source.Feed.conc.+Main.Thr.Conc.+X.F.Suc+X.VXdt+ PL+rab+SO4.ferm.+PO4.ferm.+PO4.utilise; 0.246, 0.601, Main.P-Source.Conc.+P-Source.Feed.conc.+X.F.Suc+total. cell+PL+rab+His+SO4.ferm.+PO4.ferm.+PO4.utilise; 0.272, 0.601, pH+tmp+Main.P-Source.Conc.+P-Source. Feed.conc.+yield+SO4.ferm.+PO4.ferm.+PO4.utilise; 0.246, 0.601, pH+Main.P-Source.Conc.+P-Source.Feed. conc.+X.F.Suc+Cell+total.cell+PL+rab+SO4.ferm.+ PO4.utilise; 0.232, 0.601, pH+Main.P-Source.Conc.+P-

Source.Feed.conc.+Main.Thr.Conc.+X.F.Suc+PL+rab+ Thr+SO4.ferm.+PO4.ferm.+PO4.utilise; 0.232, 0.601, tmp+ Main.P-Source.Conc.+P-Source.Feed.conc.+Nitrogen. Conc.+X.F.Suc+X.VXdt+total.Vol+PL+rab+SO4.ferm.+ PO4.utilise; 0.245, 0.601, Main.P-Source.Conc.+P-Source. Feed.conc.+X.F.Suc+PL+rab+His+lactate+SO4.ferm.+ PO4.ferm.+PO4.utilise; 0.259, 0.601, tmp+Main.P-Source. Conc.+P-Source.Feed.conc.+X.F.Suc+total.cell+PL+Thr+ SO4.ferm.+PO4.utilise; 0.259, 0.601, pH+Main.P-Source. Conc.+P-Source.Feed.conc.+Main.Thr.Conc.+X.F.Suc+ rab+Thr+SO4.ferm.+PO4.utilise; 0.231, 0.601, pH+Main.P-Source.Conc.+P-Source.Feed.conc.+Main.Thr.Conc.+X.F. Suc+PL+emission_O2+Thr+His+SO4.ferm.+PO4.utilise; 0.259, 0.601, pH+Main.P-Source.Conc.+P-Source.Feed. conc.+yield+PL+His+SO4.ferm.+PO4.ferm.+PO4.utilise; 0.272, 0.601, Main.P-Source.Conc.+P-Source.Feed.conc.+ total.Vol+PL+rab+His+SO4.ferm.+PO4.utilise; 0.284, 0.601, tmp+Main.P-Source.Conc.+P-Source.Feed.conc.+ Main.Thr.Conc.+X.F.Suc+SO4.ferm.+PO4.utilise; 0.259, 0.601, tmp+Main.P-Source.Conc.+P-Source.Feed.conc.+total.Vol+yield+rab+His+SO4.ferm.+PO4.utilise; 0.231, 0.601, pH+Main.P-Source.Conc.+P-Source.Feed.conc.+Nitrogen.Conc.+X.F.Suc+total.Vol+PL+emission_O2+Thr+ SO4.ferm.+PO4.utilise; 0.245, 0.601, Main.P-Source. Conc.+P-Source.Feed.conc.+X.F.Suc+X.VXdt+PL+rab+ lactate+SO4.ferm.+PO4.ferm.+PO4.utilise; 0.272, 0.601, tmp+Main.P-Source.Conc.+P-Source.Feed.conc.+total. Vol+PL+emission_O2+SO4.ferm.+PO4.utilise; 0.245, 0.601, Main.P-Source.Conc.+P-Source.Feed.conc.+Nitrogen.Conc.+X.F.Suc+total.Vol+PL+rab+SO4.ferm.+PO4. ferm.+PO4.utilise; 0.259, 0.601, Main.P-Source.Conc.+P-Source.Feed.conc.+X.F.Suc+X.VXdt+total.Vol+rab+Thr+ SO4.ferm.+PO4.utilise; 0.245, 0.601, tmp+Main.P-Source. Conc.+P-Source.Feed.conc.+Main.Thr.Conc.+X.F.Suc+ PL+rab+His+SO4.ferm.+PO4.utilise; 0.231, 0.601, Main.P-Source.Conc.+P-Source.Feed.conc.+OD+X.F.Suc+X. VXdt+total.Vol+total.cell+PL+emission_O2+SO4.ferm.+ PO4.utilise; 0.284, 0.601, tmp+Main.P-Source.Conc.+P-Source.Feed.conc.+yield+rab+SO4.ferm.+PO4.utilise; 0.217, 0.601, pH+tmp+Main.P-Source.Conc.+P-Source. Feed.conc.+X.F.Suc+X.VXdt+PL+emission_O2+His+lactate+SO4.ferm.+PO4.utilise; 0.259, 0.601, pH+tmp+Main. P-Source.Conc.+P-Source.Feed.conc.+X.F.Suc+Cell+PL+ SO4.ferm.+PO4.utilise; 0.217, 0.601, pH+Main.P-Source. Conc.+P-Source.Feed.conc.+Main.Thr.Conc.+X.F.Suc+X. VXdt+total.Vol+PL+emission_O2+SO4.ferm.+PO4.ferm.+ PO4.utilise; 0.272, 0.601, Main.P-Source.Conc.+P-Source. Feed.conc.+X.F.Suc+rab+lactate+SO4.ferm.+PO4.ferm.+ PO4.utilise

[15. Linear Model that Predicts Lysine Production Amount in Interval 5]

0.610, 0.826, pH+tmp+Nitrogen.Conc.+OD+Lys_conc.+X. VXdt+total.cell+emission_O2+rab+Thr+lactate+PO4. ferm.; 0.600, 0.825, pH+tmp+Nitrogen.Conc.+OD+Lys_ conc.+X.VXdt+total.cell+PL+emission_O2+rab+Thr+ lactate+PO4.ferm.; 0.598, 0.824, pH+tmp+Nitrogen.Conc.+ OD+Lys_conc.+X.F.Suc+X.VXdt+total.cell+emission_O2+ rab+Thr+lactate+PO4.ferm.; 0.612, 0.823, tmp+Nitrogen. Conc.+OD+Lys_conc.+X.VXdt+total.cell+emission_O2+ rab+Thr+lactate+PO4.ferm.; 0.588, 0.822, pH+tmp+ Nitrogen.Conc.+OD+Lys_conc.+X.VXdt+total.Vol+total. cell+PL+emission_O2+rab+Thr+lactate+PO4.ferm.; 0.595, 0.822, pH+tmp+Nitrogen.Conc.+Lys_conc.+X.VXdt+total. Vol+total.cell+PL+emission_O2+rab+Thr+lactate+PO4. ferm.; 0.595, 0.822, pH+tmp+Nitrogen.Conc.+OD+Lys_ conc.+X.VXdt+total.Vol+total.cell+emission_O2+rab+ Thr+lactate+PO4.ferm.; 0.617, 0.822, pH+tmp+Nitrogen. Conc.+Lys_conc.+X.VXdt+total.Vol+emission_O2+rab+ lactate+PO4.ferm.; 0.609, 0.822, pH+tmp+P-Source.Feed. conc.+Nitrogen.Conc.+Lys_conc.+X.VXdt+total.Vol+ emission_O2+rab+lactate+PO4.ferm.; 0.601, 0.821, pH+tmp+OD+Lys_conc.+X.VXdt+total.cell+PL+emission_O2+rab+Thr+lactate+PO4.ferm.; 0.601, 0.821, pH+tmp+Nitrogen.Conc.+Lys_conc.+X.VXdt+total.Vol+ total.cell+emission_O2+rab+Thr+lactate+PO4.ferm.; 0.593, 0.821, pH+tmp+Nitrogen.Conc.+OD+Lys_conc.+X.VXdt+ total.cell+emission_O2+rab+Thr+His+lactate+PO4.ferm.; 0.600, 0.821, pH+tmp+Nitrogen.Conc.+Lys_conc.+X. VXdt+total.Vol+PL+emission_O2+rab+Thr+lactate+PO4. ferm.; 0.608, 0.821, pH+tmp+Nitrogen.Conc.+Lys_conc.+ X.VXdt+total.Vol+emission_O2+rab+Thr+lactate+PO4. ferm.; 0.613, 0.820, tmp+OD+Lys_conc.+X.VXdt+total. cell+emission_O2+rab+Thr+lactate+PO4.ferm.; 0.606, 0.820, pH+tmp+Nitrogen.Conc.+Lys_conc.+X.F.Suc+X. VXdt+total.Vol+emission_O2+rab+lactate+PO4.ferm.; 0.599, 0.820, tmp+Nitrogen.Conc.+OD+Lys_conc.+X.F. Suc+X.VXdt+total.cell+emission_O2+rab+Thr+lactate+ PO4.ferm.; 0.606, 0.820, pH+tmp+Nitrogen.Conc.+Lys_ conc.+X.VXdt+total.Vol+emission_O2+rab+His+lactate+ PO4.ferm.; 0.582, 0.820, tmp+Nitrogen.Conc.+Lys_conc.+ X.VXdt+total.Vol+yield+PL+emission_O2+rab+Thr+ lactate+PO4.ferm.+PO4.apporte+PO4.utilise; 0.598, 0.820, pH+tmp+P-Source.Feed.conc.+Nitrogen.Conc.+Lys_ conc.+X.VXdt+total.Vol+emission_O2+rab+His+lactate+ PO4.ferm.; 0.597, 0.820, Nitrogen.Conc.+Lys_conc.+X. VXdt+total.Vol+yield+emission_O2+rab+Thr+lactate+ PO4.ferm.+PO4.apporte+PO4.utilise; 0.589, 0.819, pH+tmp+Nitrogen.Conc.+OD+Lys_conc.+X.VXdt+total. Vol+PL+emission_O2+rab+Thr+lactate+PO4.ferm.; 0.604, 0.819, pH+tmp+OD+Lys_conc.+X.VXdt+total.cell+emission_O2+rab+Thr+lactate+PO4.ferm.; 0.581, 0.819, pH+tmp+Nitrogen.Conc.+OD+Lys_conc.+X.VXdt+total. cell+PL+emission_O2+rab+Thr+His+lactate+PO4.ferm.; 0.604, 0.819, pH+tmp+OD+Lys_conc.+X.VXdt+total.cell+ PL+emission_O2+rab+Thr+PO4.ferm.; 0.581, 0.819, pH+tmp+Nitrogen.Conc.+OD+Lys_conc.+X.F.Suc+X. VXdt+total.cell+emission_O2+rab+Thr+His+lactate+PO4. ferm.; 0.589, 0.819, Nitrogen.Conc.+Lys_conc.+X.VXdt+ total.Vol+yield+PL+emission_O2+rab+Thr+lactate+PO4. ferm.+PO4.apporte+PO4.utilise; 0.604, 0.819, Nitrogen. Conc.+Lys_conc.+X.VXdt+total.Vol+yield+emission_O2+ rab+Thr+lactate+PO4.ferm.+PO4.apporte; 0.617, 0.818, tmp+Nitrogen.Conc.+OD+Lys_conc.+X.VXdt+total.cell+ Thr+lactate+PO4.ferm.; 0.595, 0.818, tmp+Nitrogen. Conc.+OD+Lys_conc.+X.VXdt+total.cell+emission_O2+ rab+Thr+His+lactate+PO4.ferm.; 0.595, 0.818, pH+tmp+ Nitrogen.Conc.+OD+Lys_conc.+X.VXdt+total.Vol+ emission_O2+rab+Thr+lactate+PO4.ferm.; 0.595, 0.818, tmp+Nitrogen.Conc.+OD+Lys_conc.+X.VXdt+total.cell+ PL+emission_O2+rab+Thr+lactate+PO4.ferm.; 0.602, 0.818, tmp+OD+Lys_conc.+X.VXdt+total.cell+PL+emission_O2+rab+Thr+lactate+PO4.ferm.; 0.602, 0.818, tmp+ Nitrogen.Conc.+Lys_conc.+X.VXdt+total.Vol+total.cell+ emission_O2+rab+Thr+lactate+PO4.ferm.; 0.586, 0.818, pH+tmp+Main.Thr.Conc.+Nitrogen.Conc.+OD+Lys_ conc.+X.VXdt+total.cell+emission_O2+rab+Thr+lactate+ PO4.ferm.; 0.578, 0.818, pH+tmp+Nitrogen.Conc.+OD+ Lys_conc.+X.F.Suc+X.VXdt+total.cell+PL+emission_O2+ rab+Thr+lactate+PO4.ferm.; 0.578, 0.818, pH+tmp+ Nitrogen.Conc.+OD+Lys_conc.+X.VXdt+total.Vol+total. cell+emission_O2+rab+Thr+His+lactate+PO4.ferm.; 0.594, 0.818, pH+tmp+Nitrogen.Conc.+OD+Lys_conc.+X.F.Suc+ X.VXdt+total.cell+emission_O2+rab+lactate+PO4.ferm.; 0.601, 0.818, pH+tmp+Nitrogen.Conc.+Lys_conc.+X.

VXdt+total.Vol+total.cell+emission_O2+rab+lactate+PO4.ferm.; 0.569, 0.818, pH+tmp+Nitrogen.Conc.+OD+Lys_conc.+X.VXdt+total.Vol+total.cell+PL+emission_O2+rab+Thr+His+lactate+PO4.ferm.; 0.593, 0.818, tmp+Nitrogen.Conc.+OD+Lys_conc.+X.VXdt+total.Vol+total.cell+emission_O2+rab+Thr+lactate+PO4.ferm.; 0.577, 0.818, pH+tmp+Nitrogen.Conc.+Lys_conc.+X.VXdt+total.Vol+total.cell+PL+emission_O2+rab+Thr+His+lactate+PO4.ferm.; 0.608, 0.818, tmp+Nitrogen.Conc.+OD+Lys_conc.+X.F.Suc+X.VXdt+total.cell+Thr+lactate+PO4.ferm.; 0.593, 0.818, pH+tmp+Nitrogen.Conc.+Lys_conc.+X.F.Suc+X.VXdt+total.Vol+emission_O2+rab+His+lactate+PO4.ferm.; 0.608, 0.817, tmp+Nitrogen.Conc.+Lys_conc.+X.VXdt+total.Vol+emission_O2+rab+Thr+lactate+PO4.ferm.; 0.593, 0.817, pH+tmp+P-Source.Feed.conc.+Nitrogen.Conc.+Lys_conc.+X.VXdt+total.Vol+emission_O2+rab+Thr+lactate+PO4.ferm.; 0.585, 0.817, tmp+Nitrogen.Conc.+Lys_conc.+X.VXdt+total.Vol+yield+emission_O2+rab+Thr+lactate+PO4.ferm.+PO4.apporte+PO4.utilise; 0.593, 0.817, pH+tmp+Main.Thr.Conc.+Nitrogen.Conc.+Lys_conc.+X.VXdt+total.Vol+emission_O2+rab+Thr+lactate+PO4.ferm.; 0.615, 0.817, tmp+OD+Lys_conc.+X.VXdt+total.cell+PL+Thr+lactate+PO4.ferm.; 0.585, 0.817, pH+tmp+Nitrogen.Conc.+Lys_conc.+X.VXdt+total.cell+emission_O2+rab+Thr+His+lactate+PO4.ferm.; 0.607, 0.817, pH+tmp+OD+Lys_conc.+X.VXdt+total.cell+emission_O2+rab+Thr+PO4.ferm.; 0.576, 0.817, pH+tmp+Nitrogen.Conc.+OD+Lys_conc.+X.F.Suc+X.VXdt+total.Vol+total.cell+emission_O2+rab+Thr+lactate+PO4.ferm.; 0.584, 0.817, pH+tmp+P-Source.Feed.conc.+Nitrogen.Conc.+OD+Lys_conc.+X.VXdt+total.cell+emission_O2+rab+Thr+lactate+PO4.ferm.; 0.600, 0.817, tmp+P-Source.Feed.conc.+Nitrogen.Conc.+Lys_conc.+X.VXdt+total.Vol+emission_O2+rab+Thr+lactate+PO4.ferm.; 0.576, 0.817, pH+tmp+Main.Thr.Conc.+Nitrogen.Conc.+OD+Lys_conc.+X.VXdt+total.cell+PL+emission_O2+rab+Thr+lactate+PO4.ferm.; 0.607, 0.817, tmp+P-Source.Feed.conc.+Nitrogen.Conc.+Lys_conc.+X.VXdt+total.Vol+emission_O2+rab+lactate+PO4.ferm.; 0.592, 0.817, tmp+P-Source.Feed.conc.+Nitrogen.Conc.+OD+Lys_conc.+X.VXdt+total.cell+emission_O2+rab+Thr+lactate+PO4.ferm.; 0.606, 0.817, tmp+Nitrogen.Conc.+OD+Lys_conc.+X.VXdt+total.cell+PL+Thr+lactate+PO4.ferm.; 0.599, 0.817, pH+tmp+Nitrogen.Conc.+OD+Lys_conc.+X.VXdt+total.Vol+emission_O2+rab+lactate+PO4.ferm.; 0.599, 0.817, tmp+Nitrogen.Conc.+Lys_conc.+X.VXdt+total.Vol+emission_O2+rab+Thr+lactate+PO4.ferm.+PO4.apporte; 0.591, 0.816, pH+tmp+Nitrogen.Conc.+OD+Lys_conc.+X.VXdt+total.cell+PL+emission_O2+rab+Thr+PO4.ferm.; 0.591, 0.816, pH+tmp+Nitrogen.Conc.+Lys_conc.+X.VXdt+total.Vol+emission_O2+rab+Thr+His+lactate+PO4.ferm.; 0.583, 0.816, pH+tmp+Main.Thr.Conc.+Nitrogen.Conc.+Lys_conc.+X.VXdt+total.Vol+PL+emission_O2+rab+Thr+lactate+PO4.ferm.; 0.591, 0.816, pH+tmp+Nitrogen.Conc.+Lys_conc.+X.VXdt+total.Vol+total.cell+emission_O2+rab+His+lactate+PO4.ferm.; 0.591, 0.816, pH+tmp+Nitrogen.Conc.+Lys_conc.+X.F.Suc+X.VXdt+total.Vol+total.cell+emission_O2+rab+lactate+PO4.ferm.; 0.566, 0.816, tmp+Nitrogen.Conc.+Lys_conc.+X.VXdt+total.Vol+yield+PL+emission_O2+rab+Thr+His+lactate+PO4.ferm.+PO4.apporte+PO4.utilise; 0.574, 0.816, pH+tmp+Nitrogen.Conc.+OD+Lys_conc.+X.VXdt+total.cell+PL+emission_O2+rab+Thr+lactate+SO4.ferm.+PO4.ferm.; 0.598, 0.816, pH+tmp+Nitrogen.Conc.+OD+Lys_conc.+X.VXdt+total.cell+emission_O2+rab+Thr+PO4.ferm.; 0.612, 0.816, tmp+OD+Lys_conc.+X.VXdt+total.cell+emission_O2+rab+Thr+PO4.ferm.; 0.619, 0.816, tmp+OD+Lys_conc.+X.VXdt+total.cell+Thr+lactate+PO4.ferm.; 0.582, 0.816, pH+tmp+Nitrogen.Conc.+OD+Lys_conc.+X.F.Suc+X.VXdt+total.Vol+total.cell+emission_O2+rab+lactate+PO4.ferm.; 0.590, 0.816, pH+tmp+P-Source.Feed.conc.+Nitrogen.Conc.+Lys_conc.+X.VXdt+total.Vol+total.cell+emission_O2+rab+lactate+PO4.ferm.; 0.582, 0.816, pH+tmp+Main.Thr.Conc.+OD+Lys_conc.+X.VXdt+total.cell+PL+emission_O2+rab+Thr+lactate+PO4.ferm.; 0.590, 0.816, pH+tmp+Nitrogen.Conc.+OD+Lys_conc.+X.VXdt+total.Vol+total.cell+emission_O2+rab+lactate+PO4.ferm.; 0.574, 0.816, pH+tmp+Nitrogen.Conc.+Lys_conc.+X.VXdt+total.Vol+total.cell+PL+emission_O2+rab+Thr+lactate+SO4.ferm.+PO4.ferm.; 0.590, 0.816, tmp+Nitrogen.Conc.+Lys_conc.+X.VXdt+total.Vol+yield+emission_O2+rab+Thr+lactate+PO4.ferm.+PO4.apporte; 0.582, 0.816, pH+tmp+Nitrogen.Conc.+Lys_conc.+X.VXdt+total.Vol+PL+emission_O2+rab+Thr+His+lactate+PO4.ferm.; 0.604, 0.816, tmp+Main.Thr.Conc.+Nitrogen.Conc.+OD+Lys_conc.+X.VXdt+total.cell+Thr+lactate+PO4.ferm.; 0.582, 0.816, Nitrogen.Conc.+Lys_conc.+X.VXdt+total.Vol+yield+emission_O2+rab+Thr+His+lactate+PO4.ferm.+PO4.apporte+PO4.utilise; 0.581, 0.815, pH+tmp+Nitrogen.Conc.+OD+Lys_conc.+X.F.Suc+X.VXdt+total.cell+emission_O2+rab+His+lactate+PO4.ferm.; 0.573, 0.815, pH+tmp+P-Source.Feed.conc.+Nitrogen.Conc.+OD+Lys_conc.+X.VXdt+total.Vol+total.cell+emission_O2+rab+Thr+lactate+PO4.ferm.; 0.597, 0.815, pH+tmp+Main.Thr.Conc.+Nitrogen.Conc.+Lys_conc.+X.VXdt+total.Vol+emission_O2+rab+lactate+PO4.ferm.; 0.581, 0.815, pH+tmp+Nitrogen.Conc.+OD+Lys_conc.+X.VXdt+total.cell+emission_O2+rab+Thr+lactate+SO4.ferm.+PO4.ferm.; 0.581, 0.815, pH+tmp+Main.P-Source.Conc.+Nitrogen.Conc.+OD+Lys_conc.+X.VXdt+total.cell+emission_O2+rab+Thr+lactate+PO4.ferm.; 0.589, 0.815, pH+tmp+Main.P-Source.Conc.+P-Source.Feed.conc.+Nitrogen.Conc.+Lys_conc.+X.VXdt+total.Vol+emission_O2+rab+lactate+PO4.ferm.; 0.581, 0.815, Nitrogen.Conc.+Lys_conc.+X.F.Suc+X.VXdt+total.Vol+yield+emission_O2+rab+Thr+lactate+PO4.ferm.+PO4.apporte+PO4.utilise; 0.573, 0.815, Nitrogen.Conc.+Lys_conc.+X.VXdt+total.Vol+yield+PL+emission_O2+rab+Thr+His+lactate+PO4.ferm.+PO4.apporte+PO4.utilise; 0.581, 0.815, tmp+Nitrogen.Conc.+OD+Lys_conc.+X.F.Suc+X.VXdt+total.cell+emission_O2+rab+Thr+His+lactate+PO4.ferm.; 0.573, 0.815, pH+tmp+Main.Thr.Conc.+Nitrogen.Conc.+Lys_conc.+X.VXdt+total.Vol+total.cell+PL+emission_O2+rab+Thr+lactate+PO4.ferm.; 0.589, 0.815, pH+tmp+Nitrogen.Conc.+Lys_conc.+X.F.Suc+X.VXdt+total.Vol+emission_O2+rab+Thr+lactate+PO4.ferm.; 0.604, 0.815, Nitrogen.Conc.+Lys_conc.+X.VXdt+total.Vol+yield+emission_O2+rab+Thr+lactate+PO4.utilise; 0.596, 0.815, pH+tmp+Nitrogen.Conc.+Lys_conc.+X.VXdt+total.Vol+PL+emission_O2+rab+lactate+PO4.ferm.; 0.589, 0.815, pH+tmp+P-Source.Feed.conc.+Nitrogen.Conc.+OD+Lys_conc.+X.VXdt+total.Vol+emission_O2+rab+lactate+PO4.ferm.; 0.564, 0.815, pH+tmp+Main.Thr.Conc.+Nitrogen.Conc.+OD+Lys_conc.+X.VXdt+total.Vol+total.cell+PL+emission_O2+rab+Thr+lactate+PO4.ferm.; 0.580, 0.815, pH+tmp+P-Source.Feed.conc.+Nitrogen.Conc.+Lys_conc.+X.VXdt+total.Vol+PL+emission_O2+rab+Thr+lactate+PO4.ferm.; 0.564, 0.815, tmp+Main.Thr.Conc.+Nitrogen.Conc.+Lys_conc.+X.VXdt+total.Vol+yield+PL+emission_O2+rab+Thr+lactate+PO4.ferm.+PO4.apporte+PO4.utilise; 0.572, 0.815, pH+tmp+Main.Thr.Conc.+Nitrogen.Conc.+OD+Lys_conc.+X.VXdt+total.Vol+total.cell+emission_O2+rab+Thr+lactate+PO4.ferm.; 0.596, 0.815, tmp+Nitrogen.Conc.+OD+Lys_conc.+X.VXdt+total.Vol+emission_O2+ rab+Thr+lactate+PO4.ferm.; 0.588, 0.815, pH+tmp+Nitrogen.Conc.+OD+Lys_conc.+X.VXdt+total.Vol+emission_O2+rab+His+lactate+PO4.ferm.; 0.580, 0.815, pH+tmp+Main.Thr.Conc.+Nitrogen.Conc.+Lys_conc.+X.VXdt+total.Vol+total.cell+emission_O2+rab+Thr+lactate+PO4.ferm.; 0.580, 0.815, pH+tmp+Nitrogen.Conc.+Lys_conc.+X.F.Suc+X.VXdt+total.Vol+total.cell+emission_O2+rab+Thr+lactate+PO4.ferm.; 0.580, 0.815, pH+tmp+OD+Lys_conc.+X.VXdt+total.Vol+total.cell+PL+emission_O2+rab+Thr+lactate+PO4.ferm.; 0.603, 0.815, tmp+Nitrogen.Conc.+OD+Lys_conc.+X.VXdt+total.cell+Thr+His+lactate+PO4.ferm.; 0.588, 0.815, pH+tmp+P-Source.Feed.conc.+Main.Thr.Conc.+Nitrogen.Conc.+Lys_conc.+X.VXdt+total.Vol+emission_O2+rab+lactate+PO4.ferm.; 0.588, 0.815, pH+tmp+Main.Thr.Conc.+OD+Lys_conc.+X.VXdt+total.cell+emission_O2+rab+Thr+lactate+PO4.ferm.; 0.563, 0.815, pH+tmp+Nitrogen.Conc.+OD+Lys_conc.+X.VXdt+total.Vol+total.cell+PL+emission_O2+rab+Thr+lactate+SO4.ferm.+PO4.ferm.; 0.588, 0.815, Nitrogen.Conc.+Lys_conc.+X.VXdt+total.Vol+yield+emission_O2+rab+Thr+His+lactate+PO4.ferm.+PO4.apporte; 0.595, 0.815, tmp+OD+Lys_conc.+X.VXdt+total.cell+emission_O2+rab+Thr+His+lactate+PO4.ferm.; 0.579, 0.815, Main.Thr.Conc.+Nitrogen.Conc.+Lys_conc.+X.VXdt+total.Vol+yield+emission_O2+rab+Thr+lactate+PO4.ferm.+PO4.apporte+PO4.utilise; 0.579, 0.815, Nitrogen.Conc.+Lys_conc.+X.VXdt+total.Vol+yield+emission_O2+rab+Thr+lactate+SO4.ferm.+PO4.ferm.+PO4.apporte+PO4.utilise; 0.571, 0.815, tmp+Main.Thr.Conc.+Nitrogen.Conc.+Lys_conc.+X.VXdt+total.Vol+yield+emission_O2+rab+Thr+lactate+PO4.ferm.+PO4.apporte+PO4.utilise; 0.587, 0.815, pH+tmp+Nitrogen.Conc.+OD+Lys_conc.+X.F.Suc+X.VXdt+total.Vol+emission_O2+rab+lactate+PO4.ferm.; 0.587, 0.815, tmp+Nitrogen.Conc.+Lys_conc.+X.VXdt+total.Vol+emission_O2+rab+Thr+lactate+PO4.ferm.+PO4.apporte+PO4.utilise; 0.587, 0.814, pH+tmp+Lys_conc.+X.VXdt+total.Vol+total.cell+PL+emission_O2+rab+Thr+lactate+PO4.ferm.; 0.579, 0.814, pH+tmp+Nitrogen.Conc.+Lys_conc.+X.VXdt+total.Vol+PL+emission_O2+rab+Thr+lactate+SO4.ferm.+PO4.ferm.; 0.579, 0.814, tmp+P-Source.Feed.conc.+Nitrogen.Conc.+OD+Lys_conc.+X.VXdt+total.Vol+total.cell+emission_O2+rab+Thr+lactate+PO4.ferm.; 0.616, 0.814, tmp+OD+Lys_conc.+X.VXdt+total.cell+PL+Thr+PO4.ferm.; 0.587, 0.814, P-Source.Feed.conc.+Nitrogen.Conc.+Lys_conc.+X.VXdt+total.Vol+yield+emission_O2+rab+Thr+lactate+PO4.ferm.+PO4.apporte; 0.579, 0.814, pH+tmp+P-Source.Feed.conc.+Nitrogen.Conc.+Lys_conc.+X.VXdt+total.Vol+total.cell+emission_O2+rab+Thr+lactate+PO4.ferm.; 0.571, 0.814, pH+tmp+Nitrogen.Conc.+OD+Lys_conc.+X.VXdt+total.Vol+PL+emission_O2+rab+Thr+His+lactate+PO4.ferm.; 0.595, 0.814, pH+tmp+Main.P-Source.Conc.+Nitrogen.Conc.+Lys_conc.+X.VXdt+total.Vol+emission_O2+rab+lactate+PO4.ferm.; 0.587, 0.814, tmp+Main.Thr.Conc.+Nitrogen.Conc.+OD+Lys_conc.+X.VXdt+total.cell+emission_O2+rab+Thr+lactate+PO4.ferm.; 0.587, 0.814, tmp+Nitrogen.Conc.+Lys_conc.+X.VXdt+total.Vol+total.cell+PL+emission_O2+rab+Thr+lactate+PO4.ferm.; 0.594, 0.814, tmp+P-Source.Feed.conc.+Nitrogen.Conc.+Lys_conc.+X.VXdt+total.Vol+emission_O2+rab+His+lactate+PO4.ferm.; 0.609, 0.814, tmp+Main.Thr.Conc.+OD+Lys_conc.+X.VXdt+total.cell+Thr+lactate+PO4.ferm.; 0.579, 0.814, pH+tmp+Nitrogen.Conc.+Lys_conc.+X.VXdt+total.Vol+PL+emission_O2+rab+Thr+lactate+PO4.ferm.+PO4.apporte; 0.587, 0.814, Nitrogen.Conc.+Lys_conc.+X.VXdt+total.Vol+yield+PL+emission_O2+rab+Thr+lactate+PO4.ferm.+PO4.apporte; 0.587, 0.814, tmp+Main.P-Source.Conc.+Nitrogen.Conc.+OD+Lys_conc.+X.VXdt+total.cell+emission_O2+rab+Thr+lactate+PO4.ferm.; 0.586, 0.814, pH+tmp+Nitrogen.Conc.+Lys_conc.+X.VXdt+total.Vol+emission_O2+rab+Thr+lactate+PO4.ferm.+PO4.apporte; 0.570, 0.814, pH+tmp+Main.Thr.Conc.+Nitrogen.Conc.+OD+Lys_conc.+X.F.Suc+X.VXdt+total.cell+emission_O2+rab+Thr+lactate+PO4.ferm.; 0.594, 0.814, tmp+Nitrogen.Conc.+OD+Lys_conc.+X.F.Suc+X.VXdt+total.cell+Thr+His+lactate+PO4.ferm.; 0.579, 0.814, pH+tmp+OD+Lys_conc.+X.VXdt+total.cell+PL+emission_O2+rab+Thr+His+lactate+PO4.ferm.; 0.586, 0.814, Nitrogen.Conc.+Lys_conc.+X.F.Suc+X.VXdt+total.Vol+yield+emission_O2+rab+Thr+lactate+PO4.ferm.+PO4.apporte; 0.586, 0.814, tmp+P-Source.Feed.conc.+Nitrogen.Conc.+Lys_conc.+X.VXdt+total.Vol+total.cell+emission_O2+rab+Thr+lactate+PO4.ferm.; 0.594, 0.814, tmp+Nitrogen.Conc.+Lys_conc.+X.VXdt+total.Vol+emission_O2+rab+Thr+lactate+PO4.ferm.+PO4.utilise; 0.594, 0.814, tmp+Main.Thr.Conc.+OD+Lys_conc.+X.VXdt+total.cell+emission_O2+rab+Thr+lactate+PO4.ferm.; 0.578, 0.814, pH+tmp+Nitrogen.Conc.+OD+Lys_conc.+X.VXdt+total.Vol+emission_O2+rab+Thr+His+lactate+PO4.ferm.; 0.578, 0.814, pH+tmp+P-Source.Feed.conc.+Nitrogen.Conc.+Lys_conc.+X.VXdt+total.Vol+total.cell+emission_O2+rab+His+lactate+PO4.ferm.; 0.578, 0.814, pH+tmp+Nitrogen.Conc.+OD+Lys_conc.+X.VXdt+total.Vol+total.cell+emission_O2+rab+His+lactate+PO4.ferm.; 0.570, 0.814, pH+tmp+Nitrogen.Conc.+OD+Lys_conc.+X.F.Suc+X.VXdt+total.cell+emission_O2+rab+Thr+lactate+SO4.ferm.+PO4.ferm.; 0.594, 0.814, tmp+OD+Lys_conc.+X.F.Suc+X.VXdt+total.cell+emission_O2+rab+Thr+lactate+PO4.ferm.; 0.601, 0.814, tmp+Main.Thr.Conc.+OD+Lys_conc.+X.VXdt+total.cell+PL+Thr+lactate+PO4.ferm.; 0.578, 0.814, pH+tmp+Nitrogen.Conc.+Lys_conc.+X.VXdt+total.Vol+total.cell+emission_O2+rab+Thr+lactate+SO4.ferm.+PO4.ferm.; 0.586, 0.814, tmp+Nitrogen.Conc.+Lys_conc.+X.VXdt+total.cell+emission_O2+rab+Thr+His+lactate+PO4.ferm.; 0.578, 0.814, pH+tmp+Nitrogen.Conc.+Lys_conc.+X.F.Suc+X.VXdt+total.Vol+total.cell+emission_O2+rab+His+lactate+PO4.ferm.; 0.586, 0.814, pH+tmp+OD+Lys_conc.+X.VXdt+total.cell+PL+emission_O2+rab+Thr+His+PO4.ferm.; 0.569, 0.814, pH+tmp+Main.P-Source.Conc.+Nitrogen.Conc.+OD+Lys_conc.+X.VXdt+total.cell+PL+emission_O2+rab+Thr+lactate+PO4.ferm.; 0.561, 0.814, pH+tmp+Nitrogen.Conc.+Lys_conc.+X.VXdt+total.Vol+yield+PL+emission_O2+rab+Thr+lactate+PO4.ferm.+PO4.apporte+PO4.utilise; 0.577, 0.814, tmp+Nitrogen.Conc.+OD+Lys_conc.+X.VXdt+total.Vol+total.cell+PL+emission_O2+rab+Thr+lactate+PO4.ferm.; 0.569, 0.814, tmp+Nitrogen.Conc.+Lys_conc.+X.VXdt+total.Vol+yield+emission_O2+rab+Thr+His+lactate+PO4.ferm.+PO4.apporte+PO4.utilise; 0.585, 0.814, Main.Thr.Conc.+Nitrogen.Conc.+Lys_conc.+X.VXdt+total.Vol+yield+emission_O2+rab+Thr+lactate+PO4.ferm.+PO4.apporte; 0.569, 0.813, pH+tmp+Nitrogen.Conc.+OD+Lys_conc.+X.F.Suc+X.VXdt+total.cell+emission_O2+rab+His+lactate+PO4.ferm.; 0.585, 0.813, pH+tmp+P-Source.Feed.conc.+Nitrogen.Conc.+Lys_conc.+X.F.Suc+X.VXdt+total.Vol+emission_O2+rab+lactate+PO4.ferm.; 0.569, 0.813, pH+tmp+Nitrogen.Conc.+OD+Lys_conc.+X.VXdt+total.Vol+total.cell+emission_O2+rab+Thr+lactate+SO4.ferm.+PO4.ferm.; 0.577, 0.813, pH+tmp+OD+Lys_conc.+X.VXdt+total.cell+PL+emission_O2+rab+Thr+lactate+SO4.ferm.+PO4.ferm.; 0.577, 0.813, pH+tmp+P-Source.Feed.conc.+Nitrogen.Conc.+OD+Lys_conc.+X.VXdt+total.Vol+total.cell+emission_O2+rab+lactate+PO4.ferm.; 0.600, 0.813, tmp+OD+Lys_ conc.+X.VXdt+total.cell+PL+Thr+His+lactate+PO4.ferm.; 0.585, 0.813, tmp+Main.P-Source.Conc.+P-Source.Feed.conc.+Nitrogen.Conc.+Lys_conc.+X.VXdt+total.Vol+emission_O2+rab+Thr+lactate+PO4.ferm.; 0.621, 0.813, tmp+OD+Lys_conc.+X.VXdt+total.cell+Thr+PO4.ferm.; 0.585, 0.813, pH+tmp+OD+Lys_conc.+X.F.Suc+X.VXdt+total.cell+emission_O2+rab+Thr+lactate+PO4.ferm.; 0.577, 0.813, pH+tmp+Main.P-Source.Conc.+P-Source.Feed.conc.+Nitrogen.Conc.+Lys_conc.+X.VXdt+total.Vol+emission_O2+rab+His+lactate+PO4.ferm.; 0.577, 0.813, pH+tmp+P-Source.Feed.conc.+Nitrogen.Conc.+OD+Lys_conc.+X.VXdt+total.Vol+emission_O2+rab+His+lactate+PO4.ferm.; 0.560, 0.813, tmp+Nitrogen.Conc.+Lys_conc.+X.VXdt+total.Vol+yield+PL+emission_O2+rab+Thr+lactate+SO4.ferm.+PO4.ferm.+PO4.apporte+PO4.utilise; 0.577, 0.813, pH+tmp+P-Source.Feed.conc.+Main.Thr.Conc.+Nitrogen.Conc.+Lys_conc.+X.VXdt+total.Vol+emission_O2+rab+Thr+lactate+PO4.ferm.; 0.568, 0.813, pH+tmp+P-Source.Feed.conc.+Nitrogen.Conc.+OD+Lys_conc.+X.VXdt+total.cell+PL+emission_O2+rab+Thr+lactate+PO4.ferm.; 0.577, 0.813, tmp+Nitrogen.Conc.+OD+Lys_conc.+X.VXdt+total.Vol+total.cell+emission_O2+rab+Thr+His+lactate+PO4.ferm.; 0.576, 0.813, tmp+Nitrogen.Conc.+OD+Lys_conc.+X.VXdt+total.cell+emission_O2+rab+Thr+His+lactate+PO4.ferm.; 0.568, 0.813, pH+tmp+Nitrogen.Conc.+Lys_conc.+X.VXdt+total.Vol+PL+emission_O2+rab+Thr+lactate+PO4.ferm.+PO4.apporte+PO4.utilise; 0.599, 0.813, tmp+Nitrogen.Conc.+OD+Lys_conc.+X.VXdt+total.cell+emission_O2+rab+Thr+PO4.ferm.; 0.592, 0.813, tmp+Nitrogen.Conc.+OD+Lys_conc.+X.VXdt+total.cell+PL+Thr+His+lactate+PO4.ferm.; 0.592, 0.813, tmp+Main.Thr.Conc.+Nitrogen.Conc.+OD+Lys_conc.+X.F.Suc+X.VXdt+total.cell+Thr+lactate+PO4.ferm.; 0.568, 0.813, Main.Thr.Conc.+Nitrogen.Conc.+Lys_conc.+X.VXdt+total.Vol+yield+PL+emission_O2+rab+Thr+lactate+PO4.ferm.+PO4.apporte+PO4.utilise; 0.568, 0.813, Nitrogen.Conc.+Lys_conc.+X.VXdt+total.Vol+yield+PL+emission_O2+rab+Thr+lactate+SO4.ferm.+PO4.ferm.+PO4.apporte+PO4.utilise; 0.568, 0.813, pH+tmp+Nitrogen.Conc.+OD+Lys_conc.+X.VXdt+total.Vol+PL+emission_O2+rab+Thr+lactate+SO4.ferm.+PO4.ferm.; 0.584, 0.813, pH+tmp+Nitrogen.Conc.+Lys_conc.+X.VXdt+total.Vol+PL+emission_O2+rab+His+lactate+PO4.ferm.; 0.599, 0.813, tmp+OD+Lys_conc.+X.VXdt+total.cell+PL+emission_O2+rab+Thr+PO4.ferm.; 0.568, 0.813, pH+tmp+Main.P-Source.Conc.+Nitrogen.Conc.+OD+Lys_conc.+X.F.Suc+X.VXdt+total.cell+emission_O2+rab+Thr+lactate+PO4.ferm.; 0.584, 0.813, pH+tmp+OD+Lys_conc.+X.VXdt+total.cell+emission_O2+rab+Thr+His+lactate+PO4.ferm.; 0.592, 0.813, tmp+Main.Thr.Conc.+Nitrogen.Conc.+OD+Lys_conc.+X.VXdt+total.cell+PL+Thr+lactate+PO4.ferm.; 0.599, 0.813, pH+tmp+Nitrogen.Conc.+OD+Lys_conc.+X.F.Suc+X.VXdt+total.cell+lactate+PO4.ferm.; 0.584, 0.813, pH+tmp+Nitrogen.Conc.+Lys_conc.+X.VXdt+total.Vol+emission_O2+rab+Thr+lactate+SO4.ferm.+PO4.ferm.; 0.606, 0.813, tmp+Nitrogen.Conc.+Lys_conc.+X.VXdt+total.Vol+emission_O2+rab+lactate+PO4.ferm.; 0.606, 0.813, tmp+Nitrogen.Conc.+OD+Lys_conc.+X.F.Suc+X.VXdt+total.cell+lactate+PO4.ferm.; 0.576, 0.813, pH+tmp+P-Source.Feed.conc.+Nitrogen.Conc.+Lys_conc.+X.VXdt+total.Vol+emission_O2+rab+Thr+His+lactate+PO4.ferm.; 0.591, 0.813, tmp+Nitrogen.Conc.+Lys_conc.+X.VXdt+total.Vol+PL+emission_O2+rab+Thr+lactate+PO4.ferm.; 0.567, 0.813, Nitrogen.Conc.+Lys_conc.+X.F.Suc+X.VXdt+total.Vol+yield+PL+emission_O2+rab+Thr+lactate+PO4.ferm.+PO4.apporte+PO4.utilise; 0.606, 0.813, tmp+OD+Lys_conc.+X.VXdt+total.cell+Thr+His+lactate+PO4.ferm.; 0.583, 0.813, pH+tmp+Main.P-Source.Conc.+Nitrogen.Conc.+Lys_conc.+X.VXdt+total.Vol+emission_O2+rab+His+lactate+PO4.ferm.; 0.567, 0.813, pH+tmp+P-Source.Feed.conc.+Nitrogen.Conc.+OD+Lys_conc.+X.VXdt+total.cell+emission_O2+rab+Thr+His+lactate+PO4.ferm.; 0.583, 0.813, pH+tmp+Main.P-Source.Conc.+Nitrogen.Conc.+Lys_conc.+X.VXdt+total.Vol+emission_O2+rab+Thr+lactate+PO4.ferm.; 0.583, 0.813, pH+tmp+Main.P-Source.Conc.+Nitrogen.Conc.+Lys_conc.+X.F.Suc+X.VXdt+total.Vol+emission_O2+rab+lactate+PO4.ferm.; 0.591, 0.813, tmp+Nitrogen.Conc.+Lys_conc.+X.VXdt+total.Vol+emission_O2+rab+Thr+His+lactate+PO4.ferm.; 0.575, 0.813, pH+tmp+Nitrogen.Conc.+Lys_conc.+X.VXdt+total.Vol+PL+emission_O2+rab+Thr+lactate+PO4.ferm.+PO4.utilise; 0.558, 0.813, pH+tmp+P-Source.Feed.conc.+Nitrogen.Conc.+OD+Lys_conc.+X.VXdt+total.Vol+total.cell+PL+emission_O2+rab+Thr+lactate+PO4.ferm.; 0.567, 0.813, pH+tmp+Main.Thr.Conc.+Nitrogen.Conc.+OD+Lys_conc.+X.VXdt+total.Vol+PL+emission_O2+rab+Thr+lactate+PO4.ferm.; 0.558, 0.813, pH+tmp+Nitrogen.Conc.+OD+Lys_conc.+X.F.Suc+X.VXdt+total.Vol+total.cell+emission_O2+rab+Thr+His+lactate+PO4.ferm.; 0.575, 0.813, tmp+P-Source.Feed.conc.+Nitrogen.Conc.+OD+Lys_conc.+X.VXdt+total.cell+emission_O2+rab+Thr+His+lactate+PO4.ferm.; 0.567, 0.812, pH+tmp+P-Source.Feed.conc.+Nitrogen.Conc.+OD+Lys_conc.+X.F.Suc+X.VXdt+total.cell+emission_O2+rab+Thr+lactate+PO4.ferm.; 0.575, 0.812, pH+tmp+Main.Thr.Conc.+Nitrogen.Conc.+OD+Lys_conc.+X.VXdt+total.Vol+emission_O2+rab+Thr+lactate+PO4.ferm.; 0.575, 0.812, tmp+Nitrogen.Conc.+Lys_conc.+X.VXdt+total.Vol+PL+emission_O2+rab+Thr+lactate+PO4.ferm.+PO4.apporte+PO4.utilise; 0.591, 0.812, pH+tmp+Nitrogen.Conc.+OD+Lys_conc.+X.F.Suc+X.VXdt+total.cell+Thr+lactate+PO4.ferm.; 0.583, 0.812, tmp+P-Source.Feed.conc.+Nitrogen.Conc.+Lys_conc.+X.VXdt+total.Vol+emission_O2+rab+Thr+His+lactate+PO4.ferm.; 0.575, 0.812, pH+tmp+OD+Lys_conc.+X.F.Suc+X.VXdt+total.cell+PL+emission_O2+rab+Thr+lactate+PO4.ferm.; 0.583, 0.812, pH+tmp+P-Source.Feed.conc.+Nitrogen.Conc.+Lys_conc.+X.VXdt+total.Vol+PL+emission_O2+rab+lactate+PO4.ferm.; 0.583, 0.812, pH+tmp+Nitrogen.Conc.+OD+Lys_conc.+X.F.Suc+X.VXdt+total.cell+emission_O2+rab+Thr+PO4.ferm.; 0.566, 0.812, pH+tmp+Main.Thr.Conc.+Nitrogen.Conc.+Lys_conc.+X.VXdt+total.Vol+PL+emission_O2+rab+Thr+lactate+SO4.ferm.+PO4.ferm.; 0.566, 0.812, pH+tmp+Main.P-Source.Conc.+Nitrogen.Conc.+Lys_conc.+X.VXdt+total.Vol+total.cell+PL+emission_O2+rab+Thr+lactate+PO4.ferm.; 0.583, 0.812, pH+tmp+Nitrogen.Conc.+Lys_conc.+X.VXdt+total.Vol+emission_O2+rab+Thr+lactate+PO4.ferm.+PO4.utilise; 0.566, 0.812, tmp+Nitrogen.Conc.+Lys_conc.+X.VXdt+total.Vol+yield+emission_O2+rab+Thr+lactate+SO4.ferm.+PO4.ferm.+PO4.apporte+PO4.utilise; 0.590, 0.812, Nitrogen.Conc.+Lys_conc.+X.VXdt+total.Vol+yield+emission_O2+rab+Thr+His+lactate+PO4.utilise; 0.574, 0.812, pH+tmp+Main.P-Source.Conc.+Nitrogen.Conc.+Lys_conc.+X.VXdt+total.Vol+total.cell+emission_O2+rab+Thr+lactate+PO4.ferm.; 0.582, 0.812, tmp+OD+Lys_conc.+X.VXdt+total.cell+PL+emission_O2+rab+Thr+His+lactate+PO4.ferm.; 0.566, 0.812, pH+tmp+P-Source.Feed.conc.+Nitrogen.Conc.+Lys_conc.+X.VXdt+total.Vol+total.cell+PL+emission_O2+rab+Thr+lactate+PO4.ferm.; 0.574, 0.812, pH+tmp+P-Source.Feed.conc.+Main.Thr.Conc.+Nitrogen.Conc.+Lys_conc.+X.VXdt+total.Vol+emission_O2+rab+His+lactate+PO4.ferm.; 0.590, 0.812, tmp+Main.Thr.Conc.+Nitrogen.Conc.+OD+Lys_conc.+X.VXdt+total.

cell+Thr+His+lactate+PO4.ferm.; 0.582, 0.812, pH+tmp+Main.Thr.Conc.+Nitrogen.Conc.+Lys_conc.+X.VXdt+total.Vol+emission_O2+rab+His+lactate+PO4.ferm.; 0.574, 0.812, pH+tmp+Nitrogen.Conc.+OD+Lys_conc.+X.F.Suc+X.VXdt+total.Vol+emission_O2+rab+His+lactate+PO4.ferm.; 0.566, 0.812, pH+tmp+Main.Thr.Conc.+Nitrogen.Conc.+OD+Lys_conc.+X.VXdt+total.cell+emission_O2+rab+Thr+His+lactate+PO4.ferm.; 0.557, 0.812, pH+tmp+Nitrogen.Conc.+OD+Lys_conc.+X.F.Suc+X.VXdt+total.cell+PL+emission_O2+rab+Thr+His+lactate+PO4.ferm.; 0.597, 0.812, tmp+Nitrogen.Conc.+OD+Lys_conc.+X.VXdt+total.cell+Thr+lactate+SO4.ferm.+PO4.ferm.; 0.574, 0.812, tmp+Nitrogen.Conc.+Lys_conc.+X.VXdt+total.Vol+yield+PL+emission_O2+rab+Thr+lactate+PO4.ferm.+PO4.apporte; 0.582, 0.812, tmp+Nitrogen.Conc.+OD+Lys_conc.+X.VXdt+total.cell+emission_O2+rab+Thr+lactate+SO4.ferm.+PO4.ferm.; 0.590, 0.812, pH+tmp+Nitrogen.Conc.+OD+Lys_conc.+X.VXdt+total.cell+emission_O2+rab+lactate+PO4.ferm.; 0.582, 0.812, tmp+Nitrogen.Conc.+Lys_conc.+X.VXdt+total.Vol+emission_O2+rab+Thr+His+lactate+PO4.ferm.+PO4.apporte; 0.589, 0.812, tmp+Main.P-Source.Conc.+P-Source.Feed.conc.+Nitrogen.Conc.+Lys_conc.+X.VXdt+total.Vol+emission_O2+rab+lactate+PO4.ferm.; 0.574, 0.812, pH+tmp+P-Source.Feed.conc.+Nitrogen.Conc.+OD+Lys_conc.+X.VXdt+total.Vol+emission_O2+rab+Thr+lactate+PO4.ferm.; 0.582, 0.812, pH+tmp+Main.Thr.Conc.+OD+Lys_conc.+X.VXdt+total.cell+PL+emission_O2+rab+Thr+PO4.ferm.; 0.573, 0.812, pH+tmp+Nitrogen.Conc.+OD+Lys_conc.+X.F.Suc+X.VXdt+total.Vol+emission_O2+rab+Thr+lactate+PO4.ferm.; 0.573, 0.812, tmp+Nitrogen.Conc.+OD+Lys_conc.+X.F.Suc+X.VXdt+total.Vol+total.cell+emission_O2+rab+Thr+lactate+PO4.ferm.; 0.581, 0.812, pH+tmp+Nitrogen.Conc.+Lys_conc.+X.VXdt+total.Vol+total.cell+PL+emission_O2+rab+lactate+PO4.ferm.; 0.573, 0.812, tmp+Main.Thr.Conc.+Nitrogen.Conc.+Lys_conc.+X.VXdt+total.Vol+yield+emission_O2+rab+Thr+lactate+PO4.ferm.+PO4.apporte; 0.589, 0.812, P-Source.Feed.conc.+Nitrogen.Conc.+OD+Lys_conc.+X.VXdt+total.cell+emission_O2+rab+Thr+lactate+PO4.ferm.; 0.581, 0.812, tmp+P-Source.Feed.conc.+Main.Thr.Conc.+Nitrogen.Conc.+Lys_conc.+X.VXdt+total.Vol+emission_O2+rab+Thr+lactate+PO4.ferm.; 0.589, 0.812, pH+tmp+OD+Lys_conc.+X.F.Suc+X.VXdt+total.cell+emission_O2+rab+Thr+PO4.ferm.; 0.565, 0.811, pH+tmp+P-Source.Feed.conc.+Nitrogen.Conc.+OD+Lys_conc.+X.VXdt+total.Vol+total.cell+emission_O2+rab+His+lactate+PO4.ferm.; 0.596, 0.811, pH+tmp+Nitrogen.Conc.+OD+Lys_conc.+X.VXdt+total.cell+Thr+lactate+PO4.ferm.; 0.573, 0.811, pH+tmp+Main.P-Source.Conc.+P-Source.Feed.conc.+Nitrogen.Conc.+Lys_conc.+X.VXdt+total.Vol+emission_O2+rab+Thr+lactate+PO4.ferm.; 0.589, 0.811, pH+tmp+OD+Lys_conc.+X.VXdt+total.cell+emission_O2+rab+Thr+His+PO4.ferm.; 0.581, 0.811, tmp+P-Source.Feed.conc.+Nitrogen.Conc.+OD+Lys_conc.+X.VXdt+total.cell+emission_O2+rab+Thr+lactate+PO4.ferm.; 0.573, 0.811, tmp+Nitrogen.Conc.+Lys_conc.+X.VXdt+total.Vol+yield+emission_O2+rab+Thr+His+lactate+PO4.ferm.+PO4.apporte; 0.589, 0.811, tmp+Main.P-Source.Conc.+OD+Lys_conc.+X.VXdt+total.cell+emission_O2+rab+Thr+lactate+PO4.ferm.; 0.589, 0.811, Nitrogen.Conc.+Lys_conc.+X.VXdt+total.Vol+yield+emission_O2+rab+Thr+lactate+PO4.ferm.+PO4.utilise; 0.610, 0.811, tmp+Nitrogen.Conc.+OD+Lys_conc.+X.VXdt+total.cell+Thr+PO4.ferm.; 0.556, 0.811, pH+tmp+Nitrogen.Conc.+OD+Lys_conc.+X.F.Suc+X.VXdt+total.Vol+total.cell+PL+emission_O2+rab+Thr+lactate+PO4.ferm.; 0.556, 0.811, pH+tmp+Main.Thr.Conc.+Nitrogen.Conc.+OD+Lys_conc.+X.VXdt+total.cell+PL+emission_O2+rab+Thr+His+lactate+PO4.ferm.; 0.596, 0.811, tmp+Main.Thr.Conc.+OD+Lys_conc.+X.VXdt+total.cell+Thr+His+lactate+PO4.ferm.; 0.588, 0.811, tmp+Nitrogen.Conc.+OD+Lys_conc.+X.F.Suc+X.VXdt+total.cell+PL+Thr+lactate+PO4.ferm.; 0.581, 0.811, tmp+Main.Thr.Conc.+OD+Lys_conc.+X.VXdt+total.cell+PL+emission_O2+rab+Thr+lactate+PO4.ferm.; 0.581, 0.811, tmp+Nitrogen.Conc.+OD+Lys_conc.+X.VXdt+total.Vol+PL+emission_O2+rab+Thr+lactate+PO4.ferm.; 0.588, 0.811, tmp+Nitrogen.Conc.+OD+Lys_conc.+X.F.Suc+X.VXdt+total.cell+Thr+lactate+SO4.ferm.+PO4.ferm.; 0.555, 0.811, pH+tmp+P-Source.Feed.conc.+Nitrogen.Conc.+OD+Lys_conc.+X.VXdt+total.Vol+total.cell+emission_O2+rab+Thr+His+lactate+PO4.ferm.; 0.596, 0.811, tmp+OD+Lys_conc.+X.VXdt+total.cell+PL+Thr+lactate+SO4.ferm.+PO4.ferm.; 0.572, 0.811, tmp+Nitrogen.Conc.+OD+Lys_conc.+X.F.Suc+X.VXdt+total.cell+PL+emission_O2+rab+Thr+lactate+PO4.ferm.; 0.603, 0.811, tmp+Nitrogen.Conc.+OD+Lys_conc.+X.VXdt+total.cell+PL+Thr+PO4.ferm.; 0.555, 0.811, pH+tmp+Nitrogen.Conc.+Lys_conc.+X.VXdt+total.Vol+total.cell+PL+emission_O2+rab+Thr+His+lactate+SO4.ferm.+PO4.ferm.; 0.555, 0.811, pH+tmp+Nitrogen.Conc.+OD+Lys_conc.+X.VXdt+total.cell+PL+emission_O2+rab+Thr+His+lactate+SO4.ferm.+PO4.ferm.; 0.588, 0.811, tmp+Main.Thr.Conc.+Nitrogen.Conc.+Lys_conc.+X.VXdt+total.Vol+emission_O2+rab+Thr+lactate+PO4.ferm.; 0.572, 0.811, pH+tmp+Nitrogen.Conc.+OD+Lys_conc.+X.VXdt+total.cell+PL+emission_O2+rab+Thr+His+PO4.ferm.; 0.564, 0.811, Nitrogen.Conc.+Lys_conc.+X.F.Suc+X.VXdt+total.Vol+yield+emission_O2+rab+Thr+His+lactate+PO4.ferm.+PO4.apporte+PO4.utilise; 0.572, 0.811, pH+tmp+Main.P-Source.Conc.+Nitrogen.Conc.+Lys_conc.+X.VXdt+total.Vol+PL+emission_O2+rab+Thr+lactate+PO4.ferm.; 0.588, 0.811, tmp+Lys_conc.+X.VXdt+total.Vol+total.cell+PL+emission_O2+rab+Thr+lactate+PO4.ferm.; 0.572, 0.811, pH+tmp+Nitrogen.Conc.+OD+Lys_conc.+X.VXdt+total.Vol+emission_O2+rab+Thr+lactate+SO4.ferm.+PO4.ferm.; 0.572, 0.811, pH+tmp+Main.P-Source.Conc.+OD+Lys_conc.+X.VXdt+total.cell+PL+emission_O2+rab+Thr+lactate+PO4.ferm.; 0.572, 0.811, pH+tmp+Main.Thr.Conc.+Nitrogen.Conc.+Lys_conc.+X.VXdt+total.Vol+emission_O2+rab+Thr+lactate+SO4.ferm.+PO4.ferm.; 0.580, 0.811, tmp+Nitrogen.Conc.+Lys_conc.+X.VXdt+total.Vol+PL+emission_O2+rab+Thr+lactate+PO4.ferm.+PO4.apporte; 0.602, 0.811, tmp+OD+Lys_conc.+X.F.Suc+X.VXdt+total.cell+Thr+lactate+PO4.ferm.; 0.546, 0.811, tmp+Main.Thr.Conc.+Nitrogen.Conc.+Lys_conc.+X.VXdt+total.Vol+yield+PL+emission_O2+rab+Thr+His+lactate+PO4.ferm.+PO4.apporte+PO4.utilise; 0.602, 0.811, tmp+OD+Lys_conc.+X.VXdt+total.cell+PL+Thr+His+PO4.ferm.; 0.580, 0.811, pH+tmp+Nitrogen.Conc.+OD+Lys_conc.+X.VXdt+total.cell+emission_O2+rab+Thr+His+PO4.ferm.; 0.572, 0.811, P-Source.Feed.conc.+Main.Thr.Conc.+Nitrogen.Conc.+Lys_conc.+X.VXdt+total.Vol+yield+emission_O2+rab+Thr+lactate+PO4.ferm.+PO4.apporte; 0.563, 0.811, pH+tmp+Nitrogen.Conc.+OD+Lys_conc.+X.VXdt+total.cell+emission_O2+rab+Thr+His+lactate+SO4.ferm.+PO4.ferm.; 0.587, 0.811, tmp+OD+Lys_conc.+X.VXdt+total.Vol+total.cell+emission_O2+rab+Thr+lactate+PO4.ferm.; 0.572, 0.811, tmp+P-Source.Feed.conc.+Nitrogen.Conc.+OD+Lys_conc.+X.F.Suc+X.VXdt+total.cell+emission_O2+rab+Thr+lactate+PO4.ferm.; 0.587, 0.811, tmp+Nitrogen.Conc.+OD+Lys_conc.+X.VXdt+total.cell+PL+Thr+lactate+SO4.ferm.+PO4.ferm.; 0.580, 0.811, pH+tmp+OD+Lys_conc.+X.F.Suc+X.VXdt+total.cell+PL+emission_O2+rab+Thr+PO4.ferm.; 0.587, 0.811, tmp+P-Source.Feed.

conc.+Nitrogen.Conc.+Lys_conc.+X.VXdt+total.Vol+total.cell+emission_O2+rab+lactate+PO4.ferm.; 0.571, 0.811, pH+tmp+P-Source.Feed.conc.+Nitrogen.Conc.+Lys_conc.+X.F.Suc+X.VXdt+total.Vol+emission_O2+rab+His+lactate+PO4.ferm.; 0.563, 0.811, pH+tmp+P-Source.Feed.conc.+Main.Thr.Conc.+Nitrogen.Conc.+Lys_conc.+X.VXdt+total.Vol+PL+emission_O2+rab+Thr+lactate+PO4.ferm.; 0.595, 0.811, tmp+OD+Lys_conc.+X.VXdt+total.cell+emission_O2+rab+Thr+His+PO4.ferm.; 0.563, 0.811, Nitrogen.Conc.+Lys_conc.+X.VXdt+total.Vol+yield+emission_O2+rab+Thr+His+lactate+SO4.ferm.+PO4.ferm.+PO4.apporte+PO4.utilise; 0.579, 0.811, tmp+P-Source.Feed.conc.+Nitrogen.Conc.+Lys_conc.+X.VXdt+total.Vol+PL+emission_O2+rab+Thr+lactate+PO4.ferm.; 0.571, 0.811, pH+tmp+Main.Thr.Conc.+Nitrogen.Conc.+Lys_conc.+X.VXdt+total.Vol+emission_O2+rab+Thr+His+lactate+PO4.ferm.; 0.554, 0.811, pH+tmp+Main.P-Source.Conc.+Nitrogen.Conc.+OD+Lys_conc.+X.VXdt+total.Vol+total.cell+PL+emission_O2+rab+Thr+lactate+PO4.ferm.; 0.595, 0.811, tmp+Lys_conc.+X.VXdt+total.Vol+total.cell+emission_O2+rab+Thr+lactate+PO4.ferm.; 0.563, 0.810, pH+tmp+Main.P-Source.Conc.+Nitrogen.Conc.+OD+Lys_conc.+X.VXdt+total.cell+emission_O2+rab+Thr+His+lactate+PO4.ferm.; 0.571, 0.810, tmp+Main.P-Source.Conc.+Nitrogen.Conc.+OD+Lys_conc.+X.F.Suc+X.VXdt+total.cell+emission_O2+rab+Thr+lactate+PO4.ferm.; 0.579, 0.810, tmp+Nitrogen.Conc.+OD+Lys_conc.+X.VXdt+total.Vol+emission_O2+rab+Thr+His+lactate+PO4.ferm.; 0.579, 0.810, pH+tmp+Nitrogen.Conc.+OD+Lys_conc.+X.VXdt+total.Vol+PL+emission_O2+rab+lactate+PO4.ferm.; 0.594, 0.810, tmp+Nitrogen.Conc.+Lys_conc.+X.F.Suc+X.VXdt+total.Vol+emission_O2+rab+lactate+PO4.ferm.; 0.579, 0.810, pH+Nitrogen.Conc.+Lys_conc.+X.VXdt+total.Vol+yield+emission_O2+rab+Thr+lactate+PO4.ferm.+PO4.apporte; 0.554, 0.810, pH+tmp+Main.Thr.Conc.+Nitrogen.Conc.+OD+Lys_conc.+X.VXdt+total.cell+PL+emission_O2+rab+Thr+lactate+SO4.ferm.+PO4.ferm.; 0.563, 0.810, pH+tmp+Main.P-Source.Conc.+Nitrogen.Conc.+OD+Lys_conc.+X.VXdt+total.Vol+total.cell+emission_O2+rab+Thr+lactate+PO4.ferm.; 0.594, 0.810, tmp+Main.Thr.Conc.+OD+Lys_conc.+X.VXdt+total.cell+emission_O2+Thr+lactate+PO4.ferm.; 0.571, 0.810, pH+tmp+Nitrogen.Conc.+Lys_conc.+X.VXdt+total.Vol+emission_O2+rab+Thr+lactate+PO4.ferm.+PO4.apporte+PO4.utilise; 0.545, 0.810, pH+tmp+Nitrogen.Conc.+OD+Lys_conc.+X.VXdt+total.Vol+total.cell+PL+emission_O2+rab+Thr+His+lactate+SO4.ferm.+PO4.ferm.; 0.579, 0.810, pH+tmp+OD+Lys_conc.+X.VXdt+total.Vol+PL+emission_O2+rab+Thr+lactate+PO4.ferm.; 0.609, 0.810, tmp+Main.Thr.Conc.+OD+Lys_conc.+X.VXdt+total.cell+Thr+PO4.ferm.; 0.579, 0.810, tmp+Nitrogen.Conc.+Lys_conc.+X.F.Suc+X.VXdt+total.Vol+total.cell+emission_O2+rab+Thr+lactate+PO4.ferm.; 0.587, 0.810, tmp+Nitrogen.Conc.+Lys_conc.+X.F.Suc+X.VXdt+total.Vol+emission_O2+rab+Thr+lactate+PO4.ferm.; 0.571, 0.810, P-Source.Feed.conc.+Nitrogen.Conc.+Lys_conc.+X.VXdt+total.Vol+yield+emission_O2+rab+Thr+His+lactate+PO4.ferm.+PO4.apporte; 0.587, 0.810, pH+tmp+Nitrogen.Conc.+OD+Lys_conc.+X.F.Suc+X.VXdt+total.cell+His+lactate+PO4.ferm.; 0.571, 0.810, P-Source.Feed.conc.+Nitrogen.Conc.+Lys_conc.+X.VXdt+total.Vol+yield+PL+emission_O2+rab+Thr+lactate+PO4.ferm.+PO4.apporte; 0.579, 0.810, pH+tmp+OD+Lys_conc.+X.VXdt+total.Vol+total.cell+emission_O2+rab+Thr+lactate+PO4.ferm.; 0.571, 0.810, tmp+Main.P-Source.Conc.+P-Source.Feed.conc.+Nitrogen.Conc.+OD+Lys_conc.+X.VXdt+total.cell+emission_O2+rab+Thr+lactate+PO4.ferm.; 0.579, 0.810, tmp+OD+Lys_conc.+X.VXdt+total.Vol+total.cell+PL+emission_O2+rab+Thr+lactate+PO4.ferm.; 0.562, 0.810, pH+tmp+Main.Thr.Conc.+Nitrogen.Conc.+Lys_conc.+X.VXdt+total.Vol+PL+emission_O2+rab+Thr+His+lactate+PO4.ferm.; 0.562, 0.810, pH+tmp+Nitrogen.Conc.+Lys_conc.+X.F.Suc+X.VXdt+total.Vol+total.cell+emission_O2+rab+Thr+His+lactate+PO4.ferm.; 0.562, 0.810, pH+tmp+Nitrogen.Conc.+Lys_conc.+X.VXdt+total.Vol+yield+PL+emission_O2+rab+Thr+lactate+PO4.ferm.+PO4.apporte; 0.601, 0.810, tmp+Main.Thr.Conc.+OD+Lys_conc.+X.VXdt+total.cell+PL+Thr+PO4.ferm.; 0.586, 0.810, tmp+Main.P-Source.Conc.+Nitrogen.Conc.+Lys_conc.+X.VXdt+total.Vol+emission_O2+rab+Thr+lactate+PO4.ferm.; 0.594, 0.810, tmp+Nitrogen.Conc.+OD+Lys_conc.+X.F.Suc+X.VXdt+total.cell+His+lactate+PO4.ferm.; 0.579, 0.810, tmp+Main.Thr.Conc.+Nitrogen.Conc.+Lys_conc.+X.VXdt+total.Vol+total.cell+emission_O2+rab+Thr+lactate+PO4.ferm.; 0.578, 0.810, pH+tmp+Main.Thr.Conc.+Nitrogen.Conc.+Lys_conc.+X.VXdt+total.Vol+total.cell+emission_O2+rab+lactate+PO4.ferm.; 0.562, 0.810, Main.Thr.Conc.+Nitrogen.Conc.+Lys_conc.+X.F.Suc+X.VXdt+total.Vol+yield+emission_O2+rab+Thr+lactate+PO4.ferm.+PO4.apporte+PO4.utilise; 0.578, 0.810, tmp+Main.Thr.Conc.+Nitrogen.Conc.+Lys_conc.+X.VXdt+total.Vol+emission_O2+rab+Thr+lactate+PO4.ferm.+PO4.apporte; 0.562, 0.810, tmp+P-Source.Feed.conc.+Nitrogen.Conc.+OD+Lys_conc.+X.VXdt+total.Vol+total.cell+emission_O2+rab+Thr+His+lactate+PO4.ferm.; 0.586, 0.810, tmp+P-Source.Feed.conc.+Nitrogen.Conc.+OD+Lys_conc.+X.VXdt+total.Vol+emission_O2+rab+lactate+PO4.ferm.; 0.562, 0.810, pH+tmp+P-Source.Feed.conc.+Nitrogen.Conc.+Lys_conc.+X.VXdt+total.Vol+total.cell+emission_O2+rab+Thr+His+lactate+PO4.ferm.; 0.562, 0.810, pH+tmp+Main.Thr.Conc.+Nitrogen.Conc.+OD+Lys_conc.+X.VXdt+total.cell+emission_O2+rab+Thr+lactate+SO4.ferm.+PO4.ferm.; 0.578, 0.810, pH+P-Source.Feed.conc.+Nitrogen.Conc.+OD+Lys_conc.+X.VXdt+total.cell+emission_O2+rab+Thr+lactate+PO4.ferm.; 0.553, 0.810, pH+tmp+Main.Thr.Conc.+Nitrogen.Conc.+Lys_conc.+X.VXdt+total.Vol+total.cell+PL+emission_O2+rab+Thr+lactate+SO4.ferm.+PO4.ferm.; 0.594, 0.810, tmp+OD+Lys_conc.+X.VXdt+total.cell+PL+emission_O2+Thr+lactate+PO4.ferm.; 0.570, 0.810, pH+tmp+P-Source.Feed.conc.+Nitrogen.Conc.+Lys_conc.+X.VXdt+total.Vol+PL+emission_O2+rab+His+lactate+PO4.ferm.; 0.544, 0.810, pH+tmp+Main.Thr.Conc.+Nitrogen.Conc.+Lys_conc.+X.VXdt+total.Vol+yield+PL+emission_O2+rab+Thr+lactate+PO4.ferm.+PO4.apporte+PO4.utilise; 0.586, 0.810, tmp+Main.Thr.Conc.+OD+Lys_conc.+X.VXdt+total.cell+PL+Thr+His+lactate+PO4.ferm.; 0.562, 0.810, pH+tmp+P-Source.Feed.conc.+Nitrogen.Conc.+Lys_conc.+X.VXdt+total.Vol+PL+emission_O2+rab+Thr+His+lactate+PO4.ferm.; 0.570, 0.810, pH+tmp+Nitrogen.Conc.+Lys_conc.+X.F.Suc+X.VXdt+total.Vol+emission_O2+rab+Thr+His+lactate+PO4.ferm.; 0.570, 0.810, pH+tmp+Main.P-Source.Conc.+Nitrogen.Conc.+Lys_conc.+X.F.Suc+X.VXdt+total.Vol+emission_O2+rab+His+lactate+PO4.ferm.; 0.586, 0.810, pH+tmp+Nitrogen.Conc.+Lys_conc.+X.VXdt+total.Vol+emission_O2+rab+lactate+SO4.ferm.+PO4.ferm.; 0.586, 0.810, Main.Thr.Conc.+Nitrogen.Conc.+Lys_conc.+X.VXdt+total.Vol+yield+emission_O2+rab+Thr+lactate+PO4.utilise; 0.562, 0.810, pH+Nitrogen.Conc.+Lys_conc.+X.VXdt+total.Vol+yield+PL+emission_O2+rab+Thr+lactate+PO4.ferm.+PO4.apporte+PO4.utilise; 0.561, 0.810, pH+tmp+Nitrogen.Conc.+Lys_conc.+X.F.Suc+X.VXdt+total.Vol+total.cell+PL+emission_O2+rab+Thr+lactate+PO4.ferm.; 0.601, 0.810, pH+tmp+Nitrogen.Conc.+Lys_conc.+X.F.Suc+X.

VXdt+total.Vol+lactate+PO4.ferm.; 0.578, 0.810, tmp+Nitrogen.Conc.+Lys_conc.+X.VXdt+total.Vol+yield+emission_O2+rab+Thr+lactate+PO4.ferm.+PO4.utilise; 0.561, 0.810, pH+tmp+Nitrogen.Conc.+Lys_conc.+X.VXdt+total.Vol+PL+emission_O2+rab+Thr+His+lactate+SO4.ferm.+PO4.ferm.; 0.608, 0.810, tmp+OD+Lys_conc.+X.VXdt+total.cell+Thr+His+PO4.ferm.; 0.586, 0.810, pH+tmp+Main.Thr.Conc.+OD+Lys_conc.+X.VXdt+total.cell+emission_O2+rab+Thr+PO4.ferm.; 0.570, 0.810, tmp+Main.Thr.Conc.+Nitrogen.Conc.+OD+Lys_conc.+X.VXdt+total.cell+PL+emission_O2+rab+Thr+lactate+PO4.ferm.; 0.570, 0.810, Nitrogen.Conc.+Lys_conc.+X.VXdt+total.Vol+yield+PL+emission_O2+rab+Thr+His+lactate+PO4.ferm.+PO4.apporte; 0.561, 0.810, pH+tmp+P-Source.Feed.conc.+Nitrogen.Conc.+OD+Lys_conc.+X.VXdt+total.Vol+PL+emission_O2+rab+Thr+lactate+PO4.ferm.; 0.593, 0.810, tmp+Nitrogen.Conc.+Lys_conc.+X.VXdt+total.Vol+emission_O2+rab+His+lactate+PO4.ferm.; 0.593, 0.810, tmp+OD+Lys_conc.+X.F.Suc+X.VXdt+total.cell+emission_O2+rab+Thr+PO4.ferm.; 0.578, 0.810, pH+tmp+Main.P-Source.Conc.+OD+Lys_conc.+X.VXdt+total.cell+emission_O2+rab+Thr+lactate+PO4.ferm.; 0.570, 0.810, tmp+P-Source.Feed.conc.+Nitrogen.Conc.+Lys_conc.+X.VXdt+total.Vol+total.cell+emission_O2+rab+Thr+His+lactate+PO4.ferm.; 0.570, 0.810, tmp+Nitrogen.Conc.+Lys_conc.+X.VXdt+total.Vol+emission_O2+rab+Thr+His+lactate+PO4.ferm.+PO4.apporte+PO4.utilise; 0.570, 0.810, pH+tmp+Main.Thr.Conc.+Lys_conc.+X.VXdt+total.Vol+total.cell+PL+emission_O2+rab+Thr+lactate+PO4.ferm.; 0.586, 0.810, pH+tmp+Nitrogen.Conc.+OD+Lys_conc.+X.VXdt+total.cell+PL+Thr+lactate+PO4.ferm.; 0.543, 0.810, pH+tmp+Main.Thr.Conc.+Nitrogen.Conc.+OD+Lys_conc.+X.VXdt+total.Vol+total.cell+PL+emission_O2+rab+Thr+His+lactate+PO4.ferm.; 0.585, 0.810, Nitrogen.Conc.+Lys_conc.+X.VXdt+total.Vol+yield+PL+emission_O2+rab+Thr+lactate+PO4.utilise; 0.578, 0.810, tmp+Main.P-Source.Conc.+Nitrogen.Conc.+Lys_conc.+X.VXdt+total.Vol+total.cell+emission_O2+rab+Thr+lactate+PO4.ferm.; 0.569, 0.810, pH+Nitrogen.Conc.+Lys_conc.+X.VXdt+total.Vol+yield+emission_O2+rab+Thr+lactate+PO4.ferm.+PO4.apporte+PO4.utilise; 0.578, 0.810, pH+tmp+Main.Thr.Conc.+Lys_conc.+X.VXdt+total.Vol+PL+emission_O2+rab+Thr+lactate+PO4.ferm.; 0.552, 0.810, pH+tmp+Main.Thr.Conc.+Nitrogen.Conc.+Lys_conc.+X.VXdt+total.Vol+total.cell+PL+emission_O2+rab+Thr+His+lactate+PO4.ferm.; 0.561, 0.810, pH+tmp+Main.Thr.Conc.+OD+Lys_conc.+X.VXdt+total.cell+PL+emission_O2+rab+Thr+lactate+SO4.ferm.+PO4.ferm.; 0.607, 0.810, tmp+Nitrogen.Conc.+Lys_conc.+X.F.Suc+X.VXdt+total.Vol+lactate+PO4.ferm.; 0.569, 0.810, tmp+Nitrogen.Conc.+Lys_conc.+X.VXdt+total.Vol+total.cell+PL+emission_O2+rab+Thr+His+lactate+PO4.ferm.; 0.585, 0.810, pH+tmp+Lys_conc.+X.VXdt+total.Vol+PL+emission_O2+rab+Thr+lactate+PO4.ferm.; 0.577, 0.810, pH+tmp+Main.P-Source.Conc.+Nitrogen.Conc.+Lys_conc.+X.VXdt+total.Vol+total.cell+emission_O2+rab+lactate+PO4.ferm.; 0.577, 0.810, pH+tmp+P-Source.Feed.conc.+Nitrogen.Conc.+Lys_conc.+X.VXdt+total.Vol+yield+emission_O2+rab+lactate+PO4.ferm.; 0.577, 0.810, tmp+Main.Thr.Conc.+Nitrogen.Conc.+OD+Lys_conc.+X.F.Suc+X.VXdt+total.cell+Thr+His+lactate+PO4.ferm.; 0.561, 0.810, pH+tmp+Nitrogen.Conc.+Lys_conc.+X.VXdt+total.Vol+total.cell+emission_O2+rab+Thr+His+lactate+SO4.ferm.+PO4.ferm.; 0.569, 0.810, pH+tmp+Nitrogen.Conc.+Lys_conc.+X.VXdt+total.Vol+total.cell+PL+emission_O2+rab+His+lactate+PO4.ferm.; 0.577, 0.810, pH+tmp+OD+Lys_conc.+X.VXdt+total.cell+PL+emission_O2+rab+Thr+SO4.ferm.+PO4.ferm.; 0.569, 0.809, pH+tmp+Nitrogen.Conc.+OD+Lys_conc.+X.VXdt+total.Vol+total.cell+PL+emission_O2+rab+lactate+PO4.ferm.; 0.543, 0.809, tmp+Nitrogen.Conc.+Lys_conc.+X.VXdt+total.Vol+yield+PL+emission_O2+rab+Thr+His+lactate+SO4.ferm.+PO4.ferm.+PO4.apporte+PO4.utilise; 0.561, 0.809, Main.Thr.Conc.+Nitrogen.Conc.+Lys_conc.+X.VXdt+total.Vol+yield+emission_O2+rab+Thr+His+lactate+PO4.ferm.+PO4.apporte+PO4.utilise; 0.585, 0.809, tmp+OD+Lys_conc.+X.VXdt+total.cell+emission_O2+rab+Thr+lactate+SO4.ferm.+PO4.ferm.; 0.543, 0.809, pH+tmp+Nitrogen.Conc.+Lys_conc.+X.VXdt+total.Vol+yield+PL+emission_O2+rab+Thr+His+lactate+PO4.ferm.+PO4.apporte+PO4.utilise; 0.585, 0.809, Nitrogen.Conc.+Lys_conc.+X.VXdt+total.Vol+yield+emission_O2+rab+Thr+lactate+PO4.apporte+PO4.utilise; 0.561, 0.809, pH+tmp+Main.Thr.Conc.+OD+Lys_conc.+X.VXdt+total.Vol+total.cell+PL+emission_O2+rab+Thr+lactate+PO4.ferm.; 0.592, 0.809, tmp+Nitrogen.Conc.+OD+Lys_conc.+X.VXdt+total.cell+emission_O2+Thr+lactate+PO4.ferm.; 0.585, 0.809, tmp+Main.Thr.Conc.+Nitrogen.Conc.+OD+Lys_conc.+X.VXdt+total.cell+Thr+lactate+SO4.ferm.+PO4.ferm.; 0.569, 0.809, pH+tmp+Nitrogen.Conc.+Lys_conc.+X.VXdt+total.Vol+emission_O2+rab+Thr+His+lactate+PO4.ferm.+PO4.apporte; 0.577, 0.809, pH+tmp+Main.Thr.Conc.+Nitrogen.Conc.+OD+Lys_conc.+X.VXdt+total.Vol+emission_O2+rab+lactate+PO4.ferm.; 0.585, 0.809, Nitrogen.Conc.+Lys_conc.+X.F.Suc+X.VXdt+total.Vol+yield+emission_O2+rab+Thr+lactate+PO4.utilise; 0.592, 0.809, tmp+OD+Lys_conc.+X.F.Suc+X.VXdt+total.cell+PL+Thr+lactate+PO4.ferm.; 0.569, 0.809, pH+tmp+P-Source.Feed.conc.+Main.Thr.Conc.+Nitrogen.Conc.+Lys_conc.+X.VXdt+total.Vol+yield+emission_O2+rab+lactate+PO4.ferm.; 0.569, 0.809, tmp+P-Source.Feed.conc.+Nitrogen.Conc.+OD+Lys_conc.+X.VXdt+total.cell+PL+emission_O2+rab+Thr+lactate+PO4.ferm.; 0.577, 0.809, P-Source.Feed.conc.+Nitrogen.Conc.+Lys_conc.+X.VXdt+total.Vol+yield+emission_O2+rab+Thr+lactate+PO4.ferm.+PO4.utilise; 0.577, 0.809, tmp+Nitrogen.Conc.+Lys_conc.+X.VXdt+total.Vol+total.cell+emission_O2+rab+Thr+lactate+SO4.ferm.+PO4.ferm.; 0.551, 0.809, pH+tmp+Nitrogen.Conc.+OD+Lys_conc.+X.VXdt+total.Vol+total.cell+emission_O2+rab+Thr+His+lactate+SO4.ferm.+PO4.ferm.; 0.569, 0.809, tmp+Main.Thr.Conc.+Nitrogen.Conc.+OD+Lys_conc.+X.VXdt+total.Vol+total.cell+emission_O2+rab+Thr+lactate+PO4.ferm.; 0.577, 0.809, pH+tmp+Nitrogen.Conc.+OD+Lys_conc.+X.VXdt+total.cell+emission_O2+rab+His+lactate+PO4.ferm.; 0.551, 0.809, pH+tmp+Main.Thr.Conc.+Nitrogen.Conc.+OD+Lys_conc.+X.VXdt+total.Vol+total.cell+emission_O2+rab+Thr+His+lactate+PO4.ferm.; 0.577, 0.809, tmp+Nitrogen.Conc.+Lys_conc.+X.VXdt+total.Vol+emission_O2+rab+Thr+His+lactate+PO4.ferm.+PO4.utilise; 0.569, 0.809, Nitrogen.Conc.+Lys_conc.+X.F.Suc+X.VXdt+total.Vol+yield+emission_O2+rab+Thr+His+lactate+PO4.ferm.+PO4.apporte; 0.592, 0.809, tmp+Main.P-Source.Conc.+Nitrogen.Conc.+OD+Lys_conc.+X.VXdt+total.cell+Thr+lactate+PO4.ferm.; 0.569, 0.809, tmp+P-Source.Feed.conc.+Nitrogen.Conc.+Lys_conc.+X.VXdt+total.Vol+yield+emission_O2+rab+Thr+lactate+PO4.ferm.+PO4.apporte; 0.592, 0.809, pH+tmp+OD+Lys_conc.+X.VXdt+total.cell+PL+Thr+lactate+PO4.ferm.; 0.551, 0.809, tmp+Main.Thr.Conc.+Nitrogen.Conc.+Lys_conc.+X.VXdt+total.Vol+yield+emission_O2+rab+Thr+His+lactate+PO4.ferm.+PO4.apporte+PO4.utilise; 0.577, 0.809, tmp+Main.Thr.Conc.+Nitrogen.Conc.+OD+Lys_conc.+X.VXdt+total.cell+PL+Thr+His+lactate+PO4.ferm.; 0.560, 0.809, pH+tmp+Main.P-Source.Conc.+Nitrogen.Conc.+OD+Lys_ conc.+X.VXdt+total.Vol+PL+emission_O2+rab+Thr+lactate+PO4.ferm.; 0.568, 0.809, tmp+Main.P-Source.Conc.+Nitrogen.Conc.+OD+Lys_conc.+X.VXdt+total.cell+emission_O2+rab+Thr+His+lactate+PO4.ferm.; 0.577, 0.809, pH+tmp+OD+Lys_conc.+X.VXdt+total.cell+emission_O2+rab+Thr+lactate+SO4.ferm.+PO4.ferm.; 0.568, 0.809, pH+tmp+Nitrogen.Conc.+Lys_conc.+X.F.Suc+X.VXdt+total.Vol+PL+emission_O2+rab+Thr+lactate+PO4.ferm.; 0.584, 0.809, tmp+Main.Thr.Conc.+OD+Lys_conc.+X.VXdt+total.cell+PL+emission_O2+Thr+lactate+PO4.ferm.; 0.551, 0.809, pH+tmp+Nitrogen.Conc.+OD+Lys_conc.+X.F.Suc+X.VXdt+total.cell+PL+emission_O2+rab+Thr+lactate+SO4.ferm.+PO4.ferm.; 0.584, 0.809, pH+tmp+Main.Thr.Conc.+Nitrogen.Conc.+OD+Lys_conc.+X.VXdt+total.cell+Thr+lactate+PO4.ferm.; 0.542, 0.809, pH+tmp+Main.Thr.Conc.+Nitrogen.Conc.+OD+Lys_conc.+X.VXdt+total.Vol+total.cell+PL+emission_O2+rab+Thr+lactate+SO4.ferm.+PO4.ferm.; 0.568, 0.809, pH+tmp+Nitrogen.Conc.+Lys_conc.+X.VXdt+total.Vol+yield+emission_O2+rab+Thr+lactate+PO4.ferm.+PO4.apporte; 0.576, 0.809, pH+tmp+Main.Thr.Conc.+Nitrogen.Conc.+Lys_conc.+X.F.Suc+X.VXdt+total.Vol+emission_O2+rab+lactate+PO4.ferm.; 0.560, 0.809, pH+tmp+Nitrogen.Conc.+Lys_conc.+X.VXdt+total.Vol+PL+emission_O2+rab+Thr+His+lactate+PO4.ferm.+PO4.apporte; 0.568, 0.809, tmp+Main.Thr.Conc.+Nitrogen.Conc.+OD+Lys_conc.+X.F.Suc+X.VXdt+total.cell+emission_O2+rab+Thr+lactate+PO4.ferm.; 0.568, 0.809, pH+tmp+Main.P-Source.Conc.+Nitrogen.Conc.+OD+Lys_conc.+X.VXdt+total.Vol+emission_O2+rab+Thr+lactate+PO4.ferm.; 0.560, 0.809, pH+tmp+P-Source.Feed.conc.+Main.Thr.Conc.+Nitrogen.Conc.+OD+Lys_conc.+X.VXdt+total.cell+emission_O2+rab+Thr+lactate+PO4.ferm.; 0.576, 0.809, pH+tmp+Nitrogen.Conc.+Lys_conc.+X.VXdt+total.Vol+emission_O2+rab+His+lactate+SO4.ferm.+PO4.ferm.; 0.551, 0.809, pH+tmp+Nitrogen.Conc.+OD+Lys_conc.+X.F.Suc+X.VXdt+total.cell+emission_O2+rab+Thr+His+lactate+SO4.ferm.+PO4.ferm.; 0.599, 0.809, tmp+OD+Lys_conc.+X.VXdt+total.cell+Thr+lactate+SO4.ferm.+PO4.ferm.; 0.576, 0.809, tmp+Main.P-Source.Conc.+P-Source.Feed.conc.+Nitrogen.Conc.+Lys_conc.+X.VXdt+total.Vol+emission_O2+rab+His+lactate+PO4.ferm.; 0.568, 0.809, tmp+Lys_conc.+X.VXdt+total.Vol+yield+PL+emission_O2+rab+Thr+lactate+PO4.ferm.+PO4.apporte+PO4.utilise; 0.576, 0.809, tmp+P-Source.Feed.conc.+Nitrogen.Conc.+Lys_conc.+X.VXdt+total.Vol+emission_O2+rab+Thr+lactate+PO4.ferm.+PO4.apporte; 0.551, 0.809, Nitrogen.Conc.+Lys_conc.+X.VXdt+total.Vol+yield+PL+emission_O2+rab+Thr+His+lactate+SO4.ferm.+PO4.ferm.+PO4.apporte+PO4.utilise; 0.584, 0.809, tmp+Nitrogen.Conc.+Lys_conc.+X.VXdt+total.Vol+emission_O2+rab+Thr+lactate+PO4.apporte+PO4.utilise; 0.568, 0.809, pH+tmp+Nitrogen.Conc.+OD+Lys_conc.+X.F.Suc+X.VXdt+total.cell+PL+emission_O2+rab+Thr+PO4.ferm.; 0.560, 0.809, P-Source.Feed.conc.+Nitrogen.Conc.+Lys_conc.+X.VXdt+total.Vol+yield+PL+emission_O2+rab+Thr+lactate+PO4.ferm.+PO4.apporte+PO4.utilise; 0.584, 0.809, tmp+Nitrogen.Conc.+OD+Lys_conc.+X.VXdt+total.cell+Thr+His+lactate+SO4.ferm.+PO4.ferm.; 0.568, 0.809, pH+tmp+P-Source.Feed.conc.+Nitrogen.Conc.+Lys_conc.+X.F.Suc+X.VXdt+total.Vol+emission_O2+rab+Thr+lactate+PO4.ferm.; 0.576, 0.809, tmp+OD+Lys_conc.+X.VXdt+total.cell+PL+emission_O2+rab+Thr+lactate+SO4.ferm.+PO4.ferm.; 0.576, 0.809, pH+tmp+Nitrogen.Conc.+Lys_conc.+X.F.Suc+X.VXdt+total.Vol+emission_O2+rab+Thr+lactate+SO4.ferm.+PO4.ferm.; 0.559, 0.809, tmp+Nitrogen.Conc.+OD+Lys_conc.+X.VXdt+total.Vol+total.cell+PL+emission_O2+rab+Thr+His+lactate+PO4.ferm.; 0.568, 0.809, tmp+Nitrogen.Conc.+OD+Lys_conc.+X.F.Suc+X.VXdt+total.cell+emission_O2+rab+Thr+lactate+SO4.ferm.+PO4.ferm.; 0.568, 0.809, P-Source.Feed.conc.+Nitrogen.Conc.+Lys_conc.+X.VXdt+total.Vol+yield+emission_O2+rab+Thr+lactate+PO4.ferm.+PO4.apporte+PO4.utilise; 0.576, 0.809, tmp+OD+Lys_conc.+X.F.Suc+X.VXdt+total.cell+PL+emission_O2+rab+Thr+lactate+PO4.ferm.; 0.584, 0.809, tmp+Nitrogen.Conc.+OD+Lys_conc.+X.VXdt+total.cell+PL+emission_O2+rab+Thr+PO4.ferm.; 0.584, 0.809, tmp+P-Source.Feed.conc.+Main.Thr.Conc.+Nitrogen.Conc.+Lys_conc.+X.VXdt+total.Vol+emission_O2+rab+lactate+PO4.ferm.; 0.612, 0.809, tmp+Nitrogen.Conc.+Lys_conc.+X.VXdt+total.Vol+lactate+PO4.ferm.; 0.576, 0.809, pH+tmp+Main.Thr.Conc.+Nitrogen.Conc.+Lys_conc.+X.VXdt+total.Vol+PL+emission_O2+rab+lactate+PO4.ferm.; 0.550, 0.809, Main.Thr.Conc.+Nitrogen.Conc.+Lys_conc.+X.VXdt+total.Vol+yield+PL+emission_O2+rab+Thr+His+lactate+PO4.ferm.+PO4.apporte+PO4.utilise; 0.584, 0.809, tmp+Nitrogen.Conc.+OD+Lys_conc.+X.F.Suc+X.VXdt+total.cell+emission_O2+Thr+lactate+PO4.ferm.; 0.559, 0.809, pH+tmp+Main.Thr.Conc.+Nitrogen.Conc.+Lys_conc.+X.VXdt+total.Vol+total.cell+emission_O2+rab+Thr+His+lactate+PO4.ferm.; 0.567, 0.809, pH+P-Source.Feed.conc.+Nitrogen.Conc.+OD+Lys_conc.+X.F.Suc+X.VXdt+total.cell+emission_O2+rab+Thr+lactate+PO4.ferm.; 0.567, 0.809, pH+tmp+Nitrogen.Conc.+Lys_conc.+X.VXdt+total.Vol+emission_O2+rab+Thr+His+lactate+SO4.ferm.+PO4.ferm.; 0.567, 0.809, tmp+Main.P-Source.Conc.+P-Source.Feed.conc.+Nitrogen.Conc.+Lys_conc.+X.VXdt+total.Vol+emission_O2+rab+Thr+His+lactate+PO4.ferm.; 0.576, 0.809, tmp+OD+Lys_conc.+X.F.Suc+X.VXdt+total.cell+emission_O2+rab+Thr+His+lactate+PO4.ferm.; 0.583, 0.809, pH+tmp+Lys_conc.+X.VXdt+total.Vol+total.cell+emission_O2+rab+Thr+lactate+PO4.ferm.; 0.567, 0.809, Main.Thr.Conc.+Nitrogen.Conc.+Lys_conc.+X.VXdt+total.Vol+yield+emission_O2+rab+Thr+His+lactate+PO4.ferm.+PO4.apporte; 0.575, 0.809, pH+tmp+Nitrogen.Conc.+OD+Lys_conc.+X.F.Suc+X.VXdt+total.cell+Thr+His+lactate+PO4.ferm.; 0.559, 0.809, tmp+Nitrogen.Conc.+Lys_conc.+X.F.Suc+X.VXdt+total.Vol+yield+emission_O2+rab+Thr+lactate+PO4.ferm.+PO4.apporte+PO4.utilise; 0.598, 0.809, pH+tmp+OD+Lys_conc.+X.VXdt+total.cell+PL+Thr+PO4.ferm.; 0.583, 0.809, tmp+Nitrogen.Conc.+Lys_conc.+X.VXdt+total.Vol+emission_O2+rab+Thr+lactate+SO4.ferm.+PO4.ferm.; 0.567, 0.809, tmp+P-Source.Feed.conc.+Main.Thr.Conc.+Nitrogen.Conc.+OD+Lys_conc.+X.VXdt+total.cell+emission_O2+rab+Thr+lactate+PO4.ferm.; 0.559, 0.809, pH+tmp+Main.Thr.Conc.+Nitrogen.Conc.+Lys_conc.+X.VXdt+total.Vol+total.cell+emission_O2+rab+Thr+lactate+SO4.ferm.+PO4.ferm.; 0.559, 0.808, pH+tmp+Main.Thr.Conc.+Nitrogen.Conc.+Lys_conc.+X.VXdt+total.Vol+PL+emission_O2+rab+Thr+lactate+PO4.ferm.+PO4.apporte; 0.591, 0.808, tmp+OD+Lys_conc.+X.F.Suc+X.VXdt+total.cell+Thr+His+lactate+PO4.ferm.; 0.583, 0.808, tmp+Main.Thr.Conc.+Nitrogen.Conc.+OD+Lys_conc.+X.VXdt+total.cell+emission_O2+Thr+lactate+PO4.ferm.; 0.583, 0.808, pH+tmp+Nitrogen.Conc.+OD+Lys_conc.+X.F.Suc+X.VXdt+total.cell+emission_O2+rab+PO4.ferm.; 0.567, 0.808, pH+tmp+Main.P-Source.Conc.+P-Source.Feed.conc.+Main.Thr.Conc.+Nitrogen.Conc.+Lys_conc.+X.VXdt+total.Vol+emission_O2+rab+lactate+PO4.ferm.; 0.567, 0.808, tmp+Nitrogen.Conc.+OD+Lys_conc.+X.VXdt+total.cell+PL+emission_O2+rab+Thr+lactate+SO4.ferm.+PO4.ferm.; 0.575, 0.808, pH+tmp+Main.P-Source.Conc.+Main.Thr.Conc.+Nitrogen.Conc.+Lys_conc.+X.

VXdt+total.Vol+emission_O2+rab+lactate+PO4.ferm.; 0.567, 0.808, pH+tmp+Main.Thr.Conc.+Nitrogen.Conc.+Lys_conc.+X.VXdt+total.Vol+emission_O2+rab+Thr+lactate+PO4.ferm.+PO4.apporte; 0.575, 0.808, pH+tmp+Main.P-Source.Conc.+Nitrogen.Conc.+OD+Lys_conc.+X.VXdt+total.Vol+emission_O2+rab+lactate+PO4.ferm.; 0.567, 0.808, tmp+Main.P-Source.Conc.+Nitrogen.Conc.+OD+Lys_conc.+X.VXdt+total.cell+PL+emission_O2+rab+Thr+lactate+PO4.ferm.; 0.575, 0.808, P-Source.Feed.conc.+Nitrogen.Conc.+OD+Lys_conc.+X.F.Suc+X.VXdt+total.cell+emission_O2+rab+Thr+lactate+PO4.ferm.; 0.567, 0.808, pH+tmp+Main.P-Source.Conc.+Main.Thr.Conc.+Nitrogen.Conc.+Lys_conc.+X.VXdt+total.Vol+emission_O2+rab+Thr+lactate+PO4.ferm.; 0.605, 0.808, tmp+OD+Lys_conc.+X.F.Suc+X.VXdt+total.cell+Thr+PO4.ferm.; 0.567, 0.808, pH+tmp+Main.P-Source.Conc.+P-Source.Feed.conc.+Nitrogen.Conc.+Lys_conc.+X.VXdt+total.Vol+total.cell+emission_O2+rab+lactate+PO4.ferm.; 0.567, 0.808, tmp+Main.Thr.Conc.+Nitrogen.Conc.+OD+Lys_conc.+X.VXdt+total.cell+emission_O2+rab+Thr+His+lactate+PO4.ferm.; 0.575, 0.808, tmp+Nitrogen.Conc.+Lys_conc.+X.VXdt+total.Vol+PL+emission_O2+rab+Thr+lactate+PO4.ferm.+PO4.utilise; 0.549, 0.808, pH+tmp+P-Source.Feed.conc.+Nitrogen.Conc.+OD+Lys_conc.+X.VXdt+total.cell+PL+emission_O2+rab+Thr+His+lactate+PO4.ferm.; 0.549, 0.808, tmp+Nitrogen.Conc.+Lys_conc.+X.VXdt+total.Vol+yield+emission_O2+rab+Thr+His+lactate+SO4.ferm.+PO4.ferm.+PO4.apporte+PO4.utilise; 0.583, 0.808, tmp+Nitrogen.Conc.+OD+Lys_conc.+X.F.Suc+X.VXdt+total.cell+emission_O2+rab+Thr+PO4.ferm.; 0.575, 0.808, pH+tmp+OD+Lys_conc.+X.VXdt+total.Vol+total.cell+PL+emission_O2+rab+Thr+PO4.ferm.; 0.567, 0.808, pH+tmp+Nitrogen.Conc.+OD+Lys_conc.+X.VXdt+total.Vol+PL+emission_O2+rab+His+lactate+PO4.ferm.; 0.558, 0.808, tmp+Main.P-Source.Conc.+P-Source.Feed.conc.+Nitrogen.Conc.+OD+Lys_conc.+X.VXdt+total.Vol+total.cell+emission_O2+rab+Thr+lactate+PO4.ferm.; 0.590, 0.808, tmp+Nitrogen.Conc.+Lys_conc.+X.VXdt+total.Vol+total.cell+emission_O2+rab+lactate+PO4.ferm.; 0.575, 0.808, pH+tmp+Main.P-Source.Conc.+OD+Lys_conc.+X.VXdt+total.cell+PL+emission_O2+rab+Thr+PO4.ferm.; 0.558, 0.808, pH+tmp+Main.Thr.Conc.+OD+Lys_conc.+X.VXdt+total.cell+PL+emission_O2+rab+Thr+His+lactate+PO4.ferm.; 0.575, 0.808, pH+tmp+Nitrogen.Conc.+Lys_conc.+X.VXdt+total.Vol+emission_O2+rab+Thr+lactate+PO4.apporte+PO4.utilise; 0.558, 0.808, pH+tmp+Main.P-Source.Conc.+P-Source.Feed.conc.+Nitrogen.Conc.+OD+Lys_conc.+X.VXdt+total.cell+emission_O2+rab+Thr+lactate+PO4.ferm.; 0.583, 0.808, tmp+Nitrogen.Conc.+OD+Lys_conc.+X.VXdt+total.cell+PL+emission_O2+rab+Thr+lactate+PO4.ferm.; 0.549, 0.808, pH+tmp+Nitrogen.Conc.+OD+Lys_conc.+X.VXdt+total.Vol+PL+emission_O2+rab+Thr+His+lactate+SO4.ferm.+PO4.ferm.; 0.575, 0.808, tmp+Nitrogen.Conc.+OD+Lys_conc.+X.F.Suc+X.VXdt+total.cell+Thr+His+lactate+SO4.ferm.+PO4.ferm.; 0.558, 0.808, pH+tmp+Nitrogen.Conc.+Lys_conc.+X.VXdt+total.Vol+yield+emission_O2+rab+Thr+lactate+PO4.ferm.+PO4.apporte+PO4.utilise; 0.567, 0.808, Main.Thr.Conc.+Nitrogen.Conc.+Lys_conc.+X.F.Suc+X.VXdt+total.Vol+yield+emission_O2+rab+Thr+lactate+PO4.ferm.+PO4.apporte; 0.549, 0.808, pH+tmp+Main.Thr.Conc.+Nitrogen.Conc.+OD+Lys_conc.+X.F.Suc+X.VXdt+total.cell+PL+emission_O2+rab+Thr+lactate+PO4.ferm.; 0.582, 0.808, tmp+Nitrogen.Conc.+OD+Lys_conc.+X.F.Suc+X.VXdt+total.cell+emission_O2+rab+lactate+PO4.ferm.; 0.549, 0.808, pH+tmp+Nitrogen.Conc.+Lys_conc.+X.VXdt+total.Vol+PL+emission_O2+rab+Thr+His+lactate+PO4.ferm.+PO4.apporte+PO4.utilise; 0.566, 0.808, tmp+Main.P-Source.Conc.+P-Source.Feed.conc.+Nitrogen.Conc.+Lys_conc.+X.VXdt+total.cell+emission_O2+rab+Thr+lactate+PO4.ferm.; 0.549, 0.808, pH+tmp+Main.Thr.Conc.+Nitrogen.Conc.+OD+Lys_conc.+X.VXdt+total.Vol+total.cell+emission_O2+rab+Thr+lactate+SO4.ferm.+PO4.ferm.; 0.558, 0.808, pH+tmp+Main.P-Source.Conc.+P-Source.Feed.conc.+Nitrogen.Conc.+Lys_conc.+X.VXdt+total.Vol+PL+emission_O2+rab+Thr+lactate+PO4.ferm.; 0.549, 0.808, pH+tmp+Main.P-Source.Conc.+Nitrogen.Conc.+OD+Lys_conc.+X.F.Suc+X.VXdt+total.cell+emission_O2+rab+Thr+His+lactate+PO4.ferm.; 0.582, 0.808, tmp+Main.Thr.Conc.+OD+Lys_conc.+X.VXdt+total.cell+PL+Thr+lactate+SO4.ferm.+PO4.ferm.; 0.549, 0.808, Nitrogen.Conc.+Lys_conc.+X.F.Suc+X.VXdt+total.Vol+yield+PL+emission_O2+rab+Thr+His+lactate+PO4.ferm.+PO4.apporte+PO4.utilise; 0.574, 0.808, tmp+Main.P-Source.Conc.+OD+Lys_conc.+X.VXdt+total.cell+PL+emission_O2+rab+Thr+lactate+PO4.ferm.; 0.549, 0.808, pH+tmp+Main.P-Source.Conc.+Nitrogen.Conc.+OD+Lys_conc.+X.VXdt+total.cell+PL+emission_O2+rab+Thr+His+lactate+PO4.ferm.; 0.566, 0.808, Main.Thr.Conc.+Nitrogen.Conc.+Lys_conc.+X.VXdt+total.Vol+yield+PL+emission_O2+rab+Thr+lactate+PO4.ferm.+PO4.apporte; 0.566, 0.808, pH+tmp+Main.P-Source.Conc.+Nitrogen.Conc.+Lys_conc.+X.VXdt+total.Vol+total.cell+emission_O2+rab+His+lactate+PO4.ferm.; 0.574, 0.808, tmp+P-Source.Feed.conc.+Nitrogen.Conc.+Lys_conc.+X.VXdt+total.Vol+total.cell+emission_O2+rab+His+lactate+PO4.ferm.; 0.590, 0.808, tmp+Main.P-Source.Conc.+OD+Lys_conc.+X.VXdt+total.cell+emission_O2+rab+Thr+PO4.ferm.; 0.597, 0.808, tmp+OD+Lys_conc.+X.VXdt+total.cell+emission_O2+Thr+lactate+PO4.ferm.; 0.566, 0.808, pH+tmp+P-Source.Feed.conc.+Nitrogen.Conc.+Lys_conc.+X.VXdt+total.Vol+emission_O2+rab+Thr+lactate+SO4.ferm.+PO4.ferm.; 0.574, 0.808, pH+tmp+Main.Thr.Conc.+Nitrogen.Conc.+OD+Lys_conc.+X.F.Suc+X.VXdt+total.cell+Thr+lactate+PO4.ferm.; 0.574, 0.808, Nitrogen.Conc.+Lys_conc.+X.VXdt+total.Vol+yield+PL+emission_O2+Thr+lactate+PO4.ferm.+PO4.apporte+PO4.utilise; 0.574, 0.808, Nitrogen.Conc.+Lys_conc.+X.VXdt+total.Vol+yield+emission_O2+rab+Thr+lactate+SO4.ferm.+PO4.ferm.+PO4.apporte; 0.597, 0.808, tmp+Main.Thr.Conc.+Nitrogen.Conc.+OD+Lys_conc.+X.VXdt+total.cell+Thr+PO4.ferm.; 0.582, 0.808, pH+tmp+Nitrogen.Conc.+Lys_conc.+X.VXdt+total.Vol+emission_O2+rab+lactate+PO4.ferm.+PO4.apporte; 0.582, 0.808, tmp+Main.P-Source.Conc.+Nitrogen.Conc.+OD+Lys_conc.+X.F.Suc+X.VXdt+total.cell+Thr+lactate+PO4.ferm.; 0.566, 0.808, pH+tmp+Lys_conc.+X.VXdt+total.Vol+total.cell+PL+emission_O2+rab+Thr+His+lactate+PO4.ferm.; 0.539, 0.808, pH+tmp+P-Source.Feed.conc.+Nitrogen.Conc.+OD+Lys_conc.+X.VXdt+total.Vol+total.cell+PL+emission_O2+rab+Thr+His+lactate+PO4.ferm.; 0.566, 0.808, pH+tmp+P-Source.Feed.conc.+Nitrogen.Conc.+Lys_conc.+X.VXdt+total.Vol+yield+emission_O2+rab+His+lactate+PO4.ferm.; 0.566, 0.808, pH+tmp+Main.Thr.Conc.+Nitrogen.Conc.+OD+Lys_conc.+X.VXdt+total.cell+PL+emission_O2+rab+Thr+PO4.ferm.; 0.566, 0.808, pH+tmp+P-Source.Feed.conc.+Main.Thr.Conc.+Nitrogen.Conc.+Lys_conc.+X.VXdt+total.Vol+total.cell+emission_O2+rab+lactate+PO4.ferm.; 0.548, 0.808, pH+tmp+P-Source.Feed.conc.+Nitrogen.Conc.+OD+Lys_conc.+X.F.Suc+X.VXdt+total.cell+emission_O2+rab+Thr+His+lactate+PO4.ferm.; 0.566, 0.808, tmp+Nitrogen.Conc.+OD+Lys_conc.+X.VXdt+total.Vol+total.cell+emission_O2+rab+Thr+lactate+SO4.ferm.+PO4.ferm.; 0.597, 0.808, tmp+Nitrogen.Conc.+OD+Lys_conc.+X.F.Suc+X.VXdt+ total.cell+Thr+PO4.ferm.; 0.574, 0.808, tmp+Main.Thr. Conc.+OD+Lys_conc.+X.VXdt+total.cell+emission_O2+rab+Thr+His+lactate+PO4.ferm.; 0.582, 0.808, pH+Nitrogen.Conc.+Lys_conc.+X.VXdt+total.Vol+yield+emission_O2+rab+Thr+lactate+PO4.utilise; 0.557, 0.808, pH+tmp+OD+Lys_conc.+X.VXdt+total.Vol+total.cell+PL+emission_O2+rab+Thr+His+lactate+PO4.ferm.; 0.548, 0.808, pH+tmp+Main.Thr.Conc.+Nitrogen.Conc.+OD+Lys_conc.+X.F.Suc+X.VXdt+total.cell+emission_O2+rab+Thr+His+lactate+PO4.ferm.; 0.557, 0.808, pH+tmp+Main.P-Source.Conc.+Nitrogen.Conc.+Lys_conc.+X.VXdt+total.Vol+total.cell+emission_O2+rab+Thr+His+lactate+PO4.ferm.; 0.597, 0.808, pH+tmp+OD+Lys_conc.+X.VXdt+total.cell+Thr+lactate+PO4.ferm.; 0.566, 0.808, pH+tmp+Lys_conc.+X.VXdt+total.Vol+total.cell+PL+emission_O2+rab+Thr+lactate+SO4.ferm.+PO4.ferm.; 0.574, 0.808, pH+tmp+P-Source.Feed.conc.+Nitrogen.Conc.+Lys_conc.+X.VXdt+total.Vol+emission_O2+rab+lactate+SO4.ferm.+PO4.ferm.; 0.597, 0.808, tmp+Nitrogen.Conc.+OD+Lys_conc.+X.VXdt+total.cell+Thr+His+PO4.ferm.; 0.582, 0.808, pH+tmp+Main.Thr.Conc.+Nitrogen.Conc.+OD+Lys_conc.+X.F.Suc+X.VXdt+total.cell+lactate+PO4.ferm.; 0.557, 0.808, Nitrogen.Conc.+Lys_conc.+X.F.Suc+X.VXdt+total.Vol+yield+emission_O2+rab+Thr+lactate+SO4.ferm.+PO4.ferm.+PO4.apporte+PO4.utilise; 0.557, 0.808, tmp+Main.Thr.Conc.+Lys_conc.+X.VXdt+total.Vol+yield+PL+emission_O2+rab+Thr+lactate+PO4.ferm.+PO4.apporte+PO4.utilise; 0.565, 0.808, tmp+Main.P-Source.Conc.+Nitrogen.Conc.+OD+Lys_conc.+X.VXdt+total.Vol+total.cell+emission_O2+rab+Thr+lactate+PO4.ferm.; 0.565, 0.808, tmp+Main.Thr.Conc.+Nitrogen.Conc.+Lys_conc.+X.VXdt+total.Vol+emission_O2+rab+Thr+lactate+PO4.ferm.+PO4.apporte+PO4.utilise; 0.565, 0.808, pH+tmp+Main.P-Source.Conc.+Nitrogen.Conc.+Lys_conc.+X.VXdt+total.Vol+emission_O2+rab+Thr+His+lactate+PO4.ferm.; 0.574, 0.808, tmp+Main.Thr.Conc.+Nitrogen.Conc.+Lys_conc.+X.VXdt+total.Vol+emission_O2+rab+Thr+lactate+PO4.ferm.+PO4.utilise; 0.548, 0.808, pH+tmp+Main.Thr.Conc.+Nitrogen.Conc.+OD+Lys_conc.+X.VXdt+total.Vol+PL+emission_O2+rab+Thr+lactate+SO4.ferm.+PO4.ferm.; 0.581, 0.808, tmp+OD+Lys_conc.+X.VXdt+total.cell+PL+Thr+His+lactate+SO4.ferm.+PO4.ferm.; 0.565, 0.808, pH+tmp+Main.P-Source.Conc.+P-Source.Feed.conc.+Nitrogen.Conc.+OD+Lys_conc.+X.VXdt+total.Vol+emission_O2+rab+lactate+PO4.ferm.; 0.574, 0.808, pH+tmp+Main.Thr.Conc.+Nitrogen.Conc.+Lys_conc.+X.VXdt+total.Vol+emission_O2+rab+lactate+SO4.ferm.+PO4.ferm.; 0.557, 0.808, tmp+Nitrogen.Conc.+Lys_conc.+X.VXdt+total.Vol+yield+PL+emission_O2+rab+Thr+His+lactate+PO4.ferm.+PO4.apporte; 0.581, 0.808, tmp+OD+Lys_conc.+X.VXdt+total.cell+PL+emission_O2+rab+Thr+His+PO4.ferm.; 0.548, 0.808, pH+tmp+P-Source.Feed.conc.+Main.Thr.Conc.+Nitrogen.Conc.+OD+Lys_conc.+X.VXdt+total.Vol+total.cell+emission_O2+rab+Thr+lactate+PO4.ferm.; 0.589, 0.808, tmp+Nitrogen.Conc.+OD+Lys_conc.+X.VXdt+total.cell+PL+Thr+His+PO4.ferm.; 0.589, 0.808, tmp+Main.Thr.Conc.+OD+Lys_conc.+X.F.Suc+X.VXdt+total.cell+Thr+lactate+PO4.ferm.; 0.574, 0.808, tmp+Nitrogen.Conc.+Lys_conc.+X.VXdt+total.Vol+yield+emission_O2+rab+lactate+PO4.ferm.+PO4.apporte+PO4.utilise; 0.565, 0.808, pH+tmp+Main.Thr.Conc.+OD+Lys_conc.+X.VXdt+total.cell+emission_O2+rab+Thr+His+lactate+PO4.ferm.; 0.557, 0.808, tmp+Nitrogen.Conc.+OD+Lys_conc.+X.VXdt+total.cell+PL+emission_O2+rab+Thr+His+lactate+PO4.ferm.+PO4.apporte+PO4.utilise; 0.565, 0.808, pH+tmp+Main.P-Source.Conc.+Nitrogen.Conc.+Lys_conc.+X.F.Suc+X.VXdt+total.Vol+total.cell+emission_O2+rab+lactate+PO4.ferm.; 0.548, 0.808, pH+tmp+Nitrogen.Conc.+OD+Lys_conc.+X.F.Suc+X.VXdt+total.Vol+total.cell+emission_O2+rab+Thr+lactate+SO4.ferm.+PO4.ferm.; 0.565, 0.808, pH+Nitrogen.Conc.+Lys_conc.+X.VXdt+total.Vol+yield+PL+emission_O2+rab+Thr+lactate+PO4.ferm.+PO4.apporte; 0.565, 0.808, pH+tmp+Main.Thr.Conc.+Lys_conc.+X.VXdt+total.Vol+PL+emission_O2+rab+Thr+lactate+SO4.ferm.+PO4.ferm.; 0.589, 0.808, tmp+Main.Thr.Conc.+Nitrogen.Conc.+OD+Lys_conc.+X.F.Suc+X.VXdt+total.cell+lactate+PO4.ferm.; 0.581, 0.808, tmp+Nitrogen.Conc.+OD+Lys_conc.+X.VXdt+total.cell+emission_O2+rab+Thr+His+PO4.ferm.; 0.573, 0.808, tmp+Nitrogen.Conc.+OD+Lys_conc.+X.F.Suc+X.VXdt+total.cell+PL+Thr+His+lactate+PO4.ferm.; 0.589, 0.807, tmp+Main.Thr.Conc.+OD+Lys_conc.+X.VXdt+total.cell+Thr+lactate+SO4.ferm.+PO4.ferm.; 0.556, 0.807, pH+tmp+Main.P-Source.Conc.+Main.Thr.Conc.+Nitrogen.Conc.+OD+Lys_conc.+X.VXdt+total.cell+emission_O2+rab+Thr+lactate+PO4.ferm.; 0.556, 0.807, pH+tmp+Nitrogen.Conc.+Lys_conc.+X.VXdt+total.Vol+PL+emission_O2+rab+Thr+His+lactate+PO4.ferm.+PO4.utilise; 0.565, 0.807, pH+tmp+Nitrogen.Conc.+Lys_conc.+X.VXdt+total.Vol+PL+emission_O2+rab+Thr+lactate+PO4.apporte+PO4.utilise; 0.573, 0.807, tmp+Nitrogen.Conc.+Lys_conc.+X.VXdt+total.Vol+PL+emission_O2+rab+Thr+His+lactate+PO4.ferm.; 0.556, 0.807, pH+tmp+P-Source.Feed.conc.+Main.Thr.Conc.+Nitrogen.Conc.+Lys_conc.+X.VXdt+total.Vol+emission_O2+rab+Thr+His+lactate+PO4.ferm.; 0.565, 0.807, pH+tmp+P-Source.Feed.conc.+Main.Thr.Conc.+Nitrogen.Conc.+OD+Lys_conc.+X.VXdt+total.Vol+emission_O2+rab+lactate+PO4.ferm.; 0.556, 0.807, pH+tmp+Nitrogen.Conc.+OD+Lys_conc.+X.VXdt+total.Vol+total.cell+PL+emission_O2+rab+His+lactate+PO4.ferm.; 0.556, 0.807, tmp+P-Source.Feed.conc.+Nitrogen.Conc.+OD+Lys_conc.+X.VXdt+total.Vol+total.cell+PL+emission_O2+rab+Thr+lactate+PO4.ferm.; 0.565, 0.807, pH+tmp+Nitrogen.Conc.+Lys_conc.+X.VXdt+total.Vol+emission_O2+rab+Thr+His+lactate+PO4.ferm.+PO4.utilise; 0.581, 0.807, pH+tmp+Nitrogen.Conc.+OD+Lys_conc.+X.VXdt+total.cell+Thr+His+lactate+PO4.ferm.; 0.596, 0.807, pH+tmp+OD+Lys_conc.+X.VXdt+total.cell+emission_O2+rab+PO4.ferm.; 0.573, 0.807, tmp+P-Source.Feed.conc.+Nitrogen.Conc.+OD+Lys_conc.+X.VXdt+total.Vol+emission_O2+rab+His+lactate+PO4.ferm.; 0.565, 0.807, pH+tmp+P-Source.Feed.conc.+Nitrogen.Conc.+Lys_conc.+X.F.Suc+X.VXdt+total.Vol+total.cell+emission_O2+rab+lactate+PO4.ferm.; 0.547, 0.807, pH+tmp+P-Source.Feed.conc.+Nitrogen.Conc.+Lys_conc.+X.VXdt+total.Vol+total.cell+PL+emission_O2+rab+Thr+His+lactate+PO4.ferm.; 0.581, 0.807, pH+tmp+Main.Thr.Conc.+Lys_conc.+X.VXdt+total.Vol+emission_O2+rab+Thr+lactate+PO4.ferm.; 0.573, 0.807, tmp+Nitrogen.Conc.+Lys_conc.+X.F.Suc+X.VXdt+total.Vol+emission_O2+rab+Thr+lactate+PO4.ferm.+PO4.apporte; 0.556, 0.807, pH+tmp+P-Source.Feed.conc.+Nitrogen.Conc.+Lys_conc.+X.VXdt+total.Vol+PL+emission_O2+rab+Thr+lactate+SO4.ferm.+PO4.ferm.; 0.565, 0.807, tmp+P-Source.Feed.conc.+Nitrogen.Conc.+Lys_conc.+X.VXdt+total.Vol+total.cell+PL+emission_O2+rab+Thr+lactate+PO4.ferm.; 0.565, 0.807, pH+tmp+Main.P-Source.Conc.+Nitrogen.Conc.+OD+Lys_conc.+X.F.Suc+X.VXdt+total.cell+emission_O2+rab+lactate+PO4.ferm.; 0.573, 0.807, tmp+Nitrogen.Conc.+OD+Lys_conc.+X.VXdt+total.cell+PL+Thr+His+lactate+SO4.ferm.+PO4.ferm.; 0.573, 0.807, pH+tmp+Nitrogen.Conc.+Lys_conc.+X.F.Suc+X.VXdt+total.Vol+PL+emission_O2+rab+lactate+PO4.ferm.; 0.573, 0.807, tmp+Main.Thr.Conc.+Nitrogen.

Conc.+OD+Lys_conc.+X.VXdt+total.Vol+emission_O2+rab+Thr+lactate+PO4.ferm.; 0.565, 0.807, pH+tmp+Main.Thr.Conc.+Nitrogen.Conc.+OD+Lys_conc.+X.VXdt+total.Vol+total.cell+emission_O2+rab+lactate+PO4.ferm.; 0.565, 0.807, pH+tmp+OD+Lys_conc.+X.F.Suc+X.VXdt+total.cell+emission_O2+rab+Thr+His+lactate+PO4.ferm.; 0.556, 0.807, pH+tmp+P-Source.Feed.conc.+Nitrogen.Conc.+OD+Lys_conc.+X.VXdt+total.Vol+emission_O2+rab+Thr+His+lactate+PO4.ferm.; 0.547, 0.807, pH+tmp+Main.Thr.Conc.+Nitrogen.Conc.+Lys_conc.+X.VXdt+total.Vol+PL+emission_O2+rab+Thr+His+lactate+SO4.ferm.+PO4.ferm.; 0.596, 0.807, tmp+OD+Lys_conc.+X.F.Suc+X.VXdt+total.cell+PL+Thr+PO4.ferm.; 0.556, 0.807, pH+tmp+OD+Lys_conc.+X.VXdt+total.Vol+total.cell+PL+emission_O2+rab+Thr+lactate+SO4.ferm.+PO4.ferm.; 0.573, 0.807, tmp+P-Source.Feed.conc.+Nitrogen.Conc.+OD+Lys_conc.+X.VXdt+total.Vol+total.cell+emission_O2+rab+lactate+PO4.ferm.; 0.573, 0.807, tmp+Main.Thr.Conc.+Nitrogen.Conc.+OD+Lys_conc.+X.F.Suc+X.VXdt+total.cell+Thr+lactate+SO4.ferm.+PO4.ferm.; 0.588, 0.807, tmp+Nitrogen.Conc.+OD+Lys_conc.+X.VXdt+total.Vol+emission_O2+rab+lactate+PO4.ferm.; 0.580, 0.807, tmp+P-Source.Feed.conc.+OD+Lys_conc.+X.VXdt+total.cell+emission_O2+rab+Thr+lactate+PO4.ferm.; 0.580, 0.807, pH+tmp+Main.P-Source.Conc.+OD+Lys_conc.+X.VXdt+total.cell+emission_O2+rab+Thr+PO4.ferm.; 0.573, 0.807, tmp+Main.Thr.Conc.+Nitrogen.Conc.+OD+Lys_conc.+X.VXdt+total.cell+PL+Thr+lactate+SO4.ferm.+PO4.ferm.; 0.616, 0.807, tmp+OD+Lys_conc.+X.VXdt+total.cell+PO4.ferm.; 0.564, 0.807, tmp+Main.P-Source.Conc.+P-Source.Feed.conc.+Main.Thr.Conc.+Nitrogen.Conc.+Lys_conc.+X.VXdt+total.Vol+emission_O2+rab+Thr+lactate+PO4.ferm.; 0.580, 0.807, pH+tmp+Lys_conc.+X.VXdt+total.Vol+total.cell+PL+emission_O2+rab+Thr+PO4.ferm.; 0.572, 0.807, tmp+P-Source.Feed.conc.+Nitrogen.Conc.+Lys_conc.+X.F.Suc+X.VXdt+total.Vol+emission_O2+rab+Thr+lactate+PO4.ferm.; 0.537, 0.807, pH+tmp+Nitrogen.Conc.+Lys_conc.+X.VXdt+total.Vol+yield+PL+emission_O2+rab+Thr+lactate+SO4.ferm.+PO4.ferm.+PO4.apporte+PO4.utilise; 0.595, 0.807, pH+tmp+Nitrogen.Conc.+Lys_conc.+X.VXdt+total.Vol+emission_O2+rab+PO4.ferm.; 0.564, 0.807, pH+tmp+Main.Thr.Conc.+Nitrogen.Conc.+Lys_conc.+X.VXdt+total.Vol+total.cell+emission_O2+rab+His+lactate+PO4.ferm.; 0.602, 0.807, pH+tmp+Nitrogen.Conc.+Lys_conc.+X.VXdt+total.Vol+lactate+PO4.ferm.; 0.588, 0.807, pH+tmp+Nitrogen.Conc.+Lys_conc.+X.F.Suc+X.VXdt+total.Vol+His+lactate+PO4.ferm.; 0.588, 0.807, tmp+OD+Lys_conc.+X.VXdt+total.cell+Thr+His+lactate+SO4.ferm.+PO4.ferm.; 0.572, 0.807, pH+tmp+Main.Thr.Conc.+Nitrogen.Conc.+OD+Lys_conc.+X.VXdt+total.cell+emission_O2+rab+Thr+PO4.ferm.; 0.555, 0.807, Main.Thr.Conc.+Nitrogen.Conc.+Lys_conc.+X.VXdt+total.Vol+yield+emission_O2+rab+Thr+lactate+SO4.ferm.+PO4.ferm.+PO4.apporte+PO4.utilise; 0.564, 0.807, tmp+P-Source.Feed.conc.+Nitrogen.Conc.+OD+Lys_conc.+X.VXdt+total.Vol+emission_O2+rab+Thr+His+lactate+PO4.ferm.; 0.564, 0.807, pH+P-Source.Feed.conc.+Nitrogen.Conc.+Lys_conc.+X.VXdt+total.Vol+yield+emission_O2+rab+Thr+lactate+PO4.ferm.+PO4.apporte; 0.555, 0.807, pH+tmp+P-Source.Feed.conc.+Main.Thr.Conc.+Nitrogen.Conc.+Lys_conc.+X.VXdt+total.Vol+total.cell+emission_O2+rab+Thr+lactate+PO4.ferm.; 0.547, 0.807, tmp+P-Source.Feed.conc.+Nitrogen.Conc.+Lys_conc.+X.VXdt+total.Vol+yield+PL+emission_O2+rab+Thr+lactate+PO4.ferm.+PO4.apporte+PO4.utilise; 0.580, 0.807, tmp+OD+Lys_conc.+X.VXdt+total.Vol+PL+emission_O2+rab+Thr+lactate+PO4.ferm.; 0.555, 0.807, pH+tmp+Main.Thr.Conc.+Nitrogen.Conc.+Lys_conc.+X.VXdt+total.Vol+PL+emission_O2+rab+Thr+lactate+PO4.ferm.+PO4.utilise; 0.588, 0.807, pH+tmp+Nitrogen.Conc.+Lys_conc.+X.VXdt+total.Vol+emission_O2+rab+His+lactate; 0.555, 0.807, pH+tmp+P-Source.Feed.conc.+Main.Thr.Conc.+Nitrogen.Conc.+Lys_conc.+X.VXdt+total.Vol+yield+emission_O2+rab+His+lactate+PO4.ferm.; 0.572, 0.807, tmp+Nitrogen.Conc.+OD+Lys_conc.+X.F.Suc+X.VXdt+total.Vol+emission_O2+rab+Thr+lactate+PO4.ferm.; 0.555, 0.807, tmp+P-Source.Feed.conc.+Main.Thr.Conc.+Nitrogen.Conc.+Lys_conc.+X.VXdt+total.Vol+yield+emission_O2+rab+Thr+lactate+PO4.ferm.+PO4.apporte; 0.572, 0.807, pH+tmp+Main.P-Source.Conc.+Nitrogen.Conc.+Lys_conc.+X.VXdt+total.Vol+PL+emission_O2+rab+lactate+PO4.ferm.; 0.546, 0.807, pH+tmp+P-Source.Feed.conc.+Nitrogen.Conc.+OD+Lys_conc.+X.F.Suc+X.VXdt+total.Vol+total.cell+emission_O2+rab+Thr+lactate+PO4.ferm.; 0.572, 0.807, pH+tmp+Nitrogen.Conc.+Lys_conc.+X.VXdt+total.Vol+PL+emission_O2+rab+lactate+SO4.ferm.+PO4.ferm.; 0.546, 0.807, pH+tmp+Main.P-Source.Conc.+Nitrogen.Conc.+Lys_conc.+X.VXdt+total.Vol+total.cell+PL+emission_O2+rab+Thr+His+lactate+PO4.ferm.; 0.602, 0.807, tmp+P-Source.Feed.conc.+Nitrogen.Conc.+Lys_conc.+X.VXdt+total.Vol+lactate+PO4.ferm.; 0.595, 0.807, tmp+Main.P-Source.Conc.+OD+Lys_conc.+X.VXdt+total.cell+Thr+lactate+PO4.ferm.; 0.546, 0.807, pH+tmp+Main.P-Source.Conc.+P-Source.Feed.conc.+Nitrogen.Conc.+OD+Lys_conc.+X.VXdt+total.Vol+total.cell+emission_O2+rab+Thr+lactate+PO4.ferm.; 0.564, 0.807, pH+tmp+Nitrogen.Conc.+Lys_conc.+X.F.Suc+X.VXdt+total.Vol+emission_O2+rab+His+lactate+SO4.ferm.+PO4.ferm.; 0.572, 0.807, P-Source.Feed.conc.+Nitrogen.Conc.+OD+Lys_conc.+X.VXdt+total.cell+emission_O2+rab+Thr+His+lactate+PO4.ferm.; 0.564, 0.807, pH+tmp+Nitrogen.Conc.+OD+Lys_conc.+X.F.Suc+X.VXdt+total.cell+emission_O2+rab+Thr+His+PO4.ferm.; 0.555, 0.807, tmp+Main.Thr.Conc.+Nitrogen.Conc.+Lys_conc.+X.VXdt+total.Vol+yield+PL+emission_O2+Thr+lactate+PO4.ferm.+PO4.apporte+PO4.utilise; 0.564, 0.807, tmp+Nitrogen.Conc.+OD+Lys_conc.+X.VXdt+total.cell+emission_O2+rab+Thr+His+lactate+SO4.ferm.+PO4.ferm.; 0.572, 0.807, tmp+P-Source.Feed.conc.+Nitrogen.Conc.+Lys_conc.+X.VXdt+total.Vol+emission_O2+rab+Thr+lactate+SO4.ferm.+PO4.ferm.; 0.564, 0.807, pH+tmp+Main.Thr.Conc.+Nitrogen.Conc.+OD+Lys_conc.+X.F.Suc+X.VXdt+total.cell+emission_O2+rab+lactate+PO4.ferm.; 0.572, 0.807, tmp+P-Source.Feed.conc.+Nitrogen.Conc.+Lys_conc.+X.VXdt+total.Vol+emission_O2+rab+Thr+lactate+PO4.ferm.+PO4.utilise; 0.595, 0.807, tmp+Main.Thr.Conc.+OD+Lys_conc.+X.VXdt+total.cell+Thr+His+PO4.ferm.; 0.580, 0.807, tmp+P-Source.Feed.conc.+Nitrogen.Conc.+Lys_conc.+X.F.Suc+X.VXdt+total.Vol+emission_O2+rab+lactate+PO4.ferm.; 0.564, 0.807, Nitrogen.Conc.+Lys_conc.+X.F.Suc+X.VXdt+total.Vol+yield+PL+emission_O2+rab+Thr+lactate+PO4.ferm.+PO4.apporte; 0.572, 0.807, Nitrogen.Conc.+Lys_conc.+X.VXdt+total.Vol+yield+emission_O2+rab+Thr+His+lactate+PO4.ferm.+PO4.utilise; 0.546, 0.807, pH+tmp+Main.Thr.Conc.+Nitrogen.Conc.+Lys_conc.+X.VXdt+total.Vol+PL+emission_O2+rab+Thr+lactate+PO4.ferm.+PO4.apporte+PO4.utilise; 0.587, 0.807, tmp+Main.Thr.Conc.+OD+Lys_conc.+X.VXdt+total.cell+emission_O2+rab+Thr+PO4.ferm.; 0.572, 0.807, tmp+Main.Thr.Conc.+Nitrogen.Conc.+OD+Lys_conc.+X.F.Suc+X.VXdt+total.cell+PL+Thr+lactate+PO4.ferm.; 0.555, 0.807, pH+tmp+Main.P-Source.Conc.+P-Source.Feed.conc.+Nitrogen.Conc.+Lys_conc.+X.VXdt+total.Vol+total.cell+emission_O2+rab+Thr+lactate+PO4.ferm.; 0.595, 0.807, tmp+Nitrogen.Conc.+Lys_conc.+X.F.Suc+X.VXdt+total. Vol+His+lactate+PO4.ferm.; 0.572, 0.807, tmp+Main.P-Source.Conc.+Nitrogen.Conc.+OD+Lys_conc.+X.VXdt+ total.Vol+emission_O2+rab+Thr+lactate+PO4.ferm.; 0.587, 0.807, pH+tmp+Main.Thr.Conc.+OD+Lys_conc.+X.VXdt+ total.cell+Thr+lactate+PO4.ferm.; 0.563, 0.807, pH+Nitrogen.Conc.+Lys_conc.+X.F.Suc+X.VXdt+total.Vol+yield+ emission_O2+rab+Thr+lactate+PO4.ferm.+PO4.apporte; 0.587, 0.807, pH+tmp+OD+Lys_conc.+X.F.Suc+X.VXdt+ total.cell+emission_O2+rab+PO4.ferm.; 0.563, 0.807, pH+tmp+Main.Thr.Conc.+OD+Lys_conc.+X.VXdt+total. Vol+total.cell+emission_O2+rab+Thr+lactate+PO4.ferm.; 0.563, 0.807, pH+tmp+P-Source.Feed.conc.+Nitrogen. Conc.+Lys_conc.+X.VXdt+total.Vol+total.cell+PL+emission_O2+rab+lactate+PO4.ferm.; 0.555, 0.807, pH+tmp+ Nitrogen.Conc.+OD+Lys_conc.+X.F.Suc+X.VXdt+total. Vol+emission_O2+rab+Thr+His+lactate+PO4.ferm.; 0.555, 0.807, pH+tmp+Nitrogen.Conc.+OD+Lys_conc.+X.VXdt+ total.Vol+emission_O2+rab+Thr+His+lactate+SO4.ferm.+ PO4.ferm.; 0.546, 0.807, pH+tmp+Main.Thr.Conc.+Nitrogen.Conc.+OD+Lys_conc.+X.VXdt+total.Vol+PL+ emission_O2+rab+Thr+His+lactate+PO4.ferm.; 0.587, 0.807, pH+tmp+Main.Thr.Conc.+Lys_conc.+X.VXdt+total. Vol+emission_O2+rab+lactate+PO4.ferm.; 0.572, 0.807, Nitrogen.Conc.+Lys_conc.+X.VXdt+total.Vol+yield+PL+ emission_O2+rab+Thr+His+lactate+PO4.utilise; 0.580, 0.807, tmp+Nitrogen.Conc.+Lys_conc.+X.F.Suc+X.VXdt+ total.Vol+emission_O2+rab+His+lactate+PO4.ferm.; 0.555, 0.807, pH+tmp+Nitrogen.Conc.+Lys_conc.+X.F.Suc+X. VXdt+total.Vol+total.cell+emission_O2+rab+Thr+lactate+ SO4.ferm.+PO4.ferm.; 0.563, 0.807, pH+tmp+Main.P-Source.Conc.+Nitrogen.Conc.+OD+Lys_conc.+X.VXdt+ total.Vol+emission_O2+rab+His+lactate+PO4.ferm.; 0.563, 0.807, pH+tmp+Main.Thr.Conc.+Nitrogen.Conc.+Lys_ conc.+X.VXdt+total.Vol+emission_O2+rab+Thr+lactate+ PO4.ferm.+PO4.utilise; 0.587, 0.807, tmp+Main.Thr. Conc.+Nitrogen.Conc.+OD+Lys_conc.+X.VXdt+total. cell+PL+Thr+PO4.ferm.; 0.563, 0.807, pH+tmp+Main.P-Source.Conc.+P-Source.Feed.conc.+Nitrogen.Conc.+Lys_ conc.+X.F.Suc+X.VXdt+total.Vol+emission_O2+rab+ lactate+PO4.ferm.; 0.563, 0.807, pH+tmp+P-Source.Feed. conc.+Nitrogen.Conc.+Lys_conc.+X.VXdt+total.Vol+ emission_O2+rab+Thr+lactate+PO4.ferm.+PO4.apporte; 0.555, 0.807, tmp+Main.Thr.Conc.+Nitrogen.Conc.+Lys_ conc.+X.VXdt+total.Vol+yield+emission_O2+rab+Thr+ His+lactate+PO4.ferm.+PO4.apporte; 0.594, 0.807, tmp+ OD+Lys_conc.+X.VXdt+total.cell+PL+Thr+SO4.ferm.+ PO4.ferm.; 0.571, 0.807, Main.Thr.Conc.+Nitrogen.Conc.+ Lys_conc.+X.VXdt+total.Vol+yield+emission_O2+rab+ Thr+His+lactate+PO4.utilise; 0.563, 0.807, tmp+Nitrogen. Conc.+Lys_conc.+X.VXdt+total.Vol+yield+PL+emission_ O2+rab+Thr+PO4.ferm.+PO4.apporte+PO4.utilise; 0.563, 0.807, pH+tmp+Main.P-Source.Conc.+Main.Thr.Conc.+ OD+Lys_conc.+X.VXdt+total.cell+emission_O2+rab+ Thr+lactate+PO4.ferm.; 0.602, 0.807, tmp+Nitrogen. Conc.+OD+Lys_conc.+X.F.Suc+X.VXdt+total.cell+PO4. ferm.; 0.587, 0.807, tmp+Main.P-Source.Conc.+OD+Lys_ conc.+X.VXdt+total.cell+PL+Thr+lactate+PO4.ferm.; 0.563, 0.807, pH+tmp+Main.Thr.Conc.+OD+Lys_conc.+X. F.Suc+X.VXdt+total.cell+emission_O2+rab+Thr+lactate+ PO4.ferm.; 0.555, 0.807, pH+tmp+Main.Thr.Conc.+Nitrogen.Conc.+Lys_conc.+X.VXdt+total.Vol+yield+emission_ O2+rab+Thr+lactate+PO4.ferm.+PO4.apporte; 0.594, 0.807, tmp+OD+Lys_conc.+X.VXdt+total.cell+PL+emission_O2+Thr+PO4.ferm.; 0.555, 0.807, pH+tmp+Main.P-Source.Conc.+P-Source.Feed.conc.+Nitrogen.Conc.+Lys_ conc.+X.VXdt+total.Vol+emission_O2+rab+Thr+His+ lactate+PO4.ferm.; 0.555, 0.807, tmp+Main.Thr.Conc.+ Nitrogen.Conc.+Lys_conc.+X.VXdt+total.Vol+yield+PL+ emission_O2+rab+Thr+lactate+PO4.ferm.+PO4.apporte; 0.579, 0.807, pH+tmp+Main.Thr.Conc.+OD+Lys_conc.+X. VXdt+total.cell+PL+Thr+lactate+PO4.ferm.; 0.555, 0.807, pH+tmp+Nitrogen.Conc.+OD+Lys_conc.+X.F.Suc+X. VXdt+total.Vol+PL+emission_O2+rab+Thr+lactate+PO4. ferm.; 0.546, 0.807, pH+tmp+Main.Thr.Conc.+Nitrogen. Conc.+Lys_conc.+X.VXdt+total.Vol+yield+emission_O2+ rab+Thr+lactate+PO4.ferm.+PO4.apporte+PO4.utilise; 0.571, 0.807, tmp+Main.Thr.Conc.+Nitrogen.Conc.+OD+ Lys_conc.+X.VXdt+total.cell+Thr+His+lactate+SO4. ferm.+PO4.ferm.; 0.563, 0.807, pH+tmp+Main.P-Source. Conc.+Nitrogen.Conc.+Lys_conc.+X.F.Suc+X.VXdt+total. Vol+emission_O2+rab+Thr+lactate+PO4.ferm.; 0.555, 0.807, pH+tmp+OD+Lys_conc.+X.VXdt+total.cell+PL+ emission_O2+rab+Thr+His+lactate+SO4.ferm.+PO4.ferm.; 0.555, 0.807, tmp+Nitrogen.Conc.+OD+Lys_conc.+X.F. Suc+X.VXdt+total.Vol+total.cell+emission_O2+rab+Thr+ His+lactate+PO4.ferm.; 0.563, 0.806, tmp+Nitrogen.Conc.+ Lys_conc.+X.VXdt+total.Vol+total.cell+PL+emission_O2+ rab+Thr+lactate+SO4.ferm.+PO4.ferm.; 0.546, 0.806, pH+tmp+Main.P-Source.Conc.+Nitrogen.Conc.+OD+Lys_ conc.+X.F.Suc+X.VXdt+total.cell+PL+emission_O2+rab+ Thr+lactate+PO4.ferm.; 0.571, 0.806, tmp+Nitrogen. Conc.+OD+Lys_conc.+X.VXdt+total.Vol+emission_O2+ rab+Thr+lactate+SO4.ferm.+PO4.ferm.; 0.571, 0.806, pH+tmp+Main.Thr.Conc.+Lys_conc.+X.VXdt+total.Vol+ total.cell+emission_O2+rab+Thr+lactate+PO4.ferm.; 0.563, 0.806, pH+tmp+Nitrogen.Conc.+OD+Lys_conc.+X.VXdt+ total.Vol+total.cell+PL+emission_O2+rab+Thr+PO4.ferm.; 0.587, 0.806, pH+tmp+Nitrogen.Conc.+OD+Lys_conc.+X. VXdt+total.cell+emission_O2+rab+PO4.ferm.; 0.587, 0.806, tmp+Lys_conc.+X.VXdt+total.Vol+PL+emission_ O2+rab+Thr+lactate+PO4.ferm.; 0.608, 0.806, tmp+OD+ Lys_conc.+X.F.Suc+X.VXdt+total.cell+PO4.ferm.; 0.545, 0.806, tmp+Nitrogen.Conc.+Lys_conc.+X.F.Suc+X.VXdt+ total.Vol+yield+PL+emission_O2+rab+Thr+lactate+PO4. ferm.+PO4.apporte+PO4.utilise; 0.587, 0.806, tmp+Main. Thr.Conc.+OD+Lys_conc.+X.VXdt+total.cell+PL+Thr+ His+PO4.ferm.; 0.563, 0.806, pH+tmp+Main.Thr.Conc.+ OD+Lys_conc.+X.VXdt+total.Vol+PL+emission_O2+rab+ Thr+lactate+PO4.ferm.; 0.554, 0.806, pH+tmp+Main.P-Source.Conc.+P-Source.Feed.conc.+Nitrogen.Conc.+Lys_ conc.+X.VXdt+total.Vol+total.cell+emission_O2+rab+His+ lactate+PO4.ferm.; 0.554, 0.806, pH+tmp+Main.P-Source. Conc.+Main.Thr.Conc.+Nitrogen.Conc.+Lys_conc.+X. VXdt+total.Vol+total.cell+emission_O2+rab+Thr+lactate+ PO4.ferm.; 0.571, 0.806, pH+tmp+Main.P-Source.Conc.+ Nitrogen.Conc.+OD+Lys_conc.+X.VXdt+total.cell+ emission_O2+rab+Thr+PO4.ferm.; 0.563, 0.806, tmp+ Nitrogen.Conc.+Lys_conc.+X.VXdt+total.Vol+yield+ emission_O2+rab+His+lactate+PO4.ferm.+PO4.apporte+ PO4.utilise; 0.563, 0.806, tmp+Nitrogen.Conc.+Lys_conc.+ X.VXdt+total.Vol+yield+PL+emission_O2+Thr+lactate+ PO4.ferm.+PO4.apporte+PO4.utilise; 0.571, 0.806, pH+tmp+Main.Thr.Conc.+Nitrogen.Conc.+OD+Lys_ conc.+X.VXdt+total.cell+PL+Thr+lactate+PO4.ferm.; 0.563, 0.806, P-Source.Feed.conc.+Nitrogen.Conc.+Lys_ conc.+X.F.Suc+X.VXdt+total.Vol+yield+emission_O2+ rab+Thr+lactate+PO4.ferm.+PO4.apporte; 0.545, 0.806, Main.Thr.Conc.+Nitrogen.Conc.+Lys_conc.+X.F.Suc+X. VXdt+total.Vol+yield+PL+emission_O2+rab+Thr+lactate+ PO4.ferm.+PO4.apporte+PO4.utilise; 0.563, 0.806, tmp+ Nitrogen.Conc.+OD+Lys_conc.+X.VXdt+total.Vol+PL+ emission_O2+rab+Thr+His+lactate+PO4.ferm.; 0.563, 0.806, pH+tmp+Nitrogen.Conc.+Lys_conc.+X.F.Suc+X.

VXdt+total.Vol+emission_O2+rab+Thr+lactate+SO4. ferm.+PO4.ferm.; 0.563, 0.806, pH+tmp+P-Source.Feed. conc.+Nitrogen.Conc.+Lys_conc.+X.VXdt+total.Vol+ emission_O2+rab+His+lactate+SO4.ferm.+PO4.ferm.; 0.545, 0.806, pH+tmp+Main.Thr.Conc.+Nitrogen.Conc.+ OD+Lys_conc.+X.F.Suc+X.VXdt+total.cell+emission_O2+ rab+Thr+lactate+SO4.ferm.+PO4.ferm.; 0.594, 0.806, pH+tmp+Lys_conc.+X.VXdt+total.Vol+emission_O2+rab+ lactate+PO4.ferm.; 0.563, 0.806, pH+tmp+P-Source.Feed. conc.+Nitrogen.Conc.+OD+Lys_conc.+X.F.Suc+X.VXdt+ total.Vol+emission_O2+rab+lactate+PO4.ferm.; 0.545, 0.806, pH+tmp+P-Source.Feed.conc.+Nitrogen.Conc.+ OD+Lys_conc.+X.VXdt+total.Vol+total.cell+emission_ O2+rab+Thr+lactate+SO4.ferm.+PO4.ferm.; 0.563, 0.806, pH+tmp+P-Source.Feed.conc.+Main.Thr.Conc.+Nitrogen. Conc.+Lys_conc.+X.VXdt+total.Vol+PL+emission_O2+ rab+lactate+PO4.ferm.; 0.545, 0.806, pH+tmp+P-Source. Feed.conc.+Main.Thr.Conc.+Nitrogen.Conc.+OD+Lys_ conc.+X.VXdt+total.cell+PL+emission_O2+rab+Thr+ lactate+PO4.ferm.; 0.554, 0.806, pH+tmp+P-Source.Feed. conc.+Nitrogen.Conc.+OD+Lys_conc.+X.VXdt+total.cell+ emission_O2+rab+Thr+lactate+SO4.ferm.+PO4.ferm.; 0.536, 0.806, tmp+Main.Thr.Conc.+Nitrogen.Conc.+Lys_ conc.+X.VXdt+total.Vol+yield+PL+emission_O2+rab+ Thr+lactate+SO4.ferm.+PO4.ferm.+PO4.apporte+PO4.utilise; 0.562, 0.806, pH+tmp+Main.Thr.Conc.+OD+Lys_ conc.+X.VXdt+total.cell+emission_O2+rab+Thr+lactate+ SO4.ferm.+PO4.ferm.; 0.601, 0.806, pH+tmp+OD+Lys_ conc.+X.VXdt+total.cell+Thr+PO4.ferm.; 0.562, 0.806, tmp+Main.Thr.Conc.+Nitrogen.Conc.+OD+Lys_conc.+X. VXdt+total.cell+emission_O2+rab+Thr+lactate+SO4. ferm.+PO4.ferm.; 0.554, 0.806, pH+tmp+P-Source.Feed. conc.+Main.Thr.Conc.+Nitrogen.Conc.+Lys_conc.+X. VXdt+total.Vol+yield+emission_O2+rab+Thr+lactate+ PO4.ferm.; 0.586, 0.806, tmp+P-Source.Feed.conc.+OD+ Lys_conc.+X.VXdt+total.cell+emission_O2+rab+Thr+ PO4.ferm.; 0.562, 0.806, pH+tmp+Nitrogen.Conc.+Lys_ conc.+X.VXdt+total.Vol+PL+emission_O2+rab+His+ lactate+SO4.ferm.+PO4.ferm.; 0.545, 0.806, pH+tmp+ Main.Thr.Conc.+Nitrogen.Conc.+Lys_conc.+X.VXdt+ total.Vol+yield+PL+emission_O2+rab+Thr+lactate+PO4. ferm.+PO4.apporte; 0.554, 0.806, pH+Nitrogen.Conc.+ Lys_conc.+X.F.Suc+X.VXdt+total.Vol+yield+emission_ O2+rab+Thr+lactate+PO4.ferm.+PO4.apporte+PO4.utilise; 0.554, 0.806, P-Source.Feed.conc.+Nitrogen.Conc.+Lys_ conc.+X.VXdt+total.Vol+yield+PL+emission_O2+rab+ Thr+His+lactate+PO4.ferm.+PO4.apporte; 0.579, 0.806, tmp+Main.Thr.Conc.+Lys_conc.+X.VXdt+total.Vol+total. cell+emission_O2+rab+Thr+lactate+PO4.ferm.; 0.562, 0.806, pH+tmp+Nitrogen.Conc.+Lys_conc.+X.F.Suc+X. VXdt+total.Vol+emission_O2+rab+Thr+lactate+PO4. ferm.+PO4.apporte; 0.594, 0.806, pH+tmp+Nitrogen. Conc.+OD+Lys_conc.+X.F.Suc+X.VXdt+total.cell+PO4. ferm.; 0.554, 0.806, pH+tmp+P-Source.Feed.conc.+ Nitrogen.Conc.+OD+Lys_conc.+X.F.Suc+X.VXdt+total. Vol+total.cell+emission_O2+rab+lactate+PO4.ferm.; 0.579, 0.806, tmp+Nitrogen.Conc.+Lys_conc.+X.F.Suc+X.VXdt+ total.Vol+total.cell+emission_O2+rab+lactate+PO4.ferm.; 0.601, 0.806, tmp+Nitrogen.Conc.+OD+Lys_conc.+X. VXdt+total.cell+lactate+PO4.ferm.; 0.571, 0.806, pH+tmp+ P-Source.Feed.conc.+Nitrogen.Conc.+Lys_conc.+X.VXdt+ total.Vol+emission_O2+rab+lactate+PO4.ferm.+PO4. apporte; 0.562, 0.806, pH+Nitrogen.Conc.+Lys_conc.+X. VXdt+total.Vol+yield+emission_O2+rab+Thr+His+ lactate+PO4.ferm.+PO4.apporte; 0.554, 0.806, pH+tmp+ Main.P-Source.Conc.+P-Source.Feed.conc.+Main.Thr. Conc.+Nitrogen.Conc.+Lys_conc.+X.VXdt+total.Vol+ emission_O2+rab+Thr+lactate+PO4.ferm.; 0.562, 0.806, pH+tmp+Main.Thr.Conc.+Nitrogen.Conc.+OD+Lys_ conc.+X.VXdt+total.Vol+emission_O2+rab+His+lactate+ PO4.ferm.; 0.554, 0.806, pH+tmp+P-Source.Feed.conc.+ Nitrogen.Conc.+Lys_conc.+X.VXdt+total.Vol+PL+ emission_O2+rab+Thr+lactate+PO4.ferm.+PO4.apporte; 0.562, 0.806, pH+tmp+Main.Thr.Conc.+Nitrogen.Conc.+ Lys_conc.+X.VXdt+total.Vol+PL+emission_O2+rab+His+ lactate+PO4.ferm.; 0.554, 0.806, P-Source.Feed.conc.+ Main.Thr.Conc.+Nitrogen.Conc.+Lys_conc.+X.VXdt+ total.Vol+yield+emission_O2+rab+Thr+His+lactate+PO4. ferm.+PO4.apporte; 0.562, 0.806, tmp+Main.Thr.Conc.+ Nitrogen.Conc.+Lys_conc.+X.VXdt+total.cell+ PL+emission_O2+rab+Thr+lactate+PO4.ferm.; 0.562, 0.806, pH+tmp+P-Source.Feed.conc.+Nitrogen.Conc.+ OD+Lys_conc.+X.VXdt+total.Vol+PL+emission_O2+rab+ lactate+PO4.ferm.; 0.570, 0.806, Nitrogen.Conc.+Lys_ conc.+X.F.Suc+X.VXdt+total.Vol+yield+emission_O2+ rab+Thr+lactate+PO4.ferm.+PO4.utilise; 0.601, 0.806, tmp+Nitrogen.Conc.+Lys_conc.+X.VXdt+total.Vol+His+ lactate+PO4.ferm.; 0.554, 0.806, pH+tmp+Main.Thr.Conc.+ Nitrogen.Conc.+OD+Lys_conc.+X.VXdt+total.Vol+emission_O2+rab+Thr+lactate+SO4.ferm.+PO4.ferm.; 0.562, 0.806, tmp+Nitrogen.Conc.+Lys_conc.+X.F.Suc+X.VXdt+ total.Vol+yield+emission_O2+rab+Thr+lactate+PO4. ferm.+PO4.apporte; 0.570, 0.806, pH+tmp+P-Source.Feed. conc.+OD+Lys_conc.+X.VXdt+total.cell+PL+emission_ O2+rab+Thr+PO4.ferm.; 0.578, 0.806, pH+tmp+Nitrogen. Conc.+Lys_conc.+X.VXdt+total.Vol+emission_O2+rab+ lactate+PO4.ferm.+PO4.utilise; 0.570, 0.806, tmp+Lys_ conc.+X.VXdt+total.Vol+PL+emission_O2+rab+Thr+ lactate+PO4.ferm.+PO4.apporte+PO4.utilise; 0.578, 0.806, tmp+Main.P-Source.Conc.+Nitrogen.Conc.+OD+Lys_ conc.+X.VXdt+total.cell+PL+Thr+lactate+PO4.ferm.; 0.570, 0.806, pH+tmp+P-Source.Feed.conc.+Nitrogen. Conc.+OD+Lys_conc.+X.VXdt+total.cell+emission_O2+ rab+Thr+PO4.ferm.; 0.553, 0.806, tmp+P-Source.Feed. conc.+Main.Thr.Conc.+Nitrogen.Conc.+OD+Lys_conc.+X. VXdt+total.Vol+total.cell+emission_O2+rab+Thr+lactate+ PO4.ferm.; 0.570, 0.806, pH+tmp+OD+Lys_conc.+X.F. Suc+X.VXdt+total.cell+emission_O2+rab+Thr+His+PO4. ferm.; 0.545, 0.806, pH+tmp+Main.P-Source.Conc.+ Nitrogen.Conc.+OD+Lys_conc.+X.VXdt+total.Vol+total. cell+emission_O2+rab+Thr+His+lactate+PO4.ferm.; 0.562, 0.806, tmp+P-Source.Feed.conc.+Main.Thr.Conc.+Nitrogen.Conc.+Lys_conc.+X.VXdt+total.Vol+emission_O2+ rab+Thr+His+lactate+PO4.ferm.; 0.562, 0.806, tmp+P-Source.Feed.conc.+Main.Thr.Conc.+Nitrogen.Conc.+Lys_ conc.+X.VXdt+total.Vol+total.cell+emission_O2+rab+ Thr+lactate+PO4.ferm.; 0.562, 0.806, pH+tmp+Main.P-Source.Conc.+Nitrogen.Conc.+OD+Lys_conc.+X.VXdt+ total.cell+PL+emission_O2+rab+Thr+PO4.ferm.; 0.562, 0.806, tmp+Nitrogen.Conc.+Lys_conc.+X.VXdt+total.Vol+ PL+emission_O2+rab+Thr+His+lactate+PO4.ferm.+PO4. apporte; 0.570, 0.806, pH+tmp+Nitrogen.Conc.+Lys_ conc.+X.VXdt+total.Vol+emission_O2+rab+His+lactate+ PO4.ferm.+PO4.apporte; 0.553, 0.806, pH+tmp+Nitrogen. Conc.+Lys_conc.+X.VXdt+total.Vol+yield+PL+emission_ O2+rab+Thr+lactate+PO4.ferm.+PO4.utilise; 0.570, 0.806, tmp+Main.Thr.Conc.+Nitrogen.Conc.+Lys_conc.+X. VXdt+total.Vol+PL+emission_O2+rab+Thr+lactate+PO4. ferm.; 0.570, 0.806, Nitrogen.Conc.+Lys_conc.+X.F.Suc+ X.VXdt+total.Vol+yield+emission_O2+rab+Thr+His+ lactate+PO4.utilise; 0.553, 0.806, tmp+P-Source.Feed. conc.+Nitrogen.Conc.+OD+Lys_conc.+X.F.Suc+X.VXdt+ total.cell+emission_O2+rab+Thr+His+lactate+PO4.ferm.; 0.586, 0.806, tmp+Main.Thr.Conc.+Lys_conc.+X.VXdt+total.Vol+emission_O2+rab+Thr+lactate+PO4.ferm.; 0.586, 0.806, pH+tmp+Lys_conc.+X.VXdt+total.Vol+PL+emission_O2+rab+Thr+PO4.ferm.; 0.553, 0.806, tmp+Main.Thr.Conc.+Nitrogen.Conc.+Lys_conc.+X.VXdt+total.Vol+PL+emission_O2+rab+Thr+lactate+PO4.ferm.+PO4.apporte+PO4.utilise; 0.544, 0.806, tmp+Main.Thr.Conc.+Nitrogen.Conc.+Lys_conc.+X.VXdt+total.Vol+yield+emission_O2+rab+Thr+lactate+SO4.ferm.+PO4.ferm.+PO4.apporte+PO4.utilise; 0.553, 0.806, pH+tmp+Main.Thr.Conc.+Nitrogen.Conc.+OD+Lys_conc.+X.VXdt+total.Vol+emission_O2+rab+Thr+His+lactate+PO4.ferm.; 0.562, 0.806, pH+tmp+Main.P-Source.Conc.+Nitrogen.Conc.+OD+Lys_conc.+X.F.Suc+X.VXdt+total.Vol+emission_O2+rab+lactate+PO4.ferm.; 0.544, 0.806, pH+Nitrogen.Conc.+Lys_conc.+X.VXdt+total.Vol+yield+PL+emission_O2+rab+Thr+His+lactate+PO4.ferm.+PO4.apporte+PO4.utilise; 0.562, 0.806, pH+tmp+Nitrogen.Conc.+OD+Lys_conc.+X.VXdt+total.cell+PL+emission_O2+rab+Thr+SO4.ferm.+PO4.ferm.; 0.553, 0.806, pH+tmp+P-Source.Feed.conc.+Nitrogen.Conc.+Lys_conc.+X.VXdt+total.Vol+total.cell+emission_O2+rab+Thr+lactate+SO4.ferm.+PO4.ferm.; 0.586, 0.806, tmp+OD+Lys_conc.+X.VXdt+total.Vol+emission_O2+rab+Thr+lactate+PO4.ferm.; 0.570, 0.806, tmp+Main.P-Source.Conc.+Main.Thr.Conc.+OD+Lys_conc.+X.VXdt+total.cell+emission_O2+rab+Thr+lactate+PO4.ferm.; 0.553, 0.806, tmp+Main.P-Source.Conc.+P-Source.Feed.conc.+Nitrogen.Conc.+OD+Lys_conc.+X.VXdt+total.cell+emission_O2+rab+Thr+His+lactate+PO4.ferm.; 0.562, 0.806, tmp+P-Source.Feed.conc.+Nitrogen.Conc.+Lys_conc.+X.VXdt+total.Vol+PL+emission_O2+rab+Thr+His+lactate+PO4.ferm.; 0.578, 0.806, pH+tmp+OD+Lys_conc.+X.F.Suc+X.VXdt+total.cell+emission_O2+rab+lactate+PO4.ferm.; 0.553, 0.806, pH+tmp+Nitrogen.Conc.+Lys_conc.+X.VXdt+total.Vol+emission_O2+rab+Thr+His+lactate+PO4.ferm.+PO4.apporte+PO4.utilise; 0.578, 0.806, tmp+OD+Lys_conc.+X.F.Suc+X.VXdt+total.cell+PL+Thr+His+lactate+PO4.ferm.; 0.553, 0.806, pH+Nitrogen.Conc.+Lys_conc.+X.VXdt+total.Vol+yield+emission_O2+rab+Thr+His+lactate+PO4.ferm.+PO4.apporte+PO4.utilise; 0.570, 0.806, tmp+Nitrogen.Conc.+Lys_conc.+X.VXdt+total.Vol+yield+emission_O2+rab+Thr+lactate+PO4.apporte+PO4.utilise; 0.585, 0.806, tmp+OD+Lys_conc.+X.VXdt+total.cell+PL+rab+Thr+lactate+PO4.ferm.; 0.561, 0.806, tmp+Main.Thr.Conc.+Nitrogen.Conc.+Lys_conc.+X.VXdt+total.Vol+yield+emission_O2+rab+Thr+lactate+PO4.ferm.+PO4.utilise; 0.578, 0.806, tmp+Lys_conc.+X.VXdt+total.Vol+total.cell+emission_O2+rab+Thr+His+lactate+PO4.ferm.; 0.570, 0.806, tmp+Lys_conc.+X.VXdt+total.Vol+total.cell+PL+emission_O2+rab+Thr+His+lactate+PO4.ferm.; 0.553, 0.806, pH+tmp+Main.P-Source.Conc.+P-Source.Feed.conc.+Main.Thr.Conc.+Nitrogen.Conc.+Lys_conc.+X.VXdt+total.Vol+emission_O2+rab+His+lactate+PO4.ferm.; 0.578, 0.806, tmp+Main.P-Source.Conc.+Nitrogen.Conc.+OD+Lys_conc.+X.VXdt+total.cell+emission_O2+rab+Thr+PO4.ferm.; 0.570, 0.806, P-Source.Feed.conc.+Nitrogen.Conc.+Lys_conc.+X.VXdt+total.Vol+yield+emission_O2+rab+Thr+lactate+PO4.apporte+PO4.utilise; 0.561, 0.806, tmp+Main.P-Source.Conc.+P-Source.Feed.conc.+Nitrogen.Conc.+Lys_conc.+X.VXdt+total.Vol+PL+emission_O2+rab+Thr+lactate+PO4.ferm.; 0.561, 0.806, tmp+Nitrogen.Conc.+Lys_conc.+X.VXdt+total.Vol+yield+PL+emission_O2+rab+Thr+lactate+PO4.ferm.+PO4.utilise; 0.561, 0.806, tmp+Main.P-Source.Conc.+P-Source.Feed.conc.+Nitrogen.Conc.+OD+Lys_conc.+X.VXdt+total.Vol+emission_O2+rab+Thr+lactate+PO4.ferm.; 0.570, 0.806, Nitrogen.Conc.+Lys_conc.+X.VXdt+total.Vol+yield+PL+emission_O2+rab+Thr+lactate+PO4.ferm.+PO4.utilise; 0.553, 0.806, pH+tmp+Main.P-Source.Conc.+P-Source.Feed.conc.+Nitrogen.Conc.+OD+Lys_conc.+X.VXdt+total.Vol+emission_O2+rab+His+lactate+PO4.ferm.; 0.561, 0.806, pH+tmp+Main.Thr.Conc.+Nitrogen.Conc.+Lys_conc.+X.F.Suc+X.VXdt+total.Vol+emission_O2+rab+Thr+lactate+PO4.ferm.; 0.561, 0.806, Main.Thr.Conc.+Nitrogen.Conc.+Lys_conc.+X.VXdt+total.Vol+yield+PL+emission_O2+Thr+lactate+PO4.ferm.+PO4.apporte+PO4.utilise; 0.525, 0.806, pH+tmp+Main.Thr.Conc.+Nitrogen.Conc.+Lys_conc.+X.VXdt+total.Vol+yield+PL+emission_O2+rab+Thr+His+lactate+PO4.ferm.+PO4.apporte+PO4.utilise; 0.544, 0.806, pH+tmp+Nitrogen.Conc.+Lys_conc.+X.VXdt+total.Vol+yield+PL+emission_O2+rab+Thr+His+lactate+PO4.ferm.+PO4.apporte; 0.577, 0.806, tmp+Main.Thr.Conc.+OD+Lys_conc.+X.F.Suc+X.VXdt+total.cell+PL+Thr+lactate+PO4.ferm.; 0.561, 0.806, pH+P-Source.Feed.conc.+Nitrogen.Conc.+OD+Lys_conc.+X.VXdt+total.cell+emission_O2+rab+Thr+His+lactate+PO4.ferm.; 0.592, 0.805, tmp+Lys_conc.+X.VXdt+total.Vol+emission_O2+rab+Thr+lactate+PO4.ferm.; 0.577, 0.805, tmp+Nitrogen.Conc.+OD+Lys_conc.+X.VXdt+total.Vol+total.cell+PL+Thr+lactate+PO4.ferm.; 0.543, 0.805, P-Source.Feed.conc.+Nitrogen.Conc.+Lys_conc.+X.VXdt+total.Vol+yield+PL+emission_O2+rab+Thr+His+lactate+PO4.ferm.+PO4.apporte+PO4.utilise; 0.577, 0.805, tmp+Nitrogen.Conc.+Lys_conc.+X.VXdt+total.Vol+total.cell+emission_O2+rab+His+lactate+PO4.ferm.; 0.552, 0.805, pH+tmp+Main.P-Source.Conc.+Main.Thr.Conc.+OD+Lys_conc.+X.VXdt+total.cell+PL+emission_O2+rab+Thr+lactate+PO4.ferm.; 0.585, 0.805, pH+tmp+Nitrogen.Conc.+OD+Lys_conc.+X.VXdt+total.cell+PL+Thr+PO4.ferm.; 0.577, 0.805, tmp+P-Source.Feed.conc.+Nitrogen.Conc.+OD+Lys_conc.+X.VXdt+total.cell+emission_O2+rab+Thr+PO4.ferm.; 0.552, 0.805, tmp+P-Source.Feed.conc.+Nitrogen.Conc.+Lys_conc.+X.VXdt+total.Vol+yield+PL+emission_O2+rab+Thr+lactate+PO4.ferm.+PO4.apporte; 0.561, 0.805, pH+tmp+Main.P-Source.Conc.+P-Source.Feed.conc.+Nitrogen.Conc.+Lys_conc.+X.VXdt+total.Vol+PL+emission_O2+rab+lactate+PO4.ferm.; 0.561, 0.805, tmp+Nitrogen.Conc.+Lys_conc.+X.VXdt+total.Vol+yield+emission_O2+rab+Thr+His+lactate+PO4.ferm.+PO4.utilise; 0.569, 0.805, tmp+Nitrogen.Conc.+Lys_conc.+X.VXdt+total.Vol+PL+emission_O2+rab+Thr+lactate+SO4.ferm.+PO4.ferm.; 0.561, 0.805, P-Source.Feed.conc.+Main.Thr.Conc.+Nitrogen.Conc.+Lys_conc.+X.VXdt+total.Vol+yield+emission_O2+rab+Thr+lactate+PO4.ferm.+PO4.utilise; 0.552, 0.805, tmp+Main.P-Source.Conc.+Nitrogen.Conc.+OD+Lys_conc.+X.F.Suc+X.VXdt+total.cell+emission_O2+rab+Thr+His+lactate+PO4.ferm.; 0.534, 0.805, pH+tmp+P-Source.Feed.conc.+Main.Thr.Conc.+Nitrogen.Conc.+OD+Lys_conc.+X.VXdt+total.Vol+total.cell+PL+emission_O2+rab+Thr+lactate+PO4.ferm.; 0.606, 0.805, tmp+Nitrogen.Conc.+OD+Lys_conc.+X.VXdt+total.cell+PO4.ferm.; 0.577, 0.805, tmp+Main.Thr.Conc.+OD+Lys_conc.+X.VXdt+total.cell+Thr+His+lactate+SO4.ferm.+PO4.ferm.; 0.569, 0.805, tmp+Main.Thr.Conc.+Nitrogen.Conc.+OD+Lys_conc.+X.VXdt+total.cell+PL+emission_O2+Thr+lactate+PO4.ferm.; 0.569, 0.805, tmp+Main.Thr.Conc.+OD+Lys_conc.+X.VXdt+total.cell+emission_O2+rab+Thr+lactate+SO4.ferm.+PO4.ferm.; 0.577, 0.805, tmp+Main.P-Source.Conc.+Nitrogen.Conc.+OD+Lys_conc.+X.VXdt+total.cell+Thr+His+lactate+PO4.ferm.; 0.569, 0.805, pH+tmp+Nitrogen.Conc.+OD+Lys_conc.+X.F.Suc+X.VXdt+total.cell+PL+Thr+lactate+PO4.ferm.; 0.592, 0.805, tmp+OD+Lys_conc.+X.F.Suc+X.VXdt+total.cell+Thr+His+PO4.ferm.; 0.599, 0.805, pH+tmp+Lys_conc.+X.

VXdt+total.Vol+emission_O2+rab+PO4.ferm.; 0.577, 0.805, tmp+P-Source.Feed.conc.+Nitrogen.Conc.+Lys_conc.+X.VXdt+total.Vol+yield+emission_O2+rab+lactate+PO4.ferm.; 0.561, 0.805, pH+tmp+Main.Thr.Conc.+OD+Lys_conc.+X.VXdt+total.cell+PL+emission_O2+rab+Thr+His+PO4.ferm.; 0.569, 0.805, tmp+Lys_conc.+X.VXdt+total.Vol+yield+PL+emission_O2+rab+Thr+PO4.ferm.+PO4.apporte+PO4.utilise; 0.561, 0.805, tmp+Nitrogen.Conc.+Lys_conc.+X.VXdt+total.Vol+yield+emission_O2+rab+Thr+lactate+SO4.ferm.+PO4.ferm.+PO4.apporte; 0.569, 0.805, pH+tmp+Nitrogen.Conc.+Lys_conc.+X.VXdt+total.Vol+total.cell+emission_O2+rab+lactate+SO4.ferm.+PO4.ferm.; 0.577, 0.805, tmp+Main.Thr.Conc.+OD+Lys_conc.+X.F.Suc+X.VXdt+total.cell+Thr+His+lactate+PO4.ferm.; 0.561, 0.805, tmp+P-Source.Feed.conc.+Nitrogen.Conc.+Lys_conc.+X.VXdt+total.Vol+yield+emission_O2+rab+Thr+lactate+PO4.ferm.+PO4.utilise; 0.569, 0.805, tmp+P-Source.Feed.conc.+Main.Thr.Conc.+Nitrogen.Conc.+Lys_conc.+X.VXdt+total.Vol+emission_O2+rab+His+lactate+PO4.ferm.; 0.552, 0.805, P-Source.Feed.conc.+Main.Thr.Conc.+Nitrogen.Conc.+Lys_conc.+X.VXdt+total.Vol+yield+emission_O2+rab+Thr+lactate+PO4.ferm.+PO4.apporte+PO4.utilise; 0.569, 0.805, tmp+Nitrogen.Conc.+OD+Lys_conc.+X.F.Suc+X.VXdt+total.cell+PL+Thr+lactate+SO4.ferm.+PO4.ferm.; 0.552, 0.805, tmp+Nitrogen.Conc.+OD+Lys_conc.+X.F.Suc+X.VXdt+total.cell+PL+emission_O2+rab+Thr+His+lactate+PO4.ferm.; 0.561, 0.805, pH+tmp+Main.Thr.Conc.+Nitrogen.Conc.+Lys_conc.+X.VXdt+total.Vol+emission_O2+rab+His+lactate+SO4.ferm.+PO4.ferm.; 0.585, 0.805, tmp+Main.P-Source.Conc.+Main.Thr.Conc.+OD+Lys_conc.+X.VXdt+total.cell+Thr+lactate+PO4.ferm.; 0.599, 0.805, tmp+Main.Thr.Conc.+Nitrogen.Conc.+Lys_conc.+X.VXdt+total.Vol+lactate+PO4.ferm.; 0.552, 0.805, P-Source.Feed.conc.+Main.Thr.Conc.+Nitrogen.Conc.+Lys_conc.+X.VXdt+total.Vol+yield+PL+emission_O2+rab+Thr+lactate+PO4.ferm.+PO4.apporte; 0.552, 0.805, pH+tmp+Main.P-Source.Conc.+Main.Thr.Conc.+Nitrogen.Conc.+Lys_conc.+X.VXdt+total.Vol+PL+emission_O2+rab+Thr+lactate+PO4.ferm.; 0.561, 0.805, tmp+Nitrogen.Conc.+Lys_conc.+X.F.Suc+X.VXdt+total.Vol+total.cell+emission_O2+rab+Thr+His+lactate+PO4.ferm.; 0.577, 0.805, pH+tmp+P-Source.Feed.conc.+OD+Lys_conc.+X.VXdt+total.cell+emission_O2+rab+Thr+PO4.ferm.; 0.561, 0.805, pH+tmp+Main.Thr.Conc.+OD+Lys_conc.+X.VXdt+total.cell+PL+emission_O2+rab+Thr+304.ferm.+PO4.ferm.; 0.569, 0.805, tmp+Main.Thr.Conc.+OD+Lys_conc.+X.VXdt+total.Vol+total.cell+emission_O2+rab+Thr+lactate+PO4.ferm.; 0.569, 0.805, pH+tmp+Nitrogen.Conc.+Lys_conc.+X.VXdt+total.Vol+emission_O2+rab+lactate+PO4.ferm.+PO4.apporte+PO4.utilise; 0.552, 0.805, P-Source.Feed.conc.+Nitrogen.Conc.+Lys_conc.+X.VXdt+total.Vol+yield+emission_O2+rab+Thr+His+lactate+PO4.ferm.+PO4.apporte+PO4.utilise; 0.585, 0.805, pH+tmp+OD+Lys_conc.+X.VXdt+total.cell+emission_O2+rab+lactate+PO4.ferm.; 0.585, 0.805, tmp+Nitrogen.Conc.+OD+Lys_conc.+X.VXdt+total.cell+rab+Thr+lactate+PO4.ferm.; 0.569, 0.805, Main.Thr.Conc.+Nitrogen.Conc.+Lys_conc.+X.VXdt+total.Vol+yield+emission_O2+rab+Thr+lactate+PO4.ferm.+PO4.utilise; 0.561, 0.805, pH+Main.Thr.Conc.+Nitrogen.Conc.+Lys_conc.+X.VXdt+total.Vol+yield+emission_O2+rab+Thr+lactate+PO4.ferm.+PO4.apporte; 0.534, 0.805, pH+tmp+Main.Thr.Conc.+OD+Lys_conc.+X.VXdt+total.cell+PL+emission_O2+rab+Thr+His+lactate+SO4.ferm.+PO4.ferm.; 0.577, 0.805, tmp+Nitrogen.Conc.+OD+Lys_conc.+X.F.Suc+X.VXdt+total.cell+rab+Thr+lactate+PO4.ferm.; 0.569, 0.805, Main.P-Source.Conc.+P-Source.Feed.conc.+Nitrogen.Conc.+OD+Lys_conc.+X.VXdt+total.cell+emission_O2+rab+Thr+lactate+PO4.ferm.; 0.534, 0.805, pH+tmp+Main.P-Source.Conc.+Nitrogen.Conc.+OD+Lys_conc.+X.VXdt+total.cell+PL+emission_O2+rab+Thr+His+lactate+PO4.ferm.; 0.552, 0.805, pH+tmp+Nitrogen.Conc.+Lys_conc.+X.VXdt+total.Vol+PL+emission_O2+rab+Thr+lactate+SO4.ferm.+PO4.ferm.+PO4.apporte; 0.561, 0.805, tmp+P-Source.Feed.conc.+Nitrogen.Conc.+OD+Lys_conc.+X.VXdt+total.cell+emission_O2+rab+Thr+lactate+SO4.ferm.+PO4.ferm.; 0.552, 0.805, tmp+P-Source.Feed.conc.+Nitrogen.Conc.+Lys_conc.+X.VXdt+total.Vol+yield+emission_O2+rab+Thr+His+lactate+PO4.ferm.+PO4.apporte; 0.599, 0.805, tmp+OD+Lys_conc.+X.F.Suc+X.VXdt+total.cell+lactate+PO4.ferm.; 0.552, 0.805, tmp+Main.Thr.Conc.+Nitrogen.Conc.+OD+Lys_conc.+X.VXdt+total.Vol+total.cell+PL+emission_O2+rab+Thr+lactate+PO4.ferm.; 0.552, 0.805, pH+tmp+Main.P-Source.Conc.+Nitrogen.Conc.+Lys_conc.+X.F.Suc+X.VXdt+total.Vol+total.cell+emission_O2+rab+His+lactate+PO4.ferm.; 0.569, 0.805, pH+tmp+Main.Thr.Conc.+Nitrogen.Conc.+OD+Lys_conc.+X.F.Suc+X.VXdt+total.cell+His+lactate+PO4.ferm.; 0.569, 0.805, tmp+OD+Lys_conc.+X.VXdt+total.Vol+total.cell+emission_O2+rab+Thr+His+lactate+PO4.ferm.; 0.560, 0.805, tmp+Main.P-Source.Conc.+Main.Thr.Conc.+Nitrogen.Conc.+OD+Lys_conc.+X.VXdt+total.cell+emission_O2+rab+Thr+lactate+PO4.ferm.; 0.569, 0.805, pH+tmp+Nitrogen.Conc.+OD+Lys_conc.+X.VXdt+total.cell+PL+Thr+His+lactate+PO4.ferm.; 0.560, 0.805, tmp+Main.P-Source.Conc.+Nitrogen.Conc.+Lys_conc.+X.VXdt+total.Vol+total.cell+emission_O2+rab+Thr+His+lactate+PO4.ferm.; 0.569, 0.805, pH+tmp+P-Source.Feed.conc.+Nitrogen.Conc.+OD+Lys_conc.+X.VXdt+total.cell+emission_O2+rab+lactate+PO4.ferm.; 0.577, 0.805, tmp+Nitrogen.Conc.+Lys_conc.+X.VXdt+total.Vol+yield+emission_O2+rab+Thr+lactate+PO4.utilise; 0.560, 0.805, tmp+P-Source.Feed.conc.+Main.Thr.Conc.+Nitrogen.Conc.+Lys_conc.+X.VXdt+total.Vol+PL+emission_O2+rab+Thr+lactate+PO4.ferm.; 0.552, 0.805, pH+tmp+P-Source.Feed.conc.+Main.Thr.Conc.+Nitrogen.Conc.+Lys_conc.+X.VXdt+total.Vol+total.cell+emission_O2+rab+His+lactate+PO4.ferm.; 0.569, 0.805, Nitrogen.Conc.+Lys_conc.+X.VXdt+total.Vol+yield+PL+emission_O2+rab+Thr+PO4.ferm.+PO4.apporte+PO4.utilise; 0.569, 0.805, tmp+Main.P-Source.Conc.+Nitrogen.Conc.+Lys_conc.+X.VXdt+total.Vol+emission_O2+rab+Thr+His+lactate+PO4.ferm.; 0.560, 0.805, P-Source.Feed.conc.+Nitrogen.Conc.+Lys_conc.+X.VXdt+total.Vol+yield+emission_O2+rab+Thr+His+lactate+PO4.ferm.+PO4.utilise; 0.569, 0.805, tmp+Main.P-Source.Conc.+OD+Lys_conc.+X.VXdt+total.cell+emission_O2+rab+Thr+His+lactate+PO4.ferm.; 0.543, 0.805, pH+tmp+P-Source.Feed.conc.+Main.Thr.Conc.+Nitrogen.Conc.+Lys_conc.+X.VXdt+total.cell+PL+emission_O2+rab+Thr+lactate+PO4.ferm.; 0.569, 0.805, pH+Nitrogen.Conc.+Lys_conc.+X.VXdt+total.Vol+yield+PL+emission_O2+rab+Thr+lactate+PO4.utilise; 0.543, 0.805, pH+tmp+Main.P-Source.Conc.+Nitrogen.Conc.+Lys_conc.+X.VXdt+total.Vol+total.cell+PL+emission_O2+rab+Thr+lactate+SO4.ferm.+PO4.ferm.; 0.569, 0.805, pH+tmp+Nitrogen.Conc.+OD+Lys_conc.+X.F.Suc+X.VXdt+total.cell+emission_O2+rab+His+PO4.ferm.; 0.552, 0.805, pH+tmp+Main.P-Source.Conc.+Nitrogen.Conc.+Lys_conc.+X.F.Suc+X.VXdt+total.Vol+total.cell+emission_O2+rab+Thr+lactate+PO4.ferm.; 0.560, 0.805, pH+tmp+P-Source.Feed.conc.+OD+Lys_conc.+X.VXdt+total.cell+PL+emission_O2+rab+Thr+lactate+PO4.ferm.; 0.569, 0.805, tmp+Main.Thr.Conc.+OD+Lys_conc.+X.F.

Suc+X.VXdt+total.cell+emission_O2+rab+Thr+lactate+PO4.ferm.; 0.584, 0.805, tmp+Main.P-Source.Conc.+Nitrogen.Conc.+Lys_conc.+X.VXdt+total.Vol+emission_O2+rab+lactate+PO4.ferm.; 0.552, 0.805, pH+tmp+P-Source.Feed.conc.+Main.Thr.Conc.+Nitrogen.Conc.+Lys_conc.+X.VXdt+total.Vol+emission_O2+rab+Thr+lactate+SO4.ferm.+PO4.ferm.; 0.552, 0.805, pH+tmp+Main.P-Source.Conc.+Nitrogen.Conc.+Lys_conc.+X.VXdt+total.Vol+PL+emission_O2+rab+Thr+His+lactate+PO4.ferm.; 0.543, 0.805, pH+tmp+P-Source.Feed.conc.+Main.Thr.Conc.+Nitrogen.Conc.+Lys_conc.+X.VXdt+total.Vol+PL+emission_O2+rab+Thr+His+lactate+PO4.ferm.; 0.560, 0.805, tmp+Nitrogen.Conc.+Lys_conc.+X.F.Suc+X.VXdt+total.Vol+emission_O2+rab+Thr+lactate+PO4.ferm.+PO4.apporte+PO4.utilise; 0.569, 0.805, pH+tmp+Main.Thr.Conc.+Nitrogen.Conc.+OD+Lys_conc.+X.VXdt+total.cell+Thr+His+lactate+PO4.ferm.; 0.569, 0.805, pH+Nitrogen.Conc.+Lys_conc.+X.VXdt+total.Vol+yield+emission_O2+rab+Thr+His+lactate+PO4.utilise; 0.569, 0.805, pH+tmp+Nitrogen.Conc.+OD+Lys_conc.+X.F.Suc+X.VXdt+total.cell+Thr+lactate+SO4.ferm.+PO4.ferm.; 0.543, 0.805, pH+tmp+Main.P-Source.Conc.+Nitrogen.Conc.+OD+Lys_conc.+X.F.Suc+X.VXdt+total.Vol+total.cell+emission_O2+rab+Thr+lactate+PO4.ferm.; 0.533, 0.805, pH+tmp+Nitrogen.Conc.+OD+Lys_conc.+X.F.Suc+X.VXdt+total.Vol+total.cell+PL+emission_O2+rab+Thr+His+lactate+PO4.ferm.; 0.576, 0.805, pH+tmp+Nitrogen.Conc.+Lys_conc.+X.VXdt+total.Vol+PL+emission_O2+rab+Thr+PO4.ferm.; 0.576, 0.805, tmp+Main.Thr.Conc.+Nitrogen.Conc.+OD+Lys_conc.+X.F.Suc+X.VXdt+total.cell+His+lactate+PO4.ferm.; 0.551, 0.805, tmp+P-Source.Feed.conc.+Nitrogen.Conc.+Lys_conc.+X.VXdt+total.Vol+yield+emission_O2+rab+Thr+lactate+PO4.ferm.+PO4.apporte+PO4.utilise; 0.568, 0.805, Nitrogen.Conc.+Lys_conc.+X.VXdt+total.Vol+yield+emission_O2+rab+Thr+His+lactate+PO4.apporte+PO4.utilise; 0.542, 0.805, pH+tmp+Main.P-Source.Conc.+Main.Thr.Conc.+Nitrogen.Conc.+OD+Lys_conc.+X.VXdt+total.cell+PL+emission_O2+rab+Thr+lactate+PO4.ferm.; 0.560, 0.805, tmp+P-Source.Feed.conc.+Nitrogen.Conc.+OD+Lys_conc.+X.VXdt+total.Vol+PL+emission_O2+rab+Thr+lactate+PO4.ferm.; 0.551, 0.805, pH+tmp+P-Source.Feed.conc.+Main.Thr.Conc.+Nitrogen.Conc.+OD+Lys_conc.+X.VXdt+total.cell+emission_O2+rab+lactate+PO4.ferm.; 0.560, 0.805, pH+tmp+Main.P-Source.Conc.+Lys_conc.+X.VXdt+total.Vol+total.cell+PL+emission_O2+rab+Thr+lactate+PO4.ferm.; 0.599, 0.805, pH+tmp+OD+Lys_conc.+X.F.Suc+X.VXdt+total.cell+PO4.ferm.; 0.551, 0.805, pH+tmp+Main.Thr.Conc.+Lys_conc.+X.VXdt+total.Vol+total.cell+PL+emission_O2+rab+Thr+lactate+SO4.ferm.+PO4.ferm.; 0.533, 0.805, pH+tmp+Main.Thr.Conc.+Nitrogen.Conc.+Lys_conc.+X.VXdt+total.Vol+total.cell+PL+emission_O2+rab+Thr+His+lactate+SO4.ferm.+PO4.ferm.; 0.584, 0.805, tmp+Nitrogen.Conc.+OD+Lys_conc.+X.VXdt+total.Vol+total.cell+Thr+lactate+PO4.ferm.; 0.576, 0.805, tmp+Main.P-Source.Conc.+Main.Thr.Conc.+Nitrogen.Conc.+OD+Lys_conc.+X.VXdt+total.cell+Thr+lactate+PO4.ferm.; 0.542, 0.805, pH+tmp+P-Source.Feed.conc.+Nitrogen.Conc.+OD+Lys_conc.+X.VXdt+total.Vol+PL+emission_O2+rab+Thr+His+lactate+PO4.ferm.; 0.560, 0.805, pH+tmp+Main.P-Source.Conc.+Nitrogen.Conc.+OD+Lys_conc.+X.VXdt+total.Vol+total.cell+emission_O2+rab+lactate+PO4.ferm.; 0.542, 0.805, pH+tmp+Main.Thr.Conc.+Nitrogen.Conc.+OD+Lys_conc.+X.F.Suc+X.VXdt+total.Vol+total.cell+emission_O2+rab+Thr+lactate+PO4.ferm.; 0.560, 0.805, tmp+Main.Thr.Conc.+OD+Lys_conc.+X.VXdt+total.cell+PL+emission_O2+rab+Thr+His+lactate+PO4.ferm.; 0.560, 0.805, Main.P-Source.Conc.+Nitrogen.Conc.+Lys_conc.+X.VXdt+total.Vol+yield+emission_O2+rab+Thr+lactate+PO4.ferm.+PO4.apporte+PO4.utilise; 0.584, 0.805, pH+tmp+Nitrogen.Conc.+Lys_conc.+X.F.Suc+X.VXdt+total.Vol+emission_O2+rab+PO4.ferm.; 0.584, 0.805, pH+tmp+Main.Thr.Conc.+OD+Lys_conc.+X.VXdt+total.cell+PL+Thr+PO4.ferm.; 0.551, 0.805, pH+tmp+Main.P-Source.Conc.+Nitrogen.Conc.+OD+Lys_conc.+X.VXdt+total.cell+emission_O2+rab+Thr+lactate+SO4.ferm.+PO4.ferm.; 0.551, 0.805, pH+tmp+Main.Thr.Conc.+Nitrogen.Conc.+Lys_conc.+X.VXdt+total.Vol+emission_O2+rab+Thr+His+lactate+SO4.ferm.+PO4.ferm.; 0.551, 0.805, pH+Main.Thr.Conc.+Nitrogen.Conc.+Lys_conc.+X.VXdt+total.Vol+yield+emission_O2+rab+Thr+lactate+PO4.ferm.+PO4.apporte+PO4.utilise; 0.560, 0.805, P-Source.Feed.conc.+Nitrogen.Conc.+Lys_conc.+X.VXdt+total.Vol+yield+PL+emission_O2+rab+Thr+lactate+PO4.ferm.+PO4.utilise; 0.598, 0.805, tmp+OD+Lys_conc.+X.VXdt+total.cell+emission_O2+Thr+PO4.ferm.; 0.560, 0.805, tmp+Main.Thr.Conc.+Nitrogen.Conc.+Lys_conc.+X.VXdt+total.Vol+PL+emission_O2+rab+Thr+lactate+PO4.ferm.+PO4.apporte; 0.551, 0.805, pH+tmp+P-Source.Feed.conc.+Main.Thr.Conc.+Nitrogen.Conc.+OD+Lys_conc.+X.VXdt+total.Vol+emission_O2+rab+Thr+lactate+PO4.ferm.; 0.551, 0.805, pH+tmp+Main.P-Source.Conc.+Nitrogen.Conc.+OD+Lys_conc.+X.F.Suc+X.VXdt+total.Vol+total.cell+emission_O2+rab+lactate+PO4.ferm.; 0.551, 0.805, pH+tmp+P-Source.Feed.conc.+Nitrogen.Conc.+Lys_conc.+X.F.Suc+X.VXdt+total.Vol+total.cell+emission_O2+rab+Thr+lactate+PO4.ferm.; 0.551, 0.805, pH+tmp+Main.P-Source.Conc.+Nitrogen.Conc.+OD+Lys_conc.+X.F.Suc+X.VXdt+total.cell+emission_O2+rab+His+lactate+PO4.ferm.; 0.542, 0.805, pH+tmp+P-Source.Feed.conc.+Nitrogen.Conc.+Lys_conc.+X.VXdt+total.Vol+total.cell+PL+emission_O2+rab+Thr+lactate+SO4.ferm.+PO4.ferm.; 0.542, 0.805, Main.Thr.Conc.+Nitrogen.Conc.+Lys_conc.+X.VXdt+total.Vol+yield+PL+emission_O2+rab+Thr+lactate+SO4.ferm.+PO4.ferm.+PO4.apporte+PO4.utilise; 0.560, 0.805, tmp+Main.Thr.Conc.+Nitrogen.Conc.+Lys_conc.+X.VXdt+total.Vol+emission_O2+rab+Thr+His+lactate+PO4.ferm.+PO4.apporte; 0.591, 0.805, pH+tmp+Main.Thr.Conc.+Nitrogen.Conc.+Lys_conc.+X.VXdt+total.Vol+lactate+PO4.ferm.; 0.551, 0.805, pH+tmp+P-Source.Feed.conc.+Nitrogen.Conc.+Lys_conc.+X.F.Suc+X.VXdt+total.Vol+total.cell+emission_O2+rab+His+lactate+PO4.ferm.; 0.560, 0.805, pH+tmp+Main.P-Source.Conc.+Main.Thr.Conc.+Nitrogen.Conc.+Lys_conc.+X.VXdt+total.Vol+emission_O2+rab+His+lactate+PO4.ferm.; 0.560, 0.805, tmp+Main.P-Source.Conc.+Nitrogen.Conc.+Lys_conc.+X.VXdt+total.Vol+total.cell+PL+emission_O2+rab+Thr+lactate+PO4.ferm.; 0.551, 0.805, pH+tmp+Main.P-Source.Conc.+P-Source.Feed.conc.+Nitrogen.Conc.+OD+Lys_conc.+X.VXdt+total.Vol+total.cell+emission_O2+rab+lactate+PO4.ferm.; 0.584, 0.805, Nitrogen.Conc.+Lys_conc.+X.VXdt+total.Vol+emission_O2+rab+Thr+lactate+PO4.ferm.+PO4.apporte; 0.584, 0.805, pH+tmp+Lys_conc.+X.VXdt+total.Vol+total.cell+emission_O2+rab+lactate+PO4.ferm.; 0.551, 0.805, tmp+P-Source.Feed.conc.+Nitrogen.Conc.+OD+Lys_conc.+X.VXdt+total.cell+PL+emission_O2+rab+Thr+His+lactate+PO4.ferm.; 0.551, 0.805, pH+tmp+Main.P-Source.Conc.+Nitrogen.Conc.+Lys_conc.+X.VXdt+total.cell+emission_O2+rab+Thr+lactate+SO4.ferm.+PO4.ferm.; 0.568, 0.805, tmp+Nitrogen.Conc.+Lys_conc.+X.F.Suc+X.VXdt+total.Vol+emission_O2+rab+Thr+His+lactate+PO4.ferm.; 0.551, 0.805, tmp+Nitrogen.Conc.+OD+Lys_conc.+X.VXdt+total.Vol+total.cell+PL+emission_O2+rab+Thr+lactate+SO4.

ferm.+PO4.ferm.; 0.532, 0.805, pH+tmp+P-Source.Feed. conc.+Nitrogen.Conc.+OD+Lys_conc.+X.VXdt+total.Vol+ total.cell+PL+emission_O2+rab+Thr+lactate+SO4.ferm.+ PO4.ferm.; 0.605, 0.805, pH+tmp+OD+Lys_conc.+X. VXdt+total.cell+PO4.ferm.; 0.551, 0.805, pH+P-Source. Feed.conc.+Nitrogen.Conc.+Lys_conc.+X.VXdt+total.Vol+ yield+PL+emission_O2+rab+Thr+lactate+PO4.ferm.+PO4. apporte; 0.559, 0.805, pH+tmp+Nitrogen.Conc.+Lys_ conc.+X.F.Suc+X.VXdt+total.Vol+total.cell+emission_O2+ rab+lactate+SO4.ferm.+PO4.ferm.; 0.559, 0.805, pH+tmp+ P-Source.Feed.conc.+Nitrogen.Conc.+Lys_conc.+X.VXdt+ total.Vol+emission_O2+rab+Thr+lactate+PO4.ferm.+PO4. utilise; 0.551, 0.805, pH+tmp+Nitrogen.Conc.+Lys_conc.+ X.VXdt+total.Vol+yield+emission_O2+rab+Thr+His+ lactate+PO4.ferm.+PO4.apporte; 0.559, 0.805, pH+tmp+ Nitrogen.Conc.+OD+Lys_conc.+X.F.Suc+X.VXdt+total. cell+emission_O2+rab+lactate+SO4.ferm.+PO4.ferm.; 0.551, 0.805, pH+tmp+P-Source.Feed.conc.+Main.Thr. Conc.+Nitrogen.Conc.+OD+Lys_conc.+X.VXdt+total.Vol+ emission_O2+rab+His+lactate+PO4.ferm.; 0.576, 0.805, tmp+Main.Thr.Conc.+OD+Lys_conc.+X.VXdt+total.cell+ emission_O2+Thr+His+lactate+PO4.ferm.; 0.542, 0.805, pH+tmp+Main.P-Source.Conc.+Nitrogen.Conc.+OD+Lys_ conc.+X.VXdt+total.cell+PL+emission_O2+rab+Thr+lactate+SO4.ferm.+PO4.ferm.; 0.559, 0.805, pH+tmp+P-Source.Feed.conc.+Nitrogen.Conc.+OD+Lys_conc.+X. VXdt+total.cell+PL+emission_O2+rab+Thr+PO4.ferm.; 0.542, 0.805, pH+tmp+Main.P-Source.Conc.+Main.Thr. Conc.+Nitrogen.Conc.+Lys_conc.+X.VXdt+total.Vol+total. cell+PL+emission_O2+rab+Thr+lactate+PO4.ferm.; 0.568, 0.805, pH+tmp+P-Source.Feed.conc.+OD+Lys_conc.+X. VXdt+total.cell+emission_O2+rab+Thr+lactate+PO4. ferm.; 0.568, 0.805, tmp+Nitrogen.Conc.+Lys_conc.+X.F. Suc+X.VXdt+total.Vol+emission_O2+rab+Thr+lactate+ PO4.ferm.+PO4.utilise; 0.583, 0.805, pH+tmp+OD+Lys_ conc.+X.VXdt+total.cell+PL+Thr+His+PO4.ferm.; 0.568, 0.805, tmp+OD+Lys_conc.+X.VXdt+total.cell+emission_ O2+rab+Thr+His+lactate+SO4.ferm.+PO4.ferm.; 0.576, 0.805, tmp+Nitrogen.Conc.+OD+Lys_conc.+X.VXdt+total. Vol+total.cell+emission_O2+rab+lactate+PO4.ferm.; 0.559, 0.805, pH+tmp+Main.P-Source.Conc.+Nitrogen.Conc.+ Lys_conc.+X.VXdt+total.Vol+PL+emission_O2+rab+His+ lactate+PO4.ferm.; 0.568, 0.805, tmp+Main.Thr.Conc.+ Lys_conc.+X.VXdt+total.Vol+total.cell+PL+emission_O2+ rab+Thr+lactate+PO4.ferm.; 0.559, 0.805, tmp+Nitrogen. Conc.+Lys_conc.+X.VXdt+total.Vol+total.cell+emission_ O2+rab+Thr+His+lactate+SO4.ferm.+PO4.ferm.; 0.591, 0.805, tmp+Main.Thr.Conc.+OD+Lys_conc.+X.VXdt+total.cell+emission_O2+Thr+PO4.ferm.; 0.551, 0.805, pH+tmp+P-Source.Feed.conc.+Nitrogen.Conc.+Lys_ conc.+X.VXdt+total.Vol+PL+emission_O2+rab+Thr+lactate+PO4.ferm.+PO4.utilise; 0.542, 0.805, Main.Thr.Conc.+ Nitrogen.Conc.+Lys_conc.+X.F.Suc+X.VXdt+total.Vol+ yield+emission_O2+rab+Thr+His+lactate+PO4.ferm.+ PO4.apporte+PO4.utilise; 0.551, 0.805, pH+tmp+P-Source. Feed.conc.+Nitrogen.Conc.+Lys_conc.+X.VXdt+total.Vol+ total.cell+PL+emission_O2+rab+His+lactate+PO4.ferm.; 0.542, 0.805, pH+tmp+Main.Thr.Conc.+Nitrogen.Conc.+ OD+Lys_conc.+X.VXdt+total.cell+emission_O2+rab+ Thr+His+lactate+SO4.ferm.+PO4.ferm.; 0.567, 0.805, tmp+ Nitrogen.Conc.+OD+Lys_conc.+X.F.Suc+X.VXdt+total. cell+emission_O2+rab+His+lactate+PO4.ferm.; 0.541, 0.805, pH+tmp+P-Source.Feed.conc.+Nitrogen.Conc.+ OD+Lys_conc.+X.VXdt+total.cell+PL+emission_O2+rab+ Thr+lactate+SO4.ferm.+PO4.ferm.; 0.559, 0.805, pH+tmp+ Nitrogen.Conc.+Lys_conc.+X.VXdt+total.Vol+yield+ emission_O2+rab+Thr+lactate+PO4.ferm.+PO4.utilise; 0.575, 0.805, tmp+OD+Lys_conc.+X.F.Suc+X.VXdt+total. cell+emission_O2+rab+Thr+His+PO4.ferm.; 0.550, 0.805, pH+tmp+Main.Thr.Conc.+Nitrogen.Conc.+OD+Lys_ conc.+X.VXdt+total.Vol+total.cell+emission_O2+rab+His+ lactate+PO4.ferm.; 0.567, 0.805, tmp+Main.Thr.Conc.+Nitrogen.Conc.+Lys_conc.+X.VXdt+total.Vol+emission_O2+ rab+Thr+lactate+SO4.ferm.+PO4.ferm.; 0.575, 0.804, tmp+ Nitrogen.Conc.+OD+Lys_conc.+X.VXdt+total.cell+ emission_O2+Thr+His+lactate+PO4.ferm.; 0.559, 0.804, tmp+P-Source.Feed.conc.+Main.Thr.Conc.+Nitrogen. Conc.+Lys_conc.+X.VXdt+total.Vol+yield+emission_O2+ rab+Thr+lactate+PO4.ferm.; 0.522, 0.804, pH+tmp+Main. Thr.Conc.+Nitrogen.Conc.+OD+Lys_conc.+X.VXdt+total. Vol+total.cell+PL+emission_O2+rab+Thr+His+lactate+ SO4.ferm.+PO4.ferm.; 0.559, 0.804, pH+tmp+Nitrogen. Conc.+Lys_conc.+X.VXdt+total.Vol+total.cell+emission_ O2+rab+His+lactate+SO4.ferm.+PO4.ferm.; 0.559, 0.804, tmp+P-Source.Feed.conc.+Nitrogen.Conc.+Lys_conc.+X. VXdt+total.Vol+emission_O2+rab+Thr+His+lactate+PO4. ferm.+PO4.apporte; 0.583, 0.804, pH+tmp+P-Source.Feed. conc.+Nitrogen.Conc.+Lys_conc.+X.VXdt+total.Vol+ emission_O2+rab+PO4.ferm.; 0.575, 0.804, pH+tmp+OD+ Lys_conc.+X.VXdt+total.cell+PL+Thr+His+lactate+PO4. ferm.; 0.590, 0.804, pH+tmp+Nitrogen.Conc.+OD+Lys_ conc.+X.VXdt+total.cell+Thr+PO4.ferm.; 0.590, 0.804, pH+tmp+Nitrogen.Conc.+OD+Lys_conc.+X.VXdt+total. cell+lactate+PO4.ferm.; 0.567, 0.804, tmp+Nitrogen. Conc.+OD+Lys_conc.+X.F.Suc+X.VXdt+total.Vol+total. cell+emission_O2+rab+lactate+PO4.ferm.; 0.583, 0.804, pH+tmp+Main.Thr.Conc.+Nitrogen.Conc.+Lys_conc.+X.F. Suc+X.VXdt+total.Vol+lactate+PO4.ferm.; 0.550, 0.804, tmp+Lys_conc.+X.VXdt+total.Vol+yield+PL+emission_ O2+rab+Thr+His+lactate+PO4.ferm.+PO4.apporte+PO4. utilise; 0.550, 0.804, pH+tmp+Main.P-Source.Conc.+Nitrogen.Conc.+OD+Lys_conc.+X.VXdt+total.Vol+emission_ O2+rab+Thr+His+lactate+PO4.ferm.; 0.575, 0.804, tmp+ Nitrogen.Conc.+OD+Lys_conc.+X.F.Suc+X.VXdt+total. Vol+emission_O2+rab+lactate+PO4.ferm.; 0.567, 0.804, pH+tmp+Nitrogen.Conc.+Lys_conc.+X.VXdt+total.Vol+ total.cell+PL+emission_O2+rab+Thr+PO4.ferm.; 0.567, 0.804, tmp+Main.Thr.Conc.+OD+Lys_conc.+X.VXdt+total.cell+PL+Thr+His+lactate+SO4.ferm.+PO4.ferm.; 0.550, 0.804, pH+tmp+Main.Thr.Conc.+OD+Lys_conc.+X.F.Suc+ X.VXdt+total.cell+PL+emission_O2+rab+Thr+lactate+ PO4.ferm.; 0.559, 0.804, tmp+OD+Lys_conc.+X.VXdt+total.Vol+total.cell+PL+emission_O2+rab+Thr+His+lactate+ PO4.ferm.; 0.559, 0.804, Nitrogen.Conc.+Lys_conc.+X.F. Suc+X.VXdt+total.Vol+yield+PL+emission_O2+Thr+ lactate+PO4.ferm.+PO4.apporte+PO4.utilise; 0.550, 0.804, pH+Nitrogen.Conc.+Lys_conc.+X.VXdt+total.Vol+yield+ emission_O2+rab+Thr+lactate+SO4.ferm.+PO4.ferm.+ PO4.apporte+PO4.utilise; 0.559, 0.804, tmp+P-Source. Feed.conc.+Nitrogen.Conc.+OD+Lys_conc.+X.VXdt+total. Vol+total.cell+emission_O2+rab+His+lactate+PO4.ferm.; 0.550, 0.804, pH+tmp+P-Source.Feed.conc.+Nitrogen. Conc.+OD+Lys_conc.+X.VXdt+total.Vol+total.cell+PL+ emission_O2+rab+lactate+PO4.ferm.; 0.567, 0.804, pH+tmp+Nitrogen.Conc.+OD+Lys_conc.+X.VXdt+total. Vol+emission_O2+rab+lactate+SO4.ferm.+PO4.ferm.; 0.550, 0.804, pH+tmp+OD+Lys_conc.+X.F.Suc+X.VXdt+ total.cell+PL+emission_O2+rab+Thr+His+lactate+PO4. ferm.; 0.559, 0.804, pH+tmp+OD+Lys_conc.+X.F.Suc+X. VXdt+total.cell+PL+emission_O2+rab+Thr+His+PO4. ferm.; 0.583, 0.804, tmp+OD+Lys_conc.+X.VXdt+total. Vol+total.cell+PL+Thr+lactate+PO4.ferm.; 0.583, 0.804, tmp+Nitrogen.Conc.+OD+Lys_conc.+X.F.Suc+X.VXdt+ total.cell+PL+Thr+PO4.ferm.; 0.550, 0.804, tmp+Main.Thr.

Conc.+Nitrogen.Conc.+OD+Lys_conc.+X.VXdt+total. cell+PL+emission_O2+rab+Thr+His+lactate+PO4.ferm.; 0.567, 0.804, pH+tmp+P-Source.Feed.conc.+Nitrogen. Conc.+Lys_conc.+X.VXdt+total.Vol+emission_O2+rab+ lactate+PO4.ferm.+PO4.utilise; 0.575, 0.804, tmp+Nitrogen.Conc.+Lys_conc.+X.VXdt+total.Vol+emission_O2+ rab+lactate+PO4.ferm.+PO4.apporte+PO4.utilise; 0.590, 0.804, pH+tmp+Nitrogen.Conc.+Lys_conc.+X.VXdt+total. Vol+His+lactate+PO4.ferm.; 0.559, 0.804, tmp+P-Source. Feed.conc.+Nitrogen.Conc.+Lys_conc.+X.VXdt+total.Vol+ total.cell+emission_O2+rab+Thr+lactate+SO4.ferm.+PO4. ferm.; 0.559, 0.804, pH+tmp+Nitrogen.Conc.+OD+Lys_ conc.+X.F.Suc+X.VXdt+total.cell+PL+emission_O2+rab+ lactate+PO4.ferm.; 0.559, 0.804, pH+tmp+Main.Thr.Conc.+ Nitrogen.Conc.+Lys_conc.+X.VXdt+total.Vol+PL+ emission_O2+rab+lactate+SO4.ferm.+PO4.ferm.; 0.559, 0.804, tmp+Nitrogen.Conc.+Lys_conc.+X.F.Suc+X.VXdt+ total.Vol+yield+emission_O2+rab+lactate+PO4.ferm.+ PO4.apporte+PO4.utilise; 0.550, 0.804, pH+tmp+Main.Thr. Conc.+Nitrogen.Conc.+Lys_conc.+X.VXdt+total.Vol+ emission_O2+rab+Thr+lactate+PO4.ferm.+PO4.apporte+ PO4.utilise; 0.567, 0.804, tmp+Main.P-Source.Conc.+ Nitrogen.Conc.+OD+Lys_conc.+X.F.Suc+X.VXdt+total. cell+Thr+His+lactate+PO4.ferm.; 0.567, 0.804, tmp+ Nitrogen.Conc.+Lys_conc.+X.VXdt+total.Vol+emission_ O2+rab+Thr+lactate+SO4.ferm.+PO4.ferm.+PO4.apporte; 0.559, 0.804, pH+tmp+P-Source.Feed.conc.+Main.Thr. Conc.+Nitrogen.Conc.+Lys_conc.+X.VXdt+total.Vol+ emission_O2+rab+lactate+SO4.ferm.+PO4.ferm.; 0.597, 0.804, tmp+Main.P-Source.Conc.+OD+Lys_conc.+X. VXdt+total.cell+Thr+PO4.ferm.; 0.567, 0.804, tmp+Main. Thr.Conc.+Nitrogen.Conc.+Lys_conc.+X.VXdt+total.Vol+ emission_O2+rab+Thr+His+lactate+PO4.ferm.; 0.550, 0.804, pH+tmp+P-Source.Feed.conc.+Nitrogen.Conc.+ Lys_conc.+X.VXdt+total.Vol+yield+PL+emission_O2+ rab+Thr+lactate+PO4.ferm.; 0.550, 0.804, pH+tmp+Nitrogen.Conc.+Lys_conc.+X.VXdt+total.Vol+PL+emission_ O2+rab+Thr+lactate+SO4.ferm.+PO4.ferm.+PO4.utilise; 0.575, 0.804, tmp+Nitrogen.Conc.+OD+Lys_conc.+X. VXdt+total.Vol+emission_O2+rab+His+lactate+PO4.ferm.; 0.567, 0.804, tmp+Main.P-Source.Conc.+OD+Lys_conc.+ X.F.Suc+X.VXdt+total.cell+emission_O2+rab+Thr+lactate+PO4.ferm.; 0.590, 0.804, tmp+Main.Thr.Conc.+OD+ Lys_conc.+X.F.Suc+X.VXdt+total.cell+Thr+PO4.ferm.; 0.559, 0.804, tmp+Main.Thr.Conc.+Nitrogen.Conc.+OD+ Lys_conc.+X.F.Suc+X.VXdt+total.cell+Thr+His+lactate+ SO4.ferm.+PO4.ferm.; 0.541, 0.804, pH+tmp+P-Source. Feed.conc.+Main.Thr.Conc.+Nitrogen.Conc.+Lys_conc.+ X.VXdt+total.Vol+PL+emission_O2+rab+Thr+lactate+ SO4.ferm.+PO4.ferm.; 0.567, 0.804, tmp+Main.Thr.Conc.+ OD+Lys_conc.+X.VXdt+total.cell+PL+emission_O2+Thr+ lactate+SO4.ferm.+PO4.ferm.; 0.575, 0.804, pH+tmp+ Main.P-Source.Conc.+Main.Thr.Conc.+Lys_conc.+X. VXdt+total.Vol+emission_O2+rab+lactate+PO4.ferm.; 0.583, 0.804, tmp+Nitrogen.Conc.+OD+Lys_conc.+X.F. Suc+X.VXdt+total.cell+Thr+His+PO4.ferm.; 0.550, 0.804, tmp+P-Source.Feed.conc.+Nitrogen.Conc.+OD+Lys_ conc.+X.VXdt+total.Vol+total.cell+emission_O2+rab+ Thr+lactate+SO4.ferm.+PO4.ferm.; 0.541, 0.804, pH+tmp+ Nitrogen.Conc.+Lys_conc.+X.VXdt+total.Vol+yield+ emission_O2+rab+Thr+His+lactate+PO4.ferm.+PO4. apporte+PO4.utilise; 0.550, 0.804, pH+tmp+Main.P-Source.Conc.+P-Source.Feed.conc.+Nitrogen.Conc.+OD+ Lys_conc.+X.VXdt+total.Vol+emission_O2+rab+Thr+ lactate+PO4.ferm.; 0.558, 0.804, tmp+Main.Thr.Conc.+ OD+Lys_conc.+X.VXdt+total.cell+PL+emission_O2+rab+ Thr+lactate+SO4.ferm.+PO4.ferm.; 0.558, 0.804, pH+tmp+ Nitrogen.Conc.+Lys_conc.+X.F.Suc+X.VXdt+total.Vol+ emission_O2+rab+Thr+lactate+PO4.ferm.+PO4.utilise; 0.567, 0.804, Main.Thr.Conc.+Nitrogen.Conc.+Lys_conc.+ X.VXdt+total.Vol+yield+emission_O2+Thr+lactate+PO4. ferm.+PO4.apporte+PO4.utilise; 0.541, 0.804, pH+tmp+ Main.P-Source.Conc.+P-Source.Feed.conc.+Nitrogen. Conc.+OD+Lys_conc.+X.VXdt+total.cell+PL+emission_ O2+rab+Thr+lactate+PO4.ferm.; 0.590, 0.804, tmp+P-Source.Feed.conc.+Nitrogen.Conc.+Lys_conc.+X.VXdt+ total.Vol+His+lactate+PO4.ferm.; 0.575, 0.804, tmp+OD+ Lys_conc.+X.VXdt+total.cell+PL+emission_O2+Thr+His+ lactate+PO4.ferm.; 0.590, 0.804, pH+tmp+Lys_conc.+X. VXdt+total.Vol+PL+emission_O2+rab+PO4.ferm.; 0.567, 0.804, tmp+Main.P-Source.Conc.+P-Source.Feed.conc.+ Nitrogen.Conc.+Lys_conc.+X.VXdt+total.Vol+total.cell+ emission_O2+rab+lactate+PO4.ferm.; 0.582, 0.804, pH+tmp+OD+Lys_conc.+X.VXdt+total.cell+Thr+His+lactate+PO4.ferm.; 0.558, 0.804, pH+tmp+OD+Lys_conc.+X. VXdt+total.cell+PL+emission_O2+rab+Thr+His+SO4. ferm.+PO4.ferm.; 0.582, 0.804, tmp+Main.Thr.Conc.+ Nitrogen.Conc.+OD+Lys_conc.+X.VXdt+total.cell+Thr+ His+PO4.ferm.; 0.558, 0.804, pH+tmp+P-Source.Feed. conc.+Nitrogen.Conc.+Lys_conc.+X.VXdt+total.Vol+ emission_O2+rab+His+lactate+PO4.ferm.+PO4.apporte; 0.550, 0.804, tmp+P-Source.Feed.conc.+Nitrogen.Conc.+ OD+Lys_conc.+X.F.Suc+X.VXdt+total.Vol+total.cell+ emission_O2+rab+Thr+lactate+PO4.ferm.; 0.590, 0.804, tmp+Nitrogen.Conc.+OD+Lys_conc.+X.F.Suc+X.VXdt+ total.cell+His+PO4.ferm.

[16. Linear Model that Predicts Lysine Production Amount in Interval 6]

0.463, 0.744, pH+Nitrogen.Conc.+OD+X.F.Suc+X.VXdt+ yield+rab+Thr+PO4.ferm.+PO4.apporte+PO4.utilise; 0.459, 0.742, pH+Nitrogen.Conc.+OD+X.F.Suc+X.VXdt+ yield+emission_O2+Thr+PO4.ferm.+PO4.apporte+PO4. utilise; 0.446, 0.740, pH+Nitrogen.Conc.+OD+X.F.Suc+X. VXdt+yield+rab+Thr+His+PO4.ferm.+PO4.apporte+PO4. utilise; 0.445, 0.740, pH+Nitrogen.Conc.+OD+X.F.Suc+X. VXdt+yield+PL+rab+Thr+PO4.ferm.+PO4.apporte+PO4. utilise; 0.443, 0.739, pH+Nitrogen.Conc.+OD+X.F.Suc+X. VXdt+yield+emission_O2+Thr+His+PO4.ferm.+PO4. apporte+PO4.utilise; 0.462, 0.738, pH+Nitrogen.Conc.+X. F.Suc+X.VXdt+yield+rab+Thr+PO4.ferm.+PO4.apporte+ PO4.utilise; 0.440, 0.737, pH+Nitrogen.Conc.+OD+X.F. Suc+X.VXdt+yield+PL+emission_O2+Thr+PO4.ferm.+ PO4.apporte+PO4.utilise; 0.470, 0.737, pH+Nitrogen. Conc.+X.F.Suc+X.VXdt+yield+rab+PO4.ferm.+PO4. apporte+PO4.utilise; 0.440, 0.737, pH+Main.P-Source. Conc.+Nitrogen.Conc.+OD+X.F.Suc+X.VXdt+yield+rab+ Thr+PO4.ferm.+PO4.apporte+PO4.utilise; 0.439, 0.736, pH+Nitrogen.Conc.+OD+X.F.Suc+X.VXdt+yield+rab+ Thr+lactate+PO4.ferm.+PO4.apporte+PO4.utilise; 0.439, 0.736, pH+Nitrogen.Conc.+OD+X.F.Suc+X.VXdt+yield+ emission_O2+rab+Thr+PO4.ferm.+PO4.apporte+PO4.utilise; 0.427, 0.736, pH+Nitrogen.Conc.+OD+X.F.Suc+X. VXdt+yield+PL+rab+Thr+His+PO4.ferm.+PO4.apporte+ PO4.utilise; 0.437, 0.736, pH+Nitrogen.Conc.+OD+X.F. Suc+X.VXdt+yield+emission_CO2+rab+Thr+PO4.ferm.+ PO4.apporte+PO4.utilise; 0.448, 0.736, pH+Nitrogen. Conc.+X.F.Suc+X.VXdt+total.cell+yield+rab+Thr+PO4. ferm.+PO4.apporte+PO4.utilise; 0.435, 0.735, pH+Nitrogen.Conc.+OD+X.F.Suc+X.VXdt+yield+emission_O2+emission_CO2+Thr+PO4.ferm.+PO4.apporte+ PO4.utilise; 0.424, 0.734, pH+tmp+Nitrogen.Conc.+X.F. Suc+X.VXdt+total.cell+yield+emission_O2+Thr+His+ PO4.ferm.+PO4.apporte+PO4.utilise; 0.435, 0.734, pH+Nitrogen.Conc.+OD+X.F.Suc+X.VXdt+yield+emission_O2+Thr+lactate+PO4.ferm.+PO4.utilise; 0.424, 0.734, pH+Nitrogen.Conc.+X.F.Suc+X.VXdt+yield+PL+emission_O2+Thr+His+PO4.ferm.+PO4.apporte+PO4.utilise; 0.455, 0.734, pH+Nitrogen.Conc.+OD+X.F.Suc+X.VXdt+yield+rab+PO4.ferm.+PO4.apporte+PO4.utilise; 0.445, 0.734, pH+Nitrogen.Conc.+X.F.Suc+X.VXdt+yield+PL+rab+Thr+PO4.ferm.+PO4.apporte+PO4.utilise; 0.445, 0.734, pH+Nitrogen.Conc.+X.F.Suc+X.VXdt+yield+rab+Thr+His+PO4.ferm.+PO4.apporte+PO4.utilise; 0.434, 0.734, pH+Main.P-Source.Conc.+Nitrogen.Conc.+OD+X.F.Suc+X.VXdt+yield+emission_O2+Thr+PO4.ferm.+PO4.apporte+PO4.utilise; 0.444, 0.734, pH+Nitrogen.Conc.+X.F.Suc+X.VXdt+yield+rab+Thr+lactate+PO4.ferm.+PO4.apporte+PO4.utilise; 0.433, 0.733, pH+tmp+Nitrogen.Conc.+X.F.Suc+X.VXdt+total.cell+yield+emission_O2+Thr+PO4.ferm.+PO4.apporte+PO4.utilise; 0.453, 0.733, pH+Nitrogen.Conc.+X.F.Suc+X.VXdt+yield+PL+rab+PO4.ferm.+PO4.apporte+PO4.utilise; 0.453, 0.733, pH+Nitrogen.Conc.+X.F.Suc+X.VXdt+yield+emission_O2+Thr+PO4.ferm.+PO4.apporte+PO4.utilise; 0.432, 0.733, pH+tmp+Nitrogen.Conc.+X.F.Suc+X.VXdt+total.cell+yield+rab+Thr+PO4.ferm.+PO4.apporte+PO4.utilise; 0.453, 0.733, pH+Nitrogen.Conc.+X.F.Suc+X.VXdt+yield+rab+His+PO4.ferm.+PO4.apporte+PO4.utilise; 0.421, 0.732, pH+Nitrogen.Conc.+OD+X.F.Suc+X.VXdt+yield+emission_O2+rab+Thr+His+PO4.ferm.+PO4.apporte+PO4.utilise; 0.409, 0.732, pH+tmp+Nitrogen.Conc.+X.F.Suc+X.VXdt+total.cell+yield+PL+emission_O2+Thr+His+PO4.ferm.+PO4.apporte+PO4.utilise; 0.452, 0.732, pH+Nitrogen.Conc.+X.F.Suc+X.VXdt+total.cell+yield+rab+PO4.ferm.+PO4.apporte+PO4.utilise; 0.421, 0.732, pH+tmp+Nitrogen.Conc.+X.F.Suc+X.VXdt+total.cell+yield+rab+Thr+His+PO4.ferm.+PO4.apporte+PO4.utilise; 0.420, 0.732, pH+Nitrogen.Conc.+OD+X.F.Suc+X.VXdt+yield+PL+rab+Thr+lactate+PO4.ferm.+PO4.apporte+PO4.utilise; 0.452, 0.732, pH+tmp+Nitrogen.Conc.+X.F.Suc+X.VXdt+yield+rab+PO4.ferm.+PO4.apporte+PO4.utilise; 0.420, 0.732, pH+Main.P-Source.Conc.+Nitrogen.Conc.+OD+X.F.Suc+X.VXdt+yield+PL+rab+Thr+PO4.ferm.+PO4.apporte+PO4.utilise; 0.442, 0.732, pH+tmp+Nitrogen.Conc.+X.F.Suc+X.VXdt+total.cell+yield+rab+PO4.ferm.+PO4.apporte+PO4.utilise; 0.451, 0.732, pH+tmp+Nitrogen.Conc.+X.F.Suc+X.VXdt+yield+emission_O2+PO4.ferm.+PO4.apporte+PO4.utilise; 0.451, 0.732, pH+Nitrogen.Conc.+X.F.Suc+X.VXdt+yield+rab+lactate+PO4.ferm.+PO4.apporte+PO4.utilise; 0.420, 0.732, pH+Nitrogen.Conc.+OD+X.F.Suc+X.VXdt+yield+PL+emission_O2+rab+Thr+PO4.ferm.+PO4.apporte+PO4.utilise; 0.419, 0.732, pH+Nitrogen.Conc.+OD+X.F.Suc+X.VXdt+yield+emission_CO2+rab+Thr+His+PO4.ferm.+PO4.apporte+PO4.utilise; 0.441, 0.732, pH+Main.P-Source.Conc.+Nitrogen.Conc.+X.F.Suc+X.VXdt+yield+rab+Thr+PO4.ferm.+PO4.apporte+PO4.utilise; 0.419, 0.732, pH+Nitrogen.Conc.+OD+X.F.Suc+X.VXdt+yield+rab+Thr+His+lactate+PO4.ferm.+PO4.apporte+PO4.utilise; 0.441, 0.732, pH+tmp+Nitrogen.Conc.+X.F.Suc+X.VXdt+yield+emission_O2+His+PO4.ferm.+PO4.apporte+PO4.utilise; 0.430, 0.731, pH+Nitrogen.Conc.+X.F.Suc+X.VXdt+total.cell+yield+PL+rab+Thr+PO4.ferm.+PO4.apporte+PO4.utilise; 0.419, 0.731, pH+tmp+Nitrogen.Conc.+X.F.Suc+X.VXdt+total.cell+yield+emission_CO2+Thr+His+PO4.ferm.+PO4.apporte+PO4.utilise; 0.419, 0.731, pH+Main.P-Source.Conc.+Nitrogen.Conc.+OD+X.F.Suc+X.VXdt+yield+rab+Thr+His+PO4.ferm.+PO4.apporte+PO4.utilise; 0.429, 0.731, pH+P-Source.Feed.conc.+Nitrogen.Conc.+OD+X.F.Suc+X.VXdt+yield+rab+Thr+PO4.ferm.+PO4.apporte+PO4.utilise; 0.429, 0.731, pH+Nitrogen.Conc.+X.F.Suc+X.VXdt+total.cell+yield+rab+Thr+His+PO4.ferm.+PO4.apporte+PO4.utilise; 0.429, 0.731, pH+Main.Thr.Conc.+Nitrogen.Conc.+OD+X.F.Suc+X.VXdt+yield+rab+Thr+PO4.ferm.+PO4.apporte+PO4.utilise; 0.418, 0.731, pH+Nitrogen.Conc.+OD+X.F.Suc+X.VXdt+yield+PL+emission_CO2+rab+Thr+PO4.ferm.+PO4.apporte+PO4.utilise; 0.418, 0.731, pH+Nitrogen.Conc.+OD+X.F.Suc+X.VXdt+yield+emission_O2+Thr+His+lactate+PO4.ferm.+PO4.apporte+PO4.utilise; 0.417, 0.731, pH+tmp+Nitrogen.Conc.+X.F.Suc+X.VXdt+total.cell+yield+PL+emission_O2+Thr+PO4.ferm.+PO4.apporte+PO4.utilise; 0.439, 0.731, pH+tmp+Nitrogen.Conc.+X.F.Suc+X.VXdt+total.cell+yield+emission_O2+PO4.ferm.+PO4.apporte+PO4.utilise; 0.428, 0.731, pH+tmp+Nitrogen.Conc.+X.F.Suc+X.VXdt+total.cell+yield+emission_O2+His+PO4.ferm.+PO4.apporte+PO4.utilise; 0.428, 0.731, pH+tmp+Nitrogen.Conc.+X.F.Suc+X.VXdt+total.cell+yield+rab+His+PO4.ferm.+PO4.apporte+PO4.utilise; 0.406, 0.731, pH+tmp+Nitrogen.Conc.+X.F.Suc+X.VXdt+total.cell+yield+PL+rab+Thr+His+PO4.ferm.+PO4.apporte+PO4.utilise; 0.439, 0.731, pH+tmp+Nitrogen.Conc.+X.F.Suc+X.VXdt+yield+rab+His+PO4.ferm.+PO4.apporte+PO4.utilise; 0.417, 0.730, pH+Nitrogen.Conc.+OD+X.F.Suc+X.VXdt+yield+emission_O2+emission_CO2+Thr+His+PO4.ferm.+PO4.apporte+PO4.utilise; 0.417, 0.730, pH+tmp+Nitrogen.Conc.+X.F.Suc+X.VXdt+total.cell+yield+PL+rab+Thr+PO4.ferm.+PO4.apporte+PO4.utilise; 0.448, 0.730, pH+Main.P-Source.Conc.+Nitrogen.Conc.+X.F.Suc+X.VXdt+yield+rab+PO4.ferm.+PO4.apporte+PO4.utilise; 0.458, 0.730, pH+Nitrogen.Conc.+X.F.Suc+X.VXdt+yield+emission_O2+PO4.ferm.+PO4.apporte+PO4.utilise; 0.427, 0.730, pH+Nitrogen.Conc.+X.F.Suc+X.VXdt+yield+PL+rab+Thr+His+PO4.ferm.+PO4.apporte+PO4.utilise; 0.438, 0.730, pH+Nitrogen.Conc.+OD+X.F.Suc+X.VXdt+yield+rab+His+PO4.ferm.+PO4.apporte+PO4.utilise; 0.416, 0.730, pH+Nitrogen.Conc.+OD+X.F.Suc+X.VXdt+yield+PL+emission_O2+Thr+lactate+PO4.ferm.+PO4.apporte+PO4.utilise; 0.438, 0.730, pH+Nitrogen.Conc.+OD+X.F.Suc+X.VXdt+yield+PL+rab+PO4.ferm.+PO4.apporte+PO4.utilise; 0.427, 0.730, pH+P-Source.Feed.conc.+Nitrogen.Conc.+OD+X.F.Suc+X.VXdt+yield+emission_O2+Thr+PO4.ferm.+PO4.apporte+PO4.utilise; 0.438, 0.730, pH+Nitrogen.Conc.+X.F.Suc+X.VXdt+yield+emission_O2+Thr+His+PO4.ferm.+PO4.apporte+PO4.utilise; 0.448, 0.730, pH+Nitrogen.Conc.+X.F.Suc+X.VXdt+yield+emission_O2+rab+PO4.ferm.+PO4.apporte+PO4.utilise; 0.438, 0.730, pH+Nitrogen.Conc.+X.F.Suc+X.VXdt+yield+emission_O2+rab+Thr+PO4.ferm.+PO4.apporte+PO4.utilise; 0.416, 0.730, pH+Nitrogen.Conc.+OD+X.F.Suc+X.VXdt+yield+PL+emission_O2+emission_CO2+Thr+PO4.ferm.+PO4.apporte+PO4.utilise; 0.416, 0.730, pH+Nitrogen.Conc.+OD+X.F.Suc+X.VXdt+yield+emission_O2+emission_CO2+rab+Thr+PO4.ferm.+PO4.apporte+PO4.utilise; 0.426, 0.729, pH+Nitrogen.Conc.+X.F.Suc+X.VXdt+yield+PL+rab+Thr+lactate+PO4.ferm.+PO4.apporte+PO4.utilise; 0.426, 0.729, pH+tmp+Nitrogen.Conc.+X.F.Suc+X.VXdt+yield+emission_O2+Thr+His+PO4.ferm.+PO4.apporte+PO4.utilise; 0.403, 0.729, pH+tmp+Nitrogen.Conc.+X.F.Suc+X.VXdt+total.cell+yield+PL+emission_CO2+Thr+His+PO4.ferm.+PO4.apporte+PO4.utilise; 0.415, 0.729, pH+Main.P-Source.Conc.+Nitrogen.Conc.+OD+X.F.Suc+X.VXdt+yield+PL+emission_O2+Thr+PO4.ferm.+PO4.apporte+PO4.utilise; 0.415, 0.729, pH+Main.P-Source.Conc.+Nitrogen.Conc.+OD+X.F.Suc+X.VXdt+yield+emission_O2+Thr+His+PO4.ferm.+PO4.apporte+PO4.utilise; 0.436, 0.729, pH+Nitrogen.Conc.+X.F.Suc+X.VXdt+yield+PL+emission_O2+

Thr+PO4.ferm.+PO4.apporte+PO4.utilise; 0.426, 0.729, pH+P-Source.Feed.conc.+Nitrogen.Conc.+X.F.Suc+X. VXdt+total.cell+yield+rab+Thr+PO4.ferm.+PO4.apporte+ PO4.utilise; 0.425, 0.729, pH+tmp+Nitrogen.Conc.+X.F. Suc+X.VXdt+total.cell+yield+PL+rab+PO4.ferm.+PO4. apporte+PO4.utilise; 0.425, 0.729, pH+Nitrogen.Conc.+X. F.Suc+X.VXdt+total.cell+yield+emission_O2+rab+Thr+ PO4.ferm.+PO4.apporte+PO4.utilise; 0.436, 0.729, pH+Nitrogen.Conc.+X.F.Suc+X.VXdt+yield+emission_ CO2+rab+Thr+PO4.ferm.+PO4.apporte+PO4.utilise; 0.425, 0.729, pH+Main.P-Source.Conc.+Nitrogen.Conc.+X.F. Suc+X.VXdt+total.cell+yield+rab+Thr+PO4.ferm.+PO4. apporte+PO4.utilise; 0.436, 0.729, pH+Nitrogen.Conc.+X. F.Suc+X.VXdt+yield+PL+rab+His+PO4.ferm.+PO4. apporte+PO4.utilise; 0.435, 0.729, pH+P-Source.Feed. conc.+Nitrogen.Conc.+X.F.Suc+X.VXdt+yield+rab+Thr+ PO4.ferm.+PO4.apporte+PO4.utilise; 0.446, 0.729, pH+Nitrogen.Conc.+OD+X.F.Suc+X.VXdt+yield+emission_O2+PO4.ferm.+PO4.apporte+PO4.utilise; 0.435, 0.729, pH+tmp+Nitrogen.Conc.+X.F.Suc+X.VXdt+yield+ PL+rab+PO4.ferm.+PO4.apporte+PO4.utilise; 0.446, 0.729, pH+Nitrogen.Conc.+X.F.Suc+X.VXdt+yield+emission_ CO2+rab+PO4.ferm.+PO4.apporte+PO4.utilise; 0.424, 0.729, pH+Main.Thr.Conc.+Nitrogen.Conc.+OD+X.F.Suc+ X.VXdt+yield+emission_O2+Thr+PO4.ferm.+PO4.apporte+PO4.utilise; 0.424, 0.728, pH+tmp+Nitrogen.Conc.+ X.F.Suc+X.VXdt+yield+PL+emission_O2+His+PO4. ferm.+PO4.apporte+PO4.utilise; 0.435, 0.728, pH+Nitrogen.Conc.+X.F.Suc+X.VXdt+total.cell+yield+ PL+rab+PO4.ferm.+PO4.apporte+PO4.utilise; 0.435, 0.728, pH+tmp+Nitrogen.Conc.+X.F.Suc+X.VXdt+yield+emission_O2+Thr+PO4.ferm.+PO4.apporte+PO4.utilise; 0.435, 0.728, pH+Nitrogen.Conc.+X.F.Suc+X.VXdt+yield+emission_O2+emission_CO2+Thr+PO4.ferm.+PO4.apporte+ PO4.utilise; 0.424, 0.728, pH+Nitrogen.Conc.+X.F.Suc+X. VXdt+yield+rab+Thr+His+lactate+PO4.ferm.+PO4. apporte+PO4.utilise; 0.435, 0.728, pH+Nitrogen.Conc.+X. F.Suc+X.VXdt+yield+PL+rab+lactate+PO4.ferm.+PO4. apporte+PO4.utilise; 0.435, 0.728, pH+tmp+Nitrogen. Conc.+X.F.Suc+X.VXdt+yield+PL+emission_O2+PO4. ferm.+PO4.apporte+PO4.utilise; 0.413, 0.728, pH+Main.P-Source.Conc.+Nitrogen.Conc.+OD+X.F.Suc+X.VXdt+ yield+rab+Thr+lactate+PO4.ferm.+PO4.apporte+PO4. utilise; 0.424, 0.728, pH+Nitrogen.Conc.+X.F.Suc+X. VXdt+total.cell+yield+rab+Thr+lactate+PO4.ferm.+PO4. apporte+PO4.utilise; 0.401, 0.728, pH+Nitrogen.Conc.+ OD+X.F.Suc+X.VXdt+yield+PL+emission_O2+rab+Thr+ His+PO4.ferm.+PO4.apporte+PO4.utilise; 0.434, 0.728, pH+Nitrogen.Conc.+X.F.Suc+X.VXdt+yield+emission_ O2+Thr+lactate+PO4.ferm.+PO4.apporte+PO4.utilise; 0.434, 0.728, pH+Nitrogen.Conc.+X.F.Suc+X.VXdt+total. cell+yield+emission_O2+Thr+PO4.ferm.+PO4.apporte+ PO4.utilise; 0.423, 0.728, pH+tmp+Nitrogen.Conc.+X.F. Suc+X.VXdt+yield+emission_CO2+Thr+His+PO4.ferm.+ PO4.apporte+PO4.utilise; 0.434, 0.728, pH+Nitrogen. Conc.+X.F.Suc+X.VXdt+total.cell+yield+rab+His+PO4. ferm.+PO4.apporte+PO4.utilise; 0.454, 0.728, pH+tmp+ Nitrogen.Conc.+X.VXdt+total.cell+yield+emission_CO2+ Thr+His; 0.412, 0.728, pH+tmp+Nitrogen.Conc.+X.F.Suc+ X.VXdt+total.cell+yield+PL+emission_O2+His+PO4. ferm.+PO4.apporte+PO4.utilise; 0.412, 0.728, pH+tmp+ Nitrogen.Conc.+X.F.Suc+X.VXdt+total.cell+yield+PL+ rab+His+PO4.ferm.+PO4.apporte+PO4.utilise; 0.412, 0.728, pH+Main.P-Source.Conc.+Nitrogen.Conc.+OD+X. F.Suc+X.VXdt+yield+emission_O2+rab+Thr+PO4.ferm.+ PO4.apporte+PO4.utilise; 0.400, 0.728, pH+Nitrogen. Conc.+OD+X.F.Suc+X.VXdt+yield+PL+rab+Thr+His+ lactate+PO4.ferm.+PO4.apporte+PO4.utilise; 0.434, 0.728, pH+Main.Thr.Conc.+Nitrogen.Conc.+X.F.Suc+X.VXdt+ yield+rab+Thr+PO4.ferm.+PO4.apporte+PO4.utilise; 0.434, 0.728, pH+Nitrogen.Conc.+OD+X.F.Suc+X.VXdt+ yield+emission_O2+rab+PO4.ferm.+PO4.apporte+PO4.utilise; 0.444, 0.728, pH+Nitrogen.Conc.+X.F.Suc+X.VXdt+ yield+emission_O2+emission_CO2+PO4.ferm.+PO4. apporte+PO4.utilise; 0.400, 0.728, pH+Nitrogen.Conc.+ OD+X.F.Suc+X.VXdt+yield+PL+emission_CO2+rab+ Thr+His+PO4.ferm.+PO4.apporte+PO4.utilise; 0.423, 0.728, pH+Main.P-Source.Conc.+Nitrogen.Conc.+X.F. Suc+X.VXdt+yield+PL+rab+Thr+PO4.ferm.+PO4.apporte+PO4.utilise; 0.423, 0.727, pH+Nitrogen.Conc.+X.F. Suc+X.VXdt+total.cell+yield+emission_CO2+rab+Thr+ PO4.ferm.+PO4.apporte+PO4.utilise; 0.422, 0.727, pH+tmp+Nitrogen.Conc.+X.F.Suc+X.VXdt+total.cell+ yield+PL+emission_O2+PO4.ferm.+PO4.apporte+PO4.utilise; 0.411, 0.727, pH+Main.Thr.Conc.+Nitrogen.Conc.+ OD+X.F.Suc+X.VXdt+yield+rab+Thr+His+PO4.ferm.+ PO4.apporte+PO4.utilise; 0.443, 0.727, pH+Nitrogen. Conc.+X.F.Suc+X.VXdt+yield+emission_O2+His+PO4. ferm.+PO4.apporte+PO4.utilise; 0.399, 0.727, pH+Nitrogen.Conc.+OD+X.F.Suc+X.VXdt+yield+emission_O2+emission_CO2+Thr+His+PO4.ferm.+PO4. apporte+PO4.utilise; 0.411, 0.727, pH+P-Source.Feed. conc.+Nitrogen.Conc.+OD+X.F.Suc+X.VXdt+yield+rab+ Thr+His+PO4.ferm.+PO4.apporte+PO4.utilise; 0.422, 0.727, pH+tmp+Nitrogen.Conc.+X.F.Suc+X.VXdt+yield+ PL+rab+His+PO4.ferm.+PO4.apporte+PO4.utilise; 0.411, 0.727, pH+Nitrogen.Conc.+X.F.Suc+X.VXdt+total.cell+ yield+PL+rab+Thr+His+PO4.ferm.+PO4.apporte+PO4.utilise; 0.411, 0.727, pH+Nitrogen.Conc.+OD+X.F.Suc+X. VXdt+yield+emission_O2+rab+Thr+lactate+PO4.ferm.+ PO4.apporte+PO4.utilise; 0.410, 0.727, pH+Main.P-Source. Conc.+Nitrogen.Conc.+OD+X.F.Suc+X.VXdt+yield+ emission_CO2+rab+Thr+PO4.ferm.+PO4.apporte+PO4. utilise; 0.410, 0.727, pH+P-Source.Feed.conc.+Nitrogen. Conc.+OD+X.F.Suc+X.VXdt+yield+emission_O2+Thr+ His+PO4.ferm.+PO4.apporte+PO4.utilise; 0.399, 0.727, pH+Main.P-Source.Conc.+Nitrogen.Conc.+OD+X.F.Suc+ X.VXdt+yield+PL+rab+Thr+His+PO4.ferm.+PO4.apporte+PO4.utilise; 0.399, 0.727, pH+Nitrogen.Conc.+OD+ X.F.Suc+X.VXdt+yield+PL+emission_O2+Thr+His+ lactate+PO4.ferm.+PO4.apporte+PO4.utilise; 0.432, 0.727, pH+Nitrogen.Conc.+X.F.Suc+X.VXdt+total.cell+yield+ emission_O2+rab+PO4.ferm.+PO4.apporte+PO4.utilise; 0.442, 0.727, pH+Nitrogen.Conc.+X.F.Suc+X.VXdt+yield+ PL+emission_O2+PO4.ferm.+PO4.apporte+PO4.utilise; 0.421, 0.726, pH+Main.P-Source.Conc.+Nitrogen.Conc.+ X.F.Suc+X.VXdt+yield+rab+Thr+His+PO4.ferm.+PO4.apporte+PO4.utilise; 0.410, 0.726, pH+P-Source.Feed.conc.+ Nitrogen.Conc.+OD+X.F.Suc+X.VXdt+yield+PL+rab+ Thr+PO4.ferm.+PO4.apporte+PO4.utilise; 0.431, 0.726, pH+Main.P-Source.Conc.+Nitrogen.Conc.+OD+X.F.Suc+ X.VXdt+yield+rab+PO4.ferm.+PO4.apporte+PO4.utilise; 0.431, 0.726, pH+tmp+Nitrogen.Conc.+X.F.Suc+X.VXdt+ yield+rab+Thr+PO4.ferm.+PO4.apporte+PO4.utilise; 0.431, 0.726, pH+Nitrogen.Conc.+OD+X.F.Suc+X.VXdt+ yield+rab+lactate+PO4.ferm.+PO4.apporte+PO4.utilise; 0.409, 0.726, pH+tmp+Nitrogen.Conc.+OD+X.F.Suc+X. VXdt+yield+emission_CO2+Thr+His+PO4.ferm.+PO4.apporte+PO4.utilise; 0.421, 0.726, pH+Nitrogen.Conc.+X.F. Suc+X.VXdt+yield+PL+emission_O2+Thr+His+PO4. ferm.+PO4.apporte+PO4.utilise; 0.431, 0.726, pH+Nitrogen.Conc.+OD+X.F.Suc+X.VXdt+yield+emission_CO2+rab+PO4.ferm.+PO4.apporte+PO4.utilise; 0.409, 0.726, pH+tmp+Nitrogen.Conc.+X.F.Suc+X.VXdt+ yield+PL+emission_O2+Thr+His+PO4.ferm.+PO4.apporte+PO4.utilise; 0.431, 0.726, pH+Nitrogen.Conc.+X.F.Suc+X.VXdt+yield+rab+His+lactate+PO4.ferm.+PO4.apporte+PO4.utilise; 0.409, 0.726, pH+Nitrogen.Conc.+OD+X.F.Suc+X.VXdt+yield+emission_CO2+rab+Thr+lactate+PO4.ferm.+PO4.apporte+PO4.utilise; 0.431, 0.726, pH+Main.P-Source.Conc.+Nitrogen.Conc.+X.F.Suc+X.VXdt+yield+PL+rab+PO4.ferm.+PO4.apporte+PO4.utilise; 0.420, 0.726, pH+Nitrogen.Conc.+X.F.Suc+X.VXdt+total.cell+yield+emission_O2+emission_CO2+Thr+PO4.ferm.+PO4.apporte+PO4.utilise; 0.397, 0.726, pH+Nitrogen.Conc.+OD+X.F.Suc+X.VXdt+yield+PL+emission_O2+emission_CO2+Thr+His+PO4.ferm.+PO4.apporte+PO4.utilise; 0.430, 0.726, pH+Nitrogen.Conc.+X.F.Suc+X.VXdt+yield+PL+emission_O2+rab+PO4.ferm.+PO4.apporte+PO4.utilise; 0.420, 0.726, pH+Nitrogen.Conc.+OD+X.F.Suc+X.VXdt+yield+PL+rab+His+PO4.ferm.+PO4.apporte+PO4.utilise; 0.408, 0.726, pH+Main.P-Source.Conc.+Nitrogen.Conc.+OD+X.F.Suc+X.VXdt+yield+emission_O2+Thr+lactate+PO4.ferm.+PO4.apporte+PO4.utilise; 0.420, 0.726, pH+tmp+Nitrogen.Conc.+X.F.Suc+X.VXdt+yield+rab+Thr+His+PO4.ferm.+PO4.apporte+PO4.utilise; 0.408, 0.726, pH+Main.P-Source.Conc.+Nitrogen.Conc.+OD+X.F.Suc+X.VXdt+yield+emission_O2+emission_CO2+Thr+PO4.ferm.+PO4.apporte+PO4.utilise; 0.441, 0.726, pH+tmp+Nitrogen.Conc.+X.VXdt+total.cell+yield+PL+emission_CO2+Thr+His; 0.430, 0.726, pH+P-Source.Feed.conc.+Nitrogen.Conc.+X.F.Suc+X.VXdt+yield+emission_O2+Thr+PO4.ferm.+PO4.apporte+PO4.utilise; 0.408, 0.726, pH+Main.Thr.Conc.+Nitrogen.Conc.+OD+X.F.Suc+X.VXdt+yield+PL+rab+Thr+PO4.ferm.+PO4.apporte+PO4.utilise; 0.419, 0.726, pH+Nitrogen.Conc.+X.F.Suc+X.VXdt+yield+PL+emission_O2+rab+Thr+PO4.ferm.+PO4.apporte+PO4.utilise; 0.430, 0.726, pH+Nitrogen.Conc.+OD+X.F.Suc+X.VXdt+yield+emission_O2+His+PO4.ferm.+PO4.apporte+PO4.utilise; 0.430, 0.725, pH+Main.P-Source.Conc.+Nitrogen.Conc.+X.F.Suc+X.VXdt+yield+emission_O2+Thr+PO4.ferm.+PO4.apporte+PO4.utilise; 0.408, 0.725, pH+tmp+Nitrogen.Conc.+OD+X.F.Suc+X.VXdt+yield+emission_O2+Thr+His+PO4.ferm.+PO4.apporte+PO4.utilise; 0.419, 0.725, pH+Nitrogen.Conc.+X.F.Suc+X.VXdt+yield+emission_O2+rab+Thr+His+PO4.ferm.+PO4.apporte+PO4.utilise; 0.396, 0.725, pH+Nitrogen.Conc.+OD+X.F.Suc+X.VXdt+yield+PL+emission_O2+emission_CO2+rab+Thr+PO4.ferm.+PO4.apporte+PO4.utilise; 0.408, 0.725, pH+Main.Thr.Conc.+Nitrogen.Conc.+OD+X.F.Suc+X.VXdt+yield+emission_O2+Thr+His+PO4.ferm.+PO4.apporte+PO4.utilise; 0.396, 0.725, pH+tmp+Nitrogen.Conc.+X.F.Suc+X.VXdt+total.cell+yield+emission_O2+rab+Thr+His+PO4.ferm.+PO4.apporte+PO4.utilise; 0.429, 0.725, pH+Nitrogen.Conc.+X.F.Suc+X.VXdt+total.cell+yield+rab+lactate+PO4.ferm.+PO4.apporte+PO4.utilise; 0.407, 0.725, pH+Nitrogen.Conc.+OD+X.F.Suc+X.VXdt+yield+emission_O2+emission_CO2+Thr+lactate+PO4.ferm.+PO4.apporte+PO4.utilise; 0.429, 0.725, pH+Main.P-Source.Conc.+Nitrogen.Conc.+X.F.Suc+X.VXdt+total.cell+yield+rab+PO4.ferm.+PO4.apporte+PO4.utilise; 0.440, 0.725, pH+P-Source.Feed.conc.+Nitrogen.Conc.+X.F.Suc+X.VXdt+yield+rab+PO4.ferm.+PO4.apporte+PO4.utilise; 0.407, 0.725, pH+P-Source.Feed.conc.+Nitrogen.Conc.+OD+X.F.Suc+X.VXdt+yield+PL+emission_O2+Thr+PO4.ferm.+PO4.apporte+PO4.utilise; 0.418, 0.725, pH+Main.Thr.Conc.+Nitrogen.Conc.+X.F.Suc+X.VXdt+yield+rab+Thr+His+PO4.ferm.+PO4.apporte+PO4.utilise; 0.418, 0.725, pH+Nitrogen.Conc.+OD+X.F.Suc+X.VXdt+yield+rab+Thr+SO4.ferm.+PO4.ferm.+PO4.apporte+PO4.utilise; 0.407, 0.725, pH+tmp+Nitrogen.Conc.+X.F.Suc+X.VXdt+yield+PL+emission_CO2+Thr+His+PO4.ferm.+PO4.apporte+PO4.utilise; 0.429, 0.725, pH+Nitrogen.Conc.+OD+X.F.Suc+X.VXdt+yield+emission_O2+emission_CO2+PO4.ferm.+PO4.apporte+PO4.utilise; 0.429, 0.725, pH+Nitrogen.Conc.+X.F.Suc+X.VXdt+total.cell+yield+emission_CO2+rab+PO4.ferm.+PO4.apporte+PO4.utilise; 0.395, 0.725, pH+Main.P-Source.Conc.+Nitrogen.Conc.+OD+X.F.Suc+X.VXdt+yield+PL+emission_O2+Thr+His+PO4.ferm.+PO4.apporte+PO4.utilise; 0.395, 0.725, pH+tmp+Nitrogen.Conc.+X.F.Suc+X.VXdt+total.cell+yield+emission_CO2+rab+Thr+His+PO4.ferm.+PO4.apporte+PO4.utilise; 0.429, 0.725, pH+Nitrogen.Conc.+X.F.Suc+X.VXdt+yield+emission_O2+rab+His+PO4.ferm.+PO4.apporte+PO4.utilise; 0.418, 0.725, pH+tmp+Nitrogen.Conc.+X.F.Suc+X.VXdt+yield+PL+emission_O2+Thr+PO4.ferm.+PO4.apporte+PO4.utilise; 0.407, 0.725, pH+P-Source.Feed.conc.+Nitrogen.Conc.+X.F.Suc+X.VXdt+total.cell+yield+PL+rab+Thr+PO4.ferm.+PO4.apporte+PO4.utilise; 0.428, 0.725, pH+tmp+Nitrogen.Conc.+X.F.Suc+X.VXdt+yield+emission_CO2+His+PO4.ferm.+PO4.apporte+PO4.utilise; 0.418, 0.725, pH+Nitrogen.Conc.+X.F.Suc+X.VXdt+total.cell+yield+emission_O2+Thr+His+PO4.ferm.+PO4.apporte+PO4.utilise; 0.428, 0.725, pH+Main.P-Source.Conc.+Nitrogen.Conc.+X.F.Suc+X.VXdt+yield+rab+His+PO4.ferm.+PO4.apporte+PO4.utilise; 0.418, 0.725, pH+tmp+Nitrogen.Conc.+OD+X.F.Suc+X.VXdt+yield+emission_O2+Thr+PO4.ferm.+PO4.apporte+PO4.utilise; 0.406, 0.725, pH+Nitrogen.Conc.+X.F.Suc+X.VXdt+total.cell+yield+PL+emission_O2+rab+Thr+PO4.ferm.+PO4.apporte+PO4.utilise; 0.418, 0.725, pH+Main.Thr.Conc.+Nitrogen.Conc.+X.F.Suc+X.VXdt+total.cell+yield+rab+Thr+PO4.ferm.+PO4.apporte+PO4.utilise; 0.428, 0.725, pH+Nitrogen.Conc.+X.F.Suc+X.VXdt+yield+PL+emission_CO2+rab+PO4.ferm.+PO4.apporte+PO4.utilise; 0.417, 0.725, pH+Nitrogen.Conc.+X.F.Suc+X.VXdt+yield+PL+emission_CO2+rab+Thr+PO4.ferm.+PO4.apporte+PO4.utilise; 0.417, 0.725, pH+Main.P-Source.Conc.+Nitrogen.Conc.+X.F.Suc+X.VXdt+yield+rab+Thr+lactate+PO4.ferm.+PO4.apporte+PO4.utilise; 0.406, 0.724, pH+Main.P-Source.Conc.+Nitrogen.Conc.+X.F.Suc+X.VXdt+total.cell+yield+PL+rab+Thr+PO4.ferm.+PO4.apporte+PO4.utilise; 0.406, 0.724, pH+P-Source.Feed.conc.+Nitrogen.Conc.+X.F.Suc+X.VXdt+total.cell+yield+rab+Thr+His+PO4.ferm.+PO4.apporte+PO4.utilise; 0.428, 0.724, pH+Nitrogen.Conc.+OD+X.F.Suc+X.VXdt+yield+PL+emission_O2+PO4.ferm.+PO4.apporte+PO4.utilise; 0.417, 0.724, pH+P-Source.Feed.conc.+Nitrogen.Conc.+X.F.Suc+X.VXdt+yield+rab+Thr+His+PO4.ferm.+PO4.apporte+PO4.utilise; 0.417, 0.724, pH+Nitrogen.Conc.+X.F.Suc+X.VXdt+yield+PL+emission_O2+Thr+lactate+PO4.ferm.+PO4.apporte+PO4.utilise; 0.417, 0.724, pH+tmp+Nitrogen.Conc.+X.F.Suc+X.VXdt+total.cell+yield+emission_CO2+Thr+PO4.ferm.+PO4.apporte+PO4.utilise; 0.417, 0.724, pH+Nitrogen.Conc.+X.F.Suc+X.VXdt+total.cell+yield+PL+emission_O2+Thr+PO4.ferm.+PO4.apporte+PO4.utilise; 0.428, 0.724, pH+Nitrogen.Conc.+X.F.Suc+X.VXdt+yield+emission_O2+rab+lactate+PO4.ferm.+PO4.apporte+PO4.utilise; 0.438, 0.724, pH+Nitrogen.Conc.+X.F.Suc+X.VXdt+yield+emission_O2+lactate+PO4.ferm.+PO4.apporte+PO4.utilise; 0.406, 0.724, pH+tmp+Nitrogen.Conc.+X.F.Suc+X.VXdt+total.cell+yield+emission_O2+rab+Thr+PO4.ferm.+PO4.apporte+PO4.utilise; 0.417, 0.724, pH+Nitrogen.Conc.+X.F.Suc+X.VXdt+yield+emission_CO2+rab+Thr+His+PO4.ferm.+PO4.apporte+PO4.utilise; 0.405, 0.724, pH+Nitrogen.Conc.+X.F.Suc+X.VXdt+yield+PL+rab+Thr+His+lactate+

PO4.ferm.+PO4.apporte+PO4.utilise; 0.417, 0.724, pH+P-Source.Feed.conc.+Nitrogen.Conc.+X.F.Suc+X.VXdt+yield+PL+rab+Thr+PO4.ferm.+PO4.apporte+PO4.utilise; 0.394, 0.724, pH+tmp+Nitrogen.Conc.+OD+X.F.Suc+X.VXdt+yield+PL+emission_CO2+Thr+His+PO4.ferm.+PO4.apporte+PO4.utilise; 0.405, 0.724, pH+Nitrogen.Conc.+X.F.Suc+X.VXdt+total.cell+yield+PL+rab+Thr+lactate+PO4.ferm.+PO4.apporte+PO4.utilise; 0.438, 0.724, pH+Nitrogen.Conc.+X.F.Suc+X.VXdt+total.cell+yield+emission_O2+PO4.ferm.+PO4.apporte+PO4.utilise; 0.416, 0.724, pH+P-Source.Feed.conc.+Nitrogen.Conc.+X.F.Suc+X.VXdt+total.cell+yield+emission_O2+Thr+PO4.ferm.+PO4.apporte+PO4.utilise; 0.416, 0.724, pH+Nitrogen.Conc.+X.F.Suc+X.VXdt+yield+PL+emission_O2+emission_CO2+Thr+PO4.ferm.+PO4.apporte+PO4.utilise; 0.448, 0.724, pH+tmp+Nitrogen.Conc.+X.VXdt+total.cell+yield+emission_O2+Thr+His; 0.416, 0.724, pH+Nitrogen.Conc.+X.F.Suc+X.VXdt+total.cell+yield+PL+rab+His+PO4.ferm.+PO4.apporte+PO4.utilise; 0.427, 0.724, pH+tmp+Nitrogen.Conc.+X.F.Suc+X.VXdt+yield+emission_O2+rab+PO4.ferm.+PO4.apporte+PO4.utilise; 0.393, 0.724, pH+tmp+Nitrogen.Conc.+X.F.Suc+X.VXdt+total.cell+yield+emission_O2+emission_CO2+Thr+His+PO4.ferm.+PO4.apporte+PO4.utilise; 0.393, 0.724, pH+Main.P-Source.Conc.+Nitrogen.Conc.+OD+X.F.Suc+X.VXdt+yield+PL+rab+Thr+lactate+PO4.ferm.+PO4.apporte+PO4.utilise; 0.416, 0.724, pH+Nitrogen.Conc.+X.F.Suc+X.VXdt+yield+emission_O2+Thr+His+lactate+PO4.ferm.+PO4.apporte+PO4.utilise; 0.427, 0.724, pH+Nitrogen.Conc.+X.F.Suc+X.VXdt+yield+PL+emission_O2+His+PO4.ferm.+PO4.apporte+PO4.utilise; 0.457, 0.724, pH+tmp+X.VXdt+total.cell+yield+emission_CO2+Thr+His; 0.416, 0.724, pH+Nitrogen.Conc.+X.F.Suc+X.VXdt+yield+emission_O2+rab+Thr+lactate+PO4.ferm.+PO4.apporte+PO4.utilise; 0.426, 0.723, pH+Nitrogen.Conc.+X.F.Suc+X.VXdt+yield+PL+emission_O2+emission_CO2+PO4.ferm.+PO4.apporte+PO4.utilise; 0.437, 0.723, pH+Main.Thr.Conc.+Nitrogen.Conc.+X.F.Suc+X.VXdt+yield+rab+PO4.ferm.+PO4.apporte+PO4.utilise; 0.380, 0.723, pH+tmp+Nitrogen.Conc.+X.F.Suc+X.VXdt+total.cell+yield+PL+emission_O2+rab+Thr+His+PO4.ferm.+PO4.apporte+PO4.utilise; 0.404, 0.723, pH+Main.P-Source.Conc.+Main.Thr.Conc.+Nitrogen.Conc.+OD+X.F.Suc+X.VXdt+yield+rab+Thr+PO4.ferm.+PO4.apporte+PO4.utilise; 0.404, 0.723, pH+Nitrogen.Conc.+X.F.Suc+X.VXdt+total.cell+yield+emission_O2+rab+Thr+His+PO4.ferm.+PO4.apporte+PO4.utilise; 0.404, 0.723, pH+Nitrogen.Conc.+X.F.Suc+X.VXdt+total.cell+yield+rab+Thr+His+lactate+PO4.ferm.+PO4.apporte+PO4.utilise; 0.426, 0.723, pH+tmp+Nitrogen.Conc.+X.F.Suc+yield+emission_CO2+Thr+His+PO4.ferm.+PO4.apporte+PO4.utilise; 0.380, 0.723, pH+Nitrogen.Conc.+OD+X.F.Suc+X.VXdt+yield+PL+emission_O2+emission_CO2+rab+Thr+His+PO4.ferm.+PO4.apporte+PO4.utilise; 0.426, 0.723, pH+Nitrogen.Conc.+X.F.Suc+X.VXdt+total.cell+yield+emission_O2+emission_CO2+PO4.ferm.+PO4.apporte+PO4.utilise; 0.415, 0.723, pH+Nitrogen.Conc.+OD+X.F.Suc+X.VXdt+yield+PL+emission_O2+rab+PO4.ferm.+PO4.apporte+PO4.utilise; 0.426, 0.723, pH+Nitrogen.Conc.+X.F.Suc+X.VXdt+yield+emission_CO2+rab+His+PO4.ferm.+PO4.apporte+PO4.utilise; 0.426, 0.723, pH+tmp+Main.P-Source.Conc.+Nitrogen.Conc.+X.F.Suc+X.VXdt+yield+rab+PO4.ferm.+PO4.apporte+PO4.utilise; 0.404, 0.723, pH+Nitrogen.Conc.+X.F.Suc+X.VXdt+total.cell+yield+PL+emission_CO2+rab+Thr+PO4.ferm.+PO4.apporte+PO4.utilise; 0.426, 0.723, pH+Main.Thr.Conc.+Nitrogen.Conc.+X.F.Suc+X.VXdt+yield+emission_O2+Thr+PO4.ferm.+PO4.apporte+PO4.utilise; 0.415, 0.723, pH+Nitrogen.Conc.+X.F.Suc+X.VXdt+yield+emission_O2+emission_CO2+Thr+His+PO4.ferm.+PO4.apporte+PO4.utilise; 0.392, 0.723, pH+Main.P-Source.Conc.+Nitrogen.Conc.+OD+X.F.Suc+X.VXdt+yield+PL+emission_O2+rab+Thr+PO4.ferm.+PO4.apporte+PO4.utilise; 0.426, 0.723, pH+Main.P-Source.Conc.+Nitrogen.Conc.+X.F.Suc+X.VXdt+yield+emission_O2+rab+PO4.ferm.+PO4.apporte+PO4.utilise; 0.415, 0.723, pH+tmp+Nitrogen.Conc.+X.F.Suc+X.VXdt+yield+emission_O2+rab+His+PO4.ferm.+PO4.apporte+PO4.utilise; 0.403, 0.723, pH+tmp+Nitrogen.Conc.+X.F.Suc+X.VXdt+total.cell+yield+emission_CO2+rab+Thr+PO4.ferm.+PO4.apporte+PO4.utilise; 0.415, 0.723, pH+Main.P-Source.Conc.+Main.Thr.Conc.+Nitrogen.Conc.+X.F.Suc+X.VXdt+yield+rab+Thr+PO4.ferm.+PO4.apporte+PO4.utilise; 0.379, 0.723, pH+tmp+Nitrogen.Conc.+X.F.Suc+X.VXdt+total.cell+yield+PL+emission_CO2+rab+Thr+His+PO4.ferm.+PO4.apporte+PO4.utilise; 0.425, 0.723, pH+Main.P-Source.Conc.+Nitrogen.Conc.+X.F.Suc+X.VXdt+yield+rab+lactate+PO4.ferm.+PO4.apporte+PO4.utilise; 0.403, 0.723, pH+Main.Thr.Conc.+Nitrogen.Conc.+OD+X.F.Suc+X.VXdt+yield+PL+emission_O2+Thr+PO4.ferm.+PO4.apporte+PO4.utilise; 0.403, 0.723, pH+Main.P-Source.Conc.+Nitrogen.Conc.+X.F.Suc+X.VXdt+total.cell+yield+rab+Thr+His+PO4.ferm.+PO4.apporte+PO4.utilise; 0.415, 0.723, pH+tmp+Nitrogen.Conc.+X.F.Suc+X.VXdt+total.cell+yield+emission_O2+rab+PO4.ferm.+PO4.apporte+PO4.utilise; 0.392, 0.723, pH+tmp+Nitrogen.Conc.+OD+X.F.Suc+X.VXdt+yield+PL+emission_O2+Thr+His+PO4.ferm.+PO4.apporte+PO4.utilise; 0.414, 0.723, pH+tmp+Nitrogen.Conc.+X.F.Suc+X.VXdt+yield+PL+rab+Thr+PO4.ferm.+PO4.apporte+PO4.utilise; 0.391, 0.723, pH+Nitrogen.Conc.+OD+X.F.Suc+X.VXdt+yield+PL+emission_O2+rab+Thr+lactate+PO4.ferm.+PO4.apporte+PO4.utilise; 0.391, 0.723, pH+Main.P-Source.Conc.+Nitrogen.Conc.+OD+X.F.Suc+X.VXdt+yield+rab+Thr+His+lactate+PO4.ferm.+PO4.apporte+PO4.utilise; 0.425, 0.723, pH+Nitrogen.Conc.+X.F.Suc+X.VXdt+yield+emission_CO2+rab+lactate+PO4.ferm.+PO4.apporte+PO4.utilise; 0.403, 0.723, pH+P-Source.Feed.conc.+Nitrogen.Conc.+OD+X.F.Suc+X.VXdt+yield+emission_O2+rab+Thr+PO4.ferm.+PO4.apporte+PO4.utilise; 0.425, 0.723, pH+tmp+Nitrogen.Conc.+X.F.Suc+X.VXdt+yield+emission_CO2+rab+PO4.ferm.+PO4.apporte+PO4.utilise; 0.414, 0.723, pH+Nitrogen.Conc.+OD+X.F.Suc+X.VXdt+yield+emission_O2+rab+His+PO4.ferm.+PO4.apporte+PO4.utilise; 0.414, 0.723, pH+tmp+Main.P-Source.Conc.+Nitrogen.Conc.+X.F.Suc+X.VXdt+total.cell+yield+rab+PO4.ferm.+PO4.apporte+PO4.utilise; 0.435, 0.723, pH+tmp+Nitrogen.Conc.+X.VXdt+total.cell+yield+PL+emission_O2+Thr+His; 0.414, 0.723, pH+Main.P-Source.Conc.+Nitrogen.Conc.+X.F.Suc+X.VXdt+yield+emission_O2+rab+Thr+PO4.ferm.+PO4.apporte+PO4.utilise; 0.414, 0.723, pH+Main.Thr.Conc.+Nitrogen.Conc.+X.F.Suc+X.VXdt+yield+rab+Thr+lactate+PO4.ferm.+PO4.apporte+PO4.utilise; 0.391, 0.723, pH+P-Source.Feed.conc.+Nitrogen.Conc.+OD+X.F.Suc+X.VXdt+yield+PL+rab+Thr+His+PO4.ferm.+PO4.apporte+PO4.utilise; 0.403, 0.723, pH+tmp+Nitrogen.Conc.+X.F.Suc+X.VXdt+yield+PL+rab+Thr+His+PO4.ferm.+PO4.apporte+PO4.utilise; 0.403, 0.723, pH+Main.Thr.Conc.+Nitrogen.Conc.+OD+X.F.Suc+X.VXdt+yield+emission_O2+rab+Thr+PO4.ferm.+PO4.apporte+PO4.utilise; 0.414, 0.723, pH+P-Source.Feed.conc.+Nitrogen.Conc.+X.F.Suc+X.VXdt+yield+emission_O2+Thr+His+PO4.ferm.+PO4.apporte+PO4.utilise; 0.435, 0.723, pH+tmp+X.F.Suc+yield+emission_CO2+Thr+His+

PO4.ferm.+PO4.apporte+PO4.utilise; 0.414, 0.723, pH+Nitrogen.Conc.+X.F.Suc+X.VXdt+yield+emission_CO2+rab+Thr+lactate+PO4.ferm.+PO4.apporte+PO4.utilise; 0.403, 0.723, pH+Main.Thr.Conc.+Nitrogen.Conc.+OD+X.F.Suc+X.VXdt+yield+rab+Thr+lactate+PO4.ferm.+PO4.apporte+PO4.utilise; 0.414, 0.723, pH+tmp+Nitrogen.Conc.+OD+X.F.Suc+X.VXdt+yield+rab+Thr+PO4.ferm.+PO4.apporte+PO4.utilise; 0.414, 0.722, pH+Nitrogen.Conc.+X.F.Suc+X.VXdt+yield+PL+rab+His+lactate+PO4.ferm.+PO4.apporte+PO4.utilise; 0.414, 0.722, pH+Nitrogen.Conc.+X.F.Suc+X.VXdt+total.cell+yield+PL+emission_O2+rab+PO4.ferm.+PO4.apporte+PO4.utilise; 0.414, 0.722, pH+Nitrogen.Conc.+OD+X.F.Suc+X.VXdt+yield+PL+rab+lactate+PO4.ferm.+PO4.apporte+PO4.utilise; 0.391, 0.722, pH+P-Source.Feed.conc.+Nitrogen.Conc.+OD+X.F.Suc+X.VXdt+yield+PL+emission_O2+Thr+His+PO4.ferm.+PO4.apporte+PO4.utilise; 0.391, 0.722, pH+Main.P-Source.Conc.+Nitrogen.Conc.+OD+X.F.Suc+X.VXdt+yield+emission_O2+rab+Thr+His+PO4.ferm.+PO4.apporte+PO4.utilise; 0.402, 0.722, pH+Main.P-Source.Conc.+Nitrogen.Conc.+X.F.Suc+X.VXdt+yield+PL+rab+Thr+His+PO4.ferm.+PO4.apporte+PO4.utilise; 0.413, 0.722, pH+tmp+Nitrogen.Conc.+X.F.Suc+X.VXdt+yield+emission_CO2+rab+His+PO4.ferm.+PO4.apporte+PO4.utilise; 0.424, 0.722, pH+tmp+Main.P-Source.Conc.+Nitrogen.Conc.+X.F.Suc+X.VXdt+yield+emission_O2+PO4.ferm.+PO4.apporte+PO4.utilise; 0.390, 0.722, pH+Main.Thr.Conc.+Nitrogen.Conc.+OD+X.F.Suc+X.VXdt+yield+PL+rab+Thr+His+PO4.ferm.+PO4.apporte+PO4.utilise; 0.390, 0.722, pH+Main.P-Source.Conc.+Nitrogen.Conc.+OD+X.F.Suc+X.VXdt+yield+PL+emission_CO2+rab+Thr+PO4.ferm.+PO4.apporte+PO4.utilise; 0.402, 0.722, pH+tmp+Nitrogen.Conc.+X.F.Suc+X.VXdt+total.cell+yield+emission_O2+emission_CO2+Thr+PO4.ferm.+PO4.apporte+PO4.utilise; 0.413, 0.722, pH+Main.Thr.Conc.+Nitrogen.Conc.+X.F.Suc+X.VXdt+yield+PL+rab+Thr+PO4.ferm.+PO4.apporte+PO4.utilise; 0.390, 0.722, pH+Nitrogen.Conc.+OD+X.F.Suc+X.VXdt+yield+PL+emission_CO2+rab+Thr+lactate+PO4.ferm.+PO4.apporte+PO4.utilise; 0.390, 0.722, pH+Nitrogen.Conc.+OD+X.F.Suc+X.VXdt+yield+emission_O2+rab+Thr+His+lactate+PO4.ferm.+PO4.apporte+PO4.utilise; 0.424, 0.722, pH+P-Source.Feed.conc.+Nitrogen.Conc.+X.F.Suc+X.VXdt+total.cell+yield+rab+PO4.ferm.+PO4.apporte+PO4.utilise; 0.424, 0.722, pH+tmp+Nitrogen.Conc.+X.F.Suc+X.VXdt+yield+emission_O2+emission_CO2+PO4.ferm.+PO4.apporte+PO4.utilise; 0.413, 0.722, pH+Main.P-Source.Conc.+Nitrogen.Conc.+OD+X.F.Suc+X.VXdt+yield+PL+rab+PO4.ferm.+PO4.apporte+PO4.utilise; 0.413, 0.722, pH+Nitrogen.Conc.+OD+X.F.Suc+X.VXdt+yield+PL+emission_CO2+rab+PO4.ferm.+PO4.apporte+PO4.utilise; 0.413, 0.722, pH+tmp+Nitrogen.Conc.+X.F.Suc+X.VXdt+total.cell+yield+emission_CO2+His+PO4.ferm.+PO4.apporte+PO4.utilise; 0.413, 0.722, pH+tmp+Nitrogen.Conc.+X.F.Suc+yield+PL+emission_CO2+Thr+His+PO4.ferm.+PO4.apporte+PO4.utilise; 0.378, 0.722, pH+tmp+Nitrogen.Conc.+X.F.Suc+X.VXdt+total.cell+yield+PL+emission_O2+emission_CO2+Thr+His+PO4.ferm.+PO4.apporte+PO4.utilise; 0.413, 0.722, pH+Nitrogen.Conc.+X.F.Suc+X.VXdt+yield+emission_O2+emission_CO2+Thr+lactate+PO4.ferm.+PO4.apporte+PO4.utilise; 0.423, 0.722, pH+Nitrogen.Conc.+X.F.Suc+X.VXdt+yield+emission_O2+emission_CO2+His+PO4.ferm.+PO4.apporte+PO4.utilise; 0.401, 0.722, pH+Nitrogen.Conc.+X.F.Suc+X.VXdt+total.cell+yield+PL+emission_O2+emission_CO2+Thr+PO4.ferm.+PO4.apporte+PO4.utilise; 0.401, 0.722, pH+Main.P-Source.Conc.+Nitrogen.Conc.+X.F.Suc+X.VXdt+total.cell+yield+emission_O2+rab+Thr+PO4.ferm.+PO4.apporte+PO4.utilise; 0.401, 0.722, pH+tmp+Nitrogen.Conc.+OD+X.F.Suc+X.VXdt+yield+rab+Thr+His+PO4.ferm.+PO4.apporte+PO4.utilise; 0.434, 0.722, pH+Main.P-Source.Conc.+Nitrogen.Conc.+X.F.Suc+X.VXdt+yield+emission_O2+PO4.ferm.+PO4.apporte+PO4.utilise; 0.423, 0.722, pH+Main.P-Source.Conc.+Nitrogen.Conc.+X.F.Suc+X.VXdt+yield+emission_CO2+rab+PO4.ferm.+PO4.apporte+PO4.utilise; 0.401, 0.722, pH+Main.Thr.Conc.+Nitrogen.Conc.+OD+X.F.Suc+X.VXdt+yield+emission_CO2+rab+Thr+PO4.ferm.+PO4.apporte+PO4.utilise; 0.401, 0.722, pH+Nitrogen.Conc.+X.F.Suc+X.VXdt+total.cell+yield+emission_CO2+rab+Thr+His+PO4.ferm.+PO4.apporte+PO4.utilise; 0.401, 0.722, pH+tmp+Nitrogen.Conc.+X.F.Suc+X.VXdt+yield+emission_O2+rab+Thr+His+PO4.ferm.+PO4.apporte+PO4.utilise; 0.389, 0.722, pH+tmp+Nitrogen.Conc.+X.F.Suc+X.VXdt+total.cell+yield+PL+emission_O2+rab+Thr+PO4.ferm.+PO4.apporte+PO4.utilise; 0.401, 0.722, pH+P-Source.Feed.conc.+Nitrogen.Conc.+OD+X.F.Suc+X.VXdt+yield+emission_CO2+rab+Thr+PO4.ferm.+PO4.apporte+PO4.utilise; 0.401, 0.722, pH+Nitrogen.Conc.+X.F.Suc+X.VXdt+total.cell+yield+emission_O2+emission_CO2+rab+Thr+PO4.ferm.+PO4.apporte+PO4.utilise; 0.412, 0.722, pH+Main.Thr.Conc.+Nitrogen.Conc.+X.F.Suc+X.VXdt+yield+emission_O2+Thr+His+PO4.ferm.+PO4.apporte+PO4.utilise; 0.389, 0.722, pH+Main.P-Source.Conc.+Nitrogen.Conc.+OD+X.F.Suc+X.VXdt+yield+emission_CO2+rab+Thr+His+PO4.ferm.+PO4.apporte+PO4.utilise; 0.412, 0.722, pH+tmp+Nitrogen.Conc.+X.F.Suc+X.VXdt+yield+PL+emission_CO2+His+PO4.ferm.+PO4.apporte+PO4.utilise; 0.412, 0.722, pH+tmp+Nitrogen.Conc.+X.F.Suc+X.VXdt+total.cell+yield+emission_CO2+rab+PO4.ferm.+PO4.apporte+PO4.utilise; 0.401, 0.722, pH+Nitrogen.Conc.+OD+X.F.Suc+X.VXdt+yield+rab+Thr+His+SO4.ferm.+PO4.ferm.+PO4.apporte+PO4.utilise; 0.412, 0.722, pH+Main.P-Source.Conc.+Nitrogen.Conc.+X.F.Suc+X.VXdt+yield+emission_CO2+rab+Thr+PO4.ferm.+PO4.apporte+PO4.utilise; 0.412, 0.722, pH+Main.P-Source.Conc.+Nitrogen.Conc.+X.F.Suc+X.VXdt+yield+PL+emission_O2+Thr+PO4.ferm.+PO4.apporte+PO4.utilise; 0.389, 0.722, pH+Main.P-Source.Conc.+Nitrogen.Conc.+OD+X.F.Suc+X.VXdt+yield+emission_O2+Thr+His+lactate+PO4.ferm.+PO4.apporte+PO4.utilise; 0.389, 0.722, pH+Nitrogen.Conc.+OD+X.F.Suc+X.VXdt+yield+emission_CO2+rab+Thr+His+lactate+PO4.ferm.+PO4.apporte+PO4.utilise; 0.412, 0.721, pH+Nitrogen.Conc.+OD+X.F.Suc+X.VXdt+yield+emission_CO2+rab+His+PO4.ferm.+PO4.apporte+PO4.utilise; 0.401, 0.721, pH+tmp+Nitrogen.Conc.+OD+X.F.Suc+X.VXdt+yield+PL+emission_O2+Thr+PO4.ferm.+PO4.apporte+PO4.utilise; 0.412, 0.721, pH+P-Source.Feed.conc.+Nitrogen.Conc.+X.F.Suc+X.VXdt+yield+PL+emission_O2+Thr+PO4.ferm.+PO4.apporte+PO4.utilise; 0.412, 0.721, pH+Nitrogen.Conc.+X.F.Suc+X.VXdt+total.cell+yield+PL+rab+lactate+PO4.ferm.+PO4.apporte+PO4.utilise; 0.412, 0.721, pH+Nitrogen.Conc.+OD+X.F.Suc+X.VXdt+yield+PL+emission_O2+His+PO4.ferm.+PO4.apporte+PO4.utilise; 0.401, 0.721, pH+Main.Thr.Conc.+Nitrogen.Conc.+X.F.Suc+X.VXdt+total.cell+yield+rab+Thr+His+PO4.ferm.+PO4.apporte+PO4.utilise; 0.423, 0.721, pH+Nitrogen.Conc.+X.F.Suc+X.VXdt+yield+emission_O2+emission_CO2+lactate+PO4.ferm.+PO4.apporte+PO4.utilise; 0.400, 0.721, pH+tmp+Nitrogen.Conc.+X.F.Suc+X.VXdt+total.cell+yield+emission_O2+rab+His+PO4.ferm.+PO4.apporte+PO4.utilise; 0.389, 0.721, pH+tmp+Main.P-Source.Conc.+Nitrogen.Conc.+X.F.Suc+X.VXdt+ total.cell+yield+emission_O2+Thr+His+PO4.ferm.+PO4.apporte+PO4.utilise; 0.412, 0.721, pH+Main.P-Source.Conc.+Nitrogen.Conc.+X.F.Suc+X.VXdt+yield+emission_O2+Thr+His+PO4.ferm.+PO4.apporte+PO4.utilise; 0.423, 0.721, pH+tmp+X.F.Suc+yield+PL+emission_CO2+Thr+His+PO4.ferm.+PO4.apporte+PO4.utilise; 0.443, 0.721, pH+tmp+X.VXdt+total.cell+yield+PL+emission_CO2+Thr+His; 0.412, 0.721, pH+tmp+Nitrogen.Conc.+X.F.Suc+X.VXdt+yield+emission_O2+emission_CO2+His+PO4.ferm.+PO4.apporte+PO4.utilise; 0.412, 0.721, pH+tmp+Main.P-Source.Conc.+Nitrogen.Conc.+X.F.Suc+X.VXdt+yield+emission_O2+His+PO4.ferm.+PO4.apporte+PO4.utilise; 0.389, 0.721, pH+Main.P-Source.Conc.+Nitrogen.Conc.+OD+X.F.Suc+X.VXdt+yield+PL+emission_O2+Thr+lactate+PO4.ferm.+PO4.apporte+PO4.utilise; 0.400, 0.721, pH+Nitrogen.Conc.+X.F.Suc+X.VXdt+yield+PL+emission_O2+rab+Thr+His+PO4.ferm.+PO4.apporte+PO4.utilise; 0.400, 0.721, pH+Main.P-Source.Conc.+Main.Thr.Conc.+Nitrogen.Conc.+OD+X.F.Suc+X.VXdt+yield+emission_O2+Thr+PO4.ferm.+PO4.apporte+PO4.utilise; 0.400, 0.721, pH+tmp+Main.P-Source.Conc.+Nitrogen.Conc.+X.F.Suc+X.VXdt+total.cell+yield+emission_O2+Thr+PO4.ferm.+PO4.apporte+PO4.utilise; 0.400, 0.721, pH+tmp+Nitrogen.Conc.+X.F.Suc+X.VXdt+total.cell+yield+PL+emission_CO2+Thr+PO4.ferm.+PO4.apporte+PO4.utilise; 0.411, 0.721, pH+Nitrogen.Conc.+OD+X.F.Suc+X.VXdt+yield+emission_O2+emission_CO2+rab+PO4.ferm.+PO4.apporte+PO4.utilise; 0.411, 0.721, pH+Nitrogen.Conc.+X.F.Suc+X.VXdt+yield+emission_O2+emission_CO2+rab+Thr+PO4.ferm.+PO4.apporte+PO4.utilise; 0.411, 0.721, pH+Main.P-Source.Conc.+Nitrogen.Conc.+X.F.Suc+X.VXdt+total.cell+yield+PL+rab+PO4.ferm.+PO4.apporte+PO4.utilise; 0.400, 0.721, pH+Nitrogen.Conc.+X.F.Suc+X.VXdt+total.cell+yield+PL+emission_O2+Thr+His+PO4.ferm.+PO4.apporte+PO4.utilise; 0.411, 0.721, pH+Nitrogen.Conc.+OD+X.F.Suc+X.VXdt+yield+rab+His+lactate+PO4.ferm.+PO4.apporte+PO4.utilise; 0.443, 0.721, pH+tmp+Nitrogen.Conc.+X.VXdt+total.cell+yield+rab+Thr+His; 0.411, 0.721, pH+Main.P-Source.Conc.+Nitrogen.Conc.+X.F.Suc+X.VXdt+yield+emission_O2+emission_CO2+Thr+PO4.ferm.+PO4.apporte+PO4.utilise; 0.422, 0.721, pH+Nitrogen.Conc.+X.F.Suc+X.VXdt+yield+emission_O2+emission_CO2+rab+PO4.ferm.+PO4.apporte+PO4.utilise; 0.388, 0.721, pH+Nitrogen.Conc.+OD+X.F.Suc+X.VXdt+yield+PL+emission_O2+emission_CO2+Thr+lactate+PO4.ferm.+PO4.apporte+PO4.utilise; 0.422, 0.721, pH+Nitrogen.Conc.+X.F.Suc+X.VXdt+total.cell+yield+emission_O2+His+PO4.ferm.+PO4.apporte+PO4.utilise; 0.400, 0.721, pH+Main.Thr.Conc.+Nitrogen.Conc.+OD+X.F.Suc+X.VXdt+yield+emission_O2+emission_CO2+Thr+PO4.ferm.+PO4.apporte+PO4.utilise; 0.422, 0.721, pH+P-Source.Feed.conc.+Nitrogen.Conc.+X.F.Suc+X.VXdt+yield+PL+rab+PO4.ferm.+PO4.apporte+PO4.utilise; 0.411, 0.721, pH+Nitrogen.Conc.+X.F.Suc+X.VXdt+yield+PL+emission_O2+rab+His+PO4.ferm.+PO4.apporte+PO4.utilise; 0.422, 0.721, pH+Nitrogen.Conc.+X.F.Suc+X.VXdt+yield+PL+emission_O2+lactate+PO4.ferm.+PO4.apporte+PO4.utilise; 0.422, 0.721, pH+tmp+Nitrogen.Conc.+OD+X.F.Suc+X.VXdt+yield+rab+PO4.ferm.+PO4.apporte+PO4.utilise; 0.399, 0.721, pH+Main.P-Source.Conc.+P-Source.Feed.conc.+Nitrogen.Conc.+OD+X.F.Suc+X.VXdt+yield+rab+Thr+PO4.ferm.+PO4.apporte+PO4.utilise; 0.388, 0.721, pH+Main.P-Source.Conc.+Nitrogen.Conc.+OD+X.F.Suc+X.VXdt+yield+PL+emission_O2+emission_CO2+Thr+PO4.ferm.+PO4.apporte+PO4.utilise; 0.411, 0.721, pH+Nitrogen.Conc.+X.F.Suc+X.VXdt+total.cell+yield+emission_O2+Thr+lactate+PO4.ferm.+PO4.apporte+PO4.utilise; 0.399, 0.721, pH+tmp+Nitrogen.Conc.+X.F.Suc+X.VXdt+yield+emission_CO2+rab+Thr+His+PO4.ferm.+PO4.apporte+PO4.utilise; 0.388, 0.721, pH+tmp+Nitrogen.Conc.+X.F.Suc+X.VXdt+total.cell+yield+rab+Thr+His+SO4.ferm.+PO4.ferm.+PO4.apporte+PO4.utilise; 0.411, 0.721, pH+Main.P-Source.Conc.+Nitrogen.Conc.+OD+X.F.Suc+X.VXdt+yield+rab+His+PO4.ferm.+PO4.apporte+PO4.utilise; 0.411, 0.721, pH+Nitrogen.Conc.+X.F.Suc+X.VXdt+total.cell+yield+PL+emission_CO2+rab+PO4.ferm.+PO4.apporte+PO4.utilise; 0.399, 0.721, pH+tmp+Main.P-Source.Conc.+Nitrogen.Conc.+X.F.Suc+X.VXdt+total.cell+yield+rab+Thr+PO4.ferm.+PO4.apporte+PO4.utilise; 0.411, 0.721, pH+Main.P-Source.Conc.+Nitrogen.Conc.+X.F.Suc+X.VXdt+yield+PL+rab+His+PO4.ferm.+PO4.apporte+PO4.utilise; 0.399, 0.721, pH+P-Source.Feed.conc.+Nitrogen.Conc.+OD+X.F.Suc+X.VXdt+yield+emission_O2+emission_CO2+Thr+PO4.ferm.+PO4.apporte+PO4.utilise; 0.421, 0.721, pH+tmp+Nitrogen.Conc.+X.VXdt+total.cell+yield+emission_O2+emission_CO2+rab+Thr+His; 0.410, 0.721, pH+Nitrogen.Conc.+X.F.Suc+X.VXdt+yield+PL+emission_O2+rab+lactate+PO4.ferm.+PO4.apporte+PO4.utilise; 0.421, 0.721, pH+Main.P-Source.Conc.+Nitrogen.Conc.+X.F.Suc+X.VXdt+yield+emission_O2+emission_CO2+PO4.ferm.+PO4.apporte+PO4.utilise; 0.421, 0.721, pH+P-Source.Feed.conc.+Nitrogen.Conc.+X.F.Suc+X.VXdt+yield+rab+His+PO4.ferm.+PO4.apporte+PO4.utilise; 0.410, 0.721, pH+Nitrogen.Conc.+X.F.Suc+X.VXdt+total.cell+yield+emission_O2+rab+His+PO4.ferm.+PO4.apporte+PO4.utilise; 0.410, 0.721, pH+tmp+Main.P-Source.Conc.+Nitrogen.Conc.+X.F.Suc+X.VXdt+yield+rab+His+PO4.ferm.+PO4.apporte+PO4.utilise; 0.421, 0.721, pH+Nitrogen.Conc.+OD+X.F.Suc+X.VXdt+yield+emission_CO2+Thr+PO4.ferm.+PO4.apporte+PO4.utilise; 0.399, 0.721, pH+tmp+Nitrogen.Conc.+X.F.Suc+X.VXdt+total.cell+yield+emission_CO2+rab+His+PO4.ferm.+PO4.apporte+PO4.utilise; 0.410, 0.721, pH+Nitrogen.Conc.+OD+X.F.Suc+X.VXdt+yield+emission_O2+Thr+SO4.ferm.+PO4.ferm.+PO4.apporte+PO4.utilise; 0.387, 0.721, pH+tmp+Nitrogen.Conc.+X.F.Suc+X.VXdt+total.cell+yield+PL+emission_CO2+rab+Thr+PO4.ferm.+PO4.apporte+PO4.utilise; 0.421, 0.720, pH+Main.Thr.Conc.+Nitrogen.Conc.+X.F.Suc+X.VXdt+yield+rab+His+PO4.ferm.+PO4.apporte+PO4.utilise; 0.375, 0.720, pH+tmp+Nitrogen.Conc.+X.F.Suc+X.VXdt+total.cell+yield+emission_O2+emission_CO2+rab+Thr+His+PO4.ferm.+PO4.apporte+PO4.utilise; 0.421, 0.720, pH+tmp+Nitrogen.Conc.+X.VXdt+total.cell+yield+PL+emission_O2+Thr+His+PO4.utilise; 0.410, 0.720, pH+tmp+Nitrogen.Conc.+X.F.Suc+X.VXdt+total.cell+yield+emission_O2+emission_CO2+PO4.ferm.+PO4.apporte+PO4.utilise; 0.387, 0.720, pH+Nitrogen.Conc.+OD+X.F.Suc+X.VXdt+yield+emission_O2+emission_CO2+Thr+His+lactate+PO4.ferm.+PO4.apporte+PO4.utilise; 0.399, 0.720, pH+Main.Thr.Conc.+Nitrogen.Conc.+OD+X.F.Suc+X.VXdt+yield+emission_O2+Thr+lactate+PO4.ferm.+PO4.apporte+PO4.utilise; 0.410, 0.720, pH+Nitrogen.Conc.+OD+X.F.Suc+X.VXdt+yield+PL+emission_O2+emission_CO2+PO4.ferm.+PO4.apporte+PO4.utilise; 0.410, 0.720, pH+tmp+Main.P-Source.Conc.+Nitrogen.Conc.+X.F.Suc+X.VXdt+total.cell+yield+emission_O2+PO4.ferm.+PO4.apporte+PO4.utilise; 0.421, 0.720, pH+tmp+Nitrogen.Conc.+X.VXdt+total.cell+yield+PL+emission_CO2+Thr+His+PO4.utilise; 0.410, 0.720, pH+tmp+Nitrogen.Conc.+OD+X.F.Suc+X.VXdt+yield+emission_O2+His+PO4.ferm.+PO4.apporte+PO4.utilise; 0.399, 0.720, pH+P-Source.Feed.conc.+Nitrogen.Conc.+X.

F.Suc+X.VXdt+total.cell+yield+emission_O2+Thr+His+PO4.ferm.+PO4.apporte+PO4.utilise; 0.399, 0.720, pH+Nitrogen.Conc.+X.F.Suc+X.VXdt+total.cell+yield+emission_O2+rab+Thr+lactate+PO4.ferm.+PO4.apporte+PO4.utilise; 0.421, 0.720, pH+Nitrogen.Conc.+OD+X.F.Suc+X.VXdt+yield+emission_O2+lactate+PO4.ferm.+PO4.apporte+PO4.utilise; 0.399, 0.720, pH+Main.P-Source.Conc.+Nitrogen.Conc.+X.F.Suc+X.VXdt+total.cell+yield+emission_CO2+rab+Thr+PO4.ferm.+PO4.apporte+PO4.utilise; 0.410, 0.720, pH+Nitrogen.Conc.+OD+X.F.Suc+X.VXdt+yield+emission_CO2+Thr+His+PO4.ferm.+PO4.apporte+PO4.utilise; 0.421, 0.720, pH+tmp+Nitrogen.Conc.+OD+X.F.Suc+X.VXdt+yield+emission_O2+PO4.ferm.+PO4.apporte+PO4.utilise; 0.421, 0.720, pH+Nitrogen.Conc.+X.F.Suc+X.VXdt+total.cell+yield+PL+emission_O2+PO4.ferm.+PO4.apporte+PO4.utilise; 0.410, 0.720, pH+tmp+Nitrogen.Conc.+X.F.Suc+X.VXdt+yield+PL+emission_O2+rab+PO4.ferm.+PO4.apporte+PO4.utilise; 0.387, 0.720, pH+Main.Thr.Conc.+Nitrogen.Conc.+OD+X.F.Suc+X.VXdt+yield+PL+emission_O2+Thr+His+PO4.ferm.+PO4.apporte+PO4.utilise; 0.387, 0.720, pH+Main.P-Source.Conc.+Nitrogen.Conc.+OD+X.F.Suc+X.VXdt+yield+emission_O2+emission_CO2+rab+Thr+PO4.ferm.+PO4.apporte+PO4.utilise; 0.398, 0.720, pH+Main.P-Source.Conc.+Nitrogen.Conc.+X.F.Suc+X.VXdt+yield+PL+rab+Thr+lactate+PO4.ferm.+PO4.apporte+PO4.utilise; 0.398, 0.720, pH+P-Source.Feed.conc.+Nitrogen.Conc.+X.F.Suc+X.VXdt+total.cell+yield+emission_O2+rab+Thr+PO4.ferm.+PO4.apporte+PO4.utilise; 0.386, 0.720, pH+Main.P-Source.Conc.+Nitrogen.Conc.+OD+X.F.Suc+X.VXdt+yield+emission_O2+emission_CO2+Thr+His+PO4.ferm.+PO4.apporte+PO4.utilise; 0.398, 0.720, pH+Nitrogen.Conc.+OD+X.F.Suc+X.VXdt+yield+PL+rab+Thr+SO4.ferm.+PO4.ferm.+PO4.apporte+PO4.utilise; 0.398, 0.720, pH+Main.P-Source.Conc.+Main.Thr.Conc.+Nitrogen.Conc.+X.F.Suc+X.VXdt+yield+rab+Thr+His+PO4.ferm.+PO4.apporte+PO4.utilise; 0.420, 0.720, pH+tmp+Nitrogen.Conc.+X.F.Suc+X.VXdt+yield+emission_CO2+Thr+PO4.ferm.+PO4.apporte+PO4.utilise; 0.398, 0.720, pH+Nitrogen.Conc.+X.F.Suc+X.VXdt+total.cell+yield+emission_O2+emission_CO2+Thr+His+PO4.ferm.+PO4.apporte+PO4.utilise; 0.398, 0.720, pH+Nitrogen.Conc.+X.F.Suc+X.VXdt+yield+PL+emission_O2+Thr+His+lactate+PO4.ferm.+PO4.apporte+PO4.utilise; 0.398, 0.720, pH+Nitrogen.Conc.+X.F.Suc+X.VXdt+yield+PL+emission_CO2+rab+Thr+His+PO4.ferm.+PO4.apporte+PO4.utilise; 0.398, 0.720, pH+tmp+Nitrogen.Conc.+X.F.Suc+X.VXdt+yield+emission_O2+emission_CO2+Thr+His+PO4.ferm.+PO4.apporte+PO4.utilise; 0.386, 0.720, pH+P-Source.Feed.conc.+Nitrogen.Conc.+X.F.Suc+X.VXdt+total.cell+yield+PL+rab+Thr+His+PO4.ferm.+PO4.apporte+PO4.utilise; 0.420, 0.720, pH+tmp+Nitrogen.Conc.+X.VXdt+total.cell+yield+PL+rab+Thr+His+PO4.utilise; 0.398, 0.720, pH+tmp+Main.P-Source.Conc.+Nitrogen.Conc.+X.F.Suc+X.VXdt+total.cell+yield+rab+His+PO4.ferm.+PO4.apporte+PO4.utilise; 0.386, 0.720, pH+tmp+Nitrogen.Conc.+X.F.Suc+X.VXdt+total.cell+yield+emission_O2+Thr+His+SO4.ferm.+PO4.ferm.+PO4.apporte+PO4.utilise; 0.420, 0.720, pH+Nitrogen.Conc.+X.F.Suc+X.VXdt+yield+emission_O2+His+lactate+PO4.ferm.+PO4.apporte+PO4.utilise; 0.398, 0.720, pH+P-Source.Feed.conc.+Nitrogen.Conc.+X.F.Suc+X.VXdt+total.cell+yield+PL+emission_O2+Thr+PO4.ferm.+PO4.apporte+PO4.utilise; 0.409, 0.720, pH+tmp+Nitrogen.Conc.+OD+X.F.Suc+X.VXdt+yield+emission_CO2+Thr+PO4.ferm.+PO4.apporte+PO4.utilise; 0.409, 0.720, pH+Nitrogen.Conc.+X.F.Suc+X.VXdt+total.cell+yield+rab+His+lactate+PO4.ferm.+PO4.apporte+PO4.utilise; 0.398, 0.720, pH+P-Source.Feed.conc.+Nitrogen.Conc.+X.F.Suc+X.VXdt+yield+PL+rab+Thr+His+PO4.ferm.+PO4.apporte+PO4.utilise; 0.398, 0.720, pH+Main.Thr.Conc.+Nitrogen.Conc.+X.F.Suc+X.VXdt+yield+PL+rab+Thr+His+PO4.ferm.+PO4.apporte+PO4.utilise; 0.398, 0.720, pH+tmp+Nitrogen.Conc.+X.F.Suc+X.VXdt+yield+PL+emission_O2+rab+His+PO4.ferm.+PO4.apporte+PO4.utilise; 0.398, 0.720, pH+tmp+Nitrogen.Conc.+X.F.Suc+X.VXdt+total.cell+yield+PL+emission_O2+rab+PO4.ferm.+PO4.apporte+PO4.utilise; 0.431, 0.720, pH+tmp+Nitrogen.Conc.+X.VXdt+total.cell+yield+PL+rab+Thr+His; 0.409, 0.720, pH+Main.P-Source.Conc.+Nitrogen.Conc.+X.F.Suc+X.VXdt+total.cell+yield+emission_O2+Thr+PO4.ferm.+PO4.apporte+PO4.utilise; 0.430, 0.720, pH+tmp+Nitrogen.Conc.+X.VXdt+total.cell+yield+emission_CO2+Thr+His+PO4.utilise; 0.398, 0.720, pH+Main.P-Source.Conc.+Main.Thr.Conc.+Nitrogen.Conc.+X.F.Suc+X.VXdt+total.cell+yield+rab+Thr+PO4.ferm.+PO4.apporte+PO4.utilise; 0.386, 0.720, pH+Nitrogen.Conc.+OD+X.F.Suc+X.VXdt+yield+emission_O2+emission_CO2+rab+Thr+lactate+PO4.ferm.+PO4.apporte+PO4.utilise; 0.409, 0.720, pH+Nitrogen.Conc.+OD+X.F.Suc+X.VXdt+yield+emission_O2+emission_CO2+His+PO4.ferm.+PO4.apporte+PO4.utilise; 0.409, 0.720, pH+Main.P-Source.Conc.+Nitrogen.Conc.+X.F.Suc+X.VXdt+total.cell+yield+emission_O2+rab+PO4.ferm.+PO4.apporte+PO4.utilise; 0.397, 0.720, pH+P-Source.Feed.conc.+Nitrogen.Conc.+OD+X.F.Suc+X.VXdt+yield+rab+Thr+lactate+PO4.ferm.+PO4.apporte+PO4.utilise; 0.409, 0.720, pH+tmp+Nitrogen.Conc.+X.F.Suc+X.VXdt+yield+emission_O2+rab+Thr+PO4.ferm.+PO4.apporte+PO4.utilise; 0.409, 0.720, pH+P-Source.Feed.conc.+Nitrogen.Conc.+X.F.Suc+X.VXdt+yield+rab+Thr+lactate+PO4.ferm.+PO4.apporte+PO4.utilise; 0.397, 0.720, pH+P-Source.Feed.conc.+Nitrogen.Conc.+OD+X.F.Suc+X.VXdt+yield+emission_O2+Thr+lactate+PO4.ferm.+PO4.apporte+PO4.utilise; 0.385, 0.720, pH+tmp+Nitrogen.Conc.+X.F.Suc+X.VXdt+total.cell+yield+PL+emission_O2+emission_CO2+Thr+PO4.ferm.+PO4.apporte+PO4.utilise; 0.419, 0.719, pH+Main.P-Source.Conc.+Nitrogen.Conc.+OD+X.F.Suc+X.VXdt+yield+emission_O2+PO4.ferm.+PO4.apporte+PO4.utilise; 0.397, 0.719, pH+Main.P-Source.Conc.+Nitrogen.Conc.+X.F.Suc+X.VXdt+total.cell+yield+rab+Thr+lactate+PO4.ferm.+PO4.apporte+PO4.utilise; 0.397, 0.719, pH+tmp+Nitrogen.Conc.+OD+X.F.Suc+X.VXdt+yield+PL+rab+Thr+PO4.ferm.+PO4.apporte+PO4.utilise; 0.397, 0.719, pH+Nitrogen.Conc.+X.F.Suc+X.VXdt+yield+PL+emission_O2+rab+Thr+lactate+PO4.ferm.+PO4.apporte+PO4.utilise; 0.408, 0.719, pH+Main.P-Source.Conc.+Nitrogen.Conc.+OD+X.F.Suc+X.VXdt+yield+emission_O2+rab+PO4.ferm.+PO4.apporte+PO4.utilise; 0.408, 0.719, pH+Nitrogen.Conc.+X.F.Suc+X.VXdt+total.cell+yield+emission_O2+emission_CO2+rab+PO4.ferm.+PO4.apporte+PO4.utilise; 0.373, 0.719, pH+tmp+Main.P-Source.Conc.+Nitrogen.Conc.+X.F.Suc+X.VXdt+total.cell+yield+PL+emission_O2+Thr+His+PO4.ferm.+PO4.apporte+PO4.utilise; 0.397, 0.719, pH+tmp+Main.P-Source.Conc.+Nitrogen.Conc.+X.F.Suc+X.VXdt+total.cell+yield+PL+rab+PO4.ferm.+PO4.apporte+PO4.utilise; 0.397, 0.719, pH+tmp+Main.P-Source.Conc.+Nitrogen.Conc.+X.F.Suc+X.VXdt+total.cell+yield+emission_O2+His+PO4.ferm.+PO4.apporte+PO4.utilise; 0.430, 0.719, pH+tmp+P-Source.Feed.conc.+Nitrogen.Conc.+X.F.Suc+X.VXdt+total.cell+yield+emission_CO2+Thr+His; 0.408, 0.719, pH+Nitrogen.Conc.+X.F.Suc+X.VXdt+yield+PL+emission_CO2+rab+His+PO4.ferm.+PO4.apporte+PO4.utilise; 0.408, 0.719, pH+Main.P-Source.Conc.+Nitrogen.Conc.+X.F.Suc+X.VXdt+total.cell+yield+rab+His+PO4.ferm.+PO4.apporte+PO4.utilise; 0.385, 0.719, pH+tmp+Main.P-Source.Conc.+Nitrogen.Conc.+X.F.Suc+X.VXdt+total.cell+yield+rab+Thr+His+PO4.ferm.+PO4.apporte+PO4.utilise; 0.408, 0.719, pH+tmp+Main.P-Source.Conc.+Nitrogen.Conc.+X.F.Suc+X.VXdt+yield+PL+rab+PO4.ferm.+PO4.apporte+PO4.utilise; 0.385, 0.719, pH+tmp+Nitrogen.Conc.+OD+X.F.Suc+X.VXdt+yield+PL+rab+Thr+His+PO4.ferm.+PO4.apporte+PO4.utilise; 0.397, 0.719, pH+tmp+Nitrogen.Conc.+X.F.Suc+X.VXdt+total.cell+yield+PL+emission_CO2+His+PO4.ferm.+PO4.apporte+PO4.utilise; 0.397, 0.719, pH+tmp+Nitrogen.Conc.+X.F.Suc+X.VXdt+total.cell+yield+emission_O2+emission_CO2+His+PO4.ferm.+PO4.apporte+PO4.utilise; 0.408, 0.719, pH+tmp+Nitrogen.Conc.+OD+X.F.Suc+X.VXdt+yield+rab+His+PO4.ferm.+PO4.apporte+PO4.utilise; 0.385, 0.719, pH+Nitrogen.Conc.+X.F.Suc+X.VXdt+total.cell+yield+PL+emission_O2+rab+Thr+His+PO4.ferm.+PO4.apporte+PO4.utilise; 0.408, 0.719, pH+P-Source.Feed.conc.+Nitrogen.Conc.+X.F.Suc+X.VXdt+yield+emission_O2+rab+Thr+PO4.ferm.+PO4.apporte+PO4.utilise; 0.385, 0.719, pH+Nitrogen.Conc.+X.F.Suc+X.VXdt+total.cell+yield+PL+rab+Thr+His+lactate+PO4.ferm.+PO4.apporte+PO4.utilise; 0.408, 0.719, pH+Nitrogen.Conc.+X.F.Suc+X.VXdt+yield+PL+emission_CO2+rab+lactate+PO4.ferm.+PO4.apporte+PO4.utilise; 0.408, 0.719, pH+tmp+Nitrogen.Conc.+X.F.Suc+X.VXdt+yield+PL+emission_CO2+rab+PO4.ferm.+PO4.apporte+PO4.utilise; 0.408, 0.719, pH+Main.P-Source.Conc.+Nitrogen.Conc.+X.F.Suc+X.VXdt+yield+PL+rab+lactate+PO4.ferm.+PO4.apporte+PO4.utilise; 0.429, 0.719, pH+P-Source.Feed.conc.+Nitrogen.Conc.+X.F.Suc+X.VXdt+yield+emission_O2+PO4.ferm.+PO4.apporte+PO4.utilise; 0.396, 0.719, pH+Main.P-Source.Conc.+P-Source.Feed.conc.+Nitrogen.Conc.+OD+X.F.Suc+X.VXdt+yield+emission_O2+Thr+PO4.ferm.+PO4.apporte+PO4.utilise; 0.396, 0.719, pH+tmp+Nitrogen.Conc.+X.F.Suc+X.VXdt+yield+PL+emission_CO2+rab+His+PO4.ferm.+PO4.apporte+PO4.utilise; 0.408, 0.719, pH+Nitrogen.Conc.+X.F.Suc+X.VXdt+total.cell+yield+PL+emission_O2+emission_CO2+PO4.ferm.+PO4.apporte+PO4.utilise; 0.396, 0.719, pH+Main.Thr.Conc.+Nitrogen.Conc.+X.F.Suc+X.VXdt+total.cell+yield+PL+rab+Thr+PO4.ferm.+PO4.apporte+PO4.utilise; 0.396, 0.719, pH+Nitrogen.Conc.+X.F.Suc+X.VXdt+yield+PL+emission_O2+emission_CO2+Thr+His+PO4.ferm.+PO4.apporte+PO4.utilise; 0.408, 0.719, pH+Main.P-Source.Conc.+Nitrogen.Conc.+X.F.Suc+X.VXdt+yield+PL+emission_O2+rab+PO4.ferm.+PO4.apporte+PO4.utilise; 0.408, 0.719, pH+Nitrogen.Conc.+X.F.Suc+X.VXdt+total.cell+yield+emission_O2+rab+lactate+PO4.ferm.+PO4.apporte+PO4.utilise; 0.418, 0.719, pH+Main.Thr.Conc.+Nitrogen.Conc.+OD+X.F.Suc+X.VXdt+yield+rab+PO4.ferm.+PO4.apporte+PO4.utilise; 0.384, 0.719, pH+tmp+Main.P-Source.Conc.+Nitrogen.Conc.+X.F.Suc+X.VXdt+total.cell+yield+emission_CO2+Thr+His+PO4.ferm.+PO4.apporte+PO4.utilise; 0.396, 0.719, pH+Main.P-Source.Conc.+Nitrogen.Conc.+X.F.Suc+X.VXdt+total.cell+yield+emission_O2+emission_CO2+Thr+PO4.ferm.+PO4.apporte+PO4.utilise; 0.407, 0.719, pH+Main.Thr.Conc.+Nitrogen.Conc.+X.F.Suc+X.VXdt+yield+emission_O2+rab+Thr+PO4.ferm.+PO4.apporte+PO4.utilise; 0.384, 0.719, pH+Main.Thr.Conc.+Nitrogen.Conc.+OD+X.F.Suc+X.VXdt+yield+emission_O2+rab+Thr+His+PO4.ferm.+PO4.apporte+PO4.utilise; 0.359, 0.719, pH+tmp+Nitrogen.Conc.+X.F.Suc+X.VXdt+total.cell+yield+PL+emission_O2+emission_CO2+rab+Thr+His+PO4.ferm.+PO4.apporte+PO4.utilise; 0.396, 0.719, pH+Nitrogen.Conc.+X.F.Suc+X.VXdt+total.cell+yield+emission_CO2+rab+Thr+lactate+PO4.ferm.+PO4.apporte+PO4.utilise; 0.407, 0.719, pH+Nitrogen.Conc.+OD+X.F.Suc+X.VXdt+yield+emission_O2+rab+lactate+PO4.ferm.+PO4.apporte+PO4.utilise; 0.407, 0.719, pH+Main.P-Source.Conc.+Main.Thr.Conc.+Nitrogen.Conc.+X.F.Suc+X.VXdt+yield+emission_O2+Thr+PO4.ferm.+PO4.apporte+PO4.utilise; 0.384, 0.719, pH+Main.P-Source.Conc.+Nitrogen.Conc.+X.F.Suc+X.VXdt+total.cell+yield+PL+rab+Thr+His+PO4.ferm.+PO4.apporte+PO4.utilise; 0.429, 0.719, pH+tmp+Nitrogen.Conc.+X.VXdt+total.cell+yield+emission_CO2+Thr+His+lactate; 0.384, 0.719, pH+tmp+Nitrogen.Conc.+X.F.Suc+X.VXdt+yield+PL+emission_O2+rab+Thr+His+PO4.ferm.+PO4.apporte+PO4.utilise; 0.407, 0.719, pH+tmp+X.F.Suc+X.VXdt+total.cell+yield+emission_CO2+Thr+His+PO4.ferm.+PO4.apporte+PO4.utilise; 0.384, 0.719, pH+P-Source.Feed.conc.+Nitrogen.Conc.+OD+X.F.Suc+X.VXdt+yield+emission_O2+rab+Thr+His+PO4.ferm.+PO4.apporte+PO4.utilise; 0.384, 0.719, pH+tmp+Nitrogen.Conc.+X.F.Suc+X.VXdt+total.cell+yield+PL+emission_O2+rab+His+PO4.ferm.+PO4.apporte+PO4.utilise; 0.384, 0.719, pH+Main.P-Source.Conc.+Main.Thr.Conc.+Nitrogen.Conc.+OD+X.F.Suc+X.VXdt+yield+rab+Thr+His+PO4.ferm.+PO4.apporte+PO4.utilise; 0.429, 0.719, pH+tmp+Nitrogen.Conc.+X.F.Suc+X.VXdt+yield+emission_CO2+PO4.ferm.+PO4.apporte+PO4.utilise; 0.418, 0.719, pH+Main.Thr.Conc.+Nitrogen.Conc.+X.F.Suc+X.VXdt+yield+PL+rab+PO4.ferm.+PO4.apporte+PO4.utilise; 0.395, 0.719, pH+P-Source.Feed.conc.+Nitrogen.Conc.+X.F.Suc+X.VXdt+yield+PL+emission_O2+Thr+His+PO4.ferm.+PO4.apporte+PO4.utilise; 0.428, 0.719, pH+tmp+Main.P-Source.Conc.+Nitrogen.Conc.+X.VXdt+total.cell+yield+emission_CO2+Thr+His; 0.371, 0.719, pH+Main.P-Source.Conc.+Nitrogen.Conc.+OD+X.F.Suc+X.VXdt+yield+PL+rab+Thr+His+lactate+PO4.ferm.+PO4.apporte+PO4.utilise; 0.407, 0.719, pH+Nitrogen.Conc.+X.F.Suc+X.VXdt+total.cell+yield+emission_CO2+rab+His+PO4.ferm.+PO4.apporte+PO4.utilise; 0.407, 0.719, pH+Main.Thr.Conc.+Nitrogen.Conc.+X.F.Suc+X.VXdt+total.cell+yield+emission_O2+Thr+PO4.ferm.+PO4.apporte+PO4.utilise; 0.395, 0.718, pH+Nitrogen.Conc.+OD+X.F.Suc+X.VXdt+yield+PL+emission_O2+rab+His+PO4.ferm.+PO4.apporte+PO4.utilise; 0.395, 0.718, pH+P-Source.Feed.conc.+Nitrogen.Conc.+X.F.Suc+X.VXdt+total.cell+yield+emission_CO2+rab+Thr+PO4.ferm.+PO4.apporte+PO4.utilise; 0.395, 0.718, pH+tmp+Nitrogen.Conc.+X.F.Suc+X.VXdt+total.cell+yield+PL+emission_CO2+rab+PO4.ferm.+PO4.apporte+PO4.utilise; 0.395, 0.718, pH+Nitrogen.Conc.+X.F.Suc+X.VXdt+yield+PL+emission_CO2+rab+Thr+lactate+PO4.ferm.+PO4.apporte+PO4.utilise; 0.418, 0.718, pH+Main.Thr.Conc.+Nitrogen.Conc.+X.F.Suc+X.VXdt+total.cell+yield+rab+PO4.ferm.+PO4.apporte+PO4.utilise; 0.383, 0.718, pH+tmp+Main.P-Source.Conc.+Nitrogen.Conc.+X.F.Suc+X.VXdt+total.cell+yield+PL+emission_O2+Thr+PO4.ferm.+PO4.apporte+PO4.utilise; 0.395, 0.718, pH+Main.P-Source.Conc.+Nitrogen.Conc.+X.F.Suc+X.VXdt+yield+rab+Thr+His+lactate+PO4.ferm.+PO4.apporte+PO4.utilise; 0.406, 0.718, pH+Main.Thr.Conc.+Nitrogen.Conc.+X.F.Suc+X.VXdt+yield+emission_O2+Thr+lactate+PO4.ferm.+PO4.apporte+PO4.utilise; 0.428, 0.718, pH+tmp+Main.P-Source.Conc.+Nitrogen.Conc.+X.VXdt+total.cell+yield+emission_O2+Thr+His; 0.406, 0.718, pH+tmp+Nitrogen.Conc.+X.F.Suc+X.VXdt+yield+PL+emission_O2+emission_CO2+PO4.ferm.+PO4.apporte+PO4.utilise; 0.395, 0.718, pH+Main.Thr.Conc.+Nitrogen.Conc.+X.F.Suc+X.VXdt+yield+rab+Thr+His+lactate+PO4.ferm.+PO4.

apporte+PO4.utilise; 0.406, 0.718, pH+tmp+Main.P-Source.Conc.+Nitrogen.Conc.+X.F.Suc+X.VXdt+yield+PL+emission_O2+PO4.ferm.+PO4.apporte+PO4.utilise; 0.395, 0.718, pH+Nitrogen.Conc.+OD+X.F.Suc+X.VXdt+yield+rab+Thr+lactate+SO4.ferm.+PO4.ferm.+PO4.apporte+PO4.utilise; 0.395, 0.718, pH+tmp+Nitrogen.Conc.+X.F.Suc+X.VXdt+total.cell+yield+rab+Thr+SO4.ferm.+PO4.ferm.+PO4.apporte+PO4.utilise; 0.417, 0.718, pH+P-Source.Feed.conc.+Nitrogen.Conc.+OD+X.F.Suc+X.VXdt+yield+rab+PO4.ferm.+PO4.apporte+PO4.utilise; 0.406, 0.718, pH+tmp+Nitrogen.Conc.+X.F.Suc+X.VXdt+yield+emission_CO2+rab+Thr+PO4.ferm.+PO4.apporte+PO4.utilise; 0.428, 0.718, pH+tmp+Nitrogen.Conc.+X.VXdt+total.cell+yield+emission_O2+Thr+His+PO4.utilise; 0.383, 0.718, pH+tmp+Nitrogen.Conc.+OD+X.F.Suc+X.VXdt+yield+emission_CO2+rab+Thr+His+PO4.ferm.+PO4.apporte+PO4.utilise; 0.406, 0.718, pH+Main.P-Source.Conc.+Nitrogen.Conc.+X.F.Suc+X.VXdt+yield+emission_O2+Thr+lactate+PO4.ferm.+PO4.apporte+PO4.utilise; 0.395, 0.718, pH+Main.P-Source.Conc.+Nitrogen.Conc.+X.F.Suc+X.VXdt+yield+PL+emission_O2+rab+Thr+PO4.ferm.+PO4.apporte+PO4.utilise; 0.406, 0.718, pH+tmp+Nitrogen.Conc.+X.VXdt+total.cell+yield+PL+emission_O2+emission_CO2+rab+Thr+His; 0.383, 0.718, pH+tmp+Main.P-Source.Conc.+Nitrogen.Conc.+X.F.Suc+X.VXdt+total.cell+yield+PL+rab+Thr+PO4.ferm.+PO4.apporte+PO4.utilise; 0.417, 0.718, pH+Main.P-Source.Conc.+Nitrogen.Conc.+X.F.Suc+X.VXdt+yield+PL+emission_O2+PO4.ferm.+PO4.apporte+PO4.utilise; 0.383, 0.718, pH+tmp+Nitrogen.Conc.+OD+X.F.Suc+X.VXdt+yield+emission_O2+rab+Thr+His+PO4.ferm.+PO4.apporte+PO4.utilise; 0.406, 0.718, pH+Main.P-Source.Conc.+Nitrogen.Conc.+OD+X.F.Suc+X.VXdt+yield+emission_CO2+rab+PO4.ferm.+PO4.apporte+PO4.utilise; 0.417, 0.718, pH+Main.Thr.Conc.+Nitrogen.Conc.+X.F.Suc+X.VXdt+yield+rab+lactate+PO4.ferm.+PO4.apporte+PO4.utilise; 0.395, 0.718, pH+P-Source.Feed.conc.+Nitrogen.Conc.+X.F.Suc+X.VXdt+total.cell+yield+rab+Thr+lactate+PO4.ferm.+PO4.apporte+PO4.utilise; 0.394, 0.718, pH+tmp+Nitrogen.Conc.+X.F.Suc+X.VXdt+yield+PL+emission_O2+emission_CO2+His+PO4.ferm.+PO4.apporte+PO4.utilise; 0.383, 0.718, pH+Main.Thr.Conc.+Nitrogen.Conc.+OD+X.F.Suc+X.VXdt+yield+emission_CO2+rab+Thr+His+PO4.ferm.+PO4.apporte+PO4.utilise; 0.370, 0.718, pH+Nitrogen.Conc.+OD+X.F.Suc+X.VXdt+yield+PL+emission_O2+rab+Thr+His+lactate+PO4.ferm.+PO4.apporte+PO4.utilise; 0.383, 0.718, pH+P-Source.Feed.conc.+Nitrogen.Conc.+OD+X.F.Suc+X.VXdt+yield+PL+emission_O2+rab+Thr+PO4.ferm.+PO4.apporte+PO4.utilise; 0.394, 0.718, pH+Nitrogen.Conc.+OD+X.F.Suc+X.VXdt+yield+emission_O2+Thr+His+SO4.ferm.+PO4.ferm.+PO4.apporte+PO4.utilise; 0.406, 0.718, pH+Main.Thr.Conc.+Nitrogen.Conc.+X.F.Suc+X.VXdt+yield+emission_CO2+rab+Thr+PO4.ferm.+PO4.apporte+PO4.utilise; 0.406, 0.718, pH+Nitrogen.Conc.+X.F.Suc+X.VXdt+yield+PL+emission_O2+emission_CO2+His+PO4.ferm.+PO4.apporte+PO4.utilise; 0.382, 0.718, pH+tmp+Nitrogen.Conc.+X.F.Suc+X.VXdt+total.cell+yield+PL+emission_CO2+rab+His+PO4.ferm.+PO4.apporte+PO4.utilise; 0.394, 0.718, pH+Main.P-Source.Conc.+P-Source.Feed.conc.+Nitrogen.Conc.+X.F.Suc+X.VXdt+total.cell+yield+rab+Thr+PO4.ferm.+PO4.apporte+PO4.utilise; 0.370, 0.718, pH+Main.P-Source.Conc.+Nitrogen.Conc.+OD+X.F.Suc+X.VXdt+yield+PL+emission_O2+rab+Thr+His+PO4.ferm.+PO4.apporte+PO4.utilise; 0.406, 0.718, pH+Main.P-Source.Conc.+Nitrogen.Conc.+X.F.Suc+X.VXdt+total.cell+yield+emission_CO2+rab+PO4.ferm.+PO4.apporte+PO4.utilise; 0.406, 0.718, pH+Main.Thr.Conc.+Nitrogen.Conc.+X.F.Suc+X.VXdt+yield+PL+emission_O2+Thr+PO4.ferm.+PO4.apporte+PO4.utilise; 0.382, 0.718, pH+tmp+Nitrogen.Conc.+X.F.Suc+X.VXdt+yield+PL+emission_CO2+rab+Thr+His+PO4.ferm.+PO4.apporte+PO4.utilise; 0.370, 0.718, pH+tmp+Nitrogen.Conc.+X.F.Suc+X.VXdt+total.cell+yield+PL+rab+Thr+His+SO4.ferm.+PO4.ferm.+PO4.apporte+PO4.utilise; 0.427, 0.718, pH+tmp+Nitrogen.Conc.+X.VXdt+total.cell+yield+emission_CO2+rab+Thr+His; 0.394, 0.718, pH+tmp+X.F.Suc+X.VXdt+total.cell+yield+PL+emission_CO2+Thr+His+PO4.ferm.+PO4.apporte+PO4.utilise; 0.406, 0.718, pH+tmp+Nitrogen.Conc.+X.F.Suc+X.VXdt+yield+emission_O2+emission_CO2+Thr+PO4.ferm.+PO4.apporte+PO4.utilise; 0.382, 0.718, pH+Main.P-Source.Conc.+Main.Thr.Conc.+Nitrogen.Conc.+OD+X.F.Suc+X.VXdt+yield+PL+rab+Thr+PO4.ferm.+PO4.apporte+PO4.utilise; 0.416, 0.718, pH+tmp+Main.P-Source.Conc.+Nitrogen.Conc.+X.VXdt+total.cell+yield+PL+emission_O2+Thr+His; 0.382, 0.718, pH+P-Source.Feed.conc.+Nitrogen.Conc.+OD+X.F.Suc+X.VXdt+yield+emission_CO2+rab+Thr+His+PO4.ferm.+PO4.apporte+PO4.utilise; 0.394, 0.718, pH+tmp+Main.P-Source.Conc.+Nitrogen.Conc.+X.F.Suc+X.VXdt+yield+PL+emission_O2+His+PO4.ferm.+PO4.apporte+PO4.utilise; 0.405, 0.718, pH+Nitrogen.Conc.+X.F.Suc+X.VXdt+yield+PL+emission_O2+emission_CO2+lactate+PO4.ferm.+PO4.apporte+PO4.utilise; 0.416, 0.718, pH+Main.P-Source.Conc.+Nitrogen.Conc.+X.F.Suc+X.VXdt+yield+emission_O2+His+PO4.ferm.+PO4.apporte+PO4.utilise; 0.447, 0.718, pH+tmp+Nitrogen.Conc.+X.VXdt+total.cell+yield+emission_O2+Thr; 0.405, 0.718, pH+P-Source.Feed.conc.+Nitrogen.Conc.+X.F.Suc+X.VXdt+yield+emission_CO2+rab+Thr+PO4.ferm.+PO4.apporte+PO4.utilise; 0.405, 0.718, pH+Main.P-Source.Conc.+Nitrogen.Conc.+OD+X.F.Suc+X.VXdt+yield+rab+lactate+PO4.ferm.+PO4.apporte+PO4.utilise; 0.405, 0.718, pH+Main.P-Source.Conc.+Nitrogen.Conc.+X.F.Suc+X.VXdt+yield+PL+emission_CO2+rab+PO4.ferm.+PO4.apporte+PO4.utilise; 0.394, 0.718, pH+Nitrogen.Conc.+X.F.Suc+X.VXdt+yield+PL+emission_O2+emission_CO2+Thr+lactate+PO4.ferm.+PO4.apporte+PO4.utilise; 0.394, 0.718, pH+Main.P-Source.Conc.+Nitrogen.Conc.+X.F.Suc+X.VXdt+yield+PL+emission_O2+Thr+His+PO4.ferm.+PO4.apporte+PO4.utilise; 0.382, 0.718, pH+Main.Thr.Conc.+Nitrogen.Conc.+OD+X.F.Suc+X.VXdt+yield+rab+Thr+His+lactate+PO4.ferm.+PO4.apporte+PO4.utilise; 0.405, 0.718, pH+P-Source.Feed.conc.+Nitrogen.Conc.+X.F.Suc+X.VXdt+total.cell+yield+PL+rab+PO4.ferm.+PO4.apporte+PO4.utilise; 0.416, 0.718, pH+tmp+Nitrogen.Conc.+X.F.Suc+yield+emission_O2+Thr+His+PO4.ferm.+PO4.apporte+PO4.utilise; 0.416, 0.718, pH+tmp+Nitrogen.Conc.+X.F.Suc+X.VXdt+yield+rab+lactate+PO4.ferm.+PO4.apporte+PO4.utilise; 0.437, 0.718, pH+tmp+Main.P-Source.Conc.+X.VXdt+total.cell+yield+emission_CO2+Thr+His; 0.394, 0.718, pH+Nitrogen.Conc.+OD+X.F.Suc+X.VXdt+yield+emission_O2+rab+Thr+SO4.ferm.+PO4.ferm.+PO4.apporte+PO4.utilise; 0.405, 0.718, pH+Main.Thr.Conc.+Nitrogen.Conc.+X.F.Suc+X.VXdt+yield+emission_O2+emission_CO2+Thr+PO4.ferm.+PO4.apporte+PO4.utilise; 0.382, 0.718, pH+Nitrogen.Conc.+X.F.Suc+X.VXdt+total.cell+yield+PL+emission_CO2+rab+Thr+His+PO4.ferm.+PO4.apporte+PO4.utilise; 0.405, 0.718, pH+tmp+Nitrogen.Conc.+X.F.Suc+X.VXdt+total.cell+yield+rab+lactate+PO4.ferm.+PO4.apporte+PO4.utilise; 0.405, 0.718, pH+Main.P-Source.Conc.+P-Source.Feed.conc.+Nitrogen.Conc.+X.F.Suc+X.VXdt+yield+rab+Thr+PO4.ferm.+PO4.apporte+PO4.utilise; 0.394, 0.718, pH+Nitrogen.Conc.+OD+X.F.Suc+X.VXdt+yield+emission_O2+emission_CO2+rab+His+PO4.ferm.+PO4.apporte+PO4.utilise; 0.369, 0.718, pH+Nitrogen.Conc.+OD+X.F.Suc+X.VXdt+yield+PL+emission_CO2+rab+Thr+His+lactate+PO4.ferm.+PO4.apporte+PO4.utilise; 0.437, 0.718, pH+tmp+X.F.Suc+yield+emission_CO2+His+PO4.ferm.+PO4.apporte+PO4.utilise; 0.394, 0.718, pH+Main.Thr.Conc.+Nitrogen.Conc.+X.F.Suc+X.VXdt+total.cell+yield+emission_O2+rab+Thr+PO4.ferm.+PO4.apporte+PO4.utilise; 0.427, 0.718, pH+tmp+Nitrogen.Conc.+X.F.Suc+yield+emission_CO2+His+PO4.ferm.+PO4.apporte+PO4.utilise; 0.427, 0.718, pH+tmp+Nitrogen.Conc.+X.F.Suc+yield+emission_O2+His+PO4.ferm.+PO4.apporte+PO4.utilise; 0.405, 0.717, pH+Nitrogen.Conc.+OD+X.F.Suc+X.VXdt+yield+emission_CO2+rab+lactate+PO4.ferm.+PO4.apporte+PO4.utilise; 0.405, 0.717, pH+P-Source.Feed.conc.+Nitrogen.Conc.+X.F.Suc+X.VXdt+yield+emission_O2+Thr+lactate+PO4.ferm.+PO4.apporte+PO4.utilise; 0.369, 0.717, pH+Main.P-Source.Conc.+Nitrogen.Conc.+OD+X.F.Suc+X.VXdt+yield+PL+emission_O2+Thr+His+lactate+PO4.ferm.+PO4.apporte+PO4.utilise; 0.381, 0.717, pH+Main.Thr.Conc.+Nitrogen.Conc.+OD+X.F.Suc+X.VXdt+yield+PL+rab+Thr+lactate+PO4.ferm.+PO4.apporte+PO4.utilise; 0.393, 0.717, pH+Nitrogen.Conc.+X.F.Suc+X.VXdt+total.cell+yield+emission_O2+emission_CO2+Thr+lactate+PO4.ferm.+PO4.apporte+PO4.utilise; 0.381, 0.717, pH+tmp+Nitrogen.Conc.+OD+X.F.Suc+X.VXdt+yield+emission_O2+emission_CO2+Thr+His+PO4.ferm.+PO4.apporte+PO4.utilise; 0.426, 0.717, pH+tmp+Nitrogen.Conc.+X.VXdt+total.cell+yield+rab+Thr+His+PO4.utilise; 0.369, 0.717, pH+tmp+Main.P-Source.Conc.+Nitrogen.Conc.+X.F.Suc+X.VXdt+total.cell+yield+PL+rab+Thr+His+PO4.ferm.+PO4.apporte+PO4.utilise; 0.393, 0.717, pH+Main.P-Source.Conc.+Main.Thr.Conc.+Nitrogen.Conc.+X.F.Suc+X.VXdt+yield+PL+rab+Thr+PO4.ferm.+PO4.apporte+PO4.utilise; 0.381, 0.717, pH+Nitrogen.Conc.+X.F.Suc+X.VXdt+total.cell+yield+PL+emission_O2+emission_CO2+rab+Thr+PO4.ferm.+PO4.apporte+PO4.utilise; 0.416, 0.717, pH+Main.P-Source.Conc.+Main.Thr.Conc.+Nitrogen.Conc.+X.F.Suc+X.VXdt+yield+rab+PO4.ferm.+PO4.apporte+PO4.utilise; 0.381, 0.717, pH+Main.P-Source.Conc.+Nitrogen.Conc.+OD+X.F.Suc+X.VXdt+yield+emission_O2+emission_CO2+Thr+lactate+PO4.ferm.+PO4.apporte+PO4.utilise; 0.381, 0.717, pH+Main.P-Source.Conc.+Nitrogen.Conc.+X.F.Suc+X.VXdt+total.cell+yield+PL+emission_O2+rab+Thr+PO4.ferm.+PO4.apporte+PO4.utilise; 0.393, 0.717, pH+Main.Thr.Conc.+Nitrogen.Conc.+X.F.Suc+X.VXdt+yield+PL+rab+Thr+lactate+PO4.ferm.+PO4.apporte+PO4.utilise; 0.426, 0.717, pH+tmp+X.VXdt+total.cell+yield+PL+emission_CO2+Thr+His+PO4.utilise; 0.393, 0.717, pH+Nitrogen.Conc.+OD+X.F.Suc+X.VXdt+yield+PL+emission_CO2+rab+His+PO4.ferm.+PO4.apporte+PO4.utilise; 0.416, 0.717, pH+P-Source.Feed.conc.+Nitrogen.Conc.+X.F.Suc+X.VXdt+yield+emission_O2+rab+PO4.ferm.+PO4.apporte+PO4.utilise; 0.404, 0.717, pH+Nitrogen.Conc.+X.F.Suc+X.VXdt+total.cell+yield+PL+emission_O2+His+PO4.ferm.+PO4.apporte+PO4.utilise; 0.381, 0.717, pH+Main.Thr.Conc.+Nitrogen.Conc.+OD+X.F.Suc+X.VXdt+yield+PL+emission_O2+rab+Thr+PO4.ferm.+PO4.apporte+PO4.utilise; 0.415, 0.717, pH+tmp+P-Source.Feed.conc.+Nitrogen.Conc.+X.VXdt+total.cell+yield+PL+emission_CO2+Thr+His; 0.393, 0.717, pH+Nitrogen.Conc.+OD+X.F.Suc+X.VXdt+yield+PL+rab+His+lactate+PO4.ferm.+PO4.apporte+PO4.utilise; 0.404, 0.717, pH+P-Source.Feed.conc.+Nitrogen.Conc.+X.F.Suc+X.VXdt+total.cell+yield+rab+His+PO4.ferm.+PO4. apporte+PO4.utilise; 0.393, 0.717, pH+tmp+Nitrogen.Conc.+X.F.Suc+X.VXdt+total.cell+yield+PL+emission_O2+emission_CO2+PO4.ferm.+PO4.apporte+PO4.utilise; 0.393, 0.717, pH+P-Source.Feed.conc.+Nitrogen.Conc.+X.F.Suc+X.VXdt+total.cell+yield+emission_O2+emission_CO2+Thr+PO4.ferm.+PO4.apporte+PO4.utilise; 0.381, 0.717, pH+tmp+Nitrogen.Conc.+X.F.Suc+X.VXdt+total.cell+yield+emission_O2+emission_CO2+rab+Thr+PO4.ferm.+PO4.apporte+PO4.utilise; 0.369, 0.717, pH+Main.P-Source.Conc.+Nitrogen.Conc.+OD+X.F.Suc+X.VXdt+yield+PL+emission_CO2+rab+Thr+His+PO4.ferm.+PO4.apporte+PO4.utilise; 0.393, 0.717, pH+Main.P-Source.Conc.+Nitrogen.Conc.+X.F.Suc+X.VXdt+yield+PL+emission_CO2+rab+Thr+PO4.ferm.+PO4.apporte+PO4.utilise; 0.393, 0.717, pH+Main.P-Source.Conc.+Nitrogen.Conc.+X.F.Suc+X.VXdt+yield+emission_O2+rab+Thr+His+PO4.ferm.+PO4.apporte+PO4.utilise; 0.381, 0.717, pH+tmp+Nitrogen.Conc.+X.F.Suc+X.VXdt+yield+PL+emission_O2+emission_CO2+Thr+His+PO4.ferm.+PO4.apporte+PO4.utilise; 0.381, 0.717, pH+tmp+Main.P-Source.Conc.+Nitrogen.Conc.+X.F.Suc+X.VXdt+total.cell+yield+PL+rab+His+PO4.ferm.+PO4.apporte+PO4.utilise; 0.404, 0.717, pH+P-Source.Feed.conc.+Nitrogen.Conc.+X.F.Suc+X.VXdt+yield+emission_O2+emission_CO2+Thr+PO4.ferm.+PO4.apporte+PO4.utilise; 0.393, 0.717, pH+P-Source.Feed.conc.+Main.Thr.Conc.+Nitrogen.Conc.+OD+X.F.Suc+X.VXdt+yield+rab+Thr+PO4.ferm.+PO4.apporte+PO4.utilise; 0.404, 0.717, pH+tmp+Nitrogen.Conc.+OD+X.F.Suc+X.VXdt+yield+PL+rab+PO4.ferm.+PO4.apporte+PO4.utilise; 0.381, 0.717, pH+tmp+Nitrogen.Conc.+X.F.Suc+X.VXdt+total.cell+yield+emission_O2+emission_CO2+rab+His+PO4.ferm.+PO4.apporte+PO4.utilise; 0.381, 0.717, pH+Main.P-Source.Conc.+Main.Thr.Conc.+Nitrogen.Conc.+OD+X.F.Suc+X.VXdt+yield+emission_O2+Thr+His+PO4.ferm.+PO4.apporte+PO4.utilise; 0.404, 0.717, pH+Nitrogen.Conc.+X.F.Suc+X.VXdt+total.cell+yield+emission_CO2+rab+lactate+PO4.ferm.+PO4.apporte+PO4.utilise; 0.404, 0.717, pH+Nitrogen.Conc.+X.F.Suc+X.VXdt+yield+emission_O2+rab+His+lactate+PO4.ferm.+PO4.apporte+PO4.utilise; 0.393, 0.717, pH+tmp+Nitrogen.Conc.+OD+X.F.Suc+X.VXdt+yield+PL+emission_O2+His+PO4.ferm.+PO4.apporte+PO4.utilise; 0.368, 0.717, pH+tmp+Nitrogen.Conc.+X.F.Suc+X.VXdt+total.cell+yield+PL+emission_O2+Thr+His+SO4.ferm.+PO4.ferm.+PO4.apporte+PO4.utilise; 0.381, 0.717, pH+Main.Thr.Conc.+Nitrogen.Conc.+OD+X.F.Suc+X.VXdt+yield+emission_O2+emission_CO2+Thr+His+PO4.ferm.+PO4.apporte+PO4.utilise; 0.393, 0.717, pH+tmp+Main.P-Source.Conc.+Nitrogen.Conc.+X.F.Suc+X.VXdt+total.cell+yield+PL+emission_O2+PO4.ferm.+PO4.apporte+PO4.utilise; 0.393, 0.717, pH+Nitrogen.Conc.+X.F.Suc+X.VXdt+total.cell+yield+PL+emission_O2+Thr+lactate+PO4.ferm.+PO4.apporte+PO4.utilise; 0.393, 0.717, pH+Nitrogen.Conc.+X.F.Suc+X.VXdt+total.cell+yield+emission_O2+Thr+His+lactate+PO4.ferm.+PO4.apporte+PO4.utilise; 0.392, 0.717, pH+tmp+Main.P-Source.Conc.+Nitrogen.Conc.+X.F.Suc+X.VXdt+yield+PL+rab+His+PO4.ferm.+PO4.apporte+PO4.utilise; 0.381, 0.717, pH+Nitrogen.Conc.+OD+X.F.Suc+X.VXdt+yield+PL+rab+Thr+His+SO4.ferm.+PO4.ferm.+PO4.apporte+PO4.utilise; 0.392, 0.717, pH+Nitrogen.Conc.+X.F.Suc+X.VXdt+yield+emission_O2+rab+Thr+His+lactate+PO4.ferm.+PO4.apporte+PO4.utilise; 0.426, 0.717, Nitrogen.Conc.+OD+X.F.Suc+X.VXdt+yield+emission_O2+Thr+PO4.ferm.+PO4.apporte+PO4.utilise; 0.380, 0.717, pH+P-Source.Feed.conc.+Nitrogen.Conc.+OD+X.F.Suc+X.VXdt+yield+PL+emission_CO2+rab+Thr+PO4.ferm.+

PO4.apporte+PO4.utilise; 0.392, 0.717, pH+Nitrogen. Conc.+OD+X.F.Suc+X.VXdt+yield+PL+emission_O2+ emission_CO2+rab+PO4.ferm.+PO4.apporte+PO4.utilise; 0.368, 0.717, pH+tmp+Main.P-Source.Conc.+Nitrogen. Conc.+X.F.Suc+X.VXdt+total.cell+yield+PL+emission_ CO2+Thr+His+PO4.ferm.+PO4.apporte+PO4.utilise; 0.392, 0.717, pH+Main.P-Source.Conc.+Main.Thr.Conc.+ Nitrogen.Conc.+X.F.Suc+X.VXdt+yield+emission_O2+ Thr+His+PO4.ferm.+PO4.apporte+PO4.utilise; 0.404, 0.717, pH+Main.P-Source.Conc.+Nitrogen.Conc.+X.F. Suc+X.VXdt+yield+emission_O2+rab+His+PO4.ferm.+ PO4.apporte+PO4.utilise; 0.404, 0.717, pH+Nitrogen. Conc.+X.F.Suc+X.VXdt+yield+PL+emission_O2+ emission_CO2+rab+PO4.ferm.+PO4.apporte+PO4.utilise; 0.415, 0.717, pH+tmp+Main.P-Source.Conc.+Nitrogen. Conc.+X.VXdt+total.cell+yield+PL+emission_CO2+Thr+ His; 0.404, 0.717, pH+tmp+Nitrogen.Conc.+X.F.Suc+ yield+PL+emission_O2+Thr+His+PO4.ferm.+PO4. apporte+PO4.utilise; 0.425, 0.717, pH+tmp+Nitrogen. Conc.+X.VXdt+total.cell+yield+emission_O2+emission_ CO2+Thr+His; 0.425, 0.717, pH+tmp+Main.P-Source. Conc.+Nitrogen.Conc.+X.VXdt+total.cell+yield+rab+Thr+ His; 0.392, 0.717, pH+tmp+Main.P-Source.Conc.+ Nitrogen.Conc.+X.F.Suc+X.VXdt+yield+emission_O2+ Thr+His+PO4.ferm.+PO4.apporte+PO4.utilise; 0.415, 0.717, pH+tmp+Nitrogen.Conc.+X.F.Suc+X.VXdt+yield+ emission_O2+lactate+PO4.ferm.+PO4.apporte+PO4.utilise; 0.392, 0.717, pH+Main.Thr.Conc.+Nitrogen.Conc.+X. F.Suc+X.VXdt+yield+PL+emission_O2+Thr+His+PO4. ferm.+PO4.apporte+PO4.utilise; 0.403, 0.717, pH+Nitrogen.Conc.+X.F.Suc+X.VXdt+total.cell+yield+ emission_O2+emission_CO2+His+PO4.ferm.+PO4.apporte+PO4.utilise; 0.392, 0.717, pH+Nitrogen.Conc.+X.F. Suc+X.VXdt+yield+PL+emission_O2+emission_CO2+ rab+Thr+PO4.ferm.+PO4.apporte+PO4.utilise; 0.415, 0.717, pH+Main.Thr.Conc.+Nitrogen.Conc.+X.F.Suc+X. VXdt+yield+emission_O2+rab+PO4.ferm.+PO4.apporte+ PO4.utilise; 0.392, 0.717, pH+P-Source.Feed.conc.+Main. Thr.Conc.+Nitrogen.Conc.+X.F.Suc+X.VXdt+total.cell+ yield+rab+Thr+PO4.ferm.+PO4.apporte+PO4.utilise; 0.380, 0.717, pH+Main.P-Source.Conc.+Nitrogen.Conc.+ OD+X.F.Suc+X.VXdt+yield+emission_CO2+rab+Thr+lactate+PO4.ferm.+PO4.apporte+PO4.utilise; 0.445, 0.717, pH+tmp+X.VXdt+total.cell+yield+emission_O2+Thr+His; 0.403, 0.717, pH+Nitrogen.Conc.+OD+X.F.Suc+X.VXdt+ yield+emission_O2+His+lactate+PO4.ferm.+PO4.apporte+ PO4.utilise; 0.403, 0.717, pH+Nitrogen.Conc.+X.F.Suc+X. VXdt+yield+PL+emission_O2+His+lactate+PO4.ferm.+ PO4.apporte+PO4.utilise; 0.380, 0.717, pH+Nitrogen. Conc.+X.F.Suc+X.VXdt+total.cell+yield+emission_O2+ emission_CO2+rab+Thr+His+PO4.ferm.+PO4.apporte+ PO4.utilise; 0.392, 0.717, pH+Nitrogen.Conc.+X.F.Suc+X. VXdt+total.cell+yield+PL+emission_O2+rab+His+PO4. ferm.+PO4.apporte+PO4.utilise; 0.435, 0.717, pH+tmp+ Nitrogen.Conc.+X.F.Suc+yield+emission_O2+PO4.ferm.+ PO4.apporte+PO4.utilise; 0.403, 0.717, pH+Main.P-Source. Conc.+Nitrogen.Conc.+X.F.Suc+X.VXdt+yield+PL+ emission_O2+emission_CO2+PO4.ferm.+PO4.apporte+ PO4.utilise; 0.425, 0.717, pH+tmp+Nitrogen.Conc.+X. VXdt+total.cell+yield+emission_CO2+Thr+His+PO4. apporte; 0.403, 0.717, pH+tmp+Nitrogen.Conc.+OD+X.F. Suc+X.VXdt+yield+PL+emission_O2+PO4.ferm.+PO4. apporte+PO4.utilise; 0.435, 0.717, pH+tmp+X.VXdt+total. cell+yield+emission_CO2+Thr+His+PO4.utilise; 0.403, 0.717, pH+Main.P-Source.Conc.+Nitrogen.Conc.+X.F. Suc+X.VXdt+yield+rab+His+lactate+PO4.ferm.+PO4.apporte+PO4.utilise; 0.380, 0.717, pH+tmp+Nitrogen.Conc.+

X.F.Suc+X.VXdt+total.cell+yield+PL+emission_O2+ emission_CO2+His+PO4.ferm.+PO4.apporte+PO4.utilise; 0.445, 0.716, pH+tmp+Nitrogen.Conc.+X.VXdt+total.cell+ yield+rab+Thr; 0.380, 0.716, pH+P-Source.Feed.conc.+Nitrogen.Conc.+OD+X.F.Suc+X.VXdt+yield+emission_O2+ emission_CO2+Thr+His+PO4.ferm.+PO4.apporte+PO4. utilise; 0.392, 0.716, pH+Main.P-Source.Conc.+Nitrogen. Conc.+X.F.Suc+X.VXdt+yield+PL+emission_O2+ emission_CO2+Thr+PO4.ferm.+PO4.apporte+PO4.utilise; 0.380, 0.716, pH+tmp+Main.P-Source.Conc.+Nitrogen. Conc.+X.F.Suc+X.VXdt+total.cell+yield+PL+emission_ O2+His+PO4.ferm.+PO4.apporte+PO4.utilise; 0.380, 0.716, pH+Main.Thr.Conc.+Nitrogen.Conc.+OD+X.F.Suc+ X.VXdt+yield+emission_O2+Thr+His+lactate+PO4.ferm.+ PO4.apporte+PO4.utilise; 0.392, 0.716, pH+tmp+Nitrogen. Conc.+OD+X.F.Suc+X.VXdt+yield+PL+emission_CO2+ Thr+PO4.ferm.+PO4.apporte+PO4.utilise; 0.380, 0.716, pH+P-Source.Feed.conc.+Nitrogen.Conc.+X.F.Suc+X. VXdt+total.cell+yield+PL+emission_O2+Thr+His+PO4. ferm.+PO4.apporte+PO4.utilise; 0.425, 0.716, Nitrogen. Conc.+OD+X.F.Suc+X.VXdt+yield+rab+Thr+PO4.ferm.+ PO4.apporte+PO4.utilise; 0.403, 0.716, pH+Nitrogen. Conc.+OD+X.F.Suc+X.VXdt+yield+PL+emission_O2+ lactate+PO4.ferm.+PO4.apporte+PO4.utilise; 0.367, 0.716, pH+Nitrogen.Conc.+OD+X.F.Suc+X.VXdt+yield+emission_O2+emission_CO2+rab+Thr+His+lactate+PO4. ferm.+PO4.apporte+PO4.utilise; 0.403, 0.716, pH+Main.P-Source.Conc.+Nitrogen.Conc.+OD+X.F.Suc+X.VXdt+ yield+emission_O2+emission_CO2+PO4.ferm.+PO4. apporte+PO4.utilise; 0.403, 0.716, pH+tmp+Nitrogen. Conc.+X.F.Suc+yield+emission_O2+rab+Thr+His+PO4. ferm.+PO4.apporte+PO4.utilise; 0.445, 0.716, pH+tmp+ Nitrogen.Conc.+X.VXdt+total.cell+yield+emission_CO2+ Thr; 0.392, 0.716, pH+Main.P-Source.Conc.+Nitrogen. Conc.+OD+X.F.Suc+X.VXdt+yield+PL+rab+His+PO4. ferm.+PO4.apporte+PO4.utilise; 0.414, 0.716, pH+Nitrogen.Conc.+X.F.Suc+X.VXdt+total.cell+yield+ emission_O2+lactate+PO4.ferm.+PO4.apporte+PO4.utilise; 0.403, 0.716, pH+tmp+Main.P-Source.Conc.+Nitrogen. Conc.+X.F.Suc+X.VXdt+yield+emission_O2+Thr+PO4. ferm.+PO4.apporte+PO4.utilise; 0.391, 0.716, pH+Nitrogen.Conc.+OD+X.F.Suc+X.VXdt+yield+PL+ emission_CO2+Thr+His+PO4.ferm.+PO4.apporte+PO4. utilise; 0.380, 0.716, pH+P-Source.Feed.conc.+Nitrogen. Conc.+OD+X.F.Suc+X.VXdt+yield+emission_O2+Thr+ His+lactate+PO4.ferm.+PO4.apporte+PO4.utilise; 0.425, 0.716, pH+Main.Thr.Conc.+Nitrogen.Conc.+X.F.Suc+X. VXdt+yield+emission_O2+PO4.ferm.+PO4.apporte+PO4. utilise; 0.391, 0.716, pH+Main.Thr.Conc.+Nitrogen.Conc.+ X.F.Suc+X.VXdt+total.cell+yield+rab+Thr+lactate+PO4. ferm.+PO4.apporte+PO4.utilise; 0.391, 0.716, pH+Main. Thr.Conc.+Nitrogen.Conc.+X.F.Suc+X.VXdt+total.cell+ yield+emission_O2+Thr+His+PO4.ferm.+PO4.apporte+ PO4.utilise; 0.403, 0.716, pH+P-Source.Feed.conc.+ Nitrogen.Conc.+X.F.Suc+X.VXdt+yield+PL+rab+His+ PO4.ferm.+PO4.apporte+PO4.utilise; 0.391, 0.716, pH+tmp+Nitrogen.Conc.+X.F.Suc+X.VXdt+total.cell+ yield+emission_O2+emission_CO2+rab+PO4.ferm.+PO4. apporte+PO4.utilise; 0.379, 0.716, pH+Main.Thr.Conc.+Nitrogen.Conc.+OD+X.F.Suc+X.VXdt+yield+PL+emission_ CO2+rab+Thr+PO4.ferm.+PO4.apporte+PO4.utilise; 0.367, 0.716, pH+Main.P-Source.Conc.+Nitrogen.Conc.+OD+X. F.Suc+X.VXdt+yield+emission_O2+emission_CO2+rab+ Thr+PO4.ferm.+PO4.apporte+PO4.utilise; 0.391, 0.716, pH+Nitrogen.Conc.+X.F.Suc+X.VXdt+yield+emission_O2+emission_CO2+rab+Thr+His+PO4.ferm.+PO4. apporte+PO4.utilise; 0.403, 0.716, pH+Main.P-Source.

Conc.+Nitrogen.Conc.+X.F.Suc+X.VXdt+total.cell+yield+rab+lactate+PO4.ferm.+PO4.apporte+PO4.utilise; 0.403, 0.716, pH+tmp+Nitrogen.Conc.+X.F.Suc+X.VXdt+yield+PL+emission_CO2+Thr+PO4.ferm.+PO4.apporte+PO4.utilise; 0.414, 0.716, pH+tmp+Main.P-Source.Conc.+Nitrogen.Conc.+X.VXdt+total.cell+yield+PL+rab+Thr+His; 0.414, 0.716, pH+tmp+Nitrogen.Conc.+X.VXdt+total.cell+yield+PL+emission_CO2+rab+Thr+His; 0.391, 0.716, pH+Main.Thr.Conc.+Nitrogen.Conc.+X.F.Suc+X.VXdt+total.cell+yield+emission_CO2+rab+Thr+PO4.ferm.+PO4.apporte+PO4.utilise; 0.403, 0.716, pH+P-Source.Feed.conc.+Main.Thr.Conc.+Nitrogen.Conc.+X.F.Suc+X.VXdt+yield+rab+Thr+PO4.ferm.+PO4.apporte+PO4.utilise; 0.367, 0.716, pH+Nitrogen.Conc.+OD+X.F.Suc+X.VXdt+yield+PL+emission_O2+emission_CO2+Thr+His+lactate+PO4.ferm.+PO4.apporte+PO4.utilise; 0.403, 0.716, pH+Nitrogen.Conc.+OD+X.F.Suc+X.VXdt+yield+PL+emission_CO2+Thr+PO4.ferm.+PO4.apporte+PO4.utilise; 0.391, 0.716, pH+tmp+Nitrogen.Conc.+OD+X.F.Suc+X.VXdt+yield+emission_O2+rab+Thr+PO4.ferm.+PO4.apporte+PO4.utilise; 0.379, 0.716, pH+Main.Thr.Conc.+Nitrogen.Conc.+X.F.Suc+X.VXdt+total.cell+yield+PL+rab+Thr+His+PO4.ferm.+PO4.apporte+PO4.utilise; 0.414, 0.716, pH+tmp+Nitrogen.Conc.+X.F.Suc+X.VXdt+total.cell+yield+emission_CO2+PO4.ferm.+PO4.apporte+PO4.utilise; 0.379, 0.716, pH+Nitrogen.Conc.+X.F.Suc+X.VXdt+total.cell+yield+PL+emission_O2+rab+Thr+lactate+PO4.ferm.+PO4.apporte+PO4.utilise; 0.391, 0.716, pH+Nitrogen.Conc.+X.F.Suc+X.VXdt+total.cell+yield+PL+rab+His+lactate+PO4.ferm.+PO4.apporte+PO4.utilise; 0.391, 0.716, pH+Main.Thr.Conc.+Nitrogen.Conc.+X.F.Suc+X.VXdt+yield+emission_O2+rab+Thr+His+PO4.ferm.+PO4.apporte+PO4.utilise; 0.402, 0.716, pH+Main.P-Source.Conc.+Nitrogen.Conc.+X.F.Suc+X.VXdt+total.cell+yield+emission_O2+emission_CO2+PO4.ferm.+PO4.apporte+PO4.utilise; 0.391, 0.716, pH+tmp+Nitrogen.Conc.+X.F.Suc+X.VXdt+total.cell+yield+emission_O2+His+lactate+PO4.ferm.+PO4.apporte+PO4.utilise; 0.391, 0.716, pH+tmp+Nitrogen.Conc.+X.F.Suc+X.VXdt+yield+PL+emission_O2+rab+Thr+PO4.ferm.+PO4.apporte+PO4.utilise; 0.391, 0.716, pH+Nitrogen.Conc.+OD+X.F.Suc+X.VXdt+yield+emission_CO2+rab+Thr+SO4.ferm.+PO4.ferm.+PO4.apporte+PO4.utilise; 0.391, 0.716, pH+tmp+Main.P-Source.Conc.+Nitrogen.Conc.+X.F.Suc+X.VXdt+yield+emission_CO2+Thr+His+PO4.ferm.+PO4.apporte+PO4.utilise; 0.413, 0.716, pH+P-Source.Feed.conc.+Nitrogen.Conc.+X.F.Suc+X.VXdt+yield+emission_O2+His+PO4.ferm.+PO4.apporte+PO4.utilise; 0.391, 0.716, pH+Main.P-Source.Conc.+Main.Thr.Conc.+Nitrogen.Conc.+X.F.Suc+X.VXdt+yield+rab+Thr+lactate+PO4.ferm.+PO4.apporte+PO4.utilise; 0.413, 0.716, pH+P-Source.Feed.conc.+Nitrogen.Conc.+X.F.Suc+X.VXdt+yield+rab+lactate+PO4.ferm.+PO4.apporte+PO4.utilise; 0.366, 0.716, pH+tmp+Nitrogen.Conc.+OD+X.F.Suc+X.VXdt+yield+PL+emission_CO2+rab+Thr+His+PO4.ferm.+PO4.apporte+PO4.utilise; 0.391, 0.716, pH+Main.P-Source.Conc.+Nitrogen.Conc.+X.F.Suc+X.VXdt+total.cell+yield+PL+emission_O2+Thr+PO4.ferm.+PO4.apporte+PO4.utilise; 0.434, 0.716, pH+tmp+Main.P-Source.Conc.+X.VXdt+total.cell+yield+emission_O2+Thr+His; 0.402, 0.716, pH+tmp+Nitrogen.Conc.+X.F.Suc+X.VXdt+total.cell+yield+emission_O2+lactate+PO4.ferm.+PO4.apporte+PO4.utilise; 0.379, 0.716, pH+Nitrogen.Conc.+X.F.Suc+X.VXdt+total.cell+yield+PL+emission_O2+emission_CO2+Thr+His+PO4.ferm.+PO4.apporte+PO4.utilise; 0.379, 0.716, pH+Main.P-Source.Conc.+Main.Thr.Conc.+Nitrogen.Conc.+X.F.Suc+X.VXdt+total.cell+yield+rab+Thr+His+PO4.ferm.+PO4.apporte+PO4.utilise; 0.391, 0.716, pH+tmp+Nitrogen.Conc.+OD+X.F.Suc+X.VXdt+yield+PL+rab+His+PO4.ferm.+PO4.apporte+PO4.utilise; 0.391, 0.716, pH+tmp+Nitrogen.Conc.+X.F.Suc+X.VXdt+total.cell+yield+rab+His+lactate+PO4.ferm.+PO4.apporte+PO4.utilise; 0.379, 0.716, pH+tmp+Nitrogen.Conc.+X.F.Suc+X.VXdt+total.cell+yield+emission_CO2+Thr+His+lactate+PO4.ferm.+PO4.apporte+PO4.utilise; 0.366, 0.716, pH+Nitrogen.Conc.+OD+X.F.Suc+X.VXdt+yield+PL+emission_O2+emission_CO2+rab+Thr+lactate+PO4.ferm.+PO4.apporte+PO4.utilise; 0.402, 0.716, pH+Nitrogen.Conc.+OD+X.F.Suc+X.VXdt+yield+emission_O2+emission_CO2+lactate+PO4.ferm.+PO4.apporte+PO4.utilise; 0.391, 0.716, pH+Main.P-Source.Conc.+Nitrogen.Conc.+X.F.Suc+X.VXdt+yield+emission_CO2+rab+Thr+His+PO4.ferm.+PO4.apporte+PO4.utilise; 0.391, 0.716, pH+tmp+Nitrogen.Conc.+X.F.Suc+X.VXdt+total.cell+yield+emission_O2+Thr+SO4.ferm.+PO4.ferm.+PO4.apporte+PO4.utilise; 0.379, 0.716, pH+Main.P-Source.Conc.+Nitrogen.Conc.+X.F.Suc+X.VXdt+total.cell+yield+PL+emission_CO2+rab+Thr+PO4.ferm.+PO4.apporte+PO4.utilise; 0.402, 0.716, pH+Nitrogen.Conc.+X.F.Suc+X.VXdt+yield+emission_O2+emission_CO2+rab+lactate+PO4.ferm.+PO4.apporte+PO4.utilise; 0.366, 0.716, pH+tmp+Nitrogen.Conc.+OD+X.F.Suc+X.VXdt+yield+PL+emission_O2+rab+Thr+His+PO4.ferm.+PO4.apporte+PO4.utilise; 0.378, 0.716, pH+P-Source.Feed.conc.+Nitrogen.Conc.+X.F.Suc+X.VXdt+total.cell+yield+PL+emission_O2+rab+Thr+PO4.ferm.+PO4.apporte+PO4.utilise; 0.390, 0.716, pH+P-Source.Feed.conc.+Nitrogen.Conc.+OD+X.F.Suc+X.VXdt+yield+rab+Thr+SO4.ferm.+PO4.ferm.+PO4.apporte+PO4.utilise; 0.378, 0.716, pH+P-Source.Feed.conc.+Nitrogen.Conc.+OD+X.F.Suc+X.VXdt+yield+PL+emission_O2+emission_CO2+Thr+PO4.ferm.+PO4.apporte+PO4.utilise; 0.402, 0.716, pH+Main.Thr.Conc.+Nitrogen.Conc.+X.F.Suc+X.VXdt+yield+PL+rab+His+PO4.ferm.+PO4.apporte+PO4.utilise; 0.402, 0.716, pH+Nitrogen.Conc.+X.F.Suc+X.VXdt+yield+emission_O2+emission_CO2+rab+His+PO4.ferm.+PO4.apporte+PO4.utilise; 0.413, 0.716, pH+tmp+X.F.Suc+yield+emission_O2+rab+Thr+His+PO4.ferm.+PO4.apporte+PO4.utilise; 0.434, 0.716, pH+tmp+Nitrogen.Conc.+X.VXdt+total.cell+yield+PL+emission_O2+Thr; 0.378, 0.716, pH+Main.P-Source.Conc.+P-Source.Feed.conc.+Nitrogen.Conc.+OD+X.F.Suc+X.VXdt+yield+PL+rab+Thr+PO4.ferm.+PO4.apporte+PO4.utilise; 0.423, 0.716, pH+tmp+Main.P-Source.Conc.+X.VXdt+total.cell+yield+PL+emission_CO2+Thr+His; 0.390, 0.716, pH+P-Source.Feed.conc.+Main.Thr.Conc.+Nitrogen.Conc.+OD+X.F.Suc+X.VXdt+yield+emission_O2+Thr+PO4.ferm.+PO4.apporte+PO4.utilise; 0.413, 0.716, pH+tmp+Nitrogen.Conc.+OD+X.VXdt+total.cell+yield+rab+Thr+His+PO4.utilise; 0.378, 0.716, pH+Main.P-Source.Conc.+P-Source.Feed.conc.+Nitrogen.Conc.+OD+X.F.Suc+X.VXdt+yield+rab+Thr+His+PO4.ferm.+PO4.apporte+PO4.utilise; 0.390, 0.716, pH+Nitrogen.Conc.+X.F.Suc+X.VXdt+yield+emission_CO2+rab+Thr+His+lactate+PO4.ferm.+PO4.apporte+PO4.utilise; 0.378, 0.716, pH+tmp+Nitrogen.Conc.+OD+X.F.Suc+X.VXdt+total.cell+yield+emission_O2+Thr+His+PO4.ferm.+PO4.apporte+PO4.utilise; 0.390, 0.716, pH+Main.P-Source.Conc.+Nitrogen.Conc.+OD+X.F.Suc+X.VXdt+yield+rab+Thr+SO4.ferm.+PO4.ferm.+PO4.apporte+PO4.utilise; 0.390, 0.716, pH+Main.Thr.Conc.+Nitrogen.Conc.+OD+X.F.Suc+X.VXdt+yield+rab+Thr+SO4.ferm.+PO4.ferm.+PO4.apporte+PO4.utilise; 0.402, 0.716, pH+tmp+Nitrogen.Conc.+OD+X.VXdt+total.cell+yield+PL+rab+Thr+His+PO4.utilise; 0.413, 0.716, pH+P-Source.Feed.conc.+

Nitrogen.Conc.+X.F.Suc+X.VXdt+yield+emission_CO2+rab+PO4.ferm.+PO4.apporte+PO4.utilise; 0.378, 0.716, pH+Main.P-Source.Conc.+Nitrogen.Conc.+OD+X.F.Suc+X.VXdt+yield+emission_O2+emission_CO2+Thr+lactate+PO4.ferm.+PO4.apporte+PO4.utilise; 0.366, 0.716, pH+Main.P-Source.Conc.+Nitrogen.Conc.+OD+X.F.Suc+X.VXdt+yield+PL+emission_O2+emission_CO2+Thr+His+PO4.ferm.+PO4.apporte+PO4.utilise; 0.378, 0.716, pH+tmp+Nitrogen.Conc.+OD+X.F.Suc+X.VXdt+total.cell+yield+rab+Thr+His+PO4.ferm.+PO4.apporte+PO4.utilise; 0.378, 0.715, pH+P-Source.Feed.conc.+Nitrogen.Conc.+OD+X.F.Suc+X.VXdt+yield+PL+rab+Thr+lactate+PO4.ferm.+PO4.apporte+PO4.utilise; 0.378, 0.715, pH+Main.P-Source.Conc.+Main.Thr.Conc.+Nitrogen.Conc.+OD+X.F.Suc+X.VXdt+yield+PL+emission_O2+Thr+PO4.ferm.+PO4.apporte+PO4.utilise; 0.390, 0.715, pH+Nitrogen.Conc.+OD+X.F.Suc+X.VXdt+yield+PL+emission_O2+Thr+SO4.ferm.+PO4.ferm.+PO4.apporte+PO4.utilise; 0.423, 0.715, pH+tmp+Nitrogen.Conc.+X.VXdt+total.cell+yield+emission_O2+rab+Thr+His; 0.390, 0.715, pH+Main.P-Source.Conc.+Nitrogen.Conc.+X.F.Suc+X.VXdt+total.cell+yield+PL+emission_O2+rab+PO4.ferm.+PO4.apporte+PO4.utilise; 0.423, 0.715, pH+tmp+Nitrogen.Conc.+X.F.Suc+yield+emission_O2+Thr+PO4.ferm.+PO4.apporte+PO4.utilise; 0.365, 0.715, pH+Main.P-Source.Conc.+Nitrogen.Conc.+OD+X.F.Suc+X.VXdt+yield+PL+emission_O2+emission_CO2+rab+Thr+PO4.ferm.+PO4.apporte+PO4.utilise; 0.401, 0.715, pH+tmp+Nitrogen.Conc.+X.F.Suc+X.VXdt+yield+emission_O2+His+lactate+PO4.ferm.+PO4.apporte+PO4.utilise; 0.378, 0.715, pH+Main.Thr.Conc.+Nitrogen.Conc.+OD+X.F.Suc+X.VXdt+yield+emission_O2+emission_CO2+rab+Thr+PO4.ferm.+PO4.apporte+PO4.utilise; 0.390, 0.715, pH+tmp+Nitrogen.Conc.+X.VXdt+total.cell+yield+PL+emission_O2+emission_CO2+rab+Thr+His+PO4.utilise; 0.390, 0.715, pH+Nitrogen.Conc.+OD+X.F.Suc+X.VXdt+yield+PL+emission_O2+emission_CO2+His+PO4.ferm.+PO4.apporte+PO4.utilise; 0.412, 0.715, pH+tmp+Nitrogen.Conc.+X.F.Suc+yield+PL+emission_O2+His+PO4.ferm.+PO4.apporte+PO4.utilise; 0.390, 0.715, pH+tmp+Nitrogen.Conc.+OD+X.F.Suc+X.VXdt+yield+emission_CO2+rab+Thr+PO4.ferm.+PO4.apporte+PO4.utilise; 0.412, 0.715, pH+Main.Thr.Conc.+Nitrogen.Conc.+X.F.Suc+X.VXdt+yield+emission_CO2+rab+PO4.ferm.+PO4.apporte+PO4.utilise; 0.378, 0.715, pH+tmp+Nitrogen.Conc.+X.F.Suc+X.VXdt+total.cell+yield+emission_O2+Thr+His+lactate+PO4.ferm.+PO4.apporte+PO4.utilise; 0.390, 0.715, pH+tmp+Nitrogen.Conc.+X.F.Suc+yield+PL+emission_O2+rab+Thr+His+PO4.ferm.+PO4.apporte+PO4.utilise; 0.433, 0.715, pH+tmp+P-Source.Feed.conc.+X.VXdt+total.cell+yield+emission_CO2+Thr+His; 0.412, 0.715, pH+tmp+Nitrogen.Conc.+X.VXdt+total.cell+yield+PL+emission_CO2+Thr+His+PO4.apporte; 0.390, 0.715, pH+Nitrogen.Conc.+X.F.Suc+X.VXdt+total.cell+yield+PL+emission_O2+emission_CO2+rab+PO4.ferm.+PO4.apporte+PO4.utilise; 0.378, 0.715, pH+tmp+Main.Thr.Conc.+Nitrogen.Conc.+X.F.Suc+X.VXdt+total.cell+yield+emission_O2+Thr+His+PO4.ferm.+PO4.apporte+PO4.utilise; 0.378, 0.715, pH+Main.Thr.Conc.+Nitrogen.Conc.+OD+X.F.Suc+X.VXdt+yield+PL+emission_O2+emission_CO2+Thr+PO4.ferm.+PO4.apporte+PO4.utilise; 0.389, 0.715, pH+Main.P-Source.Conc.+Nitrogen.Conc.+X.F.Suc+X.VXdt+total.cell+yield+emission_O2+Thr+His+PO4.ferm.+PO4.apporte+PO4.utilise; 0.389, 0.715, pH+Main.Thr.Conc.+Nitrogen.Conc.+X.F.Suc+X.VXdt+total.cell+yield+emission_O2+emission_CO2+Thr+PO4.ferm.+PO4.apporte+PO4.utilise; 0.401, 0.715, pH+Nitrogen.Conc.+X.F.Suc+X.VXdt+yield+emission_CO2+rab+His+lactate+PO4.ferm.+PO4.apporte+PO4.utilise; 0.401, 0.715, pH+Main.P-Source.Conc.+Nitrogen.Conc.+X.F.Suc+X.VXdt+yield+emission_CO2+rab+His+PO4.ferm.+PO4.apporte+PO4.utilise; 0.377, 0.715, pH+P-Source.Feed.conc.+Nitrogen.Conc.+OD+X.F.Suc+X.VXdt+yield+PL+emission_O2+Thr+lactate+PO4.ferm.+PO4.apporte+PO4.utilise; 0.423, 0.715, pH+tmp+Main.P-Source.Conc.+X.VXdt+total.cell+yield+PL+emission_O2+Thr+His; 0.389, 0.715, pH+Main.P-Source.Conc.+Nitrogen.Conc.+X.F.Suc+X.VXdt+total.cell+yield+PL+rab+His+PO4.ferm.+PO4.apporte+PO4.utilise; 0.389, 0.715, pH+Nitrogen.Conc.+X.F.Suc+X.VXdt+total.cell+yield+PL+emission_O2+rab+lactate+PO4.ferm.+PO4.apporte+PO4.utilise; 0.401, 0.715, pH+Nitrogen.Conc.+X.F.Suc+X.VXdt+total.cell+yield+emission_O2+emission_CO2+lactate+PO4.ferm.+PO4.apporte+PO4.utilise; 0.412, 0.715, pH+P-Source.Feed.conc.+Nitrogen.Conc.+X.F.Suc+X.VXdt+yield+PL+emission_O2+PO4.ferm.+PO4.'apporte+PO4.utilise; 0.377, 0.715, pH+Main.P-Source.Conc.+Nitrogen.Conc.+X.F.Suc+X.VXdt+total.cell+yield+PL+rab+Thr+lactate+PO4.ferm.+PO4.apporte+PO4.utilise; 0.365, 0.715, pH+tmp+Nitrogen.Conc.+OD+X.F.Suc+X.VXdt+yield+PL+emission_O2+emission_CO2+Thr+His+PO4.ferm.+PO4.apporte+PO4.utilise; 0.389, 0.715, pH+P-Source.Feed.conc.+Nitrogen.Conc.+X.F.Suc+X.VXdt+yield+PL+rab+Thr+lactate+PO4.ferm.+PO4.apporte+PO4.utilise; 0.423, 0.715, pH+tmp+X.F.Suc+yield+PL+emission_CO2+His+PO4.ferm.+PO4.apporte+PO4.utilise; 0.377, 0.715, pH+Main.P-Source.Conc.+Main.Thr.Conc.+Nitrogen.Conc.+OD+X.F.Suc+X.VXdt+yield+rab+Thr+lactate+PO4.ferm.+PO4.apporte+PO4.utilise; 0.401, 0.715, pH+Main.P-Source.Conc.+Nitrogen.Conc.+OD+X.F.Suc+X.VXdt+yield+emission_O2+His+PO4.ferm.+PO4.apporte+PO4.utilise; 0.433, 0.715, pH+tmp+X.VXdt+total.cell+yield+PL+emission_O2+Thr+His; 0.401, 0.715, pH+Main.P-Source.Conc.+Nitrogen.Conc.+OD+X.F.Suc+X.VXdt+yield+PL+emission_O2+PO4.ferm.+PO4.apporte+PO4.utilise; 0.412, 0.715, pH+tmp+Nitrogen.Conc.+X.F.Suc+X.VXdt+yield+PL+emission_CO2+PO4.ferm.+PO4.apporte+PO4.utilise; 0.412, 0.715, pH+tmp+Nitrogen.Conc.+X.F.Suc+yield+PL+emission_CO2+His+PO4.ferm.+PO4.apporte+PO4.utilise; 0.412, 0.715, pH+tmp+Nitrogen.Conc.+X.VXdt+total.cell+yield+PL+emission_O2+emission_CO2+Thr+His; 0.401, 0.715, pH+Main.P-Source.Conc.+Nitrogen.Conc.+X.F.Suc+X.VXdt+yield+emission_O2+rab+lactate+PO4.ferm.+PO4.apporte+PO4.utilise; 0.377, 0.715, pH+Main.Thr.Conc.+Nitrogen.Conc.+OD+X.F.Suc+X.VXdt+Yield+PL+emission_O2+Thr+lactate+PO4.ferm.+PO4.apporte+PO4.utilise; 0.389, 0.715, pH+Nitrogen.Conc.+X.F.Suc+X.VXdt+yield+emission_O2+emission_CO2+rab+Thr+lactate+PO4.ferm.+PO4.apporte+PO4.utilise; 0.389, 0.715, pH+tmp+Nitrogen.Conc.+X.F.Suc+X.VXdt+yield+emission_O2+emission_CO2+rab+His+PO4.ferm.+PO4.apporte+PO4.utilise; 0.412, 0.715, pH+tmp+Nitrogen.Conc.+X.VXdt+total.cell+yield+rab+Thr+PO4.ferm.+PO4.apporte+PO4.utilise; 0.422, 0.715, pH+tmp+X.VXdt+total.cell+yield+PL+emission_O2+Thr+His+PO4.utilise; 0.389, 0.715, pH+tmp+Nitrogen.Conc.+OD+X.F.Suc+X.VXdt+total.cell+yield+rab+His+PO4.ferm.+PO4.apporte+PO4.utilise; 0.389, 0.715, pH+Main.Thr.Conc.+Nitrogen.Conc.+X.F.Suc+X.VXdt+yield+emission_O2+Thr+His+lactate+PO4.ferm.+PO4.apporte+PO4.utilise; 0.389, 0.715, pH+Nitrogen.Conc.+OD+X.F.Suc+X.VXdt+yield+PL+emission_O2+rab+lactate+PO4.ferm.+PO4.apporte+PO4.utilise; 0.377, 0.715, pH+Main.P-Source.Conc.+Nitrogen.Conc.+X.F.Suc+X.VXdt+total.

cell+yield+emission_O2+rab+Thr+His+PO4.ferm.+PO4.apporte+PO4.utilise; 0.389, 0.715, pH+Main.P-Source.Conc.+Nitrogen.Conc.+OD+X.F.Suc+X.VXdt+yield+PL+emission_O2+rab+PO4.ferm.+PO4.apporte+PO4.utilise; 0.389, 0.715, pH+Main.Thr.Conc.+Nitrogen.Conc.+X.F.Suc+X.VXdt+yield+emission_CO2+rab+Thr+His+PO4.ferm.+PO4.apporte+PO4.utilise; 0.377, 0.715, pH+P-Source.Feed.conc.+Nitrogen.Conc.+OD+X.F.Suc+X.VXdt+yield+emission_O2+emission_CO2+rab+Thr+PO4.ferm.+PO4.apporte+PO4.utilise; 0.377, 0.715, pH+Main.P-Source.Conc.+P-Source.Feed.conc.+Nitrogen.Conc.+OD+X.F.Suc+X.VXdt+yield+emission_O2+Thr+His+PO4.ferm.+PO4.apporte+PO4.utilise; 0.411, 0.715, pH+Main.P-Source.Conc.+Nitrogen.Conc.+X.F.Suc+X.VXdt+total.cell+yield+emission_O2+PO4.ferm.+PO4.apporte+PO4.utilise; 0.377, 0.715, pH+P-Source.Feed.conc.+Nitrogen.Conc.+OD+X.F.Suc+X.VXdt+yield+rab+Thr+His+lactate+PO4.ferm.+PO4.apporte+PO4.utilise; 0.400, 0.715, pH+Main.Thr.Conc.+Nitrogen.Conc.+X.F.Suc+X.VXdt+total.cell+yield+rab+His+PO4.ferm.+PO4.apporte+PO4.utilise; 0.377, 0.715, pH+tmp+Nitrogen.Conc.+X.F.Suc+X.VXdt+total.cell+yield+PL+rab+Thr+SO4.ferm.+PO4.ferm.+PO4.apporte+PO4.utilise; 0.422, 0.715, pH+tmp+P-Source.Feed.conc.+Nitrogen.Conc.+X.VXdt+total.cell+yield+emission_O2+Thr+His; 0.400, 0.715, pH+tmp+Nitrogen.Conc.+X.F.Suc+X.VXdt+yield+emission_O2+emission_CO2+rab+PO4.ferm.+PO4.apporte+PO4.utilise; 0.364, 0.715, pH+tmp+Nitrogen.Conc.+X.F.Suc+X.VXdt+total.cell+yield+PL+emission_O2+emission_CO2+rab+Thr+PO4.ferm.+PO4.apporte+PO4.utilise; 0.389, 0.715, pH+Main.P-Source.Conc.+Nitrogen.Conc.+X.F.Suc+X.VXdt+yield+emission_O2+emission_CO2+Thr+His+PO4.ferm.+PO4.apporte+PO4.utilise; 0.411, 0.715, pH+tmp+Nitrogen.Conc.+X.VXdt+total.cell+yield+emission_O2+Thr+PO4.ferm.+PO4.apporte+PO4.utilise; 0.389, 0.715, pH+P-Source.Feed.conc.+Nitrogen.Conc.+X.F.Suc+X.VXdt+yield+PL+emission_O2+rab+Thr+PO4.ferm.+PO4.apporte+PO4.utilise; 0.389, 0.715, pH+tmp+Nitrogen.Conc.+X.F.Suc+X.VXdt+yield+PL+emission_CO2+rab+Thr+PO4.ferm.+PO4.apporte+PO4.utilise; 0.432, 0.715, pH+tmp+Nitrogen.Conc.+X.VXdt+total.cell+yield+PL+rab+Thr; 0.400, 0.715, pH+Main.Thr.Conc.+Nitrogen.Conc.+OD+X.F.Suc+X.VXdt+yield+rab+His+PO4.ferm.+PO4.apporte+PO4.utilise; 0.411, 0.715, pH+Main.P-Source.Conc.+Nitrogen.Conc.+X.VXdt+total.cell+yield+emission_CO2+Thr+His+lactate; 0.400, 0.715, pH+P-Source.Feed.conc.+Nitrogen.Conc.+X.F.Suc+X.VXdt+total.cell+yield+emission_O2+rab+PO4.ferm.+PO4.apporte+PO4.utilise; 0.364, 0.715, pH+tmp+Nitrogen.Conc.+X.F.Suc+X.VXdt+total.cell+yield+PL+emission_O2+emission_CO2+rab+His+PO4.ferm.+PO4.apporte+PO4.utilise; 0.388, 0.715, pH+tmp+Nitrogen.Conc.+OD+X.F.Suc+X.VXdt+yield+emission_O2+emission_CO2+Thr+PO4.ferm.+PO4.apporte+PO4.utilise; 0.400, 0.715, pH+tmp+X.F.Suc+yield+PL+emission_O2+rab+Thr+His+PO4.ferm.+PO4.apporte+PO4.utilise; 0.376, 0.715, pH+Main.P-Source.Conc.+Main.Thr.Conc.+Nitrogen.Conc.+X.F.Suc+X.VXdt+yield+PL+rab+Thr+His+PO4.ferm.+PO4.apporte+PO4.utilise; 0.376, 0.715, pH+Nitrogen.Conc.+X.F.Suc+X.VXdt+total.cell+yield+PL+emission_CO2+rab+Thr+lactate+PO4.ferm.+PO4.apporte+PO4.utilise; 0.388, 0.715, pH+Nitrogen.Conc.+X.F.Suc+X.VXdt+total.cell+yield+PL+emission_CO2+rab+His+PO4.ferm.+PO4.apporte+PO4.utilise; 0.388, 0.715, pH+Nitrogen.Conc.+X.F.Suc+X.VXdt+yield+emission_O2+emission_CO2+Thr+His+lactate+PO4.ferm.+PO4.apporte+PO4.utilise; 0.411, 0.715, pH+Main.Thr.Conc.+Nitrogen.Conc.+X.F.Suc+X.VXdt+yield+emission_O2+His+PO4.ferm.+PO4.apporte+PO4.utilise; 0.400, 0.715, pH+tmp+Nitrogen.Conc.+X.F.Suc+X.VXdt+yield+rab+His+lactate+PO4.ferm.+PO4.apporte+PO4.utilise; 0.400, 0.715, pH+tmp+X.F.Suc+X.VXdt+total.cell+yield+emission_O2+Thr+His+PO4.ferm.+PO4.apporte+PO4.utilise; 0.388, 0.715, pH+Nitrogen.Conc.+OD+X.F.Suc+X.VXdt+yield+emission_O2+emission_CO2+Thr+SO4.ferm.+PO4.ferm.+PO4.apporte+PO4.utilise; 0.411, 0.715, pH+Main.P-Source.Conc.+P-Source.Feed.conc.+Nitrogen.Conc.+X.F.Suc+X.VXdt+yield+rab+PO4.ferm.+PO4.apporte+PO4.utilise; 0.388, 0.715, pH+P-Source.Feed.conc.+Nitrogen.Conc.+X.F.Suc+X.VXdt+yield+emission_O2+rab+Thr+His+PO4.ferm.+PO4.apporte+PO4.utilise; 0.411, 0.714, pH+Main.Thr.Conc.+Nitrogen.Conc.+X.F.Suc+X.VXdt+yield+emission_O2+emission_CO2+PO4.ferm.+PO4.apporte+PO4.utilise; 0.411, 0.714, pH+P-Source.Feed.conc.+Nitrogen.Conc.+X.F.Suc+X.VXdt+yield+emission_O2+emission_CO2+PO4.ferm.+PO4.apporte+PO4.utilise; 0.376, 0.714, pH+Main.P-Source.Conc.+Main.Thr.Conc.+Nitrogen.Conc.+OD+X.F.Suc+X.VXdt+yield+rab+Thr+SO4.ferm.+PO4.ferm.+PO4.apporte+PO4.utilise; 0.388, 0.714, pH+tmp+Nitrogen.Conc.+X.F.Suc+X.VXdt+total.cell+yield+rab+His+SO4.ferm.+PO4.ferm.+PO4.apporte+PO4.utilise; 0.376, 0.714, pH+Main.P-Source.Conc.+Nitrogen.Conc.+X.F.Suc+X.VXdt+total.cell+yield+PL+emission_O2+emission_CO2+Thr+PO4.ferm.+PO4.apporte+PO4.utilise; 0.399, 0.714, pH+tmp+Main.P-Source.Conc.+Nitrogen.Conc.+X.F.Suc+X.VXdt+yield+emission_O2+rab+PO4.ferm.+PO4.apporte+PO4.utilise; 0.399, 0.714, pH+tmp+P-Source.Feed.conc.+Nitrogen.Conc.+X.VXdt+total.cell+yield+PL+emission_O2+Thr+His+PO4.utilise; 0.388, 0.714, pH+Main.Thr.Conc.+Nitrogen.Conc.+X.F.Suc+X.VXdt+yield+emission_O2+emission_CO2+Thr+His+PO4.ferm.+PO4.apporte+PO4.utilise; 0.363, 0.714, pH+P-Source.Feed.conc.+Nitrogen.Conc.+OD+X.F.Suc+X.VXdt+yield+PL+emission_O2+rab+Thr+His+PO4.ferm.+PO4.apporte+PO4.utilise; 0.388, 0.714, pH+tmp+Nitrogen.Conc.+X.F.Suc+X.VXdt+yield+PL+emission_O2+emission_CO2+Thr+PO4.ferm.+PO4.apporte+PO4.utilise; 0.421, 0.714, pH+tmp+Nitrogen.Conc.+X.VXdt+total.cell+yield+emission_CO2+Thr+His+PO4.ferm.; 0.410, 0.714, pH+P-Source.Feed.conc.+Nitrogen.Conc.+X.F.Suc+X.VXdt+total.cell+yield+emission_O2+PO4.ferm.+PO4.apporte+PO4.utilise; 0.410, 0.714, Nitrogen.Conc.+OD+X.F.Suc+X.VXdt+yield+PL+emission_O2+Thr+PO4.ferm.+PO4.apporte+PO4.utilise; 0.431, 0.714, pH+tmp+X.F.Suc+yield+emission_O2+His+PO4.ferm.+PO4.apporte+PO4.utilise; 0.399, 0.714, pH+tmp+Main.P-Source.Conc.+Nitrogen.Conc.+X.VXdt+total.cell+yield+emission_O2+emission_CO2+rab+Thr+His; 0.376, 0.714, pH+P-Source.Feed.conc.+Nitrogen.Conc.+X.F.Suc+X.VXdt+total.cell+yield+emission_O2+rab+Thr+His+PO4.ferm.+PO4.apporte+PO4.utilise; 0.399, 0.714, pH+tmp+Nitrogen.Conc.+X.F.Suc+X.VXdt+total.cell+yield+rab+SO4.ferm.+PO4.ferm.+PO4.apporte+PO4.utilise; 0.410, 0.714, pH+Nitrogen.Conc.+X.F.Suc+X.VXdt+yield+rab+Thr+SO4.ferm.+PO4.ferm.+PO4.apporte+PO4.utilise; 0.375, 0.714, pH+P-Source.Feed.conc.+Nitrogen.Conc.+X.F.Suc+X.VXdt+total.cell+yield+PL+emission_CO2+rab+Thr+PO4.ferm.+PO4.apporte+PO4.utilise; 0.399, 0.714, pH+tmp+Main.P-Source.Conc.+Nitrogen.Conc.+X.F.Suc+X.VXdt+yield+rab+Thr+PO4.ferm.+PO4.apporte+PO4.utilise; 0.387, 0.714, pH+Main.P-Source.Conc.+Nitrogen.Conc.+X.F.Suc+X.VXdt+yield+PL+emission_O2+Thr+lactate+PO4.ferm.+PO4.apporte+PO4.utilise; 0.399, 0.714, pH+Main.P-Source.Conc.+

Nitrogen.Conc.+X.F.Suc+X.VXdt+yield+PL+emission_O2+His+PO4.ferm.+PO4.apporte+PO4.utilise; 0.399, 0.714, pH+tmp+Nitrogen.Conc.+X.VXdt+yield+emission_O2+emission_CO2+rab+Thr+His+PO4.utilise; 0.410, 0.714, pH+tmp+Nitrogen.Conc.+X.VXdt+total.cell+yield+PL+emission_O2+rab+Thr+His; 0.410, 0.714, pH+tmp+Nitrogen.Conc.+X.F.Suc+yield+PL+emission_O2+Thr+PO4.ferm.+PO4.apporte+PO4.utilise; 0.375, 0.714, pH+Main.P-Source.Conc.+Nitrogen.Conc.+X.F.Suc+X.VXdt+yield+PL+rab+Thr+His+lactate+PO4.ferm.+PO4.apporte+PO4.utilise; 0.375, 0.714, pH+Main.P-Source.Conc.+Main.Thr.Conc.+Nitrogen.Conc.+X.F.Suc+X.VXdt+total.cell+yield+PL+rab+Thr+PO4.ferm.+PO4.apporte+PO4.utilise; 0.387, 0.714, pH+Nitrogen.Conc.+X.F.Suc+X.VXdt+total.cell+yield+emission_O2+emission_CO2+rab+His+PO4.ferm.+PO4.apporte+PO4.utilise; 0.399, 0.714, pH+P-Source.Feed.conc.+Nitrogen.Conc.+OD+X.F.Suc+X.VXdt+yield+rab+His+PO4.ferm.+PO4.apporte+PO4.utilise; 0.410, 0.714, pH+tmp+Nitrogen.Conc.+X.VXdt+total.cell+yield+emission_CO2+Thr+His+lactate+PO4.utilise; 0.421, 0.714, pH+tmp+Nitrogen.Conc.+X.F.Suc+yield+PL+emission_O2+PO4.ferm.+PO4.apporte+PO4.utilise; 0.387, 0.714, pH+tmp+X.F.Suc+X.VXdt+total.cell+yield+PL+emission_O2+Thr+His+PO4.ferm.+PO4.apporte+PO4.utilise; 0.399, 0.714, pH+Main.Thr.Conc.+Nitrogen.Conc.+OD+X.F.Suc+X.VXdt+yield+PL+rab+PO4.ferm.+PO4.apporte+PO4.utilise; 0.410, 0.714, pH+tmp+P-Source.Feed.conc.+Nitrogen.Conc.+X.VXdt+total.cell+yield+emission_CO2+Thr+His+PO4.utilise; 0.410, 0.714, pH+tmp+P-Source.Feed.conc.+Nitrogen.Conc.+X.VXdt+total.cell+yield+PL+emission_O2+Thr+His; 0.421, 0.714, pH+tmp+Nitrogen.Conc.+X.F.Suc+yield+emission_CO2+Thr+PO4.ferm.+PO4.apporte+PO4.utilise; 0.387, 0.714, pH+tmp+Nitrogen.Conc.+X.F.Suc+X.VXdt+total.cell+yield+PL+rab+lactate+PO4.ferm.+PO4.apporte+PO4.utilise; 0.387, 0.714, pH+Nitrogen.Conc.+OD+X.F.Suc+X.VXdt+yield+emission_CO2+Thr+His+lactate+PO4.ferm.+PO4.apporte+PO4.utilise; 0.375, 0.714, pH+tmp+Main.Thr.Conc.+Nitrogen.Conc.+X.F.Suc+X.VXdt+total.cell+yield+rab+Thr+His+PO4.ferm.+PO4.apporte+PO4.utilise; 0.399, 0.714, pH+Main.P-Source.Conc.+P-Source.Feed.conc.+Nitrogen.Conc.+X.F.Suc+X.VXdt+yield+emission_O2+Thr+PO4.ferm.+PO4.apporte+PO4.utilise; 0.375, 0.714, pH+Nitrogen.Conc.+X.F.Suc+X.VXdt+total.cell+yield+emission_O2+rab+Thr+His+lactate+PO4.ferm.+PO4.apporte+PO4.utilise; 0.420, 0.714, pH+tmp+X.VXdt+total.cell+yield+PL+emission_CO2+Thr+His+PO4.apporte; 0.399, 0.714, pH+tmp+P-Source.Feed.conc.+Nitrogen.Conc.+X.F.Suc+X.VXdt+total.cell+yield+PL+rab+Thr+His+PO4.utilise; 0.399, 0.714, pH+tmp+P-Source.Feed.conc.+Nitrogen.Conc.+X.F.Suc+X.VXdt+total.cell+yield+PL+emission_CO2+Thr+His+PO4.utilise; 0.375, 0.714, pH+Main.P-Source.Conc.+Nitrogen.Conc.+X.F.Suc+X.VXdt+total.cell+yield+emission_O2+emission_CO2+rab+Thr+PO4.ferm.+PO4.apporte+PO4.utilise; 0.375, 0.714, pH+Main.P-Source.Conc.+P-Source.Feed.conc.+Nitrogen.Conc.+OD+X.F.Suc+X.VXdt+yield+PL+emission_O2+Thr+PO4.ferm.+PO4.apporte+PO4.utilise; 0.387, 0.714, pH+P-Source.Feed.conc.+Nitrogen.Conc.+X.F.Suc+X.VXdt+total.cell+yield+emission_O2+Thr+lactate+PO4.ferm.+PO4.apporte+PO4.utilise; 0.398, 0.714, pH+tmp+Nitrogen.Conc.+X.F.Suc+X.VXdt+yield+PL+rab+lactate+PO4.ferm.+PO4.apporte+PO4.utilise; 0.410, 0.714, pH+Main.P-Source.Conc.+Nitrogen.Conc.+X.F.Suc+X.VXdt+yield+emission_O2+lactate+PO4.ferm.+PO4.apporte+PO4.utilise; 0.362, 0.714, pH+Main.Thr.Conc.+Nitrogen.Conc.+OD+X.F.Suc+X.VXdt+yield+PL+emission_O2+rab+Thr+His+PO4.ferm.+PO4.apporte+PO4.utilise; 0.375, 0.714, pH+P-Source.Feed.conc.+Nitrogen.Conc.+X.F.Suc+X.VXdt+total.cell+yield+PL+rab+Thr+lactate+PO4.ferm.+PO4.apporte+PO4.utilise; 0.375, 0.714, pH+Main.P-Source.Conc.+Nitrogen.Conc.+X.F.Suc+X.VXdt+total.cell+yield+rab+Thr+His+lactate+PO4.ferm.+PO4.apporte+PO4.utilise; 0.387, 0.714, pH+P-Source.Feed.conc.+Nitrogen.Conc.+X.F.Suc+X.VXdt+yield+rab+Thr+His+lactate+PO4.ferm.+PO4.apporte+PO4.utilise; 0.398, 0.714, pH+tmp+Nitrogen.Conc.+OD+X.F.Suc+X.VXdt+yield+emission_CO2+His+PO4.ferm.+PO4.apporte+PO4.utilise; 0.410, 0.714, pH+Nitrogen.Conc.+OD+X.F.Suc+X.VXdt+yield+rab+SO4.ferm.+PO4.ferm.+PO4.apporte+PO4.utilise; 0.398, 0.714, pH+Main.P-Source.Conc.+Main.Thr.Conc.+Nitrogen.Conc.+X.F.Suc+X.VXdt+yield+rab+His+PO4.ferm.+PO4.apporte+PO4.utilise; 0.431, 0.714, pH+tmp+X.VXdt+total.cell+yield+emission_CO2+Thr+His+PO4.apporte; 0.420, 0.714, pH+Nitrogen.Conc.+X.F.Suc+X.VXdt+yield+rab+SO4.ferm.+PO4.ferm.+PO4.apporte+PO4.utilise; 0.398, 0.714, pH+P-Source.Feed.conc.+Nitrogen.Conc.+OD+X.F.Suc+X.VXdt+yield+PL+rab+PO4.ferm.+PO4.apporte+PO4.utilise; 0.375, 0.714, pH+Nitrogen.Conc.+OD+X.F.Suc+X.VXdt+yield+PL+rab+Thr+lactate+SO4.ferm.+PO4.ferm.+PO4.apporte+PO4.utilise; 0.387, 0.714, pH+Main.P-Source.Conc.+Nitrogen.Conc.+X.F.Suc+X.VXdt+total.cell+yield+PL+emission_CO2+rab+PO4.ferm.+PO4.apporte+PO4.utilise; 0.387, 0.714, pH+P-Source.Feed.conc.+Main.Thr.Conc.+Nitrogen.Conc.+X.F.Suc+X.VXdt+yield+rab+Thr+His+PO4.ferm.+PO4.apporte+PO4.utilise; 0.375, 0.714, pH+Main.P-Source.Conc.+Main.Thr.Conc.+Nitrogen.Conc.+OD+X.F.Suc+X.VXdt+yield+emission_O2+Thr+lactate+PO4.ferm.+PO4.apporte+PO4.utilise; 0.387, 0.714, pH+Main.P-Source.Conc.+Nitrogen.Conc.+OD+X.F.Suc+X.VXdt+yield+PL+rab+lactate+PO4.ferm.+PO4.apporte+PO4.utilise; 0.398, 0.714, pH+Main.P-Source.Conc.+Nitrogen.Conc.+X.F.Suc+X.VXdt+yield+emission_O2+emission_CO2+His+PO4.ferm.+PO4.apporte+PO4.utilise; 0.362, 0.714, pH+tmp+Main.Thr.Conc.+Nitrogen.Conc.+X.F.Suc+X.VXdt+total.cell+yield+rab+Thr+His+SO4.ferm.+PO4.ferm.+PO4.apporte+PO4.utilise; 0.398, 0.714, pH+Main.P-Source.Conc.+Nitrogen.Conc.+X.F.Suc+X.VXdt+yield+emission_CO2+rab+lactate+PO4.ferm.+PO4.apporte+PO4.utilise; 0.398, 0.714, pH+tmp+Nitrogen.Conc.+OD+X.F.Suc+X.VXdt+total.cell+yield+rab+PO4.ferm.+PO4.apporte+PO4.utilise; 0.387, 0.714, pH+Nitrogen.Conc.+OD+X.F.Suc+X.VXdt+yield+PL+emission_CO2+rab+lactate+PO4.ferm.+PO4.apporte+PO4.utilise; 0.375, 0.714, pH+Nitrogen.Conc.+OD+X.F.Suc+X.VXdt+yield+rab+Thr+His+lactate+SO4.ferm.+PO4.ferm.+PO4.apporte+PO4.utilise; 0.398, 0.714, pH+Main.P-Source.Conc.+Nitrogen.Conc.+X.F.Suc+X.VXdt+yield+emission_O2+emission_CO2+rab+PO4.ferm.+PO4.apporte+PO4.utilise; 0.387, 0.714, pH+tmp+Main.Thr.Conc.+Nitrogen.Conc.+X.F.Suc+X.VXdt+total.cell+yield+emission_O2+Thr+PO4.ferm.+PO4.apporte+PO4.utilise; 0.386, 0.714, pH+Main.P-Source.Conc.+Nitrogen.Conc.+OD+X.F.Suc+X.VXdt+yield+PL+emission_CO2+rab+PO4.ferm.+PO4.apporte+PO4.utilise; 0.430, 0.714, pH+tmp+Main.P-Source.Conc.+Nitrogen.Conc.+X.VXdt+total.cell+yield+rab+Thr; 0.398, 0.714, pH+Nitrogen.Conc.+X.F.Suc+X.VXdt+yield+emission_O2+emission_CO2+His+lactate+PO4.ferm.+PO4.apporte+PO4.utilise; 0.374, 0.714, pH+Nitrogen.Conc.+OD+X.F.Suc+X.VXdt+yield+PL+emission_O2+emission_CO2+rab+His+PO4.ferm.+PO4.apporte+PO4.utilise; 0.420, 0.714, pH+tmp+X.VXdt+total.cell+yield+PL+rab+Thr+His+PO4.utilise; 0.362, 0.714, pH+tmp+Nitrogen.Conc.+OD+X.F.Suc+X.VXdt+yield+ emission_O2+emission_CO2+rab+Thr+His+PO4.ferm.+ PO4.apporte+PO4.utilise; 0.398, 0.714, pH+P-Source.Feed. conc.+Main.Thr.Conc.+Nitrogen.Conc.+X.F.Suc+X.VXdt+ yield+emission_O2+Thr+PO4.ferm.+PO4.apporte+PO4. utilise; 0.374, 0.714, pH+tmp+Nitrogen.Conc.+OD+X.F. Suc+X.VXdt+yield+emission_O2+Thr+His+SO4.ferm.+ PO4.ferm.+PO4.apporte+PO4.utilise; 0.398, 0.714, pH+Main.Thr.Conc.+Nitrogen.Conc.+X.F.Suc+X.VXdt+ yield+PL+rab+lactate+PO4.ferm.+PO4.apporte+PO4.utilise; 0.386, 0.714, pH+tmp+Main.Thr.Conc.+Nitrogen. Conc.+X.F.Suc+X.VXdt+total.cell+yield+rab+Thr+PO4. ferm.+PO4.apporte+PO4.utilise; 0.386, 0.713, pH+Main.P-Source.Conc.+Nitrogen.Conc.+X.F.Suc+X.VXdt+yield+ emission_O2+rab+Thr+lactate+PO4.ferm.+PO4.apporte+ PO4.utilise; 0.398, 0.713, pH+Main.Thr.Conc.+Nitrogen. Conc.+X.F.Suc+X.VXdt+total.cell+yield+PL+rab+PO4. ferm.+PO4.apporte+PO4.utilise; 0.420, 0.713, pH+tmp+X. F.Suc+yield+emission_O2+Thr+His+PO4.ferm.+PO4. apporte+PO4.utilise; 0.386, 0.713, pH+Main.P-Source. Conc.+Nitrogen.Conc.+X.F.Suc+X.VXdt+yield+emission_ O2+emission_CO2+rab+Thr+PO4.ferm.+PO4.apporte+ PO4.utilise; 0.374, 0.713, pH+tmp+Main.P-Source.Conc.+ Nitrogen.Conc.+X.F.Suc+X.VXdt+yield+PL+emission_ O2+Thr+His+PO4.ferm.+PO4.apporte+PO4.utilise; 0.398, 0.713, pH+tmp+Nitrogen.Conc.+X.F.Suc+yield+emission_ CO2+rab+Thr+His+PO4.ferm.+PO4.apporte+PO4.utilise; 0.420, 0.713, pH+tmp+Nitrogen.Conc.+X.VXdt+total.cell+ yield+PL+rab+Thr+PO4.utilise; 0.430, 0.713, pH+tmp+ Main.P-Source.Conc.+X.VXdt+total.cell+yield+rab+Thr+ His; 0.386, 0.713, pH+Nitrogen.Conc.+OD+X.F.Suc+X. VXdt+yield+emission_O2+Thr+lactate+SO4.ferm.+PO4. ferm.+PO4.apporte+PO4.utilise; 0.362, 0.713, pH+Main.P-Source.Conc.+Main.Thr.Conc.+Nitrogen.Conc.+OD+X.F. Suc+X.VXdt+yield+PL+rab+Thr+His+PO4.ferm.+PO4. apporte+PO4.utilise; 0.386, 0.713, pH+Nitrogen.Conc.+X. F.Suc+X.VXdt+yield+PL+emission_O2+rab+His+lactate+ PO4.ferm.+PO4.apporte+PO4.utilise; 0.386, 0.713, pH+Main.P-Source.Conc.+Main.Thr.Conc.+Nitrogen. Conc.+X.F.Suc+X.VXdt+total.cell+yield+emission_O2+ Thr+PO4.ferm.+PO4.apporte+PO4.utilise; 0.386, 0.713, pH+Main.Thr.Conc.+Nitrogen.Conc.+X.F.Suc+X.VXdt+ yield+PL+emission_O2+rab+Thr+PO4.ferm.+PO4.apporte+PO4.utilise; 0.362, 0.713, pH+P-Source.Feed.conc.+ Nitrogen.Conc.+OD+X.F.Suc+X.VXdt+yield+PL+ emission_CO2+rab+Thr+His+PO4.ferm.+PO4.apporte+ PO4.utilise; 0.374, 0.713, pH+tmp+Nitrogen.Conc.+X.F. Suc+X.VXdt+yield+emission_O2+emission_CO2+rab+ Thr+His+PO4.ferm.+PO4.apporte+PO4.utilise; 0.398, 0.713, pH+tmp+Nitrogen.Conc.+X.VXdt+total.cell+yield+ emission_O2+Thr+His+PO4.ferm.+PO4.apporte+PO4.utilise; 0.386, 0.713, pH+P-Source.Feed.conc.+Nitrogen. Conc.+X.F.Suc+X.VXdt+yield+PL+emission_CO2+rab+ Thr+PO4.ferm.+PO4.apporte+PO4.utilise; 0.374, 0.713, pH+tmp+Nitrogen.Conc.+X.F.Suc+X.VXdt+total.cell+ yield+PL+emission_O2+emission_CO2+rab+PO4.ferm.+ PO4.apporte+PO4.utilise; 0.374, 0.713, pH+tmp+Main.Thr. Conc.+Nitrogen.Conc.+X.F.Suc+X.VXdt+total.cell+yield+ emission_CO2+Thr+His+PO4.ferm.+PO4.apporte+PO4. utilise; 0.386, 0.713, pH+tmp+Nitrogen.Conc.+OD+X.F. Suc+X.VXdt+total.cell+yield+rab+Thr+PO4.ferm.+PO4. apporte+PO4.utilise; 0.374, 0.713, pH+Main.Thr.Conc.+ Nitrogen.Conc.+X.F.Suc+X.VXdt+total.cell+yield+ emission_O2+rab+Thr+His+PO4.ferm.+PO4.apporte+PO4. utilise; 0.386, 0.713, pH+Main.P-Source.Conc.+Main.Thr. Conc.+Nitrogen.Conc.+X.F.Suc+X.VXdt+yield+PL+ emission_O2+Thr+PO4.ferm.+PO4.apporte+PO4.utilise; 0.374, 0.713, pH+Nitrogen.Conc.+X.F.Suc+X.VXdt+total. cell+yield+PL+emission_O2+Thr+His+lactate+PO4.ferm.+ PO4.apporte+PO4.utilise; 0.420, 0.713, pH+tmp+X.VXdt+ total.cell+yield+emission_O2+emission_CO2+rab+Thr+ His; 0.386, 0.713, pH+P-Source.Feed.conc.+Nitrogen. Conc.+X.F.Suc+X.VXdt+yield+PL+emission_O2+Thr+ lactate+PO4.ferm.+PO4.apporte+PO4.utilise; 0.386, 0.713, pH+Nitrogen.Conc.+X.F.Suc+X.VXdt+total.cell+yield+ PL+emission_CO2+rab+lactate+PO4.ferm.+PO4.apporte+ PO4.utilise; 0.374, 0.713, pH+Main.P-Source.Conc.+Nitrogen.Conc.+X.F.Suc+X.VXdt+total.cell+yield+emission_ CO2+rab+Thr+His+PO4.ferm.+PO4.apporte+PO4.utilise; 0.386, 0.713, pH+P-Source.Feed.conc.+Nitrogen.Conc.+X. F.Suc+X.VXdt+yield+emission_O2+Thr+His+lactate+ PO4.ferm.+PO4.apporte+PO4.utilise; 0.374, 0.713, pH+Nitrogen.Conc.+OD+X.F.Suc+X.VXdt+yield+emission_O2+ rab+Thr+His+SO4.ferm.+PO4.ferm.+PO4.apporte+PO4. utilise; 0.374, 0.713, pH+Nitrogen.Conc.+OD+X.F.Suc+X. VXdt+yield+PL+emission_O2+Thr+His+SO4.ferm.+PO4. ferm.+PO4.apporte+PO4.utilise; 0.374, 0.713, pH+P-Source.Feed.conc.+Main.Thr.Conc.+Nitrogen.Conc.+OD+ X.F.Suc+X.VXdt+yield+rab+Thr+His+PO4.ferm.+PO4. apporte+PO4.utilise; 0.397, 0.713, pH+Main.Thr.Conc.+ Nitrogen.Conc.+OD+X.F.Suc+X.VXdt+yield+emission_ CO2+Thr+PO4.ferm.+PO4.apporte+PO4.utilise; 0.409, 0.713, Nitrogen.Conc.+OD+X.F.Suc+X.VXdt+yield+PL+ rab+PO4.ferm.+PO4.apporte+PO4.utilise; 0.386, 0.713, pH+tmp+Main.P-Source.Conc.+Nitrogen.Conc.+X. F.Suc+X.VXdt+total.cell+yield+emission_O2+rab+PO4. ferm.+PO4.apporte+PO4.utilise; 0.386, 0.713, pH+Main.P-Source.Conc.+Nitrogen.Conc.+OD+X.F.Suc+X.VXdt+ yield+emission_O2+rab+His+PO4.ferm.+PO4.apporte+ PO4.utilise; 0.419, 0.713, pH+tmp+P-Source.Feed.conc.+X. VXdt+total.cell+yield+PL+emission_CO2+Thr+His; 0.397, 0.713, pH+Nitrogen.Conc.+OD+X.F.Suc+X.VXdt+total. cell+yield+rab+Thr+PO4.ferm.+PO4.apporte+PO4.utilise; 0.430, 0.713, pH+tmp+Nitrogen.Conc.+X.VXdt+total.cell+ yield+PL+emission_CO2+Thr; 0.419, 0.713, pH+tmp+Nitrogen.Conc.+X.VXdt+total.cell+yield+rab+PO4.ferm.+ PO4.apporte+PO4.utilise; 0.408, 0.713, pH+tmp+Nitrogen. Conc.+X.VXdt+total.cell+yield+PL+emission_CO2+Thr+ His+lactate; 0.374, 0.713, pH+tmp+Nitrogen.Conc.+OD+X. F.Suc+X.VXdt+yield+PL+emission_O2+rab+Thr+PO4. ferm.+PO4.apporte+PO4.utilise; 0.386, 0.713, pH+Main.P-Source.Conc.+Nitrogen.Conc.+X.F.Suc+X.VXdt+yield+ emission_O2+Thr+His+lactate+PO4.ferm.+PO4.apporte+ PO4.utilise; 0.374, 0.713, pH+Nitrogen.Conc.+X.F.Suc+X. VXdt+total.cell+yield+PL+emission_O2+emission_CO2+ Thr+lactate+PO4.ferm.+PO4.apporte+PO4.utilise; 0.397, 0.713, pH+tmp+Main.P-Source.Conc.+Nitrogen.Conc.+X. F.Suc+X.VXdt+yield+emission_CO2+His+PO4.ferm.+ PO4.apporte+PO4.utilise; 0.397, 0.713, pH+tmp+Main.P-Source.Conc.+Nitrogen.Conc.+X.F.Suc+X.VXdt+yield+ emission_CO2+rab+PO4.ferm.+PO4.apporte+PO4.utilise; 0.361, 0.713, pH+tmp+Nitrogen.Conc.+OD+X.F.Suc+X. VXdt+total.cell+yield+PL+emission_O2+Thr+His+PO4. ferm.+PO4.apporte+PO4.utilise; 0.397, 0.713, pH+P-Source.Feed.conc.+Nitrogen.Conc.+X.F.Suc+X.VXdt+ yield+PL+emission_O2+rab+PO4.ferm.+PO4.apporte+ PO4.utilise; 0.408, 0.713, pH+tmp+X.F.Suc+yield+ emission_CO2+rab+Thr+His+PO4.ferm.+PO4.apporte+ PO4.utilise; 0.374, 0.713, pH+P-Source.Feed.conc.+ Nitrogen.Conc.+X.F.Suc+X.VXdt+total.cell+yield+rab+ Thr+His+lactate+PO4.ferm.+PO4.apporte+PO4.utilise; 0.386, 0.713, pH+Main.Thr.Conc.+Nitrogen.Conc.+X.F. Suc+X.VXdt+total.cell+yield+PL+emission_O2+Thr+PO4. ferm.+PO4.apporte+PO4.utilise; 0.374, 0.713, pH+Main.

Thr.Conc.+Nitrogen.Conc.+X.F.Suc+X.VXdt+yield+PL+ rab+Thr+His+lactate+PO4.ferm.+PO4.apporte+PO4.utilise; 0.361, 0.713, pH+tmp+Nitrogen.Conc.+OD+X.F.Suc+X. VXdt+total.cell+yield+PL+rab+Thr+His+PO4.ferm.+PO4. apporte+PO4.utilise; 0.373, 0.713, pH+P-Source.Feed. conc.+Main.Thr.Conc.+Nitrogen.Conc.+X.F.Suc+X.VXdt+ total.cell+yield+rab+Thr+His+PO4.ferm.+PO4.apporte+ PO4.utilise; 0.397, 0.713, pH+Main.Thr.Conc.+Nitrogen. Conc.+X.F.Suc+X.VXdt+total.cell+yield+emission_O2+ rab+PO4.ferm.+PO4.apporte+PO4.utilise; 0.385, 0.713, pH+Main.Thr.Conc.+Nitrogen.Conc.+X.F.Suc+X.VXdt+ yield+PL+emission_O2+Thr+lactate+PO4.ferm.+PO4.ap- porte+PO4.utilise; 0.397, 0.713, pH+Main.Thr.Conc.+Ni- trogen.Conc.+X.F.Suc+X.VXdt+yield+rab+His+lactate+ PO4.ferm.+PO4.apporte+PO4.utilise; 0.361, 0.713, pH+Main.Thr.Conc.+Nitrogen.Conc.+OD+X.F.Suc+X. VXdt+yield+PL+emission_CO2+rab+Thr+His+PO4.ferm.+ PO4.apporte+PO4.utilise; 0.429, 0.713, pH+tmp+Main.P- Source.Conc.+Nitrogen.Conc.+X.VXdt+total.cell+yield+ emission_O2+Thr; 0.373, 0.713, pH+Main.P-Source. Conc.+P-Source.Feed.conc.+Nitrogen.Conc.+X.F.Suc+X. VXdt+total.cell+yield+PL+rab+Thr+PO4.ferm.+PO4. apporte+PO4.utilise; 0.373, 0.713, pH+Nitrogen.Conc.+X. F.Suc+X.VXdt+total.cell+yield+emission_O2+emission_ CO2+rab+Thr+lactate+PO4.ferm.+PO4.apporte+PO4. utilise; 0.373, 0.713, pH+Main.P-Source.Conc.+Main.Thr. Conc.+Nitrogen.Conc.+OD+X.F.Suc+X.VXdt+yield+ emission_O2+rab+Thr+PO4.ferm.+PO4.apporte+PO4. utilise; 0.361, 0.713, pH+Main.P-Source.Conc.+Nitrogen. Conc.+OD+X.F.Suc+X.VXdt+yield+PL+emission_O2+ rab+Thr+lactate+PO4.ferm.+PO4.apporte+PO4.utilise; 0.397, 0.713, pH+tmp+Nitrogen.Conc.+X.F.Suc+yield+ emission_O2+emission_CO2+Thr+His+PO4.ferm.+PO4. apporte+PO4.utilise; 0.397, 0.713, pH+Nitrogen.Conc.+ OD+X.F.Suc+X.VXdt+yield+emission_CO2+Thr+lactate+ PO4.ferm.+PO4.apporte+PO4.utilise; 0.397, 0.713, pH+Nitrogen.Conc.+X.F.Suc+X.VXdt+total.cell+yield+ PL+emission_O2+lactate+PO4.ferm.+PO4.apporte+PO4. utilise; 0.397, 0.713, pH+tmp+Nitrogen.Conc.+X.F.Suc+X. VXdt+total.cell+yield+PL+emission_CO2+PO4.ferm.+ PO4.apporte+PO4.utilise; 0.361, 0.713, pH+tmp+Nitrogen. Conc.+X.F.Suc+X.VXdt+total.cell+yield+PL+emission_ CO2+Thr+His+lactate+PO4.ferm.+PO4.apporte+PO4. utilise; 0.373, 0.713, pH+Nitrogen.Conc.+X.F.Suc+X. VXdt+yield+PL+emission_O2+rab+Thr+His+lactate+PO4. ferm.+PO4.apporte+PO4.utilise; 0.385, 0.713, pH+Nitrogen.Conc.+OD+X.F.Suc+X.VXdt+yield+PL+ emission_O2+His+lactate+PO4.ferm.+PO4.apporte+PO4. utilise; 0.385, 0.713, pH+P-Source.Feed.conc.+Nitrogen. Conc.+X.F.Suc+X.VXdt+total.cell+yield+PL+rab+His+ PO4.ferm.+PO4.apporte+PO4.utilise; 0.385, 0.713, pH+P- Source.Feed.conc.+Nitrogen.Conc.+X.F.Suc+X.VXdt+ yield+emission_CO2+rab+Thr+His+PO4.ferm.+PO4. apporte+PO4.utilise; 0.373, 0.713, pH+tmp+Main.P- Source.Conc.+Nitrogen.Conc.+X.F.Suc+X.VXdt+yield+ PL+emission_CO2+Thr+His+PO4.ferm.+PO4.apporte+ PO4.utilise; 0.373, 0.713, pH+Main.P-Source.Conc.+ Nitrogen.Conc.+X.F.Suc+X.VXdt+yield+PL+emission_ O2+rab+Thr+His+PO4.ferm.+PO4.apporte+PO4.utilise; 0.397, 0.713, pH+tmp+Nitrogen.Conc.+X.F.Suc+X.VXdt+ yield+PL+emission_O2+lactate+PO4.ferm.+PO4.apporte+ PO4.utilise; 0.385, 0.713, pH+Main.P-Source.Conc.+Nitro- gen.Conc.+X.F.Suc+X.VXdt+yield+emission_O2+ rab+His+PO4.ferm.+PO4.apporte+PO4.utilise; 0.360, 0.713, pH+tmp+Main.Thr.Conc.+Nitrogen.Conc.+X.F.Suc+ X.VXdt+total.cell+yield+PL+emission_O2+Thr+His+PO4. ferm.+PO4.apporte+PO4.utilise; 0.385, 0.713, pH+tmp+ Main.P-Source.Conc.+Nitrogen.Conc.+X.F.Suc+X.VXdt+ yield+rab+Thr+His+PO4.ferm.+PO4.apporte+PO4.utilise; 0.373, 0.713, pH+Main.Thr.Conc.+Nitrogen.Conc.+OD+X. F.Suc+X.VXdt+yield+rab+Thr+His+SO4.ferm.+PO4. ferm.+PO4.apporte+PO4.utilise; 0.429, 0.713, pH+tmp+Ni- trogen.Conc.+X.F.Suc+yield+rab+PO4.ferm.+PO4. apporte+PO4.utilise; 0.360, 0.713, pH+Main.Thr.Conc.+ Nitrogen.Conc.+OD+X.F.Suc+X.VXdt+yield+PL+rab+ Thr+His+lactate+PO4.ferm.+PO4.apporte+PO4.utilise; 0.347, 0.713, pH+Nitrogen.Conc.+OD+X.F.Suc+X.VXdt+ yield+PL+emission_O2+emission_CO2+rab+Thr+His+lac- tate+PO4.ferm.+PO4.apporte+PO4.utilise; 0.373, 0.713, pH+P-Source.Feed.conc.+Nitrogen.Conc.+X.F.Suc+X. VXdt+total.cell+yield+PL+emission_O2+emission_CO2+ Thr+PO4.ferm.+PO4.apporte+PO4.utilise; 0.373, 0.713, pH+Nitrogen.Conc.+OD+X.F.Suc+X.VXdt+yield+PL+ emission_O2+rab+Thr+SO4.ferm.+PO4.ferm.+PO4.ap- porte+PO4.utilise; 0.385, 0.713, pH+P-Source.Feed.conc.+ Nitrogen.Conc.+X.F.Suc+X.VXdt+yield+PL+emission_ O2+emission_CO2+Thr+PO4.ferm.+PO4.apporte+PO4. utilise; 0.397, 0.713, pH+tmp+Nitrogen.Conc.+X.VXdt+ total.cell+yield+rab+Thr+His+PO4.ferm.+PO4.apporte+ PO4.utilise; 0.360, 0.713, pH+Main.Thr.Conc.+Nitrogen. Conc.+OD+X.F.Suc+X.VXdt+yield+emission_O2+ emission_CO2+rab+Thr+His+PO4.ferm.+PO4.apporte+ PO4.utilise; 0.396, 0.713, pH+Main.Thr.Conc.+Nitrogen. Conc.+X.F.Suc+X.VXdt+yield+emission_O2+rab+His+ PO4.ferm.+PO4.apporte+PO4.utilise; 0.429, 0.713, pH+tmp+X.VXdt+total.cell+yield+emission_O2+Thr+His+ PO4.utilise; 0.408, 0.713, pH+tmp+P-Source.Feed.conc.+ Nitrogen.Conc.+X.VXdt+total.cell+yield+emission_O2+ Thr+His+PO4.utilise; 0.396, 0.713, pH+P-Source.Feed. conc.+Nitrogen.Conc.+X.F.Suc+X.VXdt+total.cell+yield+ emission_CO2+rab+PO4.ferm.+PO4.apporte+PO4.utilise; 0.385, 0.713, pH+Main.P-Source.Conc.+Nitrogen.Conc.+ X.F.Suc+X.VXdt+yield+PL+rab+His+lactate+PO4.ferm.+ PO4.apporte+PO4.utilise; 0.418, 0.713, pH+tmp+Main.P- Source.Conc.+X.VXdt+total.cell+yield+PL+rab+Thr+His; 0.385, 0.713, pH+Nitrogen.Conc.+X.F.Suc+X.VXdt+total. cell+yield+PL+emission_O2+emission_CO2+His+PO4. ferm.+PO4.apporte+PO4.utilise; 0.373, 0.713, pH+tmp+ Main.P-Source.Conc.+Nitrogen.Conc.+OD+X.F.Suc+X. VXdt+yield+emission_CO2+Thr+His+PO4.ferm.+PO4. apporte+PO4.utilise; 0.373, 0.713, pH+P-Source.Feed. conc.+Nitrogen.Conc.+OD+X.F.Suc+X.VXdt+yield+rab+ Thr+His+SO4.ferm.+PO4.ferm.+PO4.apporte+PO4.utilise; 0.360, 0.713, pH+tmp+Main.Thr.Conc.+Nitrogen.Conc.+X. F.Suc+X.VXdt+total.cell+yield+emission_O2+Thr+His+ SO4.ferm.+PO4.ferm.+PO4.apporte+PO4.utilise; 0.429, 0.713, pH+tmp+X.VXdt+total.cell+yield+emission_CO2+ rab+Thr+His; 0.408, 0.713, pH+tmp+X.F.Suc+yield+PL+ emission_O2+Thr+His+PO4.ferm.+PO4.apporte+PO4.util- ise; 0.373, 0.713, pH+tmp+Nitrogen.Conc.+OD+X.F.Suc+ X.VXdt+yield+rab+Thr+His+SO4.ferm.+PO4.ferm.+PO4. apporte+PO4.utilise; 0.418, 0.713, pH+tmp+Main.P- Source.Conc.+Nitrogen.Conc.+X.VXdt+total.cell+yield+ PL+rab+Thr; 0.385, 0.713, pH+Main.P-Source.Conc.+ Nitrogen.Conc.+X.F.Suc+X.VXdt+yield+emission_CO2+ rab+Thr+lactate+PO4.ferm.+PO4.apporte+PO4.utilise; 0.407, 0.713, pH+Main.Thr.Conc.+Nitrogen.Conc.+OD+X. F.Suc+X.VXdt+yield+emission_O2+PO4.ferm.+PO4.ap- porte+PO4.utilise; 0.396, 0.713, pH+P-Source.Feed. conc.+Nitrogen.Conc.+X.VXdt+total.cell+yield+emission_ O2+emission_CO2+rab+Thr+His; 0.385, 0.713, pH+Main. P-Source.Conc.+P-Source.Feed.conc.+Nitrogen.Conc.+X. F.Suc+X.VXdt+yield+PL+rab+Thr+PO4.ferm.+PO4. apporte+PO4.utilise; 0.396, 0.713, pH+tmp+Nitrogen.

Conc.+X.VXdt+total.cell+yield+PL+rab+Thr+PO4.ferm.+ PO4.apporte+PO4.utilise; 0.385, 0.713, pH+Main.P-Source. Conc.+Main.Thr.Conc.+Nitrogen.Conc.+X.F.Suc+X. VXdt+yield+emission_O2+rab+Thr+PO4.ferm.+PO4. apporte+PO4.utilise; 0.360, 0.713, pH+Nitrogen.Conc.+X. F.Suc+X.VXdt+total.cell+yield+PL+emission_O2+ emission_CO2+rab+Thr+His+PO4.ferm.+PO4.apporte+ PO4.utilise; 0.439, 0.713, pH+tmp+X.VXdt+total.cell+ yield+rab+Thr+His; 0.407, 0.712, pH+P-Source.Feed. conc.+Nitrogen.Conc.+OD+X.F.Suc+X.VXdt+yield+ emission_O2+PO4.ferm.+PO4.apporte+PO4.utilise; 0.372, 0.712, pH+tmp+Nitrogen.Conc.+X.F.Suc+X.VXdt+total. cell+yield+PL+emission_O2+His+lactate+PO4.ferm.+PO4. apporte+PO4.utilise; 0.385, 0.712, pH+tmp+Main.P-Source.Conc.+Nitrogen.Conc.+X.F.Suc+X.VXdt+yield+ PL+emission_O2+Thr+PO4.ferm.+PO4.apporte+PO4. utilise; 0.396, 0.712, pH+Nitrogen.Conc.+X.F.Suc+X. VXdt+total.cell+yield+emission_O2+His+lactate+PO4. ferm.+PO4.apporte+PO4.utilise; 0.385, 0.712, pH+Main. Thr.Conc.+Nitrogen.Conc.+X.F.Suc+X.VXdt+yield+PL+ emission_CO2+rab+Thr+PO4.ferm.+PO4.apporte+PO4. utilise; 0.396, 0.712, pH+Main.P-Source.Conc.+Main.Thr. Conc.+Nitrogen.Conc.+X.F.Suc+X.VXdt+yield+PL+rab+ PO4.ferm.+PO4.apporte+PO4.utilise; 0.385, 0.712, pH+tmp+Main.P-Source.Conc.+Nitrogen.Conc.+X.F.Suc+ X.VXdt+yield+emission_O2+rab+His+PO4.ferm.+PO4.apporte+PO4.utilise; 0.407, 0.712, pH+tmp+X.F.Suc+yield+ emission_O2+emission_CO2+Thr+His+PO4.ferm.+PO4. apporte+PO4.utilise; 0.384, 0.712, pH+Main.P-Source. Conc.+P-Source.Feed.conc.+Nitrogen.Conc.+X.F.Suc+X. VXdt+yield+rab+Thr+His+PO4.ferm.+PO4.apporte+PO4. utilise; 0.372, 0.712, pH+P-Source.Feed.conc.+Main.Thr. Conc.+Nitrogen.Conc.+OD+X.F.Suc+X.VXdt+yield+ emission_O2+Thr+His+PO4.ferm.+PO4.apporte+PO4. utilise; 0.396, 0.712, pH+tmp+Main.P-Source.Conc.+ Nitrogen.Conc.+X.VXdt+total.cell+yield+PL+rab+Thr+ His+PO4.utilise; 0.372, 0.712, pH+Main.Thr.Conc.+ Nitrogen.Conc.+OD+X.F.Suc+X.VXdt+yield+emission_ O2+rab+Thr+lactate+PO4.ferm.+PO4.apporte+PO4.utilise; 0.384, 0.712, pH+tmp+Nitrogen.Conc.+X.F.Suc+yield+PL+ emission_CO2+rab+Thr+His+PO4.ferm.+PO4.apporte+ PO4.utilise; 0.384, 0.712, pH+Main.P-Source.Conc.+Nitrogen.Conc.+X.F.Suc+X.VXdt+total.cell+yield+PL+rab+ lactate+PO4.ferm.+PO4.apporte+PO4.utilise; 0.396, 0.712, pH+Nitrogen.Conc.+OD+X.F.Suc+X.VXdt+total.cell+ yield+emission_O2+Thr+PO4.ferm.+PO4.apporte+PO4. utilise; 0.384, 0.712, pH+tmp+Nitrogen.Conc.+OD+X.F. Suc+X.VXdt+total.cell+yield+emission_O2+His+PO4. ferm.+PO4.apporte+PO4.utilise; 0.384, 0.712, pH+Main.P-Source.Conc.+Nitrogen.Conc.+X.F.Suc+X.VXdt+total. cell+yield+emission_O2+rab+His+PO4.ferm.+PO4. apporte+PO4.utilise; 0.384, 0.712, pH+Nitrogen.Conc.+ OD+X.F.Suc+X.VXdt+yield+PL+emission_O2+emission_ CO2+rab+Thr+His+PO4.ferm.; 0.372, 0.712, pH+tmp+ Nitrogen.Conc.+OD+X.F.Suc+X.VXdt+yield+PL+ emission_CO2+rab+Thr+PO4.ferm.+PO4.apporte+PO4. utilise; 0.407, 0.712, pH+tmp+Nitrogen.Conc.+OD+X. VXdt+total.cell+yield+emission_O2+Thr+His+PO4.utilise; 0.372, 0.712, pH+Main.Thr.Conc.+Nitrogen.Conc.+X.F. Suc+X.VXdt+total.cell+yield+rab+Thr+His+lactate+PO4. ferm.+PO4.apporte+PO4.utilise; 0.372, 0.712, pH+tmp+Nitrogen.Conc.+X.F.Suc+X.VXdt+total.cell+yield+PL+rab+ His+lactate+PO4.ferm.+PO4.apporte+PO4.utilise; 0.360, 0.712, pH+P-Source.Feed.conc.+Nitrogen.Conc.+OD+X.F. Suc+X.VXdt+yield+emission_O2+emission_CO2+rab+ Thr+His+PO4.ferm.+PO4.apporte+PO4.utilise; 0.372, 0.712, pH+P-Source.Feed.conc.+Nitrogen.Conc.+X.F.Suc+ X.VXdt+total.cell+yield+emission_O2+emission_CO2+ rab+Thr+PO4.ferm.+PO4.apporte+PO4.utilise; 0.418, 0.712, pH+tmp+Nitrogen.Conc.+X.VXdt+total.cell+yield+ emission_O2+Thr+His+PO4.apporte; 0.372, 0.712, pH+P-Source.Feed.conc.+Nitrogen.Conc.+X.F.Suc+X.VXdt+total.cell+yield+emission_CO2+rab+Thr+His+PO4.ferm.+ PO4.apporte+PO4.utilise; 0.396, 0.712, pH+Main.P-Source. Conc.+Nitrogen.Conc.+X.F.Suc+X.VXdt+yield+emission_ O2+emission_CO2+lactate+PO4.ferm.+PO4.apporte+PO4. utilise; 0.418, 0.712, pH+tmp+Main.P-Source.Conc.+ Nitrogen.Conc.+X.F.Suc+yield+emission_O2+PO4.ferm.+ PO4.apporte+PO4.utilise; 0.372, 0.712, pH+tmp+Nitrogen. Conc.+X.F.Suc+X.VXdt+total.cell+yield+PL+emission_ O2+Thr+SO4.ferm.+PO4.ferm.+PO4.apporte+PO4.utilise; 0.396, 0.712, pH+tmp+Main.P-Source.Conc.+Nitrogen. Conc.+X.F.Suc+X.VXdt+yield+emission_O2+emission_ CO2+PO4.ferm.+PO4.apporte+PO4.utilise; 0.359, 0.712, pH+P-Source.Feed.conc.+Nitrogen.Conc.+OD+X.F.Suc+X. VXdt+yield+PL+emission_O2+Thr+His+lactate+PO4. ferm.+PO4.apporte+PO4.utilise; 0.384, 0.712, pH+Main.P-Source.Conc.+Main.Thr.Conc.+Nitrogen.Conc.+X.F.Suc+ X.VXdt+yield+emission_O2+Thr+lactate+PO4.ferm.+ PO4.apporte+PO4.utilise; 0.359, 0.712, pH+Main.P-Source. Conc.+Nitrogen.Conc.+OD+X.F.Suc+X.VXdt+yield+PL+ emission_CO2+rab+Thr+lactate+PO4.ferm.+PO4.apporte+ PO4.utilise

[201. Linear Model that Predicts Arginine Production Amount in Interval 1]

0.526, 0.765, tmp+pH+PL+OD+Arg_conc._cumulo+rab_ integral+emission_O2+emission_CO2+RQ; 0.518, 0.765, tmp+pH+PL+OD+Arg_conc._cumulo+cell_yield_cumulo+ rab_integral+emission_O2+emission_CO2+RQ; 0.533, 0.765, tmp+pH+PL+OD+Arg_conc._cumulo+cell_yield_ cumulo+rab_integral+emission_O2; 0.540, 0.764, tmp+pH+ PL+OD+Arg_conc._cumulo+rab_integral+emission_O2; 0.524, 0.764, tmp+pH+PL+OD+Arg_conc._cumulo+cell_ yield_cumulo+rab_integral+emission_O2+RQ; 0.531, 0.763, tmp+pH+PL+OD+Arg_conc._cumulo+rab_integral+ emission_O2+emission_CO2; 0.530, 0.763, tmp+pH+PL+ OD+Arg_conc._cumulo+rab_integral+emission_O2+RQ; 0.523, 0.763, tmp+pH+PL+OD+Arg_conc._cumulo+cell_ yield_cumulo+rab_integral+emission_O2+emission_CO2; 0.535, 0.762, tmp+pH+PL+Arg_conc._cumulo+rab_integral+emission_O2+emission_CO2; 0.527, 0.761, tmp+pH+ PL+OD+Arg_conc._cumulo+rab_integral+emission_O2+ rab; 0.512, 0.761, tmp+pH+PL+OD+Arg_conc._cumulo+ rab_integral+emission_O2+emission_CO2+RQ+rab; 0.519, 0.761, tmp+pH+PL+OD+Arg_conc._cumulo+cell_yield_ cumulo+rab_integral+emission_O2+rab; 0.541, 0.761, tmp+pH+PL+OD+rab_integral+emission_O2; 0.503, 0.761, tmp+pH+PL+OD+Arg_conc._cumulo+cell_yield_cumulo+ rab_integral+emission_O2+emission_CO2+RQ+rab; 0.526, 0.761, tmp+pH+PL+Arg_conc._cumulo+rab_integral+ emission_O2+emission_CO2+RQ; 0.526, 0.761, tmp+pH+ PL+OD+Sugar_consuming_rate_cumulo+Arg_conc._cumulo+rab_integral+emission_O2; 0.518, 0.761, tmp+pH+ PL+OD+Arg_conc._cumulo+rab_integral+emission_O2+ RQ+rab; 0.511, 0.761, tmp+pH+PL+AN+OD+Arg_conc._ cumulo+rab_integral+emission_O2+emission_CO2+RQ; 0.526, 0.760, tmp+pH+PL+AN+OD+Arg_conc._cumulo+ rab_integral+emission_O2; 0.518, 0.760, tmp+pH+PL+ OD+RS+Arg_conc._cumulo+cell_yield_cumulo+emission_CO2+RQ; 0.509, 0.760, tmp+pH+PL+OD+Arg_ conc._cumulo+cell_yield_cumulo+rab_integral+emission_ O2+RQ+rab; 0.509, 0.760, tmp+pH+PL+OD+Sugar_ consuming_rate_cumulo+Arg_conc._cumulo+rab_ integral+emission_O2+emission_CO2+RQ; 0.517, 0.760, tmp+pH+PL+OD+Arg_conc._cumulo+rab_integral+emission_O2+emission_CO2+rab; 0.517, 0.760, tmp+pH+PL+AN+OD+Arg_conc._cumulo+rab_integral+emission_O2+emission_CO2; 0.509, 0.759, tmp+pH+PL+OD+Arg_conc._cumulo+cell_yield_cumulo+rab_integral+emission_O2+emission_CO2+rab; 0.516, 0.759, tmp+pH+PL+OD+Sugar_consuming_rate_cumulo+Arg_conc._cumulo+rab_integral+emission_O2+RQ; 0.538, 0.759, tmp+pH+PL+Arg_conc._cumulo+rab_integral+emission_O2; 0.516, 0.759, tmp+pH+PL+AN+OD+Arg_conc._cumulo+cell_yield_cumulo+rab_integral+emission_O2; 0.515, 0.759, tmp+pH+PL+AN+OD+Arg_conc._cumulo+rab_integral+emission_O2+RQ; 0.507, 0.759, tmp+pH+PL+AN+OD+RS+Arg_conc._cumulo+cell_yield_cumulo+emission_CO2+RQ; 0.499, 0.759, tmp+pH+PL+AN+OD+Arg_conc._cumulo+cell_yield_cumulo+rab_integral+emission_O2+emission_CO2+RQ; 0.499, 0.759, tmp+pH+PL+OD+RS+Arg_conc._cumulo+cell_yield_cumulo+rab_integral+emission_O2+emission_CO2+RQ; 0.515, 0.759, tmp+pH+PL+AN+OD+RS+Arg_conc._cumulo+emission_CO2+RQ; 0.515, 0.758, tmp+pH+PL+OD+Sugar_consuming_rate_cumulo+Arg_conc._cumulo+rab_integral+emission_O2+emission_CO2; 0.522, 0.758, tmp+pH+PL+Arg_conc._cumulo+rab_integral+emission_O2+emission_CO2+rab; 0.514, 0.758, tmp+pH+PL+AN+OD+Arg_conc._cumulo+rab_integral+emission_O2+rab; 0.528, 0.758, tmp+pH+PL+OD+rab_integral+emission_O2+rab; 0.505, 0.758, tmp+pH+PL+AN+OD+Arg_conc._cumulo+cell_yield_cumulo+rab_integral+emission_O2+RQ; 0.505, 0.757, tmp+pH+PL+AN+OD+Arg_conc._cumulo+cell_yield_cumulo+rab_integral+emission_O2+emission_CO2; 0.528, 0.757, tmp+pH+PL+OD+rab_integral+emission_O2+RQ; 0.520, 0.757, tmp+pH+PL+AN+Arg_conc._cumulo+rab_integral+emission_O2+emission_CO2; 0.504, 0.757, tmp+pH+PL+OD+RS+Arg_conc._cumulo+rab_integral+emission_O2+emission_CO2+RQ; 0.512, 0.757, tmp+pH+PL+OD+Sugar_consuming_rate_cumulo+Arg_conc._cumulo+rab_integral+emission_O2+rab; 0.512, 0.757, tmp+pH+PL+Arg_conc._cumulo+rab_integral+emission_O2+emission_CO2+RQ+rab; 0.519, 0.757, tmp+pH+PL+OD+RS+Arg_conc._cumulo+emission_CO2+RQ; 0.512, 0.757, tmp+pH+PL+AN+OD+RS+Arg_conc._cumulo+cell_yield_cumulo+emission_CO2; 0.504, 0.757, tmp+pH+PL+OD+RS+Arg_conc._cumulo+cell_yield_cumulo+rab_integral+emission_O2+emission_CO2; 0.495, 0.757, tmp+pH+PL+AN+OD+Arg_conc._cumulo+rab_integral+emission_O2+emission_CO2+RQ+rab; 0.504, 0.757, tmp+pH+PL+OD+RS+Arg_conc._cumulo+cell_yield_cumulo+emission_CO2+RQ+rab; 0.526, 0.757, tmp+pH+PL+Arg_conc._cumulo+rab_integral+emission_O2+RQ; 0.519, 0.757, tmp+pH+PL+AN+OD+RS+Arg_conc._cumulo+emission_CO2; 0.503, 0.757, tmp+pH+PL+AN+OD+Arg_conc._cumulo+rab_integral+emission_O2+RQ+rab; 0.519, 0.756, tmp+pH+PL+Sugar_consuming_rate_cumulo+Arg_conc._cumulo+rab_integral+emission_O2+emission_CO2; 0.511, 0.756, tmp+pH+PL+OD+RS+Arg_conc._cumulo+cell_yield_cumulo+rab_integral+emission_O2; 0.518, 0.756, tmp+pH+PL+OD+RS+Arg_conc._cumulo+cell_yield_cumulo+emission_CO2; 0.502, 0.756, tmp+pH+PL+OD+Sugar_consuming_rate_cumulo+Arg_conc._cumulo+rab_integral+emission_O2+RQ+rab; 0.525, 0.756, tmp+pH+PL+Arg_conc._cumulo+rab_integral+emission_O2+rab; 0.510, 0.756, tmp+pH+PL+AN+OD+Sugar_consuming_rate_cumulo+Arg_conc._cumulo+rab_integral+emission_O2; 0.493, 0.756, tmp+pH+PL+OD+Sugar_consuming_rate_cumulo+Arg_conc._cumulo+rab_integral+emission_O2+emission_CO2+RQ+rab; 0.509, 0.755, tmp+pH+PL+AN+Arg_conc._cumulo+rab_integral+emission_O2+emission_CO2+RQ; 0.509, 0.755, tmp+pH+PL+Sugar_consuming_rate_cumulo+Arg_conc._cumulo+rab_integral+emission_O2+emission_CO2+RQ; 0.509, 0.755, tmp+pH+PL+OD+RS+Arg_conc._cumulo+rab_integral+emission_O2+emission_CO2; 0.501, 0.755, tmp+pH+PL+AN+OD+Arg_conc._cumulo+rab_integral+emission_O2+emission_CO2+rab; 0.501, 0.755, tmp+pH+PL+OD+RS+Arg_conc._cumulo+cell_yield_cumulo+rab_integral+emission_O2+RQ; 0.524, 0.755, tmp+pH+PL+Sugar_consuming_rate_cumulo+Arg_conc._cumulo+rab_integral+emission_O2; 0.501, 0.755, tmp+pH+PL+AN+OD+Arg_conc._cumulo+cell_yield_cumulo+rab_integral+emission_O2+rab; 0.516, 0.755, tmp+pH+PL+OD+RS+Arg_conc._cumulo+rab_integral+emission_O2; 0.501, 0.755, tmp+pH+PL+OD+RS+Sugar_consuming_rate_cumulo+Arg_conc._cumulo+cell_yield_cumulo+emission_CO2+RQ; 0.523, 0.755, tmp+pH+PL+OD+RS+rab_integral+emission_O2; 0.508, 0.754, tmp+pH+PL+OD+RS+Sugar_consuming_rate_cumulo+Arg_conc._cumulo+emission_CO2+RQ; 0.500, 0.754, tmp+pH+PL+OD+Sugar_consuming_rate_cumulo+Arg_conc._cumulo+rab_integral+emission_O2+emission_CO2+rab; 0.522, 0.754, tmp+pH+PL+OD+rab_integral+emission_O2+emission_CO2; 0.522, 0.754, tmp+pH+PL+AN+Arg_conc._cumulo+rab_integral+emission_O2; 0.491, 0.754, tmp+pH+PL+AN+OD+Sugar_consuming_rate_cumulo+Arg_conc._cumulo+rab_integral+emission_O2+emission_CO2+RQ; 0.482, 0.754, tmp+pH+PL+OD+RS+Arg_conc._cumulo+cell_yield_cumulo+rab_integral+emission_O2+emission_CO2+RQ+rab; 0.515, 0.754, tmp+pH+PL+OD+rab_integral+emission_O2+RQ+rab; 0.507, 0.754, tmp+pH+PL+OD+RS+Arg_conc._cumulo+cell_yield_cumulo+emission_CO2+rab; 0.499, 0.754, tmp+pH+PL+AN+OD+Sugar_consuming_rate_cumulo+Arg_conc._cumulo+rab_integral+emission_O2+RQ; 0.498, 0.754, tmp+pH+PL+AN+OD+RS+Sugar_consuming_rate_cumulo+Arg_conc._cumulo+emission_CO2+RQ; 0.490, 0.754, tmp+pH+PL+AN+OD+RS+Arg_conc._cumulo+cell_yield_cumulo+emission_CO2+RQ+rab; 0.482, 0.754, tmp+pH+PL+AN+OD+Arg_conc._cumulo+cell_yield_cumulo+rab_integral+emission_O2+emission_CO2+RQ+rab; 0.490, 0.753, tmp+pH+PL+AN+OD+Arg_conc._cumulo+cell_yield_cumulo+rab_integral+emission_O2+RQ+rab; 0.521, 0.753, tmp+pH+PL+AN+OD+rab_integral+emission_O2; 0.506, 0.753, tmp+pH+PL+OD+RS+Arg_conc._cumulo+rab_integral+emission_O2+RQ; 0.490, 0.753, tmp+pH+PL+AN+OD+RS+Arg_conc._cumulo+rab_integral+emission_O2+emission_CO2+RQ; 0.498, 0.753, tmp+pH+PL+AN+OD+Sugar_consuming_rate_cumulo+Arg_conc._cumulo+rab_integral+emission_O2+emission_CO2; 0.506, 0.753, tmp+pH+PL+Sugar_consuming_rate_cumulo+Arg_conc._cumulo+rab_integral+emission_O2+emission_CO2+rab; 0.481, 0.753, tmp+pH+PL+AN+OD+RS+Arg_conc._cumulo+cell_yield_cumulo+rab_integral+emission_O2+emission_CO2+RQ; 0.497, 0.753, tmp+pH+PL+AN+OD+RS+Arg_conc._cumulo+emission_CO2+RQ+rab; 0.497, 0.753, tmp+pH+PL+OD+RS+Arg_conc._cumulo+cell_yield_cumulo+rab_integral+emission_CO2+RQ; 0.489, 0.753, tmp+pH+PL+OD+RS+Sugar_consuming_rate_cumulo+Arg_conc._cumulo+rab_integral+emission_O2+emission_CO2+RQ; 0.489, 0.753, tmp+pH+PL+OD+RS+Arg_conc._cumulo+cell_yield_cumulo+rab_integral+emission_O2+emission_CO2+rab; 0.513, 0.753, tmp+pH+PL+Arg_conc._cumulo+rab_integral+emission_O2+RQ+rab; 0.520, 0.753, tmp+pH+PL+OD+Sugar_consuming_rate_cumulo+rab_integral+emission_O2; 0.512, 0.753, tmp+pH+PL+Sugar_consuming_rate_cumulo+Arg_conc._cumulo+rab_integral+emission_O2+RQ; 0.488, 0.752, tmp+pH+PL+AN+OD+Arg_conc._cumulo+cell_yield_cumulo+rab_integral+emission_O2+emission_CO2+rab; 0.496, 0.752, tmp+pH+PL+AN+OD+RS+Arg_conc._cumulo+rab_integral+emission_O2+emission_CO2; 0.496, 0.752, tmp+pH+PL+OD+RS+Arg_conc._cumulo+cell_yield_cumulo+rab_integral+emission_O2+rab; 0.519, 0.752, tmp+pH+PL+OD+RS+Arg_conc._cumulo+emission_CO2; 0.488, 0.752, tmp+pH+PL+OD+RS+Arg_conc._cumulo+rab_integral+emission_O2+emission_CO2+RQ+rab; 0.512, 0.752, tmp+pH+PL+Sugar_consuming_rate_cumulo+Arg_conc._cumulo+cell_yield_cumulo+rab_integral+emission_O2; 0.496, 0.752, tmp+pH+PL+AN+OD+RS+Arg_conc._cumulo+cell_yield_cumulo+emission_CO2+rab; 0.504, 0.752, tmp+pH+PL+AN+Arg_conc._cumulo+rab_integral+emission_O2+emission_CO2+rab; 0.504, 0.752, tmp+pH+PL+OD+RS+Sugar_consuming_rate_cumulo+Arg_conc._cumulo+rab_integral+emission_O2; 0.503, 0.752, tmp+pH+PL+AN+OD+RS+Sugar_consuming_rate_cumulo+Arg_conc._cumulo+emission_CO2; 0.487, 0.752, tmp+pH+PL+AN+OD+RS+Arg_conc._cumulo+cell_yield_cumulo+rab_integral+emission_O2+emission_CO2; 0.503, 0.752, tmp+pH+PL+OD+RS+Arg_conc._cumulo+emission_CO2+RQ+rab; 0.495, 0.752, tmp+pH+PL+Sugar_consuming_rate_cumulo+Arg_conc._cumulo+rab_integral+emission_O2+emission_CO2+RQ+rab; 0.495, 0.752, tmp+pH+PL+AN+OD+Sugar_consuming_rate_cumulo+Arg_conc._cumulo+rab_integral+emission_O2+rab; 0.518, 0.752, tmp+pH+PL+OD+RS+Arg_conc._cumulo+cell_yield_cumulo; 0.511, 0.752, tmp+pH+PL+OD+RS+rab_integral+emission_O2+rab; 0.486, 0.752, tmp+pH+PL+AN+OD+RS+Arg_conc._cumulo+cell_yield_cumulo+rab_integral+emission_CO2+RQ; 0.510, 0.752, tmp+pH+PL+Arg_conc._cumulo+cell_yield_cumulo+rab_integral+emission_O2+emission_CO2; 0.510, 0.751, tmp+pH+PL+Sugar_consuming_rate_cumulo+Arg_conc._cumulo+rab_integral+emission_O2+rab; 0.502, 0.751, tmp+pH+PL+AN+OD+RS+Arg_conc._cumulo+rab_integral+emission_O2; 0.494, 0.751, tmp+pH+PL+OD+RS+Arg_conc._cumulo+cell_yield_cumulo+emission_O2+emission_CO2+RQ; 0.510, 0.751, tmp+pH+PL+RS+Arg_conc._cumulo+rab_integral+emission_O2+emission_CO2; 0.494, 0.751, tmp+pH+PL+AN+OD+RS+Arg_conc._cumulo+cell_yield_cumulo+rab_integral+emission_O2; 0.502, 0.751, tmp+pH+PL+Sugar_consuming_rate_cumulo+Arg_conc._cumulo+cell_yield_cumulo+rab_integral+emission_O2+emission_CO2; 0.510, 0.751, tmp+pH+PL+AN+OD+RS+Arg_conc._cumulo+cell_yield_cumulo; 0.494, 0.751, tmp+pH+PL+OD+RS+Sugar_consuming_rate_cumulo+Arg_conc._cumulo+rab_integral+emission_O2+emission_CO2; 0.510, 0.751, tmp+pH+PL+OD+RS+rab_integral+emission_O2+RQ; 0.502, 0.751, tmp+pH+PL+OD+RS+Arg_conc._cumulo+rab_integral+emission_O2+rab; 0.510, 0.751, tmp+pH+PL+OD+Arg_conc._cumulo+cell_yield_cumulo+emission_CO2+RQ; 0.502, 0.751, tmp+pH+PL+AN+OD+RS+Arg_conc._cumulo+emission_CO2+rab; 0.510, 0.751, tmp+pH+PL+AN+Arg_conc._cumulo+rab_integral+emission_O2+RQ; 0.517, 0.751, tmp+pH+PL+AN+OD+RS+Arg_conc._cumulo; 0.517, 0.751, tmp+pH+PL+OD+cell_yield_cumulo+rab_integral+emission_O2; 0.509, 0.751, tmp+pH+PL+OD+RS+Arg_conc._cumulo+cell_yield_cumulo+RQ; 0.501, 0.751, tmp+pH+PL+AN+Sugar_consuming_rate_cumulo+Arg_conc._cumulo+rab_integral+emission_O2+emission_CO2; 0.509, 0.751, tmp+pH+PL+OD+rab_integral+emission_O2+emission_CO2+rab; 0.493, 0.751, tmp+pH+PL+Sugar_consuming_rate_cumulo+Arg_conc._cumulo+cell_yield_cumulo+rab_integral+emission_O2+emission_CO2+RQ; 0.509, 0.751, tmp+pH+PL+OD+RS+Sugar_consuming_rate_cumulo+Arg_conc._cumulo+emission_CO2; 0.509, 0.751, tmp+pH+PL+OD+rab_integral+emission_O2+emission_CO2+RQ; 0.516, 0.751, tmp+pH+PL+Arg_conc._cumulo+cell_yield_cumulo+rab_integral+emission_O2; 0.493, 0.751, tmp+pH+PL+OD+RS+Sugar_consuming_rate_cumulo+Arg_conc._cumulo+rab_integral+emission_O2+RQ; 0.493, 0.751, tmp+pH+PL+OD+RS+Arg_conc._cumulo+rab_integral+emission_O2+emission_CO2+rab; 0.484, 0.750, tmp+pH+PL+OD+RS+Arg_conc._cumulo+cell_yield_cumulo+rab_integral+emission_O2+RQ+rab; 0.501, 0.750, tmp+pH+PL+Arg_conc._cumulo+cell_yield_cumulo+rab_integral+emission_O2+emission_CO2+RQ; 0.508, 0.750, tmp+pH+PL+AN+Arg_conc._cumulo+rab_integral+emission_O2+rab; 0.508, 0.750, tmp+pH+PL+AN+OD+rab_integral+emission_O2+RQ; 0.492, 0.750, tmp+pH+PL+AN+Arg_conc._cumulo+rab_integral+emission_O2+emission_CO2+RQ+rab; 0.484, 750, tmp+pH+PL+OD+RS+Sugar_consuming_rate_cumulo+Arg_conc._cumulo+cell_yield_cumulo+emission_CO2+RQ+rab; 0.484, 0.750, tmp+pH+PL+AN+OD+Sugar_consuming_rate_cumulo+Arg_conc._cumulo+rab_integral+emission_O2+RQ+rab; 0.492, 0.750, tmp+pH+PL+OD+RS+Sugar_consuming_rate_cumulo+Arg_conc._cumulo+emission_CO2+RQ+rab; 0.500, 0.750, tmp+pH+PL+RS+Arg_conc._cumulo+rab_integral+emission_O2+emission_CO2+RQ; 0.508, 0.750, tmp+pH+PL+OD+Sugar_consuming_rate_cumulo+Arg_conc._cumulo+emission_CO2+RQ; 0.508, 0.750, tmp+pH+PL+AN+OD+rab_integral+emission_O2+rab; 0.491, 0.750, tmp+pH+PL+OD+RS+Arg_conc._cumulo+rab_integral+emission_O2+RQ+rab; 0.507, 0.750, tmp+pH+PL+OD+Sugar_consuming_rate_cumulo+rab_integral+emission_O2+rab; 0.507, 0.750, tmp+pH+PL+OD+RS+rab_integral+emission_O2+emission_CO2; 0.483, 0.750, tmp+pH+PL+AN+OD+RS+Arg_conc._cumulo+cell_yield_cumulo+emission_O2+emission_CO2+RQ; 0.491, 0.750, tmp+pH+PL+AN+OD+RS+Arg_conc._cumulo+cell_yield_cumulo+rab_integral+emission_CO2; 0.491, 0.749, tmp+pH+PL+OD+RS+Sugar_consuming_rate_cumulo+Arg_conc._cumulo+rab_integral+emission_CO2+RQ; 0.499, 0.749, tmp+pH+PL+Sugar_consuming_rate_cumulo+Arg_conc._cumulo+cell_yield_cumulo+rab_integral+emission_O2+RQ; 0.483, 0.749, tmp+pH+PL+OD+RS+Arg_conc._cumulo+cell_yield_cumulo+rab_integral+emission_CO2+RQ+rab; 0.482, 0.749, tmp+pH+PL+AN+OD+RS+Arg_conc._cumulo+cell_yield_cumulo+rab_integral+emission_O2+RQ; 0.491, 0.749, tmp+pH+PL+AN+OD+RS+Arg_conc._cumulo+rab_integral+emission_CO2+RQ; 0.506, 0.749, tmp+pH+PL+AN+Sugar_consuming_rate_cumulo+Arg_conc._cumulo+rab_integral+emission_O2; 0.490, 0.749, tmp+pH+PL+AN+OD+RS+Arg_conc._cumulo+rab_integral+emission_O2+RQ; 0.498, 0.749, tmp+pH+PL+AN+OD+RS+Arg_conc._cumulo+cell_yield_cumulo+RQ; 0.490, 0.749, tmp+pH+PL+AN+OD+RS+Arg_conc._cumulo+emission_O2+emission_CO2+RQ; 0.473, 0.749, tmp+pH+PL+AN+OD+Sugar_consuming_rate_cumulo+Arg_conc._cumulo+rab_integral+emission_O2+emission_CO2+RQ+rab; 0.506, 0.749, tmp+pH+PL+OD+RS+Sugar_consuming_rate_cumulo+rab_integral+emission_O2; 0.490, 0.749, tmp+pH+PL+AN+Sugar_consuming_rate_cumulo+Arg_conc._cumulo+rab_integral+emission_O2+emission_CO2+RQ; 0.498, 0.749, tmp+pH+PL+OD+RS+Arg_conc._cumulo+emission_O2+emission_CO2+RQ; 0.473, 0.749, tmp+pH+PL+AN+OD+RS+Arg_conc._cumulo+rab_integral+emission_O2+emission_CO2+RQ+rab; 0.498, 0.749, tmp+pH+PL+OD+RS+Sugar_consuming_rate_cumulo+Arg_conc._cumulo+cell_yield_cumulo+emission_CO2; 0.498, 0.749, tmp+pH+PL+Sugar_consuming_rate_cumulo+Arg_conc._cumulo+rab_integral+emission_O2+RQ+rab; 0.506, 0.749, tmp+pH+PL+AN+OD+RS+Arg_conc._cumulo+RQ; 0.521, 0.749, tmp+pH+PL+OD+RS+Arg_conc._cumulo; 0.528, 0.749, tmp+pH+PL+OD+RS; 0.498, 0.749, tmp+pH+PL+OD+RS+Arg_conc._cumulo+cell_yield_cumulo+rab_integral+emission_CO2; 0.505, 0.749, tmp+pH+PL+OD+Sugar_consuming_rate_cumulo+rab_integral+emission_O2+RQ; 0.498, 0.749, tmp+pH+PL+Sugar_consuming_rate_cumulo+Arg_conc._cumulo+cell_yield_cumulo+rab_integral+emission_O2+rab; 0.513, 0.749, tmp+pH+PL+RS+Arg_conc._cumulo+rab_integral+emission_O2; 0.489, 0.748, tmp+pH+PL+AN+OD+RS+Arg_conc._cumulo+rab_integral+emission_O2+rab; 0.463, 0.748, tmp+pH+PL+AN+OD+RS+Arg_conc._cumulo+cell_yield_cumulo+rab_integral+emission_O2+emission_CO2+RQ+rab; 0.505, 0.748, tmp+pH+PL+OD+RS+cell_yield_cumulo+rab_integral+emission_O2; 0.480, 0.748, tmp+pH+PL+AN+OD+RS+Sugar_consuming_rate_cumulo+Arg_conc._cumulo+rab_integral+emission_CO2+RQ; 0.505, 0.748, tmp+pH+PL+AN+OD+RS+rab_integral+emission_O2; 0.480, 0.748, tmp+pH+PL+AN+OD+Sugar_consuming_rate_cumulo+Arg_conc._cumulo+rab_integral+emission_O2+emission_CO2+rab; 0.512, 0.748, tmp+pH+PL+Sugar_consuming_rate_cumulo+cell_yield_cumulo+rab_integral+emission_O2; 0.512, 0.748, tmp+pH+PL+OD+RS+Arg_conc._cumulo+RQ; 0.480, 0.748, tmp+pH+PL+AN+OD+RS+Sugar_consuming_rate_cumulo+Arg_conc._cumulo+emission_CO2+RQ+rab; 0.471, 0.748, tmp+pH+PL+OD+RS+Sugar_consuming_rate_cumulo+Arg_conc._cumulo+rab_integral+emission_O2+emission_CO2+RQ+rab; 0.505, 0.748, tmp+pH+PL+OD+RS+Arg_conc._cumulo+emission_CO2+rab; 0.488, 0.748, tmp+pH+PL+OD+RS+Sugar_consuming_rate_cumulo+Arg_conc._cumulo+cell_yield_cumulo+emission_CO2+rab; 0.488, 0.748, tmp+pH+PL+OD+Arg_conc._cumulo+rab_integral+RQ_integral+emission_O2+emission_CO2+RQ; 0.471, 0.748, tmp+pH+PL+AN+OD+RS+Sugar_consuming_rate_cumulo+Arg_conc._cumulo+rab_integral+emission_O2+emission_CO2+RQ; 0.488, 0.748, tmp+pH+PL+OD+RS+Sugar_consuming_rate_cumulo+Arg_conc._cumulo+rab_integral+emission_O2+rab; 0.512, 0.748, tmp+pH+PL+OD+Arg_conc._cumulo+emission_CO2+RQ; 0.504, 0.748, tmp+pH+PL+OD+RS+Arg_conc._cumulo+cell_yield_cumulo+rab; 0.496, 0.748, tmp+pH+PL+OD+RS+Arg_conc._cumulo+rab_integral+emission_CO2+RQ; 0.504, 0.748, tmp+pH+PL+OD+Arg_conc._cumulo+emission_O2+emission_CO2+RQ; 0.504, 0.748, tmp+pH+PL+OD+cell_yield_cumulo+rab_integral+emission_O2+rab; 0.496, 0.748, tmp+pH+PL+OD+RS+rab_integral+emission_O2+RQ+rab; 0.479, 0.748, tmp+pH+PL+AN+OD+RS+Arg_conc._cumulo+rab_integral+emission_O2+emission_CO2+rab; 0.504, 0.748, tmp+pH+PL+AN+OD+Arg_conc._cumulo+emission_CO2+RQ; 0.488, 0.748, tmp+pH+PL+Sugar_consuming_rate_cumulo+Arg_conc._cumulo+cell_yield_cumulo+rab_integral+emission_O2+emission_CO2+rab; 0.496, 0.748, tmp+pH+PL+AN+OD+Arg_conc._cumulo+cell_yield_cumulo+emission_CO2+RQ; 0.511, 0.748, tmp+pH+PL+OD+RS+Sugar_consuming_rate_cumulo+Arg_conc._cumulo; 0.496, 0.748, tmp+pH+PL+Arg_conc._cumulo+cell_yield_cumulo+rab_integral+emission_O2+emission_CO2+rab; 0.479, 0.747, tmp+pH+PL+OD+RS+Arg_conc._cumulo+cell_yield_cumulo+emission_O2+emission_CO2+RQ+rab; 0.470, 0.747, tmp+pH+PL+AN+OD+RS+Arg_conc._cumulo+cell_yield_cumulo+rab_integral+emission_O2+emission_CO2+rab; 0.488, 0.747, tmp+pH+PL+AN+OD+RS+Arg_conc._cumulo+emission_O2+emission_CO2; 0.487, 0.747, tmp+pH+PL+OD+RS+Sugar_consuming_rate_cumulo+Arg_conc._cumulo+cell_yield_cumulo+rab_integral+emission_O2; 0.503, 0.747, tmp+pH+PL+AN+OD+RS+Sugar_consuming_rate_cumulo+Arg_conc._cumulo; 0.487, 0.747, tmp+pH+PL+AN+OD+RS+Sugar_consuming_rate_cumulo+Arg_conc._cumulo+rab_integral+emission_O2; 0.487, 0.747, tmp+pH+PL+OD+RS+Sugar_consuming_rate_cumulo+Arg_conc._cumulo+emission_O2+emission_CO2+RQ; 0.479, 0.747, tmp+pH+PL+AN+OD+RS+Sugar_consuming_rate_cumulo+Arg_conc._cumulo+cell_yield_cumulo+emission_CO2+RQ; 0.503, 0.747, tmp+pH+PL+Arg_conc._cumulo+cell_yield_cumulo+rab_integral+emission_O2+RQ; 0.495, 0.747, tmp+pH+PL+AN+OD+RS+Arg_conc._cumulo+rab_integral+emission_CO2; 0.479, 0.747, tmp+pH+PL+AN+OD+RS+Arg_conc._cumulo+cell_yield_cumulo+rab_integral+emission_O2+rab; 0.478, 0.747, tmp+pH+PL+AN+OD+RS+Sugar_consuming_rate_cumulo+Arg_conc._cumulo+rab_integral+emission_O2+emission_CO2; 0.503, 0.747, tmp+pH+PL+OD+cell_yield_cumulo+rab_integral+emission_O2+RQ; 0.495, 0.747, tmp+pH+PL+OD+RS+Arg_conc._cumulo+cell_yield_cumulo+emission_O2+emission_CO2; 0.495, 0.747, tmp+pH+PL+OD+RS+Sugar_consuming_rate_cumulo+Arg_conc._cumulo+emission_CO2+rab; 0.510, 0.747, tmp+pH+PL+OD+Arg_conc._cumulo+cell_yield_cumulo+RQ; 0.495, 0.747, tmp+pH+PL+AN+OD+Sugar_consuming_rate_cumulo+Arg_conc._cumulo+emission_CO2+RQ; 0.495, 0.747, tmp+pH+PL+AN+OD+RS+Arg_conc._cumulo+emission_O2+emission_CO2; 0.518, 0.747, tmp+pH+PL+cell_yield_cumulo+rab_integral+emission_O2; 0.495, 0.747, tmp+pH+PL+OD+rab_integral+emission_O2+emission_CO2+RQ+rab; 0.469, 0.747, tmp+pH+PL+AN+OD+RS+Arg_conc._cumulo+cell_yield_cumulo+rab_integral+emission_CO2+RQ+rab; 0.495, 0.747, tmp+pH+PL+AN+Arg_conc._cumulo+rab_integral+emission_O2+RQ+rab; 0.518, 0.747, tmp+pH+PL+OD+Sugar_consuming_rate_cumulo+Arg_conc._cumulo; 0.518, 0.747, tmp+pH+PL+AN+OD+RS; 0.478, 0.747, tmp+pH+PL+OD+RS+Sugar_consuming_rate_cumulo+Arg_conc._cumulo+rab_integral+emission_O2+emission_CO2+rab; 0.486, 0.747, tmp+pH+PL+AN+OD+RS+Arg_conc._cumulo+RQ_integral+emission_CO2+RQ; 0.486, 0.747, tmp+pH+PL+AN+OD+RS+Sugar_consuming_rate_cumulo+Arg_conc._cumulo+rab_integral+emission_CO2; 0.502, 0.747, tmp+pH+PL+AN+OD+RS+Arg_conc._cumulo+rab; 0.494, 0.747, tmp+pH+PL+RS+Arg_conc._cumulo+rab_integral+emission_O2+emission_CO2+rab; 0.502, 0.747, tmp+pH+PL+AN+OD+rab_integral+emission_O2+emission_CO2; 0.486, 0.747, tmp+pH+PL+AN+OD+RS+Sugar_consuming_rate_cumulo+Arg_conc._cumulo+emission_CO2+rab; 0.478, 0.747, tmp+pH+PL+Sugar_consuming_rate_cumulo+Arg_conc._cumulo+cell_yield_cumulo+rab_integral+emission_CO2+emission_CO2+RQ+rab; 0.486, 0.747, tmp+pH+PL+OD+RS+Arg_conc._cumulo+cell_yield_cumulo+rab_integral+emission_CO2+rab; 0.510, 0.747, tmp+pH+PL+OD+Sugar_consuming_rate_cumulo+Arg_conc._cumulo+RQ; 0.502, 0.746, tmp+pH+PL+OD+RS+Sugar_consuming_rate_cumulo+Arg_conc._cumulo+RQ; 0.494, 0.746, tmp+pH+PL+OD+RS+rab_integral+emission_CO2+RQ; 0.502, 0.746, tmp+pH+PL+Arg_conc._cumulo+cell_yield_cumulo+rab_integral+emission_O2+rab; 0.517, 0.746, tmp+pH+PL+OD+Arg_conc._cumulo+cell_yield_cumulo;

0.494, 0.746, tmp+pH+PL+OD+RS+Sugar_consuming_rate_cumulo+rab_integral+emission_O2+rab; 0.494, 0.746, tmp+pH+PL+AN+OD+RS+Arg_conc._cumulo+cell_yield_cumulo+rab; 0.477, 0.746, tmp+pH+PL+AN+OD+RS+Arg_conc._cumulo+rab_integral+emission_O2+RQ+rab; 0.517, 0.746, tmp+pH+PL+OD+RS+emission_CO2; 0.494, 0.746, tmp+pH+PL+RS+Sugar_consuming_rate_cumulo+Arg_conc._cumulo+rab_integral+emission_O2+emission_CO2; 0.494, 0.746, tmp+pH+PL+AN+OD+rab_integral+emission_O2+RQ+rab; 0.494, 0.746, tmp+pH+PL+OD+Arg_conc._cumulo+cell_yield_cumulo+emission_O2+emission_CO2+RQ; 0.477, 0.746, tmp+pH+PL+OD+RS+Sugar_consuming_rate_cumulo+Arg_conc._cumulo+cell_yield_cumulo+rab_integral+emission_O2+emission_CO2; 0.494, 0.746, tmp+pH+PL+OD+RS+Sugar_consuming_rate_cumulo+Arg_conc._cumulo+rab_integral+emission_CO2; 0.494, 0.746, tmp+pH+PL+AN+Sugar_consuming_rate_cumulo+Arg_conc._cumulo+rab_integral+emission_O2+RQ; 0.493, 0.746, tmp+pH+PL+OD+RS+rab_integral+emission_O2+emission_CO2+rab; 0.493, 0.746, tmp+pH+PL+AN+Sugar_consuming_rate_cumulo+Arg_conc._cumulo+cell_yield_cumulo+rab_integral+emission_O2; 0.477, 0.746, tmp+pH+PL+OD+RS+Sugar_consuming_rate_cumulo+Arg_conc._cumulo+rab_integral+emission_O2+RQ+rab; 0.493, 0.746, tmp+pH+PL+OD+RS+Arg_conc._cumulo+cell_yield_cumulo+RQ+rab; 0.509, 0.746, tmp+pH+PL+OD+Arg_conc._cumulo+cell_yield_cumulo+emission_CO2; 0.509, 0.746, tmp+pH+PL+OD+Sugar_consuming_rate_cumulo+Arg_conc._cumulo+emission_CO2; 0.493, 0.746, tmp+pH+PL+AN+RS+Arg_conc._cumulo+rab_integral+emission_O2+emission_CO2; 0.476, 0.746, tmp+pH+PL+AN+OD+RS+Sugar_consuming_rate_cumulo+Arg_conc._cumulo+emission_O2+emission_CO2+RQ; 0.516, 0.746, tmp+pH+PL+OD+RS+RQ; 0.485, 0.746, tmp+pH+PL+Arg_conc._cumulo+cell_yield_cumulo+rab_integral+emission_O2+emission_CO2+RQ+rab; 0.516, 0.746, tmp+pH+PL+OD+RS+rab; 0.485, 0.746, tmp+pH+PL+AN+Sugar_consuming_rate_cumulo+Arg_conc._cumulo+rab_integral+emission_O2+emission_CO2+rab; 0.493, 0.746, tmp+pH+PL+OD+Arg_conc._cumulo+cell_yield_cumulo+emission_CO2+RQ+rab; 0.493, 0.746, tmp+pH+PL+OD+RS+cell_yield_cumulo+rab_integral+emission_O2+rab; 0.492, 0.746, tmp+pH+PL+AN+OD+Arg_conc._cumulo+emission_O2+emission_CO2+RQ; 0.508, 0.746, tmp+pH+PL+AN+OD+RS+emission_CO2; 0.484, 0.745, tmp+pH+PL+Sugar_consuming_rate_cumulo+Arg_conc._cumulo+cell_yield_cumulo+rab_integral+emission_O2+RQ+rab; 0.500, 0.745, tmp+pH+PL+RS+Arg_conc._cumulo+rab_integral+emission_O2+RQ; 0.475, 0.745, tmp+pH+PL+AN+OD+RS+Arg_conc._cumulo+cell_yield_cumulo+rab_integral+emission_CO2+rab; 0.507, 0.745, tmp+pH+PL+AN+OD+Sugar_consuming_rate_cumulo+Arg_conc._cumulo; 0.492, 0.745, tmp+pH+PL+OD+Sugar_consuming_rate_cumulo+rab_integral+emission_O2+RQ+rab; 0.515, 0.745, tmp+pH+PL+OD+RS+Sugar_consuming_rate_cumulo; 0.475, 0.745, tmp+pH+PL+AN+OD+RS+Sugar_consuming_rate_cumulo+Arg_conc._cumulo+rab_integral+emission_O2+RQ; 0.499, 0.745, tmp+pH+PL+AN+OD+Sugar_consuming_rate_cumulo+Arg_conc._cumulo+emission_CO2; 0.491, 0.745, tmp+pH+PL+OD+RS+Sugar_consuming_rate_cumulo+rab_integral+emission_O2+RQ; 0.475, 0.745, tmp+pH+PL+OD+RS+Sugar_consuming_rate_cumulo+Arg_conc._cumulo+rab_integral+emission_CO2+RQ+rab; 0.491, 0.745, tmp+pH+PL+AN+OD+RS+Sugar_consuming_rate_cumulo+Arg_conc._cumulo+RQ; 0.491, 0.745, tmp+pH+PL+AN+Sugar_consuming_rate_cumulo+Arg_conc._cumulo+rab_integral+emission_O2+rab; 0.507, 0.745, tmp+pH+PL+Arg_conc._cumulo+emission_O2+emission_CO2+RQ; 0.466, 0.745, tmp+pH+PL+AN+OD+RS+Arg_conc._cumulo+cell_yield_cumulo+rab_integral+emission_O2+RQ+rab; 0.474, 0.745, tmp+pH+PL+AN+OD+Arg_conc._cumulo+rab_integral+RQ_integral+emission_O2+emission_CO2+RQ; 0.507, 0.745, tmp+pH+PL+OD+RS+emission_CO2+RQ; 0.483, 0.745, tmp+pH+PL+RS+Sugar_consuming_rate_cumulo+Arg_conc._cumulo+rab_integral+emission_O2+emission_CO2+RQ; 0.483, 0.745, tmp+pH+PL+RS+Arg_conc._cumulo+rab_integral+emission_O2+emission_CO2+RQ+rab; 0.499, 0.745, tmp+pH+PL+Sugar_consuming_rate_cumulo+cell_yield_cumulo+rab_integral+emission_O2+rab; 0.491, 0.745, tmp+pH+PL+AN+OD+RS+rab_integral+emission_O2+rab; 0.514, 0.745, tmp+pH+PL+rab_integral+emission_O2+rab; 0.483, 0.745, tmp+pH+PL+AN+Sugar_consuming_rate_cumulo+Arg_conc._cumulo+cell_yield_cumulo+rab_integral+emission_O2+emission_CO2; 0.483, 0.745, tmp+pH+PL+OD+RS+Arg_conc._cumulo+cell_yield_cumulo+emission_O2+emission_CO2+rab; 0.506, 0.745, tmp+pH+PL+AN+OD+Arg_conc._cumulo+cell_yield_cumulo; 0.499, 0.744, tmp+pH+PL+AN+OD+Arg_conc._cumulo+cell_yield_cumulo+emission_CO2; 0.474, 0.744, tmp+pH+PL+OD+Arg_conc._cumulo+cell_yield_cumulo+rab_integral+RQ_integral+emission_O2+emission_CO2+RQ; 0.490, 0.744, tmp+pH+PL+AN+OD+RS+Arg_conc._cumulo+RQ+rab; 0.506, 0.744, tmp+pH+PL+AN+OD+Arg_conc._cumulo+emission_CO2; 0.498, 0.744, tmp+pH+PL+RS+Sugar_consuming_rate_cumulo+Arg_conc._cumulo+rab_integral+emission_O2; 0.490, 0.744, tmp+pH+PL+AN+OD+RS+rab_integral+emission_O2+RQ; 0.465, 0.744, tmp+pH+PL+AN+OD+RS+Arg_conc._cumulo+cell_yield_cumulo+emission_O2+emission_CO2+RQ+rab; 0.514, 0.744, tmp+pH+PL+OD+Arg_conc._cumulo+RQ; 0.498, 0.744, tmp+pH+PL+OD+RS+Arg_conc._cumulo+emission_O2+emission_CO2; 0.498, 0.744, tmp+pH+PL+AN+OD+Sugar_consuming_rate_cumulo+rab_integral+emission_O2; 0.482, 0.744, tmp+pH+PL+AN+OD+RS+Sugar_consuming_rate_cumulo+Arg_conc._cumulo+emission_O2+emission_CO2; 0.513, 0.744, tmp+pH+PL+OD+RS+cell_yield_cumulo; 0.490, 0.744, tmp+pH+PL+OD+RS+cell_yield_cumulo+rab_integral+emission_O2+RQ; 0.490, 0.744, tmp+pH+PL+OD+Sugar_consuming_rate_cumulo+Arg_conc._cumulo+emission_O2+emission_CO2+RQ; 0.506, 0.744, tmp+pH+PL+OD+RS+Arg_conc._cumulo+rab; 0.506, 0.744, tmp+pH+PL+OD+RS+emission_CO2+rab; 0.498, 0.744, tmp+pH+PL+OD+Sugar_consuming_rate_cumulo+rab_integral+emission_O2+emission_CO2; 0.490, 0.744, tmp+pH+PL+AN+Arg_conc._cumulo+cell_yield_cumulo+rab_integral+emission_O2+emission_CO2; 0.506, 0.744, tmp+pH+PL+Sugar_consuming_rate_cumulo+Arg_conc._cumulo+emission_CO2+RQ; 0.473, 0.744, tmp+pH+PL+AN+OD+RS+Arg_conc._cumulo+rab_integral+emission_CO2+RQ+rab; 0.473, 0.744, tmp+pH+PL+AN+OD+RS+Sugar_consuming_rate_cumulo+Arg_conc._cumulo+cell_yield_cumulo+rab_integral+emission_O2; 0.490, 0.744, tmp+pH+PL+OD+Sugar_consuming_rate_cumulo+Arg_conc._cumulo+emission_CO2+RQ+rab; 0.498, 0.744, tmp+pH+PL+AN+Arg_conc._cumulo+cell_yield_cumulo+rab_integral+emission_O2; 0.513, 0.744, tmp+pH+PL+Sugar_consuming_rate_cumulo+Arg_conc._cumulo+emission_CO2; 0.513, 0.744, tmp+pH+PL+AN+OD+Arg_conc._cumulo; 0.464, 0.744, tmp+pH+PL+AN+OD+RS+Sugar_consuming_rate_cumulo+Arg_conc._cumulo+cell_yield_cumulo+rab_integral+emission_O2+emission_CO2; 0.497, 0.744, tmp+pH+PL+Sugar_consuming_rate_cumulo+cell_yield_cumulo+rab_integral+emission_O2+RQ; 0.505, 0.744, tmp+pH+PL+AN+Arg_conc._cumulo+emission_O2+emission_CO2; 0.497, 0.744, tmp+pH+PL+RS+Arg_conc._cumulo+rab_integral+emission_O2+rab; 0.497, 0.744, tmp+pH+PL+OD+RS+Arg_conc._cumulo+cell_yield_cumulo+rab_integral; 0.513, 0.744, tmp+pH+PL+Arg_conc._cumulo+emission_O2+emission_CO2; 0.473, 0.744, tmp+pH+PL+OD+Arg_conc._cumulo+rab_integral+RQ_integral+emission_O2+emission_CO2+RQ+rab; 0.473, 0.744, tmp+pH+PL+AN+Sugar_consuming_rate_cumulo+Arg_conc._cumulo+rab_integral+emission_O2+emission_CO2+RQ+rab; 0.481, 0.744, tmp+pH+PL+AN+OD+RS+Arg_conc._cumulo+cell_yield_cumulo+RQ+rab; 0.497, 0.744, tmp+pH+PL+OD+RS+Sugar_consuming_rate_cumulo+Arg_conc._cumulo+rab_integral; 0.481, 0.744, tmp+pH+PL+OD+RS+Arg_conc._cumulo+emission_O2+emission_CO2+RQ+rab; 0.497, 0.744, tmp+pH+PL+AN+OD+Arg_conc._cumulo+cell_yield_cumulo+RQ; 0.472, 0.744, tmp+pH+PL+AN+OD+RS+Arg_conc._cumulo+emission_O2+emission_CO2+RQ+rab; 0.489, 0.744, tmp+pH+PL+AN+OD+RS+Arg_conc._cumulo+cell_yield_cumulo+rab_integral; 0.489, 0.744, tmp+pH+PL+OD+RS+Sugar_consuming_rate_cumulo+Arg_conc._cumulo+emission_O2+emission_CO2; 0.472, 0.744, tmp+pH+PL+AN+Sugar_consuming_rate_cumulo+Arg_conc._cumulo+cell_yield_cumulo+rab_integral+emission_O2+emission_CO2+RQ; 0.497, 0.744, tmp+pH+PL+AN+OD+Sugar_consuming_rate_cumulo+Arg_conc._cumulo+RQ; 0.481, 0.744, tmp+pH+PL+AN+RS+Arg_conc._cumulo+rab_integral+emission_O2+emission_CO2+RQ; 0.505, 0.743, tmp+pH+PL+OD+RS+cell_yield_cumulo+rab; 0.472, 0.743, tmp+pH+PL+AN+OD+RS+Sugar_consuming_rate_cumulo+Arg_conc._cumulo+rab_integral+emission_O2+rab; 0.504, 0.743, tmp+pH+PL+AN+OD+Arg_conc._cumulo+RQ; 0.489, 0.743, tmp+pH+PL+AN+OD+rab_integral+emission_O2+emission_CO2+RQ; 0.489, 0.743, tmp+pH+PL+OD+RS+Arg_conc._cumulo+cell_yield_cumulo+rab_integral+RQ; 0.496, 0.743, tmp+pH+PL+OD+RS+Arg_conc._cumulo+RQ+rab; 0.488, 0.743, tmp+pH+PL+AN+OD+RS+rab_integral+emission_O2+emission_CO2; 0.519, 0.743, tmp+pH+PL+OD+Arg_conc._cumulo; 0.496, 0.743, tmp+pH+PL+OD+cell_yield_cumulo+rab_integral+emission_O2+emission_CO2; 0.472, 0.743, tmp+pH+PL+AN+OD+RS+Arg_conc._cumulo+cell_yield_cumulo+RQ_integral+emission_CO2+RQ; 0.496, 0.743, tmp+pH+PL+OD+RS+Arg_conc._cumulo+rab_integral+emission_CO2; 0.504, 0.743, tmp+pH+PL+AN+OD+RS+RQ; 0.488, 0.743, tmp+pH+PL+OD+cell_yield_cumulo+rab_integral+emission_O2+emission_CO2+RQ+rab; 0.504, 0.743, tmp+pH+PL+AN+OD+RS+rab; 0.496, 0.743, tmp+pH+PL+AN+RS+Arg_conc._cumulo+rab_integral+emission_O2; 0.480, 0.743, tmp+pH+PL+AN+Sugar_consuming_rate_cumulo+Arg_conc._cumulo+cell_yield_cumulo+rab_integral+emission_O2+RQ; 0.463, 0.743, tmp+pH+PL+AN+OD+RS+Sugar_consuming_rate_cumulo+Arg_conc._cumulo+rab_integral+emission_CO2+RQ+rab; 0.488, 0.743, tmp+pH+PL+AN+OD+RS+Sugar_consuming_rate_cumulo+Arg_conc._cumulo+rab_integral; 0.488, 0.743, tmp+pH+PL+OD+Arg_conc._cumulo+rab_integral+RQ_integral+emission_O2+RQ; 0.504, 0.743, tmp+pH+PL+OD+RS+Sugar_consuming_rate_cumulo+rab; 0.462, 0.743, tmp+pH+PL+AN+OD+RS+Sugar_consuming_rate_cumulo+Arg_conc._cumulo+cell_yield_cumulo+emission_CO2+RQ+rab; 0.496, 0.743, tmp+pH+PL+OD+RS+Sugar_consuming_rate_cumulo+Arg_conc._cumulo+rab; 0.504, 0.743, tmp+pH+PL+RS+Sugar_consuming_rate_cumulo+Arg_conc._cumulo+emission_CO2; 0.453, 0.743, tmp+pH+PL+AN+OD+RS+Sugar_consuming_rate_cumulo+Arg_conc._cumulo+rab_integral+emission_O2+emission_CO2+RQ+rab; 0.496, 0.743, tmp+pH+PL+AN+Arg_conc._cumulo+emission_O2+emission_CO2+RQ; 0.479, 0.743, tmp+pH+PL+OD+RS+Arg_conc._cumulo+rab_integral+emission_CO2+RQ+rab; 0.503, 0.743, tmp+pH+PL+OD+Arg_conc._cumulo+emission_O2+emission_CO2; 0.471, 0.743, tmp+pH+PL+AN+OD+RS+Arg_conc._cumulo+cell_yield_cumulo+emission_O2+emission_CO2+rab; 0.496, 0.743, tmp+pH+PL+AN+OD+RS+emission_CO2+RQ; 0.479, 0.743, tmp+pH+PL+OD+RS+rab_integral+emission_O2+emission_CO2+RQ+rab; 0.488, 0.743, tmp+pH+PL+AN+OD+rab_integral+emission_O2+emission_CO2+rab; 0.503, 0.743, tmp+pH+PL+cell_yield_cumulo+rab_integral+emission_O2+rab; 0.495, 0.743, tmp+pH+PL+AN+OD+Arg_conc._cumulo+emission_O2+emission_CO2; 0.479, 0.743, tmp+pH+PL+AN+Arg_conc._cumulo+cell_yield_cumulo+rab_integral+emission_O2+emission_CO2+RQ; 0.487, 0.743, tmp+pH+PL+Arg_conc._cumulo+cell_yield_cumulo+rab_integral+emission_O2+RQ+rab; 0.518, 0.743, tmp+pH+PL+rab_integral+emission_O2; 0.503, 0.743, tmp+pH+PL+AN+RS+Arg_conc._cumulo+emission_CO2; 0.479, 0.743, tmp+pH+PL+RS+Sugar_consuming_rate_cumulo+Arg_conc._cumulo+rab_integral+emission_O2+emission_CO2+rab; 0.470, 0.742, tmp+pH+PL+OD+RS+Sugar_consuming_rate_cumulo+Arg_conc._cumulo+emission_O2+emission_CO2+RQ+rab; 0.495, 0.742, tmp+pH+PL+RS+Sugar_consuming_rate_cumulo+Arg_conc._cumulo+emission_CO2+RQ; 0.503, 0.742, tmp+pH+PL+rab_integral+emission_O2+RQ+rab; 0.479, 0.742, tmp+pH+PL+OD+RS+Sugar_consuming_rate_cumulo+Arg_conc._cumulo+rab_integral+emission_CO2+rab; 0.487, 0.742, tmp+pH+PL+OD+RS+Sugar_consuming_rate_cumulo+Arg_conc._cumulo+rab_integral+RQ; 0.510, 0.742, tmp+pH+PL+OD+Arg_conc._cumulo+emission_CO2; 0.503, 0.742, tmp+pH+PL+OD+RS+RQ+rab; 0.495, 0.742, tmp+pH+PL+AN+OD+cell_yield_cumulo+rab_integral+emission_O2; 0.487, 0.742, tmp+pH+PL+AN+OD+RS+Sugar_consuming_rate_cumulo+Arg_conc._cumulo+rab; 0.495, 0.742, tmp+pH+PL+AN+OD+RS+emission_CO2+rab; 0.503, 0.742, tmp+pH+PL+OD+Arg_conc._cumulo+emission_O2+RQ; 0.503, 0.742, tmp+pH+PL+AN+Sugar_consuming_rate_cumulo+Arg_conc._cumulo+emission_CO2; 0.510, 0.742, tmp+pH+PL+RS+Arg_conc._cumulo+emission_CO2; 0.487, 0.742, tmp+pH+PL+OD+RS+Arg_conc._cumulo+RQ_integral+emission_CO2+RQ; 0.487, 0.742, tmp+pH+PL+OD+Sugar_consuming_rate_cumulo+Arg_conc._cumulo+rab_integral+emission_CO2+RQ; 0.487, 0.742, tmp+pH+PL+OD+RS+cell_yield_cumulo+rab_integral+emission_O2+emission_CO2; 0.495, 0.742, tmp+pH+PL+OD+Arg_conc._cumulo+emission_CO2+RQ+rab; 0.495, 0.742, tmp+pH+PL+OD+RS+cell_yield_cumulo+emission_CO2+rab; 0.461, 0.742, tmp+pH+PL+AN+OD+RS+Sugar_consuming_rate_cumulo+Arg_conc._cumulo+rab_integral+emission_O2+emission_CO2+rab; 0.495, 0.742, tmp+pH+PL+OD+RS+emission_CO2+RQ+rab; 0.486, 0.742, tmp+pH+PL+OD+RS+Sugar_consuming_rate_cumulo+rab_integral+emission_O2+emission_CO2; 0.502, 0.742, tmp+pH+PL+cell_yield_cumulo+rab_integral+emission_O2+RQ; 0.486, 0.742, tmp+pH+PL+OD+Sugar_consuming_rate_cumulo+Arg_conc._cumulo+cell_yield_cumulo+rab_integral+emission_O2; 0.478, 0.742, tmp+pH+PL+OD+RS+Sugar_consuming_rate_cumulo+rab_integral+emission_O2+RQ+rab; 0.486, 0.742, tmp+pH+PL+OD+Arg_conc._cumulo+emission_O2+emission_CO2+RQ+ rab; 0.502, 0.742, tmp+pH+PL+RS+Arg_conc._cumulo+emission_CO2+RQ; 0.509, 0.742, tmp+pH+PL+OD+Arg_conc._cumulo+emission_O2; 0.478, 0.742, tmp+pH+PL+AN+OD+RS+Arg_conc._cumulo+rab_integral+emission_CO2+rab; 0.478, 0.742, tmp+pH+PL+AN+Sugar_consuming_rate_cumulo+Arg_conc._cumulo+rab_integral+emission_O2+RQ+rab; 0.478, 0.742, tmp+pH+PL+AN+Sugar_consuming_rate_cumulo+Arg_conc._cumulo+cell_yield_cumulo+rab_integral+emission_O2+rab; 0.494, 0.742, tmp+pH+PL+AN+OD+RS+Arg_conc._cumulo+rab_integral; 0.478, 0.742, tmp+pH+PL+AN+OD+Arg_conc._cumulo+cell_yield_cumulo+emission_O2+emission_CO2+RQ; 0.502, 0.742, tmp+pH+PL+OD+RS+Sugar_consuming_rate_cumulo+emission_CO2; 0.469, 0.742, tmp+pH+PL+AN+OD+RS+Sugar_consuming_rate_cumulo+Arg_conc._cumulo+rab_integral+emission_CO2+rab; 0.502, 0.742, tmp+pH+PL+OD+RS+Sugar_consuming_rate_cumulo+RQ; 0.478, 0.742, tmp+pH+PL+AN+OD+RS+Arg_conc._cumulo+cell_yield_cumulo+rab_integral+RQ; 0.502, 0.742, tmp+pH+PL+AN+OD+Arg_conc._cumulo+emission_O2; 0.486, 0.742, tmp+pH+PL+OD+Arg_conc._cumulo+rab_integral+RQ_integral+emission_O2+emission_CO2; 0.494, 0.742, tmp+pH+PL+AN+OD+RS+Arg_conc._cumulo+emission_O2; 0.494, 0.742, tmp+pH+PL+OD+Arg_conc._cumulo+cell_yield_cumulo+emission_CO2+rab; 0.501, 0.741, tmp+pH+PL+OD+Sugar_consuming_rate_cumulo+Arg_conc._cumulo+rab; 0.477, 0.741, tmp+pH+PL+AN+OD+RS+Arg_conc._cumulo+emission_O2+emission_CO2+rab; 0.485, 0.741, tmp+pH+PL+RS+Sugar_consuming_rate_cumulo+Arg_conc._cumulo+rab_integral+emission_O2+RQ; 0.493, 0.741, tmp+pH+PL+OD+Arg_conc._cumulo+rab_integral+RQ_integral+emission_O2; 0.493, 0.741, tmp+pH+PL+OD+RS+Sugar_consuming_rate_cumulo+emission_CO2+rab; 0.493, 0.741, tmp+pH+PL+OD+RS+Arg_conc._cumulo+cell_yield_cumulo+emission_O2; 0.493, 0.741, tmp+pH+PL+OD+Arg_conc._cumulo+cell_yield_cumulo+RQ+rab; 0.477, 0.741, tmp+pH+PL+RS+Sugar_consuming_rate_cumulo+Arg_conc._cumulo+cell_yield_cumulo+rab_integral+emission_O2+emission_CO2; 0.485, 0.741, tmp+pH+PL+OD+RS+Sugar_consuming_rate_cumulo+Arg_conc._cumulo+RQ+rab; 0.493, 0.741, tmp+pH+PL+AN+RS+Sugar_consuming_rate_cumulo+Arg_conc._cumulo+emission_CO2; 0.468, 0.741, tmp+pH+PL+AN+OD+RS+Arg_conc._cumulo+RQ_integral+emission_CO2+RQ+rab; 0.501, 0.741, tmp+pH+PL+OD+Arg_conc._cumulo+cell_yield_cumulo+rab; 0.493, 0.741, tmp+pH+PL+OD+Arg_conc._cumulo+cell_yield_cumulo+emission_O2+emission_CO2; 0.485, 0.741, tmp+pH+PL+OD+Sugar_consuming_rate_cumulo+rab_integral+emission_O2+emission_CO2+rab; 0.485, 0.741, tmp+pH+PL+RS+Sugar_consuming_rate_cumulo+Arg_conc._cumulo+cell_yield_cumulo+rab_integral+emission_O2; 0.477, 0.741, tmp+pH+PL+OD+RS+Arg_conc._cumulo+cell_yield_cumulo+RQ_integral+emission_CO2+RQ; 0.516, 0.741, tmp+pH+PL+Sugar_consuming_rate_cumulo+Arg_conc._cumulo; 0.493, 0.741, tmp+pH+PL+RS+Sugar_consuming_rate_cumulo+Arg_conc._cumulo+emission_CO2+rab; 0.485, 0.741, tmp+pH+PL+AN+OD+Arg_conc._cumulo+emission_CO2+RQ+rab; 0.485, 0.741, tmp+pH+PL+AN+OD+RS+Sugar_consuming_rate_cumulo+rab_integral+emission_O2; 0.459, 0.741, tmp+pH+PL+AN+OD+RS+Sugar_consuming_rate_cumulo+Arg_conc._cumulo+rab_integral+emission_O2+RQ+rab; 0.485, 0.741, tmp+pH+PL+AN+OD+RS+Arg_conc._cumulo+RQ_integral+emission_CO2; 0.501, 0.741, tmp+pH+PL+OD+RS+cell_yield_cumulo+RQ; 0.485, 0.741, tmp+pH+PL+OD+Arg_conc._cumulo+cell_yield_cumulo+rab_integral+emission_CO2+RQ; 0.476, 0.741, tmp+pH+PL+OD+RS+cell_yield_cumulo+rab_integral+emission_O2+RQ+rab; 0.500, 0.741, tmp+pH+PL+AN+OD+RS+Sugar_consuming_rate_cumulo; 0.485, 0.741, tmp+pH+PL+RS+Sugar_consuming_rate_cumulo+Arg_conc._cumulo+cell_yield_cumulo+emission_CO2+RQ; 0.493, 0.741, tmp+pH+PL+OD+Sugar_consuming_rate_cumulo+Arg_conc._cumulo+RQ+rab; 0.500, 0.741, tmp+pH+PL+OD+RS+cell_yield_cumulo+emission_CO2; 0.508, 0.741, tmp+pH+PL+Arg_conc._cumulo+emission_CO2+RQ; 0.508, 0.741, tmp+pH+PL+rab_integral+emission_O2+RQ; 0.492, 0.741, tmp+pH+PL+OD+RS+Sugar_consuming_rate_cumulo+cell_yield_cumulo+emission_CO2; 0.500, 0.741, tmp+pH+PL+cell_yield_cumulo+rab_integral+emission_O2+emission_CO2; 0.484, 0.741, tmp+pH+PL+OD+RS+Arg_conc._cumulo+cell_yield_cumulo+emission_O2+RQ; 0.484, 0.741, tmp+pH+PL+AN+OD+Sugar_consuming_rate_cumulo+rab_integral+emission_O2+rab; 0.492, 0.741, tmp+pH+PL+AN+Sugar_consuming_rate_cumulo+Arg_conc._cumulo+emission_CO2+RQ; 0.492, 0.741, tmp+pH+PL+OD+Sugar_consuming_rate_cumulo+Arg_conc._cumulo+emission_CO2+rab; 0.484, 0.741, tmp+pH+PL+AN+OD+RS+Arg_conc._cumulo+cell_yield_cumulo+emission_O2; 0.476, 0.741, tmp+pH+PL+AN+OD+RS+rab_integral+emission_O2+RQ+rab; 0.484, 0.741, tmp+pH+PL+AN+OD+Sugar_consuming_rate_cumulo+rab_integral+emission_O2+RQ; 0.476, 0.741, tmp+pH+PL+AN+OD+RS+Sugar_consuming_rate_cumulo+Arg_conc._cumulo+rab_integral+RQ; 0.458, 0.741, tmp+pH+PL+AN+OD+RS+Sugar_consuming_rate_cumulo+Arg_conc._cumulo+cell_yield_cumulo+rab_integral+emission_O2+rab; 0.484, 0.741, tmp+pH+PL+AN+Arg_conc._cumulo+cell_yield_cumulo+rab_integral+emission_O2+RQ; 0.476, 0.741, tmp+pH+PL+OD+Arg_conc._cumulo+cell_yield_cumulo+emission_O2+emission_CO2+RQ+rab; 0.458, 0.741, tmp+pH+PL+AN+OD+Arg_conc._cumulo+rab_integral+RQ_integral+emission_O2+emission_CO2+RQ+rab; 0.492, 0.741, tmp+pH+PL+Sugar_consuming_rate_cumulo+cell_yield_cumulo+rab_integral+emission_O2+emission_CO2; 0.467, 0.741, tmp+pH+PL+RS+Sugar_consuming_rate_cumulo+Arg_conc._cumulo+cell_yield_cumulo+rab_integral+emission_O2+emission_CO2+RQ; 0.492, 0.741, tmp+pH+PL+AN+OD+Arg_conc._cumulo+emission_O2+RQ; 0.467, 0.740, tmp+pH+PL+RS+Sugar_consuming_rate_cumulo+Arg_conc._cumulo+rab_integral+emission_O2+emission_CO2+RQ+rab; 0.475, 0.740, tmp+pH+PL+AN+OD+Sugar_consuming_rate_cumulo+Arg_conc._cumulo+emission_O2+emission_CO2+RQ; 0.492, 0.740, tmp+pH+PL+OD+Sugar_consuming_rate_cumulo+Arg_conc._cumulo+emission_O2+emission_CO2; 0.458, 0.740, tmp+pH+PL+AN+OD+RS+Sugar_consuming_rate_cumulo+Arg_conc._cumulo+emission_O2+emission_CO2+RQ+rab; 0.475, 0.740, tmp+pH+PL+OD+RS+cell_yield_cumulo+rab_integral+emission_O2+emission_CO2+rab; 0.499, 0.740, tmp+pH+PL+Sugar_consuming_rate_cumulo+Arg_conc._cumulo+emission_CO2+rab; 0.475, 0.740, tmp+pH+PL+OD+Arg_conc._cumulo+cell_yield_cumulo+rab_integral+RQ_integral+emission_O2+RQ; 0.475, 0.740, tmp+pH+PL+AN+OD+Arg_conc._cumulo+cell_yield_cumulo+emission_CO2+RQ+rab; 0.483, 0.740, tmp+pH+PL+RS+Arg_conc._cumulo+cell_yield_cumulo+rab_integral+emission_O2+emission_CO2; 0.491, 0.740, tmp+pH+PL+AN+RS+Arg_conc._cumulo+emission_CO2+RQ; 0.491, 0.740, tmp+pH+PL+Sugar_consuming_rate_cumulo+Arg_conc._cumulo+emission_O2+emission_CO2+RQ; 0.491, 0.740, tmp+pH+PL+Sugar_consuming rate_cumulo+Arg_conc._cumulo+cell_yield_cumulo+emission_CO2+RQ; 0.499, 0.740, tmp+pH+PL+AN+OD+RS+cell_yield_cumulo; 0.491, 0.740, tmp+pH+PL+OD+Arg_conc._cumulo+rab_integral+emission_CO2+RQ; 0.483, 0.740, tmp+pH+PL+RS+Arg_conc._cumulo+rab_integral+emission_O2+RQ+rab; 0.483, 0.740, tmp+pH+PL+AN+OD+RS+cell_yield_cumulo+rab_integral+emission_O2; 0.507, 0.740, tmp+pH+PL+AN+Arg_conc._cumulo+emission_CO2; 0.483, 0.740, tmp+pH+PL+OD+RS+Arg_conc._cumulo+cell_yield_cumulo+rab_integral+rab; 0.507, 0.740, tmp+pH+PL+OD+RS+emission_O2; 0.483, 0.740, tmp+pH+PL+OD+cell_yield_cumulo+rab_integral+emission_O2+emission_CO2+rab; 0.499, 0.740, tmp+pH+PL+OD+RS+Arg_conc._cumulo+emission_O2; 0.483, 0.740, tmp+pH+PL+RS+Sugar_consuming_rate_cumulo+Arg_conc._cumulo+rab_integral+emission_O2+rab; 0.483, 0.740, tmp+pH+PL+Sugar_consuming_rate_cumulo+cell_yield_cumulo+rab_integral+emission_O2+RQ+rab; 0.491, 0.740, tmp+pH+PL+RS+Sugar_consuming_rate_cumulo+cell_yield_cumulo+rab_integral+emission_O2; 0.491, 0.740, tmp+pH+PL+Sugar_consuming_rate_cumulo+Arg_conc._cumulo+emission_CO2+RQ+rab; 0.475, 0.740, tmp+pH+PL+AN+OD+RS+rab_integral+emission_O2+emission_CO2+RQ; 0.475, 0.740, tmp+pH+PL+OD+RS+Sugar_consuming_rate_cumulo+rab_integral+emission_O2+emission_CO2+rab; 0.474, 0.740, tmp+pH+PL+AN+RS+Arg_conc._cumulo+rab_integral+emission_O2+emission_CO2+rab; 0.483, 0.740, tmp+pH+PL+RS+Sugar_consuming_rate_cumulo+Arg_conc._cumulo+emission_CO2+RQ+rab; 0.499, 0.740, tmp+pH+PL+OD+Sugar_consuming_rate_cumulo+Arg_conc._cumulo+emission_O2; 0.491, 0.740, tmp+pH+PL+RS+Sugar_consuming_rate_cumulo+Arg_conc._cumulo+cell_yield_cumulo+emission_O2; 0.491, 0.740, tmp+pH+PL+OD+RS+Sugar_consuming_rate_cumulo+Arg_conc._cumulo+emission_O2; 0.466, 0.740, tmp+pH+PL+OD+RS+Sugar_consuming_rate_cumulo+Arg_conc._cumulo+cell_yield_cumulo+rab_integral+emission_O2+rab; 0.457, 0.740, tmp+pH+PL+OD+Arg_conc._cumulo+cell_yield_cumulo+rab_integral+RQ_integral+emission_O2+emission_CO2+RQ+rab; 0.457, 0.740, tmp+pH+PL+AN+OD+Arg_conc._cumulo+cell_yield_cumulo+rab_integral+RQ_integral+emission_O2+emission_CO2+RQ; 0.483, 0.740, tmp+pH+PL+OD+RS+Arg_conc._cumulo+emission_O2+emission_CO2+rab; 0.499, 0.740, tmp+pH+PL+Sugar_consuming_rate_cumulo+Arg_conc._cumulo+emission_O2+emission_CO2; 0.474, 0.740, tmp+pH+PL+AN+OD+Arg_conc._cumulo+rab_integral+RQ_integral+emission_O2+emission_CO2; 0.513, 0.740, tmp+pH+PL+Arg_conc._cumulo+emission_CO2; 0.483, 0.740, tmp+pH+PL+OD+Sugar_consuming_rate_cumulo+rab_integral+emission_O2+emission_CO2+RQ; 0.491, 0.740, tmp+pH+PL+AN+Sugar_consuming_rate_cumulo+cell_yield_cumulo+rab_integral+emission_O2; 0.474, 0.740, tmp+pH+PL+AN+OD+Sugar_consuming_rate_cumulo+Arg_conc._cumulo+emission_CO2+RQ+rab; 0.498, 0.740, tmp+pH+PL+OD+RS+Sugar_consuming_rate_cumulo+rab_integral; 0.498, 0.740, tmp+pH+PL+OD+Sugar_consuming_rate_cumulo+Arg_conc._cumulo+rab_integral; 0.474, 0.740, tmp+pH+PL+OD+RS+Sugar_consuming_rate_cumulo+Arg_conc._cumulo+emission_O2+emission_CO2+rab; 0.498, 0.740, tmp+pH+PL+RS+Arg_conc._cumulo+emission_CO2+rab; 0.465, 0.740, tmp+pH+PL+OD+RS+Arg_conc._cumulo+rab_integral+RQ_integral+emission_O2+emission_CO2+RQ; 0.474, 0.740, tmp+pH+PL+OD+Arg_conc._cumulo+rab_integral+RQ_integral+emission_O2+RQ+rab; 0.474, 0.740, tmp+pH+PL+AN+OD+RS+Sugar_consuming_rate_cumulo+Arg_conc._cumulo+RQ+rab; 0.474, 0.740, tmp+pH+PL+AN+RS+Sugar_consuming_rate_cumulo+Arg_conc._cumulo+rab_integral+emission_O2+emission_CO2; 0.491, 0.740, tmp+pH+PL+Arg_conc._cumulo+emission_O2+emission_CO2+RQ+rab; 0.482, 0.740, tmp+pH+PL+AN+OD+RS+Arg_conc._cumulo+rab_integral+RQ; 0.498, 0.740, tmp+pH+PL+rab_integral+emission_O2+emission_CO2+rab; 0.498, 0.740, tmp+pH+PL+OD+Arg_conc._cumulo+RQ+rab; 0.474, 0.740, tmp+pH+PL+AN+OD+RS+rab_integral+emission_O2+emission_CO2+rab; 0.490, 0.740, tmp+pH+PL+OD+RS+Sugar_consuming_rate_cumulo+emission_CO2+RQ; 0.490, 0.739, tmp+pH+PL+OD+Arg_conc._cumulo+cell_yield_cumulo+emission_O2+RQ; 0.490, 0.739, tmp+pH+PL+OD+Arg_conc._cumulo+emission_O2+RQ; 0.498, 0.739, tmp+pH+PL+RS+Arg_conc._cumulo+emission_O2+emission_CO2; 0.490, 0.739, tmp+pH+PL+OD+Sugar_consuming_rate_cumulo+Arg_conc._cumulo+emission_O2+RQ; 0.490, 0.739, tmp+pH+PL+RS+Arg_conc._cumulo+emission_O2+emission_CO2+RQ; 0.465, 0.739, tmp+pH+PL+AN+Sugar_consuming_rate_cumulo+Arg_conc._cumulo+cell_yield_cumulo+rab_integral+emission_O2+emission_CO2+rab; 0.482, 0.739, tmp+pH+PL+AN+OD+RS+Arg_conc._cumulo+emission_O2+RQ; 0.482, 0.739, tmp+pH+PL+AN+RS+Sugar_consuming_rate_cumulo+Arg_conc._cumulo+emission_CO2+RQ; 0.482, 0.739, tmp+pH+PL+AN+OD+RS+Sugar_consuming_rate_cumulo+Arg_conc._cumulo+emission_O2; 0.482, 0.739, tmp+pH+PL+AN+RS+Arg_conc._cumulo+rab_integral+emission_O2+RQ; 0.473, 0.739, tmp+pH+PL+AN+OD+rab_integral+emission_O2+emission_CO2+RQ+rab; 0.482, 0.739, tmp+pH+PL+OD+RS+Sugar_consuming_rate_cumulo+Arg_conc._cumulo+rab_integral+rab; 0.482, 0.739, tmp+pH+PL+AN+OD+RS+emission_CO2+RQ+rab; 0.482, 0.739, tmp+pH+PL+AN+OD+Arg_conc._cumulo+rab_integral+emission_CO2+RQ; 0.490, 0.739, tmp+pH+PL+OD+Sugar_consuming_rate_cumulo+Arg_conc._cumulo+rab_integral+RQ; 0.505, 0.739, tmp+pH+PL+OD+RS+rab_integral; 0.490, 0.739, tmp+pH+PL+OD+RS+cell_yield_cumulo+RQ+rab; 0.473, 0.739, tmp+pH+PL+AN+OD+RS+Arg_conc._cumulo+cell_yield_cumulo+rab_integral+rab; 0.490, 0.739, tmp+pH+PL+AN+RS+Arg_conc._cumulo+emission_O2+emission_CO2; 0.481, 0.739, tmp+pH+PL+OD+Arg_conc._cumulo+cell_yield_cumulo+rab_integral+RQ_integral+emission_O2; 0.490, 0.739, tmp+pH+PL+AN+OD+Sugar_consuming_rate_cumulo+Arg_conc._cumulo+rab; 0.490, 0.739, tmp+pH+PL+AN+OD+RS+RQ+rab; 0.497, 0.739, tmp+pH+PL+OD+Arg_conc._cumulo+cell_yield_cumulo+emission_O2; 0.497, 0.739, tmp+pH+PL+OD+RS+Arg_conc._cumulo+rab_integral; 0.489, 0.739, tmp+pH+PL+OD+RS+Sugar_consuming_rate_cumulo+RQ+rab; 0.497, 0.739, tmp+pH+PL+AN+Arg_conc._cumulo+emission_CO2+RQ; 0.497, 0.739, tmp+pH+PL+AN+OD+Arg_conc._cumulo+rab; 0.489, 0.739, tmp+pH+PL+AN+OD+Arg_conc._cumulo+RQ+rab; 0.464, 0.739, tmp+pH+PL+AN+OD+RS+Sugar_consuming_rate_cumulo+Arg_conc._cumulo+emission_O2+emission_CO2+rab; 0.481, 0.739, tmp+pH+PL+AN+Arg_conc._cumulo+cell_yield_cumulo+rab_integral+emission_O2+rab; 0.481, 0.739, tmp+pH+PL+AN+OD+cell_yield_cumulo+rab_integral+emission_O2+RQ; 0.497, 0.739, tmp+pH+PL+Arg_conc._cumulo+emission_O2+emission_CO2+rab; 0.481, 0.739, tmp+pH+PL+OD+RS+cell_yield_cumulo+emission_CO2+RQ+rab; 0.473, 0.739, tmp+pH+PL+OD+Arg_conc._cumulo+cell_yield_cumulo+rab_integral+RQ_integral+emission_O2+emission_CO2; 0.473, 0.739, tmp+pH+PL+RS+Arg_conc._cumulo+cell_yield_cumulo+rab_integral+emission_O2+ emission_CO2+RQ; 0.481, 0.739, tmp+pH+PL+OD+cell_yield_cumulo+rab_integral+emission_O2+emission_CO2+RQ; 0.473, 0.739, tmp+pH+PL+AN+OD+Arg_conc._cumulo+rab_integral+RQ_integral+emission_O2+RQ; 0.489, 0.739, tmp+pH+PL+OD+Sugar_consuming_rate_cumulo+Arg_conc._cumulo+rab_integral+emission_CO2; 0.472, 0.739, tmp+pH+PL+OD+RS+Arg_conc._cumulo+cell_yield_cumulo+rab_integral+RQ+rab; 0.481, 0.739, tmp+pH+PL+OD+RS+Sugar_consuming_rate_cumulo+Arg_conc._cumulo+emission_O2+RQ; 0.481, 0.739, tmp+pH+PL+OD+RS+Arg_conc._cumulo+rab_integral+emission_CO2+rab; 0.481, 0.739, tmp+pH+PL+AN+OD+Arg_conc._cumulo+cell_yield_cumulo+emission_O2+emission_CO2; 0.472, 0.739, tmp+pH+PL+AN+OD+RS+Sugar_consuming_rate_cumulo+Arg_conc._cumulo+rab_integral+rab; 0.472, 0.739, tmp+pH+PL+AN+OD+RS+Arg_conc._cumulo+cell_yield_cumulo+emission_O2+RQ; 0.497, 0.739, tmp+pH+PL+Sugar_consuming_rate_cumulo+Arg_conc._cumulo+cell_yield_cumulo+emission_CO2; 0.472, 0.739, tmp+pH+PL+AN+OD+Arg_conc._cumulo+emission_O2+emission_CO2+RQ+rab; 0.504, 0.739, tmp+pH+PL+Sugar_consuming_rate_cumulo+Arg_conc._cumulo+cell_yield_cumulo; 0.489, 0.739, tmp+pH+PL+RS+Arg_conc._cumulo+cell_yield_cumulo+rab_integral+emission_O2; 0.489, 0.739, tmp+pH+PL+OD+RS+Arg_conc._cumulo+rab_integral+RQ; 0.489, 0.739, tmp+pH+PL+OD+RS+cell_yield_cumulo+emission_CO2+RQ; 0.463, 0.739, tmp+pH+PL+AN+Sugar_consuming_rate_cumulo+Arg_conc._cumulo+cell_yield_cumulo+rab_integral+emission_O2+RQ+rab; 0.489, 0.739, tmp+pH+PL+RS+Arg_conc._cumulo+emission_CO2+RQ+rab; 0.489, 0.739, tmp+pH+PL+AN+OD+RS+Sugar_consuming_rate_cumulo+emission_CO2; 0.481, 0.739, tmp+pH+PL+AN+OD+Arg_conc._cumulo+RQ_integral+emission_CO2+RQ; 0.472, 0.739, tmp+pH+PL+AN+OD+Sugar_consuming_rate_cumulo+Arg_conc._cumulo+rab_integral+emission_CO2+RQ; 0.504, 0.738, tmp+pH+PL+Sugar_consuming_rate_cumulo+Arg_conc._cumulo+RQ; 0.480, 0.738, tmp+pH+PL+OD+RS+Sugar_consuming_rate_cumulo+emission_CO2+RQ+rab; 0.480, 0.738, tmp+pH+PL+AN+RS+Sugar_consuming_rate_cumulo+Arg_conc._cumulo+cell_yield_cumulo+emission_CO2; 0.480, 0.738, tmp+pH+PL+AN+OD+Sugar_consuming_rate_cumulo+Arg_conc._cumulo+emission_O2+emission_CO2; 0.472, 0.738, tmp+pH+PL+OD+RS+cell_yield_cumulo+rab_integral+emission_O2+emission_CO2+RQ; 0.480, 0.738, tmp+pH+PL+AN+OD+Arg_conc._cumulo+rab_integral+RQ_integral+emission_O2; 0.480, 0.738, tmp+pH+PL+OD+RS+Sugar_consuming_rate_cumulo+cell_yield_cumulo+emission_CO2+rab; 0.472, 0.738, tmp+pH+PL+OD+RS+Sugar_consuming_rate_cumulo+rab_integral+emission_O2+emission_CO2+RQ; 0.496, 0.738, tmp+pH+PL+OD+RS+emission_O2+emission_CO2; 0.463, 0.738, tmp+pH+PL+AN+OD+Sugar_consuming_rate_cumulo+Arg_conc._cumulo+cell_yield_cumulo+rab_integral+emission_O2+rab; 0.472, 0.738, tmp+pH+PL+OD+Sugar_consuming_rate_cumulo+Arg_conc._cumulo+emission_O2+emission_CO2+RQ+rab; 0.480, 0.738, tmp+pH+PL+AN+OD+cell_yield_cumulo+rab_integral+emission_O2+rab; 0.472, 0.738, tmp+pH+PL+AN+Arg_conc._cumulo+cell_yield_cumulo+rab_integral+emission_O2+emission_CO2+rab; 0.480, 0.738, tmp+pH+PL+AN+RS+Sugar_consuming_rate_cumulo+Arg_conc._cumulo+rab_integral+emission_O2; 0.480, 0.738, tmp+pH+PL+AN+OD+RS+Sugar_consuming_rate_cumulo+rab_integral+rab; 0.503, 0.738, tmp+pH+PL+OD+Arg_conc._cumulo+rab; 0.488, 0.738, tmp+pH+PL+AN+OD+Arg_conc._cumulo+cell_yield_cumulo+rab; 0.454, 0.738, tmp+pH+PL+AN+Sugar_consuming_rate_cumulo+Arg_conc._cumulo+cell_yield_cumulo+rab_integral+emission_O2+emission_CO2+RQ+rab; 0.480, 0.738, tmp+pH+PL+OD+RS+Sugar_consuming_rate_cumulo+cell_yield_cumulo+emission_CO2+RQ; 0.454, 0.738, tmp+pH+PL+AN+OD+RS+Arg_conc._cumulo+cell_yield_cumulo+RQ_integral+emission_CO2+RQ+rab; 0.488, 0.738, tmp+pH+PL+AN+Sugar_consuming_rate_cumulo+Arg_conc._cumulo+emission_O2+emission_CO2; 0.480, 0.738, tmp+pH+PL+AN+RS+Arg_conc._cumulo+rab_integral+emission_O2+rab; 0.471, 0.738, tmp+pH+PL+RS+Sugar_consuming_rate_cumulo+Arg_conc._cumulo+cell_yield_cumulo+rab_integral+emission_O2+RQ; 0.496, 0.738, tmp+pH+PL+AN+cell_yield_cumulo+rab_integral+emission_O2; 0.471, 0.738, tmp+pH+PL+AN+OD+RS+Sugar_consuming_rate_cumulo+rab_integral+emission_O2+rab; 0.462, 0.738, tmp+pH+PL+OD+RS+Arg_conc._cumulo+cell_yield_cumulo+RQ_integral+emission_CO2+RQ+rab; 0.453, 0.738, tmp+pH+PL+AN+OD+RS+Arg_conc._cumulo+rab_integral+RQ_integral+emission_O2+emission_CO2+RQ; 0.471, 0.738, tmp+pH+PL+AN+OD+RS+Arg_conc._cumulo+cell_yield_cumulo+RQ_integral+emission_CO2; 0.510, 0.738, tmp+pH+PL+Arg_conc._cumulo+emission_O2; 0.462, 0.738, tmp+pH+PL+AN+OD+RS+Arg_conc._cumulo+rab_integral+RQ_integral+emission_CO2+RQ; 0.495, 0.738, tmp+pH+PL+AN+rab_integral+emission_O2+rab; 0.487, 0.738, tmp+pH+PL+OD+RS+Sugar_consuming_rate_cumulo+cell_yield_cumulo+rab; 0.487, 0.738, tmp+pH+PL+AN+OD+RS+Sugar_consuming_rate_cumulo+rab; 0.487, 0.738, tmp+pH+PL+AN+OD+Sugar_consuming_rate_cumulo+Arg_conc._cumulo+emission_O2; 0.487, 0.738, tmp+pH+PL+OD+RS+Sugar_consuming_rate_cumulo+rab_integral+rab; 0.487, 0.738, tmp+pH+PL+AN+OD+RS+cell_yield_cumulo+emission_CO2; 0.471, 0.738, tmp+pH+PL+AN+RS+Sugar_consuming_rate_cumulo+Arg_conc._cumulo+cell_yield_cumulo+emission_CO2+RQ; 0.471, 0.738, tmp+pH+PL+OD+RS+Sugar_consuming_rate_cumulo+Arg_conc._cumulo+rab_integral+RQ+rab; 0.470, 0.738, tmp+pH+PL+OD+RS+Arg_conc._cumulo+RQ_integral+emission_CO2+RQ+rab; 0.479, 0.738, tmp+pH+PL+AN+OD+Sugar_consuming_rate_cumulo+Arg_conc._cumulo+emission_CO2+rab; 0.495, 0.738, tmp+pH+PL+AN+OD+RS+rab_integral; 0.479, 0.737, tmp+pH+PL+AN+OD+Sugar_consuming_rate_cumulo+Arg_conc._cumulo+RQ+rab; 0.479, 0.737, tmp+pH+PL+AN+OD+RS+Arg_conc._cumulo+emission_O2+rab; 0.495, 0.737, tmp+pH+PL+AN+OD+RS+emission_O2; 0.487, 0.737, tmp+pH+PL+AN+OD+Sugar_consuming_rate_cumulo+Arg_conc._cumulo+rab_integral; 0.453, 0.737, tmp+pH+PL+OD+RS+Arg_conc._cumulo+cell_yield_cumulo+rab_integral+RQ_integral+emission_O2+emission_CO2+RQ; 0.479, 0.737, tmp+pH+PL+Sugar_consuming_rate_cumulo+cell_yield_cumulo+rab_integral+emission_O2+emission_CO2+rab; 0.479, 0.737, tmp+pH+PL+OD+Arg_conc._cumulo+rab_integral+RQ_integral+emission_O2+rab; 0.461, 0.737, tmp+pH+PL+RS+Sugar_consuming_rate_cumulo+Arg_conc._cumulo+cell_yield_cumulo+rab_integral+emission_O2+emission_CO2+rab; 0.461, 0.737, tmp+pH+PL+AN+RS+Sugar_consuming_rate_cumulo+Arg_conc._cumulo+rab_integral+emission_O2+emission_CO2+RQ; 0.461, 0.737, tmp+pH+PL+OD+RS+Sugar_consuming_rate_cumulo+Arg_conc._cumulo+cell_yield_cumulo+rab_integral+emission_O2+RQ; 0.470, 0.737, tmp+pH+PL+AN+OD+Sugar_consuming_rate_cumulo+Arg_conc._cumulo+cell_yield_cumulo+rab_integral+emission_O2; 0.502, 0.737, tmp+pH+PL+AN+Sugar_consuming_rate_cumulo+Arg_conc._cumulo; 0.487, 0.737, tmp+pH+PL+AN+OD+RS+cell_yield_cumulo+rab; 0.494, 0.737, tmp+pH+PL+OD+RS+emission_O2+RQ; 0.478, 0.737, tmp+pH+PL+AN+OD+Arg_conc._cumulo+cell_yield_cumulo+emission_CO2+rab; 0.486, 0.737, tmp+pH+PL+AN+OD+RS+Sugar_consuming_rate_cumulo+RQ; 0.486, 0.737, tmp+pH+PL+OD+Arg_conc._cumulo+emission_O2+RQ+rab; 0.470, 0.737, tmp+pH+PL+AN+OD+RS+Sugar_consuming_rate_cumulo+rab_integral+emission_O2+RQ; 0.461, 0.737, tmp+pH+PL+AN+RS+Arg_conc._cumulo+rab_integral+emission_O2+emission_CO2+RQ+rab; 0.494, 0.737, tmp+pH+PL+OD+RS+rab_integral+emission_CO2; 0.478, 0.737, tmp+pH+PL+AN+OD+Arg_conc._cumulo+cell_yield_cumulo+RQ+rab; 0.486, 0.737, tmp+pH+PL+cell_yield_cumulo+rab_integral+emission_O2+RQ+rab; 0.478, 0.737, tmp+pH+PL+OD+RS+Arg_conc._cumulo+cell_yield_cumulo+emission_O2+rab; 0.470, 0.737, tmp+pH+PL+AN+OD+Arg_conc._cumulo+cell_yield_cumulo+rab_integral+emission_CO2+RQ; 0.486, 0.737, tmp+pH+PL+AN+OD+Arg_conc._cumulo+emission_CO2+rab; 0.486, 0.737, tmp+pH+PL+OD+Arg_conc._cumulo+emission_O2+emission_CO2+rab; 0.452, 0.737, tmp+pH+PL+AN+OD+RS+Sugar_consuming_rate_cumulo+Arg_conc._cumulo+cell_yield_cumulo+rab_integral+emission_O2+RQ; 0.470, 0.737, tmp+pH+PL+RS+Sugar_consuming_rate_cumulo+Arg_conc._cumulo+cell_yield_cumulo+rab_integral+emission_O2+rab; 0.478, 0.737, tmp+pH+PL+AN+RS+Arg_conc._cumulo+emission_O2+emission_CO2+RQ; 0.470, 0.737, tmp+pH+PL+OD+Arg_conc._cumulo+rab_integral+RQ_integral+emission_O2+emission_CO2+rab; 0.469, 0.737, tmp+pH+PL+AN+OD+RS+Sugar_consuming_rate_cumulo+Arg_conc._cumulo+cell_yield_cumulo+emission_CO2; 0.469, 0.737, tmp+pH+PL+RS+Sugar_consuming_rate_cumulo+Arg_conc._cumulo+cell_yield_cumulo+emission_CO2+rab; 0.478, 0.737, tmp+pH+PL+RS+Sugar_consuming_rate_cumulo+Arg_conc._cumulo+cell_yield_cumulo+emission_CO2+rab; 0.442, 0.737, tmp+pH+PL+AN+OD+RS+Sugar_consuming_rate_cumulo+Arg_conc._cumulo+cell_yield_cumulo+rab_integral+emission_O2+emission_CO2+rab; 0.461, 0.737, tmp+pH+PL+AN+OD+RS+Arg_conc._cumulo+cell_yield_cumulo+rab_integral+RQ+rab; 0.460, 0.737, tmp+pH+PL+AN+OD+RS+Arg_conc._cumulo+RQ_integral+emission_O2+emission_CO2+RQ; 0.478, 0.737, tmp+pH+PL+AN+Sugar_consuming_rate_cumulo+emission_O2+emission_CO2+RQ; 0.469, 0.737, tmp+pH+PL+AN+OD+RS+Sugar_consuming_rate_cumulo+Arg_conc._cumulo+emission_O2+RQ; 0.469, 0.737, tmp+pH+PL+OD+Sugar_consuming_rate_cumulo+Arg_conc._cumulo+cell_yield_cumulo+rab_integral+emission_O2+rab; 0.477, 0.737, tmp+pH+PL+AN+OD+RS+Sugar_consuming_rate_cumulo+emission_CO2+rab; 0.516, 0.737, tmp+pH+PL+Arg_conc._cumulo; 0.486, 0.737, tmp+pH+PL+cell_yield_cumulo+rab_integral+emission_O2+emission_CO2+rab; 0.477, 0.737, tmp+pH+PL+AN+OD+RS+cell_yield_cumulo+emission_CO2+rab; 0.469, 0.737, tmp+pH+PL+AN+OD+Sugar_consuming_rate_cumulo+rab_integral+emission_O2+RQ+rab; 0.486, 0.737, tmp+pH+PL+OD+Arg_conc._cumulo+RQ_integral+emission_CO2+RQ; 0.486, 0.737, tmp+pH+PL+OD+RS+emission_O2+emission_CO2+RQ; 0.477, 0.737, tmp+pH+PL+RS+Sugar_consuming_rate_cumulo+cell_yield_cumulo+rab_integral+emission_O2+rab; 0.469, 0.737, tmp+pH+PL+AN+OD+RS+cell_yield_cumulo+rab_integral+emission_O2+rab; 0.493, 0.737, tmp+pH+PL+RS+cell_yield_cumulo+rab_integral+emission_O2; 0.486, 0.737, tmp+pH+PL+OD+Sugar_consuming_rate_cumulo+Arg_conc._cumulo+cell_yield_cumulo; 0.509, 0.737, tmp+pH+PL+OD+emission_O2; 0.493, 0.737, tmp+pH+PL+OD+Arg_conc._cumulo+emission_CO2+rab; 0.477, 0.737, tmp+pH+PL+AN+OD+Sugar_consuming_rate_cumulo+Arg_conc._cumulo+rab_integral+emission_CO2; 0.469, 0.737, tmp+pH+PL+OD+Sugar_consuming_rate_cumulo+Arg_conc._cumulo+rab_integral+emission_CO2+RQ+rab; 0.493, 0.737, tmp+pH+PL+OD+RS+emission_O2+rab; 0.501, 0.737, tmp+pH+PL+Sugar_consuming_rate_cumulo+Arg_conc._cumulo+rab; 0.485, 0.737, tmp+pH+PL+AN+OD+Arg_conc._cumulo+cell_yield_cumulo+emission_O2; 0.493, 0.737, tmp+pH+PL+OD+Arg_conc._cumulo+emission_O2+rab; 0.493, 0.737, tmp+pH+PL+OD+RS+Sugar_consuming_rate_cumulo+cell_yield_cumulo; 0.469, 0.737, tmp+pH+PL+RS+Sugar_consuming_rate_cumulo+Arg_conc._cumulo+rab_integral+emission_O2+RQ+rab; 0.485, 0.736, tmp+pH+PL+AN+OD+RS+emission_O2+emission_CO2; 0.477, 0.736, tmp+pH+PL+OD+Arg_conc._cumulo+cell_yield_cumulo+emission_O2+emission_CO2+rab; 0.469, 0.736, tmp+pH+PL+OD+Sugar_consuming_rate_cumulo+rab_integral+emission_O2+emission_CO2+RQ+rab; 0.493, 0.736, tmp+pH+PL+Sugar_consuming_rate_cumulo+Arg_conc._cumulo+cell_yield_cumulo+RQ; 0.485, 0.736, tmp+pH+PL+AN+OD+Arg_conc._cumulo+emission_O2+rab; 0.485, 0.736, tmp+pH+PL+AN+OD+RS+cell_yield_cumulo+RQ; 0.501, 0.736, tmp+pH+PL+RS+Sugar_consuming_rate_cumulo+Arg_conc._cumulo; 0.493, 0.736, tmp+pH+PL+OD+RS+rab_integral+RQ; 0.485, 0.736, tmp+pH+PL+AN+OD+RS+rab_integral+emission_CO2; 0.485, 0.736, tmp+pH+PL+AN+RS+Arg_conc._cumulo+emission_CO2+rab; 0.460, 0.736, tmp+pH+PL+AN+Arg_conc._cumulo+cell_yield_cumulo+rab_integral+emission_O2+emission_CO2+RQ+rab; 0.493, 0.736, tmp+pH+PL+OD+RS+Sugar_consuming_rate_cumulo+emission_O2; 0.468, 0.736, tmp+pH+PL+AN+OD+RS+cell_yield_cumulo+rab_integral+emission_O2+RQ; 0.485, 0.736, tmp+pH+PL+RS+Sugar_consuming_rate_cumulo+Arg_conc._cumulo+emission_O2+emission_CO2; 0.485, 0.736, tmp+pH+PL+rab_integral+emission_O2+emission_CO2+RQ+rab; 0.459, 0.736, tmp+pH+PL+AN+OD+Arg_conc._cumulo+rab_integral+RQ_integral+emission_O2+RQ+rab; 0.459, 0.736, tmp+pH+PL+AN+OD+RS+Sugar_consuming_rate_cumulo+Arg_conc._cumulo+rab_integral+RQ+rab; 0.500, 0.736, tmp+pH+PL+rab_integral+emission_O2+emission_O2; 0.468, 0.736, tmp+pH+PL+AN+OD+RS+Arg_conc._cumulo+rab_integral+RQ+rab; 0.493, 0.736, tmp+pH+PL+Sugar_consuming_rate_cumulo+rab_integral+emission_O2+rab; 0.492, 0.736, tmp+pH+PL+RS+Sugar_consuming_rate_cumulo+Arg_conc._cumulo+cell_yield_cumulo; 0.459, 0.736, tmp+pH+PL+AN+OD+RS+rab_integral+emission_O2+emission_CO2+RQ+rab; 0.484, 0.736, tmp+pH+PL+OD+RS+Sugar_consuming_rate_cumulo+rab_integral+RQ; 0.476, 0.736, tmp+pH+PL+AN+RS+Sugar_consuming_rate_cumulo+Arg_conc._cumulo+emission_CO2+rab; 0.459, 0.736, tmp+pH+PL+OD+Arg_conc._cumulo+cell_yield_cumulo+rab_integral+RQ_integral+emission_O2+RQ+rab; 0.492, 0.736, tmp+pH+PL+Arg_conc._cumulo+emission_CO2+RQ+rab; 0.450, 0.736, tmp+pH+PL+RS+Sugar_consuming_rate_cumulo+Arg_conc._cumulo+cell_yield_cumulo+rab_integral+emission_O2+emission_CO2+RQ+rab; 0.476, 0.736, tmp+pH+PL+AN+Sugar_consuming_rate_cumulo+cell_yield_cumulo+rab_integral+emission_O2+RQ; 0.476, 0.736, tmp+pH+PL+AN+OD+Sugar_consuming_rate_cumulo+Arg_conc._cumulo+emission_O2+RQ; 0.492, 0.736, tmp+pH+PL+OD+RS+rab_integral+rab; 0.476, 0.736, tmp+pH+PL+AN+OD+Arg_conc._cumulo+emission_O2+RQ+rab;

0.459, 0.736, tmp+pH+PL+OD+RS+cell_yield_cumulo+rab_integral+emission_O2+emission_CO2+RQ+rab; 0.459, 0.736, tmp+pH+PL+OD+RS+Sugar_consuming_rate_cumulo+rab_integral+emission_O2+emission_CO2+RQ+rab; 0.484, 0.736, tmp+pH+PL+Sugar_consuming_rate_cumulo+Arg_conc._cumulo+emission_O2+emission_CO2+rab; 0.484, 0.736, tmp+pH+PL+OD+RS+emission_O2+emission_CO2+rab; 0.484, 0.736, tmp+pH+PL+AN+Sugar_consuming_rate_cumulo+Arg_conc._cumulo+cell_yield_cumulo+emission_CO2; 0.450, 0.736, tmp+pH+PL+AN+OD+RS+Arg_conc._cumulo+cell_yield_cumulo+rab_integral+RQ_integral+emission_CO2+RQ; 0.484, 0.736, tmp+pH+PL+AN+OD+Arg_conc._cumulo+rab_integral+emission_CO2; 0.476, 0.736, tmp+pH+PL+RS+Sugar_consuming_rate_cumulo+Arg_conc._cumulo+emission_O2+emission_CO2+RQ; 0.476, 0.736, tmp+pH+PL+Sugar_consuming_rate_cumulo+Arg_conc._cumulo+emission_O2+emission_CO2+RQ+rab; 0.476, 0.736, tmp+pH+PL+Sugar_consuming_rate_cumulo+cell_yield_cumulo+rab_integral+emission_O2+emission_CO2+RQ; 0.467, 0.736, tmp+pH+PL+AN+OD+RS+Arg_conc._cumulo+cell_yield_cumulo+emission_O2+rab; 0.467, 0.736, tmp+pH+PL+RS+Arg_conc._cumulo+cell_yield_cumulo+rab_integral+emission_O2+emission_CO2+rab; 0.467, 0.736, tmp+pH+PL+OD+Sugar_consuming_rate_cumulo+Arg_conc._cumulo+cell_yield_cumulo+rab_integral+emission_O2+emission_CO2; 0.476, 0.736, tmp+pH+PL+AN+Sugar_consuming_rate_cumulo+Arg_conc._cumulo+cell_yield_cumulo+emission_CO2+RQ; 0.492, 0.736, tmp+pH+PL+Sugar_consuming_rate_cumulo+Arg_conc._cumulo+rab_integral+emission_CO2; 0.476, 0.736, tmp+pH+PL+Arg_conc._cumulo+rab_integral+RQ_integral+emission_O2+emission_CO2+RQ; 0.476, 0.736, tmp+pH+PL+AN+OD+Sugar_consuming_rate_cumulo+Arg_conc._cumulo+rab_integral+RQ; 0.484, 0.736, tmp+pH+PL+Sugar_consuming_rate_cumulo+Arg_conc._cumulo+rab_integral+emission_CO2+RQ; 0.467, 0.736, tmp+pH+PL+OD+RS+Arg_conc._cumulo+cell_yield_cumulo+emission_O2+RQ+rab; 0.484, 0.736, tmp+pH+PL+OD+RS+rab_integral+emission_CO2+RQ; 0.484, 0.736, tmp+pH+PL+OD+Arg_conc._cumulo+cell_yield_cumulo+rab_integral+RQ; 0.484, 0.736, tmp+pH+PL+OD+Arg_conc._cumulo+cell_yield_cumulo+rab_integral+emission_CO2; 0.484, 0.736, tmp+pH+PL+AN+Arg_conc._cumulo+emission_O2+emission_CO2+rab; 0.476, 0.736, tmp+pH+PL+AN+OD+Arg_conc._cumulo+cell_yield_cumulo+emission_O2+RQ; 0.484, 0.736, tmp+pH+PL+RS+Arg_conc._cumulo+emission_O2+emission_CO2+rab; 0.484, 0.736, tmp+pH+PL+OD+RS+Sugar_consuming_rate_cumulo+rab_integral+emission_CO2; 0.467, 0.735, tmp+pH+PL+AN+OD+RS+Arg_conc._cumulo+RQ_integral+emission_CO2+rab; 0.491, 0.735, tmp+pH+PL+OD+Arg_conc._cumulo+rab_integral+RQ; 0.467, 0.735, tmp+pH+PL+OD+Arg_conc._cumulo+cell_yield_cumulo+rab_integral+emission_CO2+RQ+rab; 0.475, 0.735, tmp+pH+PL+AN+OD+RS+Sugar_consuming_rate_cumulo+emission_CO2+RQ; 0.475, 0.735, tmp+pH+PL+AN+Sugar_consuming_rate_cumulo+cell_yield_cumulo+rab_integral+emission_O2+rab; 0.491, 0.735, tmp+pH+PL+AN+Sugar_consuming_rate_cumulo+Arg_conc._cumulo+cell_yield_cumulo; 0.475, 0.735, tmp+pH+PL+RS+Sugar_consuming_rate_cumulo+cell_yield_cumulo+rab_integral+emission_O2+RQ; 0.499, 0.735, tmp+pH+PL+Arg_conc._cumulo+emission_O2+RQ; 0.491, 0.735, tmp+pH+PL+AN+OD+Arg_conc._cumulo+rab_integral; 0.483, 0.735, tmp+pH+PL+RS+Sugar_consuming_rate_cumulo+Arg_conc._cumulo+rab_integral+emission_CO2; 0.458, 0.735, tmp+pH+PL+AN+OD+RS+Sugar_consuming_rate_cumulo+Arg_conc._cumulo+cell_yield_cumulo+emission_CO2+rab; 0.475, 0.735, tmp+pH+PL+Sugar_consuming_rate_cumulo+Arg_conc._cumulo+cell_yield_cumulo+emission_O2+emission_CO2+RQ; 0.475, 0.735, tmp+pH+PL+AN+OD+Sugar_consuming_rate_cumulo+rab_integral+emission_O2+emission_CO2; 0.467, 0.735, tmp+pH+PL+AN+OD+RS+Arg_conc._cumulo+emission_O2+RQ+rab; 0.483, 0.735, tmp+pH+PL+cell_yield_cumulo+rab_integral+emission_O2+emission_CO2+RQ; 0.466, 0.735, tmp+pH+PL+AN+OD+RS+Sugar_consuming_rate_cumulo+cell_yield_cumulo+emission_CO2+rab; 0.483, 0.735, tmp+pH+PL+OD+RS+Arg_conc._cumulo+emission_O2+rab; 0.499, 0.735, tmp+pH+PL+Arg_conc._cumulo+emission_CO2+rab; 0.458, 0.735, tmp+pH+PL+AN+OD+Arg_conc._cumulo+cell_yield_cumulo+rab_integral+RQ_integral+emission_O2+emission_CO2; 0.506, 0.735, tmp+pH+PL+OD+Sugar_consuming_rate_cumulo; 0.466, 0.735, tmp+pH+PL+OD+cell_yield_cumulo+rab_integral+emission_O2+emission_CO2+RQ+rab; 0.483, 0.735, tmp+pH+PL+AN+rab_integral+emission_O2+RQ+rab; 0.499, 0.735, tmp+pH+PL+AN+Arg_conc._cumulo+emission_O2; 0.475, 0.735, tmp+pH+PL+AN+OD+Arg_conc._cumulo+emission_O2+emission_CO2+rab; 0.475, 0.735, tmp+pH+PL+OD+RS+Sugar_consuming_rate_cumulo+cell_yield_cumulo+rab_integral+emission_O2; 0.498, 0.735, tmp+pH+PL+RS+Sugar_consuming_rate_cumulo+cell_yield_cumulo; 0.466, 0.735, tmp+pH+PL+AN+OD+Arg_conc._cumulo+rab_integral+RQ_integral+emission_O2+rab; 0.457, 0.735, tmp+pH+PL+AN+OD+Arg_conc._cumulo+cell_yield_cumulo+rab_integral+RQ_integral+emission_O2+RQ; 0.475, 0.735, tmp+pH+PL+OD+RS+Sugar_consuming_rate_cumulo+Arg_conc._cumulo+emission_O2+rab; 0.466, 0.735, tmp+pH+PL+AN+Arg_conc._cumulo+cell_yield_cumulo+rab_integral+emission_O2+RQ+rab; 0.483, 0.735, tmp+pH+PL+AN+Sugar_consuming_rate_cumulo+Arg_conc._cumulo+emission_CO2+rab; 0.474, 0.735, tmp+pH+PL+RS+Arg_conc._cumulo+cell_yield_cumulo+rab_integral+emission_O2+RQ; 0.474, 0.735, tmp+pH+PL+OD+RS+Sugar_consuming_rate_cumulo+rab_integral+emission_CO2+rab; 0.474, 0.735, tmp+pH+PL+OD+Sugar_consuming_rate_cumulo+Arg_conc._cumulo+emission_O2+emission_CO2+rab; 0.474, 0.735, tmp+pH+PL+Sugar_consuming_rate_cumulo+Arg_conc._cumulo+cell_yield_cumulo+emission_CO2+RQ+rab; 0.466, 0.735, tmp+pH+PL+OD+Arg_conc._cumulo+cell_yield_cumulo+rab_integral+RQ_integral+emission_O2+rab; 0.483, 0.735, tmp+pH+PL+OD+RS+Sugar_consuming_rate_cumulo+cell_yield_cumulo+RQ; 0.457, 0.735, tmp+pH+PL+AN+OD+Arg_conc._cumulo+rab_integral+RQ_integral+emission_O2+emission_CO2+rab; 0.474, 0.735, tmp+pH+PL+AN+OD+RS+Sugar_consuming_rate_cumulo+cell_yield_cumulo+emission_CO2; 0.466, 0.735, tmp+pH+PL+AN+RS+Sugar_consuming_rate_cumulo+Arg_conc._cumulo+cell_yield_cumulo+rab_integral+emission_O2; 0.483, 0.735, tmp+pH+PL+Arg_conc._cumulo+rab_integral+RQ_integral+emission_O2+emission_CO2; 0.498, 0.735, tmp+pH+PL+Sugar_consuming_rate_cumulo+Arg_conc._cumulo+emission_O2; 0.482, 0.735, tmp+pH+PL+AN+OD+RS+Sugar_consuming_rate_cumulo+rab_integral; 0.498, 0.735, tmp+pH+PL+AN+rab_integral+emission_O2; 0.482, 0.735, tmp+pH+PL+AN+OD+Arg_conc._cumulo+rab_integral+RQ; 0.505, 0.735, tmp+pH+PL+Arg_conc._cumulo+RQ; 0.490, 0.735, tmp+pH+PL+OD+Arg_conc._cumulo+cell_yield_cumulo+rab_integral; 0.482, 0.735, tmp+pH+PL+AN+RS+Arg_conc._cumulo+rab_integral+emission_CO2; 0.474, 0.735, tmp+ pH+PL+RS+Arg_conc._cumulo+emission_O2+emission_CO2+RQ+rab; 0.465, 0.735, tmp+pH+PL+AN+OD+Arg_conc._cumulo+cell_yield_cumulo+rab_integral+RQ_integral+emission_O2; 0.505, 0.735, tmp+pH+PL+RS+Arg_conc._cumulo; 0.482, 0.735, tmp+pH+PL+OD+RS+rab_integral+emission_CO2+rab; 0.457, 0.735, tmp+pH+PL+OD+Arg_conc._cumulo+cell_yield_cumulo+rab_integral+RQ_integral+emission_O2+emission_CO2+rab; 0.448, 0.735, tmp+pH+PL+OD+RS+Arg_conc._cumulo+rab_integral+RQ_integral+emission_O2+emission_CO2+RQ+rab; 0.457, 0.735, tmp+pH+PL+AN+OD+RS+Sugar_consuming_rate_cumulo+Arg_conc._cumulo+RQ_integral+emission_CO2+RQ; 0.438, 0.735, tmp+pH+PL+AN+OD+Arg_conc._cumulo+cell_yield_cumulo+rab_integral+RQ_integral+emission_O2+emission_CO2+RQ+rab; 0.505, 0.735, tmp+pH+PL+AN+Arg_conc._cumulo; 0.465, 0.735, tmp+pH+PL+AN+RS+Sugar_consuming_rate_cumulo+Arg_conc._cumulo+rab_integral+emission_O2+RQ; 0.482, 0.735, tmp+pH+PL+OD+RS+Arg_conc._cumulo+rab_integral+rab; 0.474, 0.735, tmp+pH+PL+AN+Arg_conc._cumulo+emission_O2+emission_CO2+RQ+rab; 0.474, 0.735, tmp+pH+PL+RS+Sugar_consuming_rate_cumulo+Arg_conc._cumulo+rab_integral+emission_CO2+RQ; 0.482, 0.735, tmp+pH+OD+RS+Sugar_consuming_rate_cumulo+Arg_conc._cumulo+emission_CO2+RQ; 0.456, 0.735, tmp+pH+PL+AN+RS+Sugar_consuming_rate_cumulo+Arg_conc._cumulo+cell_yield_cumulo+rab_integral+emission_O2+emission_CO2; 0.474, 0.735, tmp+pH+PL+OD+Arg_conc._cumulo+cell_yield_cumulo+RQ_integral+emission_CO2+RQ; 0.474, 0.735, tmp+pH+PL+AN+OD+RS+cell_yield_cumulo+emission_CO2+RQ; 0.474, 0.735, tmp+pH+PL+AN+RS+Sugar_consuming_rate_cumulo+Arg_conc._cumulo+emission_O2+emission_CO2; 0.456, 0.735, tmp+pH+PL+OD+Sugar_consuming_rate_cumulo+Arg_conc._cumulo+rab_integral+RQ_integral+emission_O2+emission_CO2+RQ; 0.482, 0.735, tmp+pH+PL+Sugar_consuming_rate_cumulo+rab_integral+emission_O2+RQ+rab; 0.438, 0.734, tmp+pH+PL+AN+OD+RS+Sugar_consuming_rate_cumulo+Arg_conc._cumulo+cell_yield_cumulo+rab_integral+emission_O2+RQ+rab; 0.490, 0.734, tmp+pH+PL+OD+Arg_conc._cumulo+rab_integral+emission_CO2; 0.456, 0.734, tmp+pH+PL+AN+RS+Sugar_consuming_rate_cumulo+Arg_conc._cumulo+rab_integral+emission_O2+emission_CO2+rab; 0.512, 0.734, tmp+pH+PL+OD; 0.482, 0.734, tmp+pH+PL+OD+Sugar_consuming_rate_cumulo+Arg_conc._cumulo+rab_integral+rab; 0.497, 0.734, tmp+pH+PL+OD+Arg_conc._cumulo+rab_integral; 0.474, 0.734, tmp+pH+PL+OD+RS+Arg_conc._cumulo+emission_O2+RQ+rab; 0.490, 0.734, tmp+pH+PL+Arg_conc._cumulo+rab_integral+emission_CO2+RQ; 0.465, 0.734, tmp+pH+PL+AN+OD+RS+Sugar_consuming_rate_cumulo+Arg_conc._cumulo+emission_O2+rab; 0.465, 0.734, tmp+pH+PL+AN+OD+Arg_conc._cumulo+RQ_integral+emission_O2+emission_CO2+RQ; 0.438, 0.734, tmp+pH+PL+AN+OD+RS+Arg_conc._cumulo+cell_yield_cumulo+rab_integral+RQ_integral+emission_O2+emission_CO2+RQ; 0.497, 0.734, tmp+pH+PL+OD+emission_O2+RQ; 0.473, 0.734, tmp+pH+PL+OD+Arg_conc._cumulo+rab_integral+emission_CO2+RQ+rab; 0.473, 0.734, tmp+pH+PL+OD+RS+Sugar_consuming_rate_cumulo+cell_yield_cumulo+RQ+rab; 0.465, 0.734, tmp+pH+PL+AN+OD+cell_yield_cumulo+rab_integral+emission_O2+RQ+rab; 0.481, 0.734, tmp+pH+PL+OD+Sugar_consuming_rate_cumulo+Arg_conc._cumulo+emission_O2+rab; 0.473, 0.734, tmp+pH+PL+OD+Arg_conc._cumulo+RQ_integral+emission_O2+emission_CO2+RQ; 0.456, 0.734, tmp+pH+PL+AN+OD+Arg_conc._cumulo+cell_yield_cumulo+emission_O2+emission_CO2+RQ+rab; 0.489, 0.734, tmp+pH+PL+AN+Sugar_consuming_rate_cumulo+Arg_conc._cumulo+RQ; 0.473, 0.734, tmp+pH+PL+RS+Sugar_consuming_rate_cumulo+cell_yield_cumulo+rab_integral+emission_O2+emission_CO2; 0.473, 0.734, tmp+pH+PL+AN+OD+cell_yield_cumulo+rab_integral+emission_O2+emission_CO2; 0.489, 0.734, tmp+pH+OD+RS+Arg_conc._cumulo+emission_CO2+RQ; 0.464, 0.734, tmp+pH+PL+AN+OD+RS+Sugar_consuming_rate_cumulo+rab_integral+emission_O2+emission_CO2; 0.481, 0.734, tmp+pH+PL+Sugar_consuming_rate_cumulo+Arg_conc._cumulo+cell_yield_cumulo+emission_CO2+rab; 0.489, 0.734, tmp+pH+PL+AN+Arg_conc._cumulo+rab_integral+emission_CO2; 0.473, 0.734, tmp+pH+PL+OD+Sugar_consuming_rate_cumulo+Arg_conc._cumulo+rab_integral+RQ+rab; 0.481, 0.734, tmp+pH+PL+OD+RS+Sugar_consuming_rate_cumulo+emission_O2+rab; 0.473, 0.734, tmp+pH+PL+RS+Sugar_consuming_rate_cumulo+Arg_conc._cumulo+emission_O2+emission_CO2+rab; 0.473, 0.734, tmp+pH+PL+OD+RS+Arg_conc._cumulo+rab_integral+RQ+rab; 0.489, 0.734, tmp+pH+PL+RS+Arg_conc._cumulo+rab_integral+emission_CO2; 0.464, 0.734, tmp+pH+PL+AN+OD+RS+cell_yield_cumulo+rab_integral+emission_O2+emission_CO2; 0.481, 0.734, tmp+pH+PL+AN+RS+Sugar_consuming_rate_cumulo+Arg_conc._cumulo+cell_yield_cumulo; 0.464, 0.734, tmp+pH+PL+AN+RS+Arg_conc._cumulo+rab_integral+emission_O2+RQ+rab; 0.446, 0.734, tmp+pH+PL+AN+OD+RS+Arg_conc._cumulo+cell_yield_cumulo+RQ_integral+emission_O2+emission_CO2+RQ; 0.481, 0.734, tmp+pH+PL+AN+OD+RS+emission_O2+RQ; 0.473, 0.734, tmp+pH+PL+RS+Arg_conc._cumulo+cell_yield_cumulo+rab_integral+emission_O2+rab; 0.481, 0.734, tmp+pH+PL+AN+OD+RS+rab_integral+RQ; 0.481, 0.734, tmp+pH+PL+Sugar_consuming_rate_cumulo+Arg_conc._cumulo+cell_yield_cumulo+emission_O2+emission_CO2; 0.472, 0.734, tmp+pH+PL+AN+OD+RS+emission_O2+emission_CO2+RQ; 0.472, 0.734, tmp+pH+PL+AN+OD+Arg_conc._cumulo+cell_yield_cumulo+rab_integral+emission_CO2; 0.464, 0.734, tmp+pH+PL+AN+OD+Arg_conc._cumulo+cell_yield_cumulo+RQ_integral+emission_CO2+RQ; 0.455, 0.734, tmp+pH+PL+AN+OD+RS+Sugar_consuming_rate_cumulo+rab_integral+emission_O2+RQ+rab; 0.481, 0.734, tmp+pH+PL+RS+Arg_conc._cumulo+rab_integral+emission_CO2+RQ; 0.481, 0.734, tmp+pH+PL+AN+cell_yield_cumulo+rab_integral+emission_O2+RQ; 0.455, 0.734, tmp+pH+PL+OD+RS+Arg_conc._cumulo+cell_yield_cumulo+rab_integral+RQ_integral+emission_CO2+RQ; 0.489, 0.734, tmp+pH+PL+Sugar_consuming_rate_cumulo+Arg_conc._cumulo+RQ+rab; 0.472, 0.734, tmp+pH+PL+OD+RS+emission_O2+emission_CO2+RQ+rab; 0.472, 0.734, tmp+pH+PL+AN+RS+Arg_conc._cumulo+emission_CO2+RQ+rab; 0.489, 0.734, tmp+pH+PL+RS+rab_integral+emission_O2+rab; 0.481, 0.734, tmp+pH+PL+OD+Arg_conc._cumulo+cell_yield_cumulo+emission_O2+rab; 0.464, 0.734, tmp+pH+PL+OD+RS+Arg_conc._cumulo+RQ_integral+emission_O2+emission_CO2+RQ; 0.488, 0.734, tmp+pH+PL+rab_integral+emission_O2+emission_CO2+RQ; 0.464, 0.734, tmp+pH+PL+AN+OD+RS+Sugar_consuming_rate_cumulo+cell_yield_cumulo+emission_CO2+RQ; 0.480, 0.734, tmp+pH+PL+AN+Sugar_consuming_rate_cumulo+Arg_conc._cumulo+rab_integral+emission_CO2; 0.480, 0.734, tmp+pH+PL+AN+OD+RS+rab_integral+rab; 0.464, 0.734, tmp+pH+PL+AN+RS+Sugar_consuming_rate_cumulo+Arg_conc._cumulo+emission_CO2+rab; 0.455, 0.734, tmp+pH+PL+RS+Arg_conc._cumulo+cell_yield_cumulo+rab_integral+ emission_O2+emission_CO2+RQ+rab; 0.472, 0.734, tmp+pH+PL+OD+Arg_conc._cumulo+cell_yield_cumulo+emission_O2+RQ+rab; 0.472, 0.734, tmp+pH+PL+OD+RS+Sugar_consuming_rate_cumulo+RQ+rab; 0.472, 0.734, tmp+pH+PL+AN+OD+RS+rab_integral+emission_CO2+RQ; 0.472, 0.734, tmp+pH+PL+AN+OD+Sugar_consuming_rate_cumulo+Arg_conc._cumulo+cell_yield_cumulo+RQ; 0.472, 0.733, tmp+pH+PL+OD+Sugar_consuming_rate_cumulo+Arg_conc._cumulo+emission_O2+RQ+rab; 0.488, 0.733, tmp+pH+PL+Sugar_consuming_rate_cumulo+Arg_conc._cumulo+cell_yield_cumulo+rab; 0.472, 0.733, tmp+pH+PL+AN+RS+Sugar_consuming_rate_cumulo+Arg_conc._cumulo+rab_integral+emission_CO2; 0.480, 0.733, tmp+pH+PL+AN+OD+RS+emission_O2+rab; 0.455, 0.733, tmp+pH+PL+AN+OD+RS+Arg_conc._cumulo+cell_yield_cumulo+RQ_integral+emission_CO2+rab; 0.472, 0.733, tmp+pH+PL+OD+RS+Sugar_consuming_rate_cumulo+rab_integral+RQ+rab; 0.463, 0.733, tmp+pH+PL+OD+RS+Sugar_consuming_rate_cumulo+Arg_conc._cumulo+emission_O2+RQ+rab; 0.463, 0.733, tmp+pH+PL+AN+OD+RS+Sugar_consuming_rate_cumulo+emission_CO2+RQ+rab; 0.454, 0.733, tmp+pH+PL+RS+Sugar_consuming_rate_cumulo+Arg_conc._cumulo+cell_yield_cumulo+rab_integral+emission_O2+RQ+rab; 0.488, 0.733, tmp+pH+PL+RS+Sugar_consuming_rate_cumulo+Arg_conc._cumulo+RQ; 0.472, 0.733, tmp+pH+PL+OD+Sugar_consuming_rate_cumulo+Arg_conc._cumulo+rab_integral+emission_CO2+rab; 0.480, 0.733, tmp+pH+PL+OD+RS+emission_O2+RQ+rab; 0.472, 0.733, tmp+pH+PL+AN+Sugar_consuming_rate_cumulo+Arg_conc._cumulo+emission_CO2+RQ+rab; 0.463, 0.733, tmp+pH+PL+AN+RS+Sugar_consuming_rate_cumulo+Arg_conc._cumulo+rab_integral+emission_O2+rab; 0.454, 0.733, tmp+pH+PL+AN+OD+RS+Arg_conc._cumulo+cell_yield_cumulo+emission_O2+RQ+rab; 0.463, 0.733, tmp+pH+PL+OD+RS+Arg_conc._cumulo+rab_integral+RQ_integral+emission_CO2+RQ; 0.480, 0.733, tmp+pH+PL+RS+Sugar_consuming_rate_cumulo+Arg_conc._cumulo+cell_yield_cumulo+RQ; 0.480, 0.733, tmp+pH+PL+OD+RS+Sugar_consuming_rate_cumulo+emission_O2+emission_CO2; 0.472, 0.733, tmp+pH+PL+RS+Sugar_consuming_rate_cumulo+Arg_conc._cumulo+rab_integral+emission_CO2+rab; 0.436, 0.733, tmp+pH+PL+AN+OD+RS+Sugar_consuming_rate_cumulo+Arg_conc._cumulo+cell_yield_cumulo+rab_integral+emission_O2+emission_CO2+RQ; 0.445, 0.733, tmp+pH+PL+OD+RS+Sugar_consuming_rate_cumulo+Arg_conc._cumulo+cell_yield_cumulo+rab_integral+emission_O2+emission_CO2+rab; 0.454, 0.733, tmp+pH+PL+AN+OD+RS+Arg_conc._cumulo+rab_integral+RQ_integral+emission_O2+emission_CO2; 0.436, 0.733, tmp+pH+PL+AN+OD+RS+Arg_conc._cumulo+rab_integral+RQ_integral+emission_O2+emission_CO2+RQ+rab; 0.471, 0.733, tmp+pH+PL+AN+OD+RS+emission_O2+emission_CO2+rab; 0.445, 0.733, tmp+pH+PL+AN+RS+Sugar_consuming_rate_cumulo+Arg_conc._cumulo+cell_yield_cumulo+rab_integral+emission_O2+emission_CO2+RQ; 0.480, 0.733, tmp+pH+PL+AN+Arg_conc._cumulo+rab_integral+emission_CO2+RQ; 0.463, 0.733, tmp+pH+PL+AN+OD+RS+cell_yield_cumulo+emission_CO2+RQ+rab; 0.463, 0.733, tmp+pH+PL+AN+RS+Sugar_consuming_rate_cumulo+Arg_conc._cumulo+cell_yield_cumulo+emission_CO2+rab; 0.463, 0.733, tmp+pH+PL+RS+Sugar_consuming_rate_cumulo+Arg_conc._cumulo+cell_yield_cumulo+rab_integral+emission_CO2+RQ; 0.495, 0.733, tmp+pH+PL+Arg_conc._cumulo+rab_integral+emission_CO2; 0.463, 0.733, tmp+pH+PL+OD+RS+Arg_conc._cumulo+rab_integral+RQ_integral+emission_O2+emission_CO2; 0.471, 0.733, tmp+pH+PL+AN+OD+RS+cell_yield_cumulo+RQ+rab; 0.471, 0.733, tmp+pH+PL+AN+OD+Sugar_consuming_rate_cumulo+Arg_conc._cumulo+cell_yield_cumulo+rab; 0.471, 0.733, tmp+pH+PL+AN+OD+RS+rab_integral+emission_CO2+rab; 0.462, 0.733, tmp+pH+PL+RS+Sugar_consuming_rate_cumulo+Arg_conc._cumulo+cell_yield_cumulo+emission_O2+emission_CO2+RQ; 0.453, 0.733, tmp+pH+PL+AN+OD+Sugar_consuming_rate_cumulo+Arg_conc._cumulo+emission_O2+emission_CO2+RQ+rab; 0.479, 0.733, tmp+pH+PL+OD+RS+Sugar_consuming_rate_cumulo+emission_O2+RQ; 0.479, 0.733, tmp+pH+PL+AN+OD+Arg_conc._cumulo+cell_yield_cumulo+rab_integral; 0.462, 0.733, tmp+pH+PL+OD+RS+Sugar_consuming_rate_cumulo+cell_yield_cumulo+emission_CO2+RQ+rab; 0.471, 0.733, tmp+pH+PL+OD+RS+Sugar_consuming_rate_cumulo+emission_O2+emission_CO2+rab; 0.471, 0.733, tmp+pH+PL+RS+Sugar_consuming_rate_cumulo+Arg_conc._cumulo+cell_yield_cumulo+rab_integral+emission_CO2; 0.487, 0.733, tmp+pH+PL+AN+rab_integral+emission_O2+RQ; 0.487, 0.733, tmp+pH+PL+RS+Sugar_consuming_rate_cumulo+Arg_conc._cumulo+rab; 0.471, 0.733, tmp+pH+PL+OD+RS+rab_integral+emission_CO2+RQ+rab; 0.435, 0.733, tmp+pH+PL+OD+RS+Arg_conc._cumulo+cell_yield_cumulo+rab_integral+RQ_integral+emission_O2+emission_CO2+RQ+rab; 0.487, 0.733, tmp+pH+PL+AN+RS+Sugar_consuming_rate_cumulo+Arg_conc._cumulo; 0.462, 0.733, tmp+pH+PL+RS+Sugar_consuming_rate_cumulo+Arg_conc._cumulo+emission_O2+emission_CO2+RQ+rab; 0.479, 0.733, tmp+pH+PL+OD+RS+rab_integral+RQ+rab; 0.495, 0.733, tmp+pH+Arg_conc._cumulo+emission_O2+emission_CO2+RQ; 0.462, 0.733, tmp+pH+PL+OD+RS+Arg_conc._cumulo+rab_integral+RQ_integral+emission_O2+RQ; 0.479, 0.733, tmp+pH+PL+Arg_conc._cumulo+cell_yield_cumulo+emission_O2+emission_CO2+RQ; 0.444, 0.733, tmp+pH+PL+AN+OD+RS+Arg_conc._cumulo+rab_integral+RQ_integral+emission_CO2+RQ+rab; 0.470, 0.733, tmp+pH+PL+OD+RS+Sugar_consuming_rate_cumulo+rab_integral+emission_CO2+RQ; 0.479, 0.733, tmp+pH+PL+AN+rab_integral+emission_O2+emission_CO2+rab; 0.502, 0.732, tmp+pH+PL+OD+RQ; 0.487, 0.732, tmp+pH+PL+RS+Sugar_consuming_rate_cumulo+cell_yield_cumulo+rab; 0.462, 0.732, tmp+pH+PL+AN+OD+Arg_conc._cumulo+rab_integral+emission_CO2+RQ+rab; 0.478, 0.732, tmp+pH+PL+AN+cell_yield_cumulo+rab_integral+emission_O2+rab; 0.470, 0.732, tmp+pH+PL+AN+RS+Arg_conc._cumulo+rab_integral+emission_CO2+RQ; 0.462, 0.732, tmp+pH+PL+AN+RS+Sugar_consuming_rate_cumulo+Arg_conc._cumulo+emission_O2+emission_CO2+RQ; 0.486, 0.732, tmp+pH+PL+RS+Sugar_consuming_rate_cumulo+cell_yield_cumulo+emission_CO2; 0.494, 0.732, tmp+pH+PL+Arg_conc._cumulo+emission_O2+rab; 0.478, 0.732, tmp+pH+PL+AN+Sugar_consuming_rate_cumulo+Arg_conc._cumulo+cell_yield_cumulo+RQ; 0.494, 0.732, tmp+pH+PL+AN+RS+Arg_conc._cumulo; 0.453, 0.732, tmp+pH+PL+AN+OD+RS+cell_yield_cumulo+rab_integral+emission_O2+RQ+rab; 0.461, 0.732, tmp+pH+PL+Sugar_consuming_rate_cumulo+cell_yield_cumulo+rab_integral+emission_O2+emission_CO2+RQ+rab; 0.461, 0.732, tmp+pH+PL+AN+RS+Arg_conc._cumulo+cell_yield_cumulo+rab_integral+emission_O2+emission_CO2; 0.478, 0.732, tmp+pH+PL+RS+cell_yield_cumulo+rab_integral+emission_O2+rab; 0.486, 0.732, tmp+pH+PL+Sugar_consuming_rate_cumulo+Arg_conc._cumulo+emission_O2+RQ; 0.452, 0.732, tmp+pH+PL+OD+RS+Arg_ conc._cumulo+cell_yield_cumulo+RQ_integral+emission_O2+emission_CO2+RQ; 0.494, 0.732, tmp+pH+PL+Sugar_consuming_rate_cumulo+Arg_conc._cumulo+rab_integral; 0.486, 0.732, tmp+pH+PL+OD+rab_integral+RQ_integral+emission_O2; 0.470, 0.732, tmp+pH+PL+AN+OD+Arg_conc._cumulo+cell_yield_cumulo+rab_integral+RQ; 0.470, 0.732, tmp+pH+PL+RS+Sugar_consuming_rate_cumulo+Arg_conc._cumulo+cell_yield_cumulo+emission_O2+emission_CO2; 0.486, 0.732, tmp+pH+PL+AN+Arg_conc._cumulo+emission_O2+RQ; 0.470, 0.732, tmp+pH+PL+AN+Sugar_consuming_rate_cumulo+Arg_conc._cumulo+rab_integral+emission_CO2+RQ; 0.494, 0.732, tmp+pH+PL+Sugar_consuming_rate_cumulo+rab_integral+emission_O2; 0.486, 0.732, tmp+pH+PL+AN+Arg_conc._cumulo+emission_CO2+rab; 0.469, 0.732, tmp+pH+PL+AN+RS+Arg_conc._cumulo+emission_O2+emission_CO2+rab; 0.461, 0.732, tmp+pH+PL+Arg_conc._cumulo+rab_integral+RQ_integral+emission_O2+emission_CO2+RQ+rab; 0.469, 0.732, tmp+pH+PL+AN+RS+Sugar_consuming_rate_cumulo+cell_yield_cumulo+rab_integral+emission_O2; 0.461, 0.732, tmp+pH+PL+AN+OD+Sugar_consuming_rate_cumulo+rab_integral+emission_O2+emission_CO2+rab; 0.452, 0.732, tmp+pH+PL+AN+RS+Sugar_consuming_rate_cumulo+Arg_conc._cumulo+cell_yield_cumulo+emission_CO2+RQ+rab; 0.493, 0.732, tmp+pH+PL+RS+rab_integral+emission_O2; 0.478, 0.732, tmp+pH+PL+RS+cell_yield_cumulo+rab_integral+emission_O2+emission_CO2; 0.486, 0.732, tmp+pH+PL+Sugar_consuming_rate_cumulo+Arg_conc._cumulo+cell_yield_cumulo+emission_O2; 0.469, 0.732, tmp+pH+PL+AN+OD+Sugar_consuming_rate_cumulo+Arg_conc._cumulo+rab_integral+rab; 0.443, 0.732, tmp+pH+PL+AN+RS+Sugar_consuming_rate_cumulo+Arg_conc._cumulo+rab_integral+emission_O2+emission_CO2+RQ+rab; 0.501, 0.732, tmp+pH+PL+Arg_conc._cumulo+rab; 0.469, 0.732, tmp+pH+PL+AN+Sugar_consuming_rate_cumulo+cell_yield_cumulo+rab_integral+emission_O2+emission_CO2; 0.469, 0.732, tmp+pH+PL+Sugar_consuming_rate_cumulo+Arg_conc._cumulo+cell_yield_cumulo+rab_integral+emission_CO2+RQ; 0.477, 0.732, tmp+pH+PL+RS+Sugar_consuming_rate_cumulo+Arg_conc._cumulo+cell_yield_cumulo+rab; 0.485, 0.732, tmp+pH+PL+OD+RS+cell_yield_cumulo+rab_integral; 0.452, 0.732, tmp+pH+PL+AN+OD+RS+Sugar_consuming_rate_cumulo+Arg_conc._cumulo+emission_O2+RQ+rab; 0.493, 0.732, tmp+pH+PL+OD+emission_O2+rab; 0.477, 0.732, tmp+pH+PL+OD+RS+Arg_conc._cumulo+RQ_integral+emission_CO2; 0.460, 0.732, tmp+pH+PL+RS+Sugar_consuming_rate_cumulo+cell_yield_cumulo+rab_integral+emission_O2+RQ+rab; 0.469, 0.732, tmp+pH+PL+OD+RS+Arg_conc._cumulo+cell_yield_cumulo+RQ_integral+emission_CO2; 0.469, 0.732, tmp+pH+PL+AN+OD+RS+Sugar_consuming_rate_cumulo+rab_integral+rab; 0.485, 0.732, tmp+pH+PL+OD+RS+cell_yield_cumulo+emission_O2; 0.469, 0.732, tmp+pH+PL+AN+RS+Arg_conc._cumulo+cell_yield_cumulo+rab_integral+emission_O2; 0.460, 0.732, tmp+pH+PL+AN+OD+RS+Arg_conc._cumulo+rab_integral+RQ_integral+emission_CO2; 0.460, 0.732, tmp+pH+PL+AN+OD+Arg_conc._cumulo+RQ_integral+emission_CO2+RQ+rab; 0.493, 0.732, tmp+pH+PL+OD+Sugar_consuming_rate_cumulo+RQ; 0.460, 0.732, tmp+pH+PL+RS+Sugar_consuming_rate_cumulo+Arg_conc._cumulo+rab_integral+emission_CO2+RQ+rab; 0.451, 0.732, tmp+pH+PL+AN+OD+Sugar_consuming_rate_cumulo+Arg_conc._cumulo+rab_integral+emission_CO2+RQ+rab; 0.451, 0.732, tmp+pH+PL+AN+OD+RS+Sugar_consuming_rate_cumulo+cell_yield_cumulo+emission_CO2+RQ+rab; 0.493, 0.732, tmp+pH+PL+AN+Arg_conc._cumulo+RQ; 0.460, 0.732, tmp+pH+PL+OD+RS+Sugar_consuming_rate_cumulo+rab_integral+emission_CO2+RQ+rab; 0.451, 0.732, tmp+pH+PL+AN+OD+RS+Sugar_consuming_rate_cumulo+rab_integral+emission_O2+emission_CO2+rab; 0.477, 0.732, tmp+pH+PL+AN+cell_yield_cumulo+rab_integral+emission_O2+emission_CO2; 0.442, 0.731, tmp+pH+PL+AN+OD+RS+Arg_conc._cumulo+RQ_integral+emission_O2+emission_CO2+RQ+rab; 0.460, 0.731, tmp+pH+PL+AN+OD+Sugar_consuming_rate_cumulo+rab_integral+emission_O2+emission_CO2+RQ; 0.477, 0.731, tmp+pH+PL+AN+OD+RS+Arg_conc._cumulo+RQ_integral; 0.469, 0.731, tmp+pH+PL+OD+RS+Arg_conc._cumulo+rab_integral+RQ_integral+emission_O2; 0.493, 0.731, tmp+pH+PL+OD+Sugar_consuming_rate_cumulo+rab; 0.477, 0.731, tmp+pH+PL+RS+Sugar_consuming_rate_cumulo+cell_yield_cumulo+emission_CO2+rab; 0.451, 0.731, tmp+pH+PL+OD+RS+Arg_conc._cumulo+cell_yield_cumulo+rab_integral+RQ_integral+emission_O2+emission_CO2; 0.493, 0.731, tmp+pH+PL+RS+Arg_conc._cumulo+RQ; 0.469, 0.731, tmp+pH+PL+Arg_conc._cumulo+rab_integral+RQ_integral+emission_O2+emission_CO2+rab; 0.477, 0.731, tmp+pH+PL+Sugar_consuming_rate_cumulo+Arg_conc._cumulo+rab_integral+emission_CO2+rab; 0.477, 0.731, tmp+pH+PL+RS+cell_yield_cumulo+rab_integral+emission_O2+RQ; 0.451, 0.731, tmp+pH+PL+AN+OD+RS+cell_yield_cumulo+rab_integral+emission_O2+emission_CO2+rab; 0.460, 0.731, tmp+pH+PL+RS+Sugar_consuming_rate_cumulo+cell_yield_cumulo+rab_integral+emission_O2+emission_CO2+rab; 0.468, 0.731, tmp+pH+PL+AN+Arg_conc._cumulo+rab_integral+RQ_integral+emission_O2+emission_CO2; 0.493, 0.731, tmp+pH+PL+AN+OD+emission_O2; 0.485, 0.731, tmp+pH+PL+Arg_conc._cumulo+cell_yield_cumulo+emission_O2+emission_CO2; 0.477, 0.731, tmp+pH+PL+RS+rab_integral+emission_O2+RQ+rab; 0.477, 0.731, tmp+pH+PL+AN+OD+RS+Sugar_consuming_rate_cumulo+emission_O2; 0.451, 0.731, tmp+pH+PL+AN+RS+Sugar_consuming_rate_cumulo+Arg_conc._cumulo+cell_yield_cumulo+rab_integral+emission_O2+RQ; 0.460, 0.731, tmp+pH+PL+AN+Sugar_consuming_rate_cumulo+cell_yield_cumulo+rab_integral+emission_O2+RQ+rab; 0.468, 0.731, tmp+pH+PL+AN+OD+Sugar_consuming_rate_cumulo+Arg_conc._cumulo+emission_O2+rab; 0.476, 0.731, tmp+pH+PL+OD+RS+cell_yield_cumulo+rab_integral+rab; 0.492, 0.731, tmp+pH+PL+OD+emission_O2+emission_CO2; 0.459, 0.731, tmp+pH+PL+AN+RS+Sugar_consuming_rate_cumulo+Arg_conc._cumulo+rab_integral+emission_CO2+RQ; 0.459, 0.731, tmp+pH+PL+OD+RS+Sugar_consuming_rate_cumulo+Arg_conc._cumulo+RQ_integral+emission_CO2+RQ; 0.476, 0.731, tmp+pH+PL+AN+OD+Arg_conc._cumulo+RQ_integral+emission_CO2; 0.459, 0.731, tmp+pH+PL+AN+OD+Arg_conc._cumulo+cell_yield_cumulo+emission_O2+emission_CO2+rab; 0.432, 0.731, tmp+pH+PL+AN+OD+RS+Arg_conc._cumulo+cell_yield_cumulo+rab_integral+RQ_integral+emission_CO2+RQ+rab; 0.468, 0.731, tmp+pH+PL+Sugar_consuming_rate_cumulo+Arg_conc._cumulo+rab_integral+emission_CO2+RQ+rab; 0.468, 0.731, tmp+pH+PL+AN+OD+RS+Sugar_consuming_rate_cumulo+rab_integral+emission_CO2; 0.484, 0.731, tmp+pH+PL+AN+Sugar_consuming_rate_cumulo+Arg_conc._cumulo+rab

[202. Linear Model that Predicts Arginine Production Amount in Interval 2]

0.791, 0.914, tmp+PL+PL_cumulo+interval_Pdt.+OD+nu_cumulo+rho_cumulo+nu_per_rho_cumulo+Arg_conc._cumulo+Accum._Yield+emission_O2+emission_CO2+consum_O2+generate_CO2; 0.801, 0.913, tmp+PL+AN+interval_Pdt.+mu_cumulo+nu_cumulo+rho_cumulo+nu_per_rho_cumulo+emission_CO2+consum_O2+generate_CO2; 0.801, 0.913, tmp+PL+interval_Pdt.+mu_cumulo+nu_cumulo+rho_cumulo+nu_per_rho_cumulo+rab_integral+emission_CO2+consum_O2+generate_CO2; 0.797, 0.913, tmp+PL+AN+interval_Pdt.+mu_cumulo+nu_cumulo+rho_cumulo+nu_per_rho_cumulo+Accum._Yield+emission_CO2+consum_O2+generate_CO2; 0.784, 0.913, tmp+PL+PL_cumulo+AN+interval_Pdt.+OD+nu_cumulo+rho_cumulo+nu_per_rho_cumulo+Arg_conc._cumulo+Accum._Yield+emission_O2+emission_CO2+consum_O2+generate_CO2; 0.792, 0.913, tmp+PL+interval_Pdt.+mu_cumulo+nu_cumulo+rho_cumulo+nu_per_rho_cumulo+rab_integral+RQ_integral+Accum._Yield+emission_CO2+consum_O2+generate_CO2; 0.787, 0.913, tmp+PL+PL_cumulo+AN+interval_Pdt.+mu_cumulo+nu_cumulo+rho_cumulo+nu_per_rho_cumulo+rab_integral+Accum._Yield+emission_CO2+consum_O2+generate_CO2; 0.795, 0.913, tmp+PL+interval_Pdt.+mu_cumulo+nu_cumulo+rho_cumulo+nu_per_rho_cumulo+cell_yield_cumulo+rab_integral+emission_CO2+consum_O2+generate_CO2; 0.783, 0.913, tmp+PL+PL_cumulo+interval_Pdt.+OD+nu_cumulo+rho_cumulo+nu_per_rho_cumulo+Arg_conc._cumulo+RQ_integral+Accum._Yield+emission_O2+emission_CO2+consum_O2+generate_CO2; 0.795, 0.913, tmp+PL+interval_Pdt.+mu_cumulo+nu_cumulo+rho_cumulo+nu_per_rho_cumulo+rab_integral+RQ_integral+emission_CO2+consum_O2+generate_CO2; 0.782, 0.912, tmp+PL+PL_cumulo+AN+interval_Pdt.+OD+nu_cumulo+rho_cumulo+nu_per_rho_cumulo+Arg_conc._cumulo+rab_integral+Accum._Yield+emission_CO2+consum_O2+generate_CO2; 0.791, 0.912, tmp+PL+PL_cumulo+AN+interval_Pdt.+mu_cumulo+nu_cumulo+rho_cumulo+nu_per_rho_cumulo+rab_integral+emission_CO2+consum_O2+generate_CO2; 0.790, 0.912, tmp+PL+interval_Pdt.+OD+nu_cumulo+rho_cumulo+nu_per_rho_cumulo+Arg_conc._cumulo+rab_integral+Accum._Yield+emission_CO2+consum_O2+generate_CO2; 0.794, 0.912, tmp+PL+interval_Pdt.+mu_cumulo+nu_cumulo+rho_cumulo+nu_per_rho_cumulo+rab_integral+Accum._Yield+emission_CO2+consum_O2+generate_CO2; 0.794, 0.912, tmp+PL+AN+interval_Pdt.+mu_cumulo+nu_cumulo+rho_cumulo+nu_per_rho_cumulo+emission_CO2+consum_O2+interval_O2+generate_CO2; 0.794, 0.912, tmp+PL+PL_cumulo+interval_Pdt.+mu_cumulo+nu_cumulo+rho_cumulo+nu_per_rho_cumulo+rab_integral+emission_CO2+consum_O2+generate_CO2; 0.782, 0.912, tmp+PL+PL_cumulo+AN+interval_Pdt.+mu_cumulo+nu_cumulo+rho_cumulo+nu_per_rho_cumulo+Accum._Yield+emission_O2+emission_CO2+consum_O2+interval_O2+generate_CO2; 0.781, 0.912, tmp+PL+PL_cumulo+interval_Pdt.+OD+nu_cumulo+rho_cumulo+nu_per_rho_cumulo+Arg_conc._cumulo+Accum._Yield+emission_O2+emission_CO2+consum_O2+interval_O2+generate_CO2; 0.789, 0.912, tmp+PL+AN+interval_Pdt.+mu_cumulo+nu_cumulo+rho_cumulo+nu_per_rho_cumulo+rab_integral+emission_CO2+consum_O2+interval_O2+generate_CO2; 0.785, 0.912, tmp+PL+PL_cumulo+interval_Pdt.+OD+nu_cumulo+rho_cumulo+nu_per_rho_cumulo+Arg_conc._cumulo+rab_integral+Accum._Yield+emission_CO2+consum_O2+generate_CO2; 0.785, 0.912, tmp+PL+PL_cumulo+AN+interval_Pdt.+mu_cumulo+nu_cumulo+rho_cumulo+nu_per_rho_cumulo+rab_integral+emission_CO2+consum_O2+interval_O2+generate_CO2; 0.785, 0.912, tmp+PL+PL_cumulo+AN+interval_Pdt.+mu_cumulo+nu_cumulo+rho_cumulo+nu_per_rho_cumulo+emission_O2+emission_CO2+consum_O2+interval_O2+generate_CO2; 0.793, 0.912, tmp+PL+AN+interval_Pdt.+mu_cumulo+nu_cumulo+rho_cumulo+nu_per_rho_cumulo+rab_integral+emission_CO2+consum_O2+generate_CO2; 0.789, 0.912, tmp+PL+interval_Pdt.+mu_cumulo+nu_cumulo+rho_cumulo+nu_per_rho_cumulo+cell_yield_cumulo+rab_integral+Accum._Yield+emission_CO2+consum_O2+generate_CO2; 0.789, 0.912, tmp+PL+AN+interval_Pdt.+mu_cumulo+nu_cumulo+rho_cumulo+nu_per_rho_cumulo+rab_integral+Accum._Yield+emission_CO2+consum_O2+generate_CO2; 0.780, 0.912, tmp+PL+PL_cumulo+AN+interval_Pdt.+mu_cumulo+nu_cumulo+rho_cumulo+nu_per_rho_cumulo+rab_integral+Accum._Yield+emission_CO2+consum_O2+interval_O2+generate_CO2; 0.780, 0.912, tmp+PL+PL_cumulo+interval_Pdt.+OD+nu_cumulo+rho_cumulo+nu_per_rho_cumulo+Arg_conc._cumulo+rab_integral+Accum._Yield+emission_O2+emission_CO2+consum_O2+generate_CO2; 0.789, 0.912, tmp+PL+AN+interval_Pdt.+mu_cumulo+nu_cumulo+rho_cumulo+nu_per_rho_cumulo+Accum._Yield+emission_CO2+consum_O2+interval_O2+generate_CO2; 0.793, 0.912, tmp+PL+interval_Pdt.+RS+mu_cumulo+nu_cumulo+rho_cumulo+nu_per_rho_cumulo+rab_integral+emission_CO2+consum_O2+generate_CO2; 0.789, 0.912, tmp+PL+interval_Pdt.+mu_cumulo+nu_cumulo+rho_cumulo+nu_per_rho_cumulo+RQ_integral+Accum._Yield+emission_O2+emission_CO2+consum_O2+generate_CO2; 0.789, 0.912, tmp+PL+AN+interval_Pdt.+mu_cumulo+nu_cumulo+rho_cumulo+nu_per_rho_cumulo+cell_yield_cumulo+rab_integral+emission_CO2+consum_O2+generate_CO2; 0.784, 0.911, tmp+PL+PL_cumulo+interval_Pdt.+mu_cumulo+nu_cumulo+rho_cumulo+nu_per_rho_cumulo+RQ_integral+Accum._Yield+emission_O2+emission_CO2+consum_O2+generate_CO2; 0.780, 0.911, tmp+PL+PL_cumulo+AN+interval_Pdt.+mu_cumulo+nu_cumulo+rho_cumulo+nu_per_rho_cumulo+Arg_conc._cumulo+rab_integral+Accum._Yield+emission_CO2+consum_O2+generate_CO2; 0.792, 0.911, tmp+PL+interval_Pdt.+OD+mu_cumulo+nu_cumulo+rho_cumulo+nu_per_rho_cumulo+rab_integral+emission_CO2+consum_O2+generate_CO2; 0.784, 0.911, tmp+PL+interval_Pdt.+mu_cumulo+nu_cumulo+rho_cumulo+nu_per_rho_cumulo+cell_yield_cumulo+RQ_integral+Accum._Yield+emission_O2+emission_CO2+consum_O2+generate_CO2; 0.788, 0.911, tmp+PL+PL_cumulo+interval_Pdt.+mu_cumulo+nu_cumulo+rho_cumulo+nu_per_rho_cumulo+rab_integral+Accum._Yield+emission_CO2+consum_O2+generate_CO2; 0.788, 0.911, tmp+PL+interval_Pdt.+OD+nu_cumulo+rho_cumulo+nu_per_rho_cumulo+Arg_conc._cumulo+Accum._Yield+emission_O2+emission_CO2+consum_O2+generate_CO2; 0.775, 0.911, tmp+PL+PL_cumulo+AN+interval_Pdt.+OD+nu_cumulo+rho_cumulo+nu_per_rho_cumulo+Arg_conc._cumulo+Accum._Yield+emission_O2+emission_CO2+consum_O2+interval_O2+generate_CO2; 0.784, 0.911, tmp+PL+AN+interval_Pdt.+mu_cumulo+nu_cumulo+rho_cumulo+nu_per_rho_cumulo+cell_yield_cumulo+rab_integral+Accum._Yield+emission_CO2+consum_O2+generate_CO2; 0.784, 0.911, tmp+PL+interval_Pdt.+mu_cumulo+nu_cumulo+rho_cumulo+nu_per_rho_cumulo+cell_yield_cumulo+rab_integral+RQ_integral+Accum._Yield+emission_CO2+consum_O2+generate_CO2; 0.784, 0.911, tmp+PL+PL_cumulo+AN+interval_Pdt.+mu_cumulo+nu_cumulo+rho_cumulo+nu_per_rho_cumulo+Accum._Yield+emission_O2+emission_CO2+consum_O2+generate_CO2; 0.795, 0.911, tmp+PL+interval_Pdt.+mu_cumulo+nu_cumulo+ rho_cumulo+nu_per_rho_cumulo+emission_O2+emission_CO2+consum_O2+generate_CO2; 0.783, 0.911, tmp+PL+AN+interval_Pdt.+mu_cumulo+nu_cumulo+rho_cumulo+nu_per_rho_cumulo+rab_integral+Accum._Yield+emission_CO2+consum_O2+interval_O2+generate_CO2; 0.788, 0.911, tmp+PL+PL_cumulo+OD+nu_cumulo+rho_cumulo+nu_per_rho_cumulo+Arg_conc._cumulo+Accum._Yield+emission_O2+emission_CO2+consum_O2+generate_CO2; 0.799, 0.911, tmp+PL+interval_Pdt.+mu_cumulo+nu_cumulo+rho_cumulo+nu_per_rho_cumulo+emission_CO2+consum_O2+generate_CO2; 0.787, 0.911, tmp+PL+AN+interval_Pdt.+mu_cumulo+nu_cumulo+rho_cumulo+nu_per_rho_cumulo+Arg_conc._cumulo+Accum._Yield+emission_CO2+consum_O2+generate_CO2; 0.783, 0.911, tmp+PL+AN+interval_Pdt.+mu_cumulo+nu_cumulo+nu_per_rho_cumulo+rab_integral+RQ_integral+Accum._Yield+emission_CO2+consum_O2+generate_CO2; 0.779, 0.911, tmp+PL+PL_cumulo+interval_Pdt.+OD+RS+nu_cumulo+rho_cumulo+nu_per_rho_cumulo+Arg_conc._cumulo+Accum._Yield+emission_O2+emission_CO2+consum_O2+generate_CO2; 0.791, 0.911, tmp+PL+PL_cumulo+interval_Pdt.+mu_cumulo+nu_cumulo+rho_cumulo+nu_per_rho_cumulo+emission_O2+emission_CO2+consum_O2+generate_CO2; 0.783, 0.911, tmp+PL+AN+interval_Pdt.+OD+nu_cumulo+rho_cumulo+nu_per_rho_cumulo+Arg_conc._cumulo+rab_integral+Accum._Yield+emission_CO2+consum_O2+generate_CO2; 0.787, 0.911, tmp+PL+interval_Pdt.+mu_cumulo+nu_cumulo+rho_cumulo+nu_per_rho_cumulo+cell_yield_cumulo+rab_integral+RQ_integral+emission_CO2+consum_O2+generate_CO2; 0.791, 0.911, tmp+PL+interval_Pdt.+mu_cumulo+nu_cumulo+rho_cumulo+nu_per_rho_cumulo+rab_integral+emission_CO2+consum_O2+interval_O2+generate_CO2; 0.791, 0.911, tmp+PL+AN+interval_Pdt.+mu_cumulo+nu_cumulo+rho_cumulo+nu_per_rho_cumulo+Arg_conc._cumulo+emission_CO2+consum_O2+generate_CO2; 0.787, 0.911, tmp+PL+PL_cumulo+interval_Pdt.+mu_cumulo+nu_cumulo+rho_cumulo+nu_per_rho_cumulo+Accum._Yield+emission_O2+emission_CO2+consum_O2+generate_CO2; 0.791, 0.911, tmp+PL+AN+interval_Pdt.+mu_cumulo+nu_cumulo+rho_cumulo+nu_per_rho_cumulo+cell_yield_cumulo+emission_CO2+consum_O2+generate_CO2; 0.791, 0.911, tmp+PL+interval_Pdt.+mu_cumulo+nu_cumulo+rho_cumulo+nu_per_rho_cumulo+cell_yield_cumulo+emission_O2+emission_CO2+consum_O2+generate_CO2; 0.787, 0.911, tmp+PL+AN+interval_Pdt.+mu_cumulo+nu_cumulo+rho_cumulo+nu_per_rho_cumulo+cell_yield_cumulo+Accum._Yield+emission_CO2+consum_O2+generate_CO2; 0.798, 0.911, tmp+PL+AN+interval_Pdt.+mu_cumulo+rho_cumulo+Accum._Yield+emission_CO2+consum_O2+generate_CO2; 0.774, 0.911, tmp+PL+PL_cumulo+AN+interval_Pdt.+OD+nu_cumulo+rho_cumulo+nu_per_rho_cumulo+Arg_conc._cumulo+rab_integral+Accum._Yield+emission_O2+emission_CO2+consum_O2+generate_CO2; 0.791, 0.911, tmp+PL+interval_Pdt.+mu_cumulo+nu_cumulo+rho_cumulo+nu_per_rho_cumulo+Arg_conc._cumulo+rab_integral+emission_CO2+consum_O2+generate_CO2; 0.773, 0.911, tmp+PL+PL_cumulo+interval_Pdt.+OD+nu_cumulo+rho_cumulo+nu_per_rho_cumulo+Arg_conc._cumulo+RQ_integral+Accum._Yield+emission_O2+emission_CO2+consum_O2+interval_O2+generate_CO2; 0.782, 0.911, tmp+PL+interval_Pdt.+OD+nu_cumulo+rho_cumulo+nu_per_rho_cumulo+Arg_conc._cumulo+rab_integral+RQ_integral+Accum._Yield+emission_CO2+consum_O2+generate_CO2; 0.790, 0.911, tmp+PL+AN+interval_Pdt.+RS+mu_cumulo+nu_cumulo+rho_cumulo+nu_per_rho_cumulo+emission_CO2+consum_O2+generate_CO2; 0.782, 0.910, tmp+PL+interval_Pdt.+RS+mu_cumulo+nu_cumulo+rho_cumulo+nu_per_rho_cumulo+rab_integral+RQ_integral+Accum._Yield+emission_CO2+consum_O2+generate_CO2; 0.786, 0.910, tmp+PL+AN+interval_Pdt.+mu_cumulo+nu_cumulo+rho_cumulo+nu_per_rho_cumulo+emission_O2+emission_CO2+consum_O2+interval_O2+generate_CO2; 0.782, 0.910, tmp+PL+interval_Pdt.+OD+nu_cumulo+rho_cumulo+nu_per_rho_cumulo+Arg_conc._cumulo+RQ_integral+Accum._Yield+emission_O2+emission_CO2+consum_O2+generate_CO2; 0.798, 0.910, tmp+PL_cumulo+interval_Pdt.+mu_cumulo+nu_cumulo+rho_cumulo+nu_per_rho_cumulo+emission_CO2+consum_O2+generate_CO2; 0.786, 0.910, tmp+PL+interval_Pdt.+RS+mu_cumulo+nu_cumulo+rho_cumulo+nu_per_rho_cumulo+rab_integral+RQ_integral+emission_CO2+consum_O2+generate_CO2; 0.786, 0.910, tmp+PL+AN+interval_Pdt.+RS+mu_cumulo+nu_cumulo+rho_cumulo+nu_per_rho_cumulo+Accum._Yield+emission_CO2+consum_O2+generate_CO2; 0.786, 0.910, tmp+PL+interval_Pdt.+RS+mu_cumulo+nu_cumulo+rho_cumulo+nu_per_rho_cumulo+rab_integral+Accum._Yield+emission_CO2+consum_O2+generate_CO2; 0.782, 0.910, tmp+PL+AN+interval_Pdt.+mu_cumulo+nu_cumulo+rho_cumulo+nu_per_rho_cumulo+cell_yield_cumulo+rab_integral+emission_CO2+consum_O2+interval_O2+generate_CO2; 0.790, 0.910, tmp+PL+AN+interval_Pdt.+OD+mu_cumulo+nu_cumulo+rho_cumulo+nu_per_rho_cumulo+emission_CO2+consum_O2+generate_CO2; 0.786, 0.910, tmp+PL+interval_Pdt.+RS+mu_cumulo+nu_cumulo+rho_cumulo+nu_per_rho_cumulo+cell_yield_cumulo+rab_integral+emission_CO2+consum_O2+generate_CO2; 0.794, 0.910, tmp+PL+AN+interval_Pdt.+mu_cumulo+rho_cumulo+Accum._Yield+emission_CO2+consum_O2+interval_O2+generate_CO2; 0.786, 0.910, tmp+PL+interval_Pdt.+mu_cumulo+nu_cumulo+rho_cumulo+nu_per_rho_cumulo+Arg_conc._cumulo+cell_yield_cumulo+rab_integral+emission_CO2+consum_O2+generate_CO2; 0.786, 0.910, tmp+PL+PL_cumulo+interval_Pdt.+mu_cumulo+nu_cumulo+rho_cumulo+nu_per_rho_cumulo+emission_O2+emission_CO2+consum_O2+interval_O2+generate_CO2; 0.773, 0.910, tmp+PL+PL_cumulo+interval_Pdt.+OD+nu_cumulo+rho_cumulo+nu_per_rho_cumulo+Arg_conc._cumulo+rab_integral+RQ_integral+Accum._Yield+emission_O2+emission_CO2+consum_O2+generate_CO2; 0.790, 0.910, tmp+PL+interval_Pdt.+mu_cumulo+nu_cumulo+rho_cumulo+nu_per_rho_cumulo+Accum._Yield+emission_O2+emission_CO2+consum_O2+generate_CO2; 0.786, 0.910, tmp+PL+AN+interval_Pdt.+OD+nu_cumulo+rho_cumulo+nu_per_rho_cumulo+Arg_conc._cumulo+Accum._Yield+emission_CO2+consum_O2+generate_CO2; 0.790, 0.910, tmp+PL+interval_Pdt.+OD+nu_cumulo+rho_cumulo+nu_per_rho_cumulo+Arg_conc._cumulo+rab_integral+emission_CO2+consum_O2+generate_CO2; 0.782, 0.910, tmp+PL+interval_Pdt.+OD+mu_cumulo+nu_cumulo+rho_cumulo+nu_per_rho_cumulo+Arg_conc._cumulo+rab_integral+Accum._Yield+emission_CO2+consum_O2+generate_CO2; 0.786, 0.910, tmp+PL+AN+interval_Pdt.+OD+mu_cumulo+nu_cumulo+rho_cumulo+nu_per_rho_cumulo+Accum._Yield+emission_CO2+consum_O2+generate_CO2; 0.786, 0.910, tmp+PL+AN+interval_Pdt.+RS+mu_cumulo+nu_cumulo+rho_cumulo+nu_per_rho_cumulo+rab_integral+emission_CO2+consum_O2+generate_CO2; 0.777, 0.910, tmp+PL+PL_cumulo+interval_Pdt.+mu_cumulo+nu_cumulo+rho_cumulo+nu_per_rho_cumulo+RQ_ integral+Accum._Yield+emission_O2+emission_CO2+ consum_O2+interval_O2+generate_CO2; 0.786, 0.910, tmp+PL+AN+interval_Pdt.+OD+mu_cumulo+nu_cumulo+ rho_cumulo+nu_per_rho_cumulo+rab_integral+emission_ CO2+consum_O2+generate_CO2; 0.790, 0.910, tmp+PL_ cumulo+interval_Pdt.+mu_cumulo+nu_cumulo+rho_ cumulo+nu_per_rho_cumulo+cell_yield_cumulo+rab_ integral+emission_CO2+consum_O2+generate_CO2; 0.790, 0.910, tmp+PL+OD+nu_cumulo+rho_cumulo+nu_ per_rho_cumulo+Arg_conc._cumulo+Accum._Yield+emission_O2+emission_CO2+consum_O2+generate_CO2; 0.781, 0.910, tmp+PL+interval_Pdt.+mu_cumulo+nu_cumulo+rho_cumulo+nu_per_rho_cumulo+Arg_conc._cumulo+rab_integral+RQ_integral+Accum._Yield+emission_ CO2+consum_O2+generate_CO2; 0.777, 0.910, tmp+pH+ PL+PL_cumulo+interval_Pdt.+OD+nu_cumulo+rho_ cumulo+nu_per_rho_cumulo+Arg_conc._cumulo+ Accum._Yield+emission_O2+emission_CO2+consum_ O2+generate_CO2; 0.785, 0.910, tmp+PL+interval_Pdt.+ OD+mu_cumulo+nu_cumulo+rho_cumulo+nu_per_rho_ cumulo+rab_integral+Accum._Yield+emission_CO2+ consum_O2+generate_CO2; 0.781, 0.910, tmp+PL+ interval_Pdt.+OD+RS+nu_cumulo+rho_cumulo+nu_per_ rho_cumulo+Arg_conc._cumulo+Arg_conc._cumulo+rab_ integral+Accum._Yield+emission_CO2+consum_O2+ generate_CO2; 0.789, 0.910, tmp+PL+OD+nu_cumulo+ rho_cumulo+nu_per_rho_cumulo+Arg_conc._cumulo+ rab_integral+Accum._Yield+emission_CO2+consum_O2+ generate_CO2; 0.785, 0.910, tmp+PL+PL_cumulo+AN+ interval_Pdt.+mu_cumulo+nu_cumulo+rho_cumulo+nu_ per_rho_cumulo+emission_O2+emission_CO2+consum_ O2+generate_CO2; 0.785, 0.910, tmp+PL+interval_Pdt.+ mu_cumulo+nu_cumulo+rho_cumulo+nu_per_rho_ cumulo+cell_yield_cumulo+Accum._Yield+emission_O2+ emission_CO2+consum_O2+generate_CO2; 0.785, 0.910, tmp+PL+interval_Pdt.+OD+mu_cumulo+nu_cumulo+rho_ cumulo+nu_per_rho_cumulo+cell_yield_cumulo+rab_integral+emission_CO2+consum_O2+generate_CO2; 0.781, 0.910, tmp+PL+PL_cumulo+AN+interval_yield+interval_ Pdt.+mu_cumulo+nu_cumulo+rho_cumulo+nu_per_rho_ cumulo+rab_integral+emission_CO2+consum_O2+generate_CO2; 0.781, 0.910, tmp+PL+interval_Pdt.+mu_ cumulo+nu_cumulo+rho_cumulo+nu_per_rho_cumulo+ Arg_conc._cumulo+cell_yield_cumulo+rab_integral+ Accum._Yield+emission_CO2+consum_O2+generate_ CO2; 0.781, 0.910, tmp+PL+AN+interval_Pdt.+RS+mu_ cumulo+nu_cumulo+rho_cumulo+nu_per_rho_cumulo+ rab_integral+Accum._Yield+emission_CO2+consum_O2+ generate_CO2; 0.772, 0.910, tmp+PL+PL_cumulo+AN+ interval_Pdt.+mu_cumulo+nu_cumulo+rho_cumulo+nu_ per_rho_cumulo+rab_integral+Accum._Yield+emission_ O2+emission_CO2+consum_O2+interval_O2+generate_ CO2; 0.781, 0.910, tmp+PL+interval_Pdt.+OD+mu_ cumulo+nu_cumulo+rho_cumulo+nu_per_rho_cumulo+ rab_integral+RQ_integral+Accum._Yield+emission_CO2+ consum_O2+generate_CO2; 0.789, 0.910, tmp+pH+PL+ interval_Pdt.+mu_cumulo+nu_cumulo+rho_cumulo+nu_ per_rho_cumulo+rab_integral+emission_CO2+consum_ O2+generate_CO2; 0.772, 0.910, tmp+PL+PL_cumulo+ AN+interval_Pdt.+mu_cumulo+nu_cumulo+rho_cumulo+ nu_per_rho_cumulo+Arg_conc._cumulo+Accum._Yield+ emission_O2+emission_CO2+consum_O2+interval_O2+ generate_CO2; 0.781, 0.910, tmp+PL+interval_Pdt.+mu_ cumulo+nu_cumulo+rho_cumulo+nu_per_rho_cumulo+ rab_integral+RQ_integral+Accum._Yield+emission_O2+ emission_CO2+consum_O2+generate_CO2; 0.789, 0.910, tmp+PL+PL+OD+mu_cumulo+nu_cumulo+rho_ cumulo+nu_per_rho_cumulo+emission_O2+emission_ CO2+consum_O2+generate_CO2; 0.789, 0.910, tmp+PL+ PL_cumulo+AN+interval_Pdt.+mu_cumulo+nu_cumulo+ rho_cumulo+nu_per_rho_cumulo+emission_CO2+ consum_O2+generate_CO2; 0.780, 0.910, tmp+PL+ interval_Pdt.+OD+mu_cumulo+nu_cumulo+rho_cumulo+ nu_per_rho_cumulo+RQ_integral+Accum._Yield+ emission_O2+emission_CO2+consum_O2+generate_CO2; 0.780, 0.910, tmp+PL+interval_Pdt.+mu_cumulo+nu_cumulo+rho_cumulo+nu_per_rho_cumulo+rab_integral+RQ_ integral+Accum._Yield+emission_CO2+consum_O2+interval_O2+generate_CO2; 0.785, 0.910, tmp+PL+interval_ Pdt.+mu_cumulo+nu_cumulo+rho_cumulo+nu_per_rho_ cumulo+rab_integral+RQ_integral+emission_CO2+ consum_O2+interval_O2+generate_CO2; 0.776, 0.910, tmp+PL+PL_cumulo+interval_Pdt.+mu_cumulo+nu_cumulo+rho_cumulo+nu_per_rho_cumulo+rab_integral+RQ_ integral+Accum._Yield+emission_O2+emission_CO2+ consum_O2+generate_CO2; 0.780, 0.910, tmp+PL+ interval_Pdt.+mu_cumulo+nu_cumulo+rho_cumulo+nu_ per_rho_cumulo+RQ_integral+Accum._Yield+emission_ O2+emission_CO2+consum_O2+interval_O2+generate_ CO2; 0.785, 0.910, tmp+PL+PL_cumulo+interval_Pdt.+ mu_cumulo+nu_cumulo+rho_cumulo+nu_per_rho_ cumulo+rab_integral+RQ_integral+emission_CO2+ consum_O2+generate_CO2; 0.780, 0.910, tmp+PL+PL_ cumulo+interval_Pdt.+mu_cumulo+nu_cumulo+rho_ cumulo+nu_per_rho_cumulo+Accum._Yield+emission_ O2+emission_CO2+consum_O2+interval_O2+generate_ CO2; 0.771, 0.910, tmp+PL+PL_cumulo+AN+interval_ Pdt.+mu_cumulo+nu_cumulo+rho_cumulo+nu_per_rho_ cumulo+RQ_integral+Accum._Yield+emission_O2+ emission_CO2+consum_O2+interval_O2+generate_CO2; 0.789, 0.910, tmp+PL+interval_Pdt.+mu_cumulo+nu_cumulo+rho_cumulo+nu_per_rho_cumulo+emission_O2+ emission_CO2+consum_O2+interval_O2+generate_CO2; 0.780, 0.910, tmp+PL+AN+interval_Pdt.+mu_cumulo+nu_ cumulo+rho_cumulo+nu_per_rho_cumulo+Accum._Yield+ emission_O2+emission_CO2+consum_O2+interval_O2+ generate_CO2; 0.780, 0.910, tmp+PL+interval_Pdt.+OD+ nu_cumulo+rho_cumulo+nu_per_rho_cumulo+Arg_conc._ cumulo+rab_integral+Accum._Yield+emission_CO2+ consum_O2+interval_O2+generate_CO2; 0.789, 0.910, tmp+PL+AN+interval_Pdt.+OD+nu_cumulo+rho_cumulo+ nu_per_rho_cumulo+rab_integral+emission_CO2+consum_O2+generate_CO2; 0.771, 0.910, tmp+PL+PL_cumulo+AN+interval_Pdt.+OD+RS+nu_cumulo+rho_ cumulo+nu_per_rho_cumulo+Arg_conc._cumulo+ Accum._Yield+emission_O2+emission_CO2+consum_ O2+generate_CO2; 0.792, 0.910, tmp+PL+interval_Pdt.+ OD+nu_cumulo+rho_cumulo+nu_per_rho_cumulo+rab_ integral+emission_CO2+consum_O2+generate_CO2; 0.788, 0.910, tmp+PL+interval_Pdt.+mu_cumulo+nu_cumulo+rho_cumulo+nu_per_rho_cumulo+RQ_integral+ emission_O2+emission_CO2+consum_O2+generate_CO2; 0.776, 0.910, tmp+PL+PL_cumulo+interval_Pdt.+OD+mu_ cumulo+nu_cumulo+rho_cumulo+nu_per_rho_cumulo+ Arg_conc._cumulo+Accum._Yield+emission_O2+emission_CO2+consum_O2+generate_CO2; 0.776, 0.910, tmp+ PL+AN+interval_Pdt.+mu_cumulo+nu_cumulo+rho_ cumulo+nu_per_rho_cumulo+cell_yield_cumulo+rab_ integral+Accum._Yield+emission_CO2+consum_O2+ interval_O2+generate_CO2; 0.780, 0.910, tmp+PL+PL_ cumulo+interval_Pdt.+mu_cumulo+nu_cumulo+rho_ cumulo+nu_per_rho_cumulo+Arg_conc._cumulo+rab_ integral+Accum._Yield+emission_CO2+consum_O2+ generate_CO2; 0.780, 0.910, tmp+PL+AN+interval_Pdt.+

OD+mu_cumulo+nu_cumulo+rho_cumulo+nu_per_rho_ cumulo+rab_integral+Accum._Yield+emission_CO2+ consum_O2+generate_CO2; 0.784, 0.910, tmp+PL+ interval_Pdt.+mu_cumulo+nu_cumulo+rho_cumulo+nu_ per_rho_cumulo+cell_yield_cumulo+rab_integral+ emission_CO2+consum_O2+interval_O2+generate_CO2; 0.780, 0.910, tmp+PL+interval_Pdt.+RS+mu_cumulo+nu_ cumulo+rho_cumulo+nu_per_rho_cumulo+RQ_integral+ Accum._Yield+emission_O2+emission_CO2+consum_ O2+generate_CO2; 0.780, 0.910, tmp+PL+AN+interval_ Pdt.+OD+mu_cumulo+nu_cumulo+rho_cumulo+nu_per_ rho_cumulo+rab_integral+emission_CO2+consum_O2+ interval_O2+generate_CO2; 0.792, 0.910, tmp+PL_ cumulo+interval_Pdt.+mu_cumulo+nu_cumulo+rho_ cumulo+nu_per_rho_cumulo+rab_integral+emission_ CO2+consum_O2+generate_CO2; 0.780, 0.910, tmp+pH+ PL+interval_Pdt.+mu_cumulo+nu_cumulo+rho_cumulo+ nu_per_rho_cumulo+rab_integral+RQ_integral+Accum._ Yield+emission_CO2+consum_O2+generate_CO2; 0.771, 0.910, tmp+PL+PL_cumulo+AN+interval_Pdt.+OD+mu_ cumulo+nu_cumulo+rho_cumulo+nu_per_rho_cumulo+ Arg_conc._cumulo+rab_integral+Accum._Yield+emis- sion_CO2+consum_O2+generate_CO2; 0.780, 0.910, tmp+ PL+AN+interval_Pdt.+mu_cumulo+nu_cumulo+rho_ cumulo+nu_per_rho_cumulo+Arg_conc._cumulo+rab_ integral+emission_CO2+consum_O2+interval_O2+ generate_CO2; 0.771, 0.910, tmp+PL+PL_cumulo+AN+ interval_Pdt.+OD+RS+nu_cumulo+rho_cumulo+nu_per_ rho_cumulo+Arg_conc._cumulo+rab_integral+Accum._ Yield+emission_CO2+consum_O2+generate_CO2; 0.780, 0.910, tmp+PL+PL_cumulo+interval_Pdt.+mu_cumulo+ nu_cumulo+rho_cumulo+nu_per_rho_cumulo+rab_inte- gral+RQ_integral+Accum._Yield+emission_CO2+con- sum_O2+generate_CO2; 0.784, 0.910, tmp+PL+interval_ Pdt.+mu_cumulo+nu_cumulo+rho_cumulo+nu_per_rho_ cumulo+rab_integral+Accum._Yield+emission_CO2+ consum_O2+interval_O2+generate_CO2; 0.784, 0.910, tmp+PL+interval_Pdt.+OD+mu_cumulo+nu_cumulo+rho_ cumulo+nu_per_rho_cumulo+rab_integral+RQ_integral+ emission_CO2+consum_O2+generate_CO2; 0.784, 0.910, tmp+PL+PL_cumulo+AN+interval_Pdt.+mu_cumulo+nu_ cumulo+rho_cumulo+nu_per_rho_cumulo+Accum._Yield+ emission_CO2+consum_O2+generate_CO2; 0.784, 0.910, tmp+PL+AN+interval_Pdt.+mu_cumulo+nu_cumulo+rho_ cumulo+nu_per_rho_cumulo+Arg_conc._cumulo+rab_in- tegral+emission_CO2+consum_O2+generate_CO2; 0.775, 0.910, tmp+PL+PL_cumulo+AN+interval_Pdt.+mu_cu- mulo+nu_cumulo+rho_cumulo+nu_per_rho_cumulo+rab_ integral+RQ_integral+Accum._Yield+emission_CO2+con- sum_O2+generate_CO2; 0.792, 0.910, tmp+PL+interval_ Pdt.+mu_cumulo+nu_cumulo+rho_cumulo+nu_per_rho_ cumulo+Accum._Yield+emission_CO2+consum_O2+ generate_CO2; 0.784, 0.910, tmp+PL+AN+interval_Pdt.+ mu_cumulo+nu_cumulo+rho_cumulo+nu_per_rho_ cumulo+Arg_conc._cumulo+emission_CO2+consum_O2+ interval_O2+generate_CO2; 0.784, 0.910, tmp+PL+PL_ cumulo+interval_Pdt.+mu_cumulo+nu_cumulo+rho_ cumulo+nu_per_rho_cumulo+cell_yield_cumulo+rab_ integral+emission_CO2+consum_O2+generate_CO2; 0.775, 0.910, tmp+PL+PL_cumulo+AN+interval_Pdt.+mu_ cumulo+nu_cumulo+rho_cumulo+nu_per_rho_cumulo+ rab_integral+Accum._Yield+emission_O2+emission_ CO2+consum_O2+generate_CO2; 0.775, 0.910, tmp+PL+ AN+interval_Pdt.+mu_cumulo+nu_cumulo+rho_cumulo+ nu_per_rho_cumulo+cell_yield_cumulo+rab_integral+RQ_ integral+Accum._Yield+emission_CO2+consum_O2+ generate_CO2; 0.784, 0.910, tmp+PL+interval_Pdt.+mu_ cumulo+nu_cumulo+rho_cumulo+nu_per_rho_cumulo+ Arg_conc._cumulo+rab_integral+Accum._Yield+emis- sion_CO2+consum_O2+generate_CO2; 0.784, 0.910, tmp+ PL+OD+RS+nu_cumulo+rho_cumulo+nu_per_rho_ cumulo+Arg_conc._cumulo+rab_integral+Accum._Yield+ emission_CO2+consum_O2+generate_CO2; 0.780, 0.909, tmp+PL+AN+interval_Pdt.+OD+mu_cumulo+nu_cumulo+ rho_cumulo+nu_per_rho_cumulo+Arg_conc._cumulo+Ac- cum._Yield+emission_CO2+consum_O2+generate_CO2; 0.780, 0.909, tmp+PL+AN+interval_Pdt.+RS+mu_cumulo+ nu_cumulo+rho_cumulo+nu_per_rho_cumulo+cell_yield_ cumulo+rab_integral+emission_CO2+consum_O2+gener- ate_CO2; 0.775, 0.909, tmp+PL+PL_cumulo+AN+ interval_Pdt.+RS+mu_cumulo+nu_cumulo+rho_cumulo+ nu_per_rho_cumulo+rab_integral+Accum._Yield+ emission_CO2+consum_O2+generate_CO2; 0.784, 0.909, tmp+PL+AN+interval_Pdt.+mu_cumulo+nu_cumulo+rho_ cumulo+nu_per_rho_cumulo+Accum._Yield+emission_ O2+emission_CO2+consum_O2+generate_CO2; 0.771, 0.909, tmp+PL+PL_cumulo+interval_Pdt.+OD+RS+nu_cu- mulo+rho_cumulo+nu_per_rho_cumulo+Arg_conc._cu- mulo+RQ_integral+Accum._Yield+emission_O2+emis- sion_CO2+consum_O2+generate_CO2; 0.771, 0.909, tmp+ PL+PL_cumulo+AN+interval_Pdt.+mu_cumulo+nu_ cumulo+rho_cumulo+nu_per_rho_cumulo+Arg_conc._ cumulo+rab_integral+Accum._Yield+emission_CO2+ consum_O2+interval_O2+generate_CO2; 0.792, 0.909, tmp+PL+OD+nu_cumulo+rho_cumulo+nu_per_rho_cu- mulo+Arg_conc._cumulo+rab_integral+emission_CO2+ consum_O2+generate_CO2; 0.780, 0.909, tmp+PL+PL_cu- mulo+AN+interval_Pdt.+mu_cumulo+nu_cumulo+rho_ cumulo+nu_per_rho_cumulo+cell_yield_cumulo+rab_ integral+emission_CO2+consum_O2+generate_CO2; 0.771, 0.909, tmp+PL+PL_cumulo+AN+interval_Pdt.+RS+ mu_cumulo+nu_cumulo+rho_cumulo+nu_per_rho_cu- mulo+Arg_conc._cumulo+rab_integral+Accum._Yield+ emission_CO2+consum_O2+generate_CO2; 0.784, 0.909, tmp+pH+PL+interval_Pdt.+mu_cumulo+nu_cumulo+rho_ cumulo+nu_per_rho_cumulo+rab_integral+RQ_integral+ emission_CO2+consum_O2+generate_CO2; 0.775, 0.909, tmp+PL+PL_cumulo+AN+interval_Pdt.+mu_cumulo+nu_ cumulo+rho_cumulo+nu_per_rho_cumulo+rab_integral+ emission_O2+emission_CO2+consum_O2+interval_O2+ generate_CO2; 0.788, 0.909, tmp+PL+AN+interval_Pdt.+ mu_cumulo+nu_cumulo+rho_cumulo+nu_per_rho_ cumulo+emission_O2+emission_CO2+consum_O2+ generate_CO2; 0.780, 0.909, tmp+PL+PL_cumulo+OD+ RS+nu_cumulo+rho_cumulo+nu_per_rho_cumulo+Arg_ conc._cumulo+Accum._Yield+emission_O2+emission_ CO2+consum_O2+generate_CO2; 0.770, 0.909, tmp+PL+ PL_cumulo+AN+interval_Pdt.+OD+nu_cumulo+rho_ cumulo+nu_per_rho_cumulo+Arg_conc._cumulo+RQ_ integral+Accum._Yield+emission_O2+emission_CO2+ consum_O2+generate_CO2; 0.770, 0.909, tmp+PL+PL_ cumulo+AN+interval_Pdt.+OD+nu_cumulo+rho_cumulo+ nu_per_rho_cumulo+Arg_conc._cumulo+rab_integral+ Accum._Yield+emission_CO2+consum_O2+interval_O2+ generate_CO2; 0.779, 0.909, tmp+PL+AN+interval_Pdt.+ mu_cumulo+nu_cumulo+rho_cumulo+nu_per_rho_ cumulo+Arg_conc._cumulo+cell_yield_cumulo+rab_ integral+emission_CO2+consum_O2+generate_CO2; 0.792, 0.909, tmp+PL_cumulo+interval_Pdt.+mu_cumulo+ nu_cumulo+rho_cumulo+nu_per_rho_cumulo+cell_yield_ cumulo+emission_CO2+consum_O2+generate_CO2; 0.784, 0.909, tmp+PL_cumulo+interval_Pdt.+mu_cumulo+ nu_cumulo+rho_cumulo+nu_per_rho_cumulo+rab_inte- gral+RQ_integral+Accum._Yield+emission_CO2+consum_O2+generate_CO2; 0.775, 0.909, tmp+PL+PL_cumulo+interval_Pdt.+mu_cumulo+nu_cumulo+rho_cumulo+nu_per_rho_cumulo+Arg_conc._cumulo+RQ_integral+Accum._Yield+emission_O2+emission_CO2+consum_O2+generate_CO2; 0.775, 0.909, tmp+PL+PL_cumulo+AN+interval_Pdt.+mu_cumulo+nu_cumulo+rho_cumulo+nu_per_rho_cumulo+Arg_conc._cumulo+Accum._Yield+emission_O2+emission_CO2+consum_O2+generate_CO2; 0.784, 0.909, tmp+PL+AN+interval_Pdt.+mu_cumulo+nu_cumulo+rho_cumulo+nu_per_rho_cumulo+rab_integral+RQ_integral+emission_CO2+consum_O2+generate_CO2; 0.784, 0.909, tmp+PL+PL_cumulo+interval_Pdt.+mu_cumulo+nu_cumulo+rho_cumulo+nu_per_rho_cumulo+rab_integral+emission_CO2+consum_O2+interval_O2+generate_CO2; 0.775, 0.909, tmp+PL+interval_Pdt.+mu_cumulo+nu_cumulo+rho_cumulo+nu_per_rho_cumulo+Arg_conc._cumulo+cell_yield_cumulo+rab_integral+RQ_integral+Accum._Yield+emission_CO2+consum_O2+generate_CO2; 0.784, 0.909, tmp+PL+interval_Pdt.+OD+mu_cumulo+nu_cumulo+rho_cumulo+nu_per_rho_cumulo+Arg_conc._cumulo+rab_integral+emission_CO2+consum_O2+generate_CO2; 0.779, 0.909, tmp+PL+PL_cumulo+AN+interval_Pdt.+mu_cumulo+nu_cumulo+rho_cumulo+nu_per_rho_cumulo+Arg_conc._cumulo+rab_integral+emission_CO2+consum_O2+generate_CO2; 0.791, 0.909, tmp+PL+OD+nu_cumulo+rho_cumulo+nu_per_rho_cumulo+Arg_conc._cumulo+emission_O2+emission_CO2+consum_O2+generate_CO2; 0.779, 0.909, tmp+PL+AN+interval_Pdt.+mu_cumulo+nu_cumulo+rho_cumulo+nu_per_rho_cumulo+cell_yield_cumulo+emission_O2+emission_CO2+consum_O2+interval_O2+generate_CO2; 0.779, 0.909, tmp+PL+interval_Pdt.+RS+mu_cumulo+nu_cumulo+rho_cumulo+nu_per_rho_cumulo+cell_yield_cumulo+rab_integral+Accum._Yield+emission_CO2+consum_O2+generate_CO2; 0.775, 0.909, tmp+PL+interval_Pdt.+RS+mu_cumulo+nu_cumulo+rho_cumulo+nu_per_rho_cumulo+Arg_conc._cumulo+rab_integral+RQ_integral+Accum._Yield+emission_CO2+consum_O2+generate_CO2; 0.775, 0.909, tmp+PL+interval_Pdt.+mu_cumulo+nu_cumulo+rho_cumulo+nu_per_rho_cumulo+cell_yield_cumulo+RQ_integral+Accum._Yield+emission_O2+emission_CO2+consum_O2+interval_O2+generate_CO2; 0.788, 0.909, tmp+PL+interval_Pdt.+OD+nu_cumulo+rho_cumulo+nu_per_rho_cumulo+Arg_conc._cumulo+emission_O2+emission_CO2+consum_O2+generate_CO2; 0.783, 0.909, tmp+PL_cumulo+interval_Pdt.+mu_cumulo+nu_cumulo+rho_cumulo+nu_per_rho_cumulo+cell_yield_cumulo+rab_integral+Accum._Yield+emission_CO2+consum_O2+generate_CO2; 0.775, 0.909, tmp+PL+AN+interval_Pdt.+mu_cumulo+nu_cumulo+rho_cumulo+nu_per_rho_cumulo+Arg_conc._cumulo+cell_yield_cumulo+rab_integral+Accum._Yield+emission_CO2+consum_O2+generate_CO2; 0.779, 0.909, tmp+PL+PL_cumulo+AN+interval_Pdt.+RS+mu_cumulo+nu_cumulo+rho_cumulo+nu_per_rho_cumulo+rab_integral+emission_CO2+consum_O2+generate_CO2; 0.775, 0.909, tmp+PL+PL_cumulo+AN+interval_Pdt.+mu_cumulo+nu_cumulo+rho_cumulo+nu_per_rho_cumulo+cell_yield_cumulo+rab_integral+Accum._Yield+emission_CO2+consum_O2+generate_CO2; 0.783, 0.909, tmp+PL+interval_Pdt.+mu_cumulo+nu_cumulo+rho_cumulo+nu_per_rho_cumulo+cell_yield_cumulo+RQ_integral+emission_CO2+emission_CO2+consum_O2+generate_CO2; 0.779, 0.909, tmp+PL+PL_cumulo+interval_Pdt.+mu_cumulo+nu_cumulo+rho_cumulo+nu_per_rho_cumulo+Arg_conc._cumulo+Accum._Yield+emission_O2+emission_CO2+consum_O2+generate_CO2; 0.775, 0.909, tmp+PL+AN+interval_Pdt.+mu_cumulo+nu_cumulo+rho_cumulo+nu_per_rho_cumulo+rab_integral+RQ_integral+Accum._Yield+emission_CO2+consum_O2+interval_O2+generate_CO2; 0.783, 0.909, tmp+PL+interval_Pdt.+mu_cumulo+nu_cumulo+rho_cumulo+nu_per_rho_cumulo+Arg_conc._cumulo+rab_integral+RQ_integral+emission_CO2+consum_O2+generate_CO2; 0.783, 0.909, tmp+PL+AN+interval_Pdt.+mu_cumulo+nu_cumulo+rho_cumulo+nu_per_rho_cumulo+cell_yield_cumulo+emission_O2+emission_CO2+consum_O2+generate_CO2; 0.775, 0.909, tmp+PL+interval_Pdt.+mu_cumulo+nu_cumulo+rho_cumulo+nu_per_rho_cumulo+Arg_conc._cumulo+cell_yield_cumulo+RQ_integral+Accum._Yield+emission_CO2+consum_O2+generate_CO2; 0.795, 0.909, tmp+interval_Pdt.+mu_cumulo+nu_cumulo+rho_cumulo+nu_per_rho_cumulo+rab_integral+emission_CO2+consum_O2+generate_CO2; 0.783, 0.909, tmp+PL+interval_Pdt.+RS+mu_cumulo+nu_cumulo+rho_cumulo+nu_per_rho_cumulo+Arg_conc._cumulo+rab_integral+emission_CO2+consum_O2+generate_CO2; 0.787, 0.909, tmp+PL+interval_Pdt.+OD+nu_cumulo+rho_cumulo+nu_per_rho_cumulo+rab_integral+RQ_integral+emission_CO2+consum_O2+generate_CO2; 0.791, 0.909, tmp+PL_cumulo+interval_Pdt.+OD+mu_cumulo+nu_cumulo+rho_cumulo+nu_per_rho_cumulo+emission_CO2+consum_O2+generate_CO2; 0.787, 0.909, tmp+PL+AN+interval_Pdt.+mu_cumulo+rho_cumulo+rab_integral+Accum._Yield+emission_CO2+consum_O2+interval_O2+generate_CO2; 0.774, 0.909, tmp+PL+PL_cumulo+AN+interval_Pdt.+mu_cumulo+nu_cumulo+rho_cumulo+nu_per_rho_cumulo+RQ_integral+Accum._Yield+emission_O2+emission_CO2+consum_O2+generate_CO2; 0.770, 0.909, tmp+PL+PL_cumulo+interval_Pdt.+mu_cumulo+nu_cumulo+rho_cumulo+nu_per_rho_cumulo+Arg_conc._cumulo+rab_integral+RQ_integral+Accum._Yield+emission_O2+emission_CO2+consum_O2+generate_CO2; 0.774, 0.909, tmp+PL+PL_cumulo+interval_Pdt.+OD+nu_cumulo+rho_cumulo+nu_per_rho_cumulo+Arg_conc._cumulo+rab_integral+Accum._Yield+emission_CO2+consum_O2+interval_O2+generate_CO2; 0.770, 0.909, tmp+PL+PL_cumulo+interval_Pdt.+OD+nu_cumulo+rho_cumulo+nu_per_rho_cumulo+Arg_conc._cumulo+rab_integral+Accum._Yield+emission_O2+emission_CO2+consum_O2+interval_O2+generate_CO2; 0.779, 0.909, tmp+PL+AN+interval_Pdt.+OD+nu_cumulo+rho_cumulo+nu_per_rho_cumulo+Arg_conc._cumulo+Accum._Yield+emission_O2+emission_CO2+consum_O2+generate_CO2; 0.774, 0.909, tmp+PL+PL_cumulo+interval_Pdt.+OD+mu_cumulo+nu_cumulo+rho_cumulo+nu_per_rho_cumulo+Arg_conc._cumulo+rab_integral+Accum._Yield+emission_CO2+consum_O2+generate_CO2; 0.774, 0.909, tmp+PL+interval_Pdt.+OD+mu_cumulo+nu_cumulo+rho_cumulo+nu_per_rho_cumulo+Arg_conc._cumulo+rab_integral+RQ_integral+Accum._Yield+emission_CO2+consum_O2+generate_CO2; 0.779, 0.909, tmp+PL+AN+interval_Pdt.+mu_cumulo+nu_cumulo+rho_cumulo+nu_per_rho_cumulo+cell_yield_cumulo+Accum._Yield+emission_O2+emission_CO2+consum_O2+generate_CO2; 0.783, 0.909, tmp+PL+AN+interval_Pdt.+mu_cumulo+nu_cumulo+rho_cumulo+nu_per_rho_cumulo+cell_yield_cumulo+emission_CO2+consum_O2+interval_O2+generate_CO2; 0.787, 0.909, tmp+pH+PL+AN+interval_Pdt.+mu_cumulo+nu_cumulo+rho_cumulo+nu_per_rho_cumulo+emission_CO2+consum_O2+generate_CO2; 0.779, 0.909, tmp+PL+AN+interval_Pdt.+RS+mu_cumulo+nu_cumulo+rho_cumulo+nu_per_rho_cumulo+rab_integral+emission_

CO2+consum_O2+interval_O2+generate_CO2; 0.783, 0.909, tmp+PL+interval_Pdt.+mu_cumulo+nu_cumulo+rho_cumulo+nu_per_rho_cumulo+cell_yield_cumulo+emission_O2+emission_CO2+consum_O2+interval_O2+generate_CO2; 0.783, 0.909, tmp+PL+PL_cumulo+interval_Pdt.+mu_cumulo+nu_cumulo+rho_cumulo+nu_per_rho_cumulo+Arg_conc._cumulo+rab_integral+emission_CO2+consum_O2+generate_CO2; 0.783, 0.909, tmp+PL+OD+RS+nu_cumulo+rho_cumulo+nu_per_rho_cumulo+Arg_conc._cumulo+Accum._Yield+emission_O2+emission_CO2+consum_O2+generate_CO2; 0.779, 0.909, tmp+PL+AN+interval_Pdt.+mu_cumulo+nu_cumulo+rho_cumulo+nu_per_rho_cumulo+Arg_conc._cumulo+cell_yield_cumulo+Accum._Yield+emission_CO2+consum_O2+generate_CO2; 0.774, 0.909, tmp+PL+AN+interval_Pdt.+RS+mu_cumulo+nu_cumulo+rho_cumulo+nu_per_rho_cumulo+rab_integral+RQ_integral+Accum._Yield+emission_CO2+consum_O2+generate_CO2; 0.783, 0.909, tmp+pH+PL+AN+interval_Pdt.+mu_cumulo+nu_cumulo+rho_cumulo+nu_per_rho_cumulo+Accum._Yield+emission_CO2+consum_O2+generate_CO2; 0.779, 0.909, tmp+PL_cumulo+interval_Pdt.+mu_cumulo+nu_cumulo+rho_cumulo+nu_per_rho_cumulo+cell_yield_cumulo+rab_integral+RQ_integral+Accum._Yield+emission_CO2+consum_O2+generate_CO2; 0.783, 0.909, tmp+PL+interval_Pdt.+OD+RS+mu_cumulo+nu_cumulo+rho_cumulo+nu_per_rho_cumulo+rab_integral+emission_CO2+consum_O2+generate_CO2; 0.787, 0.909, tmp+PL+interval_Pdt.+RS+mu_cumulo+nu_cumulo+rho_cumulo+nu_per_rho_cumulo+emission_O2+emission_CO2+consum_O2+generate_CO2; 0.779, 0.909, tmp+PL+AN+interval_Pdt.+RS+mu_cumulo+nu_cumulo+rho_cumulo+nu_per_rho_cumulo+Arg_conc._cumulo+Accum._Yield+emission_CO2+consum_O2+generate_CO2; 0.774, 0.909, tmp+PL+PL_cumulo+interval_Pdt.+OD+RS+nu_cumulo+rho_cumulo+nu_per_rho_cumulo+Arg_conc._cumulo+rab_integral+Accum._Yield+emission_CO2+consum_O2+generate_CO2; 0.769, 0.909, tmp+pH+PL+PL_cumulo+AN+interval_Pdt.+OD+nu_cumulo+rho_cumulo+nu_per_rho_cumulo+Arg_conc._cumulo+Accum._Yield+emission_O2+emission_CO2+consum_O2+generate_CO2; 0.787, 0.909, tmp+PL+AN+interval_Pdt.+mu_cumulo+nu_cumulo+rho_cumulo+nu_per_rho_cumulo+RQ_integral+emission_CO2+consum_O2+generate_CO2; 0.774, 0.909, tmp+PL+AN+interval_Pdt.+RS+mu_cumulo+nu_cumulo+rho_cumulo+nu_per_rho_cumulo+cell_yield_cumulo+rab_integral+Accum._Yield+emission_CO2+consum_O2+generate_CO2; 0.778, 0.909, tmp+PL+interval_Pdt.+OD+mu_cumulo+nu_cumulo+rho_cumulo+nu_per_rho_cumulo+cell_yield_cumulo+rab_integral+Accum._Yield+emission_CO2+consum_O2+generate_CO2; 0.791, 0.909, tmp+interval_Pdt.+mu_cumulo+nu_cumulo+rho_cumulo+nu_per_rho_cumulo+rab_integral+Accum._Yield+emission_CO2+consum_O2+generate_CO2; 0.774, 0.909, tmp+PL+interval_Pdt.+RS+mu_cumulo+nu_cumulo+rho_cumulo+nu_per_rho_cumulo+cell_yield_cumulo+RQ_integral+Accum._Yield+emission_O2+emission_CO2+consum_O2+generate_CO2; 0.778, 0.909, tmp+PL+AN+interval_Pdt.+mu_cumulo+nu_cumulo+rho_cumulo+nu_per_rho_cumulo+Arg_conc._cumulo+Accum._Yield+emission_CO2+consum_O2+interval_O2+generate_CO2; 0.769, 0.909, tmp+pH+PL+PL_cumulo+interval_Pdt.+OD+nu_cumulo+rho_cumulo+nu_per_rho_cumulo+Arg_conc._cumulo+RQ_integral+Accum._Yield+emission_O2+emission_CO2+consum_O2+generate_CO2; 0.783, 0.909, tmp+PL+PL_cumulo+interval_Pdt.+RS+mu_cumulo+nu_cumulo+rho_cumulo+nu_per_rho_cumulo+rab_integral+emission_CO2+consum_O2+generate_CO2; 0.778, 0.909, tmp+PL+interval_Pdt.+OD+nu_cumulo+rho_cumulo+nu_per_rho_cumulo+Arg_conc._cumulo+Accum._Yield+emission_O2+emission_CO2+consum_O2+interval_O2+generate_CO2; 0.774, 0.909, tmp+PL+interval_Pdt.+OD+RS+mu_cumulo+nu_cumulo+rho_cumulo+nu_per_rho_cumulo+Arg_conc._cumulo+rab_integral+Accum._Yield+emission_CO2+consum_O2+generate_CO2; 0.769, 0.909, tmp+PL+PL_cumulo+AN+interval_Pdt.+mu_cumulo+nu_cumulo+rho_cumulo+nu_per_rho_cumulo+Arg_conc._cumulo+rab_integral+Accum._Yield+emission_O2+emission_CO2+consum_O2+generate_CO2; 0.782, 0.909, tmp+PL+AN+interval_Pdt.+OD+mu_cumulo+nu_cumulo+rho_cumulo+nu_per_rho_cumulo+emission_CO2+consum_O2+interval_O2+generate_CO2; 0.782, 0.909, tmp+PL+PL_cumulo+interval_Pdt.+mu_cumulo+nu_cumulo+rho_cumulo+nu_per_rho_cumulo+rab_integral+emission_O2+emission_CO2+consum_O2+generate_CO2; 0.794, 0.909, tmp+PL+AN+interval_Pdt.+mu_cumulo+rho_cumulo+nu_per_rho_cumulo+emission_CO2+consum_O2+generate_CO2; 0.774, 0.909, tmp+PL+PL_cumulo+interval_Pdt.+mu_cumulo+nu_cumulo+rho_cumulo+nu_per_rho_cumulo+cell_yield_cumulo+RQ_integral+Accum._Yield+emission_O2+emission_CO2+consum_O2+generate_CO2; 0.787, 0.909, tmp+PL+interval_Pdt.+mu_cumulo+nu_cumulo+rho_cumulo+nu_per_rho_cumulo+rab_integral+emission_O2+emission_CO2+consum_O2+generate_CO2; 0.782, 0.909, tmp+PL+AN+interval_Pdt.+RS+mu_cumulo+nu_cumulo+rho_cumulo+nu_per_rho_cumulo+emission_CO2+consum_O2+interval_O2+generate_CO2; 0.778, 0.909, tmp+PL+AN+interval_Pdt.+OD+mu_cumulo+nu_cumulo+rho_cumulo+nu_per_rho_cumulo+cell_yield_cumulo+rab_integral+emission_CO2+consum_O2+generate_CO2; 0.787, 0.909, tmp+PL_cumulo+interval_Pdt.+mu_cumulo+nu_cumulo+rho_cumulo+nu_per_rho_cumulo+rab_integral+RQ_integral+emission_CO2+consum_O2+generate_CO2; 0.774, 0.909, tmp+PL+interval_Pdt.+OD+mu_cumulo+nu_cumulo+rho_cumulo+nu_per_rho_cumulo+cell_yield_cumulo+RQ_integral+Accum._Yield+emission_O2+emission_CO2+consum_O2+generate_CO2; 0.782, 0.909, tmp+PL+AN+interval_Pdt.+OD+nu_cumulo+rho_cumulo+nu_per_rho_cumulo+Arg_conc._cumulo+rab_integral+emission_CO2+consum_O2+generate_CO2; 0.790, 0.909, tmp+PL+interval_Pdt.+OD+nu_cumulo+rho_cumulo+nu_per_rho_cumulo+emission_O2+emission_CO2+consum_O2+generate_CO2; 0.778, 0.909, tmp+PL+interval_Pdt.+OD+RS+nu_cumulo+rho_cumulo+nu_per_rho_cumulo+Arg_conc._cumulo+Accum._Yield+emission_O2+emission_CO2+consum_O2+generate_CO2; 0.782, 0.909, tmp+PL+interval_Pdt.+OD+mu_cumulo+nu_cumulo+rho_cumulo+nu_per_rho_cumulo+Accum._Yield+emission_O2+emission_CO2+consum_O2+generate_CO2; 0.782, 0.909, tmp+pH+PL+interval_Pdt.+mu_cumulo+nu_cumulo+rho_cumulo+nu_per_rho_cumulo+rab_integral+Accum._Yield+emission_CO2+consum_O2+generate_CO2; 0.774, 0.909, tmp+PL+AN+interval_Pdt.+OD+mu_cumulo+nu_cumulo+rho_cumulo+nu_per_rho_cumulo+Arg_conc._cumulo+rab_integral+Accum._Yield+emission_CO2+consum_O2+generate_CO2; 0.778, 0.909, tmp+PL+PL_cumulo+interval_Pdt.+mu_cumulo+nu_cumulo+rho_cumulo+nu_per_rho_cumulo+rab_integral+Accum._Yield+emission_O2+emission_CO2+consum_O2+generate_CO2; 0.778, 0.909, tmp+PL+AN+interval_Pdt.+mu_cumulo+nu_cumulo+rho_cumulo+nu_per_rho_cumulo+rab_integral+RQ_integral+emission_CO2+consum_O2+interval_O2+generate_CO2; 0.764, 0.909, tmp+PL+PL_cumulo+AN+interval_Pdt.+mu_cumulo+nu_ cumulo+rho_cumulo+nu_per_rho_cumulo+Arg_conc._cumulo+rab_integral+Accum._Yield+emission_O2+emission_CO2+consum_O2+interval_O2+generate_CO2; 0.782, 0.909, tmp+PL_cumulo+interval_Pdt.+RS+mu_cumulo+nu_cumulo+rho_cumulo+nu_per_rho_cumulo+cell_yield_cumulo+rab_integral+emission_CO2+consum_O2+generate_CO2; 0.786, 0.909, tmp+PL_cumulo+interval_Pdt.+OD+mu_cumulo+nu_cumulo+rho_cumulo+nu_per_rho_cumulo+rab_integral+emission_CO2+consum_O2+generate_CO2; 0.778, 0.909, tmp+PL+AN+interval_Pdt.+OD+mu_cumulo+nu_cumulo+rho_cumulo+nu_per_rho_cumulo+emission_O2+emission_CO2+consum_O2+interval_O2+generate_CO2; 0.769, 0.909, tmp+pH+PL+PL_cumulo+AN+interval_Pdt.+OD+nu_cumulo+rho_cumulo+nu_per_rho_cumulo+Arg_conc._cumulo+rab_integral+Accum._Yield+emission_CO2+consum_O2+generate_CO2; 0.778, 0.909, tmp+pH+PL+interval_Pdt.+OD+nu_cumulo+rho_cumulo+nu_per_rho_cumulo+Arg_conc._cumulo+rab_integral+Accum._Yield+emission_CO2+consum_O2+generate_CO2; 0.773, 0.909, tmp+PL+PL_cumulo+AN+interval_Pdt.+mu_cumulo+nu_cumulo+rho_cumulo+nu_per_rho_cumulo+Arg_conc._cumulo+rab_integral+emission_CO2+consum_O2+interval_O2+generate_CO2; 0.790, 0.909, tmp+PL_cumulo+interval_Pdt.+mu_cumulo+nu_cumulo+rho_cumulo+nu_per_rho_cumulo+Accum._Yield+emission_CO2+consum_O2+generate_CO2; 0.782, 0.909, tmp+PL+PL_cumulo+interval_Pdt.+mu_cumulo+nu_cumulo+rho_cumulo+nu_per_rho_cumulo+RQ_integral+emission_O2+emission_CO2+consum_O2+generate_CO2; 0.790, 0.909, tmp+PL+AN+interval_Pdt.+mu_cumulo+rho_cumulo+nu_per_rho_cumulo+emission_CO2+consum_O2+interval_O2+generate_CO2; 0.782, 0.909, tmp+pH+PL+interval_Pdt.+mu_cumulo+nu_cumulo+rho_cumulo+nu_per_rho_cumulo+cell_yield_cumulo+rab_integral+emission_CO2+consum_O2+generate_CO2; 0.782, 0.909, tmp+PL+interval_Pdt.+OD+mu_cumulo+nu_cumulo+rho_cumulo+nu_per_rho_cumulo+rab_integral+emission_CO2+consum_O2+interval_O2+generate_CO2; 0.773, 0.909, tmp+PL+AN+interval_Pdt.+OD+RS+nu_cumulo+rho_cumulo+nu_per_rho_cumulo+Arg_conc._cumulo+rab_integral+Accum._Yield+emission_CO2+consum_O2+generate_CO2; 0.786, 0.909, tmp+PL+interval_Pdt.+OD+nu_cumulo+rho_cumulo+nu_per_rho_cumulo+RQ_integral+emission_O2+emission_CO2+consum_O2+generate_CO2; 0.773, 0.909, tmp+PL+AN+interval_Pdt.+OD+mu_cumulo+nu_cumulo+rho_cumulo+nu_per_rho_cumulo+rab_integral+Accum._Yield+emission_CO2+consum_O2+interval_O2+generate_CO2; 0.782, 0.909, tmp+PL_cumulo+interval_Pdt.+mu_cumulo+nu_cumulo+rho_cumulo+nu_per_rho_cumulo+cell_yield_cumulo+rab_integral+RQ_integral+emission_CO2+consum_O2+generate_CO2; 0.782, 0.909, tmp+PL+interval_Pdt.+mu_cumulo+nu_cumulo+rho_cumulo+nu_per_rho_cumulo+RQ_integral+emission_O2+emission_CO2+consum_O2+interval_O2+generate_CO2; 0.790, 0.909, tmp+pH+interval_Pdt.+mu_cumulo+nu_cumulo+rho_cumulo+nu_per_rho_cumulo+rab_integral+emission_CO2+consum_O2+generate_CO2; 0.773, 0.909, tmp+PL+interval_Pdt.+mu_cumulo+nu_cumulo+rho_cumulo+nu_per_rho_cumulo+cell_yield_cumulo+rab_integral+RQ_integral+Accum._Yield+emission_O2+emission_CO2+consum_O2+generate_CO2; 0.782, 0.909, tmp+PL+interval_Pdt.+mu_cumulo+nu_cumulo+rho_cumulo+nu_per_rho_cumulo+Arg_conc._cumulo+cell_yield_cumulo+emission_O2+emission_CO2+consum_O2+generate_CO2; 0.773, 0.909, tmp+PL+interval_Pdt.+RS+mu_cumulo+nu_cumulo+rho_cumulo+nu_per_rho_cumulo+Arg_conc._cumulo+cell_yield_cumulo+rab_integral+Accum._Yield+emission_CO2+consum_O2+generate_CO2; 0.778, 0.909, tmp+PL+AN+interval_Pdt.+mu_cumulo+nu_cumulo+rho_cumulo+nu_per_rho_cumulo+Arg_conc._cumulo+rab_integral+Accum._Yield+emission_CO2+consum_O2+generate_CO2; 0.773, 0.909, tmp+PL+PL_cumulo+AN+interval_Pdt.+mu_cumulo+nu_cumulo+rho_cumulo+nu_per_rho_cumulo+Arg_conc._cumulo+emission_O2+emission_CO2+consum_O2+interval_O2+generate_CO2; 0.782, 0.909, tmp+PL+PL_cumulo+AN+interval_Pdt.+mu_cumulo+nu_cumulo+rho_cumulo+nu_per_rho_cumulo+emission_CO2+consum_O2+interval_O2+generate_CO2; 0.778, 0.909, tmp+PL+interval_Pdt.+OD+mu_cumulo+nu_cumulo+rho_cumulo+nu_per_rho_cumulo+Arg_conc._cumulo+Accum._Yield+emission_O2+emission_CO2+consum_O2+generate_CO2; 0.778, 0.909, tmp+PL+interval_Pdt.+RS+mu_cumulo+nu_cumulo+rho_cumulo+nu_per_rho_cumulo+Arg_conc._cumulo+rab_integral+Accum._Yield+emission_CO2+consum_O2+generate_CO2; 0.769, 0.909, tmp+PL+PL_cumulo+AN+interval_Pdt.+OD+mu_cumulo+nu_cumulo+rho_cumulo+nu_per_rho_cumulo+Arg_conc._cumulo+Accum._Yield+emission_O2+emission_CO2+consum_O2+generate_CO2; 0.773, 0.909, tmp+PL+AN+interval_Pdt.+mu_cumulo+nu_cumulo+rho_cumulo+nu_per_rho_cumulo+cell_yield_cumulo+Accum._Yield+emission_O2+emission_CO2+consum_O2+interval_O2+generate_CO2; 0.786, 0.909, tmp+PL+interval_Pdt.+mu_cumulo+nu_cumulo+rho_cumulo+nu_per_rho_cumulo+Arg_conc._cumulo+emission_O2+emission_CO2+consum_O2+generate_CO2; 0.790, 0.909, tmp+PL+AN+interval_Pdt.+RS+mu_cumulo+rho_cumulo+Accum._Yield+emission_CO2+consum_O2+generate_CO2; 0.786, 0.909, tmp+PL_cumulo+interval_Pdt.+RS+mu_cumulo+nu_cumulo+rho_cumulo+nu_per_rho_cumulo+rab_integral+emission_CO2+consum_O2+generate_CO2; 0.782, 0.909, tmp+PL+interval_Pdt.+OD+nu_cumulo+rho_cumulo+nu_per_rho_cumulo+RQ_integral+Accum._Yield+emission_O2+emission_CO2+consum_O2+generate_CO2; 0.782, 0.909, tmp+PL+AN+interval_Pdt.+mu_cumulo+nu_cumulo+rho_cumulo+nu_per_rho_cumulo+RQ_integral+Accum._Yield+emission_CO2+consum_O2+generate_CO2; 0.773, 0.909, tmp+PL+interval_Pdt.+OD+mu_cumulo+nu_cumulo+rho_cumulo+nu_per_rho_cumulo+cell_yield_cumulo+rab_integral+RQ_integral+Accum._Yield+emission_CO2+consum_O2+generate_CO2; 0.782, 0.909, tmp+PL+PL_cumulo+interval_Pdt.+mu_cumulo+nu_cumulo+rho_cumulo+nu_per_rho_cumulo+cell_yield_cumulo+emission_O2+emission_CO2+consum_O2+generate_CO2; 0.782, 0.908, tmp+PL+PL_cumulo+interval_yield+interval_Pdt.+mu_cumulo+nu_cumulo+rho_cumulo+nu_per_rho_cumulo+rab_integral+emission_CO2+consum_O2+generate_CO2; 0.782, 0.908, tmp+PL+interval_Pdt.+mu_cumulo+nu_cumulo+rho_cumulo+nu_per_rho_cumulo+Accum._Yield+emission_O2+emission_CO2+consum_O2+interval_O2+generate_CO2; 0.782, 0.908, tmp+PL+interval_Pdt.+OD+mu_cumulo+nu_cumulo+rho_cumulo+nu_per_rho_cumulo+cell_yield_cumulo+emission_O2+emission_CO2+consum_O2+generate_CO2; 0.782, 0.908, tmp+PL+interval_Pdt.+RS+mu_cumulo+nu_cumulo+rho_cumulo+nu_per_rho_cumulo+cell_yield_cumulo+emission_O2+emission_CO2+consum_O2+generate_CO2; 0.786, 0.908, tmp+PL_cumulo+interval_Pdt.+mu_cumulo+nu_cumulo+rho_cumulo+nu_per_rho_cumulo+rab_integral+Accum._Yield+emission_CO2+consum_O2+generate_CO2; 0.777, 0.908, tmp+PL+PL_cumulo+AN+interval_Pdt.+mu_cumulo+nu_cumulo+rho_cumulo+nu_ per_rho_cumulo+rab_integral+emission_O2+emission_CO2+consum_O2+generate_CO2; 0.782, 0.908, tmp+PL+AN+interval_Pdt.+mu_cumulo+nu_cumulo+rho_cumulo+nu_per_rho_cumulo+Arg_conc._cumulo+cell_yield_cumulo+emission_CO2+consum_O2+generate_CO2; 0.773, 0.908, tmp+PL+interval_Pdt.+OD+nu_cumulo+rho_cumulo+nu_per_rho_cumulo+Arg_conc._cumulo+RQ_integral+Accum._Yield+emission_O2+emission_CO2+consum_O2+interval_O2+generate_CO2; 0.777, 0.908, tmp+pH+PL+PL_cumulo+OD+nu_cumulo+rho_cumulo+nu_per_rho_cumulo+Arg_conc._cumulo+Accum._Yield+emission_O2+emission_CO2+consum_O2+generate_CO2; 0.777, 0.908, tmp+PL+interval_Pdt.+mu_cumulo+nu_cumulo+rho_cumulo+nu_per_rho_cumulo+cell_yield_cumulo+rab_integral+Accum._Yield+emission_CO2+consum_O2+interval_O2+generate_CO2; 0.777, 0.908, tmp+PL+AN+interval_Pdt.+mu_cumulo+nu_cumulo+rho_cumulo+nu_per_rho_cumulo+cell_yield_cumulo+Accum._Yield+emission_CO2+consum_O2+interval_O2+generate_CO2; 0.773, 0.908, tmp+PL+PL_cumulo+interval_Pdt.+mu_cumulo+nu_cumulo+rho_cumulo+nu_per_rho_cumulo+Arg_conc._cumulo+rab_integral+Accum._Yield+emission_O2+emission_CO2+consum_O2+generate_CO2; 0.781, 0.908, tmp+PL+AN+interval_Pdt.+OD+mu_cumulo+nu_cumulo+rho_cumulo+nu_per_rho_cumulo+emission_O2+emission_CO2+consum_O2+generate_CO2; 0.768, 0.908, tmp+PL+PL_cumulo+interval_Pdt.+OD+mu_cumulo+nu_cumulo+rho_cumulo+nu_per_rho_cumulo+Arg_conc._cumulo+RQ_integral+Accum._Yield+emission_O2+emission_CO2+consum_O2+generate_CO2; 0.777, 0.908, tmp+PL+AN+interval_Pdt.+mu_cumulo+nu_cumulo+rho_cumulo+nu_per_rho_cumulo+Arg_conc._cumulo+emission_O2+emission_CO2+consum_O2+interval_O2+generate_CO2; 0.777, 0.908, tmp+PL+PL_cumulo+interval_Pdt.+mu_cumulo+nu_cumulo+rho_cumulo+nu_per_rho_cumulo+cell_yield_cumulo+rab_integral+Accum._Yield+emission_CO2+consum_O2+generate_CO2; 0.777, 0.908, tmp+PL+interval_Pdt.+RS+mu_cumulo+nu_cumulo+rho_cumulo+nu_per_rho_cumulo+Arg_conc._cumulo+cell_yield_cumulo+rab_integral+emission_CO2+consum_O2+generate_CO2; 0.763, 0.908, tmp+PL+PL_cumulo+AN+interval_Pdt.+OD+nu_cumulo+rho_cumulo+nu_per_rho_cumulo+Arg_conc._cumulo+rab_integral+Accum._Yield+emission_O2+emission_CO2+consum_O2+interval_O2+generate_CO2; 0.777, 0.908, tmp+PL+AN+interval_Pdt.+OD+mu_cumulo+nu_cumulo+rho_cumulo+nu_per_rho_cumulo+Accum._Yield+emission_CO2+consum_O2+interval_O2+generate_CO2; 0.781, 0.908, tmp+PL+AN+interval_Pdt.+OD+nu_cumulo+rho_cumulo+nu_per_rho_cumulo+rab_integral+emission_CO2+consum_O2+interval_O2+generate_CO2; 0.773, 0.908, tmp+PL+AN+interval_Pdt.+RS+mu_cumulo+nu_cumulo+rho_cumulo+nu_per_rho_cumulo+rab_integral+Accum._Yield+emission_CO2+consum_O2+interval_O2+generate_CO2; 0.773, 0.908, tmp+PL+interval_Pdt.+OD+RS+nu_cumulo+rho_cumulo+nu_per_rho_cumulo+Arg_conc._cumulo+RQ_integral+Accum._Yield+emission_O2+emission_CO2+consum_O2+generate_CO2; 0.768, 0.908, tmp+PL+PL_cumulo+interval_Pdt.+OD+RS+nu_cumulo+rho_cumulo+nu_per_rho_cumulo+Arg_conc._Accum._Yield+emission_O2+emission_CO2+consum_O2+interval_O2+generate_CO2; 0.773, 0.908, tmp+PL+AN+interval_Pdt.+OD+mu_cumulo+nu_cumulo+rho_cumulo+nu_per_rho_cumulo+cell_yield_cumulo+rab_integral+Accum._Yield+emission_CO2+consum_O2+generate_CO2; 0.777, 0.908, tmp+PL+interval_Pdt.+RS+mu_cumulo+nu_cumulo+rho_cumulo+nu_per_rho_cumulo+cell_yield_cumulo+rab_integral+RQ_integral+emission_CO2+consum_O2+generate_CO2; 0.777, 0.908, tmp+PL+interval_Pdt.+mu_cumulo+nu_cumulo+rho_cumulo+nu_per_rho_cumulo+Arg_conc._cumulo+RQ_integral+Accum._Yield+emission_O2+emission_CO2+consum_O2+generate_CO2; 0.772, 0.908, tmp+PL+interval_Pdt.+OD+nu_cumulo+rho_cumulo+nu_per_rho_cumulo+Arg_conc._cumulo+rab_integral+RQ_integral+Accum._Yield+emission_CO2+consum_O2+interval_O2+generate_CO2; 0.781, 0.908, tmp+PL+interval_Pdt.+OD+mu_cumulo+nu_cumulo+rho_cumulo+nu_per_rho_cumulo+RQ_integral+emission_O2+emission_CO2+consum_O2+generate_CO2; 0.772, 0.908, tmp+pH+PL+PL_cumulo+AN+interval_Pdt.+mu_cumulo+nu_cumulo+rho_cumulo+nu_per_rho_cumulo+rab_integral+Accum._Yield+emission_CO2+consum_O2+generate_CO2; 0.772, 0.908, tmp+PL+PL_cumulo+AN+interval_Pdt.+mu_cumulo+nu_cumulo+rho_cumulo+nu_per_rho_cumulo+cell_yield_cumulo+emission_O2+emission_CO2+consum_O2+interval_O2+generate_CO2; 0.789, 0.908, tmp+PL+interval_Pdt.+mu_cumulo+nu_cumulo+rho_cumulo+nu_per_rho_cumulo+emission_CO2+consum_O2+interval_O2+generate_CO2; 0.789, 0.908, tmp+PL+AN+interval_Pdt.+mu_cumulo+rho_cumulo+nu_per_rho_cumulo+Accum._Yield+emission_CO2+consum_O2+generate_CO2; 0.772, 0.908, tmp+PL+interval_Pdt.+RS+mu_cumulo+nu_cumulo+rho_cumulo+nu_per_rho_cumulo+cell_yield_cumulo+rab_integral+RQ_integral+Accum._Yield+emission_CO2+consum_O2+generate_CO2; 0.785, 0.908, tmp+interval_Pdt.+mu_cumulo+nu_cumulo+rho_cumulo+nu_per_rho_cumulo+rab_integral+RQ_integral+Accum._Yield+emission_CO2+consum_O2+generate_CO2; 0.777, 0.908, tmp+PL+AN+interval_Pdt.+RS+mu_cumulo+nu_cumulo+rho_cumulo+nu_per_rho_cumulo+Accum._Yield+emission_CO2+consum_O2+interval_O2+generate_CO2; 0.772, 0.908, tmp+PL+PL_cumulo+AN+interval_Pdt.+mu_cumulo+nu_cumulo+rho_cumulo+nu_per_rho_cumulo+cell_yield_cumulo+rab_integral+emission_CO2+consum_O2+interval_O2+generate_CO2; 0.777, 0.908, tmp+PL+PL_cumulo+AN+interval_Pdt.+mu_cumulo+nu_cumulo+rho_cumulo+nu_per_rho_cumulo+rab_integral+RQ_integral+emission_CO2+consum_O2+generate_CO2; 0.777, 0.908, tmp+PL+AN+interval_Pdt.+mu_cumulo+nu_cumulo+rho_cumulo+nu_per_rho_cumulo+cell_yield_cumulo+rab_integral+RQ_integral+emission_CO2+consum_O2+generate_CO2; 0.781, 0.908, tmp+PL+interval_Pdt.+RS+mu_cumulo+nu_cumulo+rho_cumulo+nu_per_rho_cumulo+rab_integral+emission_CO2+consum_O2+interval_O2+generate_CO2; 0.772, 0.908, tmp+PL+interval_Pdt.+OD+mu_cumulo+nu_cumulo+rho_cumulo+nu_per_rho_cumulo+Arg_conc._cumulo+RQ_integral+Accum._Yield+emission_O2+emission_CO2+consum_O2+generate_CO2; 0.768, 0.908, tmp+PL+PL_cumulo+AN+interval_Pdt.+RS+mu_cumulo+nu_cumulo+rho_cumulo+nu_per_rho_cumulo+Accum._Yield+emission_O2+emission_CO2+consum_O2+interval_O2+generate_CO2; 0.781, 0.908, tmp+PL+interval_Pdt.+OD+mu_cumulo+nu_cumulo+rho_cumulo+nu_per_rho_cumulo+emission_O2+emission_CO2+consum_O2+interval_O2+generate_CO2; 0.772, 0.908, tmp+PL+AN+interval_Pdt.+mu_cumulo+nu_cumulo+rho_cumulo+nu_per_rho_cumulo+Arg_conc._cumulo+cell_yield_cumulo+rab_integral+emission_CO2+consum_O2+interval_O2+generate_CO2; 0.772, 0.908, tmp+PL+AN+interval_Pdt.+OD+mu_cumulo+nu_cumulo+rho_cumulo+nu_per_rho_cumulo+rab_integral+RQ_integral+Accum._Yield+emission_CO2+consum_O2+generate_CO2; 0.781, 0.908, tmp+PL+AN+interval_Pdt.+RS+mu_cumulo+nu_cumulo+ rho_cumulo+nu_per_rho_cumulo+Arg_conc._cumulo+ emission_CO2+consum_O2+generate_CO2; 0.777, 0.908, tmp+PL+PL_cumulo+interval_Pdt.+mu_cumulo+nu_cumulo+rho_cumulo+nu_per_rho_cumulo+rab_integral+Accum._Yield+emission_CO2+consum_O2+interval_O2+ generate_CO2; 0.772, 0.908, tmp+pH+PL+PL_cumulo+ interval_Pdt.+OD+nu_cumulo+rho_cumulo+nu_per_rho_ cumulo+Arg_conc._cumulo+rab_integral+Accum._Yield+ emission_CO2+consum_O2+generate_CO2; 0.781, 0.908, tmp+pH+PL+PL_cumulo+interval_Pdt.+mu_cumulo+nu_ cumulo+rho_cumulo+nu_per_rho_cumulo+rab_integral+ emission_CO2+consum_O2+generate_CO2; 0.789, 0.908, tmp+PL+AN+interval_yield+interval_Pdt.+mu_cumulo+ rho_cumulo+Accum._Yield+emission_CO2+consum_O2+ generate_CO2; 0.781, 0.908, tmp+PL+interval_Pdt.+RS+ mu_cumulo+nu_cumulo+rho_cumulo+nu_per_rho_ cumulo+Accum._Yield+emission_O2+emission_CO2+ consum_O2+generate_CO2; 0.785, 0.908, tmp+PL+AN+ interval_Pdt.+OD+nu_cumulo+rho_cumulo+nu_per_rho_ cumulo+emission_O2+emission_CO2+consum_O2+ generate_CO2; 0.789, 0.908, tmp+interval_Pdt.+mu_ cumulo+nu_cumulo+rho_cumulo+nu_per_rho_cumulo+ cell_yield_cumulo+rab_integral+emission_CO2+consum_ O2+generate_CO2; 0.768, 0.908, tmp+pH+PL+PL_ cumulo+AN+interval_Pdt.+mu_cumulo+nu_cumulo+rho_ cumulo+nu_per_rho_cumulo+Arg_conc._cumulo+rab_ integral+Accum._Yield+emission_CO2+consum_O2+ generate_CO2; 0.777, 0.908, tmp+PL+PL_cumulo+ interval_Pdt.+mu_cumulo+nu_cumulo+rho_cumulo+nu_ per_rho_cumulo+RQ_integral+emission_O2+emission_ CO2+consum_O2+interval_O2+generate_CO2; 0.768, 0.908, tmp+PL+PL_cumulo+AN+interval_Pdt.+mu_cu- mulo+nu_cumulo+rho_cumulo+nu_per_rho_cumulo+Arg_ conc._cumulo+cell_yield_cumulo+rab_integral+Accum._ Yield+emission_CO2+consum_O2+generate_CO2; 0.781, 0.908, tmp+PL+interval_yield+interval_Pdt.+mu_cumulo+ nu_cumulo+rho_cumulo+nu_per_rho_cumulo+cell_yield_ cumulo+rab_integral+emission_CO2+consum_O2+gener- ate_CO2; 0.781, 0.908, tmp+pH+interval_Pdt.+mu_ cumulo+nu_cumulo+rho_cumulo+nu_per_rho_cumulo+ rab_integral+RQ_integral+Accum._Yield+emission_CO2+ consum_O2+generate_CO2; 0.768, 0.908, tmp+PL+PL_ cumulo+AN+interval_Pdt.+mu_cumulo+nu_cumulo+rho_ cumulo+nu_per_rho_cumulo+cell_yield_cumulo+Accum._ Yield+emission_O2+emission_CO2+consum_O2+interval_ O2+generate_CO2; 0.772, 0.908, tmp+PL+interval_Pdt.+ OD+RS+nu_cumulo+rho_cumulo+nu_per_rho_cumulo+ Arg_conc._cumulo+rab_integral+RQ_integral+Accum._ Yield+emission_CO2+consum_O2+generate_CO2; 0.763, 0.908, tmp+PL+PL_cumulo+interval_Pdt.+OD+nu_cu- mulo+rho_cumulo+nu_per_rho_cumulo+Arg_conc._cu- mulo+rab_integral+RQ_integral+Accum._Yield+emission_ O2+emission_CO2+consum_O2+interval_O2+generate_ CO2; 0.781, 0.908, tmp+PL+interval_yield+interval_Pdt.+ mu_cumulo+nu_cumulo+rho_cumulo+nu_per_rho_ cumulo+rab_integral+RQ_integral+emission_CO2+ consum_O2+generate_CO2; 0.781, 0.908, tmp+pH+PL+ AN+interval_Pdt.+mu_cumulo+nu_cumulo+rho_cumulo+ nu_per_rho_cumulo+rab_integral+emission_CO2+ consum_O2+generate_CO2; 0.789, 0.908, tmp+PL_ cumulo+interval_Pdt.+RS+mu_cumulo+nu_cumulo+rho_ cumulo+nu_per_rho_cumulo+emission_CO2+consum_ O2+generate_CO2; 0.767, 0.908, tmp+PL+PL_cumulo+ interval_Pdt.+mu_cumulo+nu_cumulo+rho_cumulo+nu_ per_rho_cumulo+rab_integral+RQ_integral+Accum._ Yield+emission_O2+emission_CO2+consum_O2+interval_ O2+generate_CO2; 0.781, 0.908, tmp+PL+AN+interval_ Pdt.+OD+mu_cumulo+nu_cumulo+rho_cumulo+nu_per_ rho_cumulo+cell_yield_cumulo+emission_CO2+consum_ O2+generate_CO2; 0.777, 0.908, tmp+PL_cumulo+ interval_Pdt.+RS+mu_cumulo+nu_cumulo+rho_cumulo+ nu_per_rho_cumulo+rab_integral+RQ_integral+Accum._ Yield+emission_CO2+consum_O2+generate_CO2; 0.776, 0.908, tmp+PL+interval_Pdt.+mu_cumulo+nu_cumulo+ rho_cumulo+nu_per_rho_cumulo+Arg_conc._cumulo+ cell_yield_cumulo+Accum._Yield+emission_O2+emis- sion_CO2+consum_O2+generate_CO2; 0.781, 0.908, tmp+ pH+PL+OD+nu_cumulo+rho_cumulo+nu_per_rho_ cumulo+Arg_conc._cumulo+rab_integral+Accum._Yield+ emission_CO2+consum_O2+generate_CO2; 0.772, 0.908, tmp+PL+AN+interval_Pdt.+OD+nu_cumulo+rho_cumulo+ nu_per_rho_cumulo+Arg_conc._cumulo+rab_integral+Ac- cum._Yield+emission_CO2+consum_O2+interval_O2+ generate_CO2; 0.785, 0.908, tmp+PL+AN+interval_Pdt.+ mu_cumulo+rho_cumulo+Accum._Yield+emission_O2+ emission_CO2+consum_O2+interval_O2+generate_CO2; 0.781, 0.908, tmp+PL+interval_Pdt.+mu_cumulo+nu_cu- mulo+rho_cumulo+nu_per_rho_cumulo+rab_integral+Ac- cum._Yield+emission_O2+emission_CO2+consum_O2+ generate_CO2; 0.776, 0.908, tmp+PL+PL_cumulo+ interval_Pdt.+RS+mu_cumulo+nu_cumulo+rho_cumulo+ nu_per_rho_cumulo+rab_integral+Accum._Yield+ emission_CO2+consum_O2+generate_CO2; 0.781, 0.908, tmp+PL_cumulo+interval_Pdt.+RS+mu_cumulo+nu_cu- mulo+rho_cumulo+nu_per_rho_cumulo+rab_integral+RQ_ integral+emission_CO2+consum_O2+generate_CO2; 0.776, 0.908, tmp+pH+PL+AN+interval_Pdt.+mu_cumulo+ nu_cumulo+rho_cumulo+nu_per_rho_cumulo+rab_inte- gral+Accum._Yield+emission_CO2+consum_O2+gener- ate_CO2; 0.785, 0.908, tmp+pH+interval_Pdt.+mu_ cumulo+nu_cumulo+rho_cumulo+nu_per_rho_cumulo+ rab_integral+Accum._Yield+emission_CO2+consum_O2+ generate_CO2; 0.776, 0.908, tmp+PL+interval_Pdt.+mu_ cumulo+nu_cumulo+rho_cumulo+nu_per_rho_cumulo+ cell_yield_cumulo+Accum._Yield+emission_O2+ emission_CO2+consum_O2+interval_O2+generate_CO2; 0.776, 0.908, tmp+PL+interval_Pdt.+OD+mu_cumulo+nu_ cumulo+rho_cumulo+nu_per_rho_cumulo+cell_yield_cu- mulo+rab_integral+RQ_integral+emission_CO2+consum_ O2+generate_CO2; 0.776, 0.908, tmp+PL+interval_yield+ interval_Pdt.+mu_cumulo+nu_cumulo+rho_cumulo+nu_ per_rho_cumulo+cell_yield_cumulo+rab_integral+RQ_ integral+emission_CO2+consum_O2+generate_CO2; 0.767, 0.908, tmp+PL+AN+interval_Pdt.+RS+mu_cumulo+ nu_cumulo+rho_cumulo+nu_per_rho_cumulo+Arg_conc._ cumulo+cell_yield_cumulo+rab_integral+Accum._Yield+ emission_CO2+consum_O2+generate_CO2; 0.781, 0.908, tmp+PL+interval_Pdt.+mu_cumulo+nu_cumulo+rho_cu- mulo+nu_per_rho_cumulo+Arg_conc._cumulo+rab_inte- gral+emission_CO2+consum_O2+interval_O2+generate_ CO2; 0.789, 0.908, tmp+PL_cumulo+AN+interval_Pdt.+ mu_cumulo+nu_cumulo+rho_cumulo+nu_per_rho_ cumulo+emission_CO2+consum_O2+generate_CO2; 0.781, 0.908, tmp+PL+interval_Pdt.+OD+nu_cumulo+rho_ cumulo+nu_per_rho_cumulo+Arg_conc._cumulo+rab_in- tegral+emission_CO2+consum_O2+interval_O2+generate_ CO2; 0.781, 0.908, tmp+PL+interval_Pdt.+OD+nu_ cumulo+rho_cumulo+nu_per_rho_cumulo+rab_integral+ RQ_integral+Accum._Yield+emission_CO2+consum_O2+ generate_CO2; 0.789, 0.908, tmp+PL_cumulo+OD+nu_ cumulo+rho_cumulo+nu_per_rho_cumulo+Arg_conc._ cumulo+rab_integral+emission_CO2+consum_O2+ generate_CO2; 0.789, 0.908, tmp+PL+AN+interval_Pdt.+

OD+nu_cumulo+rho_cumulo+nu_per_rho_cumulo+emission_CO2+consum_O2+generate_CO2; 0.776, 0.908, tmp+pH+PL+PL_cumulo+AN+interval_Pdt.+mu_cumulo+nu_cumulo+rho_cumulo+nu_per_rho_cumulo+rab_integral+emission_CO2+consum_O2+generate_CO2; 0.767, 0.908, tmp+PL+PL_cumulo+interval_Pdt.+OD+RS+nu_cumulo+rho_cumulo+nu_per_rho_cumulo+Arg_conc._cumulo+rab_integral+Accum._Yield+emission_O2+emission_CO2+consum_O2+generate_CO2; 0.781, 0.908, tmp+PL+PL_cumulo+interval_Pdt.+OD+mu_cumulo+nu_cumulo+rho_cumulo+nu_per_rho_cumulo+rab_integral+emission_CO2+consum_O2+generate_CO2; 0.789, 0.908, tmp+PL+AN+interval_Pdt.+mu_cumulo+nu_cumulo+rho_cumulo+Accum._Yield+emission_CO2+consum_O2+generate_CO2; 0.780, 0.908, tmp+PL_cumulo+interval_Pdt.+mu_cumulo+nu_cumulo+rho_cumulo+nu_per_rho_cumulo+Arg_conc._cumulo+cell_yield_cumulo+rab_integral+emission_CO2+consum_O2+generate_CO2; 0.767, 0.908, tmp+PL+interval_Pdt.+RS+mu_cumulo+nu_cumulo+rho_cumulo+nu_per_rho_cumulo+Arg_conc._cumulo+cell_yield_cumulo+rab_integral+RQ_integral+Accum._Yield+emission_CO2+consum_O2+generate_CO2; 0.789, 0.908, tmp+PL_cumulo+interval_Pdt.+mu_cumulo+nu_cumulo+rho_cumulo+nu_per_rho_cumulo+emission_CO2+consum_O2+interval_O2+generate_CO2; 0.785, 0.908, tmp+PL+interval_Pdt.+OD+nu_cumulo+rho_cumulo+nu_per_rho_cumulo+rab_integral+Accum._Yield+emission_CO2+consum_O2+generate_CO2; 0.772, 0.908, tmp+PL+AN+interval_Pdt.+OD+nu_cumulo+rho_cumulo+nu_per_rho_cumulo+Arg_conc._cumulo+rab_integral+RQ_integral+Accum._Yield+emission_CO2+consum_O2+generate_CO2; 0.772, 0.908, tmp+PL+AN+interval_Pdt.+mu_cumulo+nu_cumulo+rho_cumulo+nu_per_rho_cumulo+Arg_conc._cumulo+rab_integral+RQ_integral+Accum._Yield+emission_CO2+consum_O2+generate_CO2; 0.772, 0.908, tmp+PL+interval_Pdt.+OD+mu_cumulo+nu_cumulo+rho_cumulo+nu_per_rho_cumulo+RQ_integral+Accum._Yield+emission_O2+emission_CO2+consum_O2+interval_O2+generate_CO2; 0.776, 0.908, tmp+PL+PL_cumulo+AN+interval_Pdt.+mu_cumulo+nu_cumulo+rho_cumulo+nu_per_rho_cumulo+Arg_conc._cumulo+Accum._Yield+emission_CO2+consum_O2+generate_CO2; 0.776, 0.908, tmp+PL+AN+interval_Pdt.+OD+mu_cumulo+nu_cumulo+rho_cumulo+nu_per_rho_cumulo+cell_yield_cumulo+Accum._Yield+emission_CO2+consum_O2+generate_CO2; 0.772, 0.908, tmp+PL+PL_cumulo+interval_Pdt.+RS+mu_cumulo+nu_cumulo+rho_cumulo+nu_per_rho_cumulo+RQ_integral+Accum._Yield+emission_O2+emission_CO2+consum_O2+generate_CO2; 0.776, 0.908, tmp+PL+AN+interval_Pdt.+OD+mu_cumulo+nu_cumulo+rho_cumulo+nu_per_rho_cumulo+Accum._Yield+emission_O2+emission_CO2+consum_O2+generate_CO2; 0.789, 0.908, tmp+PL+AN+interval_Pdt.+mu_cumulo+rho_cumulo+rab_integral+Accum._Yield+emission_CO2+consum_O2+generate_CO2; 0.776, 0.908, tmp+PL+PL_cumulo+AN+interval_Pdt.+OD+mu_cumulo+nu_cumulo+rho_cumulo+nu_per_rho_cumulo+rab_integral+emission_CO2+consum_O2+generate_CO2; 0.780, 0.908, tmp+PL+AN+interval_Pdt.+OD+nu_cumulo+rho_cumulo+nu_per_rho_cumulo+rab_integral+Accum._Yield+emission_CO2+consum_O2+generate_CO2; 0.784, 0.908, tmp+interval_Pdt.+mu_cumulo+nu_cumulo+rho_cumulo+nu_per_rho_cumulo+cell_yield_cumulo+rab_integral+Accum._Yield+emission_CO2+consum_O2+generate_CO2; 0.776, 0.908, tmp+PL+AN+interval_Pdt.+mu_cumulo+nu_cumulo+rho_cumulo+nu_per_rho_cumulo+RQ_integral+Accum._Yield+emission_O2+emission_CO2+consum_O2+generate_CO2; 0.772, 0.908, tmp+PL+interval_Pdt.+mu_cumulo+nu_cumulo+rho_cumulo+nu_per_rho_cumulo+cell_yield_cumulo+rab_integral+RQ_integral+Accum._Yield+emission_CO2+consum_O2+interval_O2+generate_CO2; 0.776, 0.908, tmp+PL+AN+interval_Pdt.+mu_cumulo+nu_cumulo+rho_cumulo+nu_per_rho_cumulo+rab_integral+emission_CO2+consum_O2+interval_O2+generate_CO2; 0.772, 0.908, tmp+PL+PL_cumulo+AN+interval_Pdt.+RS+mu_cumulo+nu_cumulo+rho_cumulo+nu_per_rho_cumulo+rab_integral+emission_CO2+consum_O2+interval_O2+generate_CO2; 0.772, 0.908, tmp+PL+PL_cumulo+AN+interval_yield+interval_Pdt.+mu_cumulo+nu_cumulo+rho_cumulo+nu_per_rho_cumulo+cell_yield_cumulo+rab_integral+emission_CO2+consum_O2+generate_CO2; 0.788, 0.908, tmp+PL+interval_Pdt.+mu_cumulo+nu_cumulo+rho_cumulo+nu_per_rho_cumulo+Arg_conc._cumulo+emission_CO2+consum_O2+generate_CO2; 0.776, 0.908, tmp+PL+AN+interval_Pdt.+RS+mu_cumulo+nu_cumulo+rho_cumulo+nu_per_rho_cumulo+Arg_conc._cumulo+rab_integral+emission_CO2+consum_O2+generate_CO2; 0.772, 0.908, tmp+PL+PL_cumulo+AN+interval_Pdt.+OD+mu_cumulo+nu_cumulo+rho_cumulo+nu_per_rho_cumulo+rab_integral+Accum._Yield+emission_CO2+consum_O2+generate_CO2; 0.788, 0.908, tmp+PL+interval_Pdt.+RS+mu_cumulo+nu_cumulo+rho_cumulo+nu_per_rho_cumulo+emission_CO2+consum_O2+generate_CO2; 0.784, 0.908, tmp+PL_cumulo+interval_Pdt.+mu_cumulo+nu_cumulo+rho_cumulo+nu_per_rho_cumulo+cell_yield_cumulo+Accum._Yield+emission_CO2+consum_O2+generate_CO2; 0.780, 0.908, tmp+PL+AN+interval_Pdt.+mu_cumulo+nu_cumulo+rho_cumulo+nu_per_rho_cumulo+RQ_integral+emission_CO2+consum_O2+interval_O2+generate_CO2; 0.767, 0.908, tmp+PL+PL_cumulo+AN+interval_Pdt.+RS+mu_cumulo+nu_cumulo+rho_cumulo+nu_per_rho_cumulo+rab_integral+Accum._Yield+emission_CO2+consum_O2+interval_O2+generate_CO2; 0.771, 0.908, tmp+PL+PL_cumulo+interval_Pdt.+OD+nu_cumulo+rho_cumulo+nu_per_rho_cumulo+Arg_conc._cumulo+rab_integral+RQ_integral+Accum._Yield+emission_CO2+consum_O2+generate_CO2; 0.767, 0.908, tmp+PL+interval_Pdt.+RS+mu_cumulo+nu_cumulo+rho_cumulo+nu_per_rho_cumulo+Arg_conc._cumulo+cell_yield_cumulo+RQ_integral+Accum._Yield+emission_O2+emission_CO2+consum_O2+generate_CO2; 0.776, 0.908, tmp+pH+PL_cumulo+interval_Pdt.+mu_cumulo+nu_cumulo+rho_cumulo+nu_per_rho_cumulo+rab_integral+RQ_integral+Accum._Yield+emission_CO2+consum_O2+generate_CO2; 0.780, 0.908, tmp+PL_cumulo+interval_Pdt.+OD+mu_cumulo+nu_cumulo+rho_cumulo+nu_per_rho_cumulo+cell_yield_cumulo+rab_integral+emission_CO2+consum_O2+generate_CO2; 0.776, 0.908, tmp+PL+PL_cumulo+interval_Pdt.+mu_cumulo+nu_cumulo+rho_cumulo+nu_per_rho_cumulo+cell_yield_cumulo+Accum._Yield+emission_O2+emission_CO2+consum_O2+generate_CO2; 0.767, 0.908, tmp+PL+PL_cumulo+AN+interval_Pdt.+mu_cumulo+nu_cumulo+rho_cumulo+nu_per_rho_cumulo+cell_yield_cumulo+rab_integral+Accum._Yield+emission_CO2+consum_O2+interval_O2+generate_CO2; 0.788, 0.908, tmp+PL+AN+interval_yield+interval_Pdt.+mu_cumulo+rho_cumulo+emission_CO2+consum_O2+interval_O2+generate_CO2; 0.784, 0.908, tmp+PL_cumulo+AN+interval_Pdt.+mu_cumulo+nu_cumulo+rho_cumulo+nu_per_rho_cumulo+cell_yield_cumulo+emission_CO2+consum_O2+generate_CO2; 0.776, 0.908, tmp+PL+interval_Pdt.+mu_cumulo+nu_cumulo+ rho_cumulo+nu_per_rho_cumulo+cell_yield_cumulo+rab_integral+RQ_integral+emission_CO2+consum_O2+interval_O2+generate_CO2; 0.776, 0.908, tmp+pH+PL+interval_Pdt.+mu_cumulo+nu_cumulo+rho_cumulo+nu_per_rho_cumulo+RQ_integral+Accum._Yield+emission_O2+emission_CO2+consum_O2+generate_CO2; 0.780, 0.908, tmp+PL+interval_Pdt.+RS+mu_cumulo+nu_cumulo+rho_cumulo+nu_per_rho_cumulo+RQ_integral+emission_O2+emission_CO2+consum_O2+generate_CO2; 0.771, 0.908, tmp+PL+PL_cumulo+interval_Pdt.+OD+mu_cumulo+nu_cumulo+rho_cumulo+nu_per_rho_cumulo+RQ_integral+Accum._Yield+emission_O2+emission_CO2+consum_O2+generate_CO2; 0.788, 0.908, tmp+PL+AN+interval_Pdt.+mu_cumulo+rho_cumulo+Arg_conc._cumulo+Accum._Yield+emission_CO2+consum_O2+generate_CO2; 0.788, 0.908, tmp+PL_cumulo+interval_Pdt.+mu_cumulo+nu_cumulo+rho_cumulo+nu_per_rho_cumulo+Arg_conc._cumulo+emission_CO2+consum_O2+generate_CO2; 0.767, 0.908, tmp+pH+PL+PL_cumulo+interval_Pdt.+OD+nu_cumulo+rho_cumulo+nu_per_rho_cumulo+Arg_conc._cumulo+Accum._Yield+emission_O2+emission_CO2+consum_O2+interval_O2+generate_CO2; 0.776, 0.908, tmp+PL+interval_Pdt.+OD+mu_cumulo+nu_cumulo+rho_cumulo+nu_per_rho_cumulo+Arg_conc._cumulo+cell_yield_cumulo+rab_integral+emission_CO2+consum_O2+generate_CO2; 0.784, 0.908, tmp+PL+interval_Pdt.+OD+nu_cumulo+rho_cumulo+nu_per_rho_cumulo+rab_integral+emission_CO2+consum_O2+interval_O2+generate_CO2; 0.776, 0.908, tmp+PL+interval_Pdt.+mu_cumulo+nu_cumulo+rho_cumulo+nu_per_rho_cumulo+cell_yield_cumulo+RQ_integral+emission_O2+emission_CO2+consum_O2+interval_O2+generate_CO2; 0.776, 0.908, tmp+PL+interval_Pdt.+OD+RS+mu_cumulo+nu_cumulo+rho_cumulo+nu_per_rho_cumulo+cell_yield_cumulo+rab_integral+emission_CO2+consum_O2+generate_CO2; 0.784, 0.908, tmp+PL+AN+interval_yield+interval_Pdt.+mu_cumulo+rho_cumulo+Accum._Yield+emission_CO2+consum_O2+interval_O2+generate_CO2; 0.788, 0.908, tmp+PL+PL_cumulo+interval_Pdt.+mu_cumulo+nu_cumulo+rho_cumulo+nu_per_rho_cumulo+emission_CO2+consum_O2+generate_CO2; 0.776, 0.908, tmp+PL+interval_Pdt.+OD+RS+mu_cumulo+nu_cumulo+rho_cumulo+nu_per_rho_cumulo+rab_integral+Accum._Yield+emission_CO2+consum_O2+generate_CO2; 0.780, 0.908, tmp+PL+PL_cumulo+AN+interval_Pdt.+mu_cumulo+rho_cumulo+Accum._Yield+emission_O2+emission_CO2+consum_O2+interval_O2+generate_CO2; 0.780, 0.908, tmp+PL+PL_cumulo+interval_Pdt.+mu_cumulo+nu_cumulo+rho_cumulo+nu_per_rho_cumulo+Arg_conc._cumulo+emission_O2+emission_CO2+consum_O2+generate_CO2; 0.776, 0.908, tmp+PL+PL_cumulo+AN+OD+nu_cumulo+rho_cumulo+nu_per_rho_cumulo+Arg_conc._cumulo+Accum._Yield+emission_O2+emission_CO2+consum_O2+generate_CO2; 0.771, 0.908, tmp+PL+AN+interval_Pdt.+mu_cumulo+nu_cumulo+rho_cumulo+nu_per_rho_cumulo+RQ_integral+Accum._Yield+emission_O2+emission_CO2+consum_O2+interval_O2+generate_CO2; 0.771, 0.908, tmp+PL+AN+interval_Pdt.+mu_cumulo+nu_cumulo+rho_cumulo+nu_per_rho_cumulo+Arg_conc._cumulo+rab_integral+Accum._Yield+emission_CO2+consum_O2+interval_O2+generate_CO2; 0.766, 0.908, tmp+PL+PL_cumulo+AN+interval_Pdt.+mu_cumulo+nu_cumulo+rho_cumulo+nu_per_rho_cumulo+rab_integral+RQ_integral+Accum._Yield+emission_O2+emission_CO2+consum_O2+interval_O2+generate_CO2; 0.771, 0.908, tmp+PL+AN+interval_Pdt.+RS+mu_cumulo+nu_cumulo+rho_cumulo+nu_per_rho_cumulo+Arg_conc._cumulo+rab_integral+Accum._Yield+emission_CO2+consum_O2+generate_CO2; 0.771, 0.908, tmp+PL+interval_Pdt.+mu_cumulo+nu_cumulo+rho_cumulo+nu_per_rho_cumulo+rab_integral+RQ_integral+Accum._Yield+emission_O2+emission_CO2+consum_O2+interval_O2+generate_CO2; 0.771, 0.908, tmp+PL+PL_cumulo+AN+interval_Pdt.+mu_cumulo+nu_cumulo+rho_cumulo+nu_per_rho_cumulo+RQ_integral+emission_O2+emission_CO2+consum_O2+interval_O2+generate_CO2; 0.771, 0.908, tmp+pH+PL+AN+interval_Pdt.+mu_cumulo+nu_cumulo+rho_cumulo+nu_per_rho_cumulo+rab_integral+RQ_integral+Accum._Yield+emission_CO2+consum_O2+generate_CO2; 0.766, 0.908, tmp+PL+PL_cumulo+AN+interval_Pdt.+mu_cumulo+nu_cumulo+rho_cumulo+nu_per_rho_cumulo+rab_integral+RQ_integral+Accum._Yield+emission_O2+emission_CO2+consum_O2+generate_CO2; 0.771, 0.908, tmp+PL+AN+interval_Pdt.+OD+mu_cumulo+nu_cumulo+rho_cumulo+nu_per_rho_cumulo+Accum._Yield+emission_O2+emission_CO2+consum_O2+interval_O2+generate_CO2; 0.766, 0.908, tmp+PL+interval_Pdt.+OD+RS+mu_cumulo+nu_cumulo+rho_cumulo+nu_per_rho_cumulo+Arg_conc._cumulo+rab_integral+RQ_integral+Accum._Yield+emission_CO2+consum_O2+generate_CO2; 0.780, 0.908, tmp+PL+AN+interval_Pdt.+OD+mu_cumulo+nu_cumulo+rho_cumulo+nu_per_rho_cumulo+Arg_conc._cumulo+emission_CO2+consum_O2+generate_CO2; 0.780, 0.908, tmp+PL+interval_Pdt.+mu_cumulo+nu_cumulo+rho_cumulo+nu_per_rho_cumulo+rab_integral+RQ_integral+emission_O2+emission_CO2+consum_O2+generate_CO2; 0.771, 0.908, tmp+PL+AN+interval_Pdt.+OD+mu_cumulo+nu_cumulo+rho_cumulo+nu_per_rho_cumulo+cell_yield_cumulo+rab_integral+emission_CO2+consum_O2+interval_O2+generate_CO2; 0.780, 0.908, tmp+PL+AN+interval_Pdt.+RS+mu_cumulo+nu_cumulo+rho_cumulo+nu_per_rho_cumulo+cell_yield_cumulo+emission_CO2+consum_O2+generate_CO2; 0.766, 0.908, tmp+PL+PL_cumulo+interval_Pdt.+OD+mu_cumulo+nu_cumulo+rho_cumulo+nu_per_rho_cumulo+Arg_conc._cumulo+rab_integral+Accum._Yield+emission_O2+emission_CO2+consum_O2+generate_CO2; 0.776, 0.908, tmp+PL+AN+interval_Pdt.+mu_cumulo+nu_cumulo+rho_cumulo+nu_per_rho_cumulo+rab_integral+Accum._Yield+emission_O2+emission_CO2+consum_O2+generate_CO2; 0.776, 0.908, tmp+PL+AN+interval_Pdt.+OD+mu_cumulo+nu_cumulo+rho_cumulo+nu_per_rho_cumulo+Arg_conc._cumulo+rab_integral+emission_CO2+consum_O2+generate_CO2; 0.788, 0.908, tmp+PL+AN+interval_Pdt.+mu_cumulo+rho_cumulo+nu_per_rho_cumulo+Arg_conc._cumulo+emission_CO2+consum_O2+generate_CO2; 0.780, 0.908, tmp+PL+interval_Pdt.+OD+mu_cumulo+nu_cumulo+rho_cumulo+nu_per_rho_cumulo+Arg_conc._cumulo+emission_O2+emission_CO2+consum_O2+generate_CO2; 0.780, 0.908, tmp+PL+interval_Pdt.+OD+nu_cumulo+rho_cumulo+nu_per_rho_cumulo+Arg_conc._cumulo+emission_O2+emission_CO2+consum_O2+interval_O2+generate_CO2; 0.784, 0.908, tmp+pH+PL_cumulo+interval_Pdt.+mu_cumulo+nu_cumulo+rho_cumulo+nu_per_rho_cumulo+rab_integral+emission_CO2+consum_O2+generate_CO2; 0.788, 0.908, tmp+interval_Pdt.+RS+mu_cumulo+nu_cumulo+rho_cumulo+nu_per_rho_cumulo+rab_integral+emission_CO2+consum_O2+generate_CO2; 0.784, 0.908, tmp+pH+OD+nu_cumulo+rho_cumulo+nu_per_rho_cumulo+Arg_conc._cumulo+rab_integral+Accum._Yield+emission_CO2+consum_O2+generate_CO2; 0.784, 0.908, tmp+PL_cumulo+OD+nu_cumulo+rho_cumulo+nu_per_rho_ cumulo+Arg_conc._cumulo+rab_integral+Accum._Yield+emission_CO2+consum_O2+generate_CO2; 0.788, 0.908, tmp+PL+interval_Pdt.+mu_cumulo+nu_cumulo+rho_cumulo+nu_per_rho_cumulo+cell_yield_cumulo+emission_CO2+consum_O2+generate_CO2; 0.784, 0.908, tmp+PL_cumulo+AN+interval_Pdt.+OD+mu_cumulo+nu_cumulo+rho_cumulo+nu_per_rho_cumulo+emission_CO2+consum_O2+generate_CO2; 0.780, 0.908, tmp+PL+PL_cumulo+AN+interval_Pdt.+mu_cumulo+rho_cumulo+rab_integral+Accum._Yield+emission_CO2+consum_O2+interval_O2+generate_CO2; 0.775, 0.908, tmp+PL+AN+interval_Pdt.+RS+mu_cumulo+nu_cumulo+rho_cumulo+nu_per_rho_cumulo+rab_integral+RQ_integral+emission_CO2+consum_O2+generate_CO2; 0.775, 0.908, tmp+PL+interval_Pdt.+mu_cumulo+nu_cumulo+rho_cumulo+nu_per_rho_cumulo+Arg_conc._cumulo+cell_yield_cumulo+rab_integral+RQ_integral+emission_CO2+consum_O2+generate_CO2; 0.775, 0.908, tmp+PL+AN+interval_Pdt.+OD+RS+mu_cumulo+nu_cumulo+rho_cumulo+nu_per_rho_cumulo+rab_integral+emission_CO2+consum_O2+generate_CO2; 0.771, 0.908, tmp+PL+PL_cumulo+AN+interval_Pdt.+RS+mu_cumulo+nu_cumulo+rho_cumulo+nu_per_rho_cumulo+emission_O2+emission_CO2+consum_O2+interval_O2+generate_CO2; 0.775, 0.908, tmp+PL+AN+interval_Pdt.+RS+mu_cumulo+nu_cumulo+rho_cumulo+nu_per_rho_cumulo+emission_O2+emission_CO2+consum_O2+interval_O2+generate_CO2; 0.761, 0.908, tmp+PL+PL_cumulo+AN+interval_Pdt.+mu_cumulo+nu_cumulo+rho_cumulo+nu_per_rho_cumulo+rab_integral+RQ_integral+Accum._Yield+emission_O2+emission_CO2+consum_O2+interval_O2+generate_CO2; 0.775, 0.908, tmp+pH+PL+interval_Pdt.+mu_cumulo+nu_cumulo+rho_cumulo+nu_per_rho_cumulo+cell_yield_cumulo+rab_integral+Accum._Yield+emission_CO2+consum_O2+generate_CO2; 0.780, 0.908, tmp+PL+AN+interval_Pdt.+mu_cumulo+nu_cumulo+rho_cumulo+nu_per_rho_cumulo+rab_integral+emission_O2+emission_CO2+consum_O2+generate_CO2; 0.775, 0.908, tmp+PL_cumulo+interval_Pdt.+RS+mu_cumulo+nu_cumulo+rho_cumulo+nu_per_rho_cumulo+cell_yield_cumulo+rab_integral+Accum._Yield+emission_CO2+consum_O2+generate_CO2; 0.775, 0.908, tmp+PL+PL_cumulo+AN+interval_Pdt.+mu_cumulo+nu_cumulo+rho_cumulo+nu_per_rho_cumulo+Accum._Yield+emission_CO2+consum_O2+interval_O2+generate_CO2; 0.771, 0.908, tmp+pH+PL+interval_Pdt.+mu_cumulo+nu_cumulo+rho_cumulo+nu_per_rho_cumulo+Arg_conc._cumulo+rab_integral+RQ_integral+Accum._Yield+emission_CO2+consum_O2+generate_CO2; 0.775, 0.908, tmp+PL+interval_Pdt.+RS+mu_cumulo+nu_cumulo+rho_cumulo+nu_per_rho_cumulo+cell_yield_cumulo+Accum._Yield+emission_O2+emission_CO2+consum_O2+generate_CO2; 0.771, 0.908, tmp+PL+AN+interval_Pdt.+mu_cumulo+nu_cumulo+rho_cumulo+nu_per_rho_cumulo+cell_yield_cumulo+RQ_integral+Accum._Yield+emission_O2+emission_CO2+consum_O2+generate_CO2; 0.780, 0.908, tmp+PL+interval_Pdt.+mu_cumulo+nu_cumulo+rho_cumulo+nu_per_rho_cumulo+cell_yield_cumulo+rab_integral+emission_O2+emission_CO2+consum_O2+generate_CO2; 0.784, 0.908, tmp+PL_cumulo+interval_Pdt.+mu_cumulo+nu_cumulo+rho_cumulo+nu_per_rho_cumulo+cell_yield_cumulo+emission_O2+emission_CO2+consum_O2+generate_CO2; 0.775, 0.908, tmp+PL+PL_cumulo+interval_Pdt.+mu_cumulo+nu_cumulo+rho_cumulo+nu_per_rho_cumulo+rab_integral+emission_O2+emission_CO2+consum_O2+interval_O2+generate_CO2; 0.784, 0.908, tmp+PL+AN+interval_Pdt.+mu_cumulo+rho_cumulo+nu_per_rho_cumulo+Accum._Yield+emission_CO2+consum_O2+interval_O2+generate_CO2; 0.775, 0.908, tmp+PL+AN+interval_Pdt.+OD+nu_cumulo+rho_cumulo+nu_per_rho_cumulo+Arg_conc._cumulo+Accum._Yield+emission_CO2+consum_O2+interval_O2+generate_CO2; 0.766, 0.908, tmp+PL+PL_cumulo+AN+interval_Pdt.+OD+mu_cumulo+nu_cumulo+rho_cumulo+nu_per_rho_cumulo+Accum._Yield+emission_O2+emission_CO2+consum_O2+interval_O2+generate_CO2; 0.771, 0.908, tmp+PL+PL_cumulo+AN+interval_Pdt.+RS+mu_cumulo+nu_cumulo+rho_cumulo+nu_per_rho_cumulo+Accum._Yield+emission_O2+emission_CO2+consum_O2+generate_CO2; 0.771, 0.908, tmp+PL+PL_cumulo+interval_Pdt.+RS+mu_cumulo+nu_cumulo+nu_per_rho_cumulo+Arg_conc._cumulo+rab_integral+Accum._Yield+emission_CO2+consum_O2+generate_CO2; 0.784, 0.908, tmp+PL+interval_Pdt.+mu_cumulo+nu_cumulo+rho_cumulo+nu_per_rho_cumulo+Arg_conc._cumulo+Accum._Yield+emission_CO2+consum_O2+generate_CO2; 0.788, 0.908, tmp+PL+AN+interval_Pdt.+mu_cumulo+rho_cumulo+cell_yield_cumulo+Accum._Yield+emission_CO2+consum_O2+generate_CO2; 0.784, 0.908, tmp+PL_cumulo+interval_Pdt.+mu_cumulo+nu_cumulo+rho_cumulo+nu_per_rho_cumulo+rab_integral+emission_CO2+consum_O2+interval_O2+generate_CO2; 0.784, 0.908, tmp+PL+AN+interval_Pdt.+RS+mu_cumulo+rho_cumulo+Accum._Yield+emission_CO2+consum_O2+interval_O2+generate_CO2; 0.791, 0.907, tmp+PL+AN+interval_yield+interval_Pdt.+mu_cumulo+rho_cumulo+emission_CO2+consum_O2+generate_CO2; 0.784, 0.907, tmp+PL+AN+interval_yield+interval_Pdt.+mu_cumulo+nu_cumulo+rho_cumulo+nu_per_rho_cumulo+emission_CO2+consum_O2+generate_CO2; 0.775, 0.907, tmp+PL+AN+interval_Pdt.+RS+mu_cumulo+nu_cumulo+rho_cumulo+nu_per_rho_cumulo+cell_yield_cumulo+Accum._Yield+emission_CO2+consum_O2+generate_CO2; 0.771, 0.907, tmp+PL+PL_cumulo+AN+interval_Pdt.+OD+mu_cumulo+nu_cumulo+rho_cumulo+nu_per_rho_cumulo+emission_O2+emission_CO2+consum_O2+interval_O2+generate_CO2; 0.775, 0.907, tmp+PL+interval_Pdt.+OD+mu_cumulo+nu_cumulo+rho_cumulo+nu_per_rho_cumulo+cell_yield_cumulo+Accum._Yield+emission_O2+emission_CO2+consum_O2+generate_CO2; 0.779, 0.907, tmp+pH+PL_cumulo+interval_Pdt.+mu_cumulo+nu_cumulo+rho_cumulo+nu_per_rho_cumulo+rab_integral+RQ_integral+emission_CO2+consum_O2+generate_CO2; 0.791, 0.907, tmp+PL+AN+interval_Pdt.+mu_cumulo+rho_cumulo+emission_CO2+consum_O2+interval_O2+generate_CO2; 0.771, 0.907, tmp+PL+PL_cumulo+AN+interval_Pdt.+mu_cumulo+nu_cumulo+rho_cumulo+nu_per_rho_cumulo+cell_yield_cumulo+Accum._Yield+emission_O2+emission_CO2+consum_O2+generate_CO2; 0.771, 0.907, tmp+PL+PL_cumulo+AN+interval_Pdt.+mu_cumulo+nu_cumulo+rho_cumulo+nu_per_rho_cumulo+rab_integral+RQ_integral+emission_CO2+consum_O2+interval_O2+generate_CO2; 0.779, 0.907, tmp+PL+PL_cumulo+interval_Pdt.+RS+mu_cumulo+nu_cumulo+rho_cumulo+nu_per_rho_cumulo+emission_O2+emission_CO2+consum_O2+generate_CO2; 0.775, 0.907, tmp+pH+PL+AN+interval_Pdt.+mu_cumulo+nu_cumulo+rho_cumulo+nu_per_rho_cumulo+rab_integral+emission_CO2+consum_O2+interval_O2+generate_CO2; 0.775, 0.907, tmp+PL+PL_cumulo+interval_Pdt.+RS+mu_cumulo+nu_cumulo+rho_cumulo+nu_per_rho_cumulo+Accum._Yield+emission_O2+emission_CO2+consum_O2+generate_CO2; 0.779, 0.907, tmp+PL+AN+interval_Pdt.+RS+mu_cumulo+nu_cumulo+rho_cumulo+nu_per_rho_cumulo+emission O2+emission_CO2+consum_O2+generate_CO2; 0.779, 0.907, tmp+PL+interval_Pdt.+mu_cumulo+nu_cumulo+rho_cumulo+nu_per_rho_cumulo+Arg_conc._cumulo+RQ_integral+emission_O2+emission_CO2+consum_O2+generate_CO2; 0.775, 0.907, tmp+PL+AN+interval_Pdt.+RS+mu_cumulo+nu_cumulo+rho_cumulo+nu_per_rho_cumulo+Accum._Yield+emission_O2+emission_CO2+consum_O2+generate_CO2; 0.783, 0.907, tmp+PL+AN+interval_Pdt.+mu_cumulo+rho_cumulo+Arg_conc._cumulo+Accum._Yield+emission_CO2+consum_O2+interval_O2+generate_CO2; 0.766, 0.907, tmp+PL+PL_cumulo+interval_Pdt.+mu_cumulo+nu_cumulo+rho_cumulo+nu_per_rho_cumulo+cell_yield_cumulo+RQ_integral+Accum._Yield+emission_O2+emission_CO2+consum_O2+interval_O2+generate_CO2; 0.779, 0.907, tmp+PL_cumulo+interval_Pdt.+OD+mu_cumulo+nu_cumulo+rho_cumulo+nu_per_rho_cumulo+rab_integral+Accum._Yield+emission_CO2+consum_O2+generate_CO2; 0.779, 0.907, tmp+PL+AN+interval_Pdt.+mu_cumulo+nu_cumulo+rho_cumulo+nu_per_rho_cumulo+Arg_conc._cumulo+emission_O2+emission_CO2+consum_O2+generate_CO2; 0.783, 0.907, tmp+PL+AN+interval_yield+interval_Pdt.+mu_cumulo+rho_cumulo+nu_per_rho_cumulo._Yield+emission_CO2+consum_O2+generate_CO2; 0.775, 0.907, tmp+PL+PL_cumulo+interval_Pdt.+mu_cumulo+nu_cumulo+rho_cumulo+nu_per_rho_cumulo+cell_yield_cumulo+emission_O2+emission_CO2+consum_O2+interval_O2+generate_CO2; 0.787, 0.907, tmp+PL+interval_Pdt.+OD+mu_cumulo+nu_cumulo+rho_cumulo+nu_per_rho_cumulo+emission_CO2+consum_O2+generate_CO2; 0.775, 0.907, tmp+PL_cumulo+interval_Pdt.+OD+mu_cumulo+nu_cumulo+rho_cumulo+nu_per_rho_cumulo+rab_integral+RQ_integral+Accum._Yield+emission_CO2+consum_O2+generate_CO2; 0.761, 0.907, tmp+PL+PL_cumulo+AN+interval_Pdt.+OD+RS+mu_cumulo+nu_cumulo+rho_cumulo+nu_per_rho_cumulo+Arg_conc._cumulo+rab_integral+Accum._Yield+emission_CO2+consum_O2+generate_CO2; 0.775, 0.907, tmp+PL+PL_cumulo+OD+nu_cumulo+rho_cumulo+nu_per_rho_cumulo+Arg_conc._cumulo+Accum._Yield+emission_O2+emission_CO2+consum_O2+interval_O2+generate_CO2; 0.783, 0.907, tmp+PL+AN+interval_Pdt.+mu_cumulo+rho_cumulo+nu_per_rho_cumulo+rab_integral+emission_CO2+consum_O2+interval_O2+generate_CO2; 0.783, 0.907, tmp+PL_cumulo+interval_Pdt.+OD+mu_cumulo+nu_cumulo+rho_cumulo+nu_per_rho_cumulo+Accum._Yield+emission_CO2+consum_O2+generate_CO2; 0.779, 0.907, tmp+PL+interval_Pdt.+OD+nu_cumulo+rho_cumulo+nu_per_rho_cumulo+RQ_integral+emission_O2+emission_CO2+consum_O2+interval_O2+generate_CO2; 0.783, 0.907, tmp+interval_Pdt.+RS+mu_cumulo+nu_cumulo+rho_cumulo+nu_per_rho_cumulo+rab_integral+Accum._Yield+emission_CO2+consum_O2+generate_CO2; 0.787, 0.907, tmp+PL+interval_Pdt.+mu_cumulo+rho_cumulo+rab_integral+RQ_integral+Accum._Yield+emission_CO2+consum_O2+generate_CO2; 0.783, 0.907, tmp+PL_cumulo+AN+interval_Pdt.+mu_cumulo+nu_cumulo+rho_cumulo+nu_per_rho_cumulo+emission_CO2+consum_O2+interval_O2+generate_CO2; 0.779, 0.907, tmp+PL+interval_Pdt.+OD+RS+mu_cumulo+nu_cumulo+rho_cumulo+nu_per_rho_cumulo+emission_O2+emission_CO2+consum_O2+generate_CO2; 0.770, 0.907, tmp+PL+interval_Pdt.+RS+mu_cumulo+nu_cumulo+rho_cumulo+nu_per_rho_cumulo+RQ_integral+Accum._Yield+emission_O2+emission_CO2+consum_O2+interval_O2+generate_CO2; 0.779, 0.907, tmp+PL+AN+interval_Pdt.+OD+nu_cumulo+rho_cumulo+nu_per_rho_cumulo+emission_O2+emission_CO2+consum_O2+interval_O2+generate_CO2; 0.783, 0.907, tmp+PL+interval_Pdt.+OD+nu_cumulo+rho_cumulo+nu_per_rho_cumulo+emission_O2+emission_CO2+consum_O2+interval_O2+generate_CO2; 0.770, 0.907, tmp+pH+PL+AN+interval_Pdt.+OD+nu_cumulo+rho_cumulo+nu_per_rho_cumulo+Arg_conc._cumulo+rab_integral+Accum._Yield+emission_CO2+consum_O2+generate_CO2; 0.783, 0.907, tmp+PL+AN+interval_Pdt.+mu_cumulo+nu_cumulo+rho_cumulo+Accum._Yield+emission_CO2+consum_O2+interval_O2+generate_CO2; 0.783, 0.907, tmp+pH+interval_Pdt.+mu_cumulo+nu_cumulo+rho_cumulo+nu_per_rho_cumulo+rab_integral+RQ_integral+emission_CO2+consum_O2+generate_CO2; 0.779, 0.907, tmp+PL+PL_cumulo+interval_Pdt.+OD+mu_cumulo+nu_cumulo+rho_cumulo+nu_per_rho_cumulo+emission_O2+emission_CO2+consum_O2+generate_CO2; 0.770, 0.907, tmp+PL+AN+interval_Pdt.+mu_cumulo+nu_cumulo+rho_cumulo+nu_per_rho_cumulo+rab_integral+Accum._Yield+emission_O2+emission_CO2+consum_O2+interval_O2+generate_CO2; 0.770, 0.907, tmp+PL+interval_Pdt.+RS+mu_cumulo+nu_cumulo+rho_cumulo+nu_per_rho_cumulo+Arg_conc._cumulo+RQ_integral+Accum._Yield+emission_O2+emission_CO2+consum_O2+generate_CO2; 0.770, 0.907, tmp+PL+AN+interval_Pdt.+RS+mu_cumulo+nu_cumulo+rho_cumulo+nu_per_rho_cumulo+cell_yield_cumulo+rab_integral+emission_CO2+consum_O2+interval_O2+generate_CO2; 0.783, 0.907, tmp+PL_cumulo+interval_Pdt.+OD+mu_cumulo+nu_cumulo+rho_cumulo+nu_per_rho_cumulo+cell_yield_cumulo+emission_CO2+consum_O2+generate_CO2; 0.775, 0.907, tmp+PL+interval_Pdt.+RS+mu_cumulo+nu_cumulo+rho_cumulo+nu_per_rho_cumulo+Arg_conc._cumulo+rab_integral+RQ_integral+emission_CO2+consum_O2+generate_CO2; 0.779, 0.907, tmp+PL_cumulo+interval_Pdt.+mu_cumulo+nu_cumulo+rho_cumulo+nu_per_rho_cumulo+cell_yield_cumulo+rab_integral+emission_CO2+consum_O2+interval_O2+generate_CO2; 0.775, 0.907, tmp+PL+PL_cumulo+AN+interval_Pdt.+mu_cumulo+nu_cumulo+rho_cumulo+nu_per_rho_cumulo+cell_yield_cumulo+emission_O2+emission_CO2+consum_O2+generate_CO2; 0.765, 0.907, tmp+pH+PL+PL_cumulo+interval_Pdt.+OD+nu_cumulo+rho_cumulo+nu_per_rho_cumulo+Arg_conc._cumulo+rab_integral+Accum._Yield+emission_O2+emission_CO2+consum_O2+generate_CO2; 0.779, 0.907, tmp+PL_cumulo+interval_Pdt.+RS+mu_cumulo+nu_cumulo+rho_cumulo+nu_per_rho_cumulo+rab_integral+Accum._Yield+emission_CO2+consum_O2+generate_CO2; 0.779, 0.907, tmp+PL_cumulo+interval_Pdt.+OD+nu_cumulo+rho_cumulo+nu_per_rho_cumulo+Arg_conc._cumulo+rab_integral+Accum._Yield+emission_CO2+consum_O2+generate_CO2; 0.775, 0.907, tmp+pH+PL+AN+interval_Pdt.+mu_cumulo+nu_cumulo+rho_cumulo+nu_per_rho_cumulo+Arg_conc._cumulo+Accum._Yield+emission_CO2+consum_O2+generate_CO2; 0.765, 0.907, tmp+PL+AN+interval_Pdt.+mu_cumulo+nu_cumulo+rho_cumulo+nu_per_rho_cumulo+Arg_conc._cumulo+cell_yield_cumulo+rab_integral+RQ_integral+Accum._Yield+emission_CO2+consum_O2+generate_CO2; 0.770, 0.907, tmp+PL+AN+interval_Pdt.+mu_cumulo+nu_cumulo+rho_cumulo+nu_per_rho_cumulo+Arg_conc._cumulo+cell_yield_cumulo+emission_O2+emission_CO2+consum_O2+interval_O2+generate_CO2; 0.779, 0.907, tmp+PL+PL_cumulo+AN+interval_Pdt.+mu_cumulo+nu_cumulo+rho_cumulo+nu_per_rho_cumulo+Arg_conc._cumulo+emission_CO2+consum_O2+generate_CO2; 0.770, 0.907, tmp+PL+AN+interval_Pdt.+RS+mu_cumulo+nu_cumulo+ rho_cumulo+nu_per_rho_cumulo+Arg_conc._cumulo+ cell_yield_cumulo+rab_integral+emission_CO2+consum_ O2+generate_CO2; 0.779, 0.907, tmp+PL+AN+interval_ Pdt.+OD+RS+mu_cumulo+nu_cumulo+rho_cumulo+nu_ per_rho_cumulo+emission_CO2+consum_O2+generate_ CO2; 0.779, 0.907, tmp+PL+AN+interval_Pdt.+OD+nu_ cumulo+rho_cumulo+nu_per_rho_cumulo+Arg_conc._ cumulo+emission_O2+emission_CO2+consum_O2+ generate_CO2; 0.779, 0.907, tmp+PL+interval_Pdt.+OD+ RS+nu_cumulo+rho_cumulo+nu_per_rho_cumulo+Arg_ conc._cumulo+rab_integral+emission_CO2+consum_O2+ generate_CO2; 0.779, 0.907, tmp+pH+PL+OD+nu_ cumulo+rho_cumulo+nu_per_rho_cumulo+Arg_conc._ cumulo+Accum._Yield+emission_O2+emission_CO2+ consum_O2+generate_CO2; 0.783, 0.907, tmp+PL+PL_ cumulo+AN+interval_Pdt.+mu_cumulo+rho_cumulo+rab_ integral+Accum._Yield+emission_CO2+consum_O2+ generate_CO2; 0.783, 0.907, tmp+PL_cumulo+OD+RS+ nu_cumulo+rho_cumulo+nu_per_rho_cumulo+Arg_conc._ cumulo+rab_integral+Accum._Yield+emission_CO2+ generate_CO2; 0.774, 0.907, tmp+PL_cumulo+interval_ Pdt.+RS+mu_cumulo+nu_cumulo+rho_cumulo+nu_per_ rho_cumulo+cell_yield_cumulo+rab_integral+RQ_ integral+emission_CO2+consum_O2+generate_CO2; 0.774, 0.907, tmp+pH+PL+AN+interval_Pdt.+mu_cumulo+ nu_cumulo+rho_cumulo+nu_per_rho_cumulo+cell_yield_ cumulo+rab_integral+emission_CO2+consum_O2+generate_CO2; 0.783, 0.907, tmp+PL+OD+nu_cumulo+rho_ cumulo+nu_per_rho_cumulo+Arg_conc._cumulo+ emission_O2+emission_CO2+consum_O2+interval_O2+ generate_CO2; 0.783, 0.907, tmp+PL+AN+interval_Pdt.+ RS+mu_cumulo+rho_cumulo+rab_integral+Accum._ Yield+emission_CO2+consum_O2+generate_CO2; 0.765, 0.907, tmp+PL+PL_cumulo+interval_Pdt.+mu_cumulo+ nu_cumulo+rho_cumulo+nu_per_rho_cumulo+Arg_conc._ cumulo+RQ_integral+Accum._Yield+emission_O2+emission_CO2+consum_O2+interval_O2+generate_CO2; 0.770, 0.907, tmp+PL_cumulo+interval_Pdt.+RS+mu_cumulo+nu_cumulo+rho_cumulo+nu_per_rho_cumulo+cell_ yield_cumulo+rab_integral+RQ_integral+Accum._Yield+ emission_CO2+consum_O2+generate_CO2; 0.779, 0.907, tmp+pH+PL+AN+interval_Pdt.+mu_cumulo+nu_cumulo+ rho_cumulo+nu_per_rho_cumulo+emission_CO2+consum_O2+interval_O2+generate_CO2; 0.765, 0.907, tmp+ PL+AN+interval_Pdt.+OD+RS+mu_cumulo+nu_cumulo+ rho_cumulo+nu_per_rho_cumulo+Arg_conc._cumulo+ rab_integral+Accum._Yield+emission_CO2+consum_O2+ generate_CO2; 0.774, 0.907, tmp+PL_cumulo+interval_ Pdt.+mu_cumulo+nu_cumulo+rho_cumulo+nu_per_rho_ cumulo+cell_yield_cumulo+RQ_integral+Accum._Yield+ emission_O2+emission_CO2+consum_O2+generate_CO2; 0.770, 0.907, tmp+PL+interval_Pdt.+OD+RS+mu_cumulo+ nu_cumulo+rho_cumulo+nu_per_rho_cumulo+rab_integral+RQ_integral+Accum._Yield+emission_CO2+consum_O2+generate_CO2; 0.774, 0.907, tmp+pH+PL+PL_ cumulo+interval_Pdt.+mu_cumulo+nu_cumulo+rho_ cumulo+nu_per_rho_cumulo+rab_integral+Accum._Yield+ emission_CO2+consum_O2+generate_CO2; 0.779, 0.907, tmp+PL+AN+interval_Pdt.+RS+mu_cumulo+rho_cumulo+ rab_integral+Accum._Yield+emission_CO2+consum_O2+ interval_O2+generate_CO2; 0.770, 0.907, tmp+PL+PL_cumulo+AN+interval_Pdt.+OD+mu_cumulo+nu_cumulo+ rho_cumulo+nu_per_rho_cumulo+rab_integral+emission_ CO2+consum_O2+interval_O2+generate_CO2; 0.774, 0.907, tmp+interval_Pdt.+OD+mu_cumulo+nu_cumulo+rho_cumulo+nu_per_rho_cumulo+rab_integral+Accum._Yield+emission_CO2+consum_O2+interval_O2+ generate_CO2; 0.774, 0.907, tmp+PL+PL_cumulo+OD+ nu_cumulo+rho_cumulo+nu_per_rho_cumulo+Arg_conc._ cumulo+rab_integral+Accum._Yield+emission_O2+ emission_CO2+consum_O2+generate_CO2; 0.787, 0.907, tmp+PL_cumulo+OD+nu_cumulo+rho_cumulo+nu_per_ rho_cumulo+Arg_conc._cumulo+rab_integral+Accum._ Yield+emission_CO2+generate_CO2; 0.774, 0.907, tmp+ PL+AN+interval_Pdt.+mu_cumulo+nu_cumulo+rho_ cumulo+nu_per_rho_cumulo+Arg_conc._cumulo+cell_ yield_cumulo+emission_O2+emission_CO2+consum_O2+ generate_CO2; 0.760, 0.907, tmp+PL+PL_cumulo+AN+ interval_Pdt.+OD+RS+nu_cumulo+rho_cumulo+nu_per_ rho_cumulo+Arg_conc._cumulo+Accum._Yield+ emission_O2+emission_CO2+consum_O2+interval_O2+ generate_CO2; 0.774, 0.907, tmp+PL_cumulo+interval_ Pdt.+mu_cumulo+nu_cumulo+rho_cumulo+nu_per_rho_ cumulo+Arg_conc._cumulo+cell_yield_cumulo+rab_ integral+Accum._Yield+emission_CO2+consum_O2+ generate_CO2; 0.779, 0.907, tmp+PL+PL_cumulo+OD+ nu_cumulo+rho_cumulo+Arg_conc._cumulo+rab_ integral+Accum._Yield+emission_CO2+consum_O2+ generate_CO2; 0.779, 0.907, tmp+PL_cumulo+interval_ Pdt.+OD+mu_cumulo+nu_cumulo+rho_cumulo+nu_per_ rho_cumulo+rab_integral+RQ_integral+emission_CO2+ consum_O2+generate_CO2; 0.760, 0.907, tmp+PL+PL_ cumulo+AN+interval_Pdt.+OD+mu_cumulo+nu_cumulo+ rho_cumulo+nu_per_rho_cumulo+Arg_conc._cumulo+ Accum._Yield+emission_O2+emission_CO2+consum_ O2+interval_O2+generate_CO2; 0.770, 0.907, tmp+PL+ PL_cumulo+interval_Pdt.+mu_cumulo+nu_cumulo+rho_ cumulo+nu_per_rho_cumulo+Arg_conc._cumulo+ Accum._Yield+emission_O2+emission_CO2+consum_ O2+interval_O2+generate_CO2; 0.774, 0.907, tmp+pH+ PL+interval_Pdt.+OD+nu_cumulo+rho_cumulo+nu_per_ rho_cumulo+Arg_conc._cumulo+Accum._Yield+ emission_O2+emission_CO2+consum_O2+generate_CO2; 0.770, 0.907, tmp+PL+interval_Pdt.+OD+RS+mu_cumulo+ nu_cumulo+rho_cumulo+nu_per_rho_cumulo+RQ_integral+Accum._Yield+emission_O2+emission_CO2+consum_O2+generate_CO2; 0.774, 0.907, tmp+PL+interval_ Pdt.+OD+RS+mu_cumulo+nu_cumulo+rho_cumulo+nu_ per_rho_cumulo+Arg_conc._cumulo+rab_integral+ emission_CO2+consum_O2+generate_CO2; 0.783, 0.907, tmp+PL+AN+interval_Pdt.+mu_cumulo+rho_cumulo+nu_ per_rho_cumulo+Arg_conc._cumulo+emission_CO2+consum_O2+interval_O2+generate_CO2; 0.774, 0.907, tmp+ PL+AN+interval_yield+interval_Pdt.+mu_cumulo+nu_ cumulo+rho_cumulo+nu_per_rho_cumulo+cell_yield_ cumulo+rab_integral+emission_CO2+consum_O2+ generate_CO2; 0.770, 0.907, tmp+PL+PL_cumulo+ interval_Pdt.+mu_cumulo+nu_cumulo+rho_cumulo+nu_ per_rho_cumulo+rab_integral+Accum._Yield+emission_ O2+emission_CO2+consum_O2+interval_O2+generate_ CO2; 0.774, 0.907, tmp+PL+AN+interval_Pdt.+OD+nu_ cumulo+rho_cumulo+nu_per_rho_cumulo+Arg_conc._ cumulo+rab_integral+emission_CO2+consum_O2+ interval_O2+generate_CO2; 0.783, 0.907, tmp+PL_ cumulo+interval_Pdt.+mu_cumulo+nu_cumulo+rho_ cumulo+nu_per_rho_cumulo+Arg_conc._cumulo+rab_ integral+emission_CO2+consum_O2+generate_CO2; 0.765, 0.907, tmp+PL+PL_cumulo+AN+interval_Pdt.+ OD+nu_cumulo+rho_cumulo+nu_per_rho_cumulo+Arg_ conc._cumulo+rab_integral+RQ_integral+Accum._Yield+ emission_CO2+consum_O2+generate_CO2; 0.765, 0.907, tmp+PL+PL_cumulo+interval_Pdt.+RS+mu_cumulo+nu_ cumulo+rho_cumulo+nu_per_rho_cumulo+Arg_conc._cumulo+RQ_integral+Accum._Yield+emission_O2+emission_CO2+consum_O2+generate_CO2; 0.783, 0.907, tmp+PL_cumulo+AN+interval_Pdt.+mu_cumulo+nu_cumulo+rho_cumulo+nu_per_rho_cumulo+Accum._Yield+emission_CO2+consum_O2+generate_CO2; 0.770, 0.907, tmp+pH+PL+interval_Pdt.+OD+mu_cumulo+nu_cumulo+rho_cumulo+nu_per_rho_cumulo+Arg_conc._cumulo+rab_integral+Accum._Yield+emission_CO2+consum_O2+generate_CO2; 0.787, 0.907, tmp+interval_Pdt.+mu_cumulo+nu_cumulo+rho_cumulo+nu_per_rho_cumulo+rab_integral+emission_CO2+consum_O2+interval_O2+generate_CO2; 0.779, 0.907, tmp+PL+AN+interval_Pdt.+OD+nu_cumulo+rho_cumulo+nu_per_rho_cumulo+rab_integral+RQ_integral+emission_CO2+consum_O2+generate_CO2; 0.787, 0.907, tmp+PL+AN+interval_Pdt.+RS+mu_cumulo+rho_cumulo+nu_per_rho_cumulo+emission_CO2+consum_O2+generate_CO2; 0.765, 0.907, tmp+PL+PL_cumulo+interval_Pdt.+mu_cumulo+nu_cumulo+rho_cumulo+nu_per_rho_cumulo+Arg_conc._cumulo+cell_yield_cumulo+RQ_integral+Accum._Yield+emission_O2+emission_CO2+consum_O2+generate_CO2; 0.774, 0.907, tmp+PL+interval_Pdt.+OD+RS+mu_cumulo+nu_cumulo+rho_cumulo+nu_per_rho_cumulo+rab_integral+RQ_integral+emission_CO2+consum_O2+generate_CO2; 0.770, 0.907, tmp+PL+interval_Pdt.+RS+mu_cumulo+nu_cumulo+rho_cumulo+nu_per_rho_cumulo+rab_integral+RQ_integral+Accum._Yield+emission_O2+emission_CO2+consum_O2+generate_CO2; 0.783, 0.907, tmp+PL+OD+RS+nu_cumulo+rho_cumulo+nu_per_rho_cumulo+Arg_conc._cumulo+rab_integral+emission_CO2+consum_O2+generate_CO2; 0.765, 0.907, tmp+PL+AN+interval_Pdt.+mu_cumulo+nu_cumulo+rho_cumulo+nu_per_rho_cumulo+Arg_conc._cumulo+cell_yield_cumulo+rab_integral+Accum._Yield+emission_CO2+consum_O2+interval_O2+generate_CO2; 0.770, 0.907, tmp+pH+PL+interval_Pdt.+mu_cumulo+nu_cumulo+rho_cumulo+nu_per_rho_cumulo+cell_yield_cumulo+rab_integral+RQ_integral+Accum._Yield+emission_CO2+consum_O2+generate_CO2; 0.778, 0.907, tmp+PL+interval_Pdt.+mu_cumulo+nu_cumulo+rho_cumulo+nu_per_rho_cumulo+Arg_conc._cumulo+Accum._Yield+emission_O2+emission_CO2+consum_O2+generate_CO2; 0.778, 0.907, tmp+PL+interval_Pdt.+OD+nu_cumulo+rho_cumulo+nu_per_rho_cumulo+Arg_conc._cumulo+cell_yield_cumulo+rab_integral+emission_CO2+consum_O2+generate_CO2; 0.770, 0.907, tmp+PL+interval_Pdt.+OD+RS+nu_cumulo+rho_cumulo+nu_per_rho_cumulo+Arg_conc._cumulo+rab_integral+Accum._Yield+emission_CO2+consum_O2+interval_O2+generate_CO2; 0.774, 0.907, tmp+PL+interval_Pdt.+mu_cumulo+nu_cumulo+rho_cumulo+nu_per_rho_cumulo+Arg_conc._cumulo+cell_yield_cumulo+rab_integral+emission_CO2+consum_O2+interval_O2+generate_CO2; 0.778, 0.907, tmp+PL+PL_cumulo+interval_Pdt.+OD+nu_cumulo+rho_cumulo+nu_per_rho_cumulo+Arg_conc._cumulo+rab_integral+emission_CO2+consum_O2+generate_CO2; 0.778, 0.907, tmp+PL+AN+interval_Pdt.+RS+mu_cumulo+rho_cumulo+rab_integral+RQ_integral+Accum._Yield+emission_CO2+consum_O2+generate_CO2; 0.760, 0.907, tmp+PL+PL_cumulo+interval_Pdt.+OD+RS+nu_cumulo+rho_cumulo+nu_per_rho_cumulo+Arg_conc._cumulo+RQ_integral+Accum._Yield+emission_O2+emission_CO2+consum_O2+interval_O2+generate_CO2; 0.778, 0.907, tmp+PL+interval_Pdt.+mu_cumulo+nu_cumulo+rho_cumulo+nu_per_rho_cumulo+Arg_conc._cumulo+emission_O2+emission_CO2+consum_O2+interval_O2+generate_CO2; 0.765, 0.907, tmp+PL+AN+interval_Pdt.+mu_cumulo+nu_cumulo+rho_cumulo+nu_per_rho_cumulo+cell_yield_cumulo+rab_integral+RQ_integral+Accum._Yield+emission_CO2+consum_O2+interval_O2+generate_CO2; 0.778, 0.907, tmp+PL+AN+interval_Pdt.+mu_cumulo+rho_cumulo+rab_integral+RQ_integral+Accum._Yield+emission_CO2+consum_O2+interval_O2+generate_CO2; 0.783, 0.907, tmp+PL+AN+interval_Pdt.+mu_cumulo+rho_cumulo+rab_integral+RQ_integral+Accum._Yield+emission_CO2+consum_O2+generate_CO2; 0.765, 0.907, tmp+PL+AN+interval_Pdt.+RS+mu_cumulo+nu_cumulo+rho_cumulo+nu_per_rho_cumulo+Arg_conc._cumulo+rab_integral+RQ_integral+Accum._Yield+emission_CO2+consum_O2+generate_CO2; 0.778, 0.907, tmp+pH+PL+interval_Pdt.+OD+mu_cumulo+nu_cumulo+rho_cumulo+nu_per_rho_cumulo+rab_integral+emission_CO2+consum_O2+generate_CO2; 0.778, 0.907, tmp+PL+interval_Pdt.+RS+mu_cumulo+nu_cumulo+rho_cumulo+nu_per_rho_cumulo+emission_O2+emission_CO2+consum_O2+interval_O2+generate_CO2; 0.774, 0.907, tmp+PL+AN+interval_Pdt.+OD+RS+mu_cumulo+nu_cumulo+rho_cumulo+nu_per_rho_cumulo+Accum._Yield+emission_CO2+consum_O2+generate_CO2; 0.774, 0.907, tmp+PL+PL_cumulo+interval_Pdt.+mu_cumulo+nu_cumulo+rho_cumulo+nu_per_rho_cumulo+cell_yield_cumulo+rab_integral+RQ_integral+emission_CO2+consum_O2+generate_CO2; 0.765, 0.907, tmp+PL+interval_Pdt.+mu_cumulo+nu_cumulo+rho_cumulo+nu_per_rho_cumulo+Arg_conc._cumulo+cell_yield_cumulo+rab_integral+RQ_integral+Accum._Yield+emission_O2+emission_CO2+consum_O2+generate_CO2; 0.769, 0.907, tmp+PL+interval_Pdt.+mu_cumulo+nu_cumulo+rho_cumulo+nu_per_rho_cumulo+Arg_conc._cumulo+rab_integral+RQ_integral+Accum._Yield+emission_O2+emission_CO2+consum_O2+generate_CO2; 0.760, 0.907, tmp+PL+PL_cumulo+interval_Pdt.+OD+mu_cumulo+nu_cumulo+rho_cumulo+nu_per_rho_cumulo+Arg_conc._cumulo+rab_integral+RQ_integral+Accum._Yield+emission_O2+emission_CO2+consum_O2+generate_CO2; 0.765, 0.907, tmp+pH+PL+PL_cumulo+AN+interval_Pdt.+mu_cumulo+nu_cumulo+rho_cumulo+nu_per_rho_cumulo+Accum._Yield+emission_O2+emission_CO2+consum_O2+interval_O2+generate_CO2; 0.774, 0.907, tmp+PL+interval_Pdt.+mu_cumulo+nu_cumulo+rho_cumulo+nu_per_rho_cumulo+Arg_conc._cumulo+cell_yield_cumulo+RQ_integral+emission_O2+emission_CO2+consum_O2+generate_CO2; 0.778, 0.907, tmp+PL+PL_cumulo+AN+interval_Pdt.+OD+nu_cumulo+rho_cumulo+nu_per_rho_cumulo+rab_integral+emission_CO2+consum_O2+generate_CO2; 0.778, 0.907, tmp+PL+OD+nu_cumulo+rho_cumulo+nu_per_rho_cumulo+Arg_conc._cumulo+Accum._Yield+emission_O2+emission_CO2+consum_O2+interval_O2+generate_CO2; 0.769, 0.907, tmp+pH+PL+interval_Pdt.+OD+nu_cumulo+rho_cumulo+nu_per_rho_cumulo+Arg_conc._cumulo+rab_integral+RQ_integral+Accum._Yield+emission_CO2+consum_O2+generate_CO2; 0.769, 0.907, tmp+pH+PL+AN+interval_Pdt.+mu_cumulo+nu_cumulo+rho_cumulo+nu_per_rho_cumulo+cell_yield_cumulo+rab_integral+Accum._Yield+emission_CO2+consum_O2+generate_CO2; 0.760, 0.907, tmp+PL+PL_cumulo+AN+interval_Pdt.+OD+nu_cumulo+rho_cumulo+nu_per_rho_cumulo+Arg_conc._cumulo+RQ_integral+Accum._Yield+emission_O2+emission_CO2+consum_O2+interval_O2+generate_CO2; 0.760, 0.907, tmp+PL+PL_cumulo+AN+interval_Pdt.+OD+nu_cumulo+rho_cumulo+nu_per_rho_cumulo+Arg_conc._cumulo+rab_integral+RQ_integral+Accum._Yield+emission_O2+emission_CO2+consum_O2+generate_CO2; 0.786, 0.907, tmp+PL+PL_cumulo+AN+interval_Pdt.+mu_cumulo+rho_cumulo+Accum._Yield+emission_CO2+consum_O2+generate_CO2; 0.774, 0.907, tmp+PL+interval_Pdt.+RS+mu_cumulo+nu_cumulo+rho_cumulo+nu_per_rho_cumulo+cell_yield_cumulo+RQ_integral+emission_O2+emission_CO2+consum_O2+generate_CO2; 0.782, 0.907, tmp+PL_cumulo+interval_Pdt.+mu_cumulo+nu_cumulo+rho_cumulo+nu_per_rho_cumulo+Arg_conc.cumulo+cell_yield_cumulo+emission_CO2+consum_O2+generate_CO2; 0.774, 0.907, tmp+PL+PL_cumulo+interval_yield+interval_Pdt.+mu_cumulo+nu_cumulo+rho_cumulo+nu_per_rho_cumulo+rab_integral+RQ_integral+emission_CO2+consum_O2+generate_CO2; 0.769, 0.907, tmp+PL+AN+interval_Pdt.+OD+RS+mu_cumulo+nu_cumulo+rho_cumulo+nu_per_rho_cumulo+rab_integral+Accum._Yield+emission_CO2+consum_O2+generate_CO2; 0.774, 0.907, tmp+PL+AN+interval_Pdt.+mu_cumulo+nu_cumulo+rho_cumulo+nu_per_rho_cumulo+Arg_conc._cumulo+rab_integral+RQ_integral+emission_CO2+consum_O2+generate_CO2; 0.760, 0.907, tmp+PL+PL_cumulo+interval_Pdt.+RS+mu_cumulo+nu_cumulo+rho_cumulo+nu_per_rho_cumulo+Arg_conc._cumulo+rab_integral+RQ_integral+Accum._Yield+emission_CO2+emission_CO2+consum_O2+generate_CO2; 0.782, 0.907, tmp+pH+PL+interval_Pdt.+mu_cumulo+nu_cumulo+rho_cumulo+nu_per_rho_cumulo+emission_O2+emission_CO2+consum_O2+generate_CO2; 0.778, 0.907, tmp+PL+interval_Pdt.+OD+nu_cumulo+rho_cumulo+nu_per_rho_cumulo+rab_integral+RQ_integral+emission_CO2+consum_O2+interval_O2+generate_CO2; 0.774, 0.907, tmp+PL+interval_Pdt.+OD+mu_cumulo+nu_cumulo+rho_cumulo+nu_per_rho_cumulo+RQ_integral+emission_O2+emission_CO2+consum_O2+interval_O2+generate_CO2; 0.790, 0.907, tmp+PL_cumulo+OD+nu_cumulo+rho_cumulo+nu_per_rho_cumulo+Arg_conc._cumulo+rab_integral+emission_CO2+generate_CO2; 0.786, 0.907, tmp+OD+nu_cumulo+rho_cumulo+nu_per_rho_cumulo+Arg_conc._cumulo+rab_integral+Accum._Yield+emission_CO2+consum_O2+generate_CO2; 0.769, 0.907, tmp+PL+AN+interval_Pdt.+RS+mu_cumulo+nu_cumulo+rho_cumulo+nu_per_rho_cumulo+Accum._Yield+emission_O2+emission_CO2+consum_O2+interval_O2+generate_CO2; 0.769, 0.907, tmp+PL+AN+interval_Pdt.+OD+mu_cumulo+nu_cumulo+rho_cumulo+nu_per_rho_cumulo+Arg_conc._cumulo+rab_integral+emission_CO2+consum_O2+interval_O2+generate_CO2; 0.778, 0.907, tmp+PL_cumulo+OD+RS+nu_cumulo+rho_cumulo+nu_per_rho_cumulo+Arg_conc._cumulo+rab_integral+Accum._Yield+emission_CO2+consum_O2+generate_CO2; 0.774, 0.907, tmp+PL+interval_Pdt.+RS+mu_cumulo+nu_cumulo+rho_cumulo+nu_per_rho_cumulo+rab_integral+Accum._Yield+emission_CO2+consum_O2+interval_O2+generate_CO2; 0.782, 0.907, tmp+PL_cumulo+RS+mu_cumulo+nu_cumulo+rho_cumulo+nu_per_rho_cumulo+cell_yield_cumulo+rab_integral+emission_CO2+consum_O2+generate_CO2; 0.778, 0.907, tmp+PL+interval_Pdt.+mu_cumulo+nu_cumulo+rho_cumulo+nu_per_rho_cumulo+rab_integral+emission_O2+emission_CO2+consum_O2+interval_O2+generate_CO2; 0.769, 0.907, tmp+pH+PL+interval_Pdt.+mu_cumulo+nu_cumulo+rho_cumulo+nu_per_rho_cumulo+cell_yield_cumulo+RQ_integral+Accum._Yield+emission_O2+emission_CO2+consum_O2+generate_CO2; 0.774, 0.907, tmp+PL+interval_Pdt.+OD+nu_cumulo+rho_cumulo+nu_per_rho_cumulo+RQ_integral+Accum._Yield+emission_O2+emission_CO2+consum_O2+interval_O2+generate_CO2; 0.769, 0.907, tmp+PL+PL_cumulo+interval_Pdt.+mu_cumulo+nu_cumulo+rho_cumulo+nu_per_rho_cumulo+Arg_conc._cumulo+cell_yield_cumulo+rab_integral+Accum._Yield+emission_CO2+consum_O2+generate_CO2; 0.782, 0.907, tmp+PL+AN+interval_Pdt.+OD+nu_cumulo+rho_cumulo+nu_per_rho_cumulo+Arg_conc._cumulo+emission_CO2+consum_O2+generate_CO2; 0.778, 0.907, tmp+pH+PL+interval_Pdt.+RS+mu_cumulo+nu_cumulo+rho_cumulo+nu_per_rho_cumulo+rab_integral+emission_CO2+consum_O2+generate_CO2; 0.782, 0.907, tmp+PL+interval_Pdt.+OD+nu_cumulo+rho_cumulo+nu_per_rho_cumulo+Accum._Yield+emission_O2+emission_CO2+consum_O2+generate_CO2; 0.769, 0.907, tmp+PL+AN+interval_Pdt.+OD+RS+mu_cumulo+nu_cumulo+rho_cumulo+nu_per_rho_cumulo+Arg_conc._cumulo+Accum._Yield+emission_CO2+consum_O2+generate_CO2; 0.778, 0.907, tmp+PL+AN+OD+nu_cumulo+rho_cumulo+nu_per_rho_cumulo+Arg_conc._cumulo+rab_integral+Accum._Yield+emission_CO2+consum_O2+generate_CO2; 0.765, 0.907, tmp+PL+AN+interval_Pdt.+RS+mu_cumulo+nu_cumulo+rho_cumulo+nu_per_rho_cumulo+cell_yield_cumulo+rab_integral+RQ_integral+Accum._Yield+emission_CO2+consum_O2+generate_CO2; 0.778, 0.907, tmp+pH+OD+mu_cumulo+nu_cumulo+rho_cumulo+nu_per_rho_cumulo+Arg_conc._cumulo+rab_integral+Accum._Yield+emission_CO2+consum_O2+generate_CO2; 0.774, 0.907, tmp+PL+PL_cumulo+interval_Pdt.+mu_cumulo+nu_cumulo+rho_cumulo+nu_per_rho_cumulo+Arg_conc._cumulo+emission_O2+emission_CO2+consum_O2+interval_O2+generate_CO2; 0.782, 0.907, tmp+PL+interval_Pdt.+OD+nu_cumulo+rho_cumulo+nu_per_rho_cumulo+Arg_conc._cumulo+Accum._Yield+emission_CO2+consum_O2+generate_CO2; 0.774, 0.907, tmp+PL+AN+interval_Pdt.+mu_cumulo+nu_cumulo+rho_cumulo+nu_per_rho_cumulo+RQ_integral+emission_O2+emission_CO2+consum_O2+interval_O2+generate_CO2; 0.786, 0.907, tmp+PL+interval_Pdt.+mu_cumulo+nu_cumulo+rho_cumulo+nu_per_rho_cumulo+RQ_integral+emission_CO2+consum_O2+generate_CO2; 0.786, 0.907, tmp+interval_Pdt.+mu_cumulo+nu_cumulo+rho_cumulo+nu_per_rho_cumulo+rab_integral+RQ_integral+emission_CO2+consum_O2+generate_CO2; 0.769, 0.907, tmp+pH+PL+PL_cumulo+interval_Pdt.+mu_cumulo+nu_cumulo+rho_cumulo+nu_per_rho_cumulo+RQ_integral+Accum._Yield+emission_O2+emission_CO2+consum_O2+generate_CO2; 0.774, 0.907, tmp+PL+PL_cumulo+interval_Pdt.+OD+mu_cumulo+nu_cumulo+rho_cumulo+nu_per_rho_cumulo+rab_integral+Accum._Yield+emission_CO2+consum_O2+generate_CO2; 0.774, 0.907, tmp+PL+AN+interval_Pdt.+OD+mu_cumulo+nu_cumulo+rho_cumulo+nu_per_rho_cumulo+rab_integral+RQ_integral+emission_CO2+consum_O2+generate_CO2; 0.760, 0.907, tmp+PL+PL_cumulo+AN+interval_Pdt.+OD+RS+nu_cumulo+rho_cumulo+nu_per_rho_cumulo+Arg_conc._cumulo+rab_integral+Accum._Yield+emission_O2+emission_CO2+consum_O2+generate_CO2; 0.774, 0.907, tmp+PL+interval_Pdt.+OD+mu_cumulo+nu_cumulo+rho_cumulo+nu_per_rho_cumulo+cell_yield_cumulo+rab_integral+emission_CO2+consum_O2+interval_O2+generate_CO2; 0.786, 0.907, tmp+pH+PL+AN+interval_Pdt.+mu_cumulo+rho_cumulo+Accum._Yield+emission_CO2+consum_O2+generate_CO2; 0.774, 0.907, tmp+PL+PL_cumulo+AN+interval_Pdt.+mu_cumulo+nu_cumulo+rho_cumulo+nu_per_rho_cumulo+Arg_conc._cumulo+emission_O2+emission_CO2+consum_O2+generate_CO2; 0.782, 0.907, tmp+PL_cumulo+OD+mu_cumulo+nu_cumulo+rho_cumulo+nu_per_rho_cumulo+cell_yield_cumulo+rab_integral+emission_CO2+consum_O2+generate_

CO2; 0.778, 0.907, tmp+PL+PL_cumulo+interval_Pdt.+OD+nu_cumulo+rho_cumulo+nu_per_rho_cumulo+Arg_conc._cumulo+emission_O2+emission_CO2+consum_O2+generate_CO2; 0.778, 0.907, tmp+PL+AN+interval_Pdt.+mu_cumulo+nu_cumulo+rho_cumulo+nu_per_rho_cumulo+cell_yield_cumulo+Accum._Yield+emission_CO2+consum_O2+generate_CO2; 0.760, 0.907, tmp+PL+PL_cumulo+AN+interval_Pdt.+OD+mu_cumulo+nu_cumulo+rho_cumulo+nu_per_rho_cumulo+Arg_conc._cumulo+rab_integral+Accum._Yield+emission_O2+emission_CO2+consum_O2+generate_CO2; 0.782, 0.907, tmp+PL+OD+nu_cumulo+rho_cumulo+nu_per_rho_cumulo+Arg_conc._cumulo+cell_yield_cumulo+rab_integral+emission_CO2+consum_O2+generate_CO2; 0.778, 0.907, tmp+pH+PL+interval_Pdt.+mu_cumulo+nu_cumulo+rho_cumulo+nu_per_rho_cumulo+Arg_conc._cumulo+rab_integral+emission_CO2+consum_O2+generate_CO2; 0.774, 0.907, tmp+PL+interval_Pdt.+OD+mu_cumulo+nu_cumulo+rho_cumulo+nu_per_rho_cumulo+cell_yield_cumulo+RQ_integral+emission_O2+emission_CO2+consum_O2+generate_CO2; 0.782, 0.907, tmp+PL_cumulo+interval_Pdt.+OD+mu_cumulo+nu_cumulo+rho_cumulo+nu_per_rho_cumulo+Arg_conc._cumulo+emission_CO2+consum_O2+generate_CO2; 0.778, 0.907, tmp+PL_cumulo+interval_Pdt.+OD+RS+mu_cumulo+nu_cumulo+rho_cumulo+nu_per_rho_cumulo+rab_integral+emission_CO2+consum_O2+generate_CO2; 0.774, 0.907, tmp+PL+AN+interval_Pdt.+RS+mu_cumulo+nu_cumulo+rho_cumulo+nu_per_rho_cumulo+cell_yield_cumulo+emission_O2+emission_CO2+consum_O2+generate_CO2; 0.774, 0.907, tmp+pH+PL+interval_Pdt.+mu_cumulo+nu_cumulo+rho_cumulo+nu_per_rho_cumulo+cell_yield_cumulo+rab_integral+RQ_integral+emission_CO2+consum_O2+generate_CO2; 0.774, 0.907, tmp+PL+AN+interval_Pdt.+OD+mu_cumulo+nu_cumulo+rho_cumulo+nu_per_rho_cumulo+cell_yield_cumulo+emission_O2+emission_CO2+consum_O2+generate_CO2; 0.764, 0.907, tmp+PL+PL_cumulo+interval_Pdt.+OD+RS+mu_cumulo+nu_cumulo+rho_cumulo+nu_per_rho_cumulo+Arg_conc._cumulo+Accum._Yield+emission_O2+emission_CO2+consum_O2+generate_CO2; 0.764, 0.907, tmp+PL+PL_cumulo+AN+interval_Pdt.+OD+mu_cumulo+nu_cumulo+rho_cumulo+nu_per_rho_cumulo+rab_integral+Accum._Yield+emission_CO2+consum_O2+interval_O2+generate_CO2; 0.782, 0.907, tmp+PL+interval_Pdt.+OD+nu_cumulo+rho_cumulo+nu_per_rho_cumulo+Arg_conc._cumulo+rab_integral+Accum._Yield+emission_CO2+generate_CO2; 0.778, 0.907, tmp+pH+PL_cumulo+interval_Pdt.+mu_cumulo+nu_cumulo+rho_cumulo+nu_per_rho_cumulo+cell_yield_cumulo+rab_integral+emission_CO2+consum_O2+generate_CO2; 0.759, 0.907, tmp+PL+PL_cumulo+interval_Pdt.+OD+RS+nu_cumulo+rho_cumulo+nu_per_rho_cumulo+Arg_conc._cumulo+rab_integral+RQ_integral+Accum._Yield+emission_O2+emission_CO2+consum_O2+generate_CO2; 0.764, 0.907, tmp+PL+PL_cumulo+interval_Pdt.+OD+RS+mu_cumulo+nu_cumulo+rho_cumulo+nu_per_rho_cumulo+Arg_conc._cumulo+rab_integral+Accum._Yield+emission_CO2+consum_O2+generate_CO2; 0.774, 0.907, tmp+PL+PL_cumulo+interval_Pdt.+mu_cumulo+nu_cumulo+rho_cumulo+nu_per_rho_cumulo+rab_integral+RQ_integral+emission_CO2+consum_O2+interval_O2+generate_CO2; 0.774, 0.907, tmp+PL+interval_Pdt.+mu_cumulo+nu_cumulo+rho_cumulo+nu_per_rho_cumulo+cell_yield_cumulo+rab_integral+Accum._Yield+emission_O2+emission_CO2+consum_O2+generate_CO2; 0.769, 0.907, tmp+PL+interval_Pdt.+OD+mu_cumulo+nu_cumulo+rho_cumulo+nu_per_rho_cumulo+rab_integral+RQ_integral+Accum._Yield+emission_CO2+consum_O2+interval_O2+generate_CO2; 0.764, 0.907, tmp+PL+interval_Pdt.+OD+RS+mu_cumulo+nu_cumulo+rho_cumulo+nu_per_rho_cumulo+Arg_conc._cumulo+RQ_integral+Accum._Yield+emission_O2+emission_CO2+consum_O2+generate_CO2; 0.769, 0.907, tmp+PL+interval_Pdt.+RS+mu_cumulo+nu_cumulo+rho_cumulo+nu_per_rho_cumulo+rab_integral+RQ_integral+Accum._Yield+emission_CO2+consum_O2+interval_O2+generate_CO2; 0.786, 0.907, tmp+PL+AN+interval_Pdt.+mu_cumulo+rho_cumulo+RQ_integral+Accum._Yield+emission_CO2+consum_O2+generate_CO2; 0.782, 0.907, tmp+PL+interval_yield+interval_Pdt.+mu_cumulo+nu_cumulo+rho_cumulo+nu_per_rho_cumulo+rab_integral+emission_CO2+consum_O2+generate_CO2; 0.786, 0.907, tmp+pH+PL_cumulo+interval_Pdt.+mu_cumulo+nu_cumulo+rho_cumulo+nu_per_rho_cumulo+emission_CO2+consum_O2+generate_CO2; 0.769, 0.907, tmp+PL+PL_cumulo+AN+interval_yield+interval_Pdt.+mu_cumulo+nu_cumulo+rho_cumulo+nu_per_rho_cumulo+rab_integral+emission_CO2+consum_O2+interval_O2+generate_CO2; 0.769, 0.907, tmp+pH+PL+interval_Pdt.+OD+nu_cumulo+rho_cumulo+nu_per_rho_cumulo+Arg_conc._cumulo+RQ_integral+Accum._Yield+emission_O2+emission_CO2+consum_O2+generate_CO2; 0.782, 0.907, tmp+PL_cumulo+interval_Pdt.+RS+mu_cumulo+nu_cumulo+rho_cumulo+nu_per_rho_cumulo+cell_yield_cumulo+emission_CO2+consum_O2+generate_CO2; 0.790, 0.907, tmp+PL+interval_Pdt.+mu_cumulo+rho_cumulo+rab_integral+Accum._Yield+emission_CO2+consum_O2+generate_CO2; 0.778, 0.907, tmp+PL_cumulo+interval_Pdt.+mu_cumulo+nu_cumulo+rho_cumulo+nu_per_rho_cumulo+cell_yield_cumulo+Accum._Yield+emission_O2+emission_CO2+consum_O2+generate_CO2; 0.769, 0.907, tmp+PL+AN+interval_Pdt.+OD+mu_cumulo+nu_cumulo+rho_cumulo+nu_per_rho_cumulo+cell_yield_cumulo+emission_O2+emission_CO2+consum_O2+interval_O2+generate_CO2; 0.773, 0.907, tmp+PL+interval_Pdt.+OD+nu_cumulo+rho_cumulo+nu_per_rho_cumulo+Arg_conc._cumulo+rab_integral+Accum._Yield+emission_O2+emission_CO2+consum_O2+generate_CO2; 0.764, 0.907, tmp+PL+AN+interval_Pdt.+OD+mu_cumulo+nu_cumulo+rho_cumulo+nu_per_rho_cumulo+cell_yield_cumulo+rab_integral+Accum._Yield+emission_CO2+consum_O2+interval_O2+generate_CO2; 0.773, 0.907, tmp+PL+OD+RS+mu_cumulo+nu_cumulo+rho_cumulo+nu_per_rho_cumulo+Arg_conc._cumulo+rab_integral+Accum._Yield+emission_CO2+consum_O2+generate_CO2; 0.769, 0.907, tmp+PL_cumulo+interval_Pdt.+mu_cumulo+nu_cumulo+rho_cumulo+nu_per_rho_cumulo+Arg_conc._cumulo+cell_yield_cumulo+rab_integral+RQ_integral+Accum._Yield+emission_CO2+consum_O2+generate_CO2; 0.769, 0.907, tmp+PL+AN+interval_Pdt.+mu_cumulo+nu_cumulo+rho_cumulo+nu_per_rho_cumulo+Arg_conc._cumulo+cell_yield_cumulo+Accum._Yield+emission_O2+emission_CO2+consum_O2+generate_CO2; 0.778, 0.907, tmp+pH+PL+interval_Pdt.+mu_cumulo+nu_cumulo+rho_cumulo+nu_per_rho_cumulo+rab_integral+emission_CO2+consum_O2+interval_O2+generate_CO2; 0.764, 0.907, tmp+PL+PL_cumulo+AN+interval_Pdt.+mu_cumulo+nu_cumulo+rho_cumulo+nu_per_rho_cumulo+Arg_conc._cumulo+rab_integral+RQ_integral+Accum._Yield+emission_CO2+consum_O2+generate_CO2; 0.769, 0.907, tmp+PL+PL_cumulo+interval_Pdt.+mu_cumulo+nu_cumulo+rho_cumulo+nu_per_rho_cumulo+cell_yield_cumulo+rab_integral+RQ_integral+Accum._Yield+emission_CO2+ consum_O2+generate_CO2; 0.790, 0.907, tmp+PL+OD+ nu_cumulo+rho_cumulo+nu_per_rho_cumulo+emission_ O2+emission_CO2+consum_O2+generate_CO2; 0.782, 0.907, tmp+pH+interval_Pdt.+mu_cumulo+nu_cumulo+ rho_cumulo+nu_per_rho_cumulo+cell_yield_cumulo+rab_ integral+emission_CO2+consum_O2+generate_CO2; 0.773, 0.907, tmp+PL+interval_Pdt.+OD+mu_cumulo+nu_ cumulo+rho_cumulo+nu_per_rho_cumulo+Accum._Yield+ emission_O2+emission_CO2+consum_O2+interval_O2+ generate_CO2; 0.773, 0.907, tmp+PL+interval_Pdt.+RS+ mu_cumulo+nu_cumulo+rho_cumulo+nu_per_rho_ cumulo+rab_integral+RQ_integral+emission_CO2+ consum_O2+interval_O2+generate_CO2; 0.773, 0.907, tmp+PL+AN+interval_Pdt.+OD+RS+nu_cumulo+rho_cu- mulo+nu_per_rho_cumulo+Arg_conc._cumulo+Accum._ Yield+emission_CO2+consum_O2+generate_CO2; 0.773, 0.907, tmp+PL_cumulo+interval_Pdt.+OD+mu_cumulo+ nu_cumulo+rho_cumulo+nu_per_rho_cumulo+cell_yield_ cumulo+rab_integral+Accum._Yield+emission_CO2+con- sum_O2+generate_CO2; 0.782, 0.907, tmp+PL+interval_ Pdt.+OD+nu_cumulo+rho_cumulo+nu_per_rho_cumulo+ cell_yield_cumulo+rab_integral+emission_CO2+consum_ O2+generate_CO2; 0.764, 0.907, tmp+PL+PL_cumulo+ interval_Pdt.+OD+mu_cumulo+nu_cumulo+rho_cumulo+ nu_per_rho_cumulo+Arg_conc._cumulo+Accum._Yield+ emission_O2+emission_CO2+consum_O2+interval_O2+ generate_CO2; 0.790, 0.907, tmp+OD+nu_cumulo+rho_ cumulo+nu_per_rho_cumulo+Arg_conc._cumulo+rab_ integral+Accum._Yield+emission_CO2+generate_CO2; 0.782, 0.907, tmp+PL+interval_Pdt.+OD+RS+nu_cumulo+ rho_cumulo+nu_per_rho_cumulo+rab_integral+emission_ CO2+consum_O2+generate_CO2; 0.786, 0.907, tmp+PL+ AN+interval_yield+interval_Pdt.+mu_cumulo+rho_ cumulo+nu_per_rho_cumulo+emission_CO2+consum_ O2+generate_CO2; 0.782, 0.907, tmp+PL+AN+interval_ yield+interval_Pdt.+mu_cumulo+rho_cumulo+nu_per_ rho_cumulo+emission_CO2+consum_O2+interval_O2+ generate_CO2; 0.769, 0.907, tmp+pH+PL+AN+interval_ Pdt.+mu_cumulo+nu_cumulo+rho_cumulo+nu_per_rho_ cumulo+rab_integral+Accum._Yield+emission_CO2+ consum_O2+interval_O2+generate_CO2; 0.759, 0.907, tmp+pH+PL+PL_cumulo+AN+interval_Pdt.+OD+nu_cu- mulo+rho_cumulo+nu_per_rho_cumulo+Arg_conc._cu- mulo+Accum._Yield+emission_O2+emission_CO2+con- sum_O2+interval_O2+generate_CO2; 0.773, 0.907, tmp+ PL+interval_Pdt.+OD+mu_cumulo+nu_cumulo+rho_ cumulo+nu_per_rho_cumulo+rab_integral+RQ_integral+ emission_CO2+consum_O2+interval_O2+generate_CO2; 0.764, 0.907, tmp+PL+interval_Pdt.+OD+mu_cumulo+nu_ cumulo+rho_cumulo+nu_per_rho_cumulo+cell_yield_cu- mulo+RQ_integral+Accum._Yield+emission_O2+emis- sion_CO2+consum_O2+interval_O2+generate_CO2; 0.786, 0.907, tmp+PL_cumulo+interval_Pdt.+mu_cumulo+ nu_cumulo+rho_cumulo+nu_per_rho_cumulo+emission_ O2+emission_CO2+consum_O2+generate_CO2; 0.759, 0.907, tmp+pH+PL+PL_cumulo+interval_Pdt.+OD+nu_cu- mulo+rho_cumulo+nu_per_rho_cumulo+Arg_conc._cu- mulo+RQ_integral+Accum._Yield+emission_O2+emis- sion_CO2+consum_O2+interval_O2+generate_CO2; 0.773, 0.907, tmp+PL+PL_cumulo+interval_Pdt.+mu_cu- mulo+nu_cumulo+rho_cumulo+nu_per_rho_cumulo+rab_ integral+RQ_integral+emission_O2+emission_CO2+con- sum_O2+generate_CO2; 0.769, 0.907, tmp+PL+interval_ Pdt.+OD+RS+mu_cumulo+nu_cumulo+rho_cumulo+nu_ per_rho_cumulo+Arg_conc._cumulo+Accum._Yield+ emission_O2+emission_CO2+consum_O2+generate_CO2; 0.782, 0.907, tmp+PL+interval_Pdt.+mu_cumulo+nu_cu- mulo+rho_cumulo+nu_per_rho_cumulo+Accum._Yield+ emission_CO2+consum_O2+interval_O2+generate_CO2; 0.778, 0.907, tmp+PL+PL_cumulo+AN+interval_Pdt.+mu_ cumulo+nu_cumulo+rho_cumulo+nu_per_rho_cumulo+ cell_yield_cumulo+emission_CO2+consum_O2+generate_ CO2; 0.769, 0.907, tmp+PL+PL_cumulo+interval_Pdt.+ mu_cumulo+nu_cumulo+rho_cumulo+nu_per_rho_ cumulo+Arg_conc._cumulo+rab_integral+RQ_integral+ Accum._Yield+emission_CO2+consum_O2+generate_ CO2; 0.769, 0.907, tmp+PL+PL_cumulo+AN+interval_ yield+interval_Pdt.+mu_cumulo+nu_cumulo+rho_cumulo+ nu_per_rho_cumulo+Arg_conc._cumulo+rab_integral+ emission_CO2+consum_O2+generate_CO2; 0.773, 0.907, tmp+PL+interval_Pdt.+mu_cumulo+nu_cumulo+rho_cu- mulo+nu_per_rho_cumulo+Arg_conc._cumulo+cell_yield_ cumulo+emission_O2+emission_CO2+consum_O2+inter- val_O2+generate_CO2; 0.769, 0.907, tmp+PL+interval_ Pdt.+mu_cumulo+nu_cumulo+rho_cumulo+nu_per_rho_ cumulo+Arg_conc._cumulo+rab_integral+RQ_integral+ Accum._Yield+emission_CO2+consum_O2+interval_O2+ generate_CO2; 0.773, 0.907, tmp+pH+PL+AN+interval_ Pdt.+mu_cumulo+nu_cumulo+rho_cumulo+nu_per_rho_ cumulo+Accum._Yield+emission_CO2+consum_O2+ interval_O2+generate_CO2; 0.782, 0.907, tmp+PL_ cumulo+interval_Pdt.+OD+nu_cumulo+rho_cumulo+nu_ per_rho_cumulo+Arg_conc._cumulo+rab_integral+ Accum._Yield+emission_CO2+generate_CO2; 0.786, 0.907, tmp+pH+mu_cumulo+nu_cumulo+rho_cumulo+nu_ per_rho_cumulo+cell_yield_cumulo+rab_integral+emis- sion_CO2+consum_O2+generate_CO2; 0.778, 0.907, tmp+ PL_cumulo+interval_Pdt.+OD+mu_cumulo+nu_cumulo+ rho_cumulo+nu_per_rho_cumulo+Arg_conc._cumulo+ rab_integral+emission_CO2+consum_O2+generate_CO2; 0.778, 0.907, tmp+PL+interval_Pdt.+OD+nu_cumulo+rho_ cumulo+nu_per_rho_cumulo+Arg_conc._cumulo+rab_in- tegral+RQ_integral+emission_CO2+consum_O2+gener- ate_CO2; 0.769, 0.907, tmp+PL+PL_cumulo+AN+ interval_yield+interval_Pdt.+RS+mu_cumulo+nu_cumulo+ rho_cumulo+nu_per_rho_cumulo+rab_integral+emission_ CO2+consum_O2+generate_CO2; 0.773, 0.907, tmp+pH+ interval_Pdt.+OD+mu_cumulo+nu_cumulo+rho_cumulo+ nu_per_rho_cumulo+Arg_conc._cumulo+rab_integral+ Accum._Yield+emission_CO2+consum_O2+generate_ CO2; 0.790, 0.907, tmp+PL+interval_Pdt.+mu_cumulo+ rho_cumulo+nu_per_rho_cumulo+rab_integral+emission_ CO2+consum_O2+generate_CO2; 0.773, 0.907, tmp+PL_ cumulo+interval_Pdt.+RS+mu_cumulo+nu_cumulo+rho_ cumulo+nu_per_rho_cumulo+Arg_conc._cumulo+cell_ yield_cumulo+rab_integral+emission_CO2+consum_O2+ generate_CO2; 0.773, 0.907, tmp+PL+PL_cumulo+ interval_Pdt.+OD+mu_cumulo+nu_cumulo+rho_cumulo+ nu_per_rho_cumulo+Accum._Yield+emission_O2+ emission_CO2+consum_O2+generate_CO2; 0.778, 0.907, tmp+PL_cumulo+interval_Pdt.+mu_cumulo+nu_cumulo+ rho_cumulo+nu_per_rho_cumulo+Arg_conc._cumulo+ rab_integral+RQ_integral+emission_CO2+consum_O2+ generate_CO2; 0.764, 0.907, tmp+PL+PL_cumulo+AN+ interval_Pdt.+RS+mu_cumulo+nu_cumulo+rho_cumulo+ nu_per_rho_cumulo+Arg_conc._cumulo+Accum._Yield+ emission_O2+emission_CO2+consum_O2+generate_CO2; 0.769, 0.907, tmp+PL+interval_Pdt.+OD+nu_cumulo+rho_ cumulo+nu_per_rho_cumulo+Arg_conc._cumulo+rab_in- tegral+RQ_integral+Accum._Yield+emission_O2+emis- sion_CO2+consum_O2+generate_CO2; 0.769, 0.907, tmp+ PL+PL_cumulo+AN+interval_yield+interval_Pdt.+mu_ cumulo+nu_cumulo+rho_cumulo+nu_per_rho_cumulo+ rab_integral+Accum._Yield+emission_CO2+consum_O2+ generate_CO2; 0.773, 0.907, tmp+pH+interval_Pdt.+mu_cumulo+nu_cumulo+rho_cumulo+nu_per_rho_cumulo+Arg_conc._cumulo+rab_integral+RQ_integral+Accum._Yield+emission_CO2+consum_O2+generate_CO2; 0.773, 0.907, tmp+PL+interval_Pdt.+RS+mu_cumulo+nu_cumulo+rho_cumulo+nu_per_rho_cumulo+cell_yield_cumulo+rab_integral+emission_CO2+consum_O2+interval_O2+generate_CO2; 0.769, 0.907, tmp+PL+AN+interval_Pdt.+mu_cumulo+nu_cumulo+rho_cumulo+nu_per_rho_cumulo+cell_yield_cumulo+rab_integral+RQ_integral+emission_CO2+consum_O2+interval_O2+generate_CO2; 0.764, 0.907, tmp+PL+AN+interval_Pdt.+OD+mu_cumulo+nu_cumulo+rho_cumulo+nu_per_rho_cumulo+cell_yield_cumulo+rab_integral+RQ_integral+Accum._Yield+emission_CO2+consum_O2+generate_CO2; 0.769, 0.907, tmp+PL+interval_Pdt.+OD+mu_cumulo+nu_cumulo+rho_cumulo+nu_per_rho_cumulo+rab_integral+RQ_integral+Accum._Yield+emission_O2+emission_CO2+consum_O2+generate_CO2; 0.769, 0.907, tmp+PL+AN+interval_Pdt.+OD+nu_cumulo+rho_cumulo+nu_per_rho_cumulo+Arg_conc._cumulo+Accum._Yield+emission_O2+emission_CO2+consum_O2+interval_O2+generate_CO2; 0.782, 0.907, tmp+PL+AN+interval_Pdt.+mu_cumulo+rho_cumulo+cell_yield_cumulo+Accum._Yield+emission_CO2+consum_O2+interval_O2+generate_CO2; 0.769, 0.907, tmp+pH+PL+PL_cumulo+AN+interval_Pdt.+mu_cumulo+nu_cumulo+rho_cumulo+nu_per_rho_cumulo+rab_integral+emission_CO2+consum_O2+interval_O2+generate_CO2; 0.773, 0.907, tmp+PL+AN+interval_Pdt.+mu_cumulo+nu_cumulo+rho_cumulo+nu_per_rho_cumulo+RQ_integral+Accum._Yield+emission_CO2+consum_O2+interval_O2+generate_CO2; 0.773, 0.907, tmp+PL+interval_yield+interval_Pdt.+RS+mu_cumulo+nu_cumulo+rho_cumulo+nu_per_rho_cumulo+rab_integral+RQ_integral+emission_CO2+consum_O2+generate_CO2; 0.777, 0.907, tmp+PL+PL_cumulo+AN+interval_Pdt.+RS+mu_cumulo+nu_cumulo+rho_cumulo+nu_per_rho_cumulo+emission_CO2+consum_O2+generate_CO2; 0.777, 0.907, tmp+PL+interval_Pdt.+RS+mu_cumulo+nu_cumulo+rho_cumulo+nu_per_rho_cumulo+Arg_conc._cumulo+emission_O2+emission_CO2+consum_O2+generate_CO2; 0.782, 0.907, tmp+PL+interval_Pdt.+RS+mu_cumulo+nu_cumulo+rho_cumulo+nu_per_rho_cumulo+Accum._Yield+emission_CO2+consum_O2+generate_CO2; 0.768, 0.907, tmp+pH+PL+PL_cumulo+interval_Pdt.+mu_cumulo+nu_cumulo+rho_cumulo+nu_per_rho_cumulo+Arg_conc._cumulo+rab_integral+Accum._Yield+emission_CO2+consum_O2+generate_CO2; 0.786, 0.907, tmp+PL+AN+interval_Pdt.+mu_cumulo+rho_cumulo+rab_integral+emission_CO2+consum_O2+interval_O2+generate_CO2; 0.782, 0.907, tmp+PL+AN+interval_Pdt.+RS+mu_cumulo+rho_cumulo+nu_per_rho_cumulo+Accum._Yield+emission_CO2+consum_O2+generate_CO2; 0.768, 0.907, tmp+PL+PL_cumulo+interval_Pdt.+RS+mu_cumulo+nu_cumulo+rho_cumulo+nu_per_rho_cumulo+Arg_conc._cumulo+Accum._Yield+emission_O2+emission_CO2+consum_O2+generate_CO2; 0.759, 0.907, tmp+PL+PL_cumulo+interval_Pdt.+mu_cumulo+nu_cumulo+rho_cumulo+nu_per_rho_cumulo+Arg_conc._cumulo+rab_integral+RQ_integral+Accum._Yield+emission_O2+emission_CO2+consum_O2+interval_O2+generate_CO2; 0.773, 0.907, tmp+PL+interval_Pdt.+OD+mu_cumulo+nu_cumulo+rho_cumulo+nu_per_rho_cumulo+cell_yield_cumulo+emission_O2+emission_CO2+consum_O2+interval_O2+generate_CO2; 0.782, 0.907, tmp+PL+AN+interval_Pdt.+RS+mu_cumulo+nu_cumulo+rho_cumulo+nu_per_rho_cumulo+emission_CO2+consum_O2+ generate_CO2; 0.768, 0.907, tmp+PL+interval_Pdt.+OD+mu_cumulo+nu_cumulo+rho_cumulo+nu_per_rho_cumulo+Arg_conc._cumulo+rab_integral+Accum._Yield+emission_CO2+consum_O2+interval_O2+generate_CO2; 0.759, 0.907, tmp+PL+PL_cumulo+AN+interval_Pdt.+OD+mu_cumulo+nu_cumulo+rho_cumulo+nu_per_rho_cumulo+Arg_conc._cumulo+rab_integral+Accum._Yield+emission_CO2+consum_O2+interval_O2+generate_CO2; 0.781, 0.907, tmp+PL+AN+OD+nu_cumulo+rho_cumulo+nu_per_rho_cumulo+Arg_conc._cumulo+rab_integral+emission_CO2+consum_O2+generate_CO2; 0.773, 0.907, tmp+pH+PL+interval_Pdt.+mu_cumulo+nu_cumulo+rho_cumulo+nu_per_rho_cumulo+Arg_conc._cumulo+rab_integral+Accum._Yield+emission_CO2+consum_O2+generate_CO2; 0.773, 0.907, tmp+PL_cumulo+interval_Pdt.+mu_cumulo+nu_cumulo+rho_cumulo+nu_per_rho_cumulo+Arg_conc._cumulo+rab_integral+RQ_integral+Accum._Yield+emission_CO2+consum_O2+generate_CO2; 0.773, 0.907, tmp+PL+PL_cumulo+interval_Pdt.+mu_cumulo+nu_cumulo+rho_cumulo+nu_per_rho_cumulo+Arg_conc._cumulo+cell_yield_cumulo+rab_integral+emission_CO2+consum_O2+generate_CO2; 0.764, 0.907, tmp+PL+AN+interval_Pdt.+RS+mu_cumulo+nu_cumulo+rho_cumulo+nu_per_rho_cumulo+cell_yield_cumulo+rab_integral+Accum._Yield+emission_CO2+consum_O2+interval_O2+generate_CO2; 0.781, 0.907, tmp+interval_Pdt.+mu_cumulo+nu_cumulo+rho_cumulo+nu_per_rho_cumulo+rab_integral+Accum._Yield+emission_CO2+consum_O2+interval_O2+generate_CO2; 0.768, 0.907, tmp+PL_cumulo+interval_Pdt.+OD+mu_cumulo+nu_cumulo+rho_cumulo+nu_per_rho_cumulo+cell_yield_cumulo+rab_integral+RQ_integral+Accum._Yield+emission_CO2+consum_O2+generate_CO2; 0.768, 0.907, tmp+PL+PL_cumulo+interval_Pdt.+mu_cumulo+nu_cumulo+rho_cumulo+nu_per_rho_cumulo+cell_yield_cumulo+Accum._Yield+emission_O2+emission_CO2+consum_O2+interval_O2+generate_CO2; 0.773, 0.907, tmp+PL+interval_Pdt.+OD+mu_cumulo+nu_cumulo+rho_cumulo+nu_per_rho_cumulo+Arg_conc._cumulo+rab_integral+RQ_integral+emission_CO2+consum_O2+generate_CO2; 0.764, 0.907, tmp+PL+AN+interval_Pdt.+mu_cumulo+nu_cumulo+rho_cumulo+nu_per_rho_cumulo+cell_yield_cumulo+RQ_integral+Accum._Yield+emission_O2+emission_CO2+consum_O2+interval_O2+generate_CO2; 0.768, 0.907, tmp+PL+PL_cumulo+interval_Pdt.+mu_cumulo+nu_cumulo+rho_cumulo+nu_per_rho_cumulo+Arg_conc._cumulo+cell_yield_cumulo+Accum._Yield+emission_O2+emission_CO2+consum_O2+generate_CO2; 0.777, 0.907, tmp+pH+PL_cumulo+interval_Pdt.+mu_cumulo+nu_cumulo+rho_cumulo+nu_per_rho_cumulo+rab_integral+Accum._Yield+emission_CO2+consum_O2+generate_CO2; 0.764, 0.907, tmp+PL+PL_cumulo+AN+interval_Pdt.+mu_cumulo+nu_cumulo+rho_cumulo+nu_per_rho_cumulo+Arg_conc._cumulo+RQ_integral+Accum._Yield+emission_O2+emission_CO2+consum_O2+generate_CO2; 0.768, 0.907, tmp+PL+PL_cumulo+AN+interval_Pdt.+OD+mu_cumulo+nu_cumulo+rho_cumulo+nu_per_rho_cumulo+Accum._Yield+emission_O2+emission_CO2+consum_O2+generate_CO2; 0.785, 0.907, tmp+PL+AN+interval_yield+interval_Pdt.+mu_cumulo+rho_cumulo+Arg_conc._cumulo+emission_CO2+consum_O2+generate_CO2; 0.768, 0.907, tmp+PL+AN+interval_Pdt.+OD+mu_cumulo+nu_cumulo+rho_cumulo+nu_per_rho_cumulo+Arg_conc._cumulo+Accum._Yield+emission_O2+emission_CO2+consum_O2+generate_CO2; 0.777, 0.907, tmp+PL+AN+OD+nu_cumulo+rho_cumulo+nu_per_rho_cumulo+Arg_conc._cumulo+Accum._Yield+ emission_O2+emission_CO2+consum_O2+generate_CO2; 0.768, 0.907, tmp+PL+AN+interval_Pdt.+RS+mu_cumulo+nu_cumulo+rho_cumulo+nu_per_rho_cumulo+cell_yield_cumulo+Accum._Yield+emission_O2+emission_CO2+consum_O2+generate_CO2; 0.768, 0.907, tmp+PL+AN+interval_Pdt.+RS+mu_cumulo+nu_cumulo+rho_cumulo+nu_per_rho_cumulo+Arg_conc._cumulo+cell_yield_cumulo+Accum._Yield+emission_CO2+consum_O2+generate_CO2; 0.777, 0.907, tmp+PL+AN+interval_yield+interval_Pdt.+mu_cumulo+nu_cumulo+nu_per_rho_cumulo+cell_yield_cumulo+emission_CO2+consum_O2+generate_CO2; 0.768, 0.906, tmp+PL+AN+interval_Pdt.+RS+mu_cumulo+nu_cumulo+rho_cumulo+nu_per_rho_cumulo+Arg_conc._cumulo+rab_integral+emission_CO2+consum_O2+interval_O2+generate_CO2; 0.781, 0.906, tmp+PL+PL_cumulo+OD+nu_cumulo+rho_cumulo+nu_per_rho_cumulo+Arg_conc._cumulo+emission_O2+emission_CO2+consum_O2+generate_CO2; 0.781, 0.906, tmp+PL_cumulo+interval_Pdt.+mu_cumulo+nu_cumulo+rho_cumulo+nu_per_rho_cumulo+cell_yield_cumulo+emission_CO2+consum_O2+interval_O2+generate_CO2; 0.768, 0.906, tmp+PL+interval_Pdt.+OD+RS+mu_cumulo+nu_cumulo+rho_cumulo+nu_per_rho_cumulo+cell_yield_cumulo+rab_integral+Accum._Yield+emission_CO2+consum_O2+generate_CO2; 0.768, 0.906, tmp+PL_cumulo+interval_Pdt.+RS+mu_cumulo+nu_cumulo+rho_cumulo+nu_per_rho_cumulo+Arg_conc._cumulo+cell_yield_cumulo+rab_integral+Accum._Yield+emission_CO2+consum_O2+generate_CO2; 0.773, 0.906, tmp+PL+AN+interval_Pdt.+mu_cumulo+nu_cumulo+rho_cumulo+nu_per_rho_cumulo+Arg_conc._cumulo+cell_yield_cumulo+emission_CO2+consum_O2+interval_O2+generate_CO2; 0.781, 0.906, tmp+PL_cumulo+interval_Pdt.+OD+nu_cumulo+rho_cumulo+nu_per_rho_cumulo+Arg_conc._cumulo+rab_integral+emission_CO2+consum_O2+generate_CO2; 0.773, 0.906, tmp+PL+AN+interval_Pdt.+OD+nu_cumulo+rho_cumulo+nu_per_rho_cumulo+rab_integral+RQ_integral+Accum._Yield+emission_CO2+consum_O2+generate_CO2; 0.763, 0.906, tmp+PL+AN+interval_Pdt.+OD+mu_cumulo+nu_cumulo+rho_cumulo+nu_per_rho_cumulo+Arg_conc._cumulo+rab_integral+RQ_integral+Accum._Yield+emission_CO2+consum_O2+generate_CO2; 0.777, 0.906, tmp+PL_cumulo+AN+interval_Pdt.+OD+mu_cumulo+nu_cumulo+rho_cumulo+nu_per_rho_cumulo+Accum._Yield+emission_CO2+consum_O2+generate_CO2; 0.777, 0.906, tmp+PL+PL_cumulo+AN+interval_Pdt.+OD+mu_cumulo+nu_cumulo+rho_cumulo+nu_per_rho_cumulo+emission_CO2+consum_O2+generate_CO2; 0.763, 0.906, tmp+PL+interval_Pdt.+RS+mu_cumulo+nu_cumulo+rho_cumulo+nu_per_rho_cumulo+cell_yield_cumulo+RQ_integral+Accum._Yield+emission_O2+emission_CO2+consum_O2+interval_O2+generate_CO2; 0.768, 0.906, tmp+PL+PL_cumulo+AN+interval_Pdt.+RS+mu_cumulo+nu_cumulo+rho_cumulo+nu_per_rho_cumulo+Arg_conc._cumulo+rab_integral+emission_CO2+consum_O2+generate_CO2; 0.785, 0.906, tmp+PL+AN+interval_Pdt.+mu_cumulo+nu_cumulo+rho_cumulo+emission_CO2+consum_O2+interval_O2+generate_CO2; 0.763, 0.906, tmp+pH+PL+PL_cumulo+AN+interval_Pdt.+mu_cumulo+nu_cumulo+rho_cumulo+nu_per_rho_cumulo+rab_integral+Accum._Yield+emission_CO2+consum_O2+interval_O2+generate_CO2; 0.768, 0.906, tmp+pH+PL+PL_cumulo+AN+interval_Pdt.+mu_cumulo+nu_cumulo+rho_cumulo+nu_per_rho_cumulo+emission_O2+emission_CO2+consum_O2+interval_O2+generate_CO2; 0.781, 0.906, tmp+PL_cumulo+interval_Pdt.+OD+mu_cumulo+nu_cumulo+rho_cumulo+nu_per_rho_cumulo+emission_O2+emission_CO2+consum_O2+generate_CO2; 0.758, 0.906, tmp+PL+PL_cumulo+AN+interval_Pdt.+mu_cumulo+nu_cumulo+rho_cumulo+nu_per_rho_cumulo+Arg_conc._cumulo+RQ_integral+Accum._Yield+emission_O2+emission_CO2+consum_O2+interval_O2+generate_CO2; 0.785, 0.906, tmp+PL_cumulo+interval_Pdt.+mu_cumulo+nu_cumulo+rho_cumulo+nu_per_rho_cumulo+RQ_integral+emission_CO2+consum_O2+generate_CO2; 0.773, 0.906, tmp+PL_cumulo+interval_Pdt.+mu_cumulo+nu_cumulo+rho_cumulo+nu_per_rho_cumulo+rab_integral+RQ_integral+Accum._Yield+emission_CO2+consum_O2+interval_O2+generate_CO2; 0.773, 0.906, tmp+PL+PL_cumulo+interval_yield+interval_Pdt.+mu_cumulo+nu_cumulo+rho_cumulo+nu_per_rho_cumulo+cell_yield_cumulo+rab_integral+emission_CO2+consum_O2+generate_CO2; 0.768, 0.906, tmp+PL+AN+interval_Pdt.+OD+mu_cumulo+nu_cumulo+rho_cumulo+nu_per_rho_cumulo+Arg_conc._cumulo+Accum._Yield+emission_CO2+consum_O2+interval_O2+generate_CO2; 0.781, 0.906, tmp+PL_cumulo+interval_Pdt.+OD+mu_cumulo+nu_cumulo+rho_cumulo+nu_per_rho_cumulo+emission_CO2+consum_O2+interval_O2+generate_CO2; 0.773, 0.906, tmp+PL+PL_cumulo+AN+interval_Pdt.+RS+mu_cumulo+nu_cumulo+rho_cumulo+nu_per_rho_cumulo+emission_O2+emission_CO2+consum_O2+generate_CO2; 0.777, 0.906, tmp+PL_cumulo+interval_Pdt.+mu_cumulo+nu_cumulo+rho_cumulo+nu_per_rho_cumulo+rab_integral+RQ_integral+emission_CO2+consum_O2+interval_O2+generate_CO2; 0.785, 0.906, tmp+PL_cumulo+mu_cumulo+nu_cumulo+rho_cumulo+nu_per_rho_cumulo+cell_yield_cumulo+rab_integral+emission_CO2+consum_O2+generate_CO2; 0.773, 0.906, tmp+PL+AN+OD+RS+nu_cumulo+rho_cumulo+nu_per_rho_cumulo+Arg_conc._cumulo+rab_integral+Accum._Yield+emission_CO2+consum_O2+generate_CO2; 0.777, 0.906, tmp+pH+PL+interval_Pdt.+mu_cumulo+nu_cumulo+rho_cumulo+nu_per_rho_cumulo+cell_yield_cumulo+emission_CO2+consum_O2+generate_CO2; 0.781, 0.906, tmp+PL+PL_cumulo+AN+interval_Pdt.+mu_cumulo+rho_cumulo+Accum._Yield+emission_CO2+consum_O2+interval_O2+generate_CO2; 0.777, 0.906, tmp+PL+AN+interval_yield+interval_Pdt.+mu_cumulo+rho_cumulo+nu_per_rho_cumulo+Accum._Yield+emission_CO2+consum_O2+interval_O2+generate_CO2; 0.781, 0.906, tmp+PL_cumulo+interval_Pdt.+OD+RS+mu_cumulo+nu_cumulo+rho_cumulo+nu_per_rho_cumulo+emission_CO2+consum_O2+generate_CO2; 0.777, 0.906, tmp+PL+OD+mu_cumulo+nu_cumulo+rho_cumulo+nu_per_rho_cumulo+Arg_conc._cumulo+rab_integral+Accum._Yield+emission_CO2+consum_O2+generate_CO2; 0.777, 0.906, tmp+PL+AN+interval_yield+interval_Pdt.+mu_cumulo+rho_cumulo+rab_integral+Accum._Yield+emission_CO2+consum_O2+interval_O2+generate_CO2; 0.768, 0.906, tmp+PL+PL_cumulo+interval_Pdt.+mu_cumulo+nu_cumulo+rho_cumulo+nu_per_rho_cumulo+rab_integral+RQ_integral+Accum._Yield+emission_CO2+consum_O2+interval_O2+generate_CO2; 0.789, 0.906, tmp+PL_cumulo+interval_Pdt.+OD+nu_cumulo+rho_cumulo+nu_per_rho_cumulo+emission_CO2+consum_O2+generate_CO2; 0.763, 0.906, tmp+pH+PL+PL_cumulo+interval_Pdt.+OD+RS+nu_cumulo+rho_cumulo+nu_per_rho_cumulo+Arg_conc._cumulo+Accum._Yield+emission_O2+emission_CO2+consum_O2+generate_CO2; 0.785, 0.906, tmp+PL_cumulo+interval_Pdt.+OD+nu_cumulo+rho_cumulo+nu_per_rho_cumulo+Arg_conc._cumulo+emission_CO2+consum_O2+generate_CO2; 0.789, 0.906, tmp+PL+OD+ nu_cumulo+rho_cumulo+nu_per_rho_cumulo+rab_integral+emission_CO2+consum_O2+generate_CO2; 0.763, 0.906, tmp+PL+PL_cumulo+interval_Pdt.+mu_cumulo+nu_cumulo+rho_cumulo+nu_per_rho_cumulo+cell_yield_cumulo+rab_integral+RQ_integral+Accum._Yield+emission_O2+emission_CO2+consum_O2+generate_CO2; 0.773, 0.906, tmp+PL+AN+interval_Pdt.+OD+nu_cumulo+rho_cumulo+nu_per_rho_cumulo+rab_integral+Accum._Yield+emission_CO2+consum_O2+interval_O2+generate_CO2; 0.768, 0.906, tmp+PL+AN+interval_Pdt.+OD+RS+nu_cumulo+rho_cumulo+nu_per_rho_cumulo+Arg_conc._cumulo+Accum._Yield+emission_O2+emission_CO2+consum_O2+generate_CO2; 0.773, 0.906, tmp+PL+PL_cumulo+AN+interval_Pdt.+RS+mu_cumulo+nu_cumulo+rho_cumulo+nu_per_rho_cumulo+Accum._Yield+emission_CO2+consum_O2+generate_CO2; 0.768, 0.906, tmp+PL+AN+interval_Pdt.+OD+mu_cumulo+nu_cumulo+rho_cumulo+nu_per_rho_cumulo+RQ_integral+Accum._Yield+emission_O2+emission_CO2+consum_O2+generate_CO2; 0.773, 0.906, tmp+PL+PL_cumulo+OD+RS+nu_cumulo+rho_cumulo+nu_per_rho_cumulo+Arg_conc._cumulo+rab_integral+Accum._Yield+emission_CO2+consum_O2+generate_CO2; 0.768, 0.906, tmp+pH+PL+PL_cumulo+AN+interval_Pdt.+mu_cumulo+nu_cumulo+rho_cumulo+nu_per_rho_cumulo+Accum._Yield+emission_O2+emission_CO2+consum_O2+generate_CO2; 0.785, 0.906, tmp+interval_Pdt.+OD+mu_cumulo+nu_cumulo+rho_cumulo+nu_per_rho_cumulo+rab_integral+emission_CO2+consum_O2+generate_CO2; 0.785, 0.906, tmp+pH+PL+interval_Pdt.+mu_cumulo+nu_cumulo+rho_cumulo+nu_per_rho_cumulo+emission_CO2+consum_O2+generate_CO2; 0.773, 0.906, tmp+PL+interval_Pdt.+OD+mu_cumulo+nu_cumulo+rho_cumulo+nu_per_rho_cumulo+Arg_conc._cumulo+rab_integral+emission_CO2+consum_O2+interval_O2+generate_CO2; 0.768, 0.906, tmp+pH+PL+interval_Pdt.+RS+mu_cumulo+nu_cumulo+rho_cumulo+nu_per_rho_cumulo+rab_integral+RQ_integral+Accum._Yield+emission_CO2+consum_O2+generate_CO2; 0.758, 0.906, tmp+pH+PL+PL_cumulo+AN+interval_Pdt.+OD+nu_cumulo+rho_cumulo+nu_per_rho_cumulo+Arg_conc._cumulo+rab_integral+Accum._Yield+emission_O2+emission_CO2+consum_O2+generate_CO2; 0.773, 0.906, tmp+PL_cumulo+interval_Pdt.+OD+mu_cumulo+nu_cumulo+rho_cumulo+nu_per_rho_cumulo+Arg_conc._cumulo+rab_integral+Accum._Yield+emission_CO2+consum_O2+generate_CO2; 0.768, 0.906, tmp+PL_cumulo+interval_Pdt.+RS+mu_cumulo+nu_cumulo+rho_cumulo+nu_per_rho_cumulo+Arg_conc._cumulo+rab_integral+RQ_integral+Accum._Yield+emission_CO2+consum_O2+generate_CO2; 0.777, 0.906, tmp+PL+AN+interval_Pdt.+OD+nu_cumulo+rho_cumulo+nu_per_rho_cumulo+cell_yield_cumulo+rab_integral+emission_CO2+consum_O2+generate_CO2; 0.781, 0.906, tmp+PL+OD+RS+nu_cumulo+rho_cumulo+nu_per_rho_cumulo+Arg_conc._cumulo+rab_integral+Accum._Yield+emission_CO2+generate_CO2; 0.773, 0.906, tmp+PL+PL_cumulo+AN+interval_Pdt.+OD+nu_cumulo+rho_cumulo+nu_per_rho_cumulo+Arg_conc._cumulo+Accum._Yield+emission_CO2+consum_O2+generate_CO2; 0.781, 0.906, tmp+interval_Pdt.+RS+mu_cumulo+nu_cumulo+rho_cumulo+nu_per_rho_cumulo+cell_yield_cumulo+rab_integral+emission_CO2+consum_O2+generate_CO2; 0.773, 0.906, tmp+PL+PL_cumulo+interval_Pdt.+mu_cumulo+nu_cumulo+rho_cumulo+nu_per_rho_cumulo+cell_yield_cumulo+rab_integral+emission_CO2+consum_O2+generate_CO2; 0.772, 0.906, tmp+PL+interval_Pdt.+mu_cumulo+nu_cumulo+rho_cumulo+nu_per_rho_cumulo+Arg_conc._cumulo+RQ_integral+emission_O2+emission_CO2+consum_O2+interval_O2+generate_CO2; 0.768, 0.906, tmp+PL+AN+interval_Pdt.+OD+mu_cumulo+nu_cumulo+rho_cumulo+nu_per_rho_cumulo+cell_yield_cumulo+Accum._Yield+emission_O2+emission_CO2+consum_O2+generate_CO2; 0.772, 0.906, tmp+PL+PL_cumulo+interval_Pdt.+RS+mu_cumulo+nu_cumulo+rho_cumulo+nu_per_rho_cumulo+Arg_conc._cumulo+rab_integral+emission_CO2+consum_O2+generate_CO2; 0.768, 0.906, tmp+PL+AN+interval_Pdt.+OD+RS+mu_cumulo+nu_cumulo+rho_cumulo+nu_per_rho_cumulo+cell_yield_cumulo+rab_integral+emission_CO2+consum_O2+generate_CO2; 0.789, 0.906, tmp+PL_cumulo+OD+nu_cumulo+rho_cumulo+nu_per_rho_cumulo+Arg_conc._cumulo+emission_CO2+consum_O2+generate_CO2; 0.777, 0.906, tmp+PL+interval_Pdt.+OD+nu_cumulo+rho_cumulo+nu_per_rho_cumulo+Arg_conc._cumulo+RQ_integral+emission_O2+emission_CO2+consum_O2+generate_CO2; 0.772, 0.906, tmp+pH+PL+PL_cumulo+interval_Pdt.+mu_cumulo+nu_cumulo+rho_cumulo+nu_per_rho_cumulo+Accum._Yield+emission_O2+emission_CO2+consum_O2+generate_CO2; 0.781, 0.906, tmp+PL+AN+interval_yield+interval_Pdt.+mu_cumulo+rho_cumulo+Arg_conc._cumulo+emission_CO2+consum_O2+interval_O2+generate_CO2; 0.768, 0.906, tmp+PL+AN+interval_Pdt.+mu_cumulo+nu_cumulo+rho_cumulo+nu_per_rho_cumulo+cell_yield_cumulo+rab_integral+Accum._Yield+emission_CO2+consum_O2+generate_CO2; 0.781, 0.906, tmp+PL_cumulo+interval_Pdt.+RS+mu_cumulo+nu_cumulo+rho_cumulo+nu_per_rho_cumulo+Accum._Yield+emission_CO2+consum_O2+generate_CO2; 0.772, 0.906, tmp+PL+AN+interval_Pdt.+mu_cumulo+nu_cumulo+rho_cumulo+nu_per_rho_cumulo+cell_yield_cumulo+rab_integral+emission_CO2+emission_CO2+consum_O2+generate_CO2; 0.777, 0.906, tmp+pH+PL_cumulo+OD+nu_cumulo+rho_cumulo+nu_per_rho_cumulo+Arg_conc._cumulo+rab_integral+Accum._Yield+emission_CO2+consum_O2+generate_CO2; 0.777, 0.906, tmp+pH+PL+PL_cumulo+interval_Pdt.+mu_cumulo+nu_cumulo+rho_cumulo+nu_per_rho_cumulo+emission_O2+emission_CO2+consum_O2+generate_CO2; 0.772, 0.906, tmp+PL+PL_cumulo+interval_Pdt.+RS+mu_cumulo+nu_cumulo+rho_cumulo+nu_per_rho_cumulo+emission_O2+emission_CO2+consum_O2+interval_O2+generate_CO2; 0.785, 0.906, tmp+PL_cumulo+interval_Pdt.+OD+nu_cumulo+rho_cumulo+nu_per_rho_cumulo+rab_integral+emission_CO2+consum_O2+generate_CO2; 0.777, 0.906, tmp+PL+AN+interval_Pdt.+OD+RS+nu_cumulo+rho_cumulo+nu_per_rho_cumulo+rab_integral+emission_CO2+consum_O2+generate_CO2; 0.768, 0.906, tmp+pH+PL+interval_Pdt.+mu_cumulo+nu_cumulo+rho_cumulo+nu_per_rho_cumulo+Arg_conc._cumulo+cell_yield_cumulo+rab_integral+Accum._Yield+emission_CO2+consum_O2+generate_CO2; 0.781, 0.906, tmp+PL+AN+interval_Pdt.+OD+nu_cumulo+rho_cumulo+nu_per_rho_cumulo+Accum._Yield+emission_CO2+consum_O2+generate_CO2; 0.768, 0.906, tmp+PL+PL_cumulo+AN+interval_Pdt.+mu_cumulo+nu_cumulo+rho_cumulo+nu_per_rho_cumulo+Arg_conc._cumulo+cell_yield_cumulo+rab_integral+emission_CO2+consum_O2+generate_CO2; 0.772, 0.906, tmp+PL+AN+interval_Pdt.+RS+mu_cumulo+nu_cumulo+rho_cumulo+nu_per_rho_cumulo+Arg_conc._cumulo+emission_CO2+consum_O2+interval_O2+generate_CO2; 0.763, 0.906, tmp+PL+interval_Pdt.+mu_cumulo+nu_cumulo+rho_cumulo+nu_per_rho_cumulo+Arg_conc._cumulo+cell_yield_cumulo+RQ_integral+Accum._Yield+emission_O2+emission_CO2+consum_

O2+interval_O2+generate_CO2; 0.777, 0.906, tmp+pH+interval_Pdt.+mu_cumulo+nu_cumulo+rho_cumulo+nu_per_rho_cumulo+Arg_conc._cumulo+rab_integral+Accum._Yield+emission_CO2+consum_O2+generate_CO2; 0.777, 0.906, tmp+PL+OD+nu_cumulo+rho_cumulo+nu_per_rho_cumulo+Arg_conc._cumulo+rab_integral+Accum._Yield+emission_CO2+consum_O2+interval_O2+generate_CO2; 0.781, 0.906, tmp+PL+AN+interval_yield+interval_Pdt.+mu_cumulo+rho_cumulo+rab_integral+emission_CO2+consum_O2+interval_O2+generate_CO2; 0.763, 0.906, tmp+PL+PL_cumulo+interval_Pdt.+OD+mu_cumulo+nu_cumulo+rho_cumulo+nu_per_rho_cumulo+RQ_integral+Accum._Yield+emission_O2+emission_CO2+consum_O2+interval_O02+generate_CO2; 0.785, 0.906, tmp+interval_Pdt.+mu_cumulo+nu_cumulo+rho_cumulo+nu_per_rho_cumulo+rab_integral+RQ_integral+Accum._Yield+emission_CO2+consum_O2; 0.768, 0.906, tmp+PL+AN+interval_Pdt.+mu_cumulo+nu_cumulo+rho_cumulo+nu_per_rho_cumulo+rab_integral+RQ_integral+Accum._Yield+emission_O2+emission_CO2+consum_O2+generate_CO2; 0.777, 0.906, tmp+PL+AN+interval_Pdt.+OD+nu_cumulo+rho_cumulo+nu_per_rho_cumulo+Accum._Yield+emission_O2+emission_CO2+consum_O2+generate_CO2; 0.785, 0.906, tmp+PL+AN+interval_Pdt.+OD+mu_cumulo+rho_cumulo+Accum._Yield+emission_CO2+consum_O2+generate_CO2; 0.772, 0.906, tmp+PL+interval_Pdt.+mu_cumulo+nu_cumulo+rho_cumulo+nu_per_rho_cumulo+Arg_conc._cumulo+rab_integral+RQ_integral+emission_CO2+consum_O2+interval_O2+generate_CO2; 0.781, 0.906, tmp+PL+OD+mu_cumulo+nu_cumulo+rho_cumulo+nu_per_rho_cumulo+cell_yield_cumulo+emission_O2+emission_CO2+consum_O2+generate_CO2; 0.772, 0.906, tmp+PL+PL_cumulo+interval_Pdt.+mu_cumulo+nu_cumulo+rho_cumulo+nu_per_rho_cumulo+cell_yield_cumulo+RQ_integral+emission_O2+emission_CO2+consum_O2+generate_CO2; 0.781, 0.906, tmp+PL+OD+nu_cumulo+rho_cumulo+nu_per_rho_cumulo+Arg_conc._cumulo+cell_yield_cumulo+emission_O2+emission_CO2+consum_O2+generate_CO2; 0.763, 0.906, tmp+PL+interval_Pdt.+OD+RS+mu_cumulo+nu_cumulo+rho_cumulo+nu_per_rho_cumulo+cell_yield_cumulo+RQ_integral+Accum._Yield+emission_O2+emission_CO2+consum_O2+generate_CO2; 0.772, 0.906, tmp+PL+interval_yield+interval_Pdt.+mu_cumulo+nu_cumulo+rho_cumulo+nu_per_rho_cumulo+Arg_conc._cumulo+cell_yield_cumulo+rab_integral+emission_CO2+consum_O2+generate_CO2; 0.763, 0.906, tmp+pH+PL+PL_cumulo+interval_Pdt.+OD+mu_cumulo+nu_cumulo+rho_cumulo+nu_per_rho_cumulo+Arg_conc._cumulo+Accum._Yield+emission_O2+emission_CO2+consum_O2+generate_CO2; 0.781, 0.906, tmp+PL+OD+nu_cumulo+rho_cumulo+nu_per_rho_cumulo+Arg_conc._cumulo+rab_integral+emission_CO2+consum_O2+interval_O2+generate_CO2; 0.781, 0.906, tmp+PL+AN+interval_Pdt.+RS+mu_cumulo+rho_cumulo+Arg_conc._cumulo+Accum._Yield+emission_CO2+consum_O2+generate_CO2; 0.763, 0.906, tmp+PL+interval_Pdt.+mu_cumulo+nu_cumulo+rho_cumulo+nu_per_rho_cumulo+cell_yield_cumulo+rab_integral+RQ_integral+Accum._Yield+emission_O2+emission_CO2+consum_O2+interval_O2+generate_CO2; 0.781, 0.906, tmp+PL+AN+interval_Pdt.+OD+mu_cumulo+rho_cumulo+Accum._Yield+emission_CO2+consum_O2+interval_O2+generate_CO2; 0.758, 0.906, tmp+PL+PL_cumulo+AN+interval_Pdt.+RS+mu_cumulo+rho_cumulo+nu_per_rho_cumulo+Arg_conc._cumulo+rab_integral+Accum._Yield+emission_O2+emission_CO2+consum_

O2+generate_CO2; 0.772, 0.906, tmp+pH+PL+AN+interval_Pdt.+mu_cumulo+nu_cumulo+rho_cumulo+nu_per_rho_cumulo+rab_integral+RQ_integral+emission_CO2+consum_O2+generate_CO2; 0.758, 0.906, tmp+PL+PL_cumulo+AN+interval_Pdt.+mu_cumulo+nu_cumulo+rho_cumulo+nu_per_rho_cumulo+Arg_conc._cumulo+rab_integral+RQ_integral+Accum._Yield+emission_O2+emission_CO2+consum_O2+generate_CO2; 0.781, 0.906, tmp+PL+OD+mu_cumulo+nu_cumulo+rho_cumulo+nu_per_rho_cumulo+cell_yield_cumulo+rab_integral+emission_CO2+consum_O2+generate_CO2; 0.758, 0.906, tmp+PL+PL_cumulo+AN+interval_Pdt.+RS+mu_cumulo+nu_cumulo+rho_cumulo+nu_per_rho_cumulo+Arg_conc._cumulo+cell_yield_cumulo+rab_integral+Accum._Yield+emission_CO2+consum_O2+generate_CO2; 0.777, 0.906, tmp+PL+AN+interval_Pdt.+mu_cumulo+nu_cumulo+rho_cumulo+nu_per_rho_cumulo+cell_yield_cumulo+RQ_integral+emission_CO2+consum_O2+generate_CO2; 0.781, 0.906, tmp+PL+interval_Pdt.+mu_cumulo+nu_cumulo+rho_cumulo+nu_per_rho_cumulo+cell_yield_cumulo+Accum._Yield+emission_CO2+consum_O2+generate_CO2; 0.772, 0.906, tmp+PL+PL_cumulo+AN+interval_Pdt.+OD+nu_cumulo+rho_cumulo+nu_per_rho_cumulo+Arg_conc._cumulo+rab_integral+emission_CO2+consum_O2+generate_CO2; 0.772, 0.906, tmp+PL+AN+interval_Pdt.+OD+nu_cumulo+rho_cumulo+nu_per_rho_cumulo+Arg_conc._cumulo+emission_O2+emission_CO2+consum_O2+interval_O2+generate_CO2; 0.772, 0.906, tmp+PL+AN+interval_Pdt.+OD+mu_cumulo+nu_cumulo+rho_cumulo+nu_per_rho_cumulo+cell_yield_cumulo+emission_CO2+consum_O2+interval_O2+generate_CO2; 0.758, 0.906, tmp+pH+PL+PL_cumulo+AN+interval_Pdt.+OD+mu_cumulo+nu_cumulo+rho_cumulo+nu_per_rho_cumulo+Arg_conc._cumulo+rab_integral+Accum._Yield+emission_CO2+consum_O2+generate_CO2; 0.768, 0.906, tmp+PL+AN+interval_Pdt.+OD+RS+mu_cumulo+nu_cumulo+rho_cumulo+nu_per_rho_cumulo+rab_integral+emission_CO2+consum_O2+interval_O2+generate_CO2; 0.781, 0.906, tmp+PL+OD+RS+nu_cumulo+rho_cumulo+nu_per_rho_cumulo+Arg_conc._cumulo+emission_O2+emission_CO2+consum_O2+generate_CO2; 0.793, 0.906, tmp+PL+AN+interval_Pdt.+mu_cumulo+rho_cumulo+emission_CO2+consum_O2+generate_CO2; 0.772, 0.906, tmp+PL+interval_Pdt.+RS+mu_cumulo+nu_cumulo+rho_cumulo+nu_per_rho_cumulo+Arg_conc.cumulo+cell_yield_cumulo+emission_O2+emission_CO2+consum_O2+generate_CO2; 0.777, 0.906, tmp+pH+PL+interval_Pdt.+mu_cumulo+nu_cumulo+rho_cumulo+nu_per_rho_cumulo+Accum._Yield+emission_O2+emission_CO2+consum_O2+generate_CO2; 0.772, 0.906, tmp+PL+interval_Pdt.+mu_cumulo+nu_cumulo+rho_cumulo+nu_per_rho_cumulo+Arg_conc._cumulo+rab_integral+Accum._Yield+emission_CO2+consum_O2+interval_O2+generate_CO2; 0.777, 0.906, tmp+interval_Pdt.+RS+mu_cumulo+nu_cumulo+rho_cumulo+nu_per_rho_cumulo+rab_integral+RQ_integral+Accum._Yield+emission_CO2+consum_O2+generate_CO2; 0.785, 0.906, tmp+PL+AN+interval_Pdt.+mu_cumulo+rho_cumulo+Accum._Yield+emission_O2+emission_CO2+consum_O2+generate_CO2; 0.763, 0.906, tmp+PL_cumulo+interval_Pdt.+RS+mu_cumulo+nu_cumulo+rho_cumulo+nu_per_rho_cumulo+Arg_conc._cumulo+cell_yield_cumulo+rab_integral+RQ_integral+Accum._Yield+emission_CO2+consum_O2+generate_CO2; 0.768, 0.906, tmp+PL+PL_cumulo+AN+interval_yield+interval_Pdt.+mu_cumulo+nu_cumulo+rho_cumulo+nu_per_rho_cumulo+rab_integral+RQ_integral+emission_CO2+consum_O2+generate_CO2; 0.772, 0.906, tmp+PL+PL_cumulo+AN+interval_Pdt.+OD+mu_cumulo+nu_cumulo+rho_cumulo+nu_per_rho_cumulo+emission_O2+emission_CO2+consum_O2+generate_CO2; 0.777, 0.906, tmp+PL_cumulo+interval_Pdt.+OD+mu_cumulo+nu_cumulo+rho_cumulo+nu_per_rho_cumulo+rab_integral+emission_CO2+consum_O2+interval_O2+generate_CO2; 0.772, 0.906, tmp+PL+PL_cumulo+interval_Pdt.+OD+mu_cumulo+nu_cumulo+rho_cumulo+nu_per_rho_cumulo+emission_O2+emission_CO2+consum_O2+interval_O2+generate_CO2; 0.763, 0.906, tmp+PL+PL_cumulo+interval_Pdt.+RS+mu_cumulo+nu_cumulo+rho_cumulo+nu_per_rho_cumulo+RQ_integral+Accum._Yield+emission_O2+emission_CO2+consum_O2+interval_O2+generate_CO2; 0.772, 0.906, tmp+PL+PL_cumulo+AN+interval_Pdt.+mu_cumulo+nu_cumulo+rho_cumulo+nu_per_rho_cumulo+cell_yield_cumulo+Accum._Yield+emission_CO2+consum_O2+generate_CO2; 0.763, 0.906, tmp+PL+PL_cumulo+AN+interval_Pdt.+mu_cumulo+nu_cumulo+rho_cumulo+nu_per_rho_cumulo+Arg_conc._cumulo+cell_yield_cumulo+Accum._Yield+emission_O2+emission_CO2+consum_O2+generate_CO2; 0.785, 0.906, tmp+PL+mu_cumulo+nu_cumulo+rho_cumulo+nu_per_rho_cumulo+cell_yield_cumulo+emission_O2+emission_CO2+consum_O2+generate_CO2; 0.758, 0.906, tmp+PL+PL_cumulo+interval_Pdt.+mu_cumulo+nu_cumulo+rho_cumulo+nu_per_rho_cumulo+Arg_conc._cumulo+cell_yield_cumulo+rab_integral+RQ_integral+Accum._Yield+emission_O2+emission_CO2+consum_O2+generate_CO2; 0.777, 0.906, tmp+PL_cumulo+interval_Pdt.+mu_cumulo+nu_cumulo+rho_cumulo+nu_per_rho_cumulo+RQ_integral+Accum._Yield+emission_O2+emission_CO2+consum_O2+generate_CO2; 0.781, 0.906, tmp+PL+PL_cumulo+interval_Pdt.+OD+nu_cumulo+rho_cumulo+nu_per_rho_cumulo+emission_O2+emission_CO2+consum_O2+generate_CO2; 0.777, 0.906, tmp+interval_Pdt.+mu_cumulo+nu_cumulo+rho_cumulo+nu_per_rho_cumulo+Arg_conc._cumulo+cell_yield_cumulo+rab_integral+Accum._Yield+emission_CO2+consum_O2+generate_CO2; 0.781, 0.906, tmp+pH+PL+AN+interval_Pdt.+mu_cumulo+rho_cumulo+Accum._Yield+emission_CO2+consum_O2+interval_O2+generate_CO2; 0.777, 0.906, tmp+PL_cumulo+AN+interval_Pdt.+mu_cumulo+nu_cumulo+rho_cumulo+nu_per_rho_cumulo+cell_yield_cumulo+rab_integral+emission_CO2+consum_O2+generate_CO2; 0.763, 0.906, tmp+PL+AN+interval_Pdt.+OD+mu_cumulo+nu_cumulo+rho_cumulo+nu_per_rho_cumulo+rab_integral+RQ_integral+Accum._Yield+emission_CO2+consum_O2+interval_O2+generate_CO2; 0.776, 0.906, tmp+PL+AN+interval_Pdt.+mu_cumulo+rho_cumulo+nu_cumulo+nu_per_rho_cumulo+Arg_conc._cumulo+rab_integral+emission_CO2+consum_O2+interval_O2+generate_CO2; 0.768, 0.906, tmp+PL+interval_Pdt.+RS+mu_cumulo+nu_cumulo+rho_cumulo+nu_per_rho_cumulo+Arg_conc._cumulo+cell_yield_cumulo+Accum._Yield+emission_O2+emission_CO2+consum_O2+generate_CO2; 0.776, 0.906, tmp+pH+interval_Pdt.+mu_cumulo+nu_cumulo+rho_cumulo+nu_per_rho_cumulo+cell_yield_cumulo+rab_integral+Accum._Yield+emission_CO2+consum_O2+generate_CO2; 0.772, 0.906, tmp+PL+PL_cumulo+interval_Pdt.+RS+mu_cumulo+nu_cumulo+rho_cumulo+nu_per_rho_cumulo+rab_integral+RQ_integral+emission_CO2+consum_O2+generate_CO2; 0.781, 0.906, tmp+interval_Pdt.+OD+mu_cumulo+nu_cumulo+rho_cumulo+nu_per_rho_cumulo+rab_integral+Accum._Yield+emission_CO2+consum_O2+generate_CO2; 0.776, 0.906, tmp+interval_Pdt.+mu_cumulo+nu_cumulo+rho_cumulo+nu_per_rho_cumulo+cell_yield_cumulo+rab_integral+RQ_integral+Accum._Yield+emission_CO2+consum_O2+generate_CO2; 0.776, 0.906, tmp+interval_Pdt.+OD+mu_cumulo+nu_cumulo+rho_cumulo+nu_per_rho_cumulo+Arg_conc._cumulo+rab_integral+Accum._Yield+emission_CO2+consum_O2+generate_CO2; 0.792, 0.906, tmp+PL+interval_Pdt.+mu_cumulo+rho_cumulo+nu_per_rho_cumulo+emission_CO2+consum_O2+generate_CO2; 0.763, 0.906, tmp+PL+AN+interval_Pdt.+OD+mu_cumulo+nu_cumulo+rho_cumulo+nu_per_rho_cumulo+Arg_conc._cumulo+rab_integral+Accum._Yield+emission_CO2+consum_O2+interval_O2+generate_CO2; 0.781, 0.906, tmp+PL_cumulo+AN+interval_Pdt.+mu_cumulo+nu_cumulo+rho_cumulo+nu_per_rho_cumulo+Arg_conc._cumulo+emission_CO2+consum_O2+generate_CO2; 0.767, 0.906, tmp+PL+AN+interval_Pdt.+OD+mu_cumulo+nu_cumulo+rho_cumulo+nu_per_rho_cumulo+Arg_conc._cumulo+cell_yield_cumulo+rab_integral+emission_CO2+consum_O2+generate_CO2; 0.781, 0.906, tmp+PL+AN+interval_Pdt.+mu_cumulo+rho_cumulo+RQ_integral+Accum._Yield+emission_CO2+consum_O2+interval_O2+generate_CO2; 0.789, 0.906, tmp+PL_cumulo+OD+nu_cumulo+rho_cumulo+nu_per_rho_cumulo+rab_integral+emission_CO2+consum_O2+generate_CO2; 0.772, 0.906, tmp+PL_cumulo+interval_Pdt.+mu_cumulo+nu_cumulo+rho_cumulo+nu_per_rho_cumulo+Arg_conc._cumulo+cell_yield_cumulo+rab_integral+RQ_integral+emission_CO2+consum_O2+generate_CO2; 0.785, 0.906, tmp+OD+RS+nu_cumulo+rho_cumulo+nu_per_rho_cumulo+Arg_conc._cumulo+rab_integral+Accum._Yield+emission_CO2+generate_CO2; 0.772, 0.906, tmp+PL+AN+interval_Pdt.+mu_cumulo+nu_cumulo+rho_cumulo+nu_per_rho_cumulo+Arg_conc._cumulo+Accum._Yield+emission_O2+emission_CO2+consum_O2+generate_CO2; 0.785, 0.906, tmp+PL_cumulo+OD+nu_cumulo+rho_cumulo+nu_per_rho_cumulo+Arg_conc._cumulo+emission_O2+emission_CO2+consum_O2+generate_CO2; 0.785, 0.906, tmp+interval_Pdt.+mu_cumulo+nu_cumulo+rho_cumulo+nu_per_rho_cumulo+Arg_conc._cumulo+rab_integral+emission_CO2+consum_O2+generate_CO2; 0.776, 0.906, tmp+PL_cumulo+interval_Pdt.+RS+mu_cumulo+nu_cumulo+rho_cumulo+nu_per_rho_cumulo+Arg_conc._cumulo+rab_integral+emission_CO2+consum_O2+generate_CO2; 0.767, 0.906, tmp+PL+AN+interval_Pdt.+RS+mu_cumulo+nu_cumulo+rho_cumulo+nu_per_rho_cumulo+cell_yield_cumulo+emission_O2+emission_CO2+consum_O2+interval_O2+generate_CO2; 0.781, 0.906, tmp+PL+AN+interval_Pdt.+mu_cumulo+rho_cumulo+nu_per_rho_cumulo+emission_O2+emission_CO2+consum_O2+interval_O2+generate_CO2; 0.763, 0.906, tmp+pH+PL+interval_Pdt.+OD+mu_cumulo+nu_cumulo+rho_cumulo+nu_per_rho_cumulo+Arg_conc._cumulo+rab_integral+RQ_integral+Accum._Yield+emission_CO2+consum_O2+generate_CO2; 0.772, 0.906, tmp+PL+interval_Pdt.+OD+RS+mu_cumulo+nu_cumulo+rho_cumulo+nu_per_rho_cumulo+Accum._Yield+emission_O2+emission_CO2+consum_O2+generate_CO2; 0.767, 0.906, tmp+PL+PL_cumulo+AN+interval_Pdt.+RS+mu_cumulo+nu_cumulo+rho_cumulo+nu_per_rho_cumulo+cell_yield_cumulo+rab_integral+emission_CO2+consum_O2+generate_CO2; 0.767, 0.906, tmp+PL+AN+interval_Pdt.+mu_cumulo+nu_cumulo+rho_cumulo+nu_per_rho_cumulo+Arg_conc._cumulo+rab_integral+RQ_integral+emission_CO2+consum_O2+interval_O2+generate_CO2; 0.785, 0.906, tmp+PL_cumulo+OD+nu_cumulo+rho_cumulo+nu_per_rho_cumulo+Arg_conc._cumulo+rab_integral+emission_CO2+interval_O2+generate_CO2; 0.763, 0.906, tmp+PL+PL_cumulo+AN+interval_Pdt.+mu_cumulo+nu_cumulo+rho_ cumulo+nu_per_rho_cumulo+cell_yield_cumulo+rab_integral+RQ_integral+Accum._Yield+emission_CO2+consum_O2+generate_CO2; 0.776, 0.906, tmp+PL_cumulo+AN+interval_Pdt.+OD+mu_cumulo+nu_cumulo+rho_cumulo+nu_per_rho_cumulo+emission_CO2+consum_O2+interval_O2+generate_CO2; 0.772, 0.906, tmp+PL+interval_Pdt.+RS+mu_cumulo+nu_cumulo+rho_cumulo+nu_per_rho_cumulo+cell_yield_cumulo+emission_O2+emission_CO2+consum_O2+interval_O2+generate_CO2; 0.781, 0.906, tmp+PL_cumulo+interval_Pdt.+OD+nu_cumulo+rho_cumulo+nu_per_rho_cumulo+rab_integral+RQ_integral+emission_CO2+consum_O2+generate_CO2; 0.781, 0.906, tmp+PL+AN+OD+nu_cumulo+rho_cumulo+nu_per_rho_cumulo+Arg_conc._cumulo+emission_O2+emission_CO2+consum_O2+generate_CO2; 0.776, 0.906, tmp+PL+interval_Pdt.+OD+mu_cumulo+nu_cumulo+rho_cumulo+nu_per_rho_cumulo+Arg_conc._cumulo+Accum._Yield+emission_CO2+consum_O2+generate_CO2; 0.758, 0.906, tmp+PL+PL_cumulo+AN+interval_Pdt.+mu_cumulo+nu_cumulo+rho_cumulo+nu_per_rho_cumulo+Arg_conc._cumulo+cell_yield_cumulo+Accum._Yield+emission_O2+emission_CO2+consum_O2+interval_O2+generate_CO2; 0.792, 0.906, tmp+PL_cumulo+interval_Pdt.+mu_cumulo+rho_cumulo+nu_per_rho_cumulo+emission_CO2+consum_O2+generate_CO2; 0.767, 0.906, tmp+PL+interval_Pdt.+mu_cumulo+nu_cumulo+rho_cumulo+nu_per_rho_cumulo+Arg_conc._cumulo+cell_yield_cumulo+rab_integral+Accum._Yield+emission_CO2+consum_O2+interval_O2+generate_CO2; 0.772, 0.906, tmp+pH+PL+interval_Pdt.+mu_cumulo+nu_cumulo+rho_cumulo+nu_per_rho_cumulo+Arg_conc._cumulo+cell_yield_cumulo+rab_integral+emission_CO2+consum_O2+generate_CO2; 0.792, 0.906, tmp+PL+interval_Pdt.+mu_cumulo+rho_cumulo+Accum._Yield+emission_CO2+consum_O2+generate_CO2; 0.767, 0.906, tmp+PL+PL_cumulo+interval_Pdt.+RS+mu_cumulo+nu_cumulo+rho_cumulo+nu_per_rho_cumulo+Accum._Yield+emission_O2+emission_CO2+consum_O2+interval_O2+generate_CO2; 0.772, 0.906, tmp+PL+interval_Pdt.+mu_cumulo+nu_cumulo+rho_cumulo+nu_per_rho_cumulo+cell_yield_cumulo+rab_integral+RQ_integral+emission_O2+emission_CO2+consum_O2+generate_CO2; 0.781, 0.906, tmp+PL+PL_cumulo+interval_Pdt.+OD+nu_cumulo+rho_cumulo+nu_per_rho_cumulo+rab_integral+emission_CO2+consum_O2+generate_CO2; 0.780, 0.906, tmp+PL+AN+interval_Pdt.+RS+mu_cumulo+rho_cumulo+nu_per_rho_cumulo+rab_integral+emission_CO2+consum_O2+generate_CO2; 0.780, 0.906, tmp+PL+AN+interval_yield+interval_Pdt.+RS+mu_cumulo+rho_cumulo+Accum._Yield+emission_CO2+consum_O2+generate_CO2; 0.772, 0.906, tmp+PL_cumulo+interval_Pdt.+OD+RS+mu_cumulo+nu_cumulo+rho_cumulo+nu_per_rho_cumulo+cell_yield_cumulo+rab_integral+emission_CO2+consum_O2+generate_CO2; 0.776, 0.906, tmp+pH+PL+AN+interval_Pdt.+mu_cumulo+nu_cumulo+rho_cumulo+nu_per_rho_cumulo+Arg_conc._cumulo+emission_CO2+consum_O2+generate_CO2; 0.772, 0.906, tmp+PL+interval_yield+interval_Pdt.+RS+mu_cumulo+nu_cumulo+rho_cumulo+nu_per_rho_cumulo+cell_yield_cumulo+rab_integral+emission_CO2+consum_O2+generate_CO2; 0.776, 0.906, tmp+PL+AN+interval_yield+interval_Pdt.+mu_cumulo+rho_cumulo+nu_per_rho_cumulo+rab_integral+emission_CO2+consum_O2+interval_O2+generate_CO2; 0.767, 0.906, tmp+PL+AN+interval_Pdt.+mu_cumulo+nu_cumulo+rho_cumulo+nu_per_rho_cumulo+Arg_conc._cumulo+cell_yield_cumulo+Accum._Yield+emission_CO2+consum_O2+interval_O2+generate_CO2; 0.763, 0.906, tmp+PL+AN+interval_Pdt.+RS+mu_cumulo+nu_cumulo+rho_cumulo+nu_per_rho_cumulo+rab_integral+RQ_integral+Accum._Yield+emission_CO2+consum_O2+interval_O2+generate_CO2; 0.772, 0.906, tmp+PL_cumulo+interval_Pdt.+mu_cumulo+nu_cumulo+rho_cumulo+nu_per_rho_cumulo+cell_yield_cumulo+rab_integral+Accum._Yield+emission_CO2+consum_O2+interval_O2+generate_CO2; 0.763, 0.906, tmp+PL+PL_cumulo+AN+interval_Pdt.+RS+mu_cumulo+nu_cumulo+rho_cumulo+nu_per_rho_cumulo+rab_integral+RQ_integral+Accum._Yield+emission_CO2+consum_O2+generate_CO2; 0.780, 0.906, tmp+PL+interval_Pdt.+RS+mu_cumulo+rho_cumulo+rab_integral+RQ_integral+Accum._Yield+emission_CO2+consum_O2+generate_CO2; 0.785, 0.906, tmp+PL+OD+nu_cumulo+rho_cumulo+nu_per_rho_cumulo+Arg_conc._cumulo+rab_integral+Accum._Yield+emission_CO2+generate_CO2; 0.772, 0.906, tmp+PL+PL_cumulo+interval_Pdt.+RS+mu_cumulo+nu_cumulo+rho_cumulo+nu_per_rho_cumulo+cell_yield_cumulo+rab_integral+emission_CO2+consum_O2+generate_CO2; 0.776, 0.906, tmp+PL+interval_Pdt.+RS+mu_cumulo+nu_cumulo+rho_cumulo+nu_per_rho_cumulo+rab_integral+emission_O2+emission_CO2+consum_O2+generate_CO2; 0.767, 0.906, tmp+PL+PL_cumulo+interval_Pdt.+RS+mu_cumulo+nu_cumulo+rho_cumulo+nu_per_rho_cumulo+rab_integral+RQ_integral+Accum._Yield+emission_CO2+consum_O2+generate_CO2; 0.762, 0.906, tmp+pH+PL+PL_cumulo+interval_Pdt.+mu_cumulo+nu_cumulo+rho_cumulo+nu_per_rho_cumulo+Arg_conc._cumulo+RQ_integral+Accum._Yield+emission_O2+emission_CO2+consum_O2+generate_CO2; 0.788, 0.906, tmp+mu_cumulo+nu_cumulo+rho_cumulo+nu_per_rho_cumulo+cell_yield_cumulo+rab_integral+emission_CO2+consum_O2+generate_CO2; 0.776, 0.906, tmp+PL+interval_Pdt.+mu_cumulo+nu_cumulo+rho_cumulo+nu_per_rho_cumulo+Arg_conc._cumulo+rab_integral+emission_O2+emission_CO2+consum_O2+generate_CO2; 0.776, 0.906, tmp+PL+AN+interval_Pdt.+mu_cumulo+rho_cumulo+Arg_conc._cumulo+rab_integral+Accum._Yield+emission_CO2+consum_O2+interval_O2+generate_CO2; 0.772, 0.906, tmp+PL_cumulo+interval_Pdt.+OD+mu_cumulo+nu_cumulo+rho_cumulo+nu_per_rho_cumulo+cell_yield_cumulo+rab_integral+RQ_integral+emission_CO2+consum_O2+generate_CO2; 0.776, 0.906, tmp+PL+interval_Pdt.+OD+nu_cumulo+rho_cumulo+nu_per_rho_cumulo+cell_yield_cumulo+rab_integral+RQ_integral+emission_CO2+consum_O2+generate_CO2; 0.757, 0.906, tmp+PL+PL_cumulo+AN+interval_Pdt.+mu_cumulo+nu_cumulo+rho_cumulo+nu_per_rho_cumulo+cell_yield_cumulo+RQ_integral+Accum._Yield+emission_O2+emission_CO2+consum_O2+interval_O2+generate_CO2; 0.776, 0.906, tmp+PL_cumulo+AN+interval_Pdt.+RS+mu_cumulo+nu_cumulo+rho_cumulo+nu_per_rho_cumulo+cell_yield_cumulo+emission_CO2+consum_O2+generate_CO2; 0.776, 0.906, tmp+PL+AN+interval_Pdt.+mu_cumulo+rho_cumulo+nu_per_rho_cumulo+rab_integral+Accum._Yield+emission_CO2+consum_O2+interval_O2+generate_CO2; 0.776, 0.906, tmp+PL_cumulo+AN+interval_Pdt.+mu_cumulo+nu_cumulo+rho_cumulo+nu_per_rho_cumulo+cell_yield_cumulo+emission_CO2+consum_O2+interval_O2+generate_CO2; 0.762, 0.906, tmp+PL+PL_cumulo+AN+interval_Pdt.+mu_cumulo+nu_cumulo+rho_cumulo+nu_per_rho_cumulo+Arg_conc._cumulo+rab_integral+emission_O2+emission_CO2+consum_O2+interval_O2+generate_CO2; 0.772, 0.906, tmp+PL+PL_cumulo+AN+interval_yield+interval_Pdt.+mu_cumulo+nu_cumulo+rho_cumulo+nu_per_rho_cumulo+emission_O2+emission_

CO2+consum_O2+generate_CO2; 0.757, 0.906, tmp+PL+ PL_cumulo+AN+interval_Pdt.+RS+mu_cumulo+nu_ cumulo+rho_cumulo+nu_per_rho_cumulo+Arg_conc._ cumulo+Accum._Yield+emission_O2+emission_CO2+ consum_O2+interval_O2+generate_CO2; 0.780, 0.906, tmp+interval_Pdt.+mu_cumulo+nu_cumulo+rho_cumulo+ nu_per_rho_cumulo+Arg_conc._cumulo+rab_integral+Ac- cum._Yield+emission_CO2+consum_O2+generate_CO2; 0.780, 0.906, tmp+PL+AN+interval_Pdt.+mu_cumulo+ rho_cumulo+nu_per_rho_cumulo+Arg_conc._cumulo+Ac- cum._Yield+emission_CO2+consum_O2+generate_CO2; 0.780, 0.906, tmp+PL+OD+mu_cumulo+nu_cumulo+rho_ cumulo+nu_per_rho_cumulo+Arg_conc._cumulo+rab_in- tegral+emission_CO2+consum_O2+generate_CO2; 0.772, 0.906, tmp+PL+AN+interval_Pdt.+mu_cumulo+nu_cu- mulo+nu_per_rho_cumulo+Arg_conc._cumulo+RQ_inte- gral+Accum._Yield+emission_CO2+consum_O2+gener- ate_CO2; 0.788, 0.906, tmp+PL+AN+interval_Pdt.+mu_ cumulo+nu_cumulo+rho_cumulo+emission_CO2+ consum_O2+generate_CO2; 0.767, 0.906, tmp+PL+ interval_Pdt.+OD+RS+nu_cumulo+rho_cumulo+nu_per_ rho_cumulo+Arg_conc._cumulo+Accum._Yield+ emission_O2+emission_CO2+consum_O2+interval_O2+ generate_CO2; 0.772, 0.906, tmp+pH+PL+interval_Pdt.+ RS+mu_cumulo+nu_cumulo+rho_cumulo+nu_per_rho_ cumulo+rab_integral+RQ_integral+emission_CO2+ consum_O2+generate_CO2; 0.776, 0.906, tmp+PL+AN+ interval_Pdt.+RS+mu_cumulo+nu_cumulo+rho_cumulo+ nu_per_rho_cumulo+RQ_integral+emission_CO2+ consum_O2+generate_CO2; 0.767, 0.906, tmp+PL+AN+ interval_Pdt.+RS+mu_cumulo+nu_cumulo+rho_cumulo+ nu_per_rho_cumulo+RQ_integral+Accum._Yield+ emission_O2+emission_CO2+consum_O2+generate_CO2; 0.784, 0.906, tmp+PL+interval_Pdt.+mu_cumulo+rho_cu- mulo+RQ_integral+Accum._Yield+emission_O2+emis- sion_CO2+consum_O2+generate_CO2; 0.772, 0.906, tmp+ PL+interval_Pdt.+mu_cumulo+nu_cumulo+rho_cumulo+ nu_per_rho_cumulo+rab_integral+RQ_integral+emission_ O2+emission_CO2+consum_O2+interval_O2+generate_ CO2; 0.776, 0.906, tmp+PL+AN+interval_Pdt.+RS+mu_ cumulo+rho_cumulo+Accum._Yield+emission_O2+ emission_CO2+consum_O2+interval_O2+generate_CO2; 0.772, 0.906, tmp+PL+PL_cumulo+interval_Pdt.+mu_cu- mulo+nu_cumulo+rho_cumulo+nu_per_rho_cumulo+Arg_ conc._cumulo+rab_integral+emission_CO2+consum_O2+ interval_O2+generate_CO2; 0.780, 0.906, tmp+PL+ interval_Pdt.+OD+mu_cumulo+nu_cumulo+rho_cumulo+ nu_per_rho_cumulo+Accum._Yield+emission_CO2+ consum_O2+generate_CO2; 0.762, 0.906, tmp+PL+ interval_Pdt.+OD+RS+nu_cumulo+rho_cumulo+nu_per_ rho_cumulo+Arg_conc._cumulo+RQ_integral+Accum._ Yield+emission_O2+emission_CO2+consum_O2+interval_ O2+generate_CO2; 0.792, 0.906, tmp+PL_cumulo+OD+ nu_cumulo+rho_cumulo+nu_per_rho_cumulo+Arg_conc._ cumulo+emission_CO2+generate_CO2; 0.780, 0.906, tmp+ PL_cumulo+OD+nu_cumulo+rho_cumulo+nu_per_rho_ cumulo+Arg_conc._cumulo+Accum._Yield+emission_O2+ emission_CO2+consum_O2+generate_CO2; 0.772, 0.906, tmp+PL+AN+interval_Pdt.+OD+mu_cumulo+nu_cumulo+ rho_cumulo+nu_per_rho_cumulo+Arg_conc._cumulo+ emission_CO2+consum_O2+interval_O2+generate_CO2; 0.757, 0.906, tmp+pH+PL+PL_cumulo+interval_Pdt.+OD+ nu_cumulo+rho_cumulo+nu_per_rho_cumulo+Arg_conc._ cumulo+rab_integral+RQ_integral+Accum._Yield+emis- sion_O2+emission_CO2+consum_O2+generate_CO2; 0.762, 0.906, tmp+PL+interval_Pdt.+RS+mu_cumulo+nu_ cumulo+rho_cumulo+nu_per_rho_cumulo+Arg_conc._cu- mulo+rab_integral+RQ_integral+Accum._Yield+emission_ O2+emission_CO2+consum_O2+generate_CO2; 0.776, 0.906, tmp+PL+interval_yield+interval_Pdt.+OD+nu_cu- mulo+rho_cumulo+nu_per_rho_cumulo+Arg_conc._cu- mulo+rab_integral+emission_CO2+consum_O2+generate_ CO2; 0.757, 0.906, tmp+PL+AN+interval_Pdt.+RS+mu_ cumulo+nu_cumulo+rho_cumulo+nu_per_rho_cumulo+ Arg_conc._cumulo+cell_yield_cumulo+rab_integral+RQ_ integral+Accum._Yield+emission_CO2+consum_O2+ generate_CO2; 0.784, 0.906, tmp+PL+interval_Pdt.+RS+ mu_cumulo+rho_cumulo+nu_per_rho_cumulo+rab_ integral+emission_CO2+consum_O2+generate_CO2; 0.762, 0.906, tmp+PL+PL_cumulo+AN+interval_Pdt.+mu_ cumulo+nu_cumulo+rho_cumulo+nu_per_rho_cumulo+ cell_yield_cumulo+RQ_integral+Accum._Yield+emission_ O2+emission_CO2+consum_O2+generate_CO2; 0.772, 0.906, tmp+PL+interval_Pdt.+OD+mu_cumulo+nu_cu- mulo+rho_cumulo+nu_per_rho_cumulo+Arg_conc._cu- mulo+cell_yield_cumulo+emission_O2+emission_CO2+ consum_O2+generate_CO2; 0.776, 0.906, tmp+PL_ cumulo+AN+interval_Pdt.+mu_cumulo+nu_cumulo+rho_ cumulo+nu_per_rho_cumulo+Arg_conc._cumulo+cell_ yield_cumulo+emission_CO2+consum_O2+generate_CO2; 0.776, 0.906, tmp+PL+AN+interval_Pdt.+OD+mu_cu- mulo+nu_cumulo+rho_cumulo+nu_per_rho_cumulo+RQ_ integral+emission_CO2+consum_O2+generate_CO2; 0.757, 0.906, tmp+PL+PL_cumulo+AN+interval_Pdt.+RS+ mu_cumulo+nu_cumulo+rho_cumulo+nu_per_rho_cu- mulo+Arg_conc._cumulo+rab_integral+Accum._Yield+ emission_CO2+consum_O2+interval_O2+generate_CO2; 0.776, 0.906, tmp+PL+interval_yield+interval_Pdt.+OD+ nu_cumulo+rho_cumulo+nu_per_rho_cumulo+rab_inte- gral+RQ_integral+emission_CO2+consum_O2+generate_ CO2; 0.772, 0.906, tmp+pH+PL+interval_Pdt.+RS+mu_ cumulo+nu_cumulo+rho_cumulo+nu_per_rho_cumulo+ rab_integral+Accum._Yield+emission_CO2+consum_O2+ generate_CO2; 0.780, 0.906, tmp+PL+AN+interval_Pdt.+ OD+nu_cumulo+rho_cumulo+nu_per_rho_cumulo+ emission_CO2+consum_O2+interval_O2+generate_CO2; 0.772, 0.906, tmp+PL+PL_cumulo+interval_Pdt.+OD+mu_ cumulo+nu_cumulo+rho_cumulo+nu_per_rho_cumulo+ cell_yield_cumulo+rab_integral+emission_CO2+consum_ O2+generate_CO2; 0.772, 0.906, tmp+PL+interval_Pdt.+ RS+mu_cumulo+nu_cumulo+rho_cumulo+nu_per_rho_ cumulo+RQ_integral+emission_O2+emission_CO2+ consum_O2+interval_O2+generate_CO2; 0.784, 0.906, tmp+PL_cumulo+interval_Pdt.+OD+nu_cumulo+rho_cu- mulo+nu_per_rho_cumulo+Arg_conc.cumulo+Accum._ Yield+emission_CO2+generate_CO2; 0.772, 0.906, tmp+ PL+PL_cumulo+AN+interval_Pdt.+OD+mu_cumulo+nu_ cumulo+rho_cumulo+nu_per_rho_cumulo+Accum._Yield+ emission_CO2+consum_O2+generate_CO2; 0.772, 0.906, tmp+PL+PL_cumulo+interval_Pdt.+OD+nu_cumulo+rho_ cumulo+nu_per_rho_cumulo+RQ_integral+Accum._ Yield+emission_O2+emission_CO2+consum_O2+gener- ate_CO2; 0.772, 0.906, tmp+pH+PL+OD+RS+nu_cumulo+ rho_cumulo+nu_per_rho_cumulo+Arg_conc._cumulo+ rab_integral+Accum._Yield+emission_CO2+consum_O2+ generate_CO2

[203. Linear Model that Predicts Arginine Production Amount in Interval 3]

0.711, 0.864, tmp+AN_cumulo+interval_Pdt.+RS+Feed_ Vol+mu_cumulo+Sugar_consuming_rate_cumulo+rab_in- tegral+AS_Vol.; 0.705, 0.864, tmp+AN_cumulo+interval_ Pdt.+RS+Feed_Vol+mu_cumulo+Sugar_consuming_rate_ cumulo+rab_integral+AS_Vol.+emission_O2; 0.699, 0.863, tmp+AN_cumulo+RS+Feed_Vol+mu_cumulo+Sugar_consuming_rate_cumulo+RQ_integral+AS_Vol.+emission_O2+emission_CO2+generate_CO2; 0.698, 0.862, tmp+AN_cumulo+interval_yield+interval_Pdt.+RS+Feed_Vol+mu_cumulo+Sugar_consuming_rate_cumulo+rab_integral+AS_Vol.+emission_O2; 0.702, 0.862, tmp+RS+Feed_Vol+mu_cumulo+Sugar_consuming_rate_cumulo+RQ_integral+AS_Vol.+emission_O2+emission_CO2+generate_CO2; 0.702, 0.862, tmp+AN_cumulo+interval_Pdt.+RS+Feed_Vol+mu_cumulo+nu_per_rho_cumulo+Sugar_consuming_rate_cumulo+rab_integral+AS_Vol.; 0.710, 0.861, tmp+AN_cumulo+RS+Feed_Vol+mu_cumulo+Sugar_consuming_rate_cumulo+rab_integral+AS_Vol.; 0.701, 0.861, tmp+AN_cumulo+interval_yield+interval_Pdt.+RS+Feed_Vol+mu_cumulo+Sugar_consuming_rate_cumulo+rab_integral+AS_Vol; 0.696, 0.861, tmp+AN_cumulo+interval_Pdt.+RS+Feed_Vol+mu_cumulo+nu_per_rho_cumulo+Sugar_consuming_rate_cumulo+rab_integral+AS_Vol.+emission_O2; 0.691, 0.861, tmp+PL+interval_Pdt.+RS+Feed_Vol+mu_cumulo+nu_per_rho_cumulo+Sugar_consuming_rate_cumulo+RQ_integral+AS_Vol.+emission_O2+emission_CO2; 0.696, 0.861, tmp+interval_Pdt.+RS+Feed_Vol+mu_cumulo+Sugar_consuming_rate_cumulo+RQ_integral+AS_Vol.+emission_O2+emission_CO2+generate_CO2; 0.690, 0.861, tmp+AN_cumulo+interval_yield+interval_Pdt.+RS+Feed_Vol+mu_cumulo+Sugar_consuming_rate_cumulo+rab_integral+AS_Vol.+emission_O2+emission_CO2; 0.690, 0.861, tmp+AN_cumulo+RS+Feed_Vol+mu_cumulo+nu_per_rho_cumulo+Sugar_consuming_rate_cumulo+RQ_integral+AS_Vol.+emission_O2+emission_CO2+generate_CO2; 0.695, 0.861, tmp+RS+Feed_Vol+mu_cumulo+rho_cumulo+Sugar_consuming_rate_cumulo+RQ_integral+AS_Vol.+emission_O2+emission_CO2+generate_CO2; 0.690, 0.861, tmp+interval_Pdt.+RS+Feed_Vol+mu_cumulo+nu_per_rho_cumulo+Sugar_consuming_rate_cumulo+RQ_integral+AS_Vol.+emission_O2+emission_CO2+generate_CO2; 0.695, 0.861, tmp+RS+Feed_Vol+mu_cumulo+nu_per_rho_cumulo+Sugar_consuming_rate_cumulo+RQ_integral+AS_Vol.+emission_O2+emission_CO2+generate_CO2; 0.704, 0.860, tmp+AN_cumulo+interval_Pdt.+RS+Feed_Vol+mu_cumulo+Sugar_consuming_rate_cumulo+rab_integral+emission_O2; 0.708, 0.860, tmp+interval_Pdt.+RS+Feed_Vol+mu_cumulo+Sugar_consuming_rate_cumulo+rab_integral+AS_Vol.; 0.684, 0.860, tmp+PL+interval_Pdt.+OD+RS+Feed_Vol+mu_cumulo+rho_cumulo+Sugar_consuming_rate_cumulo+RQ_integral+AS_Vol.+emission_O2+emission_CO2; 0.689, 0.860, tmp+PL+interval_Pdt.+RS+Feed_Vol+mu_cumulo+rho_cumulo+Sugar_consuming_rate_cumulo+RQ_integral+AS_Vol.+emission_O2+emission_CO2; 0.699, 0.860, tmp+AN_cumulo+RS+Feed_Vol+mu_cumulo+Sugar_consuming_rate_cumulo+RQ_integral+AS_Vol.+emission_CO2+generate_CO2; 0.708, 0.860, tmp+RS+Feed_Vol+mu_cumulo+Sugar_consuming_rate_cumulo+AS_Vol.+emission_CO2+generate_CO2; 0.694, 0.860, tmp+PL+AN_cumulo+interval_Pdt.+RS+Feed_Vol+mu_cumulo+Sugar_consuming_rate_cumulo+rab_integral+AS_Vol.+emission_O2; 0.703, 0.860, tmp+AN_cumulo+interval_Pdt.+RS+Feed_Vol+mu_cumulo+Sugar_consuming_rate_cumulo+RQ_integral+AS_Vol.; 0.703, 0.860, tmp+AN_cumulo+interval_yield+RS+Feed_Vol+mu_cumulo+Sugar_consuming_rate_cumulo+rab_integral+AS_Vol.; 0.698, 0.860, tmp+PL+AN_cumulo+interval_Pdt.+RS+Feed_Vol+mu_cumulo+Sugar_consuming_rate_cumulo+rab_integral+AS_Vol.; 0.703, 0.860, tmp+AN_cumulo+RS+Feed_Vol+mu_cumulo+Sugar_consuming_rate_cumulo+rab_integral+AS_Vol.+emission_CO2; 0.703, 0.860, tmp+interval_Pdt.+RS+Feed_Vol+mu_cumulo+Sugar_consuming_rate_cumulo+AS_Vol.+emission_CO2+generate_CO2; 0.693, 0.860, tmp+interval_Pdt.+RS+Feed_Vol+mu_cumulo+nu_per_rho_cumulo+Sugar_consuming_rate_cumulo+rab_integral+AS_Vol.+emission_O2+emission_CO2; 0.693, 0.860, tmp+interval_Pdt.+RS+Feed_Vol+mu_cumulo+rho_cumulo+Sugar_consuming_rate_cumulo+rab_integral+AS_Vol.+emission_O2+emission_CO2; 0.683, 0.860, tmp+PL+interval_Pdt.+RS+Feed_Vol+mu_cumulo+nu_per_rho_cumulo+Sugar_consuming_rate_cumulo+RQ_integral+AS_Vol.+emission_O2+emission_CO2+generate_CO2; 0.688, 0.860, tmp+AN_cumulo+RS+Feed_Vol+mu_cumulo+rho_cumulo+Sugar_consuming_rate_cumulo+RQ_integral+AS_Vol.+emission_O2+emission_CO2+generate_CO2; 0.703, 0.860, tmp+interval_Pdt.+OD+RS+Feed_Vol+mu_cumulo+rho_cumulo+Sugar_consuming_rate_cumulo+AS_Vol.; 0.683, 0.860, tmp+PL+AN+interval_Pdt.+RS+Feed_Vol+mu_cumulo+nu_per_rho_cumulo+Sugar_consuming_rate_cumulo+RQ_integral+AS_Vol.+emission_O2+emission_CO2; 0.702, 0.860, tmp+AN_cumulo+RS+Feed_Vol+mu_cumulo+Sugar_consuming_rate_cumulo+RQ_integral+AS_Vol.+emission_CO2; 0.693, 0.860, tmp+PL+RS+Feed_Vol+mu_cumulo+rho_cumulo+Sugar_consuming_rate_cumulo+RQ_integral+AS_Vol.+emission_O2+emission_CO2; 0.698, 0.860, tmp+AN_cumulo+RS+Feed_Vol+mu_cumulo+Sugar_consuming_rate_cumulo+RQ_integral+AS_Vol.+emission_O2+emission_CO2; 0.688, 0.860, tmp+AN_cumulo+interval_yield+interval_Pdt.+OD+RS+Feed_Vol+mu_cumulo+Sugar_consuming_rate_cumulo+rab_integral+AS_Vol.+emission_O2; 0.688, 0.860, tmp+PL+AN_cumulo+interval_yield+interval_Pdt.+RS+Feed_Vol+mu_cumulo+Sugar_consuming_rate_cumulo+rab_integral+AS_Vol.+emission_O2; 0.697, 0.860, tmp+AN_cumulo+interval_Pdt.+RS+Feed_Vol+mu_cumulo+rho_cumulo+Sugar_consuming_rate_cumulo+rab_integral+AS_Vol.; 0.688, 0.860, tmp+AN_cumulo+interval_Pdt.+RS+Feed_Vol+mu_cumulo+nu_per_rho_cumulo+Sugar_consuming_rate_cumulo+rab_integral+AS_Vol.+emission_O2+emission_CO2; 0.687, 0.860, tmp+PL+AN_cumulo+RS+Feed_Vol+mu_cumulo+Sugar_consuming_rate_cumulo+RQ_integral+AS_Vol.+emission_O2+emission_CO2+generate_CO2; 0.697, 0.860, tmp+AN_cumulo+interval_Pdt.+RS+Feed_Vol+mu_cumulo+Sugar_consuming_rate_cumulo+rab_integral+AS_Vol.+generate_CO2; 0.682, 0.859, tmp+PL+interval_Pdt.+RS+Feed_Vol+mu_cumulo+rho_cumulo+Sugar_consuming_rate_cumulo+RQ_integral+AS_Vol.+emission_O2+emission_CO2+generate_CO2; 0.706, 0.859, tmp+AN_cumulo+RS+Feed_Vol+mu_cumulo+Sugar_consuming_rate_cumulo+RQ_integral+AS_Vol.; 0.706, 0.859, tmp+AN_cumulo+interval_Pdt.+RS+Feed_Vol+mu_cumulo+Sugar_consuming_rate_cumulo+AS_Vol.; 0.692, 0.859, tmp+AN_cumulo+interval_Pdt.+RS+Feed_Vol+mu_cumulo+Sugar_consuming_rate_cumulo+rab_integral+AS_Vol.+emission_O2+emission_CO2; 0.687, 0.859, tmp+AN_cumulo+interval_Pdt.+RS+Feed_Vol+mu_cumulo+Sugar_consuming_rate_cumulo+RQ_integral+AS_Vol.+emission_O2+emission_CO2+generate_CO2; 0.697, 0.859, tmp+interval_Pdt.+OD+RS+Feed_Vol+mu_cumulo+rho_cumulo+Sugar_consuming_rate_cumulo+rab_integral+AS_Vol.; 0.697, 0.859, tmp+AN+AN_cumulo+interval_Pdt.+RS+Feed_Vol+mu_cumulo+Sugar_consuming_rate_cumulo+rab_integral+AS_Vol.; 0.682, 0.859, tmp+PL+AN+interval_Pdt.+RS+Feed_Vol+mu_cumulo+rho_cumulo+Sugar_consuming_rate_cumulo+RQ_integral+AS_Vol.+emission_O2+emission_CO2; 0.701, 0.859, tmp+interval_Pdt.+RS+Feed_Vol+mu_cumulo+nu_per_rho_cumulo+Sugar_consuming_rate_ cumulo+rab_integral+AS_Vol.; 0.692, 0.859, tmp+AN+RS+Feed_Vol+mu_cumulo+Sugar_consuming_rate_cumulo+RQ_integral+AS_Vol.+emission_O2+emission_CO2+generate_CO2; 0.701, 0.859, tmp+RS+Feed_Vol+mu_cumulo+Sugar_consuming_rate_cumulo+RQ_integral+AS_Vol.+emission_O2+emission_CO2; 0.701, 0.859, tmp+AN_cumulo+interval_Pdt.+RS+Feed_Vol+mu_cumulo+Sugar_consuming_rate_cumulo+AS_Vol.+generate_CO2; 0.686, 0.859, tmp+interval_Pdt.+RS+Feed_Vol+mu_cumulo+rho_cumulo+Sugar_consuming_rate_cumulo+RQ_integral+AS_Vol.+emission_O2+emission_CO2+generate_CO2; 0.701, 0.859, tmp+AN+interval_Pdt.+RS+Feed_Vol+mu_cumulo+Sugar_consuming_rate_cumulo+rab_integral+AS_Vol.; 0.701, 0.859, tmp+AN_cumulo+RS+Feed_Vol+mu_cumulo+nu_per_rho_cumulo+Sugar_consuming_rate_cumulo+rab_integral+AS_Vol.; 0.701, 0.859, tmp+AN_cumulo+RS+Feed_Vol+mu_cumulo+Sugar_consuming_rate_cumulo+AS_Vol.+emission_CO2+generate_CO2; 0.681, 0.859, tmp+PL+AN_cumulo+interval_Pdt.+RS+Feed_Vol+mu_cumulo+nu_per_rho_cumulo+Sugar_consuming_rate_cumulo+RQ_integral+AS_Vol.+emission_O2+emission_CO2; 0.686, 0.859, tmp+PL+RS+Feed_Vol+mu_cumulo+rho_cumulo+Sugar_consuming_rate_cumulo+RQ_integral+AS_Vol.+emission_O2+emission_CO2+generate_CO2; 0.686, 0.859, tmp+AN+AN_cumulo+RS+Feed_Vol+mu_cumulo+Sugar_consuming_rate_cumulo+RQ_integral+AS_Vol.+emission_O2+emission_CO2+generate_CO2; 0.696, 0.859, tmp+interval_Pdt.+OD+RS+Feed_Vol+mu_cumulo+rho_cumulo+Sugar_consuming_rate_cumulo+AS_Vol.+consum_O2; 0.696, 0.859, tmp+AN_cumulo+interval_yield+interval_Pdt.+RS+Feed_Vol+mu_cumulo+Sugar_consuming_rate_cumulo+rab_integral+emission_O2; 0.675, 0.859, tmp+PL+AN+interval_Pdt.+OD+RS+Feed_Vol+mu_cumulo+rho_cumulo+Sugar_consuming_rate_cumulo+RQ_integral+AS_Vol.+emission_O2+emission_CO2; 0.691, 0.859, tmp+interval_yield+interval_Pdt.+RS+Feed_Vol+mu_cumulo+Sugar_consuming_rate_cumulo+rab_integral+AS_Vol.+emission_O2+emission_CO2; 0.696, 0.859, tmp+AN_cumulo+interval_Pdt.+RS+Feed_Vol+mu_cumulo+Sugar_consuming_rate_cumulo+rab_integral+AS_Vol.+emission_CO2; 0.691, 0.859, tmp+AN_cumulo+interval_Pdt.+RS+Feed_Vol+mu_cumulo+Sugar_consuming_rate_cumulo+rab_integral+RQ_integral+AS_Vol.+emission_O2; 0.686, 0.859, tmp+AN_cumulo+interval_yield+interval_Pdt.+RS+Feed_Vol+mu_cumulo+nu_per_rho_cumulo+Sugar_consuming_rate_cumulo+rab_integral+AS_Vol.+emission_O2; 0.675, 0.859, tmp+PL+AN_cumulo+interval_Pdt.+OD+RS+Feed_Vol+mu_cumulo+rho_cumulo+Sugar_consuming_rate_cumulo+RQ_integral+AS_Vol.+emission_O2+emission_CO2; 0.701, 0.859, tmp+RS+Feed_Vol+mu_cumulo+Sugar_consuming_rate_cumulo+RQ_integral+AS_Vol.+emission_CO2+generate_CO2; 0.686, 0.859, tmp+PL+interval_Pdt.+RS+Feed_Vol+mu_cumulo+Sugar_consuming_rate_cumulo+RQ_integral+AS_Vol.+emission_O2+emission_CO2+generate_CO2; 0.691, 0.859, tmp+AN+AN_cumulo+interval_Pdt.+RS+Feed_Vol+mu_cumulo+Sugar_consuming_rate_cumulo+rab_integral+AS_Vol.+emission_O2; 0.709, 0.859, tmp+interval_Pdt.+RS+Feed_Vol+mu_cumulo+Sugar_consuming_rate_cumulo+AS_Vol.; 0.696, 0.859, tmp+AN_cumulo+interval_Pdt.+RS+Feed_Vol+mu_cumulo+Sugar_consuming_rate_cumulo+rab_integral+RQ_integral+AS_Vol.; 0.696, 0.859, tmp+interval_Pdt.+RS+Feed_Vol+mu_cumulo+Sugar_consuming_rate_cumulo+rab_integral+AS_Vol.+emission_O2+emission_CO2; 0.691, 0.859, tmp+AN_cumulo+interval_yield+interval_Pdt.+RS+Feed_Vol+mu_cumulo+nu_per_rho_cumulo+Sugar_consuming_rate_cumulo+rab_integral+AS_Vol.; 0.686, 0.859, tmp+PL+AN_cumulo+interval_Pdt.+RS+Feed_Vol+mu_cumulo+nu_per_rho_cumulo+Sugar_consuming_rate_cumulo+rab_integral+AS_Vol.+emission_O2; 0.691, 0.859, tmp+PL+AN_cumulo+RS+Feed_Vol+mu_cumulo+Sugar_consuming_rate_cumulo+RQ_integral+AS_Vol.+emission_O2+emission_CO2; 0.695, 0.859, tmp+AN_cumulo+interval_yield+RS+Feed_Vol+mu_cumulo+nu_per_rho_cumulo+Sugar_consuming_rate_cumulo+rab_integral+AS_Vol.; 0.690, 0.859, tmp+PL+RS+Feed_Vol+mu_cumulo+Sugar_consuming_rate_cumulo+RQ_integral+AS_Vol.+emission_O2+emission_CO2+generate_CO2; 0.685, 0.859, tmp+AN+interval_Pdt.+RS+Feed_Vol+mu_cumulo+rho_cumulo+Sugar_consuming_rate_cumulo+rab_integral+AS_Vol.+emission_O2+emission_CO2; 0.700, 0.858, tmp+AN_cumulo+interval_yield+RS+Feed_Vol+mu_cumulo+Sugar_consuming_rate_cumulo+RQ_integral+AS_Vol.; 0.695, 0.858, tmp+AN_cumulo+interval_Pdt.+RS+Feed_Vol+mu_cumulo+Sugar_consuming_rate_cumulo+rab_integral+RQ_integral+emission_O2; 0.690, 0.858, tmp+AN_cumulo+interval_Pdt.+RS+Feed_Vol+mu_cumulo+rho_cumulo+Sugar_consuming_rate_cumulo+rab_integral+AS_Vol.+emission_O2; 0.685, 0.858, tmp+AN+interval_Pdt.+RS+Feed_Vol+mu_cumulo+nu_per_rho_cumulo+Sugar_consuming_rate_cumulo+rab_integral+AS_Vol.+emission_CO2; 0.695, 0.858, tmp+AN+AN_cumulo+interval_Pdt.+RS+Feed_Vol+mu_cumulo+Sugar_consuming_rate_cumulo+rab_integral+emission_O2; 0.695, 0.858, tmp+AN_cumulo+interval_Pdt.+RS+Feed_Vol+mu_cumulo+nu_per_rho_cumulo+Sugar_consuming_rate_cumulo+rab_integral+emission_O2; 0.685, 0.858, tmp+AN+interval_yield+interval_Pdt.+RS+Feed_Vol+mu_cumulo+Sugar_consuming_rate_cumulo+rab_integral+AS_Vol.+emission_O2+emission_CO2; 0.690, 0.858, tmp+AN_cumulo+RS+Feed_Vol+mu_cumulo+nu_per_rho_cumulo+Sugar_consuming_rate_cumulo+RQ_integral+AS_Vol.+emission_CO2+generate_CO2; 0.695, 0.858, tmp+interval_Pdt.+RS+Feed_Vol+mu_cumulo+nu_per_rho_cumulo+Sugar_consuming_rate_cumulo+AS_Vol.+emission_CO2+generate_CO2; 0.680, 0.858, tmp+AN_cumulo+interval_Pdt.+RS+Feed_Vol+mu_cumulo+nu_per_rho_cumulo+Sugar_consuming_rate_cumulo+RQ_integral+AS_Vol.+emission_O2+emission_CO2+generate_CO2; 0.700, 0.858, tmp+interval_Pdt.+RS+Feed_Vol+mu_cumulo+rho_cumulo+Sugar_consuming_rate_cumulo+rab_integral+AS_Vol.; 0.695, 0.858, tmp+RS+Feed_Vol+mu_cumulo+nu_per_rho_cumulo+Sugar_consuming_rate_cumulo+RQ_integral+AS_Vol.+emission_O2+emission_CO2; 0.704, 0.858, tmp+RS+Feed_Vol+mu_cumulo+Sugar_consuming_rate_cumulo+rab_integral+AS_Vol.+emission_CO2; 0.685, 0.858, tmp+AN_cumulo+interval_Pdt.+OD+RS+Feed_Vol+mu_cumulo+rho_cumulo+Sugar_consuming_rate_cumulo+RQ_integral+AS_Vol.+emission_O2; 0.690, 0.858, tmp+AN_cumulo+RS+Feed_Vol+mu_cumulo+nu_per_rho_cumulo+Sugar_consuming_rate_cumulo+RQ_integral+AS_Vol.+emission_O2+emission_CO2; 0.695, 0.858, tmp+AN_cumulo+RS+Feed_Vol+mu_cumulo+nu_per_rho_cumulo+Sugar_consuming_rate_cumulo+rab_integral+AS_Vol.+emission_CO2; 0.699, 0.858, tmp+RS+Feed_Vol+mu_cumulo+nu_per_rho_cumulo+Sugar_consuming_rate_cumulo+AS_Vol.+emission_CO2+generate_CO2; 0.690, 0.858, tmp+OD+RS+Feed_Vol+mu_cumulo+Sugar_consuming_rate_cumulo+RQ_integral+AS_Vol.+emission_O2+emission_CO2+generate_CO2; 0.679, 0.858, tmp+AN_cumulo+interval_yield+interval_Pdt.+OD+RS+Feed_Vol+mu_ cumulo+Sugar_consuming_rate_cumulo+rab_integral+AS_Vol.+emission_O2+emission_CO2; 0.674, 0.858, tmp+PL+AN_cumulo+interval_Pdt.+RS+Feed_Vol+mu_cumulo+nu_per_rho_cumulo+Sugar_consuming_rate_cumulo+RQ_integral+AS_Vol.+emission_O2+emission_CO2+generate_CO2; 0.689, 0.858, tmp+PL+interval_Pdt.+RS+Feed_Vol+mu_cumulo+Sugar_consuming_rate_cumulo+RQ_integral+AS_Vol.+emission_O2+emission_CO2; 0.684, 0.858, tmp+interval_Pdt.+OD+RS+Feed_Vol+mu_cumulo+rho_cumulo+Sugar_consuming_rate_cumulo+rab_integral+AS_Vol.+emission_O2+emission_CO2; 0.684, 0.858, tmp+AN_cumulo+interval_Pdt.+OD+RS+Feed_Vol+mu_cumulo+rho_cumulo+Sugar_consuming_rate_cumulo+rab_integral+AS_Vol.+emission_O2; 0.684, 0.858, tmp+AN+interval_Pdt.+RS+Feed_Vol+mu_cumulo+Sugar_consuming_rate_cumulo+RQ_integral+AS_Vol.+emission_O2+emission_CO2+generate_CO2; 0.689, 0.858, tmp+PL+AN_cumulo+interval_Pdt.+RS+Feed_Vol+mu_cumulo+nu_per_rho_cumulo+Sugar_consuming_rate_cumulo+rab_integral+AS_Vol.; 0.679, 0.858, tmp+AN_cumulo+interval_yield+interval_Pdt.+RS+Feed_Vol+mu_cumulo+nu_per_rho_cumulo+Sugar_consuming_rate_cumulo+rab_integral+AS_Vol.+emission_O2+emission_CO2; 0.689, 0.858, tmp+RS+Feed_Vol+mu_cumulo+nu_cumulo+Sugar_consuming_rate_cumulo+RQ_integral+AS_Vol.+emission_O2+emission_CO2+generate_CO2; 0.684, 0.858, tmp+AN+RS+Feed_Vol+mu_cumulo+rho_cumulo+Sugar_consuming_rate_cumulo+RQ_integral+AS_Vol.+emission_O2+emission_CO2+generate_CO2; 0.679, 0.858, tmp+PL+interval_Pdt.+RS+Feed_Vol+mu_cumulo+rho_cumulo+Sugar_consuming_rate_cumulo+rab_integral+RQ_integral+AS_Vol.+emission_O2+emission_CO2; 0.689, 0.858, tmp+AN_cumulo+interval_Pdt.+OD+RS+Feed_Vol+mu_cumulo+rho_cumulo+Sugar_consuming_rate_cumulo+RQ_integral+AS_Vol.; 0.689, 0.858, tmp+interval_Pdt.+RS+Feed_Vol+mu_cumulo+nu_per_rho_cumulo+Sugar_consuming_rate_cumulo+RQ_integral+AS_Vol.+emission_O2+emission_CO2; 0.684, 0.858, tmp+AN_cumulo+interval_Pdt.+RS+Feed_Vol+mu_cumulo+rho_cumulo+Sugar_consuming_rate_cumulo+rab_integral+AS_Vol.+emission_O2+emission_CO2; 0.679, 0.858, tmp+AN_cumulo+interval_yield+interval_Pdt.+RS+Feed_Vol+mu_cumulo+Sugar_consuming_rate_cumulo+rab_integral+AS_Vol.+emission_O2+emission_CO2+generate_CO2; 0.684, 0.858, tmp+PL+AN+RS+Feed_Vol+mu_cumulo+rho_cumulo+Sugar_consuming_rate_cumulo+RQ_integral+AS_Vol.+emission_O2+emission_CO2; 0.694, 0.858, tmp+PL+RS+Feed_Vol+mu_cumulo+Sugar_consuming_rate_cumulo+RQ_integral+AS_Vol.+emission_O2+emission_CO2; 0.694, 0.858, tmp+AN_cumulo+RS+Feed_Vol+mu_cumulo+nu_per_rho_cumulo+Sugar_consuming_rate_cumulo+RQ_integral+AS_Vol.+emission_CO2; 0.694, 0.858, tmp+AN_cumulo+interval_Pdt.+RS+Feed_Vol+mu_cumulo+Sugar_consuming_rate_cumulo+AS_Vol.+emission_CO2+generate_CO2; 0.679, 0.858, tmp+PL+AN_cumulo+RS+Feed_Vol+mu_cumulo+nu_per_rho_cumulo+Sugar_consuming_rate_cumulo+RQ_integral+AS_Vol.+emission_O2+emission_CO2+generate_CO2; 0.684, 0.858, tmp+interval_yield+interval_Pdt.+RS+Feed_Vol+mu_cumulo+Sugar_consuming_rate_cumulo+RQ_integral+AS_Vol.+emission_O2+emission_CO2+generate_CO2; 0.689, 0.858, tmp+PL+AN_cumulo+interval_yield+interval_Pdt.+RS+Feed_Vol+mu_cumulo+Sugar_consuming_rate_cumulo+rab_integral+AS_Vol.; 0.679, 0.858, tmp+PL+interval_Pdt.+RS+Feed_Vol+mu_cumulo+nu_per_rho_cumulo+Sugar_consuming_rate_cumulo+rab_integral+RQ_integral+AS_Vol.+emission_O2+emission_CO2; 0.679, 0.858, tmp+PL+AN_cumulo+interval_yield+interval_Pdt.+RS+Feed_Vol+mu_cumulo+Sugar_consuming_rate_cumulo+rab_integral+AS_Vol.+emission_O2+emission_CO2; 0.699, 0.858, tmp+RS+Feed_Vol+mu_cumulo+rho_cumulo+Sugar_consuming_rate_cumulo+rab_integral+AS_Vol.+emission_CO2; 0.694, 0.858, tmp+AN_cumulo+interval_Pdt.+RS+Feed_Vol+mu_cumulo+nu_cumulo+Sugar_consuming_rate_cumulo+rab_integral+AS_Vol.; 0.679, 0.858, tmp+PL+AN_cumulo+interval_Pdt.+OD+RS+Feed_Vol+mu_cumulo+rho_cumulo+Sugar_consuming_rate_cumulo+RQ_integral+AS_Vol.+emission_O2; 0.694, 0.858, tmp+RS+Feed_Vol+mu_cumulo+rho_cumulo+Sugar_consuming_rate_cumulo+RQ_integral+AS_Vol.+emission_O2+emission_CO2; 0.699, 0.858, tmp+AN_cumulo+RS+Feed_Vol+mu_cumulo+rho_cumulo+Sugar_consuming_rate_cumulo+rab_integral+AS_Vol.; 0.699, 0.858, tmp+AN_cumulo+interval_Pdt.+RS+Feed_Vol+mu_cumulo+Sugar_consuming_rate_cumulo+RQ_integral+emission_O2; 0.684, 0.858, tmp+PL+AN+RS+Feed_Vol+mu_cumulo+rho_cumulo+Sugar_consuming_rate_cumulo+RQ_integral+AS_Vol.+emission_O2+emission_CO2; 0.699, 0.858, tmp+AN+RS+Feed_Vol+mu_cumulo+Sugar_consuming_rate_cumulo+AS_Vol.+emission_CO2+generate_CO2; 0.694, 0.858, tmp+AN_cumulo+interval_Pdt.+RS+Feed_Vol+mu_cumulo+nu_per_rho_cumulo+Sugar_consuming_rate_cumulo+RQ_integral+AS_Vol.; 0.678, 0.858, tmp+PL+AN_cumulo+interval_Pdt.+RS+Feed_Vol+mu_cumulo+Sugar_consuming_rate_cumulo+RQ_integral+AS_Vol.+emission_O2+emission_CO2+generate_CO2; 0.694, 0.858, tmp+AN_cumulo+RS+Feed_Vol+mu_cumulo+Sugar_consuming_rate_cumulo+rab_integral+AS_Vol.+emission_CO2+generate_CO2; 0.678, 0.858, tmp+AN+interval_Pdt.+RS+Feed_Vol+mu_cumulo+nu_per_rho_cumulo+Sugar_consuming_rate_cumulo+RQ_integral+AS_Vol.+emission_O2+emission_CO2+generate_CO2; 0.694, 0.858, tmp+AN+interval_Pdt.+RS+Feed_Vol+mu_cumulo+nu_per_rho_cumulo+Sugar_consuming_rate_cumulo+rab_integral+AS_Vol; 0.684, 0.858, tmp+PL+interval_yield+RS+Feed_Vol+mu_cumulo+rho_cumulo+Sugar_consuming_rate_cumulo+RQ_integral+AS_Vol.+emission_O2+emission_CO2; 0.689, 0.858, tmp+interval_yield+RS+Feed_Vol+mu_cumulo+Sugar_consuming_rate_cumulo+RQ_integral+AS_Vol.+emission_O2+emission_CO2+generate_CO2; 0.689, 0.858, tmp+AN_cumulo+interval_Pdt.+RS+Feed_Vol+mu_cumulo+nu_per_rho_cumulo+Sugar_consuming_rate_cumulo+rab_integral+AS_Vol.+emission_CO2; 0.698, 0.858, tmp+AN+AN_cumulo+RS+Feed_Vol+mu_cumulo+Sugar_consuming_rate_cumulo+rab_integral+AS_Vol.; 0.689, 0.858, tmp+PL+AN_cumulo+interval_Pdt.+RS+Feed_Vol+mu_cumulo+Sugar_consuming_rate_cumulo+RQ_integral+AS_Vol.+emission_O2; 0.684, 0.858, tmp+AN+RS+Feed_Vol+mu_cumulo+nu_per_rho_cumulo+Sugar_consuming_rate_cumulo+RQ_integral+AS_Vol.+emission_O2+emission_CO2+generate_CO2; 0.694, 0.858, tmp+AN_cumulo+RS+Feed_Vol+mu_cumulo+rho_cumulo+Sugar_consuming_rate_cumulo+rab_integral+AS_Vol.+emission_CO2; 0.694, 0.858, tmp+AN+interval_Pdt.+RS+Feed_Vol+mu_cumulo+Sugar_consuming_rate_cumulo+AS_Vol.+emission_CO2+generate_CO2; 0.693, 0.858, tmp+AN+interval_Pdt.+OD+RS+Feed_Vol+mu_cumulo+rho_cumulo+Sugar_consuming_rate_cumulo+AS_Vol.; 0.689, 0.858, tmp+AN_cumulo+interval_Pdt.+RS+Feed_Vol+mu_cumulo+nu_per_rho_cumulo+Sugar_consuming_rate_cumulo+rab_integral+AS_Vol.+generate_CO2; 0.698, 0.858, tmp+interval_yield+RS+Feed_Vol+mu_cumulo+Sugar_consuming_rate_cumulo+AS_Vol.+emission_CO2+ generate_CO2; 0.693, 0.858, tmp+AN_cumulo+interval_Pdt.+OD+RS+Feed_Vol+mu_cumulo+rho_cumulo+Sugar_consuming_rate_cumulo+AS_Vol.; 0.678, 0.858, tmp+PL+AN_cumulo+RS+Feed_Vol+mu_cumulo+rho_cumulo+Sugar_consuming_rate_cumulo+RQ_integral+AS_Vol.+emission_O2+emission_CO2+generate_CO2; 0.683, 0.858, tmp+PL+AN_cumulo+RS+Feed_Vol+mu_cumulo+nu_per_rho_cumulo+Sugar_consuming_rate_cumulo+RQ_integral+AS_Vol.+emission_O2+emission_CO2; 0.678, 0.858, tmp+AN_cumulo+interval_yield+interval_Pdt.+OD+RS+Feed_Vol+mu_cumulo+rho_cumulo+Sugar_consuming_rate_cumulo+rab_integral+AS_Vol.+emission_O2; 0.688, 0.858, tmp+AN+AN_cumulo+interval_Pdt.+RS+Feed_Vol+mu_cumulo+nu_per_rho_cumulo+Sugar_consuming_rate_cumulo+rab_integral+AS_Vol; 0.698, 0.858, tmp+PL+AN_cumulo+RS+Feed_Vol+mu_cumulo+Sugar_consuming_rate_cumulo+rab_integral+AS_Vol.; 0.688, 0.857, tmp+AN_cumulo+interval_Pdt.+OD+RS+Feed_Vol+mu_cumulo+Sugar_consuming_rate_cumulo+RQ_integral+AS_Vol.+emission_O2; 0.698, 0.857, tmp+RS+Feed_Vol+mu_cumulo+Sugar_consuming_rate_cumulo+rab_integral+AS_Vol.+emission_CO2+generate_CO2; 0.683, 0.857, tmp+interval_yield+RS+Feed_Vol+mu_cumulo+nu_per_rho_cumulo+Sugar_consuming_rate_cumulo+RQ_integral+AS_Vol.+emission_O2+emission_CO2+generate_CO2; 0.688, 0.857, tmp+PL+RS+Feed_Vol+mu_cumulo+nu_per_rho_cumulo+Sugar_consuming_rate_cumulo+RQ_integral+AS_Vol.+emission_O2+emission_CO2; 0.698, 0.857, tmp+AN_cumulo+interval_Pdt.+RS+Feed_Vol+mu_cumulo+nu_per_rho_cumulo+Sugar_consuming_rate_cumulo+AS_Vol.; 0.698, 0.857, tmp+interval_yield+interval_Pdt.+RS+Feed_Vol+mu_cumulo+Sugar_consuming_rate_cumulo+rab_integral+AS_Vol.; 0.693, 0.857, tmp+AN_cumulo+interval_Pdt.+OD+RS+Feed_Vol+mu_cumulo+Sugar_consuming_rate_cumulo+AS_Vol.+generate_CO2; 0.698, 0.857, tmp+RS+Feed_Vol+mu_cumulo+rho_cumulo+Sugar_consuming_rate_cumulo+AS_Vol.+emission_CO2+generate_CO2; 0.698, 0.857, tmp+interval_Pdt.+RS+Feed_Vol+mu_cumulo+Sugar_consuming_rate_cumulo+rab_integral+AS_Vol.+emission_CO2; 0.703, 0.857, tmp+AN+interval_Pdt.+RS+Feed_Vol+mu_cumulo+Sugar_consuming_rate_cumulo+AS_Vol.; 0.698, 0.857, tmp+AN_cumulo+RS+Feed_Vol+mu_cumulo+Sugar_consuming_rate_cumulo+rab_integral+RQ_integral+AS_Vol.; 0.693, 0.857, tmp+interval_Pdt.+RS+Feed_Vol+mu_cumulo+nu_per_rho_cumulo+Sugar_consuming_rate_cumulo+rab_integral+AS_Vol.+emission_CO2; 0.702, 0.857, tmp+interval_Pdt.+RS+Feed_Vol+mu_cumulo+nu_per_rho_cumulo+Sugar_consuming_rate_cumulo+AS_Vol.; 0.683, 0.857, tmp+AN_cumulo+RS+Feed_Vol+mu_cumulo+nu_cumulo+Sugar_consuming_rate_cumulo+RQ_integral+AS_Vol.+emission_O2+emission_CO2+generate_CO2; 0.688, 0.857, tmp+AN+AN_cumulo+RS+Feed_Vol+mu_cumulo+Sugar_consuming_rate_cumulo+RQ_integral+AS_Vol.+emission_CO2+generate_CO2; 0.688, 0.857, tmp+interval_Pdt.+RS+Feed_Vol+mu_cumulo+Sugar_consuming_rate_cumulo+rab_integral+AS_Vol.+emission_O2+emission_CO2+generate_CO2; 0.683, 0.857, tmp+interval_Pdt.+RS+Feed_Vol+mu_cumulo+nu_per_rho_cumulo+Sugar_consuming_rate_cumulo+rab_integral+RQ_integral+AS_Vol.+emission_O2+emission_CO2; 0.693, 0.857, tmp+AN_cumulo+interval_Pdt.+OD+RS+Feed_Vol+mu_cumulo+Sugar_consuming_rate_cumulo+RQ_integral+AS_Vol.; 0.688, 0.857, tmp+AN+AN_cumulo+interval_yield+interval_Pdt.+RS+Feed_Vol+mu_cumulo+Sugar_consuming_rate_cumulo+rab_integral+emission_O2; 0.672, 0.857, tmp+PL+AN+interval_Pdt.+RS+Feed_Vol+mu_cumulo+nu_per_rho_cumulo+Sugar_consuming_rate_cumulo+RQ_integral+AS_Vol.+emission_O2+emission_CO2+generate_CO2; 0.693, 0.857, tmp+AN_cumulo+interval_Pdt.+RS+Feed_Vol+mu_cumulo+Sugar_consuming_rate_cumulo+RQ_integral+AS_Vol.+emission_O2; 0.683, 0.857, tmp+PL+interval_Pdt.+RS+Feed_Vol+mu_cumulo+rho_cumulo+Sugar_consuming_rate_cumulo+rab_integral+AS_Vol.+emission_O2+emission_CO2; 0.672, 0.857, tmp+PL+interval_Pdt.+OD+RS+Feed_Vol+mu_cumulo+rho_cumulo+Sugar_consuming_rate_cumulo+RQ_integral+AS_Vol.+emission_O2+emission_CO2+generate_CO2; 0.682, 0.857, tmp+PL+RS+Feed_Vol+mu_cumulo+nu_per_rho_cumulo+Sugar_consuming_rate_cumulo+RQ_integral+AS_Vol.+emission_O2+emission_CO2+generate_CO2; 0.682, 0.857, tmp+interval_Pdt.+RS+Feed_Vol+mu_cumulo+rho_cumulo+Sugar_consuming_rate_cumulo+rab_integral+AS_Vol.+emission_O2+emission_CO2+generate_CO2; 0.682, 0.857, tmp+AN_cumulo+OD+RS+Feed_Vol+mu_cumulo+Sugar_consuming_rate_cumulo+RQ_integral+AS_Vol.+emission_O2+emission_CO2+generate_CO2; 0.682, 0.857, tmp+interval_Pdt.+RS+Feed_Vol+mu_cumulo+nu_per_rho_cumulo+Sugar_consuming_rate_cumulo+rab_integral+AS_Vol.+emission_O2+emission_CO2+generate_CO2; 0.688, 0.857, tmp+AN+interval_Pdt.+RS+Feed_Vol+mu_cumulo+Sugar_consuming_rate_cumulo+rab_integral+AS_Vol.+emission_O2+emission_CO2; 0.682, 0.857, tmp+interval_yield+interval_Pdt.+RS+Feed_Vol+mu_cumulo+Sugar_consuming_rate_cumulo+rab_integral+AS_Vol.+emission_O2+emission_CO2+generate_CO2; 0.682, 0.857, tmp+AN+AN_cumulo+interval_yield+interval_Pdt.+RS+Feed_Vol+mu_cumulo+Sugar_consuming_rate_cumulo+rab_integral+AS_Vol.+emission_O2; 0.682, 0.857, tmp+RS+Feed_Vol+mu_cumulo+rho_cumulo+nu_per_rho_cumulo+Sugar_consuming_rate_cumulo+RQ_integral+AS_Vol.+emission_O2+emission_CO2+generate_CO2; 0.677, 0.857, tmp+AN_cumulo+interval_yield+interval_Pdt.+RS+Feed_Vol+mu_cumulo+rho_cumulo+Sugar_consuming_rate_cumulo+rab_integral+AS_Vol.+emission_O2+emission_CO2; 0.672, 0.857, tmp+PL+AN+interval_Pdt.+RS+Feed_Vol+mu_cumulo+rho_cumulo+Sugar_consuming_rate_cumulo+RQ_integral+AS_Vol.+emission_O2+emission_CO2+generate_CO2; 0.687, 0.857, tmp+AN_cumulo+RS+Feed_Vol+mu_cumulo+rho_cumulo+Sugar_consuming_rate_cumulo+RQ_integral+AS_Vol.+emission_CO2+generate_CO2; 0.677, 0.857, tmp+PL+interval_yield+interval_Pdt.+RS+Feed_Vol+mu_cumulo+nu_per_rho_cumulo+Sugar_consuming_rate_cumulo+RQ_integral+AS_Vol.+emission_O2+emission_CO2; 0.682, 0.857, tmp+PL+interval_yield+RS+Feed_Vol+mu_cumulo+nu_per_rho_cumulo+Sugar_consuming_rate_cumulo+RQ_integral+AS_Vol.+emission_O2+emission_CO2; 0.682, 0.857, tmp+PL+AN_cumulo+interval_Pdt.+RS+Feed_Vol+mu_cumulo+Sugar_consuming_rate_cumulo+RQ_integral+AS_Vol.+emission_O2+emission_CO2; 0.687, 0.857, tmp+AN_cumulo+RS+Feed_Vol+mu_cumulo+Sugar_consuming_rate_cumulo+rab_integral+RQ_integral+AS_Vol.+emission_O2+emission_CO2; 0.687, 0.857, tmp+AN+interval_Pdt.+OD+RS+Feed_Vol+mu_cumulo+rho_cumulo+Sugar_consuming_rate_cumulo+rab_integral+AS_Vol.; 0.692, 0.857, tmp+RS+Feed_Vol+mu_cumulo+nu_per_rho_cumulo+Sugar_consuming_rate_cumulo+RQ_integral+AS_Vol.+emission_CO2+generate_CO2; 0.697, 0.857, tmp+pH+AN_cumulo+RS+Feed_Vol+mu_cumulo+Sugar_consuming_rate_cumulo+rab_integral+AS_Vol.; 0.687, 0.857, tmp+AN_cumulo+interval_yield+interval_Pdt.+RS+

Feed_Vol+mu_cumulo+Sugar_consuming_rate_cumulo+rab_integral+AS_Vol.+generate_CO2; 0.692, 0.857, tmp+interval_Pdt.+RS+Feed_Vol+mu_cumulo+Sugar_consuming_rate_cumulo+RQ_integral+AS_Vol.+emission_O2+emission_CO2; 0.692, 0.857, tmp+AN_cumulo+RS+Feed_Vol+mu_cumulo+Sugar_consuming_rate_cumulo+rab_integral+RQ_integral+AS_Vol.+emission_CO2; 0.671, 0.857, tmp+PL+AN+interval_Pdt.+RS+Feed_Vol+mu_cumulo+rho_cumulo+Sugar_consuming_rate_cumulo+rab_integral+RQ_integral+AS_Vol.+emission_O2+emission_CO2; 0.692, 0.857, tmp+AN+interval_Pdt.+RS+Feed_Vol+mu_cumulo+rho_cumulo+Sugar_consuming_rate_cumulo+rab_integral+AS_Vol.; 0.692, 0.857, tmp+PL+AN_cumulo+interval_Pdt.+RS+Feed_Vol+mu_cumulo+Sugar_consuming_rate_cumulo+RQ_integral+AS_Vol.; 0.677, 0.857, tmp+AN+AN_cumulo+RS+Feed_Vol+mu_cumulo+nu_per_rho_cumulo+Sugar_consuming_rate_cumulo+RQ_integral+AS_Vol.+emission_O2+emission_CO2+generate_CO2; 0.677, 0.857, tmp+PL+interval_yield+interval_Pdt.+RS+Feed_Vol+mu_cumulo+Sugar_consuming_rate_cumulo+RQ_integral+AS_Vol.+emission_O2+emission_CO2+generate_CO2; 0.692, 0.857, tmp+AN+RS+Feed_Vol+mu_cumulo+Sugar_consuming_rate_cumulo+RQ_integral+AS_Vol.+emission_O2+emission_CO2; 0.687, 0.857, tmp+AN+AN_cumulo+interval_yield+interval_Pdt.+RS+Feed_Vol+mu_cumulo+Sugar_consuming_rate_cumulo+rab_integral+AS_Vol.; 0.677, 0.857, tmp+PL+interval_Pdt.+RS+Feed_Vol+mu_cumulo+rho_cumulo+nu_per_rho_cumulo+Sugar_consuming_rate_cumulo+RQ_integral+AS_Vol.+emission_O2+emission_CO2; 0.692, 0.857, tmp+AN_cumulo+RS+Feed_Vol+mu_cumulo+nu_per_rho_cumulo+Sugar_consuming_rate_cumulo+AS_Vol.+emission_CO2+generate_CO2; 0.692, 0.857, tmp+AN_cumulo+interval_yield+RS+Feed_Vol+mu_cumulo+nu_per_rho_cumulo+Sugar_consuming_rate_cumulo+RQ_integral+AS_Vol.; 0.687, 0.857, tmp+AN+RS+Feed_Vol+mu_cumulo+rho_cumulo+Sugar_consuming_rate_cumulo+RQ_integral+AS_Vol.+emission_O2+emission_CO2; 0.682, 0.857, tmp+OD+RS+Feed_Vol+mu_cumulo+rho_cumulo+Sugar_consuming_rate_cumulo+RQ_integral+AS_Vol.+emission_O2+emission_CO2+generate_CO2; 0.697, 0.857, tmp+RS+Feed_Vol+mu_cumulo+nu_per_rho_cumulo+Sugar_consuming_rate_cumulo+rab_integral+AS_Vol.+emission_CO2; 0.682, 0.857, tmp+AN+AN_cumulo+interval_Pdt.+RS+Feed_Vol+mu_cumulo+nu_per_rho_cumulo+Sugar_consuming_rate_cumulo+rab_integral+AS_Vol.+emission_O2; 0.701, 0.857, tmp+AN_cumulo+interval_yield+RS+Feed_Vol+mu_cumulo+Sugar_consuming_rate_cumulo+AS_Vol.; 0.687, 0.857, tmp+AN_cumulo+interval_yield+interval_Pdt.+RS+Feed_Vol+mu_cumulo+rho_cumulo+Sugar_consuming_rate_cumulo+rab_integral+AS_Vol.; 0.682, 0.857, tmp+AN_cumulo+interval_yield+interval_Pdt.+RS+Feed_Vol+mu_cumulo+rho_cumulo+Sugar_consuming_rate_cumulo+rab_integral+AS_Vol.+emission_O2; 0.687, 0.857, tmp+AN_cumulo+interval_Pdt.+RS+Feed_Vol+mu_cumulo+Sugar_consuming_rate_cumulo+rab_integral+AS_Vol.+emission_O2+generate_CO2; 0.687, 0.857, tmp+AN_cumulo+interval_yield+interval_Pdt.+RS+Feed_Vol+mu_cumulo+Sugar_consuming_rate_cumulo+rab_integral+AS_Vol.+emission_CO2; 0.676, 0.857, tmp+interval_Pdt.+OD+RS+Feed_Vol+mu_cumulo+rho_cumulo+Sugar_consuming_rate_cumulo+RQ_integral+AS_Vol.+emission_O2+emission_CO2+generate_CO2; 0.682, 0.857, tmp+interval_yield+interval_Pdt.+RS+Feed_Vol+mu_cumulo+nu_per_rho_cumulo+Sugar_consuming_rate_cumulo+rab_integral+AS_Vol.+emission_O2+emission_CO2; 0.692, 0.857, tmp+PL+AN_cumulo+interval_Pdt.+RS+Feed_Vol+mu_cumulo+Sugar_consuming_rate_cumulo+rab_integral+emission_O2; 0.692, 0.857, tmp+RS+Feed_Vol+mu_cumulo+rho_cumulo+Sugar_consuming_rate_cumulo+RQ_integral+AS_Vol.+emission_CO2+generate_CO2; 0.687, 0.857, tmp+RS+Feed_Vol+mu_cumulo+rho_cumulo+Sugar_consuming_rate_cumulo+rab_integral+RQ_integral+AS_Vol.+emission_O2+emission_CO2; 0.701, 0.857, tmp+RS+Feed_Vol+mu_cumulo+Sugar_consuming_rate_cumulo+RQ_integral+AS_Vol.+emission_CO2; 0.701, 0.857, tmp+interval_yield+RS+Feed_Vol+mu_cumulo+nu_per_rho_cumulo+Sugar_consuming_rate_cumulo+AS_Vol.; 0.692, 0.857, tmp+interval_Pdt.+RS+Feed_Vol+mu_cumulo+Sugar_consuming_rate_cumulo+AS_Vol.+emission_O2+emission_CO2+generate_CO2; 0.696, 0.857, tmp+AN_cumulo+RS+Feed_Vol+mu_cumulo+nu_per_rho_cumulo+Sugar_consuming_rate_cumulo+RQ_integral+AS_Vol.; 0.687, 0.857, tmp+AN_cumulo+interval_Pdt.+RS+Feed_Vol+mu_cumulo+nu_cumulo+Sugar_consuming_rate_cumulo+rab_integral+AS_Vol.+emission_O2; 0.687, 0.857, tmp+AN_cumulo+interval_Pdt.+OD+RS+Feed_Vol+mu_cumulo+rho_cumulo+Sugar_consuming_rate_cumulo+rab_integral+AS_Vol.; 0.692, 0.857, tmp+RS+Feed_Vol+mu_cumulo+Sugar_consuming_rate_cumulo+rab_integral+RQ_integral+AS_Vol.+emission_O2+emission_CO2; 0.681, 0.857, tmp+AN_cumulo+interval_yield+interval_Pdt.+OD+RS+Feed_Vol+mu_cumulo+Sugar_consuming_rate_cumulo+RQ_integral+AS_Vol.+emission_O2; 0.681, 0.857, tmp+interval_yield+RS+Feed_Vol+mu_cumulo+rho_cumulo+Sugar_consuming_rate_cumulo+RQ_integral+AS_Vol.+emission_O2+emission_CO2+generate_CO2; 0.692, 0.857, tmp+interval_Pdt.+RS+Feed_Vol+mu_cumulo+rho_cumulo+Sugar_consuming_rate_cumulo+rab_integral+AS_Vol.+emission_CO2; 0.681, 0.857, tmp+PL+interval_Pdt.+RS+Feed_Vol+mu_cumulo+nu_per_rho_cumulo+Sugar_consuming_rate_cumulo+rab_integral+AS_Vol.+emission_O2+emission_CO2; 0.681, 0.857, tmp+PL+AN_cumulo+interval_Pdt.+RS+Feed_Vol+mu_cumulo+Sugar_consuming_rate_cumulo+rab_integral+RQ_integral+AS_Vol.+emission_O2; 0.681, 0.857, tmp+AN_cumulo+interval_yield+interval_Pdt.+RS+Feed_Vol+mu_cumulo+Sugar_consuming_rate_cumulo+rab_integral+RQ_integral+AS_Vol.+emission_O2; 0.681, 0.857, tmp+interval_yield+interval_Pdt.+RS+Feed_Vol+mu_cumulo+rho_cumulo+Sugar_consuming_rate_cumulo+rab_integral+AS_Vol.+emission_O2+emission_CO2; 0.691, 0.857, tmp+interval_Pdt.+RS+Feed_Vol+mu_cumulo+rho_cumulo+Sugar_consuming_rate_cumulo+AS_Vol.+emission_CO2+generate_CO2; 0.686, 0.857, tmp+interval_Pdt.+OD+RS+Feed_Vol+mu_cumulo+rho_cumulo+Sugar_consuming_rate_cumulo+rab_integral+AS_Vol.+consum_O2; 0.691, 0.857, tmp+AN_cumulo+interval_Pdt.+RS+Feed_Vol+mu_cumulo+Sugar_consuming_rate_cumulo+RQ_integral+AS_Vol.+generate_CO2; 0.691, 0.857, tmp+AN_cumulo+RS+Feed_Vol+mu_cumulo+rho_cumulo+Sugar_consuming_rate_cumulo+RQ_integral+AS_Vol.+emission_CO2; 0.681, 0.857, tmp+PL+AN+interval_Pdt.+RS+Feed_Vol+mu_cumulo+Sugar_consuming_rate_cumulo+RQ_integral+AS_Vol.+emission_O2+emission_CO2; 0.676, 0.857, tmp+AN_cumulo+interval_yield+interval_Pdt.+RS+Feed_Vol+mu_cumulo+Sugar_consuming_rate_cumulo+RQ_integral+AS_Vol.+emission_O2+emission_CO2+generate_CO2; 0.681, 0.857, tmp+interval_Pdt.+OD+RS+Feed_Vol+mu_cumulo+Sugar_consuming_rate_cumulo+RQ_integral+AS_Vol.+emission_O2+emission_CO2+generate_CO2; 0.681, 0.857, tmp+AN_ cumulo+interval_Pdt.+RS+Feed_Vol+mu_cumulo+Sugar_consuming_rate_cumulo+rab_integral+AS_Vol.+emission_O2+emission_CO2+generate_CO2; 0.670, 0.857, tmp+PL+AN+interval_Pdt.+RS+Feed_Vol+mu_cumulo+nu_per_rho_cumulo+Sugar_consuming_rate_cumulo+rab_integral+RQ_integral+AS_Vol.+emission_O2+emission_CO2; 0.696, 0.856, tmp+AN_cumulo+RS+Feed_Vol+mu_cumulo+Sugar_consuming_rate_cumulo+rab_integral+AS_Vol.+generate_CO2; 0.670, 0.856, tmp+PL+AN_cumulo+interval_yield+interval_Pdt.+RS+Feed_Vol+mu_cumulo+Sugar_consuming_rate_cumulo+RQ_integral+AS_Vol.+emission_O2+emission_CO2+generate_CO2; 0.686, 0.856, tmp+interval_yield+RS+Feed_Vol+mu_cumulo+nu_per_rho_cumulo+Sugar_consuming_rate_cumulo+RQ_integral+AS_Vol.+emission_O2+emission_CO2; 0.676, 0.856, tmp+PL+interval_Pdt.+OD+RS+Feed_Vol+mu_cumulo+nu_per_rho_cumulo+Sugar_consuming_rate_cumulo+RQ_integral+AS_Vol.+emission_O2+emission_CO2; 0.686, 0.856, tmp+AN_cumulo+interval_Pdt.+OD+RS+Feed_Vol+mu_cumulo+rho_cumulo+Sugar_consuming_rate_cumulo+AS_Vol.+generate_CO2; 0.696, 0.856, tmp+AN_cumulo+OD+RS+Feed_Vol+mu_cumulo+Sugar_consuming_rate_cumulo+RQ_integral+AS_Vol.; 0.681, 0.856, tmp+RS+Feed_Vol+mu_cumulo+nu_cumulo+nu_per_rho_cumulo+Sugar_consuming_rate_cumulo+RQ_integral+AS_Vol.+emission_O2+emission_CO2+generate_CO2; 0.681, 0.856, tmp+interval_Pdt.+OD+RS+Feed_Vol+mu_cumulo+rho_cumulo+Sugar_consuming_rate_cumulo+RQ_integral+AS_Vol.+emission_O2+emission_CO2; 0.676, 0.856, tmp+AN_cumulo+interval_yield+interval_Pdt.+OD+RS+Feed_Vol+mu_cumulo+nu_cumulo+Sugar_consuming_rate_cumulo+rab_integral+AS_Vol.+emission_O2; 0.681, 0.856, tmp+PL+RS+Feed_Vol+mu_cumulo+rho_cumulo+Sugar_consuming_rate_cumulo+rab_integral+RQ_integral+AS_Vol.+emission_O2+emission_CO2; 0.691, 0.856, tmp+AN+interval_yield+interval_Pdt.+RS+Feed_Vol+mu_cumulo+Sugar_consuming_rate_cumulo+rab_integral+AS_Vol.; 0.691, 0.856, tmp+interval_yield+RS+Feed_Vol+mu_cumulo+nu_per_rho_cumulo+Sugar_consuming_rate_cumulo+AS_Vol.+emission_CO2+generate_CO2; 0.670, 0.856, tmp+PL+interval_Pdt.+OD+RS+Feed_Vol+mu_cumulo+rho_cumulo+Sugar_consuming_rate_cumulo+rab_integral+RQ_integral+AS_Vol.+emission_O2+emission_CO2; 0.686, 0.856, tmp+AN+interval_Pdt.+OD+RS+Feed_Vol+mu_cumulo+rho_cumulo+Sugar_consuming_rate_cumulo+AS_Vol.+consum_O2; 0.691, 0.856, tmp+interval_Pdt.+OD+RS+Feed_Vol+mu_cumulo+rho_cumulo+Sugar_consuming_rate_cumulo+AS_Vol.+generate_CO2; 0.691, 0.856, tmp+AN_cumulo+interval_Pdt.+RS+Feed_Vol+mu_cumulo+nu_per_rho_cumulo+Sugar_consuming_rate_cumulo+AS_Vol.+generate_CO2; 0.686, 0.856, tmp+AN_cumulo+interval_Pdt.+RS+Feed_Vol+mu_cumulo+nu_per_rho_cumulo+Sugar_consuming_rate_cumulo+rab_integral+RQ_integral+AS_Vol.; 0.691, 0.856, tmp+PL+AN_cumulo+interval_Pdt.+RS+Feed_Vol+mu_cumulo+Sugar_consuming_rate_cumulo+RQ_integral+emission_O2; 0.696, 0.856, tmp+AN_cumulo+interval_Pdt.+OD+RS+Feed_Vol+mu_cumulo+Sugar_consuming_rate_cumulo+AS_Vol.; 0.681, 0.856, tmp+PL+OD+RS+Feed_Vol+mu_cumulo+rho_cumulo+Sugar_consuming_rate_cumulo+RQ_integral+AS_Vol.+emission_O2+emission_CO2; 0.696, 0.856, tmp+AN+RS+Feed_Vol+mu_cumulo+Sugar_consuming_rate_cumulo+rab_integral+AS_Vol.+emission_CO2; 0.691, 0.856, tmp+AN_cumulo+interval_yield+RS+Feed_Vol+mu_cumulo+Sugar_consuming_rate_cumulo+rab_integral+AS_Vol.+emission_CO2; 0.696, 0.856, tmp+PL+AN_cumulo+RS+Feed_Vol+mu_cumulo+Sugar_consuming_rate_cumulo+RQ_integral+AS_Vol.; 0.681, 0.856, tmp+OD+RS+Feed_Vol+mu_cumulo+nu_per_rho_cumulo+Sugar_consuming_rate_cumulo+RQ_integral+AS_Vol.+emission_O2+emission_CO2+generate_CO2; 0.686, 0.856, tmp+AN_cumulo+interval_Pdt.+RS+Feed_Vol+mu_cumulo+rho_cumulo+nu_per_rho_cumulo+Sugar_consuming_rate_cumulo+rab_integral+AS_Vol.; 0.696, 0.856, tmp+interval_yield+RS+Feed_Vol+mu_cumulo+nu_per_rho_cumulo+Sugar_consuming_rate_cumulo+rab_integral+AS_Vol.; 0.675, 0.856, tmp+AN_cumulo+interval_Pdt.+OD+RS+Feed_Vol+mu_cumulo+rho_cumulo+Sugar_consuming_rate_cumulo+RQ_integral+AS_Vol.+emission_O2+emission_CO2; 0.681, 0.856, tmp+AN_cumulo+RS+Feed_Vol+mu_cumulo+Sugar_consuming_rate_cumulo+rab_integral+RQ_integral+AS_Vol.+emission_O2+emission_CO2+generate_CO2; 0.675, 0.856, tmp+PL+AN+interval_Pdt.+RS+Feed_Vol+mu_cumulo+rho_cumulo+Sugar_consuming_rate_cumulo+rab_integral+AS_Vol.+emission_O2+emission_CO2; 0.675, 0.856, tmp+PL+interval_Pdt.+RS+Feed_Vol+mu_cumulo+nu_cumulo+nu_per_rho_cumulo+Sugar_consuming_rate_cumulo+RQ_integral+AS_Vol.+emission_O2+emission_CO2; 0.691, 0.856, tmp+AN+interval_Pdt.+RS+Feed_Vol+mu_cumulo+Sugar_consuming_rate_cumulo+rab_integral+AS_Vol.+emission_CO2; 0.675, 0.856, tmp+PL+AN+RS+Feed_Vol+mu_cumulo+rho_cumulo+Sugar_consuming_rate_cumulo+RQ_integral+AS_Vol.+emission_O2+emission_CO2+generate_CO2; 0.700, 0.856, tmp+interval_yield+RS+Feed_Vol+mu_cumulo+Sugar_consuming_rate_cumulo+rab_integral+AS_Vol.; 0.681, 0.856, tmp+RS+Feed_Vol+mu_cumulo+nu_cumulo+rho_cumulo+Sugar_consuming_rate_cumulo+RQ_integral+AS_Vol.+emission_O2+emission_CO2+generate_CO2; 0.675, 0.856, tmp+PL+AN_cumulo+interval_Pdt.+RS+Feed_Vol+mu_cumulo+rho_cumulo+Sugar_consuming_rate_cumulo+RQ_integral+AS_Vol.+emission_O2+emission_CO2; 0.670, 0.856, tmp+AN_cumulo+interval_yield+interval_Pdt.+OD+RS+Feed_Vol+mu_cumulo+rho_cumulo+Sugar_consuming_rate_cumulo+rab_integral+AS_Vol.+emission_O2+emission_CO2; 0.675, 0.856, tmp+AN_cumulo+interval_Pdt.+OD+RS+Feed_Vol+mu_cumulo+rho_cumulo+Sugar_consuming_rate_cumulo+rab_integral+AS_Vol.+emission_O2+emission_CO2; 0.686, 0.856, tmp+AN+AN_cumulo+interval_Pdt.+RS+Feed_Vol+mu_cumulo+nu_per_rho_cumulo+Sugar_consuming_rate_cumulo+rab_integral+emission_O2; 0.686, 0.856, tmp+AN+interval_Pdt.+RS+Feed_Vol+mu_cumulo+nu_per_rho_cumulo+Sugar_consuming_rate_cumulo+rab_integral+AS_Vol.+emission_CO2; 0.675, 0.856, tmp+interval_Pdt.+OD+RS+Feed_Vol+mu_cumulo+nu_per_rho_cumulo+Sugar_consuming_rate_cumulo+RQ_integral+AS_Vol.+emission_O2+emission_CO2+generate_CO2; 0.691, 0.856, tmp+AN_cumulo+interval_Pdt.+OD+RS+Feed_Vol+mu_cumulo+Sugar_consuming_rate_cumulo+RQ_integral+emission_O2; 0.675, 0.856, tmp+AN+interval_Pdt.+OD+RS+Feed_Vol+mu_cumulo+rho_cumulo+Sugar_consuming_rate_cumulo+rab_integral+AS_Vol.+emission_O2+emission_CO2; 0.695, 0.856, tmp+AN_cumulo+interval_yield+RS+Feed_Vol+mu_cumulo+nu_per_rho_cumulo+Sugar_consuming_rate_cumulo+AS_Vol.; 0.690, 0.856, tmp+interval_Pdt.+OD+RS+Feed_Vol+mu_cumulo+rho_cumulo+Sugar_consuming_rate_cumulo+RQ_integral+AS_Vol.; 0.675, 0.856, tmp+PL+AN_cumulo+interval_yield+interval_Pdt.+RS+Feed_Vol+mu_cumulo+nu_per_rho_cumulo+Sugar_consuming_rate_cumulo+rab_integral+AS_Vol.+emission_O2; 0.690, 0.856, tmp+AN+

RS+Feed_Vol+mu_cumulo+Sugar_consuming_rate_cumulo+RQ_integral+AS_Vol.+emission_CO2+generate_CO2; 0.695, 0.856, tmp+PL+interval_Pdt.+RS+Feed_Vol+mu_cumulo+Sugar_consuming_rate_cumulo+rab_integral+AS_Vol.; 0.700, 0.856, tmp+interval_Pdt.+OD+RS+Feed_Vol+mu_cumulo+Sugar_consuming_rate_cumulo+AS_Vol.; 0.685, 0.856, tmp+interval_Pdt.+RS+Feed_Vol+mu_cumulo+Sugar_consuming_rate_cumulo+rab_integral+RQ_integral+AS_Vol.+emission_O2+emission_CO2; 0.680, 0.856, tmp+AN_cumulo+interval_yield+RS+Feed_Vol+mu_cumulo+Sugar_consuming_rate_cumulo+RQ_integral+AS_Vol.+emission_O2+emission_CO2+generate_CO2; 0.690, 0.856, tmp+PL+AN_cumulo+interval_yield+RS+Feed_Vol+mu_cumulo+Sugar_consuming_rate_cumulo+rab_integral+AS_Vol.; 0.680, 0.856, tmp+AN_cumulo+interval_yield+interval_Pdt.+RS+Feed_Vol+mu_cumulo+nu_cumulo+Sugar_consuming_rate_cumulo+rab_integral+AS_Vol.+emission_O2; 0.690, 0.856, tmp+AN+RS+Feed_Vol+mu_cumulo+rho_cumulo+Sugar_consuming_rate_cumulo+rab_integral+AS_Vol.+emission_CO2; 0.675, 0.856, tmp+PL+interval_Pdt.+RS+Feed_Vol+mu_cumulo+nu_cumulo+rho_cumulo+Sugar_consuming_rate_cumulo+RQ_integral+AS_Vol.+emission_O2+emission_CO2; 0.675, 0.856, tmp+AN+interval_Pdt.+RS+Feed_Vol+mu_cumulo+rho_cumulo+Sugar_consuming_rate_cumulo+RQ_integral+AS_Vol.+emission_O2+emission_CO2+generate_CO2; 0.690, 0.856, tmp+AN_cumulo+interval_yield+RS+Feed_Vol+mu_cumulo+Sugar_consuming_rate_cumulo+AS_Vol.+emission_CO2+generate_CO2; 0.690, 0.856, tmp+interval_Pdt.+RS+Feed_Vol+mu_cumulo+Sugar_consuming_rate_cumulo+rab_integral+AS_Vol.+emission_CO2+generate_CO2; 0.685, 0.856, tmp+AN_cumulo+interval_yield+interval_Pdt.+RS+Feed_Vol+mu_cumulo+nu_cumulo+Sugar_consuming_rate_cumulo+rab_integral+AS_Vol; 0.680, 0.856, tmp+AN_cumulo+interval_Pdt.+RS+Feed_Vol+mu_cumulo+nu_per_rho_cumulo+Sugar_consuming_rate_cumulo+rab_integral+RQ_integral+AS_Vol.+emission_O2; 0.680, 0.856, tmp+PL+interval_yield+interval_Pdt.+RS+Feed_Vol+mu_cumulo+Sugar_consuming_rate_cumulo+rab_integral+AS_Vol.+emission_O2+emission_CO2; 0.680, 0.856, tmp+PL+AN+interval_Pdt.+RS+Feed_Vol+mu_cumulo+rho_cumulo+Sugar_consuming_rate_cumulo+RQ_integral+emission_O2+emission_CO2; 0.675, 0.856, tmp+PL+AN_cumulo+interval_yield+interval_Pdt.+OD+RS+Feed_Vol+mu_cumulo+Sugar_consuming_rate_cumulo+rab_integral+AS_Vol.+emission_O2; 0.685, 0.856, tmp+AN+RS+Feed_Vol+mu_cumulo+nu_per_rho_cumulo+Sugar_consuming_rate_cumulo+RQ_integral+AS_Vol.+emission_O2+emission_CO2; 0.675, 0.856, tmp+PL+AN+interval_Pdt.+RS+Feed_Vol+mu_cumulo+Sugar_consuming_rate_cumulo+RQ_integral+AS_Vol.+emission_O2+emission_CO2+generate_CO2; 0.690, 0.856, tmp+interval_yield+interval_Pdt.+RS+Feed_Vol+mu_cumulo+Sugar_consuming_rate_cumulo+AS_Vol.+emission_CO2+generate_CO2; 0.685, 0.856, tmp+AN_cumulo+interval_Pdt.+RS+Feed_Vol+mu_cumulo+nu_cumulo+nu_per_rho_cumulo+Sugar_consuming_rate_cumulo+rab_integral+AS_Vol.; 0.690, 0.856, tmp+pH+AN_cumulo+interval_Pdt.+RS+Feed_Vol+mu_cumulo+Sugar_consuming_rate_cumulo+rab_integral+AS_Vol.; 0.680, 0.856, tmp+PL+interval_yield+interval_Pdt.+RS+Feed_Vol+mu_cumulo+Sugar_consuming_rate_cumulo+RQ_integral+AS_Vol.+emission_O2+emission_CO2; 0.680, 0.856, tmp+AN_cumulo+interval_yield+interval_Pdt.+RS+Feed_Vol+mu_cumulo+Sugar_consuming_rate_cumulo+rab_integral+AS_Vol.+emission_O2+emission_CO2; 0.695, 0.856, tmp+AN_cumulo+RS+Feed_Vol+mu_cumulo+nu_cumulo+Sugar_consuming_rate_cumulo+rab_integral+AS_Vol.; 0.675, 0.856, tmp+AN+AN_cumulo+RS+Feed_Vol+mu_cumulo+rho_cumulo+Sugar_consuming_rate_cumulo+RQ_integral+AS_Vol.+emission_O2+emission_CO2+generate_CO2; 0.690, 0.856, tmp+AN_cumulo+interval_yield+interval_Pdt.+RS+Feed_Vol+mu_cumulo+Sugar_consuming_rate_cumulo+RQ_integral+AS_Vol; 0.685, 0.856, tmp+PL+AN_cumulo+RS+Feed_Vol+mu_cumulo+Sugar_consuming_rate_cumulo+RQ_integral+AS_Vol.+emission_CO2+generate_CO2; 0.685, 0.856, tmp+AN_cumulo+interval_Pdt.+OD+RS+Feed_Vol+mu_cumulo+nu_per_rho_cumulo+Sugar_consuming_rate_cumulo+RQ_integral+AS_Vol.; 0.690, 0.856, tmp+AN+AN_cumulo+interval_yield+RS+Feed_Vol+mu_cumulo+Sugar_consuming_rate_cumulo+rab_integral+AS_Vol.; 0.695, 0.856, tmp+AN+interval_Pdt.+RS+Feed_Vol+mu_cumulo+nu_per_rho_cumulo+Sugar_consuming_rate_cumulo+AS_Vol.; 0.690, 0.856, tmp+AN+AN_cumulo+RS+Feed_Vol+mu_cumulo+Sugar_consuming_rate_cumulo+AS_Vol.+emission_CO2+generate_CO2; 0.685, 0.856, tmp+interval_yield+interval_Pdt.+OD+RS+Feed_Vol+mu_cumulo+rho_cumulo+Sugar_consuming_rate_cumulo+AS_Vol.+consum_O2; 0.675, 0.856, tmp+interval_yield+interval_Pdt.+RS+Feed_Vol+mu_cumulo+nu_per_rho_cumulo+Sugar_consuming_rate_cumulo+RQ_integral+AS_Vol.+emission_O2+emission_CO2+generate_CO2; 0.685, 0.856, tmp+AN_cumulo+interval_Pdt.+OD+RS+Feed_Vol+mu_cumulo+Sugar_consuming_rate_cumulo+rab_integral+AS_Vol.+emission_O2; 0.690, 0.856, tmp+interval_Pdt.+OD+RS+Feed_Vol+mu_cumulo+nu_per_rho_cumulo+Sugar_consuming_rate_cumulo+AS_Vol.+consum_O2; 0.675, 0.856, tmp+AN_cumulo+RS+Feed_Vol+mu_cumulo+rho_cumulo+nu_per_rho_cumulo+Sugar_consuming_rate_cumulo+RQ_integral+AS_Vol.+emission_O2+emission_CO2+generate_CO2; 0.685, 0.856, tmp+AN+interval_Pdt.+RS+Feed_Vol+mu_cumulo+nu_per_rho_cumulo+Sugar_consuming_rate_cumulo+AS_Vol.+emission_CO2+generate_CO2; 0.675, 0.856, tmp+PL+AN+interval_yield+interval_Pdt.+RS+Feed_Vol+mu_cumulo+Sugar_consuming_rate_cumulo+rab_integral+AS_Vol.+emission_O2+emission_CO2; 0.690, 0.856, tmp+AN_cumulo+interval_Pdt.+OD+RS+Feed_Vol+mu_cumulo+nu_per_rho_cumulo+Sugar_consuming_rate_cumulo+AS_Vol.; 0.674, 0.856, tmp+AN+AN_cumulo+interval_yield+interval_Pdt.+OD+RS+Feed_Vol+mu_cumulo+Sugar_consuming_rate_cumulo+rab_integral+AS_Vol.+emission_O2; 0.674, 0.856, tmp+PL+interval_yield+RS+Feed_Vol+mu_cumulo+rho_cumulo+Sugar_consuming_rate_cumulo+RQ_integral+AS_Vol.+emission_O2+emission_CO2+generate_CO2; 0.674, 0.856, tmp+PL+AN_cumulo+interval_Pdt.+RS+Feed_Vol+mu_cumulo+nu_per_rho_cumulo+Sugar_consuming_rate_cumulo+rab_integral+AS_Vol.+emission_O2+emission_CO2; 0.690, 0.856, tmp+AN_cumulo+RS+Feed_Vol+mu_cumulo+rho_cumulo+Sugar_consuming_rate_cumulo+AS_Vol.+emission_CO2+generate_CO2; 0.690, 0.856, tmp+RS+Feed_Vol+mu_cumulo+rho_cumulo+Sugar_consuming_rate_cumulo+rab_integral+AS_Vol.+emission_CO2+generate_CO2; 0.685, 0.856, tmp+AN_cumulo+interval_Pdt.+RS+Feed_Vol+mu_cumulo+nu_cumulo+rho_cumulo+Sugar_consuming_rate_cumulo+rab_integral+AS_Vol.; 0.674, 0.856, tmp+AN_cumulo+interval_Pdt.+RS+Feed_Vol+mu_cumulo+nu_per_rho_cumulo+Sugar_consuming_rate_cumulo+rab_integral+AS_Vol.+emission_O2+emission_CO2+generate_CO2; 0.695, 0.856, tmp+AN+AN_cumulo+RS+Feed_Vol+mu_cumulo+Sugar_consuming_rate_cumulo+RQ_ integral+AS_Vol.; 0.695, 0.856, tmp+interval_Pdt.+OD+ RS+Feed_Vol+mu_cumulo+nu_per_rho_cumulo+Sugar_ consuming_rate_cumulo+AS_Vol.; 0.690, 0.856, tmp+PL+ AN_cumulo+RS+Feed_Vol+mu_cumulo+Sugar_ consuming_rate_cumulo+rab_integral+AS_Vol.+emission_ CO2; 0.685, 0.856, tmp+PL+AN+AN_cumulo+interval_ Pdt.+RS+Feed_Vol+mu_cumulo+Sugar_consuming_rate_ cumulo+rab_integral+AS_Vol.; 0.695, 0.856, tmp+AN_ cumulo+interval_yield+RS+Feed_Vol+mu_cumulo+Sugar_ consuming_rate_cumulo+AS_Vol.+generate_CO2; 0.685, 0.856, tmp+PL+AN+RS+Feed_Vol+mu_cumulo+Sugar_ consuming_rate_cumulo+RQ_integral+AS_Vol.+emission_ O2+emission_CO2; 0.695, 0.856, tmp+PL+AN_cumulo+ interval_Pdt.+RS+Feed_Vol+mu_cumulo+Sugar_ consuming_rate_cumulo+AS_Vol.; 0.690, 0.856, tmp+AN+ AN_cumulo+RS+Feed_Vol+mu_cumulo+Sugar_ consuming_rate_cumulo+rab_integral+AS_Vol.+emission_ CO2; 0.690, 0.856, tmp+AN_cumulo+interval_yield+RS+ Feed_Vol+mu_cumulo+Sugar_consuming_rate_cumulo+ rab_integral+AS_Vol.+generate_CO2; 0.685, 0.856, tmp+ AN_cumulo+RS+Feed_Vol+mu_cumulo+nu_per_rho_ cumulo+Sugar_consuming_rate_cumulo+rab_integral+AS_ Vol.+emission_CO2+generate_CO2; 0.680, 0.856, tmp+ AN+interval_Pdt.+RS+Feed_Vol+mu_cumulo+nu_per_ rho_cumulo+Sugar_consuming_rate_cumulo+RQ_ integral+AS_Vol.+emission_O2+emission_CO2; 0.685, 0.856, tmp+OD+RS+Feed_Vol+mu_cumulo+rho_cumulo+ Sugar_consuming_rate_cumulo+RQ_integral+AS_Vol.+ emission_CO2+consum_O2; 0.674, 0.856, tmp+AN_cu- mulo+interval_Pdt.+OD+RS+Feed_Vol+mu_cumulo+ Sugar_consuming_rate_cumulo+RQ_integral+AS_Vol.+ emission_O2+emission_CO2+generate_CO2; 0.699, 0.856, tmp+PL+interval_Pdt.+RS+Feed_Vol+mu_cumulo+Sugar_ consuming_rate_cumulo+AS_Vol.; 0.690, 0.856, tmp+AN_ cumulo+interval_yield+RS+Feed_Vol+mu_cumulo+Sugar_ consuming_rate_cumulo+rab_integral+RQ_integral+AS_ Vol.; 0.685, 0.856, tmp+AN_cumulo+interval_Pdt.+RS+ Feed_Vol+mu_cumulo+rho_cumulo+Sugar_consuming_ rate_cumulo+rab_integral+AS_Vol.+emission_CO2; 0.690, 0.856, tmp+AN+AN_cumulo+RS+Feed_Vol+mu_cumulo+ Sugar_consuming_rate_cumulo+RQ_integral+AS_Vol.+ emission_CO2; 0.680, 0.856, tmp+PL+AN_cumulo+inter- val_Pdt.+RS+Feed_Vol+mu_cumulo+rho_cumulo+Sugar_ consuming_rate_cumulo+rab_integral+AS_Vol.+emission_ O2; 0.674, 0.856, tmp+AN+AN_cumulo+interval_Pdt.+ OD+RS+Feed_Vol+mu_cumulo+rho_cumulo+Sugar_ consuming_rate_cumulo+RQ_integral+AS_Vol.+emission_ O2; 0.674, 0.856, tmp+AN+interval_yield+interval_Pdt.+ RS+Feed_Vol+mu_cumulo+rho_cumulo+Sugar_ consuming_rate_cumulo+rab_integral+AS_Vol.+emission_ O2+emission_CO2; 0.690, 0.856, tmp+PL+AN_cumulo+ RS+Feed_Vol+mu_cumulo+Sugar_consuming_rate_ cumulo+RQ_integral+AS_Vol.+emission_CO2; 0.685, 0.856, tmp+AN_cumulo+interval_yield+interval_Pdt.+ OD+RS+Feed_Vol+mu_cumulo+Sugar_consuming_rate_ cumulo+rab_integral+AS_Vol.; 0.669, 0.856, tmp+PL+in- terval_yield+interval_Pdt.+OD+RS+Feed_Vol+mu_ cumulo+rho_cumulo+Sugar_consuming_rate_cumulo+ RQ_integral+AS_Vol.+emission_O2+emission_CO2; 0.680, 0.856, tmp+interval_Pdt.+RS+Feed_Vol+mu_cu- mulo+rho_cumulo+nu_per_rho_cumulo+Sugar_consum- ing_rate_cumulo+rab_integral+AS_Vol.+emission_O2+ emission_CO2; 0.685, 0.856, tmp+AN_cumulo+interval_ yield+interval_Pdt.+OD+RS+Feed_Vol+mu_cumulo+ Sugar_consuming_rate_cumulo+AS_Vol.+generate_CO2; 0.690, 0.856, tmp+AN+interval_yield+RS+Feed_ Vol+mu_cumulo+rho_cumulo+Sugar_consuming_rate_cu- mulo+rab_integral+AS_Vol.; 0.685, 0.856, tmp+AN_cu- mulo+interval_yield+interval_Pdt.+RS+Feed_Vol+mu_ cumulo+nu_per_rho_cumulo+Sugar_consuming_rate_ cumulo+rab_integral+emission_O2; 0.685, 0.856, tmp+ AN_cumulo+interval_yield+interval_Pdt.+RS+Feed_Vol+ mu_cumulo+Sugar_consuming_rate_cumulo+rab_integral+ RQ_integral+AS_Vol.; 0.674, 0.856, tmp+PL+interval_ yield+interval_Pdt.+RS+Feed_Vol+mu_cumulo+rho_ cumulo+Sugar_consuming_rate_cumulo+RQ_integral+ AS_Vol.+emission_O2+emission_CO2; 0.694, 0.856, tmp+ AN_cumulo+RS+Feed_Vol+mu_cumulo+rho_cumulo+ Sugar_consuming_rate_cumulo+RQ_integral+AS_Vol.; 0.694, 0.856, tmp+interval_yield+RS+Feed_Vol+mu_cu- mulo+rho_cumulo+Sugar_consuming_rate_cumulo+rab_ integral+AS_Vol.; 0.685, 0.856, tmp+RS+Feed_Vol+mu_ cumulo+Sugar_consuming_rate_cumulo+rab_integral+ RQ_integral+AS_Vol.+emission_O2+emission_CO2+ generate_CO2; 0.690, 0.856, tmp+AN_cumulo+interval_ Pdt.+RS+Feed_Vol+mu_cumulo+rho_cumulo+Sugar_ consuming_rate_cumulo+RQ_integral+AS_Vol.; 0.669, 0.856, tmp+AN_cumulo+interval_yield+interval_Pdt.+ OD+RS+Feed_Vol+mu_cumulo+Sugar_consuming_rate_ cumulo+RQ_integral+AS_Vol.+emission_O2+emission_ CO2+generate_CO2; 0.685, 0.856, tmp+interval_Pdt.+OD+ RS+Feed_Vol+mu_cumulo+rho_cumulo+Sugar_ consuming_rate_cumulo+RQ_integral+AS_Vol.+consum_ O2; 0.679, 0.856, tmp+interval_Pdt.+RS+Feed_Vol+mu_ cumulo+rho_cumulo+Sugar_consuming_rate_cumulo+rab_ integral+RQ_integral+AS_Vol.+emission_O2+emission_ CO2; 0.704, 0.856, tmp+interval_yield+RS+Feed_Vol+mu_ cumulo+Sugar_consuming_rate_cumulo+AS_Vol.; 0.685, 0.856, tmp+AN_cumulo+interval_Pdt.+OD+RS+Feed_ Vol+mu_cumulo+rho_cumulo+Sugar_consuming_rate_cu- mulo+RQ_integral+emission_O2; 0.668, 0.856, tmp+pH+ PL+interval_Pdt.+OD+RS+Feed_Vol+mu_cumulo+rho_ cumulo+Sugar_consuming_rate_cumulo+RQ_integral+ AS_Vol.+emission_O2+emission_CO2; 0.704, 0.856, tmp+ AN_cumulo+RS+Feed_Vol+mu_cumulo+Sugar_ consuming_rate_cumulo+AS_Vol.; 0.685, 0.856, tmp+OD+ RS+Feed_Vol+mu_cumulo+rho_cumulo+Sugar_ consuming_rate_cumulo+RQ_integral+AS_Vol.+emission_ O2+emission_CO2; 0.694, 0.856, tmp+PL+RS+Feed_Vol+ mu_cumulo+Sugar_consuming_rate_cumulo+AS_Vol.+ emission_CO2+generate_CO2; 0.690, 0.856, tmp+AN+ AN_cumulo+interval_Pdt.+RS+Feed_Vol+mu_cumulo+ Sugar_consuming_rate_cumulo+RQ_integral+AS_Vol.; 0.668, 0.856, tmp+PL+AN_cumulo+interval_Pdt.+OD+ RS+Feed_Vol+mu_cumulo+nu_per_rho_cumulo+Sugar_ consuming_rate_cumulo+RQ_integral+AS_Vol.+emission_ O2+emission_CO2; 0.685, 0.856, tmp+AN+RS+Feed_Vol+ mu_cumulo+rho_cumulo+Sugar_consuming_rate_cumulo+ RQ_integral+AS_Vol.+emission_O2+emission_CO2; 0.699, 0.856, tmp+AN+interval_Pdt.+RS+Feed_Vol+mu_ cumulo+Sugar_consuming_rate_cumulo+rab_integral; 0.674, 0.856, tmp+pH+PL+interval_Pdt.+RS+Feed_Vol+ mu_cumulo+nu_per_rho_cumulo+Sugar_consuming_rate_ cumulo+RQ_integral+AS_Vol.+emission_O2+emission_ CO2; 0.668, 0.856, tmp+PL+AN+interval_Pdt.+RS+Feed_ Vol+mu_cumulo+rho_cumulo+nu_per_rho_cumulo+ Sugar_consuming_rate_cumulo+RQ_integral+AS_Vol.+ emission_O2+emission_CO2; 0.674, 0.856, tmp+AN+ interval_yield+interval_Pdt.+RS+Feed_Vol+mu_cumulo+ nu_per_rho_cumulo+Sugar_consuming_rate_cumulo+rab_ integral+AS_Vol.+emission_O2+emission_CO2; 0.679, 0.856, tmp+AN_cumulo+interval_Pdt.+OD+RS+Feed_ Vol+mu_cumulo+nu_per_rho_cumulo+Sugar_consuming_ rate_cumulo+RQ_integral+AS_Vol.+emission_O2; 0.679, 0.856, tmp+AN_cumulo+interval_Pdt.+RS+Feed_Vol+mu_cumulo+nu_per_rho_cumulo+Sugar_consuming_rate_cumulo+rab_integral+AS_Vol.+emission_O2+generate_CO2; 0.679, 0.856, tmp+PL+AN+RS+Feed_Vol+mu_cumulo+Sugar_consuming_rate_cumulo+RQ_integral+AS_Vol.+emission_O2+emission_CO2+generate_CO2; 0.684, 0.856, tmp+AN_cumulo+interval_yield+interval_Pdt.+RS+Feed_Vol+mu_cumulo+Sugar_consuming_rate_cumulo+rab_integral+RQ_integral+emission_O2; 0.679, 0.856, tmp+PL+RS+Feed_Vol+mu_cumulo+rho_cumulo+nu_per_rho_cumulo+Sugar_consuming_rate_cumulo+RQ_integral+AS_Vol.+emission_O2+emission_CO2; 0.684, 0.856, tmp+RS+Feed_Vol+mu_cumulo+nu_per_rho_cumulo+Sugar_consuming_rate_cumulo+rab_integral+RQ_integral+AS_Vol.+emission_O2+emission_CO2; 0.679, 0.856, tmp+pH+AN_cumulo+RS+Feed_Vol+mu_cumulo+Sugar_consuming_rate_cumulo+RQ_integral+AS_Vol.+emission_O2+emission_CO2+generate_CO2; 0.674, 0.856, tmp+AN_cumulo+RS+Feed_Vol+mu_cumulo+nu_cumulo+nu_per_rho_cumulo+Sugar_consuming_rate_cumulo+RQ_integral+AS_Vol.+emission_O2+emission_CO2+generate_CO2; 0.689, 0.856, tmp+AN+RS+Feed_Vol+mu_cumulo+nu_per_rho_cumulo+Sugar_consuming_rate_cumulo+AS_Vol.+emission_CO2+generate_CO2; 0.674, 0.856, tmp+AN+interval_Pdt.+RS+Feed_Vol+mu_cumulo+nu_per_rho_cumulo+Sugar_consuming_rate_cumulo+RQ_integral+AS_Vol.+emission_O2+emission_CO2; 0.689, 0.856, tmp+RS+Feed_Vol+mu_cumulo+nu_per_rho_cumulo+Sugar_consuming_rate_cumulo+rab_integral+AS_Vol.+emission_CO2+generate_CO2; 0.674, 0.856, tmp+AN_cumulo+interval_yield+interval_Pdt.+RS+Feed_Vol+mu_cumulo+nu_cumulo+Sugar_consuming_rate_cumulo+rab_integral+AS_Vol.+emission_O2+emission_CO2; 0.684, 0.856, tmp+AN+AN_cumulo+interval_Pdt.+RS+Feed_Vol+mu_cumulo+Sugar_consuming_rate_cumulo+rab_integral+RQ_integral+emission_O2; 0.668, 0.856, tmp+PL+AN+interval_yield+interval_Pdt.+RS+Feed_Vol+mu_cumulo+nu_per_rho_cumulo+Sugar_consuming_rate_cumulo+RQ_integral+AS_Vol.+emission_O2+emission_CO2; 0.694, 0.856, tmp+RS+Feed_Vol+mu_cumulo+nu_cumulo+Sugar_consuming_rate_cumulo+AS_Vol.+emission_CO2+generate_CO2; 0.668, 0.856, tmp+PL+interval_Pdt.+RS+Feed_Vol+mu_cumulo+rho_cumulo+nu_per_rho_cumulo+Sugar_consuming_rate_cumulo+RQ_integral+AS_Vol.+emission_O2+emission_CO2+generate_CO2; 0.689, 0.855, tmp+interval_yield+interval_Pdt.+OD+RS+Feed_Vol+mu_cumulo+Sugar_consuming_rate_cumulo+AS_Vol.+consum_O2; 0.684, 0.855, tmp+interval_Pdt.+OD+RS+Feed_Vol+mu_cumulo+rho_cumulo+Sugar_consuming_rate_cumulo+rab_integral+AS_Vol.+emission_O2; 0.684, 0.855, tmp+AN+interval_Pdt.+RS+Feed_Vol+mu_cumulo+rho_cumulo+Sugar_consuming_rate_cumulo+rab_integral+AS_Vol.+emission_O2; 0.684, 0.855, tmp+PL+AN_cumulo+interval_Pdt.+RS+Feed_Vol+mu_cumulo+Sugar_consuming_rate_cumulo+rab_integral+AS_Vol.+generate_CO2; 0.684, 0.855, tmp+AN_cumulo+interval_Pdt.+RS+Feed_Vol+mu_cumulo+nu_per_rho_cumulo+Sugar_consuming_rate_cumulo+AS_Vol.+emission_CO2+generate_CO2; 0.668, 0.855, tmp+PL+AN_cumulo+interval_Pdt.+RS+Feed_Vol+mu_cumulo+rho_cumulo+Sugar_consuming_rate_cumulo+RQ_integral+AS_Vol.+emission_O2+emission_CO2+generate_CO2; 0.679, 0.855, tmp+PL+AN_cumulo+interval_Pdt.+RS+Feed_Vol+mu_cumulo+Sugar_consuming_rate_cumulo+rab_integral+AS_Vol.+emission_O2+emission_CO2; 0.694, 0.855, tmp+RS+Feed_Vol+mu_cumulo+nu_per_rho_cumulo+Sugar_consuming_rate_cumulo+RQ_integral+AS_Vol.+emission_O2+emission_CO2+generate_CO2; 0.674, 0.855, tmp+AN_cumulo+interval_Pdt.+RS+Feed_Vol+mu_cumulo+rho_cumulo+Sugar_consuming_rate_cumulo+RQ_integral+AS_Vol.+emission_O2+emission_CO2+generate_CO2; 0.689, 0.855, tmp+PL+AN_cumulo+interval_Pdt.+RS+Feed_Vol+mu_cumulo+Sugar_consuming_rate_cumulo+AS_Vol.+generate_CO2; 0.689, 0.855, tmp+AN_cumulo+interval_Pdt.+RS+Feed_Vol+mu_cumulo+Sugar_consuming_rate_cumulo+rab_integral+AS_Vol.+consum_O2; 0.674, 0.855, tmp+PL+AN_cumulo+interval_yield+interval_Pdt.+RS+Feed_Vol+mu_cumulo+Sugar_consuming_rate_cumulo+RQ_integral+AS_Vol.+emission_O2+emission_CO2; 0.689, 0.855, tmp+AN_cumulo+interval_Pdt.+RS+Feed_Vol+mu_cumulo+nu_cumulo+Sugar_consuming_rate_cumulo+RQ_integral+AS_Vol; 0.679, 0.855, tmp+PL+AN+AN_cumulo+interval_Pdt.+RS+Feed_Vol+mu_cumulo+Sugar_consuming_rate_cumulo+rab_integral+AS_Vol.+emission_O2; 0.674, 0.855, tmp+interval_Pdt.+RS+Feed_Vol+mu_cumulo+rho_cumulo+nu_per_rho_cumulo+Sugar_consuming_rate_cumulo+RQ_integral+AS_Vol.+emission_O2+emission_CO2+generate_CO2; 0.679, 0.855, tmp+PL+AN_cumulo+interval_Pdt.+RS+Feed_Vol+mu_cumulo+nu_per_rho_cumulo+Sugar_consuming_rate_cumulo+RQ_integral+AS_Vol.+emission_O2; 0.668, 0.855, tmp+PL+interval_yield+interval_Pdt.+RS+Feed_Vol+mu_cumulo+nu_per_rho_cumulo+Sugar_consuming_rate_cumulo+RQ_integral+AS_Vol.+emission_O2+emission_CO2+generate_CO2; 0.679, 0.855, tmp+AN+RS+Feed_Vol+mu_cumulo+nu_per_rho_cumulo+Sugar_consuming_rate_cumulo+rab_integral+RQ_integral+AS_Vol.+emission_O2+emission_CO2; 0.694, 0.855, tmp+RS+Feed_Vol+mu_cumulo+Sugar_consuming_rate_cumulo+AS_Vol.+emission_CO2+consum_O2+generate_CO2; 0.674, 0.855, tmp+PL+AN+interval_yield+RS+Feed_Vol+mu_cumulo+rho_cumulo+Sugar_consuming_rate_cumulo+RQ_integral+AS_Vol.+emission_O2+emission_CO2; 0.679, 0.855, tmp+PL+AN+RS+Feed_Vol+mu_cumulo+nu_per_rho_cumulo+Sugar_consuming_rate_cumulo+RQ_integral+AS_Vol.+emission_O2+emission_CO2; 0.679, 0.855, tmp+interval_Pdt.+RS+Feed_Vol+mu_cumulo+nu_cumulo+Sugar_consuming_rate_cumulo+RQ_integral+AS_Vol.+emission_O2+emission_CO2+generate_CO2; 0.684, 0.855, tmp+AN_cumulo+interval_Pdt.+RS+Feed_Vol+mu_cumulo+rho_cumulo+Sugar_consuming_rate_cumulo+rab_integral+AS_Vol.+generate_CO2; 0.673, 0.855, tmp+PL+AN+AN_cumulo+RS+Feed_Vol+mu_cumulo+Sugar_consuming_rate_cumulo+RQ_integral+AS_Vol.+emission_O2+emission_CO2+generate_CO2; 0.684, 0.855, tmp+AN_cumulo+interval_Pdt.+RS+Feed_Vol+mu_cumulo+Sugar_consuming_rate_cumulo+rab_integral+AS_Vol.+emission_CO2+generate_CO2; 0.689, 0.855, tmp+interval_Pdt.+RS+Feed_Vol+mu_cumulo+Sugar_consuming_rate_cumulo+RQ_integral+AS_Vol.+emission_CO2+generate_CO2; 0.694, 0.855, tmp+pH+AN_cumulo+RS+Feed_Vol+mu_cumulo+Sugar_consuming_rate_cumulo+RQ_integral+AS_Vol.; 0.689, 0.855, tmp+RS+Feed_Vol+mu_cumulo+Sugar_consuming_rate_cumulo+RQ_integral+AS_Vol.+emission_CO2+consum_O2+generate_CO2; 0.703, 0.855, tmp+interval_yield+RS+Feed_Vol+mu_cumulo+nu_per_rho_cumulo+AS_Vol.; 0.673, 0.855, tmp+PL+AN+interval_Pdt.+RS+Feed_Vol+mu_cumulo+nu_per_rho_cumulo+Sugar_consuming_rate_cumulo+rab_integral+AS_Vol.+emission_O2+emission_CO2; 0.684, 0.855, tmp+AN_cumulo+interval_Pdt.+RS+Feed_Vol+mu_cumulo+nu_per_rho_cumulo+Sugar_consuming_rate_cumulo+rab_integral+RQ_integral+emission_O2; 0.694, 0.855, tmp+

AN_cumulo+interval_yield+interval_Pdt.+RS+Feed_Vol+mu_cumulo+Sugar_consuming_rate_cumulo+AS_Vol.; 0.689, 0.855, tmp+interval_yield+interval_Pdt.+RS+Feed_Vol+mu_cumulo+nu_per_rho_cumulo+Sugar_consuming_rate_cumulo+rab_integral+AS_Vol.; 0.673, 0.855, tmp+PL+interval_Pdt.+OD+RS+Feed_Vol+mu_cumulo+rho_cumulo+Sugar_consuming_rate_cumulo+rab_integral+AS_Vol.+emission_O2+emission_CO2; 0.679, 0.855, tmp+PL+RS+Feed_Vol+mu_cumulo+nu_cumulo+Sugar_consuming_rate_cumulo+RQ_integral+AS_Vol.+emission_O2+emission_CO2+generate_CO2; 0.673, 0.855, tmp+AN_cumulo+RS+Feed_Vol+mu_cumulo+nu_cumulo+rho_cumulo+Sugar_consuming_rate_cumulo+RQ_integral+AS_Vol.+emission_O2+emission_CO2+generate_CO2; 0.689, 0.855, tmp+AN_cumulo+interval_Pdt.+RS+Feed_Vol+mu_cumulo+rho_cumulo+Sugar_consuming_rate_cumulo+rab_integral+emission_O2; 0.684, 0.855, tmp+AN_cumulo+interval_Pdt.+OD+RS+Feed_Vol+mu_cumulo+nu_per_rho_cumulo+Sugar_consuming_rate_cumulo+AS_Vol.+generate_CO2; 0.684, 0.855, tmp+AN_cumulo+interval_Pdt.+RS+Feed_Vol+mu_cumulo+Sugar_consuming_rate_cumulo+RQ_integral+AS_Vol.+emission_CO2+generate_CO2; 0.679, 0.855, tmp+AN+AN_cumulo+interval_Pdt.+OD+RS+Feed_Vol+mu_cumulo+rho_cumulo+Sugar_consuming_rate_cumulo+RQ_integral+AS_Vol; 0.679, 0.855, tmp+AN+AN_cumulo+RS+Feed_Vol+mu_cumulo+nu_per_rho_cumulo+Sugar_consuming_rate_cumulo+RQ_integral+AS_Vol.+emission_CO2+generate_CO2; 0.684, 0.855, tmp+AN_cumulo+interval_Pdt.+RS+Feed_Vol+mu_cumulo+Sugar_consuming_rate_cumulo+RQ_integral+AS_Vol.+emission_O2+emission_CO2; 0.684, 0.855, tmp+PL+AN_cumulo+interval_yield+interval_Pdt.+RS+Feed_Vol+mu_cumulo+Sugar_consuming_rate_cumulo+rab_integral+emission_O2; 0.679, 0.855, tmp+interval_Pdt.+RS+Feed_Vol+mu_cumulo+nu_cumulo+nu_per_rho_cumulo+Sugar_consuming_rate_cumulo+rab_integral+AS_Vol.+emission_O2+emission_CO2; 0.679, 0.855, tmp+RS+Feed_Vol+mu_cumulo+rho_cumulo+Sugar_consuming_rate_cumulo+rab_integral+RQ_integral+AS_Vol.+emission_O2+emission_CO2+generate_CO2; 0.673, 0.855, tmp+AN_cumulo+interval_yield+interval_Pdt.+OD+RS+Feed_Vol+mu_cumulo+nu_per_rho_cumulo+Sugar_consuming_rate_cumulo+rab_integral+AS_Vol.+emission_O2; 0.679, 0.855, tmp+interval_yield+interval_Pdt.+RS+Feed_Vol+mu_cumulo+Sugar_consuming_rate_cumulo+rab_integral+RQ_integral+AS_Vol.+emission_O2+emission_CO2; 0.673, 0.855, tmp+PL+AN+interval_yield+interval_Pdt.+RS+Feed_Vol+mu_cumulo+Sugar_consuming_rate_cumulo+RQ_integral+AS_Vol.+emission_O2+emission_CO2; 0.684, 0.855, tmp+interval_Pdt.+OD+RS+Feed_Vol+mu_cumulo+rho_cumulo+Sugar_consuming_rate_cumulo+AS_Vol.+consum_O2+generate_CO2; 0.689, 0.855, tmp+PL+interval_Pdt.+RS+Feed_Vol+mu_cumulo+nu_per_rho_cumulo+Sugar_consuming_rate_cumulo+rab_integral+AS_Vol.; 0.694, 0.855, tmp+interval_Pdt.+RS+Feed_Vol+mu_cumulo+Sugar_consuming_rate_cumulo+rab_integral+AS_Vol.+emission_O2; 0.678, 0.855, tmp+AN+AN_cumulo+interval_Pdt.+OD+RS+Feed_Vol+mu_cumulo+Sugar_consuming_rate_cumulo+RQ_integral+AS_Vol.+emission_O2; 0.684, 0.855, tmp+PL+AN_cumulo+interval_Pdt.+RS+Feed_Vol+mu_cumulo+Sugar_consuming_rate_cumulo+rab_integral+RQ_integral+emission_O2; 0.693, 0.855, tmp+PL+interval_Pdt.+RS+Feed_Vol+mu_cumulo+nu_per_rho_cumulo+Sugar_consuming_rate_cumulo+AS_Vol.; 0.673, 0.855, tmp+AN+interval_yield+interval_Pdt.+RS+Feed_Vol+mu_cumulo+Sugar_consuming_rate_cumulo+RQ_integral+AS_Vol.+emission_O2+emission_CO2+generate_CO2; 0.693, 0.855, tmp+interval_Pdt.+RS+Feed_Vol+mu_cumulo+nu_cumulo+Sugar_consuming_rate_cumulo+rab_integral+AS_Vol.; 0.693, 0.855, tmp+pH+RS+Feed_Vol+mu_cumulo+Sugar_consuming_rate_cumulo+AS_Vol.+emission_CO2+generate_CO2; 0.689, 0.855, tmp+PL+interval_Pdt.+OD+RS+Feed_Vol+mu_cumulo+rho_cumulo+Sugar_consuming_rate_cumulo+AS_Vol.; 0.678, 0.855, tmp+AN_cumulo+interval_Pdt.+RS+Feed_Vol+mu_cumulo+nu_per_rho_cumulo+Sugar_consuming_rate_cumulo+RQ_integral+AS_Vol.+emission_O2+emission_CO2; 0.673, 0.855, tmp+AN_cumulo+OD+RS+Feed_Vol+mu_cumulo+nu_per_rho_cumulo+Sugar_consuming_rate_cumulo+RQ_integral+AS_Vol.+emission_O2+emission_CO2+generate_CO2; 0.684, 0.855, tmp+AN+AN_cumulo+interval_Pdt.+RS+Feed_Vol+mu_cumulo+rho_cumulo+Sugar_consuming_rate_cumulo+rab_integral+AS_Vol.; 0.689, 0.855, tmp+interval_yield+interval_Pdt.+OD+RS+Feed_Vol+mu_cumulo+rho_cumulo+Sugar_consuming_rate_cumulo+AS_Vol.; 0.698, 0.855, tmp+interval_Pdt.+RS+Feed_Vol+mu_cumulo+Sugar_consuming_rate_cumulo+AS_Vol.+generate_CO2; 0.673, 0.855, tmp+PL+RS+Feed_Vol+mu_cumulo+rho_cumulo+nu_per_rho_cumulo+Sugar_consuming_rate_cumulo+RQ_integral+AS_Vol.+emission_O2+emission_CO2+generate_CO2; 0.673, 0.855, tmp+AN_cumulo+OD+RS+Feed_Vol+mu_cumulo+rho_cumulo+Sugar_consuming_rate_cumulo+RQ_integral+AS_Vol.+emission_O2+emission_CO2+generate_CO2; 0.678, 0.855, tmp+AN+OD+RS+Feed_Vol+mu_cumulo+Sugar_consuming_rate_cumulo+RQ_integral+AS_Vol.+emission_O2+emission_CO2+generate_CO2; 0.688, 0.855, tmp+AN+AN_cumulo+RS+Feed_Vol+mu_cumulo+nu_per_rho_cumulo+Sugar_consuming_rate_cumulo+rab_integral+AS_Vol; 0.683, 0.855, tmp+interval_Pdt.+RS+Feed_Vol+mu_cumulo+rho_cumulo+Sugar_consuming_rate_cumulo+RQ_integral+AS_Vol.+emission_O2+emission_CO2; 0.683, 0.855, tmp+interval_Pdt.+RS+Feed_Vol+mu_cumulo+nu_per_rho_cumulo+Sugar_consuming_rate_cumulo+AS_Vol.+emission_O2+emission_CO2+generate_CO2; 0.678, 0.855, tmp+AN_cumulo+OD+RS+Feed_Vol+mu_cumulo+rho_cumulo+Sugar_consuming_rate_cumulo+RQ_integral+AS_Vol.+emission_O2+emission_CO2; 0.667, 0.855, tmp+PL+AN+interval_Pdt.+RS+Feed_Vol+mu_cumulo+nu_cumulo+nu_per_rho_cumulo+Sugar_consuming_rate_cumulo+RQ_integral+AS_Vol.+emission_O2+emission_CO2; 0.667, 0.855, tmp+AN_cumulo+interval_Pdt.+OD+RS+Feed_Vol+mu_cumulo+nu_per_rho_cumulo+Sugar_consuming_rate_cumulo+RQ_integral+AS_Vol.+emission_O2+emission_CO2+generate_CO2; 0.678, 0.855, tmp+AN+RS+Feed_Vol+mu_cumulo+nu_cumulo+Sugar_consuming_rate_cumulo+RQ_integral+AS_Vol.+emission_O2+emission_CO2+generate_CO2; 0.683, 0.855, tmp+AN_cumulo+interval_yield+interval_Pdt.+OD+RS+Feed_Vol+mu_cumulo+Sugar_consuming_rate_cumulo+RQ_integral+AS_Vol.; 0.667, 0.855, tmp+PL+interval_Pdt.+RS+Feed_Vol+mu_cumulo+nu_cumulo+nu_per_rho_cumulo+Sugar_consuming_rate_cumulo+RQ_integral+AS_Vol.+emission_O2+emission_CO2+generate_CO2; 0.683, 0.855, tmp+AN_cumulo+OD+RS+Feed_Vol+mu_cumulo+Sugar_consuming_rate_cumulo+RQ_integral+AS_Vol.+emission_O2+emission_CO2; 0.683, 0.855, tmp+interval_yield+interval_Pdt.+OD+RS+Feed_Vol+mu_cumulo+rho_cumulo+Sugar_consuming_rate_cumulo+rab_integral+AS_Vol.; 0.673, 0.855, tmp+interval_Pdt.+RS+Feed_Vol+mu_cumulo+nu_cumulo+nu_per_rho_cumulo+Sugar_consuming_rate_cumulo+RQ_integral+

AS_Vol.+emission_O2+emission_CO2+generate_CO2; 0.698, 0.855, tmp+AN_cumulo+interval_Pdt.+RS+Feed_Vol+mu_cumulo+Sugar_consuming_rate_cumulo+rab_integral; 0.678, 0.855, tmp+AN_cumulo+interval_Pdt.+OD+RS+Feed_Vol+mu_cumulo+nu_per_rho_cumulo+Sugar_consuming_rate_cumulo+rab_integral+AS_Vol.+emission_O2; 0.688, 0.855, tmp+pH+AN_cumulo+RS+Feed_Vol+mu_cumulo+rho_cumulo+Sugar_consuming_rate_cumulo+rab_integral+AS_Vol.; 0.678, 0.855, tmp+PL+interval_Pdt.+RS+Feed_Vol+mu_cumulo+Sugar_consuming_rate_cumulo+rab_integral+RQ_integral+AS_Vol.+emission_O2+emission_CO2; 0.683, 0.855, tmp+AN_cumulo+interval_yield+RS+Feed_Vol+mu_cumulo+nu_per_rho_cumulo+Sugar_consuming_rate_cumulo+rab_integral+AS_Vol.+emission_CO2; 0.683, 0.855, tmp+AN+AN_cumulo+interval_Pdt.+OD+RS+Feed_Vol+mu_cumulo+Sugar_consuming_rate_cumulo+AS_Vol.+generate_CO2; 0.683, 0.855, tmp+AN_cumulo+RS+Feed_Vol+mu_cumulo+nu_cumulo+Sugar_consuming_rate_cumulo+RQ_integral+AS_Vol.+emission_CO2+generate_CO2; 0.683, 0.855, tmp+PL+AN_cumulo+interval_Pdt.+RS+Feed_Vol+mu_cumulo+Sugar_consuming_rate_cumulo+rab_integral+RQ_integral+AS_Vol.; 0.688, 0.855, tmp+PL+interval_Pdt.+RS+Feed_Vol+mu_cumulo+Sugar_consuming_rate_cumulo+AS_Vol.+emission_CO2+generate_CO2; 0.673, 0.855, tmp+interval_yield+interval_Pdt.+OD+RS+Feed_Vol+mu_cumulo+rho_cumulo+Sugar_consuming_rate_cumulo+rab_integral+AS_Vol.+emission_O2+emission_CO2; 0.683, 0.855, tmp+AN_cumulo+RS+Feed_Vol+mu_cumulo+nu_per_rho_cumulo+Sugar_consuming_rate_cumulo+rab_integral+RQ_integral+AS_Vol.+emission_CO2; 0.688, 0.855, tmp+PL+AN_cumulo+RS+Feed_Vol+mu_cumulo+nu_per_rho_cumulo+Sugar_consuming_rate_cumulo+rab_integral+AS_Vol.; 0.688, 0.855, tmp+AN_cumulo+interval_Pdt.+RS+Feed_Vol+mu_cumulo+nu_cumulo+Sugar_consuming_rate_cumulo+AS_Vol.+generate_CO2; 0.667, 0.855, tmp+AN_cumulo+interval_Pdt.+OD+RS+Feed_Vol+mu_cumulo+rho_cumulo+Sugar_consuming_rate_cumulo+RQ_integral+AS_Vol.+emission_O2+emission_CO2+generate_CO2; 0.688, 0.855, tmp+interval_yield+RS+Feed_Vol+mu_cumulo+nu_per_rho_cumulo+Sugar_consuming_rate_cumulo+rab_integral+AS_Vol.+emission_CO2; 0.667, 0.855, tmp+PL+interval_Pdt.+OD+RS+Feed_Vol+mu_cumulo+nu_per_rho_cumulo+Sugar_consuming_rate_cumulo+RQ_integral+AS_Vol.+emission_O2+emission_CO2+generate_CO2; 0.698, 0.855, tmp+interval_Pdt.+RS+Feed_Vol+mu_cumulo+rho_cumulo+Sugar_consuming_rate_cumulo+AS_Vol.; 0.693, 0.855, tmp+interval_Pdt.+OD+RS+Feed_Vol+mu_cumulo+Sugar_consuming_rate_cumulo+AS_Vol.+consum_O2; 0.661, 0.855, tmp+PL+AN_cumulo+interval_Pdt.+OD+RS+Feed_Vol+mu_cumulo+rho_cumulo+Sugar_consuming_rate_cumulo+RQ_integral+AS_Vol.+emission_O2+emission_CO2+generate_CO2; 0.661, 0.855, tmp+PL+AN_cumulo+interval_yield+interval_Pdt.+OD+RS+Feed_Vol+mu_cumulo+rho_cumulo+Sugar_consuming_rate_cumulo+RQ_integral+AS_Vol.+emission_O2+emission_CO2; 0.673, 0.855, tmp+PL+interval_yield+OD+RS+Feed_Vol+mu_cumulo+rho_cumulo+Sugar_consuming_rate_cumulo+RQ_integral+AS_Vol.+emission_O2+emission_CO2; 0.678, 0.855, tmp+interval_yield+interval_Pdt.+OD+RS+Feed_Vol+mu_cumulo+Sugar_consuming_rate_cumulo+rab_integral+AS_Vol.+emission_O2+emission_CO2; 0.673, 0.855, tmp+AN_cumulo+interval_Pdt.+OD+RS+Feed_Vol+mu_cumulo+nu_per_rho_cumulo+Sugar_consuming_rate_cumulo+RQ_integral+AS_Vol.+emission_O2+emission_CO2; 0.688, 0.855, tmp+AN_cumulo+OD+RS+Feed_Vol+mu_cumulo+nu_cumulo+Sugar_consuming_rate_cumulo+RQ_integral+AS_Vol.; 0.688, 0.855, tmp+AN_cumulo+OD+RS+Feed_Vol+mu_cumulo+Sugar_consuming_rate_cumulo+RQ_integral+AS_Vol.+consum_O2; 0.678, 0.855, tmp+PL+OD+RS+Feed_Vol+mu_cumulo+Sugar_consuming_rate_cumulo+RQ_integral+AS_Vol.+emission_O2+emission_CO2+generate_CO2; 0.688, 0.855, tmp+AN+RS+Feed_Vol+mu_cumulo+nu_per_rho_cumulo+Sugar_consuming_rate_cumulo+rab_integral+AS_Vol.+emission_CO2; 0.688, 0.855, tmp+AN_cumulo+interval_yield+interval_Pdt.+RS+Feed_Vol+mu_cumulo+Sugar_consuming_rate_cumulo+AS_Vol.+generate_CO2; 0.683, 0.855, tmp+pH+RS+Feed_Vol+mu_cumulo+Sugar_consuming_rate_cumulo+RQ_integral+AS_Vol.+emission_O2+emission_CO2+generate_CO2; 0.688, 0.855, tmp+interval_yield+interval_Pdt.+RS+Feed_Vol+mu_cumulo+Sugar_consuming_rate_cumulo+rab_integral+AS_Vol.+emission_CO2; 0.688, 0.855, tmp+AN_cumulo+interval_Pdt.+OD+RS+Feed_Vol+mu_cumulo+Sugar_consuming_rate_cumulo+rab_integral+AS_Vol; 0.678, 0.855, tmp+AN_cumulo+RS+Feed_Vol+mu_cumulo+rho_cumulo+Sugar_consuming_rate_cumulo+rab_integral+RQ_integral+AS_Vol.+emission_O2+emission_CO2; 0.693, 0.855, tmp+RS+Feed_Vol+mu_cumulo+rho_cumulo+Sugar_consuming_rate_cumulo+RQ_integral+AS_Vol.+emission_CO2; 0.683, 0.855, tmp+PL+interval_Pdt.+RS+Feed_Vol+mu_cumulo+Sugar_consuming_rate_cumulo+rab_integral+AS_Vol.+emission_O2+emission_CO2; 0.688, 0.855, tmp+interval_yield+RS+Feed_Vol+mu_cumulo+rho_cumulo+Sugar_consuming_rate_cumulo+rab_integral+AS_Vol.+emission_CO2; 0.667, 0.855, tmp+PL+AN_cumulo+interval_yield+interval_Pdt.+RS+Feed_Vol+mu_cumulo+nu_per_rho_cumulo+Sugar_consuming_rate_cumulo+RQ_integral+AS_Vol.+emission_O2+emission_CO2; 0.688, 0.855, tmp+AN_cumulo+interval_yield+interval_Pdt.+OD+RS+Feed_Vol+mu_cumulo+Sugar_consuming_rate_cumulo+AS_Vol.; 0.693, 0.855, tmp+interval_Pdt.+OD+RS+Feed_Vol+mu_cumulo+Sugar_consuming_rate_cumulo+rab_integral+AS_Vol.; 0.678, 0.855, tmp+pH+interval_Pdt.+RS+Feed_Vol+mu_cumulo+rho_cumulo+Sugar_consuming_rate_cumulo+rab_integral+AS_Vol.+emission_O2+emission_CO2; 0.672, 0.855, tmp+PL+AN_cumulo+interval_Pdt.+OD+RS+Feed_Vol+mu_cumulo+rho_cumulo+Sugar_consuming_rate_cumulo+rab_integral+AS_Vol.+emission_O2; 0.693, 0.855, tmp+AN+RS+Feed_Vol+mu_cumulo+Sugar_consuming_rate_cumulo+RQ_integral+AS_Vol.+emission_CO2; 0.688, 0.855, tmp+AN+RS+Feed_Vol+mu_cumulo+rho_cumulo+Sugar_consuming_rate_cumulo+AS_Vol.+emission_CO2+generate_CO2; 0.688, 0.855, tmp+AN_cumulo+interval_Pdt.+RS+Feed_Vol+mu_cumulo+rho_cumulo+Sugar_consuming_rate_cumulo+AS_Vol.+generate_CO2; 0.683, 0.855, tmp+AN+interval_Pdt.+RS+Feed_Vol+mu_cumulo+Sugar_consuming_rate_cumulo+RQ_integral+AS_Vol.+emission_O2+emission_CO2; 0.698, 0.855, tmp+interval_Pdt.+RS+Feed_Vol+mu_cumulo+Sugar_consuming_rate_cumulo+RQ_integral+AS_Vol.; 0.672, 0.855, tmp+PL+interval_yield+interval_Pdt.+RS+Feed_Vol+mu_cumulo+Sugar_consuming_rate_cumulo+rab_integral+RQ_integral+AS_Vol.+emission_O2+emission_CO2; 0.678, 0.855, tmp+interval_Pdt.+RS+Feed_Vol+mu_cumulo+nu_cumulo+rho_cumulo+Sugar_consuming_rate_cumulo+rab_integral+AS_Vol.+emission_O2+emission_CO2; 0.683, 0.855, tmp+PL+AN_cumulo+interval_Pdt.+RS+Feed_Vol+mu_cumulo+rho_cumulo+Sugar_consuming_rate_cumulo+rab_integral+AS_Vol.; 0.693, 0.855, tmp+AN_cumulo+interval_Pdt.+RS+Feed_Vol+mu_cumulo+nu_cumulo+

Sugar_consuming_rate_cumulo+AS_Vol.; 0.688, 0.855, tmp+interval_yield+RS+Feed_Vol+mu_cumulo+Sugar_consuming_rate_cumulo+RQ_integral+AS_Vol.+emission_O2+emission_CO2; 0.667, 0.855, tmp+PL+AN+interval_Pdt.+OD+RS+Feed_Vol+mu_cumulo+nu_per_rho_cumulo+Sugar_consuming_rate_cumulo+RQ_integral+AS_Vol.+emission_O2+emission_CO2; 0.672, 0.855, tmp+AN+interval_yield+interval_Pdt.+RS+Feed_Vol+mu_cumulo+Sugar_consuming_rate_cumulo+rab_integral+AS_Vol.+emission_O2+emission_CO2+generate_CO2; 0.667, 0.855, tmp+PL+AN+interval_yield+interval_Pdt.+RS+Feed_Vol+mu_cumulo+Sugar_consuming_rate_cumulo+RQ_integral+AS_Vol.+emission_O2+emission_CO2+generate_CO2; 0.683, 0.855, tmp+interval_Pdt.+RS+Feed_Vol+mu_cumulo+nu_per_rho_cumulo+Sugar_consuming_rate_cumulo+rab_integral+AS_Vol.+emission_CO2+generate_CO2; 0.678, 0.855, tmp+PL+RS+Feed_Vol+mu_cumulo+nu_cumulo+rho_cumulo+Sugar_consuming_rate_cumulo+RQ_integral+AS_Vol.+emission_O2+emission_CO2; 0.683, 0.855, tmp+AN_cumulo+interval_yield+RS+Feed_Vol+mu_cumulo+Sugar_consuming_rate_cumulo+RQ_integral+AS_Vol.+emission_CO2+generate_CO2; 0.693, 0.855, tmp+pH+interval_Pdt.+RS+Feed_Vol+mu_cumulo+Sugar_consuming_rate_cumulo+rab_integral+AS_Vol.; 0.678, 0.855, tmp+AN_cumulo+interval_Pdt.+RS+Feed_Vol+mu_cumulo+rho_cumulo+nu_per_rho_cumulo+Sugar_consuming_rate_cumulo+rab_integral+AS_Vol.+emission_O2; 0.688, 0.855, tmp+AN+AN_cumulo+OD+RS+Feed_Vol+mu_cumulo+Sugar_consuming_rate_cumulo+RQ_integral+AS_Vol.; 0.678, 0.855, tmp+PL+AN+interval_Pdt.+RS+Feed_Vol+mu_cumulo+nu_per_rho_cumulo+Sugar_consuming_rate_cumulo+RQ_integral+emission_O2+emission_CO2; 0.667, 0.855, tmp+PL+AN+interval_Pdt.+RS+Feed_Vol+mu_cumulo+nu_cumulo+rho_cumulo+Sugar_consuming_rate_cumulo+RQ_integral+AS_Vol.+emission_O2+emission_CO2; 0.702, 0.855, tmp+RS+Feed_Vol+mu_cumulo+Sugar_consuming_rate_cumulo+rab_integral+AS_Vol.; 0.678, 0.855, tmp+interval_Pdt.+RS+Feed_Vol+mu_cumulo+Sugar_consuming_rate_cumulo+rab_integral+RQ_integral+AS_Vol.+emission_O2+emission_CO2+generate_CO2; 0.688, 0.855, tmp+AN_cumulo+RS+Feed_Vol+mu_cumulo+nu_per_rho_cumulo+Sugar_consuming_rate_cumulo+rab_integral+RQ_integral+AS_Vol.; 0.688, 0.855, tmp+PL+AN+interval_Pdt.+RS+Feed_Vol+mu_cumulo+Sugar_consuming_rate_cumulo+rab_integral+AS_Vol.; 0.683, 0.855, tmp+PL+AN+AN_cumulo+interval_Pdt.+RS+Feed_Vol+mu_cumulo+Sugar_consuming_rate_cumulo+rab_integral+emission_O2; 0.688, 0.855, tmp+interval_Pdt.+RS+Feed_Vol+mu_cumulo+nu_cumulo+Sugar_consuming_rate_cumulo+AS_Vol.+emission_CO2+generate_CO2; 0.688, 0.855, tmp+PL+AN_cumulo+interval_yield+RS+Feed_Vol+mu_cumulo+Sugar_consuming_rate_cumulo+RQ_integral+AS_Vol.; 0.667, 0.855, tmp+PL+AN+AN_cumulo+interval_Pdt.+OD+RS+Feed_Vol+mu_cumulo+rho_cumulo+Sugar_consuming_rate_cumulo+RQ_integral+AS_Vol.+emission_O2; 0.672, 0.855, tmp+PL+AN_cumulo+interval_yield+interval_Pdt.+OD+RS+Feed_Vol+mu_cumulo+Sugar_consuming_rate_cumulo+RQ_integral+AS_Vol.+emission_O2; 0.697, 0.855, tmp+interval_yield+interval_Pdt.+RS+Feed_Vol+mu_cumulo+Sugar_consuming_rate_cumulo+AS_Vol.; 0.688, 0.855, tmp+OD+RS+Feed_Vol+mu_cumulo+Sugar_consuming_rate_cumulo+RQ_integral+AS_Vol.+emission_O2+emission_CO2; 0.661, 0.855, tmp+PL+AN+interval_Pdt.+OD+RS+Feed_Vol+mu_cumulo+rho_cumulo+Sugar_consuming_rate_cumulo+RQ_integral+AS_Vol.+emission_O2+emission_CO2+generate_CO2; 0.683, 0.855, tmp+AN+AN_cumulo+interval_Pdt.+RS+Feed_Vol+mu_cumulo+Sugar_consuming_rate_cumulo+rab_integral+AS_Vol.+generate_CO2; 0.697, 0.855, tmp+AN_cumulo+interval_Pdt.+RS+Feed_Vol+mu_cumulo+Sugar_consuming_rate_cumulo+RQ_integral; 0.693, 0.855, tmp+AN+AN_cumulo+interval_Pdt.+RS+Feed_Vol+mu_cumulo+Sugar_consuming_rate_cumulo+AS_Vol.; 0.693, 0.855, tmp+interval_yield+RS+Feed_Vol+mu_cumulo+Sugar_consuming_rate_cumulo+rab_integral+AS_Vol.+emission_CO2; 0.661, 0.855, tmp+PL+AN+interval_Pdt.+OD+RS+Feed_Vol+mu_cumulo+rho_cumulo+Sugar_consuming_rate_cumulo+rab_integral+RQ_integral+AS_Vol.+emission_O2+emission_CO2; 0.683, 0.855, tmp+PL+AN_cumulo+interval_Pdt.+RS+Feed_Vol+mu_cumulo+nu_per_rho_cumulo+Sugar_consuming_rate_cumulo+RQ_integral+AS_Vol.; 0.693, 0.855, tmp+PL+AN+interval_Pdt.+RS+Feed_Vol+mu_cumulo+Sugar_consuming_rate_cumulo+AS_Vol.; 0.688, 0.855, tmp+AN+AN_cumulo+interval_Pdt.+RS+Feed_Vol+mu_cumulo+Sugar_consuming_rate_cumulo+RQ_integral+emission_O2; 0.677, 0.855, tmp+AN+RS+Feed_Vol+mu_cumulo+rho_cumulo+Sugar_consuming_rate_cumulo+rab_integral+RQ_integral+AS_Vol.+emission_O2+emission_CO2; 0.693, 0.855, tmp+AN_cumulo+interval_Pdt.+RS+Feed_Vol+mu_cumulo+rho_cumulo+Sugar_consuming_rate_cumulo+AS_Vol.; 0.688, 0.855, tmp+AN+interval_yield+RS+Feed_Vol+mu_cumulo+Sugar_consuming_rate_cumulo+AS_Vol.+emission_CO2+generate_CO2; 0.688, 0.855, tmp+AN_cumulo+interval_yield+RS+Feed_Vol+mu_cumulo+Sugar_consuming_rate_cumulo+RQ_integral+AS_Vol.+emission_CO2; 0.677, 0.855, tmp+AN_cumulo+interval_Pdt.+OD+RS+Feed_Vol+mu_cumulo+rho_cumulo+Sugar_consuming_rate_cumulo+RQ_integral+AS_Vol.+consum_O2; 0.688, 0.855, tmp+AN_cumulo+RS+Feed_Vol+mu_cumulo+nu_cumulo+Sugar_consuming_rate_cumulo+rab_integral+AS_Vol.+emission_CO2; 0.666, 0.855, tmp+AN_cumulo+interval_yield+interval_Pdt.+RS+Feed_Vol+mu_cumulo+nu_per_rho_cumulo+Sugar_consuming_rate_cumulo+rab_integral+AS_Vol.+emission_O2+emission_CO2+generate_CO2; 0.672, 0.855, tmp+PL+OD+RS+Feed_Vol+mu_cumulo+rho_cumulo+Sugar_consuming_rate_cumulo+RQ_integral+AS_Vol.+emission_O2+emission_CO2+generate_CO2; 0.688, 0.855, tmp+pH+AN_cumulo+RS+Feed_Vol+mu_cumulo+nu_per_rho_cumulo+Sugar_consuming_rate_cumulo+rab_integral+AS_Vol.; 0.672, 0.855, tmp+interval_Pdt.+RS+Feed_Vol+mu_cumulo+nu_per_rho_cumulo+Sugar_consuming_rate_cumulo+rab_integral+RQ_integral+AS_Vol.+emission_O2+emission_CO2+generate_CO2; 0.672, 0.855, tmp+PL+AN_cumulo+interval_yield+interval_Pdt.+RS+Feed_Vol+mu_cumulo+Sugar_consuming_rate_cumulo+rab_integral+RQ_integral+AS_Vol.+emission_O2; 0.672, 0.855, tmp+PL+AN_cumulo+OD+RS+Feed_Vol+mu_cumulo+rho_cumulo+Sugar_consuming_rate_cumulo+RQ_integral+AS_Vol.+emission_O2+emission_CO2; 0.682, 0.855, tmp+AN_cumulo+RS+Feed_Vol+mu_cumulo+rho_cumulo+Sugar_consuming_rate_cumulo+rab_integral+AS_Vol.+emission_CO2+generate_CO2; 0.677, 0.855, tmp+PL+AN_cumulo+interval_Pdt.+OD+RS+Feed_Vol+mu_cumulo+Sugar_consuming_rate_cumulo+RQ_integral+AS_Vol.+emission_O2; 0.688, 0.855, tmp+pH+AN_cumulo+RS+Feed_Vol+mu_cumulo+Sugar_consuming_rate_cumulo+AS_Vol.+emission_CO2+generate_CO2; 0.677, 0.855, tmp+PL+AN_cumulo+interval_yield+interval_Pdt.+RS+Feed_Vol+mu_cumulo+nu_per_rho_cumulo+Sugar_consuming_rate_cumulo+rab_integral+AS_Vol.; 0.666, 0.855, tmp+PL+interval_Pdt.+RS+Feed_Vol+mu_cumulo+nu_cumulo+rho_cumulo+Sugar_consuming_rate_cumulo+RQ_integral+AS_Vol.+emission_O2+emission_CO2+generate_CO2; 0.687, 0.855, tmp+interval_yield+RS+Feed_Vol+mu_cumulo+rho_cumulo+Sugar_consuming_rate_cumulo+AS_Vol.+emission_CO2+generate_CO2; 0.677, 0.855, tmp+pH+RS+Feed_Vol+mu_cumulo+rho_cumulo+Sugar_consuming_rate_cumulo+RQ_integral+AS_Vol.+emission_O2+emission_CO2+generate_CO2; 0.692, 0.855, tmp+RS+Feed_Vol+mu_cumulo+nu_cumulo+Sugar_consuming_rate_cumulo+rab_integral+AS_Vol.+emission_CO2; 0.672, 0.855, tmp+PL+interval_yield+RS+Feed_Vol+mu_cumulo+nu_per_rho_cumulo+Sugar_consuming_rate_cumulo+RQ_integral+AS_Vol.+emission_O2+emission_CO2+generate_CO2; 0.666, 0.855, tmp+PL+interval_yield+interval_Pdt.+RS+Feed_Vol+mu_cumulo+rho_cumulo+Sugar_consuming_rate_cumulo+RQ_integral+AS_Vol.+emission_O2+emission_CO2+generate_CO2; 0.672, 0.855, tmp+PL+AN_cumulo+interval_Pdt.+RS+Feed_Vol+mu_cumulo+rho_cumulo+Sugar_consuming_rate_cumulo+rab_integral+AS_Vol.+emission_O2+emission_CO2; 0.672, 0.855, tmp+PL+AN+AN_cumulo+interval_yield+interval_Pdt.+RS+Feed_Vol+mu_cumulo+Sugar_consuming_rate_cumulo+rab_integral+AS_Vol.+emission_O2; 0.666, 0.855, tmp+PL+interval_Pdt.+OD+RS+Feed_Vol+mu_cumulo+rho_cumulo+nu_per_rho_cumulo+Sugar_consuming_rate_cumulo+RQ_integral+AS_Vol.+emission_O2+emission_CO2; 0.687, 0.855, tmp+AN_cumulo+OD+RS+Feed_Vol+mu_cumulo+rho_cumulo+Sugar_consuming_rate_cumulo+RQ_integral+AS_Vol.; 0.677, 0.855, tmp+interval_Pdt.+OD+RS+Feed_Vol+mu_cumulo+nu_per_rho_cumulo+Sugar_consuming_rate_cumulo+RQ_integral+AS_Vol.+emission_O2+emission_CO2; 0.687, 0.855, tmp+AN_cumulo+RS+Feed_Vol+mu_cumulo+nu_cumulo+Sugar_consuming_rate_cumulo+RQ_integral+AS_Vol.+emission_CO2; 0.672, 0.855, tmp+AN_cumulo+interval_yield+interval_Pdt.+OD+RS+Feed_Vol+mu_cumulo+rho_cumulo+Sugar_consuming_rate_cumulo+RQ_integral+AS_Vol.+emission_O2; 0.687, 0.855, tmp+AN_cumulo+interval_Pdt.+RS+Feed_Vol+mu_cumulo+Sugar_consuming_rate_cumulo+RQ_integral+AS_Vol.+emission_CO2; 0.666, 0.855, tmp+PL+AN+interval_yield+interval_Pdt.+RS+Feed_Vol+mu_cumulo+Sugar_consuming_rate_cumulo+rab_integral+RQ_integral+AS_Vol.+emission_O2+emission_CO2; 0.677, 0.855, tmp+AN_cumulo+interval_Pdt.+RS+Feed_Vol+mu_cumulo+nu_cumulo+nu_per_rho_cumulo+Sugar_consuming_rate_cumulo+rab_integral+AS_Vol.+emission_O2; 0.687, 0.855, tmp+AN+RS+Feed_Vol+mu_cumulo+Sugar_consuming_rate_cumulo+rab_integral+AS_Vol.+emission_CO2+generate_CO2; 0.682, 0.855, tmp+PL+AN_cumulo+interval_Pdt.+RS+Feed_Vol+mu_cumulo+nu_per_rho_cumulo+Sugar_consuming_rate_cumulo+rab_integral+emission_O2; 0.672, 0.854, tmp+interval_Pdt.+RS+Feed_Vol+mu_cumulo+nu_cumulo+rho_cumulo+Sugar_consuming_rate_cumulo+RQ_integral+AS_Vol.+emission_O2+emission_CO2+generate_CO2; 0.672, 0.854, tmp+PL+AN+RS+Feed_Vol+mu_cumulo+rho_cumulo+Sugar_consuming_rate_cumulo+rab_integral+RQ_integral+AS_Vol.+emission_O2+emission_CO2; 0.682, 0.854, tmp+AN+RS+Feed_Vol+mu_cumulo+Sugar_consuming_rate_cumulo+rab_integral+RQ_integral+AS_Vol.+emission_O2+emission_CO2; 0.692, 0.854, tmp+AN_cumulo+RS+Feed_Vol+mu_cumulo+Sugar_consuming_rate_cumulo+RQ_integral+AS_Vol.+generate_CO2; 0.697, 0.854, tmp+AN+interval_Pdt.+RS+Feed_Vol+mu_cumulo+Sugar_consuming_rate_cumulo+generate_CO2; 0.672, 0.854, tmp+interval_yield+interval_Pdt.+RS+Feed_Vol+mu_cumulo+rho_cumulo+Sugar_consuming_rate_cumulo+RQ_integral+AS_Vol.+emission_O2+emission_CO2+generate_CO2; 0.666, 0.854, tmp+PL+AN+interval_yield+interval_Pdt.+RS+Feed_Vol+mu_cumulo+rho_cumulo+Sugar_consuming_rate_cumulo+RQ_integral+AS_Vol.+emission_O2+emission_CO2; 0.672, 0.854, tmp+AN+AN_cumulo+interval_Pdt.+OD+RS+Feed_Vol+mu_cumulo+rho_cumulo+Sugar_consuming_rate_cumulo+rab_integral+AS_Vol.+emission_O2; 0.682, 0.854, tmp+AN+AN_cumulo+interval_Pdt.+OD+RS+Feed_Vol+mu_cumulo+rho_cumulo+Sugar_consuming_rate_cumulo+AS_Vol.; 0.687, 0.854, tmp+interval_Pdt.+OD+RS+Feed_Vol+mu_cumulo+nu_cumulo+nu_per_rho_cumulo+Sugar_consuming_rate_cumulo+AS_Vol.; 0.682, 0.854, tmp+AN+AN_cumulo+interval_Pdt.+OD+RS+Feed_Vol+mu_cumulo+Sugar_consuming_rate_cumulo+RQ_integral+AS_Vol.; 0.682, 0.854, tmp+PL+RS+Feed_Vol+mu_cumulo+nu_cumulo+Sugar_consuming_rate_cumulo+RQ_integral+AS_Vol.+emission_O2+emission_CO2; 0.682, 0.854, tmp+interval_Pdt.+OD+RS+Feed_Vol+mu_cumulo+rho_cumulo+Sugar_consuming_rate_cumulo+AS_Vol.+emission_CO2+generate_CO2; 0.687, 0.854, tmp+pH+interval_Pdt.+RS+Feed_Vol+mu_cumulo+rho_cumulo+Sugar_consuming_rate_cumulo+rab_integral+AS_Vol.; 0.666, 0.854, tmp+PL+AN_cumulo+interval_yield+interval_Pdt.+RS+Feed_Vol+mu_cumulo+nu_per_rho_cumulo+Sugar_consuming_rate_cumulo+rab_integral+AS_Vol.+emission_O2+emission_CO2; 0.687, 0.854, tmp+AN_cumulo+RS+Feed_Vol+mu_cumulo+nu_per_rho_cumulo+Sugar_consuming_rate_cumulo+rab_integral+AS_Vol.+generate_CO2; 0.682, 0.854, tmp+AN_cumulo+RS+Feed_Vol+mu_cumulo+rho_cumulo+Sugar_consuming_rate_cumulo+rab_integral+RQ_integral+AS_Vol.+emission_CO2; 0.682, 0.854, tmp+AN+interval_Pdt.+RS+Feed_Vol+mu_cumulo+rho_cumulo+Sugar_consuming_rate_cumulo+rab_integral+emission_O2+emission_CO2; 0.671, 0.854, tmp+pH+PL+interval_Pdt.+RS+Feed_Vol+mu_cumulo+rho_cumulo+Sugar_consuming_rate_cumulo+RQ_integral+AS_Vol.+emission_O2+emission_CO2; 0.687, 0.854, tmp+AN_cumulo+interval_Pdt.+RS+Feed_Vol+mu_cumulo+nu_per_rho_cumulo+Sugar_consuming_rate_cumulo+RQ_integral+emission_O2; 0.677, 0.854, tmp+AN_cumulo+interval_yield+interval_Pdt.+OD+RS+Feed_Vol+mu_cumulo+rho_cumulo+Sugar_consuming_rate_cumulo+rab_integral+AS_Vol.; 0.677, 0.854, tmp+pH+interval_Pdt.+RS+Feed_Vol+mu_cumulo+Sugar_consuming_rate_cumulo+RQ_integral+AS_Vol.+emission_O2+emission_CO2+generate_CO2; 0.671, 0.854, tmp+AN_cumulo+interval_yield+RS+Feed_Vol+mu_cumulo+nu_per_rho_cumulo+Sugar_consuming_rate_cumulo+RQ_integral+AS_Vol.+emission_O2+emission_CO2+generate_CO2; 0.687, 0.854, tmp+interval_Pdt.+OD+RS+Feed_Vol+mu_cumulo+rho_cumulo+Sugar_consuming_rate_cumulo+AS_Vol.+emission_CO2; 0.660, 0.854, tmp+pH+PL+AN_cumulo+interval_Pdt.+OD+RS+Feed_Vol+mu_cumulo+rho_cumulo+Sugar_consuming_rate_cumulo+RQ_integral+AS_Vol.+emission_O2+emission_CO2; 0.677, 0.854, tmp+interval_Pdt.+OD+RS+Feed_Vol+mu_cumulo+nu_per_rho_cumulo+Sugar_consuming_rate_cumulo+rab_integral+AS_Vol.+emission_O2+emission_CO2; 0.671, 0.854, tmp+AN_cumulo+RS+Feed_Vol+mu_cumulo+nu_per_rho_cumulo+Sugar_consuming_rate_cumulo+rab_integral+RQ_integral+AS_Vol.+emission_O2+emission_CO2+generate_CO2; 0.682, 0.854, tmp+interval_Pdt.+OD+RS+Feed_Vol+mu_cumulo+rho_cumulo+Sugar_consuming_rate_cumulo+AS_Vol.+emission_CO2+ consum_O2; 0.671, 0.854, tmp+PL+AN+interval_yield+ RS+Feed_Vol+mu_cumulo+nu_per_rho_cumulo+Sugar_ consuming_rate_cumulo+RQ_integral+AS_Vol.+emission_ O2+emission_CO2; 0.682, 0.854, tmp+AN_cumulo+ interval_Pdt.+OD+RS+Feed_Vol+mu_cumulo+Sugar_ consuming_rate_cumulo+AS_Vol.+emission_CO2+ generate_CO2; 0.666, 0.854, tmp+AN_cumulo+interval_ yield+interval_Pdt.+OD+RS+Feed_Vol+mu_cumulo+ Sugar_consuming_rate_cumulo+rab_integral+AS_Vol.+ emission_O2+emission_CO2+generate_CO2; 0.682, 0.854, tmp+AN_cumulo+interval_Pdt.+OD+RS+Feed_Vol+mu_ cumulo+rho_cumulo+Sugar_consuming_rate_cumulo+AS_ Vol.+consum_O2; 0.692, 0.854, tmp+interval_yield+OD+ RS+Feed_Vol+mu_cumulo+rho_cumulo+Sugar_ consuming_rate_cumulo+AS_Vol.; 0.687, 0.854, tmp+ interval_Pdt.+OD+RS+Feed_Vol+mu_cumulo+Sugar_ consuming_rate_cumulo+AS_Vol.+emission_CO2+ generate_CO2; 0.687, 0.854, tmp+AN_cumulo+OD+RS+ Feed_Vol+mu_cumulo+Sugar_consuming_rate_cumulo+ RQ_integral+AS_Vol.+emission_CO2; 0.682, 0.854, tmp+ AN_cumulo+interval_Pdt.+OD+RS+Feed_Vol+mu_ cumulo+rho_cumulo+Sugar_consuming_rate_cumulo+AS_ Vol.+emission_CO2; 0.687, 0.854, tmp+PL+AN_cumulo+ RS+Feed_Vol+mu_cumulo+Sugar_consuming_rate_ cumulo+AS_Vol.+emission_CO2+generate_CO2; 0.671, 0.854, tmp+AN+interval_yield+interval_Pdt.+RS+Feed_ Vol+mu_cumulo+Sugar_consuming_rate_cumulo+rab_in- tegral+RQ_integral+AS_Vol.+emission_O2+emission_ CO2; 0.677, 0.854, tmp+PL+RS+Feed_Vol+mu_cumulo+ nu_cumulo+nu_per_rho_cumulo+Sugar_consuming_rate_ cumulo+RQ_integral+AS_Vol.+emission_O2+emission_ CO2; 0.687, 0.854, tmp+RS+Feed_Vol+mu_cumulo+nu_ cumulo+Sugar_consuming_rate_cumulo+RQ_integral+ AS_Vol.+emission_CO2+generate_CO2; 0.671, 0.854, tmp+interval_Pdt.+OD+RS+Feed_Vol+mu_cumulo+rho_ cumulo+Sugar_consuming_rate_cumulo+rab_integral+ RQ_integral+AS_Vol.+emission_O2+emission_CO2; 0.671, 0.854, tmp+AN_cumulo+interval_Pdt.+RS+Feed_ Vol+mu_cumulo+rho_cumulo+nu_per_rho_cumulo+ Sugar_consuming_rate_cumulo+rab_integral+AS_Vol.+ emission_O2+emission_CO2; 0.677, 0.854, tmp+AN+ interval_Pdt.+RS+Feed_Vol+mu_cumulo+Sugar_ consuming_rate_cumulo+rab_integral+AS_Vol.+emission_ O2+emission_CO2+generate_CO2; 0.666, 0.854, tmp+PL+ AN_cumulo+interval_yield+interval_Pdt.+OD+RS+Feed_ Vol+mu_cumulo+rho_cumulo+Sugar_consuming_rate_ cumulo+rab_integral+AS_Vol.+emission_O2; 0.687, 0.854, tmp+pH+AN_cumulo+RS+Feed_Vol+mu_cumulo+Sugar_ consuming_rate_cumulo+rab_integral+AS_Vol.+emission_ CO2; 0.687, 0.854, tmp+interval_yield+interval_Pdt.+RS+ Feed_Vol+mu_cumulo+rho_cumulo+Sugar_consuming_ rate_cumulo+rab_integral+AS_Vol.; 0.692, 0.854, tmp+ OD+RS+Feed_Vol+mu_cumulo+Sugar_consuming_rate_ cumulo+AS_Vol.+emission_CO2+generate_CO2; 0.677, 0.854, tmp+AN+interval_Pdt.+RS+Feed_Vol+mu_cumulo+ Sugar_consuming_rate_cumulo+rab_integral+RQ_inte- gral+AS_Vol.+emission_O2+emission_CO2; 0.682, 0.854, tmp+AN+RS+Feed_Vol+mu_cumulo+nu_per_rho_cu- mulo+Sugar_consuming_rate_cumulo+RQ_integral+AS_ Vol.+emission_CO2+generate_CO2; 0.671, 0.854, tmp+in- terval_yield+interval_Pdt.+OD+RS+Feed_Vol+mu_ cumulo+Sugar_consuming_rate_cumulo+RQ_integral+ AS_Vol.+emission_O2+emission_CO2+generate_CO2; 0.677, 0.854, tmp+AN_cumulo+interval_Pdt.+OD+RS+ Feed_Vol+mu_cumulo+Sugar_consuming_rate_cumulo+ RQ_integral+AS_Vol.+emission_O2+emission_CO2; 0.687, 0.854, tmp+AN_cumulo+interval_yield+RS+Feed_ Vol+mu_cumulo+Sugar_consuming_rate_cumulo+RQ_in- tegral+AS_Vol.+generate_CO2; 0.666, 0.854, tmp+PL+ AN_cumulo+interval_yield+interval_Pdt.+RS+Feed_Vol+ mu_cumulo+Sugar_consuming_rate_cumulo+rab_integral+ AS_Vol.+emission_O2+emission_CO2+generate_CO2; 0.677, 0.854, tmp+OD+RS+Feed_Vol+mu_cumulo+nu_cu- mulo+Sugar_consuming_rate_cumulo+RQ_integral+AS_ Vol.+emission_O2+emission_CO2+generate_CO2; 0.671, 0.854, tmp+PL+AN_cumulo+RS+Feed_Vol+mu_cumulo+ nu_cumulo+Sugar_consuming_rate_cumulo+RQ_integral+ AS_Vol.+emission_O2+emission_CO2+generate_CO2; 0.666, 0.854, tmp+AN_cumulo+interval_yield+interval_ Pdt.+OD+RS+Feed_Vol+mu_cumulo+nu_per_rho_cu- mulo+Sugar_consuming_rate_cumulo+rab_integral+AS_ Vol.+emission_O2+emission_CO2; 0.682, 0.854, tmp+AN_ cumulo+interval_yield+interval_Pdt.+OD+RS+Feed_Vol+ mu_cumulo+Sugar_consuming_rate_cumulo+AS_Vol.+ consum_O2; 0.682, 0.854, tmp+AN_cumulo+interval_Pdt.+ OD+RS+Feed_Vol+mu_cumulo+Sugar_consuming_rate_ cumulo+RQ_integral+AS_Vol.+generate_CO2; 0.692, 0.854, tmp+AN_cumulo+RS+Feed_Vol+mu_cumulo+nu_ cumulo+Sugar_consuming_rate_cumulo+RQ_integral+ AS_Vol.; 0.671, 0.854, tmp+interval_yield+interval_Pdt.+ RS+Feed_Vol+mu_cumulo+nu_per_rho_cumulo+Sugar_ consuming_rate_cumulo+rab_integral+AS_Vol.+emission_ O2+emission_CO2+generate_CO2; 0.671, 0.854, tmp+PL+ interval_yield+RS+Feed_Vol+mu_cumulo+rho_cumulo+ nu_per_rho_cumulo+Sugar_consuming_rate_cumulo+RQ_ integral+AS_Vol.+emission_O2+emission_CO2; 0.671, 0.854, tmp+AN+interval_Pdt.+RS+Feed_Vol+mu_cumulo+ rho_cumulo+Sugar_consuming_rate_cumulo+rab_inte- gral+AS_Vol.+emission_O2+emission_CO2+generate_ CO2; 0.682, 0.854, tmp+AN+AN_cumulo+interval_yield+ RS+Feed_Vol+mu_cumulo+nu_per_rho_cumulo+Sugar_ consuming_rate_cumulo+rab_integral+AS_Vol; 0.671, 0.854, tmp+PL+AN+RS+Feed_Vol+mu_cumulo+nu_per_ rho_cumulo+Sugar_consuming_rate_cumulo+RQ_inte- gral+AS_Vol.+emission_O2+emission_CO2+generate_ CO2; 0.671, 0.854, tmp+AN+interval_Pdt.+RS+Feed_Vol+ mu_cumulo+rho_cumulo+nu_per_rho_cumulo+Sugar_ consuming_rate_cumulo+rab_integral+AS_Vol.+emission_ O2+emission_CO2; 0.671, 0.854, tmp+PL+AN_cumulo+ interval_Pdt.+RS+Feed_Vol+mu_cumulo+nu_per_rho_ cumulo+Sugar_consuming_rate_cumulo+rab_integral+ RQ_integral+AS_Vol.+emission_O2; 0.676, 0.854, tmp+ AN+interval_yield+RS+Feed_Vol+mu_cumulo+Sugar_ consuming_rate_cumulo+RQ_integral+AS_Vol.+emission_ O2+emission_CO2+generate_CO2; 0.660, 0.854, tmp+PL+ AN+interval_yield+interval_Pdt.+OD+RS+Feed_Vol+mu_ cumulo+rho_cumulo+Sugar_consuming_rate_cumulo+ RQ_integral+AS_Vol.+emission_O2+emission_CO2; 0.687, 0.854, tmp+AN_cumulo+interval_yield+RS+Feed_ Vol+mu_cumulo+nu_per_rho_cumulo+Sugar_consuming_ rate_cumulo+AS_Vol.+generate_CO2; 0.671, 0.854, tmp+ AN+interval_yield+interval_Pdt.+OD+RS+Feed_Vol+mu_ cumulo+Sugar_consuming_rate_cumulo+rab_integral+AS_ Vol.+emission_O2+emission_CO2; 0.692, 0.854, tmp+ interval_Pdt.+RS+Feed_Vol+mu_cumulo+Sugar_ consuming_rate_cumulo+rab_integral+AS_Vol.+generate_ CO2; 0.687, 0.854, tmp+PL+RS+Feed_Vol+mu_cumulo+ Sugar_consuming_rate_cumulo+RQ_integral+AS_Vol.+ emission_CO2+generate_CO2; 0.687, 0.854, tmp+pH+ interval_Pdt.+OD+RS+Feed_Vol+mu_cumulo+rho_ cumulo+Sugar_consuming_rate_cumulo+AS_Vol.; 0.682, 0.854, tmp+AN+AN_cumulo+RS+Feed_Vol+mu_cumulo+ Sugar_consuming_rate_cumulo+rab_integral+AS_Vol.+ emission_CO2+generate_CO2; 0.687, 0.854, tmp+AN+

AN_cumulo+interval_Pdt.+RS+Feed_Vol+mu_cumulo+Sugar_consuming_rate_cumulo+AS_Vol.+generate_CO2; 0.671, 0.854, tmp+AN+AN_cumulo+interval_yield+interval_Pdt.+RS+Feed_Vol+mu_cumulo+Sugar_consuming_rate_cumulo+rab_integral+AS_Vol.+emission_O2+emission_CO2; 0.671, 0.854, tmp+pH+interval_Pdt.+RS+Feed_Vol+mu_cumulo+nu_per_rho_cumulo+Sugar_consuming_rate_cumulo+RQ_integral+AS_Vol.+emission_O2+emission_CO2+generate_CO2; 0.671, 0.854, tmp+interval_yield+interval_Pdt.+RS+Feed_Vol+mu_cumulo+rho_cumulo+Sugar_consuming_rate_cumulo+rab_integral+AS_Vol.+emission_O2+emission_CO2+generate_CO2; 0.676, 0.854, tmp+AN_cumulo+interval_yield+interval_Pdt.+RS+Feed_Vol+mu_cumulo+nu_per_rho_cumulo+Sugar_consuming_rate_cumulo+rab_integral+AS_Vol.+generate_CO2; 0.671, 0.854, tmp+PL+RS+Feed_Vol+mu_cumulo+nu_cumulo+nu_per_rho_cumulo+Sugar_consuming_rate_cumulo+RQ_integral+AS_Vol.+emission_O2+emission_CO2+generate_CO2; 0.682, 0.854, tmp+PL+AN_cumulo+interval_yield+RS+Feed_Vol+mu_cumulo+nu_per_rho_cumulo+Sugar_consuming_rate_cumulo+rab_integral+AS_Vol.; 0.682, 0.854, tmp+interval_Pdt.+OD+RS+Feed_Vol+mu_cumulo+rho_cumulo+Sugar_consuming_rate_cumulo+rab_integral+AS_Vol.+emission_CO2; 0.687, 0.854, tmp+interval_Pdt.+RS+Feed_Vol+mu_cumulo+rho_cumulo+nu_per_rho_cumulo+Sugar_consuming_rate_cumulo+rab_integral+AS_Vol.; 0.671, 0.854, tmp+PL+RS+Feed_Vol+mu_cumulo+nu_cumulo+rho_cumulo+Sugar_consuming_rate_cumulo+RQ_integral+AS_Vol.+emission_O2+emission_CO2+generate_CO2; 0.692, 0.854, tmp+AN+AN_cumulo+interval_Pdt.+RS+Feed_Vol+mu_cumulo+Sugar_consuming_rate_cumulo+rab_integral; 0.682, 0.854, tmp+AN+interval_yield+interval_Pdt.+RS+Feed_Vol+mu_cumulo+Sugar_consuming_rate_cumulo+rab_integral+AS_Vol.+emission_CO2; 0.682, 0.854, tmp+AN+interval_Pdt.+RS+Feed_Vol+mu_cumulo+rho_cumulo+Sugar_consuming_rate_cumulo+AS_Vol.+emission_CO2+generate_CO2; 0.687, 0.854, tmp+PL+AN_cumulo+interval_Pdt.+RS+Feed_Vol+mu_cumulo+nu_per_rho_cumulo+Sugar_consuming_rate_cumulo+AS_Vol.; 0.676, 0.854, tmp+PL+AN+AN_cumulo+interval_yield+interval_Pdt.+RS+Feed_Vol+mu_cumulo+Sugar_consuming_rate_cumulo+rab_integral+emission_O2; 0.676, 0.854, tmp+PL+AN_cumulo+interval_yield+interval_Pdt.+RS+Feed_Vol+mu_cumulo+Sugar_consuming_rate_cumulo+RQ_integral+AS_Vol.+emission_O2; 0.687, 0.854, tmp+AN+AN_cumulo+interval_yield+RS+Feed_Vol+mu_cumulo+Sugar_consuming_rate_cumulo+RQ_integral+AS_Vol.; 0.671, 0.854, tmp+AN+RS+Feed_Vol+mu_cumulo+rho_cumulo+nu_per_rho_cumulo+Sugar_consuming_rate_cumulo+RQ_integral+AS_Vol.+emission_O2+emission_CO2+generate_CO2; 0.665, 0.854, tmp+PL+AN_cumulo+interval_yield+interval_Pdt.+OD+RS+Feed_Vol+mu_cumulo+rho_cumulo+Sugar_consuming_rate_cumulo+RQ_integral+AS_Vol.+emission_O2; 0.682, 0.854, tmp+AN+interval_Pdt.+RS+Feed_Vol+mu_cumulo+Sugar_consuming_rate_cumulo+AS_Vol.+emission_O2+emission_CO2+generate_CO2; 0.682, 0.854, tmp+PL+AN_cumulo+interval_Pdt.+RS+Feed_Vol+mu_cumulo+Sugar_consuming_rate_cumulo+rab_integral+AS_Vol.+emission_CO2; 0.682, 0.854, tmp+pH+AN_cumulo+interval_Pdt.+RS+Feed_Vol+mu_cumulo+Sugar_consuming_rate_cumulo+rab_integral+AS_Vol.+emission_O2; 0.687, 0.854, tmp+interval_Pdt.+OD+RS+Feed_Vol+mu_cumulo+nu_per_rho_cumulo+Sugar_consuming_rate_cumulo+rab_integral+AS_Vol.; 0.696, 0.854, tmp+interval_Pdt.+RS+Feed_Vol+mu_cumulo+Sugar_consuming_rate_cumulo+AS_Vol.+emission_CO2; 0.687, 0.854, tmp+AN_cumulo+interval_Pdt.+RS+Feed_Vol+mu_cumulo+Sugar_consuming_rate_cumulo+rab_integral+emission_O2+generate_CO2; 0.681, 0.854, tmp+PL+RS+Feed_Vol+mu_cumulo+Sugar_consuming_rate_cumulo+rab_integral+RQ_integral+AS_Vol.+emission_O2+emission_CO2; 0.671, 0.854, tmp+pH+AN_cumulo+interval_yield+interval_Pdt.+RS+Feed_Vol+mu_cumulo+Sugar_consuming_rate_cumulo+rab_integral+AS_Vol.+emission_O2+emission_CO2; 0.691, 0.854, tmp+RS+Feed_Vol+mu_cumulo+Sugar_consuming_rate_cumulo+RQ_integral+AS_Vol.+emission_CO2+consum_O2; 0.665, 0.854, tmp+PL+AN_cumulo+interval_yield+interval_Pdt.+OD+RS+Feed_Vol+mu_cumulo+Sugar_consuming_rate_cumulo+RQ_integral+AS_Vol.+emission_O2+emission_CO2; 0.681, 0.854, tmp+AN_cumulo+RS+Feed_Vol+mu_cumulo+nu_cumulo+Sugar_consuming_rate_cumulo+RQ_integral+AS_Vol.+emission_O2+emission_CO2; 0.681, 0.854, tmp+AN_cumulo+interval_yield+RS+Feed_Vol+mu_cumulo+nu_per_rho_cumulo+Sugar_consuming_rate_cumulo+rab_integral+AS_Vol.+generate_CO2; 0.676, 0.854, tmp+AN_cumulo+interval_yield+interval_Pdt.+OD+RS+Feed_Vol+mu_cumulo+Sugar_consuming_rate_cumulo+RQ_integral+AS_Vol.+consum_O2; 0.665, 0.854, tmp+PL+AN_cumulo+interval_yield+interval_Pdt.+OD+RS+Feed_Vol+mu_cumulo+Sugar_consuming_rate_cumulo+rab_integral+AS_Vol.+emission_O2+emission_CO2; 0.687, 0.854, tmp+PL+AN+AN_cumulo+RS+Feed_Vol+mu_cumulo+Sugar_consuming_rate_cumulo+rab_integral+AS_Vol.; 0.681, 0.854, tmp+pH+AN_cumulo+interval_Pdt.+RS+Feed_Vol+mu_cumulo+nu_per_rho_cumulo+Sugar_consuming_rate_cumulo+rab_integral+AS_Vol.; 0.687, 0.854, tmp+RS+Feed_Vol+mu_cumulo+nu_cumulo+Sugar_consuming_rate_cumulo+RQ_integral+AS_Vol.+emission_O2+emission_CO2; 0.676, 0.854, tmp+AN+AN_cumulo+RS+Feed_Vol+mu_cumulo+rho_cumulo+Sugar_consuming_rate_cumulo+RQ_integral+AS_Vol.+emission_CO2+generate_CO2; 0.676, 0.854, tmp+pH+interval_Pdt.+RS+Feed_Vol+mu_cumulo+nu_per_rho_cumulo+Sugar_consuming_rate_cumulo+rab_integral+AS_Vol.+emission_O2+emission_CO2; 0.671, 0.854, tmp+AN+interval_Pdt.+RS+Feed_Vol+mu_cumulo+nu_per_rho_cumulo+Sugar_consuming_rate_cumulo+rab_integral+AS_Vol.+emission_O2+emission_CO2+generate_CO2; 0.671, 0.854, tmp+AN+interval_Pdt.+OD+RS+Feed_Vol+mu_cumulo+rho_cumulo+Sugar_consuming_rate_cumulo+RQ_integral+AS_Vol.+emission_O2+emission_CO2; 0.681, 0.854, tmp+AN_cumulo+interval_Pdt.+RS+Feed_Vol+mu_cumulo+nu_per_rho_cumulo+Sugar_consuming_rate_cumulo+RQ_integral+AS_Vol.+generate_CO2; 0.665, 0.854, tmp+pH+PL+AN+interval_Pdt.+RS+Feed_Vol+mu_cumulo+nu_per_rho_cumulo+Sugar_consuming_rate_cumulo+RQ_integral+AS_Vol.+emission_O2+emission_CO2; 0.676, 0.854, tmp+AN_cumulo+interval_yield+interval_Pdt.+RS+Feed_Vol+mu_cumulo+nu_per_rho_cumulo+Sugar_consuming_rate_cumulo+rab_integral+AS_Vol.+emission_CO2; 0.665, 0.854, tmp+PL+interval_Pdt.+OD+RS+Feed_Vol+mu_cumulo+nu_per_rho_cumulo+Sugar_consuming_rate_cumulo+RQ_integral+AS_Vol.+emission_O2+emission_CO2; 0.671, 0.854, tmp+PL+AN+OD+RS+Feed_Vol+mu_cumulo+rho_cumulo+Sugar_consuming_rate_cumulo+RQ_integral+AS_Vol.+emission_O2+emission_CO2; 0.691, 0.854, tmp+AN+interval_Pdt.+OD+RS+Feed_Vol+mu_cumulo+Sugar_consuming_rate_cumulo+AS_Vol.; 0.676, 0.854, tmp+PL+interval_yield+RS+Feed_Vol+mu_cumulo+Sugar_consuming_rate_cumulo+RQ_integral+AS_Vol.+emission_O2+emission_CO2+generate_

CO2; 0.681, 0.854, tmp+interval_Pdt.+RS+Feed_Vol+mu_cumulo+nu_per_rho_cumulo+Sugar_consuming_rate_cumulo+RQ_integral+AS_Vol.+emission_CO2+generate_CO2; 0.671, 0.854, tmp+AN_cumulo+interval_Pdt.+RS+Feed_Vol+mu_cumulo+rho_cumulo+Sugar_consuming_rate_cumulo+rab_integral+AS_Vol.+emission_O2+emission_CO2+generate_CO2; 0.686, 0.854, tmp+PL+AN+interval_Pdt.+RS+Feed_Vol+mu_cumulo+nu_per_rho_cumulo+Sugar_consuming_rate_cumulo+AS_Vol.; 0.671, 0.854, tmp+AN+AN_cumulo+OD+RS+Feed_Vol+mu_cumulo+Sugar_consuming_rate_cumulo+RQ_integral+AS_Vol.+emission_O2+emission_CO2+generate_CO2; 0.681, 0.854, tmp+AN+interval_yield+interval_Pdt.+RS+Feed_Vol+mu_cumulo+Sugar_consuming_rate_cumulo+rab_integral+emission_O2+emission_CO2; 0.681, 0.854, tmp+AN+AN_cumulo+interval_Pdt.+RS+Feed_Vol+mu_cumulo+Sugar_consuming_rate_cumulo+rab_integral+RQ_integral+AS_Vol.; 0.681, 0.854, tmp+AN+RS+Feed_Vol+mu_cumulo+rho_cumulo+Sugar_consuming_rate_cumulo+RQ_integral+AS_Vol.+emission_CO2+generate_CO2; 0.681, 0.854, tmp+AN_cumulo+interval_Pdt.+OD+RS+Feed_Vol+mu_cumulo+nu_per_rho_cumulo+Sugar_consuming_rate_cumulo+rab_integral+AS_Vol.; 0.671, 0.854, tmp+AN_cumulo+interval_Pdt.+RS+Feed_Vol+mu_cumulo+nu_cumulo+nu_per_rho_cumulo+Sugar_consuming_rate_cumulo+rab_integral+AS_Vol.+emission_O2+emission_CO2; 0.681, 0.854, tmp+AN+interval_yield+interval_Pdt.+OD+RS+Feed_Vol+mu_cumulo+Sugar_consuming_rate_cumulo+AS_Vol.+consum_O2; 0.676, 0.854, tmp+AN+interval_Pdt.+OD+RS+Feed_Vol+mu_cumulo+rho_cumulo+Sugar_consuming_rate_cumulo+rab_integral+AS_Vol.+consum_O2; 0.676, 0.854, tmp+RS+Feed_Vol+mu_cumulo+nu_per_rho_cumulo+Sugar_consuming_rate_cumulo+rab_integral+RQ_integral+AS_Vol.+emission_O2+emission_CO2+generate_CO2; 0.671, 0.854, tmp+PL+AN+interval_Pdt.+OD+RS+Feed_Vol+mu_cumulo+rho_cumulo+Sugar_consuming_rate_cumulo+RQ_integral+emission_O2+emission_CO2; 0.681, 0.854, tmp+AN_cumulo+interval_Pdt.+RS+Feed_Vol+mu_cumulo+nu_per_rho_cumulo+Sugar_consuming_rate_cumulo+RQ_integral+AS_Vol.+emission_O2; 0.671, 0.854, tmp+AN_cumulo+interval_yield+interval_Pdt.+OD+RS+Feed_Vol+mu_cumulo+Sugar_consuming_rate_cumulo+RQ_integral+AS_Vol.+emission_O2+emission_CO2; 0.691, 0.854, tmp+AN+interval_Pdt.+RS+Feed_Vol+mu_cumulo+rho_cumulo+Sugar_consuming_rate_cumulo+rab_integral; 0.676, 0.854, tmp+AN_cumulo+interval_Pdt.+RS+Feed_Vol+mu_cumulo+nu_cumulo+rho_cumulo+Sugar_consuming_rate_cumulo+rab_integral+AS_Vol.+emission_O2; 0.671, 0.854, tmp+PL+interval_Pdt.+OD+RS+Feed_Vol+mu_cumulo+Sugar_consuming_rate_cumulo+RQ_integral+AS_Vol.+emission_O2+emission_CO2+generate_CO2; 0.659, 0.854, tmp+PL+AN_cumulo+interval_yield+interval_Pdt.+RS+Feed_Vol+mu_cumulo+nu_per_rho_cumulo+Sugar_consuming_rate_cumulo+RQ_integral+AS_Vol.+emission_O2+emission_CO2+generate_CO2; 0.686, 0.854, tmp+RS+Feed_Vol+mu_cumulo+rho_cumulo+nu_per_rho_cumulo+Sugar_consuming_rate_cumulo+rab_integral+AS_Vol.+emission_CO2; 0.671, 0.854, tmp+AN+interval_Pdt.+RS+Feed_Vol+mu_cumulo+rho_cumulo+Sugar_consuming_rate_cumulo+rab_integral+RQ_integral+AS_Vol.+emission_O2+emission_CO2; 0.686, 0.854, tmp+pH+interval_Pdt.+RS+Feed_Vol+mu_cumulo+Sugar_consuming_rate_cumulo+AS_Vol.+emission_CO2+generate_CO2; 0.681, 0.854, tmp+PL+AN_cumulo+RS+Feed_Vol+mu_cumulo+nu_per_rho_cumulo+Sugar_consuming_rate_cumulo+RQ_integral+AS_Vol.+emission_CO2; 0.681, 0.854, tmp+interval_Pdt.+RS+Feed_Vol+mu_cumulo+nu_cumulo+Sugar_consuming_rate_cumulo+rab_integral+AS_Vol.+emission_O2+emission_CO2; 0.691, 0.854, tmp+RS+Feed_Vol+mu_cumulo+Sugar_consuming_rate_cumulo+rab_integral+AS_Vol.+emission_CO2+consum_O2; 0.659, 0.854, tmp+pH+PL+AN+interval_Pdt.+OD+RS+Feed_Vol+mu_cumulo+rho_cumulo+Sugar_consuming_rate_cumulo+RQ_integral+AS_Vol.+emission_O2+emission_CO2; 0.676, 0.854, tmp+PL+AN_cumulo+RS+Feed_Vol+mu_cumulo+nu_per_rho_cumulo+Sugar_consuming_rate_cumulo+RQ_integral+AS_Vol.+emission_CO2+generate_CO2; 0.676, 0.854, tmp+AN+AN_cumulo+interval_Pdt.+RS+Feed_Vol+mu_cumulo+Sugar_consuming_rate_cumulo+rab_integral+RQ_integral+AS_Vol.+emission_O2; 0.691, 0.854, tmp+AN+interval_yield+RS+Feed_Vol+mu_cumulo+nu_per_rho_cumulo+Sugar_consuming_rate_cumulo+AS_Vol.; 0.676, 0.854, tmp+AN_cumulo+interval_Pdt.+OD+RS+Feed_Vol+mu_cumulo+rho_cumulo+Sugar_consuming_rate_cumulo+RQ_integral+AS_Vol.+generate_CO2; 0.665, 0.854, tmp+pH+PL+interval_Pdt.+RS+Feed_Vol+mu_cumulo+nu_per_rho_cumulo+Sugar_consuming_rate_cumulo+RQ_integral+AS_Vol.+emission_O2+emission_CO2+generate_CO2; 0.681, 0.854, tmp+AN_cumulo+interval_Pdt.+RS+Feed_Vol+mu_cumulo+rho_cumulo+Sugar_consuming_rate_cumulo+AS_Vol.+emission_CO2+generate_CO2; 0.686, 0.854, tmp+AN+AN_cumulo+RS+Feed_Vol+mu_cumulo+rho_cumulo+Sugar_consuming_rate_cumulo+rab_integral+AS_Vol.; 0.676, 0.854, tmp+AN+interval_yield+interval_Pdt.+OD+RS+Feed_Vol+mu_cumulo+rho_cumulo+Sugar_consuming_rate_cumulo+AS_Vol.+consum_O2; 0.665, 0.854, tmp+PL+interval_yield+interval_Pdt.+RS+Feed_Vol+mu_cumulo+nu_per_rho_cumulo+Sugar_consuming_rate_cumulo+rab_integral+RQ_integral+AS_Vol.+emission_O2+emission_CO2; 0.700, 0.854, tmp+AN+interval_Pdt.+RS+Feed_Vol+mu_cumulo+Sugar_consuming_rate_cumulo; 0.686, 0.854, tmp+interval_yield+RS+Feed_Vol+mu_cumulo+Sugar_consuming_rate_cumulo+RQ_integral+AS_Vol.+emission_CO2+generate_CO2; 0.670, 0.854, tmp+PL+AN+AN_cumulo+interval_Pdt.+RS+Feed_Vol+mu_cumulo+nu_per_rho_cumulo+Sugar_consuming_rate_cumulo+rab_integral+AS_Vol.+emission_O2; 0.670, 0.854, tmp+PL+AN_cumulo+interval_yield+interval_Pdt.+RS+Feed_Vol+mu_cumulo+rho_cumulo+Sugar_consuming_rate_cumulo+rab_integral+AS_Vol.+emission_O2; 0.681, 0.854, tmp+AN_cumulo+interval_Pdt.+RS+Feed_Vol+mu_cumulo+rho_cumulo+Sugar_consuming_rate_cumulo+rab_integral+RQ_integral+AS_Vol.; 0.681, 0.854, tmp+PL+AN+AN_cumulo+interval_Pdt.+RS+Feed_Vol+mu_cumulo+Sugar_consuming_rate_cumulo+RQ_integral+emission_O2; 0.681, 0.854, tmp+AN+AN_cumulo+RS+Feed_Vol+mu_cumulo+Sugar_consuming_rate_cumulo+RQ_integral+AS_Vol.+emission_O2+emission_CO2; 0.681, 0.854, tmp+pH+interval_Pdt.+OD+RS+Feed_Vol+mu_cumulo+rho_cumulo+Sugar_consuming_rate_cumulo+rab_integral+AS_Vol.; 0.665, 0.854, tmp+PL+AN_cumulo+interval_Pdt.+RS+Feed_Vol+mu_cumulo+rho_cumulo+nu_per_rho_cumulo+Sugar_consuming_rate_cumulo+RQ_integral+AS_Vol.+emission_O2+emission_CO2; 0.681, 0.854, tmp+AN+interval_Pdt.+OD+RS+Feed_Vol+mu_cumulo+rho_cumulo+Sugar_consuming_rate_cumulo+AS_Vol.+generate_CO2; 0.691, 0.854, tmp+interval_Pdt.+RS+Feed_Vol+mu_cumulo+Sugar_consuming_rate_cumulo+rab_integral+RQ_integral+AS_Vol.; 0.686, 0.854, tmp+interval_Pdt.+OD+RS+Feed_Vol+mu_cumulo+rho_cumulo+nu_per_rho_cumulo+Sugar_consuming_rate_ cumulo+AS_Vol.; 0.670, 0.854, tmp+AN+OD+RS+Feed_Vol+mu_cumulo+rho_cumulo+Sugar_consuming_rate_cumulo+RQ_integral+AS_Vol.+emission_O2+emission_CO2+generate_CO2; 0.670, 0.854, tmp+AN+interval_Pdt.+RS+Feed_Vol+mu_cumulo+nu_per_rho_cumulo+Sugar_consuming_rate_cumulo+rab_integral+AS_Vol.+emission_O2+emission_CO2; 0.665, 0.854, tmp+PL+interval_Pdt.+RS+Feed_Vol+mu_cumulo+rho_cumulo+Sugar_consuming_rate_cumulo+rab_integral+RQ_integral+AS_Vol.+emission_O2+emission_CO2+generate_CO2; 0.686, 0.854, tmp+interval_yield+RS+Feed_Vol+mu_cumulo+Sugar_consuming_rate_cumulo+rab_integral+AS_Vol.+emission_CO2+generate_CO2; 0.681, 0.854, tmp+PL+AN_cumulo+RS+Feed_Vol+mu_cumulo+nu_per_rho_cumulo+Sugar_consuming_rate_cumulo+rab_integral+AS_Vol.+emission_CO2; 0.681, 0.854, tmp+interval_Pdt.+RS+Feed_Vol+mu_cumulo+rho_cumulo+Sugar_consuming_rate_cumulo+rab_integral+AS_Vol.+emission_CO2+generate_CO2; 0.670, 0.854, tmp+RS+Feed_Vol+mu_cumulo+nu_cumulo+rho_cumulo+nu_per_rho_cumulo+Sugar_consuming_rate_cumulo+RQ_integral+AS_Vol.+emission_O2+emission_CO2+generate_CO2; 0.681, 0.854, tmp+AN_cumulo+interval_yield+interval_Pdt.+RS+Feed_Vol+mu_cumulo+Sugar_consuming_rate_cumulo+AS_Vol.+emission_CO2+generate_CO2; 0.681, 0.854, tmp+AN+AN_cumulo+RS+Feed_Vol+mu_cumulo+nu_per_rho_cumulo+Sugar_consuming_rate_cumulo+rab_integral+AS_Vol.+emission_CO2; 0.676, 0.854, tmp+PL+AN_cumulo+RS+Feed_Vol+mu_cumulo+Sugar_consuming_rate_cumulo+rab_integral+RQ_integral+AS_Vol.+emission_O2+emission_CO2; 0.676, 0.854, tmp+AN+AN_cumulo+interval_yield+interval_Pdt.+RS+Feed_Vol+mu_cumulo+nu_per_rho_cumulo+Sugar_consuming_rate_cumulo+rab_integral+AS_Vol.; 0.681, 0.854, tmp+RS+Feed_Vol+mu_cumulo+rho_cumulo+nu_per_rho_cumulo+Sugar_consuming_rate_cumulo+RQ_integral+AS_Vol.+emission_O2+emission_CO2; 0.676, 0.854, tmp+interval_yield+interval_Pdt.+RS+Feed_Vol+mu_cumulo+nu_cumulo+Sugar_consuming_rate_cumulo+rab_integral+AS_Vol.+emission_O2+emission_CO2; 0.681, 0.854, tmp+AN+AN_cumulo+RS+Feed_Vol+mu_cumulo+nu_per_rho_cumulo+Sugar_consuming_rate_cumulo+RQ_integral+AS_Vol.+emission_CO2; 0.691, 0.854, tmp+AN+interval_Pdt.+RS+Feed_Vol+mu_cumulo+nu_per_rho_cumulo+Sugar_consuming_rate_cumulo+rab_integral; 0.686, 0.854, tmp+OD+RS+Feed_Vol+mu_cumulo+Sugar_consuming_rate_cumulo+RQ_integral+AS_Vol.+emission_CO2+consum_O2; 0.670, 0.854, tmp+PL+interval_yield+interval_Pdt.+RS+Feed_Vol+mu_cumulo+rho_cumulo+Sugar_consuming_rate_cumulo+rab_integral+AS_Vol.+emission_O2+emission_CO2; 0.670, 0.854, tmp+interval_Pdt.+OD+RS+Feed_Vol+mu_cumulo+rho_cumulo+Sugar_consuming_rate_cumulo+rab_integral+AS_Vol.+emission_O2+emission_CO2+generate_CO2; 0.676, 0.854, tmp+PL+AN+AN_cumulo+interval_Pdt.+RS+Feed_Vol+mu_cumulo+nu_per_rho_cumulo+Sugar_consuming_rate_cumulo+rab_integral+AS_Vol.; 0.686, 0.854, tmp+AN+interval_Pdt.+RS+Feed_Vol+mu_cumulo+nu_cumulo+Sugar_consuming_rate_cumulo+rab_integral+AS_Vol.; 0.670, 0.854, tmp+AN+interval_yield+RS+Feed_Vol+mu_cumulo+nu_per_rho_cumulo+Sugar_consuming_rate_cumulo+RQ_integral+AS_Vol.+emission_O2+emission_CO2+generate_CO2; 0.691, 0.854, tmp+interval_Pdt.+RS+Feed_Vol+mu_cumulo+nu_per_rho_cumulo+Sugar_consuming_rate_cumulo+AS_Vol.+emission_CO2; 0.659, 0.854, tmp+PL+AN_cumulo+interval_yield+interval_Pdt.+OD+RS+Feed_Vol+mu_cumulo+Sugar_consuming_rate_cumulo+RQ_integral+AS_Vol.+emission_O2+emission_CO2+generate_CO2; 0.670, 0.854, tmp+AN_cumulo+interval_Pdt.+OD+RS+Feed_Vol+mu_cumulo+nu_per_rho_cumulo+Sugar_consuming_rate_cumulo+rab_integral+AS_Vol.+emission_O2+emission_CO2; 0.665, 0.854, tmp+AN_cumulo+interval_yield+interval_Pdt.+OD+RS+Feed_Vol+mu_cumulo+nu_cumulo+Sugar_consuming_rate_cumulo+rab_integral+AS_Vol.+emission_O2+emission_CO2; 0.686, 0.854, tmp+interval_Pdt.+RS+Feed_Vol+mu_cumulo+nu_cumulo+nu_per_rho_cumulo+Sugar_consuming_rate_cumulo+rab_integral+AS_Vol.; 0.686, 0.854, tmp+AN_cumulo+interval_yield+RS+Feed_Vol+mu_cumulo+nu_cumulo+Sugar_consuming_rate_cumulo+rab_integral+AS_Vol.; 0.681, 0.854, tmp+PL+AN+interval_Pdt.+RS+Feed_Vol+mu_cumulo+nu_per_rho_cumulo+Sugar_consuming_rate_cumulo+rab_integral+AS_Vol.; 0.670, 0.854, tmp+AN_cumulo+interval_yield+interval_Pdt.+RS+Feed_Vol+mu_cumulo+Sugar_consuming_rate_cumulo+rab_integral+RQ_integral+AS_Vol.+emission_O2+emission_CO2; 0.681, 0.854, tmp+AN+interval_Pdt.+OD+RS+Feed_Vol+mu_cumulo+rho_cumulo+Sugar_consuming_rate_cumulo+RQ_integral+AS_Vol.; 0.686, 0.854, tmp+AN_cumulo+RS+Feed_Vol+mu_cumulo+rho_cumulo+Sugar_consuming_rate_cumulo+rab_integral+RQ_integral+AS_Vol.; 0.681, 0.854, tmp+PL+interval_Pdt.+RS+Feed_Vol+mu_cumulo+nu_per_rho_cumulo+RQ_integral+AS_Vol.+emission_O2+emission_CO2; 0.686, 0.854, tmp+AN_cumulo+RS+Feed_Vol+mu_cumulo+rho_cumulo+nu_per_rho_cumulo+Sugar_consuming_rate_cumulo+rab_integral+AS_Vol.; 0.676, 0.854, tmp+interval_yield+interval_Pdt.+OD+RS+Feed_Vol+mu_cumulo+rho_cumulo+Sugar_consuming_rate_cumulo+rab_integral+AS_Vol.+consum_O2; 0.686, 0.854, tmp+pH+interval_Pdt.+RS+Feed_Vol+mu_cumulo+nu_per_rho_cumulo+Sugar_consuming_rate_cumulo+rab_integral+AS_Vol.; 0.686, 0.854, tmp+RS+Feed_Vol+mu_cumulo+rho_cumulo+nu_per_rho_cumulo+Sugar_consuming_rate_cumulo+AS_Vol.+emission_CO2+generate_CO2; 0.670, 0.854, tmp+AN+AN_cumulo+interval_Pdt.+OD+RS+Feed_Vol+mu_cumulo+nu_per_rho_cumulo+Sugar_consuming_rate_cumulo+RQ_integral+AS_Vol.+emission_O2; 0.670, 0.854, tmp+pH+AN_cumulo+interval_yield+interval_Pdt.+OD+RS+Feed_Vol+mu_cumulo+Sugar_consuming_rate_cumulo+rab_integral+AS_Vol.+emission_O2; 0.691, 0.854, tmp+AN_cumulo+interval_Pdt.+RS+Feed_Vol+mu_cumulo+Sugar_consuming_rate_cumulo+AS_Vol.+emission_CO2; 0.686, 0.854, tmp+interval_Pdt.+OD+RS+Feed_Vol+mu_cumulo+nu_cumulo+rho_cumulo+Sugar_consuming_rate_cumulo+AS_Vol.; 0.681, 0.854, tmp+pH+AN_cumulo+interval_yield+interval_Pdt.+RS+Feed_Vol+mu_cumulo+Sugar_consuming_rate_cumulo+rab_integral+AS_Vol.; 0.681, 0.854, tmp+AN_cumulo+interval_Pdt.+OD+RS+Feed_Vol+mu_cumulo+Sugar_consuming_rate_cumulo+RQ_integral+AS_Vol.+consum_O2; 0.686, 0.854, tmp+pH+AN_cumulo+interval_Pdt.+RS+Feed_Vol+mu_cumulo+Sugar_consuming_rate_cumulo+AS_Vol.+generate_CO2; 0.681, 0.854, tmp+AN_cumulo+interval_yield+interval_Pdt.+OD+RS+Feed_Vol+mu_cumulo+Sugar_consuming_rate_cumulo+RQ_integral+emission_O2; 0.681, 0.854, tmp+AN_cumulo+interval_Pdt.+RS+Feed_Vol+mu_cumulo+Sugar_consuming_rate_cumulo+rab_integral+RQ_integral+AS_Vol.+generate_CO2; 0.681, 0.854, tmp+PL+interval_yield+RS+Feed_Vol+mu_cumulo+Sugar_consuming_rate_cumulo+RQ_integral+AS_Vol.+emission_O2+emission_CO2; 0.681, 0.854, tmp+OD+RS+Feed_Vol+mu_cumulo+nu_per_rho_cumulo+Sugar_consuming_rate_ cumulo+RQ_integral+AS_Vol.+emission_O2+emission_CO2; 0.681, 0.854, tmp+AN+interval_yield+interval_Pdt.+RS+Feed_Vol+mu_cumulo+Sugar_consuming_rate_cumulo+AS_Vol.+emission_CO2+generate_CO2; 0.681, 0.854, tmp+AN_cumulo+interval_Pdt.+OD+RS+Feed_Vol+mu_cumulo+nu_per_rho_cumulo+Sugar_consuming_rate_cumulo+RQ_integral+emission_O2; 0.691, 0.854, tmp+AN+interval_yield+RS+Feed_Vol+mu_cumulo+Sugar_consuming_rate_cumulo+rab_integral+AS_Vol.; 0.681, 0.854, tmp+AN_cumulo+OD+RS+Feed_Vol+mu_cumulo+Sugar_consuming_rate_cumulo+RQ_integral+AS_Vol.+emission_CO2+generate_CO2; 0.664, 0.854, tmp+PL+interval_Pdt.+OD+RS+Feed_Vol+mu_cumulo+nu_cumulo+rho_cumulo+Sugar_consuming_rate_cumulo+RQ_integral+AS_Vol.+emission_O2+emission_CO2; 0.664, 0.854, tmp+AN_cumulo+interval_yield+interval_Pdt.+RS+Feed_Vol+mu_cumulo+nu_per_rho_cumulo+Sugar_consuming_rate_cumulo+RQ_integral+AS_Vol.+emission_O2+emission_CO2+generate_CO2; 0.691, 0.854, tmp+interval_Pdt.+OD+RS+Feed_Vol+mu_cumulo+nu_cumulo+Sugar_consuming_rate_cumulo+AS_Vol.; 0.686, 0.854, tmp+interval_Pdt.+RS+Feed_Vol+mu_cumulo+nu_per_rho_cumulo+Sugar_consuming_rate_cumulo+rab_integral+AS_Vol.+emission_O2; 0.686, 0.854, tmp+PL+AN_cumulo+RS+Feed_Vol+mu_cumulo+Sugar_consuming_rate_cumulo+rab_integral+RQ_integral+AS_Vol.; 0.691, 0.854, tmp+RS+Feed_Vol+mu_cumulo+Sugar_consuming_rate_cumulo+rab_integral+RQ_integral+AS_Vol.+emission_CO2; 0.670, 0.854, tmp+AN_cumulo+interval_Pdt.+RS+Feed_Vol+mu_cumulo+nu_cumulo+Sugar_consuming_rate_cumulo+RQ_integral+AS_Vol.+emission_O2+emission_CO2+generate_CO2; 0.670, 0.854, tmp+PL+interval_yield+interval_Pdt.+RS+Feed_Vol+mu_cumulo+nu_per_rho_cumulo+Sugar_consuming_rate_cumulo+rab_integral+AS_Vol.+emission_O2+emission_CO2; 0.670, 0.854, tmp+PL+AN+RS+Feed_Vol+mu_cumulo+rho_cumulo+nu_per_rho_cumulo+Sugar_consuming_rate_cumulo+RQ_integral+AS_Vol.+emission_O2+emission_CO2; 0.681, 0.854, tmp+PL+interval_Pdt.+OD+RS+Feed_Vol+mu_cumulo+rho_cumulo+Sugar_consuming_rate_cumulo+rab_integral+AS_Vol.; 0.664, 0.854, tmp+AN_cumulo+interval_yield+interval_Pdt.+RS+Feed_Vol+mu_cumulo+rho_cumulo+Sugar_consuming_rate_cumulo+rab_integral+AS_Vol.+emission_O2+emission_CO2+generate_CO2; 0.675, 0.854, tmp+AN+AN_cumulo+interval_Pdt.+OD+RS+Feed_Vol+mu_cumulo+rho_cumulo+Sugar_consuming_rate_cumulo+AS_Vol.+generate_CO2; 0.681, 0.854, tmp+AN_cumulo+interval_yield+interval_Pdt.+OD+RS+Feed_Vol+mu_cumulo+rho_cumulo+Sugar_consuming_rate_cumulo+AS_Vol.; 0.681, 0.854, tmp+AN+AN_cumulo+RS+Feed_Vol+mu_cumulo+nu_per_rho_cumulo+Sugar_consuming_rate_cumulo+AS_Vol.+emission_CO2+generate_CO2; 0.670, 0.854, tmp+AN+AN_cumulo+interval_yield+interval_Pdt.+OD+RS+Feed_Vol+mu_cumulo+Sugar_consuming_rate_cumulo+RQ_integral+AS_Vol.+emission_O2; 0.691, 0.854, tmp+interval_yield+interval_Pdt.+RS+Feed_Vol+mu_cumulo+nu_per_rho_cumulo+Sugar_consuming_rate_cumulo+AS_Vol.; 0.670, 0.854, tmp+PL+AN_cumulo+RS+Feed_Vol+mu_cumulo+rho_cumulo+nu_per_rho_cumulo+Sugar_consuming_rate_cumulo+RQ_integral+AS_Vol.+emission_O2+emission_CO2; 0.670, 0.854, tmp+AN+AN_cumulo+interval_yield+interval_Pdt.+RS+Feed_Vol+mu_cumulo+nu_per_rho_cumulo+Sugar_consuming_rate_cumulo+rab_integral+AS_Vol.+emission_O2+emission_CO2; 0.681, 0.854, tmp+interval_Pdt.+OD+RS+Feed_Vol+mu_cumulo+nu_cumulo+nu_per_rho_cumulo+Sugar_consuming_rate_cumulo+rab_integral+AS_Vol.; 0.664, 0.854, tmp+PL+AN_cumulo+interval_Pdt.+RS+Feed_Vol+mu_cumulo+nu_per_rho_cumulo+Sugar_consuming_rate_cumulo+rab_integral+RQ_integral+AS_Vol.+emission_O2+emission_CO2; 0.686, 0.854, tmp+AN+AN_cumulo+RS+Feed_Vol+mu_cumulo+Sugar_consuming_rate_cumulo+rab_integral+RQ_integral+AS_Vol.; 0.681, 0.854, tmp+interval_yield+RS+Feed_Vol+mu_cumulo+rho_cumulo+Sugar_consuming_rate_cumulo+RQ_integral+AS_Vol.+emission_O2+emission_CO2; 0.686, 0.854, tmp+AN_cumulo+interval_yield+interval_Pdt.+RS+Feed_Vol+mu_cumulo+Sugar_consuming_rate_cumulo+RQ_integral+emission_O2; 0.675, 0.854, tmp+AN+AN_cumulo+interval_yield+interval_Pdt.+RS+Feed_Vol+mu_cumulo+nu_per_rho_cumulo+Sugar_consuming_rate_cumulo+rab_integral+emission_O2; 0.675, 0.854, tmp+AN_cumulo+interval_yield+interval_Pdt.+OD+RS+Feed_Vol+mu_cumulo+rho_cumulo+Sugar_consuming_rate_cumulo+RQ_integral+AS_Vol.; 0.675, 0.854, tmp+AN_cumulo+interval_Pdt.+RS+Feed_Vol+mu_cumulo+nu_cumulo+Sugar_consuming_rate_cumulo+rab_integral+AS_Vol.+emission_O2+emission_CO2; 0.664, 0.854, tmp+AN+interval_Pdt.+OD+RS+Feed_Vol+mu_cumulo+rho_cumulo+Sugar_consuming_rate_cumulo+RQ_integral+AS_Vol.+emission_O2+emission_CO2+generate_CO2; 0.681, 0.854, tmp+AN_cumulo+RS+Feed_Vol+mu_cumulo+Sugar_consuming_rate_cumulo+RQ_integral+AS_Vol.+emission_CO2+consum_O2+generate_CO2; 0.675, 0.854, tmp+AN_cumulo+interval_yield+interval_Pdt.+OD+RS+Feed_Vol+mu_cumulo+Sugar_consuming_rate_cumulo+AS_Vol.+consum_O2+generate_CO2; 0.681, 0.854, tmp+AN_cumulo+interval_yield+RS+Feed_Vol+mu_cumulo+nu_per_rho_cumulo+Sugar_consuming_rate_cumulo+AS_Vol.+emission_CO2+generate_CO2; 0.686, 0.854, tmp+AN_cumulo+RS+Feed_Vol+mu_cumulo+nu_cumulo+Sugar_consuming_rate_cumulo+AS_Vol.+emission_CO2+generate_CO2; 0.675, 0.854, tmp+AN_cumulo+OD+RS+Feed_Vol+mu_cumulo+nu_per_rho_cumulo+Sugar_consuming_rate_cumulo+RQ_integral+AS_Vol.+emission_O2+emission_CO2; 0.686, 0.854, tmp+interval_Pdt.+OD+RS+Feed_Vol+mu_cumulo+rho_cumulo+Sugar_consuming_rate_cumulo+AS_Vol.+emission_O2; 0.664, 0.854, tmp+PL+interval_Pdt.+RS+Feed_Vol+mu_cumulo+nu_per_rho_cumulo+Sugar_consuming_rate_cumulo+rab_integral+RQ_integral+AS_Vol.+emission_O2+emission_CO2+generate_CO2; 0.686, 0.854, tmp+AN+RS+Feed_Vol+mu_cumulo+nu_per_rho_cumulo+Sugar_consuming_rate_cumulo+RQ_integral+AS_Vol.+emission_CO2; 0.670, 0.854, tmp+PL+interval_yield+RS+Feed_Vol+mu_cumulo+rho_cumulo+Sugar_consuming_rate_cumulo+rab_integral+RQ_integral+AS_Vol.+emission_O2+emission_CO2; 0.695, 0.854, tmp+AN_cumulo+interval_yield+RS+Feed_Vol+mu_cumulo+nu_per_rho_cumulo+AS_Vol.; 0.690, 0.854, tmp+AN+interval_Pdt.+RS+Feed_Vol+mu_cumulo+rho_cumulo+Sugar_consuming_rate_cumulo+AS_Vol.; 0.675, 0.854, tmp+AN+AN_cumulo+interval_Pdt.+RS+Feed_Vol+mu_cumulo+rho_cumulo+Sugar_consuming_rate_cumulo+rab_integral+AS_Vol.+emission_O2; 0.680, 0.854, tmp+AN_cumulo+RS+Feed_Vol+mu_cumulo+Sugar_consuming_rate_cumulo+rab_integral+RQ_integral+AS_Vol.+emission_CO2+generate_CO2; 0.680, 0.854, tmp+PL+AN_cumulo+RS+Feed_Vol+mu_cumulo+Sugar_consuming_rate_cumulo+rab_integral+AS_Vol.+emission_CO2+generate_CO2; 0.664, 0.854, tmp+PL+AN+interval_Pdt.+OD+RS+Feed_Vol+mu_cumulo+rho_cumulo+Sugar_consuming_rate_cumulo+rab_integral+AS_Vol.+emission_O2+emission_CO2; 0.670, 0.854, tmp+pH+AN_cumulo+RS+Feed_Vol+mu_cumulo+ nu_per_rho_cumulo+Sugar_consuming_rate_cumulo+RQ_ integral+AS_Vol.+emission_O2+emission_CO2+generate_ CO2; 0.680, 0.854, tmp+AN_cumulo+interval_yield+RS+ Feed_Vol+mu_cumulo+Sugar_consuming_rate_cumulo+ rab_integral+AS_Vol.+emission_CO2+generate_CO2; 0.686, 0.854, tmp+interval_Pdt.+RS+Feed_Vol+mu_cumulo+nu_cumulo+rho_cumulo+Sugar_consuming_rate_cumulo+rab_integral+AS_Vol.; 0.670, 0.854, tmp+PL+AN_ cumulo+OD+RS+Feed_Vol+mu_cumulo+Sugar_ consuming_rate_cumulo+RQ_integral+AS_Vol.+emission_ O2+emission_CO2+generate_CO2; 0.670, 0.854, tmp+PL+ AN_cumulo+interval_yield+RS+Feed_Vol+mu_cumulo+ nu_per_rho_cumulo+Sugar_consuming_rate_cumulo+RQ_ integral+AS_Vol.+emission_O2+emission_CO2; 0.664, 0.854, tmp+PL+AN_cumulo+interval_yield+interval_Pdt.+ OD+RS+Feed_Vol+mu_cumulo+nu_cumulo+Sugar_consuming_rate_cumulo+rab_integral+AS_Vol.+emission_O2; 0.680, 0.854, tmp+AN_cumulo+interval_yield+RS+Feed_ Vol+mu_cumulo+nu_per_rho_cumulo+Sugar_consuming_ rate_cumulo+rab_integral+RQ_integral+AS_Vol.; 0.675, 0.854, tmp+PL+AN_cumulo+RS+Feed_Vol+mu_cumulo+ nu_cumulo+Sugar_consuming_rate_cumulo+RQ_integral+ AS_Vol.+emission_O2+emission_CO2; 0.664, 0.854, tmp+ PL+AN_cumulo+interval_Pdt.+RS+Feed_Vol+mu_ cumulo+nu_cumulo+nu_per_rho_cumulo+Sugar_ consuming_rate_cumulo+RQ_integral+AS_Vol.+emission_ O2+emission_CO2; 0.685, 0.854, tmp+AN+interval_Pdt.+ RS+Feed_Vol+mu_cumulo+Sugar_consuming_rate_ cumulo+rab_integral+AS_Vol.+emission_O2; 0.680, 0.854, tmp+AN+interval_yield+interval_Pdt.+RS+Feed_Vol+mu_ cumulo+nu_per_rho_cumulo+Sugar_consuming_rate_cumulo+rab_integral+AS_Vol.; 0.664, 0.854, tmp+PL+AN_ cumulo+interval_yield+interval_Pdt.+RS+Feed_Vol+mu_ cumulo+rho_cumulo+Sugar_consuming_rate_cumulo+rab_ integral+AS_Vol.+emission_O2+emission_CO2; 0.690, 0.854, tmp+AN_cumulo+interval_Pdt.+RS+Feed_Vol+mu_ cumulo+Sugar_consuming_rate_cumulo+rab_integral+generate_CO2; 0.675, 0.854, tmp+pH+AN_cumulo+interval_ yield+interval_Pdt.+RS+Feed_Vol+mu_cumulo+Sugar_ consuming_rate_cumulo+rab_integral+AS_Vol.+emission_ O2; 0.670, 0.854, tmp+interval_Pdt.+RS+Feed_Vol+mu_ cumulo+rho_cumulo+Sugar_consuming_rate_cumulo+rab_ integral+RQ_integral+AS_Vol.+emission_O2+emission_ CO2+generate_CO2; 0.664, 0.854, tmp+AN+AN_cumulo+ interval_yield+interval_Pdt.+OD+RS+Feed_Vol+mu_ cumulo+rho_cumulo+Sugar_consuming_rate_cumulo+rab_ integral+AS_Vol.+emission_O2; 0.670, 0.854, tmp+PL+ AN+interval_Pdt.+RS+Feed_Vol+mu_cumulo+Sugar_ consuming_rate_cumulo+rab_integral+RQ_integral+AS_ Vol.+emission_O2+emission_CO2; 0.664, 0.854, tmp+PL+ interval_Pdt.+RS+Feed_Vol+mu_cumulo+rho_cumulo+ nu_per_rho_cumulo+Sugar_consuming_rate_cumulo+rab_ integral+RQ_integral+AS_Vol.+emission_O2+emission_ CO2; 0.664, 0.854, tmp+AN+interval_yield+interval_Pdt.+ OD+RS+Feed_Vol+mu_cumulo+rho_cumulo+Sugar_ consuming_rate_cumulo+rab_integral+AS_Vol.+emission_ O2+emission_CO2; 0.680, 0.854, tmp+AN_cumulo+ interval_Pdt.+RS+Feed_Vol+mu_cumulo+nu_per_rho_ cumulo+Sugar_consuming_rate_cumulo+rab_integral+AS_ Vol.+consum_O2; 0.680, 0.854, tmp+interval_Pdt.+OD+ RS+Feed_Vol+mu_cumulo+rho_cumulo+Sugar_ consuming_rate_cumulo+rab_integral+AS_Vol.+generate_ CO2; 0.685, 0.854, tmp+pH+AN_cumulo+interval_yield+ RS+Feed_Vol+mu_cumulo+Sugar_consuming_rate_ cumulo+rab_integral+AS_Vol.; 0.670, 0.854, tmp+AN+ AN_cumulo+RS+Feed_Vol+mu_cumulo+nu_cumulo+ Sugar_consuming_rate_cumulo+RQ_integral+AS_Vol.+ emission_O2+emission_CO2+generate_CO2; 0.685, 0.854, tmp+PL+interval_yield+interval_Pdt.+RS+Feed_Vol+mu_ cumulo+Sugar_consuming_rate_cumulo+rab_integral+AS_ Vol.; 0.658, 0.854, tmp+PL+AN_cumulo+interval_Pdt.+ OD+RS+Feed_Vol+mu_cumulo+nu_per_rho_cumulo+ Sugar_consuming_rate_cumulo+RQ_integral+AS_Vol.+ emission_O2+emission_CO2+generate_CO2; 0.685, 0.854, tmp+AN+interval_Pdt.+OD+RS+Feed_Vol+mu_cumulo+ nu_per_rho_cumulo+Sugar_consuming_rate_cumulo+AS_ Vol.; 0.685, 0.854, tmp+interval_Pdt.+RS+Feed_Vol+mu_ cumulo+Sugar_consuming_rate_cumulo+AS_Vol.+ emission_CO2+consum_O2+generate_CO2; 0.690, 0.854, tmp+AN+interval_Pdt.+RS+Feed_Vol+mu_cumulo+ Sugar_consuming_rate_cumulo+AS_Vol.+generate_CO2; 0.695, 0.853, tmp+pH+interval_Pdt.+RS+Feed_Vol+mu_ cumulo+Sugar_consuming_rate_cumulo+AS_Vol.; 0.670, 0.853, tmp+AN_cumulo+interval_Pdt.+RS+Feed_Vol+mu_ cumulo+nu_per_rho_cumulo+Sugar_consuming_rate_cumulo+rab_integral+RQ_integral+AS_Vol.+emission_O2+ emission_CO2; 0.680, 0.853, tmp+PL+AN_cumulo+ interval_Pdt.+RS+Feed_Vol+mu_cumulo+nu_per_rho_ cumulo+Sugar_consuming_rate_cumulo+RQ_integral+ emission_O2; 0.670, 0.853, tmp+PL+AN_cumulo+RS+ Feed_Vol+mu_cumulo+rho_cumulo+Sugar_consuming_ rate_cumulo+rab_integral+RQ_integral+AS_Vol.+ emission_O2+emission_CO2; 0.675, 0.853, tmp+PL+AN+ AN_cumulo+interval_yield+interval_Pdt.+RS+Feed_Vol+ mu_cumulo+Sugar_consuming_rate_cumulo+rab_integral+ AS_Vol.; 0.675, 0.853, tmp+PL+AN_cumulo+interval_ Pdt.+RS+Feed_Vol+mu_cumulo+Sugar_consuming_rate_ cumulo+rab_integral+AS_Vol.+emission_O2+generate_ CO2; 0.670, 0.853, tmp+AN+RS+Feed_Vol+mu_cumulo+ nu_cumulo+nu_per_rho_cumulo+Sugar_consuming_rate_ cumulo+RQ_integral+AS_Vol.+emission_O2+emission_ CO2+generate_CO2; 0.675, 0.853, tmp+PL+AN_cumulo+ interval_Pdt.+RS+Feed_Vol+mu_cumulo+nu_cumulo+ Sugar_consuming_rate_cumulo+rab_integral+AS_Vol.+ emission_O2; 0.680, 0.853, tmp+AN_cumulo+OD+RS+ Feed_Vol+mu_cumulo+rho_cumulo+Sugar_consuming_ rate_cumulo+RQ_integral+AS_Vol.+emission_CO2; 0.670, 0.853, tmp+AN_cumulo+RS+Feed_Vol+mu_cumulo+rho_ cumulo+Sugar_consuming_rate_cumulo+rab_integral+ RQ_integral+AS_Vol.+emission_O2+emission_CO2+generate_CO2; 0.675, 0.853, tmp+PL+AN_cumulo+interval_ Pdt.+RS+Feed_Vol+mu_cumulo+nu_per_rho_cumulo+ Sugar_consuming_rate_cumulo+rab_integral+AS_Vol.+ generate_CO2; 0.670, 0.853, tmp+PL+interval_Pdt.+RS+ Feed_Vol+mu_cumulo+nu_cumulo+Sugar_consuming_ rate_cumulo+RQ_integral+AS_Vol.+emission_O2+ emission_CO2+generate_CO2; 0.695, 0.853, tmp+interval_ yield+RS+Feed_Vol+mu_cumulo+rho_cumulo+Sugar_ consuming_rate_cumulo+AS_Vol.; 0.680, 0.853, tmp+AN+ AN_cumulo+interval_Pdt.+RS+Feed_Vol+mu_cumulo+ Sugar_consuming_rate_cumulo+rab_integral+AS_Vol.+ emission_CO2; 0.670, 0.853, tmp+PL+AN_cumulo+ interval_yield+interval_Pdt.+RS+Feed_Vol+mu_cumulo+ Sugar_consuming_rate_cumulo+rab_integral+AS_Vol.+ emission_O2+generate_CO2; 0.664, 0.853, tmp+PL+AN+ interval_yield+interval_Pdt.+RS+Feed_Vol+mu_cumulo+ rho_cumulo+Sugar_consuming_rate_cumulo+rab_ integral+AS_Vol.+emission_O2+emission_CO2; 0.680, 0.853, tmp+AN+AN_cumulo+interval_Pdt.+RS+Feed_ Vol+mu_cumulo+nu_cumulo+Sugar_consuming_rate_cumulo+rab_integral+AS_Vol.; 0.690, 0.853, tmp+interval_ yield+interval_Pdt.+OD+RS+Feed_Vol+mu_cumulo+ Sugar_consuming_rate_cumulo+AS_Vol.; 0.670, 0.853, tmp+PL+interval_yield+interval_Pdt.+RS+Feed_Vol+mu_cumulo+Sugar_consuming_rate_cumulo+rab_integral+AS_Vol.+emission_O2+emission_CO2+generate_CO2; 0.670, 0.853, tmp+interval_yield+interval_Pdt.+RS+Feed_Vol+mu_cumulo+Sugar_consuming_rate_cumulo+rab_integral+RQ_integral+AS_Vol.+emission_O2+emission_CO2+generate_CO2; 0.675, 0.853, tmp+PL+AN+interval_Pdt.+RS+Feed_Vol+mu_cumulo+Sugar_consuming_rate_cumulo+rab_integral+AS_Vol.+emission_O2+emission_CO2; 0.690, 0.853, tmp+AN+interval_Pdt.+RS+Feed_Vol+mu_cumulo+Sugar_consuming_rate_cumulo+RQ_integral+AS_Vol.; 0.664, 0.853, tmp+PL+interval_yield+interval_Pdt.+RS+Feed_Vol+mu_cumulo+rho_cumulo+Sugar_consuming_rate_cumulo+rab_integral+RQ_integral+AS_Vol.+emission_O2+emission_CO2; 0.675, 0.853, tmp+AN+interval_yield+RS+Feed_Vol+mu_cumulo+nu_per_rho_cumulo+Sugar_consuming_rate_cumulo+RQ_integral+AS_Vol.+emission_O2+emission_CO2; 0.700, 0.853, tmp+AN_cumulo+interval_Pdt.+RS+Feed_Vol+mu_cumulo+AS_Vol.; 0.675, 0.853, tmp+AN+AN_cumulo+interval_Pdt.+OD+RS+Feed_Vol+mu_cumulo+nu_per_rho_cumulo+Sugar_consuming_rate_cumulo+RQ_integral+AS_Vol; 0.670, 0.853, tmp+PL+interval_yield+RS+Feed_Vol+mu_cumulo+nu_cumulo+rho_cumulo+Sugar_consuming_rate_cumulo+RQ_integral+AS_Vol.+emission_O2+emission_CO2; 0.685, 0.853, tmp+AN+interval_yield+RS+Feed_Vol+mu_cumulo+nu_per_rho_cumulo+Sugar_consuming_rate_cumulo+rab_integral+AS_Vol.; 0.675, 0.853, tmp+AN_cumulo+interval_Pdt.+RS+Feed_Vol+mu_cumulo+nu_per_rho_cumulo+Sugar_consuming_rate_cumulo+rab_integral+AS_Vol.+emission_CO2+generate_CO2; 0.690, 0.853, tmp+PL+RS+Feed_Vol+mu_cumulo+Sugar_consuming_rate_cumulo+rab_integral+AS_Vol.+emission_CO2; 0.680, 0.853, tmp+RS+Feed_Vol+mu_cumulo+nu_per_rho_cumulo+Sugar_consuming_rate_cumulo+RQ_integral+AS_Vol.+emission_CO2+consum_O2+generate_CO2; 0.675, 0.853, tmp+AN+RS+Feed_Vol+mu_cumulo+nu_per_rho_cumulo+Sugar_consuming_rate_cumulo+rab_integral+RQ_integral+AS_Vol.+emission_O2+emission_CO2; 0.685, 0.853, tmp+AN_cumulo+interval_Pdt.+OD+RS+Feed_Vol+mu_cumulo+Sugar_consuming_rate_cumulo+AS_Vol.+emission_CO2; 0.695, 0.853, tmp+pH+AN_cumulo+RS+Feed_Vol+mu_cumulo+Sugar_consuming_rate_cumulo+AS_Vol.; 0.680, 0.853, tmp+AN_cumulo+interval_yield+interval_Pdt.+RS+Feed_Vol+mu_cumulo+nu_per_rho_cumulo+Sugar_consuming_rate_cumulo+RQ_integral+AS_Vol.; 0.680, 0.853, tmp+AN_cumulo+RS+Feed_Vol+mu_cumulo+rho_cumulo+nu_per_rho_cumulo+Sugar_consuming_rate_cumulo+rab_integral+AS_Vol.+emission_CO2; 0.685, 0.853, tmp+PL+interval_Pdt.+RS+Feed_Vol+mu_cumulo+rho_cumulo+Sugar_consuming_rate_cumulo+rab_integral+AS_Vol.; 0.669, 0.853, tmp+interval_yield+interval_Pdt.+RS+Feed_Vol+mu_cumulo+nu_per_rho_cumulo+Sugar_consuming_rate_cumulo+rab_integral+RQ_integral+AS_Vol.+emission_O2+emission_CO2; 0.680, 0.853, tmp+interval_Pdt.+RS+Feed_Vol+mu_cumulo+rho_cumulo+nu_per_rho_cumulo+Sugar_consuming_rate_cumulo+AS_Vol.+emission_CO2+generate_CO2; 0.669, 0.853, tmp+AN+AN_cumulo+interval_Pdt.+RS+Feed_Vol+mu_cumulo+nu_per_rho_cumulo+Sugar_consuming_rate_cumulo+rab_integral+AS_Vol.+emission_O2+emission_CO2; 0.680, 0.853, tmp+PL+OD+RS+Feed_Vol+mu_cumulo+Sugar_consuming_rate_cumulo+RQ_integral+AS_Vol.+emission_O2+emission_CO2; 0.680, 0.853, tmp+AN+AN_cumulo+interval_Pdt.+RS+Feed_Vol+mu_cumulo+Sugar_consuming_rate_cumulo+AS_Vol.+emission_CO2+generate_CO2; 0.669, 0.853, tmp+AN_cumulo+interval_Pdt.+RS+Feed_Vol+mu_cumulo+nu_cumulo+rho_cumulo+Sugar_consuming_rate_cumulo+rab_integral+AS_Vol.+emission_O2+emission_CO2; 0.685, 0.853, tmp+AN_cumulo+interval_Pdt.+RS+Feed_Vol+mu_cumulo+rho_cumulo+nu_per_rho_cumulo+Sugar_consuming_rate_cumulo+AS_Vol.; 0.669, 0.853, tmp+AN+AN_cumulo+interval_Pdt.+RS+Feed_Vol+mu_cumulo+Sugar_consuming_rate_cumulo+RQ_integral+AS_Vol.+emission_O2+emission_CO2+generate_CO2; 0.685, 0.853, tmp+PL+AN_cumulo+RS+Feed_Vol+mu_cumulo+nu_per_rho_cumulo+Sugar_consuming_rate_cumulo+RQ_integral+AS_Vol.; 0.680, 0.853, tmp+interval_yield+interval_Pdt.+RS+Feed_Vol+mu_cumulo+nu_per_rho_cumulo+Sugar_consuming_rate_cumulo+AS_Vol.+emission_CO2+generate_CO2; 0.669, 0.853, tmp+PL+AN+interval_Pdt.+RS+Feed_Vol+mu_cumulo+rho_cumulo+Sugar_consuming_rate_cumulo+rab_integral+RQ_integral+emission_O2+emission_CO2; 0.685, 0.853, tmp+AN_cumulo+RS+Feed_Vol+mu_cumulo+nu_cumulo+nu_per_rho_cumulo+Sugar_consuming_rate_cumulo+rab_integral+AS_Vol.; 0.685, 0.853, tmp+AN_cumulo+interval_yield+RS+Feed_Vol+mu_cumulo+rho_cumulo+Sugar_consuming_rate_cumulo+RQ_integral+AS_Vol.; 0.690, 0.853, tmp+AN+interval_yield+interval_Pdt.+RS+Feed_Vol+mu_cumulo+Sugar_consuming_rate_cumulo+AS_Vol.; 0.675, 0.853, tmp+AN_cumulo+interval_Pdt.+RS+Feed_Vol+mu_cumulo+rho_cumulo+Sugar_consuming_rate_cumulo+rab_integral+AS_Vol.+emission_O2+generate_CO2; 0.690, 0.853, tmp+PL+interval_yield+RS+Feed_Vol+mu_cumulo+nu_per_rho_cumulo+Sugar_consuming_rate_cumulo+AS_Vol.; 0.680, 0.853, tmp+AN_cumulo+interval_Pdt.+RS+Feed_Vol+mu_cumulo+nu_cumulo+Sugar_consuming_rate_cumulo+AS_Vol.+emission_CO2+generate_CO2; 0.664, 0.853, tmp+PL+AN+AN_cumulo+RS+Feed_Vol+mu_cumulo+nu_per_rho_cumulo+Sugar_consuming_rate_cumulo+RQ_integral+AS_Vol.+emission_O2+emission_CO2+generate_CO2; 0.680, 0.853, tmp+pH+AN_cumulo+RS+Feed_Vol+mu_cumulo+Sugar_consuming_rate_cumulo+RQ_integral+AS_Vol.+emission_CO2+generate_CO2; 0.685, 0.853, tmp+AN_cumulo+interval_yield+RS+Feed_Vol+mu_cumulo+Sugar_consuming_rate_cumulo+rab_integral+AS_Vol.+emission_O2; 0.680, 0.853, tmp+AN_cumulo+interval_Pdt.+RS+Feed_Vol+mu_cumulo+nu_cumulo+Sugar_consuming_rate_cumulo+rab_integral+AS_Vol.+generate_CO2; 0.680, 0.853, tmp+AN_cumulo+interval_yield+RS+Feed_Vol+mu_cumulo+nu_per_rho_cumulo+Sugar_consuming_rate_cumulo+RQ_integral+AS_Vol.+emission_CO2; 0.680, 0.853, tmp+AN+AN_cumulo+RS+Feed_Vol+mu_cumulo+rho_cumulo+Sugar_consuming_rate_cumulo+rab_integral+AS_Vol.+emission_CO2; 0.669, 0.853, tmp+PL+AN_cumulo+interval_yield+interval_Pdt.+RS+Feed_Vol+mu_cumulo+nu_cumulo+Sugar_consuming_rate_cumulo+rab_integral+AS_Vol.+emission_O2; 0.690, 0.853, tmp+AN_cumulo+RS+Feed_Vol+mu_cumulo+Sugar_consuming_rate_cumulo+rab_integral+AS_Vol.+consum_O2; 0.695, 0.853, tmp+AN+interval_yield+RS+Feed_Vol+mu_cumulo+Sugar_consuming_rate_cumulo+RQ_integral; 0.675, 0.853, tmp+PL+RS+Feed_Vol+mu_cumulo+nu_per_rho_cumulo+Sugar_consuming_rate_cumulo+rab_integral+RQ_integral+AS_Vol.+emission_O2+emission_CO2; 0.685, 0.853, tmp+RS+Feed_Vol+mu_cumulo+nu_cumulo+Sugar_consuming_rate_cumulo+rab_integral+AS_Vol.+emission_CO2+generate_CO2; 0.695, 0.853, tmp+interval_Pdt.+OD+RS+Feed_Vol+mu_cumulo+nu_per_rho_cumulo+AS_Vol.; 0.680, 0.853, tmp+OD+RS+Feed_

Vol+mu_cumulo+nu_per_rho_cumulo+Sugar_consuming_rate_cumulo+RQ_integral+AS_Vol.+emission_CO2+consum_O2; 0.664, 0.853, tmp+PL+AN_cumulo+RS+Feed_Vol+mu_cumulo+rho_cumulo+nu_per_rho_cumulo+Sugar_consuming_rate_cumulo+RQ_integral+AS_Vol.+emission_O2+emission_CO2+generate_CO2; 0.669, 0.853, tmp+AN+interval_Pdt.+RS+Feed_Vol+mu_cumulo+nu_cumulo+rho_cumulo+Sugar_consuming_rate_cumulo+rab_integral+AS_Vol.+emission_O2+emission_CO2; 0.690, 0.853, tmp+AN_cumulo+interval_Pdt.+OD+RS+Feed_Vol+mu_cumulo+nu_per_rho_cumulo+AS_Vol.; 0.680, 0.853, tmp+AN_cumulo+interval_Pdt.+OD+RS+Feed_Vol+mu_cumulo+Sugar_consuming_rate_cumulo+AS_Vol.+consum_O2+generate_CO2; 0.685, 0.853, tmp+interval_yield+interval_Pdt.+OD+RS+Feed_Vol+mu_cumulo+Sugar_consuming_rate_cumulo+rab_integral+AS_Vol.; 0.704, 0.853, tmp+interval_Pdt.+RS+Feed_Vol+mu_cumulo+AS_Vol.; 0.680, 0.853, tmp+PL+AN_cumulo+interval_Pdt.+RS+Feed_Vol+mu_cumulo+nu_cumulo+Sugar_consuming_rate_cumulo+rab_integral+AS_Vol.; 0.685, 0.853, tmp+AN_cumulo+OD+RS+Feed_Vol+mu_cumulo+nu_per_rho_cumulo+Sugar_consuming_rate_cumulo+RQ_integral+AS_Vol.; 0.669, 0.853, tmp+PL+OD+RS+Feed_Vol+mu_cumulo+nu_per_rho_cumulo+Sugar_consuming_rate_cumulo+RQ_integral+AS_Vol.+emission_O2+emission_CO2+generate_CO2; 0.669, 0.853, tmp+PL+interval_yield+RS+Feed_Vol+mu_cumulo+nu_cumulo+nu_per_rho_cumulo+Sugar_consuming_rate_cumulo+RQ_integral+AS_Vol.+emission_O2+emission_CO2; 0.685, 0.853, tmp+AN_cumulo+RS+Feed_Vol+mu_cumulo+Sugar_consuming_rate_cumulo+RQ_integral+AS_Vol.+emission_CO2+consum_O2; 0.675, 0.853, tmp+PL+AN_cumulo+interval_Pdt.+OD+RS+Feed_Vol+mu_cumulo+rho_cumulo+Sugar_consuming_rate_cumulo+RQ_integral+emission_O2; 0.669, 0.853, tmp+PL+RS+Feed_Vol+mu_cumulo+rho_cumulo+Sugar_consuming_rate_cumulo+rab_integral+RQ_integral+AS_Vol.+emission_O2+emission_CO2+generate_CO2; 0.699, 0.853, tmp+interval_Pdt.+RS+Feed_Vol+mu_cumulo+nu_per_rho_cumulo+AS_Vol.; 0.675, 0.853, tmp+PL+interval_Pdt.+OD+RS+Feed_Vol+mu_cumulo+rho_cumulo+Sugar_consuming_rate_cumulo+rab_integral+AS_Vol.+emission_O2; 0.685, 0.853, tmp+PL+RS+Feed_Vol+mu_cumulo+nu_per_rho_cumulo+Sugar_consuming_rate_cumulo+AS_Vol.+emission_CO2+generate_CO2; 0.685, 0.853, tmp+pH+RS+Feed_Vol+mu_cumulo+rho_cumulo+Sugar_consuming_rate_cumulo+AS_Vol.+emission_CO2+generate_CO2; 0.680, 0.853, tmp+AN_cumulo+OD+RS+Feed_Vol+mu_cumulo+rho_cumulo+Sugar_consuming_rate_cumulo+RQ_integral+AS_Vol.+consum_O2; 0.685, 0.853, tmp+interval_Pdt.+OD+RS+Feed_Vol+mu_cumulo+nu_cumulo+Sugar_consuming_rate_cumulo+rab_integral+AS_Vol.; 0.685, 0.853, tmp+AN+interval_yield+RS+Feed_Vol+mu_cumulo+rho_cumulo+Sugar_consuming_rate_cumulo+rab_integral+AS_Vol.; 0.690, 0.853, tmp+interval_Pdt.+RS+Feed_Vol+mu_cumulo+Sugar_consuming_rate_cumulo+rab_integral+AS_Vol.+consum_O2; 0.669, 0.853, tmp+AN_cumulo+interval_yield+interval_Pdt.+OD+RS+Feed_Vol+mu_cumulo+Sugar_consuming_rate_cumulo+rab_integral+AS_Vol.+emission_O2+generate_CO2; 0.675, 0.853, tmp+AN_cumulo+RS+Feed_Vol+mu_cumulo+rho_cumulo+nu_per_rho_cumulo+Sugar_consuming_rate_cumulo+RQ_integral+AS_Vol.+emission_CO2+generate_CO2; 0.669, 0.853, tmp+AN+interval_Pdt.+OD+RS+Feed_Vol+mu_cumulo+Sugar_consuming_rate_cumulo+RQ_integral+AS_Vol.+emission_O2+emission_CO2+generate_CO2; 0.680, 0.853, tmp+pH+AN_cumulo+interval_Pdt.+RS+Feed_Vol+mu_cumulo+rho_cumulo+Sugar_consuming_rate_cumulo+rab_integral+AS_Vol.; 0.680, 0.853, tmp+AN_cumulo+interval_Pdt.+RS+Feed_Vol+mu_cumulo+rho_cumulo+nu_per_rho_cumulo+Sugar_consuming_rate_cumulo+RQ_integral+AS_Vol.; 0.690, 0.853, tmp+interval_Pdt.+OD+RS+Feed_Vol+mu_cumulo+Sugar_consuming_rate_cumulo+AS_Vol.+generate_CO2; 0.675, 0.853, tmp+AN+OD+RS+Feed_Vol+mu_cumulo+rho_cumulo+Sugar_consuming_rate_cumulo+RQ_integral+AS_Vol.+emission_CO2+consum_O2; 0.680, 0.853, tmp+AN+interval_yield+RS+Feed_Vol+mu_cumulo+nu_per_rho_cumulo+Sugar_consuming_rate_cumulo+AS_Vol.+emission_CO2+generate_CO2; 0.680, 0.853, tmp+AN+interval_Pdt.+RS+Feed_Vol+mu_cumulo+Sugar_consuming_rate_cumulo+RQ_integral+emission_O2+emission_CO2+generate_CO2; 0.685, 0.853, tmp+interval_yield+OD+RS+Feed_Vol+mu_cumulo+rho_cumulo+Sugar_consuming_rate_cumulo+rab_integral+AS_Vol.; 0.685, 0.853, tmp+pH+AN+AN_cumulo+RS+Feed_Vol+mu_cumulo+Sugar_consuming_rate_cumulo+rab_integral+AS_Vol.; 0.685, 0.853, tmp+interval_Pdt.+RS+Feed_Vol+mu_cumulo+nu_per_rho_cumulo+Sugar_consuming_rate_cumulo+rab_integral+AS_Vol.+generate_CO2; 0.680, 0.853, tmp+PL+AN+interval_Pdt.+RS+Feed_Vol+mu_cumulo+Sugar_consuming_rate_cumulo+RQ_integral+emission_O2+emission_CO2; 0.669, 0.853, tmp+pH+AN_cumulo+RS+Feed_Vol+mu_cumulo+rho_cumulo+Sugar_consuming_rate_cumulo+RQ_integral+AS_Vol.+emission_O2+emission_CO2+generate_CO2; 0.685, 0.853, tmp+RS+Feed_Vol+mu_cumulo+nu_cumulo+nu_per_rho_cumulo+Sugar_consuming_rate_cumulo+AS_Vol.+emission_CO2+generate_CO2; 0.669, 0.853, tmp+pH+interval_Pdt.+RS+Feed_Vol+mu_cumulo+rho_cumulo+Sugar_consuming_rate_cumulo+RQ_integral+AS_Vol.+emission_O2+emission_CO2+generate_CO2; 0.690, 0.853, tmp+interval_yield+RS+Feed_Vol+mu_cumulo+nu_per_rho_cumulo+Sugar_consuming_rate_cumulo+AS_Vol.+emission_CO2; 0.669, 0.853, tmp+pH+AN+interval_Pdt.+RS+Feed_Vol+mu_cumulo+rho_cumulo+Sugar_consuming_rate_cumulo+rab_integral+AS_Vol.+emission_O2+emission_CO2; 0.680, 0.853, tmp+interval_yield+interval_Pdt.+RS+Feed_Vol+mu_cumulo+Sugar_consuming_rate_cumulo+RQ_integral+AS_Vol.+emission_O2+emission_CO2; 0.669, 0.853, tmp+AN+OD+RS+Feed_Vol+mu_cumulo+nu_per_rho_cumulo+Sugar_consuming_rate_cumulo+RQ_integral+AS_Vol.+emission_O2+emission_CO2+generate_CO2; 0.675, 0.853, tmp+pH+RS+Feed_Vol+mu_cumulo+nu_per_rho_cumulo+Sugar_consuming_rate_cumulo+RQ_integral+AS_Vol.+emission_O2+emission_CO2+generate_CO2; 0.669, 0.853, tmp+PL+interval_Pdt.+RS+Feed_Vol+mu_cumulo+rho_cumulo+Sugar_consuming_rate_cumulo+rab_integral+AS_Vol.+emission_O2+emission_CO2+generate_CO2; 0.680, 0.853, tmp+AN+interval_Pdt.+OD+RS+Feed_Vol+mu_cumulo+nu_per_rho_cumulo+Sugar_consuming_rate_cumulo+AS_Vol.+consum_O2; 0.680, 0.853, tmp+interval_Pdt.+OD+RS+Feed_Vol+mu_cumulo+rho_cumulo+nu_per_rho_cumulo+Sugar_consuming_rate_cumulo+rab_integral+AS_Vol.; 0.690, 0.853, tmp+AN_cumulo+OD+RS+Feed_Vol+mu_cumulo+Sugar_consuming_rate_cumulo+rab_integral+AS_Vol.; 0.658, 0.853, tmp+PL+AN+AN_cumulo+interval_Pdt.+OD+RS+Feed_Vol+mu_cumulo+rho_cumulo+Sugar_consuming_rate_cumulo+RQ_integral+AS_Vol.+emission_O2+emission_CO2; 0.669, 0.853, tmp+AN+interval_yield+interval_Pdt.+RS+Feed_Vol+mu_cumulo+nu_cumulo+Sugar_consuming_rate_cumulo+rab_integral+AS_Vol.+emission_O2+emission_CO2; 0.690, 0.853, tmp+interval_Pdt.+RS+Feed_Vol+ mu_cumulo+nu_per_rho_cumulo+Sugar_consuming_rate_cumulo+AS_Vol.+generate_CO2

[204. Linear Model that Predicts Arginine Production Amount in Interval 4]
0.386, 0.697, tmp_cumulo+PL_cumulo+AN_cumulo+interval_yield+interval_Pdt.+Feed_Vol+RS_cumulo+rab_integral+RQ_integral+AS_Vol.+emission_CO2+interval_O2; 0.405, 0.697, tmp_cumulo+PL_cumulo+AN_cumulo+interval_yield+Feed_Vol+RS_cumulo+rab_integral+RQ_integral+AS_Vol.+emission_CO2; 0.394, 0.696, tmp_cumulo+PL_cumulo+AN_cumulo+interval_yield+Feed_Vol+RS_cumulo+rab_integral+RQ_integral+AS_Vol.+emission_CO2+interval_O2; 0.413, 0.696, tmp_cumulo+AN_cumulo+interval_yield+Feed_Vol+RS_cumulo+rab_integral+RQ_integral+AS_Vol.+emission_CO2; 0.403, 0.695, PL_cumulo+AN_cumulo+interval_yield+interval_Pdt.+RS_cumulo+rab_integral+RQ_integral+AS_Vol.+emission_CO2+interval_O2; 0.383, 0.695, tmp_cumulo+PL_cumulo+AN_cumulo+interval_yield+interval_Pdt.+Feed_Vol+RS_cumulo+rab_integral+RQ_integral+AS_Vol.+emission_CO2+consum_O2; 0.392, 0.695, tmp_cumulo+PL_cumulo+AN_cumulo+interval_yield+interval_Pdt.+Feed_Vol+RS_cumulo+rab_integral+RQ_integral+AS_Vol.+emission_CO2; 0.410, 0.694, PL_cumulo+AN_cumulo+interval_yield+interval_Pdt.+RS_cumulo+rab_integral+RQ_integral+AS_Vol.+emission_CO2; 0.390, 0.693, tmp_cumulo+PL_cumulo+AN_cumulo+interval_yield+interval_Pdt.+RS_cumulo+rab_integral+RQ_integral+AS_Vol.+emission_CO2+interval_O2; 0.408, 0.693, tmp_cumulo+PL_cumulo+interval_yield+Feed_Vol+RS_cumulo+rab_integral+RQ_integral+AS_Vol.+emission_CO2; 0.399, 0.693, tmp_cumulo+AN_cumulo+interval_yield+interval_Pdt.+Feed_Vol+RS_cumulo+rab_integral+RQ_integral+AS_Vol.+emission_CO2; 0.399, 0.693, tmp_cumulo+AN_cumulo+interval_yield+Feed_Vol+RS_cumulo+rab_integral+RQ_integral+AS_Vol.+emission_CO2+interval_O2; 0.399, 0.693, tmp_cumulo+AN_cumulo+interval_yield+RS+Feed_Vol+RS_cumulo+rab_integral+RQ_integral+AS_Vol.+emission_CO2; 0.389, 0.693, tmp_cumulo+PL+PL_cumulo+AN_cumulo+interval_yield+Feed_Vol+RS_cumulo+rab_integral+RQ_integral+AS_Vol.+emission_CO2; 0.379, 0.692, tmp_cumulo+AN+AN_cumulo+interval_yield+RS+Feed_Vol+RS_cumulo+rab_integral+RQ_integral+AS_Vol.+emission_CO2+consum_O2; 0.389, 0.692, tmp_cumulo+PL_cumulo+AN_cumulo+interval_yield+Feed_Vol+RS_cumulo+rab_integral+RQ_integral+AS_Vol.+emission_CO2+consum_O2; 0.398, 0.692, O2+PL_cumulo+AN_cumulo+interval_yield+interval_Pdt.+RS_cumulo+rab_integral+RQ_integral+AS_Vol.+emission_CO2; 0.407, 0.692, tmp_cumulo+PL_cumulo+interval_yield+interval_Pdt.+RS_cumulo+rab_integral+RQ_integral+AS_Vol.+emission_CO2; 0.397, 0.692, tmp_cumulo+PL_cumulo+AN_cumulo+interval_yield+interval_Pdt.+RS_cumulo+rab_integral+RQ_integral+AS_Vol.+emission_CO2; 0.397, 0.692, tmp_cumulo+AN+AN_cumulo+interval_yield+Feed_Vol+RS_cumulo+rab_integral+RQ_integral+AS_Vol.+emission_CO2; 0.387, 0.691, tmp_cumulo+AN_cumulo+interval_yield+interval_Pdt.+Feed_Vol+RS_cumulo+rab_integral+RQ_integral+AS_Vol.+emission_CO2+interval_O2; 0.387, 0.691, tmp_cumulo+AN_cumulo+interval_yield+interval_Pdt.+Feed_Vol+RS_cumulo+rab_integral+RQ_integral+AS_Vol.+emission_CO2+consum_O2; 0.367, 0.691, tmp_cumulo+PL_cumulo+AN_cumulo+interval_yield+interval_Pdt.+Feed_Vol+RS_cumulo+rab_integral+RQ_integral+AS_Vol.+emission_CO2+consum_O2+interval_O2; 0.377, 0.691, tmp_cumulo+PL_cumulo+AN+AN_cumulo+interval_yield+Feed_Vol+RS_cumulo+rab_integral+RQ_integral+AS_Vol.+emission_CO2+interval_O2; 0.387, 0.691, tmp_cumulo+AN_cumulo+interval_yield+RS+Feed_Vol+RS_cumulo+rab_integral+RQ_integral+AS_Vol.+emission_CO2+consum_O2; 0.396, 0.691, tmp_cumulo+PL_cumulo+interval_yield+interval_Pdt.+Feed_Vol+RS_cumulo+rab_integral+RQ_integral+AS_Vol.+emission_CO2; 0.396, 0.691, tmp_cumulo+AN_cumulo+interval_yield+RS+Feed_Vol+RS_cumulo+rab_integral+RQ_integral+AS_Vol.+emission_O2; 0.376, 0.691, tmp_cumulo+PL_cumulo+AN+AN_cumulo+interval_yield+Feed_Vol+RS_cumulo+rab_integral+RQ_integral+AS_Vol.+emission_CO2+consum_O2; 0.386, 0.691, tmp_cumulo+PL_cumulo+AN+AN_cumulo+interval_yield+Feed_Vol+RS_cumulo+rab_integral+RQ_integral+AS_Vol.+emission_CO2; 0.386, 0.691, tmp_cumulo+PL_cumulo+AN_cumulo+interval_yield+RS+Feed_Vol+RS_cumulo+rab_integral+RQ_integral+AS_Vol.+emission_CO2; 0.395, 0.691, tmp_cumulo+AN_cumulo+interval_yield+Feed_Vol+RS_cumulo+rab_integral+RQ_integral+AS_Vol.+emission_CO2+consum_O2; 0.386, 0.691, tmp_cumulo+AN+AN_cumulo+interval_yield+Feed_Vol+RS_cumulo+rab_integral+RQ_integral+AS_Vol.+emission_CO2+consum_O2; 0.386, 0.691, tmp_cumulo+pH+PL_cumulo+AN_cumulo+interval_yield+Feed_Vol+RS_cumulo+rab_integral+RQ_integral+AS_Vol.+emission_CO2; 0.376, 0.691, tmp_cumulo+PL_cumulo+AN_cumulo+interval_yield+RS+Feed_Vol+RS_cumulo+rab_integral+RQ_integral+AS_Vol.+emission_CO2+interval_O2; 0.385, 0.690, tmp_cumulo+AN_cumulo+interval_yield+RS+Feed_Vol+RS_cumulo+rab_integral+RQ_integral+AS_Vol.+emission_CO2+interval_O2; 0.375, 0.690, tmp_cumulo+pH+PL_cumulo+AN_cumulo+interval_yield+Feed_Vol+RS_cumulo+rab_integral+RQ_integral+AS_Vol.+emission_CO2+interval_O2; 0.385, 0.690, tmp_cumulo+PL_cumulo+AN_cumulo+interval_yield+RS+Feed_Vol+RS_cumulo+rab_integral+RQ_integral+AS_Vol.+emission_O2; 0.375, 0.690, tmp_cumulo+PL_cumulo+AN_cumulo+interval_yield+RS+Feed_Vol+RS_cumulo+rab_integral+RQ_integral+AS_Vol.+emission_CO2+consum_O2; 0.365, 0.690, tmp_cumulo+PL_cumulo+AN+AN_cumulo+interval_yield+RS+Feed_Vol+RS_cumulo+rab_integral+RQ_integral+AS_Vol.+emission_CO2+consum_O2; 0.375, 0.690, tmp_cumulo+PL+PL_cumulo+AN_cumulo+interval_yield+interval_Pdt.+Feed_Vol+RS_cumulo+rab_integral+RQ_integral+AS_Vol.+emission_CO2; 0.384, 0.690, tmp_cumulo+PL_cumulo+AN_cumulo+interval_yield+interval_Pdt.+Feed_Vol+RS_cumulo+rab_integral+RQ_integral+AS_Vol.+emission_O2; 0.364, 0.690, tmp_cumulo+pH+PL_cumulo+AN_cumulo+interval_yield+interval_Pdt.+Feed_Vol+RS_cumulo+rab_integral+RQ_integral+AS_Vol.+emission_CO2+interval_O2; 0.394, 0.690, tmp_cumulo+pH+AN_cumulo+interval_yield+Feed_Vol+RS_cumulo+rab_integral+RQ_integral+AS_Vol.+emission_CO2; 0.384, 0.690, tmp_cumulo+AN+AN_cumulo+interval_yield+Feed_Vol+RS_cumulo+rab_integral+RQ_integral+AS_Vol.+emission_CO2+interval_O2; 0.364, 0.689, tmp_cumulo+PL_cumulo+AN+AN_cumulo+interval_yield+interval_Pdt.+Feed_Vol+RS_cumulo+rab_integral+RQ_integral+AS_Vol.+emission_CO2+consum_O2; 0.393, 0.689, PL_cumulo+AN_cumulo+interval_yield+interval_Pdt.+RS_cumulo+rab_integral+RQ_integral+AS_Vol.+emission_CO2+consum_O2; 0.383, 0.689, tmp+PL_cumulo+AN_cumulo+interval_yield+interval_Pdt.+RS_cumulo+rab_integral+RQ_integral+AS_Vol.+emission_CO2+interval_O2; 0.373, 0.689, tmp_cumulo+PL_cumulo+

AN+AN_cumulo+interval_yield+interval_Pdt.+RS_cumulo+rab_integral+RQ_integral+AS_Vol.+emission_CO2+interval_O2; 0.383, 0.689, PL_cumulo+AN+AN_cumulo+interval_yield+interval_Pdt.+RS_cumulo+rab_integral+RQ_integral+AS_Vol.+emission_CO2+interval_O2; 0.363, 0.689, tmp_cumulo+PL_cumulo+AN+AN_cumulo+interval_yield+interval_Pdt.+Feed_Vol+RS_cumulo+rab_integral+RQ_integral+AS_Vol.+emission_CO2+interval_O2; 0.363, 0.689, tmp_cumulo+PL_cumulo+AN_cumulo+interval_yield+interval_Pdt.+RS+Feed_Vol+RS_cumulo+rab_integral+RQ_integral+AS_Vol.+emission_CO2+consum_O2; 0.373, 0.689, tmp_cumulo+PL_cumulo+AN_cumulo+interval_yield+Feed_Vol+RS_cumulo+rab_integral+RQ_integral+AS_Vol.+emission_CO2+consum_O2+interval_O2; 0.411, 0.689, PL_cumulo+interval_yield+interval_Pdt.+RS_cumulo+rab_integral+RQ_integral+AS_Vol.+emission_CO2; 0.383, 0.689, tmp_cumulo+AN+AN_cumulo+interval_yield+RS+Feed_Vol+RS_cumulo+rab_integral+RQ_integral+AS_Vol.+emission_CO2; 0.383, 0.689, PL_cumulo+AN_cumulo+interval_yield+interval_Pdt.+Feed_Vol+RS_cumulo+rab_integral+RQ_integral+AS_Vol.+emission_CO2+interval_O2; 0.362, 0.688, tmp_cumulo+PL_cumulo+AN_cumulo+interval_yield+interval_Pdt.+RS+Feed_Vol+RS_cumulo+rab_integral+RQ_integral+AS_Vol.+emission_CO2+interval_O2; 0.372, 0.688, tmp_cumulo+pH+PL+PL_cumulo+AN_cumulo+interval_yield+Feed_Vol+RS_cumulo+rab_integral+RQ_integral+AS_Vol.+emission_CO2; 0.372, 0.688, tmp_cumulo+PL_cumulo+AN_cumulo+interval_yield+interval_Pdt.+RS+Feed_Vol+RS_cumulo+rab_integral+RQ_integral+AS_Vol.+emission_O2; 0.372, 0.688, tmp_cumulo+AN_cumulo+interval_yield+interval_Pdt.+RS+Feed_Vol+RS_cumulo+rab_integral+RQ_integral+AS_Vol.+emission_CO2+consum_O2; 0.382, 0.688, O2+PL_cumulo+AN_cumulo+interval_yield+interval_Pdt.+RS_cumulo+rab_integral+RQ_integral+AS_Vol.+emission_CO2+interval_O2; 0.382, 0.688, tmp_cumulo+PL_cumulo+AN_cumulo+interval_yield+interval_Pdt.+RS_cumulo+rab_integral+RQ_integral+AS_Vol.+emission_CO2+consum_O2; 0.391, 0.688, O2+PL_cumulo+AN_cumulo+interval_yield+Feed_Vol+RS_cumulo+rab_integral+RQ_integral+AS_Vol.+emission_CO2; 0.372, 0.688, tmp_cumulo+PL+PL_cumulo+AN_cumulo+interval_yield+Feed_Vol+RS_cumulo+rab_integral+RQ_integral+AS_Vol.+emission_CO2+interval_O2; 0.381, 0.688, tmp_cumulo+pH_cumulo+PL_cumulo+AN_cumulo+interval_yield+Feed_Vol+RS_cumulo+rab_integral+RQ_integral+AS_Vol.+emission_CO2; 0.361, 0.688, tmp+tmp_cumulo+PL_cumulo+AN_cumulo+interval_yield+interval_Pdt.+Feed_Vol+RS_cumulo+rab_integral+RQ_integral+AS_Vol.+emission_CO2+interval_O2; 0.371, 0.688, tmp_cumulo+AN+AN_cumulo+interval_yield+interval_Pdt.+Feed_Vol+RS_cumulo+rab_integral+RQ_integral+AS_Vol.+emission_CO2+consum_O2; 0.361, 0.688, tmp_cumulo+PL+PL_cumulo+AN_cumulo+interval_yield+interval_Pdt.+Feed_Vol+RS_cumulo+rab_integral+RQ_integral+AS_Vol.+emission_CO2+interval_O2; 0.371, 0.688, tmp_cumulo+PL+PL_cumulo+AN+AN_cumulo+interval_yield+Feed_Vol+RS_cumulo+rab_integral+RQ_integral+AS_Vol.+emission_CO2; 0.390, 0.688, tmp+PL_cumulo+AN_cumulo+interval_yield+interval_Pdt.+RS_cumulo+rab_integral+RQ_integral+AS_Vol.+emission_CO2; 0.381, 0.688, tmp_cumulo+PL+PL_cumulo+AN_cumulo+interval_yield+interval_Pdt.+RS_cumulo+rab_integral+RQ_integral+AS_Vol.+emission_CO2; 0.381, 0.688, tmp_cumulo+AN_cumulo+interval_yield+interval_Pdt.+RS+Feed_Vol+RS_cumulo+rab_integral+RQ_integral+AS_Vol.+emission_CO2; 0.371, 0.688, tmp_cumulo+pH+PL_cumulo+AN_cumulo+interval_yield+interval_Pdt.+Feed_Vol+RS_cumulo+rab_integral+RQ_integral+AS_Vol.+emission_CO2; 0.381, 0.688, pH+PL_cumulo+AN_cumulo+interval_yield+interval_Pdt.+RS_cumulo+rab_integral+RQ_integral+AS_Vol.+emission_CO2+interval_O2; 0.390, 0.688, tmp_cumulo+PL_cumulo+interval_yield+Feed_Vol+RS_cumulo+rab_integral+RQ_integral+AS_Vol.+emission_CO2+interval_O2; 0.371, 0.688, tmp_cumulo+pH_cumulo+PL_cumulo+AN_cumulo+interval_yield+Feed_Vol+RS_cumulo+rab_integral+RQ_integral+AS_Vol.+emission_CO2+interval_O2; 0.400, 0.687, PL_cumulo+AN_cumulo+interval_yield+Feed_Vol+RS_cumulo+rab_integral+RQ_integral+AS_Vol.+emission_CO2; 0.390, 0.687, tmp_cumulo+pH_cumulo+AN_cumulo+interval_yield+Feed_Vol+RS_cumulo+rab_integral+RQ_integral+AS_Vol.+emission_CO2; 0.360, 0.687, tmp_cumulo+pH+PL_cumulo+AN_cumulo+interval_yield+interval_Pdt.+Feed_Vol+RS_cumulo+rab_integral+RQ_integral+AS_Vol.+emission_CO2+consum_O2; 0.370, 0.687, tmp_cumulo+AN+AN_cumulo+interval_yield+RS+Feed_Vol+RS_cumulo+rab_integral+RQ_integral+AS_Vol.+emission_CO2+interval_O2; 0.390, 0.687, PL_cumulo+AN+AN_cumulo+interval_yield+interval_Pdt.+RS_cumulo+rab_integral+RQ_integral+AS_Vol.+emission_CO2; 0.390, 0.687, tmp_cumulo+pH+PL_cumulo+interval_yield+Feed_Vol+RS_cumulo+rab_integral+RQ_integral+AS_Vol.+emission_CO2; 0.380, 0.687, tmp_cumulo+PL_cumulo+AN+AN_cumulo+interval_yield+interval_Pdt.+RS_cumulo+rab_integral+RQ_integral+AS_Vol.+emission_CO2; 0.380, 0.687, tmp_cumulo+AN_cumulo+interval_yield+interval_Pdt.+RS+Feed_Vol+RS_cumulo+rab_integral+RQ_integral+AS_Vol.+emission_O2; 0.390, 0.687, tmp_cumulo+PL+AN_cumulo+interval_yield+Feed_Vol+RS_cumulo+rab_integral+RQ_integral+AS_Vol.+emission_CO2; 0.380, 0.687, O2+PL_cumulo+AN_cumulo+interval_yield+interval_Pdt.+Feed_Vol+RS_cumulo+rab_integral+RQ_integral+AS_Vol.+emission_CO2; 0.380, 0.687, tmp+tmp_cumulo+PL_cumulo+AN_cumulo+interval_yield+Feed_Vol+RS_cumulo+rab_integral+RQ_integral+AS_Vol.+emission_CO2; 0.360, 0.687, tmp_cumulo+AN+AN_cumulo+interval_yield+RS+Feed_Vol+RS_cumulo+rab_integral+RQ_integral+AS_Vol.+emission_CO2+consum_O2+interval_O2; 0.380, 0.687, O2+PL_cumulo+AN+AN_cumulo+interval_yield+interval_Pdt.+RS_cumulo+rab_integral+RQ_integral+AS_Vol.+emission_CO2; 0.370, 0.687, tmp_cumulo+PL_cumulo+AN_cumulo+interval_yield+interval_Pdt.+OD+Feed_Vol+RS_cumulo+rab_integral+RQ_integral+AS_Vol.+emission_CO2; 0.370, 0.687, tmp_cumulo+AN_cumulo+interval_yield+RS+Feed_Vol+RS_cumulo+rab_integral+RQ_integral+AS_Vol.+emission_CO2+consum_O2+interval_O2; 0.370, 0.687, tmp_cumulo+PL+PL_cumulo+AN_cumulo+interval_yield+RS+Feed_Vol+RS_cumulo+rab_integral+RQ_integral+AS_Vol.+emission_CO2; 0.380, 0.687, PL_cumulo+AN_cumulo+interval_yield+interval_Pdt.+RS_cumulo+rab_integral+RQ_integral+AS_Vol.+emission_CO2+consum_O2+interval_O2; 0.389, 0.687, tmp_cumulo+PL_cumulo+interval_yield+Feed_Vol+RS_cumulo+rab_integral+RQ_integral+AS_Vol.+emission_O2+emission_CO2; 0.380, 0.687, tmp_cumulo+pH+AN_cumulo+interval_yield+Feed_Vol+RS_cumulo+rab_integral+RQ_integral+AS_Vol.+emission_CO2+interval_O2; 0.359, 0.687, tmp_cumulo+pH_cumulo+PL_cumulo+AN_cumulo+interval_yield+interval_Pdt.+Feed_Vol+RS_cumulo+rab_integral+RQ_integral+AS_Vol.+emission_CO2+interval_O2; 0.389, 0.687, tmp_cumulo+PL+PL_cumulo+interval_yield+Feed_Vol+RS_cumulo+rab_integral+RQ_integral+AS_Vol.+emission_CO2; 0.408, 0.687, tmp_cumulo+PL_cumulo+interval_yield+RS+Feed_Vol+RS_cumulo+AS_Vol.+emission_O2; 0.369, 0.687, tmp+tmp_cumulo+PL_cumulo+AN_cumulo+interval_yield+interval_Pdt.+RS_cumulo+rab_integral+RQ_integral+AS_Vol.+emission_CO2+interval_O2; 0.408, 0.687, tmp_cumulo+PL_cumulo+interval_yield+Feed_Vol+RS_cumulo+RQ_integral+AS_Vol.+emission_CO2; 0.417, 0.687, PL_cumulo+interval_yield+interval_Pdt.+RS_cumulo+RQ_integral+AS_Vol.+emission_CO2; 0.389, 0.687, tmp_cumulo+PL_cumulo+interval_yield+interval_Pdt.+RS_cumulo+rab_integral+RQ_integral+AS_Vol.+emission_CO2+interval_O2; 0.389, 0.687, PL_cumulo+AN_cumulo+interval_yield+Feed_Vol+RS_cumulo+rab_integral+RQ_integral+AS_Vol.+emission_CO2+interval_O2; 0.398, 0.687, tmp_cumulo+PL_cumulo+interval_yield+RS+Feed_Vol+RS_cumulo+AS_Vol.+emission_O2+interval_O2; 0.359, 0.687, tmp_cumulo+PL+PL_cumulo+AN_cumulo+interval_yield+interval_Pdt.+Feed_Vol+RS_cumulo+rab_integral+RQ_integral+AS_Vol.+emission_CO2+consum_O2; 0.379, 0.687, tmp+PL+PL_cumulo+AN_cumulo+interval_yield+interval_Pdt.+RS_cumulo+rab_integral+RQ_integral+AS_Vol.+emission_CO2; 0.369, 0.687, tmp_cumulo+PL_cumulo+AN+AN_cumulo+interval_yield+interval_Pdt.+RS_cumulo+rab_integral+RQ_integral+AS_Vol.+emission_CO2+consum_O2; 0.359, 0.687, tmp_cumulo+AN+AN_cumulo+interval_yield+interval_Pdt.+RS+Feed_Vol+RS_cumulo+rab_integral+RQ_integral+AS_Vol.+emission_CO2+consum_O2; 0.389, 0.687, PL_cumulo+AN_cumulo+interval_yield+interval_Pdt.+Feed_Vol+RS_cumulo+rab_integral+RQ_integral+AS_Vol.+emission_CO2; 0.389, 0.686, tmp_cumulo+PL_cumulo+interval_yield+RS+Feed_Vol+RS_cumulo+rab_integral+RQ_integral+AS_Vol.+emission_CO2; 0.389, 0.686, tmp+tmp_cumulo+AN_cumulo+interval_yield+Feed_Vol+RS_cumulo+rab_integral+RQ_integral+AS_Vol.+emission_CO2; 0.369, 0.686, tmp_cumulo+AN_cumulo+interval_yield+interval_Pdt.+Feed_Vol+RS_cumulo+rab_integral+RQ_integral+AS_Vol.+emission_CO2+consum_O2+interval_O2; 0.379, 0.686, PL_cumulo+AN_cumulo+interval_yield+interval_Pdt.+RS+RS_cumulo+rab_integral+RQ_integral+AS_Vol.+emission_CO2+interval_O2; 0.369, 0.686, tmp+tmp_cumulo+PL_cumulo+AN_cumulo+interval_yield+Feed_Vol+RS_cumulo+rab_integral+RQ_integral+AS_Vol.+emission_CO2+interval_O2; 0.369, 0.686, tmp_cumulo+PL_cumulo+AN_cumulo+interval_yield+interval_Pdt.+RS+Feed_Vol+RS_cumulo+rab_integral+RQ_integral+AS_Vol.+emission_CO2; 0.379, 0.686, tmp_cumulo+AN_cumulo+interval_yield+Feed_Vol+RS_cumulo+rab_integral+RQ_integral+AS_Vol.+emission_CO2+consum_O2+interval_O2; 0.379, 0.686, tmp_cumulo+AN+AN_cumulo+interval_yield+interval_Pdt.+Feed_Vol+RS_cumulo+rab_integral+RQ_integral+AS_Vol.+emission_CO2; 0.358, 0.686, tmp_cumulo+PL_cumulo+AN_cumulo+interval_yield+interval_Pdt.+OD+Feed_Vol+RS_cumulo+rab_integral+RQ_integral+AS_Vol.+emission_CO2+interval_O2; 0.416, 0.686, O2+PL_cumulo+AN_cumulo+interval_yield+RS+Feed_Vol+AS_Vol.; 0.369, 0.686, tmp_cumulo+AN_cumulo+interval_yield+interval_Pdt.+RS+Feed_Vol+RS_cumulo+rab_integral+RQ_integral+AS_Vol.+emission_CO2+interval_O2; 0.358, 0.686, tmp_cumulo+PL_cumulo+AN+AN_cumulo+interval_yield+Feed_Vol+RS_cumulo+rab_integral+RQ_integral+AS_Vol.+emission_CO2+consum_O2+interval_O2; 0.388, 0.686, pH+PL_cumulo+AN_cumulo+interval_yield+interval_Pdt.+RS_cumulo+rab_integral+RQ_integral+AS_Vol.+emission_CO2; 0.358, 0.686, tmp_cumulo+PL_cumulo+AN_cumulo+interval_yield+RS+Feed_Vol+RS_cumulo+rab_integral+RQ_integral+AS_Vol.+emission_CO2+consum_O2+interval_O2; 0.358, 0.686, tmp_cumulo+PL_cumulo+AN+AN_cumulo+interval_yield+RS+Feed_Vol+RS_cumulo+rab_integral+RQ_integral+AS_Vol.+emission_CO2+interval_O2; 0.388, 0.686, tmp_cumulo+PL_cumulo+interval_yield+RS+Feed_Vol+RS_cumulo+AS_Vol.+emission_O2+consum_O2+interval_O2; 0.388, 0.686, tmp_cumulo+PL+PL_cumulo+interval_yield+interval_Pdt.+RS_cumulo+rab_integral+RQ_integral+AS_Vol.+emission_CO2; 0.368, 0.686, tmp_cumulo+PL_cumulo+AN+AN_cumulo+interval_yield+interval_Pdt.+Feed_Vol+RS_cumulo+rab_integral+RQ_integral+AS_Vol.+emission_CO2; 0.378, 0.686, tmp_cumulo+pH+AN_cumulo+interval_yield+RS+Feed_Vol+RS_cumulo+rab_integral+RQ_integral+AS_Vol.+emission_CO2; 0.378, 0.686, tmp_cumulo+pH+AN_cumulo+interval_yield+interval_Pdt.+Feed_Vol+RS_cumulo+rab_integral+RQ_integral+AS_Vol.+emission_CO2; 0.358, 0.686, tmp_cumulo+PL_cumulo+AN_cumulo+interval_yield+interval_Pdt.+Feed_Vol+RS_cumulo+rab_integral+RQ_integral+AS_Vol.+emission_O2+emission_CO2+interval_O2; 0.378, 0.686, tmp_cumulo+PL_cumulo+AN_cumulo+interval_yield+OD+Feed_Vol+RS_cumulo+rab_integral+RQ_integral+AS_Vol.+emission_CO2; 0.368, 0.686, tmp+tmp_cumulo+PL_cumulo+AN_cumulo+interval_yield+interval_Pdt.+Feed_Vol+RS_cumulo+rab_integral+RQ_integral+AS_Vol.+emission_CO2; 0.406, 0.686, tmp_cumulo+interval_yield+Feed_Vol+RS_cumulo+rab_integral+RQ_integral+AS_Vol.+emission_CO2; 0.357, 0.686, tmp+tmp_cumulo+PL_cumulo+AN_cumulo+interval_yield+interval_Pdt.+Feed_Vol+RS_cumulo+rab_integral+RQ_integral+AS_Vol.+emission_CO2+consum_O2; 0.378, 0.686, pH+PL+PL_cumulo+AN_cumulo+interval_yield+interval_Pdt.+RS_cumulo+rab_integral+RQ_integral+AS_Vol.+emission_CO2; 0.378, 0.686, tmp_cumulo+PL_cumulo+interval_yield+interval_Pdt.+Feed_Vol+RS_cumulo+rab_integral+RQ_integral+AS_Vol.+emission_O2+emission_CO2; 0.378, 0.686, tmp_cumulo+PL_cumulo+AN_cumulo+interval_yield+Feed_Vol+RS_cumulo+rab_integral+RQ_integral+AS_Vol.+emission_O2+emission_CO2; 0.397, 0.686, tmp_cumulo+PL_cumulo+AN_cumulo+interval_yield+RS+Feed_Vol+RS_cumulo+AS_Vol.+emission_O2; 0.397, 0.686, O2+PL_cumulo+interval_yield+interval_Pdt.+RS_cumulo+rab_integral+RQ_integral+AS_Vol.+emission_CO2; 0.368, 0.686, tmp_cumulo+PL_cumulo+AN_cumulo+interval_yield+interval_Pdt.+RS_cumulo+rab_integral+RQ_integral+AS_Vol.+emission_CO2+consum_O2+interval_O2; 0.378, 0.686, PL_cumulo+AN_cumulo+interval_yield+interval_Pdt.+OD+RS_cumulo+rab_integral+RQ_integral+AS_Vol.+emission_CO2+interval_O2; 0.367, 0.686, tmp_cumulo+AN+AN_cumulo+interval_yield+interval_Pdt.+Feed_Vol+RS_cumulo+rab_integral+RQ_integral+AS_Vol.+emission_CO2+interval_O2; 0.406, 0.686, tmp_cumulo+PL_cumulo+interval_yield+interval_Pdt.+RS_cumulo+RQ_integral+AS_Vol.+emission_CO2; 0.387, 0.686, PL_cumulo+AN_cumulo+interval_yield+interval_Pdt.+OD+RS_cumulo+rab_integral+RQ_integral+AS_Vol.+emission_CO2; 0.377, 0.686, pH_cumulo+PL_cumulo+AN_cumulo+interval_yield+interval_Pdt.+RS_cumulo+rab_integral+RQ_integral+AS_Vol.+emission_CO2+interval_O2; 0.387, 0.686, tmp_cumulo+AN_cumulo+interval_yield+interval_Pdt.+Feed_Vol+RS_cumulo+rab_integral+RQ_integral+AS_Vol.+emission_O2; 0.367, 0.685, tmp_cumulo+pH+PL_cumulo+AN_cumulo+interval_yield+Feed_Vol+RS_cumulo+rab_integral+RQ_integral+AS_Vol.+emission_CO2+consum_O2; 0.396, 0.685, tmp_cumulo+AN_cumulo+interval_yield+interval_Pdt.+RS_cumulo+rab_integral+RQ_integral+AS_Vol.+emission_CO2; 0.367, 0.685, tmp_cumulo+pH+PL_cumulo+AN_cumulo+interval_yield+interval_Pdt.+RS_cumulo+rab_integral+RQ_integral+AS_Vol.+emission_CO2+interval_O2; 0.377, 0.685, tmp+tmp_cumulo+PL_cumulo+AN_cumulo+interval_yield+interval_Pdt.+RS_cumulo+rab_integral+RQ_integral+AS_Vol.+emission_CO2; 0.346, 0.685, tmp_cumulo+PL_cumulo+AN+AN_cumulo+interval_yield+RS+Feed_Vol+RS_cumulo+rab_integral+RQ_integral+AS_Vol.+emission_CO2+consum_O2+interval_O2; 0.367, 0.685, tmp_cumulo+PL_cumulo+AN_cumulo+interval_yield+interval_Pdt.+RS+RS_cumulo+rab_integral+RQ_integral+AS_Vol.+emission_CO2+interval_O2; 0.387, 0.685, tmp_cumulo+AN_cumulo+interval_yield+OD+Feed_Vol+RS_cumulo+rab_integral+RQ_integral+AS_Vol.+emission_CO2; 0.367, 0.685, tmp_cumulo+AN+AN_cumulo+interval_yield+Feed_Vol+RS_cumulo+rab_integral+RQ_integral+AS_Vol.+emission_CO2+consum_O2+interval_O2; 0.356, 0.685, tmp_cumulo+PL_cumulo+AN_cumulo+interval_yield+interval_Pdt.+Feed_Vol+RS_cumulo+rab_integral+RQ_integral+AS_Vol.+emission_O2+emission_CO2+consum_O2; 0.367, 0.685, tmp_cumulo+PL_cumulo+AN+AN_cumulo+interval_yield+RS+Feed_Vol+RS_cumulo+rab_integral+RQ_integral+AS_Vol.+emission_CO2; 0.356, 0.685, tmp_cumulo+pH+AN+AN_cumulo+interval_yield+RS+Feed_Vol+RS_cumulo+rab_integral+RQ_integral+AS_Vol.+emission_CO2+consum_O2; 0.386, 0.685, PL_cumulo+AN_cumulo+interval_yield+interval_Pdt.+RS+RS_cumulo+rab_integral+RQ_integral+AS_Vol.+emission_CO2; 0.386, 0.685, tmp_cumulo+PL_cumulo+AN_cumulo+interval_yield+Feed_Vol+RS_cumulo+rab_integral+RQ_integral+AS_Vol.+emission_O2; 0.345, 0.685, tmp_cumulo+PL_cumulo+AN+AN_cumulo+interval_yield+interval_Pdt.+Feed_Vol+RS_cumulo+rab_integral+RQ_integral+AS_Vol.+emission_CO2+consum_O2+interval_O2; 0.345, 0.685, tmp_cumulo+PL_cumulo+AN+AN_cumulo+interval_yield+interval_Pdt.+RS+Feed_Vol+RS_cumulo+rab_integral+RQ_integral+AS_Vol.+emission_CO2+consum_O2; 0.356, 0.685, tmp_cumulo+PL_cumulo+AN_cumulo+interval_yield+interval_Pdt.+OD+Feed_Vol+RS_cumulo+rab_integral+RQ_integral+AS_Vol.+emission_CO2+consum_O2; 0.405, 0.685, PL_cumulo+AN_cumulo+interval_yield+RS+Feed_Vol+RS_cumulo+AS_Vol.+emission_O2; 0.366, 0.685, tmp_cumulo+PL_cumulo+AN_cumulo+interval_yield+Feed_Vol+RS_cumulo+rab_integral+RQ_integral+AS_Vol.+emission_O2+emission_CO2+interval_O2; 0.366, 0.685, tmp_cumulo+pH_cumulo+PL_cumulo+AN_cumulo+interval_yield+interval_Pdt.+Feed_Vol+RS_cumulo+rab_integral+RQ_integral+AS_Vol.+emission_CO2; 0.405, 0.685, O2+PL_cumulo+interval_yield+interval_Pdt.+RS_cumulo+RQ_integral+AS_Vol.+emission_CO2; 0.376, 0.685, tmp_cumulo+PL_cumulo+interval_yield+interval_Pdt.+Feed_Vol+RS_cumulo+rab_integral+RQ_integral+AS_Vol.+emission_CO2+interval_O2; 0.376, 0.685, tmp_cumulo+pH+AN+AN_cumulo+interval_yield+Feed_Vol+RS_cumulo+rab_integral+RQ_integral+AS_Vol.+emission_CO2; 0.356, 0.685, tmp_cumulo+pH+PL+PL_cumulo+AN_cumulo+interval_yield+interval_Pdt.+Feed_Vol+RS_cumulo+rab_integral+RQ_integral+AS_Vol.+emission_CO2; 0.386, 0.685, tmp+tmp_cumulo+PL_cumulo+interval_yield+interval_Pdt.+RS_cumulo+rab_integral+RQ_integral+AS_Vol.+emission_CO2; 0.366, 0.685, tmp_cumulo+PL+PL_cumulo+AN_cumulo+interval_yield+Feed_Vol+RS_cumulo+rab_integral+RQ_integral+AS_Vol.+emission_CO2+consum_O2; 0.366, 0.685, tmp_cumulo+PL_cumulo+AN_cumulo+interval_yield+interval_Pdt.+Feed_Vol+RS_cumulo+rab_integral+RQ_integral+AS_Vol.+emission_O2+emission_CO2; 0.376, 0.685, tmp_cumulo+AN_cumulo+interval_yield+interval_Pdt.+OD+Feed_Vol+RS_cumulo+rab_integral+RQ_integral+AS_Vol.+emission_CO2; 0.355, 0.685, tmp_cumulo+pH+PL_cumulo+AN+AN_cumulo+interval_yield+Feed_Vol+RS_cumulo+rab_integral+RQ_integral+AS_Vol.+emission_CO2+interval_O2; 0.376, 0.685, O2+PL_cumulo+AN_cumulo+interval_yield+interval_Pdt.+RS+RS_cumulo+rab_integral+RQ_integral+AS_Vol.+emission_CO2; 0.376, 0.685, PL_cumulo+AN+AN_cumulo+interval_yield+interval_Pdt.+RS_cumulo+rab_integral+RQ_integral+AS_Vol.+emission_CO2+consum_O2; 0.386, 0.685, tmp_cumulo+pH+PL_cumulo+interval_yield+interval_Pdt.+RS_cumulo+rab_integral+RQ_integral+AS_Vol.+emission_CO2; 0.345, 0.684, tmp_cumulo+PL_cumulo+AN_cumulo+interval_yield+interval_Pdt.+RS+Feed_Vol+RS_cumulo+rab_integral+RQ_integral+AS_Vol.+emission_CO2+consum_O2+interval_O2; 0.376, 0.684, tmp_cumulo+PL+PL_cumulo+interval_yield+interval_Pdt.+Feed_Vol+RS_cumulo+rab_integral+RQ_integral+AS_Vol.+emission_CO2; 0.376, 0.684, tmp_cumulo+pH_cumulo+AN_cumulo+interval_yield+Feed_Vol+RS_cumulo+rab_integral+RQ_integral+AS_Vol.+emission_CO2+interval_O2; 0.365, 0.684, tmp_cumulo+pH+AN_cumulo+interval_yield+interval_Pdt.+Feed_Vol+RS_cumulo+rab_integral+RQ_integral+AS_Vol.+emission_CO2+interval_O2; 0.376, 0.684, tmp_cumulo+AN+AN_cumulo+interval_yield+RS+Feed_Vol+RS_cumulo+rab_integral+RQ_integral+AS_Vol.+emission_O2; 0.365, 0.684, tmp_cumulo+PL+PL_cumulo+AN_cumulo+interval_yield+interval_Pdt.+RS_cumulo+rab_integral+RQ_integral+AS_Vol.+emission_CO2+interval_O2; 0.355, 0.684, tmp_cumulo+pH+PL_cumulo+AN_cumulo+interval_yield+RS+Feed_Vol+RS_cumulo+rab_integral+RQ_integral+AS_Vol.+emission_CO2+interval_O2; 0.375, 0.684, tmp_cumulo+AN_cumulo+interval_yield+RS+Feed_Vol+RS_cumulo+rab_integral+RQ_integral+AS_Vol.+emission_O2+consum_O2; 0.395, 0.684, O2+PL_cumulo+AN_cumulo+interval_yield+RS+Feed_Vol+AS_Vol.+consum_O2+interval_O2; 0.385, 0.684, tmp_cumulo+PL_cumulo+interval_yield+interval_Pdt.+RS_cumulo+rab_integral+RQ_integral+AS_Vol.+emission_O2+emission_CO2; 0.365, 0.684, tmp_cumulo+pH+AN_cumulo+interval_yield+RS+Feed_Vol+RS_cumulo+rab_integral+RQ_integral+AS_Vol.+emission_CO2+consum_O2; 0.404, 0.684, O2+PL_cumulo+interval_yield+OD+RS+Feed_Vol+AS_Vol.+interval_O2; 0.385, 0.684, tmp_cumulo+pH_cumulo+PL_cumulo+interval_yield+Feed_Vol+RS_cumulo+rab_integral+RQ_integral+AS_Vol.+emission_CO2; 0.365, 0.684, tmp_cumulo+pH_cumulo+PL+PL_cumulo+AN_cumulo+interval_yield+Feed_Vol+RS_cumulo+rab_integral+AS_Vol.+emission_CO2; 0.375, 0.684, tmp+tmp_cumulo+AN_cumulo+interval_yield+interval_Pdt.+Feed_Vol+RS_cumulo+rab_integral+RQ_integral+AS_Vol.+emission_CO2; 0.365, 0.684, tmp_cumulo+pH+PL_cumulo+AN_cumulo+interval_yield+RS+Feed_Vol+RS_cumulo+rab_integral+RQ_integral+AS_Vol.+emission_CO2; 0.394, 0.684, tmp_cumulo+AN_cumulo+interval_yield+Feed_Vol+RS_cumulo+rab_integral+RQ_integral+AS_Vol.+emission_O2; 0.375, 0.684, tmp_cumulo+AN+AN_cumulo+interval_yield+RS+Feed_Vol+ rab_integral+RQ_integral+AS_Vol.+emission_CO2+consum_O2; 0.375, 0.684, tmp_cumulo+pH+PL_cumulo+interval_yield+interval_Pdt.+Feed_Vol+RS_cumulo+rab_integral+RQ_integral+AS_Vol.+emission_CO2; 0.365, 0.684, tmp_cumulo+pH+AN_cumulo+interval_yield+interval_Pdt.+Feed_Vol+RS_cumulo+rab_integral+RQ_integral+AS_Vol.+emission_CO2+consum_O2; 0.375, 0.684, tmp_cumulo+pH+PL_cumulo+AN_cumulo+interval_yield+interval_Pdt.+RS_cumulo+rab_integral+RQ_integral+AS_Vol.+emission_CO2; 0.365, 0.684, tmp_cumulo+PL_cumulo+AN_cumulo+interval_yield+OD+Feed_Vol+RS_cumulo+rab_integral+RQ_integral+AS_Vol.+emission_CO2+interval_O2; 0.385, 0.684, pH_cumulo+PL_cumulo+AN_cumulo+interval_yield+interval_Pdt.+RS_cumulo+rab_integral+RQ_integral+AS_Vol.+emission_CO2; 0.403, 0.684, PL_cumulo+interval_yield+OD+RS+Feed_Vol+AS_Vol.+emission_O2+interval_O2; 0.375, 0.684, tmp_cumulo+AN_cumulo+interval_yield+RS+Feed_Vol+RS_cumulo+rab_integral+RQ_integral+AS_Vol.+emission_O2+interval_O2; 0.365, 0.684, tmp_cumulo+pH+PL_cumulo+AN+AN_cumulo+interval_yield+Feed_Vol+RS_cumulo+rab_integral+RQ_integral+AS_Vol.+emission_CO2; 0.375, 0.684, tmp_cumulo+pH+AN_cumulo+interval_yield+Feed_Vol+RS_cumulo+rab_integral+RQ_integral+AS_Vol.+emission_CO2+consum_O2; 0.343, 0.684, tmp_cumulo+pH+PL_cumulo+AN_cumulo+interval_yield+interval_Pdt.+Feed_Vol+RS_cumulo+rab_integral+RQ_integral+AS_Vol.+emission_CO2+consum_O2+interval_O2; 0.354, 0.684, tmp_cumulo+pH_cumulo+PL_cumulo+AN_cumulo+interval_yield+interval_Pdt.+Feed_Vol+RS_cumulo+rab_integral+RQ_integral+AS_Vol.+emission_CO2+consum_O2; 0.364, 0.684, tmp_cumulo+pH+AN_cumulo+interval_yield+RS+Feed_Vol+RS_cumulo+rab_integral+RQ_integral+AS_Vol.+emission_CO2+interval_O2; 0.375, 0.684, tmp+tmp_cumulo+AN_cumulo+interval_yield+RS+Feed_Vol+RS_cumulo+rab_integral+RQ_integral+AS_Vol.+emission_CO2; 0.384, 0.684, tmp_cumulo+PL_cumulo+interval_yield+interval_Pdt.+Feed_Vol+RS_cumulo+rab_integral+RQ_integral+AS_Vol.+emission_O2; 0.394, 0.684, O2+PL_cumulo+AN_cumulo+interval_yield+RS+Feed_Vol+RS_cumulo+AS_Vol.+emission_CO2; 0.394, 0.684, tmp+PL_cumulo+interval_yield+interval_Pdt.+RS_cumulo+rab_integral+RQ_integral+AS_Vol.+emission_CO2; 0.364, 0.684, O2+PL_cumulo+AN_cumulo+interval_yield+interval_Pdt.+Feed_Vol+RS_cumulo+rab_integral+RQ_integral+AS_Vol.+emission_CO2+interval_O2; 0.374, 0.684, tmp_cumulo+PL_cumulo+AN_cumulo+interval_yield+interval_Pdt.+RS+RS_cumulo+rab_integral+RQ_integral+AS_Vol.+emission_CO2; 0.354, 0.684, tmp_cumulo+PL_cumulo+AN_cumulo+interval_yield+interval_Pdt.+RS+Feed_Vol+RS_cumulo+rab_integral+RQ_integral+AS_Vol.+emission_O2+consum_O2; 0.384, 0.684, tmp_cumulo+PL_cumulo+interval_yield+RS+Feed_Vol+RS_cumulo+rab_integral+RQ_integral+AS_Vol.+emission_O2; 0.364, 0.684, tmp_cumulo+PL+PL_cumulo+AN+AN_cumulo+interval_yield+interval_Pdt.+RS_cumulo+rab_integral+RQ_integral+AS_Vol.+emission_CO2; 0.364, 0.684, tmp_cumulo+AN_cumulo+interval_yield+RS+Feed_Vol+RS_cumulo+rab_integral+RQ_integral+AS_Vol.+emission_O2+consum_O2+interval_O2; 0.364, 0.684, tmp_cumulo+PL_cumulo+AN_cumulo+interval_yield+Feed_Vol+RS_cumulo+rab_integral+RQ_integral+Accum._Yield+AS_Vol.+emission_CO2+interval_O2; 0.374, 0.684, O2+PL_cumulo+AN_cumulo+interval_yield+RS+Feed_Vol+RS_cumulo+rab_integral+RQ_integral+AS_Vol.+emission_CO2; 0.374, 0.683, tmp+tmp_cumulo+AN_cumulo+interval_yield+Feed_Vol+RS_cumulo+rab_integral+RQ_integral+AS_Vol.+emission_CO2+interval_O2; 0.374, 0.683, tmp_cumulo+pH_cumulo+AN_cumulo+interval_yield+interval_Pdt.+Feed_Vol+RS_cumulo+rab_integral+RQ_integral+AS_Vol.+emission_CO2; 0.374, 0.683, tmp_cumulo+PL+AN_cumulo+interval_yield+RS+Feed_Vol+RS_cumulo+rab_integral+RQ_integral+AS_Vol.+emission_CO2; 0.402, 0.683, O2+PL_cumulo+interval_yield+RS+Feed_Vol+AS_Vol.+consum_O2+interval_O2; 0.374, 0.683, O2+PL_cumulo+AN_cumulo+interval_yield+interval_Pdt.+RS_cumulo+rab_integral+RQ_integral+AS_Vol.+emission_CO2+consum_O2; 0.411, 0.683, O2+PL_cumulo+interval_yield+RS+Feed_Vol+AS_Vol.+interval_O2; 0.374, 0.683, tmp+PL_cumulo+AN_cumulo+interval_yield+interval_Pdt.+RS_cumulo+rab_integral+RQ_integral+AS_Vol.+emission_CO2+consum_O2; 0.353, 0.683, tmp_cumulo+AN_cumulo+interval_yield+interval_Pdt.+RS+Feed_Vol+RS_cumulo+rab_integral+RQ_integral+AS_Vol.+emission_CO2+consum_O2+interval_O2; 0.393, 0.683, PL_cumulo+interval_yield+interval_Pdt.+RS_cumulo+rab_integral+RQ_integral+AS_Vol.+emission_CO2+interval_O2; 0.353, 0.683, tmp_cumulo+pH+PL+PL_cumulo+AN_cumulo+interval_yield+Feed_Vol+RS_cumulo+rab_integral+RQ_integral+AS_Vol.+emission_CO2+interval_O2; 0.393, 0.683, O2+PL_cumulo+AN_cumulo+interval_yield+interval_Pdt.+RS_cumulo+RQ_integral+AS_Vol.+emission_CO2; 0.393, 0.683, O2+PL_cumulo+interval_yield+OD+RS+Feed_Vol+AS_Vol.+consum_O2+interval_O2; 0.364, 0.683, tmp+tmp_cumulo+PL+PL_cumulo+AN_cumulo+interval_yield+Feed_Vol+RS_cumulo+rab_integral+RQ_integral+AS_Vol.+emission_CO2; 0.374, 0.683, PL_cumulo+AN_cumulo+interval_yield+interval_Pdt.+Feed_Vol+RS_cumulo+rab_integral+RQ_integral+AS_Vol.+emission_CO2+consum_O2; 0.393, 0.683, tmp_cumulo+AN_cumulo+interval_yield+RS+Feed_Vol+rab_integral+RQ_integral+AS_Vol.+emission_O2; 0.383, 0.683, pH_cumulo+PL+PL_cumulo+interval_yield+OD+RS+Feed_Vol+AS_Vol.+consum_O2+interval_O2; 0.353, 0.683, tmp_cumulo+pH+PL_cumulo+AN+AN_cumulo+interval_yield+Feed_Vol+RS_cumulo+rab_integral+RQ_integral+AS_Vol.+emission_CO2+consum_O2; 0.383, 0.683, tmp_cumulo+PL_cumulo+interval_yield+interval_Pdt.+RS+RS_cumulo+rab_integral+RQ_integral+AS_Vol.+emission_CO2; 0.353, 0.683, tmp_cumulo+PL+PL_cumulo+AN+AN_cumulo+interval_yield+Feed_Vol+RS_cumulo+rab_integral+RQ_integral+AS_Vol.+emission_CO2+interval_O2; 0.374, 0.683, tmp_cumulo+PL+AN_cumulo+interval_yield+Feed_Vol+RS_cumulo+rab_integral+RQ_integral+AS_Vol.+emission_CO2+interval_O2; 0.383, 0.683, tmp+tmp_cumulo+PL_cumulo+interval_yield+Feed_Vol+RS_cumulo+rab_integral+RQ_integral+AS_Vol.+emission_CO2; 0.402, 0.683, PL_cumulo+AN_cumulo+interval_yield+interval_Pdt.+RS_cumulo+RQ_integral+AS_Vol.+emission_CO2; 0.374, 0.683, tmp_cumulo+pH_cumulo+AN_cumulo+interval_yield+RS+Feed_Vol+RS_cumulo+rab_integral+RQ_integral+AS_Vol.+emission_CO2; 0.383, 0.683, tmp_cumulo+AN_cumulo+interval_yield+interval_Pdt.+RS_cumulo+rab_integral+RQ_integral+AS_Vol.+emission_CO2+interval_O2; 0.374, 0.683, pH+PL+PL_cumulo+AN_cumulo+interval_yield+Feed_Vol+RS_cumulo+rab_integral+RQ_integral+AS_Vol.+emission_CO2; 0.363, 0.683, tmp_cumulo+pH+AN+AN_cumulo+interval_yield+Feed_Vol+RS_cumulo+rab_integral+RQ_integral+AS_Vol.+emission_CO2+consum_O2; 0.353, 0.683, tmp_cumulo+pH+PL_cumulo+AN_cumulo+interval_yield+RS+Feed_Vol+RS_cumulo+rab_integral+RQ_integral+AS_

Vol.+emission_CO2+consum_O2; 0.383, 0.683, tmp_cumulo+AN+AN_cumulo+interval_yield+interval_Pdt.+RS_cumulo+rab_integral+RQ_integral+AS_Vol.+emission_CO2; 0.402, 0.683, O2+PL_cumulo+AN_cumulo+interval_yield+RS+Feed_Vol+RS_cumulo+AS_Vol.; 0.353, 0.683, tmp_cumulo+PL_cumulo+AN_cumulo+interval_yield+interval_Pdt.+Feed_Vol+RS_cumulo+rab_integral+RQ_integral+Accum._Yield+AS_Vol.+emission_CO2+consum_O2; 0.353, 0.683, tmp+tmp_cumulo+AN+AN_cumulo+interval_yield+RS+Feed_Vol+RS_cumulo+rab_integral+RQ_integral+AS_Vol.+emission_CO2+consum_O2; 0.353, 0.683, tmp_cumulo+PL+PL_cumulo+AN+AN_cumulo+interval_yield+Feed_Vol+RS_cumulo+rab_integral+RQ_integral+AS_Vol.+emission_CO2+consum_O2; 0.373, 0.683, tmp+PL+PL_cumulo+AN_cumulo+interval_yield+Feed_Vol+RS_cumulo+rab_integral+RQ_integral+AS_Vol.+emission_CO2; 0.373, 0.683, O2+PL_cumulo+AN_cumulo+interval_yield+interval_Pdt.+OD+RS_cumulo+rab_integral+RQ_integral+AS_Vol.+emission_CO2; 0.363, 0.683, tmp_cumulo+PL_cumulo+AN_cumulo+interval_yield+interval_Pdt.+OD+RS_cumulo+rab_integral+RQ_integral+AS_Vol.+emission_CO2+interval_O2; 0.353, 0.683, tmp_cumulo+PL_cumulo+AN_cumulo+interval_yield+interval_Pdt.+Feed_Vol+RS_cumulo+rab_integral+RQ_integral+Accum._Yield+AS_Vol.+emission_CO2+interval_O2; 0.363, 0.683, tmp+PL_cumulo+AN_cumulo+interval_yield+interval_Pdt.+Feed_Vol+RS_cumulo+rab_integral+RQ_integral+AS_Vol.+emission_CO2+interval_O2; 0.373, 0.683, tmp_cumulo+PL+AN+AN_cumulo+interval_yield+Feed_Vol+RS_cumulo+rab_integral+RQ_integral+AS_Vol.+emission_CO2; 0.373, 0.683, tmp_cumulo+PL+AN_cumulo+interval_yield+interval_Pdt.+Feed_Vol+RS_cumulo+rab_integral+RQ_integral+AS_Vol.+emission_CO2; 0.363, 0.683, tmp_cumulo+AN_cumulo+interval_yield+interval_Pdt.+RS+Feed_Vol+RS_cumulo+rab_integral+RQ_integral+AS_Vol.+emission_O2+consum_O2; 0.363, 0.683, tmp_cumulo+PL_cumulo+AN_cumulo+interval_yield+RS+Feed_Vol+RS_cumulo+rab_integral+RQ_integral+AS_Vol.+emission_O2+interval_O2; 0.363, 0.683, tmp_cumulo+pH+AN+AN_cumulo+interval_yield+Feed_Vol+RS_cumulo+rab_integral+RQ_integral+AS_Vol.+emission_CO2+interval_O2; 0.373, 0.683, tmp_cumulo+AN_cumulo+interval_yield+OD+RS+Feed_Vol+RS_cumulo+rab_integral+RQ_integral+AS_Vol.+emission_CO2; 0.363, 0.683, tmp_cumulo+PL_cumulo+AN_cumulo+interval_yield+RS+Feed_Vol+RS_cumulo+rab_integral+RQ_integral+AS_Vol.+emission_O2+consum_O2; 0.383, 0.683, tmp_cumulo+PL_cumulo+interval_yield+interval_Pdt.+RS_cumulo+rab_integral+RQ_integral+AS_Vol.+emission_CO2+consum_O2; 0.363, 0.683, tmp+tmp_cumulo+AN_cumulo+interval_yield+interval_Pdt.+Feed_Vol+RS_cumulo+rab_integral+RQ_integral+AS_Vol.+emission_CO2+interval_O2; 0.363, 0.683, O2+PL_cumulo+AN+AN_cumulo+interval_yield+interval_Pdt.+RS_cumulo+rab_integral+RQ_integral+AS_Vol.+emission_CO2+interval_O2; 0.383, 0.683, tmp_cumulo+PL_cumulo+interval_yield+Feed_Vol+RS_cumulo+rab_integral+RQ_integral+AS_Vol.+emission_CO2+consum_O2; 0.392, 0.683, O2+PL_cumulo+AN_cumulo+interval_yield+Feed_Vol+RS_cumulo+RQ_integral+AS_Vol.+emission_CO2; 0.392, 0.683, tmp_cumulo+PL+PL_cumulo+interval_yield+Feed_Vol+RS_cumulo+RQ_integral+AS_Vol.+emission_CO2; 0.373, 0.683, tmp_cumulo+PL_cumulo+interval_yield+interval_Pdt.+Feed_Vol+RS_cumulo+rab_integral+RQ_integral+AS_Vol.+emission_CO2+consum_O2; 0.341, 0.683, tmp_cumulo+PL+PL_cumulo+AN_cumulo+interval_yield+interval_Pdt.+Feed_Vol+RS_cumulo+rab_integral+RQ_integral+AS_Vol.+emission_CO2+consum_O2+interval_O2; 0.362, 0.683, tmp_cumulo+pH_cumulo+PL_cumulo+AN_cumulo+interval_yield+interval_Pdt.+RS_cumulo+rab_integral+RQ_integral+AS_Vol.+emission_CO2+interval_O2; 0.362, 0.682, tmp+PL+PL_cumulo+AN_cumulo+interval_yield+interval_Pdt.+RS_cumulo+rab_integral+RQ_integral+AS_Vol.+emission_CO2+interval_O2; 0.372, 0.682, O2+PL_cumulo+AN_cumulo+interval_yield+Feed_Vol+RS_cumulo+rab_integral+RQ_integral+AS_Vol.+emission_CO2+interval_O2; 0.352, 0.682, tmp_cumulo+PL_cumulo+AN+AN_cumulo+interval_yield+interval_Pdt.+RS_cumulo+rab_integral+RQ_integral+AS_Vol.+emission_CO2+consum_O2+interval_O2; 0.382, 0.682, PL_cumulo+AN_cumulo+interval_yield+interval_Pdt.+RS_cumulo+rab_integral+RQ_integral+AS_Vol.+emission_CO2+generate_CO2; 0.382, 0.682, tmp_cumulo+PL_cumulo+AN+AN_cumulo+interval_yield+interval_Pdt.+RS_cumulo+rab_integral+RQ_integral+emission_CO2; 0.352, 0.682, tmp_cumulo+PL+PL_cumulo+AN_cumulo+interval_yield+RS+Feed_Vol+RS_cumulo+rab_integral+RQ_integral+AS_Vol.+emission_CO2+interval_O2; 0.352, 0.682, tmp_cumulo+pH+PL+PL_cumulo+AN+AN_cumulo+interval_yield+Feed_Vol+RS_cumulo+rab_integral+RQ_integral+AS_Vol.+emission_CO2; 0.341, 0.682, tmp_cumulo+pH+PL_cumulo+AN+AN_cumulo+interval_yield+RS+Feed_Vol+RS_cumulo+rab_integral+RQ_integral+AS_Vol.+emission_CO2+consum_O2; 0.372, 0.682, tmp_cumulo+pH+AN_cumulo+interval_yield+RS+Feed_Vol+RS_cumulo+rab_integral+RQ_integral+AS_Vol.+emission_O2; 0.362, 0.682, tmp_cumulo+PL_cumulo+AN_cumulo+interval_yield+Feed_Vol+RS_cumulo+rab_integral+RQ_integral+AS_Vol.+emission_O2+emission_CO2+consum_O2; 0.362, 0.682, tmp+tmp_cumulo+PL_cumulo+AN_cumulo+interval_yield+Feed_Vol+RS_cumulo+rab_integral+RQ_integral+AS_Vol.+emission_CO2+consum_O2; 0.382, 0.682, tmp_cumulo+PL_cumulo+AN+interval_yield+Feed_Vol+RS_cumulo+rab_integral+RQ_integral+AS_Vol.+emission_CO2; 0.362, 0.682, tmp_cumulo+pH_cumulo+PL_cumulo+AN_cumulo+interval_yield+interval_Pdt.+Feed_Vol+RS_cumulo+rab_integral+RQ_integral+AS_Vol.+emission_O2; 0.352, 0.682, tmp_cumulo+pH+PL+PL_cumulo+AN_cumulo+interval_yield+RS+Feed_Vol+RS_cumulo+rab_integral+RQ_integral+AS_Vol.+emission_CO2; 0.372, 0.682, tmp_cumulo+pH+PL+PL_cumulo+interval_yield+Feed_Vol+RS_cumulo+rab_integral+RQ_integral+AS_Vol.+emission_CO2; 0.362, 0.682, tmp_cumulo+PL_cumulo+AN+AN_cumulo+interval_yield+RS+Feed_Vol+RS_cumulo+rab_integral+RQ_integral+AS_Vol.+emission_O2; 0.372, 0.682, tmp_cumulo+PL_cumulo+AN_cumulo+interval_yield+RS+Feed_Vol+RS_cumulo+AS_Vol.+emission_O2+consum_O2+interval_O2; 0.382, 0.682, tmp_cumulo+AN+AN_cumulo+interval_yield+RS+Feed_Vol+rab_integral+RQ_integral+AS_Vol.+emission_O2; 0.372, 0.682, tmp_cumulo+PL_cumulo+AN+interval_yield+interval_Pdt.+Feed_Vol+RS_cumulo+rab_integral+RQ_integral+AS_Vol.+emission_CO2; 0.372, 0.682, tmp_cumulo+PL_cumulo+interval_yield+interval_Pdt.+RS+Feed_Vol+RS_cumulo+rab_integral+RQ_integral+AS_Vol.+emission_CO2; 0.372, 0.682, pH_cumulo+PL+PL_cumulo+AN_cumulo+interval_yield+interval_Pdt.+RS_cumulo+rab_integral+RQ_integral+AS_Vol.+emission_CO2; 0.362, 0.682, tmp+tmp_cumulo+AN_cumulo+interval_yield+interval_Pdt.+Feed_Vol+RS_cumulo+rab_integral+RQ_integral+AS_Vol.+emission_CO2+consum_O2; 0.351, 0.682, tmp_cumulo+PL+PL_cumulo+AN+AN_cumulo+interval_yield+interval_Pdt.+Feed_Vol+RS_cumulo+rab_integral+RQ_integral+AS_Vol.+emission_CO2; 0.362, 0.682, tmp_cumulo+PL_cumulo+AN_cumulo+interval_yield+Feed_Vol+RS_cumulo+rab_integral+RQ_integral+Accum._Yield+AS_Vol.+emission_CO2+consum_O2; 0.391, 0.682, tmp_cumulo+interval_yield+interval_Pdt.+Feed_Vol+RS_cumulo+rab_integral+RQ_integral+AS_Vol.+emission_CO2; 0.418, 0.682, PL_cumulo+interval_yield+RS_cumulo+RQ_integral+AS_Vol.+emission_CO2; 0.351, 0.682, tmp_cumulo+PL+PL_cumulo+AN+AN_cumulo+interval_yield+RS+Feed_Vol+RS_cumulo+rab_integral+RQ_integral+AS_Vol.+emission_CO2; 0.391, 0.682, tmp_cumulo+PL_cumulo+AN+AN_cumulo+interval_yield+RS_cumulo+rab_integral+RQ_integral+emission_CO2; 0.418, 0.682, tmp_cumulo+interval_yield+RS+Feed_Vol+RS_cumulo+AS_Vol.; 0.409, 0.682, O2+PL_cumulo+interval_yield+RS+Feed_Vol+RS_cumulo+AS_Vol.; 0.351, 0.682, tmp_cumulo+PL+PL_cumulo+AN_cumulo+interval_yield+interval_Pdt.+RS+Feed_Vol+RS_cumulo+rab_integral+RQ_integral+AS_Vol.+emission_CO2; 0.362, 0.682, tmp_cumulo+AN_cumulo+interval_yield+interval_Pdt.+OD+Feed_Vol+RS_cumulo+rab_integral+RQ_integral+AS_Vol.+emission_CO2+consum_O2; 0.391, 0.682, tmp_cumulo+PL_cumulo+interval_yield+OD+RS+Feed_Vol+AS_Vol.+emission_O2+interval_O2; 0.372, 0.682, pH+PL_cumulo+AN_cumulo+interval_yield+interval_Pdt.+RS_cumulo+rab_integral+RQ_integral+AS_Vol.+emission_CO2+consum_O2; 0.362, 0.682, tmp+tmp_cumulo+pH+PL_cumulo+AN_cumulo+interval_yield+Feed_Vol+RS_cumulo+rab_integral+RQ_integral+AS_Vol.+emission_CO2; 0.351, 0.682, tmp_cumulo+PL_cumulo+AN_cumulo+interval_yield+RS+Feed_Vol+RS_cumulo+rab_integral+RQ_integral+AS_Vol.+emission_O2+consum_O2+interval_O2; 0.372, 0.682, tmp+tmp_cumulo+AN+AN_cumulo+interval_yield+Feed_Vol+RS_cumulo+rab_integral+AS_Vol.+emission_CO2; 0.351, 0.682, tmp_cumulo+AN+AN_cumulo+interval_yield+OD+RS+Feed_Vol+RS_cumulo+rab_integral+RQ_integral+AS_Vol.+emission_CO2+consum_O2; 0.372, 0.682, PL_cumulo+AN_cumulo+interval_yield+interval_Pdt.+RS_cumulo+rab_integral+RQ_integral+AS_Vol.+emission_CO2+interval_O2+generate_CO2; 0.340, 0.682, tmp_cumulo+pH+PL+PL_cumulo+AN_cumulo+interval_yield+interval_Pdt.+Feed_Vol+RS_cumulo+rab_integral+RQ_integral+AS_Vol.+emission_CO2+interval_O2; 0.351, 0.682, tmp_cumulo+AN+AN_cumulo+interval_yield+interval_Pdt.+Feed_Vol+RS_cumulo+rab_integral+RQ_integral+AS_Vol.+emission_CO2+consum_O2+interval_O2; 0.409, 0.682, tmp_cumulo+PL_cumulo+interval_yield+RS+Feed_Vol+RS_cumulo+AS_Vol.; 0.381, 0.682, tmp_cumulo+PL_cumulo+AN_cumulo+interval_yield+RS+Feed_Vol+rab_integral+RQ_integral+AS_Vol.+emission_O2; 0.372, 0.682, tmp_cumulo+PL_cumulo+AN_cumulo+interval_yield+interval_Pdt.+OD+RS_cumulo+rab_integral+RQ_integral+AS_Vol.+emission_CO2; 0.340, 0.682, tmp+tmp_cumulo+PL_cumulo+AN_cumulo+interval_yield+interval_Pdt.+Feed_Vol+RS_cumulo+rab_integral+RQ_integral+AS_Vol.+emission_CO2+consum_O2+interval_O2; 0.351, 0.682, tmp_cumulo+pH+PL+PL_cumulo+AN_cumulo+interval_yield+Feed_Vol+RS_cumulo+rab_integral+RQ_integral+AS_Vol.+emission_CO2+consum_O2+interval_O2; 0.361, 0.682, tmp+tmp_cumulo+interval_yield+RS+Feed_Vol+RS_cumulo+rab_integral+RQ_integral+AS_Vol.+emission_CO2+consum_O2; 0.361, 0.682, tmp+PL_cumulo+AN+AN_cumulo+interval_yield+interval_Pdt.+RS_cumulo+rab_integral+RQ_integral+AS_Vol.+emission_CO2+interval_O2; 0.361, 0.682, tmp_cumulo+pH_cumulo+AN_cumulo+interval_yield+interval_Pdt.+Feed_Vol+RS_cumulo+rab_integral+RQ_integral+AS_Vol.+emission_CO2+interval_O2; 0.371, 0.682, tmp_cumulo+pH+PL_cumulo+interval_yield+Feed_Vol+RS_cumulo+rab_integral+RQ_integral+AS_Vol.+emission_CO2+interval_O2; 0.371, 0.682, O2+PL_cumulo+AN+AN_cumulo+interval_yield+Feed_Vol+RS_cumulo+rab_integral+RQ_integral+AS_Vol.+emission_CO2; 0.391, 0.682, tmp_cumulo+interval_yield+RS+Feed_Vol+RS_cumulo+rab_integral+RQ_integral+AS_Vol.+emission_CO2; 0.400, 0.682, tmp_cumulo+PL_cumulo+AN+AN_cumulo+interval_yield+RS_cumulo+RQ_integral+emission_CO2; 0.400, 0.682, tmp_cumulo+PL+PL_cumulo+interval_yield+RS+Feed_Vol+RS_cumulo+AS_Vol.; 0.371, 0.682, tmp+tmp_cumulo+PL_cumulo+interval_yield+interval_Pdt.+Feed_Vol+RS_cumulo+rab_integral+RQ_integral+AS_Vol.+emission_CO2; 0.340, 0.682, tmp_cumulo+PL_cumulo+AN+AN_cumulo+interval_yield+RS+Feed_Vol+RS_cumulo+rab_integral+RQ_integral+AS_Vol.+emission_O2+emission_CO2+consum_O2; 0.361, 0.682, pH+PL_cumulo+AN_cumulo+interval_yield+interval_Pdt.+Feed_Vol+RS_cumulo+rab_integral+RQ_integral+AS_Vol.+emission_CO2+interval_O2; 0.361, 0.682, tmp_cumulo+pH_cumulo+PL_cumulo+AN_cumulo+interval_yield+Feed_Vol+RS_cumulo+rab_integral+RQ_integral+AS_Vol.+emission_CO2+consum_O2; 0.361, 0.682, tmp+PL+PL_cumulo+AN_cumulo+interval_yield+interval_Pdt.+Feed_Vol+RS_cumulo+rab_integral+RQ_integral+AS_Vol.+emission_CO2; 0.371, 0.682, tmp_cumulo+PL_cumulo+AN_cumulo+interval_yield+Feed_Vol+RS_cumulo+rab_integral+RQ_integral+Accum._Yield+AS_Vol.+emission_CO2; 0.371, 0.682, tmp_cumulo+pH+PL+AN_cumulo+interval_yield+Feed_Vol+RS_cumulo+rab_integral+RQ_integral+AS_Vol.+emission_CO2; 0.381, 0.682, tmp_cumulo+PL_cumulo+interval_yield+interval_Pdt.+OD+RS_cumulo+rab_integral+RQ_integral+AS_Vol.+emission_CO2; 0.340, 0.682, tmp_cumulo+pH+PL_cumulo+AN+AN_cumulo+interval_yield+interval_Pdt.+Feed_Vol+RS_cumulo+rab_integral+RQ_integral+AS_Vol.+emission_CO2+consum_O2; 0.400, 0.682, O2+PL_cumulo+AN_cumulo+interval_yield+RS+Feed_Vol+AS_Vol.+interval_O2; 0.371, 0.682, tmp_cumulo+AN_cumulo+interval_yield+OD+Feed_Vol+RS_cumulo+rab_integral+RQ_integral+AS_Vol.+emission_CO2+interval_O2; 0.381, 0.682, tmp_cumulo+pH_cumulo+PL_cumulo+interval_yield+interval_Pdt.+RS_cumulo+rab_integral+RQ_integral+AS_Vol.+emission_CO2; 0.350, 0.682, tmp_cumulo+PL_cumulo+AN_cumulo+interval_yield+interval_Pdt.+RS+Feed_Vol+RS_cumulo+rab_integral+RQ_integral+AS_Vol.+emission_O2+interval_O2; 0.409, 0.682, PL_cumulo+interval_yield+Feed_Vol+RS_cumulo+RQ_integral+AS_Vol.+emission_CO2; 0.381, 0.682, PL_cumulo+AN_cumulo+interval_yield+RS+Feed_Vol+RS_cumulo+rab_integral+RQ_integral+AS_Vol.+emission_CO2; 0.371, 0.682, tmp_cumulo+PL_cumulo+AN+interval_yield+interval_Pdt.+Feed_Vol+RS_cumulo+rab_integral+RQ_integral+AS_Vol.+emission_O2; 0.350, 0.682, tmp_cumulo+PL+PL_cumulo+AN_cumulo+interval_yield+RS+Feed_Vol+RS_cumulo+rab_integral+RQ_integral+AS_Vol.+emission_CO2+consum_O2; 0.361, 0.681, tmp+tmp_cumulo+PL_cumulo+AN_cumulo+interval_yield+interval_Pdt.+RS_cumulo+rab_integral+RQ_integral+AS_Vol.+emission_CO2+consum_O2; 0.350, 0.681, tmp+tmp_cumulo+pH+PL_cumulo+AN_cumulo+interval_yield+Feed_Vol+RS_cumulo+rab_integral+RQ_integral+AS_Vol.+emission_CO2+interval_O2; 0.350, 0.681, tmp+tmp_ cumulo+PL_cumulo+AN+AN_cumulo+interval_yield+interval_Pdt.+RS_cumulo+rab_integral+RQ_integral+AS_Vol.+emission_CO2+interval_O2; 0.350, 0.681, tmp_cumulo+AN+AN_cumulo+interval_yield+RS+Feed_Vol+RS_cumulo+rab_integral+RQ_integral+AS_Vol.+emission_O2+emission_CO2+consum_O2; 0.390, 0.681, tmp_cumulo+interval_yield+Feed_Vol+RS_cumulo+rab_integral+RQ_integral+AS_Vol.+emission_CO2+interval_O2; 0.361, 0.681, tmp_cumulo+AN_cumulo+interval_yield+interval_Pdt.+OD+Feed_Vol+RS_cumulo+rab_integral+RQ_integral+AS_Vol.+emission_CO2+interval_O2; 0.371, 0.681, tmp+tmp_cumulo+pH+AN_cumulo+interval_yield+Feed_Vol+RS_cumulo+rab_integral+RQ_integral+AS_Vol.+emission_CO2; 0.381, 0.681, tmp+PL_cumulo+AN_cumulo+interval_yield+Feed_Vol+RS_cumulo+rab_integral+RQ_integral+AS_Vol.+emission_CO2; 0.339, 0.681, tmp_cumulo+pH+PL_cumulo+AN+AN_cumulo+interval_yield+interval_Pdt.+Feed_Vol+RS_cumulo+rab_integral+RQ_integral+AS_Vol.+emission_CO2+interval_O2; 0.371, 0.681, tmp_cumulo+AN_cumulo+interval_yield+RS+Feed_Vol+RS_cumulo+rab_integral+RQ_integral+AS_Vol.+consum_O2+generate_CO2; 0.381, 0.681, tmp_cumulo+AN_cumulo+interval_yield+Feed_Vol+RS_cumulo+rab_integral+RQ_integral+AS_Vol.+emission_CO2+generate_CO2; 0.350, 0.681, tmp_cumulo+PL_cumulo+AN_cumulo+interval_yield+RS+Feed_Vol+RS_cumulo+rab_integral+RQ_integral+AS_Vol.+emission_O2+emission_CO2+consum_O2; 0.361, 0.681, tmp+tmp_cumulo+PL_cumulo+AN_cumulo+interval_yield+RS+Feed_Vol+RS_cumulo+rab_integral+RQ_integral+AS_Vol.+emission_CO2; 0.371, 0.681, PL_cumulo+AN_cumulo+interval_yield+RS+Feed_Vol+RS_cumulo+rab_integral+RQ_integral+AS_Vol.+emission_CO2+interval_O2; 0.381, 0.681, tmp_cumulo+PL_cumulo+interval_yield+OD+RS+Feed_Vol+RS_cumulo+AS_Vol.+emission_O2+interval_O2; 0.371, 0.681, PL_cumulo+AN_cumulo+interval_yield+interval_Pdt.+RS_cumulo+rab_integral+RQ_integral+AS_Vol.+emission_O2+emission_CO2+interval_O2; 0.361, 0.681, tmp_cumulo+pH+PL_cumulo+AN_cumulo+interval_yield+RS+Feed_Vol+RS_cumulo+rab_integral+RQ_integral+AS_Vol.+emission_O2; 0.339, 0.681, tmp_cumulo+PL+PL_cumulo+AN+AN_cumulo+interval_yield+RS+Feed_Vol+RS_cumulo+rab_integral+RQ_integral+AS_Vol.+emission_CO2+consum_O2; 0.390, 0.681, PL_cumulo+AN+interval_yield+interval_Pdt.+RS_cumulo+rab_integral+RQ_integral+AS_Vol.+emission_CO2; 0.399, 0.681, O2+PL_cumulo+interval_yield+RS+Feed_Vol+RS_cumulo+AS_Vol.+interval_O2; 0.361, 0.681, pH+PL+PL_cumulo+AN_cumulo+interval_yield+interval_Pdt.+Feed_Vol+RS_cumulo+rab_integral+RQ_integral+AS_Vol.+emission_CO2; 0.380, 0.681, tmp_cumulo+AN_cumulo+interval_yield+RS+Feed_Vol+RS_cumulo+rab_integral+RQ_integral+AS_Vol.+consum_O2; 0.371, 0.681, tmp_cumulo+PL_cumulo+AN_cumulo+interval_yield+RS+Feed_Vol+RS_cumulo+rab_integral+AS_Vol.+emission_O2+generate_CO2; 0.360, 0.681, tmp_cumulo+AN+AN_cumulo+interval_yield+interval_Pdt.+RS+Feed_Vol+RS_cumulo+rab_integral+RQ_integral+AS_Vol.+emission_CO2; 0.371, 0.681, tmp_cumulo+AN_cumulo+interval_yield+RS+Feed_Vol+RS_cumulo+rab_integral+AS_Vol.+emission_O2+consum_O2+interval_O2; 0.360, 0.681, tmp+tmp_cumulo+AN_cumulo+interval_yield+RS+Feed_Vol+RS_cumulo+rab_integral+RQ_integral+AS_Vol.+emission_CO2+interval_O2; 0.360, 0.681, tmp_cumulo+PL_cumulo+AN_cumulo+interval_yield+RS+Feed_Vol+RS_cumulo+rab_integral+RQ_integral+AS_Vol.+emission_O2+emission_CO2; 0.390, 0.681, O2+PL_cumulo+interval_yield+OD+RS+Feed_Vol+AS_Vol.+emission_O2+interval_O2; 0.370, 0.681, tmp_cumulo+pH_cumulo+AN+AN_cumulo+interval_yield+Feed_Vol+RS_cumulo+rab_integral+RQ_integral+AS_Vol.+emission_CO2; 0.339, 0.681, tmp_cumulo+pH+PL_cumulo+AN_cumulo+interval_yield+interval_Pdt.+RS+Feed_Vol+RS_cumulo+rab_integral+RQ_integral+AS_Vol.+emission_CO2+consum_O2; 0.370, 0.681, tmp_cumulo+pH_cumulo+PL_cumulo+AN_cumulo+interval_yield+interval_Pdt.+RS_cumulo+rab_integral+RQ_integral+AS_Vol.+emission_CO2; 0.360, 0.681, PL_cumulo+AN+AN_cumulo+interval_yield+interval_Pdt.+RS+Feed_Vol+RS_cumulo+rab_integral+RQ_integral+AS_Vol.+emission_CO2+consum_O2+interval_O2; 0.390, 0.681, tmp_cumulo+PL_cumulo+interval_yield+Feed_Vol+RS_cumulo+RQ_integral+AS_Vol.+emission_CO2+interval_O2; 0.360, 0.681, pH+PL+PL_cumulo+AN_cumulo+interval_yield+interval_Pdt.+RS_cumulo+rab_integral+RQ_integral+AS_Vol.+emission_CO2+interval_O2; 0.370, 0.681, tmp+tmp_cumulo+AN_cumulo+interval_yield+RS+Feed_Vol+RS_cumulo+rab_integral+RQ_integral+AS_Vol.+emission_O2; 0.350, 0.681, tmp_cumulo+pH+AN_cumulo+interval_yield+interval_Pdt.+RS+Feed_Vol+RS_cumulo+rab_integral+RQ_integral+AS_Vol.+emission_CO2+consum_O2; 0.370, 0.681, tmp_cumulo+AN+AN_cumulo+interval_yield+interval_Pdt.+RS_cumulo+rab_integral+RQ_integral+AS_Vol.+emission_CO2+interval_O2; 0.350, 0.681, tmp+tmp_cumulo+PL_cumulo+AN+AN_cumulo+interval_yield+Feed_Vol+RS_cumulo+rab_integral+RQ_integral+AS_Vol.+emission_CO2+interval_O2; 0.339, 0.681, tmp_cumulo+PL_cumulo+AN+AN_cumulo+interval_yield+interval_Pdt.+RS+Feed_Vol+RS_cumulo+rab_integral+RQ_integral+AS_Vol.+emission_CO2+interval_O2; 0.380, 0.681, tmp+PL+PL_cumulo+interval_yield+interval_Pdt.+RS_cumulo+rab_integral+RQ_integral+AS_Vol.+emission_CO2; 0.350, 0.681, tmp+tmp_cumulo+PL_cumulo+AN_cumulo+interval_yield+RS+Feed_Vol+RS_cumulo+rab_integral+RQ_integral+AS_Vol.+emission_CO2+interval_O2; 0.350, 0.681, tmp_cumulo+PL+PL_cumulo+AN_cumulo+interval_yield+interval_Pdt.+OD+Feed_Vol+RS_cumulo+rab_integral+RQ_integral+AS_Vol.+emission_CO2; 0.390, 0.681, tmp_cumulo+PL+PL_cumulo+interval_yield+interval_Pdt.+RS_cumulo+RQ_integral+AS_Vol.+emission_CO2; 0.339, 0.681, tmp_cumulo+pH+PL_cumulo+AN_cumulo+interval_yield+interval_Pdt.+RS+Feed_Vol+RS_cumulo+rab_integral+RQ_integral+AS_Vol.+emission_CO2+interval_O2; 0.360, 0.681, tmp_cumulo+pH+AN+AN_cumulo+interval_yield+RS+Feed_Vol+RS_cumulo+rab_integral+RQ_integral+AS_Vol.+emission_CO2; 0.370, 0.681, tmp+PL_cumulo+AN_cumulo+interval_yield+Feed_Vol+RS_cumulo+rab_integral+RQ_integral+AS_Vol.+emission_CO2+interval_O2; 0.360, 0.681, tmp_cumulo+pH_cumulo+PL_cumulo+AN_cumulo+interval_yield+RS+Feed_Vol+RS_cumulo+rab_integral+RQ_integral+AS_Vol.+emission_CO2; 0.350, 0.681, tmp_cumulo+pH_cumulo+PL_cumulo+AN_cumulo+interval_yield+RS+Feed_Vol+RS_cumulo+rab_integral+RQ_integral+AS_Vol.+emission_CO2+interval_O2; 0.360, 0.681, pH+PL_cumulo+AN+AN_cumulo+interval_yield+interval_Pdt.+RS_cumulo+rab_integral+RQ_integral+AS_Vol.+emission_CO2+interval_O2; 0.339, 0.681, tmp_cumulo+PL+PL_cumulo+AN+AN_cumulo+interval_yield+interval_Pdt.+Feed_Vol+RS_cumulo+rab_integral+RQ_integral+AS_Vol.+emission_CO2+consum_O2; 0.389, 0.681, tmp_cumulo+pH+PL_cumulo+interval_yield+Feed_Vol+RS_cumulo+RQ_integral+AS_Vol.+emission_CO2;

0.370, 0.681, tmp_cumulo+AN+AN_cumulo+interval_yield+RS+Feed_Vol+rab_integral+RQ_integral+AS_Vol.+emission_O2+consum_O2; 0.339, 0.681, tmp_cumulo+PL_cumulo+AN_cumulo+interval_yield+interval_Pdt.+RS+Feed_Vol+RS_cumulo+rab_integral+RQ_integral+AS_Vol.+emission_O2+consum_O2+interval_O2; 0.370, 0.681, tmp_cumulo+PL_cumulo+interval_yield+interval_Pdt.+RS+Feed_Vol+RS_cumulo+rab_integral+RQ_integral+AS_Vol.+emission_O2; 0.380, 0.681, pH+PL_cumulo+AN_cumulo+interval_yield+Feed_Vol+RS_cumulo+rab_integral+RQ_integral+AS_Vol.+emission_CO2; 0.360, 0.681, tmp+PL_cumulo+AN_cumulo+interval_yield+interval_Pdt.+RS_cumulo+rab_integral+RQ_integral+AS_Vol.+emission_CO2+consum_O2+interval_O2; 0.349, 0.681, tmp_cumulo+PL_cumulo+AN+AN_cumulo+interval_yield+Feed_Vol+RS_cumulo+rab_integral+RQ_integral+AS_Vol.+emission_O2+emission_CO2+consum_O2; 0.370, 0.681, tmp_cumulo+pH+PL_cumulo+interval_yield+Feed_Vol+RS_cumulo+rab_integral+RQ_integral+AS_Vol.+emission_O2+emission_CO2; 0.360, 0.681, tmp+PL_cumulo+AN_cumulo+interval_yield+interval_Pdt.+RS+RS_cumulo+rab_integral+RQ_integral+AS_Vol.+emission_CO2+interval_O2; 0.370, 0.681, tmp_cumulo+pH_cumulo+PL_cumulo+interval_yield+interval_Pdt.+Feed_Vol+RS_cumulo+rab_integral+RQ_integral+AS_Vol.+emission_CO2; 0.349, 0.681, tmp_cumulo+AN+AN_cumulo+interval_yield+interval_Pdt.+RS+Feed_Vol+RS_cumulo+rab_integral+RQ_integral+AS_Vol.+emission_CO2+interval_O2; 0.360, 0.681, tmp_cumulo+pH+PL+PL_cumulo+AN_cumulo+interval_yield+interval_Pdt.+RS_cumulo+rab_integral+RQ_integral+AS_Vol.+emission_CO2; 0.370, 0.681, tmp_cumulo+PL_cumulo+interval_yield+RS+Feed_Vol+RS_cumulo+rab_integral+RQ_integral+AS_Vol.+emission_O2+emission_CO2; 0.338, 0.681, tmp+tmp_cumulo+pH+PL_cumulo+AN_cumulo+interval_yield+interval_Pdt.+Feed_Vol+RS_cumulo+rab_integral+RQ_integral+AS_Vol.+emission_CO2+interval_O2; 0.360, 0.681, tmp_cumulo+PL_cumulo+AN_cumulo+interval_yield+OD+RS+Feed_Vol+RS_cumulo+rab_integral+RQ_integral+AS_Vol.+emission_CO2; 0.370, 0.681, tmp_cumulo+PL+AN_cumulo+interval_yield+Feed_Vol+RS_cumulo+rab_integral+RQ_integral+AS_Vol.+emission_CO2+consum_O2; 0.370, 0.681, PL_cumulo+AN_cumulo+interval_yield+interval_Pdt.+OD+Feed_Vol+RS_cumulo+rab_integral+RQ_integral+AS_Vol.+emission_CO2; 0.360, 0.681, tmp_cumulo+AN_cumulo+interval_yield+OD+RS+Feed_Vol+RS_cumulo+rab_integral+RQ_integral+AS_Vol.+emission_CO2+consum_O2; 0.360, 0.681, tmp_cumulo+PL+AN_cumulo+interval_yield+interval_Pdt.+Feed_Vol+RS_cumulo+rab_integral+RQ_integral+AS_Vol.+emission_CO2+interval_O2; 0.349, 0.681, tmp_cumulo+pH+PL_cumulo+AN+AN_cumulo+interval_yield+interval_Pdt.+RS_cumulo+rab_integral+RQ_integral+AS_Vol.+emission_CO2+interval_O2; 0.349, 0.681, tmp+tmp_cumulo+PL+PL_cumulo+AN_cumulo+interval_yield+interval_Pdt.+Feed_Vol+RS_cumulo+rab_integral+RQ_integral+AS_Vol.+emission_CO2; 0.398, 0.681, PL_cumulo+interval_yield+interval_Pdt.+RS_cumulo+RQ_integral+AS_Vol.+emission_CO2+interval_O2; 0.360, 0.681, tmp_cumulo+PL+PL_cumulo+AN_cumulo+interval_yield+OD+Feed_Vol+RS_cumulo+rab_integral+RQ_integral+AS_Vol.+emission_CO2; 0.360, 0.681, tmp+tmp_cumulo+PL_cumulo+AN+AN_cumulo+interval_yield+Feed_Vol+RS_cumulo+rab_integral+RQ_integral+AS_Vol.+emission_CO2; 0.370, 0.681, PL_cumulo+AN_cumulo+interval_yield+interval_Pdt.+RS+RS_cumulo+rab_integral+RQ_integral+AS_Vol.+emission_CO2+consum_O2; 0.360, 0.681, tmp_cumulo+AN+AN_cumulo+interval_yield+OD+Feed_Vol+RS_cumulo+rab_integral+RQ_integral+AS_Vol.+emission_CO2+consum_O2; 0.389, 0.681, pH_cumulo+PL+PL_cumulo+interval_yield+OD+RS+Feed_Vol+AS_Vol.+interval_O2; 0.349, 0.681, tmp_cumulo+PL+PL_cumulo+AN_cumulo+interval_yield+Feed_Vol+RS_cumulo+rab_integral+RQ_integral+AS_Vol.+emission_CO2+consum_O2+interval_O2; 0.360, 0.681, tmp_cumulo+pH_cumulo+AN_cumulo+interval_yield+RS+Feed_Vol+RS_cumulo+rab_integral+RQ_integral+AS_Vol.+emission_CO2+interval_O2; 0.370, 0.681, tmp_cumulo+pH_cumulo+AN_cumulo+interval_yield+RS+Feed_Vol+RS_cumulo+rab_integral+RQ_integral+AS_Vol.+emission_O2; 0.389, 0.681, tmp_cumulo+PL_cumulo+interval_yield+RS+Feed_Vol+RS_cumulo+RQ_integral+AS_Vol.+emission_CO2; 0.359, 0.681, tmp_cumulo+PL_cumulo+AN_cumulo+interval_yield+OD+Feed_Vol+RS_cumulo+rab_integral+RQ_integral+AS_Vol.+emission_CO2+consum_O2; 0.398, 0.681, O2+PL_cumulo+interval_yield+Feed_Vol+RS_cumulo+RQ_integral+AS_Vol.+emission_CO2; 0.370, 0.681, tmp_cumulo+PL_cumulo+AN_cumulo+interval_yield+interval_Pdt.+RS_cumulo+rab_integral+RQ_integral+AS_Vol.+emission_CO2+generate_CO2; 0.359, 0.681, tmp_cumulo+PL+AN_cumulo+interval_yield+interval_Pdt.+Feed_Vol+RS_cumulo+rab_integral+RQ_integral+AS_Vol.+emission_CO2+consum_O2; 0.370, 0.681, tmp+tmp_cumulo+AN_cumulo+interval_yield+Feed_Vol+RS_cumulo+rab_integral+RQ_integral+AS_Vol.+emission_CO2+consum_O2; 0.379, 0.681, tmp_cumulo+AN_cumulo+interval_yield+Feed_Vol+RS_cumulo+rab_integral+RQ_integral+AS_Vol.+emission_O2+emission_CO2; 0.359, 0.681, tmp+tmp_cumulo+PL+PL_cumulo+AN_cumulo+interval_yield+interval_Pdt.+RS_cumulo+rab_integral+RQ_integral+AS_Vol.+emission_CO2; 0.379, 0.681, tmp_cumulo+PL_cumulo+interval_yield+OD+RS+Feed_Vol+AS_Vol.+emission_O2+consum_O2+interval_O2; 0.379, 0.681, tmp_cumulo+PL_cumulo+interval_yield+interval_Pdt.+RS_cumulo+rab_integral+RQ_integral+AS_Vol.+emission_CO2+generate_CO2; 0.349, 0.681, tmp_cumulo+pH_cumulo+PL_cumulo+AN+AN_cumulo+interval_yield+Feed_Vol+RS_cumulo+rab_integral+RQ_integral+AS_Vol.+emission_CO2+interval_O2; 0.338, 0.681, tmp_cumulo+AN+AN_cumulo+interval_yield+interval_Pdt.+RS+Feed_Vol+RS_cumulo+rab_integral+RQ_integral+AS_Vol.+emission_CO2+consum_O2+interval_O2; 0.369, 0.681, tmp_cumulo+PL_cumulo+AN_cumulo+interval_yield+Feed_Vol+RS_cumulo+rab_integral+RQ_integral+AS_Vol.+emission_CO2+generate_CO2; 0.359, 0.681, tmp_cumulo+pH+PL_cumulo+AN_cumulo+interval_yield+interval_Pdt.+Feed_Vol+RS_cumulo+rab_integral+RQ_integral+AS_Vol.+emission_O2; 0.389, 0.681, tmp_cumulo+PL_cumulo+interval_yield+Feed_Vol+RS_cumulo+rab_integral+RQ_integral+AS_Vol.+emission_O2; 0.338, 0.681, tmp_cumulo+PL_cumulo+AN_cumulo+interval_yield+interval_Pdt.+Feed_Vol+RS_cumulo+rab_integral+RQ_integral+AS_Vol.+emission_O2+emission_CO2+consum_O2+interval_O2; 0.389, 0.681, pH+PL_cumulo+interval_yield+interval_Pdt.+RS_cumulo+rab_integral+RQ_integral+AS_Vol.+emission_CO2; 0.416, 0.681, O2+PL_cumulo+interval_yield+RS+Feed_Vol+AS_Vol.; 0.369, 0.680, tmp_cumulo+AN+AN_cumulo+interval_yield+OD+Feed_Vol+RS_cumulo+rab_integral+RQ_integral+AS_Vol.+emission_CO2; 0.379, 0.680, tmp_cumulo+PL_cumulo+interval_yield+OD+Feed_Vol+RS_cumulo+rab_integral+RQ_integral+AS_Vol.+emission_CO2; 0.369, 0.680, tmp_ cumulo+PL_cumulo+interval_yield+OD+RS+Feed_Vol+ RS_cumulo+AS_Vol.+emission_O2+consum_O2+interval_ O2; 0.379, 0.680, tmp_cumulo+PL_cumulo+AN_cumulo+ interval_yield+RS+Feed_Vol+RS_cumulo+AS_Vol.+ emission_O2+interval_O2; 0.379, 0.680, O2+PL_cumulo+ AN_cumulo+interval_yield+RS+Feed_Vol+rab_integral+ RQ_integral+AS_Vol.+emission_CO2; 0.369, 0.680, tmp_ cumulo+PL_cumulo+interval_yield+interval_Pdt.+OD+ Feed_Vol+RS_cumulo+rab_integral+RQ_integral+AS_ Vol.+emission_CO2; 0.348, 0.680, tmp+tmp_cumulo+PL_ cumulo+AN_cumulo+interval_yield+RS+Feed_Vol+RS_ cumulo+rab_integral+RQ_integral+AS_Vol.+emission_ CO2+consum_O2; 0.398, 0.680, O2+PL_cumulo+AN_ cumulo+interval_yield+RS+Feed_Vol+AS_Vol.+emission_ CO2; 0.348, 0.680, tmp_cumulo+PL_cumulo+AN+AN_ cumulo+interval_yield+interval_Pdt.+RS+RS_cumulo+ rab_integral+RQ_integral+AS_Vol.+emission_CO2+ interval_O2; 0.369, 0.680, pH+PL_cumulo+AN_cumulo+ interval_yield+Feed_Vol+RS_cumulo+rab_integral+RQ_ integral+AS_Vol.+emission_CO2+interval_O2; 0.389, 0.680, tmp_cumulo+PL_cumulo+interval_yield+interval_ Pdt.+Feed_Vol+RS_cumulo+RQ_integral+AS_Vol.+emission_CO2; 0.389, 0.680, PL_cumulo+interval_yield+interval_Pdt.+RS_cumulo+rab_integral+RQ_integral+AS_Vol.+ emission_O2+emission_CO2; 0.369, 0.680, tmp_cumulo+ pH+PL_cumulo+interval_yield+RS+Feed_Vol+RS_ cumulo+rab_integral+RQ_integral+AS_Vol.+emission_ CO2; 0.348, 0.680, tmp_cumulo+PL+AN+AN_cumulo+ interval_yield+RS+Feed_Vol+RS_cumulo+rab_integral+ RQ_integral+AS_Vol.+emission_CO2+consum_O2; 0.359, 0.680, tmp_cumulo+pH+PL_cumulo+AN_cumulo+interval_yield+interval_Pdt.+RS_cumulo+rab_integral+RQ_integral+AS_Vol.+emission_CO2+consum_O2; 0.369, 0.680, tmp_cumulo+PL+PL_cumulo+interval_yield+Feed_Vol+ RS_cumulo+rab_integral+RQ_integral+AS_Vol.+emission_CO2+interval_O2; 0.359, 0.680, tmp_cumulo+PL_cumulo+AN_cumulo+interval_yield+interval_Pdt.+RS_ cumulo+rab_integral+RQ_integral+AS_Vol.+emission_ CO2+interval_O2+generate_CO2; 0.348, 0.680, tmp+tmp_ cumulo+PL_cumulo+AN+AN_cumulo+interval_yield+ Feed_Vol+RS_cumulo+rab_integral+RQ_integral+AS_ Vol.+emission_CO2+consum_O2; 0.359, 0.680, tmp_ cumulo+pH+PL_cumulo+AN_cumulo+interval_yield+ OD+Feed_Vol+RS_cumulo+rab_integral+RQ_integral+ AS_Vol.+emission_CO2; 0.398, 0.680, PL_cumulo+AN_ cumulo+interval_yield+Feed_Vol+RS_cumulo+RQ_ integral+AS_Vol.+emission_CO2; 0.359, 0.680, tmp_ cumulo+PL_cumulo+AN_cumulo+interval_yield+interval_ Pdt.+RS_cumulo+rab_integral+RQ_integral+AS_Vol.+ emission_O2+emission_CO2+interval_O2; 0.359, 0.680, PL_cumulo+AN_cumulo+interval_yield+interval_Pdt.+ Feed_Vol+RS_cumulo+rab_integral+RQ_integral+AS_ Vol.+emission_CO2+consum_O2+interval_O2; 0.359, 0.680, tmp_cumulo+PL_cumulo+AN+AN_cumulo+interval_yield+RS+Feed_Vol+rab_integral+RQ_integral+AS_ Vol.+emission_CO2+consum_O2; 0.348, 0.680, tmp_cumulo+PL_cumulo+AN+AN_cumulo+interval_yield+Feed_ Vol+RS_cumulo+rab_integral+RQ_integral+AS_Vol.+ emission_O2+emission_CO2; 0.369, 0.680, tmp_cumulo+AN_cumulo+interval_yield+OD+Feed_Vol+ RS_cumulo+rab_integral+RQ_integral+AS_Vol.+emission_CO2+consum_O2; 0.348, 0.680, tmp_cumulo+AN_ cumulo+interval_yield+interval_Pdt.+RS+Feed_Vol+RS_ cumulo+rab_integral+RQ_integral+AS_Vol.+emission_ O2+consum_O2+interval_O2; 0.398, 0.680, O2+PL_ cumulo+AN_cumulo+interval_yield+RS+Feed_Vol+AS_ Vol.+consum_O2; 0.348, 0.680, tmp_cumulo+pH_cumulo+ PL+PL_cumulo+AN_cumulo+interval_yield+interval_ Pdt.+Feed_Vol+RS_cumulo+rab_integral+RQ_integral+ AS_Vol.+emission_CO2; 0.359, 0.680, tmp_cumulo+PL_ cumulo+AN_cumulo+interval_yield+interval_Pdt.+Feed_ Vol+RS_cumulo+rab_integral+RQ_integral+AS_Vol.+ emission_O2+interval_O2; 0.359, 0.680, tmp+tmp_ cumulo+AN+AN_cumulo+interval_yield+Feed_Vol+RS_ cumulo+rab_integral+RQ_integral+AS_Vol.+emission_ CO2+consum_O2; 0.337, 0.680, tmp_cumulo+PL_cumulo+ AN_cumulo+interval_yield+interval_Pdt.+RS+Feed_Vol+ RS_cumulo+rab_integral+RQ_integral+AS_Vol.+ emission_O2+emission_CO2+consum_O2; 0.348, 0.680, tmp_cumulo+PL_cumulo+AN+AN_cumulo+interval_ yield+Feed_Vol+RS_cumulo+rab_integral+RQ_integral+ Accum._Yield+AS_Vol.+emission_CO2+consum_O2; 0.398, 0.680, PL_cumulo+interval_yield+interval_Pdt.+ OD+RS_cumulo+RQ_integral+AS_Vol.+emission_CO2; 0.359, 0.680, PL_cumulo+AN_cumulo+interval_yield+interval_Pdt.+OD+Feed_Vol+RS_cumulo+rab_integral+RQ_ integral+AS_Vol.+emission_CO2+interval_O2; 0.359, 0.680, tmp+pH+PL_cumulo+AN_cumulo+interval_yield+ interval_Pdt.+RS_cumulo+rab_integral+RQ_integral+AS_ Vol.+emission_CO2+interval_O2; 0.348, 0.680, tmp_cumulo+pH+AN+AN_cumulo+interval_yield+interval_Pdt.+ Feed_Vol+RS_cumulo+rab_integral+RQ_integral+AS_ Vol.+emission_CO2+consum_O2; 0.359, 0.680, tmp_ cumulo+pH_cumulo+PL_cumulo+AN_cumulo+interval_ yield+RS+Feed_Vol+RS_cumulo+rab_integral+RQ_ integral+AS_Vol.+emission_O2; 0.379, 0.680, tmp_ cumulo+AN_cumulo+interval_yield+Feed_Vol+RS_ cumulo+rab_integral+RQ_integral+Accum._Yield+AS_ Vol.+emission_CO2; 0.359, 0.680, tmp_cumulo+AN_ cumulo+interval_yield+interval_Pdt.+RS+Feed_Vol+RS_ cumulo+rab_integral+RQ_integral+AS_Vol.+emission_ O2+interval_O2; 0.388, 0.680, tmp_cumulo+PL_cumulo+ interval_yield+Feed_Vol+RS_cumulo+RQ_integral+AS_ Vol.+emission_O2+emission_CO2; 0.369, 0.680, tmp_ cumulo+PL+PL_cumulo+interval_yield+RS+Feed_Vol+ RS_cumulo+rab_integral+RQ_integral+AS_Vol.+ emission_CO2; 0.348, 0.680, tmp_cumulo+PL+PL_ cumulo+AN+AN_cumulo+interval_yield+interval_Pdt.+ RS_cumulo+rab_integral+RQ_integral+AS_Vol.+ emission_CO2+interval_O2; 0.359, 0.680, tmp_cumulo+ AN_cumulo+interval_yield+RS+Feed_Vol+RS_cumulo+ rab_integral+RQ_integral+AS_Vol.+emission_O2+ emission_CO2+consum_O2; 0.369, 0.680, pH_cumulo+ PL_cumulo+AN_cumulo+interval_yield+interval_Pdt.+ RS_cumulo+rab_integral+RQ_integral+AS_Vol.+ emission_CO2+consum_O2; 0.369, 0.680, tmp_cumulo+ AN_cumulo+interval_yield+RS+Feed_Vol+RS_cumulo+ rab_integral+RQ_integral+AS_Vol.+emission_O2+ generate_CO2; 0.369, 0.680, O2+PL_cumulo+AN_ cumulo+interval_yield+interval_Pdt.+RS_cumulo+rab_ integral+RQ_integral+AS_Vol.+emission_CO2+generate_ CO2; 0.369, 0.680, tmp+PL_cumulo+AN_cumulo+ interval_yield+interval_Pdt.+Feed_Vol+RS_cumulo+rab_ integral+RQ_integral+AS_Vol.+emission_CO2; 0.337, 0.680, tmp_cumulo+PL_cumulo+AN_cumulo+interval_ yield+interval_Pdt.+OD+Feed_Vol+RS_cumulo+rab_integral+RQ_integral+AS_Vol.+emission_CO2+consum_O2+ interval_O2; 0.358, 0.680, tmp_cumulo+pH+PL_cumulo+ AN_cumulo+interval_yield+Feed_Vol+RS_cumulo+rab_ integral+RQ_integral+AS_Vol.+emission_O2+emission_ CO2; 0.379, 0.680, tmp_cumulo+AN_cumulo+interval_ yield+RS+Feed_Vol+rab_integral+RQ_integral+AS_Vol.+ emission_O2+consum_O2; 0.337, 0.680, tmp+tmp_ cumulo+PL_cumulo+AN+AN_cumulo+interval_yield+

RS+Feed_Vol+RS_cumulo+rab_integral+RQ_integral+ AS_Vol.+emission_CO2+consum_O2; 0.358, 0.680, PL_cumulo+AN_cumulo+interval_yield+interval_Pdt.+ RS+Feed_Vol+RS_cumulo+rab_integral+RQ_integral+ AS_Vol.+emission_CO2+interval_O2; 0.358, 0.680, O2+PL_cumulo+AN_cumulo+interval_yield+interval_ Pdt.+RS+RS_cumulo+rab_integral+RQ_integral+AS_Vol.+ emission_CO2+interval_O2; 0.388, 0.680, tmp_cumulo+ AN_cumulo+interval_yield+RS+Feed_Vol+rab_integral+ RQ_integral+AS_Vol.+consum_O2; 0.358, 0.680, tmp_ cumulo+PL+AN_cumulo+interval_yield+RS+Feed_Vol+ RS_cumulo+rab_integral+RQ_integral+AS_Vol.+ emission_CO2+consum_O2; 0.378, 0.680, tmp_cumulo+ PL_cumulo+AN+AN_cumulo+interval_yield+RS+RS_ cumulo+rab_integral+RQ_integral+emission_CO2; 0.348, 0.680, tmp_cumulo+pH+AN_cumulo+interval_yield+RS+ Feed_Vol+RS_cumulo+rab_integral+RQ_integral+AS_ Vol.+emission_CO2+consum_O2+interval_O2; 0.358, 0.680, tmp+PL+PL_cumulo+AN+AN_cumulo+interval_ yield+interval_Pdt.+RS_cumulo+rab_integral+RQ_inte- gral+AS_Vol.+emission_CO2; 0.358, 0.680, tmp_cumulo+ PL+PL_cumulo+AN_cumulo+interval_yield+interval_ Pdt.+RS_cumulo+rab_integral+RQ_integral+AS_Vol.+ emission_CO2+consum_O2; 0.369, 0.680, tmp_cumulo+ PL_cumulo+interval_yield+RS+Feed_Vol+RS_cumulo+ rab_integral+RQ_integral+AS_Vol.+emission_CO2+ interval_O2; 0.388, 0.680, tmp_cumulo+AN_cumulo+ interval_yield+RS+Feed_Vol+RS_cumulo+rab_integral+ RQ_integral+AS_Vol.; 0.388, 0.680, tmp_cumulo+PL_ cumulo+AN_cumulo+interval_yield+Feed_Vol+RS_ cumulo+RQ_integral+AS_Vol.+emission_CO2; 0.358, 0.680, PL_cumulo+AN+AN_cumulo+interval_yield+inter- val_Pdt.+RS+RS_cumulo+rab_integral+AS_Vol.+emis- sion_CO2+interval_O2; 0.388, 0.680, PL_cumulo+AN_cu- mulo+interval_yield+interval_Pdt.+RS_cumulo+RQ_ integral+AS_Vol.+emission_CO2+interval_O2; 0.358, 0.680, tmp_cumulo+AN+AN_cumulo+interval_yield+RS+ Feed_Vol+rab_integral+RQ_integral+AS_Vol.+emission_ O2+consum_O2+interval_O2; 0.337, 0.680, tmp_cumulo+ PL+PL_cumulo+AN+AN_cumulo+interval_yield+ interval_Pdt.+Feed_Vol+RS_cumulo+rab_integral+RQ_ integral+AS_Vol.+emission_CO2+interval_O2; 0.337, 0.680, tmp_cumulo+pH_cumulo+PL_cumulo+AN_cu- mulo+interval_yield+interval_Pdt.+Feed_Vol+RS_cu- mulo+rab_integral+RQ_integral+AS_Vol.+emission_CO2+ consum_O2+interval_O2; 0.337, 0.680, tmp_cumulo+pH+ PL_cumulo+AN_cumulo+interval_yield+interval_Pdt.+ OD+Feed_Vol+RS_cumulo+rab_integral+RQ_integral+ AS_Vol.+emission_CO2+interval_O2; 0.358, 0.680, tmp_ cumulo+pH_cumulo+AN_cumulo+interval_yield+interval_ Pdt.+Feed_Vol+RS_cumulo+rab_integral+RQ_integral+ AS_Vol.+emission_CO2+consum_O2; 0.358, 0.680, pH+PL+PL_cumulo+AN+AN_cumulo+interval_yield+in- terval_Pdt.+RS_cumulo+rab_integral+RQ_integral+AS_ Vol.+emission_CO2; 0.358, 0.680, tmp_cumulo+pH+AN_ cumulo+interval_yield+interval_Pdt.+RS+Feed_Vol+RS_ cumulo+rab_integral+RQ_integral+AS_Vol.+emission_ CO2; 0.368, 0.680, tmp_cumulo+PL_cumulo+AN+AN_ cumulo+interval_yield+RS+Feed_Vol+rab_integral+RQ_ integral+AS_Vol.+emission_O2; 0.397, 0.680, tmp_ cumulo+interval_yield+RS+Feed_Vol+RS_cumulo+AS_ Vol.+emission_O2+interval_O2; 0.358, 0.680, tmp_ cumulo+PL_cumulo+AN+AN_cumulo+interval_yield+ Feed_Vol+RS_cumulo+rab_integral+RQ_integral+AS_ Vol.+emission_O2+emission_CO2; 0.348, 0.680, tmp_ cumulo+pH+AN_cumulo+interval_yield+RS+Feed_ Vol+RS_cumulo+rab_integral+RQ_integral+AS_Vol.+ emission_CO2+interval_O2; 0.326, 0.680, tmp_cumulo+ PL_cumulo+AN+AN_cumulo+interval_yield+interval_ Pdt.+RS+Feed_Vol+RS_cumulo+rab_integral+RQ_ integral+AS_Vol.+emission_CO2+consum_O2+interval_ O2; 0.348, 0.680, tmp_cumulo+PL_cumulo+AN_cumulo+ interval_yield+RS+Feed_Vol+RS_cumulo+rab_integral+ RQ_integral+AS_Vol.+emission_O2+emission_CO2+ interval_O2; 0.348, 0.680, tmp_cumulo+pH+PL_cumulo+ AN_cumulo+interval_yield+interval_Pdt.+OD+Feed_Vol+ RS_cumulo+rab_integral+RQ_integral+AS_Vol.+ emission_CO2; 0.388, 0.680, PL_cumulo+interval_yield+ OD+RS+Feed_Vol+AS_Vol.+emission_O2+consum_O2+ interval_O2; 0.358, 0.680, tmp+tmp_cumulo+PL_cumulo+ AN_cumulo+interval_yield+interval_Pdt.+Feed_Vol+RS_ cumulo+rab_integral+RQ_integral+AS_Vol.+emission_O2; 0.358, 0.680, tmp_cumulo+pH_cumulo+PL_cumulo+AN+ AN_cumulo+interval_yield+Feed_Vol+RS_cumulo+rab_ integral+RQ_integral+AS_Vol.+emission_CO2; 0.348, 0.680, tmp_cumulo+pH_cumulo+AN+AN_cumulo+inter- val_yield+RS+Feed_Vol+RS_cumulo+rab_integral+RQ_ integral+AS_Vol.+emission_CO2+consum_O2; 0.368, 0.680, tmp_cumulo+pH_cumulo+AN_cumulo+interval_ yield+Feed_Vol+RS_cumulo+rab_integral+RQ_integral+ AS_Vol.+emission_CO2+consum_O2; 0.358, 0.680, tmp_ cumulo+PL_cumulo+AN_cumulo+interval_yield+interval_ Pdt.+RS+RS_cumulo+rab_integral+RQ_integral+AS_Vol.+ emission_CO2+consum_O2; 0.358, 0.680, tmp+tmp_ cumulo+AN+AN_cumulo+interval_yield+Feed_Vol+RS_ cumulo+rab_integral+RQ_integral+AS_Vol.+emission_ CO2+interval_O2; 0.358, 0.680, O2+PL_cumulo+AN_ cumulo+interval_yield+interval_Pdt.+OD+Feed_Vol+RS_ cumulo+rab_integral+RQ_integral+AS_Vol.+emission_ CO2; 0.358, 0.680, tmp+tmp_cumulo+PL_cumulo+AN_ cumulo+interval_yield+RS+Feed_Vol+RS_cumulo+rab_ integral+RQ_integral+AS_Vol.+emission_O2; 0.368, 0.680, tmp_cumulo+AN_cumulo+interval_yield+Feed_Vol+RS_ cumulo+rab_integral+RQ_integral+Accum._Yield+AS_ Vol.+emission_CO2+consum_O2; 0.337, 0.680, tmp_cu- mulo+PL_cumulo+AN+AN_cumulo+interval_yield+ interval_Pdt.+Feed_Vol+RS_cumulo+rab_integral+RQ_ integral+AS_Vol.+emission_O2+emission_CO2+consum_ O2; 0.358, 0.680, tmp+PL+PL_cumulo+AN_cumulo+ interval_yield+RS+Feed_Vol+RS_cumulo+rab_integral+ RQ_integral+AS_Vol.+emission_CO2; 0.337, 0.680, tmp_ cumulo+pH+AN+AN_cumulo+interval_yield+RS+Feed_ Vol+RS_cumulo+rab_integral+RQ_integral+AS_Vol.+ emission_CO2+consum_O2+interval_O2; 0.337, 0.680, tmp_cumulo+PL+PL_cumulo+AN_cumulo+interval_ yield+interval_Pdt.+RS+Feed_Vol+RS_cumulo+rab_inte- gral+RQ_integral+AS_Vol.+emission_CO2+consum_O2; 0.358, 0.680, tmp_cumulo+PL+AN+AN_cumulo+interval_ yield+Feed_Vol+RS_cumulo+rab_integral+RQ_integral+ AS_Vol.+emission_CO2+consum_O2; 0.368, 0.680, PL_cumulo+AN+AN_cumulo+interval_yield+Feed_Vol+ RS_cumulo+rab_integral+RQ_integral+AS_Vol.+emis- sion_CO2+interval_O2; 0.388, 0.680, PL_cumulo+inter- val_yield+interval_Pdt.+OD+RS_cumulo+rab_integral+ RQ_integral+AS_Vol.+emission_CO2; 0.388, 0.680, PL_cumulo+AN_cumulo+interval_yield+RS+Feed_Vol+ RS_cumulo+AS_Vol.+emission_O2+emission_CO2; 0.397, 0.680, tmp_cumulo+AN_cumulo+interval_yield+RS+ Feed_Vol+RS_cumulo+AS_Vol.+emission_O2; 0.358, 0.680, pH+PL_cumulo+AN_cumulo+interval_yield+inter- val_Pdt.+RS_cumulo+rab_integral+RQ_integral+AS_Vol.+ emission_CO2+consum_O2+interval_O2; 0.358, 0.680, tmp+pH_cumulo+PL_cumulo+AN_cumulo+interval_ yield+interval_Pdt.+RS_cumulo+rab_integral+RQ_integral+AS_Vol.+emission_CO2+interval_O2; 0.378, 0.680, PL_cumulo+AN+AN_cumulo+interval_yield+Feed_Vol+RS_cumulo+rab_integral+RQ_integral+AS_Vol.+emission_CO2; 0.397, 0.680, O2+PL_cumulo+interval_yield+RS_cumulo+RQ_integral+AS_Vol.+emission_O2+emission_CO2; 0.358, 0.680, O2+PL_cumulo+AN_cumulo+interval_yield+interval_Pdt.+RS+Feed_Vol+RS_cumulo+rab_integral+RQ_integral+AS_Vol.+emission_CO2; 0.336, 0.680, tmp_cumulo+pH+PL+PL_cumulo+AN_cumulo+interval_yield+interval_Pdt.+Feed_Vol+RS_cumulo+rab_integral+RQ_integral+AS_Vol.+emission_CO2+consum_O2; 0.347, 0.680, tmp_cumulo+PL_cumulo+AN+AN_cumulo+interval_yield+OD+Feed_Vol+RS_cumulo+rab_integral+RQ_integral+AS_Vol.+emission_CO2+consum_O2; 0.387, 0.680, PL_cumulo+AN_cumulo+interval_yield+OD+RS+Feed_Vol+AS_Vol.+emission_O2+interval_O2; 0.358, 0.680, tmp_cumulo+PL+PL_cumulo+AN_cumulo+interval_yield+interval_Pdt.+RS+RS_cumulo+rab_integral+RQ_integral+AS_Vol.+emission_CO2; 0.397, 0.680, PL_cumulo+interval_yield+interval_Pdt.+RS_cumulo+RQ_integral+AS_Vol.+emission_O2+emission_CO2; 0.387, 0.680, tmp_cumulo+interval_yield+RS+Feed_Vol+RS_cumulo+rab_integral+RQ_integral+AS_Vol.+emission_O2; 0.358, 0.680, tmp_cumulo+AN_cumulo+interval_yield+interval_Pdt.+RS+Feed_Vol+RS_cumulo+rab_integral+RQ_integral+AS_Vol.+consum_O2+generate_CO2; 0.368, 0.680, tmp_cumulo+PL_cumulo+AN+AN_cumulo+interval_yield+interval_Pdt.+RS_cumulo+rab_integral+RQ_integral+emission_CO2+interval_O2; 0.368, 0.680, tmp+PL_cumulo+AN+AN_cumulo+interval_yield+interval_Pdt.+RS_cumulo+rab_integral+RQ_integral+AS_Vol.+emission_CO2; 0.397, 0.680, tmp+PL_cumulo+interval_yield+interval_Pdt.+RS_cumulo+RQ_integral+AS_Vol.+emission_CO2; 0.368, 0.680, PL_cumulo+AN_cumulo+interval_yield+interval_Pdt.+OD+RS_cumulo+rab_integral+RQ_integral+AS_Vol.+emission_CO2+consum_O2; 0.336, 0.680, tmp_cumulo+PL+PL_cumulo+AN_cumulo+interval_yield+interval_Pdt.+RS+Feed_Vol+RS_cumulo+rab_integral+RQ_integral+AS_Vol.+emission_CO2+interval_O2; 0.387, 0.680, tmp_cumulo+interval_yield+RS+Feed_Vol+RS_cumulo+AS_Vol.+emission_O2+consum_O2+interval_O2; 0.336, 0.680, tmp+tmp_cumulo+PL_cumulo+AN+AN_cumulo+interval_yield+interval_Pdt.+Feed_Vol+RS_cumulo+rab_integral+RQ_integral+AS_Vol.+emission_CO2+consum_O2; 0.397, 0.680, tmp_cumulo+PL_cumulo+interval_yield+Feed_Vol+RS_cumulo+AS_Vol.+emission_O2+interval_O2; 0.378, 0.680, tmp_cumulo+AN_cumulo+interval_yield+interval_Pdt.+RS+RS_cumulo+rab_integral+RQ_integral+AS_Vol.+emission_CO2; 0.358, 0.679, tmp_cumulo+PL_cumulo+AN+AN_cumulo+interval_yield+OD+Feed_Vol+RS_cumulo+rab_integral+RQ_integral+AS_Vol.+emission_CO2; 0.378, 0.679, PL_cumulo+AN_cumulo+interval_yield+Feed_Vol+RS_cumulo+rab_integral+RQ_integral+AS_Vol.+emission_CO2+consum_O2; 0.378, 0.679, O2+PL_cumulo+AN_cumulo+interval_yield+OD+RS+Feed_Vol+AS_Vol.+consum_O2+interval_O2; 0.396, 0.679, tmp_cumulo+interval_yield+interval_Pdt.+RS_cumulo+rab_integral+RQ_integral+AS_Vol.+emission_CO2; 0.357, 0.679, PL_cumulo+AN+AN_cumulo+interval_yield+interval_Pdt.+Feed_Vol+RS_cumulo+rab_integral+RQ_integral+AS_Vol.+emission_CO2+interval_O2; 0.387, 0.679, tmp_cumulo+pH+interval_yield+Feed_Vol+RS_cumulo+rab_integral+RQ_integral+AS_Vol.+emission_CO2; 0.357, 0.679, tmp+tmp_cumulo+PL+AN+AN_cumulo+interval_yield+interval_Pdt.+RS_cumulo+rab_integral+RQ_integral+AS_Vol.+emission_CO2; 0.357, 0.679, tmp+tmp_cumulo+AN+AN_cumulo+interval_yield+RS+Feed_Vol+RS_cumulo+rab_integral+RQ_integral+AS_Vol.+emission_CO2; 0.396, 0.679, tmp_cumulo+PL_cumulo+interval_yield+RS+Feed_Vol+RS_cumulo+AS_Vol.+emission_CO2; 0.405, 0.679, PL_cumulo+AN_cumulo+interval_yield+RS+Feed_Vol+AS_Vol.+emission_O2; 0.357, 0.679, tmp_cumulo+AN+AN_cumulo+interval_yield+Feed_Vol+RS_cumulo+rab_integral+RQ_integral+Accum._Yield+AS_Vol.+emission_CO2+consum_O2; 0.387, 0.679, tmp_cumulo+PL+PL_cumulo+AN+AN_cumulo+interval_yield+RS_cumulo+RQ_integral+emission_CO2; 0.357, 0.679, tmp_cumulo+pH_cumulo+AN_cumulo+interval_yield+RS+Feed_Vol+RS_cumulo+rab_integral+RQ_integral+AS_Vol.+emission_CO2+consum_O2; 0.357, 0.679, tmp_cumulo+PL_cumulo+AN_cumulo+interval_yield+interval_Pdt.+Feed_Vol+RS_cumulo+rab_integral+RQ_integral+AS_Vol.+emission_O2+consum_O2; 0.336, 0.679, tmp+tmp_cumulo+PL_cumulo+AN+AN_cumulo+interval_yield+interval_Pdt.+Feed_Vol+RS_cumulo+rab_integral+RQ_integral+AS_Vol.+emission_CO2+interval_O2; 0.357, 0.679, tmp_cumulo+AN_cumulo+interval_yield+interval_Pdt.+OD+RS+Feed_Vol+RS_cumulo+rab_integral+RQ_integral+AS_Vol.+emission_CO2; 0.387, 0.679, tmp_cumulo+PL_cumulo+interval_yield+interval_Pdt.+RS_cumulo+RQ_integral+AS_Vol.+emission_CO2+interval_O2; 0.347, 0.679, tmp_cumulo+pH+PL_cumulo+AN_cumulo+interval_yield+OD+Feed_Vol+RS_cumulo+rab_integral+RQ_integral+AS_Vol.+emission_CO2+interval_O2; 0.368, 0.679, tmp_cumulo+pH+AN_cumulo+interval_yield+OD+Feed_Vol+RS_cumulo+rab_integral+RQ_integral+AS_Vol.+emission_CO2; 0.357, 0.679, tmp_cumulo+PL+AN_cumulo+interval_yield+RS+Feed_Vol+RS_cumulo+rab_integral+RQ_integral+AS_Vol.+emission_CO2+interval_O2; 0.336, 0.679, tmp_cumulo+pH+PL_cumulo+AN_cumulo+interval_yield+RS+Feed_Vol+RS_cumulo+rab_integral+RQ_integral+AS_Vol.+emission_CO2+consum_O2+interval_O2; 0.405, 0.679, tmp_cumulo+interval_yield+RS+Feed_Vol+RS_cumulo+AS_Vol.+emission_O2; 0.336, 0.679, tmp_cumulo+PL_cumulo+AN_cumulo+interval_yield+interval_Pdt.+Feed_Vol+RS_cumulo+rab_integral+RQ_integral+Accum._Yield+AS_Vol.+emission_CO2+consum_O2+interval_O2; 0.347, 0.679, tmp+tmp_cumulo+AN_cumulo+interval_yield+interval_Pdt.+RS+Feed_Vol+RS_cumulo+rab_integral+RQ_integral+AS_Vol.+emission_CO2+consum_O2; 0.387, 0.679, tmp_cumulo+interval_yield+Feed_Vol+RS_cumulo+rab_integral+RQ_integral+AS_Vol.+emission_O2+emission_CO2; 0.387, 0.679, O2+PL_cumulo+interval_yield+RS+Feed_Vol+RS_cumulo+AS_Vol.+consum_O2+interval_O2; 0.336, 0.679, tmp+tmp_cumulo+PL_cumulo+AN_cumulo+interval_yield+interval_Pdt.+RS+Feed_Vol+RS_cumulo+rab_integral+RQ_integral+AS_Vol.+emission_CO2+consum_O2; 0.396, 0.679, PL_cumulo+interval_yield+Feed_Vol+RS_cumulo+rab_integral+RQ_integral+AS_Vol.+emission_CO2; 0.357, 0.679, tmp_cumulo+pH+AN_cumulo+interval_yield+Feed_Vol+RS_cumulo+rab_integral+RQ_integral+AS_Vol.+emission_CO2+consum_O2+interval_O2; 0.347, 0.679, tmp_cumulo+pH+PL_cumulo+AN_cumulo+interval_yield+Feed_Vol+RS_cumulo+rab_integral+RQ_integral+AS_Vol.+emission_O2+emission_CO2+interval_O2; 0.336, 0.679, tmp+tmp_cumulo+PL_cumulo+AN_cumulo+interval_yield+interval_Pdt.+RS+Feed_Vol+RS_cumulo+rab_integral+RQ_integral+AS_Vol.+emission_CO2+interval_O2; 0.387, 0.679, tmp_cumulo+PL_cumulo+interval_yield+interval_Pdt.+RS+

Feed_Vol+RS_cumulo+AS_Vol.+emission_O2; 0.347, 0.679, tmp_cumulo+pH_cumulo+PL+PL_cumulo+AN_cumulo+interval_yield+Feed_Vol+RS_cumulo+rab_integral+RQ_integral+AS_Vol.+emission_CO2+interval_O2; 0.367, 0.679, pH+PL_cumulo+AN+AN_cumulo+interval_yield+interval_Pdt.+RS_cumulo+rab_integral+RQ_integral+AS_Vol.+emission_CO2; 0.357, 0.679, pH+pH_cumulo+PL_cumulo+AN_cumulo+interval_yield+interval_Pdt.+RS_cumulo+rab_integral+RQ_integral+AS_Vol.+emission_CO2+interval_O2; 0.347, 0.679, tmp+tmp_cumulo+pH+PL+PL_cumulo+AN_cumulo+interval_yield+Feed_Vol+RS_cumulo+rab_integral+RQ_integral+AS_Vol.+emission_CO2; 0.367, 0.679, tmp_cumulo+PL_cumulo+interval_yield+RS+Feed_Vol+RS_cumulo+rab_integral+RQ_integral+AS_Vol.+emission_O2+interval_O2; 0.367, 0.679, tmp_cumulo+AN_cumulo+interval_yield+Feed_Vol+RS_cumulo+rab_integral+RQ_integral+Accum._Yield+AS_Vol.+emission_CO2+interval_O2; 0.367, 0.679, tmp_cumulo+AN+AN_cumulo+interval_yield+interval_Pdt.+RS_cumulo+rab_integral+RQ_integral+AS_Vol.+emission_CO2+consum_O2; 0.367, 0.679, tmp_cumulo+AN_cumulo+interval_yield+Feed_Vol+RS_cumulo+rab_integral+RQ_integral+AS_Vol.+emission_O2+emission_CO2+consum_O2; 0.357, 0.679, O2+PL_cumulo+AN_cumulo+interval_yield+interval_Pdt.+RS_cumulo+rab_integral+RQ_integral+AS_Vol.+emission_CO2+consum_O2+interval_O2; 0.357, 0.679, tmp_cumulo+pH_cumulo+AN+AN_cumulo+interval_yield+Feed_Vol+RS_cumulo+rab_integral+RQ_integral+AS_Vol.+emission_CO2+interval_O2; 0.377, 0.679, tmp_cumulo+PL_cumulo+AN_cumulo+interval_yield+RS+Feed_Vol+RS_cumulo+AS_Vol.+emission_O2+emission_CO2; 0.367, 0.679, pH+PL_cumulo+AN_cumulo+interval_yield+interval_Pdt.+Feed_Vol+RS_cumulo+rab_integral+RQ_integral+AS_Vol.+emission_CO2; 0.367, 0.679, tmp_cumulo+pH+PL+PL_cumulo+interval_yield+interval_Pdt.+RS_cumulo+rab_integral+RQ_integral+AS_Vol.+emission_CO2; 0.387, 0.679, tmp_cumulo+PL_cumulo+interval_yield+OD+Feed_Vol+RS_cumulo+RQ_integral+AS_Vol.+emission_CO2; 0.357, 0.679, tmp+PL+PL_cumulo+AN_cumulo+interval_yield+interval_Pdt.+RS+RS_cumulo+rab_integral+RQ_integral+AS_Vol.+emission_CO2; 0.367, 0.679, tmp+tmp_cumulo+PL_cumulo+interval_yield+interval_Pdt.+RS_cumulo+rab_integral+RQ_integral+AS_Vol.+emission_CO2+interval_O2; 0.377, 0.679, tmp_cumulo+PL_cumulo+AN+interval_yield+interval_Pdt.+RS_cumulo+rab_integral+RQ_integral+AS_Vol.+emission_CO2; 0.387, 0.679, tmp_cumulo+PL_cumulo+AN+AN_cumulo+interval_yield+RS+RS_cumulo+RQ_integral+emission_CO2; 0.336, 0.679, tmp_cumulo+pH+AN+AN_cumulo+interval_yield+interval_Pdt.+RS+Feed_Vol+RS_cumulo+rab_integral+RQ_integral+AS_Vol.+emission_CO2+consum_O2; 0.387, 0.679, PL_cumulo+AN_cumulo+interval_yield+RS+Feed_Vol+RS_cumulo+AS_Vol.+emission_CO2+consum_O2; 0.377, 0.679, O2+PL_cumulo+interval_yield+interval_Pdt.+RS_cumulo+rab_integral+RQ_integral+AS_Vol.+emission_CO2+interval_O2; 0.367, 0.679, tmp_cumulo+AN_cumulo+interval_yield+RS+Feed_Vol+RS_cumulo+rab_integral+RQ_integral+AS_Vol.+emission_CO2+generate_CO2; 0.357, 0.679, pH_cumulo+PL_cumulo+AN_cumulo+interval_yield+interval_Pdt.+Feed_Vol+RS_cumulo+rab_integral+RQ_integral+AS_Vol.+emission_CO2+interval_O2; 0.396, 0.679, O2+PL_cumulo+AN_cumulo+interval_yield+OD+RS+Feed_Vol+AS_Vol.; 0.357, 0.679, tmp_cumulo+PL+AN+AN_cumulo+interval_yield+RS+Feed_Vol+RS_cumulo+rab_integral+RQ_integral+AS_Vol.+emission_CO2; 0.367, 0.679, tmp_cumulo+PL_cumulo+AN+AN_cumulo+interval_yield+interval_Pdt.+RS+RS_cumulo+rab_integral+RQ_integral+emission_CO2; 0.367, 0.679, tmp+PL_cumulo+AN_cumulo+interval_yield+interval_Pdt.+RS+RS_cumulo+rab_integral+RQ_integral+AS_Vol.+emission_CO2; 0.357, 0.679, tmp_cumulo+AN+AN_cumulo+interval_yield+Feed_Vol+RS_cumulo+rab_integral+RQ_integral+AS_Vol.+emission_O2+emission_CO2+consum_O2; 0.346, 0.679, tmp_cumulo+pH_cumulo+PL_cumulo+AN+AN_cumulo+interval_yield+Feed_Vol+RS_cumulo+rab_integral+RQ_integral+AS_Vol.+emission_CO2+consum_O2; 0.367, 0.679, tmp_cumulo+AN+interval_yield+Feed_Vol+RS_cumulo+rab_integral+RQ_integral+AS_Vol.+emission_O2+emission_CO2+interval_O2; 0.357, 0.679, PL_cumulo+AN+AN_cumulo+interval_yield+interval_Pdt.+OD+RS_cumulo+rab_integral+RQ_integral+AS_Vol.+emission_CO2+interval_O2; 0.346, 0.679, tmp_cumulo+PL_cumulo+AN+AN_cumulo+interval_yield+interval_Pdt.+OD+RS_cumulo+rab_integral+RQ_integral+AS_Vol.+emission_CO2+interval_O2; 0.357, 0.679, tmp_cumulo+AN+AN_cumulo+interval_yield+RS+Feed_Vol+RS_cumulo+rab_integral+RQ_integral+AS_Vol.+emission_O2+consum_O2; 0.346, 0.679, tmp_cumulo+pH+AN_cumulo+interval_yield+interval_Pdt.+Feed_Vol+RS_cumulo+rab_integral+RQ_integral+AS_Vol.+emission_CO2+consum_O2+interval_O2; 0.357, 0.679, tmp_cumulo+PL_cumulo+AN+AN_cumulo+interval_yield+interval_Pdt.+Feed_Vol+RS_cumulo+rab_integral+RQ_integral+AS_Vol.+emission_O2; 0.377, 0.679, tmp_cumulo+AN_cumulo+interval_yield+RS+Feed_Vol+RS_cumulo+rab_integral+AS_Vol.+emission_O2+generate_CO2; 0.405, 0.679, PL_cumulo+interval_yield+RS+Feed_Vol+RS_cumulo+AS_Vol.+emission_O2; 0.357, 0.679, O2+PL_cumulo+AN+AN_cumulo+interval_yield+interval_Pdt.+RS+RS_cumulo+rab_integral+RQ_integral+AS_Vol.+emission_CO2; 0.357, 0.679, O2+PL_cumulo+AN_cumulo+interval_yield+interval_Pdt.+Feed_Vol+RS_cumulo+rab_integral+RQ_integral+AS_Vol.+emission_CO2+consum_O2; 0.346, 0.679, tmp+tmp_cumulo+pH+PL_cumulo+AN_cumulo+interval_yield+interval_Pdt.+Feed_Vol+RS_cumulo+rab_integral+RQ_integral+AS_Vol.+emission_CO2; 0.367, 0.679, pH_cumulo+PL+PL_cumulo+AN_cumulo+interval_yield+OD+RS+Feed_Vol+AS_Vol.+consum_O2+interval_O2; 0.386, 0.679, O2+PL_cumulo+AN_cumulo+interval_yield+RS+Feed_Vol+RS_cumulo+AS_Vol.+emission_O2; 0.377, 0.679, tmp+tmp_cumulo+AN_cumulo+interval_yield+interval_Pdt.+RS_cumulo+rab_integral+RQ_integral+AS_Vol.+emission_CO2; 0.346, 0.679, tmp_cumulo+AN_cumulo+interval_yield+interval_Pdt.+OD+RS+Feed_Vol+RS_cumulo+rab_integral+RQ_integral+AS_Vol.+emission_CO2+consum_O2; 0.335, 0.679, tmp+tmp_cumulo+PL+PL_cumulo+AN_cumulo+interval_yield+interval_Pdt.+Feed_Vol+RS_cumulo+rab_integral+RQ_integral+AS_Vol.+emission_CO2+interval_O2; 0.335, 0.679, tmp_cumulo+pH+PL_cumulo+AN+AN_cumulo+interval_yield+RS+Feed_Vol+RS_cumulo+rab_integral+RQ_integral+AS_Vol.+emission_CO2+interval_O2; 0.367, 0.679, pH+PL+PL_cumulo+AN_cumulo+interval_yield+RS+Feed_Vol+rab_integral+RQ_integral+AS_Vol.+emission_CO2; 0.357, 0.679, tmp_cumulo+pH+PL_cumulo+AN+AN_cumulo+interval_yield+interval_Pdt.+RS_cumulo+rab_integral+RQ_integral+AS_Vol.+emission_CO2; 0.396, 0.679, pH+PL_cumulo+interval_yield+interval_Pdt.+RS_cumulo+RQ_integral+AS_Vol.+emission_CO2; 0.357, 0.679, tmp_cumulo+PL+AN+AN_cumulo+interval_yield+Feed_Vol+

RS_cumulo+rab_integral+RQ_integral+AS_Vol.+emission_CO2+interval_O2; 0.357, 0.679, tmp_cumulo+pH_cumulo+AN+AN_cumulo+interval_yield+Feed_Vol+RS_cumulo+rab_integral+RQ_integral+AS_Vol.+emission_CO2+consum_O2; 0.377, 0.679, tmp_cumulo+PL+PL_cumulo+AN_cumulo+interval_yield+Feed_Vol+RS_cumulo+RQ_integral+AS_Vol.+emission_CO2; 0.367, 0.679, tmp_cumulo+pH+PL_cumulo+interval_yield+interval_Pdt.+RS_cumulo+rab_integral+RQ_integral+AS_Vol.+emission_CO2+interval_O2; 0.346, 0.679, tmp_cumulo+pH+PL_cumulo+AN_cumulo+interval_yield+interval_Pdt.+RS+Feed_Vol+RS_cumulo+rab_integral+RQ_integral+AS_Vol.+emission_O2; 0.377, 0.679, tmp_cumulo+AN_cumulo+interval_yield+interval_Pdt.+RS_cumulo+rab_integral+RQ_integral+AS_Vol.+emission_CO2+consum_O2; 0.357, 0.679, O2+PL_cumulo+AN+AN_cumulo+interval_yield+interval_Pdt.+RS_cumulo+rab_integral+RQ_integral+AS_Vol.+emission_CO2+consum_O2; 0.357, 0.679, pH_cumulo+PL_cumulo+AN+AN_cumulo+interval_yield+interval_Pdt.+RS_cumulo+rab_integral+RQ_integral+AS_Vol.+emission_CO2+interval_O2; 0.367, 0.679, tmp_cumulo+PL_cumulo+interval_yield+Feed_Vol+RS_cumulo+rab_integral+RQ_integral+AS_Vol.+emission_CO2+consum_O2+interval_O2; 0.346, 0.679, tmp+tmp_cumulo+PL_cumulo+AN_cumulo+interval_yield+interval_Pdt.+RS_cumulo+rab_integral+RQ_integral+AS_Vol.+emission_CO2+consum_O2+interval_O2; 0.377, 0.679, O2+PL_cumulo+AN+interval_yield+interval_Pdt.+RS_cumulo+rab_integral+RQ_integral+AS_Vol.+emission_CO2; 0.356, 0.679, tmp+PL_cumulo+AN_cumulo+interval_yield+interval_Pdt.+OD+RS_cumulo+rab_integral+RQ_integral+AS_Vol.+emission_CO2+interval_O2; 0.395, 0.679, PL_cumulo+interval_yield+RS+Feed_Vol+RS_cumulo+AS_Vol.+emission_O2+interval_O2; 0.346, 0.679, tmp_cumulo+PL_cumulo+AN_cumulo+interval_yield+interval_Pdt.+OD+RS+Feed_Vol+RS_cumulo+rab_integral+RQ_integral+AS_Vol.+emission_CO2; 0.356, 0.679, tmp_cumulo+pH+AN+AN_cumulo+interval_yield+interval_Pdt.+Feed_Vol+RS_cumulo+rab_integral+RQ_integral+AS_Vol.+emission_CO2; 0.356, 0.679, tmp_cumulo+AN_cumulo+interval_yield+interval_Pdt.+Feed_Vol+RS_cumulo+rab_integral+RQ_integral+Accum._Yield+AS_Vol.+emission_CO2+consum_O2; 0.356, 0.679, tmp_cumulo+pH+PL+PL_cumulo+interval_yield+interval_Pdt.+Feed_Vol+RS_cumulo+rab_integral+RQ_integral+AS_Vol.+emission_CO2; 0.346, 0.679, tmp_cumulo+pH+AN_cumulo+interval_yield+interval_Pdt.+RS+Feed_Vol+RS_cumulo+rab_integral+RQ_integral+AS_Vol.+emission_CO2+interval_O2; 0.367, 0.679, O2+PL_cumulo+AN+AN_cumulo+interval_yield+RS+Feed_Vol+rab_integral+RQ_integral+AS_Vol.+emission_CO2; 0.346, 0.679, tmp_cumulo+PL_cumulo+AN_cumulo+interval_yield+OD+RS+Feed_Vol+RS_cumulo+rab_integral+RQ_integral+AS_Vol.+emission_CO2+consum_O2; 0.386, 0.679, PL_cumulo+AN_cumulo+interval_yield+RS+Feed_Vol+rab_integral+RQ_integral+AS_Vol.+emission_O2; 0.367, 0.679, tmp_cumulo+PL+PL_cumulo+AN+AN_cumulo+interval_yield+interval_Pdt.+RS_cumulo+rab_integral+RQ_integral+emission_CO2; 0.346, 0.679, tmp_cumulo+PL_cumulo+AN+AN_cumulo+interval_yield+OD+Feed_Vol+RS_cumulo+rab_integral+RQ_integral+AS_Vol.+emission_CO2+interval_O2; 0.356, 0.679, tmp+tmp_cumulo+AN_cumulo+interval_yield+interval_Pdt.+RS+Feed_Vol+RS_cumulo+rab_integral+RQ_integral+AS_Vol.+emission_CO2; 0.395, 0.679, tmp_cumulo+interval_yield+RS+Feed_Vol+RS_cumulo+rab_integral+RQ_integral+AS_Vol.; 0.356, 0.679, tmp_cumulo+AN_cumulo+interval_yield+RS+Feed_Vol+RS_cumulo+rab_integral+AS_Vol.+emission_O2+consum_O2+interval_O2+generate_CO2; 0.346, 0.679, tmp_cumulo+pH+PL_cumulo+AN_cumulo+interval_yield+interval_Pdt.+RS+Feed_Vol+RS_cumulo+rab_integral+RQ_integral+AS_Vol.+emission_CO2; 0.366, 0.679, tmp_cumulo+pH_cumulo+PL+AN_cumulo+interval_yield+Feed_Vol+RS_cumulo+rab_integral+RQ_integral+AS_Vol.+emission_CO2; 0.335, 0.679, tmp_cumulo+pH+PL_cumulo+AN_cumulo+interval_yield+interval_Pdt.+Feed_Vol+RS_cumulo+rab_integral+RQ_integral+AS_Vol.+emission_O2+emission_CO2+interval_O2; 0.386, 0.679, tmp_cumulo+PL_cumulo+interval_yield+interval_Pdt.+RS_cumulo+RQ_integral+AS_Vol.+emission_O2+emission_CO2; 0.335, 0.679, tmp_cumulo+PL_cumulo+AN_cumulo+interval_yield+interval_Pdt.+OD+RS+Feed_Vol+RS_cumulo+rab_integral+RQ_integral+AS_Vol.+emission_CO2+consum_O2; 0.346, 0.679, tmp+tmp_cumulo+PL+PL_cumulo+AN_cumulo+interval_yield+Feed_Vol+RS_cumulo+rab_integral+RQ_integral+AS_Vol.+emission_CO2+interval_O2; 0.376, 0.679, tmp_cumulo+AN_cumulo+interval_yield+RS+Feed_Vol+rab_integral+RQ_integral+AS_Vol.+consum_O2+generate_CO2; 0.356, 0.679, tmp+pH+PL+PL_cumulo+AN_cumulo+interval_yield+interval_Pdt.+RS_cumulo+rab_integral+RQ_integral+AS_Vol.+emission_CO2; 0.395, 0.679, tmp_cumulo+interval_yield+RS+Feed_Vol+RS_cumulo+AS_Vol.+consum_O2+interval_O2; 0.335, 0.679, tmp_cumulo+pH+PL_cumulo+AN+AN_cumulo+interval_yield+Feed_Vol+RS_cumulo+rab_integral+RQ_integral+AS_Vol.+emission_CO2+consum_O2+interval_O2; 0.346, 0.679, tmp+tmp_cumulo+PL_cumulo+AN_cumulo+interval_yield+interval_Pdt.+OD+Feed_Vol+RS_cumulo+rab_integral+RQ_integral+AS_Vol.+emission_CO2; 0.345, 0.679, tmp_cumulo+pH_cumulo+PL_cumulo+AN_cumulo+interval_yield+interval_Pdt.+RS+Feed_Vol+RS_cumulo+rab_integral+RQ_integral+AS_Vol.+emission_O2; 0.366, 0.679, tmp_cumulo+pH_cumulo+PL_cumulo+interval_yield+Feed_Vol+RS_cumulo+rab_integral+RQ_integral+AS_Vol.+emission_CO2+interval_O2; 0.386, 0.679, tmp_cumulo+pH+PL_cumulo+interval_yield+interval_Pdt.+RS_cumulo+RQ_integral+AS_Vol.+emission_CO2; 0.356, 0.679, tmp_cumulo+AN+AN_cumulo+interval_yield+interval_Pdt.+RS+Feed_Vol+RS_cumulo+rab_integral+RQ_integral+AS_Vol.+emission_O2; 0.366, 0.679, tmp_cumulo+AN_cumulo+interval_yield+interval_Pdt.+Feed_Vol+RS_cumulo+rab_integral+RQ_integral+AS_Vol.+emission_CO2+generate_CO2; 0.366, 0.679, PL_cumulo+AN_cumulo+interval_yield+interval_Pdt.+RS_cumulo+rab_integral+RQ_integral+AS_Vol.+emission_CO2+consum_O2+generate_CO2; 0.376, 0.679, PL_cumulo+AN_cumulo+interval_yield+OD+RS+Feed_Vol+AS_Vol.+emission_O2+consum_O2+interval_O2; 0.356, 0.679, O2+PL_cumulo+AN_cumulo+interval_yield+interval_Pdt.+OD+RS_cumulo+rab_integral+RQ_integral+AS_Vol.+emission_CO2+interval_O2; 0.356, 0.679, tmp_cumulo+PL_cumulo+AN+interval_yield+interval_Pdt.+Feed_Vol+RS_cumulo+rab_integral+RQ_integral+AS_Vol.+emission_CO2+interval_O2; 0.345, 0.679, tmp+tmp_cumulo+PL_cumulo+AN_cumulo+interval_yield+Feed_Vol+RS_cumulo+rab_integral+RQ_integral+AS_Vol.+emission_CO2+consum_O2+interval_O2; 0.345, 0.679, tmp+tmp_cumulo+PL_cumulo+AN+AN_cumulo+interval_yield+interval_Pdt.+RS_cumulo+rab_integral+RQ_integral+AS_Vol.+emission_CO2+consum_O2; 0.356, 0.679, pH+PL_cumulo+AN_cumulo+interval_yield+interval_

Pdt.+OD+RS_cumulo+rab_integral+RQ_integral+AS_Vol.+emission_CO2+interval_O2; 0.334, 0.679, tmp_cumulo+PL_cumulo+AN+AN_cumulo+interval_yield+interval_Pdt.+OD+Feed_Vol+RS_cumulo+rab_integral+RQ_integral+AS_Vol.+emission_CO2+consum_O2; 0.386, 0.678, PL_cumulo+AN+AN_cumulo+interval_yield+RS_cumulo+rab_integral+RQ_integral+AS_Vol.+emission_CO2; 0.366, 0.678, pH_cumulo+PL+PL_cumulo+AN_cumulo+interval_yield+Feed_Vol+RS_cumulo+rab_integral+RQ_integral+AS_Vol.+emission_CO2; 0.386, 0.678, O2+PL_cumulo+interval_yield+interval_Pdt.+RS_cumulo+RQ_integral+AS_Vol.+emission_CO2+interval_O2; 0.356, 0.678, O2+PL_cumulo+AN+AN_cumulo+interval_yield+interval_Pdt.+Feed_Vol+RS_cumulo+rab_integral+RQ_integral+AS_Vol.+emission_CO2; 0.345, 0.678, tmp_cumulo+pH_cumulo+PL_cumulo+AN_cumulo+interval_yield+RS+Feed_Vol+RS_cumulo+rab_integral+RQ_integral+AS_Vol.+emission_CO2+consum_O2; 0.345, 0.678, tmp_cumulo+pH+PL+PL_cumulo+AN_cumulo+interval_yield+Feed_Vol+RS_cumulo+rab_integral+RQ_integral+AS_Vol.+emission_CO2+consum_O2; 0.345, 0.678, tmp_cumulo+pH+PL_cumulo+AN+AN_cumulo+interval_yield+interval_Pdt.+RS_cumulo+rab_integral+RQ_integral+AS_Vol.+emission_CO2+consum_O2; 0.356, 0.678, tmp+tmp_cumulo+pH+AN_cumulo+interval_yield+Feed_Vol+RS_cumulo+rab_integral+RQ_integral+AS_Vol.+emission_CO2+interval_O2; 0.356, 0.678, tmp_cumulo+AN_cumulo+interval_yield+interval_Pdt.+Feed_Vol+RS_cumulo+rab_integral+RQ_integral+AS_Vol.+emission_O2+emission_CO2+consum_O2; 0.356, 0.678, pH+PL+PL_cumulo+AN_cumulo+interval_yield+RS+Feed_Vol+RS_cumulo+rab_integral+RQ_integral+AS_Vol.+emission_CO2; 0.345, 0.678, tmp_cumulo+AN+AN_cumulo+interval_yield+RS+Feed_Vol+RS_cumulo+rab_integral+RQ_integral+AS_Vol.+emission_O2+consum_O2+interval_O2; 0.385, 0.678, PL_cumulo+interval_yield+interval_Pdt.+Feed_Vol+RS_cumulo+rab_integral+RQ_integral+AS_Vol.+emission_CO2; 0.376, 0.678, PL_cumulo+AN_cumulo+interval_yield+OD+Feed_Vol+RS_cumulo+rab_integral+RQ_integral+AS_Vol.+emission_CO2; 0.366, 0.678, tmp+pH+PL_cumulo+AN_cumulo+interval_yield+interval_Pdt.+RS_cumulo+rab_integral+RQ_integral+AS_Vol.+emission_CO2; 0.345, 0.678, tmp_cumulo+pH+PL_cumulo+AN+AN_cumulo+interval_yield+interval_Pdt.+Feed_Vol+RS_cumulo+rab_integral+RQ_integral+AS_Vol.+emission_CO2; 0.356, 0.678, pH+PL_cumulo+AN_cumulo+interval_yield+interval_Pdt.+RS+RS_cumulo+rab_integral+RQ_integral+AS_Vol.+emission_CO2+interval_O2; 0.395, 0.678, pH+PL+PL_cumulo+AN_cumulo+interval_yield+RS+Feed_Vol+AS_Vol.; 0.366, 0.678, tmp+PL_cumulo+AN_cumulo+interval_yield+interval_Pdt.+OD+RS_cumulo+rab_integral+RQ_integral+AS_Vol.+emission_CO2; 0.356, 0.678, tmp_cumulo+AN_cumulo+interval_yield+OD+RS+Feed_Vol+RS_cumulo+rab_integral+RQ_integral+AS_Vol.+emission_CO2+interval_O2; 0.366, 0.678, PL_cumulo+AN+AN_cumulo+interval_yield+interval_Pdt.+OD+RS_cumulo+rab_integral+RQ_integral+AS_Vol.+emission_CO2; 0.356, 0.678, PL_cumulo+AN_cumulo+interval_yield+interval_Pdt.+RS+RS_cumulo+rab_integral+RQ_integral+AS_Vol.+emission_CO2+consum_O2+interval_O2; 0.385, 0.678, PL_cumulo+AN_cumulo+interval_yield+RS+Feed_Vol+RS_cumulo+AS_Vol.+emission_O2+interval_O2; 0.366, 0.678, tmp+tmp_cumulo+PL+PL_cumulo+interval_yield+interval_Pdt.+RS_cumulo+rab_integral+RQ_integral+AS_Vol.+emission_CO2; 0.345, 0.678, tmp_cumulo+PL_cumulo+AN+AN_cumulo+interval_yield+Feed_Vol+RS_cumulo+rab_integral+RQ_integral+Accum._Yield+AS_Vol.+emission_CO2+interval_O2; 0.395, 0.678, PL_cumulo+AN_cumulo+interval_yield+OD+RS+Feed_Vol+AS_Vol.+emission_O2; 0.356, 0.678, pH_cumulo+PL+PL_cumulo+AN_cumulo+interval_yield+interval_Pdt.+RS_cumulo+rab_integral+RQ_integral+AS_Vol.+emission_CO2+interval_O2; 0.385, 0.678, O2+PL_cumulo+AN+interval_yield+OD+RS+Feed_Vol+AS_Vol.+interval_O2; 0.334, 0.678, tmp_cumulo+PL_cumulo+AN+AN_cumulo+interval_yield+OD+RS+Feed_Vol+RS_cumulo+rab_integral+RQ_integral+AS_Vol.+emission_CO2+consum_O2; 0.334, 0.678, tmp_cumulo+PL_cumulo+AN+AN_cumulo+interval_yield+interval_Pdt.+Feed_Vol+RS_cumulo+rab_integral+RQ_integral+AS_Vol.+emission_O2+emission_CO2+interval_O2; 0.345, 0.678, tmp+tmp_cumulo+PL_cumulo+AN_cumulo+interval_yield+interval_Pdt.+RS+Feed_Vol+RS_cumulo+rab_integral+RQ_integral+AS_Vol.+emission_O2; 0.376, 0.678, pH+pH_cumulo+PL+PL_cumulo+interval_yield+OD+RS+Feed_Vol+AS_Vol.+interval_O2; 0.376, 0.678, pH+PL+PL_cumulo+interval_yield+interval_Pdt.+RS_cumulo+rab_integral+RQ_integral+AS_Vol.+emission_CO2; 0.376, 0.678, tmp+PL_cumulo+interval_yield+interval_Pdt.+RS_cumulo+rab_integral+RQ_integral+AS_Vol.+emission_CO2+interval_O2; 0.356, 0.678, tmp_cumulo+PL_cumulo+AN+AN_cumulo+interval_yield+interval_Pdt.+RS+RS_cumulo+rab_integral+RQ_integral+AS_Vol.+emission_CO2; 0.356, 0.678, tmp_cumulo+PL_cumulo+AN_cumulo+interval_yield+interval_Pdt.+Feed_Vol+RS_cumulo+rab_integral+RQ_integral+AS_Vol.+emission_CO2+generate_CO2; 0.345, 0.678, tmp_cumulo+PL_cumulo+AN_cumulo+interval_yield+interval_Pdt.+Feed_Vol+RS_cumulo+rab_integral+RQ_integral+AS_Vol.+emission_CO2+consum_O2+generate_CO2; 0.366, 0.678, tmp_cumulo+PL_cumulo+AN+AN_cumulo+interval_yield+interval_Pdt.+RS_cumulo+rab_integral+RQ_integral+emission_CO2+consum_O2; 0.355, 0.678, tmp_cumulo+pH+pH_cumulo+PL_cumulo+AN_cumulo+interval_yield+Feed_Vol+RS_cumulo+rab_integral+RQ_integral+AS_Vol.+emission_CO2; 0.334, 0.678, tmp_cumulo+pH+pH_cumulo+PL_cumulo+AN_cumulo+interval_yield+interval_Pdt.+Feed_Vol+RS_cumulo+rab_integral+RQ_integral+AS_Vol.+emission_CO2+interval_O2; 0.345, 0.678, tmp_cumulo+PL_cumulo+AN+AN_cumulo+interval_yield+interval_Pdt.+RS+Feed_Vol+RS_cumulo+rab_integral+RQ_integral+AS_Vol.+emission_O2; 0.355, 0.678, tmp_cumulo+pH+PL_cumulo+interval_yield+interval_Pdt.+Feed_Vol+RS_cumulo+rab_integral+RQ_integral+AS_Vol.+emission_O2+emission_CO2; 0.366, 0.678, tmp_cumulo+AN_cumulo+interval_yield+RS+Feed_Vol+rab_integral+RQ_integral+AS_Vol.+emission_O2+consum_O2+interval_O2; 0.385, 0.678, tmp+PL+PL_cumulo+interval_yield+interval_Pdt.+RS_cumulo+RQ_integral+AS_Vol.+emission_CO2; 0.366, 0.678, PL_cumulo+AN+AN_cumulo+interval_yield+interval_Pdt.+RS+RS_cumulo+rab_integral+RQ_integral+AS_Vol.+emission_CO2; 0.334, 0.678, tmp_cumulo+PL+PL_cumulo+AN_cumulo+interval_yield+RS+Feed_Vol+RS_cumulo+rab_integral+RQ_integral+AS_Vol.+emission_CO2+consum_O2+interval_O2; 0.366, 0.678, tmp_cumulo+PL_cumulo+AN_cumulo+interval_yield+RS+Feed_Vol+rab_integral+RQ_integral+AS_Vol.+emission_O2+consum_O2; 0.385, 0.678, PL_cumulo+interval_yield+interval_Pdt.+RS_cumulo+rab_integral+RQ_integral+AS_Vol.+emission_CO2+consum_O2; 0.334, 0.678, tmp_cumulo+PL_cumulo+AN_cumulo+interval_yield+interval_Pdt.+RS+Feed_Vol+RS_cumulo+rab_integral+RQ_integral+AS_Vol.+emission_

O2+emission_CO2+interval_O2; 0.345, 0.678, tmp+tmp_cumulo+pH+PL_cumulo+AN_cumulo+interval_yield+interval_Pdt.+RS_cumulo+rab_integral+RQ_integral+AS_Vol.+emission_CO2+interval_O2; 0.366, 0.678, tmp_cumulo+PL_cumulo+interval_yield+interval_Pdt.+RS_cumulo+rab_integral+RQ_integral+AS_Vol.+emission_CO2+consum_O2+interval_O2; 0.385, 0.678, O2+PL_cumulo+AN+AN_cumulo+interval_yield+RS_cumulo+RQ_integral+AS_Vol.+emission_CO2; 0.375, 0.678, tmp_cumulo+pH+AN_cumulo+interval_yield+RS+Feed_Vol+rab_integral+RQ_integral+AS_Vol.+emission_O2; 0.394, 0.678, PL_cumulo+AN_cumulo+interval_yield+RS+Feed_Vol+RS_cumulo+AS_Vol.+emission_CO2; 0.345, 0.678, tmp_cumulo+PL_cumulo+AN_cumulo+interval_yield+OD+RS+Feed_Vol+RS_cumulo+rab_integral+RQ_integral+AS_Vol.+emission_CO2+interval_O2; 0.385, 0.678, PL_cumulo+interval_yield+interval_Pdt.+RS+RS_cumulo+rab_integral+RQ_integral+AS_Vol.+emission_CO2; 0.403, 0.678, PL_cumulo+interval_yield+RS_cumulo+RQ_integral+AS_Vol.+emission_O2+emission_CO2; 0.345, 0.678, tmp_cumulo+PL_cumulo+AN_cumulo+interval_yield+Feed_Vol+RS_cumulo+rab_integral+RQ_integral+Accum._Yield+AS_Vol.+emission_CO2+consum_O2+interval_O2; 0.345, 0.678, tmp_cumulo+PL_cumulo+AN_cumulo+interval_yield+interval_Pdt.+Feed_Vol+RS_cumulo+rab_integral+RQ_integral+AS_Vol.+emission_CO2+interval_O2+generate_CO2; 0.394, 0.678, O2+PL_cumulo+AN+AN_cumulo+interval_yield+RS+RQ_integral+emission_CO2; 0.355, 0.678, O2+PL_cumulo+AN_cumulo+interval_yield+RS+Feed_Vol+RS_cumulo+rab_integral+RQ_integral+AS_Vol.+emission_CO2+interval_O2; 0.345, 0.678, tmp_cumulo+PL_cumulo+AN+AN_cumulo+interval_yield+interval_Pdt.+RS+Feed_Vol+RS_cumulo+rab_integral+RQ_integral+AS_Vol.+emission_CO2; 0.355, 0.678, tmp+tmp_cumulo+pH_cumulo+PL_cumulo+AN_cumulo+interval_yield+Feed_Vol+RS_cumulo+rab_integral+RQ_integral+AS_Vol.+emission_CO2; 0.394, 0.678, O2+PL_cumulo+AN_cumulo+interval_yield+Feed_Vol+RS_cumulo+AS_Vol.+emission_CO2; 0.365, 0.678, pH+PL_cumulo+AN_cumulo+interval_yield+interval_Pdt.+OD+RS_cumulo+rab_integral+RQ_integral+AS_Vol.+emission_CO2; 0.345, 0.678, tmp_cumulo+PL_cumulo+AN+AN_cumulo+interval_yield+interval_Pdt.+RS+RS_cumulo+rab_integral+RQ_integral+AS_Vol.+emission_CO2+consum_O2; 0.345, 0.678, tmp+PL+PL_cumulo+AN_cumulo+interval_yield+interval_Pdt.+Feed_Vol+RS_cumulo+rab_integral+RQ_integral+AS_Vol.+emission_CO2+interval_O2; 0.355, 0.678, tmp_cumulo+PL_cumulo+AN+AN_cumulo+interval_yield+RS+Feed_Vol+rab_integral+RQ_integral+AS_Vol.+emission_O2+consum_O2; 0.345, 0.678, tmp_cumulo+AN+AN_cumulo+interval_yield+RS+Feed_Vol+RS_cumulo+rab_integral+RQ_integral+AS_Vol.+emission_CO2+consum_O2+generate_CO2; 0.375, 0.678, tmp_cumulo+PL+PL_cumulo+AN+AN_cumulo+interval_yield+RS_cumulo+rab_integral+RQ_integral+emission_CO2; 0.375, 0.678, tmp_cumulo+pH+PL+PL_cumulo+interval_yield+Feed_Vol+RS_cumulo+RQ_integral+AS_Vol.+emission_CO2; 0.375, 0.678, O2+PL_cumulo+interval_yield+OD+RS+Feed_Vol+AS_Vol.+emission_O2+consum_O2+interval_O2; 0.345, 0.678, tmp_cumulo+pH+AN+AN_cumulo+interval_yield+interval_Pdt.+Feed_Vol+RS_cumulo+rab_integral+RQ_integral+AS_Vol.+emission_CO2+interval_O2; 0.375, 0.678, tmp_cumulo+PL_cumulo+interval_yield+interval_Pdt.+RS+Feed_Vol+RS_cumulo+AS_Vol.+emission_O2+interval_O2; 0.375, 0.678, tmp_cumulo+PL+PL_cumulo+interval_yield+RS+Feed_Vol+RS_cumulo+AS_Vol.+consum_O2+interval_O2; 0.355, 0.678, tmp_cumulo+PL+PL_cumulo+AN_cumulo+interval_yield+RS+Feed_Vol+RS_cumulo+rab_integral+RQ_integral+AS_Vol.+emission_O2; 0.375, 0.678, PL_cumulo+AN_cumulo+interval_yield+interval_Pdt.+RS_cumulo+rab_integral+RQ_integral+AS_Vol.+emission_O2+emission_CO2; 0.375, 0.678, tmp_cumulo+AN_cumulo+interval_yield+interval_Pdt.+RS_cumulo+rab_integral+RQ_integral+AS_Vol.+emission_CO2+generate_CO2; 0.345, 0.678, tmp+tmp_cumulo+AN+AN_cumulo+interval_yield+RS+Feed_Vol+RS_cumulo+rab_integral+RQ_integral+AS_Vol.+emission_CO2+interval_O2; 0.394, 0.678, tmp_cumulo+AN_cumulo+interval_yield+RS+Feed_Vol+rab_integral+RQ_integral+AS_Vol.; 0.344, 0.678, tmp+tmp_cumulo+AN+AN_cumulo+interval_yield+interval_Pdt.+Feed_Vol+RS_cumulo+rab_integral+RQ_integral+AS_Vol.+emission_CO2+consum_O2; 0.344, 0.678, tmp_cumulo+pH+pH_cumulo+PL_cumulo+AN_cumulo+interval_yield+Feed_Vol+RS_cumulo+rab_integral+RQ_integral+AS_Vol.+emission_CO2+interval_O2; 0.334, 0.678, tmp_cumulo+pH_cumulo+PL_cumulo+AN+AN_cumulo+interval_yield+interval_Pdt.+Feed_Vol+RS_cumulo+rab_integral+RQ_integral+AS_Vol.+emission_CO2+consum_O2; 0.394, 0.678, AN_cumulo+interval_yield+interval_Pdt.+RS_cumulo+rab_integral+RQ_integral+AS_Vol.+emission_CO2; 0.375, 0.678, O2+PL_cumulo+AN_cumulo+interval_yield+RS+Feed_Vol+RS_cumulo+AS_Vol.+consum_O2+interval_O2; 0.355, 0.678, tmp_cumulo+PL_cumulo+AN_cumulo+interval_yield+interval_Pdt.+RS_cumulo+rab_integral+RQ_integral+AS_Vol.+emission_CO2+consum_O2+generate_CO2; 0.355, 0.678, tmp_cumulo+pH+AN_cumulo+interval_yield+interval_Pdt.+RS+Feed_Vol+RS_cumulo+rab_integral+RQ_integral+AS_Vol.+emission_O2; 0.365, 0.678, tmp_cumulo+AN_cumulo+interval_yield+RS+Feed_Vol+RS_cumulo+rab_integral+RQ_integral+AS_Vol.+emission_O2+emission_CO2; 0.344, 0.678, tmp_cumulo+pH+PL_cumulo+AN_cumulo+interval_yield+interval_Pdt.+RS_cumulo+rab_integral+RQ_integral+AS_Vol.+emission_CO2+consum_O2+interval_O2; 0.344, 0.678, tmp_cumulo+PL+PL_cumulo+AN+AN_cumulo+interval_yield+interval_Pdt.+RS_cumulo+rab_integral+RQ_integral+AS_Vol.+emission_CO2+consum_O2; 0.385, 0.678, pH_cumulo+PL_cumulo+interval_yield+interval_Pdt.+RS_cumulo+rab_integral+RQ_integral+AS_Vol.+emission_CO2; 0.355, 0.678, tmp_cumulo+pH+PL_cumulo+interval_yield+interval_Pdt.+Feed_Vol+RS_cumulo+rab_integral+RQ_integral+AS_Vol.+emission_CO2+interval_O2; 0.365, 0.678, tmp+tmp_cumulo+pH+PL_cumulo+interval_yield+Feed_Vol+RS_cumulo+rab_integral+RQ_integral+AS_Vol.+emission_CO2; 0.385, 0.678, pH+PL+PL_cumulo+interval_yield+interval_Pdt.+RS_cumulo+RQ_integral+AS_Vol.+emission_CO2; 0.385, 0.678, O2+PL_cumulo+AN_cumulo+interval_yield+RS+Feed_Vol+rab_integral+RQ_integral+AS_Vol.; 0.355, 0.678, tmp_cumulo+PL_cumulo+AN_cumulo+interval_yield+RS+Feed_Vol+RS_cumulo+rab_integral+RQ_integral+AS_Vol.+emission_O2+generate_CO2; 0.333, 0.678, tmp_cumulo+PL+PL_cumulo+AN+AN_cumulo+interval_yield+RS+Feed_Vol+RS_cumulo+rab_integral+RQ_integral+AS_Vol.+emission_CO2+interval_O2; 0.355, 0.678, tmp_cumulo+PL_cumulo+AN_cumulo+interval_yield+RS+Feed_Vol+RS_cumulo+rab_integral+AS_Vol.+emission_O2+consum_O2+interval_O2; 0.394, 0.678, PL_cumulo+AN+AN_cumulo+interval_yield+RS_cumulo+RQ_integral+AS_Vol.+emission_CO2; 0.333, 0.678, tmp_cumulo+PL+PL_cumulo+AN_cumulo+interval_yield+ interval_Pdt.+OD+Feed_Vol+RS_cumulo+rab_integral+RQ_integral+AS_Vol.+emission_CO2+interval_O2; 0.344, 0.678, tmp_cumulo+AN+AN_cumulo+interval_yield+interval_Pdt.+OD+Feed_Vol+RS_cumulo+rab_integral+RQ_integral+AS_Vol.+emission_CO2+consum_O2; 0.385, 0.678, O2+PL_cumulo+AN_cumulo+interval_yield+OD+RS+Feed_Vol+AS_Vol.+interval_O2; 0.333, 0.678, tmp_cumulo+pH_cumulo+PL+PL_cumulo+AN_cumulo+interval_yield+interval_Pdt.+Feed_Vol+RS_cumulo+rab_integral+AS_Vol.+emission_CO2+interval_O2; 0.365, 0.678, pH+pH_cumulo+PL+PL_cumulo+interval_yield+OD+RS+Feed_Vol+AS_Vol.+consum_O2+interval_O2; 0.333, 0.678, tmp_cumulo+PL+PL_cumulo+AN+AN_cumulo+interval_yield+Feed_Vol+RS_cumulo+rab_integral+RQ_integral+AS_Vol.+emission_CO2+consum_O2+interval_O2; 0.365, 0.678, tmp_cumulo+AN+AN_cumulo+interval_yield+Feed_Vol+RS_cumulo+rab_integral+RQ_integral+AS_Vol.+emission_CO2+generate_CO2; 0.394, 0.678, O2+PL_cumulo+AN_cumulo+interval_yield+RS+Feed_Vol+AS_Vol.+emission_O2; 0.355, 0.678, tmp_cumulo+PL_cumulo+AN_cumulo+interval_yield+interval_Pdt.+OD+RS_cumulo+rab_integral+RQ_integral+AS_Vol.+emission_CO2+consum_O2; 0.365, 0.678, tmp_cumulo+pH_cumulo+PL+PL_cumulo+interval_yield+Feed_Vol+RS_cumulo+rab_integral+RQ_integral+AS_Vol.+emission_CO2; 0.344, 0.678, tmp_cumulo+pH_cumulo+PL_cumulo+AN_cumulo+interval_yield+Feed_Vol+RS_cumulo+rab_integral+RQ_integral+AS_Vol.+emission_CO2+consum_O2+interval_O2; 0.322, 0.678, tmp_cumulo+pH+PL_cumulo+AN+AN_cumulo+interval_yield+RS+Feed_Vol+RS_cumulo+rab_integral+RQ_integral+AS_Vol.+emission_CO2+consum_O2+interval_O2; 0.384, 0.678, PL_cumulo+AN_cumulo+interval_yield+Feed_Vol+RS_cumulo+RQ_integral+AS_Vol.+emission_CO2+interval_O2; 0.344, 0.678, tmp_cumulo+PL_cumulo+AN+AN_cumulo+interval_yield+RS+Feed_Vol+rab_integral+RQ_integral+AS_Vol.+emission_O2+consum_O2+interval_O2; 0.333, 0.678, tmp_cumulo+pH_cumulo+PL_cumulo+AN_cumulo+interval_yield+interval_Pdt.+RS+Feed_Vol+RS_cumulo+rab_integral+RQ_integral+AS_Vol.+emission_CO2+interval_O2; 0.375, 0.678, tmp_cumulo+PL_cumulo+AN_cumulo+interval_yield+RS+Feed_Vol+RS_cumulo+AS_Vol.+emission_O2+consum_O2; 0.375, 0.678, tmp_cumulo+AN_cumulo+interval_yield+RS+Feed_Vol+RS_cumulo+rab_integral+RQ_integral+AS_Vol.+generate_CO2; 0.355, 0.678, tmp_cumulo+AN+AN_cumulo+interval_yield+OD+RS+Feed_Vol+RS_cumulo+rab_integral+RQ_integral+AS_Vol.+emission_CO2; 0.344, 0.678, tmp+tmp_cumulo+PL_cumulo+AN_cumulo+interval_yield+interval_Pdt.+RS+RS_cumulo+rab_integral+RQ_integral+AS_Vol.+emission_CO2+interval_O2; 0.365, 0.678, O2+PL_cumulo+AN_cumulo+interval_yield+RS+Feed_Vol+RS_cumulo+AS_Vol.+emission_CO2+consum_O2+interval_O2; 0.355, 0.678, tmp_cumulo+PL+PL_cumulo+AN_cumulo+interval_yield+Feed_Vol+RS_cumulo+rab_integral+RQ_integral+Accum._Yield+AS_Vol.+emission_CO2; 0.365, 0.678, PL_cumulo+AN_cumulo+interval_yield+interval_Pdt.+RS+Feed_Vol+RS_cumulo+rab_integral+RQ_integral+AS_Vol.+emission_CO2; 0.365, 0.678, tmp_cumulo+PL_cumulo+AN+interval_yield+Feed_Vol+RS_cumulo+rab_integral+RQ_integral+AS_Vol.+emission_CO2+interval_O2; 0.394, 0.678, O2+PL_cumulo+AN+AN_cumulo+interval_yield+RS+Feed_Vol+AS_Vol.; 0.375, 0.678, O2+PL_cumulo+AN_cumulo+interval_yield+RS+Feed_Vol+AS_Vol.+emission_CO2+consum_O2+interval_O2; 0.365, 0.678, tmp_cumulo+PL_cumulo+interval_yield+Feed_Vol+RS_cumulo+rab_integral+RQ_integral+AS_Vol.+emission_O2+emission_CO2+interval_O2; 0.375, 0.678, tmp_cumulo+PL_cumulo+interval_yield+Feed_Vol+RS_cumulo+rab_integral+RQ_integral+AS_Vol.+emission_CO2+generate_CO2; 0.365, 0.678, tmp_cumulo+PL+PL_cumulo+interval_yield+interval_Pdt.+RS_cumulo+rab_integral+RQ_integral+AS_Vol.+emission_CO2+interval_O2; 0.375, 0.678, pH_cumulo+PL_cumulo+AN_cumulo+interval_yield+Feed_Vol+RS_cumulo+rab_integral+RQ_integral+AS_Vol.+emission_CO2; 0.375, 0.678, tmp_cumulo+pH_cumulo+AN_cumulo+interval_yield+RS+Feed_Vol+rab_integral+RQ_integral+AS_Vol.+emission_O2; 0.394, 0.678, PL_cumulo+interval_yield+interval_Pdt.+RS+RS_cumulo+RQ_integral+AS_Vol.+emission_CO2; 0.355, 0.678, pH_cumulo+PL_cumulo+AN_cumulo+interval_yield+interval_Pdt.+RS_cumulo+rab_integral+RQ_integral+AS_Vol.+emission_CO2+consum_O2+interval_O2; 0.344, 0.678, tmp+tmp_cumulo+PL+PL_cumulo+AN_cumulo+interval_yield+interval_Pdt.+RS_cumulo+rab_integral+RQ_integral+AS_Vol.+emission_CO2+interval_O2; 0.375, 0.678, PL_cumulo+AN+interval_yield+interval_Pdt.+RS_cumulo+rab_integral+RQ_integral+AS_Vol.+emission_CO2+interval_O2; 0.355, 0.678, tmp+tmp_cumulo+pH+AN_cumulo+interval_yield+interval_Pdt.+Feed_Vol+RS_cumulo+rab_integral+RQ_integral+AS_Vol.+emission_CO2; 0.365, 0.678, tmp+tmp_cumulo+PL_cumulo+interval_yield+Feed_Vol+RS_cumulo+rab_integral+RQ_integral+AS_Vol.+emission_CO2+interval_O2; 0.365, 0.678, tmp_cumulo+PL_cumulo+interval_yield+interval_Pdt.+Feed_Vol+RS_cumulo+rab_integral+RQ_integral+AS_Vol.+emission_O2+interval_O2; 0.354, 0.678, pH+PL+PL_cumulo+AN_cumulo+interval_yield+interval_Pdt.+RS+RS_cumulo+rab_integral+RQ_integral+AS_Vol.+emission_CO2; 0.384, 0.678, tmp_cumulo+AN+interval_yield+Feed_Vol+RS_cumulo+rab_integral+RQ_integral+AS_Vol.+emission_CO2; 0.344, 0.678, tmp_cumulo+PL_cumulo+AN+AN_cumulo+interval_yield+interval_Pdt.+OD+RS_cumulo+rab_integral+RQ_integral+AS_Vol.+emission_CO2+consum_O2; 0.365, 0.678, tmp+pH_cumulo+PL_cumulo+AN_cumulo+interval_yield+interval_Pdt.+RS_cumulo+rab_integral+RQ_integral+AS_Vol.+emission_CO2; 0.354, 0.678, tmp_cumulo+PL_cumulo+AN_cumulo+interval_yield+interval_Pdt.+Feed_Vol+RS_cumulo+rab_integral+RQ_integral+Accum._Yield+AS_Vol.+emission_CO2; 0.375, 0.678, tmp_cumulo+AN_cumulo+interval_yield+RS+Feed_Vol+rab_integral+RQ_integral+AS_Vol.+emission_CO2+consum_O2; 0.333, 0.678, tmp+tmp_cumulo+PL_cumulo+AN_cumulo+interval_yield+interval_Pdt.+OD+Feed_Vol+RS_cumulo+rab_integral+RQ_integral+AS_Vol.+emission_CO2+interval_O2; 0.354, 0.678, tmp+tmp_cumulo+AN_cumulo+interval_yield+interval_Pdt.+RS+Feed_Vol+RS_cumulo+rab_integral+RQ_integral+AS_Vol.+emission_O2; 0.394, 0.678, pH+PL+PL_cumulo+interval_yield+RS+Feed_Vol+AS_Vol.+interval_O2; 0.344, 0.678, tmp_cumulo+PL_cumulo+AN_cumulo+interval_yield+Feed_Vol+RS_cumulo+rab_integral+RQ_integral+AS_Vol.+emission_O2+emission_CO2+consum_O2+interval_O2; 0.365, 0.678, tmp_cumulo+AN_cumulo+interval_yield+interval_Pdt.+RS+Feed_Vol+RS_cumulo+rab_integral+RQ_integral+AS_Vol.+consum_O2; 0.365, 0.678, tmp_cumulo+AN_cumulo+interval_yield+OD+RS+Feed_Vol+RS_cumulo+rab_integral+RQ_integral+AS_Vol.+emission_O2; 0.384, 0.678, O2+PL_cumulo+interval_yield+interval_Pdt.+RS_cumulo+RQ_integral+AS_Vol.+emission_O2+emission_CO2; 0.365, 0.678, tmp+tmp_cumulo+pH_cumulo+AN_cumulo+interval_yield+Feed_Vol+RS_cumulo+rab_integral+ RQ_integral+AS_Vol.+emission_CO2; 0.354, 0.678, tmp_cumulo+PL_cumulo+AN+AN_cumulo+interval_yield+interval_Pdt.+RS+RS_cumulo+rab_integral+RQ_integral+emission_CO2+consum_O2; 0.354, 0.678, tmp+PL+PL_cumulo+AN_cumulo+interval_yield+interval_Pdt.+RS_cumulo+rab_integral+RQ_integral+AS_Vol.+emission_CO2+consum_O2; 0.354, 0.678, tmp_cumulo+AN+AN_cumulo+interval_yield+OD+Feed_Vol+RS_cumulo+rab_integral+RQ_integral+AS_Vol.+emission_CO2+interval_O2; 0.365, 0.678, O2+PL_cumulo+AN_cumulo+interval_yield+OD+Feed_Vol+RS_cumulo+rab_integral+RQ_integral+AS_Vol.+emission_CO2; 0.393, 0.678, O2+PL_cumulo+interval_yield+RS+Feed_Vol+RS_cumulo+AS_Vol.+emission_CO2; 0.393, 0.678, O2+PL_cumulo+AN+interval_yield+RS+Feed_Vol+RS_cumulo+AS_Vol.; 0.354, 0.678, tmp_cumulo+pH+AN_cumulo+interval_yield+interval_Pdt.+OD+Feed_Vol+RS_cumulo+rab_integral+RQ_integral+AS_Vol.+emission_CO2; 0.344, 0.678, tmp_cumulo+PL_cumulo+AN_cumulo+interval_yield+RS+Feed_Vol+RS_cumulo+rab_integral+AS_Vol.+emission_O2+consum_O2+interval_O2+generate_CO2; 0.354, 0.678, tmp+PL_cumulo+AN_cumulo+interval_yield+interval_Pdt.+Feed_Vol+RS_cumulo+rab_integral+RQ_integral+AS_Vol.+emission_CO2+consum_O2; 0.344, 0.678, tmp+tmp_cumulo+PL+PL_cumulo+AN_cumulo+interval_yield+RS+Feed_Vol+RS_cumulo+rab_integral+RQ_integral+AS_Vol.+emission_CO2; 0.365, 0.678, tmp_cumulo+PL_cumulo+interval_yield+interval_Pdt.+RS+Feed_Vol+RS_cumulo+AS_Vol.+emission_O2+consum_O2+interval_O2; 0.374, 0.678, tmp_cumulo+AN_cumulo+interval_yield+OD+RS+Feed_Vol+rab_integral+RQ_integral+AS_Vol.+emission_O2; 0.384, 0.677, tmp+tmp_cumulo+PL_cumulo+interval_yield+interval_Pdt.+RS_cumulo+RQ_integral+AS_Vol.+emission_CO2; 0.344, 0.677, tmp_cumulo+pH+PL_cumulo+AN_cumulo+interval_yield+interval_Pdt.+Feed_Vol+RS_cumulo+rab_integral+RQ_integral+AS_Vol.+emission_O2+emission_CO2; 0.374, 0.677, tmp_cumulo+PL_cumulo+AN+AN_cumulo+interval_yield+RS_cumulo+rab_integral+RQ_integral+emission_CO2+interval_O2; 0.365, 0.677, tmp_cumulo+pH_cumulo+AN_cumulo+interval_yield+interval_Pdt.+Feed_Vol+RS_cumulo+rab_integral+RQ_integral+AS_Vol.+emission_O2; 0.333, 0.677, tmp_cumulo+PL_cumulo+AN+AN_cumulo+interval_yield+interval_Pdt.+Feed_Vol+RS_cumulo+rab_integral+RQ_integral+Accum._Yield+AS_Vol.+emission_CO2+consum_O2; 0.333, 0.677, tmp_cumulo+pH+PL_cumulo+AN_cumulo+interval_yield+interval_Pdt.+OD+Feed_Vol+RS_cumulo+rab_integral+RQ_integral+AS_Vol.+emission_CO2+consum_O2; 0.344, 0.677, tmp_cumulo+PL_cumulo+AN_cumulo+interval_yield+interval_Pdt.+RS+Feed_Vol+RS_cumulo+rab_integral+RQ_integral+AS_Vol.+emission_O2+emission_CO2; 0.354, 0.677, tmp_cumulo+AN+AN_cumulo+interval_yield+RS+Feed_Vol+rab_integral+RQ_integral+AS_Vol.+emission_CO2+consum_O2+interval_O2; 0.393, 0.677, tmp_cumulo+interval_yield+OD+RS+Feed_Vol+AS_Vol.+emission_O2+interval_O2; 0.374, 0.677, O2+PL_cumulo+AN_cumulo+interval_yield+RS+Feed_Vol+RS_cumulo+AS_Vol.+emission_CO2+interval_O2; 0.344, 0.677, tmp_cumulo+pH+AN+AN_cumulo+interval_yield+Feed_Vol+RS_cumulo+rab_integral+RQ_integral+AS_Vol.+emission_CO2+consum_O2+interval_O2; 0.354, 0.677, tmp+PL_cumulo+AN+AN_cumulo+interval_yield+interval_Pdt.+RS_cumulo+rab_integral+RQ_integral+AS_Vol.+emission_CO2+consum_O2; 0.384, 0.677, PL_cumulo+AN+interval_yield+OD+RS+Feed_Vol+AS_Vol.+emission_O2+interval_O2; 0.354, 0.677, pH+pH_cumulo+PL+PL_cumulo+AN_cumulo+interval_yield+interval_Pdt.+RS_cumulo+rab_integral+RQ_integral+AS_Vol.+emission_CO2; 0.354, 0.677, O2+PL_cumulo+AN+AN_cumulo+interval_yield+RS+Feed_Vol+RS_cumulo+rab_integral+RQ_integral+AS_Vol.+emission_CO2; 0.402, 0.677, tmp_cumulo+interval_yield+RS+Feed_Vol+RS_cumulo+AS_Vol.+emission_CO2; 0.393, 0.677, pH_cumulo+PL+PL_cumulo+AN_cumulo+interval_yield+RS+Feed_Vol+AS_Vol.; 0.344, 0.677, tmp+tmp_cumulo+PL+PL_cumulo+AN+AN_cumulo+interval_yield+Feed_Vol+RS_cumulo+rab_integral+RQ_integral+AS_Vol.+emission_CO2; 0.344, 0.677, tmp+tmp_cumulo+AN_cumulo+interval_yield+interval_Pdt.+RS+Feed_Vol+RS_cumulo+rab_integral+RQ_integral+AS_Vol.+emission_CO2+interval_O2; 0.344, 0.677, tmp_cumulo+pH+PL_cumulo+AN+AN_cumulo+interval_yield+RS+Feed_Vol+RS_cumulo+rab_integral+RQ_integral+AS_Vol.+emission_CO2; 0.374, 0.677, tmp_cumulo+PL_cumulo+AN_cumulo+interval_yield+Feed_Vol+RS_cumulo+RQ_integral+AS_Vol.+emission_CO2+interval_O2; 0.374, 0.677, tmp_cumulo+pH+AN_cumulo+interval_yield+interval_Pdt.+RS_cumulo+rab_integral+RQ_integral+AS_Vol.+emission_CO2; 0.354, 0.677, tmp_cumulo+AN_cumulo+interval_yield+RS+Feed_Vol+RS_cumulo+rab_integral+RQ_integral+AS_Vol.+consum_O2+interval_O2+generate_CO2; 0.384, 0.677, pH_cumulo+PL_cumulo+interval_yield+OD+RS+Feed_Vol+AS_Vol.+emission_O2+interval_O2; 0.384, 0.677, O2+PL_cumulo+interval_yield+Feed_Vol+RS_cumulo+rab_integral+RQ_integral+AS_Vol.+emission_CO2; 0.364, 0.677, tmp_cumulo+pH_cumulo+PL_cumulo+interval_yield+Feed_Vol+RS_cumulo+rab_integral+RQ_integral+AS_Vol.+emission_O2+emission_CO2; 0.333, 0.677, tmp_cumulo+pH+PL+PL_cumulo+AN_cumulo+interval_yield+RS+Feed_Vol+RS_cumulo+rab_integral+RQ_integral+AS_Vol.+emission_CO2+interval_O2; 0.364, 0.677, tmp_cumulo+AN_cumulo+interval_yield+interval_Pdt.+RS+RS_cumulo+rab_integral+RQ_integral+AS_Vol.+emission_CO2+interval_O2; 0.374, 0.677, tmp_cumulo+AN_cumulo+interval_yield+OD+RS+Feed_Vol+rab_integral+RQ_integral+AS_Vol.+emission_CO2; 0.402, 0.677, tmp_cumulo+PL_cumulo+interval_yield+RS_cumulo+RQ_integral+AS_Vol.+emission_CO2; 0.374, 0.677, tmp_cumulo+PL+AN_cumulo+interval_yield+interval_Pdt.+RS_cumulo+rab_integral+RQ_integral+AS_Vol.+emission_CO2; 0.364, 0.677, tmp_cumulo+PL+AN_cumulo+interval_yield+RS+Feed_Vol+RS_cumulo+rab_integral+RQ_integral+AS_Vol.+emission_O2; 0.333, 0.677, tmp_cumulo+pH_cumulo+PL_cumulo+AN+AN_cumulo+interval_yield+interval_Pdt.+Feed_Vol+RS_cumulo+rab_integral+RQ_integral+AS_Vol.+emission_CO2+interval_O2; 0.333, 0.677, tmp+tmp_cumulo+pH_cumulo+PL_cumulo+AN_cumulo+interval_yield+interval_Pdt.+Feed_Vol+RS_cumulo+rab_integral+RQ_integral+AS_Vol.+emission_CO2+interval_O2; 0.344, 0.677, tmp+tmp_cumulo+pH_cumulo+PL_cumulo+AN_cumulo+interval_yield+Feed_Vol+RS_cumulo+rab_integral+RQ_integral+AS_Vol.+emission_CO2+interval_O2; 0.374, 0.677, pH+PL+PL_cumulo+AN_cumulo+interval_yield+Feed_Vol+RS_cumulo+RQ_integral+AS_Vol.+emission_CO2; 0.364, 0.677, tmp+tmp_cumulo+PL+AN_cumulo+interval_yield+Feed_Vol+RS_cumulo+rab_integral+RQ_integral+AS_Vol.+emission_CO2; 0.354, 0.677, tmp_cumulo+PL_cumulo+AN_cumulo+interval_yield+interval_Pdt.+OD+Feed_Vol+RS_cumulo+rab_integral+RQ_integral+AS_Vol.+emission_O2; 0.343, 0.677, tmp+tmp_cumulo+AN_ cumulo+interval_yield+RS+Feed_Vol+RS_cumulo+rab_integral+RQ_integral+AS_Vol.+emission_CO2+consum_O2+interval_O2; 0.343, 0.677, pH+PL+PL_cumulo+AN_cumulo+interval_yield+interval_Pdt.+Feed_Vol+RS_cumulo+rab_integral+RQ_integral+AS_Vol.+emission_CO2+interval_O2; 0.343, 0.677, tmp_cumulo+PL_cumulo+AN_cumulo+interval_yield+interval_Pdt.+RS+RS_cumulo+rab_integral+RQ_integral+AS_Vol.+emission_CO2+consum_O2+interval_O2; 0.384, 0.677, O2+PL_cumulo+AN_cumulo+interval_yield+RS+Feed_Vol+RS_cumulo+AS_Vol.+interval_O2; 0.354, 0.677, tmp+tmp_cumulo+pH+AN_cumulo+interval_yield+RS+Feed_Vol+RS_cumulo+rab_integral+RQ_integral+AS_Vol.+emission_CO2; 0.332, 0.677, tmp+tmp_cumulo+AN+AN_cumulo+interval_yield+RS+Feed_Vol+RS_cumulo+rab_integral+RQ_integral+AS_Vol.+emission_CO2+consum_O2+interval_O2; 0.354, 0.677, tmp_cumulo+pH+PL+AN_cumulo+interval_yield+RS+Feed_Vol+RS_cumulo+rab_integral+RQ_integral+AS_Vol.+emission_CO2; 0.354, 0.677, tmp_cumulo+pH+AN+AN_cumulo+interval_yield+RS+Feed_Vol+rab_integral+RQ_integral+AS_Vol.+emission_CO2+consum_O2; 0.332, 0.677, tmp_cumulo+pH+PL_cumulo+AN_cumulo+interval_yield+interval_Pdt.+Feed_Vol+RS_cumulo+rab_integral+RQ_integral+AS_Vol.+emission_O2+emission_CO2+consum_O2; 0.354, 0.677, tmp_cumulo+pH+AN_cumulo+interval_yield+RS+Feed_Vol+RS_cumulo+rab_integral+RQ_integral+AS_Vol.+emission_O2+consum_O2; 0.364, 0.677, tmp_cumulo+PL_cumulo+AN_cumulo+interval_yield+interval_Pdt.+RS_cumulo+rab_integral+RQ_integral+AS_Vol.+emission_O2+emission_CO2; 0.343, 0.677, tmp_cumulo+pH_cumulo+PL_cumulo+AN+AN_cumulo+interval_yield+interval_Pdt.+RS_cumulo+rab_integral+RQ_integral+AS_Vol.+emission_CO2+interval_O2; 0.332, 0.677, tmp_cumulo+pH+PL+PL_cumulo+AN+AN_cumulo+interval_yield+Feed_Vol+RS_cumulo+rab_integral+RQ_integral+AS_Vol.+emission_CO2+interval_O2; 0.364, 0.677, tmp_cumulo+PL+PL_cumulo+AN+interval_yield+Feed_Vol+RS_cumulo+rab_integral+RQ_integral+AS_Vol.+emission_CO2; 0.354, 0.677, tmp+PL_cumulo+AN_cumulo+interval_yield+RS+Feed_Vol+RS_cumulo+rab_integral+RQ_integral+AS_Vol.+emission_CO2+interval_O2; 0.354, 0.677, O2+PL_cumulo+AN+AN_cumulo+interval_yield+interval_Pdt.+OD+RS_cumulo+rab_integral+RQ_integral+AS_Vol.+emission_CO2; 0.332, 0.677, tmp_cumulo+pH_cumulo+PL_cumulo+AN+AN_cumulo+interval_yield+RS+Feed_Vol+RS_cumulo+rab_integral+RQ_integral+AS_Vol.+emission_CO2+consum_O2; 0.384, 0.677, tmp_cumulo+pH_cumulo+PL_cumulo+interval_yield+Feed_Vol+RS_cumulo+RQ_integral+AS_Vol.+emission_CO2; 0.354, 0.677, pH+PL+AN+AN_cumulo+interval_yield+interval_Pdt.+RS_cumulo+rab_integral+RQ_integral+AS_Vol.+emission_CO2+consum_O2; 0.384, 0.677, tmp_cumulo+PL_cumulo+interval_yield+interval_Pdt.+RS+RS_cumulo+RQ_integral+AS_Vol.+emission_CO2; 0.384, 0.677, tmp_cumulo+PL_cumulo+AN+AN_cumulo+interval_yield+RS_cumulo+RQ_integral+emission_CO2+interval_O2; 0.354, 0.677, tmp_cumulo+PL_cumulo+interval_yield+interval_Pdt.+RS+Feed_Vol+RS_cumulo+rab_integral+RQ_integral+AS_Vol.+emission_O2+emission_CO2; 0.321, 0.677, tmp_cumulo+pH+PL_cumulo+AN+AN_cumulo+interval_yield+interval_Pdt.+Feed_Vol+RS_cumulo+rab_integral+RQ_integral+AS_Vol.+emission_CO2+consum_O2+interval_O2; 0.332, 0.677, tmp_cumulo+PL_cumulo+AN+AN_cumulo+interval_yield+interval_Pdt.+OD+Feed_Vol+RS_cumulo+rab_integral+RQ_integral+AS_Vol.+ emission_CO2+interval_O2; 0.411, 0.677, PL_cumulo+interval_yield+RS+Feed_Vol+RS_cumulo+AS_Vol.; 0.332, 0.677, tmp+tmp_cumulo+PL+PL_cumulo+AN_cumulo+interval_yield+interval_Pdt.+Feed_Vol+RS_cumulo+rab_integral+RQ_integral+AS_Vol.+emission_CO2+consum_O2; 0.354, 0.677, tmp_cumulo+PL_cumulo+AN_cumulo+interval_yield+Feed_Vol+RS_cumulo+rab_integral+RQ_integral+AS_Vol.+emission_CO2+interval_O2+generate_CO2; 0.374, 0.677, tmp_cumulo+PL_cumulo+AN_cumulo+interval_yield+interval_Pdt.+RS+Feed_Vol+RS_cumulo+AS_Vol.+emission_O2; 0.332, 0.677, tmp_cumulo+PL_cumulo+AN_cumulo+interval_yield+interval_Pdt.+OD+RS+Feed_Vol+RS_cumulo+rab_integral+RQ_integral+AS_Vol.+emission_CO2+interval_O2; 0.343, 0.677, tmp_cumulo+PL_cumulo+AN+AN_cumulo+interval_yield+interval_Pdt.+RS_cumulo+rab_integral+RQ_integral+AS_Vol.+emission_O2+emission_CO2+interval_O2; 0.343, 0.677, tmp+tmp_cumulo+PL_cumulo+AN_cumulo+interval_yield+interval_Pdt.+RS+Feed_Vol+RS_cumulo+rab_integral+RQ_integral+AS_Vol.+emission_CO2; 0.354, 0.677, tmp_cumulo+PL+PL_cumulo+AN_cumulo+interval_yield+interval_Pdt.+Feed_Vol+RS_cumulo+rab_integral+RQ_integral+AS_Vol.+emission_O2; 0.364, 0.677, tmp_cumulo+pH+PL_cumulo+AN_cumulo+interval_yield+RS+Feed_Vol+rab_integral+RQ_integral+AS_Vol.+emission_O2; 0.364, 0.677, PL_cumulo+AN_cumulo+interval_yield+RS+Feed_Vol+RS_cumulo+rab_integral+AS_Vol.+emission_CO2+consum_O2; 0.374, 0.677, tmp_cumulo+pH+PL_cumulo+interval_yield+RS+Feed_Vol+RS_cumulo+AS_Vol.+emission_O2+interval_O2; 0.321, 0.677, tmp_cumulo+pH+PL_cumulo+AN+AN_cumulo+interval_yield+interval_Pdt.+RS+Feed_Vol+RS_cumulo+rab_integral+RQ_integral+AS_Vol.+emission_CO2+consum_O2; 0.343, 0.677, tmp_cumulo+pH_cumulo+PL+PL_cumulo+AN_cumulo+interval_yield+RS+Feed_Vol+RS_cumulo+rab_integral+RQ_integral+AS_Vol.+emission_CO2; 0.364, 0.677, pH_cumulo+PL_cumulo+AN_cumulo+interval_yield+Feed_Vol+RS_cumulo+rab_integral+RQ_integral+AS_Vol.+emission_CO2+interval_O2; 0.354, 0.677, tmp_cumulo+PL_cumulo+AN_cumulo+interval_yield+RS+Feed_Vol+rab_integral+RQ_integral+AS_Vol.+emission_O2+consum_O2+interval_O2; 0.364, 0.677, tmp_cumulo+PL+PL_cumulo+interval_yield+interval_Pdt.+RS+RS_cumulo+rab_integral+RQ_integral+AS_Vol.+emission_CO2; 0.354, 0.677, tmp_cumulo+PL_cumulo+interval_yield+interval_Pdt.+Feed_Vol+RS_cumulo+rab_integral+RQ_integral+AS_Vol.+emission_CO2+consum_O2+interval_O2; 0.374, 0.677, O2+PL_cumulo+AN_cumulo+interval_yield+RS+Feed_Vol+RS_cumulo+RQ_integral+AS_Vol.+emission_CO2; 0.354, 0.677, tmp_cumulo+pH+PL+AN_cumulo+interval_yield+Feed_Vol+RS_cumulo+rab_integral+RQ_integral+AS_Vol.+emission_CO2+interval_O2; 0.364, 0.677, tmp_cumulo+PL_cumulo+interval_yield+interval_Pdt.+RS+RS_cumulo+rab_integral+RQ_integral+AS_Vol.+emission_CO2+interval_O2; 0.364, 0.677, pH+pH_cumulo+PL_cumulo+AN_cumulo+interval_yield+interval_Pdt.+RS_cumulo+rab_integral+RQ_integral+AS_Vol.+emission_CO2; 0.393, 0.677, tmp+PL+PL_cumulo+AN_cumulo+interval_yield+RS+Feed_Vol+AS_Vol.; 0.383, 0.677, tmp_cumulo+AN_cumulo+interval_yield+RS+Feed_Vol+rab_integral+RQ_integral+AS_Vol.+emission_CO2; 0.383, 0.677, tmp_cumulo+PL+PL_cumulo+interval_yield+RS+Feed_Vol+RS_cumulo+AS_Vol.+interval_O2; 0.332, 0.677, tmp_cumulo+pH_cumulo+PL_cumulo+AN_cumulo+interval_yield+interval_Pdt.+RS+Feed_Vol+RS_cumulo+rab_integral+RQ_integral+AS_Vol.+emission_CO2+ consum_O2; 0.374, 0.677, tmp_cumulo+AN+AN_cumulo+interval_yield+RS+Feed_Vol+rab_integral+RQ_integral+AS_Vol.+emission_CO2; 0.321, 0.677, tmp_cumulo+pH+PL_cumulo+AN_cumulo+interval_yield+interval_Pdt.+RS+Feed_Vol+RS_cumulo+rab_integral+RQ_integral+AS_Vol.+emission_CO2+consum_O2+interval_O2; 0.354, 0.677, tmp_cumulo+PL+AN_cumulo+interval_yield+interval_Pdt.+RS+Feed_Vol+RS_cumulo+rab_integral+RQ_integral+AS_Vol.+emission_CO2; 0.353, 0.677, tmp+PL+PL_cumulo+AN_cumulo+interval_yield+Feed_Vol+RS_cumulo+rab_integral+RQ_integral+AS_Vol.+emission_CO2+interval_O2; 0.343, 0.677, tmp_cumulo+pH+PL+PL_cumulo+AN_cumulo+interval_yield+interval_Pdt.+RS_cumulo+rab_integral+RQ_integral+AS_Vol.+emission_CO2+interval_O2; 0.374, 0.677, O2+PL_cumulo+AN_cumulo+interval_yield+RS+Feed_Vol+AS_Vol.+emission_O2+consum_O2+interval_O2; 0.343, 0.677, tmp+tmp_cumulo+AN_cumulo+interval_yield+interval_Pdt.+Feed_Vol+RS_cumulo+rab_integral+RQ_integral+AS_Vol.+emission_CO2+consum_O2+interval_O2; 0.383, 0.677, pH+PL+PL_cumulo+interval_yield+RS_cumulo+RQ_integral+AS_Vol.+emission_O2+emission_CO2; 0.353, 0.677, tmp_cumulo+pH_cumulo+PL_cumulo+AN_cumulo+interval_yield+interval_Pdt.+RS_cumulo+rab_integral+RQ_integral+AS_Vol.+emission_CO2+consum_O2; 0.364, 0.677, tmp+PL_cumulo+AN_cumulo+interval_yield+RS+Feed_Vol+RS_cumulo+rab_integral+RQ_integral+AS_Vol.+emission_CO2; 0.374, 0.677, tmp_cumulo+PL+PL_cumulo+interval_yield+RS+Feed_Vol+RS_cumulo+AS_Vol.+emission_O2+interval_O2; 0.402, 0.677, O2+PL_cumulo+interval_yield+RS_cumulo+RQ_integral+AS_Vol.+emission_CO2; 0.393, 0.677, O2+PL_cumulo+AN+AN_cumulo+interval_yield+RS_cumulo+RQ_integral+emission_CO2; 0.343, 0.677, tmp_cumulo+pH+PL+PL_cumulo+AN_cumulo+interval_yield+OD+Feed_Vol+RS_cumulo+rab_integral+RQ_integral+AS_Vol.+emission_CO2; 0.353, 0.677, tmp+tmp_cumulo+AN+AN_cumulo+interval_yield+interval_Pdt.+Feed_Vol+RS_cumulo+rab_integral+RQ_integral+AS_Vol.+emission_CO2; 0.353, 0.677, pH_cumulo+PL+PL_cumulo+AN_cumulo+interval_yield+interval_Pdt.+Feed_Vol+RS_cumulo+rab_integral+RQ_integral+AS_Vol.+emission_CO2; 0.364, 0.677, tmp+tmp_cumulo+PL+PL_cumulo+interval_yield+Feed_Vol+RS_cumulo+rab_integral+RQ_integral+AS_Vol.+emission_CO2; 0.332, 0.677, tmp+tmp_cumulo+AN+AN_cumulo+interval_yield+interval_Pdt.+RS+Feed_Vol+RS_cumulo+rab_integral+RQ_integral+AS_Vol.+emission_CO2+consum_O2; 0.374, 0.677, O2+PL_cumulo+AN_cumulo+interval_yield+RS+Feed_Vol+RS_cumulo+AS_Vol.+emission_CO2+consum_O2; 0.320, 0.677, tmp_cumulo+PL+PL_cumulo+AN+AN_cumulo+interval_yield+RS+Feed_Vol+RS_cumulo+rab_integral+RQ_integral+AS_Vol.+emission_CO2+consum_O2+interval_O2; 0.374, 0.677, tmp_cumulo+PL+PL_cumulo+AN+AN_cumulo+interval_yield+RS+RS_cumulo+RQ_integral+emission_CO2; 0.374, 0.677, tmp_cumulo+PL_cumulo+interval_yield+RS+Feed_Vol+RS_cumulo+AS_Vol.+emission_O2+emission_CO2+interval_O2; 0.343, 0.677, tmp_cumulo+pH_cumulo+PL+PL_cumulo+AN+AN_cumulo+interval_yield+Feed_Vol+RS_cumulo+rab_integral+RQ_integral+AS_Vol.+emission_CO2; 0.353, 0.677, tmp+tmp_cumulo+pH+PL_cumulo+AN_cumulo+interval_yield+interval_Pdt.+RS_cumulo+rab_integral+RQ_integral+AS_Vol.+emission_CO2; 0.383, 0.677, tmp_cumulo+PL_cumulo+interval_yield+interval_Pdt.+OD+RS_cumulo+RQ_integral+AS_Vol.+emission_CO2; 0.373, 0.677, pH+PL+PL_cumulo+AN_cumulo+interval_yield+interval_Pdt.+RS_cumulo+RQ_integral+AS_Vol.+emission_CO2; 0.364, 0.677, pH+PL_cumulo+AN_cumulo+interval_yield+interval_Pdt.+RS+RS_cumulo+rab_integral+RQ_integral+AS_Vol.+emission_CO2; 0.353, 0.677, tmp_cumulo+PL_cumulo+AN_cumulo+interval_yield+interval_Pdt.+Feed_Vol+RS_cumulo+rab_integral+RQ_integral+AS_Vol.+emission_O2+generate_CO2; 0.383, 0.677, PL_cumulo+AN_cumulo+interval_yield+OD+Feed_Vol+RS_cumulo+RQ_integral+AS_Vol.+emission_CO2; 0.343, 0.677, tmp_cumulo+PL_cumulo+AN+AN_cumulo+interval_yield+interval_Pdt.+OD+Feed_Vol+RS_cumulo+rab_integral+RQ_integral+AS_Vol.+emission_CO2; 0.353, 0.677, tmp_cumulo+PL+PL_cumulo+AN+interval_yield+interval_Pdt.+Feed_Vol+RS_cumulo+rab_integral+RQ_integral+AS_Vol.+emission_CO2; 0.383, 0.677, tmp_cumulo+pH_cumulo+interval_yield+Feed_Vol+RS_cumulo+rab_integral+RQ_integral+AS_Vol.+emission_CO2; 0.363, 0.677, O2+PL_cumulo+AN_cumulo+interval_yield+OD+RS+Feed_Vol+rab_integral+RQ_integral+AS_Vol.+emission_CO2; 0.373, 0.677, O2+PL_cumulo+AN+AN_cumulo+interval_yield+interval_Pdt.+RS_cumulo+RQ_integral+AS_Vol.+emission_CO2; 0.363, 0.677, tmp_cumulo+pH+PL_cumulo+interval_yield+RS+Feed_Vol+RS_cumulo+AS_Vol.+emission_O2+consum_O2+interval_O2; 0.353, 0.677, tmp_cumulo+AN_cumulo+interval_yield+RS+Feed_Vol+RS_cumulo+rab_integral+RQ_integral+AS_Vol.+emission_CO2+consum_O2+generate_CO2; 0.373, 0.677, tmp_cumulo+interval_yield+RS+Feed_Vol+RS_cumulo+rab_integral+RQ_integral+AS_Vol.+emission_CO2+interval_O2; 0.401, 0.677, PL_cumulo+AN_cumulo+interval_yield+RS_cumulo+RQ_integral+AS_Vol.+emission_CO2; 0.383, 0.677, tmp+tmp_cumulo+PL_cumulo+interval_yield+Feed_Vol+RS_cumulo+RQ_integral+AS_Vol.+emission_CO2; 0.353, 0.677, tmp_cumulo+AN+AN_cumulo+interval_yield+interval_Pdt.+RS+Feed_Vol+rab_integral+RQ_integral+AS_Vol.+emission_CO2+consum_O2; 0.363, 0.677, tmp+tmp_cumulo+AN_cumulo+interval_yield+interval_Pdt.+RS_cumulo+rab_integral+RQ_integral+AS_Vol.+emission_CO2+interval_O2; 0.353, 0.677, pH+PL+PL_cumulo+AN_cumulo+interval_yield+Feed_Vol+RS_cumulo+rab_integral+RQ_integral+AS_Vol.+emission_CO2+interval_O2; 0.383, 0.677, O2+PL_cumulo+AN+AN_cumulo+interval_yield+RS+RS_cumulo+RQ_integral+emission_CO2; 0.373, 0.677, pH_cumulo+PL_cumulo+interval_yield+OD+RS+Feed_Vol+AS_Vol.+emission_O2+consum_O2+interval_O2; 0.353, 0.677, tmp_cumulo+pH_cumulo+AN_cumulo+interval_yield+interval_Pdt.+RS+Feed_Vol+RS_cumulo+rab_integral+RQ_integral+AS_Vol.+emission_CO2; 0.353, 0.677, tmp_cumulo+PL+PL_cumulo+AN_cumulo+interval_yield+Feed_Vol+RS_cumulo+rab_integral+RQ_integral+AS_Vol.+emission_O2+emission_CO2; 0.392, 0.677, tmp_cumulo+PL_cumulo+AN_cumulo+interval_yield+Feed_Vol+RS_cumulo+AS_Vol.+emission_O2; 0.342, 0.677, tmp_cumulo+pH+PL_cumulo+AN_cumulo+interval_yield+interval_Pdt.+RS+RS_cumulo+rab_integral+RQ_integral+AS_Vol.+emission_CO2+interval_O2; 0.363, 0.677, tmp_cumulo+PL_cumulo+interval_yield+interval_Pdt.+OD+RS_cumulo+rab_integral+RQ_integral+AS_Vol.+emission_CO2+interval_O2; 0.353, 0.677, tmp_cumulo+PL_cumulo+AN+AN_cumulo+interval_yield+interval_Pdt.+OD+RS_cumulo+rab_integral+RQ_integral+AS_Vol.+emission_CO2; 0.401, 0.677, tmp_cumulo+PL_cumulo+interval_yield+Feed_Vol+RS_cumulo+AS_Vol.+emission_O2; 0.353, 0.677, tmp_cumulo+PL+AN_cumulo+interval_yield+Feed_Vol+RS_cumulo+rab_integral+RQ_ integral+AS_Vol.+emission_CO2+consum_O2+interval_O2; 0.383, 0.677, O2+PL_cumulo+interval_yield+OD+RS+Feed_Vol+AS_Vol.+emission_CO2+interval_O2; 0.353, 0.677, tmp_cumulo+pH_cumulo+PL_cumulo+AN_cumulo+interval_yield+Feed_Vol+RS_cumulo+rab_integral+RQ_integral+AS_Vol.+emission_O2+emission_CO2; 0.353, 0.677, pH+PL+PL_cumulo+AN_cumulo+interval_yield+interval_Pdt.+OD+RS_cumulo+rab_integral+RQ_integral+AS_Vol.+emission_CO2; 0.363, 0.677, tmp_cumulo+pH_cumulo+PL_cumulo+interval_yield+RS+Feed_Vol+RS_cumulo+rab_integral+RQ_integral+AS_Vol.+emission_CO2; 0.373, 0.677, tmp_cumulo+PL_cumulo+AN_cumulo+interval_yield+RS+Feed_Vol+RS_cumulo+AS_Vol.+emission_CO2+consum_O2; 0.363, 0.677, tmp_cumulo+pH_cumulo+PL_cumulo+AN_cumulo+interval_yield+Feed_Vol+RS_cumulo+rab_integral+RQ_integral+AS_Vol.+emission_O2; 0.373, 0.677, O2+PL_cumulo+AN_cumulo+interval_yield+Feed_Vol+RS_cumulo+RQ_integral+AS_Vol.+emission_CO2+interval_O2; 0.353, 0.677, tmp_cumulo+PL+PL_cumulo+AN_cumulo+interval_yield+interval_Pdt.+OD+RS_cumulo+rab_integral+RQ_integral+AS_Vol.+emission_CO2; 0.373, 0.677, PL_cumulo+AN_cumulo+interval_yield+RS+Feed_Vol+RS_cumulo+AS_Vol.+emission_O2+consum_O2+interval_O2; 0.363, 0.677, tmp_cumulo+pH+PL_cumulo+AN+interval_yield+Feed_Vol+RS_cumulo+rab_integral+RQ_integral+AS_Vol.+emission_CO2; 0.373, 0.677, O2+PL_cumulo+interval_yield+interval_Pdt.+Feed_Vol+RS_cumulo+rab_integral+RQ_integral+AS_Vol.+emission_CO2

[205. Linear Model that Predicts Arginine Production Amount in Interval 5]

0.490, 0.743, tmp_cumulo+pH+pH_cumulo+AN_cumulo+interval_yield+RS+Feed_Vol+Cell_conc._interval+AS_Vol.; 0.497, 0.742, tmp_cumulo+pH+pH_cumulo+AN_cumulo+interval_yield+RS+Cell_conc._interval+AS_Vol.; 0.485, 0.740, tmp_cumulo+pH+pH_cumulo+AN_cumulo+interval_yield+RS+Cell_conc._interval+rab_integral+AS_Vol.; 0.476, 0.739, tmp_cumulo+pH+pH_cumulo+AN_cumulo+interval_yield+RS+Feed_Vol+Cell_conc._interval+AS_Vol.+generate_CO2; 0.482, 0.738, tmp_cumulo+pH+pH_cumulo+AN+AN_cumulo+interval_yield+RS+Cell_conc._interval+AS_Vol.; 0.474, 0.738, tmp_cumulo+pH+pH_cumulo+AN+AN_cumulo+interval_yield+RS+Feed_Vol+Cell_conc._interval+AS_Vol.; 0.481, 0.738, tmp_cumulo+pH+pH_cumulo+AN_cumulo+interval_yield+RS+Cell_conc._interval+AS_Vol.+generate_CO2; 0.473, 0.738, tmp_cumulo+pH+pH_cumulo+AN_cumulo+interval_yield+RS+Feed_Vol+Cell_conc._interval+AS_Vol.+emission_CO2; 0.473, 0.738, tmp_cumulo+pH+pH_cumulo+AN_cumulo+interval_yield+RS+Feed_Vol+Cell_conc._interval+rab_integral+AS_Vol.; 0.489, 0.738, tmp_cumulo+pH+pH_cumulo+AN+interval_yield+RS+Cell_conc._interval+AS_Vol.; 0.473, 0.738, tmp+tmp_cumulo+pH+pH_cumulo+AN_cumulo+interval_yield+RS+Feed_Vol+Cell_conc._interval+AS_Vol.; 0.473, 0.737, tmp_cumulo+pH+pH_cumulo+AN_cumulo+interval_yield+interval_Pdt.+RS+Feed_Vol+Cell_conc._interval+AS_Vol.; 0.472, 0.737, tmp_cumulo+pH+pH_cumulo+PL_cumulo+AN_cumulo+interval_yield+RS+Feed_Vol+Cell_conc._interval+AS_Vol.; 0.480, 0.737, tmp_cumulo+pH+pH_cumulo+AN_cumulo+interval_yield+RS+Cell_conc._interval+AS_Vol.+emission_CO2; 0.480, 0.737, tmp_cumulo+pH+pH_cumulo+AN+interval_yield+RS+Feed_Vol+Cell_conc._interval+AS_Vol.; 0.480, 0.737, tmp+tmp_cumulo+pH+pH_cumulo+AN_cumulo+interval_yield+RS+Cell_conc._interval+AS_Vol.; 0.478, 0.736, tmp_cumulo+pH+pH_cumulo+AN_cumulo+interval_yield+interval_Pdt.+RS+Cell_conc._interval+AS_Vol.; 0.470, 0.736, tmp_cumulo+pH+pH_cumulo+AN_cumulo+interval_yield+RS+Feed_Vol+Cell_conc._interval+RQ_integral+AS_Vol.; 0.461, 0.736, tmp_cumulo+pH+pH_cumulo+AN_cumulo+interval_yield+RS+Feed_Vol+Cell_conc._interval+AS_Vol.+emission_CO2+generate_CO2; 0.469, 0.735, tmp_cumulo+pH+pH_cumulo+AN_cumulo+interval_yield+RS+Cell_conc._interval+rab_integral+AS_Vol.+generate_CO2; 0.461, 0.735, tmp_cumulo+pH+pH_cumulo+AN+AN_cumulo+interval_yield+RS+Feed_Vol+Cell_conc._interval+AS_Vol.+generate_CO2; 0.477, 0.735, tmp_cumulo+pH+pH_cumulo+PL_cumulo+AN_cumulo+interval_yield+RS+Cell_conc._interval+AS_Vol.; 0.469, 0.735, tmp_cumulo+pH+pH_cumulo+AN_cumulo+interval_yield+RS+Cell_conc._interval+AS_Vol.+emission_CO2+generate_CO2; 0.468, 0.735, tmp_cumulo+pH+pH_cumulo+AN_cumulo+interval_yield+RS+Feed_Vol+Cell_conc._interval+AS_Vol.+emission_O2; 0.476, 0.735, tmp_cumulo+pH+pH_cumulo+PL+AN_cumulo+interval_yield+RS+Cell_conc._interval+AS_Vol.; 0.484, 0.735, tmp_cumulo+pH+pH_cumulo+interval_yield+RS+Feed_Vol+Cell_conc._interval+AS_Vol.; 0.468, 0.735, tmp_cumulo+pH+pH_cumulo+PL+AN_cumulo+interval_yield+RS+Cell_conc._interval+rab_integral+AS_Vol.; 0.468, 0.735, tmp_cumulo+pH+pH_cumulo+PL_cumulo+AN_cumulo+interval_yield+RS+Cell_conc._interval+rab_integral+AS_Vol.; 0.468, 0.735, tmp_cumulo+pH+pH_cumulo+AN+AN_cumulo+interval_yield+RS+Cell_conc._interval+rab_integral+AS_Vol.; 0.492, 0.735, tmp_cumulo+pH+pH_cumulo+interval_yield+RS+Feed_Vol+Cell_conc._interval; 0.459, 0.735, tmp_cumulo+pH+pH_cumulo+AN_cumulo+interval_yield+RS+Feed_Vol+Cell_conc._interval+rab_integral+AS_Vol.+generate_CO2; 0.468, 0.735, tmp_cumulo+pH+pH_cumulo+AN_cumulo+interval_yield+RS+Feed_Vol+Cell_conc._interval+AS_Vol.+consum_O2; 0.476, 0.734, tmp_cumulo+pH+pH_cumulo+AN_cumulo+interval_yield+RS+Cell_conc._interval+AS_Vol.+consum_O2; 0.467, 0.734, tmp_cumulo+pH+pH_cumulo+AN+interval_yield+RS+Feed_Vol+Cell_conc._interval+AS_Vol.+generate_CO2; 0.467, 0.734, tmp_cumulo+pH+pH_cumulo+AN_cumulo+interval_yield+RS+Cell_conc._interval+rab_integral+AS_Vol.+emission_CO2; 0.459, 0.734, tmp_cumulo+pH+pH_cumulo+PL+AN_cumulo+interval_yield+RS+Cell_conc._interval+rab_integral+AS_Vol.+emission_CO2; 0.467, 0.734, tmp_cumulo+pH+pH_cumulo+AN+AN_cumulo+interval_yield+RS+Cell_conc._interval+AS_Vol.+generate_CO2; 0.475, 0.734, tmp_cumulo+pH+pH_cumulo+AN_cumulo+interval_yield+RS+RS_cumulo+Cell_conc._interval+AS_Vol.; 0.467, 0.734, tmp+tmp_cumulo+pH+pH_cumulo+AN_cumulo+interval_yield+RS+Cell_conc._interval+rab_integral+AS_Vol.; 0.467, 0.734, tmp_cumulo+pH+pH_cumulo+AN_cumulo+interval_yield+RS+Feed_Vol+RS_cumulo+Cell_conc._interval+AS_Vol.; 0.475, 0.734, tmp_cumulo+pH+pH_cumulo+AN+interval_yield+RS+Cell_conc._interval+AS_Vol.+generate_CO2; 0.475, 0.734, tmp_cumulo+pH+pH_cumulo+AN_cumulo+interval_yield+RS+Cell_conc._interval+RQ_integral+AS_Vol.; 0.458, 0.734, tmp+tmp_cumulo+pH+pH_cumulo+AN_cumulo+interval_yield+RS+Feed_Vol+Cell_conc._interval+AS_Vol.+generate_CO2; 0.482, 0.734, tmp_cumulo+pH+pH_cumulo+AN_cumulo+interval_yield+RS+Feed_Vol+Cell_conc._interval; 0.474, 0.734, tmp_cumulo+pH+pH_cumulo+AN+interval_yield+RS+Cell_conc._interval+rab_integral+AS_Vol.; 0.457, 0.733, tmp_cumulo+pH+pH_cumulo+PL_cumulo+AN_cumulo+interval_yield+RS+Feed_Vol+Cell_conc._interval+

AS_Vol.+generate_CO2; 0.474, 0.733, tmp_cumulo+pH+pH_cumulo+AN_cumulo+interval_yield+OD+RS+Cell_conc._interval+AS_Vol.; 0.465, 0.733, tmp_cumulo+pH+pH_cumulo+AN_cumulo+interval_yield+interval_Pdt.+RS+Cell_conc._interval+rab_integral+AS_Vol.; 0.457, 0.733, tmp_cumulo+pH+pH_cumulo+PL_cumulo+AN_cumulo+interval_yield+RS+Feed_Vol+Cell_conc._interval+rab_integral+AS_Vol.; 0.465, 0.733, tmp_cumulo+pH+pH_cumulo+PL+AN_cumulo+interval_yield+RS+Cell_conc._interval+AS_Vol.+emission_CO2; 0.465, 0.733, tmp_cumulo+pH+pH_cumulo+AN_cumulo+interval_yield+RS+Cell_conc._interval+rab_integral+RQ_integral+AS_Vol.; 0.456, 0.733, tmp_cumulo+pH+pH_cumulo+AN+AN_cumulo+interval_yield+RS+Feed_Vol+Cell_conc._interval+AS_Vol.+emission_CO2; 0.456, 0.733, tmp_cumulo+pH+pH_cumulo+AN_cumulo+interval_yield+RS+Feed_Vol+Cell_conc._interval+rab_integral+RQ_integral+AS_Vol.; 0.456, 0.733, tmp+tmp_cumulo+pH+pH_cumulo+AN+AN_cumulo+interval_yield+RS+Feed_Vol+Cell_conc._interval+AS_Vol.; 0.465, 0.733, tmp+tmp_cumulo+pH+pH_cumulo+AN+AN_cumulo+interval_yield+RS+Cell_conc._interval+AS_Vol.; 0.456, 0.733, tmp_cumulo+pH+pH_cumulo+AN+AN_cumulo+interval_yield+RS+Feed_Vol+Cell_conc._interval+rab_integral+AS_Vol.; 0.456, 0.733, tmp_cumulo+pH+pH_cumulo+AN_cumulo+interval_yield+interval_Pdt.+RS+Feed_Vol+Cell_conc._interval+rab_integral+AS_Vol.; 0.456, 0.733, tmp+tmp_cumulo+pH+pH_cumulo+AN_cumulo+interval_yield+RS+Feed_Vol+Cell_conc._interval+AS_Vol.+emission_CO2; 0.456, 0.733, tmp_cumulo+pH+pH_cumulo+PL_cumulo+AN+AN_cumulo+interval_yield+RS+Feed_Vol+Cell_conc._interval+AS_Vol.; 0.456, 0.732, tmp_cumulo+pH+pH_cumulo+AN_cumulo+interval_yield+RS+Feed_Vol+Cell_conc._interval+rab_integral+AS_Vol.+emission_CO2; 0.455, 0.732, tmp+tmp_cumulo+pH+pH_cumulo+AN_cumulo+interval_yield+RS+Feed_Vol+Cell_conc._interval+rab_integral+AS_Vol.; 0.455, 0.732, tmp_cumulo+pH+pH_cumulo+AN+AN_cumulo+interval_yield+interval_Pdt.+RS+Feed_Vol+Cell_conc._interval+AS_Vol.; 0.464, 0.732, tmp_cumulo+pH+pH_cumulo+AN+AN_cumulo+interval_yield+RS+Cell_conc._interval+AS_Vol.+emission_CO2; 0.464, 0.732, tmp+tmp_cumulo+pH+pH_cumulo+AN_cumulo+interval_yield+RS+Cell_conc._interval+AS_Vol.+generate_CO2; 0.472, 0.732, tmp+tmp_cumulo+pH+pH_cumulo+AN+interval_yield+RS+Cell_conc._interval+AS_Vol.; 0.455, 0.732, tmp_cumulo+pH+pH_cumulo+PL+AN_cumulo+interval_yield+RS+Feed_Vol+Cell_conc._interval+AS_Vol.+interval_O2; 0.455, 0.732, tmp_cumulo+pH+pH_cumulo+AN_cumulo+interval_yield+interval_Pdt.+RS+Feed_Vol+Cell_conc._interval+AS_Vol.+generate_CO2; 0.464, 0.732, tmp_cumulo+pH+pH_cumulo+AN_cumulo+interval_yield+RS+Cell_conc._interval+rab_integral+AS_Vol.+consum_O2; 0.455, 0.732, tmp_cumulo+pH+pH_cumulo+AN_cumulo+interval_yield+interval_Pdt.+RS+Feed_Vol+Cell_conc._interval+AS_Vol.+emission_CO2; 0.455, 0.732, tmp_cumulo+pH+pH_cumulo+AN_cumulo+interval_yield+RS+Cell_conc._interval+rab_integral+AS_Vol.+emission_CO2+generate_CO2; 0.454, 0.732, tmp_cumulo+pH+pH_cumulo+AN+AN_cumulo+interval_yield+RS+Feed_Vol+Cell_conc._interval+RQ_integral+AS_Vol.; 0.463, 0.732, tmp_cumulo+pH+pH_cumulo+PL+AN+AN_cumulo+interval_yield+RS+Cell_conc._interval+AS_Vol.; 0.463, 0.732, tmp_cumulo+pH+pH_cumulo+PL+AN+interval_yield+RS+Cell_conc._interval+AS_Vol.+interval_O2; 0.463, 0.732, tmp+tmp_cumulo+pH+pH_cumulo+AN_cumulo+interval_yield+RS+Cell_conc._interval+AS_Vol.+emission_CO2; 0.463, 0.732, tmp+tmp_cumulo+pH+pH_cumulo+AN+interval_yield+RS+Feed_Vol+Cell_conc._interval+AS_Vol.; 0.454, 0.732, tmp_cumulo+pH+pH_cumulo+PL_cumulo+AN_cumulo+interval_yield+RS+Feed_Vol+Cell_conc._interval+RQ_integral+AS_Vol.; 0.463, 0.732, tmp_cumulo+pH+pH_cumulo+AN_cumulo+interval_yield+RS+RS_cumulo+Cell_conc._interval+rab_integral+AS_Vol.; 0.487, 0.732, tmp_cumulo+pH+pH_cumulo+interval_yield+RS+Cell_conc._interval+AS_Vol.; 0.454, 0.731, tmp+tmp_cumulo+pH+pH_cumulo+PL_cumulo+AN_cumulo+interval_yield+RS+Feed_Vol+Cell_conc._interval+AS_Vol.; 0.462, 0.731, tmp_cumulo+pH+pH_cumulo+AN+interval_yield+RS+Feed_Vol+Cell_conc._interval+AS_Vol.+emission_CO2; 0.462, 0.731, tmp_cumulo+pH+pH_cumulo+AN_cumulo+interval_yield+OD+RS+Feed_Vol+Cell_conc._interval+AS_Vol.; 0.454, 0.731, tmp_cumulo+pH+pH_cumulo+PL+AN+interval_yield+RS+Feed_Vol+Cell_conc._interval+AS_Vol.+interval_O2; 0.454, 0.731, tmp_cumulo+pH+pH_cumulo+PL_cumulo+AN_cumulo+interval_yield+interval_Pdt.+RS+Feed_Vol+Cell_conc._interval+AS_Vol.; 0.462, 0.731, tmp_cumulo+pH+pH_cumulo+PL_cumulo+AN+AN_cumulo+interval_yield+RS+Cell_conc._interval+AS_Vol.; 0.454, 0.731, tmp_cumulo+pH+pH_cumulo+AN_cumulo+interval_yield+RS+Feed_Vol+Cell_conc._interval+RQ_integral+AS_Vol.+generate_CO2; 0.462, 0.731, tmp_cumulo+pH+pH_cumulo+AN+interval_yield+RS+Feed_Vol+Cell_conc._interval+rab_integral+AS_Vol.; 0.462, 0.731, tmp_cumulo+pH+pH_cumulo+AN+interval_yield+interval_Pdt.+RS+Feed_Vol+Cell_conc._interval+AS_Vol; 0.453, 0.731, tmp+tmp_cumulo+pH+pH_cumulo+AN+cumulo+interval_yield+interval_Pdt.+RS+Feed_Vol+Cell_conc._interval+AS_Vol.; 0.462, 0.731, tmp_cumulo+pH+pH_cumulo+PL+AN_cumulo+interval_yield+RS+Feed_Vol+Cell_conc._interval+AS_Vol.; 0.444, 0.731, tmp_cumulo+pH+pH_cumulo+AN_cumulo+interval_yield+RS+Feed_Vol+Cell_conc._interval+rab_integral+AS_Vol.+emission_CO2+generate_CO2; 0.470, 0.731, tmp_cumulo+pH+pH_cumulo+AN+interval_yield+RS+Cell_conc._interval+AS_Vol.+emission_CO2; 0.453, 0.731, tmp_cumulo+pH+pH_cumulo+PL_cumulo+AN_cumulo+interval_yield+RS+Feed_Vol+Cell_conc._interval+AS_Vol.+emission_CO2; 0.461, 0.731, tmp_cumulo+pH+pH_cumulo+AN+AN_cumulo+interval_yield+interval_Pdt.+RS+Cell_conc._interval+AS_Vol.; 0.453, 0.731, tmp+tmp_cumulo+pH+pH_cumulo+AN_cumulo+interval_yield+RS+Feed_Vol+Cell_conc._interval+RQ_integral+AS_Vol.; 0.470, 0.731, tmp_cumulo+pH+pH_cumulo+AN_cumulo+interval_yield+RS+Cell_conc._interval+AS_Vol.+emission_O2; 0.478, 0.731, tmp_cumulo+pH+pH_cumulo+interval_yield+RS+Feed_Vol+Cell_conc._interval+rab_integral; 0.461, 0.731, tmp_cumulo+pH+pH_cumulo+AN+interval_yield+RS+Feed_Vol+Cell_conc._interval+RQ_integral+AS_Vol.; 0.478, 0.731, tmp_cumulo+pH+pH_cumulo+interval_yield+RS+Feed_Vol+Cell_conc._interval+consum_O2; 0.444, 0.731, tmp_cumulo+pH+pH_cumulo+AN+AN_cumulo+interval_yield+RS+Feed_Vol+Cell_conc._interval+AS_Vol.+emission_CO2+generate_CO2; 0.453, 0.731, tmp_cumulo+pH+pH_cumulo+PL+AN_cumulo+interval_yield+RS+Cell_conc._interval+RQ_integral+AS_Vol.+emission_CO2; 0.461, 0.731, tmp_cumulo+pH+pH_cumulo+AN+interval_yield+RS+Feed_Vol+Cell_conc._interval+AS_Vol.+emission_O2; 0.461, 0.731, tmp_cumulo+pH+pH_cumulo+AN+AN_cumulo+interval_yield+RS+Cell_conc._interval+RQ_integral+AS_Vol.; 0.452, 0.731, tmp_cumulo+pH+pH_cumulo+AN+AN_cumulo+interval_yield+RS+Feed_Vol+Cell_conc._interval+AS_Vol.+emission_O2; 0.477, 0.730, tmp_cumulo+pH+AN_cumulo+interval_yield+RS+Feed_Vol+Cell_conc._interval+AS_Vol.; 0.461, 0.730, tmp_cumulo+pH+pH_cumulo+PL_cumulo+AN+interval_yield+RS+Feed_Vol+Cell_conc._interval+AS_Vol.; 0.469, 0.730, tmp_cumulo+pH+pH_cumulo+AN+interval_yield+interval_Pdt.+RS+Cell_conc._interval+AS_Vol.; 0.461, 0.730, tmp_cumulo+pH+pH_cumulo+AN+AN_cumulo+interval_yield+RS+Cell_conc._interval+AS_Vol.+consum_O2; 0.443, 0.730, tmp_cumulo+pH+pH_cumulo+PL_cumulo+AN_cumulo+interval_yield+RS+Feed_Vol+Cell_conc._interval+AS_Vol.+emission_CO2+generate_CO2; 0.452, 0.730, tmp_cumulo+pH+pH_cumulo+AN_cumulo+interval_yield+RS+Feed_Vol+Cell_conc._interval+AS_Vol.+consum_O2+generate_CO2; 0.452, 0.730, tmp_cumulo+pH+pH_cumulo+PL+AN+AN_cumulo+interval_yield+RS+Cell_conc._interval+rab_integral+AS_Vol.; 0.452, 0.730, tmp+tmp_cumulo+pH+pH_cumulo+AN_cumulo+interval_yield+RS+Feed_Vol+Cell_conc._interval+AS_Vol.+emission_O2; 0.452, 0.730, tmp_cumulo+pH+pH_cumulo+AN_cumulo+interval_yield+RS+Feed_Vol+RS_cumulo+Cell_conc._interval+AS_Vol.+generate_CO2; 0.443, 0.730, tmp_cumulo+pH+pH_cumulo+AN+AN_cumulo+interval_yield+RS+Feed_Vol+Cell_conc._interval+rab_integral+AS_Vol.+generate_CO2; 0.460, 0.730, tmp+tmp_cumulo+pH+pH_cumulo+AN_cumulo+interval_yield+interval_Pdt.+RS+Cell_conc._interval+AS_Vol.; 0.452, 0.730, tmp_cumulo+pH+pH_cumulo+AN+AN_cumulo+interval_yield+RS+Cell_conc._interval+AS_Vol.+emission_CO2+generate_CO2; 0.460, 0.730, tmp_cumulo+pH+pH_cumulo+PL_cumulo+AN_cumulo+interval_yield+RS+Cell_conc._interval+AS_Vol.+generate_CO2; 0.452, 0.730, tmp_cumulo+pH+pH_cumulo+PL_cumulo+AN+AN_cumulo+interval_yield+RS+Cell_conc._interval+rab_integral+AS_Vol.; 0.468, 0.730, tmp_cumulo+pH+pH_cumulo+AN+interval_yield+RS+Cell_conc._interval+RQ_integral+AS_Vol.; 0.468, 0.730, tmp_cumulo+pH+pH_cumulo+PL+AN+interval_yield+RS+Cell_conc._interval+AS_Vol.; 0.451, 0.730, tmp_cumulo+pH+pH_cumulo+AN_cumulo+interval_yield+RS+Feed_Vol+Cell_conc._interval+rab_integral+AS_Vol.+emission_O2; 0.468, 0.730, tmp_cumulo+pH+pH_cumulo+PL_cumulo+AN+interval_yield+RS+Cell_conc._interval+AS_Vol.; 0.451, 0.730, tmp_cumulo+pH+pH_cumulo+PL_cumulo+AN_cumulo+interval_yield+RS+Cell_conc._interval+rab_integral+AS_Vol.+generate_CO2; 0.460, 0.730, tmp_cumulo+pH+pH_cumulo+AN_cumulo+interval_yield+interval_Pdt.+RS+Cell_conc._interval+AS_Vol.+emission_CO2; 0.442, 0.730, tmp_cumulo+pH+pH_cumulo+PL_cumulo+AN+AN_cumulo+interval_yield+RS+Feed_Vol+Cell_conc._interval+AS_Vol.+generate_CO2; 0.476, 0.730, tmp_cumulo+pH+pH_cumulo+interval_yield+RS+Feed_Vol+Cell_conc._interval+emission_CO2; 0.468, 0.730, tmp_cumulo+pH+pH_cumulo+AN_cumulo+interval_yield+RS+Feed_Vol+Cell_conc._interval+rab_integral; 0.460, 0.730, tmp_cumulo+pH+pH_cumulo+AN+AN_cumulo+interval_yield+OD+RS+Cell_conc._interval+AS_Vol.; 0.451, 0.730, tmp_cumulo+pH+pH_cumulo+AN+AN_cumulo+interval_yield+RS+Cell_conc._interval+rab_integral+AS_Vol.+generate_CO2; 0.442, 0.730, tmp_cumulo+pH+pH_cumulo+PL+AN_cumulo+interval_yield+RS+Cell_conc._interval+rab_integral+AS_Vol.+emission_CO2+generate_CO2; 0.468, 0.730, tmp_cumulo+pH+pH_cumulo+AN+interval_yield+OD+RS+Cell_conc._interval+AS_Vol.; 0.468, 0.730, tmp_cumulo+pH+pH_cumulo+AN_cumulo+interval_yield+interval_Pdt.+RS+Feed_Vol+Cell_conc._interval; 0.451, 0.730, tmp_cumulo+pH+pH_cumulo+AN_cumulo+interval_yield+interval_Pdt.+RS+Feed_Vol+Cell_conc._interval+RQ_integral+AS_Vol.; 0.468, 0.730, tmp_cumulo+pH+pH_cumulo+AN_cumulo+interval_yield+RS+Cell_conc._interval+Accum._Yield+AS_Vol.; 0.460, 0.730, tmp_cumulo+pH+pH_cumulo+AN+AN_cumulo+interval_yield+RS+RS_cumulo+Cell_conc._interval+AS_Vol.; 0.468, 0.730, tmp_cumulo+pH+pH_cumulo+AN+interval_yield+RS+Cell_conc._interval+AS_Vol.+consum_O2; 0.468, 0.730, tmp_cumulo+pH+pH_cumulo+interval_yield+RS+Feed_Vol+Cell_conc._interval+AS_Vol.+emission_CO2; 0.459, 0.730, tmp_cumulo+pH+pH_cumulo+AN_cumulo+interval_yield+interval_Pdt.+RS+Cell_conc._interval+AS_Vol.+generate_CO2; 0.451, 0.730, tmp_cumulo+pH+pH_cumulo+AN+interval_yield+RS+Cell_conc._interval+RQ_integral+AS_Vol.+emission_O2+emission_CO2; 0.459, 0.730, tmp_cumulo+pH+pH_cumulo+AN+interval_yield+OD+RS+Cell_conc._interval+rab_integral+AS_Vol.; 0.451, 0.730, tmp_cumulo+pH+pH_cumulo+PL_cumulo+AN_cumulo+interval_yield+RS+Cell_conc._interval+rab_integral+AS_Vol.+emission_CO2; 0.451, 0.730, tmp_cumulo+pH+pH_cumulo+AN+interval_yield+RS+Feed_Vol+Cell_conc._interval+rab_integral+AS_Vol.+generate_CO2; 0.451, 0.730, tmp+tmp_cumulo+pH+pH_cumulo+AN+interval_yield+RS+Cell_conc._interval+rab_integral+AS_Vol.+generate_CO2; 0.459, 0.730, tmp_cumulo+pH+pH_cumulo+PL+interval_yield+RS+Feed_Vol+Cell_conc._interval+AS_Vol.+interval_O2; 0.451, 0.730, tmp_cumulo+pH+pH_cumulo+AN+AN_cumulo+interval_yield+RS+Feed_Vol+Cell_conc._interval+AS_Vol.+consum_O2; 0.467, 0.730, tmp_cumulo+pH+pH_cumulo+AN_cumulo+interval_yield+RS+Feed_Vol+Cell_conc._interval+generate_CO2; 0.475, 0.729, tmp_cumulo+pH+pH_cumulo+interval_yield+RS+Feed_Vol+Cell_conc._interval+generate_CO2; 0.450, 0.729, tmp_cumulo+pH+pH_cumulo+AN_cumulo+interval_yield+RS+Feed_Vol+Cell_conc._interval+rab_integral+AS_Vol.+consum_O2; 0.467, 0.729, tmp_cumulo+pH+pH_cumulo+interval_yield+RS+Feed_Vol+Cell_conc._interval+AS_Vol.+generate_CO2; 0.441, 0.729, tmp+tmp_cumulo+pH+pH_cumulo+AN_cumulo+interval_yield+RS+Feed_Vol+Cell_conc._interval+AS_Vol.+emission_CO2+generate_CO2; 0.441, 0.729, tmp+pH+pH_cumulo+PL+AN+AN_cumulo+interval_yield+RS+Cell_conc._interval+rab_integral+AS_Vol.+emission_CO2; 0.450, 0.729, tmp_cumulo+pH+pH_cumulo+PL+AN+interval_yield+RS+Cell_conc._interval+rab_integral+AS_Vol.+interval_O2; 0.450, 0.729, tmp_cumulo+pH+pH_cumulo+PL+AN_cumulo+interval_yield+RS+Cell_conc._interval+AS_Vol.+emission_CO2+generate_CO2; 0.459, 0.729, tmp_cumulo+pH+pH_cumulo+AN_cumulo+interval_yield+RS+Cell_conc._interval+rab_integral+AS_Vol.+emission_O2; 0.441, 0.729, tmp+tmp_cumulo+pH+pH_cumulo+AN+AN_cumulo+interval_yield+RS+Feed_Vol+Cell_conc._interval+AS_Vol.+generate_CO2; 0.459, 0.729, tmp_cumulo+pH+pH_cumulo+AN_cumulo+interval_yield+RS+RS_cumulo+Cell_conc._interval+AS_Vol.+generate_CO2; 0.459, 0.729, tmp_cumulo+pH+pH_cumulo+PL_cumulo+AN_cumulo+interval_yield+RS+Cell_conc._interval+AS_Vol.+emission_CO2; 0.475, 0.729, tmp_cumulo+pH+pH_cumulo+interval_yield+interval_Pdt.+RS+Feed_Vol+Cell_conc._interval; 0.441, 0.729, tmp_cumulo+pH+pH_cumulo+PL+AN_cumulo+interval_yield+RS+Cell_conc._interval+rab_integral+AS_Vol.+emission_CO2+interval_O2; 0.467, 0.729, tmp_cumulo+pH+pH_cumulo+AN+interval_yield+RS+RS_cumulo+Cell_conc._interval+AS_Vol.; 0.459, 0.729, tmp+tmp_cumulo+pH+pH_cumulo+PL+AN_cumulo+interval_yield+RS+Cell_conc._interval+AS_Vol.; 0.450, 0.729, tmp_cumulo+pH+ pH_cumulo+AN+AN_cumulo+interval_yield+RS+Feed_Vol+RS_cumulo+Cell_conc._interval+AS_Vol.; 0.450, 0.729, tmp_cumulo+pH+pH_cumulo+AN_cumulo+interval_yield+RS+Feed_Vol+Cell_conc._interval+AS_Vol.+emission_O2+emission_CO2; 0.450, 0.729, tmp_cumulo+pH+pH_cumulo+AN_cumulo+interval_yield+RS+Feed_Vol+Cell_conc._interval+AS_Vol.+emission_O2+generate_CO2; 0.467, 0.729, tmp_cumulo+pH+pH_cumulo+AN+interval_yield+RS+Cell_conc._interval+AS_Vol.+emission_O2; 0.441, 0.729, tmp_cumulo+pH+pH_cumulo+PL_cumulo+AN_cumulo+interval_yield+RS+Feed_Vol+Cell_conc._interval+rab_integral+AS_Vol.+generate_CO2; 0.475, 0.729, tmp_cumulo+pH+pH_cumulo+AN+interval_yield+RS+Feed_Vol+Cell_conc._interval; 0.450, 0.729, tmp_cumulo+pH+pH_cumulo+AN+interval_yield+RS+Feed_Vol+Cell_conc._interval+AS_Vol.+emission_CO2+generate_CO2; 0.458, 0.729, tmp_cumulo+pH+pH_cumulo+PL+AN_cumulo+interval_yield+RS+Cell_conc._interval+AS_Vol.+interval_O2; 0.490, 0.729, tmp_cumulo+pH+interval_yield+RS+Feed_Vol+Cell_conc._interval; 0.441, 0.729, tmp_cumulo+pH+pH_cumulo+AN_cumulo+interval_yield+RS+Feed_Vol+Cell_conc._interval+RQ_integral+AS_Vol.+emission_O2+emission_CO2; 0.475, 0.729, tmp_cumulo+pH+pH_cumulo+interval_yield+RS+Feed_Vol+Cell_conc._interval+interval_O2; 0.450, 0.729, tmp_cumulo+pH+pH_cumulo+AN_cumulo+interval_yield+RS+Feed_Vol+Cell_conc._interval+AS_Vol.+emission_CO2+consum_O2; 0.458, 0.729, tmp+tmp_cumulo+pH+pH_cumulo+PL_cumulo+AN_cumulo+interval_yield+RS+Cell_conc._interval+AS_Vol.; 0.458, 0.729, tmp_cumulo+pH+pH_cumulo+AN+interval_yield+RS+Cell_conc._interval+rab_integral+AS_Vol.+generate_CO2; 0.450, 0.729, tmp_cumulo+pH+pH_cumulo+PL+AN_cumulo+interval_yield+RS+Cell_conc._interval+rab_integral+RQ_integral+AS_Vol.; 0.458, 0.729, tmp+tmp_cumulo+pH+pH_cumulo+AN_cumulo+interval_yield+RS+Cell_conc._interval+AS_Vol.+consum_O2; 0.450, 0.729, tmp+tmp_cumulo+pH+pH_cumulo+AN_cumulo+interval_yield+RS+Feed_Vol+Cell_conc._interval+AS_Vol.+consum_O2; 0.458, 0.729, tmp_cumulo+pH+pH_cumulo+AN+interval_yield+RS+Cell_conc._interval+AS_Vol.+emission_CO2+generate_CO2; 0.458, 0.729, tmp_cumulo+pH+pH_cumulo+PL+AN_cumulo+interval_yield+interval_Pdt.+RS+Cell_conc._interval+AS_Vol.; 0.458, 0.729, tmp_cumulo+pH+pH_cumulo+AN_cumulo+interval_yield+RS+Cell_conc._interval+AS_Vol.+consum_O2+generate_CO2; 0.450, 0.729, tmp_cumulo+pH+pH_cumulo+PL+AN+AN_cumulo+interval_yield+RS+Cell_conc._interval+AS_Vol.+emission_CO2; 0.458, 0.729, tmp_cumulo+pH+pH_cumulo+AN+interval_yield+RS+Feed_Vol+Cell_conc._interval+AS_Vol.+consum_O2; 0.441, 0.729, tmp+tmp_cumulo+pH+pH_cumulo+AN_cumulo+interval_yield+RS+Feed_Vol+Cell_conc._interval+rab_integral+AS_Vol.+generate_CO2; 0.449, 0.729, tmp_cumulo+pH+pH_cumulo+PL_cumulo+AN_cumulo+interval_yield+RS+Cell_conc._interval+AS_Vol.+emission_CO2+generate_CO2; 0.466, 0.729, tmp+tmp_cumulo+pH+pH_cumulo+interval_yield+RS+Feed_Vol+Cell_conc._interval+AS_Vol.; 0.440, 0.729, tmp_cumulo+pH+pH_cumulo+AN_cumulo+interval_yield+interval_Pdt.+RS+Feed_Vol+Cell_conc._interval+AS_Vol.+emission_CO2+generate_CO2; 0.466, 0.729, tmp_cumulo+pH+pH_cumulo+AN_cumulo+interval_yield+RS+Feed_Vol+Cell_conc._interval+emission_CO2; 0.449, 0.729, tmp_cumulo+pH+pH_cumulo+AN_cumulo+interval_yield+RS+Feed_Vol+RS_cumulo+Cell_conc._interval+AS_Vol.+emission_CO2; 0.449, 0.729, tmp+tmp_cumulo+pH+pH_cumulo+AN+AN_cumulo+interval_yield+RS+Cell_conc._interval+rab_integral+AS_Vol.; 0.449, 0.729, tmp_cumulo+pH+pH_cumulo+AN+AN_cumulo+interval_yield+RS+Cell_conc._interval+rab_integral+RQ_integral+AS_Vol.; 0.449, 0.729, tmp+tmp_cumulo+pH+pH_cumulo+AN_cumulo+interval_yield+RS+Feed_Vol+RS_cumulo+Cell_conc._interval+AS_Vol.; 0.458, 0.729, tmp_cumulo+pH+pH_cumulo+AN_cumulo+interval_yield+RS+RS_cumulo+Cell_conc._interval+AS_Vol.+emission_CO2; 0.458, 0.729, tmp+tmp_cumulo+pH+pH_cumulo+AN_cumulo+interval_yield+RS+RS_cumulo+Cell_conc._interval+AS_Vol; 0.449, 0.729, tmp_cumulo+pH+pH_cumulo+PL+AN_cumulo+interval_yield+RS+Cell_conc._interval+rab_integral+AS_Vol.+interval_O2; 0.449, 0.729, tmp_cumulo+pH+pH_cumulo+AN_cumulo+interval_yield+RS+Feed_Vol+RS_cumulo+Cell_conc._interval+rab_integral+AS_Vol.; 0.449, 0.729, tmp+tmp_cumulo+pH+pH_cumulo+AN_cumulo+interval_yield+RS+Cell_conc._interval+AS_Vol.+emission_CO2+generate_CO2; 0.466, 0.729, tmp_cumulo+pH+pH_cumulo+interval_yield+RS+Feed_Vol+Cell_conc._interval+AS_Vol.+consum_O2; 0.449, 0.729, tmp+tmp_cumulo+pH+pH_cumulo+AN_cumulo+interval_yield+RS+Cell_conc._interval+rab_integral+AS_Vol.+emission_CO2; 0.458, 0.729, tmp_cumulo+pH+pH_cumulo+AN_cumulo+interval_yield+RS+Cell_conc._interval+AS_Vol.+emission_CO2+consum_O2; 0.458, 0.729, tmp+tmp_cumulo+pH+pH_cumulo+AN_cumulo+interval_yield+RS+Cell_conc._interval+RQ_integral+AS_Vol.; 0.458, 0.729, tmp_cumulo+pH+pH_cumulo+PL+AN_cumulo+interval_yield+interval_Pdt.+RS+Cell_conc._interval+AS_Vol.; 0.440, 0.729, tmp_cumulo+pH+pH_cumulo+PL+AN_cumulo+interval_yield+RS+Cell_conc._interval+rab_integral+RQ_integral+AS_Vol.+emission_CO2; 0.474, 0.729, tmp_cumulo+pH+pH_cumulo+interval_yield+RS+Cell_conc._interval+rab_integral+AS_Vol.; 0.466, 0.729, tmp_cumulo+pH+pH_cumulo+interval_yield+RS+Feed_Vol+Cell_conc._interval+rab_integral+AS_Vol.; 0.474, 0.729, tmp+pH+pH_cumulo+AN_cumulo+interval_yield+RS+Cell_conc._interval+AS_Vol.; 0.440, 0.729, tmp_cumulo+pH+pH_cumulo+AN_cumulo+interval_yield+RS+Feed_Vol+Cell_conc._interval+rab_integral+RQ_integral+AS_Vol.+generate_CO2; 0.449, 0.729, tmp+tmp_cumulo+pH+pH_cumulo+PL+AN_cumulo+interval_yield+RS+Cell_conc._interval+rab_integral+AS_Vol.; 0.440, 0.729, tmp_cumulo+pH+pH_cumulo+PL_cumulo+AN+interval_yield+RS+Feed_Vol+Cell_conc._interval+AS_Vol.+interval_O2+generate_CO2; 0.457, 0.729, tmp_cumulo+pH+pH_cumulo+AN_cumulo+interval_yield+OD+RS+Cell_conc._interval+AS_Vol.+generate_CO2; 0.449, 0.729, tmp_cumulo+pH+pH_cumulo+AN+AN_cumulo+interval_yield+RS+Cell_conc._interval+rab_integral+AS_Vol.+emission_CO2; 0.449, 0.728, tmp_cumulo+pH+pH_cumulo+PL+AN_cumulo+interval_yield+RS+Cell_conc._interval+rab_integral+AS_Vol.+generate_CO2; 0.449, 0.728, tmp_cumulo+pH+pH_cumulo+PL+AN_cumulo+interval_yield+interval_Pdt.+RS+Cell_conc._interval+rab_integral+AS_Vol.; 0.440, 0.728, tmp_cumulo+pH+pH_cumulo+AN+AN_cumulo+interval_yield+RS+Feed_Vol+Cell_conc._interval+rab_integral+RQ_integral+AS_Vol.; 0.466, 0.728, tmp_cumulo+pH+pH_cumulo+AN+AN_cumulo+interval_yield+RS+Feed_Vol+Cell_conc._interval; 0.449, 0.728, tmp_cumulo+pH+pH_cumulo+AN_cumulo+interval_yield+RS+Cell_conc._interval+rab_integral+AS_Vol.+emission_O2+emission_CO2; 0.474, 0.728, tmp_cumulo+pH+pH_cumulo+interval_yield+RS+Feed_Vol+Cell_conc._interval+RQ_integral; 0.440, 0.728, tmp_cumulo+pH+pH_cumulo+PL_cumulo+AN_cumulo+ interval_yield+RS+Cell_conc._interval+rab_integral+AS_Vol.+emission_CO2+generate_CO2; 0.440, 0.728, tmp_cumulo+pH+pH_cumulo+PL_cumulo+AN_cumulo+interval_yield+RS+Feed_Vol+Cell_conc._interval+rab_integral+RQ_integral+AS_Vol.; 0.457, 0.728, tmp_cumulo+pH+pH_cumulo+PL+AN_cumulo+interval_yield+RS+Cell_conc._interval+RQ_integral+AS_Vol.; 0.448, 0.728, tmp+tmp_cumulo+pH+pH_cumulo+AN+interval_yield+RS+Feed_Vol+Cell_conc._interval+AS_Vol.+generate_CO2; 0.448, 0.728, tmp_cumulo+pH+pH_cumulo+AN_cumulo+interval_yield+RS+Feed_Vol+Cell_conc._interval+RQ_integral+AS_Vol.+emission_CO2; 0.473, 0.728, tmp_cumulo+pH+pH_cumulo+interval_yield+RS+Feed_Vol+Cell_conc._interval+emission_O2; 0.465, 0.728, tmp_cumulo+pH+pH_cumulo+interval_yield+RS+Feed_Vol+Cell_conc._interval+interval_O2+generate_CO2; 0.448, 0.728, tmp_cumulo+pH+pH_cumulo+PL_cumulo+AN+interval_yield+RS+Feed_Vol+Cell_conc._interval+AS_Vol.+generate_CO2; 0.439, 0.728, tmp_cumulo+pH+pH_cumulo+AN_cumulo+interval_yield+RS+Cell_conc._interval+rab_integral+RQ_integral+AS_Vol.+emission_O2+emission_CO2; 0.465, 0.728, tmp_cumulo+pH+pH_cumulo+AN_cumulo+interval_yield+RS+Feed_Vol+Cell_conc._interval+consum_O2; 0.465, 0.728, tmp_cumulo+pH+pH_cumulo+interval_yield+RS+Feed_Vol+Cell_conc._interval+rab_integral+consum_O2; 0.448, 0.728, tmp_cumulo+pH+pH_cumulo+PL_cumulo+AN_cumulo+interval_yield+RS+Cell_conc._interval+rab_integral+RQ_integral+AS_Vol.; 0.448, 0.728, tmp_cumulo+pH+pH_cumulo+AN_cumulo+interval_yield+interval_Pdt.+RS+Feed_Vol+Cell_conc._interval+AS_Vol.+consum_O2; 0.439, 0.728, tmp_cumulo+pH+pH_cumulo+PL+AN_cumulo+interval_yield+RS+Feed_Vol+Cell_conc._interval+rab_integral+AS_Vol.+interval_O2; 0.448, 0.728, tmp+tmp_cumulo+pH+pH_cumulo+PL+AN_cumulo+interval_yield+RS+Cell_conc._interval+rab_integral+AS_Vol.; 0.457, 0.728, tmp_cumulo+pH+pH_cumulo+AN+AN_cumulo+interval_yield+RS+Cell_conc._interval+AS_Vol.+emission_O2; 0.448, 0.728, tmp_cumulo+pH+pH_cumulo+PL_cumulo+AN_cumulo+interval_yield+interval_Pdt.+RS+Cell_conc._interval+rab_integral+AS_Vol.; 0.439, 0.728, tmp_cumulo+pH+pH_cumulo+PL_cumulo+AN+AN_cumulo+interval_yield+RS+Feed_Vol+Cell_conc._interval+rab_integral+AS_Vol.; 0.457, 0.728, tmp+tmp_cumulo+pH+pH_cumulo+AN_cumulo+interval_yield+OD+RS+Cell_conc._interval+AS_Vol.; 0.457, 0.728, tmp_cumulo+pH+pH_cumulo+AN+interval_yield+RS+Feed_Vol+RS_cumulo+Cell_conc._interval+AS_Vol.; 0.448, 0.728, tmp+tmp_cumulo+pH+pH_cumulo+AN+AN_cumulo+interval_yield+RS+Cell_conc._interval+AS_Vol.+generate_CO2; 0.473, 0.728, tmp+tmp_cumulo+pH+pH_cumulo+interval_yield+RS+Feed_Vol+Cell_conc._interval; 0.465, 0.728, tmp_cumulo+pH+pH_cumulo+interval_yield+interval_Pdt.+RS+Feed_Vol+Cell_conc._interval+AS_Vol.; 0.448, 0.728, tmp_cumulo+pH+pH_cumulo+PL_cumulo+AN_cumulo+interval_yield+RS+Feed_Vol+Cell_conc._interval+AS_Vol.+consum_O2; 0.439, 0.728, tmp_cumulo+pH+pH_cumulo+AN+AN_cumulo+interval_yield+RS+Feed_Vol+Cell_conc._interval+RQ_integral+AS_Vol.+generate_CO2; 0.448, 0.728, tmp_cumulo+pH+pH_cumulo+AN_cumulo+interval_yield+RS+Feed_Vol+Cell_conc._interval+RQ_integral+AS_Vol.+emission_O2; 0.465, 0.728, tmp_cumulo+pH+pH_cumulo+interval_yield+RS+Feed_Vol+Cell_conc._interval+RQ_integral+AS_Vol.; 0.456, 0.728, tmp_cumulo+pH+pH_cumulo+AN_cumulo+interval_yield+OD+RS+Cell_conc._interval+AS_Vol.+emission_CO2; 0.456, 0.728, tmp_cumulo+pH+pH_cumulo+PL+AN+interval_yield+RS+Cell_conc._interval+rab_integral+AS_Vol.; 0.439, 0.728, tmp+tmp_cumulo+pH+pH_cumulo+PL+AN_cumulo+interval_yield+RS+Cell_conc._interval+rab_integral+AS_Vol.+emission_CO2; 0.448, 0.728, tmp_cumulo+pH+pH_cumulo+AN+interval_yield+RS+Feed_Vol+Cell_conc._interval+RQ_integral+AS_Vol.+generate_CO2; 0.439, 0.728, tmp_cumulo+pH+pH_cumulo+AN+AN_cumulo+interval_yield+interval_Pdt.+RS+Feed_Vol+Cell_conc._interval+AS_Vol.+generate_CO2; 0.448, 0.728, tmp_cumulo+pH+pH_cumulo+PL+AN_cumulo+interval_yield+RS+Feed_Vol+Cell_conc._interval+rab_integral+AS_Vol.; 0.456, 0.728, tmp_cumulo+pH+pH_cumulo+interval_yield+RS+Feed_Vol+Cell_conc._interval+rab_integral+interval_O2+generate_CO2; 0.448, 0.728, tmp_cumulo+pH+pH_cumulo+AN_cumulo+interval_yield+RS+Feed_Vol+Cell_conc._interval+RQ_integral+AS_Vol.+consum_O2; 0.456, 0.728, tmp_cumulo+pH+pH_cumulo+AN_cumulo+interval_yield+RS+Feed_Vol+Cell_conc._interval+AS_Vol.+interval_O2; 0.439, 0.728, tmp_cumulo+pH+pH_cumulo+AN_cumulo+interval_yield+RS+Feed_Vol+Cell_conc._interval+AS_Vol.+emission_O2+emission_CO2+generate_CO2; 0.456, 0.728, tmp_cumulo+pH+pH_cumulo+AN_cumulo+interval_yield+RS+Feed_Vol+Cell_conc._interval+rab_integral+generate_CO2; 0.447, 0.728, tmp_cumulo+pH+pH_cumulo+PL+AN_cumulo+interval_yield+RS+Cell_conc._interval+AS_Vol.+emission_CO2+interval_O2; 0.438, 0.728, tmp+tmp_cumulo+pH+pH_cumulo+AN+AN_cumulo+interval_yield+RS+Feed_Vol+Cell_conc._interval+AS_Vol.+emission_CO2; 0.456, 0.728, tmp_cumulo+pH+pH_cumulo+AN_cumulo+interval_yield+RS+Cell_conc._interval+AS_Vol.+emission_O2+emission_CO2; 0.456, 0.728, tmp_cumulo+pH+pH_cumulo+PL_cumulo+AN_cumulo+interval_yield+RS+Cell_conc._interval+RQ_integral+AS_Vol.; 0.456, 0.728, tmp+tmp_cumulo+pH+pH_cumulo+AN+interval_yield+RS+Cell_conc._interval+AS_Vol.+generate_CO2; 0.456, 0.728, tmp_cumulo+pH+pH_cumulo+AN+interval_yield+RS+Cell_conc._interval+rab_integral+RQ_integral+AS_Vol.; 0.438, 0.728, tmp+tmp_cumulo+pH+pH_cumulo+AN_cumulo+interval_yield+RS+Feed_Vol+Cell_conc._interval+rab_integral+RQ_integral+AS_Vol.; 0.456, 0.728, tmp+tmp_cumulo+pH+pH_cumulo+AN+interval_yield+RS+Cell_conc._interval+rab_integral+AS_Vol.; 0.447, 0.728, tmp_cumulo+pH+pH_cumulo+PL_cumulo+AN_cumulo+interval_yield+RS+Feed_Vol+RS_cumulo+Cell_conc._interval+AS_Vol.; 0.447, 0.728, tmp_cumulo+pH+pH_cumulo+AN_cumulo+interval_yield+interval_Pdt.+RS+Feed_Vol+Cell_conc._interval+AS_Vol.+emission_O2; 0.447, 0.728, tmp_cumulo+pH+pH_cumulo+PL_cumulo+AN+AN_cumulo+interval_yield+RS+Cell_conc._interval+AS_Vol.+generate_CO2; 0.438, 0.728, tmp_cumulo+pH+pH_cumulo+PL_cumulo+AN_cumulo+interval_yield+RS+Feed_Vol+Cell_conc._interval+AS_Vol.+interval_O2+generate_CO2; 0.456, 0.728, tmp_cumulo+pH+pH_cumulo+PL_cumulo+AN+interval_yield+RS+Cell_conc._interval+rab_integral+AS_Vol.; 0.447, 0.728, tmp_cumulo+pH+pH_cumulo+PL+AN+interval_yield+RS+Cell_conc._interval+AS_Vol.+emission_CO2+interval_O2; 0.447, 0.728, tmp_cumulo+pH+pH_cumulo+AN+AN_cumulo+interval_yield+interval_Pdt.+RS+Cell_conc._interval+rab_integral+AS_Vol.; 0.438, 0.728, tmp_cumulo+pH+pH_cumulo+PL_cumulo+AN_cumulo+interval_yield+interval_Pdt.+RS+Feed_Vol+Cell_conc._interval+rab_integral+AS_Vol.; 0.447, 0.728, tmp_cumulo+pH+pH_cumulo+AN_cumulo+interval_yield+interval_Pdt.+RS+Cell_conc._interval+rab_integral+AS_Vol.+emission_CO2; 0.447, 0.727, tmp_cumulo+pH+pH_cumulo+AN_cumulo+interval_yield+interval_Pdt.+RS+Feed_Vol+RS_cumulo+Cell_conc._interval+AS_Vol.; 0.438, 0.727, tmp_cumulo+pH+pH_cumulo+PL+AN_cumulo+interval_yield+interval_Pdt.+RS+Cell_conc._interval+rab_integral+AS_Vol.+emission_CO2; 0.456, 0.727, tmp_cumulo+pH+pH_cumulo+AN_cumulo+interval_yield+RS+Feed_Vol+Cell_conc._interval+Accum._Yield+AS_Vol.; 0.447, 0.727, tmp_cumulo+pH+pH_cumulo+PL_cumulo+AN_cumulo+interval_yield+RS+Feed_Vol+Cell_conc._interval+AS_Vol.+interval_O2; 0.447, 0.727, tmp+tmp_cumulo+pH+pH_cumulo+AN_cumulo+interval_yield+RS+Cell_conc._interval+rab_integral+RQ_integral+AS_Vol.; 0.447, 0.727, tmp_cumulo+pH+pH_cumulo+AN+interval_yield+RS+Feed_Vol+Cell_conc._interval+rab_integral+RQ_integral+AS_Vol.; 0.464, 0.727, tmp_cumulo+pH+pH_cumulo+AN_cumulo+interval_yield+RS+Feed_Vol+Cell_conc._interval+RQ_integral; 0.447, 0.727, tmp_cumulo+pH+pH_cumulo+AN_cumulo+interval_yield+OD+RS+Feed_Vol+Cell_conc._interval+AS_Vol.+generate_CO2; 0.464, 0.727, tmp_cumulo+pH+pH_cumulo+interval_yield+RS+Feed_Vol+Cell_conc._interval+rab_integral+RQ_integral; 0.464, 0.727, tmp+tmp_cumulo+pH+pH_cumulo+AN_cumulo+interval_yield+RS+Feed_Vol+Cell_conc._interval; 0.438, 0.727, tmp+tmp_cumulo+pH+pH_cumulo+AN+AN_cumulo+interval_yield+RS+Feed_Vol+Cell_conc._interval+rab_integral+AS_Vol.; 0.438, 0.727, tmp+tmp_cumulo+pH+pH_cumulo+PL_cumulo+AN_cumulo+interval_yield+RS+Feed_Vol+Cell_conc._interval+AS_Vol.+generate_CO2; 0.447, 0.727, tmp_cumulo+pH+pH_cumulo+PL+AN+AN_cumulo+interval_yield+RS+Cell_conc._interval+AS_Vol.+interval_O2; 0.438, 0.727, tmp_cumulo+pH+pH_cumulo+PL_cumulo+AN+AN_cumulo+interval_yield+RS+Feed_Vol+Cell_conc._interval+RQ_integral+AS_Vol.; 0.455, 0.727, tmp_cumulo+pH+pH_cumulo+AN_cumulo+interval_yield+interval_Pdt.+OD+RS+Cell_conc._interval+AS_Vol.; 0.447, 0.727, tmp_cumulo+pH+pH_cumulo+AN_cumulo+interval_yield+RS+Cell_conc._interval+AS_Vol.+emission_CO2+consum_O2+generate_CO2; 0.438, 0.727, tmp_cumulo+pH+pH_cumulo+AN+AN_cumulo+interval_yield+interval_Pdt.+RS+Feed_Vol+Cell_conc._interval+rab_integral+AS_Vol.; 0.447, 0.727, tmp+tmp_cumulo+pH+pH_cumulo+PL+AN_cumulo+interval_yield+RS+Cell_conc._interval+AS_Vol.+emission_CO2; 0.472, 0.727, pH+pH_cumulo+PL_cumulo+AN_cumulo+interval_yield+RS+Cell_conc._interval+AS_Vol.; 0.446, 0.727, tmp_cumulo+pH+pH_cumulo+AN_cumulo+interval_yield+interval_Pdt.+RS+Cell_conc._interval+AS_Vol.+emission_CO2+generate_CO2; 0.455, 0.727, tmp_cumulo+pH+pH_cumulo+AN_cumulo+interval_yield+interval_Pdt.+RS+RS_cumulo+Cell_conc._interval+AS_Vol.; 0.437, 0.727, tmp+tmp_cumulo+pH+pH_cumulo+AN_cumulo+interval_yield+RS+Feed_Vol+Cell_conc._interval+rab_integral+AS_Vol.+emission_CO2; 0.446, 0.727, tmp_cumulo+pH+pH_cumulo+AN_cumulo+interval_yield+RS+Feed_Vol+Cell_conc._interval+AS_Vol.+interval_O2+generate_CO2; 0.455, 0.727, tmp_cumulo+pH+pH_cumulo+interval_yield+RS+Feed_Vol+Cell_conc._interval+AS_Vol.+emission_CO2+generate_CO2; 0.437, 0.727, tmp_cumulo+pH+pH_cumulo+AN+AN_cumulo+interval_yield+RS+Feed_Vol+Cell_conc._interval+rab_integral+AS_Vol.+emission_CO2; 0.455, 0.727, tmp_cumulo+pH+pH_cumulo+AN_cumulo+interval_yield+RS+Cell_conc._interval+RQ_integral+AS_Vol.+generate_CO2; 0.437, 0.727, tmp_cumulo+pH+pH_cumulo+AN_cumulo+interval_yield+interval_Pdt.+RS+Feed_Vol+Cell_conc._interval+rab_integral+AS_Vol.+generate_CO2; 0.446, 0.727, tmp+tmp_cumulo+pH+pH_cumulo+AN_cumulo+interval_yield+interval_Pdt.+RS+Cell_conc._interval+rab_integral+AS_Vol.; 0.463, 0.727, tmp_cumulo+pH+pH_cumulo+PL_cumulo+interval_yield+RS+Feed_Vol+Cell_conc._interval+AS_Vol.; 0.437, 0.727, tmp_cumulo+pH+pH_cumulo+AN_cumulo+interval_yield+interval_Pdt.+RS+Feed_Vol+Cell_conc._interval+rab_integral+RQ_integral+AS_Vol.; 0.446, 0.727, tmp_cumulo+pH+pH_cumulo+AN+AN_cumulo+interval_yield+RS+Cell_conc._interval+rab_integral+AS_Vol.+consum_O2; 0.463, 0.727, tmp_cumulo+pH+pH_cumulo+interval_yield+RS+Feed_Vol+Cell_conc._interval+AS_Vol.+emission_O2; 0.446, 0.727, tmp_cumulo+pH+pH_cumulo+AN+interval_yield+interval_Pdt.+RS+Feed_Vol+Cell_conc._interval+AS_Vol.+generate_CO2; 0.437, 0.727, tmp+tmp_cumulo+pH+pH_cumulo+PL_cumulo+AN_cumulo+interval_yield+RS+Feed_Vol+Cell_conc._interval+rab_integral+AS_Vol.; 0.446, 0.727, tmp_cumulo+pH+pH_cumulo+AN_cumulo+interval_yield+RS+RS_cumulo+Cell_conc._interval+rab_integral+AS_Vol.+generate_CO2; 0.437, 0.727, tmp_cumulo+pH+pH_cumulo+PL+AN+interval_yield+RS+Cell_conc._interval+rab_integral+AS_Vol.+emission_CO2+interval_O2; 0.455, 0.727, tmp_cumulo+pH+pH_cumulo+PL+AN_cumulo+interval_yield+RS+Cell_conc._interval+AS_Vol.+generate_CO2; 0.437, 0.727, tmp_cumulo+pH+pH_cumulo+PL+AN+interval_yield+RS+Feed_Vol+Cell_conc._interval+rab_integral+AS_Vol.+interval_O2; 0.446, 0.727, tmp_cumulo+pH+pH_cumulo+AN_cumulo+interval_yield+RS+Cell_conc._interval+rab_integral+RQ_integral+AS_Vol.+generate_CO2; 0.463, 0.727, tmp_cumulo+pH+pH_cumulo+interval_yield+RS+Feed_Vol+Cell_conc._interval+emission_CO2+generate_CO2; 0.463, 0.727, tmp_cumulo+pH+pH_cumulo+AN_cumulo+interval_yield+RS+Feed_Vol+Cell_conc._interval+emission_O2; 0.479, 0.727, tmp_cumulo+pH+AN_cumulo+interval_yield+RS+Feed_Vol+Cell_conc._interval; 0.463, 0.727, tmp_cumulo+pH+pH_cumulo+interval_yield+RS+Feed_Vol+Cell_conc._interval+rab_integral+generate_CO2; 0.446, 0.727, tmp_cumulo+pH+pH_cumulo+AN_cumulo+interval_yield+RS+RS_cumulo+Cell_conc._interval+AS_Vol.+emission_CO2+generate_CO2; 0.479, 0.727, tmp_cumulo+pH+interval_yield+RS+Feed_Vol+Cell_conc._interval+AS_Vol.; 0.437, 0.727, tmp+tmp_cumulo+pH+pH_cumulo+PL+AN_cumulo+interval_yield+RS+Feed_Vol+Cell_conc._interval+AS_Vol.+interval_O2; 0.454, 0.727, tmp_cumulo+pH+pH_cumulo+AN_cumulo+interval_yield+RS+Feed_Vol+Cell_conc._interval+rab_integral+RQ_integral; 0.437, 0.727, tmp_cumulo+pH+pH_cumulo+AN_cumulo+interval_yield+RS+Feed_Vol+Cell_conc._interval+RQ_integral+AS_Vol.+emission_CO2+generate_CO2; 0.446, 0.727, tmp_cumulo+pH+pH_cumulo+AN_cumulo+interval_yield+interval_Pdt.+RS+Cell_conc._interval+rab_integral+AS_Vol.+generate_CO2; 0.437, 0.727, tmp_cumulo+pH+pH_cumulo+PL+AN+AN_cumulo+interval_yield+RS+Feed_Vol+Cell_conc._interval+AS_Vol.+interval_O2; 0.437, 0.727, tmp_cumulo+pH+pH_cumulo+AN_cumulo+interval_yield+interval_Pdt.+RS+Feed_Vol+Cell_conc._interval+rab_integral+AS_Vol.+emission_CO2; 0.437, 0.727, tmp_cumulo+pH+pH_cumulo+AN_cumulo+interval_yield+RS+Feed_Vol+RS_cumulo+Cell_conc._interval+AS_Vol.+emission_CO2+generate_CO2; 0.446, 0.727, tmp_cumulo+pH+pH_cumulo+PL_cumulo+AN_cumulo+interval_yield+RS+Cell_conc._interval+rab_integral+AS_Vol.+consum_O2; 0.446, 0.727, tmp_cumulo+pH+pH_cumulo+AN+AN_cumulo+interval_yield+OD+RS+Feed_Vol+Cell_conc._interval+AS_Vol.; 0.437, 0.727, tmp_cumulo+pH+pH_cumulo+

AN_cumulo+interval_yield+RS+Feed_Vol+Cell_conc._interval+AS_Vol.+emission_CO2+consum_O2+generate_CO2; 0.454, 0.727, tmp_cumulo+pH+pH_cumulo+AN_cumulo+interval_yield+RS+Cell_conc._interval+AS_Vol.+consum_O2; 0.446, 0.727, tmp_cumulo+pH+_pH_cumulo+AN_cumulo+interval_yield+RS+Feed_Vol+RS_cumulo+Cell_conc._interval+RQ_integral+AS_Vol.; 0.437, 0.727, tmp_cumulo+pH+pH_cumulo+AN+AN_cumulo+interval_yield+interval_Pdt.+RS+Feed_Vol+Cell_conc._interval+AS_Vol.+emission_CO2; 0.446, 0.727, tmp+tmp_cumulo+pH+pH_cumulo+AN+AN_cumulo+interval_yield+RS+Cell_conc._interval+AS_Vol.+emission_CO2; 0.454, 0.727, tmp_cumulo+pH+pH_cumulo+AN_cumulo+interval_yield+interval_Pdt.+RS+Cell_conc._interval+AS_Vol.+consum_O2; 0.454, 0.727, tmp_cumulo+pH+pH_cumulo+AN_cumulo+interval_yield+RS+Cell_conc._interval+RQ_integral+AS_Vol.+consum_O2; 0.479, 0.727, tmp_cumulo+pH+interval_yield+RS+Feed_Vol+Cell_conc._interval+interval_O2; 0.437, 0.727, tmp+tmp_cumulo+pH+pH_cumulo+AN+AN_cumulo+interval_yield+RS+Feed_Vol+Cell_conc._interval+RQ_integral+AS_Vol.; 0.454, 0.727, tmp_cumulo+pH+pH_cumulo+AN+interval_yield+RS+Cell_conc._interval+rab_integral+AS_Vol.+emission_CO2; 0.454, 0.727, tmp_cumulo+pH+pH_cumulo+PL+AN_cumulo+interval_yield+OD+RS+Cell_conc._interval+AS_Vol.; 0.471, 0.727, tmp_cumulo+pH+pH_cumulo+interval_yield+RS+Cell_conc._interval+AS_Vol.+emission_CO2; 0.454, 0.727, tmp_cumulo+pH+pH_cumulo+AN_cumulo+interval_yield+interval_Pdt.+RS+Cell_conc._interval+RQ_integral+AS_Vol.; 0.454, 0.727, tmp_cumulo+pH+pH_cumulo+PL_cumulo+AN+interval_yield+RS+Cell_conc._interval+AS_Vol.+generate_CO2; 0.454, 0.726, tmp_cumulo+pH+pH_cumulo+AN+interval_yield+interval_Pdt.+RS+Cell_conc._interval+rab_integral+AS_Vol.; 0.436, 0.726, tmp_cumulo+pH+pH_cumulo+PL+AN+interval_yield+RS+Cell_conc._interval+AS_Vol.+emission_CO2+interval_O2+generate_CO2; 0.436, 0.726, tmp_cumulo+pH+pH_cumulo+PL_cumulo+AN_cumulo+interval_yield+RS+Feed_Vol+Cell_conc._interval+rab_integral+AS_Vol.+emission_CO2; 0.445, 0.726, tmp+tmp_cumulo+pH+pH_cumulo+AN_cumulo+interval_yield+RS+Cell_conc._interval+rab_integral+AS_Vol.+consum_O2; 0.436, 0.726, tmp_cumulo+pH+pH_cumulo+PL_cumulo+AN_cumulo+interval_yield+RS+Feed_Vol+Cell_conc._interval+RQ_integral+AS_Vol.+generate_CO2; 0.445, 0.726, tmp_cumulo+pH_cumulo+AN+interval_yield+RS+Cell_conc._interval+rab_integral+AS_Vol.+consum_O2+generate_CO2; 0.436, 0.726, tmp+tmp_cumulo+pH+pH_cumulo+AN_cumulo+interval_yield+RS+Feed_Vol+Cell_conc._interval+RQ_integral+AS_Vol.+generate_CO2; 0.436, 0.726, tmp_cumulo+pH+pH_cumulo+PL+AN+AN_cumulo+interval_yield+RS+Cell_conc._interval+RQ_integral+AS_Vol.+emission_CO2; 0.445, 0.726, tmp_cumulo+pH+pH_cumulo+AN_cumulo+interval_yield+RS+Cell_conc._interval+AS_Vol.+emission_O2+emission_CO2+generate_CO2; 0.436, 0.726, tmp+tmp_cumulo+pH+pH_cumulo+AN+AN_cumulo+interval_yield+RS+Feed_Vol+Cell_conc._interval+AS_Vol.; 0.445, 0.726, tmp_cumulo+pH+pH_cumulo+PL_cumulo+AN_cumulo+interval_yield+RS+Feed_Vol+Cell_conc._interval+AS_Vol.+emission_O2; 0.436, 0.726, tmp_cumulo+pH+pH_cumulo+AN_cumulo+interval_yield+RS+Feed_Vol+RS_cumulo+Cell_conc._interval+AS_Vol.+generate_CO2; 0.436, 0.726, tmp_cumulo+pH+pH_cumulo+AN_cumulo+interval_yield+RS+Cell_conc._interval+rab_integral+AS_Vol.+emission_O2+emission_CO2+generate_CO2; 0.445, 0.726, tmp_cumulo+pH+pH_cumulo+AN_cumulo+interval_yield+RS+RS_cumulo+Cell_conc._interval+rab_integral+AS_Vol.+emission_CO2; 0.445, 0.726, tmp_cumulo+pH+pH_cumulo+AN_cumulo+interval_yield+RS+Cell_conc._interval+rab_integral+AS_Vol.+emission_CO2+consum_O2; 0.445, 0.726, tmp_cumulo+pH+pH_cumulo+AN+interval_yield+RS+Feed_Vol+Cell_conc._interval+AS_Vol.+interval_O2+generate_CO2; 0.445, 0.726, tmp+tmp_cumulo+pH+pH_cumulo+AN+interval_yield+RS+Feed_Vol+Cell_conc._interval+AS_Vol.+emission_CO2; 0.445, 0.726, tmp+tmp_cumulo+pH+pH_cumulo+AN_cumulo+interval_yield+OD+RS+Feed_Vol+Cell_conc._interval+AS_Vol.; 0.445, 0.726, tmp_cumulo+pH+pH_cumulo+PL+AN_cumulo+interval_yield+RS+Feed_Vol+Cell_conc._interval+RQ_integral+AS_Vol.; 0.436, 0.726, tmp_cumulo+pH+pH_cumulo+AN_cumulo+interval_yield+RS+Feed_Vol+Cell_conc._interval+rab_integral+AS_Vol.+emission_O2+emission_CO2; 0.453, 0.726, tmp_cumulo+pH+pH_cumulo+AN+interval_yield+RS+Feed_Vol+Cell_conc._interval+emission_CO2+generate_CO2; 0.436, 0.726, tmp_cumulo+pH+pH_cumulo+AN+AN_cumulo+interval_yield+RS+Feed_Vol+Cell_conc._interval+AS_Vol.+consum_O2+generate_CO2; 0.426, 0.726, tmp_cumulo+pH+pH_cumulo+AN_cumulo+interval_yield+RS+Feed_Vol+Cell_conc._interval+rab_integral+RQ_integral+AS_Vol.+emission_O2+emission_CO2; 0.445, 0.726, tmp_cumulo+pH+pH_cumulo+AN_cumulo+interval_yield+RS+Feed_Vol+RS_cumulo+Cell_conc._interval+AS_Vol.+emission_O2; 0.436, 0.726, tmp_cumulo+pH+pH_cumulo+AN_cumulo+interval_yield+RS+Feed_Vol+Cell_conc._interval+rab_integral+AS_Vol.+emission_O2+generate_CO2; 0.445, 0.726, tmp_cumulo+pH+pH_cumulo+AN+AN_cumulo+interval_yield+RS+RS_cumulo+Cell_conc._interval+rab_integral+AS_Vol.; 0.426, 0.726, tmp_cumulo+pH+pH_cumulo+PL_cumulo+AN_cumulo+interval_yield+RS+Feed_Vol+Cell_conc._interval+rab_integral+AS_Vol.+emission_CO2+generate_CO2; 0.453, 0.726, tmp_cumulo+pH+pH_cumulo+AN+interval_yield+OD+RS+Feed_Vol+Cell_conc._interval+AS_Vol.; 0.453, 0.726, tmp_cumulo+pH+pH_cumulo+AN_cumulo+interval_yield+interval_Pdt.+RS+Feed_Vol+Cell_conc._interval+rab_integral; 0.470, 0.726, tmp_cumulo+pH+pH_cumulo+PL_cumulo+interval_yield+RS+Feed_Vol+Cell_conc._interval; 0.445, 0.726, tmp_cumulo+pH+pH_cumulo+AN_cumulo+interval_yield+RS+Feed_Vol+Cell_conc._interval+AS_Vol.+emission_O2+consum_O2; 0.445, 0.726, tmp_cumulo+pH+pH_cumulo+AN_cumulo+interval_yield+OD+RS+Feed_Vol+Cell_conc._interval+rab_integral+AS_Vol.; 0.453, 0.726, tmp_cumulo+pH+pH_cumulo+PL+AN_cumulo+interval_yield+RS+Cell_conc._interval+AS_Vol.+consum_O2; 0.436, 0.726, tmp_cumulo+pH+pH_cumulo+PL_cumulo+AN+AN_cumulo+interval_yield+RS+Feed_Vol+Cell_conc._interval+AS_Vol.+emission_CO2; 0.436, 0.726, tmp+tmp_cumulo+pH+pH_cumulo+AN_cumulo+interval_yield+interval_Pdt.+RS+Feed_Vol+Cell_conc._interval+rab_integral+AS_Vol.; 0.445, 0.726, tmp_cumulo+pH+pH_cumulo+AN_cumulo+interval_yield+interval_Pdt.+OD+RS+Feed_Vol+Cell_conc._interval+AS_Vol.; 0.436, 0.726, tmp_cumulo+pH+pH_cumulo+PL_cumulo+AN_cumulo+interval_yield+interval_Pdt.+RS+Feed_Vol+Cell_conc._interval+AS_Vol.+generate_CO2; 0.436, 0.726, tmp+tmp_cumulo+pH+pH_cumulo+PL+AN+interval_yield+RS+Feed_Vol+Cell_conc._interval+AS_Vol.+interval_O2; 0.444, 0.726, tmp_cumulo+pH+pH_cumulo+AN+interval_yield+RS+Feed_Vol+Cell_conc._interval+AS_Vol.+consum_O2+generate_CO2; 0.462, 0.726, tmp_cumulo+pH+AN_cumulo+interval_yield+RS+Feed_Vol+Cell_conc._interval+AS_Vol.+generate_CO2; 0.444, 0.726, tmp_cumulo+pH+ pH_cumulo+AN+interval_yield+RS+Feed_Vol+Cell_conc._interval+AS_Vol.+emission_O2+generate_CO2; 0.436, 0.726, tmp_cumulo+pH+pH_cumulo+PL_cumulo+AN+AN_cumulo+interval_yield+interval_Pdt.+RS+Feed_Vol+Cell_conc._interval+AS_Vol.; 0.444, 0.726, tmp_cumulo+pH+pH_cumulo+AN_cumulo+interval_yield+interval_Pdt.+RS+Cell_conc._interval+rab_integral+RQ_integral+AS_Vol.; 0.462, 0.726, tmp_cumulo+pH+pH_cumulo+AN+interval_yield+RS+Cell_conc._interval+Accum._Yield+AS_Vol.; 0.453, 0.726, tmp_cumulo+pH+pH_cumulo+PL_cumulo+AN_cumulo+interval_yield+RS+RS_cumulo+Cell_conc._interval+AS_Vol.; 0.453, 0.726, tmp_cumulo+pH+pH_cumulo+AN+interval_yield+OD+RS+Cell_conc._interval+AS_Vol.+generate_CO2; 0.461, 0.726, tmp+pH+pH_cumulo+PL_cumulo+AN_cumulo+interval_yield+RS+Cell_conc._interval+AS_Vol.; 0.461, 0.726, tmp_cumulo+pH+pH_cumulo+interval_yield+RS+Feed_Vol+Cell_conc._interval+rab_integral+emission_CO2; 0.444, 0.726, tmp+tmp_cumulo+pH+pH_cumulo+AN_cumulo+interval_yield+RS+RS_cumulo+Cell_conc._interval+rab_integral+AS_Vol.; 0.444, 0.726, tmp_cumulo+pH+pH_cumulo+AN+AN_cumulo+interval_yield+RS+Cell_conc._interval+AS_Vol.+consum_O2+generate_CO2; 0.435, 0.726, tmp+tmp_cumulo+pH+pH_cumulo+AN+AN_cumulo+interval_yield+RS+Feed_Vol+Cell_conc._interval+AS_Vol.+emission_O2; 0.426, 0.726, tmp_cumulo+pH+pH_cumulo+PL_cumulo+AN+AN_cumulo+interval_yield+RS+Feed_Vol+Cell_conc._interval+AS_Vol.+emission_CO2+generate_CO2; 0.444, 0.726, tmp_cumulo+pH+pH_cumulo+PL_cumulo+AN_cumulo+interval_yield+RS+RS_cumulo+Cell_conc._interval+rab_integral+AS_Vol.; 0.453, 0.726, tmp_cumulo+pH+pH_cumulo+AN+interval_yield+RS+Cell_conc._interval+rab_integral+AS_Vol.+emission_O2; 0.461, 0.726, tmp_cumulo+pH+pH_cumulo+interval_yield+RS+Feed_Vol+Cell_conc._interval+rab_integral+interval_O2; 0.461, 0.726, tmp_cumulo+pH+AN_cumulo+interval_yield+RS+Feed_Vol+Cell_conc._interval+AS_Vol.+emission_CO2; 0.444, 0.726, tmp+tmp_cumulo+pH+pH_cumulo+PL+AN+interval_yield+RS+Cell_conc._interval+AS_Vol.+interval_O2; 0.444, 0.726, tmp_cumulo+pH+pH_cumulo+PL_cumulo+AN+interval_yield+RS+Feed_Vol+Cell_conc._interval+RQ_integral+AS_Vol.; 0.453, 0.726, tmp+tmp_cumulo+pH+pH_cumulo+AN_cumulo+interval_yield+RS+Cell_conc._interval+AS_Vol.+emission_O2; 0.435, 0.726, tmp_cumulo+pH_cumulo+PL_cumulo+AN_cumulo+interval_yield+RS+Cell_conc._interval+AS_Vol.+emission_CO2+interval_O2+generate_CO2; 0.444, 0.726, tmp_cumulo+pH+pH_cumulo+AN_cumulo+interval_yield+OD+RS+Feed_Vol+Cell_conc._interval+AS_Vol.+emission_CO2; 0.444, 0.726, tmp_cumulo+pH+pH_cumulo+PL+AN_cumulo+interval_yield+RS+Cell_conc._interval+rab_integral+AS_Vol.+consum_O2; 0.444, 0.726, tmp_cumulo+pH+pH_cumulo+AN+AN_cumulo+interval_yield+OD+RS+Cell_conc._interval+AS_Vol.+generate_CO2; 0.444, 0.726, tmp+tmp_cumulo+pH+pH_cumulo+AN+interval_yield+RS+Feed_Vol+Cell_conc._interval+AS_Vol.+emission_O2; 0.435, 0.726, tmp+tmp_cumulo+pH+pH_cumulo+AN_cumulo+interval_yield+interval_Pdt.+RS+Feed_Vol+Cell_conc._interval+AS_Vol.+generate_CO2; 0.435, 0.726, tmp+tmp_cumulo+pH+pH_cumulo+PL_cumulo+AN_cumulo+interval_yield+RS+Feed_Vol+Cell_conc._interval+RQ_integral+AS_Vol.; 0.435, 0.726, tmp+tmp_cumulo+pH+pH_cumulo+AN+AN_cumulo+interval_yield+interval_Pdt.+RS+Feed_Vol+Cell_conc._interval+AS_Vol; 0.444, 0.726, tmp_cumulo+pH+pH_cumulo+AN_cumulo+interval_yield+OD+RS+Cell_conc._interval+AS_Vol.+emission_CO2+generate_CO2; 0.444, 0.726, tmp_cumulo+pH+pH_cumulo+AN+interval_yield+interval_Pdt.+RS+Feed_Vol+Cell_conc._interval+rab_integral+AS_Vol.; 0.453, 0.726, tmp_cumulo+pH+pH_cumulo+AN_cumulo+interval_yield+RS+Feed_Vol+Cell_conc._interval+rab_integral+consum_O2; 0.435, 0.726, tmp_cumulo+pH+pH_cumulo+AN+AN_cumulo+interval_yield+RS+Feed_Vol+Cell_conc._interval+AS_Vol.+emission_O2+generate_CO2; 0.453, 0.726, tmp_cumulo+pH+pH_cumulo+AN+interval_yield+RS+Cell_conc._interval+AS_Vol.+consum_O2+generate_CO2; 0.435, 0.726, tmp_cumulo+pH+pH_cumulo+PL+AN_cumulo+interval_yield+RS+Cell_conc._interval+rab_integral+AS_Vol.+emission_CO2+consum_O2; 0.453, 0.726, tmp_cumulo+pH+pH_cumulo+AN_cumulo+interval_yield+RS+RS_cumulo+Cell_conc._interval+AS_Vol.+consum_O2; 0.444, 0.726, tmp+tmp_cumulo+pH+pH_cumulo+AN+interval_yield+RS+Feed_Vol+Cell_conc._interval+rab_integral+AS_Vol.; 0.444, 0.726, tmp+tmp_cumulo+pH+pH_cumulo+PL+AN+AN_cumulo+interval_yield+RS+Cell_conc._interval+AS_Vol.; 0.444, 0.726, tmp_cumulo+pH+pH_cumulo+AN+interval_yield+RS+Feed_Vol+RS_cumulo+Cell_conc._interval+AS_Vol.+generate_CO2; 0.469, 0.726, tmp_cumulo+pH+pH_cumulo+interval_yield+interval_Pdt.+RS+Cell_conc._interval+AS_Vol.; 0.453, 0.726, tmp_cumulo+pH+pH_cumulo+AN+interval_yield+RS+Cell_conc._interval+rab_integral+AS_Vol.+consum_O2; 0.435, 0.726, tmp_cumulo+pH+pH_cumulo+AN_cumulo+interval_yield+RS+Feed_Vol+Cell_conc._interval+rab_integral+AS_Vol.+consum_O2+generate_CO2; 0.426, 0.726, tmp_cumulo+pH+pH_cumulo+AN+AN_cumulo+interval_yield+RS+Feed_Vol+Cell_conc._interval+rab_integral+AS_Vol.+emission_CO2+generate_CO2; 0.453, 0.726, tmp_cumulo+pH+pH_cumulo+AN+AN_cumulo+interval_yield+RS+Cell_conc._interval+Accum._Yield+AS_Vol.; 0.435, 0.726, tmp+tmp_cumulo+pH+pH_cumulo+AN+interval_yield+interval_Pdt.+RS+Feed_Vol+Cell_conc._interval+AS_Vol.+emission_CO2; 0.453, 0.726, tmp_cumulo+pH+pH_cumulo+PL+AN+interval_yield+RS+Cell_conc._interval+AS_Vol.+emission_CO2; 0.444, 0.726, tmp+tmp_cumulo+pH+pH_cumulo+PL+AN_cumulo+interval_yield+RS+Feed_Vol+Cell_conc._interval+AS_Vol.; 0.453, 0.726, tmp_cumulo+pH+pH_cumulo+AN+interval_yield+RS+Cell_conc._interval+RQ_integral+AS_Vol.+generate_CO2; 0.444, 0.726, tmp_cumulo+pH+pH_cumulo+AN_cumulo+interval_yield+RS+Cell_conc._interval+rab_integral+RQ_integral+AS_Vol.+consum_O2; 0.444, 0.726, tmp_cumulo+pH+pH_cumulo+PL_cumulo+AN_cumulo+interval_yield+OD+RS+Feed_Vol+Cell_conc._interval+AS_Vol.; 0.461, 0.726, tmp_cumulo+pH+pH_cumulo+interval_yield+RS+Feed_Vol+RS_cumulo+Cell_conc._interval+AS_Vol.; 0.435, 0.726, tmp_cumulo+pH+pH_cumulo+PL_cumulo+AN+AN_cumulo+interval_yield+RS+Cell_conc._interval+rab_integral+AS_Vol.+generate_CO2; 0.425, 0.726, tmp_cumulo+pH+pH_cumulo+PL+AN_cumulo+interval_yield+RS+Cell_conc._interval+rab_integral+AS_Vol.+emission_CO2+interval_O2+generate_CO2; 0.444, 0.726, tmp_cumulo+pH+pH_cumulo+AN+AN_cumulo+interval_yield+interval_Pdt.+RS+Cell_conc._interval+AS_Vol.+generate_CO2; 0.444, 0.726, tmp_cumulo+pH+pH_cumulo+AN+AN_cumulo+interval_yield+RS+Cell_conc._interval+rab_integral+AS_Vol.+emission_O2; 0.435, 0.725, tmp_cumulo+pH+pH_cumulo+AN+AN_cumulo+interval_yield+RS+Cell_conc._interval+rab_integral+AS_Vol.+emission_CO2+generate_CO2; 0.444, 0.725, tmp_cumulo+pH+pH_cumulo+PL+AN+AN_cumulo+interval_yield+

RS+Cell_conc._interval+RQ_integral+AS_Vol.; 0.444, 0.725, tmp_cumulo+pH+pH_cumulo+AN_cumulo+interval_yield+RS+Feed_Vol+RS_cumulo+Cell_conc._interval+AS_Vol.+consum_O2; 0.461, 0.725, tmp_cumulo+pH+pH_cumulo+interval_yield+interval_Pdt.+RS+Feed_Vol+Cell_conc._interval+rab_integral; 0.469, 0.725, tmp+tmp_cumulo+pH+pH_cumulo+interval_yield+RS+Cell_conc._interval+AS_Vol.; 0.444, 0.725, tmp_cumulo+pH+pH_cumulo+AN+AN_cumulo+interval_yield+RS+RS_cumulo+Cell_conc._interval+AS_Vol.+generate_CO2; 0.461, 0.725, tmp_cumulo+pH+pH_cumulo+PL_cumulo+AN_cumulo+interval_yield+RS+Feed_Vol+Cell_conc._interval; 0.452, 0.725, tmp+tmp_cumulo+pH+pH_cumulo+AN+interval_yield+RS+Cell_conc._interval+AS_Vol.+emission_CO2; 0.425, 0.725, tmp_cumulo+pH+pH_cumulo+PL_cumulo+AN+AN_cumulo+interval_yield+RS+Feed_Vol+Cell_conc._interval+AS_Vol.+interval_O2+generate_CO2; 0.461, 0.725, tmp_cumulo+pH+pH_cumulo+interval_yield+RS+Feed_Vol+Cell_conc._interval+consum_O2+generate_CO2; 0.443, 0.725, tmp_cumulo+pH+pH_cumulo+AN+interval_yield+RS+Feed_Vol+Cell_conc._interval+rab_integral+AS_Vol.+emission_CO2; 0.434, 0.725, tmp_cumulo+pH+pH_cumulo+AN_cumulo+interval_yield+RS+Feed_Vol+RS_cumulo+Cell_conc._interval+rab_integral+AS_Vol.+generate_CO2; 0.452, 0.725, tmp_cumulo+pH+pH_cumulo+AN_cumulo+interval_yield+RS+Cell_conc._interval+rab_integral+Accum._Yield+AS_Vol.; 0.461, 0.725, tmp_cumulo+pH+pH_cumulo+interval_yield+RS+Feed_Vol+Cell_conc._interval+emission_CO2+consum_O2; 0.443, 0.725, tmp+tmp_cumulo+pH+pH_cumulo+AN+interval_yield+RS+Feed_Vol+Cell_conc._interval+RQ_integral+AS_Vol.; 0.434, 0.725, tmp_cumulo+pH+pH_cumulo+AN+AN_cumulo+interval_yield+RS+Feed_Vol+Cell_conc._interval+rab_integral+AS_Vol.+emission_O2; 0.443, 0.725, tmp_cumulo+pH+pH_cumulo+PL+AN+AN_cumulo+interval_yield+RS+Feed_Vol+Cell_conc._interval+AS_Vol.; 0.452, 0.725, tmp_cumulo+pH+pH_cumulo+AN+interval_yield+interval_Pdt.+RS+Cell_conc._interval+AS_Vol.+generate_CO2; 0.443, 0.725, tmp_cumulo+pH+pH_cumulo+PL+AN_cumulo+interval_yield+interval_Pdt.+RS+Cell_conc._interval+AS_Vol.+emission_CO2; 0.452, 0.725, tmp_cumulo+pH+pH_cumulo+AN_cumulo+interval_yield+interval_Pdt.+RS+Feed_Vol+Cell_conc._interval+emission_CO2; 0.460, 0.725, tmp_cumulo+pH+pH_cumulo+AN+interval_yield+RS+Feed_Vol+Cell_conc._interval+generate_CO2; 0.452, 0.725, tmp_cumulo+pH+pH_cumulo+AN+interval_yield+RS+RS_cumulo+Cell_conc._interval+AS_Vol.+generate_CO2; 0.443, 0.725, tmp+tmp_cumulo+pH+pH_cumulo+AN+AN_cumulo+interval_yield+RS+Cell_conc._interval+RQ_integral+AS_Vol.; 0.443, 0.725, tmp_cumulo+pH+pH_cumulo+PL_cumulo+AN+interval_yield+RS+Feed_Vol+Cell_conc._interval+rab_integral+AS_Vol.; 0.434, 0.725, tmp_cumulo+pH+pH_cumulo+PL+AN+AN_cumulo+interval_yield+RS+Cell_conc._interval+rab_integral+AS_Vol.+interval_O2; 0.434, 0.725, tmp+tmp_cumulo+pH+pH_cumulo+AN_cumulo+interval_yield+RS+Cell_conc._interval+rab_integral+AS_Vol.+emission_CO2+generate_CO2; 0.469, 0.725, tmp_cumulo+pH+interval_yield+RS+Feed_Vol+Cell_conc._interval+interval_O2+generate_CO2; 0.476, 0.725, tmp_cumulo+pH+interval_yield+RS+Feed_Vol+Cell_conc._interval+consum_O2; 0.434, 0.725, tmp+tmp_cumulo+pH+pH_cumulo+AN+AN_cumulo+interval_yield+RS+Feed_Vol+Cell_conc._interval+rab_integral+AS_Vol.+emission_O2; 0.434, 0.725, tmp_cumulo+pH+pH_cumulo+PL+AN+AN_cumulo+interval_yield+RS+Cell_conc._interval+AS_Vol.+emission_CO2+generate_CO2; 0.443, 0.725, tmp_cumulo+pH+pH_cumulo+AN+interval_yield+RS+Feed_Vol+Cell_conc._interval+rab_integral+AS_Vol.+emission_O2; 0.434, 0.725, tmp_cumulo+pH+pH_cumulo+PL_cumulo+AN+AN_cumulo+interval_yield+RS+Cell_conc._interval+AS_Vol.+emission_CO2+generate_CO2; 0.434, 0.725, tmp_cumulo+pH+pH_cumulo+AN+AN_cumulo+interval_yield+interval_Pdt.+RS+Feed_Vol+Cell_conc._interval+RQ_integral+AS_Vol.; 0.443, 0.725, tmp_cumulo+pH+pH_cumulo+AN+interval_yield+interval_Pdt.+RS+Feed_Vol+Cell_conc._interval+AS_Vol.+emission_CO2; 0.425, 0.725, tmp_cumulo+pH+pH_cumulo+PL_cumulo+AN+AN_cumulo+interval_yield+RS+Feed_Vol+Cell_conc._interval+rab_integral+AS_Vol.+generate_CO2; 0.468, 0.725, tmp+pH+pH_cumulo+AN+interval_yield+RS+Cell_conc._interval+AS_Vol.; 0.452, 0.725, tmp_cumulo+pH+pH_cumulo+AN_cumulo+interval_yield+RS+Cell_conc._interval+RQ_integral+AS_Vol.+emission_CO2; 0.443, 0.725, tmp_cumulo+pH+pH_cumulo+PL+AN_cumulo+interval_yield+interval_Pdt.+RS+Feed_Vol+Cell_conc._interval+AS_Vol.; 0.443, 0.725, tmp_cumulo+pH+pH_cumulo+AN_cumulo+interval_yield+RS+Cell_conc._interval+rab_integral+AS_Vol.+emission_O2+generate_CO2; 0.476, 0.725, tmp_cumulo+pH+interval_yield+RS+Feed_Vol+Cell_conc._interval+emission_CO2; 0.460, 0.725, tmp_cumulo+pH+pH_cumulo+AN+interval_yield+RS+Feed_Vol+Cell_conc._interval+rab_integral; 0.443, 0.725, tmp_cumulo+pH+pH_cumulo+AN+AN_cumulo+interval_yield+OD+RS+Cell_conc._interval+rab_integral+AS_Vol.; 0.443, 0.725, tmp_cumulo+pH+pH_cumulo+PL+AN+interval_yield+RS+Cell_conc._interval+AS_Vol.+interval_O2+generate_CO2; 0.460, 0.725, tmp_cumulo+pH+pH_cumulo+interval_yield+RS+Feed_Vol+Cell_conc._interval+AS_Vol.+interval_O2; 0.468, 0.725, tmp_cumulo+pH+pH_cumulo+interval_yield+RS+Cell_conc._interval+AS_Vol.+generate_CO2; 0.452, 0.725, tmp_cumulo+pH+pH_cumulo+AN_cumulo+interval_yield+RS+Feed_Vol+Cell_conc._interval+rab_integral+emission_CO2; 0.443, 0.725, tmp_cumulo+pH+pH_cumulo+AN_cumulo+interval_yield+OD+RS+Cell_conc._interval+rab_integral+AS_Vol.+generate_CO2; 0.443, 0.725, tmp_cumulo+pH+pH_cumulo+AN+AN_cumulo+interval_yield+RS+Cell_conc._interval+RQ_integral+AS_Vol.+generate_CO2; 0.460, 0.725, tmp+pH+AN+AN_cumulo+interval_yield+RS+Feed_Vol+Cell_conc._interval+AS_Vol.; 0.443, 0.725, tmp_cumulo+pH+pH_cumulo+PL_cumulo+AN_cumulo+interval_yield+OD+RS+Cell_conc._interval+rab_integral+AS_Vol.; 0.434, 0.725, tmp_cumulo+pH+pH_cumulo+AN_cumulo+interval_yield+RS+Feed_Vol+Cell_conc._interval+rab_integral+RQ_integral+AS_Vol.+emission_O2; 0.425, 0.725, tmp_cumulo+pH+pH_cumulo+AN+AN_cumulo+interval_yield+RS+Feed_Vol+Cell_conc._interval+rab_integral+RQ_integral+AS_Vol.+generate_CO2; 0.460, 0.725, tmp_cumulo+pH+pH_cumulo+interval_yield+interval_Pdt.+RS+Feed_Vol+Cell_conc._interval+emission_CO2; 0.451, 0.725, tmp_cumulo+pH+pH_cumulo+AN+interval_yield+RS+RS_cumulo+Cell_conc._interval+rab_integral+AS_Vol.; 0.434, 0.725, tmp_cumulo+pH+pH_cumulo+AN+AN_cumulo+interval_yield+RS+Feed_Vol+Cell_conc._interval+rab_integral+RQ_integral+AS_Vol.+emission_CO2; 0.443, 0.725, tmp+tmp_cumulo+pH+pH_cumulo+PL_cumulo+AN+AN_cumulo+interval_yield+RS+Cell_conc._interval+AS_Vol.; 0.424, 0.725, tmp_cumulo+pH+pH_cumulo+AN_cumulo+interval_yield+RS+Feed_Vol+Cell_conc._interval+rab_integral+AS_Vol.+emission_O2+emission_CO2+generate_CO2; 0.434, 0.725, tmp+tmp_cumulo+pH+ pH_cumulo+PL_cumulo+AN_cumulo+interval_yield+RS+Feed_Vol+Cell_conc._interval+AS_Vol.+emission_CO2; 0.451, 0.725, tmp_cumulo+pH+AN_cumulo+interval_yield+RS+Feed_Vol+Cell_conc._interval+AS_Vol.+emission_CO2+generate_CO2; 0.443, 0.725, tmp_cumulo+pH+pH_cumulo+AN_cumulo+interval_yield+RS+Feed_Vol+Cell_conc._interval+rab_integral+emission_CO2+generate_CO2; 0.434, 0.725, tmp_cumulo+pH+pH_cumulo+AN_cumulo+interval_yield+RS+Cell_conc._interval+RQ_integral+AS_Vol.+emission_O2+emission_CO2+generate_CO2; 0.434, 0.725, tmp_cumulo+pH+pH_cumulo+AN+AN_cumulo+interval_yield+RS+Cell_conc._interval+RQ_integral+AS_Vol.+emission_O2+emission_CO2; 0.443, 0.725, tmp_cumulo+pH+pH_cumulo+PL+AN_cumulo+interval_yield+RS+RS_cumulo+Cell_conc._interval+rab_integral+AS_Vol.; 0.443, 0.725, tmp_cumulo+pH+pH_cumulo+PL_cumulo+AN+AN_cumulo+interval_yield+RS+Cell_conc._interval+AS_Vol.+emission_CO2; 0.460, 0.725, tmp_cumulo+pH+pH_cumulo+interval_yield+RS+Feed_Vol+Cell_conc._interval+RQ_integral+consum_O2; 0.451, 0.725, tmp_cumulo+pH+pH_cumulo+interval_yield+RS+Feed_Vol+Cell_conc._interval+rab_integral+emission_CO2+generate_CO2; 0.451, 0.725, tmp_cumulo+pH+pH_cumulo+AN_cumulo+interval_yield+OD+RS+RS_cumulo+Cell_conc._interval+AS_Vol.; 0.434, 0.725, tmp_cumulo+pH+pH_cumulo+PL+AN_cumulo+interval_yield+RS+Feed_Vol+Cell_conc._interval+AS_Vol.+emission_CO2+interval_O2; 0.460, 0.725, tmp_cumulo+pH+pH_cumulo+interval_yield+RS+Feed_Vol+Cell_conc._interval+rab_integral+emission_O2; 0.433, 0.725, tmp_cumulo+pH+pH_cumulo+PL_cumulo+AN_cumulo+interval_yield+interval_Pdt.+RS+Feed_Vol+Cell_conc._interval+AS_Vol.+emission_CO2; 0.433, 0.725, tmp_cumulo+pH+pH_cumulo+PL_cumulo+AN_cumulo+interval_yield+interval_Pdt.+RS+Feed_Vol+Cell_conc._interval+RQ_integral+AS_Vol.; 0.433, 0.725, tmp_cumulo+pH+pH_cumulo+AN+AN_cumulo+interval_yield+RS+Feed_Vol+Cell_conc._interval+AS_Vol.+emission_O2+emission_CO2; 0.451, 0.725, tmp_cumulo+pH+pH_cumulo+AN_cumulo+interval_yield+RS+Cell_conc._interval+AS_Vol.+emission_O2+generate_CO2; 0.442, 0.725, tmp_cumulo+pH+pH_cumulo+PL+AN+interval_yield+RS+Cell_conc._interval+rab_integral+AS_Vol.+emission_CO2; 0.460, 0.725, tmp_cumulo+pH+pH_cumulo+interval_yield+RS+Feed_Vol+Cell_conc._interval+emission_CO2+interval_O2; 0.442, 0.725, tmp_cumulo+pH+pH_cumulo+AN_cumulo+interval_yield+interval_Pdt.+RS+Cell_conc._interval+rab_integral+AS_Vol.+consum_O2; 0.451, 0.725, tmp_cumulo+pH+pH_cumulo+PL+AN_cumulo+interval_yield+RS+RS_cumulo+Cell_conc._interval+AS_Vol.; 0.451, 0.725, tmp_cumulo+pH+pH_cumulo+AN_cumulo+interval_yield+RS+RS_cumulo+Cell_conc._interval+RQ_integral+AS_Vol.; 0.442, 0.725, tmp_cumulo+pH+pH_cumulo+PL_cumulo+AN+AN_cumulo+interval_yield+RS+Cell_conc._interval+RQ_integral+AS_Vol.; 0.451, 0.725, tmp_cumulo+pH+pH_cumulo+AN+interval_yield+OD+RS+Cell_conc._interval+rab_integral+AS_Vol.; 0.433, 0.725, tmp_cumulo+pH+pH_cumulo+AN_cumulo+interval_yield+RS+Feed_Vol+Cell_conc._interval+rab_integral+RQ_integral+AS_Vol.+consum_O2; 0.433, 0.725, tmp+tmp_cumulo+pH+pH_cumulo+AN_cumulo+interval_yield+RS+Feed_Vol+RS_cumulo+Cell_conc._interval+AS_Vol.+generate_CO2; 0.442, 0.725, tmp+tmp_cumulo+pH+pH_cumulo+AN+AN_cumulo+interval_yield+interval_Pdt.+RS+Cell_conc._interval+AS_Vol.; 0.424, 0.725, tmp_cumulo+pH+pH_cumulo+PL+AN+AN_cumulo+interval_yield+RS+Cell_conc._interval+rab_integral+AS_Vol.+emission_CO2+generate_CO2; 0.442, 0.725, tmp+tmp_cumulo+pH+pH_cumulo+AN+AN_cumulo+interval_yield+RS+Cell_conc._interval+AS_Vol.+consum_O2; 0.424, 0.725, tmp+tmp_cumulo+pH+pH_cumulo+AN_cumulo+interval_yield+RS+Feed_Vol+Cell_conc._interval+rab_integral+AS_Vol.+emission_CO2+generate_CO2; 0.433, 0.725, tmp+tmp_cumulo+pH+pH_cumulo+PL_cumulo+AN_cumulo+interval_yield+interval_Pdt.+RS+Feed_Vol+Cell_conc._interval+AS_Vol.; 0.442, 0.725, tmp_cumulo+pH+pH_cumulo+PL+AN+interval_yield+RS+Cell_conc._interval+RQ_integral+AS_Vol.+emission_CO2; 0.451, 0.725, tmp_cumulo+pH+pH_cumulo+interval_yield+RS+Feed_Vol+Cell_conc._interval+rab_integral+RQ_integral+AS_Vol.; 0.433, 0.725, tmp+tmp_cumulo+pH+pH_cumulo+AN_cumulo+interval_yield+RS+Feed_Vol+Cell_conc._interval+AS_Vol.+consum_O2+generate_CO2; 0.459, 0.725, tmp_cumulo+pH+pH_cumulo+AN+interval_yield+RS+Feed_Vol+Cell_conc._interval+consum_O2; 0.451, 0.725, tmp+tmp_cumulo+pH+pH_cumulo+AN+interval_yield+RS+Cell_conc._interval+RQ_integral+AS_Vol.; 0.442, 0.725, tmp_cumulo+pH+pH_cumulo+AN+interval_yield+RS+Feed_Vol+Cell_conc._interval+RQ_integral+AS_Vol.+emission_O2; 0.451, 0.725, tmp_cumulo+pH+pH_cumulo+PL+AN+interval_yield+RS+Cell_conc._interval+RQ_integral+AS_Vol.; 0.442, 0.725, tmp_cumulo+pH+pH_cumulo+AN_cumulo+interval_yield+interval_Pdt.+RS+RS_cumulo+Cell_conc._interval+rab_integral+AS_Vol.; 0.442, 0.725, tmp+tmp_cumulo+pH+pH_cumulo+AN+interval_yield+interval_Pdt.+RS+Feed_Vol+Cell_conc._interval+AS_Vol.; 0.475, 0.725, tmp+pH+pH_cumulo+interval_yield+RS+Cell_conc._interval+AS_Vol.; 0.433, 0.725, tmp+tmp_cumulo+pH+pH_cumulo+AN_cumulo+interval_yield+RS+Feed_Vol+Cell_conc._interval+AS_Vol.+emission_O2+emission_CO2; 0.451, 0.725, tmp+tmp_cumulo+pH+pH_cumulo+AN+interval_yield+OD+RS+Cell_conc._interval+AS_Vol.; 0.424, 0.725, tmp_cumulo+pH+pH_cumulo+AN_cumulo+interval_yield+RS+Feed_Vol+Cell_conc._interval+RQ_integral+AS_Vol.+emission_O2+emission_CO2+generate_CO2; 0.442, 0.725, tmp+tmp_cumulo+pH+pH_cumulo+AN+AN_cumulo+interval_yield+OD+RS+Cell_conc._interval+AS_Vol.; 0.433, 0.724, tmp_cumulo+pH+pH_cumulo+AN+interval_yield+RS+Feed_Vol+Cell_conc._interval+rab_integral+RQ_integral+AS_Vol.+generate_CO2; 0.459, 0.724, tmp+tmp_cumulo+pH+AN_cumulo+interval_yield+RS+Feed_Vol+Cell_conc._interval+AS_Vol.; 0.433, 0.724, tmp_cumulo+pH+pH_cumulo+PL+AN_cumulo+interval_yield+RS+RS_cumulo+Cell_conc._interval+rab_integral+AS_Vol.+emission_CO2; 0.442, 0.724, tmp_cumulo+pH+pH_cumulo+PL+interval_yield+RS+Feed_Vol+Cell_conc._interval+rab_integral+AS_Vol.+interval_O2; 0.475, 0.724, pH+pH_cumulo+AN_cumulo+interval_yield+RS+Cell_conc._interval+AS_Vol.; 0.451, 0.724, tmp_cumulo+pH+pH_cumulo+interval_yield+RS+Feed_Vol+Cell_conc._interval+rab_integral+AS_Vol.+generate_CO2; 0.433, 0.724, tmp_cumulo+pH+pH_cumulo+PL_cumulo+AN+AN_cumulo+interval_yield+RS+Cell_conc._interval+rab_integral+RQ_integral+AS_Vol.; 0.459, 0.724, tmp_cumulo+pH+pH_cumulo+AN+interval_yield+interval_Pdt.+RS+Feed_Vol+Cell_conc._interval; 0.442, 0.724, tmp_cumulo+pH+pH_cumulo+PL+AN+AN_cumulo+interval_yield+interval_Pdt.+RS+Cell_conc._interval+AS_Vol.; 0.450, 0.724, tmp_cumulo+pH+pH_cumulo+AN+AN_cumulo+interval_yield+RS+Feed_Vol+Cell_conc._interval+generate_CO2; 0.442, 0.724, tmp_cumulo+pH+pH_cumulo+PL+AN_cumulo+interval_yield+RS+Cell_conc._interval+AS_Vol.+emission_CO2+consum_O2;

0.423, 0.724, tmp_cumulo+pH+pH_cumulo+PL+AN+AN_cumulo+interval_yield+RS+Cell_conc._interval+rab_integral+AS_Vol.+emission_CO2+interval_O2; 0.450, 0.724, tmp_cumulo+pH+pH_cumulo+AN_cumulo+interval_yield+interval_Pdt.+RS+Feed_Vol+Cell_conc._interval+generate_CO2; 0.442, 0.724, tmp_cumulo+pH+pH_cumulo+PL+AN+AN_cumulo+interval_yield+RS+Cell_conc._interval+AS_Vol.+generate_CO2; 0.442, 0.724, tmp_cumulo+pH+pH_cumulo+AN_cumulo+interval_yield+RS+RS_cumulo+Cell_conc._interval+rab_integral+RQ_integral+AS_Vol.; 0.450, 0.724, tmp+tmp_cumulo+pH+pH_cumulo+AN_cumulo+interval_yield+RS+Cell_conc._interval+Accum._Yield+AS_Vol.; 0.433, 0.724, tmp_cumulo+pH+pH_cumulo+AN+AN_cumulo+interval_yield+RS+Feed_Vol+Cell_conc._interval+RQ_integral+AS_Vol.+emission_O2; 0.450, 0.724, tmp_cumulo+pH+pH_cumulo+AN_cumulo+interval_yield+OD+RS+Cell_conc._interval+RQ_integral+AS_Vol; 0.459, 0.724, tmp+tmp_cumulo+pH+pH_cumulo+interval_yield+RS+Feed_Vol+Cell_conc._interval+rab_integral; 0.442, 0.724, tmp_cumulo+pH+pH_cumulo+AN+AN_cumulo+interval_yield+interval_Pdt.+RS+Cell_conc._interval+AS_Vol.+emission_CO2; 0.433, 0.724, tmp_cumulo+pH+pH_cumulo+PL+AN+AN_cumulo+interval_yield+RS+Cell_conc._interval+AS_Vol.+emission_CO2+interval_O2; 0.433, 0.724, tmp_cumulo+pH+pH_cumulo+AN+interval_yield+RS+Feed_Vol+Cell_conc._interval+rab_integral+AS_Vol.+emission_CO2+generate_CO2; 0.459, 0.724, tmp+tmp_cumulo+pH+pH_cumulo+interval_yield+RS+Feed_Vol+Cell_conc._interval+consum_O2; 0.433, 0.724, tmp_cumulo+pH+pH_cumulo+PL+AN+AN_cumulo+interval_yield+RS+Cell_conc._interval+rab_integral+AS_Vol.+generate_CO2; 0.450, 0.724, tmp_cumulo+pH+pH_cumulo+AN+AN_cumulo+interval_yield+RS+Feed_Vol+Cell_conc._interval+rab_integral; 0.459, 0.724, pH+pH_cumulo+PL_cumulo+AN_cumulo+interval_yield+RS+Cell_conc._interval+rab_integral+AS_Vol.; 0.433, 0.724, tmp+tmp_cumulo+pH+pH_cumulo+AN_cumulo+interval_yield+RS+Feed_Vol+Cell_conc._interval+AS_Vol.+emission_O2+generate_CO2; 0.442, 0.724, tmp+tmp_cumulo+pH+pH_cumulo+AN+AN_cumulo+interval_yield+RS+RS_cumulo+Cell_conc._interval+AS_Vol.; 0.433, 0.724, tmp_cumulo+pH+pH_cumulo+PL+cumulo+AN_cumulo+interval_yield+RS+Feed_Vol+Cell_conc._interval+rab_integral+AS_Vol.+consum_O2; 0.441, 0.724, tmp+tmp_cumulo+pH+pH_cumulo+AN_cumulo+interval_yield+OD+RS+Cell_conc._interval+rab_integral+AS_Vol.; 0.450, 0.724, tmp+tmp_cumulo+pH+pH_cumulo+AN+interval_yield+interval_Pdt.+RS+Cell_conc._interval+AS_Vol.; 0.423, 0.724, tmp+tmp_cumulo+pH+pH_cumulo+AN+AN_cumulo+interval_yield+RS+Feed_Vol+Cell_conc._interval+rab_integral+AS_Vol.+generate_CO2; 0.459, 0.724, tmp_cumulo+pH+pH_cumulo+PL_cumulo+interval_yield+RS+Feed_Vol+Cell_conc._interval+interval_O2; 0.483, 0.724, pH+pH_cumulo+interval_yield+RS+Cell_conc._interval+AS_Vol.; 0.441, 0.724, tmp_cumulo+pH+pH_cumulo+AN+interval_yield+interval_Pdt.+RS+Feed_Vol+Cell_conc._interval+RQ_integral+AS_Vol.; 0.432, 0.724, tmp_cumulo+pH+pH_cumulo+PL+AN+interval_yield+RS+Feed_Vol+Cell_conc._interval+AS_Vol.+emission_CO2+interval_O2; 0.441, 0.724, tmp+tmp_cumulo+pH+pH_cumulo+PL_cumulo+AN+interval_yield+RS+Feed_Vol+Cell_conc._interval+AS_Vol.; 0.432, 0.724, tmp_cumulo+pH+pH_cumulo+PL+AN+AN_cumulo+interval_yield+RS+Cell_conc._interval+rab_integral+RQ_integral+AS_Vol.; 0.459, 0.724, tmp_cumulo+pH+pH_cumulo+AN+interval_yield+RS+Feed_Vol+Cell_conc._interval+emission_CO2; 0.441, 0.724, tmp_cumulo+pH+pH_cumulo+AN_cumulo+interval_yield+RS+Feed_Vol+Cell_conc._interval+rab_integral+interval_O2+generate_CO2; 0.441, 0.724, tmp_cumulo+pH+pH_cumulo+PL+AN_cumulo+interval_yield+RS+Feed_Vol+Cell_conc._interval+AS_Vol.+consum_O2; 0.441, 0.724, tmp_cumulo+pH+pH_cumulo+PL+AN_cumulo+interval_yield+RS+Feed_Vol+Cell_conc._interval+AS_Vol.+emission_CO2; 0.423, 0.724, tmp_cumulo+pH+pH_cumulo+AN_cumulo+interval_yield+RS+Feed_Vol+Cell_conc._interval+rab_integral+RQ_integral+AS_Vol.+emission_CO2+generate_CO2; 0.432, 0.724, tmp_cumulo+pH+pH_cumulo+AN+AN_cumulo+interval_yield+RS+Feed_Vol+Cell_conc._interval+rab_integral+AS_Vol.+consum_O2; 0.450, 0.724, tmp_cumulo+pH+pH_cumulo+PL_cumulo+interval_yield+RS+Feed_Vol+Cell_conc._interval+interval_O2+generate_CO2; 0.432, 0.724, tmp_cumulo+pH+pH_cumulo+PL+AN_cumulo+interval_yield+RS+Feed_Vol+Cell_conc._interval+rab_integral+RQ_integral+AS_Vol.; 0.441, 0.724, tmp_cumulo+pH+pH_cumulo+PL+AN+interval_yield+RS+Cell_conc._interval+Accum._Yield+AS_Vol.+interval_O2; 0.450, 0.724, tmp_cumulo+pH+pH_cumulo+AN_cumulo+interval_yield+RS+Cell_conc._interval+Accum._Yield+AS_Vol.+generate_CO2; 0.441, 0.724, tmp_cumulo+pH+pH_cumulo+PL+interval_yield+RS+Cell_conc._interval+rab_integral+AS_Vol.+emission_CO2+interval_O2; 0.441, 0.724, tmp_cumulo+pH+pH_cumulo+PL_cumulo+AN+interval_yield+RS+Feed_Vol+Cell_conc._interval+AS_Vol.+interval_O2; 0.441, 0.724, tmp_cumulo+pH+pH_cumulo+AN+interval_yield+RS+Feed_Vol+Cell_conc._interval+AS_Vol.+emission_O2+emission_CO2; 0.423, 0.724, tmp+tmp_cumulo+pH+pH_cumulo+AN+AN_cumulo+interval_yield+RS+Feed_Vol+Cell_conc._interval+AS_Vol.+emission_CO2+generate_CO2; 0.441, 0.724, tmp_cumulo+pH+pH_cumulo+PL+AN+interval_yield+RS+Cell_conc._interval+AS_Vol.+consum_O2+interval_O2; 0.432, 0.724, tmp+tmp_cumulo+pH+pH_cumulo+PL+AN_cumulo+interval_yield+RS+Cell_conc._interval+RQ_integral+AS_Vol.+emission_CO2; 0.450, 0.724, tmp+tmp_cumulo+pH+pH_cumulo+AN+interval_yield+RS+Cell_conc._interval+AS_Vol.+consum_O2; 0.450, 0.724, tmp_cumulo+pH+pH_cumulo+AN+interval_yield+RS+Feed_Vol+Cell_conc._interval+AS_Vol.+interval_O2; 0.441, 0.724, tmp_cumulo+pH+pH_cumulo+PL_cumulo+AN+interval_yield+interval_Pdt.+RS+Feed_Vol+Cell_conc._interval+AS_Vol.; 0.432, 0.724, tmp_cumulo+pH+pH_cumulo+PL+AN+interval_yield+RS+Feed_Vol+Cell_conc._interval+AS_Vol.+interval_O2+generate_CO2; 0.432, 0.724, tmp_cumulo+pH+pH_cumulo+AN+AN_cumulo+interval_yield+RS+Feed_Vol+Cell_conc._interval+AS_Vol.+emission_CO2+consum_O2; 0.450, 0.724, tmp+tmp_cumulo+pH+pH_cumulo+PL+AN+interval_yield+RS+Cell_conc._interval+AS_Vol.; 0.423, 0.724, tmp_cumulo+pH+pH_cumulo+PL_cumulo+AN_cumulo+interval_yield+RS+Feed_Vol+Cell_conc._interval+AS_Vol.+emission_CO2+interval_O2+generate_CO2; 0.441, 0.724, tmp+tmp_cumulo+pH+pH_cumulo+AN_cumulo+interval_yield+RS+Cell_conc._interval+rab_integral+AS_Vol.+emission_O2; 0.441, 0.724, tmp+tmp_cumulo+pH+pH_cumulo+AN_cumulo+interval_yield+interval_Pdt.+RS+Cell_conc._interval+AS_Vol.+emission_CO2; 0.458, 0.724, tmp_cumulo+pH+pH_cumulo+AN_cumulo+interval_yield+RS+Feed_Vol+Cell_conc._interval+interval_O2; 0.441, 0.724, tmp_cumulo+pH+pH_cumulo+AN_cumulo+interval_yield+interval_Pdt.+OD+RS+Cell_conc._interval+rab_integral+AS_Vol.; 0.441, 0.724, tmp_cumulo+pH+pH_cumulo+AN_cumulo+interval_yield+OD+RS+Cell_conc._ interval+rab_integral+AS_Vol.+emission_CO2; 0.432, 0.724, tmp_cumulo+pH+pH_cumulo+PL_cumulo+AN+AN_cumulo+interval_yield+RS+Cell_conc._interval+rab_integral+AS_Vol.+emission_CO2; 0.458, 0.724, tmp_cumulo+pH+AN_cumulo+interval_yield+RS+Feed_Vol+Cell_conc._interval+RQ_integral+AS_Vol.; 0.432, 0.724, tmp_cumulo+pH+pH_cumulo+AN_cumulo+interval_yield+RS+Feed_Vol+Cell_conc._interval+rab_integral+AS_Vol.+emission_CO2+consum_O2; 0.450, 0.724, tmp+tmp_cumulo+pH+pH_cumulo+AN+interval_yield+RS+Cell_conc._interval+AS_Vol.+emission_O2; 0.441, 0.724, tmp_cumulo+pH+pH_cumulo+AN_cumulo+interval_yield+RS+Cell_conc._interval+rab_integral+RQ_integral+AS_Vol.+emission_CO2; 0.423, 0.724, tmp_cumulo+pH+pH_cumulo+AN+AN_cumulo+interval_yield+RS+Feed_Vol+Cell_conc._interval+RQ_integral+AS_Vol.+emission_O2+emission_CO2; 0.441, 0.724, tmp+tmp_cumulo+pH+pH_cumulo+PL_cumulo+AN_cumulo+interval_yield+RS+Cell_conc._interval+AS_Vol.+generate_CO2; 0.441, 0.724, tmp+tmp_cumulo+pH+pH_cumulo+AN_cumulo+interval_yield+interval_Pdt.+RS+Cell_conc._interval+AS_Vol.+generate_CO2; 0.423, 0.724, tmp_cumulo+pH+pH_cumulo+PL_cumulo+AN+AN_cumulo+interval_yield+RS+Feed_Vol+Cell_conc._interval+rab_integral+RQ_integral+AS_Vol.; 0.432, 0.724, tmp+tmp_cumulo+pH+pH_cumulo+AN+AN_cumulo+interval_yield+RS+Feed_Vol+Cell_conc._interval+AS_Vol.+consum_O2; 0.441, 0.724, tmp_cumulo+pH+pH_cumulo+AN+AN_cumulo+interval_yield+RS+Cell_conc._interval+AS_Vol.+emission_CO2+consum_O2; 0.458, 0.724, tmp+pH+pH_cumulo+AN_cumulo+interval_yield+RS+RS_cumulo+Cell_conc._interval+AS_Vol.; 0.432, 0.724, tmp+tmp_cumulo+pH+pH_cumulo+AN+AN_cumulo+interval_yield+RS+Feed_Vol+RS_cumulo+Cell_conc._interval+AS_Vol.; 0.441, 0.724, tmp+tmp_cumulo+pH+pH_cumulo+PL+interval_yield+RS+Feed_Vol+Cell_conc._interval+AS_Vol.+interval_O2; 0.432, 0.724, tmp_cumulo+pH+pH_cumulo+PL+AN_cumulo+interval_yield+RS+Feed_Vol+Cell_conc._interval+AS_Vol.+consum_O2+interval_O2; 0.466, 0.724, tmp_cumulo+pH+pH_cumulo+interval_yield+RS+Cell_conc._interval+AS_Vol.+consum_O2; 0.458, 0.724, tmp_cumulo+pH+pH_cumulo+interval_yield+interval_Pdt.+RS+Feed_Vol+Cell_conc._interval+consum_O2; 0.432, 0.724, tmp_cumulo+pH+pH_cumulo+AN_cumulo+interval_yield+RS+Feed_Vol+RS_cumulo+Cell_conc._interval+rab_integral+RQ_integral+AS_Vol.; 0.441, 0.724, tmp_cumulo+pH+pH_cumulo+AN+AN_cumulo+interval_yield+RS+Cell_conc._interval+AS_Vol.+emission_O2+emission_CO2; 0.450, 0.724, tmp_cumulo+pH+pH_cumulo+AN_cumulo+interval_yield+RS+Feed_Vol+Cell_conc._interval+consum_O2+generate_CO2; 0.432, 0.724, tmp+tmp_cumulo+pH+pH_cumulo+AN_cumulo+interval_yield+RS+Feed_Vol+Cell_conc._interval+rab_integral+AS_Vol.+consum_O2; 0.458, 0.724, tmp_cumulo+pH+pH_cumulo+interval_yield+RS+Feed_Vol+Cell_conc._interval+RQ_integral+generate_CO2; 0.474, 0.724, tmp_cumulo+pH+interval_yield+RS+Feed_Vol+Cell_conc._interval+RQ_integral; 0.450, 0.724, tmp_cumulo+pH+pH_cumulo+AN_cumulo+interval_yield+RS+Feed_Vol+Cell_conc._interval+RQ_integral+generate_CO2; 0.432, 0.724, tmp_cumulo+pH+pH_cumulo+AN_cumulo+interval_yield+OD+RS+Feed_Vol+Cell_conc._interval+AS_Vol.+emission_CO2+generate_CO2; 0.441, 0.724, tmp_cumulo+pH+pH_cumulo+AN+interval_yield+RS+Cell_conc._interval+rab_integral+AS_Vol.+emission_CO2+generate_CO2; 0.432, 0.724, tmp_cumulo+pH+pH_cumulo+AN+AN_cumulo+interval_yield+RS+Feed_Vol+RS_cumulo+Cell_conc._interval+AS_Vol.+emission_CO2; 0.449, 0.724, tmp_cumulo+pH+pH_cumulo+interval_yield+RS+Feed_Vol+Cell_conc._interval+rab_integral+consum_O2+generate_CO2; 0.458, 0.724, tmp_cumulo+pH+pH_cumulo+interval_yield+RS+Cell_conc._interval+rab_integral+AS_Vol.+emission_CO2; 0.449, 0.724, tmp_cumulo+pH+pH_cumulo+interval_yield+RS+Feed_Vol+Cell_conc._interval+emission_CO2+interval_O2+generate_CO2; 0.432, 0.724, tmp_cumulo+pH+pH_cumulo+AN+AN_cumulo+interval_yield+RS+Cell_conc._interval+rab_integral+RQ_integral+AS_Vol.+generate_CO2; 0.458, 0.724, tmp_cumulo+pH+pH_cumulo+interval_yield+RS+Cell_conc._interval+AS_Vol.+emission_CO2+generate_CO2; 0.441, 0.724, tmp_cumulo+pH+pH_cumulo+PL+AN+interval_yield+interval_Pdt.+RS+Cell_conc._interval+AS_Vol.+interval_O2; 0.441, 0.724, tmp_cumulo+pH+pH_cumulo+PL_cumulo+AN+AN_cumulo+interval_yield+interval_Pdt.+RS+Cell_conc._interval+AS_Vol.; 0.432, 0.724, tmp+tmp_cumulo+pH+pH_cumulo+AN_cumulo+interval_yield+interval_Pdt.+RS+Feed_Vol+Cell_conc._interval+RQ_integral+AS_Vol.; 0.449, 0.724, tmp_cumulo+pH+pH_cumulo+AN+interval_yield+RS+Feed_Vol+Cell_conc._interval+rab_integral+generate_CO2; 0.449, 0.724, tmp_cumulo+pH+pH_cumulo+interval_yield+RS+Feed_Vol+Cell_conc._interval+rab_integral+AS_Vol.+emission_CO2; 0.449, 0.724, tmp+pH+pH_cumulo+PL_cumulo+AN_cumulo+interval_yield+RS+Cell_conc._interval+rab_integral+AS_Vol.; 0.449, 0.724, tmp_cumulo+pH+pH_cumulo+AN+interval_yield+RS+Feed_Vol+Cell_conc._interval+interval_O2+generate_CO2; 0.432, 0.724, tmp+tmp_cumulo+pH+pH_cumulo+PL+AN+AN_cumulo+interval_yield+RS+Cell_conc._interval+rab_integral+AS_Vol.; 0.449, 0.724, tmp_cumulo+pH+pH_cumulo+PL_cumulo+AN+interval_yield+RS+Cell_conc._interval+RQ_integral+AS_Vol.; 0.449, 0.724, tmp+tmp_cumulo+pH+pH_cumulo+AN_cumulo+interval_yield+RS+Feed_Vol+Cell_conc._interval+rab_integral; 0.449, 0.724, tmp_cumulo+pH+pH_cumulo+interval_yield+RS+Feed_Vol+Cell_conc._interval+AS_Vol.+interval_O2+generate_CO2; 0.432, 0.724, tmp_cumulo+pH+pH_cumulo+PL_cumulo+AN_cumulo+interval_yield+RS+Feed_Vol+RS_cumulo+Cell_conc._interval+rab_integral+AS_Vol.; 0.441, 0.724, tmp+tmp_cumulo+pH+pH_cumulo+AN_cumulo+interval_yield+RS+RS_cumulo+Cell_conc._interval+AS_Vol.+generate_CO2; 0.432, 0.724, tmp_cumulo+pH+pH_cumulo+AN_cumulo+interval_yield+RS+Cell_conc._interval+rab_integral+AS_Vol.+emission_CO2+consum_O2+generate_CO2; 0.449, 0.724, tmp+tmp_cumulo+pH+pH_cumulo+AN+interval_yield+RS+RS_cumulo+Cell_conc._interval+AS_Vol.; 0.441, 0.724, tmp_cumulo+pH+pH_cumulo+interval_yield+RS+Feed_Vol+Cell_conc._interval+rab_integral+emission_CO2+interval_O2+generate_CO2; 0.422, 0.724, tmp_cumulo+pH+pH_cumulo+PL_cumulo+AN+interval_yield+RS+Feed_Vol+Cell_conc._interval+AS_Vol.+emission_CO2+interval_O2+generate_CO2; 0.466, 0.724, tmp_cumulo+pH+pH_cumulo+interval_yield+OD+RS+Feed_Vol+Cell_conc._interval; 0.449, 0.724, tmp_cumulo+pH+pH_cumulo+AN+AN_cumulo+interval_yield+RS+Feed_Vol+Cell_conc._interval+emission_CO2; 0.449, 0.724, tmp_cumulo+pH+pH_cumulo+AN+AN_cumulo+interval_yield+interval_Pdt.+RS+Feed_Vol+Cell_conc._interval; 0.466, 0.724, tmp_cumulo+pH+pH_cumulo+interval_yield+OD+RS+Cell_conc._interval+AS_Vol.; 0.431, 0.724, tmp_cumulo+pH+pH_cumulo+AN+AN_cumulo+interval_yield+RS+Feed_Vol+Cell_conc._interval+RQ_integral+AS_Vol.+emission_CO2; 0.449, 0.724, tmp_cumulo+pH+pH_cumulo+PL_cumulo+interval_yield+RS+Feed_Vol+Cell_conc._interval+AS_Vol.+interval_O2; 0.440, 0.724, tmp_cumulo+pH+pH_cumulo+AN+AN_cumulo+interval_yield+OD+RS+Cell_conc._interval+AS_Vol.+emission_CO2; 0.431, 0.724, tmp+tmp_cumulo+pH+pH_cumulo+AN_cumulo+interval_yield+RS+Feed_Vol+RS_cumulo+Cell_conc._interval+AS_Vol.+emission_CO2; 0.431, 0.724, tmp_cumulo+pH+pH_cumulo+AN+AN_cumulo+interval_yield+RS+Feed_Vol+Cell_conc._interval+AS_Vol.+interval_O2+generate_CO2; 0.431, 0.724, tmp_cumulo+pH+pH_cumulo+PL_cumulo+AN_cumulo+interval_yield+RS+Feed_Vol+RS_cumulo+Cell_conc._interval+AS_Vol.+generate_CO2; 0.466, 0.724, pH+pH_cumulo+PL_cumulo+AN+interval_yield+RS+Cell_conc._interval+AS_Vol.; 0.449, 0.724, tmp_cumulo+pH+pH_cumulo+AN_cumulo+interval_yield+OD+RS+Cell_conc._interval+AS_Vol.+consum_O2; 0.431, 0.724, tmp+tmp_cumulo+pH+pH_cumulo+AN_cumulo+interval_yield+RS+Feed_Vol+Cell_conc._interval+RQ_integral+AS_Vol.+emission_O2; 0.431, 0.724, tmp_cumulo+pH+pH_cumulo+PL_cumulo+AN_cumulo+interval_yield+RS+Feed_Vol+Cell_conc._interval+AS_Vol.+consum_O2+generate_CO2; 0.431, 0.724, tmp+tmp_cumulo+pH+pH_cumulo+AN_cumulo+interval_yield+RS+Feed_Vol+Cell_conc._interval+AS_Vol.+emission_CO2+consum_O2; 0.422, 0.724, tmp_cumulo+pH+pH_cumulo+AN_cumulo+interval_yield+interval_Pdt.+RS+Feed_Vol+Cell_conc._interval+rab_integral+AS_Vol.+emission_CO2+generate_CO2; 0.449, 0.724, tmp+tmp_cumulo+pH+pH_cumulo+interval_yield+RS+Feed_Vol+Cell_conc._interval+AS_Vol.+emission_CO2; 0.449, 0.724, tmp_cumulo+pH+pH_cumulo+AN_cumulo+interval_yield+RS+Feed_Vol+Cell_conc._interval+rab_integral+emission_O2; 0.458, 0.724, tmp+pH+pH_cumulo+AN+AN_cumulo+interval_yield+RS+Cell_conc._interval+AS_Vol; 0.449, 0.724, tmp+tmp_cumulo+pH+pH_cumulo+PL_cumulo+AN+interval_yield+RS+Cell_conc._interval+AS_Vol.; 0.431, 0.724, tmp_cumulo+pH+pH_cumulo+AN_cumulo+interval_yield+RS+RS_cumulo+Cell_conc._interval+rab_integral+AS_Vol.+emission_CO2+generate_CO2; 0.440, 0.724, tmp_cumulo+pH+pH_cumulo+AN+AN_cumulo+interval_yield+RS+RS_cumulo+Cell_conc._interval+AS_Vol.+emission_CO2; 0.440, 0.724, tmp_cumulo+pH+pH_cumulo+AN_cumulo+interval_yield+RS+RS_cumulo+Cell_conc._interval+rab_integral+AS_Vol.+consum_O2; 0.440, 0.724, tmp_cumulo+pH+pH_cumulo+PL_cumulo+AN+interval_yield+RS+Feed_Vol+Cell_conc._interval+AS_Vol.+emission_CO2; 0.422, 0.724, tmp_cumulo+pH+pH_cumulo+PL+AN+interval_yield+RS+Cell_conc._interval+rab_integral+AS_Vol.+emission_CO2+interval_O2+generate_CO2; 0.440, 0.723, tmp_cumulo+pH+pH_cumulo+AN+interval_yield+RS+Cell_conc._interval+RQ_integral+AS_Vol.+emission_O2+emission_CO2; 0.440, 0.723, tmp_cumulo+pH+pH_cumulo+AN_cumulo+interval_yield+OD+RS+Feed_Vol+Cell_conc._interval+RQ_integral+AS_Vol.; 0.422, 0.723, tmp_cumulo+pH+pH_cumulo+AN+AN_cumulo+interval_yield+RS+Feed_Vol+Cell_conc._interval+AS_Vol.+emission_O2+emission_CO2+generate_CO2; 0.457, 0.723, tmp_cumulo+pH+pH_cumulo+interval_yield+RS+Cell_conc._interval+rab_integral+AS_Vol.+generate_CO2; 0.431, 0.723, tmp_cumulo+pH+pH_cumulo+AN+AN_cumulo+interval_yield+OD+RS+Feed_Vol+Cell_conc._interval+AS_Vol.+generate_CO2; 0.431, 0.723, tmp_cumulo+pH+pH_cumulo+AN+AN_cumulo+interval_yield+RS+Feed_Vol+RS_cumulo+Cell_conc._interval+rab_integral+AS_Vol.; 0.440, 0.723, tmp_cumulo+pH+pH_cumulo+PL_cumulo+AN+AN_cumulo+interval_yield+OD+RS+Cell_conc._interval+AS_Vol.; 0.440, 0.723, tmp_cumulo+pH+pH_cumulo+AN+interval_yield+RS+Feed_Vol+Cell_conc._interval+rab_integral+interval_O2+generate_CO2; 0.440, 0.723, tmp_cumulo+pH+pH_cumulo+AN+interval_yield+interval_Pdt.+RS+Feed_Vol+Cell_conc._interval+AS_Vol.+emission_O2; 0.422, 0.723, tmp_cumulo+pH+pH_cumulo+AN+AN_cumulo+interval_yield+interval_Pdt.+RS+Feed_Vol+Cell_conc._interval+AS_Vol.+emission_CO2+generate_CO2; 0.431, 0.723, tmp_cumulo+pH+pH_cumulo+AN+AN_cumulo+interval_yield+RS+Cell_conc._interval+rab_integral+AS_Vol.+emission_O2+emission_CO2; 0.431, 0.723, tmp+tmp_cumulo+pH+pH_cumulo+AN_cumulo+interval_yield+RS+Feed_Vol+Cell_conc._interval+RQ_integral+AS_Vol.+emission_CO2; 0.474, 0.723, tmp_cumulo+pH+interval_yield+RS+Feed_Vol+Cell_conc._interval+generate_CO2; 0.431, 0.723, tmp_cumulo+pH+pH_cumulo+AN_cumulo+interval_yield+interval_Pdt.+RS+Cell_conc._interval+rab_integral+AS_Vol.+emission_CO2+generate_CO2; 0.431, 0.723, tmp+tmp_cumulo+pH+pH_cumulo+AN_cumulo+interval_yield+RS+Cell_conc._interval+RQ_integral+AS_Vol.+emission_O2+emission_CO2; 0.440, 0.723, tmp+tmp_cumulo+pH+pH_cumulo+PL+AN_cumulo+interval_yield+RS+Cell_conc._interval+AS_Vol.+interval_O2; 0.431, 0.723, tmp+tmp_cumulo+pH+pH_cumulo+PL_cumulo+AN_cumulo+interval_yield+RS+Cell_conc._interval+rab_integral+AS_Vol.+generate_CO2; 0.449, 0.723, tmp_cumulo+pH+pH_cumulo+interval_yield+RS+Feed_Vol+Cell_conc._interval+rab_integral+RQ_integral+consum_O2; 0.466, 0.723, tmp_cumulo+pH+pH_cumulo+interval_yield+RS+Feed_Vol+RS_cumulo+Cell_conc._interval; 0.449, 0.723, tmp+pH+pH_cumulo+AN+interval_yield+RS+Cell_conc._interval+AS_Vol.+emission_O2+generate_CO2; 0.431, 0.723, tmp+tmp_cumulo+pH+pH_cumulo+AN+interval_yield+RS+Feed_Vol+Cell_conc._interval+rab_integral+AS_Vol.+generate_CO2; 0.457, 0.723, tmp_cumulo+pH+pH_cumulo+interval_yield+OD+RS+Feed_Vol+Cell_conc._interval+AS_Vol.; 0.422, 0.723, tmp_cumulo+pH+pH_cumulo+AN_cumulo+interval_yield+RS+Cell_conc._interval+rab_integral+RQ_integral+AS_Vol.+emission_O2+emission_CO2+generate_CO2; 0.457, 0.723, tmp_cumulo+pH+pH_cumulo+interval_yield+RS+Feed_Vol+Cell_conc._interval+RQ_integral+emission_CO2; 0.431, 0.723, tmp+tmp_cumulo+pH+pH_cumulo+AN_cumulo+interval_yield+RS+Feed_Vol+RS_cumulo+Cell_conc._interval+rab_integral+AS_Vol.; 0.431, 0.723, tmp_cumulo+pH+pH_cumulo+AN_cumulo+interval_yield+interval_Pdt.+RS+Feed_Vol+Cell_conc._interval+rab_integral+AS_Vol.+consum_O2; 0.431, 0.723, tmp_cumulo+pH+pH_cumulo+PL+AN_cumulo+interval_yield+RS+Cell_conc._interval+RQ_integral+AS_Vol.+emission_CO2+generate_CO2; 0.440, 0.723, tmp_cumulo+pH+pH_cumulo+AN_cumulo+interval_yield+RS+Cell_conc._interval+RQ_integral+AS_Vol.+emission_CO2+generate_CO2; 0.440, 0.723, tmp_cumulo+pH+pH_cumulo+AN_cumulo+interval_yield+RS+Feed_Vol+Cell_conc._interval+AS_Vol.+emission_CO2+interval_O2; 0.457, 0.723, tmp_cumulo+pH+pH_cumulo+AN+interval_yield+RS+Feed_Vol+Cell_conc._interval+RQ_integral; 0.440, 0.723, tmp_cumulo+pH+pH_cumulo+AN+interval_yield+RS+Feed_Vol+Cell_conc._interval+rab_integral+AS_Vol.+consum_O2; 0.440, 0.723, tmp_cumulo+pH+pH_cumulo+AN+interval_yield+RS+Cell_conc._interval+rab_integral+RQ_integral+AS_Vol.+generate_CO2; 0.449, 0.723, tmp_cumulo+pH+pH_cumulo+AN+interval_yield+RS+Feed_Vol+Cell_conc._interval+Accum._Yield+AS_Vol.; 0.449, 0.723, tmp_cumulo+pH+pH_cumulo+AN+interval_yield+interval_Pdt.+OD+RS+Cell_conc._interval+AS_Vol.;

0.431, 0.723, tmp_cumulo+pH+pH_cumulo+AN_cumulo+interval_yield+RS+Feed_Vol+RS_cumulo+Cell_conc._interval+rab_integral+AS_Vol.+emission_CO2; 0.440, 0.723, tmp+tmp_cumulo+pH+pH_cumulo+AN_cumulo+interval_yield+RS+Cell_conc._interval+AS_Vol.+consum_O2+generate_CO2; 0.440, 0.723, tmp+tmp_cumulo+pH+pH_cumulo+AN+interval_yield+RS+Feed_Vol+Cell_conc._interval+AS_Vol.+consum_O2; 0.431, 0.723, tmp+tmp_cumulo+pH+pH_cumulo+AN+AN_cumulo+interval_yield+RS+Cell_conc._interval+rab_integral+AS_Vol.+generate_CO2; 0.431, 0.723, tmp_cumulo+pH+pH_cumulo+PL+AN_cumulo+interval_yield+interval_Pdt.+RS+Feed_Vol+Cell_conc._interval+AS_Vol.+interval_O2; 0.422, 0.723, tmp+tmp_cumulo+pH+pH_cumulo+PL_cumulo+AN+AN_cumulo+interval_yield+RS+Feed_Vol+Cell_conc._interval+AS_Vol.+generate_CO2; 0.440, 0.723, tmp_cumulo+pH+pH_cumulo+AN_cumulo+interval_yield+RS+Feed_Vol+Cell_conc._interval+rab_integral+RQ_integral+generate_CO2; 0.431, 0.723, tmp_cumulo+pH+pH_cumulo+AN_cumulo+interval_yield+RS+Feed_Vol+Cell_conc._interval+RQ_integral+AS_Vol.+emission_O2+generate_CO2; 0.440, 0.723, tmp_cumulo+pH+pH_cumulo+AN+interval_yield+RS+Feed_Vol+Cell_conc._interval+AS_Vol.+emission_CO2+consum_O2; 0.421, 0.723, tmp+tmp_cumulo+pH+pH_cumulo+AN_cumulo+interval_yield+RS+Feed_Vol+Cell_conc._interval+rab_integral+RQ_integral+AS_Vol.+generate_CO2; 0.431, 0.723, tmp_cumulo+pH+pH_cumulo+PL+AN_cumulo+interval_yield+RS+Cell_conc._interval+rab_integral+AS_Vol.+interval_O2+generate_CO2; 0.449, 0.723, tmp_cumulo+pH+pH_cumulo+PL+AN+interval_yield+RS+Feed_Vol+Cell_conc._interval+AS_Vol.; 0.421, 0.723, tmp_cumulo+pH+pH_cumulo+PL_cumulo+AN_cumulo+interval_yield+RS+Feed_Vol+Cell_conc._interval+rab_integral+RQ_integral+AS_Vol.+generate_CO2; 0.440, 0.723, tmp+tmp_cumulo+pH+pH_cumulo+AN_cumulo+interval_yield+RS+RS_cumulo+Cell_conc._interval+AS_Vol.+emission_CO2; 0.457, 0.723, tmp+tmp_cumulo+pH+pH_cumulo+interval_yield+RS+Feed_Vol+Cell_conc._interval+emission_CO2; 0.449, 0.723, tmp_cumulo+pH+pH_cumulo+AN_cumulo+interval_yield+RS+Cell_conc._interval+Accum._Yield+AS_Vol.+emission_CO2; 0.465, 0.723, tmp_cumulo+pH+interval_yield+RS+Feed_Vol+Cell_conc._interval+emission_CO2+generate_CO2; 0.440, 0.723, tmp+tmp_cumulo+pH+pH_cumulo+AN_cumulo+interval_yield+OD+RS+Cell_conc._interval+AS_Vol.+generate_CO2; 0.440, 0.723, tmp_cumulo+pH+pH_cumulo+AN+interval_yield+RS+Cell_conc._interval+rab_integral+RQ_integral+AS_Vol.+emission_O2; 0.457, 0.723, tmp_cumulo+pH+AN_cumulo+interval_yield+RS+Feed_Vol+Cell_conc._interval+rab_integral+AS_Vol.; 0.440, 0.723, tmp_cumulo+pH+pH_cumulo+PL+AN+interval_yield+OD+RS+Cell_conc._interval+AS_Vol.+interval_O2; 0.431, 0.723, tmp+tmp_cumulo+pH+pH_cumulo+AN+AN_cumulo+interval_yield+RS+Cell_conc._interval+AS_Vol.+emission_CO2+generate_CO2; 0.448, 0.723, tmp_cumulo+pH+pH_cumulo+AN+interval_yield+RS+Cell_conc._interval+AS_Vol.+emission_O2+emission_CO2; 0.448, 0.723, tmp_cumulo+pH+pH_cumulo+AN+interval_yield+interval_Pdt.+RS+Cell_conc._interval+AS_Vol.+emission_CO2; 0.421, 0.723, tmp+tmp_cumulo+pH+pH_cumulo+AN_cumulo+interval_yield+RS+Feed_Vol+Cell_conc._interval+RQ_integral+AS_Vol.+emission_O2+emission_CO2; 0.440, 0.723, tmp_cumulo+pH+pH_cumulo+PL+AN_cumulo+interval_yield+interval_Pdt.+RS+Cell_conc._interval+AS_Vol.; 0.421, 0.723, tmp_cumulo+pH+pH_cumulo+PL_cumulo+AN_cumulo+interval_yield+interval_Pdt.+RS+Feed_Vol+Cell_conc._interval+AS_Vol.+emission_CO2+generate_CO2; 0.431, 0.723, tmp_cumulo+pH+pH_cumulo+PL_cumulo+AN+interval_yield+RS+Feed_Vol+Cell_conc._interval+AS_Vol.+emission_CO2+generate_CO2; 0.457, 0.723, tmp+pH+pH_cumulo+AN_cumulo+interval_yield+RS+Cell_conc._interval+rab_integral+AS_Vol.; 0.431, 0.723, tmp_cumulo+pH+pH_cumulo+AN_cumulo+interval_yield+RS+Cell_conc._interval+RQ_integral+AS_Vol.+emission_O2+emission_CO2+consum_O2; 0.431, 0.723, tmp_cumulo+pH+pH_cumulo+PL+AN+AN_cumulo+interval_yield+interval_Pdt.+RS+Cell_conc._interval+rab_integral+AS_Vol.; 0.440, 0.723, tmp_cumulo+pH+pH_cumulo+AN+interval_yield+RS+Feed_Vol+Cell_conc._interval+RQ_integral+AS_Vol.+emission_CO2; 0.421, 0.723, tmp_cumulo+pH+pH_cumulo+PL_cumulo+AN+AN_cumulo+interval_yield+RS+Feed_Vol+Cell_conc._interval+RQ_integral+AS_Vol.+generate_CO2; 0.431, 0.723, tmp+tmp_cumulo+pH+pH_cumulo+PL_cumulo+AN+AN_cumulo+interval_yield+RS+Cell_conc._interval+rab_integral+AS_Vol.; 0.457, 0.723, tmp_cumulo+pH+pH_cumulo+interval_yield+interval_Pdt.+RS+Feed_Vol+Cell_conc._interval+generate_CO2; 0.440, 0.723, tmp_cumulo+pH+pH_cumulo+AN_cumulo+interval_yield+RS+Feed_Vol+Cell_conc._interval+rab_integral+consum_O2+generate_CO2; 0.448, 0.723, tmp_cumulo+pH+pH_cumulo+AN_cumulo+interval_yield+RS+Feed_Vol+Cell_conc._interval+emission_CO2+consum_O2; 0.421, 0.723, tmp+tmp_cumulo+pH+pH_cumulo+PL_cumulo+AN_cumulo+interval_yield+RS+Feed_Vol+Cell_conc._interval+AS_Vol.+emission_CO2+generate_CO2; 0.457, 0.723, tmp+tmp_cumulo+pH+pH_cumulo+interval_yield+RS+Feed_Vol+Cell_conc._interval+interval_O2; 0.440, 0.723, tmp_cumulo+pH+pH_cumulo+AN+AN_cumulo+interval_yield+RS+Feed_Vol+Cell_conc._interval+Accum._Yield+AS_Vol.; 0.457, 0.723, tmp+pH+pH_cumulo+AN+interval_yield+RS+Cell_conc._interval+AS_Vol.+generate_CO2; 0.448, 0.723, tmp_cumulo+pH+pH_cumulo+AN+AN_cumulo+interval_yield+RS+Feed_Vol+Cell_conc._interval+consum_O2; 0.440, 0.723, tmp+tmp_cumulo+pH+pH_cumulo+AN_cumulo+interval_yield+RS+Cell_conc._interval+AS_Vol.+emission_CO2+consum_O2; 0.440, 0.723, tmp_cumulo+pH+pH_cumulo+PL+AN+interval_yield+RS+Cell_conc._interval+rab_integral+AS_Vol.+generate_CO2; 0.430, 0.723, tmp_cumulo+pH+pH_cumulo+PL_cumulo+AN_cumulo+interval_yield+RS+Feed_Vol+Cell_conc._interval+RQ_integral+AS_Vol.+emission_CO2; 0.430, 0.723, tmp+tmp_cumulo+pH+pH_cumulo+AN+AN_cumulo+interval_yield+RS+Cell_conc._interval+rab_integral+RQ_integral+AS_Vol.; 0.421, 0.723, tmp_cumulo+pH+pH_cumulo+PL+AN+AN_cumulo+interval_yield+RS+Cell_conc._interval+rab_integral+RQ_integral+AS_Vol.+emission_CO2; 0.439, 0.723, tmp_cumulo+pH+pH_cumulo+AN+interval_yield+OD+RS+Feed_Vol+Cell_conc._interval+AS_Vol.+generate_CO2; 0.421, 0.723, tmp_cumulo+pH+pH_cumulo+PL+AN+AN_cumulo+interval_yield+RS+Cell_conc._interval+AS_Vol.+emission_CO2+interval_O2+generate_CO2; 0.448, 0.723, tmp+tmp_cumulo+pH+pH_cumulo+interval_yield+RS+Feed_Vol+Cell_conc._interval+AS_Vol.+generate_CO2; 0.473, 0.723, tmp_cumulo+pH+interval_yield+RS+Feed_Vol+Cell_conc._interval+emission_O2; 0.448, 0.723, tmp_cumulo+pH+pH_cumulo+PL+AN+interval_yield+interval_Pdt.+RS+Cell_conc._interval+AS_Vol.; 0.430, 0.723, tmp_cumulo+pH+pH_cumulo+PL+AN+interval_yield+RS+Feed_Vol+Cell_conc._interval+AS_Vol.+consum_O2+interval_O2; 0.439, 0.723, tmp+tmp_cumulo+pH+pH_ cumulo+AN+AN_cumulo+interval_yield+RS+Cell_conc._interval+AS_Vol.+emission_O2; 0.439, 0.723, tmp_cumulo+pH+pH_cumulo+AN+AN_cumulo+interval_yield+interval_Pdt.+OD+RS+Cell_conc._interval+AS_Vol.; 0.465, 0.723, tmp_cumulo+pH+AN+interval_yield+RS+Feed_Vol+Cell_conc._interval+AS_Vol.; 0.439, 0.723, tmp+tmp_cumulo+pH+pH_cumulo+PL_cumulo+AN_cumulo+interval_yield+RS+Cell_conc._interval+AS_Vol.+emission_CO2; 0.430, 0.723, tmp_cumulo+pH+pH_cumulo+AN+AN_cumulo+interval_yield+RS+Feed_Vol+Cell_conc._interval+RQ_integral+AS_Vol.+consum_O2; 0.448, 0.723, tmp_cumulo+pH+pH_cumulo+AN+interval_yield+RS+Feed_Vol+Cell_conc._interval+rab_integral+RQ_integral; 0.421, 0.723, tmp_cumulo+pH+pH_cumulo+PL_cumulo+AN+AN_cumulo+interval_yield+RS+Cell_conc._interval+rab_integral+AS_Vol.+emission_CO2+generate_CO2; 0.421, 0.723, tmp+tmp_cumulo+pH+pH_cumulo+AN+AN_cumulo+interval_yield+RS+Feed_Vol+Cell_conc._interval+rab_integral+RQ_integral+AS_Vol.; 0.430, 0.723, tmp+tmp_cumulo+pH+pH_cumulo+PL+AN+interval_yield+RS+Cell_conc._interval+rab_integral+AS_Vol.+interval_O2; 0.430, 0.723, tmp+tmp_cumulo+pH+pH_cumulo+AN+AN_cumulo+interval_yield+RS+Cell_conc._interval+rab_integral+AS_Vol.+emission_O2+emission_CO2; 0.430, 0.723, tmp_cumulo+pH+pH_cumulo+AN+AN_cumulo+interval_yield+RS+Cell_conc._interval+AS_Vol.+emission_CO2+consum_O2+generate_CO2; 0.473, 0.723, tmp_cumulo+pH+interval_yield+RS+Feed_Vol+Cell_conc._interval+rab_integral; 0.448, 0.723, tmp_cumulo+pH+pH_cumulo+interval_yield+interval_Pdt.+RS+Feed_Vol+Cell_conc._interval+AS_Vol.+emission_CO2; 0.439, 0.723, tmp_cumulo+pH+pH_cumulo+AN+AN_cumulo+interval_yield+RS+Feed_Vol+Cell_conc._interval+AS_Vol.+interval_O2; 0.448, 0.723, tmp_cumulo+pH+pH_cumulo+interval_yield+RS+Feed_Vol+Cell_conc._interval+AS_Vol.+emission_CO2+consum_O2; 0.430, 0.723, tmp_cumulo+pH+pH_cumulo+AN+AN_cumulo+interval_yield+interval_Pdt.+RS+Feed_Vol+Cell_conc._interval+AS_Vol.+emission_O2; 0.430, 0.723, tmp_cumulo+pH+pH_cumulo+PL_cumulo+AN+AN_cumulo+interval_yield+RS+Feed_Vol+Cell_conc._interval+AS_Vol.+consum_O2; 0.448, 0.723, tmp_cumulo+pH+pH_cumulo+AN+interval_yield+OD+RS+Cell_conc._interval+AS_Vol.+emission_CO2; 0.430, 0.723, tmp_cumulo+pH+pH_cumulo+PL+AN+interval_yield+RS+Cell_conc._interval+rab_integral+AS_Vol.+interval_O2+generate_CO2; 0.430, 0.723, tmp+tmp_cumulo+pH+pH_cumulo+PL+AN_cumulo+interval_yield+RS+Cell_conc._interval+rab_integral+RQ_integral+AS_Vol.; 0.430, 0.723, tmp_cumulo+pH+pH_cumulo+PL_cumulo+AN+interval_yield+RS+Feed_Vol+Cell_conc._interval+rab_integral+AS_Vol.+generate_CO2; 0.421, 0.723, tmp_cumulo+pH+pH_cumulo+AN_cumulo+interval_yield+interval_Pdt.+RS+Feed_Vol+Cell_conc._interval+RQ_integral+AS_Vol.+emission_O2+emission_CO2; 0.439, 0.723, tmp_cumulo+pH+pH_cumulo+PL+AN_cumulo+interval_yield+RS+RS_cumulo+Cell_conc._interval+AS_Vol.+emission_CO2; 0.439, 0.723, tmp_cumulo+pH+pH_cumulo+AN+AN_cumulo+interval_yield+RS+Cell_conc._interval+RQ_integral+AS_Vol.+consum_O2; 0.430, 0.723, tmp+tmp_cumulo+pH+pH_cumulo+PL_cumulo+AN_cumulo+interval_yield+RS+Cell_conc._interval+rab_integral+AS_Vol.+emission_CO2; 0.439, 0.723, tmp_cumulo+pH+pH_cumulo+AN_cumulo+interval_yield+RS+Feed_Vol+Cell_conc._interval+Accum._Yield+AS_Vol.+generate_CO2; 0.439, 0.723, tmp_cumulo+pH+pH_cumulo+PL_cumulo+interval_yield+RS+Feed_Vol+Cell_conc._interval+AS_Vol.+interval_O2+generate_CO2; 0.430, 0.723, tmp_cumulo+pH+pH_cumulo+AN+AN_cumulo+interval_yield+RS+Cell_conc._interval+AS_Vol.+emission_O2+emission_CO2+generate_CO2; 0.456, 0.723, tmp_cumulo+pH+interval_yield+RS+Feed_Vol+Cell_conc._interval+emission_CO2+interval_O2+generate_CO2; 0.456, 0.723, pH+pH_cumulo+PL_cumulo+AN+AN_cumulo+interval_yield+RS+Cell_conc._interval+AS_Vol.; 0.465, 0.723, tmp_cumulo+pH+pH_cumulo+interval_yield+RS+RS_cumulo+Cell_conc._interval+AS_Vol.; 0.430, 0.723, tmp_cumulo+pH+pH_cumulo+AN_cumulo+interval_yield+RS+Cell_conc._interval+rab_integral+RQ_integral+AS_Vol.+emission_CO2+generate_CO2; 0.430, 0.723, tmp_cumulo+pH+pH_cumulo+PL+AN_cumulo+interval_yield+RS+Cell_conc._interval+rab_integral+Accum._Yield+AS_Vol.+emission_CO2; 0.456, 0.723, tmp_cumulo+pH+pH_cumulo+AN+interval_yield+RS+Feed_Vol+Cell_conc._interval+emission_O2; 0.439, 0.723, tmp_cumulo+pH+pH_cumulo+interval_yield+RS+Feed_Vol+Cell_conc._interval+RQ_integral+AS_Vol.+emission_O2+emission_CO2; 0.430, 0.723, tmp+tmp_cumulo+pH+pH_cumulo+PL+AN+AN_cumulo+interval_yield+RS+Cell_conc._interval+AS_Vol.+emission_CO2; 0.439, 0.723, tmp_cumulo+pH+pH_cumulo+PL_cumulo+AN+interval_yield+RS+Cell_conc._interval+AS_Vol.+emission_CO2+generate_CO2; 0.448, 0.723, tmp_cumulo+pH+pH_cumulo+PL+AN_cumulo+interval_yield+RS+Cell_conc._interval+Accum._Yield+AS_Vol.; 0.448, 0.723, tmp_cumulo+pH+pH_cumulo+AN_cumulo+interval_yield+interval_Pdt.+RS+Feed_Vol+Cell_conc._interval+RQ_integral; 0.430, 0.723, tmp_cumulo+pH+pH_cumulo+AN_cumulo+interval_yield+interval_Pdt.+RS+Feed_Vol+Cell_conc._interval+RQ_integral+AS_Vol.+generate_CO2; 0.439, 0.723, tmp+tmp_cumulo+pH+pH_cumulo+PL+AN_cumulo+interval_yield+RS+Cell_conc._interval+RQ_integral+AS_Vol; 0.456, 0.723, tmp+pH+pH_cumulo+AN_cumulo+interval_yield+RS+Cell_conc._interval+AS_Vol.+emission_CO2; 0.456, 0.723, tmp_cumulo+pH+AN_cumulo+interval_yield+RS+Feed_Vol+Cell_conc._interval+AS_Vol.+consum_O2; 0.439, 0.723, tmp_cumulo+pH+pH_cumulo+PL+AN+AN_cumulo+interval_yield+RS+Cell_conc._interval+AS_Vol.+consum_O2; 0.430, 0.723, tmp_cumulo+pH+pH_cumulo+AN+interval_yield+RS+Feed_Vol+Cell_conc._interval+AS_Vol.+emission_O2+emission_CO2+generate_CO2; 0.421, 0.723, tmp+tmp_cumulo+pH+pH_cumulo+PL_cumulo+AN_cumulo+interval_yield+RS+Feed_Vol+Cell_conc._interval+rab_integral+AS_Vol.+generate_CO2; 0.430, 0.723, tmp_cumulo+pH+pH_cumulo+AN_cumulo+interval_yield+interval_Pdt.+RS+Feed_Vol+Cell_conc._interval+rab_integral+AS_Vol.+emission_O2; 0.448, 0.723, tmp_cumulo+pH+pH_cumulo+interval_yield+RS+Feed_Vol+Cell_conc._interval+rab_integral+emission_CO2+consum_O2; 0.430, 0.723, tmp_cumulo+pH+pH_cumulo+PL_cumulo+AN_cumulo+interval_yield+interval_Pdt.+RS+Cell_conc._interval+rab_integral+AS_Vol.+emission_CO2; 0.448, 0.723, tmp+tmp_cumulo+pH+pH_cumulo+interval_yield+RS+Feed_Vol+Cell_conc._interval+AS_Vol.+consum_O2; 0.430, 0.723, tmp_cumulo+pH+pH_cumulo+PL+AN+interval_yield+RS+Feed_Vol+Cell_conc._interval+Accum._Yield+AS_Vol.+interval_O2; 0.430, 0.723, tmp_cumulo+pH+pH_cumulo+PL_cumulo+AN+AN_cumulo+interval_yield+interval_Pdt.+RS+Cell_conc._interval+rab_integral+AS_Vol.; 0.439, 0.723, tmp+tmp_cumulo+pH+pH_cumulo+AN_cumulo+interval_yield+RS+Feed_Vol+Cell_conc._interval+AS_Vol.+interval_O2; 0.430, 0.723, tmp_cumulo+pH+pH_cumulo+AN_cumulo+interval_ yield+interval_Pdt.+RS+Feed_Vol+RS_cumulo+Cell_conc._interval+rab_integral+AS_Vol.; 0.420, 0.723, tmp+tmp_cumulo+pH+pH_cumulo+PL+AN_cumulo+interval_yield+RS+Cell_conc._interval+rab_integral+AS_Vol.+emission_CO2+generate_CO2; 0.420, 0.723, tmp+tmp_cumulo+pH+pH_cumulo+PL+AN_cumulo+interval_yield+RS+Cell_conc._interval+rab_integral+AS_Vol.+emission_CO2+interval_O2; 0.448, 0.723, tmp_cumulo+pH+pH_cumulo+interval_yield+RS+Feed_Vol+Cell_conc._interval+AS_Vol.+consum_O2+generate_CO2; 0.439, 0.723, tmp_cumulo+pH+pH_cumulo+PL+interval_yield+RS+Feed_Vol+Cell_conc._interval+AS_Vol.+emission_CO2+interval_O2; 0.430, 0.723, tmp+tmp_cumulo+pH+pH_cumulo+PL+AN_cumulo+interval_yield+RS+Cell_conc._interval+AS_Vol.+emission_CO2+generate_CO2; 0.464, 0.723, tmp_cumulo+pH+interval_yield+RS+Feed_Vol+Cell_conc._interval+AS_Vol.+emission_CO2; 0.439, 0.723, tmp+tmp_cumulo+pH+pH_cumulo+AN+interval_yield+RS+Feed_Vol+RS_cumulo+Cell_conc._interval+AS_Vol.; 0.430, 0.723, tmp_cumulo+pH+pH_cumulo+AN_cumulo+interval_yield+RS+Feed_Vol+Cell_conc._interval+AS_Vol.+emission_CO2+interval_O2+generate_CO2; 0.448, 0.723, tmp+tmp_cumulo+pH+pH_cumulo+AN_cumulo+interval_yield+RS+Feed_Vol+Cell_conc._interval+generate_CO2; 0.420, 0.723, tmp+tmp_cumulo+pH+pH_cumulo+AN+AN_cumulo+interval_yield+RS+Feed_Vol+Cell_conc._interval+RQ_integral+AS_Vol.+generate_CO2; 0.439, 0.723, tmp_cumulo+pH+pH_cumulo+PL_cumulo+interval_yield+RS+Feed_Vol+Cell_conc._interval+rab_integral+interval_O2+generate_CO2; 0.448, 0.723, tmp_cumulo+pH+pH_cumulo+PL_cumulo+AN+interval_yield+OD+RS+Cell_conc._interval+AS_Vol.; 0.420, 0.723, tmp_cumulo+pH+pH_cumulo+PL_cumulo+AN+interval_yield+RS+Feed_Vol+Cell_conc._interval+rab_integral+AS_Vol.+interval_O2+generate_CO2; 0.430, 0.723, tmp+tmp_cumulo+pH+pH_cumulo+PL+AN_cumulo+interval_yield+RS+Cell_conc._interval+rab_integral+AS_Vol.+generate_CO2; 0.472, 0.723, tmp+tmp_cumulo+pH+interval_yield+RS+Feed_Vol+Cell_conc._interval; 0.420, 0.723, tmp_cumulo+pH+pH_cumulo+AN+AN_cumulo+interval_yield+RS+Cell_conc._interval+rab_integral+RQ_integral+AS_Vol.+emission_O2+emission_CO2; 0.430, 0.723, tmp_cumulo+pH+pH_cumulo+AN+interval_yield+RS+Feed_Vol+Cell_conc._interval+RQ_integral+AS_Vol.+emission_O2+emission_CO2; 0.439, 0.723, tmp+tmp_cumulo+pH+pH_cumulo+AN_cumulo+interval_yield+OD+RS+Cell_conc._interval+AS_Vol.+emission_CO2; 0.448, 0.723, tmp_cumulo+pH+pH_cumulo+AN+interval_yield+RS+Cell_conc._interval+AS_Vol.+emission_CO2+consum_O2; 0.464, 0.723, tmp_cumulo+pH+AN_cumulo+interval_yield+RS+Feed_Vol+Cell_conc._interval+emission_CO2; 0.420, 0.723, tmp+tmp_cumulo+pH+pH_cumulo+PL+AN+AN_cumulo+interval_yield+RS+Cell_conc._interval+rab_integral+AS_Vol.+emission_CO2; 0.430, 0.723, tmp_cumulo+pH+pH_cumulo+PL_cumulo+AN_cumulo+interval_yield+RS+Feed_Vol+Cell_conc._interval+rab_integral+AS_Vol.+interval_O2; 0.456, 0.723, tmp+tmp_cumulo+pH+pH_cumulo+AN+interval_yield+RS+Feed_Vol+Cell_conc._interval; 0.447, 0.723, tmp_cumulo+pH+pH_cumulo+AN_cumulo+interval_yield+RS+Cell_conc._interval+RQ_integral+AS_Vol.+emission_O2; 0.439, 0.723, tmp_cumulo+pH+pH_cumulo+PL+AN_cumulo+interval_yield+interval_Pdt.+RS+Cell_conc._interval+AS_Vol.+interval_O2; 0.456, 0.723, tmp_cumulo+pH+AN_cumulo+interval_yield+OD+RS+Feed_Vol+Cell_conc._interval+AS_Vol.; 0.420, 0.723, tmp_cumulo+pH+pH_cumulo+PL_cumulo+AN+interval_yield+RS+Feed_Vol+Cell_conc._interval+AS_Vol.+consum_O2+interval_O2+generate_CO2; 0.447, 0.723, tmp_cumulo+pH+pH_cumulo+AN+AN_cumulo+interval_yield+RS+Feed_Vol+Cell_conc._interval+RQ_integral; 0.439, 0.723, tmp_cumulo+pH+pH_cumulo+AN+AN_cumulo+interval_yield+RS+Cell_conc._interval+AS_Vol.+emission_O2+generate_CO2; 0.430, 0.723, tmp+tmp_cumulo+pH+pH_cumulo+AN_cumulo+interval_yield+RS+Feed_Vol+Cell_conc._interval+RQ_integral+AS_Vol.+consum_O2; 0.430, 0.723, tmp_cumulo+pH+pH_cumulo+PL_cumulo+AN+AN_cumulo+interval_yield+RS+Feed_Vol+Cell_conc._interval+AS_Vol.+interval_O2; 0.439, 0.723, tmp_cumulo+pH+pH_cumulo+AN+interval_yield+RS+Feed_Vol+RS_cumulo+Cell_conc._interval+AS_Vol.+emission_CO2; 0.430, 0.723, tmp_cumulo+pH+pH_cumulo+AN+AN_cumulo+interval_yield+interval_Pdt.+RS+Feed_Vol+Cell_conc._interval+AS_Vol.+consum_O2; 0.439, 0.723, tmp+tmp_cumulo+pH+pH_cumulo+AN_cumulo+interval_yield+RS+Cell_conc._interval+AS_Vol.+emission_O2+emission_CO2; 0.420, 0.723, tmp_cumulo+pH+pH_cumulo+PL_cumulo+AN_cumulo+interval_yield+RS+Feed_Vol+Cell_conc._interval+rab_integral+AS_Vol.+interval_O2+generate_CO2; 0.447, 0.723, tmp+tmp_cumulo+pH+pH_cumulo+AN_cumulo+interval_yield+RS+Feed_Vol+Cell_conc._interval+emission_CO2; 0.447, 0.723, tmp_cumulo+pH+pH_cumulo+interval_yield+RS+Feed_Vol+Cell_conc._interval+rab_integral+RQ_integral+generate_CO2; 0.447, 0.723, tmp+tmp_cumulo+pH+pH_cumulo+interval_yield+RS+Feed_Vol+Cell_conc._interval+rab_integral+AS_Vol.; 0.430, 0.723, tmp_cumulo+pH+pH_cumulo+PL+AN+interval_yield+interval_Pdt.+RS+Feed_Vol+Cell_conc._interval+AS_Vol.+interval_O2; 0.429, 0.722, tmp+tmp_cumulo+pH+pH_cumulo+AN+AN_cumulo+interval_yield+RS+Cell_conc._interval+rab_integral+AS_Vol.+emission_CO2; 0.447, 0.722, tmp_cumulo+pH+pH_cumulo+AN_cumulo+interval_yield+RS+Cell_conc._interval+AS_Vol.+emission_O2+consum_O2; 0.429, 0.722, tmp_cumulo+pH+pH_cumulo+PL+AN_cumulo+interval_yield+RS+Feed_Vol+Cell_conc._interval+AS_Vol.+interval_O2+generate_CO2; 0.420, 0.722, tmp_cumulo+pH+pH_cumulo+PL_cumulo+AN_cumulo+interval_yield+RS+Feed_Vol+Cell_conc._interval+RQ_integral+AS_Vol.+emission_CO2+generate_CO2; 0.420, 0.722, tmp+tmp_cumulo+pH+pH_cumulo+PL+AN_cumulo+interval_yield+RS+Feed_Vol+Cell_conc._interval+rab_integral+AS_Vol.+interval_O2; 0.429, 0.722, tmp_cumulo+pH+pH_cumulo+PL_cumulo+AN_cumulo+interval_yield+RS+Feed_Vol+Cell_conc._interval+RQ_integral+AS_Vol.+consum_O2; 0.438, 0.722, tmp_cumulo+pH+pH_cumulo+AN+AN_cumulo+interval_yield+RS+Feed_Vol+Cell_conc._interval+rab_integral+generate_CO2; 0.429, 0.722, tmp_cumulo+pH+pH_cumulo+PL+AN_cumulo+interval_yield+interval_Pdt.+RS+Cell_conc._interval+RQ_integral+AS_Vol.+emission_CO2; 0.447, 0.722, tmp_cumulo+pH+pH_cumulo+PL+AN_cumulo+interval_yield+interval_Pdt.+RS+Cell_conc._interval+AS_Vol.; 0.429, 0.722, tmp+tmp_cumulo+pH+pH_cumulo+PL+AN_cumulo+interval_yield+RS+Cell_conc._interval+rab_integral+AS_Vol.+interval_O2; 0.447, 0.722, tmp_cumulo+pH+pH_cumulo+PL_cumulo+AN+interval_yield+RS+Cell_conc._interval+AS_Vol.+emission_CO2; 0.438, 0.722, tmp_cumulo+pH+pH_cumulo+AN_cumulo+interval_yield+OD+RS+Feed_Vol+RS_cumulo+Cell_conc._interval+AS_Vol.; 0.447, 0.722, tmp_cumulo+pH+pH_cumulo+AN+interval_yield+OD+RS+Cell_conc._interval+RQ_integral+AS_Vol.; 0.429, 0.722, tmp_cumulo+pH+pH_cumulo+AN_cumulo+interval_yield+interval_Pdt.+RS+

Feed_Vol+Cell_conc._interval+AS_Vol.+emission_O2+ emission_CO2; 0.429, 0.722, tmp_cumulo+pH+pH_cumulo+PL+AN_cumulo+interval_yield+RS+Cell_conc._interval+rab_integral+AS_Vol.+consum_O2+interval_O2; 0.456, 0.722, tmp+tmp_cumulo+pH+pH_cumulo+interval_yield+RS+Feed_Vol+Cell_conc._interval+generate_CO2; 0.447, 0.722, tmp+tmp_cumulo+pH+pH_cumulo+AN_cumulo+interval_yield+interval_Pdt.+RS+Feed_Vol+Cell_conc._interval; 0.438, 0.722, tmp+tmp_cumulo+pH+pH_cumulo+PL_cumulo+AN_cumulo+interval_yield+interval_Pdt.+RS+Cell_conc._interval+AS_Vol.; 0.429, 0.722, tmp_cumulo+pH+pH_cumulo+AN_cumulo+interval_yield+RS+Feed_Vol+Cell_conc._interval+RQ_integral+AS_Vol.+consum_O2+generate_CO2; 0.420, 0.722, tmp_cumulo+pH+pH_cumulo+PL+AN+AN_cumulo+interval_yield+RS+Feed_Vol+Cell_conc._interval+rab_integral+AS_Vol.+interval_O2; 0.438, 0.722, tmp_cumulo+pH+pH_cumulo+PL+AN+AN_cumulo+interval_yield+RS+Cell_conc._interval+AS_Vol.+consum_O2; 0.429, 0.722, tmp_cumulo+pH+pH_cumulo+AN+AN_cumulo+interval_yield+RS+Feed_Vol+RS_cumulo+Cell_conc._interval+RQ_integral+AS_Vol.; 0.429, 0.722, tmp_cumulo+pH+pH_cumulo+PL_cumulo+AN+AN_cumulo+interval_yield+RS+Feed_Vol+RS_cumulo+Cell_conc._interval+AS_Vol.; 0.472, 0.722, pH+pH_cumulo+AN+interval_yield+RS+Cell_conc._interval+AS_Vol.; 0.447, 0.722, tmp_cumulo+pH+pH_cumulo+AN_cumulo+interval_yield+RS+Feed_Vol+Cell_conc._interval+RQ_integral+consum_O2; 0.420, 0.722, tmp_cumulo+pH+pH_cumulo+PL+AN+interval_yield+RS+Feed_Vol+Cell_conc._interval+AS_Vol.+emission_CO2+interval_O2+generate_CO2; 0.429, 0.722, tmp_cumulo+pH+pH_cumulo+AN_cumulo+interval_yield+interval_Pdt.+RS+Feed_Vol+Cell_conc._interval+AS_Vol.+consum_O2+generate_CO2; 0.429, 0.722, tmp+tmp_cumulo+pH+pH_cumulo+AN+interval_yield+RS+Feed_Vol+Cell_conc._interval+AS_Vol.+emission_CO2+generate_CO2; 0.438, 0.722, tmp_cumulo+pH+pH_cumulo+AN+AN_cumulo+interval_yield+interval_Pdt.+RS+Cell_conc._interval+RQ_integral+AS_Vol.; 0.447, 0.722, tmp_cumulo+pH+pH_cumulo+interval_yield+RS+Feed_Vol+Cell_conc._interval+rab_integral+AS_Vol.+consum_O2; 0.429, 0.722, tmp_cumulo+pH+pH_cumulo+PL+AN_cumulo+interval_yield+RS+Feed_Vol+Cell_conc._interval+rab_integral+AS_Vol.+emission_CO2; 0.429, 0.722, tmp_cumulo+pH+pH_cumulo+AN_cumulo+interval_yield+OD+RS+Feed_Vol+Cell_conc._interval+rab_integral+AS_Vol.+generate_CO2; 0.438, 0.722, tmp_cumulo+pH+pH_cumulo+AN+interval_yield+RS+Feed_Vol+Cell_conc._interval+AS_Vol.+emission_O2+consum_O2; 0.429, 0.722, tmp_cumulo+pH+pH_cumulo+PL+AN_cumulo+interval_yield+interval_Pdt.+RS+Cell_conc._interval+rab_integral+RQ_integral+AS_Vol.; 0.456, 0.722, tmp_cumulo+pH+pH_cumulo+interval_yield+interval_Pdt.+RS+Feed_Vol+Cell_conc._interval+RQ_integral; 0.447, 0.722, tmp_cumulo+pH+pH_cumulo+AN+interval_yield+RS+RS_cumulo+Cell_conc._interval+AS_Vol.+emission_CO2; 0.438, 0.722, tmp_cumulo+pH+pH_cumulo+PL+AN_cumulo+interval_yield+RS+Cell_conc._interval+AS_Vol.+consum_O2+interval_O2; 0.438, 0.722, tmp+tmp_cumulo+pH+pH_cumulo+AN+interval_yield+RS+Cell_conc._interval+rab_integral+AS_Vol.+generate_CO2; 0.455, 0.722, tmp_cumulo+pH+pH_cumulo+PL_cumulo+interval_yield+RS+Feed_Vol+Cell_conc._interval+rab_integral; 0.438, 0.722, tmp_cumulo+pH+pH_cumulo+AN+interval_yield+RS+Cell_conc._interval+AS_Vol.+emission_O2+emission_CO2+generate_CO2; 0.429, 0.722, tmp_cumulo+pH+pH_cumulo+AN+interval_yield+RS+Feed_Vol+Cell_conc._interval+rab_integral+AS_Vol.+emission_O2+generate_CO2; 0.447, 0.722, tmp_cumulo+pH+pH_cumulo+interval_yield+RS+Feed_Vol+Cell_conc._interval+RQ_integral+AS_Vol.+generate_CO2; 0.447, 0.722, tmp_cumulo+pH+pH_cumulo+AN+interval_yield+RS+Feed_Vol+Cell_conc._interval+interval_O2+generate_CO2; 0.438, 0.722, tmp_cumulo+pH+pH_cumulo+PL_cumulo+AN+interval_yield+RS+Cell_conc._interval+rab_integral+RQ_integral+AS_Vol.; 0.438, 0.722, tmp_cumulo+pH+pH_cumulo+PL+interval_yield+RS+Feed_Vol+Cell_conc._interval+Accum._Yield+AS_Vol.+interval_O2; 0.420, 0.722, tmp_cumulo+pH+pH_cumulo+AN+AN_cumulo+interval_yield+RS+Feed_Vol+Cell_conc._interval+rab_integral+AS_Vol.+emission_O2+generate_CO2; 0.429, 0.722, tmp_cumulo+pH+pH_cumulo+AN_cumulo+interval_yield+interval_Pdt.+RS+Cell_conc._interval+RQ_integral+AS_Vol.+emission_O2+emission_CO2; 0.464, 0.722, tmp_cumulo+pH+AN_cumulo+interval_yield+RS+Feed_Vol+Cell_conc._interval+generate_CO2; 0.438, 0.722, tmp_cumulo+pH+pH_cumulo+PL+AN_cumulo+interval_yield+interval_Pdt.+RS+Cell_conc._interval+RQ_integral+AS_Vol.; 0.420, 0.722, tmp_cumulo+pH+pH_cumulo+PL+AN_cumulo+interval_yield+RS+Feed_Vol+Cell_conc._interval+rab_integral+AS_Vol.+emission_CO2+interval_O2; 0.447, 0.722, tmp_cumulo+pH+pH_cumulo+interval_yield+RS+Feed_Vol+Cell_conc._interval+rab_integral+emission_CO2+interval_O2; 0.420, 0.722, tmp_cumulo+pH+pH_cumulo+AN+AN_cumulo+interval_yield+interval_Pdt.+RS+Feed_Vol+Cell_conc._interval+rab_integral+AS_Vol.+generate_CO2; 0.420, 0.722, tmp_cumulo+pH+pH_cumulo+PL+AN_cumulo+interval_yield+RS+Feed_Vol+Cell_conc._interval+AS_Vol.+emission_CO2+interval_O2+generate_CO2; 0.447, 0.722, tmp_cumulo+pH+pH_cumulo+AN_cumulo+interval_yield+interval_Pdt.+RS+Cell_conc._interval+AS_Vol.+emission_O2; 0.447, 0.722, tmp_cumulo+pH+pH_cumulo+PL+interval_yield+RS+Cell_conc._interval+AS_Vol.+emission_CO2+interval_O2; 0.464, 0.722, tmp_cumulo+pH+interval_yield+RS+Feed_Vol+Cell_conc._interval+emission_CO2+interval_O2; 0.438, 0.722, tmp_cumulo+pH+pH_cumulo+PL_cumulo+AN_cumulo+interval_yield+interval_Pdt.+RS+Cell_conc._interval+AS_Vol.+generate_CO2; 0.447, 0.722, tmp_cumulo+pH+pH_cumulo+AN_cumulo+interval_yield+interval_Pdt.+RS+Feed_Vol+Cell_conc._interval+consum_O2; 0.420, 0.722, tmp_cumulo+pH+pH_cumulo+AN+AN_cumulo+interval_yield+interval_Pdt.+RS+Feed_Vol+Cell_conc._interval+rab_integral+RQ_integral+AS_Vol.; 0.455, 0.722, tmp+tmp_cumulo+pH+pH_cumulo+interval_yield+RS+Cell_conc._interval+rab_integral+AS_Vol.; 0.438, 0.722, tmp_cumulo+pH+pH_cumulo+AN+interval_yield+RS+Feed_Vol+Cell_conc._interval+RQ_integral+AS_Vol.+consum_O2; 0.447, 0.722, tmp_cumulo+pH+pH_cumulo+PL+PL_cumulo+AN+interval_yield+RS+Cell_conc._interval+AS_Vol.; 0.455, 0.722, tmp_cumulo+pH+pH_cumulo+interval_yield+interval_Pdt.+RS+Cell_conc._interval+rab_integral+AS_Vol.; 0.419, 0.722, tmp+tmp_cumulo+pH+pH_cumulo+AN_cumulo+interval_yield+RS+Feed_Vol+Cell_conc._interval+AS_Vol.+emission_O2+emission_CO2+generate_CO2; 0.429, 0.722, tmp_cumulo+pH+pH_cumulo+PL_cumulo+AN+interval_yield+RS+Feed_Vol+Cell_conc._interval+RQ_integral+AS_Vol.+generate_CO2; 0.419, 0.722, tmp_cumulo+pH+pH_cumulo+PL_cumulo+AN+AN_cumulo+interval_yield+interval_Pdt.+RS+Feed_Vol+Cell_conc._interval+AS_Vol.+generate_CO2; 0.447, 0.722, tmp+tmp_cumulo+pH+pH_cumulo+interval_yield+RS+Feed_Vol+Cell_conc._interval+RQ_integral+AS_Vol.;

0.447, 0.722, tmp_cumulo+pH+pH_cumulo+interval_yield+RS+Feed_Vol+Cell_conc._interval+AS_Vol.+emission_O2+emission_CO2; 0.455, 0.722, tmp_cumulo+pH+pH_cumulo+AN_cumulo+interval_yield+OD+RS+Feed_Vol+Cell_conc._interval; 0.429, 0.722, tmp_cumulo+pH+pH_cumulo+PL_cumulo+AN+interval_yield+RS+Feed_Vol+Cell_conc._interval+rab_integral+RQ_integral+AS_Vol; 0.429, 0.722, tmp_cumulo+pH+pH_cumulo+AN_cumulo+interval_yield+interval_Pdt.+RS+Cell_conc._interval+rab_integral+AS_Vol.+emission_O2+emission_CO2; 0.429, 0.722, tmp_cumulo+pH+pH_cumulo+PL+AN+interval_yield+RS+Cell_conc._interval+rab_integral+Accum._Yield+AS_Vol.+interval_O2; 0.429, 0.722, tmp+tmp_cumulo+pH+pH_cumulo+AN_cumulo+interval_yield+interval_Pdt.+RS+Feed_Vol+Cell_conc._interval+AS_Vol.+emission_O2; 0.429, 0.722, tmp_cumulo+pH+pH_cumulo+PL+AN+interval_yield+RS+Cell_conc._interval+rab_integral+AS_Vol.+consum_O2+interval_O2; 0.438, 0.722, tmp_cumulo+pH+pH_cumulo+PL_cumulo+AN_cumulo+interval_yield+interval_Pdt.+RS+Cell_conc._interval+AS_Vol.+emission_CO2; 0.429, 0.722, tmp+tmp_cumulo+pH+pH_cumulo+AN+interval_yield+RS+Feed_Vol+Cell_conc._interval+RQ_integral+AS_Vol.+generate_CO2; 0.455, 0.722, tmp_cumulo+pH+interval_yield+RS+Feed_Vol+Cell_conc._interval+rab_integral+interval_O2+generate_CO2; 0.447, 0.722, tmp_cumulo+pH+pH_cumulo+AN_cumulo+interval_yield+RS+RS_cumulo+Cell_conc._interval+AS_Vol.+emission_O2; 0.447, 0.722, tmp_cumulo+pH+pH_cumulo+PL+AN+interval_yield+RS+Cell_conc._interval+AS_Vol.+generate_CO2; 0.419, 0.722, tmp+tmp_cumulo+pH+pH_cumulo+PL_cumulo+AN_cumulo+interval_yield+RS+Feed_Vol+Cell_conc._interval+rab_integral+RQ_integral+AS_Vol.; 0.455, 0.722, tmp_cumulo+pH+PL_cumulo+AN_cumulo+interval_yield+RS+Feed_Vol+Cell_conc._interval+AS_Vol.; 0.438, 0.722, tmp_cumulo+pH+pH_cumulo+AN+interval_yield+RS+Feed_Vol+RS_cumulo+Cell_conc._interval+rab_integral+AS_Vol.; 0.447, 0.722, tmp_cumulo+pH+pH_cumulo+interval_yield+interval_Pdt.+RS+Feed_Vol+Cell_conc._interval+rab_integral+AS_Vol.; 0.438, 0.722, tmp_cumulo+pH+pH_cumulo+AN_cumulo+interval_yield+OD+RS+Feed_Vol+Cell_conc._interval+AS_Vol.+consum_O2; 0.429, 0.722, tmp+tmp_cumulo+pH+pH_cumulo+PL+AN_cumulo+interval_yield+RS+Feed_Vol+Cell_conc._interval+rab_integral+AS_Vol.; 0.429, 0.722, tmp_cumulo+pH+pH_cumulo+PL+AN_cumulo+interval_yield+interval_Pdt.+RS+Feed_Vol+Cell_conc._interval+rab_integral+AS_Vol.; 0.455, 0.722, tmp_cumulo+pH+pH_cumulo+interval_yield+RS+Feed_Vol+Cell_conc._interval+emission_O2+emission_CO2; 0.419, 0.722, tmp_cumulo+pH+pH_cumulo+AN+AN_cumulo+interval_yield+RS+Feed_Vol+Cell_conc._interval+RQ_integral+AS_Vol.+emission_CO2+generate_CO2; 0.446, 0.722, tmp+tmp_cumulo+pH+pH_cumulo+AN+AN_cumulo+interval_yield+RS+Feed_Vol+Cell_conc._interval; 0.438, 0.722, tmp_cumulo+pH+pH_cumulo+PL+AN+interval_yield+RS+Cell_conc._interval+rab_integral+RQ_integral+AS_Vol.; 0.455, 0.722, tmp+tmp_cumulo+pH+pH_cumulo+interval_yield+RS+Feed_Vol+Cell_conc._interval+emission_O2; 0.419, 0.722, tmp_cumulo+pH+pH_cumulo+PL+AN+AN_cumulo+interval_yield+interval_Pdt.+RS+Cell_conc._interval+rab_integral+AS_Vol.+emission_CO2; 0.455, 0.722, tmp+pH_cumulo+AN+pH_cumulo+interval_yield+RS+Feed_Vol+Cell_conc._interval+AS_Vol.; 0.438, 0.722, tmp_cumulo+pH+pH_cumulo+PL+AN_cumulo+interval_yield+RS+Cell_conc._interval+Accum._Yield+AS_Vol.+emission_CO2; 0.419, 0.722, tmp_cumulo+pH+pH_cumulo+PL_cumulo+AN+AN_cumulo+interval_yield+interval_Pdt.+RS+Feed_Vol+Cell_conc._interval+rab_integral+AS_Vol.; 0.463, 0.722, tmp_cumulo+pH+interval_yield+RS+Feed_Vol+Cell_conc._interval+AS_Vol.+interval_O2; 0.438, 0.722, tmp_cumulo+pH+pH_cumulo+interval_yield+RS+Feed_Vol+Cell_conc._interval+rab_integral+AS_Vol.+emission_CO2+generate_CO2; 0.446, 0.722, tmp+tmp_cumulo+pH+pH_cumulo+interval_yield+RS+Feed_Vol+Cell_conc._interval+rab_integral+consum_O2; 0.429, 0.722, tmp_cumulo+pH+pH_cumulo+AN+interval_yield+interval_Pdt.+RS+Feed_Vol+Cell_conc._interval+AS_Vol.+emission_CO2+generate_CO2; 0.446, 0.722, tmp_cumulo+pH+pH_cumulo+interval_yield+RS+Feed_Vol+Cell_conc._interval+rab_integral+RQ_integral+emission_CO2; 0.438, 0.722, tmp+tmp_cumulo+pH+pH_cumulo+AN+interval_yield+RS+Feed_Vol+Cell_conc._interval+Accum._Yield+AS_Vol.; 0.428, 0.722, tmp_cumulo+pH+pH_cumulo+AN+interval_yield+OD+RS+Cell_conc._interval+rab_integral+AS_Vol.+emission_CO2+generate_CO2; 0.428, 0.722, tmp_cumulo+pH+pH_cumulo+PL_cumulo+AN_cumulo+interval_yield+RS+Cell_conc._interval+rab_integral+RQ_integral+AS_Vol.+generate_CO2; 0.446, 0.722, tmp_cumulo+pH+pH_cumulo+AN+interval_yield+RS+Feed_Vol+Cell_conc._interval+rab_integral+consum_O2; 0.455, 0.722, tmp_cumulo+pH+pH_cumulo+interval_yield+interval_Pdt.+RS+Feed_Vol+Cell_conc._interval+interval_O2; 0.455, 0.722, tmp+pH+pH_cumulo+AN+cumulo+interval_yield+interval_Pdt.+RS+Cell_conc._interval+AS_Vol.; 0.428, 0.722, tmp_cumulo+pH+pH_cumulo+AN+AN_cumulo+interval_yield+interval_Pdt.+RS+Feed_Vol+RS_cumulo+Cell_conc._interval+AS_Vol.; 0.419, 0.722, tmp_cumulo+pH+pH_cumulo+PL+AN+interval_yield+RS+Cell_conc._interval+rab_integral+Accum._Yield+AS_Vol.+emission_CO2+interval_O2; 0.428, 0.722, tmp_cumulo+pH+pH_cumulo+PL+AN_cumulo+interval_yield+RS+Cell_conc._interval+RQ_integral+AS_Vol.+emission_CO2+consum_O2; 0.446, 0.722, tmp_cumulo+pH+pH_cumulo+AN+interval_yield+RS+Cell_conc._interval+RQ_integral+AS_Vol.+consum_O2; 0.419, 0.722, tmp_cumulo+pH+pH_cumulo+AN_cumulo+interval_yield+RS+Feed_Vol+Cell_conc._interval+rab_integral+AS_Vol.+emission_CO2+consum_O2+generate_CO2; 0.428, 0.722, tmp_cumulo+pH+pH_cumulo+PL_cumulo+AN+AN_cumulo+interval_yield+RS+Cell_conc._interval+rab_integral+AS_Vol.+consum_O2; 0.446, 0.722, tmp_cumulo+pH+pH_cumulo+PL+AN+interval_yield+RS+Cell_conc._interval+AS_Vol.+consum_O2; 0.428, 0.722, tmp_cumulo+pH+pH_cumulo+AN_cumulo+interval_yield+interval_Pdt.+RS+Feed_Vol+RS_cumulo+Cell_conc._interval+AS_Vol.+emission_CO2; 0.455, 0.722, tmp+tmp_cumulo+pH+pH_cumulo+interval_yield+RS+Feed_Vol+Cell_conc._interval+RQ_integral; 0.437, 0.722, tmp+tmp_cumulo+pH+pH_cumulo+AN+interval_yield+RS+Cell_conc._interval+AS_Vol.+emission_CO2+generate_CO2; 0.437, 0.722, tmp_cumulo+pH+pH_cumulo+PL+AN_cumulo+interval_yield+RS+Cell_conc._interval+AS_Vol.+interval_O2+generate_CO2; 0.455, 0.722, pH+pH_cumulo+PL_cumulo+AN_cumulo+interval_yield+RS+Cell_conc._interval+AS_Vol.+generate_CO2; 0.437, 0.722, tmp_cumulo+pH+pH_cumulo+AN+AN_cumulo+interval_yield+OD+RS+Cell_conc._interval+RQ_integral+AS_Vol.; 0.437, 0.722, tmp_cumulo+pH+pH_cumulo+AN_cumulo+interval_yield+OD+RS+Cell_conc._interval+rab_integral+RQ_integral+AS_Vol.; 0.428, 0.722, tmp_cumulo+pH+pH_cumulo+PL+AN+AN_cumulo+interval_yield+RS+Feed_Vol+Cell_conc._interval+rab_integral+AS_Vol.; 0.463, 0.722, tmp_cumulo+pH+AN+AN_cumulo+interval_yield+RS+Feed_Vol+Cell_conc._interval;
0.428, 0.722, tmp_cumulo+pH+pH_cumulo+PL_cumulo+
AN_cumulo+interval_yield+RS+Feed_Vol+Cell_conc._interval+rab_integral+AS_Vol.+emission_O2; 0.446, 0.722, tmp_cumulo+pH+pH_cumulo+interval_yield+RS+Feed_Vol+Cell_conc._interval+RQ_integral+AS_Vol.+emission_CO2; 0.428, 0.722, tmp+tmp_cumulo+pH+pH_cumulo+PL_cumulo+AN_cumulo+interval_yield+RS+Feed_Vol+RS_cumulo+Cell_conc._interval+AS_Vol.; 0.419, 0.722, tmp_cumulo+pH+pH_cumulo+PL_cumulo+AN_cumulo+interval_yield+interval_Pdt.+RS+Feed_Vol+Cell_conc._interval+rab_integral+RQ_integral+AS_Vol.; 0.446, 0.722, tmp+tmp_cumulo+pH+pH_cumulo+AN_cumulo+interval_yield+RS+Feed_Vol+Cell_conc._interval+consum_O2; 0.437, 0.722, tmp+tmp_cumulo+pH+pH_cumulo+AN_cumulo+interval_yield+RS+Cell_conc._interval+RQ_integral+AS_Vol.+generate_CO2; 0.437, 0.722, tmp_cumulo+pH+pH_cumulo+AN+interval_yield+interval_Pdt.+RS+Feed_Vol+Cell_conc._interval+AS_Vol.+consum_O2; 0.428, 0.722, tmp_cumulo+pH+pH_cumulo+AN_cumulo+interval_yield+interval_Pdt.+RS+Feed_Vol+Cell_conc._interval+AS_Vol.+emission_CO2+consum_O2; 0.455, 0.722, pH+pH_cumulo+PL_cumulo+AN_cumulo+interval_yield+RS+RS_cumulo+Cell_conc._interval+AS_Vol.; 0.446, 0.722, tmp_cumulo+pH+pH_cumulo+AN+interval_yield+interval_Pdt.+RS+Cell_conc._interval+RQ_integral+AS_Vol.; 0.437, 0.722, tmp_cumulo+pH+pH_cumulo+AN+interval_yield+RS+Feed_Vol+RS_cumulo+Cell_conc._interval+RQ_integral+AS_Vol.; 0.455, 0.722, tmp_cumulo+pH+pH_cumulo+interval_yield+RS+Feed_Vol+Cell_conc._interval+emission_O2+consum_O2; 0.428, 0.722, tmp+tmp_cumulo+pH+pH_cumulo+PL_cumulo+AN_cumulo+interval_yield+RS+Feed_Vol+Cell_conc._interval+AS_Vol.+consum_O2; 0.428, 0.722, tmp_cumulo+pH+pH_cumulo+AN+interval_yield+interval_Pdt.+RS+Feed_Vol+Cell_conc._interval+rab_integral+AS_Vol.+generate_CO2; 0.437, 0.722, tmp+tmp_cumulo+pH+pH_cumulo+PL_cumulo+AN_cumulo+interval_yield+RS+Cell_conc._interval+RQ_integral+AS_Vol.; 0.463, 0.722, tmp_cumulo+pH+pH_cumulo+PL_cumulo+interval_yield+RS+Cell_conc._interval+AS_Vol.; 0.419, 0.722, tmp_cumulo+pH+pH_cumulo+AN_cumulo+interval_yield+RS+Feed_Vol+RS_cumulo+Cell_conc._interval+rab_integral+AS_Vol.+emission_CO2+generate_CO2; 0.446, 0.722, tmp_cumulo+pH+pH_cumulo+AN+interval_yield+RS+Cell_conc._interval+RQ_integral+AS_Vol.+emission_O2; 0.428, 0.722, tmp+tmp_cumulo+pH+pH_cumulo+AN+interval_yield+RS+Feed_Vol+Cell_conc._interval+rab_integral+RQ_integral+AS_Vol.; 0.428, 0.722, tmp+tmp_cumulo+pH+pH_cumulo+AN_cumulo+interval_yield+OD+RS+Feed_Vol+Cell_conc._interval+AS_Vol.+generate_CO2; 0.455, 0.722, tmp_cumulo+pH+pH_cumulo+AN_cumulo+interval_yield+RS+Feed_Vol+RS_cumulo+Cell_conc._interval; 0.428, 0.722, tmp_cumulo+pH+pH_cumulo+PL_cumulo+AN+AN_cumulo+interval_yield+RS+Feed_Vol+Cell_conc._interval+AS_Vol.+emission_O2; 0.428, 0.722, tmp+tmp_cumulo+pH+pH_cumulo+AN_cumulo+interval_yield+interval_Pdt.+RS+Feed_Vol+Cell_conc._interval+AS_Vol.+consum_O2; 0.437, 0.722, tmp_cumulo+pH+pH_cumulo+PL+AN_cumulo+interval_yield+RS+Cell_conc._interval+rab_integral+Accum._Yield+AS_Vol.; 0.437, 0.722, tmp_cumulo+pH+pH_cumulo+PL_cumulo+AN+interval_yield+RS+Feed_Vol+Cell_conc._interval+AS_Vol.+consum_O2

[206. Linear Model that Predicts Arginine Production Amount in Interval 6]
0.394, 0.678, tmp_cumulo+pH_cumulo+interval_yield+OD+RQ_integral+AS_Vol.+consum_O2+generate_CO2; 0.384, 0.677, tmp_cumulo+pH_cumulo+interval_yield+OD+RQ_integral+AS_Vol.+consum_O2+interval_O2+generate_CO2; 0.379, 0.674, tmp_cumulo+pH_cumulo+interval_yield+OD+rab_integral+RQ_integral+AS_Vol.+consum_O2+generate_CO2; 0.379, 0.674, tmp_cumulo+pH_cumulo+interval_yield+interval_Pdt.+OD+RQ_integral+AS_Vol.+consum_O2+generate_CO2; 0.368, 0.674, tmp_cumulo+pH_cumulo+interval_yield+OD+rab_integral+RQ_integral+AS_Vol.+consum_O2+interval_O2+generate_CO2; 0.367, 0.673, tmp_cumulo+pH_cumulo+interval_yield+interval_Pdt.+OD+RQ_integral+AS_Vol.+consum_O2+interval_O2+generate_CO2; 0.386, 0.673, tmp_cumulo+interval_yield+interval_Pdt.+RS_cumulo+RQ_integral+emission_CO2+consum_O2+generate_CO2; 0.366, 0.672, tmp_cumulo+pH_cumulo+interval_yield+interval_Pdt.+OD+RQ_integral+AS_Vol.+emission_CO2+consum_O2+generate_CO2; 0.375, 0.672, tmp_cumulo+interval_yield+interval_Pdt.+RS_cumulo+RQ_integral+AS_Vol.+emission_CO2+consum_O2+generate_CO2; 0.374, 0.671, tmp_cumulo+pH_cumulo+interval_yield+interval_Pdt.+RQ_integral+AS_Vol.+consum_O2+interval_O2+generate_CO2; 0.374, 0.671, tmp_cumulo+pH_cumulo+interval_yield+OD+RQ_integral+AS_Vol.+emission_CO2+consum_O2+generate_CO2; 0.373, 0.670, tmp_cumulo+interval_yield+interval_Pdt.+RS_cumulo+rab_integral+RQ_integral+emission_CO2+consum_O2+generate_CO2; 0.373, 0.670, tmp_cumulo+pH_cumulo+interval_yield+OD+RS_cumulo+RQ_integral+AS_Vol.+consum_O2+generate_CO2; 0.373, 0.670, tmp_cumulo+pH_cumulo+AN+interval_yield+OD+RQ_integral+AS_Vol.+consum_O2+generate_CO2; 0.363, 0.670, tmp_cumulo+pH_cumulo+AN+interval_yield+OD+RQ_integral+AS_Vol.+consum_O2+interval_O2+generate_CO2; 0.352, 0.670, tmp_cumulo+pH_cumulo+interval_yield+interval_Pdt.+OD+rab_integral+RQ_integral+AS_Vol.+emission_CO2+consum_O2+generate_CO2; 0.362, 0.670, tmp_cumulo+pH_cumulo+interval_yield+interval_Pdt.+OD+rab_integral+RQ_integral+AS_Vol.+consum_O2+generate_CO2; 0.372, 0.669, tmp_cumulo+pH_cumulo+interval_yield+OD+Feed_Vol+RQ_integral+AS_Vol.+consum_O2+generate_CO2; 0.362, 0.669, tmp_cumulo+pH_cumulo+interval_yield+OD+Feed_Vol+RQ_integral+AS_Vol.+consum_O2+interval_O2+generate_CO2; 0.371, 0.669, tmp_cumulo+pH_cumulo+interval_yield+OD+RQ_integral+AS_Vol.+emission_O2+consum_O2+generate_CO2; 0.361, 0.669, tmp_cumulo+pH_cumulo+interval_yield+OD+rab_integral+RQ_integral+AS_Vol.+emission_CO2+consum_O2+generate_CO2; 0.371, 0.669, tmp_cumulo+pH_cumulo+interval_yield+OD+Cell_conc._interval+RQ_integral+AS_Vol.+consum_O2+generate_CO2; 0.390, 0.669, tmp_cumulo+interval_yield+interval_Pdt.+RS_cumulo+RQ_integral+consum_O2+generate_CO2; 0.371, 0.669, tmp_cumulo+pH_cumulo+AN_cumulo+interval_yield+OD+RQ_integral+AS_Vol.+consum_O2+generate_CO2; 0.361, 0.669, tmp_cumulo+pH_cumulo+AN_cumulo+interval_yield+OD+RQ_integral+AS_Vol.+consum_O2+interval_O2+generate_CO2; 0.371, 0.669, tmp_cumulo+interval_yield+interval_Pdt.+OD+RS_cumulo+RQ_integral+emission_CO2+consum_O2+generate_CO2; 0.380, 0.668, tmp_cumulo+pH_cumulo+interval_yield+OD+RS_cumulo+RQ_integral+consum_O2+generate_CO2; 0.360, 0.668, tmp_cumulo+pH_cumulo+interval_yield+OD+RQ_integral+AS_Vol.+emission_O2+consum_O2+interval_O2+generate_CO2; 0.370, 0.668, tmp_cumulo+pH+pH_cumulo+interval_yield+OD+RQ_ integral+AS_Vol.+consum_O2+generate_CO2; 0.360, 0.668, tmp_cumulo+interval_yield+interval_Pdt.+RS_cumulo+rab_integral+RQ_integral+AS_Vol.+emission_CO2+consum_O2+generate_CO2; 0.360, 0.668, tmp_cumulo+pH_cumulo+interval_yield+OD+RQ_integral+AS_Vol.+emission_CO2+consum_O2+interval_O2+generate_CO2; 0.379, 0.668, tmp+interval_yield+interval_Pdt.+RS_cumulo+RQ_integral+emission_CO2+consum_O2+generate_CO2; 0.370, 0.668, tmp_cumulo+pH_cumulo+PL_cumulo+interval_yield+OD+RQ_integral+AS_Vol.+consum_O2+generate_CO2; 0.360, 0.668, tmp_cumulo+pH+pH_cumulo+interval_yield+OD+RQ_integral+AS_Vol.+consum_O2+interval_O2+generate_CO2; 0.360, 0.668, tmp_cumulo+pH_cumulo+interval_yield+OD+RS_cumulo+RQ_integral+AS_Vol.+consum_O2+interval_O2+generate_CO2; 0.379, 0.668, tmp+interval_yield+interval_Pdt.+RQ_integral+AS_Vol.+emission_CO2+consum_O2+generate_CO2; 0.349, 0.668, tmp_cumulo+pH_cumulo+interval_yield+interval_Pdt.+OD+Feed_Vol+RQ_integral+AS_Vol.+consum_O2+interval_O2+generate_CO2; 0.359, 0.668, tmp_cumulo+pH_cumulo+interval_yield+interval_Pdt.+OD+Feed_Vol+RQ_integral+AS_Vol.+consum_O2+generate_CO2; 0.369, 0.668, tmp_cumulo+pH_cumulo+interval_yield+interval_Pdt.+RQ_integral+AS_Vol.+emission_CO2+consum_O2+generate_CO2; 0.359, 0.668, tmp_cumulo+pH_cumulo+interval_yield+OD+Cell_conc._interval+RQ_integral+AS_Vol.+consum_O2+interval_O2+generate_CO2; 0.359, 0.668, tmp_cumulo+pH_cumulo+interval_yield+interval_Pdt.+OD+RQ_integral+AS_Vol.+emission_O2+consum_O2+generate_CO2; 0.359, 0.667, tmp_cumulo+pH_cumulo+interval_yield+OD+Feed_Vol+rab_integral+RQ_integral+AS_Vol.+consum_O2+generate_CO2; 0.369, 0.667, tmp_cumulo+pH_cumulo+interval_yield+interval_Pdt.+OD+RS_cumulo+RQ_integral+consum_O2+generate_CO2; 0.349, 0.667, tmp_cumulo+pH_cumulo+interval_yield+OD+Feed_Vol+rab_integral+RQ_integral+AS_Vol.+consum_O2+interval_O2+generate_CO2; 0.348, 0.667, tmp_cumulo+pH_cumulo+interval_yield+interval_Pdt.+OD+RQ_integral+AS_Vol.+emission_CO2+consum_O2+interval_O2+generate_CO2; 0.358, 0.667, tmp_cumulo+pH_cumulo+interval_yield+interval_Pdt.+OD+RS_cumulo+RQ_integral+AS_Vol.+consum_O2+generate_CO2; 0.368, 0.667, tmp+tmp_cumulo+pH_cumulo+interval_yield+OD+RQ_integral+AS_Vol.+consum_O2+generate_CO2; 0.358, 0.667, tmp_cumulo+pH_cumulo+PL_cumulo+interval_yield+OD+RQ_integral+AS_Vol.+consum_O2+interval_O2+generate_CO2; 0.368, 0.667, tmp_cumulo+interval_yield+interval_Pdt.+RS_cumulo+RQ_integral+emission_O2+emission_CO2+consum_O2+generate_CO2; 0.347, 0.667, tmp_cumulo+pH_cumulo+interval_yield+interval_Pdt.+OD+rab_integral+RQ_integral+AS_Vol.+consum_O2+interval_O2+generate_CO2; 0.357, 0.667, tmp_cumulo+pH_cumulo+AN+interval_yield+OD+rab_integral+RQ_integral+AS_Vol.+consum_O2+generate_CO2; 0.357, 0.666, tmp_cumulo+pH_cumulo+interval_yield+interval_Pdt.+RQ_integral+AS_Vol.+emission_CO2+consum_O2+interval_O2+generate_CO2; 0.347, 0.666, tmp_cumulo+pH_cumulo+interval_yield+OD+rab_integral+RQ_integral+AS_Vol.+emission_CO2+consum_O2+interval_O2+generate_CO2; 0.357, 0.666, tmp_cumulo+pH_cumulo+interval_yield+interval_Pdt.+rab_integral+RQ_integral+AS_Vol.+emission_CO2+consum_O2+generate_CO2; 0.357, 0.666, tmp_cumulo+pH_cumulo+interval_yield+interval_Pdt.+OD+RS_cumulo+RQ_integral+AS_Vol.+emission_CO2+consum_O2+generate_CO2; 0.357, 0.666, tmp_cumulo+pH_cumulo+AN+interval_yield+interval_Pdt.+OD+RQ_integral+AS_Vol.+consum_O2+generate_CO2; 0.376, 0.666, tmp_cumulo+pH_cumulo+interval_yield+interval_Pdt.+RQ_integral+AS_Vol.+consum_O2+generate_CO2; 0.357, 0.666, tmp_cumulo+pH_cumulo+interval_yield+OD+RS_cumulo+rab_integral+RQ_integral+AS_Vol.+consum_O2+generate_CO2; 0.347, 0.666, tmp_cumulo+pH_cumulo+AN+interval_yield+OD+rab_integral+RQ_integral+AS_Vol.+consum_O2+interval_O2+generate_CO2; 0.357, 0.666, tmp_cumulo+interval_yield+interval_Pdt.+OD+RS_cumulo+rab_integral+RQ_integral+emission_CO2+consum_O2+generate_CO2; 0.357, 0.666, tmp+pH_cumulo+interval_yield+interval_Pdt.+OD+RQ_integral+AS_Vol.+emission_CO2+consum_O2+generate_CO2; 0.357, 0.666, tmp_cumulo+pH_cumulo+interval_yield+OD+rab_integral+RQ_integral+AS_Vol.+emission_O2+consum_O2+generate_CO2; 0.346, 0.666, tmp_cumulo+pH_cumulo+interval_yield+interval_Pdt.+OD+RS_cumulo+RQ_integral+AS_Vol.+emission_CO2+consum_O2+generate_CO2; 0.346, 0.666, tmp+pH_cumulo+interval_yield+interval_Pdt.+OD+Feed_Vol+RQ_integral+AS_Vol.+consum_O2+interval_O2+generate_CO2; 0.356, 0.666, tmp+pH_cumulo+interval_yield+interval_Pdt.+OD+Feed_Vol+RQ_integral+AS_Vol.+consum_O2+generate_CO2; 0.356, 0.666, tmp_cumulo+pH_cumulo+AN_cumulo+interval_yield+interval_Pdt.+OD+RQ_integral+AS_Vol.+consum_O2+generate_CO2; 0.356, 0.666, tmp_cumulo+pH_cumulo+AN_cumulo+interval_yield+OD+rab_integral+RQ_integral+AS_Vol.+consum_O2+generate_CO2; 0.356, 0.666, tmp_cumulo+pH_cumulo+interval_yield+interval_Pdt.+RS_cumulo+RQ_integral+AS_Vol.+emission_CO2+consum_O2+generate_CO2; 0.366, 0.665, tmp+pH_cumulo+interval_yield+interval_Pdt.+RQ_integral+AS_Vol.+emission_CO2+consum_O2+generate_CO2; 0.356, 0.665, tmp+tmp_cumulo+pH_cumulo+interval_yield+OD+RQ_integral+AS_Vol.+consum_O2+interval_O2+generate_CO2; 0.366, 0.665, tmp_cumulo+AN+interval_yield+interval_Pdt.+RS_cumulo+RQ_integral+emission_CO2+consum_O2+generate_CO2; 0.345, 0.665, tmp_cumulo+pH_cumulo+AN_cumulo+interval_yield+OD+rab_integral+RQ_integral+AS_Vol.+consum_O2+interval_O2+generate_CO2; 0.355, 0.665, tmp_cumulo+interval_yield+interval_Pdt.+RS_cumulo+rab_integral+RQ_integral+emission_O2+emission_CO2+consum_O2+generate_CO2; 0.355, 0.665, tmp_cumulo+pH+pH_cumulo+interval_yield+OD+rab_integral+RQ_integral+AS_Vol.+consum_O2+generate_CO2; 0.375, 0.665, tmp_cumulo+interval_yield+interval_Pdt.+RQ_integral+AS_Vol.+emission_CO2+consum_O2+generate_CO2; 0.355, 0.665, tmp_cumulo+pH_cumulo+interval_yield+interval_Pdt.+OD+Cell_conc._interval+RQ_integral+AS_Vol.+consum_O2+generate_CO2; 0.365, 0.665, tmp_cumulo+pH_cumulo+interval_yield+OD+RS_cumulo+rab_integral+RQ_integral+consum_O2+generate_CO2; 0.345, 0.665, tmp_cumulo+pH_cumulo+interval_yield+interval_Pdt.+OD+RQ_integral+AS_Vol.+emission_O2+consum_O2+interval_O2+generate_CO2; 0.345, 0.665, tmp_cumulo+pH_cumulo+AN+interval_yield+interval_Pdt.+OD+RQ_integral+AS_Vol.+consum_O2+interval_O2+generate_CO2; 0.365, 0.665, tmp+interval_yield+interval_Pdt.+RS_cumulo+RQ_integral+AS_Vol.+emission_CO2+consum_O2+generate_CO2; 0.365, 0.665, tmp+interval_yield+interval_Pdt.+RS_cumulo+rab_integral+RQ_integral+emission_CO2+consum_O2+generate_CO2; 0.345, 0.665, tmp_cumulo+pH_cumulo+interval_yield+OD+rab_integral+RQ_integral+AS_Vol.+emission_O2+consum_O2+interval_O2+generate_CO2; 0.355, 0.665, tmp_cumulo+pH_cumulo+interval_yield+OD+Cell_conc._ interval+rab_integral+RQ_integral+AS_Vol.+consum_O2+ generate_CO2; 0.355, 0.665, tmp_cumulo+interval_yield+ interval_Pdt.+RS_cumulo+RQ_integral+AS_Vol.+ emission_O2+emission_CO2+consum_O2+generate_CO2; 0.344, 0.665, tmp_cumulo+pH+pH_cumulo+interval_ yield+OD+rab_integral+RQ_integral+AS_Vol.+consum_ O2+interval_O2+generate_CO2; 0.374, 0.665, tmp_cumulo+interval_yield+interval_Pdt.+OD+RS_cumulo+RQ_ integral+consum_O2+generate_CO2; 0.374, 0.664, tmp_ cumulo+interval_yield+interval_Pdt.+RS_cumulo+RQ_ integral+AS_Vol.+consum_O2+generate_CO2; 0.344, 0.664, tmp_cumulo+pH_cumulo+interval_yield+interval_ Pdt.+OD+RQ_integral+AS_Vol.+emission_O2+emission_ CO2+consum_O2+generate_CO2; 0.383, 0.664, tmp_cumulo+pH_cumulo+interval_yield+OD+RQ_integral+ consum_O2+generate_CO2; 0.344, 0.664, tmp_cumulo+ pH_cumulo+interval_yield+interval_Pdt.+OD+Feed_Vol+ rab_integral+RQ_integral+AS_Vol.+consum_O2+ generate_CO2; 0.354, 0.664, tmp_cumulo+pH_cumulo+ PL_cumulo+interval_yield+interval_Pdt.+OD+RQ_ integral+AS_Vol.+consum_O2+generate_CO2; 0.354, 0.664, tmp_cumulo+pH_cumulo+interval_yield+interval_ Pdt.+OD+RS_cumulo+RQ_integral+emission_CO2+consum_O2+generate_CO2; 0.354, 0.664, tmp_cumulo+pH_ cumulo+AN+interval_yield+interval_Pdt.+RQ_integral+ AS_Vol.+consum_O2+interval_O2+generate_CO2; 0.354, 0.664, tmp_cumulo+pH_cumulo+interval_yield+interval_ Pdt.+RQ_integral+AS_Vol.+emission_O2+consum_O2+interval_O2+generate_CO2; 0.364, 0.664, tmp_cumulo+AN_ cumulo+interval_yield+interval_Pdt.+RS_cumulo+RQ_ integral+emission_CO2+consum_O2+generate_CO2; 0.364, 0.664, tmp_cumulo+pH_cumulo+PL+interval_ yield+OD+RQ_integral+AS_Vol.+consum_O2+generate_ CO2; 0.373, 0.664, tmp_cumulo+interval_yield+interval_ Pdt.+RS_cumulo+RQ_integral+emission_O2+consum_ O2+generate_CO2; 0.353, 0.664, tmp_cumulo+pH_ cumulo+PL_cumulo+interval_yield+OD+rab_integral+ RQ_integral+AS_Vol.+consum_O2+generate_CO2; 0.353, 0.664, tmp+tmp_cumulo+pH_cumulo+interval_yield+interval_Pdt.+OD+RQ_integral+AS_Vol.+consum_O2+generate_CO2; 0.332, 0.664, tmp_cumulo+pH_cumulo+interval_ yield+interval_Pdt.+OD+rab_integral+RQ_integral+AS_ Vol.+emission_CO2+consum_O2+interval_O2+generate_ CO2; 0.363, 0.664, tmp+interval_yield+interval_Pdt.+OD+ RS_cumulo+RQ_integral+emission_CO2+consum_O2+ generate_CO2; 0.373, 0.664, tmp+pH_cumulo+interval_ yield+interval_Pdt.+OD+RQ_integral+consum_O2+ generate_CO2; 0.353, 0.664, tmp_cumulo+pH_cumulo+ interval_yield+interval_Pdt.+Feed_Vol+RQ_integral+AS_ Vol.+consum_O2+interval_O2+generate_CO2; 0.343, 0.664, tmp_cumulo+pH_cumulo+AN_cumulo+interval_ yield+interval_Pdt.+OD+RQ_integral+AS_Vol.+consum_ O2+interval_O2+generate_CO2; 0.343, 0.664, tmp_cumulo+pH_cumulo+AN+interval_yield+interval_Pdt.+OD+ RQ_integral+AS_Vol.+emission_CO2+consum_O2+ generate_CO2; 0.353, 0.664, tmp_cumulo+pH_cumulo+ PL+interval_yield+OD+RQ_integral+AS_Vol.+consum_ O2+interval_O2+generate_CO2; 0.363, 0.664, tmp+pH_ cumulo+interval_yield+interval_Pdt.+OD+RQ_integral+ AS_Vol.+consum_O2+generate_CO2; 0.353, 0.664, tmp_ cumulo+pH_cumulo+interval_yield+interval_Pdt.+rab_ integral+RQ_integral+AS_Vol.+consum_O2+interval_O2+ generate_CO2; 0.332, 0.663, tmp_cumulo+pH_cumulo+ interval_yield+interval_Pdt.+OD+Feed_Vol+rab_integral+ RQ_integral+AS_Vol.+consum_O2+interval_O2+ generate_CO2; 0.372, 0.663, tmp_cumulo+pH_cumulo+ interval_yield+interval_Pdt.+OD+RQ_integral+consum_ O2+generate_CO2; 0.342, 0.663, tmp_cumulo+pH_cumulo+interval_yield+OD+RS_cumulo+rab_integral+RQ_ integral+AS_Vol.+consum_O2+interval_O2+generate_ CO2; 0.363, 0.663, tmp+interval_yield+interval_Pdt.+RS_ cumulo+RQ_integral+emission_O2+emission_CO2+ consum_O2+generate_CO2; 0.353, 0.663, tmp_cumulo+ interval_yield+interval_Pdt.+Feed_Vol+RS_cumulo+RQ_ integral+AS_Vol.+emission_CO2+consum_O2+generate_ CO2; 0.362, 0.663, tmp+interval_yield+interval_Pdt.+rab_ integral+RQ_integral+AS_Vol.+emission_CO2+consum_ O2+generate_CO2; 0.352, 0.663, tmp_cumulo+pH_ cumulo+interval_yield+OD+RS_cumulo+RQ_integral+ AS_Vol.+emission_CO2+consum_O2+generate_CO2; 0.342, 0.663, tmp_cumulo+pH_cumulo+interval_yield+interval_Pdt.+OD+Feed_Vol+RQ_integral+AS_Vol.+emission_CO2+consum_O2+generate_CO2; 0.352, 0.663, tmp_ cumulo+pH+pH_cumulo+interval_yield+interval_Pdt.+ OD+RQ_integral+AS_Vol.+consum_O2+generate_CO2; 0.362, 0.663, tmp_cumulo+PL_cumulo+interval_yield+interval_Pdt.+RS_cumulo+RQ_integral+emission_CO2+consum_O2+generate_CO2; 0.342, 0.663, tmp_cumulo+pH_ cumulo+interval_yield+interval_Pdt.+rab_integral+RQ_ integral+AS_Vol.+emission_CO2+consum_O2+interval_ O2+generate_CO2; 0.352, 0.663, tmp_cumulo+interval_ yield+interval_Pdt.+OD+RS_cumulo+RQ_integral+ emission_O2+emission_CO2+consum_O2+generate_CO2; 0.342, 0.663, tmp_cumulo+pH_cumulo+AN_cumulo+interval_yield+interval_Pdt.+OD+RQ_integral+AS_Vol.+emission_CO2+consum_O2+generate_CO2; 0.342, 0.663, tmp_ cumulo+pH_cumulo+AN+interval_yield+OD+Feed_Vol+ RQ_integral+AS_Vol.+consum_O2+interval_O2+ generate_CO2; 0.372, 0.663, tmp_cumulo+interval_yield+ interval_Pdt.+RS_cumulo+rab_integral+RQ_integral+ consum_O2+generate_CO2; 0.352, 0.663, tmp_cumulo+ pH_cumulo+interval_yield+interval_Pdt.+OD+RS_ cumulo+rab_integral+RQ_integral+consum_O2+generate_ CO2; 0.342, 0.663, tmp_cumulo+pH_cumulo+interval_ yield+OD+Cell_conc._interval+rab_integral+RQ_integral+ AS_Vol.+consum_O2+interval_O2+generate_CO2; 0.331, 0.663, tmp_cumulo+pH_cumulo+interval_yield+interval_ Pdt.+OD+RS_cumulo+rab_integral+RQ_integral+AS_ Vol.+emission_CO2+consum_O2+generate_CO2; 0.362, 0.663, tmp_cumulo+pH+interval_yield+interval_Pdt.+RS_ cumulo+RQ_integral+emission_CO2+consum_O2+generate_CO2; 0.342, 0.663, tmp_cumulo+pH_cumulo+interval_ yield+interval_Pdt.+RS_cumulo+rab_integral+RQ_ integral+AS_Vol.+emission_CO2+consum_O2+generate_ CO2; 0.352, 0.663, tmp+tmp_cumulo+pH_cumulo+ interval_yield+OD+rab_integral+RQ_integral+AS_Vol.+ consum_O2+generate_CO2; 0.342, 0.663, tmp_cumulo+ pH_cumulo+interval_yield+interval_Pdt.+OD+rab_ integral+RQ_integral+AS_Vol.+emission_O2+consum_ O2+generate_CO2; 0.352, 0.663, tmp_cumulo+AN+ interval_yield+interval_Pdt.+RS_cumulo+rab_integral+ RQ_integral+emission_CO2+consum_O2+generate_CO2; 0.331, 0.663, tmp_cumulo+pH_cumulo+interval_yield+interval_Pdt.+OD+rab_integral+RQ_integral+AS_Vol.+emission_O2+emission_CO2+consum_O2+generate_CO2; 0.362, 0.663, tmp_cumulo+pH_cumulo+ interval_yield+interval_Pdt.+RS_cumulo+RQ_integral+ AS_Vol.+consum_O2+generate_CO2; 0.362, 0.663, tmp_ cumulo+interval_yield+interval_Pdt.+Feed_Vol+RS_ cumulo+RQ_integral+emission_CO2+consum_O2+ generate_CO2; 0.352, 0.663, tmp_cumulo+pH+interval_ yield+interval_Pdt.+RS_cumulo+RQ_integral+AS_Vol.+ emission_CO2+consum_O2+generate_CO2; 0.362, 0.663, tmp+tmp_cumulo+interval_yield+interval_Pdt.+RS_cumulo+RQ_integral+emission_CO2+consum_O2+generate_CO2; 0.362, 0.663, tmp+interval_yield+interval_Pdt.+OD+RQ_integral+AS_Vol.+emission_CO2+consum_O2+generate_CO2; 0.352, 0.663, tmp_cumulo+pH_cumulo+interval_yield+OD+Cell_conc._interval+RQ_integral+AS_Vol.+emission_CO2+consum_O2+generate_CO2; 0.341, 0.663, tmp_cumulo+pH_cumulo+interval_yield+interval_Pdt.+OD+RS_cumulo+RQ_integral+AS_Vol.+consum_O2+interval_O2+generate_CO2; 0.341, 0.663, tmp_cumulo+pH_cumulo+interval_yield+interval_Pdt.+OD+Cell_conc._interval+RQ_integral+AS_Vol.+consum_O2+interval_O2+generate_CO2; 0.341, 0.663, tmp_cumulo+interval_yield+interval_Pdt.+OD+RS_cumulo+rab_integral+RQ_integral+AS_Vol.+emission_CO2+consum_O2+generate_CO2; 0.351, 0.663, tmp_cumulo+AN+interval_yield+interval_Pdt.+RS_cumulo+RQ_integral+AS_Vol.+emission_CO2+consum_O2+generate_CO2; 0.351, 0.663, tmp+pH_cumulo+interval_yield+interval_Pdt.+rab_integral+RQ_integral+AS_Vol.+emission_CO2+consum_O2+generate_CO2; 0.361, 0.662, tmp_cumulo+pH_cumulo+interval_yield+interval_Pdt.+RQ_integral+AS_Vol.+emission_O2+consum_O2+generate_CO2; 0.341, 0.662, tmp_cumulo+pH_cumulo+interval_yield+interval_Pdt.+OD+Cell_conc._interval+RQ_integral+AS_Vol.+emission_CO2+consum_O2+generate_CO2; 0.341, 0.662, tmp_cumulo+pH_cumulo+PL_cumulo+interval_yield+OD+rab_integral+RQ_integral+AS_Vol.+consum_O2+interval_O2+generate_CO2; 0.351, 0.662, tmp_cumulo+pH_cumulo+AN+interval_yield+OD+RQ_integral+AS_Vol.+emission_CO2+consum_O2+generate_CO2; 0.341, 0.662, tmp_cumulo+pH_cumulo+interval_yield+interval_Pdt.+OD+Feed_Vol+RS_cumulo+RQ_integral+AS_Vol.+consum_O2+generate_CO2; 0.361, 0.662, tmp+interval_yield+interval_Pdt.+Cell_conc._interval+RQ_integral+AS_Vol.+emission_CO2+consum_O2+generate_CO2; 0.361, 0.662, tmp_cumulo+pH_cumulo+interval_yield+OD+RS_cumulo+RQ_integral+consum_O2+interval_O2+generate_CO2; 0.340, 0.662, tmp_cumulo+pH+pH_cumulo+interval_yield+interval_Pdt.+OD+RQ_integral+AS_Vol.+consum_O2+interval_O2+generate_CO2; 0.340, 0.662, tmp_cumulo+interval_yield+interval_Pdt.+RS_cumulo+rab_integral+RQ_integral+AS_Vol.+emission_O2+emission_CO2+consum_O2+generate_CO2; 0.351, 0.662, tmp_cumulo+pH_cumulo+interval_yield+interval_Pdt.+RS_cumulo+RQ_integral+AS_Vol.+consum_O2+interval_O2+generate_CO2; 0.351, 0.662, tmp_cumulo+pH_cumulo+AN_cumulo+interval_yield+interval_Pdt.+RQ_integral+AS_Vol.+consum_O2+interval_O2+generate_CO2; 0.351, 0.662, tmp_cumulo+pH_cumulo+AN+interval_yield+OD+Feed_Vol+RQ_integral+AS_Vol.+consum_O2+generate_CO2; 0.340, 0.662, tmp_cumulo+pH_cumulo+interval_yield+interval_Pdt.+OD+RS_cumulo+rab_integral+RQ_integral+emission_CO2+consum_O2+generate_CO2; 0.360, 0.662, tmp_cumulo+pH_cumulo+interval_yield+interval_Pdt.+RS_cumulo+RQ_integral+emission_CO2+consum_O2+generate_CO2; 0.350, 0.662, tmp_cumulo+AN_cumulo+interval_yield+interval_Pdt.+RS_cumulo+RQ_integral+AS_Vol.+emission_CO2+consum_O2+generate_CO2; 0.340, 0.662, tmp+pH_cumulo+interval_yield+interval_Pdt.+OD+rab_integral+RQ_integral+AS_Vol.+emission_CO2+consum_O2+generate_CO2; 0.350, 0.662, tmp_cumulo+pH_cumulo+interval_yield+OD+RS_cumulo+RQ_integral+AS_Vol.+emission_O2+consum_O2+generate_CO2; 0.360, 0.662, tmp_cumulo+pH_cumulo+interval_yield+OD+RQ_integral+Accum._Yield+AS_Vol.+consum_O2+generate_CO2; 0.350, 0.662, tmp+tmp_cumulo+interval_yield+interval_Pdt.+RS_cumulo+RQ_integral+AS_Vol.+emission_CO2+consum_O2+generate_CO2; 0.329, 0.662, tmp_cumulo+pH_cumulo+interval_yield+interval_Pdt.+OD+Feed_Vol+rab_integral+AS_Vol.+emission_CO2+consum_O2+generate_CO2; 0.370, 0.662, tmp_cumulo+pH_cumulo+interval_yield+OD+Feed_Vol+RQ_integral+consum_O2+generate_CO2; 0.360, 0.662, tmp_cumulo+interval_yield+interval_Pdt.+rab_integral+RQ_integral+AS_Vol.+emission_CO2+consum_O2+generate_CO2; 0.350, 0.662, tmp_cumulo+pH_cumulo+AN+interval_yield+OD+RS_cumulo+RQ_integral+AS_Vol.+consum_O2+generate_CO2; 0.329, 0.662, tmp_cumulo+pH_cumulo+AN+interval_yield+interval_Pdt.+OD+rab_integral+RQ_integral+AS_Vol.+emission_CO2+consum_O2+generate_CO2; 0.370, 0.662, tmp_cumulo+pH_cumulo+OD+RQ_integral+AS_Vol.+consum_O2+interval_O2+generate_CO2; 0.360, 0.662, tmp_cumulo+pH+interval_yield+interval_Pdt.+RQ_integral+AS_Vol.+emission_CO2+consum_O2+generate_CO2; 0.350, 0.662, tmp_cumulo+pH_cumulo+AN_cumulo+interval_yield+OD+RQ_integral+AS_Vol.+emission_CO2+consum_O2+generate_CO2; 0.350, 0.662, tmp_cumulo+pH_cumulo+interval_yield+OD+Feed_Vol+RS_cumulo+RQ_integral+AS_Vol.+consum_O2+generate_CO2; 0.360, 0.662, tmp_cumulo+interval_yield+interval_Pdt.+RS_cumulo+RQ_integral+AS_Vol.+emission_O2+consum_O2+generate_CO2; 0.350, 0.662, tmp_cumulo+AN_cumulo+interval_yield+interval_Pdt.+RS_cumulo+rab_integral+RQ_integral+emission_CO2+consum_O2+generate_CO2; 0.350, 0.661, tmp_cumulo+pH_cumulo+interval_yield+OD+RQ_integral+AS_Vol.+emission_O2+emission_CO2+consum_O2+generate_CO2; 0.339, 0.661, tmp_cumulo+pH_cumulo+PL_cumulo+interval_yield+interval_Pdt.+OD+RQ_integral+AS_Vol.+consum_O2+interval_O2+generate_CO2; 0.350, 0.661, tmp_cumulo+pH_cumulo+interval_yield+OD+Feed_Vol+RQ_integral+AS_Vol.+emission_CO2+consum_O2+generate_CO2; 0.339, 0.661, tmp+pH_cumulo+interval_yield+interval_Pdt.+OD+Feed_Vol+RQ_integral+AS_Vol.+emission_CO2+consum_O2+generate_CO2; 0.360, 0.661, tmp+interval_yield+interval_Pdt.+RQ_integral+AS_Vol.+emission_O2+emission_CO2+consum_O2+generate_CO2; 0.329, 0.661, tmp_cumulo+pH_cumulo+AN+interval_yield+OD+Feed_Vol+rab_integral+RQ_integral+AS_Vol.+consum_O2+interval_O2+generate_CO2; 0.339, 0.661, tmp+tmp_cumulo+pH_cumulo+interval_yield+interval_Pdt.+OD+RQ_integral+AS_Vol.+emission_CO2+consum_O2+generate_CO2; 0.369, 0.661, tmp_cumulo+pH_cumulo+interval_yield+interval_Pdt.+RS_cumulo+RQ_integral+consum_O2+generate_CO2; 0.339, 0.661, tmp_cumulo+pH_cumulo+AN+interval_yield+interval_Pdt.+OD+rab_integral+RQ_integral+AS_Vol.+consum_O2+generate_CO2; 0.328, 0.661, tmp_cumulo+pH_cumulo+AN+interval_yield+interval_Pdt.+OD+Feed_Vol+RQ_integral+AS_Vol.+consum_O2+interval_O2+generate_CO2; 0.349, 0.661, tmp_cumulo+pH_cumulo+AN+interval_yield+OD+RQ_integral+AS_Vol.+emission_O2+consum_O2+generate_CO2; 0.339, 0.661, tmp+tmp_cumulo+pH_cumulo+interval_yield+interval_Pdt.+OD+RQ_integral+AS_Vol.+consum_O2+interval_O2+generate_CO2; 0.339, 0.661, tmp_cumulo+interval_yield+interval_Pdt.+OD+RS_cumulo+rab_integral+RQ_integral+emission_O2+emission_CO2+consum_O2+generate_CO2; 0.359, 0.661, tmp_cumulo+pH_cumulo+AN+interval_yield+OD+RS_cumulo+RQ_integral+consum_O2+generate_CO2; 0.349, 0.661, tmp_cumulo+interval_yield+interval_Pdt.+RS_cumulo+RQ_integral+AS_Vol.+emission_CO2+consum_O2+interval_O2+generate_CO2; 0.339, 0.661, tmp_cumulo+pH_cumulo+ interval_yield+interval_Pdt.+OD+RS_cumulo+rab_integral+RQ_integral+AS_Vol.+consum_O2+generate_CO2; 0.339, 0.661, tmp+tmp_cumulo+pH_cumulo+interval_yield+OD+rab_integral+RQ_integral+AS_Vol.+consum_O2+interval_O2+generate_CO2; 0.378, 0.661, tmp+pH_cumulo+interval_yield+OD+RQ_integral+consum_O2+generate_CO2; 0.349, 0.661, tmp+interval_yield+interval_Pdt.+RS_cumulo+rab_integral+RQ_integral+emission_O2+emission_CO2+consum_O2+generate_CO2; 0.349, 0.661, tmp_cumulo+pH_cumulo+interval_yield+interval_Pdt.+Feed_Vol+RQ_integral+AS_Vol.+emission_CO2+consum_O2+generate_CO2; 0.339, 0.661, tmp+pH_cumulo+interval_yield+interval_Pdt.+OD+Feed_Vol+rab_integral+RQ_integral+AS_Vol.+consum_O2+generate_CO2; 0.339, 0.661, tmp_cumulo+pH_cumulo+interval_yield+OD+RS_cumulo+rab_integral+RQ_integral+AS_Vol.+emission_CO2+consum_O2+generate_CO2; 0.359, 0.661, tmp+AN_cumulo+interval_yield+interval_Pdt.+RS_cumulo+RQ_integral+emission_CO2+consum_O2+generate_CO2; 0.349, 0.661, tmp_cumulo+pH_cumulo+interval_yield+OD+RQ_integral+Accum._Yield+AS_Vol.+consum_O2+interval_O2+generate_CO2; 0.339, 0.661, tmp_cumulo+pH_cumulo+interval_yield+OD+Cell_conc._interval+rab_integral+RQ_integral+AS_Vol.+emission_CO2+consum_O2+generate_CO2; 0.378, 0.661, tmp+interval_yield+interval_Pdt.+RS_cumulo+RQ_integral+consum_O2+generate_CO2; 0.369, 0.661, tmp+pH_cumulo+interval_yield+OD+RQ_integral+AS_Vol.+consum_O2+generate_CO2; 0.349, 0.661, tmp_cumulo+pH+interval_yield+interval_Pdt.+OD+RQ_integral+AS_Vol.+emission_CO2+consum_O2+generate_CO2; 0.328, 0.661, tmp_cumulo+pH_cumulo+AN_cumulo+interval_yield+interval_Pdt.+OD+rab_integral+RQ_integral+AS_Vol.+emission_CO2+consum_O2+generate_CO2; 0.349, 0.661, tmp_cumulo+pH_cumulo+AN+interval_yield+interval_Pdt.+OD+RS_cumulo+RQ_integral+consum_O2+generate_CO2; 0.349, 0.661, tmp_cumulo+pH+pH_cumulo+interval_yield+OD+RQ_integral+AS_Vol.+emission_CO2+consum_O2+generate_CO2; 0.369, 0.661, tmp_cumulo+interval_yield+interval_Pdt.+RS_cumulo+RQ_integral+consum_O2+interval_O2+generate_CO2; 0.349, 0.661, tmp_cumulo+pH_cumulo+AN+interval_yield+OD+Cell_conc._interval+RQ_integral+AS_Vol.+consum_O2+generate_CO2; 0.338, 0.661, tmp_cumulo+pH_cumulo+AN_cumulo+interval_yield+OD+Feed_Vol+RQ_integral+AS_Vol.+consum_O2+interval_O2+generate_CO2; 0.349, 0.661, tmp_cumulo+PL_cumulo+interval_yield+interval_Pdt.+RS_cumulo+rab_integral+RQ_integral+emission_CO2+consum_O2+generate_CO2; 0.359, 0.661, tmp+AN+interval_yield+interval_Pdt.+RS_cumulo+RQ_integral+emission_CO2+consum_O2+generate_CO2; 0.359, 0.661, tmp+pH_cumulo+interval_yield+interval_Pdt.+OD+RQ_integral+emission_CO2+consum_O2+generate_CO2; 0.338, 0.661, tmp_cumulo+pH_cumulo+AN+interval_yield+OD+rab_integral+RQ_integral+AS_Vol.+emission_CO2+consum_O2+generate_CO2; 0.368, 0.661, tmp_cumulo+pH_cumulo+interval_yield+OD+rab_integral+RQ_integral+consum_O2+generate_CO2; 0.338, 0.661, tmp_cumulo+pH_cumulo+AN+interval_yield+OD+RQ_integral+AS_Vol.+emission_CO2+consum_O2+interval_O2+generate_CO2; 0.359, 0.661, tmp_cumulo+pH_cumulo+interval_yield+interval_Pdt.+rab_integral+RQ_integral+AS_Vol.+consum_O2+generate_CO2; 0.338, 0.661, tmp_cumulo+pH_cumulo+AN+interval_yield+OD+RQ_integral+AS_Vol.+emission_O2+consum_O2+interval_O2+generate_CO2; 0.328, 0.661, tmp+pH_cumulo+AN+interval_yield+interval_Pdt.+OD+Feed_Vol+RQ_integral+AS_Vol.+consum_O2+interval_O2+generate_CO2; 0.349, 0.661, tmp_cumulo+pH_cumulo+interval_yield+OD+Cell_conc._interval+RQ_integral+AS_Vol.+emission_O2+consum_O2+generate_CO2; 0.359, 0.661, tmp+AN+interval_yield+interval_Pdt.+RQ_integral+AS_Vol.+emission_CO2+consum_O2+generate_CO2; 0.368, 0.661, tmp_cumulo+AN+interval_yield+interval_Pdt.+RS_cumulo+RQ_integral+consum_O2+generate_CO2; 0.358, 0.661, tmp+interval_yield+interval_Pdt.+Feed_Vol+RQ_integral+AS_Vol.+emission_CO2+consum_O2+generate_CO2; 0.338, 0.661, tmp_cumulo+pH_cumulo+interval_yield+interval_Pdt.+OD+RS_cumulo+RQ_integral+AS_Vol.+emission_O2+consum_O2+generate_CO2; 0.348, 0.661, tmp_cumulo+AN+interval_yield+interval_Pdt.+OD+RS_cumulo+RQ_integral+emission_CO2+consum_O2+generate_CO2; 0.358, 0.661, tmp+pH+interval_yield+interval_Pdt.+RQ_integral+AS_Vol.+emission_CO2+consum_O2+generate_CO2; 0.358, 0.661, tmp_cumulo+interval_yield+interval_Pdt.+RS_cumulo+Cell_conc._interval+RQ_integral+emission_CO2+consum_O2+generate_CO2; 0.338, 0.661, tmp_cumulo+pH_cumulo+AN_cumulo+interval_yield+interval_Pdt.+OD+rab_integral+RQ_integral+AS_Vol.+consum_O2+generate_CO2; 0.348, 0.661, tmp_cumulo+pH_cumulo+PL_cumulo+interval_yield+OD+RS_cumulo+RQ_integral+AS_Vol.+consum_O2+generate_CO2; 0.348, 0.661, tmp_cumulo+pH+pH_cumulo+interval_yield+OD+RS_cumulo+RQ_integral+AS_Vol.+consum_O2+generate_CO2; 0.348, 0.661, tmp_cumulo+pH+interval_yield+interval_Pdt.+OD+RS_cumulo+RQ_integral+emission_CO2+consum_O2+generate_CO2; 0.348, 0.661, tmp_cumulo+pH+interval_yield+interval_Pdt.+RS_cumulo+rab_integral+RQ_integral+emission_CO2+consum_O2+generate_CO2; 0.368, 0.661, tmp_cumulo+AN_cumulo+interval_yield+interval_Pdt.+RS_cumulo+RQ_integral+consum_O2+generate_CO2; 0.348, 0.661, tmp_cumulo+pH_cumulo+PL+interval_yield+OD+rab_integral+RQ_integral+AS_Vol.+consum_O2+generate_CO2; 0.348, 0.661, tmp_cumulo+pH_cumulo+interval_yield+OD+Feed_Vol+Cell_conc._interval+RQ_integral+AS_Vol.+consum_O2+generate_CO2; 0.358, 0.660, tmp_cumulo+interval_yield+interval_Pdt.+RQ_integral+AS_Vol.+emission_CO2+consum_O2+interval_O2+generate_CO2; 0.348, 0.660, tmp+tmp_cumulo+pH_cumulo+interval_yield+OD+RS_cumulo+RQ_integral+AS_Vol.+consum_O2+generate_CO2; 0.348, 0.660, tmp_cumulo+pH_cumulo+AN_cumulo+interval_yield+OD+Feed_Vol+RQ_integral+AS_Vol.+consum_O2+generate_CO2; 0.377, 0.660, tmp_cumulo+pH_cumulo+OD+RQ_integral+AS_Vol.+consum_O2+generate_CO2; 0.358, 0.660, tmp+interval_yield+interval_Pdt.+RQ_integral+AS_Vol.+emission_CO2+consum_O2+interval_O2+generate_CO2; 0.368, 0.660, tmp_cumulo+interval_yield+interval_Pdt.+RQ_integral+AS_Vol.+consum_O2+interval_O2+generate_CO2; 0.348, 0.660, tmp_cumulo+pH_cumulo+AN_cumulo+interval_yield+OD+RS_cumulo+RQ_integral+AS_Vol.+consum_O2+generate_CO2; 0.338, 0.660, tmp_cumulo+interval_yield+interval_Pdt.+Feed_Vol+RS_cumulo+rab_integral+RQ_integral+AS_Vol.+emission_CO2+consum_O2+generate_CO2; 0.338, 0.660, tmp_cumulo+pH_cumulo+AN+interval_yield+interval_Pdt.+RQ_integral+AS_Vol.+emission_CO2+consum_O2+interval_O2+generate_CO2; 0.348, 0.660, tmp_cumulo+pH_cumulo+AN_cumulo+interval_yield+OD+RQ_integral+AS_Vol.+emission_O2+consum_O2+generate_CO2; 0.338, 0.660, tmp_cumulo+pH_cumulo+interval_yield+OD+Feed_Vol+rab_integral+RQ_integral+AS_Vol.+emission_CO2+consum_O2+generate_

CO2; 0.358, 0.660, tmp+AN_cumulo+interval_yield+interval_Pdt.+RQ_integral+AS_Vol.+emission_CO2+consum_O2+generate_CO2; 0.338, 0.660, tmp_cumulo+pH_cumulo+interval_yield+OD+rab_integral+RQ_integral+AS_Vol.+emission_O2+emission_CO2+consum_O2+generate_CO2; 0.348, 0.660, tmp+pH_cumulo+interval_yield+interval_Pdt.+Feed_Vol+RQ_integral+AS_Vol.+consum_O2+interval_O2+generate_CO2; 0.348, 0.660, tmp_cumulo+interval_yield+interval_Pdt.+Feed_Vol+RS_cumulo+rab_integral+RQ_integral+emission_CO2+consum_O2+generate_CO2; 0.358, 0.660, tmp_cumulo+pH+pH_cumulo+interval_yield+OD+RS_cumulo+RQ_integral+consum_O2+generate_CO2; 0.348, 0.660, tmp+tmp_cumulo+interval_yield+interval_Pdt.+RS_cumulo+rab_integral+RQ_integral+emission_CO2+consum_O2+generate_CO2; 0.348, 0.660, tmp_cumulo+pH+pH_cumulo+AN+interval_yield+OD+RQ_integral+AS_Vol.+consum_O2+generate_CO2; 0.358, 0.660, tmp_cumulo+interval_yield+interval_Pdt.+RS_cumulo+RQ_integral+AS_Vol.+consum_O2+interval_O2+generate_CO2; 0.327, 0.660, tmp+pH_cumulo+interval_yield+interval_Pdt.+OD+Feed_Vol+rab_integral+RQ_integral+AS_Vol.+consum_O2+interval_O2+generate_CO2; 0.327, 0.660, tmp_cumulo+pH_cumulo+interval_yield+interval_Pdt.+OD+Cell_conc._interval+rab_integral+RQ_integral+AS_Vol.+emission_CO2+consum_O2+generate_CO2; 0.367, 0.660, tmp+pH_cumulo+interval_yield+interval_Pdt.+RQ_integral+AS_Vol.+consum_O2+generate_CO2; 0.348, 0.660, tmp_cumulo+pH_cumulo+interval_yield+interval_Pdt.+RQ_integral+AS_Vol.+emission_O2+emission_CO2+consum_O2+generate_CO2; 0.367, 0.660, tmp_cumulo+PL_cumulo+interval_yield+interval_Pdt.+RS_cumulo+RQ_integral+consum_O2+generate_CO2; 0.358, 0.660, tmp_cumulo+pH_cumulo+interval_yield+OD+RS_cumulo+RQ_integral+emission_CO2+consum_O2+generate_CO2; 0.337, 0.660, tmp_cumulo+pH+pH_cumulo+AN+interval_yield+OD+RQ_integral+AS_Vol.+consum_O2+interval_O2+generate_CO2; 0.348, 0.660, tmp_cumulo+pH_cumulo+AN+interval_yield+interval_Pdt.+RQ_integral+AS_Vol.+emission_CO2+consum_O2+generate_CO2; 0.337, 0.660, tmp_cumulo+pH_cumulo+AN+interval_yield+OD+Feed_Vol+rab_integral+RQ_integral+AS_Vol.+consum_O2+generate_CO2; 0.348, 0.660, tmp+interval_yield+interval_Pdt.+RS_cumulo+rab_integral+RQ_integral+AS_Vol.+emission_CO2+consum_O2+generate_CO2; 0.337, 0.660, tmp_cumulo+pH_cumulo+AN_cumulo+interval_yield+OD+RQ_integral+AS_Vol.+emission_CO2+consum_O2+interval_O2+generate_CO2; 0.337, 0.660, tmp_cumulo+pH_cumulo+AN+interval_yield+interval_Pdt.+OD+Feed_Vol+RQ_integral+AS_Vol.+consum_O2+generate_CO2; 0.337, 0.660, tmp_cumulo+pH_cumulo+PL_cumulo+interval_yield+interval_Pdt.+OD+RQ_integral+AS_Vol.+emission_CO2+consum_O2+generate_CO2; 0.337, 0.660, tmp_cumulo+pH_cumulo+AN_cumulo+interval_yield+OD+rab_integral+RQ_integral+AS_Vol.+emission_CO2+consum_O2+generate_CO2; 0.347, 0.660, tmp+tmp_cumulo+pH_cumulo+interval_yield+OD+Cell_conc._interval+RQ_integral+AS_Vol.+consum_O2+generate_CO2; 0.337, 0.660, tmp_cumulo+pH_cumulo+AN+interval_yield+OD+Cell_conc._interval+RQ_integral+AS_Vol.+consum_O2+interval_O2+generate_CO2; 0.357, 0.660, tmp_cumulo+pH+interval_yield+interval_Pdt.+RQ_integral+AS_Vol.+consum_O2+interval_O2+generate_CO2; 0.347, 0.660, tmp+interval_yield+interval_Pdt.+OD+RS_cumulo+rab_integral+RQ_integral+emission_CO2+consum_O2+generate_CO2; 0.367, 0.660, tmp_cumulo+pH+interval_yield+interval_Pdt.+RS_cumulo+RQ_integral+consum_O2+generate_CO2; 0.367, 0.660, tmp_cumulo+pH_cumulo+AN+interval_yield+OD+RQ_integral+consum_O2+generate_CO2; 0.347, 0.660, tmp_cumulo+pH_cumulo+interval_yield+interval_Pdt.+Cell_conc._interval+RQ_integral+AS_Vol.+consum_O2+interval_O2+generate_CO2; 0.347, 0.660, tmp_cumulo+pH+pH_cumulo+interval_yield+OD+RQ_integral+AS_Vol.+emission_O2+consum_O2+generate_CO2; 0.357, 0.660, tmp_cumulo+pH_cumulo+AN+interval_yield+interval_Pdt.+OD+RQ_integral+consum_O2+generate_CO2; 0.347, 0.660, tmp+tmp_cumulo+pH_cumulo+interval_yield+OD+RQ_integral+AS_Vol.+emission_CO2+consum_O2+generate_CO2; 0.347, 0.660, tmp_cumulo+pH_cumulo+AN_cumulo+interval_yield+OD+Cell_conc._interval+RQ_integral+AS_Vol.+consum_O2+generate_CO2; 0.337, 0.660, tmp_cumulo+pH_cumulo+PL+interval_yield+OD+rab_integral+RQ_integral+AS_Vol.+consum_O2+interval_O2+generate_CO2; 0.337, 0.660, tmp_cumulo+pH+pH_cumulo+interval_yield+interval_Pdt.+OD+RQ_integral+AS_Vol.+emission_CO2+consum_O2+generate_CO2; 0.357, 0.660, tmp_cumulo+interval_yield+interval_Pdt.+OD+RQ_integral+AS_Vol.+emission_CO2+consum_O2+generate_CO2; 0.347, 0.660, tmp+interval_yield+interval_Pdt.+OD+RS_cumulo+RQ_integral+AS_Vol.+emission_CO2+consum_O2+generate_CO2; 0.347, 0.660, tmp_cumulo+pH_cumulo+interval_yield+interval_Pdt.+RS_cumulo+rab_integral+RQ_integral+emission_CO2+consum_O2+generate_CO2; 0.326, 0.660, tmp_cumulo+pH_cumulo+interval_yield+interval_Pdt.+OD+Feed_Vol+RQ_integral+AS_Vol.+emission_CO2+consum_O2+interval_O2+generate_CO2; 0.367, 0.660, tmp_cumulo+pH_cumulo+interval_yield+OD+RS+RQ_integral+consum_O2+generate_CO2; 0.367, 0.660, tmp_cumulo+pH_cumulo+interval_yield+OD+RQ_integral+consum_O2+interval_O2+generate_CO2; 0.357, 0.660, tmp_cumulo+pH+interval_yield+interval_Pdt.+OD+RQ_integral+AS_Vol.+consum_O2+generate_CO2; 0.347, 0.660, tmp_cumulo+AN_cumulo+interval_yield+interval_Pdt.+OD+RS_cumulo+RQ_integral+emission_CO2+consum_O2+generate_CO2; 0.347, 0.660, tmp_cumulo+pH_cumulo+AN_cumulo+interval_yield+interval_Pdt.+RQ_integral+AS_Vol.+emission_CO2+consum_O2+generate_CO2; 0.347, 0.660, tmp+interval_yield+interval_Pdt.+Feed_Vol+RS_cumulo+RQ_integral+AS_Vol.+emission_CO2+consum_O2+generate_CO2; 0.336, 0.660, tmp_cumulo+interval_yield+interval_Pdt.+OD+RS_cumulo+RQ_integral+AS_Vol.+emission_O2+emission_CO2+consum_O2+generate_CO2; 0.336, 0.660, tmp_cumulo+pH_cumulo+AN_cumulo+interval_yield+OD+RQ_integral+AS_Vol.+emission_CO2+consum_O2+interval_O2+generate_CO2; 0.357, 0.660, tmp_cumulo+interval_yield+interval_Pdt.+OD+RS_cumulo+RQ_integral+emission_O2+consum_O2+generate_CO2; 0.347, 0.660, tmp_cumulo+pH_cumulo+PL_cumulo+interval_yield+interval_Pdt.+RQ_integral+AS_Vol.+consum_O2+interval_O2+generate_CO2; 0.347, 0.660, tmp_cumulo+pH+pH_cumulo+interval_yield+interval_Pdt.+RQ_integral+AS_Vol.+consum_O2+interval_O2+generate_CO2; 0.347, 0.660, tmp_cumulo+pH_cumulo+PL_cumulo+AN+interval_yield+OD+RQ_integral+AS_Vol.+consum_O2+generate_CO2; 0.347, 0.660, tmp_cumulo+interval_yield+interval_Pdt.+RS_cumulo+Cell_conc._interval+RQ_integral+AS_Vol.+emission_CO2+consum_O2+generate_CO2; 0.336, 0.659, tmp_cumulo+pH_cumulo+interval_yield+interval_Pdt.+OD+Feed_Vol+RQ_integral+AS_Vol.+emission_O2+consum_O2+generate_CO2; 0.347, 0.659, tmp_cumulo+pH_cumulo+interval_yield+OD+Feed_Vol+RQ_integral+

AS_Vol.+emission_O2+consum_O2+generate_CO2; 0.336, 0.659, tmp_cumulo+pH_cumulo+AN+interval_yield+OD+RS_cumulo+RQ_integral+AS_Vol.+consum_O2+interval_O2+generate_CO2; 0.336, 0.659, tmp_cumulo+pH+pH_cumulo+interval_yield+OD+RQ_integral+AS_Vol.+emission_O2+consum_O2+interval_O2+generate_CO2; 0.347, 0.659, tmp_cumulo+pH_cumulo+PL_cumulo+interval_yield+OD+RQ_integral+AS_Vol.+emission_CO2+consum_O2+generate_CO2; 0.366, 0.659, tmp_cumulo+pH_cumulo+interval_yield+RQ_integral+AS_Vol.+consum_O2+interval_O2+generate_CO2; 0.336, 0.659, tmp_cumulo+pH_cumulo+AN+interval_yield+interval_Pdt.+OD+RQ_integral+AS_Vol.+emission_O2+consum_O2+generate_CO2; 0.357, 0.659, tmp_cumulo+pH+interval_yield+interval_Pdt.+OD+RS_cumulo+RQ_integral+consum_O2+generate_CO2; 0.336, 0.659, tmp_cumulo+pH_cumulo+interval_yield+interval_Pdt.+Feed_Vol+rab_integral+RQ_integral+AS_Vol.+emission_CO2+consum_O2+generate_CO2; 0.357, 0.659, tmp+pH_cumulo+interval_yield+interval_Pdt.+RQ_integral+AS_Vol.+consum_O2+interval_O2+generate_CO2; 0.336, 0.659, tmp_cumulo+pH_cumulo+interval_yield+interval_Pdt.+OD+Cell_conc._interval+rab_integral+RQ_integral+AS_Vol.+consum_O2+generate_CO2; 0.336, 0.659, tmp_cumulo+pH_cumulo+interval_yield+OD+Feed_Vol+RQ_integral+AS_Vol.+emission_CO2+consum_O2+interval_O2+generate_CO2; 0.336, 0.659, tmp_cumulo+pH_cumulo+interval_yield+OD+Feed_Vol+RS_cumulo+rab_integral+RQ_integral+AS_Vol.+consum_O2+generate_CO2; 0.346, 0.659, tmp_cumulo+PL_cumulo+interval_yield+interval_Pdt.+RS_cumulo+RQ_integral+AS_Vol.+emission_CO2+consum_O2+generate_CO2; 0.336, 0.659, tmp_cumulo+pH_cumulo+interval_yield+OD+Feed_Vol+Cell_conc._interval+RQ_integral+AS_Vol.+consum_O2+interval_O2+generate_CO2; 0.336, 0.659, tmp_cumulo+pH+pH_cumulo+AN_cumulo+interval_yield+OD+RQ_integral+AS_Vol.+consum_O2+interval_O2+generate_CO2; 0.336, 0.659, tmp_cumulo+pH+pH_cumulo+interval_yield+OD+rab_integral+RQ_integral+AS_Vol.+emission_CO2+consum_O2+generate_CO2; 0.325, 0.659, tmp_cumulo+pH_cumulo+AN+interval_yield+interval_Pdt.+OD+RQ_integral+AS_Vol.+emission_CO2+consum_O2+interval_O2+generate_CO2; 0.356, 0.659, tmp_cumulo+pH_cumulo+interval_yield+interval_Pdt.+OD+rab_integral+RQ_integral+consum_O2+generate_CO2; 0.356, 0.659, tmp_cumulo+interval_yield+interval_Pdt.+OD+RS_cumulo+RQ_integral+AS_Vol.+consum_O2+generate_CO2; 0.346, 0.659, tmp+tmp_cumulo+interval_yield+interval_Pdt.+OD+RS_cumulo+RQ_integral+emission_CO2+consum_O2+generate_CO2; 0.336, 0.659, tmp_cumulo+pH_cumulo+interval_yield+interval_Pdt.+rab_integral+RQ_integral+AS_Vol.+emission_O2+emission_CO2+consum_O2+generate_CO2; 0.366, 0.659, tmp+pH_cumulo+interval_yield+OD+Cell_conc._interval+RQ_integral+consum_O2+generate_CO2; 0.356, 0.659, tmp_cumulo+pH_cumulo+interval_yield+rab_integral+RQ_integral+AS_Vol.+consum_O2+interval_O2+generate_CO2; 0.336, 0.659, tmp_cumulo+AN+interval_yield+interval_Pdt.+RS_cumulo+rab_integral+RQ_integral+AS_Vol.+emission_CO2+consum_O2+generate_CO2; 0.346, 0.659, tmp_cumulo+pH_cumulo+AN_cumulo+interval_yield+interval_Pdt.+OD+RS_cumulo+RQ_integral+consum_O2+generate_CO2; 0.356, 0.659, tmp_cumulo+pH+interval_yield+OD+RQ_integral+AS_Vol.+consum_O2+interval_O2+generate_CO2; 0.336, 0.659, tmp_cumulo+pH_cumulo+interval_yield+OD+Feed_Vol+RS_cumulo+RQ_integral+AS_Vol.+consum_O2+interval_O2+generate_CO2; 0.346, 0.659, tmp_cumulo+pH+pH_cumulo+interval_yield+OD+Feed_Vol+RQ_integral+AS_Vol.+consum_O2+generate_CO2; 0.336, 0.659, tmp_cumulo+pH_cumulo+interval_yield+OD+RS_cumulo+RQ_integral+AS_Vol.+emission_O2+consum_O2+interval_O2+generate_CO2; 0.346, 0.659, tmp+pH_cumulo+interval_yield+interval_Pdt.+RQ_integral+AS_Vol.+emission_CO2+consum_O2+interval_O2+generate_CO2; 0.336, 0.659, tmp_cumulo+pH+interval_yield+interval_Pdt.+RS_cumulo+rab_integral+RQ_integral+AS_Vol.+emission_CO2+consum_O2+generate_CO2; 0.376, 0.659, tmp+interval_yield+interval_Pdt.+RQ_integral+AS_Vol.+consum_O2+generate_CO2; 0.366, 0.659, tmp+tmp_cumulo+interval_yield+interval_Pdt.+RS_cumulo+RQ_integral+consum_O2+generate_CO2; 0.356, 0.659, tmp+pH_cumulo+AN_cumulo+interval_yield+interval_Pdt.+OD+RQ_integral+consum_O2+generate_CO2; 0.346, 0.659, tmp+interval_yield+interval_Pdt.+OD+RS_cumulo+RQ_integral+emission_O2+emission_CO2+consum_O2+generate_CO2; 0.346, 0.659, tmp+tmp_cumulo+pH_cumulo+interval_yield+interval_Pdt.+RQ_integral+AS_Vol.+consum_O2+interval_O2+generate_CO2; 0.336, 0.659, tmp_cumulo+pH_cumulo+PL_cumulo+AN+interval_yield+OD+RQ_integral+AS_Vol.+consum_O2+interval_O2+generate_CO2; 0.336, 0.659, tmp_cumulo+pH+interval_yield+interval_Pdt.+OD+RS_cumulo+RQ_integral+AS_Vol.+emission_CO2+consum_O2+generate_CO2; 0.346, 0.659, tmp_cumulo+pH_cumulo+interval_yield+OD+RS_cumulo+Cell_conc._interval+RQ_integral+AS_Vol.+consum_O2+generate_CO2; 0.325, 0.659, tmp+pH_cumulo+interval_yield+interval_Pdt.+OD+Feed_Vol+rab_integral+RQ_integral+AS_Vol.+emission_CO2+consum_O2+generate_CO2; 0.336, 0.659, tmp_cumulo+pH+pH_cumulo+interval_yield+OD+Feed_Vol+RQ_integral+AS_Vol.+consum_O2+interval_O2+generate_CO2; 0.346, 0.659, tmp_cumulo+pH_cumulo+interval_yield+OD+rab_integral+RQ_integral+Accum._Yield+AS_Vol.+consum_O2+generate_CO2; 0.356, 0.659, tmp_cumulo+pH_cumulo+AN_cumulo+interval_yield+OD+RS_cumulo+RQ_integral+consum_O2+generate_CO2; 0.346, 0.659, tmp_cumulo+pH+pH_cumulo+AN_cumulo+interval_yield+OD+RQ_integral+AS_Vol.+consum_O2+generate_CO2; 0.336, 0.659, tmp_cumulo+pH_cumulo+interval_yield+OD+Feed_Vol+RQ_integral+AS_Vol.+emission_O2+consum_O2+interval_O2+generate_CO2; 0.346, 0.659, tmp_cumulo+pH_cumulo+interval_yield+interval_Pdt.+RS_cumulo+RQ_integral+AS_Vol.+emission_O2+consum_O2+generate_CO2; 0.356, 0.659, tmp_cumulo+pH_cumulo+AN_cumulo+interval_yield+interval_Pdt.+OD+RQ_integral+consum_O2+generate_CO2; 0.336, 0.659, tmp+pH_cumulo+interval_yield+interval_Pdt.+OD+RQ_integral+AS_Vol.+emission_O2+emission_CO2+consum_O2+generate_CO2; 0.335, 0.659, tmp_cumulo+pH_cumulo+AN+interval_yield+interval_Pdt.+rab_integral+RQ_integral+AS_Vol.+emission_CO2+consum_O2+generate_CO2; 0.335, 0.659, tmp_cumulo+pH_cumulo+interval_yield+OD+Cell_conc._interval+RQ_integral+AS_Vol.+emission_CO2+consum_O2+interval_O2+generate_CO2; 0.325, 0.659, tmp_cumulo+pH_cumulo+AN_cumulo+interval_yield+OD+Feed_Vol+rab_integral+RQ_integral+AS_Vol.+consum_O2+interval_O2+generate_CO2; 0.325, 0.659, tmp_cumulo+pH_cumulo+interval_yield+interval_Pdt.+OD+Feed_Vol+RS_cumulo+RQ_integral+AS_Vol.+consum_O2+interval_O2+generate_CO2; 0.335, 0.659, tmp_cumulo+pH_cumulo+interval_yield+interval_Pdt.+Feed_Vol+RQ_integral+AS_Vol.+emission_CO2+consum_O2+interval_O2+generate_CO2; 0.375, 0.659, tmp_cumulo+interval_yield+OD+RS_cumulo+RQ_integral+ consum_O2+generate_CO2; 0.346, 0.659, tmp+tmp_cumulo+pH_cumulo+AN+interval_yield+OD+RQ_integral+AS_Vol.+consum_O2+generate_CO2; 0.346, 0.659, tmp_cumulo+pH_cumulo+PL_cumulo+AN_cumulo+interval_yield+OD+RQ_integral+AS_Vol.+consum_O2+generate_CO2; 0.335, 0.659, tmp_cumulo+pH_cumulo+interval_yield+OD+RS_cumulo+RQ_integral+AS_Vol.+emission_CO2+consum_O2+interval_O2+generate_CO2; 0.325, 0.659, tmp_cumulo+pH_cumulo+AN+interval_yield+OD+rab_integral+RQ_integral+AS_Vol.+emission_CO2+consum_O2+interval_O2+generate_CO2; 0.335, 0.659, tmp_cumulo+pH+pH_cumulo+interval_yield+OD+RQ_integral+AS_Vol.+emission_CO2+consum_O2+interval_O2+generate_CO2; 0.325, 0.659, tmp_cumulo+pH_cumulo+interval_yield+interval_Pdt.+OD+rab_integral+RQ_integral+AS_Vol.+emission_O2+consum_O2+interval_O2+generate_CO2; 0.356, 0.659, tmp+tmp_cumulo+pH_cumulo+interval_yield+OD+RS_cumulo+RQ_integral+consum_O2+generate_CO2; 0.346, 0.659, tmp_cumulo+pH_cumulo+interval_yield+OD+RS_cumulo+rab_integral+RQ_integral+consum_O2+interval_O2+generate_CO2; 0.335, 0.659, tmp_cumulo+pH_cumulo+PL_cumulo+interval_yield+interval_Pdt.+OD+rab_integral+RQ_integral+AS_Vol.+consum_O2+generate_CO2; 0.335, 0.659, tmp_cumulo+pH_cumulo+AN_cumulo+interval_yield+interval_Pdt.+OD+RQ_integral+AS_Vol.+emission_O2+consum_O2+generate_CO2; 0.335, 0.659, tmp_cumulo+pH_cumulo+AN_cumulo+interval_yield+interval_Pdt.+OD+Feed_Vol+RQ_integral+AS_Vol.+consum_O2+generate_CO2; 0.346, 0.659, tmp+interval_yield+interval_Pdt.+RS_cumulo+RQ_integral+AS_Vol.+emission_O2+emission_CO2+consum_O2+generate_CO2; 0.324, 0.659, tmp_cumulo+pH_cumulo+interval_yield+interval_Pdt.+OD+Feed_Vol+RQ_integral+AS_Vol.+emission_O2+consum_O2+interval_O2+generate_CO2; 0.324, 0.659, tmp_cumulo+pH_cumulo+interval_yield+interval_Pdt.+OD+RS_cumulo+RQ_integral+AS_Vol.+emission_O2+emission_CO2+consum_O2+generate_CO2; 0.346, 0.659, tmp+pH_cumulo+interval_yield+interval_Pdt.+RQ_integral+AS_Vol.+emission_O2+emission_CO2+consum_O2+generate_CO2; 0.324, 0.659, tmp+tmp_cumulo+pH_cumulo+interval_yield+interval_Pdt.+OD+rab_integral+RQ_integral+AS_Vol.+emission_CO2+consum_O2+generate_CO2; 0.346, 0.659, tmp_cumulo+pH_cumulo+interval_yield+interval_Pdt.+OD+RS_cumulo+RQ_integral+emission_CO2+consum_O2+generate_CO2; 0.345, 0.659, tmp_cumulo+pH+interval_yield+interval_Pdt.+rab_integral+RQ_integral+AS_Vol.+emission_CO2+consum_O2+generate_CO2; 0.356, 0.659, tmp_cumulo+interval_yield+interval_Pdt.+RS_cumulo+RQ_integral+emission_CO2+consum_O2+interval_O2+generate_CO2; 0.345, 0.659, tmp_cumulo+pH_cumulo+PL+interval_yield+interval_Pdt.+OD+RQ_integral+AS_Vol.+consum_O2+generate_CO2; 0.324, 0.659, tmp_cumulo+pH_cumulo+AN_cumulo+interval_yield+interval_Pdt.+OD+Feed_Vol+RQ_integral+AS_Vol.+consum_O2+interval_O2+generate_CO2; 0.356, 0.659, tmp+pH_cumulo+AN+interval_yield+interval_Pdt.+OD+RQ_integral+consum_O2+generate_CO2; 0.335, 0.659, tmp_cumulo+pH_cumulo+interval_yield+OD+Cell_conc._interval+RQ_integral+AS_Vol.+emission_O2+consum_O2+interval_O2+generate_CO2; 0.335, 0.659, tmp_cumulo+pH_cumulo+interval_yield+interval_Pdt.+RS_cumulo+RQ_integral+AS_Vol.+emission_CO2+consum_O2+interval_O2+generate_CO2; 0.324, 0.659, tmp_cumulo+pH_cumulo+interval_yield+interval_Pdt.+OD+Feed_Vol+RS_cumulo+rab_integral+RQ_integral+AS_Vol.+consum_O2+generate_CO2; 0.355, 0.659, tmp_cumulo+interval_yield+interval_Pdt.+RS_cumulo+rab_integral+RQ_integral+emission_O2+consum_O2+generate_CO2; 0.355, 0.659, tmp_cumulo+pH_cumulo+interval_yield+OD+RS_cumulo+RQ_integral+emission_O2+consum_O2+generate_CO2; 0.335, 0.659, tmp_cumulo+pH_cumulo+AN_cumulo+interval_yield+OD+Cell_conc._interval+RQ_integral+AS_Vol.+consum_O2+interval_O2+generate_CO2; 0.355, 0.659, tmp+pH_cumulo+interval_yield+OD+RQ_integral+AS_Vol.+consum_O2+interval_O2+generate_CO2; 0.335, 0.659, tmp_cumulo+pH+pH_cumulo+interval_yield+interval_Pdt.+OD+rab_integral+RQ_integral+AS_Vol.+consum_O2+generate_CO2; 0.355, 0.659, tmp+pH_cumulo+interval_yield+OD+Cell_conc._interval+RQ_integral+AS_Vol.+consum_O2+generate_CO2; 0.335, 0.659, tmp_cumulo+pH_cumulo+AN+AN_cumulo+interval_yield+OD+RQ_integral+AS_Vol.+consum_O2+interval_O2+generate_CO2; 0.345, 0.659, tmp_cumulo+pH+pH_cumulo+interval_yield+OD+Cell_conc._interval+RQ_integral+AS_Vol.+consum_O2+generate_CO2; 0.355, 0.659, tmp+pH+interval_yield+interval_Pdt.+RS_cumulo+RQ_integral+emission_CO2+consum_O2+generate_CO2; 0.345, 0.659, tmp+tmp_cumulo+pH_cumulo+interval_yield+OD+RQ_integral+AS_Vol.+emission_O2+consum_O2+generate_CO2; 0.324, 0.659, tmp_cumulo+pH_cumulo+AN+interval_yield+interval_Pdt.+OD+rab_integral+RQ_integral+AS_Vol.+consum_O2+interval_O2+generate_CO2; 0.345, 0.659, tmp_cumulo+pH_cumulo+PL_cumulo+interval_yield+OD+Feed_Vol+RQ_integral+AS_Vol.+consum_O2+generate_CO2; 0.335, 0.659, tmp_cumulo+pH_cumulo+interval_yield+OD+RQ_integral+AS_Vol.+emission_O2+emission_CO2+consum_O2+interval_O2+generate_CO2; 0.355, 0.658, tmp+interval_yield+interval_Pdt.+RS_cumulo+Cell_conc._interval+RQ_integral+emission_CO2+consum_O2+generate_CO2; 0.324, 0.658, tmp_cumulo+pH_cumulo+interval_yield+interval_Pdt.+OD+RQ_integral+AS_Vol.+emission_O2+emission_CO2+consum_O2+interval_O2+generate_CO2; 0.335, 0.658, tmp_cumulo+AN_cumulo+interval_yield+interval_Pdt.+RS_cumulo+rab_integral+RQ_integral+AS_Vol.+emission_CO2+consum_O2+generate_CO2; 0.345, 0.658, tmp+pH_cumulo+interval_yield+interval_Pdt.+OD+RQ_integral+AS_Vol.+consum_O2+interval_O2+generate_CO2; 0.365, 0.658, tmp_cumulo+pH_cumulo+AN_cumulo+interval_yield+OD+RQ_integral+consum_O2+generate_CO2; 0.345, 0.658, tmp_cumulo+pH_cumulo+AN+AN_cumulo+interval_yield+OD+RQ_integral+AS_Vol.+consum_O2+generate_CO2; 0.335, 0.658, tmp_cumulo+pH_cumulo+interval_yield+interval_Pdt.+RS_cumulo+RQ_integral+AS_Vol.+emission_O2+emission_CO2+consum_O2+generate_CO2; 0.355, 0.658, tmp_cumulo+interval_yield+interval_Pdt.+Feed_Vol+RS_cumulo+RQ_integral+AS_Vol.+consum_O2+generate_CO2; 0.365, 0.658, tmp_cumulo+interval_yield+interval_Pdt.+Feed_Vol+RS_cumulo+RQ_integral+consum_O2+generate_CO2; 0.335, 0.658, tmp_cumulo+pH_cumulo+AN_cumulo+interval_yield+interval_Pdt.+rab_integral+RQ_integral+AS_Vol.+emission_CO2+consum_O2+generate_CO2; 0.335, 0.658, tmp_cumulo+pH_cumulo+PL_cumulo+AN_cumulo+interval_yield+OD+RQ_integral+AS_Vol.+consum_O2+interval_O2+generate_CO2; 0.345, 0.658, tmp_cumulo+pH_cumulo+PL_cumulo+interval_yield+OD+Cell_conc._interval+RQ_integral+AS_Vol.+consum_O2+generate_CO2; 0.355, 0.658, tmp_cumulo+pH_cumulo+interval_yield+interval_Pdt.+Feed_

Vol+RQ_integral+AS_Vol.+consum_O2+generate_CO2; 0.355, 0.658, tmp_cumulo+pH_cumulo+PL_cumulo+interval_yield+OD+RS_cumulo+RQ_integral+consum_O2+generate_CO2; 0.335, 0.658, tmp_cumulo+pH_cumulo+AN_cumulo+interval_yield+OD+Feed_Vol+rab_integral+RQ_integral+AS_Vol.+consum_O2+generate_CO2; 0.345, 0.658, tmp+pH_cumulo+interval_yield+interval_Pdt.+Feed_Vol+RQ_integral+AS_Vol.+emission_CO2+consum_O2+generate_CO2; 0.335, 0.658, tmp_cumulo+pH+pH_cumulo+interval_yield+OD+RS_cumulo+RQ_integral+AS_Vol.+consum_O2+interval_O2+generate_CO2; 0.334, 0.658, tmp+tmp_cumulo+interval_yield+interval_Pdt.+RS_cumulo+rab_integral+RQ_integral+AS_Vol.+emission_CO2+consum_O2+generate_CO2; 0.334, 0.658, tmp_cumulo+pH_cumulo+interval_yield+interval_Pdt.+OD+RS_cumulo+RQ_integral+emission_O2+emission_CO2+consum_O2+generate_CO2; 0.355, 0.658, tmp_cumulo+interval_yield+interval_Pdt.+Feed_Vol+RQ_integral+AS_Vol.+emission_CO2+consum_O2+generate_CO2; 0.355, 0.658, tmp_cumulo+interval_yield+interval_Pdt.+OD+RS_cumulo+rab_integral+RQ_integral+consum_O2+generate_CO2; 0.355, 0.658, tmp+pH_cumulo+interval_yield+interval_Pdt.+OD+rab_integral+RQ_integral+consum_O2+generate_CO2; 0.334, 0.658, tmp_cumulo+pH_cumulo+AN+interval_yield+interval_Pdt.+OD+RS_cumulo+RQ_integral+AS_Vol.+consum_O2+generate_CO2; 0.334, 0.658, tmp_cumulo+pH_cumulo+AN_cumulo+interval_yield+OD+RS_cumulo+RQ_integral+AS_Vol.+consum_O2+interval_O2+generate_CO2; 0.324, 0.658, tmp_cumulo+pH_cumulo+interval_yield+OD+Feed_Vol+rab_integral+RQ_integral+AS_Vol.+emission_CO2+consum_O2+interval_O2+generate_CO2; 0.334, 0.658, tmp+tmp_cumulo+pH_cumulo+interval_yield+interval_Pdt.+OD+rab_integral+RQ_integral+AS_Vol.+consum_O2+generate_CO2; 0.334, 0.658, tmp+pH_cumulo+interval_yield+interval_Pdt.+OD+Cell_conc._interval+RQ_integral+AS_Vol.+emission_CO2+consum_O2+generate_CO2; 0.323, 0.658, tmp_cumulo+pH_cumulo+AN_cumulo+interval_yield+OD+rab_integral+RQ_integral+AS_Vol.+emission_CO2+consum_O2+interval_O2+generate_CO2; 0.345, 0.658, tmp+tmp_cumulo+pH_cumulo+interval_yield+OD+Feed_Vol+RQ_integral+AS_Vol.+consum_O2+generate_CO2; 0.323, 0.658, tmp_cumulo+pH_cumulo+AN_cumulo+interval_yield+interval_Pdt.+OD+RQ_integral+AS_Vol.+emission_CO2+consum_O2+interval_O2+generate_CO2; 0.334, 0.658, tmp_cumulo+pH_cumulo+PL_cumulo+interval_yield+OD+Feed_Vol+RQ_integral+AS_Vol.+consum_O2+interval_O2+generate_CO2; 0.334, 0.658, tmp_cumulo+pH_cumulo+AN_cumulo+interval_yield+interval_Pdt.+RQ_integral+AS_Vol.+emission_CO2+consum_O2+interval_O2+generate_CO2; 0.364, 0.658, tmp+interval_yield+interval_Pdt.+RQ_integral+AS_Vol.+consum_O2+interval_O2+generate_CO2; 0.344, 0.658, tmp+tmp_cumulo+pH_cumulo+AN_cumulo+interval_yield+OD+RQ_integral+AS_Vol.+consum_O2+generate_CO2; 0.334, 0.658, tmp+pH_cumulo+AN+interval_yield+interval_Pdt.+OD+Feed_Vol+RQ_integral+AS_Vol.+consum_O2+generate_CO2; 0.334, 0.658, tmp_cumulo+pH_cumulo+AN+interval_yield+OD+rab_integral+RQ_integral+AS_Vol.+emission_O2+consum_O2+generate_CO2; 0.334, 0.658, tmp_cumulo+pH_cumulo+interval_yield+interval_Pdt.+OD+Cell_conc._interval+RQ_integral+AS_Vol.+emission_O2+consum_O2+generate_CO2; 0.354, 0.658, tmp_cumulo+pH_cumulo+AN+interval_yield+interval_Pdt.+RQ_integral+AS_Vol.+consum_O2+generate_CO2; 0.334, 0.658, tmp_cumulo+pH_cumulo+interval_yield+OD+rab_integral+RQ_integral+AS_Vol.+consum_O2+generate_CO2; 0.334, 0.658, tmp_cumulo+pH_cumulo+interval_yield+OD+rab_integral+RQ_integral+AS_Vol.+consum_O2+generate_CO2; 0.334, 0.658, tmp_cumulo+pH_cumulo+interval_yield+OD+rab_integral+RQ_integral+AS_Vol.+consum_O2+generate_CO2; 0.334, 0.658, tmp_cumulo+pH_cumulo+interval_yield+OD+rab_integral+RQ_integral+AS_Vol.+consum_O2+generate_CO2; 0.334, 0.658, tmp_cumulo+pH_cumulo+interval_yield+OD+rab-integral+RQ_integral+Accum._Yield+AS_Vol.+consum_O2+interval_O2+generate_CO2; 0.334, 0.658, tmp_cumulo+pH_cumulo+AN+interval_yield+interval_Pdt.+Feed_Vol+RQ_integral+AS_Vol.+consum_O2+interval_O2+generate_CO2; 0.334, 0.658, tmp+tmp_cumulo+pH_cumulo+AN+interval_yield+OD+RQ_integral+AS_Vol.+consum_O2+interval_O2+generate_CO2; 0.364, 0.658, tmp_cumulo+pH+interval_yield+interval_Pdt.+RQ_integral+AS_Vol.+consum_O2+generate_CO2; 0.344, 0.658, tmp_cumulo+pH_cumulo+interval_yield+interval_Pdt.+rab_integral+RQ_integral+AS_Vol.+emission_O2+consum_O2+generate_CO2; 0.334, 0.658, tmp_cumulo+pH_cumulo+interval_yield+OD+Feed_Vol+Cell_conc._interval+rab_integral+RQ_integral+AS_Vol.+consum_O2+generate_CO2; 0.344, 0.658, tmp+tmp_cumulo+pH_cumulo+interval_yield+interval_Pdt.+OD+RS_cumulo+RQ_integral+consum_O2+generate_CO2; 0.344, 0.658, tmp+pH_cumulo+AN+interval_yield+interval_Pdt.+RQ_integral+AS_Vol.+emission_CO2+consum_O2+generate_CO2; 0.334, 0.658, tmp_cumulo+pH_cumulo+interval_yield+interval_Pdt.+OD+Feed_Vol+Cell_conc._interval+RQ_integral+AS_Vol.+consum_O2+generate_CO2; 0.323, 0.658, tmp_cumulo+pH+pH_cumulo+interval_yield+interval_Pdt.+OD+rab_integral+RQ_integral+AS_Vol.+emission_CO2+consum_O2+generate_CO2; 0.344, 0.658, tmp+interval_yield+interval_Pdt.+rab_integral+RQ_integral+AS_Vol.+emission_O2+emission_CO2+consum_O2+generate_CO2; 0.344, 0.658, tmp_cumulo+AN+interval_yield+interval_Pdt.+RS_cumulo+RQ_integral+emission_O2+emission_CO2+consum_O2+generate_CO2; 0.323, 0.658, tmp_cumulo+pH_cumulo+interval_yield+interval_Pdt.+OD+Feed_Vol+RS_cumulo+RQ_integral+AS_Vol.+emission_CO2+consum_O2+generate_CO2; 0.344, 0.658, tmp+interval_yield+interval_Pdt.+OD+Cell_conc._interval+RQ_integral+AS_Vol.+emission_CO2+consum_O2+generate_CO2; 0.354, 0.658, tmp_cumulo+pH_cumulo+AN_cumulo+interval_yield+interval_Pdt.+RQ_integral+AS_Vol.+consum_O2+generate_CO2; 0.334, 0.658, tmp_cumulo+pH_cumulo+interval_yield+OD+RS_cumulo+rab_integral+RQ_integral+AS_Vol.+emission_O2+consum_O2+generate_CO2; 0.334, 0.658, tmp+tmp_cumulo+pH_cumulo+interval_yield+OD+rab_integral+RQ_integral+AS_Vol.+emission_CO2+consum_O2+generate_CO2; 0.344, 0.658, tmp+pH_cumulo+AN_cumulo+interval_yield+interval_Pdt.+RQ_integral+AS_Vol.+emission_CO2+consum_O2+generate_CO2; 0.364, 0.658, tmp+interval_yield+interval_Pdt.+OD+RQ_integral+emission_CO2+consum_O2+generate_CO2; 0.334, 0.658, tmp+tmp_cumulo+pH_cumulo+interval_yield+interval_Pdt.+OD+Feed_Vol+RQ_integral+AS_Vol.+consum_O2+generate_CO2; 0.364, 0.658, tmp_cumulo+pH+interval_yield+OD+RQ_integral+AS_Vol.+consum_O2+generate_CO2; 0.334, 0.658, tmp+pH_cumulo+AN+interval_yield+interval_Pdt.+OD+RQ_integral+AS_Vol.+emission_CO2+consum_O2+generate_CO2; 0.354, 0.658, tmp_cumulo+interval_yield+interval_Pdt.+RQ_integral+AS_Vol.+emission_O2+emission_CO2+consum_O2+generate_CO2; 0.344, 0.658, tmp_cumulo+pH+pH_cumulo+interval_yield+interval_Pdt.+OD+RS_cumulo+RQ_integral+consum_O2+generate_CO2; 0.334, 0.658, tmp+pH_cumulo+interval_yield+interval_Pdt.+OD+Feed_Vol+RS_cumulo+RQ_integral+AS_Vol.+consum_O2+generate_CO2; 0.354, 0.658, tmp_cumulo+pH_cumulo+interval_yield+OD+Feed_Vol+rab_integral+RQ_integral+consum_O2+generate_CO2; 0.354, 0.658, tmp_cumulo+pH_cumulo+interval_yield+interval_Pdt.+OD+Feed_Vol+RQ_integral+consum_O2+generate_CO2; 0.334, 0.658, tmp_cumulo+AN+interval_yield+interval_Pdt.+OD+RS_cumulo+rab_integral+RQ_integral+ emission_CO2+consum_O2+generate_CO2; 0.354, 0.658, tmp_cumulo+pH_cumulo+interval_yield+OD+RS_cumulo+Cell_conc._interval+RQ_integral+consum_O2+generate_CO2; 0.333, 0.658, tmp+pH_cumulo+AN_cumulo+interval_yield+interval_Pdt.+OD+RQ_integral+AS_Vol.+emission_CO2+consum_O2+generate_CO2; 0.354, 0.658, tmp+pH_cumulo+interval_yield+OD+Feed_Vol+RQ_integral+AS_Vol.+consum_O2+generate_CO2; 0.333, 0.658, tmp_cumulo+pH_cumulo+interval_yield+interval_Pdt.+RQ_integral+AS_Vol.+emission_O2+emission_CO2+consum_O2+interval_O2+generate_CO2; 0.344, 0.658, tmp_cumulo+pH+interval_yield+interval_Pdt.+RQ_integral+AS_Vol.+emission_CO2+consum_O2+interval_O2+generate_CO2; 0.373, 0.658, tmp_cumulo+interval_yield+interval_Pdt.+RQ_integral+AS_Vol.+consum_O2+generate_CO2; 0.323, 0.658, tmp+pH_cumulo+interval_yield+interval_Pdt.+OD+Feed_Vol+RQ_integral+AS_Vol.+emission_CO2+consum_O2+interval_O2+generate_CO2; 0.333, 0.658, tmp+pH_cumulo+PL_cumulo+interval_yield+interval_Pdt.+OD+Feed_Vol+RQ_integral+AS_Vol.+consum_O2+generate_CO2; 0.344, 0.658, tmp_cumulo+pH_cumulo+AN+interval_yield+OD+RS_cumulo+rab_integral+RQ_integral+consum_O2+generate_CO2; 0.373, 0.658, tmp_cumulo+pH_cumulo+RQ_integral+AS_Vol.+consum_O2+interval_O2+generate_CO2; 0.333, 0.658, tmp_cumulo+pH_cumulo+interval_yield+OD+Feed_Vol+rab_integral+RQ_integral+AS_Vol.+emission_CO2+consum_O2+generate_CO2; 0.333, 0.658, tmp_cumulo+pH_cumulo+PL_cumulo+interval_yield+OD+RQ_integral+AS_Vol.+emission_CO2+consum_O2+interval_O2+generate_CO2; 0.333, 0.658, tmp_cumulo+pH+interval_yield+interval_Pdt.+OD+RS_cumulo+rab_integral+RQ_integral+emission_CO2+consum_O2+generate_CO2; 0.344, 0.658, tmp_cumulo+interval_yield+interval_Pdt.+OD+Feed_Vol+RS_cumulo+RQ_integral+emission_CO2+consum_O2+generate_CO2; 0.364, 0.658, tmp+interval_yield+interval_Pdt.+Feed_Vol+RQ_integral+emission_CO2+consum_O2+generate_CO2; 0.344, 0.658, tmp+pH_cumulo+PL_cumulo+interval_yield+interval_Pdt.+OD+RQ_integral+AS_Vol.+consum_O2+generate_CO2; 0.333, 0.658, tmp+tmp_cumulo+pH_cumulo+interval_yield+OD+RS_cumulo+RQ_integral+AS_Vol.+consum_O2+interval_O2+generate_CO2; 0.344, 0.658, tmp_cumulo+pH_cumulo+interval_yield+interval_Pdt.+Cell_conc._interval+RQ_integral+AS_Vol.+emission_CO2+consum_O2+generate_CO2; 0.344, 0.658, tmp+pH+interval_yield+interval_Pdt.+OD+RQ_integral+AS_Vol.+emission_CO2+consum_O2+generate_CO2; 0.344, 0.658, tmp_cumulo+pH_cumulo+interval_yield+OD+RS_cumulo+rab_integral+RQ_integral+emission_CO2+consum_O2+generate_CO2; 0.333, 0.658, tmp_cumulo+pH_cumulo+AN+interval_yield+OD+RS_cumulo+rab_integral+RQ_integral+AS_Vol.+consum_O2+generate_CO2; 0.354, 0.658, tmp_cumulo+interval_yield+interval_Pdt.+Cell_conc._interval+RQ_integral+AS_Vol.+emission_CO2+consum_O2+generate_CO2; 0.333, 0.658, tmp_cumulo+pH_cumulo+interval_yield+interval_Pdt.+rab_integral+RQ_integral+AS_Vol.+emission_O2+consum_O2+interval_O2+generate_CO2; 0.344, 0.658, tmp_cumulo+pH_cumulo+interval_yield+interval_Pdt.+OD+RS_cumulo+RQ_integral+consum_O2+interval_O2+generate_CO2; 0.354, 0.658, tmp_cumulo+AN+interval_yield+interval_Pdt.+RQ_integral+AS_Vol.+emission_CO2+consum_O2+generate_CO2; 0.344, 0.658, tmp_cumulo+interval_yield+interval_Pdt.+RS_cumulo+Cell_conc._interval+rab_integral+RQ_integral+emission_CO2+consum_O2+generate_CO2; 0.333, 0.658, tmp+tmp_cumulo+pH_cumulo+interval_yield+interval_Pdt.+OD+RS_cumulo+RQ_integral+AS_Vol.+consum_O2+generate_CO2; 0.363, 0.657, tmp_cumulo+pH_cumulo+interval_yield+OD+Cell_conc._interval+RQ_integral+consum_O2+generate_CO2; 0.322, 0.657, tmp_cumulo+pH_cumulo+interval_yield+interval_Pdt.+OD+Feed_Vol+Cell_conc._interval+RQ_integral+AS_Vol.+consum_O2+interval_O2+generate_CO2; 0.343, 0.657, tmp_cumulo+PL_cumulo+interval_yield+interval_Pdt.+OD+RS_cumulo+RQ_integral+emission_CO2+consum_O2+generate_CO2; 0.333, 0.657, tmp_cumulo+interval_yield+interval_Pdt.+OD+Feed_Vol+RS_cumulo+RQ_integral+AS_Vol.+emission_CO2+consum_O2+generate_CO2; 0.322, 0.657, tmp+pH_cumulo+AN_cumulo+interval_yield+interval_Pdt.+OD+Feed_Vol+RQ_integral+AS_Vol.+consum_O2+interval_O2+generate_CO2; 0.354, 0.657, tmp_cumulo+pH_cumulo+interval_yield+interval_Pdt.+OD+RQ_integral+emission_CO2+consum_O2+generate_CO2; 0.333, 0.657, tmp+tmp_cumulo+pH_cumulo+AN_cumulo+interval_yield+OD+RQ_integral+AS_Vol.+consum_O2+interval_O2+generate_CO2; 0.343, 0.657, tmp_cumulo+pH+interval_yield+interval_Pdt.+OD+RQ_integral+AS_Vol.+consum_O2+interval_O2+generate_CO2; 0.333, 0.657, tmp_cumulo+pH+pH_cumulo+interval_yield+OD+Cell_conc._interval+RQ_integral+AS_Vol.+consum_O2+interval_O2+generate_CO2; 0.322, 0.657, tmp_cumulo+pH_cumulo+interval_yield+interval_Pdt.+OD+RS_cumulo+RQ_integral+AS_Vol.+emission_CO2+consum_O2+interval_O2+generate_CO2; 0.322, 0.657, tmp+tmp_cumulo+pH_cumulo+interval_yield+interval_Pdt.+OD+Feed_Vol+RQ_integral+AS_Vol.+consum_O2+interval_O2+generate_CO2; 0.353, 0.657, tmp+interval_yield+interval_Pdt.+Feed_Vol+RQ_integral+AS_Vol.+consum_O2+interval_O2+generate_CO2; 0.343, 0.657, tmp+AN+interval_yield+interval_Pdt.+RS_cumulo+rab_integral+RQ_integral+emission_CO2+consum_O2+generate_CO2; 0.382, 0.657, tmp+interval_yield+interval_Pdt.+RQ_integral+consum_O2+generate_CO2; 0.322, 0.657, tmp_cumulo+pH_cumulo+AN_cumulo+interval_yield+interval_Pdt.+OD+rab_integral+RQ_integral+AS_Vol.+consum_O2+interval_O2+generate_CO2; 0.353, 0.657, tmp+tmp_cumulo+interval_yield+interval_Pdt.+RQ_integral+AS_Vol.+emission_CO2+consum_O2+generate_CO2; 0.333, 0.657, tmp+pH_cumulo+AN_cumulo+interval_yield+interval_Pdt.+OD+Feed_Vol+RQ_integral+AS_Vol.+consum_O2+generate_CO2; 0.333, 0.657, tmp_cumulo+pH_cumulo+AN+interval_yield+interval_Pdt.+OD+RS_cumulo+RQ_integral+emission_CO2+consum_O2+generate_CO2; 0.333, 0.657, tmp_cumulo+pH_cumulo+PL_cumulo+interval_yield+OD+RS_cumulo+RQ_integral+AS_Vol.+consum_O2+interval_O2+generate_CO2; 0.343, 0.657, tmp+AN_cumulo+interval_yield+interval_Pdt.+RS_cumulo+rab_integral+RQ_integral+emission_CO2+consum_O2+generate_CO2; 0.333, 0.657, tmp_cumulo+pH_cumulo+interval_yield+interval_Pdt.+Feed_Vol+rab_integral+RQ_integral+AS_Vol.+consum_O2+interval_O2+generate_CO2; 0.333, 0.657, tmp+tmp_cumulo+pH_cumulo+interval_yield+interval_Pdt.+OD+RQ_integral+AS_Vol.+emission_O2+consum_O2+generate_CO2; 0.311, 0.657, tmp_cumulo+pH_cumulo+interval_yield+interval_Pdt.+OD+Feed_Vol+rab_integral+RQ_integral+AS_Vol.+emission_CO2+consum_O2+interval_O2+generate_CO2; 0.333, 0.657, tmp+tmp_cumulo+pH_cumulo+interval_yield+OD+Cell_conc._interval+RQ_integral+AS_Vol.+consum_O2+interval_O2+generate_CO2; 0.333, 0.657, tmp+pH_cumulo+interval_yield+interval_Pdt.+OD+RQ_ integral+AS_Vol.+emission_CO2+consum_O2+interval_O2+generate_CO2; 0.322, 0.657, tmp_cumulo+pH_cumulo+interval_yield+OD+Feed_Vol+rab_integral+RQ_integral+AS_Vol.+emission_O2+consum_O2+interval_O2+generate_CO2; 0.333, 0.657, tmp_cumulo+pH_cumulo+AN_cumulo+interval_yield+interval_Pdt.+OD+RS_cumulo+RQ_integral+AS_Vol.+consum_O2+generate_CO2; 0.373, 0.657, tmp+interval_yield+interval_Pdt.+RQ_integral+emission_CO2+consum_O2+generate_CO2; 0.343, 0.657, tmp+pH_cumulo+interval_yield+interval_Pdt.+OD+rab_integral+RQ_integral+emission_CO2+consum_O2+generate_CO2; 0.353, 0.657, tmp_cumulo+pH_cumulo+interval_yield+OD+Feed_Vol+RS_cumulo+RQ_integral+consum_O2+generate_CO2; 0.343, 0.657, tmp_cumulo+pH+pH_cumulo+interval_yield+OD+RS_cumulo+rab_integral+RQ_integral+consum_O2+generate_CO2; 0.333, 0.657, tmp_cumulo+pH_cumulo+PL_cumulo+interval_yield+OD+rab_integral+RQ_integral+AS_Vol.+emission_CO2+consum_O2+generate_CO2; 0.343, 0.657, tmp+interval_yield+interval_Pdt.+OD+rab_integral+RQ_integral+AS_Vol.+emission_CO2+consum_O2+generate_CO2; 0.343, 0.657, tmp_cumulo+pH_cumulo+PL+interval_yield+OD+RS_cumulo+RQ_integral+AS_Vol.+consum_O2+generate_CO2; 0.322, 0.657, tmp_cumulo+pH_cumulo+PL_cumulo+interval_yield+interval_Pdt.+OD+rab_integral+RQ_integral+AS_Vol.+emission_CO2+consum_O2+generate_CO2; 0.343, 0.657, tmp+tmp_cumulo+pH_cumulo+interval_yield+interval_Pdt.+RQ_integral+AS_Vol.+emission_CO2+consum_O2+generate_CO2; 0.322, 0.657, tmp_cumulo+pH_cumulo+AN+interval_yield+OD+rab_integral+RQ_integral+AS_Vol.+emission_O2+consum_O2+interval_O2+generate_CO2; 0.333, 0.657, tmp_cumulo+pH_cumulo+AN+interval_yield+interval_Pdt.+RQ_integral+AS_Vol.+emission_O2+consum_O2+interval_O2+generate_CO2; 0.353, 0.657, tmp_cumulo+pH+interval_yield+interval_Pdt.+RS_cumulo+RQ_integral+AS_Vol.+consum_O2+generate_CO2; 0.353, 0.657, tmp_cumulo+pH_cumulo+interval_yield+OD+Feed_Vol+RQ_integral+consum_O2+interval_O2+generate_CO2; 0.353, 0.657, tmp+interval_yield+interval_Pdt.+RQ_integral+Accum._Yield+AS_Vol.+emission_CO2+consum_O2+generate_CO2; 0.322, 0.657, tmp_cumulo+pH_cumulo+interval_yield+OD+Feed_Vol+RS_cumulo+rab_integral+RQ_integral+AS_Vol.+consum_O2+interval_O2+generate_CO2; 0.343, 0.657, tmp+pH_cumulo+interval_yield+interval_Pdt.+Cell_conc._interval+RQ_integral+AS_Vol.+emission_CO2+consum_O2+generate_CO2; 0.343, 0.657, tmp_cumulo+pH_cumulo+interval_yield+interval_Pdt.+OD+RQ_integral+Accum._Yield+AS_Vol.+consum_O2+generate_CO2; 0.343, 0.657, tmp_cumulo+interval_yield+interval_Pdt.+OD+RS_cumulo+Cell_conc._interval+RQ_integral+emission_CO2+consum_O2+generate_CO2; 0.333, 0.657, tmp+tmp_cumulo+pH_cumulo+interval_yield+OD+Feed_Vol+RQ_integral+AS_Vol.+consum_O2+interval_O2+generate_CO2; 0.333, 0.657, tmp_cumulo+pH_cumulo+PL_cumulo+interval_yield+interval_Pdt.+RQ_integral+AS_Vol.+emission_CO2+consum_O2+interval_O2+generate_CO2; 0.322, 0.657, tmp_cumulo+pH+pH_cumulo+interval_yield+OD+rab_integral+RQ_integral+AS_Vol.+emission_CO2+consum_O2+interval_O2+generate_CO2; 0.343, 0.657, tmp_cumulo+pH+pH_cumulo+PL_cumulo+interval_yield+OD+RQ_integral+AS_Vol.+consum_O2+generate_CO2; 0.343, 0.657, tmp+interval_yield+interval_Pdt.+Cell_conc._interval+rab_integral+RQ_integral+AS_Vol.+emission_CO2+consum_O2+generate_CO2; 0.332, 0.657, tmp_cumulo+pH+pH_cumulo+AN+interval_yield+OD+rab_integral+RQ_integral+AS_Vol.+consum_O2+generate_CO2; 0.363, 0.657, tmp_cumulo+interval_yield+interval_Pdt.+Feed_Vol+RQ_integral+emission_CO2+consum_O2+generate_CO2; 0.343, 0.657, tmp_cumulo+pH_cumulo+PL_cumulo+interval_yield+OD+RQ_integral+AS_Vol.+emission_O2+consum_O2+generate_CO2; 0.332, 0.657, tmp_cumulo+AN+interval_yield+interval_Pdt.+OD+RS_cumulo+RQ_integral+AS_Vol.+emission_CO2+consum_O2+generate_CO2; 0.353, 0.657, tmp_cumulo+AN_cumulo+interval_yield+interval_Pdt.+RQ_integral+AS_Vol.+emission_CO2+consum_O2+generate_CO2; 0.332, 0.657, tmp_cumulo+pH_cumulo+AN_cumulo+interval_yield+OD+rab_integral+RQ_integral+AS_Vol.+emission_O2+consum_O2+generate_CO2; 0.343, 0.657, tmp_cumulo+pH_cumulo+PL_cumulo+interval_yield+interval_Pdt.+OD+RS_cumulo+RQ_integral+consum_O2+generate_CO2; 0.332, 0.657, tmp_cumulo+pH+pH_cumulo+interval_yield+OD+Feed_Vol+rab_integral+RQ_integral+AS_Vol.+consum_O2+generate_CO2; 0.310, 0.657, tmp_cumulo+pH_cumulo+AN+interval_yield+interval_Pdt.+OD+Feed_Vol+rab_integral+RQ_integral+AS_Vol.+consum_O2+interval_O2+generate_CO2; 0.322, 0.657, tmp_cumulo+pH_cumulo+AN+interval_yield+interval_Pdt.+rab_integral+RQ_integral+AS_Vol.+emission_CO2+consum_O2+interval_O2+generate_CO2; 0.332, 0.657, tmp_cumulo+pH_cumulo+PL_cumulo+interval_yield+interval_Pdt.+OD+RS_cumulo+RQ_integral+AS_Vol.+consum_O2+generate_CO2; 0.353, 0.657, tmp_cumulo+pH_cumulo+AN+interval_yield+OD+Feed_Vol+RQ_integral+consum_O2+generate_CO2; 0.322, 0.657, tmp_cumulo+pH_cumulo+interval_yield+OD+Feed_Vol+Cell_conc._interval+rab_integral+RQ_integral+AS_Vol.+consum_O2+interval_O2+generate_CO2; 0.343, 0.657, tmp+pH_cumulo+interval_yield+interval_Pdt.+OD+RS_cumulo+RQ_integral+emission_CO2+consum_O2+generate_CO2; 0.322, 0.657, tmp_cumulo+pH_cumulo+interval_yield+interval_Pdt.+OD+Cell_conc._interval+RQ_integral+AS_Vol.+emission_CO2+consum_O2+interval_O2+generate_CO2; 0.353, 0.657, tmp_cumulo+pH_cumulo+interval_yield+Feed_Vol+RQ_integral+AS_Vol.+consum_O2+interval_O2+generate_CO2; 0.332, 0.657, tmp_cumulo+pH+interval_yield+interval_Pdt.+OD+rab_integral+RQ_integral+AS_Vol.+emission_CO2+consum_O2+generate_CO2; 0.321, 0.657, tmp_cumulo+pH_cumulo+AN+interval_yield+interval_Pdt.+OD+RS_cumulo+RQ_integral+AS_Vol.+emission_CO2+consum_O2+generate_CO2; 0.332, 0.657, tmp_cumulo+pH+pH_cumulo+interval_yield+OD+rab_integral+RQ_integral+AS_Vol.+emission_O2+consum_O2+generate_CO2; 0.353, 0.657, tmp+pH_cumulo+interval_yield+interval_Pdt.+OD+Cell_conc._interval+RQ_integral+consum_O2+generate_CO2; 0.363, 0.657, tmp+pH_cumulo+interval_yield+OD+RQ_integral+consum_O2+interval_O2+generate_CO2; 0.343, 0.657, tmp+tmp_cumulo+interval_yield+interval_Pdt.+RS_cumulo+RQ_integral+emission_O2+emission_CO2+consum_O2+generate_CO2; 0.332, 0.657, tmp_cumulo+pH_cumulo+AN+interval_yield+interval_Pdt.+RS_cumulo+RQ_integral+AS_Vol.+emission_CO2+consum_O2+generate_CO2; 0.321, 0.657, tmp_cumulo+pH+pH_cumulo+interval_yield+OD+Feed_Vol+rab_integral+RQ_integral+AS_Vol.+consum_O2+interval_O2+generate_CO2; 0.321, 0.657, tmp_cumulo+pH_cumulo+interval_yield+OD+rab_integral+RQ_integral+AS_Vol.+emission_O2+emission_CO2+consum_O2+generate_CO2; 0.332, 0.657, tmp+tmp_cumulo+pH_cumulo+interval_yield+OD+RQ_integral+AS_Vol.+emission_O2+consum_O2+interval_O2+generate_CO2; 0.343, 0.657, tmp+pH_cumulo+interval_yield+interval_Pdt.+RS_cumulo+RQ_integral+AS_Vol.+emission_CO2+consum_O2+generate_CO2; 0.332, 0.657, tmp_cumulo+pH_cumulo+interval_yield+interval_Pdt.+Feed_Vol+RQ_integral+AS_Vol.+emission_O2+consum_O2+interval_O2+generate_CO2; 0.353, 0.657, tmp_cumulo+pH_cumulo+OD+rab_integral+RQ_integral+AS_Vol.+consum_O2+interval_O2+generate_CO2; 0.353, 0.657, tmp+interval_yield+interval_Pdt.+Feed_Vol+RS_cumulo+RQ_integral+emission_CO2+consum_O2+generate_CO2; 0.321, 0.657, tmp_cumulo+pH_cumulo+AN+interval_yield+interval_Pdt.+OD+RQ_integral+AS_Vol.+emission_O2+consum_O2+interval_O2+generate_CO2; 0.362, 0.657, tmp_cumulo+interval_yield+interval_Pdt.+RS_cumulo+Cell_conc._interval+RQ_integral+consum_O2+generate_CO2; 0.353, 0.657, tmp_cumulo+interval_yield+interval_Pdt.+RS_cumulo+rab_integral+RQ_integral+AS_Vol.+consum_O2+generate_CO2; 0.332, 0.657, tmp+tmp_cumulo+interval_yield+interval_Pdt.+OD+RS_cumulo+RQ_integral+AS_Vol.+emission_CO2+consum_O2+generate_CO2; 0.321, 0.657, tmp_cumulo+pH_cumulo+interval_yield+interval_Pdt.+OD+RS_cumulo+rab_integral+RQ_integral+emission_O2+emission_CO2+consum_O2+generate_CO2; 0.332, 0.657, tmp_cumulo+pH_cumulo+interval_yield+interval_Pdt.+Feed_Vol+RS_cumulo+RQ_integral+AS_Vol.+emission_CO2+consum_O2+generate_CO2; 0.342, 0.657, tmp+tmp_cumulo+pH_cumulo+PL_cumulo+interval_yield+OD+RQ_integral+AS_Vol.+consum_O2+generate_CO2; 0.332, 0.657, tmp+pH_cumulo+interval_yield+interval_Pdt.+rab_integral+RQ_integral+AS_Vol.+emission_O2+emission_CO2+consum_O2+generate_CO2; 0.353, 0.657, tmp_cumulo+pH_cumulo+interval_Pdt.+OD+RQ_integral+AS_Vol.+consum_O2+interval_O2+generate_CO2; 0.321, 0.657, tmp_cumulo+pH_cumulo+AN+interval_yield+interval_Pdt.+OD+Feed_Vol+rab_integral+RQ_integral+AS_Vol.+consum_O2+generate_CO2; 0.332, 0.657, tmp_cumulo+pH_cumulo+AN+interval_yield+interval_Pdt.+rab_integral+RQ_integral+AS_Vol.+consum_O2+interval_O2+generate_CO2; 0.342, 0.657, tmp+pH_cumulo+interval_yield+OD+Feed_Vol+RQ_integral+AS_Vol.+consum_O2+interval_O2+generate_CO2; 0.321, 0.657, tmp_cumulo+pH_cumulo+interval_yield+OD+Cell_conc._interval+rab_integral+RQ_integral+AS_Vol.+emission_CO2+consum_O2+interval_O2+generate_CO2; 0.342, 0.657, tmp+AN_cumulo+interval_yield+interval_Pdt.+RS_cumulo+RQ_integral+AS_Vol.+emission_CO2+consum_O2+generate_CO2; 0.332, 0.657, tmp_cumulo+AN_cumulo+interval_yield+interval_Pdt.+OD+RS_cumulo+rab_integral+RQ_integral+emission_CO2+consum_O2+generate_CO2; 0.352, 0.657, tmp+pH_cumulo+PL_cumulo+interval_yield+OD+RQ_integral+AS_Vol.+consum_O2+generate_CO2; 0.321, 0.657, tmp_cumulo+interval_yield+interval_Pdt.+OD+RS_cumulo+rab_integral+RQ_integral+AS_Vol.+emission_O2+emission_CO2+consum_O2+generate_CO2; 0.321, 0.657, tmp_cumulo+pH+pH_cumulo+AN+interval_yield+OD+rab_integral+RQ_integral+AS_Vol.+consum_O2+interval_O2+generate_CO2; 0.332, 0.657, tmp_cumulo+pH_cumulo+PL_cumulo+interval_yield+OD+Cell_conc._interval+RQ_integral+AS_Vol.+consum_O2+interval_O2+generate_CO2; 0.332, 0.657, tmp_cumulo+pH_cumulo+PL_cumulo+interval_yield+OD+RQ_integral+AS_Vol.+emission_O2+consum_O2+interval_O2+generate_CO2; 0.332, 0.657, tmp_cumulo+pH_cumulo+interval_yield+OD+Cell_conc._interval+rab_integral+RQ_integral+AS_Vol.+emission_O2+consum_O2+generate_CO2; 0.332, 0.657, tmp_cumulo+pH_cumulo+AN+interval_yield+OD+Cell_conc._interval+rab_integral+RQ_integral+AS_Vol.+consum_O2+generate_CO2; 0.342, 0.657, tmp_cumulo+pH+interval_yield+interval_Pdt.+RS_cumulo+RQ_integral+emission_O2+emission_CO2+consum_O2+generate_CO2; 0.332, 0.657, tmp_cumulo+pH_cumulo+PL_cumulo+interval_yield+OD+Feed_Vol+rab_integral+RQ_integral+AS_Vol.+consum_O2+generate_CO2; 0.332, 0.657, tmp+pH_cumulo+interval_yield+interval_Pdt.+OD+Feed_Vol+Cell_conc._interval+RQ_integral+AS_Vol.+consum_O2+generate_CO2; 0.342, 0.657, tmp_cumulo+interval_yield+interval_Pdt.+Feed_Vol+RS_cumulo+RQ_integral+AS_Vol.+consum_O2+interval_O2+generate_CO2; 0.352, 0.657, tmp+pH_cumulo+interval_yield+interval_Pdt.+OD+RQ_integral+consum_O2+interval_O2+generate_CO2; 0.342, 0.657, tmp+AN+interval_yield+interval_Pdt.+RS_cumulo+RQ_integral+AS_Vol.+emission_CO2+consum_O2+generate_CO2; 0.342, 0.657, tmp_cumulo+pH_cumulo+PL+interval_yield+OD+Feed_Vol+RQ_integral+AS_Vol.+consum_O2+generate_CO2; 0.332, 0.656, tmp_cumulo+interval_yield+interval_Pdt.+Feed_Vol+RS_cumulo+RQ_integral+AS_Vol.+emission_O2+emission_CO2+consum_O2+generate_CO2; 0.332, 0.656, tmp+tmp_cumulo+pH_cumulo+interval_yield+OD+RQ_integral+AS_Vol.+emission_CO2+consum_O2+interval_O2+generate_CO2; 0.342, 0.656, tmp+AN+interval_yield+interval_Pdt.+Cell_conc._interval+RQ_integral+AS_Vol.+emission_CO2+consum_O2+generate_CO2; 0.332, 0.656, tmp+tmp_cumulo+interval_yield+interval_Pdt.+OD+RS_cumulo+rab_integral+RQ_integral+emission_CO2+consum_O2+generate_CO2; 0.362, 0.656, tmp_cumulo+interval_yield+OD+RS_cumulo+RQ_integral+consum_O2+interval_O2+generate_CO2; 0.332, 0.656, tmp_cumulo+pH_cumulo+PL_cumulo+interval_yield+interval_Pdt.+OD+Feed_Vol+RQ_integral+AS_Vol.+consum_O2+generate_CO2; 0.332, 0.656, tmp_cumulo+pH+pH_cumulo+interval_yield+OD+RS_cumulo+rab_integral+RQ_integral+AS_Vol.+consum_O2+generate_CO2; 0.332, 0.656, tmp_cumulo+interval_yield+interval_Pdt.+RS_cumulo+rab_integral+RQ_integral+AS_Vol.+emission_CO2+consum_O2+interval_O2+generate_CO2; 0.342, 0.656, tmp+interval_yield+interval_Pdt.+OD+RQ_integral+AS_Vol.+emission_O2+emission_CO2+consum_O2+generate_CO2; 0.362, 0.656, tmp+pH_cumulo+interval_yield+OD+rab_integral+RQ_integral+consum_O2+generate_CO2; 0.332, 0.656, tmp_cumulo+pH_cumulo+AN+interval_yield+interval_Pdt.+OD+RS_cumulo+rab_integral+RQ_integral+consum_O2+generate_CO2; 0.332, 0.656, tmp_cumulo+pH+pH_cumulo+PL_cumulo+interval_yield+OD+RQ_integral+AS_Vol.+consum_O2+interval_O2+generate_CO2; 0.362, 0.656, tmp_cumulo+pH_cumulo+OD+rab_integral+RQ_integral+AS_Vol.+consum_O2+generate_CO2; 0.321, 0.656, tmp_cumulo+pH_cumulo+interval_yield+interval_Pdt.+OD+Feed_Vol+rab_integral+RQ_integral+AS_Vol.+emission_O2+consum_O2+generate_CO2; 0.310, 0.656, tmp_cumulo+pH_cumulo+interval_yield+interval_Pdt.+OD+RS_cumulo+rab_integral+RQ_integral+AS_Vol.+emission_O2+emission_CO2+consum_O2+generate_CO2; 0.331, 0.656, tmp+pH_cumulo+interval_yield+interval_Pdt.+OD+Feed_Vol+RQ_integral+AS_Vol.+emission_O2+consum_O2+generate_CO2; 0.331, 0.656, tmp_cumulo+pH_cumulo+AN+interval_yield+interval_Pdt.+OD+Cell_conc._interval+RQ_integral+AS_Vol.+consum_O2+generate_CO2; 0.331, 0.656, tmp_cumulo+pH+pH_cumulo+interval_yield+interval_Pdt.+OD+RQ_integral+AS_Vol.+emission_O2+consum_O2+generate_CO2; 0.321, 0.656, tmp_cumulo+pH_cumulo+interval_yield+OD+RS_cumulo+rab_integral+RQ_integral+AS_Vol.+emission_

CO2+consum_O2+interval_O2+generate_CO2; 0.352, 0.656, tmp_cumulo+pH_cumulo+interval_yield+interval_Pdt.+OD+RQ_integral+consum_O2+interval_O2+generate_CO2; 0.321, 0.656, tmp_cumulo+pH+pH_cumulo+interval_yield+OD+rab_integral+RQ_integral+AS_Vol.+emission_O2+consum_O2+interval_O2+generate_CO2; 0.352, 0.656, tmp_cumulo+pH_cumulo+interval_yield+OD+rab_integral+RQ_integral+consum_O2+interval_O2+generate_CO2; 0.331, 0.656, tmp_cumulo+AN_cumulo+interval_yield+interval_Pdt.+OD+RS_cumulo+RQ_integral+AS_Vol.+emission_CO2+consum_O2+generate_CO2; 0.342, 0.656, tmp_cumulo+interval_yield+interval_Pdt.+Feed_Vol+RS_cumulo+RQ_integral+emission_O2+emission_CO2+consum_O2+generate_CO2; 0.321, 0.656, tmp_cumulo+pH_cumulo+interval_yield+interval_Pdt.+OD+Feed_Vol+RQ_integral+AS_Vol.+emission_O2+emission_CO2+consum_O2+generate_CO2; 0.342, 0.656, tmp+AN_cumulo+interval_yield+interval_Pdt.+OD+RS_cumulo+RQ_integral+emission_CO2+consum_O2+generate_CO2; 0.352, 0.656, tmp_cumulo+AN_cumulo+interval_yield+interval_Pdt.+RS_cumulo+RQ_integral+emission_O2+consum_O2+generate_CO2; 0.352, 0.656, tmp+pH_cumulo+interval_yield+interval_Pdt.+RS_cumulo+RQ_integral+emission_CO2+consum_O2+generate_CO2; 0.321, 0.656, tmp_cumulo+pH+pH_cumulo+interval_yield+interval_Pdt.+OD+rab_integral+RQ_integral+AS_Vol.+consum_O2+interval_O2+generate_CO2; 0.331, 0.656, tmp_cumulo+pH_cumulo+interval_yield+interval_Pdt.+Cell_conc._interval+rab_integral+RQ_integral+AS_Vol.+emission_CO2+consum_O2+generate_CO2; 0.321, 0.656, tmp_cumulo+pH_cumulo+interval_yield+interval_Pdt.+RS_cumulo+rab_integral+RQ_integral+AS_Vol.+emission_O2+emission_CO2+consum_O2+generate_CO2; 0.331, 0.656, tmp+interval_yield+interval_Pdt.+OD+RS_cumulo+rab_integral+RQ_integral+emission_O2+emission_CO2+consum_O2+generate_CO2; 0.352, 0.656, tmp_cumulo+AN+interval_yield+interval_Pdt.+RS_cumulo+RQ_integral+emission_CO2+consum_O2+generate_CO2; 0.331, 0.656, tmp+pH_cumulo+AN+interval_yield+interval_Pdt.+Feed_Vol+RQ_integral+AS_Vol.+consum_O2+interval_O2+generate_CO2; 0.331, 0.656, tmp_cumulo+pH_cumulo+AN_cumulo+interval_yield+OD+RS_cumulo+rab_integral+RQ_integral+AS_Vol.+consum_O2+generate_CO2; 0.320, 0.656, tmp_cumulo+pH_cumulo+PL_cumulo+interval_yield+interval_Pdt.+OD+RQ_integral+AS_Vol.+emission_CO2+consum_O2+interval_O2+generate_CO2; 0.352, 0.656, tmp_cumulo+pH_cumulo+interval_yield+OD+RS+rab_integral+RQ_integral+consum_O2+generate_CO2; 0.342, 0.656, tmp_cumulo+pH_cumulo+PL_cumulo+interval_yield+interval_Pdt.+RQ_integral+AS_Vol.+emission_CO2+consum_O2+generate_CO2; 0.352, 0.656, tmp_cumulo+pH_cumulo+AN+interval_yield+OD+rab_integral+RQ_integral+consum_O2+generate_CO2; 0.342, 0.656, tmp+AN+interval_yield+interval_Pdt.+rab_integral+RQ_integral+AS_Vol.+emission_CO2+consum_O2+generate_CO2; 0.342, 0.656, tmp_cumulo+pH_cumulo+interval_yield+interval_Pdt.+OD+Feed_Vol+RS_cumulo+RQ_integral+consum_O2+generate_CO2; 0.342, 0.656, tmp+pH+interval_yield+interval_Pdt.+rab_integral+RQ_integral+AS_Vol.+emission_CO2+consum_O2+generate_CO2; 0.352, 0.656, tmp_cumulo+pH_cumulo+AN+interval_yield+RQ_integral+AS_Vol.+consum_O2+interval_O2+generate_CO2; 0.331, 0.656, tmp_cumulo+pH+pH_cumulo+interval_yield+interval_Pdt.+OD+RS_cumulo+RQ_integral+AS_Vol.+consum_O2+generate_CO2; 0.331, 0.656, tmp_cumulo+pH_cumulo+AN_cumulo+interval_yield+interval_Pdt.+RS_cumulo+RQ_integral+AS_Vol.+emission_CO2+consum_O2+generate_CO2; 0.361, 0.656, tmp_cumulo+pH+interval_yield+OD+RS_cumulo+RQ_integral+consum_O2+generate_CO2; 0.331, 0.656, tmp_cumulo+pH_cumulo+interval_yield+OD+RS_cumulo+Cell_conc._interval+RQ_integral+AS_Vol.+consum_O2+interval_O2+generate_CO2; 0.331, 0.656, tmp_cumulo+AN+interval_yield+interval_Pdt.+RS_cumulo+rab_integral+RQ_integral+emission_O2+emission_CO2+consum_O2+generate_CO2; 0.331, 0.656, tmp+tmp_cumulo+pH_cumulo+interval_yield+OD+Feed_Vol+rab_integral+RQ_integral+AS_Vol.+consum_O2+generate_CO2; 0.341, 0.656, tmp+AN+interval_yield+interval_Pdt.+OD+RS_cumulo+RQ_integral+emission_CO2+consum_O2+generate_CO2; 0.331, 0.656, tmp_cumulo+pH_cumulo+PL+interval_yield+OD+Feed_Vol+RQ_integral+AS_Vol.+consum_O2+interval_O2+generate_CO2; 0.341, 0.656, tmp+pH_cumulo+interval_yield+interval_Pdt.+OD+Cell_conc._interval+RQ_integral+AS_Vol.+consum_O2+generate_CO2; 0.341, 0.656, tmp+interval_yield+interval_Pdt.+Feed_Vol+rab_integral+RQ_integral+AS_Vol.+emission_CO2+consum_O2+generate_CO2; 0.320, 0.656, tmp+pH_cumulo+interval_yield+interval_Pdt.+OD+Feed_Vol+RQ_integral+AS_Vol.+emission_O2+consum_O2+interval_O2+generate_CO2; 0.341, 0.656, tmp_cumulo+AN_cumulo+interval_yield+interval_Pdt.+RS_cumulo+RQ_integral+emission_O2+emission_CO2+consum_O2+generate_CO2; 0.320, 0.656, tmp+tmp_cumulo+pH_cumulo+interval_yield+interval_Pdt.+OD+RS_cumulo+RQ_integral+AS_Vol.+emission_CO2+consum_O2+generate_CO2; 0.341, 0.656, tmp_cumulo+interval_yield+interval_Pdt.+OD+RS_cumulo+RQ_integral+AS_Vol.+emission_O2+consum_O2+generate_CO2; 0.320, 0.656, tmp+pH_cumulo+interval_yield+interval_Pdt.+OD+rab_integral+RQ_integral+AS_Vol.+emission_O2+emission_CO2+consum_O2+generate_CO2; 0.351, 0.656, tmp+PL_cumulo+interval_yield+interval_Pdt.+RS_cumulo+RQ_integral+emission_CO2+consum_O2+generate_CO2; 0.320, 0.656, tmp_cumulo+pH_cumulo+AN_cumulo+interval_yield+OD+rab_integral+RQ_integral+AS_Vol.+emission_O2+consum_O2+interval_O2+generate_CO2; 0.320, 0.656, tmp_cumulo+pH_cumulo+AN_cumulo+interval_yield+interval_Pdt.+OD+RS_cumulo+RQ_integral+AS_Vol.+emission_CO2+consum_O2+generate_CO2; 0.341, 0.656, tmp_cumulo+pH_cumulo+interval_yield+interval_Pdt.+RS_cumulo+rab_integral+RQ_integral+AS_Vol.+consum_O2+generate_CO2; 0.331, 0.656, tmp+tmp_cumulo+pH_cumulo+interval_yield+OD+RS_cumulo+rab_integral+RQ_integral+AS_Vol.+consum_O2+generate_CO2; 0.361, 0.656, tmp+pH+interval_yield+OD+RS+RQ_integral+consum_O2+generate_CO2; 0.309, 0.656, tmp_cumulo+pH_cumulo+AN+interval_yield+interval_Pdt.+OD+rab_integral+RQ_integral+AS_Vol.+emission_CO2+consum_O2+interval_O2+generate_CO2; 0.351, 0.656, tmp_cumulo+pH_cumulo+interval_yield+interval_Pdt.+Cell_conc._interval+RQ_integral+AS_Vol.+consum_O2+generate_CO2; 0.351, 0.656, tmp_cumulo+pH_cumulo+PL_cumulo+interval_yield+interval_Pdt.+RQ_integral+AS_Vol.+consum_O2+generate_CO2; 0.320, 0.656, tmp_cumulo+pH_cumulo+PL_cumulo+interval_yield+OD+Feed_Vol+rab_integral+RQ_integral+AS_Vol.+consum_O2+interval_O2+generate_CO2; 0.320, 0.656, tmp_cumulo+pH_cumulo+interval_yield+interval_Pdt.+OD+Cell_conc._interval+rab_integral+RQ_integral+AS_Vol.+consum_O2+interval_O2+generate_CO2; 0.351, 0.656, tmp_cumulo+pH_cumulo+interval_yield+interval_Pdt.+RS_cumulo+rab_integral+RQ_integral+consum_O2+ generate_CO2; 0.341, 0.656, tmp_cumulo+pH_cumulo+interval_yield+interval_Pdt.+RS_cumulo+RQ_integral+emission_O2+emission_CO2+consum_O2+generate_CO2; 0.361, 0.656, tmp+interval_yield+interval_Pdt.+OD+RS_cumulo+RQ_integral+consum_O2+generate_CO2; 0.309, 0.656, tmp_cumulo+pH_cumulo+interval_yield+interval_Pdt.+OD+Feed_Vol+RS_cumulo+rab_integral+RQ_integral+AS_Vol.+emission_CO2+consum_O2+generate_CO2; 0.341, 0.656, tmp+pH_cumulo+AN_cumulo+interval_yield+interval_Pdt.+OD+RQ_integral+AS_Vol.+consum_O2+generate_CO2; 0.331, 0.656, tmp+pH_cumulo+interval_yield+interval_Pdt.+Feed_Vol+rab_integral+RQ_integral+AS_Vol.+emission_CO2+consum_O2+generate_CO2; 0.320, 0.656, tmp_cumulo+pH+pH_cumulo+AN_cumulo+interval_yield+OD+rab_integral+RQ_integral+AS_Vol.+consum_O2+interval_O2+generate_CO2; 0.351, 0.656, tmp+tmp_cumulo+pH_cumulo+interval_yield+interval_Pdt.+RQ_integral+AS_Vol.+consum_O2+generate_CO2; 0.370, 0.656, tmp+interval_yield+interval_Pdt.+OD+RQ_integral+consum_O2+generate_CO2; 0.331, 0.656, tmp_cumulo+pH_cumulo+PL_cumulo+interval_yield+OD+RS_cumulo+rab_integral+RQ_integral+AS_Vol.+consum_O2+generate_CO2; 0.320, 0.656, tmp_cumulo+pH_cumulo+interval_yield+interval_Pdt.+Feed_Vol+rab_integral+RQ_integral+AS_Vol.+emission_CO2+consum_O2+interval_O2+generate_CO2; 0.330, 0.656, tmp_cumulo+pH_cumulo+interval_yield+interval_Pdt.+Cell_conc._interval+RQ_integral+AS_Vol.+emission_CO2+consum_O2+interval_O2+generate_CO2; 0.320, 0.656, tmp_cumulo+pH_cumulo+AN+interval_yield+interval_Pdt.+OD+Feed_Vol+RQ_integral+AS_Vol.+emission_CO2+consum_O2+generate_CO2; 0.330, 0.656, tmp_cumulo+pH+pH_cumulo+AN_cumulo+interval_yield+OD+rab_integral+RQ_integral+AS_Vol.+consum_O2+generate_CO2; 0.341, 0.656, tmp+AN_cumulo+interval_yield+interval_Pdt.+rab_integral+RQ_integral+AS_Vol.+emission_CO2+consum_O2+generate_CO2; 0.330, 0.656, tmp+tmp_cumulo+pH_cumulo+interval_yield+interval_Pdt.+OD+Cell_conc._interval+RQ_integral+AS_Vol.+consum_O2+generate_CO2; 0.341, 0.656, tmp+interval_yield+interval_Pdt.+RS_cumulo+Cell_conc._interval+RQ_integral+AS_Vol.+emission_CO2+consum_O2+generate_CO2; 0.341, 0.656, tmp+pH_cumulo+AN+interval_yield+interval_Pdt.+OD+RQ_integral+emission_CO2+consum_O2+generate_CO2; 0.361, 0.656, tmp+interval_yield+interval_Pdt.+RQ_integral+AS_Vol.+emission_O2+consum_O2+generate_CO2; 0.330, 0.656, tmp+interval_yield+interval_Pdt.+Feed_Vol+RS_cumulo+rab_integral+RQ_integral+AS_Vol.+emission_CO2+consum_O2+generate_CO2; 0.320, 0.656, tmp_cumulo+pH_cumulo+PL_cumulo+interval_yield+interval_Pdt.+OD+Feed_Vol+RQ_integral+AS_Vol.+consum_O2+interval_O2+generate_CO2; 0.320, 0.656, tmp_cumulo+pH_cumulo+AN+interval_yield+interval_Pdt.+OD+RQ_integral+AS_Vol.+emission_O2+emission_CO2+consum_O2+generate_CO2; 0.330, 0.656, tmp_cumulo+pH_cumulo+PL_cumulo+AN+interval_yield+interval_Pdt.+OD+RQ_integral+AS_Vol.+consum_O2+generate_CO2; 0.341, 0.656, tmp_cumulo+interval_yield+interval_Pdt.+OD+rab_integral+RQ_integral+AS_Vol.+emission_CO2+consum_O2+generate_CO2; 0.330, 0.656, tmp+pH_cumulo+interval_yield+interval_Pdt.+OD+RS_cumulo+RQ_integral+AS_Vol.+emission_CO2+consum_O2+generate_CO2; 0.341, 0.656, tmp_cumulo+pH+interval_yield+interval_Pdt.+OD+RS_cumulo+RQ_integral+AS_Vol.+consum_O2+generate_CO2; 0.351, 0.656, tmp+pH_cumulo+interval_yield+interval_Pdt.+OD+RS_cumulo+RQ_integral+consum_O2+generate_CO2; 0.330, 0.656, tmp+tmp_cumulo+pH_cumulo+AN+interval_yield+interval_Pdt.+OD+RQ_integral+AS_Vol.+consum_O2+generate_CO2; 0.330, 0.656, tmp_cumulo+pH_cumulo+PL_cumulo+interval_yield+interval_Pdt.+RQ_integral+AS_Vol.+emission_O2+consum_O2+interval_O2+generate_CO2; 0.319, 0.656, tmp+tmp_cumulo+pH_cumulo+interval_yield+interval_Pdt.+OD+RQ_integral+AS_Vol.+emission_CO2+consum_O2+interval_O2+generate_CO2; 0.341, 0.656, tmp_cumulo+pH_cumulo+interval_yield+interval_Pdt.+OD+RS_cumulo+Cell_conc._interval+RQ_integral+consum_O2+generate_CO2; 0.341, 0.656, tmp+pH_cumulo+interval_yield+interval_Pdt.+OD+rab_integral+RQ_integral+AS_Vol.+consum_O2+generate_CO2; 0.330, 0.656, tmp+interval_yield+interval_Pdt.+OD+Feed_Vol+RS_cumulo+RQ_integral+AS_Vol.+emission_CO2+consum_O2+generate_CO2; 0.330, 0.656, tmp_cumulo+pH_cumulo+AN_cumulo+interval_yield+interval_Pdt.+OD+Cell_conc._interval+RQ_integral+AS_Vol.+consum_O2+generate_CO2; 0.319, 0.656, tmp_cumulo+pH+pH_cumulo+interval_yield+interval_Pdt.+OD+RQ_integral+AS_Vol.+emission_CO2+consum_O2+interval_O2+generate_CO2; 0.330, 0.656, tmp_cumulo+pH_cumulo+interval_yield+interval_Pdt.+Feed_Vol+RS_cumulo+RQ_integral+AS_Vol.+consum_O2+interval_O2+generate_CO2; 0.341, 0.656, tmp_cumulo+PL_cumulo+AN+interval_yield+interval_Pdt.+RS_cumulo+RQ_integral+emission_CO2+consum_O2+generate_CO2; 0.330, 0.656, tmp_cumulo+pH_cumulo+interval_yield+interval_Pdt.+RS_cumulo+RQ_integral+AS_Vol.+emission_O2+consum_O2+interval_O2+generate_CO2; 0.351, 0.656, tmp_cumulo+AN+interval_yield+interval_Pdt.+OD+RS_cumulo+RQ_integral+consum_O2+generate_CO2; 0.330, 0.656, tmp_cumulo+pH_cumulo+PL_cumulo+AN+interval_yield+OD+rab_integral+RQ_integral+AS_Vol.+consum_O2+generate_CO2; 0.341, 0.656, tmp+pH_cumulo+AN_cumulo+interval_yield+interval_Pdt.+OD+RQ_integral+emission_CO2+consum_O2+generate_CO2; 0.341, 0.656, tmp+pH_cumulo+interval_yield+interval_Pdt.+OD+RQ_integral+AS_Vol.+emission_O2+consum_O2+generate_CO2; 0.341, 0.656, tmp_cumulo+pH_cumulo+PL+AN+interval_yield+OD+RQ_integral+AS_Vol.+consum_O2+generate_CO2; 0.330, 0.656, tmp_cumulo+pH_cumulo+PL+AN_cumulo+interval_yield+OD+RQ_integral+AS_Vol.+consum_O2+interval_O2+generate_CO2; 0.330, 0.656, tmp_cumulo+pH_cumulo+AN_cumulo+interval_yield+OD+Cell_conc._interval+rab_integral+RQ_integral+AS_Vol.+consum_O2+generate_CO2; 0.330, 0.655, tmp_cumulo+pH_cumulo+interval_yield+interval_Pdt.+OD+RS_cumulo+Cell_conc._interval+RQ_integral+AS_Vol.+consum_O2+generate_CO2; 0.341, 0.655, tmp_cumulo+pH_cumulo+PL+interval_yield+OD+RQ_integral+AS_Vol.+emission_CO2+consum_O2+generate_CO2; 0.308, 0.655, tmp_cumulo+pH_cumulo+interval_yield+interval_Pdt.+OD+rab_integral+RQ_integral+AS_Vol.+emission_O2+emission_CO2+consum_O2+interval_O2+generate_CO2; 0.319, 0.655, tmp_cumulo+pH_cumulo+interval_yield+interval_Pdt.+OD+RS_cumulo+rab_integral+RQ_integral+AS_Vol.+consum_O2+interval_O2+generate_CO2; 0.351, 0.655, tmp_cumulo+pH_cumulo+interval_yield+OD+RS+RQ_integral+consum_O2+interval_O2+generate_CO2; 0.341, 0.655, tmp_cumulo+pH_cumulo+AN+interval_yield+interval_Pdt.+OD+rab_integral+RQ_integral+consum_O2+generate_CO2; 0.360, 0.655, tmp_cumulo+pH_cumulo+interval_yield+OD+RQ_integral+emission_CO2+consum_O2+generate_CO2; 0.330, 0.655, tmp_cumulo+pH+pH_ cumulo+interval_yield+interval_Pdt.+OD+Feed_Vol+RQ_integral+AS_Vol.+consum_O2+generate_CO2; 0.340, 0.655, tmp_cumulo+pH+interval_yield+interval_Pdt.+OD+Feed_Vol+RQ_integral+AS_Vol.+consum_O2+generate_CO2; 0.330, 0.655, tmp_cumulo+interval_yield+interval_Pdt.+RS_cumulo+Cell_conc._interval+rab_integral+RQ_integral+AS_Vol.+emission_CO2+consum_O2+generate_CO2; 0.330, 0.655, tmp_cumulo+pH+interval_yield+interval_Pdt.+RS_cumulo+RQ_integral+AS_Vol.+emission_O2+emission_CO2+consum_O2+generate_CO2; 0.351, 0.655, tmp_cumulo+AN_cumulo+interval_yield+interval_Pdt.+OD+RS_cumulo+RQ_integral+consum_O2+generate_CO2; 0.340, 0.655, tmp+interval_yield+interval_Pdt.+Feed_Vol+RQ_integral+AS_Vol.+emission_CO2+consum_O2+interval_O2+generate_CO2; 0.360, 0.655, tmp_cumulo+interval_yield+RS_cumulo+RQ_integral+AS_Vol.+consum_O2+interval_O2+generate_CO2; 0.340, 0.655, tmp_cumulo+interval_yield+interval_Pdt.+RS_cumulo+rab_integral+RQ_integral+emission_CO2+consum_O2+interval_O2+generate_CO2; 0.330, 0.655, tmp_cumulo+pH_cumulo+PL+AN+interval_yield+OD+RQ_integral+AS_Vol.+consum_O2+interval_O2+generate_CO2; 0.330, 0.655, tmp_cumulo+pH_cumulo+AN_cumulo+interval_yield+interval_Pdt.+OD+RS_cumulo+RQ_integral+emission_CO2+consum_O2+generate_CO2; 0.330, 0.655, tmp+tmp_cumulo+pH_cumulo+interval_yield+interval_Pdt.+rab_integral+RQ_integral+AS_Vol.+emission_CO2+consum_O2+generate_CO2; 0.340, 0.655, tmp_cumulo+pH_cumulo+PL+AN_cumulo+interval_yield+OD+RQ_integral+AS_Vol.+consum_O2+generate_CO2; 0.319, 0.655, tmp_cumulo+pH_cumulo+AN_cumulo+interval_yield+interval_Pdt.+OD+Feed_Vol+rab_integral+RQ_integral+AS_Vol.+consum_O2+generate_CO2; 0.330, 0.655, tmp_cumulo+PL_cumulo+interval_yield+interval_Pdt.+RS_cumulo+rab_integral+RQ_integral+AS_Vol.+emission_CO2+consum_O2+generate_CO2; 0.319, 0.655, tmp_cumulo+pH+pH_cumulo+interval_yield+interval_Pdt.+OD+Feed_Vol+RQ_integral+AS_Vol.+consum_O2+interval_O2+generate_CO2; 0.340, 0.655, tmp_cumulo+pH_cumulo+AN_cumulo+interval_yield+OD+RS_cumulo+rab_integral+RQ_integral+consum_O2+generate_CO2; 0.360, 0.655, tmp_cumulo+pH_cumulo+interval_Pdt.+OD+RQ_integral+AS_Vol.+consum_O2+generate_CO2; 0.350, 0.655, tmp_cumulo+interval_yield+interval_Pdt.+OD+Feed_Vol+RS_cumulo+RQ_integral+consum_O2+generate_CO2; 0.340, 0.655, tmp+pH+interval_yield+interval_Pdt.+RS_cumulo+rab_integral+RQ_integral+emission_CO2+consum_O2+generate_CO2; 0.360, 0.655, tmp_cumulo+interval_yield+interval_Pdt.+RQ_integral+AS_Vol.+emission_O2+consum_O2+generate_CO2; 0.330, 0.655, tmp+pH_cumulo+interval_yield+interval_Pdt.+Feed_Vol+RQ_integral+AS_Vol.+emission_CO2+consum_O2+interval_O2+generate_CO2; 0.330, 0.655, tmp_cumulo+pH_cumulo+PL+interval_yield+OD+RS_cumulo+RQ_integral+AS_Vol.+consum_O2+interval_O2+generate_CO2; 0.340, 0.655, tmp+tmp_cumulo+pH_cumulo+interval_yield+OD+RS_cumulo+rab_integral+RQ_integral+consum_O2+generate_CO2; 0.340, 0.655, tmp+pH_cumulo+AN+interval_yield+interval_Pdt.+OD+RQ_integral+AS_Vol.+consum_O2+generate_CO2; 0.350, 0.655, tmp+PL_cumulo+interval_yield+interval_Pdt.+RQ_integral+AS_Vol.+emission_CO2+consum_O2+generate_CO2; 0.360, 0.655, tmp+interval_yield+interval_Pdt.+RS_cumulo+RQ_integral+emission_O2+consum_O2+generate_CO2; 0.330, 0.655, tmp_cumulo+AN+interval_yield+interval_Pdt.+RS_cumulo+RQ_integral+AS_Vol.+emission_O2+emission_CO2+consum_O2+generate_CO2; 0.340, 0.655, tmp+interval_yield+interval_Pdt.+OD+RS_cumulo+Cell_conc._interval+RQ_integral+emission_CO2+consum_O2+generate_CO2; 0.330, 0.655, tmp_cumulo+pH_cumulo+PL_cumulo+AN_cumulo+interval_yield+interval_Pdt.+OD+RQ_integral+AS_Vol.+consum_O2+generate_CO2; 0.350, 0.655, tmp_cumulo+interval_yield+interval_Pdt.+RS_cumulo+rab_integral+RQ_integral+consum_O2+interval_O2+generate_CO2; 0.319, 0.655, tmp+tmp_cumulo+pH_cumulo+interval_yield+OD+Feed_Vol+rab_integral+RQ_integral+AS_Vol.+consum_O2+interval_O2+generate_CO2; 0.330, 0.655, tmp+tmp_cumulo+pH_cumulo+interval_yield+interval_Pdt.+RS_cumulo+RQ_integral+AS_Vol.+emission_CO2+consum_O2+generate_CO2; 0.330, 0.655, tmp+tmp_cumulo+interval_yield+interval_Pdt.+RS_cumulo+rab_integral+RQ_integral+emission_O2+emission_CO2+consum_O2+generate_CO2; 0.340, 0.655, tmp_cumulo+pH+AN+interval_yield+interval_Pdt.+RS_cumulo+RQ_integral+emission_CO2+consum_O2+generate_CO2; 0.330, 0.655, tmp_cumulo+pH_cumulo+PL+interval_yield+interval_Pdt.+OD+RQ_integral+AS_Vol.+consum_O2+interval_O2+generate_CO2; 0.340, 0.655, tmp+AN+interval_yield+interval_Pdt.+OD+RQ_integral+AS_Vol.+emission_CO2+consum_O2+generate_CO2; 0.319, 0.655, tmp_cumulo+pH_cumulo+AN+interval_yield+OD+Cell_conc._interval+rab_integral+RQ_integral+AS_Vol.+consum_O2+interval_O2+generate_CO2; 0.308, 0.655, tmp+pH_cumulo+AN+interval_yield+interval_Pdt.+OD+Feed_Vol+rab_integral+RQ_integral+AS_Vol.+consum_O2+interval_O2+generate_CO2; 0.350, 0.655, tmp+pH_cumulo+interval_yield+OD+RQ_integral+AS_Vol.+emission_CO2+consum_O2+generate_CO2; 0.350, 0.655, tmp+tmp_cumulo+interval_yield+interval_Pdt.+OD+RS_cumulo+RQ_integral+consum_O2+generate_CO2; 0.340, 0.655, tmp_cumulo+interval_yield+interval_Pdt.+rab_integral+RQ_integral+AS_Vol.+emission_O2+emission_CO2+consum_O2+generate_CO2; 0.319, 0.655, tmp_cumulo+pH+interval_yield+interval_Pdt.+OD+RS_cumulo+rab_integral+RQ_integral+AS_Vol.+emission_CO2+consum_O2+generate_CO2; 0.340, 0.655, tmp_cumulo+pH_cumulo+AN+interval_yield+rab_integral+RQ_integral+AS_Vol.+consum_O2+interval_O2+generate_CO2; 0.319, 0.655, tmp+pH_cumulo+interval_yield+interval_Pdt.+OD+Feed_Vol+RS_cumulo+RQ_integral+AS_Vol.+consum_O2+interval_O2+generate_CO2; 0.340, 0.655, tmp+interval_yield+interval_Pdt.+Feed_Vol+Cell_conc._interval+RQ_integral+AS_Vol.+emission_CO2+consum_O2+generate_CO2; 0.329, 0.655, tmp_cumulo+pH+interval_yield+interval_Pdt.+OD+Feed_Vol+RQ_integral+AS_Vol.+consum_O2+interval_O2+generate_CO2; 0.340, 0.655, tmp_cumulo+pH_cumulo+interval_yield+OD+RS_cumulo+rab_integral+RQ_integral+emission_O2+consum_O2+generate_CO2; 0.319, 0.655, tmp_cumulo+pH_cumulo+AN_cumulo+interval_yield+interval_Pdt.+OD+RQ_integral+AS_Vol.+emission_O2+consum_O2+interval_O2+generate_CO2; 0.350, 0.655, tmp+pH_cumulo+interval_yield+interval_Pdt.+OD+Feed_Vol+RQ_integral+consum_O2+generate_CO2; 0.340, 0.655, tmp+pH_cumulo+interval_yield+OD+Feed_Vol+rab_integral+RQ_integral+AS_Vol.+consum_O2+generate_CO2; 0.340, 0.655, tmp+interval_yield+interval_Pdt.+OD+Feed_Vol+RQ_integral+AS_Vol.+emission_CO2+consum_O2+generate_CO2; 0.350, 0.655, tmp+pH_cumulo+interval_yield+interval_Pdt.+RQ_integral+AS_Vol.+emission_O2+consum_O2+generate_CO2; 0.350, 0.655, tmp_cumulo+PL_cumulo+interval_yield+interval_Pdt.+OD+RS_cumulo+RQ_integral+consum_O2+generate_CO2; 0.329, 0.655, tmp_cumulo+pH+pH_cumulo+AN+interval_yield+interval_Pdt.+OD+RQ_integral+AS_Vol.+consum_O2+generate_CO2; 0.340, 0.655, tmp+tmp_cumulo+AN+interval_yield+interval_Pdt.+RS_cumulo+RQ_integral+emission_CO2+consum_O2+generate_CO2; 0.360, 0.655, tmp+tmp_cumulo+pH_cumulo+interval_yield+OD+RQ_integral+consum_O2+generate_CO2; 0.329, 0.655, tmp+interval_yield+interval_Pdt.+RS_cumulo+rab_integral+RQ_integral+AS_Vol.+emission_O2+emission_CO2+consum_O2+generate_CO2; 0.319, 0.655, tmp_cumulo+pH_cumulo+interval_yield+interval_Pdt.+OD+RS_cumulo+rab_integral+RQ_integral+AS_Vol.+emission_O2+consum_O2+generate_CO2; 0.340, 0.655, tmp+pH+interval_yield+interval_Pdt.+RS_cumulo+RQ_integral+AS_Vol.+emission_CO2+consum_O2+generate_CO2; 0.329, 0.655, tmp+pH_cumulo+AN+interval_yield+interval_Pdt.+rab_integral+RQ_integral+AS_Vol.+emission_CO2+consum_O2+generate_CO2; 0.360, 0.655, tmp+pH_cumulo+AN_cumulo+interval_yield+OD+RQ_integral+consum_O2+generate_CO2; 0.318, 0.655, tmp+pH_cumulo+interval_yield+interval_Pdt.+OD+Feed_Vol+Cell_conc._interval+RQ_integral+AS_Vol.+consum_O2+interval_O2+generate_CO2; 0.318, 0.655, tmp_cumulo+pH_cumulo+interval_yield+OD+RS_cumulo+rab_integral+AS_Vol.+emission_O2+consum_O2+interval_O2+generate_CO2; 0.340, 0.655, tmp_cumulo+AN+interval_yield+interval_Pdt.+RQ_integral+AS_Vol.+emission_CO2+consum_O2+interval_O2+generate_CO2; 0.329, 0.655, tmp+pH_cumulo+interval_yield+interval_Pdt.+OD+Feed_Vol+RQ_integral+Accum._Yield+AS_Vol.+consum_O2+generate_CO2; 0.329, 0.655, tmp+tmp_cumulo+pH_cumulo+AN_cumulo+interval_yield+interval_Pdt.+OD+RQ_integral+AS_Vol.+consum_O2+generate_CO2; 0.350, 0.655, tmp_cumulo+pH_cumulo+interval_yield+interval_Pdt.+OD+RS+RQ_integral+consum_O2+generate_CO2; 0.340, 0.655, tmp_cumulo+AN+interval_yield+interval_Pdt.+Feed_Vol+RS_cumulo+RQ_integral+emission_CO2+consum_O2+generate_CO2; 0.340, 0.655, tmp+interval_yield+interval_Pdt.+Cell_conc._interval+RQ_integral+AS_Vol.+emission_O2+emission_CO2+consum_O2+generate_CO2; 0.329, 0.655, tmp_cumulo+pH_cumulo+PL_cumulo+interval_yield+interval_Pdt.+OD+RQ_integral+AS_Vol.+emission_O2+consum_O2+generate_CO2; 0.318, 0.655, tmp_cumulo+pH_cumulo+AN+interval_yield+OD+RS_cumulo+rab_integral+RQ_integral+AS_Vol.+consum_O2+interval_O2+generate_CO2; 0.329, 0.655, tmp+tmp_cumulo+interval_yield+interval_Pdt.+RS_cumulo+RQ_integral+AS_Vol.+emission_O2+emission_CO2+consum_O2+generate_CO2; 0.350, 0.655, tmp+pH_cumulo+interval_yield+interval_Pdt.+Feed_Vol+RQ_integral+AS_Vol.+consum_O2+generate_CO2; 0.329, 0.655, tmp+tmp_cumulo+pH_cumulo+interval_yield+interval_Pdt.+RQ_integral+AS_Vol.+emission_CO2+consum_O2+interval_O2+generate_CO2; 0.350, 0.655, tmp_cumulo+pH_cumulo+PL+interval_yield+OD+RS_cumulo+RQ_integral+consum_O2+generate_CO2; 0.329, 0.655, tmp_cumulo+pH+interval_yield+interval_Pdt.+RS_cumulo+rab_integral+RQ_integral+emission_O2+emission_CO2+consum_O2+generate_CO2; 0.360, 0.655, tmp+pH_cumulo+AN+interval_yield+OD+RQ_integral+consum_O2+generate_CO2; 0.350, 0.655, tmp+pH_cumulo+PL_cumulo+interval_yield+interval_Pdt.+OD+RQ_integral+consum_O2+generate_CO2; 0.307, 0.655, tmp_cumulo+pH_cumulo+interval_yield+interval_Pdt.+OD+Feed_Vol+rab_integral+RQ_integral+AS_Vol.+emission_O2+emission_CO2+consum_O2+generate_CO2; 0.340, 0.655, tmp_cumulo+pH_cumulo+AN+interval_yield+interval_Pdt.+RS_cumulo+RQ_integral+emission_CO2+consum_O2+generate_CO2; 0.329, 0.655, tmp_cumulo+interval_yield+interval_Pdt.+OD+Feed_Vol+RS_cumulo+rab_integral+RQ_integral+emission_CO2+consum_O2+generate_CO2; 0.329, 0.655, tmp+tmp_cumulo+pH_cumulo+interval_yield+OD+Cell_conc._interval+rab_integral+RQ_integral+AS_Vol.+consum_O2+generate_CO2; 0.329, 0.655, tmp_cumulo+pH_cumulo+AN+AN_cumulo+interval_yield+OD+rab_integral+RQ_integral+AS_Vol.+consum_O2+generate_CO2; 0.350, 0.655, tmp+tmp_cumulo+pH_cumulo+interval_yield+interval_Pdt.+OD+RQ_integral+consum_O2+generate_CO2; 0.329, 0.655, tmp_cumulo+pH_cumulo+PL+interval_yield+OD+Feed_Vol+rab_integral+RQ_integral+AS_Vol.+consum_O2+generate_CO2; 0.350, 0.655, tmp+interval_yield+interval_Pdt.+Feed_Vol+RS_cumulo+RQ_integral+AS_Vol.+consum_O2+generate_CO2; 0.340, 0.655, tmp_cumulo+interval_yield+interval_Pdt.+rab_integral+RQ_integral+AS_Vol.+emission_CO2+consum_O2+interval_O2+generate_CO2; 0.318, 0.655, tmp_cumulo+pH_cumulo+AN+interval_yield+interval_Pdt.+OD+rab_integral+RQ_integral+AS_Vol.+emission_O2+consum_O2+generate_CO2; 0.329, 0.655, tmp_cumulo+PL_cumulo+interval_yield+interval_Pdt.+OD+RS_cumulo+rab_integral+RQ_integral+emission_CO2+consum_O2+generate_CO2; 0.318, 0.655, tmp_cumulo+pH_cumulo+PL_cumulo+interval_yield+OD+rab_integral+RQ_integral+AS_Vol.+emission_CO2+consum_O2+interval_O2+generate_CO2; 0.329, 0.655, tmp+tmp_cumulo+pH_cumulo+AN+interval_yield+OD+rab_integral+RQ_integral+AS_Vol.+consum_O2+generate_CO2; 0.318, 0.655, tmp_cumulo+pH_cumulo+AN+interval_yield+interval_Pdt.+OD+RS_cumulo+rab_integral+RQ_integral+emission_CO2+consum_O2+generate_CO2; 0.339, 0.655, tmp+pH_cumulo+interval_yield+interval_Pdt.+OD+RQ_integral+emission_O2+emission_CO2+consum_O2+generate_CO2; 0.339, 0.655, tmp+interval_yield+interval_Pdt.+Feed_Vol+RQ_integral+AS_Vol.+emission_O2+emission_CO2+consum_O2+generate_CO2; 0.329, 0.655, tmp_cumulo+pH+interval_yield+interval_Pdt.+OD+RS_cumulo+RQ_integral+emission_O2+emission_CO2+consum_O2+generate_CO2; 0.329, 0.655, tmp+pH_cumulo+AN_cumulo+interval_yield+interval_Pdt.+rab_integral+RQ_integral+AS_Vol.+emission_CO2+consum_O2+generate_CO2; 0.329, 0.655, tmp_cumulo+pH_cumulo+PL_cumulo+AN_cumulo+interval_yield+OD+rab_integral+RQ_integral+AS_Vol.+consum_O2+generate_CO2; 0.318, 0.655, tmp_cumulo+pH_cumulo+AN+AN_cumulo+interval_yield+OD+rab_integral+RQ_integral+AS_Vol.+consum_O2+interval_O2+generate_CO2; 0.329, 0.655, tmp_cumulo+pH_cumulo+AN_cumulo+interval_yield+interval_Pdt.+Feed_Vol+RQ_integral+AS_Vol.+consum_O2+interval_O2+generate_CO2; 0.359, 0.655, tmp_cumulo+pH_cumulo+rab_integral+RQ_integral+AS_Vol.+consum_O2+interval_O2+generate_CO2; 0.350, 0.655, tmp+tmp_cumulo+interval_yield+interval_Pdt.+RS_cumulo+RQ_integral+AS_Vol.+consum_O2+generate_CO2; 0.359, 0.655, tmp+interval_yield+interval_Pdt.+Cell_conc._interval+RQ_integral+AS_Vol.+consum_O2+generate_CO2; 0.350, 0.655, tmp_cumulo+PL_cumulo+interval_yield+interval_Pdt.+RS_cumulo+RQ_integral+AS_Vol.+consum_O2+generate_CO2; 0.339, 0.655, tmp_cumulo+pH_cumulo+interval_yield+interval_Pdt.+Feed_Vol+RS_cumulo+RQ_integral+AS_Vol.+consum_O2+generate_CO2; 0.350, 0.655, tmp_cumulo+AN+interval_yield+interval_Pdt.+RS_cumulo+rab_integral+RQ_integral+consum_O2+generate_CO2;

0.329, 0.655, tmp_cumulo+pH_cumulo+interval_yield+interval_Pdt.+OD+RS_cumulo+rab_integral+RQ_integral+emission_O2+consum_O2+generate_CO2; 0.350, 0.655, tmp+pH_cumulo+interval_yield+OD+rab_integral+RQ_integral+AS_Vol.+consum_O2+generate_CO2; 0.329, 0.655, tmp_cumulo+AN+interval_yield+interval_Pdt.+Feed_Vol+RS_cumulo+RQ_integral+AS_Vol.+emission_CO2+consum_O2+generate_CO2; 0.329, 0.655, tmp_cumulo+pH_cumulo+AN_cumulo+interval_yield+interval_Pdt.+rab_integral+RQ_integral+AS_Vol.+consum_O2+interval_O2+generate_CO2; 0.339, 0.655, tmp_cumulo+pH_cumulo+interval_yield+interval_Pdt.+OD+Feed_Vol+RQ_integral+emission_CO2+consum_O2+generate_CO2; 0.339, 0.655, tmp+AN_cumulo+interval_yield+interval_Pdt.+OD+RQ_integral+AS_Vol.+emission_CO2+consum_O2+generate_CO2; 0.339, 0.655, tmp_cumulo+pH+interval_yield+interval_Pdt.+Feed_Vol+RQ_integral+AS_Vol.+emission_CO2+consum_O2+generate_CO2; 0.349, 0.655, tmp_cumulo+pH_cumulo+AN_cumulo+interval_yield+OD+Feed_Vol+RQ_integral+consum_O2+generate_CO2; 0.318, 0.655, tmp+pH_cumulo+interval_yield+interval_Pdt.+OD+Feed_Vol+RQ_integral+AS_Vol.+emission_O2+emission_CO2+consum_O2+generate_CO2; 0.329, 0.655, tmp+pH_cumulo+PL_cumulo+interval_yield+interval_Pdt.+OD+RQ_integral+AS_Vol.+emission_CO2+consum_O2+generate_CO2; 0.349, 0.655, tmp_cumulo+interval_yield+interval_Pdt.+OD+RS_cumulo+RQ_integral+consum_O2+interval_O2+generate_CO2; 0.329, 0.655, tmp_cumulo+interval_yield+interval_Pdt.+Feed_Vol+RS_cumulo+rab_integral+RQ_integral+emission_O2+emission_CO2+consum_O2+generate_CO2; 0.329, 0.655, tmp+tmp_cumulo+pH_cumulo+interval_yield+interval_Pdt.+OD+RS_cumulo+RQ_integral+emission_CO2+consum_O2+generate_CO2; 0.318, 0.655, tmp_cumulo+pH_cumulo+interval_yield+interval_Pdt.+RS_cumulo+rab_integral+RQ_integral+AS_Vol.+emission_CO2+consum_O2+interval_O2+generate_CO2; 0.349, 0.655, tmp_cumulo+pH_cumulo+AN+interval_yield+OD+RS+RQ_integral+consum_O2+generate_CO2; 0.318, 0.655, tmp_cumulo+pH_cumulo+interval_yield+interval_Pdt.+rab_integral+AS_Vol.+emission_O2+emission_CO2+consum_O2+interval_O2+generate_CO2; 0.329, 0.655, tmp+tmp_cumulo+pH_cumulo+interval_yield+OD+rab_integral+RQ_integral+AS_Vol.+emission_O2+consum_O2+generate_CO2; 0.329, 0.655, tmp_cumulo+pH_cumulo+AN+AN_cumulo+interval_yield+interval_Pdt.+OD+RQ_integral+AS_Vol.+consum_O2+generate_CO2; 0.339, 0.655, tmp_cumulo+pH+pH_cumulo+interval_yield+interval_Pdt.+RQ_integral+AS_Vol.+emission_CO2+consum_O2+generate_CO2; 0.329, 0.655, tmp_cumulo+pH_cumulo+AN_cumulo+interval_yield+interval_Pdt.+RQ_integral+AS_Vol.+emission_O2+consum_O2+interval_O2+generate_CO2; 0.349, 0.655, tmp_cumulo+interval_yield+OD+RS_cumulo+RQ_integral+AS_Vol.+consum_O2+interval_O2+generate_CO2; 0.359, 0.655, tmp_cumulo+pH+pH_cumulo+interval_yield+OD+RQ_integral+consum_O2+generate_CO2; 0.318, 0.655, tmp_cumulo+pH_cumulo+AN_cumulo+interval_yield+interval_Pdt.+OD+RQ_integral+AS_Vol.+emission_O2+emission_CO2+consum_O2+generate_CO2; 0.318, 0.655, tmp_cumulo+pH_cumulo+interval_yield+interval_Pdt.+OD+RS_cumulo+RQ_integral+AS_Vol.+emission_O2+consum_O2+interval_O2+generate_CO2; 0.339, 0.655, tmp_cumulo+pH_cumulo+interval_yield+interval_Pdt.+Feed_Vol+RQ_integral+AS_Vol.+emission_O2+consum_O2+generate_CO2; 0.349, 0.655, tmp_cumulo+pH_cumulo+interval_yield+OD+Feed_Vol+RQ_integral+emission_CO2+consum_O2+generate_CO2; 0.318, 0.655, tmp_cumulo+pH_cumulo+AN_cumulo+interval_yield+interval_Pdt.+rab_integral+RQ_integral+AS_Vol.+emission_CO2+consum_O2+interval_O2+generate_CO2; 0.349, 0.655, tmp_cumulo+pH+pH_cumulo+OD+RQ_integral+AS_Vol.+consum_O2+interval_O2+generate_CO2; 0.339, 0.655, tmp+AN+interval_yield+interval_Pdt.+RQ_integral+AS_Vol.+emission_CO2+consum_O2+interval_O2+generate_CO2; 0.359, 0.655, tmp+pH+pH_cumulo+interval_yield+OD+RQ_integral+consum_O2+generate_CO2; 0.329, 0.655, tmp_cumulo+pH+interval_yield+interval_Pdt.+Feed_Vol+RS_cumulo+RQ_integral+AS_Vol.+emission_CO2+consum_O2+generate_CO2; 0.339, 0.655, tmp_cumulo+pH+pH_cumulo+interval_yield+OD+RS_cumulo+RQ_integral+consum_O2+interval_O2+generate_CO2; 0.349, 0.654, tmp_cumulo+AN+interval_yield+interval_Pdt.+RS_cumulo+RQ_integral+AS_Vol.+consum_O2+generate_CO2; 0.329, 0.654, tmp_cumulo+pH+pH_cumulo+interval_yield+OD+Cell_conc._interval+rab_integral+RQ_integral+AS_Vol.+consum_O2+generate_CO2; 0.318, 0.654, tmp_cumulo+pH_cumulo+interval_yield+interval_Pdt.+OD+Cell_conc._interval+RQ_integral+AS_Vol.+emission_O2+consum_O2+interval_O2+generate_CO2; 0.339, 0.654, tmp_cumulo+pH_cumulo+interval_yield+interval_Pdt.+OD+rab_integral+RQ_integral+emission_CO2+consum_O2+generate_CO2; 0.329, 0.654, tmp_cumulo+pH_cumulo+AN_cumulo+interval_yield+interval_Pdt.+OD+RS_cumulo+rab_integral+RQ_integral+consum_O2+generate_CO2; 0.318, 0.654, tmp_cumulo+pH_cumulo+PL_cumulo+AN+interval_yield+OD+rab_integral+RQ_integral+AS_Vol.+consum_O2+interval_O2+generate_CO2; 0.307, 0.654, tmp_cumulo+pH_cumulo+interval_yield+interval_Pdt.+OD+Feed_Vol+rab_integral+RQ_integral+AS_Vol.+emission_O2+consum_O2+interval_O2+generate_CO2; 0.339, 0.654, tmp+interval_yield+interval_Pdt.+rab_integral+RQ_integral+Accum._Yield+AS_Vol.+emission_CO2+consum_O2+generate_CO2; 0.329, 0.654, tmp_cumulo+interval_yield+interval_Pdt.+OD+RS_cumulo+Cell_conc._interval+RQ_integral+AS_Vol.+emission_CO2+consum_O2+generate_CO2; 0.307, 0.654, tmp_cumulo+pH_cumulo+AN_cumulo+interval_yield+interval_Pdt.+OD+rab_integral+RQ_integral+AS_Vol.+emission_CO2+consum_O2+interval_O2+generate_CO2; 0.349, 0.654, tmp_cumulo+AN_cumulo+interval_yield+interval_Pdt.+RS_cumulo+RQ_integral+AS_Vol.+consum_O2+generate_CO2; 0.339, 0.654, tmp_cumulo+PL_cumulo+interval_yield+interval_Pdt.+RS_cumulo+RQ_integral+emission_O2+emission_CO2+consum_O2+generate_CO2; 0.318, 0.654, tmp_cumulo+pH_cumulo+PL+interval_yield+OD+Feed_Vol+rab_integral+RQ_integral+AS_Vol.+consum_O2+interval_O2+generate_CO2; 0.318, 0.654, tmp_cumulo+pH_cumulo+interval_yield+interval_Pdt.+Feed_Vol+RS_cumulo+rab_integral+RQ_integral+AS_Vol.+emission_CO2+consum_O2+generate_CO2; 0.318, 0.654, tmp_cumulo+pH_cumulo+interval_yield+interval_Pdt.+OD+Cell_conc._interval+RQ_integral+AS_Vol.+emission_O2+emission_CO2+consum_O2+generate_CO2; 0.318, 0.654, tmp_cumulo+pH+pH_cumulo+interval_yield+interval_Pdt.+OD+RS_cumulo+RQ_integral+AS_Vol.+emission_CO2+consum_O2+generate_CO2; 0.349, 0.654, tmp_cumulo+pH_cumulo+interval_yield+interval_Pdt.+OD+Cell_conc._interval+RQ_integral+consum_O2+generate_CO2; 0.318, 0.654, tmp_cumulo+pH+pH_cumulo+interval_yield+interval_Pdt.+OD+RQ_integral+AS_Vol.+emission_O2+consum_O2+interval_O2+generate_CO2; 0.328, 0.654, tmp_cumulo+pH+pH_cumulo+interval_yield+interval_

Pdt.+RQ_integral+AS_Vol.+emission_CO2+consum_O2+ interval_O2+generate_CO2; 0.349, 0.654, tmp_cumulo+ pH_cumulo+AN_cumulo+interval_yield+RQ_integral+ AS_Vol.+consum_O2+interval_O2+generate_CO2; 0.339, 0.654, tmp_cumulo+interval_yield+interval_Pdt.+Feed_ Vol+RS_cumulo+RQ_integral+AS_Vol.+emission_O2+ consum_O2+generate_CO2; 0.328, 0.654, tmp_cumulo+ pH+interval_yield+interval_Pdt.+OD+RQ_integral+AS_ Vol.+emission_CO2+consum_O2+interval_O2+generate_ CO2; 0.339, 0.654, tmp_cumulo+pH+interval_yield+ interval_Pdt.+Feed_Vol+RQ_integral+AS_Vol.+consum_ O2+interval_O2+generate_CO2; 0.339, 0.654, tmp_ cumulo+pH_cumulo+PL_cumulo+interval_yield+OD+RS_ cumulo+rab_integral+RQ_integral+consum_O2+generate_ CO2; 0.359, 0.654, tmp+AN_cumulo+interval_yield+ interval_Pdt.+RS_cumulo+RQ_integral+consum_O2+ generate_CO2; 0.339, 0.654, tmp+pH_cumulo+interval_ yield+OD+Cell_conc._interval+RQ_integral+AS_Vol.+ consum_O2+interval_O2+generate_CO2; 0.328, 0.654, tmp_cumulo+pH_cumulo+interval_yield+interval_Pdt.+ Feed_Vol+RQ_integral+AS_Vol.+emission_O2+emission_ CO2+consum_O2+generate_CO2; 0.339, 0.654, tmp_cu- mulo+interval_yield+interval_Pdt.+Feed_Vol+rab_ integral+RQ_integral+AS_Vol.+emission_CO2+consum_ O2+generate_CO2; 0.349, 0.654, tmp_cumulo+pH_ cumulo+AN_cumulo+interval_yield+OD+rab_integral+ RQ_integral+consum_O2+generate_CO2; 0.359, 0.654, tmp+interval_yield+interval_Pdt.+RS_cumulo+RQ_inte- gral+AS_Vol.+consum_O2+generate_CO2; 0.349, 0.654, tmp_cumulo+pH_cumulo+interval_yield+interval_Pdt.+ RS_cumulo+RQ_integral+emission_O2+consum_O2+gen- erate_CO2; 0.368, 0.654, tmp+interval_yield+interval_ Pdt.+RQ_integral+consum_O2+interval_O2+generate_ CO2; 0.349, 0.654, tmp+pH+pH_cumulo+interval_yield+ interval_Pdt.+OD+RQ_integral+AS_Vol.+consum_generate_ CO2; 0.339, 0.654, tmp+AN_cumulo+interval_yield+ interval_Pdt.+Cell_conc._interval+RQ_integral+AS_Vol.+ emission_CO2+consum_O2+generate_CO2; 0.339, 0.654, tmp_cumulo+pH+AN+interval_yield+interval_Pdt.+RQ_ integral+AS_Vol.+emission_CO2+consum_O2+generate_ CO2; 0.328, 0.654, tmp_cumulo+pH+pH_cumulo+interval_ yield+interval_Pdt.+OD+RS_cumulo+RQ_integral+ emission_CO2+consum_O2+generate_CO2; 0.317, 0.654, tmp+tmp_cumulo+pH_cumulo+interval_yield+interval_ Pdt.+OD+rab_integral+RQ_integral+AS_Vol.+consum_ O2+interval_O2+generate_CO2; 0.317, 0.654, tmp_cu- mulo+pH_cumulo+AN_cumulo+interval_yield+interval_ Pdt.+OD+Feed_Vol+RQ_integral+AS_Vol.+emission_ CO2+consum_O2+generate_CO2; 0.359, 0.654, tmp_ cumulo+interval_yield+OD+RS_cumulo+RQ_integral+ AS_Vol.+consum_O2+generate_CO2; 0.306, 0.654, tmp_ cumulo+pH_cumulo+interval_yield+interval_Pdt.+OD+ Feed_Vol+RS_cumulo+rab_integral+RQ_integral+AS_ Vol.+consum_O2+interval_O2+generate_CO2; 0.349, 0.654, tmp_cumulo+pH_cumulo+AN+interval_yield+inter- val_Pdt.+RS_cumulo+RQ_integral+consum_O2+generate_ CO2; 0.317, 0.654, tmp+tmp_cumulo+pH_cumulo+inter- val_yield+interval_Pdt.+OD+Feed_Vol+rab_integral+RQ_ integral+AS_Vol.+consum_O2+generate_CO2; 0.339, 0.654, tmp_cumulo+pH_cumulo+PL+interval_yield+OD+ Cell_conc._interval+RQ_integral+AS_Vol.+consum_O2+ generate_CO2; 0.317, 0.654, tmp_cumulo+pH_cumulo+ AN+interval_yield+interval_Pdt.+RS_cumulo+rab_ integral+RQ_integral+AS_Vol.+emission_CO2+consum_ O2+generate_CO2; 0.339, 0.654, tmp_cumulo+pH_ cumulo+AN_cumulo+interval_yield+interval_Pdt.+RQ_ integral+AS_Vol.+emission_CO2+consum_O2+generate_ CO2; 0.317, 0.654, tmp_cumulo+pH_cumulo+PL_cumulo+ interval_yield+interval_Pdt.+OD+rab_integral+RQ_inte- gral+AS_Vol.+consum_O2+interval_O2+generate_CO2; 0.328, 0.654, tmp_cumulo+pH_cumulo+interval_yield+in- terval_Pdt.+RS_cumulo+rab_integral+RQ_integral+emis- sion_O2+emission_CO2+consum_O2+generate_CO2; 0.339, 0.654, tmp_cumulo+pH_cumulo+interval_yield+ OD+RQ_integral+Accum._Yield+AS_Vol.+emission_ CO2+consum_O2+generate_CO2; 0.349, 0.654, tmp_cu- mulo+PL_cumulo+interval_yield+interval_Pdt.+RS_ cumulo+rab_integral+RQ_integral+consum_O2+generate_ CO2; 0.328, 0.654, tmp_cumulo+pH_cumulo+AN+ interval_yield+OD+RS_cumulo+RQ_integral+AS_Vol.+ emission_CO2+consum_O2+generate_CO2; 0.339, 0.654, tmp_cumulo+pH+pH_cumulo+AN+interval_yield+OD+ RS_cumulo+RQ_integral+consum_O2+generate_CO2; 0.317, 0.654, tmp_cumulo+pH_cumulo+interval_yield+ OD+Cell_conc._interval+rab_integral+RQ_integral+AS_ Vol.+emission_O2+consum_O2+interval_O2+generate_ CO2; 0.339, 0.654, tmp+pH+interval_yield+interval_Pdt.+ OD+RS_cumulo+RQ_integral+emission_CO2+consum_ O2+generate_CO2; 0.339, 0.654, tmp_cumulo+pH_ cumulo+AN+interval_yield+interval_Pdt.+RQ_integral+ AS_Vol.+emission_O2+consum_O2+generate_CO2; 0.339, 0.654, tmp_cumulo+interval_yield+interval_Pdt.+OD+ Feed_Vol+RS_cumulo+RQ_integral+AS_Vol.+consum_ O2+generate_CO2; 0.339, 0.654, tmp_cumulo+AN+AN_ cumulo+interval_yield+interval_Pdt.+RS_cumulo+RQ_ integral+emission_CO2+consum_O2+generate_CO2; 0.328, 0.654, tmp+interval_yield+interval_Pdt.+OD+RS_ cumulo+rab_integral+RQ_integral+AS_Vol.+emission_ CO2+consum_O2+generate_CO2; 0.328, 0.654, tmp_cu- mulo+pH+interval_yield+interval_Pdt.+OD+Feed_Vol+ RS_cumulo+RQ_integral+AS_Vol.+consum_O2+generate_ CO2; 0.339, 0.654, tmp_cumulo+interval_yield+interval_ Pdt.+RS_cumulo+rab_integral+RQ_integral+AS_Vol.+ emission_O2+consum_O2+generate_CO2; 0.317, 0.654, tmp_cumulo+pH_cumulo+AN+interval_yield+interval_ Pdt.+OD+Cell_conc._interval+RQ_integral+AS_Vol.+con- sum_O2+interval_O2+generate_CO2; 0.317, 0.654, tmp_ cumulo+pH_cumulo+interval_yield+interval_Pdt.+OD+ Feed_Vol+Cell_conc._interval+rab_integral+RQ_integral+ AS_Vol.+consum_O2+generate_CO2; 0.359, 0.654, tmp+ interval_yield+interval_Pdt.+OD+RQ_integral+AS_Vol.+ consum_O2+generate_CO2; 0.349, 0.654, tmp_cumulo+ interval_yield+interval_Pdt.+RQ_integral+AS_Vol.+ emission_O2+consum_O2+interval_O2+generate_CO2; 0.328, 0.654, tmp_cumulo+pH_cumulo+interval_yield+ OD+RS_cumulo+RQ_integral+AS_Vol.+emission_O2+ emission_CO2+consum_O2+generate_CO2; 0.306, 0.654, tmp_cumulo+pH_cumulo+AN+interval_yield+interval_ Pdt.+OD+Feed_Vol+rab_integral+RQ_integral+AS_Vol.+ emission_CO2+consum_O2+generate_CO2; 0.339, 0.654, tmp+interval_yield+interval_Pdt.+Cell_conc._interval+ RQ_integral+AS_Vol.+emission_CO2+consum_O2+inter- val_O2+generate_CO2; 0.317, 0.654, tmp_cumulo+pH_cu- mulo+interval_yield+interval_Pdt.+OD+RS_cumulo+Cell_ conc._interval+RQ_integral+AS_Vol.+emission_CO2+ consum_O2+generate_CO2; 0.328, 0.654, tmp_cumulo+ pH_cumulo+PL+interval_yield+OD+rab_integral+RQ_ integral+AS_Vol.+emission_CO2+consum_O2+generate_ CO2; 0.306, 0.654, tmp_cumulo+pH_cumulo+AN_ cumulo+interval_yield+interval_Pdt.+OD+Feed_Vol+rab_ integral+RQ_integral+AS_Vol.+consum_O2+interval_O2+ generate_CO2; 0.328, 0.654, tmp+pH_cumulo+interval_ yield+OD+Feed_Vol+rab_integral+RQ_integral+AS_Vol.+ consum_O2+interval_O2+generate_CO2; 0.377, 0.654, tmp_cumulo+RQ_integral+AS_Vol.+consum_O2+interval_O2+generate_CO2; 0.339, 0.654, tmp_cumulo+interval_yield+interval_Pdt.+RS_cumulo+Cell_conc._interval+RQ_integral+emission_O2+emission_CO2+consum_O2+generate_CO2; 0.328, 0.654, tmp_cumulo+pH_cumulo+AN+interval_yield+OD+Cell_conc._interval+RQ_integral+AS_Vol.+emission_CO2+consum_O2+generate_CO2; 0.339, 0.654, tmp_cumulo+AN+interval_yield+interval_Pdt.+rab_integral+RQ_integral+AS_Vol.+emission_CO2+consum_O2+generate_CO2; 0.349, 0.654, tmp_cumulo+pH_cumulo+OD+Feed_Vol+RQ_integral+AS_Vol.+consum_O2+interval_O2+generate_CO2; 0.349, 0.654, tmp_cumulo+pH+interval_yield+interval_Pdt.+RQ_integral+AS_Vol.+emission_O2+consum_O2+generate_CO2; 0.328, 0.654, tmp_cumulo+AN_cumulo+interval_yield+interval_Pdt.+RS_cumulo+rab_integral+emission_O2+emission_CO2+consum_O2+generate_CO2; 0.339, 0.654, tmp_cumulo+pH_cumulo+interval_yield+Feed_Vol+rab_integral+RQ_integral+AS_Vol.+consum_O2+interval_O2+generate_CO2; 0.317, 0.654, tmp+tmp_cumulo+pH_cumulo+interval_yield+OD+rab_integral+RQ_integral+AS_Vol.+emission_CO2+consum_O2+interval_O2+generate_CO2; 0.349, 0.654, tmp_cumulo+AN_cumulo+interval_yield+interval_Pdt.+RS_cumulo+rab_integral+RQ_integral+consum_O2+generate_CO2; 0.338, 0.654, tmp+pH_cumulo+interval_yield+OD+Feed_Vol+Cell_conc._interval+RQ_integral+AS_Vol.+consum_O2+generate_CO2; 0.338, 0.654, tmp+AN+interval_yield+interval_Pdt.+RS_cumulo+RQ_integral+emission_CO2+emission_CO2+consum_O2+generate_CO2; 0.317, 0.654, tmp_cumulo+pH_cumulo+interval_yield+interval_Pdt.+OD+Feed_Vol+RS_cumulo+RQ_integral+AS_Vol.+emission_O2+consum_O2+generate_CO2; 0.338, 0.654, tmp_cumulo+pH_cumulo+AN_cumulo+interval_yield+interval_Pdt.+OD+rab_integral+RQ_integral+consum_O2+generate_CO2; 0.328, 0.654, tmp_cumulo+pH_cumulo+PL_cumulo+interval_yield+interval_Pdt.+OD+Cell_conc._interval+RQ_integral+AS_Vol.+consum_O2+generate_CO2; 0.328, 0.654, tmp_cumulo+pH_cumulo+AN+interval_yield+interval_Pdt.+RS_cumulo+RQ_integral+AS_Vol.+consum_O2+interval_O2+generate_CO2; 0.306, 0.654, tmp_cumulo+pH_cumulo+AN+interval_yield+interval_Pdt.+OD+rab_integral+RQ_integral+AS_Vol.+emission_O2+emission_CO2+consum_O2+generate_CO2; 0.338, 0.654, tmp_cumulo+interval_yield+interval_Pdt.+RS_cumulo+RQ_integral+AS_Vol.+emission_O2+consum_O2+interval_O2+generate_CO2; 0.317, 0.654, tmp+tmp_cumulo+pH_cumulo+interval_yield+interval_Pdt.+OD+RQ_integral+AS_Vol.+emission_O2+emission_CO2+consum_O2+generate_CO2; 0.338, 0.654, tmp_cumulo+PL_cumulo+AN_cumulo+interval_yield+interval_Pdt.+RS_cumulo+RQ_integral+emission_CO2+consum_O2+generate_CO2; 0.317, 0.654, tmp+pH_cumulo+AN+interval_yield+interval_Pdt.+OD+Feed_Vol+RQ_integral+AS_Vol.+emission_CO2+consum_O2+generate_CO2; 0.328, 0.654, tmp_cumulo+pH+pH_cumulo+interval_yield+interval_Pdt.+OD+RS_cumulo+rab_integral+RQ_integral+consum_O2+generate_CO2; 0.338, 0.654, tmp_cumulo+pH_cumulo+AN+interval_yield+OD+RS_cumulo+RQ_integral+consum_O2+interval_O2+generate_CO2; 0.358, 0.654, tmp_cumulo+interval_yield+OD+RS_cumulo+rab_integral+RQ_integral+consum_O2+generate_CO2; 0.317, 0.654, tmp_cumulo+interval_yield+interval_Pdt.+OD+Feed_Vol+RS_cumulo+rab_integral+RQ_integral+AS_Vol.+emission_CO2+consum_O2+generate_CO2; 0.328, 0.654, tmp_cumulo+interval_yield+interval_Pdt.+Feed_Vol+RS_cumulo+RQ_integral+AS_Vol.+emission_CO2+consum_O2+interval_O2+generate_CO2; 0.317, 0.654, tmp_cumulo+pH_cumulo+AN_cumulo+interval_yield+interval_Pdt.+OD+rab_integral+RQ_integral+AS_Vol.+emission_O2+consum_O2+generate_CO2; 0.349, 0.654, tmp+tmp_cumulo+interval_yield+interval_Pdt.+RS_cumulo+RQ_integral+emission_O2+consum_O2+generate_CO2; 0.349, 0.654, tmp_cumulo+pH+interval_yield+interval_Pdt.+RS_cumulo+RQ_integral+emission_O2+consum_O2+generate_CO2; 0.306, 0.654, tmp+pH_cumulo+interval_yield+interval_Pdt.+OD+Feed_Vol+rab_integral+RQ_integral+AS_Vol.+emission_CO2+consum_O2+interval_O2+generate_CO2; 0.306, 0.654, tmp_cumulo+pH_cumulo+AN+interval_yield+interval_Pdt.+OD+RS_cumulo+rab_integral+RQ_integral+AS_Vol.+emission_CO2+consum_O2+generate_CO2; 0.328, 0.654, tmp_cumulo+pH+pH_cumulo+AN_cumulo+interval_yield+interval_Pdt.+OD+RQ_integral+AS_Vol.+consum_O2+generate_CO2; 0.358, 0.654, tmp_cumulo+interval_yield+OD+RS_cumulo+RQ_integral+emission_CO2+consum_O2+generate_CO2; 0.328, 0.654, tmp_cumulo+pH_cumulo+interval_yield+OD+RS_cumulo+Cell_conc._interval+rab_integral+RQ_integral+AS_Vol.+consum_O2+generate_CO2; 0.338, 0.654, tmp_cumulo+pH+AN_cumulo+interval_yield+interval_Pdt.+RQ_integral+AS_Vol.+emission_CO2+consum_O2+generate_CO2; 0.328, 0.654, tmp+tmp_cumulo+pH_cumulo+AN_cumulo+interval_yield+OD+rab_integral+RQ_integral+AS_Vol.+consum_O2+generate_CO2; 0.317, 0.654, tmp_cumulo+pH+pH_cumulo+interval_yield+OD+RS_cumulo+rab_integral+RQ_integral+AS_Vol.+consum_O2+interval_O2+generate_CO2; 0.338, 0.654, tmp_cumulo+interval_yield+interval_Pdt.+OD+RS_cumulo+rab_integral+RQ_integral+emission_O2+consum_O2+generate_CO2; 0.338, 0.654, tmp+pH_cumulo+interval_yield+interval_Pdt.+OD+RS+RQ_integral+emission_CO2+consum_O2+generate_CO2; 0.338, 0.654, tmp_cumulo+pH_cumulo+interval_yield+OD+Feed_Vol+RS_cumulo+rab_integral+RQ_integral+consum_O2+generate_CO2; 0.338, 0.654, tmp+pH_cumulo+interval_yield+OD+Cell_conc._interval+RQ_integral+AS_Vol.+emission_CO2+consum_O2+generate_CO2; 0.328, 0.654, tmp_cumulo+interval_yield+interval_Pdt.+OD+RS_cumulo+RQ_integral+AS_Vol.+emission_CO2+consum_O2+interval_O2+generate_CO2; 0.338, 0.654, tmp+interval_yield+interval_Pdt.+OD+Feed_Vol+RS_cumulo+RQ_integral+emission_CO2+consum_O2+generate_CO2; 0.338, 0.654, tmp_cumulo+pH+AN_cumulo+interval_yield+interval_Pdt.+RS_cumulo+RQ_integral+emission_CO2+consum_O2+generate_CO2; 0.328, 0.654, tmp+pH_cumulo+interval_yield+interval_Pdt.+Cell_conc._interval+rab_integral+RQ_integral+AS_Vol.+emission_CO2+consum_O2+generate_CO2; 0.338, 0.654, tmp+tmp_cumulo+AN_cumulo+interval_yield+interval_Pdt.+RS_cumulo+RQ_integral+emission_CO2+consum_O2+generate_CO2; 0.338, 0.654, tmp+pH_cumulo+PL_cumulo+interval_yield+interval_Pdt.+RQ_integral+AS_Vol.+emission_CO2+consum_O2+generate_CO2; 0.358, 0.654, tmp_cumulo+pH_cumulo+PL_cumulo+interval_yield+OD+RQ_integral+consum_O2+generate_CO2; 0.358, 0.654, tmp+interval_yield+interval_Pdt.+RQ_integral+Accum._Yield+AS_Vol.+consum_O2+generate_CO2; 0.328, 0.654, tmp_cumulo+pH+AN+interval_yield+interval_Pdt.+RS_cumulo+RQ_integral+AS_Vol.+emission_CO2+consum_O2+generate_CO2; 0.328, 0.654, tmp_cumulo+pH_cumulo+PL_cumulo+interval_yield+interval_Pdt.+rab_integral+RQ_integral+AS_Vol.+emission_CO2+consum_O2+generate_CO2; 0.328, 0.654, tmp_cumulo+pH_cumulo+PL_cumulo+interval_yield+interval_Pdt.+RS_ cumulo+RQ_integral+AS_Vol.+emission_CO2+consum_O2+generate_CO2; 0.317, 0.654, tmp_cumulo+interval_yield+interval_Pdt.+Feed_Vol+RS_cumulo+rab_integral+RQ_integral+AS_Vol.+emission_O2+emission_CO2+consum_O2+generate_CO2; 0.328, 0.654, tmp_cumulo+pH_cumulo+interval_yield+interval_Pdt.+RS_cumulo+rab_integral+RQ_integral+AS_Vol.+consum_O2+interval_O2+generate_CO2; 0.317, 0.654, tmp+pH_cumulo+PL_cumulo+interval_yield+interval_Pdt.+OD+Feed_Vol+rab_integral+RQ_integral+AS_Vol.+consum_O2+generate_CO2; 0.348, 0.654, tmp_cumulo+pH+pH_cumulo+interval_yield+interval_Pdt.+RQ_integral+AS_Vol.+consum_O2+generate_CO2; 0.328, 0.654, tmp_cumulo+AN_cumulo+interval_yield+interval_Pdt.+RS_cumulo+RQ_integral+AS_Vol.+emission_O2+emission_CO2+consum_O2+generate_CO2; 0.348, 0.654, tmp_cumulo+AN+interval_yield+interval_Pdt.+RQ_integral+AS_Vol.+consum_O2+interval_O2+generate_CO2; 0.328, 0.654, tmp+tmp_cumulo+pH_cumulo+PL_cumulo+interval_yield+interval_Pdt.+OD+RQ_integral+AS_Vol.+consum_O2+interval_O2+generate_CO2; 0.338, 0.654, tmp_cumulo+pH+AN+interval_yield+interval_Pdt.+RQ_integral+AS_Vol.+consum_O2+interval_O2+generate_CO2; 0.328, 0.654, tmp_cumulo+pH+pH_cumulo+interval_yield+interval_Pdt.+RS_cumulo+RQ_integral+AS_Vol.+emission_CO2+consum_O2+generate_CO2; 0.338, 0.654, tmp+interval_yield+interval_Pdt.+RS_cumulo+Cell_conc._interval+rab_integral+RQ_integral+emission_CO2+consum_O2+generate_CO2; 0.338, 0.654, tmp+pH_cumulo+interval_yield+interval_Pdt.+OD+Cell_conc._interval+RQ_integral+emission_CO2+consum_O2+generate_CO2; 0.328, 0.654, tmp+tmp_cumulo+pH_cumulo+PL_cumulo+interval_yield+interval_Pdt.+OD+RQ_integral+AS_Vol.+consum_O2+generate_CO2; 0.338, 0.654, tmp_cumulo+AN_cumulo+interval_yield+interval_Pdt.+Feed_Vol+RS_cumulo+RQ_integral+emission_CO2+consum_O2+generate_CO2; 0.328, 0.654, tmp+interval_yield+interval_Pdt.+OD+RS_cumulo+RQ_integral+AS_Vol.+emission_O2+emission_CO2+consum_O2+generate_CO2; 0.348, 0.654, tmp_cumulo+interval_yield+interval_Pdt.+RS_cumulo+RQ_integral+Accum._Yield+emission_CO2+consum_O2+generate_CO2; 0.338, 0.654, tmp_cumulo+pH+interval_yield+interval_Pdt.+OD+RQ_integral+AS_Vol.+emission_O2+consum_O2+generate_CO2; 0.328, 0.654, tmp_cumulo+pH_cumulo+AN+interval_yield+interval_Pdt.+Feed_Vol+RQ_integral+AS_Vol.+emission_CO2+consum_O2+generate_CO2; 0.338, 0.654, tmp+AN+interval_yield+interval_Pdt.+RQ_integral+AS_Vol.+emission_O2+emission_CO2+consum_O2+generate_CO2; 0.338, 0.654, tmp_cumulo+pH+interval_yield+interval_Pdt.+RS_cumulo+RQ_integral+AS_Vol.+consum_O2+interval_O2+generate_CO2; 0.317, 0.654, tmp+tmp_cumulo+pH_cumulo+interval_yield+interval_Pdt.+OD+RQ_integral+AS_Vol.+emission_O2+consum_O2+interval_O2+generate_CO2; 0.317, 0.654, tmp_cumulo+pH_cumulo+PL_cumulo+interval_yield+interval_Pdt.+OD+RS_cumulo+RQ_integral+AS_Vol.+emission_CO2+consum_O2+generate_CO2; 0.348, 0.654, tmp_cumulo+pH+interval_yield+interval_Pdt.+RS_cumulo+rab_integral+RQ_integral+consum_O2+generate_CO2; 0.338, 0.654, tmp+tmp_cumulo+pH+pH_cumulo+interval_yield+OD+RQ_integral+AS_Vol.+consum_O2+generate_CO2; 0.338, 0.654, tmp+interval_yield+interval_Pdt.+rab_integral+RQ_integral+AS_Vol.+emission_CO2+consum_O2+interval_O2+generate_CO2; 0.317, 0.654, tmp_cumulo+pH_cumulo+AN_cumulo+interval_yield+OD+Cell_conc._interval+rab_integral+RQ_integral+AS_Vol.+consum_O2+interval_O2+generate_CO2; 0.327, 0.654, tmp+pH_cumulo+interval_yield+interval_Pdt.+rab_integral+AS_Vol.+emission_CO2+consum_O2+interval_O2+generate_CO2; 0.348, 0.654, tmp+interval_yield+interval_Pdt.+OD+Cell_conc._interval+RQ_integral+emission_CO2+consum_O2+generate_CO2; 0.338, 0.654, tmp+interval_yield+interval_Pdt.+Feed_Vol+RS_cumulo+RQ_integral+AS_Vol.+consum_O2+interval_O2+generate_CO2; 0.327, 0.654, tmp_cumulo+pH_cumulo+AN+interval_yield+OD+Feed_Vol+RQ_integral+AS_Vol.+emission_CO2+consum_O2+generate_CO2; 0.317, 0.654, tmp_cumulo+pH+pH_cumulo+AN+interval_yield+interval_Pdt.+OD+RQ_integral+AS_Vol.+consum_O2+interval_O2+generate_CO2

[207. Linear Model that Predicts Arginine Production Amount in Interval 7]

0.316, 0.661, pH_cumulo+PL+AN+interval_yield+OD+RS+Feed_Vol+RS_cumulo+Accum._Yield+AS_Vol.+emission_CO2+consum_O2+generate_CO2; 0.324, 0.658, pH_cumulo+PL+AN+interval_yield+OD+RS+Feed_Vol+RS_cumulo+Accum._Yield+AS_Vol.+consum_O2+generate_CO2; 0.319, 0.656, pH_cumulo+PL+AN+interval_yield+OD+RS+RS_cumulo+Accum._Yield+AS_Vol.+emission_CO2+consum_O2+generate_CO2; 0.330, 0.655, pH_cumulo+PL+AN+interval_yield+OD+RS+RS_cumulo+Accum._Yield+AS_Vol.+consum_O2+generate_CO2; 0.329, 0.655, pH_cumulo+PL+AN+interval_yield+OD+RS+RS_cumulo+AS_Vol.+emission_CO2+consum_O2+generate_CO2; 0.305, 0.654, pH_cumulo+PL+AN+interval_yield+OD+RS+Feed_Vol+RS_cumulo+rab_integral+Accum._Yield+AS_Vol.+consum_O2+generate_CO2; 0.314, 0.652, pH_cumulo+PL+AN+interval_yield+OD+RS+Feed_Vol+RS_cumulo+AS_Vol.+emission_CO2+consum_O2+generate_CO2; 0.292, 0.652, pH_cumulo+PL+AN+AN_cumulo+interval_yield+OD+RS+Feed_Vol+RS_cumulo+Accum._Yield+AS_Vol.+emission_CO2+consum_O2+generate_CO2; 0.334, 0.651, pH_cumulo+PL+interval_yield+OD+RS+RS_cumulo+AS_Vol.+emission_CO2+consum_O2+generate_CO2; 0.301, 0.651, pH_cumulo+PL+AN+AN_cumulo+interval_yield+OD+RS+Feed_Vol+RS_cumulo+Accum._Yield+AS_Vol.+consum_O2+generate_CO2; 0.289, 0.651, pH_cumulo+PL+AN+interval_yield+OD+RS+Feed_Vol+RS_cumulo+rab_integral+Accum._Yield+AS_Vol.+emission_CO2+consum_O2+generate_CO2; 0.311, 0.650, pH_cumulo+PL+AN+interval_yield+OD+RS+Feed_Vol+RS_cumulo+RQ_integral+Accum._Yield+AS_Vol.+consum_O2; 0.286, 0.649, pH+pH_cumulo+PL+AN+interval_yield+OD+RS+Feed_Vol+RS_cumulo+Accum._Yield+AS_Vol.+emission_CO2+consum_O2+generate_CO2; 0.319, 0.648, pH_cumulo+PL+AN_cumulo+interval_yield+OD+RS+RS_cumulo+AS_Vol.+emission_CO2+consum_O2+generate_CO2; 0.308, 0.648, pH_cumulo+PL+AN_cumulo+interval_yield+OD+RS+RS_cumulo+Accum._Yield+AS_Vol.+emission_CO2+consum_O2+generate_CO2; 0.306, 0.647, pH_cumulo+PL+AN+interval_yield+OD+RS+RS_cumulo+rab_integral+Accum._Yield+AS_Vol.+consum_O2+generate_CO2; 0.306, 0.647, pH_cumulo+PL+AN+AN_cumulo+interval_yield+OD+RS+RS_cumulo+Accum._Yield+AS_Vol.+consum_O2+generate_CO2; 0.294, 0.647, pH_cumulo+PL+AN+AN_cumulo+interval_yield+OD+RS+RS_cumulo+Accum._Yield+AS_Vol.+emission_CO2+consum_O2+generate_CO2; 0.294, 0.646, pH_cumulo+PL+AN+interval_yield+OD+RS+Feed_Vol+RS_cumulo+Cell_conc._interval+Accum._Yield+AS_Vol.+consum_O2+generate_CO2; 0.294, 0.646, pH_cumulo+PL+AN+interval_yield+OD+RS+Feed_Vol+RS_cumulo+Accum._Yield+AS_Vol.+consum_O2+interval_O2+generate_CO2;

0.305, 0.646, pH_cumulo+PL+AN+interval_yield+OD+RS+RS_cumulo+Cell_conc._interval+Accum._Yield+AS_Vol.+consum_O2+generate_CO2; 0.305, 0.646, pH_cumulo+PL+AN+interval_yield+OD+RS+RS_cumulo+Accum._Yield+AS_Vol.+consum_O2+interval_O2+generate_CO2; 0.281, 0.646, pH_cumulo+PL+AN+interval_yield+OD+RS+Feed_Vol+RS_cumulo+Accum._Yield+AS_Vol.+emission_CO2+consum_O2+interval_O2+generate_CO2; 0.315, 0.646, pH_cumulo+PL+interval_yield+OD+RS+RS_cumulo+Accum._Yield+AS_Vol.+emission_CO2+consum_O2+generate_CO2; 0.293, 0.646, pH_cumulo+PL+AN_cumulo+interval_yield+OD+RS+Feed_Vol+RS_cumulo+Accum._Yield+AS_Vol.+emission_CO2+consum_O2+generate_CO2; 0.281, 0.646, tmp+pH_cumulo+PL+AN+interval_yield+OD+RS+Feed_Vol+RS_cumulo+Accum._Yield+AS_Vol.+emission_CO2+consum_O2+generate_CO2; 0.292, 0.646, pH+pH_cumulo+PL+AN+interval_yield+OD+RS+Feed_Vol+RS_cumulo+Accum._Yield+AS_Vol.+consum_O2+generate_CO2; 0.280, 0.645, pH_cumulo+PL+AN+interval_yield+OD+RS+Feed_Vol+RS_cumulo+Cell_conc._interval+Accum._Yield+AS_Vol.+emission_CO2+consum_O2+generate_CO2; 0.304, 0.645, pH_cumulo+PL+AN+OD+RS+Feed_Vol+RS_cumulo+Accum._Yield+AS_Vol.+emission_CO2+consum_O2+generate_CO2; 0.315, 0.645, pH_cumulo+PL+interval_yield+OD+RS+Feed_Vol+RS_cumulo+AS_Vol.+emission_CO2+consum_O2+generate_CO2; 0.292, 0.645, pH_cumulo+PL+AN+interval_yield+interval_Pdt.+OD+RS+Feed_Vol+RS_cumulo+Accum._Yield+AS_Vol.+consum_O2+generate_CO2; 0.280, 0.645, pH_cumulo+PL+AN+AN_cumulo+interval_yield+OD+RS+Feed_Vol+RS_cumulo+rab_integral+Accum._Yield+AS_Vol.+consum_O2+generate_CO2; 0.314, 0.645, pH_cumulo+PL+AN+OD+RS+Feed_Vol+RS_cumulo+Accum._Yield+AS_Vol.+consum_O2+generate_CO2; 0.290, 0.644, tmp+pH_cumulo+PL+AN+interval_yield+OD+RS+Feed_Vol+RS_cumulo+Accum._Yield+AS_Vol.+consum_O2+generate_CO2; 0.290, 0.644, pH_cumulo+PL+AN+interval_yield+OD+RS+Feed_Vol+RS_cumulo+rab_integral+RQ_integral+Accum._Yield+AS_Vol.+consum_O2; 0.302, 0.644, pH_cumulo+PL+AN+AN_cumulo+interval_yield+OD+RS+RS_cumulo+AS_Vol.+emission_CO2+consum_O2+generate_CO2; 0.290, 0.644, pH_cumulo+PL+AN+interval_yield+OD+RS+Feed_Vol+RS_cumulo+Accum._Yield+AS_Vol.+emission_O2+consum_O2+generate_CO2; 0.290, 0.644, pH_cumulo+PL+AN+AN_cumulo+interval_yield+OD+RS+Feed_Vol+RS_cumulo+RQ_integral+Accum._Yield+AS_Vol.+consum_O2; 0.290, 0.644, pH_cumulo+PL+AN+interval_yield+OD+RS+RS_cumulo+Accum._Yield+AS_Vol.+emission_CO2+consum_O2+interval_O2+generate_CO2; 0.323, 0.644, pH_cumulo+PL+AN+OD+RS+RS_cumulo+Accum._Yield+AS_Vol.+consum_O2+generate_CO2; 0.289, 0.644, pH_cumulo+PL+AN+interval_yield+OD+RS+RS_cumulo+rab_integral+Accum._Yield+AS_Vol.+emission_CO2+consum_O2+generate_CO2; 0.289, 0.643, pH_cumulo+PL+AN+interval_yield+OD+RS+Feed_Vol+RS_cumulo+RQ_integral+Accum._Yield+AS_Vol.+emission_O2+consum_O2; 0.289, 0.643, pH_cumulo+PL+AN+AN_cumulo+OD+RS+Feed_Vol+RS_cumulo+Accum._Yield+AS_Vol.+emission_CO2+consum_O2+generate_CO2; 0.311, 0.643, pH_cumulo+PL+AN+interval_yield+OD+RS+RS_cumulo+RQ_integral+Accum._Yield+AS_Vol.+consum_O2; 0.300, 0.643, pH_cumulo+PL+AN+interval_yield+OD+RS+RS_cumulo+rab_integral+AS_Vol.+emission_CO2+consum_O2+generate_CO2; 0.300, 0.643, pH_cumulo+PL+AN_cumulo+interval_yield+OD+RS+Feed_Vol+RS_cumulo+AS_Vol.+emission_CO2+consum_O2+generate_CO2; 0.276, 0.643, tmp_cumulo+pH_cumulo+PL+AN+interval_yield+OD+RS+Feed_Vol+RS_cumulo+Accum._Yield+AS_Vol.+emission_CO2+consum_O2+generate_CO2; 0.310, 0.643, pH_cumulo+PL+AN+OD+RS+RS_cumulo+Accum._Yield+AS_Vol.+emission_CO2+consum_O2+generate_CO2; 0.288, 0.642, pH_cumulo+PL+AN+AN_cumulo+interval_yield+OD+RS+Feed_Vol+RS_cumulo+AS_Vol.+emission_CO2+consum_O2+generate_CO2; 0.288, 0.642, tmp_cumulo+pH_cumulo+PL+AN+interval_yield+OD+RS+Feed_Vol+RS_cumulo+Accum._Yield+AS_Vol.+consum_O2+generate_CO2; 0.287, 0.642, pH_cumulo+PL+AN+interval_yield+OD+RS+Feed_Vol+RS_cumulo+rab_integral+AS_Vol.+emission_CO2+consum_O2+generate_CO2; 0.310, 0.642, pH_cumulo+PL+AN+OD+RS+RS_cumulo+Accum._Yield+AS_Vol.+consum_O2+interval_O2+generate_CO2; 0.263, 0.642, pH_cumulo+PL+AN+AN_cumulo+interval_yield+OD+RS+Feed_Vol+RS_cumulo+rab_integral+Accum._Yield+AS_Vol.+emission_CO2+consum_O2+generate_CO2; 0.287, 0.642, pH_cumulo+PL+AN+interval_yield+OD+RS+RS_cumulo+Cell_conc._interval+Accum._Yield+AS_Vol.+emission_CO2+consum_O2+generate_CO2; 0.298, 0.642, pH_cumulo+PL+AN+AN_cumulo+OD+RS+Feed_Vol+RS_cumulo+Accum._Yield+AS_Vol.+consum_O2+generate_CO2; 0.298, 0.642, pH_cumulo+PL+AN+interval_yield+OD+RS+RS_cumulo+Accum._Yield+AS_Vol.+emission_O2+consum_O2+generate_CO2; 0.309, 0.642, pH_cumulo+PL+AN+interval_yield+OD+RS+Feed_Vol+RS_cumulo+Accum._Yield+AS_Vol.+consum_O2; 0.274, 0.642, pH+pH_cumulo+PL+AN+interval_yield+OD+RS+Feed_Vol+RS_cumulo+rab_integral+Accum._Yield+AS_Vol.+consum_O2+generate_CO2; 0.319, 0.641, pH_cumulo+PL+AN+interval_yield+OD+RS+RS_cumulo+AS_Vol.+consum_O2+generate_CO2; 0.274, 0.641, pH_cumulo+PL+AN+interval_yield+OD+RS+Feed_Vol+RS_cumulo+Cell_conc._interval+rab_integral+Accum._Yield+AS_Vol.+consum_O2+generate_CO2; 0.319, 0.641, pH_cumulo+PL+AN+interval_yield+OD+RS+RS_cumulo+RQ_integral+AS_Vol.+consum_O2; 0.297, 0.641, pH_cumulo+PL+interval_yield+OD+RS+Feed_Vol+RS_cumulo+Accum._Yield+AS_Vol.+emission_CO2+consum_O2+generate_CO2; 0.297, 0.641, pH_cumulo+PL+AN+OD+RS+Feed_Vol+RS_cumulo+Accum._Yield+AS_Vol.+consum_O2+interval_O2+generate_CO2; 0.261, 0.641, pH+pH_cumulo+PL+AN+AN_cumulo+interval_yield+OD+RS+Feed_Vol+RS_cumulo+Accum._Yield+AS_Vol.+emission_CO2+consum_O2+generate_CO2; 0.285, 0.641, pH+pH_cumulo+PL+AN+interval_yield+OD+RS+RS_cumulo+Accum._Yield+AS_Vol.+emission_CO2+consum_O2+generate_CO2; 0.328, 0.640, pH_cumulo+PL+interval_yield+OD+RS+RS_cumulo+emission_CO2+consum_O2+generate_CO2; 0.296, 0.640, pH_cumulo+PL+AN+interval_yield+OD+RS+Feed_Vol+RS_cumulo+rab_integral+Accum._Yield+AS_Vol.+consum_O2; 0.296, 0.640, pH_cumulo+PL+AN+interval_yield+interval_Pdt.+OD+RS+Feed_Vol+Accum._Yield+AS_Vol.+consum_O2+generate_CO2; 0.272, 0.640, pH_cumulo+PL+AN+interval_yield+OD+RS+Feed_Vol+RS_cumulo+rab_integral+Accum._Yield+AS_Vol.+consum_O2+interval_O2+generate_CO2; 0.295, 0.640, pH_cumulo+PL+AN+interval_yield+OD+RS+RS_cumulo+Cell_conc._interval+AS_Vol.+emission_CO2+consum_O2+generate_CO2; 0.295, 0.640, tmp+pH_cumulo+PL+AN+interval_yield+OD+RS+RS_cumulo+Accum._Yield+AS_Vol.+consum_O2+generate_CO2; 0.295, 0.640, pH_cumulo+PL+AN+interval_yield+OD+RS+RS_cumulo+AS_Vol.+emission_CO2+consum_O2+interval_O2+ generate_CO2; 0.295, 0.640, tmp+pH_cumulo+PL+AN+interval_yield+OD+RS+RS_cumulo+AS_Vol.+emission_CO2+consum_O2+generate_CO2; 0.306, 0.640, pH_cumulo+PL+interval_yield+OD+RS+RS_cumulo+rab_integral+AS_Vol.+emission_CO2+consum_O2+generate_CO2; 0.283, 0.639, tmp+pH_cumulo+PL+AN+interval_yield+OD+RS+RS_cumulo+Accum._Yield+AS_Vol.+emission_CO2+consum_O2+generate_CO2; 0.271, 0.639, pH_cumulo+PL+AN+interval_yield+interval_Pdt.+OD+RS+Feed_Vol+RS_cumulo+rab_integral+Accum._Yield+AS_Vol.+consum_O2+generate_CO2; 0.294, 0.639, pH_cumulo+PL+AN+OD+RS+RS_cumulo+Accum._Yield+AS_Vol.+emission_CO2+consum_O2+interval_O2+generate_CO2; 0.306, 0.639, pH_cumulo+PL+AN_cumulo+interval_yield+OD+RS+RS_cumulo+Accum._Yield+AS_Vol.+consum_O2+generate_CO2; 0.306, 0.639, pH_cumulo+PL+interval_yield+OD+RS+RS_cumulo+AS_Vol.+emission_CO2+consum_O2+interval_O2+generate_CO2; 0.294, 0.639, pH_cumulo+PL+AN+AN_cumulo+OD+RS+RS_cumulo+Accum._Yield+AS_Vol.+emission_CO2+consum_O2+generate_CO2; 0.294, 0.639, tmp_cumulo+pH_cumulo+PL+AN+interval_yield+OD+RS+RS_cumulo+Accum._Yield+AS_Vol.+consum_O2+generate_CO2; 0.294, 0.639, pH+pH_cumulo+PL+AN+interval_yield+OD+RS+RS_cumulo+AS_Vol.+emission_CO2+consum_O2+generate_CO2; 0.283, 0.639, pH_cumulo+PL+AN+OD+RS+Feed_Vol+RS_cumulo+Accum._Yield+AS_Vol.+emission_CO2+consum_O2+interval_O2+generate_CO2; 0.305, 0.639, pH_cumulo+PL+AN+AN_cumulo+OD+RS+RS_cumulo+Accum._Yield+AS_Vol.+consum_O2+generate_CO2; 0.294, 0.639, pH+pH_cumulo+PL+AN+interval_yield+OD+RS+RS_cumulo+Accum._Yield+AS_Vol.+consum_O2+generate_CO2; 0.305, 0.639, pH_cumulo+PL+AN_cumulo+OD+RS+RS_cumulo+Accum._Yield+AS_Vol.+emission_CO2+consum_O2+generate_CO2; 0.258, 0.639, pH+pH_cumulo+PL+AN+interval_yield+OD+RS+Feed_Vol+RS_cumulo+rab_integral+Accum._Yield+AS_Vol.+emission_CO2+consum_O2+generate_CO2; 0.282, 0.639, tmp+pH_cumulo+PL+AN+interval_yield+OD+RS+Feed_Vol+RS_cumulo+AS_Vol.+emission_CO2+consum_O2+generate_CO2; 0.270, 0.639, pH_cumulo+PL+AN+interval_yield+interval_Pdt.+OD+RS+Feed_Vol+RS_cumulo+Accum._Yield+AS_Vol.+emission_CO2+consum_O2+generate_CO2; 0.270, 0.639, pH_cumulo+PL+AN+interval_yield+OD+RS+Feed_Vol+RS_cumulo+rab_integral+Accum._Yield+AS_Vol.+emission_O2+consum_O2+generate_CO2; 0.269, 0.639, tmp+pH_cumulo+PL+AN+interval_yield+OD+RS+Feed_Vol+RS_cumulo+rab_integral+Accum._Yield+AS_Vol.+consum_O2+generate_CO2; 0.281, 0.638, pH+pH_cumulo+PL+AN+interval_yield+OD+RS+Feed_Vol+RS_cumulo+AS_Vol.+emission_CO2+consum_O2+generate_CO2; 0.269, 0.638, pH+pH_cumulo+PL+AN+AN_cumulo+interval_yield+OD+RS+Feed_Vol+RS_cumulo+Accum._Yield+AS_Vol.+consum_O2+generate_CO2; 0.281, 0.638, pH_cumulo+PL+AN+interval_yield+OD+RS+Feed_Vol+RS_cumulo+RQ_integral+Accum._Yield+AS_Vol.+emission_CO2+consum_O2; 0.269, 0.638, pH_cumulo+PL+AN+interval_yield+OD+RS+Feed_Vol+RS_cumulo+RQ_integral+Accum._Yield+AS_Vol.+emission_O2+emission_CO2+consum_O2; 0.269, 0.638, pH_cumulo+PL+AN+AN_cumulo+interval_yield+OD+RS+Feed_Vol+RS_cumulo+Cell_conc._interval+Accum._Yield+AS_Vol.+consum_O2+generate_CO2; 0.281, 0.638, tmp_cumulo+pH_cumulo+PL+AN+interval_yield+OD+RS+RS_cumulo+Accum._Yield+AS_Vol.+emission_CO2+consum_O2+generate_CO2; 0.292, 0.638, tmp_cumulo+pH_cumulo+PL+AN+interval_yield+OD+RS+RS_cumulo+AS_Vol.+emission_CO2+consum_O2+generate_CO2; 0.256, 0.638, tmp+pH_cumulo+PL+AN+AN_cumulo+interval_yield+OD+RS+Feed_Vol+RS_cumulo+Accum._Yield+AS_Vol.+emission_CO2+consum_O2+generate_CO2; 0.292, 0.638, pH_cumulo+PL+AN+OD+RS+Feed_Vol+RS_cumulo+rab_integral+Accum._Yield+AS_Vol.+consum_O2+generate_CO2; 0.303, 0.638, pH+pH_cumulo+PL+interval_yield+OD+RS+RS_cumulo+AS_Vol.+emission_CO2+consum_O2+generate_CO2; 0.280, 0.638, pH_cumulo+PL+AN+interval_yield+OD+RS+RS_cumulo+Cell_conc._interval+rab_integral+Accum._Yield+AS_Vol.+consum_O2+generate_CO2; 0.280, 0.638, pH_cumulo+PL+AN+interval_yield+OD+RS+RS_cumulo+rab_integral+Accum._Yield+AS_Vol.+consum_O2+interval_O2+generate_CO2; 0.268, 0.638, pH_cumulo+PL+PL_cumulo+AN+interval_yield+OD+RS+Feed_Vol+RS_cumulo+Accum._Yield+AS_Vol.+emission_CO2+consum_O2+generate_CO2; 0.280, 0.638, pH_cumulo+PL+AN+AN_cumulo+interval_yield+OD+RS+RS_cumulo+Cell_conc._interval+Accum._Yield+AS_Vol.+consum_O2+generate_CO2; 0.292, 0.637, pH_cumulo+PL+AN+interval_yield+OD+RS+RS_cumulo+rab_integral+RQ_integral+Accum._Yield+AS_Vol.+consum_O2; 0.267, 0.637, pH_cumulo+PL+AN+AN_cumulo+interval_yield+OD+RS+Feed_Vol+RS_cumulo+RQ_integral+Accum._Yield+AS_Vol.+emission_O2+consum_O2; 0.279, 0.637, pH_cumulo+PL+AN+AN_cumulo+interval_yield+OD+RS+RS_cumulo+rab_integral+Accum._Yield+AS_Vol.+consum_O2+generate_CO2; 0.279, 0.637, pH_cumulo+PL+AN_cumulo+interval_yield+OD+RS+RS_cumulo+rab_integral+Accum._Yield+AS_Vol.+emission_CO2+consum_O2+generate_CO2; 0.255, 0.637, pH_cumulo+PL+AN+AN_cumulo+interval_yield+OD+RS+Feed_Vol+RS_cumulo+Cell_conc._interval+Accum._Yield+AS_Vol.+emission_CO2+consum_O2+generate_CO2; 0.267, 0.637, pH_cumulo+PL+AN+AN_cumulo+interval_yield+OD+RS+Feed_Vol+RS_cumulo+rab_integral+RQ_integral+Accum._Yield+AS_Vol.+consum_O2; 0.291, 0.637, pH_cumulo+PL+AN_cumulo+interval_yield+OD+RS+RS_cumulo+rab_integral+AS_Vol.+emission_CO2+consum_O2+generate_CO2; 0.279, 0.637, pH+pH_cumulo+PL+AN+interval_yield+OD+RS+Feed_Vol+RS_cumulo+RQ_integral+Accum._Yield+AS_Vol.+consum_O2; 0.267, 0.637, tmp+pH_cumulo+PL+AN+AN_cumulo+interval_yield+OD+RS+Feed_Vol+RS_cumulo+Accum._Yield+AS_Vol.+consum_O2+generate_CO2; 0.291, 0.637, pH_cumulo+PL+AN+interval_yield+OD+RS+RS_cumulo+RQ_integral+Accum._Yield+AS_Vol.+emission_O2+consum_O2; 0.267, 0.637, pH_cumulo+PL+AN+AN_cumulo+interval_yield+OD+RS+Feed_Vol+RS_cumulo+Accum._Yield+AS_Vol.+consum_O2+interval_O2+generate_CO2; 0.267, 0.637, pH_cumulo+PL+AN+interval_yield+OD+RS+Feed_Vol+RS_cumulo+rab_integral+RQ_integral+Accum._Yield+AS_Vol.+emission_O2+consum_O2; 0.279, 0.637, tmp_cumulo+pH_cumulo+PL+AN+interval_yield+OD+RS+Feed_Vol+RS_cumulo+AS_Vol.+emission_CO2+consum_O2+generate_CO2; 0.313, 0.637, pH_cumulo+PL+AN_cumulo+interval_yield+OD+RS+RS_cumulo+emission_CO2+consum_O2+generate_CO2; 0.279, 0.637, pH_cumulo+PL+AN+interval_yield+OD+RS+Feed_Vol+RS_cumulo+Cell_conc._interval+AS_Vol.+emission_CO2+consum_O2+generate_CO2; 0.290, 0.636, pH_cumulo+PL+AN+AN_cumulo+interval_yield+OD+RS+Feed_Vol+RS_cumulo+Accum._Yield+AS_Vol.+consum_O2; 0.290, 0.636, pH_cumulo+

PL+AN+AN_cumulo+interval_yield+OD+RS+RS_cumulo+RQ_integral+Accum._Yield+AS_Vol.+consum_O2; 0.290, 0.636, pH_cumulo+PL+interval_yield+OD+RS+RS_cumulo+Accum._Yield+AS_Vol.+emission_CO2+consum_O2+interval_O2+generate_CO2; 0.253, 0.636, pH_cumulo+PL+AN+AN_cumulo+interval_yield+OD+RS+Feed_Vol+RS_cumulo+Accum._Yield+AS_Vol.+emission_CO2+consum_O2+interval_O2+generate_CO2; 0.301, 0.636, pH_cumulo+PL+interval_yield+OD+RS+RS_cumulo+Cell_conc._interval+AS_Vol.+emission_CO2+consum_O2+generate_CO2; 0.253, 0.636, pH_cumulo+PL+AN+interval_yield+OD+RS+Feed_Vol+RS_cumulo+rab_integral+Accum._Yield+AS_Vol.+emission_CO2+consum_O2+interval_O2+generate_CO2; 0.278, 0.636, pH+pH_cumulo+PL+AN+OD+RS+Feed_Vol+RS_cumulo+Accum._Yield+AS_Vol.+emission_CO2+consum_O2+generate_CO2; 0.300, 0.636, pH_cumulo+PL+AN+interval_yield+OD+RS+Feed_Vol+RS_cumulo+RQ_integral+AS_Vol.+consum_O2; 0.265, 0.636, tmp_cumulo+pH_cumulo+PL+AN+interval_yield+OD+RS+Feed_Vol+RS_cumulo+rab_integral+Accum._Yield+AS_Vol.+consum_O2+generate_CO2; 0.322, 0.636, pH_cumulo+PL+interval_yield+OD+RS+RS_cumulo+RQ_integral+AS_Vol.+consum_O2; 0.300, 0.636, pH_cumulo+PL+AN+OD+RS+RS_cumulo+Cell_conc._interval+Accum._Yield+AS_Vol.+consum_O2+generate_CO2; 0.265, 0.636, pH_cumulo+PL+AN+AN_cumulo+interval_yield+OD+RS+Feed_Vol+RS_cumulo+Accum._Yield+AS_Vol.+emission_O2+consum_O2+generate_CO2; 0.277, 0.636, pH_cumulo+PL+PL_cumulo+AN+interval_yield+OD+RS+Feed_Vol+RS_cumulo+Accum._Yield+AS_Vol.+consum_O2+generate_CO2; 0.300, 0.636, tmp+pH_cumulo+PL+interval_yield+OD+RS+RS_cumulo+AS_Vol.+emission_CO2+consum_O2+generate_CO2; 0.277, 0.636, pH_cumulo+PL+AN+AN_cumulo+interval_yield+OD+RS+Feed_Vol+RS_cumulo+rab_integral+Accum._Yield+AS_Vol.+consum_O2; 0.311, 0.636, pH_cumulo+PL+AN+interval_yield+OD+RS+RS_cumulo+emission_CO2+consum_O2+generate_CO2; 0.300, 0.635, pH_cumulo+PL+AN+interval_yield+OD+RS+Feed_Vol+Accum._Yield+AS_Vol.+consum_O2+generate_CO2; 0.252, 0.635, tmp_cumulo+pH_cumulo+PL+AN+AN_cumulo+interval_yield+OD+RS+Feed_Vol+RS_cumulo+Accum._Yield+AS_Vol.+emission_CO2+consum_O2+generate_CO2; 0.264, 0.635, pH_cumulo+PL+AN+interval_yield+OD+RS+Feed_Vol+RS_cumulo+Accum._Yield+AS_Vol.+emission_O2+emission_CO2+consum_O2+generate_CO2; 0.288, 0.635, pH_cumulo+PL+AN+interval_yield+interval_Pdt.+OD+RS+RS_cumulo+Accum._Yield+AS_Vol.+consum_O2+generate_CO2; 0.252, 0.635, pH_cumulo+PL+AN+interval_yield+OD+RS+Feed_Vol+RS_cumulo+Cell_conc._interval+rab_integral+Accum._Yield+AS_Vol.+emission_CO2+consum_O2+generate_CO2; 0.276, 0.635, pH_cumulo+PL+AN+AN_cumulo+interval_yield+OD+RS+RS_cumulo+Accum._Yield+AS_Vol.+consum_O2+interval_O2+generate_CO2; 0.299, 0.635, pH_cumulo+PL+AN+interval_yield+OD+RS+RS_cumulo+rab_integral+RQ_integral+AS_Vol.+consum_O2; 0.310, 0.635, pH_cumulo+PL+interval_yield+OD+RS+RS_cumulo+RQ_integral+Accum._Yield+AS_Vol.+consum_O2; 0.276, 0.635, pH_cumulo+PL+AN+interval_yield+interval_Pdt.+OD+RS+Feed_Vol+RS_cumulo+RQ_integral+Accum._Yield+AS_Vol.+consum_O2; 0.264, 0.635, tmp_cumulo+pH_cumulo+PL+AN+AN_cumulo+interval_yield+OD+RS+Feed_Vol+RS_cumulo+Accum._Yield+AS_Vol.+consum_O2+generate_CO2; 0.252, 0.635, tmp+pH_cumulo+PL+AN+interval_yield+OD+RS+Feed_Vol+RS_cumulo+rab_integral+Accum._Yield+AS_Vol.+emission_CO2+consum_O2+generate_CO2; 0.264, 0.635, pH_cumulo+PL+AN+interval_yield+OD+RS+Feed_Vol+RS_cumulo+Cell_conc._interval+Accum._Yield+AS_Vol.+consum_O2+generate_CO2; 0.276, 0.635, pH_cumulo+PL+AN+interval_yield+OD+RS+Feed_Vol+RS_cumulo+Cell_conc._interval+RQ_integral+Accum._Yield+AS_Vol.+consum_O2; 0.287, 0.635, pH+pH_cumulo+PL+AN+OD+RS+Feed_Vol+RS_cumulo+Accum._Yield+AS_Vol.+consum_O2+generate_CO2; 0.251, 0.635, tmp+tmp_cumulo+pH_cumulo+PL+AN+interval_yield+OD+RS+Feed_Vol+RS_cumulo+Accum._Yield+AS_Vol.+emission_CO2+consum_O2+generate_CO2; 0.276, 0.635, pH_cumulo+PL+AN+interval_yield+OD+RS+RS_cumulo+Cell_conc._interval+Accum._Yield+AS_Vol.+consum_O2+interval_O2+generate_CO2; 0.276, 0.635, pH_cumulo+PL+AN+interval_yield+OD+RS+Feed_Vol+RS_cumulo+AS_Vol.+emission_CO2+consum_O2+interval_O2+generate_CO2; 0.287, 0.635, pH_cumulo+PL+AN+interval_yield+OD+RS+Feed_Vol+Accum._Yield+AS_Vol.+emission_CO2+consum_O2+generate_CO2; 0.287, 0.635, pH_cumulo+PL+AN+OD+RS+Feed_Vol+RS_cumulo+Cell_conc._interval+Accum._Yield+AS_Vol.+consum_O2+generate_CO2; 0.287, 0.635, pH_cumulo+PL+AN_cumulo+OD+RS+Feed_Vol+RS_cumulo+Accum._Yield+AS_Vol.+emission_CO2+consum_O2+generate_CO2; 0.263, 0.634, pH_cumulo+PL+AN+AN_cumulo+interval_yield+OD+RS+RS_cumulo+rab_integral+Accum._Yield+AS_Vol.+emission_CO2+consum_O2+generate_CO2; 0.298, 0.634, pH_cumulo+PL+AN+interval_yield+OD+RS+Feed_Vol+RS_cumulo+AS_Vol.+consum_O2+generate_CO2; 0.251, 0.634, pH+pH_cumulo+PL+AN+interval_yield+OD+RS+Feed_Vol+RS_cumulo+Cell_conc._interval+Accum._Yield+AS_Vol.+emission_CO2+consum_O2+generate_CO2; 0.263, 0.634, pH_cumulo+PL+AN_cumulo+interval_yield+OD+RS+Feed_Vol+RS_cumulo+rab_integral+Accum._Yield+AS_Vol.+emission_CO2+consum_O2+generate_CO2; 0.275, 0.634, pH_cumulo+PL+PL_cumulo+AN+interval_yield+OD+RS+Feed_Vol+RS_cumulo+RQ_integral+Accum._Yield+AS_Vol.+consum_O2; 0.275, 0.634, pH+pH_cumulo+PL+AN_cumulo+interval_yield+OD+RS+RS_cumulo+Accum._Yield+AS_Vol.+emission_CO2+consum_O2+generate_CO2; 0.275, 0.634, pH_cumulo+PL+AN+AN_cumulo+OD+RS+Feed_Vol+RS_cumulo+Accum._Yield+AS_Vol.+consum_O2+interval_O2+generate_CO2; 0.286, 0.634, pH_cumulo+PL+interval_yield+OD+RS+Feed_Vol+RS_cumulo+rab_integral+AS_Vol.+emission_CO2+consum_O2+generate_CO2; 0.263, 0.634, pH+pH_cumulo+PL+AN+AN_cumulo+OD+RS+Feed_Vol+RS_cumulo+Accum._Yield+AS_Vol.+emission_CO2+consum_O2+generate_CO2; 0.286, 0.634, pH_cumulo+PL+interval_yield+OD+RS+RS_cumulo+rab_integral+Accum._Yield+AS_Vol.+emission_CO2+consum_O2+generate_CO2; 0.250, 0.634, pH+pH_cumulo+PL+AN+interval_yield+OD+RS+Feed_Vol+RS_cumulo+Accum._Yield+AS_Vol.+emission_CO2+consum_O2+interval_O2+generate_CO2; 0.286, 0.634, pH_cumulo+PL+AN+AN_cumulo+OD+RS+RS_cumulo+Accum._Yield+AS_Vol.+consum_O2+interval_O2+generate_CO2; 0.298, 0.634, pH_cumulo+PL+AN+OD+RS+RS_cumulo+rab_integral+Accum._Yield+AS_Vol.+consum_O2+generate_CO2; 0.262, 0.634, pH_cumulo+PL+AN+AN_cumulo+interval_yield+interval_Pdt.+OD+RS+Feed_Vol+RS_cumulo+Accum._Yield+AS_Vol.+consum_O2+generate_CO2; 0.286, 0.634, pH+pH_cumulo+PL+AN_cumulo+interval_yield+OD+RS+RS_cumulo+AS_Vol.+emission_CO2+consum_O2+ generate_CO2; 0.308, 0.634, pH_cumulo+PL+interval_yield+OD+RS+RS_cumulo+Accum._Yield+emission_CO2+consum_O2+generate_CO2; 0.297, 0.634, pH_cumulo+PL+AN+interval_yield+OD+RS+RS_cumulo+AS_Vol.+emission_O2+consum_O2+generate_CO2; 0.297, 0.634, tmp_cumulo+pH_cumulo+PL+interval_yield+OD+RS+RS_cumulo+AS_Vol.+emission_CO2+consum_O2+generate_CO2; 0.262, 0.634, tmp+tmp_cumulo+pH_cumulo+PL+AN+interval_yield+OD+RS+Feed_Vol+RS_cumulo+Accum._Yield+AS_Vol.+consum_O2+generate_CO2; 0.274, 0.634, pH_cumulo+PL+AN+OD+RS+Feed_Vol+RS_cumulo+rab_integral+Accum._Yield+AS_Vol.+emission_CO2+consum_O2+generate_CO2; 0.297, 0.634, pH_cumulo+PL+AN+interval_yield+OD+RS+RS_cumulo+rab_integral+AS_Vol.+consum_O2+generate_CO2; 0.297, 0.634, pH_cumulo+PL+AN+AN_cumulo+interval_yield+OD+RS+RS_cumulo+RQ_integral+AS_Vol.+consum_O2; 0.262, 0.634, pH+pH_cumulo+PL+AN+interval_yield+OD+RS+Feed_Vol+RS_cumulo+Accum._Yield+AS_Vol.+consum_O2+interval_O2+generate_CO2; 0.297, 0.633, pH_cumulo+PL+AN+interval_Pdt.+OD+RS+RS_cumulo+RQ_integral+Accum._Yield+AS_Vol.+consum_O2; 0.262, 0.633, pH_cumulo+PL+AN+AN_cumulo+OD+RS+Feed_Vol+RS_cumulo+Accum._Yield+AS_Vol.+emission_CO2+consum_O2+interval_O2+generate_CO2; 0.297, 0.633, pH_cumulo+PL+AN_cumulo+interval_yield+OD+RS+RS_cumulo+Accum._Yield+emission_CO2+consum_O2+generate_CO2; 0.285, 0.633, pH+PL+AN+interval_yield+OD+RS+Feed_Vol+RS_cumulo+Accum._Yield+AS_Vol.+consum_O2+generate_CO2; 0.249, 0.633, pH+pH_cumulo+PL+AN+AN_cumulo+interval_yield+OD+RS+Feed_Vol+RS_cumulo+rab_integral+Accum._Yield+AS_Vol.+consum_O2+generate_CO2; 0.273, 0.633, pH_cumulo+PL+AN+interval_yield+OD+RS+RS_cumulo+Accum._Yield+AS_Vol.+emission_O2+consum_O2+interval_O2+generate_CO2; 0.261, 0.633, pH_cumulo+PL+AN+interval_yield+OD+RS+Feed_Vol+RS_cumulo+Cell_conc._interval+Accum._Yield+AS_Vol.+consum_O2+interval_O2+generate_CO2; 0.296, 0.633, pH_cumulo+PL+AN_cumulo+interval_yield+OD+RS+RS_cumulo+RQ_integral+Accum._Yield+AS_Vol.+consum_O2; 0.273, 0.633, pH_cumulo+PL+AN_cumulo+interval_yield+OD+RS+RS_cumulo+Accum._Yield+AS_Vol.+emission_CO2+consum_O2+interval_O2+generate_CO2; 0.273, 0.633, pH_cumulo+PL+AN_cumulo+interval_yield+OD+RS+RS_cumulo+Cell_conc._interval+Accum._Yield+AS_Vol.+emission_CO2+consum_O2+generate_CO2; 0.273, 0.633, pH_cumulo+PL+AN+interval_yield+OD+RS+Feed_Vol+RS_cumulo+rab_integral+Accum._Yield+AS_Vol.+emission_CO2+consum_O2; 0.285, 0.633, pH_cumulo+PL+AN+interval_yield+OD+RS+Feed_Vol+RS_cumulo+Accum._Yield+AS_Vol.+emission_CO2+consum_O2; 0.261, 0.633, pH_cumulo+PL+AN+AN_cumulo+interval_yield+OD+RS+RS_cumulo+Accum._Yield+AS_Vol.+emission_CO2+consum_O2+interval_O2+generate_CO2; 0.296, 0.633, pH_cumulo+PL+interval_yield+OD+RS+RS_cumulo+RQ_integral+AS_Vol.+emission_O2+emission_CO2+consum_O2; 0.273, 0.633, pH_cumulo+PL+AN+AN_cumulo+OD+RS+Feed_Vol+RS_cumulo+rab_integral+Accum._Yield+AS_Vol.+consum_O2+generate_CO2; 0.261, 0.633, pH+pH_cumulo+PL+AN_cumulo+interval_yield+OD+RS+Feed_Vol+RS_cumulo+Accum._Yield+AS_Vol.+emission_CO2+consum_O2+generate_CO2; 0.261, 0.633, pH_cumulo+PL+AN+AN_cumulo+interval_yield+OD+RS+RS_cumulo+Cell_conc._interval+Accum._Yield+AS_Vol.+emission_CO2+consum_O2+generate_CO2; 0.284, 0.633, pH_cumulo+PL+AN+OD+RS+RS_cumulo+rab_integral+Accum._Yield+AS_Vol.+consum_O2+interval_O2+generate_CO2; 0.284, 0.633, pH_cumulo+PL+AN_cumulo+interval_yield+OD+RS+RS_cumulo+Cell_conc._interval+AS_Vol.+emission_CO2+consum_O2+generate_CO2; 0.284, 0.633, pH_cumulo+PL+AN_cumulo+interval_yield+OD+RS+Feed_Vol+RS_cumulo+Accum._Yield+AS_Vol.+consum_O2+generate_CO2; 0.284, 0.633, tmp+pH_cumulo+PL+AN_cumulo+interval_yield+OD+RS+RS_cumulo+AS_Vol.+emission_CO2+consum_O2+generate_CO2; 0.272, 0.633, pH_cumulo+PL+AN+AN_cumulo+interval_yield+OD+RS+RS_cumulo+Accum._Yield+AS_Vol.+emission_O2+consum_O2+generate_CO2; 0.260, 0.633, pH_cumulo+PL+AN+interval_yield+OD+RS+Feed_Vol+RS_cumulo+Accum._Yield+AS_Vol.+emission_O2+consum_O2+interval_O2+generate_CO2; 0.260, 0.632, pH_cumulo+PL+AN+interval_yield+interval_Pdt.+OD+RS+Feed_Vol+RS_cumulo+Accum._Yield+AS_Vol.+consum_O2+interval_O2+generate_CO2; 0.272, 0.632, pH_cumulo+PL+AN+OD+RS+Feed_Vol+RS_cumulo+rab_integral+Accum._Yield+AS_Vol.+consum_O2+interval_O2+generate_CO2; 0.272, 0.632, tmp+pH_cumulo+PL+AN+interval_yield+OD+RS+Feed_Vol+RS_cumulo+RQ_integral+Accum._Yield+AS_Vol.+consum_O2; 0.260, 0.632, pH_cumulo+PL+AN+interval_yield+OD+RS+RS_cumulo+rab_integral+Accum._Yield+AS_Vol.+emission_CO2+consum_O2+interval_O2+generate_CO2; 0.284, 0.632, pH+pH_cumulo+PL+interval_yield+OD+RS+RS_cumulo+Accum._Yield+AS_Vol.+emission_CO2+consum_O2+generate_CO2; 0.284, 0.632, pH_cumulo+PL+AN+interval_yield+interval_Pdt.+OD+RS+RS_cumulo+RQ_integral+Accum._Yield+AS_Vol.+consum_O2; 0.272, 0.632, pH_cumulo+PL+AN+interval_yield+OD+RS+RS_cumulo+rab_integral+Accum._Yield+AS_Vol.+emission_O2+consum_O2+generate_CO2; 0.284, 0.632, pH+pH_cumulo+PL+interval_yield+OD+RS+Feed_Vol+RS_cumulo+AS_Vol.+emission_CO2+consum_O2+generate_CO2; 0.260, 0.632, pH_cumulo+PL+AN+AN_cumulo+interval_yield+OD+RS+Feed_Vol+RS_cumulo+rab_integral+AS_Vol.+emission_CO2+consum_O2+generate_CO2; 0.306, 0.632, pH_cumulo+PL+interval_yield+OD+RS+Feed_Vol+RS_cumulo+emission_CO2+consum_O2+generate_CO2; 0.272, 0.632, pH_cumulo+PL+AN+AN_cumulo+OD+RS+RS_cumulo+Accum._Yield+AS_Vol.+emission_CO2+consum_O2+interval_O2+generate_CO2; 0.272, 0.632, pH_cumulo+PL+AN+AN_cumulo+interval_yield+OD+RS+RS_cumulo+rab_integral+AS_Vol.+emission_CO2+consum_O2+generate_CO2; 0.272, 0.632, pH+pH_cumulo+PL+AN+interval_yield+OD+RS+RS_cumulo+Cell_conc._interval+Accum._Yield+AS_Vol.+consum_O2+generate_CO2; 0.272, 0.632, pH+pH_cumulo+PL+AN+AN_cumulo+OD+RS+Feed_Vol+RS_cumulo+Accum._Yield+AS_Vol.+consum_O2+generate_CO2; 0.247, 0.632, tmp+pH+pH_cumulo+PL+AN+interval_yield+OD+RS+Feed_Vol+RS_cumulo+Accum._Yield+AS_Vol.+emission_CO2+consum_O2+generate_CO2; 0.259, 0.632, pH+pH_cumulo+PL+AN+AN_cumulo+interval_yield+OD+RS+RS_cumulo+Accum._Yield+AS_Vol.+emission_CO2+consum_O2+generate_CO2; 0.259, 0.632, pH_cumulo+PL+AN+AN_cumulo+interval_yield+OD+RS+Feed_Vol+RS_cumulo+RQ_integral+Accum._Yield+AS_Vol.+emission_CO2+consum_O2; 0.271, 0.632, pH+pH_cumulo+PL+AN+interval_yield+OD+RS+RS_cumulo+rab_integral+Accum._Yield+AS_Vol.+consum_O2+generate_CO2; 0.259, 0.632, pH+pH_cumulo+PL+AN+interval_yield+OD+RS+Feed_Vol+RS_cumulo+Accum._

Yield+AS_Vol.+emission_O2+consum_O2+generate_CO2; 0.271, 0.632, tmp+pH_cumulo+PL+AN_cumulo+interval_yield+OD+RS+RS_cumulo+Accum._Yield+AS_Vol.+emission_CO2+consum_O2+generate_CO2; 0.259, 0.632, pH_cumulo+PL+PL_cumulo+AN+interval_yield+OD+RS+Feed_Vol+RS_cumulo+rab_integral+Accum._Yield+AS_Vol.+consum_O2+generate_CO2; 0.271, 0.632, tmp_cumulo+pH_cumulo+PL+AN_cumulo+interval_yield+OD+RS+RS_cumulo+Accum._Yield+AS_Vol.+emission_CO2+consum_O2+generate_CO2; 0.283, 0.632, pH_cumulo+PL+interval_yield+OD+RS+Feed_Vol+RS_cumulo+AS_Vol.+emission_CO2+consum_O2+interval_O2+generate_CO2; 0.246, 0.632, pH_cumulo+PL+AN+AN_cumulo+interval_yield+OD+RS+Feed_Vol+RS_cumulo+RQ_integral+Accum._Yield+AS_Vol.+emission_O2+emission_CO2+consum_O2; 0.283, 0.632, pH_cumulo+PL+AN+AN_cumulo+interval_yield+OD+RS+Feed_Vol+Accum._Yield+AS_Vol.+consum_O2+generate_CO2; 0.294, 0.632, pH_cumulo+PL+AN+interval_yield+OD+RS+RS_cumulo+RQ_integral+AS_Vol.+emission_O2+consum_O2; 0.246, 0.632, pH_cumulo+PL+AN+AN_cumulo+interval_yield+OD+RS+Feed_Vol+RS_cumulo+Cell_conc._interval+rab_integral+Accum._Yield+AS_Vol.+consum_O2+generate_CO2; 0.283, 0.632, pH_cumulo+PL+AN+AN_cumulo+OD+RS+RS_cumulo+Cell_conc._interval+Accum._Yield+AS_Vol.+consum_O2+generate_CO2; 0.259, 0.632, tmp+pH_cumulo+PL+AN+interval_yield+interval_Pdt.+OD+RS+Feed_Vol+RS_cumulo+Accum._Yield+AS_Vol.+consum_O2+generate_CO2; 0.271, 0.632, pH_cumulo+PL+AN_cumulo+interval_yield+OD+RS+Feed_Vol+RS_cumulo+rab_integral+AS_Vol.+emission_CO2+consum_O2+generate_CO2; 0.271, 0.632, tmp+tmp_cumulo+pH_cumulo+PL+AN+interval_yield+OD+RS+RS_cumulo+Accum._Yield+AS_Vol.+consum_O2+generate_CO2; 0.294, 0.632, pH_cumulo+PL+AN+interval_yield+OD+RS+RS_cumulo+Cell_conc._interval+AS_Vol.+consum_O2+generate_CO2; 0.283, 0.632, pH_cumulo+PL+AN+OD+RS+RS_cumulo+Cell_conc._interval+Accum._Yield+AS_Vol.+consum_O2+interval_O2+generate_CO2; 0.271, 0.632, pH_cumulo+PL+PL_cumulo+AN+interval_yield+OD+RS+RS_cumulo+Accum._Yield+AS_Vol.+emission_CO2+consum_O2+generate_CO2; 0.258, 0.631, tmp+pH_cumulo+PL+AN+interval_yield+OD+RS+Feed_Vol+RS_cumulo+Cell_conc._interval+Accum._Yield+AS_Vol.+consum_O2+generate_CO2; 0.246, 0.631, pH+pH_cumulo+PL+PL_cumulo+AN+interval_yield+OD+RS+Feed_Vol+RS_cumulo+Accum._Yield+AS_Vol.+emission_CO2+consum_O2+generate_CO2; 0.271, 0.631, tmp+pH_cumulo+PL+AN+AN_cumulo+interval_yield+OD+RS+RS_cumulo+Accum._Yield+AS_Vol.+consum_O2+generate_CO2; 0.271, 0.631, pH_cumulo+PL+AN+AN_cumulo+interval_yield+interval_Pdt.+OD+RS+Feed_Vol+Accum._Yield+AS_Vol.+consum_O2+generate_CO2; 0.305, 0.631, pH_cumulo+PL+AN_cumulo+OD+RS+RS_cumulo+Accum._Yield+AS_Vol.+consum_O2+generate_CO2; 0.282, 0.631, pH_cumulo+PL+PL_cumulo+AN+interval_yield+OD+RS+RS_cumulo+Accum._Yield+AS_Vol.+consum_O2+generate_CO2; 0.305, 0.631, pH_cumulo+PL+interval_yield+OD+RS+RS_cumulo+Accum._Yield+AS_Vol.+consum_O2+generate_CO2; 0.246, 0.631, tmp_cumulo+pH_cumulo+PL+AN+interval_yield+OD+RS+Feed_Vol+RS_cumulo+rab_integral+Accum._Yield+AS_Vol.+emission_CO2+consum_O2+generate_CO2; 0.258, 0.631, pH+pH_cumulo+PL+AN+interval_yield+interval_Pdt.+OD+RS+Feed_Vol+RS_cumulo+Accum._Yield+AS_Vol.+consum_O2+generate_CO2; 0.270, 0.631, tmp_cumulo+pH_cumulo+PL+AN+AN_cumulo+interval_yield+OD+RS+RS_cumulo+Accum._Yield+AS_Vol.+consum_O2+generate_CO2; 0.270, 0.631, pH_cumulo+PL+AN+interval_yield+OD+RS+RS_cumulo+rab_integral+RQ_integral+Accum._Yield+AS_Vol.+emission_O2+consum_O2; 0.304, 0.631, pH_cumulo+PL+interval_yield+OD+RS+RS_cumulo+rab_integral+emission_CO2+consum_O2+generate_CO2; 0.282, 0.631, tmp_cumulo+pH_cumulo+PL+AN_cumulo+interval_yield+OD+RS+RS_cumulo+AS_Vol.+emission_CO2+consum_O2+generate_CO2; 0.293, 0.631, pH_cumulo+PL+AN+interval_yield+OD+RS+RS_cumulo+Accum._Yield+emission_CO2+consum_O2+generate_CO2; 0.270, 0.631, pH+pH_cumulo+PL+AN+OD+RS+Feed_Vol+RS_cumulo+Accum._Yield+AS_Vol.+consum_O2+interval_O2+generate_CO2; 0.258, 0.631, pH_cumulo+PL+AN+interval_yield+interval_Pdt.+OD+RS+Feed_Vol+RS_cumulo+Accum._Yield+AS_Vol.+emission_O2+consum_O2+generate_CO2; 0.282, 0.631, pH_cumulo+PL+interval_Pdt.+OD+RS+RS_cumulo+RQ_integral+Accum._Yield+AS_Vol.+emission_O2+emission_CO2+consum_O2; 0.270, 0.631, pH_cumulo+PL+AN+AN_cumulo+OD+RS+Feed_Vol+RS_cumulo+Cell_conc._interval+Accum._Yield+AS_Vol.+consum_O2+generate_CO2; 0.257, 0.631, pH+pH_cumulo+PL+AN+interval_yield+OD+RS+Feed_Vol+RS_cumulo+rab_integral+RQ_integral+Accum._Yield+AS_Vol.+consum_O2; 0.257, 0.631, tmp+pH_cumulo+PL+AN+AN_cumulo+interval_yield+OD+RS+RS_cumulo+Accum._Yield+AS_Vol.+emission_CO2+consum_O2+generate_CO2; 0.257, 0.631, pH_cumulo+PL+AN+AN_cumulo+OD+RS+Feed_Vol+RS_cumulo+rab_integral+Accum._Yield+AS_Vol.+emission_CO2+consum_O2+generate_CO2; 0.269, 0.631, pH+pH_cumulo+PL+AN+AN_cumulo+interval_yield+OD+RS+RS_cumulo+Accum._Yield+AS_Vol.+consum_O2+generate_CO2; 0.257, 0.631, pH+pH_cumulo+PL+AN+AN_cumulo+interval_yield+OD+RS+Feed_Vol+RS_cumulo+RQ_integral+Accum._Yield+AS_Vol.+consum_O2; 0.281, 0.631, pH_cumulo+PL+AN_cumulo+OD+RS+RS_cumulo+Accum._Yield+AS_Vol.+emission_CO2+consum_O2+interval_O2+generate_CO2; 0.269, 0.631, pH_cumulo+PL+AN+OD+RS+Feed_Vol+RS_cumulo+Cell_conc._interval+Accum._Yield+AS_Vol.+emission_CO2+consum_O2+generate_CO2; 0.304, 0.631, pH_cumulo+PL+interval_yield+OD+RS+RS_cumulo+emission_CO2+consum_O2+interval_O2+generate_CO2; 0.245, 0.631, tmp_cumulo+pH+pH_cumulo+PL+AN+interval_yield+OD+RS+Feed_Vol+RS_cumulo+Accum._Yield+AS_Vol.+emission_CO2+consum_O2+generate_CO2; 0.269, 0.631, pH_cumulo+PL+AN+interval_yield+interval_Pdt.+OD+RS+RS_cumulo+Accum._Yield+AS_Vol.+emission_CO2+consum_O2+generate_CO2; 0.232, 0.631, pH+pH_cumulo+PL+AN+AN_cumulo+interval_yield+OD+RS+Feed_Vol+RS_cumulo+rab_integral+Accum._Yield+AS_Vol.+emission_CO2+consum_O2+generate_CO2; 0.269, 0.631, pH_cumulo+PL+AN+interval_yield+interval_Pdt.+OD+RS+Feed_Vol+rab_integral+Accum._Yield+AS_Vol.+consum_O2+generate_CO2; 0.269, 0.631, tmp+pH_cumulo+PL+AN+interval_yield+OD+RS+RS_cumulo+Cell_conc._interval+Accum._Yield+AS_Vol.+consum_O2+generate_CO2; 0.257, 0.631, tmp+tmp_cumulo+pH_cumulo+PL+AN+interval_yield+OD+RS+RS_cumulo+Accum._Yield+AS_Vol.+emission_CO2+consum_O2+generate_CO2; 0.257, 0.631, pH_cumulo+PL+AN+interval_yield+OD+RS+Feed_Vol+RS_cumulo+Cell_conc._interval+Accum._Yield+AS_Vol.+emission_O2+consum_O2+generate_CO2; 0.269, 0.631, pH+PL+AN+interval_yield+OD+RS+Feed_Vol+RS_cumulo+Cell_ conc._interval+Accum._Yield+AS_Vol.+consum_O2+generate_CO2; 0.281, 0.630, pH_cumulo+PL+AN_cumulo+interval_yield+OD+RS+RS_cumulo+AS_Vol.+emission_CO2+consum_O2+interval_O2+generate_CO2; 0.244, 0.630, pH_cumulo+PL+AN+interval_yield+OD+RS+Feed_Vol+RS_cumulo+Cell_conc._interval+Accum._Yield+AS_Vol.+emission_CO2+consum_O2+interval_O2+generate_CO2; 0.281, 0.630, pH_cumulo+PL+interval_yield+OD+RS+RS_cumulo+Cell_conc._interval+Accum._Yield+AS_Vol.+emission_CO2+consum_O2+generate_CO2; 0.269, 0.630, pH+PL+AN+interval_yield+interval_Pdt.+OD+RS+Feed_Vol+RS_cumulo+Accum._Yield+AS_Vol.+consum_O2+generate_CO2; 0.244, 0.630, pH+pH_cumulo+PL+AN+interval_yield+OD+RS+Feed_Vol+RS_cumulo+Cell_conc._interval+rab_integral+Accum._Yield+AS_Vol.+consum_O2+generate_CO2; 0.303, 0.630, pH_cumulo+PL+AN_cumulo+interval_yield+OD+RS+RS_cumulo+RQ_integral+AS_Vol.+consum_O2; 0.269, 0.630, tmp+pH_cumulo+PL+AN+interval_yield+OD+RS+RS_cumulo+rab_integral+Accum._Yield+AS_Vol.+consum_O2+generate_CO2; 0.244, 0.630, tmp+pH_cumulo+PL+AN+AN_cumulo+interval_yield+OD+RS+Feed_Vol+RS_cumulo+rab_integral+Accum._Yield+AS_Vol.+consum_O2+generate_CO2; 0.269, 0.630, pH_cumulo+PL+AN+interval_yield+OD+RS+Feed_Vol+RS_cumulo+RQ_integral+AS_Vol.+emission_O2+emission_CO2+consum_O2; 0.269, 0.630, pH+PL+AN+AN_cumulo+interval_yield+OD+RS+Feed_Vol+RS_cumulo+Accum._Yield+AS_Vol.+consum_O2+generate_CO2; 0.256, 0.630, tmp_cumulo+pH_cumulo+PL+AN+interval_yield+OD+RS+Feed_Vol+RS_cumulo+Cell_conc._interval+Accum._Yield+AS_Vol.+consum_O2+generate_CO2; 0.280, 0.630, pH_cumulo+PL+interval_yield+OD+RS+Feed_Vol+RS_cumulo+Cell_conc._interval+AS_Vol.+emission_CO2+consum_O2+generate_CO2; 0.244, 0.630, pH_cumulo+PL+AN+AN_cumulo+interval_yield+OD+RS+Feed_Vol+RS_cumulo+rab_integral+Accum._Yield+AS_Vol.+emission_O2+consum_O2+generate_CO2; 0.244, 0.630, pH_cumulo+PL+AN+AN_cumulo+interval_yield+OD+RS+Feed_Vol+RS_cumulo+rab_integral+Accum._Yield+AS_Vol.+consum_O2+interval_O2+generate_CO2; 0.280, 0.630, tmp+pH_cumulo+PL+interval_yield+OD+RS+Feed_Vol+RS_cumulo+AS_Vol.+emission_CO2+consum_O2+generate_CO2; 0.280, 0.630, pH_cumulo+PL+AN+OD+RS+Feed_Vol+RS_cumulo+Accum._Yield+AS_Vol.+emission_O2+consum_O2+generate_CO2; 0.268, 0.630, pH_cumulo+PL+AN+AN_cumulo+interval_yield+OD+RS+RS_cumulo+rab_integral+RQ_integral+Accum._Yield+AS_Vol.+consum_O2; 0.268, 0.630, pH_cumulo+PL+AN+interval_yield+OD+RS+RS_cumulo+Cell_conc._interval+Accum._Yield+AS_Vol.+emission_O2+consum_O2+generate_CO2; 0.280, 0.630, tmp+pH_cumulo+PL+AN+OD+RS+Feed_Vol+RS_cumulo+Accum._Yield+AS_Vol.+consum_O2+generate_CO2; 0.256, 0.630, pH+pH_cumulo+PL+AN+OD+RS+Feed_Vol+RS_cumulo+Accum._Yield+AS_Vol.+emission_CO2+consum_O2+interval_O2+generate_CO2; 0.280, 0.630, pH_cumulo+PL+AN+OD+RS+RS_cumulo+Cell_conc._interval+Accum._Yield+AS_Vol.+emission_CO2+consum_O2+generate_CO2; 0.268, 0.630, pH+pH_cumulo+PL+AN+interval_yield+OD+RS+RS_cumulo+AS_Vol.+emission_O2+consum_O2; 0.280, 0.630, pH+pH_cumulo+PL+AN+OD+RS+RS_cumulo+Accum._Yield+AS_Vol.+emission_CO2+consum_O2+generate_CO2; 0.268, 0.630, tmp_cumulo+pH_cumulo+PL+AN+interval_yield+OD+RS+Feed_Vol+RS_cumulo+RQ_integral+Accum._Yield+AS_Vol.+consum_O2; 0.256, 0.630, tmp_cumulo+pH_cumulo+PL+AN+AN_cumulo+interval_yield+OD+RS+RS_cumulo+Accum._Yield+AS_Vol.+emission_CO2+consum_O2+generate_CO2; 0.256, 0.630, pH+pH_cumulo+PL+AN+interval_yield+OD+RS+Feed_Vol+RS_cumulo+RQ_integral+Accum._Yield+AS_Vol.+emission_O2+consum_O2; 0.243, 0.630, tmp+pH_cumulo+PL+AN+interval_yield+OD+RS+Feed_Vol+RS_cumulo+Cell_conc._interval+Accum._Yield+AS_Vol.+emission_CO2+consum_O2+generate_CO2; 0.291, 0.630, pH+pH_cumulo+PL+AN+OD+RS+RS_cumulo+Accum._Yield+AS_Vol.+consum_O2+generate_CO2; 0.256, 0.630, pH_cumulo+PL+AN_cumulo+interval_yield+OD+RS+Feed_Vol+RS_cumulo+Cell_conc._interval+Accum._Yield+AS_Vol.+emission_CO2+consum_O2+generate_CO2; 0.280, 0.630, pH_cumulo+PL+AN+interval_Pdt.+OD+RS+RS_cumulo+Accum._Yield+AS_Vol.+emission_CO2+consum_O2+generate_CO2; 0.268, 0.630, tmp+tmp_cumulo+pH_cumulo+PL+AN+interval_yield+OD+RS+RS_cumulo+AS_Vol.+emission_CO2+consum_O2+generate_CO2; 0.268, 0.630, pH_cumulo+PL+interval_yield+OD+RS+Feed_Vol+RS_cumulo+Accum._Yield+AS_Vol.+emission_CO2+consum_O2+interval_O2+generate_CO2; 0.280, 0.630, pH_cumulo+PL+interval_yield+OD+RS+Feed_Vol+RS_cumulo+RQ_integral+AS_Vol.+emission_O2+emission_CO2+consum_O2; 0.280, 0.630, pH_cumulo+PL+AN+OD+RS+RS_cumulo+rab_integral+Accum._Yield+AS_Vol.+emission_CO2+consum_O2+generate_CO2; 0.256, 0.630, pH+pH_cumulo+PL+AN+interval_yield+OD+RS+RS_cumulo+rab_integral+Accum._Yield+AS_Vol.+emission_CO2+consum_O2+generate_CO2; 0.268, 0.630, pH_cumulo+PL+interval_yield+OD+RS+Feed_Vol+RS_cumulo+rab_integral+Accum._Yield+AS_Vol.+emission_CO2+consum_O2+generate_CO2; 0.256, 0.630, tmp+pH_cumulo+PL+AN_cumulo+interval_yield+OD+RS+Feed_Vol+RS_cumulo+Accum._Yield+AS_Vol.+emission_CO2+consum_O2+generate_CO2; 0.268, 0.630, tmp_cumulo+pH_cumulo+PL+AN+interval_yield+OD+RS+RS_cumulo+Cell_conc._interval+Accum._Yield+AS_Vol.+consum_O2+generate_CO2; 0.243, 0.630, pH_cumulo+PL+PL_cumulo+AN+interval_yield+OD+RS+Feed_Vol+RS_cumulo+rab_integral+Accum._Yield+AS_Vol.+emission_CO2+consum_O2+generate_CO2; 0.280, 0.630, pH_cumulo+PL+AN+interval_Pdt.+OD+RS+Feed_Vol+RS_cumulo+RQ_integral+Accum._Yield+AS_Vol.+consum_O2; 0.243, 0.630, pH_cumulo+PL+AN+AN_cumulo+interval_yield+OD+RS+Feed_Vol+RS_cumulo+rab_integral+RQ_integral+Accum._Yield+AS_Vol.+emission_O2+consum_O2; 0.268, 0.630, tmp+pH_cumulo+PL+AN+OD+RS+Feed_Vol+RS_cumulo+Accum._Yield+AS_Vol.+emission_CO2+consum_O2+generate_CO2; 0.268, 0.630, pH_cumulo+PL+AN+AN_cumulo+interval_yield+OD+RS+RS_cumulo+RQ_integral+Accum._Yield+AS_Vol.+emission_O2+consum_O2; 0.280, 0.630, pH_cumulo+PL+AN_cumulo+interval_yield+OD+RS+RS_cumulo+Cell_conc._interval+Accum._Yield+AS_Vol.+consum_O2+generate_CO2; 0.268, 0.630, pH_cumulo+PL+AN+AN_cumulo+interval_yield+OD+RS+Feed_Vol+Accum._Yield+AS_Vol.+emission_CO2+consum_O2+generate_CO2; 0.268, 0.630, tmp_cumulo+pH_cumulo+PL+AN+interval_yield+OD+RS+RS_cumulo+Accum._Yield+AS_Vol.+consum_O2+interval_O2+generate_CO2; 0.255, 0.630, pH_cumulo+PL+AN+interval_yield+OD+RS+RS_cumulo+Cell_conc._interval+rab_integral+Accum._Yield+

AS_Vol.+emission_CO2+consum_O2+generate_CO2; 0.279, 0.629, pH_cumulo+PL+AN+AN_cumulo+interval_yield+OD+RS+Feed_Vol+RS_cumulo+RQ_integral+AS_Vol.+consum_O2; 0.268, 0.629, pH_cumulo+PL+AN+interval_Pdt.+OD+RS+Feed_Vol+RS_cumulo+Accum._Yield+AS_Vol.+emission_CO2+consum_O2+generate_CO2; 0.302, 0.629, pH_cumulo+PL+interval_yield+OD+RS+RS_cumulo+rab_integral+RQ_integral+AS_Vol.+consum_O2; 0.255, 0.629, tmp+pH_cumulo+PL+AN+AN_cumulo+interval_yield+OD+RS+Feed_Vol+RS_cumulo+AS_Vol.+emission_CO2+consum_O2+generate_CO2; 0.279, 0.629, pH_cumulo+PL+interval_yield+interval_Pdt.+OD+RS+RS_cumulo+RQ_integral+AS_Vol.+emission_O2+emission_CO2+consum_O2; 0.279, 0.629, pH_cumulo+PL+AN+interval_yield+OD+RS+RS_cumulo+RQ_integral+Accum._Yield+AS_Vol.+emission_CO2+consum_O2; 0.255, 0.629, tmp+pH_cumulo+PL+AN+interval_yield+OD+RS+Feed_Vol+RS_cumulo+Accum._Yield+AS_Vol.+consum_O2+interval_O2+generate_CO2; 0.279, 0.629, pH_cumulo+PL+AN+AN_cumulo+interval_Pdt.+OD+RS+RS_cumulo+RQ_integral+Accum._Yield+AS_Vol.+consum_O2; 0.255, 0.629, pH_cumulo+PL+AN+interval_yield+OD+RS+RS_cumulo+Cell_conc._interval+Accum._Yield+AS_Vol.+emission_CO2+consum_O2+interval_O2+generate_CO2; 0.267, 0.629, tmp+pH_cumulo+PL+AN+interval_yield+interval_Pdt.+OD+RS+Feed_Vol+Accum._Yield+AS_Vol.+consum_O2+generate_CO2; 0.267, 0.629, pH+pH_cumulo+PL+AN_cumulo+interval_yield+OD+RS+Feed_Vol+RS_cumulo+AS_Vol.+emission_CO2+consum_O2+generate_CO2; 0.279, 0.629, pH_cumulo+PL+AN+interval_yield+interval_Pdt.+OD+RS+RS_cumulo+AS_Vol.+emission_CO2+consum_O2+generate_CO2; 0.279, 0.629, pH_cumulo+PL+AN_cumulo+interval_yield+OD+RS+RS_cumulo+Accum._Yield+AS_Vol.+emission_O2+consum_O2+generate_CO2; 0.267, 0.629, tmp+pH_cumulo+PL+AN+AN_cumulo+interval_yield+OD+RS+RS_cumulo+AS_Vol.+emission_CO2+consum_O2+generate_CO2; 0.290, 0.629, pH_cumulo+PL+AN+OD+RS+RS_cumulo+Accum._Yield+AS_Vol.+emission_CO2+consum_O2+generate_CO2; 0.279, 0.629, pH_cumulo+PL+AN_cumulo+interval_yield+OD+RS+RS_cumulo+rab_integral+Accum._Yield+AS_Vol.+consum_O2+generate_CO2; 0.255, 0.629, pH_cumulo+PL+AN+interval_yield+interval_Pdt.+OD+RS+Feed_Vol+RS_cumulo+Cell_conc._interval+Accum._Yield+AS_Vol.+consum_O2+generate_CO2; 0.255, 0.629, tmp_cumulo+pH_cumulo+PL+AN+interval_yield+OD+RS+Feed_Vol+RS_cumulo+Accum._Yield+AS_Vol.+consum_O2+interval_O2+generate_CO2; 0.267, 0.629, pH_cumulo+PL+AN+AN_cumulo+interval_yield+OD+RS+RS_cumulo+Cell_conc._interval+AS_Vol.+emission_CO2+consum_O2+generate_CO2; 0.279, 0.629, pH_cumulo+PL+AN+interval_yield+OD+RS+Feed_Vol+RS_cumulo+rab_integral+AS_Vol.+consum_O2+generate_CO2; 0.279, 0.629, pH+pH_cumulo+PL+AN+OD+RS+RS_cumulo+Accum._Yield+AS_Vol.+consum_O2+interval_O2+generate_CO2; 0.279, 0.629, tmp_cumulo+pH_cumulo+PL+AN+OD+RS+Feed_Vol+RS_cumulo+Accum._Yield+AS_Vol.+consum_O2+generate_CO2; 0.279, 0.629, tmp+pH_cumulo+PL+interval_yield+OD+RS+RS_cumulo+Accum._Yield+AS_Vol.+emission_CO2+consum_O2+generate_CO2; 0.279, 0.629, pH+pH_cumulo+PL+AN+interval_yield+OD+RS+RS_cumulo+RQ_integral+Accum._Yield+AS_Vol.+consum_O2; 0.267, 0.629, tmp_cumulo+pH_cumulo+PL+AN+interval_yield+OD+RS+RS_cumulo+rab_integral+Accum._Yield+AS_Vol.+consum_O2+generate_CO2; 0.267, 0.629, pH_cumulo+PL+AN+interval_yield+OD+RS+RS_cumulo+Accum._Yield+AS_Vol.+emission_O2+emission_CO2+consum_O2+generate_CO2; 0.255, 0.629, tmp_cumulo+pH_cumulo+PL+AN+interval_yield+interval_Pdt.+OD+RS+Feed_Vol+RS_cumulo+Accum._Yield+AS_Vol.+consum_O2+generate_CO2; 0.279, 0.629, pH_cumulo+PL+PL_cumulo+AN+interval_yield+OD+RS+RS_cumulo+AS_Vol.+emission_CO2+consum_O2+generate_CO2; 0.290, 0.629, pH_cumulo+PL+interval_yield+OD+RS+RS_cumulo+rab_integral+RQ_integral+Accum._Yield+AS_Vol.+consum_O2; 0.278, 0.629, pH_cumulo+PL+AN+OD+RS+RS_cumulo+Accum._Yield+AS_Vol.+emission_O2+consum_O2+interval_O2+generate_CO2; 0.290, 0.629, pH_cumulo+PL+AN+AN_cumulo+interval_yield+OD+RS+RS_cumulo+AS_Vol.+consum_O2+generate_CO2; 0.254, 0.629, pH_cumulo+PL+AN+interval_yield+OD+RS+Feed_Vol+RS_cumulo+Cell_conc._interval+rab_integral+RQ_integral+Accum._Yield+AS_Vol.+consum_O2; 0.278, 0.629, pH_cumulo+PL+AN_cumulo+interval_yield+OD+RS+Feed_Vol+RS_cumulo+RQ_integral+Accum._Yield+AS_Vol.+consum_O2; 0.278, 0.629, pH_cumulo+PL+AN+interval_yield+OD+RS+Feed_Vol+rab_integral+Accum._Yield+AS_Vol.+consum_O2+generate_CO2; 0.266, 0.629, pH_cumulo+PL+AN+interval_yield+interval_Pdt.+OD+RS+Feed_Vol+RS_cumulo+AS_Vol.+emission_CO2+consum_O2+generate_CO2; 0.301, 0.629, pH+pH_cumulo+PL+interval_yield+OD+RS+RS_cumulo+emission_CO2+consum_O2+generate_CO2; 0.254, 0.629, pH_cumulo+PL+AN+AN_cumulo+interval_yield+interval_Pdt.+OD+RS+Feed_Vol+RS_cumulo+RQ_integral+Accum._Yield+AS_Vol.+consum_O2; 0.266, 0.629, pH+pH_cumulo+PL+AN+AN_cumulo+interval_yield+OD+RS+RS_cumulo+AS_Vol.+emission_CO2+consum_O2+generate_CO2; 0.278, 0.629, pH_cumulo+PL+AN+AN_cumulo+OD+RS+RS_cumulo+rab_integral+Accum._Yield+AS_Vol.+consum_O2+generate_CO2; 0.266, 0.629, pH+pH_cumulo+PL+AN+interval_yield+OD+RS+RS_cumulo+rab_integral+AS_Vol.+emission_CO2+consum_O2+generate_CO2; 0.301, 0.629, pH_cumulo+PL+AN+interval_yield+OD+RS+RS_cumulo+Accum._Yield+AS_Vol.+consum_O2; 0.254, 0.629, pH+pH_cumulo+PL+AN+interval_yield+OD+RS+RS_cumulo+Accum._Yield+AS_Vol.+emission_CO2+consum_O2+interval_O2+generate_CO2; 0.266, 0.629, pH_cumulo+PL+AN+interval_yield+OD+RS+RS_cumulo+rab_integral+AS_Vol.+emission_CO2+consum_O2+interval_O2+generate_CO2; 0.241, 0.629, tmp+pH_cumulo+PL+AN+interval_yield+OD+RS+Feed_Vol+RS_cumulo+Accum._Yield+AS_Vol.+emission_CO2+consum_O2+interval_O2+generate_CO2; 0.254, 0.629, pH+pH_cumulo+PL+AN+interval_yield+OD+RS+RS_cumulo+Cell_conc._interval+Accum._Yield+AS_Vol.+emission_CO2+consum_O2+generate_CO2; 0.289, 0.628, pH_cumulo+PL+AN_cumulo+interval_yield+OD+RS+Feed_Vol+RS_cumulo+emission_CO2+consum_O2+generate_CO2; 0.266, 0.628, pH_cumulo+PL+AN+OD+RS+Feed_Vol+RS_cumulo+Cell_conc._interval+Accum._Yield+AS_Vol.+consum_O2+interval_O2+generate_CO2; 0.254, 0.628, pH_cumulo+PL+AN_cumulo+interval_yield+OD+RS+Feed_Vol+RS_cumulo+Accum._Yield+AS_Vol.+emission_CO2+consum_O2+interval_O2+generate_CO2; 0.254, 0.628, pH_cumulo+PL+AN+interval_yield+OD+RS+Feed_Vol+RS_cumulo+Cell_conc._interval+RQ_integral+Accum._Yield+AS_Vol.+emission_O2+consum_O2; 0.254, 0.628, tmp+pH_cumulo+PL+AN+interval_yield+OD+RS+Feed_Vol+RS_cumulo+Accum._Yield+AS_Vol.+consum_O2+generate_CO2; 0.254, 0.628, pH+pH_cumulo+PL+AN+interval_yield+OD+RS+Feed_Vol+RS_cumulo+rab_integral+AS_Vol.+emission_CO2+consum_O2+generate_CO2; 0.254, 0.628, pH_cumulo+PL+AN+AN_cumulo+interval_yield+OD+RS+Feed_Vol+RS_cumulo+Cell_conc._interval+RQ_integral+Accum._Yield+AS_Vol.+consum_O2; 0.289, 0.628, pH_cumulo+PL+interval_yield+OD+RS+RS_cumulo+Accum._Yield+AS_Vol.+consum_O2+interval_O2+generate_CO2; 0.254, 0.628, tmp_cumulo+pH+pH_cumulo+PL+AN+interval_yield+OD+RS+Feed_Vol+RS_cumulo+Accum._Yield+AS_Vol.+consum_O2+generate_CO2; 0.254, 0.628, pH+pH_cumulo+PL+AN+AN_cumulo+interval_yield+OD+RS+Feed_Vol+RS_cumulo+AS_Vol.+emission_CO2+consum_O2+generate_CO2; 0.266, 0.628, tmp+pH_cumulo+PL+AN+interval_yield+OD+RS+RS_cumulo+Accum._Yield+AS_Vol.+consum_O2+interval_O2+generate_CO2; 0.278, 0.628, pH_cumulo+PL+AN+interval_yield+OD+RS+Feed_Vol+RS_cumulo+RQ_integral+AS_Vol.+emission_CO2+consum_O2; 0.278, 0.628, pH_cumulo+PL+interval_yield+OD+RS+RS_cumulo+rab_integral+AS_Vol.+emission_CO2+consum_O2+interval_O2+generate_CO2; 0.253, 0.628, tmp+tmp_cumulo+pH_cumulo+PL+AN+interval_yield+OD+RS+Feed_Vol+RS_cumulo+AS_Vol.+emission_CO2+consum_O2+generate_CO2; 0.289, 0.628, pH_cumulo+PL+AN+interval_yield+OD+RS+RS_cumulo+RQ_integral+AS_Vol.+emission_CO2+consum_O2; 0.289, 0.628, pH_cumulo+PL+AN_cumulo+interval_yield+OD+RS+RS_cumulo+rab_integral+emission_CO2+consum_O2+generate_CO2; 0.266, 0.628, pH+pH_cumulo+PL+AN+OD+RS+Feed_Vol+RS_cumulo+rab_integral+Accum._Yield+AS_Vol.+consum_O2+generate_CO2; 0.253, 0.628, tmp_cumulo+pH_cumulo+PL+AN_cumulo+interval_yield+OD+RS+Feed_Vol+RS_cumulo+Accum._Yield+AS_Vol.+emission_CO2+consum_O2+generate_CO2; 0.300, 0.628, tmp+pH_cumulo+PL+interval_yield+OD+RS+RS_cumulo+emission_CO2+consum_O2+generate_CO2; 0.289, 0.628, tmp_cumulo+pH_cumulo+PL+AN+OD+RS+RS_cumulo+Accum._Yield+AS_Vol.+consum_O2+generate_CO2; 0.277, 0.628, pH_cumulo+PL+PL_cumulo+AN+interval_yield+OD+RS+RS_cumulo+RQ_integral+Accum._Yield+AS_Vol.+consum_O2; 0.253, 0.628, pH_cumulo+PL+AN+AN_cumulo+OD+RS+Feed_Vol+RS_cumulo+Cell_conc._interval+Accum._Yield+AS_Vol.+emission_CO2+consum_O2+generate_CO2; 0.253, 0.628, pH_cumulo+PL+AN+interval_yield+OD+RS+Feed_Vol+RS_cumulo+rab_integral+RQ_integral+Accum._Yield+AS_Vol.+emission_CO2+consum_O2; 0.265, 0.628, pH_cumulo+PL+AN+interval_yield+OD+RS+RS_cumulo+Cell_conc._interval+rab_integral+AS_Vol.+emission_CO2+consum_O2+generate_CO2; 0.265, 0.628, pH+pH_cumulo+PL+interval_yield+OD+RS+Feed_Vol+RS_cumulo+Accum._Yield+AS_Vol.+emission_CO2+consum_O2+generate_CO2; 0.253, 0.628, pH_cumulo+PL+AN+AN_cumulo+interval_yield+OD+RS+RS_cumulo+Cell_conc._interval+rab_integral+Accum._Yield+AS_Vol.+consum_O2+generate_CO2; 0.277, 0.628, pH_cumulo+PL+AN+interval_yield+OD+RS+RS_cumulo+RQ_integral+AS_Vol.+emission_O2+emission_CO2+consum_O2; 0.253, 0.628, tmp_cumulo+pH_cumulo+PL+AN+AN_cumulo+interval_yield+OD+RS+Feed_Vol+RS_cumulo+AS_Vol.+emission_CO2+consum_O2+generate_CO2; 0.277, 0.628, pH_cumulo+PL+AN_cumulo+OD+RS+RS_cumulo+rab_integral+Accum._Yield+AS_Vol.+emission_CO2+consum_O2+generate_CO2; 0.240, 0.628, tmp_cumulo+pH_cumulo+PL+AN+AN_cumulo+interval_yield+OD+RS+AS_Vol.+consum_O2+generate_CO2; 0.240, 0.628, pH_cumulo+PL+AN+AN_cumulo+interval_yield+interval_Pdt.+OD+RS+Feed_Vol+RS_cumulo+rab_integral+Accum._Yield+AS_Vol.+consum_O2+generate_CO2; 0.240, 0.628, pH_cumulo+PL+PL_cumulo+AN+AN_cumulo+interval_yield+OD+RS+Feed_Vol+RS_cumulo+Accum._Yield+AS_Vol.+emission_CO2+consum_O2+generate_CO2; 0.277, 0.628, pH_cumulo+PL+interval_yield+OD+RS+RS_cumulo+RQ_integral+Accum._Yield+AS_Vol.+emission_O2+emission_CO2+consum_O2; 0.240, 0.628, pH_cumulo+PL+AN+interval_yield+OD+RS+Feed_Vol+RS_cumulo+rab_integral+Accum._Yield+AS_Vol.+emission_O2+emission_CO2+consum_O2+generate_CO2; 0.277, 0.628, tmp_cumulo+pH_cumulo+PL+interval_yield+OD+RS+Feed_Vol+RS_cumulo+AS_Vol.+emission_CO2+consum_O2+generate_CO2; 0.265, 0.628, tmp_cumulo+pH_cumulo+PL+AN+OD+RS+Feed_Vol+RS_cumulo+Accum._Yield+AS_Vol.+emission_CO2+consum_O2+generate_CO2; 0.277, 0.628, pH_cumulo+PL+AN+interval_yield+OD+RS+Feed_Vol+RS_cumulo+rab_integral+RQ_integral+AS_Vol.+consum_O2; 0.253, 0.628, tmp+pH_cumulo+PL+AN+interval_yield+OD+RS+Feed_Vol+RS_cumulo+rab_integral+AS_Vol.+emission_CO2+consum_O2+generate_CO2; 0.253, 0.628, pH_cumulo+PL+PL_cumulo+AN+interval_yield+OD+RS+Feed_Vol+RS_cumulo+Accum._Yield+AS_Vol.+consum_O2+interval_O2+generate_CO2; 0.277, 0.628, pH_cumulo+PL+AN_cumulo+interval_yield+OD+RS+RS_cumulo+rab_integral+RQ_integral+Accum._Yield+AS_Vol.+consum_O2; 0.240, 0.628, pH_cumulo+PL+AN+interval_yield+interval_Pdt.+OD+RS+Feed_Vol+RS_cumulo+rab_integral+Accum._Yield+AS_Vol.+emission_CO2+consum_O2+generate_CO2; 0.277, 0.628, pH_cumulo+PL+AN+interval_Pdt.+OD+RS+RS_cumulo+RQ_integral+Accum._Yield+AS_Vol.+emission_CO2+consum_O2; 0.277, 0.628, pH+PL+AN+interval_yield+OD+RS+RS_cumulo+Cell_conc._interval+Accum._Yield+AS_Vol.+consum_O2+generate_CO2; 0.240, 0.628, pH+pH_cumulo+PL+AN+interval_yield+OD+RS+Feed_Vol+RS_cumulo+rab_integral+Accum._Yield+AS_Vol.+consum_O2+interval_O2+generate_CO2; 0.227, 0.628, tmp+tmp_cumulo+pH_cumulo+PL+AN+AN_cumulo+interval_yield+OD+RS+Feed_Vol+RS_cumulo+Accum._Yield+AS_Vol.+emission_CO2+consum_O2+generate_CO2; 0.252, 0.628, pH_cumulo+PL+PL_cumulo+AN+AN_cumulo+interval_yield+OD+RS+Feed_Vol+RS_cumulo+RQ_integral+Accum._Yield+AS_Vol.+consum_O2; 0.252, 0.628, tmp+pH_cumulo+PL+AN+interval_yield+OD+RS+Feed_Vol+RS_cumulo+Accum._Yield+AS_Vol.+emission_O2+consum_O2+generate_CO2; 0.288, 0.628, tmp+pH_cumulo+PL+AN+OD+RS+RS_cumulo+Accum._Yield+AS_Vol.+consum_O2+generate_CO2; 0.265, 0.628, tmp+pH_cumulo+PL+AN_cumulo+interval_yield+OD+RS+Feed_Vol+RS_cumulo+AS_Vol.+emission_CO2+consum_O2+generate_CO2; 0.265, 0.628, pH+pH_cumulo+PL+AN+interval_yield+OD+RS+Feed_Vol+RS_cumulo+rab_integral+Accum._Yield+AS_Vol.+consum_O2; 0.252, 0.627, tmp+pH_cumulo+PL+AN+AN_cumulo+OD+RS+Feed_Vol+RS_cumulo+Accum._Yield+AS_Vol.+emission_CO2+consum_O2+generate_CO2; 0.299, 0.627, pH_cumulo+PL+AN+interval_yield+OD+RS+Feed_Vol+RS_cumulo+AS_Vol.+consum_O2; 0.264, 0.627, pH+PL+AN+interval_yield+OD+RS+Feed_Vol+RS_cumulo+Accum._Yield+AS_Vol.+emission_CO2+consum_O2+generate_

CO2; 0.264, 0.627, pH_cumulo+PL+AN+interval_yield+interval_Pdt.+OD+RS+RS_cumulo+rab_integral+Accum._Yield+AS_Vol.+consum_O2+generate_CO2; 0.240, 0.627, tmp+tmp_cumulo+pH_cumulo+PL+AN+interval_yield+OD+RS+Feed_Vol+RS_cumulo+rab_integral+Accum._Yield+AS_Vol.+consum_O2+generate_CO2; 0.264, 0.627, pH_cumulo+PL+AN+AN_cumulo+interval_yield+OD+RS+RS_cumulo+AS_Vol.+emission_CO2+consum_O2+interval_O2+generate_CO2; 0.252, 0.627, pH_cumulo+PL+AN+AN_cumulo+interval_yield+OD+RS+Feed_Vol+RS_cumulo+rab_integral+Accum._Yield+AS_Vol.+emission_CO2+consum_O2; 0.276, 0.627, pH_cumulo+PL+AN+interval_yield+OD+RS+RS_cumulo+Cell_conc._interval+RQ_integral+Accum._Yield+AS_Vol.+consum_O2; 0.264, 0.627, tmp_cumulo+pH_cumulo+PL+AN+AN_cumulo+interval_yield+OD+RS+RS_cumulo+AS_Vol.+emission_CO2+consum_O2+generate_CO2; 0.239, 0.627, tmp_cumulo+pH_cumulo+PL+AN+interval_yield+OD+RS+Feed_Vol+RS_cumulo+Cell_conc._interval+Accum._Yield+AS_Vol.+emission_CO2+consum_O2+generate_CO2; 0.276, 0.627, pH_cumulo+PL+AN+interval_yield+OD+RS+RS_cumulo+AS_Vol.+emission_O2+emission_CO2+consum_O2+generate_CO2; 0.264, 0.627, tmp+pH_cumulo+PL+AN+interval_yield+OD+RS+RS_cumulo+rab_integral+AS_Vol.+emission_CO2+consum_O2+generate_CO2; 0.264, 0.627, pH_cumulo+PL+PL_cumulo+AN+interval_yield+OD+RS+Feed_Vol+RS_cumulo+AS_Vol.+emission_CO2+consum_O2+generate_CO2; 0.276, 0.627, pH_cumulo+PL+AN+interval_yield+OD+RS+Feed_Vol+RS_cumulo+AS_Vol.+emission_O2+consum_O2+generate_CO2; 0.276, 0.627, pH+pH_cumulo+PL+AN+interval_yield+OD+RS+Feed_Vol+RS_cumulo+Accum._Yield+AS_Vol.+consum_O2; 0.288, 0.627, pH_cumulo+PL+AN+interval_yield+OD+RS+Feed_Vol+RS_cumulo+emission_CO2+consum_O2+generate_CO2; 0.288, 0.627, tmp+pH_cumulo+PL+AN+interval_yield+OD+RS+RS_cumulo+AS_Vol.+consum_O2+generate_CO2; 0.264, 0.627, pH_cumulo+PL+AN+AN_cumulo+OD+RS+Feed_Vol+RS_cumulo+Accum._Yield+AS_Vol.+emission_O2+consum_O2+generate_CO2; 0.276, 0.627, pH+pH_cumulo+PL+interval_yield+OD+RS+RS_cumulo+rab_integral+AS_Vol.+emission_CO2+consum_O2+generate_CO2; 0.239, 0.627, pH+pH_cumulo+PL+AN+AN_cumulo+interval_yield+OD+RS+Feed_Vol+RS_cumulo+Cell_conc._interval+Accum._Yield+AS_Vol.+consum_O2+generate_CO2; 0.276, 0.627, tmp_cumulo+pH_cumulo+PL+interval_yield+OD+RS+RS_cumulo+Accum._Yield+AS_Vol.+emission_CO2+consum_O2+generate_CO2; 0.309, 0.627, pH_cumulo+PL+AN+interval_yield+OD+RS+RS_cumulo+AS_Vol.+consum_O2; 0.309, 0.627, pH_cumulo+PL+interval_yield+OD+RS+RS_cumulo+AS_Vol.+consum_O2+generate_CO2; 0.252, 0.627, pH_cumulo+PL+AN+OD+RS+Feed_Vol+RS_cumulo+rab_integral+Accum._Yield+AS_Vol.+emission_CO2+consum_O2+interval_O2+generate_CO2; 0.276, 0.627, tmp+pH_cumulo+PL+AN+interval_yield+OD+RS+Feed_Vol+RS_cumulo+Accum._Yield+AS_Vol.+consum_O2; 0.276, 0.627, pH_cumulo+PL+AN+AN_cumulo+interval_yield+OD+RS+RS_cumulo+rab_integral+RQ_integral+AS_Vol.+consum_O2; 0.264, 0.627, pH_cumulo+PL+interval_yield+OD+RS+Feed_Vol+RS_cumulo+RQ_integral+Accum._Yield+AS_Vol.+emission_O2+emission_CO2+consum_O2; 0.298, 0.627, pH_cumulo+PL+interval_yield+OD+RS+RS_cumulo+RQ_integral+AS_Vol.+emission_CO2+consum_O2; 0.226, 0.627, tmp+pH_cumulo+PL+AN+AN_cumulo+interval_yield+OD+RS+Feed_Vol+RS_cumulo+rab_integral+Accum._Yield+AS_Vol.+emission_CO2+consum_O2+generate_CO2; 0.252, 0.627, pH+pH_cumulo+PL+PL_cumulo+AN+interval_yield+OD+RS+Feed_Vol+RS_cumulo+Accum._Yield+AS_Vol.+consum_O2+generate_CO2; 0.264, 0.627, pH_cumulo+PL+AN+interval_yield+interval_Pdt.+OD+RS+Feed_Vol+Accum._Yield+AS_Vol.+consum_O2+interval_O2+generate_CO2; 0.276, 0.627, pH+PL+AN+interval_yield+interval_Pdt.+OD+RS+Feed_Vol+Accum._Yield+AS_Vol.+consum_O2+generate_CO2; 0.264, 0.627, pH_cumulo+PL+AN_cumulo+interval_yield+OD+RS+Feed_Vol+RS_cumulo+Cell_conc._interval+AS_Vol.+emission_CO2+consum_O2+generate_CO2; 0.264, 0.627, pH_cumulo+PL+AN+OD+RS+RS_cumulo+rab_integral+Accum._Yield+AS_Vol.+emission_CO2+consum_O2+interval_O2+generate_CO2; 0.239, 0.627, tmp_cumulo+pH_cumulo+PL+AN+interval_yield+OD+RS+Feed_Vol+RS_cumulo+Accum._Yield+AS_Vol.+emission_CO2+consum_O2+interval_O2+generate_CO2; 0.239, 0.627, pH_cumulo+PL+AN+AN_cumulo+interval_yield+OD+RS+Feed_Vol+RS_cumulo+Accum._Yield+AS_Vol.+emission_O2+emission_CO2+consum_O2+generate_CO2; 0.264, 0.627, pH+pH_cumulo+PL+AN+OD+RS+RS_cumulo+Accum._Yield+AS_Vol.+emission_CO2+consum_O2+interval_O2+generate_CO2; 0.239, 0.627, tmp+tmp_cumulo+pH_cumulo+PL+AN+AN_cumulo+interval_yield+OD+RS+Feed_Vol+RS_cumulo+Accum._Yield+AS_Vol.+consum_O2+generate_CO2; 0.264, 0.627, pH_cumulo+PL+AN+AN_cumulo+interval_yield+OD+RS+Feed_Vol+RS_cumulo+Accum._Yield+AS_Vol.+emission_CO2+consum_O2; 0.275, 0.627, tmp_cumulo+pH_cumulo+PL+AN+OD+RS+RS_cumulo+Accum._Yield+AS_Vol.+consum_O2+interval_O2+generate_CO2; 0.251, 0.627, pH_cumulo+PL+AN+interval_yield+interval_Pdt.+OD+RS+Feed_Vol+RS_cumulo+RQ_integral+Accum._Yield+AS_Vol.+emission_O2+consum_O2; 0.264, 0.627, pH_cumulo+PL+AN+AN_cumulo+OD+RS+RS_cumulo+rab_integral+Accum._Yield+AS_Vol.+emission_CO2+consum_O2+generate_CO2; 0.251, 0.627, tmp+pH_cumulo+PL+AN+interval_yield+OD+RS+RS_cumulo+rab_integral+Accum._Yield+AS_Vol.+emission_CO2+consum_O2+generate_CO2; 0.263, 0.627, tmp+pH_cumulo+PL+AN+AN_cumulo+OD+RS+Feed_Vol+RS_cumulo+Accum._Yield+AS_Vol.+consum_O2+generate_CO2; 0.263, 0.627, pH+pH_cumulo+PL+AN+interval_yield+OD+RS+RS_cumulo+Accum._Yield+AS_Vol.+emission_O2+consum_O2+generate_CO2; 0.263, 0.627, tmp_cumulo+pH_cumulo+PL+AN+AN_cumulo+OD+RS+Feed_Vol+RS_cumulo+Accum._Yield+AS_Vol.+consum_O2+generate_CO2; 0.263, 0.627, pH_cumulo+PL+PL_cumulo+AN+interval_yield+OD+RS+RS_cumulo+Accum._Yield+AS_Vol.+consum_O2+interval_O2+generate_CO2; 0.251, 0.627, pH+PL+AN+AN_cumulo+interval_yield+OD+RS+Feed_Vol+RS_cumulo+Cell_conc._interval+Accum._Yield+AS_Vol.+consum_O2+generate_CO2; 0.263, 0.627, pH_cumulo+PL+AN+OD+RS+Feed_Vol+RS_cumulo+Accum._Yield+AS_Vol.+emission_O2+consum_O2+interval_O2+generate_CO2; 0.251, 0.627, tmp_cumulo+pH_cumulo+PL+AN+AN_cumulo+OD+RS+Feed_Vol+RS_cumulo+Accum._Yield+AS_Vol.+emission_CO2+consum_O2+generate_CO2; 0.263, 0.627, pH_cumulo+PL+AN+OD+RS+Feed_Vol+RS_cumulo+Cell_conc._interval+rab_integral+Accum._Yield+AS_Vol.+consum_O2+generate_CO2; 0.287, 0.627, pH_cumulo+PL+OD+RS+RS_cumulo+Accum._Yield+AS_Vol.+emission_CO2+consum_O2+interval_O2+generate_CO2; 0.263, 0.627, pH+pH_cumulo+PL+AN+AN_cumulo+OD+RS+RS_cumulo+Accum._Yield+AS_Vol.+emission_CO2+consum_O2+generate_CO2; 0.263, 0.627, pH_cumulo+PL+AN+AN_cumulo+OD+RS+RS_cumulo+Cell_conc._interval+Accum._Yield+AS_Vol.+emission_CO2+consum_O2+generate_CO2; 0.275, 0.627, pH_cumulo+PL+AN+interval_yield+OD+RS+Feed_Vol+RS_cumulo+RQ_integral+AS_Vol.+emission_O2+consum_O2; 0.238, 0.626, pH+pH_cumulo+PL+AN+interval_yield+OD+RS+Feed_Vol+RS_cumulo+rab_integral+Accum._Yield+AS_Vol.+emission_O2+consum_O2+generate_CO2; 0.275, 0.626, pH_cumulo+PL+AN_cumulo+interval_Pdt.+OD+RS+RS_cumulo+Accum._Yield+AS_Vol.+emission_CO2+consum_O2+generate_CO2; 0.286, 0.626, tmp_cumulo+pH_cumulo+PL+AN+interval_yield+OD+RS+RS_cumulo+AS_Vol.+consum_O2+generate_CO2; 0.238, 0.626, pH_cumulo+PL+AN+interval_yield+OD+RS+Feed_Vol+RS_cumulo+Cell_conc._interval+rab_integral+Accum._Yield+AS_Vol.+consum_O2+interval_O2+generate_CO2; 0.225, 0.626, pH_cumulo+PL+AN+AN_cumulo+interval_yield+OD+RS+Feed_Vol+RS_cumulo+Cell_conc._interval+rab_integral+Accum._Yield+AS_Vol.+emission_CO2+consum_O2+generate_CO2; 0.251, 0.626, pH_cumulo+PL+AN+AN_cumulo+interval_yield+OD+RS+Feed_Vol+RS_cumulo+Cell_conc._interval+AS_Vol.+emission_CO2+consum_O2+generate_CO2; 0.238, 0.626, pH_cumulo+PL+AN+AN_cumulo+interval_yield+interval_Pdt.+OD+RS+Feed_Vol+RS_cumulo+Accum._Yield+AS_Vol.+emission_CO2+consum_O2+generate_CO2; 0.238, 0.626, pH_cumulo+PL+AN+interval_yield+interval_Pdt.+OD+RS+Feed_Vol+RS_cumulo+RQ_integral+Accum._Yield+AS_Vol.+emission_O2+emission_CO2+consum_O2; 0.263, 0.626, pH_cumulo+PL+AN+interval_yield+OD+RS+RS_cumulo+RQ_integral+Accum._Yield+AS_Vol.+emission_O2+emission_CO2+consum_O2; 0.275, 0.626, pH+pH_cumulo+PL+AN+AN_cumulo+OD+RS+RS_cumulo+Accum._Yield+AS_Vol.+emission_CO2+consum_O2+generate_CO2; 0.286, 0.626, pH_cumulo+PL+AN+interval_yield+OD+RS+RS_cumulo+rab_integral+emission_CO2+consum_O2+generate_CO2; 0.225, 0.626, pH+pH_cumulo+PL+AN+AN_cumulo+interval_yield+OD+RS+Feed_Vol+RS_cumulo+Cell_conc._interval+Accum._Yield+AS_Vol.+emission_CO2+consum_O2+generate_CO2; 0.250, 0.626, pH_cumulo+PL+AN+interval_yield+OD+RS+Feed_Vol+RS_cumulo+Cell_conc._interval+rab_integral+AS_Vol.+emission_CO2+consum_O2+generate_CO2; 0.297, 0.626, tmp_cumulo+pH_cumulo+PL+interval_yield+OD+RS+RS_cumulo+emission_CO2+consum_O2+generate_CO2; 0.286, 0.626, pH+pH_cumulo+PL+AN+interval_yield+OD+RS+RS_cumulo+RQ_integral+AS_Vol.+consum_O2; 0.286, 0.626, pH_cumulo+PL+interval_yield+OD+RS+Feed_Vol+RS_cumulo+RQ_integral+Accum._Yield+AS_Vol.+consum_O2; 0.274, 0.626, pH_cumulo+PL+AN+interval_yield+OD+RS+RS_cumulo+rab_integral+AS_Vol.+emission_O2+consum_O2+generate_CO2; 0.237, 0.626, pH+pH_cumulo+PL+AN+interval_yield+interval_Pdt.+OD+RS+Feed_Vol+RS_cumulo+Accum._Yield+AS_Vol.+emission_CO2+consum_O2+generate_CO2; 0.262, 0.626, pH_cumulo+PL+interval_yield+interval_Pdt.+OD+RS+RS_cumulo+RQ_integral+Accum._Yield+AS_Vol.+emission_O2+emission_CO2+consum_O2; 0.274, 0.626, pH_cumulo+PL+AN_cumulo+interval_yield+OD+RS+RS_cumulo+Accum._Yield+AS_Vol.+consum_O2+interval_O2+generate_CO2; 0.286, 0.626, pH_cumulo+PL+interval_Pdt.+OD+RS+RS_cumulo+RQ_integral+AS_Vol.+emission_O2+emission_CO2+consum_O2; 0.286, 0.626, pH_cumulo+PL+interval_yield+OD+RS+RS_cumulo+Accum._Yield+emission_CO2+consum_O2+interval_O2+generate_CO2; 0.274, 0.626, tmp+tmp_cumulo+pH_cumulo+PL+interval_yield+OD+RS+RS_cumulo+AS_Vol.+emission_CO2+consum_O2+generate_CO2; 0.262, 0.626, pH_cumulo+PL+AN+interval_yield+interval_Pdt.+OD+RS+RS_cumulo+Accum._Yield+AS_Vol.+consum_O2+interval_O2+generate_CO2; 0.286, 0.626, pH_cumulo+PL+AN+interval_yield+interval_Pdt.+OD+RS+RS_cumulo+AS_Vol.+consum_O2+generate_CO2; 0.274, 0.626, pH_cumulo+PL+interval_yield+OD+RS+RS_cumulo+rab_integral+RQ_integral+AS_Vol.+emission_O2+emission_CO2+consum_O2; 0.250, 0.626, pH_cumulo+PL+PL_cumulo+AN+AN_cumulo+interval_yield+OD+RS+Feed_Vol+RS_cumulo+Accum._Yield+AS_Vol.+consum_O2+generate_CO2; 0.297, 0.626, pH_cumulo+PL+interval_yield+OD+RS+RS_cumulo+Cell_conc._interval+emission_CO2+consum_O2+generate_CO2; 0.250, 0.626, pH_cumulo+PL+AN+AN_cumulo+interval_yield+OD+RS+RS_cumulo+rab_integral+Accum._Yield+AS_Vol.+consum_O2+interval_O2+generate_CO2; 0.262, 0.626, pH_cumulo+PL+AN+AN_cumulo+interval_yield+interval_Pdt.+OD+RS+RS_cumulo+RQ_integral+Accum._Yield+AS_Vol.+consum_O2; 0.250, 0.626, pH_cumulo+PL+AN+interval_yield+OD+RS+RS_cumulo+Cell_conc._interval+rab_integral+Accum._Yield+AS_Vol.+consum_O2+interval_O2+generate_CO2; 0.250, 0.626, tmp+pH_cumulo+PL+AN+AN_cumulo+interval_yield+OD+RS+Feed_Vol+RS_cumulo+RQ_integral+Accum._Yield+AS_Vol.+consum_O2; 0.250, 0.626, tmp_cumulo+pH_cumulo+PL+AN+interval_yield+OD+RS+RS_cumulo+Accum._Yield+AS_Vol.+emission_CO2+consum_O2+interval_O2+generate_CO2; 0.274, 0.626, pH_cumulo+PL+AN_cumulo+interval_yield+OD+RS+RS_cumulo+rab_integral+Accum._Yield+emission_CO2+consum_O2+generate_CO2; 0.262, 0.626, pH_cumulo+PL+interval_yield+OD+RS+Feed_Vol+RS_cumulo+Cell_conc._interval+Accum._Yield+AS_Vol.+emission_CO2+consum_O2+generate_CO2; 0.274, 0.626, tmp_cumulo+pH_cumulo+PL+AN_cumulo+OD+RS+RS_cumulo+Accum._Yield+AS_Vol.+emission_CO2+consum_O2+generate_CO2; 0.262, 0.626, pH_cumulo+PL+AN+interval_Pdt.+OD+RS+RS_cumulo+RQ_integral+Accum._Yield+AS_Vol.+emission_O2+emission_CO2+consum_O2; 0.250, 0.626, tmp+tmp_cumulo+pH_cumulo+PL+AN_cumulo+interval_yield+OD+RS+RS_cumulo+Accum._Yield+AS_Vol.+emission_CO2+consum_O2+generate_CO2; 0.274, 0.626, pH_cumulo+PL+AN+OD+RS+RS_cumulo+Cell_conc._interval+rab_integral+Accum._Yield+AS_Vol.+consum_O2+generate_CO2; 0.262, 0.626, pH+pH_cumulo+PL+AN+OD+RS+Feed_Vol+RS_cumulo+Cell_conc._interval+Accum._Yield+AS_Vol.+consum_O2+generate_CO2; 0.262, 0.626, pH_cumulo+PL+AN+interval_yield+OD+RS+Feed_Vol+RS_cumulo+AS_Vol.+emission_O2+emission_CO2+consum_O2+generate_CO2; 0.237, 0.626, pH+pH_cumulo+PL+AN+interval_yield+interval_Pdt.+OD+RS+Feed_Vol+RS_cumulo+rab_integral+Accum._Yield+AS_Vol.+consum_O2+generate_CO2; 0.224, 0.626, pH_cumulo+PL+AN+AN_cumulo+interval_yield+OD+RS+Feed_Vol+RS_cumulo+rab_integral+Accum._Yield+AS_Vol.+emission_CO2+consum_O2+interval_O2+generate_CO2; 0.249, 0.626, pH_cumulo+PL+AN+interval_yield+interval_Pdt.+OD+RS+Feed_Vol+RS_cumulo+RQ_integral+Accum._Yield+AS_Vol.+emission_CO2+consum_O2; 0.274, 0.626, tmp+pH_cumulo+PL+AN+OD+RS+RS_cumulo+Accum._Yield+AS_Vol.+emission_CO2+consum_O2+generate_CO2; 0.249, 0.626, tmp+pH_cumulo+PL+AN+interval_yield+OD+RS+RS_cumulo+Accum._Yield+AS_Vol.+emission_CO2+consum_O2+interval_O2+generate_CO2;

0.285, 0.626, pH_cumulo+PL+AN+AN_cumulo+interval_yield+OD+RS+RS_cumulo+emission_CO2+consum_O2+generate_CO2; 0.274, 0.626, pH+pH_cumulo+PL+AN+AN_cumulo+OD+RS+RS_cumulo+Accum._Yield+AS_Vol.+consum_O2+generate_CO2; 0.249, 0.626, pH_cumulo+PL+AN+AN_cumulo+interval_Pdt.+OD+RS+Feed_Vol+RS_cumulo+Accum._Yield+AS_Vol.+emission_CO2+consum_O2+generate_CO2; 0.262, 0.626, pH_cumulo+PL+AN+AN_cumulo+interval_Pdt.+OD+RS+Feed_Vol+RS_cumulo+RQ_integral+Accum._Yield+AS_Vol.+consum_O2; 0.249, 0.626, tmp+pH_cumulo+PL+AN+interval_yield+OD+RS+Feed_Vol+RS_cumulo+RQ_integral+Accum._Yield+AS_Vol.+emission_O2+consum_O2; 0.274, 0.626, tmp_cumulo+pH_cumulo+PL+AN+OD+RS+RS_cumulo+Accum._Yield+AS_Vol.+emission_CO2+consum_O2+generate_CO2; 0.249, 0.626, tmp+pH_cumulo+PL+AN+interval_yield+OD+RS+Feed_Vol+RS_cumulo+rab_integral+RQ_integral+Accum._Yield+AS_Vol.+consum_O2; 0.249, 0.626, tmp+pH_cumulo+PL+AN+interval_yield+OD+RS+RS_cumulo+Cell_conc._interval+Accum._Yield+AS_Vol.+emission_CO2+consum_O2+generate_CO2; 0.262, 0.626, pH+pH_cumulo+PL+AN+interval_yield+OD+RS+RS_cumulo+Cell_conc._interval+AS_Vol.+emission_CO2+consum_O2+generate_CO2; 0.273, 0.626, tmp_cumulo+pH_cumulo+PL+AN+AN_cumulo+OD+RS+RS_cumulo+Accum._Yield+AS_Vol.+consum_O2+generate_CO2; 0.273, 0.625, pH_cumulo+PL+AN_cumulo+interval_yield+OD+RS+Feed_Vol+Accum._Yield+AS_Vol.+emission_CO2+consum_O2+generate_CO2; 0.273, 0.625, pH_cumulo+PL+AN+interval_yield+OD+RS+Feed_Vol+RS_cumulo+Cell_conc._interval+Accum._Yield+AS_Vol.+consum_O2; 0.261, 0.625, pH_cumulo+PL+AN+AN_cumulo+interval_Pdt.+OD+RS+RS_cumulo+Accum._Yield+AS_Vol.+emission_CO2+consum_O2+generate_CO2; 0.273, 0.625, pH_cumulo+PL+AN+interval_yield+OD+RS+RS_cumulo+rab_integral+RQ_integral+AS_Vol.+emission_O2+consum_O2; 0.273, 0.625, pH_cumulo+PL+AN+AN_cumulo+OD+RS+RS_cumulo+Accum._Yield+AS_Vol.+emission_O2+consum_O2+generate_CO2; 0.249, 0.625, pH_cumulo+PL+AN+interval_yield+interval_Pdt.+OD+RS+Feed_Vol+RS_cumulo+rab_integral+RQ_integral+Accum._Yield+AS_Vol.+consum_O2; 0.273, 0.625, pH_cumulo+PL+AN_cumulo+interval_yield+OD+RS+RS_cumulo+RQ_integral+Accum._Yield+AS_Vol.+emission_O2+consum_O2; 0.285, 0.625, pH_cumulo+PL+AN+interval_yield+OD+RS+RS_cumulo+Cell_conc._interval+RQ_integral+AS_Vol.+consum_O2; 0.285, 0.625, pH_cumulo+PL+AN_cumulo+OD+RS+RS_cumulo+Accum._Yield+AS_Vol.+consum_O2+interval_O2+generate_CO2; 0.261, 0.625, tmp_cumulo+pH_cumulo+PL+AN_cumulo+interval_yield+OD+RS+Feed_Vol+RS_cumulo+AS_Vol.+emission_CO2+consum_O2+generate_CO2; 0.285, 0.625, pH_cumulo+AN+interval_yield+OD+RS+Feed_Vol+RS_cumulo+RQ_integral+Accum._Yield+AS_Vol.+consum_O2; 0.236, 0.625, pH_cumulo+PL+AN+interval_yield+interval_Pdt.+OD+RS+Feed_Vol+RS_cumulo+rab_integral+Accum._Yield+AS_Vol.+consum_O2+interval_O2+generate_CO2; 0.296, 0.625, pH_cumulo+PL+interval_yield+OD+RS+RS_cumulo+RQ_integral+AS_Vol.+emission_O2+consum_O2; 0.284, 0.625, pH_cumulo+PL+interval_yield+OD+RS+RS_cumulo+RQ_integral+Accum._Yield+AS_Vol.+emission_O2+consum_O2; 0.236, 0.625, pH_cumulo+PL+AN+interval_yield+OD+RS+Feed_Vol+RS_cumulo+rab_integral+Accum._Yield+AS_Vol.+emission_CO2+consum_O2+interval_O2+generate_CO2; 0.236, 0.625, pH_cumulo+PL+PL_cumulo+AN+interval_yield+OD+RS+Feed_Vol+RS_cumulo+Accum._Yield+AS_Vol.+emission_CO2+consum_O2+interval_O02+generate_CO2; 0.261, 0.625, pH_cumulo+PL+interval_yield+OD+RS+RS_cumulo+rab_integral+Accum._Yield+AS_Vol.+emission_CO2+consum_O2+interval_O2+generate_CO2; 0.261, 0.625, pH_cumulo+PL+AN+OD+RS+RS_cumulo+Cell_conc._interval+Accum._Yield+AS_Vol.+emission_CO2+consum_O2+interval_O2+generate_CO2; 0.261, 0.625, tmp+pH_cumulo+PL+AN+interval_yield+OD+RS+RS_cumulo+Cell_conc._interval+AS_Vol.+emission_CO2+consum_O2+generate_CO2; 0.273, 0.625, tmp_cumulo+pH_cumulo+PL+AN_cumulo+interval_yield+OD+RS+RS_cumulo+Accum._Yield+AS_Vol.+consum_O2+generate_CO2; 0.284, 0.625, pH_cumulo+PL+AN+interval_yield+OD+RS+RS_cumulo+AS_Vol.+consum_O2+interval_O2+generate_CO2; 0.261, 0.625, tmp+pH_cumulo+PL+AN+interval_yield+OD+RS+Feed_Vol+RS_cumulo+rab_integral+Accum._Yield+AS_Vol.+consum_O2; 0.249, 0.625, pH_cumulo+PL+AN+interval_yield+OD+RS+Feed_Vol+RS_cumulo+rab_integral+AS_Vol.+emission_CO2+consum_O2+interval_O2+generate_CO2; 0.284, 0.625, pH_cumulo+PL+AN+interval_Pdt.+OD+RS+RS_cumulo+Accum._Yield+AS_Vol.+consum_O2+generate_CO2; 0.248, 0.625, tmp_cumulo+pH_cumulo+PL+AN+interval_yield+OD+RS+Feed_Vol+RS_cumulo+rab_integral+AS_Vol.+emission_CO2+consum_O2+generate_CO2; 0.284, 0.625, pH_cumulo+PL+interval_yield+OD+RS+RS_cumulo+rab_integral+Accum._Yield+emission_CO2+consum_O2+generate_CO2; 0.295, 0.625, pH_cumulo+PL+interval_yield+OD+RS+RS_cumulo+RQ_integral+emission_O2+emission_CO2+consum_O2; 0.273, 0.625, tmp+pH_cumulo+PL+AN+OD+RS+RS_cumulo+Accum._Yield+AS_Vol.+consum_O2+interval_O2+generate_CO2; 0.273, 0.625, pH_cumulo+PL+AN+interval_yield+OD+RS+RS_cumulo+Cell_conc._interval+rab_integral+AS_Vol.+consum_O2+generate_CO2; 0.236, 0.625, tmp+pH_cumulo+PL+AN+interval_yield+OD+RS+Feed_Vol+RS_cumulo+Cell_conc._interval+rab_integral+Accum._Yield+AS_Vol.+consum_O2+generate_CO2; 0.261, 0.625, tmp+pH_cumulo+PL+AN+interval_yield+OD+RS+RS_cumulo+Accum._Yield+AS_Vol.+emission_O2+consum_O2+generate_CO2; 0.272, 0.625, pH+pH_cumulo+PL+interval_yield+OD+RS+RS_cumulo+AS_Vol.+emission_CO2+consum_O2+interval_O2+generate_CO2; 0.272, 0.625, pH_cumulo+PL+AN+interval_yield+interval_Pdt.+OD+RS+Feed_Vol+RS_cumulo+AS_Vol.+consum_O2+generate_CO2; 0.235, 0.625, tmp+pH_cumulo+PL+AN+interval_yield+interval_Pdt.+OD+RS+Feed_Vol+RS_cumulo+Accum._Yield+AS_Vol.+emission_CO2+consum_O2+generate_CO2; 0.235, 0.625, pH_cumulo+PL+AN+interval_yield+OD+RS+Feed_Vol+RS_cumulo+Cell_conc._interval+rab_integral+Accum._Yield+AS_Vol.+emission_O2+consum_O2+generate_CO2; 0.248, 0.625, pH_cumulo+PL+AN+AN_cumulo+OD+RS+Feed_Vol+RS_cumulo+rab_integral+Accum._Yield+AS_Vol.+consum_O2+interval_O2+generate_CO2; 0.272, 0.625, pH_cumulo+PL+PL_cumulo+AN+OD+RS+RS_cumulo+Accum._Yield+AS_Vol.+consum_O2+interval_O2+generate_CO2; 0.260, 0.625, tmp_cumulo+pH_cumulo+PL+AN+interval_yield+OD+RS+RS_cumulo+rab_integral+AS_Vol.+emission_CO2+consum_O2+generate_CO2; 0.235, 0.625, pH+pH_cumulo+PL+AN+interval_yield+OD+RS+Feed_Vol+RS_cumulo+Accum._Yield+AS_Vol.+emission_CO2+emission_CO2+consum_O2+generate_CO2; 0.260, 0.625, tmp_cumulo+pH_cumulo+PL+AN+OD+RS+Feed_Vol+RS_cumulo+Accum._Yield+AS_Vol.+consum_O2+interval_O2+generate_CO2; 0.272, 0.625, pH_cumulo+PL+AN+interval_Pdt.+OD+RS+Feed_Vol+RS_cumulo+Accum._Yield+AS_Vol.+consum_O2+generate_CO2; 0.248, 0.625, pH_cumulo+PL+AN+AN_cumulo+interval_yield+OD+RS+Feed_Vol+RS_cumulo+RQ_integral+AS_Vol.+emission_O2+emission_CO2+consum_O2; 0.235, 0.625, tmp+pH_cumulo+PL+AN+interval_yield+interval_Pdt.+OD+RS+Feed_Vol+RS_cumulo+rab_integral+Accum._Yield+AS_Vol.+consum_O2+generate_CO2; 0.272, 0.625, tmp_cumulo+pH_cumulo+PL+AN+interval_yield+OD+RS+Feed_Vol+RS_cumulo+Accum._Yield+AS_Vol.+consum_O2; 0.284, 0.625, pH_cumulo+PL+interval_yield+OD+RS+Feed_Vol+RS_cumulo+Accum._Yield+emission_CO2+consum_O2+generate_CO2; 0.222, 0.625, tmp+pH+pH_cumulo+PL+AN+AN_cumulo+interval_yield+OD+RS+Feed_Vol+RS_cumulo+Accum._Yield+AS_Vol.+emission_CO2+consum_O2+generate_CO2; 0.248, 0.624, pH+pH_cumulo+PL+AN+interval_yield+OD+RS+RS_cumulo+Cell_conc._interval+rab_integral+Accum._Yield+AS_Vol.+consum_O2+generate_CO2; 0.248, 0.624, pH+pH_cumulo+PL+AN+AN_cumulo+OD+RS+Feed_Vol+RS_cumulo+Accum._Yield+AS_Vol.+consum_O2+interval_O2+generate_CO2; 0.272, 0.624, pH_cumulo+PL+AN+interval_yield+OD+RS+Feed_Vol+Accum._Yield+AS_Vol.+consum_O2+interval_O2+generate_CO2; 0.272, 0.624, pH_cumulo+PL+AN_cumulo+OD+RS+RS_cumulo+Cell_conc._interval+Accum._Yield+AS_Vol.+emission_CO2+consum_O2+generate_CO2; 0.235, 0.624, pH+pH_cumulo+PL+AN+interval_yield+OD+RS+Feed_Vol+RS_cumulo+RQ_integral+Accum._Yield+AS_Vol.+emission_O2+emission_CO2+consum_O2; 0.283, 0.624, pH_cumulo+PL+interval_yield+OD+RS+RS_cumulo+AS_Vol.+emission_O2+emission_CO2+consum_O2+generate_CO2; 0.248, 0.624, tmp_cumulo+pH_cumulo+PL+AN+interval_yield+OD+RS+RS_cumulo+rab_integral+Accum._Yield+AS_Vol.+emission_CO2+consum_O2+generate_CO2; 0.260, 0.624, tmp+pH_cumulo+PL+interval_yield+OD+RS+Feed_Vol+RS_cumulo+Accum._Yield+AS_Vol.+emission_CO2+consum_O2+generate_CO2; 0.235, 0.624, pH+pH_cumulo+PL+AN+AN_cumulo+interval_yield+OD+RS+Feed_Vol+RS_cumulo+Accum._Yield+AS_Vol.+consum_O2+interval_O2+generate_CO2; 0.283, 0.624, pH+pH_cumulo+PL+AN_cumulo+interval_yield+OD+RS+RS_cumulo+emission_CO2+consum_O2+generate_CO2; 0.260, 0.624, pH_cumulo+PL+AN+interval_yield+OD+RS+Feed_Vol+RS_cumulo+Cell_conc._interval+rab_integral+Accum._Yield+AS_Vol.+consum_O2; 0.283, 0.624, tmp+pH_cumulo+PL+AN_cumulo+interval_yield+OD+RS+RS_cumulo+emission_CO2+consum_O2+generate_CO2; 0.221, 0.624, pH+pH_cumulo+PL+AN+AN_cumulo+interval_yield+OD+RS+Feed_Vol+RS_cumulo+Accum._Yield+AS_Vol.+emission_CO2+consum_O2+interval_O2+generate_CO2; 0.235, 0.624, pH+pH_cumulo+PL+AN+AN_cumulo+OD+RS+Feed_Vol+RS_cumulo+Accum._Yield+AS_Vol.+emission_CO2+consum_O2+interval_O2+generate_CO2; 0.247, 0.624, tmp+tmp_cumulo+pH_cumulo+PL+AN+AN_cumulo+interval_yield+OD+RS+RS_cumulo+Accum._Yield+AS_Vol.+consum_O2+generate_CO2; 0.283, 0.624, pH_cumulo+PL+AN+interval_yield+OD+RS+RS_cumulo+emission_CO2+consum_O2+interval_O2+generate_CO2; 0.260, 0.624, tmp+pH_cumulo+PL+AN+OD+RS+Feed_Vol+RS_cumulo+Accum._Yield+AS_Vol.+consum_O2+interval_O2+generate_CO2; 0.294, 0.624, pH_cumulo+PL+OD+RS+RS_cumulo+Accum._Yield+AS_Vol.+emission_CO2+consum_O2+generate_CO2; 0.260, 0.624, pH_cumulo+PL+AN_cumulo+OD+RS+Feed_Vol+RS_cumulo+Accum._Yield+AS_Vol.+emission_CO2+consum_O2+interval_O2+generate_CO2; 0.316, 0.624, pH_cumulo+PL+interval_yield+OD+RS+RS_cumulo+AS_Vol.+consum_O2; 0.260, 0.624, pH_cumulo+PL+AN+interval_yield+interval_Pdt.+OD+RS+RS_cumulo+Cell_conc._interval+Accum._Yield+AS_Vol.+consum_O2+generate_CO2; 0.234, 0.624, pH+pH_cumulo+PL+PL_cumulo+AN+interval_yield+OD+RS+Feed_Vol+RS_cumulo+rab_integral+Accum._Yield+AS_Vol.+consum_O2+generate_CO2; 0.271, 0.624, pH+pH_cumulo+PL+AN+OD+RS+RS_cumulo+Cell_conc._interval+Accum._Yield+AS_Vol.+consum_O2+generate_CO2; 0.271, 0.624, tmp+pH_cumulo+PL+AN+interval_yield+OD+RS+RS_cumulo+RQ_integral+Accum._Yield+AS_Vol.+consum_O2; 0.283, 0.624, tmp+pH_cumulo+PL+AN+interval_yield+OD+RS+RS_cumulo+emission_CO2+consum_O2+generate_CO2; 0.260, 0.624, pH_cumulo+PL+AN+AN_cumulo+OD+RS+RS_cumulo+rab_integral+Accum._Yield+AS_Vol.+consum_O2+interval_O2+generate_CO2; 0.283, 0.624, pH_cumulo+PL+AN+interval_yield+OD+RS+Feed_Vol+RS_cumulo+rab_integral+AS_Vol.+consum_O2; 0.259, 0.624, pH_cumulo+PL+AN+interval_yield+OD+RS+RS_cumulo+Cell_conc._interval+AS_Vol.+emission_CO2+consum_O2+interval_O2+generate_CO2; 0.271, 0.624, pH_cumulo+PL+interval_yield+OD+RS+RS_cumulo+Cell_conc._interval+rab_integral+AS_Vol.+emission_CO2+consum_O2+generate_CO2; 0.283, 0.624, pH+PL+AN+interval_yield+OD+RS+RS_cumulo+Accum._Yield+AS_Vol.+consum_O2+generate_CO2; 0.259, 0.624, pH_cumulo+PL+PL_cumulo+AN+interval_yield+OD+RS+RS_cumulo+rab_integral+Accum._Yield+AS_Vol.+consum_O2+generate_CO2; 0.283, 0.624, pH_cumulo+PL+AN_cumulo+interval_yield+OD+RS+RS_cumulo+rab_integral+RQ_integral+AS_Vol.+consum_O2; 0.247, 0.624, tmp_cumulo+pH_cumulo+PL+AN+interval_yield+OD+RS+RS_cumulo+Cell_conc._interval+Accum._Yield+AS_Vol.+emission_CO2+consum_O2+generate_CO2; 0.221, 0.624, pH_cumulo+PL+AN+interval_yield+OD+RS+Feed_Vol+RS_cumulo+Cell_conc._interval+rab_integral+Accum._Yield+AS_Vol.+emission_CO2+consum_O2+generate_CO2; 0.259, 0.624, tmp_cumulo+pH_cumulo+PL+AN+interval_yield+OD+RS+RS_cumulo+Cell_conc._interval+AS_Vol.+emission_CO2+consum_O2+generate_CO2; 0.259, 0.624, tmp_cumulo+pH_cumulo+PL+AN+AN_cumulo+OD+RS+RS_cumulo+Accum._Yield+AS_Vol.+emission_CO2+consum_O2+generate_CO2; 0.294, 0.624, pH_cumulo+PL+interval_yield+OD+RS+Feed_Vol+RS_cumulo+RQ_integral+AS_Vol.+consum_O2; 0.283, 0.624, pH_cumulo+PL+AN+interval_yield+OD+RS+Feed_Vol+AS_Vol.+emission_CO2+consum_O2+generate_CO2; 0.247, 0.624, pH+pH_cumulo+PL+AN+interval_yield+OD+RS+Feed_Vol+RS_cumulo+RQ_integral+Accum._Yield+AS_Vol.+emission_CO2+consum_O2; 0.247, 0.624, pH+pH_cumulo+PL+AN_cumulo+interval_yield+OD+RS+RS_cumulo+rab_integral+Accum._Yield+AS_Vol.+emission_CO2+consum_O2+generate_CO2; 0.247, 0.624, tmp_cumulo+pH_cumulo+PL+AN+interval_yield+OD+RS+Feed_Vol+RS_cumulo+Accum._Yield+AS_Vol.+emission_O2+consum_O2+generate_CO2; 0.247, 0.624, pH+pH_cumulo+PL+AN+AN_cumulo+interval_yield+OD+RS+RS_cumulo+Cell_conc._interval+Accum._Yield+AS_Vol.+consum_O2+generate_CO2; 0.259, 0.624, pH_cumulo+PL+PL_cumulo+AN+OD+RS+Feed_Vol+RS_cumulo+Accum._Yield+AS_Vol.+emission_CO2+consum_O2+generate_CO2; 0.234, 0.624, pH+pH_cumulo+PL+AN+AN_cumulo+interval_yield+OD+RS+Feed_Vol+RS_ cumulo+Accum._Yield+AS_Vol.+emission_O2+consum_ O2+generate_CO2; 0.247, 0.624, tmp_cumulo+pH_ cumulo+PL+AN+interval_yield+OD+RS+Feed_Vol+RS_ cumulo+RQ_integral+Accum._Yield+AS_Vol.+emission_ O2+consum_O2; 0.283, 0.624, pH_cumulo+PL+interval_ yield+interval_Pdt.+OD+RS+RS_cumulo+AS_Vol.+ emission_CO2+consum_O2+generate_CO2; 0.247, 0.624, pH+pH_cumulo+PL+AN+OD+RS+Feed_Vol+RS_cumulo+rab_integral+Accum._Yield+AS_Vol.+emission_ CO2+consum_O2+generate_CO2; 0.271, 0.624, pH_cumulo+PL+AN_cumulo+interval_yield+OD+RS+Feed_ Vol+RS_cumulo+Accum._Yield+emission_CO2+consum_ O2+generate_CO2; 0.247, 0.624, pH_cumulo+PL+PL_ cumulo+AN+interval_yield+OD+RS+Feed_Vol+RS_ cumulo+rab_integral+RQ_integral+Accum._Yield+AS_ Vol.+consum_O2; 0.221, 0.624, pH+pH_cumulo+PL+AN+ interval_yield+OD+RS+Feed_Vol+RS_cumulo+rab_ integral+Accum._Yield+AS_Vol.+emission_CO2+ consum_O2+interval_O2+generate_CO2; 0.271, 0.624, pH_cumulo+PL+AN+interval_yield+OD+RS+Feed_Vol+ RS_cumulo+Accum._Yield+AS_Vol.+emission_O2+consum_O2; 0.259, 0.624, pH_cumulo+PL+AN+interval_ yield+interval_Pdt.+OD+RS+Feed_Vol+Accum._Yield+ AS_Vol.+emission_O2+consum_O2+generate_CO2; 0.282, 0.624, pH_cumulo+PL+PL_cumulo+interval_yield+OD+ RS+RS_cumulo+AS_Vol.+emission_CO2+consum_O2+ generate_CO2; 0.259, 0.624, pH_cumulo+PL+AN+interval_Pdt.+OD+RS+Feed_Vol+RS_cumulo+RQ_integral+ Accum._Yield+AS_Vol.+emission_CO2+consum_O2; 0.271, 0.624, tmp_cumulo+pH_cumulo+PL+AN+interval_ yield+OD+RS+RS_cumulo+RQ_integral+Accum._Yield+ AS_Vol.+consum_O2; 0.271, 0.624, pH_cumulo+PL+interval_yield+OD+RS+RS_cumulo+Cell_conc._interval+AS_ Vol.+emission_CO2+consum_O2+interval_O2+generate_ CO2; 0.234, 0.624, pH_cumulo+PL+AN+interval_yield+ OD+RS+Feed_Vol+RS_cumulo+RQ_integral+Accum._ Yield+AS_Vol.+emission_O2+emission_CO2+consum_ O2+interval_O2; 0.246, 0.624, pH_cumulo+PL+AN+ interval_Pdt.+OD+RS+Feed_Vol+RS_cumulo+RQ_ integral+Accum._Yield+AS_Vol.+emission_O2+emission_ CO2+consum_O2; 0.220, 0.624, tmp_cumulo+pH_ cumulo+PL+AN+AN_cumulo+interval_yield+OD+RS+ Feed_Vol+RS_cumulo+rab_integral+Accum._Yield+AS_ Vol.+emission_CO2+consum_O2+generate_CO2; 0.246, 0.624, pH_cumulo+PL+AN+interval_yield+OD+RS+RS_ cumulo+rab_integral+Accum._Yield+AS_Vol.+emission_ O2+consum_O2+interval_O2+generate_CO2; 0.246, 0.624, pH_cumulo+PL+AN+OD+RS+Feed_Vol+RS_cumulo+ Cell_conc._interval+Accum._Yield+AS_Vol.+emission_ CO2+consum_O2+interval_O2+generate_CO2; 0.259, 0.624, pH+pH_cumulo+PL+AN+interval_yield+OD+RS+ RS_cumulo+AS_Vol.+emission_CO2+consum_O2+interval_O2+generate_CO2; 0.234, 0.624, pH+pH_cumulo+PL+ AN+AN_cumulo+interval_yield+OD+RS+Feed_Vol+RS_ cumulo+rab_integral+RQ_integral+Accum._Yield+AS_ Vol.+consum_O2; 0.259, 0.624, pH_cumulo+PL+AN+ interval_yield+interval_Pdt.+OD+RS+RS_cumulo+RQ_ integral+Accum._Yield+AS_Vol.+emission_CO2+ consum_O2; 0.293, 0.624, pH_cumulo+PL+AN_cumulo+ interval_yield+OD+RS+RS_cumulo+AS_Vol.+consum_ O2+generate_CO2; 0.282, 0.624, pH_cumulo+PL+AN_ cumulo+OD+RS+Feed_Vol+RS_cumulo+Accum._Yield+ AS_Vol.+consum_O2+generate_CO2; 0.234, 0.624, pH+pH_cumulo+PL+AN+AN_cumulo+interval_yield+ OD+RS+Feed_Vol+RS_cumulo+RQ_integral+Accum._ Yield+AS_Vol.+emission_O2+consum_O2; 0.259, 0.624, pH_cumulo+PL+AN+interval_yield+interval_Pdt.+OD+ RS+RS_cumulo+Accum._Yield+AS_Vol.+emission_O2+ consum_O2+generate_CO2; 0.259, 0.624, pH+PL+AN+ AN_cumulo+interval_yield+OD+RS+RS_cumulo+Cell_ conc._interval+Accum._Yield+AS_Vol.+consum_O2+ generate_CO2; 0.293, 0.624, pH_cumulo+PL+interval_ yield+OD+RS+RS_cumulo+AS_Vol.+emission_O2+ consum_O2+generate_CO2; 0.246, 0.624, pH+pH_ cumulo+PL+AN+AN_cumulo+OD+RS+Feed_Vol+RS_ cumulo+rab_integral+Accum._Yield+AS_Vol.+consum_ O2+generate_CO2; 0.233, 0.624, tmp+pH+pH_cumulo+ PL+AN+interval_yield+OD+RS+Feed_Vol+RS_cumulo+ rab_integral+Accum._Yield+AS_Vol.+consum_O2+ generate_CO2; 0.259, 0.624, tmp+tmp_cumulo+pH_ cumulo+PL+AN_cumulo+interval_yield+OD+RS+RS_ cumulo+AS_Vol.+emission_CO2+consum_O2+generate_ CO2; 0.233, 0.624, pH_cumulo+PL+AN+interval_yield+ interval_Pdt.+OD+RS+Feed_Vol+RS_cumulo+rab_ integral+Accum._Yield+AS_Vol.+emission_O2+consum_ O2+generate_CO2; 0.259, 0.624, pH+pH_cumulo+PL+ AN_cumulo+interval_yield+OD+RS+RS_cumulo+rab_ integral+AS_Vol.+emission_CO2+consum_O2+generate_ CO2; 0.246, 0.624, pH_cumulo+PL+AN+AN_cumulo+ interval_yield+OD+RS+Feed_Vol+RS_cumulo+AS_Vol.+ emission_CO2+consum_O2+interval_O2+generate_CO2; 0.259, 0.624, pH_cumulo+PL+AN+AN_cumulo+interval_ yield+interval_Pdt.+OD+RS+RS_cumulo+Accum._Yield+ AS_Vol.+consum_O2+generate_CO2; 0.220, 0.624, pH+pH_cumulo+PL+PL_cumulo+AN+interval_yield+ OD+RS+Feed_Vol+RS_cumulo+rab_integral+Accum._ Yield+AS_Vol.+emission_CO2+consum_O2+generate_ CO2; 0.258, 0.624, pH_cumulo+PL+PL_cumulo+AN+OD+ RS+Feed_Vol+RS_cumulo+Accum._Yield+AS_Vol.+ consum_O2+interval_O2+generate_CO2; 0.270, 0.623, pH_cumulo+PL+AN+interval_yield+OD+RS+Feed_Vol+ RS_cumulo+Cell_conc._interval+AS_Vol.+consum_O2+ generate_CO2; 0.282, 0.623, pH_cumulo+PL+interval_ yield+OD+RS+RS_cumulo+rab_integral+RQ_integral+ emission_O2+emission_CO2+consum_O2; 0.246, 0.623, pH_cumulo+PL+AN+interval_yield+OD+RS+Feed_Vol+ RS_cumulo+Cell_conc._interval+RQ_integral+Accum._ Yield+AS_Vol.+emission_CO2+consum_O2; 0.282, 0.623, pH_cumulo+PL+PL_cumulo+AN+interval_yield+OD+ RS+RS_cumulo+RQ_integral+AS_Vol.+consum_O2; 0.258, 0.623, pH+pH_cumulo+PL+AN+interval_yield+ OD+RS+RS_cumulo+rab_integral+RQ_integral+Accum._ Yield+AS_Vol.+consum_O2; 0.282, 0.623, pH_cumulo+ PL+interval_yield+OD+RS+RS_cumulo+rab_integral+ Accum._Yield+AS_Vol.+consum_O2+generate_CO2; 0.282, 0.623, tmp+pH_cumulo+PL+AN+interval_yield+ OD+RS+RS_cumulo+RQ_integral+AS_Vol.+consum_O2; 0.282, 0.623, pH_cumulo+PL+interval_yield+OD+RS+ Feed_Vol+RS_cumulo+rab_integral+emission_CO2+consum_O2+generate_CO2; 0.282, 0.623, pH_cumulo+PL+ AN+interval_yield+OD+RS+Feed_Vol+RQ_integral+ Accum._Yield+AS_Vol.+consum_O2; 0.270, 0.623, pH_cumulo+PL+AN+AN_cumulo+interval_yield+OD+ RS+RS_cumulo+RQ_integral+AS_Vol.+emission_O2+ consum_O2; 0.258, 0.623, pH_cumulo+PL+AN_cumulo+ interval_Pdt.+OD+RS+RS_cumulo+RQ_integral+Accum._ Yield+AS_Vol.+emission_O2+emission_CO2+consum_ O2; 0.246, 0.623, pH+pH_cumulo+PL+PL_cumulo+AN+ interval_yield+OD+RS+Feed_Vol+RS_cumulo+RQ_ integral+Accum._Yield+AS_Vol.+consum_O2; 0.246, 0.623, pH_cumulo+PL+AN+AN_cumulo+interval_yield+ OD+RS+RS_cumulo+Cell_conc._interval+Accum._Yield+ AS_Vol.+consum_O2+interval_O2+generate_CO2; 0.233, 0.623, tmp+pH_cumulo+PL+AN+AN_cumulo+interval_ yield+OD+RS+Feed_Vol+RS_cumulo+Cell_conc._interval+Accum._Yield+AS_Vol.+consum_O2+generate_CO2; 0.258, 0.623, pH_cumulo+PL+AN_cumulo+interval_yield+OD+RS+Feed_Vol+RS_cumulo+AS_Vol.+emission_CO2+consum_O2+interval_O2+generate_CO2; 0.233, 0.623, pH_cumulo+PL+AN+interval_yield+OD+RS+Feed_Vol+RS_cumulo+Cell_conc._interval+RQ_integral+Accum._Yield+AS_Vol.+emission_O2+emission_CO2+consum_O2; 0.220, 0.623, tmp+tmp_cumulo+pH_cumulo+PL+AN+interval_yield+OD+RS+Feed_Vol+RS_cumulo+rab_integral+Accum._Yield+AS_Vol.+emission_CO2+consum_O2+generate_CO2; 0.233, 0.623, tmp+pH_cumulo+PL+PL_cumulo+AN+interval_yield+OD+RS+Feed_Vol+RS_cumulo+Accum._Yield+AS_Vol.+emission_CO2+consum_O2+generate_CO2; 0.270, 0.623, tmp+pH_cumulo+PL+interval_yield+OD+RS+RS_cumulo+rab_integral+AS_Vol.+emission_CO2+consum_O2+generate_CO2; 0.246, 0.623, tmp_cumulo+pH_cumulo+PL+AN+interval_yield+OD+RS+Feed_Vol+RS_cumulo+rab_integral+RQ_integral+Accum._Yield+AS_Vol.+consum_O2; 0.282, 0.623, pH_cumulo+PL+interval_yield+OD+RS+Feed_Vol+RS_cumulo+emission_CO2+consum_O2+interval_O2+generate_CO2; 0.258, 0.623, pH+PL+AN+interval_yield+OD+RS+Feed_Vol+RS_cumulo+rab_integral+Accum._Yield+AS_Vol.+consum_O2+generate_CO2; 0.270, 0.623, pH_cumulo+PL+AN_cumulo+interval_yield+OD+RS+RS_cumulo+RQ_integral+AS_Vol.+emission_O2+emission_CO2+consum_O2; 0.293, 0.623, pH+pH_cumulo+PL+interval_yield+OD+RS+RS_cumulo+RQ_integral+AS_Vol.+consum_O2; 0.270, 0.623, tmp+pH_cumulo+PL+AN+AN_cumulo+OD+RS+RS_cumulo+Accum._Yield+AS_Vol.+consum_O2+generate_CO2; 0.233, 0.623, pH+pH_cumulo+PL+AN+interval_yield+OD+RS+Feed_Vol+RS_cumulo+rab_integral+RQ_integral+Accum._Yield+AS_Vol.+emission_O2+consum_O2; 0.246, 0.623, pH_cumulo+PL+AN+AN_cumulo+interval_yield+OD+RS+RS_cumulo+rab_integral+RQ_integral+Accum._Yield+AS_Vol.+emission_O2+consum_O2; 0.282, 0.623, pH+pH_cumulo+PL+AN+interval_yield+OD+RS+RS_cumulo+emission_CO2+consum_O2+generate_CO2; 0.270, 0.623, tmp+pH_cumulo+PL+AN+interval_yield+OD+RS+RS_cumulo+Accum._Yield+AS_Vol.+consum_O2+generate_CO2; 0.258, 0.623, pH_cumulo+PL+AN+AN_cumulo+interval_yield+OD+RS+Feed_Vol+rab_integral+Accum._Yield+AS_Vol.+consum_O2+generate_CO2; 0.282, 0.623, pH_cumulo+PL+AN_cumulo+OD+RS+RS_cumulo+Cell_conc._interval+Accum._Yield+AS_Vol.+consum_O2+generate_CO2; 0.220, 0.623, tmp_cumulo+pH+pH_cumulo+PL+AN+AN_cumulo+interval_yield+OD+RS+Feed_Vol+RS_cumulo+Accum._Yield+AS_Vol.+emission_CO2+consum_O2+generate_CO2; 0.258, 0.623, tmp_cumulo+pH_cumulo+PL+AN+interval_yield+OD+RS+RS_cumulo+Accum._Yield+AS_Vol.+emission_O2+consum_O2+generate_CO2; 0.246, 0.623, pH_cumulo+PL+PL_cumulo+AN+interval_yield+OD+RS+Feed_Vol+RS_cumulo+Cell_conc._interval+Accum._Yield+AS_Vol.+consum_O2+generate_CO2; 0.246, 0.623, pH+PL+AN+AN_cumulo+interval_yield+interval_Pdt.+OD+RS+Feed_Vol+RS_cumulo+Accum._Yield+AS_Vol.+consum_O2+generate_CO2; 0.258, 0.623, pH_cumulo+PL+AN+interval_yield+OD+RS+Feed_Vol+RS_cumulo+rab_integral+Accum._Yield+AS_Vol.+emission_O2+consum_O2; 0.246, 0.623, pH+pH_cumulo+PL+AN+interval_yield+OD+RS+Feed_Vol+RS_cumulo+Cell_conc._interval+AS_Vol.+emission_CO2+consum_O2+generate_CO2; 0.233, 0.623, pH_cumulo+PL+AN+interval_yield+interval_Pdt.+OD+RS+Feed_Vol+RS_cumulo+Cell_conc._interval+rab_integral+Accum._Yield+AS_Vol.+consum_O2+generate_CO2; 0.246, 0.623, pH+pH_cumulo+PL+PL_cumulo+AN+OD+RS+Feed_Vol+RS_cumulo+Accum._Yield+AS_Vol.+emission_CO2+consum_O2+generate_CO2; 0.258, 0.623, pH_cumulo+PL+AN+AN_cumulo+OD+RS+RS_cumulo+Cell_conc._interval+Accum._Yield+AS_Vol.+consum_O2+interval_O2+generate_CO2; 0.270, 0.623, pH+pH_cumulo+PL+interval_yield+OD+RS+RS_cumulo+Cell_conc._interval+AS_Vol.+emission_CO2+consum_O2+generate_CO2; 0.270, 0.623, pH_cumulo+PL+AN_cumulo+interval_Pdt.+OD+RS+RS_cumulo+RQ_integral+Accum._Yield+AS_Vol.+emission_CO2+consum_O2; 0.245, 0.623, pH_cumulo+PL+AN+AN_cumulo+interval_yield+OD+RS+RS_cumulo+rab_integral+Accum._Yield+AS_Vol.+emission_O2+consum_O2+generate_CO2; 0.258, 0.623, tmp+pH_cumulo+PL+AN+interval_yield+OD+RS+RS_cumulo+AS_Vol.+emission_CO2+consum_O2+interval_O2+generate_CO2; 0.258, 0.623, pH_cumulo+PL+AN+AN_cumulo+interval_Pdt.+OD+RS+RS_cumulo+RQ_integral+Accum._Yield+AS_Vol.+emission_CO2+consum_O2; 0.219, 0.623, pH_cumulo+PL+AN+AN_cumulo+interval_yield+OD+RS+Feed_Vol+RS_cumulo+rab_integral+RQ_integral+Accum._Yield+AS_Vol.+emission_O2+emission_CO2+consum_O2; 0.245, 0.623, pH+pH_cumulo+PL+AN+AN_cumulo+OD+RS+Feed_Vol+RS_cumulo+Cell_conc._interval+Accum._Yield+AS_Vol.+consum_O2+generate_CO2; 0.245, 0.623, pH+pH_cumulo+PL+AN+AN_cumulo+interval_yield+OD+RS+Feed_Vol+RS_cumulo+rab_integral+Accum._Yield+AS_Vol.+consum_O2; 0.281, 0.623, pH+pH_cumulo+PL+interval_yield+OD+RS+RS_cumulo+RQ_integral+Accum._Yield+AS_Vol.+consum_O2; 0.245, 0.623, tmp+pH+pH_cumulo+PL+AN+interval_yield+OD+RS+RS_cumulo+Accum._Yield+AS_Vol.+emission_CO2+consum_O2+generate_CO2; 0.258, 0.623, pH_cumulo+PL+AN+OD+RS+Feed_Vol+RS_cumulo+rab_integral+Accum._Yield+AS_Vol.+emission_O2+consum_O2+generate_CO2; 0.232, 0.623, tmp+tmp_cumulo+pH_cumulo+PL+AN+AN_cumulo+interval_yield+OD+RS+RS_cumulo+Accum._Yield+AS_Vol.+emission_CO2+consum_O2+generate_CO2; 0.245, 0.623, tmp+pH+pH_cumulo+PL+AN+interval_yield+OD+RS+Feed_Vol+RS_cumulo+AS_Vol.+emission_CO2+consum_O2+generate_CO2; 0.281, 0.623, pH_cumulo+PL+interval_yield+OD+RS+RS_cumulo+Accum._Yield+AS_Vol.+emission_O2+consum_O2+generate_CO2; 0.292, 0.623, pH_cumulo+PL+AN+interval_yield+OD+RS+Feed_Vol+Accum._Yield+AS_Vol.+consum_O2; 0.257, 0.623, tmp+pH+pH_cumulo+PL+AN+interval_yield+OD+RS+RS_cumulo+AS_Vol.+emission_CO2+consum_O2+generate_CO2; 0.245, 0.623, pH_cumulo+PL+PL_cumulo+AN+interval_yield+OD+RS+RS_cumulo+Accum._Yield+AS_Vol.+emission_CO2+consum_O2+interval_O2+generate_CO2; 0.281, 0.623, pH_cumulo+PL+AN_cumulo+interval_Pdt.+OD+RS+RS_cumulo+RQ_integral+Accum._Yield+AS_Vol.+consum_O2; 0.245, 0.623, tmp_cumulo+pH+pH_cumulo+PL+AN+interval_yield+OD+RS+RS_cumulo+Accum._Yield+AS_Vol.+emission_CO2+consum_O2+generate_CO2; 0.269, 0.623, pH+pH_cumulo+PL+AN_cumulo+interval_yield+OD+RS+RS_cumulo+Accum._Yield+AS_Vol.+consum_O2+generate_CO2; 0.257, 0.623, pH+pH_cumulo+PL+AN_cumulo+OD+RS+Feed_Vol+RS_cumulo+Accum._Yield+AS_Vol.+emission_CO2+consum_O2+generate_CO2; 0.269, 0.623, pH_cumulo+PL+AN+AN_cumulo+interval_yield+OD+RS+RS_cumulo+Accum._Yield+emission_CO2+consum_O2+generate_CO2; 0.232, 0.623, tmp_cumulo+pH_cumulo+PL+AN+ interval_yield+OD+RS+Feed_Vol+RS_cumulo+Cell_ conc._interval+rab_integral+Accum._Yield+AS_Vol.+ consum_O2+generate_CO2; 0.232, 0.623, tmp_cumulo+ pH+pH_cumulo+PL+AN+interval_yield+OD+RS+Feed_ Vol+RS_cumulo+rab_integral+Accum._Yield+AS_Vol.+ consum_O2+generate_CO2; 0.257, 0.623, tmp_cumulo+ pH_cumulo+PL+AN+interval_yield+OD+RS+RS_ cumulo+AS_Vol.+emission_CO2+consum_O2+interval_ O2+generate_CO2; 0.219, 0.623, pH+pH_cumulo+PL+PL_ cumulo+AN+AN_cumulo+interval_yield+OD+RS+Feed_ Vol+RS_cumulo+Accum._Yield+AS_Vol.+emission_CO2+ consum_O2+generate_CO2; 0.257, 0.623, pH_cumulo+ PL+AN+AN_cumulo+interval_yield+OD+RS+Feed_Vol+ RS_cumulo+RQ_integral+AS_Vol.+emission_CO2+ consum_O2; 0.281, 0.623, pH_cumulo+PL+interval_yield+ OD+RS+RS_cumulo+rab_integral+emission_CO2+ consum_O2+interval_O2+generate_CO2; 0.257, 0.623, pH_cumulo+PL+AN+interval_yield+OD+RS+Feed_Vol+ rab_integral+Accum._Yield+AS_Vol.+emission_CO2+consum_O2+generate_CO2; 0.232, 0.623, pH_cumulo+PL+ AN+interval_yield+interval_Pdt.+OD+RS+Feed_Vol+RS_ cumulo+Cell_conc._interval+Accum._Yield+AS_Vol.+ emission_CO2+consum_O2+generate_CO2; 0.281, 0.623, pH_cumulo+PL+AN+AN_cumulo+interval_yield+OD+ RS+Feed_Vol+RS_cumulo+AS_Vol.+consum_O2; 0.245, 0.623, tmp_cumulo+pH+pH_cumulo+PL+AN+interval_ yield+OD+RS+Feed_Vol+RS_cumulo+AS_Vol.+emission_ CO2+consum_O2+generate_CO2; 0.281, 0.623, tmp_cumulo+pH_cumulo+PL+AN_cumulo+interval_yield+OD+ RS+RS_cumulo+emission_CO2+consum_O2+generate_ CO2; 0.232, 0.623, pH_cumulo+PL+AN+AN_cumulo+ interval_yield+OD+RS+Feed_Vol+RS_cumulo+Accum._ Yield+AS_Vol.+emission_O2+consum_O2+interval_O2+ generate_CO2; 0.303, 0.623, pH_cumulo+PL+interval_ yield+OD+RS+RS_cumulo+Accum._Yield+AS_Vol.+ consum_O2; 0.257, 0.623, tmp+pH_cumulo+PL+AN+AN_ cumulo+OD+RS+RS_cumulo+Accum._Yield+AS_Vol.+ emission_CO2+consum_O2+generate_CO2; 0.257, 0.623, pH_cumulo+PL+AN_cumulo+interval_yield+OD+RS+ Feed_Vol+RS_cumulo+rab_integral+Accum._Yield+AS_ Vol.+consum_O2+generate_CO2; 0.245, 0.623, pH_cumulo+PL+PL_cumulo+AN+interval_yield+interval_Pdt.+ OD+RS+Feed_Vol+RS_cumulo+Accum._Yield+AS_Vol.+ consum_O2+generate_CO2; 0.257, 0.623, pH_cumulo+ PL+AN+interval_yield+interval_Pdt.+OD+RS+RS_ cumulo+RQ_integral+Accum._Yield+AS_Vol.+emission_ O2+consum_O2; 0.232, 0.623, pH_cumulo+PL+AN+AN_ cumulo+interval_yield+OD+RS+Feed_Vol+RS_cumulo+ Cell_conc._interval+Accum._Yield+AS_Vol.+consum_ O2+interval_O2+generate_CO2; 0.257, 0.622, tmp_ cumulo+pH_cumulo+PL+AN+OD+RS+RS_cumulo+ Accum._Yield+AS_Vol.+emission_CO2+consum_O2+ interval_O2+generate_CO2; 0.257, 0.622, pH+pH_ cumulo+PL+AN+interval_yield+interval_Pdt.+OD+RS+ Feed_Vol+Accum._Yield+AS_Vol.+consum_O2+generate_ CO2; 0.257, 0.622, pH_cumulo+PL+interval_yield+OD+ RS+Feed_Vol+RS_cumulo+rab_integral+RQ_integral+ AS_Vol.+emission_O2+emission_CO2+consum_O2; 0.244, 0.622, pH+pH_cumulo+PL+AN+AN_cumulo+interval_yield+OD+RS+RS_cumulo+rab_integral+Accum._ Yield+AS_Vol.+emission_O2+consum_O2+generate_CO2; 0.280, 0.622, pH_cumulo+PL+AN+interval_yield+interval_Pdt.+OD+ RS+RS_cumulo+RQ_integral+AS_Vol.+consum_O2; 0.232, 0.622, tmp+pH_cumulo+PL+AN+interval_yield+ OD+RS+Feed_Vol+RS_cumulo+rab_integral+Accum._ Yield+AS_Vol.+consum_O2+interval_O2+generate_CO2; 0.244, 0.622, pH+PL+AN+interval_yield+

OD+RS+Feed_Vol+RS_cumulo+Cell_conc._interval+AS_ Vol.+emission_CO2+consum_O2+generate_CO2; 0.269, 0.622, pH_cumulo+PL+AN+interval_Pdt.+OD+RS+RS_ cumulo+rab_integral+RQ_integral+Accum._Yield+AS_ Vol.+consum_O2; 0.244, 0.622, pH+pH_cumulo+PL+AN+ OD+RS+Feed_Vol+RS_cumulo+rab_integral+Accum._ Yield+AS_Vol.+consum_O2+interval_O2+generate_CO2; 0.244, 0.622, pH+pH_cumulo+PL+AN+interval_yield+ OD+RS+RS_cumulo+rab_integral+Accum._Yield+AS_ Vol.+consum_O2+interval_O2+generate_CO2; 0.244, 0.622, pH+PL+AN+AN_cumulo+interval_yield+OD+RS+ Feed_Vol+RS_cumulo+Accum._Yield+AS_Vol.+emission_ CO2+consum_O2+generate_CO2; 0.244, 0.622, pH_cumulo+PL+AN_cumulo+interval_yield+OD+RS+RS_ cumulo+rab_integral+Accum._Yield+AS_Vol.+emission_ CO2+consum_O2+interval_O2+generate_CO2; 0.269, 0.622, tmp+pH_cumulo+PL+AN+interval_yield+OD+RS+ Feed_Vol+Accum._Yield+AS_Vol.+consum_O2+generate_ CO2; 0.280, 0.622, tmp_cumulo+pH_cumulo+PL+AN+interval_yield+OD+RS+RS_cumulo+emission_CO2+ consum_O2+generate_CO2; 0.291, 0.622, pH_cumulo+ AN+interval_yield+OD+RS+RS_cumulo+RQ_integral+ Accum._Yield+AS_Vol.+consum_O2; 0.269, 0.622, tmp+ pH_cumulo+PL+interval_yield+OD+RS+RS_cumulo+AS_ Vol.+emission_CO2+consum_O2+interval_O2+generate_ CO2; 0.231, 0.622, pH_cumulo+PL+AN+interval_yield+ interval_Pdt.+OD+RS+Feed_Vol+RS_cumulo+Accum._ Yield+AS_Vol.+emission_CO2+consum_O2+interval_O2+ generate_CO2; 0.244, 0.622, pH+pH_cumulo+PL+AN+ interval_yield+interval_Pdt.+OD+RS+Feed_Vol+RS_ cumulo+RQ_integral+Accum._Yield+AS_Vol.+consum_ O2; 0.280, 0.622, pH_cumulo+PL+interval_Pdt.+OD+RS+ RS_cumulo+RQ_integral+Accum._Yield+AS_Vol.+ emission_CO2+consum_O2; 0.268, 0.622, pH_cumulo+ PL+AN+AN_cumulo+interval_yield+OD+RS+Feed_Vol+ RS_cumulo+AS_Vol.+consum_O2+generate_CO2; 0.244, 0.622, pH_cumulo+PL+AN+AN_cumulo+interval_yield+ OD+RS+RS_cumulo+Accum._Yield+AS_Vol.+emission_ O2+consum_O2+interval_O2+generate_CO2; 0.256, 0.622, pH_cumulo+PL+AN_cumulo+interval_yield+OD+RS+ Feed_Vol+RS_cumulo+Accum._Yield+AS_Vol.+emission_ O2+consum_O2+generate_CO2; 0.256, 0.622, pH_cumulo+PL+AN_cumulo+OD+RS+Feed_Vol+RS_cumulo+ rab_integral+Accum._Yield+AS_Vol.+emission_CO2+ consum_O2+generate_CO2; 0.268, 0.622, pH_cumulo+ PL+AN+interval_yield+OD+RS+RS_cumulo+Accum._ Yield+emission_CO2+consum_O2+interval_O2+generate_ CO2; 0.256, 0.622, pH_cumulo+PL+AN+interval_yield+ OD+RS+RS_cumulo+Cell_conc._interval+RQ_integral+ Accum._Yield+AS_Vol.+emission_O2+consum_O2; 0.244, 0.622, pH+pH_cumulo+PL+AN+interval_yield+OD+RS+ Feed_Vol+RS_cumulo+Cell_conc._interval+RQ_integral+ Accum._Yield+AS_Vol.+consum_O2; 0.280, 0.622, pH_cumulo+PL+AN+OD+RS+Feed_Vol+RS_cumulo+ RQ_integral+Accum._Yield+AS_Vol.+consum_O2; 0.244, 0.622, pH_cumulo+PL+AN_cumulo+interval_yield+OD+ RS+Feed_Vol+RS_cumulo+RQ_integral+Accum._Yield+ AS_Vol.+emission_O2+emission_CO2+consum_O2; 0.268, 0.622, pH_cumulo+PL+AN+interval_yield+OD+ RS+RS_cumulo+rab_integral+Accum._Yield+emission_ CO2+consum_O2+generate_CO2; 0.268, 0.622, tmp+pH_ cumulo+PL+AN_cumulo+OD+RS+RS_cumulo+Accum._ Yield+AS_Vol.+emission_CO2+consum_O2+generate_ CO2; 0.256, 0.622, pH_cumulo+PL+AN+interval_yield+ interval_Pdt.+OD+RS+Feed_Vol+Cell_conc._interval+ Accum._Yield+AS_Vol.+consum_O2+generate_CO2; 0.256, 0.622, tmp_cumulo+pH+pH_cumulo+PL+AN+inter-

501 val_yield+OD+RS+RS_cumulo+AS_Vol.+emission_CO2+consum_O2+generate_CO2; 0.280, 0.622, pH_cumulo+PL+interval_yield+OD+RS+RS_cumulo+RQ_integral+Accum._Yield+AS_Vol.+emission_CO2+consum_O2; 0.256, 0.622, pH+pH_cumulo+PL+AN+AN_cumulo+interval_yield+OD+RS+RS_cumulo+RQ_integral+Accum._Yield+AS_Vol.+consum_O2; 0.244, 0.622, tmp+pH_cumulo+PL+AN+AN_cumulo+interval_yield+OD+RS+RS_cumulo+Cell_conc._interval+Accum._Yield+AS_Vol.+consum_O2+generate_CO2; 0.256, 0.622, tmp_cumulo+pH+pH_cumulo+PL+AN+interval_yield+OD+RS+RS_cumulo+Accum._Yield+AS_Vol.+consum_O2+generate_CO2; 0.244, 0.622, tmp+pH_cumulo+PL+AN+OD+RS+Feed_Vol+RS_cumulo+Accum._Yield+AS_Vol.+emission_CO2+consum_O2+interval_O2+generate_CO2; 0.256, 0.622, pH+pH_cumulo+PL+AN+AN_cumulo+interval_yield+OD+RS+Feed_Vol+RS_cumulo+Accum._Yield+AS_Vol.+consum_O2; 0.231, 0.622, pH_cumulo+PL+AN+AN_cumulo+interval_yield+OD+RS+Feed_Vol+RS_cumulo+Cell_conc._interval+RQ_integral+Accum._Yield+AS_Vol.+emission_O2+consum_O2; 0.256, 0.622, tmp+pH_cumulo+PL+AN+OD+RS+Feed_Vol+RS_cumulo+rab_integral+Accum._Yield+AS_Vol.+consum_O2+generate_CO2; 0.244, 0.622, pH+pH_cumulo+PL+PL_cumulo+AN+interval_yield+OD+RS+RS_cumulo+Accum._Yield+AS_Vol.+emission_CO2+consum_O2+generate_CO2; 0.256, 0.622, pH_cumulo+PL+AN+interval_yield+interval_Pdt.+OD+RS+RS_cumulo+RQ_integral+AS_Vol.+emission_O2+emission_CO2+consum_O2; 0.280, 0.622, pH+pH_cumulo+PL+interval_yield+OD+RS+RS_cumulo+Accum._Yield+emission_CO2+consum_O2+generate_CO2; 0.280, 0.622, pH_cumulo+PL+AN+AN_cumulo+interval_yield+OD+RS+RS_cumulo+Accum._Yield+AS_Vol.+consum_O2; 0.280, 0.622, pH_cumulo+PL+AN_cumulo+interval_yield+OD+RS+RS_cumulo+Cell_conc._interval+emission_CO2+consum_O2+generate_CO2; 0.268, 0.622, pH_cumulo+PL+AN+interval_Pdt.+OD+RS+RS_cumulo+RQ_integral+Accum._Yield+AS_Vol.+emission_O2+consum_O2; 0.280, 0.622, pH_cumulo+PL+AN+interval_yield+OD+RS+RS_cumulo+Accum._Yield+AS_Vol.+emission_CO2+consum_O2; 0.256, 0.622, tmp+pH_cumulo+PL+AN+AN_cumulo+interval_yield+OD+RS+Feed_Vol+RS_cumulo+Accum._Yield+AS_Vol.+consum_O2; 0.244, 0.622, pH+pH_cumulo+PL+AN+OD+RS+Feed_Vol+RS_cumulo+Cell_conc._interval+Accum._Yield+AS_Vol.+emission_CO2+consum_O2+generate_CO2; 0.256, 0.622, pH+pH_cumulo+PL+AN+interval_yield+OD+RS+RS_cumulo+RQ_integral+Accum._Yield+AS_Vol.+emission_O2+consum_O2; 0.231, 0.622, tmp_cumulo+pH_cumulo+PL+AN+AN_cumulo+interval_yield+OD+RS+Feed_Vol+RS_cumulo+Cell_conc._interval+Accum._Yield+AS_Vol.+consum_O2+generate_CO2; 0.256, 0.622, pH_cumulo+PL+AN_cumulo+interval_yield+OD+RS+Feed_Vol+RS_cumulo+Cell_conc._interval+Accum._Yield+AS_Vol.+consum_O2+generate_CO2; 0.231, 0.622, pH+pH_cumulo+PL+AN+AN_cumulo+interval_yield+OD+RS+Feed_Vol+RS_cumulo+rab_integral+Accum._Yield+AS_Vol.+emission_CO2+consum_O2+generate_CO2; 0.231, 0.622, pH+pH_cumulo+PL+AN+interval_yield+OD+RS+Feed_Vol+RS_cumulo+Cell_conc._interval+Accum._Yield+AS_Vol.+consum_O2+interval_O2+generate_CO2; 0.256, 0.622, pH+PL+AN+AN_cumulo+OD+RS+Feed_Vol+RS_cumulo+Cell_conc._interval+Accum._Yield+AS_Vol.+consum_O2+generate_CO2; 0.217, 0.622, tmp+pH_cumulo+PL+AN+AN_cumulo+interval_yield+OD+RS+Feed_Vol+RS_cumulo+Cell_conc._interval+Accum._

502

Yield+AS_Vol.+emission_CO2+consum_O2+generate_CO2; 0.256, 0.622, pH_cumulo+PL+AN_cumulo+interval_yield+OD+RS+RS_cumulo+Accum._Yield+AS_Vol.+emission_CO2+consum_O2+generate_CO2; 0.256, 0.622, pH_cumulo+PL+PL_cumulo+AN+OD+RS+RS_cumulo+Accum._Yield+AS_Vol.+emission_CO2+consum_O2+interval_O2+generate_CO2; 0.279, 0.622, pH_cumulo+PL+interval_yield+OD+RS+Feed_Vol+RS_cumulo+RQ_integral+AS_Vol.+emission_CO2+consum_O2; 0.231, 0.622, tmp+tmp_cumulo+pH_cumulo+PL+AN_cumulo+interval_yield+OD+RS+Feed_Vol+RS_cumulo+Accum._Yield+AS_Vol.+emission_CO2+consum_O2+generate_CO2; 0.279, 0.622, pH_cumulo+PL+AN+AN_cumulo+OD+RS+Feed_Vol+Accum._Yield+AS_Vol.+consum_O2+generate_CO2; 0.268, 0.622, tmp_cumulo+pH_cumulo+PL+interval_yield+OD+RS+RS_cumulo+AS_Vol.+emission_CO2+consum_O2+interval_O2+generate_CO2; 0.231, 0.622, pH_cumulo+PL+AN+interval_yield+OD+RS+Feed_Vol+RS_cumulo+Cell_conc._interval+rab_integral+RQ_integral+Accum._Yield+AS_Vol.+emission_O2+consum_O2; 0.268, 0.622, pH_cumulo+PL+AN+AN_cumulo+interval_yield+OD+RS+Feed_Vol+RS_cumulo+rab_integral+AS_Vol.+consum_O2; 0.256, 0.622, tmp_cumulo+pH_cumulo+PL+interval_yield+OD+RS+Feed_Vol+RS_cumulo+Accum._Yield+AS_Vol.+emission_CO2+consum_O2+generate_CO2; 0.256, 0.622, pH_cumulo+PL+AN+AN_cumulo+interval_yield+OD+RS+RS_cumulo+RQ_integral+Accum._Yield+AS_Vol.+emission_CO2+consum_O2; 0.256, 0.622, tmp_cumulo+pH_cumulo+PL+AN+interval_yield+OD+RS+Feed_Vol+RS_cumulo+rab_integral+Accum._Yield+AS_Vol.+consum_O2; 0.256, 0.622, pH_cumulo+PL+AN+interval_yield+interval_Pdt.+OD+RS+RS_cumulo+rab_integral+RQ_integral+Accum._Yield+AS_Vol.+consum_O2; 0.256, 0.622, pH_cumulo+PL+AN+interval_yield+OD+RS+RS_cumulo+Cell_conc._interval+rab_integral+RQ_integral+Accum._Yield+AS_Vol.+consum_O2; 0.268, 0.622, pH_cumulo+PL+PL_cumulo+AN+OD+RS+Feed_Vol+RS_cumulo+Accum._Yield+AS_Vol.+consum_O2+generate_CO2; 0.256, 0.622, pH+pH_cumulo+PL+interval_yield+OD+RS+RS_cumulo+rab_integral+Accum._Yield+AS_Vol.+emission_CO2+consum_O2+generate_CO2; 0.230, 0.622, pH_cumulo+PL+PL_cumulo+AN+AN_cumulo+interval_yield+OD+RS+Feed_Vol+RS_cumulo+rab_integral+Accum._Yield+AS_Vol.+consum_O2+generate_CO2; 0.268, 0.622, pH_cumulo+PL+AN+AN_cumulo+interval_yield+OD+RS+RS_cumulo+AS_Vol.+emission_O2+consum_O2+generate_CO2; 0.268, 0.622, pH_cumulo+PL+AN+interval_Pdt.+OD+RS+RS_cumulo+Accum._Yield+AS_Vol.+consum_O2+interval_O2+generate_CO2; 0.230, 0.622, tmp+pH_cumulo+PL+AN+interval_yield+OD+RS+Feed_Vol+RS_cumulo+rab_integral+Accum._Yield+AS_Vol.+emission_O2+consum_O2+generate_CO2; 0.256, 0.622, pH_cumulo+PL+AN+interval_yield+OD+RS+RS_cumulo+rab_integral+RQ_integral+Accum._Yield+AS_Vol.+emission_CO2+consum_O2; 0.243, 0.622, pH_cumulo+PL+AN+interval_yield+interval_Pdt.+OD+RS+RS_cumulo+RQ_integral+Accum._Yield+AS_Vol.+emission_O2+emission_CO2+consum_O2; 0.243, 0.622, pH_cumulo+PL+PL_cumulo+AN+OD+RS+Feed_Vol+RS_cumulo+Accum._Yield+AS_Vol.+emission_CO2+consum_O2+interval_O2+generate_CO2; 0.243, 0.622, tmp_cumulo+pH_cumulo+PL+AN+AN_cumulo+interval_yield+OD+RS+Feed_Vol+RS_cumulo+RQ_integral+Accum._Yield+AS_Vol.+consum_O2; 0.256, 0.622, pH+pH_cumulo+PL+interval_yield+OD+RS+Feed_Vol+RS_cumulo+rab_integral+AS_Vol.+ emission_CO2+consum_O2+generate_CO2; 0.256, 0.622, pH+pH_cumulo+PL+interval_yield+OD+RS+RS_cumulo+Accum._Yield+AS_Vol.+emission_CO2+consum_O2+interval_O2+generate_CO2; 0.290, 0.622, pH_cumulo+interval_Pdt.+OD+RS+RS_cumulo+RQ_integral+AS_Vol.+emission_O2+emission_CO2+consum_O2; 0.243, 0.622, pH_cumulo+PL+PL_cumulo+AN+interval_yield+OD+RS+RS_cumulo+rab_integral+Accum._Yield+AS_Vol.+emission_CO2+consum_O2+generate_CO2; 0.230, 0.621, pH_cumulo+PL+AN+AN_cumulo+interval_yield+OD+RS+Feed_Vol+RS_cumulo+Cell_conc._interval+Accum._Yield+AS_Vol.+emission_O2+consum_O2+generate_CO2; 0.230, 0.621, pH_cumulo+PL+AN+AN_cumulo+interval_yield+OD+RS+Feed_Vol+RS_cumulo+Cell_conc._interval+rab_integral+RQ_integral+Accum._Yield+AS_Vol.+consum_O2; 0.279, 0.621, pH_cumulo+PL+interval_yield+OD+RS+Feed_Vol+RS_cumulo+Accum._Yield+AS_Vol.+consum_O2+generate_CO2; 0.243, 0.621, pH_cumulo+PL+AN_cumulo+interval_yield+OD+RS+RS_cumulo+Cell_conc._interval+rab_integral+Accum._Yield+AS_Vol.+emission_CO2+consum_O2+generate_CO2; 0.267, 0.621, tmp+pH_cumulo+PL+AN+interval_yield+OD+RS+Feed_Vol+RS_cumulo+AS_Vol.+consum_O2+generate_CO2; 0.243, 0.621, pH_cumulo+PL+AN+interval_yield+OD+RS+Feed_Vol+RS_cumulo+rab_integral+RQ_integral+AS_Vol.+emission_O2+emission_CO2+consum_O2; 0.230, 0.621, tmp+pH+pH_cumulo+PL+AN+AN_cumulo+interval_yield+OD+RS+Feed_Vol+RS_cumulo+Accum._Yield+AS_Vol.+consum_O2+generate_CO2; 0.279, 0.621, pH_cumulo+PL+AN_cumulo+interval_yield+OD+RS+RS_cumulo+emission_CO2+consum_O2+interval_O2+generate_CO2; 0.255, 0.621, pH_cumulo+PL+AN+OD+RS+RS_cumulo+Cell_conc._interval+rab_integral+Accum._Yield+AS_Vol.+consum_O2+interval_O2+generate_CO2; 0.217, 0.621, pH+pH_cumulo+PL+AN+AN_cumulo+interval_yield+OD+RS+Feed_Vol+RS_cumulo+Cell_conc._interval+rab_integral+Accum._Yield+AS_Vol.+consum_O2+generate_CO2; 0.267, 0.621, pH+pH_cumulo+PL+AN+interval_Pdt.+OD+RS+RS_cumulo+RQ_integral+Accum._Yield+AS_Vol.+consum_O2; 0.279, 0.621, tmp_cumulo+pH_cumulo+PL+AN+interval_yield+OD+RS+RS_cumulo+RQ_integral+AS_Vol.+consum_O2; 0.243, 0.621, tmp+pH_cumulo+PL+PL_cumulo+AN+interval_yield+OD+RS+Feed_Vol+RS_cumulo+Accum._Yield+AS_Vol.+consum_O2+generate_CO2; 0.255, 0.621, tmp+pH_cumulo+PL+AN+OD+RS+RS_cumulo+Accum._Yield+AS_Vol.+emission_CO2+consum_O2+interval_O2+generate_CO2; 0.243, 0.621, tmp_cumulo+pH_cumulo+PL+AN+OD+RS+Feed_Vol+RS_cumulo+Accum._Yield+AS_Vol.+emission_CO2+consum_O2+interval_O2+generate_CO2; 0.230, 0.621, tmp_cumulo+pH_cumulo+PL+AN+interval_yield+interval_Pdt.+OD+RS+Feed_Vol+RS_cumulo+Accum._Yield+AS_Vol.+emission_CO2+consum_O2+generate_CO2; 0.255, 0.621, pH_cumulo+PL+AN_cumulo+interval_yield+OD+RS+Feed_Vol+RS_cumulo+rab_integral+RQ_integral+Accum._Yield+AS_Vol.+consum_O2; 0.230, 0.621, tmp_cumulo+pH_cumulo+PL+AN+interval_yield+OD+RS+Feed_Vol+RS_cumulo+rab_integral+Accum._Yield+AS_Vol.+consum_O2+interval_O2+generate_CO2; 0.267, 0.621, pH_cumulo+PL+AN_cumulo+interval_yield+OD+RS+RS_cumulo+AS_Vol.+emission_O2+emission_CO2+consum_O2+generate_CO2; 0.255, 0.621, pH_cumulo+PL+AN+interval_yield+OD+RS+Feed_Vol+RQ_integral+Accum._Yield+AS_Vol.+emission_O2+emission_CO2+consum_O2; 0.243, 0.621, pH_cumulo+PL+AN+AN_cumulo+interval_yield+interval_Pdt.+OD+RS+Feed_Vol+rab_integral+Accum._Yield+AS_Vol.+consum_O2+generate_CO2; 0.217, 0.621, tmp+tmp_cumulo+pH+pH_cumulo+PL+AN+interval_yield+OD+RS+Feed_Vol+RS_cumulo+Accum._Yield+AS_Vol.+emission_CO2+consum_O2+generate_CO2; 0.230, 0.621, pH+pH_cumulo+PL+PL_cumulo+AN+OD+RS+Feed_Vol+RS_cumulo+Accum._Yield+AS_Vol.+emission_CO2+consum_O2+interval_O2+generate_CO2; 0.243, 0.621, tmp_cumulo+pH_cumulo+PL+AN+interval_yield+OD+RS+Feed_Vol+RS_cumulo+Cell_conc._interval+AS_Vol.+emission_CO2+consum_O2+generate_CO2; 0.255, 0.621, pH_cumulo+PL+PL_cumulo+AN+interval_yield+OD+RS+RS_cumulo+Cell_conc._interval+Accum._Yield+AS_Vol.+consum_O2+generate_CO2; 0.279, 0.621, pH+pH_cumulo+PL+AN+interval_yield+OD+RS+RS_cumulo+AS_Vol.+consum_O2+generate_CO2; 0.267, 0.621, pH+PL+AN+interval_yield+OD+RS+Feed_Vol+RS_cumulo+AS_Vol.+emission_CO2+consum_O2+generate_CO2; 0.255, 0.621, pH_cumulo+PL+AN+interval_yield+OD+RS+Feed_Vol+RS_cumulo+rab_integral+AS_Vol.+emission_O2+consum_O2+generate_CO2; 0.255, 0.621, pH_cumulo+PL+interval_yield+OD+RS+RS_cumulo+rab_integral+RQ_integral+Accum._Yield+AS_Vol.+emission_CO2+emission_CO2+consum_O2; 0.243, 0.621, tmp+tmp_cumulo+pH_cumulo+PL+AN+interval_yield+OD+RS+RS_cumulo+rab_integral+Accum._Yield+AS_Vol.+consum_O2+generate_CO2; 0.217, 0.621, tmp+pH+pH_cumulo+PL+AN+interval_yield+OD+RS+Feed_Vol+RS_cumulo+rab_integral+Accum._Yield+AS_Vol.+emission_CO2+consum_O2+generate_CO2; 0.243, 0.621, pH_cumulo+PL+AN+AN_cumulo+OD+RS+Feed_Vol+RS_cumulo+Cell_conc._interval+rab_integral+Accum._Yield+AS_Vol.+consum_O2+generate_CO2; 0.255, 0.621, pH_cumulo+PL+interval_yield+OD+RS+Feed_Vol+RS_cumulo+rab_integral+AS_Vol.+emission_CO2+consum_O2+interval_O2+generate_CO2; 0.230, 0.621, tmp_cumulo+pH+pH_cumulo+PL+AN+AN_cumulo+interval_yield+OD+RS+Feed_Vol+RS_cumulo+Accum._Yield+AS_Vol.+consum_O2+generate_CO2; 0.243, 0.621, tmp+tmp_cumulo+pH_cumulo+PL+AN+interval_yield+OD+RS+RS_cumulo+Cell_conc._interval+Accum._Yield+AS_Vol.+consum_O2+generate_CO2; 0.255, 0.621, tmp_cumulo+pH_cumulo+PL+AN+interval_yield+interval_Pdt.+OD+RS+Feed_Vol+Accum._Yield+AS_Vol.+consum_O2+generate_CO2; 0.230, 0.621, pH_cumulo+PL+AN+AN_cumulo+interval_yield+OD+RS+Feed_Vol+RS_cumulo+rab_integral+RQ_integral+Accum._Yield+AS_Vol.+emission_CO2+consum_O2; 0.267, 0.621, tmp+pH+pH_cumulo+PL+interval_yield+OD+RS+RS_cumulo+AS_Vol.+emission_CO2+consum_O2+generate_CO2; 0.267, 0.621, pH_cumulo+PL+AN+interval_yield+OD+RS+Feed_Vol+RS_cumulo+Accum._Yield+emission_CO2+consum_O2+generate_CO2; 0.255, 0.621, pH_cumulo+PL+AN_cumulo+interval_yield+OD+RS+RS_cumulo+Cell_conc._interval+rab_integral+AS_Vol.+emission_CO2+consum_O2+generate_CO2; 0.267, 0.621, pH_cumulo+PL+AN+interval_yield+OD+RS+RS_cumulo+Cell_conc._interval+AS_Vol.+emission_O2+consum_O2+generate_CO2; 0.230, 0.621, tmp+pH_cumulo+PL+AN+AN_cumulo+interval_yield+interval_Pdt.+OD+RS+Feed_Vol+RS_cumulo+Accum._Yield+AS_Vol.+consum_O2+generate_CO2; 0.242, 0.621, tmp_cumulo+pH_cumulo+PL+AN+AN_cumulo+interval_yield+OD+RS+RS_cumulo+Cell_conc._interval+Accum._Yield+AS_Vol.+consum_O2+generate_CO2; 0.255, 0.621, pH_cumulo+PL+interval_yield+interval_Pdt.+OD+RS+Feed_Vol+RS_cumulo+RQ_integral+AS_Vol.+emission_

O2+emission_CO2+consum_O2; 0.255, 0.621, pH_cumulo+PL+AN+AN_cumulo+OD+RS+RS_cumulo+Accum._Yield+AS_Vol.+emission_O2+consum_O2+interval_O2+generate_CO2; 0.230, 0.621, tmp+tmp_cumulo+pH_cumulo+PL+AN+interval_yield+OD+RS+Feed_Vol+RS_cumulo+Cell.conc._interval+Accum._Yield+AS_Vol.+consum_O2+generate_CO2; 0.230, 0.621, pH_cumulo+PL+PL_cumulo+AN+interval_yield+OD+RS+Feed_Vol+RS_cumulo+rab_integral+Accum._Yield+AS_Vol.+consum_O2+interval_O2+generate_CO2; 0.230, 0.621, pH_cumulo+PL+AN+AN_cumulo+interval_yield+OD+RS+RS_cumulo+rab_integral+Accum._Yield+AS_Vol.+emission_CO2+consum_O2+interval_O2+generate_CO2; 0.242, 0.621, pH_cumulo+PL+PL_cumulo+AN+AN_cumulo+interval_yield+OD+RS+RS_cumulo+Accum._Yield+AS_Vol.+emission_CO2+consum_O2+generate_CO2; 0.255, 0.621, pH_cumulo+PL+AN_cumulo+interval_yield+OD+RS+RS_cumulo+rab_integral+Accum._Yield+AS_Vol.+emission_O2+consum_O2+generate_CO2; 0.267, 0.621, tmp+tmp_cumulo+pH_cumulo+PL+AN+OD+RS+RS_cumulo+Accum._Yield+AS_Vol.+consum_O2+generate_CO2; 0.278, 0.621, pH_cumulo+PL+AN+interval_yield+OD+RS+RS_cumulo+Cell_conc._interval+emission_CO2+consum_O2+generate_CO2; 0.278, 0.621, pH_cumulo+PL+interval_yield+interval_Pdt.+OD+RS+RS_cumulo+RQ_integral+AS_Vol.+emission_CO2+consum_O2; 0.229, 0.621, pH+pH_cumulo+PL+AN+AN_cumulo+OD+RS+Feed_Vol+RS_cumulo+rab_integral+Accum._Yield+AS_Vol.+emission_CO2+consum_O2+generate_CO2; 0.242, 0.621, tmp+pH_cumulo+PL+AN+AN_cumulo+interval_yield+interval_Pdt.+OD+RS+Feed_Vol+Accum._Yield+AS_Vol.+consum_O2+generate_CO2; 0.267, 0.621, tmp_cumulo+pH_cumulo+PL+AN+interval_yield+OD+RS+Feed_Vol+RS_cumulo+AS_Vol.+consum_O2+generate_CO2; 0.278, 0.621, pH_cumulo+PL+AN+interval_yield+interval_Pdt.+OD+RS+Feed_Vol+AS_Vol.+consum_O2+generate_CO2; 0.267, 0.621, pH+pH_cumulo+PL+AN+OD+RS+RS_cumulo+rab_integral+Accum._Yield+AS_Vol.+consum_O2+generate_CO2; 0.255, 0.621, tmp+pH+pH_cumulo+PL+AN+interval_yield+OD+RS+RS_cumulo+Accum._Yield+AS_Vol.+consum_O2+generate_CO2; 0.289, 0.621, pH_cumulo+PL+OD+RS+RS_cumulo+Accum._Yield+AS_Vol.+consum_O2+interval_O2+generate_CO2; 0.255, 0.621, pH_cumulo+PL+AN_cumulo+interval_yield+OD+RS+Feed_Vol+RS_cumulo+RQ_integral+AS_Vol.+emission_O2+emission_CO2+consum_O2; 0.267, 0.621, pH+pH_cumulo+PL+interval_yield+OD+RS+RS_cumulo+RQ_integral+AS_Vol.+emission_O2+emission_CO2+consum_O2; 0.267, 0.621, pH_cumulo+PL+AN+AN_cumulo+interval_yield+OD+RS+RS_cumulo+rab_integral+AS_Vol.+consum_O2+generate_CO2; 0.267, 0.621, pH_cumulo+PL+AN+OD+RS+Feed_Vol+RS_cumulo+RQ_integral+Accum._Yield+AS_Vol.+emission_O2+consum_O2; 0.255, 0.621, pH_cumulo+PL+AN+AN_cumulo+OD+RS+RS_cumulo+Cell_conc._interval+rab_integral+Accum._Yield+AS_Vol.+consum_O2+generate_CO2; 0.242, 0.621, pH+pH_cumulo+PL+PL_cumulo+AN+OD+RS+Feed_Vol+RS_cumulo+Accum._Yield+AS_Vol.+consum_O2+interval_O2+generate_CO2; 0.254, 0.621, tmp+tmp_cumulo+pH_cumulo+PL+AN+OD+RS+Feed_Vol+RS_cumulo+Accum._Yield+AS_Vol.+consum_O2+generate_CO2; 0.242, 0.621, pH_cumulo+PL+AN+AN_cumulo+OD+RS+Feed_Vol+RS_cumulo+Cell_conc._interval+Accum._Yield+AS_Vol.+consum_O2+interval_O2+generate_CO2; 0.242, 0.621, pH_cumulo+PL+AN+interval_yield+OD+RS+RS_cumulo+Cell_conc._interval+Accum._Yield+AS_Vol.+consum_O2+interval_O2+generate_CO2; 0.229, 0.621, pH+pH_cumulo+PL+AN+AN_cumulo+interval_yield+OD+RS+RS_cumulo+rab_integral+Accum._Yield+AS_Vol.+emission_CO2+consum_O2+generate_CO2; 0.242, 0.621, tmp+pH_cumulo+PL+AN+AN_cumulo+interval_yield+OD+RS+Feed_Vol+RS_cumulo+rab_integral+Accum._Yield+AS_Vol.+consum_O2; 0.254, 0.621, pH+pH_cumulo+PL+AN+AN_cumulo+OD+RS+RS_cumulo+Accum._Yield+AS_Vol.+consum_O2+interval_O2+generate_CO2; 0.229, 0.621, tmp_cumulo+pH_cumulo+PL+AN+interval_yield+interval_Pdt.+OD+RS+Feed_Vol+RS_cumulo+rab_integral+Accum._Yield+AS_Vol.+consum_O2+generate_CO2; 0.242, 0.621, pH_cumulo+PL+AN+interval_Pdt.+OD+RS+Feed_Vol+RS_cumulo+rab_integral+Accum._Yield+AS_Vol.+emission_CO2+consum_O2+generate_CO2; 0.254, 0.621, pH+pH_cumulo+PL+AN+OD+RS+Feed_Vol+RS_cumulo+Accum._Yield+AS_Vol.+emission_O2+consum_O2+generate_CO2; 0.254, 0.621, pH_cumulo+PL+PL_cumulo+AN+AN_cumulo+interval_yield+OD+RS+RS_cumulo+Accum._Yield+AS_Vol.+consum_O2+generate_CO2; 0.254, 0.621, pH_cumulo+PL+AN+interval_Pdt.+OD+RS+Feed_Vol+RS_cumulo+rab_integral+Accum._Yield+AS_Vol.+consum_O2+generate_CO2; 0.254, 0.621, tmp_cumulo+pH_cumulo+PL+AN+OD+RS+Feed_Vol+RS_cumulo+rab_integral+Accum._Yield+AS_Vol.+consum_O2+generate_CO2; 0.242, 0.621, tmp+pH_cumulo+PL+AN+AN_cumulo+interval_yield+OD+RS+RS_cumulo+rab_integral+Accum._Yield+AS_Vol.+consum_O2+generate_CO2; 0.266, 0.621, pH+pH_cumulo+PL+AN_cumulo+interval_yield+OD+RS+RS_cumulo+Accum._Yield+emission_CO2+consum_O2+generate_CO2; 0.229, 0.621, tmp+tmp_cumulo+pH_cumulo+PL+AN+interval_yield+interval_Pdt.+OD+RS+Feed_Vol+RS_cumulo+Accum._Yield+AS_Vol.+consum_O2+generate_CO2; 0.242, 0.621, tmp+pH_cumulo+PL+AN+interval_yield+OD+RS+RS_cumulo+Cell_conc._interval+rab_integral+Accum._Yield+AS_Vol.+consum_O2+generate_CO2; 0.229, 0.621, pH_cumulo+PL+AN+AN_cumulo+OD+RS+Feed_Vol+RS_cumulo+rab_integral+Accum._Yield+AS_Vol.+emission_CO2+consum_O2+interval_O2+generate_CO2; 0.266, 0.621, tmp+pH_cumulo+PL+interval_yield+OD+RS+RS_cumulo+Cell_conc._interval+AS_Vol.+emission_CO2+consum_O2+generate_CO2; 0.311, 0.621, pH_cumulo+PL+interval_yield+OD+RS+emission_CO2+consum_O2+generate_CO2; 0.242, 0.621, tmp+tmp_cumulo+pH_cumulo+PL+AN+interval_yield+OD+RS+Feed_Vol+RS_cumulo+RQ_integral+Accum._Yield+AS_Vol.+consum_O2; 0.278, 0.621, tmp_cumulo+pH_cumulo+PL+AN_cumulo+OD+RS+RS_cumulo+Accum._Yield+AS_Vol.+consum_O2+generate_CO2; 0.242, 0.621, pH_cumulo+PL+AN+interval_yield+OD+RS+RS_cumulo+Cell_conc._interval+rab_integral+Accum._Yield+AS_Vol.+emission_O2+consum_O2+generate_CO2; 0.254, 0.621, pH+pH_cumulo+PL+AN+AN_cumulo+OD+RS+RS_cumulo+Cell_conc._interval+Accum._Yield+AS_Vol.+consum_O2+generate_CO2; 0.254, 0.621, pH_cumulo+PL+PL_cumulo+AN_cumulo+interval_yield+OD+RS+RS_cumulo+Accum._Yield+AS_Vol.+emission_CO2+consum_O2+generate_CO2; 0.266, 0.621, pH_cumulo+PL+AN_cumulo+interval_yield+OD+RS+Feed_Vol+RS_cumulo+rab_integral+emission_CO2+consum_O2+generate_CO2; 0.266, 0.621, pH+pH_cumulo+PL+AN+interval_yield+OD+RS+Feed_Vol+RS_cumulo+RQ_integral+AS_Vol.+consum_O2; 0.254, 0.621, pH+pH_cumulo+PL+interval_Pdt.+OD+RS+RS_cumulo+RQ_integral+Accum._Yield+AS_Vol.+emission_O2+emission_CO2+consum_O2; 0.254, 0.621, pH_cumulo+PL+AN+interval_yield+OD+RS+Feed_Vol+Accum._Yield+AS_Vol.+emission_CO2+consum_O2+interval_O2+generate_CO2; 0.254, 0.621, tmp+pH_cumulo+PL+AN_cumulo+interval_yield+OD+RS+RS_cumulo+rab_integral+AS_Vol.emission_CO2+consum_O2+generate_CO2; 0.242, 0.621, pH_cumulo+PL+PL_cumulo+AN+interval_yield+OD+RS+Feed_Vol+RS_cumulo+Accum._Yield+AS_Vol.+emission_O2+consum_O2+generate_CO2; 0.242, 0.621, pH_cumulo+PL+AN+AN_cumulo+interval_yield+OD+RS+RS_cumulo+Cell_conc._interval+Accum._Yield+AS_Vol.+emission_O2+consum_O2+generate_CO2; 0.266, 0.621, pH_cumulo+PL+PL_cumulo+AN+OD+RS+RS_cumulo+Accum._Yield+AS_Vol.+emission_CO2+consum_O2+generate_CO2; 0.289, 0.621, pH_cumulo+PL+AN+AN_cumulo+interval_yield+OD+RS+RS_cumulo+AS_Vol.+consum_O2; 0.278, 0.621, pH_cumulo+PL+AN_cumulo+interval_yield+OD+RS+RS_cumulo+AS_Vol.+emission_O2+consum_O2+generate_CO2; 0.278, 0.621, pH_cumulo+PL+AN_cumulo+OD+RS+RS_cumulo+rab_integral+Accum._Yield+AS_Vol.+consum_O2+generate_CO2; 0.254, 0.621, pH_cumulo+PL+AN_cumulo+interval_yield+OD+RS+Feed_Vol+RS_cumulo+RQ_integral+Accum._Yield+AS_Vol.+emission_O2+consum_O2; 0.242, 0.621, pH+PL+PL_cumulo+AN+interval_yield+OD+RS+Feed_Vol+RS_cumulo+Accum._Yield+AS_Vol.+emission_CO2+consum_O2+generate_CO2; 0.266, 0.621, pH_cumulo+PL+AN+AN_cumulo+interval_yield+OD+RS+RS_cumulo+RQ_integral+AS_Vol.+emission_CO2+consum_O2; 0.266, 0.620, pH_cumulo+PL+AN_cumulo+interval_yield+OD+RS+RS_cumulo+Accum._Yield+emission_CO2+consum_O2+interval_O2+generate_CO2; 0.254, 0.620, pH_cumulo+PL+interval_Pdt.+OD+RS+RS_cumulo+rab_integral+RQ_integral+Accum._Yield+AS_Vol.+emission_O2+emission_CO2+consum_O2; 0.266, 0.620, pH_cumulo+PL+AN+interval_yield+interval_Pdt.+OD+RS+RS_cumulo+RQ_integral+AS_Vol.+emission_CO2+consum_O2; 0.254, 0.620, pH_cumulo+PL+interval_yield+OD+RS+RS_cumulo+Cell_conc._interval+Accum._Yield+AS_Vol.+emission_CO2+consum_O2+interval_O2+generate_CO2; 0.266, 0.620, pH+PL+AN+AN_cumulo+interval_yield+OD+RS+RS_cumulo+Accum._Yield+AS_Vol.+consum_O2+generate_CO2; 0.229, 0.620, tmp+pH_cumulo+PL+AN+AN_cumulo+interval_yield+OD+RS+Feed_Vol+RS_cumulo+Accum._Yield+AS_Vol.+consum_O2+interval_O2+generate_CO2; 0.229, 0.620, pH+pH_cumulo+PL+AN+AN_cumulo+interval_yield+interval_Pdt.+OD+RS+Feed_Vol+RS_cumulo+Accum._Yield+AS_Vol.+consum_O2+generate_CO2; 0.229, 0.620, pH_cumulo+PL+AN+AN_cumulo+interval_yield+OD+RS+RS_cumulo+Cell_conc._interval+rab_integral+Accum._Yield+AS_Vol.+emission_CO2+consum_O2+generate_CO2; 0.277, 0.620, pH_cumulo+PL+AN+interval_yield+OD+RS+Feed_Vol+rab_integral+Accum._Yield+AS_Vol.+consum_O2; 0.228, 0.620, pH+pH_cumulo+PL+AN+interval_yield+OD+RS+Feed_Vol+RS_cumulo+Accum._Yield+AS_Vol.+emission_CO2+consum_O2+interval_O2+generate_CO2; 0.241, 0.620, pH_cumulo+PL+interval_yield+OD+RS+Feed_Vol+RS_cumulo+rab_integral+RQ_integral+Accum._Yield+AS_Vol.+emission_O2+emission_CO2+consum_O2; 0.254, 0.620, pH_cumulo+PL+PL_cumulo+AN+AN_cumulo+interval_yield+OD+RS+RS_cumulo+RQ_integral+Accum._Yield+AS_Vol.+consum_O2; 0.254, 0.620, pH_cumulo+PL+AN+AN_cumulo+interval_yield+OD+RS+RS_cumulo+RQ_integral+AS_Vol.+emission_O2+emission_CO2+consum_O2; 0.228, 0.620, tmp_cumulo+pH_cumulo+PL+AN+AN_cumulo+interval_yield+OD+RS+Feed_Vol+RS_cumulo+Accum._Yield+AS_Vol.+consum_O2+interval_O2+generate_CO2; 0.266, 0.620, tmp_cumulo+pH_cumulo+PL+interval_yield+OD+RS+RS_cumulo+rab_integral+AS_Vol.+emission_CO2+consum_O2+generate_CO2; 0.254, 0.620, pH_cumulo+PL+AN+interval_Pdt.+OD+RS+RS_cumulo+rab_integral+Accum._Yield+AS_Vol.+emission_CO2+consum_O2+generate_CO2; 0.266, 0.620, pH_cumulo+PL+AN+interval_yield+OD+RS+Feed_Vol+Cell_conc._interval+Accum._Yield+AS_Vol.+consum_O2+generate_CO2; 0.254, 0.620, pH_cumulo+PL+AN+AN_cumulo+interval_yield+OD+RS+Feed_Vol+RS_cumulo+rab_integral+RQ_integral+AS_Vol.+consum_O2; 0.241, 0.620, pH+pH_cumulo+PL+AN+interval_yield+OD+RS+Feed_Vol+RS_cumulo+AS_Vol.+emission_CO2+consum_O2+interval_O2+generate_CO2; 0.277, 0.620, pH_cumulo+PL+AN_cumulo+OD+RS+RS_cumulo+Accum._Yield+AS_Vol.+emission_O2+consum_O2+generate_CO2; 0.254, 0.620, pH+pH_cumulo+PL+AN+OD+RS+RS_cumulo+Cell_conc._interval+Accum._Yield+AS_Vol.+consum_O2+interval_O2+generate_CO2; 0.254, 0.620, tmp+pH_cumulo+PL+AN+interval_yield+OD+RS+Feed_Vol+Accum._Yield+AS_Vol.+emission_CO2+consum_O2+generate_CO2; 0.266, 0.620, pH_cumulo+PL+AN+interval_yield+OD+RS+RS_cumulo+AS_Vol.+emission_O2+consum_O2+interval_O2+generate_CO2; 0.266, 0.620, pH_cumulo+PL+AN_cumulo+interval_yield+interval_Pdt.+OD+RS+RS_cumulo+AS_Vol.+emission_CO2+consum_O2+generate_CO2; 0.254, 0.620, pH_cumulo+PL+AN+AN_cumulo+interval_yield+OD+RS+RS_cumulo+Cell_conc._interval+RQ_integral+Accum._Yield+AS_Vol.+consum_O2; 0.254, 0.620, pH_cumulo+PL+AN_cumulo+OD+RS+RS_cumulo+rab_integral+Accum._Yield+AS_Vol.+emission_CO2+consum_O2+interval_O2+generate_CO2; 0.254, 0.620, pH_cumulo+PL+AN+AN_cumulo+interval_Pdt.+OD+RS+Feed_Vol+RS_cumulo+Accum._Yield+AS_Vol.+consum_O2+generate_CO2; 0.266, 0.620, pH_cumulo+PL+interval_yield+OD+RS+RS_cumulo+Accum._Yield+AS_Vol.+emission_O2+consum_O2+interval_O2+generate_CO2; 0.241, 0.620, tmp+tmp_cumulo+pH_cumulo+PL+AN+interval_yield+OD+RS+RS_cumulo+Accum._Yield+AS_Vol.+consum_O2+interval_O2+generate_CO2; 0.253, 0.620, pH_cumulo+PL+AN+interval_yield+OD+RS+RS_cumulo+rab_integral+RQ_integral+AS_Vol.+emission_O2+emission_CO2+consum_O2; 0.215, 0.620, pH_cumulo+PL+AN+AN_cumulo+interval_yield+OD+RS+Feed_Vol+RS_cumulo+Cell_conc._interval+Accum._Yield+AS_Vol.+emission_CO2+consum_O2+interval_O2+generate_CO2; 0.253, 0.620, tmp_cumulo+pH_cumulo+PL+AN+AN_cumulo+OD+RS+RS_cumulo+Accum._Yield+AS_Vol.+consum_O2+interval_O2+generate_CO2; 0.265, 0.620, pH+pH_cumulo+PL+AN+interval_yield+OD+RS+RS_cumulo+rab_integral+RQ_integral+AS_Vol.+consum_O2; 0.241, 0.620, tmp+pH_cumulo+PL+AN_cumulo+interval_yield+OD+RS+RS_cumulo+rab_integral+Accum._Yield+AS_Vol.+emission_CO2+consum_O2+generate_CO2; 0.253, 0.620, tmp_cumulo+pH_cumulo+PL+AN_cumulo+OD+RS+Feed_Vol+RS_cumulo+Accum._Yield+AS_Vol.+emission_CO2+consum_O2+generate_CO2; 0.241, 0.620, pH+PL+AN+interval_yield+interval_Pdt.+OD+RS+Feed_Vol+RS_cumulo+Accum._Yield+AS_Vol.+emission_CO2+consum_O2+generate_CO2; 0.265, 0.620, pH_cumulo+PL+PL_cumulo+AN_cumulo+interval_yield+OD+RS+RS_cumulo+AS_Vol.+emission_CO2+consum_O2+generate_CO2; 0.241, 0.620, tmp_cumulo+pH_cumulo+PL+AN+AN_cumulo+interval_yield+OD+RS+RS_cumulo+rab_ integral+Accum._Yield+AS_Vol.+consum_O2+generate_CO2; 0.265, 0.620, tmp_cumulo+pH+pH_cumulo+PL+interval_yield+OD+RS+RS_cumulo+AS_Vol.+emission_CO2+consum_O2+generate_CO2; 0.241, 0.620, pH_cumulo+PL+AN+AN_cumulo+OD+RS+Feed_Vol+RS_cumulo+Accum._Yield+AS_Vol.+emission_O2+consum_O2+interval_O2+generate_CO2; 0.215, 0.620, pH_cumulo+PL+AN+interval_yield+OD+RS+Feed_Vol+RS_cumulo+Cell_conc._interval+rab_integral+Accum._Yield+AS_Vol.+emission_CO2+consum_O2+interval_O2+generate_CO2; 0.253, 0.620, pH+PL+AN+AN_cumulo+interval_yield+interval_Pdt.+OD+RS+Feed_Vol+Accum._Yield+AS_Vol.+consum_O2+generate_CO2; 0.265, 0.620, pH_cumulo+PL+PL_cumulo+AN+interval_yield+OD+RS+Feed_Vol+RS_cumulo+Accum._Yield+AS_Vol.+consum_O2; 0.241, 0.620, pH_cumulo+PL+AN+AN_cumulo+OD+RS+RS_cumulo+rab_integral+Accum._Yield+AS_Vol.+emission_CO2+consum_O2+interval_O2+generate_CO2; 0.253, 0.620, pH+pH_cumulo+PL+AN+OD+RS+RS_cumulo+rab_integral+Accum._Yield+AS_Vol.+consum_O2+interval_O2+generate_CO2; 0.253, 0.620, pH_cumulo+PL+AN+AN_cumulo+interval_yield+OD+RS+Feed_Vol+RS_cumulo+Cell_conc._interval+Accum._Yield+AS_Vol.+consum_O2; 0.277, 0.620, pH+pH_cumulo+PL+interval_yield+OD+RS+RS_cumulo+rab_integral+emission_CO2+consum_O2+generate_CO2; 0.265, 0.620, pH_cumulo+PL+AN+AN_cumulo+interval_Pdt.+OD+RS+RS_cumulo+Accum._Yield+AS_Vol.+consum_O2+generate_CO2; 0.288, 0.620, pH_cumulo+PL+interval_yield+OD+RS+RS_cumulo+Cell_conc._interval+RQ_integral+AS_Vol.+consum_O2; 0.265, 0.620, pH_cumulo+PL+interval_yield+OD+RS+RS_cumulo+rab_integral+Accum._Yield+AS_Vol.+consum_O2+interval_O2+generate_CO2; 0.265, 0.620, pH_cumulo+PL+AN+interval_Pdt.+OD+RS+RS_cumulo+Cell_conc._interval+Accum._Yield+AS_Vol.+consum_O2+generate_CO2; 0.228, 0.620, pH+pH_cumulo+PL+PL_cumulo+AN+interval_yield+OD+RS+Feed_Vol+RS_cumulo+Accum._Yield+AS_Vol.+consum_O2+interval_O2+generate_CO2; 0.228, 0.620, pH+pH_cumulo+PL+AN+interval_yield+OD+RS+Feed_Vol+RS_cumulo+Cell_conc._interval+Accum._Yield+AS_Vol.+emission_O2+consum_O2+generate_CO2; 0.288, 0.620, pH_cumulo+PL+AN+OD+RS+Feed_Vol+Accum._Yield+AS_Vol.+consum_O2+generate_CO2; 0.241, 0.620, pH+PL+AN+interval_yield+OD+RS+Feed_Vol+RS_cumulo+Cell_conc._interval+rab_integral+Accum._Yield+AS_Vol.+consum_O2+generate_CO2; 0.277, 0.620, tmp+pH_cumulo+PL+interval_yield+OD+RS+RS_cumulo+Accum._Yield+emission_CO2+consum_O2+generate_CO2; 0.228, 0.620, pH_cumulo+PL+AN+interval_yield+OD+RS+Feed_Vol+RS_cumulo+Cell_conc._interval+Accum._Yield+AS_Vol.+emission_O2+emission_CO2+consum_O2+generate_CO2; 0.214, 0.620, pH+pH_cumulo+PL+PL_cumulo+AN+interval_yield+OD+RS+Feed_Vol+RS_cumulo+Accum._Yield+AS_Vol.+emission_CO2+consum_O2+interval_O2+generate_CO2; 0.228, 0.620, pH_cumulo+PL+AN+AN_cumulo+interval_yield+interval_Pdt.+OD+RS+Feed_Vol+RS_cumulo+RQ_integral+Accum._Yield+AS_Vol.+emission_O2+consum_O2; 0.288, 0.620, pH_cumulo+PL+interval_yield+OD+RS+RS_cumulo+rab_integral+AS_Vol.+consum_O2+generate_CO2; 0.265, 0.620, pH_cumulo+PL+AN+interval_yield+OD+RS+RS_cumulo+rab_integral+RQ_integral+AS_Vol.+emission_CO2+consum_O2; 0.253, 0.620, tmp+tmp_cumulo+pH_cumulo+PL+AN_cumulo+OD+RS+RS_cumulo+Accum._Yield+AS_Vol.+emission_CO2+consum_O2+generate_CO2; 0.253, 0.620, pH_cumulo+PL+AN_cumulo+interval_Pdt.+OD+RS+Feed_Vol+RS_cumulo+Accum._Yield+AS_Vol.+emission_CO2+consum_O2+generate_CO2; 0.253, 0.620, pH_cumulo+PL+AN_cumulo+interval_yield+OD+RS+RS_cumulo+RQ_integral+Accum._Yield+AS_Vol.+emission_O2+emission_CO2+consum_O2; 0.277, 0.620, pH_cumulo+PL+AN_cumulo+interval_yield+OD+RS+RS_cumulo+RQ_integral+AS_Vol.+emission_O2+consum_O2; 0.214, 0.620, tmp+tmp_cumulo+pH_cumulo+PL+AN+AN_cumulo+interval_yield+OD+RS+Feed_Vol+RS_cumulo+rab_integral+Accum._Yield+AS_Vol.+consum_O2+generate_CO2; 0.277, 0.620, pH+pH_cumulo+PL+interval_yield+OD+RS+Feed_Vol+RS_cumulo+emission_CO2+consum_O2+generate_CO2; 0.228, 0.620, tmp+pH_cumulo+PL+AN+interval_yield+OD+RS+Feed_Vol+RS_cumulo+Accum._Yield+AS_Vol.+emission_O2+emission_CO2+consum_O2+generate_CO2; 0.265, 0.620, pH_cumulo+PL+AN+interval_yield+OD+RS+Feed_Vol+RS_cumulo+Cell_conc._interval+RQ_integral+AS_Vol.+consum_O2; 0.265, 0.620, pH+pH_cumulo+PL+AN_cumulo+interval_yield+OD+RS+RS_cumulo+RQ_integral+Accum._Yield+AS_Vol.+consum_O2; 0.265, 0.620, pH+PL+AN+AN_cumulo+OD+RS+Feed_Vol+RS_cumulo+Accum._Yield+AS_Vol.+consum_O2+generate_CO2; 0.240, 0.620, pH+pH_cumulo+PL+AN_cumulo+interval_yield+OD+RS+RS_cumulo+Cell_conc._interval+Accum._Yield+AS_Vol.+emission_CO2+consum_O2+generate_CO2; 0.240, 0.620, tmp+tmp_cumulo+pH_cumulo+PL+AN+OD+RS+Feed_Vol+RS_cumulo+Accum._Yield+AS_Vol.+emission_CO2+consum_O2+generate_CO2; 0.240, 0.620, pH+pH_cumulo+PL+AN+interval_Pdt.+OD+RS+Feed_Vol+RS_cumulo+Accum._Yield+AS_Vol.+emission_CO2+consum_O2+generate_CO2; 0.253, 0.620, pH_cumulo+PL+AN+OD+RS+Feed_Vol+RS_cumulo+Accum._Yield+AS_Vol.+emission_O2+emission_CO2+consum_O2+generate_CO2; 0.240, 0.620, pH+pH_cumulo+PL+AN+OD+RS+Feed_Vol+RS_cumulo+Cell_conc._interval+Accum._Yield+AS_Vol.+consum_O2+interval_O2+generate_CO2; 0.240, 0.620, pH_cumulo+PL+AN+AN_cumulo+interval_yield+OD+RS+Feed_Vol+RS_cumulo+Cell_conc._interval+rab_integral+Accum._Yield+AS_Vol.+consum_O2; 0.253, 0.620, tmp+tmp_cumulo+pH_cumulo+PL+interval_yield+OD+RS+Feed_Vol+RS_cumulo+AS_Vol.+emission_CO2+consum_O2+generate_CO2; 0.253, 0.620, pH_cumulo+PL+AN+interval_yield+OD+RS+Feed_Vol+RS_cumulo+RQ_integral+Accum._Yield+AS_Vol.+consum_O2+interval_O2; 0.277, 0.620, pH_cumulo+PL+interval_yield+OD+RS+RS_cumulo+Cell_conc._interval+Accum._Yield+AS_Vol.+consum_O2+generate_CO2; 0.277, 0.620, pH_cumulo+PL+AN_cumulo+interval_yield+OD+RS+Feed_Vol+RS_cumulo+RQ_integral+AS_Vol.+consum_O2; 0.240, 0.620, tmp+pH_cumulo+PL+AN+interval_yield+OD+RS+Feed_Vol+RS_cumulo+RQ_integral+Accum._Yield+AS_Vol.+emission_CO2+consum_O2; 0.227, 0.620, pH+pH_cumulo+PL+AN+AN_cumulo+OD+RS+Feed_Vol+RS_cumulo+Cell_conc._interval+Accum._Yield+AS_Vol.+emission_CO2+consum_O2+generate_CO2

[208. Linear Model that Predicts Arginine Production Amount in Interval 8]

0.478, 0.783, pH_cumulo+PL+PL_cumulo+AN+AN_cumulo+interval_yield+OD+Cell_conc._interval+rab_integral+RQ_integral+Arg_conc.+emission_O2+consum_O2+interval_CO2; 0.477, 0.783, pH_cumulo+PL+PL_cumulo+AN+AN_cumulo+interval_yield+OD+Cell_conc._interval+rab_integral+RQ_integral+Arg_conc.+emission_O2+consum_O2+generate_CO2+interval_CO2; 0.459, 0.781, pH_cumulo+PL+PL_cumulo+AN+AN_cumulo+interval_yield+OD+Cell_conc._interval+rab_integral+RQ_integral+Arg_conc.+emission_O2+consum_O2+generate_CO2+interval_CO2; 0.472, 0.780, pH_cumulo+PL+PL_cumulo+AN+AN_cumulo+interval_yield+OD+Feed_Vol+Cell_conc._interval+rab_integral+RQ_integral+Arg_conc.+emission_O2+consum_O2; 0.485, 0.780, pH_cumulo+PL_cumulo+AN+AN_cumulo+interval_yield+OD+Cell_conc._interval+rab_integral+RQ_integral+Arg_conc.+emission_O2+consum_O2+interval_CO2; 0.472, 0.780, pH_cumulo+PL_cumulo+AN+AN_cumulo+interval_yield+OD+Feed_Vol+Cell_conc._interval+rab_integral+RQ_integral+Arg_conc.+emission_O2+consum_O2+interval_O2; 0.484, 0.780, pH_cumulo+PL_cumulo+AN+AN_cumulo+interval_yield+OD+Feed_Vol+Cell_conc._interval+rab_integral+RQ_integral+Arg_conc.+emission_O2+consum_O2; 0.457, 0.780, pH_cumulo+PL+PL_cumulo+AN+AN_cumulo+interval_yield+OD+RS_cumulo+Cell_conc._interval+rab_integral+RQ_integral+Arg_conc.+emission_O2+consum_O2+interval_CO2; 0.456, 0.779, pH+pH_cumulo+PL+PL_cumulo+AN+AN_cumulo+interval_yield+OD+Cell_conc._interval+rab_integral+RQ_integral+Arg_conc.+emission_O2+consum_O2+interval_CO2; 0.482, 0.779, pH_cumulo+PL+AN+AN_cumulo+interval_yield+OD+Feed_Vol+Cell_conc._interval+rab_integral+RQ_integral+Arg_conc.+emission_O2+consum_O2; 0.455, 0.779, pH+pH_cumulo+PL_cumulo+AN+AN_cumulo+interval_yield+OD+Cell_conc._interval+rab_integral+RQ_integral+Arg_conc.+emission_O2+consum_O2+generate_CO2+interval_CO2; 0.468, 0.779, pH_cumulo+PL_cumulo+AN+AN_cumulo+interval_yield+OD+Cell_conc._interval+rab_integral+RQ_integral+Arg_conc.+emission_O2+interval_O2+generate_CO2+interval_CO2; 0.454, 0.778, pH_cumulo+PL+PL_cumulo+AN+AN_cumulo+interval_yield+OD+Cell_conc._interval+rab_integral+RQ_integral+Arg_conc.+emission_O2+consum_O2+interval_O2+interval_CO2; 0.454, 0.778, pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_O2; 0.493, 0.778, pH_cumulo+AN+AN_cumulo+interval_yield+OD+Feed_Vol+Cell_conc._interval+rab_integral+RQ_integral+Arg_conc.+emission_O2+consum_O2; 0.453, 0.778, pH_cumulo+PL_cumulo+AN+AN_cumulo+interval_yield+OD+Feed_Vol+Cell_conc._interval+rab_integral+RQ_integral+Arg_conc.+emission_O2+consum_O2+generate_CO2+interval_CO2; 0.466, 0.778, pH_cumulo+PL_cumulo+AN+AN_cumulo+interval_yield+OD+Cell_conc._interval+rab_integral+RQ_integral+Arg_conc.+emission_O2+consum_O2+interval_O2+interval_CO2; 0.491, 0.777, pH_cumulo+PL_cumulo+AN+AN_cumulo+OD+Feed_Vol+Cell_conc._interval+rab_integral+RQ_integral+Arg_conc.+emission_O2+consum_O2; 0.451, 0.777, pH+pH_cumulo+PL_cumulo+AN+AN_cumulo+interval_yield+OD+Feed_Vol+Cell_conc._interval+rab_integral+RQ_integral+Arg_conc.+emission_O2+consum_O2+interval_O2; 0.502, 0.777, pH_cumulo+AN+AN_cumulo+OD+Feed_Vol+Cell_conc._interval+rab_integral+RQ_integral+Arg_conc.+emission_O2+consum_O2; 0.524, 0.777, pH_cumulo+AN+AN_cumulo+OD+Feed_Vol+Cell_conc._interval+Arg_conc.+emission_CO2+consum_O2; 0.450, 0.777, pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_CO2; 0.463, 0.776, pH+pH_cumulo+PL_cumulo+AN+AN_cumulo+interval_yield+OD+Cell_conc._interval+rab_integral+RQ_integral+Arg_conc.+emission_O2+consum_O2+interval_CO2; 0.463, 0.776, pH+pH_cumulo+PL_cumulo+AN+AN_cumulo+interval_yield+OD+Feed_Vol+Cell_conc._interval+rab_integral+RQ_integral+Arg_conc.+emission_O2+consum_O2; 0.462, 0.776, pH_cumulo+PL_cumulo+AN+AN_cumulo+interval_yield+OD+Feed_Vol+Cell_conc._interval+rab_integral+RQ_integral+Arg_conc.+emission_O2+consum_O2+interval_CO2; 0.448, 0.776, pH+pH_cumulo+PL+PL_cumulo+AN+AN_cumulo+interval_yield+OD+Feed_Vol+Cell_conc._interval+rab_integral+RQ_integral+Arg_conc.+emission_O2+consum_O2; 0.434, 0.776, pH+pH_cumulo+PL+PL_cumulo+AN+AN_cumulo+interval_yield+OD+Cell_conc._interval+rab_integral+RQ_integral+Arg_conc.+emission_O2+consum_O2+generate_CO2+interval_CO2; 0.462, 0.776, pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+generate_CO2; 0.510, 0.775, pH_cumulo+PL+AN+AN_cumulo+OD+Feed_Vol+Cell_conc._interval+Arg_conc.+emission_CO2+consum_O2; 0.475, 0.775, pH+pH_cumulo+AN+AN_cumulo+interval_yield+OD+Feed_Vol+Cell_conc._interval+rab_integral+RQ_integral+Arg_conc.+emission_O2+consum_O2; 0.486, 0.775, pH_cumulo+PL+AN+AN_cumulo+OD+Feed_Vol+Cell_conc._interval+rab_integral+RQ_integral+Arg_conc.+emission_O2+consum_O2; 0.474, 0.775, pH_cumulo+PL+PL_cumulo+AN+AN_cumulo+OD+Feed_Vol+Cell_conc._interval+rab_integral+RQ_integral+Arg_conc.+emission_O2+consum_O2; 0.486, 0.775, pH+pH_cumulo+AN+AN_cumulo+OD+Feed_Vol+Cell_conc._interval+rab_integral+RQ_integral+Arg_conc.+emission_O2+consum_O2; 0.432, 0.775, pH+pH_cumulo+PL+PL_cumulo+AN+AN_cumulo+interval_yield+OD+RS_cumulo+Cell_conc._interval+rab_integral+RQ_integral+Arg_conc.+emission_O2+consum_O2+interval_CO2; 0.460, 0.775, pH+pH_cumulo+PL+AN+AN_cumulo+interval_yield+OD+Feed_Vol+Cell_conc._interval+rab_integral+RQ_integral+Arg_conc.+emission_O2+consum_O2; 0.446, 0.775, tmp_cumulo+pH_cumulo+PL_cumulo+AN+AN_cumulo+interval_yield+OD+Cell_conc._interval+rab_integral+RQ_integral+Arg_conc.+emission_O2+consum_O2+generate_CO2+interval_CO2; 0.446, 0.775, pH_cumulo+PL+PL_cumulo+AN+AN_cumulo+interval_yield+OD+Cell_conc._interval+rab_integral+RQ_integral+Arg_conc.+emission_O2+interval_O2+generate_CO2+interval_CO2; 0.460, 0.775, pH_cumulo+PL+AN+AN_cumulo+interval_yield+OD+Feed_Vol+RS_cumulo+Cell_conc._interval+rab_integral+RQ_integral+Arg_conc.+emission_O2+consum_O2; 0.446, 0.775, pH+pH_cumulo+PL_cumulo+AN+AN_cumulo+interval_yield+OD+Cell_conc._interval+rab_integral+RQ_integral+Arg_conc.+emission_O2+interval_O2+generate_CO2+interval_CO2; 0.473, 0.774, pH+pH_cumulo+PL_cumulo+AN+AN_cumulo+OD+Feed_Vol+Cell_conc._interval+rab_integral+RQ_integral+Arg_conc.+emission_O2+consum_O2; 0.530, 0.774, pH_cumulo+AN_cumulo+OD+Feed_Vol+Cell_conc._interval+Arg_conc.+emission_CO2+consum_O2; 0.445, 0.774, pH_cumulo+PL_cumulo+AN+AN_cumulo+interval_yield+OD+Feed_Vol+Cell_conc._interval+rab_integral+RQ_integral+Arg_conc.+emission_O2+consum_O2+interval_O2+interval_CO2; 0.430, 0.774, pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+generate_CO2+interval_CO2; 0.430, 0.774, pH+pH_cumulo+PL_cumulo+AN+AN_cumulo+interval_yield+OD+Feed_Vol+Cell_conc._interval+rab_integral+RQ_integral+Arg_conc.+ emission_O2+consum_O2+generate_CO2+interval_CO2; 0.458, 0.774, tmp_cumulo+pH_cumulo+PL_cumulo+AN+AN_cumulo+interval_yield+OD+Cell_conc._interval+rab_integral+RQ_integral+Arg_conc.+emission_O2+consum_O2+interval_CO2; 0.444, 0.774, tmp_cumulo+pH_cumulo+PL+PL_cumulo+AN+AN_cumulo+interval_yield+OD+Cell_conc._interval+rab_integral+RQ_integral+Arg_conc.+emission_O2+consum_O2+interval_CO2; 0.430, 0.774, pH+pH_cumulo+PL+PL_cumulo+AN+AN_cumulo+interval_yield+OD+Cell_conc._interval+rab_integral+RQ_integral+Arg_conc.+emission_O2+consum_O2+interval_O2+interval_CO2; 0.458, 0.774, pH_cumulo+PL+AN+AN_cumulo+interval_yield+OD+RS_cumulo+Cell_conc._interval+rab_integral+RQ_integral+Arg_conc.+emission_O2+consum_O2+interval_CO2; 0.444, 0.774, tmp+pH_cumulo+PL+PL_cumulo+AN+AN_cumulo+interval_yield+OD+Cell_conc._interval+rab_integral+RQ_integral+Arg_conc.+emission_O2+consum_O2+interval_CO2; 0.507, 0.774, pH_cumulo+AN+AN_cumulo+OD+Feed_Vol+Cell_conc._interval+RQ_integral+Arg_conc.+emission_CO2+consum_O2; 0.429, 0.773, pH_cumulo+PL+PL_cumulo+AN+AN_cumulo+interval_yield+OD+RS_cumulo+Cell_conc._interval+rab_integral+RQ_integral+Arg_conc.+emission_O2+consum_O2+generate_CO2+interval_CO2; 0.443, 0.773, pH_cumulo+PL_cumulo+AN+AN_cumulo+interval_yield+OD+Cell_conc._interval+rab_integral+RQ_integral+Arg_conc.+emission_O2+consum_O2+interval_O2+generate_CO2+interval_CO2; 0.507, 0.773, pH+pH_cumulo+AN+AN_cumulo+OD+Feed_Vol+Cell_conc._interval+Arg_conc.+emission_CO2+consum_O2; 0.443, 0.773, pH_cumulo+PL+PL_cumulo+AN+AN_cumulo+interval_yield+OD+Feed_Vol+RS_cumulo+Cell_conc._interval+rab_integral+RQ_integral+Arg_conc.+emission_O2+consum_O2; 0.443, 0.773, pH+pH_cumulo+PL_cumulo+AN+AN_cumulo+interval_yield+OD+Cell_conc._interval+rab_integral+RQ_integral+Arg_conc.+emission_O2+consum_O2+interval_O2+interval_CO2; 0.470, 0.773, pH_cumulo+AN+AN_cumulo+interval_yield+OD+Feed_Vol+Cell_conc._interval+rab_integral+RQ_integral+Arg_conc.+emission_O2+emission_CO2+consum_O2; 0.428, 0.773, pH+pH_cumulo+PL+PL_cumulo+AN++AN_cumulo+interval_yield+OD+Feed_Vol+Cell_conc._interval+rab_integral+RQ_integral+Arg_conc.+emission_O2+consum_O2+interval_O2; 0.443, 0.773, pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+generate_CO2; 0.470, 0.773, pH_cumulo+PL+AN+AN_cumulo+interval_yield+OD+Cell_conc._interval+rab_integral+RQ_integral+Arg_conc.+emission_O2+consum_O2+interval_CO2; 0.457, 0.773, pH_cumulo+PL+AN+AN_cumulo+interval_yield+OD+Feed_Vol+Cell_conc._interval+rab_integral+RQ_integral+Arg_conc.+emission_O2+emission_CO2+consum_O2; 0.443, 0.773, pH_cumulo+PL_cumulo+AN+AN_cumulo+interval_yield+OD+Cell_conc._interval+rab_integral+RQ_integral+Arg_conc.+emission_O2+emission_CO2+consum_O2+generate_CO2+interval_CO2; 0.443, 0.773, tmp+pH_cumulo+PL_cumulo+AN+AN_cumulo+interval_yield+OD+Cell_conc._interval+rab_integral+RQ_integral+Arg_conc.+emission_O2+consum_O2+generate_CO2+interval_CO2; 0.482, 0.773, pH_cumulo+AN+AN_cumulo+OD+Feed_Vol+Cell_conc._interval+rab_integral+RQ_integral+Arg_conc.+emission_O2+emission_CO2+consum_O2; 0.469, 0.773, pH_cumulo+PL_cumulo+AN+AN_cumulo+interval_yield+OD+Cell_conc._interval+rab_integral+RQ_integral+Arg_conc.+emission_CO2+generate_CO2+interval_CO2; 0.469, 0.773, pH_cumulo+AN+AN_cumulo+interval_yield+OD+Cell_conc._interval+rab_integral+RQ_integral+Arg_conc.+emission_O2+interval_O2+generate_CO2+interval_CO2; 0.442, 0.772, pH_cumulo+PL_cumulo+AN+AN_cumulo+interval_yield+OD+RS_cumulo+Cell_conc._interval+rab_integral+RQ_integral+Arg_conc.+emission_O2+consum_O2+generate_CO2+interval_CO2; 0.427, 0.772, pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_O2+interval_CO2; 0.427, 0.772, pH_cumulo+PL+PL_cumulo+AN+AN_cumulo+interval_yield+OD+RS_cumulo+Cell_conc._interval+rab_integral+RQ_integral+Arg_conc.+emission_O2+consum_O2+interval_O2+interval_CO2; 0.426, 0.772, pH_cumulo+PL+PL_cumulo+AN+AN_cumulo+interval_yield+OD+Feed_Vol+RS_cumulo+Cell_conc._interval+rab_integral+RQ_integral+Arg_conc.+emission_O2+consum_O2+interval_CO2; 0.504, 0.772, pH_cumulo+AN+AN_cumulo+OD+Cell_conc._interval+Arg_conc.+emission_CO2+interval_O2+generate_CO2+interval_CO2; 0.426, 0.772, pH+pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_CO2; 0.441, 0.772, pH_cumulo+PL+PL_cumulo+AN+AN_cumulo+interval_yield+OD+RS+Cell_conc._interval+rab_integral+RQ_integral+Arg_conc.+emission_O2+consum_O2+interval_CO2; 0.515, 0.772, pH_cumulo+PL+AN_cumulo+OD+Feed_Vol+Cell_conc._interval+Arg_conc.+emission_CO2+consum_O2; 0.441, 0.772, pH+pH_cumulo+PL+AN+AN_cumulo+interval_yield+OD+Feed_Vol+Cell_conc._interval+rab_integral+RQ_integral+Arg_conc.+emission_O2+consum_O2+generate_CO2; 0.426, 0.772, tmp_cumulo+pH+pH_cumulo+PL_cumulo+AN+AN_cumulo+interval_yield+OD+Cell_conc._interval+rab_integral+RQ_integral+Arg_conc.+emission_O2+consum_O2+generate_CO2+interval_CO2; 0.440, 0.772, tmp_cumulo+pH_cumulo+PL_cumulo+AN+AN_cumulo+interval_yield+OD+Cell_conc._interval+rab_integral+RQ_integral+Arg_conc.+emission_O2+consum_O2+interval_O2+interval_CO2; 0.468, 0.772, pH_cumulo+PL_cumulo+AN+AN_cumulo+OD+Feed_Vol+Cell_conc._interval+rab_integral+RQ_integral+Arg_conc.+emission_O2+consum_O2+interval_CO2; 0.440, 0.772, pH_cumulo+PL_cumulo+AN+AN_cumulo+interval_yield+OD+Feed_Vol+Cell_conc._interval+rab_integral+RQ_integral+Arg_conc.+emission_O2+interval_O2+generate_CO2+interval_CO2; 0.454, 0.772, tmp+pH_cumulo+PL_cumulo+AN+AN_cumulo+interval_yield+OD+Cell_conc._interval+rab_integral+RQ_integral+Arg_conc.+emission_O2+consum_O2+interval_CO2; 0.492, 0.772, pH_cumulo+PL+AN+AN_cumulo+OD+Feed_Vol+Cell_conc._interval+RQ_integral+Arg_conc.+emission_CO2+consum_O2; 0.454, 0.772, pH_cumulo+PL_cumulo+AN+AN_cumulo+interval_yield+OD+RS_cumulo+Cell_conc._interval+rab_integral+RQ_integral+Arg_conc.+emission_O2+consum_O2+interval_CO2; 0.440, 0.772, pH+pH_cumulo+PL+AN+AN_cumulo+interval_yield+OD+Feed_Vol+Cell_conc._interval+rab_integral+RQ_integral+Arg_conc.+emission_O2+consum_O2+interval_CO2; 0.514, 0.771, pH_cumulo+AN+AN_cumulo+OD+Cell_conc._interval+Arg_conc.+emission_CO2+consum_O2+interval_CO2; 0.467, 0.771, pH+pH_cumulo+PL+AN+AN_cumulo+OD+Feed_Vol+Cell_conc._interval+rab_integral+RQ_integral+Arg_conc.+emission_O2+consum_O2; 0.453, 0.771, pH_cumulo+PL+AN+AN_cumulo+interval_yield+OD+Feed_Vol+Cell_conc._ interval+rab_integral+RQ_integral+Arg_conc.+emission_O2+consum_O2+interval_CO2; 0.491, 0.771, pH_cumulo+PL+AN+AN_cumulo+interval_yield+OD+Feed_Vol+Cell_conc._interval+Arg_conc.+emission_CO2+consum_O2; 0.491, 0.771, pH+pH_cumulo+PL+AN+AN_cumulo+OD+Feed_Vol+Cell_conc._interval+Arg_conc.+emission_CO2+consum_O2; 0.503, 0.771, pH_cumulo+AN+AN_cumulo+OD+Feed_Vol+Cell_conc._interval+rab_integral+Arg_conc.+emission_CO2+consum_O2; 0.439, 0.771, pH_cumulo+PL+PL_cumulo+AN+AN_cumulo+interval_yield+OD+Cell_conc._interval+rab_integral+RQ_integral+Arg_conc.+emission_O2+emission_CO2+consum_O2+interval_CO2; 0.466, 0.771, pH_cumulo+AN+AN_cumulo+interval_yield+OD+Feed_Vol+Cell_conc._interval+rab_integral+RQ_integral+Arg_conc.+emission_O2+consum_O2+generate_CO2; 0.424, 0.771, tmp_cumulo+pH_cumulo+PL+PL_cumulo+AN+AN_cumulo+interval_yield+OD+Cell_conc._interval+rab_integral+RQ_integral+Arg_conc.+emission_O2+consum_O2+generate_CO2+interval_CO2; 0.438, 0.771, pH_cumulo+PL_cumulo+AN+AN_cumulo+interval_yield+OD+Feed_Vol+Cell_conc._interval+rab_integral+RQ_integral+Arg_conc.+emission_O2+emission_CO2+consum_O2+interval_O2; 0.452, 0.771, pH_cumulo+PL_cumulo+AN+AN_cumulo+interval_yield+OD+RS+Cell_conc._interval+rab_integral+RQ_integral+Arg_conc.+emission_O2+consum_O2+interval_CO2; 0.491, 0.771, pH_cumulo+AN+AN_cumulo+interval_yield+OD+Cell_conc._interval+Arg_conc.+emission_CO2+interval_O2+generate_CO2+interval_CO2; 0.424, 0.771, tmp+pH_cumulo+PL+PL_cumulo+AN+AN_cumulo+interval_yield+OD+Cell_conc._interval+rab_integral+RQ_integral+Arg_conc.+emission_O2+consum_O2+generate_CO2+interval_CO2; 0.466, 0.771, tmp_cumulo+pH_cumulo+AN+AN_cumulo+interval_yield+OD+Cell_conc._interval+rab_integral+RQ_integral+Arg_conc.+emission_O2+consum_O2+interval CO2; 0.452, 0.771, pH_cumulo+PL_cumulo+AN+AN_cumulo+interval_yield+OD+Feed_Vol+RS_cumulo+Cell_conc._interval+rab_integral+RQ_integral+Arg_conc.+emission_O2+consum_O2; 0.452, 0.771, pH_cumulo+PL+AN+AN_cumulo+interval_yield+OD+Cell_conc._interval+rab_integral+RQ_integral+Arg_conc.+emission_O2+interval_O2+generate_CO2+interval_CO2; 0.452, 0.771, pH+pH_cumulo+PL+PL_cumulo+AN+AN_cumulo+OD+Feed_Vol+Cell_conc._interval+rab_integral+RQ_integral+Arg_conc.+emission_O2+consum_O2; 0.465, 0.771, pH_cumulo+AN+AN_cumulo+interval_yield+OD+Feed_Vol+Cell_conc._interval+rab_integral+RQ_integral+Arg_conc.+emission_O2+consum_O2+interval_CO2; 0.438, 0.771, tmp_cumulo+pH+pH_cumulo+PL_cumulo+AN+AN_cumulo+interval_yield+OD+Cell_conc._interval+rab_integral+RQ_integral+Arg_conc.+emission_O2+consum_O2+interval_CO2; 0.490, 0.771, pH_cumulo+AN+AN_cumulo+OD+Feed_Vol+Cell_conc._interval+rab_integral+RQ_integral+Arg_conc.+emission_CO2+consum_O2; 0.465, 0.771, pH_cumulo+AN+AN_cumulo+interval_yield+OD+Feed_Vol+Cell_conc._interval+rab_integral+RQ_integral+Arg_conc.+emission_O2+consum_O2+interval_O2; 0.438, 0.771, pH_cumulo+PL_cumulo+AN+AN_cumulo+interval_yield+OD+Feed_Vol+Cell_conc._interval+rab_integral+RQ_integral+Arg_conc.+emission_O2+consum_O2+interval_O2+generate_CO2; 0.502, 0.771, pH_cumulo+PL+AN+AN_cumulo+OD+Cell_conc._interval+Arg_conc.+emission_CO2+consum_O2+interval_CO2; 0.478, 0.771, pH_cumulo+PL_cumulo+AN+AN_cumulo+interval_yield+OD+Cell_conc._interval+Arg_conc.+emission_CO2+consum_O2+generate_CO2+interval_CO2; 0.490, 0.771, pH_cumulo+AN+AN_cumulo+OD+Feed_Vol+Cell_conc._interval+RQ_integral+Arg_conc.+emission_O2+emission_CO2+consum_O2; 0.501, 0.771, pH_cumulo+AN+AN_cumulo+interval_yield+OD+Feed_Vol+Cell_conc._interval+Arg_conc.+emission_CO2+consum_O2; 0.451, 0.771, pH_cumulo+PL_cumulo+AN+AN_cumulo+interval_yield+OD+Cell_conc._interval+rab_integral+RQ_integral+Arg_conc.+emission_O2+emission_CO2+consum_O02+interval_CO2; 0.512, 0.770, pH+pH_cumulo+AN_cumulo+OD+Feed_Vol+Cell_conc._interval+Arg_conc.+emission_CO2+consum_O2; 0.465, 0.770, pH_cumulo+PL+AN+AN_cumulo+OD+Feed_Vol+Cell_conc._interval+rab_integral+RQ_integral+Arg_conc.+emission_O2+emission_CO2+consum_O2; 0.490, 0.770, pH_cumulo+AN+AN_cumulo+OD+Feed_Vol+Cell_conc._interval+RQ_integral+Arg_conc.+emission_CO2+consum_O2+generate_CO2; 0.451, 0.770, pH_cumulo+PL+AN+AN_cumulo+interval_yield+OD+Feed_Vol+Cell_conc._interval+rab_integral+RQ_integral+Arg_conc.+emission_O2+consum_O2+interval_O2; 0.501, 0.770, pH_cumulo+AN+AN_cumulo+OD+Feed_Vol+Cell_conc._interval+Arg_conc.+emission_O2+emission_CO2+consum_O2; 0.501, 0.770, pH_cumulo+PL+AN+AN_cumulo+OD+Feed_Vol+Cell_conc._interval+Arg_conc.+emission_CO2+consum_O2; 0.437, 0.770, pH_cumulo+PL_cumulo+AN+AN_cumulo+interval_yield+OD+Feed_Vol+RS_cumulo+Cell_conc._interval+rab_integral+RQ_integral+Arg_conc.+emission_O2+consum_O2+interval_O2; 0.477, 0.770, pH_cumulo+AN+AN_cumulo+interval_yield+OD+Cell_conc._interval+rab_integral+RQ_integral+Arg_conc.+emission_O2+consum_O2+interval_CO2; 0.422, 0.770, pH+pH_cumulo+PL_cumulo+AN+AN_cumulo+interval_yield+OD+Feed_Vol+Cell_conc._interval+rab_integral+RQ_integral+Arg_conc.+emission_O2+consum_O2+interval_O2+interval_CO2; 0.451, 0.770, pH_cumulo+PL_cumulo+AN+AN_cumulo+interval_yield+OD+Feed_Vol+Cell_conc._interval+rab_integral+RQ_integral+Arg_conc.+emission_O2+emission_CO2+consum_O2; 0.437, 0.770, pH_cumulo+PL+AN+AN_cumulo+interval_yield+OD+Feed_Vol+RS_cumulo+Cell_conc._interval+rab_integral+RQ_integral+Arg_conc.+emission_O2+consum_O2+interval_CO2; 0.451, 0.770, tmp_cumulo+pH_cumulo+PL+AN+AN_cumulo+interval_yield+OD+Cell_conc._interval+rab_integral+RQ_integral+Arg_conc.+emission_O2+consum_O2+interval_CO2; 0.500, 0.770, tmp_cumulo+pH_cumulo+AN+AN_cumulo+OD+Cell_conc._interval+Arg_conc.+emission_CO2+consum_O2+interval_CO2; 0.450, 0.770, pH_cumulo+PL+PL_cumulo+AN+AN_cumulo+OD+Feed_Vol+Cell_conc._interval+rab_integral+RQ_integral+Arg_conc.+emission_O2+consum_O2+interval_CO2; 0.421, 0.770, tmp+pH+pH_cumulo+PL+PL_cumulo+AN+AN_cumulo+interval_yield+OD+Cell_conc._interval+rab_integral+RQ_integral+Arg_conc.+emission_O2+consum_O2+interval_CO2; 0.464, 0.770, pH_cumulo+AN+AN_cumulo+interval_yield+OD+Feed_Vol+RS_cumulo+Cell_conc._interval+rab_integral+RQ_integral+Arg_conc.+emission_O2+consum_O2; 0.464, 0.770, pH+pH_cumulo+AN+AN_cumulo+OD+Feed_Vol+Cell_conc._interval+rab_integral+RQ_integral+Arg_conc.+emission_O2+emission_CO2+consum_O2; 0.421, 0.770, tmp_cumulo+pH_cumulo+PL+PL_cumulo+AN+AN_cumulo+interval_yield+OD+Cell_conc._interval+rab_integral+RQ_integral+Arg_conc.+emission_O2+consum_O2+interval_O2+interval_CO2; 0.488, 0.770, pH_cumulo+PL_cumulo+AN+AN_cumulo+interval_yield+OD+Cell_conc._interval+Arg_conc.+emission_CO2+generate_CO2+interval_CO2; 0.450, 0.770, pH_cumulo+PL+AN+AN_ cumulo+interval_yield+OD+Feed_Vol+Cell_conc._interval+rab_integral+RQ_integral+Arg_conc.+emission_O2+consum_O2+generate_CO2; 0.421, 0.770, tmp+pH+pH_cumulo+PL_cumulo+AN+AN_cumulo+interval_yield+OD+Cell_conc._interval+rab_integral+RQ_integral+Arg_conc.+emission_O2+consum_O2+generate_CO2+interval_CO2; 0.488, 0.770, pH_cumulo+AN+AN_cumulo+OD+Feed_Vol+Cell_conc._interval+RQ_integral+Arg_conc.+emission_CO2+consum_O2+interval_O2; 0.436, 0.770, pH+pH_cumulo+PL+AN+AN_cumulo+interval_yield+OD+Feed_Vol+RS_cumulo+Cell_conc._interval+rab_integral+RQ_integral+Arg_conc.+emission_O2+consum_O2; 0.500, 0.770, pH_cumulo+AN+AN_cumulo+OD+Feed_Vol+Cell_conc._interval+Arg_conc.+emission_CO2+consum_O2+interval_CO2; 0.476, 0.769, pH_cumulo+AN+AN_cumulo+OD+Feed_Vol+RS_cumulo+Cell_conc._interval+rab_integral+RQ_integral+Arg_conc.+emission_O2+consum_O2; 0.449, 0.769, pH+pH_cumulo+AN+AN_cumulo+interval_yield+OD+Feed_Vol+Cell_conc._interval+rab_integral+RQ_integral+Arg_conc.+emission_O2+emission_CO2+consum_O2; 0.420, 0.769, tmp_cumulo+pH+pH_cumulo+PL+PL_cumulo+AN+AN_cumulo+interval_yield+OD+Cell_conc._interval+rab_integral+RQ_integral+Arg_conc.+emission_O2+consum_O2+interval_CO2; 0.476, 0.769, pH_cumulo+AN+AN_cumulo+OD+Feed_Vol+Cell_conc._interval+rab_integral+RQ_integral+Arg_conc.+emission_O2+consum_O2+interval_O2; 0.463, 0.769, pH_cumulo+PL_cumulo+AN+AN_cumulo+OD+Feed_Vol+RS_cumulo+Cell_conc._interval+rab_integral+RQ_integral+Arg_conc.+emission_O2+consum_O2; 0.488, 0.769, pH+pH_cumulo+AN+AN_cumulo+OD+Feed_Vol+Cell_conc._interval+RQ_integral+Arg_conc.+emission_CO2+consum_O2; 0.435, 0.769, pH_cumulo+PL_cumulo+AN+AN_cumulo+interval_yield+OD+RS+Cell_conc._interval+rab_integral+RQ_integral+Arg_conc.+emission_O2+consum_O2+generate_CO2+interval_CO2; 0.475, 0.769, pH_cumulo+AN+AN_cumulo+OD+Feed_Vol+Cell_conc._interval+rab_integral+RQ_integral+Arg_conc.+emission_O2+consum_O2+generate_CO2; 0.499, 0.769, pH_cumulo+AN+AN_cumulo+OD+Feed_Vol+Cell_conc._interval+Arg_conc.+emission_CO2+consum_O2+generate_CO2; 0.487, 0.769, pH_cumulo+PL+AN+AN_cumulo+OD+Feed_Vol+Cell_conc._interval+rab_integral+Arg_conc.+emission_CO2+consum_O2; 0.420, 0.769, tmp_cumulo+pH+pH_cumulo+PL_cumulo+AN+AN_cumulo+interval_yield+OD+Cell_conc._interval+rab_integral+RQ_integral+Arg_conc.+emission_O2+consum_O2+interval_O2+interval_CO2; 0.420, 0.769, pH+pH_cumulo+PL+PL_cumulo+AN+AN_cumulo+interval_yield+OD+Cell_conc._interval+rab_integral+RQ_integral+Arg_conc.+emission_O2+interval_O2+generate_CO2+interval_CO2; 0.499, 0.769, pH_cumulo+AN+AN_cumulo+OD+Feed_Vol+Cell_conc._interval+Arg_conc.+emission_CO2+consum_O2+interval_O2; 0.448, 0.769, pH+pH_cumulo+AN+AN_cumulo+interval_yield+OD+Cell_conc._interval+rab_integral+RQ_integral+Arg_conc.+emission_O2+interval_O2+generate_CO2+interval_CO2; 0.419, 0.769, pH+pH_cumulo+PL_cumulo+AN+AN_cumulo+interval_yield+OD+Cell_conc._interval+rab_integral+RQ_integral+Arg_conc.+emission_O2+consum_O2+interval_O2+generate_CO2+interval_CO2; 0.510, 0.769, pH_cumulo+PL_cumulo+AN_cumulo+OD+Feed_Vol+Cell_conc._interval+Arg_conc.+emission_CO2+consum_O2; 0.419, 0.769, pH_cumulo+PL+PL_cumulo+AN+AN_cumulo+interval_yield+OD+Cell_conc._interval+rab_integral+RQ_integral+Arg_conc.+emission_O2+consum_O2+interval_O2+generate_CO2+interval_CO2;
0.462, 0.769, pH_cumulo+PL_cumulo+AN+AN_cumulo+OD+Feed_Vol+Cell_conc._interval+rab_integral+RQ_integral+Arg_conc.+emission_O2+consum_O2+consum_O2+generate_CO2; 0.448, 0.769, tmp_cumulo+pH_cumulo+PL_cumulo+AN+AN_cumulo+interval_yield+OD+Cell_conc._interval+rab_integral+RQ_integral+Arg_conc.+emission_CO2+generate_CO2+interval_CO2; 0.419, 0.769, tmp+pH_cumulo+PL+PL_cumulo+AN+AN_cumulo+interval_yield+OD+Cell_conc._interval+rab_integral+RQ_integral+Arg_conc.+emission_O2+consum_O2+interval_O2+interval_CO2; 0.475, 0.769, pH_cumulo+AN+AN_cumulo+OD+Feed_Vol+Cell_conc._interval+rab_integral+RQ_integral+Arg_conc.+emission_O2+consum_O2+interval_CO2; 0.462, 0.769, pH_cumulo+PL_cumulo+AN+AN_cumulo+OD+Feed_Vol+Cell_conc._interval+rab_integral+RQ_integral+Arg_conc.+emission_O2+consum_O2+interval_O2; 0.487, 0.769, pH_cumulo+PL+AN+AN_cumulo+OD+Feed_Vol+Cell_conc._interval+Arg_conc.+emission_O2+emission_CO2+consum_O2; 0.474, 0.769, pH_cumulo+PL+AN+AN_cumulo+OD+Feed_Vol+Cell_conc._interval+rab_integral+RQ_integral+Arg_conc.+emission_CO2+consum_O2; 0.448, 0.769, pH+pH_cumulo+PL_cumulo+AN+AN_cumulo+OD+Feed_Vol+Cell_conc._interval+rab_integral+RQ_integral+Arg_conc.+emission_O2+consum_O2+interval_CO2; 0.434, 0.769, tmp+pH_cumulo+PL_cumulo+AN+AN_cumulo+interval_yield+OD+Cell_conc._interval+rab_integral+RQ_integral+Arg_conc.+emission_O2+consum_O2+interval_O2+interval_CO2; 0.419, 0.769, pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_O2+generate_CO2; 0.448, 0.769, tmp_cumulo+pH+pH_cumulo+AN+AN_cumulo+interval_yield+OD+Cell_conc._interval+rab_integral+RQ_integral+Arg_conc.+emission_O2+consum_O2+interval_CO2; 0.448, 0.769, pH+pH_cumulo+PL+AN+AN_cumulo+interval_yield+OD+Cell_conc._interval+rab_integral+RQ_integral+Arg_conc.+emission_O2+consum_O2+interval_CO2; 0.498, 0.769, pH_cumulo+AN+AN_cumulo+OD+Feed_Vol+RS_cumulo+Cell_conc._interval+Arg_conc.+emission_CO2+consum_O2; 0.461, 0.769, pH_cumulo+PL+AN+AN_cumulo+OD+Feed_Vol+RS_cumulo+Cell_conc._interval+rab_integral+RQ_integral+Arg_conc.+emission_O2+consum_O2; 0.419, 0.769, pH_cumulo+PL+PL_cumulo+AN+AN_cumulo+interval_yield+OD+Cell_conc._interval+rab_integral+RQ_integral+Arg_conc.+emission_O2+emission_CO2+consum_O2+generate_CO2+interval_CO2; 0.448, 0.769, pH+pH_cumulo+AN+AN_cumulo+interval_yield+OD+Feed_Vol+Cell_conc._interval+rab_integral+RQ_integral+Arg_conc.+emission_O2+consum_O2+generate_CO2; 0.461, 0.769, pH_cumulo+PL+AN+AN_cumulo+interval_yield+OD+Feed_Vol+Cell_conc._interval+rab_integral+RQ_integral+Arg_conc.+emission_CO2+consum_O2; 0.418, 0.769, pH_cumulo+PL+PL_cumulo+AN+AN_cumulo+interval_yield+OD+Feed_Vol+RS_cumulo+Cell_conc._interval+rab_integral+RQ_integral+Arg_conc.+emission_O2+consum_O2+interval_O2; 0.433, 0.769, pH+pH_cumulo+PL+AN+AN_cumulo+interval_yield+OD+Feed_Vol+Cell_conc._interval+rab_integral+RQ_integral+Arg_conc.+emission_O2+emission_CO2+consum_O2; 0.433, 0.769, pH_cumulo+PL+PL_cumulo+AN+AN_cumulo+interval_yield+OD+Feed_Vol+Cell_conc._interval+rab_integral+RQ_integral+Arg_conc.+emission_O2+emission_CO2+consum_O2; 0.447, 0.768, pH_cumulo+AN+AN_cumulo+interval_yield+OD+Feed_Vol+Cell_conc._interval+rab_integral+RQ_integral+Arg_conc.+emission_O2+interval_O2+generate_CO2+interval_CO2; 0.418, 0.768, pH+pH_cumulo+PL_cumulo+ AN+AN_cumulo+interval_yield+OD+Cell_conc._interval+ rab_integral+RQ_integral+Arg_conc.+emission_O2+ emission_CO2+consum_O2+generate_CO2+interval_CO2; 0.402, 0.768, pH+pH_cumulo+PL+PL_cumulo+AN+AN_ cumulo+interval_yield+OD+Feed_Vol+Cell_conc._interval+rab_integral+RQ_integral+Arg_conc.+emission_O2+ consum_O2+generate_CO2+interval_CO2; 0.447, 0.768, pH_cumulo+AN+AN_cumulo+interval_yield+OD+Cell_ conc._interval+rab_integral+RQ_integral+Arg_conc.+ emission_O2+consum_O2+interval_O2+generate_CO2+interval_CO2; 0.486, 0.768, pH_cumulo+PL+AN+AN_ cumulo+OD+Feed_Vol+Cell_conc._interval+Arg_conc.+ emission_CO2+consum_O2+interval_CO2; 0.418, 0.768, pH_cumulo+PL+PL_cumulo+AN+AN_cumulo+interval_ yield+OD+RS_cumulo+Cell_conc._interval+rab_integral+ RQ_integral+Arg_conc.+emission_O2+emission_CO2+ consum_O2+interval_CO2; 0.473, 0.768, pH_cumulo+AN+ AN_cumulo+interval_yield+OD+Feed_Vol+Cell_conc._ interval+rab_integral+RQ_integral+Arg_conc.+emission_ CO2+consum_O2; 0.473, 0.768, pH_cumulo+PL_cumulo+ AN+AN_cumulo+interval_yield+OD+Cell_conc._interval+ Arg_conc.+emission_CO2+interval_O2+generate_CO2+ interval_CO2; 0.485, 0.768, tmp_cumulo+pH_cumulo+ AN+AN_cumulo+OD+Cell_conc._interval+Arg_conc.+ emission_CO2+interval_O2+generate_CO2+interval_CO2; 0.447, 0.768, pH_cumulo+PL_cumulo+AN+AN_cumulo+ interval_yield+OD+Cell_conc._interval+rab_integral+RQ_ integral+Arg_conc.+emission_CO2+consum_O2+generate_CO2+interval CO2; 0.433, 0.768, pH_cumulo+PL_ cumulo+AN+AN_cumulo+interval_yield+OD+RS_ cumulo+Cell_conc._interval+rab_integral+RQ_integral+ Arg_conc.+emission_O2+interval_O2+generate_CO2+ interval_CO2; 0.433, 0.768, pH_cumulo+PL+AN+AN_ cumulo+interval_yield+OD+Feed_Vol+RS_cumulo+Cell_ conc._interval+rab_integral+RQ_integral+Arg_conc.+ emission_O2+emission_CO2+consum_O2; 0.433, 0.768, pH_cumulo+PL_cumulo+AN+AN_cumulo+interval_ yield+OD+Cell_conc._interval+rab_integral+RQ_integral+ Arg_conc.+emission_O2+emission_CO2+interval_O2+ generate_CO2+interval_CO2; 0.418, 0.768, pH_cumulo+ PL_cumulo+AN+AN_cumulo+interval_yield+OD+Feed_ Vol+Cell_conc._interval+rab_integral+RQ_integral+Arg_ conc.+emission_O2+emission_CO2+consum_O2+ generate_CO2+interval_CO2; 0.485, 0.768, pH+pH_ cumulo+AN+AN_cumulo+OD+Cell_conc._interval+Arg_ conc.+emission_CO2+interval_O2+generate_CO2+ interval_CO2; 0.432, 0.768, pH+pH_cumulo+PL+AN+ AN_cumulo+interval_yield+OD+RS_cumulo+Cell_conc._ interval+rab_integral+RQ_integral+Arg_conc.+emission_ O2+consum_O2+interval_CO2; 0.485, 0.768, tmp_ cumulo+pH_cumulo+AN+AN_cumulo+OD+Cell_conc._ interval+Arg_conc.+emission_CO2+consum_O2+ generate_CO2+interval_CO2; 0.473, 0.768, pH_cumulo+ PL+AN+AN_cumulo+OD+Feed_Vol+Cell_conc._interval+ RQ_integral+Arg_conc.+emission_O2+emission_CO2+ consum_O2; 0.485, 0.768, pH_cumulo+PL_cumulo+AN+ cumulo+OD+Feed_Vol+Cell_conc._interval+rab_integral+ RQ_integral+Arg_conc.+emission_O2+consum_O2; 0.485, 0.768, tmp_cumulo+pH_cumulo+PL+AN+AN_cumulo+ OD+Cell_conc._interval+Arg_conc.+emission_CO2+consum_O2+interval_CO2; 0.447, 0.768, pH_cumulo+PL+PL_ cumulo+AN+AN_cumulo+interval_yield+OD+Cell_conc._ interval+rab_integral+RQ_integral+Arg_conc.+emission_ CO2+generate_CO2+interval_CO2; 0.432, 0.768, tmp+pH+ pH_cumulo+PL_cumulo+AN+AN_cumulo+interval_ yield+OD+Cell_conc._interval+rab_integral+RQ_integral+ Arg_conc.+emission_O2+consum_O2+interval_CO2; 0.432, 0.768, pH_cumulo+PL_cumulo+AN+AN_cumulo+ interval_yield+OD+Cell_conc._interval+rab_integral+RQ_ integral+Arg_conc.+emission_O2+emission_CO2+consum_O2+interval_O2+interval_CO2; 0.460, 0.768, pH_cumulo+PL+AN+AN_cumulo+OD+Feed_Vol+Cell_ conc._interval+rab_integral+RQ_integral+Arg_conc.+ emission_O2+consum_O2+interval_O2; 0.460, 0.768, pH_cumulo+PL_cumulo+AN+AN_cumulo+OD+Feed_ Vol+Cell_conc._interval+rab_integral+RQ_integral+Arg_ conc.+emission_O2+emission_CO2+consum_O2; 0.446, 0.768, pH+pH_cumulo+AN+AN_cumulo+interval_yield+ OD+Feed_Vol+Cell_conc._interval+rab_integral+RQ_integral+Arg_conc.+emission_O2+consum_O2+interval_O2; 0.446, 0.768, pH_cumulo+PL+AN+AN_cumulo+interval_ yield+OD+Feed_Vol+Cell_conc._interval+rab_integral+ RQ_integral+Accum._Yield+Arg_conc.+emission_O2+ consum_O2; 0.417, 0.768, tmp+pH_cumulo+PL+PL_ cumulo+AN+AN_cumulo+interval_yield+OD+RS_ cumulo+Cell_conc._interval+rab_integral+RQ_integral+ Arg_conc.+emission_O2+consum_O2+interval_CO2; 0.496, 0.768, pH_cumulo+AN+AN_cumulo+OD+Cell_ conc._interval+Arg_conc.+emission_CO2+consum_O2+ generate_CO2+interval_CO2; 0.417, 0.768, pH+pH_cumulo+PL+PL_cumulo+AN+AN_cumulo+interval_yield+ OD+RS+Cell_conc._interval+rab_integral+RQ_integral+ Arg_conc.+emission_O2+consum_O2+interval_CO2; 0.401, 0.768, pH+pH_cumulo+PL+PL_cumulo+AN+AN_ cumulo+interval_yield+OD+RS_cumulo+Cell_conc._interval+rab_integral+RQ_integral+Arg_conc.+emission_O2+ consum_O2+generate_CO2+interval_CO2; 0.459, 0.768, tmp_cumulo+pH_cumulo+PL+PL_cumulo+AN+AN_cumulo+ OD+Cell_conc._interval+rab_integral+RQ_integral+Arg_ conc.+emission_O2+consum_O2+interval_CO2; 0.496, 0.768, pH+pH_cumulo+PL+AN_cumulo+OD+Feed_Vol+ Cell_conc._interval+Arg_conc.+emission_CO2+consum_ O2; 0.432, 0.768, tmp+pH_cumulo+PL+PL_cumulo+AN+ AN_cumulo+interval_yield+OD+Feed_Vol+Cell_conc._ interval+rab_integral+RQ_integral+Arg_conc.+emission_ O2+consum_O2; 0.496, 0.768, pH+pH_cumulo+AN+AN_ cumulo+OD+Cell_conc._interval+Arg_conc.+emission_ CO2+consum_O2+interval_CO2; 0.417, 0.768, pH+pH_ cumulo+PL_cumulo+AN+AN_cumulo+interval_yield+ OD+RS_cumulo+Cell_conc._interval+rab_integral+RQ_ integral+Arg_conc.+emission_O2+consum_O2+generate_ CO2+interval_CO2; 0.507, 0.768, pH_cumulo+AN+ cumulo+interval_yield+OD+Feed_Vol+Cell_conc._ interval+Arg_conc.+emission_CO2+consum_O2; 0.416, 0.768, pH_cumulo+PL_cumulo+AN+AN_cumulo+interval_yield+OD+Feed_Vol+RS_cumulo+Cell_conc._interval+rab_integral+RQ_integral+Arg_conc.+emission_O2+ consum_O2+generate_CO2+interval_CO2; 0.484, 0.768, pH_cumulo+PL+AN+AN_cumulo+OD+Cell_conc._interval+Arg_conc.+emission_CO2+interval_O2+generate_ CO2+interval_CO2; 0.484, 0.768, pH_cumulo+PL+AN+ AN_cumulo+OD+Feed_Vol+RS_cumulo+Cell_conc._ interval+Arg_conc.+emission_CO2+consum_O2; 0.496, 0.768, pH_cumulo+AN+AN_cumulo+OD+Feed_Vol+Cell_ conc._interval+RQ_integral+Arg_conc.+emission_O2+ consum_O2; 0.431, 0.768, pH_cumulo+PL_cumulo+AN+ AN_cumulo+interval_yield+OD+RS_cumulo+Cell_conc._ interval+rab_integral+RQ_integral+Arg_conc.+emission_ O2+consum_O2+interval_O2+interval_CO2; 0.416, 0.768, pH+pH_cumulo+PL_cumulo+AN+AN_cumulo+interval_ yield+OD+Feed_Vol+Cell_conc._interval+rab_integral+ RQ_integral+Arg_conc.+emission_O2+emission_CO2+ consum_O2+interval_O2; 0.445, 0.768, pH_cumulo+PL+

PL_cumulo+AN+AN_cumulo+OD+Feed_Vol+RS_cumulo+Cell_conc._interval+rab_integral+RQ_integral+Arg_conc.+emission_O2+consum_O2; 0.416, 0.768, pH+pH_cumulo+PL+PL_cumulo+AN+AN_cumulo+interval_yield+OD+Feed_Vol+RS_cumulo+Cell_conc._interval+rab_integral+RQ_integral+Arg_conc.+emission_O2+consum_O2; 0.507, 0.768, pH_cumulo+AN_cumulo+OD+Feed_Vol+Cell_conc._interval+Arg_conc.+emission_CO2+consum_O2+interval_O2; 0.472, 0.768, pH_cumulo+PL_cumulo+AN_cumulo+interval_yield+OD+Feed_Vol+Cell_conc._interval+rab_integral+RQ_integral+Arg_conc.+emission_O2+consum_O2; 0.431, 0.768, tmp_cumulo+pH_cumulo+PL_cumulo+AN+AN_cumulo+interval_yield+OD+Cell_conc._interval+rab_integral+RQ_integral+Arg_conc.+emission_O2+interval_O2+generate_CO2+interval_CO2; 0.445, 0.768, pH+pH_cumulo+AN+AN_cumulo+interval_yield+OD+Feed_Vol+Cell_conc._interval+rab_integral+RQ_integral+Arg_conc.+emission_O2+consum_O2+interval_CO2; 0.507, 0.767, pH_cumulo+AN_cumulo+OD+Feed_Vol+Cell_conc._interval+Arg_conc.+emission_CO2+consum_O2+generate_CO2; 0.445, 0.767, pH_cumulo+AN+AN_cumulo+interval_yield+OD+Cell_conc._interval+rab_integral+RQ_integral+Arg_conc.+emission_CO2+emission_O2+generate_CO2+interval_CO2; 0.445, 0.767, pH_cumulo+PL+AN+AN_cumulo+interval_yield+OD+Cell_conc._interval+rab_integral+RQ_integral+Arg_conc.+emission_O2+emission_CO2+consum_O2+interval_CO2; 0.416, 0.767, pH+pH_cumulo+PL_cumulo+AN+AN_cumulo+interval_yield+OD+Feed_Vol+Cell_conc._interval+rab_integral+RQ_integral+Arg_conc.+emission_O2+interval_O2+generate_CO2+interval_CO2; 0.458, 0.767, pH_cumulo+PL+AN+AN_cumulo+OD+Feed_Vol+Cell_conc._interval+rab_integral+RQ_integral+Arg_conc.+emission_O2+consum_O2+generate_CO2; 0.416, 0.767, pH+pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+generate_CO2; 0.484, 0.767, pH_cumulo+AN+AN_cumulo+interval_yield+OD+Cell_conc._interval+Arg_conc.+emission_CO2+consum_O2+generate_CO2+interval_CO2; 0.471, 0.767, pH+pH_cumulo+PL+AN+AN_cumulo+OD+Feed_Vol+Cell_conc._interval+RQ_integral+Arg_conc.+emission_CO2+consum_O2; 0.431, 0.767, pH_cumulo+PL_cumulo+AN+AN_cumulo+interval_yield+OD+Feed_Vol+RS_cumulo+Cell_conc._interval+rab_integral+RQ_integral+Arg_conc.+emission_O2+consum_O2+interval_CO2; 0.416, 0.767, pH_cumulo+PL+PL_cumulo+AN+AN_cumulo+interval_yield+OD+RS_cumulo+Cell_conc._interval+rab_integral+RQ_integral+Arg_conc.+emission_O2+interval_O2+generate_CO2+interval_CO2; 0.483, 0.767, pH_cumulo+PL+AN+AN_cumulo+OD+Feed_Vol+Cell_conc._interval+Arg_conc.+emission_CO2+consum_O2+generate_CO2; 0.495, 0.767, pH_cumulo+PL+AN_cumulo+interval_yield+OD+Feed_Vol+Cell_conc._interval+Arg_conc.+emission_CO2+consum_O2; 0.445, 0.767, pH_cumulo+AN+AN_cumulo+interval_yield+OD+Feed_Vol+Cell_conc._interval+rab_integral+RQ_integral+Arg_conc.+emission_O2+emission_CO2+consum_O2+generate_CO2; 0.483, 0.767, pH+pH_cumulo+PL+AN+AN_cumulo+OD+Cell_conc._interval+Arg_conc.+emission_CO2+consum_O2+interval_CO2; 0.415, 0.767, pH+pH_cumulo+PL+AN+AN_cumulo+interval_yield+OD+Feed_Vol+Cell_conc._interval+rab_integral+RQ_integral+Arg_conc.+emission_O2+consum_O2+interval_O2+generate_CO2; 0.483, 0.767, pH+pH_cumulo+AN+AN_cumulo+OD+Feed_Vol+Cell_conc._interval+rab_integral+Arg_conc.+emission_CO2+consum_O2; 0.471, 0.767, pH_cumulo+AN+AN_cumulo+OD+Feed_Vol+Cell_conc._interval+RQ_integral+Arg_conc.+emission_O2+emission_CO2+consum_O2+generate_CO2; 0.430, 0.767, tmp+pH_cumulo+PL_cumulo+AN+AN_cumulo+interval_yield+OD+Cell_conc._interval+rab_integral+RQ_integral+Arg_conc.+emission_O2+interval_O2+generate_CO2+interval_CO2; 0.471, 0.767, tmp_cumulo+pH_cumulo+AN+AN_cumulo+OD+Cell_conc._interval+rab_integral+RQ_integral+Arg_conc.+emission_CO2+consum_O2+interval_CO2; 0.399, 0.767, pH+pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_O2+interval_CO2; 0.430, 0.767, pH_cumulo+PL+PL_cumulo+AN+AN_cumulo+interval_yield+OD+Feed_Vol+Cell_conc._interval+rab_integral+RQ_integral+Accum._Yield+Arg_conc.+emission_O2+consum_O2; 0.495, 0.767, tmp+pH_cumulo+AN+AN_cumulo+OD+Feed_Vol+Cell_conc._interval+Arg_conc.+emission_CO2+consum_O2; 0.430, 0.767, pH+pH_cumulo+PL+AN+AN_cumulo+interval_yield+OD+Feed_Vol+Cell_conc._interval+rab_integral+RQ_integral+Arg_conc.+emission_O2+consum_O2+interval_CO2; 0.483, 0.767, pH_cumulo+PL+AN+AN_cumulo+OD+Feed_Vol+Cell_conc._interval+Arg_conc.+emission_CO2+consum_O2+interval_O2; 0.483, 0.767, pH_cumulo+PL+PL_cumulo+AN+AN_cumulo+OD+Feed_Vol+Cell_conc._interval+Arg_conc.+emission_CO2+consum_O2; 0.458, 0.767, pH_cumulo+PL+PL_cumulo+AN_cumulo+interval_yield+OD+Feed_Vol+Cell_conc._interval+rab_integral+RQ_integral+Arg_conc.+emission_O2+consum_O2; 0.506, 0.767, pH_cumulo+AN_cumulo+OD+Feed_Vol+Cell_conc._interval+Arg_conc.+emission_O2+emission_CO2+consum_O2; 0.399, 0.767, pH+pH_cumulo+PL+PL_cumulo+AN+AN_cumulo+interval_yield+OD+RS_cumulo+Cell_conc._interval+rab_integral+RQ_integral+Arg_conc.+emission_O2+consum_O2+interval_O2+interval_CO2; 0.430, 0.767, pH_cumulo+PL+AN+AN_cumulo+interval_yield+OD+RS_cumulo+Cell_conc._interval+rab_integral+RQ_integral+Arg_conc.+emission_O2+interval_O2+generate_CO2+interval_CO2; 0.471, 0.767, pH_cumulo+AN+AN_cumulo+interval_yield+OD+Feed_Vol+Cell_conc._interval+RQ_integral+Arg_conc.+emission_CO2+consum_O2+generate_CO2; 0.471, 0.767, pH+pH_cumulo+AN+AN_cumulo+OD+Feed_Vol+Cell_conc._interval+RQ_integral+Arg_conc.+emission_O2+emission_CO2+consum_O2; 0.430, 0.767, tmp+pH_cumulo+PL_cumulo+AN+AN_cumulo+interval_yield+OD+Feed_Vol+Cell_conc._interval+rab_integral+RQ_integral+Arg_conc.+emission_O2+consum_O2+interval_O2; 0.458, 0.767, pH+pH_cumulo+AN+AN_cumulo+OD+Feed_Vol+RS_cumulo+Cell_conc._interval+rab_integral+RQ_integral+Arg_conc.+emission_O2+consum_O2; 0.458, 0.767, pH+pH_cumulo+AN+AN_cumulo+OD+Feed_Vol+Cell_conc._interval+rab_integral+RQ_integral+Arg_conc.+emission_O2+consum_O2+interval_O2; 0.470, 0.767, pH_cumulo+PL_cumulo+AN+AN_cumulo+OD+Cell_conc._interval+rab_integral+RQ_integral+Arg_conc.+emission_O2+consum_O2+interval_CO2; 0.444, 0.767, tmp+pH_cumulo+PL+AN+AN_cumulo+interval_yield+OD+Feed_Vol+Cell_conc._interval+rab_integral+RQ_integral+Arg_conc.+emission_O2+consum_O2; 0.470, 0.767, tmp+pH_cumulo+AN+AN_cumulo+OD+Feed_Vol+Cell_conc._interval+rab_integral+RQ_integral+Arg_conc.+emission_O2+consum_O2; 0.457, 0.767, pH_cumulo+PL+AN+AN_cumulo+OD+Feed_Vol+Cell_conc._interval+rab_integral+RQ_integral+Arg_conc.+emission_O2+ consum_O2+interval_CO2; 0.444, 0.767, pH+pH_cumulo+ AN+AN_cumulo+interval_yield+OD+Feed_Vol+RS_ cumulo+Cell_conc._interval+rab_integral+RQ_integral+ Arg_conc.+emission_O2+consum_O2; 0.457, 0.767, pH_cumulo+PL+PL_cumulo+AN+AN_cumulo+interval_ yield+OD+Cell_conc._interval+rab_integral+RQ_integral+ Arg_conc.+emission_O2+consum_O2; 0.494, 0.767, pH_cumulo+AN_cumulo+OD+Feed_Vol+Cell_conc._interval+rab_integral+RQ_integral+Arg_conc.+emission_ O2+consum_O2; 0.470, 0.767, pH+pH_cumulo+AN+AN_ cumulo+OD+Feed_Vol+Cell_conc._interval+rab_integral+ RQ_integral+Arg_conc.+emission_CO2+consum_O2; 0.399, 0.767, pH+pH_cumulo+PL+PL_cumulo++AN+AN_ cumulo+interval_yield+OD+Feed_Vol+RS_cumulo+Cell_ conc._interval+rab_integral+RQ_integral+Arg_conc.+ emission_O2+consum_O2+interval_CO2; 0.414, 0.767, pH_cumulo+PL+PL_cumulo+AN+AN_cumulo+interval_ yield+OD+Cell_conc._interval+rab_integral+RQ_integral+ Arg_conc.+emission_O2+emission_CO2+consum_O2+interval_O2+interval_CO2; 0.482, 0.767, pH_cumulo+PL+ AN+AN_cumulo+interval_yield+OD+Cell_conc._interval+ Arg_conc.+emission_CO2+consum_O2+interval_CO2; 0.429, 0.767, pH_cumulo+PL+AN+AN_cumulo+interval_ yield+OD+RS_cumulo+Cell_conc._interval+rab_integral+ RQ_integral+Arg_conc.+emission_O2+emission_CO2+ consum_O2+interval_CO2; 0.429, 0.767, pH+pH_cumulo+ PL_cumulo+AN+AN_cumulo+interval_yield+OD+RS_ cumulo+Cell_conc._interval+rab_integral+RQ_integral+ Arg_conc.+emission_O2+consum_O2+interval_CO2; 0.457, 0.767, pH+pH_cumulo+AN+AN_cumulo+OD+ Feed_Vol+Cell_conc._interval+rab_integral+RQ_integral+ Arg_conc.+emission_O2+consum_O2+generate_CO2; 0.482, 0.767, pH+pH_cumulo+AN+AN_cumulo+OD+ Feed_Vol+Cell_conc._interval+RQ_integral+Arg_conc.+ emission_O2+consum_O2; 0.505, 0.767, pH_cumulo+AN_ cumulo+OD+Feed_Vol+RS_cumulo+Cell_conc._interval+ Arg_conc.+emission_CO2+consum_O2; 0.429, 0.767, pH_cumulo+PL+PL_cumulo+AN+AN_cumulo+interval_ yield+OD+Cell_conc._interval+rab_integral+RQ_integral+ Accum._Yield+Arg_conc.+emission_O2+consum_O2+interval_CO2; 0.443, 0.767, pH_cumulo+AN+AN_cumulo+ interval_yield+OD+Feed_Vol+Cell_conc._interval+rab_ integral+RQ_integral+Arg_conc.+emission_O2+emission_ CO2+consum_O2+interval_O2; 0.414, 0.767, pH_cumulo+ PL+PL_cumulo+AN+AN_cumulo+interval_yield+OD+ Feed_Vol+Cell_conc._interval+rab_integral+RQ_integral+ Arg_conc.+emission_O2+emission_CO2+consum_O2+ interval_O2; 0.470, 0.767, pH_cumulo+AN+AN_cumulo+ OD+Feed_Vol+Cell_conc._interval+RQ_integral+Arg_ conc.+emission_O2+emission_CO2+consum_O2+interval_ O2; 0.470, 0.767, pH_cumulo+PL+AN+AN_cumulo+OD+ Feed_Vol+Cell_conc._interval+RQ_integral+Arg_conc.+ emission_CO2+consum_O2+generate_CO2; 0.482, 0.767, pH+pH_cumulo+PL+PL_cumulo+AN+AN_cumulo+OD+ Feed_Vol+Cell_conc._interval+Arg_conc.+emission_CO2+ consum_O2; 0.414, 0.767, pH_cumulo+PL+PL_cumulo+ AN+AN_cumulo+interval_yield+OD+Feed_Vol+Cell_ conc._interval+rab_integral+RQ_integral+Arg_conc.+ emission_O2+interval_O2+generate_CO2+interval_CO2; 0.457, 0.767, pH+pH_cumulo+AN+AN_cumulo+OD+ Feed_Vol+Cell_conc._interval+rab_integral+RQ_integral+ Arg_conc.+emission_O2+consum_O2+interval_CO2; 0.414, 0.767, pH_cumulo+PL+AN+AN_cumulo+ interval_yield+OD+Feed_Vol+Cell_conc._interval+rab_integral+RQ_integral+Arg_conc.+emission_O2+consum_ O2+interval_O2+generate_CO2+interval_CO2; 0.443, 0.767, pH_cumulo+PL+PL_cumulo+AN+AN_cumulo+ OD+Feed_Vol+Cell_conc._interval+rab_integral+RQ_integral+Arg_conc.+emission_O2+consum_O2+generate_ CO2; 0.470, 0.767, pH_cumulo+PL+AN+AN_cumulo+ interval_yield+OD+Cell_conc._interval+Arg_conc.+ emission_CO2+interval_O2+generate_CO2+interval_CO2; 0.414, 0.767, pH+pH_cumulo+PL+PL_cumulo+AN+AN_ cumulo+interval_yield+OD+Cell_conc._interval+rab_integral+RQ_integral+Arg_conc.+emission_O2+emission_ CO2+consum_O2+interval_CO2; 0.457, 0.766, tmp+pH_ cumulo+PL_cumulo+AN+AN_cumulo+OD+Feed_Vol+ Cell_conc._interval+rab_integral+RQ_integral+Arg_ conc.+emission_O2+consum_O2; 0.443, 0.766, pH+pH_ cumulo+PL_cumulo+AN+AN_cumulo+interval_yield+ OD+Cell_conc._interval+rab_integral+RQ_integral+Arg_ conc.+emission_CO2+generate_CO2+interval_CO2; 0.457, 0.766, pH+pH_cumulo+AN+AN_cumulo+interval_yield+ OD+Cell_conc._interval+rab_integral+RQ_integral+Arg_ conc.+emission_O2+consum_O2+interval_CO2; 0.443, 0.766, pH+pH_cumulo+PL+AN+AN_cumulo+OD+Feed_ Vol+Cell_conc._interval+rab_integral+RQ_integral+Arg_ conc.+emission_O2+emission_CO2+consum_O2; 0.470, 0.766, pH+pH_cumulo+PL+AN+AN_cumulo+interval_ yield+OD+Feed_Vol+Cell_conc._interval+Arg_conc.+ emission_CO2+consum_O2; 0.482, 0.766, pH+pH_cumulo+AN+AN_cumulo+interval_yield+OD+Feed_Vol+ Cell_conc._interval+Arg_conc.+emission_CO2+consum_ O2; 0.482, 0.766, tmp_cumulo+pH+pH_cumulo+AN+AN_ cumulo+OD+Cell_conc._interval+Arg_conc.+emission_ CO2+consum_O2+interval_CO2; 0.470, 0.766, pH_cumulo+AN+AN_cumulo+interval_yield+OD+Feed_ Vol+Cell_conc._interval+RQ_integral+Arg_conc.+emission_CO2+consum_O2+interval_O2; 0.429, 0.766, pH+pH_cumulo+PL_cumulo+AN+AN_cumulo+interval_ yield+OD+RS+Cell_conc._interval+rab_integral+RQ_integral+Arg_conc.+emission_O2+consum_O2+interval_CO2; 0.443, 0.766, pH_cumulo+PL+PL_cumulo+AN+AN_cumulo+OD+Feed_Vol+Cell_conc._interval+rab_integral+ RQ_integral+Arg_conc.+emission_O2+consum_O2+interval_O2; 0.482, 0.766, pH_cumulo+AN+AN_cumulo+OD+ Feed_Vol+Cell_conc._interval+Arg_conc.+emission_CO2+ interval_O2+generate_CO2+interval_CO2; 0.414, 0.766, pH+pH_cumulo+PL+AN+AN_cumulo+interval_ yield+OD+Feed_Vol+RS_cumulo+Cell_conc._interval+ rab_integral+RQ_integral+Arg_conc.+emission_O2+consum_O2+interval_O2; 0.469, 0.766, pH_cumulo+PL+AN+ AN_cumulo+OD+Feed_Vol+Cell_conc._interval+RQ_ integral+Arg_conc.+emission_CO2+consum_O2+interval_ O2; 0.429, 0.766, pH+pH_cumulo+PL_cumulo+AN+AN_ cumulo+interval_yield+OD+Feed_Vol+Cell_conc._ interval+rab_integral+RQ_integral+Arg_conc.+emission_ O2+emission_CO2+consum_O2; 0.443, 0.766, tmp+pH_ cumulo+PL_cumulo+AN+AN_cumulo+interval_yield+ OD+Feed_Vol+Cell_conc._interval+rab_integral+RQ_ integral+Arg_conc.+emission_O2+consum_O2; 0.429, 0.766, pH_cumulo+PL_cumulo+AN+AN_cumulo+interval_yield+OD+Feed_Vol+Cell_conc._interval+rab_integral+RQ_integral+Arg_conc.+emission_O2+emission_ CO2+consum_O2+interval_CO2; 0.456, 0.766, pH_cumulo+PL+AN+AN_cumulo+interval_yield+OD+ Cell_conc._interval+rab_integral+RQ_integral+Arg_ conc.+emission_CO2+consum_O2+interval_CO2; 0.443, 0.766, pH+pH_cumulo+PL_cumulo+AN+AN_cumulo+ OD+Feed_Vol+Cell_conc._interval+rab_integral+RQ_integral+Arg_conc.+emission_O2+consum_O2+interval_O2; 0.428, 0.766, pH+pH_cumulo+PL_cumulo+AN+AN_cumulo+interval_yield+OD+Feed_Vol+RS_cumulo+Cell_ conc._interval+rab_integral+RQ_integral+Arg_conc.+ emission_O2+consum_O2; 0.469, 0.766, pH+pH_cumulo+AN+AN_cumulo+OD+Feed_Vol+Cell_conc._interval+RQ_integral+Arg_conc.+emission_CO2+consum_O2+generate_CO2; 0.456, 0.766, pH_cumulo+AN+AN_cumulo+interval_yield+OD+Feed_Vol+Cell_conc._interval+rab_integral+RQ_integral+Accum._Yield+Arg_conc.+emission_O2+consum_O2; 0.482, 0.766, pH_cumulo+AN+AN_cumulo+OD+Feed_Vol+Cell_conc._interval+rab_integral+Arg_conc.+emission_CO2+consum_O2+generate_CO2; 0.456, 0.766, pH_cumulo+PL+PL_cumulo+AN+AN_cumulo+OD+Cell_conc._interval+rab_integral+RQ_integral+Arg_conc.+emission_O2+consum_O2+interval_CO2; 0.481, 0.766, pH_cumulo+PL_cumulo+AN+AN_cumulo+OD+Feed_Vol+Cell_conc._interval+RQ_integral+Arg_conc.+emission_CO2+consum_O2; 0.456, 0.766, tmp+pH_cumulo+AN+AN_cumulo+interval_yield+OD+Feed_Vol+Cell_conc._interval+rab_integral+RQ_integral+Arg_conc.+emission_O2+consum_O2; 0.481, 0.766, pH+pH_cumulo+AN+AN_cumulo+OD+Feed_Vol+Cell_conc._interval+Arg_conc.+emission_O2+emission_CO2+consum_O2; 0.428, 0.766, pH_cumulo+PL_cumulo+AN+AN_cumulo+interval_yield+OD+Feed_Vol+Cell_conc._interval+rab_integral+RQ_integral+Accum._Yield+Arg_conc.+emission_O2+consum_O2+interval_O2; 0.397, 0.766, tmp+pH+pH_cumulo+PL+PL_cumulo+AN+AN_cumulo+interval_yield+OD+Cell_conc._interval+rab_integral+RQ_integral+Arg_conc.+emission_O2+consum_O2+generate_CO2+interval_CO2; 0.397, 0.766, tmp_cumulo+pH+pH_cumulo+PL+PL_cumulo+AN+AN_cumulo+interval_yield+OD+Cell_conc._interval+rab_integral+RQ_integral+Arg_conc.+emission_O2+consum_O2+generate_CO2+interval_CO2; 0.469, 0.766, pH+pH_cumulo+AN+AN_cumulo+interval_yield+OD+Cell_conc._interval+Arg_conc.+emission_CO2+interval_O2+generate_CO2+interval_CO2; 0.469, 0.766, pH_cumulo+PL+AN+AN_cumulo+interval_yield+OD+Feed_Vol+RS_cumulo+Cell_conc._interval+Arg_conc.+emission_CO2+consum_O2; 0.413, 0.766, tmp+tmp_cumulo+pH_cumulo+PL+PL_cumulo+AN+AN_cumulo+interval_yield+OD+Cell_conc._interval+rab_integral+Arg_conc.+emission_O2+consum_O2+interval_CO2; 0.481, 0.766, pH_cumulo+AN+AN_cumulo+OD+Cell_conc._interval+Arg_conc.+emission_CO2+consum_O2+interval_O2+generate_CO2+interval_CO2; 0.428, 0.766, pH+pH_cumulo+PL+AN+AN_cumulo+interval_yield+OD+Cell_conc._interval+rab_integral+RQ_integral+Arg_conc.+emission_O2+interval_O2+generate_CO2+interval_CO2; 0.469, 0.766, pH+pH_cumulo+AN+AN_cumulo+OD+Feed_Vol+Cell_conc._interval+RQ_integral+Arg_conc.+emission_CO2+consum_O2+interval_O2; 0.481, 0.766, pH_cumulo+AN+AN_cumulo+OD+Feed_Vol+Cell_conc._interval+rab_integral+Arg_conc.+emission_CO2+consum_O2+interval_O2; 0.413, 0.766, tmp+pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_O2; 0.428, 0.766, pH+pH_cumulo+PL_cumulo+AN+AN_cumulo+interval_yield+OD+Cell_conc._interval+rab_integral+RQ_integral+Arg_conc.+emission_O2+emission_CO2+consum_O2+interval_CO2; 0.442, 0.766, pH+pH_cumulo+PL+AN+AN_cumulo+OD+Feed_Vol+Cell_conc._interval+rab_integral+RQ_integral+Arg_conc.+emission_O2+consum_O2+generate_CO2; 0.428, 0.766, pH+pH_cumulo+PL+PL_cumulo+AN+AN_cumulo+OD+Feed_Vol+Cell_conc._interval+rab_integral+RQ_integral+Arg_conc.+emission_O2+consum_O2+interval_CO2; 0.397, 0.766, pH_cumulo+PL+PL_cumulo+AN+AN_cumulo+interval_yield+OD+Feed_Vol+RS_cumulo+Cell_conc._interval+rab_integral+RQ_integral+Arg_conc.+emission_O2+consum_O2+generate_CO2+interval_CO2; 0.481, 0.766, pH+pH_cumulo+AN+AN_cumulo+OD+Feed_Vol+Cell_conc._interval+Arg_conc.+emission_CO2+consum_O2+interval_CO2; 0.455, 0.766, pH_cumulo+PL_cumulo+AN+AN_cumulo+interval_yield+OD+Feed_Vol+Cell_conc._interval+RQ_integral+Arg_conc.+emission_CO2+consum_O2+interval_O2; 0.455, 0.766, pH_cumulo+AN+AN_cumulo+interval_yield+OD+Cell_conc._interval+rab_integral+RQ_integral+Arg_conc.+emission_CO2+interval_O2+generate_CO2+interval_CO2; 0.442, 0.766, pH_cumulo+AN+AN_cumulo+interval_yield+OD+Feed_Vol+Cell_conc._interval+rab_integral+RQ_integral+Arg_conc.+emission_O2+emission_CO2+consum_O2+interval_CO2; 0.455, 0.766, pH_cumulo+AN+AN_cumulo+interval_yield+OD+Cell_conc._interval+rab_integral+RQ_integral+Arg_conc.+emission_O2+emission_CO2+consum_O2+interval_CO2; 0.481, 0.766, pH_cumulo+PL+AN+AN_cumulo+OD+Feed_Vol+Cell_conc._interval+RQ_integral+Arg_conc.+emission_O2+consum_O2; 0.427, 0.766, tmp_cumulo+pH+pH_cumulo+PL+AN+AN_cumulo+interval_yield+OD+Cell_conc._interval+rab_integral+RQ_integral+Arg_conc.+emission_O2+consum_O2+interval_CO2; 0.427, 0.766, pH+pH_cumulo+PL+AN+AN_cumulo+interval_yield+OD+Feed_Vol+Cell_conc._interval+rab_integral+RQ_integral+Arg_conc.+emission_O2+consum_O2+interval_O2; 0.427, 0.766, pH_cumulo+PL+AN+AN_cumulo+interval_yield+OD+Feed_Vol+Cell_conc._interval+rab_integral+RQ_integral+Arg_conc.+emission_O2+emission_CO2+consum_O2+interval_CO2; 0.427, 0.766, pH_cumulo+PL_cumulo+AN+AN_cumulo+interval_yield+OD+RS+Feed_Vol+Cell_conc._interval+rab_integral+RQ_integral+Arg_conc.+emission_O2+consum_O2+interval_O2; 0.480, 0.766, tmp_cumulo+pH_cumulo+AN+AN_cumulo+OD+Cell_conc._interval+Arg_conc.+emission_CO2+consum_O2+interval_O2+interval_CO2; 0.492, 0.766, pH_cumulo+PL+PL_cumulo+AN+AN_cumulo+OD+Feed_Vol+Cell_conc._interval+Arg_conc.+emission_CO2+consum_O2; 0.441, 0.766, pH+pH_cumulo+PL_cumulo+AN+AN_cumulo+OD+Feed_Vol+RS_cumulo+Cell_conc._interval+rab_integral+RQ_integral+Arg_conc.+emission_O2+consum_O2; 0.412, 0.766, tmp+pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_CO2; 0.492, 0.766, tmp_cumulo+pH_cumulo+AN+AN_cumulo+OD+Feed_Vol+Cell_conc._interval+Arg_conc.+emission_CO2+consum_O2; 0.427, 0.766, pH_cumulo+PL_cumulo+AN+AN_cumulo+interval_yield+OD+RS+Cell_conc._interval+rab_integral+RQ_integral+Arg_conc.+emission_O2+consum_O2+interval_O2+interval_CO2; 0.480, 0.766, pH+pH_cumulo+AN+AN_cumulo+OD+Feed_Vol+Cell_conc._interval+Arg_conc.+emission_CO2+consum_O2+interval_O2; 0.480, 0.765, tmp_cumulo+pH_cumulo+AN+AN_cumulo+OD+Feed_Vol+Cell_conc._interval+Arg_conc.+emission_CO2+consum_O2+interval_CO2; 0.455, 0.765, pH_cumulo+AN+AN_cumulo+OD+Feed_Vol+Cell_conc._interval+rab_integral+RQ_integral+Arg_conc.+emission_O2+emission_CO2+consum_O2+generate_CO2; 0.441, 0.765, pH_cumulo+PL_cumulo+AN+AN_cumulo+interval_yield+OD+Feed_Vol+Cell_conc._interval+rab_integral+RQ_integral+Arg_conc.+emission_CO2+consum_O2+interval_O2; 0.441, 0.765, tmp_cumulo+pH+pH_cumulo+PL_cumulo+AN+AN_cumulo+OD+Cell_conc._interval+rab_integral+RQ_integral+Arg_conc.+emission_O2+consum_O2+interval_CO2; 0.427, 0.765, pH_cumulo+

PL_cumulo+AN+AN_cumulo+interval_yield+OD+Feed_Vol+Cell_conc._interval+rab_integral+RQ_integral+Arg_conc.+emission_O2+emission_CO2+consum_O2+generate_CO2; 0.412, 0.765, tmp+pH_cumulo+PL_cumulo+AN+AN_cumulo+interval_yield+OD+Feed_Vol+Cell_conc._interval+rab_integral+RQ_integral+Arg_conc.+emission_O2+consum_O2+generate_CO2+interval_CO2; 0.411, 0.765, tmp+pH+pH_cumulo+PL_cumulo+AN+AN_cumulo+interval_yield+OD+Cell_conc._interval+rab_integral+RQ_integral+Arg_conc.+emission_O2+consum_O2+interval_O2+interval_CO2; 0.396, 0.765, pH_cumulo+PL+PL_cumulo+AN+AN_cumulo+interval_yield+OD+Feed_Vol+RS_cumulo+Cell_conc._interval+rab_integral+RQ_integral+Arg_conc.+emission_O2+consum_O2+interval_O2+interval_CO2; 0.411, 0.765, tmp_cumulo+pH_cumulo+PL_cumulo+AN+AN_cumulo+interval_yield+OD+Feed_Vol+Cell_conc._interval+rab_integral+RQ+RQ_integral+Arg_conc.+emission_O2+consum_O2+generate_CO2+interval_CO2; 0.480, 0.765, pH_cumulo+AN+AN_cumulo+OD+Feed_Vol+Cell_conc._interval+rab_integral+Arg_conc.+emission_O2+emission_CO2+consum_O2; 0.441, 0.765, pH_cumulo+PL_cumulo+AN+AN_cumulo+interval_yield+OD+Feed_Vol+Cell_conc._interval+rab_integral+RQ_integral+Accum._Yield+Arg_conc.+emission_O2+consum_O2; 0.467, 0.765, tmp_cumulo+pH_cumulo+AN+AN_cumulo+interval_yield+OD+Cell_conc._interval+Arg_conc.+emission_CO2+interval_O2+generate_CO2+interval_CO2; 0.480, 0.765, tmp+pH_cumulo+PL+AN+AN_cumulo+OD+Feed_Vol+Cell_conc._interval+Arg_conc.+emission_CO2+consum_O2; 0.426, 0.765, pH_cumulo+PL+AN+AN_cumulo+interval_yield+OD+Feed_Vol+Cell_conc._interval+rab_integral+RQ_integral+Arg_conc.+emission_O2+interval_O2+generate_CO2+interval_CO2; 0.426, 0.765, pH_cumulo+PL+AN+AN_cumulo+interval_yield+OD+Feed_Vol+RS_cumulo+Cell_conc._interval+rab_integral+RQ_integral+Accum._Yield+Arg_conc.+emission_O2+consum_O2; 0.441, 0.765, tmp_cumulo+pH_cumulo+AN+AN_cumulo+interval_yield+OD+Cell_conc._interval+rab_integral+RQ_integral+Arg_conc.+emission_O2+emission_CO2+consum_O2+interval_CO2; 0.491, 0.765, pH_cumulo+AN+AN_cumulo+OD+Cell_conc._interval+Arg_conc.+emission_CO2+consum_O2+interval_O2+interval_CO2; 0.411, 0.765, pH_cumulo+PL+PL_cumulo+AN+AN_cumulo+interval_yield+OD+Feed_Vol+Cell_conc._interval+rab_integral+RQ_integral+Accum._Yield+Arg_conc.+emission_O2+consum_O2+interval_O2; 0.467, 0.765, pH_cumulo+PL+AN+AN_cumulo+interval_yield+OD+Feed_Vol+Cell_conc._interval+Arg_conc.+emission_O2+emission_CO2+consum_O2; 0.480, 0.765, pH+pH_cumulo+AN+AN_cumulo+OD+Feed_Vol+Cell_conc._interval+Arg_conc.+emission_CO2+consum_O2+generate_CO2; 0.411, 0.765, pH_cumulo+PL+PL_cumulo+AN+AN_cumulo+interval_yield+OD+Feed_Vol+Cell_conc._interval+rab_integral+RQ_integral+Arg_conc.+emission_O2+emission_CO2+consum_O2+interval_CO2; 0.467, 0.765, tmp_cumulo+pH_cumulo+AN+AN_cumulo+OD+Cell_conc._interval+rab_integral+RQ_integral+Arg_conc.+emission_O2+consum_O2+interval_CO2; 0.441, 0.765, pH_cumulo+PL_cumulo+AN+AN_cumulo+OD+Feed_Vol+Cell_conc._interval+rab_integral+RQ_integral+Arg_conc.+emission_O2+consum_O2+generate_CO2+interval_CO2; 0.454, 0.765, pH_cumulo+AN+AN_cumulo+OD+Feed_Vol+Cell_conc._interval+rab_integral+RQ_integral+Arg_conc.+emission_O2+emission_CO2+consum_O2+interval_CO2; 0.426, 0.765, pH_cumulo+PL_cumulo+AN+AN_cumulo+interval_yield+OD+Feed_Vol+RS_cumulo+Cell_conc._interval+rab_integral+RQ_integral+Arg_conc.+emission_O2+consum_O2+generate_CO2; 0.454, 0.765, pH_cumulo+AN+AN_cumulo+OD+Feed_Vol+RS_cumulo+Cell_conc._interval+rab_integral+RQ_integral+Arg_conc.+emission_O2+emission_CO2+consum_O2; 0.454, 0.765, pH+pH_cumulo+PL_cumulo+AN+AN_cumulo+interval_yield+OD+Cell_conc._interval+Arg_conc.+emission_CO2+consum_O2+generate_CO2+interval_CO2; 0.479, 0.765, tmp+pH_cumulo+AN+AN_cumulo+OD+Cell_conc._interval+Arg_conc.+emission_CO2+interval_O2+generate_CO2+interval_CO2; 0.467, 0.765, pH_cumulo+PL+PL_cumulo+AN+AN_cumulo+OD+Feed_Vol+Cell_conc._interval+rab_integral+RQ_integral+Arg_conc.+emission_O2+consum_O2; 0.479, 0.765, pH_cumulo+PL+AN+AN_cumulo+OD+Cell_conc._interval+Arg_conc.+emission_CO2+consum_O2+generate_CO2+interval_CO2; 0.454, 0.765, pH_cumulo+AN+AN_cumulo+OD+Feed_Vol+Cell_conc._interval+rab_integral+RQ_integral+Arg_conc.+emission_O2+emission_CO2+consum_O2+interval_O2; 0.467, 0.765, tmp_cumulo+pH+pH_cumulo+AN+AN_cumulo+OD+Cell_conc._interval+Arg_conc.+emission_CO2+consum_O2+generate_CO2+interval_CO2; 0.479, 0.765, pH_cumulo+AN+AN_cumulo+OD+Feed_Vol+Cell_conc._interval+Arg_conc.+emission_CO2+consum_O2+generate_CO2+interval_CO2; 0.479, 0.765, pH_cumulo+PL_cumulo+AN+AN_cumulo+OD+Cell_conc._interval+Arg_conc.+emission_CO2+interval_O2+generate_CO2+interval_CO2; 0.454, 0.765, pH_cumulo+PL+PL_cumulo+AN+AN_cumulo+interval_yield+OD+Cell_conc._interval+Arg_conc.+emission_CO2+consum_O2+generate_CO2+interval_CO2; 0.440, 0.765, pH_cumulo+AN+AN_cumulo+interval_yield+OD+Feed_Vol+Cell_conc._interval+rab_integral+RQ_integral+Arg_conc.+emission_O2+consum_O2+generate_CO2+interval_CO2; 0.440, 0.765, pH+pH_cumulo+PL_cumulo+AN+AN_cumulo+OD+Feed_Vol+Cell_conc._interval+rab_integral+RQ_integral+Arg_conc.+emission_O2+emission_CO2+consum_O2; 0.411, 0.765, pH_cumulo+PL+PL_cumulo+AN+AN_cumulo+interval_yield+OD+RS+Cell_conc._interval+rab_integral+RQ_integral+Arg_conc.+emission_O2+consum_O2+generate_CO2+interval_CO2; 0.411, 0.765, tmp+tmp_cumulo+pH_cumulo+PL_cumulo+AN+AN_cumulo+interval_yield+OD+Cell_conc._interval+rab_integral+RQ_integral+Arg_conc.+emission_O2+consum_O2+generate_CO2+interval_CO2; 0.426, 0.765, tmp+tmp_cumulo+pH_cumulo+PL_cumulo+AN+AN_cumulo+interval_yield+OD+Cell_conc._interval+rab_integral+RQ_integral+Arg_conc.+emission_O2+consum_O2+interval_CO2; 0.479, 0.765, pH_cumulo+AN+AN_cumulo+OD+Feed_Vol+RS_cumulo+Cell_conc._interval+RQ_integral+Arg_conc.+emission_CO2+consum_O2; 0.426, 0.765, pH+pH_cumulo+AN+AN_cumulo+interval_yield+OD+Feed_Vol+Cell_conc._interval+rab_integral+RQ_integral+Arg_conc.+emission_O2+interval_O2+generate_CO2+interval_CO2; 0.467, 0.765, pH_cumulo+AN+AN_cumulo+interval_yield+OD+Cell_conc._interval+Arg_conc.+emission_CO2+consum_O2+interval_O2+generate_CO2+interval_CO2; 0.467, 0.765, tmp_cumulo+pH_cumulo+AN+AN_cumulo+OD+Feed_Vol+Cell_conc._interval+rab_integral+RQ_integral+Arg_conc.+emission_O2+consum_O2; 0.440, 0.765, tmp+pH_cumulo+PL_cumulo+AN+AN_cumulo+interval_yield+OD+Cell_conc._interval+rab_integral+RQ_integral+Arg_conc.+emission_CO2+generate_CO2+interval_CO2; 0.440, 0.765, pH_cumulo+PL_cumulo+AN+AN_cumulo+interval_yield+OD+RS+Feed_Vol+Cell_conc._interval+rab_integral+RQ_integral+Arg_conc.+emission_O2+consum_O2;

0.394, 0.765, tmp_cumulo+pH+pH_cumulo+PL+PL_cumulo+AN+AN_cumulo+interval_yield+OD+Cell_conc._interval+rab_integral+RQ_integral+Arg_conc.+emission_O2+consum_O2+interval_O2+interval_CO2; 0.491, 0.765, pH_cumulo+PL+AN+AN_cumulo+OD+Feed_Vol+Cell_conc._interval+Arg_conc.+emission_O2+emission_CO2+consum_O2; 0.491, 0.765, pH+pH_cumulo+PL_cumulo+AN_cumulo+OD+Feed_Vol+Cell_conc._interval+Arg_conc.+emission_CO2+consum_O2; 0.491, 0.765, pH_cumulo+PL_cumulo+AN+AN_cumulo+OD+Cell_conc._interval+Arg_conc.+emission_CO2+consum_O2+interval_CO2; 0.467, 0.765, pH+pH_cumulo+PL_cumulo+AN_cumulo+OD+Feed_Vol+Cell_conc._interval+rab_integral+RQ_integral+Arg_conc.+emission_O2+consum_O2; 0.425, 0.765, pH_cumulo+PL_cumulo+AN+AN_cumulo+interval_yield+OD+RS+Cell_conc._interval+rab_integral+RQ_integral+Arg_conc.+emission_O2+interval_O2+generate_CO2+interval_CO2; 0.491, 0.765, pH_cumulo+PL+AN_cumulo+OD+Feed_Vol+Cell_conc._interval+Arg_conc.+emission_CO2+consum_O2+interval_O2; 0.466, 0.765, pH+pH_cumulo+PL+AN+AN_cumulo+OD+Feed_Vol+Cell_conc._interval+rab_integral+Arg_conc.+emission_CO2+consum_O2; 0.453, 0.765, pH+pH_cumulo+PL+AN+AN_cumulo+OD+Feed_Vol+Cell_conc._interval+rab_integral+RQ_integral+Arg_conc.+emission_CO2+consum_O2; 0.479, 0.765, pH_cumulo+AN+AN_cumulo+interval_yield+OD+Feed_Vol+Cell_conc._interval+Arg_conc.+emission_O2+emission_CO2+consum_O2; 0.425, 0.765, tmp+tmp_cumulo+pH_cumulo+PL+AN+AN_cumulo+interval_yield+OD+Cell_conc._interval+rab_integral+RQ_integral+Arg_conc.+emission_O2+consum_O2+interval_CO2; 0.453, 0.765, tmp+pH+pH_cumulo+AN+AN_cumulo+OD+Feed_Vol+Cell_conc._interval+rab_integral+RQ_integral+Arg_conc.+emission_O2+consum_O2; 0.425, 0.765, pH_cumulo+PL+AN+AN_cumulo+interval_yield+OD+Feed_Vol+Cell_conc._interval+rab_integral+RQ_integral+Arg_conc.+emission_O2+emission_CO2+consum_O2+interval_O2; 0.453, 0.765, pH_cumulo+PL_cumulo+AN+AN_cumulo+interval_yield+OD+Cell_conc._interval+rab_integral+RQ_integral+Arg_conc.+emission_O2+generate_CO2+interval_CO2; 0.466, 0.765, pH_cumulo+PL+AN+AN_cumulo+interval_yield+OD+Cell_conc._interval+Arg_conc.+emission_CO2+consum_O2+generate_CO2+interval_CO2; 0.440, 0.765, pH_cumulo+AN+AN_cumulo+interval_yield+OD+Feed_Vol+Cell_conc._interval+rab_integral+RQ_integral+Arg_conc.+emission_O2+consum_O2+interval_O2+generate_CO2; 0.440, 0.765, pH+pH_cumulo+PL+AN+AN_cumulo+OD+Feed_Vol+RS_cumulo+Cell_conc._interval+rab_integral+RQ_integral+Arg_conc.+emission_O2+consum_O2; 0.491, 0.765, pH_cumulo+AN+AN_cumulo+interval_yield+OD+Cell_conc._interval+Arg_conc.+emission_CO2+consum_O2+interval_CO2; 0.440, 0.765, pH_cumulo+PL+AN+AN_cumulo+interval_yield+OD+Cell_conc._interval+rab_integral+RQ_integral+Arg_conc.+emission_CO2+consum_O2+interval_O2+interval_CO2; 0.440, 0.765, pH_cumulo+AN+AN_cumulo+interval_yield+OD+Feed_Vol+RS_cumulo+Cell_conc._interval+rab_integral+RQ_integral+Arg_conc.+emission_O2+emission_CO2+consum_O2; 0.479, 0.765, pH_cumulo+AN+AN_cumulo+OD+Feed_Vol+Cell_conc._interval+RQ_integral+Arg_conc.+emission_CO2+consum_O2+interval_CO2; 0.466, 0.765, tmp_cumulo+pH_cumulo+AN+AN_cumulo+interval_yield+OD+Cell_conc._interval+Arg_conc.+emission_CO2+consum_O2+generate_CO2+interval_CO2; 0.425, 0.765, pH+pH_cumulo+PL+AN+AN_cumulo+interval_yield+OD+Feed_Vol+Cell_conc._interval+rab_integral+RQ_integral+Arg_conc.+emission_O2+consum_O2+generate_CO2; 0.453, 0.765, tmp_cumulo+pH_cumulo+AN+AN_cumulo+interval_yield+OD+Cell_conc._interval+rab_integral+RQ_integral+Arg_conc.+emission_CO2+consum_O2+interval_CO2; 0.410, 0.765, pH_cumulo+PL_cumulo+AN+AN_cumulo+interval_yield+OD+Feed_Vol+Cell_conc._interval+rab_integral+RQ_integral+Arg_conc.+emission_O2+emission_CO2+consum_O2+interval_O2+interval_CO2; 0.479, 0.765, pH+pH_cumulo+AN+AN_cumulo+OD+Feed_Vol+RS_cumulo+Cell_conc._interval+Arg_conc.+emission_CO2+consum_O2; 0.440, 0.765, pH_cumulo+PL_cumulo+AN+AN_cumulo+interval_yield+OD+Cell_conc._interval+rab_integral+RQ_integral+Arg_conc.+emission_CO2+interval_O2+generate_CO2+interval_CO2; 0.466, 0.765, pH_cumulo+PL+AN+AN_cumulo+interval_yield+OD+Cell_conc._interval+rab_integral+RQ_integral+Arg_conc.+emission_O2+consum_O2; 0.425, 0.765, pH_cumulo+PL+AN+AN_cumulo+interval_yield+OD+RS_cumulo+Cell_conc._interval+rab_integral+RQ_integral+Arg_conc.+emission_O2+consum_O2+interval_O2+interval_CO2; 0.453, 0.765, tmp_cumulo+pH_cumulo+PL+AN+AN_cumulo+interval_yield+OD+Cell_conc._interval+Arg_conc.+emission_CO2+consum_O2+generate_CO2+interval_CO2; 0.410, 0.765, pH+pH_cumulo+PL_cumulo+AN+AN_cumulo+interval_yield+OD+RS+Cell_conc._interval+rab_integral+RQ_integral+Arg_conc.+emission_O2+consum_O2+generate_CO2+interval CO2; 0.466, 0.765, tmp_cumulo+pH+pH_cumulo+AN+AN_cumulo+OD+Cell_conc._interval+Arg_conc.+emission_CO2+interval_O2+generate_CO2+interval_CO2; 0.502, 0.765, tmp+pH_cumulo+AN_cumulo+OD+Feed_Vol+Cell_conc._interval+Arg_conc.+emission_CO2+consum_O2; 0.425, 0.765, pH+pH_cumulo+AN+AN_cumulo+interval_yield+OD+Cell_conc._interval+rab_integral+RQ_integral+Arg_conc.+emission_O2+consum_O2+interval_O2+generate_CO2+interval_CO2; 0.453, 0.765, pH_cumulo+AN+AN_cumulo+interval_yield+OD+Feed_Vol+Cell_conc._interval+rab_integral+RQ_integral+Arg_conc.+emission_CO2+consum_O2+generate_CO2; 0.410, 0.765, pH+pH_cumulo+PL+AN+AN_cumulo+interval_yield+OD+Feed_Vol+RS_cumulo+Cell_conc._interval+rab_integral+RQ_integral+Arg_conc.+emission_O2+consum_O2+interval_CO2; 0.410, 0.765, tmp_cumulo+pH_cumulo+PL_cumulo+AN+AN_cumulo+interval_yield+OD+Cell_conc._interval+rab_integral+RQ_integral+Arg_conc.+emission_O2+emission_CO2+consum_O2+generate_CO2+interval_CO2; 0.453, 0.765, tmp+pH_cumulo+PL+AN+AN_cumulo+OD+Feed_Vol+Cell_conc._interval+rab_integral+RQ_integral+Arg_conc.+emission_O2+consum_O2; 0.466, 0.765, pH_cumulo+PL+AN_cumulo+OD+Feed_Vol+Cell_conc._interval+rab_integral+RQ_integral+Arg_conc.+emission_CO2+consum_O2; 0.466, 0.765, pH_cumulo+AN+AN_cumulo+OD+Feed_Vol+Cell_conc._interval+RQ_integral+Arg_conc.+emission_CO2+consum_O2+interval_O2+generate_CO2; 0.490, 0.765, pH_cumulo+PL+AN_cumulo+OD+Feed_Vol+Cell_conc._interval+Arg_conc.+emission_CO2+consum_O2+generate_CO2; 0.502, 0.765, pH_cumulo+AN+AN_cumulo+OD+Feed_Vol+Cell_conc._interval+rab_integral+Arg_conc.+emission_CO2+consum_O2; 0.410, 0.765, pH_cumulo+PL+PL_cumulo+AN+AN_cumulo+interval_yield+OD+RS_cumulo+Cell_conc._interval+rab_integral+RQ_integral+Accum._Yield+Arg_conc.+emission_O2+consum_O2+interval_CO2; 0.425, 0.765, tmp_cumulo+pH_cumulo+PL_cumulo+AN+AN_cumulo+interval_yield+OD+Feed_Vol+Cell_conc._interval+rab_integral+

RQ_integral+Arg_conc.+emission_O2+consum_O2+ interval_CO2; 0.439, 0.765, pH_cumulo+PL+AN+AN_cumulo+interval_yield+OD+Cell_conc._interval+rab_integral+RQ_integral+Arg_conc.+emission_O2+consum_O2+generate_CO2+interval_CO2; 0.490, 0.765, tmp+pH_cumulo+AN+AN_cumulo+OD+Cell_conc._interval+Arg_conc.+emission_CO2+consum_O2+interval_CO2; 0.425, 0.765, pH_cumulo+PL+AN+AN_cumulo+interval_yield+OD+Feed_Vol+RS_cumulo+Cell_conc._interval+rab_integral+RQ_integral+Arg_conc.+emission_O2+consum_O2+interval_O2; 0.439, 0.765, tmp_cumulo+pH_cumulo+AN+AN_cumulo+interval_yield+OD+Cell_conc._interval+rab_integral+RQ_integral+Arg_conc.+emission_O2+interval_O2+generate_CO2+interval_CO2; 0.439, 0.765, tmp_cumulo+pH_cumulo+PL+PL_cumulo+AN+AN_cumulo+OD+Cell_conc._interval+rab_integral+RQ_integral+Arg_conc.+emission_O2+consum_O2+interval_CO2; 0.439, 0.765, tmp+pH_cumulo+PL+PL_cumulo+AN+AN_cumulo+OD+Feed_Vol+Cell_conc._interval+rab_integral+RQ_integral+Arg_conc.+emission_O2+consum_O2; 0.466, 0.765, tmp_cumulo+pH_cumulo+PL+AN+AN_cumulo+OD+Cell_conc._interval+Arg_conc.+emission_CO2+consum_O2+generate_CO2+interval_CO2; 0.425, 0.765, tmp+pH_cumulo+PL+AN+AN_cumulo+interval_yield+OD+Feed_Vol+Cell_conc._interval+rab_integral+RQ_integral+Arg_conc.+emission_O2+consum_O2+interval_CO2; 0.410, 0.765, pH_cumulo+PL_cumulo+AN+AN_cumulo+interval_yield+OD+Feed_Vol+RS_cumulo+Cell_conc._interval+rab_integral+RQ_integral+Arg_conc.+emission_O2+consum_O2+interval_O2+interval_CO2; 0.478, 0.765, pH+pH_cumulo+AN_cumulo+OD+Feed_Vol+Cell_conc._interval+rab_integral+RQ_integral+Arg_conc.+emission_O2+consum_O2; 0.394, 0.764, tmp+pH+pH_cumulo+PL+PL_cumulo+AN+AN_cumulo+interval_yield+OD+Cell_conc._interval+rab_integral+RQ_integral+Arg_conc.+emission_O2+consum_O2+interval_O2+interval_CO2; 0.501, 0.764, pH_cumulo+AN_cumulo+OD+Feed_Vol+Cell_conc._interval+RQ_integral+Arg_conc.+emission_O2+consum_O2; 0.439, 0.764, pH_cumulo+PL_cumulo+AN+AN_cumulo+OD+Feed_Vol+RS_cumulo+Cell_conc._interval+rab_integral+RQ_integral+Arg_conc.+emission_O2+consum_O2+interval_CO2; 0.490, 0.764, pH_cumulo+PL+AN_cumulo+OD+Feed_Vol+RS_cumulo+Cell_conc._interval+Arg_conc.+emission_CO2+consum_O2; 0.409, 0.764, tmp_cumulo+pH+pH_cumulo+PL+AN+AN_cumulo+interval_yield+OD+Cell_conc._interval+rab_integral+RQ_integral+Arg_conc.+emission_O2+interval_O2+generate_CO2+interval_CO2; 0.466, 0.764, pH_cumulo+AN+AN_cumulo+interval_yield+OD+Cell_conc._interval+rab_integral+RQ_integral+Arg_conc.+emission_CO2+consum_O2+interval_CO2; 0.424, 0.764, pH_cumulo+PL+AN+AN_cumulo+interval_yield+OD+Cell_conc._interval+rab_integral+RQ_integral+Arg_conc.+emission_O2+consum_O2+interval_O2+generate_CO2+interval_CO2; 0.409, 0.764, tmp+pH+pH_cumulo+PL+AN+AN_cumulo+interval_yield+OD+Feed_Vol+Cell_conc._interval+rab_integral+RQ_integral+Arg_conc.+emission_O2+consum_O2+interval_O2; 0.424, 0.764, pH_cumulo+PL+AN+AN_cumulo+interval_yield+OD+Feed_Vol+Cell_conc._interval+rab_integral+RQ_integral+Arg_conc.+emission_O2+emission_CO2+consum_O2+generate_CO2; 0.465, 0.764, pH+pH_cumulo+PL+AN+AN_cumulo+OD+Feed_Vol+Cell_conc._interval+Arg_conc.+emission_CO2+consum_O2+interval_CO2; 0.478, 0.764, pH_cumulo+PL_cumulo+AN+AN_cumulo+OD+Cell_conc._interval+Arg_conc.+emission_CO2+consum_O2+generate_CO2+interval_CO2; 0.465, 0.764, pH_cumulo+PL_cumulo+AN+AN_cumulo+OD+Feed_Vol+Cell_conc._interval+RQ_integral+Arg_conc.+emission_CO2+consum_O2+interval_CO2; 0.452, 0.764, pH_cumulo+AN+AN_cumulo+interval_yield+OD+Feed_Vol+Cell_conc._interval+rab_integral+RQ_integral+Arg_conc.+emission_O2+interval_O2+generate_CO2; 0.478, 0.764, pH+pH_cumulo+AN+AN_cumulo+OD+Cell_conc._interval+Arg_conc.+emission_CO2+consum_O2+generate_CO2+interval_CO2; 0.465, 0.764, pH_cumulo+PL+AN+AN_cumulo+OD+Feed_Vol+Cell_conc._interval+RQ_integral+Arg_conc.+emission_CO2+consum_O2+generate_CO2; 0.439, 0.764, pH_cumulo+AN+AN_cumulo+interval_yield+OD+Feed_Vol+Cell_conc._interval+rab_integral+RQ_integral+Accum._Yield+Arg_conc.+emission_O2+emission_CO2+consum_O2; 0.424, 0.764, pH_cumulo+PL+AN+AN_cumulo+interval_yield+OD+Feed_Vol+Cell_conc._interval+rab_integral+RQ_integral+Accum._Yield+Arg_conc.+emission_O2+emission_CO2+consum_O2; 0.465, 0.764, pH_cumulo+AN+AN_cumulo+OD+Cell_conc._interval+rab_integral+RQ_integral+Arg_conc.+emission_O2+interval_O2+generate_CO2+interval_CO2; 0.439, 0.764, tmp+pH_cumulo+PL_cumulo+AN+AN_cumulo+OD+Feed_Vol+Cell_conc._interval+rab_integral+RQ_integral+Arg_conc.+emission_O2+consum_O2+interval_CO2; 0.501, 0.764, pH_cumulo+AN_cumulo+OD+Feed_Vol+Cell_conc._interval+Arg_conc.+emission_CO2+interval_O2+generate_CO2; 0.478, 0.764, pH_cumulo+AN_cumulo+interval_yield+OD+Feed_Vol+Cell_conc._interval+rab_integral+RQ_integral+Arg_conc.+emission_O2+consum_O2; 0.501, 0.764, pH_cumulo+AN+AN_cumulo+OD+Feed_Vol+Cell_conc._interval+RQ_integral+Arg_conc.+emission_CO2+consum_O2; 0.452, 0.764, pH_cumulo+AN+AN_cumulo+OD+Feed_Vol+Cell_conc._interval+rab_integral+RQ_integral+Arg_conc.+emission_O2+interval_O2+generate_CO2+interval_CO2; 0.438, 0.764, pH_cumulo+AN+AN_cumulo+interval_yield+OD+RS_cumulo+Cell_conc._interval+rab_integral+RQ_integral+Arg_conc.+emission_O2+interval_O2+generate_CO2+interval_CO2; 0.438, 0.764, tmp_cumulo+pH_cumulo+PL_cumulo+AN+AN_cumulo+OD+Feed_Vol+Cell_conc._interval+rab_integral+RQ_integral+Arg_conc.+emission_O2+consum_O2+interval_CO2; 0.424, 0.764, pH_cumulo+PL+AN+AN_cumulo+interval_yield+OD+Cell_conc._interval+rab_integral+RQ_integral+Arg_conc.+emission_O2+emission_CO2+interval_O2+generate_CO2+interval_CO2; 0.409, 0.764, tmp_cumulo+pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_CO2; 0.424, 0.764, pH_cumulo+PL_cumulo+AN+AN_cumulo+interval_yield+OD+RS+Feed_Vol+Cell_conc._interval+rab_integral+RQ_integral+Arg_conc.+emission_O2+consum_O2+interval_CO2; 0.452, 0.764, pH_cumulo+AN+AN_cumulo+interval_yield+OD+Cell_conc._interval+rab_integral+RQ_integral+Arg_conc.+emission_O2+consum_O2+generate_CO2+interval_CO2; 0.438, 0.764, pH_cumulo+PL+PL_cumulo+AN+AN_cumulo+OD+Feed_Vol+Cell_conc._interval+rab_integral+RQ_integral+Arg_conc.+emission_O2+emission_CO2+consum_O2; 0.477, 0.764, pH_cumulo+PL_cumulo+AN+AN_cumulo+OD+Feed_Vol+Cell_conc._interval+Arg_conc.+emission_CO2+consum_O2+interval_O2; 0.452, 0.764, tmp_cumulo+pH_cumulo+AN+AN_cumulo+OD+Feed_Vol+Cell_conc._interval+rab_integral+RQ_integral+Arg_conc.+emission_O2+consum_O2+interval_CO2; 0.452, 0.764, pH_cumulo+AN+AN_cumulo+interval_yield+OD+Feed_

Vol+Cell_conc._interval+rab_integral+RQ_integral+Arg_conc.+emission_CO2+consum_O2+interval_O2; 0.452, 0.764, tmp_cumulo+pH+pH_cumulo+AN+AN_cumulo+OD+Cell_conc._interval+rab_integral+RQ_integral+Arg_conc.+emission_CO2+consum_O2+interval_CO2; 0.424, 0.764, pH_cumulo+PL+PL_cumulo+AN+AN_cumulo+OD+Feed_Vol+RS_cumulo+Cell_conc._interval+rab_integral+RQ_integral+Arg_conc.+emission_O2+consum_O2+interval_CO2; 0.477, 0.764, pH_cumulo+PL_cumulo+AN+AN_cumulo+OD+Feed_Vol+Cell_conc._interval+Arg_conc.+emission_CO2+consum_O2+generate_CO2; 0.438, 0.764, tmp_cumulo+pH_cumulo+PL+AN+AN_cumulo+interval_yield+OD+Feed_Vol+Cell_conc._interval+rab_integral+RQ_integral+Arg_conc.+emission_O2+consum_O2; 0.393, 0.764, pH+pH_cumulo+PL_cumulo+AN+AN_cumulo+interval_yield+OD+Feed_Vol+Cell_conc._interval+rab_integral+RQ_integral+Arg_conc.+emission_O2+emission_CO2+consum_O2+generate_CO2+interval_CO2; 0.438, 0.764, tmp_cumulo+pH_cumulo+AN+AN_cumulo+interval_yield+OD+Feed_Vol+Cell_conc._interval+rab_integral+RQ_integral+Arg_conc.+emission_O2+consum_O2+interval_CO2; 0.465, 0.764, pH+pH_cumulo+PL+AN+AN_cumulo+OD+Feed_Vol+Cell_conc._interval+Arg_conc.+emission_O2+emission_CO2+consum_O2; 0.452, 0.764, pH+pH_cumulo+AN+AN_cumulo+OD+Feed_Vol+Cell_conc._interval+RQ_integral+Arg_conc.+emission_O2+emission_CO2+consum_O2+generate_CO2; 0.477, 0.764, tmp_cumulo+pH_cumulo+AN+AN_cumulo+OD+Cell_conc._interval+rab_integral+Arg_conc.+emission_CO2+consum_O2+interval_CO2; 0.438, 0.764, tmp_cumulo+pH_cumulo+AN+AN_cumulo+interval_yield+OD+Cell_conc._interval+rab_integral+RQ_integral+Arg_conc.+emission_O2+consum_O2+generate_CO2+interval_CO2; 0.452, 0.764, tmp_cumulo+pH_cumulo+PL+AN+AN_cumulo+OD+Cell_conc._interval+rab_integral+RQ_integral+Arg_conc.+emission_O2+consum_O2+interval_CO2; 0.438, 0.764, tmp+tmp_cumulo+pH_cumulo+AN+AN_cumulo+interval_yield+OD+Cell_conc._interval+rab_integral+RQ_integral+Arg_conc.+emission_O2+consum_O2+interval_CO2; 0.465, 0.764, tmp_cumulo+pH+pH_cumulo+PL+AN+AN_cumulo+OD+Cell_conc._interval+Arg_conc.+emission_CO2+consum_O2+interval_CO2; 0.465, 0.764, pH+pH_cumulo+PL+AN+AN_cumulo+interval_yield+OD+Cell_conc._interval+Arg_conc.+emission_CO2+generate_CO2+interval_CO2; 0.477, 0.764, pH_cumulo+PL_cumulo+AN+AN_cumulo+OD+Feed_Vol+Cell_conc._interval+rab_integral+Arg_conc.+emission_CO2+consum_O2; 0.424, 0.764, tmp_cumulo+pH_cumulo+PL+AN+AN_cumulo+interval_yield+OD+Cell_conc._interval+rab_integral+RQ_integral+Arg_conc.+emission_O2+emission_CO2+consum_O2+interval_CO2; 0.452, 0.764, pH+pH_cumulo+PL+AN+AN_cumulo+OD+Feed_Vol+Cell_conc._interval+RQ_integral+Arg_conc.+emission_O2+emission_CO2+consum_O2; 0.423, 0.764, pH_cumulo+PL+AN+AN_cumulo+interval_yield+OD+Cell_conc._interval+rab_integral+RQ_integral+Accum._Yield+Arg_conc.+emission_O2+consum_O2+generate_CO2+interval_CO2; 0.465, 0.764, pH_cumulo+PL+AN+AN_cumulo+OD+Cell_conc._interval+rab_integral+RQ_integral+Arg_conc.+emission_O2+interval_O2+interval_CO2; 0.423, 0.764, tmp_cumulo+pH+pH_cumulo+PL_cumulo+AN+AN_cumulo+interval_yield+OD+Cell_conc._interval+rab_integral+RQ_integral+Arg_conc.+emission_CO2+generate_CO2+interval_CO2; 0.438, 0.764, pH+pH_cumulo+PL+AN+AN_cumulo+interval_yield+OD+Feed_Vol+Cell_conc._interval+rab_integral+RQ_integral+Arg_conc.+emission_O2+consum_O2; 0.408, 0.764, tmp+pH+pH_cumulo+PL_cumulo+AN+AN_cumulo+interval_yield+OD+Cell_conc._interval+rab_integral+RQ_integral+Arg_conc.+emission_O2+interval_O2+generate_CO2+interval_CO2; 0.477, 0.764, tmp+tmp_cumulo+pH_cumulo+AN+AN_cumulo+OD+Cell_conc._interval+Arg_conc.+emission_CO2+consum_O2+interval_CO2; 0.477, 0.764, pH_cumulo+PL_cumulo+AN+AN_cumulo+OD+Feed_Vol+Cell_conc._interval+Arg_conc.+emission_CO2+consum_O2+interval_CO2; 0.423, 0.764, tmp_cumulo+pH_cumulo+PL_cumulo+AN+AN_cumulo+interval_yield+OD+Cell_conc._interval+rab_integral+RQ_integral+Arg_conc.+emission_O2+emission_CO2+consum_O2+interval_CO2; 0.423, 0.764, pH_cumulo+PL+AN+AN_cumulo+interval_yield+OD+RS+Feed_Vol+RS_cumulo+Cell_conc._interval+rab_integral+RQ_integral+Arg_conc.+emission_O2+consum_O2; 0.438, 0.764, tmp+pH+pH_cumulo+PL_cumulo+AN+AN_cumulo+OD+Feed_Vol+Cell_conc._interval+rab_integral+RQ_integral+Arg_conc.+emission_O2+consum_O2; 0.477, 0.764, tmp+pH+pH_cumulo+AN+AN_cumulo+OD+Feed_Vol+Cell_conc._interval+Arg_conc.+emission_CO2+consum_O2; 0.408, 0.764, pH_cumulo+PL+PL_cumulo+AN+AN_cumulo+interval_yield+OD+Cell_conc._interval+rab_integral+RQ_integral+Accum._Yield+Arg_conc.+emission_O2+consum_O2+generate_CO2+interval_CO2; 0.438, 0.764, pH_cumulo+PL+PL_cumulo+AN+AN_cumulo+interval_yield+OD+Cell_conc._interval+rab_integral+RQ_integral+Arg_conc.+emission_O2+generate_CO2+interval_CO2; 0.464, 0.764, pH_cumulo+AN+AN_cumulo+interval_yield+OD+Cell_conc._interval+RQ_integral+Arg_conc.+emission_CO2+interval_O2+generate_CO2+interval_CO2; 0.438, 0.764, tmp_cumulo+pH_cumulo+PL+AN+AN_cumulo+interval_yield+OD+Cell_conc._interval+rab_integral+RQ_integral+Arg_conc.+emission_CO2+consum_O2+interval_CO2; 0.408, 0.764, pH+pH_cumulo+PL_cumulo+AN+AN_cumulo+interval_yield+OD+Cell_conc._interval+rab_integral+RQ_integral+Arg_conc.+emission_O2+emission_CO2+interval_O2+generate_CO2+interval_CO2; 0.477, 0.764, pH_cumulo+AN+AN_cumulo+interval_yield+OD+Feed_Vol+Cell_conc._interval+RQ_integral+Arg_conc.+emission_CO2+consum_O2; 0.489, 0.764, pH_cumulo+AN+AN_cumulo+OD+Feed_Vol+Cell_conc._interval+Arg_conc.+emission_CO2+interval_O2+generate_CO2; 0.477, 0.764, tmp_cumulo+pH_cumulo+PL+AN+AN_cumulo+OD+Feed_Vol+Cell_conc._interval+Arg_conc.+emission_CO2+consum_O2; 0.392, 0.764, pH+pH_cumulo+PL+PL_cumulo+AN+AN_cumulo+interval_yield+OD+Cell_conc._interval+rab_integral+RQ_integral+Arg_conc.+emission_O2+consum_O2+interval_O2+generate_CO2+interval_CO2; 0.408, 0.764, tmp+pH_cumulo+PL+PL_cumulo+AN+AN_cumulo+interval_yield+OD+Cell_conc._interval+rab_integral+RQ_integral+Arg_conc.+emission_O2+interval_O2+generate_CO2+interval_CO2; 0.408, 0.764, pH_cumulo+PL+PL_cumulo+AN+AN_cumulo+interval_yield+OD+RS+Feed_Vol+Cell_conc._interval+rab_integral+RQ_integral+Arg_conc.+emission_O2+consum_O2+interval_CO2; 0.408, 0.764, pH_cumulo+PL+AN+AN_cumulo+interval_yield+OD+Feed_Vol+RS_cumulo+Cell_conc._interval+rab_integral+RQ_integral+Arg_conc.+emission_O2+emission_CO2+consum_O2+interval_CO2; 0.423, 0.764, pH_cumulo+PL+PL_cumulo+AN+AN_cumulo+interval_yield+OD+RS+Feed_Vol+Cell_conc._interval+rab_integral+RQ_integral+Arg_conc.+emission_O2+consum_O2; 0.464, 0.764, pH_cumulo+PL_cumulo+AN+AN_cumulo+OD+Feed_Vol+Cell_conc._interval+RQ_integral+Arg_conc.+emission_O2+emission_CO2+consum_O2; 0.451, 0.764, pH_cumulo+PL_cumulo+AN+AN_cumulo+interval_yield+OD+Feed_Vol+Cell_conc._interval+Arg_conc.+emission_CO2+consum_O2+generate_CO2+interval_CO2; 0.477, 0.764, pH_cumulo+AN+AN_cumulo+OD+Cell_conc._interval+Arg_conc.+emission_O2+emission_CO2+interval_O2+generate_CO2+interval_CO2; 0.437, 0.764, pH+pH_cumulo+AN+AN_cumulo+interval_yield+OD+Feed_Vol+Cell_conc._interval+rab_integral+RQ_integral+Accum._Yield+Arg_conc.+emission_O2+consum_O2; 0.423, 0.764, pH+pH_cumulo+PL+AN+AN_cumulo+interval_yield+OD+Feed_Vol+Cell_conc._interval+rab_integral+RQ_integral+Accum._Yield+Arg_conc.+emission_O2+consum_O2; 0.408, 0.764, pH+pH_cumulo+PL_cumulo+AN+AN_cumulo+interval_yield+OD+RS_cumulo+Cell_conc._interval+rab_integral+RQ_integral+Arg_conc.+emission_O2+interval_O2+generate_CO2+interval_CO2; 0.408, 0.764, tmp_cumulo+pH_cumulo+PL+PL_cumulo+AN+AN_cumulo+interval_yield+OD+RS_cumulo+Cell_conc._interval+rab_integral+RQ_integral+Arg_conc.+emission_O2+consum_O2+interval_CO2; 0.437, 0.764, pH+pH_cumulo+PL+AN+AN_cumulo+OD+Feed_Vol+Cell_conc._interval+rab_integral+RQ_integral+Arg_conc.+emission_O2+consum_O2+interval_O2; 0.451, 0.764, pH+pH_cumulo+PL_cumulo+AN+AN_cumulo+OD+Cell_conc._interval+rab_integral+RQ_integral+Arg_conc.+emission_O2+consum_O2+interval_CO2; 0.437, 0.764, tmp+pH+pH_cumulo+AN+AN_cumulo+interval_yield+OD+Feed_Vol+Cell_conc._interval+rab_integral+RQ_integral+Arg_conc.+emission_O2+consum_O2; 0.476, 0.764, pH_cumulo+PL+AN_cumulo+OD+Feed_Vol+Cell_conc._interval+rab_integral+RQ_integral+Arg_conc.+emission_O2+consum_O2; 0.408, 0.764, pH_cumulo+PL+PL_cumulo+AN+AN_cumulo+interval_yield+OD+RS+Cell_conc._interval+rab_integral+RQ_integral+Arg_conc.+emission_O2+consum_O2+interval_O2+interval_CO2; 0.451, 0.764, pH_cumulo+AN+AN_cumulo+OD+Feed_Vol+Cell_conc._interval+rab_integral+RQ_integral+Arg_conc.+emission_O2+consum_O2+interval_O2+generate_CO2; 0.488, 0.764, pH+pH_cumulo+AN_cumulo+OD+Feed_Vol+Cell_conc._interval+Arg_conc.+emission_CO2+consum_O2+interval_O2; 0.423, 0.764, pH_cumulo+PL+AN+AN_cumulo+interval_yield+OD+Feed_Vol+RS_cumulo+Cell_conc._interval+rab_integral+RQ_integral+Arg_conc.+emission_O2+consum_O2+generate_CO2; 0.451, 0.764, tmp+pH_cumulo+PL_cumulo+AN+AN_cumulo+OD+Cell_conc._interval+rab_integral+RQ_integral+Arg_conc.+emission_O2+consum_O2+interval_CO2; 0.476, 0.764, pH_cumulo+PL+AN+AN_cumulo+OD+Cell_conc._interval+Arg_conc.+emission_CO2+consum_O2+interval_O2+interval_CO2; 0.451, 0.764, pH+pH_cumulo+AN+AN_cumulo+OD+Feed_Vol+Cell_conc._interval+RQ_integral+Arg_conc.+emission_O2+emission_CO2+consum_O2+interval_O2; 0.437, 0.764, pH_cumulo+AN+AN_cumulo+interval_yield+OD+Feed_Vol+RS_cumulo+Cell_conc._interval+rab_integral+RQ_integral+Arg_conc.+emission_O2+consum_O2+interval_CO2; 0.451, 0.764, pH_cumulo+PL_cumulo+AN+AN_cumulo+OD+RS+Feed_Vol+Cell_conc._interval+rab_integral+RQ_integral+Arg_conc.+emission_O2+consum_O2; 0.451, 0.764, tmp_cumulo+pH_cumulo+AN+AN_cumulo+interval_yield+OD+Feed_Vol+Cell_conc._interval+rab_integral+RQ_integral+Arg_conc.+emission_O2+consum_O2; 0.464, 0.764, pH_cumulo+AN+AN_cumulo+OD+Feed_Vol+Cell_conc._interval+rab_integral+RQ_integral+Arg_conc.+emission_O2+emission_CO2+consum_O2+generate_CO2; 0.423, 0.763, pH+pH_cumulo+AN+AN_cumulo+interval_yield+OD+Feed_Vol+Cell_conc._interval+rab_integral+RQ_integral+Arg_conc.+emission_O2+emission_CO2+consum_O2+generate_CO2; 0.451, 0.763, pH_cumulo+PL+AN_cumulo+OD+RS_cumulo+Cell_conc._interval+rab_integral+RQ_integral+Arg_conc.+emission_O2+interval_O2+interval_CO2; 0.464, 0.763, pH_cumulo+AN+AN_cumulo+interval_yield+OD+Feed_Vol+Cell_conc._interval+Arg_conc.+emission_CO2+interval_O2+generate_CO2+interval_CO2; 0.451, 0.763, tmp_cumulo+pH+pH_cumulo+AN+AN_cumulo+OD+Cell_conc._interval+rab_integral+RQ_integral+Arg_conc.+emission_O2+consum_O2+interval_CO2; 0.464, 0.763, tmp_cumulo+pH_cumulo+PL+AN+AN_cumulo+OD+Feed_Vol+Cell_conc._interval+Arg_conc.+emission_CO2+consum_O2+interval_CO2; 0.476, 0.763, pH_cumulo+PL+AN+AN_cumulo+OD+Feed_Vol+Cell_conc._interval+Arg_conc.+emission_O2+emission_CO2+consum_O2; 0.464, 0.763, pH_cumulo+PL+AN+AN_cumulo+interval_yield+OD+Feed_Vol+Cell_conc._interval+RQ_integral+Arg_conc.+emission_CO2+consum_O2; 0.488, 0.763, pH_cumulo+AN_cumulo+OD+Feed_Vol+Cell_conc._interval+RQ_integral+Arg_conc.+emission_O2+emission_CO2+consum_O2; 0.488, 0.763, pH_cumulo+PL_cumulo+AN_cumulo+OD+Feed_Vol+Cell_conc._interval+Arg_conc.+emission_CO2+consum_O2+generate_CO2; 0.464, 0.763, tmp_cumulo+pH_cumulo+PL+AN+AN_cumulo+OD+Cell_conc._interval+Arg_conc.+emission_CO2+interval_O2+generate_CO2+interval_CO2; 0.476, 0.763, tmp+pH_cumulo+PL+AN+AN_cumulo+OD+Cell_conc._interval+Arg_conc.+emission_CO2+consum_O2+interval_CO2; 0.407, 0.763, pH_cumulo+PL_cumulo+AN+AN_cumulo+interval_yield+OD+RS+Feed_Vol+Cell_conc._interval+rab_integral+RQ_integral+Arg_conc.+emission_O2+consum_O2+generate_CO2+interval_CO2; 0.450, 0.763, pH+pH_cumulo+PL_cumulo+AN+AN_cumulo+interval_yield+OD+Feed_Vol+Cell_conc._interval+rab_integral+RQ_integral+Arg_conc.+emission_O2+consum_O2; 0.437, 0.763, pH_cumulo+PL+AN+AN_cumulo+OD+Feed_Vol+Cell_conc._interval+rab_integral+RQ_integral+Arg_conc.+emission_O2+consum_O2+interval_O2+interval_CO2; 0.476, 0.763, tmp+pH_cumulo+AN+AN_cumulo+OD+Feed_Vol+Cell_conc._interval+RQ_integral+Arg_conc.+emission_CO2+consum_O2; 0.463, 0.763, pH+pH_cumulo+PL+AN+AN_cumulo+OD+Cell_conc._interval+Arg_conc.+emission_CO2+interval_O2+generate_CO2+interval_CO2; 0.463, 0.763, pH_cumulo+PL+PL_cumulo+AN+AN_cumulo+interval_yield+OD+Cell_conc._interval+Arg_conc.+emission_CO2+generate_CO2+interval_CO2; 0.407, 0.763, pH+pH_cumulo+PL+PL_cumulo+AN+AN_cumulo+interval_yield+OD+Feed_Vol+Cell_conc._interval+rab_integral+RQ_integral+Arg_conc.+emission_O2+emission_CO2+consum_O2; 0.476, 0.763, pH_cumulo+PL_cumulo+AN+AN_cumulo+interval_yield+OD+Feed_Vol+Cell_conc._interval+Arg_conc.+emission_CO2+consum_O2; 0.407, 0.763, tmp+pH+pH_cumulo+PL+PL_cumulo+AN+AN_cumulo+interval_yield+OD+Feed_Vol+Cell_conc._interval+rab_integral+RQ_integral+Arg_conc.+emission_O2+consum_O2; 0.422, 0.763, pH_cumulo+PL+AN+AN_cumulo+interval_yield+OD+RS_cumulo+Cell_conc._interval+rab_integral+RQ_integral+Arg_conc.+emission_O2+consum_O2+generate_CO2+interval_CO2; 0.476, 0.763, pH_cumulo+AN+AN_cumulo+OD+Feed_Vol+Cell_conc._interval+RQ_integral+Arg_conc.+emission_CO2+interval_O2+generate_CO2; 0.407, 0.763, pH+pH_cumulo+AN+AN_cumulo+interval_yield+OD+Cell_conc._interval+rab_integral+RQ_integral+Arg_conc.+emission_O2+emission_

CO2+consum_O2+interval_O2+interval CO2; 0.422, 0.763, pH_cumulo+PL+PL_cumulo+AN+AN_cumulo+interval_yield+OD+Cell_conc._interval+rab_integral+RQ_integral+Arg_conc.+emission_CO2+consum_O2+generate_CO2+interval_CO2; 0.436, 0.763, pH_cumulo+PL+PL_cumulo+AN+AN_cumulo+interval_yield+OD+Cell_conc._interval+rab_integral+RQ_integral+Arg_conc.+emission_CO2+consum_O2+interval_CO2; 0.422, 0.763, pH_cumulo+AN+AN_cumulo+interval_yield+OD+Feed_Vol+Cell_conc._interval+rab_integral+RQ_integral+Arg_conc.+emission_O2+emission_CO2+interval_O2+generate_CO2+interval_CO2; 0.422, 0.763, tmp_cumulo+pH_cumulo+PL_cumulo+AN+AN_cumulo+interval_yield+OD+Feed_Vol+Cell_conc._interval+rab_integral+RQ_integral+Arg_conc.+emission_O2+consum_O2+interval_O2; 0.463, 0.763, pH+pH_cumulo+PL+AN+AN_cumulo+OD+Feed_Vol+RS_cumulo+Cell_conc._interval+Arg_conc.+emission_CO2+consum_O2; 0.391, 0.763, pH+pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_O2+generate_CO2; 0.476, 0.763, pH_cumulo+PL_cumulo+AN+AN_cumulo+OD+Feed_Vol+Cell_conc._interval+RQ_integral+Arg_conc.+emission_O2+consum_O2; 0.422, 0.763, pH_cumulo+PL+AN+AN_cumulo+interval_yield+OD+Feed_Vol+Cell_conc._interval+rab_integral+RQ_integral+Arg_conc.+emission_O2+consum_O2+generate_CO2+interval_CO2; 0.436, 0.763, pH_cumulo+PL_cumulo+AN+AN_cumulo+interval_yield+OD+Cell_conc._interval+rab_integral+RQ_integral+Arg_conc.+emission_CO2+consum_O2+interval_O02+interval_CO2; 0.488, 0.763, pH_cumulo+PL_cumulo+AN_cumulo+OD+Feed_Vol+Cell_conc._interval+Arg_conc.+emission_CO2+consum_O2+interval_O2; 0.463, 0.763, pH+pH_cumulo+PL+AN+AN_cumulo+OD+Feed_Vol+Cell_conc._interval+RQ_integral+Arg_conc.+emission_O2+consum_O2; 0.436, 0.763, pH+pH_cumulo+PL+PL_cumulo+AN+AN_cumulo+interval_yield+OD+Cell_conc._interval+rab_integral+RQ_integral+Arg_conc.+emission_O2+consum_O2; 0.463, 0.763, pH_cumulo+PL+AN+AN_cumulo+OD+Feed_Vol+Cell_conc._interval+RQ_integral+Arg_conc.+emission_CO2+consum_O2+interval_CO2; 0.487, 0.763, pH+pH_cumulo+AN+AN_cumulo+interval_yield+OD+Feed_Vol+Cell_conc._interval+Arg_conc.+emission_CO2+consum_O2; 0.436, 0.763, pH+pH_cumulo+PL+AN+AN_cumulo+OD+Feed_Vol+Cell_conc._interval+rab_integral+RQ_integral+Arg_conc.+emission_O2+consum_O2+interval_CO2; 0.463, 0.763, pH_cumulo+PL+AN+AN_cumulo+OD+Feed_Vol+Cell_conc._interval+rab_integral+Arg_conc.+emission_O2+emission_CO2+consum_O2; 0.463, 0.763, pH_cumulo+AN+AN_cumulo+OD+Feed_Vol+Cell_conc._interval+rab_integral+RQ_integral+Arg_conc.+emission_CO2+consum_O2+interval_O2; 0.487, 0.763, pH+pH_cumulo+AN+AN_cumulo+OD+Feed_Vol+Cell_conc._interval+Arg_conc.+emission_CO2+consum_O2+generate_CO2; 0.450, 0.763, pH+pH_cumulo+AN+AN_cumulo+interval_yield+OD+Feed_Vol+Cell_conc._interval+rab_integral+RQ_integral+Arg_conc.+emission_CO2+consum_O2; 0.390, 0.763, pH+pH_cumulo+PL_cumulo+AN+AN_cumulo+interval_yield+OD+Feed_Vol+RS_cumulo+Cell_conc._interval+rab_integral+RQ_integral+Arg_conc.+emission_O2+consum_O2+generate CO2+interval_CO2; 0.406, 0.763, pH+pH_cumulo+PL_cumulo+AN+AN_cumulo+interval_yield+OD+Feed_Vol+Cell_conc._interval+rab_integral+RQ_integral+Accum._Yield+Arg_conc.+emission_O2+consum_O2+interval_O2; 0.450, 0.763, pH_cumulo+PL+AN+AN_cumulo+OD+Feed_Vol+Cell_conc._interval+RQ_integral+Arg_conc.+emission_O2+emission_CO2+consum_O2+interval_O2; 0.463, 0.763, pH_cumulo+PL+AN_cumulo+interval_yield+OD+Feed_Vol+Cell_conc._interval+rab_integral+RQ_integral+Arg_conc.+emission_CO2+consum_O2+interval_CO2; 0.450, 0.763, pH_cumulo+PL_cumulo+AN+AN_cumulo+interval_yield+OD+Cell_conc._interval+rab_integral+RQ_integral+Arg_conc.+emission_CO2+consum_O2+interval_CO2; 0.487, 0.763, pH_cumulo+AN+AN_cumulo+OD+RS+Feed_Vol+Cell_conc._interval+Arg_conc.+emission_CO2+consum_O2; 0.487, 0.763, pH+pH_cumulo+AN_cumulo+OD+Feed_Vol+Cell_conc._interval+Arg_conc.+emission_O2+emission_CO2+consum_O2; 0.463, 0.763, pH_cumulo+AN+AN_cumulo+OD+Feed_Vol+Cell_conc._interval+rab_integral+RQ_integral+Arg_conc.+emission_CO2+consum_O2+interval_CO2; 0.450, 0.763, pH_cumulo+PL+AN+AN_cumulo+interval_yield+OD+Feed_Vol+Cell_conc._interval+RQ_integral+Arg_conc.+emission_CO2+consum_O2+interval_O2; 0.436, 0.763, pH_cumulo+PL+AN+AN_cumulo+OD+Feed_Vol+RS_cumulo+Cell_conc._interval+rab_integral+RQ_integral+Arg_conc.+emission_O2+emission_CO2+consum_O2; 0.475, 0.763, pH_cumulo+AN+AN_cumulo+OD+Feed_Vol+Cell_conc._interval+Arg_conc.+emission_O2+emission_CO2+consum_O2+generate_CO2; 0.463, 0.763, pH_cumulo+PL+AN+AN_cumulo+interval_yield+OD+RS_cumulo+Cell_conc._interval+Arg_conc.+emission_CO2+consum_O2+interval_CO2; 0.487, 0.763, pH+pH_cumulo+AN_cumulo+OD+Feed_Vol+Cell_conc._interval+RQ_integral+Arg_conc.+emission_O2+consum_O2; 0.463, 0.763, pH+pH_cumulo+AN+AN_cumulo+interval_yield+OD+Cell_conc._interval+Arg_conc.+emission_CO2+consum_O2+generate_CO2+interval_CO2; 0.450, 0.763, pH_cumulo+PL+AN+AN_cumulo+OD+Feed_Vol+Cell_conc._interval+RQ_integral+Arg_conc.+emission_O2+emission_CO2+consum_O2+generate_CO2; 0.390, 0.763, pH+pH_cumulo+PL+PL_cumulo+AN+AN_cumulo+interval_yield+OD+Cell_conc._interval+rab_integral+RQ_integral+Arg_conc.+emission_O2+emission_CO2+consum_O2+generate_CO2+interval_CO2; 0.421, 0.763, tmp_cumulo+pH_cumulo+PL+AN+AN_cumulo+interval_yield+OD+Feed_Vol+Cell_conc._interval+rab_integral+RQ_integral+Arg_conc.+emission_O2+consum_O2+interval_CO2; 0.406, 0.763, pH_cumulo+PL+PL_cumulo+AN+AN_cumulo+interval_yield+OD+Feed_Vol+RS_cumulo+Cell_conc._interval+rab_integral+RQ_integral+Arg_conc.+emission_O2+consum_O2+generate_CO2; 0.406, 0.763, pH+pH_cumulo+PL+AN+AN_cumulo+interval_yield+OD+Feed_Vol+RS_cumulo+Cell_conc._interval+rab_integral+RQ_integral+Arg_conc.+emission_CO2+consum_O2; 0.475, 0.763, pH_cumulo+AN+AN_cumulo+OD+Feed_Vol+Cell_conc._interval+RQ_integral+Arg_conc.+emission_O2+consum_O2+generate_CO2; 0.390, 0.763, tmp+pH+pH_cumulo+PL+PL_cumulo+AN+AN_cumulo+interval_yield+OD+RS_cumulo+Cell_conc._interval+rab_integral+RQ_integral+Arg_conc.+emission_O2+consum_O2+interval_CO2; 0.421, 0.763, tmp_cumulo+pH_cumulo+PL+PL_cumulo+AN+AN_cumulo+interval_yield+OD+Cell_conc._interval+rab_integral+RQ_integral+Arg_conc.+emission_CO2+generate_CO2+interval_CO2; 0.450, 0.763, pH_cumulo+PL+AN+AN_cumulo+OD+Feed_Vol+Cell_conc._interval+RQ_integral+Arg_conc.+emission_O2+emission_CO2+consum_O2+interval_O2; 0.436, 0.763, pH_cumulo+PL_cumulo+AN+AN_cumulo+OD+Feed_Vol+Cell_conc._interval+rab_integral+RQ_integral+Arg_conc.+emission_O2+emission_CO2+consum_O2+interval_CO2; 0.449, 0.763, pH_cumulo+AN+AN_cumulo+interval_yield+OD+ RS+Feed_Vol+Cell_conc._interval+rab_integral+RQ_integral+Arg_conc.+emission_O2+consum_O2; 0.449, 0.763, pH_cumulo+AN+AN_cumulo+interval_yield+OD+RS_cumulo+Cell_conc._interval+rab_integral+RQ_integral+Arg_conc.+emission_O2+consum_O2+interval_CO2; 0.463, 0.763, pH_cumulo+AN+AN_cumulo+OD+Feed_Vol+Cell_conc._interval+RQ_integral+Arg_conc.+emission_CO2+consum_O2+generate_CO2+interval_CO2; 0.421, 0.763, pH+pH_cumulo+AN+AN_cumulo+interval_yield+OD+Cell_conc._interval+rab_integral+RQ_integral+Arg_conc.+emission_O2+emission_CO2+interval_O2+generate_CO2+interval_CO2; 0.390, 0.763, pH+pH_cumulo+PL+PL_cumulo+AN+AN_cumulo+interval_yield+OD+Feed_Vol+RS_cumulo+Cell_conc._interval+rab_integral+RQ_integral+Arg_conc.+emission_O2+consum_O2+interval_O2; 0.475, 0.763, pH_cumulo+AN+AN_cumulo+OD+Feed_Vol+Cell_conc._interval+Arg_conc.+emission_CO2+consum_O2+interval_O2+interval_CO2; 0.449, 0.763, pH_cumulo+PL_cumulo+AN_cumulo+interval_yield+OD+Feed_Vol+Cell_conc._interval+rab_integral+RQ_integral+Arg_conc.+emission_O2+consum_O2+interval_O2; 0.462, 0.763, pH_cumulo+PL+AN+AN_cumulo+OD+Feed_Vol+RS_cumulo+Cell_conc._interval+RQ_integral+Arg_conc.+emission_CO2+consum_O2; 0.406, 0.763, pH_cumulo+PL+PL_cumulo+AN+AN_cumulo+interval_yield+OD+Feed_Vol+Cell_conc._interval+rab_integral+RQ_integral+Accum._Yield+Arg_conc.+emission_O2+consum_O2+interval_CO2; 0.462, 0.763, pH_cumulo+AN+AN_cumulo+OD+RS+Feed_Vol+Cell_conc._interval+rab_integral+RQ_integral+Arg_conc.+emission_O2+consum_O2; 0.475, 0.763, pH_cumulo+AN+AN_cumulo+OD+Feed_Vol+RS_cumulo+Cell_conc._interval+rab_integral+Arg_conc.+emission_CO2+consum_O2; 0.406, 0.763, tmp_cumulo+pH_cumulo+PL+PL_cumulo+AN+AN_cumulo+interval_yield+OD+Cell_conc._interval+rab_integral+RQ_integral+Arg_conc.+emission_O2+interval_O2+generate_CO2+interval_CO2; 0.421, 0.763, pH+pH_cumulo+AN+AN_cumulo+interval_yield+OD+Feed_Vol+Cell_conc._interval+rab_integral+RQ_integral+Arg_conc.+emission_O2+emission_CO2+consum_O2+interval_O2; 0.449, 0.763, tmp_cumulo+pH+pH_cumulo+AN+AN_cumulo+OD+Feed_Vol+Cell_conc._interval+rab_integral+RQ_integral+Arg_conc.+emission_O2+consum_O2; 0.421, 0.763, pH+pH_cumulo+PL+AN+AN_cumulo+interval_yield+OD+Cell_conc._interval+rab_integral+RQ_integral+Arg_conc.+emission_O2+emission_CO2+consum_O2+interval_CO2; 0.421, 0.763, tmp+pH+pH_cumulo+PL+AN+AN_cumulo+interval_yield+OD+Feed_Vol+Cell_conc._interval+rab_integral+RQ_integral+Arg_conc.+emission_O2+consum_O2; 0.475, 0.763, pH_cumulo+AN+AN_cumulo+OD+Feed_Vol+Cell_conc._interval+rab_integral+Arg_conc.+emission_CO2+consum_O2+interval_CO2; 0.462, 0.763, pH+pH_cumulo+AN+AN_cumulo+OD+Feed_Vol+Cell_conc._interval+RQ_integral+Arg_conc.+emission_O2+consum_O2+generate_CO2; 0.435, 0.763, pH_cumulo+PL+AN+AN_cumulo+OD+Feed_Vol+Cell_conc._interval+rab_integral+RQ_integral+Arg_conc.+emission_O2+emission_CO2+consum_O2+interval_CO2; 0.421, 0.763, tmp+pH+pH_cumulo+PL_cumulo+AN+AN_cumulo+interval_yield+OD+Feed_Vol+Cell_conc._interval+rab_integral+RQ_integral+Arg_conc.+emission_O2+consum_O2; 0.421, 0.763, tmp_cumulo+pH_cumulo+PL+AN+AN_cumulo+interval_yield+OD+RS_cumulo+Cell_conc._interval+rab_integral+RQ_integral+Arg_conc.+emission_O2+consum_O2+interval_CO2; 0.421, 0.763, pH_cumulo+AN+AN_cumulo+interval_yield+OD+Feed_Vol+Cell_conc._interval+rab_integral+RQ_integral+Arg_conc.+emission_O2+consum_O2+interval_O2+generate_CO2+interval_CO2; 0.462, 0.763, pH_cumulo+AN+AN_cumulo+OD+Feed_Vol+RS_cumulo+Cell_conc._interval+RQ_integral+Arg_conc.+emission_O2+emission_CO2+consum_O2; 0.406, 0.763, pH_cumulo+PL_cumulo+AN+AN_cumulo+interval_yield+OD+Cell_conc._interval+rab_integral+RQ_integral+Arg_conc.+emission_O2+emission_CO2+consum_O2+interval_O2+generate_CO2+interval_CO2; 0.435, 0.763, tmp+pH_cumulo+PL+AN+AN_cumulo+interval_yield+OD+Cell_conc._interval+rab_integral+RQ_integral+Arg_conc.+emission_O2+consum_O2+interval_CO2; 0.406, 0.763, tmp_cumulo+pH_cumulo+PL_cumulo+AN+AN_cumulo+interval_yield+OD+Feed_Vol+Cell_conc._interval+rab_integral+RQ_integral+Arg_conc.+emission_O2+consum_O2+interval_O2+interval_CO2; 0.462, 0.763, pH_cumulo+PL+AN+AN_cumulo+OD+Feed_Vol+RS_cumulo+Cell_conc._interval+RQ_integral+Arg_conc.+emission_O2+consum_O2; 0.449, 0.763, pH+pH_cumulo+PL+AN+AN_cumulo+interval_yield+OD+Cell_conc._interval+Arg_conc.+emission_CO2+interval_O2+generate_CO2+interval CO2; 0.449, 0.763, pH_cumulo+PL+AN+AN_cumulo+OD+Cell_conc._interval+rab_integral+RQ_integral+Arg_conc.+emission_O2+interval_O2+generate_CO2+interval_CO2; 0.435, 0.763, pH_cumulo+PL+AN+AN_cumulo+interval_yield+OD+Feed_Vol+Cell_conc._interval+rab_integral+RQ_integral+Arg_conc.+emission_O2+interval_O2+generate_CO2; 0.421, 0.763, tmp_cumulo+pH+pH_cumulo+AN+AN_cumulo+interval_yield+OD+Cell_conc._interval+rab_integral+RQ_integral+Arg_conc.+emission_O2+interval_O2+generate_CO2+interval_CO2; 0.405, 0.763, pH+pH_cumulo++PL_cumulo+AN+AN_cumulo+interval_yield+OD+RS_cumulo+Cell_conc._interval+rab_integral+RQ_integral+Arg_conc.+emission_O2+consum_O2+interval_O2+interval_CO2; 0.405, 0.763, pH_cumulo+PL_cumulo+AN+AN_cumulo+interval_yield+OD+RS_cumulo+Cell_conc._interval+rab_integral+RQ_integral+Arg_conc.+emission_O2+consum_O2+interval_O2+generate_CO2+interval_CO2; 0.435, 0.763, pH+pH_cumulo+PL+PL_cumulo+AN+AN_cumulo+OD+Cell_conc._interval+rab_integral+RQ_integral+Arg_conc.+emission_O2+consum_O2+interval_CO2; 0.405, 0.763, pH+pH_cumulo+PL+PL_cumulo+AN+AN_cumulo+interval_yield+OD+Cell_conc._interval+rab_integral+RQ_integral+Accum._Yield+Arg_conc.+emission_O2+consum_O2+interval_CO2; 0.475, 0.763, pH_cumulo+AN+AN_cumulo+OD+RS_cumulo+Cell_conc._interval+Arg_conc.+emission_CO2+interval_O2+generate_CO2+interval_CO2; 0.475, 0.763, pH_cumulo+PL+PL_cumulo+AN+AN_cumulo+OD+Cell_conc._interval+Arg_conc.+emission_CO2+consum_O2+interval_CO2; 0.421, 0.763, pH+pH_cumulo+PL+PL_cumulo+AN+AN_cumulo+OD+Feed_Vol+RS_cumulo+Cell_conc._interval+rab_integral+RQ_integral+Arg_conc.+emission_O2+consum_O2; 0.449, 0.763, tmp_cumulo+pH_cumulo+PL+AN+AN_cumulo+OD+Feed_Vol+Cell_conc._interval+rab_integral+RQ_integral+Arg_conc.+emission_O2+consum_O2; 0.405, 0.763, tmp_cumulo+pH_cumulo+PL_cumulo+AN+AN_cumulo+interval_yield+OD+Cell_conc._interval+rab_integral+RQ_integral+Arg_conc.+emission_O2+consum_O2+interval_O2+generate_CO2+interval_CO2; 0.435, 0.763, pH+pH_cumulo+PL+AN+AN_cumulo+interval_yield+OD+Cell_conc._interval+rab_integral+RQ_integral+Arg_conc.+emission_CO2+consum_O2+interval_CO2; 0.474, 0.763, pH_cumulo+AN+AN_cumulo+OD+Feed_Vol+Cell_conc._interval+Arg_conc.+ emission_O2+emission_CO2+consum_O2+interval_O2; 0.435, 0.763, pH_cumulo+PL+AN+AN_cumulo+OD+ Feed_Vol+Cell_conc._interval+rab_integral+RQ_integral+ Arg_conc.+emission_O2+emission_CO2+consum_O2+interval_O2; 0.486, 0.763, pH_cumulo+AN+AN_cumulo+ OD+RS_cumulo+Cell_conc._interval+Arg_conc.+ emission_CO2+consum_O2+interval_CO2; 0.389, 0.763, tmp+pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+ generate_CO2+interval_CO2; 0.421, 0.763, pH_cumulo+ PL+AN+AN_cumulo+interval_yield+OD+Feed_Vol+Cell_ conc._interval+rab_integral+RQ_integral+Arg_conc.+ emission_O2+consum_O2+interval_O2+generate_CO2; 0.462, 0.763, pH_cumulo+PL+AN+AN_cumulo+OD+ Feed_Vol+Cell_conc._interval+rab_integral+Arg_conc.+ emission_CO2+consum_O2+interval_O2; 0.449, 0.763, pH_cumulo+PL+AN+AN_cumulo+interval_yield+OD+ Feed_Vol+Cell_conc._interval+RQ_integral+Arg_conc.+ emission_CO2+consum_O2+generate_CO2; 0.462, 0.763, pH+pH_cumulo+PL+PL_cumulo+AN+AN_cumulo+OD+ Feed_Vol+Cell_conc._interval+Arg_conc.+emission_CO2+ consum_O2; 0.420, 0.762, pH_cumulo+AN+AN_cumulo+ interval_yield+OD+Cell_conc._interval+rab_integral+RQ_ integral+Arg_conc.+emission_O2+emission_CO2+ consum_O2+interval_O2+generate_CO2+interval_CO2; 0.405, 0.762, tmp+tmp_cumulo+pH_cumulo+PL_cumulo+ AN+AN_cumulo+interval_yield+OD+Cell_conc._interval+ rab_integral+RQ_integral+Arg_conc.+emission_O2+consum_O2+interval_O2+interval_CO2; 0.474, 0.762, pH_cumulo+AN+AN_cumulo+interval_yield+OD+Feed_ Vol+Cell_conc._interval+Arg_conc.+emission_O2+consum_O2+interval_O2; 0.462, 0.762, pH_cumulo+PL+PL_ cumulo+AN+AN_cumulo+OD+Feed_Vol+Cell_conc._ interval+RQ_integral+Arg_conc.+emission_CO2+consum_ O2; 0.462, 0.762, pH_cumulo+AN+AN_cumulo+OD+ Feed_Vol+RS_cumulo+Cell_conc._interval+rab_integral+ RQ_integral+Arg_conc.+emission_CO2+consum_O2; 0.420, 0.762, pH_cumulo+PL+PL_cumulo+AN+AN_cumulo+OD+Feed_Vol+Cell_conc._interval+rab_integral+ RQ_integral+Arg_conc.+emission_O2+consum_O2+generate_CO2+interval_CO2; 0.462, 0.762, pH_cumulo+PL+ AN+AN_cumulo+OD+Feed_Vol+Cell_conc._interval+ rab_integral+Arg_conc.+emission_CO2+consum_O2+ generate_CO2; 0.462, 0.762, tmp_cumulo+pH_cumulo+ AN+AN_cumulo+OD+Feed_Vol+Cell_conc._interval+ Arg_conc.+emission_CO2+consum_O2+generate_CO2+ interval_CO2; 0.435, 0.762, pH_cumulo+PL+AN+AN_ cumulo+OD+Feed_Vol+Cell_conc._interval+rab_integral+ RQ_integral+Arg_conc.+emission_O2+emission_CO2+ consum_O2+generate_CO2; 0.462, 0.762, pH_cumulo+ AN+AN_cumulo+interval_yield+OD+Cell_conc._interval+ Arg_conc.+emission_O2+emission_CO2+interval_O2+ generate_CO2+interval_CO2; 0.462, 0.762, pH_cumulo+ PL+AN+AN_cumulo+interval_yield+OD+Feed_Vol+Cell_ conc._interval+Arg_conc.+emission_CO2+consum_O2+ interval_CO2; 0.420, 0.762, tmp_cumulo+pH_cumulo+PL+ PL_cumulo+AN+AN_cumulo+interval_yield+OD+Feed_ Vol+Cell_conc._interval+rab_integral+RQ_integral+Arg_ conc.+emission_O2+consum_O2; 0.435, 0.762, pH_cumulo+PL_cumulo+AN+AN_cumulo+interval_ yield+OD+Feed_Vol+Cell_conc._interval+RQ_integral+ Arg_conc.+emission_O2+emission_CO2+consum_O2+interval_O2; 0.462, 0.762, tmp_cumulo+pH_cumulo+PL+ cumulo+AN+AN_cumulo+OD+Cell_conc._interval+Arg_ conc.+emission_CO2+consum_O2+generate_CO2+ interval_CO2; 0.462, 0.762, tmp_cumulo+pH_cumulo+PL+

AN+AN_cumulo+OD+Cell_conc._interval+Arg_conc.+ emission_CO2+consum_O2+interval_O2+interval_CO2; 0.449, 0.762, tmp+pH_cumulo+AN+AN_cumulo+OD+ Feed_Vol+Cell_conc._interval+rab_integral+RQ_integral+ Arg_conc.+emission_O2+emission_CO2+consum_O2; 0.405, 0.762, tmp+pH_cumulo+PL_cumulo+AN+AN_cumulo+interval_yield+OD+Feed_Vol+Cell_conc._interval+ rab_integral+RQ_integral+Arg_conc.+emission_O2+consum_O2+interval_O2+interval_CO2; 0.462, 0.762, pH_cumulo+PL+AN+AN_cumulo+OD+Feed_Vol+Cell_ conc._interval+Arg_conc.+emission_CO2+consum_O2+ generate_CO2+interval_CO2; 0.448, 0.762, tmp_cumulo+ pH_cumulo+PL_cumulo+AN+AN_cumulo+OD+Feed_ Vol+Cell_conc._interval+rab_integral+RQ_integral+Arg_ conc.+emission_O2+consum_O2; 0.435, 0.762, pH_cumulo+PL_cumulo+AN+AN_cumulo+interval_ yield+OD+RS_cumulo+Cell_conc._interval+rab_integral+ RQ_integral+Arg_conc.+emission_CO2+generate_CO2+ interval_CO2; 0.462, 0.762, tmp_cumulo+pH+pH_cumulo+ AN+AN_cumulo+OD+Cell_conc._interval+Arg_conc.+ emission_CO2+consum_O2+interval_O2+interval_CO2; 0.435, 0.762, pH_cumulo+PL+AN+AN_cumulo+interval_ yield+OD+RS_cumulo+Cell_conc._interval+rab_integral+ RQ_integral+Arg_conc.+emission_O2+interval_O2+interval_CO2; 0.474, 0.762, pH_cumulo+AN+AN_cumulo+ OD+Feed_Vol+Cell_conc._interval+RQ_integral+Arg_ conc.+emission_O2+consum_O2+interval_O2; 0.474, 0.762, tmp_cumulo+pH_cumulo+PL_cumulo+AN+AN_ cumulo+OD+Cell_conc._interval+Arg_conc.+emission_ CO2+consum_O2+interval_CO2; 0.448, 0.762, tmp_cumulo+pH_cumulo+AN+AN_cumulo+OD+Cell_conc._ interval+rab_integral+RQ_integral+Arg_conc.+emission_ O2+emission_CO2+consum_O2+interval_CO2; 0.474, 0.762, pH_cumulo+AN+AN_cumulo+OD+Feed_Vol+Cell_ conc._interval+Arg_conc.+emission_CO2+consum_O2+interval_O2+generate_CO2; 0.462, 0.762, tmp+tmp_cumulo+ pH_cumulo+AN+AN_cumulo+OD+Cell_conc._interval+ Arg_conc.+emission_CO2+consum_O2+generate_CO2+ interval_CO2; 0.405, 0.762, pH+pH_cumulo+PL_cumulo+ AN+AN_cumulo+interval_yield+OD+Feed_Vol+RS_ cumulo+Cell_conc._interval+rab_integral+RQ_integral+ Arg_conc.+emission_O2+consum_O2+interval CO2; 0.462, 0.762, pH+pH_cumulo+AN+AN_cumulo+OD+ Feed_Vol+Cell_conc._interval+rab_integral+Arg_conc.+ emission_CO2+consum_O2+interval_O2; 0.461, 0.762, pH_cumulo+PL_cumulo+AN+AN_cumulo+OD+Feed_ Vol+Cell_conc._interval+Arg_conc.+emission_CO2+consum_O2+generate_CO2+interval_CO2; 0.389, 0.762, tmp+ pH+pH_cumulo+PL_cumulo+AN+AN_cumulo+interval_ yield+OD+Feed_Vol+Cell_conc._interval+rab_integral+ RQ_integral+Arg_conc.+emission_O2+consum_O2+ generate_CO2+interval_CO2; 0.420, 0.762, pH_cumulo+ PL+AN+AN_cumulo+interval_yield+OD+Feed_Vol+Cell_ conc._interval+rab_integral+RQ_integral+Arg_conc.+ emission_O2+consum_O2+interval_O2+interval_CO2; 0.435, 0.762, pH+pH_cumulo+PL+AN+AN_cumulo+OD+ Feed_Vol+Cell_conc._interval+rab_integral+RQ_integral+ Arg_conc.+emission_O2+consum_O2+generate_CO2; 0.420, 0.762, tmp_cumulo+pH+pH_cumulo+AN+AN_cumulo+interval_yield+OD+Cell_conc._interval+rab_integral+RQ_integral+Arg_conc.+emission_O2+consum_O2+ generate_CO2+interval_CO2; 0.448, 0.762, tmp_cumulo+ pH_cumulo+PL_cumulo+AN+AN_cumulo+OD+Cell_ conc._interval+rab_integral+RQ_integral+Arg_conc.+ emission_CO2+consum_O2+interval_CO2; 0.435, 0.762, pH_cumulo+AN+AN_cumulo+interval_yield+OD+Feed_ Vol+RS_cumulo+Cell_conc._interval+rab_integral+RQ_integral+Arg_conc.+emission_O2+consum_O2+interval_O2; 0.434, 0.762, pH_cumulo+PL+AN+AN_cumulo+OD+Feed_Vol+RS_cumulo+Cell_conc._interval+rab_integral+RQ_integral+Arg_conc.+emission_O2+consum_O2+interval_CO2; 0.461, 0.762, pH_cumulo+AN+AN_cumulo+OD+Feed_Vol+Cell_conc._interval+RQ_integral+Arg_conc.+emission_CO2+interval_O2+generate_CO2+interval_CO2; 0.461, 0.762, pH+pH_cumulo+PL+AN+AN_cumulo+OD+Feed_Vol+Cell_conc._interval+Arg_conc.+emission_CO2+consum_O2+interval_O2; 0.420, 0.762, tmp_cumulo+pH+pH_cumulo+AN+AN_cumulo+interval_yield+OD+Cell_conc._interval+rab_integral+RQ_integral+Arg_conc.+emission_O2+emission_CO2+consum_O2+interval_CO2; 0.434, 0.762, tmp_cumulo+pH+pH_cumulo+AN+AN_cumulo+OD+Feed_Vol+Cell_conc._interval+rab_integral+RQ_integral+Arg_conc.+emission_O2+consum_O2+interval_CO2; 0.389, 0.762, pH+pH_cumulo+PL_cumulo+AN+AN_cumulo+interval_yield+OD+Feed_Vol+Cell_conc._interval+rab_integral+RQ_integral+Arg_conc.+emission_O2+consum_O2+interval_O2+generate_CO2+interval_CO2; 0.461, 0.762, pH+pH_cumulo+AN+AN_cumulo+OD+Feed_Vol+Cell_conc._interval+rab_integral+Arg_conc.+emission_CO2+consum_O2+generate_CO2; 0.389, 0.762, tmp_cumulo+pH+pH_cumulo+PL_cumulo+AN+AN_cumulo+interval_yield+OD+Feed_Vol+Cell_conc._interval+rab_integral+RQ_integral+Arg_conc.+emission_O2+consum_O2+generate_CO2+interval_CO2; 0.474, 0.762, pH_cumulo+AN+AN_cumulo+interval_yield+OD+Feed_Vol+RS_cumulo+Cell_conc._interval+Arg_conc.+emission_CO2+consum_O2; 0.448, 0.762, pH_cumulo+PL_cumulo+AN+AN_cumulo+interval_yield+OD+Feed_Vol+Cell_conc._interval+rab_integral+RQ_integral+Arg_conc.+emission_CO2+consum_O2; 0.388, 0.762, pH_cumulo+PL+PL_cumulo+AN+AN_cumulo+interval_yield+OD+Feed_Vol+Cell_conc._interval+rab_integral+RQ_integral+Arg_conc.+emission_O2+emission_CO2+consum_O2+generate_CO2+interval_CO2; 0.434, 0.762, pH_cumulo+PL+AN+AN_cumulo+interval_yield+OD+Cell_conc._interval+rab_integral+RQ_integral+Arg_conc.+emission_O2+interval_O2+generate_CO2+interval_CO2; 0.420, 0.762, tmp+pH_cumulo+PL+PL_cumulo+AN+AN_cumulo+OD+Feed_Vol+Cell_conc._interval+rab_integral+RQ_integral+Arg_conc.+emission_O2+consum_O2+interval_CO2; 0.405, 0.762, tmp_cumulo+pH_cumulo+PL_cumulo+AN+AN_cumulo+interval_yield+OD+Cell_conc._interval+rab_integral+RQ_integral+Arg_conc.+emission_O2+emission_CO2+consum_O2+interval_O2+interval_CO2; 0.474, 0.762, pH+pH_cumulo+PL+AN_cumulo+interval_yield+OD+Feed_Vol+Cell_conc._interval+Arg_conc.+emission_CO2+consum_O2; 0.420, 0.762, tmp_cumulo+pH_cumulo+PL_cumulo+AN+AN_cumulo+interval_yield+OD+Cell_conc._interval+rab_integral+RQ_integral+Arg_conc.+emission_CO2+consum_O2+generate_CO2+interval_CO2; 0.461, 0.762, pH+pH_cumulo+AN+AN_cumulo+OD+Feed_Vol+Cell_conc._interval+Arg_conc.+emission_CO2+interval_O2+generate_CO2+interval_CO2; 0.420, 0.762, pH+pH_cumulo+PL+AN+AN_cumulo+interval_yield+OD+Feed_Vol+Cell_conc._interval+rab_integral+RQ_integral+Arg_conc.+emission_CO2+consum_O2+interval_CO2; 0.461, 0.762, pH_cumulo+PL+AN+AN_cumulo+OD+Feed_Vol+Cell_conc._interval+RQ_integral+Arg_conc.+emission_O2+consum_O2+interval_O2; 0.486, 0.762, pH+pH_cumulo+AN+AN_cumulo+OD+Feed_Vol+RS_cumulo+Cell_conc._interval+Arg_conc.+emission_O2+consum_O2; 0.434, 0.762, pH+pH_cumulo+PL+PL_cumulo+AN_cumulo+interval_yield+OD+Feed_Vol+Cell_conc._interval+rab_integral+RQ_integral+Arg_conc.+emission_O2+consum_O2; 0.474, 0.762, pH_cumulo+AN+AN_cumulo+OD+Cell_conc._interval+rab_integral+Arg_conc.+emission_CO2+interval_O2+generate_CO2+interval_CO2; 0.448, 0.762, pH_cumulo+PL_cumulo+AN+AN_cumulo+OD+Feed_Vol+Cell_conc._interval+RQ_integral+Arg_conc.+emission_O2+emission_CO2+consum_O2+generate_CO2; 0.461, 0.762, pH+pH_cumulo+PL+AN+AN_cumulo+interval_yield+OD+Cell_conc._interval+Arg_conc.+emission_CO2+consum_O2+interval_CO2; 0.434, 0.762, pH_cumulo+AN+AN_cumulo+interval_yield+OD+Feed_Vol+RS_cumulo+Cell_conc._interval+rab_integral+RQ_integral+Arg_conc.+emission_O2+consum_O2+generate_CO2; 0.486, 0.762, pH_cumulo+PL_cumulo+AN_cumulo+OD+Feed_Vol+Cell_conc._interval+Arg_conc.+emission_O2+emission_CO2+consum_O2; 0.434, 0.762, pH_cumulo+AN+AN_cumulo+interval_yield+OD+Feed_Vol+Cell_conc._interval+rab_integral+RQ_integral+Arg_conc.+emission_O2+consum_O2+interval_O2+interval_CO2; 0.420, 0.762, pH+pH_cumulo+AN+AN_cumulo+interval_yield+OD+Feed_Vol+Cell_conc._interval+rab_integral+RQ_integral+Arg_conc.+emission_O2+consum_O2+interval_O2+generate_CO2; 0.404, 0.762, tmp_cumulo+pH_cumulo+PL_cumulo+AN+AN_cumulo+interval_yield+OD+RS_cumulo+Cell_conc._interval+rab_integral+RQ_integral+Arg_conc.+emission_O2+consum_O2+generate_CO2+interval_CO2; 0.461, 0.762, pH_cumulo+AN+AN_cumulo+interval_yield+OD+RS_cumulo+Cell_conc._interval+Arg_conc.+emission_CO2+interval_O2+generate_CO2+interval_CO2; 0.461, 0.762, pH+pH_cumulo+AN+AN_cumulo+OD+Feed_Vol+Cell_conc._interval+RQ_integral+Arg_conc.+emission_O2+consum_O2+interval_O2; 0.388, 0.762, pH+pH_cumulo+PL+PL_cumulo+AN+AN_cumulo+interval_yield+OD+RS_cumulo+Cell_conc._interval+rab_integral+RQ_integral+Arg_conc.+emission_O2+emission_CO2+consum_O2+interval_CO2; 0.388, 0.762, tmp+tmp_cumulo+pH_cumulo+PL+PL_cumulo+AN+AN_cumulo+interval_yield+OD+Cell_conc._interval+rab_integral+RQ_integral+Arg_conc.+emission_O2+consum_O2+generate_CO2+interval_CO2; 0.485, 0.762, tmp+pH_cumulo+PL+AN_cumulo+OD+Feed_Vol+Cell_conc._interval+Arg_conc.+emission_CO2+consum_O2; 0.448, 0.762, pH_cumulo+PL_cumulo+AN+AN_cumulo+OD+Cell_conc._interval+rab_integral+RQ_integral+Arg_conc.+emission_O2+interval_O2+generate_CO2+interval_CO2; 0.448, 0.762, pH_cumulo+AN+AN_cumulo+OD+Feed_Vol+RS_cumulo+Cell_conc._interval+rab_integral+RQ_integral+Arg_conc.+emission_O2+consum_O2+interval_CO2; 0.419, 0.762, pH+pH_cumulo+AN+AN_cumulo+interval_yield+OD+Feed_Vol+Cell_conc._interval+rab_integral+RQ_integral+Arg_conc.+emission_O2+consum_O2+generate_CO2+interval_CO2; 0.404, 0.762, pH_cumulo+PL+PL_cumulo+AN+AN_cumulo+interval_yield+OD+Cell_conc._interval+rab_integral+RQ_integral+Arg_conc.+emission_O2+emission_CO2+interval_O2+generate_CO2+interval_CO2; 0.473, 0.762, pH_cumulo+AN+AN_cumulo+OD+Feed_Vol+RS_cumulo+Cell_conc._interval+Arg_conc.+emission_O2+emission_CO2+consum_O2; 0.434, 0.762, pH_cumulo+PL+AN+AN_cumulo+interval_yield+OD+Feed_Vol+Cell_conc._interval+rab_integral+RQ_integral+Accum._Yield+Arg_conc.+emission_CO2+consum_O2; 0.419, 0.762, pH+pH_cumulo+PL_cumulo+AN+AN_cumulo+OD+Feed_Vol+Cell_conc._interval+rab_integral+RQ_integral+Arg_conc.+emission_O2+consum_O2+generate_CO2+interval_

CO2; 0.419, 0.762, tmp+pH_cumulo+PL_cumulo+AN+ AN_cumulo+interval_yield+OD+RS_cumulo+Cell_conc._ interval+rab_integral+RQ_integral+Arg_conc.+emission_ O2+consum_O2+interval_CO2; 0.473, 0.762, pH_cumulo+ AN+AN_cumulo+interval_yield+OD+Feed_Vol+Cell_ conc._interval+Arg_conc.+emission_CO2+consum_O2+ interval_CO2; 0.448, 0.762, pH_cumulo+AN+AN_ cumulo+interval_yield+OD+Feed_Vol+Cell_conc._ interval+RQ_integral+Arg_conc.+emission_O2+emission_ CO2+consum_O2+generate_CO2; 0.404, 0.762, pH+pH_ cumulo+PL+PL_cumulo+AN+AN_cumulo+interval_ yield+OD+Feed_Vol+Cell_conc._interval+rab_integral+ RQ_integral+Accum._Yield+Arg_conc.+emission_O2+ consum_O2; 0.473, 0.762, tmp_cumulo+pH_cumulo+AN+ AN_cumulo+OD+Cell_conc._interval+Arg_conc.+ emission_O2+emission_CO2+consum_O2+interval_CO2; 0.434, 0.762, pH+pH_cumulo+AN+AN_cumulo+OD+ Feed_Vol+Cell_conc._interval+rab_integral+RQ_integral+ Arg_conc.+emission_O2+emission_CO2+consum_O2+ generate_CO2; 0.404, 0.762, tmp+pH_cumulo+PL_ cumulo+AN+AN_cumulo+interval_yield+OD+Cell_conc._ interval+rab_integral+RQ_integral+Arg_conc.+emission_ O2+consum_O2+interval_O2+generate_CO2+interval_ CO2; 0.404, 0.762, pH+pH_cumulo+PL_cumulo+AN+AN_ cumulo+interval_yield+OD+Feed_Vol+Cell_conc._ interval+rab_integral+RQ_integral+Arg_conc.+emission_ O2+emission_CO2+consum_O2+interval_CO2; 0.448, 0.762, pH_cumulo+PL_cumulo+AN+AN_cumulo+inter- val_yield+OD+Cell_conc._interval+RQ_integral+Arg_ conc.+emission_CO2+consum_O2+generate_CO2+inter- val_CO2; 0.461, 0.762, pH_cumulo+AN+AN_cumulo+ OD+Feed_Vol+Cell_conc._interval+rab_integral+RQ_ integral+Arg_conc.+emission_O2+interval_O2+generate_ CO2; 0.461, 0.762, tmp_cumulo+pH_cumulo+AN+AN_ cumulo+interval_yield+OD+rab_integral+RQ_integral+ Arg_conc.+emission_O2+consum_O2+interval_CO2; 0.448, 0.762, pH+pH_cumulo+AN+AN_cumulo+interval_ yield+OD+Feed_Vol+Cell_conc._interval+RQ_integral+ Arg_conc.+emission_CO2+consum_O2+generate_CO2; 0.473, 0.762, tmp_cumulo+pH+pH_cumulo+AN+AN_cu- mulo+OD+Feed_Vol+Cell_conc._interval+Arg_conc.+ emission_CO2+consum_O2; 0.461, 0.762, tmp_cumulo+ pH+pH_cumulo+AN+AN_cumulo+OD+Feed_Vol+Cell_ conc._interval+Arg_conc.+emission_CO2+consum_O2+ interval_CO2; 0.448, 0.762, pH_cumulo+PL_cumulo+AN+ AN_cumulo+interval_yield+OD+Feed_Vol+Cell_conc._ interval+RQ_integral+Arg_conc.+emission_CO2+consum_ O2+generate_CO2; 0.461, 0.762, pH+pH_cumulo+PL_ cumulo+AN+AN_cumulo+OD+Feed_Vol+Cell_conc._ interval+RQ_integral+Arg_conc.+emission_CO2+consum_ O2; 0.404, 0.762, tmp_cumulo+pH_cumulo+PL+PL_ cumulo+AN+AN_cumulo+interval_yield+OD+Cell_conc._ interval+rab_integral+RQ_integral+Arg_conc.+emission_ O2+emission_CO2+consum_O2+interval_CO2; 0.461, 0.762, pH+pH_cumulo+PL+AN+AN_cumulo+OD+Feed_ Vol+Cell_conc._interval+Arg_conc.+emission_CO2+con- sum_O2+generate_CO2; 0.448, 0.762, pH_cumulo+AN+ AN_cumulo+interval_yield+OD+Cell_conc._interval+rab_ integral+RQ_integral+Arg_conc.+emission_CO2+consum_ O2+generate_CO2+interval_CO2; 0.434, 0.762, pH+pH_ cumulo+AN+AN_cumulo+OD+Feed_Vol+Cell_conc._ interval+rab_integral+RQ_integral+Arg_conc.+emission_ O2+emission_CO2+consum_O2+interval_O2; 0.473, 0.762, pH_cumulo+AN+AN_cumulo+OD+Feed_Vol+RS_ cumulo+Cell_conc._interval+Arg_conc.+emission_CO2+ consum_O2+interval_CO2; 0.447, 0.762, pH_cumulo+AN+ AN_cumulo+OD+Feed_Vol+RS_cumulo+Cell_conc._ interval+rab_integral+RQ_integral+Arg_conc.+emission_ O2+consum_O2+interval_O2; 0.473, 0.762, tmp+pH_ cumulo+AN+AN_cumulo+OD+Feed_Vol+Cell_conc._ interval+Arg_conc.+emission_CO2+consum_O2+interval_ CO2; 0.461, 0.762, tmp+tmp_cumulo+pH_cumulo+PL+ AN+AN_cumulo+OD+Cell_conc._interval+Arg_conc.+ emission_CO2+consum_O2+interval_CO2; 0.460, 0.762, pH_cumulo+PL+AN+AN_cumulo+OD+Feed_Vol+RS_cu- mulo+Cell_conc._interval+Arg_conc.+emission_CO2+ consum_O2+interval CO2; 0.473, 0.762, pH_cumulo+AN+ AN_cumulo+OD+Cell_conc._interval+RQ_integral+Arg_ conc.+emission_CO2+interval_O2+generate_CO2+ interval_CO2; 0.419, 0.762, pH+pH_cumulo+PL+PL_ cumulo+AN+AN_cumulo+interval_yield+OD+Cell_conc._ interval+rab_integral+RQ_integral+Arg_conc.+emission_ CO2+generate_CO2+interval_CO2; 0.485, 0.762, pH_cumulo+PL+AN+AN_cumulo+OD+Feed_Vol+Cell_conc._ interval+rab_integral+Arg_conc.+emission_CO2+consum_ O2; 0.447, 0.762, pH_cumulo+AN+AN_cumulo+interval_ yield+OD+Feed_Vol+Cell_conc._interval+RQ_integral+ Arg_conc.+emission_CO2+consum_O2+interval_O2+ generate_CO2; 0.433, 0.762, pH_cumulo+PL+PL_cumulo+ AN+AN_cumulo+interval_yield+OD+RS_cumulo+rab_ integral+RQ_integral+Arg_conc.+emission_O2+consum_ O2+interval_CO2; 0.460, 0.762, pH_cumulo+PL_cumulo+ AN+AN_cumulo+interval_yield+OD+Cell_conc._interval+ rab_integral+Arg_conc.+emission_CO2+generate_CO2+ interval_CO2; 0.404, 0.762, pH+pH_cumulo+PL_cumulo+ AN+AN_cumulo+interval_yield+OD+RS+Feed_Vol+Cell_ conc._interval+rab_integral+RQ_integral+Arg_conc.+ emission_O2+consum_O2+interval_O2; 0.447, 0.762, pH_cumulo+AN+AN_cumulo+OD+Feed_Vol+Cell_conc._ interval+rab_integral+RQ_integral+Arg_conc.+emission_ O2+consum_O2+interval_O2+interval_CO2; 0.404, 0.762, pH_cumulo+PL+PL_cumulo+AN+AN_cumulo+interval_ yield+OD+Feed_Vol+RS_cumulo+Cell_conc._interval+ rab_integral+RQ_integral+Arg_conc.+emission_O2+emis- sion_CO2+consum_O2; 0.485, 0.762, pH_cumulo+PL_ cumulo+AN+interval_yield+OD+Feed_Vol+Cell_ conc._interval+Arg_conc.+emission_CO2+consum_O2; 0.460, 0.762, pH+pH_cumulo+AN+AN_cumulo+OD+ Cell_conc._interval+Arg_conc.+emission_CO2+consum_ O2+interval_O2+generate_CO2+interval_CO2; 0.460, 0.762, pH_cumulo+PL+AN+AN_cumulo+OD+Feed_Vol+ Cell_conc._interval+Arg_conc.+emission_CO2+interval_ O2+generate_CO2+interval_CO2; 0.447, 0.762, pH+pH_ cumulo+PL+AN+AN_cumulo+OD+Cell_conc._interval+ rab_integral+RQ_integral+Arg_conc.+emission_O2+ interval_O2+interval_CO2; 0.447, 0.762, pH_cumulo+AN+ AN_cumulo+interval_yield+OD+Cell_conc._interval+rab_ integral+RQ_integral+Arg_conc.+emission_O2+consum_ O2+interval_O2+interval_CO2; 0.447, 0.762, tmp_ cumulo+pH+pH_cumulo+AN+AN_cumulo+interval_ yield+OD+Cell_conc._interval+Arg_conc.+emission_ CO2+consum_O2+generate_CO2+interval_CO2; 0.433, 0.762, pH_cumulo+PL+AN+AN_cumulo+interval_yield+ OD+Feed_Vol+Cell_conc._interval+rab_integral+RQ_inte- gral+Arg_conc.+emission_CO2+consum_O2+interval_O2; 0.433, 0.762, tmp_cumulo+pH_cumulo+PL_cumulo+AN+ AN_cumulo+interval_yield+OD+Cell_conc._interval+rab_ integral+RQ_integral+Arg_conc.+emission_O2+generate_ CO2+interval_CO2; 0.433, 0.762, pH+pH_cumulo+AN+ AN_cumulo+OD+Feed_Vol+Cell_conc._interval+rab_ integral+RQ_integral+Arg_conc.+emission_O2+emission_ CO2+consum_O2+interval_CO2; 0.419, 0.762, tmp_ cumulo+pH+pH_cumulo+AN+AN_cumulo+interval_ yield+OD+Feed_Vol+Cell_conc._interval+rab_integral+

RQ_integral+Arg_conc.+emission_O2+consum_O2+interval_CO2; 0.460, 0.762, tmp+pH_cumulo+AN+AN_cumulo+OD+Feed_Vol+Cell_conc._interval+rab_integral+RQ_integral+Arg_conc.+emission_CO2+consum_O2; 0.460, 0.762, pH_cumulo+PL_cumulo+AN+AN_cumulo+interval_yield+OD+Cell_conc._interval+Arg_conc.+emission_CO2+consum_O2+interval_O2+interval_CO2; 0.403, 0.762, pH+pH_cumulo+PL_cumulo+AN+AN_cumulo+interval_yield+OD+Feed_Vol+Cell_conc._interval+rab_integral+RQ_integral+Arg_conc.+emission_O2+emission_CO2+consum_O2+generate_CO2; 0.387, 0.762, pH_cumulo+PL+PL_cumulo+AN+AN_cumulo+interval_yield+OD+Feed_Vol+RS_cumulo+Cell_conc._interval+rab_integral+RQ_integral+Arg_conc.+emission_O2+emission_CO2+consum_O2+interval_CO2; 0.387, 0.762, tmp+tmp_cumulo+pH+pH_cumulo+PL_cumulo+AN+AN_cumulo+interval_yield+OD+Cell_conc._interval+rab_integral+RQ_integral+Arg_conc.+emission_O2+consum_O2+generate_CO2+interval_CO2; 0.473, 0.762, pH_cumulo+PL+AN+AN_cumulo+OD+RS_cumulo+Cell_conc._interval+Arg_conc.+emission_CO2+consum_O2+interval_CO2; 0.419, 0.762, pH+pH_cumulo+PL+PL_cumulo+AN+AN_cumulo+OD+Feed_Vol+Cell_conc._interval+rab_integral+RQ_integral+Arg_conc.+emission_O2+consum_O2+interval_O2; 0.403, 0.762, pH_cumulo+PL+PL_cumulo+AN+AN_cumulo+interval_yield+OD+Cell_conc._interval+rab_integral+RQ_integral+Accum._Yield+Arg_conc.+emission_O2+consum_O2+interval_O2+interval_CO2; 0.419, 0.762, tmp+pH+pH_cumulo+PL_cumulo+AN+AN_cumulo+OD+Feed_Vol+Cell_conc._interval+rab_integral+RQ_integral+Arg_conc.+emission_O2+consum_O2+interval_O2; 0.447, 0.762, pH+pH_cumulo+AN+AN_cumulo+interval_yield+OD+Feed_Vol+Cell_conc._interval+RQ_integral+Arg_conc.+emission_CO2+consum_O2+interval_O2; 0.460, 0.762, pH_cumulo+PL+PL_cumulo+AN+AN_cumulo+interval_yield+OD+Feed_Vol+Cell_conc._interval+Arg_conc.+emission_CO2+consum_O2; 0.460, 0.762, tmp+pH+pH_cumulo+AN+AN_cumulo+OD+Cell_conc._interval+Arg_conc.+emission_CO2+interval_O2+generate_CO2+interval_CO2; 0.460, 0.762, pH_cumulo+PL+AN+AN_cumulo+interval_yield+OD+Feed_Vol+Cell_conc._interval+Arg_conc.+emission_CO2+consum_O2+interval_O2; 0.433, 0.762, pH_cumulo+PL_cumulo+AN+AN_cumulo+interval_yield+OD+Feed_Vol+Cell_conc._interval+rab_integral+RQ_integral+Arg_conc.+emission_CO2+generate_CO2+interval_CO2; 0.447, 0.762, pH+pH_cumulo+PL+AN+AN_cumulo+OD+Feed_Vol+Cell_conc._interval+RQ_integral+Arg_conc.+emission_CO2+consum_O2+interval_O2; 0.485, 0.762, pH_cumulo+PL+AN_cumulo+OD+Feed_Vol+Cell_conc._interval+RQ_integral+Arg_conc.+emission_O2+consum_O2; 0.473, 0.762, pH_cumulo+PL+AN_cumulo+interval_yield+OD+Feed_Vol+RS_cumulo+Cell_conc._interval+Arg_conc.+emission_CO2+consum_O2; 0.433, 0.762, pH_cumulo+PL+AN+AN_cumulo+interval_yield+OD+Cell_conc._interval+rab_integral+RQ_integral+Accum._Yield+Arg_conc.+emission_O2+consum_O2+interval_CO2; 0.433, 0.762, pH_cumulo+PL+AN+AN_cumulo+interval_yield+OD+Feed_Vol+Cell_conc._interval+rab_integral+RQ_integral+Arg_conc.+emission_CO2+consum_O2+generate_CO2; 0.433, 0.762, tmp_cumulo+pH_cumulo+AN+AN_cumulo+interval_yield+OD+Cell_conc._interval+rab_integral+RQ_integral+Arg_conc.+emission_O2+consum_O2+interval_O2+interval_CO2; 0.403, 0.762, tmp_cumulo+pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_O2; 0.418, 0.762, pH+pH_cumulo+PL_cumulo+AN+AN_cumulo+interval_yield+OD+Feed_Vol+Cell_conc._interval+rab_integral+RQ_integral+Accum._Yield+Arg_conc.+emission_O2+consum_O2; 0.433, 0.762, tmp_cumulo+pH_cumulo+AN+AN_cumulo+interval_yield+OD+Cell_conc._interval+rab_integral+RQ_integral+Arg_conc.+emission_CO2+consum_O2+generate_CO2+interval_CO2; 0.433, 0.762, tmp+pH_cumulo+PL+PL_cumulo+AN+AN_cumulo+OD+Cell_conc._interval+rab_integral+RQ_integral+Arg_conc.+emission_O2+consum_O2+interval_CO2; 0.447, 0.762, pH_cumulo+AN+AN_cumulo+OD+Feed_Vol+Cell_conc._interval+RQ_integral+Arg_conc.+emission_O2+emission_CO2+consum_O2+interval_O2+generate_CO2; 0.460, 0.762, pH_cumulo+AN+AN_cumulo+interval_yield+OD+Feed_Vol+Cell_conc._interval+Arg_conc.+emission_CO2+consum_O2+generate_CO2+interval_CO2; 0.418, 0.762, tmp_cumulo+pH+pH_cumulo+PL_cumulo+AN+AN_cumulo+OD+Feed_Vol+Cell_conc._interval+rab_integral+RQ_integral+Arg_conc.+emission_O2+consum_O2+interval_CO2; 0.433, 0.762, pH_cumulo+PL+AN+AN_cumulo+OD+Feed_Vol+RS_cumulo+Cell_conc._interval+rab_integral+RQ_integral+Arg_conc.+emission_O2+consum_O2+interval_O2; 0.433, 0.762, pH_cumulo+PL+AN+AN_cumulo+interval_yield+OD+RS_cumulo+Cell_conc._interval+rab_integral+RQ_integral+Arg_conc.+emission_CO2+consum_O2+interval_CO2; 0.447, 0.762, tmp+pH_cumulo+PL_cumulo+AN+AN_cumulo+interval_yield+OD+Cell_conc._interval+Arg_conc.+emission_CO2+consum_O2+generate_CO2+interval_CO2; 0.433, 0.762, pH_cumulo+PL+AN+AN_cumulo+interval_yield+OD+RS+Cell_conc._interval+rab_integral+RQ_integral+Arg_conc.+emission_CO2+generate_CO2+interval_CO2; 0.418, 0.762, pH_cumulo+AN+AN_cumulo+interval_yield+OD+Feed_Vol+Cell_conc._interval+rab_integral+RQ_integral+Arg_conc.+emission_O2+emission_CO2+consum_O2+generate_CO2+interval_CO2; 0.472, 0.762, tmp+pH_cumulo+AN+AN_cumulo+OD+Feed_Vol+Cell_conc._interval+rab_integral+Arg_conc.+emission_CO2+consum_O2; 0.447, 0.762, pH_cumulo+PL_cumulo+AN+AN_cumulo+interval_yield+OD+Cell_conc._interval+Arg_conc.+emission_O2+emission_CO2+consum_O2+generate_CO2+interval_CO2; 0.460, 0.762, pH+pH_cumulo+PL_cumulo+AN+AN_cumulo+OD+Feed_Vol+Cell_conc._interval+RQ_integral+Arg_conc.+emission_O2+consum_O2; 0.387, 0.762, tmp_cumulo+pH+pH_cumulo+PL_cumulo+AN+AN_cumulo+interval_yield+OD+Cell_conc._interval+rab_integral+RQ_integral+Arg_conc.+emission_O2+emission_CO2+consum_O2+generate_CO2+interval_CO2; 0.418, 0.762, tmp_cumulo+pH_cumulo+PL+AN+AN_cumulo+interval_yield+OD+Cell_conc._interval+rab_integral+RQ_integral+Arg_conc.+emission_O2+consum_O2+generate_CO2+interval_CO2; 0.403, 0.762, pH_cumulo+PL+PL_cumulo+AN+AN_cumulo+interval_yield+OD+RS+RS_cumulo+Cell_conc._interval+rab_integral+RQ_integral+Arg_conc.+emission_O2+consum_O2+interval_CO2; 0.484, 0.761, pH_cumulo+PL+AN_cumulo+OD+Feed_Vol+Cell_conc._interval+RQ_integral+Arg_conc.+emission_CO2+consum_O2; 0.418, 0.761, pH+pH_cumulo+AN+AN_cumulo+interval_yield+OD+Feed_Vol+Cell_conc._interval+rab_integral+RQ_integral+Arg_conc.+emission_O2+emission_CO2+consum_O2+interval_CO2; 0.447, 0.761, pH+pH_cumulo+PL_cumulo+AN+AN_cumulo+OD+Feed_Vol+Cell_conc._interval+RQ_integral+Arg_conc.+emission_O2+consum_O2+interval_O2; 0.460, 0.761, pH_cumulo+PL+AN+AN_cumulo+interval_yield+OD+

Cell_conc._interval+rab_integral+RQ_integral+Arg_conc.+emission_CO2+consum_O2; 0.472, 0.761, tmp+pH_cumulo+AN+AN_cumulo+OD+Cell_conc._interval+Arg_conc.+emission_CO2+consum_O2+generate_CO2+interval_CO2; 0.418, 0.761, tmp+pH_cumulo+PL+AN+AN_cumulo+interval_yield+OD+Feed_Vol+RS_cumulo+Cell_conc._interval+rab_integral+RQ_integral+Arg_conc.+emission_O2+consum_O2; 0.418, 0.761, pH_cumulo+PL_cumulo+AN+AN_cumulo+interval_yield+OD+RS+Cell_conc._interval+rab_integral+RQ_integral+Arg_conc.+emission_O2+emission_CO2+consum_O2+interval_CO2; 0.472, 0.761, pH_cumulo+PL_cumulo+AN+AN_cumulo+OD+Feed_Vol+RS_cumulo+Cell_conc._interval+Arg_conc.+emission_CO2+consum_O2; 0.418, 0.761, tmp_cumulo+pH_cumulo+PL+AN+AN_cumulo+interval_yield+OD+Cell_conc._interval+rab_integral+RQ_integral+Arg_conc.+emission_O2+interval_O2+generate_CO2+interval_CO2; 0.447, 0.761, tmp_cumulo+pH+pH_cumulo+AN+AN_cumulo+interval_yield+OD+Cell_conc._interval+Arg_conc.+emission_CO2+interval_O2+generate_CO2+interval_CO2; 0.447, 0.761, tmp+pH_cumulo+AN+AN_cumulo+interval_yield+OD+Cell_conc._interval+rab_integral+RQ_integral+Arg_conc.+emission_O2+consum_O2+interval_CO2; 0.403, 0.761, pH_cumulo+PL_cumulo+AN+AN_cumulo+interval_yield+OD+Feed_Vol+Cell_conc._interval+rab_integral+RQ_integral+Accum._Yield+Arg_conc.+emission_O2+consum_O2+generate_CO2+interval_CO2; 0.403, 0.761, pH_cumulo+PL_cumulo+AN+AN_cumulo+interval_yield+OD+Feed_Vol+Cell_conc._interval+rab_integral+RQ_integral+Arg_conc.+emission_O2+emission_CO2+interval_O2+generate_CO2+interval_CO2; 0.472, 0.761, pH+pH_cumulo+AN+AN_cumulo+OD+Cell_conc._interval+Arg_conc.+emission_CO2+consum_O2+interval_O2+interval_CO2; 0.433, 0.761, tmp+pH_cumulo+AN+AN_cumulo+interval_yield+OD+Cell_conc._interval+rab_integral+RQ_integral+Arg_conc.+emission_O2+interval_O2+generate_CO2+interval_CO2; 0.387, 0.761, tmp+tmp_cumulo+pH_cumulo+PL+PL_cumulo+AN+AN_cumulo+interval_yield+OD+Cell_conc._interval+rab_integral+RQ_integral+Arg_conc.+emission 2+consum_O2+interval_O2+interval_CO2; 0.387, 0.761, pH+pH_cumulo+PL+PL_cumulo+AN+AN_cumulo+interval_yield+OD+Cell_conc._interval+rab_integral+RQ_integral+Arg_conc.+emission_O2+emission_CO2+consum_O2+interval_O2+interval_CO2; 0.460, 0.761, pH+pH_cumulo+AN+AN_cumulo+OD+Feed_Vol+Cell_conc._interval+Arg_conc.+emission_CO2+consum_O2+generate_CO2+interval_CO2; 0.403, 0.761, pH_cumulo+PL_cumulo+AN+AN_cumulo+interval_yield+OD+Feed_Vol+RS_cumulo+Cell_conc._interval+rab_integral+RQ_integral+Arg_conc.+emission_O2+interval_O2+generate_CO2+interval_CO2; 0.446, 0.761, pH_cumulo+AN+AN_cumulo+interval_yield+OD+Feed_Vol+Cell_conc._interval+RQ_integral+Arg_conc.+emission_O2+emission_CO2+consum_O2+interval_O2; 0.403, 0.761, pH_cumulo+PL+PL_cumulo+AN+AN_cumulo+interval_yield+OD+Feed_Vol+RS_cumulo+Cell_conc._interval+rab_integral+RQ_integral+Accum._Yield+Arg_conc.+emission_O2+consum_O2; 0.446, 0.761, tmp_cumulo+pH_cumulo+PL+AN+AN_cumulo+OD+Cell_conc._interval+rab_integral+RQ_integral+Arg_conc.+emission_O2+consum_O2+interval_CO2; 0.387, 0.761, pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_O2+generate_CO2+interval_CO2; 0.387, 0.761, tmp+pH+pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_CO2; 0.472, 0.761, pH_cumulo+AN+AN_cumulo+OD+Feed_Vol+RS_cumulo+Cell_conc._interval+RQ_integral+Arg_conc.+emission_O2+consum_O2; 0.446, 0.761, pH_cumulo+PL+PL_cumulo+AN+AN_cumulo+OD+Feed_Vol+Cell_conc._interval+rab_integral+RQ_integral+Arg_conc.+emission_CO2+consum_O2; 0.403, 0.761, tmp+pH_cumulo+PL_cumulo+AN+AN_cumulo+interval_yield+OD+RS_cumulo+Cell_conc._interval+rab_integral+RQ_integral+Arg_conc.+emission_O2+consum_O2+generate_CO2+interval_CO2; 0.418, 0.761, pH_cumulo+PL+PL_cumulo+AN+AN_cumulo+OD+Feed_Vol+Cell_conc._interval+rab_integral+RQ_integral+Arg_conc.+emission_O2+consum_O2+interval_O2+interval_CO2; 0.446, 0.761, pH_cumulo+AN+AN_cumulo+OD+Feed_Vol+RS_cumulo+Cell_conc._interval+rab_integral+RQ_integral+Arg_conc.+emission_O2+consum_O2+generate_CO2; 0.460, 0.761, pH_cumulo+PL_cumulo+AN+AN_cumulo+interval_yield+OD+Feed_Vol+Cell_conc._interval+Arg_conc.+emission_CO2+generate_CO2+interval_CO2; 0.472, 0.761, pH_cumulo+AN+AN_cumulo+interval_yield+OD+Feed_Vol+Cell_conc._interval+Arg_conc.+emission_CO2+consum_O2+generate_CO2; 0.387, 0.761, tmp_cumulo+pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+generate CO2+interval_CO2; 0.460, 0.761, tmp_cumulo+pH_cumulo+AN+AN_cumulo+OD+Cell_conc._interval+rab_integral+RQ_integral+Arg_conc.+emission_CO2+interval_O2+interval_CO2; 0.460, 0.761, pH+pH_cumulo+AN_cumulo+interval_yield+OD+Feed_Vol+Cell_conc._interval+rab_integral+RQ_integral+Arg_conc.+emission_O2+consum_O2; 0.386, 0.761, pH_cumulo+PL+PL_cumulo+AN+AN_cumulo+interval_yield+OD+RS_cumulo+Cell_conc._interval+rab_integral+RQ_integral+Arg_conc.+emission_O2+consum_O2+interval_O2+generate_CO2+interval_CO2; 0.433, 0.761, pH_cumulo+AN+AN_cumulo+interval_yield+OD+Cell_conc._interval+rab_integral+RQ_integral+Arg_conc.+emission_O2+emission_CO2+consum_O2+generate_CO2+interval_CO2; 0.459, 0.761, pH_cumulo+AN+AN_cumulo+OD+Feed_Vol+Cell_conc._interval+rab_integral+Accum._Yield+Arg_conc.+emission_O2+consum_O2; 0.446, 0.761, pH+pH_cumulo+PL+AN+AN_cumulo+OD+Feed_Vol+Cell_conc._interval+RQ_integral+Arg_conc.+emission_CO2+consum_O2+generate_CO2; 0.403, 0.761, pH+pH_cumulo+PL+AN+AN_cumulo+interval_yield+OD+RS_cumulo+Cell_conc._interval+rab_integral+RQ_integral+Arg_conc.+emission_O2+interval_O2+generate_CO2+interval_CO2; 0.418, 0.761, tmp_cumulo+pH_cumulo+PL+PL_cumulo+AN+AN_cumulo+OD+Feed_Vol+Cell_conc._interval+rab_integral+RQ_integral+Arg_conc.+emission_O2+consum_O2+interval_CO2; 0.459, 0.761, pH+pH_cumulo+AN+AN_cumulo+OD+Feed_Vol+Cell_conc._interval+rab_integral+Arg_conc.+emission_O2+emission_CO2+consum_O2; 0.446, 0.761, pH_cumulo+AN+AN_cumulo+OD+Feed_Vol+Cell_conc._interval+rab_integral+RQ_integral+Arg_conc.+emission_O2+consum_O2+generate_CO2+interval_CO2; 0.386, 0.761, pH+pH_cumulo+PL+PL_cumulo+AN+AN_cumulo+interval_yield+OD+Feed_Vol+Cell_conc._interval+rab_integral+RQ_integral+Arg_conc.+emission_O2+emission_CO2+consum_O2+interval_O2; 0.459, 0.761, pH_cumulo+AN+AN_cumulo+OD+Feed_Vol+RS_cumulo+Cell_conc._interval+RQ_integral+Arg_conc.+emission_CO2+consum_O2+generate_CO2; 0.386, 0.761, tmp+pH_cumulo+PL+

PL_cumulo+AN+AN_cumulo+interval_yield+OD+Feed_Vol+Cell_conc._interval+rab_integral+RQ_integral+Arg_conc.+emission_O2+consum_O2+interval_O2+interval_CO2; 0.472, 0.761, pH_cumulo+AN+AN_cumulo+OD+Cell_conc._interval+rab_integral+RQ_integral+Arg_conc.+emission_CO2+consum_O2+interval_CO2; 0.446, 0.761, pH_cumulo+PL+PL_cumulo+AN+AN_cumulo+interval_yield+OD+Cell_conc._interval+Arg_conc.+emission_CO2+interval_O2+generate_CO2+interval_CO2; 0.386, 0.761, pH+pH_cumulo+PL+PL_cumulo+AN+AN_cumulo+interval_yield+OD+RS_cumulo+Cell_conc._interval+rab_integral+RQ_integral+Arg_conc.+emission_O2+interval_O2+generate_CO2+interval CO2; 0.446, 0.761, pH_cumulo+PL+AN+AN_cumulo+OD+Feed_Vol+Cell_conc._interval+rab_integral+RQ_integral+Arg_conc.+emission_CO2+consum_O2+interval_CO2; 0.459, 0.761, tmp_cumulo+pH+pH_cumulo+AN+AN_cumulo+OD+Cell_conc._interval+rab_integral+Arg_conc.+emission_CO2+consum_O2+interval_CO2; 0.402, 0.761, tmp_cumulo+pH+pH_cumulo+PL_cumulo+AN+AN_cumulo+interval_yield+OD+Feed_Vol+Cell_conc._interval+rab_integral+RQ_integral+Arg_conc.+emission_O2+consum_O2+interval_CO2; 0.459, 0.761, pH_cumulo+PL_cumulo+AN+AN_cumulo+interval_yield+OD+Feed_Vol+Cell_conc._interval+Arg_conc.+emission_CO2+consum_O2+interval_O2; 0.484, 0.761, pH_cumulo+AN_cumulo+OD+Feed_Vol+Cell_conc._interval+Arg_conc.+emission_CO2+consum_O2+interval_O2+generate_CO2; 0.459, 0.761, pH_cumulo+PL+AN+AN_cumulo+OD+Feed_Vol+Cell_conc._interval+rab_integral+Arg_conc.+emission_CO2+consum_O2+interval_CO2; 0.418, 0.761, tmp+pH_cumulo+PL+AN+AN_cumulo+interval_yield+OD+RS_cumulo+Cell_conc._interval+rab_integral+RQ_integral+Arg_conc.+emission_O2+consum_O2+interval_CO2; 0.418, 0.761, pH_cumulo+PL+PL_cumulo+AN+AN_cumulo+interval_yield+OD+Cell_conc._interval+rab_integral+RQ_integral+Arg_conc.+emission_CO2+consum_O2+interval_O2+interval_CO2; 0.459, 0.761, tmp_cumulo+pH_cumulo+AN+AN_cumulo+OD+Cell_conc._interval+Arg_conc.+emission_CO2+emission_CO2+interval_O2+generate_CO2+interval_CO2; 0.459, 0.761, tmp_cumulo+pH_cumulo+PL_cumulo+AN+N+AN_cumulo+interval_yield+OD+Cell_conc._interval+Arg_conc.+emission_CO2+generate_CO2+interval_CO2; 0.402, 0.761, tmp+tmp_cumulo+pH+pH_cumulo+PL_cumulo+AN+AN_cumulo+interval_yield+OD+Cell_conc._interval+rab_integral+RQ_integral+Arg_conc.+emission_CO2+consum_O2+interval_CO2; 0.484, 0.761, pH_cumulo+PL_cumulo+AN_cumulo+OD+Feed_Vol+Cell_conc._interval+RQ_integral+Arg_conc.+emission_O2+consum_O2; 0.459, 0.761, pH_cumulo+PL_cumulo+AN+AN_cumulo+interval_yield+OD+Cell_conc._interval+Arg_conc.+emission_O2+emission_CO2+generate_CO2+interval_CO2; 0.432, 0.761, tmp+pH+pH_cumulo+PL+AN+AN_cumulo+OD+Feed_Vol+Cell_conc._interval+rab_integral+RQ_integral+Arg_conc.+emission_O2+consum_O2; 0.459, 0.761, tmp+pH_cumulo+PL+AN+AN_cumulo+OD+Feed_Vol+Cell_conc._interval+RQ_integral+Arg_conc.+emission_CO2+consum_O2; 0.459, 0.761, pH_cumulo+AN+AN_cumulo+OD+Feed_Vol+RS_cumulo+Cell_conc._interval+RQ_integral+Arg_conc.+emission_CO2+consum_O2+interval_O2; 0.459, 0.761, tmp+pH+pH_cumulo+PL+AN+AN_cumulo+OD+Feed_Vol+Cell_conc._interval+Arg_conc.+emission_CO2+consum_O2; 0.446, 0.761, pH_cumulo+AN+AN_cumulo+interval_yield+OD+Feed_Vol+Cell_conc._interval+RQ_integral+Arg_conc.+emission_CO2+consum_O2+generate_CO2+interval_CO2; 0.446, 0.761, tmp_cumulo+pH_cumulo+PL+AN+AN_cumulo+OD+Cell_conc._interval+rab_integral+RQ_integral+Arg_conc.+emission_O2+interval_O2+interval_CO2; 0.484, 0.761, pH_cumulo+AN+AN_cumulo+OD+Cell_conc._interval+rab_integral+Arg_conc.+emission_CO2+consum_O2+interval_CO2; 0.495, 0.761, tmp_cumulo+pH_cumulo+AN_cumulo+OD+Feed_Vol+Cell_conc._interval+Arg_conc.+emission_CO2+consum_O2; 0.402, 0.761, pH_cumulo+PL_cumulo+AN+AN_cumulo+interval_yield+OD+RS_cumulo+Cell_conc._interval+rab_integral+RQ_integral+Arg_conc.+emission_O2+emission_CO2+consum_O2+generate_CO2+interval_CO2; 0.402, 0.761, pH_cumulo+PL+PL_cumulo+AN+AN_cumulo+interval_yield+OD+RS+Cell_conc._interval+rab_integral+RQ_integral+Arg_conc.+emission_O2+emission_CO2+consum_O2+interval_CO2; 0.459, 0.761, tmp_cumulo+pH_cumulo+AN+AN_cumulo+OD+Cell_conc._interval+Arg_conc.+emission_CO2+consum_O2+interval_O2+generate_CO2+interval_CO2; 0.432, 0.761, pH+pH_cumulo+AN+AN_cumulo+OD+Feed_Vol+RS_cumulo+Cell_conc._interval+rab_integral+RQ_integral+Arg_conc.+emission_O2+emission_CO2+consum_O2; 0.417, 0.761, pH+pH_cumulo+PL+PL_cumulo+AN+AN_cumulo+OD+Feed_Vol+Cell_conc._interval+rab_integral+RQ_integral+Arg_conc.+emission_O2+consum_O2+generate_CO2; 0.386, 0.761, pH_cumulo+PL+PL_cumulo+AN+AN_cumulo+interval_yield+OD+Feed_Vol+Cell_conc._interval+rab_integral+RQ_integral+Arg_conc.+emission_O2+emission_CO2+consum_O2+interval_O2+interval_CO2; 0.484, 0.761, pH_cumulo+AN_cumulo+OD+Feed_Vol+Cell_conc._interval+rab_integral+Arg_conc.+emission_O2+emission_CO2+consum_O2; 0.386, 0.761, tmp+pH+pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_O2; 0.472, 0.761, tmp+pH_cumulo+AN+AN_cumulo+OD+Feed_Vol+Cell_conc._interval+Arg_conc.+emission_O2+emission_CO2+consum_O2; 0.402, 0.761, pH_cumulo+PL+AN+AN_cumulo+interval_yield+OD+Feed_Vol+RS_cumulo+Cell_conc._interval+rab_integral+RQ_integral+Accum._Yield+Arg_conc.+emission_O2+consum_O2+interval_CO2; 0.472, 0.761, pH_cumulo+AN_cumulo+OD+Feed_Vol+Cell_conc._interval+rab_integral+RQ_integral+Arg_conc.+emission_O2+emission_CO2+consum_O2; 0.446, 0.761, tmp_cumulo+pH_cumulo+AN+AN_cumulo+OD+Cell_conc._interval+rab_integral+RQ_integral+Arg_conc.+emission_O2+interval_O2+generate_CO2+interval_CO2; 0.483, 0.761, pH_cumulo+AN_cumulo+interval_yield+OD+Feed_Vol+Cell_conc._interval+Arg_conc.+emission_O2+emission_CO2+consum_O2; 0.432, 0.761, tmp_cumulo+pH_cumulo+PL+AN+AN_cumulo+OD+Feed_Vol+Cell_conc._interval+rab_integral+RQ_integral+Arg_conc.+emission_O2+consum_O2+interval_CO2; 0.483, 0.761, pH_cumulo+PL_cumulo+AN_cumulo+OD+Feed_Vol+RS_cumulo+Cell_conc._interval+Arg_conc.+emission_CO2+consum_O2; 0.432, 0.761, pH_cumulo+PL_cumulo+AN+AN_cumulo+OD+Feed_Vol+Cell_conc._interval+rab_integral+RQ_integral+Arg_conc.+emission_O2+consum_O2+interval_O2+generate_CO2; 0.446, 0.761, pH+pH_cumulo+PL+AN+AN_cumulo+interval_yield+OD+Cell_conc._interval+Arg_conc.+emission_CO2+interval_O2+generate_CO2+interval_CO2; 0.446, 0.761, pH_cumulo+PL+AN+AN_cumulo+OD+Feed_Vol+RS_cumulo+Cell_conc._interval+RQ_integral+Arg_conc.+emission_O2+emission_CO2+consum_O2; 0.432, 0.761, tmp_cumulo+pH_cumulo+PL_cumulo+AN+AN_cumulo+interval_yield+OD+Feed_Vol+Cell_conc._interval+rab_integral+RQ_integral+Arg_ conc.+emission_O2+consum_O2; 0.471, 0.761, pH_cumulo+AN+AN_cumulo+OD+Feed_Vol+RS_cumulo+Cell_conc._interval+Arg_conc.+emission_CO2+consum_O2+generate_CO2; 0.402, 0.761, tmp+pH+pH_cumulo+PL_cumulo+AN+AN_cumulo+interval_yield+OD+Feed_Vol+Cell_conc._interval+rab_integral+RQ_integral+Arg_conc.+emission_O2+consum_O2+interval_CO2; 0.386, 0.761, pH_cumulo+PL+PL_cumulo+AN+AN_cumulo+interval_yield+OD+Feed_Vol+RS_cumulo+Cell_conc._interval+rab_integral+RQ_integral+Accum._Yield+Arg_conc.+emission_O2+consum_O2+interval_CO2; 0.459, 0.761, pH+pH_cumulo+PL+AN+AN_cumulo+OD+Cell_conc._interval+Arg_conc.+emission_CO2+consum_O2+generate_CO2+interval_CO2; 0.417, 0.761, tmp+tmp_cumulo+pH+pH_cumulo+AN+AN_cumulo+interval_yield+OD+Cell_conc._interval+rab_integral+RQ_integral+Arg_conc.+emission_O2+consum_O2+interval_CO2; 0.459, 0.761, pH_cumulo+PL+AN+AN_cumulo+OD+Feed_Vol+RS_cumulo+Cell_conc._interval+rab_integral+Arg_conc.+emission_CO2+consum_O2; 0.471, 0.761, pH_cumulo+AN+AN_cumulo+OD+Feed_Vol+RS_cumulo+Cell_conc._interval+Arg_conc.+emission_CO2+consum_O2+interval_O2; 0.459, 0.761, pH_cumulo+PL+PL_cumulo+AN+AN_cumulo+OD+Feed_Vol+Cell_conc._interval+RQ_integral+Arg_conc.+emission_O2+consum_O2; 0.459, 0.761, tmp_cumulo+pH_cumulo+PL+AN+AN_cumulo+OD+Cell_conc._interval+rab_integral+Arg_conc.+emission_CO2+consum_O2+interval_CO2; 0.432, 0.761, pH_cumulo+PL+AN+AN_cumulo+OD+Feed_Vol+Cell_conc._interval+rab_integral+RQ_integral+Arg_conc.+emission_O2+consum_O2+interval_O2+generate_CO2; 0.459, 0.761, pH_cumulo+PL+AN+AN_cumulo+OD+Feed_Vol+Cell_conc._interval+Arg_conc.+emission_O2+emission_CO2+consum_O2+generate_CO2; 0.471, 0.761, pH+pH_cumulo+PL+PL_cumulo+AN_cumulo+OD+Feed_Vol+Cell_conc._interval+Arg_conc.+emission_CO2+consum_O2; 0.432, 0.761, pH+pH_cumulo+AN+AN_cumulo+interval_yield+OD+Feed_Vol+Cell_conc._interval+rab_integral+RQ_integral+Arg_conc.+emission_O2+interval_O2+generate_CO2; 0.432, 0.761, tmp_cumulo+pH+pH_cumulo+AN+AN_cumulo+interval_yield+OD+Feed_Vol+Cell_conc._interval+rab_integral+RQ_integral+Arg_conc.+emission_O2+consum_O2; 0.446, 0.761, tmp_cumulo+pH+pH_cumulo+PL+AN+AN_cumulo+interval_yield+OD+Cell_conc._interval+Arg_conc.+emission_CO2+consum_O2+generate_CO2+interval_CO2; 0.386, 0.761, pH_cumulo+PL+PL_cumulo+AN+AN_cumulo+interval_yield+OD+RS_cumulo+Cell_conc._interval+rab_integral+RQ_integral+Arg_conc.+emission_O2+emission_CO2+consum_O2+generate_CO2+interval_CO2; 0.459, 0.761, pH+pH_cumulo+PL+AN+AN_cumulo+OD+Cell_conc._interval+Arg_conc.+emission_CO2+interval_O2+generate_CO2+interval_CO2; 0.483, 0.761, pH_cumulo+AN+AN_cumulo+OD+RS+Cell_conc._interval+Arg_conc.+emission_CO2+consum_O2+interval_CO2; 0.471, 0.761, tmp+pH+pH_cumulo+AN+AN_cumulo+OD+Cell_conc._interval+Arg_conc.+emission_CO2+consum_O2+interval_CO2; 0.459, 0.761, tmp_cumulo+pH_cumulo+PL+AN+AN_cumulo+interval_yield+OD+Cell_conc._interval+Arg_conc.+emission_CO2+consum_O2+interval_CO2; 0.417, 0.761, pH_cumulo+PL+PL_cumulo+AN+AN_cumulo+interval_yield+OD+Feed_Vol+Cell_conc._interval+rab_integral+RQ_integral+Arg_conc.+emission_CO2+consum_O2+interval_O2; 0.402, 0.761, tmp+pH_cumulo+PL+PL_cumulo+AN+AN_cumulo+interval_yield+OD+RS+Cell_conc._interval+rab_integral+RQ_integral+Arg_conc.+emission_O2+consum_O2+interval_CO2; 0.471, 0.761, tmp+pH_cumulo+PL_cumulo+AN+AN_cumulo+OD+Feed_Vol+Cell_conc._interval+Arg_conc.+emission_CO2+consum_O2; 0.432, 0.761, pH+pH_cumulo+AN+AN_cumulo+OD+Feed_Vol+Cell_conc._interval+rab_integral+RQ_integral+Arg_conc.+emission_O2+interval_O2+generate_CO2+interval_CO2; 0.459, 0.761, pH_cumulo+PL_cumulo+AN_cumulo+OD+Feed_Vol+RS_cumulo+Cell_conc._interval+rab_integral+RQ_integral+Arg_conc.+emission_O2+consum_O2; 0.459, 0.761, tmp+pH_cumulo+AN+AN_cumulo+interval_yield+OD+Cell_conc._interval+Arg_conc.+emission_CO2+interval_O2+generate_CO2+interval_CO2; 0.445, 0.761, pH_cumulo+PL+AN+AN_cumulo+interval_yield+OD+RS_cumulo+rab_integral+RQ_integral+Arg_conc.+emission_O2+consum_O2+interval_CO2; 0.402, 0.761, tmp+pH_cumulo+PL_cumulo+AN+AN_cumulo+interval_yield+OD+Cell_conc._interval+rab_integral+RQ_integral+Arg_conc.+emission_O2+emission_CO2+consum_O2+generate_CO2+interval_CO2; 0.445, 0.761, tmp_cumulo+pH_cumulo+PL_cumulo+AN+AN_cumulo+interval_yield+OD+Cell_conc._interval+Arg_conc.+emission_CO2+interval_O2+generate_CO2+interval_CO2; 0.432, 0.761, tmp+pH+pH_cumulo+PL_cumulo+AN+AN_cumulo+OD+Cell_conc._interval+rab_integral+RQ_integral+Arg_conc.+emission_O2+consum_O2+interval_CO2; 0.459, 0.761, pH_cumulo+PL+PL_cumulo+AN+AN_cumulo+OD+Feed_Vol+Cell_conc._interval+Arg_conc.+emission_CO2+consum_O2+interval_CO2; 0.432, 0.761, pH_cumulo+PL+AN+AN_cumulo+OD+Feed_Vol+Cell_conc._interval+rab_integral+RQ_integral+Arg_conc.+emission_O2+consum_O2+interval_O2+interval_CO2; 0.459, 0.761, tmp+pH_cumulo+PL+AN+AN_cumulo+OD+Cell_conc._interval+Arg_conc.+emission_CO2+interval_O2+generate_CO2+interval_CO2; 0.445, 0.761, pH_cumulo+AN+AN_cumulo+interval_yield+OD+Feed_Vol+Cell_conc._interval+RQ_integral+Arg_conc.+emission_CO2+interval_O2+generate_CO2+interval_CO2; 0.432, 0.761, pH_cumulo+PL+AN+AN_cumulo+OD+Feed_Vol+Cell_conc._interval+rab_integral+RQ_integral+Arg_conc.+emission_O2+interval_O2+generate_CO2+interval_CO2; 0.432, 0.761, pH_cumulo+PL_cumulo+AN+AN_cumulo+OD+Feed_Vol+RS_cumulo+Cell_conc._interval+rab_integral+RQ_integral+Arg_conc.+emission_O2+consum_O2+interval_O2; 0.483, 0.761, tmp+pH+pH_cumulo+AN+AN_cumulo+OD+Feed_Vol+Cell_conc._interval+Arg_conc.+emission_CO2+consum_O2; 0.459, 0.761, tmp+tmp_cumulo+pH_cumulo+AN+AN_cumulo+OD+Cell_conc._interval+Arg_conc.+emission_CO2+interval_O2+generate_CO2+interval_CO2; 0.459, 0.761, pH_cumulo+PL_cumulo+AN+AN_cumulo+OD+Feed_Vol+Cell_conc._interval+RQ_integral+Arg_conc.+emission_O2+consum_O2+generate_CO2; 0.431, 0.761, pH_cumulo+PL+PL_cumulo+AN+AN_cumulo+interval_yield+OD+Feed_Vol+Cell_conc._interval+RQ_integral+Arg_conc.+emission_CO2+consum_O2+interval_O2; 0.431, 0.761, tmp+pH_cumulo+AN+AN_cumulo+interval_yield+OD+Feed_Vol+Cell_conc._interval+rab_integral+RQ_integral+Arg_conc.+emission_O2+emission_CO2+consum_O2; 0.402, 0.761, pH+pH_cumulo+PL+AN+AN_cumulo+interval_yield+OD+Feed_Vol+Cell_conc._interval+rab_integral+RQ_integral+Arg_conc.+emission_O2+emission_CO2+consum_O2+interval_CO2; 0.431, 0.761, pH+pH_cumulo+AN+AN_cumulo+interval_yield+OD+Cell_conc._interval+rab_integral+RQ_integral+Arg_conc.+emission_O2+emission_CO2+consum_O2+interval_CO2; 0.471, 0.761, tmp_cumulo+pH_cumulo+AN+AN_cumulo+OD+

Feed_Vol+Cell_conc._interval+RQ_integral+Arg_conc.+ emission_CO2+consum_O2; 0.385, 0.761, tmp+pH_cumulo+PL+PL_cumulo+AN+AN_cumulo+interval_yield+ OD+RS_cumulo+Cell_conc._interval+rab_integral+RQ_ integral+Arg_conc.+emission_O2+consum_O2+generate_ CO2+interval_CO2; 0.417, 0.761, tmp+pH_cumulo+PL_ cumulo+AN+AN_cumulo+interval_yield+OD+Feed_Vol+ Cell_conc._interval+rab_integral+RQ_integral+Arg_ conc.+emission_O2+consum_O2+generate_CO2; 0.445, 0.761, pH_cumulo+AN+AN_cumulo+interval_yield+OD+ Feed_Vol+Cell_conc._interval+rab_integral+RQ_integral+ Accum._Yield+Arg_conc.+emission_CO2+consum_O2; 0.471, 0.761, pH+pH_cumulo+PL_cumulo+AN+AN_cumulo+OD+Cell_conc._interval+Arg_conc.+emission_ CO2+consum_O2+interval_CO2; 0.417, 0.761, tmp+pH_ cumulo+PL+AN+AN_cumulo+interval_yield+OD+Feed_ Vol+Cell_conc._interval+rab_integral+RQ_integral+Arg_ conc.+emission_O2+emission_CO2+consum_O2; 0.431, 0.761, pH+pH_cumulo+PL_cumulo+AN+AN_cumulo+interval_yield+OD+Feed_Vol+Cell_conc._interval+RQ_integral+Arg_conc.+emission_CO2+consum_O2+interval_O2; 0.483, 0.761, pH_cumulo+AN+AN_cumulo+OD+Feed_ Vol+Cell_conc._interval+Accum._Yield+Arg_conc.+emission_CO2+consum_O2; 0.385, 0.761, tmp+tmp_cumulo+ pH+pH_cumulo+PL+PL_cumulo+AN+AN_cumulo+ interval_yield+OD+Cell_conc._interval+rab_integral+RQ_ integral+Arg_conc.+emission_O2+consum_O2+interval_ CO2; 0.385, 0.761, pH_cumulo+PL+PL_cumulo+AN+AN_ cumulo+interval_yield+OD+RS_cumulo+Cell_conc._ interval+rab_integral+RQ_integral+Arg_conc.+emission_ O2+emission_CO2+consum_O2+interval_O2+interval_ CO2; 0.458, 0.761, pH_cumulo+PL+AN+AN_cumulo+ OD+Feed_Vol+Cell_conc._interval+Arg_conc.+emission_ CO2+consum_O2+interval_O2+interval_CO2; 0.401, 0.761, pH_cumulo+PL_cumulo+AN+AN_cumulo+interval_yield+OD+Feed_Vol+Cell_conc._interval+rab_integral+RQ_integral+Arg_conc.+emission_O2+emission_ CO2+consum_O2+interval_O2+generate_CO2; 0.431, 0.761, pH_cumulo+PL_cumulo+AN+AN_cumulo+interval_yield+OD+Feed_Vol+Cell_conc._interval+rab_integral+RQ_integral+Arg_conc.+emission_CO2+consum_ O2+generate_CO2; 0.445, 0.761, tmp_cumulo+pH_ cumulo+PL+AN+AN_cumulo+interval_yield+OD+rab_ integral+RQ_integral+Arg_conc.+emission_O2+consum_ O2+interval_CO2; 0.445, 0.761, pH+pH_cumulo+PL_ cumulo+AN+AN_cumulo+OD+Feed_Vol+Cell_conc._ interval+rab_integral+RQ_integral+Arg_conc.+emission_ CO2+consum_O2; 0.431, 0.761, pH+pH_cumulo+AN+ AN_cumulo+OD+Feed_Vol+Cell_conc._interval+rab_ integral+RQ_integral+Arg_conc.+emission_CO2+consum_ O2+interval_O2+generate_CO2; 0.401, 0.761, pH+pH_ cumulo+PL_cumulo+AN+AN_cumulo+interval_yield+ OD+RS+Cell_conc._interval+rab_integral+RQ_integral+ Arg_conc.+emission_O2+consum_O2+interval_O2+ interval_CO2; 0.445, 0.761, pH+pH_cumulo+AN+AN_ cumulo+OD+Cell_conc._interval+rab_integral+RQ_ integral+Arg_conc.+emission_O2+interval_O2+generate_ CO2+interval_CO2; 0.458, 0.761, pH+pH_cumulo+AN+ AN_cumulo+OD+Feed_Vol+RS_cumulo+Cell_conc._ interval+RQ_integral+Arg_conc.+emission_O2+consum_ O2; 0.431, 0.761, pH_cumulo+PL+AN+AN_cumulo+ interval_yield+OD+RS+Feed_Vol+Cell_conc._interval+ rab_integral+RQ_integral+Arg_conc.+emission_O2+ consum_O2; 0.401, 0.761, tmp_cumulo+pH+pH_cumulo+ PL_cumulo+AN+AN_cumulo+interval_yield+OD+Cell_ conc._interval+rab_integral+RQ_integral+Arg_conc.+ emission_CO2+emission_CO2+consum_O2+interval_CO2; 0.401, 0.761, pH_cumulo+PL_cumulo+AN+AN_cumulo+ interval_yield+OD+RS+Feed_Vol+Cell_conc._interval+ rab_integral+RQ_integral+Arg_conc.+emission_O2+consum_O2+interval_O2+interval_CO2; 0.445, 0.761, pH_cumulo+PL_cumulo+AN+AN_cumulo+interval_yield+ OD+Feed_Vol+Cell_conc._interval+rab_integral+RQ_integral+Arg_conc.+emission_O2+consum_O2+generate_ CO2; 0.401, 0.761, pH+pH_cumulo+PL_cumulo+AN+AN_ cumulo+interval_yield+OD+Feed_Vol+RS_cumulo+Cell_ conc._interval+rab_integral+RQ_integral+Arg_conc.+ emission_O2+consum_O2+generate_CO2; 0.431, 0.761, pH_cumulo+PL_cumulo+AN+AN_cumulo+OD+Feed_ Vol+Cell_conc._interval+rab_integral+RQ_integral+Arg_ conc.+emission_O2+interval_O2+generate_CO2+interval_ CO2; 0.401, 0.761, pH+pH_cumulo+PL+AN+AN_ cumulo+interval_yield+OD+RS_cumulo+Cell_conc._ interval+rab_integral+RQ_integral+Arg_conc.+emission_ O2+emission_CO2+consum_O2+interval_CO2; 0.471, 0.761, pH_cumulo+PL+AN_cumulo+interval_yield+OD+ Feed_Vol+Cell_conc._interval+Arg_conc.+emission_O2+ emission_CO2+consum_O2; 0.471, 0.761, tmp_cumulo+ pH_cumulo+AN+AN_cumulo+interval_yield+OD+Cell_ conc._interval+Arg_conc.+emission_CO2+consum_O2+ interval_CO2; 0.445, 0.761, tmp+pH_cumulo+AN+AN_ cumulo+OD+Feed_Vol+Cell_conc._interval+rab_integral+ RQ_integral+Arg_conc.+emission_O2+consum_O2+ interval_CO2; 0.401, 0.761, pH_cumulo+PL+PL_cumulo+ AN+AN_cumulo+interval_yield+OD+Feed_Vol+Cell_ conc._interval+rab_integral+RQ_integral+Arg_conc.+ emission_O2+emission_CO2+consum_O2+generate_CO2; 0.458, 0.761, pH_cumulo+PL+AN+AN_cumulo+OD+ Feed_Vol+Cell_conc._interval+Arg_conc.+emission_O2+ emission_CO2+consum_O2+interval_O2; 0.458, 0.761, tmp+pH_cumulo+PL+AN+AN_cumulo+interval_yield+ OD+Feed_Vol+Cell_conc._interval+Arg_conc.+emission_ CO2+consum_O2; 0.445, 0.761, pH+pH_cumulo+PL+PL_ cumulo+AN_cumulo+OD+Feed_Vol+Cell_conc._interval+ rab_integral+RQ_integral+Arg_conc.+emission_O2+ consum_O2; 0.458, 0.761, pH_cumulo+PL+AN+AN+ AN_cumulo+OD+Feed_Vol+Cell_conc._interval+rab_ integral+Arg_conc.+emission_CO2+consum_O2+interval_ O2; 0.458, 0.761, pH_cumulo+PL+AN+AN_cumulo+OD+ Feed_Vol+RS_cumulo+Cell_conc._interval+Arg_conc.+ emission_O2+emission_CO2+consum_O2; 0.458, 0.761, pH+pH_cumulo+AN+AN_cumulo+OD+Feed_Vol+Cell_ conc._interval+RQ_integral+Arg_conc.+emission_CO2+ consum_O2+interval_CO2; 0.385, 0.761, pH+pH_cumulo+ PL_cumulo+AN+AN_cumulo+interval_yield+OD+Feed_ Vol+Cell_conc._interval+rab_integral+RQ_integral+Arg_ conc.+emission_O2+emission_CO2+consum_O2+interval_ O2+interval_CO2; 0.458, 0.761, tmp_cumulo+pH_cumulo+ AN+AN_cumulo+OD+Cell_conc._interval+rab_integral+ RQ_integral+Arg_conc.+emission_O2+interval_O2+ interval_CO2; 0.431, 0.761, pH_cumulo+PL_cumulo+AN+ AN_cumulo+interval_yield+OD+Feed_Vol+Cell_conc._ interval+RQ_integral+Arg_conc.+emission_CO2+consum_ O2+generate_CO2+interval_CO2; 0.483, 0.761, pH+pH_ cumulo+AN_cumulo+OD+Feed_Vol+Cell_conc._interval+ rab_integral+Arg_conc.+emission_CO2+consum_O2; 0.431, 0.761, pH+pH_cumulo+PL+AN+AN_cumulo+OD+ RS_cumulo+Cell_conc._interval+rab_integral+RQ_integral+Arg_conc.+emission_O2+interval_O2+interval_CO2; 0.458, 0.761, pH_cumulo+PL+PL_cumulo+AN+AN_cumulo+OD+Feed_Vol+Cell_conc._interval+Arg_conc.+ emission_CO2+consum_O2+interval_O2; 0.431, 0.761, tmp_cumulo+pH_cumulo+AN+AN_cumulo+interval_ yield+OD+Cell_conc._interval+rab_integral+RQ_integral+ Arg_conc.+emission_CO2+interval_O2+generate_CO2+interval_CO2; 0.458, 0.761, pH+pH_cumulo+PL_cumulo+ AN+AN_cumulo+OD+Cell_conc._interval+Arg_conc.+ emission_CO2+consum_O2+generate_CO2+interval_CO2; 0.431, 0.761, tmp_cumulo+pH+pH_cumulo+AN+AN_cumulo+interval_yield+OD+Cell_conc._interval+rab_integral+RQ_integral+Arg_conc.+emission_CO2+consum_O2+interval_CO2; 0.416, 0.761, pH_cumulo+PL_cumulo+AN+AN_cumulo+interval_yield+OD+RS_cumulo+Cell_conc._interval+rab_integral+RQ_integral+Arg_conc.+emission_O2+emission_CO2+consum_O2+interval_CO2; 0.445, 0.761, pH_cumulo+PL_cumulo+AN+AN_cumulo+interval_yield+OD+Cell_conc._interval+Arg_conc.+emission_O2+emission_CO2+interval_O2+generate_CO2+interval_CO2; 0.445, 0.761, pH+pH_cumulo+PL_cumulo+AN+AN_cumulo+OD+Feed_Vol+Cell_conc._interval+RQ_integral+Arg_conc.+emission_CO2+consum_O2+interval_O2; 0.431, 0.761, pH_cumulo+PL+AN+AN_cumulo+OD+Feed_Vol+RS_cumulo+Cell_conc._interval+rab_integral+RQ_integral+Arg_conc.+emission_O2+consum_O2+generate_CO2; 0.416, 0.761, pH+pH_cumulo+AN+AN_cumulo+interval_yield+OD+RS_cumulo+Cell_conc._interval+rab_integral+RQ_integral+Arg_conc.+emission_O2+interval_O2+generate_CO2+interval_CO2; 0.416, 0.761, tmp_cumulo+pH_cumulo+PL_cumulo+AN+AN_cumulo+interval_yield+OD+Cell_conc._interval+rab_integral+RQ_integral+Arg_conc.+emission_CO2+consum_O2+interval_O2+interval_CO2; 0.431, 0.760, tmp_cumulo+pH+pH_cumulo+PL_cumulo+AN+AN_cumulo+interval_yield+OD+Cell_conc._interval+Arg_conc.+emission_CO2+consum_O2+generate_CO2+interval_CO2; 0.431, 0.760, pH_cumulo+PL+PL_cumulo+AN+AN_cumulo+interval_yield+OD+Feed_Vol+Cell_conc._interval+rab_integral+RQ_integral+Arg_conc.+emission_CO2+consum_O2; 0.458, 0.760, pH_cumulo+AN+AN_cumulo+interval_yield+OD+Cell_conc._interval+rab_integral+Arg_conc.+emission_CO2+interval_O2+generate_CO2+interval_CO2; 0.431, 0.760, pH_cumulo+PL+AN+AN_cumulo+OD+Feed_Vol+RS_cumulo+Cell_conc._interval+rab_integral+RQ_integral+Arg_conc.+emission_O2+consum_O2+generate_CO2; 0.431, 0.760, pH_cumulo+PL+PL_cumulo+AN+AN_cumulo+interval_yield+OD+Feed_Vol+Cell_conc._interval+rab_integral+RQ_integral+Arg_conc.+emission_O2+consum_O2+interval_O2; 0.416, 0.760, pH+pH_cumulo+PL_cumulo+AN+AN_cumulo+OD+Feed_Vol+RS_cumulo+Cell_conc._interval+rab_integral+RQ_integral+Arg_conc.+emission_O2+consum_O2+interval_CO2; 0.385, 0.760, pH_cumulo+PL+PL_cumulo+AN+AN_cumulo+interval_yield+OD+Feed_Vol+Cell_conc._interval+rab_integral+RQ_integral+Arg_conc.+emission_O2+interval_O2+generate_CO2+interval_CO2; 0.458, 0.760, tmp_cumulo+pH_cumulo+AN+AN_cumulo+OD+Feed_Vol+Cell_conc._interval+Arg_conc.+emission_CO2+interval_O2+generate_CO2+interval_CO2; 0.445, 0.760, tmp+tmp_cumulo+pH_cumulo+AN+AN_cumulo+OD+Cell_conc._interval+rab_integral+RQ_integral+Arg_conc.+emission_CO2+consum_O2+interval_CO2

[209. Linear Model that Predicts Arginine Production Amount in Interval 9]
0.238, 0.604, tmp_cumulo+pH+pH_cumulo+PL_cumulo+RS_cumulo+Cell_conc._interval+rab_integral+Arg_conc.+emission_CO2+interval_O2; 0.233, 0.601, tmp+PL_cumulo+Feed_Vol+RS_cumulo+Cell_conc._interval+培養液中A中酸素濃度+interval_O2+generate_CO2; 0.233, 0.600, tmp_cumulo+PL_cumulo+Feed_Vol+RS_cumulorg濃度+排気ガス+ Cell_conc._interval+RQ_integral+Arg_conc.+emission_CO2+interval_O2; 0.215, 0.600, tmp_cumulo+pH+PL_cumulo+Feed_Vol+RS_cumulo+Cell_conc._interval+RQ_integral+Arg_conc.+emission_CO2+interval_O2; 0.232, 0.600, tmp+PL_cumulo+Feed_Vol+RS_cumulo+Cell_conc._interval+Arg_conc.+emission_O2+consum_O2+generate_CO2; 0.231, 0.600, tmp_cumulo+pH_cumulo+PL_cumulo+RS_cumulo+Cell_conc._interval+rab_integral+Arg_conc.+emission_CO2+interval_O2; 0.212, 0.598, tmp+PL_cumulo+AN_cumulo+Feed_Vol+RS_cumulo+Cell_conc._interval+Arg_conc.+emission_O2+interval_O2+generate_CO2; 0.212, 0.598, tmp_cumulo+pH+PL_cumulo+AN_cumulo+RS_cumulo+Cell_conc._interval+rab_integral+Arg_conc.+emission_CO2+interval_O2; 0.210, 0.597, tmp_cumulo+pH+PL_cumulo+Feed_Vol+RS_cumulo+Cell_conc._interval+Arg_conc.+emission_O2+consum_O2+interval_O2; 0.192, 0.597, tmp_cumulo+pH+PL_cumulo+AN_cumulo+Feed_Vol+RS_cumulo+Cell_conc._interval+Arg_conc.+emission_O2+consum_O2+interval_O2; 0.227, 0.597, tmp_cumulo+PL_cumulo+Feed_Vol+RS_cumulo+Cell_conc._interval+Arg_conc.+emission_O2+interval_O2+generate_CO2; 0.210, 0.597, tmp_cumulo+pH+PL_cumulo+Feed_Vol+RS_cumulo+Cell_conc._interval+rab_integral+Arg_conc.+emission_CO2+interval_O2; 0.207, 0.595, tmp_cumulo+pH_cumulo+PL_cumulo+Feed_Vol+RS_cumulo+Cell_conc._interval+RQ_integral+Arg_conc.+emission_CO2+interval_O2; 0.207, 0.595, tmp_cumulo+pH+PL_cumulo+RS+RS_cumulo+Cell_conc._interval+rab_integral+Arg_conc.+emission_CO2+interval_O2; 0.207, 0.595, tmp_cumulo+pH_cumulo+PL_cumulo+Feed_Vol+RS_cumulo+Cell_conc._interval+rab_integral+Arg_conc.+emission_CO2+interval_O2; 0.207, 0.595, tmp_cumulo+pH_cumulo+PL_cumulo+Feed_Vol+RS_cumulo+Cell_conc._interval+Arg_conc.+emission_O2+consum_O2+interval_O2; 0.206, 0.594, tmp_cumulo+pH+PL_cumulo+Feed_Vol+RS_cumulo+Cell_conc._interval+Arg_conc.+emission_O2+interval_O2+generate_CO2; 0.188, 0.594, tmp_cumulo+pH+PL_cumulo+AN_cumulo+Feed_Vol+RS_cumulo+Cell_conc._interval+rab_integral+Arg_conc.+emission_CO2+interval_O2; 0.221, 0.593, tmp_cumulo+pH+PL_cumulo+Feed_Vol+RS_cumulo+Cell_conc._interval+Arg_conc.+emission_O2+interval_O2; 0.185, 0.592, tmp_cumulo+pH+PL_cumulo+AN_cumulo+Feed_Vol+RS_cumulo+Cell_conc._interval+RQ_integral+Arg_conc.+emission_CO2+interval_O2; 0.185, 0.592, tmp_cumulo+pH+PL_cumulo+AN_cumulo+RS+RS_cumulo+Cell_conc._interval+rab_integral+Arg_conc.+emission_CO2+interval_O2; 0.203, 0.592, tmp_cumulo+PL_cumulo+Feed_Vol+RS_cumulo+Cell_conc._interval+RQ_integral+Arg_conc.+emission_CO2+interval_O2+generate_CO2; 0.202, 0.592, tmp_cumulo+PL_cumulo+AN_cumulo+Feed_Vol+RS_cumulo+Cell_conc._interval+RQ_integral+Arg_conc.+emission_CO2+interval_O2; 0.202, 0.591, tmp+PL_cumulo+Feed_Vol+RS_cumulo+Cell_conc._interval+Arg_conc.+emission_O2+emission_CO2+interval_O2+generate_CO2; 0.202, 0.591, tmp_cumulo+PL_cumulo+AN_cumulo+Feed_Vol+RS_cumulo+Cell_conc._interval+Arg_conc.+emission_O2+consum_O2+generate_CO2; 0.220, 0.591, tmp_cumulo+pH+PL_cumulo+RS_cumulo+Cell_conc._interval+RQ_integral+Arg_conc.+emission_CO2+interval_O2; 0.219, 0.591, tmp_cumulo+PL_cumulo+Feed_Vol+RS_cumulo+Cell_conc._interval+Arg_conc.+emission_O2+consum_O2+generate_CO2; 0.201, 0.591, tmp_cumulo+pH_cumulo+PL_cumulo+Feed_Vol+RS_cumulo+Cell_conc._interval+Arg_conc.+emission_O2+interval_O2+generate_

CO2; 0.201, 0.591, tmp_cumulo+pH+PL_cumulo+RS_cumulo+Cell_conc._interval+rab_integral+Arg_conc.+emission_CO2+interval_O2+generate_CO2; 0.201, 0.591, tmp+pH+PL_cumulo+Feed_Vol+RS_cumulo+Cell_conc._interval+Arg_conc.+emission_O2+interval_O2+generate_CO2; 0.200, 0.590, tmp+PL_cumulo+Feed_Vol+RS_cumulo+Cell_conc._interval+Arg_conc.+emission_O2+emission_CO2+consum_O2+generate_CO2; 0.182, 0.590, tmp_cumulo+pH_cumulo+PL_cumulo+AN_cumulo+Feed_Vol+RS_cumulo+Cell_conc._interval+Arg_conc.+emission_O2+consum_O2+interval_O2; 0.200, 0.590, tmp_cumulo+pH_cumulo+PL_cumulo+AN_cumulo+RS_cumulo+Cell_conc._interval+rab_integral+Arg_conc.+emission_CO2+interval_O2; 0.199, 0.589, tmp_cumulo+PL+PL_cumulo+Feed_Vol+RS_cumulo+Cell_conc._interval+RQ_integral+Arg_conc.+emission_CO2+interval_O2; 0.180, 0.589, tmp+pH+PL_cumulo+AN_cumulo+Feed_Vol+RS_cumulo+Cell_conc._interval+Arg_conc.+emission_O2+interval_O2+generate_CO2; 0.234, 0.589, tmp_cumulo+PL_cumulo+RS_cumulo+Cell_conc._interval+rab_integral+Arg_conc.+emission_CO2+interval_O2; 0.199, 0.589, tmp_cumulo+PL_cumulo+AN_cumulo+Feed_Vol+RS_cumulo+Cell_conc._interval+Arg_conc.+emission_O2+interval_O2+generate_CO2; 0.198, 0.589, tmp+pH_cumulo+PL_cumulo+Feed_Vol+RS_cumulo+Cell_conc._interval+Arg_conc.+emission_O2+interval_O2+generate_CO2; 0.180, 0.589, tmp_cumulo+pH+PL_cumulo+AN_cumulo+Feed_Vol+RS_cumulo+Cell_conc._interval+Arg_conc.+emission_O2+interval_O2+generate_CO2; 0.216, 0.589, tmp_cumulo+PL_cumulo+Feed_Vol+RS_cumulo+Cell_conc._interval+Arg_conc.+emission_O2+consum_O2+interval_O2; 0.179, 0.589, tmp_cumulo+pH_cumulo+PL_cumulo+AN_cumulo+Feed_Vol+RS_cumulo+Cell_conc._interval+rab_integral+Arg_conc.+emission_CO2+interval_O2; 0.179, 0.589, tmp+PL+PL_cumulo+AN_cumulo+Feed_Vol+RS_cumulo+Cell_conc._interval+Arg_conc.+emission_O2+interval_O2+generate_CO2; 0.179, 0.588, tmp+pH+PL_cumulo+AN_cumulo+Feed_Vol+RS_cumulo+Cell_conc._interval+Arg_conc.+emission_O2+consum_O2+interval_O2; 0.179, 0.588, tmp+PL_cumulo+AN_cumulo+Feed_Vol+RS_cumulo+Cell_conc._interval+Arg_conc.+emission_O2+emission_CO2+interval_O2+generate_CO2; 0.197, 0.588, tmp_cumulo+pH_cumulo+PL_cumulo+RS_cumulo+Cell_conc._interval+rab_integral+Arg_conc.+emission_CO2+interval_O2+generate_CO2; 0.214, 0.587, tmp_cumulo+PL_cumulo+RS+RS_cumulo+Cell_conc._interval+rab_integral+Arg_conc.+emission_CO2+interval_O2; 0.196, 0.587, tmp_cumulo+pH_cumulo+PL_cumulo+RS+RS_cumulo+Cell_conc._interval+rab_integral+Arg_conc.+emission_CO2+interval_O2; 0.196, 0.587, tmp_cumulo+pH+PL_cumulo+RS_cumulo+Cell_conc._interval+rab_integral+Arg_conc.+emission_CO2+consum_O2+interval_O2; 0.213, 0.587, tmp+PL_cumulo+RS+Feed_Vol+Cell_conc._interval+Arg_conc.+emission_O2+consum_O2+generate_CO2; 0.195, 0.1587, tmp_cumulo+PL_cumulo+Feed_Vol+RS_cumulo+Cell_conc._interval+RQ_integral+Arg_conc.+emission_CO2+consum_O2+interval_O2; 0.213, 0.587, tmp+PL_cumulo+Feed_Vol+RS_cumulo+Cell_conc._interval+RQ_integral+Arg_conc.+emission_CO2+interval_O2; 0.195, 0.587, tmp_cumulo+pH+PL+PL_cumulo+RS_cumulo+Cell_conc._interval+rab_integral+Arg_conc.+emission_CO2+interval_O2; 0.176, 0.586, tmp_cumulo+PL_cumulo+AN_cumulo+Feed_Vol+RS_cumulo+Cell_conc._interval+RQ_integral+Arg_conc.+emission_CO2+interval_O2+generate_CO2; 0.175, 0.586, tmp+pH_cumulo+PL_cumulo+AN_cumulo+Feed_Vol+RS_cumulo+Cell_conc._interval+Arg_conc.+emission_O2+interval_O2+generate_CO2; 0.194, 0.586, tmp_cumulo+PL_cumulo+Feed_Vol+RS_cumulo+Cell_conc._interval+Arg_conc.+emission_O2+emission_CO2+interval_O2+generate_CO2; 0.229, 0.586, tmp_cumulo+PL_cumulo+RS_cumulo+Cell_conc._interval+RQ_integral+Arg_conc.+emission_CO2+interval_O2; 0.194, 0.586, tmp_cumulo+PL_cumulo+Feed_Vol+RS_cumulo+Cell_conc._interval+RQ_integral+Arg_conc.+emission_O2+emission_CO2+interval_O2; 0.194, 0.586, tmp+PL_cumulo+AN_cumulo+Feed_Vol+RS_cumulo+Cell_conc._interval+Arg_conc.+emission_O2+consum_O2+interval_O2; 0.175, 0.586, tmp_cumulo+pH_cumulo+PL_cumulo+AN_cumulo+Feed_Vol+RS_cumulo+Cell_conc._interval+RQ_integral+Arg_conc.+emission_CO2+interval_O2; 0.193, 0.586, tmp+PL+PL_cumulo+Feed_Vol+RS_cumulo+Cell_conc._interval+Arg_conc.+emission_O2+interval_O2+generate_CO2; 0.193, 0.585, tmp_cumulo+pH+pH_cumulo+PL_cumulo+RS_cumulo+Cell_conc._interval+rab_integral+Arg_conc.+emission_CO2+interval_O2; 0.193, 0.585, tmp_cumulo+pH+PL_cumulo+AN+RS_cumulo+Cell_conc._interval+rab_integral+Arg_conc.+emission_CO2+interval_O2; 0.193, 0.585, tmp+PL_cumulo+Feed_Vol+RS_cumulo+Cell_conc._interval+rab_integral+Arg_conc.+emission_O2+interval_O2+generate_CO2; 0.211, 0.585, tmp+PL_cumulo+Feed_Vol+RS_cumulo+Cell_conc._interval+Arg_conc.+emission_O2+consum_O2+interval_O2; 0.174, 0.585, tmp_cumulo+pH+PL_cumulo+Feed_Vol+RS_cumulo+Cell_conc._interval+Arg_conc.+emission_O2+emission_CO2+consum_O2+interval_O2; 0.211, 0.585, tmp_cumulo+PL_cumulo+Feed_Vol+RS_cumulo+Cell_conc._interval+rab_integral+Arg_conc.+emission_CO2+interval_O2; 0.192, 0.585, tmp_cumulo+pH+PL_cumulo+Feed_Vol+RS_cumulo+Cell_conc._interval+rab_integral+Arg_conc.+emission_O2+interval_O2; 0.154, 0.585, tmp_cumulo+pH+PL_cumulo+AN_cumulo+Feed_Vol+RS_cumulo+Cell_conc._interval+Arg_conc.+emission_O2+emission_CO2+consum_O2+interval_O2; 0.173, 0.584, tmp+pH_cumulo+PL_cumulo+AN_cumulo+Feed_Vol+RS_cumulo+Cell_conc._interval+Arg_conc.+emission_O2+consum_O2+interval_O2; 0.173, 0.584, tmp_cumulo+pH+PL+PL_cumulo+AN_cumulo+RS_cumulo+Cell_conc._interval+rab_integral+Arg_conc.+emission_CO2+interval_O2; 0.192, 0.584, tmp_cumulo+PL_cumulo+interval_yield+Feed_Vol+RS_cumulo+Cell_conc._interval+Arg_conc.+emission_O2+interval_O2+generate_CO2; 0.191, 0.584, tmp+PL+PL_cumulo+Feed_Vol+RS_cumulo+Cell_conc._interval+Arg_conc.+emission_O2+consum_O2+generate_CO2; 0.191, 0.584, tmp+pH+PL_cumulo+Feed_Vol+RS_cumulo+Cell_conc._interval+Arg_conc.+emission_O2+consum_O2+interval_O2; 0.172, 0.584, tmp_cumulo+pH+PL_cumulo+AN_cumulo+RS_cumulo+Cell_conc._interval+rab_integral+Arg_conc.+emission_CO2+interval_O2+generate_CO2; 0.191, 0.584, tmp_cumulo+pH+PL_cumulo+RS_cumulo+Cell_conc._cumulo+Cell_conc._interval+rab_integral+Arg_conc.+emission_CO2+interval_O2; 0.191, 0.584, tmp_cumulo+PL_cumulo+AN_cumulo+Feed_Vol+RS_cumulo+Cell_conc._interval+Arg_conc.+emission_O2+consum_O2+interval_O2; 0.226, 0.584, tmp_cumulo+pH+PL_cumulo+RS_cumulo+Cell_conc._interval+Arg_conc.+emission_O2+interval_O2; 0.209, 0.584, tmp_cumulo+pH_cumulo+PL_cumulo+Feed_Vol+RS_cumulo+Cell_conc._interval+Arg_conc.+emission_O2+interval_O2; 0.172, 0.584, tmp_cumulo+PL_cumulo+AN_cumulo+Feed_Vol+RS_cumulo+Cell_conc._interval+RQ_integral+Arg_conc.+emission_CO2+consum_O2+interval_O2; 0.171, 0.583, tmp+PL_cumulo+AN_cumulo+Feed_Vol+RS_cumulo+Cell_conc._interval+rab_integral+Arg_conc.+emission_O2+interval_O2+generate_CO2; 0.190, 0.583, tmp+PL_cumulo+Feed_Vol+RS_cumulo+Cell_conc._interval+RQ_integral+Arg_conc.+emission_O2+interval_O2+generate_CO2; 0.190, 0.583, tmp+pH+PL_cumulo+Feed_Vol+RS_cumulo+Cell_conc._interval+

Arg_conc.+emission_O2+consum_O2+generate_CO2; 0.171, 0.583, tmp_cumulo+PL+PL_cumulo+AN_cumulo+Feed_Vol+RS_cumulo+Cell_conc._interval+RQ_integral+Arg_conc.+emission_CO2+interval_O2; 0.151, 0.583, tmp_cumulo+pH+PL_cumulo+AN_cumulo+RS+Feed_Vol+RS_cumulo+Cell_conc._interval+Arg_conc.+emission_O2+consum_O2+interval_O2; 0.190, 0.583, tmp_cumulo+pH_cumulo+PL_cumulo+Feed_Vol+RS_cumulo+Cell_conc._interval+rab_integral+Arg_conc.+emission_O2+interval_O2; 0.190, 0.583, tmp_cumulo+PL_cumulo+RS+Feed_Vol+RS_cumulo+Cell_conc._interval+Arg_conc.+emission_O2+interval_O2+generate_CO2; 0.208, 0.583, tmp+pH+PL_cumulo+RS_cumulo+Cell_conc._interval+rab_integral+Arg_conc.+emission_CO2+interval_O2; 0.171, 0.583, tmp_cumulo+pH+PL+PL_cumulo+Feed_Vol+RS_cumulo+Cell_conc._interval+RQ_integral+Arg_conc.+emission_CO2+interval_O2; 0.190, 0.583, tmp+PL_cumulo+RS+Feed_Vol+RS_cumulo+Cell_conc._interval+Arg_conc.+emission_O2+interval_O2+generate_CO2; 0.171, 0.583, tmp_cumulo+pH+PL_cumulo+RS+Feed_Vol+RS_cumulo+Cell_conc._interval+Arg_conc.+emission_O2+consum_O2+interval_O2; 0.190, 0.583, tmp+pH_cumulo+PL_cumulo+Feed_Vol+RS_cumulo+Cell_conc._interval+Arg_conc.+emission_O2+consum_O2+interval_O2; 0.189, 0.583, tmp_cumulo+PL_cumulo+interval_yield+Feed_Vol+RS_cumulo+Cell_conc._interval+RQ_integral+Arg_conc.+emission_CO2+interval_O2; 0.170, 0.583, tmp_cumulo+pH+PL_cumulo+RS+Feed_Vol+RS_cumulo+Cell_conc._interval+rab_integral+Arg_conc.+emission_CO2+interval_O2; 0.189, 0.582, tmp_cumulo+pH_cumulo+PL_cumulo+RS_cumulo+Cell_conc._interval+rab_integral+Arg_conc.+emission_CO2+consum_O2+interval_O2; 0.170, 0.582, tmp_cumulo+pH+PL_cumulo+Feed_Vol+RS_cumulo+Cell_conc._interval+Arg_conc.+emission_O2+emission_CO2+interval_O2+generate_CO2; 0.170, 0.582, tmp_cumulo+pH+PL_cumulo+interval_yield+Feed_Vol+RS_cumulo+Cell_conc._interval+RQ_integral+Arg_conc.+emission_CO2+interval_O2; 0.170, 0.582, tmp+PL_cumulo+AN_cumulo+Feed_Vol+RS_cumulo+Cell_conc._interval+RQ_integral+Arg_conc.+emission_O2+interval_O2+generate_CO2; 0.170, 0.582, tmp_cumulo+pH_cumulo+PL_cumulo+Feed_Vol+RS_cumulo+Cell_conc._interval+Arg_conc.+emission_O2+emission_CO2+consum_O2+interval_O2; 0.188, 0.582, tmp+PL_cumulo+Feed_Vol+RS_cumulo+Cell_conc._interval+rab_integral+Arg_conc.+emission_O2+consum_O2+generate_CO2; 0.188, 0.582, tmp_cumulo+PL_cumulo+AN_cumulo+RS+RS_cumulo+Cell_conc._interval+rab_integral+Arg_conc.+emission_CO2+interval_O2; 0.169, 0.582, tmp_cumulo+pH_cumulo+PL_cumulo+AN_cumulo+Feed_Vol+RS_cumulo+Cell_conc._interval+Arg_conc.+emission_O2+interval_O2+generate_CO2; 0.188, 0.582, tmp_cumulo+pH+PL_cumulo+AN_cumulo+Feed_Vol+RS_cumulo+Cell_conc._interval+Arg_conc.+emission_O2+interval_O2; 0.169, 0.582, tmp+PL_cumulo+AN_cumulo+RS+Feed_Vol+RS_cumulo+Cell_conc._interval+Arg_conc.+emission_O2+interval_O2+generate_CO2; 0.149, 0.582, tmp_cumulo+pH+PL_cumulo+AN_cumulo+RS+Feed_Vol+RS_cumulo+Cell_conc._interval+rab_integral+Arg_conc.+emission_CO2+interval_O2; 0.188, 0.582, tmp+PL_cumulo+Feed_Vol+RS_cumulo+Cell_conc._interval+RQ_integral+Arg_conc.+emission_CO2+interval_O2+generate_CO2; 0.169, 0.582, tmp+PL_cumulo+AN_cumulo+Feed_Vol+RS_cumulo+Cell_conc._interval+Arg_conc.+emission_O2+emission_CO2+consum_O2+generate_CO2; 0.187, 0.581, tmp_cumulo+PL_cumulo+Feed_Vol+RS_cumulo+Cell_conc._interval+RQ_integral+Arg_conc.+emission_O2+interval_O2+generate_CO2; 0.187, 0.581, tmp+PL_cumulo+RS+Feed_Vol+RS_cumulo+Cell_conc._interval+Arg_conc.+emission_O2+consum_O2+generate_CO2; 0.187, 0.581, tmp+PL_cumulo+interval_yield+Feed_Vol+RS_cumulo+Cell_conc._interval+Arg_conc.+emission_O2+interval_O2+generate_CO2; 0.187, 0.581, tmp+PL+PL_cumulo+Feed_Vol+RS_cumulo+Cell_conc._interval+RQ_integral+Arg_conc.+emission_CO2+interval_O2; 0.168, 0.581, tmp_cumulo+pH+pH_cumulo+PL_cumulo+Feed_Vol+RS_cumulo+Cell_conc._interval+RQ_integral+Arg_conc.+emission_CO2+interval_O2; 0.187, 0.581, tmp_cumulo+pH_cumulo+PL+PL_cumulo+RS_cumulo+Cell_conc._interval+rab_integral+Arg_conc.+emission_CO2+interval_O2; 0.205, 0.581, tmp+pH_cumulo+PL_cumulo+RS_cumulo+Cell_conc._interval+rab_integral+Arg_conc.+emission_CO2+interval_O2; 0.187, 0.581, tmp+pH_cumulo+PL_cumulo+Feed_Vol+RS_cumulo+Cell_conc._interval+Arg_conc.+emission_O2+consum_O2+generate_CO2; 0.187, 0.581, tmp_cumulo+pH+PL_cumulo+interval_yield+RS_cumulo+Cell_conc._interval+rab_integral+Arg_conc.+emission_CO2+interval_O2; 0.222, 0.581, tmp+PL_cumulo+RS_cumulo+Cell_conc._interval+rab_integral+Arg_conc.+emission_CO2+interval_O2; 0.205, 0.581, tmp_cumulo+pH_cumulo+PL_cumulo+RS_cumulo+Cell_conc._interval+RQ_integral+Arg_conc.+emission_CO2+interval_O2; 0.205, 0.581, tmp+PL_cumulo+AN_cumulo+Feed_Vol+Cell_conc._interval+Arg_conc.+emission_O2+consum_O2+generate_CO2; 0.186, 0.581, tmp_cumulo+PL_cumulo+Feed_Vol+RS_cumulo+Cell_conc._interval+rab_integral+Arg_conc.+emission_O2+interval_O2+generate_CO2; 0.186, 0.581, tmp+PL_cumulo+interval_yield+Feed_Vol+RS_cumulo+Cell_conc._interval+Arg_conc.+emission_O2+consum_O2+generate_CO2; 0.167, 0.580, tmp_cumulo+pH+PL_cumulo+AN_cumulo+RS_cumulo+Cell_conc._interval+rab_integral+Arg_conc.+emission_CO2+consum_O2+interval_O2; 0.167, 0.580, tmp_cumulo+pH+PL_cumulo+Feed_Vol+RS_cumulo+Cell_conc._interval+RQ_integral+Arg_conc.+emission_CO2+consum_O2+interval_O2; 0.186, 0.580, tmp_cumulo+PL_cumulo+Feed_Vol+RS_cumulo+Cell_conc._interval+Arg_conc.+emission_CO2+consum_O2+generate_CO2; 0.186, 0.580, tmp_cumulo+pH+PL_cumulo+Feed_Vol+RS_cumulo+Cell_conc._interval+RQ_integral+Arg_conc.+emission_O2+interval_O2; 0.221, 0.580, tmp+PL_cumulo+Feed_Vol+Cell_conc._interval+Arg_conc.+emission_O2+consum_O2+generate_CO2; 0.186, 0.580, tmp+PL_cumulo+Feed_Vol+RS_cumulo+Cell_conc._interval+RQ_integral+Arg_conc.+emission_O2+consum_O2+generate_CO2; 0.167, 0.580, tmp_cumulo+pH_cumulo+PL_cumulo+AN_cumulo+RS+RS_cumulo+Cell_conc._interval+rab_integral+Arg_conc.+emission_CO2+interval_O2; 0.186, 0.580, tmp_cumulo+pH+PL_cumulo+interval_yield+RS_cumulo+Cell_conc._interval+rab_integral+Arg_conc.+emission_CO2+interval_O2; 0.186, 0.580, tmp_cumulo+PL_cumulo+RS+Feed_Vol+RS_cumulo+Cell_conc._interval+RQ_integral+Arg_conc.+emission_CO2+interval_O2; 0.147, 0.580, tmp_cumulo+pH+PL+PL_cumulo+AN_cumulo+Feed_Vol+RS_cumulo+Cell_conc._interval+Arg_conc.+emission_O2+consum_O2+interval_O2; 0.186, 0.580, tmp+PL_cumulo+AN_cumulo+RS+Feed_Vol+Cell_conc._interval+Arg_conc.+emission_O2+consum_O2+generate_CO2; 0.167, 0.580, tmp_cumulo+pH+PL_cumulo+Feed_Vol+RS_cumulo+Cell_conc._interval+rab_integral+Arg_conc.+emission_CO2+interval_O2+generate_CO2; 0.166, 0.580, tmp_cumulo+pH+PL_cumulo+RS+Feed_Vol+RS_cumulo+Cell_conc._interval+RQ_integral+Arg_conc.+emission_CO2+interval_O2; 0.146, 0.580, tmp_cumulo+pH+PL+PL_cumulo+AN_cumulo+Feed_Vol+RS_cumulo+Cell_conc._interval+rab_integral+Arg_conc.+emission_CO2+interval_O2; 0.185, 0.580, tmp+PL_cumulo+AN_cumulo+Feed_Vol+RS_cumulo+Cell_conc._interval+RQ_ integral+Arg_conc.+emission_CO2+interval_O2; 0.185, 0.580, tmp_cumulo+PL_cumulo+Feed_Vol+RS_cumulo+Cell_conc._interval+RQ_integral+Arg_conc.+emission_CO2+consum_O2+generate_CO2; 0.185, 0.580, tmp+PL_cumulo+Feed_Vol+RS_cumulo+Cell_conc._interval+Arg_conc.+emission_O2+consum_O2+interval_O2+generate_CO2; 0.166, 0.580, tmp_cumulo+pH+PL_cumulo+RS+Feed_Vol+RS_cumulo+Cell_conc._interval+Arg_conc.+emission_O2+interval_O2+generate_CO2; 0.203, 0.579, tmp_cumulo+pH+PL_cumulo+RS_cumulo+Cell_conc._interval+rab_integral+Arg_conc.+emission_O2+interval_O2; 0.185, 0.579, tmp+tmp_cumulo+pH+PL_cumulo+RS_cumulo+Cell_conc._interval+rab_integral+Arg_conc.+emission_CO2+interval_O2; 0.203, 0.579, tmp_cumulo+PL_cumulo+RS_cumulo+Cell_conc._interval+rab_integral+Arg_conc.+emission_CO2+interval_O2+generate_CO2; 0.166, 0.579, tmp_cumulo+pH_cumulo+PL_cumulo+interval_yield+Feed_Vol+RS_cumulo+Cell_conc._interval+Arg_conc.+emission_O2+consum_O2+interval_O2; 0.146, 0.579, tmp_cumulo+pH+PL_cumulo+AN_cumulo+Feed_Vol+RS_cumulo+Cell_conc._interval+RQ_integral+Arg_conc.+emission_CO2+consum_O2+interval_O2; 0.203, 0.579, tmp_cumulo+PL_cumulo+Feed_Vol+RS_cumulo+Cell_conc._interval+RQ_integral+Arg_conc.+emission_O2+interval_O2; 0.166, 0.579, tmp+PL+PL_cumulo+AN_cumulo+Feed_Vol+RS_cumulo+Cell_conc._interval+Arg_conc.+emission_O2+consum_O2+generate_CO2; 0.166, 0.579, tmp+PL_cumulo+AN_cumulo+interval_yield+Feed_Vol+RS_cumulo+Cell_conc._interval+Arg_conc.+emission_O2+interval_O2+generate_CO2; 0.165, 0.579, tmp+PL_cumulo+AN_cumulo+Feed_Vol+RS_cumulo+Cell_conc._interval+RQ_integral+Arg_conc.+emission_CO2+interval_O2+generate_CO2; 0.165, 0.579, tmp_cumulo+PL_cumulo+AN_cumulo+Feed_Vol+RS_cumulo+Cell_conc._interval+Arg_conc.+emission_O2+emission_CO2+interval_O2+generate_CO2; 0.165, 0.579, tmp_cumulo+pH+PL_cumulo+AN+Feed_Vol+RS_cumulo+Cell_conc._interval+RQ_integral+Arg_conc.+emission_CO2+interval_O2; 0.202, 0.579, tmp_cumulo+PL_cumulo+AN_cumulo+RS_cumulo+Cell_conc._interval+rab_integral+Arg_conc.+emission_CO2+interval_O2; 0.184, 0.579, tmp_cumulo+pH+PL_cumulo+RS_cumulo+Cell_conc._interval+rab_integral+Arg_conc.+emission_O2+emission_CO2+interval_O2; 0.165, 0.579, tmp+pH+PL_cumulo+Feed_Vol+RS_cumulo+Cell_conc._interval+Arg_conc.+emission_O2+emission_CO2+interval_O2+generate_CO2; 0.145, 0.579, tmp_cumulo+pH+PL_cumulo+AN_cumulo+Feed_Vol+RS_cumulo+Cell_conc._interval+rab_integral+Arg_conc.+emission_O2+consum_O2+interval_O2; 0.184, 0.579, tmp+PL_cumulo+RS+Feed_Vol+Cell_conc._interval+Arg_conc.+emission_O2+emission_CO2+consum_O2+generate_CO2; 0.184, 0.579, tmp_cumulo+pH+PL_cumulo+Feed_Vol+RS_cumulo+Cell_conc._interval+Arg_conc.+emission_O2+emission_CO2+interval_O2; 0.202, 0.579, tmp_cumulo+PL_cumulo+interval_yield+Feed_Vol+RS_cumulo+Cell_conc._interval+RQ_integral+Arg_conc.+interval_O2; 0.184, 0.579, tmp_cumulo+PL_cumulo+RS+RS_cumulo+Cell_conc._interval+rab_integral+Arg_conc.+emission_CO2+interval_O2+generate_CO2; 0.165, 0.579, tmp_cumulo+pH+PL_cumulo+AN_cumulo+RS_cumulo+Cell_conc._cumulo+Cell_conc._interval+rab_integral+Arg_conc.+emission_CO2+interval_O2; 0.165, 0.579, tmp_cumulo+PL+PL_cumulo+Feed_Vol+RS_cumulo+Cell_conc._interval+RQ_integral+Arg_conc.+emission_CO2+interval_O2+generate_CO2; 0.165, 0.579, tmp_cumulo+pH+pH_cumulo+PL_cumulo+Feed_Vol+RS_cumulo+Cell_conc._interval+rab_integral+Arg_conc.+emission_CO2+interval_O2; 0.184, 0.579, tmp_cumulo+PL_cumulo+AN_cumulo+Feed_Vol+RS_cumulo+Cell_conc._interval+Arg_conc.+emission_O2+consum_O2+generate_CO2; 0.145, 0.579, tmp+PL+PL_cumulo+AN_cumulo+Feed_Vol+RS_cumulo+Cell_conc._interval+Arg_conc.+emission_O2+emission_CO2+interval_O2+generate_CO2; 0.219, 0.579, tmp_cumulo+PL_cumulo+Feed_Vol+RS_cumulo+Cell_conc._interval+RQ_integral+Arg_conc.+interval_O2; 0.183, 0.579, tmp+PL_cumulo+Feed_Vol+RS_cumulo+Cell_conc._interval+RQ_integral+Arg_conc.+emission_CO2+consum_O2+generate_CO2; 0.164, 0.578, tmp_cumulo+pH_cumulo+PL_cumulo+interval_yield+Feed_Vol+RS_cumulo+Cell_conc._interval+rab_integral+Arg_conc.+emission_CO2+interval_O2; 0.183, 0.578, tmp_cumulo+pH+PL_cumulo+Feed_Vol+RS_cumulo+Cell_conc._interval+Arg_conc.+emission_O2+consum_O2+generate_CO2; 0.164, 0.578, tmp_cumulo+pH_cumulo+PL_cumulo+interval_yield+Feed_Vol+RS_cumulo+Cell_conc._interval+RQ_integral+Arg_conc.+emission_CO2+interval_O2; 0.164, 0.578, tmp_cumulo+pH+PL_cumulo+RS+RS_cumulo+Cell_conc._interval+rab_integral+Arg_conc.+emission_CO2+interval_O2+generate_CO2; 0.183, 0.578, tmp_cumulo+pH+PL_cumulo+RS+RS_cumulo+Cell_conc._interval+RQ_integral+Arg_conc.+emission_CO2+interval_O2; 0.164, 0.578, tmp_cumulo+pH+PL_cumulo+RS+Feed_Vol+RS_cumulo+Cell_conc._interval+Arg_conc.+emission_O2+consum_O2+interval_O2; 0.144, 0.578, tmp_cumulo+pH+PL_cumulo+AN_cumulo+Feed_Vol+RS_cumulo+Cell_conc._interval+rab_integral+Arg_conc.+emission_CO2+consum_O2+interval_O2; 0.144, 0.578, tmp_cumulo+pH_cumulo+PL_cumulo+AN_cumulo+Feed_Vol+RS_cumulo+Cell_conc._interval+Arg_conc.+emission_O2+emission_CO2+consum_O2+interval_O2; 0.164, 0.578, tmp_cumulo+pH_cumulo+PL_cumulo+AN_cumulo+RS_cumulo+Cell_conc._interval+rab_integral+Arg_conc.+emission_CO2+interval_O2+generate_CO2; 0.201, 0.578, tmp_cumulo+pH+PL_cumulo+RS_cumulo+Cell_conc._interval+Arg_conc.+emission_O2+consum_O2+interval_O2; 0.164, 0.578, tmp_cumulo+pH_cumulo+PL+PL_cumulo+Feed_Vol+RS_cumulo+Cell_conc._interval+RQ_integral+Arg_conc.+emission_CO2+interval_O2; 0.164, 0.578, tmp_cumulo+pH_cumulo+PL_cumulo+interval_yield+Feed_Vol+RS_cumulo+Cell_conc._interval+Arg_conc.+emission_O2+interval_O2+generate_CO2; 0.164, 0.578, tmp_cumulo+pH+PL_cumulo+AN_cumulo+Feed_Vol+RS_cumulo+Cell_conc._interval+rab_integral+Arg_conc.+emission_O2+interval_O2; 0.144, 0.578, tmp_cumulo+pH+PL+PL_cumulo+AN_cumulo+Feed_Vol+RS_cumulo+Cell_conc._interval+RQ_integral+Arg_conc.+emission_CO2+interval_O2; 0.183, 0.578, tmp+pH+PL_cumulo+AN_cumulo+RS_cumulo+Cell_conc._interval+rab_integral+Arg_conc.+emission_CO2+interval_O2; 0.164, 0.578, tmp_cumulo+PL_cumulo+AN_cumulo+Feed_Vol+RS_cumulo+Cell_conc._interval+RQ_integral+Arg_conc.+emission_O2+emission_CO2+interval_O2; 0.144, 0.578, tmp_cumulo+pH+PL_cumulo+AN_cumulo+Feed_Vol+RS_cumulo+Cell_conc._interval+RQ_integral+Arg_conc.+emission_O2+consum_O2+interval_O2; 0.164, 0.578, tmp+PL+PL_cumulo+AN_cumulo+Feed_Vol+RS_cumulo+Cell_conc._interval+RQ_integral+Arg_conc.+emission_CO2+interval_O2; 0.164, 0.578, tmp_cumulo+pH_cumulo+PL_cumulo+Feed_Vol+RS_cumulo+Cell_conc._interval+Arg_conc.+emission_O2+emission_CO2+interval_O2+generate_CO2; 0.163, 0.578, tmp_cumulo+PL_cumulo+AN_cumulo+interval_yield+Feed_Vol+RS_cumulo+Cell_conc._interval+Arg_conc.+emission_O2+interval_O2+generate_CO2; 0.163, 0.578, tmp_cumulo+pH_cumulo+PL_cumulo+Feed_Vol+RS_cumulo+Cell_conc._interval+rab_integral+Arg_conc.+emission_CO2+interval_O2+generate_CO2; 0.182, 0.578, tmp_cumulo+PL_cumulo+interval_yield+Feed_Vol+RS_cumulo+Cell_conc._interval+Arg_conc.+emission_

O2+consum_O2+generate_CO2; 0.182, 0.578, tmp+tmp_cumulo+PL_cumulo+Feed_Vol+RS_cumulo+Cell_conc._interval+Arg_conc.+emission_O2+interval_O2+generate_CO2; 0.163, 0.578, tmp_cumulo+PL_cumulo+interval_yield+Feed_Vol+RS_cumulo+Cell_conc._interval+RQ_integral+Arg_conc.+emission_CO2+interval_O2+generate_CO2; 0.143, 0.578, tmp_cumulo+pH+PL_cumulo+AN_cumulo+interval_yield+Feed_Vol+RS_cumulo+Cell_conc._interval+Arg_conc.+emission_O2+consum_O2+interval_O2; 0.163, 0.578, tmp_cumulo+PL_cumulo+AN_cumulo+RS+Feed_Vol+RS_cumulo+Cell_conc._interval+Arg_conc.+emission_O2+interval_O2+generate_CO2; 0.163, 0.578, tmp_cumulo+pH+PL_cumulo+interval_yield+Feed_Vol+RS_cumulo+Cell_conc._interval+Arg_conc.+emission_O2+consum_O2+interval_O2; 0.163, 0.578, tmp_cumulo+pH_cumulo+PL_cumulo+Feed_Vol+RS_cumulo+Cell_conc._interval+RQ_integral+Arg_conc.+emission_CO2+consum_O2+interval_O2; 0.143, 0.578, tmp_cumulo+pH+PL_cumulo+AN_cumulo+Feed_Vol+RS_cumulo+Cell_conc._interval+rab_integral+Arg_conc.+emission_CO2+interval_O2+generate_CO2; 0.143, 0.578, tmp_cumulo+pH+PL+PL_cumulo+AN_cumulo+RS+RS_cumulo+Cell_conc._interval+rab_integral+Arg_conc.+emission_CO2+interval_O2; 0.163, 0.578, tmp_cumulo+pH+PL_cumulo+Feed_Vol+RS_cumulo+Cell_conc._interval+rab_integral+Arg_conc.+emission_CO2+consum_O2+interval_O2; 0.163, 0.578, tmp_cumulo+pH+pH_cumulo+PL_cumulo+AN_cumulo+RS_cumulo+Cell_conc._interval+rab_integral+Arg_conc.+emission_CO2+interval_O2; 0.182, 0.577, tmp_cumulo+PL_cumulo+AN_cumulo+Feed_Vol+RS_cumulo+Cell_conc._interval+rab_integral+Arg_conc.+emission_CO2+interval_O2; 0.163, 0.577, tmp+pH_cumulo+PL_cumulo+Feed_Vol+RS_cumulo+Cell_conc._interval+Arg_conc.+emission_O2+emission_CO2+interval_O2+generate_CO2; 0.182, 0.577, tmp_cumulo+PL_cumulo+Feed_Vol+RS_cumulo+Cell_conc._interval+rab_integral+Arg_conc.+emission_CO2+interval_O2+generate_CO2; 0.163, 0.577, tmp+PL+PL_cumulo+AN_cumulo+Feed_Vol+RS_cumulo+Cell_conc._interval+Arg_conc.+emission_O2+consum_O2+interval_O2; 0.163, 0.577, tmp_cumulo+pH+PL_cumulo+interval_yield+Feed_Vol+RS_cumulo+Cell_conc._interval+Arg_conc.+emission_O2+interval_O2+generate_CO2; 0.182, 0.577, tmp+pH+PL_cumulo+Feed_Vol+RS_cumulo+Cell_conc._interval+RQ_integral+Arg_conc.+emission_CO2+interval_O2; 0.163, 0.577, tmp_cumulo+pH+PL+PL_cumulo+Feed_Vol+RS_cumulo+Cell_conc._interval+rab_integral+Arg_conc.+emission_CO2+interval_O2; 0.182, 0.577, tmp_cumulo+PL_cumulo+RS+Feed_Vol+RS_cumulo+Cell_conc._interval+Arg_conc.+emission_O2+consum_O2+generate_CO2; 0.163, 0.577, tmp_cumulo+pH+PL_cumulo+Feed_Vol+RS_cumulo+Cell_conc._interval+RQ_integral+Arg_conc.+emission_O2+emission_CO2+interval_O2; 0.200, 0.577, tmp+pH+PL_cumulo+Feed_Vol+RS_cumulo+Cell_conc._interval+Arg_conc.+emission_O2+interval_O2; 0.182, 0.577, tmp_cumulo+pH+PL_cumulo+AN_cumulo+RS+Cell_conc._interval+RQ_integral+Arg_conc.+emission_CO2+interval_O2; 0.162, 0.577, tmp_cumulo+pH+PL_cumulo+Feed_Vol+RS_cumulo+Cell_conc._interval+rab_integral+Arg_conc.+emission_O2+consum_O2+interval_O2; 0.199, 0.577, tmp_cumulo+PL_cumulo+RS+RS_cumulo+Cell_conc._interval+RQ_integral+Arg_conc.+emission_CO2+interval_O2; 0.162, 0.577, tmp_cumulo+pH+pH_cumulo+PL_cumulo+Feed_Vol+RS_cumulo+Cell_conc._interval+Arg_conc.+emission_O2+consum_O2+interval_O2; 0.162, 0.577, tmp_cumulo+pH+PL_cumulo+Feed_Vol+RS_cumulo+Cell_conc._interval+RQ_integral+Arg_conc.+emission_CO2+interval_O2+generate_CO2; 0.181, 0.577, tmp+tmp_cumulo+pH_cumulo+PL_cumulo+RS_cumulo+Cell_conc._interval+rab_integral+Arg_conc.+emission_CO2+interval_O2; 0.181, 0.577, tmp+tmp_cumulo+PL_cumulo+Feed_Vol+RS_cumulo+Cell_conc._interval+RQ_integral+Arg_conc.+emission_CO2+interval_O2; 0.181, 0.577, tmp_cumulo+PL_cumulo+Feed_Vol+RS_cumulo+Cell_conc._interval+Arg_conc.+emission_O2+emission_CO2+consum_O2+interval_O2; 0.142, 0.577, tmp_cumulo+pH+PL_cumulo+AN_cumulo+Feed_Vol+RS_cumulo+Cell_conc._interval+Arg_conc.+emission_O2+emission_CO2+interval_O2+generate_CO2; 0.181, 0.577, tmp_cumulo+PL_cumulo+RS+Feed_Vol+RS_cumulo+Cell_conc._interval+rab_integral+Arg_conc.+emission_CO2+interval_O2; 0.142, 0.577, tmp_cumulo+pH+pH_cumulo+PL_cumulo+AN_cumulo+Feed_Vol+RS_cumulo+Cell_conc._interval+Arg_conc.+emission_O2+consum_O2+interval_O2; 0.180, 0.576, tmp_cumulo+pH+pH_cumulo+PL_cumulo+RS_cumulo+Cell_conc._cumulo+Cell_conc._interval+rab_integral+Arg_conc.+emission_CO2+interval_O2; 0.141, 0.576, tmp+PL+PL_cumulo+AN_cumulo+Feed_Vol+RS_cumulo+Cell_conc._interval+RQ_integral+Arg_conc.+emission_CO2+interval_O2+generate_CO2; 0.161, 0.576, tmp+PL+PL_cumulo+Feed_Vol+RS_cumulo+Cell_conc._interval+Arg_conc.+emission_O2+emission_CO2+interval_O2+generate_CO2; 0.180, 0.576, tmp_cumulo+pH_cumulo+PL_cumulo+AN+RS_cumulo+Cell_conc._interval+rab_integral+Arg_conc.+emission_CO2+interval_O2; 0.216, 0.576, tmp_cumulo+PL_cumulo+Feed_Vol+RS_cumulo+Cell_conc._interval+Arg_conc.+emission_O2+interval_O2; 0.141, 0.576, tmp_cumulo+pH_cumulo+PL_cumulo+AN_cumulo+interval_yield+Feed_Vol+RS_cumulo+Cell_conc._interval+Arg_conc.+emission_O2+consum_O2+interval_O2; 0.198, 0.576, tmp_cumulo+PL+PL_cumulo+RS_cumulo+Cell_conc._interval+RQ_integral+Arg_conc.+emission_CO2+interval_O2; 0.161, 0.576, tmp_cumulo+pH+PL_cumulo+AN+AN_cumulo+RS_cumulo+Cell_conc._interval+rab_integral+Arg_conc.+emission_CO2+interval_O2; 0.161, 0.576, tmp_cumulo+pH+PL_cumulo+AN+Feed_Vol+RS_cumulo+Cell_conc._interval+rab_integral+Arg_conc.+emission_CO2+interval_O2; 0.161, 0.576, tmp_cumulo+pH+PL_cumulo+RS+RS_cumulo+Cell_conc._interval+rab_integral+Arg_conc.+emission_CO2+consum_O2+interval_O2; 0.161, 0.576, tmp_cumulo+pH+PL_cumulo+Feed_Vol+RS_cumulo+Cell_conc._interval+rab_integral+Arg_conc.+emission_O2+emission_CO2+interval_O2; 0.141, 0.576, tmp_cumulo+PL+PL_cumulo+AN_cumulo+Feed_Vol+RS_cumulo+Cell_conc._interval+RQ_integral+Arg_conc.+emission_CO2+interval_O2+generate_CO2; 0.180, 0.576, tmp_cumulo+PL_cumulo+Feed_Vol+RS_cumulo+Cell_conc._interval+Arg_conc.+emission_O2+consum_O2+interval_O2+generate_CO2; 0.161, 0.576, tmp_cumulo+pH_cumulo+PL+PL_cumulo+AN_cumulo+RS_cumulo+Cell_conc._interval+rab_integral+Arg_conc.+emission_CO2+interval_O2; 0.180, 0.576, tmp+PL_cumulo+Feed_Vol+RS_cumulo+Cell_conc._interval+rab_integral+Arg_conc.+emission_CO2+consum_O2+generate_CO2; 0.161, 0.576, tmp_cumulo+pH+PL+PL_cumulo+RS+RS_cumulo+Cell_conc._interval+rab_integral+Arg_conc.+emission_CO2+interval_O2; 0.141, 0.576, tmp+pH+PL_cumulo+AN_cumulo+Feed_Vol+RS_cumulo+Cell_conc._interval+Arg_conc.+emission_O2+emission_CO2+interval_O2+generate_CO2; 0.179, 0.576, tmp_cumulo+PL_cumulo+Feed_Vol+RS_cumulo+Cell_conc._interval+RQ_integral+Arg_conc.+emission_O2+consum_O2+interval_O2; 0.198, 0.576, tmp_cumulo+PL+PL_cumulo+RS_cumulo+Cell_conc._interval+rab_integral+Arg_conc.+emission_CO2+interval_O2; 0.198, 0.576, tmp+PL_cumulo+Feed_Vol+RS_cumulo+Cell_conc._interval+rab_integral+Arg_conc.+emission_O2+interval_O2; 0.160, 0.576, tmp_cumulo+ pH+PL_cumulo+interval_yield+Feed_Vol+RS_cumulo+ Cell_conc._interval+rab_integral+Arg_conc.+emission_ CO2+interval_O2; 0.179, 0.576, tmp+pH+PL_cumulo+ Feed_Vol+RS_cumulo+Cell_conc._interval+rab_integral+ Arg_conc.+emission_CO2+interval_O2; 0.160, 0.576, tmp_ cumulo+pH_cumulo+PL_cumulo+RS+Feed_Vol+RS_ cumulo+Cell_conc._interval+rab_integral+Arg_conc.+ emission_CO2+interval_O2; 0.160, 0.576, tmp_cumulo+ pH_cumulo+PL_cumulo+Feed_Vol+RS_cumulo+Cell_ conc._interval+rab_integral+Arg_conc.+emission_CO2+ consum_O2+interval_O2; 0.160, 0.576, tmp+PL_cumulo+ AN_cumulo+Feed_Vol+RS_cumulo+Cell_conc._interval+ Arg_conc.+emission_O2+emission_CO2+consum_O2+ interval_O2; 0.179, 0.575, tmp_cumulo+PL+PL_cumulo+ Feed_Vol+RS_cumulo+Cell_conc._interval+Arg_conc.+ emission_O2+interval_O2+generate_CO2; 0.160, 0.575, tmp_cumulo+PL_cumulo+AN_cumulo+Feed_Vol+RS_cu- mulo+Cell_conc._interval+RQ_integral+Arg_conc.+emis- sion_O2+interval_O2+generate_CO2; 0.160, 0.575, tmp+ tmp_cumulo+pH+PL_cumulo+Feed_Vol+RS_cumulo+ Cell_conc._interval+RQ_integral+Arg_conc.+emission_ CO2+interval_O2; 0.160, 0.575, tmp_cumulo+pH+PL_ cumulo+Feed_Vol+RS_cumulo+Cell_conc._interval+RQ_ integral+Arg_conc.+emission_O2+consum_O2+interval_ O2; 0.179, 0.575, tmp_cumulo+pH+PL_cumulo+RS+Feed_ Vol+RS_cumulo+Cell_conc._interval+Arg_conc.+ emission_O2+interval_O2; 0.160, 0.575, tmp_cumulo+pH+ PL+PL_cumulo+Feed_Vol+RS_cumulo+Cell_conc._ interval+Arg_conc.+emission_O2+consum_O2+interval_ O2; 0.179, 0.575, tmp_cumulo+pH_cumulo+PL_cumulo+ Feed_Vol+RS_cumulo+Cell_conc._interval+RQ_integral+ Arg_conc.+emission_O2+interval_O2; 0.197, 0.575, tmp_ cumulo+pH_cumulo+PL_cumulo+RS_cumulo+Cell_ conc._interval+rab_integral+Arg_conc.+emission_O2+ interval_O2; 0.160, 0.575, tmp_cumulo+pH+pH_cumulo+ PL_cumulo+RS+RS_cumulo+Cell_conc._interval+rab_ integral+Arg_conc.+emission_CO2+interval_O2; 0.160, 0.575, tmp+PL_cumulo+AN_cumulo+Feed_Vol+RS_cu- mulo+Cell_conc._interval+Arg_conc.+emission_O2+con- sum_O2+interval_O2+generate_CO2; 0.197, 0.575, tmp_ cumulo+PL_cumulo+Feed_Vol+RS_cumulo+Cell_conc._ interval+rab_integral+Arg_conc.+emission_O2+interval_ O2; 0.140, 0.575, tmp_cumulo+pH+PL_cumulo+AN_ cumulo+RS+RS_cumulo+Cell_conc._interval+rab_ integral+Arg_conc.+emission_CO2+interval_O2+ generate_CO2; 0.139, 0.575, tmp+PL+PL_cumulo+AN_ cumulo+Feed_Vol+RS_cumulo+Cell_conc._interval+RQ_ integral+Arg_conc.+emission_O2+interval_O2+generate_ CO2; 0.139, 0.575, tmp+pH_cumulo+AN_cumulo+ Feed_Vol+RS_cumulo+Cell_conc._interval+Arg_conc.+ emission_O2+emission_CO2+consum_O2+interval_O2; 0.197, 0.575, tmp+PL_cumulo+RS+RS_cumulo+Cell_ conc._interval+rab_integral+Arg_conc.+emission_CO2+in- terval_O2; 0.139, 0.575, tmp_cumulo+pH+pH_cumulo+ PL_cumulo+AN_cumulo+Feed_Vol+RS_cumulo+Cell_ conc._interval+rab_integral+Arg_conc.+emission_CO2+ interval_O2; 0.178, 0.575, tmp+PL_cumulo+Feed_Vol+ RS_cumulo+Cell_conc._interval+Arg_conc.+emission_ O2+emission_CO2+consum_O2+interval_O2; 0.159, 0.575, tmp_cumulo+pH_cumulo+PL_cumulo+Feed_Vol+ RS_cumulo+Cell_conc._interval+rab_integral+Arg_conc.+ emission_O2+consum_O2+interval_O2; 0.159, 0.575, tmp_ cumulo+pH+PL_cumulo+AN_cumulo+interval_yield+RS_ cumulo+Cell_conc._interval+rab_integral+Arg_conc.+ emission_CO2+interval_O2; 0.159, 0.575, tmp_cumulo+ PL+PL_cumulo+Feed_Vol+RS_cumulo+Cell_conc._ interval+RQ_integral+Arg_conc.+emission_O2+emission_ CO2+interval_O2; 0.178, 0.575, tmp_cumulo+PL_cumulo+ RS+Feed_Vol+RS_cumulo+Cell_conc._interval+Arg_ conc.+emission_O2+consum_O2+interval_O2; 0.159, 0.575, tmp_cumulo+PL_cumulo+Feed_Vol+RS_cumulo+ Cell_conc._interval+RQ_integral+Arg_conc.+emission_ O2+emission_CO2+interval_O2+generate_CO2; 0.196, 0.575, tmp+PL_cumulo+RS+Feed_Vol+Cell_conc._inter- val+Arg_conc.+emission_O2+interval_O2+generate_CO2; 0.139, 0.575, tmp_cumulo+pH+PL_cumulo+AN_cumulo+ RS+Feed_Vol+RS_cumulo+Cell_conc._interval+Arg_ conc.+emission_O2+interval_O2+generate_CO2; 0.139, 0.574, tmp+PL+PL_cumulo+AN_cumulo+Feed_Vol+RS_ cumulo+Cell_conc._interval+rab_integral+Arg_conc.+ emission_O2+interval_O2+generate_CO2; 0.159, 0.574, tmp_cumulo+PL+PL_cumulo+Feed_Vol+RS_cumulo+ Cell_conc._interval+RQ_integral+Arg_conc.+emission_ CO2+consum_O2+interval_O2; 0.138, 0.574, tmp_cu- mulo+pH_cumulo+PL_cumulo+AN_cumulo+Feed_Vol+ RS_cumulo+Cell_conc._interval+RQ_integral+Arg_conc.+ emission_CO2+consum_O2+interval_O2; 0.177, 0.574, tmp+PL_cumulo+AN_cumulo+RS+Feed_Vol+Cell_conc._ interval+Arg_conc.+emission_O2+interval_O2+generate_ CO2; 0.177, 0.574, tmp+pH_cumulo+PL_cumulo+RS+ Feed_Vol+Cell_conc._interval+Arg_conc.+emission_O2+ interval_O2+generate_CO2; 0.138, 0.574, tmp_cumulo+ PL+PL_cumulo+AN_cumulo+Feed_Vol+RS_cumulo+ Cell_conc._interval+RQ_integral+Arg_conc.+emission_ CO2+consum_O2+interval_O2; 0.158, 0.574, tmp+PL+PL_ cumulo+Feed_Vol+RS_cumulo+Cell_conc._interval+Arg_ conc.+emission_O2+emission_CO2+consum_O2+ generate_CO2; 0.158, 0.574, tmp+pH+PL_cumulo+AN_ cumulo+Feed_Vol+RS_cumulo+Cell_conc._interval+rab_ integral+Arg_conc.+emission_CO2+interval_O2; 0.177, 0.574, tmp_cumulo+PL_cumulo+AN+Feed_Vol+RS_cu- mulo+Cell_conc._interval+RQ_integral+Arg_conc.+emis- sion_CO2+interval_O2; 0.177, 0.574, tmp_cumulo+PL_cu- mulo+Feed_Vol+RS_cumulo+Cell_conc._interval+rab_ integral+RQ_integral+Arg_conc.+emission_CO2+interval_ O2; 0.158, 0.574, tmp+PL_cumulo+Feed_Vol+RS_ cumulo+Cell_conc._interval+rab_integral+Arg_conc.+ emission_CO2+interval_O2+generate_CO2; 0.138, 0.574, tmp_cumulo+pH+PL_cumulo+AN_cumulo+ RS+RS_cumulo+Cell_conc._interval+rab_integral+Arg_ conc.+emission_CO2+consum_O2+interval_O2; 0.138, 0.574, tmp_cumulo+pH_cumulo+PL_cumulo+AN_cu- mulo+RS+Feed_Vol+RS_cumulo+Cell_conc._interval+ Arg_conc.+emission_O2+consum_O2+interval_O2; 0.177, 0.574, tmp+pH_cumulo+PL_cumulo+Feed_Vol+RS_cu- mulo+Cell_conc._interval+rab_integral+Arg_conc.+emis- sion_CO2+interval_O2; 0.213, 0.574, tmp+PL_cumulo+ RS_cumulo+Cell_conc._interval+RQ_integral+Arg_conc.+ emission_CO2+interval_O2; 0.158, 0.574, tmp+PL_ cumulo+AN_cumulo+Feed_Vol+RS_cumulo+Cell_conc._ interval+RQ_integral+Arg_conc.+emission_O2+consum_ O2+generate_CO2; 0.158, 0.574, tmp_cumulo+pH+PL_ cumulo+RS+RS_cumulo+Cell_conc._cumulo+Cell_conc._ interval+rab_integral+Arg_conc.+emission_CO2+interval_ O2; 0.138, 0.574, tmp_cumulo+pH+PL_cumulo+AN+AN_ cumulo+Feed_Vol+RS_cumulo+Cell_conc._interval+Arg_ conc.+emission_O2+consum_O2+interval_O2; 0.177, 0.574, tmp+PL_cumulo+RS+Feed_Vol+Cell_conc._inter- val+RQ_integral+Arg_conc.+emission_O2+consum_O2+ generate_CO2; 0.138, 0.574, tmp_cumulo+pH+PL_cu- mulo+AN_cumulo+Feed_Vol+RS_cumulo+Cell_conc._ interval+rab_integral+Arg_conc.+emission_O2+emission_ CO2+interval_O2; 0.158, 0.574, tmp+tmp_cumulo+pH+ PL_cumulo+AN_cumulo+RS+Cell_conc._ interval+rab_integral+Arg_conc.+emission_CO2+interval_ O2; 0.177, 0.574, tmp+pH_cumulo+PL_cumulo+Feed_ Vol+RS_cumulo+Cell_conc._interval+RQ_integral+Arg_ conc.+emission_CO2+interval_O2; 0.158, 0.574, tmp+PL_ cumulo+AN_cumulo+Feed_Vol+RS_cumulo+Cell_conc._ interval+rab_integral+Arg_conc.+emission_O2+consum_

O2+generate_CO2; 0.158, 0.574, tmp_cumulo+pH_cumulo+PL_cumulo+RS+Feed_Vol+RS_cumulo+Cell_conc._interval+Arg_conc.+emission_O2+interval_O2+generate_CO2; 0.195, 0.574, tmp_cumulo+PL_cumulo+RS_cumulo+Cell_conc._interval+rab_integral+Arg_conc.+emission_CO2+consum_O2+interval_O2; 0.177, 0.574, tmp_cumulo+pH_cumulo+PL_cumulo+interval_yield+Feed_Vol+RS_cumulo+Cell_conc._interval+RQ_integral+Arg_conc.+interval_O2; 0.177, 0.574, tmp+pH_cumulo+PL_cumulo+AN_cumulo+RS_cumulo+Cell_conc._interval+rab_integral+Arg_conc.+emission_CO2+interval_O2; 0.158, 0.574, tmp_cumulo+pH+PL_cumulo+Feed_Vol+RS_cumulo+Cell_conc._interval+rab_integral+Arg_conc.+emission_O2+interval_O2+generate_CO2; 0.138, 0.574, tmp_cumulo+pH+PL_cumulo+AN_cumulo+interval_yield+Feed_Vol+RS_cumulo+Cell_conc._interval+RQ_integral+Arg_conc.+emission_CO2+interval_O2; 0.177, 0.574, tmp+pH+PL_cumulo+RS+Feed_Vol+Cell_conc._interval+Arg_conc.+emission_O2+consum_O2+generate_CO2; 0.157, 0.574, tmp_cumulo+pH_cumulo+PL_cumulo+AN_cumulo+Feed_Vol+RS_cumulo+Cell_conc._interval+rab_integral+Arg_conc.+emission_O2+interval_O2; 0.157, 0.574, tmp_cumulo+PL_cumulo+AN_cumulo+Feed_Vol+RS_cumulo+Cell_conc._interval+rab_integral+Arg_conc.+emission_O2+interval_O2+generate_CO2; 0.137, 0.574, tmp_cumulo+pH+PL_cumulo+AN_cumulo+interval_yield+Feed_Vol+RS_cumulo+Cell_conc._interval+rab_integral+Arg_conc.+emission_CO2+interval_O2; 0.176, 0.574, tmp_cumulo+pH_cumulo+PL_cumulo+Feed_Vol+RS_cumulo+Cell_conc._interval+Arg_conc.+emission_O2+consum_O2+generate_CO2; 0.157, 0.574, tmp_cumulo+pH+PL+PL_cumulo+RS_cumulo+Cell_conc._interval+rab_integral+Arg_conc.+emission_CO2+interval_O2+generate_CO2; 0.157, 0.574, tmp+PL+PL_cumulo+Feed_Vol+RS_cumulo+Cell_conc._interval+RQ_integral+Arg_conc.+emission_CO2+interval_O2+generate_CO2; 0.195, 0.574, tmp+PL_cumulo+Feed_Vol+Cell_conc._interval+Arg_conc.+emission_O2+emission_CO2+consum_O2+generate_CO2; 0.157, 0.574, tmp_cumulo+pH+pH_cumulo+PL_cumulo+Feed_Vol+RS_cumulo+Cell_conc._interval+Arg_conc.+emission_O2+interval_O2+generate_CO2; 0.137, 0.573, tmp+pH_cumulo+PL_cumulo+AN_cumulo+Feed_Vol+RS_cumulo+Cell_conc._interval+Arg_conc.+emission_O2+emission_CO2+interval_O2+generate_CO2; 0.157, 0.573, tmp_cumulo+pH+PL_cumulo+AN+Feed_Vol+RS_cumulo+Cell_conc._interval+Arg_conc.+emission_O2+consum_O2+interval_O2; 0.157, 0.573, tmp_cumulo+pH+PL_cumulo+AN_cumulo+Feed_Vol+RS_cumulo+Cell_conc._interval+Arg_conc.+emission_O2+emission_CO2+consum_O2+interval_O2; 0.137, 0.573, tmp+tmp_cumulo+pH+PL_cumulo+AN_cumulo+Feed_Vol+RS_cumulo+Cell_conc._interval+Arg_conc.+emission_O2+consum_O2+interval_O2; 0.176, 0.573, tmp_cumulo+pH+PL+PL_cumulo+RS_cumulo+Cell_conc._interval+RQ_integral+Arg_conc.+emission_CO2+interval_O2; 0.137, 0.573, tmp_cumulo+PL_cumulo+AN_cumulo+interval_yield+Feed_Vol+RS_cumulo+Cell_conc._interval+RQ_integral+Arg_conc.+emission_CO2+interval_O2+generate_CO2; 0.157, 0.573, tmp_cumulo+pH+pH_cumulo+PL_cumulo+RS_cumulo+Cell_conc._interval+rab_integral+Arg_conc.+emission_CO2+interval_O2+generate_CO2; 0.157, 0.573, tmp_cumulo+pH_cumulo+PL_cumulo+Feed_Vol+RS_cumulo+Cell_conc._interval+rab_integral+Arg_conc.+emission_O2+emission_CO2+interval_O2; 0.157, 0.573, tmp+PL_cumulo+AN_cumulo+RS+Feed_Vol+RS_cumulo+Cell_conc._interval+Arg_conc.+emission_O2+consum_O2+generate_CO2; 0.157, 0.573, tmp_cumulo+pH_cumulo+PL_cumulo+AN_cumulo+RS_cumulo+Cell_conc._interval+rab_integral+Arg_conc.+emission_CO2+consum_O2+interval_O2; 0.157, 0.573, tmp_cumulo+pH_cumulo+PL_cumulo+Feed_Vol+RS_cumulo+Cell_conc._interval+RQ_integral+Arg_conc.+emission_O2+consum_O2+interval_O2; 0.157, 0.573, tmp_cumulo+PL_cumulo+AN_cumulo+Feed_Vol+RS_cumulo+Cell_conc._interval+RQ_integral+Arg_conc.+emission_O2+consum_O2+interval_O2; 0.137, 0.573, tmp_cumulo+pH+PL_cumulo+AN_cumulo+interval_yield+Feed_Vol+RS_cumulo+Cell_conc._interval+Arg_conc.+emission_O2+interval_O2+generate_CO2; 0.137, 0.573, tmp_cumulo+pH+pH_cumulo+PL_cumulo+AN_cumulo+Cell_conc._interval+RQ_integral+Arg_conc.+emission_CO2+interval_O2; 0.157, 0.573, tmp+pH+PL_cumulo+AN_cumulo+Feed_Vol+RS_cumulo+Cell_conc._interval+Arg_conc.+emission_O2+consum_O2+generate_CO2; 0.157, 0.573, tmp+pH+PL_cumulo+AN_cumulo+RS+Feed_Vol+Cell_conc._interval+Arg_conc.+emission_O2+interval_O2+generate_CO2; 0.194, 0.573, tmp_cumulo+PL_cumulo+AN_cumulo+RS_cumulo+Cell_conc._interval+RQ_integral+Arg_conc.+emission_CO2+interval_O2; 0.157, 0.573, tmp_cumulo+pH+PL_cumulo+Feed_Vol+RS_cumulo+Cell_conc._interval+rab_integral+RQ_integral+Arg_conc.+emission_CO2+interval_O2; 0.157, 0.573, tmp+tmp_cumulo+PL_cumulo+AN_cumulo+Feed_Vol+RS_cumulo+Cell_conc._interval+Arg_conc.+emission_O2+interval_O2+generate_CO2; 0.156, 0.573, tmp_cumulo+PL_cumulo+AN_cumulo+interval_yield+Feed_Vol+RS_cumulo+Cell_conc._interval+RQ_integral+Arg_conc.+emission_CO2+interval_O2; 0.176, 0.573, tmp+pH+PL_cumulo+RS+Feed_Vol+Cell_conc._interval+Arg_conc.+emission_O2+interval_O2+generate_CO2; 0.175, 0.573, tmp_cumulo+pH+PL_cumulo+interval_yield+Feed_Vol+RS_cumulo+Cell_conc._interval+Arg_conc.+emission_O2+interval_O2; 0.136, 0.573, tmp_cumulo+pH+PL_cumulo+AN_cumulo+RS+RS_cumulo+Cell_conc._cumulo+Cell_conc._interval+rab_integral+Arg_conc.+emission_CO2+interval_O2; 0.136, 0.573, tmp+pH_cumulo+PL_cumulo+AN_cumulo+Feed_Vol+RS_cumulo+Cell_conc._interval+Arg_conc.+emission_O2+emission_CO2+consum_O2+interval_O2; 0.156, 0.573, tmp_cumulo+pH+PL_cumulo+AN+RS+RS_cumulo+Cell_conc._interval+rab_integral+Arg_conc.+emission_CO2+interval_O2; 0.156, 0.573, tmp_cumulo+PL_cumulo+AN_cumulo+RS+RS_cumulo+Cell_conc._interval+rab_integral+Arg_conc.+emission_CO2+interval_O2+generate_CO2; 0.175, 0.573, tmp+pH+Feed_Vol+RS_cumulo+Cell_conc._interval+rab_integral+Arg_conc.+emission_CO2+interval_O2+generate_CO2; 0.211, 0.573, tmp_cumulo+pH+PL_cumulo+RS_cumulo+Cell_conc._interval+Arg_conc.+emission_CO2+interval_O2; 0.156, 0.573, tmp_cumulo+PL_cumulo+AN_cumulo+RS+Feed_Vol+RS_cumulo+Cell_conc._interval+rab_integral+Arg_conc.+emission_CO2+interval_O2; 0.156, 0.573, tmp_cumulo+pH_cumulo+PL+PL_cumulo+Feed_Vol+RS_cumulo+Cell_conc._interval+rab_integral+Arg_conc.+emission_CO2+interval_O2; 0.136, 0.573, tmp_cumulo+pH_cumulo+PL_cumulo+AN_cumulo+Feed_Vol+RS_cumulo+Cell_conc._interval+rab_integral+Arg_conc.+emission_O2+consum_O2+interval_O2; 0.175, 0.573, tmp+PL+PL_cumulo+RS+Feed_Vol+Cell_conc._interval+Arg_conc.+emission_O2+consum_O2+generate_CO2; 0.194, 0.573, tmp+PL_cumulo+AN_cumulo+RS_cumulo+Cell_conc._interval+rab_integral+Arg_conc.+emission_CO2+interval_O2; 0.136, 0.573, tmp_cumulo+pH_cumulo+PL_cumulo+AN_cumulo+Feed_Vol+RS_cumulo+Cell_conc._interval+rab_integral+Arg_conc.+emission_CO2+consum_O2+interval_O2; 0.175, 0.573, tmp+PL_cumulo+AN_cumulo+Feed_Vol+Cell_conc._interval+Arg_conc.+emission_O2+ emission_CO2+consum_O2+generate_CO2; 0.136, 0.573, tmp_cumulo+pH+PL_cumulo+AN+AN_cumulo+Feed_Vol+RS_cumulo+Cell_conc._interval+rab_integral+Arg_conc.+emission_CO2+interval_O2; 0.136, 0.573, tmp_cumulo+pH_cumulo+PL_cumulo+AN_cumulo+interval_yield+Feed_Vol+RS_cumulo+Cell_conc._interval+rab_integral+Arg_conc.+emission_CO2+interval_O2; 0.136, 0.573, tmp+pH+PL+PL_cumulo+AN_cumulo+Feed_Vol+RS_cumulo+Cell_conc._interval+Arg_conc.+emission_O2+consum_O2+interval_O2; 0.156, 0.573, tmp+tmp_cumulo+pH+PL_cumulo+Feed_Vol+RS_cumulo+Cell_conc._interval+rab_integral+Arg_conc.+emission_CO2+interval_O2; 0.175, 0.573, tmp_cumulo+PL+PL_cumulo+RS+RS_cumulo+Cell_conc._interval+rab_integral+Arg_conc.+emission_CO2+interval_O2; 0.156, 0.573, tmp+pH+PL_cumulo+Feed_Vol+RS_cumulo+Cell_conc._interval+Arg_conc.+emission_O2+emission_CO2+consum_O2+interval_O2; 0.156, 0.573, tmp+PL_cumulo+AN_cumulo+interval_yield+Feed_Vol+RS_cumulo+Cell_conc._interval+Arg_conc.+emission_O2+consum_O2+generate_CO2; 0.193, 0.573, tmp_cumulo+PL_cumulo+RS_cumulo+Cell_conc._interval+RQ_integral+Arg_conc.+emission_CO2+interval_O2+generate_CO2; 0.136, 0.572, tmp+PL_cumulo+AN_cumulo+Feed_Vol+RS_cumulo+Cell_conc._interval+rab_integral+Arg_conc.+emission_O2+emission_CO2+interval_O2+generate_CO2; 0.175, 0.572, tmp_cumulo+pH+PL_cumulo+RS_cumulo+Cell_conc._interval+rab_integral+RQ_integral+Arg_conc.+emission_CO2+interval_O2; 0.156, 0.572, tmp_cumulo+pH+PL_cumulo+Feed_Vol+RS_cumulo+Cell_conc._interval+Arg_conc.+emission_O2+consum_O2+interval_O2+generate_CO2; 0.156, 0.572, tmp_cumulo+PL_cumulo+AN_cumulo+RS+Feed_Vol+RS_cumulo+Cell_conc._interval+Arg_conc.+emission_O2+consum_O2+interval_O2; 0.156, 0.572, tmp+pH+PL_cumulo+RS+Feed_Vol+RS_cumulo+Cell_conc._interval+Arg_conc.+emission_O2+interval_O2+generate_CO2; 0.175, 0.572, tmp_cumulo+PL_cumulo+RS+RS_cumulo+Cell_conc._interval+rab_integral+Arg_conc.+emission_CO2+consum_O2+interval_O2; 0.156, 0.572, tmp_cumulo+PL+PL_cumulo+AN_cumulo+RS+RS_cumulo+Cell_conc._interval+rab_integral+Arg_conc.+emission_CO2+interval_O2; 0.156, 0.572, tmp+pH_cumulo+PL_cumulo+AN_cumulo+RS+Feed_Vol+Cell_conc._interval+Arg_conc.+emission_O2+interval_O2+generate_CO2; 0.156, 0.572, tmp_cumulo+PL_cumulo+RS+Feed_Vol+RS_cumulo+Cell_conc._interval+RQ_integral+Arg_conc.+emission_CO2+interval_O2+generate_CO2; 0.155, 0.572, tmp+pH_cumulo+PL_cumulo+Feed_Vol+RS_cumulo+Cell_conc._interval+Arg_conc.+emission_O2+emission_CO2+consum_O2+interval_O2; 0.175, 0.572, tmp_cumulo+pH_cumulo+PL_cumulo+RS_cumulo+Cell_conc._interval+rab_integral+Arg_conc.+emission_O2+emission_CO2+interval_O2; 0.155, 0.572, tmp_cumulo+pH_cumulo+PL_cumulo+Feed_Vol+RS_cumulo+Cell_conc._interval+RQ_integral+Arg_conc.+emission_CO2+interval_O2+generate_CO2; 0.135, 0.572, tmp_cumulo+pH_cumulo+PL_cumulo+AN_cumulo+Feed_Vol+RS_cumulo+Cell_conc._interval+rab_integral+Arg_conc.+emission_CO2+interval_O2+generate_CO2; 0.135, 0.572, tmp_cumulo+pH+PL_cumulo+AN_cumulo+Feed_Vol+RS_cumulo+Cell_conc._interval+RQ_integral+Arg_conc.+emission_CO2+interval_O2+generate_CO2; 0.174, 0.572, tmp_cumulo+PL_cumulo+Feed_Vol+RS_cumulo+Cell_conc._interval+rab_integral+Arg_conc.+emission_O2+consum_O2+interval_O2; 0.135, 0.572, tmp_cumulo+pH_cumulo+PL_cumulo+AN_cumulo+Feed_Vol+RS_cumulo+Cell_conc._interval+rab_integral+Arg_conc.+emission_CO2+interval_O2; 0.155, 0.572, tmp_cumulo+PL_cumulo+AN_cumulo+RS+RS_cumulo+Cell_conc._interval+rab_integral+Arg_conc.+emission_CO2+interval_O2;

CO2+interval_O2; 0.174, 0.572, tmp_cumulo+PL_cumulo+interval_yield+Feed_Vol+RS_cumulo+Cell_conc._interval+Arg_conc.+emission_O2+consum_O2+interval_O2; 0.135, 0.572, tmp_cumulo+pH+pH_cumulo+PL_cumulo+AN_cumulo+RS+RS_cumulo+Cell_conc._interval+rab_integral+Arg_conc.+emission_CO2+interval_O2; 0.155, 0.572, tmp+PL+PL_cumulo+Feed_Vol+RS_cumulo+Cell_conc._interval+RQ_integral+Arg_conc.+emission_O2+interval_O2+generate_CO2; 0.155, 0.572, tmp+PL_cumulo+Feed_Vol+RS_cumulo+Cell_conc._interval+rab_integral+Arg_conc.+emission_O2+emission_CO2+consum_O2+generate_CO2; 0.135, 0.572, tmp+pH+PL+PL_cumulo+AN_cumulo+Feed_Vol+RS_cumulo+Cell_conc._interval+Arg_conc.+emission_O2+interval_O2+generate_CO2; 0.174, 0.572, tmp_cumulo+PL_cumulo+Feed_Vol+RS_cumulo+Cell_conc._interval+rab_integral+Arg_conc.+emission_O2+consum_O2+generate_CO2; 0.135, 0.572, tmp_cumulo+pH_cumulo+PL_cumulo+AN_cumulo+RS_cumulo+Cell_conc._interval+RQ_integral+Arg_conc.+emission_O2+consum_O2+interval_O2; 0.135, 0.572, tmp_cumulo+pH+PL_cumulo+AN_cumulo+RS+Feed_Vol+RS_cumulo+Cell_conc._interval+RQ_integral+Arg_conc.+emission_CO2+interval_O2; 0.155, 0.572, tmp_cumulo+pH_cumulo+PL_cumulo+Feed_Vol+RS_cumulo+Cell_conc._interval+RQ_integral+Arg_conc.+emission_O2+emission_CO2+interval_O2; 0.174, 0.572, tmp_cumulo+pH+PL_cumulo+RS_cumulo+Cell_conc._cumulo+Cell_conc._interval+RQ_integral+Arg_conc.+emission_CO2+interval_O2; 0.155, 0.572, tmp_cumulo+PL_cumulo+interval_yield+Feed_Vol+RS_cumulo+Cell_conc._interval+Arg_conc.+emission_O2+emission_CO2+interval_O2+generate_CO2; 0.135, 0.572, tmp_cumulo+pH_cumulo+PL+PL_cumulo+AN_cumulo+Feed_Vol+RS_cumulo+Cell_conc._interval+RQ_integral+Arg_conc.+emission_CO2+interval_O2; 0.135, 0.572, tmp+PL+PL_cumulo+AN_cumulo+RS+Feed_Vol+RS_cumulo+Cell_conc._interval+Arg_conc.+emission_O2+interval_O2+generate_CO2; 0.155, 0.572, tmp_cumulo+PL+PL_cumulo+AN_cumulo+Feed_Vol+RS_cumulo+Cell_conc._interval+Arg_conc.+emission_O2+interval_O2+generate_CO2; 0.192, 0.572, tmp+PL_cumulo+RS_cumulo+Cell_conc._interval+rab_integral+Arg_conc.+emission_CO2+interval_O2+generate_CO2; 0.155, 0.572, tmp+pH+PL_cumulo+Feed_Vol+RS_cumulo+Cell_conc._interval+Arg_conc.+emission_O2+emission_CO2+consum_O2+generate_CO2; 0.155, 0.572, tmp+tmp_cumulo+pH+PL_cumulo+Feed_Vol+RS_cumulo+Cell_conc._interval+Arg_conc.+emission_O2+consum_O2+interval_O2; 0.155, 0.572, tmp_cumulo+PL_cumulo+AN_cumulo+Feed_Vol+RS_cumulo+Cell_conc._interval+rab_integral+Arg_conc.+emission_CO2+interval_O2+generate_CO2; 0.154, 0.572, tmp_cumulo+pH_cumulo+PL_cumulo+RS+Feed_Vol+RS_cumulo+Cell_conc._interval+RQ_integral+Arg_conc.+emission_CO2+interval_O2; 0.154, 0.572, tmp+PL_cumulo+AN_cumulo+Feed_Vol+RS_cumulo+Cell_conc._interval+RQ_integral+Arg_conc.+emission_O2+consum_O2+interval_O2; 0.154, 0.572, tmp+tmp_cumulo+pH_cumulo+PL_cumulo+Feed_Vol+RS_cumulo+Cell_conc._interval+rab_integral+Arg_conc.+emission_CO2+interval_O2; 0.154, 0.572, tmp_cumulo+PL+PL_cumulo+interval_yield+Feed_Vol+RS_cumulo+Cell_conc._interval+RQ_integral+Arg_conc.+emission_CO2+interval_O2; 0.154, 0.572, tmp_cumulo+pH+PL_cumulo+interval_yield+RS+RS_cumulo+Cell_conc._interval+rab_integral+Arg_conc.+emission_CO2+interval_O2; 0.174, 0.572, tmp_cumulo+PL_cumulo+Feed_Vol+RS_cumulo+Cell_conc._interval+RQ_integral+Arg_conc.+emission_O2+consum_O2+generate_CO2; 0.174, 0.571, tmp_cumulo+PL_cumulo+Feed_Vol+RS_cumulo+Cell_conc._interval+rab_integral+Arg_conc.+emission_CO2+consum_O2+generate_CO2;

0.154, 0.571, tmp_cumulo+pH+PL_cumulo+AN+RS_cumulo+Cell_conc._interval+rab_integral+Arg_conc.+emission_CO2+interval_O2+generate_CO2; 0.134, 0.571, tmp+pH_cumulo+PL+PL_cumulo+AN_cumulo+Feed_Vol+RS_cumulo+Cell_conc._interval+Arg_conc.+emission_O2+interval_O2+generate_CO2; 0.192, 0.571, tmp_cumulo+PL_cumulo+RS_cumulo+Cell_conc._interval+RQ_integral+Arg_conc.+emission_O2+emission_CO2+interval_O2; 0.154, 0.571, tmp_cumulo+pH+PL+PL_cumulo+Feed_Vol+RS_cumulo+Cell_conc._interval+Arg_conc.+emission_O2+interval_O2+generate_CO2; 0.154, 0.571, tmp+PL_cumulo+AN_cumulo+RS+Feed_Vol+Cell_conc._interval+Arg_conc.+emission_O2+emission_CO2+consum_O2+generate_CO2; 0.154, 0.571, tmp+PL+PL_cumulo+Feed_Vol+RS_cumulo+Cell_conc._interval+rab_integral+Arg_conc.+emission_O2+interval_O2+generate_CO2; 0.173, 0.571, tmp+tmp_cumulo+PL_cumulo+Feed_Vol+RS_cumulo+Cell_conc._interval+Arg_conc.+emission_O2+consum_O2+generate_CO2; 0.192, 0.571, tmp+PL+PL_cumulo+RS_cumulo+Cell_conc._interval+rab_integral+Arg_conc.+emission_CO2+interval_O2; 0.192, 0.571, tmp_cumulo+pH+PL_cumulo+RS_cumulo+Cell_conc._interval+Arg_conc.+emission_O2+interval_O2+generate_CO2; 0.154, 0.571, tmp+PL_cumulo+interval_yield+Feed_Vol+RS_cumulo+Cell_conc._interval+Arg_conc.+emission_O2+emission_CO2+interval_O2+generate_CO2; 0.154, 0.571, tmp_cumulo+pH+PL_cumulo+AN_cumulo+RS_cumulo+Cell_conc._interval+rab_integral+Arg_conc.+emission_O2+emission_CO2+interval_O2; 0.173, 0.571, tmp+PL_cumulo+AN_cumulo+RS+RS_cumulo+Cell_conc._interval+rab_integral+Arg_conc.+emission_CO2+interval_O2; 0.209, 0.571, tmp_cumulo+pH_cumulo+PL_cumulo+RS_cumulo+Cell_conc._interval+Arg_conc.+emission_O2+interval_O2; 0.173, 0.571, tmp+pH+PL_cumulo+RS+RS_cumulo+Cell_conc._interval+rab_integral+Arg_conc.+emission_CO2+interval_O2; 0.134, 0.571, tmp+pH+PL_cumulo+AN_cumulo+RS+Feed_Vol+RS_cumulo+Cell_conc._interval+Arg_conc.+emission_O2+interval_O2+generate_CO2; 0.173, 0.571, tmp+PL_cumulo+AN+Feed_Vol+RS_cumulo+Cell_conc._interval+Arg_conc.+emission_O2+interval_O2+generate_CO2; 0.154, 0.571, tmp+tmp_cumulo+pH+PL_cumulo+Feed_Vol+RS_cumulo+Cell_conc._interval+Arg_conc.+emission_O2+interval_O2+generate_CO2; 0.134, 0.571, tmp+tmp_cumulo+pH+PL_cumulo+AN_cumulo+Feed_Vol+RS_cumulo+Cell_conc._interval+rab_integral+Arg_conc.+emission_CO2+interval_O2; 0.209, 0.571, tmp+PL_cumulo+Feed_Vol+RS_cumulo+Cell_conc._interval+Arg_conc.+emission_O2+interval_O2; 0.134, 0.571, tmp+pH_cumulo+PL+PL_cumulo+AN_cumulo+Feed_Vol+RS_cumulo+Cell_conc._interval+Arg_conc.+emission_O2+consum_O2+interval_O2; 0.173, 0.571, tmp_cumulo+pH+pH_cumulo+PL_cumulo+RS_cumulo+Cell_conc._interval+RQ_integral+Arg_conc.+emission_CO2+interval_O2; 0.173, 0.571, tmp_cumulo+pH+PL+PL_cumulo+Feed_Vol+RS_cumulo+Cell_conc._interval+Arg_conc.+emission_O2+interval_O2; 0.154, 0.571, tmp+PL_cumulo+RS+Feed_Vol+RS_cumulo+Cell_conc._interval+Arg_conc.+emission_O2+emission_CO2+interval_O2+generate_CO2; 0.154, 0.571, tmp_cumulo+pH+PL_cumulo+AN_cumulo+Feed_Vol+RS_cumulo+Cell_conc._interval+RQ_integral+Arg_conc.+emission_O2+interval_O2; 0.173, 0.571, tmp+PL_cumulo+AN_cumulo+Feed_Vol+RS_cumulo+Cell_conc._interval+rab_integral+Arg_conc.+emission_CO2+interval_O2; 0.191, 0.571, tmp_cumulo+pH_cumulo+PL_cumulo+Feed_Vol+RS_cumulo+Cell_conc._interval+RQ_integral+Arg_conc.+interval_O2; 0.191, 0.571, tmp+PL_cumulo+Feed_Vol+RS_cumulo+Cell_conc._interval+RQ_integral+Arg_conc.+emission_O2+interval_O2; 0.153, 0.571, tmp_cumulo+PL_cumulo+RS+Feed_Vol+RS_cumulo+Cell_conc._interval+Arg_conc.+emission_O2+emission_CO2+interval_O2+generate_CO2; 0.153, 0.571, tmp+PL_cumulo+interval_yield+Feed_Vol+RS_cumulo+Cell_conc._interval+Arg_conc.+emission_O2+emission_CO2+consum_O2+generate_CO2; 0.133, 0.571, tmp_cumulo+pH_cumulo+PL_cumulo+AN_cumulo+interval_yield+Feed_Vol+RS_cumulo+Cell_conc._interval+Arg_conc.+emission_O2+interval_O2+generate_CO2; 0.153, 0.571, tmp_cumulo+PL_cumulo+RS+Feed_Vol+RS_cumulo+Cell_conc._interval+rab_integral+Arg_conc.+emission_CO2+interval_O2+generate_CO2; 0.133, 0.571, tmp_cumulo+pH+PL_cumulo+AN_cumulo+Feed_Vol+RS_cumulo+Cell_conc._interval+rab_integral+RQ_integral+Arg_conc.+emission_CO2+interval_O2; 0.153, 0.571, tmp+PL_cumulo+Feed_Vol+RS_cumulo+Cell_conc._interval+RQ_integral+Arg_conc.+emission_O2+emission_CO2+interval_O2+generate_CO2; 0.153, 0.571, tmp+PL_cumulo+AN_cumulo+Feed_Vol+RS_cumulo+Cell_conc._interval+RQ_integral+Arg_conc.+emission_CO2+consum_O2+generate_CO2; 0.153, 0.571, tmp+tmp_cumulo+PL_cumulo+Feed_Vol+RS_cumulo+Cell_conc._interval+RQ_integral+Arg_conc.+emission_CO2+interval_O2+generate_CO2; 0.153, 0.571, tmp+PL_cumulo+AN_cumulo+Feed_Vol+RS_cumulo+Cell_conc._interval+rab_integral+Arg_conc.+emission_O2+consum_O2+interval_O2; 0.133, 0.571, tmp_cumulo+pH_cumulo+PL_cumulo+AN_cumulo+RS+Feed_Vol+RS_cumulo+Cell_conc._interval+rab_integral+Arg_conc.+emission_CO2+interval_O2; 0.153, 0.571, tmp+tmp_cumulo+pH_cumulo+PL_cumulo+Feed_Vol+RS_cumulo+Cell_conc._interval+RQ_integral+Arg_conc.+emission_CO2+interval_O2; 0.153, 0.571, tmp+pH_cumulo+PL_cumulo+AN_cumulo+Feed_Vol+RS_cumulo+Cell_conc._interval+rab_integral+Arg_conc.+emission_CO2+interval_O2; 0.153, 0.571, tmp_cumulo+PL_cumulo+Feed_Vol+RS_cumulo+Cell_conc._interval+rab_integral+RQ_integral+Arg_conc.+emission_CO2+consum_O2+interval_O2; 0.172, 0.570, tmp+PL_cumulo+AN+Feed_Vol+RS_cumulo+Cell_conc._interval+Arg_conc.+emission_O2+consum_O2+generate_CO2; 0.153, 0.570, tmp_cumulo+PL_cumulo+Feed_Vol+RS_cumulo+Cell_conc._interval+RQ_integral+Arg_conc.+emission_O2+emission_CO2+consum_O2+interval_O2; 0.153, 0.570, tmp+PL_cumulo+AN_cumulo+Feed_Vol+RS_cumulo+Cell_conc._interval+rab_integral+Arg_conc.+emission_CO2+interval_O2+generate_CO2; 0.172, 0.570, tmp+PL+PL_cumulo+Feed_Vol+RS_cumulo+Cell_conc._interval+Arg_conc.+emission_O2+consum_O2+interval_O2; 0.153, 0.570, tmp_cumulo+PL_cumulo+Feed_Vol+RS_cumulo+Cell_conc._interval+RQ_integral+Arg_conc.+emission_CO2+consum_O2+interval_O2+generate_CO2; 0.133, 0.570, tmp+pH+PL_cumulo+AN_cumulo+RS+Feed_Vol+RS_cumulo+Cell_conc._interval+Arg_conc.+emission_O2+consum_O2+interval_O2; 0.153, 0.570, tmp+pH_cumulo+PL_cumulo+AN_cumulo+Feed_Vol+RS_cumulo+Cell_conc._interval+Arg_conc.+emission_O2+consum_O2+generate_CO2; 0.172, 0.570, tmp+pH_cumulo+PL_cumulo+RS+Feed_Vol+Cell_conc._interval+Arg_conc.+emission_O2+consum_O2+generate_CO2; 0.172, 0.570, tmp+PL_cumulo+RS+Feed_Vol+Cell_conc._interval+rab_integral+Arg_conc.+emission_O2+consum_O2+generate_CO2; 0.153, 0.570, tmp_cumulo+PL_cumulo+interval_yield+Feed_Vol+RS_cumulo+Cell_conc._interval+RQ_integral+Arg_conc.+emission_CO2+consum_O2+interval_O2; 0.172, 0.570, tmp_cumulo+pH_cumulo+PL_cumulo+AN_cumulo+Feed_Vol+RS_cumulo+Cell_conc._interval+Arg_conc.+emission_O2+interval_O2; 0.172, 0.570, tmp_cumulo+pH+PL_cumulo+AN+RS_cumulo+Cell_conc._interval+RQ_integral+Arg_conc.+emission_CO2+interval_O2; 0.172, 0.570, tmp+PL_cumulo+

RS+Feed_Vol+Cell_conc._interval+Arg_conc.+emission_O2+emission_CO2+interval_O2+generate_CO2; 0.152, 0.570, tmp+pH+PL_cumulo+AN_cumulo+Feed_Vol+RS_cumulo+Cell_conc._interval+RQ_integral+Arg_conc.+emission_CO2+interval_O2; 0.152, 0.570, tmp_cumulo+pH_cumulo+PL+PL_cumulo+RS_cumulo+Cell_conc._interval+rab_integral+Arg_conc.+emission_CO2+interval_O2+generate_CO2; 0.132, 0.570, tmp_cumulo+pH_cumulo+PL+PL_cumulo+AN_cumulo+Feed_Vol+RS_cumulo+Cell_conc._interval+Arg_conc.+emission_O2+consum_O2+interval_O2; 0.172, 0.570, tmp_cumulo+pH+PL_cumulo+OD+RS_cumulo+Cell_conc._interval+rab_integral+Arg_conc.+emission_CO2+interval_O2; 0.171, 0.570, tmp_cumulo+pH+pH_cumulo+PL_cumulo+Feed_Vol+RS_cumulo+Cell_conc._interval+Arg_conc.+emission_O2+interval_O2; 0.152, 0.570, tmp_cumulo+pH+PL_cumulo+AN+Feed_Vol+RS_cumulo+Cell_conc._interval+Arg_conc.+emission_O2+interval_O2+generate_CO2; 0.152, 0.570, tmp_cumulo+PL_cumulo+interval_yield+RS+Feed_Vol+RS_cumulo+Cell_conc._interval+Arg_conc.+emission_O2+interval_O2+generate_CO2; 0.132, 0.570, tmp_cumulo+pH+PL_cumulo+AN_cumulo+Feed_Vol+RS_cumulo+Cell_conc._interval+RQ_integral+Arg_conc.+emission_CO2+emission_CO2+interval_O2; 0.132, 0.570, tmp_cumulo+PL_cumulo+AN_cumulo+RS+Feed_Vol+RS_cumulo+Cell_conc._interval+rab_integral+Arg_conc.+emission_CO2+interval_O2+generate_CO2; 0.152, 0.570, tmp+PL_cumulo+Feed_Vol+RS_cumulo+Cell_conc._interval+Arg_conc.+emission_O2+emission_CO2+consum_O2+interval_O2+generate_CO2; 0.190, 0.570, tmp+pH_cumulo+PL_cumulo+Feed_Vol+RS_cumulo+Cell_conc._interval+Arg_conc.+emission_O2+interval_O2; 0.132, 0.570, tmp_cumulo+pH+PL+PL_cumulo+AN_cumulo+RS_cumulo+Cell_conc._interval+rab_integral+Arg_conc.+emission_CO2+interval_O2+generate_CO2; 0.190, 0.570, tmp_cumulo+pH_cumulo+PL_cumulo+RS_cumulo+Cell_conc._interval+Arg_conc.+emission_O2+consum_O2+interval_O2; 0.171, 0.570, tmp_cumulo+pH_cumulo+PL_cumulo+interval_yield+Feed_Vol+RS_cumulo+Cell_conc._interval+rab_integral+Arg_conc.+interval_O2; 0.132, 0.570, tmp_cumulo+PL+PL_cumulo+AN_cumulo+Feed_Vol+RS_cumulo+Cell_conc._interval+RQ_integral+Arg_conc.+emission_O2+emission_CO2+interval_O2; 0.152, 0.570, tmp_cumulo+pH_cumulo+PL_cumulo+AN+Feed_Vol+RS_cumulo+Cell_conc._interval+rab_integral+Arg_conc.+emission_CO2+interval_O2; 0.171, 0.570, tmp_cumulo+PL+PL_cumulo+Feed_Vol+RS_cumulo+Cell_conc._interval+Arg_conc.+emission_O2+consum_O2+generate_CO2; 0.152, 0.570, tmp_cumulo+pH+PL_cumulo+AN_cumulo+RS_cumulo+Cell_conc._interval+rab_integral+RQ_integral+Arg_conc.+emission_CO2+interval_O2; 0.152, 0.570, tmp_cumulo+PL_cumulo+interval_yield+Feed_Vol+RS_cumulo+Cell_conc._interval+RQ_integral+Arg_conc.+emission_O2+interval_O2+generate_CO2; 0.152, 0.570, tmp+pH_cumulo+PL_cumulo+RS+Feed_Vol+Cell_conc._interval+Arg_conc.+emission_O2+emission_CO2+interval_O2+generate_CO2; 0.132, 0.570, tmp_cumulo+pH+PL+PL_cumulo+AN_cumulo+Feed_Vol+RS_cumulo+Cell_conc._interval+Arg_conc.+emission_O2+interval_O2+generate_CO2; 0.152, 0.570, tmp+PL_cumulo+AN_cumulo+Feed_Vol+RS_cumulo+Cell_conc._interval+RQ_integral+Arg_conc.+emission_CO2+consum_O2+interval_O2; 0.152, 0.570, tmp_cumulo+pH_cumulo+PL_cumulo+AN_cumulo+interval_yield+RS_cumulo+Cell_conc._interval+rab_integral+Arg_conc.+emission_CO2+interval_O2; 0.189, 0.570, tmp_cumulo+pH+PL_cumulo+RS+RS_cumulo+Cell_conc._interval+Arg_conc.+emission_O2+interval_O2; 0.207, 0.570, tmp+pH+PL_cumulo+RS_cumulo+Cell_conc._interval+Arg_conc.+emission_O2+interval_O2; 0.131, 0.570, tmp_cumulo+pH_cumulo+PL_cumulo+AN_cumulo+Feed_Vol+RS_cumulo+Cell_conc._interval+Arg_conc.+emission_O2+emission_CO2+interval_O2+generate_CO2; 0.171, 0.570, tmp+PL_cumulo+Feed_Vol+RS_cumulo+Cell_conc._interval+RQ_integral+Arg_conc.+emission_CO2+consum_O2+interval_O2; 0.131, 0.570, tmp+PL+PL_cumulo+AN_cumulo+Feed_Vol+RS_cumulo+Cell_conc._interval+Arg_conc.+emission_O2+emission_CO2+consum_O2+generate_CO2; 0.152, 0.570, tmp+tmp_cumulo+PL+PL_cumulo+Feed_Vol+RS_cumulo+Cell_conc._interval+RQ_integral+Arg_conc.+emission_CO2+interval_O2; 0.152, 0.570, tmp+PL_cumulo+RS+Feed_Vol+RS_cumulo+Cell_conc._interval+Arg_conc.+emission_O2+emission_CO2+consum_O2+generate_CO2; 0.171, 0.570, tmp_cumulo+pH+PL_cumulo+RS_cumulo+Cell_conc._interval+RQ_integral+Arg_conc.+emission_CO2+interval_O2+generate_CO2; 0.189, 0.569, tmp+PL_cumulo+Feed_Vol+Cell_conc._interval+RQ_integral+Arg_conc.+emission_O2+consum_O2+generate_CO2; 0.151, 0.569, tmp+pH_cumulo+PL_cumulo+Feed_Vol+RS_cumulo+Cell_conc._interval+Arg_conc.+emission_O2+emission_CO2+consum_O2+generate_CO2; 0.131, 0.569, tmp+PL_cumulo+AN_cumulo+interval_yield+Feed_Vol+RS_cumulo+Cell_conc._interval+Arg_conc.+emission_O2+emission_CO2+interval_O2+generate_CO2; 0.151, 0.569, tmp+PL_cumulo+AN_cumulo+RS+Feed_Vol+RS_cumulo+Cell_conc._interval+Arg_conc.+emission_O2+consum_O2+interval_O2; 0.189, 0.569, tmp+PL_cumulo+AN_cumulo+Feed_Vol+Cell_conc._interval+Arg_conc.+emission_O2+interval_O2+generate_CO2; 0.151, 0.569, tmp_cumulo+pH_cumulo+PL_cumulo+Feed_Vol+RS_cumulo+Cell_conc._interval+rab_integral+Arg_conc.+emission_O2+interval_O2+generate_CO2; 0.189, 0.569, tmp+PL_cumulo+Feed_Vol+RS_cumulo+Cell_conc._interval+rab_integral+Arg_conc.+emission_O2+interval_O2; 0.131, 0.569, tmp+PL_cumulo+AN_cumulo+RS+Feed_Vol+RS_cumulo+Cell_conc._interval+Arg_conc.+emission_O2+emission_CO2+interval_O2+generate_CO2; 0.110, 0.569, tmp_cumulo+pH+PL_cumulo+AN_cumulo+RS+Feed_Vol+RS_cumulo+Cell_conc._interval+Arg_conc.+emission_O2+emission_CO2+consum_O2+interval_O2; 0.189, 0.569, tmp_cumulo+PL_cumulo+RS_cumulo+Cell_conc._interval+RQ_integral+Arg_conc.+emission_CO2+consum_O2+interval_O2; 0.151, 0.569, tmp+tmp_cumulo+pH_cumulo+PL_cumulo+Feed_Vol+RS_cumulo+Cell_conc._interval+Arg_conc.+emission_O2+consum_O2+interval_O2; 0.151, 0.569, tmp+pH+PL_cumulo+interval_yield+Feed_Vol+RS_cumulo+Cell_conc._interval+Arg_conc.+emission_O2+interval_O2+generate_CO2; 0.151, 0.569, tmp_cumulo+pH+PL+PL_cumulo+RS_cumulo+Cell_conc._interval+rab_integral+Arg_conc.+emission_CO2+consum_O2+interval_O2; 0.151, 0.569, tmp_cumulo+PL_cumulo+AN_cumulo+Feed_Vol+RS_cumulo+Cell_conc._interval+RQ_integral+Arg_conc.+emission_CO2+consum_O2+generate_CO2; 0.151, 0.569, tmp_cumulo+pH+PL_cumulo+AN_cumulo+Feed_Vol+RS_cumulo+Cell_conc._interval+Arg_conc.+emission_O2+emission_CO2+interval_O2; 0.151, 0.569, tmp_cumulo+pH+PL_cumulo+Feed_Vol+RS_cumulo+Cell_conc._interval+RQ_integral+Arg_conc.+emission_O2+interval_O2+generate_CO2; 0.131, 0.569, tmp_cumulo+PL_cumulo+AN_cumulo+RS+Feed_Vol+RS_cumulo+Cell_conc._interval+RQ_integral+Arg_conc.+emission_CO2+interval_O2+generate_CO2; 0.170, 0.569, tmp+PL_cumulo+Feed_Vol+RS_cumulo+Cell_conc._interval+RQ_integral+Arg_conc.+emission_O2+consum_O2+interval_O2; 0.170, 0.569, tmp_cumulo+pH+PL_cumulo+RS_cumulo+Cell_conc._interval+RQ_integral+Arg_conc.+emission_CO2+consum_O2+interval_O2; 0.131, 0.569, tmp+PL+PL_cumulo+AN_cumulo+interval_yield+Feed_Vol+RS_cumulo+Cell_conc._ interval+Arg_conc.+emission_O2+interval_O2+generate_CO2; 0.170, 0.569, tmp_cumulo+PL+PL_cumulo+AN_cumulo+RS_cumulo+Cell_conc._interval+rab_integral+Arg_conc.+emission_CO2+interval_O2; 0.170, 0.569, tmp+PL+PL_cumulo+AN_cumulo+RS_cumulo+Cell_conc._interval+rab_integral+Arg_conc.+emission_CO2+interval_O2; 0.151, 0.569, tmp_cumulo+PL_cumulo+Feed_Vol+RS_cumulo+Cell_conc._interval+rab_integral+RQ_integral+Arg_conc.+emission_CO2+interval_O2+generate_CO2; 0.151, 0.569, tmp+PL+PL_cumulo+AN_cumulo+RS+Feed_Vol+Cell_conc._interval+Arg_conc.+emission_O2+consum_O2+generate_CO2; 0.170, 0.569, tmp_cumulo+PL_cumulo+AN_cumulo+Feed_Vol+RS_cumulo+Cell_conc._interval+RQ_integral+Arg_conc.+emission_O2+interval_O2; 0.151, 0.569, tmp+pH_cumulo+PL_cumulo+interval_yield+Feed_Vol+RS_cumulo+Cell_conc._interval+Arg_conc.+emission_O2+interval_O2+generate_CO2; 0.131, 0.569, tmp_cumulo+pH+PL_cumulo+AN_cumulo+Feed_Vol+RS_cumulo+Cell_conc._interval+rab_integral+Arg_conc.+emission_O2+interval_O2+generate_CO2; 0.131, 0.569, tmp_cumulo+pH+PL_cumulo+RS+Feed_Vol+RS_cumulo+Cell_conc._interval+Arg_conc.+emission_O2+emission_CO2+consum_O2+interval_O2; 0.151, 0.569, tmp_cumulo+pH+PL_cumulo+AN+Feed_Vol+RS_cumulo+Cell_conc._interval+RQ_integral+Arg_conc.+emission_CO2+interval_O2; 0.170, 0.569, tmp_cumulo+pH+PL_cumulo+interval_yield+RS_cumulo+Cell_conc._interval+RQ_integral+Arg_conc.+emission_CO2+interval_O2; 0.170, 0.569, tmp_cumulo+PL_cumulo+AN_cumulo+interval_yield+Feed_Vol+RS_cumulo+Cell_conc._interval+RQ_integral+Arg_conc.+interval_O2; 0.151, 0.569, tmp_cumulo+PL_cumulo+AN_cumulo+RS+RS_cumulo+Cell_conc._interval+rab_integral+Arg_conc.+emission_CO2+consum_O2+interval_O2; 0.151, 0.569, tmp+pH_cumulo+PL_cumulo+RS+Feed_Vol+RS_cumulo+Cell_conc._interval+Arg_conc.+emission_O2+interval_O2+generate_CO2; 0.189, 0.569, tmp_cumulo+PL_cumulo+interval_yield+RS_cumulo+Cell_conc._interval+rab_integral+Arg_conc.+emission_CO2+interval_O2; 0.151, 0.569, tmp_cumulo+pH_cumulo+PL+PL_cumulo+Feed_Vol+RS_cumulo+Cell_conc._interval+Arg_conc.+emission_O2+consum_O2+interval_O2; 0.170, 0.569, tmp+PL_cumulo+AN_cumulo+Feed_Vol+Cell_conc._interval+RQ_integral+Arg_conc.+emission_O2+consum_O2+generate_CO2; 0.170, 0.569, tmp+PL_cumulo+Feed_Vol+RS_cumulo+Cell_conc._interval+rab_integral+Arg_conc.+emission_O2+consum_O2+interval_O2; 0.130, 0.569, tmp+pH+PL_cumulo+AN_cumulo+Feed_Vol+RS_cumulo+Cell_conc._interval+rab_integral+Arg_conc.+emission_O2+consum_O2+interval_O2; 0.151, 0.569, tmp_cumulo+PL_cumulo+AN_cumulo+Feed_Vol+RS_cumulo+Cell_conc._interval+rab_integral+Arg_conc.+emission_O2+consum_O2+interval_O2; 0.130, 0.569, tmp_cumulo+PL_cumulo+AN_cumulo+Feed_Vol+RS_cumulo+Cell_conc._interval+RQ_integral+Arg_conc.+emission_O2+emission_CO2+interval_O2+generate_CO2; 0.151, 0.569, tmp_cumulo+pH_cumulo+PL_cumulo+interval_yield+Feed_Vol+RS_cumulo+Cell_conc._interval+rab_integral+Arg_conc.+emission_O2+interval_O2; 0.130, 0.569, tmp+PL_cumulo+AN_cumulo+Feed_Vol+RS_cumulo+Cell_conc._interval+RQ_integral+Arg_conc.+emission_O2+emission_CO2+interval_O2+generate_CO2; 0.150, 0.569, tmp_cumulo+PL_cumulo+AN_cumulo+Feed_Vol+RS_cumulo+Cell_conc._interval+Arg_conc.+emission_O2+consum_O2+interval_O2+generate_CO2; 0.150, 0.569, tmp+pH+PL_cumulo+Feed_Vol+RS_cumulo+Cell_conc._interval+rab_integral+Arg_conc.+emission_O2+interval_O2+generate_CO2; 0.150, 0.569, tmp+pH+PL_cumulo+AN_cumulo+RS+RS_cumulo+Cell_conc._interval+Arg_conc.+emission_O2+interval_O2+generate_CO2; 0.170, 0.569, tmp_cumulo+pH_cumulo+PL_cumulo+Feed_Vol+RS_cumulo+Cell_conc._interval+Arg_conc.+emission_O2+emission_CO2+interval_O2; 0.130, 0.569, tmp_cumulo+pH+PL_cumulo+AN_cumulo+interval_yield+RS+RS_cumulo+Cell_conc._interval+rab_integral+Arg_conc.+emission_CO2+interval_O2; 0.170, 0.569, tmp_cumulo+pH+PL_cumulo+RS+RS_cumulo+Cell_conc._interval+rab_integral+Arg_conc.+emission_O2+interval_O2; 0.130, 0.569, tmp_cumulo+pH_cumulo+PL_cumulo+AN_cumulo+Feed_Vol+RS_cumulo+Cell_conc._interval+Arg_conc.+emission_O2+consum_O2+interval_O2+generate_CO2; 0.170, 0.569, tmp_cumulo+pH+PL_cumulo+AN+Feed_Vol+RS_cumulo+Cell_conc._interval+Arg_conc.+emission_O2+interval_O2; 0.150, 0.569, tmp_cumulo+pH+PL_cumulo+AN+RS_cumulo+Cell_conc._interval+rab_integral+Arg_conc.+emission_CO2+interval_O2; 0.150, 0.569, tmp_cumulo+pH_cumulo+PL_cumulo+Feed_Vol+RS_cumulo+Cell_conc._interval+rab_integral+RQ_integral+Arg_conc.+emission_CO2+interval_O2; 0.169, 0.569, tmp+pH+PL_cumulo+AN_cumulo+Feed_Vol+RS_cumulo+Cell_conc._interval+Arg_conc.+emission_O2+interval_O2; 0.150, 0.569, tmp_cumulo+pH_cumulo+PL_cumulo+AN_cumulo+RS_cumulo+Cell_conc._cumulo+Cell_conc._interval+rab_integral+Arg_conc.+emission_CO2+interval_O2; 0.150, 0.569, tmp+PL+PL_cumulo+Feed_Vol+RS_cumulo+Cell_conc._interval+RQ_integral+Arg_conc.+emission_CO2+consum_O2+generate_CO2; 0.150, 0.569, tmp_cumulo+pH_cumulo+PL_cumulo+RS+RS_cumulo+Cell_conc._interval+rab_integral+Arg_conc.+emission_CO2+interval_O2+generate_CO2; 0.150, 0.569, tmp_cumulo+PL_cumulo+AN_cumulo+Feed_Vol+RS_cumulo+Cell_conc._interval+Arg_conc.+emission_O2+emission_CO2+consum_O2+generate_CO2; 0.169, 0.569, tmp_cumulo+PL_cumulo+Feed_Vol+RS_cumulo+Cell_conc._interval+rab_integral+Arg_conc.+emission_CO2+consum_O2+interval_O2; 0.169, 0.568, tmp+pH+PL_cumulo+Feed_Vol+RS_cumulo+Cell_conc._interval+rab_integral+Arg_conc.+emission_O2+interval_O2; 0.150, 0.568, tmp_cumulo+PL_cumulo+interval_yield+Feed_Vol+RS_cumulo+Cell_conc._interval+rab_integral+Arg_conc.+emission_O2+interval_O2+generate_CO2; 0.150, 0.568, tmp_cumulo+PL+PL_cumulo+RS+Feed_Vol+RS_cumulo+Cell_conc._interval+RQ_integral+Arg_conc.+emission_CO2+interval_O2; 0.130, 0.568, tmp+PL+PL_cumulo+AN_cumulo+Feed_Vol+RS_cumulo+Cell_conc._interval+RQ_integral+Arg_conc.+emission_CO2+consum_O2+interval_O2; 0.150, 0.568, tmp+PL_cumulo+AN_cumulo+RS+Feed_Vol+Cell_conc._interval+Arg_conc.+emission_O2+emission_CO2+interval_O2+generate_CO2; 0.188, 0.568, tmp+PL+PL_cumulo+RS+RS_cumulo+Cell_conc._interval+RQ_integral+Arg_conc.+emission_CO2+interval_O2; 0.130, 0.568, tmp+pH+pH_cumulo+PL_cumulo+AN_cumulo+Feed_Vol+RS_cumulo+Cell_conc._interval+Arg_conc.+emission_O2+interval_O2+generate_CO2; 0.150, 0.568, tmp+PL+PL_cumulo+AN_cumulo+RS+RS_cumulo+Cell_conc._interval+rab_integral+Arg_conc.+emission_CO2+interval_O2; 0.150, 0.568, tmp+pH_cumulo+PL+PL_cumulo+Feed_Vol+RS_cumulo+Cell_conc._interval+Arg_conc.+emission_O2+interval_O2+generate_CO2; 0.169, 0.568, tmp_cumulo+pH_cumulo+PL_cumulo+RS+Feed_Vol+Cell_conc._interval+Arg_conc.+emission_O2+consum_O2+interval_O2; 0.169, 0.568, tmp_cumulo+pH+PL_cumulo+RS_cumulo+Cell_conc._interval+rab_integral+Accum._Yield+Arg_conc.+emission_CO2+interval_O2; 0.187, 0.568, tmp_cumulo+PL_cumulo+RS_cumulo+Cell_conc._interval+rab_integral+Arg_conc.+ emission_O2+emission_CO2+interval_O2; 0.150, 0.568, tmp+pH+pH_cumulo+PL_cumulo+Feed_Vol+RS_cumulo+Cell_conc._interval+Arg_conc.+emission_O2+interval_O2+generate_CO2; 0.150, 0.568, tmp_cumulo+pH+PL_cumulo+Feed_Vol+RS_cumulo+Cell_conc._cumulo+Cell_conc._interval+RQ_integral+Arg_conc.+emission_CO2+interval_O2; 0.187, 0.568, tmp+pH+PL_cumulo+RS_cumulo+Cell_conc._interval+RQ_integral+Arg_conc.+emission_CO2+interval_O2; 0.129, 0.568, tmp_cumulo+pH_cumulo+PL_cumulo+AN_cumulo+interval_yield+Feed_Vol+RS_cumulo+Cell_conc._interval+RQ_integral+Arg_conc.+emission_CO2+interval_O2; 0.187, 0.568, tmp_cumulo+PL_cumulo+Feed_Vol+RS_cumulo+Cell_conc._interval+Arg_conc.+emission_CO2+interval_O2+generate_CO2; 0.129, 0.568, tmp_cumulo+pH+pH_cumulo+PL_cumulo+AN_cumulo+Feed_Vol+RS_cumulo+Cell_conc._interval+Arg_conc.+emission_O2+interval_O2+generate_CO2; 0.169, 0.568, tmp+PL_cumulo+RS+RS_cumulo+Cell_conc._interval+rab_integral+Arg_conc.+emission_CO2+interval_O2+generate_CO2; 0.149, 0.568, tmp+tmp_cumulo+pH_cumulo+PL_cumulo+Feed_Vol+RS_cumulo+Cell_conc._interval+Arg_conc.+emission_O2+interval_O2+generate_CO2; 0.149, 0.568, tmp_cumulo+pH+pH_cumulo+PL_cumulo+RS_cumulo+Cell_conc._interval+rab_integral+Arg_conc.+emission_CO2+consum_O2+interval_O2; 0.149, 0.568, tmp+pH+PL+PL_cumulo+Feed_Vol+RS_cumulo+Cell_conc._interval+Arg_conc.+emission_O2+interval_O2+generate_CO2; 0.169, 0.568, tmp+PL+PL_cumulo+AN_cumulo+Feed_Vol+Cell_conc._interval+Arg_conc.+emission_O2+consum_O2+generate_CO2; 0.149, 0.568, tmp_cumulo+pH+PL+PL_cumulo+RS_cumulo+Cell_conc._cumulo+Cell_conc._interval+rab_integral+Arg_conc.+emission_CO2+interval_O2; 0.149, 0.568, tmp_cumulo+pH+PL_cumulo+AN+RS_cumulo+Cell_conc._interval+rab_integral+Arg_conc.+emission_CO2+consum_O2+interval_O2; 0.169, 0.568, tmp_cumulo+PL_cumulo+AN_cumulo+RS_cumulo+Cell_conc._interval+rab_integral+Arg_conc.+emission_CO2+interval_O2+generate_CO2; 0.149, 0.568, tmp_cumulo+pH+PL_cumulo+AN_cumulo+OD+RS_cumulo+Cell_conc._interval+rab_integral+Arg_conc.+emission_CO2+interval_O2; 0.129, 0.568, tmp_cumulo+pH+PL_cumulo+AN_cumulo+OD+Feed_Vol+RS_cumulo+Cell_conc._interval+rab_integral+Arg_conc.+emission_CO2+interval_O2; 0.169, 0.568, tmp_cumulo+PL+PL_cumulo+Feed_Vol+RS_cumulo+Cell_conc._interval+Arg_conc.+emission_O2+consum_O2+interval_O2; 0.149, 0.568, tmp_cumulo+pH_cumulo+PL_cumulo+interval_yield+RS_cumulo+Cell_conc._interval+rab_integral+Arg_conc.+emission_CO2+interval_O2+generate_CO2; 0.168, 0.568, tmp+pH+PL_cumulo+RS_cumulo+Cell_conc._interval+rab_integral+Arg_conc.+emission_CO2+interval_O2+generate_CO2; 0.149, 0.568, tmp_cumulo+pH+PL_cumulo+RS+Feed_Vol+RS_cumulo+Cell_conc._interval+rab_integral+Arg_conc.+emission_O2+interval_O2; 0.149, 0.568, tmp_cumulo+PL_cumulo+interval_yield+Feed_Vol+RS_cumulo+Cell_conc._interval+RQ_integral+Arg_conc.+emission_O2+emission_CO2+interval_O2; 0.168, 0.568, tmp_cumulo+pH_cumulo+PL_cumulo+RS_cumulo+Cell_conc._interval+rab_integral+RQ_integral+Arg_conc.+emission_CO2+interval_O2; 0.149, 0.568, tmp_cumulo+PL_cumulo+Feed_Vol+RS_cumulo+Cell_conc._interval+rab_integral+Arg_conc.+emission_O2+emission_CO2+interval_O2+generate_CO2; 0.129, 0.568, tmp_cumulo+PL_cumulo+AN_cumulo+Feed_Vol+RS_cumulo+Cell_conc._interval+RQ_integral+Arg_conc.+emission_O2+emission_CO2+consum_O2+interval_O2; 0.149, 0.568, tmp_cumulo+pH+PL+RS_cumulo+Cell_conc._interval+rab_integral+Arg_conc.+emission_O2+emission_CO2+interval_O2; 0.149, 0.568, tmp_cumulo+

PL+PL_cumulo+AN_cumulo+Feed_Vol+RS_cumulo+Cell_conc._interval+Arg_conc.+emission_O2+consum_O2+interval_O2; 0.107, 0.568, tmp_cumulo+pH+PL_cumulo+AN_cumulo+Feed_Vol+RS_cumulo+Cell_conc._interval+rab_integral+Arg_conc.+emission_O2+emission_CO2+consum_O2+interval_O2; 0.129, 0.568, tmp+pH+PL_cumulo+AN_cumulo+Feed_Vol+RS_cumulo+Cell_conc._interval+rab_integral+Arg_conc.+emission_O2+interval_O2+generate_CO2; 0.149, 0.568, tmp+PL+PL_cumulo+Feed_Vol+RS_cumulo+Cell_conc._interval+rab_integral+Arg_conc.+emission_O2+consum_O2+generate_CO2; 0.129, 0.568, tmp+tmp_cumulo+pH+PL_cumulo+AN_cumulo+Feed_Vol+RS_cumulo+Cell_conc._interval+Arg_conc.+emission_O2+interval_O2+generate_CO2; 0.168, 0.568, tmp+PL_cumulo+Feed_Vol+RS_cumulo+Cell_conc._interval+RQ_integral+Arg_conc.+emission_O2+emission_CO2+interval_O2; 0.149, 0.568, tmp_cumulo+pH_cumulo+PL_cumulo+RS+RS_cumulo+Cell_conc._interval+rab_integral+Arg_conc.+emission_CO2+interval_O2; 0.187, 0.568, tmp+PL_cumulo+RS_cumulo+Cell_conc._interval+rab_integral+Arg_conc.+emission_CO2+consum_O2+generate_CO2; 0.168, 0.568, tmp_cumulo+PL+PL_cumulo+Feed_Vol+RS_cumulo+Cell_conc._interval+rab_integral+Arg_conc.+emission_CO2+interval_O2; 0.149, 0.568, tmp_cumulo+PL_cumulo+AN_cumulo+interval_yield+Feed_Vol+RS_cumulo+Cell_conc._interval+Arg_conc.+emission_O2+consum_O2+interval_O2; 0.149, 0.568, tmp+PL_cumulo+RS+Feed_Vol+RS_cumulo+Cell_conc._interval+rab_integral+Arg_conc.+emission_O2+interval_O2+generate_CO2; 0.187, 0.568, tmp+PL_cumulo+Feed_Vol+RS_cumulo+Cell_conc._interval+Arg_conc.+emission_CO2+consum_O2+generate_CO2; 0.128, 0.568, tmp_cumulo+PL_cumulo+AN_cumulo+interval_yield+Feed_Vol+RS_cumulo+Cell_conc._interval+RQ_integral+Arg_conc.+emission_CO2+consum_O2+interval_O2; 0.149, 0.568, tmp+PL_cumulo+AN_cumulo+RS+Feed_Vol+Cell_conc._interval+RQ_integral+Arg_conc.+emission_O2+consum_O2+generate_CO2; 0.128, 0.568, tmp_cumulo+pH_cumulo+PL_cumulo+AN_cumulo+Feed_Vol+RS_cumulo+Cell_conc._interval+rab_integral+Arg_conc.+emission_O2+emission_CO2+interval_O2; 0.168, 0.567, tmp+PL_cumulo+RS+Feed_Vol+RS_cumulo+Cell_conc._interval+Arg_conc.+emission_O2+consum_O2+interval_O2; 0.128, 0.567, tmp_cumulo+PL_cumulo+AN_cumulo+interval_yield+Feed_Vol+RS_cumulo+Cell_conc._interval+Arg_conc.+emission_O2+emission_CO2+interval_O2+generate_CO2; 0.149, 0.567, tmp_cumulo+pH_cumulo+PL_cumulo+RS_cumulo+Cell_conc._interval+rab_integral+Arg_conc.+emission_CO2+consum_O2+interval_O2+generate_CO2; 0.149, 0.567, tmp+PL+PL_cumulo+Feed_Vol+RS_cumulo+Cell_conc._interval+RQ_integral+Arg_conc.+emission_O2+consum_O2+generate_CO2; 0.186, 0.567, tmp_cumulo+pH+PL_cumulo+RS_cumulo+Cell_conc._interval+Arg_conc.+emission_O2+emission_CO2+interval_O2; 0.168, 0.567, tmp+pH+PL_cumulo+AN_cumulo+Feed_Vol+Cell_conc._interval+Arg_conc.+emission_O2+interval_O2+generate_CO2; 0.128, 0.567, tmp+PL+PL_cumulo+AN_cumulo+Feed_Vol+RS_cumulo+Cell_conc._interval+Arg_conc.+emission_O2+emission_CO2+consum_O2+interval_O2; 0.128, 0.567, tmp_cumulo+pH+PL_cumulo+AN+AN_cumulo+Feed_Vol+RS_cumulo+Cell_conc._interval+RQ_integral+Arg_conc.+emission_CO2+interval_O2; 0.186, 0.567, tmp_cumulo+pH+PL_cumulo+Feed_Vol+RS_cumulo+Cell_conc._interval+rab_integral+Arg_conc.+interval_O2; 0.148, 0.567, tmp+tmp_cumulo+PL_cumulo+AN_cumulo+Feed_Vol+RS_cumulo+Cell_conc._interval+RQ_integral+Arg_conc.+emission_CO2+interval_O2; 0.148, 0.567, tmp_cumulo+pH+PL_cumulo+Feed_Vol+RS_cumulo+Cell_ conc._cumulo+Cell_conc._interval+rab_integral+Arg_
conc.+emission_CO2+interval_O2; 0.128, 0.567, tmp+tmp_
cumulo+pH+PL_cumulo+AN_cumulo+Feed_Vol+RS_
cumulo+Cell_conc._interval+RQ_integral+Arg_conc.+
emission_CO2+interval_O2; 0.148, 0.567, tmp+PL_
cumulo+Feed_Vol+RS_cumulo+Cell_conc._interval+RQ_
integral+Arg_conc.+emission_O2+emission_CO2+
consum_O2+generate_CO2; 0.148, 0.567, tmp+tmp_
cumulo+pH+PL_cumulo+RS_cumulo+Cell_conc._
interval+rab_integral+Arg_conc.+emission_CO2+interval_
O2+generate_CO2; 0.204, 0.567, tmp+PL_cumulo+Feed_
Vol+RS_cumulo+Cell_conc._interval+RQ_integral+Arg_
conc.+interval_O2; 0.148, 0.567, tmp+tmp_cumulo+pH_
cumulo+PL_cumulo+AN_cumulo+RS_cumulo+Cell_
conc._interval+rab_integral+Arg_conc.+emission_CO2+
interval_O2; 0.148, 0.567, tmp_cumulo+pH_cumulo+PL_
cumulo+interval_yield+RS+RS_cumulo+Cell_conc._
interval+rab_integral+Arg_conc.+emission_CO2+interval_
O2; 0.186, 0.567, tmp_cumulo+pH+PL_cumulo+Feed_
Vol+RS_cumulo+Cell_conc._interval+Arg_conc.+
emission_CO2+interval_O2; 0.148, 0.567, tmp_cumulo+
pH_cumulo+PL_cumulo+RS+RS_cumulo+Cell_conc._
interval+rab_integral+Arg_conc.+emission_CO2+consum_
O2+interval_O2; 0.148, 0.567, tmp+pH_cumulo+PL_
cumulo+AN_cumulo+RS+Feed_Vol+Cell_conc._interval+
Arg_conc.+emission_O2+consum_O2+interval_O2; 0.128,
0.567, tmp+tmp_cumulo+pH_cumulo+PL_cumulo+AN_
cumulo+Feed_Vol+RS_cumulo+Cell_conc._interval+Arg_
conc.+emission_O2+consum_O2+interval_O2; 0.128,
0.567, tmp_cumulo+PL_cumulo+AN_cumulo+Feed_Vol+
RS_cumulo+Cell_conc._interval+rab_integral+RQ_inte-
gral+Arg_conc.+emission_CO2+consum_O2+interval_O2;
0.167, 0.567, tmp_cumulo+pH_cumulo+PL_cumulo+RS+
RS_cumulo+Cell_conc._interval+RQ_integral+Arg_conc.+
emission_CO2+interval_O2; 0.148, 0.567, tmp+PL+PL_cu-
mulo+RS+Feed_Vol+RS_cumulo+Cell_conc._interval+
Arg_conc.+emission_O2+interval_O2+generate_CO2;
0.128, 0.567, tmp_cumulo+pH+PL_cumulo+AN_cumulo+
RS+RS_cumulo+Cell_conc._interval+rab_integral+RQ_in-
tegral+Arg_conc.+emission_CO2+interval_O2; 0.148,
0.567, tmp+tmp_cumulo+pH+PL_cumulo+RS+RS_cu-
mulo+Cell_conc._interval+rab_integral+Arg_conc.+emis-
sion_CO2+interval_O2; 0.148, 0.567, tmp+PL_cumulo+
AN_cumulo+Feed_Vol+RS_cumulo+Cell_conc._interval+
rab_integral+Arg_conc.+emission_CO2+consum_O2+
generate_CO2; 0.148, 0.567, tmp_cumulo+pH+PL+PL_
cumulo+Feed_Vol+RS_cumulo+Cell_conc._interval+rab_
integral+Arg_conc.+emission_O2+interval_O2; 0.167,
0.567, tmp_cumulo+PL_cumulo+interval_yield+RS+RS_
cumulo+Cell_conc._interval+rab_integral+Arg_conc.+
emission_CO2+interval_O2; 0.148, 0.567, tmp_cumulo+
PL_cumulo+AN_cumulo+Feed_Vol+RS_cumulo+Cell_
conc._interval+rab_integral+RQ_integral+Arg_conc.+
emission_CO2+interval_O2; 0.186, 0.567, tmp_cumulo+
PL_cumulo+RS_cumulo+Cell_conc._interval+rab_
integral+Arg_conc.+emission_CO2+consum_O2+
generate_CO2; 0.148, 0.567, tmp_cumulo+pH+PL_
cumulo+AN+RS_cumulo+Cell_conc._cumulo+Cell_conc._
interval+rab_integral+Arg_conc.+emission_CO2+interval_
O2; 0.167, 0.567, tmp_cumulo+pH+PL_cumulo+interval_
yield+Feed_Vol+RS_cumulo+Cell_conc._interval+RQ_
integral+Arg_conc.+interval_O2; 0.148, 0.567, tmp_
cumulo+PL_cumulo+RS+Feed_Vol+RS_cumulo+Cell_
conc._interval+rab_integral+Arg_conc.+emission_O2+
interval_O2+generate_CO2; 0.186, 0.567, tmp_cumulo+
PL_cumulo+AN_cumulo+Feed_Vol+RS_cumulo+Cell_
conc._interval+RQ_integral+Arg_conc.+interval_O2;
0.127, 0.567, tmp_cumulo+pH+PL_cumulo+AN_cumulo+
Feed_Vol+RS_cumulo+Cell_conc._interval+Arg_conc.+
emission_O2+consum_O2+interval_O2+generate_CO2;
0.185, 0.567, tmp+PL_cumulo+Feed_Vol+Cell_conc._in-
terval+RQ_integral+Arg_conc.+emission_CO2+consum_
O2+generate_CO2; 0.127, 0.567, tmp_cumulo+PL_cu-
mulo+AN_cumulo+RS+Feed_Vol+RS_cumulo+Cell_
conc._interval+Arg_conc.+emission_O2+emission_CO2+
interval_O2+generate_CO2; 0.127, 0.567, tmp+pH+pH_
cumulo+PL_cumulo+AN_cumulo+Feed_Vol+RS_cumulo+
Cell_conc._interval+Arg_conc.+emission_O2+consum_
O2+interval_O2; 0.127, 0.567, tmp+pH_cumulo+PL_
cumulo+AN_cumulo+interval_yield+Feed_Vol+RS_
cumulo+Cell_conc._interval+Arg_conc.+emission_O2+
interval_O2+generate_CO2; 0.147, 0.567, tmp+pH+PL_
cumulo+RS+Feed_Vol+Cell_conc._interval+Arg_conc.+
emission_O2+emission_CO2+interval_O2+generate_CO2;
0.185, 0.567, tmp_cumulo+pH+PL_cumulo+Feed_Vol+
RS_cumulo+Cell_conc._interval+RQ_integral+Arg_conc.+
interval_O2; 0.167, 0.567, tmp_cumulo+PL+PL_cumulo+
Feed_Vol+RS_cumulo+Cell_conc._interval+RQ_integral+
Arg_conc.+emission_O2+interval_O2; 0.147, 0.567, tmp+
tmp_cumulo+PL_cumulo+Feed_Vol+RS_cumulo+Cell_
conc._interval+Arg_conc.+emission_O2+emission_CO2+
interval_O2+generate_CO2; 0.127, 0.567, tmp_cumulo+
PL_cumulo+AN_cumulo+interval_yield+RS+Feed_Vol+
RS_cumulo+Cell_conc._interval+Arg_conc.+emission_
O2+interval_O2+generate_CO2; 0.127, 0.567, tmp+PL+
PL_cumulo+AN_cumulo+Feed_Vol+RS_cumulo+Cell_
conc._interval+RQ_integral+Arg_conc.+emission_O2+
consum_O2+interval_O2; 0.185, 0.567, tmp_cumulo+pH+
PL_cumulo+AN_cumulo+RS_cumulo+Cell_conc._
interval+Arg_conc.+emission_O2+interval_O2; 0.147,
0.567, tmp_cumulo+PL_cumulo+RS+Feed_Vol+RS_cu-
mulo+Cell_conc._interval+RQ_integral+Arg_conc.+emis-
sion_CO2+consum_O2+interval_O2; 0.185, 0.567, tmp_cu-
mulo+PL_cumulo+RS_cumulo+Cell_conc._cumulo+Cell_
conc._interval+rab_integral+Arg_conc.+emission_CO2+
interval_O2; 0.106, 0.567, tmp_cumulo+pH+PL+PL_
cumulo+AN_cumulo+Feed_Vol+RS_cumulo+Cell_conc._
interval+Arg_conc.+emission_O2+emission_CO2+
consum_O2+interval_O2; 0.167, 0.567, tmp_cumulo+pH+
PL_cumulo+RS_cumulo+Cell_conc._interval+RQ_
integral+Arg_conc.+emission_O2+emission_CO2+
interval_O2; 0.147, 0.567, tmp_cumulo+pH+PL_cumulo+
RS_cumulo+Cell_conc._cumulo+Cell_conc._interval+rab_
integral+Arg_conc.+emission_CO2+interval_O2+
generate_CO2; 0.167, 0.567, tmp+pH_cumulo+PL_
cumulo+RS+RS_cumulo+Cell_conc._interval+rab_
integral+Arg_conc.+emission_CO2+interval_O2; 0.167,
0.567, tmp+PL_cumulo+RS+Feed_Vol+Cell_conc._inter-
val+RQ_integral+Arg_conc.+emission_CO2+consum_O2+
generate_CO2; 0.167, 0.567, tmp_cumulo+PL_cumulo+
AN+Feed_Vol+RS_cumulo+Cell_conc._interval+Arg_
conc.+emission_O2+interval_O2+generate_CO2; 0.127,
0.566, tmp_cumulo+pH_cumulo+PL_cumulo+AN_cu-
mulo+Feed_Vol+RS_cumulo+Cell_conc._interval+RQ_in-
tegral+Arg_conc.+emission_CO2+interval_O2+generate_
CO2; 0.147, 0.566, tmp_cumulo+pH+PL_cumulo+Feed_
Vol+RS_cumulo+Cell_conc._interval+Arg_conc.+
emission_O2+emission_CO2+consum_O2+generate_CO2;
0.127, 0.566, tmp_cumulo+PL_cumulo+AN_cumulo+RS+
Feed_Vol+RS_cumulo+Cell_conc._interval+RQ_integral+
Arg_conc.+emission_CO2+consum_O2+interval_O2;
0.147, 0.566, tmp+pH_cumulo+PL_cumulo+AN_cumulo+
Feed_Vol+RS_cumulo+Cell_conc._interval+RQ_integral+
Arg_conc.+emission_CO2+interval_O2; 0.185, 0.566, tmp+
tmp_cumulo+PL_cumulo+RS_cumulo+Cell_conc._
interval+rab_integral+Arg_conc.+emission_CO2+interval_
O2; 0.166, 0.566, tmp_cumulo+PL_cumulo+interval_
yield+Feed_Vol+RS_cumulo+Cell_conc._interval+RQ_
integral+Arg_conc.+interval_O2+generate_CO2; 0.127,
0.566, tmp_cumulo+pH+PL+PL_cumulo+AN_cumulo+

RS_cumulo+Cell_conc._cumulo+Cell_conc._interval+rab_integral+Arg_conc.+emission_CO2+interval_O2; 0.127, 0.566, tmp_cumulo+pH_cumulo+PL_cumulo+interval_yield+Feed_Vol+RS_cumulo+Cell_conc._interval+Arg_conc.+emission_O2+emission_CO2+consum_O2+interval_O2; 0.147, 0.566, tmp+pH+PL_cumulo+RS+Feed_Vol+RS_cumulo+Cell_conc._interval+Arg_conc.+emission_O2+consum_O2+interval_O2; 0.147, 0.566, tmp_cumulo+pH+PL_cumulo+interval_yield+RS_cumulo+Cell_conc._interval+rab_integral+Arg_conc.+emission_CO2+interval_O2+generate_CO2; 0.166, 0.566, tmp+pH_cumulo+PL_cumulo+RS+Feed_Vol+Cell_conc._interval+Arg_conc.+emission_O2+consum_O2+interval_O2; 0.127, 0.566, tmp_cumulo+pH+PL_cumulo+AN_cumulo+OD+Feed_Vol+RS_cumulo+Cell_conc._interval+Arg_conc.+emission_O2+consum_O2+interval_O2; 0.166, 0.566, tmp_cumulo+pH+PL_cumulo+RS_cumulo+Cell_conc._interval+rab_integral+Arg_conc.+emission_O2+consum_O2+interval_O2; 0.166, 0.566, tmp+tmp_cumulo+PL_cumulo+Feed_Vol+RS_cumulo+Cell_conc._interval+Arg_conc.+emission_O2+consum_O2+interval_O2; 0.166, 0.566, tmp_cumulo+pH_cumulo+PL_cumulo+interval_yield+Feed_Vol+RS_cumulo+Cell_conc._interval+Arg_conc.+emission_O2+interval_O2; 0.166, 0.566, tmp_cumulo+pH+PL_cumulo+RS+Feed_Vol+Cell_conc._interval+Arg_conc.+emission_O2+interval_O2+generate_CO2; 0.166, 0.566, tmp_cumulo+PL_cumulo+RS+RS_cumulo+Cell_conc._interval+rab_integral+Arg_conc.+emission_CO2+consum_O2+generate_CO2; 0.166, 0.566, tmp_cumulo+pH_cumulo+PL_cumulo+AN_cumulo+RS_cumulo+Cell_conc._interval+RQ_integral+Arg_conc.+emission_CO2+interval_O2; 0.202, 0.566, PL_cumulo+Feed_Vol+RS_cumulo+Cell_conc._interval+Arg_conc.+emission_O2+consum_O2+generate_CO2; 0.126, 0.566, tmp_cumulo+pH+PL_cumulo+RS+Feed_Vol+RS_cumulo+Cell_conc._interval+Arg_conc.+emission_O2+emission_CO2+interval_O2+generate_CO2; 0.166, 0.566, tmp+pH_cumulo+PL_cumulo+Feed_Vol+RS_cumulo+Cell_conc._interval+rab_integral+Arg_conc.+emission_CO2+interval_O2; 0.185, 0.566, tmp+pH+PL_cumulo+Feed_Vol+Cell_conc._interval+Arg_conc.+emission_O2+consum_O2+generate_CO2; 0.126, 0.566, tmp+PL_cumulo+AN_cumulo+RS+Feed_Vol+RS_cumulo+Cell_conc._interval+rab_integral+Arg_conc.+emission_O2+interval_O2+generate_CO2; 0.166, 0.566, tmp_cumulo+pH_cumulo+PL_cumulo+RS+Feed_Vol+Cell_conc._interval+Arg_conc.+emission_O2+interval_O2+generate_CO2; 0.126, 0.566, tmp+pH_cumulo+PL_cumulo+AN_cumulo+RS+Feed_Vol+RS_cumulo+Cell_conc._interval+Arg_conc.+emission_O2+interval_O2+generate_CO2; 0.185, 0.566, tmp_cumulo+PL_cumulo+Feed_Vol+RS_cumulo+Cell_conc._interval+rab_integral+RQ_integral+Arg_conc.+interval_O2; 0.147, 0.566, tmp_cumulo+PL_cumulo+AN_cumulo+RS+Feed_Vol+RS_cumulo+Cell_conc._interval+Arg_conc.+emission_O2+consum_O2+generate_CO2; 0.126, 0.566, tmp+tmp_cumulo+pH_cumulo+PL_cumulo+AN_cumulo+Feed_Vol+RS_cumulo+Cell_conc._interval+rab_integral+Arg_conc.+emission_CO2+interval_O2; 0.126, 0.566, tmp_cumulo+pH_cumulo+PL+PL_cumulo+AN_cumulo+RS+RS_cumulo+Cell_conc._interval+rab_integral+Arg_conc.+emission_CO2+interval_O2; 0.126, 0.566, tmp_cumulo+pH+PL_cumulo+AN_cumulo+Feed_Vol+RS_cumulo+Cell_conc._interval+RQ_integral+Arg_conc.+emission_O2+interval_O2+generate_CO2; 0.146, 0.566, tmp_cumulo+pH+PL_cumulo+RS_cumulo+Cell_conc._cumulo+Cell_conc._interval+rab_integral+Arg_conc.+emission_CO2+consum_O2+interval_O2; 0.184, 0.566, tmp+pH+PL_cumulo+RS_cumulo+Cell_conc._interval+Arg_conc.+emission_O2+consum_O2+interval_O2; 0.105, 0.566, tmp_cumulo+pH+PL+PL_cumulo+AN_cumulo+RS+Feed_Vol+RS_cumulo+Cell_conc._interval+rab_integral+Arg_conc.+emission_CO2+interval_O2; 0.126, 0.566, tmp_cumulo+pH+PL+PL_cumulo+AN_cumulo+RS_cumulo+Cell_conc._interval+rab_integral+Arg_conc.+emission_CO2+consum_O2+interval_O2; 0.166, 0.566, tmp+pH_cumulo+PL_cumulo+RS_cumulo+Cell_conc._interval+rab_integral+Arg_conc.+emission_CO2+interval_O2+generate_CO2; 0.126, 0.566, tmp_cumulo+PL_cumulo+AN_cumulo+Feed_Vol+RS_cumulo+Cell_conc._interval+RQ_integral+Arg_conc.+emission_CO2+consum_O2+interval_O2+generate_CO2; 0.166, 0.566, tmp_cumulo+PL+PL_cumulo+RS+RS_cumulo+Cell_conc._interval+RQ_integral+Arg_conc.+emission_CO2+interval_O2; 0.146, 0.566, tmp+pH+PL_cumulo+AN_cumulo+RS+Feed_Vol+Cell_conc._interval+Arg_conc.+emission_O2+consum_O2+interval_O2; 0.105, 0.566, tmp_cumulo+pH+PL_cumulo+AN_cumulo+interval_yield+Feed_Vol+RS_cumulo+Cell_conc._interval+Arg_conc.+emission_O2+emission_CO2+consum_O2+interval_O2; 0.146, 0.566, tmp+tmp_cumulo+pH_cumulo+PL_cumulo+RS_cumulo+Cell_conc._interval+rab_integral+Arg_conc.+emission_CO2+interval_O2+generate_CO2; 0.126, 0.566, tmp+pH+PL_cumulo+AN_cumulo+Feed_Vol+RS_cumulo+Cell_conc._interval+RQ_integral+Arg_conc.+emission_O2+consum_O2+interval_O2; 0.126, 0.566, tmp_cumulo+pH_cumulo+PL_cumulo+AN_cumulo+RS+Feed_Vol+RS_cumulo+Cell_conc._interval+Arg_conc.+emission_O2+interval_O2+generate_CO2; 0.165, 0.566, tmp+PL_cumulo+interval_yield+RS+Feed_Vol+Cell_conc._interval+Arg_conc.+emission_O2+consum_O2+generate_CO2; 0.165, 0.566, tmp+pH_cumulo+PL+PL_cumulo+RS_cumulo+Cell_conc._interval+rab_integral+Arg_conc.+emission_CO2+interval_O2; 0.146, 0.566, tmp_cumulo+PL_cumulo+RS+Feed_Vol+RS_cumulo+Cell_conc._interval+Arg_conc.+emission_O2+emission_CO2+consum_O2+generate_CO2; 0.146, 0.566, tmp+pH+PL+PL_cumulo+AN_cumulo+RS+Cell_conc._interval+rab_integral+Arg_conc.+emission_CO2+interval_O2; 0.165, 0.566, tmp_cumulo+PL_cumulo+interval_yield+Feed_Vol+RS_cumulo+Cell_conc._interval+rab_integral+Arg_conc.+emission_CO2+interval_O2; 0.146, 0.566, tmp+pH_cumulo+PL_cumulo+RS+Feed_Vol+Cell_conc._interval+Arg_conc.+emission_O2+emission_CO2+consum_O2+interval_O2; 0.126, 0.566, tmp_cumulo+PL_cumulo+AN_cumulo+interval_yield+Feed_Vol+RS_cumulo+Cell_conc._interval+RQ_integral+Arg_conc.+emission_O2+interval_O2+generate_CO2; 0.146, 0.566, tmp_cumulo+PL_cumulo+AN_cumulo+interval_yield+Feed_Vol+RS_cumulo+Cell_conc._interval+Arg_conc.+emission_O2+consum_O2+generate_CO2; 0.126, 0.566, tmp+tmp_cumulo+PL_cumulo+AN_cumulo+Feed_Vol+RS_cumulo+Cell_conc._interval+RQ_integral+Arg_conc.+emission_CO2+interval_O2+generate_CO2; 0.146, 0.566, tmp_cumulo+pH_cumulo+PL_cumulo+AN+Feed_Vol+RS_cumulo+Cell_conc._interval+Arg_conc.+emission_O2+consum_O2+interval_O2; 0.165, 0.566, tmp+PL_cumulo+RS+Feed_Vol+Cell_conc._interval+RQ_integral+Arg_conc.+emission_O2+interval_O2+generate_CO2; 0.165, 0.566, tmp+pH+PL_cumulo+AN_cumulo+Feed_Vol+Cell_conc._interval+Arg_conc.+emission_O2+consum_O2+generate_CO2; 0.146, 0.566, tmp+PL+PL_cumulo+RS+Feed_Vol+Cell_conc._interval+Arg_conc.+emission_O2+emission_CO2+consum_O2+generate_CO2; 0.126, 0.566, tmp_cumulo+pH+PL_cumulo+interval_yield+Feed_Vol+RS_cumulo+Cell_conc._interval+Arg_conc.+emission_O2+emission_CO2+consum_O2+interval_O2; 0.165, 0.566, tmp+pH+PL+PL_cumulo+RS_cumulo+Cell_conc._interval+rab_integral+Arg_conc.+emission_CO2+interval_O2; 0.125, 0.566, tmp_cumulo+pH+PL_cumulo+interval_yield+Feed_Vol+RS_cumulo+Cell_ conc._interval+Arg_conc.+emission_O2+emission_CO2+interval_O2+generate_CO2; 0.146, 0.566, tmp_cumulo+PL+PL_cumulo+Feed_Vol+RS_cumulo+Cell_conc._interval+RQ_integral+Arg_conc.+emission_O2+interval_O2+generate_CO2; 0.146, 0.565, tmp_cumulo+PL_cumulo+interval_yield+Feed_Vol+RS_cumulo+Cell_conc._interval+Arg_conc.+emission_O2+emission_CO2+consum_O2+generate_CO2; 0.146, 0.565, tmp_cumulo+PL_cumulo+AN+Feed_Vol+RS_cumulo+Cell_conc._interval+RQ_integral+Arg_conc.+emission_CO2+interval_O2+generate_CO2; 0.146, 0.565, tmp_cumulo+pH+PL_cumulo+Feed_Vol+RS_cumulo+Cell_conc._cumulo+Cell_conc._interval+Arg_conc.+emission_O2+consum_O2+interval_O2; 0.146, 0.565, tmp_cumulo+pH_cumulo+PL_cumulo+RS+Feed_Vol+Cell_conc._interval+Arg_conc.+emission_O2+emission_CO2+consum_O2+interval_O2; 0.146, 0.565, tmp+PL+PL_cumulo+AN_cumulo+Feed_Vol+RS_cumulo+Cell_conc._interval+rab_integral+Arg_conc.+emission_CO2+interval_O2; 0.165, 0.565, tmp_cumulo+PL_cumulo+Feed_Vol+RS_cumulo+Cell_conc._interval+rab_integral+Arg_conc.+emission_O2+emission_CO2+interval_O2; 0.125, 0.565, tmp_cumulo+pH+PL_cumulo+AN_cumulo+Feed_Vol+RS_cumulo+Cell_conc._cumulo+Cell_conc._interval+Arg_conc.+emission_O2+consum_O2+interval_O2; 0.146, 0.565, tmp+PL_cumulo+AN+AN_cumulo+Feed_Vol+RS_cumulo+Cell_conc._interval+Arg_conc.+emission_O2+interval_O2+generate_CO2; 0.165, 0.565, tmp_cumulo+PL_cumulo+Feed_Vol+RS_cumulo+Cell_conc._cumulo+Cell_conc._interval+RQ_integral+Arg_conc.+emission_CO2+interval_O2; 0.146, 0.565, tmp_cumulo+PL_cumulo+RS+Feed_Vol+RS_cumulo+Cell_conc._interval+RQ_integral+Arg_conc.+emission_O2+emission_CO2+interval_O2; 0.146, 0.565, tmp_cumulo+PL_cumulo+AN_cumulo+Feed_Vol+RS_cumulo+Cell_conc._interval+rab_integral+Arg_conc.+emission_CO2+consum_O2+interval_O2; 0.146, 0.565, tmp+pH_cumulo+PL+PL_cumulo+AN+RS_cumulo+Cell_conc._interval+rab_integral+Arg_conc.+emission_CO2+interval_O2; 0.125, 0.565, tmp_cumulo+pH+PL_cumulo+AN+AN_cumulo+RS+RS_cumulo+Cell_conc._interval+rab_integral+Arg_conc.+emission_CO2+interval_O2; 0.201, 0.565, tmp_cumulo+PL_cumulo+RS_cumulo+Cell_conc._interval+rab_integral+Arg_conc.+emission_O2+interval_O2; 0.145, 0.565, tmp_cumulo+pH+pH_cumulo+PL+PL_cumulo+RS_cumulo+Cell_conc._interval+rab_integral+Arg_conc.+emission_CO2+interval_O2; 0.165, 0.565, tmp_cumulo+PL_cumulo+AN_cumulo+Feed_Vol+RS_cumulo+Cell_conc._interval+rab_integral+Arg_conc.+emission_O2+interval_O2; 0.183, 0.565, tmp_cumulo+PL_cumulo+Feed_Vol+RS_cumulo+Cell_conc._interval+Arg_conc.+emission_CO2+consum_O2+generate_CO2; 0.165, 0.565, tmp_cumulo+PL+PL_cumulo+RS_cumulo+Cell_conc._interval+rab_integral+Arg_conc.+emission_CO2+interval_O2+generate_CO2; 0.145, 0.565, tmp_cumulo+pH+PL_cumulo+interval_yield+Feed_Vol+RS_cumulo+Cell_conc._interval+rab_integral+Arg_conc.+emission_O2+interval_O2; 0.145, 0.565, tmp_cumulo+pH+PL_cumulo+OD+Feed_Vol+RS_cumulo+Cell_conc._interval+RQ_integral+Arg_conc.+emission_CO2+interval_O2; 0.145, 0.565, tmp_cumulo+pH_cumulo+PL_cumulo+RS_cumulo+Cell_conc._interval+rab_integral+Arg_conc.+emission_O2+emission_CO2+interval_O2+generate_CO2; 0.165, 0.565, tmp_cumulo+pH+PL_cumulo+AN_cumulo+RS_cumulo+Cell_conc._interval+rab_integral+Arg_conc.+emission_O2+interval_O2; 0.201, 0.565, tmp+PL_cumulo+RS_cumulo+Cell_conc._interval+Arg_conc.+emission_O2+interval_O2+generate_CO2; 0.145, 0.565, tmp+pH_cumulo+PL_cumulo+Feed_Vol+RS_cumulo+Cell_conc._interval+Arg_conc.+emission_O2+consum_O2+interval_O2+generate_CO2; 0.125, 0.565, tmp_cumulo+pH+PL_cumulo+AN_cumulo+Feed_Vol+RS_cumulo+Cell_conc._cumulo+Cell_conc._interval+rab_integral+Arg_conc.+emission_CO2+interval_O2; 0.145, 0.565, tmp_cumulo+PL_cumulo+Feed_Vol+RS_cumulo+Cell_conc._interval+Arg_conc.+emission_O2+emission_CO2+consum_O2+interval_O2+generate_CO2; 0.165, 0.565, tmp_cumulo+pH+PL_cumulo+RS+RS_cumulo+Cell_conc._interval+Arg_conc.+emission_O2+consum_O2+interval_O2; 0.125, 0.565, tmp+pH_cumulo+PL_cumulo+AN_cumulo+RS+Feed_Vol+Cell_conc._interval+Arg_conc.+emission_O2+emission_CO2+interval_O2+generate_CO2; 0.165, 0.565, tmp_cumulo+PL_cumulo+AN_cumulo+RS+RS_cumulo+Cell_conc._interval+RQ_integral+Arg_conc.+emission_CO2+interval_O2; 0.145, 0.565, tmp_cumulo+pH_cumulo+PL+PL_cumulo+Feed_Vol+RS_cumulo+Cell_conc._interval+Arg_conc.+emission_O2+interval_O2+generate_CO2; 0.145, 0.565, tmp_cumulo+PL+PL_cumulo+Feed_Vol+RS_cumulo+Cell_conc._interval+Arg_conc.+emission_O2+emission_CO2+interval_O2+generate_CO2; 0.165, 0.565, tmp+PL_cumulo+AN_cumulo+Feed_Vol+Cell_conc._interval+rab_integral+Arg_conc.+emission_O2+consum_O2+generate_CO2; 0.145, 0.565, tmp+PL+PL_cumulo+interval_yield+Feed_Vol+RS_cumulo+Cell_conc._interval+Arg_conc.+emission_O2+interval_O2+generate_CO2; 0.183, 0.565, tmp_cumulo+pH+PL+PL_cumulo+RS_cumulo+Cell_conc._interval+Arg_conc.+emission_O2+interval_O2; 0.125, 0.565, tmp_cumulo+PL+PL_cumulo+AN_cumulo+interval_yield+Feed_Vol+RS_cumulo+Cell_conc._interval+RQ_integral+Arg_conc.+emission_CO2+interval_O2; 0.103, 0.565, tmp_cumulo+pH+PL_cumulo+AN_cumulo+RS+Feed_Vol+RS_cumulo+Cell_conc._interval+rab_integral+Arg_conc.+emission_CO2+consum_O2+interval_O2; 0.145, 0.565, tmp_cumulo+pH+PL_cumulo+AN_cumulo+RS+RS_cumulo+Cell_conc._interval+RQ_integral+Arg_conc.+emission_CO2+interval_O2; 0.145, 0.565, tmp+PL+PL_cumulo+AN_cumulo+RS+Feed_Vol+Cell_conc._interval+Arg_conc.+emission_O2+interval_O2+generate_CO2; 0.145, 0.565, tmp_cumulo+pH+PL_cumulo+AN_cumulo+Feed_Vol+RS_cumulo+Cell_conc._interval+Arg_conc.+emission_O2+consum_O2+generate_CO2; 0.125, 0.565, tmp_cumulo+pH+PL_cumulo+Feed_Vol+RS_cumulo+Cell_conc._interval+rab_integral+Arg_conc.+emission_O2+emission_CO2+consum_O2+interval_O2; 0.183, 0.565, tmp_cumulo+PL_cumulo+interval_yield+RS_cumulo+Cell_conc._interval+RQ_integral+Arg_conc.+emission_CO2+interval_O2; 0.164, 0.565, tmp+PL_cumulo+AN_cumulo+Feed_Vol+Cell_conc._interval+Arg_conc.+emission_O2+emission_CO2+interval_O2+generate_CO2; 0.145, 0.565, tmp_cumulo+PL_cumulo+interval_yield+Feed_Vol+RS_cumulo+Cell_conc._interval+RQ_integral+Arg_conc.+emission_CO2+consum_O2+generate_CO2; 0.145, 0.565, tmp+pH+PL_cumulo+Feed_Vol+RS_cumulo+Cell_conc._interval+Arg_conc.+emission_O2+consum_O2+interval_O2+generate_CO2; 0.164, 0.565, tmp+pH_cumulo+PL_cumulo+AN_cumulo+Feed_Vol+Cell_conc._interval+Arg_conc.+emission_O2+interval_O2+generate_CO2; 0.145, 0.565, tmp+PL+PL_cumulo+RS+Feed_Vol+RS_cumulo+Cell_conc._interval+Arg_conc.+emission_O2+consum_O2+generate_CO2; 0.125, 0.565, tmp+pH+PL+PL_cumulo+interval_yield+Feed_Vol+RS_cumulo+Cell_conc._interval+RQ_integral+Arg_conc.+emission_CO2+interval_O2; 0.164, 0.565, tmp+PL_cumulo+Feed_Vol+RS_cumulo+Cell_conc._cumulo+Cell_conc._interval+Arg_conc.+emission_O2+interval_O2+generate_CO2; 0.145, 0.565, tmp_cumulo+PL+PL_cumulo+Feed_Vol+RS_cumulo+Cell_conc._interval+rab_integral+RQ_integral+Arg_conc.+emission_CO2+interval_O2; 0.183, 0.565, tmp+pH+PL_cumulo+RS_cumulo+Cell_conc._interval+rab_integral+Arg_conc.+emission_O2+ interval_O2; 0.201, 0.565, tmp_cumulo+pH+PL_cumulo+RS_cumulo+Cell_conc._interval+Accum._Yield+emission_O2+interval_O2; 0.124, 0.565, tmp_cumulo+pH+pH_cumulo+PL_cumulo+AN_cumulo+RS_cumulo+Cell_conc._interval+rab_integral+Arg_conc.+emission_CO2+interval_O2+generate_CO2; 0.164, 0.565, tmp_cumulo+PL+PL_cumulo+AN_cumulo+RS_cumulo+Cell_conc._interval+RQ_integral+Arg_conc.+emission_CO2+interval_O2; 0.145, 0.565, tmp_cumulo+pH+PL_cumulo+AN_cumulo+RS+Feed_Vol+Cell_conc._interval+Arg_conc.+emission_O2+consum_O2+interval_O2; 0.164, 0.565, tmp_cumulo+pH+PL_cumulo+RS_cumulo+Cell_conc._interval+rab_integral+Arg_conc.+emission_O2+interval_O2+generate_CO2; 0.145, 0.565, tmp_cumulo+pH+pH_cumulo+PL_cumulo+Feed_Vol+RS_cumulo+Cell_conc._interval+rab_integral+Arg_conc.+emission_O2+interval_O2; 0.200, 0.565, tmp_cumulo+PL_cumulo+RS_cumulo+Cell_conc._interval+Arg_conc.+emission_O2+consum_O2+interval_O2; 0.145, 0.565, tmp_cumulo+PL+PL_cumulo+AN_cumulo+Feed_Vol+RS_cumulo+Cell_conc._interval+rab_integral+Arg_conc.+emission_CO2+interval_O2; 0.164, 0.565, tmp_cumulo+PL_cumulo+interval_yield+Feed_Vol+RS_cumulo+Cell_conc._interval+RQ_integral+Arg_conc.+emission_O2+interval_O2; 0.183, 0.565, tmp+PL_cumulo+Feed_Vol+Cell_conc._interval+rab_integral+Arg_conc.+emission_O2+consum_O2+generate_CO2; 0.103, 0.565, tmp_cumulo+pH+PL+PL_cumulo+AN_cumulo+RS+Feed_Vol+RS_cumulo+Cell_conc._interval+Arg_conc.+emission_O2+consum+interval_O2; 0.124, 0.565, tmp_cumulo+pH_cumulo+PL_cumulo+interval_yield+Feed_Vol+RS_cumulo+Cell_conc._interval+Arg_conc.+emission_O2+emission_CO2+interval_O2+generate_CO2; 0.124, 0.565, tmp+PL_cumulo+AN_cumulo+Feed_Vol+RS_cumulo+Cell_conc._interval+Arg_conc.+emission_O2+emission_CO2+consum_O2+interval_O2+generate_CO2; 0.144, 0.565, tmp+pH+PL_cumulo+AN_cumulo+RS+Feed_Vol+Cell_conc._interval+Arg_conc.+emission_O2+consum_O2+generate_CO2; 0.144, 0.565, tmp_cumulo+pH+PL_cumulo+AN_cumulo+RS+Feed_Vol+RS_cumulo+Cell_conc._interval+Arg_conc.+emission_O2+interval_O2; 0.164, 0.565, tmp_cumulo+pH_cumulo+PL_cumulo+RS+Feed_Vol+Cell_conc._interval+RQ_integral+Arg_conc.+emission_CO2+interval_O2; 0.164, 0.565, tmp+tmp_cumulo+pH+PL_cumulo+RS_cumulo+Cell_conc._interval+RQ_integral+Arg_conc.+emission_CO2+interval_O2; 0.144, 0.565, tmp_cumulo+PL+PL_cumulo+Feed_Vol+RS_cumulo+Cell_conc._interval+RQ_integral+Arg_conc.+emission_CO2+consum_O2+generate_CO2; 0.164, 0.564, tmp+PL+PL_cumulo+RS+RS_cumulo+Cell_conc._interval+rab_integral+Arg_conc.+emission_CO2+interval_O2; 0.124, 0.564, tmp+PL+PL_cumulo+AN_cumulo+Feed_Vol+RS_cumulo+Cell_conc._interval+Arg_conc.+emission_O2+consum_O2+interval_O2+generate_CO2; 0.103, 0.564, tmp+PL+PL_cumulo+AN_cumulo+Feed_Vol+RS_cumulo+Cell_conc._interval+rab_integral+Arg_conc.+emission_O2+emission_CO2+interval_O2+generate_CO2; 0.164, 0.564, tmp_cumulo+pH_cumulo+PL+PL_cumulo+RS_cumulo+Cell_conc._interval+RQ_integral+Arg_conc.+emission_CO2+interval_O2; 0.144, 0.564, tmp+pH+PL_cumulo+RS+Feed_Vol+Cell_conc._interval+Arg_conc.+emission_O2+emission_CO2+consum_O2+generate_CO2; 0.103, 0.564, tmp_cumulo+pH+PL_cumulo+AN_cumulo+Feed_Vol+RS_cumulo+Cell_conc._interval+RQ_integral+Arg_conc.+emission_O2+emission_CO2+consum_O2+interval_O2; 0.144, 0.564, tmp+PL+AN_cumulo+RS+Feed_Vol+Cell_conc._interval+RQ_integral+Arg_conc.+emission_O2+interval_O2+generate_CO2; 0.124, 0.564, tmp_cumulo+pH+pH_cumulo+PL_cumulo+Feed_Vol+RS_cumulo+Cell_conc._interval+Arg_conc.+emission_O2+emission_CO2+consum_O2+interval_O2; 0.124, 0.564, tmp_cumulo+pH_cumulo+PL+PL_cumulo+AN_cumulo+RS_cumulo+Cell_conc._interval+rab_integral+Arg_conc.+emission_CO2+interval_O2+generate_CO2; 0.144, 0.564, tmp_cumulo+pH_cumulo+PL_cumulo+AN_cumulo+Feed_Vol+RS_cumulo+Cell_conc._interval+RQ_integral+Arg_conc.+emission_O2+interval_O2; 0.164, 0.564, tmp_cumulo+PL_cumulo+AN_cumulo+RS_cumulo+Cell_conc._interval+rab_integral+Arg_conc.+emission_CO2+consum_O2+interval_O2; 0.102, 0.564, tmp_cumulo+pH_cumulo+PL_cumulo+AN_cumulo+interval_yield+Feed_Vol+RS_cumulo+Cell_conc._interval+Arg_conc.+emission_O2+emission_CO2+consum_O2+interval_O2; 0.124, 0.564, tmp_cumulo+pH_cumulo+PL_cumulo+AN_cumulo+Feed_Vol+RS_cumulo+Cell_conc._interval+rab_integral+RQ_integral+Arg_conc.+emission_CO2+interval_O2; 0.164, 0.564, tmp_cumulo+pH_cumulo+PL_cumulo+RS_cumulo+Cell_conc._interval+rab_integral+RQ_integral+Arg_conc.+emission_O2+interval_O2; 0.144, 0.564, tmp+PL_cumulo+interval_yield+Feed_Vol+RS_cumulo+Cell_conc._interval+rab_integral+Arg_conc.+emission_O2+interval_O2+generate_CO2; 0.124, 0.564, tmp_cumulo+pH+PL+PL_cumulo+AN+AN_cumulo+RS_cumulo+Cell_conc._interval+rab_integral+Arg_conc.+emission_CO2+interval_O2; 0.124, 0.564, tmp+PL_cumulo+AN_cumulo+Feed_Vol+RS_cumulo+Cell_conc._interval+rab_integral+Arg_conc.+emission_O2+emission_CO2+consum_O2+generate_CO2; 0.124, 0.564, tmp_cumulo+pH+PL_cumulo+AN+RS+RS_cumulo+Cell_conc._interval+rab_integral+Arg_conc.+emission_O2+emission_CO2+interval_O2; 0.163, 0.564, tmp+tmp_cumulo+pH+PL_cumulo+Feed_Vol+RS_cumulo+Cell_conc._interval+Arg_conc.+emission_O2+interval_O2; 0.144, 0.564, tmp+tmp_cumulo+PL_cumulo+AN_cumulo+Feed_Vol+RS_cumulo+Cell_conc._interval+Arg_conc.+emission_O2+consum_O2+interval_O2; 0.123, 0.564, tmp+pH_cumulo+PL_cumulo+AN_cumulo+RS+Feed_Vol+RS_cumulo+Cell_conc._interval+Arg_conc.+emission_O2+consum_O2+interval_O2; 0.144, 0.564, tmp_cumulo+pH_cumulo+PL_cumulo+AN_cumulo+interval_yield+Feed_Vol+RS_cumulo+Cell_conc._interval+rab_integral+Arg_conc.+interval_O2; 0.182, 0.564, PL_cumulo+RS+Feed_Vol+RS_cumulo+Cell_conc._interval+Arg_conc.+emission_O2+consum_O2+generate_CO2; 0.163, 0.564, tmp_cumulo+pH+PL_cumulo+RS+Feed_Vol+Cell_conc._interval+Arg_conc.+emission_O2+consum_O2+interval_O2; 0.182, 0.564, tmp_cumulo+PL_cumulo+AN+RS_cumulo+Cell_conc._interval+rab_integral+Arg_conc.+emission_CO2+interval_O2; 0.144, 0.564, tmp_cumulo+pH_cumulo+PL+PL_cumulo+RS_cumulo+Cell_conc._interval+rab_integral+Arg_conc.+emission_CO2+consum_O2+interval_O2; 0.163, 0.564, tmp_cumulo+PL_cumulo+RS+RS_cumulo+Cell_conc._interval+rab_integral+Arg_conc.+emission_O2+emission_CO2+interval_O2; 0.163, 0.564, tmp+pH_cumulo+PL_cumulo+Feed_Vol+RS_cumulo+Cell_conc._interval+Arg_conc.+emission_O2+emission_CO2+interval_O2; 0.102, 0.564, tmp_cumulo+pH+PL_cumulo+AN_cumulo+interval_yield+RS+Feed_Vol+RS_cumulo+Cell_conc._interval+Arg_conc.+emission_O2+consum_O2+interval_O2; 0.144, 0.564, tmp_cumulo+pH_cumulo+PL_cumulo+Feed_Vol+RS_cumulo+Cell_conc._interval+RQ_integral+Arg_conc.+emission_O2+interval_O2+generate_CO2; 0.144, 0.564, tmp+pH+PL_cumulo+AN+Feed_Vol+RS_cumulo+Cell_conc._interval+Arg_conc.+emission_O2+interval_O2+generate_CO2; 0.123, 0.564, tmp+PL+PL_cumulo+AN_cumulo+Feed_Vol+RS_cumulo+Cell_conc._interval+RQ_integral+Arg_conc.+emission_CO2+consum_O2+generate_CO2; 0.102, 0.564, tmp_cumulo+pH+pH_cumulo+PL_cumulo+AN_cumulo+Feed_Vol+RS_cumulo+Cell_conc._interval+Arg_conc.+ emission_O2+emission_CO2+consum_O2+interval_O2; 0.123, 0.564, tmp+tmp_cumulo+pH+PL_cumulo+AN_cumulo+RS+RS_cumulo+Cell_conc._interval+rab_integral+Arg_conc.+emission_CO2+interval_O2; 0.144, 0.564, tmp_cumulo+pH+PL_cumulo+RS_cumulo+Cell_conc._interval+rab_integral+Arg_conc.+emission_CO2+consum_O2+interval_O2+generate_CO2; 0.123, 0.564, tmp_cumulo+PL_cumulo+AN_cumulo+Feed_Vol+RS_cumulo+Cell_conc._interval+rab_integral+RQ_integral+Arg_conc.+emission_CO2+interval_O2+generate_CO2; 0.102, 0.564, tmp_cumulo+pH+PL+PL_cumulo+AN_cumulo+Feed_Vol+RS_cumulo+Cell_conc._interval+RQ_integral+Arg_conc.+emission_CO2+consum_O2+interval_O2; 0.144, 0.564, tmp_cumulo+pH+PL+PL_cumulo+AN_cumulo+Feed_Vol+RS_cumulo+Cell_conc._interval+Arg_conc.+emission_O2+interval_O2; 0.144, 0.564, tmp_cumulo+pH+PL_cumulo+OD+Feed_Vol+RS_cumulo+Cell_conc._interval+rab_integral+Arg_conc.+emission_CO2+interval_O2; 0.102, 0.564, tmp+PL+PL_cumulo+AN_cumulo+Feed_Vol+RS_cumulo+Cell_conc._interval+RQ_integral+Arg_conc.+emission_O2+emission_CO2+interval_O2+generate_CO2; 0.163, 0.564, tmp+PL_cumulo+AN_cumulo+Feed_Vol+Cell_conc._interval+RQ_integral+Arg_conc.+emission_CO2+consum_O2+generate_CO2; 0.123, 0.564, tmp+PL+PL_cumulo+AN_cumulo+Feed_Vol+RS_cumulo+Cell_conc._interval+rab_integral+Arg_conc.+emission_O2+consum_O2+interval_O2; 0.143, 0.564, tmp_cumulo+PL+PL_cumulo+AN+Feed_Vol+RS_cumulo+Cell_conc._interval+RQ_integral+Arg_conc.+emission_CO2+interval_O2; 0.123, 0.564, tmp_cumulo+pH+PL_cumulo+RS+Feed_Vol+RS_cumulo+Cell_conc._interval+rab_integral+Arg_conc.+emission_CO2+interval_O2+generate_CO2; 0.123, 0.564, tmp_cumulo+PL+PL_cumulo+interval_yield+Feed_Vol+RS_cumulo+Cell_conc._interval+RQ_integral+Arg_conc.+emission_CO2+interval_O2+generate_CO2; 0.143, 0.564, tmp+pH+PL_cumulo+AN_cumulo+Feed_Vol+RS_cumulo+Cell_conc._interval+rab_integral+Arg_conc.+emission_O2+interval_O2; 0.123, 0.564, tmp+PL+PL_cumulo+AN_cumulo+Feed_Vol+RS_cumulo+Cell_conc._interval+RQ_integral+Arg_conc.+emission_O2+consum_O2+generate_CO2; 0.123, 0.564, tmp_cumulo+pH_cumulo+PL_cumulo+RS+Feed_Vol+RS_cumulo+Cell_conc._interval+Arg_conc.+emission_O2+emission_CO2+consum_O2+interval_O2; 0.143, 0.564, tmp_cumulo+pH_cumulo+PL_cumulo+AN_cumulo+RS+Feed_Vol+Cell_conc._interval+Arg_conc.+emission_O2+consum_O2+interval_O2; 0.143, 0.564, tmp_cumulo+pH+PL_cumulo+RS_cumulo+Cell_conc._interval+rab_integral+Arg_conc.+emission_O2+emission_CO2+consum_O2+interval_O2; 0.143, 0.564, tmp_cumulo+pH+PL_cumulo+OD+Feed_Vol+RS_cumulo+Cell_conc._interval+Arg_conc.+emission_O2+consum_O2+interval_O2; 0.143, 0.564, tmp+tmp_cumulo+PL_cumulo+Feed_Vol+RS_cumulo+Cell_conc._interval+rab_integral+Arg_conc.+emission_O2+interval_O2+generate_CO2; 0.163, 0.564, tmp_cumulo+pH+PL+PL_cumulo+RS_cumulo+Cell_conc._interval+rab_integral+Arg_conc.+emission_O2+interval_O2; 0.123, 0.564, tmp_cumulo+pH_cumulo+PL_cumulo+interval_yield+RS+Feed_Vol+RS_cumulo+Cell_conc._interval+Arg_conc.+emission_O2+consum_O2+interval_O2; 0.123, 0.564, tmp+pH_cumulo+PL_cumulo+AN_cumulo+RS+Feed_Vol+Cell_conc._interval+Arg_conc.+emission_O2+emission_CO2+consum_O2+interval_O2; 0.143, 0.564, tmp+pH+PL_cumulo+RS+Feed_Vol+RS_cumulo+Cell_conc._interval+Arg_conc.+emission_O2+consum_O2+generate_CO2; 0.143, 0.564, tmp_cumulo+PL_cumulo+interval_yield+RS+Feed_Vol+RS_cumulo+Cell_conc._interval+Arg_conc.+emission_O2+consum_O2+generate_CO2; 0.123, 0.564, tmp+tmp_cumulo+PL+PL_cumulo+AN_cumulo+Feed_Vol+RS_cumulo+Cell_conc._interval+RQ_integral+Arg_conc.+emission_CO2+interval_O2; 0.163, 0.564, tmp_cumulo+pH_cumulo+PL_cumulo+RS+Feed_Vol+RS_cumulo+Cell_conc._interval+Arg_conc.+emission_O2+interval_O2; 0.143, 0.564, tmp_cumulo+pH+PL_cumulo+RS+RS_cumulo+Cell_conc._interval+rab_integral+RQ_integral+Arg_conc.+emission_CO2+interval_O2; 0.123, 0.564, tmp_cumulo+PL+PL_cumulo+AN_cumulo+RS+Feed_Vol+RS_cumulo+Cell_conc._interval+RQ_integral+Arg_conc.+emission_CO2+interval_O2; 0.123, 0.564, tmp_cumulo+pH+PL_cumulo+interval_yield+Feed_Vol+RS_cumulo+Cell_conc._interval+RQ_integral+Arg_conc.+emission_CO2+consum_O2+interval_O2; 0.143, 0.564, tmp+PL+PL_cumulo+interval_yield+Feed_Vol+RS_cumulo+Cell_conc._interval+Arg_conc.+emission_O2+consum_O2+generate_CO2; 0.181, 0.564, tmp+PL_cumulo+Feed_Vol+Cell_conc._interval+Arg_conc.+emission_O2+consum_O2+generate_CO2; 0.163, 0.564, tmp+PL_cumulo+interval_yield+Feed_Vol+RS_cumulo+Cell_conc._interval+RQ_integral+Arg_conc.+emission_CO2+interval_O2; 0.101, 0.564, tmp_cumulo+pH+PL+PL_cumulo+AN_cumulo+Feed_Vol+RS_cumulo+Cell_conc._interval+rab_integral+Arg_conc.+emission_O2+consum_O2+interval_O2; 0.123, 0.564, tmp_cumulo+PL_cumulo+AN_cumulo+interval_yield+Feed_Vol+RS_cumulo+Cell_conc._interval+rab_integral+Arg_conc.+emission_O2+interval_O2+generate_CO2; 0.181, 0.564, tmp_cumulo+PL_cumulo+RS+Feed_Vol+Cell_conc._interval+Arg_conc.+emission_O2+consum_O2+generate_CO2; 0.123, 0.563, tmp_cumulo+pH+PL_cumulo+Feed_Vol+RS_cumulo+Cell_conc._interval+RQ_integral+Arg_conc.+emission_O2+emission_CO2+consum_O2+interval_O2; 0.162, 0.563, tmp+PL+PL_cumulo+Feed_Vol+RS_cumulo+Cell_conc._interval+rab_integral+Arg_conc.+emission_CO2+interval_O2; 0.122, 0.563, tmp_cumulo+pH+PL+PL_cumulo+AN_cumulo+Feed_Vol+RS_cumulo+Cell_conc._interval+rab_integral+Arg_conc.+emission_O2+interval_O2; 0.122, 0.563, tmp+pH_cumulo+PL_cumulo+AN_cumulo+Feed_Vol+RS_cumulo+Cell_conc._interval+rab_integral+Arg_conc.+emission_O2+consum_O2+interval_O2; 0.143, 0.563, tmp_cumulo+pH_cumulo+PL_cumulo+RS+RS_cumulo+Cell_conc._cumulo+Cell_conc._interval+rab_integral+Arg_conc.+emission_CO2+interval_O2; 0.143, 0.563, tmp_cumulo+pH_cumulo+PL_cumulo+AN_cumulo+interval_yield+Feed_Vol+RS_cumulo+Cell_conc._interval+RQ_integral+Arg_conc.+interval_O2; 0.181, 0.563, tmp+PL_cumulo+RS_cumulo+Cell_conc._interval+rab_integral+Arg_conc.+emission_CO2+consum_O2+interval_O2; 0.122, 0.563, tmp+PL_cumulo+AN_cumulo+RS+Feed_Vol+RS_cumulo+Cell_conc._interval+rab_integral+Arg_conc.+emission_CO2+interval_O2+generate_CO2; 0.143, 0.563, tmp+PL_cumulo+interval_yield+Feed_Vol+RS_cumulo+Cell_conc._interval+RQ_integral+Arg_conc.+emission_O2+interval_O2+generate_CO2; 0.181, 0.563, tmp_cumulo+PL_cumulo+AN_cumulo+Feed_Vol+RS_cumulo+Cell_conc._interval+Arg_conc.+emission_O2+interval_O2; 0.181, 0.563, tmp_cumulo+pH+PL_cumulo+interval_yield+RS_cumulo+Cell_conc._interval+Arg_conc.+emission_O2+interval_O2; 0.122, 0.563, tmp_cumulo+PL_cumulo+AN_cumulo+RS+Feed_Vol+RS_cumulo+Cell_conc._interval+rab_integral+Arg_conc.+emission_CO2+consum_O2+interval_O2; 0.122, 0.563, tmp+pH+PL_cumulo+AN_cumulo+interval_yield+Feed_Vol+RS_cumulo+Cell_conc._interval+Arg_conc.+emission_O2+consum_O2+interval_O2; 0.162, 0.563, tmp_cumulo+pH+PL_cumulo+RS_cumulo+Cell_conc._interval+rab_integral+Arg_conc.+emission_CO2+consum_O2+generate_CO2; 0.122, 0.563, tmp_cumulo+pH_cumulo+PL_cumulo+AN_cumulo+Feed_Vol+RS_cumulo+Cell_ conc._interval+RQ_integral+Arg_conc.+emission_O2+ emission_CO2+interval_O2; 0.162, 0.563, tmp+pH+PL_ cumulo+Feed_Vol+RS_cumulo+Cell_conc._interval+RQ_ integral+Arg_conc.+emission_O2+interval_O2; 0.101, 0.563, tmp_cumulo+pH+PL_cumulo+AN_cumulo+RS+ Feed_Vol+RS_cumulo+Cell_conc._interval+rab_integral+ Arg_conc.+emission_O2+consum_O2+interval_O2; 0.143, 0.563, tmp+pH_cumulo+PL_cumulo+Feed_Vol+RS_cu- mulo+Cell_conc._interval+rab_integral+Arg_conc.+emis- sion_O2+interval_O2+generate_CO2; 0.143, 0.563, tmp_ cumulo+pH_cumulo+PL+PL_cumulo+Feed_Vol+RS_ cumulo+Cell_conc._interval+rab_integral+Arg_conc.+ emission_O2+interval_O2; 0.122, 0.563, tmp+PL_cumulo+ AN_cumulo+interval_yield+Feed_Vol+RS_cumulo+Cell_ conc._interval+rab_integral+Arg_conc.+emission_O2+ interval_O2+generate_CO2; 0.143, 0.563, tmp_cumulo+ pH+PL_cumulo+AN_cumulo+Feed_Vol+RS_cumulo+Cell_conc._ interval+rab_integral+Accum._Yield+Arg_conc.+ emission_CO2+interval_O2; 0.162, 0.563, tmp+pH+PL_ cumulo+RS_cumulo+Cell_conc._cumulo+Cell_conc._ interval+rab_integral+Arg_conc.+emission_CO2+interval_ O2; 0.162, 0.563, tmp_cumulo+PL_cumulo+RS+RS_ cumulo+Cell_conc._interval+RQ_integral+Arg_conc.+ emission_CO2+interval_O2+generate_CO2; 0.143, 0.563, tmp+PL+PL_cumulo+RS+Feed_Vol+Cell_conc._interval+ RQ_integral+Arg_conc.+emission_O2+consum_O2+gener- ate_CO2; 0.143, 0.563, tmp+pH_cumulo+PL_cumulo+RS+ Feed_Vol+RS_cumulo+Cell_conc._interval+Arg_conc.+ emission_O2+consum_O2+interval_O2; 0.143, 0.563, tmp+ PL_cumulo+AN_cumulo+RS+Feed_Vol+Cell_conc._ interval+rab_integral+Arg_conc.+emission_O2+consum_ O2+generate_CO2; 0.143, 0.563, tmp+PL+PL_cumulo+ Feed_Vol+RS_cumulo+Cell_conc._interval+Arg_conc.+ emission_O2+consum_O2+interval_O2+generate_CO2; 0.143, 0.563, tmp+tmp_cumulo+pH+PL+PL_cumulo+RS_ cumulo+Cell_conc._interval+rab_integral+Arg_conc.+ emission_CO2+interval_O2; 0.143, 0.563, tmp_cumulo+ pH+PL_cumulo+AN+Feed_Vol+RS_cumulo+Cell_conc._ interval+rab_integral+Arg_conc.+emission_O2+interval_ O2; 0.122, 0.563, tmp+pH+PL_cumulo+AN_cumulo+RS+ Feed_Vol+Cell_conc._interval+Arg_conc.+emission_O2+ emission_CO2+interval_O2+generate_CO2; 0.122, 0.563, tmp+pH+PL_cumulo+AN_cumulo+Feed_Vol+RS_cu- mulo+Cell_conc._interval+RQ_integral+Arg_conc.+emis- sion_O2+interval_O2+generate_CO2; 0.162, 0.563, tmp_ cumulo+PL+PL_cumulo+interval_yield+Feed_Vol+RS_ cumulo+Cell_conc._interval+RQ_integral+Arg_conc.+ interval_O2; 0.142, 0.563, tmp+PL_cumulo+RS+Feed_ Vol+RS_cumulo+Cell_conc._interval+rab_integral+Arg_ conc.+emission_O2+consum_O2+generate_CO2; 0.142, 0.563, tmp_cumulo+PL+PL_cumulo+RS+RS_cumulo+ Cell_conc._interval+rab_integral+Arg_conc.+emission_ CO2+interval_O2+generate_CO2; 0.215, 0.563, tmp_cu- mulo+PL_cumulo+RS_cumulo+Cell_conc._interval+Arg_ conc.+emission_O2+interval_O2; 0.142, 0.563, tmp_ cumulo+pH+PL_cumulo+interval_yield+RS_cumulo+ Cell_conc._interval+rab_integral+Arg_conc.+emission_ CO2+consum_O2+interval_O2; 0.142, 0.563, tmp_ cumulo+pH_cumulo+PL_cumulo+AN+RS_cumulo+Cell_ conc._interval+rab_integral+Arg_conc.+emission_CO2+ interval_O2+generate_CO2; 0.181, 0.563, tmp+PL_ cumulo+Feed_Vol+RS_cumulo+Cell_conc._interval+Arg_ conc.+emission_CO2+interval_O2+generate_CO2; 0.122, 0.563, tmp_cumulo+PL_cumulo+AN+Feed_Vol+ RS_cumulo+Cell_conc._interval+rab_integral+Arg_conc.+ emission_O2+emission_CO2+interval_O2+generate_CO2; 0.142, 0.563, tmp_cumulo+pH_cumulo+PL_cumulo+AN_ cumulo+RS_cumulo+Cell_conc._interval+rab_integral+ RQ_integral+Arg_conc.+emission_CO2+interval_O2; 0.162, 0.563, tmp_cumulo+pH+PL_cumulo+RS+Feed_ Vol+Cell_conc._interval+RQ_integral+Arg_conc.+emis- sion_CO2+interval_O2; 0.142, 0.563, tmp_cumulo+pH+ PL_cumulo+RS+Feed_Vol+RS_cumulo+Cell_conc._ interval+Arg_conc.+emission_O2+consum_O2+generate_ CO2; 0.101, 0.563, tmp_cumulo+PL+PL_cumulo+AN_ cumulo+interval_yield+Feed_Vol+RS_cumulo+Cell_ conc._interval+RQ_integral+Arg_conc.+emission_CO2+ interval_O2+generate_CO2; 0.142, 0.563, tmp+PL_ cumulo+Feed_Vol+RS_cumulo+Cell_conc._interval+rab_ integral+RQ_integral+Arg_conc.+emission_O2+interval_ O2+generate_CO2; 0.122, 0.563, tmp+PL+PL_cumulo+ AN_cumulo+Feed_Vol+RS_cumulo+Cell_conc._interval+ rab_integral+Arg_conc.+emission_CO2+interval_O2+ generate_CO2; 0.142, 0.563, tmp+pH+PL_cumulo+Feed_ Vol+RS_cumulo+Cell_conc._interval+rab_integral+Arg_ conc.+emission_O2+consum_O2+interval_O2; 0.142, 0.563, tmp+PL+PL_cumulo+Feed_Vol+RS_cumulo+Cell_ conc._interval+RQ_integral+Arg_conc.+emission_CO2+ consum_O2+interval_O2; 0.142, 0.563, tmp+tmp_cumulo+ PL_cumulo+Feed_Vol+RS_cumulo+Cell_conc._interval+ RQ_integral+Arg_conc.+emission_O2+interval_O2+ generate_CO2; 0.122, 0.563, tmp_cumulo+pH+PL_ cumulo+interval_yield+RS+Feed_Vol+RS_cumulo+Cell_ conc._interval+Arg_conc.+emission_O2+consum_O2+ interval_O2; 0.180, 0.563, tmp+pH+PL_cumulo+RS_ cumulo+Cell_conc._interval+Arg_conc.+emission_O2+ interval_O2+generate_CO2; 0.122, 0.563, tmp+PL_ cumulo+AN_cumulo+interval_yield+Feed_Vol+RS_ cumulo+Cell_conc._interval+Arg_conc.+emission_O2+ emission_CO2+consum_O2+generate_CO2; 0.122, 0.563, tmp_cumulo+pH_cumulo+PL_cumulo+AN_cumulo+RS_ cumulo+Cell_conc._interval+rab_integral+Arg_conc.+ emission_CO2+consum_O2+interval_O2+generate_CO2; 0.162, 0.563, tmp+PL_cumulo+RS+Feed_Vol+RS_cu- mulo+Cell_conc._interval+RQ_integral+Arg_conc.+emis- sion_CO2+interval_O2; 0.198, 0.563, tmp_cumulo+PL_cu- mulo+Feed_Vol+RS_cumulo+Cell_conc._interval+rab_ integral+Arg_conc.+interval_O2; 0.142, 0.563, tmp_ cumulo+PL_cumulo+Feed_Vol+RS_cumulo+Cell_conc._ interval+rab_integral+RQ_integral+Arg_conc.+emission_ O2+emission_CO2+interval_O2; 0.122, 0.563, tmp_ cumulo+pH+PL+PL_cumulo+Feed_Vol+RS_cumulo+ Cell_conc._interval+Arg_conc.+emission_O2+emission_ CO2+consum_O2+interval_O2; 0.122, 0.563, tmp+PL_ cumulo+AN_cumulo+interval_yield+Feed_Vol+RS_ cumulo+Cell_conc._interval+RQ_integral+Arg_conc.+ emission_O2+interval_O2+generate_CO2; 0.162, 0.563, tmp_cumulo+pH_cumulo+PL_cumulo+RS_cumulo+Cell_ conc._interval+rab_integral+Accum._Yield+Arg_conc.+ emission_CO2+interval_O2; 0.122, 0.563, tmp+PL_cu- mulo+AN_cumulo+interval_yield+RS+Feed_Vol+RS_ cumulo+Cell_conc._interval+Arg_conc.+emission_O2+ interval_O2+generate_CO2; 0.100, 0.563, tmp_cumulo+ pH+PL_cumulo+AN_cumulo+RS+Feed_Vol+RS_cumulo+ Cell_conc._interval+rab_integral+Arg_conc.+emission_ CO2+interval_O2+generate_CO2; 0.198, 0.563, tmp_ cumulo+PL_cumulo+RS_cumulo+Cell_conc._interval+ Arg_conc.+emission_O2+interval_O2+generate_CO2; 0.162, 0.563, tmp+PL+PL_cumulo+Feed_Vol+RS_cu- mulo+Cell_conc._interval+RQ_integral+Arg_conc.+emis- sion_O2+interval_O2; 0.122, 0.563, tmp_cumulo+pH+PL_ cumulo+AN+AN_cumulo+Feed_Vol+RS_cumulo+Cell_ conc._interval+Arg_conc.+emission_O2+interval_O2+ generate_CO2; 0.162, 0.563, tmp_cumulo+pH+PL_ cumulo+AN_cumulo+RS_cumulo+Cell_conc._interval+ Arg_conc.+emission_O2+consum_O2+interval_O2; 0.122, 0.563, tmp+PL+PL_cumulo+AN_cumulo+Feed_Vol+RS_ cumulo+Cell_conc._interval+rab_integral+Arg_conc.+ emission_O2+consum_O2+generate_CO2; 0.142, 0.563, tmp_cumulo+pH+PL_cumulo+Feed_Vol+RS_cumulo+

Cell_conc._interval+RQ_integral+Accum._Yield+Arg_conc.+emission_CO2+interval_O2; 0.142, 0.563, tmp_cumulo+pH+PL+PL_cumulo+Feed_Vol+RS_cumulo+Cell_conc._interval+RQ_integral+Arg_conc.+emission_O2+interval_O2; 0.162, 0.563, tmp+pH+PL_cumulo+RS_cumulo+Cell_conc._interval+rab_integral+Arg_conc.+emission_CO2+consum_O2+interval_O2; 0.122, 0.563, tmp_cumulo+pH+PL_cumulo+Feed_Vol+RS_cumulo+Cell_conc._interval+rab_integral+Arg_conc.+emission_O2+emission_CO2+interval_O2+generate_CO2; 0.161, 0.563, tmp+PL_cumulo+AN_cumulo+Feed_Vol+RS_cumulo+Cell_conc._interval+RQ_integral+Arg_conc.+emission_O2+interval_O2; 0.161, 0.563, tmp+PL_cumulo+RS+Feed_Vol+RS_cumulo+Cell_conc._interval+rab_integral+Arg_conc.+emission_CO2+interval_O2; 0.142, 0.563, tmp_cumulo+pH+PL+PL_cumulo+interval_yield+RS_cumulo+Cell_conc._interval+rab_integral+Arg_conc.+emission_CO2+interval_O2; 0.122, 0.563, tmp_cumulo+pH_cumulo+PL_cumulo+interval_yield+Feed_Vol+RS_cumulo+Cell_conc._interval+RQ_integral+Arg_conc.+emission_CO2+consum_O2+interval_O2; 0.142, 0.563, tmp_cumulo+pH_cumulo+PL_cumulo+AN+AN_cumulo+RS_cumulo+Cell_conc._interval+rab_integral+Arg_conc.+emission_CO2+interval_O2; 0.142, 0.563, tmp_cumulo+pH+PL_cumulo+interval_yield+Feed_Vol+RS_cumulo+Cell_conc._interval+RQ_integral+Arg_conc.+emission_O2+interval_O2; 0.142, 0.563, tmp_cumulo+pH_cumulo+PL_cumulo+interval_yield+RS_cumulo+Cell_conc._interval+rab_integral+Arg_conc.+emission_CO2+consum_O2+interval_O2; 0.198, 0.563, tmp+PL_cumulo+RS_cumulo+Cell_conc._interval+Arg_conc.+emission_O2+consum_O2+interval_O2; 0.142, 0.563, tmp+PL_cumulo+AN_cumulo+RS+RS_cumulo+Cell_conc._interval+rab_integral+Arg_conc.+emission_CO2+interval_O2+generate_CO2; 0.161, 0.563, tmp_cumulo+PL_cumulo+RS+Feed_Vol+RS_cumulo+Cell_conc._interval+Arg_conc.+emission_CO2+interval_O2+generate_CO2; 0.121, 0.563, tmp_cumulo+PL+PL_cumulo+AN_cumulo+RS+RS_cumulo+Cell_conc._interval+rab_integral+Arg_conc.+emission_CO2+interval_O2+generate_CO2; 0.121, 0.563, tmp+PL_cumulo+AN_cumulo+Feed_Vol+RS_cumulo+Cell_conc._interval+rab_integral+RQ_integral+Arg_conc.+emission_O2+interval_O2+generate_CO2; 0.180, 0.563, tmp+pH_cumulo+PL_cumulo+Feed_Vol+Cell_conc._interval+Arg_conc.+emission_O2+consum_O2+generate_CO2; 0.142, 0.563, tmp_cumulo+pH_cumulo+PL_cumulo+RS+Feed_Vol+RS_cumulo+Cell_conc._interval+rab_integral+Arg_conc.+emission_O2+interval_O2; 0.142, 0.563, tmp_cumulo+pH+PL_cumulo+AN_cumulo+RS+Feed_Vol+Cell_conc._interval+Arg_conc.+emission_O2+interval_O2+generate_CO2; 0.142, 0.563, tmp_cumulo+PL_cumulo+RS+Feed_Vol+RS_cumulo+Cell_conc._interval+rab_integral+Arg_conc.+emission_CO2+consum_O2+generate_CO2; 0.121, 0.563, tmp_cumulo+pH+PL+PL_cumulo+Feed_Vol+RS_cumulo+Cell_conc._interval+RQ_integral+Arg_conc.+emission_CO2+consum_O2+interval_O2; 0.121, 0.563, tmp_cumulo+pH+pH_cumulo+PL+PL_cumulo+Feed_Vol+RS_cumulo+Cell_conc._interval+RQ_integral+Arg_conc.+emission_CO2+interval_O2; 0.161, 0.562, tmp+tmp_cumulo+PL_cumulo+Feed_Vol+RS_cumulo+Cell_conc._interval+rab_integral+Arg_conc.+emission_CO2+interval_O2; 0.100, 0.562, tmp_cumulo+pH+PL_cumulo+AN_cumulo+interval_yield+Feed_Vol+RS_cumulo+Cell_conc._interval+RQ_integral+Arg_conc.+emission_CO2+consum_O2+interval_O2; 0.161, 0.562, tmp_cumulo+PL_cumulo+RS+RS_cumulo+Cell_conc._interval+RQ_integral+Arg_conc.+emission_O2+emission_CO2+interval_O2; 0.121, 0.562, tmp_cumulo+pH+pH_cumulo+PL_cumulo+RS+Feed_Vol+RS_cumulo+Cell_conc._interval+Arg_conc.+emission_O2+consum_O2+interval_O2; 0.121, 0.562, tmp_cumulo+pH_cumulo+PL_cumulo+AN+AN_cumulo+Feed_Vol+RS_cumulo+Cell_conc._interval+Arg_conc.+emission_O2+consum_O2+interval_O2; 0.141, 0.562, tmp+pH+PL_cumulo+Feed_Vol+RS_cumulo+Cell_conc._interval+RQ_integral+Arg_conc.+emission_O2+interval_O2+generate_CO2; 0.161, 0.562, tmp_cumulo+PL+PL_cumulo+RS_cumulo+Cell_conc._interval+RQ_integral+Arg_conc.+emission_CO2+interval_O2+generate_CO2; 0.121, 0.562, tmp_cumulo+pH_cumulo+PL_cumulo+Feed_Vol+RS_cumulo+Cell_conc._interval+rab_integral+Arg_conc.+emission_CO2+consum_O2+interval_O2; 0.161, 0.562, tmp+PL_cumulo+RS+RS_cumulo+Cell_conc._interval+rab_integral+Arg_conc.+emission_CO2+consum_O2+generate_CO2; 0.141, 0.562, tmp+PL_cumulo+Feed_Vol+RS_cumulo+Cell_conc._interval+rab_integral+Arg_conc.+emission_O2+consum_O2+interval_O2+generate_CO2; 0.141, 0.562, tmp+PL_cumulo+AN_cumulo+Feed_Vol+RS_cumulo+Cell_conc._cumulo+Cell_conc._interval+Arg_conc.+emission_O2+interval_O2+generate_CO2; 0.099, 0.562, tmp_cumulo+pH+PL+PL_cumulo+AN_cumulo+Feed_Vol+RS_cumulo+Cell_conc._interval+rab_integral+Arg_conc.+emission_CO2+consum_O2+interval_O2; 0.141, 0.562, tmp+pH+PL+PL_cumulo+Feed_Vol+RS_cumulo+Cell_conc._interval+Arg_conc.+emission_O2+consum_O2+interval_O2; 0.141, 0.562, tmp+PL_cumulo+interval_yield+RS+Feed_Vol+RS_cumulo+Cell_conc._interval+Arg_conc.+emission_O2+interval_O2+generate_CO2; 0.141, 0.562, tmp+PL_cumulo+PL_cumulo+RS+Feed_Vol+RS_cumulo+Cell_conc._interval+Arg_conc.+emission_O2+consum_O2+interval_O2+generate_CO2; 0.121, 0.562, tmp_cumulo+pH+PL_cumulo+interval_yield+RS+Feed_Vol+RS_cumulo+Cell_conc._interval+Arg_conc.+emission_O2+interval_O2+generate_CO2; 0.099, 0.562, tmp_cumulo+pH+pH_cumulo+PL_cumulo+AN_cumulo+RS+Feed_Vol+RS_cumulo+Cell_conc._interval+Arg_conc.+emission_O2+consum_O2+interval_O2; 0.121, 0.562, tmp_cumulo+pH_cumulo+PL_cumulo+interval_yield+Feed_Vol+RS_cumulo+Cell_conc._interval+rab_integral+Arg_conc.+emission_CO2+interval_O2+generate_CO2; 0.179, 0.562, tmp+pH_cumulo+PL_cumulo+RS_cumulo+Cell_conc._interval+rab_integral+Arg_conc.+emission_O2+interval_O2; 0.141, 0.562, tmp+PL_cumulo+RS+Feed_Vol+RS_cumulo+Cell_conc._interval+rab_integral+Arg_conc.+emission_CO2+interval_O02+generate_CO2; 0.197, 0.562, tmp_cumulo+PL_cumulo+Feed_Vol+Cell_conc._interval+Arg_conc.+emission_O2+consum_O2+generate_CO2; 0.121, 0.562, tmp_cumulo+pH+pH_cumulo+PL_cumulo+Feed_Vol+RS_cumulo+Cell_conc._interval+rab_integral+Arg_conc.+emission_CO2+interval_O2+generate_CO2; 0.121, 0.562, tmp+tmp_cumulo+PL+PL_cumulo+AN_cumulo+Feed_Vol+RS_cumulo+Cell_conc._interval+Arg_conc.+emission_O2+interval_O2+generate_CO2; 0.121, 0.562, tmp_cumulo+pH_cumulo+PL_cumulo+AN_cumulo+Feed_Vol+RS_cumulo+Cell_conc._interval+rab_integral+Arg_conc.+emission_O2+interval_O2+generate_CO2; 0.141, 0.562, tmp_cumulo+PL+PL_cumulo+interval_yield+Feed_Vol+RS_cumulo+Cell_conc._interval+Arg_conc.+emission_O2+interval_O2+generate_CO2; 0.161, 0.562, tmp_cumulo+PL_cumulo+RS+RS_cumulo+Cell_conc._cumulo+Cell_conc._interval+rab_integral+Arg_conc.+emission_CO2+interval_O2; 0.141, 0.562, tmp+pH+PL_cumulo+interval_yield+Feed_Vol+RS_cumulo+Cell_conc._interval+Arg_conc.+emission_O2+consum_O2+generate_CO2; 0.121, 0.562, tmp_cumulo+pH_cumulo+PL_cumulo+AN+AN_cumulo+Feed_Vol+RS_cumulo+Cell_conc._interval+rab_integral+Arg_conc.+emission_CO2+interval_O2; 0.121, 0.562, tmp_cumulo+pH_cumulo+PL_cumulo+AN_cumulo+RS+Feed_Vol+RS_cumulo+Cell_conc._ interval+RQ_integral+Arg_conc.+emission_CO2+interval_O2; 0.141, 0.562, tmp+tmp_cumulo+PL_cumulo+Feed_Vol+RS_cumulo+Cell_conc._interval+RQ_integral+Arg_conc.+emission_CO2+consum_O2+interval_O2; 0.099, 0.562, tmp_cumulo+pH+PL+PL_cumulo+AN_cumulo+Feed_Vol+RS_cumulo+Cell_conc._interval+RQ_integral+Arg_conc.+emission_O2+consum_O2+interval_O2; 0.160, 0.562, tmp+PL_cumulo+AN_cumulo+Feed_Vol+RS_cumulo+Cell_conc._interval+rab_integral+Arg_conc.+emission_O2+interval_O2; 0.141, 0.562, tmp+pH_cumulo+PL+PL_cumulo+Feed_Vol+RS_cumulo+Cell_conc._interval+Arg_conc.+emission_O2+consum_O2+interval_O2; 0.120, 0.562, tmp_cumulo+PL+PL_cumulo+AN_cumulo+Feed_Vol+RS_cumulo+Cell_conc._interval+RQ_integral+Arg_conc.+emission_O2+interval_O2+generate_CO2; 0.141, 0.562, tmp+pH_cumulo+PL+PL_cumulo+Feed_Vol+RS_cumulo+Cell_conc._interval+RQ_integral+Arg_conc.+emission_CO2+interval_O2; 0.160, 0.562, tmp+PL_cumulo+interval_yield+Feed_Vol+RS_cumulo+Cell_conc._interval+Arg_conc.+emission_O2+consum_O2+interval_O2; 0.141, 0.562, tmp_cumulo+PL_cumulo+interval_yield+RS+Feed_Vol+RS_cumulo+Cell_conc._interval+RQ_integral+Arg_conc.+emission_CO2+interval_O2; 0.141, 0.562, tmp+PL_cumulo+interval_yield+Feed_Vol+RS_cumulo+Cell_conc._interval+rab_integral+Arg_conc.+emission_O2+consum_O2+generate_CO2; 0.120, 0.562, tmp_cumulo+pH+PL+PL_cumulo+AN+Feed_Vol+RS_cumulo+Cell_conc._interval+RQ_integral+Arg_conc.+emission_CO2+interval_O2; 0.141, 0.562, tmp_cumulo+pH_cumulo+PL_cumulo+AN_cumulo+RS_cumulo+Cell_conc._interval+rab_integral+Arg_conc.+emission_O2+emission_CO2+interval_O2; 0.160, 0.562, tmp_cumulo+PL_cumulo+interval_yield+Feed_Vol+RS_cumulo+Cell_conc._interval+rab_integral+RQ_integral+Arg_conc.+interval_O2; 0.120, 0.562, tmp_cumulo+pH+PL_cumulo+interval_yield+RS+Feed_Vol+RS_cumulo+Cell_conc._interval+RQ_integral+Arg_conc.+emission_CO2+interval_O2; 0.179, 0.562, tmp+pH_cumulo+PL_cumulo+RS_cumulo+Cell_conc._interval+RQ_integral+Arg_conc.+emission_CO2+interval_O2; 0.120, 0.562, tmp_cumulo+pH_cumulo+PL_cumulo+AN_cumulo+RS+RS_cumulo+Cell_conc._interval+rab_integral+Arg_conc.+emission_CO2+interval_O2+generate_CO2; 0.120, 0.562, tmp_cumulo+PL_cumulo+AN_cumulo+RS+Feed_Vol+RS_cumulo+Cell_conc._interval+rab_integral+Arg_conc.+emission_O2+interval_O2+generate_CO2; 0.120, 0.562, tmp+PL_cumulo+AN_cumulo+RS+Feed_Vol+RS_cumulo+Cell_conc._interval+RQ_integral+Arg_conc.+emission_O2+interval_O2+generate_CO2; 0.120, 0.562, tmp+PL_cumulo+AN_cumulo+RS+Feed_Vol+RS_cumulo+Cell_conc._interval+Arg_conc.+emission_O2+emission_CO2+consum_O2+generate_CO2; 0.160, 0.562, tmp_cumulo+pH+PL_cumulo+RS_cumulo+Cell_conc._interval+Arg_conc.+emission_O2+emission_CO2+consum_O2+interval_O2; 0.141, 0.562, tmp_cumulo+PL+PL_cumulo+Feed_Vol+RS_cumulo+Cell_conc._interval+rab_integral+Arg_conc.+emission_O2+interval_O2+generate_CO2; 0.160, 0.562, tmp_cumulo+pH+PL_cumulo+AN+RS_cumulo+Cell_conc._interval+rab_integral+Arg_conc.+emission_O2+interval_O2; 0.120, 0.562, tmp_cumulo+pH+PL_cumulo+RS+Feed_Vol+RS_cumulo+Cell_conc._interval+rab_integral+Arg_conc.+emission_O2+consum_O2+interval_O2; 0.141, 0.562, tmp+PL+PL_cumulo+Feed_Vol+RS_cumulo+Cell_conc._interval+RQ_integral+Arg_conc.+emission_O2+emission_CO2+interval_O2; 0.141, 0.562, tmp_cumulo+PL_cumulo+AN_cumulo+Feed_Vol+RS_cumulo+Cell_conc._interval+RQ_integral+Arg_conc.+emission_O2+consum_O2+generate_CO2; 0.179, 0.562, tmp_cumulo+pH+PL_cumulo+RS+Cell_conc._interval+Arg_conc.+emission_CO2+consum_O2+interval_O2; 0.120, 0.562, tmp+tmp_cumulo+pH+PL+PL_cumulo+AN_cumulo+RS_cumulo+Cell_conc._interval+rab_integral+Arg_conc.+emission_CO2+interval_O2; 0.141, 0.562, tmp_cumulo+PL_cumulo+RS+Feed_Vol+RS_cumulo+Cell_conc._interval+RQ_integral+Arg_conc.+emission_O2+interval_O2+generate_CO2; 0.179, 0.562, tmp_cumulo+pH+PL_cumulo+RS+RS_cumulo+Cell_conc._interval+Arg_conc.+emission_CO2+interval_O2; 0.120, 0.562, tmp_cumulo+PL+PL_cumulo+AN_cumulo+Feed_Vol+RS_cumulo+Cell_conc._interval+Arg_conc.+emission_O2+emission_CO2+interval_O2+generate_CO2; 0.141, 0.562, tmp_cumulo+pH_cumulo+PL_cumulo+AN_cumulo+RS_cumulo+Cell_conc._interval+rab_integral+RQ_integral+Arg_conc.+emission_O2+interval_O2; 0.120, 0.562, tmp+tmp_cumulo+PL_cumulo+AN_cumulo+Feed_Vol+RS_cumulo+Cell_conc._interval+Arg_conc.+emission_CO2+interval_O2+generate_CO2; 0.120, 0.562, tmp_cumulo+pH+pH_cumulo+PL_cumulo+RS+Feed_Vol+RS_cumulo+Cell_conc._interval+rab_integral+Arg_conc.+emission_CO2+interval_O2; 0.160, 0.562, tmp_cumulo+pH+PL_cumulo+Feed_Vol+RS_cumulo+Cell_conc._interval+Arg_conc.+emission_CO2+interval_O2+generate_CO2; 0.141, 0.562, tmp+tmp_cumulo+pH+PL_cumulo+RS_cumulo+Cell_conc._interval+rab_integral+Arg_conc.+emission_CO2+consum_O2+interval_O2; 0.160, 0.562, tmp_cumulo+pH_cumulo+PL_cumulo+RS+RS_cumulo+Cell_conc._interval+rab_integral+Arg_conc.+emission_O2+interval_O2; 0.140, 0.562, tmp_cumulo+pH+pH_cumulo+PL_cumulo+AN+RS_cumulo+Cell_conc._interval+rab_integral+Arg_conc.+emission_CO2+interval_O2; 0.120, 0.562, tmp+tmp_cumulo+pH_cumulo+PL_cumulo+AN_cumulo+Feed_Vol+RS_cumulo+Cell_conc._interval+Arg_conc.+emission_O2+interval_O2+generate_CO2; 0.140, 0.562, tmp+pH+PL+PL_cumulo+Feed_Vol+RS_cumulo+Cell_conc._interval+RQ_integral+Arg_conc.+emission_CO2+interval_O2; 0.120, 0.562, tmp+pH_cumulo+PL_cumulo+AN_cumulo+Feed_Vol+RS_cumulo+Cell_conc._interval+RQ_integral+Arg_conc.+emission_O2+consum_O2+interval_O2; 0.160, 0.562, tmp+pH_cumulo+PL_cumulo+RS+cumulo+Cell_conc._cumulo+Cell_conc._interval+rab_integral+Arg_conc.+emission_CO2+interval_O2; 0.179, 0.562, tmp_cumulo+pH+PL_cumulo+RS+Cell_conc._cumulo+Cell_conc._interval+Arg_conc.+emission_O2+interval_O2; 0.140, 0.562, tmp_cumulo+pH_cumulo+PL_cumulo+RS_cumulo+Cell_conc._cumulo+Cell_conc._interval+rab_integral+Arg_conc.+emission_CO2+interval_O2+generate_CO2; 0.140, 0.562, tmp+pH_cumulo+PL_cumulo+RS+Feed_Vol+Cell_conc._interval+Arg_conc.+emission_O2+emission_CO2+consum_O2+generate_CO2; 0.120, 0.562, tmp_cumulo+pH+PL_cumulo+AN_cumulo+OD+Feed_Vol+RS_cumulo+Cell_conc._interval+RQ_integral+Arg_conc.+emission_CO2+interval_O2; 0.098, 0.562, tmp_cumulo+pH+PL_cumulo+AN_cumulo+interval_yield+Feed_Vol+RS_cumulo+Cell_conc._interval+Arg_conc.+emission_O2+emission_CO2+interval_O2+generate_CO2; 0.140, 0.562, tmp_cumulo+PL_cumulo+interval_yield+Feed_Vol+RS_cumulo+Cell_conc._interval+RQ_integral+Arg_conc.+emission_O2+consum_O2+interval_O2; 0.120, 0.562, tmp_cumulo+pH_cumulo+PL_cumulo+AN+RS+RS_cumulo+Cell_conc._interval+rab_integral+Arg_conc.+emission_CO2+consum_O2+interval_O2; 0.120, 0.562, tmp_cumulo+pH_cumulo+PL_cumulo+interval_yield+Feed_Vol+RS_cumulo+Cell_conc._interval+rab_integral+Arg_conc.+emission_O2+consum_O2+interval_O2; 0.120, 0.562, tmp_cumulo+pH+pH_cumulo+PL+PL_cumulo+AN_cumulo+RS_cumulo+Cell_conc._interval+rab_integral+Arg_conc.+emission_CO2+interval_O2

[210. Linear Model that Predicts Arginine Production Amount in Interval 10]

0.577, 0.814, pH+PL_cumulo+AN+AN_cumulo+Feed_Vol+RS_cumulo+rab_integral+RQ_integral+Arg_conc.+emission_O2+emission_CO2; 0.586, 0.814, pH+AN+AN_cumulo+Feed_Vol+RS_cumulo+rab_integral+RQ_integral+Arg_conc.+emission_O2+emission_CO2; 0.566, 0.814, pH+PL+PL_cumulo+AN+AN_cumulo+Feed_Vol+RS_cumulo+rab_integral+RQ_integral+Arg_conc.+emission_O2+emission_CO2; 0.575, 0.813, pH+PL+AN+AN_cumulo+Feed_Vol+RS_cumulo+rab_integral+RQ_integral+Arg_conc.+emission_O2+emission_CO2; 0.547, 0.810, pH+PL+PL_cumulo+AN+AN_cumulo+Feed_Vol+RS_cumulo+rab_integral+RQ_integral+Arg_conc.+emission_O2+emission_CO2+consum_O2; 0.557, 0.810, pH+PL_cumulo+AN+AN_cumulo+Feed_Vol+RS_cumulo+rab_integral+RQ_integral+Accum._Yield+Arg_conc.+emission_O2+emission_CO2; 0.567, 0.809, pH+AN+AN_cumulo+Feed_Vol+RS_cumulo+rab_integral+RQ_integral+Accum._Yield+Arg_conc.+emission_O2+emission_CO2; 0.545, 0.809, pH+PL+PL_cumulo+AN+AN_cumulo+interval_yield+Feed_Vol+RS_cumulo+rab_integral+RQ_integral+Arg_conc.+emission_O2+emission_CO2; 0.566, 0.809, tmp_cumulo+pH+AN+AN_cumulo+Feed_Vol+RS_cumulo+rab_integral+RQ_integral+Arg_conc.+emission_O2+emission_CO2; 0.556, 0.809, tmp_cumulo+pH+PL+AN+AN_cumulo+Feed_Vol+RS_cumulo+rab_integral+RQ_integral+Arg_conc.+emission_O2+emission_CO2; 0.574, 0.808, pH+PL+AN+Feed_Vol+RS_cumulo+rab_integral+RQ_integral+Arg_conc.+emission_O2+emission_CO2; 0.543, 0.808, pH+PL+PL_cumulo+AN+AN_cumulo+Feed_Vol+RS_cumulo+rab_integral+RQ_integral+Arg_conc.+emission_O2+emission_CO2+interval_O2; 0.563, 0.808, tmp+pH+AN+AN_cumulo+Feed_Vol+RS_cumulo+rab_integral+RQ_integral+Arg_conc.+emission_O2+emission_CO2; 0.553, 0.808, tmp+pH+PL+AN+AN_cumulo+Feed_Vol+RS_cumulo+rab_integral+RQ_integral+Arg_conc.+emission_O2+emission_CO2; 0.563, 0.808, pH+PL+PL_cumulo+AN+Feed_Vol+RS_cumulo+rab_integral+RQ_integral+Arg_conc.+emission_O2+emission_CO2; 0.542, 0.808, tmp+pH+PL+PL_cumulo+AN+AN_cumulo+Feed_Vol+RS_cumulo+rab_integral+RQ_integral+Arg_conc.+emission_O2+emission_CO2; 0.553, 0.808, pH+PL+PL_cumulo+AN+AN_cumulo+interval_yield+Feed_Vol+RS_cumulo+rab_integral+RQ_integral+Arg_conc.+emission_O2+emission_CO2; 0.582, 0.807, pH+AN+Feed_Vol+RS_cumulo+rab_integral+RQ_integral+Arg_conc.+emission_O2+emission_CO2; 0.541, 0.807, tmp_cumulo+pH+PL+PL_cumulo+AN+AN_cumulo+Feed_Vol+RS_cumulo+rab_integral+RQ_integral+Arg_conc.+emission_O2+emission_CO2; 0.562, 0.807, pH+AN+AN_cumulo+Feed_Vol+RS_cumulo+rab_integral+RQ_integral+Arg_conc.+emission_O2+emission_CO2+interval_O2; 0.529, 0.807, pH+PL+PL_cumulo+AN+AN_cumulo+interval_yield+Feed_Vol+RS_cumulo+rab_integral+RQ_integral+Arg_conc.+emission_O2+emission_CO2+interval_O2; 0.562, 0.807, pH+AN+AN_cumulo+Feed_Vol+RS_cumulo+rab_integral+RQ_integral+Arg_conc.+emission_O2+emission_CO2+generate_CO2; 0.551, 0.807, tmp+pH+PL_cumulo+AN+AN_cumulo+Feed_Vol+RS_cumulo+rab_integral+RQ_integral+Arg_conc.+emission_O2+emission_CO2; 0.551, 0.807, pH+PL+AN+AN_cumulo+Feed_Vol+RS_cumulo+rab_integral+RQ_integral+Arg_conc.+emission_O2+emission_CO2+interval_O2; 0.551, 0.807, tmp_cumulo+pH+PL_cumulo+AN+AN_cumulo+Feed_Vol+RS_cumulo+rab_integral+RQ_integral+Arg_conc.+emission_O2+emission_CO2; 0.528, 0.806, pH+PL+PL_cumulo+AN+AN_cumulo+interval_yield+Feed_Vol+RS_cumulo+rab_integral+RQ_integral+Arg_conc.+emission_O2+emission_CO2+consum_O2; 0.550, 0.806, pH+PL+AN+AN_cumulo+Feed_Vol+RS_cumulo+rab_integral+RQ_integral+Accum._Yield+Arg_conc.+emission_O2+emission_CO2; 0.550, 0.806, pH+PL_cumulo+AN+AN_cumulo+Feed_Vol+RS_cumulo+rab_integral+RQ_integral+Arg_conc.+emission_O2+emission_CO2+generate_CO2; 0.550, 0.806, pH+PL+AN+AN_cumulo+interval_yield+Feed_Vol+RS_cumulo+rab_integral+RQ_integral+Arg_conc.+emission_O2+emission_CO2; 0.550, 0.806, pH+PL_cumulo+AN+AN_cumulo+Feed_Vol+RS_cumulo+rab_integral+RQ_integral+Arg_conc.+emission_O2+emission_CO2+interval_O2; 0.549, 0.806, pH+PL+PL_cumulo+AN+Feed_Vol+RS_cumulo+rab_integral+RQ_integral+Arg_conc.+emission_O2+emission_CO2+consum_O2; 0.549, 0.806, pH+PL+AN+AN_cumulo+Feed_Vol+RS_cumulo+rab_integral+RQ_integral+Arg_conc.+emission_O2+emission_CO2+generate_CO2; 0.549, 0.806, pH+PL+PL_cumulo+AN+interval_yield+Feed_Vol+RS_cumulo+rab_integral+RQ_integral+Arg_conc.+emission_O2+emission_CO2; 0.560, 0.806, pH+AN+AN_cumulo+interval_yield+Feed_Vol+RS_cumulo+rab_integral+RQ_integral+Arg_conc.+emission_O2+emission_CO2; 0.538, 0.806, pH+PL+PL_cumulo+AN+AN_cumulo+Feed_Vol+RS_cumulo+rab_integral+RQ_integral+Arg_conc.+emission_O2+emission_CO2+generate_CO2; 0.560, 0.806, pH+AN+AN_cumulo+Feed_Vol+RS_cumulo+Cell_conc._interval+rab_integral+RQ_integral+Arg_conc.+emission_O2+emission_CO2; 0.526, 0.806, tmp+pH+PL+PL_cumulo+AN+interval_yield+Feed_Vol+RS_cumulo+rab_integral+RQ_integral+Arg_conc.+emission_O2+emission_CO2+consum_O2; 0.526, 0.806, tmp_cumulo+pH+PL+PL_cumulo+AN+interval_yield+Feed_Vol+RS_cumulo+rab_integral+RQ_integral+Arg_conc.+emission_O2+emission_CO2+consum_O2; 0.549, 0.806, pH+PL_cumulo+AN+AN_cumulo+Feed_Vol+RS_cumulo+Cell_conc._cumulo+rab_integral+RQ_integral+Arg_conc.+emission_O2+emission_CO2; 0.548, 0.805, pH+PL_cumulo+AN+AN_cumulo+Feed_Vol+RS_cumulo+rab_integral+RQ_integral+Arg_conc.+emission_O2+emission_CO2+consum_O2; 0.537, 0.805, pH+PL+PL_cumulo+AN+AN_cumulo+Feed_Vol+RS_cumulo+rab_integral+RQ_integral+Accum._Yield+Arg_conc.+emission_O2+emission_CO2; 0.569, 0.805, pH+PL_cumulo+AN+Feed_Vol+RS_cumulo+rab_integral+RQ_integral+Arg_conc.+emission_O2+emission_CO2; 0.537, 0.805, pH+PL_cumulo+AN+AN_cumulo+interval_yield+Feed_Vol+RS_cumulo+rab_integral+Accum._Yield+Arg_conc.+emission_O2+emission_CO2; 0.537, 0.805, pH+PL+PL_cumulo+AN+AN_cumulo+Feed_Vol+RS_cumulo+Cell_conc._cumulo+rab_integral+RQ_integral+Arg_conc.+emission_O2+emission_CO2; 0.537, 0.805, pH+PL+PL_cumulo+AN+interval_yield+Feed_Vol+RS_cumulo+rab_integral+RQ_integral+Arg_conc.+emission_O2+emission_CO2+consum_O2; 0.548, 0.805, pH+AN+interval_yield+Feed_Vol+RS_cumulo+Cell_conc._interval+rab_integral+RQ_integral+Accum._Yield+Arg_conc.+emission_O2+emission_CO2; 0.536, 0.805, pH+AN+AN_cumulo+interval_yield+Feed_Vol+RS_cumulo+Cell_conc._interval+rab_integral+RQ_integral+Accum._Yield+Arg_conc.+emission_O2+emission_CO2; 0.547, 0.805, pH+PL+AN+AN_cumulo+Feed_Vol+RS_cumulo+Cell_conc._cumulo+rab_integral+RQ_integral+Arg_conc.+emission_O2+emission_CO2; 0.558, 0.805, pH_cumulo+PL_cumulo+AN+AN_cumulo+Feed_Vol+RS_cumulo+rab_ integral+RQ_integral+Arg_conc.+emission_O2+emission_CO2; 0.524, 0.805, tmp_cumulo+pH+PL+PL_cumulo+AN+AN_cumulo+Feed_Vol+RS_cumulo+rab_integral+RQ_integral+Arg_conc.+emission_O2+emission_CO2+consum_O2; 0.512, 0.805, tmp_cumulo+pH+PL+PL_cumulo+AN+AN_cumulo+interval_yield+Feed_Vol+RS_cumulo+rab_integral+RQ_integral+Arg_conc.+emission_O2+emission_CO2+interval_O2; 0.524, 0.805, tmp+pH+PL+PL_cumulo+AN+AN_cumulo+Feed_Vol+RS_cumulo+rab_integral+RQ_integral+Arg_conc.+emission_O2+emission_CO2+consum_O2; 0.512, 0.805, tmp_cumulo+pH+PL+PL_cumulo+AN+AN_cumulo+interval_yield+Feed_Vol+RS_cumulo+rab_integral+RQ_integral+Arg_conc.+emission_O2+emission_CO2+consum_O2; 0.546, 0.804, pH+pH_cumulo+PL+AN+AN_cumulo+Feed_Vol+RS_cumulo+rab_integral+RQ_integral+Arg_conc.+emission_O2+emission_CO2; 0.535, 0.804, pH+pH_cumulo+PL+PL_cumulo+AN+AN_cumulo+Feed_Vol+RS_cumulo+rab_integral+RQ_integral+Arg_conc.+emission_O2+emission_CO2; 0.535, 0.804, tmp+tmp_cumulo+pH+PL+AN+AN_cumulo+Feed_Vol+RS_cumulo+rab_integral+RQ_integral+Arg_conc.+emission_O2+emission_CO2; 0.556, 0.804, pH+AN+AN_cumulo+Feed_Vol+RS_cumulo+Cell_conc._cumulo+rab_integral+RQ_integral+Arg_conc.+emission_O2+emission_CO2; 0.546, 0.804, tmp_cumulo+pH+AN+AN_cumulo+Feed_Vol+RS_cumulo+rab_integral+RQ_integral+Accum._Yield+Arg_conc.+emission_O2+emission_CO2; 0.556, 0.804, pH+PL+AN+interval_yield+Feed_Vol+RS_cumulo+rab_integral+RQ_integral+Arg_conc.+emission_O2+emission_CO2; 0.556, 0.804, pH+pH_cumulo+AN+AN_cumulo+Feed_Vol+RS_cumulo+rab_integral+RQ_integral+Arg_conc.+emission_O2+emission_CO2; 0.555, 0.804, pH+AN+interval_yield+Feed_Vol+RS_cumulo+Cell_conc._interval+rab_integral+RQ_integral+Arg_conc.+emission_O2+emission_CO2; 0.544, 0.803, pH+pH_cumulo+PL_cumulo+AN+AN_cumulo+Feed_Vol+RS_cumulo+rab_integral+RQ_integral+Arg_conc.+emission_O2+emission_CO2; 0.555, 0.803, tmp_cumulo+pH+PL+AN+Feed_Vol+RS_cumulo+rab_integral+RQ_integral+Arg_conc.+emission_O2+emission_CO2; 0.544, 0.803, pH+PL_cumulo+AN+AN_cumulo+Feed_Vol+RS_cumulo+Cell_conc._interval+rab_integral+RQ_integral+Arg_conc.+emission_O2+emission_CO2; 0.544, 0.803, tmp+tmp_cumulo+pH+AN+AN_cumulo+Feed_Vol+RS_cumulo+rab_integral+RQ_integral+Arg_conc.+emission_O2+emission_CO2; 0.544, 0.803, pH+PL+AN+interval_yield+Feed_Vol+RS_cumulo+Cell_conc._interval+rab_integral+RQ_integral+Arg_conc.+emission_O2+emission_CO2; 0.521, 0.803, tmp+pH+PL+PL_cumulo+AN+AN_cumulo+interval_yield+Feed_Vol+RS_cumulo+rab_integral+RQ_integral+Arg_conc.+emission_O2+emission_CO2; 0.555, 0.803, pH+AN+AN_cumulo+Feed_Vol+RS_cumulo+rab_integral+RQ_integral+Arg_conc.+emission_O2+emission_CO2+consum_O2; 0.544, 0.803, pH+PL+AN+AN_cumulo+Feed_Vol+RS_cumulo+rab_integral+RQ_integral+Arg_conc.+emission_O2+emission_CO2+consum_O2; 0.521, 0.803, tmp_cumulo+pH+PL+PL_cumulo+AN+AN_cumulo+interval_yield+Feed_Vol+RS_cumulo+rab_integral+RQ_integral+Arg_conc.+emission_O2+emission_CO2; 0.521, 0.803, pH+PL+PL_cumulo+AN+AN_cumulo+interval_yield+Feed_Vol+RS_cumulo+rab_integral+RQ_integral+Accum._Yield+Arg_conc.+emission_O2+emission_CO2; 0.574, 0.803, pH+AN_cumulo+Feed_Vol+RS_cumulo+rab_integral+RQ_integral+Arg_conc.+emission_O2+emission_CO2; 0.508, 0.803, tmp+pH+PL+PL_cumulo+AN+AN_cumulo+interval_yield+Feed_Vol+RS_cumulo+rab_integral+RQ_integral+Arg_conc.+emission_O2+emission_CO2+consum_O2; 0.508, 0.803, tmp+pH+PL+PL_cumulo+AN+AN_cumulo+interval_yield+Feed_Vol+RS_cumulo+rab_integral+RQ_integral+Arg_conc.+emission_O2+emission_CO2+interval_O2; 0.544, 0.803, pH+AN+AN_cumulo+Feed_Vol+RS_cumulo+rab_integral+RQ_integral+Accum._Yield+Arg_conc.+emission_O2+emission_CO2+generate_CO2; 0.532, 0.803, tmp_cumulo+pH+PL+AN+AN_cumulo+interval_yield+Feed_Vol+RS_cumulo+rab_integral+RQ_integral+Arg_conc.+emission_O2+emission_CO2; 0.532, 0.803, pH+PL+AN+interval_yield+Feed_Vol+RS_cumulo+Cell_conc._interval+rab_integral+RQ_integral+Accum._Yield+Arg_conc.+emission_O2+emission_CO2; 0.543, 0.803, pH+PL+AN+AN_cumulo+Feed_Vol+RS_cumulo+Cell_conc._interval+rab_integral+RQ_integral+Arg_conc.+emission_O2+emission_CO2; 0.543, 0.803, pH+AN+AN_cumulo+interval_yield+Feed_Vol+RS_cumulo+rab_integral+RQ_integral+Accum._Yield+Arg_conc.+emission_O2+emission_CO2; 0.553, 0.803, tmp+pH+PL+AN+Feed_Vol+RS_cumulo+rab_integral+RQ_integral+Arg_conc.+emission_O2+emission_CO2; 0.543, 0.803, tmp+pH+AN+AN_cumulo+Feed_Vol+RS_cumulo+rab_integral+RQ_integral+Accum._Yield+Arg_conc.+emission_O2+emission_CO2; 0.532, 0.803, tmp+pH+PL+PL_cumulo+AN+Feed_Vol+RS_cumulo+rab_integral+RQ_integral+Arg_conc.+emission_O2+emission_CO2+consum_O2; 0.520, 0.803, pH+PL+PL_cumulo+AN+AN_cumulo+Feed_Vol+RS_cumulo+Cell_conc._cumulo+rab_integral+RQ_integral+Arg_conc.+emission_O2+emission_CO2+consum_O2; 0.563, 0.803, pH+PL_cumulo+AN_cumulo+Feed_Vol+RS_cumulo+rab_integral+RQ_integral+Arg_conc.+emission_O2+emission_CO2; 0.519, 0.802, pH+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2; 0.531, 0.802, pH+PL_cumulo+AN+AN_cumulo+Feed_Vol+RS_cumulo+rab_integral+RQ_integral+Accum._Yield+Arg_conc.+emission_O2+emission_CO2+generate_CO2; 0.542, 0.802, pH+AN+AN_cumulo+Feed_Vol+RS_cumulo+Cell_conc._interval+rab_integral+RQ_integral+Accum._Yield+Arg_conc.+emission_O2+emission_CO2; 0.542, 0.802, pH+AN+AN_cumulo+interval_yield+Feed_Vol+RS_cumulo+Cell_conc._interval+rab_integral+RQ_integral+Arg_conc.+emission_O2+emission_CO2; 0.518, 0.802, pH+PL+PL_cumulo+AN+AN_cumulo+Feed_Vol+RS_cumulo+rab_integral+RQ_integral+Arg_conc.+emission_O2+emission_CO2+consum_O2+generate_CO2; 0.541, 0.802, pH+AN+AN_cumulo+Feed_Vol+RS_cumulo+rab_integral+RQ_integral+Accum._Yield+Arg_conc.+emission_O2+emission_CO2+interval_O2; 0.541, 0.802, tmp+pH+PL+PL_cumulo+AN+Feed_Vol+RS_cumulo+rab_integral+RQ_integral+Arg_conc.+emission_O2+emission_CO2; 0.562, 0.802, pH+AN+interval_yield+Feed_Vol+RS_cumulo+rab_integral+RQ_integral+Arg_conc.+emission_O2+emission_CO2; 0.562, 0.802, tmp_cumulo+pH+AN+Feed_Vol+RS_cumulo+rab_integral+RQ_integral+Arg_conc.+emission_O2+emission_CO2; 0.562, 0.802, pH+AN+Feed_Vol+RS_cumulo+Cell_conc._interval+rab_integral+RQ_integral+Arg_conc.+emission_O2+emission_CO2; 0.518, 0.802, tmp_cumulo+pH+PL+PL_cumulo+AN+AN_cumulo+Feed_Vol+RS_cumulo+rab_integral+RQ_integral+Arg_conc.+emission_O2+emission_CO2+interval_O2; 0.530, 0.802, pH+PL+PL_cumulo+AN+interval_yield+Feed_Vol+RS_cumulo+rab_integral+RQ_integral+Arg_conc.+emission_O2+emission_CO2+ interval_O2; 0.530, 0.802, tmp+pH+PL+PL_cumulo+AN+interval_yield+Feed_Vol+RS_cumulo+rab_integral+RQ_integral+Arg_conc.+emission_O2+emission_CO2; 0.541, 0.802, tmp_cumulo+pH+PL+AN+interval_yield+Feed_Vol+RS_cumulo+rab_integral+RQ_integral+Arg_conc.+emission_O2+emission_CO2; 0.518, 0.802, pH+pH_cumulo+PL+PL_cumulo+AN+AN_cumulo+interval_yield+Feed_Vol+RS_cumulo+rab_integral+RQ_integral+Arg_conc.+emission_O2+emission_CO2; 0.540, 0.802, tmp_cumulo+pH+AN+AN_cumulo+interval_yield+Feed_Vol+RS_cumulo+rab_integral+RQ_integral+Arg_conc.+emission_O2+emission_CO2; 0.551, 0.802, pH+PL+AN+Feed_Vol+RS_cumulo+rab_integral+RQ_integral+Accum._Yield+Arg_conc.+emission_O2+emission_CO2; 0.561, 0.802, pH+AN+Feed_Vol+RS_cumulo+rab_integral+RQ_integral+Accum._Yield+Arg_conc.+emission_O2+emission_CO2; 0.529, 0.802, tmp_cumulo+pH+PL+AN+AN_cumulo+Feed_Vol+RS_cumulo+rab_integral+RQ_integral+Accum._Yield+Arg_conc.+emission_O2+emission_CO2; 0.529, 0.801, pH+PL_cumulo+AN+AN_cumulo+interval_yield+Feed_Vol+RS_cumulo+rab_integral+RQ_integral+Arg_conc.+emission_O2+emission_CO2+interval_O2; 0.529, 0.801, tmp+pH+PL_cumulo+AN+AN_cumulo+Feed_Vol+RS_cumulo+rab_integral+RQ_integral+Accum._Yield+Arg_conc.+emission_O2+emission_CO2; 0.517, 0.801, tmp+pH+PL+PL_cumulo+AN+interval_yield+Feed_Vol+RS_cumulo+rab_integral+RQ_integral+Arg_conc.+emission_O2+emission_CO2+interval_O2; 0.551, 0.801, pH+PL+AN+Feed_Vol+RS_cumulo+rab_integral+RQ_integral+Arg_conc.+emission_O2+emission_CO2+interval_O2; 0.551, 0.801, pH+PL_cumulo+AN+interval_yield+Feed_Vol+RS_cumulo+rab_integral+RQ_integral+Arg_conc.+emission_O2+emission_CO2; 0.505, 0.801, pH+PL+PL_cumulo+AN+AN_cumulo+interval_yield+Feed_Vol+RS_cumulo+rab_integral+RQ_integral+Accum._Yield+Arg_conc.+emission_O2+emission_CO2+consum_O2; 0.529, 0.801, tmp_cumulo+pH+PL_cumulo+AN+AN_cumulo+Feed_Vol+RS_cumulo+rab_integral+RQ_integral+Accum._Yield+Arg_conc.+emission_O2+emission_CO2; 0.517, 0.801, tmp+pH+PL+PL_cumulo+AN+AN_cumulo+Feed_Vol+RS_cumulo+rab_integral+RQ_integral+Arg_conc.+emission_O2+emission_CO2+interval_O2; 0.529, 0.801, tmp_cumulo+pH+PL+AN+AN_cumulo+Feed_Vol+RS_cumulo+rab_integral+RQ_integral+Arg_conc.+emission_O2+emission_CO2+interval_O2; 0.540, 0.801, pH_cumulo+PL_cumulo+AN+AN_cumulo+interval_yield+Feed_Vol+RS_cumulo+rab_integral+RQ_integral+Arg_conc.+emission_O2+emission_CO2; 0.517, 0.801, pH_cumulo+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2; 0.517, 0.801, pH+pH_cumulo+PL+PL_cumulo+AN+AN_cumulo+Feed_Vol+RS_cumulo+rab_integral+RQ_integral+Arg_conc.+emission_O2+emission_CO2+consum_O2; 0.504, 0.801, tmp+pH+PL+PL_cumulo+AN+interval_yield+Feed_Vol+RS_cumulo+rab_integral+RQ_integral+Accum._Yield+Arg_conc.+emission_O2+emission_CO2+consum_O2; 0.560, 0.801, tmp+pH+AN+Feed_Vol+RS_cumulo+rab_integral+RQ_integral+Arg_conc.+emission_O2+emission_CO2; 0.516, 0.801, pH+PL+PL_cumulo+AN+AN_cumulo+Feed_Vol+RS_cumulo+rab_integral+RQ_integral+Arg_conc.+emission_O2+emission_CO2+interval_O2+generate_CO2; 0.528, 0.801, pH_cumulo+PL+PL_cumulo+AN+AN_cumulo+interval_yield+Feed_Vol+RS_cumulo+rab_integral+RQ_integral+Arg_conc.+emission_O2+emission_CO2;

0.504, 0.801, pH+PL_cumulo+AN+AN_cumulo+interval_yield+Feed_Vol+RS_cumulo+rab_integral+RQ_integral+Accum._Yield+Arg_conc.+emission_O2+emission_CO2+interval_O2; 0.528, 0.801, pH+PL+PL_cumulo+AN+AN_cumulo+Feed_Vol+RS_cumulo+Cell_conc._interval+rab_integral+RQ_integral+Arg_conc.+emission_O2+emission_CO2; 0.528, 0.801, pH+PL_cumulo+AN+AN_cumulo+Feed_Vol+RS_cumulo+rab_integral+RQ_integral+Accum._Yield+Arg_conc.+emission_O2+emission_CO2+interval_O2; 0.516, 0.801, tmp_cumulo+pH+PL+PL_cumulo+AN+interval_yield+Feed_Vol+RS_cumulo+rab_integral+RQ_integral+Arg_conc.+emission_O2+emission_CO2+interval_O2; 0.516, 0.801, pH+PL+PL_cumulo+AN+interval_yield+Feed_Vol+RS_cumulo+rab_integral+RQ_integral+Accum._Yield+Arg_conc.+emission_O2+emission_CO2+consum_O2; 0.528, 0.801, tmp+pH+PL+AN+AN_cumulo+interval_yield+Feed_Vol+RS_cumulo+rab_integral+RQ_integral+Arg_conc.+emission_O2+emission_CO2; 0.539, 0.801, tmp_cumulo+pH+AN+AN_cumulo+Feed_Vol+RS_cumulo+rab_integral+RQ_integral+Arg_conc.+emission_O2+emission_CO2+generate_CO2; 0.550, 0.801, pH+PL+AN+Feed_Vol+RS_cumulo+rab_integral+RQ_integral+Arg_conc.+emission_O2+emission_CO2+generate_CO2; 0.539, 0.801, pH_cumulo+PL+PL_cumulo+AN+AN_cumulo+Feed_Vol+RS_cumulo+rab_integral+RQ_integral+Arg_conc.+emission_O2+emission_CO2; 0.528, 0.801, pH+PL_cumulo+AN+AN_cumulo+Feed_Vol+RS_cumulo+rab_integral+RQ_integral+Accum._Yield+Arg_conc.+emission_O2+emission_CO2+consum_O2; 0.549, 0.801, pH+PL+AN+Feed_Vol+RS_cumulo+Cell_conc._interval+rab_integral+RQ_integral+Arg_conc.+emission_O2+emission_CO2; 0.539, 0.801, tmp_cumulo+pH+AN+AN_cumulo+Feed_Vol+RS_cumulo+rab_integral+RQ_integral+Arg_conc.+emission_O2+emission_CO2+interval_O2; 0.527, 0.801, tmp_cumulo+pH+PL+PL_cumulo+AN+Feed_Vol+RS_cumulo+rab_integral+RQ_integral+Arg_conc.+emission_O2+emission_CO2+consum_O2; 0.516, 0.801, pH+PL+PL_cumulo+AN+AN_cumulo+Feed_Vol+RS_cumulo+rab_integral+RQ_integral+Arg_conc.+emission_O2+emission_CO2+consum_O2+interval_O2; 0.527, 0.801, pH+PL+AN+AN_cumulo+interval_yield+Feed_Vol+RS_cumulo+rab_integral+RQ_integral+Accum._Yield+Arg_conc.+emission_O2+emission_CO2; 0.515, 0.801, pH+PL+PL_cumulo+AN+AN_cumulo+Feed_Vol+RS_cumulo+rab_integral+RQ_integral+Accum._Yield+Arg_conc.+emission_O2+emission_CO2+consum_O2; 0.527, 0.801, pH+PL_cumulo+AN+interval_yield+Feed_Vol+RS_cumulo+Cell_conc._interval+rab_integral+RQ_integral+Accum._Yield+Arg_conc.+emission_O2+emission_CO2; 0.559, 0.801, pH+AN+Feed_Vol+RS_cumulo+rab_integral+RQ_integral+Arg_conc.+emission_O2+emission_CO2+interval_O2; 0.527, 0.801, tmp+pH+PL+AN+AN_cumulo+Feed_Vol+RS_cumulo+rab_integral+RQ_integral+Arg_conc.+emission_O2+emission_CO2+interval_O2; 0.538, 0.801, pH+PL+PL_cumulo+AN+Feed_Vol+RS_cumulo+rab_integral+RQ_integral+Accum._Yield+Arg_conc.+emission_O2+emission_CO2; 0.549, 0.800, pH+PL_cumulo+AN_cumulo+Feed_Vol+RS_cumulo+rab_integral+RQ_integral+Accum._Yield+Arg_conc.+emission_O2+emission_CO2; 0.527, 0.800, pH+PL+PL_cumulo+AN+interval_yield+Feed_Vol+RS_cumulo+rab_integral+RQ_integral+Accum._Yield+Arg_conc.+emission_O2+emission_CO2; 0.503, 0.800, tmp_cumulo+pH+PL+PL_cumulo+AN+interval_yield+Feed_Vol+RS_cumulo+rab_integral+RQ_integral+Accum._Yield+Arg_conc.+emission_O2+emission_CO2+consum_O2; 0.527, 0.800, tmp_cumulo+pH+PL_cumulo+AN+AN_cumulo+interval_yield+Feed_Vol+RS_cumulo+rab_integral+RQ_integral+Arg_conc.+emission_O2+emission_CO2; 0.527, 0.800, tmp+pH+PL_cumulo+AN+AN_cumulo+interval_yield+Feed_Vol+RS_cumulo+rab_integral+RQ_integral+Arg_conc.+emission_O2+emission_CO2; 0.527, 0.800, pH+PL+PL_cumulo+AN+interval_yield+Feed_Vol+RS_cumulo+Cell_conc._interval+rab_integral+RQ_integral+Arg_conc.+emission_O2+emission_CO2; 0.527, 0.800, tmp_cumulo+pH+PL+PL_cumulo+AN+interval_yield+Feed_Vol+RS_cumulo+rab_integral+RQ_integral+Arg_conc.+emission_O2+emission_CO2; 0.559, 0.800, pH+AN_cumulo+Feed_Vol+RS_cumulo+rab_integral+RQ_integral+Accum._Yield+Arg_conc.+emission_O2+emission_CO2; 0.526, 0.800, tmp+pH+PL+AN+AN_cumulo+Feed_Vol+RS_cumulo+rab_integral+RQ_integral+Accum._Yield+Arg_conc.+emission_O2+emission_CO2; 0.526, 0.800, tmp_cumulo+pH+PL+AN+AN_cumulo+Feed_Vol+RS_cumulo+rab_integral+RQ_integral+Arg_conc.+emission_O2+emission_CO2+generate_CO2; 0.537, 0.800, tmp+pH+AN+AN_cumulo+Feed_Vol+RS_cumulo+rab_integral+RQ_integral+Arg_conc.+emission_O2+emission_CO2+interval_O2; 0.537, 0.800, tmp+pH+AN+AN_cumulo+Feed_Vol+RS_cumulo+rab_integral+RQ_integral+Arg_conc.+emission_O2+emission_CO2+generate_CO2; 0.558, 0.800, pH+AN+Feed_Vol+RS_cumulo+rab_integral+RQ_integral+Arg_conc.+emission_O2+emission_CO2+generate_CO2; 0.526, 0.800, pH+PL+AN+AN_cumulo+interval_yield+Feed_Vol+RS_cumulo+Cell_conc._interval+rab_integral+RQ_integral+Arg_conc.+emission_O2+emission_CO2; 0.526, 0.800, pH+PL_cumulo+AN+AN_cumulo+interval_yield+Feed_Vol+RS_cumulo+Cell_conc._interval+rab_integral+RQ_integral+Arg_conc.+emission_O2+emission_CO2; 0.514, 0.800, pH+PL_cumulo+AN+AN_cumulo+interval_yield+Feed_Vol+RS_cumulo+rab_integral+RQ_integral+Accum._Yield+Arg_conc.+emission_O2+emission_CO2+interval_O2; 0.537, 0.800, tmp_cumulo+pH+AN+AN_cumulo+Feed_Vol+RS_cumulo+Cell_conc._interval+rab_integral+RQ_integral+Arg_conc.+emission_O2+emission_CO2; 0.537, 0.800, tmp+pH+AN+AN_cumulo+interval_yield+Feed_Vol+RS_cumulo+rab_integral+RQ_integral+Arg_conc.+emission_O2+emission_CO2; 0.537, 0.800, pH+PL+PL_cumulo+AN+Feed_Vol+RS_cumulo+rab_integral+RQ_integral+Arg_conc.+emission_O2+emission_CO2+interval_O2; 0.537, 0.800, tmp_cumulo+pH+PL+PL_cumulo+AN+Feed_Vol+RS_cumulo+rab_integral+RQ_integral+Arg_conc.+emission_O2+emission_CO2; 0.501, 0.800, pH+pH_cumulo+PL+PL_cumulo+AN+AN_cumulo+interval_yield+Feed_Vol+RS_cumulo+rab_integral+RQ_integral+Arg_conc.+emission_O2+emission_CO2+interval_O2; 0.537, 0.800, tmp+pH+PL+AN+interval_yield+Feed_Vol+RS_cumulo+rab_integral+RQ_integral+Arg_conc.+emission_O2+emission_CO2; 0.525, 0.800, tmp+pH+AN+interval_yield+Feed_Vol+RS_cumulo+Cell_conc._interval+rab_integral+RQ_integral+Accum._Yield+Arg_conc.+emission_O2+emission_CO2; 0.525, 0.800, tmp+pH+PL+AN+AN_cumulo+Feed_Vol+RS_cumulo+rab_integral+RQ_integral+Arg_conc.+emission_O2+emission_CO2+generate_CO2; 0.547, 0.800, tmp+tmp_cumulo+pH+AN_cumulo+Feed_Vol+RS_cumulo+rab_integral+RQ_integral+Arg_conc.+emission_O2+emission_CO2; 0.513, 0.800, pH+PL+PL_cumulo+AN+AN_cumulo+Feed_Vol+RS_cumulo+Cell_conc._cumulo+rab_integral+RQ_integral+Arg_conc.+emission_O2+emission_CO2+interval_O2; 0.513, 0.800, pH+PL+PL_cumulo+AN+interval_yield+Feed_Vol+RS_cumulo+Cell_conc._interval+rab_integral+RQ_integral+Accum._Yield+Arg_conc.+emission_O2+emission_CO2; 0.536, 0.800, pH+AN+AN_cumulo+Feed_Vol+RS_cumulo+Cell_conc._interval+rab_integral+RQ_integral+Arg_conc.+emission_O2+emission_CO2+generate_CO2; 0.547, 0.800, pH+PL+AN+Feed_Vol+RS_cumulo+Cell_conc._cumulo+rab_integral+RQ_integral+Arg_conc.+emission_O2+emission_CO2; 0.525, 0.800, pH+PL+AN+AN_cumulo+Feed_Vol+RS_cumulo+rab_integral+RQ_integral+Accum._Yield+Arg_conc.+emission_O2+emission_CO2+generate_CO2; 0.513, 0.799, pH+PL+PL_cumulo+AN+AN_cumulo+interval_yield+Feed_Vol+RS_cumulo+rab_integral+RQ_integral+Arg_conc.+emission_O2+emission_CO2+generate_CO2; 0.557, 0.799, tmp+pH+AN_cumulo+Feed_Vol+RS_cumulo+rab_integral+RQ_integral+Arg_conc.+emission_O2+emission_CO2; 0.547, 0.799, pH+PL+AN+Feed_Vol+RS_cumulo+rab_integral+RQ_integral+Arg_conc.+emission_O2+emission_CO2+consum_O2; 0.513, 0.799, tmp_cumulo+pH+AN+AN_cumulo+interval_yield+Feed_Vol+RS_cumulo+Cell_conc._interval+rab_integral+RQ_integral+Accum._Yield+Arg_conc.+emission_O2+emission_CO2; 0.546, 0.799, pH+PL_cumulo+AN+Feed_Vol+RS_cumulo+rab_integral+RQ_integral+Accum._Yield+Arg_conc.+emission_O2+emission_CO2; 0.536, 0.799, pH+PL+PL_cumulo+AN+Feed_Vol+RS_cumulo+rab_integral+RQ_integral+Arg_conc.+emission_O2+emission_CO2+generate_CO2; 0.546, 0.799, pH+pH_cumulo+PL+AN+Feed_Vol+RS_cumulo+rab_integral+RQ_integral+Arg_conc.+emission_O2+emission_CO2; 0.512, 0.799, tmp+tmp_cumulo+pH+PL+PL_cumulo+AN+AN_cumulo+Feed_Vol+RS_cumulo+rab_integral+RQ_integral+Arg_conc.+emission_O2+emission_CO2; 0.524, 0.799, tmp_cumulo+pH+pH_cumulo+PL+AN+AN_cumulo+Feed_Vol+RS_cumulo+rab_integral+RQ_integral+Arg_conc.+emission_O2+emission_CO2; 0.524, 0.799, tmp+pH+PL+AN+interval_yield+Feed_Vol+RS_cumulo+Cell_conc._interval+rab_integral+RQ_integral+Arg_conc.+emission_O2+emission_CO2; 0.535, 0.799, tmp+pH+AN+AN_cumulo+Feed_Vol+RS_cumulo+Cell_conc._interval+rab_integral+RQ_integral+Arg_conc.+emission_O2+emission_CO2; 0.535, 0.799, pH+pH_cumulo+AN+AN_cumulo+Feed_Vol+RS_cumulo+rab_integral+RQ_integral+Accum._Yield+Arg_conc.+emission_O2+emission_CO2; 0.512, 0.799, pH+PL+PL_cumulo+AN+AN_cumulo+interval_yield+Feed_Vol+RS_cumulo+Cell_conc._interval+rab_integral+RQ_integral+Arg_conc.+emission_O2+emission_CO2; 0.512, 0.799, tmp+tmp_cumulo+pH+PL+AN+AN_cumulo+interval_yield+Feed_Vol+RS_cumulo+rab_integral+RQ_integral+Arg_conc.+emission_O2+emission_CO2; 0.499, 0.799, pH+PL+PL_cumulo+AN+AN_cumulo+interval_yield+Feed_Vol+RS_cumulo+rab_integral+RQ_integral+Arg_conc.+emission_O2+emission_CO2+consum_O2+generate_CO2; 0.524, 0.799, pH+PL+AN+AN_cumulo+interval_yield+Feed_Vol+RS_cumulo+rab_integral+RQ_integral+Arg_conc.+emission_O2+emission_CO2+interval_O2; 0.524, 0.799, pH+PL+PL_cumulo+AN+Feed_Vol+RS_cumulo+rab_integral+RQ_integral+Accum._Yield+Arg_conc.+emission_O2+emission_CO2+consum_O2; 0.524, 0.799, pH+PL+AN+AN_cumulo+Feed_Vol+RS_cumulo+rab_integral+RQ_integral+Accum._Yield+Arg_conc.+emission_O2+emission_CO2+interval_O2; 0.524, 0.799, pH+PL_cumulo+AN+AN_cumulo+interval_yield+Feed_Vol+RS_cumulo+rab_integral+RQ_integral+Arg_conc.+emission_O2+emission_CO2+generate_CO2; 0.556, 0.799, pH_cumulo+AN+AN_cumulo+Feed_Vol+RS_cumulo+rab_integral+RQ_integral+Arg_conc.+emission_O2+emission_CO2; 0.523, 0.799, tmp_cumulo+pH+AN+interval_yield+Feed_Vol+ RS_cumulo+Cell_conc._interval+rab_integral+RQ_integral+Accum._Yield+Arg_conc.+emission_O2+emission_CO2; 0.523, 0.799, pH+PL_cumulo+AN+AN_cumulo+ Feed_Vol+RS_cumulo+Cell_conc._interval+rab_integral+ RQ_integral+Accum._Yield+Arg_conc.+emission_O2+ emission_CO2; 0.511, 0.799, tmp+pH+AN+AN_cumulo+ interval_yield+Feed_Vol+RS_cumulo+Cell_conc._ interval+rab_integral+RQ_integral+Accum._Yield+Arg_ conc.+emission_O2+emission_CO2; 0.523, 0.799, pH+PL_ cumulo+AN+AN_cumulo+interval_yield+Feed_Vol+RS_ cumulo+rab_integral+RQ_integral+Arg_conc.+emission_ O2+emission_CO2+consum_O2; 0.523, 0.799, tmp_ cumulo+pH+PL+AN+interval_yield+Feed_Vol+RS_ cumulo+Cell_conc._interval+rab_integral+RQ_integral+ Arg_conc.+emission_O2+emission_CO2; 0.535, 0.799, pH+PL_cumulo+AN+interval_yield+Feed_Vol+RS_cumulo+Cell_conc._interval+rab_integral+RQ_integral+Arg_ conc.+emission_O2+emission_CO2; 0.511, 0.799, pH+AN+AN_cumulo+interval_yield+Feed_Vol+RS_cumulo+Cell_conc._interval+rab_integral+RQ_integral+Accum._Yield+Arg_conc.+emission_O2+emission_CO2+ generate_CO2; 0.499, 0.799, tmp+tmp_cumulo+pH+PL+ PL_cumulo+AN+interval_yield+Feed_Vol+RS_cumulo+ rab_integral+RQ_integral+Arg_conc.+emission_O2+ emission_CO2+consum_O2; 0.485, 0.799, tmp_cumulo+ pH+PL+PL_cumulo+AN+AN_cumulo+interval_yield+ Feed_Vol+RS_cumulo+rab_integral+RQ_integral+ Accum._Yield+Arg_conc.+emission_O2+emission_CO2+ consum_O2; 0.556, 0.799, tmp_cumulo+pH+AN_cumulo+ Feed_Vol+RS_cumulo+rab_integral+RQ_integral+Arg_ conc.+emission_O2+emission_CO2; 0.511, 0.799, pH_cumulo+PL+PL_cumulo+AN+AN_cumulo+interval_ yield+Feed_Vol+RS_cumulo+rab_integral+RQ_integral+ Arg_conc.+emission_O2+emission_CO2+interval_O2; 0.511, 0.799, pH+PL+AN+AN_cumulo+interval_yield+ Feed_Vol+RS_cumulo+Cell_conc._interval+rab_integral+ RQ_integral+Accum._Yield+Arg_conc.+emission_O2+ emission_CO2; 0.534, 0.799, pH+AN+AN_cumulo+Feed_ Vol+RS_cumulo+Cell_conc._interval+rab_integral+RQ_ integral+Arg_conc.+emission_O2+emission_CO2+ interval_O2; 0.534, 0.799, tmp+pH+AN+interval_yield+ Feed_Vol+RS_cumulo+Cell_conc._interval+rab_integral+ RQ_integral+Arg_conc.+emission_O2+emission_CO2; 0.523, 0.799, pH+pH_cumulo+PL_cumulo+AN+AN_cumulo+interval_yield+Feed_Vol+RS_cumulo+rab_integral+ RQ_integral+Arg_conc.+emission_O2+emission_CO2; 0.523, 0.799, tmp_cumulo+pH+PL+AN+AN_cumulo+ Feed_Vol+RS_cumulo+Cell_conc._cumulo+rab_integral+ RQ_integral+Arg_conc.+emission_O2+emission_CO2; 0.523, 0.799, tmp_cumulo+pH+PL+AN+AN_cumulo+ Feed_Vol+RS_cumulo+rab_integral+RQ_integral+Arg_ conc.+emission_O2+emission_CO2+consum_O2; 0.498, 0.799, pH+pH_cumulo+PL+PL_cumulo+AN+AN_cumulo+interval_yield+Feed_Vol+RS_cumulo+rab_integral+ RQ_integral+Arg_conc.+emission_O2+emission_CO2+ consum_O2; 0.523, 0.799, pH+AN+interval_yield+Feed_ Vol+RS_cumulo+Cell_conc._interval+rab_integral+RQ_ integral+Accum._Yield+Arg_conc.+emission_O2+ emission_CO2+interval_O2; 0.511, 0.799, pH+pH_ cumulo+PL+PL_cumulo+AN+AN_cumulo+Feed_Vol+ RS_cumulo+rab_integral+RQ_integral+Arg_conc.+ emission_O2+emission_CO2+interval_O2; 0.511, 0.799, tmp+pH+PL+PL_cumulo+AN+AN_cumulo+Feed_Vol+ RS_cumulo+rab_integral+RQ_integral+Accum._Yield+ Arg_conc.+emission_O2+emission_CO2; 0.511, 0.798, pH+AN+AN_cumulo+interval_yield+Feed_Vol+RS_cumulo+Cell_conc._interval+rab_integral+RQ_integral+Accum._Yield+Arg_conc.+emission_O2+emission_CO2+interval_O2; 0.534, 0.798, pH+PL+AN+interval_yield+Feed_ Vol+RS_cumulo+rab_integral+RQ_integral+Accum._ Yield+Arg_conc.+emission_O2+emission_CO2; 0.534, 0.798, pH+AN+AN_cumulo+Feed_Vol+RS_cumulo+rab_ integral+RQ_integral+Arg_conc.+emission_O2+emission_ CO2+consum_O2+interval_O2; 0.545, 0.798, tmp+pH+ PL_cumulo+AN+Feed_Vol+RS_cumulo+rab_integral+ RQ_integral+Arg_conc.+emission_O2+emission_CO2; 0.534, 0.798, pH+AN+AN_cumulo+interval_yield+Feed_ Vol+RS_cumulo+rab_integral+RQ_integral+Arg_conc.+ emission_O2+emission_CO2+interval_O2; 0.522, 0.798, pH+pH_cumulo+PL+AN+AN_cumulo+Feed_Vol+RS_cumulo+rab_integral+RQ_integral+Arg_conc.+emission_ O2+emission_CO2+interval_O2; 0.534, 0.798, pH_cumulo+PL_cumulo+AN+AN_cumulo+Feed_Vol+RS_ cumulo+rab_integral+RQ_integral+Accum._Yield+Arg_ conc.+emission_O2+emission_CO2; 0.522, 0.798, tmp_ cumulo+pH+PL_cumulo+AN+AN_cumulo+Feed_Vol+ RS_cumulo+rab_integral+RQ_integral+Arg_conc.+ emission_O2+emission_CO2+interval_O2; 0.534, 0.798, tmp_cumulo+pH_cumulo+PL_cumulo+AN+AN_cumulo+ Feed_Vol+RS_cumulo+rab_integral+RQ_integral+Arg_ conc.+emission_O2+emission_CO2; 0.510, 0.798, tmp+ pH+PL+PL_cumulo+AN+AN_cumulo+Feed_Vol+RS_ cumulo+rab_integral+RQ_integral+Arg_conc.+emission_ O2+emission_CO2+generate_CO2; 0.522, 0.798, pH_cumulo+PL_cumulo+AN+AN_cumulo+interval_ yield+Feed_Vol+RS_cumulo+Cell_conc._interval+rab_integral+RQ_integral+Arg_conc.+emission_O2+emission_ CO2; 0.534, 0.798, pH+AN+AN_cumulo+Feed_Vol+RS_ cumulo+rab_integral+RQ_integral+Accum._Yield+Arg_ conc.+emission_O2+emission_CO2+consum_O2; 0.544, 0.798, tmp_cumulo+pH+AN+interval_yield+Feed_Vol+ RS_cumulo+rab_integral+RQ_integral+Arg_conc.+emission_O2+emission_CO2; 0.522, 0.798, pH_cumulo+PL_cumulo+AN+AN_cumulo+interval_yield+Feed_Vol+RS_ cumulo+rab_integral+RQ_integral+Accum._Yield+Arg_ conc.+emission_O2+emission_CO2; 0.522, 0.798, tmp_ cumulo+pH+AN+AN_cumulo+interval_yield+Feed_Vol+ RS_cumulo+rab_integral+RQ_integral+Accum._Yield+ Arg_conc.+emission_O2+emission_CO2; 0.510, 0.798, pH+PL+PL_cumulo+AN+AN_cumulo+Feed_Vol+RS_cumulo+Cell_conc._interval+rab_integral+RQ_integral+Arg_ conc.+emission_O2+emission_CO2+consum_O2; 0.510, 0.798, tmp+pH+PL+AN+interval_yield+Feed_Vol+RS_cumulo+Cell_conc._interval+rab_integral+RQ_integral+Accum._Yield+Arg_conc.+emission_O2+emission_CO2; 0.522, 0.798, pH+AN+interval_yield+Feed_Vol+RS_cumulo+Cell_conc._interval+rab_integral+RQ_integral+Accum._Yield+Arg_conc.+emission_O2+emission_CO2+ generate_CO2; 0.522, 0.798, pH+PL+AN+AN_cumulo+ Feed_Vol+RS_cumulo+Cell_conc._cumulo+rab_integral+ RQ_integral+Arg_conc.+emission_O2+emission_CO2+ interval_O2; 0.510, 0.798, pH+PL+PL_cumulo+AN+AN_ cumulo+Feed_Vol+RS_cumulo+rab_integral+RQ_ integral+Accum._Yield+Arg_conc.+emission_O2+ emission_CO2+interval_O2; 0.522, 0.798, tmp+tmp_ cumulo+pH+AN+AN_cumulo+Feed_Vol+RS_cumulo+ rab_integral+RQ_integral+Accum._Yield+Arg_conc.+ emission_O2+emission_CO2; 0.533, 0.798, pH+AN+AN_ cumulo+Feed_Vol+RS_cumulo+rab_integral+RQ_ integral+Arg_conc.+emission_O2+emission_CO2+ interval_O2+generate_CO2; 0.510, 0.798, tmp_cumulo+ pH+PL+PL_cumulo+AN+AN_cumulo+Feed_Vol+RS_ cumulo+rab_integral+RQ_integral+Accum._Yield+Arg_ conc.+emission_O2+emission_CO2; 0.510, 0.798, pH+PL+PL_cumulo+AN+interval_yield+Feed_Vol+RS_cumulo+Cell_conc._interval+rab_integral+RQ_integral+Arg_conc.+emission_O2+emission_CO2+consum_O2; 0.533, 0.798, tmp_cumulo+pH+AN+interval_yield+Feed_Vol+RS_cumulo+Cell_conc._interval+rab_integral+RQ_integral+Arg_conc.+emission_O2+emission_CO2; 0.522, 0.798, pH+pH_cumulo+PL+AN+AN_cumulo+interval_yield+Feed_Vol+RS_cumulo+rab_integral+RQ_integral+Arg_conc.+emission_O2+emission_CO2; 0.497, 0.798, tmp+pH+PL+PL_cumulo+AN+interval_yield+Feed_Vol+RS_cumulo+Cell_conc._interval+rab_integral+RQ_integral+Arg_conc.+emission_O2+emission_CO2+consum_O2; 0.544, 0.798, pH+PL_cumulo+AN+AN_cumulo+Feed_Vol+RS_cumulo+Cell_conc._cumulo+rab_integral+RQ_integral+Arg_conc.+emission_O2+emission_CO2; 0.521, 0.798, pH+PL+AN+AN_cumulo+Feed_Vol+RS_cumulo+rab_integral+RQ_integral+Arg_conc.+emission_O2+emission_CO2+consum_O2+generate_CO2; 0.521, 0.798, pH+PL_cumulo+AN+AN_cumulo+Feed_Vol+RS_cumulo+rab_integral+RQ_integral+Arg_conc.+emission_O2+emission_CO2+consum_O2+interval_O2; 0.533, 0.798, tmp+pH_cumulo+PL_cumulo+AN+AN_cumulo+Feed_Vol+RS_cumulo+rab_integral+RQ_integral+Arg_conc.+emission_O2+emission_CO2; 0.521, 0.798, pH+PL+AN+AN_cumulo+Feed_Vol+RS_cumulo+rab_integral+RQ_integral+Arg_conc.+emission_O2+emission_CO2+consum_O2+interval_O2; 0.484, 0.798, tmp+pH+PL+PL_cumulo+AN+AN_cumulo+interval_yield+Feed_Vol+RS_cumulo+rab_integral+RQ_integral+Accum._Yield+Arg_conc.+emission_O2+emission_CO2+consum_O2; 0.521, 0.798, tmp+pH+PL+AN+AN_cumulo+Feed_Vol+RS_cumulo+Cell_conc._cumulo+rab_integral+RQ_integral+Arg_conc.+emission_O2+emission_CO2; 0.533, 0.798, pH+AN+interval_yield+RS+Feed_Vol+Cell_conc._interval+rab_integral+RQ_integral+Accum._Yield+Arg_conc.+emission_O2+emission_CO2; 0.509, 0.798, pH+PL+PL_cumulo+AN+AN_cumulo+Feed_Vol+RS_cumulo+rab_integral+RQ_integral+Accum._Yield+Arg_conc.+emission_O2+emission_CO2+generate_CO2; 0.521, 0.798, tmp+pH+PL_cumulo+AN+AN_cumulo+Feed_Vol+RS_cumulo+rab_integral+RQ_integral+Arg_conc.+emission_O2+emission_CO2+generate_CO2; 0.543, 0.798, pH+AN+Feed_Vol+RS_cumulo+Cell_conc._interval+rab_integral+RQ_integral+Accum._Yield+Arg_conc.+emission_O2+emission_CO2; 0.533, 0.798, tmp_cumulo+pH+pH_cumulo+AN+AN_cumulo+Feed_Vol+RS_cumulo+rab_integral+RQ_integral+Arg_conc.+emission_O2+emission_CO2; 0.509, 0.798, pH+PL_cumulo+AN+AN_cumulo+interval_yield+Feed_Vol+RS_cumulo+rab_integral+RQ_integral+Accum._Yield+Arg_conc.+emission_O2+emission_CO2+consum_O2; 0.521, 0.798, tmp_cumulo+pH+PL_cumulo+AN+AN_cumulo+Feed_Vol+RS_cumulo+rab_integral+RQ_integral+Arg_conc.+emission_O2+emission_CO2+consum_O2; 0.509, 0.798, tmp_cumulo+pH+PL+AN+AN_cumulo+interval_yield+Feed_Vol+RS_cumulo+rab_integral+RQ_integral+Accum._Yield+Arg_conc.+emission_O2+emission_CO2; 0.521, 0.798, pH+pH_cumulo+PL_cumulo+AN+AN_cumulo+Feed_Vol+RS_cumulo+rab_integral+RQ_integral+Accum._Yield+Arg_conc.+emission_O2+emission_CO2; 0.509, 0.798, tmp+pH+PL+AN+AN_cumulo+interval_yield+Feed_Vol+RS_cumulo+rab_integral+RQ_integral+Accum._Yield+Arg_conc.+emission_O2+emission_CO2; 0.532, 0.798, pH+AN+AN_cumulo+interval_yield+Feed_Vol+RS_cumulo+rab_integral+RQ_integral+Arg_conc.+emission_O2+emission_CO2+generate_CO2; 0.521, 0.798, pH+PL_cumulo+AN+AN_cumulo+Feed_Vol+RS_cumulo+rab_integral+RQ_integral+Arg_conc.+emission_O2+emission_CO2+interval_O2+generate_CO2; 0.521, 0.798, tmp_cumulo+pH+PL+AN+AN_cumulo+Feed_Vol+RS_cumulo+Cell_conc._interval+rab_integral+RQ_integral+Arg_conc.+emission_O2+emission_CO2; 0.521, 0.798, pH_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2; 0.521, 0.798, pH+PL_cumulo+AN+AN_cumulo+Feed_Vol+RS_cumulo+Cell_conc._cumulo+rab_integral+RQ_integral+Accum._Yield+Arg_conc.+emission_O2+emission_CO2; 0.496, 0.798, pH+PL+PL_cumulo+AN+AN_cumulo+interval_yield+Feed_Vol+RS_cumulo+rab_integral+RQ_integral+Arg_conc.+emission_O2+emission_CO2+consum_O2+interval_O2; 0.496, 0.798, pH+PL+PL_cumulo+AN+interval_yield+Feed_Vol+RS_cumulo+Cell_conc._interval+rab_integral+RQ_integral+Accum._Yield+Arg_conc.+emission_O2+emission_CO2+consum_O2; 0.532, 0.798, pH+AN+AN_cumulo+Feed_Vol+RS_cumulo+Cell_conc._cumulo+rab_integral+RQ_integral+Accum._Yield+Arg_conc.+emission_O2+emission_CO2; 0.532, 0.798, pH+PL_cumulo+AN+AN_cumulo+interval_yield+Feed_Vol+RS_cumulo+rab_integral+RQ_integral+Accum._Yield+Arg_conc.+emission_O2+emission_CO2; 0.483, 0.798, tmp_cumulo+pH+PL+PL_cumulo+AN+AN_cumulo+interval_yield+Feed_Vol+RS_cumulo+rab_integral+RQ_integral+Accum._Yield+Arg_conc.+emission_O2+emission_CO2+interval_O2; 0.521, 0.798, pH+PL_cumulo+AN+AN_cumulo+Feed_Vol+RS_cumulo+Cell_conc._cumulo+rab_integral+RQ_integral+Arg_conc.+emission_O2+emission_CO2+interval_O2; 0.521, 0.797, tmp+pH+PL_cumulo+AN+AN_cumulo+Feed_Vol+RS_cumulo+rab_integral+RQ_integral+Arg_conc.+emission_O2+emission_CO2+interval_O2; 0.509, 0.797, tmp+tmp_cumulo+pH+PL+AN+AN_cumulo+Feed_Vol+RS_cumulo+rab_integral+RQ_integral+Arg_conc.+emission_O2+emission_CO2+interval_O2; 0.532, 0.797, tmp_cumulo+pH+AN+AN_cumulo+Feed_Vol+RS_cumulo+rab_integral+RQ_integral+Arg_conc.+emission_O2+emission_CO2+consum_O2; 0.521, 0.797, tmp+pH+pH_cumulo+PL+AN+AN_cumulo+Feed_Vol+RS_cumulo+rab_integral+RQ_integral+Arg_conc.+emission_O2+emission_CO2; 0.532, 0.797, pH+pH_cumulo+AN+AN_cumulo+Feed_Vol+RS_cumulo+rab_integral+RQ_integral+Arg_conc.+emission_O2+emission_CO2+interval_O2; 0.508, 0.797, tmp_cumulo+pH+PL+AN+interval_yield+Feed_Vol+RS_cumulo+Cell_conc._interval+rab_integral+RQ_integral+Accum._Yield+Arg_conc.+emission_O2+emission_CO2; 0.520, 0.797, pH+PL+AN+AN_cumulo+Feed_Vol+RS_cumulo+rab_integral+RQ_integral+Arg_conc.+emission_O2+emission_CO2+interval_O2+generate_CO2; 0.508, 0.797, pH+PL_cumulo+AN+AN_cumulo+interval_yield+Feed_Vol+RS_cumulo+rab_integral+RQ_integral+Accum._Yield+Arg_conc.+emission_O2+emission_CO2+generate_CO2; 0.543, 0.797, pH+AN+interval_yield+Feed_Vol+RS_cumulo+rab_integral+RQ_integral+Accum._Yield+Arg_conc.+emission_O2+emission_CO2; 0.520, 0.797, pH+PL_cumulo+AN+AN_cumulo+Feed_Vol+RS_cumulo+Cell_conc._cumulo+rab_integral+RQ_integral+Arg_conc.+emission_O2+emission_CO2+generate_CO2; 0.532, 0.797, tmp_cumulo+pH+AN+AN_cumulo+Feed_Vol+RS_cumulo+Cell_conc._cumulo+rab_integral+RQ_integral+Arg_conc.+emission_O2+emission_CO2; 0.520, 0.797, tmp+tmp_cumulo+pH+PL_cumulo+AN+AN_cumulo+Feed_Vol+RS_cumulo+rab_integral+RQ_integral+Arg_conc.+emission_O2+ emission_CO2; 0.543, 0.797, pH+PL_cumulo+AN+Feed_Vol+RS_cumulo+rab_integral+RQ_integral+Arg_conc.+emission_O2+emission_CO2+generate_CO2; 0.532, 0.797, pH+AN+AN_cumulo+Feed_Vol+RS_cumulo+rab_integral+RQ_integral+Arg_conc.+emission_O2+emission_CO2+consum_O2+generate_CO2; 0.532, 0.797, pH+PL_cumulo+AN+interval_yield+Feed_Vol+RS_cumulo+rab_integral+RQ_integral+Accum._Yield+Arg_conc.+emission_O2+emission_CO2; 0.542, 0.797, pH+PL_cumulo+AN+Feed_Vol+RS_cumulo+rab_integral+RQ_integral+Arg_conc.+emission_O2+emission_CO2+consum_O2; 0.482, 0.797, tmp+tmp_cumulo+pH+PL_cumulo+AN+AN_cumulo+interval_yield+Feed_Vol+RS_cumulo+rab_integral+RQ_integral+Arg_conc.+emission_O2+emission_CO2+consum_O2; 0.496, 0.797, tmp+tmp_cumulo+pH+PL+PL_cumulo+AN+AN_cumulo+Feed_Vol+RS_cumulo+rab_integral+RQ_integral+Arg_conc.+emission_O2+emission_CO2+consum_O2; 0.508, 0.797, tmp_cumulo+pH+PL+AN+AN_cumulo+interval_yield+Feed_Vol+RS_cumulo+rab_integral+RQ_integral+Accum._Yield+Arg_conc.+emission_O2+emission_CO2; 0.508, 0.797, pH+pH_cumulo+PL+PL_cumulo+AN+interval_yield+Feed_Vol+RS_cumulo+rab_integral+RQ_integral+Arg_conc.+emission_O2+emission_CO2+consum_O2; 0.520, 0.797, tmp+pH+PL_cumulo+AN+AN_cumulo+Feed_Vol+RS_cumulo+rab_integral+RQ_integral+Arg_conc.+emission_O2+emission_CO2+consum_O2; 0.495, 0.797, pH+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2+interval_O2; 0.508, 0.797, tmp+pH+PL+PL_cumulo+AN+AN_cumulo+Feed_Vol+RS_cumulo+Cell_conc._cumulo+rab_integral+RQ_integral+Arg_conc.+emission_O2+emission_CO2; 0.508, 0.797, pH+pH_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2; 0.495, 0.797, pH+PL+PL_cumulo+AN+AN_cumulo+interval_yield+Feed_Vol+RS_cumulo+rab_integral+RQ_integral+Arg_conc.+emission_O2+emission_CO2+interval_O2+generate_CO2; 0.495, 0.797, tmp+pH+PL+PL_cumulo+AN+AN_cumulo+interval_yield+Feed_Vol+RS_cumulo+rab_integral+RQ_integral+Accum._Yield+Arg_conc.+emission_O2+emission_CO2; 0.508, 0.797, pH+PL+PL_cumulo+AN+AN_cumulo+interval_yield+Feed_Vol+RS_cumulo+Cell_conc._cumulo+rab_integral+RQ_integral+Arg_conc.+emission_O2+emission_CO2; 0.520, 0.797, tmp_cumulo+pH+PL_cumulo+AN+AN_cumulo+Feed_Vol+RS_cumulo+rab_integral+RQ_integral+Arg_conc.+emission_O2+emission_CO2+generate_CO2; 0.520, 0.797, pH+PL+AN+AN_cumulo+interval_yield+Feed_Vol+RS_cumulo+rab_integral+RQ_integral+Arg_conc.+emission_O2+emission_CO2+generate_CO2; 0.520, 0.797, pH+PL+AN+AN_cumulo+Feed_Vol+RS_cumulo+rab_integral+RQ_integral+Arg_conc.+emission_O2+emission_CO2+consum_O2+generate_CO2; 0.553, 0.797, pH+AN+Feed_Vol+RS_cumulo+rab_integral+RQ_integral+Arg_conc.+emission_O2+emission_CO2+consum_O2; 0.520, 0.797, pH+PL_cumulo+AN+AN_cumulo+Feed_Vol+RS_cumulo+Cell_conc._cumulo+rab_integral+RQ_integral+Arg_conc.+emission_O2+emission_CO2+consum_O2; 0.520, 0.797, pH+PL+AN+AN_cumulo+Feed_Vol+RS_cumulo+Cell_conc._cumulo+rab_integral+RQ_integral+Arg_conc.+emission_O2+emission_CO2+generate_CO2; 0.520, 0.797, pH+pH_cumulo+PL+AN+AN_cumulo+Feed_Vol+RS_cumulo+rab_integral+RQ_integral+Accum._Yield+Arg_conc.+emission_O2+emission_CO2; 0.508, 0.797, tmp_cumulo+pH+PL+PL_cumulo+AN+AN_cumulo+Feed_Vol+RS_cumulo+Cell_conc._cumulo+rab_integral+RQ_integral+Arg_conc.+emission_O2+emission_CO2; 0.495, 0.797, pH+PL+PL_cumulo+AN+AN_cumulo+interval_yield+Feed_Vol+RS_cumulo+Cell_conc._interval+rab_integral+RQ_integral+Arg_conc.+emission_O2+emission_CO2+interval_O2; 0.520, 0.797, tmp+pH+PL+AN+AN_cumulo+Feed_Vol+RS_cumulo+rab_integral+RQ_integral+Arg_conc.+emission_O2+emission_CO2+consum_O2; 0.531, 0.797, tmp+tmp_cumulo+pH+PL+AN+Feed_Vol+RS_cumulo+rab_integral+RQ_integral+Arg_conc.+emission_O2+emission_CO2; 0.519, 0.797, pH+pH_cumulo+PL+PL_cumulo+AN+Feed_Vol+RS_cumulo+rab_integral+RQ_integral+Arg_conc.+emission_O2+emission_CO2+consum_O2; 0.495, 0.797, tmp_cumulo+pH+pH_cumulo+PL+PL_cumulo+AN+interval_yield+Feed_Vol+RS_cumulo+rab_integral+RQ_integral+Arg_conc.+emission_O2+emission_CO2+consum_O2; 0.495, 0.797, tmp_cumulo+pH+PL+PL_cumulo+AN+AN_cumulo+interval_yield+Feed_Vol+RS_cumulo+rab_integral+RQ_integral+Accum._Yield+Arg_conc.+emission_O2+emission_CO2; 0.519, 0.797, tmp_cumulo+pH+AN+AN_cumulo+Feed_Vol+RS_cumulo+rab_integral+RQ_integral+Accum._Yield+Arg_conc.+emission_O2+emission_CO2+generate_CO2; 0.552, 0.797, pH+pH_cumulo+AN+Feed_Vol+RS_cumulo+rab_integral+RQ_integral+Arg_conc.+emission_O2+emission_CO2; 0.519, 0.797, pH+pH_cumulo+PL+PL_cumulo+AN+interval_yield+Feed_Vol+RS_cumulo+rab_integral+RQ_integral+Arg_conc.+emission_O2+emission_CO2; 0.507, 0.797, pH+PL+PL_cumulo+AN+AN_cumulo+Feed_Vol+RS_cumulo+Cell_conc._cumulo+rab_integral+RQ_integral+Arg_conc.+emission_O2+emission_CO2+generate_CO2; 0.481, 0.797, tmp+tmp_cumulo+pH+PL+PL_cumulo+AN+AN_cumulo+interval_yield+Feed_Vol+RS_cumulo+rab_integral+RQ_integral+Arg_conc.+emission_O2+emission_CO2+interval_O2; 0.531, 0.797, pH+PL+PL_cumulo+AN+Feed_Vol+RS_cumulo+Cell_conc._interval+rab_integral+RQ_integral+Arg_conc.+emission_O2+emission_CO2; 0.542, 0.797, pH+AN+interval_yield+RS+Feed_Vol+Cell_conc._interval+rab_integral+RQ_integral+Arg_conc.+emission_O2+emission_CO2; 0.519, 0.797, pH+AN+AN_cumulo+Feed_Vol+RS_cumulo+Cell_conc._interval+rab_integral+RQ_integral+Accum._Yield+Arg_conc.+emission_O2+emission_CO2+generate_CO2; 0.542, 0.797, pH+PL_cumulo+AN+Feed_Vol+RS_cumulo+Cell_conc._interval+rab_integral+RQ_integral+Arg_conc.+emission_O2+emission_CO2; 0.507, 0.797, tmp_cumulo+pH+PL+PL_cumulo+AN+AN_cumulo+Feed_Vol+RS_cumulo+rab_integral+RQ_integral+Arg_conc.+emission_O2+emission_CO2+generate_CO2; 0.481, 0.797, tmp+pH+PL+PL_cumulo+AN+interval_yield+Feed_Vol+RS_cumulo+Cell_conc._interval+rab_integral+RQ_integral+Accum._Yield+Arg_conc.+emission_O2+emission_CO2+consum_O2; 0.519, 0.797, tmp_cumulo+pH+AN+AN_cumulo+interval_yield+Feed_Vol+RS_cumulo+Cell_conc._interval+rab_integral+RQ_integral+Arg_conc.+emission_O2+emission_CO2; 0.519, 0.797, tmp_cumulo+pH+PL_cumulo+AN+AN_cumulo+Feed_Vol+RS_cumulo+Cell_conc._cumulo+rab_integral+RQ_integral+Arg_conc.+emission_O2+emission_CO2; 0.541, 0.797, tmp+pH+AN+interval_yield+Feed_Vol+RS_cumulo+rab_integral+RQ_integral+Arg_conc.+emission_O2+emission_CO2; 0.519, 0.797, tmp+pH+PL+AN+AN_cumulo+Feed_Vol+RS_cumulo+Cell_conc._interval+rab_integral+RQ_integral+Arg_conc.+emission_O2+emission_CO2; 0.541, 0.797, tmp_cumulo+pH+PL_cumulo+AN+Feed_Vol+RS_cumulo+rab_integral+

RQ_integral+Arg_conc.+emission_O2+emission_CO2; 0.494, 0.797, pH+PL+PL_cumulo+AN+AN_cumulo+interval_yield+Feed_Vol+RS_cumulo+Cell_conc._cumulo+rab_integral+RQ_integral+Arg_conc.+emission_O2+emission_CO2+consum_O2; 0.530, 0.797, pH+AN+AN_cumulo+Feed_Vol+RS_cumulo+Cell_conc._cumulo+rab_integral+RQ_integral+Arg_conc.+emission_O2+emission_CO2+interval_O2; 0.530, 0.797, tmp_cumulo+pH+PL+AN+Feed_Vol+RS_cumulo+rab_integral+RQ_integral+Accum._Yield+Arg_conc.+emission_O2+emission_CO2; 0.494, 0.797, tmp_cumulo+pH+PL+PL_cumulo+AN+interval_yield+Feed_Vol+RS_cumulo+Cell_conc._interval+rab_integral+RQ_integral+Arg_conc.+emission_O2+emission_CO2+consum_O2; 0.481, 0.797, tmp+pH+PL+PL_cumulo+AN+AN_cumulo+interval_yield+Feed_Vol+RS_cumulo+rab_integral+RQ_integral+Accum._Yield+Arg_conc.+emission_O2+emission_CO2+interval_O2; 0.494, 0.797, tmp_cumulo+pH+PL+PL_cumulo+AN+AN_cumulo+Feed_Vol+RS_cumulo+Cell_conc._cumulo+rab_integral+RQ_integral+Arg_conc.+emission_O2+emission_CO2+consum_O2; 0.481, 0.797, tmp_cumulo+pH+pH_cumulo+PL+PL_cumulo+AN+AN_cumulo+interval_yield+Feed_Vol+RS_cumulo+rab_integral+RQ_integral+Arg_conc.+emission_O2+emission_CO2+interval_O2; 0.530, 0.797, pH+AN+AN_cumulo+Feed_Vol+RS_cumulo+Cell_conc._cumulo+rab_integral+RQ_integral+Arg_conc.+emission_O2+emission_CO2+generate_CO2; 0.507, 0.797, tmp+tmp_cumulo+pH+PL+AN+AN_cumulo+Feed_Vol+RS_cumulo+rab_integral+RQ_integral+Accum._Yield+Arg_conc.+emission_O2+emission_CO2; 0.519, 0.797, pH+pH_cumulo+AN+interval_yield+Feed_Vol+RS_cumulo+Cell_conc._interval+rab_integral+RQ_integral+Accum._Yield+Arg_conc.+emission_O2+emission_CO2; 0.519, 0.797, pH+PL+AN+AN_cumulo+interval_yield+Feed_Vol+RS_cumulo+Cell_conc._cumulo+rab_integral+RQ_integral+Arg_conc.+emission_O2+emission_CO2; 0.530, 0.797, pH+AN+AN_cumulo+Feed_Vol+RS_cumulo+Cell_conc._interval+rab_integral+RQ_integral+Arg_conc.+emission_O2+emission_CO2+consum_O2; 0.519, 0.797, tmp+pH+PL_cumulo+AN+AN_cumulo+Feed_Vol+RS_cumulo+Cell_conc._cumulo+rab_integral+RQ_integral+Arg_conc.+emission_O2+emission_CO2; 0.519, 0.797, pH+PL+AN+AN_cumulo+Feed_Vol+RS_cumulo+Cell_conc._interval+rab_integral+RQ_integral+Arg_conc.+emission_O2+emission_CO2+generate_CO2; 0.506, 0.797, pH+pH_cumulo+PL+PL_cumulo+AN+AN_cumulo+Feed_Vol+RS_cumulo+Cell_conc._cumulo+rab_integral+RQ_integral+Arg_conc.+emission_O2+emission_CO2; 0.506, 0.797, tmp+pH+pH_cumulo+PL+PL_cumulo+AN+AN_cumulo+Feed_Vol+RS_cumulo+rab_integral+RQ_integral+Arg_conc.+emission_O2+emission_CO2; 0.506, 0.796, tmp_cumulo+pH+pH_cumulo+PL+PL_cumulo+AN+AN_cumulo+Feed_Vol+RS_cumulo+rab_integral+RQ_integral+Arg_conc.+emission_O2+emission_CO2; 0.518, 0.796, tmp+pH+AN+AN_cumulo+interval_yield+Feed_Vol+RS_cumulo+rab_integral+RQ_integral+Accum._Yield+Arg_conc.+emission_O2+emission_CO2; 0.530, 0.796, pH+pH_cumulo+PL+PL_cumulo+AN+Feed_Vol+RS_cumulo+rab_integral+RQ_integral+Arg_conc.+emission_O2+emission_CO2; 0.494, 0.796, pH+PL+PL_cumulo+AN+AN_cumulo+interval_yield+Feed_Vol+RS_cumulo+Cell_conc._interval+rab_integral+RQ_integral+Arg_conc.+emission_O2+emission_CO2+consum_O2; 0.518, 0.796, pH+PL+AN+interval_yield+Feed_Vol+RS_cumulo+Cell_conc._interval+rab_integral+RQ_integral+Arg_conc.+emission_O2+emission_CO2+interval_O2; 0.530, 0.796, tmp+pH+AN+AN_cumulo+Feed_Vol+RS_cumulo+Cell_conc._cumulo+rab_integral+RQ_integral+Arg_conc.+emission_O2+emission_CO2; 0.541, 0.796, tmp+pH+PL_cumulo+AN_cumulo+Feed_Vol+RS_cumulo+rab_integral+RQ_integral+Arg_conc.+emission_O2+emission_CO2; 0.530, 0.796, pH+pH_cumulo+AN+AN_cumulo+interval_yield+Feed_Vol+RS_cumulo+rab_integral+RQ_integral+Arg_conc.+emission_O2+emission_CO2; 0.506, 0.796, pH+PL+PL_cumulo+AN+interval_yield+Feed_Vol+RS_cumulo+rab_integral+RQ_integral+Accum._Yield+Arg_conc.+emission_O2+emission_CO2+interval_O2; 0.494, 0.796, pH+pH_cumulo+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2; 0.518, 0.796, tmp+tmp_cumulo+pH+AN+AN_cumulo+interval_yield+Feed_Vol+RS_cumulo+rab_integral+RQ_integral+Arg_conc.+emission_O2+emission_CO2; 0.518, 0.796, tmp+tmp_cumulo+pH+PL+AN+interval_yield+Feed_Vol+RS_cumulo+rab_integral+RQ_integral+Arg_conc.+emission_O2+emission_CO2; 0.530, 0.796, pH+AN+interval_yield+Feed_Vol+RS_cumulo+Cell_conc._interval+rab_integral+RQ_integral+Arg_conc.+emission_O2+emission_CO2+interval_O2; 0.530, 0.796, tmp+pH+AN+AN_cumulo+Feed_Vol+RS_cumulo+rab_integral+RQ_integral+Arg_conc.+emission_O2+emission_CO2+consum_O2; 0.506, 0.796, pH+PL+AN+interval_yield+Feed_Vol+RS_cumulo+Cell_conc._interval+rab_integral+RQ_integral+Accum._Yield+Arg_conc.+emission_O2+emission_CO2+interval_O2; 0.551, 0.796, pH+AN+Feed_Vol+RS_cumulo+Cell_conc._cumulo+rab_integral+RQ_integral+Arg_conc.+emission_O2+emission_CO2; 0.518, 0.796, tmp+pH+AN+AN_cumulo+interval_yield+Feed_Vol+RS_cumulo+Cell_conc._interval+rab_integral+RQ_integral+Arg_conc.+emission_O2+emission_CO2; 0.540, 0.796, tmp+pH+AN+Feed_Vol+RS_cumulo+rab_integral+RQ_integral+Accum._Yield+Arg_conc.+emission_O2+emission_CO2; 0.518, 0.796, pH+PL+AN+AN_cumulo+Feed_Vol+RS_cumulo+Cell_conc._interval+rab_integral+RQ_integral+Arg_conc.+emission_O2+emission_CO2+interval_O2; 0.493, 0.796, pH+PL+PL_cumulo+AN+AN_cumulo+interval_yield+Feed_Vol+RS_cumulo+Cell_conc._cumulo+rab_integral+RQ_integral+Arg_conc.+emission_O2+emission_CO2+interval_O2; 0.518, 0.796, tmp_cumulo+pH+AN+AN_cumulo+Feed_Vol+RS_cumulo+Cell_conc._interval+rab_integral+RQ_integral+Accum._Yield+Arg_conc.+emission_O2+emission_CO2; 0.540, 0.796, pH+PL_cumulo+AN_cumulo+interval_yield+Feed_Vol+RS_cumulo+rab_integral+RQ_integral+Arg_conc.+emission_O2+emission_CO2; 0.529, 0.796, pH+PL+AN+interval_yield+Feed_Vol+RS_cumulo+rab_integral+RQ_integral+Arg_conc.+emission_O2+emission_CO2+interval_O2; 0.518, 0.796, pH+pH_cumulo+PL_cumulo+AN+AN_cumulo+Feed_Vol+RS_cumulo+Cell_conc._cumulo+rab_integral+RQ_integral+Arg_conc.+emission_O2+emission_CO2; 0.518, 0.796, tmp+pH+AN+AN_cumulo+Feed_Vol+RS_cumulo+rab_integral+RQ_integral+Accum._Yield+Arg_conc.+emission_O2+emission_CO2+generate_CO2; 0.493, 0.796, pH+PL+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2; 0.505, 0.796, tmp+pH+PL+PL_cumulo+AN+interval_yield+Feed_Vol+RS_cumulo+Cell_conc._interval+rab_integral+RQ_integral+Arg_conc.+emission_O2+emission_CO2; 0.505, 0.796, tmp_cumulo+pH+PL+AN+AN_cumulo+interval_yield+Feed_Vol+RS_cumulo+rab_integral+RQ_integral+Arg_conc.+emission_O2+emission_

CO2+interval_O2; 0.517, 0.796, pH+AN+interval_yield+Feed_Vol+RS_cumulo+Cell_conc._interval+rab_integral+RQ_integral+Accum._Yield+Arg_conc.+emission_O2+emission_CO2+consum_O2; 0.529, 0.796, pH+PL+AN+interval_yield+Feed_Vol+RS_cumulo+Cell_conc._cumulo+rab_integral+RQ_integral+Arg_conc.+emission_O2+emission_CO2; 0.517, 0.796, pH_cumulo+PL_cumulo+AN+interval_yield+Feed_Vol+RS_cumulo+Cell_conc._interval+rab_integral+RQ_integral+Accum._Yield+Arg_conc.+emission_O2+emission_CO2; 0.529, 0.796, pH+AN+interval_yield+Feed_Vol+RS_cumulo+Cell_conc._interval+rab_integral+RQ_integral+Arg_conc.+emission_O2+emission_CO2+generate_CO2; 0.517, 0.796, pH+PL_cumulo+AN+AN_cumulo+interval_yield+Feed_Vol+RS_cumulo+Cell_conc._cumulo+rab_integral+RQ_integral+Arg_conc.+emission_O2+emission_CO2; 0.505, 0.796, tmp+pH+PL+PL_cumulo+AN+interval_yield+Feed_Vol+RS_cumulo+rab_integral+RQ_integral+Accum._Yield+Arg_conc.+emission_O2+emission_CO2; 0.493, 0.796, tmp+pH+pH_cumulo+PL+PL_cumulo+AN+interval_yield+Feed_Vol+RS_cumulo+rab_integral+RQ_integral+Arg_conc.+emission_O2+emission_CO2+consum_O2; 0.517, 0.796, pH+PL_cumulo+AN+AN_cumulo+Feed_Vol+RS_cumulo+Cell_conc._interval+rab_integral+RQ_integral+Arg_conc.+emission_O2+emission_CO2+generate_CO2; 0.529, 0.796, tmp+pH+PL+AN+Feed_Vol+RS_cumulo+rab_integral+RQ_integral+Accum._Yield+Arg_conc.+emission_O2+emission_CO2; 0.505, 0.796, pH+PL+PL_cumulo+AN+interval_yield+Feed_Vol+RS_cumulo+Cell_conc._interval+rab_integral+RQ_integral+Arg_conc.+emission_O2+emission_CO2+interval_O2; 0.540, 0.796, PL_cumulo+AN_cumulo+interval_yield+Feed_Vol+RS_cumulo+rab_integral+Accum._Yield+Arg_conc.+emission_O2+emission_CO2+consum_O2; 0.517, 0.796, pH+pH_cumulo+PL+AN+AN_cumulo+Feed_Vol+RS_cumulo+rab_integral+RQ_integral+Arg_conc.+emission_O2+emission_CO2+generate_CO2; 0.505, 0.796, pH_cumulo+PL+PL_cumulo+AN+AN_cumulo+interval_yield+Feed_Vol+RS_cumulo+Cell_conc._interval+rab_integral+RQ_integral+Arg_conc.+emission_O2+emission_CO2; 0.539, 0.796, tmp_cumulo+pH+AN+Feed_Vol+RS_cumulo+rab_integral+RQ_integral+Accum._Yield+Arg_conc.+emission_O2+emission_CO2; 0.492, 0.076, pH+PL+PL_cumulo+AN+AN_cumulo+Feed_Vol+RS_cumulo+rab_integral+RQ_integral+Arg_conc.+emission_O2+emission_CO2+consum_O2+interval_O2+generate_CO2; 0.517, 0.796, tmp+tmp_cumulo+pH+AN+AN_cumulo+Feed_Vol+RS_cumulo+rab_integral+RQ_integral+Arg_conc.+emission_O2+emission_CO2+interval_O2; 0.517, 0.796, pH+PL+AN+AN_cumulo+Feed_Vol+RS_cumulo+Cell_conc._cumulo+rab_integral+RQ_integral+Arg_conc.+emission_O2+emission_CO2+consum_O2; 0.505, 0.796, tmp+tmp_cumulo+pH+PL+AN+AN_cumulo+Feed_Vol+RS_cumulo+rab_integral+RQ_integral+Arg_conc.+emission_O2+emission_CO2+consum_O2; 0.517, 0.796, pH+AN+AN_cumulo+interval_yield+Feed_Vol+RS_cumulo+Cell_conc._interval+rab_integral+RQ_integral+Arg_conc.+emission_O2+emission_CO2+generate_CO2; 0.492, 0.796, tmp+pH+PL+PL_cumulo+AN+AN_cumulo+Feed_Vol+RS_cumulo+Cell_conc._cumulo+rab_integral+RQ_integral+Arg_conc.+emission_O2+emission_CO2+consum_O2; 0.528, 0.796, tmp+pH+PL_cumulo+AN+interval_yield+Feed_Vol+RS_cumulo+rab_integral+RQ_integral+Arg_conc.+emission_O2+emission_CO2; 0.505, 0.796, tmp_cumulo+pH+PL+AN+AN_cumulo+interval_yield+Feed_Vol+RS_cumulo+Cell_conc._interval+rab_integral+RQ_integral+Arg_conc.+emission_O2+emission_CO2;

0.517, 0.796, pH+pH_cumulo+PL+AN+AN_cumulo+Feed_Vol+RS_cumulo+Cell_conc._cumulo+rab_integral+RQ_integral+Arg_conc.+emission_O2+emission_CO2; 0.505, 0.796, pH+AN+AN_cumulo+interval_yield+Feed_Vol+RS_cumulo+Cell_conc._interval+rab_integral+RQ_integral+Accum._Yield+Arg_conc.+emission_O2+emission_CO2+consum_O2; 0.505, 0.796, tmp_cumulo+pH+PL_cumulo+AN+AN_cumulo+interval_yield+Feed_Vol+RS_cumulo+rab_integral+RQ_integral+Arg_conc.+emission_O2+emission_CO2+interval_O2; 0.528, 0.796, tmp+pH+pH_cumulo+AN+AN_cumulo+Feed_Vol+RS_cumulo+rab_integral+RQ_integral+Arg_conc.+emission_O2+emission_CO2; 0.505, 0.796, tmp_cumulo+pH_cumulo+PL+PL_cumulo+AN+AN_cumulo+interval_yield+Feed_Vol+RS_cumulo+rab_integral+RQ_integral+Arg_conc.+emission_O2+emission_CO2; 0.550, 0.796, pH+AN_cumulo+interval_yield+Feed_Vol+RS_cumulo+rab_integral+RQ_integral+Arg_conc.+emission_O2+emission_CO2; 0.517, 0.796, pH+PL+PL_cumulo+AN+Feed_Vol+RS_cumulo+rab_integral+RQ_integral+Arg_conc.+emission_O2+emission_CO2+consum_O2+generate_CO2; 0.528, 0.796, tmp+pH+PL+AN+Feed_Vol+RS_cumulo+rab_integral+RQ_integral+Arg_conc.+emission_O2+emission_CO2+interval_O2; 0.528, 0.796, tmp_cumulo+pH+PL+AN+Feed_Vol+RS_cumulo+rab_integral+RQ_integral+Arg_conc.+emission_O2+emission_CO2+interval_O2; 0.539, 0.796, tmp_cumulo+pH+PL_cumulo+AN_cumulo+Feed_Vol+RS_cumulo+rab_integral+RQ_integral+Arg_conc.+emission_O2+emission_CO2; 0.528, 0.796, pH+pH_cumulo+PL+AN+interval_yield+Feed_Vol+RS_cumulo+rab_integral+RQ_integral+Arg_conc.+emission_O2+emission_CO2; 0.517, 0.796, tmp+pH+PL_cumulo+AN+AN_cumulo+Feed_Vol+RS_cumulo+Cell_conc._interval+rab_integral+RQ_integral+Arg_conc.+emission_O2+emission_CO2; 0.517, 0.796, pH+PL+AN+AN_cumulo+Feed_Vol+RS_cumulo+Cell_conc._cumulo+rab_integral+RQ_integral+Accum._Yield+Arg_conc.+emission_O2+emission_CO2; 0.517, 0.796, tmp_cumulo+pH+PL+AN+interval_yield+Feed_Vol+RS_cumulo+rab_integral+RQ_integral+Accum._Yield+Arg_conc.+emission_O2+emission_CO2; 0.478, 0.796, tmp_cumulo+pH+pH_cumulo+PL+PL_cumulo+AN+AN_cumulo+interval_yield+Feed_Vol+RS_cumulo+rab_integral+RQ_integral+Arg_conc.+emission_O2+emission_CO2+consum_O2; 0.539, 0.796, tmp_cumulo+pH+AN_cumulo+Feed_Vol+RS_cumulo+rab_integral+RQ_integral+Accum._Yield+Arg_conc.+emission_O2+emission_CO2; 0.504, 0.796, pH+pH_cumulo+PL_cumulo+AN+AN_cumulo+interval_yield+Feed_Vol+RS_cumulo+rab_integral+RQ_integral+Accum._Yield+Arg_conc.+emission_O2+emission_CO2; 0.549, 0.796, pH+AN+AN_cumulo+RS+Feed_Vol+rab_integral+RQ_integral+Arg_conc.+emission_O2+emission_CO2; 0.516, 0.796, tmp_cumulo+pH+PL_cumulo+AN+AN_cumulo+Feed_Vol+RS_cumulo+Cell_conc._interval+rab_integral+RQ_integral+Arg_conc.+emission_O2+emission_CO2; 0.539, 0.796, pH+AN+Feed_Vol+RS_cumulo+rab_integral+RQ_integral+Accum._Yield+Arg_conc.+emission_O2+emission_CO2+generate_CO2; 0.478, 0.795, tmp_cumulo+pH+PL+PL_cumulo+AN+AN_cumulo+interval_yield+Feed_Vol+RS_cumulo+rab_integral+RQ_integral+Arg_conc.+emission_O2+emission_CO2+consum_O02+generate_CO2; 0.528, 0.795, tmp_cumulo+pH+PL+AN+Feed_Vol+RS_cumulo+rab_integral+RQ_integral+Arg_conc.+emission_O2+emission_CO2+consum_O2; 0.516, 0.795, pH+pH_cumulo+PL+AN+interval_yield+Feed_Vol+RS_cumulo+Cell_conc._interval+rab_integral+RQ_integral+

Arg_conc.+emission_O2+emission_CO2; 0.539, 0.795, tmp+pH+AN+Feed_Vol+RS_cumulo+Cell_conc._interval+rab_integral+RQ_integral+Arg_conc.+emission_O2+emission_CO2; 0.516, 0.795, pH+AN+AN_cumulo+interval_yield+Feed_Vol+RS_cumulo+rab_integral+RQ_integral+Accum._Yield+Arg_conc.+emission_O2+emission_CO2+generate_CO2; 0.491, 0.795, pH+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2+consum_O2; 0.539, 0.795, pH+PL_cumulo+AN+Feed_Vol+RS_cumulo+rab_integral+RQ_integral+Arg_conc.+emission_O2+emission_CO2+interval_O2; 0.516, 0.795, pH+pH_cumulo+PL+AN+AN_cumulo+Feed_Vol+RS_cumulo+rab_integral+RQ_integral+Arg_conc.+emission_O2+emission_CO2+consum_O2; 0.491, 0.795, pH+PL_cumulo+AN+AN_cumulo+interval_yield+Feed_Vol+RS_cumulo+Cell_conc._interval+rab_integral+RQ_integral+Accum._Yield+Arg_conc.+emission_CO2+generate_CO2; 0.516, 0.795, pH+PL_cumulo+AN+AN_cumulo+Feed_Vol+RS_cumulo+Cell_conc._cumulo+Cell_conc._interval+rab_integral+RQ_integral+Arg_conc.+emission_O2+emission_CO2; 0.491, 0.795, tmp_cumulo+pH_cumulo+PL+PL_cumulo+AN+AN_cumulo+interval_yield+Feed_Vol+RS_cumulo+rab_integral+RQ_integral+Arg_conc.+emission_O2+emission_CO2+interval_O2; 0.491, 0.795, tmp+pH+PL+PL_cumulo+AN+interval_yield+Feed_Vol+RS_cumulo+rab_integral+RQ_integral+Accum._Yield+Arg_conc.+emission_O2+emission_CO2+interval_O2; 0.516, 0.795, pH+PL+PL_cumulo+AN+Feed_Vol+RS_cumulo+Cell_conc._cumulo+rab_integral+RQ_integral+Arg_conc.+emission_O2+emission_CO2+consum_O2; 0.516, 0.795, pH+PL+AN+AN_cumulo+Feed_Vol+RS_cumulo+Cell_conc._interval+rab_integral+RQ_integral+Accum._Yield+Arg_conc.+emission_O2+emission_CO2; 0.528, 0.795, tmp+tmp_cumulo+pH+AN_cumulo+Feed_Vol+RS_cumulo+rab_integral+RQ_integral+Accum._Yield+Arg_conc.+emission_O2+emission_CO2; 0.539, 0.795, pH+AN_cumulo+interval_yield+Feed_Vol+RS_cumulo+rab_integral+RQ_integral+Accum._Yield+Arg_conc.+emission_O2+emission_CO2; 0.516, 0.795, pH+PL+AN+AN_cumulo+Feed_Vol+RS_cumulo+rab_integral+RQ_integral+Accum._Yield+Arg_conc.+emission_O2+emission_CO2+consum_O2; 0.491, 0.795, tmp+pH+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2; 0.527, 0.795, pH+PL+AN+Feed_Vol+RS_cumulo+Cell_conc._interval+rab_integral+RQ_integral+Accum._Yield+Arg_conc.+emission_O2+emission_CO2; 0.491, 0.795, tmp+tmp_cumulo+pH+PL+PL_cumulo+AN+AN_cumulo+interval_yield+Feed_Vol+RS_cumulo+rab_integral+RQ_integral+Arg_conc.+emission_O2+emission_CO2; 0.491, 0.795, tmp+pH+PL+PL_cumulo+AN+AN_cumulo+Feed_Vol+RS_cumulo+rab_integral+RQ_integral+Arg_conc.+emission_O2+emission_CO2+consum_O2+generate_CO2; 0.538, 0.795, pH+AN+Feed_Vol+RS_cumulo+Cell_conc._interval+rab_integral+RQ_integral+Arg_conc.+emission_O2+emission_CO2+generate_CO2; 0.516, 0.795, pH+AN+AN_cumulo+interval_yield+Feed_Vol+RS_cumulo+rab_integral+RQ_integral+Accum._Yield+Arg_conc.+emission_O2+emission_CO2+interval_O2; 0.538, 0.795, tmp_cumulo+pH+AN+Feed_Vol+RS_cumulo+Cell_conc._interval+rab_integral+RQ_integral+Arg_conc.+emission_O2+emission_CO2; 0.504, 0.795, pH+PL_cumulo+AN+interval_yield+Feed_Vol+RS_cumulo+Cell_conc._cumulo+rab_integral+RQ_integral+Arg_conc.+emission_O2+emission_CO2+consum_O2; 0.491, 0.795, tmp_cumulo+pH+pH_cumulo+PL+PL_cumulo+AN+AN_cumulo+interval_yield+Feed_Vol+RS_cumulo+rab_integral+RQ_integral+Arg_conc.+emission_O2+emission_CO2; 0.549, 0.795, pH+AN_cumulo+Feed_Vol+RS_cumulo+rab_integral+RQ_integral+Arg_conc.+emission_O2+emission_CO2+generate_CO2; 0.504, 0.795, tmp+pH+PL+AN+AN_cumulo+interval_yield+Feed_Vol+RS_cumulo+rab_integral+RQ_integral+Accum._Yield+Arg_conc.+emission_O2+emission_CO2; 0.527, 0.795, pH+PL+AN+Feed_Vol+RS_cumulo+rab_integral+RQ_integral+Accum._Yield+Arg_conc.+emission_O2+emission_CO2+generate_CO2; 0.527, 0.795, pH_cumulo+AN+interval_yield+Feed_Vol+RS_cumulo+Cell_conc._interval+rab_integral+RQ_integral+Accum._Yield+Arg_conc.+emission_O2+emission_CO2; 0.516, 0.795, tmp_cumulo+pH+AN+AN_cumulo+Feed_Vol+RS_cumulo+rab_integral+RQ_integral+Accum._Yield+Arg_conc.+emission_O2+emission_CO2+interval_O2; 0.491, 0.795, tmp_cumulo+pH+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2; 0.516, 0.795, pH+AN+AN_cumulo+Feed_Vol+RS_cumulo+Cell_conc._interval+rab_integral+RQ_integral+Accum._Yield+Arg_conc.+emission_O2+emission_CO2+interval_O2; 0.491, 0.795, pH_cumulo+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2+interval_O2; 0.538, 0.795, pH+AN+Feed_Vol+RS_cumulo+Cell_conc._interval+rab_integral+RQ_integral+Arg_conc.+emission_O2+emission_CO2+interval_O2; 0.504, 0.795, pH+PL+PL_cumulo+AN+AN_cumulo+Feed_Vol+RS_cumulo+Cell_conc._interval+rab_integral+RQ_integral+Arg_conc.+emission_O2+emission_CO2+interval_O2; 0.527, 0.795, pH_cumulo+PL_cumulo+AN+AN_cumulo+Feed_Vol+RS_cumulo+rab_integral+RQ_integral+Arg_conc.+emission_O2+emission_CO2+interval_O2; 0.527, 0.795, pH+pH_cumulo+AN+interval_yield+Feed_Vol+RS_cumulo+Cell_conc._interval+rab_integral+RQ_integral+Arg_conc.+emission_O2+emission_CO2; 0.491, 0.795, tmp_cumulo+pH+pH_cumulo+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2; 0.503, 0.795, tmp+pH+PL+PL_cumulo+AN+Feed_Vol+RS_cumulo+rab_integral+RQ_integral+Accum._Yield+Arg_conc.+emission_O2+emission_CO2+consum_O2; 0.516, 0.795, pH+AN+AN_cumulo+interval_yield+Feed_Vol+RS_cumulo+Cell_conc._interval+rab_integral+RQ_integral+Arg_conc.+emission_O2+emission_CO2+interval_O2; 0.477, 0.795, tmp+pH+PL+PL_cumulo+AN+AN_cumulo+interval_yield+Feed_Vol+RS_cumulo+rab_integral+RQ_integral+Arg_conc.+emission_O2+emission_CO2+consum_O2+generate_CO2; 0.527, 0.795, tmp+pH+PL+AN+Feed_Vol+RS_cumulo+Cell_conc._interval+rab_integral+RQ_integral+Arg_conc.+emission_O2+emission_CO2; 0.515, 0.795, pH+PL+PL_cumulo+AN+interval_yield+Feed_Vol+RS_cumulo+rab_integral+RQ_integral+Arg_conc.+emission_O2+emission_CO2+generate_CO2; 0.515, 0.795, tmp+pH+PL+PL_cumulo+AN+Feed_Vol+RS_cumulo+rab_integral+RQ_integral+Arg_conc.+emission_O2+emission_CO2+interval_O2; 0.515, 0.795, tmp+pH+AN+AN_cumulo+Feed_Vol+RS_cumulo+Cell_conc._interval+rab_integral+RQ_integral+Accum._Yield+Arg_conc.+emission_O2+emission_CO2; 0.527, 0.795, tmp+pH+PL+AN+Feed_Vol+RS_cumulo+rab_integral+RQ_ integral+Arg_conc.+emission_O2+emission_CO2+generate_CO2; 0.538, 0.795, tmp+pH+AN+Feed_Vol+RS_cumulo+rab_integral+RQ_integral+Accum._Yield+Arg_conc.+emission_O2+emission_CO2; 0.527, 0.795, pH+PL+PL_cumulo+AN+Feed_Vol+RS_cumulo+Cell_conc._cumulo+rab_integral+RQ_integral+Arg_conc.+emission_O2+emission_CO2; 0.490, 0.795, pH+pH_cumulo+PL+PL_cumulo+AN+AN_cumulo+interval_yield+Feed_Vol+RS_cumulo+rab_integral+RQ_integral+Accum._Yield+Arg_conc.+emission_O2+emission_CO2; 0.515, 0.795, tmp_cumulo+pH_cumulo+PL_cumulo+AN+AN_cumulo+interval_yield+Feed_Vol+RS_cumulo+rab_integral+RQ_integral+Arg_conc.+emission_O2+emission_CO2; 0.538, 0.795, pH_cumulo+PL+AN+AN_cumulo+Feed_Vol+RS_cumulo+rab_integral+RQ_integral+Arg_conc.+emission_O2+emission_CO2; 0.515, 0.795, pH+pH_cumulo+PL_cumulo+AN+AN_cumulo+Feed_Vol+RS_cumulo+rab_integral+RQ_integral+Arg_conc.+emission_O2+emission_CO2+interval_O2; 0.490, 0.795, tmp+pH+pH_cumulo+PL+PL_cumulo+AN+AN_cumulo+interval_yield+Feed_Vol+RS_cumulo+rab_integral+RQ_integral+Arg_conc.+emission_O2+emission_CO2; 0.503, 0.795, pH+pH_cumulo+PL+PL_cumulo+AN+AN_cumulo+Feed_Vol+RS_cumulo+rab_integral+RQ_integral+Accum._Yield+Arg_conc.+emission_O2+emission_CO2; 0.527, 0.795, pH+AN+AN_cumulo+Feed_Vol+RS_cumulo+Cell_conc._cumulo+Cell_conc._interval+rab_integral+RQ_integral+Arg_conc.+emission_O2+emission_CO2; 0.548, 0.795, pH+AN_cumulo+Feed_Vol+RS_cumulo+rab_integral+RQ_integral+Arg_conc.+emission_O2+emission_CO2+interval_O2; 0.490, 0.795, pH+PL+PL_cumulo+AN+interval_yield+Feed_Vol+RS_cumulo+Cell_conc._interval+rab_integral+RQ_integral+Accum._Yield+Arg_conc.+emission_O2+emission_CO2+interval_O2; 0.503, 0.795, pH+PL+PL_cumulo+AN+interval_yield+Feed_Vol+RS_cumulo+rab_integral+RQ_integral+Arg_conc.+emission_O2+emission_CO2+consum_O2+generate_CO2; 0.503, 0.795, tmp+pH+PL+AN+AN_cumulo+interval_yield+Feed_Vol+RS_cumulo+Cell_conc._interval+rab_integral+RQ_integral+Arg_conc.+emission_O2+emission_CO2; 0.515, 0.795, pH+PL_cumulo+AN+AN_cumulo+Feed_Vol+RS_cumulo+Cell_conc._interval+rab_integral+RQ_integral+Arg_conc.+emission_O2+emission_CO2+interval_O2; 0.490, 0.795, tmp_cumulo+pH+PL_cumulo+AN+AN_cumulo+Feed_Vol+RS_cumulo+rab_integral+RQ_integral+Arg_conc.+emission_O2+emission_CO2+consum_O2+generate_CO2; 0.537, 0.795, tmp+tmp_cumulo+pH+AN+Feed_Vol+RS_cumulo+rab_integral+RQ_integral+Arg_conc.+emission_O2+emission_CO2; 0.503, 0.795, pH+PL+AN+interval_yield+Feed_Vol+RS_cumulo+Cell_conc._interval+rab_integral+RQ_integral+Accum._Yield+Arg_conc.+emission_O2+emission_CO2+generate_CO2; 0.548, 0.795, pH+pH_cumulo+AN_cumulo+Feed_Vol+RS_cumulo+rab_integral+RQ_integral+Arg_conc.+emission_O2+emission_CO2; 0.526, 0.795, pH+pH_cumulo+AN+AN_cumulo+Feed_Vol+RS_cumulo+Cell_conc._interval+rab_integral+RQ_integral+Arg_conc.+emission_O2+emission_CO2; 0.490, 0.795, tmp+pH+PL+PL_cumulo+AN+interval_yield+Feed_Vol+RS_cumulo+Cell_conc._interval+rab_integral+RQ_integral+Arg_conc.+emission_O2+emission_CO2+interval_O2; 0.490, 0.795, tmp_cumulo+pH+PL+PL_cumulo+AN+interval_yield+Feed_Vol+RS_cumulo+Cell_conc._interval+rab_integral+RQ_integral+Arg_conc.+emission_O2+emission_CO2+consum_O2; 0.515, 0.795, tmp+tmp_cumulo+pH+AN+AN_cumulo+Feed_Vol+RS_cumulo+rab_integral+RQ_integral+Arg_conc.+emission_O2+emission_CO2+generate_CO2; 0.537, 0.795, pH+AN+Feed_Vol+RS_cumulo+rab_integral+RQ_integral+Accum._Yield+Arg_conc.+emission_O2+emission_CO2+interval_O2; 0.526, 0.795, tmp_cumulo+pH+PL+AN+Feed_Vol+RS_cumulo+Cell_conc._interval+rab_integral+RQ_integral+Arg_conc.+emission_O2+emission_CO2; 0.515, 0.795, pH+PL_cumulo+AN+AN_cumulo+Feed_Vol+RS_cumulo+Cell_conc._interval+rab_integral+RQ_integral+Arg_conc.+emission_O2+emission_CO2+consum_O2; 0.515, 0.795, tmp+pH+AN+AN_cumulo+Feed_Vol+RS_cumulo+rab_integral+RQ_integral+Accum._Yield+Arg_conc.+emission_O2+emission_CO2+interval_O2; 0.515, 0.795, tmp_cumulo+pH+pH_cumulo+PL_cumulo+AN+AN_cumulo+Feed_Vol+RS_cumulo+rab_integral+RQ_integral+Arg_conc.+emission_O2+emission_CO2; 0.526, 0.795, pH_cumulo+AN+AN_cumulo+interval_yield+Feed_Vol+RS_cumulo+Cell_conc._interval+rab_integral+RQ_integral+Arg_conc.+emission_O2+emission_CO2; 0.526, 0.795, pH+pH_cumulo+AN+AN_cumulo+Feed_Vol+RS_cumulo+rab_integral+RQ_integral+Arg_conc.+emission_O2+emission_CO2+generate_CO2; 0.503, 0.795, tmp+pH_cumulo+PL+PL_cumulo+AN+AN_cumulo+interval_yield+Feed_Vol+RS_cumulo+rab_integral+RQ_integral+Arg_conc.+emission_O2+emission_CO2; 0.526, 0.795, pH_cumulo+PL_cumulo+AN+AN_cumulo+Feed_Vol+RS_cumulo+Cell_conc._interval+rab_integral+RQ_integral+Arg_conc.+emission_O2+emission_CO2; 0.503, 0.795, pH+pH_cumulo+PL+AN+interval_yield+Feed_Vol+RS_cumulo+Cell_conc._interval+rab_integral+RQ_integral+Accum._Yield+Arg_conc.+emission_O2+emission_CO2; 0.537, 0.795, pH+PL_cumulo+AN_cumulo+Feed_Vol+RS_cumulo+rab_integral+RQ_integral+Arg_conc.+emission_O2+emission_CO2+interval_O2; 0.490, 0.795, tmp+pH+PL+PL_cumulo+AN+interval_yield+Feed_Vol+RS_cumulo+Cell_conc._interval+rab_integral+RQ_integral+Accum._Yield+Arg_conc.+emission_O2+emission_CO2; 0.490, 0.795, tmp_cumulo+pH+pH_cumulo+PL+PL_cumulo+AN+AN_cumulo+Feed_Vol+RS_cumulo+rab_integral+RQ_integral+Arg_conc.+emission_O2+emission_CO2+consum_O2; 0.558, 0.795, pH+AN+RS+Feed_Vol+rab_integral+RQ_integral+Arg_conc.+emission_O2+emission_CO2; 0.548, 0.795, pH+PL+AN_cumulo+Feed_Vol+RS_cumulo+rab_integral+RQ_integral+Arg_conc.+emission_O2+emission_CO2; 0.526, 0.795, pH+AN_cumulo+interval_yield+Feed_Vol+RS_cumulo+Cell_conc._interval+rab_integral+RQ_integral+Accum._Yield+Arg_conc.+emission_O2+emission_CO2; 0.526, 0.795, tmp_cumulo+pH+PL+AN+Feed_Vol+RS_cumulo+rab_integral+RQ_integral+Arg_conc.+emission_O2+emission_CO2+generate_CO2; 0.476, 0.795, tmp+pH+pH_cumulo+PL+PL_cumulo+AN+AN_cumulo+interval_yield+Feed_Vol+RS_cumulo+rab_integral+RQ_integral+Arg_conc.+emission_O2+emission_CO2+interval_O2; 0.526, 0.795, pH+PL+AN+Feed_Vol+RS_cumulo+rab_integral+RQ_integral+Accum._Yield+Arg_conc.+emission_O2+emission_CO2+interval_O2; 0.514, 0.795, tmp_cumulo+pH+PL+AN+interval_yield+Feed_Vol+RS_cumulo+rab_integral+RQ_integral+Arg_conc.+emission_O2+emission_CO2+interval_O2; 0.502, 0.795, pH_cumulo+PL+PL_cumulo+AN+AN_cumulo+interval_yield+Feed_Vol+RS_cumulo+rab_integral+RQ_integral+Accum._Yield+Arg_conc.+emission_O2+emission_CO2; 0.502, 0.795, tmp+pH+PL_cumulo+AN+AN_cumulo+interval_yield+Feed_Vol+RS_cumulo+rab_integral+RQ_integral+Arg_conc.+emission_O2+emission_CO2+interval_O2; 0.489, 0.795, tmp_cumulo+pH+PL+PL_cumulo+AN+AN_cumulo+Feed_

Vol+RS_cumulo+rab_integral+RQ_integral+Accum._Yield+Arg_conc.+emission_O2+emission_CO2+consum_O2; 0.514, 0.795, pH+pH_cumulo+AN+AN_cumulo+interval_yield+Feed_Vol+RS_cumulo+Cell_conc._interval+rab_integral+RQ_integral+Arg_conc.+emission_O2+emission_CO2; 0.514, 0.794, pH+PL+AN+interval_yield+Feed_Vol+RS_cumulo+Cell_conc._interval+rab_integral+RQ_integral+Arg_conc.+emission_O2+emission_CO2+generate_CO2; 0.514, 0.794, pH+pH_cumulo+PL_cumulo+AN+AN_cumulo+Feed_Vol+RS_cumulo+rab_integral+RQ_integral+Arg_conc.+emission_O2+emission_CO2+consum_O2; 0.502, 0.794, tmp+tmp_cumulo+pH+PL+AN+AN_cumulo+Feed_Vol+RS_cumulo+rab_integral+RQ_integral+Arg_conc.+emission_O2+emission_CO2+generate_CO2; 0.502, 0.794, tmp+pH+PL+PL_cumulo+AN+AN_cumulo+Feed_Vol+RS_cumulo+Cell_conc._interval+rab_integral+RQ_integral+Arg_conc.+emission_O2+emission_CO2; 0.514, 0.794, pH+PL+AN+AN_cumulo+Feed_Vol+RS_cumulo+Cell_conc._interval+rab_integral+RQ_integral+Arg_conc.+emission_O2+emission_CO2+consum_O2; 0.502, 0.794, tmp+pH+PL_cumulo+AN+interval_yield+Feed_Vol+RS_cumulo+Cell_conc._interval+rab_integral+RQ_integral+Accum._Yield+Arg_conc.+emission_O2+emission_CO2; 0.489, 0.794, tmp+pH+PL+PL_cumulo+AN+interval_yield+Feed_Vol+RS_cumulo+rab_integral+RQ_integral+Arg_conc.+emission_O2+emission_CO2+consum_O2+generate_CO2; 0.476, 0.794, tmp_cumulo+pH+PL+PL_cumulo+AN+AN_cumulo+interval_yield+Feed_Vol+RS_cumulo+rab_integral+RQ_integral+Arg_conc.+emission_O2+emission_CO2+interval_O2+generate_CO2; 0.526, 0.794, pH+AN+AN_cumulo+interval_yield+Feed_Vol+RS_cumulo+Cell_conc._cumulo+rab_integral+RQ_integral+Arg_conc.+emission_O2+emission_CO2; 0.514, 0.794, tmp_cumulo+pH_cumulo+PL+PL_cumulo+AN+AN_cumulo+Feed_Vol+RS_cumulo+rab_integral+RQ_integral+Arg_conc.+emission_O2+emission_CO2; 0.489, 0.794, tmp+pH+PL+PL_cumulo+AN+AN_cumulo+Feed_Vol+RS_cumulo+rab_integral+RQ_integral+Accum._Yield+Arg_conc.+emission_O2+emission_CO2+consum_O2; 0.526, 0.794, pH+PL+AN+interval_yield+Feed_Vol+RS_cumulo+rab_integral+RQ_integral+Arg_conc.+emission_O2+emission_CO2+generate_CO2; 0.526, 0.794, pH+PL+AN+Feed_Vol+RS_cumulo+rab_integral+RQ_integral+Arg_conc.+emission_O2+emission_CO2+consum_O2+interval_O2; 0.489, 0.794, pH+PL+PL_cumulo+AN+AN_cumulo+interval_yield+Feed_Vol+RS_cumulo+rab_integral+RQ_integral+Accum._Yield+Arg_conc.+emission_O2+emission_CO2+generate_CO2; 0.476, 0.794, tmp_cumulo+pH+PL+PL_cumulo+AN+interval_yield+Feed_Vol+RS_cumulo+Cell_conc._interval+rab_integral+RQ_integral+Accum._Yield+Arg_conc.+emission_O2+emission_CO2+consum_O2; 0.525, 0.794, pH_cumulo+PL_cumulo+AN+AN_cumulo+Feed_Vol+RS_cumulo+Cell_conc._cumulo+rab_integral+RQ_integral+Arg_conc.+emission_O2+emission_CO2; 0.525, 0.794, tmp_cumulo+pH+PL_cumulo+AN+interval_yield+Feed_Vol+RS_cumulo+rab_integral+RQ_integral+Arg_conc.+emission_O2+emission_CO2; 0.525, 0.794, pH+pH_cumulo+AN+AN_cumulo+Feed_Vol+RS_cumulo+Cell_conc._cumulo+rab_integral+RQ_integral+Arg_conc.+emission_O2+emission_CO2; 0.475, 0.794, tmp_cumulo+pH+PL+PL_cumulo+AN+AN_cumulo+interval_yield+Feed_Vol+RS_cumulo+Cell_conc._cumulo+rab_integral+RQ_integral+Arg_conc.+emission_O2+emission_CO2+consum_O2; 0.475, 0.794, tmp_cumulo+pH+PL+PL_cumulo+AN+AN_cumulo+interval_yield+Feed_Vol+RS_cumulo+rab_integral+RQ_integral+Accum._Yield+Arg_conc.+emission_O2+emission_CO2+consum_O2+interval_O2; 0.489, 0.794, tmp_cumulo+pH+PL+PL_cumulo+AN+interval_yield+Feed_Vol+RS_cumulo+rab_integral+RQ_integral+Accum._Yield+Arg_conc.+emission_O2+emission_CO2+interval_O2; 0.514, 0.794, tmp+pH+PL+PL_cumulo+AN+Feed_Vol+RS_cumulo+rab_integral+RQ_integral+Accum._Yield+Arg_conc.+emission_O2+emission_CO2; 0.489, 0.794, tmp+pH+PL+PL_cumulo+AN+AN_cumulo+Feed_Vol+RS_cumulo+rab_integral+RQ_integral+Arg_conc.+emission_O2+emission_CO2+interval_O2+generate_CO2; 0.514, 0.794, pH_cumulo+PL_cumulo+AN+AN_cumulo+interval_yield+Feed_Vol+RS_cumulo+rab_integral+RQ_integral+Arg_conc.+emission_O2+emission_CO2+interval_O2; 0.525, 0.794, tmp+pH+PL+AN+Feed_Vol+RS_cumulo+rab_integral+RQ_integral+Arg_conc.+emission_O2+emission_CO2+consum_O2; 0.489, 0.794, tmp+pH_cumulo+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2; 0.514, 0.794, tmp+pH_cumulo+PL_cumulo+AN+AN_cumulo+interval_yield+Feed_Vol+RS_cumulo+rab_integral+RQ_integral+Arg_conc.+emission_O2+emission_CO2; 0.489, 0.794, tmp_cumulo+pH+PL+PL_cumulo+AN+AN_cumulo+Feed_Vol+RS_cumulo+rab_integral+RQ_integral+Arg_conc.+emission_O2+emission_CO2+interval_O2+generate_CO2; 0.489, 0.794, pH+PL+PL_cumulo+AN+AN_cumulo+Feed_Vol+RS_cumulo+Cell_conc._cumulo+rab_integral+RQ_integral+Arg_conc.+emission_O2+emission_CO2+consum_O2+generate_CO2; 0.489, 0.794, pH+pH_cumulo+PL+PL_cumulo+AN+AN_cumulo+Feed_Vol+RS_cumulo+Cell_conc._cumulo+rab_integral+RQ_integral+Arg_conc.+emission_O2+emission_CO2+consum_O2; 0.536, 0.794, pH+AN+interval_yield+Feed_Vol+RS_cumulo+rab_integral+RQ_integral+Arg_conc.+emission_O2+emission_CO2+interval_O2; 0.501, 0.794, pH+pH_cumulo+PL_cumulo+AN+AN_cumulo+interval_yield+Feed_Vol+RS_cumulo+Cell_conc._interval+rab_integral+RQ_integral+Arg_conc.+emission_O2+emission_CO2; 0.513, 0.794, tmp+pH_cumulo+PL+PL_cumulo+AN+AN_cumulo+Feed_Vol+RS_cumulo+rab_integral+RQ_integral+Arg_conc.+emission_O2+emission_CO2; 0.501, 0.794, pH_cumulo+PL+PL_cumulo+AN+AN_cumulo+interval_yield+Feed_Vol+RS_cumulo+rab_integral+RQ_integral+Arg_conc.+emission_O2+emission_CO2+consum_O2; 0.525, 0.794, tmp+tmp_cumulo+pH+AN_cumulo+interval_yield+Feed_Vol+RS_cumulo+rab_integral+RQ_integral+Arg_conc.+emission_O2+emission_CO2; 0.547, 0.794, pH+PL_cumulo+AN_cumulo+Feed_Vol+RS_cumulo+rab_integral+Accum._Yield+Arg_conc.+emission_O2+emission_CO2; 0.513, 0.794, pH+AN+AN_cumulo+Feed_Vol+RS_cumulo+rab_integral+RQ_integral+Accum._Yield+Arg_conc.+emission_O2+emission_CO2+consum_O2+interval_O2; 0.501, 0.794, tmp_cumulo+pH+PL+PL_cumulo+AN+interval_yield+Feed_Vol+RS_cumulo+rab_integral+RQ_integral+Accum._Yield+Arg_conc.+emission_O2+emission_CO2; 0.525, 0.794, pH+PL+AN+Feed_Vol+RS_cumulo+Cell_conc._interval+rab_integral+RQ_integral+Arg_conc.+emission_O2+emission_CO2+interval_O2; 0.501, 0.794, tmp_cumulo+pH+PL+PL_cumulo+AN+AN_cumulo+Feed_Vol+RS_cumulo+Cell_conc._interval+rab_integral+RQ_integral+Arg_conc.+emission_O2+emission_CO2; 0.536, 0.794, tmp+pH+AN+Feed_Vol+RS_cumulo+rab_integral+RQ_integral+Arg_conc.+emission_O2+emission_CO2+interval_O2; 0.513, 0.794, pH+AN+AN_cumulo+Feed_Vol+RS_cumulo+rab_integral+RQ_integral+Accum._Yield+Arg_conc.+emission_O2+ emission_CO2+interval_O2+generate_CO2; 0.501, 0.794, tmp_cumulo+pH+pH_cumulo+PL+AN+AN_cumulo+interval_yield+Feed_Vol+RS_cumulo+rab_integral+RQ_integral+Arg_conc.+emission_O2+emission_CO2; 0.513, 0.794, pH+PL+PL_cumulo+AN+Feed_Vol+RS_cumulo+Cell_conc._interval+rab_integral+RQ_integral+Arg_conc.+emission_O2+emission_CO2+consum_O2; 0.488, 0.794, tmp_cumulo+pH+PL+AN+AN_cumulo+interval_yield+Feed_Vol+RS_cumulo+Cell_conc._interval+rab_integral+RQ_integral+Accum._Yield+Arg_conc.+emission_O2+emission_CO2; 0.501, 0.794, pH+PL_cumulo+AN+AN_cumulo+interval_yield+Feed_Vol+RS_cumulo+Cell_conc._interval+rab_integral+RQ_integral+Arg_conc.+emission_O2+emission_CO2+interval_O2; 0.536, 0.794, pH+PL+PL_cumulo+AN_cumulo+Feed_Vol+RS_cumulo+rab_integral+RQ_integral+Arg_conc.+emission_O2+emission_CO2; 0.525, 0.794, pH+PL+AN+Feed_Vol+RS_cumulo+Cell_conc._interval+rab_integral+RQ_integral+Arg_conc.+emission_O2+emission_CO2+generate_CO2; 0.475, 0.794, tmp_cumulo+pH+PL+PL_cumulo+AN+AN_cumulo+interval_yield+Feed_Vol+RS_cumulo+Cell_conc._interval+rab_integral+RQ_integral+Arg_conc.+emission_O2+emission_CO2+consum_O2; 0.525, 0.794, tmp+pH+PL_cumulo+AN_cumulo+Feed_Vol+RS_cumulo+rab_integral+RQ_integral+Accum._Yield+Arg_conc.+emission_O2+emission_CO2; 0.536, 0.794, tmp_cumulo+pH+AN+Feed_Vol+RS_cumulo+rab_integral+RQ_integral+Arg_conc.+emission_O2+emission_CO2+generate_CO2; 0.501, 0.794, pH+PL+PL_cumulo+AN+AN_cumulo+Feed_Vol+RS_cumulo+Cell_conc._cumulo+rab_integral+RQ_integral+Accum._Yield+Arg_conc.+emission_O2+emission_CO2; 0.513, 0.794, pH+AN+AN_cumulo+Feed_Vol+RS_cumulo+rab_integral+RQ_integral+Arg_conc.+emission_O2+emission_CO2+consum_O2+interval_O2+generate_CO2; 0.525, 0.794, pH_cumulo+PL_cumulo+AN+AN_cumulo+Feed_Vol+RS_cumulo+rab_integral+RQ_integral+Arg_conc.+emission_O2+emission_CO2+generate_CO2; 0.536, 0.794, tmp_cumulo+pH+AN+Feed_Vol+RS_cumulo+rab_integral+RQ_integral+Arg_conc.+emission_O2+emission_CO2+interval_O2; 0.475, 0.794, pH+PL+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2+consum_O2; 0.525, 0.794, pH+AN+interval_yield+Feed_Vol+RS_cumulo+Cell_conc._interval+rab_integral+RQ_integral+Arg_conc.+emission_O2+emission_CO2+consum_O2; 0.513, 0.794, tmp+pH+PL+AN+interval_yield+Feed_Vol+RS_cumulo+rab_integral+RQ_integral+Accum._Yield+Arg_conc.+emission_O2+emission_CO2; 0.488, 0.794, tmp+tmp_cumulo+pH+PL+PL_cumulo+AN+AN_cumulo+Feed_Vol+RS_cumulo+rab_integral+RQ_integral+Arg_conc.+emission_O2+emission_CO2+interval_O2; 0.501, 0.794, pH+PL+AN+interval_yield+Feed_Vol+RS_cumulo+Cell_conc._interval+rab_integral+RQ_integral+Accum._Yield+Arg_conc.+emission_O2+emission_CO2+consum_O2; 0.524, 0.794, pH+PL_cumulo+AN+interval_yield+Feed_Vol+RS_cumulo+rab_integral+RQ_integral+Arg_conc.+emission_O2+emission_CO2+consum_O2; 0.474, 0.794, tmp_cumulo+pH+PL+PL_cumulo+AN+AN_cumulo+interval_yield+Feed_Vol+RS_cumulo+Cell_conc._interval+rab_integral+RQ_integral+Arg_conc.+emission_O2+emission_CO2+interval_O2; 0.474, 0.794, pH+PL+PL_cumulo+AN_cumulo+interval_yield+Feed_Vol+RS_cumulo+Cell_conc._interval+rab_integral+RQ_integral+Accum._Yield+Arg_conc.+emission_O2+emission_CO2+interval_O2; 0.513, 0.794, pH+PL_cumulo+AN_cumulo+interval_yield+Feed_Vol+RS_cumulo+rab_integral+RQ_integral+Accum._Yield+Arg_conc.+emission_O2+emission_CO2+interval_O2; 0.501, 0.794, pH+PL_cumulo+AN+AN_cumulo+Feed_Vol+RS_cumulo+rab_integral+RQ_integral+Accum._Yield+Arg_conc.+emission_O2+emission_CO2+interval_O2+generate_CO2; 0.513, 0.794, tmp+pH+pH_cumulo+PL_cumulo+AN+AN_cumulo+Feed_Vol+RS_cumulo+rab_integral+RQ_integral+Arg_conc.+emission_O2+emission_CO2; 0.524, 0.794, pH+PL+AN+interval_yield+RS+Feed_Vol+Cell_conc._interval+rab_integral+RQ_integral+Arg_conc.+emission_O2+emission_CO2; 0.535, 0.794, tmp+pH+AN+Feed_Vol+RS_cumulo+rab_integral+RQ_integral+Arg_conc.+emission_O2+emission_CO2+generate_CO2; 0.500, 0.794, tmp_cumulo+pH+PL+PL_cumulo+AN+interval_yield+Feed_Vol+RS_cumulo+Cell_conc._interval+rab_integral+RQ_integral+Arg_conc.+emission_O2+emission_CO2; 0.488, 0.794, pH+pH_cumulo+PL+PL_cumulo+AN+AN_cumulo+interval_yield+Feed_Vol+RS_cumulo+Cell_conc._interval+rab_integral+RQ_integral+Arg_conc.+emission_O2+emission_CO2; 0.513, 0.794, pH+PL+AN+interval_yield+Feed_Vol+RS_cumulo+Cell_conc._interval+rab_integral+RQ_integral+Arg_conc.+emission_O2+emission_CO2+consum_O2; 0.546, 0.794, pH+AN+interval_yield+RS+Feed_Vol+rab_integral+RQ_integral+Arg_conc.+emission_O2+emission_CO2; 0.500, 0.794, pH+PL+PL_cumulo+AN+interval_yield+Feed_Vol+RS_cumulo+rab_integral+RQ_integral+Arg_conc.+emission_O2+emission_CO2+consum_O2+interval_O2; 0.513, 0.794, tmp_cumulo+pH+AN+AN_cumulo+interval_yield+Feed_Vol+RS_cumulo+rab_integral+RQ_integral+Arg_conc.+emission_O2+emission_CO2+interval_O2; 0.513, 0.794, pH+PL+PL_cumulo+AN+Feed_Vol+RS_cumulo+rab_integral+RQ_integral+Arg_conc.+emission_O2+emission_CO2+consum_O2+interval_O2; 0.524, 0.794, pH+PL_cumulo+AN+interval_yield+Feed_Vol+RS_cumulo+rab_integral+RQ_integral+Arg_conc.+emission_O2+emission_CO2+interval_O2; 0.500, 0.794, pH+PL+AN+AN_cumulo+interval_yield+Feed_Vol+RS_cumulo+Cell_conc._interval+rab_integral+RQ_integral+Arg_conc.+emission_O2+emission_CO2+interval_O2; 0.500, 0.794, pH+PL+PL_cumulo+AN+AN_cumulo+Feed_Vol+RS_cumulo+Cell_conc._interval+rab_integral+RQ_integral+Arg_conc.+emission_O2+emission_CO2+generate_CO2; 0.488, 0.794, tmp+pH+PL+PL_cumulo+AN+AN_cumulo+Feed_Vol+RS_cumulo+rab_integral+RQ_integral+Arg_conc.+emission_O2+emission_CO2+consum_O2+interval_O2; 0.524, 0.794, pH+pH_cumulo+AN+AN_cumulo+Feed_Vol+RS_cumulo+rab_integral+RQ_integral+Arg_conc.+emission_O2+emission_CO2+consum_O2; 0.500, 0.794, tmp+pH+PL_cumulo+AN+AN_cumulo+Feed_Vol+RS_cumulo+rab_integral+RQ_integral+Accum._Yield+Arg_conc.+emission_O2+emission_CO2+generate_CO2; 0.524, 0.794, pH_cumulo+PL_cumulo+AN+interval_yield+Feed_Vol+RS_cumulo+Cell_conc._interval+rab_integral+RQ_integral+Arg_conc.+emission_O2+emission_CO2; 0.500, 0.794, tmp+tmp_cumulo+pH+pH_cumulo+PL+AN+AN_cumulo+Feed_Vol+RS_cumulo+rab_integral+RQ_integral+Arg_conc.+emission_O2+emission_CO2; 0.500, 0.794, tmp+tmp_cumulo+pH+PL+AN+AN_cumulo+Feed_Vol+RS_cumulo+Cell_conc._cumulo+rab_integral+RQ_integral+Arg_conc.+emission_O2+emission_CO2; 0.524, 0.794, pH+AN+AN_cumulo+interval_yield+Feed_Vol+RS_cumulo+rab_integral+RQ_integral+Arg_conc.+emission_O2+emission_CO2+consum_O2; 0.500, 0.794, tmp+pH+PL+AN+AN_cumulo+interval_yield+Feed_Vol+RS_ cumulo+rab_integral+RQ_integral+Arg_conc.+emission_ O2+emission_CO2+interval_O2; 0.487, 0.794, tmp+pH+ PL+PL_cumulo+AN+interval_yield+Feed_Vol+RS_ cumulo+Cell_conc._cumulo+rab_integral+RQ_integral+ Arg_conc.+emission_O2+emission_CO2+consum_O2; 0.474, 0.794, tmp+pH+pH_cumulo+PL+PL_cumulo+AN+ AN_cumulo+interval_yield+Feed_Vol+RS_cumulo+rab_ integral+RQ_integral+Arg_conc.+emission_O2+emission_ CO2+consum_O2; 0.474, 0.794, tmp+pH+PL+PL_cumulo+ AN+AN_cumulo+interval_yield+Feed_Vol+RS_cumulo+ rab_integral+RQ_integral+Arg_conc.+emission_O2+ emission_CO2+consum_O2+interval_O2; 0.535, 0.794, pH_cumulo+AN+AN_cumulo+interval_yield+Feed_Vol+ RS_cumulo+rab_integral+RQ_integral+Arg_conc.+emission_O2+emission_CO2; 0.512, 0.794, pH+PL+AN+AN_ cumulo+interval_yield+Feed_Vol+RS_cumulo+rab_ integral+RQ_integral+Arg_conc.+emission_O2+emission_ CO2+consum_O2; 0.487, 0.794, pH_cumulo+PL+PL_ cumulo+AN+AN_cumulo+interval_yield+Feed_Vol+RS_ cumulo+Cell_conc._interval+rab_integral+RQ_integral+ Arg_conc.+emission_O2+emission_CO2+interval_O2; 0.512, 0.794, pH+PL_cumulo+AN_cumulo+interval_yield+ Feed_Vol+RS_cumulo+Cell_conc._interval+rab_integral+ RQ_integral+Accum._Yield+Arg_conc.+emission_O2+ emission_CO2; 0.524, 0.793, tmp+tmp_cumulo+pH+PL+ AN_cumulo+Feed_Vol+RS_cumulo+rab_integral+RQ_ integral+Arg_conc.+emission_O2+emission_CO2; 0.500, 0.793, tmp_cumulo+pH+PL+AN+AN_cumulo+Feed_Vol+ RS_cumulo+rab_integral+RQ_integral+Accum._Yield+ Arg_conc.+emission_O2+emission_CO2+generate_CO2; 0.524, 0.793, tmp_cumulo+pH+PL_cumulo+AN_cumulo+ Feed_Vol+RS_cumulo+rab_integral+RQ_integral+Accum._Yield+Arg_conc.+emission_O2+emission_CO2; 0.473, 0.793, pH+pH_cumulo+PL+PL_cumulo+AN+AN_ cumulo+interval_yield+Feed_Vol+RS_cumulo+rab_integral+RQ_integral+Accum._Yield+Arg_conc.+emission_ O2+emission_CO2+consum_O2; 0.500, 0.793, pH+PL_ cumulo+AN+AN_cumulo+Feed_Vol+RS_cumulo+rab_ integral+RQ_integral+Accum._Yield+Arg_conc.+ emission_O2+emission_CO2+consum_O2+interval_O2; 0.487, 0.793, tmp+pH+pH_cumulo+PL+PL_cumulo+AN+ AN_cumulo+Feed_Vol+RS_cumulo+rab_integral+RQ_integral+Arg_conc.+emission_O2+emission_CO2+consum_ O2; 0.487, 0.793, tmp_cumulo+pH+PL+PL_cumulo+AN+ AN_cumulo+Feed_Vol+RS_cumulo+rab_integral+RQ_ integral+Arg_conc.+emission_O2+emission_CO2+ consum_O2+interval_O2; 0.535, 0.793, pH+AN+Feed_ Vol+RS_cumulo+rab_integral+RQ_integral+Arg_conc.+ emission_O2+emission_CO2+consum_O2+interval_O2; 0.535, 0.793, pH+PL_cumulo+AN_cumulo+Feed_Vol+RS_ cumulo+rab_integral+RQ_integral+Arg_conc.+emission_ O2+emission_CO2+generate_CO2; 0.512, 0.793, pH_cumulo+PL+PL_cumulo+AN+interval_yield+Feed_Vol+RS_ cumulo+Cell_conc._interval+rab_integral+RQ_integral+ Arg_conc.+emission_O2+emission_CO2; 0.512, 0.793, pH+PL+PL_cumulo+AN+Feed_Vol+RS_cumulo+rab_integral+RQ_integral+Arg_conc.+emission_O2+emission_ CO2+interval_O2+generate_CO2; 0.535, 0.793, tmp+pH_ cumulo+AN+AN_cumulo+Feed_Vol+RS_cumulo+rab_ integral+RQ_integral+Arg_conc.+emission_O2+emission_ CO2; 0.500, 0.793, pH+pH_cumulo+PL+PL_cumulo+AN+ interval_yield+Feed_Vol+RS_cumulo+Cell_conc._ interval+rab_integral+RQ_integral+Arg_conc.+emission_ O2+emission_CO2; 0.523, 0.793, pH+pH_cumulo+PL+ AN+Feed_Vol+RS_cumulo+rab_integral+RQ_integral+ Arg_conc.+emission_O2+emission_CO2+generate_CO2; 0.512, 0.793, pH+PL+AN+interval_yield+RS+Feed_Vol+ Cell_conc._interval+rab_integral+RQ_integral+Accum._ Yield+Arg_conc.+emission_O2+emission_CO2; 0.535, 0.793, pH_cumulo+AN+interval_yield+Feed_Vol+RS_cumulo+Cell_conc._interval+rab_integral+RQ_integral+Arg_ conc.+emission_O2+emission_CO2; 0.523, 0.793, tmp_cumulo+pH+pH_cumulo+PL+AN+Feed_Vol+RS_cumulo+ rab_integral+RQ_integral+Arg_conc.+emission_O2+ emission_CO2; 0.535, 0.793, tmp_cumulo+pH_cumulo+ AN+AN_cumulo+Feed_Vol+RS_cumulo+rab_integral+ RQ_integral+Arg_conc.+emission_O2+emission_CO2; 0.500, 0.793, pH+pH_cumulo+PL+PL_cumulo+AN+AN_ cumulo+Feed_Vol+RS_cumulo+rab_integral+RQ_integral+Arg_conc.+emission_O2+emission_CO2+generate_ CO2; 0.473, 0.793, pH+pH_cumulo+PL+PL_cumulo+AN+ AN_cumulo+interval_yield+Feed_Vol+RS_cumulo+rab_ integral+RQ_integral+Accum._Yield+Arg_conc.+ emission_O2+emission_CO2+interval_O2; 0.487, 0.793, tmp+pH+PL+AN+AN_cumulo+interval_yield+Feed_Vol+ RS_cumulo+Cell_conc._interval+rab_integral+RQ_integral+Accum._Yield+Arg_conc.+emission_O2+emission_ CO2; 0.487, 0.793, tmp+tmp_cumulo+pH+PL+AN+AN_ cumulo+interval_yield+Feed_Vol+RS_cumulo+rab_ integral+RQ_integral+Arg_conc.+emission_O2+emission_ CO2+interval_O2; 0.534, 0.793, pH+AN+interval_yield+ Feed_Vol+RS_cumulo+rab_integral+RQ_integral+Arg_ conc.+emission_O2+emission_CO2+generate_CO2; 0.523, 0.793, pH_cumulo+PL_cumulo+AN+AN_cumulo+Feed_ Vol+RS_cumulo+rab_integral+RQ_integral+Arg_conc.+ emission_O2+emission_CO2+consum_O2; 0.499, 0.793, tmp+pH+AN+interval_yield+Feed_Vol+RS_cumulo+Cell_ conc._interval+rab_integral+RQ_integral+Accum._Yield+ Arg_conc.+emission_O2+emission_CO2+interval_O2; 0.487, 0.793, tmp+pH+PL+PL_cumulo+AN+AN_cumulo+ interval_yield+Feed_Vol+RS_cumulo+Cell_conc._interval+rab_integral+RQ_integral+Arg_conc.+emission_O2+ emission_CO2; 0.499, 0.793, pH+PL+AN+AN_cumulo+ interval_yield+Feed_Vol+RS_cumulo+rab_integral+RQ_ integral+Accum._Yield+Arg_conc.+emission_O2+ emission_CO2+interval_O2; 0.486, 0.793, tmp_cumulo+ pH+PL+PL_cumulo+AN+AN_cumulo+Feed_Vol+RS_ cumulo+Cell_conc._interval+rab_integral+RQ_integral+ Arg_conc.+emission_O2+emission_CO2+consum_O2; 0.486, 0.793, pH_cumulo+PL+PL_cumulo+AN+AN_cumulo+interval_yield+Feed_Vol+RS_cumulo+Cell_conc._ interval+rab_integral+RQ_integral+Accum._Yield+Arg_ conc.+emission_O2+emission_CO2; 0.499, 0.793, pH+PL_ cumulo+AN+interval_yield+Feed_Vol+RS_cumulo+Cell_ conc._interval+rab_integral+RQ_integral+Accum._Yield+ Arg_conc.+emission_O2+emission_CO2+consum_O2; 0.555, 0.793, pH+PL_cumulo+AN_cumulo+Feed_Vol+RS_ cumulo+rab_integral+Arg_conc.+emission_O2+emission_ CO2; 0.523, 0.793, pH+PL+AN+Feed_Vol+RS_cumulo+ Cell_conc._cumulo+rab_integral+RQ_integral+Arg_conc.+ emission_O2+emission_CO2+consum_O2; 0.545, 0.793, PL_cumulo+AN_cumulo+interval_yield+Feed_Vol+RS_ cumulo+rab_integral+Accum._Yield+Arg_conc.+emission_O2+emission_CO2; 0.486, 0.793, tmp_cumulo+pH+ PL_cumulo+AN+AN_cumulo+interval_yield+Feed_Vol+ RS_cumulo+rab_integral+RQ_integral+Accum._Yield+ Arg_conc.+emission_O2+emission_CO2+interval_O2; 0.486, 0.793, tmp+tmp_cumulo+pH+PL+PL_cumulo+AN+ interval_yield+Feed_Vol+RS_cumulo+rab_integral+RQ_ integral+Arg_conc.+emission_O2+emission_CO2+interval_O2; 0.473, 0.793, tmp+pH+PL+PL_cumulo+AN+AN_ cumulo+interval_yield+Feed_Vol+RS_cumulo+Cell_ conc._interval+rab_integral+RQ_integral+Arg_conc.+ emission_O2+emission_CO2+consum_O2; 0.499, 0.793, tmp_cumulo+pH+PL_cumulo+AN+AN_cumulo+Feed_Vol+RS_cumulo+rab_integral+RQ_integral+Accum._Yield+Arg_conc.+emission_O2+emission_CO2+generate_CO2; 0.523, 0.793, tmp_cumulo+pH+AN+interval_yield+Feed_Vol+RS_cumulo+rab_integral+RQ_integral+Accum._Yield+Arg_conc.+emission_O2+emission_CO2; 0.473, 0.793, tmp+pH+PL+PL_cumulo+AN+AN_cumulo+interval_yield+Feed_Vol+RS_cumulo+Cell_conc._interval+rab_integral+RQ_integral+Arg_conc.+emission_O2+emission_CO2+interval_O2; 0.511, 0.793, pH+pH_cumulo+AN+AN_cumulo+interval_yield+Feed_Vol+RS_cumulo+rab_integral+RQ_integral+Accum._Yield+Arg_conc.+emission_O2+emission_CO2; 0.511, 0.793, tmp_cumulo+pH+PL+PL_cumulo+AN+Feed_Vol+RS_cumulo+rab_integral+RQ_integral+Arg_conc.+emission_O2+emission_CO2+interval_O2; 0.499, 0.793, pH+pH_cumulo+PL+AN+AN_cumulo+interval_yield+Feed_Vol+RS_cumulo+Cell_conc._interval+rab_integral+RQ_integral+Arg_conc.+emission_O2+emission_CO2; 0.486, 0.793, tmp_cumulo+pH+PL+PL_cumulo+AN+interval_yield+Feed_Vol+RS_cumulo+rab_integral+RQ_integral+Arg_conc.+emission_O2+emission_CO2+consum_O2+generate_CO2; 0.473, 0.793, tmp+pH+PL+PL_cumulo+AN+AN_cumulo+interval_yield+Feed_Vol+RS_cumulo+rab_integral+RQ_integral+Arg_conc.+emission_O2+emission_CO2+interval_O2+generate_CO2; 0.511, 0.793, tmp_cumulo+pH+AN+AN_cumulo+Feed_Vol+RS_cumulo+Cell_conc._interval+rab_integral+RQ_integral+Arg_conc.+emission_O2+emission_CO2+generate_CO2; 0.523, 0.793, pH+PL_cumulo+AN_cumulo+interval_yield+Feed_Vol+RS_cumulo+rab_integral+Accum._Yield+Arg_conc.+emission_O2+emission_CO2+consum_O2; 0.499, 0.793, pH+PL_cumulo+AN+interval_yield+Feed_Vol+RS_cumulo+Cell_conc._interval+rab_integral+RQ_integral+Accum._Yield+Arg_conc.+emission_O2+emission_CO2+interval_O2; 0.511, 0.793, tmp+pH+PL_cumulo+AN+interval_yield+Feed_Vol+RS_cumulo+Cell_conc._interval+rab_integral+RQ_integral+Arg_conc.+emission_O2+emission_CO2; 0.523, 0.793, pH+PL+AN+Feed_Vol+RS_cumulo+Cell_conc._interval+rab_integral+RQ_integral+Arg_conc.+emission_O2+emission_CO2+consum_O2; 0.499, 0.793, pH+PL+AN+AN_cumulo+Feed_Vol+RS_cumulo+rab_integral+RQ_integral+Arg_conc.+emission_O2+emission_CO2+consum_O2+interval_O2+generate_CO2; 0.473, 0.793, tmp_cumulo+pH+PL+PL_cumulo+AN+AN_cumulo+interval_yield+Feed_Vol+RS_cumulo+Cell_conc._cumulo+rab_integral+RQ_integral+Arg_conc.+emission_O2+emission_CO2+interval_O2; 0.486, 0.793, pH+PL+PL_cumulo+AN+AN_cumulo+Feed_Vol+RS_cumulo+Cell_conc._cumulo+rab_integral+RQ_integral+Arg_conc.+emission_O2+emission_CO2+consum_O2+interval_O2; 0.523, 0.793, pH_cumulo+PL+PL_cumulo+AN+interval_yield+Feed_Vol+RS_cumulo+rab_integral+RQ_integral+Arg_conc.+emission_O2+emission_CO2; 0.486, 0.793, pH+pH_cumulo+PL+PL_cumulo+AN+interval_yield+Feed_Vol+RS_cumulo+rab_integral+RQ_integral+Accum._Yield+Arg_conc.+emission_O2+emission_CO2+consum_O2; 0.523, 0.793, pH+pH_cumulo+PL+AN+Feed_Vol+RS_cumulo+rab_integral+RQ_integral+Arg_conc.+emission_O2+emission_CO2+interval_O2; 0.499, 0.793, tmp+pH+PL+AN+AN_cumulo+Feed_Vol+RS_cumulo+rab_integral+RQ_integral+Accum._Yield+Arg_conc.+emission_O2+emission_CO2+generate_CO2; 0.534, 0.793, pH+AN+Feed_Vol+RS_cumulo+Cell_conc._interval+rab_integral+RQ_integral+Arg_conc.+emission_O2+emission_CO2+consum_O2; 0.499, 0.793, tmp+tmp_cumulo+pH+PL+PL_cumulo+AN+Feed_Vol+RS_cumulo+rab_integral+RQ_integral+Arg_conc.+emission_O2+emission_CO2+consum_O2; 0.511, 0.793, pH+AN+AN_cumulo+Feed_Vol+RS_cumulo+Cell_conc._interval+rab_integral+RQ_integral+Accum._Yield+Arg_conc.+emission_O2+emission_CO2+consum_O2; 0.486, 0.793, pH+PL+PL_cumulo+AN+AN_cumulo+Feed_Vol+RS_cumulo+Cell_conc._cumulo+rab_integral+RQ_integral+Arg_conc.+emission_O2+emission_CO2+interval_O2+generate_CO2; 0.499, 0.793, tmp_cumulo+pH+PL+PL_cumulo+AN+Feed_Vol+RS_cumulo+rab_integral+RQ_integral+Accum._Yield+Arg_conc.+emission_O2+emission_CO2+consum_O2; 0.473, 0.793, pH+PL+PL_cumulo+AN+AN_cumulo+interval_yield+Feed_Vol+RS_cumulo+rab_integral+RQ_integral+Accum._Yield+Arg_conc.+emission_O2+emission_CO2+consum_O2+generate_CO2; 0.511, 0.793, pH+PL+PL_cumulo+AN+Feed_Vol+RS_cumulo+rab_integral+RQ_integral+Accum._Yield+Arg_conc.+emission_O2+emission_CO2+generate_CO2; 0.511, 0.793, tmp_cumulo+pH+PL+AN+interval_yield+Feed_Vol+RS_cumulo+rab_integral+RQ_integral+Arg_conc.+emission_O2+emission_CO2+consum_O2; 0.523, 0.793, pH_cumulo+AN+interval_yield+RS+Feed_Vol+Cell_conc._interval+rab_integral+RQ_integral+Accum._Yield+Arg_conc.+emission_O2+emission_CO2; 0.499, 0.793, tmp+pH+PL_cumulo+AN+AN_cumulo+interval_yield+Feed_Vol+RS_cumulo+Cell_conc._interval+rab_integral+RQ_integral+Arg_conc.+emission_O2+emission_CO2; 0.499, 0.793, pH+pH_cumulo+PL+PL_cumulo+AN+interval_yield+Feed_Vol+RS_cumulo+rab_integral+RQ_integral+Arg_conc.+emission_O2+emission_CO2+interval_O2; 0.523, 0.793, pH+AN+AN_cumulo+Feed_Vol+RS_cumulo+Cell_conc._cumulo+rab_integral+RQ_integral+Arg_conc.+emission_O2+emission_CO2+consum_O2; 0.499, 0.793, pH+PL_cumulo+AN+AN_cumulo+Feed_Vol+RS_cumulo+rab_integral+RQ_integral+Arg_conc.+emission_O2+emission_CO2+consum_O2+interval_O2+generate_CO2; 0.534, 0.793, pH+pH_cumulo+PL_cumulo+AN_cumulo+Feed_Vol+RS_cumulo+rab_integral+RQ_integral+Arg_conc.+emission_O2+emission_CO2; 0.499, 0.793, pH_cumulo+PL+PL_cumulo+AN+interval_yield+Feed_Vol+RS_cumulo+Cell_conc._interval+rab_integral+RQ_integral+Accum._Yield+Arg_conc.+emission_O2+emission_CO2; 0.486, 0.793, tmp_cumulo+pH+PL+PL_cumulo+AN+interval_yield+Feed_Vol+RS_cumulo+Cell_conc._interval+rab_integral+RQ_integral+Arg_conc.+emission_O2+emission_CO2+interval_O2; 0.499, 0.793, pH+pH_cumulo+PL+PL_cumulo+AN+interval_yield+Feed_Vol+RS_cumulo+Cell_conc._interval+rab_integral+RQ_integral+Accum._Yield+Arg_conc.+emission_O2+emission_CO2; 0.534, 0.793, pH+AN_cumulo+Feed_Vol+RS_cumulo+rab_integral+RQ_integral+Accum._Yield+Arg_conc.+emission_O2+emission_CO2+generate_CO2; 0.486, 0.793, tmp_cumulo+pH+PL+PL_cumulo+AN+AN_cumulo+Feed_Vol+RS_cumulo+Cell_conc._cumulo+rab_integral+RQ_integral+Arg_conc.+emission_O2+emission_CO2+interval_O2; 0.486, 0.793, tmp+pH_cumulo+PL+PL_cumulo+AN+AN_cumulo+interval_yield+Feed_Vol+RS_cumulo+rab_integral+RQ_integral+Arg_conc.+emission_O2+emission_CO2+interval_O2; 0.499, 0.793, tmp_cumulo+pH+PL+AN+AN_cumulo+Feed_Vol+RS_cumulo+rab_integral+RQ_integral+Accum._Yield+Arg_conc.+emission_O2+emission_CO2+interval_O2; 0.544, 0.793, pH_cumulo+PL_cumulo+AN_cumulo+Feed_Vol+RS_cumulo+rab_integral+RQ_integral+Arg_conc.+emission_O2+emission_CO2; 0.534, 0.793, PL_cumulo+AN_cumulo+interval_yield+Feed_Vol+RS_cumulo+rab_ integral+Accum._Yield+Arg_conc.+emission_O2+ emission_CO2+interval_O2; 0.499, 0.793, pH+PL_cumulo+AN+AN_cumulo+Feed_Vol+RS_cumulo+rab_integral+RQ_integral+Accum._Yield+Arg_conc.+emission_O2+emission_CO2+consum_O2+generate_CO2; 0.486, 0.793, tmp+tmp_cumulo+pH+PL+AN+AN_cumulo+interval_yield+Feed_Vol+RS_cumulo+rab_integral+RQ_integral+Accum._Yield+Arg_conc.+emission_O2+emission_CO2; 0.472, 0.793, pH+PL+PL_cumulo+AN+AN_cumulo+interval_yield+Feed_Vol+RS_cumulo+rab_integral+RQ_integral+Accum._Yield+Arg_conc.+emission_O2+emission_CO2+interval_O2+generate_CO2; 0.511, 0.793, pH_cumulo+PL+PL_cumulo+AN+AN_cumulo+Feed_Vol+RS_cumulo+rab_integral+RQ_integral+Arg_conc.+emission_O2+emission_CO2+interval_O2; 0.533, 0.793, pH+PL_cumulo+AN_cumulo+interval_yield+Feed_Vol+RS_cumulo+rab_integral+Accum._Yield+Arg_conc.+emission_O2+emission_CO2; 0.498, 0.793, pH+PL_cumulo+AN+interval_yield+Feed_Vol+RS_cumulo+Cell_conc._interval+rab_integral+RQ_integral+Accum._Yield+Arg_conc.+emission_O2+emission_CO2+generate_CO2; 0.472, 0.793, pH+PL+PL_cumulo+AN+AN_cumulo+interval_yield+Feed_Vol+RS_cumulo+rab_integral+RQ_integral+Accum._Yield+Arg_conc.+emission_O2+emission_CO2+consum_O2+interval_O2; 0.472, 0.793, tmp+pH+PL+PL_cumulo+AN+interval_yield+Feed_Vol+RS_cumulo+Cell_conc._interval+rab_integral+RQ_integral+Accum._Yield+Arg_conc.+emission_O2+emission_CO2+interval_O2; 0.486, 0.793, tmp+pH+PL+PL_cumulo+AN+interval_yield+Feed_Vol+RS_cumulo+rab_integral+RQ_integral+Arg_conc.+emission_O2+emission_CO2+consum_O2+interval_O2; 0.522, 0.793, pH+pH_cumulo+PL+AN+Feed_Vol+RS_cumulo+rab_integral+RQ_integral+Arg_conc.+emission_O2+emission_CO2+consum_O2; 0.533, 0.793, pH+PL_cumulo+AN_cumulo+Feed_Vol+RS_cumulo+rab_integral+RQ_integral+Arg_conc.+emission_O2+emission_CO2+consum_O2; 0.486, 0.793, tmp_cumulo+pH+AN+AN_cumulo+interval_yield+Feed_Vol+RS_cumulo+Cell_conc._interval+rab_integral+RQ_integral+Accum._Yield+Arg_conc.+emission_O2+emission_CO2+generate_CO2; 0.485, 0.793, tmp_cumulo+pH+PL+PL_cumulo+AN+AN_cumulo+interval_yield+Feed_Vol+RS_cumulo+Cell_conc._interval+rab_integral+RQ_integral+Arg_conc.+emission_O2+emission_CO2; 0.544, 0.793, pH+AN_cumulo+Feed_Vol+RS_cumulo+Cell_conc._cumulo+rab_integral+RQ_integral+Arg_conc.+emission_O2+emission_CO2; 0.533, 0.793, pH_cumulo+AN+AN_cumulo+Feed_Vol+RS_cumulo+rab_integral+RQ_integral+Accum._Yield+Arg_conc.+emission_O2+emission_CO2; 0.522, 0.793, pH+PL+AN+Feed_Vol+RS_cumulo+Cell_conc._cumulo+rab_integral+RQ_integral+Arg_conc.+emission_O2+emission_CO2+interval_O2; 0.511, 0.793, pH+AN+AN_cumulo+Feed_Vol+RS_cumulo+rab_integral+RQ_integral+Accum._Yield+Arg_conc.+emission_O2+emission_CO2+consum_O2+generate_CO2; 0.511, 0.793, tmp_cumulo+pH+AN+AN_cumulo+interval_yield+Feed_Vol+RS_cumulo+rab_integral+RQ_integral+Arg_conc.+emission_O2+emission_CO2+generate_CO2; 0.485, 0.793, pH+PL+AN+AN_cumulo+interval_yield+Feed_Vol+RS_cumulo+Cell_conc._interval+rab_integral+RQ_integral+Accum._Yield+Arg_conc.+emission_O2+emission_CO2+interval_O2; 0.498, 0.793, tmp+pH+PL+AN+AN_cumulo+interval_yield+Feed_Vol+RS_cumulo+rab_integral+RQ_integral+Arg_conc.+emission_O2+emission_CO2+generate_CO2; 0.533, 0.793, pH+pH_cumulo+PL+AN+Feed_Vol+RS_cumulo+rab_integral+RQ_integral+Arg_conc.+emission_O2+emission_CO2; 0.510, 0.793, pH+pH_cumulo+PL+AN+AN_cumulo+Feed_Vol+RS_cumulo+Cell_conc._interval+rab_integral+RQ_integral+Arg_conc.+emission_O2+emission_CO2; 0.510, 0.793, tmp+pH+AN+AN_cumulo+Feed_Vol+RS_cumulo+Cell_conc._interval+rab_integral+RQ_integral+Arg_conc.+emission_O2+emission_CO2+generate_CO2; 0.485, 0.793, tmp+pH+PL+PL_cumulo+AN+AN_cumulo+Feed_Vol+RS_cumulo+Cell_conc._interval+rab_integral+RQ_integral+Arg_conc.+emission_O2+emission_CO2+consum_O2; 0.485, 0.793, tmp+pH+PL+PL_cumulo+AN+AN_cumulo+interval_yield+Feed_Vol+RS_cumulo+rab_integral+RQ_integral+Arg_conc.+emission_O2+emission_CO2+generate_CO2; 0.522, 0.793, pH+PL+AN+Feed_Vol+RS_cumulo+rab_integral+RQ_integral+Accum._Yield+Arg_conc.+emission_O2+emission_CO2+consum_O2; 0.522, 0.793, pH+pH_cumulo+PL+AN+Feed_Vol+RS_cumulo+rab_integral+RQ_integral+Accum._Yield+Arg_conc.+emission_O2+emission_CO2; 0.498, 0.793, tmp+tmp_cumulo+pH+AN+AN_cumulo+interval_yield+Feed_Vol+RS_cumulo+rab_integral+RQ_integral+Accum._Yield+Arg_conc.+emission_O2+emission_CO2; 0.510, 0.793, tmp+pH+PL+PL_cumulo+AN+Feed_Vol+RS_cumulo+rab_integral+RQ_integral+Arg_conc.+emission_O2+emission_CO2+generate_CO2; 0.498, 0.793, pH+PL+AN+AN_cumulo+interval_yield+Feed_Vol+RS_cumulo+rab_integral+RQ_integral+Accum._Yield+Arg_conc.+emission_O2+emission_CO2+generate_CO2; 0.522, 0.793, pH+PL_cumulo+AN+Feed_Vol+RS_cumulo+rab_integral+RQ_integral+Accum._Yield+Arg_conc.+emission_O2+emission_CO2+generate_CO2; 0.498, 0.793, pH+PL+AN+AN_cumulo+interval_yield+Feed_Vol+RS_cumulo+Cell_conc._interval+rab_integral+RQ_integral+Arg_conc.+emission_O2+emission_CO2+generate_CO2; 0.498, 0.793, tmp_cumulo+pH+PL_cumulo+AN+AN_cumulo+interval_yield+Feed_Vol+RS_cumulo+rab_integral+RQ_integral+Arg_conc.+emission_O2+emission_CO2+consum_O2; 0.522, 0.793, pH+PL+AN+Feed_Vol+RS_cumulo+rab_integral+RQ_integral+Arg_conc.+emission_O2+emission_CO2+consum_O2+generate_CO2; 0.533, 0.793, pH+PL+AN+AN_cumulo+RS+Feed_Vol+rab_integral+RQ_integral+Arg_conc.+emission_O2+emission_CO2; 0.498, 0.793, tmp_cumulo+pH+PL_cumulo+AN+AN_cumulo+interval_yield+Feed_Vol+RS_cumulo+Cell_conc._interval+rab_integral+RQ_integral+Arg_conc.+emission_O2+emission_CO2; 0.510, 0.793, tmp_cumulo+pH+pH_cumulo+AN+AN_cumulo+Feed_Vol+RS_cumulo+rab_integral+RQ_integral+Accum._Yield+Arg_conc.+emission_O2+emission_CO2; 0.498, 0.793, tmp_cumulo+pH+PL_cumulo+AN+AN_cumulo+Feed_Vol+RS_cumulo+rab_integral+RQ_integral+Accum._Yield+Arg_conc.+emission_O2+emission_CO2+consum_O2; 0.510, 0.793, pH+AN+interval_yield+RS+Feed_Vol+Cell_conc._interval+rab_integral+RQ_integral+Accum._Yield+Arg_conc.+emission_O2+emission_CO2+interval_O2; 0.510, 0.792, tmp+tmp_cumulo+pH+AN+AN_cumulo+Feed_Vol+RS_cumulo+rab_integral+RQ_integral+Arg_conc.+emission_O2+emission_CO2+consum_O2; 0.498, 0.792, tmp+pH+AN+interval_yield+Feed_Vol+RS_cumulo+Cell_conc._interval+rab_integral+RQ_integral+Accum._Yield+Arg_conc.+emission_O2+emission_CO2+generate_CO2; 0.498, 0.792, tmp_cumulo+pH+PL_cumulo+AN+AN_cumulo+Feed_Vol+RS_cumulo+rab_integral+RQ_integral+Accum._Yield+Arg_conc.+emission_O2+emission_CO2+interval_O2; 0.522, 0.792, pH+PL_cumulo+AN_cumulo+Feed_Vol+RS_cumulo+rab_integral+RQ_integral+Accum._Yield+Arg_conc.+emission_O2+emission_CO2+ interval_O2; 0.498, 0.792, pH+PL_cumulo+AN+AN_cumulo+interval_yield+Feed_Vol+RS_cumulo+Cell_conc._interval+rab_integral+RQ_integral+Arg_conc.+emission_O2+emission_CO2+generate_CO2; 0.498, 0.792, pH+PL_cumulo+AN+AN_cumulo+interval_yield+Feed_Vol+RS_cumulo+rab_integral+RQ_integral+Arg_conc.+emission_O2+emission_CO2+consum_O2+generate_CO2; 0.485, 0.792, tmp+pH+AN+AN_cumulo+interval_yield+Feed_Vol+RS_cumulo+Cell_conc._interval+rab_integral+RQ_integral+Accum._Yield+Arg_conc.+emission_O2+emission_CO2+generate_CO2; 0.498, 0.792, tmp_cumulo+pH+PL+AN+interval_yield+Feed_Vol+RS_cumulo+Cell_conc._interval+rab_integral+RQ_integral+Arg_conc.+emission_O2+emission_CO2+interval_O2; 0.510, 0.792, pH+pH_cumulo+PL_cumulo+AN+AN_cumulo+Feed_Vol+RS_cumulo+Cell_conc._interval+rab_integral+RQ_integral+Arg_conc.+emission_O2+emission_CO2; 0.533, 0.792, pH+pH_cumulo+AN+interval_yield+Feed_Vol+RS_cumulo+rab_integral+RQ_integral+Arg_conc.+emission_O2+emission_CO2; 0.485, 0.792, pH+PL+PL_cumulo+AN+AN_cumulo+Feed_Vol+RS_cumulo+rab_integral+RQ_integral+Accum._Yield+Arg_conc.+emission_O2+emission_CO2+interval_O2+generate_CO2; 0.498, 0.792, tmp+pH+PL+AN+interval_yield+Feed_Vol+RS_cumulo+Cell_conc._interval+rab_integral+RQ_integral+Arg_conc.+emission_O2+emission_CO2+interval_O2; 0.485, 0.792, tmp_cumulo+pH+AN+AN_cumulo+interval_yield+Feed_Vol+RS_cumulo+Cell_conc._interval+rab_integral+RQ_integral+Accum._Yield+Arg_conc.+emission_O2+emission_CO2+interval_O2; 0.485, 0.792, tmp+pH+PL_cumulo+AN+AN_cumulo+interval_yield+Feed_Vol+RS_cumulo+rab_integral+RQ_integral+Accum._Yield+Arg_conc.+emission_O2+emission_CO2+interval_O2; 0.471, 0.792, pH+PL+PL_cumulo+AN+AN_cumulo+interval_yield+Feed_Vol+RS_cumulo+rab_integral+RQ_integral+Arg_conc.+emission_O2+emission_CO2+consum_O2+interval_O2+generate_CO2; 0.521, 0.792, pH+PL+AN+interval_yield+Feed_Vol+RS_cumulo+rab_integral+RQ_integral+Arg_conc.+emission_O2+emission_CO2+consum_O2; 0.497, 0.792, tmp+tmp_cumulo+pH+PL+PL_cumulo+AN+interval_yield+Feed_Vol+RS_cumulo+rab_integral+RQ_integral+Arg_conc.+emission_O2+emission_CO2; 0.497, 0.792, pH+PL+cumulo+AN+AN_cumulo+Feed_Vol+RS_cumulo+Cell_conc._interval+rab_integral+RQ_integral+Accum._Yield+Arg_conc.+emission_O2+emission_CO2+generate_CO2; 0.485, 0.792, pH_cumulo+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2+generate_CO2; 0.521, 0.792, pH+AN+Feed_Vol+RS_cumulo+Cell_conc._interval+rab_integral+RQ_integral+Accum._Yield+Arg_conc.+emission_O2+emission_CO2+generate_CO2; 0.510, 0.792, tmp_cumulo+pH+pH_cumulo+PL+AN+interval_yield+Feed_Vol+RS_cumulo+rab_integral+RQ_integral+Arg_conc.+emission_O2+emission_CO2; 0.521, 0.792, pH_cumulo+PL+AN+AN_cumulo+interval_yield+Feed_Vol+RS_cumulo+rab_integral+RQ_integral+Arg_conc.+emission_O2+emission_CO2; 0.497, 0.792, pH+PL_cumulo+AN+AN_cumulo+interval_yield+Feed_Vol+RS_cumulo+rab_integral+RQ_integral+Arg_conc.+emission_O2+emission_CO2+consum_O2+interval_O2; 0.510, 0.792, pH+pH_cumulo+AN+AN_cumulo+Feed_Vol+RS_cumulo+rab_integral+RQ_integral+Accum._Yield+Arg_conc.+emission_O2+emission_CO2+interval_O2; 0.497, 0.792, tmp+pH+PL+AN_cumulo+Feed_Vol+RS_cumulo+rab_integral+RQ_integral+Accum._Yield+Arg_conc.+emission_O2+emission_CO2+interval_O2; 0.510, 0.792, pH+PL+PL_cumulo+AN+Feed_Vol+RS_cumulo+rab_integral+RQ_integral+Accum._Yield+Arg_conc.+emission_O2+emission_CO2+interval_O2; 0.543, 0.792, pH+AN+RS+Feed_Vol+Cell_conc._interval+rab_integral+RQ_integral+Arg_conc.+emission_O2+emission_CO2; 0.471, 0.792, tmp+tmp_cumulo+pH+PL+PL_cumulo+AN+interval_yield+Feed_Vol+RS_cumulo+rab_integral+RQ_integral+Accum._Yield+Arg_conc.+emission_O2+emission_CO2+consum_O2; 0.521, 0.792, tmp_cumulo+pH+PL+AN+Feed_Vol+RS_cumulo+Cell_conc._cumulo+rab_integral+RQ_integral+Arg_conc.+emission_O2+emission_CO2; 0.510, 0.792, pH_cumulo+PL+PL_cumulo+AN+AN_cumulo+Feed_Vol+RS_cumulo+rab_integral+RQ_integral+Arg_conc.+emission_O2+emission_CO2+consum_O2; 0.521, 0.792, pH+PL_cumulo+AN_cumulo+interval_yield+Feed_Vol+RS_cumulo+rab_integral+Accum._Yield+Arg_conc.+emission_O2+emission_CO2+interval_O2; 0.532, 0.792, pH+PL+AN+interval_yield+RS+Feed_Vol+rab_integral+RQ_integral+Arg_conc.+emission_O2+emission_CO2; 0.497, 0.792, pH+pH_cumulo+PL+AN+AN_cumulo+interval_yield+Feed_Vol+RS_cumulo+rab_integral+RQ_integral+Accum._Yield+Arg_conc.+emission_O2+emission_CO2; 0.497, 0.792, pH+PL+PL_cumulo+AN+AN_cumulo+interval_yield+Feed_Vol+RS_cumulo+rab_integral+Accum._Yield+Arg_conc.+emission_O2+emission_CO2+consum_O2; 0.484, 0.792, pH+pH_cumulo+PL+PL_cumulo+AN+interval_yield+Feed_Vol+RS_cumulo+Cell_conc._interval+rab_integral+RQ_integral+Accum._Yield+Arg_conc.+emission_O2+emission_CO2; 0.510, 0.792, pH+pH_cumulo+PL_cumulo+AN+AN_cumulo+Feed_Vol+RS_cumulo+rab_integral+RQ_integral+Arg_conc.+emission_O2+emission_CO2+generate_CO2; 0.521, 0.792, pH+PL_cumulo+AN+Feed_Vol+RS_cumulo+Cell_conc._interval+rab_integral+RQ_integral+Accum._Yield+Arg_conc.+emission_O2+emission_CO2; 0.497, 0.792, pH+PL_cumulo+AN+AN_cumulo+interval_yield+Feed_Vol+RS_cumulo+rab_integral+RQ_integral+Arg_conc.+emission_O2+emission_CO2+interval_O2+generate_CO2; 0.543, 0.792, pH+PL+AN+RS+Feed_Vol+rab_integral+RQ_integral+Arg_conc.+emission_O2+emission_CO2; 0.497, 0.792, tmp_cumulo+pH_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2; 0.484, 0.792, tmp_cumulo+pH+PL+PL_cumulo+AN+interval_yield+Feed_Vol+RS_cumulo+Cell_conc._interval+rab_integral+RQ_integral+Accum._Yield+Arg_conc.+emission_O2+emission_CO2; 0.509, 0.792, pH+PL+PL_cumulo+AN+AN_cumulo+interval_yield+Feed_Vol+RS_cumulo+rab_integral+Arg_conc.+emission_O2+emission_CO2+consum_O2; 0.497, 0.792, tmp_cumulo+pH+PL_cumulo+AN+interval_yield+Feed_Vol+RS_cumulo+Cell_conc._interval+rab_integral+RQ_integral+Accum._Yield+Arg_conc.+emission_O2+emission_CO2; 0.509, 0.792, pH+AN+AN_cumulo+interval_yield+Feed_Vol+RS_cumulo+Cell_conc._interval+rab_integral+RQ_integral+Arg_conc.+emission_O2+emission_CO2+consum_O2; 0.484, 0.792, pH_cumulo+PL+PL_cumulo+AN+AN_cumulo+interval_yield+Feed_Vol+RS_cumulo+rab_integral+RQ_integral+Accum._Yield+Arg_conc.+emission_O2+emission_CO2+interval_O2; 0.509, 0.792, tmp+pH+AN+AN_cumulo+interval_yield+Feed_Vol+RS_cumulo+rab_integral+RQ_integral+Arg_conc.+emission_O2+emission_CO2+interval_O2; 0.509, 0.792, tmp+pH+PL+AN+interval_yield+Feed_Vol+RS_cumulo+rab_integral+RQ_integral+Arg_conc.+emission_O2+emission_

CO2+interval_O2; 0.521, 0.792, pH+PL+AN+Feed_Vol+ RS_cumulo+rab_integral+RQ_integral+Arg_conc.+ emission_O2+emission_CO2+interval_O2+generate_CO2; 0.521, 0.792, tmp+tmp_cumulo+pH+AN+interval_yield+ Feed_Vol+RS_cumulo+rab_integral+RQ_integral+Arg_ conc.+emission_O2+emission_CO2; 0.484, 0.792, tmp+ pH+AN+AN_cumulo+interval_yield+Feed_Vol+RS_ cumulo+Cell_conc._interval+rab_integral+RQ_integral+ Accum._Yield+Arg_conc.+emission_O2+emission_CO2+ interval_O2; 0.521, 0.792, pH+PL+AN+Feed_Vol+RS_ cumulo+Cell_conc._cumulo+rab_integral+RQ_integral+ Arg_conc.+emission_O2+emission_CO2+generate_CO2; 0.497, 0.792, tmp+pH+PL_cumulo+AN+AN_cumulo+ Feed_Vol+RS_cumulo+rab_integral+RQ_integral+Accum._Yield+Arg_conc.+emission_O2+emission_CO2+ consum_O2; 0.497, 0.792, tmp_cumulo+pH+AN+interval_ yield+Feed_Vol+RS_cumulo+Cell_conc._interval+rab_ integral+RQ_integral+Accum._Yield+Arg_conc.+ emission_O2+emission_CO2+interval_O2; 0.470, 0.792, tmp+pH+PL+PL_cumulo+AN+AN_cumulo+interval_ yield+Feed_Vol+RS_cumulo+Cell_conc._cumulo+rab_integral+RQ_integral+Arg_conc.+emission_O2+emission_ CO2+consum_O2; 0.484, 0.792, pH+PL+PL_cumulo+AN+ AN_cumulo+Feed_Vol+RS_cumulo+rab_integral+RQ_ integral+Accum._Yield+Arg_conc.+emission_O2+ emission_CO2+consum_O2+generate_CO2; 0.497, 0.792, tmp_cumulo+pH+pH_cumulo+PL+AN+AN_cumulo+ Feed_Vol+RS_cumulo+rab_integral+RQ_integral+Arg_ conc.+emission_O2+emission_CO2+interval_O2; 0.521, 0.792, pH+PL_cumulo+AN_cumulo+Feed_Vol+RS_cumulo+rab_integral+RQ_integral+Accum._Yield+Arg_ conc.+emission_O2+emission_CO2+generate_CO2; 0.509, 0.792, tmp+tmp_cumulo+pH+AN_cumulo+interval_yield+ Feed_Vol+RS_cumulo+rab_integral+RQ_integral+Accum._Yield+Arg_conc.+emission_O2+emission_CO2; 0.532, 0.792, tmp_cumulo+pH+AN_cumulo+interval_ yield+Feed_Vol+RS_cumulo+rab_integral+RQ_integral+ Arg_conc.+emission_O2+emission_CO2; 0.497, 0.792, tmp+pH_cumulo+AN+AN_cumulo+interval_yield+Feed_ Vol+RS_cumulo+Cell_conc._interval+rab_integral+RQ_integral+Accum._Yield+Arg_conc.+emission_O2+emission_ CO2; 0.509, 0.792, tmp_cumulo+pH+AN+AN_cumulo+ Feed_Vol+RS_cumulo+rab_integral+RQ_integral+ Accum._Yield+Arg_conc.+emission_O2+emission_CO2+ consum_O2; 0.509, 0.792, tmp_cumulo+pH_cumulo+PL_ cumulo+AN+AN_cumulo+Feed_Vol+RS_cumulo+rab_ integral+RQ_integral+Accum._Yield+Arg_conc.+ emission_O2+emission_CO2; 0.521, 0.792, tmp+pH+PL+ AN+Feed_Vol+RS_cumulo+Cell_conc._cumulo+rab_ integral+RQ_integral+Arg_conc.+emission_O2+emission_ CO2; 0.509, 0.792, tmp_cumulo+pH+PL_cumulo+ AN+Feed_Vol+RS_cumulo+rab_integral+RQ_integral+ Accum._Yield+Arg_conc.+emission_O2+emission_CO2; 0.497, 0.792, pH_cumulo+PL_cumulo+AN+AN_cumulo+ interval_yield+Feed_Vol+RS_cumulo+rab_integral+RQ_ integral+Accum._Yield+Arg_conc.+emission_O2+emission_CO2+interval_O2; 0.532, 0.792, pH+pH_cumulo+ AN_cumulo+Feed_Vol+RS_cumulo+rab_integral+RQ_ integral+Accum._Yield+Arg_conc.+emission_O2+ emission_CO2; 0.497, 0.792, pH+pH_cumulo+PL_ cumulo+AN+AN_cumulo+interval_yield+Feed_Vol+RS_ cumulo+rab_integral+RQ_integral+Arg_conc.+emission_ O2+emission_CO2+interval_O2; 0.532, 0.792, tmp+pH+ AN_cumulo+interval_yield+Feed_Vol+RS_cumulo+rab_ integral+RQ_integral+Arg_conc.+emission_O2+emission_ CO2; 0.509, 0.792, tmp_cumulo+pH+AN+AN_cumulo+ Feed_Vol+RS_cumulo+Cell_conc._interval+rab_integral+ RQ_integral+Arg_conc.+emission_O2+emission_CO2+ interval_O2; 0.521, 0.792, pH+PL_cumulo+AN+interval_ yield+Feed_Vol+RS_cumulo+rab_integral+RQ_integral+ Arg_conc.+emission_O2+emission_CO2+generate_CO2; 0.532, 0.792, pH_cumulo+AN+AN_cumulo+Feed_Vol+ RS_cumulo+rab_integral+RQ_integral+Arg_conc.+emission_O2+emission_CO2+interval_O2; 0.496, 0.792, tmp_ cumulo+pH_cumulo+PL_cumulo+AN+AN_cumulo+ interval_yield+Feed_Vol+RS_cumulo+rab_integral+RQ_ integral+Accum._Yield+Arg_conc.+emission_O2+ emission_CO2; 0.520, 0.792, tmp+pH+AN+interval_yield+ Feed_Vol+RS_cumulo+rab_integral+RQ_integral+ Accum._Yield+Arg_conc.+emission_O2+emission_CO2; 0.470, 0.792, pH+pH_cumulo+PL+PL_cumulo+AN+AN_ cumulo+interval_yield+Feed_Vol+RS_cumulo+Cell_ conc._interval+rab_integral+RQ_integral+Arg_conc.+ emission_O2+emission_CO2+interval_O2; 0.532, 0.792, pH_cumulo+AN+interval_yield+RS+Feed_Vol+Cell_ conc._interval+rab_integral+RQ_integral+Arg_conc.+ emission_O2+emission_CO2; 0.483, 0.792, tmp+pH+PL+ AN+interval_yield+Feed_Vol+RS_cumulo+Cell_conc._ interval+rab_integral+RQ_integral+Accum._Yield+Arg_ conc.+emission_O2+emission_CO2+interval_O2; 0.509, 0.792, tmp+tmp_cumulo+pH+AN+AN_cumulo+Feed_ Vol+RS_cumulo+Cell_conc._cumulo+rab_integral+RQ_integral+Arg_conc.+emission_O2+emission_CO2; 0.520, 0.792, pH+PL_cumulo+AN_cumulo+interval_yield+Feed_ Vol+RS_cumulo+rab_integral+RQ_integral+Arg_conc.+ emission_O2+emission_CO2+interval_O2; 0.496, 0.792, tmp+pH+PL_cumulo+AN+AN_cumulo+interval_yield+ Feed_Vol+RS_cumulo+rab_integral+RQ_integral+Arg_ conc.+emission_O2+emission_CO2+consum_O2; 0.496, 0.792, tmp_cumulo+pH+pH_cumulo+PL+PL_cumulo+ AN+interval_yield+Feed_Vol+RS_cumulo+Accum._ Yield+Arg_conc.+emission_O2+emission_CO2+consum_ O2; 0.520, 0.792, pH+pH_cumulo+PL_cumulo+AN_ cumulo+Feed_Vol+RS_cumulo+Cell_conc._cumulo+rab_ integral+RQ_integral+Arg_conc.+emission_O2+emission_ CO2; 0.496, 0.792, tmp_cumulo+pH+PL+AN+AN_ cumulo+interval_yield+Feed_Vol+RS_cumulo+rab_ integral+RQ_integral+Arg_conc.+emission_O2+emission_ CO2+consum_O2; 0.483, 0.792, pH+PL+AN+AN_ cumulo+interval_yield+Feed_Vol+RS_cumulo+Cell_ conc._interval+rab_integral+RQ_integral+Accum._Yield+ Arg_conc.+emission_O2+emission_CO2+generate_CO2; 0.520, 0.792, tmp+pH+pH_cumulo+PL+AN+Feed_Vol+ RS_cumulo+rab_integral+RQ_integral+Arg_conc.+emission_CO2; 0.520, 0.792, pH+PL+AN+Feed_ Vol+RS_cumulo+Cell_conc._cumulo+rab_integral+RQ_ integral+Accum._Yield+Arg_conc.+emission_O2+ emission_CO2; 0.470, 0.792, tmp_cumulo+pH+pH_ cumulo+PL+PL_cumulo+AN+interval_yield+Feed_Vol+ RS_cumulo+rab_integral+RQ_integral+Accum._Yield+ Arg_conc.+emission_O2+emission_CO2+consum_O2; 0.496, 0.792, tmp+pH+PL_cumulo+AN+AN_cumulo+ Feed_Vol+RS_cumulo+rab_integral+RQ_integral+Accum._Yield+Arg_conc.+emission_O2+emission_CO2+interval_O2; 0.483, 0.792, tmp_cumulo+pH+PL+PL_ cumulo+AN+AN_cumulo+interval_yield+Feed_Vol+RS_ cumulo+rab_integral+RQ_integral+Arg_conc.+emission_ O2+emission_CO2+generate_CO2; 0.520, 0.792, tmp+pH+ PL_cumulo+AN+Feed_Vol+RS_cumulo+rab_integral+ RQ_integral+Accum._Yield+Arg_conc.+emission_O2+ emission_CO2; 0.531, 0.792, pH+AN_cumulo+Feed_Vol+ RS_cumulo+rab_integral+RQ_integral+Accum._Yield+ Arg_conc.+emission_O2+emission_CO2+interval_O2; 0.531, 0.792, pH+PL_cumulo+AN+Feed_Vol+RS_cumulo+Cell_conc._cumulo+rab_integral+RQ_integral+Arg_conc.+emission_O2+emission_CO2; 0.496, 0.792, pH+PL_cumulo+AN+AN_cumulo+interval_yield+Feed_Vol+RS_cumulo+Cell_conc._interval+rab_integral+RQ_integral+Arg_conc.+emission_O2+emission_CO2+consum_O2; 0.496, 0.792, tmp_cumulo+pH_cumulo+PL_cumulo+AN+AN_cumulo+interval_yield+Feed_Vol+RS_cumulo+Cell_conc._interval+rab_integral+RQ_integral+Arg_conc.+emission_O2+emission_CO2; 0.483, 0.792, pH+pH_cumulo+PL+PL_cumulo+AN+AN_cumulo+Feed_Vol+RS_cumulo+rab_integral+RQ_integral+Accum._Yield+Arg_conc.+emission_O2+emission_CO2+consum_O2; 0.483, 0.792, tmp+pH+PL+PL_cumulo+AN+AN_cumulo+Feed_Vol+RS_cumulo+Cell_conc._cumulo+rab_integral+RQ_integral+Arg_conc.+emission_O2+emission_CO2+interval_O2; 0.496, 0.792, tmp+pH+pH_cumulo+PL+PL_cumulo+AN+interval_yield+Feed_Vol+RS_cumulo+rab_integral+RQ_integral+Arg_conc.+emission_O2+emission_CO2; 0.508, 0.792, tmp_cumulo+pH+AN+AN_cumulo+Feed_Vol+RS_cumulo+rab_integral+RQ_integral+Arg_conc.+emission_O2+emission_CO2+consum_O2+interval_O2; 0.496, 0.792, pH+PL+PL_cumulo+AN+AN_cumulo+Feed_Vol+RS_cumulo+Cell_conc._cumulo+Cell_conc._interval+rab_integral+RQ_integral+Arg_conc.+emission_O2+emission_CO2; 0.542, 0.792, pH+AN_cumulo+Feed_Vol+RS_cumulo+Cell_conc._interval+rab_integral+RQ_integral+Arg_conc.+emission_O2+emission_CO2; 0.531, 0.792, pH+AN+AN_cumulo+interval_yield+RS+Feed_Vol+rab_integral+RQ_integral+Arg_conc.+emission_O2+emission_CO2; 0.496, 0.792, tmp+pH+pH_cumulo+PL+AN+AN_cumulo+interval_yield+Feed_Vol+RS_cumulo+rab_integral+RQ_integral+Arg_conc.+emission_O2+emission_CO2; 0.483, 0.792, pH+pH_cumulo+PL+AN+AN_cumulo+interval_yield+Feed_Vol+RS_cumulo+Cell_conc._interval+rab_integral+RQ_integral+Accum._Yield+Arg_conc.+emission_O2+emission_CO2; 0.542, 0.792, pH+AN_cumulo+Feed_Vol+RS_cumulo+rab_integral+RQ_integral+Arg_conc.+emission_O2+emission_CO2+consum_O2; 0.508, 0.792, tmp+pH+AN+interval_yield+Feed_Vol+RS_cumulo+Cell_conc._interval+rab_integral+RQ_integral+Arg_conc.+emission_O2+emission_CO2+interval_O2; 0.496, 0.792, pH_cumulo+PL_cumulo+AN+AN_cumulo+interval_yield+Feed_Vol+RS_cumulo+Cell_conc._interval+rab_integral+RQ_integral+Arg_conc.+emission_O2+emission_CO2+generate_CO2; 0.496, 0.792, pH_cumulo+PL+AN+AN_cumulo+interval_yield+Feed_Vol+RS_cumulo+Cell_conc._interval+rab_integral+RQ_integral+Arg_conc.+emission_O2+emission_CO2+interval_O2; 0.508, 0.791, tmp+pH+AN+AN_cumulo+Feed_Vol+RS_cumulo+Cell_conc._interval+rab_integral+RQ_integral+Arg_conc.+emission_O2+emission_CO2+interval_O2; 0.531, 0.791, tmp_cumulo+pH+AN+Feed_Vol+RS_cumulo+rab_integral+RQ_integral+Arg_conc.+emission_O2+emission_CO2+consum_O2; 0.496, 0.791, tmp+tmp_cumulo+pH+AN+interval_yield+Feed_Vol+RS_cumulo+Cell_conc._interval+rab_integral+RQ_integral+Accum._Yield+Arg_conc.+emission_O2+emission_CO2; 0.483, 0.791, pH+PL_cumulo+AN+AN_cumulo+interval_yield+Feed_Vol+RS_cumulo+rab_integral+RQ_integral+Accum._Yield+Arg_conc.+emission_O2+emission_CO2+interval_O2+generate_CO2; 0.496, 0.791, tmp_cumulo+pH+PL+AN+AN_cumulo+interval_yield+Feed_Vol+RS_cumulo+Cell_conc._cumulo+rab_integral+RQ_integral+Arg_conc.+emission_O2+emission_CO2; 0.520, 0.791, pH_cumulo+PL+AN+interval_yield+Feed_Vol+RS_cumulo+Cell_conc._interval+rab_integral+RQ_integral+Arg_conc.+emission_O2+emission_CO2; 0.496, 0.791, tmp_cumulo+pH+pH_cumulo+PL+AN+AN_cumulo+Feed_Vol+RS_cumulo+rab_integral+RQ_integral+Accum._Yield+Arg_conc.+emission_O2+emission_CO2; 0.483, 0.791, tmp_cumulo+pH+PL+PL_cumulo+AN+inter-val_yield+Feed_Vol+RS_cumulo+rab_integral+RQ_integral+Arg_conc.+emission_O2+emission_CO2+consum_O2+interval_O2; 0.508, 0.791, pH+AN+AN_cumulo+interval_yield+RS+Feed_Vol+Cell_conc._interval+rab_integral+RQ_integral+Accum._Yield+Arg_conc.+emission_O2+emission_CO2; 0.508, 0.791, pH+AN+AN_cumulo+Feed_Vol+RS_cumulo+Cell_conc._interval+rab_integral+RQ_integral+Arg_conc.+emission_O2+emission_CO2+consum_O2+interval_O2; 0.508, 0.791, tmp+pH+AN+AN_cumulo+interval_yield+Feed_Vol+RS_cumulo+rab_integral+RQ_integral+Arg_conc.+emission_O2+emission_CO2+generate_CO2; 0.483, 0.791, tmp_cumulo+pH+pH_cumulo+PL+PL_cumulo+AN+AN_cumulo+Feed_Vol+RS_cumulo+rab_integral+RQ_integral+Arg_conc.+emission_O2+emission_CO2+interval_O2; 0.519, 0.791, pH+PL_cumulo+AN_cumulo+Feed_Vol+RS_cumulo+Cell_conc._cumulo+rab_integral+RQ_integral+Accum._Yield+Arg_conc.+emission_O2+emission_CO2; 0.482, 0.791, pH_cumulo+PL+AN+AN_cumulo+inter-val_yield+Feed_Vol+RS_cumulo+Cell_conc._interval+rab_integral+RQ_integral+Accum._Yield+Arg_conc.+emission_O2+emission_CO2+consum_O2; 0.531, 0.791, pH+AN+Feed_Vol+RS_cumulo+rab_integral+RQ_integral+Arg_conc.+emission_O2+emission_CO2+interval_O2+generate_CO2; 0.508, 0.791, pH+AN+AN_cumulo+Feed_Vol+RS_cumulo+Cell_conc._interval+rab_integral+RQ_integral+Arg_conc.+emission_O2+emission_CO2+interval_O2+generate_CO2; 0.519, 0.791, tmp+pH+AN_cumulo+interval_yield+Feed_Vol+RS_cumulo+rab_integral+RQ_integral+Accum._Yield+Arg_conc.+emission_O2+emission_CO2; 0.508, 0.791, pH+PL+AN+AN_cumulo+Feed_Vol+RS_cumulo+Cell_conc._cumulo+Cell_conc._interval+rab_integral+RQ_integral+Arg_conc.+emission_O2+emission_CO2; 0.519, 0.791, pH+AN+Feed_Vol+RS_cumulo+Cell_conc._interval+rab_integral+RQ_integral+Accum._Yield+Arg_conc.+emission_O2+emission_CO2+interval_O2; 0.519, 0.791, tmp_cumulo+pH+AN+interval_yield+Feed_Vol+RS_cumulo+rab_integral+RQ_integral+Accum._Yield+Arg_conc.+emission_O2+emission_CO2; 0.482, 0.791, tmp+tmp_cumulo+pH+AN+AN_cumulo+interval_yield+Feed_Vol+RS_cumulo+Cell_conc._interval+rab_integral+RQ_integral+Accum._Yield+Arg_conc.+emission_O2+emission_CO2; 0.482, 0.791, tmp_cumulo+pH+pH_cumulo+PL+PL_cumulo+AN+interval_yield+Feed_Vol+RS_cumulo+rab_integral+RQ_integral+Arg_conc.+emission_O2+emission_CO2+interval_O2; 0.495, 0.791, pH+PL+PL_cumulo+AN+AN_cumulo+Feed_Vol+RS_cumulo+Cell_conc._interval+rab_integral+RQ_integral+Accum._Yield+Arg_conc.+emission_O2+emission_CO2; 0.482, 0.791, pH+PL_cumulo+AN+AN_cumulo+interval_yield+Feed_Vol+RS_cumulo+rab_integral+RQ_integral+Accum._Yield+Arg_conc.+emission_O2+emission_CO2+consum_O2+interval_O2; 0.531, 0.791, tmp+pH+AN_cumulo+Feed_Vol+RS_cumulo+rab_integral+RQ_integral+Arg_conc.+emission_O2+emission_CO2+generate_CO2; 0.495, 0.791, tmp+pH_cumulo+PL_cumulo+AN+AN_cumulo+interval_yield+Feed_Vol+RS_cumulo+Cell_conc._interval+rab_integral+RQ_integral+Arg_conc.+emission_O2+emission_CO2; 0.519, 0.791, tmp+tmp_cumulo+pH+AN_cumulo+Feed_Vol+RS_cumulo+rab_integral+RQ_integral+Arg_conc.+emission_O2+emission_CO2+interval_O2; 0.495, 0.791, tmp_cumulo+pH+AN+interval_yield+Feed_Vol+RS_cumulo+ Cell_conc._interval+rab_integral+RQ_integral+Accum._ Yield+Arg_conc.+emission_O2+emission_CO2+generate_ CO2; 0.508, 0.791, pH_cumulo+PL+AN+AN_cumulo+ interval_yield+Feed_Vol+RS_cumulo+Cell_conc._ interval+rab_integral+RQ_integral+Arg_conc.+emission_ O2+emission_CO2; 0.508, 0.791, pH+PL+AN+interval_ yield+Feed_Vol+RS_cumulo+Cell_conc._cumulo+Cell_ conc._interval+rab_integral+RQ_integral+Arg_conc.+ emission_O2+emission_CO2; 0.530, 0.791, pH+pH_ cumulo+AN+Feed_Vol+RS_cumulo+rab_integral+RQ_ integral+Accum._Yield+Arg_conc.+emission_O2+ emission_CO2; 0.519, 0.791, pH+AN+interval_yield+RS+ Feed_Vol+Cell_conc._interval+rab_integral+RQ+RQ_ integral+Arg_conc.+emission_O2+emission_CO2+ interval_O2; 0.507, 0.791, tmp+tmp_cumulo+pH+PL+PL_ cumulo+AN+Feed_Vol+RS_cumulo+rab_integral+RQ_ integral+Arg_conc.+emission_O2+emission_CO2; 0.507, 0.791, tmp+tmp_cumulo+pH+AN+AN_cumulo+Feed_ Vol+RS_cumulo+Cell_conc._interval+rab_integral+RQ_integral+Arg_conc.+emission_O2+emission_CO2; 0.495, 0.791, tmp+pH+PL+AN+AN_cumulo+interval_yield+ Feed_Vol+RS_cumulo+rab_integral+RQ_integral+Arg_ conc.+emission_O2+emission_CO2+generate_CO2; 0.507, 0.791, tmp+pH_cumulo+PL_cumulo+AN+AN_cumulo+ Feed_Vol+RS_cumulo+rab_integral+RQ_integral+Accum._Yield+Arg_conc.+emission_O2+emission_CO2; 0.495, 0.791, tmp_cumulo+pH+PL+AN+AN_cumulo+ Feed_Vol+RS_cumulo+rab_integral+RQ_integral+Arg_ conc.+emission_O2+emission_CO2+consum_O2+generate_CO2; 0.482, 0.791, pH+PL+PL_cumulo+AN+AN_ cumulo+Feed_Vol+RS_cumulo+rab_integral+RQ_ integral+Accum._Yield+Arg_conc.+emission_O2+ emission_CO2+consum_O2+interval_O2; 0.519, 0.791, pH+PL_cumulo+AN_cumulo+Feed_Vol+RS_cumulo+rab_ integral+RQ_integral+Accum._Yield+Arg_conc.+emission_O2+emission_CO2+consum_O2; 0.519, 0.791, pH+PL_cumulo+AN+Feed_Vol+RS_cumulo+rab_integral+ RQ_integral+Accum._Yield+Arg_conc.+emission_O2+ emission_CO2+consum_O2; 0.495, 0.791, tmp+tmp_cumulo+pH+PL+AN+interval_yield+Feed_Vol+RS_cumulo+ Cell_conc._interval+rab_integral+RQ_integral+Arg_ conc.+emission_O2+emission_CO2; 0.530, 0.791, pH+AN+Feed_Vol+RS_cumulo+rab_integral+RQ_integral+Accum._Yield+Arg_conc.+emission_O2+emission_ CO2+consum_O2; 0.507, 0.791, tmp_cumulo+pH+pH_cumulo+AN+AN_cumulo+interval_yield+Feed_Vol+RS_ cumulo+rab_integral+RQ_integral+Arg_conc.+emission_ O2+emission_CO2; 0.507, 0.791, pH+pH_cumulo+PL_ cumulo+AN+interval_yield+Feed_Vol+RS_cumulo+Cell_ conc._interval+rab_integral+RQ_integral+Arg_conc.+ emission_O2+emission_CO2; 0.482, 0.791, pH+AN+AN_ cumulo+interval_yield+Feed_Vol+RS_cumulo+Cell_ conc._interval+rab_integral+RQ_integral+Accum._Yield+ Arg_conc.+emission_O2+emission_CO2+consum_O2+ interval_O2; 0.495, 0.791, tmp_cumulo+pH+PL+AN+AN_ cumulo+Feed_Vol+RS_cumulo+rab_integral+RQ_ integral+Arg_conc.+emission_O2+emission_CO2+ consum_O2+interval_O2; 0.507, 0.791, pH+PL+PL_ cumulo+AN+interval_yield+Feed_Vol+RS_cumulo+Cell_ conc._cumulo+rab_integral+RQ_integral+Arg_conc.+ emission_O2+emission_CO2; 0.507, 0.791, tmp+pH+AN+ AN_cumulo+Feed_Vol+RS_cumulo+rab_integral+RQ_ integral+Arg_conc.+emission_O2+emission_CO2+ consum_O2+interval_O2; 0.530, 0.791, tmp+pH+PL+AN_ cumulo+Feed_Vol+RS_cumulo+rab_integral+RQ_ integral+Arg_conc.+emission_O2+emission_CO2; 0.507, 0.791, tmp+pH+PL_cumulo+AN+interval_yield+Feed_ Vol+RS_cumulo+rab_integral+RQ_integral+Accum._ Yield+Arg_conc.+emission_O2+emission_CO2; 0.507, 0.791, pH_cumulo+PL+AN+interval_yield+Feed_Vol+RS_ cumulo+Cell_conc._interval+rab_integral+RQ_integral+ Accum._Yield+Arg_conc.+emission_O2+emission_CO2; 0.530, 0.791, pH+PL_cumulo+AN_cumulo+Feed_Vol+RS_ cumulo+rab_integral+Accum._Yield+Arg_conc.+emission_O2+emission_CO2+consum_O2; 0.495, 0.791, tmp+ pH+pH_cumulo+PL+PL_cumulo+AN+Feed_Vol+RS_ cumulo+rab_integral+RQ_integral+Arg_conc.+emission_ O2+emission_CO2+consum_O2; 0.495, 0.791, pH+AN+ AN_cumulo+interval_yield+Feed_Vol+RS_cumulo+Cell_ conc._cumulo+Cell_conc._interval+rab_integral+RQ_ integral+Accum._Yield+Arg_conc.+emission_O2+ emission_CO2; 0.495, 0.791, tmp_cumulo+pH+PL+AN+ AN_cumulo+Feed_Vol+RS_cumulo+Cell_conc._cumulo+ rab_integral+RQ_integral+Arg_conc.+emission_O2+ emission_CO2+interval_O2; 0.495, 0.791, tmp+tmp_ cumulo+pH+PL_cumulo+AN+AN_cumulo+interval_ yield+Feed_Vol+RS_cumulo+rab_integral+RQ_integral+ Arg_conc.+emission_O2+emission_CO2; 0.482, 0.791, tmp_cumulo+pH+PL+PL_cumulo+AN+AN_cumulo+ Feed_Vol+RS_cumulo+rab_integral+RQ_integral+Accum._Yield+Arg_conc.+emission_O2+emission_CO2+interval_O2; 0.495, 0.791, tmp_cumulo+pH+PL+AN+AN_ cumulo+Feed_Vol+RS_cumulo+rab_integral+RQ_ integral+Arg_conc.+emission_O2+emission_CO2+ interval_O2+generate_CO2; 0.482, 0.791, pH+pH_ cumulo+PL+PL_cumulo+AN+AN_cumulo+Feed_Vol+ RS_cumulo+Cell_conc._cumulo+rab_integral+RQ_ integral+Arg_conc.+emission_O2+emission_CO2+ interval_O2; 0.482, 0.791, tmp_cumulo+pH+PL+AN+ interval_yield+Feed_Vol+RS_cumulo+Cell_conc._ interval+rab_integral+RQ_integral+Accum._Yield+Arg_ conc.+emission_O2+emission_CO2+interval_O2; 0.519, 0.791, pH+pH_cumulo+PL+AN+interval_yield+ Feed_Vol+RS_cumulo+rab_integral+RQ_integral+Arg_ conc.+emission_O2+emission_CO2; 0.507, 0.791, tmp+ pH+PL_cumulo+AN+cumulo+interval_yield+Feed_Vol+ RS_cumulo+rab_integral+RQ_integral+Accum._Yield+ Arg_conc.+emission_O2+emission_CO2; 0.507, 0.791, pH+pH_cumulo+AN+AN_cumulo+Feed_Vol+RS_cumulo+rab_integral+RQ_integral+Accum._Yield+Arg_ conc.+emission_O2+emission_CO2+generate_CO2; 0.495, 0.791, tmp_cumulo+pH+PL+AN+interval_yield+Feed_ Vol+RS_cumulo+Cell_conc._interval+rab_integral+RQ_integral+Arg_conc.+emission_O2+emission_CO2+consum_ O2; 0.519, 0.791, tmp+pH+PL_cumulo+AN+Feed_Vol+ RS_cumulo+rab_integral+RQ_integral+Arg_conc.+ emission_O2+emission_CO2+consum_O2; 0.495, 0.791, tmp+pH+PL+AN+AN_cumulo+Feed_Vol+RS_cumulo+ rab_integral+RQ_integral+Arg_conc.+emission_O2+emission_CO2+consum_O2+interval_O2; 0.468, 0.791, tmp+ pH+pH_cumulo+PL+PL_cumulo+AN+interval_yield+ Feed_Vol+RS_cumulo+rab_integral+RQ_integral+ Accum._Yield+Arg_conc.+emission_O2+emission_CO2+ consum_O2; 0.495, 0.791, tmp+pH+PL_cumulo+AN+ Feed_Vol+RS_cumulo+rab_integral+RQ_integral+Arg_ conc.+emission_O2+emission_CO2+consum_O2+ generate_CO2; 0.495, 0.791, pH+pH_cumulo+PL+PL_ cumulo+AN+interval_yield+Feed_Vol+RS_cumulo+rab_ integral+RQ_integral+Accum._Yield+Arg_conc.+ emission_O2+emission_CO2; 0.519, 0.791, pH+PL_ cumulo+AN_cumulo+Feed_Vol+RS_cumulo+Cell_conc._ cumulo+rab_integral+RQ_integral+Arg_conc.+emission_ O2+emission_CO2+interval_O2; 0.507, 0.791, pH+AN+

AN_cumulo+Feed_Vol+RS_cumulo+Cell_conc._cumulo+rab_integral+RQ_integral+Accum._Yield+Arg_conc.+emission_O2+emission_CO2+generate_CO2; 0.495, 0.791, tmp+pH+PL_cumulo+AN+AN_cumulo+interval_yield+Feed_Vol+RS_cumulo+rab_integral+RQ_integral+Arg_conc.+emission_O2+emission_CO2+generate_CO2; 0.495, 0.791, tmp_cumulo+pH+PL_cumulo+AN+AN_cumulo+Feed_Vol+RS_cumulo+Cell_conc._interval+rab_integral+RQ_integral+Accum._Yield+Arg_conc.+emission_O2+emission_CO2; 0.507, 0.791, pH+PL_cumulo+AN+interval_yield+Feed_Vol+RS_cumulo+Cell_conc._interval+rab_integral+RQ_integral+Arg_conc.+emission_O2+emission_CO2+interval_O2; 0.507, 0.791, pH_cumulo+PL+PL_cumulo+AN+AN_cumulo+Feed_Vol+RS_cumulo+Cell_conc._cumulo+rab_integral+RQ_integral+Arg_conc.+emission_O2+emission_CO2; 0.507, 0.791, tmp_cumulo+pH+AN+AN_cumulo+Feed_Vol+RS_cumulo+rab_integral+RQ_integral+Arg_conc.+emission_O2+emission_CO2+interval_O2+generate_CO2; 0.482, 0.791, tmp_cumulo+pH+pH_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2; 0.495, 0.791, pH+AN+interval_yield+Feed_Vol+RS_cumulo+Cell_conc._interval+rab_integral+RQ_integral+Accum._Yield+Arg_conc.+emission_O2+emission_CO2+consum_O2+interval_O2; 0.495, 0.791, tmp_cumulo+pH+pH_cumulo+PL+PL_cumulo+AN+Feed_Vol+RS_cumulo+rab_integral+RQ_integral+Arg_conc.+emission_O2+emission_CO2+consum_O2; 0.507, 0.791, pH+pH_cumulo+AN+interval_yield+RS+Feed_Vol+Cell_conc._interval+rab_integral+RQ_integral+Accum._Yield+Arg_conc.+emission_O2+emission_CO2; 0.507, 0.791, tmp+pH+AN+AN_cumulo+Feed_Vol+RS_cumulo+rab_integral+RQ_integral+Accum._Yield+Arg_conc.+emission_O2+emission_CO2+consum_O2; 0.507, 0.791, tmp+pH+PL+PL_cumulo+AN+Feed_Vol+RS_cumulo+Cell_conc._interval+rab_integral+RQ_integral+Arg_conc.+emission_O2+emission_CO2; 0.507, 0.791, pH+AN+interval_yield+Feed_Vol+RS_cumulo+Cell_conc._cumulo+Cell_conc._interval+rab_integral+RQ_integral+Accum._Yield+Arg_conc.+emission_O2+emission_CO2; 0.507, 0.791, tmp_cumulo+pH+PL_cumulo+AN_cumulo+interval_yield+Feed_Vol+RS_cumulo+rab_integral+RQ_integral+Accum._Yield+Arg_conc.+emission_O2+emission_CO2; 0.507, 0.791, tmp+pH+AN_cumulo+Feed_Vol+RS_cumulo+rab_integral+RQ_integral+Arg_conc.+emission_O2+emission_CO2+interval_O2+generate_CO2; 0.494, 0.791, tmp+tmp_cumulo+pH+PL_cumulo+AN+AN_cumulo+Feed_Vol+RS_cumulo+rab_integral+RQ_integral+Accum._Yield+Arg_conc.+emission_O2+emission_CO2; 0.530, 0.791, pH+AN+Feed_Vol+RS_cumulo+rab_integral+RQ_integral+Arg_conc.+emission_O2+emission_CO2+consum_O2+generate_CO2; 0.507, 0.791, tmp_cumulo+pH+PL_cumulo+AN+interval_yield+Feed_Vol+RS_cumulo+Cell_conc._interval+rab_integral+RQ_integral+Arg_conc.+emission_O2+emission_CO2; 0.481, 0.791, pH+AN+AN_cumulo+interval_yield+Feed_Vol+RS_cumulo+Cell_conc._interval+rab_integral+RQ_integral+Accum._Yield+Arg_conc.+emission_O2+emission_CO2+interval_O2+generate_CO2; 0.481, 0.791, tmp_cumulo+pH+PL_cumulo+AN+AN_cumulo+interval_yield+Feed_Vol+RS_cumulo+rab_integral+RQ_integral+Accum._Yield+Arg_conc.+emission_O2+emission_CO2+consum_O2; 0.530, 0.791, pH+AN+AN_cumulo+RS+Feed_Vol+RS_cumulo+rab_integral++RQ_integral+Arg_conc.+emission_O2+emission_CO2; 0.530, 0.791, tmp+pH+AN+Feed_Vol+RS_cumulo+rab_integral+RQ_integral+Arg_conc.+emission_O2+emission_CO2+consum_O2; 0.481, 0.791, tmp+pH+pH_cumulo+PL+PL_cumulo+AN+interval_yield+Feed_Vol+RS_cumulo+rab_integral+RQ_integral+Arg_conc.+emission_O2+emission_CO2+interval_O2; 0.494, 0.791, tmp+pH_cumulo+PL_cumulo+AN+AN_cumulo+interval_yield+Feed_Vol+RS_cumulo+rab_integral+RQ_integral+Accum._Yield+Arg_conc.+emission_O2+emission_CO2; 0.494, 0.791, tmp+pH+AN+interval_yield+Feed_Vol+RS_cumulo+Cell_conc._interval+rab_integral+RQ_integral+Accum._Yield+Arg_conc.+emission_O2+emission_CO2+consum_O2; 0.507, 0.791, pH_cumulo+PL_cumulo+AN+AN_cumulo+interval_yield+Feed_Vol+RS_cumulo+rab_integral+RQ_integral+Arg_conc.+emission_O2+emission_CO2+generate_CO2; 0.518, 0.791, pH+AN+AN_cumulo+interval_yield+RS+Feed_Vol+Cell_conc._interval+rab_integral+RQ_integral+Arg_conc.+emission_O2+emission_CO2; 0.494, 0.791, pH+PL+PL_cumulo+AN+interval_yield+Feed_Vol+RS_cumulo+rab_integral+RQ_integral+Accum._Yield+Arg_conc.+emission_O2+emission_CO2+generate_CO2; 0.481, 0.791, pH+pH_cumulo+PL+PL_cumulo+AN+interval_yield+Feed_Vol+RS_cumulo+Cell_conc._interval+rab_integral+RQ_integral+Arg_conc.+emission_O2+emission_CO2+consum_O2; 0.494, 0.791, tmp+pH+PL+PL_cumulo+AN+Feed_Vol+RS_cumulo+Cell_conc._interval+rab_integral+RQ_integral+Arg_conc.+emission_O2+emission_CO2+consum_O2; 0.494, 0.791, tmp+pH+PL+AN+AN_cumulo+Feed_Vol+RS_cumulo+rab_integral+RQ_integral+Arg_conc.+emission_O2+emission_CO2+interval_O2+generate_CO2; 0.494, 0.791, pH+PL+PL_cumulo+AN+interval_yield+Feed_Vol+RS_cumulo+rab_integral+RQ_integral+Arg_conc.+emission_O2+emission_CO2+interval_O2+generate_CO2; 0.506, 0.791, pH+AN+AN_cumulo+Feed_Vol+RS_cumulo+Cell_conc._interval+rab_integral+RQ_integral+Arg_conc.+emission_O2+emission_CO2+consum_O2+generate_CO2; 0.529, 0.791, pH+pH_cumulo+AN+Feed_Vol+RS_cumulo+rab_integral+RQ_integral+Arg_conc.+emission_O2+emission_CO2+interval_O2; 0.506, 0.791, tmp_cumulo+pH+AN+interval_yield+Feed_Vol+RS_cumulo+Cell_conc._interval+rab_integral+RQ_integral+Arg_conc.+emission_O2+emission_CO2+interval_O2; 0.506, 0.791, tmp+pH+AN+interval_yield+Feed_Vol+RS_cumulo+Cell_conc._interval+rab_integral+RQ_integral+Arg_conc.+emission_O2+emission_CO2+generate_CO2; 0.494, 0.791, tmp_cumulo+pH+pH_cumulo+PL_cumulo+AN+AN_cumulo+interval_yield+Feed_Vol+RS_cumulo+rab_integral+RQ_integral+Arg_conc.+emission_O2+emission_CO2; 0.481, 0.791, tmp+pH+PL+PL_cumulo+AN+AN_cumulo+Feed_Vol+RS_cumulo+rab_integral+RQ_integral+Accum._Yield+Arg_conc.+emission_O2+emission_CO2+interval_O2; 0.494, 0.791, tmp+pH+pH_cumulo+PL+AN+AN_cumulo+Feed_Vol+RS_cumulo+rab_integral+RQ_integral+Arg_conc.+emission_O2+emission_CO2+interval_O2; 0.529, 0.791, tmp+pH+AN_cumulo+Feed_Vol+RS_cumulo+rab_integral+RQ_integral+Arg_conc.+emission_O2+emission_CO2+interval_O2; 0.518, 0.791, pH+PL_cumulo+AN_cumulo+interval_yield+Feed_Vol+RS_cumulo+Cell_conc._interval+rab_integral+Accum._Yield+Arg_conc.+emission_O2+emission_CO2; 0.518, 0.791, pH+AN+interval_yield+Feed_Vol+RS_cumulo+Cell_conc._cumulo+Cell_conc._interval+rab_integral+RQ_integral+Arg_conc.+emission_O2+emission_CO2; 0.506, 0.791, pH+PL_cumulo+AN+interval_yield+Feed_Vol+RS_cumulo+Cell_conc._interval+rab_integral+RQ_integral+Arg_conc.+emission_O2+emission_CO2+consum_O2; 0.494, 0.791, tmp_cumulo+pH+pH_cumulo+PL+PL_cumulo+AN+interval_yield+Feed_Vol+RS_cumulo+rab_integral+RQ_integral+Arg_conc.+emission_O2+emission_CO2; 0.506, 0.791, pH+AN+AN_cumulo+interval_yield+Feed_Vol+RS_cumulo+Cell_conc._cumulo+Cell_conc._interval+rab_integral+RQ_integral+Arg_conc.+emission_O2+emission_CO2; 0.467, 0.791, pH_cumulo+PL+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2+interval_O2; 0.494, 0.791, pH+pH_cumulo+PL+AN+AN_cumulo+interval_yield+Feed_Vol+RS_cumulo+rab_integral+RQ_integral+Arg_conc.+emission_O2+emission_CO2+interval_O2; 0.467, 0.791, tmp+pH+PL+PL_cumulo+AN+AN_cumulo+interval_yield+Feed_Vol+RS_cumulo+Cell_conc._cumulo+rab_integral+RQ_integral+Arg_conc.+emission_O2+emission_CO2+interval_O2; 0.494, 0.791, pH+pH_cumulo+PL+PL_cumulo+AN+AN_cumulo+Feed_Vol+RS_cumulo+Cell_conc._interval+rab_integral+RQ_integral+Arg_conc.+emission_O2+emission_CO2; 0.453, 0.791, tmp+tmp_cumulo+pH+PL+PL_cumulo+AN+AN_cumulo+interval_yield+Feed_Vol+RS_cumulo+rab_integral+RQ_integral+Accum._Yield+Arg_conc.+emission_O2+emission_CO2+consum_O2; 0.518, 0.791, tmp_cumulo+pH+AN+Feed_Vol+RS_cumulo+Cell_conc._interval+rab_integral+RQ_integral+Accum._Yield+Arg_conc.+emission_O2+emission_CO2; 0.481, 0.791, pH+pH_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2+interval_O2; 0.529, 0.791, tmp_cumulo+pH+PL+AN_cumulo+Feed_Vol+RS_cumulo+rab_integral+RQ_integral+Arg_conc.+emission_O2+emission_CO2; 0.506, 0.791, tmp_cumulo+pH+AN+AN_cumulo+Feed_Vol+RS_cumulo+rab_integral+RQ_integral+Arg_conc.+emission_O2+emission_CO2+consum_O2+generate_CO2; 0.506, 0.791, pH_cumulo+PL+PL_cumulo+AN+AN_cumulo+Feed_Vol+RS_cumulo+rab_integral+RQ_integral+Accum._Yield+Arg_conc.+emission_O2+emission_CO2; 0.506, 0.791, tmp_cumulo+pH+PL+AN+interval_yield+Feed_Vol+RS_cumulo+Cell_conc._cumulo+rab_integral+RQ_integral+Arg_conc.+emission_O2+emission_CO2; 0.494, 0.791, tmp+pH+PL+AN+AN_cumulo+Feed_Vol+RS_cumulo+Cell_conc._interval+rab_integral+RQ_integral+Accum._Yield+Arg_conc.+emission_O2+emission_CO2; 0.506, 0.791, pH+AN+interval_yield+RS+Feed_Vol+Cell_conc._interval+rab_integral+RQ_integral+Accum._Yield+Arg_conc.+emission_O2+emission_CO2+consum_O2; 0.518, 0.791, tmp+pH+AN+Feed_Vol+RS_cumulo+Cell_conc._interval+rab_integral+RQ_integral+Accum._Yield+Arg_conc.+emission_O2+emission_CO2; 0.529, 0.791, pH_cumulo+AN+AN_cumulo+Feed_Vol+RS_cumulo+Cell_conc._interval+rab_integral+RQ_integral+Arg_conc.+emission_O2+emission_CO2; 0.506, 0.791, tmp+pH+AN_cumulo+interval_yield+Feed_Vol+RS_cumulo+Cell_conc._interval+rab_integral+RQ_integral+Accum._Yield+Arg_conc.+emission_O2+emission_CO2; 0.481, 0.791, pH+PL+PL_cumulo+AN+AN_cumulo+Feed_Vol+RS_cumulo+Cell_conc._cumulo+rab_integral+RQ_integral+Accum._Yield+Arg_conc.+emission_O2+emission_CO2+consum_O2; 0.506, 0.791, pH+PL+PL_cumulo+AN+Feed_Vol+RS_cumulo+Cell_conc._interval+rab_integral+RQ_integral+Accum._Yield+Arg_conc.+emission_O2+emission_CO2; 0.506, 0.791, pH+pH_cumulo+AN+AN_cumulo+Feed_Vol+RS_cumulo+Cell_conc._interval+rab_integral+RQ_integral+Accum._Yield+Arg_conc.+emission_O2+emission_CO2; 0.494, 0.791, tmp+pH+PL+AN+AN_cumulo+Feed_Vol+RS_cumulo+Cell_conc._cumulo+rab_integral+RQ_integral+Arg_conc.+emission_O2+emission_CO2+interval_O2; 0.518, 0.791, tmp+tmp_cumulo+pH+cumulo+AN+AN_cumulo+Feed_Vol+RS_cumulo+rab_integral+RQ_integral+Arg_conc.+emission_O2+emission_CO2; 0.506, 0.791, tmp+tmp_cumulo+pH+pH_cumulo+AN+AN_cumulo+Feed_Vol+RS_cumulo+rab_integral+RQ_integral+Arg_conc.+emission_O2+emission_CO2; 0.529, 0.791, pH_cumulo+PL_cumulo+AN+interval_yield+Feed_Vol+RS_cumulo+rab_integral+RQ_integral+Arg_conc.+emission_O2+emission_CO2; 0.506, 0.791, pH+AN+interval_yield+RS+Feed_Vol+Cell_conc._interval+rab_integral+RQ_integral+Accum._Yield+Arg_conc.+emission_O2+emission_CO2+generate_CO2; 0.506, 0.791, pH+AN+AN_cumulo+interval_yield+Feed_Vol+RS_cumulo+rab_integral+RQ_integral+Accum._Yield+Arg_conc.+emission_O2+emission_CO2+consum_O2; 0.467, 0.791, pH+pH_cumulo+PL_cumulo+AN+AN_cumulo+interval_yield+Feed_Vol+RS_cumulo+Cell_conc._interval+rab_integral+RQ_integral+Accum._Yield+Arg_conc.+emission_O2+emission_CO2+interval_O2; 0.494, 0.791, pH+PL_cumulo+AN_cumulo+interval_yield+Feed_Vol+RS_cumulo+Cell_conc._interval+rab_integral+RQ_integral+Accum._Yield+Arg_conc.+emission_O2+emission_CO2+interval_O2; 0.481, 0.791, pH+PL+PL_cumulo+AN+interval_yield+Feed_Vol+RS_cumulo+Cell_conc._interval+rab_integral+RQ_integral+Accum._Yield+Arg_conc.+emission_O2+emission_CO2+generate_CO2; 0.481, 0.790, tmp_cumulo+pH_cumulo+PL+PL_cumulo+AN+AN_cumulo+interval_yield+Feed_Vol+RS_cumulo+rab_integral+RQ_integral+Arg_conc.+emission_O2+emission_CO2+consum_O2; 0.481, 0.790, pH+PL+PL_cumulo+AN+AN_cumulo+interval_yield+Feed_Vol+RS_cumulo+Cell_conc._interval+rab_integral+RQ_integral+Arg_conc.+emission_O2+emission_CO2+generate_CO2; 0.494, 0.790, pH+PL_cumulo+AN+AN_cumulo+Feed_Vol+RS_cumulo+Cell_conc._interval+rab_integral+RQ_integral+Accum._Yield+Arg_conc.+emission_O2+emission_CO2+consum_O2; 0.506, 0.790, tmp+pH+AN+interval_yield+RS+Feed_Vol+Cell_conc._interval+rab_integral+RQ_integral+Accum._Yield+Arg_conc.+emission_O2+emission_CO2; 0.493, 0.790, tmp_cumulo+pH+PL_cumulo+AN+AN_cumulo+interval_yield+Feed_Vol+RS_cumulo+rab_integral+RQ_integral+Arg_conc.+emission_O2+emission_CO2+generate_CO2; 0.493, 0.790, pH+pH_cumulo+PL+AN+AN_cumulo+Feed_Vol+RS_cumulo+rab_integral+RQ_integral+Accum._Yield+Arg_conc.+emission_O2+emission_CO2+interval_O2; 0.506, 0.790, pH+PL_cumulo+AN+AN_cumulo+interval_yield+Feed_Vol+RS_cumulo+Cell_conc._interval+rab_integral+Accum._Yield+Arg_conc.+emission_O2+emission_CO2+interval_O2; 0.506, 0.790, pH+PL_cumulo+AN+interval_yield+Feed_Vol+RS_cumulo+rab_integral+RQ_integral+Accum._Yield+Arg_conc.+emission_O2+emission_CO2+consum_O2; 0.493, 0.790, tmp_cumulo+pH+PL+AN+AN_cumulo+Feed_Vol+RS_cumulo+Cell_conc._interval+rab_integral+RQ_integral+Arg_conc.+emission_O2+emission_CO2+generate_CO2; 0.506, 0.790, pH+PL+AN+interval_yield+Feed_Vol+RS_cumulo+rab_integral+RQ_integral+Accum._Yield+Arg_conc.+emission_O2+emission_CO2+interval_O2; 0.493, 0.790, tmp+pH+PL+AN+AN_cumulo+Feed_Vol+RS_cumulo+rab_integral+RQ_integral+Arg_conc.+emission_O2+emission_CO2+consum_O2+generate_CO2; 0.506, 0.790, tmp+tmp_cumulo+pH+AN+interval_yield+Feed_Vol+RS_cumulo+Cell_conc._interval+rab_integral+RQ_integral+Arg_conc.+emission_O2+emission_CO2; 0.480, 0.790, pH+pH_cumulo+PL+

PL_cumulo+AN+AN_cumulo+Feed_Vol+RS_cumulo+ rab_integral+RQ_integral+Arg_conc.+emission_O2+ emission_CO2+consum_O2+interval_O2; 0.506, 0.790, pH_cumulo+PL_cumulo+AN_cumulo+interval_yield+ Feed_Vol+RS_cumulo+Cell_conc._interval+rab_integral+ RQ_integral+Accum._Yield+Arg_conc.+emission_O2+ emission_CO2; 0.493, 0.790, pH+PL+PL_cumulo+AN+ interval_yield+Feed_Vol+RS_cumulo+Cell_conc._ interval+rab_integral+RQ_integral+Arg_conc.+emission_ O2+emission_CO2+generate_CO2; 0.493, 0.790, tmp_ cumulo+pH+AN+AN_cumulo+Feed_Vol+RS_cumulo+ Cell_conc._interval+rab_integral+RQ_integral+Accum._ Yield+Arg_conc.+emission_O2+emission_CO2+generate_ CO2; 0.506, 0.790, tmp_cumulo+pH+PL+AN+interval_ yield+Feed_Vol+RS_cumulo+rab_integral+RQ_integral+ Arg_conc.+emission_O2+emission_CO2+generate_CO2; 0.480, 0.790, tmp+pH+PL_cumulo+AN+AN_cumulo+in- terval_yield+Feed_Vol+RS_cumulo+rab_integral+RQ_in- tegral+Accum._Yield+Arg_conc.+emission_O2+emission_ CO2+consum_O2; 0.493, 0.790, tmp_cumulo+pH+PL+ AN+AN_cumulo+Feed_Vol+RS_cumulo+Cell_conc._ interval+rab_integral+RQ_integral+Arg_conc.+emission_ O2+emission_CO2+interval_O2; 0.493, 0.790, tmp+tmp_ cumulo+pH+AN+AN_cumulo+Feed_Vol+RS_cumulo+ rab_integral+RQ_integral+Accum._Yield+Arg_conc.+ emission_O2+emission_CO2+generate_CO2; 0.529, 0.790, tmp+pH+pH_cumulo+AN_cumulo+Feed_Vol+RS_cu- mulo+rab_integral+RQ_integral+Arg_conc.+emission_ O2+emission_CO2; 0.493, 0.790, pH+PL+AN+AN_cu- mulo+Feed_Vol+RS_cumulo+rab_integral+RQ_integral+ Accum._Yield+Arg_conc.+emission_O2+emission_CO2+ interval_O2+generate_CO2; 0.493, 0.790, pH+PL_cumulo+ AN+AN_cumulo+interval_yield+Feed_Vol+RS_cumulo+ Cell_conc._cumulo+rab_integral+RQ_integral+Arg_conc.+ emission_O2+emission_CO2+interval_O2; 0.539, 0.790, PL_cumulo+AN_cumulo+Feed_Vol+RS_cumulo+Cell_ conc._cumulo+rab_integral+RQ_integral+Arg_conc.+ emission_O2+emission_CO2; 0.480, 0.790, pH+pH_cu- mulo+PL+PL_cumulo+AN+AN_cumulo+Feed_Vol+RS_ cumulo+rab_integral+RQ_integral+Arg_conc.+emission_ O2+emission_CO2+consum_O2+generate_CO2; 0.539, 0.790, pH+PL_cumulo+AN+AN_cumulo+Feed_Vol+RS_cu- mulo+rab_integral+Arg_conc.+emission_O2+emission_ CO2+consum_O2; 0.505, 0.790, pH+PL_cumulo+AN_cu- mulo+interval_yield+Feed_Vol+RS_cumulo+rab_integral+ RQ_integral+Accum._Yield+Arg_conc.+emission_O2+ emission_CO2+consum_O2; 0.528, 0.790, pH+PL+AN_ cumulo+Feed_Vol+RS_cumulo+rab_integral+RQ_ integral+Accum._Yield+Arg_conc.+emission_O2+ emission_CO2; 0.517, 0.790, tmp_cumulo+pH+AN+ interval_yield+Feed_Vol+RS_cumulo+rab_integral+RQ_ integral+Arg_conc.+emission_O2+emission_CO2+ interval_O2; 0.480, 0.790, pH+PL_cumulo+AN+AN_ cumulo+interval_yield+Feed_Vol+RS_cumulo+rab_ integral+RQ_integral+Accum._Yield+Arg_conc.+ emission_O2+emission_CO2+consum_O2+generate_CO2; 0.528, 0.790, pH+AN+AN_cumulo+RS+Feed_Vol+Cell_ conc._interval+rab_integral+RQ_integral+Arg_conc.+ emission_O2+emission_CO2; 0.505, 0.790, tmp+tmp_cu- mulo+pH+PL+AN+Feed_Vol+RS_cumulo+rab_integral+ RQ_integral+Arg_conc.+emission_O2+emission_CO2+ consum_O2; 0.466, 0.790, pH+pH_cumulo+PL+PL_ cumulo+AN+AN_cumulo+interval_yield+Feed_Vol+RS_ cumulo+Cell_conc._interval+rab_integral+RQ_integral+ Accum._Yield+Arg_conc.+emission_O2+emission_CO2; 0.505, 0.790, tmp_cumulo+pH+AN+interval_yield+RS+ Feed_Vol+Cell_conc._interval+rab_integral+RQ_integral+ Accum._Yield+Arg_conc.+emission_O2+emission_CO2; 0.466, 0.790, pH+pH_cumulo+PL+PL_cumulo+AN+AN_ cumulo+interval_yield+Feed_Vol+RS_cumulo+Cell_ conc._interval+rab_integral+RQ_integral+Arg_conc.+ emission_O2+emission_CO2+consum_O2; 0.517, 0.790, pH+PL+PL_cumulo+AN_cumulo+Feed_Vol+RS_cumulo+ Cell_conc._cumulo+rab_integral+RQ_integral+Arg_conc.+ emission_O2+emission_CO2; 0.493, 0.790, pH+PL_cu- mulo+AN+AN_cumulo+Feed_Vol+RS_cumulo+Cell_ conc._cumulo+rab_integral+RQ_integral+Accum._Yield+ Arg_conc.+emission_O2+emission_CO2+generate_CO2; 0.528, 0.790, pH+AN+interval_yield+Feed_Vol+RS_cu- mulo+Cell_conc._cumulo+rab_integral+RQ_integral+Arg_ conc.+emission_O2+emission_CO2; 0.517, 0.790, pH+pH_ cumulo+AN+interval_yield+RS+Feed_Vol+Cell_conc._ interval+rab_integral+RQ_integral+Arg_conc.+emission_ O2+emission_CO2

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A control device comprising circuitry or a processor configured to perform control of a culture condition in production of an organic compound by a fermentation method,
   the circuitry or the processor of the control device being configured to execute processing a plurality of times to acquire culture data, to calculate, using the acquired culture data, a plurality of candidates for a culture condition set in advance, and a linear model set in advance that outputs a production amount of an organic compound at a future time, the production amount at the future time for each of the candidates, to determine an optimum candidate out of the candidates using the calculated production amount at the future time for each of the candidates and a target production amount of the organic compound at the future time set in advance, and to change the culture condition to the determined candidate, and
   the linear model and the target production amount being set for each time.

2. The control device according to claim 1, wherein the future time is a time when next time processing is executed.

3. The control device according to claim 1, determining a candidate corresponding to a production amount at the future time closest to the target production amount to be the optimum candidate.

4. The control device according to claim 1, wherein
   a plurality of the linear models are set for each time, and
   the optimum candidate is determined out of the candidates using a sample statistical amount for each of the candidates based on a plurality of production amounts at the future time for each of the candidates and the target production amount.

5. The control device according to claim 1, wherein the linear model is a multiple regression formula.

6. The control device according to claim 1, wherein the organic compound is an amino acid.

7. The control device according to claim 6, wherein the amino acid is a basic amino acid.

8. The control device according to claim 7, wherein the basic amino acid is lysine or arginine.

9. The control device according to claim 1, wherein the culture condition includes a condition on temperature, pH, or a phosphoric acid concentration.

10. A control method executed by a control device that performs control of a culture condition in production of an organic compound by a fermentation method, the control device executing processing a plurality of times to acquire culture data, to calculate, using the acquired culture data, a plurality of candidates for a culture condition set in advance, and a linear model set in advance that outputs a production amount of an organic compound at a future time, the production amount at the future time for each of the candidates, to determine an optimum candidate out of the candidates using the calculated production amount at the future time for each of the candidates and a target production amount of the organic compound at the future time set in advance, and to change the culture condition to the determined candidate, and the linear model and the target production amount being set for each time.

11. A non-transitory computer-readable storage medium storing computer-readable instructions that, when executed by a computer, cause the computer to cause a control device that performs control of a culture condition in production of an organic compound by a fermentation method to execute processing a plurality of times to acquire culture data, to calculate, using the acquired culture data, a plurality of candidates for a culture condition set in advance, and a linear model set in advance that outputs a production amount of an organic compound at a future time, the production amount at the future time for each of the candidates, to determine an optimum candidate out of the candidates using the calculated production amount at the future time for each of the candidates and a target production amount of the organic compound at the future time set in advance, and to change the culture condition to the determined candidate, and the linear model and the target production amount being set for each time.

12. A method for producing an organic compound, the method comprising producing an organic compound with a production system having the control device according to claim 1.

13. The method according to claim 12, wherein the organic compound is an amino acid.

14. The method according to claim 13, wherein the amino acid is a basic amino acid.

15. The method according to claim 14, wherein the basic acid is lysine or arginine.

* * * * *